US009169254B2

(12) United States Patent
Esaki et al.

(10) Patent No.: US 9,169,254 B2
(45) Date of Patent: Oct. 27, 2015

(54) SPIROIMIDAZOLONE DERIVATIVE

(75) Inventors: Toru Esaki, Shizuoka (JP); Yoshikazu Nishimura, Shizuoka (JP); Yoshiaki Isshiki, Shizuoka (JP); Naoki Okamoto, Shizuoka (JP); Yoshiyuki Furuta, Shizuoka (JP); Akemi Mizutani, Shizuoka (JP); Masateru Ohta, Shizuoka (JP); Wayne Wen Lai, Wuxi (CN); Tomoya Kotake, Shizuoka (JP)

(73) Assignee: Chugai Seiyaku Kabushiki Kaisha, Tokyo (JP)

( * ) Notice: Subject to any disclaimer, the term of this patent is extended or adjusted under 35 U.S.C. 154(b) by 635 days.

(21) Appl. No.: 13/266,517

(22) PCT Filed: Apr. 27, 2010

(86) PCT No.: PCT/JP2010/057432
§ 371 (c)(1), (2), (4) Date: Feb. 24, 2012

(87) PCT Pub. No.: WO2010/126030
PCT Pub. Date: Nov. 4, 2010

(65) Prior Publication Data

US 2012/0270838 A1 Oct. 25, 2012

(30) Foreign Application Priority Data

Apr. 28, 2009 (JP) ................................ 2009-109256

(51) Int. Cl.

| | |
|---|---|
| *C07D 487/10* | (2006.01) |
| *C07D 491/107* | (2006.01) |
| *A61K 31/5377* | (2006.01) |
| *A61K 31/4545* | (2006.01) |
| *C07D 515/20* | (2006.01) |
| *C07D 471/10* | (2006.01) |
| *C07D 513/20* | (2006.01) |
| *C07D 513/22* | (2006.01) |

(52) U.S. Cl.
CPC ............ *C07D 471/10* (2013.01); *C07D 513/20* (2013.01); *C07D 513/22* (2013.01); *C07D 515/20* (2013.01)

(58) Field of Classification Search
CPC .. C07D 471/10; C07D 515/20; C07D 513/22; C07D 513/20; A61K 31/438
USPC ............ 546/20, 14; 544/230, 70; 514/278, 63
See application file for complete search history.

(56) References Cited

U.S. PATENT DOCUMENTS

| | | | | |
|---|---|---|---|---|
| 7,666,892 | B2 * | 2/2010 | Eriksson et al. | 514/389 |
| 7,981,904 | B2 * | 7/2011 | Chang et al. | 514/278 |

FOREIGN PATENT DOCUMENTS

| | | | |
|---|---|---|---|
| JP | 2004-523583 | A | 8/2004 |
| JP | 2008-515895 | A | 5/2008 |
| WO | WO 02/074751 | A1 | 9/2002 |
| WO | WO 2006/041830 | A2 | 4/2005 |
| WO | WO 2007/135417 | A1 | 11/2007 |
| WO | WO 2007/149873 | A2 | 12/2007 |
| WO | WO 2008/148689 | A1 | 12/2008 |
| WO | WO 2009/074575 | A2 | 6/2009 |

OTHER PUBLICATIONS

Peter Cross et al, Cerebrovasodilatation through selective inhibition of the enzymes carbonic Anhydrase, 1978.*

Patani et al, 1996, Bioisoterism.*

Abou-Samra et al., "Expression cloning of a common receptor for parathyroid hormone and parathyroid hormone-related peptide from rat osteoblast-like cells: a single receptor stimulates intracellular accumulation of both cAMP and inositol trisphosphates and increases intracellular free calcium," Proc. Nat. Acad. Sci. USA, Apr. 1992, 89(7):2732-2736.

Bergwitz et al., "Full Activation of Chimeric Receptors by Hybrids between Parathyroid Hormone and Calcitonin," J. Biol. Chem., Oct. 25, 1996, 271(43):26469-26472.

Bringhurst et al., "Cloned, Stably Expressed Parathyroid Hormone (PTH)/PTH-Related Peptide Receptors Activate Multiple Messenger Signals and Biological Responses in LLC-PKI Kidney Cells," Endocrinology, May 1993, 132(5):2090-2098.

Broadus et al., "Parathyroid Hormone-Related Protein," the Parathyroids, J.P. Bilezikian et al., Eds., 1994, Chapter 17, 259-294.

Greenspan et al., "Effect of Recombinant Human Parathyroid Hormone (1-84) on Vertebral Fracture and Bone Mineral Density in Postmenopausal Women with Osteoporosis," Annals of Internal Medicine, Mar. 6, 2007, 146(5):326-339.

Hoare, Sam R.J., "Mechanisms of peptide and nonpeptide ligand binding to Class B G-protein-coupled receptors," Drug Discovery Today, Mar. 15, 2005, 10(6):417-427.

(Continued)

*Primary Examiner* — Rita Desai
(74) *Attorney, Agent, or Firm* — Foley & Lardner LLP

(57) ABSTRACT

The present invention relates to a compound represented by the following formula (1):

(1)

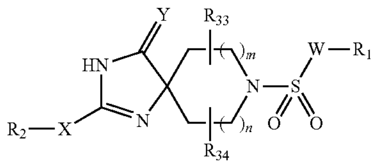

wherein W, X, Y, $R_1$, $R_2$, $R_{33}$, $R_{34}$, m and n are as defined in the claims, or a pharmacologically acceptable salt thereof.

5 Claims, No Drawings

(56) References Cited

OTHER PUBLICATIONS

Ishihara et al., "Molecular cloning and expression of a cDNA encoding the secretin receptor," The EMBO Journal, Jul. 1991, 10(7):1635-1641.
Jelinek et al., "Expression Cloning and Signaling Properties of the Rat Glucagon Receptor," Science, Mar. 12, 1993, 259(5101):1614-1616.
Karaplis et al., "Letah skeletal dysplasia from targeted disruption of the parathyroid hormone-related peptide gene," Genes & Development, Feb. 1, 1994, 8(3):277-289.
Kolakowski, Lee F., Jr., "GCRDb: A G-Protein-Coupled Receptor Database," Receptors and Channels, 1994, 2(1):1-7.
Kronenberg et al,. "Parathyroid Hormone: Biosynthesis, Secretion, Chemistry, and Action," Handbook of Experimental Pharmacology: Physiology and Pharmacology of Bone, 1993, 507-567.
Lanske et al., "PTH/PTHrP Receptor in Early Development and Indian Hedgehog-Regulated Bone Growth," Science, Aug. 2, 1996, 273(5275):663-666.
Lin et al., "Expression Cloning of an Adenylate Cyclase-Coupled Calcitonin Receptor," Science, Nov. 15, 1991, 254(5034):1022-1024.
Neer et al., "Effect of Parathyroid Hormone (1-34) on Fractures and Bone Mineral Density in Postmenopausal Women with Osteoporosis," New England Journal of Medicine, May 10, 2001, 344(19):1434-1441.
Tashjian et al.,. "Perspective: Teriparatide [Human PTH(1-34)]: 2.5 Years of Experience on the Use and Safety of the Drug for the Treatment of Osteoporosis," Journal of Bone and Mineral Research, Mar. 2006, 21(3):354-365, Epub Nov. 11, 2005.
Urena et al., "Regulation of Parathyroid Hormone (PTH)/PTH-Related Peptide Receptor Messenger Ribonucleic Acid by Glucocorticoids and PTH in ROS 17/2.8 and OK Cells," Endocrinology, Jan. 1994, 134(1):451-456.
Usdin et al., "Identification and Functional Expression of a Receptor Selectively Recognizing Parathyroid Hormone, the PTH2 Receptor," J. Biol. Chem., Jun. 30, 1995, 270(26):15455-15458.

* cited by examiner

SPIROIMIDAZOLONE DERIVATIVE

CROSS-REFERENCE TO RELATED APPLICATIONS

This application is a National Stage application of PCT/JP2010/057432, filed Apr. 27, 2010, which claims priority from Japanese application JP 2009-109256, filed Apr. 28, 2009.

TECHNICAL FIELD

The present invention relates to spiroimidazolone derivatives and use thereof.

BACKGROUND ART

Parathyroid hormone (PTH) is a major regulator of calcium homeostasis and its main target organs are considered to be the bones and kidneys. Native human parathyroid hormone is a polypeptide consisting of 84 amino acids. This hormone is secreted from the parathyroid gland in response to low blood calcium levels, and acts on osteoblasts (bone-building cells) in the bones and tubular epithelial cells in the kidneys. This hormone interacts with a cell surface receptor molecule called PTH-1 receptor or PTH/PTHrP receptor, which is expressed by both osteoblasts and renal tubular cells.

PTHrP (PTH-related protein), the major cause of humoral hypercalcemia of malignancy (HHM), also has normal functions including developmental roles. PTHrP has 141 amino acids, although mutants also occur that result from alternative gene splicing mechanisms. PTHrP plays a key role in the formation of the skeleton through a process that also involves binding to the PTH-1 receptor (Non Patent Literature 1, Non Patent Literature 2).

Regulation of calcium concentrations is necessary for normal functions of the gastrointestinal system, skeletal system, nervous system, neuromuscular system and cardiovascular system. Synthesis and release of PTH are primarily controlled by the serum calcium level. Synthesis and release of PTH are stimulated at low serum calcium levels, and synthesis and release of PTH are suppressed at high serum calcium levels. PTH, in turn, maintains the serum calcium level by directly or indirectly promoting calcium entry into the blood at three calcium exchange sites: intestine, bone and kidney. PTH contributes to net gastrointestinal absorption of calcium by assisting in the renal synthesis of active vitamin D. PTH promotes calcium mobilization from the bone to serum by stimulating differentiation of osteoclasts that are bone-resorbing cells. This also mediates at least three main effects in the kidney (stimulation of tubular calcium resorption; enhancement of phosphate clearance; and promotion of an increase in the enzyme that completes the synthesis of active vitamin D). PTH is considered to exert these effects primarily through receptor-mediated activation of adenylate cyclase and/or phospholipase C.

Disruption of calcium homeostasis may produce many clinical disorders (e.g., serious bone disease, anemia, renal dysfunction, ulcers, myopathy and neuropathy), and this usually results from conditions that produce an alteration in the level of parathyroid hormone. Hypercalcemia is a condition characterized by an elevated serum calcium level. This is often associated with primary hyperparathyroidism in which excessive PTH production occurs as a result of parathyroid gland lesions (e.g., adenoma, hyperplasia or carcinoma). Humoral hypercalcemia of malignancy (HHM), another type of hypercalcemia, is the most common paraneoplastic syndrome. This appears to result in most instances from the production of a certain protein hormone that shares amino acid homology with PTH by tumors (e.g., squamous cell carcinoma, renal carcinoma, ovarian carcinoma or bladder carcinoma). These PTHrPs appear to mimic the effects of PTH on the kidney and skeleton in some degree, and are considered to interact with the PTH receptor in these tissues. PTHrP is usually found at low levels in many tissues including keratinocytes, brain, pituitary gland, parathyroid gland, adrenal cortex, medulla, fetal liver, osteoblast-like cells and lactating mammary tissues. For many HHM malignant tumors, high levels of PTHrP are observed in the circulatory system, and this leads to elevated calcium levels associated with HHM.

The pharmacological profiles of PTH and PTHrP are nearly identical in most in vitro assay systems, and elevated blood levels of PTH (i.e., primary hyperparathyroidism) or PTHrP (i.e., HHM) have comparable effects on inorganic ion homeostasis (Non Patent Literature 3, Non Patent Literature 4). The similarities in the biological activities of the two ligands can be explained by their interaction with the PTH/PTHrP receptor, a common receptor expressed abundantly in the bones and kidneys (Non Patent Literature 5).

The PTH-1 receptor is homologous in primary structure to some other receptors binding to peptide hormones, such as secretin (Non Patent Literature 6), calcitonin (Non Patent Literature 7) and glucagon (Non Patent Literature 8); these receptors together form a distinct family called receptor family B (Non Patent Literature 9). Within this family, the PTH-1 receptor is unique in that it binds to two peptide ligands and thereby regulates two separate biological processes. A recently identified PTH receptor subtype called PTH-2 receptor binds to PTH but not to PTHrP (Non Patent Literature 10). This finding has implied that the structural differences in the PTH and PTHrP ligands determine the selectivity for interaction with the PTH-2 receptor. The PTH-2 receptor has been detected by RNA methods in the brain, pancreas and vasculature; however, its biological functions have not been determined (Non Patent Literature 10). The family B receptors are assumed to use a common molecular mechanism for engagement with their own cognate peptide hormone (Non Patent Literature 11).

The PTH-1 receptor binds to both PTH and PTHrP and causes not only intracellular cAMP accumulation and adenyl cyclase (AC) activation but also signal transduction to phospholipase C (PLC), thereby leading to the production of inositol trisphosphate (IP3), diacylglycerol (DAG) and intracellular calcium ($iCa^{2+}$) (Non Patent Literature 12, Non Patent Literature 13).

Osteoporosis is a potentially crippling bone disease and is observed in a substantial portion of the elderly population, in pregnant women and even in juveniles. The term "osteoporosis" refers to a group of disorders consisting of different constituents. Osteoporosis is clinically classified into type I and type II. Type I osteoporosis occurs primarily in middle-aged women and is associated with menopausal estrogen loss, while type II osteoporosis is associated with the elderly. Patients with osteoporosis are considered to benefit from novel therapies designed to promote fracture repair, or therapies designed to prevent or reduce fractures associated with the disease.

This disease is characterized by reduced bone mass, decreased bone mineral density (BMD), decreased bone strength and an increased risk of fracture. Currently, there is no effective cure for osteoporosis, although estrogen, calcitonin, and etidronate and alendronate that are bisphosphonates are used to treat the disease with various levels of success. These agents act to decrease bone resorption.

PTH(1-34) (teriparatide) has a strong bone anabolic effect and induces significant increases in bone mineral density and bone strength. Subcutaneous administration of human PTH (1-34) increased the spine bone mineral density (BMD) by 8% in one year and decreased the risks of vertebral fracture and nonvertebral fracture by 65% and 55% in two years, respectively (Non Patent Literature 14). Subcutaneous administration of human PTH(1-84) also increased the spine bone mineral density (BMD) by 6.9% in 18 months and decreased the risk of vertebral fracture by 58% (Non Patent Literature 15). Parathyroid hormone is currently believed to be one of the most effective treatments for osteoporosis (Non Patent Literature 16). Importantly, hPTH(1-34) must be administered in a pulsed manner (e.g., subcutaneous injection once daily) to achieve its bone-forming effect. Longer administration of PTH(1-34) such as by use of a continuous infusion pump mechanism activates bone-resorptive responses mediated by osteoclasts much stronger than bone-forming responses mediated by osteoblasts, and thus PTH(1-34) exerts a net degradation effect on the bone.

Although parathyroid hormone is believed to be one of the most effective treatments for osteoporosis, only less than 1% of patients with osteoporosis use teriparatide and the average duration of teriparatide is 12 months (Non Patent Literature 16). Teriparatide must be administered by self-injection. The fact that it is difficult to use a pen-type device for self-administration is the principal cause of the low compliance of teriparatide-administered patients. It is obvious that noninvasively, preferably orally, available compounds having a PTH-like effect with clinical efficacy in osteoporosis similar to that of parathyroid hormone can considerably improve the compliance of patients with regard to the administration, and that the compounds can be the most useful therapeutic option for patients with osteoporosis.

There are many low molecular weight agonists for the GPCR family A; however, only a limited number of low molecular weight ligands for the GPCR family B have been reported (Non Patent Literature 17). Low molecular weight agonists have been reported for the GLP-1 receptor, calcitonin receptor and PTH1 receptor belonging to the GPCR family B; however, there is no compound used in clinical applications for the treatment of diseases.

CITATION LIST

Non Patent Literature

[Non Patent Literature 1] Karaplis, A. C. et al., Genes and Dev. 8:277-289 (1994)

[Non Patent Literature 2] Lanske, B. et al., Science 273:663-666 (1996)

[Non Patent Literature 3] Broadus, A. E. & Stewart, A. F., "Parathyroid hormone-related protein: Structure, processing and physiological actions," in Basic and Clinical Concepts, Bilzikian, J. P. et al., eds., Raven Press, New York (1994), pp. 259-294

[Non Patent Literature 4] Kronenberg, H. M. et al., "Parathyroid hormone: Biosynthesis, secretion, chemistry and action," in Handbook of Experimental Pharmacology, Mundy, G. R. & Martin, T. J., eds., Springer-Verlag, Heidelberg (1993), pp. 185-201

[Non Patent Literature 5] Urena, P. et al., Endocrinology 134:451-456 (1994)

[Non Patent Literature 6] Ishihara, T. et al., EMBO J. 10:1635-1641 (1991)

[Non Patent Literature 7] Lin, H. Y. et al., Science 254:1022-1024 (1991)

[Non Patent Literature 8] Jelinek, L. J. et al., Science 259: 1614-1616 (1993)

[Non Patent Literature 9] Kolakowski, L. F., Receptors and Channels 2:1-7 (1994)

[Non Patent Literature 10] Usdin, T. et al., J. Biol. Chem. 270:15455-15458 (1995)

[Non Patent Literature 11] Bergwitz, C. et al., J. Biol. Chem. 271:26469-26472 (1996)

[Non Patent Literature 12] Abou-Samra, A. B et al., Pro. Natl. Acad. Sci. USA, 89:2732-2736, 1992

[Non Patent Literature 13] Bringhurst F. R. et al., Endocrinology 132:2090-2098, 1993

[Non Patent Literature 14] Neer R M et al., N. Eng. J. Med. 344:1434-1441, 2003

[Non Patent Literature 15] Greenspan S L et al., Ann of Intern Med. 146:326-339, 2007

[Non Patent Literature 16] Tashjian and Gagel, J. Bone Miner. Res 21:354-365 (2006)

[Non Patent Literature 17] Hoare S R J. et al., Drug Discov. Today 10:417-427 (2005)

SUMMARY OF THE INVENTION

Problems to Solved by the Invention

An object of the present invention is to provide a noninvasively, preferably orally, available low molecular weight compound having a parathyroid hormone-like effect involving bone anabolism which can considerably improve the compliance of patients as compared with a parathyroid hormone peptide agonist.

Means for Solving the Problems

Specifically, the present invention includes:

[1]

A compound represented by the following general formula (1):

(1)

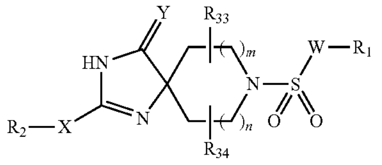

[wherein

W is selected from:

1) a single bond,

2) C1-C10 alkylene optionally containing a carbonyl group, wherein the alkylene is optionally substituted with a halogen atom(s) and/or a hydroxyl group(s), 3) C2-C10 alkenylene optionally substituted with a halogen atom(s), 4) C2-C10 alkynylene, 5) arylene optionally substituted with a halogen atom(s), 6) heteroarylene optionally substituted with a halogen atom(s), 7) C1-C10 heteroalkylene optionally substituted with a halogen atom(s), 8) $—NH—$, $—NHCH_2—$ or $—NHCH_2CH_2—$, 9) cycloalkylene and 10) -(cycloalkylene)-$CH_2$—;

X is selected from the following bond or groups:
1) a single bond,
2) C1-C10 alkylene optionally substituted with a halogen atom(s) or cycloalkyl,
3) C2-C10 alkenylene optionally substituted with a halogen atom(s),
4) C2-C10 alkynylene optionally substituted with a halogen atom(s),
5) C1-10 oxyalkylene optionally substituted with a halogen atom(s) and
6) —$NR_{47}$—
wherein $R_{47}$ is selected from:
i) a hydrogen atom and
ii) C1-C10 alkyl optionally substituted with a halogen atom(s);
Y is selected from:
1) an oxygen atom,
2) a sulfur atom and
3) =$NR_{37}$,
or 4) Y is —$NR_{38}R_{39}$ shown in the following formula (A):

(A)

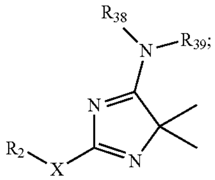

which can be tautomeric;
$R_{37}$ is selected from:
1) hydrogen,
2) hydroxy and
3) C1-C10 alkoxy;
$R_{38}$ and $R_{39}$ are independently selected from hydrogen or C1-C10 alkyl optionally substituted with cycloalkyl, or
$R_{38}$ and $R_{39}$ may be bonded to each other to form a ring selected from the group consisting of azetidinyl, pyrrolidinyl, piperidinyl, piperazinyl and morpholinyl, and the ring is optionally substituted with C1-C10 alkyl;
m represents an integer of 0 to 2;
n represents an integer of 0 to 2;
$R_1$ is selected from:
1) hydrogen,
2) cycloalkyl optionally substituted with a group(s) selected from $R_4$, $R_5$ and $R_6$,
3) a heterocycle optionally substituted with a group(s) selected from $R_{25}$, $R_4$, $R_5$ and $R_6$,
4) aryl optionally substituted with a group(s) selected from $R_3$, $R_4$, $R_5$ and $R_6$ and
5) heteroaryl optionally substituted with a group(s) selected from $R_{25}$, $R_4$, $R_5$ and $R_6$;
$R_3$ is selected from:
1) —$CONR_7R_8$,
2) —$OR_9$,
3) —$NR_9R_{10}$.
4) —$N(R_9)$ $COR_{11}$.
5) —$N(R_9)SO_2R_{12}$.
6) —$SO_2R_{15}$.
7) C1-10 alkyl optionally substituted with a group(s) independently selected from a halogen atom, a hydroxyl group, —$COR_{16}$ and —$NR_{13}R_{14}$,
8) heteroaryl optionally having C1-10 alkyl and/or C1-10 alkoxy as a substituent and
9) —$N(R_9)$ $CSR_{11}$;
$R_4$ is selected from:
1) a halogen atom,
2) cyano,
3) nitro,
4) amino,
5) —$NHCOR_{26}$,
6) C1-C10 alkyl optionally substituted with a group(s) independently selected from hydroxycarbonyl, C1-C10 alkoxycarbonyl and aminocarbonyl,
7) C1-C10 haloalkyl,
8) C1-C10 alkoxy,
9) C1-C10 haloalkylcarbonyl,
10) —$COR_{16}$,
11) C1-C10 hydroxyalkyl and
12) C1-C10 heteroalkyl;
$R_5$ is selected from a halogen atom, C1-C10 alkyl, C1-C10 haloalkyl and C1-C10 alkoxy;
$R_6$ is selected from a halogen atom, C1-C10 alkyl and C1-C10 haloalkyl;
$R_7$ is selected from:
1) hydrogen,
2) C1-C10 alkyl optionally substituted with a group(s) independently selected from amino and C1-C10 alkylamino,
3) C1-C10 hydroxyalkyl,
4) C1-C10 haloalkyl,
5) C1-C10 heteroalkyl,
6) C1-C10 heteroalkyl optionally substituted with a group(s) selected from a hydroxyl group, C1-C10 alkylamino and C2-C10 alkenyl,
7) aryl,
8) heteroaryl,
9) aryl C1-C10 alkyl,
10) a heterocycle optionally substituted with C1-C10 alkyl,
11) —$(CH_2)_LCOR_{16}$ (wherein L represents an integer of 1 to 4),
12) C1-C10 alkoxy,
13) C2-C10 alkenyl and
14) —$NR_{40}R_{41}$;
$R_{40}$ and $R_{41}$ are independently selected from hydrogen, C1-C10 alkyl and C1-C10 alkylcarbonyl, or $R_{40}$ and $R_{41}$ may be bonded to each other to form a ring selected from azetidinyl, pyrrolidinyl, piperidinyl, piperazinyl and morpholinyl, and the heterocycle is optionally substituted with C1-C10 alkyl;
$R_8$ is selected from hydrogen and C1-C10 alkyl optionally substituted with a halogen atom(s) and/or a hydroxyl group(s);
$R_7$ and $R_8$ may be bonded to form a 4- to 7-membered heterocycle optionally containing an additional element(s) or group(s) independently selected from O, N, S, SO and $SO_2$, and the heterocycle optionally contains carbonyl, and the heterocycle is optionally substituted with a substituent(s) independently selected from:
1) a halogen atom,
2) C1-C10 alkyl optionally having C1-C10 alkylamino as a substituent,
3) C1-C10 haloalkyl,
4) a hydroxyl group,
5) C1-C10 hydroxyalkyl,
6) C1-C10 alkoxy optionally substituted with a group(s) independently selected from a halogen atom, a hydroxyl group, amino and C1-C10 alkylamino,
7) aryl optionally substituted with a group(s) selected from a halogen atom, a hydroxyl group, amino and C1-C10 alkylamino, 8) C1-C10 heteroalkyl optionally substituted with a group(s) independently selected from a halogen atom, a hydroxyl group, amino and C1-C10 alkylamino, 9) a heterocycle optionally substituted with C1-C10 alkyl, 10) heteroaryl optionally substituted with C1-C10 alkyl, 11) heterocyclyl C1-C10 alkyl,

12) —$COR_{16}$,

13) —$NR_{19}R_{20}$.

14) —$SO_2R_{21}$,

15) C1-C10 alkoxy-C1-C10 alkyl optionally having a hydroxyl group(s) as a substituent(s) and 16) C1-C10 hydroxyalkyloxy, wherein the hydrogen atom of the hydroxyl group is optionally replaced by C1-C10 hydroxyalkyl, and the heterocycle may further form a spiro ring together with a 4- to 6-membered heterocycle, and the bonded 4- to 6-membered heterocycle optionally contains O and N as ring-forming elements in addition to carbon atoms, and the carbon atom(s) may be oxidized to form carbonyl, and the 4- to 6-membered heterocycle is optionally further substituted with C1-C10 alkyl;

$R_{16}$ is selected from:

1) a hydroxyl group,

2) C1-C10 alkoxy,

3) $NR_{17}R_{18}$ and

4) C1-C10 alkyl optionally substituted with a substituent(s) selected from a halogen atom, a hydroxyl group, C1-C10 alkoxycarbonyl or C1-C10 alkylamino;

$R_{17}$ is selected from:

1) hydrogen,

2) C1-C10 alkyl optionally substituted with a group(s) selected from aryl, amino, C1-C10 alkylamino, C1-C10 alkylcarbonylamino and a hydroxyl group, 3) heteroaryl and 4) C1-C10 alkoxy;

$R_{18}$ is selected from hydrogen, C1-C10 alkyl and C1-C10 hydroxyalkyl;

$R_{17}$ and $R_{18}$ may be bonded to each other to form a ring selected from azetidinyl, pyrrolidinyl, piperidinyl, piperazinyl and morpholinyl, and the ring is optionally substituted with a group(s) selected independently of each other from C1-C10 alkyl, a halogen atom and C1-C10 alkoxycarbonyl;

$R_{19}$ is selected from hydrogen, C1-C10 alkyl, C1-C10 haloalkyl, C1-C10 alkylcarbonyl, C1-C10 hydroxyalkyl, C1-C10 aminoalkyl, C1-C10 alkoxycarbonyl and C1-C10 heteroalkyl;

$R_{20}$ is selected from hydrogen and C1-C10 alkyl;

$R_{19}$ and $R_{20}$ may be bonded to form a ring selected from azetidinyl, pyrrolidinyl, piperidinyl, piperazinyl and morpholinyl, and the ring is optionally substituted with a group(s) selected independently of each other from C1-C10 alkyl and a halogen atom;

$R_{21}$ is selected from:

1) C1-C10 alkyl optionally substituted with aryl, 2) amino,

3) C1-C10 alkylamino and 4) aryl optionally substituted with C1-C10 alkyl;

$R_9$ is selected from:

1) hydrogen,

2) C1-C10 alkyl optionally substituted with a group(s) independently selected from $R_{23}$, 3) aryl optionally substituted with a group(s) selected from a halogen atom, a hydroxyl group, amino and C1-C10 alkylamino, 4) cycloalkyl optionally substituted with a halogen atom(s) or a hydroxyl group(s), 5) a heterocycle optionally substituted with a group(s) independently selected from C1-C10 alkyl, C1-C10 alkylcarbonyl, C1-C10 alkoxy, C1-C10 alkoxycarbonyl, amino and a halogen atom, 6) C1-C10 heteroalkyl optionally substituted with a group(s) independently selected from a halogen atom and a hydroxyl group, 7) heteroaryl optionally substituted with a group(s) selected from C1-C10 alkyl, C1-C10 alkylcarbonyl, C1-C10 alkoxycarbonyl and a halogen atom and 8) cycloalkenyl optionally substituted with a group(s) selected from C1-C10 alkoxy, C1-C10 alkylamino, amino, a hydroxyl group and a halogen atom, wherein the cycloalkenyl optionally contains a carbonyl group;

$R_{23}$ is independently selected from:

1) a halogen atom, 2) a hydroxyl group, 3) a C1-C10 alkylcarbonyloxy group,

4) —$COR_{16}$, 5) amino,

6) C1-C10 alkylamino, 7) a heterocycle optionally substituted with a group(s) selected from C1-C10 alkyl, C1-C10 alkylcarbonyl, C1-C10 alkoxycarbonyl and a halogen atom and 8) cyano;

$R_{10}$ is selected from:

1) hydrogen and

2) C1-C10 alkyl optionally substituted with a group(s) selected from a halogen atom, a hydroxyl group and aryl;

$R_9$ and $R_{10}$ may be bonded to form a 4- to 7-membered heterocycle optionally containing an additional element(s) or group(s) independently selected from N, O, S, SO, $SO_2$, carbonyl and thiocarbonyl, and the heterocycle is optionally substituted with a substituent(s) independently selected from $R_{24}$;

$R_{24}$ is independently selected from:

1) a halogen atom,

2) C1-C10 alkyl optionally substituted with a group(s) independently selected from C1-C10 alkylamino and C1-C10 alkylcarbonylamino, 3) C1-C10 haloalkyl, 4) a hydroxyl group, 5) C1-C10 hydroxyalkyl, 6) C1-C10 alkoxy optionally substituted with a group(s) independently selected from a halogen atom, a hydroxyl group, amino and C1-C10 alkylamino, 7) aryl optionally substituted with a group(s) independently selected from a halogen atom, a hydroxyl group, amino and C1-C10 alkylamino, 8) C1-C10 heteroalkyl optionally substituted with a group(s) independently selected from a halogen atom, a hydroxyl group, amino and C1-C10 alkylamino, 9) a heterocycle optionally substituted with C1-C10 alkyl, 10) heteroaryl, 11) heterocyclyl C1-C10 alkyl,

12) —$COR_{16}$,

13) —$NR_{19}R_{20}$ and

14) —$SO_2R_{21}$;

$R_{11}$ is selected from:

1) C1-C10 alkyl optionally substituted with a group(s) independently selected from:

i) a hydroxyl group, ii) —$NR_{17}R_{18}$, iii) a C1-C10 alkoxy group, iv) a halogen atom, v) C1-C10 alkoxycarbonyl, vi) aminocarbonyl and vii) aryl optionally substituted with a group(s) independently selected from a halogen atom, a hydroxyl group, C1-C10 alkoxy, amino, C1-C10 alkylamino and —$COR_{22}$, 2) aryl optionally substituted with a group(s) independently selected from a halogen atom, a hydroxyl group, C1-C10 alkoxy, amino, C1-C10 alkylamino and —$COR_{22}$, 3) cycloalkyl optionally substituted with a halogen atom(s), 4) a heterocycle optionally substituted with a group(s) selected from C1-C10 alkyl, C1-C10 alkylcarbonyl, C1-C10 alkoxycarbonyl and a halogen atom, 5) C1-C10 alkoxy, wherein the alkyl group is optionally substituted with a group(s) independently selected from C1-C10 alkylcarbonylamino, amino, C1-C10 alkylamino and a hydroxyl group, 6) amino, 7) C1-C10 alkylamino, wherein the alkyl group is optionally substituted with a group(s) independently selected from C1-C10 alkylcarbonylamino, amino, C1-C10 alkylamino, hydroxycarbonyl and a hydroxyl group and 8) C2-C10 alkenyl;

$R_{22}$ is selected from C1-C10 alkoxy, a hydroxyl group, amino and C1-C10 alkylamino;

$R_{12}$ is selected from:

1) C1-C10 alkyl, 2) amino and

3) C1-C10 alkylamino, wherein the alkyl group is optionally substituted with a group(s) independently selected from amino, C1-C10 alkylamino and a hydroxyl group;

$R_{13}$ is selected from:

1) hydrogen,

2) C1-C10 alkyl,

3) C1-C10 alkylcarbonyl, wherein the alkyl is optionally substituted with a hydroxyl group(s), 4) C1-C10 alkoxycarbonyl, 5) aminocarbonyl, 6) C1-C10 alkylaminocarbonyl and 7) heterocyclic carbonyl optionally substituted with C1-C10 alkyl;

$R_{14}$ is selected from:

1) hydrogen and

2) C1-C10 alkyl optionally substituted with a group(s) independently selected from a halogen atom, a hydroxyl group, amino and C1-C10 alkylamino;

$R_{13}$ and $R_{14}$ may be bonded to form a 4- to 7-membered heterocycle optionally containing an additional element(s) or group(s) independently selected from O, N, S, SO and $SO_2$, and the heterocycle optionally contains carbonyl, and the heterocycle is optionally substituted with C1-C10 alkyl;

$R_{15}$ is selected from:

1) C1-C10 alkyl and

2) —$NR_{35}R_{36}$;

$R_{35}$ is selected from:

1) hydrogen,

2) C1-C10 alkyl optionally substituted with a group(s) independently selected from:

i) a halogen atom, ii) a hydroxyl group, iii) C1-C10 alkylcarbonylamino, iv) —$COR_{16}$, v) amino, vi) C1-C10 alkylamino, vii) C1-C10 alkoxy optionally substituted with a halogen atom(s), viii) heteroaryl optionally substituted with a C1-C10 alkyl group(s) and ix) a heterocycle, 3) aryl optionally substituted with a group(s) independently selected from a halogen atom, a hydroxyl group, amino and C1-C10 alkylamino, 4) cycloalkyl optionally substituted with a group(s) independently selected from a halogen atom and a hydroxyl group, 5) a heterocycle optionally substituted with a group(s) independently selected from C1-C10 alkyl, a halogen atom and aryl C1-C10 alkyl, 6) heteroaryl optionally substituted with C1-C10 alkyl and 7) C1-C10 alkylcarbonyl;

$R_{36}$ is selected from:

1) hydrogen and

2) C1-C10 alkyl optionally substituted with a group(s) independently selected from a halogen atom, a hydroxyl group and aryl;

$R_{35}$ and $R_{36}$ may be bonded to each other to form a ring selected from azetidinyl, pyrrolidinyl, piperidinyl, piperazinyl and morpholinyl, and the ring is optionally substituted with a group(s) selected independently of each other from C1-C10 alkyl and a halogen atom;

$R_{25}$ is selected from:

1) a halogen atom,

2) C1-C10 alkyl optionally substituted with a group(s) independently selected from:

i) a halogen atom, ii) aryl, iii) heteroaryl, iv) a heterocycle optionally substituted with a C1-C10 alkyl group(s), v) —$COR_{16}$, vi) —$NR_{13}R_{14}$ and vii) —$SO_2R_{21}$.

3) C1-C10 heteroalkyl optionally substituted with a hydroxyl group(s),

4) C1-C10 hydroxyalkyl, wherein each hydroxyl group may be independently substituted with a group(s) selected from C1-C10 alkyl, aryl C1-C10 alkyl and C1-C10 alkylcarbonyl,

5) —$COR_{16}$,

6) —$SO_2R_{21}$, 7) aryl and 8) cyano;

$R_2$ is selected from:

1) C1-C10 alkyl optionally substituted with a halogen atom(s), wherein the alkyl group is optionally further substituted with a substituent(s) independently selected from $R_{42}$, 2) C2-C10 alkenyl optionally substituted with a halogen atom(s), wherein the alkenyl group is optionally further substituted with a substituent(s) independently selected from $R_{42}$, 3) C2-C10 alkynyl optionally substituted with a halogen atom(s), wherein the alkynyl group is optionally further substituted with a substituent(s) independently selected from $R_{42}$, 4) cycloalkyl optionally substituted with a group(s) independently selected from:

i) a halogen atom, ii) C2-C10 alkenyl or C1-C10 alkyl, iii) aryl optionally substituted with 1 to 3 substituents independently selected from C1-C10 alkyl, a halogen atom, C1-C10 alkoxy, C1-C10 alkylamino and C1-C10 alkylcarbonyl, iv) cycloalkyl, v) C2-C10 alkenyl optionally substituted with halogen, vi) C1-C10 alkylidene, wherein the alkylidene is bonded to the cycloalkyl by a double bond and the alkylidene is optionally substituted with a halogen atom(s), vii) C1-C10 alkoxy optionally substituted with a halogen atom(s), viii) C1-C10 alkyl optionally substituted with a group(s) independently selected from a halogen atom or C1-C10 alkoxy optionally substituted with a halogen atom(s), ix) C2-C10 alkynyl and X) —$Si(R_{43})_3$, 5) a heterocycle, wherein the heterocycle is optionally substituted with a group(s) independently selected from:

i) a C1-C10 alkyl group, ii) C1-C10 alkylcarbonyl, wherein the alkyl group is optionally substituted with $R_{27}$, iii) arylcarbonyl, wherein the aryl group is optionally substituted with a group(s) independently selected from a halogen atom, C1-C10 alkyl and C1-C10 alkoxy, iv) heteroarylcarbonyl, v) C1-C10 alkoxycarbonyl, wherein the alkyl group is optionally substituted with a group(s) independently selected from a halogen atom, aryl and C1-C10 alkoxy, vi) aryloxycarbonyl, wherein the aryl group is optionally substituted with a halogen atom(s) and/or C1-C10 alkyl, vii) —$CONR_{28}R_{29}$, viii) —$SO_2R_{21}$, ix) a halogen atom, x) cycloalkylcarbonyl optionally fused with an aryl group and xi) C2-C10 alkenylcarbonyl, wherein the alkenyl group is optionally substituted with aryl, wherein the aryl is optionally substituted with a group(s) independently selected from a halogen atom, C1-C10 alkyl or C1-C10 alkoxy, 6) aryl optionally substituted with a group(s) independently selected from $R_{44}$, 7) heteroaryl optionally substituted with a group(s) independently selected from:

i) a halogen atom, ii) C1-C10 alkyl and iii) C1-C10 alkoxy;

8) C1-C10 alkoxy optionally substituted with a halogen atom(s), wherein the alkoxy group is optionally further substituted with a substituent(s) independently selected from $R_{42}$, 9) —$S(O)_qR_{43}$ (wherein q is an integer of 0 to 2) and 10) cycloalkenyl optionally substituted with C1-C10 alkyl;

$R_{44}$ is selected from:

1) a halogen atom, 2) cyano,

3) C1-C10 alkyl optionally substituted with a group(s) independently selected from:

i) a hydroxyl group, ii) —$OR_{26}$, iii) cyano, iv) aryloxy optionally substituted with a group(s) independently selected from a halogen atom, C1-C10 alkyl optionally substituted with a halogen atom(s) or C1-C10 alkoxy optionally substituted with a halogen atom(s) and v) a halogen atom, 4) cycloalkyl optionally substituted with a group(s) independently selected from a halogen atom or C1-C10 alkyl optionally substituted with a halogen atom(s), 5) C1-C10 alkoxy optionally substituted with a halogen atom(s) or a C2-C6 alkenyl group,

6) —$COR_{30}$,

7) C1-C10 alkylcarbonylamino,

8) C1-C10 alkoxycarbonylamino, wherein the alkoxy group is optionally substituted with aryl, 9) C1-C10 heteroalkyl optionally substituted with a halogen atom(s), 10) aryl optionally substituted with a substituent(s) independently selected from:

i) a halogen atom, ii) C1-C10 alkyl, iii) C1-C10 alkoxy and iv) aryl optionally substituted with aryl optionally substituted with C1-C10 alkyl, 11) heteroaryl optionally substituted with a C1-C10 alkyl group(s),

12) —$SO_2R_{43}$,

13) —$SOR_{43}$.

14) C1-C10 alkylthio optionally substituted with a halogen atom(s),

15) —$Si(R_{43})_3$ and

16) —$SF_5$;

$R_{42}$ is selected from:

1) hydrogen, 2) aryl optionally substituted with a group(s) independently selected from C1-C10 alkyl optionally substituted with halogen, a halogen atom and C1-C10 alkoxy, 3) hydroxycarbonyl, 4) C1-C10 alkoxycarbonyl, 5) aminocarbonyl, 6) C1-C10 alkylaminocarbonyl, 7) C1-C10 alkoxycarbonylamino, 8) amino, 9) a hydroxyl group and 10) oxetane, tetrahydrofuran or tetrahydropyran optionally substituted with C1-C10 alkyl;

$R_{43}$ represents a C1-C10 alkyl group;

$R_{26}$ is aryl, or C1-C10 alkyl optionally substituted with a halogen atom(s);

$R_{27}$ is selected from:

1) aryl optionally substituted with a group(s) independently selected from a halogen atom, C1-C10 alkyl and C1-C10 alkoxy, 2) C1-C10 alkoxy, wherein the alkyl group is optionally substituted with aryl, 3) a hydroxyl group, 4) amino, 5) C1-C10 alkylamino, 6) hydroxycarbonyl, 7) heteroaryl optionally substituted with a group(s) independently selected from C1-C10 alkyl and/or aryl, and 8) heteroaryloxy;

$R_{28}$ is selected from hydrogen or C1-C10 alkyl optionally substituted with aryl;

$R_{29}$ is selected from hydrogen or C1-C10 alkyl optionally substituted with aryl;

$R_{28}$ and $R_{29}$ may be bonded to form a ring selected from azetidinyl, pyrrolidinyl, piperidinyl, piperazinyl and morpholinyl, and the ring is optionally substituted with a group(s) selected independently of each other from C1-C10 alkyl and a halogen atom;

$R_{30}$ is selected from a hydroxyl group, C1-C10 alkoxy and —$NR_{31}R_{32}$;

$R_{31}$ and $R_{32}$ are independently selected from:

1) hydrogen,

2) C1-C10 alkyl optionally substituted with aryl and 3) aryl;

$R_{31}$ and $R_{32}$ may be bonded to form a ring selected from azetidinyl, pyrrolidinyl, piperidinyl, piperazinyl and morpholinyl, and the ring is optionally substituted with a group(s) selected independently of each other from C1-C10 alkyl, a halogen atom and C1-C10 alkoxycarbonyl; and $R_{33}$ and $R_{34}$ are independently selected from:

1) hydrogen and

2) C1-C10 alkyl], or a pharmacologically acceptable salt thereof; or a compound represented by the following general formula (2):

(2)

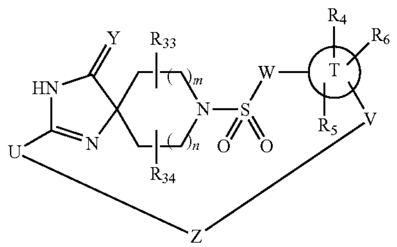

[wherein W, Y, m, n, $R_4$, $R_5$, $R_6$, $R_7$, $R_{11}$, $R_{16}$, $R_{19}$, $R_{20}$, $R_{21}$, $R_{33}$, $R_{34}$ and $R_{44}$ are as defined for the formula (1);

U represents a bond, C1-C10 alkylene or any group selected from groups represented by the following formula:

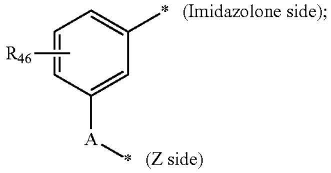

A is selected from O, NH and $CH_2$;

$R_{46}$ is selected from hydrogen or $R_{44}$;

T is selected from aryl and heteroaryl;

V is selected from:

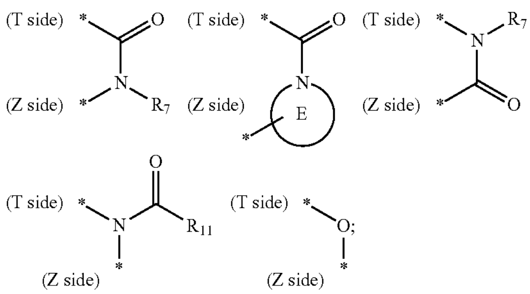

E is a 4- to 7-membered heterocycle optionally containing an additional element(s) or group(s) selected from O, N, S, SO and $SO_2$, and the heterocycle is optionally substituted with a group(s) selected from:

1) hydrogen, 2) a halogen atom,

3) C1-C10 alkyl optionally having a group(s) independently selected from C1-C10 alkylamino, a halogen atom and a hydroxyl group, 4) a hydroxyl group, 5) C1-C10 alkoxy optionally substituted with a group(s) independently selected from a halogen atom, a hydroxyl group, amino and C1-C10 alkylamino, 6) aryl optionally substituted with a group(s) independently selected from a halogen atom, a hydroxyl group, amino and C1-C10 alkylamino, 7) C1-C10 heteroalkyl optionally substituted with a group(s) independently selected from a halogen atom, a hydroxyl group, amino and C1-C10 alkylamino, 8) a heterocycle optionally substituted with C1-C10 alkyl, 9) heteroaryl optionally substituted with C1-C10 alkyl, 10) heterocyclyl C1-C10 alkyl,

11) $—COR_{16}$,

12) $—NR_{19}R_{20}$ and

13) $—SO_2R_{21}$;

Z is a divalent group selected from:

1) C1-C10 alkylene or C1-C10 heteroalkylene optionally substituted with a halogen atom(s) and/or a hydroxyl group(s), wherein the carbon atom(s) may be oxidized to form carbonyl;

2) C2-C10 alkenylene or C2-C10 heteroalkenylene optionally substituted with a halogen atom(s) and/or a hydroxyl group(s), wherein the carbon atom(s) may be oxidized to form carbonyl; and 3) a group selected from:

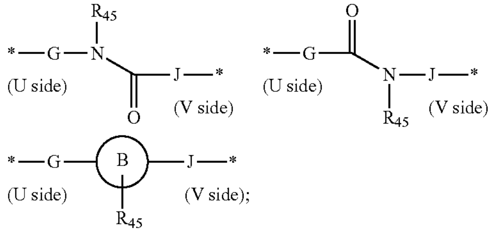

G is a divalent group selected from:

1) C1-C10 alkylene or C1-C10 heteroalkylene optionally substituted with a halogen atom(s); and 2) C2-C10 alkenylene or C2-C10 heteroalkenylene optionally substituted with a halogen atom(s);

J is a divalent group selected from:

1) C1-C10 alkylene or C1-C10 heteroalkylene optionally substituted with a halogen atom(s); and 2) C2-C10 alkenylene or C2-C10 heteroalkenylene optionally substituted with a halogen atom(s);

B is selected from a heterocycle or heteroaryl; and $R_{45}$ is selected from hydrogen or C1-C10 alkyl], or a pharmacologically acceptable salt thereof.

[2]

The compound or a pharmacologically acceptable salt thereof according to [1], wherein W is selected from:

1) a single bond,

2) C1-C10 alkylene optionally containing a carbonyl group, wherein the alkylene is optionally substituted with a halogen atom(s) or hydroxy, 3) C2-C10 alkenylene optionally substituted with a halogen atom(s), 4) C2-C10 alkynylene, 5) arylene, 6) heteroarylene, 7) —NH—, $—NHCH_2—$ or $—NHCH_2CH_2—$, 8) cycloalkylene and 9) $-(cycloalkylene)-CH_2—$;

X is selected from the following bond or groups:

1) a single bond,

2) C1-C10 alkylene optionally substituted with cycloalkyl,

3) C2-C10 alkenylene,

4) C2-C10 alkynylene and

5) C1-C10 oxyalkylene;

$R_1$ is selected from:
1) hydrogen,
2) cycloalkyl optionally substituted with a group selected from $R_4$,
3) a heterocycle optionally substituted with a group(s) selected from $R_{25}$ and $R_4$,
4) aryl optionally substituted with a group(s) selected from $R_3$, $R_4$, $R_5$ and $R_6$ and
5) heteroaryl optionally substituted with a group(s) selected from $R_{25}$, $R_4$ and $R_5$;
$R_9$ is selected from:
1) hydrogen,
2) C1-C10 alkyl optionally substituted with a group(s) independently selected from $R_{23}$,
3) cycloalkyl optionally substituted with a halogen atom(s) or a hydroxyl group(s),
4) a heterocycle optionally substituted with a group(s) selected from C1-C10 alkyl, C1-C10 alkylcarbonyl, C1-C10 alkoxy, C1-C10 alkoxycarbonyl, amino and a halogen atom,
5) C1-C10 heteroalkyl optionally substituted with a group(s) selected from a halogen atom and a hydroxyl group,
6) heteroaryl optionally substituted with a group(s) independently selected from C1-C10 alkyl, C1-C10 alkylcarbonyl, C1-C10 alkoxycarbonyl and a halogen atom and
7) cycloalkenyl optionally substituted with a group(s) selected from C1-C10 alkoxy, C1-C10 alkylamino, amino, 1 to 3 hydroxyl groups and 1 to 4 halogen atoms, wherein the cycloalkenyl optionally contains a carbonyl group;
$R_{10}$ is selected from:
1) hydrogen and
2) C1-C10 alkyl optionally substituted with a group(s) independently selected from a halogen atom, a hydroxyl group and aryl;
$R_9$ and $R_{10}$ may be bonded to form a 4- to 7-membered heterocycle optionally containing an additional element(s) or group(s) independently selected from N, O, S, SO, $SO_2$, carbonyl and thiocarbonyl, and the heterocycle is optionally substituted with a substituent(s) independently selected from $R_{24}$;
$R_{24}$ is selected from:
1) a halogen atom,
2) C1-C10 alkyl optionally substituted with a group(s) independently selected from C1-C10 alkylamino and C1-C10 alkylcarbonylamino,
3) C1-C10 haloalkyl,
4) a hydroxyl group,
5) C1-C10 hydroxyalkyl,
6) C1-C10 alkoxy optionally substituted with a group(s) independently selected from a halogen atom, a hydroxyl group, amino and C1-C10 alkylamino,
7) aryl optionally substituted with a group(s) selected from a halogen atom, a hydroxyl group, amino and C1-C10 alkylamino,
8) C1-C10 heteroalkyl optionally substituted with 1 to 2 groups selected from a halogen atom, a hydroxyl group, amino and C1-C10 alkylamino,
9) —$COR_{26}$ and
10) —$NR_{19}R_{20}$;
$R_{11}$ is selected from:
1) C1-C10 alkyl optionally substituted with 1 to 3 substituents independently selected from:
i) a hydroxyl group,
ii) —$NR_{17}R_{18}$,
iii) a C1-C10 alkoxy group,
iv) a halogen atom,
v) C1-C10 alkoxycarbonyl and
vi) aminocarbonyl,
2) aryl,
3) aryl C1-C10 alkyl,
4) cycloalkyl optionally substituted with a halogen atom(s),
5) a heterocycle optionally substituted with C1-C10 alkyl,
6) C1-C10 alkoxy, wherein the alkyl group is optionally substituted with a group(s) independently selected from C1-C10 alkylcarbonylamino, amino, C1-C10 alkylamino and a hydroxyl group,
7) amino,
8) C1-C10 alkylamino, wherein the alkyl group is optionally substituted with a group(s) independently selected from C1-C10 alkylcarbonylamino, amino, C1-C10 alkylamino, hydroxycarbonyl and a hydroxyl group and
9) C2-C10 alkenyl; and
$R_{33}$ and $R_{34}$ are hydrogen,
wherein $R_3$, $R_4$, $R_5$, $R_6$, $R_{16}$, $R_{17}$, $R_{18}$, $R_{19}$, $R_{20}$, $R_{23}$ and $R_{25}$ are as defined in [1], respectively.

[3]

The compound or a pharmacologically acceptable salt thereof according to [1] or [2], wherein
W is selected from:
1) a single bond,
2) C1-C10 alkylene optionally substituted with a halogen atom(s),
3) C2-C10 alkenylene,
4) C2-C10 alkynylene and
5) heteroarylene,
X is selected from the following bond or groups:
1) a single bond,
2) C1-C10 alkylene,
3) C2-C10 alkenylene,
4) C2-C10 alkynylene and
5) C1-C10 oxyalkylene, wherein the oxyalkylene is bonded to a 1,3,8-triaza-spiro[4.5]dec-1-en-4-one ring or a 1,3,8-triaza-spiro[4.5]dec-1-ene-4-thione ring through a carbon atom in the oxyalkylene;
$R_1$ is selected from:
1) aryl optionally substituted with a group(s) selected from $R_3$, $R_4$ and $R_5$ and
2) heteroaryl optionally substituted with a group(s) selected from $R_{25}$ and $R_4$;
$R_3$ is selected from:
1) —$CONR_7R_8$,
2) —$OR_8$,
3) —$NR_9R_{10}$,
4) —$N(R_8)$ $COR_{11}$,
5) —$N(R_8)$ $SO_2R_{12}$,
6) —$SO_2R_{15}$,
7) C1-C10 alkyl optionally substituted with a group(s) selected from —$COR_{16}$ and —$NR_{13}R_{14}$ and
8) —$N(R_9)CSNH_2$;
$R_4$ is selected from:
1) halogen,
2) cyano,
3) amino,
4) C1-C10 alkyl,
5) C1-C10 haloalkyl,
6) C1-C10 alkoxy,
7) C1-C10 haloalkylcarbonyl,
8) —$COR_{16}$ and
9) C1-C10 heteroalkyl;
$R_2$ is selected from:
1) C1-C10 alkyl optionally substituted with a halogen atom(s), wherein the alkyl group is optionally further substituted with a group selected from $R_{42}$,
2) C2-C10 alkenyl optionally substituted with a halogen atom(s), wherein the alkenyl group is optionally further substituted with a group selected from $R_{42}$, 3) C2-C10 alkynyl optionally substituted with a halogen atom(s), wherein the alkynyl group is optionally further substituted with a group selected from $R_{42}$, 4) cycloalkyl optionally substituted with a group(s) independently selected from:

i) a halogen atom, ii) C2-C10 alkenyl or C1-C10 alkyl, iii) aryl optionally substituted with a group(s) independently selected from C1-C10 alkyl, a halogen atom and C1-C10 alkoxy, iv) cycloalkyl, v) C2-C10 haloalkenyl or C1-C10 haloalkyl, vi) C1-C10 alkylidene, wherein the alkylidene is bonded to the cycloalkyl by a double bond and the alkylidene is optionally substituted with a halogen atom(s), vii) C1-C10 alkoxy optionally substituted with a halogen atom(s), viii) C1-C10 alkyl substituted with C1-C10 alkoxy, wherein the alkyl and/or the alkyl in the alkoxy is optionally substituted with a halogen atom(s), ix) C2-C10 alkynyl and x) —$Si(R_{43})_3$, 5) a heterocycle, wherein the heterocycle is optionally substituted with a group(s) selected from:

i) a C1-C10 alkyl group, ii) C1-C10 alkylcarbonyl, wherein the alkyl group is optionally substituted with $R_{27}$, iii) arylcarbonyl, wherein the aryl group is optionally substituted with a group(s) independently selected from a halogen atom, C1-C10 alkyl and C1-C10 alkoxy, iv) heteroarylcarbonyl, v) C1-C10 alkoxycarbonyl, wherein the alkyl group is optionally substituted with a group(s) independently selected from a halogen atom, aryl and C1-C10 alkoxy, vi) aryloxycarbonyl, wherein the aryl group is optionally substituted with a halogen atom(s) and/or C1-C10 alkyl, vii) —$CONR_{28}R_{29}$ and viii) —$SO_2R_{21}$, 6) aryl optionally substituted with a group(s) independently selected from $R_{44}$, 7) heteroaryl optionally substituted with any of the following groups:

i) C1-C10 alkyl,

8) C1-C10 alkoxy optionally substituted with a halogen atom(s), wherein the alkoxy group is optionally further substituted with a group selected from $R_{42}$, 9) —$S(O)_qR_{43}$ (wherein q is an integer of 0 to 2) and 10) cycloalkenyl optionally substituted with C1-C10 alkyl, $R_{44}$ is selected from:

1) a halogen atom, 2) cyano,

3) C1-C10 alkyl optionally substituted with any of the following groups:

i) a hydroxyl group, ii) —$OR_{26}$, iii) cyano and iv) aryloxy optionally substituted with a group(s) selected from a halogen atom, C1-C10 alkyl, C1-C10 haloalkyl or C1-C10 haloalkoxy, 4) C1-C10 haloalkyl, 5) cycloalkyl optionally substituted with a group(s) selected from a halogen atom and C1-C10 haloalkyl, 6) C1-C10 alkoxy optionally substituted with a halogen atom(s) or a C2-C6 alkenyl group,

7) —$COR_{30}$,

8) C1-C10 heteroalkyl optionally substituted with a halogen atom(s), 9) aryl optionally substituted with a group(s) independently selected from:

i) C1-C10 alkyl and ii) aryl, 10) heteroaryl optionally substituted with a C1-C10 alkyl group(s),

11) —$SO_2R_{43}$,

12) C1-C10 alkylthio optionally substituted with a halogen atom(s),

13) —$Si(R_{43})_3$ and

14) —$SF_5$; and $R_{27}$ is selected from:

1) aryl optionally substituted with a group(s) independently selected from a halogen atom, C1-C10 alkyl and C1-C10 alkoxy, 2) C1-C10 alkoxy, wherein the alkyl group is optionally substituted with aryl, 3) heteroaryl optionally substituted with a group(s) independently selected from C1-C10 alkyl and aryl and 4) heteroaryloxy, wherein $R_5$, $R_7$, $R_8$, $R_9$, $R_{10}$, $R_{11}$, $R_{12}$, $R_{13}$, $R_{14}$, $R_{15}$, $R_{16}$, $R_{21}$, $R_{25}$, $R_{26}$, $R_{28}$, $R_{29}$, $R_{90}$, $R_{42}$ and $R_{43}$ are as defined in [1] or [2] from which [3] depends, respectively.

[4]

The compound or a pharmacologically acceptable salt thereof according to any of [1] to [3], wherein W is selected from:

1) C1-C6 alkylene optionally substituted with a fluorine atom(s),

2) C1-C6 alkenylene and 3) thiophene,

X is selected from the following bond or groups:

1) a single bond,

2) C1-C6 alkylene and

3) C1-C6 oxyalkylene optionally substituted with a halogen atom(s), wherein the oxyalkylene is bonded to a 1,3,8-triaza-spiro[4.5]dec-1-en-4-one ring or a 1,3,8-triaza-spiro[4.5]dec-1-ene-4-thione ring through a carbon atom in the oxyalkylene;

Y represents an oxygen atom;

m represents 1; and n represents 1.

[5]

The compound or a pharmacologically acceptable salt thereof according to any of [1] to [4], wherein W is selected from:

1) ethylene, 2) vinylene and 3) thiophene,

X represents a single bond;

$R_3$ is selected from:

1) —$CONR_7R_8$,

2) —$OR_9$,

3) —$NR_9R_{10}$,

4) —$N(R_9)COR_{11}$,

5) —$N(R_9)\ SO_2R_{12}$,

6) —$SO_2R_{15}$ and

7) C1-C6 alkyl optionally substituted with a group(s) selected from —$COR_{16}$ and —$NR_{13}R_{14}$;

$R_2$ is selected from:

1) C1-C10 alkyl optionally substituted with a halogen atom(s), wherein the alkyl group is optionally further substituted with a group selected from $R_{42}$, 2) C2-C10 alkenyl optionally substituted with a halogen atom(s), wherein the alkenyl group is optionally further substituted with a group selected from $R_{42}$, 3) C2-C10 alkynyl optionally substituted with a halogen atom(s), wherein the alkynyl group is optionally further substituted with a group selected from $R_{42}$, 4) cycloalkyl optionally substituted with a group(s) independently selected from:

i) a halogen atom, ii) C2-C6 alkenyl or C1-C6 alkyl, iii) aryl optionally substituted with a group(s) independently selected from C1-C6 alkyl, a halogen atom, C1-C6 alkoxy, C1-C6 alkylamino and C1-C6 alkylcarbonyl, iv) cycloalkyl, v) C2-C6 haloalkenyl or C1-C6 haloalkyl, vi) C1-C6 alkylidene, wherein the alkylidene is bonded to the cycloalkyl by a double bond and the alkylidene is optionally substituted with a halogen atom(s), vii) C1-C6 alkoxy optionally substituted with a halogen atom(s), viii) C1-C6 alkyl substituted with C1-C6 alkoxy, wherein the alkyl and/or the alkyl in the alkoxy is optionally substituted with halogen, ix) C2-C6 alkynyl and x) —Si($R_{43}$)$_3$, 5) a group represented by the following general formula (B):

(B)

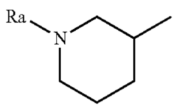

(wherein Ra represents a group selected from:

i) C1-C6 alkylcarbonyl, wherein the alkyl group is optionally substituted with $R_{27}$, ii) arylcarbonyl, wherein the aryl group is optionally substituted with a group(s) independently selected from a halogen atom, C1-C6 alkyl and C1-C6 alkoxy, iii) C1-C6 alkoxycarbonyl, wherein the alkyl group is optionally substituted with a group(s) selected from a halogen atom, aryl and C1-C6 alkoxy, iv) aryloxycarbonyl, wherein the aryl group is optionally substituted with a halogen atom(s) or C1-C6 alkyl, v) —CON$R_{28}R_{29}$ and vi) —$SO_2R_{21}$), 6) aryl optionally substituted with a group(s) independently selected from $R_{44}$, 7) heteroaryl optionally substituted with any of the following groups:

i) a halogen atom, ii) C1-C6 alkyl and iii) C1-C6 alkoxy;

8) C1-C6 alkoxy optionally substituted with a halogen atom(s), wherein the alkoxy group is optionally further substituted with a group selected from $R_{42}$.

9) —S(O)$_q R_{43}$ (wherein q is an integer of 0 to 2) and 10) cycloalkenyl optionally substituted with C1-C6 alkyl; and $R_{44}$ is selected from:

1) a halogen atom, 2) cyano,

3) C1-C6 alkyl optionally substituted with any of the following groups:

i) a hydroxyl group, ii) —$OR_{26}$, iii) cyano and iv) aryloxy optionally substituted with a group(s) selected from a halogen atom, C1-C6 alkyl, C1-C6 haloalkyl or C1-C6 haloalkoxy, 4) C1-C6 haloalkyl, 5) cycloalkyl optionally substituted with a group(s) selected from a halogen atom and C1-C6 haloalkyl, 6) C1-C6 alkoxy optionally substituted with a halogen atom(s),

7) —$COR_{30}$,

8) C1-C6 heteroalkyl optionally substituted with a halogen atom(s), 9) aryl optionally substituted with a group(s) independently selected from:

i) C1-C6 alkyl and ii) aryl, 10) heteroaryl optionally substituted with a C1-C6 alkyl group(s),

11) —$SO_2R_{43}$,

12) C1-C6 alkylthio optionally substituted with a halogen atom(s),

13) —Si($R_{43}$)$_3$ and

14) —$SF_5$, wherein $R_7$, $R_8$, $R_9$, $R_{10}$, $R_{11}$, $R_{12}$, $R_{13}$, $R_{14}$, $R_{15}$, $R_{16}$, $R_{21}$, $R_{26}$, $R_{27}$, $R_{28}$, $R_{29}$, $R_{30}$, $R_{42}$ and $R_{43}$ are as defined in [1] to [4] from which [5] depends, respectively.

[6]

The compound or a pharmacologically acceptable salt thereof according to [3], wherein $R_1$ is a group represented by the following general formula (3):

(3)

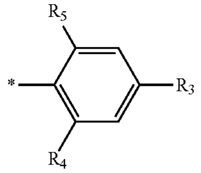

wherein $R_3$, $R_4$ and $R_5$ are as defined for $R_3$, $R_4$ and $R_5$ in [3].

[7]

The compound or a pharmacologically acceptable salt thereof according to [3], wherein $R_1$ is a group represented by the following general formula (4):

(4)

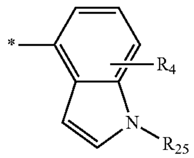

wherein $R_4$ and $R_{25}$ are as defined for $R_4$ and $R_{25}$ in [3].

[8]

The compound or a pharmacologically acceptable salt thereof according to [5], wherein $R_1$ is a group represented by the following general formula (3):

(3)

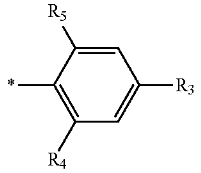

wherein $R_3$, $R_4$ and $R_5$ are as defined for $R_3$, $R_4$ and $R_5$ in [5].

[9]

The compound or a pharmacologically acceptable salt thereof according to [5], wherein $R_1$ is a group represented by the following general formula (4):

(4)

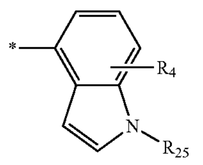

wherein $R_4$ and $R_{25}$ are as defined for $R_4$ and $R_{25}$ in [5].

[10]

Compounds of Compound Nos. (1) to (1446) described herein or pharmacologically acceptable salts thereof.

[11]

The compound or a pharmacologically acceptable salt thereof according to any of [1] to [5], wherein U represents C1-C6 alkylene or any group selected from groups represented by the following formula:

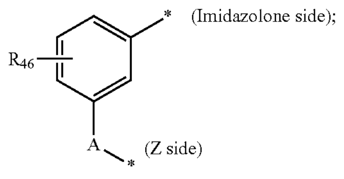

A is O;

$R_{46}$ is selected from hydrogen, C1-C10 alkyl, C1-C10 haloalkyl and C1-C10 hydroxyalkyl;

V is selected from:

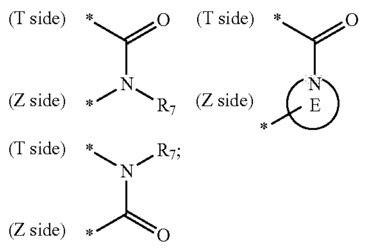

E is pyrrolidine or piperidine optionally substituted with a hydroxyl group(s); and $R_7$ is selected from:

1) hydrogen,

2) C1-C10 alkyl and

3) C1-C10 hydroxyalkyl.

[12]

A pharmaceutical composition comprising the compound or a pharmacologically acceptable salt thereof according to any of [1] to [11] as an active ingredient.

[13]

A pharmaceutical composition for activating intracellular cAMP response, comprising the compound or a pharmacologically acceptable salt thereof according to any of [1] to [11] as an active ingredient.

[14]

A prophylactic or therapeutic agent for osteoporosis, fracture, osteomalacia, arthritis, thrombocytopenia, hypoparathyroidism, hyperphosphatemia or tumoral calcinosis, or a stem cell mobilizing agent, comprising the compound or a pharmacologically acceptable salt thereof according to any of [1] to [11] as an active ingredient.

[15]

A method for the prevention or treatment of osteoporosis, fracture, osteomalacia, arthritis, thrombocytopenia, hypoparathyroidism, hyperphosphatemia or tumoral calcinosis, or stem cell mobilization, comprising administering a pharmaceutically effective amount of a composition comprising the compound or a pharmacologically acceptable salt thereof according to any of [1] to [11] to a patient in need of prevention or treatment of the disease or stem cell mobilization.

[16]

Use of the compound or a pharmacologically acceptable salt thereof according to any of [1] to [11] for the manufacture of a prophylactic or therapeutic agent for osteoporosis, fracture, osteomalacia, arthritis, thrombocytopenia, hypoparathyroidism, hyperphosphatemia or tumoral calcinosis, or a stem cell mobilizing agent.

[17]

The compound or a pharmacologically acceptable salt thereof according to any of [1] to [11] for the treatment or prevention of osteoporosis, fracture, osteomalacia, arthritis, thrombocytopenia, hypoparathyroidism, hyperphosphatemia or tumoral calcinosis, or stem cell mobilization.

In the description of each claim, a substituent not particularly defined is as defined for the same substituent in another claim from which the claim depends.

In the present specification and claims translated into languages such as English, description with indefinite articles (e.g., "a", "an" in English), definite articles (e.g., "the" in English) and the like includes singular and plural aspects unless otherwise defined. For example, "a group" in English includes one or more groups.

Advantageous Effects of Invention

The compounds or pharmacologically acceptable salts thereof according to the present invention have a parathyroid hormone-like effect involving bone anabolism which can considerably improve the compliance of patients as compared with parathyroid hormone peptide agonists.

DESCRIPTION OF EMBODIMENTS

The present invention relates to spiroimidazolone derivatives and use thereof. The present inventors have synthesized a compound represented by the above formula (1) or (2) or a pharmacologically acceptable salt thereof for the first time and have found that the compound or a salt thereof is a compound having a parathyroid hormone (PTH)-like effect.

The "alkyl" herein refers to a monovalent group derived by removing any one hydrogen atom from an aliphatic hydrocarbon, and covers a subset of hydrocarbyl or hydrocarbon group structures not containing a heteroatom or an unsaturated carbon-carbon bond and containing hydrogen and carbon atoms in the backbone. Examples of the alkyl group include those of linear or branched structures. The alkyl group is preferably an alkyl group having 1 to 10 carbon atoms (C1-C10; "Cp-Cq" hereinafter means that the group has p to q carbon atoms), more preferably a C1-C6 alkyl group. In particular, it is preferably a C1-C3 alkyl group in $R_{38}$ and $R_{39}$, a C1-C3 alkyl group in $R_3$, a C1-C3 alkyl group in $R_4$, a C1-C3 alkyl group in $R_5$, a C1-C3 alkyl group in $R_6$, a C1-C3 alkyl group in $R_7$, a C1-C3 alkyl group in $R_{40}$ and $R_{41}$, a C1-C3 alkyl group in $R_9$, a C1-C3 alkyl group in a substituent on a heterocycle where $R_7$ and $R_8$ are bonded to each other to form the heterocycle or a substituent on a spiro ring where the spiro ring is formed with the heterocycle, a C1-C3 alkyl group in $R_{16}$, a C1-C5 alkyl group in $R_{17}$, a C1-C3 alkyl group in $R_{18}$, a C1-C3 alkyl group in a substituent on a heterocycle where $R_{17}$ and $R_{18}$ are bonded to each other to form the heterocycle, a C1-C3 alkyl group in $R_{19}$, a C1-C3 alkyl group in $R_{20}$, a C1-C3 alkyl group in $R_{21}$, a C1-C4 alkyl group in $R_9$, a C1-C3 alkyl group in $R_{23}$, a C1-C3 alkyl group in $R_{10}$, a C1-C3 alkyl group in $R_{24}$, a C1-C4 alkyl group in $R_{11}$, a C1-C3 alkyl group in $R_{12}$, a C1-C3 alkyl group in $R_{13}$, a C1-C4 alkyl group in $R_{14}$, a C1-C3 alkyl group in a substituent on a heterocycle where $R_{13}$ and $R_{14}$ are bonded to each other to form the heterocycle, a C1-C3 alkyl group in $R_{15}$, a C1-C4 alkyl group in $R_{35}$, a C1-C3 alkyl group in $R_{36}$, a C1-C4 alkyl group in $R_{25}$, a C1-C13 alkyl group in $R_2$, a C1-C5 alkyl group in $R_{44}$, a C1-C3 alkyl group in $R_{42}$, a C1-C3 alkyl group in $R_{43}$, a C1-C3 alkyl group in $R_{26}$, a C1-C3 alkyl group in $R_{27}$ and a C1-C6 alkyl group in $R_{28}$.

Specific examples of the alkyl include a methyl group, an ethyl group, an n-propyl group, an isopropyl group, an n-butyl group, an isobutyl group, an s-butyl group, a t-butyl group, a pentyl group, an isopentyl group, a 2,3-dimethylpropyl group, a 3,3-dimethylbutyl group, a hexyl group, a 2,3-dimethylhexyl group, a 1,1-dimethylpentyl group, a heptyl group and an octyl group.

The "alkenyl" herein refers to a monovalent group having at least one double bond (two adjacent SP2 carbon atoms). Depending on the configuration of the double bond and the substituent (if present), the geometry of the double bond can be an entgegen (E) or zuzammen (Z) configuration or a cis or trans configuration. Examples of the alkenyl group include linear or branched groups, including straight chains that include internal olefins. Preferred examples include C2-C10 alkenyl groups, and more preferred examples include C2-C6 alkenyl groups. In particular, it is preferably a C2-C5 alkenyl group in $R_7$ and a C1-C9 alkenyl group in $R_2$.

Specific examples of such alkenyl include a vinyl group, an allyl group, a 1-propenyl group, a 2-propenyl group, a 1-butenyl group, a 2-butenyl group (including cis and trans), a 3-butenyl group, a pentenyl group and a hexenyl group.

The "alkynyl" herein refers to a monovalent group having at least one triple bond (two adjacent SP carbon atoms). Examples include linear or branched alkynyl groups, including internal alkylenes. Preferred examples include C2-C10 alkynyl groups, and more preferred examples include C2-C6 alkynyl groups. In particular, it is preferably a C2-C9 alkynyl group in $R_2$.

Specific examples of the alkynyl include an ethynyl group, a 1-propynyl group, a propargyl group, a 3-butynyl group, a pentynyl group, a hexynyl group, a 3-phenyl-2-propynyl group, a 3-(2'-fluorophenyl)-2-propynyl group, a 2-hydroxy-2-propynyl group, a 3-(3-fluorophenyl)-2-propynyl group and a 3-methyl-(5-phenyl)-4-pentynyl group.

The alkenyl or alkynyl can have one or more double bonds or triple bonds, respectively.

The "cycloalkyl" herein refers to a saturated cyclic monovalent aliphatic hydrocarbon group and includes single rings, fused rings, bicyclo rings and spiro rings. Preferred examples include C3-C10 cycloalkyl groups. Specific examples of the cycloalkyl group include a cyclopropyl group, a cyclobutyl group, a cyclopentyl group, a cyclohexyl group, a cycloheptyl group, a cyclooctyl group and a bicyclo [2.2.1]heptyl group.

The "cycloalkenyl" herein refers to a cyclic aliphatic hydrocarbon group having at least one double bond and includes single rings, fused rings, bicyclo rings and spiro rings. Preferred examples include C3-C10 cycloalkynyl groups, and more preferred examples include C3-C6 alkenyl groups. It is preferably C3-C5 cycloalkenyl in $R_9$. Specific examples of the cycloalkenyl group include a cyclopropenyl group, a cyclobutenyl group, a cyclopentenyl group, a cyclohexenyl group, a cycloheptenyl group, a cyclooctenyl group and a tetralinyl group.

The "heteroatom" herein refers to a nitrogen atom (N), an oxygen atom (O) or a sulfur atom (S).

The "halogen atom" herein refers to a fluorine atom, a chlorine atom, a bromine atom or an iodine atom.

The "haloalkyl" herein represents a group in which preferably 1 to 9, more preferably 1 to 5, of the same or different above "halogen atoms" are bonded to the above "alkyl". The haloalkyl is preferably C1-C10 haloalkyl, more preferably C1-C6 haloalkyl. In particular, it is preferably C1-C3 haloalkyl in $R_4$ and C1-C3 haloalkyl in $R_{44}$.

Specific examples include a fluoromethyl group, a difluoromethyl group and a trifluoromethyl group.

The "haloalkenyl" herein represents a group in which preferably 1 to 9, more preferably 1 to 5, of the same or different above "halogen atoms" are bonded to the above "alkenyl".

The "alkylcarbonyl" herein refers to a carbonyl group to which the above-defined "alkyl" is bonded, and is preferably C1-C10 alkylcarbonyl, more preferably C1-C6 alkylcarbonyl. In particular, it is preferably C1-C3 alkylcarbonyl in $R_{40}$ and $R_{41}$, C1-C3 alkylcarbonyl in $R_{19}$, C1-C3 alkylcarbonyl in $R_9$, C1-C3 alkylcarbonyl in $R_{23}$, C1-C3 alkylcarbonyl in $R_{12}$, C1-C3 alkylcarbonyl in $R_{35}$ and C1-C5 alkylcarbonyl in $R_2$.

The "Cn-Cm alkylcarbonyl" herein means that the alkyl therein is a "Cn-Cm" alkyl in terms of the number of carbon atoms. Hereinafter, the same applies to a group containing "alkylcarbonyl".

Specific examples include an acetyl group, an ethylcarbonyl group, a 1-propylcarbonyl group, a 2-propylcarbonyl group and a 2,2-dimethylpropylcarbonyl group.

The "haloalkylcarbonyl" herein refers to a carbonyl group to which the above-defined "haloalkyl" is bonded. The haloalkylcarbonyl is preferably C1-C10 haloalkylcarbonyl, more preferably C1-C6 haloalkylcarbonyl. In particular, it is preferably C1-C3 haloalkylcarbonyl in $R_4$.

The "cycloalkylcarbonyl" herein refers to a carbonyl group to which the above-defined "cycloalkyl" is bonded.

The "alkenylcarbonyl" herein refers to a carbonyl group to which the above-defined "alkenyl" is bonded, and is preferably C2-C10 alkenyl, more preferably C2-C6 alkenylcarbonyl. In particular, it is preferably C2-C3 alkenylcarbonyl in $R_2$.

The "Cn-Cm alkenylcarbonyl" herein means that it includes an alkenyl having "Cn-Cm" carbon atoms. Hereinafter, the same applies to a group containing "alkenylcarbonyl".

The "alkoxy" herein refers to an oxy group to which the above-defined "alkyl" is bonded, and is preferably a C1-C10 alkoxy group, more preferably a C1-C6 alkoxy group. In particular, it is preferably a C1-C3 alkoxy group in $R_{37}$, a C1-C3 alkoxy group in $R_3$, a C1-C3 alkoxy group in $R_4$, a C1-C3 alkoxy group in $R_5$, a C1-C3 alkoxy group in $R_7$, a C1-C3 alkoxy group in a substituent on a heterocycle where $R_7$ and $R_8$ are bonded to each other to form the heterocycle, a C1-C4 alkoxy group in $R_{16}$, a C1-C3 alkoxy group in $R_{17}$, a C1-C3 alkoxy group in $R_{11}$, a C1-C4 alkoxy group in $R_2$ and a C1-C4 alkoxy group in $R_{27}$. Specific examples include a methoxy group, an ethoxy group, a 1-propoxy group, a 2-propoxy group, an n-butoxy group, an i-butoxy group, a sec-butoxy group, a t-butoxy group, a 1-pentyloxy group, a 2-pentyloxy group, a 3-pentyloxy group, a 2-methyl-1-butyloxy group, a 3-methyl-1-butyloxy group, a 2-methyl-2-butyloxy group, a 3-methyl-2-butyloxy group, a 2,2-dimethyl-1-propyloxy group, a 1-hexyloxy group, a 2-hexyloxy group, a 3-hexyloxy group, a 2-methyl-1-pentyloxy group, a 3-methyl-1-pentyloxy group, a 4-methyl-1-pentyloxy group, a 2-methyl-2-pentyloxy group, a 3-methyl-2-pentyloxy group, a 4-methyl-2-pentyloxy group, a 2-methyl-3-pentyloxy group, a 3-methyl-3-pentyloxy group, a 2,3-dimethyl-1-butyloxy group, a 3,3-dimethyl-1-butyloxy group, a 2,2-dimethyl-1-butyloxy group, a 2-ethyl-1-butyloxy group, a 3,3-dimethyl-2-butyloxy group, a 2,3-dimethyl-2-butyloxy group and a 1-methyl-cyclopropylmethoxy group.

The "alkylcarbonyloxy" herein refers to an oxy group to which the above-defined "alkylcarbonyl" is bonded, and is preferably a C1-C10 alkylcarbonyloxy group, more preferably a C1-C6 alkylcarbonyloxy group. In particular, it is preferably a C1-C3 alkylcarbonyloxy group in $R_{23}$.

The "alkoxycarbonyl" herein refers to a carbonyl group to which the above-defined "alkoxy" is bonded. The alkoxycarbonyl is preferably C1-C10 alkoxycarbonyl, more preferably C1-C6 alkoxycarbonyl. It is preferably C1-C3 alkoxycarbonyl in $R_4$, C1-C3 alkoxycarbonyl in $R_{16}$, C1-C4 alkoxycarbonyl in $R_{19}$, C1-C4 alkoxycarbonyl in $R_9$, C1-C3 alkoxycarbonyl in $R_{23}$, C1-C3 alkoxycarbonyl in $R_{11}$, C1-C4 alkoxycarbonyl in $R_{13}$, C1-C5 alkoxycarbonyl in $R_2$ and C1-C3 alkoxycarbonyl in $R_{42}$. Examples include $-CO_2tBu$ (t-butoxycarbonyl) and $-CO_2Me$ (methoxycarbonyl).

The "Cn-Cm alkoxycarbonyl" herein means that the alkyl in the alkoxy is a "Cn-Cm" alkyl in terms of the number of carbon atoms. Hereinafter, the same applies to a group containing "alkoxycarbonyl".

The "heteroalkyl" herein refers to a group containing preferably 1 to 5 heteroatoms in the above-defined "alkyl" backbone and is preferably C1-C10 heteroalkyl, more preferably C1-C6 heteroalkyl. In particular, it is preferably C1-C5 heteroalkyl in $R_9$, C1-C5 heteroalkyl in $R_{11}$ and C1-C6 heteroalkyl in $R_{25}$. Examples include $-CH_2OCH_3$, $-CH_2OCH_2CH_3$, $-CH(Me)OCH_3$ and $-CH_2CH_2NMe_2$.

The "heteroalkenyl" herein refers to a group containing preferably 1 to 5 heteroatoms in the above-defined "alkenyl" backbone.

The "alkylene" herein refers to a divalent group having a basic skeleton represented by $-(CH_2)n-$ (preferably n=1 to 10), and may contain a branched chain. Specific examples include C1-C5 alkylene (n=1 to 5). More specific examples include a methylene group, a dimethylmethylene group, an ethylene group, a propylene group, a butylene group and a pentamethylene group. In particular, it is preferably C2-C5 alkylene in W, C1-C9 alkylene in X, C1-C10 alkylene in U, C1-C10 alkylene in Z and C1-C5 alkylene in G.

The "alkylidene" herein refers to a divalent group produced by removing two hydrogen atoms from the same carbon atom of a ring, the free valencies of which are part of a double bond. The geometry of the double bond can be an entgegen (E) or zuzammen (Z) configuration or a cis or trans configuration. Examples of the alkylidene include linear or branched groups. Preferred examples include C1-C10 alkylidene, and more preferred examples include C1-C6 alkylidene. In particular, it is preferably C1-C4 alkylidene in $R_2$. Specific examples include methylene ($=CH_2$), ethylidene ($=CHCH_3$), isopropylidene ($=C(CH_3)_2$) and propylidene ($=CHCH_2CH_3$).

The "alkenylene" herein refers to a divalent group having at least one double bond (two adjacent SP2 carbon atoms). Depending on the configuration of the double bond and the substituent (if present), the geometry of the double bond can be an entgegen (E) or zuzammen (Z) configuration or a cis or trans configuration. Examples of the alkenylene include linear or branched groups. Preferred examples include C2-C10 alkenylene, and more preferred examples include C2-C6 alkenylene. Specific examples include a vinylene group, a 1-propenylene group, a 1-butenylene group and a 1-pentenylene group. In particular, it is preferably C2-C5 alkenylene in W, C2-C9 alkenylene in X, C2-C10 alkenylene in Z and C2-C5 alkenylene in G.

The "alkynylene" herein refers to a divalent group having at least one triple bond (two adjacent SP carbon atoms). Examples include linear or branched alkynylenes. Preferred examples include C2-C10 alkynylene, and more preferred examples include C2-C6 alkynylene. In particular, it is preferably C2-C5 alkynylene in W and C2-C9 alkynylene in X.

The "cycloalkylene" herein refers to a saturated cyclic divalent aliphatic hydrocarbon group and includes single rings, bicyclo rings and spiro rings. Preferred examples include C3-C10 cycloalkylene. Specific examples of the cycloalkyl group include a cyclopropylene group, a cyclobutylene group, a cyclopentylene group, a cyclohexylene group, a cycloheptylene group, a cyclooctylene group and a bicyclo[2.2.1]heptylene group.

The "oxyalkylene" herein refers to a divalent C1-C10 group in which one end of the above-defined alkylene is an oxygen atom. Examples include $-CH_2O-$, $-C(Me)_2O-$, $-CH_2CH_2O-$, $-CH_2CH(Me)O-$ and $-CH_2C(Me)_2O-$. In X, the oxyalkylene is preferably bonded to a 1,3,8-triaza-spiro[4.5]dec-1-en-4-one ring or a 1,3,8-triaza-spiro[4.5]dec-1-ene-4-thione ring through a carbon atom in the oxyalkylene. In particular, it is preferably C1-C5 oxyalkylene in X.

The "heteroalkylene" herein refers to a divalent, preferably C1-C10, group containing preferably 1 to 5 heteroatoms in the above-defined "alkylene" backbone, and may contain a branched chain. Examples include $-CH_2OCH_2-$, $-CH_2OCH_2CH_2-$, $-CH(Me)OCH_2-$, $-CH_2CH_2NHCH_2-$ and $-CH_2CH_2N(Me)CH_2-$. In particular, it is preferably C2-C5 heteroalkylene in W, C1-C8 heteroalkylene in Z and C1-C4 heteroalkylene in G.

The "heteroalkenylene" herein refers to a divalent, preferably C1-C10, group containing preferably 1 to 5 heteroatoms in the above-defined "alkenylene" backbone, and may contain a branched chain. In particular, it is preferably C2-C8 heteroalkenylene in Z.

The "aryl" herein refers to a monovalent aromatic hydrocarbon ring, and may be partially saturated insofar as it is aromatic. Preferred examples include C6-C10 aryl. Specific examples of the aryl include a phenyl group, a naphthyl group (e.g., a 1-naphthyl group, a 2-naphthyl group) and a tetrahydronaphthyl group.

The "heteroaryl" herein refers to a monovalent group of an aromatic ring containing preferably 1 to 5 heteroatoms in the ring-forming atoms, and may be partially saturated. The saturated carbon atom(s) may be oxidized to form carbonyl. The ring may be a single ring or two fused rings (e.g., a bicyclic heteroaryl obtained by fusion with a benzene ring or monocyclic heteroaryl ring). The number of the ring-forming carbon atoms is preferably 1 to 10 (C1-C10 heteroaryl).

Specific examples of the heteroaryl include a furyl group, a thienyl group, a pyrrolyl group, an imidazolyl group, a pyrazolyl group, a triazolyl group, an isothiazolyl group, an oxazolyl group, an isoxazolyl group, an oxadiazolyl group, a thiadiazolyl group, a triazolyl group, a tetrazolyl group, a pyridyl group, a pyrimidyl group, a pyridazinyl group, a pyrazinyl group, a triazinyl group, a benzofuranyl group, a benzothienyl group, a benzothiadiazolyl group, a benzothiazolyl group, a benzoxazolyl group, a benzoxadiazolyl group, a benzimidazolyl group, an indolyl group, an isoindolyl group, an indazolyl group, a quinolyl group, an isoquinolyl group, a cinnolinyl group, a quinazolinyl group, a quinoxalinyl group, a benzodioxolyl group, an indolizinyl group and an imidazopyridyl group.

The "arylene" herein refers to a divalent group derived by further removing any one hydrogen atom from the above-defined "aryl". Preferred examples include C6-C10 arylene. Specific examples include a 1,3-phenylene group and a 1,4-phenylene group.

The "heteroarylene" herein refers to a divalent group derived by further removing any one hydrogen atom from the above-defined "heteroaryl". Specific examples include a 2,5-thiophenediyl group and a 2,6-pyridinediyl group.

The "heterocycle" herein refers to a C1-10 nonaromatic cycloalkyl, wherein the cycloalkyl is a monovalent group containing preferably 1 to 5 heteroatoms in the ring-forming atoms, the cycloalkyl may have a double bond in the ring, the carbon atom(s) may be oxidized to form carbonyl, the heteroatoms may form an oxo group, and the cycloalkyl may contain two fused rings. Specific examples of the heterocycle include azetidinyl, pyrrolidinyl, piperidinyl, piperazinyl, morpholinyl, oxazolidone, a 1,4-benzodioxanyl group, a tetrahydropyranyl group, a 1,3-dioxolanyl group, a 1,3-thiazolidinyl group, a hydantoyl group, a benzoxazolinonyl group, a benzothiazolonyl group, a 2,4-(1H,3H)quinazolinedionyl group, an indolinyl group, an oxindolyl group, a 1,3-benzoxolyl group, an imidazolidinyl group, a pyrazolidinyl group, an oxazolidinyl group, an isoxazolidinyl group, a thiomorpholinyl group, a dihydrothiazolyl group, an oxetanyl group, a 2-oxa-6-aza-spiro[3.3]heptanyl group, a 1,2,3,4-tetrahydroquinolyl group, an imidazolidonyl group, a pyrazolidonyl group, an oxazolidonyl group, a succinimidyl group, a 2-azetidinoyl group, a 2-oxopiperazinyl group, a 3,5-dioxomorpholinyl group, a 2-oxomorpholinyl group, a 2,5-dehydrouracinyl group, a 2-pyrrolidonyl group, a 2-piperidonyl group, a 4-piperidonyl group, a 3-isoxazolidone group, a 1,1,3-trioxo[1,2,5]thiadiazolidinone group, a 1,1-dioxo-1$\lambda^6$-thiomorphonyl group and an imidazolidine-2,4-dione group. In these groups, the carbon atom(s) may be oxidized to form carbonyl, and the heteroatoms may have an oxo group.

The "heterocyclic carbonyl" herein refers to a carbonyl group to which the above-defined "heterocycle" is bonded.

The "alkylamino" herein refers to an amino group to which one or two of the above-defined "alkyl" groups are bonded. Preferred examples include C1-C10 monoalkylamino and C1-C10 dialkylamino, and more preferred examples include C1-C6 monoalkylamino and C1-C6 dialkylamino. Two alkyl groups in the dialkylamino may be the same or different. In particular, it is preferably C1-C3 monoalkylamino or C1-C3 dialkylamino in $R_7$, C1-C3 monoalkylamino or dialkylamino in a substituent on a heterocycle where $R_7$ and $R_8$ are bonded to each other to form the heterocycle, C1-C3 monoalkylamino or C1-C3 dialkylamino in $R_{16}$, C1-C3 monoalkylamino or C1-C3 dialkylamino in $R_{17}$, C1-C3 monoalkylamino or C1-C3 dialkylamino in $R_{21}$, C1-C3 monoalkylamino or C1-C3 dialkylamino in $R_{23}$, C1-C3 monoalkylamino or C1-C3 dialkylamino in $R_{24}$, C1-C3 monoalkylamino or C1-C3 dialkylamino in $R_{11}$, C1-C3 monoalkylamino or C1-C3 dialkylamino in $R_{12}$, C1-C3 monoalkylamino or C1-C3 dialkylamino in $R_{14}$ and C1-C3 monoalkylamino or C1-C3 dialkylamino in $R_{35}$. The "alkyl" in the alkylamino may have the above-defined "aryl" as a substituent(s). Examples of the alkylamino include $—NHCH_3$, $—N(CH_3)_2$, $—N(CH_3)CH_2CH_3$ and $—NHCH_2Ph$.

The "amino" herein refers to a monovalent group having two hydrogen atoms on a nitrogen atom (a group represented by $—NH_2$).

The "arylalkyl" herein refers to a group in which any hydrogen atom in the above-defined "alkyl" is replaced by the above-defined "aryl". Preferred examples of the arylalkyl include C6-C10 aryl C1-C10 alkyl. In particular, it is preferably C6-C10 aryl C1-C3 alkyl in $R_{21}$, C6-C10 aryl C1-C3 alkyl in $R_{35}$ and C6-C10 aryl C1-C3 alkyl in $R_{25}$. Specific examples include a benzyl group, a phenethyl group and a 3-phenyl-1-propyl group.

The "heterocyclic alkyl" herein refers to a group in which any hydrogen atom in the above-defined "alkyl" is replaced by the above-defined "heterocycle". Specific examples include a morpholin-4-yl-methyl group, a 2-(morpholin-4-yl) ethyl group, a 4-hydroxy-piperidin-1-yl-methyl group, a 2-(4-hydroxy-piperidin-1-yl)ethyl group, a 4-methyl-piperazin-1-yl-methyl group and a 2-(4-methyl-piperazin-1-yl-) ethyl group.

The "hydroxyalkyl" herein refers to a group in which any hydrogen atom(s) in the above-defined "alkyl" is replaced by preferably 1 to 4 hydroxyl groups, and it is preferably a C1-C10 hydroxyalkyl group, more preferably a C1-C6 hydroxyalkyl group. In particular, it is preferably a C1-C4 hydroxyalkyl group in $R_{25}$. Specific examples include hydroxymethyl, 2-hydroxyethyl, 3-hydroxypropyl and 2,3-dihydroxypropyl.

The "alkylcarbonylamino" herein refers to an amino group to which one or two of the above-defined "alkylcarbonyl" groups are bonded. Preferred examples include C1-C10 monoalkylcarbonylamino and C1-C10 dialkylcarbonylamino, and more preferred examples include C1-C6 monoalkylcarbonylamino and C1-C6 dialkylcarbonylamino. Two alkyl groups in the dialkylcarbonylamino may be the same or different. In particular, it is preferably C1-C3 alkylcarbonylamino in $R_{17}$, C1-C3 alkylcarbonylamino in $R_{24}$ and C1-C3 alkylcarbonylamino in $R_{35}$. Examples include $CH_3CONH—$.

The "alkoxycarbonylamino" herein refers to an amino group to which one or two of the above-defined "alkoxycarbonyl" groups are bonded. Preferred examples include C1-C10 monoalkoxycarbonylamino and C1-C10 dialkoxycarbonylamino. Two alkoxy groups in the dialkoxycarbonylamino may be the same or different. In particular, it is preferably C1-C4 monoalkoxycarbonyl or C1-C4 dialkoxycarbonylamino in $R_{42}$.

The "alkylaminocarbonyl" herein refers to a carbonyl group to which the above-defined "alkylamino" is bonded, and is preferably C1-C10 alkylaminocarbonyl, more preferably C1-C6 alkylaminocarbonyl. In particular, it is preferably C1-C3 alkylaminocarbonyl in $R_{13}$. Examples include $CH_3NHCO—$.

The "Cn-Cm alkylaminocarbonyl" herein means that the alkyl therein is a "Cn-Cm" alkyl in terms of the number of carbon atoms. Hereinafter, the same applies to a group containing "alkylaminocarbonyl".

The "arylcarbonyl" herein refers to a carbonyl group to which the above-defined "aryl" is bonded.

The "aryloxy" herein refers to an oxy group to which the above-defined "aryl" is bonded.

The "aryloxycarbonyl" herein refers to a carbonyl group to which the above-defined "aryloxy" is bonded.

The "heteroaryloxy" herein refers to an oxy group to which the above-defined "heteroaryl" is bonded.

The "heteroarylcarbonyl" herein refers to a carbonyl group to which the above-defined "heteroaryl" is bonded.

The "hydroxycarbonyl" herein refers to —$CO_2H$ (carboxyl).

The "aminocarbonyl" herein refers to a carbonyl group to which the above-defined "amino" is bonded.

The "hydroxyalkylamino" herein refers to an amino group to which one or two of the above-defined "hydroxyalkyl" groups are bonded. Examples include mono(hydroxyalkyl) amino and di(hydroxyalkyl)amino. Two hydroxyalkyl groups in the di(hydroxyalkyl)amino may be the same or different. "—$NHCH_2$— or —$NHCH_2CH_2$—" in W herein is preferably bonded through the nitrogen atom to the sulfonyl group in the formula (1).

The "hydroxyalkylaminoalkyl" herein refers to a group in which any hydrogen atom in the above-defined "alkyl" is replaced by the above-defined "hydroxyalkylamino".

The "alkoxyalkyl" herein refers to a group in which any hydrogen atom in the above-defined "alkyl" is replaced by the above-defined "alkoxy", and is preferably C1-C10 alkoxy-C1-C10 alkyl, more preferably C1-C6 alkoxy-C1-C6 alkyl. In particular, it is preferably C1-C3 alkoxy-C1-C3 alkyl in a substituent on a heterocycle where $R_7$ and $R_8$ are bonded to each other to form the heterocycle.

The "hydroxyalkyloxy" herein refers to a group in which any hydrogen atom in the above-defined "alkoxy" is replaced by a hydroxyl group, and is preferably C1-C10 hydroxyalkyloxy, more preferably C1-C6 hydroxyalkyloxy.

The "thiocarbonyl" herein refers to a group represented by C═S.

The "alkylthio" herein refers to a thio group to which the above-defined "alkyl" is bonded, and is preferably a C1-C10 alkylthio group, more preferably a C1-C6 alkylthio group.

The "B optionally substituted with A" herein denotes that any hydrogen atom(s) in B may be replaced with any number of As.

In the present invention, the number of substituents is not limited unless otherwise indicated. For example, the number of substituents may be 1 to 7, 1 to 4, 1 to 3, 1 to 2, or 1.

The "PTH-like effect" herein refers to activity of increasing intracellular cAMP (cAMP: cyclic adenosine monophosphate) by action on the PTH receptor or action on the signal transduction pathway through the PTH receptor.

Herein, "*" in a chemical formula denotes a bonding position.

The compounds according to the present invention, whether free forms or pharmacologically acceptable salts, are included in the present invention. Examples of such "salts" include inorganic acid salts, organic acid salts, inorganic base salts, organic base salts and acidic or basic amino acid salts.

Preferred examples of the inorganic acid salts include hydrochlorides, hydrobromides, sulfates, nitrates and phosphates. Preferred examples of the organic acid salts include acetates, succinates, fumarates, maleates, tartrates, citrates, lactates, stearates, benzoates, methanesulfonates and p-toluenesulfonates.

Preferred examples of the inorganic base salts include alkali metal salts such as sodium salts and potassium salts, alkaline earth metal salts such as calcium salts and magnesium salts, aluminum salts and ammonium salts. Preferred examples of the organic base salts include diethylamine salts, diethanolamine salts, meglumine salts and N,N-dibenzylethylenediamine salts.

Preferred examples of the acidic amino acid salts include aspartates and glutamates. Preferred examples of the basic amino acid salts include arginine salts, lysine salts and ornithine salts.

The compounds of the present invention may absorb moisture, have adsorbed water or form hydrates when left in the air. Such hydrates are also included in the salts of the present invention.

Further, the compounds I of the present invention may absorb certain other solvents to form solvates. Such salts are also encompassed in the present invention as salts of the compounds of the formula (1) or (2).

Herein, a structural formula of a compound may represent a certain isomer for the sake of convenience. However, the compounds of the present invention include all isomers such as geometric isomers, optical isomers based on asymmetric carbons, stereoisomers and tautomers as well as mixtures of these isomers which occur due to the structures of the compounds, without being limited to the formulas described for the sake of convenience, and may be either one of isomers or a mixture thereof. Thus, the compounds of the present invention may have an asymmetric carbon atom in the molecule and may be present as optically active forms and racemates, but the present invention is not limited to either of them and includes both of them.

The present invention includes all isotopes of the compounds represented by the formula (1) or (2). In the isotopes of the compounds of the present invention, at least one atom is replaced by an atom having the same atomic number (proton number) but having a different mass number (sum of the number of protons and the number of neutrons). Examples of the isotopes contained in the compounds of the present invention include a hydrogen atom, a carbon atom, a nitrogen atom, an oxygen atom, a phosphorus atom, a sulfur atom, a fluorine atom and a chlorine atom, including 2H, 3H, 13C, 14C, 15N, 17O, 18O, 31P, 32P, 35S, 18F and 36Cl, respectively. In particular, radioisotopes that decay by emitting radioactivity such as 3H and 14C are useful in body tissue distribution tests for pharmaceuticals or compounds. Stable isotopes do not decay, are almost equal in abundance and do not emit radioactivity, and thus they can be used safely. The isotopes of the compounds of the present invention can be converted according to conventional methods by substituting a reagent containing a corresponding isotope for a reagent used for synthesis.

The compounds according to the present invention may exhibit crystalline polymorphism, but are not particularly limited to any one of these, but may be in any one of these crystal forms or exist as a mixture of two or more crystal forms.

The compounds according to the present invention include prodrugs thereof. The prodrugs are derivatives of the compounds of the present invention which have chemically or metabolically decomposable groups and are converted back to the original compounds after administration in vivo to exhibit their original efficacy, including complexes not formed with covalent bonds, and salts.

The compounds represented by the above formula (1) or (2) according to the present invention are preferably as follows.

W is preferably selected from:

1) a single bond,

2) C1-C10 alkylene optionally containing a carbonyl group, wherein the alkylene is optionally substituted with a halogen atom(s) and/or a hydroxyl group(s), 3) C2-C10 alkenylene optionally substituted with a halogen atom(s), 4) C2-C10 alkynylene, 5) arylene optionally substituted with a halogen atom(s), 6) heteroarylene optionally substituted with a halogen atom(s), 7) C1-C10 heteroalkylene optionally substituted with a halogen atom(s),
8) —NH—, —$NHCH_2$— or —$NHCH_2CH_2$—,
9) cycloalkylene and
10) -(cycloalkylene)-$CH_2$—.

More preferably, the above W is selected from:
1) a single bond,
2) C1-C10 alkylene optionally containing a carbonyl group, wherein the alkylene is optionally substituted with a halogen atom(s) or hydroxy,
3) C2-C10 alkenylene optionally substituted with a halogen atom(s),
4) C2-C10 alkynylene,
5) arylene,
6) heteroarylene,
7) —NH—, —$NHCH_2$— or —$NHCH_2CH_2$—,
8) cycloalkylene and
9) -(cycloalkylene)-$CH_2$—.

Still more preferably, the above W is selected from:
1) a single bond,
2) C1-C10 alkylene optionally substituted with a halogen atom(s),
3) C2-C10 alkenylene,
4) C2-C10 alkynylene and
5) heteroarylene.

Particularly preferably, the above W is selected from:
1) C1-C6 alkylene optionally substituted with a fluorine atom(s),
2) C1-C6 alkenylene and
3) thiophene.

More particularly preferably, the above W is selected from:
1) ethylene,
2) vinylene and
3) thiophene.

The above X is preferably selected from the following bond or groups:
1) a single bond,
2) C1-C10 alkylene optionally substituted with a halogen atom(s) or cycloalkyl,
3) C2-C10 alkenylene optionally substituted with a halogen atom(s),
4) C2-C10 alkynylene optionally substituted with a halogen atom(s),
5) C1-10 oxyalkylene optionally substituted with a halogen atom(s) and
6) —$NR_{47}$— wherein $R_{47}$ is selected from:

i) a hydrogen atom and ii) C1-C10 alkyl optionally substituted with a halogen atom(s).

More preferably, the above X is selected from the following bond or groups:
1) a single bond,
2) C1-C10 alkylene optionally substituted with cycloalkyl,
3) C2-C10 alkenylene,
4) C2-C10 alkynylene and
5) C1-C10 oxyalkylene.

Still more preferably, the above X is selected from the following bond or groups:
1) a single bond,
2) C1-C10 alkylene,
3) C2-C10 alkenylene,
4) C2-C10 alkynylene and
5) C1-C10 oxyalkylene, wherein the oxyalkylene is bonded to a 1,3,8-triaza-spiro[4.5]dec-1-en-4-one ring or a 1,3,8-triaza-spiro[4.5]dec-1-ene-4-thione ring through a carbon atom in the oxyalkylene.

Particularly preferably, the above X is selected from the following bond or groups:
1) a single bond,
2) C1-C6 alkylene and
3) C1-C6 oxyalkylene optionally substituted with a halogen atom(s), wherein the oxyalkylene is bonded to a 1,3,8-triaza-spiro[4.5]dec-1-en-4-one ring or a 1,3,8-triaza-spiro[4.5]dec-1-ene-4-thione ring through a carbon atom in the oxyalkylene.

More particularly preferably, the above X is a single bond.

The above Y is preferably selected from:
1) an oxygen atom,
2) a sulfur atom and
3) =$NR_{37}$, or 4) Y is —$NR_{38}R_{39}$ represented by the following formula (A):

(A)

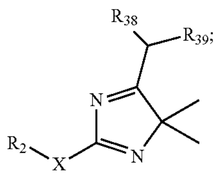

and can form tautomers;

$R_{37}$ is selected from:
1) hydrogen,
2) hydroxy and
3) C1-C10 alkoxy; and $R_{38}$ and $R_{39}$ are independently selected from hydrogen or C1-C10 alkyl optionally substituted with cycloalkyl, or $R_{38}$ and $R_{39}$ may be bonded to each other to form a ring selected from the group consisting of azetidinyl, pyrrolidinyl, piperidinyl, piperazinyl and morpholinyl, and the ring is optionally substituted with C1-C10 alkyl.

More preferably, the above Y is an oxygen atom.

The above m is preferably an integer of 0 to 2, more preferably 1.

The above n is preferably an integer of 0 to 2, more preferably 1.

The above $R_1$ is preferably selected from:
1) hydrogen,
2) cycloalkyl optionally substituted with a group(s) selected from $R_4$, $R_5$ and $R_6$,
3) a heterocycle optionally substituted with a group(s) selected from $R_{25}$, $R_4$, $R_5$ and $R_6$,
4) aryl optionally substituted with a group(s) selected from $R_3$, $R_4$, $R_5$ and $R_6$ and
5) heteroaryl optionally substituted with a group(s) selected from $R_{25}$, $R_4$, $R_5$ and $R_6$.

More preferably, the above $R_1$ is selected from:
1) hydrogen,
2) cycloalkyl optionally substituted with a group selected from $R_4$,
3) a heterocycle optionally substituted with a group(s) selected from $R_{25}$ and $R_4$,
4) aryl optionally substituted with a group(s) selected from $R_3$, $R_4$, $R_5$ and $R_6$ and
5) heteroaryl optionally substituted with a group(s) selected from $R_{25}$, $R_4$ and $R_5$.

Still more preferably, the above $R_1$ is selected from:
1) aryl optionally substituted with a group(s) selected from $R_3$, $R_4$ and $R_5$ and 2) heteroaryl optionally substituted with a group(s) selected from $R_{25}$ and $R_4$.

Particularly preferably, the above $R_1$ is the following general formula (3) or (4).

(3)

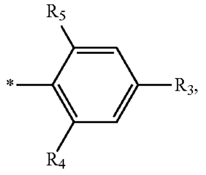

(4)

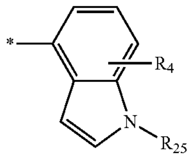

The above $R_3$ is preferably selected from:
1) —$CONR_7R_8$,
2) —$OR_9$,
3) —$NR_9R_{10}$,
4) —$N(R_9)COR_{11}$,
5) —$N(R_9)$ $SO_2R_{12}$,
6) —$SO_2R_{15}$,
7) C1-10 alkyl optionally substituted with a group(s) independently selected from a halogen atom, a hydroxyl group, —$COR_{16}$ and —$NR_{13}R_{14}$,
8) heteroaryl optionally having C1-10 alkyl and/or C1-10 alkoxy as a substituent(s) and
9) —$N(R_9)CSR_{11}$.

More preferably, the above $R_3$ is selected from:
1) —$CONR_7R_8$,
2) —$OR_9$,
3) —$NR_9R_{10}$,
4) —$N(R_9)COR_{11}$,
5) —$N(R_9)SO_2R_{12}$,
6) —$SO_2R_{15}$,
7) C1-C10 alkyl optionally substituted with a group(s) selected from —$COR_{26}$ and —$NR_{13}R_{14}$ and
8) —$N(R_9)CSNH_2$.

Still more preferably, the above $R_3$ is selected from:
1) —$CONR_2R_9$,
2) —$OR_9$,
3) —$NR_9R_{10}$,
4) —$N(R_9)COR_{11}$,
5) —$N(R_9)SO_2R_{12}$,
6) —$SO_2R_{15}$ and
7) C1-C6 alkyl optionally substituted with a group(s) selected from —$COR_{16}$ and —$NR_{13}R_{14}$.

The above $R_4$ is preferably selected from:
1) halogen,
2) cyano,
3) nitro,
4) amino,
5) —$NHCOR_{26}$,
6) C1-C10 alkyl optionally substituted with a group(s) independently selected from hydroxycarbonyl, C1-C10 alkoxycarbonyl and aminocarbonyl,
7) C1-C10 haloalkyl,
8) C1-C10 alkoxy,
9) C1-C10 haloalkylcarbonyl,
10) —$COR_{16}$,
11) C1-C10 hydroxyalkyl and
12) C1-C10 heteroalkyl.

More preferably, the above $R_4$ is selected from:
1) halogen,
2) cyano,
3) amino,
4) C1-C10 alkyl,
5) C1-C10 haloalkyl,
6) C1-C10 alkoxy,
7) C1-C10 haloalkylcarbonyl,
8) —$COR_{16}$ and
9) C1-C10 heteroalkyl.

The above $R_5$ is preferably selected from a halogen atom, C1-C10 alkyl, C1-C10 haloalkyl and C1-C10 alkoxy.

The above $R_6$ is preferably selected from a halogen atom, C1-C10 alkyl and C1-C10 haloalkyl.

The above $R_7$ is preferably selected from:
1) hydrogen,
2) C1-C10 alkyl optionally substituted with a group(s) independently selected from amino and C1-C10 alkylamino,
3) C1-C10 hydroxyalkyl,
4) C1-C10 haloalkyl,
5) C1-C10 heteroalkyl,
6) C1-C10 heteroalkyl optionally substituted with a group(s) selected from a hydroxyl group, C1-C10 alkylamino and C2-C10 alkenyl,
7) aryl,
8) heteroaryl,
9) aryl C1-C10 alkyl,
10) a heterocycle optionally substituted with C1-C10 alkyl,
11) —$(CH_2)_LCOR_{16}$ (wherein L represents an integer of 1 to 4),
12) C1-C10 alkoxy,
13) C2-C10 alkenyl and
14) —$NR_{40}R_{41}$; and $R_{40}$ and $R_{41}$ are independently selected from hydrogen, C1-C10 alkyl and C1-C10 alkylcarbonyl, or $R_{40}$ and $R_{41}$ may be bonded to each other to form a ring selected from azetidinyl, pyrrolidinyl, piperidinyl, piperazinyl and morpholinyl, and the heterocycle is optionally substituted with C1-C10 alkyl.

The above $R_8$ is preferably selected from hydrogen and C1-C10 alkyl optionally substituted with a halogen atom(s) and/or a hydroxyl group(s).

The above $R_7$ and $R_8$ may be bonded to form a 4- to 7-membered heterocycle optionally containing an additional element(s) or group(s) independently selected from O, N, S, SO and $SO_2$, and the heterocycle optionally contains carbonyl, and the heterocycle is optionally substituted with a substituent(s) independently selected from:
1) a halogen atom,
2) C1-C10 alkyl optionally having C1-C10 alkylamino as a substituent(s),
3) C1-C10 haloalkyl,
4) a hydroxyl group,
5) C1-C10 hydroxyalkyl,
6) C1-C10 alkoxy optionally substituted with a group(s) independently selected from a halogen atom, a hydroxyl group, amino and C1-C10 alkylamino,
7) aryl optionally substituted with a group(s) selected from a halogen atom, a hydroxyl group, amino and C1-C10 alkylamino,
8) C1-C10 heteroalkyl optionally substituted with a group(s) independently selected from a halogen atom, a hydroxyl group, amino and C1-C10 alkylamino,
9) a heterocycle optionally substituted with C1-C10 alkyl,
10) heteroaryl optionally substituted with C1-C10 alkyl, 11) heterocyclyl C1-C10 alkyl,
12) —$COR_{16}$,
13) —$NR_{19}R_{20}$.
14) —$SO_2R_{21}$.
15) C1-C10 alkoxy-C1-C10 alkyl optionally having a hydroxyl group(s) as a substituent(s) and
16) C1-C10 hydroxyalkyloxy, wherein the hydrogen atom of the hydroxyl group may be replaced by C1-C10 hydroxyalkyl, and the heterocycle may further form a spiro ring together with a 4- to 6-membered heterocycle, and the bonded 4- to 6-membered heterocycle optionally contains O and N as ring-forming elements in addition to carbon atoms, and the carbon atom(s) may be oxidized to form carbonyl, and the 4- to 6-membered heterocycle is optionally further substituted with C1-C10 alkyl.

The above $R_{16}$ is preferably selected from:
1) a hydroxyl group,
2) C1-C10 alkoxy,
3) $NR_{17}R_{18}$ and
4) C1-C10 alkyl optionally substituted with a substituent(s) selected from a halogen atom, a hydroxyl group, C1-C10 alkoxycarbonyl or C1-C10 alkylamino.

The above $R_{17}$ is preferably selected from:
1) hydrogen,
2) C1-C10 alkyl optionally substituted with a group(s) selected from aryl, amino, C1-C10 alkylamino, C1-C10 alkylcarbonylamino and a hydroxyl group,
3) heteroaryl and
4) C1-C10 alkoxy.

The above $R_{18}$ is preferably selected from hydrogen, C1-C10 alkyl and C1-C10 hydroxyalkyl.

The above $R_{17}$ and $R_{18}$ may be bonded to each other to form a ring selected from azetidinyl, pyrrolidinyl, piperidinyl, piperazinyl and morpholinyl, and the ring is optionally substituted with a group(s) selected independently of each other from C1-C10 alkyl, a halogen atom and C1-C10 alkoxycarbonyl.

The above $R_{19}$ is preferably selected from hydrogen, C1-C10 alkyl, C1-C10 haloalkyl, C1-C10 alkylcarbonyl, C1-C10 hydroxyalkyl, C1-C10 aminoalkyl, C1-C10 alkoxycarbonyl and C1-C10 heteroalkyl.

The above $R_{20}$ is preferably selected from hydrogen and C1-C10 alkyl.

The above $R_{19}$ and $R_{20}$ may be bonded to form a ring selected from azetidinyl, pyrrolidinyl, piperidinyl, piperazinyl and morpholinyl, and the ring is optionally substituted with a group(s) selected independently of each other from C1-C10 alkyl and a halogen atom.

The above $R_{21}$ is preferably selected from:
1) C1-C10 alkyl optionally substituted with aryl,
2) amino,
3) C1-C10 alkylamino and
4) aryl optionally substituted with C1-C10 alkyl.

The above $R_9$ is preferably selected from:
1) hydrogen,
2) C1-C10 alkyl optionally substituted with a group(s) independently selected from $R_{23}$,
3) aryl optionally substituted with a group(s) selected from a halogen atom, a hydroxyl group, amino and C1-C10 alkylamino,
4) cycloalkyl optionally substituted with a halogen atom(s) or a hydroxyl group(s),
5) a heterocycle optionally substituted with a group(s) independently selected from C1-C10 alkyl, C1-C10 alkylcarbonyl, C1-C10 alkoxy, C1-C10 alkoxycarbonyl, amino and a halogen atom,
6) C1-C10 heteroalkyl optionally substituted with a group(s) independently selected from a halogen atom and a hydroxyl group,
7) heteroaryl optionally substituted with a group(s) selected from C1-C10 alkyl, C1-C10 alkylcarbonyl, C1-C10 alkoxycarbonyl and a halogen atom and
8) cycloalkenyl optionally substituted with a group(s) selected from C1-C10 alkoxy, C1-C10 alkylamino, amino, a hydroxyl group and a halogen atom, wherein the cycloalkenyl may contain a carbonyl group.

More preferably, the above $R_9$ is selected from:
1) hydrogen,
2) C1-C10 alkyl optionally substituted with a group(s) independently selected from $R_{23}$,
3) cycloalkyl optionally substituted with a halogen atom(s) or a hydroxyl group(s),
4) a heterocycle optionally substituted with a group(s) selected from C1-C10 alkyl, C1-C10 alkylcarbonyl, C1-C10 alkoxy, C1-C10 alkoxycarbonyl, amino and a halogen atom,
5) C1-C10 heteroalkyl optionally substituted with a group(s) selected from a halogen atom and a hydroxyl group,
6) heteroaryl optionally substituted with a group(s) independently selected from C1-C10 alkyl, C1-C10 alkylcarbonyl, C1-C10 alkoxycarbonyl and a halogen atom and
7) cycloalkenyl optionally substituted with a group(s) selected from C1-C10 alkoxy, C1-C10 alkylamino, amino, 1 to 3 hydroxyl groups and 1 to 4 halogen atoms, wherein the cycloalkenyl may contain a carbonyl group.

The above $R_{23}$ is preferably selected from:
1) a halogen atom,
2) a hydroxyl group,
3) a C1-C10 alkylcarbonyloxy group,
4) —$COR_{16}$,
5) amino,
6) C1-C10 alkylamino,
7) a heterocycle optionally substituted with a group(s) selected from C1-C10 alkyl, C1-C10 alkylcarbonyl, C1-C10 alkoxycarbonyl and a halogen atom and
8) cyano.

The above $R_{10}$ is preferably selected from:
1) hydrogen and
2) C1-C10 alkyl optionally substituted with a group(s) selected from a halogen atom, a hydroxyl group and aryl.

$R_9$ and $R_{10}$ may be bonded to form a 4- to 7-membered heterocycle optionally containing an additional element(s) or group(s) independently selected from N, O, S, SO, $SO_2$, carbonyl and thiocarbonyl, and the heterocycle is optionally substituted with a substituent(s) independently selected from $R_{24}$.

The above $R_{24}$ is preferably selected from:
1) a halogen atom,
2) C1-C10 alkyl optionally substituted with a group(s) independently selected from C1-C10 alkylamino and C1-C10 alkylcarbonylamino,
3) C1-C10 haloalkyl,
4) a hydroxyl group,
5) C1-C10 hydroxyalkyl,
6) C1-C10 alkoxy optionally substituted with a group(s) independently selected from a halogen atom, a hydroxyl group, amino and C1-C10 alkylamino,
7) aryl optionally substituted with a group(s) independently selected from a halogen atom, a hydroxyl group, amino and C1-C10 alkylamino,
8) C1-C10 heteroalkyl optionally substituted with a group(s) independently selected from a halogen atom, a hydroxyl group, amino and C1-C10 alkylamino,
9) a heterocycle optionally substituted with C1-C10 alkyl, 10) heteroaryl,
11) heterocyclyl C1-C10 alkyl,
12) —$COR_{16}$,
13) —$NR_{19}R_{20}$ and
14) —$SO_2R_{21}$.

More preferably, the above $R_{24}$ is selected from:
1) a halogen atom,
2) C1-C10 alkyl optionally substituted with a group(s) independently selected from C1-C10 alkylamino and C1-C10 alkylcarbonylamino,
3) C1-C10 haloalkyl,
4) a hydroxyl group,
5) C1-C10 hydroxyalkyl,
6) C1-C10 alkoxy optionally substituted with a group(s) independently selected from a halogen atom, a hydroxyl group, amino and C1-C10 alkylamino,
7) aryl optionally substituted with a group(s) selected from a halogen atom, a hydroxyl group, amino and C1-C10 alkylamino,
8) C1-C10 heteroalkyl optionally substituted with one to two types of groups selected from a halogen atom, a hydroxyl group, amino and C1-C10 alkylamino,
9) —$COR_{16}$ and
10) —$NR_{19}R_{20}$.

The above $R_{11}$ is preferably selected from:
1) C1-C10 alkyl optionally substituted with a group(s) independently selected from:
i) a hydroxyl group,
ii) —$NR_{17}R_{18}$,
iii) a C1-C10 alkoxy group,
iv) a halogen atom,
v) C1-C10 alkoxycarbonyl,
vi) aminocarbonyl and
vii) aryl optionally substituted with a group(s) independently selected from a halogen atom, a hydroxyl group, C1-C10 alkoxy, amino, C1-C10 alkylamino and —$COR_{22}$,
2) aryl optionally substituted with a group(s) independently selected from a halogen atom, a hydroxyl group, C1-C10 alkoxy, amino, C1-C10 alkylamino and —$COR_{22}$,
3) cycloalkyl optionally substituted with a halogen atom(s),
4) a heterocycle optionally substituted with a group(s) selected from C1-C10 alkyl, C1-C10 alkylcarbonyl, C1-C10 alkoxycarbonyl and a halogen atom,
5) C1-C10 alkoxy, wherein the alkyl group is optionally substituted with a group(s) independently selected from C1-C10 alkylcarbonylamino, amino, C1-C10 alkylamino and a hydroxyl group,
6) amino,
7) C1-C10 alkylamino, wherein the alkyl group is optionally substituted with a group(s) independently selected from C1-C10 alkylcarbonylamino, amino, C1-C10 alkylamino, hydroxycarbonyl and a hydroxyl group and
8) C2-C10 alkenyl.

More preferably, the above $R_{11}$ is selected from:
1) C1-C10 alkyl optionally substituted with 1 to 3 substituents independently selected from:
i) a hydroxyl group,
ii) —$NR_{17}R_{18}$,
iii) a C1-C10 alkoxy group,
iv) a halogen atom,
v) C1-C10 alkoxycarbonyl and
vi) aminocarbonyl,
2) aryl,
3) aryl C1-C10 alkyl,
4) cycloalkyl optionally substituted with a halogen atom(s),
5) a heterocycle optionally substituted with C1-C10 alkyl,
6) C1-C10 alkoxy, wherein the alkyl group is optionally substituted with a group(s) independently selected from C1-C10 alkylcarbonylamino, amino, C1-C10 alkylamino and a hydroxyl group,
7) amino,
8) C1-C10 alkylamino, wherein the alkyl group is optionally substituted with a group(s) independently selected from C1-C10 alkylcarbonylamino, amino, C1-C10 alkylamino, hydroxycarbonyl and a hydroxyl group and
9) C2-C10 alkenyl.

The above $R_{22}$ is preferably selected from C1-C10 alkoxy, a hydroxyl group, amino and C1-C10 alkylamino.

The above $R_{12}$ is preferably selected from:
1) C1-C10 alkyl,
2) amino and
3) C1-C10 alkylamino, wherein the alkyl group is optionally substituted with a group(s) independently selected from amino, C1-C10 alkylamino and a hydroxyl group.

The above $R_{13}$ is preferably selected from:
1) hydrogen,
2) C1-C10 alkyl,
3) C1-C10 alkylcarbonyl, wherein the alkyl is optionally substituted with a hydroxyl group(s),
4) C1-C10 alkoxycarbonyl,
5) aminocarbonyl,
6) C1-C10 alkylaminocarbonyl and
7) heterocyclic carbonyl optionally substituted with C1-C10 alkyl.

The above $R_{14}$ is preferably selected from:
1) hydrogen and
2) C1-C10 alkyl optionally substituted with a group(s) independently selected from a halogen atom, a hydroxyl group, amino and C1-C10 alkylamino.

Further, $R_{13}$ and $R_{14}$ may be bonded to form a 4- to 7-membered heterocycle optionally containing an additional element(s) or group(s) independently selected from O, N, S, SO and $SO_2$, and the heterocycle optionally contains carbonyl, and the heterocycle is optionally substituted with C1-C10 alkyl.

The above $R_{15}$ is preferably selected from:
1) C1-C10 alkyl and
2) —$NR_{35}R_{36}$.

The above $R_{35}$ is preferably selected from:
1) hydrogen,
2) C1-C10 alkyl optionally substituted with a group(s) independently selected from:
i) a halogen atom,
ii) a hydroxyl group,
iii) C1-C10 alkylcarbonylamino,
iv) —$COR_{16}$,
v) amino,
vi) C1-C10 alkylamino,
vii) C1-C10 alkoxy optionally substituted with a halogen atom(s),
viii) heteroaryl optionally substituted with a C1-C10 alkyl group(s) and
ix) a heterocycle,
3) aryl optionally substituted with a group(s) independently selected from a halogen atom, a hydroxyl group, amino and C1-C10 alkylamino,
4) cycloalkyl optionally substituted with a group(s) independently selected from a halogen atom and a hydroxyl group,
5) a heterocycle optionally substituted with a group(s) independently selected from C1-C10 alkyl, a halogen atom and aryl C1-C10 alkyl,
6) heteroaryl optionally substituted with C1-C10 alkyl and
7) C1-C10 alkylcarbonyl.

The above $R_{36}$ is preferably selected from:
1) hydrogen and
2) C1-C10 alkyl optionally substituted with a group(s) independently selected from a halogen atom, a hydroxyl group and aryl.

The above $R_{35}$ and $R_{36}$ may be bonded to each other to form a ring selected from azetidinyl, pyrrolidinyl, piperidinyl, piperazinyl and morpholinyl, and the ring is optionally substituted with a group(s) selected independently of each other from C1-C10 alkyl and a halogen atom.

The above $R_{25}$ is preferably selected from:
1) a halogen atom,
2) C1-C10 alkyl optionally substituted with a group(s) independently selected from:
i) a halogen atom,
ii) aryl,
iii) heteroaryl,
iv) a heterocycle optionally substituted with a C1-C10 alkyl group(s),
v) —$COR_{16}$,
vi) —$NR_{13}R_{14}$ and
vii) —$SO_2R_{21}$.
3) C1-C10 heteroalkyl optionally substituted with a hydroxyl group(s),
4) C1-C10 hydroxyalkyl, wherein each hydroxyl group may be independently substituted with a group(s) selected from C1-C10 alkyl, aryl C1-C10 alkyl and C1-C10 alkylcarbonyl,
5) —$COR_{16}$,
6) —$SO_2R_{21}$,
7) aryl and
8) cyano.

The above $R_2$ is preferably selected from:
1) C1-C10 alkyl optionally substituted with a halogen atom(s), wherein the alkyl group is optionally further substituted with a substituent(s) independently selected from $R_{42}$,
2) C2-C10 alkenyl optionally substituted with a halogen atom(s), wherein the alkenyl group is optionally further substituted with a substituent(s) independently selected from $R_{42}$,
3) C2-C10 alkynyl optionally substituted with a halogen atom(s), wherein the alkynyl group is optionally further substituted with a substituent(s) independently selected from $R_{42}$,
4) cycloalkyl optionally substituted with a group(s) independently selected from:
i) a halogen atom,
ii) C2-C10 alkenyl or C1-C10 alkyl,
iii) aryl optionally substituted with 1 to 3 substituents independently selected from C1-C10 alkyl, a halogen atom, C1-C10 alkoxy, C1-C10 alkylamino and C1-C10 alkylcarbonyl,
iv) cycloalkyl,
v) C2-C10 alkenyl optionally substituted with halogen,
vi) C1-C10 alkylidene, wherein the alkylidene is bonded to the cycloalkyl by a double bond and the alkylidene is optionally substituted with a halogen atom(s),
vii) C1-C10 alkoxy optionally substituted with a halogen atom(s),
viii) C1-C10 alkyl optionally substituted with a group(s) independently selected from a halogen atom or C1-C10 alkoxy optionally substituted with a halogen atom(s),
ix) C2-C10 alkynyl and
x) —$Si(R_{43})_3$,
5) a heterocycle, wherein the heterocycle is optionally substituted with a group(s) independently selected from:
i) a C1-C10 alkyl group,
ii) C1-C10 alkylcarbonyl, wherein the alkyl group is optionally substituted with $R_{27}$,
iii) arylcarbonyl, wherein the aryl group is optionally substituted with a group(s) independently selected from a halogen atom, C1-C10 alkyl and C1-C10 alkoxy,
iv) heteroarylcarbonyl,
v) C1-C10 alkoxycarbonyl, wherein the alkyl group is optionally substituted with a group(s) independently selected from a halogen atom, aryl and C1-C10 alkoxy,
vi) aryloxycarbonyl, wherein the aryl group is optionally substituted with a halogen atom(s) and/or C1-C10 alkyl,
vii) —$CONR_{28}R_{29}$,
viii) —$SO_2R_{21}$,
ix) a halogen atom,
x) cycloalkylcarbonyl optionally fused with an aryl group and
xi) C2-C10 alkenylcarbonyl, wherein the alkenyl group is optionally substituted with aryl, wherein the aryl is optionally substituted with a group(s) independently selected from a halogen atom, C1-C10 alkyl or C1-C10 alkoxy,
6) aryl optionally substituted with a group(s) independently selected from $R_{44}$,
7) heteroaryl optionally substituted with a group(s) independently selected from:
i) a halogen atom,
ii) C1-C10 alkyl and
iii) C1-C10 alkoxy;
8) C1-C10 alkoxy optionally substituted with a halogen atom(s), wherein the alkoxy group is optionally further substituted with a substituent(s) independently selected from $R_{42}$,
9) —$S(O)_qR^{43}$ (wherein q is an integer of 0 to 2) and
10) cycloalkenyl optionally substituted with C1-C10 alkyl.

More preferably, the above $R_2$ is selected from:
1) C1-C10 alkyl optionally substituted with a halogen atom(s), wherein the alkyl group is optionally further substituted with a group selected from $R_{42}$,
2) C2-C10 alkenyl optionally substituted with a halogen atom(s), wherein the alkenyl group is optionally further substituted with a group selected from $R_{42}$,
3) C2-C10 alkynyl optionally substituted with a halogen atom(s), wherein the alkynyl group is optionally further substituted with a group selected from $R_{42}$,
4) cycloalkyl optionally substituted with a group(s) independently selected from:
i) a halogen atom,
ii) C2-C10 alkenyl or C1-C10 alkyl,
iii) aryl optionally substituted with a group(s) independently selected from C1-C10 alkyl, a halogen atom and C1-C10 alkoxy,
iv) cycloalkyl,
v) C2-C10 haloalkenyl or C1-C10 haloalkyl,
vi) C1-C10 alkylidene, wherein the alkylidene is bonded to the cycloalkyl by a double bond and the alkylidene is optionally substituted with a halogen atom(s),
vii) C1-C10 alkoxy optionally substituted with a halogen atom(s),
viii) C1-C10 alkyl substituted with C1-C10 alkoxy,
wherein the alkyl and/or the alkyl in the alkoxy is optionally substituted with a halogen atom(s),
ix) C2-C10 alkynyl and
x) —$Si(R_{43})_{3r}$
5) a heterocycle, wherein the heterocycle is optionally substituted with a group(s) selected from:
i) a C1-C10 alkyl group,
ii) C1-C10 alkylcarbonyl, wherein the alkyl group is optionally substituted with $R_{27}$,
iii) arylcarbonyl, wherein the aryl group is optionally substituted with a group(s) independently selected from a halogen atom, C1-C10 alkyl and C1-C10 alkoxy, iv) heteroarylcarbonyl, v) C1-C10 alkoxycarbonyl, wherein the alkyl group is optionally substituted with a group(s) independently selected from a halogen atom, aryl and C1-C10 alkoxy, vi) aryloxycarbonyl, wherein the aryl group is optionally substituted with a halogen atom(s) and/or C1-C10 alkyl, vii) —$CONR_{28}R_{29}$ and viii) —$SO_2R_{21}$, 6) aryl optionally substituted with a group(s) independently selected from $R_{44}$, 7) heteroaryl optionally substituted with any of the following groups:

i) C1-C10 alkyl,

8) C1-C10 alkoxy optionally substituted with a halogen atom(s), wherein the alkoxy group is optionally further substituted with a group selected from $R_{42}$, 9) —$S(O)_qR_{43}$ (wherein q is an integer of 0 to 2) and 10) cycloalkenyl optionally substituted with C1-C10 alkyl.

Still more preferably, the above $R_2$ is selected from:

1) C1-C13 alkyl optionally substituted with a halogen atom(s), wherein the alkyl group is optionally further substituted with a group selected from $R_{42}$, 2) C2-C13 alkenyl optionally substituted with a halogen atom(s), wherein the alkenyl group is optionally further substituted with a group selected from $R_{42}$, 3) C2-C13 alkynyl optionally substituted with a halogen atom(s), wherein the alkynyl group is optionally further substituted with a group selected from $R_{42}$.

4) cycloalkyl optionally substituted with a group(s) independently selected from:

i) a halogen atom, ii) C2-C6 alkenyl or C1-C6 alkyl, iii) aryl optionally substituted with a group(s) independently selected from C1-C6 alkyl, a halogen atom, C1-C6 alkoxy, C1-C6 alkylamino and C1-C6 alkylcarbonyl, iv) cycloalkyl, v) C2-C6 haloalkenyl or C1-C6 haloalkyl, vi) C1-C6 alkylidene, wherein the alkylidene is bonded to the cycloalkyl by a double bond and the alkylidene is optionally substituted with a halogen atom(s), vii) C1-C6 alkoxy optionally substituted with a halogen atom(s), viii) C1-C6 alkyl substituted with C1-C6 alkoxy, wherein the alkyl and/or the alkyl in the alkoxy is optionally substituted with halogen, ix) C2-C6 alkynyl and x) —$Si(R_{43})_3$, 5) a group represented by the following general formula (B):

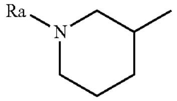

(B)

(wherein Ra represents a group selected from:

i) C1-C6 alkylcarbonyl, wherein the alkyl group is optionally substituted with $R_{27}$, ii) arylcarbonyl, wherein the aryl group is optionally substituted with a group(s) independently selected from a halogen atom, C1-C6 alkyl and C1-C6 alkoxy, iii) C1-C6 alkoxycarbonyl, wherein the alkyl group is optionally substituted with a group(s) selected from a halogen atom, aryl and C1-C6 alkoxy, iv) aryloxycarbonyl, wherein the aryl group is optionally substituted with a halogen atom(s) or C1-C6 alkyl, v) —$CONR_{28}R_{29}$ and vi) —$SO_2R_{21}$), 6) aryl optionally substituted with a group(s) independently selected from $R_{44}$, 7) heteroaryl optionally substituted with any of the following groups:

i) a halogen atom, ii) C1-C6 alkyl and iii) C1-C6 alkoxy;

8) C1-C6 alkoxy optionally substituted with a halogen atom(s), wherein the alkoxy group is optionally further substituted with a group selected from $R_{42}$, 9) —$S(O)_qR_{43}$ (wherein q is an integer of 0 to 2) and 10) cycloalkenyl optionally substituted with C1-C6 alkyl.

When the above $R_2$ is a "cycloalkyl optionally substituted with 1 to 3 substituents" and the substituent is "alkylidene (wherein the alkylidene is bonded to the cycloalkyl by a double bond and the alkylidene is optionally substituted with 1 to 5 halogen atoms)", examples of the $R_2$ include the following groups.

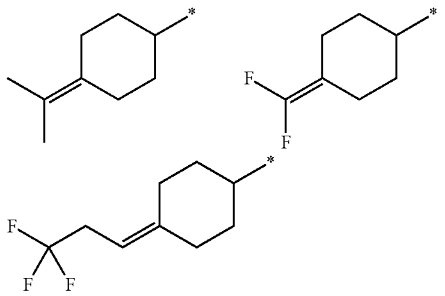

$R_{44}$ is preferably selected from:

1) a halogen atom, 2) cyano,

3) C1-C10 alkyl optionally substituted with a group(s) independently selected from:

i) a hydroxyl group, ii) —$OR_{26}$, iii) cyano, iv) aryloxy optionally substituted with a group(s) independently selected from a halogen atom, C1-C10 alkyl optionally substituted with a halogen atom(s) or C1-C10 alkoxy optionally substituted with a halogen atom(s) and v) a halogen atom, 4) cycloalkyl optionally substituted with a group(s) independently selected from a halogen atom or C1-C10 alkyl optionally substituted with a halogen atom(s), 5) C1-C10 alkoxy optionally substituted with a halogen atom(s) or a C2-C6 alkenyl group(s),

6) —$COR_{30}$,

7) C1-C10 alkylcarbonylamino,

8) C1-C10 alkoxycarbonylamino, wherein the alkoxy group is optionally substituted with aryl, 9) C1-C10 heteroalkyl optionally substituted with a halogen atom(s), 10) aryl optionally substituted with a substituent(s) independently selected from:

i) a halogen atom, ii) C1-C10 alkyl, iii) C1-C10 alkoxy and iv) aryl optionally substituted with aryl optionally substituted with C1-C10 alkyl, 11) heteroaryl optionally substituted with a C1-C10 alkyl group(s),
12) —$SO_2R_{43}$,
13) —$SOR_{43}$.
14) C1-C10 alkylthio optionally substituted with a halogen atom(s),
15) —$Si(R_{43})_3$ and
16) —$SF_5$.

More preferably, $R_{44}$ is selected from:
1) a halogen atom,
2) cyano,
3) C1-C10 alkyl optionally substituted with any of the following groups:
 i) a hydroxyl group,
 ii) —$OR_{26}$,
 iii) cyano and
 iv) aryloxy optionally substituted with a group(s) selected from a halogen atom, C1-C10 alkyl, C1-C10 haloalkyl or C1-C10 haloalkoxy,
4) C1-C10 haloalkyl,
5) cycloalkyl optionally substituted with a group(s) selected from a halogen atom and C1-C10 haloalkyl,
6) C1-C10 alkoxy optionally substituted with a halogen atom(s) or a C2-C6 alkenyl group(s),
7) —$COR_{30}$.
8) C1-C10 heteroalkyl optionally substituted with a halogen atom(s),
9) aryl optionally substituted with a group(s) independently selected from:
 i) C1-C10 alkyl and
 ii) aryl,
10) heteroaryl optionally substituted with a C1-C10 alkyl group(s),
11) —$SO_2R_{43}$,
12) C1-C10 alkylthio optionally substituted with a halogen atom(s),
13) —$Si(R_{43})_3$ and
14) —$SF_5$.

Still more preferably, $R_{44}$ is selected from:
1) a halogen atom,
2) cyano,
3) C1-C6 alkyl optionally substituted with any of the following groups:
 i) a hydroxyl group,
 ii) —$OR_{26}$,
 iii) cyano and
 iv) aryloxy optionally substituted with a group(s) selected from a halogen atom, C1-C6 alkyl, C1-C6 haloalkyl or C1-C6 haloalkoxy,
4) C1-C6 haloalkyl,
5) cycloalkyl optionally substituted with a group(s) selected from a halogen atom and C1-C6 haloalkyl,
6) C1-C6 alkoxy optionally substituted with a halogen atom(s),
7) —$COR_{30}$,
8) C1-C6 heteroalkyl optionally substituted with a halogen atom(s),
9) aryl optionally substituted with a group(s) independently selected from:
 i) C1-C6 alkyl and
 ii) aryl,
10) heteroaryl optionally substituted with a C1-C6 alkyl group(s),
11) —$SO_2R_{43}$,
12) C1-C6 alkylthio optionally substituted with a halogen atom(s),
13) —$Si(R_{43})_3$ and
14) —$SF_5$.

$R_{42}$ is preferably selected from:
1) hydrogen,
2) aryl optionally substituted with a group(s) independently selected from C1-C10 alkyl optionally substituted with halogen, a halogen atom and C1-C10 alkoxy,
3) hydroxycarbonyl,
4) C1-C10 alkoxycarbonyl,
5) aminocarbonyl,
6) C1-C10 alkylaminocarbonyl,
7) C1-C10 alkoxycarbonylamino,
8) amino,
9) a hydroxyl group and
10) oxetane, tetrahydrofuran or tetrahydropyran optionally substituted with C1-C10 alkyl.

$R_{43}$ preferably represents a C1-C10 alkyl group.

$R_{26}$ is preferably aryl, or C1-C10 alkyl optionally substituted with a halogen atom(s).

$R_{27}$ is preferably selected from:
1) aryl optionally substituted with a group(s) independently selected from a halogen atom, C1-C10 alkyl and C1-C10 alkoxy,
2) C1-C10 alkoxy, wherein the alkyl group is optionally substituted with aryl,
3) a hydroxyl group,
4) amino,
5) C1-C10 alkylamino,
6) hydroxycarbonyl,
7) heteroaryl optionally substituted with a group(s) independently selected from C1-C10 alkyl and/or aryl, and
8) heteroaryloxy.

More preferably, $R_{27}$ is selected from:
1) aryl optionally substituted with a group(s) independently selected from a halogen atom, C1-C10 alkyl and C1-C10 alkoxy,
2) C1-C10 alkoxy, wherein the alkyl group is optionally substituted with aryl,
3) heteroaryl optionally substituted with a group(s) independently selected from C1-C10 alkyl and aryl and
4) heteroaryloxy.

The above $R_{28}$ is preferably selected from hydrogen or C1-C10 alkyl optionally substituted with aryl.

The above $R_{29}$ is preferably selected from hydrogen or C1-C10 alkyl optionally substituted with aryl.

The above $R_{28}$ and $R_{29}$ may be bonded to form a ring selected from azetidinyl, pyrrolidinyl, piperidinyl, piperazinyl and morpholinyl, and the ring is optionally substituted with a group(s) selected independently of each other from C1-C10 alkyl and a halogen atom.

The above $R_{30}$ is preferably selected from a hydroxyl group, C1-C10 alkoxy and —$NR_{31}R_{32}$.

Preferably, the above $R_{31}$ and $R_{32}$ are independently selected from:
1) hydrogen,
2) C1-C10 alkyl optionally substituted with aryl and
3) aryl.

The above $R_{31}$ and $R_{32}$ may be bonded to form a ring selected from azetidinyl, pyrrolidinyl, piperidinyl, piperazinyl and morpholinyl, and the ring is optionally substituted with a group(s) selected independently of each other from C1-C10 alkyl, a halogen atom and C1-C10 alkoxycarbonyl.

Preferably, the above $R_{33}$ and $R_{34}$ are independently selected from:
1) hydrogen and
2) C1-C10 alkyl.

More preferably, the above $R_{33}$ and $R_{34}$ are hydrogen.

In the above formula (2), U preferably represents a bond, C1-C10 alkylene or any group selected from groups represented by the following formula.

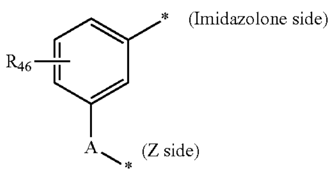

More preferably, U is C1-C6 alkylene or any group selected from groups represented by the following formula.

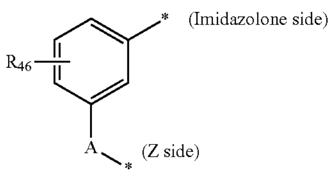

A is preferably selected from O, NH and $CH_2$ and is more preferably O.

$R_{46}$ is preferably selected from hydrogen or $R_{44}$, more preferably selected from hydrogen, C1-C10 alkyl, C1-C10 haloalkyl and C1-C10 hydroxyalkyl, and still more preferably selected from C1-C10 alkyl, C1-C10 haloalkyl and C1-C10 hydroxyalkyl.

T is preferably selected from aryl and heteroaryl.

V is preferably selected from:

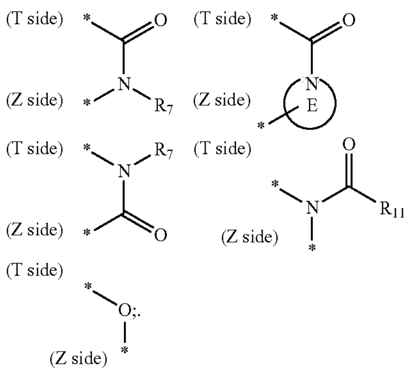

More preferably, V is selected from:

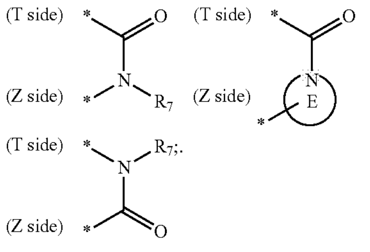

E is preferably a 4- to 7-membered heterocycle optionally containing 1 to 2 additional elements or groups selected from O, N, S, SO and $SO_2$, and the heterocycle is optionally substituted with one substituent selected from:

1) hydrogen,
2) a halogen atom,
3) C1-C10 alkyl optionally having a group(s) independently selected from C1-C10 alkylamino, a halogen atom and a hydroxyl group,
4) a hydroxyl group,
5) C1-C10 alkoxy optionally substituted with a group(s) independently selected from a halogen atom, a hydroxyl group, amino and C1-C10 alkylamino,
6) aryl optionally substituted with a group(s) independently selected from a halogen atom, a hydroxyl group, amino and C1-C10 alkylamino,
7) C1-C10 heteroalkyl optionally substituted with a group(s) independently selected from a halogen atom, a hydroxyl group, amino and C1-C10 alkylamino,
8) a heterocycle optionally substituted with C1-C10 alkyl,
9) heteroaryl optionally substituted with C1-C10 alkyl,
10) heterocyclyl C1-C10 alkyl,
11) —$COR_{16}$,
12) —$NR_{19}R_{20}$ and
13) —$SO_2R_{21}$.

More preferably, E is pyrrolidine or piperidine optionally substituted with a hydroxyl group.

Z is preferably a divalent group selected from:

1) C1-C10 alkylene or C1-C10 heteroalkylene optionally substituted with a halogen atom(s) and/or a hydroxyl group(s), wherein the carbon atom(s) may be oxidized to form carbonyl;
2) C1-C10 alkenylene or C1-C10 heteroalkenylene optionally substituted with a halogen atom(s) and/or a hydroxyl group(s), wherein the carbon atom(s) may be oxidized to form carbonyl; and
3) a group selected from:

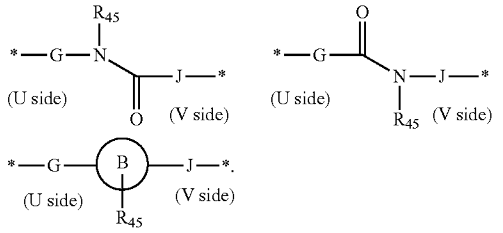

G is preferably a divalent group selected from:

1) C1-C10 alkylene or C1-C10 heteroalkylene optionally substituted with a halogen atom(s); and
2) C1-C10 alkenylene or a C1-C10 heteroalkenylene optionally substituted with a halogen atom(s).

J is preferably a divalent group selected from:

1) C1-C10 alkylene or C1-C10 heteroalkylene optionally substituted with a halogen atom(s); and
2) C1-C10 alkenylene or a C1-C10 heteroalkenylene optionally substituted with a halogen atom(s).

B is preferably selected from a heterocycle or heteroaryl.

$R_{45}$ is preferably selected from hydrogen or C1-C10 alkyl.

$R_7$ is preferably selected from:

1) hydrogen,
2) C1-C10 alkyl optionally substituted with a group(s) independently selected from amino and C1-C10 alkylamino,
3) C1-C10 hydroxyalkyl,
4) C1-C10 heteroalkyl, 5) C1-C10 heteroalkyl optionally substituted with 1 to 3 groups selected from a hydroxyl group, C1-C10 alkylamino and C2-C10 alkenyl,
6) aryl,
7) heteroaryl,
8) aryl C1-C10 alkyl,
9) a heterocycle optionally substituted with C1-C10 alkyl,
10) —$(CH_2)_L COR_{16}$ (wherein L represents an integer of 1 to 4),
11) C1-C10 alkoxy,
12) C2-C10 alkenyl and
13) —$NR_{40}R_{41}$.

More preferably, $R_7$ is selected from:
1) hydrogen,
2) C1-C10 alkyl and
3) C1-C10 hydroxyalkyl.

Specific examples of the compound represented by the formula (1) according to the present invention include the following compounds:

(1) 8-(3-chloro-benzenesulfonyl)-2-cyclohexyl-1,3,8-triaza-spiro[4.5]dec-1-en-4-one;
(2) 8-(3-chloro-benzenesulfonyl)-2-pyridin-4-yl-1,3,8-triaza-spiro[4.5]dec-1-en-4-one;
(3) 8-(3-chloro-benzenesulfonyl)-2-propyl-1,3,8-triaza-spiro[4.5]dec-1-en-4-one;
(4) 8-(3-chloro-benzenesulfonyl)-2-isopropyl-1,3,8-triaza-spiro[4.5]dec-1-en-4-one;
(5) 8-(3-chloro-benzenesulfonyl)-2-(3-methoxy-phenyl)-1,3,8-triaza-spiro[4.5]dec-1-en-4-one;
(6) 8-(3-chloro-benzenesulfonyl)-2-(3-chloro-phenyl)-1,3,8-triaza-spiro[4.5]dec-1-en-4-one;
(7) 2-benzyl-8-(3-chloro-benzenesulfonyl)-1,3,8-triaza-spiro[4.5]dec-1-en-4-one;
(8) 8-(3-chloro-benzenesulfonyl)-2-methyl-1,3,8-triaza-spiro[4.5]dec-1-en-4-one;
(10) 2-biphenyl-2-yl-8-(3-chloro-benzenesulfonyl)-1,3,8-triaza-spiro[4.5]dec-1-en-4-one;
(11) 8-(3-chloro-benzenesulfonyl)-2-o-tolyl-1,3,8-triaza-spiro[4.5]dec-1-en-4-one;
(12) 8-(3-chloro-benzenesulfonyl)-2-(4-trifluoromethyl-phenyl)-1,3,8-triaza-spiro[4.5]dec-1-en-4-one;
(13) 8-(3-chloro-benzenesulfonyl)-2-(3-trifluoromethoxy-phenyl)-1,3,8-triaza-spiro[4.5]dec-1-en-4-one;
(14) 8-(3-chloro-benzenesulfonyl)-2-(1-methyl-cyclohexyl)-1,3,8-triaza-spiro[4.5]dec-1-en-4-one;
(15) 2-(1-acetyl-piperidin-4-yl)-8-(3-chloro-benzenesulfonyl)-1,3,8-triaza-spiro[4.5]dec-1-en-4-one;
(16) 2-tert-butyl-8-(3-chloro-benzenesulfonyl)-1,3,8-triaza-spiro[4.5]dec-1-en-4-one;
(17) 8-(3-chloro-benzenesulfonyl)-2-(4-trifluoromethyl-cyclohexyl)-1,3,8-triaza-spiro[4.5]dec-1-en-4-one;
(18) 3-[8-(3-chloro-benzenesulfonyl)-4-oxo-1,3,8-triaza-spiro[4.5]dec-1-en-2-yl]-piperidine-1-carboxylic acid tert-butyl ester;
(19) 8-(3-chloro-benzenesulfonyl)-2-(3-methyl-cyclohexyl)-1,3,8-triaza-spiro[4.5]dec-1-en-4-one;
(20) 8-(3-chloro-benzenesulfonyl)-2-(2-methyl-cyclohexyl)-1,3,8-triaza-spiro[4.5]dec-1-en-4-one;
(21) 8-(3-chloro-benzenesulfonyl)-2-(4-propyl-cyclohexyl)-1,3,8-triaza-spiro[4.5]dec-1-en-4-one;
(22) 2-(1R,2S,4S)-bicyclo[2.2.1]hept-2-yl-8-(3-chloro-benzenesulfonyl)-1,3,8-triaza-spiro[4.5]dec-1-en-4-one;
(23) 2-(1R,2R,4S)-bicyclo[2.2.1]hept-2-yl-8-(3-chloro-benzenesulfonyl)-1,3,8-triaza-spiro[4.5]dec-1-en-4-one;
(24) 8-(3-chloro-benzenesulfonyl)-2-(4-methoxy-cyclohexyl)-1,3,8-triaza-spiro[4.5]dec-1-en-4-one;
(25) 8-(3-chloro-benzenesulfonyl)-2-(4-methoxy-cyclohexyl)-1,3,8-triaza-spiro[4.5]dec-1-en-4-one;
(26) 2-(4-tert-butyl-cyclohexyl)-8-(3-chloro-benzenesulfonyl)-1,3,8-triaza-spiro[4.5]dec-1-en-4-one;
(27) 8-(3-chloro-benzenesulfonyl)-2-(4-fluoromethyl-cyclohexyl)-1,3,8-triaza-spiro[4.5]dec-1-en-4-one;
(28) 8-(3-chloro-benzenesulfonyl)-2-cyclohexylmethyl-1,3,8-triaza-spiro[4.5]dec-1-en-4-one;
(29) 8-(3-chloro-benzenesulfonyl)-2-phenethyl-1,3,8-triaza-spiro[4.5]dec-1-en-4-one;
(30) 8-(3-chloro-benzenesulfonyl)-2-(2-cyclohexyl-ethyl)-1,3,8-triaza-spiro[4.5]dec-1-en-4-one;
(31) 8-(3-chloro-benzenesulfonyl)-2-(3-trifluoromethyl-phenyl)-1,3,8-triaza-spiro[4.5]dec-1-en-4-one;
(32) 8-(3-chloro-benzenesulfonyl)-2-(3-methanesulfonyl-phenyl)-1,3,8-triaza-spiro[4.5]dec-1-en-4-one;
(33) 8-(3-chloro-benzenesulfonyl)-2-(1-phenyl-cyclohexyl)-1,3,8-triaza-spiro[4.5]dec-1-en-4-one;
(34) 8-(3-chloro-benzenesulfonyl)-2-(2-naphthalen-1-yl-ethyl)-1,3,8-triaza-spiro[4.5]dec-1-en-4-one;
(35) 8-(2-naphthalen-1-yl-ethanesulfonyl)-2-(3-trifluoromethyl-phenyl)-1,3,8-triaza-spiro[4.5]dec-1-en-4-one;
(36) 2-tert-butyl-8-(2-naphthalen-1-yl-ethanesulfonyl)-1,3,8-triaza-spiro[4.5]dec-1-en-4-one;
(37) 8-(2-naphthalen-1-yl-ethanesulfonyl)-2-(4-trifluoromethyl-cyclohexyl)-1,3,8-triaza-spiro[4.5]dec-1-en-4-one;
(38) 3-[8-(2-naphthalen-1-yl-ethanesulfonyl)-4-oxo-1,3,8-triaza-spiro[4.5]dec-1-en-2-yl]-piperidine-1-carboxylic acid tert-butyl ester;
(39) 8-(2-naphthalen-1-yl-ethanesulfonyl)-2-[1-(2-naphthalen-1-yl-ethanesulfonyl)-piperidin-3-yl]-1,3,8-triaza-spiro[4.5]dec-1-en-4-one;
(40) 8-(3-chloro-benzenesulfonyl)-2-[1-(propane-1-sulfonyl)-piperidin-3-yl]-1,3,8-triaza-spiro[4.5]dec-1-en-4-one;
(41) 2-(1-benzenesulfonyl-piperidin-3-yl)-8-(3-chloro-benzenesulfonyl)-1,3,8-triaza-spiro[4.5]dec-1-en-4-one;
(42) 8-(3-chloro-benzenesulfonyl)-2-(1-phenylmethanesulfonyl-piperidin-3-yl)-1,3,8-triaza-spiro[4.5]dec-1-en-4-one;
(43) 8-(2-naphthalen-1-yl-ethanesulfonyl)-2-(1-phenylmethanesulfonyl-piperidin-3-yl)-1,3,8-triaza-spiro[4.5]dec-1-en-4-one;
(44) 8-(4-chloro-benzenesulfonyl)-2-(2,4-dichloro-phenyl)-1,3,8-triaza-spiro[4.5]dec-1-en-4-one;
(45) 2-(2,4-dichloro-phenyl)-8-(2-trifluoromethyl-benzenesulfonyl)-1,3,8-triaza-spiro[4.5]dec-1-en-4-one;
(46) 8-(butane-1-sulfonyl)-2-(2,4-dichloro-phenyl)-1,3,8-triaza-spiro[4.5]dec-1-en-4-one;
(47) 2-(2,4-dichloro-phenyl)-8-(2-naphthalen-1-yl-ethanesulfonyl)-1,3,8-triaza-spiro[4.5]dec-1-en-4-one;
(48) 2-(2,4-dichloro-phenyl)-8-(quinoline-8-sulfonyl)-1,3,8-triaza-spiro[4.5]dec-1-en-4-one;
(49) 8-(3-chloro-4-fluoro-benzenesulfonyl)-2-(2,4-dichloro-phenyl)-1,3,8-triaza-spiro[4.5]dec-1-en-4-one;
(50) 8-(3-chloro-benzenesulfonyl)-2-(2,4-dichloro-phenyl)-1,3,8-triaza-spiro[4.5]dec-1-en-4-one;
(51) 2-(2-cyclohexyl-4-oxo-1,3,8-triaza-spiro[4.5]dec-1-ene-8-sulfonyl)-benzoic acid methyl ester;
(52) 2-cyclohexyl-8-(5-methyl-3-phenyl-isoxazole-4-sulfonyl)-1,3,8-triaza-spiro[4.5]dec-1-en-4-one;
(53) 8-(benzo[b]thiophene-3-sulfonyl)-2-cyclohexyl-1,3,8-triaza-spiro[4.5]dec-1-en-4-one;
(54) 8-(benzo[b]thiophene-2-sulfonyl)-2-cyclohexyl-1,3,8-triaza-spiro[4.5]dec-1-en-4-one;
(55) 8-(5-chloro-thiophene-2-sulfonyl)-2-cyclohexyl-1,3,8-triaza-spiro[4.5]dec-1-en-4-one;

(56) 2-cyclohexyl-8-(thiophene-2-sulfonyl)-1,3,8-triaza-spiro[4.5]dec-1-en-4-one;

(57) 2-cyclohexyl-8-(naphthalene-1-sulfonyl)-1,3,8-triaza-spiro[4.5]dec-1-en-4-one;

(58) 2-cyclohexyl-8-(2,4-dimethyl-thiazole-5-sulfonyl)-1,3,8-triaza-spiro[4.5]dec-1-en-4-one;

(59) 2-cyclohexyl-8-(3,5-dimethyl-isoxazole-4-sulfonyl)-1,3,8-triaza-spiro[4.5]dec-1-en-4-one;

(60) 2-cyclohexyl-8-(2,3-dihydro-benzo[1,4]dioxine-6-sulfonyl)-1,3,8-triaza-spiro[4.5]dec-1-en-4-one;

(61) 2-cyclohexyl-8-(2-naphthalen-1-yl-ethanesulfonyl)-1,3,8-triaza-spiro[4.5]dec-1-en-4-one;

(62) 3-(2-cyclohexyl-4-oxo-1,3,8-triaza-spiro[4.5]dec-1-ene-8-sulfonyl)-thiophene-2-carboxylic acid methyl ester;

(63) 5-(2-cyclohexyl-4-oxo-1,3,8-triaza-spiro[4.5]dec-1-ene-8-sulfonyl)-4-methyl-thiophene-2-carboxylic acid methyl ester;

(64) 2-cyclohexyl-8-(2,5-dimethyl-thiophene-3-sulfonyl)-1,3,8-triaza-spiro[4.5]dec-1-en-4-one;

(65) 8-(5-bromo-thiophene-2-sulfonyl)-2-cyclohexyl-1,3,8-triaza-spiro[4.5]dec-1-en-4-one;

(66) 8-(5-chloro-thiophene-2-sulfonyl)-2-(3-trifluoromethyl-phenyl)-1,3,8-triaza-spiro[4.5]dec-1-en-4-one;

(67) 8-(naphthalene-2-sulfonyl)-2-(3-trifluoromethyl-phenyl)-1,3,8-triaza-spiro[4.5]dec-1-en-4-one;

(68) 8-(benzo[b]thiophene-2-sulfonyl)-2-(3-trifluoromethyl-phenyl)-1,3,8-triaza-spiro[4.5]dec-1-en-4-one;

(69) 8-(5-bromo-thiophene-2-sulfonyl)-2-(3-trifluoromethyl-phenyl)-1,3,8-triaza-spiro[4.5]dec-1-en-4-one;

(70) 8-(3-chloro-benzenesulfonyl)-2-cyclohexyl-1,3,8-triaza-spiro[4.6]undec-1-en-4-one;

(71) 7-(3-chloro-benzenesulfonyl)-2-cyclohexyl-1,3,7-triaza-spiro[4.5]dec-1-en-4-one;

(72) 7-(3-chloro-benzenesulfonyl)-2-cyclohexyl-1,3,7-triaza-spiro[4.4]non-1-en-4-one;

(73) 4-{2-[2-(2,4-dichloro-phenyl)-4-oxo-1,3,8-triaza-spiro[4.5]dec-1-ene-8-sulfonyl]-ethyl}-3,N,N-trimethyl-benzamide;

(74) 4-[2-(2-tert-butyl-4-oxo-1,3,8-triaza-spiro[4.5]dec-1-ene-8-sulfonyl)-ethyl]-3,N,N-trimethyl-benzamide;

(75) 3,N,N-trimethyl-4-{2-[4-oxo-2-(4-trifluoromethyl-phenyl)-1,3,8-triaza-spiro[4.5]dec-1-ene-8-sulfonyl]-ethyl}-benzamide;

(76) 3,N,N-trimethyl-4-{2-[2-(4-methyl-cyclohexyl)-4-oxo-1,3,8-triaza-spiro[4.5]dec-1-ene-8-sulfonyl]-ethyl}-benzamide;

(77) 4-[2-(2-cyclopentyl-4-oxo-1,3,8-triaza-spiro[4.5]dec-1-ene-8-sulfonyl)-ethyl]-3,N,N-trimethyl-benzamide;

(78) 4-{2-[2-(2,6-difluoro-phenyl)-4-oxo-1,3,8-triaza-spiro[4.5]dec-1-ene-8-sulfonyl]-ethyl}-3,N,N-trimethyl-benzamide;

(79) 4-{2-[2-(2,6-dimethoxy-phenyl)-4-oxo-1,3,8-triaza-spiro[4.5]dec-1-ene-8-sulfonyl]-ethyl}-3,N,N-trimethyl-benzamide;

(80) 4-{2-[2-(3-methoxy-phenyl)-4-oxo-1,3,8-triaza-spiro[4.5]dec-1-ene-8-sulfonyl]-ethyl}-3,N,N-trimethyl-benzamide;

(81) 4-{2-[2-(3-chloro-phenyl)-4-oxo-1,3,8-triaza-spiro[4.5]dec-1-ene-8-sulfonyl]-ethyl}-3,N,N-trimethyl-benzamide;

(82) 4-{2-[2-(3,5-bis-trifluoromethyl-phenyl)-4-oxo-1,3,8-triaza-spiro[4.5]dec-1-ene-8-sulfonyl]-ethyl}-3,N,N-trimethyl-benzamide;

(83) 4-[2-(2-benzyl-4-oxo-1,3,8-triaza-spiro[4.5]dec-1-ene-8-sulfonyl)-ethyl]-3,N,N-trimethyl-benzamide;

(84) 3,N,N-trimethyl-4-[2-(4-oxo-2-m-tolyl-1,3,8-triaza-spiro[4.5]dec-1-ene-8-sulfonyl)-ethyl]-benzamide;

(85) 4-{2-[2-(2-chloro-5-trifluoromethyl-phenyl)-4-oxo-1,3,8-triaza-spiro[4.5]dec-1-ene-8-sulfonyl]-ethyl}-3,N,N-trimethyl-benzamide;

(86) 3,N,N-trimethyl-4-{2-[4-oxo-2-(3-trifluoromethyl-phenyl)-1,3,8-triaza-spiro[4.5]dec-1-ene-8-sulfonyl]-ethyl}-benzamide;

(87) 4-{2-[2-(4-chloro-phenyl)-4-oxo-1,3,8-triaza-spiro[4.5]dec-1-ene-8-sulfonyl]-ethyl}-3,N,N-trimethyl-benzamide;

(88) 4-{2-[2-(2,3-dichloro-phenyl)-4-oxo-1,3,8-triaza-spiro[4.5]dec-1-ene-8-sulfonyl]-ethyl}-3,N,N-trimethyl-benzamide;

(89) 4-{2-[2-(3-chloro-4-fluoro-phenyl)-4-oxo-1,3,8-triaza-spiro[4.5]dec-1-ene-8-sulfonyl]-ethyl}-3,N,N-trimethyl-benzamide;

(90) 4-{2-[2-(2-chloro-4-fluoro-phenyl)-4-oxo-1,3,8-triaza-spiro[4.5]dec-1-ene-8-sulfonyl]-ethyl}-3,N,N-trimethyl-benzamide;

(91) 4-{2-[2-(3-bromo-phenyl)-4-oxo-1,3,8-triaza-spiro[4.5]dec-1-ene-8-sulfonyl]-ethyl}-3,N,N-trimethyl-benzamide;

(92) 4-{2-[2-(2,2-difluoro-benzo[1,3]dioxol-4-yl)-4-oxo-1,3,8-triaza-spiro[4.5]dec-1-ene-8-sulfonyl]-ethyl}-3,N,N-trimethyl-benzamide;

(93) 4-{2-[2-(3-chloro-2-fluoro-phenyl)-4-oxo-1,3,8-triaza-spiro[4.5]dec-1-ene-8-sulfonyl]-ethyl}-3,N,N-trimethyl-benzamide;

(94) 3,N,N-trimethyl-4-(2-{4-oxo-2-[4-(1,1,2,2-tetrafluoro-ethoxy)-phenyl]-1,3,8-triaza-spiro[4.5]dec-1-ene-8-sulfonyl}-ethyl)-benzamide;

(95) 4-{2-[2-(4-chloro-3-methyl-phenyl)-4-oxo-1,3,8-triaza-spiro[4.5]dec-1-ene-8-sulfonyl]-ethyl}-3,N,N-trimethyl-benzamide;

(96) 4-{2-[2-(3-fluoro-4-trifluoromethyl-phenyl)-4-oxo-1,3,8-triaza-spiro[4.5]dec-1-ene-8-sulfonyl]-ethyl}-3,N,N-trimethyl-benzamide;

(97) 3,N,N-trimethyl-4-{2-[2-(6-methyl-pyridin-2-yl)-4-oxo-1,3,8-triaza-spiro[4.5]dec-1-ene-8-sulfonyl]-ethyl}-benzamide;

(98) 4-{2-[2-(3,4-dichloro-phenyl)-4-oxo-1,3,8-triaza-spiro[4.5]dec-1-ene-8-sulfonyl]-ethyl}-3,N,N-trimethyl-benzamide;

(99) 3,N,N-trimethyl-4-{2-[4-oxo-2-(3-trifluoromethoxy-phenyl)-1,3,8-triaza-spiro[4.5]dec-1-ene-8-sulfonyl]-ethyl}-benzamide;

(100) 4-{2-[2-(2,4-bis-trifluoromethyl-phenyl)-4-oxo-1,3,8-triaza-spiro[4.5]dec-1-ene-8-sulfonyl]-ethyl}-3,N,N-trimethyl-benzamide;

(101) 3,N,N-trimethyl-4-[2-(4-oxo-2-phenethyl-1,3,8-triaza-spiro[4.5]dec-1-ene-8-sulfonyl)-ethyl]-benzamide;

(102) 4-{2-[2-(2,4-dimethyl-thiazol-5-yl)-4-oxo-1,3,8-triaza-spiro[4.5]dec-1-ene-8-sulfonyl]-ethyl}-3,N,N-trimethyl-benzamide;

(103) 4-[2-(2-cyclohexylmethyl-4-oxo-1,3,8-triaza-spiro[4.5]dec-1-ene-8-sulfonyl)-ethyl]-3,N,N-trimethyl-benzamide;

(104) 3,N,N-trimethyl-4-{2-[4-oxo-2-(4-trifluoromethyl-cyclohexyl)-1,3,8-triaza-spiro[4.5]dec-1-ene-8-sulfonyl]-ethyl}-benzamide;

(105) 3,N,N-trimethyl-4-{2-[4-oxo-2-(2-trifluoromethoxy-phenyl)-1,3,8-triaza-spiro[4.5]dec-1-ene-8-sulfonyl]-ethyl}-benzamide;

(106) 3,N,N-trimethyl-4-{2-[4-oxo-2-(4-trifluoromethoxy-phenyl)-1,3,8-triaza-spiro[4.5]dec-1-ene-8-sulfonyl]-ethyl}-benzamide;

(107) 4-{2-[2-(4-fluoro-3-trifluoromethyl-phenyl)-4-oxo-1,3,8-triaza-spiro[4.5]dec-1-ene-8-sulfonyl]-ethyl}-3,N,N-trimethyl-benzamide;
(108) 4-{2-[2-(2-cyclohexyl-ethyl)-4-oxo-1,3,8-triaza-spiro[4.5]dec-1-ene-8-sulfonyl]-ethyl}-3,N,N-trimethyl-benzamide;
(109) 4-{2-[2-(3-fluoro-phenyl)-4-oxo-1,3,8-triaza-spiro[4.5]dec-1-ene-8-sulfonyl]-ethyl}-3,N,N-trimethyl-benzamide;
(110) 4-{2-[2-(3-methanesulfonyl-phenyl)-4-oxo-1,3,8-triaza-spiro[4.5]dec-1-ene-8-sulfonyl]-ethyl}-3,N,N-trimethyl-benzamide;
(111) 3,N,N-trimethyl-4-{2-[2-(2-methyl-3-trifluoromethyl-phenyl)-4-oxo-1,3,8-triaza-spiro[4.5]dec-1-ene-8-sulfonyl]-ethyl}-benzamide;
(112) 3,N,N-trimethyl-4-{2-[2-(2-methyl-5-trifluoromethyl-phenyl)-4-oxo-1,3,8-triaza-spiro[4.5]dec-1-ene-8-sulfonyl]-ethyl}-benzamide;
(113) 4-{2-[2-(2,3-dimethyl-phenyl)-4-oxo-1,3,8-triaza-spiro[4.5]dec-1-ene-8-sulfonyl]-ethyl}-3,N,N-trimethyl-benzamide;
(114) 4-{2-[2-(3-fluoro-2-methyl-phenyl)-4-oxo-1,3,8-triaza-spiro[4.5]dec-1-ene-8-sulfonyl]-ethyl}-3,N,N-trimethyl-benzamide;
(115) 4-{2-[2-(3-fluoro-5-trifluoromethyl-phenyl)-4-oxo-1,3,8-triaza-spiro[4.5]dec-1-ene-8-sulfonyl]-ethyl}-3,N,N-trimethyl-benzamide;
(116) 4-{2-[2-(2-fluoro-3-trifluoromethyl-phenyl)-4-oxo-1,3,8-triaza-spiro[4.5]dec-1-ene-8-sulfonyl]-ethyl}-3,N,N-trimethyl-benzamide;
(117) 4-{2-[2-(4-fluoro-3-methyl-phenyl)-4-oxo-1,3,8-triaza-spiro[4.5]dec-1-ene-8-sulfonyl]-ethyl}-3,N,N-trimethyl-benzamide;
(118) 4-{2-[2-(4-difluoromethoxy-phenyl)-4-oxo-1,3,8-triaza-spiro[4.5]dec-1-ene-8-sulfonyl]-ethyl}-3,N,N-trimethyl-benzamide;
(119) 4-{2-[2-(2-methoxy-pyridin-4-yl)-4-oxo-1,3,8-triaza-spiro[4.5]dec-1-ene-8-sulfonyl]-ethyl}-3,N,N-trimethyl-benzamide;
(120) 3,N,N-trimethyl-4-{2-[2-(5-methyl-pyrazin-2-yl)-4-oxo-1,3,8-triaza-spiro[4.5]dec-1-ene-8-sulfonyl]-ethyl}-benzamide;
(121) 3,N,N-trimethyl-4-[2-(4-oxo-2-thiazol-4-yl-1,3,8-triaza-spiro[4.5]dec-1-ene-8-sulfonyl)-ethyl]-benzamide;
(122) 3,N,N-trimethyl-4-{2-[2-(1-methyl-1H-imidazol-2-yl)-4-oxo-1,3,8-triaza-spiro[4.5]dec-1-ene-8-sulfonyl]-ethyl}-benzamide;
(123) 3,N,N-trimethyl-4-{2-[4-oxo-2-(tetrahydro-pyran-4-yl)-1,3,8-triaza-spiro[4.5]dec-1-ene-8-sulfonyl]-ethyl}-benzamide;
(124) 4-{2-[2-(4-chloro-phenoxymethyl)-4-oxo-1,3,8-triaza-spiro[4.5]dec-1-ene-8-sulfonyl]-ethyl}-3,N,N-trimethyl-benzamide;
(125) 4-{2-[2-(4-fluoro-phenoxymethyl)-4-oxo-1,3,8-triaza-spiro[4.5]dec-1-ene-8-sulfonyl]-ethyl}-3,N,N-trimethyl-benzamide;
(126) 4-{2-[2-(4-chloro-3-trifluoromethyl-phenyl)-4-oxo-1,3,8-triaza-spiro[4.5]dec-1-ene-8-sulfonyl]-ethyl}-3,N,N-trimethyl-benzamide;
(127) 4-{2-[2-(3-chloro-5-trifluoromethyl-phenyl)-4-oxo-1,3,8-triaza-spiro[4.5]dec-1-ene-8-sulfonyl]-ethyl}-3,N,N-trimethyl-benzamide;
(128) 4-{2-[2-(4-chloro-2-methyl-phenyl)-4-oxo-1,3,8-triaza-spiro[4.5]dec-1-ene-8-sulfonyl]-ethyl}-3,N,N-trimethyl-benzamide;
(129) 4-{2-[2-(4-chloro-2-fluoro-phenyl)-4-oxo-1,3,8-triaza-spiro[4.5]dec-1-ene-8-sulfonyl]-ethyl}-3,N,N-trimethyl-benzamide;
(130) 4-{2-[2-(3-isopropoxymethyl-phenyl)-4-oxo-1,3,8-triaza-spiro[4.5]dec-1-ene-8-sulfonyl]-ethyl}-3,N,N-trimethyl-benzamide;
(131) 4-{2-[2-(2,4-dichloro-phenoxymethyl)-4-oxo-1,3,8-triaza-spiro[4.5]dec-1-ene-8-sulfonyl]-ethyl}-3,N,N-trimethyl-benzamide;
(133) 4-{2-[2-(3-chloro-2-methyl-phenyl)-4-oxo-1,3,8-triaza-spiro[4.5]dec-1-ene-8-sulfonyl]-ethyl}-3,N,N-trimethyl-benzamide;
(134) 4-{2-[2-(2,4-dichloro-benzyl)-4-oxo-1,3,8-triaza-spiro[4.5]dec-1-ene-8-sulfonyl]-ethyl}-3,N,N-trimethyl-benzamide;
(135) 3,N,N-trimethyl-4-{2-[4-oxo-2-(3-trifluoromethyl-benzyl)-1,3,8-triaza-spiro[4.5]dec-1-ene-8-sulfonyl]-ethyl}-benzamide;
(136) 3,N,N-trimethyl-4-{2-[4-oxo-2-(1-trifluoromethyl-cyclopropyl)-1,3,8-triaza-spiro[4.5]dec-1-ene-8-sulfonyl]-ethyl}-benzamide;
(137) 3,N,N-trimethyl-4-{2-[4-oxo-2-(1-trifluoromethyl-cyclobutyl)-1,3,8-triaza-spiro[4.5]dec-1-ene-8-sulfonyl]-ethyl}-benzamide;
(138) 3,N,N-trimethyl-4-{2-[4-oxo-2-(1-trifluoromethyl-cyclopentyl)-1,3,8-triaza-spiro[4.5]dec-1-ene-8-sulfonyl]-ethyl}-benzamide;
(139) 4-{2-[2-(2-fluoro-4-trifluoromethyl-phenyl)-4-oxo-1,3,8-triaza-spiro[4.5]dec-1-ene-8-sulfonyl]-ethyl}-3,N,N-trimethyl-benzamide;
(140) 3,N,N-trimethyl-4-(2-{4-oxo-2-[3-(1,1,2,2-tetrafluoro-ethoxy)-phenyl]-1,3,8-triaza-spiro[4.5]dec-1-ene-8-sulfonyl}-ethyl)-benzamide;
(141) 3,N,N-trimethyl-4-{2-[4-oxo-2-((E)-propenyl)-1,3,8-triaza-spiro[4.5]dec-1-ene-8-sulfonyl]-ethyl}-benzamide;
(142) 3,N,N-trimethyl-4-{2-[4-oxo-2-((E)-styryl)-1,3,8-triaza-spiro[4.5]dec-1-ene-8-sulfonyl]-ethyl}-benzamide;
(143) 4-[2-(2-benzothiazol-6-yl-4-oxo-1,3,8-triaza-spiro[4.5]dec-1-ene-8-sulfonyl)-ethyl]-3,N,N-trimethyl-benzamide;
(144) 4-{2-[2-(4-methoxy-3-trifluoromethyl-phenyl)-4-oxo-1,3,8-triaza-spiro[4.5]dec-1-ene-8-sulfonyl]-ethyl}-3,N,N-trimethyl-benzamide;
(145) N-{3-methyl-4-[2-(4-oxo-2-m-tolyl-1,3,8-triaza-spiro[4.5]dec-1-ene-8-sulfonyl)-ethyl]-phenyl}-acetamide;
(146) N-(4-{2-[2-(2,3-dimethyl-phenyl)-4-oxo-1,3,8-triaza-spiro[4.5]dec-1-ene-8-sulfonyl]-ethyl}-3-methyl-phenyl)-acetamide;
(147) N-(4-{2-[2-(2,3-dichloro-phenyl)-4-oxo-1,3,8-triaza-spiro[4.5]dec-1-ene-8-sulfonyl]-ethyl}-3-methyl-phenyl)-acetamide;
(148) N-(3-methyl-4-{2-[2-(4-methyl-cyclohexyl)-4-oxo-1,3,8-triaza-spiro[4.5]dec-1-ene-8-sulfonyl]-ethyl}-phenyl)-acetamide;
(149) N-(2-hydroxy-ethyl)-N-(3-methyl-4-{2-[4-oxo-2-(3-trifluoromethoxy-phenyl)-1,3,8-triaza-spiro[4.5]dec-1-ene-8-sulfonyl]-ethyl}-phenyl)-acetamide;
(150) acetic acid (S)-1-acetoxymethyl-2-[acetyl-(3-methyl-4-{2-[4-oxo-2-(3-trifluoromethyl-phenyl)-1,3,8-triaza-spiro[4.5]dec-1-ene-8-sulfonyl]-ethyl}-phenyl)-amino]-ethyl ester;
(151) acetic acid (S)-1-acetoxymethyl-2-[acetyl-(3-methyl-4-{2-[4-oxo-2-(4-trifluoromethyl-phenyl)-1,3,8-triaza-spiro[4.5]dec-1-ene-8-sulfonyl]-ethyl}-phenyl)-amino]-ethyl ester;

(152) acetic acid (S)-1-acetoxymethyl-2-[acetyl-(3-methyl-4-{2-[4-oxo-2-(4-trifluoromethoxy-phenyl)-1,3,8-triaza-spiro[4.5]dec-1-ene-8-sulfonyl]-ethyl}-phenyl)-amino]-ethyl ester;

(153) acetic acid (S)-1-acetoxymethyl-2-[acetyl-(4-{2-[2-(4-fluoro-3-trifluoromethyl-phenyl)-4-oxo-1,3,8-triaza-spiro[4.5]dec-1-ene-8-sulfonyl]-ethyl}-3-methyl-phenyl)-amino]-ethyl ester;

(154) 8-{2-[4-((S)-2,3-dihydroxy-propylamino)-2-methyl-phenyl]-ethanesulfonyl}-2-(4-trifluoromethyl-phenyl)-1,3,8-triaza-spiro[4.5]dec-1-en-4-one;

(155) 8-{2-[4-((S)-2,3-dihydroxy-propylamino)-2-methyl-phenyl]-ethanesulfonyl}-2-(3-trifluoromethyl-phenyl)-1,3,8-triaza-spiro[4.5]dec-1-en-4-one;

(156) 8-{2-[4-((S)-2,3-dihydroxy-propylamino)-2-methyl-phenyl]-ethanesulfonyl}-2-(4-trifluoromethoxy-phenyl)-1,3,8-triaza-spiro[4.5]dec-1-en-4-one;

(157) 2-(3-chloro-phenyl)-8-{2-[4-((S)-2,3-dihydroxy-propylamino)-2-methyl-phenyl]-ethanesulfonyl}-1,3,8-triaza-spiro[4.5]dec-1-en-4-one;

(158) 2-(4-chloro-phenyl)-8-{2-[4-((S)-2,3-dihydroxy-propylamino)-2-methyl-phenyl]-ethanesulfonyl}-1,3,8-triaza-spiro[4.5]dec-1-en-4-one;

(159) 8-{2-[4-(2-hydroxy-ethylamino)-2-methyl-phenyl]-ethanesulfonyl}-2-(3-trifluoromethoxy-phenyl)-1,3,8-triaza-spiro[4.5]dec-1-en-4-one;

(160) 8-{2-[4-(2-hydroxy-ethylamino)-2-methyl-phenyl]-ethanesulfonyl}-2-(3-trifluoromethyl-phenyl)-1,3,8-triaza-spiro[4.5]dec-1-en-4-one;

(161) 8-{2-[4-(2-hydroxy-ethylamino)-2-methyl-phenyl]-ethanesulfonyl}-2-(4-trifluoromethyl-phenyl)-1,3,8-triaza-spiro[4.5]dec-1-en-4-one;

(162) {4-[2-(2-tert-butyl-4-oxo-1,3,8-triaza-spiro[4.5]dec-1-ene-8-sulfonyl)-ethyl]-3-methyl-benzyl}-carbamic acid tert-butyl ester;

(163) (4-{2-[2-(4,4-difluoro-cyclohexyl)-4-oxo-1,3,8-triaza-spiro[4.5]dec-1-ene-8-sulfonyl]-ethyl}-3-methyl-benzyl)-carbamic acid tert-butyl ester;

(164) (4-{2-[2-(4-fluoro-3-trifluoromethyl-phenyl)-4-oxo-1,3,8-triaza-spiro[4.5]dec-1-ene-8-sulfonyl]-ethyl}-3-methyl-benzyl)-carbamic acid tert-butyl ester;

(165) (3-methyl-4-{2-[4-oxo-2-(tetrahydro-pyran-4-yl)-1,3,8-triaza-spiro[4.5]dec-1-ene-8-sulfonyl]-ethyl}-benzyl)-carbamic acid tert-butyl ester;

(166) 8-[2-(3-amino-phenyl)-ethanesulfonyl]-2-cyclohexyl-1,3,8-triaza-spiro[4.5]dec-1-en-4-one;

(167) N-{4-[2-(2-cyclohexyl-4-oxo-1,3,8-triaza-spiro[4.5]dec-1-ene-8-sulfonyl)-ethyl]-phenyl}-acetamide;

(168) 3,N,N-trimethyl-4-(2-{4-oxo-2-[3-(2,2,2-trifluoro-ethoxymethyl)-phenyl]-1,3,8-triaza-spiro[4.5]dec-1-ene-8-sulfonyl}-ethyl)-benzamide;

(169) 4-(2-{2-[3-(2,2-difluoro-ethoxymethyl)-phenyl]-4-oxo-1,3,8-triaza-spiro[4.5]dec-1-ene-8-sulfonyl}-ethyl)-3,N,N-trimethyl-benzamide;

(170) 3,N,N-trimethyl-4-(2-{4-oxo-2-[3-(2,2,3,3-tetrafluoro-propoxymethyl)-phenyl]-1,3,8-triaza-spiro[4.5]dec-1-ene-8-sulfonyl}-ethyl)-benzamide;

(171) 4-(2-{2-[3-(3,5-dimethyl-isoxazol-4-yl)-phenyl]-4-oxo-1,3,8-triaza-spiro[4.5]dec-1-ene-8-sulfonyl}-ethyl)-3,N,N-trimethyl-benzamide;

(172) 4-[2-(2-biphenyl-3-yl-4-oxo-1,3,8-triaza-spiro[4.5]dec-1-ene-8-sulfonyl)-ethyl]-3,N,N-trimethyl-benzamide;

(173) 3,N,N-trimethyl-4-{2-[4-oxo-2-(3-pyridin-3-yl-phenyl)-1,3,8-triaza-spiro[4.5]dec-1-ene-8-sulfonyl]-ethyl}-benzamide;

(174) 3-{8-[2-(4-dimethylcarbamoyl-2-methyl-phenyl)-ethanesulfonyl]-4-oxo-1,3,8-triaza-spiro[4.5]dec-1-en-2-yl}-benzoic acid methyl ester;

(175) 4-(2-{2-[1-(2,4-dichloro-phenoxy)-1-methyl-ethyl]-4-oxo-1,3,8-triaza-spiro[4.5]dec-1-ene-8-sulfonyl}-ethyl)-3,N,N-trimethyl-benzamide;

(176) 3,N,N-trimethyl-4-{2-[4-oxo-2-(2,3,4-trifluoro-phenoxymethyl)-1,3,8-triaza-spiro[4.5]dec-1-ene-8-sulfonyl]-ethyl}-benzamide;

(177) 2-cyclohexyl-4-oxo-1,3,8-triaza-spiro[4.5]dec-1-ene-8-sulfonic acid (3-ethyl-phenyl)-amide;

(178) 2-cyclohexyl-8-[(E)-2-(1H-indol-5-yl)-ethenesulfonyl]-1,3,8-triaza-spiro[4.5]dec-1-en-4-one;

(179) 2-cyclohexyl-8-[(E)-2-(2-trifluoromethyl-phenyl)-ethenesulfonyl]-1,3,8-triaza-spiro[4.5]dec-1-en-4-one;

(180) 2-cyclohexyl-8-[(E)-2-(3-methoxy-phenyl)-ethenesulfonyl]-1,3,8-triaza-spiro[4.5]dec-1-en-4-one;

(181) 2-cyclohexyl-8-[(E)-2-(2-methoxy-phenyl)-ethenesulfonyl]-1,3,8-triaza-spiro[4.5]dec-1-en-4-one;

(182) 2-cyclohexyl-8-[(E)-2-(1H-indol-4-yl)-ethenesulfonyl]-1,3,8-triaza-spiro[4.5]dec-1-en-4-one;

(183) 2-cyclohexyl-8-[(E)-2-(2-fluoro-6-trifluoromethyl-phenyl)-ethenesulfonyl]-1,3,8-triaza-spiro[4.5]dec-1-en-4-one;

(184) 2-cyclohexyl-8-[(E)-2-(2,3-difluoro-phenyl)-ethenesulfonyl]-1,3,8-triaza-spiro[4.5]dec-1-en-4-one;

(185) 2-cyclohexyl-8-[(E)-2-(3-fluoro-2-trifluoromethyl-phenyl)-ethenesulfonyl]-1,3,8-triaza-spiro[4.5]dec-1-en-4-one;

(186) 2-cyclohexyl-8-((E)-2-o-tolyl-ethenesulfonyl)-1,3,8-triaza-spiro[4.5]dec-1-en-4-one;

(187) 2-cyclohexyl-8-{(E)-2-[4-(2-hydroxy-ethyl)-phenyl]-ethenesulfonyl}-1,3,8-triaza-spiro[4.5]dec-1-en-4-one;

(188) 2-cyclohexyl-8-[(E)-2-(2-oxo-2,3-dihydro-benzoxazol-7-yl)-ethenesulfonyl]-1,3,8-triaza-spiro[4.5]dec-1-en-4-one;

(189) 4-[(E)-2-(2-cyclohexyl-4-oxo-1,3,8-triaza-spiro[4.5]dec-1-ene-8-sulfonyl)-vinyl]-indole-1-carboxylic acid dimethylamide;

(190) N-{2-[(E)-2-(2-cyclohexyl-4-oxo-1,3,8-triaza-spiro[4.5]dec-1-ene-8-sulfonyl)-vinyl]-3-methyl-phenyl}-acetamide;

(191) 2-cyclohexyl-8-{(E)-2-[1-((S)-2,3-dihydroxy-propyl)-1H-indol-4-yl]-ethenesulfonyl}-1,3,8-triaza-spiro[4.5]dec-1-en-4-one;

(192) 2-cyclohexyl-8-{(E)-2-[1-(2-morpholin-4-yl-ethyl)-1H-indol-4-yl]-ethenesulfonyl}-1,3,8-triaza-spiro[4.5]dec-1-en-4-one;

(193) 2-{4-[(E)-2-(2-cyclohexyl-4-oxo-1,3,8-triaza-spiro[4.5]dec-1-ene-8-sulfonyl)-vinyl]-indol-1-yl}-N,N-dimethyl-acetamide;

(194) 3-{4-[(E)-2-(2-cyclohexyl-4-oxo-1,3,8-triaza-spiro[4.5]dec-1-ene-8-sulfonyl)-vinyl]-3-trifluoromethyl-phenyl}-1,1-dimethyl-urea;

(195) cyclopropanecarboxylic acid {4-[(E)-2-(2-cyclohexyl-4-oxo-1,3,8-triaza-spiro[4.5]dec-1-ene-8-sulfonyl)-vinyl]-3-trifluoromethyl-phenyl}-amide;

(196) N-{4-[(E)-2-(2-cyclohexyl-4-oxo-1,3,8-triaza-spiro[4.5]dec-1-ene-8-sulfonyl)-vinyl]-3-trifluoromethyl-phenyl}-2-hydroxy-acetamide;

(197) {3-[(E)-2-(2-cyclohexyl-4-oxo-1,3,8-triaza-spiro[4.5]dec-1-ene-8-sulfonyl)-vinyl]-4-methyl-phenyl}-carbamic acid methyl ester;

(198) 1-{4-[(E)-2-(2-cyclohexyl-4-oxo-1,3,8-triaza-spiro[4.5]dec-1-ene-8-sulfonyl)-vinyl]-3-trifluoromethyl-phenyl}-3-(2-hydroxy-ethyl)-urea;

(199) 2-cyclohexyl-8-{(E)-2-[5-(2-hydroxy-ethylamino)-2-methyl-phenyl]-ethenesulfonyl}-1,3,8-triaza-spiro[4.5]dec-1-en-4-one;

(200) 2-cyclohexyl-8-{(E)-2-[2-(2-hydroxy-ethylamino)-6-methyl-phenyl]-ethenesulfonyl}-1,3,8-triaza-spiro[4.5]dec-1-en-4-one;

(201) 2-{4-[(E)-2-(2-cyclohexyl-4-oxo-1,3,8-triaza-spiro[4.5]dec-1-ene-8-sulfonyl)-vinyl]-3-trifluoromethyl-phenylamino}-N,N-dimethyl-acetamide;

(202) 2-cyclohexyl-8-{(E)-2-[1-((S)-2,2-dimethyl-[1,3]dioxolan-4-ylmethyl)-3-fluoro-1H-indol-4-yl]-ethenesulfonyl}-1,3,8-triaza-spiro[4.5]dec-1-en-4-one;

(203) 2-cyclohexyl-8-{(E)-2-[2-methyl-4-(3,3,4,4-tetrafluoro-pyrrolidine-1-carbonyl)-phenyl]-ethenesulfonyl}-1,3,8-triaza-spiro[4.5]dec-1-en-4-one;

(204) N-{4-[(E)-2-(2-cyclohexyl-4-oxo-1,3,8-triaza-spiro[4.5]dec-1-ene-8-sulfonyl)-vinyl]-3,5-dimethyl-phenyl}-acetamide;

(205) {4-[(E)-2-(2-cyclohexyl-4-oxo-1,3,8-triaza-spiro[4.5]dec-1-ene-8-sulfonyl)-vinyl]-3-trifluoromethyl-benzyl}-carbamic acid tert-butyl ester;

(206) 2-cyclohexyl-8-{(E)-2-[4-((R)-2,3-dihydroxy-propoxy)-2,6-dimethyl-phenyl]-ethenesulfonyl}-1,3,8-triaza-spiro[4.5]dec-1-en-4-one;

(207) 2-cyclohexyl-8-((E)-2-{2-methyl-4-[(2-oxo-oxazolidin-5-ylmethyl)-amino]-phenyl}-ethenesulfonyl)-1,3,8-triaza-spiro[4.5]dec-1-en-4-one;

(208) 2-{4-[(E)-2-(2-cyclohexyl-4-oxo-1,3,8-triaza-spiro[4.5]dec-1-ene-8-sulfonyl)-vinyl]-phenyl}-N-(2-dimethylamino-ethyl)-acetamide;

(209) 3-{(E)-2-[2-(4-methyl-cyclohexyl)-4-oxo-1,3,8-triaza-spiro[4.5]dec-1-ene-8-sulfonyl]-vinyl}-benzonitrile;

(210) 8-{(E)-2-[4-(3,4-dihydroxy-butoxy)-2-methyl-phenyl]-ethenesulfonyl}-2-(3-trifluoromethyl-phenyl)-1,3,8-triaza-spiro[4.5]dec-1-en-4-one;

(211) 8-{(E)-2-[4-(2-hydroxy-ethylamino)-2-trifluoromethyl-phenyl]-ethenesulfonyl}-2-(3-trifluoromethyl-phenyl)-1,3,8-triaza-spiro[4.5]dec-1-en-4-one;

(212) 8-{(E)-2-[2-methyl-4-(pyrrolidine-1-carbonyl)-phenyl]-ethenesulfonyl}-2-(3-trifluoromethyl-phenyl)-1,3,8-triaza-spiro[4.5]dec-1-en-4-one;

(213) 3-methyl-4-{(E)-2-[4-oxo-2-(3-trifluoromethyl-phenyl)-1,3,8-triaza-spiro[4.5]dec-1-ene-8-sulfonyl]-vinyl}-benzenesulfonamide;

(214) N-(2-hydroxy-ethyl)-3,N-dimethyl-4-{(E)-2-[4-oxo-2-(3-trifluoromethyl-phenyl)-1,3,8-triaza-spiro[4.5]dec-1-ene-8-sulfonyl]-vinyl}-benzamide;

(215) N-(3-methyl-4-{(E)-2-[4-oxo-2-(3-trifluoromethyl-phenyl)-1,3,8-triaza-spiro[4.5]dec-1-ene-8-sulfonyl]-vinyl}-phenyl)-acetamide;

(216) 8-{(E)-2-[2-methyl-4-(4-methyl-piperazine-1-carbonyl)-phenyl]-ethenesulfonyl}-2-(3-trifluoromethyl-phenyl)-1,3,8-triaza-spiro[4.5]dec-1-en-4-one;

(217) 3-methyl-4-{(E)-2-[4-oxo-2-(3-trifluoromethyl-phenyl)-1,3,8-triaza-spiro[4.5]dec-1-ene-8-sulfonyl]-vinyl}-N-(2,2,2-trifluoro-ethyl)-benzenesulfonamide;

(218) 3-methyl-N-(2-morpholin-4-yl-ethyl)-4-{(E)-2-[4-oxo-2-(3-trifluoromethyl-phenyl)-1,3,8-triaza-spiro[4.5]dec-1-ene-8-sulfonyl]-vinyl}-benzenesulfonamide;

(219) 3-methyl-4-{(E)-2-[4-oxo-2-(3-trifluoromethyl-phenyl)-1,3,8-triaza-spiro[4.5]dec-1-ene-8-sulfonyl]-vinyl}-N-pyridin-3-yl-benzenesulfonamide;

(220) 8-{(E)-2-[4-((R)-4-hydroxy-2-oxo-pyrrolidin-1-yl)-2-methyl-phenyl]-ethenesulfonyl}-2-(3-trifluoromethyl-phenyl)-1,3,8-triaza-spiro[4.5]dec-1-en-4-one;

(221) 8-{(E)-2-[4-((R)-2-hydroxymethyl-5-oxo-pyrrolidin-1-yl)-2-methyl-phenyl]-ethenesulfonyl}-2-(3-trifluoromethyl-phenyl)-1,3,8-triaza-spiro[4.5]dec-1-en-4-one;

(222) 8-{(E)-2-[4-((R)-5-hydroxymethyl-2-oxo-oxazolidin-3-yl)-2-methyl-phenyl]-ethenesulfonyl}-2-(3-trifluoromethyl-phenyl)-1,3,8-triaza-spiro[4.5]dec-1-en-4-one;

(223) 8-((E)-2-{4-[3-(3-dimethylamino-propoxy)-azetidine-1-carbonyl]-2,6-dimethyl-phenyl}-ethenesulfonyl)-2-(3-trifluoromethyl-phenyl)-1,3,8-triaza-spiro[4.5]dec-1-en-4-one;

(224) N-(4-hydroxy-butyl)-3-methyl-4-{(E)-2-[4-oxo-2-(3-trifluoromethoxy-phenyl)-1,3,8-triaza-spiro[4.5]dec-1-ene-8-sulfonyl]-vinyl}-benzenesulfonamide;

(225) N-methyl-N-(4-methyl-3-{(E)-2-[4-oxo-2-(3-trifluoromethoxy-phenyl)-1,3,8-triaza-spiro[4.5]dec-1-ene-8-sulfonyl]-vinyl}-phenyl)-acetamide;

(226) 8-[(E)-2-(3-hydroxy-2-methyl-phenyl)-ethenesulfonyl]-2-(3-trifluoromethoxy-phenyl)-1,3,8-triaza-spiro[4.5]dec-1-en-4-one;

(227) 8-[(E)-2-(5-hydroxy-2-methyl-phenyl)-ethenesulfonyl]-2-(3-trifluoromethoxy-phenyl)-1,3,8-triaza-spiro[4.5]dec-1-en-4-one;

(228) N-(3-methyl-4-{(E)-2-[4-oxo-2-(3-trifluoromethoxy-phenyl)-1,3,8-triaza-spiro[4.5]dec-1-ene-8-sulfonyl]-vinyl}-phenyl)-N-(1-methyl-piperidin-4-yl)-acetamide;

(229) N-(3,5-dimethyl-4-{(E)-2-[4-oxo-2-(3-trifluoromethoxy-phenyl)-1,3,8-triaza-spiro[4.5]dec-1-ene-8-sulfonyl]-vinyl}-phenyl)-methanesulfonamide;

(230) 8-{(E)-2-[4-(4-hydroxy-piperidine-1-carbonyl)-2-methyl-phenyl]-ethenesulfonyl}-2-(3-trifluoromethoxy-phenyl)-1,3,8-triaza-spiro[4.5]dec-1-en-4-one;

(231) 3,N,N-trimethyl-4-{(E)-2-[4-oxo-2-(3-trifluoromethoxy-phenyl)-1,3,8-triaza-spiro[4.5]dec-1-ene-8-sulfonyl]-vinyl}-benzamide;

(232) N-(2-hydroxy-ethyl)-N-(3-methyl-4-{(E)-2-[4-oxo-2-(3-trifluoromethoxy-phenyl)-1,3,8-triaza-spiro[4.5]dec-1-ene-8-sulfonyl]-vinyl}-phenyl)-acetamide;

(233) 3-fluoro-N,N-dimethyl-4-{(E)-2-[4-oxo-2-(3-trifluoromethoxy-phenyl)-1,3,8-triaza-spiro[4.5]dec-1-ene-8-sulfonyl]-vinyl}-benzamide;

(234) 8-{(E)-2-[2,5-dichloro-4-(3,4-dihydroxy-butoxy)-phenyl]-ethenesulfonyl}-2-(3-trifluoromethoxy-phenyl)-1,3,8-triaza-spiro[4.5]dec-1-en-4-one;

(235) 8-{(E)-2-[4-(3-dimethylamino-propoxy)-2-methyl-phenyl]-ethenesulfonyl}-2-(3-trifluoromethoxy-phenyl)-1,3,8-triaza-spiro[4.5]dec-1-en-4-one;

(236) N-methyl-N-(2-methyl-3-{(E)-2-[4-oxo-2-(3-trifluoromethoxy-phenyl)-1,3,8-triaza-spiro[4.5]dec-1-ene-8-sulfonyl]-vinyl}-phenyl)-acetamide;

(237) N-methyl-N-(3-methyl-4-{(E)-2-[4-oxo-2-(3-trifluoromethoxy-phenyl)-1,3,8-triaza-spiro[4.5]dec-1-ene-8-sulfonyl]-vinyl}-phenyl)-acetamide;

(238) N-(3,5-dimethyl-4-{(E)-2-[4-oxo-2-(3-trifluoromethoxy-phenyl)-1,3,8-triaza-spiro[4.5]dec-1-ene-8-sulfonyl]-vinyl}-phenyl)-acetamide;

(239) N-(3,5-dimethyl-4-{(E)-2-[4-oxo-2-(3-trifluoromethoxy-phenyl)-1,3,8-triaza-spiro[4.5]dec-1-ene-8-sulfonyl]-vinyl}-phenyl)-N-methyl-acetamide;

(240) 2-cycloheptyl-8-{(E)-2-[1-((S)-2,3-dihydroxy-propyl)-1H-indol-4-yl]-ethenesulfonyl}-1,3,8-triaza-spiro[4.5]dec-1-en-4-one;

(241) 2-(4,4-difluoro-cyclohexyl)-8-{(E)-2-[1-((S)-2,3-dihydroxy-propyl)-1H-indol-4-yl]-ethenesulfonyl}-1,3,8-triaza-spiro[4.5]dec-1-en-4-one;

(242) 8-{(E)-2-[4-((R)-2,3-dihydroxy-propoxy)-2,6-dimethyl-phenyl]-ethenesulfonyl}-2-(4-fluoro-3-trifluoromethyl-phenyl)-1,3,8-triaza-spiro[4.5]dec-1-en-4-one;

(243) 8-{(E)-2-[4-((R)-2,3-dihydroxy-propoxy)-2,6-dimethyl-phenyl]-ethenesulfonyl}-2-(2-fluoro-3-trifluoromethyl-phenyl)-1,3,8-triaza-spiro[4.5]dec-1-en-4-one;

(244) 2-(2-fluoro-3-trifluoromethyl-phenyl)-8-{(E)-2-[4-(4-hydroxy-piperidine-1-carbonyl)-2,6-dimethyl-phenyl]-ethenesulfonyl}-1,3,8-triaza-spiro[4.5]dec-1-en-4-one;

(245) 8-{(E)-2-[1-((S)-2,2-dimethyl-[1,3]dioxolan-4-ylmethyl)-1H-indol-4-yl]-ethenesulfonyl}-2-(4-trifluoromethyl-cyclohexyl)-1,3,8-triaza-spiro[4.5]dec-1-en-4-one;

(246) 8-{(E)-2-[1-(2,2-dimethyl-[1,3]dioxolan-4-ylmethyl)-1H-indol-4-yl]-ethenesulfonyl}-2-(tetrahydro-pyran-4-yl)-1,3,8-triaza-spiro[4.5]dec-1-en-4-one;

(247) 8-{(E)-2-[4-(3,4-dihydroxy-butoxy)-2-methyl-phenyl]-ethenesulfonyl}-2-(2-fluoro-3-trifluoromethyl-phenyl)-1,3,8-triaza-spiro[4.5]dec-1-en-4-one;

(248) 2-(2-fluoro-3-trifluoromethyl-phenyl)-8-{(E)-2-[2-methyl-4-(pyrrolidine-1-carbonyl)-phenyl]-ethenesulfonyl}-1,3,8-triaza-spiro[4.5]dec-1-en-4-one;

(249) 2-(2,4-dichloro-phenyl)-8-{(E)-2-[1-((S)-2,3-dihydroxy-propyl)-1H-indol-4-yl]-ethenesulfonyl}-1,3,8-triaza-spiro[4.5]dec-1-en-4-one;

(250) 2-(4-chloro-phenyl)-8-{(E)-2-[1-((S)-2,3-dihydroxy-propyl)-1H-indol-4-yl]-ethenesulfonyl}-1,3,8-triaza-spiro[4.5]dec-1-en-4-one;

(251) 2-cyclohexyl-8-[(E)-4-(1H-indol-4-yl)-but-3-ene-1-sulfonyl]-1,3,8-triaza-spiro[4.5]dec-1-en-4-one;

(252) 2-cyclohexyl-8-[(E)-5-(1H-indol-4-yl)-pent-4-ene-1-sulfonyl]-1,3,8-triaza-spiro[4.5]dec-1-en-4-one;

(253) 2-cyclohexyl-8-{(E)-3-[1-(2,3-dihydroxy-propyl)-1H-indol-4-yl]-prop-2-ene-1-sulfonyl}-1,3,8-triaza-spiro[4.5]dec-1-en-4-one;

(254) 8-{(E)-2-[3-(3,4-dihydroxy-butoxy)-2-methyl-phenyl]-ethenesulfonyl}-2-(3-trifluoromethoxy-phenyl)-1,3,8-triaza-spiro[4.5]dec-1-en-4-one;

(255) 8-{(E)-2-[5-(3,4-dihydroxy-butoxy)-2-methyl-phenyl]-ethenesulfonyl}-2-(3-trifluoromethoxy-phenyl)-1,3,8-triaza-spiro[4.5]dec-1-en-4-one;

(256) 8-{(E)-2-[3-(2-hydroxy-ethoxy)-2-methyl-phenyl]-ethenesulfonyl}-2-(3-trifluoromethoxy-phenyl)-1,3,8-triaza-spiro[4.5]dec-1-en-4-one;

(257) N-(2-hydroxy-ethyl)-N-(4-methyl-3-{(E)-2-[4-oxo-2-(3-trifluoromethoxy-phenyl)-1,3,8-triaza-spiro[4.5]dec-1-ene-8-sulfonyl]-vinyl}-phenyl)-acetamide;

(258) 8-{(E)-2-[4-((R)-2-hydroxymethyl-5-oxo-pyrrolidin-1-yl)-2,6-dimethyl-phenyl]-ethenesulfonyl}-2-(3-trifluoromethoxy-phenyl)-1,3,8-triaza-spiro[4.5]dec-1-en-4-one;

(259) N-(4-{(E)-2-[2-(2-fluoro-3-trifluoromethyl-phenyl)-4-oxo-1,3,8-triaza-spiro[4.5]dec-1-ene-8-sulfonyl]-vinyl}-3-methyl-phenyl)-N-(2-hydroxy-ethyl)-acetamide;

(260) N-(3-methyl-4-{(E)-2-[4-oxo-2-(3-trifluoromethoxy-phenyl)-1,3,8-triaza-spiro[4.5]dec-1-ene-8-sulfonyl]-vinyl}-phenyl)-N-piperidin-4-yl-acetamide;

(261) 2-cyclohexyl-8-[2-(2-oxo-2,3-dihydro-benzoxazol-7-yl)-ethanesulfonyl]-1,3,8-triaza-spiro[4.5]dec-1-en-4-one;

(262) 2-cyclohexyl-8-[5-(1H-indol-4-yl)-pentane-1-sulfonyl]-1,3,8-triaza-spiro[4.5]dec-1-en-4-one;

(263) 2-cyclohexyl-8-[4-(1H-indol-4-yl)-butane-1-sulfonyl]-1,3,8-triaza-spiro[4.5]dec-1-en-4-one;

(264) N-methyl-N-(2-methyl-3-{2-[4-oxo-2-(3-trifluoromethoxy-phenyl)-1,3,8-triaza-spiro[4.5]dec-1-ene-8-sulfonyl]-ethyl}-phenyl)-acetamide;

(265) N-methyl-N-(4-methyl-3-{2-[4-oxo-2-(3-trifluoromethoxy-phenyl)-1,3,8-triaza-spiro[4.5]dec-1-ene-8-sulfonyl]-ethyl}-phenyl)-acetamide;

(266) 8-{2-[3-(3,4-dihydroxy-butoxy)-2-methyl-phenyl]-ethanesulfonyl}-2-(3-trifluoromethoxy-phenyl)-1,3,8-triaza-spiro[4.5]dec-1-en-4-one;

(267) 8-{2-[5-(3,4-dihydroxy-butoxy)-2-methyl-phenyl]-ethanesulfonyl}-2-(3-trifluoromethoxy-phenyl)-1,3,8-triaza-spiro[4.5]dec-1-en-4-one;

(268) 8-{2-[4-((R)-2-hydroxymethyl-5-oxo-pyrrolidin-1-yl)-2-methyl-phenyl]-ethanesulfonyl}-2-(3-trifluoromethyl-phenyl)-1,3,8-triaza-spiro[4.5]dec-1-en-4-one;

(269) 2-cyclohexyl-8-[2-(1H-indol-5-yl)-ethanesulfonyl]-1,3,8-triaza-spiro[4.5]dec-1-en-4-one;

(270) 2-{4-[2-(2-cyclohexyl-4-oxo-1,3,8-triaza-spiro[4.5]dec-1-ene-8-sulfonyl)-ethyl]-3-trifluoromethyl-phenylamino}-N,N-dimethyl-acetamide;

(271) cyclopropanecarboxylic acid {4-[2-(2-cyclohexyl-4-oxo-1,3,8-triaza-spiro[4.5]dec-1-ene-8-sulfonyl)-ethyl]-3-trifluoromethyl-phenyl}-amide;

(272) {4-[2-(2-cyclohexyl-4-oxo-1,3,8-triaza-spiro[4.5]dec-1-ene-8-sulfonyl)-ethyl]-3-trifluoromethyl-benzyl}-carbamic acid tert-butyl ester;

(273) 3-{4-[2-(2-cyclohexyl-4-oxo-1,3,8-triaza-spiro[4.5]dec-1-ene-8-sulfonyl)-ethyl]-3-trifluoromethyl-phenyl}-1,1-dimethyl-urea;

(274) {3-[2-(2-cyclohexyl-4-oxo-1,3,8-triaza-spiro[4.5]dec-1-ene-8-sulfonyl)-ethyl]-4-methyl-phenyl}-carbamic acid methyl ester;

(275) 2-cyclohexyl-8-{2-[5-(2-hydroxy-ethylamino)-2-methyl-phenyl]-ethanesulfonyl}-1,3,8-triaza-spiro[4.5]dec-1-en-4-one;

(276) N-{2-[2-(2-cyclohexyl-4-oxo-1,3,8-triaza-spiro[4.5]dec-1-ene-8-sulfonyl)-ethyl]-3-methyl-phenyl}-acetamide;

(277) 2-cyclohexyl-8-(2-o-tolyl-ethanesulfonyl)-1,3,8-triaza-spiro[4.5]dec-1-en-4-one;

(278) 1-{4-[2-(2-cyclohexyl-4-oxo-1,3,8-triaza-spiro[4.5]dec-1-ene-8-sulfonyl)-ethyl]-3-trifluoromethyl-phenyl}-3-(2-hydroxy-ethyl)-urea;

(279) 2-cyclohexyl-8-{2-[4-((R)-2,3-dihydroxy-propoxy)-2,6-dimethyl-phenyl]-ethanesulfonyl}-1,3,8-triaza-spiro[4.5]dec-1-en-4-one;

(280) 2-cyclohexyl-8-{2-[4-(2-hydroxy-ethyl)-phenyl]-ethanesulfonyl}-1,3,8-triaza-spiro[4.5]dec-1-en-4-one;

(281) 2-cyclohexyl-8-(2-{2-methyl-4-[(2-oxo-oxazolidin-5-ylmethyl)-amino]-phenyl}-ethanesulfonyl)-1,3,8-triaza-spiro[4.5]dec-1-en-4-one;

(282) 2-{4-[2-(2-cyclohexyl-4-oxo-1,3,8-triaza-spiro[4.5]dec-1-ene-8-sulfonyl)-ethyl]-phenyl}-N-(2-dimethylamino-ethyl)-acetamide;

(283) 2-cyclohexyl-8-{2-[2-methyl-4-(3,3,4,4-tetrafluoro-pyrrolidine-1-carbonyl)-phenyl]-ethanesulfonyl}-1,3,8-triaza-spiro[4.5]dec-1-en-4-one;

(284) 8-{2-[4-(3,4-dihydroxy-butoxy)-2-methyl-phenyl]-ethanesulfonyl}-2-(3-trifluoromethyl-phenyl)-1,3,8-triaza-spiro[4.5]dec-1-en-4-one;

(285) 8-{2-[4-(4-hydroxy-piperidine-1-carbonyl)-2-methyl-phenyl]-ethanesulfonyl}-2-(3-trifluoromethoxy-phenyl)-1,3,8-triaza-spiro[4.5]dec-1-en-4-one;

(286) 8-{2-[4-(2-hydroxy-ethylamino)-2-trifluoromethyl-phenyl]-ethanesulfonyl}-2-(3-trifluoromethyl-phenyl)-1,3,8-triaza-spiro[4.5]dec-1-en-4-one;

(287) N-(4-hydroxy-butyl)-3-methyl-4-{2-[4-oxo-2-(3-trifluoromethoxy-phenyl)-1,3,8-triaza-spiro[4.5]dec-1-ene-8-sulfonyl]-ethyl}-benzenesulfonamide;

(288) 8-{2-[2-methyl-4-(pyrrolidine-1-carbonyl)-phenyl]-ethanesulfonyl}-2-(3-trifluoromethyl-phenyl)-1,3,8-triaza-spiro[4.5]dec-1-en-4-one;

(289) 8-{2-[2-methyl-4-(4-methyl-piperazine-1-carbonyl)-phenyl]-ethanesulfonyl}-2-(3-trifluoromethyl-phenyl)-1,3,8-triaza-spiro[4.5]dec-1-en-4-one;

(290) 3-methyl-4-{2-[4-oxo-2-(3-trifluoromethyl-phenyl)-1,3,8-triaza-spiro[4.5]dec-1-ene-8-sulfonyl]-ethyl}-N-(2,2,2-trifluoro-ethyl)-benzenesulfonamide;

(291) 3-methyl-4-{2-[4-oxo-2-(3-trifluoromethyl-phenyl)-1,3,8-triaza-spiro[4.5]dec-1-ene-8-sulfonyl]-ethyl}-benzenesulfonamide;

(292) 3-methyl-N-(2-morpholin-4-yl-ethyl)-4-{2-[4-oxo-2-(3-trifluoromethyl-phenyl)-1,3,8-triaza-spiro[4.5]dec-1-ene-8-sulfonyl]-ethyl}-benzenesulfonamide;

(293) 3-fluoro-N,N-dimethyl-4-{2-[4-oxo-2-(3-trifluoromethoxy-phenyl)-1,3,8-triaza-spiro[4.5]dec-1-ene-8-sulfonyl]-ethyl}-benzamide;

(294) 3-methyl-4-{2-[4-oxo-2-(3-trifluoromethyl-phenyl)-1,3,8-triaza-spiro[4.5]dec-1-ene-8-sulfonyl]-ethyl}-N-pyridin-3-yl-benzenesulfonamide;

(295) 8-{2-[4-(3-dimethylamino-propoxy)-2-methyl-phenyl]-ethanesulfonyl}-2-(3-trifluoromethoxy-phenyl)-1,3,8-triaza-spiro[4.5]dec-1-en-4-one;

(296) 8-{2-[4-((R)-5-hydroxymethyl-2-oxo-oxazolidin-3-yl)-2-methyl-phenyl]-ethanesulfonyl}-2-(3-trifluoromethyl-phenyl)-1,3,8-triaza-spiro[4.5]dec-1-en-4-one;

(297) 8-{2-[4-((R)-4-hydroxy-2-oxo-pyrrolidin-1-yl)-2-methyl-phenyl]-ethanesulfonyl}-2-(3-trifluoromethyl-phenyl)-1,3,8-triaza-spiro[4.5]dec-1-en-4-one;

(298) N-(3-methyl-4-{2-[4-oxo-2-(3-trifluoromethyl-phenyl)-1,3,8-triaza-spiro[4.5]dec-1-ene-8-sulfonyl]-ethyl}-phenyl)-acetamide;

(299) N-methyl-N-(3-methyl-4-{2-[4-oxo-2-(3-trifluoromethoxy-phenyl)-1,3,8-triaza-spiro[4.5]dec-1-ene-8-sulfonyl]-ethyl}-phenyl)-acetamide;

(300) 2-hydroxy-N-methyl-N-(3-methyl-4-{2-[4-oxo-2-(3-trifluoromethoxy-phenyl)-1,3,8-triaza-spiro[4.5]dec-1-ene-8-sulfonyl]-ethyl}-phenyl)-acetamide;

(301) 1-methyl-1-(3-methyl-4-{2-[4-oxo-2-(3-trifluoromethoxy-phenyl)-1,3,8-triaza-spiro[4.5]dec-1-ene-8-sulfonyl]-ethyl}-phenyl)-urea;

(302) N-{4-[2-(2-cyclohexyl-4-oxo-1,3,8-triaza-spiro[4.5]dec-1-ene-8-sulfonyl)-ethyl]-3,5-dimethyl-phenyl}-acetamide;

(303) 2-cyclohexyl-8-[2-(1H-indol-4-yl)-ethanesulfonyl]-1,3,8-triaza-spiro[4.5]dec-1-en-4-one;

(304) 2-(3-trifluoromethoxy-phenyl)-8-[2-(2-trifluoromethyl-phenyl)-ethanesulfonyl]-1,3,8-triaza-spiro[4.5]dec-1-en-4-one;

(305) 8-[2-(1H-indol-4-yl)-ethanesulfonyl]-2-(3-trifluoromethoxy-phenyl)-1,3,8-triaza-spiro[4.5]dec-1-en-4-one;

(306) 8-[2-(1H-indol-4-yl)-ethanesulfonyl]-2-(4-methyl-cyclohexyl)-1,3,8-triaza-spiro[4.5]dec-1-en-4-one;

(307) 8-[2-(2,2-difluoro-benzo[1,3]dioxol-4-yl)-ethanesulfonyl]-2-(3-trifluoromethoxy-phenyl)-1,3,8-triaza-spiro[4.5]dec-1-en-4-one;

(308) 8-[2-(1-methyl-1H-indol-7-yl)-ethanesulfonyl]-2-(3-trifluoromethoxy-phenyl)-1,3,8-triaza-spiro[4.5]dec-1-en-4-one;

(309) 2-cyclohexyl-8-{2-[1-((S)-2,3-dihydroxy-propyl)-1H-indol-4-yl]-ethanesulfonyl}-1,3,8-triaza-spiro[4.5]dec-1-en-4-one;

(310) 4-[2-(2-cyclohexyl-4-oxo-1,3,8-triaza-spiro[4.5]dec-1-ene-8-sulfonyl)-ethyl]-indole-1-carboxylic acid dimethylamide;

(311) 8-[3-(1H-indol-4-yl)-propane-1-sulfonyl]-2-(4-methyl-cyclohexyl)-1,3,8-triaza-spiro[4.5]dec-1-en-4-one;

(312) 2-cyclohexyl-8-[2-(1-methanesulfonyl-1H-indol-4-yl)-ethanesulfonyl]-1,3,8-triaza-spiro[4.5]dec-1-en-4-one;

(313) 2-cyclohexyl-8-{2-[1-(2-dimethylamino-ethyl)-1H-indol-4-yl]-ethanesulfonyl}-1,3,8-triaza-spiro[4.5]dec-1-en-4-one;

(314) 8-[2-(4-amino-2-trifluoromethyl-phenyl)-ethanesulfonyl]-2-cyclohexyl-1,3,8-triaza-spiro[4.5]dec-1-en-4-one;

(315) 2-cyclohexyl-8-[3-(3-trifluoromethyl-phenyl)-propane-1-sulfonyl]-1,3,8-triaza-spiro[4.5]dec-1-en-4-one;

(316) 2-cyclohexyl-8-(3-m-tolyl-propane-1-sulfonyl)-1,3,8-triaza-spiro[4.5]dec-1-en-4-one;

(317) 2-cyclohexyl-8-[3-(3-hydroxy-phenyl)-propane-1-sulfonyl]-1,3,8-triaza-spiro[4.5]dec-1-en-4-one;

(318) 2-cyclohexyl-8-[3-(2-hydroxy-phenyl)-propane-1-sulfonyl]-1,3,8-triaza-spiro[4.5]dec-1-en-4-one;

(319) 8-(2-benzo[b]thiophen-3-yl-ethanesulfonyl)-2-cyclohexyl-1,3,8-triaza-spiro[4.5]dec-1-en-4-one;

(320) 2-cyclohexyl-8-(2-isoquinolin-5-yl-ethanesulfonyl)-1,3,8-triaza-spiro[4.5]dec-1-en-4-one;

(321) 2-cyclohexyl-8-{2-[4-((S)-2,3-dihydroxy-propylamino)-2-methyl-phenyl]-ethanesulfonyl}-1,3,8-triaza-spiro[4.5]dec-1-en-4-one;

(322) 8-{2-[1-((S)-2,3-dihydroxy-propyl)-1H-indol-4-yl]-ethanesulfonyl}-2-(4-trifluoromethyl-cyclohexyl)-1,3,8-triaza-spiro[4.5]dec-1-en-4-one;

(323) 2-cyclohexyl-8-[2-(2-trifluoromethyl-phenyl)-ethanesulfonyl]-1,3,8-triaza-spiro[4.5]dec-1-en-4-one;

(324) 4-[3-(2-cyclohexyl-4-oxo-1,3,8-triaza-spiro[4.5]dec-1-ene-8-sulfonyl)-propyl]-N,N-dimethyl-benzamide;

(325) 8-{2-[4-((R)-2,3-dihydroxy-propoxy)-2-methyl-phenyl]-ethanesulfonyl}-2-(3-trifluoromethoxy-phenyl)-1,3,8-triaza-spiro[4.5]dec-1-en-4-one;

(326) N-(2-hydroxy-ethyl)-N-(4-methyl-3-{2-[4-oxo-2-(3-trifluoromethoxy-phenyl)-1,3,8-triaza-spiro[4.5]dec-1-ene-8-sulfonyl]-ethyl}-phenyl)-acetamide;

(327) N-(2-hydroxy-ethyl)-N-(2-methyl-3-{2-[4-oxo-2-(3-trifluoromethoxy-phenyl)-1,3,8-triaza-spiro[4.5]dec-1-ene-8-sulfonyl]-ethyl}-phenyl)-acetamide;

(328) 8-[3-(3-amino-phenyl)-propane-1-sulfonyl]-2-cyclohexyl-1,3,8-triaza-spiro[4.5]dec-1-en-4-one;

(329) N,N-dimethyl-4-{5-[4-oxo-2-(3-trifluoromethyl-phenyl)-1,3,8-triaza-spiro[4.5]dec-1-ene-8-sulfonyl]-thiophen-2-yl}-benzamide;

(330) N,N-dimethyl-3-{5-[4-oxo-2-(3-trifluoromethyl-phenyl)-1,3,8-triaza-spiro[4.5]dec-1-ene-8-sulfonyl]-thiophen-2-yl}-benzamide;

(331) 3,N,N-trimethyl-4-{5-[4-oxo-2-(3-trifluoromethyl-phenyl)-1,3,8-triaza-spiro[4.5]dec-1-ene-8-sulfonyl]-thiophen-2-yl}-benzamide;

(332) N-{4-[5-(2-cyclohexyl-4-oxo-1,3,8-triaza-spiro[4.5]dec-1-ene-8-sulfonyl)-thiophen-2-yl]-3-methyl-phenyl}-acetamide;

(333) 4-{5-[2-(4-fluoro-3-trifluoromethyl-phenyl)-4-oxo-1,3,8-triaza-spiro[4.5]dec-1-ene-8-sulfonyl]-thiophen-2-yl}-3,N,N-trimethyl-benzamide;

(334) 3-{5-[2-(4-fluoro-3-trifluoromethyl-phenyl)-4-oxo-1,3,8-triaza-spiro[4.5]dec-1-ene-8-sulfonyl]-thiophen-2-yl}-4,N,N-trimethyl-benzamide;

(335) 2-methyl-3'-[4-oxo-2-(3-trifluoromethoxy-phenyl)-1,3,8-triaza-spiro[4.5]dec-1-ene-8-sulfonyl]-biphenyl-4-carboxylic acid dimethylamide;

(336) 2-methyl-4'-[4-oxo-2-(3-trifluoromethoxy-phenyl)-1,3,8-triaza-spiro[4.5]dec-1-ene-8-sulfonyl]-biphenyl-4-carboxylic acid dimethylamide;

(337) 3,N,N-trimethyl-4-{6-[4-oxo-2-(3-trifluoromethoxy-phenyl)-1,3,8-triaza-spiro[4.5]dec-1-ene-8-sulfonyl]-pyridin-2-yl}-benzamide;
(338) 2-cyclohexyl-8-{2-[2-(3,5-dimethyl-isoxazol-4-yl)-phenyl]-ethanesulfonyl}-1,3,8-triaza-spiro[4.5]dec-1-en-4-one;
(339) 2-cyclohexyl-8-{2-[2-(6-methoxy-pyridin-3-yl)-phenyl]-ethanesulfonyl}-1,3,8-triaza-spiro[4.5]dec-1-en-4-one;
(340) 2-cyclohexyl-8-{2-[2-(1-methyl-1H-pyrazol-4-yl)-phenyl]-ethanesulfonyl}-1,3,8-triaza-spiro[4.5]dec-1-en-4-one;
(341) 8-{5-[4-(3,4-dihydroxy-butoxy)-2-methyl-phenyl]-thiophene-2-sulfonyl}-2-(4-fluoro-3-trifluoromethyl-phenyl)-1,3,8-triaza-spiro[4.5]dec-1-en-4-one;
(342) N-(4-{5-[2-(4-fluoro-3-trifluoromethyl-phenyl)-4-oxo-1,3,8-triaza-spiro[4.5]dec-1-ene-8-sulfonyl]-thiophen-2-yl}-3-methyl-phenyl)-N-(2-hydroxy-ethyl)-acetamide;
(343) 2-cyclohexyl-8-((E)-2-thiazol-2-yl-ethenesulfonyl)-1,3,8-triaza-spiro[4.5]dec-1-en-4-one;
(344) 2-cyclohexyl-8-((E)-2-cyclopentyl-ethenesulfonyl)-1,3,8-triaza-spiro[4.5]dec-1-en-4-one;
(345) 2-cyclohexyl-8-(2-thiazol-2-yl-ethanesulfonyl)-1,3,8-triaza-spiro[4.5]dec-1-en-4-one;
(346) 2-cyclohexyl-8-[3-(4-methoxy-phenyl)-propane-1-sulfonyl]-1,3,8-triaza-spiro[4.5]dec-1-en-4-one;
(347) N-benzyl-2-(2-cyclohexyl-4-oxo-1,3,8-triaza-spiro[4.5]dec-1-ene-8-sulfonyl)-benzamide;
(348) 8-(3-chloro-benzenesulfonyl)-2-[3-(morpholine-4-carbonyl)-phenyl]-1,3,8-triaza-spiro[4.5]dec-1-en-4-one;
(349) 3-[8-(3-chloro-benzenesulfonyl)-4-oxo-1,3,8-triaza-spiro[4.5]dec-1-en-2-yl]-N-methyl-N-phenyl-benzamide;
(350) N-benzyl-3-[8-(3-chloro-benzenesulfonyl)-4-oxo-1,3,8-triaza-spiro[4.5]dec-1-en-2-yl]-benzamide;
(351) 3-[8-(3-chloro-benzenesulfonyl)-4-oxo-1,3,8-triaza-spiro[4.5]dec-1-en-2-yl]-N,N-dimethyl-benzamide;
(352) 8-{2-[4-(4-methanesulfonyl-piperazine-1-carbonyl)-2-methyl-phenyl]-ethanesulfonyl}-2-(3-trifluoromethyl-phenyl)-1,3,8-triaza-spiro[4.5]dec-1-en-4-one;
(353) N—[(R)-1-(3-methyl-4-{2-[4-oxo-2-(3-trifluoromethyl-phenyl)-1,3,8-triaza-spiro[4.5]dec-1-ene-8-sulfonyl]-ethyl}-benzoyl)-pyrrolidin-3-yl]-acetamide;
(354) 8-{2-[2-methyl-4-((S)-2-trifluoromethyl-pyrrolidine-1-carbonyl)-phenyl]-ethanesulfonyl}-2-(3-trifluoromethyl-phenyl)-1,3,8-triaza-spiro[4.5]dec-1-en-4-one;
(355) 8-{2-[4-((R)-3-hydroxy-pyrrolidine-1-carbonyl)-2-methyl-phenyl]-ethanesulfonyl}-2-(3-trifluoromethyl-phenyl)-1,3,8-triaza-spiro[4.5]dec-1-en-4-one;
(356) 8-{2-[4-((S)-2-hydroxymethyl-pyrrolidine-1-carbonyl)-2-methyl-phenyl]-ethanesulfonyl}-2-(3-trifluoromethyl-phenyl)-1,3,8-triaza-spiro[4.5]dec-1-en-4-one;
(357) 8-(2-{4-[4-(2-hydroxy-ethyl)-piperidine-1-carbonyl]-2-methyl-phenyl}-ethanesulfonyl)-2-(3-trifluoromethyl-phenyl)-1,3,8-triaza-spiro[4.5]dec-1-en-4-one;
(358) 8-(2-{2-methyl-4-[4-(3-methyl-[1,2,4]oxadiazol-5-yl)-piperidine-1-carbonyl]-phenyl}-ethanesulfonyl)-2-(3-trifluoromethyl-phenyl)-1,3,8-triaza-spiro[4.5]dec-1-en-4-one;
(359) 8-{2-[2-methyl-4-(4-pyrimidin-2-yl-piperazine-1-carbonyl)-phenyl]-ethanesulfonyl}-2-(3-trifluoromethyl-phenyl)-1,3,8-triaza-spiro[4.5]dec-1-en-4-one;
(360) 4-(3-methyl-4-{2-[4-oxo-2-(3-trifluoromethyl-phenyl)-1,3,8-triaza-spiro[4.5]dec-1-ene-8-sulfonyl]-ethyl}-benzoyl)-piperazine-1-sulfonic acid dimethylamide;
(361) 8-{2-[2-methyl-4-(4-pyridin-2-yl-piperazine-1-carbonyl)-phenyl]-ethanesulfonyl}-2-(3-trifluoromethyl-phenyl)-1,3,8-triaza-spiro[4.5]dec-1-en-4-one;
(362) 8-[2-(4-{4-[2-(2-hydroxy-ethoxy)-ethyl]-piperazine-1-carbonyl}-2-methyl-phenyl)-ethanesulfonyl]-2-(3-trifluoromethyl-phenyl)-1,3,8-triaza-spiro[4.5]dec-1-en-4-one;
(363) 8-(2-{2-methyl-4-[4-(2-morpholin-4-yl-ethyl)-piperazine-1-carbonyl]-phenyl}-ethanesulfonyl)-2-(3-trifluoromethyl-phenyl)-1,3,8-triaza-spiro[4.5]dec-1-en-4-one;
(364) 8-{2-[2-methyl-4-(4-thiazol-2-yl-piperazine-1-carbonyl)-phenyl]-ethanesulfonyl}-2-(3-trifluoromethyl-phenyl)-1,3,8-triaza-spiro[4.5]dec-1-en-4-one;
(365) 8-{2-[4-(4,4-difluoro-piperidine-1-carbonyl)-2-methyl-phenyl]-ethanesulfonyl}-2-(3-trifluoromethyl-phenyl)-1,3,8-triaza-spiro[4.5]dec-1-en-4-one;
(366) 8-(2-{4-[4-(3-hydroxy-propyl)-piperazine-1-carbonyl]-2-methyl-phenyl}-ethanesulfonyl)-2-(3-trifluoromethyl-phenyl)-1,3,8-triaza-spiro[4.5]dec-1-en-4-one;
(367) (S)-1-(3-methyl-4-{2-[4-oxo-2-(3-trifluoromethyl-phenyl)-1,3,8-triaza-spiro[4.5]dec-1-ene-8-sulfonyl]-ethyl}-benzoyl)-pyrrolidine-2-carboxylic acid amide;
(368) 8-{2-[2-methyl-4-(3,3,4,4-tetrafluoro-pyrrolidine-1-carbonyl)-phenyl]-ethanesulfonyl}-2-(3-trifluoromethyl-phenyl)-1,3,8-triaza-spiro[4.5]dec-1-en-4-one;
(369) (R)-1-(3-methyl-4-{2-[4-oxo-2-(3-trifluoromethyl-phenyl)-1,3,8-triaza-spiro[4.5]dec-1-ene-8-sulfonyl]-ethyl}-benzoyl)-pyrrolidine-2-carboxylic acid amide;
(370) 8-{2-[4-((S)-3-hydroxy-pyrrolidine-1-carbonyl)-2-methyl-phenyl]-ethanesulfonyl}-2-(3-trifluoromethyl-phenyl)-1,3,8-triaza-spiro[4.5]dec-1-en-4-one;
(371) 8-{2-[4-((R)-2-hydroxymethyl-pyrrolidine-1-carbonyl)-2-methyl-phenyl]-ethanesulfonyl}-2-(3-trifluoromethyl-phenyl)-1,3,8-triaza-spiro[4.5]dec-1-en-4-one;
(372) 8-{2-[4-((S)-3-dimethylamino-pyrrolidine-1-carbonyl)-2-methyl-phenyl]-ethanesulfonyl}-2-(3-trifluoromethyl-phenyl)-1,3,8-triaza-spiro[4.5]dec-1-en-4-one;
(373) 8-{2-[4-(4-tert-butyl-piperazine-1-carbonyl)-2-methyl-phenyl]-ethanesulfonyl}-2-(3-trifluoromethyl-phenyl)-1,3,8-triaza-spiro[4.5]dec-1-en-4-one;
(374) 8-(2-{4-[4-(3-dimethylamino-propyl)-piperazine-1-carbonyl]-2-methyl-phenyl}-ethanesulfonyl)-2-(3-trifluoromethyl-phenyl)-1,3,8-triaza-spiro[4.5]dec-1-en-4-one;
(375) 8-(2-{4-[4-(4-fluoro-phenyl)-piperazine-1-carbonyl]-2-methyl-phenyl}-ethanesulfonyl)-2-(3-trifluoromethyl-phenyl)-1,3,8-triaza-spiro[4.5]dec-1-en-4-one;
(376) 8-{2-[4-(4-isopropyl-piperazine-1-carbonyl)-2-methyl-phenyl]-ethanesulfonyl}-2-(3-trifluoromethyl-phenyl)-1,3,8-triaza-spiro[4.5]dec-1-en-4-one;
(377) 8-{2-[4-(3-hydroxy-azetidine-1-carbonyl)-2-methyl-phenyl]-ethanesulfonyl}-2-(3-trifluoromethyl-phenyl)-1,3,8-triaza-spiro[4.5]dec-1-en-4-one;
(378) 8-{2-[4-(3-fluoro-pyrrolidine-1-carbonyl)-2-methyl-phenyl]-ethanesulfonyl}-2-(3-trifluoromethyl-phenyl)-1,3,8-triaza-spiro[4.5]dec-1-en-4-one;
(379) 8-{2-[4-(3-fluoro-azetidine-1-carbonyl)-2-methyl-phenyl]-ethanesulfonyl}-2-(3-trifluoromethyl-phenyl)-1,3,8-triaza-spiro[4.5]dec-1-en-4-one;
(380) 8-{2-[2-methyl-4-(piperidine-1-carbonyl)-phenyl]-ethanesulfonyl}-2-(3-trifluoromethyl-phenyl)-1,3,8-triaza-spiro[4.5]dec-1-en-4-one;
(381) 8-{2-[4-(azetidine-1-carbonyl)-2-methyl-phenyl]-ethanesulfonyl}-2-(3-trifluoromethyl-phenyl)-1,3,8-triaza-spiro[4.5]dec-1-en-4-one;
(382) 4-(3-methyl-4-{2-[4-oxo-2-(3-trifluoromethyl-phenyl)-1,3,8-triaza-spiro[4.5]dec-1-ene-8-sulfonyl]-ethyl}-benzoyl)-piperazine-1-carboxylic acid dimethylamide;

(383) 3,5,N,N-tetramethyl-4-{(E)-2-[4-oxo-2-(3-trifluoromethyl-phenyl)-1,3,8-triaza-spiro[4.5]dec-1-ene-8-sulfonyl]-vinyl}-benzamide;

(384) 8-{(E)-2-[4-(4-hydroxy-piperidine-1-carbonyl)-2,6-dimethyl-phenyl]-ethenesulfonyl}-2-(3-trifluoromethyl-phenyl)-1,3,8-triaza-spiro[4.5]dec-1-en-4-one;

(385) 8-{(E)-2-[4-(3-hydroxy-azetidine-1-carbonyl)-2,6-dimethyl-phenyl]-ethenesulfonyl}-2-(3-trifluoromethyl-phenyl)-1,3,8-triaza-spiro[4.5]dec-1-en-4-one;

(386) 8-{(E)-2-[4-(4-hydroxy-4-hydroxymethyl-piperidine-1-carbonyl)-2,6-dimethyl-phenyl]-ethenesulfonyl}-2-(3-trifluoromethyl-phenyl)-1,3,8-triaza-spiro[4.5]dec-1-en-4-one;

(387) 8-{(E)-2-[4-((3R,4R)-3-dimethylamino-4-hydroxy-pyrrolidine-1-carbonyl)-2,6-dimethyl-phenyl]-ethenesulfonyl}-2-(3-trifluoromethyl-phenyl)-1,3,8-triaza-spiro[4.5]dec-1-en-4-one;

(388) 8-{(E)-2-[2,6-dimethyl-4-(pyrrolidine-1-carbonyl)-phenyl]-ethenesulfonyl}-2-(3-trifluoromethyl-phenyl)-1,3,8-triaza-spiro[4.5]dec-1-en-4-one;

(389) N-(3-hydroxy-propyl)-3,5,N-trimethyl-4-{(E)-2-[4-oxo-2-(3-trifluoromethyl-phenyl)-1,3,8-triaza-spiro[4.5]dec-1-ene-8-sulfonyl]-vinyl}-benzamide;

(390) N-(2-dimethylamino-ethyl)-3,5,N-trimethyl-4-{(E)-2-[4-oxo-2-(3-trifluoromethyl-phenyl)-1,3,8-triaza-spiro[4.5]dec-1-ene-8-sulfonyl]-vinyl}-benzamide;

(391) N-(3-dimethylamino-propyl)-3,5,N-trimethyl-4-{(E)-2-[4-oxo-2-(3-trifluoromethyl-phenyl)-1,3,8-triaza-spiro[4.5]dec-1-ene-8-sulfonyl]-vinyl}-benzamide;

(392) N-carbamoylmethyl-3,5,N-trimethyl-4-{(E)-2-[4-oxo-2-(3-trifluoromethyl-phenyl)-1,3,8-triaza-spiro[4.5]dec-1-ene-8-sulfonyl]-vinyl}-benzamide;

(393) 3,5,N-trimethyl-N-(1-methyl-piperidin-4-yl)-4-{(E)-2-[4-oxo-2-(3-trifluoromethyl-phenyl)-1,3,8-triaza-spiro[4.5]dec-1-ene-8-sulfonyl]-vinyl}-benzamide;

(394) 8-{(E)-2-[4-(4-acetyl-piperazine-1-carbonyl)-2,6-dimethyl-phenyl]-ethenesulfonyl}-2-(3-trifluoromethoxy-phenyl)-1,3,8-triaza-spiro[4.5]dec-1-en-4-one;

(395) 4-(3,5-dimethyl-4-{(E)-2-[4-oxo-2-(3-trifluoromethoxy-phenyl)-1,3,8-triaza-spiro[4.5]dec-1-ene-8-sulfonyl]-vinyl}-benzoyl)-piperazine-1-carboxylic acid dimethylamide;

(396) 4-(3,5-dimethyl-4-{(E)-2-[4-oxo-2-(3-trifluoromethoxy-phenyl)-1,3,8-triaza-spiro[4.5]dec-1-ene-8-sulfonyl]-vinyl}-benzoyl)-piperazine-1-carboxylic acid amide;

(397) 8-((E)-2-{4-[4-(3-dimethylamino-propyl)-piperazine-1-carbonyl]-2,6-dimethyl-phenyl}-ethenesulfonyl)-2-(3-trifluoromethoxy-phenyl)-1,3,8-triaza-spiro[4.5]dec-1-en-4-one;

(398) 8-{(E)-2-[2,6-dimethyl-4-((R)-3-methylamino-pyrrolidine-1-carbonyl)-phenyl]-ethenesulfonyl}-2-(3-trifluoromethoxy-phenyl)-1,3,8-triaza-spiro[4.5]dec-1-en-4-one;

(399) 8-{(E)-2-[4-((R)-3-dimethylamino-pyrrolidine-1-carbonyl)-2,6-dimethyl-phenyl]-ethenesulfonyl}-2-(3-trifluoromethoxy-phenyl)-1,3,8-triaza-spiro[4.5]dec-1-en-4-one;

(400) 8-{(E)-2-[4-(4-hydroxy-piperidine-1-carbonyl)-2,6-dimethyl-phenyl]-ethenesulfonyl}-2-(3-trifluoromethoxy-phenyl)-1,3,8-triaza-spiro[4.5]dec-1-en-4-one;

(401) 8-{(E)-2-[4-((R)-3-hydroxy-pyrrolidine-1-carbonyl)-2,6-dimethyl-phenyl]-ethenesulfonyl}-2-(3-trifluoromethoxy-phenyl)-1,3,8-triaza-spiro[4.5]dec-1-en-4-one;

(402) 8-{(E)-2-[4-((S)-3-hydroxy-pyrrolidine-1-carbonyl)-2,6-dimethyl-phenyl]-ethenesulfonyl}-2-(3-trifluoromethoxy-phenyl)-1,3,8-triaza-spiro[4.5]dec-1-en-4-one;

(403) 8-{(E)-2-[4-(4-hydroxy-4-hydroxymethyl-piperidine-1-carbonyl)-2,6-dimethyl-phenyl]-ethenesulfonyl}-2-(3-trifluoromethoxy-phenyl)-1,3,8-triaza-spiro[4.5]dec-1-en-4-one;

(404) 8-{(E)-2-[4-((R)-3-amino-pyrrolidine-1-carbonyl)-2,6-dimethyl-phenyl]-ethenesulfonyl}-2-(3-trifluoromethoxy-phenyl)-1,3,8-triaza-spiro[4.5]dec-1-en-4-one;

(405) 8-{(E)-2-[4-(4-dimethylamino-piperidine-1-carbonyl)-2,6-dimethyl-phenyl]-ethenesulfonyl}-2-(3-trifluoromethoxy-phenyl)-1,3,8-triaza-spiro[4.5]dec-1-en-4-one;

(406) 8-{(E)-2-[4-((3S,4S)-3-hydroxy-4-isopropylamino-pyrrolidine-1-carbonyl)-2,6-dimethyl-phenyl]-ethenesulfonyl}-2-(3-trifluoromethoxy-phenyl)-1,3,8-triaza-spiro[4.5]dec-1-en-4-one;

(407) 8-((E)-2-{4-[4-(2-dimethylamino-ethoxy)-piperidine-1-carbonyl]-2,6-dimethyl-phenyl}-ethenesulfonyl)-2-(3-trifluoromethoxy-phenyl)-1,3,8-triaza-spiro[4.5]dec-1-en-4-one;

(408) 8-{(E)-2-[4-(3-hydroxy-azetidine-1-carbonyl)-2,6-dimethyl-phenyl]-ethenesulfonyl}-2-(3-trifluoromethoxy-phenyl)-1,3,8-triaza-spiro[4.5]dec-1-en-4-one;

$(409)_2$,N,N-trimethyl-3-{2-[4-oxo-2-(3-trifluoromethoxy-phenyl)-1,3,8-triaza-spiro[4.5]dec-1-ene-8-sulfonyl]-ethyl}-benzamide;

(410) 2-methyl-3-{2-[4-oxo-2-(3-trifluoromethoxy-phenyl)-1,3,8-triaza-spiro[4.5]dec-1-ene-8-sulfonyl]-ethyl}-benzamide;

(411) 8-{2-[2-methyl-3-(morpholine-4-carbonyl)-phenyl]-ethanesulfonyl}-2-(3-trifluoromethoxy-phenyl)-1,3,8-triaza-spiro[4.5]dec-1-en-4-one;

$(412)_4$,N,N-trimethyl-3-{2-[4-oxo-2-(3-trifluoromethoxy-phenyl)-1,3,8-triaza-spiro[4.5]dec-1-ene-8-sulfonyl]-ethyl}-benzamide;

(413) N-(2-hydroxy-ethyl)-4,N-dimethyl-3-{2-[4-oxo-2-(3-trifluoromethoxy-phenyl)-1,3,8-triaza-spiro[4.5]dec-1-ene-8-sulfonyl]-ethyl}-benzamide;

(414) 8-{2-[2-methyl-5-(4-methyl-piperazine-1-carbonyl)-phenyl]-ethanesulfonyl}-2-(3-trifluoromethoxy-phenyl)-1,3,8-triaza-spiro[4.5]dec-1-en-4-one;

$(415)_4$,N-dimethyl-3-{2-[4-oxo-2-(3-trifluoromethoxy-phenyl)-1,3,8-triaza-spiro[4.5]dec-1-ene-8-sulfonyl]-ethyl}-benzamide;

(416) 8-(2-{4-[4-(2-hydroxy-ethyl)-piperazine-1-carbonyl]-2-methyl-phenyl}-ethanesulfonyl)-2-(3-trifluoromethoxy-phenyl)-1,3,8-triaza-spiro[4.5]dec-1-en-4-one;

(417) 8-{2-[2-methyl-4-(thiazolidine-3-carbonyl)-phenyl]-ethanesulfonyl}-2-(3-trifluoromethoxy-phenyl)-1,3,8-triaza-spiro[4.5]dec-1-en-4-one;

(418) 2-fluoro-5,N,N-trimethyl-4-{2-[4-oxo-2-(3-trifluoromethyl-phenyl)-1,3,8-triaza-spiro[4.5]dec-1-ene-8-sulfonyl]-ethyl}-benzamide;

(419) 8-{2-[5-fluoro-4-(4-hydroxy-piperidine-1-carbonyl)-2-methyl-phenyl]-ethanesulfonyl}-2-(3-trifluoromethyl-phenyl)-1,3,8-triaza-spiro[4.5]dec-1-en-4-one;

(420) N-benzyl-2-{4-[2-(2-cyclohexyl-4-oxo-1,3,8-triaza-spiro[4.5]dec-1-ene-8-sulfonyl)-ethyl]-1H-indol-3-yl}-acetamide;

(421) 2-[2-(2-cyclohexyl-4-oxo-1,3,8-triaza-spiro[4.5]dec-1-ene-8-sulfonyl)-ethyl]-N-methyl-benzamide;

(422) 3-[2-(2-cyclohexyl-4-oxo-1,3,8-triaza-spiro[4.5]dec-1-ene-8-sulfonyl)-ethyl]-N-pyridin-4-yl-benzamide;

(423) 8-(3-chloro-benzenesulfonyl)-2-[1-(3,3-dimethyl-butyryl)-piperidin-3-yl]-1,3,8-triaza-spiro[4.5]dec-1-en-4-one;

(424) 8-(3-chloro-benzenesulfonyl)-2-[1-(2-hydroxy-acetyl)-piperidin-3-yl]-1,3,8-triaza-spiro[4.5]dec-1-en-4-one;

(425) 8-(3-chloro-benzenesulfonyl)-2-[1-(4-chloro-benzoyl)-piperidin-3-yl]-1,3,8-triaza-spiro[4.5]dec-1-en-4-one;

(426) 8-(3-chloro-benzenesulfonyl)-2-[1-(3-methoxy-benzoyl)-piperidin-3-yl]-1,3,8-triaza-spiro[4.5]dec-1-en-4-one;

(428) 2-[1-(1H-indole-5-carbonyl)-piperidin-3-yl]-8-(2-naphthalen-1-yl-ethanesulfonyl)-1,3,8-triaza-spiro[4.5]dec-1-en-4-one;

(429) 8-(2-naphthalen-1-yl-ethanesulfonyl)-2-[1-(3-phenyl-propionyl)-piperidin-3-yl]-1,3,8-triaza-spiro[4.5]dec-1-en-4-one;

(430) 8-(2-naphthalen-1-yl-ethanesulfonyl)-2-[1-(1,2,3,4-tetrahydro-naphthalene-2-carbonyl)-piperidin-3-yl]-1,3,8-triaza-spiro[4.5]dec-1-en-4-one;

(431) 8-(2-naphthalen-1-yl-ethanesulfonyl)-2-[1-(quinoline-6-carbonyl)-piperidin-3-yl]-1,3,8-triaza-spiro[4.5]dec-1-en-4-one;

(432) 2-[1-(2-3H-imidazol-4-yl-acetyl)-piperidin-3-yl]-8-(2-naphthalen-1-yl-ethanesulfonyl)-1,3,8-triaza-spiro[4.5]dec-1-en-4-one;

(433) 2-{1-[2-(2,5-dimethyl-thiazol-4-yl)-acetyl]-piperidin-3-yl}-8-(2-naphthalen-1-yl-ethanesulfonyl)-1,3,8-triaza-spiro[4.5]dec-1-en-4-one;

(434) 2-{1-[2-(5-methyl-2-phenyl-oxazol-4-yl)-acetyl]-piperidin-3-yl}-8-(2-naphthalen-1-yl-ethanesulfonyl)-1,3,8-triaza-spiro[4.5]dec-1-en-4-one;

(435) 8-(2-naphthalen-1-yl-ethanesulfonyl)-2-[1-(2-pyridin-2-yl-acetyl)-piperidin-3-yl]-1,3,8-triaza-spiro[4.5]dec-1-en-4-one;

(436) 2-[1-(4-benzyloxy-butyryl)-piperidin-3-yl]-8-(2-naphthalen-1-yl-ethanesulfonyl)-1,3,8-triaza-spiro[4.5]dec-1-en-4-one;

(437) 8-(2-naphthalen-1-yl-ethanesulfonyl)-2-[1-(4-phenyl-butyryl)-piperidin-3-yl]-1,3,8-triaza-spiro[4.5]dec-1-en-4-one;

(438) 8-(2-naphthalen-1-yl-ethanesulfonyl)-2-[1-(2-pyridin-4-yl-acetyl)-piperidin-3-yl]-1,3,8-triaza-spiro[4.5]dec-1-en-4-one;

(439) 2-[1-(2-tert-butoxy-acetyl)-piperidin-3-yl]-8-(2-naphthalen-1-yl-ethanesulfonyl)-1,3,8-triaza-spiro[4.5]dec-1-en-4-one;

(441) 8-(2-naphthalen-1-yl-ethanesulfonyl)-2-{1-[(E)-(3-phenyl-acryloyl)]-piperidin-3-yl}-1,3,8-triaza-spiro[4.5]dec-1-en-4-one;

(442) 2-[1-(2-amino-acetyl)-piperidin-3-yl]-8-(3-chloro-benzenesulfonyl)-1,3,8-triaza-spiro[4.5]dec-1-en-4-one;

(444) 8-{2-[2-methyl-4-(3-methylamino-pyrrolidine-1-carbonyl)-phenyl]-ethanesulfonyl}-2-(3-trifluoromethyl-phenyl)-1,3,8-triaza-spiro[4.5]dec-1-en-4-one;

(445) 8-{2-[4-(3-amino-pyrrolidine-1-carbonyl)-2-methyl-phenyl]-ethanesulfonyl}-2-(3-trifluoromethyl-phenyl)-1,3,8-triaza-spiro[4.5]dec-1-en-4-one hydrochloride;

(446) 8-{(E)-2-[2,6-dimethyl-4-(piperazine-1-carbonyl)-phenyl]-ethenesulfonyl}-2-(3-trifluoromethoxy-phenyl)-1,3,8-triaza-spiro[4.5]dec-1-en-4-one hydrochloride;

(447) 8-((E)-2-{4-[4-(2-hydroxy-acetyl)-piperazine-1-carbonyl]-2,6-dimethyl-phenyl}-ethenesulfonyl)-2-(3-trifluoromethoxy-phenyl)-1,3,8-triaza-spiro[4.5]dec-1-en-4-one;

(448) 4-[4-(3,5-dimethyl-4-{(E)-2-[4-oxo-2-(3-trifluoromethoxy-phenyl)-1,3,8-triaza-spiro[4.5]dec-1-ene-8-sulfonyl]-vinyl}-benzoyl)-piperazin-1-yl]-4-oxo-butyric acid methyl ester;

(449) 8-((E)-2-{4-[4-(4-dimethylamino-butyryl)-piperazine-1-carbonyl]-2,6-dimethyl-phenyl}-ethenesulfonyl)-2-(3-trifluoromethoxy-phenyl)-1,3,8-triaza-spiro[4.5]dec-1-en-4-one;

(450) 2-methoxy-N-methyl-N-(3-methyl-4-{(E)-2-[4-oxo-2-(3-trifluoromethoxy-phenyl)-1,3,8-triaza-spiro[4.5]dec-1-ene-8-sulfonyl]-vinyl}-phenyl)-acetamide;

(451) 2-hydroxy-N-methyl-N-(3-methyl-4-{(E)-2-[4-oxo-2-(3-trifluoromethoxy-phenyl)-1,3,8-triaza-spiro[4.5]dec-1-ene-8-sulfonyl]-vinyl}-phenyl)-acetamide;

(452) [(3,5-dimethyl-4-{(E)-2-[4-oxo-2-(3-trifluoromethyl-phenyl)-1,3,8-triaza-spiro[4.5]dec-1-ene-8-sulfonyl]-vinyl}-benzoyl)-methyl-amino]-acetic acid;

(453) 8-(3-chloro-benzenesulfonyl)-2-[1-(3,3-dimethyl-butyl)-piperidin-3-yl]-1,3,8-triaza-spiro[4.5]dec-1-en-4-one;

(454) 3-[8-(3-chloro-benzenesulfonyl)-4-oxo-1,3,8-triaza-spiro[4.5]dec-1-en-2-yl]-piperidine-1-carboxylic acid tert-butylamide;

(455) 3-[8-(2-naphthalen-1-yl-ethanesulfonyl)-4-oxo-1,3,8-triaza-spiro[4.5]dec-1-en-2-yl]-piperidine-1-carboxylic acid phenethyl-amide;

(456) 8-(3-chloro-benzenesulfonyl)-2-[1-(piperidine-1-carbonyl)-piperidin-3-yl]-1,3,8-triaza-spiro[4.5]dec-1-en-4-one;

(457) 3-(2-dimethylamino-ethyl)-1-methyl-1-(3-methyl-4-{(E)-2-[4-oxo-2-(3-trifluoromethoxy-phenyl)-1,3,8-triaza-spiro[4.5]dec-1-ene-8-sulfonyl]-vinyl}-phenyl)-urea;

(458) 1-methyl-1-(3-methyl-4-{(E)-2-[4-oxo-2-(3-trifluoromethoxy-phenyl)-1,3,8-triaza-spiro[4.5]dec-1-ene-8-sulfonyl]-vinyl}-phenyl)-urea;

(459) 1-{3-[2-(2-cyclohexyl-4-oxo-1,3,8-triaza-spiro[4.5]dec-1-ene-8-sulfonyl)-ethyl]-2-methyl-phenyl}-3-methyl-urea;

(460) 3-[8-(3-chloro-benzenesulfonyl)-4-oxo-1,3,8-triaza-spiro[4.5]dec-1-en-2-yl]-piperidine-1-carboxylic acid 2-methoxy-ethyl ester;

(461) 3-[8-(3-chloro-benzenesulfonyl)-4-oxo-1,3,8-triaza-spiro[4.5]dec-1-en-2-yl]-piperidine-1-carboxylic acid benzyl ester;

(462) 3-[8-(3-chloro-benzenesulfonyl)-4-oxo-1,3,8-triaza-spiro[4.5]dec-1-en-2-yl]-piperidine-1-carboxylic acid isobutyl ester;

(463) 3-[8-(3-chloro-benzenesulfonyl)-4-oxo-1,3,8-triaza-spiro[4.5]dec-1-en-2-yl]-piperidine-1-carboxylic acid methyl ester;

(464) 3-[8-(2-naphthalen-1-yl-ethanesulfonyl)-4-oxo-1,3,8-triaza-spiro[4.5]dec-1-en-2-yl]-piperidine-1-carboxylic acid benzyl ester;

(465) 3-[8-(2-naphthalen-1-yl-ethanesulfonyl)-4-oxo-1,3,8-triaza-spiro[4.5]dec-1-en-2-yl]-piperidine-1-carboxylic acid 2,2-dimethyl-propyl ester;

(466) methyl-(3-methyl-4-{(E)-2-[4-oxo-2-(3-trifluoromethoxy-phenyl)-1,3,8-triaza-spiro[4.5]dec-1-ene-8-sulfonyl]-vinyl}-phenyl)-carbamic acid 2-dimethylamino-ethyl ester;

(467) methyl-(3-methyl-4-{(E)-2-[4-oxo-2-(3-trifluoromethoxy-phenyl)-1,3,8-triaza-spiro[4.5]dec-1-ene-8-sulfonyl]-vinyl}-phenyl)-carbamic acid methyl ester;

(468) methyl-(3-methyl-4-{2-[4-oxo-2-(3-trifluoromethoxy-phenyl)-1,3,8-triaza-spiro[4.5]dec-1-ene-8-sulfonyl]-ethyl}-phenyl)-carbamic acid methyl ester;

(469) 2-cyclohexyl-8-(2-o-tolyl-ethanesulfonyl)-1,3,8-triaza-spiro[4.5]dec-1-ene-4-thione;

(470) 1-(3,5-dimethyl-4-{2-[2-(4-methyl-cyclohexyl)-4-oxo-1,3,8-triaza-spiro[4.5]dec-1-ene-8-sulfonyl]-ethyl}-phenyl)-1-methyl-urea;

(471) 1-(3,5-dimethyl-4-{(E)-2-[4-oxo-2-(4-trifluoromethyl-cyclohexyl)-1,3,8-triaza-spiro[4.5]dec-1-ene-8-sulfonyl]-vinyl}-phenyl)-1-methyl-urea;

(472) 1-(3,5-dimethyl-4-{2-[4-oxo-2-(4-trifluoromethyl-cyclohexyl)-1,3,8-triaza-spiro[4.5]dec-1-ene-8-sulfonyl]-ethyl}-phenyl)-1-methyl-urea;

(474) 1-(3,5-dimethyl-4-{2-[2-(4-methyl-cyclohexyl)-4-oxo-1,3,8-triaza-spiro[4.5]dec-1-ene-8-sulfonyl]-ethyl}-phenyl)-1-methyl-thiourea;

(475) 8-{2-[2,6-dimethyl-4-(methyl-thiazol-2-yl-amino)-phenyl]-ethanesulfonyl}-2-(4-methyl-cyclohexyl)-1,3,8-triaza-spiro[4.5]dec-1-en-4-one;

(476) {4-[(E)-2-(2-cyclohexyl-4-oxo-1,3,8-triaza-spiro[4.5]dec-1-ene-8-sulfonyl)-vinyl]-indol-1-yl}-acetic acid methyl ester;

(477) 2-cyclohexyl-8-{(E)-2-[1-(morpholine-4-carbonyl)-1H-indol-4-yl]-ethenesulfonyl}-1,3,8-triaza-spiro[4.5]dec-1-en-4-one;

(478) 2-cyclohexyl-8-{(E)-2-[1-(4-hydroxy-butyl)-1H-indol-4-yl]-ethenesulfonyl}-1,3,8-triaza-spiro[4.5]dec-1-en-4-one;

(479) 2-cyclohexyl-8-[(E)-2-(1H-indol-7-yl)-ethenesulfonyl]-1,3,8-triaza-spiro[4.5]dec-1-en-4-one;

(480) 2-cyclohexyl-8-{(E)-2-[1-(3,4-dihydroxy-butyl)-1H-indol-4-yl]-ethenesulfonyl}-1,3,8-triaza-spiro[4.5]dec-1-en-4-one;

(481) N-(2-{4-[(E)-2-(2-cyclohexyl-4-oxo-1,3,8-triaza-spiro[4.5]dec-1-ene-8-sulfonyl)-vinyl]-phenyl}-ethyl)-acetamide;

(482) N-(1-{4-[(E)-2-(2-cyclohexyl-4-oxo-1,3,8-triaza-spiro[4.5]dec-1-ene-8-sulfonyl)-vinyl]-phenyl}-ethyl)-acetamide;

(483) 2-cyclohexyl-8-[(E)-2-(1-thiazol-2-ylmethyl-1H-indol-4-yl)-ethenesulfonyl]-1,3,8-triaza-spiro[4.5]dec-1-en-4-one;

(484) 3-{4-[(E)-2-(2-cyclohexyl-4-oxo-1,3,8-triaza-spiro[4.5]dec-1-ene-8-sulfonyl)-vinyl]-indol-1-yl}-propane-1-sulfonic acid amide;

(485) 4-methyl-piperazine-1-carboxylic acid {4-[(E)-2-(2-cyclohexyl-4-oxo-1,3,8-triaza-spiro[4.5]dec-1-ene-8-sulfonyl)-vinyl]-3-trifluoromethyl-phenyl}-amide;

(486) {4-[(E)-2-(2-cyclohexyl-4-oxo-1,3,8-triaza-spiro[4.5]dec-1-ene-8-sulfonyl)-vinyl]-benzyl}-carbamic acid isobutyl ester;

(487) 2-cyclohexyl-8-((E)-2-{1-[2-(2-hydroxy-ethoxy)-ethyl]-1H-indol-5-yl}-ethenesulfonyl)-1,3,8-triaza-spiro[4.5]dec-1-en-4-one;

(488) 2-cyclohexyl-8-[(E)-2-(6-methyl-1H-indol-5-yl)-ethenesulfonyl]-1,3,8-triaza-spiro[4.5]dec-1-en-4-one;

(489) N-{4-[(E)-2-(2-cyclohexyl-4-oxo-1,3,8-triaza-spiro[4.5]dec-1-ene-8-sulfonyl)-vinyl]-benzyl}-2-hydroxy-acetamide;

(490) 3-(2-{4-[(E)-2-(2-cyclohexyl-4-oxo-1,3,8-triaza-spiro[4.5]dec-1-ene-8-sulfonyl)-vinyl]-phenyl}-ethyl)-1,1-dimethyl-urea;

(491) 8-[(E)-2-(4-amino-2,6-bis-trifluoromethyl-phenyl)-ethenesulfonyl]-2-cyclohexyl-1,3,8-triaza-spiro[4.5]dec-1-en-4-one;

(492) 2-cyclohexyl-8-[(E)-2-(6-trifluoromethyl-1H-indol-5-yl)-ethenesulfonyl]-1,3,8-triaza-spiro[4.5]dec-1-en-4-one;

(493) {4-[(E)-2-(2-cyclohexyl-4-oxo-1,3,8-triaza-spiro[4.5]dec-1-ene-8-sulfonyl)-vinyl]-3-trifluoromethyl-phenylamino}-acetic acid methyl ester;

(494) 2-{4-[(E)-2-(2-cyclohexyl-4-oxo-1,3,8-triaza-spiro[4.5]dec-1-ene-8-sulfonyl)-vinyl]-3-trifluoromethyl-phenylamino}-N-(2-hydroxy-ethyl)-acetamide;

(495) 4-[(E)-2-(2-cyclohexyl-4-oxo-1,3,8-triaza-spiro[4.5]dec-1-ene-8-sulfonyl)-vinyl]-N-(2-hydroxy-ethyl)-N-methyl-3-trifluoromethyl-benzenesulfonamide;

(496) 4-[(E)-2-(2-cyclohexyl-4-oxo-1,3,8-triaza-spiro[4.5]dec-1-ene-8-sulfonyl)-vinyl]-N,N-bis-(2-hydroxy-ethyl)-3-trifluoromethyl-benzenesulfonamide;

(497) 2-cyclohexyl-8-{(E)-2-[4-(2-dimethylamino-ethylamino)-2-methyl-phenyl]-ethenesulfonyl}-1,3,8-triaza-spiro[4.5]dec-1-en-4-one;

(498) N-(2-acetylamino-ethyl)-2-{4-[(E)-2-(2-cyclohexyl-4-oxo-1,3,8-triaza-spiro[4.5]dec-1-ene-8-sulfonyl)-vinyl]-3-trifluoromethyl-phenylamino}-acetamide;

(499) 2-cyclohexyl-8-[(E)-2-(6-trifluoromethyl-1H-benzimidazol-5-yl)-ethenesulfonyl]-1,3,8-triaza-spiro[4.5]dec-1-en-4-one;

(500) 2-cyclohexyl-8-{(E)-2-[1-((S)-2,2-dimethyl-[1,3]dioxolan-4-ylmethyl)-5-fluoro-1H-indol-4-yl]-ethenesulfonyl}-1,3,8-triaza-spiro[4.5]dec-1-en-4-one;

(501) 2-cyclohexyl-8-((E)-2-{4-[(2-hydroxy-ethyl)-methyl-amino]-2-trifluoromethyl-phenyl}-ethenesulfonyl)-1,3,8-triaza-spiro[4.5]dec-1-en-4-one;

(502) 2-cyclohexyl-8-{(E)-2-[4-(1,1-dioxo-1$\lambda^6$-thiomorpholine-4-carbonyl)-2-methyl-phenyl]-ethenesulfonyl}-1,3,8-triaza-spiro[4.5]dec-1-en-4-one;

(503) 4-[(E)-2-(2-cyclohexyl-4-oxo-1,3,8-triaza-spiro[4.5]dec-1-ene-8-sulfonyl)-vinyl]-N-(2-dimethylamino-ethyl)-3-methyl-benzenesulfonamide;

(504) 3-(3-methyl-4-{(E)-2-[2-(4-methyl-cyclohexyl)-4-oxo-1,3,8-triaza-spiro[4.5]dec-1-ene-8-sulfonyl]-vinyl}-phenyl)-imidazolidine-2,4-dione;

(505) 1-methyl-3-(3-methyl-4-{(E)-2-[2-(4-methyl-cyclohexyl)-4-oxo-1,3,8-triaza-spiro[4.5]dec-1-ene-8-sulfonyl]-vinyl}-phenyl)-imidazolidine-2,4-dione;

(506) N-(3-isopropoxy-4-{(E)-2-[2-(4-methyl-cyclohexyl)-4-oxo-1,3,8-triaza-spiro[4.5]dec-1-ene-8-sulfonyl]-vinyl}-phenyl)-acetamide;

(507) 3-(3,5-dimethyl-4-{(E)-2-[2-(4-methyl-cyclohexyl)-4-oxo-1,3,8-triaza-spiro[4.5]dec-1-ene-8-sulfonyl]-vinyl}-phenyl)-5,5-dimethyl-imidazolidine-2,4-dione;

(508) 3-(3,5-dimethyl-4-{(E)-2-[2-(4-methyl-cyclohexyl)-4-oxo-1,3,8-triaza-spiro[4.5]dec-1-ene-8-sulfonyl]-vinyl}-phenyl)-1,5,5-trimethyl-imidazolidine-2,4-dione;

(509) N-(3-ethoxy-4-{(E)-2-[2-(4-methyl-cyclohexyl)-4-oxo-1,3,8-triaza-spiro[4.5]dec-1-ene-8-sulfonyl]-vinyl}-phenyl)-acetamide;

(510) N-(3-ethyl-4-{(E)-2-[2-(4-methyl-cyclohexyl)-4-oxo-1,3,8-triaza-spiro[4.5]dec-1-ene-8-sulfonyl]-vinyl}-phenyl)-acetamide;

(511) 5,5-dimethyl-3-(3-methyl-4-{(E)-2-[2-(4-methyl-cyclohexyl)-4-oxo-1,3,8-triaza-spiro[4.5]dec-1-ene-8-sulfonyl]-vinyl}-phenyl)-imidazolidine-2,4-dione;

(512) N-(3-methoxymethyl-4-{(E)-2-[2-(4-methyl-cyclohexyl)-4-oxo-1,3,8-triaza-spiro[4.5]dec-1-ene-8-sulfonyl]-vinyl}-phenyl)-acetamide;

(513) 2-(4-methyl-cyclohexyl)-8-{(E)-2-[2-methyl-4-(2-oxo-oxazolidin-3-yl)-phenyl]-ethenesulfonyl}-1,3,8-triaza-spiro[4.5]dec-1-en-4-one;

(514) N-(3,5-dimethyl-4-{(E)-2-[2-(4-methyl-cyclohexyl)-4-oxo-1,3,8-triaza-spiro[4.5]dec-1-ene-8-sulfonyl]-vinyl}-phenyl)-N-(2-methoxy-ethyl)-acetamide;

(515) 8-{(E)-2-[2,6-dimethyl-4-(3-oxo-morpholin-4-yl)-phenyl]-ethenesulfonyl}-2-(4-methyl-cyclohexyl)-1,3,8-triaza-spiro[4.5]dec-1-en-4-one;

(516) 8-{(E)-2-[2,6-dimethyl-4-(2-oxo-piperidin-1-yl)-phenyl]-ethenesulfonyl}-2-(4-methyl-cyclohexyl)-1,3,8-triaza-spiro[4.5]dec-1-en-4-one;

(517) N-(3,5-dimethyl-4-{(E)-2-[2-(4-methyl-cyclohexyl)-4-oxo-1,3,8-triaza-spiro[4.5]dec-1-ene-8-sulfonyl]-vinyl}-benzyl)-N-methyl-acetamide;

(518) 3-(3,5-dimethyl-4-{(E)-2-[2-(4-methyl-cyclohexyl)-4-oxo-1,3,8-triaza-spiro[4.5]dec-1-ene-8-sulfonyl]-vinyl}-benzyl)-imidazolidine-2,4-dione;

(519) 3-(3,5-dimethyl-4-{(E)-2-[2-(4-methyl-cyclohexyl)-4-oxo-1,3,8-triaza-spiro[4.5]dec-1-ene-8-sulfonyl]-vinyl}-benzyl)-5,5-dimethyl-imidazolidine-2,4-dione;

(520) 8-{(E)-2-[2,6-dimethyl-4-(2-oxo-pyrrolidin-1-ylmethyl)-phenyl]-ethenesulfonyl}-2-(4-methyl-cyclohexyl)-1,3,8-triaza-spiro[4.5]dec-1-en-4-one;

(521) 1-(3,5-dimethyl-4-{(E)-2-[2-(4-methyl-cyclohexyl)-4-oxo-1,3,8-triaza-spiro[4.5]dec-1-ene-8-sulfonyl]-vinyl}-benzyl)-pyrrolidine-2,5-dione;

(522) N-(3,5-dimethyl-4-{(E)-2-[2-(4-methyl-cyclohexyl)-4-oxo-1,3,8-triaza-spiro[4.5]dec-1-ene-8-sulfonyl]-vinyl}-benzyl)-acetamide;

(523) N-(3,5-difluoro-4-{(E)-2-[2-(4-methyl-cyclohexyl)-4-oxo-1,3,8-triaza-spiro[4.5]dec-1-ene-8-sulfonyl]-vinyl}-phenyl)-N-methyl-acetamide;

(524) 8-{(E)-2-[1-((S)-2,3-dihydroxy-propyl)-1H-indol-4-yl]-ethenesulfonyl}-2-(3-trifluoromethyl-phenyl)-1,3,8-triaza-spiro[4.5]dec-1-en-4-one;

(525) [(S)-1-(3-methyl-4-{(E)-2-[4-oxo-2-(3-trifluoromethyl-phenyl)-1,3,8-triaza-spiro[4.5]dec-1-ene-8-sulfonyl]-vinyl}-phenyl)-2,5-dioxo-pyrrolidin-3-yl]-carbamic acid tert-butyl ester;

(526) 8-{(E)-2-[1-((S)-2,3-dihydroxy-propyl)-1H-indol-4-yl]-ethenesulfonyl}-2-(3-trifluoromethoxy-phenyl)-1,3,8-triaza-spiro[4.5]dec-1-en-4-one;

(527) 8-{(E)-2-[2-methyl-4-(4-methyl-piperazine-1-carbonyl)-phenyl]-ethenesulfonyl}-2-(3-trifluoromethoxy-phenyl)-1,3,8-triaza-spiro[4.5]dec-1-en-4-one;

(528) 8-((E)-2-{2-methyl-4-[2-(4-methyl-piperazin-1-yl)-2-oxo-ethylamino]-phenyl}-ethenesulfonyl)-2-(3-trifluoromethoxy-phenyl)-1,3,8-triaza-spiro[4.5]dec-1-en-4-one;

(529) 2-(3-methyl-4-{(E)-2-[4-oxo-2-(3-trifluoromethoxy-phenyl)-1,3,8-triaza-spiro[4.5]dec-1-ene-8-sulfonyl]-vinyl}-phenylamino)-acetamide;

(530) 3-methyl-4-{(E)-2-[4-oxo-2-(3-trifluoromethoxy-phenyl)-1,3,8-triaza-spiro[4.5]dec-1-ene-8-sulfonyl]-vinyl}-N-pyridin-4-yl-benzenesulfonamide;

(531) 8-{(E)-2-[4-(3,4-dihydroxy-butoxy)-2-methyl-phenyl]-ethenesulfonyl}-2-(3-trifluoromethoxy-phenyl)-1,3,8-triaza-spiro[4.5]dec-1-en-4-one;

(532) 1-(3,5-dimethyl-4-{(E)-2-[4-oxo-2-(3-trifluoromethoxy-phenyl)-1,3,8-triaza-spiro[4.5]dec-1-ene-8-sulfonyl]-vinyl}-phenyl)-1,3-bis-(2-hydroxy-ethyl)-urea;

(533) 1-(3,5-dimethyl-4-{(E)-2-[4-oxo-2-(3-trifluoromethoxy-phenyl)-1,3,8-triaza-spiro[4.5]dec-1-ene-8-sulfonyl]-vinyl}-phenyl)-1,3-bis-(2-hydroxy-ethyl)-3-methyl-urea;

(534) N-(3,5-dimethyl-4-{(E)-2-[4-oxo-2-(3-trifluoromethoxy-phenyl)-1,3,8-triaza-spiro[4.5]dec-1-ene-8-sulfonyl]-vinyl}-phenyl)-N-(tetrahydro-pyran-4-yl)-methane sulfonamide;

(535) 2-(4-fluoro-3-trifluoromethyl-phenyl)-8-{(E)-2-[4-(4-hydroxy-piperidine-1-carbonyl)-2,6-dimethyl-phenyl]-ethenesulfonyl}-1,3,8-triaza-spiro[4.5]dec-1-en-4-one;

(536) 3-{3-methyl-4-[(E)-2-(2-nonyl-4-oxo-1,3,8-triaza-spiro[4.5]dec-1-ene-8-sulfonyl)-vinyl]-phenyl}-imidazolidine-2,4-dione;

(537) 3-{4-[(E)-2-(2-nonyl-4-oxo-1,3,8-triaza-spiro[4.5]dec-1-ene-8-sulfonyl)-vinyl]-3-trifluoromethyl-phenyl}-imidazolidine-2,4-dione;

(538) 4-{3-methyl-4-[(E)-2-(2-nonyl-4-oxo-1,3,8-triaza-spiro[4.5]dec-1-ene-8-sulfonyl)-vinyl]-phenyl}-morpholine-3,5-dione;

(539) 3-{3,5-dimethyl-4-[(E)-2-(2-nonyl-4-oxo-1,3,8-triaza-spiro[4.5]dec-1-ene-8-sulfonyl)-vinyl]-phenyl}-imidazolidine-2,4-dione;

(540) 5,5-dimethyl-3-[3-methyl-4-((E)-2-{4-oxo-2-[4-(3,3,3-trifluoro-propyl)-cyclohexyl]-1,3,8-triaza-spiro[4.5]dec-1-ene-8-sulfonyl}-vinyl)-phenyl]-imidazolidine-2,4-dione;

(541) 8-{(E)-2-[1-((R)-2,3-dihydroxy-propyl)-1H-indol-4-yl]-ethenesulfonyl}-2-[4-(3,3,3-trifluoro-propyl)-cyclohexyl]-1,3,8-triaza-spiro[4.5]dec-1-en-4-one;

(542) N-(2-methoxy-ethyl)-N-[3-methyl-4-((E)-2-{4-oxo-2-[4-(3,3,3-trifluoro-propyl)-cyclohexyl]-1,3,8-triaza-spiro[4.5]dec-1-ene-8-sulfonyl}-vinyl)-phenyl]-acetamide;

(543) N-[3,5-dimethyl-4-((E)-2-{4-oxo-2-[4-(3,3,3-trifluoro-propyl)-cyclohexyl]-1,3,8-triaza-spiro[4.5]dec-1-ene-8-sulfonyl}-vinyl)-phenyl]-N-(2-methoxy-ethyl)-acetamide;

(544) N-[2-(2-hydroxy-ethoxy)-ethyl]-N-[3-methyl-4-((E)-2-{4-oxo-2-[4-(3,3,3-trifluoro-propyl)-cyclohexyl]-1,3,8-triaza-spiro[4.5]dec-1-ene-8-sulfonyl}-vinyl)-phenyl]-acetamide;

(545) N-[2-(2-fluoro-ethoxy)-ethyl]-N-[3-methyl-4-((E)-2-{4-oxo-2-[4-(3,3,3-trifluoro-propyl)-cyclohexyl]-1,3,8-triaza-spiro[4.5]dec-1-ene-8-sulfonyl}-vinyl)-phenyl]-acetamide;

(546) N-[3,5-dimethyl-4-((E)-2-{4-oxo-2-[4-(3,3,3-trifluoro-propyl)-cyclohexyl]-1,3,8-triaza-spiro[4.5]dec-1-ene-8-sulfonyl}-vinyl)-phenyl]-N-methyl-acetamide;

(547) 3,5-dimethyl-4-((E)-2-{4-oxo-2-[4-(3,3,3-trifluoro-propyl)-cyclohexyl]-1,3,8-triaza-spiro[4.5]dec-1-ene-8-sulfonyl}-vinyl)-benzoic acid;

(548) 3-[3,5-dimethyl-4-((E)-2-{4-oxo-2-[4-(3,3,3-trifluoro-propyl)-cyclohexyl]-1,3,8-triaza-spiro[4.5]dec-1-ene-8-sulfonyl}-vinyl)-phenyl]-1-methyl-imidazolidine-2,4-dione;

(549) 8-((E)-2-{4-[4-(2-fluoro-ethyl)-piperazine-1-carbonyl]-2,6-dimethyl-phenyl}-ethenesulfonyl)-2-[4-(3,3,3-trifluoro-propyl)-cyclohexyl]-1,3,8-triaza-spiro[4.5]dec-1-en-4-one;

(550) 8-{(E)-2-[2,6-dimethyl-4-(3-oxo-morpholin-4-yl)-phenyl]-ethenesulfonyl}-2-[4-(3,3,3-trifluoro-propyl)-cyclohexyl]-1,3,8-triaza-spiro[4.5]dec-1-en-4-one;

(551) N-[3,5-dimethyl-4-((E)-2-{4-oxo-2-[4-(3,3,3-trifluoro-propyl)-cyclohexyl]-1,3,8-triaza-spiro[4.5]dec-1-ene-8-sulfonyl}-vinyl)-phenyl]-N-[2-(2-fluoro-ethoxy)-ethyl]-acetamide;

(552) 3,5-dimethyl-4-((E)-2-{4-oxo-2-[4-(3,3,3-trifluoro-propyl)-cyclohexyl]-1,3,8-triaza-spiro[4.5]dec-1-ene-8-sulfonyl}-vinyl)-benzoic acid N'-acetyl-hydrazide;

(553) 8-[(E)-2-(4-hydroxymethyl-2,6-dimethyl-phenyl)-ethenesulfonyl]-2-[4-(3,3,3-trifluoro-propyl)-cyclohexyl]-1,3,8-triaza-spiro[4.5]dec-1-en-4-one;

(554) 3-[3,5-dimethyl-4-((E)-2-{4-oxo-2-[4-(3,3,3-trifluoro-propyl)-cyclohexyl]-1,3,8-triaza-spiro[4.5]dec-1-ene-8-sulfonyl}-vinyl)-benzyl]-imidazolidine-2,4-dione;

(555) 3-[3,5-dimethyl-4-((E)-2-{4-oxo-2-[4-(3,3,3-trifluoro-propyl)-cyclohexyl]-1,3,8-triaza-spiro[4.5]dec-1-ene-8-sulfonyl}-vinyl)-benzyl]-5,5-dimethyl-imidazolidine-2,4-dione;

(556) 8-{(E)-2-[2,6-dimethyl-4-(2-oxo-pyrrolidin-1-ylmethyl)-phenyl]-ethenesulfonyl}-2-[4-(3,3,3-trifluoro-propyl)-cyclohexyl]-1,3,8-triaza-spiro[4.5]dec-1-en-4-one;

(557) 1-[3,5-dimethyl-4-((E)-2-{4-oxo-2-[4-(3,3,3-trifluoro-propyl)-cyclohexyl]-1,3,8-triaza-spiro[4.5]dec-1-ene-8-sulfonyl}-vinyl)-benzyl]-pyrrolidine-2,5-dione;

(558) N-[3,5-dimethyl-4-((E)-2-{4-oxo-2-[4-(3,3,3-trifluoro-propyl)-cyclohexyl]-1,3,8-triaza-spiro[4.5]dec-1-ene-8-sulfonyl}-vinyl)-benzyl]-acetamide;

(559) N-[3,5-dimethyl-4-((E)-2-{4-oxo-2-[4-(3,3,3-trifluoro-propyl)-cyclohexyl]-1,3,8-triaza-spiro[4.5]dec-1-ene-8-sulfonyl}-vinyl)-benzyl]-N-methyl-acetamide;

(560) 3-(4-{(E)-2-[2-(4-butyl-cyclohexyl)-4-oxo-1,3,8-triaza-spiro[4.5]dec-1-ene-8-sulfonyl]-vinyl}-3-methyl-phenyl)-imidazolidine-2,4-dione;

(561) N-(4-{(E)-2-[2-(4-butyl-cyclohexyl)-4-oxo-1,3,8-triaza-spiro[4.5]dec-1-ene-8-sulfonyl]-vinyl}-3,5-dimethyl-phenyl)-N-[2-(2-methoxy-ethoxy)-ethyl]-acetamide;

(562) N-(4-{(E)-2-[2-(4-butyl-cyclohexyl)-4-oxo-1,3,8-triaza-spiro[4.5]dec-1-ene-8-sulfonyl]-vinyl}-3,5-dimethyl-phenyl)-N-[2-(2-fluoro-ethoxy)-ethyl]-acetamide;

(563) 3-(4-{(E)-2-[2-(4-isopropyl-cyclohexyl)-4-oxo-1,3,8-triaza-spiro[4.5]dec-1-ene-8-sulfonyl]-vinyl}-3-methyl-phenyl)-imidazolidine-2,4-dione;

(564) 3-(4-{(E)-2-[2-(4-isopropyl-cyclohexyl)-4-oxo-1,3,8-triaza-spiro[4.5]dec-1-ene-8-sulfonyl]-vinyl}-3,5-dimethyl-phenyl)-imidazolidine-2,4-dione;

(565) 3-{4-[(E)-2-(2-cyclohexyl-4-oxo-1,3,8-triaza-spiro[4.5]dec-1-ene-8-sulfonyl)-vinyl]-benzyl}-1,1-dimethyl-urea;

(566) (2-{4-[(E)-2-(2-cyclohexyl-4-oxo-1,3,8-triaza-spiro[4.5]dec-1-ene-8-sulfonyl)-vinyl]-phenyl}-ethyl)-carbamic acid methyl ester;

(567) 4-methyl-piperazine-1-carboxylic acid 4-[(E)-2-(2-cyclohexyl-4-oxo-1,3,8-triaza-spiro[4.5]dec-1-ene-8-sulfonyl)-vinyl]-benzylamide;

(568) N-{4-[(E)-2-(2-cyclohexyl-4-oxo-1,3,8-triaza-spiro[4.5]dec-1-ene-8-sulfonyl)-vinyl]-3-methyl-phenyl}-N',N'-dimethyl-sulfamide;

(569) {4-[(E)-2-(2-cyclohexyl-4-oxo-1,3,8-triaza-spiro[4.5]dec-1-ene-8-sulfonyl)-vinyl]-3-methyl-benzyl}-(3-dimethylamino-propyl)-carbamic acid tert-butyl ester;

(570) 2-{4-[(E)-2-(2-cyclohexyl-4-oxo-1,3,8-triaza-spiro[4.5]dec-1-ene-8-sulfonyl)-vinyl]-phenyl}-N-(2,2-dimethyl-propyl)-acetamide;

(571) 2-{4-[(E)-2-(2-cyclohexyl-4-oxo-1,3,8-triaza-spiro[4.5]dec-1-ene-8-sulfonyl)-vinyl]-phenyl}-N-(2-diisopropylamino-ethyl)-acetamide;

(572) 2-cyclohexyl-8-{(E)-2-[2-methyl-4-(2-oxo-azetidin-1-yl)-phenyl]-ethenesulfonyl}-1,3,8-triaza-spiro[4.5]dec-1-en-4-one;

(573) 2-cyclohexyl-8-{(E)-2-[2,6-dimethyl-4-(thiazol-2-ylamino)-phenyl]-ethenesulfonyl}-1,3,8-triaza-spiro[4.5]dec-1-en-4-one;

(574) N-{4-[(E)-2-(2-cyclohexyl-4-oxo-1,3,8-triaza-spiro[4.5]dec-1-ene-8-sulfonyl)-vinyl]-3,5-dimethyl-phenyl}-N-(3-methyl-oxetan-3-ylmethyl)-acetamide;

(575) 3-(3,5-dimethyl-4-{(E)-2-[2-(4-methyl-cyclohexyl)-4-oxo-1,3,8-triaza-spiro[4.5]dec-1-ene-8-sulfonyl]-vinyl}-phenyl)-imidazolidine-2,4-dione;

(576) N-(3-ethoxymethyl-4-{(E)-2-[2-(4-methyl-cyclohexyl)-4-oxo-1,3,8-triaza-spiro[4.5]dec-1-ene-8-sulfonyl]-vinyl}-phenyl)-acetamide;

(577) 2-(4-methyl-cyclohexyl)-8-{(E)-2-[2-methyl-4-(4-oxo-oxazolidin-3-yl)-phenyl]-ethenesulfonyl}-1,3,8-triaza-spiro[4.5]dec-1-en-4-one;

(578) 4-(3-methyl-4-{(E)-2-[2-(4-methyl-cyclohexyl)-4-oxo-1,3,8-triaza-spiro[4.5]dec-1-ene-8-sulfonyl]-vinyl}-phenyl)-3-oxo-piperazine-1-carboxylic acid tert-butyl ester;

(579) 2-(4-methyl-cyclohexyl)-8-{(E)-2-[2-methyl-4-(4-methyl-2-oxo-oxazolidin-3-yl)-phenyl]-ethenesulfonyl}-1,3,8-triaza-spiro[4.5]dec-1-en-4-one;

(580) 2-(4-methyl-cyclohexyl)-8-{(E)-2-[2-methyl-4-(3-oxo-isoxazolidin-2-yl)-phenyl]-ethenesulfonyl}-1,3,8-triaza-spiro[4.5]dec-1-en-4-one;

(581) 3-(2,5-dimethyl-4-{(E)-2-[2-(4-methyl-cyclohexyl)-4-oxo-1,3,8-triaza-spiro[4.5]dec-1-ene-8-sulfonyl]-vinyl}-phenyl)-imidazolidine-2,4-dione;

(582) 3-(3,5-dimethyl-4-{(E)-2-[2-(4-methyl-cyclohexyl)-4-oxo-1,3,8-triaza-spiro[4.5]dec-1-ene-8-sulfonyl]-vinyl}-phenyl)-5-methyl-imidazolidine-2,4-dione;

(583) 3-(2,6-dimethyl-4-{(E)-2-[2-(4-methyl-cyclohexyl)-4-oxo-1,3,8-triaza-spiro[4.5]dec-1-ene-8-sulfonyl]-vinyl}-phenyl)-imidazolidine-2,4-dione;

(584) N-(2,6-dimethyl-4-{(E)-2-[2-(4-methyl-cyclohexyl)-4-oxo-1,3,8-triaza-spiro[4.5]dec-1-ene-8-sulfonyl]-vinyl}-phenyl)-N-methyl-acetamide;

(585) 8-[(E)-2-(3-methoxy-2-methyl-phenyl)-ethenesulfonyl]-2-(4-methyl-cyclohexyl)-1,3,8-triaza-spiro[4.5]dec-1-en-4-one;

(586) 8-((E)-2-{4-[(1H-imidazol-2-yl)-methyl-amino]-2,6-dimethyl-phenyl}-ethenesulfonyl)-2-(4-methyl-cyclohexyl)-1,3,8-triaza-spiro[4.5]dec-1-en-4-one;

(587) 1-(3,5-dimethyl-4-{(E)-2-[2-(4-methyl-cyclohexyl)-4-oxo-1,3,8-triaza-spiro[4.5]dec-1-ene-8-sulfonyl]-vinyl}-phenyl)-dihydro-pyrimidine-2,4-dione;

(588) 2-(4-methyl-cyclohexyl)-8-{(E)-2-[2-methyl-4-(5-oxo-pyrazolidin-1-yl)-phenyl]-ethenesulfonyl}-1,3,8-triaza-spiro[4.5]dec-1-en-4-one;

(589) 5-tert-butoxymethyl-3-(3,5-dimethyl-4-{(E)-2-[2-(4-methyl-cyclohexyl)-4-oxo-1,3,8-triaza-spiro[4.5]dec-1-ene-8-sulfonyl]-vinyl}-phenyl)-imidazolidine-2,4-dione;

(590) N,N-dimethyl-2-(3-methyl-4-{(E)-2-[4-oxo-2-(3-trifluoromethyl-phenyl)-1,3,8-triaza-spiro[4.5]dec-1-ene-8-sulfonyl]-vinyl}-benzenesulfonylamino)-acetamide;

(591) 3-methyl-4-{(E)-2-[4-oxo-2-(3-trifluoromethyl-phenyl)-1,3,8-triaza-spiro[4.5]dec-1-ene-8-sulfonyl]-vinyl}-N-pyridin-3-ylmethyl-benzenesulfonamide;

(592) N-(4-hydroxy-cyclohexyl)-3-methyl-4-{(E)-2-[4-oxo-2-(3-trifluoromethyl-phenyl)-1,3,8-triaza-spiro[4.5]dec-1-ene-8-sulfonyl]-vinyl}-benzenesulfonamide;

(593) 8-[(E)-2-(4-methanesulfonyl-2-methyl-phenyl)-ethenesulfonyl]-2-(3-trifluoromethyl-phenyl)-1,3,8-triaza-spiro[4.5]dec-1-en-4-one;

(594) N-acetyl-3-methyl-4-{(E)-2-[4-oxo-2-(3-trifluoromethyl-phenyl)-1,3,8-triaza-spiro[4.5]dec-1-ene-8-sulfonyl]-vinyl}-benzenesulfonamide;

(595) N-(2-hydroxy-1,1-bis-hydroxymethyl-ethyl)-3-methyl-4-{(E)-2-[4-oxo-2-(3-trifluoromethyl-phenyl)-1,3,8-triaza-spiro[4.5]dec-1-ene-8-sulfonyl]-vinyl}-benzenesulfonamide;

(596) N-(1-benzyl-piperidin-4-yl)-3-methyl-4-{(E)-2-[4-oxo-2-(3-trifluoromethoxy-phenyl)-1,3,8-triaza-spiro[4.5]dec-1-ene-8-sulfonyl]-vinyl}-benzenesulfonamide;

(597) 8-{(E)-2-[1-((S)-2,3-dihydroxy-propyl)-1H-indol-5-yl]-ethenesulfonyl}-2-(3-trifluoromethoxy-phenyl)-1,3,8-triaza-spiro[4.5]dec-1-en-4-one;

(598) 8-{(E)-2-[4-(4-isopropyl-piperazine-1-carbonyl)-2-methyl-phenyl]-ethenesulfonyl}-2-(3-trifluoromethoxy-phenyl)-1,3,8-triaza-spiro[4.5]dec-1-en-4-one;

(599) N—((R)-2,3-dihydroxy-propyl)-3-methyl-4-{(E)-2-[4-oxo-2-(3-trifluoromethoxy-phenyl)-1,3,8-triaza-spiro[4.5]dec-1-ene-8-sulfonyl]-vinyl}-benzenesulfonamide;

(600) 8-{(E)-2-[4-(3,4-dihydroxy-butoxy)-3,5-difluoro-phenyl]-ethenesulfonyl}-2-(3-trifluoromethoxy-phenyl)-1,3,8-triaza-spiro[4.5]dec-1-en-4-one;

(601) 8-{(E)-2-[4-(3,4-dihydroxy-butoxy)-3,5-dimethyl-phenyl]-ethenesulfonyl}-2-(3-trifluoromethoxy-phenyl)-1,3,8-triaza-spiro[4.5]dec-1-en-4-one;

(602) 4-(3-methyl-4-{(E)-2-[4-oxo-2-(3-trifluoromethoxy-phenyl)-1,3,8-triaza-spiro[4.5]dec-1-ene-8-sulfonyl]-vinyl}-phenoxy)-piperidine-1-carboxylic acid tert-butyl ester;

(603) N-isopropyl-N-(3-methyl-4-{(E)-2-[4-oxo-2-(3-trifluoromethoxy-phenyl)-1,3,8-triaza-spiro[4.5]dec-1-ene-8-sulfonyl]-vinyl}-phenyl)-acetamide;

(604) 4-[acetyl-(3-methyl-4-{(E)-2-[4-oxo-2-(3-trifluoromethoxy-phenyl)-1,3,8-triaza-spiro[4.5]dec-1-ene-8-sulfonyl]-vinyl}-phenyl)-amino]-piperidine-1-carboxylic acid tert-butyl ester;

(605) 1-(3,5-dimethyl-4-{(E)-2-[4-oxo-2-(3-trifluoromethoxy-phenyl)-1,3,8-triaza-spiro[4.5]dec-1-ene-8-sulfonyl]-vinyl}-phenyl)-1-(2-hydroxy-ethyl)-urea;

(606) 8-((E)-2-{4-[(R)-2-(isopropylamino-methyl)-5-oxo-pyrrolidin-1-yl]-2,6-dimethyl-phenyl}-ethenesulfonyl)-2-(3-trifluoromethoxy-phenyl)-1,3,8-triaza-spiro[4.5]dec-1-en-4-one;

(607) N-(2-dimethylamino-ethyl)-N-(3,5-dimethyl-4-{(E)-2-[4-oxo-2-(3-trifluoromethoxy-phenyl)-1,3,8-triaza-spiro[4.5]dec-1-ene-8-sulfonyl]-vinyl}-phenyl)-acetamide;

(608) 2-dimethylamino-N-(3,5-dimethyl-4-{(E)-2-[4-oxo-2-(3-trifluoromethoxy-phenyl)-1,3,8-triaza-spiro[4.5]dec-1-ene-8-sulfonyl]-vinyl}-phenyl)-N-methyl-acetamide;

(609) N-(2-dimethylamino-ethyl)-N-(3,5-dimethyl-4-{(E)-2-[4-oxo-2-(3-trifluoromethoxy-phenyl)-1,3,8-triaza-spiro[4.5]dec-1-ene-8-sulfonyl]-vinyl}-phenyl)-methane sulfonamide;

(610) N—[(R)-1-(3,5-dimethyl-4-{(E)-2-[4-oxo-2-(3-trifluoromethoxy-phenyl)-1,3,8-triaza-spiro[4.5]dec-1-ene-8-sulfonyl]-vinyl}-phenyl)-5-oxo-pyrrolidin-2-ylmethyl]-acetamide;

(611) 8-{(E)-2-[4-((R)-2-dimethylaminomethyl-5-oxo-pyrrolidin-1-yl)-2,6-dimethyl-phenyl]-ethenesulfonyl}-2-(3-trifluoromethoxy-phenyl)-1,3,8-triaza-spiro[4.5]dec-1-en-4-one;

(612) N-cyanomethyl-N-(3-methyl-4-{(E)-2-[4-oxo-2-(3-trifluoromethoxy-phenyl)-1,3,8-triaza-spiro[4.5]dec-1-ene-8-sulfonyl]-vinyl}-phenyl)-acetamide;

(613) N-(3-methyl-4-{(E)-2-[4-oxo-2-(3-trifluoromethoxy-phenyl)-1,3,8-triaza-spiro[4.5]dec-1-ene-8-sulfonyl]-vinyl}-phenyl)-N-(2,2,2-trifluoro-ethyl)-acetamide;

(614) 3-(3,5-dimethyl-4-{(E)-2-[4-oxo-2-(3-trifluoromethoxy-phenyl)-1,3,8-triaza-spiro[4.5]dec-1-ene-8-sulfonyl]-vinyl}-phenyl)-1,5,5-trimethyl-imidazolidine-2,4-dione;

(615) 3-(3,5-dimethyl-4-{(E)-2-[4-oxo-2-(3-trifluoromethoxy-phenyl)-1,3,8-triaza-spiro[4.5]dec-1-ene-8-sulfonyl]-vinyl}-phenyl)-5,5-dimethyl-imidazolidine-2,4-dione;

(616) N-(3,5-dimethyl-4-{(E)-2-[4-oxo-2-(3-trifluoromethoxy-phenyl)-1,3,8-triaza-spiro[4.5]dec-1-ene-8-sulfonyl]-vinyl}-phenyl)-N-(tetrahydro-pyran-4-yl)-acetamide;

(617) 8-{(E)-2-[2-methyl-4-(3-oxo-morpholin-4-yl)-phenyl]-ethenesulfonyl}-2-(3-trifluoromethoxy-phenyl)-1,3,8-triaza-spiro[4.5]dec-1-en-4-one;

(618) 3-(3-methyl-4-{(E)-2-[4-oxo-2-(3-trifluoromethoxy-phenyl)-1,3,8-triaza-spiro[4.5]dec-1-ene-8-sulfonyl]-vinyl}-phenyl)-imidazolidine-2,4-dione;

(619) 2-(4-fluoro-3-trifluoromethyl-phenyl)-8-{(E)-2-[2-methyl-4-(pyrrolidine-1-carbonyl)-phenyl]-ethenesulfonyl}-1,3,8-triaza-spiro[4.5]dec-1-en-4-one;

(620) 2-(4-fluoro-3-trifluoromethyl-phenyl)-8-{(E)-2-[4-((R)-2-hydroxymethyl-5-oxo-pyrrolidin-1-yl)-2-methyl-phenyl]-ethenesulfonyl}-1,3,8-triaza-spiro[4.5]dec-1-en-4-one;

(621) 2-(4-fluoro-3-trifluoromethyl-phenyl)-8-{(E)-2-[4-((S)-2-hydroxymethyl-5-oxo-pyrrolidin-1-yl)-2-methyl-phenyl]-ethenesulfonyl}-1,3,8-triaza-spiro[4.5]dec-1-en-4-one;

(622) 8-{(E)-2-[1-((S)-2,3-dihydroxy-propyl)-1H-indol-4-yl]-ethenesulfonyl}-2-(9,9,9-trifluoro-nonyl)-1,3,8-triaza-spiro[4.5]dec-1-en-4-one;

(623) 8-{(E)-2-[1-((S)-2,3-dihydroxy-propyl)-1H-indol-4-yl]-ethenesulfonyl}-2-(8,8,9,9,9-pentafluoro-nonyl)-1,3,8-triaza-spiro[4.5]dec-1-en-4-one;

(624) 1-(4-{(E)-2-[2-(4-ethyl-cyclohexyl)-4-oxo-1,3,8-triaza-spiro[4.5]dec-1-ene-8-sulfonyl]-vinyl}-3-methyl-phenyl)-imidazolidine-2,4-dione;

(625) 1-(4-{(E)-2-[2-(4-ethyl-cyclohexyl)-4-oxo-1,3,8-triaza-spiro[4.5]dec-1-ene-8-sulfonyl]-vinyl}-3-methyl-phenyl)-5-methyl-imidazolidine-2,4-dione;

(626) 1-(4-{(E)-2-[2-(4-ethyl-cyclohexyl)-4-oxo-1,3,8-triaza-spiro[4.5]dec-1-ene-8-sulfonyl]-vinyl}-3-methyl-phenyl)-5,5-dimethyl-imidazolidine-2,4-dione;

(627) 8-{(E)-2-[4-(3,4-dihydroxy-butoxy)-2,6-dimethyl-phenyl]-ethenesulfonyl}-2-nonyl-1,3,8-triaza-spiro[4.5]dec-1-en-4-one;

(628) 3,5-dimethyl-4-[(E)-2-(2-nonyl-4-oxo-1,3,8-triaza-spiro[4.5]dec-1-ene-8-sulfonyl)-vinyl]-benzoic acid;

(629) 3,5-dimethyl-4-((E)-2-{4-oxo-2-[4-(3,3,3-trifluoro-propyl)-cyclohexyl]-1,3,8-triaza-spiro[4.5]dec-1-ene-8-sulfonyl}-vinyl)-benzoic acid trimethylhydrazide;

(630) 8-{(E)-2-[1-((R)-2,3-dihydroxy-propyl)-4,6-dimethyl-1H-indol-5-yl]-ethenesulfonyl}-2-[4-(3,3,3-trifluoro-propyl)-cyclohexyl]-1,3,8-triaza-spiro[4.5]dec-1-en-4-one;

(631) 3-(4-{(E)-2-[2-(4-butyl-cyclohexyl)-4-oxo-1,3,8-triaza-spiro[4.5]dec-1-ene-8-sulfonyl]-vinyl}-3,5-dimethyl-phenyl)-imidazolidine-2,4-dione;

(632) N-(4-{(E)-2-[2-(4-butyl-cyclohexyl)-4-oxo-1,3,8-triaza-spiro[4.5]dec-1-ene-8-sulfonyl]-vinyl}-3,5-dimethyl-phenyl)-N-(3-methyl-oxetan-3-ylmethyl)-acetamide;

(633) 2-cyclohexyl-8-((E)-2-quinolin-8-yl-ethenesulfonyl)-1,3,8-triaza-spiro[4.5]dec-1-en-4-one;

(634) 2-cyclohexyl-8-[(E)-2-(2-oxo-2,3-dihydro-1H-indol-4-yl)-ethenesulfonyl]-1,3,8-triaza-spiro[4.5]dec-1-en-4-one;

(635) 3-(3,5-dimethyl-4-{(E)-2-[4-oxo-2-(3-trifluoromethoxy-phenyl)-1,3,8-triaza-spiro[4.5]dec-1-ene-8-sulfonyl]-vinyl}-phenyl)-imidazolidine-2,4-dione;

(636) 3-(4-{(E)-2-[2-(4-fluoro-3-trifluoromethyl-phenyl)-4-oxo-1,3,8-triaza-spiro[4.5]dec-1-ene-8-sulfonyl]-vinyl}-3,5-dimethyl-phenyl)-imidazolidine-2,4-dione;

(637) 2-cyclohexyl-8-[(E)-2-(2-methyl-1H-indol-4-yl)-ethenesulfonyl]-1,3,8-triaza-spiro[4.5]dec-1-en-4-one;

(638) 2-cyclohexyl-8-[(E)-2-(1-methyl-1,2,3,4-tetrahydro-quinolin-5-yl)-ethenesulfonyl]-1,3,8-triaza-spiro[4.5]dec-1-en-4-one;

(639) 8-{(E)-2-[4-(3,4-dihydroxy-butoxy)-2,6-dimethyl-phenyl]-ethenesulfonyl}-2-(4-fluoro-3-trifluoromethyl-phenyl)-1,3,8-triaza-spiro[4.5]dec-1-en-4-one;

(640) (4-{(E)-2-[2-(4-fluoro-3-trifluoromethyl-phenyl)-4-oxo-1,3,8-triaza-spiro[4.5]dec-1-ene-8-sulfonyl]-vinyl}-3,5-dimethyl-phenyl)-[1,1,1-$^{2}H_{3}$]methyl-carbamic acid tert-butyl ester;

(641) 8-{(E)-2-[4-(4-fluoromethyl-4-hydroxy-piperidine-1-carbonyl)-2,6-dimethyl-phenyl]-ethenesulfonyl}-2-(4-fluoro-3-trifluoromethyl-phenyl)-1,3,8-triaza-spiro[4.5]dec-1-en-4-one;

(642) 2-(4-fluoro-3-trifluoromethyl-phenyl)-8-{(E)-2-[4-(4-hydroxy-4-methyl-piperidine-1-carbonyl)-2,6-dimethyl-phenyl]-ethenesulfonyl}-1,3,8-triaza-spiro[4.5]dec-1-en-4-one;

(643) 8-{(E)-2-[1-((S)-2,3-dihydroxy-propyl)-1H-indol-4-yl]-ethenesulfonyl}-2-(4-fluoro-3-trifluoromethyl-phenyl)-1,3,8-triaza-spiro[4.5]dec-1-en-4-one;

(644) 8-{(E)-2-[2,6-dimethyl-4-(2-oxa-7-aza-spiro[3.5]nonane-7-carbonyl)-phenyl]-ethenesulfonyl}-2-(4-fluoro-3-trifluoromethyl-phenyl)-1,3,8-triaza-spiro[4.5]dec-1-en-4-one;

(645) 2-cyclohexyl-8-[2-(1,2,3,4-tetrahydro-quinolin-5-yl)-ethanesulfonyl]-1,3,8-triaza-spiro[4.5]dec-1-en-4-one;

(646) 4-[2-(2-cyclohexyl-4-oxo-1,3,8-triaza-spiro[4.5]dec-1-ene-8-sulfonyl)-ethyl]-1H-indole-3-carbonitrile;

(647) 7-[2-(2-cyclohexyl-4-oxo-1,3,8-triaza-spiro[4.5]dec-1-ene-8-sulfonyl)-ethyl]-indole-1-carboxylic acid dimethylamide;

(648) 2-cyclohexyl-8-(2-quinolin-5-yl-ethanesulfonyl)-1,3,8-triaza-spiro[4.5]dec-1-en-4-one;

(649) 2-cyclohexyl-8-{2-[3-(2,2,2-trifluoro-acetyl)-1H-indol-4-yl]-ethanesulfonyl}-1,3,8-triaza-spiro[4.5]dec-1-en-4-one;

(650) 2-cyclohexyl-8-[2-(1-isopropyl-1H-indol-4-yl)-ethanesulfonyl]-1,3,8-triaza-spiro[4.5]dec-1-en-4-one;

(651) 2-cyclohexyl-8-{2-[1-(4-hydroxy-butyl)-1H-indol-4-yl]-ethanesulfonyl}-1,3,8-triaza-spiro[4.5]dec-1-en-4-one;

(652) N-{3-cyano-4-[2-(2-cyclohexyl-4-oxo-1,3,8-triaza-spiro[4.5]dec-1-ene-8-sulfonyl)-ethyl]-phenyl}-acetamide;

(653) 8-(2-isoquinolin-5-yl-ethanesulfonyl)-2-(3-trifluoromethoxy-phenyl)-1,3,8-triaza-spiro[4.5]dec-1-en-4-one;

(654) 8-(2-quinolin-5-yl-ethanesulfonyl)-2-(3-trifluoromethoxy-phenyl)-1,3,8-triaza-spiro[4.5]dec-1-en-4-one;

(655) N-(3-methoxy-4-{2-[2-(4-methyl-cyclohexyl)-4-oxo-1,3,8-triaza-spiro[4.5]dec-1-ene-8-sulfonyl]-ethyl}-phenyl)-acetamide;

(656) 8-{2-[4-(3,3-dimethyl-1,1,4-trioxo-1λ$^{6}$-[1,2,5]thiadiazolidin-2-yl)-2,6-dimethyl-phenyl]-ethanesulfonyl}-2-(4-methyl-cyclohexyl)-1,3,8-triaza-spiro[4.5]dec-1-en-4-one;

(657) 8-{2-[2-methyl-4-(3-oxo-morpholin-4-yl)-phenyl]-ethanesulfonyl}-2-nonyl-1,3,8-triaza-spiro[4.5]dec-1-en-4-one;

(658) {4-[2-(2-cyclohexyl-4-oxo-1,3,8-triaza-spiro[4.5]dec-1-ene-8-sulfonyl)-ethyl]-benzyl}-carbamic acid isobutyl ester;

(659) N-{4-[2-(2-cyclohexyl-4-oxo-1,3,8-triaza-spiro[4.5]dec-1-ene-8-sulfonyl)-ethyl]-benzyl}-2-hydroxy-acetamide;

(660) 2-{4-[2-(2-cyclohexyl-4-oxo-1,3,8-triaza-spiro[4.5]dec-1-ene-8-sulfonyl)-ethyl]-3-trifluoromethyl-phenylamino}-N-(4-hydroxy-butyl)-acetamide;

(661) {4-[2-(2-cyclohexyl-4-oxo-1,3,8-triaza-spiro[4.5]dec-1-ene-8-sulfonyl)-ethyl]-3-trifluoromethyl-phenyl}-carbamic acid isobutyl ester;

(662) N-{4-[2-(2-cyclohexyl-4-oxo-1,3,8-triaza-spiro[4.5]dec-1-ene-8-sulfonyl)-ethyl]-3-trifluoromethyl-phenyl}-benzamide;

(663) 2-cyclohexyl-8-[2-(2-oxo-2,3-dihydro-benzothiazol-6-yl)-ethanesulfonyl]-1,3,8-triaza-spiro[4.5]dec-1-en-4-one;

(664) N-(2-{4-[2-(2-cyclohexyl-4-oxo-1,3,8-triaza-spiro[4.5]dec-1-ene-8-sulfonyl)-ethyl]-3-methyl-benzenesulfonylamino}-ethyl)-acetamide;

(665) N-(2-dimethylamino-ethyl)-2-(3-methyl-4-{2-[4-oxo-2-(3-trifluoromethoxy-phenyl)-1,3,8-triaza-spiro[4.5]dec-1-ene-8-sulfonyl]-ethyl}-phenylamino)-acetamide;

(666) 8-{2-[4-((2R,6S)-2,6-dimethyl-morpholine-4-carbonyl)-2-methyl-phenyl]-ethanesulfonyl}-2-(3-trifluoromethoxy-phenyl)-1,3,8-triaza-spiro[4.5]dec-1-en-4-one;

(667) N-(2,2,3,3,4,4,4-heptafluoro-butyl)-3-methyl-4-{2-[4-oxo-2-(3-trifluoromethyl-phenyl)-1,3,8-triaza-spiro[4.5]dec-1-ene-8-sulfonyl]-ethyl}-benzenesulfonamide;

(668) 8-[2-(3-methoxy-2-methyl-phenyl)-ethanesulfonyl]-2-(4-methyl-cyclohexyl)-1,3,8-triaza-spiro[4.5]dec-1-en-4-one;

(669) (2-methoxy-3,5-dimethyl-4-{2-[2-(4-methyl-cyclohexyl)-4-oxo-1,3,8-triaza-spiro[4.5]dec-1-ene-8-sulfonyl]-ethyl}-phenyl)-methyl-carbamic acid tert-butyl ester;

(670) 8-{2-[4-((S)-2-hydroxymethyl-5-oxo-pyrrolidin-1-yl)-2-methyl-phenyl]-ethanesulfonyl}-2-nonyl-1,3,8-triaza-spiro[4.5]dec-1-en-4-one;

(671) 8-[2-(5,7-dimethyl-2-oxo-2,3-dihydro-benzoxazol-6-yl)-ethanesulfonyl]-2-(4-methyl-cyclohexyl)-1,3,8-triaza-spiro[4.5]dec-1-en-4-one;

(672) (2-{4-[2-(2-cyclohexyl-4-oxo-1,3,8-triaza-spiro[4.5]dec-1-ene-8-sulfonyl)-ethyl]-phenyl}-ethyl)-carbamic acid methyl ester;

(673) {4-[2-(2-cyclohexyl-4-oxo-1,3,8-triaza-spiro[4.5]dec-1-ene-8-sulfonyl)-ethyl]-3-methyl-benzyl}-methyl-carbamic acid tert-butyl ester;

(674) 8-(2-{4-[3-(2-hydroxy-ethyl)-2-oxo-imidazolidin-1-yl]-2-methyl-phenyl}-ethanesulfonyl)-2-(3-trifluoromethyl-phenyl)-1,3,8-triaza-spiro[4.5]dec-1-en-4-one;

(675) 2-(3-methyl-4-{2-[4-oxo-2-(3-trifluoromethoxy-phenyl)-1,3,8-triaza-spiro[4.5]dec-1-ene-8-sulfonyl]-ethyl}-benzenesulfonylamino)-acetamide;

(676) 8-{2-[4-(3,4-dihydroxy-butoxy)-2,6-dimethyl-phenyl]-ethanesulfonyl}-2-(3-trifluoromethoxy-phenyl)-1,3,8-triaza-spiro[4.5]dec-1-en-4-one;

(677) 3-(4-{2-[2-(4-butyl-cyclohexyl)-4-oxo-1,3,8-triaza-spiro[4.5]dec-1-ene-8-sulfonyl]-ethyl}-3,5-dimethyl-phenyl)-imidazolidine-2,4-dione;

(678) N-cyclopentyl-N-(3-methyl-4-{2-[4-oxo-2-(3-trifluoromethoxy-phenyl)-1,3,8-triaza-spiro[4.5]dec-1-ene-8-sulfonyl]-ethyl}-phenyl)-acetamide;

(679) 1-(2,3-dimethyl-4-{2-[2-(4-methyl-cyclohexyl)-4-oxo-1,3,8-triaza-spiro[4.5]dec-1-ene-8-sulfonyl]-ethyl}-phenyl)-1-methyl-urea;

(680) 1-(2,5-dimethyl-4-{2-[2-(4-methyl-cyclohexyl)-4-oxo-1,3,8-triaza-spiro[4.5]dec-1-ene-8-sulfonyl]-ethyl}-phenyl)-1-methyl-urea;

(681) {4-[2-(2-cyclohexyl-4-oxo-1,3,8-triaza-spiro[4.5]dec-1-ene-8-sulfonyl)-ethyl]-3-methyl-benzyl}-(2-hydroxy-ethyl)-carbamic acid tert-butyl ester;

(682) 1-(3-methoxy-5-methyl-4-{2-[2-(4-methyl-cyclohexyl)-4-oxo-1,3,8-triaza-spiro[4.5]dec-1-ene-8-sulfonyl]-ethyl}-phenyl)-1-methyl-urea;

(683) 1-(3-chloro-5-methyl-4-{2-[2-(4-methyl-cyclohexyl)-4-oxo-1,3,8-triaza-spiro[4.5]dec-1-ene-8-sulfonyl]-ethyl}-phenyl)-1-methyl-urea;

(684) 1-(2-methoxy-3,5-dimethyl-4-{2-[2-(4-methyl-cyclohexyl)-4-oxo-1,3,8-triaza-spiro[4.5]dec-1-ene-8-sulfonyl]-ethyl}-phenyl)-1-methyl-urea;

(685) 5,7-dimethyl-6-{2-[2-(4-methyl-cyclohexyl)-4-oxo-1,3,8-triaza-spiro[4.5]dec-1-ene-8-sulfonyl]-ethyl}-1H-quinazoline-2,4-dione;

(686) 8-{(E)-2-[1-(2-amino-ethyl)-1H-indol-4-yl]-ethenesulfonyl}-2-cyclohexyl-1,3,8-triaza-spiro[4.5]dec-1-en-4-one;

(687) 8-[(E)-2-(4-aminomethyl-phenyl)-ethenesulfonyl]-2-cyclohexyl-1,3,8-triaza-spiro[4.5]dec-1-en-4-one;

(688) (S)-2-amino-3-hydroxy-N-(3-methyl-4-{(E)-2-[4-oxo-2-(3-trifluoromethyl-phenyl)-1,3,8-triaza-spiro[4.5]dec-1-ene-8-sulfonyl]-vinyl}-phenyl)-propionamide;

(689) N-(3,5-dimethyl-4-{(E)-2-[4-oxo-2-(3-trifluoromethoxy-phenyl)-1,3,8-triaza-spiro[4.5]dec-1-ene-8-sulfonyl]-vinyl}-phenyl)-N-piperidin-4-yl-methane sulfonamide;

(690) 8-[(E)-2-(2,6-dimethyl-4-methylamino-phenyl)-ethenesulfonyl]-2-(9,9,9-trifluoro-nonyl)-1,3,8-triaza-spiro[4.5]dec-1-en-4-one;

(691) 8-[(E)-2-(2,6-dimethyl-4-methylamino-phenyl)-ethenesulfonyl]-2-(8,8,9,9,9-pentafluoro-nonyl)-1,3,8-triaza-spiro[4.5]dec-1-en-4-one;

(692) 1-{3,5-dimethyl-4-[(E)-2-(2-nonyl-4-oxo-1,3,8-triaza-spiro[4.5]dec-1-ene-8-sulfonyl)-vinyl]-phenyl}-1-methyl-urea;

(693) 1-(2-methoxy-3,5-dimethyl-4-{(E)-2-[2-(4-methyl-cyclohexyl)-4-oxo-1,3,8-triaza-spiro[4.5]dec-1-ene-8-sulfonyl]-vinyl}-phenyl)-1-methyl-urea;

(694) 1-[3,5-dimethyl-4-((E)-2-{4-oxo-2-[4-(3,3,3-trifluoro-propyl)-cyclohexyl]-1,3,8-triaza-spiro[4.5]dec-1-ene-8-sulfonyl}-vinyl)-phenyl]-1-(2-fluoro-ethyl)-urea;

(695) 1-(3-chloro-5-methyl-4-{(E)-2-[2-(4-methyl-cyclohexyl)-4-oxo-1,3,8-triaza-spiro[4.5]dec-1-ene-8-sulfonyl]-vinyl}-phenyl)-1-methyl-urea;

(696) 1-[3,5-dimethyl-4-(2-{4-oxo-2-[4-(3,3,3-trifluoro-propyl)-cyclohexyl]-1,3,8-triaza-spiro[4.5]dec-1-ene-8-sulfonyl}-ethyl)-phenyl]-1-methyl-urea;

(697) 8-{(E)-2-[4-((R)-2,3-dihydroxy-propoxy)-2,6-dimethyl-phenyl]-ethenesulfonyl}-2-[4-(3,3,3-trifluoro-propyl)-cyclohexyl]-1,3,8-triaza-spiro[4.5]dec-1-en-4-one;

(698) 8-((E)-2-{4-[2-((R)-2,3-dihydroxy-propoxy)-ethoxy]-2,6-dimethyl-phenyl}-ethenesulfonyl)-2-[4-(3,3,3-trifluoro-propyl)-cyclohexyl]-1,3,8-triaza-spiro[4.5]dec-1-en-4-one;

(699) N-[3,5-dimethyl-4-((E)-2-{4-oxo-2-[4-(3,3,3-trifluoro-propyl)-cyclohexyl]-1,3,8-triaza-spiro[4.5]dec-1-ene-8-sulfonyl}-vinyl)-phenyl]-N-[2-(2-hydroxy-ethoxy)-ethyl]-acetamide;

(700) N-[2-(2-hydroxy-ethoxy)-ethyl]-N-{3-methyl-4-[(E)-2-(2-nonyl-4-oxo-1,3,8-triaza-spiro[4.5]dec-1-ene-8-sulfonyl)-vinyl]-phenyl}-acetamide;

(701) N-{3,5-dimethyl-4-[(E)-2-(2-nonyl-4-oxo-1,3,8-triaza-spiro[4.5]dec-1-ene-8-sulfonyl)-vinyl]-phenyl}-N-(2-hydroxy-ethyl)-acetamide;

(702) 2-cyclohexyl-8-{(E)-2-[1-((S)-2,3-dihydroxy-propyl)-1H-indol-5-yl]-ethenesulfonyl}-1,3,8-triaza-spiro[4.5]dec-1-en-4-one;

(704) 8-((E)-2-{1-[2-((S)-2,3-dihydroxy-propoxy)-ethyl]-1H-indol-4-yl}-ethenesulfonyl)-2-[4-(3,3,3-trifluoro-propyl)-cyclohexyl]-1,3,8-triaza-spiro[4.5]dec-1-en-4-one;

(705) 8-{(E)-2-[2,6-dimethyl-4-((2S,3S)-2,3,4-trihydroxy-butoxy)-phenyl]-ethenesulfonyl}-2-[4-(3,3,3-trifluoro-propyl)-cyclohexyl]-1,3,8-triaza-spiro[4.5]dec-1-en-4-one;

(706) 2-[4-(3,3,3-trifluoro-propyl)-cyclohexyl]-8-((E)-2-{1-[2-((2S,3S)-2,3,4-trihydroxy-butoxy)-ethyl]-1H-indol-4-yl}-ethenesulfonyl)-1,3,8-triaza-spiro[4.5]dec-1-en-4-one;

(707) N—((S)-2,3-dihydroxy-propyl)-N-(3,5-dimethyl-4-{(E)-2-[4-oxo-2-(9,9,9-trifluoro-nonyl)-1,3,8-triaza-spiro[4.5]dec-1-ene-8-sulfonyl]-vinyl}-phenyl)-acetamide;

(708) {4-[(E)-2-(2-cyclohexyl-4-oxo-1,3,8-triaza-spiro[4.5]dec-1-ene-8-sulfonyl)-vinyl]-3-methyl-benzyl}-(2-hydroxy-ethyl)-carbamic acid tert-butyl ester;

(709) N-{4-[(E)-2-(2-cyclohexyl-4-oxo-1,3,8-triaza-spiro[4.5]dec-1-ene-8-sulfonyl)-vinyl]-3,5-dimethyl-phenyl}-N-(4-hydroxy-cyclohexyl)-acetamide;

(710) 2-cyclohexyl-8-((E)-2-{4-[(R)-2-(2-hydroxy-ethoxymethyl)-5-oxo-pyrrolidin-1-yl]-2,6-dimethyl-phenyl}-ethenesulfonyl)-1,3,8-triaza-spiro[4.5]dec-1-en-4-one;

(711) N-(2-hydroxy-ethyl)-N-(3-methyl-4-{(E)-2-[4-oxo-2-(3-trifluoromethoxy-phenyl)-1,3,8-triaza-spiro[4.5]dec-1-ene-8-sulfonyl]-vinyl}-phenyl)-isobutylamide;

(712) 8-{(E)-2-[4-((R)-5-hydroxymethyl-3,3-dimethyl-2-oxo-pyrrolidin-1-yl)-2,6-dimethyl-phenyl]-ethenesulfonyl}-2-(3-trifluoromethoxy-phenyl)-1,3,8-triaza-spiro[4.5]dec-1-en-4-one;

(713) 8-{(E)-2-[4-((R)-5-hydroxymethyl-3-methyl-2-oxo-pyrrolidin-1-yl)-2,6-dimethyl-phenyl]-ethenesulfonyl}-2-(3-trifluoromethoxy-phenyl)-1,3,8-triaza-spiro[4.5]dec-1-en-4-one;

(714) 3-(3,5-dimethyl-4-{(E)-2-[4-oxo-2-(3-trifluoromethoxy-phenyl)-1,3,8-triaza-spiro[4.5]dec-1-ene-8-sulfonyl]-vinyl}-phenyl)-1-(2-hydroxy-ethyl)-5,5-dimethyl-imidazolidine-2,4-dione;

(715) N-(3,5-dimethyl-4-{(E)-2-[4-oxo-2-(3-trifluoromethoxy-phenyl)-1,3,8-triaza-spiro[4.5]dec-1-ene-8-sulfonyl]-vinyl}-phenyl)-N-(4-hydroxy-cyclohexyl)-methane sulfonamide;

(716) N-(4-{(E)-2-[2-(4-butyl-cyclohexyl)-4-oxo-1,3,8-triaza-spiro[4.5]dec-1-ene-8-sulfonyl]-vinyl}-3,5-dimethyl-phenyl)-N-[2-(2-hydroxy-ethoxy)-ethyl]-acetamide;

(717) N-(2-fluoro-5-methyl-4-{(E)-2-[4-oxo-2-(3-trifluoromethoxy-phenyl)-1,3,8-triaza-spiro[4.5]dec-1-ene-8-sulfonyl]-vinyl}-phenyl)-N-(2-hydroxy-ethyl)-acetamide;

(718) N-(4-{(E)-2-[2-(4-fluoro-3-trifluoromethyl-phenyl)-4-oxo-1,3,8-triaza-spiro[4.5]dec-1-ene-8-sulfonyl]-vinyl}-3,5-dimethyl-phenyl)-N-(2-hydroxy-ethyl)-acetamide;

(719) N-(2-hydroxy-ethyl)-N-(3-methyl-4-{(E)-2-[4-oxo-2-(3-trifluoromethoxy-phenyl)-1,3,8-triaza-spiro[4.5]dec-1-ene-8-sulfonyl]-vinyl}-phenyl)-methanesulfonamide;

(720) N-(2-hydroxy-ethyl)-N-{3-methyl-4-[2-(2-nonyl-4-oxo-1,3,8-triaza-spiro[4.5]dec-1-ene-8-sulfonyl)-ethyl]-phenyl}-methanesulfonamide;

(721) N-(4-{2-[2-(4-fluoro-3-trifluoromethyl-phenyl)-4-oxo-1,3,8-triaza-spiro[4.5]dec-1-ene-8-sulfonyl]-ethyl}-3-methyl-phenyl)-N-(2-hydroxy-ethyl)-acetamide;

(722) 2-hydroxy-N-(2-hydroxy-ethyl)-N-(3-methyl-4-{(E)-2-[4-oxo-2-(3-trifluoromethoxy-phenyl)-1,3,8-triaza-spiro[4.5]dec-1-ene-8-sulfonyl]-vinyl}-phenyl)-acetamide;

(723) 1-[3,5-dimethyl-4-((E)-2-{4-oxo-2-[4-(3,3,3-trifluoro-propyl)-cyclohexyl]-1,3,8-triaza-spiro[4.5]dec-1-ene-8-sulfonyl}-vinyl)-phenyl]-1-methyl-urea;

(724) 1-[3,5-dimethyl-4-((E)-2-{4-oxo-2-[4-(3,3,3-trifluoro-propyl)-cyclohexyl]-1,3,8-triaza-spiro[4.5]dec-1-ene-8-sulfonyl}-vinyl)-phenyl]-1-[2-(2-hydroxy-ethoxy)-ethyl]-urea;

(725) 1-[3,5-dimethyl-4-((E)-2-{4-oxo-2-[4-(3,3,3-trifluoro-propyl)-cyclohexyl]-1,3,8-triaza-spiro[4.5]dec-1-ene-8-sulfonyl}-vinyl)-phenyl]-1-(2-methoxy-ethyl)-urea;

(726) 1-(3,5-dimethyl-4-{(E)-2-[2-(4-methyl-cyclohexyl)-4-oxo-1,3,8-triaza-spiro[4.5]dec-1-ene-8-sulfonyl]-vinyl}-phenyl)-1-isopropyl-urea;

(727) 1-(3-ethyl-4-{(E)-2-[2-(4-methyl-cyclohexyl)-4-oxo-1,3,8-triaza-spiro[4.5]dec-1-ene-8-sulfonyl]-vinyl}-phenyl)-1-methyl-urea;

(728) 1-(3-methoxy-5-methyl-4-{(E)-2-[2-(4-methyl-cyclohexyl)-4-oxo-1,3,8-triaza-spiro[4.5]dec-1-ene-8-sulfonyl]-vinyl}-phenyl)-1-methyl-urea;

(729) 1-cyanomethyl-1-(3-methyl-4-{(E)-2-[4-oxo-2-(3-trifluoromethoxy-phenyl)-1,3,8-triaza-spiro[4.5]dec-1-ene-8-sulfonyl]-vinyl}-phenyl)-urea;

(730) 1-cyclopentyl-1-(3-methyl-4-{(E)-2-[4-oxo-2-(3-trifluoromethoxy-phenyl)-1,3,8-triaza-spiro[4.5]dec-1-ene-8-sulfonyl]-vinyl}-phenyl)-urea;

(731) 1-(3-methyl-4-{(E)-2-[4-oxo-2-(3-trifluoromethoxy-phenyl)-1,3,8-triaza-spiro[4.5]dec-1-ene-8-sulfonyl]-vinyl}-phenyl)-1-(2,2,2-trifluoro-ethyl)-urea;

(732) 1-(4-{2-[2-(4-ethyl-cyclohexyl)-4-oxo-1,3,8-triaza-spiro[4.5]dec-1-ene-8-sulfonyl]-ethyl}-3,5-dimethyl-phenyl)-1-methyl-urea;

(733) 1-((S)-2,3-dihydroxy-propyl)-1-(3,5-dimethyl-4-{(E)-2-[2-(4-methyl-cyclohexyl)-4-oxo-1,3,8-triaza-spiro[4.5]dec-1-ene-8-sulfonyl]-vinyl}-phenyl)-urea;

(734) N-{4-[(E)-2-(2-cyclohexyl-4-oxo-1,3,8-triaza-spiro[4.5]dec-1-ene-8-sulfonyl)-vinyl]-3-methyl-phenyl}-N-cyclopentyl-acetamide;

(735) (S)-2-amino-N-{4-[(E)-2-(2-cyclohexyl-4-oxo-1,3,8-triaza-spiro[4.5]dec-1-ene-8-sulfonyl)-vinyl]-3,5-dimethyl-phenyl}-3-methyl-butylamide;

(736) 2-{4-[(E)-2-(2-cyclohexyl-4-oxo-1,3,8-triaza-spiro[4.5]dec-1-ene-8-sulfonyl)-vinyl]-indol-1-yl}-N-pyridin-4-yl-acetamide;

(737) 2-(3-methyl-4-{(E)-2-[2-(4-methyl-cyclohexyl)-4-oxo-1,3,8-triaza-spiro[4.5]dec-1-ene-8-sulfonyl]-vinyl}-phenyl)-acetamide;

(738) 2-cyclohexyl-8-{(E)-2-[4-(4,5-dihydro-thiazol-2-ylamino)-2,6-dimethyl-phenyl]-ethenesulfonyl}-1,3,8-triaza-spiro[4.5]dec-1-en-4-one;

(739) 2-cyclohexyl-8-{(E)-2-[2-methyl-4-(3-methyl-oxetan-3-ylmethoxy)-phenyl]-ethenesulfonyl}-1,3,8-triaza-spiro[4.5]dec-1-en-4-one;

(740) 1-(3,5-dimethyl-4-{2-[2-(4-methyl-cyclohexyl)-4-oxo-1,3,8-triaza-spiro[4.5]dec-1-ene-8-sulfonyl]-cyclopropyl}-phenyl)-1-methyl-urea;

(741) 1-(3,5-dimethyl-4-{(E)-1-methyl-2-[2-(4-methyl-cyclohexyl)-4-oxo-1,3,8-triaza-spiro[4.5]dec-1-ene-8-sulfonyl]-vinyl}-phenyl)-1-methyl-urea;

(742) N-(3-methyl-4-{(E)-2-[4-oxo-2-(3-trifluoromethoxy-phenyl)-1,3,8-triaza-spiro[4.5]dec-1-ene-8-sulfonyl]-vinyl}-phenyl)-sulfamide;

(743) N-(3-hydroxy-propyl)-N'-(3-methyl-4-{(E)-2-[4-oxo-2-(3-trifluoromethoxy-phenyl)-1,3,8-triaza-spiro[4.5]dec-1-ene-8-sulfonyl]-vinyl}-phenyl)-sulfamide;

(744) N-methyl-N-(3-methyl-4-{(E)-3-[2-(4-methyl-cyclohexyl)-4-oxo-1,3,8-triaza-spiro[4.5]dec-1-ene-8-sulfonyl]-propenyl}-phenyl)-acetamide;

(745) 2-cyclohexyl-8-[2-(2-methyl-1H-indol-4-yl)-ethanesulfonyl]-1,3,8-triaza-spiro[4.5]dec-1-en-4-one;

(746) 8-{2-[1-((S)-2,3-dihydroxy-propyl)-1H-indol-4-yl]-ethanesulfonyl}-2-(3-trifluoromethoxy-phenyl)-1,3,8-triaza-spiro[4.5]dec-1-en-4-one;

(747) 2-cyclohexyl-8-[2-(1-methyl-1,2,3,4-tetrahydro-quinolin-5-yl)-ethanesulfonyl]-1,3,8-triaza-spiro[4.5]dec-1-en-4-one;

(748) 2-cyclohexyl-8-{2-[1-(3,4-dihydroxy-butyl)-1H-indol-4-yl]-ethanesulfonyl}-1,3,8-triaza-spiro[4.5]dec-1-en-4-one;

(749) 3-(2,6-dimethyl-4-{2-[2-(4-methyl-cyclohexyl)-4-oxo-1,3,8-triaza-spiro[4.5]dec-1-ene-8-sulfonyl]-ethyl}-phenyl)-imidazolidine-2,4-dione;

(750) 2-(3-methyl-4-{2-[2-(4-methyl-cyclohexyl)-4-oxo-1,3,8-triaza-spiro[4.5]dec-1-ene-8-sulfonyl]-ethyl}-phenyl)-acetamide;

(751) N-(3-ethoxy-4-{2-[2-(4-methyl-cyclohexyl)-4-oxo-1,3,8-triaza-spiro[4.5]dec-1-ene-8-sulfonyl]-ethyl}-phenyl)-acetamide;

(752) N-(3-ethyl-4-{2-[2-(4-methyl-cyclohexyl)-4-oxo-1,3,8-triaza-spiro[4.5]dec-1-ene-8-sulfonyl]-ethyl}-phenyl)-acetamide;

(753) N-(3-ethoxymethyl-4-{2-[2-(4-methyl-cyclohexyl)-4-oxo-1,3,8-triaza-spiro[4.5]dec-1-ene-8-sulfonyl]-ethyl}-phenyl)-acetamide;

(754) N-(3-methoxymethyl-4-{2-[2-(4-methyl-cyclohexyl)-4-oxo-1,3,8-triaza-spiro[4.5]dec-1-ene-8-sulfonyl]-ethyl}-phenyl)-acetamide;

(755) N-(2-methoxy-ethyl)-N-[3-methyl-4-(2-{4-oxo-2-[4-(3,3,3-trifluoro-propyl)-cyclohexyl]-1,3,8-triaza-spiro[4.5]dec-1-ene-8-sulfonyl}-ethyl)-phenyl]-acetamide;

(756) N-[3,5-dimethyl-4-(2-{4-oxo-2-[4-(3,3,3-trifluoro-propyl)-cyclohexyl]-1,3,8-triaza-spiro[4.5]dec-1-ene-8-sulfonyl}-ethyl)-phenyl]-N-(2-methoxy-ethyl)-acetamide;

(757) N-[2-(2-fluoro-ethoxy)-ethyl]-N-[3-methyl-4-(2-{4-oxo-2-[4-(3,3,3-trifluoro-propyl)-cyclohexyl]-1,3,8-triaza-spiro[4.5]dec-1-ene-8-sulfonyl}-ethyl)-phenyl]-acetamide;

(758) N-[2-(2-hydroxy-ethoxy)-ethyl]-N-[3-methyl-4-(2-{4-oxo-2-[4-(3,3,3-trifluoro-propyl)-cyclohexyl]-1,3,8-triaza-spiro[4.5]dec-1-ene-8-sulfonyl}-ethyl)-phenyl]-acetamide;

(759) N-[3,5-dimethyl-4-(2-{4-oxo-2-[4-(3,3,3-trifluoro-propyl)-cyclohexyl]-1,3,8-triaza-spiro[4.5]dec-1-ene-8-sulfonyl}-ethyl)-phenyl]-N-methyl-acetamide;

(760) 3-[3,5-dimethyl-4-(2-{4-oxo-2-[4-(3,3,3-trifluoro-propyl)-cyclohexyl]-1,3,8-triaza-spiro[4.5]dec-1-ene-8-sulfonyl}-ethyl)-phenyl]-1-methyl-imidazolidine-2,4-dione;

(761) 8-(2-{4-[4-(2-fluoro-ethyl)-piperazine-1-carbonyl]-2,6-dimethyl-phenyl}-ethanesulfonyl)-2-[4-(3,3,3-trifluoro-propyl)-cyclohexyl]-1,3,8-triaza-spiro[4.5]dec-1-en-4-one;

(764) 8-{2-[2,6-dimethyl-4-(3-oxo-morpholin-4-yl)-phenyl]-ethanesulfonyl}-2-[4-(3,3,3-trifluoro-propyl)-cyclohexyl]-1,3,8-triaza-spiro[4.5]dec-1-en-4-one;

(765) 8-{2-[2,6-dimethyl-4-(3-oxo-morpholin-4-yl)-phenyl]-ethanesulfonyl}-2-(4-methyl-cyclohexyl)-1,3,8-triaza-spiro[4.5]dec-1-en-4-one;

(766) N-[3,5-dimethyl-4-(2-{4-oxo-2-[4-(3,3,3-trifluoro-propyl)-cyclohexyl]-1,3,8-triaza-spiro[4.5]dec-1-ene-8-sulfonyl}-ethyl)-phenyl]-N-[2-(2-fluoro-ethoxy)-ethyl]-acetamide;

(767) 3-(3,5-dimethyl-4-{2-[2-(4-methyl-cyclohexyl)-4-oxo-1,3,8-triaza-spiro[4.5]dec-1-ene-8-sulfonyl]-ethyl}-phenyl)-5-methyl-imidazolidine-2,4-dione;

(768) 3,5-dimethyl-4-(2-{4-oxo-2-[4-(3,3,3-trifluoro-propyl)-cyclohexyl]-1,3,8-triaza-spiro[4.5]dec-1-ene-8-sulfonyl}-ethyl)-benzoic acid;

(769) 3,5-dimethyl-4-(2-{4-oxo-2-[4-(3,3,3-trifluoro-propyl)-cyclohexyl]-1,3,8-triaza-spiro[4.5]dec-1-ene-8-sulfonyl}-ethyl)-benzoic acid N'-acetyl-hydrazide;

(770) 8-[2-(4-hydroxymethyl-2,6-dimethyl-phenyl)-ethanesulfonyl]-2-[4-(3,3,3-trifluoro-propyl)-cyclohexyl]-1,3,8-triaza-spiro[4.5]dec-1-en-4-one;

(771) 8-{2-[2,6-dimethyl-4-(2-oxo-piperidin-1-yl)-phenyl]-ethanesulfonyl}-2-(4-methyl-cyclohexyl)-1,3,8-triaza-spiro[4.5]dec-1-en-4-one;

(772) N-[3,5-dimethyl-4-(2-{4-oxo-2-[4-(3,3,3-trifluoro-propyl)-cyclohexyl]-1,3,8-triaza-spiro[4.5]dec-1-ene-8-sulfonyl}-ethyl)-benzyl]-acetamide;

(773) N-(3,5-dimethyl-4-{2-[2-(4-methyl-cyclohexyl)-4-oxo-1,3,8-triaza-spiro[4.5]dec-1-ene-8-sulfonyl]-ethyl}-benzyl)-acetamide;

(774) 3-[3,5-dimethyl-4-(2-{4-oxo-2-[4-(3,3,3-trifluoro-propyl)-cyclohexyl]-1,3,8-triaza-spiro[4.5]dec-1-ene-8-sulfonyl}-ethyl)-benzyl]-imidazolidine-2,4-dione;

(775) 3-[3,5-dimethyl-4-(2-{4-oxo-2-[4-(3,3,3-trifluoro-propyl)-cyclohexyl]-1,3,8-triaza-spiro[4.5]dec-1-ene-8-sulfonyl}-ethyl)-benzyl]-5,5-dimethyl-imidazolidine-2,4-dione;

(776) 8-{2-[2,6-dimethyl-4-(2-oxo-pyrrolidin-1-ylmethyl)-phenyl]-ethanesulfonyl}-2-[4-(3,3,3-trifluoro-propyl)-cyclohexyl]-1,3,8-triaza-spiro[4.5]dec-1-en-4-one;

(777) 1-[3,5-dimethyl-4-(2-{4-oxo-2-[4-(3,3,3-trifluoro-propyl)-cyclohexyl]-1,3,8-triaza-spiro[4.5]dec-1-ene-8-sulfonyl}-ethyl)-benzyl]-pyrrolidine-2,5-dione;

(778) 3-(2,5-dimethyl-4-{2-[2-(4-methyl-cyclohexyl)-4-oxo-1,3,8-triaza-spiro[4.5]dec-1-ene-8-sulfonyl]-ethyl}-phenyl)-imidazolidine-2,4-dione;

(779) 3-(3,5-dimethyl-4-{2-[2-(4-methyl-cyclohexyl)-4-oxo-1,3,8-triaza-spiro[4.5]dec-1-ene-8-sulfonyl]-ethyl}-benzyl)-imidazolidine-2,4-dione;

(780) 3-(3,5-dimethyl-4-{2-[2-(4-methyl-cyclohexyl)-4-oxo-1,3,8-triaza-spiro[4.5]dec-1-ene-8-sulfonyl]-ethyl}-benzyl)-5,5-dimethyl-imidazolidine-2,4-dione;

(781) 8-{2-[2,6-dimethyl-4-(2-oxo-pyrrolidin-1-ylmethyl)-phenyl]-ethanesulfonyl}-2-(4-methyl-cyclohexyl)-1,3,8-triaza-spiro[4.5]dec-1-en-4-one;

(782) 1-(3,5-dimethyl-4-{2-[2-(4-methyl-cyclohexyl)-4-oxo-1,3,8-triaza-spiro[4.5]dec-1-ene-8-sulfonyl]-ethyl}-benzyl)-pyrrolidine-2,5-dione;

(783) N-(2,6-dimethyl-4-{2-[2-(4-methyl-cyclohexyl)-4-oxo-1,3,8-triaza-spiro[4.5]dec-1-ene-8-sulfonyl]-ethyl}-phenyl)-N-methyl-acetamide;

(784) N-[3,5-dimethyl-4-(2-{4-oxo-2-[4-(3,3,3-trifluoro-propyl)-cyclohexyl]-1,3,8-triaza-spiro[4.5]dec-1-ene-8-sulfonyl}-ethyl)-benzyl]-N-methyl-acetamide;

(785) N-(3,5-dimethyl-4-{2-[2-(4-methyl-cyclohexyl)-4-oxo-1,3,8-triaza-spiro[4.5]dec-1-ene-8-sulfonyl]-ethyl}-benzyl)-N-methyl-acetamide;

(786) 1-(3,5-dimethyl-4-{2-[2-(4-methyl-cyclohexyl)-4-oxo-1,3,8-triaza-spiro[4.5]dec-1-ene-8-sulfonyl]-ethyl}-phenyl)-dihydro-pyrimidine-2,4-dione;

(787) 3,5-dimethyl-4-(2-{4-oxo-2-[4-(3,3,3-trifluoro-propyl)-cyclohexyl]-1,3,8-triaza-spiro[4.5]dec-1-ene-8-sulfonyl}-ethyl)-benzoic acid trimethylhydrazide;

(788) 8-{2-[1-((S)-2,3-dihydroxy-propyl)-1H-indol-4-yl]-ethanesulfonyl}-2-(8,8,9,9,9-pentafluoro-nonyl)-1,3,8-triaza-spiro[4.5]dec-1-en-4-one;

(789) 8-{2-[1-((S)-2,3-dihydroxy-propyl)-1H-indol-4-yl]-ethanesulfonyl}-2-(9,9,9-trifluoro-nonyl)-1,3,8-triaza-spiro[4.5]dec-1-en-4-one;

(790) 3-{3-methyl-4-[2-(2-nonyl-4-oxo-1,3,8-triaza-spiro[4.5]dec-1-ene-8-sulfonyl)-ethyl]-phenyl}-imidazolidine-2,4-dione;

(791) 8-{2-[1-((R)-2,3-dihydroxy-propyl)-4,6-dimethyl-1H-indol-5-yl]-ethanesulfonyl}-2-[4-(3,3,3-trifluoro-propyl)-cyclohexyl]-1,3,8-triaza-spiro[4.5]dec-1-en-4-one;

(792) 3-(3-methyl-4-{2-[4-oxo-2-(3-trifluoromethoxy-phenyl)-1,3,8-triaza-spiro[4.5]dec-1-ene-8-sulfonyl]-ethyl}-phenyl)-imidazolidine-2,4-dione;

(793) 8-{2-[2-methyl-4-(3-oxo-morpholin-4-yl)-phenyl]-ethanesulfonyl}-2-(3-trifluoromethoxy-phenyl)-1,3,8-triaza-spiro[4.5]dec-1-en-4-one;

(794) N-(4-{2-[2-(4-fluoro-3-trifluoromethyl-phenyl)-4-oxo-1,3,8-triaza-spiro[4.5]dec-1-ene-8-sulfonyl]-ethyl}-3,5-dimethyl-phenyl)-N-(2-hydroxy-ethyl)-acetamide;

(795) 3-{4-[2-(2-nonyl-4-oxo-1,3,8-triaza-spiro[4.5]dec-1-ene-8-sulfonyl)-ethyl]-3-trifluoromethyl-phenyl}-imidazolidine-2,4-dione;

(796) 3,5-dimethyl-4-[2-(2-nonyl-4-oxo-1,3,8-triaza-spiro[4.5]dec-1-ene-8-sulfonyl)-ethyl]-benzoic acid;

(797) 2-(4-fluoro-3-trifluoromethyl-phenyl)-8-{2-[4-(4-hydroxy-piperidine-1-carbonyl)-2,6-dimethyl-phenyl]-ethanesulfonyl}-1,3,8-triaza-spiro[4.5]dec-1-en-4-one;

(798) 8-{2-[4-(3,4-dihydroxy-butoxy)-2,6-dimethyl-phenyl]-ethanesulfonyl}-2-nonyl-1,3,8-triaza-spiro[4.5]dec-1-en-4-one;

(799) 3-(3,5-dimethyl-4-{2-[4-oxo-2-(3-trifluoromethoxy-phenyl)-1,3,8-triaza-spiro[4.5]dec-1-ene-8-sulfonyl]-ethyl}-phenyl)-imidazolidine-2,4-dione;

(800) 3-(4-{2-[2-(4-fluoro-3-trifluoromethyl-phenyl)-4-oxo-1,3,8-triaza-spiro[4.5]dec-1-ene-8-sulfonyl]-ethyl}-3,5-dimethyl-phenyl)-imidazolidine-2,4-dione;

(801) 8-{2-[4-(3,4-dihydroxy-butoxy)-2,6-dimethyl-phenyl]-ethanesulfonyl}-2-(4-fluoro-3-trifluoromethyl-phenyl)-1,3,8-triaza-spiro[4.5]dec-1-en-4-one;

(802) 8-{2-[4-(4-fluoromethyl-4-hydroxy-piperidine-1-carbonyl)-2,6-dimethyl-phenyl]-ethanesulfonyl}-2-(4-fluoro-3-trifluoromethyl-phenyl)-1,3,8-triaza-spiro[4.5]dec-1-en-4-one;

(803) 2-(4-fluoro-3-trifluoromethyl-phenyl)-8-{2-[4-(4-hydroxy-4-methyl-piperidine-1-carbonyl)-2,6-dimethyl-phenyl]-ethanesulfonyl}-1,3,8-triaza-spiro[4.5]dec-1-en-4-one;

(804) 8-{2-[2,6-dimethyl-4-(2-oxa-7-aza-spiro[3.5]nonane-7-carbonyl)-phenyl]-ethanesulfonyl}-2-(4-fluoro-3-trifluoromethyl-phenyl)-1,3,8-triaza-spiro[4.5]dec-1-en-4-one;

(812) N-(3-isopropoxy-4-{2-[2-(4-methyl-cyclohexyl)-4-oxo-1,3,8-triaza-spiro[4.5]dec-1-ene-8-sulfonyl]-ethyl}-phenyl)-acetamide;

(817) 1-{3,5-dimethyl-4-[2-(2-nonyl-4-oxo-1,3,8-triaza-spiro[4.5]dec-1-ene-8-sulfonyl)-ethyl]-phenyl}-1-methyl-urea;

(818) 1-[3,5-dimethyl-4-(2-{4-oxo-2-[4-(3,3,3-trifluoro-propyl)-cyclohexyl]-1,3,8-triaza-spiro[4.5]dec-1-ene-8-sulfonyl}-ethyl)-phenyl]-1-(2-fluoro-ethyl)-urea;

(820) N-[3,5-dimethyl-4-(2-{4-oxo-2-[4-(3,3,3-trifluoro-propyl)-cyclohexyl]-1,3,8-triaza-spiro[4.5]dec-1-ene-8-sulfonyl}-ethyl)-phenyl]-N-[2-(2-hydroxy-ethoxy)-ethyl]-acetamide;

(821) 8-{2-[4-((R)-2,3-dihydroxy-propoxy)-2,6-dimethyl-phenyl]-ethanesulfonyl}-2-[4-(3,3,3-trifluoro-propyl)-cyclohexyl]-1,3,8-triaza-spiro[4.5]dec-1-en-4-one;

(822) 8-(2-{1-[2-((S)-2,3-dihydroxy-propoxy)-ethyl]-1H-indol-4-yl}-ethanesulfonyl)-2-[4-(3,3,3-trifluoro-propyl)-cyclohexyl]-1,3,8-triaza-spiro[4.5]dec-1-en-4-one;

(823) 2-[4-(3,3,3-trifluoro-propyl)-cyclohexyl]-8-(2-{1-[2-((2S,3S)-2,3,4-trihydroxy-butoxy)-ethyl]-1H-indol-4-yl}-ethanesulfonyl)-1,3,8-triaza-spiro[4.5]dec-1-en-4-one;

(824) N—((S)-2,3-dihydroxy-propyl)-N-(3,5-dimethyl-4-{2-[4-oxo-2-(9,9,9-trifluoro-nonyl)-1,3,8-triaza-spiro[4.5]dec-1-ene-8-sulfonyl]-ethyl}-phenyl)-acetamide;

(825) N-[2-(2-hydroxy-ethoxy)-ethyl]-N-{3-methyl-4-[2-(2-nonyl-4-oxo-1,3,8-triaza-spiro[4.5]dec-1-ene-8-sulfonyl)-ethyl]-phenyl}-acetamide;

(826) 1-[3,5-dimethyl-4-(2-{4-oxo-2-[4-(3,3,3-trifluoro-propyl)-cyclohexyl]-1,3,8-triaza-spiro[4.5]dec-1-ene-8-sulfonyl}-ethyl)-phenyl]-1-[2-(2-hydroxy-ethoxy)-ethyl]-urea;

(827) 1-[3,5-dimethyl-4-(2-{4-oxo-2-[4-(3,3,3-trifluoro-propyl)-cyclohexyl]-1,3,8-triaza-spiro[4.5]dec-1-ene-8-sulfonyl}-ethyl)-phenyl]-1-(2-methoxy-ethyl)-urea;

(828) 1-(3,5-dimethyl-4-{2-[2-(4-methyl-cyclohexyl)-4-oxo-1,3,8-triaza-spiro[4.5]dec-1-ene-8-sulfonyl]-ethyl}-phenyl)-1-isopropyl-urea;

(829) 1-(3-ethyl-4-{2-[2-(4-methyl-cyclohexyl)-4-oxo-1,3,8-triaza-spiro[4.5]dec-1-ene-8-sulfonyl]-ethyl}-phenyl)-1-methyl-urea;

(830) 1-((S)-2,3-dihydroxy-propyl)-1-(3,5-dimethyl-4-{2-[2-(4-methyl-cyclohexyl)-4-oxo-1,3,8-triaza-spiro[4.5]dec-1-ene-8-sulfonyl]-ethyl}-phenyl)-urea;

(831) 8-{2-[4-(4-hydroxy-4-hydroxymethyl-piperidine-1-carbonyl)-2,6-dimethyl-phenyl]-ethanesulfonyl}-2-(3-trifluoromethoxy-phenyl)-1,3,8-triaza-spiro[4.5]dec-1-en-4-one;

(832) 3-{3,5-dimethyl-4-[2-(2-nonyl-4-oxo-1,3,8-triaza-spiro[4.5]dec-1-ene-8-sulfonyl)-ethyl]-phenyl}-imidazolidine-2,4-dione;

(833) 5-tert-butoxymethyl-3-(3,5-dimethyl-4-{2-[2-(4-methyl-cyclohexyl)-4-oxo-1,3,8-triaza-spiro[4.5]dec-1-ene-8-sulfonyl]-ethyl}-phenyl)-imidazolidine-2,4-dione;

(834) 2-(4-methyl-cyclohexyl)-8-{2-[2-methyl-4-(5-oxo-pyrazolidin-1-yl)-phenyl]-ethanesulfonyl}-1,3,8-triaza-spiro[4.5]dec-1-en-4-one;

(835) 2-cyclohexyl-8-[2-(1H-indol-7-yl)-ethanesulfonyl]-1,3,8-triaza-spiro[4.5]dec-1-en-4-one;

(836) 2-cyclohexyl-8-[2-(6-trifluoromethyl-1H-indol-5-yl)-ethanesulfonyl]-1,3,8-triaza-spiro[4.5]dec-1-en-4-one;

(837) 2-cyclohexyl-8-[2-(6-methyl-1H-indol-5-yl)-ethanesulfonyl]-1,3,8-triaza-spiro[4.5]dec-1-en-4-one;

(838) 2-cyclohexyl-8-(2-{1-[2-(2-hydroxy-ethoxy)-ethyl]-1H-indol-5-yl}-ethanesulfonyl)-1,3,8-triaza-spiro[4.5]dec-1-en-4-one;

(839) 2-cyclohexyl-8-[2-(6-trifluoromethyl-1H-benzimidazol-5-yl)-ethanesulfonyl]-1,3,8-triaza-spiro[4.5]dec-1-en-4-one;

(840) 8-{2-[1-((S)-2,3-dihydroxy-propyl)-1H-indol-4-yl]-ethanesulfonyl}-2-(3-trifluoromethyl-phenyl)-1,3,8-triaza-spiro[4.5]dec-1-en-4-one;

(841) 2-cyclohexyl-8-{2-[4-(1,1-dioxo-1$\lambda^6$-thiomorpholine-4-carbonyl)-2-methyl-phenyl]-ethanesulfonyl}-1,3,8-triaza-spiro[4.5]dec-1-en-4-one;

(842) 2-cyclohexyl-8-{2-[4-(2-dimethylamino-ethylamino)-2-methyl-phenyl]-ethanesulfonyl}-1,3,8-triaza-spiro[4.5]dec-1-en-4-one;

(843) 8-{2-[2-methyl-4-(4-methyl-piperazine-1-carbonyl)-phenyl]-ethanesulfonyl}-2-(3-trifluoromethoxy-phenyl)-1,3,8-triaza-spiro[4.5]dec-1-en-4-one;

(844) 4-[2-(2-cyclohexyl-4-oxo-1,3,8-triaza-spiro[4.5]dec-1-ene-8-sulfonyl)-ethyl]-N-(2-dimethylamino-ethyl)-3-methyl-benzenesulfonamide;

(845) 8-(2-{2-methyl-4-[2-(4-methyl-piperazin-1-yl)-2-oxo-ethylamino]-phenyl}-ethanesulfonyl)-2-(3-trifluoromethoxy-phenyl)-1,3,8-triaza-spiro[4.5]dec-1-en-4-one;

(846) 3-methyl-4-{2-[4-oxo-2-(3-trifluoromethoxy-phenyl)-1,3,8-triaza-spiro[4.5]dec-1-ene-8-sulfonyl]-ethyl}-N-pyridin-4-yl-benzenesulfonamide;

(847) 2-(3-methyl-4-{2-[4-oxo-2-(3-trifluoromethoxy-phenyl)-1,3,8-triaza-spiro[4.5]dec-1-ene-8-sulfonyl]-ethyl}-phenylamino)-acetamide;

(848) N-(1-benzyl-piperidin-4-yl)-3-methyl-4-{2-[4-oxo-2-(3-trifluoromethoxy-phenyl)-1,3,8-triaza-spiro[4.5]dec-1-ene-8-sulfonyl]-ethyl}-benzenesulfonamide;

(849) 8-{2-[4-(4-isopropyl-piperazine-1-carbonyl)-2-methyl-phenyl]-ethanesulfonyl}-2-(3-trifluoromethoxy-phenyl)-1,3,8-triaza-spiro[4.5]dec-1-en-4-one;

(850) 8-{2-[1-((S)-2,3-dihydroxy-propyl)-1H-indol-5-yl]-ethanesulfonyl}-2-(3-trifluoromethoxy-phenyl)-1,3,8-triaza-spiro[4.5]dec-1-en-4-one;

(851) N—((R)-2,3-dihydroxy-propyl)-3-methyl-4-{2-[4-oxo-2-(3-trifluoromethoxy-phenyl)-1,3,8-triaza-spiro[4.5]dec-1-ene-8-sulfonyl]-ethyl}-benzenesulfonamide;

(852) 3-methyl-4-{2-[4-oxo-2-(3-trifluoromethyl-phenyl)-1,3,8-triaza-spiro[4.5]dec-1-ene-8-sulfonyl]-ethyl}-N-pyridin-3-ylmethyl-benzenesulfonamide;

(853) N-(4-hydroxy-cyclohexyl)-3-methyl-4-{2-[4-oxo-2-(3-trifluoromethyl-phenyl)-1,3,8-triaza-spiro[4.5]dec-1-ene-8-sulfonyl]-ethyl}-benzenesulfonamide;

(854) N-(2-hydroxy-1,1-bis-hydroxymethyl-ethyl)-3-methyl-4-{2-[4-oxo-2-(3-trifluoromethyl-phenyl)-1,3,8-triaza-spiro[4.5]dec-1-ene-8-sulfonyl]-ethyl}-benzenesulfonamide;

(855) 8-{2-[4-(3,4-dihydroxy-butoxy)-3,5-dimethyl-phenyl]-ethanesulfonyl}-2-(3-trifluoromethoxy-phenyl)-1,3,8-triaza-spiro[4.5]dec-1-en-4-one;

(856) 2-(4-fluoro-3-trifluoromethyl-phenyl)-8-{2-[2-methyl-4-(pyrrolidine-1-carbonyl)-phenyl]-ethanesulfonyl}-1,3,8-triaza-spiro[4.5]dec-1-en-4-one;

(857) 2-(4-fluoro-3-trifluoromethyl-phenyl)-8-{2-[4-((R)-2-hydroxymethyl-5-oxo-pyrrolidin-1-yl)-2-methyl-phenyl]-ethanesulfonyl}-1,3,8-triaza-spiro[4.5]dec-1-en-4-one;

(858) 2-(4-fluoro-3-trifluoromethyl-phenyl)-8-{2-[4-((S)-2-hydroxymethyl-5-oxo-pyrrolidin-1-yl)-2-methyl-phenyl]-ethanesulfonyl}-1,3,8-triaza-spiro[4.5]dec-1-en-4-one;

(859) 4-(3-methyl-4-{2-[4-oxo-2-(3-trifluoromethoxy-phenyl)-1,3,8-triaza-spiro[4.5]dec-1-ene-8-sulfonyl]-ethyl}-phenoxy)-piperidine-1-carboxylic acid tert-butyl ester;

(860) 8-{2-[4-(3,4-dihydroxy-butoxy)-3,5-difluoro-phenyl]-ethanesulfonyl}-2-(3-trifluoromethoxy-phenyl)-1,3,8-triaza-spiro[4.5]dec-1-en-4-one;

(861) 2-cyclohexyl-8-{2-[2-methyl-4-(2-oxo-azetidin-1-yl)-phenyl]-ethanesulfonyl}-1,3,8-triaza-spiro[4.5]dec-1-en-4-one;

(862) 1-methyl-3-(3-methyl-4-{2-[2-(4-methyl-cyclohexyl)-4-oxo-1,3,8-triaza-spiro[4.5]dec-1-ene-8-sulfonyl]-ethyl}-phenyl)-imidazolidine-2,4-dione;

(863) 5,5-dimethyl-3-(3-methyl-4-{2-[2-(4-methyl-cyclohexyl)-4-oxo-1,3,8-triaza-spiro[4.5]dec-1-ene-8-sulfonyl]-ethyl}-phenyl)-imidazolidine-2,4-dione;

(864) 5,5-dimethyl-3-[3-methyl-4-(2-{4-oxo-2-[4-(3,3,3-trifluoro-propyl)-cyclohexyl]-1,3,8-triaza-spiro[4.5]dec-1-ene-8-sulfonyl}-ethyl)-phenyl]-imidazolidine-2,4-dione;

(865) 2-(4-methyl-cyclohexyl)-8-{2-[2-methyl-4-(2-oxo-oxazolidin-3-yl)-phenyl]-ethanesulfonyl}-1,3,8-triaza-spiro[4.5]dec-1-en-4-one;

(866) 2-(4-methyl-cyclohexyl)-8-{2-[2-methyl-4-(4-oxo-oxazolidin-3-yl)-phenyl]-ethanesulfonyl}-1,3,8-triaza-spiro[4.5]dec-1-en-4-one;

(867) 8-{2-[1-((R)-2,3-dihydroxy-propyl)-1H-indol-4-yl]-ethanesulfonyl}-2-[4-(3,3,3-trifluoro-propyl)-cyclohexyl]-1,3,8-triaza-spiro[4.5]dec-1-en-4-one;

(868) 8-(2-{4-[(1H-imidazol-2-yl)-methyl-amino]-2,6-dimethyl-phenyl}-ethanesulfonyl)-2-(4-methyl-cyclohexyl)-1,3,8-triaza-spiro[4.5]dec-1-en-4-one;

(869) 3-(3,5-dimethyl-4-{2-[2-(4-methyl-cyclohexyl)-4-oxo-1,3,8-triaza-spiro[4.5]dec-1-ene-8-sulfonyl]-ethyl}-phenyl)-5,5-dimethyl-imidazolidine-2,4-dione;

(870) 2-(4-methyl-cyclohexyl)-8-{2-[2-methyl-4-(2-oxo-piperazin-1-yl)-phenyl]-ethanesulfonyl}-1,3,8-triaza-spiro[4.5]dec-1-en-4-one;

(872) 2-cyclohexyl-8-{2-[1-((S)-2,3-dihydroxy-propyl)-1H-indol-5-yl]-ethanesulfonyl}-1,3,8-triaza-spiro[4.5]dec-1-en-4-one;

(873) N-(2-fluoro-5-methyl-4-{2-[4-oxo-2-(3-trifluoromethoxy-phenyl)-1,3,8-triaza-spiro[4.5]dec-1-ene-8-sulfonyl]-ethyl}-phenyl)-N-(2-hydroxy-ethyl)-acetamide;

(874) N-(3-methyl-4-{2-[4-oxo-2-(3-trifluoromethoxy-phenyl)-1,3,8-triaza-spiro[4.5]dec-1-ene-8-sulfonyl]-ethyl}-phenyl)-sulfamide;

(875) N-(3-hydroxy-propyl)-N'-(3-methyl-4-{2-[4-oxo-2-(3-trifluoromethoxy-phenyl)-1,3,8-triaza-spiro[4.5]dec-1-ene-8-sulfonyl]-ethyl}-phenyl)-sulfamide;

(876) 1-cyanomethyl-1-(3-methyl-4-{2-[4-oxo-2-(3-trifluoromethoxy-phenyl)-1,3,8-triaza-spiro[4.5]dec-1-ene-8-sulfonyl]-ethyl}-phenyl)-urea;

(877) 1-(3-methyl-4-{2-[4-oxo-2-(3-trifluoromethoxy-phenyl)-1,3,8-triaza-spiro[4.5]dec-1-ene-8-sulfonyl]-ethyl}-phenyl)-1-(2,2,2-trifluoro-ethyl)-urea;

(878) 1-(4-{2-[2-(4-ethyl-cyclohexyl)-4-oxo-1,3,8-triaza-spiro[4.5]dec-1-ene-8-sulfonyl]-ethyl}-3-methyl-phenyl)-imidazolidine-2,4-dione;

(879) 1-(4-{2-[2-(4-ethyl-cyclohexyl)-4-oxo-1,3,8-triaza-spiro[4.5]dec-1-ene-8-sulfonyl]-ethyl}-3-methyl-phenyl)-5-methyl-imidazolidine-2,4-dione;

(880) 3-(4-{2-[2-(4-butyl-cyclohexyl)-4-oxo-1,3,8-triaza-spiro[4.5]dec-1-ene-8-sulfonyl]-ethyl}-3-methyl-phenyl)-imidazolidine-2,4-dione;

(881) 3-(3-methyl-4-{2-[2-(4-methyl-cyclohexyl)-4-oxo-1,3,8-triaza-spiro[4.5]dec-1-ene-8-sulfonyl]-ethyl}-phenyl)-imidazolidine-2,4-dione;

(882) 3-(4-{2-[2-(4-isopropyl-cyclohexyl)-4-oxo-1,3,8-triaza-spiro[4.5]dec-1-ene-8-sulfonyl]-ethyl}-3-methyl-phenyl)-imidazolidine-2,4-dione;

(883) 3-(3,5-dimethyl-4-{2-[2-(4-methyl-cyclohexyl)-4-oxo-1,3,8-triaza-spiro[4.5]dec-1-ene-8-sulfonyl]-ethyl}-phenyl)-imidazolidine-2,4-dione;

(884) 3-(4-{2-[2-(4-isopropyl-cyclohexyl)-4-oxo-1,3,8-triaza-spiro[4.5]dec-1-ene-8-sulfonyl]-ethyl}-3,5-dimethyl-phenyl)-imidazolidine-2,4-dione;

(885) 3-(3,5-dimethyl-4-{2-[2-(4-methyl-cyclohexyl)-4-oxo-1,3,8-triaza-spiro[4.5]dec-1-ene-8-sulfonyl]-ethyl}-phenyl)-1,5,5-trimethyl-imidazolidine-2,4-dione;

(886) (S)-2-amino-3-hydroxy-N-(3-methyl-4-{2-[4-oxo-2-(3-trifluoromethyl-phenyl)-1,3,8-triaza-spiro[4.5]dec-1-ene-8-sulfonyl]-ethyl}-phenyl)-propionamide;

(887) 1-(4-{2-[2-(4-ethyl-cyclohexyl)-4-oxo-1,3,8-triaza-spiro[4.5]dec-1-ene-8-sulfonyl]-ethyl}-3-methyl-phenyl)-5,5-dimethyl-imidazolidine-2,4-dione;

(888) 3,5-dimethyl-4-(2-{4-oxo-2-[4-(3,3,3-trifluoro-propyl)-cyclohexyl]-1,3,8-triaza-spiro[4.5]dec-1-ene-8-sulfonyl}-ethyl)-benzoic acid N,N'-dimethyl-hydrazide;

(889) 8-{2-[2-methyl-4-(piperidin-4-yloxy)-phenyl]-ethanesulfonyl}-2-(3-trifluoromethoxy-phenyl)-1,3,8-triaza-spiro[4.5]dec-1-en-4-one hydrochloride;

(890) 4-{2-[2-(4,4-difluoro-cyclohexyl)-4-oxo-1,3,8-triaza-spiro[4.5]dec-1-ene-8-sulfonyl]-ethyl}-3,N,N-trimethyl-benzamide;

(891) 4-{2-[2-(4-methanesulfonyl-phenyl)-4-oxo-1,3,8-triaza-spiro[4.5]dec-1-ene-8-sulfonyl]-ethyl}-3,N,N-trimethyl-benzamide;

(892) 3,N,N-trimethyl-4-(2-{4-oxo-2-[(E)-2-(3-trifluoromethyl-phenyl)-vinyl]-1,3,8-triaza-spiro[4.5]dec-1-ene-8-sulfonyl}-ethyl)-benzamide;

(893) 3,N,N-trimethyl-4-[2-(4-oxo-2-phenylethynyl-1,3,8-triaza-spiro[4.5]dec-1-ene-8-sulfonyl)-ethyl]-benzamide;

(894) 4-{2-[2-(4-butyl-cyclohexyl)-4-oxo-1,3,8-triaza-spiro[4.5]dec-1-ene-8-sulfonyl]-ethyl}-3,N,N-trimethyl-benzamide;

(895) 4-{2-[2-(4-tert-butyl-cyclohexyl)-4-oxo-1,3,8-triaza-spiro[4.5]dec-1-ene-8-sulfonyl]-ethyl}-3,N,N-trimethyl-benzamide;

(896) 4-{2-[2-(4-ethyl-cyclohexyl)-4-oxo-1,3,8-triaza-spiro[4.5]dec-1-ene-8-sulfonyl]-ethyl}-3,N,N-trimethyl-benzamide;

(897) 3,N,N-trimethyl-4-(2-{4-oxo-2-[4-(4,4,4-trifluoro-butyl)-cyclohexyl]-1,3,8-triaza-spiro[4.5]dec-1-ene-8-sulfonyl}-ethyl)-benzamide;

(898) 4-{2-[4-(cyclohexylmethyl-amino)-2-(3-trifluoromethoxy-phenyl)-1,3,8-triaza-spiro[4.5]deca-1,3-diene-8-sulfonyl]-ethyl}-3,N,N-trimethyl-benzamide;

(899) 4-{2-[4-dimethylamino-2-(3-trifluoromethoxy-phenyl)-1,3,8-triaza-spiro[4.5]deca-1,3-diene-8-sulfonyl]-ethyl}-3,N,N-trimethyl-benzamide;

(900) 4-{2-[4-[(Z)-hydroxyimino]-2-(3-trifluoromethoxy-phenyl)-1,3,8-triaza-spiro[4.5]dec-1-ene-8-sulfonyl]-ethyl}-3,N,N-trimethyl-benzamide;

(901) 4-{2-[4-[(Z)-methoxyimino]-2-(3-trifluoromethoxy-phenyl)-1,3,8-triaza-spiro[4.5]dec-1-ene-8-sulfonyl]-ethyl}-3,N,N-trimethyl-benzamide;

(902) 4-(2-{2-[4-(2-methoxy-ethyl)-cyclohexyl]-4-oxo-1,3,8-triaza-spiro[4.5]dec-1-ene-8-sulfonyl}-ethyl)-3,N,N-trimethyl-benzamide;

(903) N-{4-[2-(2-cyclopentyl-4-oxo-1,3,8-triaza-spiro[4.5]dec-1-ene-8-sulfonyl)-ethyl]-3-methyl-phenyl}-acetamide;

(904) N-(3-methyl-4-{2-[4-oxo-2-(4-trifluoromethyl-cyclohexyl)-1,3,8-triaza-spiro[4.5]dec-1-ene-8-sulfonyl]-ethyl}-phenyl)-acetamide;

(905) N-(4-{2-[2-(4-butyl-cyclohexyl)-4-oxo-1,3,8-triaza-spiro[4.5]dec-1-ene-8-sulfonyl]-ethyl}-3-methyl-phenyl)-acetamide;

(906) N-(4-{2-[2-(4-cyano-phenyl)-4-oxo-1,3,8-triaza-spiro[4.5]dec-1-ene-8-sulfonyl]-ethyl}-3-methyl-phenyl)-acetamide;

(907) N-(4-{2-[2-(3-cyano-phenyl)-4-oxo-1,3,8-triaza-spiro[4.5]dec-1-ene-8-sulfonyl]-ethyl}-3-methyl-phenyl)-acetamide;

(908) N-(4-{2-[2-(2-cyano-phenyl)-4-oxo-1,3,8-triaza-spiro[4.5]dec-1-ene-8-sulfonyl]-ethyl}-3-methyl-phenyl)-acetamide;

(909) N-(4-{2-[2-(4-tert-butyl-cyclohexyl)-4-oxo-1,3,8-triaza-spiro[4.5]dec-1-ene-8-sulfonyl]-ethyl}-3-methyl-phenyl)-acetamide;

(910) N-(4-{2-[2-(4-ethoxymethyl-cyclohexyl)-4-oxo-1,3,8-triaza-spiro[4.5]dec-1-ene-8-sulfonyl]-ethyl}-3-methyl-phenyl)-acetamide;

(911) N-(3-methyl-4-{2-[4-oxo-2-(4-propoxy-cyclohexyl)-1,3,8-triaza-spiro[4.5]dec-1-ene-8-sulfonyl]-ethyl}-phenyl)-acetamide;

(912) N-(4-{2-[2-(4-butoxy-cyclohexyl)-4-oxo-1,3,8-triaza-spiro[4.5]dec-1-ene-8-sulfonyl]-ethyl}-3-methyl-phenyl)-acetamide;

(913) N-(4-{2-[2-(4-isopropoxymethyl-cyclohexyl)-4-oxo-1,3,8-triaza-spiro[4.5]dec-1-ene-8-sulfonyl]-ethyl}-3-methyl-phenyl)-acetamide;

(914) N-[4-(2-{2-[4-(3-fluoro-propoxy)-cyclohexyl]-4-oxo-1,3,8-triaza-spiro[4.5]dec-1-ene-8-sulfonyl}-ethyl)-3-methyl-phenyl]-acetamide;

(915) N-[4-(2-{2-[4-(3-fluoro-propoxy)-cyclohexyl]-4-oxo-1,3,8-triaza-spiro[4.5]dec-1-ene-8-sulfonyl}-ethyl)-3-methyl-phenyl]-acetamide;

(916) N-[4-(2-{2-[4-((E)-3,3-difluoro-propenyl)-cyclohexyl]-4-oxo-1,3,8-triaza-spiro[4.5]dec-1-ene-8-sulfonyl}-ethyl)-3-methyl-phenyl]-acetamide;

(917) N-{4-[2-(2-cycloheptyl-4-oxo-1,3,8-triaza-spiro[4.5]dec-1-ene-8-sulfonyl)-ethyl]-3-methyl-phenyl}-acetamide;

(918) N-{4-[2-(2-adamantan-1-yl-4-oxo-1,3,8-triaza-spiro[4.5]dec-1-ene-8-sulfonyl)-ethyl]-3-methyl-phenyl}-acetamide;

(919) N-[3-methyl-4-(2-{4-oxo-2-[4-(2,2,2-trifluoro-ethoxymethyl)-cyclohexyl]-1,3,8-triaza-spiro[4.5]dec-1-ene-8-sulfonyl}-ethyl)-phenyl]-acetamide;

(920) N-[4-(2-{2-[4-(4-chloro-phenyl)-cyclohexyl]-4-oxo-1,3,8-triaza-spiro[4.5]dec-1-ene-8-sulfonyl}-ethyl)-3-methyl-phenyl]-acetamide;

(921) N-[3-methyl-4-(2-{4-oxo-2-[4-(3,3,3-trifluoro-propoxy)-cyclohexyl]-1,3,8-triaza-spiro[4.5]dec-1-ene-8-sulfonyl}-ethyl)-phenyl]-acetamide;

(922) N-[3-methyl-4-(2-{4-oxo-2-[4-(2,2,2-trifluoro-ethyl)-cyclohexyl]-1,3,8-triaza-spiro[4.5]dec-1-ene-8-sulfonyl}-ethyl)-phenyl]-acetamide;

(923) N-(3-methyl-4-{2-[4-oxo-2-((1S,3R)-3-propyl-cyclohexyl)-1,3,8-triaza-spiro[4.5]dec-1-ene-8-sulfonyl]-ethyl}-phenyl)-acetamide;

(924) N-(3-methyl-4-{2-[2-((1S,3R)-3-methyl-cyclohexyl)-4-oxo-1,3,8-triaza-spiro[4.5]dec-1-ene-8-sulfonyl]-ethyl}-phenyl)-acetamide;

(925) N-(4-{2-[2-(4,4-dimethyl-cyclohexyl)-4-oxo-1,3,8-triaza-spiro[4.5]dec-1-ene-8-sulfonyl]-ethyl}-3-methyl-phenyl)-acetamide;

(926) N-(3-methyl-4-{2-[4-oxo-2-(3,3,5,5-tetramethyl-cyclohexyl)-1,3,8-triaza-spiro[4.5]dec-1-ene-8-sulfonyl]-ethyl}-phenyl)-acetamide;

(927) N-[4-(2-{2-[4-(2-methoxy-ethyl)-cyclohexyl]-4-oxo-1,3,8-triaza-spiro[4.5]dec-1-ene-8-sulfonyl}-ethyl)-3-methyl-phenyl]-acetamide;

(928) [3-methyl-4-(2-{4-oxo-2-[4-(3,3,3-trifluoro-propyl)-cyclohexyl]-1,3,8-triaza-spiro[4.5]dec-1-ene-8-sulfonyl}-ethyl)-benzyl]-carbamic acid tert-butyl ester;

(929) N-(2-hydroxy-ethyl)-N-(3-methyl-4-{2-[4-oxo-2-(3-trifluoromethoxy-phenyl)-1,3,8-triaza-spiro[4.5]dec-1-ene-8-sulfonyl]-ethyl}-phenyl)-isobutylamide;

(930) 2-hydroxy-N-(2-hydroxy-ethyl)-N-(3-methyl-4-{2-[4-oxo-2-(3-trifluoromethoxy-phenyl)-1,3,8-triaza-spiro[4.5]dec-1-ene-8-sulfonyl]-ethyl}-phenyl)-acetamide;

(931) N-(3,5-dimethyl-4-{2-[2-(4-methyl-cyclohexyl)-4-oxo-1,3,8-triaza-spiro[4.5]dec-1-ene-8-sulfonyl]-ethyl}-phenyl)-2,2,2-trifluoro-N-methyl-acetamide;

(932) N-(3,5-dimethyl-4-{2-[2-((1S,3R)-3-methyl-cyclohexyl)-4-oxo-1,3,8-triaza-spiro[4.5]dec-1-ene-8-sulfonyl]-ethyl}-phenyl)-2,2,2-trifluoro-N-methyl-acetamide;

(933) N-(3,5-dimethyl-4-{2-[4-oxo-2-(3,3,5,5-tetramethyl-cyclohexyl)-1,3,8-triaza-spiro[4.5]dec-1-ene-8-sulfonyl]-ethyl}-phenyl)-2,2,2-trifluoro-N-methyl-acetamide;

(934) 1-{4-[2-(2-cycloheptyl-4-oxo-1,3,8-triaza-spiro[4.5]dec-1-ene-8-sulfonyl)-ethyl]-3,5-dimethyl-phenyl}-1-methyl-urea;

(935) 1-(3,5-dimethyl-4-{2-[4-oxo-2-(3-trifluoromethoxy-phenyl)-1,3,8-triaza-spiro[4.5]dec-1-ene-8-sulfonyl]-ethyl}-phenyl)-1-methyl-urea;

(936) 1-[3,5-dimethyl-4-(2-{4-oxo-2-[4-(2,2,2-trifluoro-ethyl)-cyclohexyl]-1,3,8-triaza-spiro[4.5]dec-1-ene-8-sulfonyl}-ethyl)-phenyl]-1-methyl-urea;

(937) 1-[2-chloro-3,5-dimethyl-4-(2-{4-oxo-2-[4-(2,2,2-trifluoro-ethyl)-cyclohexyl]-1,3,8-triaza-spiro[4.5]dec-1-ene-8-sulfonyl}-ethyl)-phenyl]-1-methyl-urea;

(938) 1-(4-{2-[2-(4,4-dimethyl-cyclohexyl)-4-oxo-1,3,8-triaza-spiro[4.5]dec-1-ene-8-sulfonyl]-ethyl}-3,5-dimethyl-phenyl)-1-methyl-urea;

(939) 1-[3,5-dimethyl-4-(2-{4-oxo-2-[4-(3,3,3-trifluoro-propylidene)-cyclohexyl]-1,3,8-triaza-spiro[4.5]dec-1-ene-8-sulfonyl}-ethyl)-phenyl]-1-methyl-urea;

(940) 1-[4-(2-{2-[4-(3,3-difluoro-allyl)-cyclohexyl]-4-oxo-1,3,8-triaza-spiro[4.5]dec-1-ene-8-sulfonyl}-ethyl)-3,5-dimethyl-phenyl]-1-methyl-urea;

(941) 1-(3,5-dimethyl-4-{2-[8-oxo-6-(3-trifluoromethoxy-phenyl)-2,5,7-triaza-spiro[3.4]oct-5-ene-2-sulfonyl]-ethyl}-phenyl)-1-methyl-urea;

(942) N-(4-{(E)-1-fluoro-2-[2-(4-methyl-cyclohexyl)-4-oxo-1,3,8-triaza-spiro[4.5]dec-1-ene-8-sulfonyl]-vinyl}-3-methyl-phenyl)-N-methyl-acetamide;

(943) 3-[3-methyl-4-(2-{4-oxo-2-[4-(3,3,3-trifluoro-propyl)-cyclohexyl]-1,3,8-triaza-spiro[4.5]dec-1-ene-8-sulfonyl}-ethyl)-phenyl]-imidazolidine-2,4-dione;

(944) 3-[3-methyl-4-(2-{4-oxo-2-[4-(4,4,4-trifluoro-butyl)-cyclohexyl]-1,3,8-triaza-spiro[4.5]dec-1-ene-8-sulfonyl}-ethyl)-phenyl]-imidazolidine-2,4-dione;

(945) 3-[4-(2-{2-[4-((E)-3,3-difluoro-propenyl)-cyclohexyl]-4-oxo-1,3,8-triaza-spiro[4.5]dec-1-ene-8-sulfonyl}-ethyl)-3-methyl-phenyl]-imidazolidine-2,4-dione;

(946) 3-[4-(2-{2-[4-(3,3-difluoro-allyl)-cyclohexyl]-4-oxo-1,3,8-triaza-spiro[4.5]dec-1-ene-8-sulfonyl}-ethyl)-3-methyl-phenyl]-imidazolidine-2,4-dione;

(947) 3-(3-methyl-4-{2-[4-oxo-2-(4-trifluoromethyl-cyclohexyl)-1,3,8-triaza-spiro[4.5]dec-1-ene-8-sulfonyl]-ethyl}-phenyl)-imidazolidine-2,4-dione;

(948) 3-[3-methyl-4-(2-{4-oxo-2-[4-(2,2,2-trifluoro-ethyl)-cyclohexyl]-1,3,8-triaza-spiro[4.5]dec-1-ene-8-sulfonyl}-ethyl)-phenyl]-imidazolidine-2,4-dione;

(949) 3-(3-methyl-4-{2-[4-oxo-2-((1S,3R)-3-propyl-cyclohexyl)-1,3,8-triaza-spiro[4.5]dec-1-ene-8-sulfonyl]-ethyl}-phenyl)-imidazolidine-2,4-dione;

(950) 3-(3-methyl-4-{2-[2-((1S,3R)-3-methyl-cyclohexyl)-4-oxo-1,3,8-triaza-spiro[4.5]dec-1-ene-8-sulfonyl]-ethyl}-phenyl)-imidazolidine-2,4-dione;

(951) 3-(4-{2-[2-(4,4-dimethyl-cyclohexyl)-4-oxo-1,3,8-triaza-spiro[4.5]dec-1-ene-8-sulfonyl]-ethyl}-3-methyl-phenyl)-imidazolidine-2,4-dione;

(952) 3-(3-methyl-4-{2-[4-oxo-2-(3,3,5,5-tetramethyl-cyclohexyl)-1,3,8-triaza-spiro[4.5]dec-1-ene-8-sulfonyl]-ethyl}-phenyl)-imidazolidine-2,4-dione;

(953) N-(2-chloro-4-{2-[2-(4-ethyl-cyclohexyl)-4-oxo-1,3,8-triaza-spiro[4.5]dec-1-ene-8-sulfonyl]-ethyl}-5-methyl-phenyl)-acetamide;

(954) N-(2-chloro-4-{2-[2-(4-ethyl-cyclohexyl)-4-oxo-1,3,8-triaza-spiro[4.5]dec-1-ene-8-sulfonyl]-ethyl}-3-methyl-phenyl)-acetamide;

(955) N-[4-(2-{2-[4-(3,3-difluoro-propyl)-cyclohexyl]-4-oxo-1,3,8-triaza-spiro[4.5]dec-1-ene-8-sulfonyl}-ethyl)-3-methyl-phenyl]-acetamide;

(956) 3-[4-(2-{2-[4-(3,3-difluoro-propyl)-cyclohexyl]-4-oxo-1,3,8-triaza-spiro[4.5]dec-1-ene-8-sulfonyl}-ethyl)-3-methyl-phenyl]-imidazolidine-2,4-dione;

(957) 2-(2-cyclohexyl-4-oxo-1,3,8-triaza-spiro[4.5]dec-1-ene-8-sulfonyl)-N-phenyl-benzamide;

(958) 8-(2-{2-methyl-4-[4-(1-methyl-piperidin-4-yl)-piperazine-1-carbonyl]-phenyl}-ethanesulfonyl-2-(3-trifluoromethyl-phenyl)-1,3,8-triaza-spiro[4.5]dec-1-en-4-one;

(959) 8-{(E)-2-[4-((R)-3-fluoro-pyrrolidine-1-carbonyl)-2,6-dimethyl-phenyl]-ethenesulfonyl}-2-(3-trifluoromethoxy-phenyl)-1,3,8-triaza-spiro[4.5]dec-1-en-4-one;

(960) 8-{(E)-2-[4-(4-hydroxymethyl-piperidine-1-carbonyl)-2,6-dimethyl-phenyl]-ethenesulfonyl}-2-(3-trifluoromethoxy-phenyl)-1,3,8-triaza-spiro[4.5]dec-1-en-4-one;

(961) 3,5,N,N-tetramethyl-4-{(E)-2-[4-oxo-2-(3-trifluoromethoxy-phenyl)-1,3,8-triaza-spiro[4.5]dec-1-ene-8-sulfonyl]-vinyl}-benzamide;

(962) 3,5-dimethyl-4-{(E)-2-[4-oxo-2-(3-trifluoromethoxy-phenyl)-1,3,8-triaza-spiro[4.5]dec-1-ene-8-sulfonyl]-vinyl}-benzamide;

(963) 8-{(E)-2-[4-(3-fluoro-azetidine-1-carbonyl)-2,6-dimethyl-phenyl]-ethenesulfonyl}-2-(3-trifluoromethoxy-phenyl)-1,3,8-triaza-spiro[4.5]dec-1-en-4-one;

(964) 8-{2-[4-(4-hydroxy-piperidine-1-carbonyl)-2,6-dimethyl-phenyl]-ethanesulfonyl}-2-(3-trifluoromethoxy-phenyl)-1,3,8-triaza-spiro[4.5]dec-1-en-4-one;

(965) 8-{2-[4-(3-hydroxy-azetidine-1-carbonyl)-2,6-dimethyl-phenyl]-ethanesulfonyl}-2-(3-trifluoromethoxy-phenyl)-1,3,8-triaza-spiro[4.5]dec-1-en-4-one;

(966) 8-{2-[4-(4-hydroxymethyl-piperidine-1-carbonyl)-2,6-dimethyl-phenyl]-ethanesulfonyl}-2-(3-trifluoromethoxy-phenyl)-1,3,8-triaza-spiro[4.5]dec-1-en-4-one;

(967) 8-{(E)-2-[2,6-dimethyl-4-(2-oxa-6-aza-spiro[3.3]heptane-6-carbonyl)-phenyl]-ethenesulfonyl}-2-(4-fluoro-3-trifluoromethyl-phenyl)-1,3,8-triaza-spiro[4.5]dec-1-en-4-one;

(968) 8-{(E)-2-[2,6-dimethyl-4-(3-oxo-piperazine-1-carbonyl)-phenyl]-ethenesulfonyl}-2-(4-fluoro-3-trifluoromethyl-phenyl)-1,3,8-triaza-spiro[4.5]dec-1-en-4-one;

(969) 8-{(E)-2-[4-((3R,5S)-3,5-dimethyl-piperazine-1-carbonyl)-2,6-dimethyl-phenyl]-ethenesulfonyl}-2-(4-fluoro-3-trifluoromethyl-phenyl)-1,3,8-triaza-spiro[4.5]dec-1-en-4-one;

(970) 2-(4-fluoro-3-trifluoromethyl-phenyl)-8-{(E)-2-[4-(3-hydroxy-3-methyl-azetidine-1-carbonyl)-2,6-dimethyl-phenyl]-ethenesulfonyl}-1,3,8-triaza-spiro[4.5]dec-1-en-4-one;

(971) 2-(4-fluoro-3-trifluoromethyl-phenyl)-8-{(E)-2-[4-(4-hydroxy-4-hydroxymethyl-piperidine-1-carbonyl)-2,6-dimethyl-phenyl]-ethenesulfonyl}-1,3,8-triaza-spiro[4.5]dec-1-en-4-one;

(972) 8-{(E)-2-[2,6-dimethyl-4-(4-oxo-piperidine-1-carbonyl)-phenyl]-ethenesulfonyl}-2-(4-fluoro-3-trifluoromethyl-phenyl)-1,3,8-triaza-spiro[4.5]dec-1-en-4-one;

(973) 2-[4-(3,3-difluoro-allyl)-cyclohexyl]-8-{2-[4-(4-fluoro-4-hydroxymethyl-piperidine-1-carbonyl)-2-methyl-phenyl]-ethanesulfonyl}-1,3,8-triaza-spiro[4.5]dec-1-en-4-one;

(974) 2-[4-(3,3-difluoro-allyl)-cyclohexyl]-8-{2-[4-(4-fluoromethyl-4-hydroxy-piperidine-1-carbonyl)-2-methyl-phenyl]-ethanesulfonyl}-1,3,8-triaza-spiro[4.5]dec-1-en-4-one;

(975) 2-(4-ethyl-cyclohexyl)-8-(2-{4-[4-(2-fluoro-ethyl)-piperazine-1-carbonyl]-2-methyl-phenyl}-ethanesulfonyl)-1,3,8-triaza-spiro[4.5]dec-1-en-4-one;

(976) 2-(4-ethyl-cyclohexyl)-8-{2-[2-methyl-4-(4-oxetan-3-yl-piperazine-1-carbonyl)-phenyl]-ethanesulfonyl}-1,3,8-triaza-spiro[4.5]dec-1-en-4-one;

(977) 8-{2-[2-methyl-4-(pyrrolidine-1-carbonyl)-phenyl]-ethanesulfonyl}-2-nonyl-1,3,8-triaza-spiro[4.5]dec-1-en-4-one;

(978) 8-{2-[4-(azetidine-1-carbonyl)-2-methyl-phenyl]-ethanesulfonyl}-2-nonyl-1,3,8-triaza-spiro[4.5]dec-1-en-4-one;

(979) 8-{2-[4-((R)-3-hydroxy-pyrrolidine-1-carbonyl)-2-methyl-phenyl]-ethanesulfonyl}-2-nonyl-1,3,8-triaza-spiro[4.5]dec-1-en-4-one;

(980) 8-{2-[2,6-dimethyl-4-(pyrrolidine-1-carbonyl)-phenyl]-ethanesulfonyl}-2-nonyl-1,3,8-triaza-spiro[4.5]dec-1-en-4-one;

(981) 8-{2-[4-((R)-3-hydroxy-pyrrolidine-1-carbonyl)-2,6-dimethyl-phenyl]-ethanesulfonyl}-2-nonyl-1,3,8-triaza-spiro[4.5]dec-1-en-4-one;

(982) 8-{2-[4-(azetidine-1-carbonyl)-2,6-dimethyl-phenyl]-ethanesulfonyl}-2-nonyl-1,3,8-triaza-spiro[4.5]dec-1-en-4-one;

(983) 8-{2-[2,6-dimethyl-4-(piperidine-1-carbonyl)-phenyl]-ethanesulfonyl}-2-nonyl-1,3,8-triaza-spiro[4.5]dec-1-en-4-one;

(984) 8-{2-[4-(4-hydroxy-piperidine-1-carbonyl)-2,6-dimethyl-phenyl]-ethanesulfonyl}-2-nonyl-1,3,8-triaza-spiro[4.5]dec-1-en-4-one;

(985) 8-{2-[4-(3-hydroxy-azetidine-1-carbonyl)-2,6-dimethyl-phenyl]-ethanesulfonyl}-2-nonyl-1,3,8-triaza-spiro[4.5]dec-1-en-4-one;

(986) 8-{2-[2,6-dimethyl-4-(4-methyl-piperazine-1-carbonyl)-phenyl]-ethanesulfonyl}-2-nonyl-1,3,8-triaza-spiro[4.5]dec-1-en-4-one;

(987) N,N-dimethyl-2-(3-methyl-4-{(E)-2-[2-(4-methyl-cyclohexyl)-4-oxo-1,3,8-triaza-spiro[4.5]dec-1-ene-8-sulfonyl]-vinyl}-phenyl)-acetamide;

(988) N-methoxy-2-(3-methyl-4-{(E)-2-[2-(4-methyl-cyclohexyl)-4-oxo-1,3,8-triaza-spiro[4.5]dec-1-ene-8-sulfonyl]-vinyl}-phenyl)-acetamide;

(989) 8-{(E)-2-[4-(4-hydroxy-4-methyl-piperidine-1-carbonyl)-2,6-dimethyl-phenyl]-ethenesulfonyl}-2-[4-(3,3,3-trifluoro-propyl)-cyclohexyl]-1,3,8-triaza-spiro[4.5]dec-1-en-4-one;

(990) 8-{(E)-2-[4-(4-fluoromethyl-4-hydroxy-piperidine-1-carbonyl)-2,6-dimethyl-phenyl]-ethenesulfonyl}-2-[4-(3,3,3-trifluoro-propyl)-cyclohexyl]-1,3,8-triaza-spiro[4.5]dec-1-en-4-one;

(991) 8-{(E)-2-[2,6-dimethyl-4-(4-methyl-piperazine-1-carbonyl)-phenyl]-ethenesulfonyl}-2-[4-(3,3,3-trifluoro-propyl)-cyclohexyl]-1,3,8-triaza-spiro[4.5]dec-1-en-4-one;

(992) 8-{(E)-2-[4-(isoxazolidine-2-carbonyl)-2,6-dimethyl-phenyl]-ethenesulfonyl}-2-[4-(3,3,3-trifluoro-propyl)-cyclohexyl]-1,3,8-triaza-spiro[4.5]dec-1-en-4-one;

(993) 8-((E)-2-{4-[4-((R)-2,3-dihydroxy-propoxy)-piperidine-1-carbonyl]-2,6-dimethyl-phenyl}-ethenesulfonyl)-2-[4-(3,3,3-trifluoro-propyl)-cyclohexyl]-1,3,8-triaza-spiro[4.5]dec-1-en-4-one;

(994) 3,5,N,N-tetramethyl-4-((E)-2-{4-oxo-2-[4-(3,3,3-trifluoro-propyl)-cyclohexyl]-1,3,8-triaza-spiro[4.5]dec-1-ene-8-sulfonyl}-vinyl)-benzamide;

(995) 8-{2-[2,6-dimethyl-4-(4-methyl-piperazine-1-carbonyl)-phenyl]-ethanesulfonyl}-2-[4-(3,3,3-trifluoro-propyl)-cyclohexyl]-1,3,8-triaza-spiro[4.5]dec-1-en-4-one;

(996) 3,5-dimethyl-4-((E)-2-{4-oxo-2-[4-(3,3,3-trifluoro-propyl)-cyclohexyl]-1,3,8-triaza-spiro[4.5]dec-1-ene-8-sulfonyl}-vinyl)-benzoic acid hydrazide;

(997) 8-{(E)-2-[2,6-dimethyl-4-(pyrazolidine-1-carbonyl)-phenyl]-ethenesulfonyl}-2-[4-(3,3,3-trifluoro-propyl)-cyclohexyl]-1,3,8-triaza-spiro[4.5]dec-1-en-4-one;

(998) N-methoxy-3,5,N-trimethyl-4-{(E)-2-[2-(4-methyl-cyclohexyl)-4-oxo-1,3,8-triaza-spiro[4.5]dec-1-ene-8-sulfonyl]-vinyl}-benzamide;

(999) 8-{(E)-2-[4-(4-hydroxy-4-methyl-piperidine-1-carbonyl)-2,6-dimethyl-phenyl]-ethenesulfonyl}-2-(4-methyl-cyclohexyl)-1,3,8-triaza-spiro[4.5]dec-1-en-4-one;

(1000) 8-{(E)-2-[4-(4-fluoromethyl-4-hydroxy-piperidine-1-carbonyl)-2,6-dimethyl-phenyl]-ethenesulfonyl}-2-(4-methyl-cyclohexyl)-1,3,8-triaza-spiro[4.5]dec-1-en-4-one;

(1001) 8-{(E)-2-[4-(isoxazolidine-2-carbonyl)-2,6-dimethyl-phenyl]-ethenesulfonyl}-2-(4-methyl-cyclohexyl)-1,3,8-triaza-spiro[4.5]dec-1-en-4-one;

(1002) 8-{(E)-2-[4-(1,1-dioxo-1$\lambda^6$-thiomorpholine-4-carbonyl)-2,6-dimethyl-phenyl]-ethenesulfonyl}-2-(4-methyl-cyclohexyl)-1,3,8-triaza-spiro[4.5]dec-1-en-4-one;

(1003) 3,5,N,N-tetramethyl-4-{(E)-2-[2-(4-methyl-cyclohexyl)-4-oxo-1,3,8-triaza-spiro[4.5]dec-1-ene-8-sulfonyl]-vinyl}-benzamide;

(1006) 2-cyclohexyl-8-{(E)-2-[4-(4-hydroxy-4-trifluoromethyl-piperidine-1-carbonyl)-2,6-dimethyl-phenyl]-ethenesulfonyl}-1,3,8-triaza-spiro[4.5]dec-1-en-4-one;

(1007) 2-cyclohexyl-8-{(E)-2-[2,6-dimethyl-4-(2-oxo-oxazolidine-3-carbonyl)-phenyl]-ethenesulfonyl}-1,3,8-triaza-spiro[4.5]dec-1-en-4-one;

(1008) 2-(4-butyl-cyclohexyl)-8-((E)-2-{4-[4-(2-hydroxy-ethoxy)-piperidine-1-carbonyl]-2,6-dimethyl-phenyl}-ethenesulfonyl)-1,3,8-triaza-spiro[4.5]dec-1-en-4-one;

(1009) 2-(4-butyl-cyclohexyl)-8-[(E)-2-(4-{4-[2-(2-hydroxy-ethoxy)-ethoxy]-piperidine-1-carbonyl}-2,6-dimethyl-phenyl)-ethenesulfonyl]-1,3,8-triaza-spiro[4.5]dec-1-en-4-one;

(1010) 8-((E)-2-{4-[4-((R)-2,3-dihydroxy-propoxy)-piperidine-1-carbonyl]-2,6-dimethyl-phenyl}-ethenesulfonyl)-2-(9,9,9-trifluoro-nonyl)-1,3,8-triaza-spiro[4.5]dec-1-en-4-one;

(1011) 2-amino-N-(3,5-dimethyl-4-{(E)-2-[4-oxo-2-(3-trifluoromethoxy-phenyl)-1,3,8-triaza-spiro[4.5]dec-1-ene-8-sulfonyl]-vinyl}-phenyl)-N-methyl-acetamide;

(1012) (3,5-dimethyl-4-{(E)-2-[4-oxo-2-(3-trifluoromethoxy-phenyl)-1,3,8-triaza-spiro[4.5]dec-1-ene-8-sulfonyl]-vinyl}-phenyl)-methyl-carbamic acid 2-hydroxy-ethyl ester;

(1013) 1-(3,5-dimethyl-4-{(E)-2-[4-oxo-2-(3-trifluoromethoxy-phenyl)-1,3,8-triaza-spiro[4.5]dec-1-ene-8-sulfonyl]-vinyl}-phenyl)-1,3,3-trimethyl-urea;

(1014) 1-(3,5-dimethyl-4-{(E)-2-[4-oxo-2-(3-trifluoromethoxy-phenyl)-1,3,8-triaza-spiro[4.5]dec-1-ene-8-sulfonyl]-vinyl}-phenyl)-1,3-dimethyl-urea;

(1015) 1-(3,5-dimethyl-4-{(E)-2-[4-oxo-2-(3-trifluoromethoxy-phenyl)-1,3,8-triaza-spiro[4.5]dec-1-ene-8-sulfonyl]-vinyl}-phenyl)-1-methyl-urea;

(1016) 8-[(E)-2-(2,6-dimethyl-4-methylamino-phenyl)-ethenesulfonyl]-2-(3-trifluoromethylsulfanyl-phenyl)-1,3,8-triaza-spiro[4.5]dec-1-en-4-one;

(1017) 1-(4-{(E)-2-[2-(4-fluoro-3-trifluoromethyl-phenyl)-4-oxo-1,3,8-triaza-spiro[4.5]dec-1-ene-8-sulfonyl]-vinyl}-3,5-dimethyl-phenyl)-1-methyl-urea;

(1018) 1-[3,5-dimethyl-4-((E)-2-{4-oxo-2-[3-(1,1,2,2-tetrafluoro-ethoxy)-phenyl]-1,3,8-triaza-spiro[4.5]dec-1-ene-8-sulfonyl}-vinyl)-phenyl]-1-methyl-urea;

(1019) 1-[3,5-dimethyl-4-((E)-2-{4-oxo-2-[3-(4,4,4-trifluoro-butoxy)-phenyl]-1,3,8-triaza-spiro[4.5]dec-1-ene-8-sulfonyl}-vinyl)-phenyl]-1-methyl-urea;

(1020) 1-[3,5-dimethyl-4-((E)-2-{4-oxo-2-[4-(4,4,4-trifluoro-butoxy)-phenyl]-1,3,8-triaza-spiro[4.5]dec-1-ene-8-sulfonyl}-vinyl)-phenyl]-1-methyl-urea;

(1021) 1-(3,5-dimethyl-4-{(E)-2-[4-oxo-2-(4-pentyl-phenyl)-1,3,8-triaza-spiro[4.5]dec-1-ene-8-sulfonyl]-vinyl}-phenyl)-1-methyl-urea;

(1022) 1-(3,5-dimethyl-4-{(E)-2-[2-(7-methylsulfanyl-heptyl)-4-oxo-1,3,8-triaza-spiro[4.5]dec-1-ene-8-sulfonyl]-vinyl}-phenyl)-1-methyl-urea;

(1023) 1-[3,5-dimethyl-4-((E)-2-{2-[8-(3-methyl-oxetan-3-yl)-octyl]-4-oxo-1,3,8-triaza-spiro[4.5]dec-1-ene-8-sulfonyl}-vinyl)-phenyl]-1-methyl-urea;

(1024) 1-{3,5-dimethyl-4-[(E)-2-(2-non-4-ynyl-4-oxo-1,3,8-triaza-spiro[4.5]dec-1-ene-8-sulfonyl)-vinyl]-phenyl}-1-methyl-urea;

(1025) 1-{3,5-dimethyl-4-[(E)-2-(2-non-3-ynyl-4-oxo-1,3,8-triaza-spiro[4.5]dec-1-ene-8-sulfonyl)-vinyl]-phenyl}-1-methyl-urea;

(1026) 1-[3,5-dimethyl-4-((E)-2-{2-[10-(3-methyl-oxetan-3-yl)-decyl]-4-oxo-1,3,8-triaza-spiro[4.5]dec-1-ene-8-sulfonyl}-vinyl)-phenyl]-1-methyl-urea;

(1027) 1-{3,5-dimethyl-4-[(E)-2-(2-non-1-ynyl-4-oxo-1,3,8-triaza-spiro[4.5]dec-1-ene-8-sulfonyl)-vinyl]-phenyl}-1-methyl-urea;

(1028) 1-(4-{2-[2-(4-fluoro-3-trifluoromethoxy-phenyl)-4-oxo-1,3,8-triaza-spiro[4.5]dec-1-ene-8-sulfonyl]-ethyl}-3,5-dimethyl-phenyl)-1-methyl-urea;

(1029) 1-(4-{2-[2-(2,2-difluoro-benzo[1,3]dioxol-5-yl)-4-oxo-1,3,8-triaza-spiro[4.5]dec-1-ene-8-sulfonyl]-ethyl}-3,5-dimethyl-phenyl)-1-methyl-urea;

(1030) 1-(4-{2-[2-(4-tert-butyl-phenyl)-4-oxo-1,3,8-triaza-spiro[4.5]dec-1-ene-8-sulfonyl]-ethyl}-3,5-dimethyl-phenyl)-1-methyl-urea;

(1031) 1-[3,5-dimethyl-4-(2-{2-[8-(3-methyl-oxetan-3-yl)-octyl]-4-oxo-1,3,8-triaza-spiro[4.5]dec-1-ene-8-sulfonyl}-ethyl)-phenyl]-1-methyl-urea;

(1032) 1-[3,5-dimethyl-4-(2-{2-[10-(3-methyl-oxetan-3-yl)-decyl]-4-oxo-1,3,8-triaza-spiro[4.5]dec-1-ene-8-sulfonyl}-ethyl)-phenyl]-1-methyl-urea;

(1033) 2-(8-{2-[4-(tert-butoxycarbonyl-methyl-amino)-2,6-dimethyl-phenyl]-ethanesulfonyl}-4-oxo-1,3,8-triaza-spiro[4.5]dec-1-en-2-yl)-pyrrolidine-1-carboxylic acid tert-butyl ester;

(1034) (4-{2-[2-(1,1-difluoro-ethyl)-4-oxo-1,3,8-triaza-spiro[4.5]dec-1-ene-8-sulfonyl]-ethyl}-3,5-dimethyl-phenyl)-methyl-carbamic acid tert-butyl ester;

(1035) 8-[2-(2,6-dimethyl-4-methylamino-phenyl)-ethanesulfonyl]-2-(8,8,9,9,9-pentafluoro-nonyl)-1,3,8-triaza-spiro[4.5]dec-1-en-4-one;

(1036) 8-[2-(2,6-dimethyl-4-methylamino-phenyl)-ethanesulfonyl]-2-(3-trifluoromethylsulfanyl-phenyl)-1,3,8-triaza-spiro[4.5]dec-1-en-4-one;

(1037) 8-[2-(2,6-dimethyl-4-methylamino-phenyl)-ethane-sulfonyl]-2-(4-isopropylidene-cyclohexyl)-1,3,8-triaza-spiro[4.5]dec-1-en-4-one;

(1038) 1-[3,5-dimethyl-4-(2-{4-oxo-2-[3-(1,1,2,2-tetrafluoro-ethoxy)-phenyl]-1,3,8-triaza-spiro[4.5]dec-1-ene-8-sulfonyl}-ethyl)-phenyl]-1-methyl-urea;

(1039) 1-(3,5-dimethyl-4-{2-[4-oxo-2-(5,6,7,8-tetrahydro-naphthalen-2-yl)-1,3,8-triaza-spiro[4.5]dec-1-ene-8-sulfonyl]-ethyl}-phenyl)-1-methyl-urea;

(1040) 1-(4-{2-[2-((1S,3S,5R)-3,5-dimethyl-cyclohexyl)-4-oxo-1,3,8-triaza-spiro[4.5]dec-1-ene-8-sulfonyl]-ethyl}-3,5-dimethyl-phenyl)-1-methyl-urea;

(1041) 1-(3,5-dimethyl-4-{2-[4-oxo-2-(1-propyl-butyl)-1,3,8-triaza-spiro[4.5]dec-1-ene-8-sulfonyl]-ethyl}-phenyl)-1-methyl-urea;

(1042) 1-[3,5-dimethyl-4-(2-{4-oxo-2-[4-(2,2,3,3,3-pentafluoro-propyl)-cyclohexyl]-1,3,8-triaza-spiro[4.5]dec-1-ene-8-sulfonyl}-ethyl)-phenyl]-1-methyl-urea;

(1043) 1-(3,5-dimethyl-4-{2-[4-oxo-2-(6,6,7,7,7-pentafluoro-heptyl)-1,3,8-triaza-spiro[4.5]dec-1-ene-8-sulfonyl]-ethyl}-phenyl)-1-methyl-urea;

(1044) N-(3,5-dimethyl-4-{2-[4-oxo-2-(7,7,7-trifluoro-heptyl)-1,3,8-triaza-spiro[4.5]dec-1-ene-8-sulfonyl]-ethyl}-phenyl)-N-methyl-acetamide;

(1045) 1-(3,5-dimethyl-4-{2-[4-oxo-2-(7,7,7-trifluoro-heptyl)-1,3,8-triaza-spiro[4.5]dec-1-ene-8-sulfonyl]-ethyl}-phenyl)-1-methyl-urea;

(1046) 1-(3,5-dimethyl-4-{2-[4-oxo-2-(9,9,9-trifluoro-nonyl)-1,3,8-triaza-spiro[4.5]dec-1-ene-8-sulfonyl]-ethyl}-phenyl)-1-methyl-urea;

(1047) N-(3,5-dimethyl-4-{2-[4-oxo-2-(9,9,9-trifluoro-nonyl)-1,3,8-triaza-spiro[4.5]dec-1-ene-8-sulfonyl]-ethyl}-phenyl)-N-methyl-acetamide;

(1048) 1-[3,5-dimethyl-4-(2-{4-oxo-2-[1-(4,4,4-trifluoro-butyl)-cyclopropyl]-1,3,8-triaza-spiro[4.5]dec-1-ene-8-sulfonyl}-ethyl)-phenyl]-1-methyl-urea;

(1050) 1-(3,5-dimethyl-4-{2-[4-oxo-2-(3-trifluoromethyl-cyclohexyl)-1,3,8-triaza-spiro[4.5]dec-1-ene-8-sulfonyl]-ethyl}-phenyl)-1-methyl-urea;

(1051) 1-(4-{2-[2-(cis-3,4-dimethyl-cyclopentyl)-4-oxo-1,3,8-triaza-spiro[4.5]dec-1-ene-8-sulfonyl]-ethyl}-3,5-dimethyl-phenyl)-1-methyl-urea;

(1052) 1-{4-[2-(2-dicyclopropylmethyl-4-oxo-1,3,8-triaza-spiro[4.5]dec-1-ene-8-sulfonyl)-ethyl]-3,5-dimethyl-phenyl}-1-methyl-urea;

(1053) 1-{4-[2-(2-bicyclo[3.3.1]non-9-yl-4-oxo-1,3,8-triaza-spiro[4.5]dec-1-ene-8-sulfonyl)-ethyl]-3,5-dimethyl-phenyl}-1-methyl-urea;

(1054) 1-{4-[2-((1R,5S)-2-bicyclo[3.2.1]oct-3-yl-4-oxo-1,3,8-triaza-spiro[4.5]dec-1-ene-8-sulfonyl)-ethyl]-3,5-dimethyl-phenyl}-1-methyl-urea;

(1055) 1-(3,5-dimethyl-4-{2-[2-(3-methyl-cyclopentyl)-4-oxo-1,3,8-triaza-spiro[4.5]dec-1-ene-8-sulfonyl]-ethyl}-phenyl)-1-methyl-urea;

(1056) 1-{4-[2-(2-bicyclo[2.2.1]hept-7-yl-4-oxo-1,3,8-triaza-spiro[4.5]dec-1-ene-8-sulfonyl)-ethyl]-3,5-dimethyl-phenyl}-1-methyl-urea;

(1057) 1-(4-{2-[2-((1S,2S)-2-hexyl-cyclohexyl)-4-oxo-1,3,8-triaza-spiro[4.5]dec-1-ene-8-sulfonyl]-ethyl}-3,5-dimethyl-phenyl)-1-methyl-urea;

(1058) 1-{3,5-dimethyl-4-[2-(4-oxo-2-spiro[2.5]oct-6-yl-1,3,8-triaza-spiro[4.5]dec-1-ene-8-sulfonyl)-ethyl]-phenyl}-1-methyl-urea;

(1059) 1-(4-{2-[2-(4-difluoromethylene-cyclohexyl)-4-oxo-1,3,8-triaza-spiro[4.5]dec-1-ene-8-sulfonyl]-ethyl}-3,5-dimethyl-phenyl)-1-methyl-urea;

(1060) N-[4-(2-{2-[4-(2,2-difluoro-ethyl)-cyclohexyl]-4-oxo-1,3,8-triaza-spiro[4.5]dec-1-ene-8-sulfonyl}-ethyl)-3-methyl-phenyl]-acetamide;

(1061) N-[4-(2-{2-[4-(2-fluoro-ethyl)-cyclohexyl]-4-oxo-1,3,8-triaza-spiro[4.5]dec-1-ene-8-sulfonyl}-ethyl)-3-methyl-phenyl]-acetamide;

(1062) N-(4-{2-[2-(4-butyl-4-fluoro-cyclohexyl)-4-oxo-1,3,8-triaza-spiro[4.5]dec-1-ene-8-sulfonyl]-ethyl}-3-methyl-phenyl)-acetamide;

(1063) N-[4-(2-{2-[4-((E)-3-fluoro-propenyl)-cyclohexyl]-4-oxo-1,3,8-triaza-spiro[4.5]dec-1-ene-8-sulfonyl}-ethyl)-3-methyl-phenyl]-acetamide;

(1064) N-[4-(2-{2-[4-(3-fluoro-propyl)-cyclohexyl]-4-oxo-1,3,8-triaza-spiro[4.5]dec-1-ene-8-sulfonyl}-ethyl)-3-methyl-phenyl]-acetamide;

(1065) N-[4-(2-{2-[4-(3-chloro-propyl)-cyclohexyl]-4-oxo-1,3,8-triaza-spiro[4.5]dec-1-ene-8-sulfonyl}-ethyl)-3-methyl-phenyl]-acetamide;

(1066) N-[4-(2-{2-[4-(3-fluoro-propylidene)-cyclohexyl]-4-oxo-1,3,8-triaza-spiro[4.5]dec-1-ene-8-sulfonyl}-ethyl)-3-methyl-phenyl]-acetamide;

(1067) N-[4-(2-{2-[4-(3,3-difluoro-allyl)-cyclohexyl]-4-oxo-1,3,8-triaza-spiro[4.5]dec-1-ene-8-sulfonyl}-ethyl)-3-methyl-phenyl]-acetamide;

(1068) N-[4-(2-{2-[4-(3,3-difluoro-allyl)-cyclohexyl]-4-oxo-1,3,8-triaza-spiro[4.5]dec-1-ene-8-sulfonyl}-ethyl)-3-methyl-phenyl]-acetamide;

(1069) N-[3-methyl-4-(2-{4-oxo-2-[4-(2,2,3,3,3-pentafluoro-propyl)-cyclohexyl]-1,3,8-triaza-spiro[4.5]dec-1-ene-8-sulfonyl}-ethyl)-phenyl]-acetamide;

(1070) N-[4-(2-{2-[4-((E)-3-fluoro-allyl)-cyclohexyl]-4-oxo-1,3,8-triaza-spiro[4.5]dec-1-ene-8-sulfonyl}-ethyl)-3-methyl-phenyl]-acetamide;

(1071) N-[4-(2-{2-[4-(2,2-difluoro-ethyl)-cyclohexyl]-4-oxo-1,3,8-triaza-spiro[4.5]dec-1-ene-8-sulfonyl}-ethyl)-3-methyl-phenyl]-acetamide;

(1072) N-[4-(2-{2-[4-(2-fluoro-ethyl)-cyclohexyl]-4-oxo-1,3,8-triaza-spiro[4.5]dec-1-ene-8-sulfonyl}-ethyl)-3-methyl-phenyl]-acetamide;

(1073) N-[4-(2-{2-[4-fluoro-4-(3-fluoro-propyl)-cyclohexyl]-4-oxo-1,3,8-triaza-spiro[4.5]dec-1-ene-8-sulfonyl}-ethyl)-3-methyl-phenyl]-acetamide;

(1074) N-(4-{2-[2-(4-ethynyl-cyclohexyl)-4-oxo-1,3,8-triaza-spiro[4.5]dec-1-ene-8-sulfonyl]-ethyl}-3-methyl-phenyl)-acetamide;

(1075) N-(4-{2-[2-(4-difluoromethyl-cyclohexyl)-4-oxo-1,3,8-triaza-spiro[4.5]dec-1-ene-8-sulfonyl]-ethyl}-3-methyl-phenyl)-acetamide;

(1076) N-[4-(2-{2-[4-(3,3-difluoro-propylidene)-cyclohexyl]-4-oxo-1,3,8-triaza-spiro[4.5]dec-1-ene-8-sulfonyl}-ethyl)-3-methyl-phenyl]-acetamide;

(1077) N-[4-(2-{2-[4-(2-fluoro-propyl)-cyclohexyl]-4-oxo-1,3,8-triaza-spiro[4.5]dec-1-ene-8-sulfonyl}-ethyl)-3-methyl-phenyl]-acetamide;

(1078) N-[4-(2-{2-[4-(1-fluoro-1-methyl-ethyl)-cyclohexyl]-4-oxo-1,3,8-triaza-spiro[4.5]dec-1-ene-8-sulfonyl}-ethyl)-3-methyl-phenyl]-acetamide;

(1079) N-(4-{2-[2-(4-butylidene-cyclohexyl)-4-oxo-1,3,8-triaza-spiro[4.5]dec-1-ene-8-sulfonyl]-ethyl}-3-methyl-phenyl)-acetamide;

(1080) N-[3-methyl-4-(2-{4-oxo-2-[4-(2,2,3,3,3-pentafluoro-propyl)-cyclohexyl]-1,3,8-triaza-spiro[4.5]dec-1-ene-8-sulfonyl}-ethyl)-phenyl]-acetamide;

(1081) 1-{3,5-dimethyl-4-[2-(2-non-4-ynyl-4-oxo-1,3,8-triaza-spiro[4.5]dec-1-ene-8-sulfonyl)-ethyl]-phenyl}-1-methyl-urea;

(1082) 1-{3,5-dimethyl-4-[2-(2-non-3-ynyl-4-oxo-1,3,8-triaza-spiro[4.5]dec-1-ene-8-sulfonyl)-ethyl]-phenyl}-1-methyl-urea;

(1083) 1-{3,5-dimethyl-4-[2-(2-non-1-ynyl-4-oxo-1,3,8-triaza-spiro[4.5]dec-1-ene-8-sulfonyl)-ethyl]-phenyl}-1-methyl-urea;

(1084) 1-(3,5-dimethyl-4-{1-[4-oxo-2-(3-trifluoromethoxy-phenyl)-1,3,8-triaza-spiro[4.5]dec-1-ene-8-sulfonyl]-cyclopropylmethyl}-phenyl)-1-methyl-urea;

(1085) 1-(4-{2,2-difluoro-2-[4-oxo-2-(3-trifluoromethoxy-phenyl)-1,3,8-triaza-spiro[4.5]dec-1-ene-8-sulfonyl]-ethyl}-3,5-dimethyl-phenyl)-1-methyl-urea;

(1086) 1-{4-[2,2-difluoro-2-(2-nonyl-4-oxo-1,3,8-triaza-spiro[4.5]dec-1-ene-8-sulfonyl)-ethyl]-3,5-dimethyl-phenyl}-1-methyl-urea;

(1087) 1-{3,5-dimethyl-4-[2-(4-oxo-2-[1,1';2',1"]terphenyl-3-yl-1,3,8-triaza-spiro[4.5]dec-1-ene-8-sulfonyl)-ethyl]-phenyl}-1-methyl-urea;

(1088) 1-[3,5-dimethyl-4-((E)-2-{4-oxo-2-[4-(4,4,4-trifluoro-butyl)-phenyl]-1,3,8-triaza-spiro[4.5]dec-1-ene-8-sulfonyl}-vinyl)-phenyl]-1-methyl-urea;

(1089) 1-[3,5-dimethyl-4-((E)-2-{4-oxo-2-[3-(4,4,4-trifluoro-butyl)-phenyl]-1,3,8-triaza-spiro[4.5]dec-1-ene-8-sulfonyl}-vinyl)-phenyl]-1-methyl-urea;

(1090) 1-(3,5-dimethyl-4-{2-[4-oxo-2-(3-trifluoromethoxy-phenyl)-1,3,8-triaza-spiro[4.5]dec-1-ene-8-sulfonyl]-propyl}-phenyl)-1-methyl-urea;

(1091) 2-[4-fluoro-3-(4,4,5,5,5-pentafluoro-pentyloxy)-phenyl]-8-{(E)-2-[4-(4-hydroxy-piperidine-1-carbonyl)-2,6-dimethyl-phenyl]-ethenesulfonyl}-1,3,8-triaza-spiro[4.5]dec-1-en-4-one;

(1092) 2-[4-fluoro-3-(4,4,5,5,5-pentafluoro-pentyloxy)-phenyl]-8-{(E)-2-[4-(4-hydroxy-4-methyl-piperidine-1-carbonyl)-2,6-dimethyl-phenyl]-ethenesulfonyl}-1,3,8-triaza-spiro[4.5]dec-1-en-4-one;

(1093) 2-(4-chloro-3-trifluoromethoxy-phenyl)-8-{(E)-2-[4-(4-hydroxy-4-methyl-piperidine-1-carbonyl)-2,6-dimethyl-phenyl]-ethenesulfonyl}-1,3,8-triaza-spiro[4.5]dec-1-en-4-one;

(1094) 2-(3-fluoro-4-trifluoromethoxy-phenyl)-8-{(E)-2-[4-(4-hydroxy-4-methyl-piperidine-1-carbonyl)-2,6-dimethyl-phenyl]-ethenesulfonyl}-1,3,8-triaza-spiro[4.5]dec-1-en-4-one;

(1095) 2-(3,4-bis-trifluoromethyl-phenyl)-8-{(E)-2-[4-(4-hydroxy-4-methyl-piperidine-1-carbonyl)-2,6-dimethyl-phenyl]-ethenesulfonyl}-1,3,8-triaza-spiro[4.5]dec-1-en-4-one;

(1096) 8-{(E)-2-[4-(4-hydroxy-4-methyl-piperidine-1-carbonyl)-2,6-dimethyl-phenyl]-ethenesulfonyl}-2-[3-(4,4,5,5,5-pentafluoro-pentyloxy)-phenyl]-1,3,8-triaza-spiro[4.5]dec-1-en-4-one;

(1097) 8-{(E)-2-[4-(4-hydroxy-4-methyl-piperidine-1-carbonyl)-2,6-dimethyl-phenyl]-ethenesulfonyl}-2-[3-(2,2,2-trifluoro-ethyl)-phenyl]-1,3,8-triaza-spiro[4.5]dec-1-en-4-one;

(1098) 2-(4-fluoro-3-methyl-phenyl)-8-{(E)-2-[4-(4-hydroxy-4-methyl-piperidine-1-carbonyl)-2,6-dimethyl-phenyl]-ethenesulfonyl}-1,3,8-triaza-spiro[4.5]dec-1-en-4-one;

(1099) 2-(4-fluoro-3-trifluoromethoxy-phenyl)-8-{(E)-2-[4-(4-hydroxy-4-methyl-piperidine-1-carbonyl)-2,6-dimethyl-phenyl]-ethenesulfonyl}-1,3,8-triaza-spiro[4.5]dec-1-en-4-one;

(1100) 8-{(E)-2-[4-(4-hydroxy-4-methyl-piperidine-1-carbonyl)-2,6-dimethyl-phenyl]-ethenesulfonyl}-2-[3-(1,1,2,2-tetrafluoro-ethoxy)-phenyl]-1,3,8-triaza-spiro[4.5]dec-1-en-4-one;

(1101) 8-{1,1-difluoro-2-[4-(4-hydroxy-piperidine-1-carbonyl)-2,6-dimethyl-phenyl]-ethanesulfonyl}-2-(3-trifluoromethoxy-phenyl)-1,3,8-triaza-spiro[4.5]dec-1-en-4-one;

(1102) 2-(4-fluoro-3-trifluoromethoxy-phenyl)-8-{(E)-2-[4-(3-hydroxy-azetidine-1-carbonyl)-2,6-dimethyl-phenyl]-ethenesulfonyl}-1,3,8-triaza-spiro[4.5]dec-1-en-4-one;

(1103) 8-{(E)-2-[4-((R)-2,3-dihydroxy-propoxy)-2,6-dimethyl-phenyl]-ethenesulfonyl}-2-[3-(4,4,5,5,5-pentafluoro-pentyloxy)-phenyl]-1,3,8-triaza-spiro[4.5]dec-1-en-4-one;

(1104) 6-(4-methyl-cyclohexyl)-2-(2-naphthalen-1-yl-ethanesulfonyl)-2,5,7-triaza-spiro[3.4]oct-5-en-8-one;

(1106) (11-{8-[(E)-2-(2,6-dimethyl-4-methylamino-phenyl)-ethenesulfonyl]-4-oxo-1,3,8-triaza-spiro[4.5]dec-1-en-2-yl}-undecyl)-carbamic acid tert-butyl ester;

(1107) 8-[(E)-2-(2,6-dimethyl-4-methylamino-phenyl)-ethenesulfonyl]-2-(9-hydroxy-nonyl)-1,3,8-triaza-spiro[4.5]dec-1-en-4-one;

(1108) 1-(3,5-dimethyl-4-{(E)-2-[4-oxo-2-((1S,3R)-3-propyl-cyclohexyl)-1,3,8-triaza-spiro[4.5]dec-1-ene-8-sulfonyl]-vinyl}-phenyl)-1-methyl-urea;

(1109) 14-(8-{(E)-2-[2,6-dimethyl-4-(1-methyl-ureido)-phenyl]-ethenesulfonyl}-4-oxo-1,3,8-triaza-spiro[4.5]dec-1-en-2-yl)-tetradecanoic acid;

(1110) 1-(3,5-dimethyl-4-{(E)-2-[2-(4-[1,1,1-$^{2}H_{3}$]methyl-[4-$^{2}H_{1}$]cyclohexyl)-4-oxo-1,3,8-triaza-spiro[4.5]dec-1-ene-8-sulfonyl]-vinyl}-phenyl)-1-methyl-urea;

(1111) 1-(4-{(E)-2-[2-(4-fluoro-3-trifluoromethoxy-phenyl)-4-oxo-1,3,8-triaza-spiro[4.5]dec-1-ene-8-sulfonyl]-vinyl}-3,5-dimethyl-phenyl)-1-methyl-urea;

(1112) 1-(3,5-dimethyl-4-{(E)-2-[2-(3-nonafluorobutyl-phenyl)-4-oxo-1,3,8-triaza-spiro[4.5]dec-1-ene-8-sulfonyl]-vinyl}-phenyl)-1-methyl-urea;

(1113) 1-(4-{(E)-2-[2-(4-chloro-3-trifluoromethyl-phenyl)-4-oxo-1,3,8-triaza-spiro[4.5]dec-1-ene-8-sulfonyl]-vinyl}-3,5-dimethyl-phenyl)-1-methyl-urea;

(1114) 1-(3,5-dimethyl-4-{(E)-2-[4-oxo-2-(4'-propyl-biphenyl-3-yl)-1,3,8-triaza-spiro[4.5]dec-1-ene-8-sulfonyl]-vinyl}-phenyl)-1-methyl-urea;

(1115) 1-(4-{(E)-2-[2-(6-ethoxy-hexyl)-4-oxo-1,3,8-triaza-spiro[4.5]dec-1-ene-8-sulfonyl]-vinyl}-3,5-dimethyl-phenyl)-1-methyl-urea;

(1116) 1-[3,5-dimethyl-4-((E)-2-{4-oxo-2-[3-(6,6,6-trifluoro-hexyl)-phenyl]-1,3,8-triaza-spiro[4.5]dec-1-ene-8-sulfonyl}-vinyl)-phenyl]-1-methyl-urea;

(1117) 1-[3,5-dimethyl-4-((E)-2-{4-oxo-2-[4-(6,6,6-trifluoro-hexyl)-phenyl]-1,3,8-triaza-spiro[4.5]dec-1-ene-8-sulfonyl}-vinyl)-phenyl]-1-methyl-urea;

(1118) 1-(4-{(E)-2-[2-(11-fluoro-undecyl)-4-oxo-1,3,8-triaza-spiro[4.5]dec-1-ene-8-sulfonyl]-vinyl}-3,5-dimethyl-phenyl)-1-methyl-urea;

(1119) 1-{4-[(E)-2-(2-hex-5-enyl-4-oxo-1,3,8-triaza-spiro[4.5]dec-1-ene-8-sulfonyl)-vinyl]-3,5-dimethyl-phenyl}-1-methyl-urea;

(1120) 1-(3,5-dimethyl-4-{(E)-2-[4-oxo-2-((E)-6-phenyl-hex-5-enyl)-1,3,8-triaza-spiro[4.5]dec-1-ene-8-sulfonyl]-vinyl}-phenyl)-1-methyl-urea;

(1121) 1-(3,5-dimethyl-4-{(E)-2-[4-oxo-2-((E)-9-phenyl-non-8-enyl)-1,3,8-triaza-spiro[4.5]dec-1-ene-8-sulfonyl]-vinyl}-phenyl)-1-methyl-urea;

(1122) 1-(3,5-dimethyl-4-{(E)-2-[4-oxo-2-(5-propylsulfanyl-pentyl)-1,3,8-triaza-spiro[4.5]dec-1-ene-8-sulfonyl]-vinyl}-phenyl)-1-methyl-urea;

(1123) 1-(4-{(E)-2-[2-(7-methoxy-heptyl)-4-oxo-1,3,8-triaza-spiro[4.5]dec-1-ene-8-sulfonyl]-vinyl}-3,5-dimethyl-phenyl)-1-methyl-urea;

(1124) 1-(3,5-dimethyl-4-{(E)-2-[4-oxo-2-(5-propoxy-pentyl)-1,3,8-triaza-spiro[4.5]dec-1-ene-8-sulfonyl]-vinyl}-phenyl)-1-methyl-urea;

(1125) 1-(4-{(E)-2-[2-(11,11-difluoro-undecyl)-4-oxo-1,3,8-triaza-spiro[4.5]dec-1-ene-8-sulfonyl]-vinyl}-3,5-dimethyl-phenyl)-1-methyl-urea;

(1126) 1-(3,5-dimethyl-4-{(E)-2-[4-oxo-2-(3-propyl-nonyl)-1,3,8-triaza-spiro[4.5]dec-1-ene-8-sulfonyl]-vinyl}-phenyl)-1-methyl-urea;

(1127) 1-(3,5-dimethyl-4-{(E)-2-[4-oxo-2-(2-propyl-benzofuran-6-yl)-1,3,8-triaza-spiro[4.5]dec-1-ene-8-sulfonyl]-vinyl}-phenyl)-1-methyl-urea;

(1128) 1-(4-{(E)-2-[2-(3-methoxy-4-pentyl-phenyl)-4-oxo-1,3,8-triaza-spiro[4.5]dec-1-ene-8-sulfonyl]-vinyl}-3,5-dimethyl-phenyl)-1-methyl-urea;

(1129) 1-(4-{(E)-2-[2-(4-[1,1,2,2,2-$^2H_5$]ethyl-cyclohex-3-enyl)-4-oxo-1,3,8-triaza-spiro[4.5]dec-1-ene-8-sulfonyl]-vinyl}-3,5-dimethyl-phenyl)-1-methyl-urea;

(1130) 1-(4-{(E)-2-[2-(4-[1,1,2,2,2-$^2H_5$]ethyl-[4-$^2H_1$]cyclohexyl)-4-oxo-1,3,8-triaza-spiro[4.5]dec-1-ene-8-sulfonyl]-vinyl}-3,5-dimethyl-phenyl)-1-methyl-urea;

(1131) 12-(8-{(E)-2-[2,6-dimethyl-4-(1-methyl-ureido)-phenyl]-ethenesulfonyl}-4-oxo-1,3,8-triaza-spiro[4.5]dec-1-en-2-yl)-dodecanoic acid;

(1132) 12-(8-{(E)-2-[2,6-dimethyl-4-(1-methyl-ureido)-phenyl]-ethenesulfonyl}-4-oxo-1,3,8-triaza-spiro[4.5]dec-1-en-2-yl)-dodecanoic acid ethyl ester;

(1133) 1-(3,5-dimethyl-4-{(E)-2-[4-oxo-2-(5-phenyl-pentyl)-1,3,8-triaza-spiro[4.5]dec-1-ene-8-sulfonyl]-vinyl}-phenyl)-1-methyl-urea;

(1134) 1-(3,5-dimethyl-4-{(Z)-2-[4-oxo-2-(5-phenyl-pentyl)-1,3,8-triaza-spiro[4.5]dec-1-ene-8-sulfonyl]-vinyl}-phenyl)-1-methyl-urea;

(1135) 1-[3,5-dimethyl-4-(2-{4-oxo-2-[3-(4,4,5,5,5-pentafluoro-pentyloxy)-phenyl]-1,3,8-triaza-spiro[4.5]dec-1-ene-8-sulfonyl}-ethyl)-phenyl]-1-methyl-urea;

(1136) 1-(3,5-dimethyl-4-{2-[4-oxo-2-(3'-propyl-biphenyl-3-yl)-1,3,8-triaza-spiro[4.5]dec-1-ene-8-sulfonyl]-ethyl}-phenyl)-1-methyl-urea;

(1137) 1-(3,5-dimethyl-4-{2-[4-oxo-2-(4-trimethylsilanyl-cyclohexyl)-1,3,8-triaza-spiro[4.5]dec-1-ene-8-sulfonyl]-ethyl}-phenyl)-1-methyl-urea;

(1138) 1-(4-{2-[2-((1R,3R,5S)-3,5-bis-trifluoromethyl-cyclohexyl)-4-oxo-1,3,8-triaza-spiro[4.5]dec-1-ene-8-sulfonyl]-ethyl}-3,5-dimethyl-phenyl)-1-methyl-urea;

(1139) 1-(3,5-dimethyl-4-{2-[4-oxo-2-(4-trimethylsilanyl-phenyl)-1,3,8-triaza-spiro[4.5]dec-1-ene-8-sulfonyl]-ethyl}-phenyl)-1-methyl-urea;

(1140) 1-{3,5-dimethyl-4-[2-(4-oxo-2-tridecyl-1,3,8-triaza-spiro[4.5]dec-1-ene-8-sulfonyl)-ethyl]-phenyl}-1-methyl-urea;

(1141) 1-{3,5-dimethyl-4-[2-(4-oxo-2-undecyl-1,3,8-triaza-spiro[4.5]dec-1-ene-8-sulfonyl)-ethyl]-phenyl}-1-methyl-urea;

(1142) 1-{3,5-dimethyl-4-[2-(2-octyl-4-oxo-1,3,8-triaza-spiro[4.5]dec-1-ene-8-sulfonyl)-ethyl]-phenyl}-1-methyl-urea;

(1143) 1-(4-{2-[2-((1S,3R)-3-hexyl-cyclohexyl)-4-oxo-1,3,8-triaza-spiro[4.5]dec-1-ene-8-sulfonyl]-ethyl}-3,5-dimethyl-phenyl)-1-methyl-urea;

(1144) 1-[3,5-dimethyl-4-(2-{2-[3-(3-methyl-butyl)-phenyl]-4-oxo-1,3,8-triaza-spiro[4.5]dec-1-ene-8-sulfonyl}-ethyl)-phenyl]-1-methyl-urea;

(1145) 1-(4-{2-[2-((1S,3R)-3-butyl-cyclohexyl)-4-oxo-1,3,8-triaza-spiro[4.5]dec-1-ene-8-sulfonyl]-ethyl}-3,5-dimethyl-phenyl)-1-methyl-urea;

(1146) 1-[3,5-dimethyl-4-(2-{2-[(1S,3S)-3-(3-methyl-butyl)-cyclohexyl]-4-oxo-1,3,8-triaza-spiro[4.5]dec-1-ene-8-sulfonyl}-ethyl)-phenyl]-1-methyl-urea;

(1147) 1-(3,5-dimethyl-4-{2-[4-oxo-2-(3,3,9,9,9-pentafluoro-nonyl)-1,3,8-triaza-spiro[4.5]dec-1-ene-8-sulfonyl]-ethyl}-phenyl)-1-methyl-urea;

(1148) 1-(4-{2-[2-(4-[1,1,2,2,2-$^2H_5$]ethyl-[4-$^2H_1$]cyclohexyl)-4-oxo-1,3,8-triaza-spiro[4.5]dec-1-ene-8-sulfonyl]-ethyl}-3,5-dimethyl-phenyl)-1-methyl-urea;

(1149) 1-(4-{2-[2-(4-[1,1,2,2,2-$^2H_5$]ethyl-cyclohex-3-enyl)-4-oxo-1,3,8-triaza-spiro[4.5]dec-1-ene-8-sulfonyl]-ethyl}-3,5-dimethyl-phenyl)-1-methyl-urea;

(1150) 1-(4-{2-[2-(4-chloro-3-trifluoromethyl-phenyl)-4-oxo-1,3,8-triaza-spiro[4.5]dec-1-ene-8-sulfonyl]-ethyl}-3,5-dimethyl-phenyl)-1-methyl-urea;

(1151) 1-(3,5-dimethyl-4-{2-[4-oxo-2-(1,9,9,9-tetrafluoro-nonyl)-1,3,8-triaza-spiro[4.5]dec-1-ene-8-sulfonyl]-ethyl}-phenyl)-1-methyl-urea;

(1152) 1-(3,5-dimethyl-4-{2-[4-oxo-2-(4'-propyl-biphenyl-3-yl)-1,3,8-triaza-spiro[4.5]dec-1-ene-8-sulfonyl]-ethyl}-phenyl)-1-methyl-urea;

(1153) 1-(4-{2-[2-(11-fluoro-undecyl)-4-oxo-1,3,8-triaza-spiro[4.5]dec-1-ene-8-sulfonyl]-ethyl}-3,5-dimethyl-phenyl)-1-methyl-urea;

(1154) 1-(4-{2-[2-(6-ethylsulfanyl-hexyl)-4-oxo-1,3,8-triaza-spiro[4.5]dec-1-ene-8-sulfonyl]-ethyl}-3,5-dimethyl-phenyl)-1-methyl-urea;

(1155) 1-{3,5-dimethyl-4-[2-(4-oxo-2-[1,1';3',1"]terphenyl-3-yl-1,3,8-triaza-spiro[4.5]dec-1-ene-8-sulfonyl)-ethyl]-phenyl}-1-methyl-urea;

(1156) 1-(4-{2-[2-(11,11-difluoro-undecyl)-4-oxo-1,3,8-triaza-spiro[4.5]dec-1-ene-8-sulfonyl]-ethyl}-3,5-dimethyl-phenyl)-1-methyl-urea;

(1157) 1-{3,5-dimethyl-4-[(E)-2-(4-oxo-2-[1,1';3',1"]terphenyl-3-yl-1,3,8-triaza-spiro[4.5]dec-1-ene-8-sulfonyl)-vinyl]-phenyl}-1-methyl-urea;

(1158) 8-{(E)-2-[4-(4-hydroxy-piperidine-1-carbonyl)-2,6-dimethyl-phenyl]-ethenesulfonyl}-2-[3-(4,4,5,5,5-pentafluoro-pentyloxy)-phenyl]-1,3,8-triaza-spiro[4.5]dec-1-en-4-one;

(1159) 2-(4-fluoro-3-trifluoromethoxy-phenyl)-8-{(E)-2-[4-(4-hydroxy-piperidine-1-carbonyl)-2,6-dimethyl-phenyl]-ethenesulfonyl}-1,3,8-triaza-spiro[4.5]dec-1-en-4-one;

(1160) 2-(2,2-difluoro-benzo[1,3]dioxol-5-yl)-8-{(E)-2-[4-(4-hydroxy-piperidine-1-carbonyl)-2,6-dimethyl-phenyl]-ethenesulfonyl}-1,3,8-triaza-spiro[4.5]dec-1-en-4-one;

(1161) 2-(4-fluoro-3-trifluoromethoxy-phenyl)-8-{(E)-2-[4-(4-hydroxymethyl-piperidine-1-carbonyl)-2,6-dimethyl-phenyl]-ethenesulfonyl}-1,3,8-triaza-spiro[4.5]dec-1-en-4-one;

(1162) 2-(4-fluoro-3-trifluoromethyl-phenyl)-8-{(E)-2-[4-(4-hydroxymethyl-piperidine-1-carbonyl)-2,6-dimethyl-phenyl]-ethenesulfonyl}-1,3,8-triaza-spiro[4.5]dec-1-en-4-one;

(1163) 2-(2,2-difluoro-benzo[1,3]dioxol-5-yl)-8-{(E)-2-[4-(4-hydroxy-4-methyl-piperidine-1-carbonyl)-2,6-dimethyl-phenyl]-ethenesulfonyl}-1,3,8-triaza-spiro[4.5]dec-1-en-4-one;

(1164) 8-{(E)-2-[4-((R)-2,3-dihydroxy-propoxy)-2,6-dimethyl-phenyl]-ethenesulfonyl}-2-(4-fluoro-3-trifluoromethoxy-phenyl)-1,3,8-triaza-spiro[4.5]dec-1-en-4-one;

(1165) 2-(2,2-difluoro-benzo[1,3]dioxol-5-yl)-8-{(E)-2-[4-((R)-2,3-dihydroxy-propoxy)-2,6-dimethyl-phenyl]-ethenesulfonyl}-1,3,8-triaza-spiro[4.5]dec-1-en-4-one;

(1166) 8-{(E)-2-[4-(3,4-dihydroxy-butoxy)-2-methyl-phenyl]-ethenesulfonyl}-2-(4-fluoro-3-trifluoromethoxy-phenyl)-1,3,8-triaza-spiro[4.5]dec-1-en-4-one;

(1167) 2-(2,2-difluoro-benzo[1,3]dioxol-5-yl)-8-{(E)-2-[4-(3,4-dihydroxy-butoxy)-2-methyl-phenyl]-ethenesulfonyl}-1,3,8-triaza-spiro[4.5]dec-1-en-4-one;

(1168) {4-[(E)-2-(2-cyclohexyl-4-oxo-1,3,8-triaza-spiro[4.5]dec-1-ene-8-sulfonyl)-vinyl]-indol-1-yl}-acetic acid;

(1169) [3-(3-methyl-4-{(E)-2-[2-(4-methyl-cyclohexyl)-4-oxo-1,3,8-triaza-spiro[4.5]dec-1-ene-8-sulfonyl]-vinyl}-phenyl)-ureido]-acetic acid;

(1170) 12-(8-{2-[2,6-dimethyl-4-(1-methyl-ureido)-phenyl]-ethanesulfonyl}-4-oxo-1,3,8-triaza-spiro[4.5]dec-1-en-2-yl)-dodecanoic acid;

(1171) 10-(8-{(E)-2-[2,6-dimethyl-4-(1-methyl-ureido)-phenyl]-ethenesulfonyl}-4-oxo-1,3,8-triaza-spiro[4.5]dec-1-en-2-yl)-decanoic acid;

(1172) 10-(8-{(E)-2-[2,6-dimethyl-4-(1-methyl-ureido)-phenyl]-ethenesulfonyl}-4-oxo-1,3,8-triaza-spiro[4.5]dec-1-en-2-yl)-decanoic acid amide;

(1173) 12-(8-{(E)-2-[2,6-dimethyl-4-(1-methyl-ureido)-phenyl]-ethenesulfonyl}-4-oxo-1,3,8-triaza-spiro[4.5]dec-1-en-2-yl)-dodecanoic acid amide;

(1174) 12-(8-{2-[2,6-dimethyl-4-(1-methyl-ureido)-phenyl]-ethanesulfonyl}-4-oxo-1,3,8-triaza-spiro[4.5]dec-1-en-2-yl)-dodecanoic acid amide;

(1175) 14-(8-{(E)-2-[2,6-dimethyl-4-(1-methyl-ureido)-phenyl]-ethenesulfonyl}-4-oxo-1,3,8-triaza-spiro[4.5]dec-1-en-2-yl)-tetradecanoic acid amide;

(1176) 14-(8-{2-[2,6-dimethyl-4-(1-methyl-ureido)-phenyl]-ethanesulfonyl}-4-oxo-1,3,8-triaza-spiro[4.5]dec-1-en-2-yl)-tetradecanoic acid amide;

(1178) 8-[2-(2-amino-5,7-dimethyl-benzoxazol-6-yl)-ethanesulfonyl]-2-(4-methyl-cyclohexyl)-1,3,8-triaza-spiro[4.5]dec-1-en-4-one;

(1179) 2-cyclohexyl-8-{2-[2,6-dimethyl-4-(2-oxo-oxazolidine-3-carbonyl)-phenyl]-ethanesulfonyl}-1,3,8-triaza-spiro[4.5]dec-1-en-4-one;

(1180) N-methoxy-3,5,N-trimethyl-4-{2-[2-(4-methyl-cyclohexyl)-4-oxo-1,3,8-triaza-spiro[4.5]dec-1-ene-8-sulfonyl]-ethyl}-benzamide;

(1181) 8-{2-[4-(isoxazolidine-2-carbonyl)-2,6-dimethyl-phenyl]-ethanesulfonyl}-2-[4-(3,3,3-trifluoro-propyl)-cyclohexyl]-1,3,8-triaza-spiro[4.5]dec-1-en-4-one;

(1182) 8-{2-[4-(isoxazolidine-2-carbonyl)-2,6-dimethyl-phenyl]-ethanesulfonyl}-2-(4-methyl-cyclohexyl)-1,3,8-triaza-spiro[4.5]dec-1-en-4-one;

(1183) 8-{2-[4-(1,1-dioxo-1$\lambda^6$-thiomorpholine-4-carbonyl)-2,6-dimethyl-phenyl]-ethanesulfonyl}-2-(4-methyl-cyclohexyl)-1,3,8-triaza-spiro[4.5]dec-1-en-4-one;

(1184) 8-(2-{4-[4-((R)-2,3-dihydroxy-propoxy)-piperidine-1-carbonyl]-2,6-dimethyl-phenyl}-ethanesulfonyl)-2-(9,9,9-trifluoro-nonyl)-1,3,8-triaza-spiro[4.5]dec-1-en-4-one;

(1185) 2-(3,4-dichloro-phenyl)-8-{(E)-2-[4-(4-hydroxy-4-methyl-piperidine-1-carbonyl)-2,6-dimethyl-phenyl]-ethenesulfonyl}-1,3,8-triaza-spiro[4.5]dec-1-en-4-one;

(1186) 2-(3-chloro-4-fluoro-phenyl)-8-{(E)-2-[4-(4-hydroxy-4-methyl-piperidine-1-carbonyl)-2,6-dimethyl-phenyl]-ethenesulfonyl}-1,3,8-triaza-spiro[4.5]dec-1-en-4-one;

(1187) [3-(8-{(E)-2-[4-(4-hydroxy-4-methyl-piperidine-1-carbonyl)-2,6-dimethyl-phenyl]-ethenesulfonyl}-4-oxo-1,3,8-triaza-spiro[4.5]dec-1-en-2-yl)-phenyl]-acetonitrile;

(1188) 2-(3-chloro-4-trifluoromethyl-phenyl)-8-{(E)-2-[4-(4-hydroxy-4-methyl-piperidine-1-carbonyl)-2,6-dimethyl-phenyl]-ethenesulfonyl}-1,3,8-triaza-spiro[4.5]dec-1-en-4-one;

(1189) 8-{(E)-2-[4-(4-hydroxy-4-methyl-piperidine-1-carbonyl)-2,6-dimethyl-phenyl]-ethenesulfonyl}-2-(4-pentafluorosulfanyl-phenyl)-1,3,8-triaza-spiro[4.5]dec-1-en-4-one;

(1190) 8-{(E)-2-[4-(4-hydroxy-4-methyl-piperidine-1-carbonyl)-2,6-dimethyl-phenyl]-ethenesulfonyl}-2-(3-pentafluorosulfanyl-phenyl)-1,3,8-triaza-spiro[4.5]dec-1-en-4-one;

(1191) 8-{(E)-2-[4-(4-hydroxy-4-methyl-piperidine-1-carbonyl)-2,6-dimethyl-phenyl]-ethenesulfonyl}-2-[4-(3-trifluoromethyl-phenoxymethyl)-phenyl]-1,3,8-triaza-spiro[4.5]dec-1-en-4-one;

(1192) 2-(4-fluoro-2,3-dimethyl-phenyl)-8-{(E)-2-[4-(4-hydroxy-4-methyl-piperidine-1-carbonyl)-2,6-dimethyl-phenyl]-ethenesulfonyl}-1,3,8-triaza-spiro[4.5]dec-1-en-4-one;

(1193) 8-{(E)-2-[4-(4-hydroxy-4-methyl-piperidine-1-carbonyl)-2,6-dimethyl-phenyl]-ethenesulfonyl}-2-(3-methyl-4-trifluoromethyl-phenyl)-1,3,8-triaza-spiro[4.5]dec-1-en-4-one;

(1194) 2-benzo[1,3]dioxol-5-yl-8-{(E)-2-[4-(4-hydroxy-4-methyl-piperidine-1-carbonyl)-2,6-dimethyl-phenyl]-ethenesulfonyl}-1,3,8-triaza-spiro[4.5]dec-1-en-4-one;

(1195) 8-{(E)-2-[4-(4-hydroxy-4-methyl-piperidine-1-carbonyl)-2,6-dimethyl-phenyl]-ethenesulfonyl}-2-(4-pentafluoroethyl-phenyl)-1,3,8-triaza-spiro[4.5]dec-1-en-4-one;

(1196) 8-{(E)-2-[4-(4-hydroxy-4-methyl-piperidine-1-carbonyl)-2,6-dimethyl-phenyl]-ethenesulfonyl}-2-(3-pentafluoroethyl-phenyl)-1,3,8-triaza-spiro[4.5]dec-1-en-4-one;

(1197) 8-{(E)-2-[4-(4-hydroxy-4-methyl-piperidine-1-carbonyl)-2,6-dimethyl-phenyl]-ethenesulfonyl}-2-[4-(2,2,2-trifluoro-1,1-dimethyl-ethoxy)-3-trifluoromethyl-phenyl]-1,3,8-triaza-spiro[4.5]dec-1-en-4-one;

(1198) 8-{(E)-2-[4-(4-hydroxy-4-methyl-piperidine-1-carbonyl)-2,6-dimethyl-phenyl]-ethenesulfonyl}-2-(4-trifluoromethoxy-phenyl)-1,3,8-triaza-spiro[4.5]dec-1-en-4-one;

(1199) 8-{(E)-2-[4-(4-hydroxy-4-methyl-piperidine-1-carbonyl)-2,6-dimethyl-phenyl]-ethenesulfonyl}-2-[4-(2,2,3,3-tetrafluoro-propoxy)-3-trifluoromethyl-phenyl]-1,3,8-triaza-spiro[4.5]dec-1-en-4-one;

(1200) 8-{(E)-2-[4-(4-hydroxy-4-methyl-piperidine-1-carbonyl)-2,6-dimethyl-phenyl]-ethenesulfonyl}-2-[4-(2,2,2-trifluoro-ethoxy)-3-trifluoromethyl-phenyl]-1,3,8-triaza-spiro[4.5]dec-1-en-4-one;

(1201) 2-[3-chloro-4-(2,2,3,3-tetrafluoro-propoxy)-phenyl]-8-{(E)-2-[4-(4-hydroxy-4-methyl-piperidine-1-carbonyl)-2,6-dimethyl-phenyl]-ethenesulfonyl}-1,3,8-triaza-spiro[4.5]dec-1-en-4-one;

(1202) 8-{(E)-2-[4-(4-hydroxy-4-methyl-piperidine-1-carbonyl)-2,6-dimethyl-phenyl]-ethenesulfonyl}-2-[4-(4,4,5,5,5-pentafluoro-pentyloxy)-3-trifluoromethyl-phenyl]-1,3,8-triaza-spiro[4.5]dec-1-en-4-one;

(1203) 8-{(E)-2-[4-(4-hydroxy-4-methyl-piperidine-1-carbonyl)-2,6-dimethyl-phenyl]-ethenesulfonyl}-2-[4-(2,2,3,3,3-pentafluoro-propoxy)-3-trifluoromethyl-phenyl]-1,3,8-triaza-spiro[4.5]dec-1-en-4-one;

(1204) 8-{(E)-2-[4-(4-hydroxy-4-methyl-piperidine-1-carbonyl)-2,6-dimethyl-phenyl]-ethenesulfonyl}-2-[4-(4,4,4-trifluoro-butoxy)-3-trifluoromethyl-phenyl]-1,3,8-triaza-spiro[4.5]dec-1-en-4-one;

(1205) 8-{(E)-2-[4-(4-hydroxy-4-methyl-piperidine-1-carbonyl)-2,6-dimethyl-phenyl]-ethenesulfonyl}-2-[3-(3-trifluoromethyl-phenoxymethyl)-phenyl]-1,3,8-triaza-spiro[4.5]dec-1-en-4-one;

(1206) 2-[3-(1,1-difluoro-ethyl)-phenyl]-8-{(E)-2-[4-(4-hydroxy-4-methyl-piperidine-1-carbonyl)-2,6-dimethyl-phenyl]-ethenesulfonyl}-1,3,8-triaza-spiro[4.5]dec-1-en-4-one;

(1207) 2-[3-fluoro-4-(4,4,5,5,5-pentafluoro-pentyloxy)-phenyl]-8-{(E)-2-[4-(4-hydroxy-4-methyl-piperidine-1-carbonyl)-2,6-dimethyl-phenyl]-ethenesulfonyl}-1,3,8-triaza-spiro[4.5]dec-1-en-4-one;

(1208) 8-{(E)-2-[4-(4-hydroxy-4-methyl-piperidine-1-carbonyl)-2,6-dimethyl-phenyl]-ethenesulfonyl}-2-(1H-indol-6-yl)-1,3,8-triaza-spiro[4.5]dec-1-en-4-one;

(1209) 8-{(E)-2-[4-(4-hydroxy-4-methyl-piperidine-1-carbonyl)-2,6-dimethyl-phenyl]-ethenesulfonyl}-2-[3-(2,2,2-trifluoro-1,1-dimethyl-ethoxy)-4-trifluoromethyl-phenyl]-1,3,8-triaza-spiro[4.5]dec-1-en-4-one;

(1210) 2-[4-chloro-3-(2,2,2-trifluoro-1,1-dimethyl-ethoxy)-phenyl]-8-{(E)-2-[4-(4-hydroxy-4-methyl-piperidine-1-carbonyl)-2,6-dimethyl-phenyl]-ethenesulfonyl}-1,3,8-triaza-spiro[4.5]dec-1-en-4-one;

(1211) 2-(3-[1,1,2,2,3,3,4,4,4-$^2H_9$]butoxy-4-fluoro-phenyl)-8-{(E)-2-[4-(4-hydroxy-4-methyl-piperidine-1-carbonyl)-2,6-dimethyl-phenyl]-ethenesulfonyl}-1,3,8-triaza-spiro[4.5]dec-1-en-4-one;

(1212) 8-{(E)-2-[4-(4-hydroxy-4-methyl-piperidine-1-carbonyl)-2,6-dimethyl-phenyl]-ethenesulfonyl}-2-(2,2,3,3-tetrafluoro-2,3-dihydro-benzo[1,4]dioxin-6-yl)-1,3,8-triaza-spiro[4.5]dec-1-en-4-one;

(1213) 8-{(E)-2-[4-(4-hydroxy-4-methyl-piperidine-1-carbonyl)-2,6-dimethyl-phenyl]-ethenesulfonyl}-2-[4-(1,1,2,2-tetrafluoro-ethoxy)-phenyl]-1,3,8-triaza-spiro[4.5]dec-1-en-4-one;

(1214) 8-{(E)-2-[4-(4-hydroxy-4-methyl-piperidine-1-carbonyl)-2,6-dimethyl-phenyl]-ethenesulfonyl}-2-(3-methyl-4-trifluoromethoxy-phenyl)-1,3,8-triaza-spiro[4.5]dec-1-en-4-one;

(1215) 2-[4-fluoro-3-(3-fluoro-propoxy)-phenyl]-8-{(E)-2-[4-(4-hydroxy-4-methyl-piperidine-1-carbonyl)-2,6-dimethyl-phenyl}-ethenesulfonyl]-1,3,8-triaza-spiro[4.5]dec-1-en-4-one;

(1216) 2-[3-chloro-4-(2,2,2-trifluoro-ethoxy)-phenyl]-8-{(E)-2-[4-(4-hydroxy-4-methyl-piperidine-1-carbonyl)-2,6-dimethyl-phenyl]-ethenesulfonyl}-1,3,8-triaza-spiro[4.5]dec-1-en-4-one;

(1217) 2-(3-difluoromethyl-4-fluoro-phenyl)-8-{(E)-2-[4-(4-hydroxy-4-methyl-piperidine-1-carbonyl)-2,6-dimethyl-phenyl]-ethenesulfonyl}-1,3,8-triaza-spiro[4.5]dec-1-en-4-one;

(1218) 2-[4-fluoro-3-(4,4,4-trifluoro-butoxy)-phenyl]-8-{(E)-2-[4-(4-hydroxy-4-methyl-piperidine-1-carbonyl)-2,6-dimethyl-phenyl]-ethenesulfonyl}-1,3,8-triaza-spiro[4.5]dec-1-en-4-one;

(1219) 2-(4-difluoromethyl-3-fluoro-phenyl)-8-{(E)-2-[4-(4-hydroxy-4-methyl-piperidine-1-carbonyl)-2,6-dimethyl-phenyl]-ethenesulfonyl}-1,3,8-triaza-spiro[4.5]dec-1-en-4-one;

(1220) 2-(4-[1,1,2,2,3,3,4,4,4-$^2H_9$]butoxy-3-trifluoromethyl-phenyl)-8-{(E)-2-[4-(4-hydroxy-4-methyl-piperidine-1-carbonyl)-2,6-dimethyl-phenyl]-ethenesulfonyl}-1,3,8-triaza-spiro[4.5]dec-1-en-4-one;

(1221) 2-(4-[1,1,2,2,2-$^2H_5$]ethoxy-3-trifluoromethyl-phenyl)-8-{(E)-2-[4-(4-hydroxy-4-methyl-piperidine-1-carbonyl)-2,6-dimethyl-phenyl]-ethenesulfonyl}-1,3,8-triaza-spiro[4.5]dec-1-en-4-one;

(1222) 8-{(E)-2-[4-(4-hydroxy-4-methyl-piperidine-1-carbonyl)-2,6-dimethyl-phenyl]-ethenesulfonyl}-2-(4-[1,2,2,2,2,2,2-$^2H_7$]isopropoxy-3-trifluoromethyl-phenyl)-1,3,8-triaza-spiro[4.5]dec-1-en-4-one;

(1223) 8-{(E)-2-[4-(4-hydroxy-4-methyl-piperidine-1-carbonyl)-2,6-dimethyl-phenyl]-ethenesulfonyl}-2-[3-(2,2,3,3-tetrafluoro-propoxy)-4-trifluoromethyl-phenyl]-1,3,8-triaza-spiro[4.5]dec-1-en-4-one;

(1224) 2-(3-[1,1,2,2,2-$^2H_5$]ethoxy-4-fluoro-phenyl)-8-{(E)-2-[4-(4-hydroxy-4-methyl-piperidine-1-carbonyl)-2,6-dimethyl-phenyl]-ethenesulfonyl}-1,3,8-triaza-spiro[4.5]dec-1-en-4-one;

(1225) 2-(4-fluoro-3-[1,2,2,2,2,2,2-$^2H_7$]isopropoxy-phenyl)-8-{(E)-2-[4-(4-hydroxy-4-methyl-piperidine-1-carbonyl)-2,6-dimethyl-phenyl]-ethenesulfonyl}-1,3,8-triaza-spiro[4.5]dec-1-en-4-one;

(1226) 8-{(E)-2-[4-(4-hydroxy-4-methyl-piperidine-1-carbonyl)-2,6-dimethyl-phenyl]-ethenesulfonyl}-2-[3-(2,2,3,3-tetrafluoro-propoxy)-5-trifluoromethyl-phenyl]-1,3,8-triaza-spiro[4.5]dec-1-en-4-one;

(1227) 2-[4-chloro-3-(4,4,4-trifluoro-butoxy)-phenyl]-8-{(E)-2-[4-(4-hydroxy-4-methyl-piperidine-1-carbonyl)-2,6-dimethyl-phenyl]-ethenesulfonyl}-1,3,8-triaza-spiro[4.5]dec-1-en-4-one;

(1228) 8-{(E)-2-[4-(4-hydroxy-4-methyl-piperidine-1-carbonyl)-2,6-dimethyl-phenyl]-ethenesulfonyl}-2-[3-(2,2,3,3,3-pentafluoro-propoxy)-4-trifluoromethyl-phenyl]-1,3,8-triaza-spiro[4.5]dec-1-en-4-one;

(1229) 2-[4-chloro-3-(2,2,3,3-tetrafluoro-propoxy)-phenyl]-8-{(E)-2-[4-(4-hydroxy-4-methyl-piperidine-1-carbonyl)-2,6-dimethyl-phenyl]-ethenesulfonyl}-1,3,8-triaza-spiro[4.5]dec-1-en-4-one;

(1230) 2-[4-chloro-3-(2,2,3,3,3-pentafluoro-propoxy)-phenyl]-8-{(E)-2-[4-(4-hydroxy-4-methyl-piperidine-1-carbonyl)-2,6-dimethyl-phenyl]-ethenesulfonyl}-1,3,8-triaza-spiro[4.5]dec-1-en-4-one;

(1231) 2-(3-[1,1,2,2,3,3,4,4,4-$^2H_9$]butoxy-4-chloro-phenyl)-8-{(E)-2-[4-(4-hydroxy-4-methyl-piperidine-1-carbonyl)-2,6-dimethyl-phenyl]-ethenesulfonyl}-1,3,8-triaza-spiro[4.5]dec-1-en-4-one;

(1232) 8-{(E)-2-[4-(4-hydroxy-4-methyl-piperidine-1-carbonyl)-2,6-dimethyl-phenyl]-ethenesulfonyl}-2-[3-(4,4,4-trifluoro-butoxy)-4-trifluoromethoxy-phenyl]-1,3,8-triaza-spiro[4.5]dec-1-en-4-one;

(1233) 2-(3-[1,1,2,2,3,3,4,4,4-$^2H_9$]butoxy-5-trifluoromethyl-phenyl)-8-{(E)-2-[4-(4-hydroxy-4-methyl-piperidine-1-carbonyl)-2,6-dimethyl-phenyl]-ethenesulfonyl}-1,3,8-triaza-spiro[4.5]dec-1-en-4-one;

(1234) 8-{2-[4-(4-hydroxy-4-methyl-piperidine-1-carbonyl)-2,6-dimethyl-phenyl]-ethanesulfonyl}-2-(4-trifluoromethoxy-phenyl)-1,3,8-triaza-spiro[4.5]dec-1-en-4-one;

(1235) 8-{2-[4-(4-hydroxy-4-methyl-piperidine-1-carbonyl)-2,6-dimethyl-phenyl]-ethanesulfonyl}-2-(3-methyl-4-trifluoromethyl-phenyl)-1,3,8-triaza-spiro[4.5]dec-1-en-4-one;

(1236) 2-(3-chloro-4-trifluoromethyl-phenyl)-8-{2-[4-(4-hydroxy-4-methyl-piperidine-1-carbonyl)-2,6-dimethyl-phenyl]-ethanesulfonyl}-1,3,8-triaza-spiro[4.5]dec-1-en-4-one;

(1237) 2-(3,4-dimethyl-phenyl)-8-{(E)-2-[4-(4-hydroxy-4-methyl-piperidine-1-carbonyl)-2,6-dimethyl-phenyl]-ethenesulfonyl}-1,3,8-triaza-spiro[4.5]dec-1-en-4-one;

(1238) 8-{(E)-2-[4-(4-hydroxy-4-methyl-piperidine-1-carbonyl)-2,6-dimethyl-phenyl]-ethenesulfonyl}-2-(4-methoxy-3-methyl-phenyl)-1,3,8-triaza-spiro[4.5]dec-1-en-4-one;

(1239) 2-(4-fluoro-2,5-dimethyl-phenyl)-8-{(E)-2-[4-(4-fluoromethyl-4-hydroxy-piperidine-1-carbonyl)-2,6-dimethyl-phenyl]-ethenesulfonyl}-1,3,8-triaza-spiro[4.5]dec-1-en-4-one;

(1240) 2-(4-fluoro-2,3-dimethyl-phenyl)-8-{(E)-2-[4-(4-fluoromethyl-4-hydroxy-piperidine-1-carbonyl)-2,6-dimethyl-phenyl]-ethenesulfonyl}-1,3,8-triaza-spiro[4.5]dec-1-en-4-one;

(1241) 2-(3-chloro-4-trifluoromethyl-phenyl)-8-{(E)-2-[4-(4-fluoromethyl-4-hydroxy-piperidine-1-carbonyl)-2,6-dimethyl-phenyl]-ethenesulfonyl}-1,3,8-triaza-spiro[4.5]dec-1-en-4-one;

(1242) 2-(3-chloro-4-fluoro-phenyl)-8-{(E)-2-[4-(4-fluoromethyl-4-hydroxy-piperidine-1-carbonyl)-2,6-dimethyl-phenyl]-ethenesulfonyl}-1,3,8-triaza-spiro[4.5]dec-1-en-4-one;

(1243) 8-{(E)-2-[4-(4-fluoromethyl-4-hydroxy-piperidine-1-carbonyl)-2,6-dimethyl-phenyl]-ethenesulfonyl}-2-(3-pentafluoroethyl-phenyl)-1,3,8-triaza-spiro[4.5]dec-1-en-4-one;

(1244) 8-{(E)-2-[4-(4-fluoromethyl-4-hydroxy-piperidine-1-carbonyl)-2,6-dimethyl-phenyl]-ethenesulfonyl}-2-(4-pentafluoroethyl-phenyl)-1,3,8-triaza-spiro[4.5]dec-1-en-4-one;

(1245) 8-{(E)-2-[4-(4-fluoromethyl-4-hydroxy-piperidine-1-carbonyl)-2,6-dimethyl-phenyl]-ethenesulfonyl}-2-(4-pentafluorosulfanyl-phenyl)-1,3,8-triaza-spiro[4.5]dec-1-en-4-one;

(1246) 2-[3-chloro-4-(2,2,2-trifluoro-ethoxy)-phenyl]-8-{(E)-2-[4-(4-fluoromethyl-4-hydroxy-piperidine-1-carbonyl)-2,6-dimethyl-phenyl]-ethenesulfonyl}-1,3,8-triaza-spiro[4.5]dec-1-en-4-one;

(1247) 2-[3-chloro-4-(2,2,3,3-tetrafluoro-propoxy)-phenyl]-8-{(E)-2-[4-(4-fluoromethyl-4-hydroxy-piperidine-1-carbonyl)-2,6-dimethyl-phenyl]-ethenesulfonyl}-1,3,8-triaza-spiro[4.5]dec-1-en-4-one;

(1248) 8-{(E)-2-[4-(4-fluoromethyl-4-hydroxy-piperidine-1-carbonyl)-2,6-dimethyl-phenyl]-ethenesulfonyl}-2-[4-(2,2,2-trifluoro-ethoxy)-3-trifluoromethyl-phenyl]-1,3,8-triaza-spiro[4.5]dec-1-en-4-one;

(1249) 8-{(E)-2-[4-(4-fluoromethyl-4-hydroxy-piperidine-1-carbonyl)-2,6-dimethyl-phenyl]-ethenesulfonyl}-2-[4-(2,2,3,3,3-pentafluoro-propoxy)-3-trifluoromethyl-phenyl]-1,3,8-triaza-spiro[4.5]dec-1-en-4-one;

(1250) 8-{(E)-2-[4-(4-fluoromethyl-4-hydroxy-piperidine-1-carbonyl)-2,6-dimethyl-phenyl]-ethenesulfonyl}-2-[4-(4,4,4-trifluoro-butoxy)-3-trifluoromethyl-phenyl]-1,3,8-triaza-spiro[4.5]dec-1-en-4-one;

(1251) 8-{(E)-2-[4-(4-fluoromethyl-4-hydroxy-piperidine-1-carbonyl)-2,6-dimethyl-phenyl]-ethenesulfonyl}-2-[4-(2,2,3,3-tetrafluoro-propoxy)-3-trifluoromethyl-phenyl]-1,3,8-triaza-spiro[4.5]dec-1-en-4-one;

(1252) 8-{(E)-2-[4-(4-fluoromethyl-4-hydroxy-piperidine-1-carbonyl)-2,6-dimethyl-phenyl]-ethenesulfonyl}-2-[4-(4,4,5,5,5-pentafluoro-pentyloxy)-3-trifluoromethyl-phenyl]-1,3,8-triaza-spiro[4.5]dec-1-en-4-one;

(1253) 2-(4-[1,1,2,2,2-$^{2}H_{5}$]ethoxy-3-trifluoromethyl-phenyl)-8-{(E)-2-[4-(4-fluoromethyl-4-hydroxy-piperidine-1-carbonyl)-2,6-dimethyl-phenyl]-ethenesulfonyl}-1,3,8-triaza-spiro[4.5]dec-1-en-4-one;

(1254) 8-{(E)-2-[4-(4-fluoromethyl-4-hydroxy-piperidine-1-carbonyl)-2,6-dimethyl-phenyl]-ethenesulfonyl}-2-(3-methyl-4-trifluoromethyl-phenyl)-1,3,8-triaza-spiro[4.5]dec-1-en-4-one;

(1255) 2-(4-difluoromethyl-3-fluoro-phenyl)-8-{(E)-2-[4-(4-fluoromethyl-4-hydroxy-piperidine-1-carbonyl)-2,6-dimethyl-phenyl]-ethenesulfonyl}-1,3,8-triaza-spiro[4.5]dec-1-en-4-one;

(1256) 2-(3-difluoromethyl-4-fluoro-phenyl)-8-{(E)-2-[4-(4-fluoromethyl-4-hydroxy-piperidine-1-carbonyl)-2,6-dimethyl-phenyl]-ethenesulfonyl}-1,3,8-triaza-spiro[4.5]dec-1-en-4-one;

(1257) 2-(3,4-dichloro-phenyl)-8-{(E)-2-[4-(4-fluoromethyl-4-hydroxy-piperidine-1-carbonyl)-2,6-dimethyl-phenyl]-ethenesulfonyl}-1,3,8-triaza-spiro[4.5]dec-1-en-4-one;

(1258) 8-{(E)-2-[4-(4-fluoromethyl-4-hydroxy-piperidine-1-carbonyl)-2,6-dimethyl-phenyl]-ethenesulfonyl}-2-(3-methyl-4-trifluoromethoxy-phenyl)-1,3,8-triaza-spiro[4.5]dec-1-en-4-one;

(1259) 8-{(E)-2-[4-(4-fluoromethyl-4-hydroxy-piperidine-1-carbonyl)-2,6-dimethyl-phenyl]-ethenesulfonyl}-2-(2-methyl-4-trifluoromethyl-phenyl)-1,3,8-triaza-spiro[4.5]dec-1-en-4-one;

(1260) 8-{(E)-2-[4-(4-fluoromethyl-4-hydroxy-piperidine-1-carbonyl)-2,6-dimethyl-phenyl]-ethenesulfonyl}-2-[3-fluoro-4-(2,2,2-trifluoro-ethoxy)-phenyl]-1,3,8-triaza-spiro[4.5]dec-1-en-4-one;

(1261) 2-(4-[1,1,2,2,3,3,4,4,4-$^{2}H_{9}$]butoxy-3-trifluoromethyl-phenyl)-8-{(E)-2-[4-(4-fluoromethyl-4-hydroxy-piperidine-1-carbonyl)-2,6-dimethyl-phenyl]-ethenesulfonyl}-1,3,8-triaza-spiro[4.5]dec-1-en-4-one;

(1262) 8-{(E)-2-[4-(4-fluoromethyl-4-hydroxy-piperidine-1-carbonyl)-2,6-dimethyl-phenyl]-ethenesulfonyl}-2-(4-[1,2,2,2,2,2,2-$^{2}H_{7}$]isopropoxy-3-trifluoromethyl-phenyl)-1,3,8-triaza-spiro[4.5]dec-1-en-4-one;

(1263) 8-{(E)-2-[4-(4-fluoromethyl-4-hydroxy-piperidine-1-carbonyl)-2,6-dimethyl-phenyl]-ethenesulfonyl}-2-[4-fluoro-3-(4,4,5,5,5-pentafluoro-pentyloxy)-phenyl]-1,3,8-triaza-spiro[4.5]dec-1-en-4-one;

(1264) 2-[4-fluoro-3-(3-fluoro-propoxy)-phenyl]-8-{(E)-2-[4-(4-fluoromethyl-4-hydroxy-piperidine-1-carbonyl)-2,6-dimethyl-phenyl]-ethenesulfonyl}-1,3,8-triaza-spiro[4.5]dec-1-en-4-one;

(1265) 8-{(E)-2-[4-(4-fluoromethyl-4-hydroxy-piperidine-1-carbonyl)-2,6-dimethyl-phenyl]-ethenesulfonyl}-2-[4-(2,2,2-trifluoro-1,1-dimethyl-ethoxy)-3-trifluoromethyl-phenyl]-1,3,8-triaza-spiro[4.5]dec-1-en-4-one;

(1266) 8-{(E)-2-[4-(4-fluoromethyl-4-hydroxy-piperidine-1-carbonyl)-2,6-dimethyl-phenyl]-ethenesulfonyl}-2-[3-(2,2,2-trifluoro-1,1-dimethyl-ethoxy)-4-trifluoromethyl-phenyl]-1,3,8-triaza-spiro[4.5]dec-1-en-4-one;

(1267) 2-[3-(1,1-difluoro-ethyl)-phenyl]-8-{(E)-2-[4-(4-fluoromethyl-4-hydroxy-piperidine-1-carbonyl)-2,6-dimethyl-phenyl]-ethenesulfonyl}-1,3,8-triaza-spiro[4.5]dec-1-en-4-one;

(1268) 8-{(E)-2-[4-(4-fluoromethyl-4-hydroxy-piperidine-1-carbonyl)-2,6-dimethyl-phenyl]-ethenesulfonyl}-2-(1H-indol-6-yl)-1,3,8-triaza-spiro[4.5]dec-1-en-4-one;

(1269) 8-{(E)-2-[4-(4-fluoromethyl-4-hydroxy-piperidine-1-carbonyl)-2,6-dimethyl-phenyl]-ethenesulfonyl}-2-(4-trifluoromethoxy-phenyl)-1,3,8-triaza-spiro[4.5]dec-1-en-4-one;

(1270) 2-[4-chloro-3-(2,2,3,3,3-pentafluoro-propoxy)-phenyl]-8-{(E)-2-[4-(4-fluoromethyl-4-hydroxy-piperidine-1-carbonyl)-2,6-dimethyl-phenyl]-ethenesulfonyl}-1,3,8-triaza-spiro[4.5]dec-1-en-4-one;

(1271) 2-[4-chloro-3-(2,2,2-trifluoro-1,1-dimethyl-ethoxy)-phenyl]-8-{(E)-2-[4-(4-fluoromethyl-4-hydroxy-piperidine-1-carbonyl)-2,6-dimethyl-phenyl]-ethenesulfonyl}-1,3,8-triaza-spiro[4.5]dec-1-en-4-one;

(1272) 2-(3-[1,1,2,2,2-$^2H_5$]ethoxy-4-fluoro-phenyl)-8-{(E)-2-[4-(4-fluoromethyl-4-hydroxy-piperidine-1-carbonyl)-2,6-dimethyl-phenyl]-ethenesulfonyl}-1,3,8-triaza-spiro[4.5]dec-1-en-4-one;

(1273) 8-{(E)-2-[4-(4-fluoromethyl-4-hydroxy-piperidine-1-carbonyl)-2,6-dimethyl-phenyl]-ethenesulfonyl}-2-[3-(4,4,4-trifluoro-butoxy)-4-trifluoromethoxy-phenyl]-1,3,8-triaza-spiro[4.5]dec-1-en-4-one;

(1274) 8-{(E)-2-[4-(4-fluoromethyl-4-hydroxy-piperidine-1-carbonyl)-2,6-dimethyl-phenyl]-ethenesulfonyl}-2-[3-(2,2,3,3-tetrafluoro-propoxy)-4-trifluoromethyl-phenyl]-1,3,8-triaza-spiro[4.5]dec-1-en-4-one;

(1275) 2-(2,2-difluoro-benzo[1,3]dioxol-5-yl)-8-{2-[4-(4-fluoromethyl-4-hydroxy-piperidine-1-carbonyl)-2,6-dimethyl-phenyl]-ethanesulfonyl}-1,3,8-triaza-spiro[4.5]dec-1-en-4-one;

(1276) 8-{2-[4-(4-fluoromethyl-4-hydroxy-piperidine-1-carbonyl)-2,6-dimethyl-phenyl]-ethanesulfonyl}-2-(4-trifluoromethoxy-phenyl)-1,3,8-triaza-spiro[4.5]dec-1-en-4-one;

(1277) 8-{2-[4-(4-fluoromethyl-4-hydroxy-piperidine-1-carbonyl)-2,6-dimethyl-phenyl]-ethanesulfonyl}-2-(3-methyl-4-trifluoromethyl-phenyl)-1,3,8-triaza-spiro[4.5]dec-1-en-4-one;

(1278) 2-(3-chloro-4-trifluoromethyl-phenyl)-8-{2-[4-(4-fluoromethyl-4-hydroxy-piperidine-1-carbonyl)-2,6-dimethyl-phenyl]-ethanesulfonyl}-1,3,8-triaza-spiro[4.5]dec-1-en-4-one;

(1279) 8-{2-[4-(4-fluoromethyl-4-hydroxy-piperidine-1-carbonyl)-2,6-dimethyl-phenyl]-ethanesulfonyl}-2-[3-(2,2,3,3-tetrafluoro-propoxy)-4-trifluoromethyl-phenyl]-1,3,8-triaza-spiro[4.5]dec-1-en-4-one;

(1280) 2-(2,2-difluoro-benzo[1,3]dioxol-5-yl)-8-{(E)-2-[4-(4-fluoromethyl-4-hydroxy-piperidine-1-carbonyl)-2,6-dimethyl-phenyl]-ethenesulfonyl}-1,3,8-triaza-spiro[4.5]dec-1-en-4-one;

(1281) 8-{2-[4-(4-fluoromethyl-4-hydroxy-piperidine-1-carbonyl)-2,6-dimethyl-phenyl]-ethanesulfonyl}-2-(2,2,3,3-tetrafluoro-2,3-dihydro-benzo[1,4]dioxin-6-yl)-1,3,8-triaza-spiro[4.5]dec-1-en-4-one;

(1282) [3-(8-{(E)-2-[4-(4-hydroxy-piperidine-1-carbonyl)-2,6-dimethyl-phenyl]-ethenesulfonyl}-4-oxo-1,3,8-triaza-spiro[4.5]dec-1-en-2-yl)-phenyl]-acetonitrile;

(1283) 8-{(E)-2-[2-methyl-4-(piperidin-4-yloxy)-phenyl]-ethenesulfonyl}-2-(3-trifluoromethoxy-phenyl)-1,3,8-triaza-spiro[4.5]dec-1-en-4-one;

(1284) 8-[2-(4-aminomethyl-2-methyl-phenyl)-ethanesulfonyl]-2-[4-(3,3,3-trifluoro-propyl)-cyclohexyl]-1,3,8-triaza-spiro[4.5]dec-1-en-4-one;

(1285) 2-(4-methyl-cyclohexyl)-8-{(E)-2-[2-methyl-4-(2-oxo-piperazin-1-yl)-phenyl]-ethenesulfonyl}-1,3,8-triaza-spiro[4.5]dec-1-en-4-one;

(1286) 8-[2-(2,6-dimethyl-4-methylamino-phenyl)-ethanesulfonyl]-2-pyrrolidin-2-yl-1,3,8-triaza-spiro[4.5]dec-1-en-4-one hydrochloride;

(1287) 2-(1,1-difluoro-ethyl)-8-[2-(2,6-dimethyl-4-methylamino-phenyl)-ethanesulfonyl]-1,3,8-triaza-spiro[4.5]dec-1-en-4-one hydrochloride;

(1288) 8-[(E)-2-(2,6-dimethyl-4-[1,1,1-$^2H_3$]methylamino-phenyl)-ethenesulfonyl]-2-(4-fluoro-3-trifluoromethyl-phenyl)-1,3,8-triaza-spiro[4.5]dec-1-en-4-one hydrochloride;

(1289) 8-[(E)-2-(2,6-dimethyl-4-methylaminomethyl-phenyl)-ethenesulfonyl]-2-(4-methyl-cyclohexyl)-1,3,8-triaza-spiro[4.5]dec-1-en-4-one;

(1290) 8-[(E)-2-(4-aminomethyl-2,6-dimethyl-phenyl)-ethenesulfonyl]-2-[4-(3,3,3-trifluoro-propyl)-cyclohexyl]-1,3,8-triaza-spiro[4.5]dec-1-en-4-one;

(1291) 8-[(E)-2-(4-aminomethyl-2,6-dimethyl-phenyl)-ethenesulfonyl]-2-(4-methyl-cyclohexyl)-1,3,8-triaza-spiro[4.5]dec-1-en-4-one;

(1292) 8-[(E)-2-(2,6-dimethyl-4-methylaminomethyl-phenyl)-ethenesulfonyl]-2-[4-(3,3,3-trifluoro-propyl)-cyclohexyl]-1,3,8-triaza-spiro[4.5]dec-1-en-4-one;

(1293) 8-[2-(4-amino-3-chloro-2-methyl-phenyl)-ethanesulfonyl]-2-(4-ethyl-cyclohexyl)-1,3,8-triaza-spiro[4.5]dec-1-en-4-one;

(1294) N-(1-acetyl-piperidin-4-yl)-N-(3-methyl-4-{(E)-2-[4-oxo-2-(3-trifluoromethoxy-phenyl)-1,3,8-triaza-spiro[4.5]dec-1-ene-8-sulfonyl]-vinyl}-phenyl)-acetamide;

(1295) 8-{2-[4-(4,5-dihydro-thiazol-2-ylamino)-2-methyl-phenyl]-ethanesulfonyl}-2-(4-ethyl-cyclohexyl)-1,3,8-triaza-spiro[4.5]dec-1-en-4-one;

(1296) N-[4-(2-{2-[4-(4-fluoro-butyl)-cyclohexyl]-4-oxo-1,3,8-triaza-spiro[4.5]dec-1-ene-8-sulfonyl}-ethyl)-3-methyl-phenyl]-acetamide;

(1297) 1-(3,5-dimethyl-4-{2-[2-((1S,3R)-3-methyl-cyclohexyl)-4-oxo-1,3,8-triaza-spiro[4.5]dec-1-ene-8-sulfonyl]-ethyl}-phenyl)-1-methyl-urea;

(1298) 1-(3,5-dimethyl-4-{2-[4-oxo-2-(3,3,5,5-tetramethyl-cyclohexyl)-1,3,8-triaza-spiro[4.5]dec-1-ene-8-sulfonyl]-ethyl}-phenyl)-1-methyl-urea;

(1299) 3-(3,5-dimethyl-4-{2-[2-(4-methyl-cyclohexyl)-4-oxo-1,3,8-triaza-spiro[4.5]dec-1-ene-8-sulfonyl]-ethyl}-phenyl)-5-hydroxymethyl-imidazolidine-2,4-dione;

(1300) 1-[3,5-dimethyl-4-((E)-2-{4-oxo-2-[4-(3,3,3-trifluoro-propyl)-cyclohexyl]-1,3,8-triaza-spiro[4.5]dec-1-ene-8-sulfonyl}-vinyl)-benzyl]-1-methyl-urea;

(1301) 1-(3,5-dimethyl-4-{(E)-2-[2-(4-methyl-cyclohexyl)-4-oxo-1,3,8-triaza-spiro[4.5]dec-1-ene-8-sulfonyl]-vinyl}-benzyl)-1-methyl-urea;

(1302) 1-(3,5-dimethyl-4-{2-[4-oxo-2-(8,8,9,9,9-pentafluoro-nonyl)-1,3,8-triaza-spiro[4.5]dec-1-ene-8-sulfonyl]-ethyl}-phenyl)-1-methyl-urea;

(1303) 1-(3,5-dimethyl-4-{(E)-2-[4-oxo-2-(8,8,9,9,9-pentafluoro-nonyl)-1,3,8-triaza-spiro[4.5]dec-1-ene-8-sulfonyl]-vinyl}-phenyl)-1-methyl-urea;

(1304) 1-(3,5-dimethyl-4-{(E)-2-[4-oxo-2-(9,9,9-trifluoro-nonyl)-1,3,8-triaza-spiro[4.5]dec-1-ene-8-sulfonyl]-vinyl}-phenyl)-1-methyl-urea;

(1305) 1-(3,5-dimethyl-4-{(E)-2-[4-oxo-2-(3-trifluoromethylsulfanyl-phenyl)-1,3,8-triaza-spiro[4.5]dec-1-ene-8-sulfonyl]-vinyl}-phenyl)-1-methyl-urea;

(1306) 1-(3,5-dimethyl-4-{2-[4-oxo-2-(3-trifluoromethylsulfanyl-phenyl)-1,3,8-triaza-spiro[4.5]dec-1-ene-8-sulfonyl]-ethyl}-phenyl)-1-methyl-urea;

(1307) 1-(4-{(E)-2-[2-(11-hydroxy-undecyl)-4-oxo-1,3,8-triaza-spiro[4.5]dec-1-ene-8-sulfonyl]-vinyl}-3,5-dimethyl-phenyl)-1-methyl-urea;

(1308) [11-(8-{(E)-2-[2,6-dimethyl-4-(1-methyl-ureido)-phenyl]-ethenesulfonyl}-4-oxo-1,3,8-triaza-spiro[4.5]dec-1-en-2-yl)-undecyl]-carbamic acid tert-butyl ester;

(1309) 1-(4-{(E)-2-[2-(9-hydroxy-nonyl)-4-oxo-1,3,8-triaza-spiro[4.5]dec-1-ene-8-sulfonyl]-vinyl}-3,5-dimethyl-phenyl)-1-methyl-urea;

(1310) 1-(4-{2-[2-(4-isopropylidene-cyclohexyl)-4-oxo-1,3,8-triaza-spiro[4.5]dec-1-ene-8-sulfonyl]-ethyl}-3,5-dimethyl-phenyl)-1-methyl-urea;

(1311) 1-(4-{2-[2-(1,1-difluoro-ethyl)-4-oxo-1,3,8-triaza-spiro[4.5]dec-1-ene-8-sulfonyl]-ethyl}-3,5-dimethyl-phenyl)-1-methyl-urea;

(1312) 1-(4-{(E)-2-[2-(4-fluoro-3-trifluoromethyl-phenyl)-4-oxo-1,3,8-triaza-spiro[4.5]dec-1-ene-8-sulfonyl]-vinyl}-3,5-dimethyl-phenyl)-1-[1,1,1-$^{2}H_3$]methyl-urea;

(1313) [3,5-dimethyl-4-(2-{4-oxo-2-[4-(3,3,3-trifluoro-propyl)-cyclohexyl]-1,3,8-triaza-spiro[4.5]dec-1-ene-8-sulfonyl}-ethyl)-benzyl]-urea;

(1314) (3,5-dimethyl-4-{2-[2-(4-methyl-cyclohexyl)-4-oxo-1,3,8-triaza-spiro[4.5]dec-1-ene-8-sulfonyl]-ethyl}-benzyl)-urea;

(1315) 1-(4-{(E)-2-[2-(11-amino-undecyl)-4-oxo-1,3,8-triaza-spiro[4.5]dec-1-ene-8-sulfonyl]-vinyl}-3,5-dimethyl-phenyl)-1-methyl-urea;

(1316) 1-[3,5-dimethyl-4-((E)-2-{4-oxo-2-[5-(propane-1-sulfinyl)-pentyl]-1,3,8-triaza-spiro[4.5]dec-1-ene-8-sulfonyl}-vinyl)-phenyl]-1-methyl-urea;

(1317) 1-(4-{2-[2-(6-ethanesulfinyl-hexyl)-4-oxo-1,3,8-triaza-spiro[4.5]dec-1-ene-8-sulfonyl]-ethyl}-3,5-dimethyl-phenyl)-1-methyl-urea;

(1318) 1-[3,5-dimethyl-4-((E)-2-{4-oxo-2-[5-(propane-1-sulfonyl)-pentyl]-1,3,8-triaza-spiro[4.5]dec-1-ene-8-sulfonyl}-vinyl)-phenyl]-1-methyl-urea;

(1319) 1-(4-{(E)-2-[2-(7-methanesulfonyl-heptyl)-4-oxo-1,3,8-triaza-spiro[4.5]dec-1-ene-8-sulfonyl]-vinyl}-3,5-dimethyl-phenyl)-1-methyl-urea;

(1320) 1-(4-{2-[2-(6-ethanesulfonyl-hexyl)-4-oxo-1,3,8-triaza-spiro[4.5]dec-1-ene-8-sulfonyl]-ethyl}-3,5-dimethyl-phenyl)-1-methyl-urea;

(1321) 1-(4-{(E)-2-[2-(9,9-difluoro-nonyl)-4-oxo-1,3,8-triaza-spiro[4.5]dec-1-ene-8-sulfonyl]-vinyl}-3,5-dimethyl-phenyl)-1-methyl-urea;

(1322) 1-(4-{2-[2-(9-hydroxy-nonyl)-4-oxo-1,3,8-triaza-spiro[4.5]dec-1-ene-8-sulfonyl]-ethyl}-3,5-dimethyl-phenyl)-1-methyl-urea;

(1323) 1-(4-{2-[2-(9,9-difluoro-nonyl)-4-oxo-1,3,8-triaza-spiro[4.5]dec-1-ene-8-sulfonyl]-ethyl}-3,5-dimethyl-phenyl)-1-methyl-urea;

(1324) 1-(4-{2-[2-(9-amino-nonyl)-4-oxo-1,3,8-triaza-spiro[4.5]dec-1-ene-8-sulfonyl]-ethyl}-3,5-dimethyl-phenyl)-1-methyl-urea;

(1325) 1-(4-{(E)-2-[2-(9-fluoro-nonyl)-4-oxo-1,3,8-triaza-spiro[4.5]dec-1-ene-8-sulfonyl]-vinyl}-3,5-dimethyl-phenyl)-1-methyl-urea;

(1326) 1-(4-{(Z)-2-[2-(9-fluoro-nonyl)-4-oxo-1,3,8-triaza-spiro[4.5]dec-1-ene-8-sulfonyl]-vinyl}-3,5-dimethyl-phenyl)-1-methyl-urea;

(1327) 1-(4-{2-[2-(9-fluoro-nonyl)-4-oxo-1,3,8-triaza-spiro[4.5]dec-1-ene-8-sulfonyl]-ethyl}-3,5-dimethyl-phenyl)-1-methyl-urea;

(1328) 8-{2-[4-((R)-2,3-dihydroxy-propoxy)-2,6-dimethyl-phenyl]-ethanesulfonyl}-2-[3-(4,4,5,5,5-pentafluoro-pentyloxy)-phenyl]-1,3,8-triaza-spiro[4.5]dec-1-en-4-one;

(1329) 8-{2-[4-((R)-2,3-dihydroxy-propoxy)-2,6-dimethyl-phenyl]-ethanesulfonyl}-2-(4-fluoro-3-trifluoromethoxy-phenyl)-1,3,8-triaza-spiro[4.5]dec-1-en-4-one;

(1330) 2-(2,2-difluoro-benzo[1,3]dioxol-5-yl)-8-{2-[4-((R)-2,3-dihydroxy-propoxy)-2,6-dimethyl-phenyl]-ethanesulfonyl}-1,3,8-triaza-spiro[4.5]dec-1-en-4-one;

(1331) 2-(2,2-difluoro-benzo[1,3]dioxol-5-yl)-8-{2-[4-(3,4-dihydroxy-butoxy)-2-methyl-phenyl]-ethanesulfonyl}-1,3,8-triaza-spiro[4.5]dec-1-en-4-one;

(1332) 8-{2-[4-(3,4-dihydroxy-butoxy)-2-methyl-phenyl]-ethanesulfonyl}-2-(4-fluoro-3-trifluoromethoxy-phenyl)-1,3,8-triaza-spiro[4.5]dec-1-en-4-one;

(1333) 2-(2,2-difluoro-benzo[1,3]dioxol-5-yl)-8-{2-[4-(4-hydroxy-piperidine-1-carbonyl)-2,6-dimethyl-phenyl]-ethanesulfonyl}-1,3,8-triaza-spiro[4.5]dec-1-en-4-one;

(1334) 2-(4-fluoro-3-trifluoromethoxy-phenyl)-8-{2-[4-(4-hydroxy-piperidine-1-carbonyl)-2,6-dimethyl-phenyl]-ethanesulfonyl}-1,3,8-triaza-spiro[4.5]dec-1-en-4-one;

(1335) 2-(4-fluoro-3-trifluoromethoxy-phenyl)-8-{2-[4-(4-hydroxy-4-methyl-piperidine-1-carbonyl)-2,6-dimethyl-phenyl]-ethanesulfonyl}-1,3,8-triaza-spiro[4.5]dec-1-en-4-one;

(1336) 2-(2,2-difluoro-benzo[1,3]dioxol-5-yl)-8-{2-[4-(4-hydroxy-4-methyl-piperidine-1-carbonyl)-2,6-dimethyl-phenyl]-ethanesulfonyl}-1,3,8-triaza-spiro[4.5]dec-1-en-4-one;

(1337) 2-(4-fluoro-3-trifluoromethoxy-phenyl)-8-{2-[4-(3-hydroxy-azetidine-1-carbonyl)-2,6-dimethyl-phenyl]-ethanesulfonyl}-1,3,8-triaza-spiro[4.5]dec-1-en-4-one;

(1338) 1-[3,5-dimethyl-4-(2-{4-oxo-2-[3-(4,4,4-trifluoro-butoxy)-phenyl]-1,3,8-triaza-spiro[4.5]dec-1-ene-8-sulfonyl}-ethyl)-phenyl]-1-methyl-urea;

(1339) 1-[3,5-dimethyl-4-(2-{4-oxo-2-[4-(4,4,4-trifluoro-butoxy)-phenyl]-1,3,8-triaza-spiro[4.5]dec-1-ene-8-sulfonyl}-ethyl)-phenyl]-1-methyl-urea;

(1340) 1-(3,5-dimethyl-4-{2-[4-oxo-2-(5-phenyl-pentyl)-1,3,8-triaza-spiro[4.5]dec-1-ene-8-sulfonyl]-ethyl}-phenyl)-1-methyl-urea;

(1341) 1-(3,5-dimethyl-4-{2-[2-(3-nonafluorobutyl-phenyl)-4-oxo-1,3,8-triaza-spiro[4.5]dec-1-ene-8-sulfonyl]-ethyl}-phenyl)-1-methyl-urea;

(1342) 1-(3,5-dimethyl-4-{2-[4-oxo-2-(4-pentyl-phenyl)-1,3,8-triaza-spiro[4.5]dec-1-ene-8-sulfonyl]-ethyl}-phenyl)-1-methyl-urea;

(1343) 1-(3,5-dimethyl-4-{2-[4-oxo-2-((1S,3R)-3-propyl-cyclohexyl)-1,3,8-triaza-spiro[4.5]dec-1-ene-8-sulfonyl]-ethyl}-phenyl)-1-methyl-urea;

(1344) 1-(4-{2-[2-(6-ethoxy-hexyl)-4-oxo-1,3,8-triaza-spiro[4.5]dec-1-ene-8-sulfonyl]-ethyl}-3,5-dimethyl-phenyl)-1-methyl-urea;

(1345) 1-[3,5-dimethyl-4-(2-{4-oxo-2-[3-(6,6,6-trifluoro-hexyl)-phenyl]-1,3,8-triaza-spiro[4.5]dec-1-ene-8-sulfonyl}-ethyl)-phenyl]-1-methyl-urea;

(1346) 1-[3,5-dimethyl-4-(2-{4-oxo-2-[4-(6,6,6-trifluoro-hexyl)-phenyl]-1,3,8-triaza-spiro[4.5]dec-1-ene-8-sulfonyl}-ethyl)-phenyl]-1-methyl-urea;

(1347) 12-(8-{2-[2,6-dimethyl-4-(1-methyl-ureido)-phenyl]-ethanesulfonyl}-4-oxo-1,3,8-triaza-spiro[4.5]dec-1-en-2-yl)-dodecanoic acid ethyl ester;

(1348) 1-(3,5-dimethyl-4-{2-[4-oxo-2-(9-phenyl-nonyl)-1,3,8-triaza-spiro[4.5]dec-1-ene-8-sulfonyl]-ethyl}-phenyl)-1-methyl-urea;

(1349) 1-(3,5-dimethyl-4-{2-[4-oxo-2-(6-phenyl-hexyl)-1,3,8-triaza-spiro[4.5]dec-1-ene-8-sulfonyl]-ethyl}-phenyl)-1-methyl-urea;

(1350) 14-(8-{2-[2,6-dimethyl-4-(1-methyl-ureido)-phenyl]-ethanesulfonyl}-4-oxo-1,3,8-triaza-spiro[4.5]dec-1-en-2-yl)-tetradecanoic acid;

(1351) 1-(4-{2-[2-(7-methoxy-heptyl)-4-oxo-1,3,8-triaza-spiro[4.5]dec-1-ene-8-sulfonyl]-ethyl}-3,5-dimethyl-phenyl)-1-methyl-urea;

(1352) 1-(3,5-dimethyl-4-{2-[4-oxo-2-(5-propoxy-pentyl)-1,3,8-triaza-spiro[4.5]dec-1-ene-8-sulfonyl]-ethyl}-phenyl)-1-methyl-urea;

(1353) 1-(3,5-dimethyl-4-{2-[4-oxo-2-(3-propyl-nonyl)-1,3,8-triaza-spiro[4.5]dec-1-ene-8-sulfonyl]-ethyl}-phenyl)-1-methyl-urea;

(1354) 1-(4-{2-[2-(3-methoxy-4-pentyl-phenyl)-4-oxo-1,3,8-triaza-spiro[4.5]dec-1-ene-8-sulfonyl]-ethyl}-3,5-dimethyl-phenyl)-1-methyl-urea;

(1355) 1-(3,5-dimethyl-4-{2-[4-oxo-2-(2-propyl-benzofuran-6-yl)-1,3,8-triaza-spiro[4.5]dec-1-ene-8-sulfonyl]-ethyl}-phenyl)-1-methyl-urea;

(1356) 1-[3,5-dimethyl-4-(2-{4-oxo-2-[5-(propane-1-sulfonyl)-pentyl]-1,3,8-triaza-spiro[4.5]dec-1-ene-8-sulfonyl}-ethyl)-phenyl]-1-methyl-urea;

(1357) 1-(4-{2-[2-(7-methanesulfonyl-heptyl)-4-oxo-1,3,8-triaza-spiro[4.5]dec-1-ene-8-sulfonyl]-ethyl}-3,5-dimethyl-phenyl)-1-methyl-urea;

(1358) 1-[3,5-dimethyl-4-(2-{4-oxo-2-[4-(4,4,4-trifluoro-butyl)-phenyl]-1,3,8-triaza-spiro[4.5]dec-1-ene-8-sulfonyl}-ethyl)-phenyl]-1-methyl-urea;

(1359) 1-[3,5-dimethyl-4-(2-{4-oxo-2-[3-(4,4,4-trifluoro-butyl)-phenyl]-1,3,8-triaza-spiro[4.5]dec-1-ene-8-sulfonyl}-ethyl)-phenyl]-1-methyl-urea;

(1360) [11-(8-{2-[2,6-dimethyl-4-(1-methyl-ureido)-phenyl]-ethanesulfonyl}-4-oxo-1,3,8-triaza-spiro[4.5]dec-1-en-2-yl)-undecyl]-carbamic acid tert-butyl ester;

(1361) 1-(4-{2-[2-(11-hydroxy-undecyl)-4-oxo-1,3,8-triaza-spiro[4.5]dec-1-ene-8-sulfonyl]-ethyl}-3,5-dimethyl-phenyl)-1-methyl-urea;

(1362) 10-(8-{2-[2,6-dimethyl-4-(1-methyl-ureido)-phenyl]-ethanesulfonyl}-4-oxo-1,3,8-triaza-spiro[4.5]dec-1-en-2-yl)-decanoic acid;

(1363) 10-(8-{2-[2,6-dimethyl-4-(1-methyl-ureido)-phenyl]-ethanesulfonyl}-4-oxo-1,3,8-triaza-spiro[4.5]dec-1-en-2-yl)-decanoic acid amide;

(1364) 1-(3,5-dimethyl-4-{2-[2-(4-[1,1,1-$^{2}H_{3}$]-methyl-[4-$^{2}H_{1}$]cyclohexyl)-4-oxo-1,3,8-triaza-spiro[4.5]dec-1-ene-8-sulfonyl]-ethyl}-phenyl)-1-methyl-urea;

(1365) 1-(3,5-dimethyl-4-{(E)-2-[4-oxo-2-(9-phenyl-nonyl)-1,3,8-triaza-spiro[4.5]dec-1-ene-8-sulfonyl]-vinyl}-phenyl)-1-methyl-urea;

(1366) 1-(4-{2-[2-(11-amino-undecyl)-4-oxo-1,3,8-triaza-spiro[4.5]dec-1-ene-8-sulfonyl]-ethyl}-3,5-dimethyl-phenyl)-1-methyl-urea;

(1367) 3-[(3,5-dimethyl-4-{2-[2-(4-methyl-cyclohexyl)-4-oxo-1,3,8-triaza-spiro[4.5]dec-1-ene-8-sulfonyl]-ethyl}-phenyl)-methyl-amino]-4-ethoxy-cyclobut-3-ene-1,2-dione;

(1368) 3-amino-4-[(3,5-dimethyl-4-{2-[2-(4-methyl-cyclohexyl)-4-oxo-1,3,8-triaza-spiro[4.5]dec-1-ene-8-sulfonyl]-ethyl}-phenyl)-methyl-amino]-cyclobut-3-ene-1,2-dione;

(1369) 3-dimethylamino-4-[(3,5-dimethyl-4-{2-[2-(4-methyl-cyclohexyl)-4-oxo-1,3,8-triaza-spiro[4.5]dec-1-ene-8-sulfonyl]-ethyl}-phenyl)-methyl-amino]-cyclobut-3-ene-1,2-dione;

(1370) N-(4-{2-[2-(4-ethynyl-cyclohexyl)-4-oxo-1,3,8-triaza-spiro[4.5]dec-1-ene-8-sulfonyl]-ethyl}-3-methyl-phenyl)-acetamide;

(1371) 1-(4-{2-[4-[(Z)-hydroxyimino]-2-(4-methyl-cyclohexyl)-1,3,8-triaza-spiro[4.5]dec-1-ene-8-sulfonyl]-ethyl}-3,5-dimethyl-phenyl)-1-methyl-urea;

(1372) 2-(4-methyl-cyclohexyl)-4-oxo-1,3,8-triaza-spiro[4.5]dec-1-ene-8-sulfonic acid 2-methyl-benzylamide;

(1373) 2-(4-methyl-cyclohexyl)-4-oxo-1,3,8-triaza-spiro[4.5]dec-1-ene-8-sulfonic acid (2-o-tolyl-ethyl)-amide;

(1374) 2-cyclohexyl-8-{2-[1-((S)-2,3-dihydroxy-propyl)-1H-indol-4-yl]-2-hydroxy-ethanesulfonyl}-1,3,8-triaza-spiro[4.5]dec-1-en-4-one;

(1375) 2-cyclohexyl-8-(2-oxo-2-o-tolyl-ethanesulfonyl)-1,3,8-triaza-spiro[4.5]dec-1-en-4-one;

(1376) 2-cyclohexyl-8-(2-o-tolyl-ethynesulfonyl)-1,3,8-triaza-spiro[4.5]dec-1-en-4-one;

(1377) 2-cyclohexyl-8-[2-(1H-indol-4-yl)-ethynesulfonyl]-1,3,8-triaza-spiro[4.5]dec-1-en-4-one;

(1378) 3,5,N,N-tetramethyl-4-(2-{4-oxo-2-[4-(3,3,3-trifluoro-propyl)-cyclohexyl]-1,3,8-triaza-spiro[4.5]dec-1-ene-8-sulfonyl}-ethyl)-benzamide;

(1379) 3,5,N,N-tetramethyl-4-{2-[2-(4-methyl-cyclohexyl)-4-oxo-1,3,8-triaza-spiro[4.5]dec-1-ene-8-sulfonyl]-ethyl}-benzamide;

(1380) 8-{2-[4-(4-hydroxy-4-methyl-piperidine-1-carbonyl)-2,6-dimethyl-phenyl]-ethanesulfonyl}-2-[4-(3,3,3-trifluoro-propyl)-cyclohexyl]-1,3,8-triaza-spiro[4.5]dec-1-en-4-one;

(1381) 8-{2-[4-(4-fluoromethyl-4-hydroxy-piperidine-1-carbonyl)-2,6-dimethyl-phenyl]-ethanesulfonyl}-2-[4-(3,3,3-trifluoro-propyl)-cyclohexyl]-1,3,8-triaza-spiro[4.5]dec-1-en-4-one;

(1382) 8-{2-[4-(4-hydroxy-4-methyl-piperidine-1-carbonyl)-2,6-dimethyl-phenyl]-ethanesulfonyl}-2-(4-methyl-cyclohexyl)-1,3,8-triaza-spiro[4.5]dec-1-en-4-one;

(1383) 8-{2-[4-(4-fluoromethyl-4-hydroxy-piperidine-1-carbonyl)-2,6-dimethyl-phenyl]-ethanesulfonyl}-2-(4-methyl-cyclohexyl)-1,3,8-triaza-spiro[4.5]dec-1-en-4-one;

(1384) 8-(2-{4-[4-((R)-2,3-dihydroxy-propoxy)-piperidine-1-carbonyl]-2,6-dimethyl-phenyl}-ethanesulfonyl)-2-[4-(3,3,3-trifluoro-propyl)-cyclohexyl]-1,3,8-triaza-spiro[4.5]dec-1-en-4-one;

(1385) 3,5-dimethyl-4-(2-{4-oxo-2-[4-(3,3,3-trifluoro-propyl)-cyclohexyl]-1,3,8-triaza-spiro[4.5]dec-1-ene-8-sulfonyl}-ethyl)-benzoic acid hydrazide;

(1386) 8-{2-[2,6-dimethyl-4-(pyrazolidine-1-carbonyl)-phenyl]-ethanesulfonyl}-2-[4-(3,3,3-trifluoro-propyl)-cyclohexyl]-1,3,8-triaza-spiro[4.5]dec-1-en-4-one;

(1387) N,N-dimethyl-2-(3-methyl-4-{2-[2-(4-methyl-cyclohexyl)-4-oxo-1,3,8-triaza-spiro[4.5]dec-1-ene-8-sulfonyl]-ethyl}-phenyl)-acetamide;

(1388) N-methoxy-2-(3-methyl-4-{2-[2-(4-methyl-cyclohexyl)-4-oxo-1,3,8-triaza-spiro[4.5]dec-1-ene-8-sulfonyl]-ethyl}-phenyl)-acetamide;

(1389) 1-[3,5-dimethyl-4-(2-{4-oxo-2-[4-(3,3,3-trifluoro-propyl)-cyclohexyl]-1,3,8-triaza-spiro[4.5]dec-1-ene-8-sulfonyl}-ethyl)-benzyl]-1-methyl-urea;

(1390) 1-(3,5-dimethyl-4-{2-[2-(4-methyl-cyclohexyl)-4-oxo-1,3,8-triaza-spiro[4.5]dec-1-ene-8-sulfonyl]-ethyl}-benzyl)-1-methyl-urea;

(1391) 1-(4-{2-[2-(4-fluoro-3-trifluoromethyl-phenyl)-4-oxo-1,3,8-triaza-spiro[4.5]dec-1-ene-8-sulfonyl]-ethyl}-3,5-dimethyl-phenyl)-1-[1,1,1-$^{2}H_{3}$]methyl-urea;

(1392) 2-cyclohexyl-8-{2-[1-((2S,3S)-2,3,4-trihydroxy-butyl)-1H-indol-4-yl]-ethanesulfonyl}-1,3,8-triaza-spiro[4.5]dec-1-en-4-one;

(1393) 8-{2-[1-((2S,3S)-4-benzyloxy-2,3-dihydroxy-butyl)-1H-indol-4-yl]-ethanesulfonyl}-2-cyclohexyl-1,3,8-triaza-spiro[4.5]dec-1-en-4-one;

(1394) N-[3-methyl-4-(2-{4-oxo-2-[4-(3,3,3-trifluoro-propyl)-cyclohexyl]-1,3,8-triaza-spiro[4.5]dec-1-ene-8-sulfonyl}-ethyl)-benzyl]-acetamide;

(1395) 3,N,N-trimethyl-4-{2-[4-oxo-2-(3-trifluoromethyl-phenylamino)-1,3,8-triaza-spiro[4.5]dec-1-ene-8-sulfonyl]-ethyl}-benzamide;

(1396) 3,N,N-trimethyl-4-{2-[4-oxo-2-(4-trifluoromethyl-phenylamino)-1,3,8-triaza-spiro[4.5]dec-1-ene-8-sulfonyl]-ethyl}-benzamide;

(1397) 3,N,N-trimethyl-4-{2-[2-(methyl-phenyl-amino)-4-oxo-1,3,8-triaza-spiro[4.5]dec-1-ene-8-sulfonyl]-ethyl}-benzamide;

(1398) 4-{2-[2-(benzyl-methyl-amino)-4-oxo-1,3,8-triaza-spiro[4.5]dec-1-ene-8-sulfonyl]-ethyl}-3,N,N-trimethyl-benzamide;

(1399) 4-{2-[2-(cyclohexylmethyl-amino)-4-oxo-1,3,8-triaza-spiro[4.5]dec-1-ene-8-sulfonyl]-ethyl}-3,N,N-trimethyl-benzamide;

(1400) 3,N,N-trimethyl-4-(2-{2-[methyl-(4-trifluoromethyl-phenyl)-amino]-4-oxo-1,3,8-triaza-spiro[4.5]dec-1-ene-8-sulfonyl}-ethyl)-benzamide;

(1401) N-(3-methyl-4-{2-[4-oxo-2-(4-trifluoromethyl-phenylamino)-1,3,8-triaza-spiro[4.5]dec-1-ene-8-sulfonyl]-ethyl}-phenyl)-acetamide;

(1402) N-(3-methyl-4-{2-[4-oxo-2-(3-trifluoromethyl-phenylamino)-1,3,8-triaza-spiro[4.5]dec-1-ene-8-sulfonyl]-ethyl}-phenyl)-acetamide;

(1403) 4-{2-[2-(4-butyl-piperidin-1-yl)-4-oxo-1,3,8-triaza-spiro[4.5]dec-1-ene-8-sulfonyl]-ethyl}-3,N,N-trimethyl-benzamide;

(1404) 4-{2-[2-(4-butyl-cyclohexylamino)-4-oxo-1,3,8-triaza-spiro[4.5]dec-1-ene-8-sulfonyl]-ethyl}-3,N,N-trimethyl-benzamide;

(1405) 4-{2-[2-(3-but-3-enyloxy-5-trifluoromethyl-phenyl)-4-oxo-1,3,8-triaza-spiro[4.5]dec-1-ene-8-sulfonyl]-ethyl}-3,N-dimethyl-N-pent-4-enyl-benzamide;

(1419) N-(2-allyloxy-ethyl)-4-{2-[2-(3-but-3-enyloxy-5-trifluoromethyl-phenyl)-4-oxo-1,3,8-triaza-spiro[4.5]dec-1-ene-8-sulfonyl]-ethyl}-3,N-dimethyl-benzamide;

(1443) dec-9-enoic acid {4-[2-(2-hex-5-enyl-4-oxo-1,3,8-triaza-spiro[4.5]dec-1-ene-8-sulfonyl)-ethyl]-3,5-dimethyl-phenyl}-methyl-amide; or (1446) hept-6-enoic acid {4-[2-(2-hex-5-enyl-4-oxo-1,3,8-triaza-spiro[4.5]dec-1-ene-8-sulfonyl)-ethyl]-3,5-dimethyl-phenyl}-methyl-amide, or a pharmacologically acceptable salt thereof.

Such compounds represented by the above formula (1) or pharmacologically acceptable salts thereof according to the present invention are useful as compounds having a PTH-like effect, preferably PTH1 receptor agonists, and are useful for the prevention and/or treatment of osteoporosis, fracture, osteomalacia, arthritis, thrombocytopenia, hypoparathyroidism, hyperphosphatemia, tumoral calcinosis or the like, or stem cell mobilization.

The compounds or salts thereof according to the present invention can be formulated by conventional methods into tablets, powders, fine granules, granules, coated tablets, capsules, syrups, troches, inhalations, suppositories, injections, ointments, ophthalmic ointments, ophthalmic preparations, nasal preparations, ear preparations, cataplasms, lotions and the like. Commonly used excipients, binders, lubricants, colorants, correctives, and as necessary, stabilizers, emulsifiers, absorption promoters, surfactants, pH adjusters, preservatives, antioxidants and the like can be used for formulation, and they are blended with ingredients commonly used as raw materials of pharmaceutical preparations and formulated by conventional methods.

For example, oral preparations are manufactured by adding, to the compound or a pharmacologically acceptable salt thereof according to the present invention, an excipient, and as necessary, a binder, a disintegrant, a lubricant, a colorant, a corrective and the like and then formulating them into powder, fine granules, granules, tablets, coated tablets, capsules and the like by a conventional method.

Examples of these ingredients include animal and vegetable oils such as soybean oil, beef tallow and synthetic glyceride; hydrocarbons such as liquid paraffin, squalane and solid paraffin; ester oils such as octyldodecyl myristate and isopropyl myristate; higher alcohols such as cetostearyl alcohol and behenyl alcohol; silicone resin; silicone oil; surfactants such as polyoxyethylene fatty acid ester, sorbitan fatty acid ester, glycerol fatty acid ester, polyoxyethylene sorbitan fatty acid ester, polyoxyethylene hydrogenated castor oil and a polyoxyethylene-polyoxypropylene block copolymer; water-soluble polymers such as hydroxyethylcellulose, polyacrylic acid, a carboxyvinyl polymer, polyethylene glycol, polyvinylpyrrolidone and methylcellulose; lower alcohols such as ethanol and isopropanol; polyhydric alcohols such as glycerol, propylene glycol, dipropylene glycol and sorbitol; sugars such as glucose and sucrose; inorganic powders such as silicic anhydride, magnesium aluminum silicate and aluminum silicate; and purified water.

Examples of the excipients include lactose, corn starch, white soft sugar, glucose, mannitol, sorbitol, microcrystalline cellulose and silicon dioxide.

Examples of the binders include polyvinyl alcohol, polyvinyl ether, methylcellulose, ethylcellulose, acacia, tragacanth, gelatin, shellac, hydroxypropylmethylcellulose, hydroxypropylcellulose, polyvinylpyrrolidone, a polypropylene glycol-polyoxyethylene block polymer and meglumine.

Examples of the disintegrants include starch, agar, gelatin powder, microcrystalline cellulose, calcium carbonate, sodium bicarbonate, calcium citrate, dextrin, pectin and carboxymethylcellulose calcium.

Examples of the lubricants include magnesium stearate, talc, polyethylene glycol, silica and hydrogenated vegetable oil.

Colorants used are those approved as additives to pharmaceuticals. Correctives used are cocoa powder, peppermint camphor, empasm, mentha oil, borneol, powdered cinnamon bark and the like.

Obviously, these tablets and granules may be sugar-coated or otherwise coated appropriately as necessary. Liquid preparations such as syrups and injectable preparations are manufactured by adding a pH adjuster, a solubilizer, a tonicity adjusting agent and the like, and as necessary, a solubilizing agent, a stabilizer and the like to the compound or a pharmacologically acceptable salt thereof according to the present invention and formulating them by a conventional method.

The method of manufacturing external preparations is not limited and they can be manufactured by conventional methods. Specifically, various raw materials commonly used for pharmaceuticals, quasi drugs, cosmetics and the like can be used as base materials for formulation. Specific examples of the base materials used include raw materials such as animal and vegetable oils, mineral oils, ester oils, waxes, higher alcohols, fatty acids, silicone oil, surfactants, phospholipids, alcohols, polyhydric alcohols, water-soluble polymers, clay minerals and purified water. Further, pH adjusters, antioxidants, chelators, preservatives and fungicides, colorants, flavors and the like may be added as necessary. The base materials for external preparations according to the present invention are not limited to these materials.

Ingredients such as ingredients having a differentiation-inducing effect, blood flow promoters, bactericides, anti-inflammatory agents, cell activators, vitamins, amino acids, humectants and keratolytic agents may also be blended as necessary. The aforementioned base materials are added in an amount corresponding to the concentration usually chosen for the manufacture of external preparations.

The mode of administration of the compounds or salts thereof, or hydrates of the compounds or salts according to the present invention is not particularly limited, and they may be orally or parenterally administered by methods commonly used. For example, they can be formulated into preparations such as tablets, powders, granules, capsules, syrups, troches, inhalations, suppositories, injections, ointments, ophthalmic ointments, ophthalmic preparations, nasal preparations, ear preparations, cataplasms and lotions and administered.

The dosage of the medicine according to the present invention can be appropriately selected depending on the severity of the symptom, the age, the sex, the body weight, the mode of administration, the type of the salt, the specific type of the disease, and the like.

Although the dosage significantly varies according to the type of the disease and the severity of the symptom of the patient, the age of the patient, the sex difference and the difference in sensitivity to drugs between the patients, and the like, the dosage is usually about 0.03 to 1000 mg, preferably 0.1 to 500 mg and more preferably 0.1 to 100 mg per day for adults and is administered divided into one to several doses a day. For injections, the dosage is usually about 1 μg/kg to 3000 μg/kg, preferably about 3 μg/kg to 1000 μg/kg.

In the manufacture of the compounds of the present invention represented by the above formula (1), raw material compounds and various reagents may form salts, hydrates or solvates, all vary according to the starting material, the solvent used, and the like, and are not particularly limited insofar as they do not inhibit the reaction.

The solvent used also varies according to the starting material, the reagent and the like, and is not particularly limited insofar as it does not inhibit the reaction and dissolves the starting material to a certain extent, obviously.

Various isomers (e.g., geometric isomers, optical isomers based on asymmetric carbons, rotamers, stereoisomers and tautomers) can be purified and isolated using common separation means, e.g., recrystallization, diastereomeric salt methods, enzymatic resolution methods and various chromatography methods (e.g., thin-layer chromatography, column chromatography, high performance liquid chromatography and gas chromatography).

The compounds according to the present invention obtained as free forms can be converted to salts that may be formed by the compounds or to hydrates of the compounds according to conventional methods. The compounds according to the present invention obtained as salts or hydrates of the compounds can also be converted to free forms of the compounds according to conventional methods.

The compounds according to the present invention can be isolated and purified by applying common chemical operations such as extraction, concentration, evaporation, crystallization, filtration, recrystallization and various chromatography methods.

All prior art documents cited herein are hereby incorporated by reference.

General manufacturing methods for the compounds of the present invention and examples will be shown below.

General Synthesis Methods

The compounds of the present invention can be synthesized by various methods, some of which will be described with reference to the following schemes. The schemes are illustrative and the present invention is not limited only by the chemical reactions and conditions explicitly indicated. Although some substituents are excluded in the following schemes for the sake of clarity, such exclusion is not intended to limit the disclosure of the schemes. Representative compounds of the present invention can be synthesized using appropriate intermediates, known compounds, and reagents. $R_1$, $R_2$, $R_{33}$, $R_{34}$, W, X, Y, m and n in the formulas in the following general synthesis methods are as defined for $R_1$, $R_2$, $R_{33}$, $R_{34}$, W, X, Y, m and n in the compounds represented by the above general formula (1) (compounds represented by the formula I in the following general synthesis methods).

The compounds of the general formula (1) according to the present invention can be synthesized by the manufacturing methods shown below.

Scheme 1 (Method A)

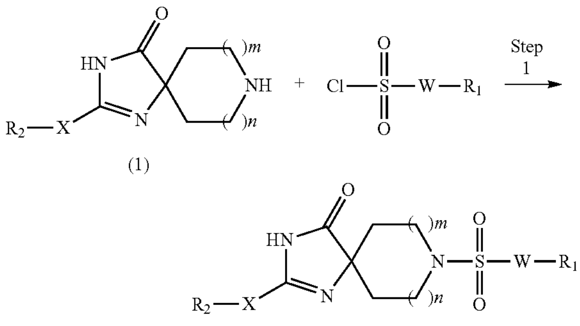

(1)

Formula I

Scheme 1 (Method A) is a method of reacting a spiro-amine derivative (1) with various sulfonyl chlorides (2) in an appropriate solvent such as dichloromethane or tetrahydrofuran in the presence of an appropriate base such as triethylamine or pyridine. The reaction temperature is 0° C. to room temperature, for example, and the reaction time is 0.5 to 24 hours. The resulting sulfonamide derivative (formula I) is isolated by a common technique and, if necessary, may be purified by crystallization or chromatography.

The spiro-amine derivative (1) shown in Scheme 1 can be synthesized from an acylamino-nitrile derivative (3) or acylamino-amide derivative (4). Scheme 2 shows a method of synthesizing the spiro-amine derivative (1).

Scheme 2

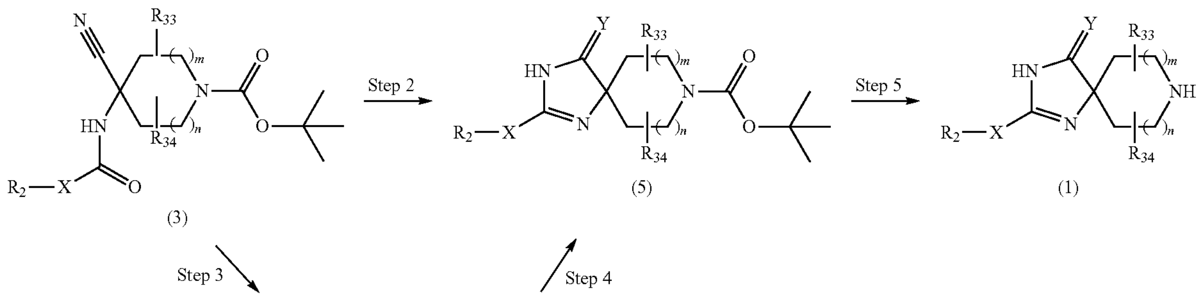

(3)

(5)

(1)

-continued

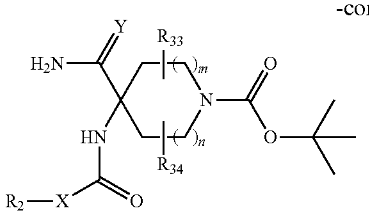

(In the scheme, Y = O.)

Step 2 is a method of cyclizing an acylamino-nitrile derivative (3) in an appropriate solvent such as an aqueous ethanol solution or an aqueous dimethyl sulfoxide solution in the presence of an aqueous sodium hydroxide solution and aqueous hydrogen peroxide solution. The reaction temperature is reflux temperature, for example, and the reaction time is 1 to 24 hours. The resulting cyclized derivative (5) is isolated by a common technique and, if necessary, may be purified by crystallization or chromatography.

The cyclized derivative (5) can also be synthesized by two-step reaction (Step 3, Step 4). Step 3 is a method of converting the nitrile group to an amido group under basic hydrolysis conditions in the presence of hydrogen peroxide. (This reaction can be performed with reference to Chemistry—A European Journal (2002), 8(2), 439-450, for example.) Step 4 is a method of cyclizing an acylamino-amide derivative (4) in an appropriate solvent such as ethanol, tert-butanol or dimethyl sulfoxide in the presence of an appropriate base such as an aqueous sodium hydroxide solution or potassium t-butoxide. The reaction temperature is room temperature to reflux temperature, for example, and the reaction time is 1 to 24 hours. The resulting cyclized derivative (5) is isolated by a common technique and, if necessary, may be purified by crystallization or chromatography.

Step 5 is a reaction of deprotecting the t-butoxycarbonyl group with an appropriate acid such as trifluoroacetic acid or hydrochloric acid in an appropriate solvent such as dichloromethane, dioxane or methanol. (This reaction can be performed with reference to Protective Groups in Organic Synthesis, Wiley-Interscience, for example.)

The acylamino-nitrile derivative (3) or acylamino-amide derivative (4) shown in Scheme 2 can be synthesized from an amino-nitrile derivative (8a) or amino-amide derivative (8b). Scheme 3 shows a method of synthesizing the acylamino-nitrile derivative (3) or acylamino-amide derivative (4).

Scheme 3

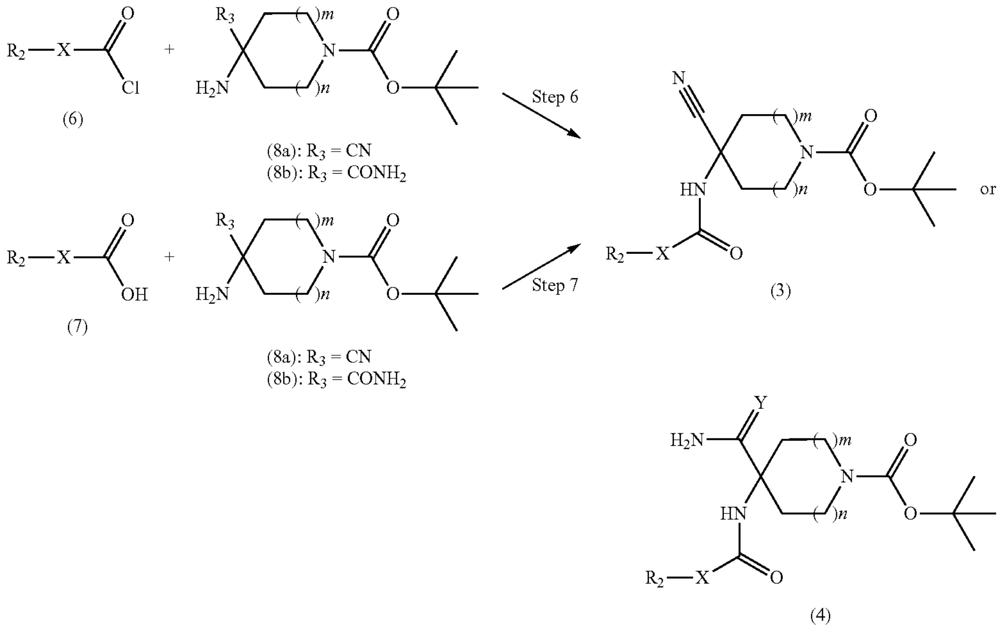

(In the scheme, Y = O.)

Step 6 is a method of reacting an acid chloride derivative (6) with an amino-nitrile derivative (8a) or amino-amide derivative (8b), respectively, in an appropriate solvent such as dichloromethane or tetrahydrofuran in the presence of an appropriate base such as triethylamine or pyridine. The reaction temperature is 0° C. to room temperature, for example, and the reaction time is 0.5 to 24 hours. The resulting acylamino-nitrile derivative (3) or acylamino-amide derivative (4) is isolated by a common technique and, if necessary, may be purified by crystallization or chromatography. The acid chloride derivative (6) used for the reaction can be purchased or can be synthesized from a carboxylic acid derivative (7) by the method described in March, Advanced Organic Chemistry, 5th Edition, John Wiley and Sons, New York, P 523-P 524, for example.

Step 7 is a method of reacting a carboxylic acid derivative (7) with amino-nitrile (8a) or amino-amide (8b). Examples of the coupling reagent include N,N'-dicyclohexylcarbodiimide (DCC), 1-ethyl-3-(3-dimethylaminopropyl)carbodiimide hydrochloride (EDC), O-(7-azabenzotriazol-1-yl)-1,1,3,3-tetramethyluronium hexafluorophosphate (HATU) and 4-(4,6-dimethoxy-1,3,5-triazin-2-yl)-4-methylmorpholinium chloride n-hydrate (DMT-MM). Examples of the base include triethylamine or N,N-diisopropylethylamine. If necessary, 4-(dimethylamino)pyridine (DMAP) may be used as a catalyst. Examples of the appropriate solvent include dichloromethane or N,N-dimethylformamide. Examples of the appropriate solvent used in the case of DMT-MM include methanol, ethanol and acetonitrile. The reaction temperature is 0° C. to room temperature, for example, and the reaction time is 0.5 to 24 hours. The resulting acylamino-nitrile derivative (3) or acylamino-amide derivative (4) is isolated by a common technique and, if necessary, may be purified by crystallization or chromatography.

The sulfonyl chloride derivative (2) shown in Scheme 1 can be purchased or can be synthesized as shown in Scheme 4a and Scheme 4b.

Scheme 4a

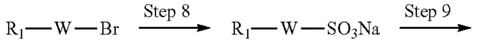

(9) (10)

-continued

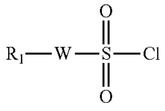

(2)

Scheme 4a is a method of synthesizing a sulfonyl chloride derivative (2) from a bromide derivative (9) through a sodium salt derivative of sulfonic acid (10). This method of providing a sulfonyl chloride can be performed with reference to J. Org. Chem. 1985, 50(12), 2066-2073 or J. Org. Chem. 1984, 49(26), 5124-5131, for example.

Scheme 4b

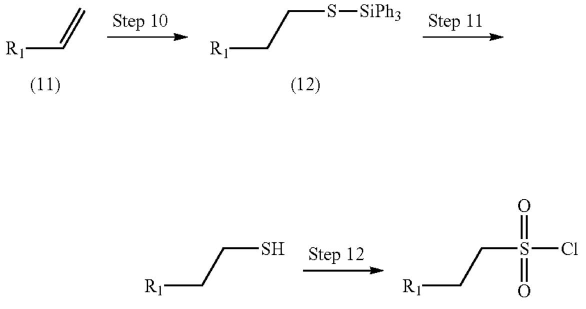

(11) (12) (13) (14)

Scheme 4b is a method of synthesizing a sulfonyl chloride derivative, in particular, an ethylsulfonyl chloride derivative (14) from a styrene derivative (11). This reaction can be performed with reference to Tetrahedron Lett., Vol 35, 1837-1840 (1994) or Chemistry Lett., 1483-1486 (1992), for example.

The spiro-amine structure of the formula I can be synthesized by cyclization of an amide derivative such as (15) or (16) of Scheme 5 (Method B).

Scheme 5 (Method B)

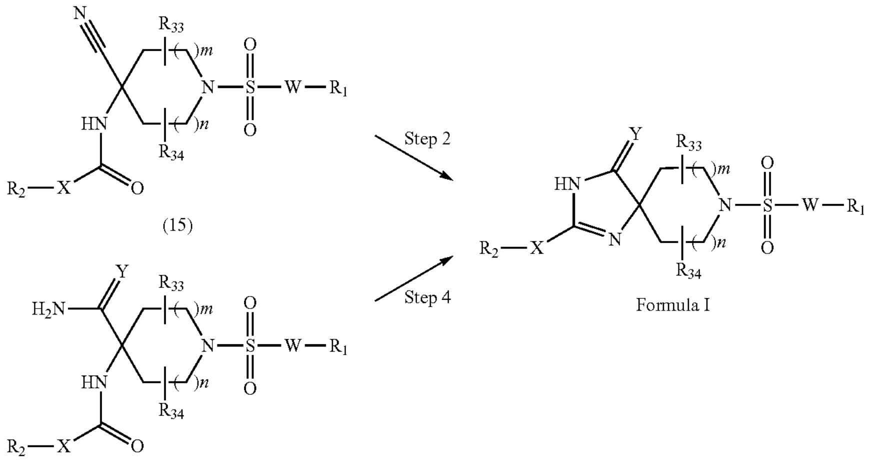

(15) (16) Formula I (In the scheme, Y = O.)

The compound I is synthedized by cyclizing an amide derivative represented by (15) or (16) using the above-described method of Step 2 or Step 4.

The amide derivative ((15) or (16)) shown in Scheme 5 can be derived from a keto-amine derivative (17). Scheme 6 shows a method of synthesizing the amide derivative ((15) or (16)).

Scheme 6

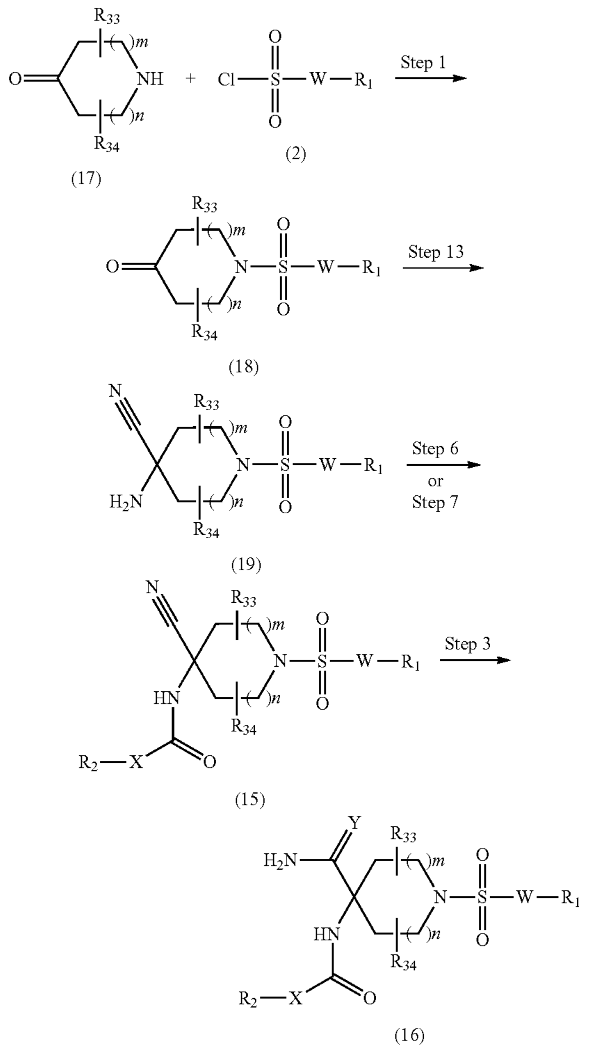

(In the scheme, Y = O.)

Step 1 is a method of reacting a keto-amine derivative (17) with a sulfonyl chloride derivative (2). Step 13 is a Strecker synthesis of converting a ketone derivative (18) to an amino-nitrile derivative (19). Specifically, this is a method of reacting a ketone derivative (18) with sodium cyanide or potassium cyanide and ammonium chloride or ammonium acetate in an appropriate solvent such as methanol, ethanol or tetrahydrofuran in the presence/absence of water. The reaction temperature is room temperature to 80° C., for example, and the reaction time is 2 to 72 hours. The resulting amino-nitrile derivative (19) is isolated by a common technique and, if necessary, may be purified by crystallization or chromatography.

The cyano-amide derivative (15) can be synthesized by the same method as in Step 6 or Step 7 in Scheme 3. Step 3 is a method of synthesizing an amido-amide compound (16) by hydrolysis of the cyano-amide derivative (15).

The spiro-amine derivative of the formula I, in particular, the aryl-ethenylsulfonamide derivative of the formula II (o=0) and the aryl-propenylsulfonamide derivative of the formula II (o=1), can be synthesized by a Heck reaction of an olefinated sulfonamide derivative (20) with an aryl halide (21) in Scheme 7.

Scheme 7 (Method C)

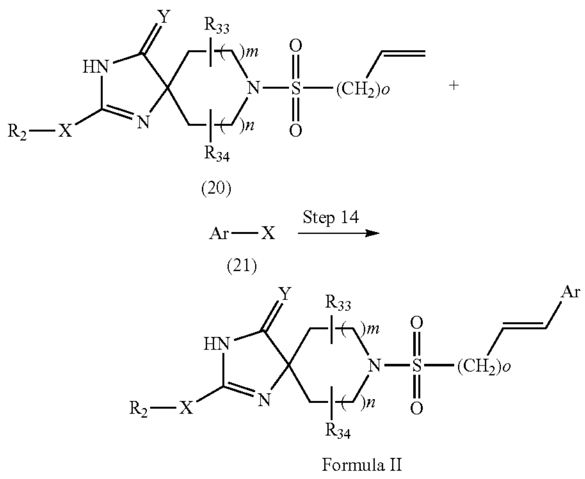

(In the scheme, Y = O.)

Step 14 is a method of synthesizing an arylethenylsulfonamide derivative (formula II) by coupling an olefinated sulfonamide derivative (20) with an aryl halide derivative (21) in an appropriate solvent such as N,N-dimethylacetamide (DMA), N,N-dimethylformamide (DMF) or 1,4-dioxane in the presence of a palladium catalyst such as palladium(II) acetate ($Pd(OAc)_2$) or tetrakis(triphenylphosphine)palladium (0) ($Pd(PPh_3)_4$), in the presence or absence of a phosphine ligand such as triphenylphosphine ($PPh_3$) or tri-o-tolylphosphine ($(o\text{-tol})_3P$) and in the presence of an appropriate base such as triethylamine, respectively, in an $N_2$ atmosphere. The reaction temperature is 90° C. to reflux temperature. This reaction can be performed under microwave irradiation. The resulting arylethenylsulfonamide derivative (formula II) is isolated by a common technique and, if necessary, may be purified by crystallization or chromatography.

The spiro-amine derivative (formula I), in particular, the ethenylsulfonamide derivative (formula III), can also be synthesized by coupling a Horner-Wadsworth-Emmons reagent with an aldehyde derivative (24) as shown in Scheme 8.

Scheme 8 (Method D)

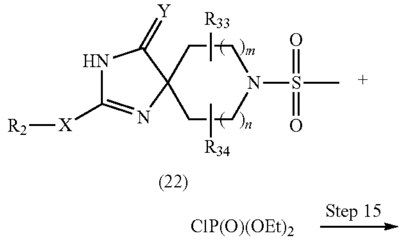

-continued

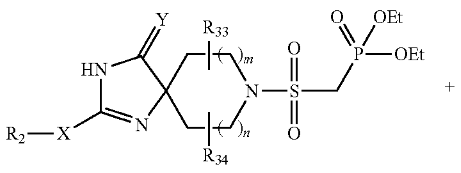

(23)

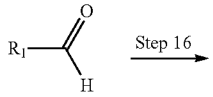

(24)

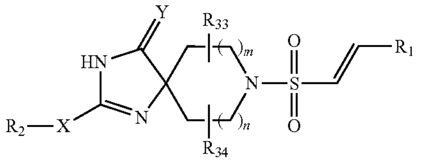

Formula III (In the scheme, Y = O.)

Step 15 is a method of synthesizing a Horner-Wadsworth-Emmons reagent (23) by coupling a methanesulfonamide derivative (22) with diethyl chlorophosphate in an appropriate solvent such as tetrahydrofuran or diethyl ether in the presence of a base such as lithium hexamethyldisilazide (LHMDS) or lithium diisopropylamide (LDA). The reaction is performed at −78° C. to room temperature for 1 to 24 hours in an $N_2$ atmosphere. The resulting Horner-Wadsworth-Emmons reagent (23) is isolated by a common technique and, if necessary, may be purified by crystallization or chromatography. This reaction can be performed with reference to Tetrahedron 2001, 57(37), 7899-7907, for example.

Step 16 is a method of synthesizing an ethenylsulfonamide derivative (formula III) by reacting the Horner-Wadsworth-Emmons reagent (23) with an aldehyde derivative (24) under Horner-Wadsworth-Emmons reaction conditions. This reaction can be performed with reference to Synlett 2005, 5, 834-838; Tetrahedron 2001, 57(37), 7899-7907, for example.

The spiro-amine derivative (formula I), in particular, the aryl-alkylsulfonamide derivative (formula IV), can be synthesized by reduction of an olefin of the formula II in Scheme 9.

Scheme 9 (Method E)

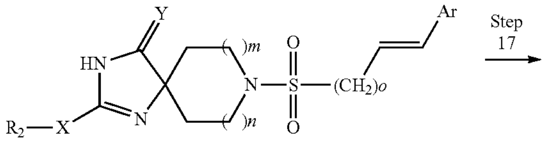

Formula II

-continued

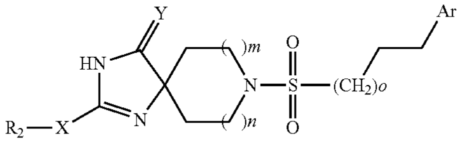

Formula IV (In the scheme, Y = O.)

Step 17 is a method of hydrogenating an olefin of the formula II in an inert solvent such as methanol, ethanol, dimethylformamide or dimethylacetamide in the presence of a catalyst such as palladium carbon or palladium hydroxide carbon, respectively, under an $H_2$ atmosphere. The reaction temperature is room temperature to 80° C., and the reaction may be performed under pressure. The resulting aryl-alkylsulfonamide derivative (formula IV) is isolated by a common technique and, if necessary, may be purified by crystallization or chromatography.

The cyclized derivative (5) amide used in the above reaction can be converted to a thioamide (Step 18) and used for the reaction of Step 5 or Step 1. This reaction can be performed with reference to March, Advanced Organic Chemistry, $5^{th}$ Edition, for example.

Scheme 10

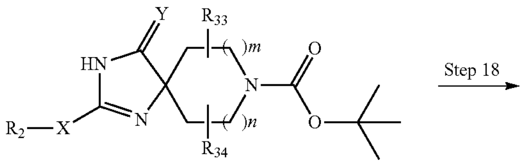

(5)

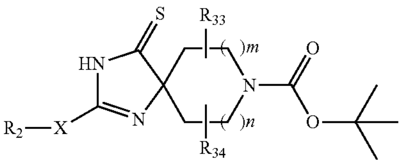

(25)

(In the scheme, Y = O.)

The ketone derivative (18) shown in Scheme 6 can be derived from a keto-amine derivative (17) through an ethenesulfonamide derivative (26). It can also be derived from a ketal-amine derivative (27) through a ketal-ethenesulfonamide derivative (28).

Scheme 11

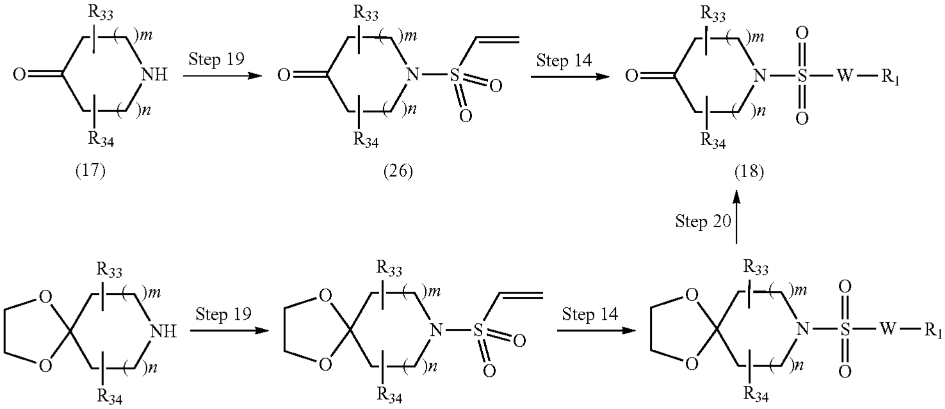

(17) (26) (18) (27) (28) (29)

Step 19 is a method of reacting a keto-amine derivative (17) or ketal-amine derivative (27) with chloroethanesulfonyl chloride in an appropriate solvent such as dichloromethane in the presence of an appropriate base such as triethylamine. The reaction temperature is 0° C. to 40° C., for example, and the reaction time is 0.1 to 1 hour. The resulting ethenesulfonamide derivative (26) or ketal-ethenesulfonamide derivative (28) is isolated by a common technique and, if necessary, may be purified by crystallization or chromatography.

The ketone derivative (18) can be synthesized from the ethenesulfonamide derivative (26) by the same method as in Step 14 in Scheme 7.

The ketone derivative (18) can also be synthesized by converting the ketal-ethenesulfonamide derivative (28) to a ketal-sulfonamide derivative (29) by the same method as in Step 14 in Scheme 7 and then deprotecting the ketal by the method of Step 20. Step 20 is a method of reacting the ketal-sulfonamide derivative (29) with an acid such as trifluoroacetic acid or hydrochloric acid in an appropriate solvent such as aqueous acetone or aqueous ethanol. The reaction temperature is 55° C. to 80° C. (boiling point of the solvent), for example, and the reaction time is 1 to 24 hours. The resulting ketone derivative (18) is isolated by a common technique and, if necessary, may be purified by crystallization or chromatography.

The olefinated sulfonamide derivative (20) shown in Scheme 7 can be derived from a spiro-amine derivative (1).

Scheme 12

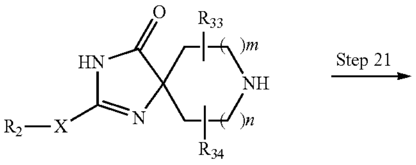

(1)

-continued

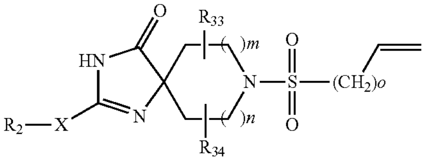

(20)

Step 21 is a method of reacting a spiro-amine derivative (1) with a sulfonyl chloride reagent (e.g., chloroethanesulfonyl chloride or 2-propene-1-sulfonyl chloride) in an appropriate solvent such as dichloromethane in the presence of an appropriate base such as triethylamine. The reaction temperature is 0° C. to 40° C., for example, and the reaction time is 0.1 to 1 hour. The resulting olefinated sulfonamide derivative (20) is isolated by a common technique and, if necessary, may be purified by crystallization or chromatography.

The methanesulfonamide derivative (22) shown in Scheme 8 can be derived from a spiro-amine derivative (1).

Scheme 13

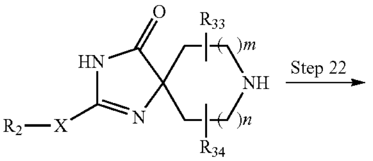

(1)

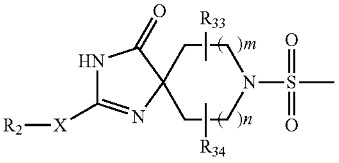

(22)

Step 22 is a method of reacting a spiro-amine derivative (1) with methanesulfonyl chloride in an appropriate solvent such as dichloromethane in the presence of an appropriate base such as triethylamine. The reaction temperature is 0° C. to room temperature, for example, and the reaction time is 0.1 to 1 hour. The methanesulfonamide derivative (22) is isolated by a common technique and, if necessary, may be purified by crystallization or chromatography.

The compound of the general formula (1) wherein Y is a sulfur atom (formula VI) can be synthesized from a thioamide intermediate (25) in Scheme 10 by the reactions of Step 5-Step 1 as in the case of the compound wherein Y is an oxygen atom, for example. It can also be synthesized from an amide derivative wherein Y is an oxygen atom (formula V) by Step 18.

Scheme 14

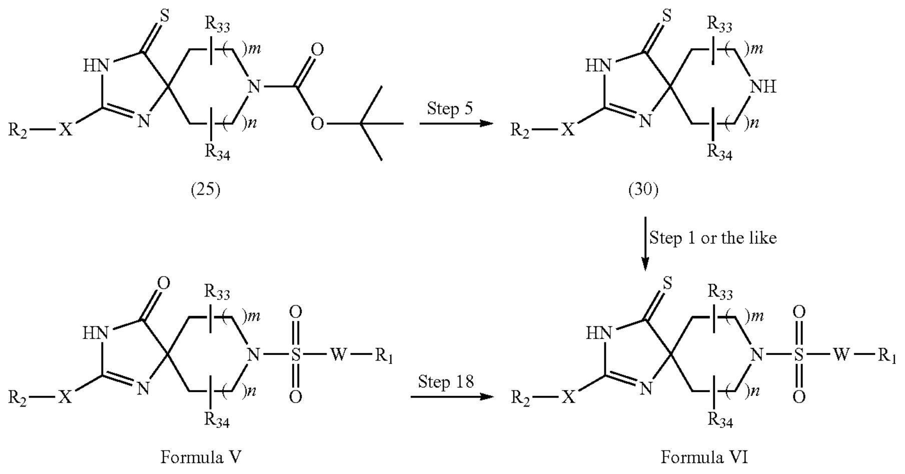

Step 18 is a method of reacting an amide derivative (formula V) with a Lawesson's reagent in an appropriate solvent such as toluene. The reaction temperature is room temperature to the boiling point of the solvent, for example, and the reaction time is several hours to 24 hours. The thioamide derivative (formula VI) is isolated by a common technique and, if necessary, may be purified by crystallization or chromatography. This conversion reaction of carbonyl to thiocarbonyl can be performed with reference to March, Advanced Organic Chemistry, $5^{th}$ Edition, for example.

The compound of the general formula (1) wherein Y is a nitrogen atom (formula VII, formula VIII) can be synthesized by converting the thioamido group of a thioamide intermediate (25) to an amidino group (step 23) to provide an amidino intermediate (31, 32) and then subjecting the intermediate to the reactions of Step 5 and subsequent Step 1 as in the case of the compound of the general formula (1) wherein Y is an oxygen atom, for example.

Scheme 15

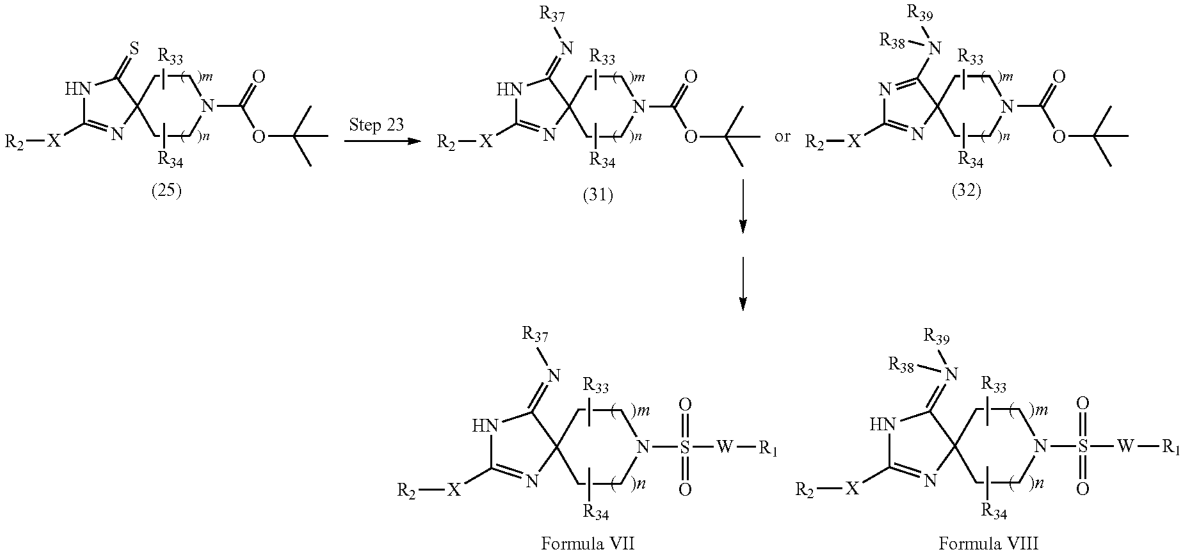

Step 23 is a method of reacting a thioamide intermediate (25) with a primary amine or secondary amine in an appropriate solvent such as methanol. The reaction temperature is room temperature to the boiling point of the solvent, for example, and the reaction time is several hours to 24 hours. The amidino intermediate (31, 32) is isolated by a common technique and, if necessary, may be purified by crystallization or chromatography.

The derivative of the general formula (1) wherein X is a single bond and $R_2$ is optionally substituted aryl or heteroaryl (formula IX) can also be synthesized from a thiohydantoin derivative (33).

Scheme 16

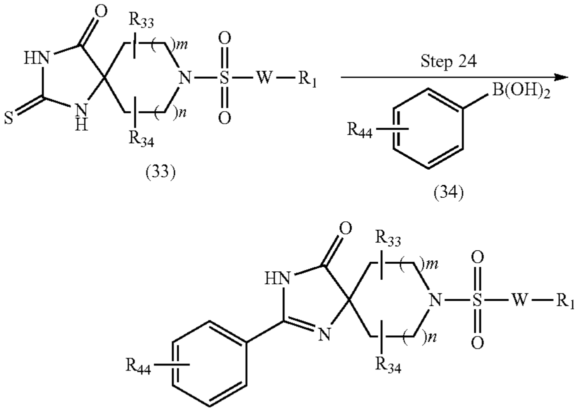

(33)

(34)

Formula IX

Step 24 is a method of reacting a thiohydantoin derivative (33) with an optionally substituted arylboronic acid (34) in an appropriate solvent such as N-methylpyrolidone in the presence of a copper catalyst such as CuTC or a palladium catalyst such as tetrakis(triphenylphosphine)palladium(0). The reaction temperature is room temperature to the boiling point of the solvent, for example, and the reaction time is 0.5 to 24 hours. The substituted phenyl derivative (formula IX) is isolated by a common technique and, if necessary, may be purified by crystallization or chromatography.

The thiohydantoin derivative (33) can be synthesized from an amino-nitrile derivative (19) through Step 3 and Step 25.

Scheme 17

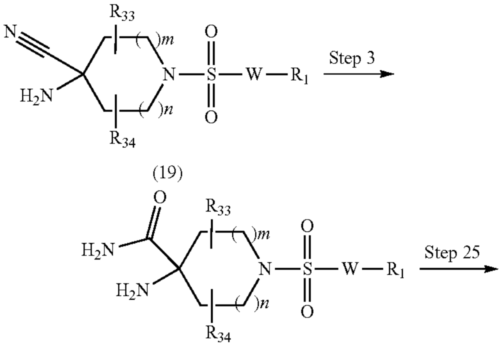

(19)

(35)

-continued

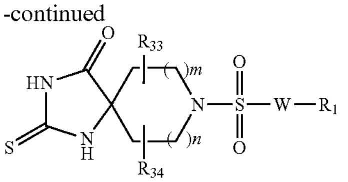

(33)

Step 3 is a method of synthesizing an amino-amide derivative (35) by hydrolyzing an amino-nitrile derivative (19). Step 25 is a reaction of converting the amino-amide derivative (35) to a thiohydantoin derivative (33). Step 25 is a method of reacting the amino-amide derivative (35) with a thiocarbonylating reagent such as di(2-pyridyl)thionocarbonate in an appropriate solvent such as tetrahydrofuran. The reaction temperature is 0° C. to room temperature, for example, and the reaction time is 0.5 hour to several hours. The thiohydantoin derivative (33) is isolated by a common technique and, if necessary, may be purified by crystallization or chromatography.

The alkynyl derivative of the general formula (1) wherein W is acetylene and $R_1$ is optionally substituted aryl or heteroaryl (formula XI) can be synthesized through an acetophenone derivative (formula X).

Scheme 18

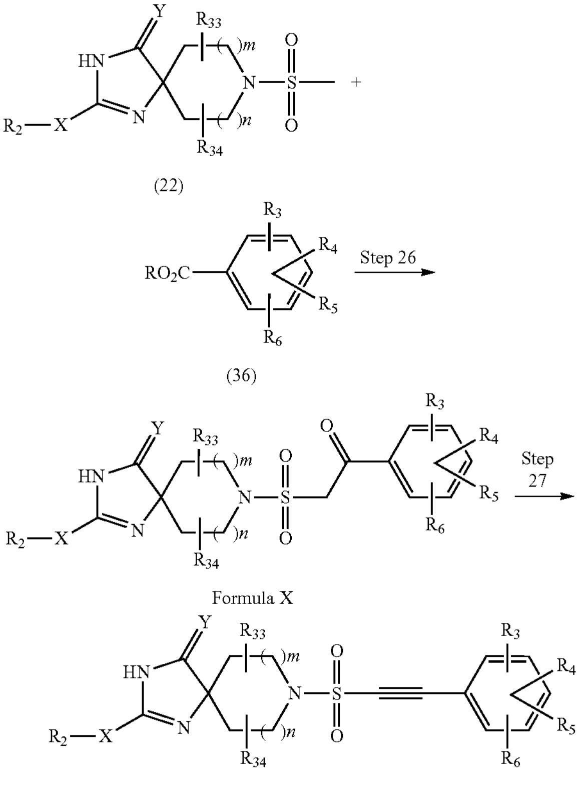

(22)

(36)

Formula X

Formula XI

Step 26 is a method of condensation with an aryl ester (36) in an appropriate solvent such as tetrahydrofuran or diethyl ether in the presence of a base such as lithium hexamethyldisilazide (LHMDS) or lithium diisopropylamide (LDA) preferably with the addition of DMPU. The reaction is performed at −78° C. to room temperature for 1 to 24 hours in an $N_2$ atmosphere. The resulting acetophenone derivative (formula X) is isolated by a common technique and, if necessary, may be purified by crystallization or chromatography.

Step 27 is a method of synthesizing an alkynyl derivative (formula XI) by subjecting the acetophenone derivative (formula X) to dehydration reaction. Specifically, 1 to 10 equivalents of a dehydrating agent, preferably 2-chloro-1-methylpyridinium iodide, and an appropriate base, preferably triethylamine, are added and reacted in an appropriate solvent such as dichloromethane at 0° C. to a temperature under heating. The resulting alkynyl derivative (formula XI) is isolated by a common technique and, if necessary, may be purified by crystallization or chromatography.

The substituted alkylene derivative of the general formula (1) wherein W is branched alkylene or haloalkylene (formula XII) can be synthesized as follows, for example.

The substituted alkylene derivative (formula XII) can be obtained by nucleophilic substitution reaction with a ketal-sulfonamide derivative (37) as a raw material to introduce an alkyl group or a halogen atom onto the carbon adjacent to the sulfonyl group (Step 28), ketal deprotection reaction (Step 20) and the steps shown in Schemes 5 and 6.

Scheme 19

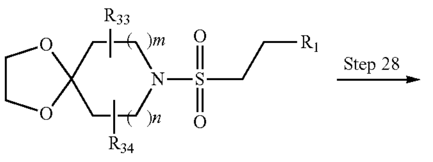

(37)

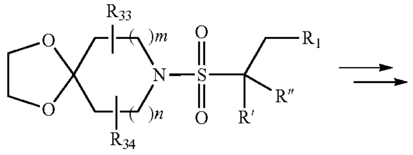

(38)

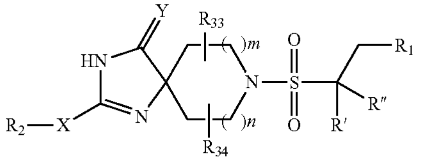

Formula XII

Step 28 is a reaction of a ketal-alkylenesulfonamide derivative (37) with an electrophilic reagent such as an alkyl halide or NFSI (N-fluorodibenzenesulfonimide) in an appropriate solvent such as tetrahydrofuran in the presence of a base such as n-butyllithium or lithium diisopropylamide. The reaction temperature is −78° C. to room temperature, for example, and the reaction time is 0.5 hour to several hours. The ketal-sulfonamide derivative (38) is isolated by a common technique and, if necessary, may be purified by crystallization or chromatography. In this reaction, one or two substituents are introduced onto the carbon atom adjacent to the sulfonyl group, and the equivalents of the base are controlled according to need. In the introduction of two substituents, two substituents can be introduced all at once using an excess of a base; however, it is desirable to once obtain a compound having one substituent introduced thereinto by purification and then introduce the other substituent.

The guanidine derivative of the general formula (1) wherein X is a nitrogen atom (formula XIII) can be synthesized through a guanidine intermediate (41).

The guanidine intermediate (41) can be synthesized from a thiohydantoin derivative (39) through an isothiourea derivative (40). The guanidine derivative (formula XIII) can be synthesized from the guanidine intermediate (41) by the reactions of Step 5 and subsequent Step 1, for example.

Scheme 20

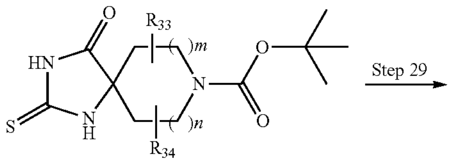

(39)

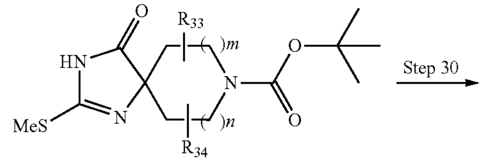

(40)

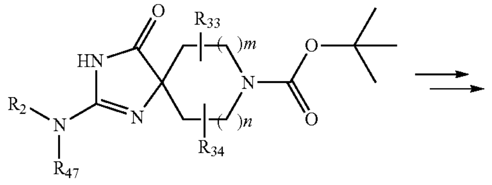

(41)

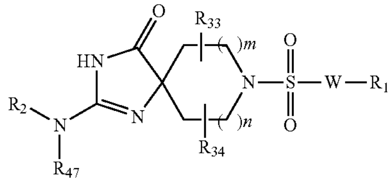

Formula XIII

Step 29 is S-alkylation reaction of a thiohydantoin derivative (39). Specifically, this is a method of reacting a thiohydantoin derivative (39) with an alkyl halide reagent such as methyl iodide in an appropriate solvent such as methanol in the presence of a base such as sodium hydroxide. The reaction temperature is room temperature to the boiling point of the solvent, for example, and the reaction time is several hours to 24 hours. The isothiourea derivative (40) is isolated by a common technique and, if necessary, may be purified by crystallization or chromatography.

Step 30 is a reaction of converting isothiourea to guanidine. Specifically, this is a method of reacting the isothiourea derivative (40) with a substituted primary amine or substituted secondary amine in an appropriate solvent such as dimethylacetamide in the presence of an acid catalyst such as acetic acid. The reaction temperature is room temperature to the boiling point of the solvent, for example, and the reaction time is 0.5 hour to several hours. The guanidine derivative (41) is isolated by a common technique and, if necessary, may be purified by crystallization or chromatography.

The derivative compound represented by the general formula (2), wherein Z includes alkenylene, can be synthesized from a diolefin derivative (formula XIV) by olefin metathesis reaction (Step 31).

Scheme 21

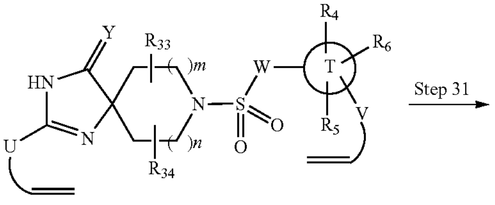

Formula XIV

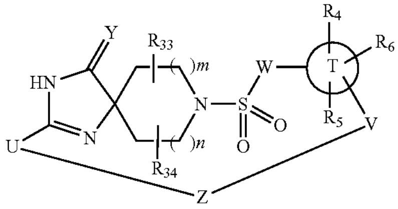

General formula (2)

Step 31 is a method of cyclizing a diolefin derivative (formula XIV) using a Grubbs reagent in an appropriate solvent such as dichloroethane. The reaction temperature is room temperature to the boiling point of the solvent, for example, and the reaction time is several hours to 24 hours. The macrocyclic derivative (formula (2)) is isolated by a common technique and, if necessary, may be purified by crystallization or chromatography.

The derivative compound represented by the general formula (2), wherein Z includes an amido group, can also be synthesized from a derivative having a primary amine or secondary amine at one end of the compound and a carboxylic acid at the other end (formula XV) by amidation reaction (Step 7).

Scheme 22

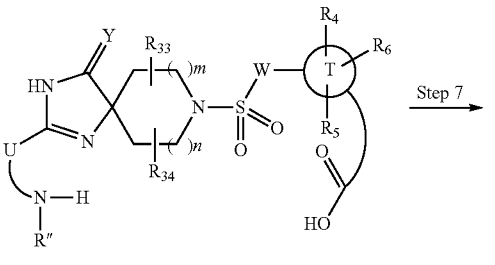

Formula XV

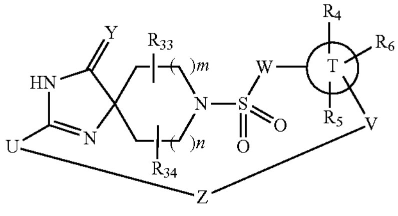

General formula (2)

The compound of the formula (2) is synthesized by cyclizing a derivative having an amine and a carboxylic acid at the ends (formula XV) using the above-described method of Step 7.

The derivative compound represented by the general formula (2), wherein Z includes triazole, can also be synthesized from a derivative (42) having an alkyne at one end of the compound and an azide at the other end using click chemistry (Step 32).

Scheme 23

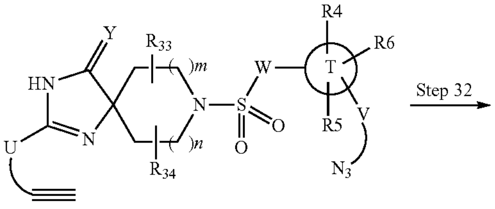

(42)

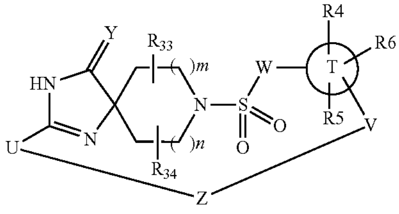

General formula (2)

Step 32 is a method of reacting an azide and an alkyne in a derivative (42) having the alkyne and the azide at the ends in an appropriate solvent such as acetonitrile or tetrahydrofuran in the presence of a copper catalyst such as CuI with the addition of a base such as diisopropylethylamine or 2,6-lutidine and ascorbic acid if necessary. The reaction temperature is room temperature to the boiling point of the solvent, for example, and the reaction time is 1 to 24 hours. The derivative represented by the general formula (2) is isolated by a common technique and, if necessary, may be purified by crystallization or chromatography.

Derivatives can be synthesized from compounds obtained in Schemes 21, 22 and 23 by olefin hydrogenation reaction, olefin oxidation reaction, sulfur atom oxidation reaction, deprotection reaction of various protecting groups and the like as necessary.

Compounds containing functional groups such as alkenyl, amine, carboxylic acid, alkynyl and azido functional groups at the ends, the raw materials used in Schemes 21, 22 and 23 and the like for synthesizing the general formula (2), may be synthesized by previously introducing these functional groups into a carboxylic acid derivative (7), a bromide derivative (9), a styrene derivative (11), an aryl halide derivative (21), an aldehyde derivative (24), a substituted phenylboronic acid (34) and the like and subjecting them to the same method as the method of manufacturing the general formula (1), or may be synthesized by synthesizing intermediates of the general formula (1), in which functional groups such as carboxylic acid and phenol functional groups are introduced into $R_1$ or $R_2$, and introducing the functional groups from these intermediates into these derivatives by an appropriate reaction.

If the functional groups introduced at the ends are previously introduced into a carboxylic acid derivative (7), a bromide derivative (9), a styrene derivative (11), an aryl halide derivative (21), an aldehyde derivative (24), a substituted phenylboronic acid (34) and the like, then these functional groups are protected and deprotected by an appropriate method as necessary in a process of synthesis by the same method as the method of manufacturing the general formula (1).

If the functional groups introduced at the ends are introduced into these derivatives by synthesizing intermediates of the general formula (1), in which a functional group such as carboxylic acid and phenol functional groups is introduced into $R_1$ or $R_2$, and introducing the functional groups from these intermediates by an appropriate reaction, then amidation, Mitsunobu reaction or the like is preferred as such an appropriate reaction. The functional groups are protected and deprotected by an appropriate method as necessary. For example, to introduce alkenyl or azido into $R_1$, amidation reaction is performed between a compound of the general formula (1), in which carboxylic acid is introduced into $R_1$, and an alkylamine with alkenyl or azido bonded thereto. To introduce alkenyl or alkynyl into $R_2$, Mitsunobu reaction is performed between a compound of the general formula (1), in which phenol is introduced into $R_2$, and an alkylamine with alkenyl, alkynyl or a protected amine bonded thereto. Raw materials for synthesizing the general formula (2) can be synthesized by combining these reactions of introducing functional groups into $R_1$ or $R_2$.

The compound (7), compound (9), compound (11), compound (21), compound (24) or compound (34) used in the above reactions can be synthesized from known compounds using appropriate reagents and reactions. For example, an amino group, if present in $R_1$ or $R_2$, may be alkylated, acylated, carbamated, converted to ureas or sulfonamidated from known compounds. Carboxylic acids or esters, if present, may be amidated under general conditions. Sulfonyl chlorides, if present, may be condensed with amines and sulfonamidated. Alcohols, if present, may be etherified or carbamated. Aryl halides, if present, may be coupled with arylboric acids or aryl boronates under general Suzuki conditions. Olefins, if present, may be reduced or converted to diols. Thioether groups, if present, may be oxidized to sulfoxides or sulfones. If ketones or carbonyl groups are present, the carbon chain may be extended by Wittig reaction, Horner-Wadsworth-Emmons reaction, aldol reaction or the like. In the introduction of fluorine atoms, reagents containing fluorine atoms may be introduced by these reactions, or aldehydes, ketones or carboxylic acids may be reacted with diethylaminosulfur trifluoride, for example.

The techniques for introducing these groups can be performed with reference to March, Advanced Organic Chemistry, 5$^{th}$ Edition, John Wiley and Sons, New York; J. Med. Chem., 2005, 48, 6066-6083; Organic Syntheses (1951), 31, 8-11; Bioorg. Med. Chem. Lett., 2003, 13, 837-840; Chem. Rev. 2002, 102, 1359; J. Organomet. Chem. 1999, 576, 147; Chem. Rev. 1995, 95, 2457, for example. These groups may be protected with protecting groups under general conditions, if necessary. This can be performed with reference to Protective Groups in Organic Synthesis, Wiley-Interscience, for example.

Some of the compounds of the present invention are useful not only as compounds having a PTH-like effect but also as intermediates for the synthesis of additional compounds of the present invention. For example, amines may be alkylated, acylated, carbamated, converted to ureas, sulfonamidated or sulfamidated under general conditions. Carboxylic acid and ester moieties may be converted to amides under general conditions. Amido groups may be converted to thioamido groups. Olefins may be reduced or converted to diols. Thioether groups, if present, may be oxidized to sulfoxides or sulfones. The techniques for introducing these groups can be performed with reference to March, Advanced Organic Chemistry, 5$^{th}$ Edition, John Wiley and Sons, New York; J. Med. Chem., 2005, 48, 6066-6083; Organic Syntheses (1951), 31, 8-11; Bioorg. Med. Chem. Lett., 2003, 13, 837-840, for example. Protecting groups may be deprotected under general conditions. This can be performed with reference to Protective Groups in Organic Synthesis, Wiley-Interscience, for example. Aryl halides may be coupled with arylboric acids or aryl boronates under general Suzuki conditions. This can be performed with reference to Chem. Rev. 2002, 102, 1359; J. Organomet. Chem. 1999, 576, 147; Chem. Rev. 1995, 95, 2457, for example.

EXAMPLES

The content of the present invention will be described in more detail by the following examples and test example; however, the present invention is not limited to the content of the examples and test example. All starting materials and reagents were obtained from commercial suppliers or synthesized using known methods. $^1$H-NMR spectra were measured using EX270 (manufactured by JEOL), Mercury300 (manufactured by Varian), ARX-3000 (manufactured by Bruker), ECP-400 (manufactured by JEOL) or 400-MR (manufactured by Varian) with or without $Me_4Si$ as the internal standard (s=singlet, d=doublet, t=triplet, brs=broad singlet, m=multiplet). Mass spectrometry measurement was performed using a mass spectrometer, LCQ Classic (manufactured by Thermo Electron), ZQ2000 (manufactured by Waters), 3100 (manufactured by Waters), ZMD4000 (manufactured by Waters), SQD (manufactured by Waters) or 2020 (manufactured by Shimazu). Microwave irradiation was performed using Initiator™ (manufactured by Biotage). In LCMS and HPLC, measurement of the retention time and mass spectrometry were performed by the following apparatuses and analysis conditions.

TABLE 1

| LCMS, HPLC condition No. | Apparatus | Column (I.D. × length) (mm) | Mobile phase | Gradient (A/B) | Flow rate | Column temperature (° C.) | Wavelength |
|---|---|---|---|---|---|---|---|
| LCMS-A-1 | Agilent 1100/ LCQ Classic | Cadenza CD-C18 3 um (3.0 × 30) | A) 0.05% TFA, H2O B) 0.05% TFA, MeCN | 95/5 => 0/100 (3.5 min) 0/100 (1 min) | 1.5 mL/min | 35 | 210-400 nm PDA total |
| LCMS-A-2 | Agilent 1100/ LCQ Classic | Cadenza CD-C18 3 um (3.0 × 30) | A) 0.05% TFA, H2O B) 0.05% TFA, MeCN | 95/5 => 0/100 (9.5 min) 0/100 (2.5 min) | 1.0 mL/min | 35 | 210-400 nm PDA total |

TABLE 1-continued

| LCMS, HPLC condition No. | Apparatus | Column (I.D. × length) (mm) | Mobile phase | Gradient (A/B) | Flow rate | Column temperature (° C.) | Wavelength |
|---|---|---|---|---|---|---|---|
| LCMS-B-1 | Alliance 2795 HT/ 996 PDA/ ZMD4000 | Cadenza CD-C18 3 um (3.0 × 30) | A) 0.05% TFA, H2O B) 0.05% TFA, MeCN | 95/5 => 0/100 (3.5 min) 0/100 (1 min) | 1.5 mL/min | 35 | 210-400 nm PDA total |
| LCMS-C-1 | 2525 BGM/ 2996 PDA/ ZQ2000 | Chromolith Flash RP-18e (4.6 × 25) | A) 10 mM AcONH4, H2O B) MeOH | 95/5 => 0/100 (3 min) 0/100 (2 min) | 2.0 mL/min | Room temperature | 210-400 nm PDA total |
| LCMS-C-2 | 2525 BGM/ 2996 PDA/ ZQ2000 | Chromolith Flash RP-18e (4.6 × 25) | A) 10 mM AcONH4, H2O B) MeOH | 95/5 => 0/100 (3 min) 0/100 (2 min) | 2.0 mL/min | Room temperature | 210-400 nm PDA total |
| LCMS-C-3 | 2525 BGM/ 2996 PDA/ ZQ2000 | Chromolith Flash RP-18e (4.6 × 25) | A) 10 mM AcONH4, H2O B) MeOH | 50/50 => 0/100 (3 min) 0/100 (2 min) | 2.0 mL/min | Room temperature | 210-400 nm PDA total |
| LCMS-D-1 | 2545 BGM/ 2996 PDA/ 3100 | SunfireTM C18 5 um (4.6 × 50) | A) 0.05% TFA, H2O B) 0.05% TFA, MeCN | 90/10 => 10/90 (5 min) | 4.0 mL/min | 25 | 210-400 nm PDA total |
| LCMS-E-1 | Agilent 1100 | Waters X-Bridge C18 5 um (2.1 × 50) | A) 0.01% NH3, H2O B) 0.01% NH3, MeCN | 95/5 => 5/95 (5 min) | 1.2 mL/min | 40 | 190-400 nm PDA total |
| LCMS-E-2 | Alliance 2795/ ZQ2000 | Waters X-Bridge C18 5 um (2.1 × 50) | A) 0.1% TFA, H2O B) 0.1% TFA, MeCN | 95/5 => 35/65 (5 min) | 1.2 mL/min | 40 | 190-400 nm PDA total |
| LCMS-E-3 | Alliance 2795/ ZQ2000 | Waters X-Bridge C18 5 um (2.1 × 50) | A) 0.1% TFA, H2O B) 0.1% TFA, MeCN | 95/5 (0 min) => 95/5 (0.5 min) => 5/95 (5 min) | 1.2 mL/min | 45 | 190-400 nm PDA total |
| LCMS-E-4 | Alliance 2795/ ZQ2000 | Waters X-Bridge C18 5 um (2.1 × 50) | A) 0.1% TFA, H2O B) 0.1% TFA, MeCN | 95/5 (0 min) => 95/5 (0.5 min) => 5/95 (5 min) | 1.2 mL/min | 45 | 190-400 nm PDA total |
| LCMS-E-5 | Alliance 2795/ ZQ2000 | Waters X-Bridge C18 5 um (2.1 × 50) | A) 0.01% NH3, H2O B) 0.01% NH3, MeCN | 95/5 (0 min) => 95/5 (0.5 min) => 35/65 (5 min) => 5/95 (5.5 min) | 1.2 mL/min | 45 | 190-400 nm PDA total |
| LCMS-E-6 | Alliance 2795/ ZQ2000 | Waters X-Bridge C18 5 um (2.1 × 50) | A) 0.1% TFA, H2O B) 0.1% TFA, MeCN | 95/5 => 5/95 (5 min) | 1.2 mL/min | 40 | 190-400 nm PDA total |
| LCMS-E-7 | Alliance 2795/ ZQ2000 | Waters X-Bridge C18 3.5 um (2.1 × 50) | A) 0.1% TFA, H2O B) 0.1% TFA, MeCN | 95/5 (0 min) => 95/5 (3 min) | 1.2 mL/min | 45 | 190-400 nm PDA total |
| LCMS-E-8 | Alliance 2795/ ZQ2000 | Waters X-Bridge C18 5 um (2.1 × 50) | A) 0.1% TFA, H2O B) 0.1% TFA, MeCN | 95/5 (0 min) => 95/5 (0.5 min) => 35/65 (5 min) => 5/95 (5.5 min) | 1.2 mL/min | 45 | 190-400 nm PDA total |
| LCMS-F-1 | Acquity/ SQD | Ascentis Express C18 (2.1 × 50) | A) 10 mM AcONH4, H2O B) MeOH | 95/5 => 0/100 (1 min) 0/100 (0.4 min) | 1.0 mL/min | 35 | 210-400 nm PDA total |
| LCMS-F-2 | Acquity/ SQD | Ascends Express C18 (2.1 × 50) | A) 0.1% HCO2H, H2O B) 0.1% HCO2H, MeCN | 95/5 => 0/100 (1 min) 0/100 (0.4 min) | 1.0 mL/min | 35 | 210-400 nm PDA total |
| LCMS-G-1 | UFLC XR/2020 | Acquity (2.1 × 50) | A) 0.1% TFA, H2O B) 0.1% TFA, MeCN | 95/5 => 0/100 (1.5 min) 0/100 (0.5 min) | 1.0 mL/min | 35 | 305 nm, bandwidth 95 nm |
| HPLC-A-1 | LC-2010A (SHIMAZU) | YMC-ODSA (6.0 × 150) | A) 0.1% TFA, H2O B) 0.1% TFA, MeCN | 90/20 => 10/80 (40 min) | 1.0 mL/min | 25 | UV 254, 225 nm |
| HPLC-A-2 | LC-2010A (SHIMAZU) | YMC-ODSA (6.0 × 150) | A) 0.1% TFA, H2O B) 0.1% TFA, MeCN | 90/30 => 10/70 (40 min) | 1.0 mL/min | 25 | UV 254, 225 nm |
| HPLC-A-3 | LC-2010A (SHIMAZU) | YMC-ODSA (6.0 × 150) | A) 0.1% TFA, H2O B) 0.1% TFA, MeCN | 90/10 => 10/90 (25 min) | 1.0 mL/min | 25 | UV 254, 225 nm |

Example 1

8-(3-Chloro-benzenesulfonyl)-2-cyclohexyl-1,3,8-triaza-spiro[4.5]dec-1-en-4-one (Compound 1)

(Reaction 1-1)

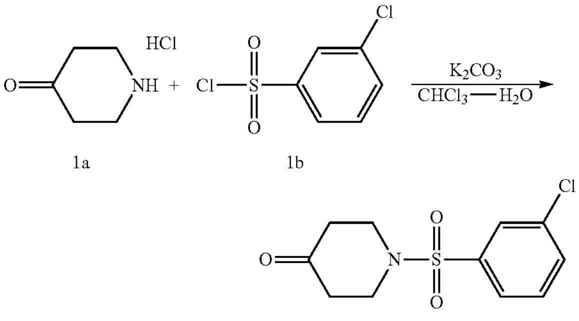

1a 1b

1c

Potassium carbonate (13.96 g, 101.1 mmol) and 3-chlorobenzenesulfonyl chloride were continuously added to a two-phase solution of 4-piperidone hydrochloride hydrate (6.06 g, 39.48 mmol) in chloroform (47.4 mL) and water (47.4 mL), and the mixture was stirred at room temperature. A saturated aqueous sodium bicarbonate solution was added, and the organic layer and the aqueous layer were separated. The aqueous layer was then further extracted with dichloromethane. The organic layers were combined, dried over anhydrous sodium sulfate and then concentrated under reduced pressure. The resulting solid was washed with n-hexane and then collected by filtration and dried under reduced pressure to give 1-(3-chloro-benzenesulfonyl)-piperidin-4-one as a white solid (10.5 g, 97%).

$^1$H-NMR (300 MHz, $CDCl_3$) δ 2.55 (4H, t, J=6.3 Hz), 3.42 (4H, t, J=6.0 Hz), 7.48 (1H, t, J=8.0 Hz), 7.58 (1H, dt, J=8.0, 1.7 Hz), 7.67 (1H, dt, J=7.7, 1.7 Hz), 7.77 (1H, t, J=1.9 Hz).

(Reaction 1-2)

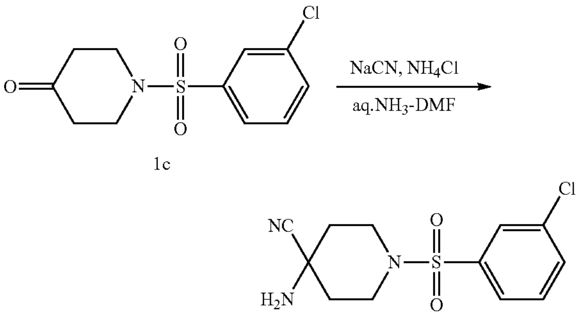

1c

1d

Ammonium chloride (790 mg, 14.77 mmol) and a 28% aqueous ammonia solution (2.2 mL) were added to a solution of 1-(3-chloro-benzenesulfonyl)-piperidin-4-one (3.11 g, 11.36 mmol) in dimethylformamide (15 mL), and the mixture was stirred at room temperature for one hour. Thereafter, sodium cyanide (724 mg, 14.77 mmol) was added, and the mixture was further stirred for 17 hours and then quenched with a saturated aqueous sodium carbonate solution. The organic layer and the aqueous layer were separated, and the aqueous layer was then further extracted with ethyl acetate: n-hexane (4:1). The organic layers were combined, washed with water (×4), and then dried over anhydrous sodium sulfate and concentrated under reduced pressure. The residue was purified by silica gel column chromatography (n-hexane: ethyl acetate=1:3) to give 4-amino-1-(3-chloro-benzenesulfonyl)-piperidine-4-carbonitrile as a white solid (2.41 g, 71%).

$^1$H-NMR (300 MHz, $CDCl_3$) δ 1.75 (2H, s), 1.80-1.90 (2H, m), 2.11-2.14 (2H, m), 2.87-2.96 (2H, m), 3.54-3.62 (2H, m), 7.47 (1H, t, J=8.1 Hz), 7.58-7.66 (2H, m), 7.75 (1H, t, J=1.8 Hz).

(Reaction 1-3)

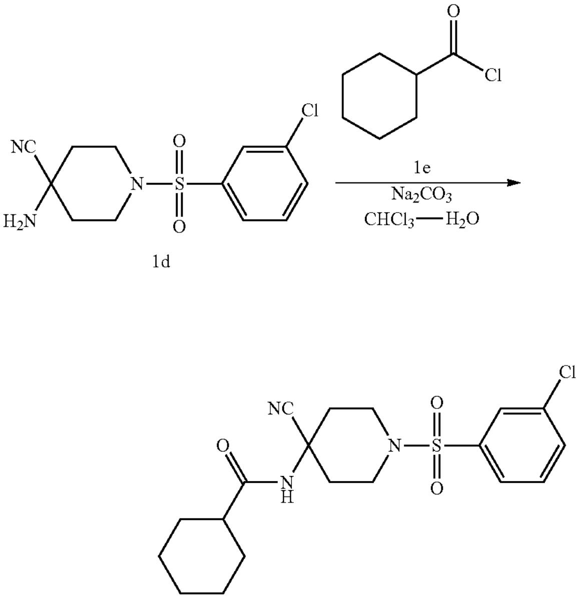

1d

1f

A solution of cyclohexanecarbonyl chloride (118 μL, 0.880 mmol) in chloroform (0.25 mL) was added to a mixed solution of 4-amino-1-(3-chloro-benzenesulfonyl)-piperidine-4-carbonitrile (120 mg, 0.400 mmol) in chloroform (1.25 mL) and a saturated aqueous sodium carbonate solution (1.25 mL), and the mixture was vigorously stirred at room temperature for 16 hours. Cyclohexanecarbonyl chloride (51 μL) was further added and the mixture was stirred for 2.5 hours. The organic layer and the aqueous layer were then separated, and the aqueous layer was further extracted with chloroform. The organic layers were combined, dried over anhydrous sodium sulfate and then concentrated under reduced pressure. The residue was washed with n-hexane to give cyclohexanecarboxylic[1-(3-chloro-benzenesulfonyl)-4-cyano-piperidin-4-yl]-amide as a white solid. This was used in the next step without further purification.

$^1$H-NMR (300 MHz, $CDCl_3$) δ 1.20-1.96 (14H, m), 2.04-2.14 (1H, m), 2.55 (2H, brd, J=13 Hz), 2.76-2.87 (2H, m), 5.58 (1H, s), 7.51 (1H, t, J=7.9 Hz), 7.60-7.66 (2H, m), 7.75 (1H, t, J=1.8 Hz). MS (ESI) m/z=410 (M+H)+.

(Reaction 1-4)

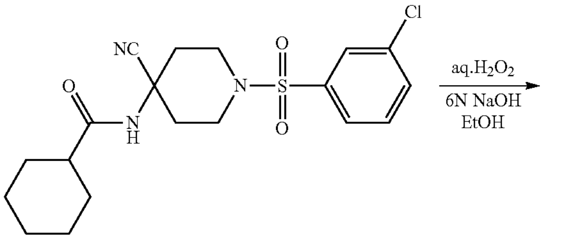

1f

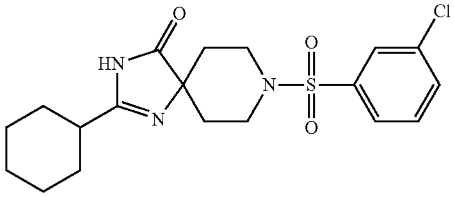

Compound 1

A 6 M aqueous sodium hydroxide solution (0.74 mL) and a 30% aqueous hydrogen peroxide solution (0.25 mL) were added to a solution of cyclohexanecarboxylic[1-(3-chloro-benzenesulfonyl)-4-cyano-piperidin-4-yl]-amide (100 mg, 0.244 mmol) in ethanol (1.60 mL), and the mixture was heated under reflux for 4.5 hours. The reaction mixture was cooled to room temperature and water was then added, followed by concentration under reduced pressure. The residue was neutralized with a saturated aqueous ammonium chloride solution, followed by extraction with dichloromethane. The organic layer was dried over anhydrous sodium sulfate and concentrated under reduced pressure. The residue was purified by silica gel column chromatography (dichloromethane: methanol=90:10) to give 8-(3-chloro-benzenesulfonyl)-2-cyclohexyl-1,3,8-triaza-spiro[4.5]dec-1-en-4-one as a white solid (52 mg, 52%).

$^1$H-NMR (270 MHz, $CDCl_3$) δ 1.13-1.40 (7H, m), 1.54-1.75 (7H, m), 2.22-2.30 (1H, m), 2.72-2.80 (2H, m), 3.53-3.59 (2H, m), 7.67-7.85 (4H, m), 10.80 (1H, s). MS (ESI) m/z=410 (M+H)+.

The example compounds shown below were synthesized by operations similar to those in Example 1 using appropriate reagents and starting materials.

TABLE 2

| Compound | Structure | LCMS or HPLC condition | Retention time (min) | MS (m/z) |
|---|---|---|---|---|
| 2 | 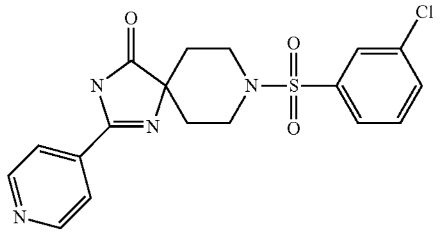 [SMILES: O=C1NC(c2ccncc2)=NC12CCN(S(=O)(=O)c1cccc(Cl)c1)CC2] | LCMS-A-1 | 1.92 | 405 (M + H)+ |
| 3 | 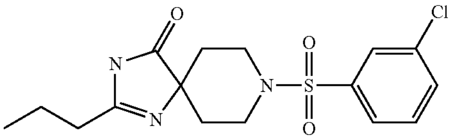 [SMILES: CCCC1=NC2(CCN(S(=O)(=O)c3cccc(Cl)c3)CC2)C(=O)N1] | LCMS-A-1 | 1.9 | 370 (M + H)+ |
| 4 | 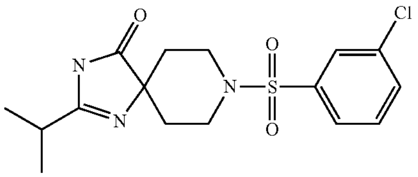 [SMILES: CC(C)C1=NC2(CCN(S(=O)(=O)c3cccc(Cl)c3)CC2)C(=O)N1] | LCMS-A-1 | 1.87 | 370 (M + H)+ |
| 5 | 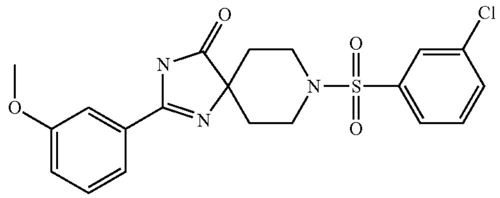 [SMILES: COc1cccc(C2=NC3(CCN(S(=O)(=O)c4cccc(Cl)c4)CC3)C(=O)N2)c1] | LCMS-A-1 | 2.32 | 434 (M + H)+ |

TABLE 2-continued
| Compound | Structure | LCMS or HPLC condition | Retention time (min) | MS (m/z) |
|---|---|---|---|---|
| 6 | 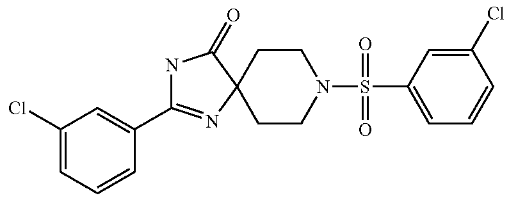 [SMILES: O=C1NC(c2cccc(Cl)c2)=NC12CCN(S(=O)(=O)c1cccc(Cl)c1)CC2] | LCMS-A-1 | 2.65 | 438 (M + H)+ |
| 7 | 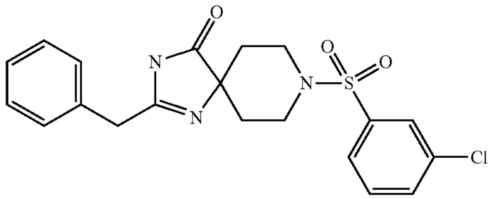 [SMILES: O=C1NC(Cc2ccccc2)=NC12CCN(S(=O)(=O)c1cccc(Cl)c1)CC2] | LCMS-A-1 | 2.22 | 418 (M + H)+ |
| 8 | 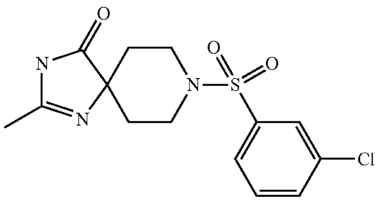 [SMILES: CC1=NC2(CCN(S(=O)(=O)c3cccc(Cl)c3)CC2)C(=O)N1] | LCMS-A-1 | 1.79 | 342 (M + H)+ |
| 10 | 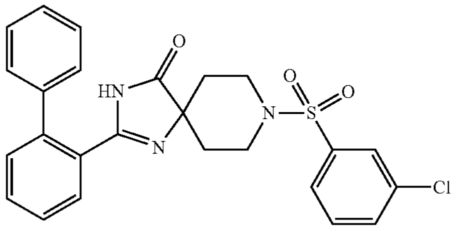 [SMILES: O=C1NC(c2ccccc2-c2ccccc2)=NC12CCN(S(=O)(=O)c1cccc(Cl)c1)CC2] | LCMS-C-1 | 2.82 | 480 (M + H)+ |
| 11 | 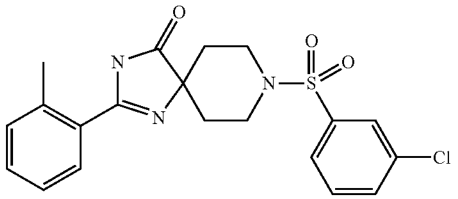 [SMILES: Cc1ccccc1C1=NC2(CCN(S(=O)(=O)c3cccc(Cl)c3)CC2)C(=O)N1] | LCMS-C-1 | 2.66 | 418 (M + H)+ |
| 12 | 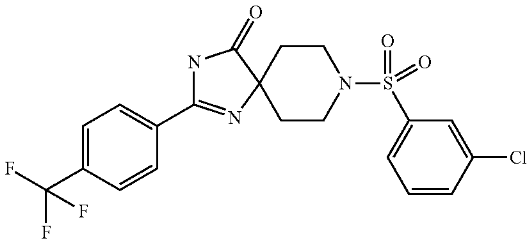 [SMILES: O=C1NC(c2ccc(C(F)(F)F)cc2)=NC12CCN(S(=O)(=O)c1cccc(Cl)c1)CC2] | LCMS-C-1 | 2.89 | 472 (M + H)+ |
| 13 | 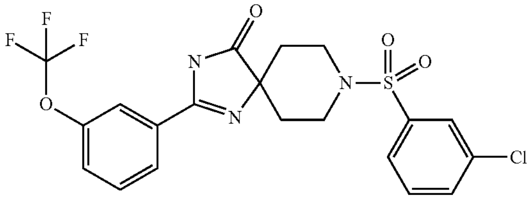 [SMILES: O=C1NC(c2cccc(OC(F)(F)F)c2)=NC12CCN(S(=O)(=O)c1cccc(Cl)c1)CC2] | LCMS-A-1 | 2.82 | 488 (M + H)+ |

TABLE 2-continued
| Compound | Structure | LCMS or HPLC condition | Retention time (min) | MS (m/z) |
|---|---|---|---|---|
| 14 | 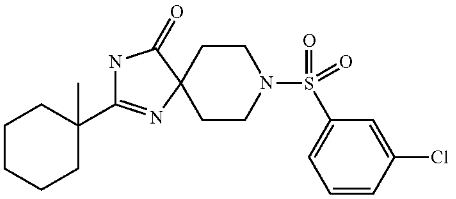 [SMILES: CC1(C2=NC3(CCN(S(=O)(=O)c4cccc(Cl)c4)CC3)C(=O)N2)CCCCC1] | LCMS-C-1 | 2.86 | 424 (M + H)+ |
| 15 | 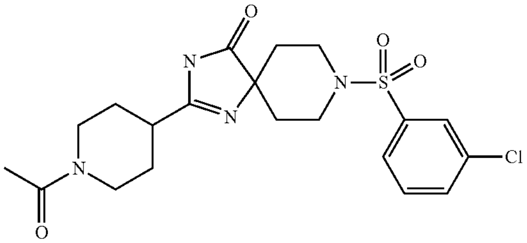 [SMILES: CC(=O)N1CCC(C2=NC3(CCN(S(=O)(=O)c4cccc(Cl)c4)CC3)C(=O)N2)CC1] | LCMS-A-1 | 1.84 | 453 (M + H)+ |
| 16 | 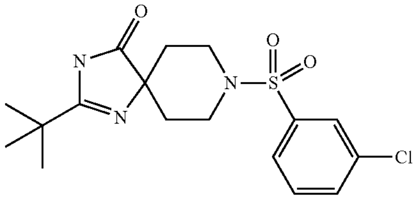 [SMILES: CC(C)(C)C1=NC2(CCN(S(=O)(=O)c3cccc(Cl)c3)CC2)C(=O)N1] | LCMS-A-1 | 1.97 | 384 (M + H)+ |
| 17 | 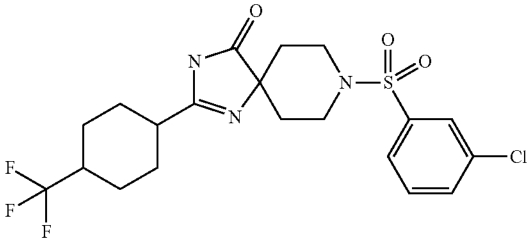 [SMILES: O=C1NC(C2CCC(C(F)(F)F)CC2)=NC12CCN(S(=O)(=O)c1cccc(Cl)c1)CC2] | LCMS-C-1 | 2.81 | 478 (M + H)+ |
| 18 | 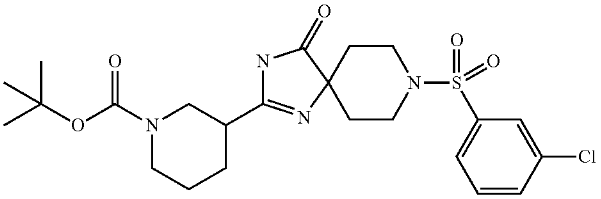 [SMILES: CC(C)(C)OC(=O)N1CCCC(C2=NC3(CCN(S(=O)(=O)c4cccc(Cl)c4)CC3)C(=O)N2)C1] | LCMS-C-1 | 2.8 | 511 (M + H)+ |
| 19 | 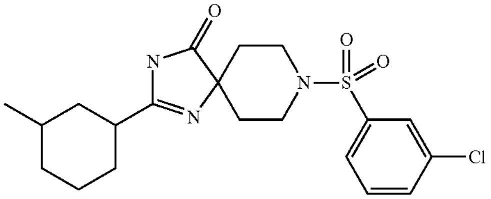 [SMILES: CC1CCCC(C2=NC3(CCN(S(=O)(=O)c4cccc(Cl)c4)CC3)C(=O)N2)C1] | LCMS-A-1 | 2.22 | 424 (M + H)+ |
| 20 | 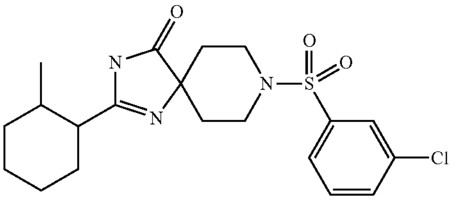 [SMILES: CC1CCCCC1C1=NC2(CCN(S(=O)(=O)c3cccc(Cl)c3)CC2)C(=O)N1] | LCMS-C-1 | 2.78 | 424 (M + H)+ |

TABLE 2-continued
| Compound | Structure | LCMS or HPLC condition | Retention time (min) | MS (m/z) |
|---|---|---|---|---|
| 21 | 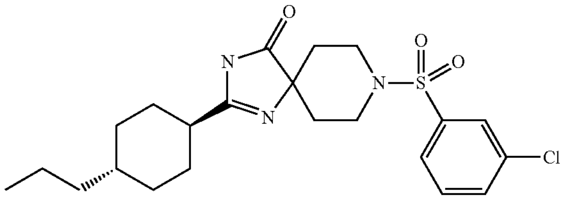 [SMILES: CCC[C@H]1CC[C@H](C2=NC3(CCN(S(=O)(=O)c4cccc(Cl)c4)CC3)C(=O)N2)CC1] | LCMS-C-1 | 3.1 | 452 (M + H)+ |
| 22 | 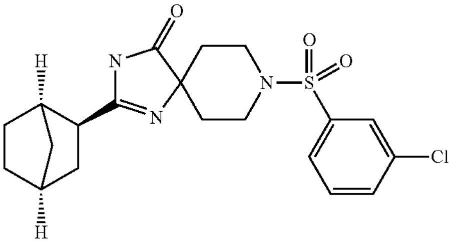 [SMILES: O=C1NC([C@H]2C[C@H]3CC[C@@H]2C3)=NC12CCN(S(=O)(=O)c1cccc(Cl)c1)CC2] | LCMS-C-1 | 2.76 | 422 (M + H)+ |
| 23 | 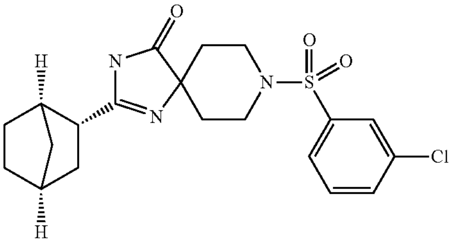 [SMILES: O=C1NC([C@@H]2C[C@H]3CC[C@@H]2C3)=NC12CCN(S(=O)(=O)c1cccc(Cl)c1)CC2] | LCMS-C-1 | 2.74 | 422 (M + H)+ |
| 24 | 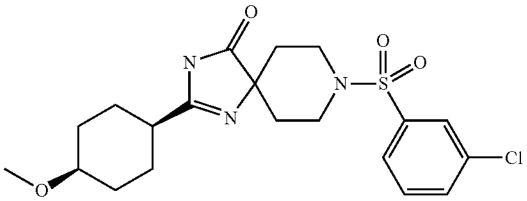 [SMILES: CO[C@H]1CC[C@@H](C2=NC3(CCN(S(=O)(=O)c4cccc(Cl)c4)CC3)C(=O)N2)CC1] | LCMS-C-1 | 2.47 | 440 (M + H)+ |
| 25 | 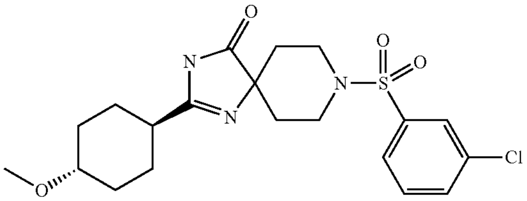 [SMILES: CO[C@H]1CC[C@H](C2=NC3(CCN(S(=O)(=O)c4cccc(Cl)c4)CC3)C(=O)N2)CC1] | LCMS-C-1 | 2.45 | 440 (M + H)+ |
| 26 | 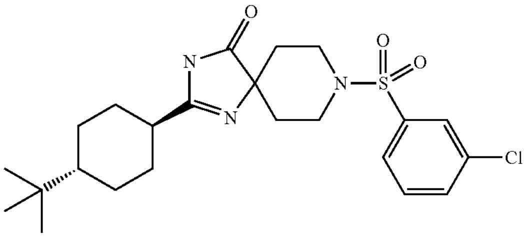 [SMILES: CC(C)(C)[C@H]1CC[C@H](C2=NC3(CCN(S(=O)(=O)c4cccc(Cl)c4)CC3)C(=O)N2)CC1] | LCMS-C-1 | 3.14 | 466 (M + H)+ |
| 27 | 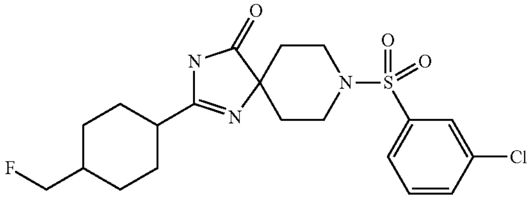 [SMILES: O=C1NC(C2CCC(CF)CC2)=NC12CCN(S(=O)(=O)c1cccc(Cl)c1)CC2] | LCMS-C-1 | 2.61 | 442 (M + H)+ |

TABLE 2-continued
| Compound | Structure | LCMS or HPLC condition | Retention time (min) | MS (m/z) |
|---|---|---|---|---|
| 28 | 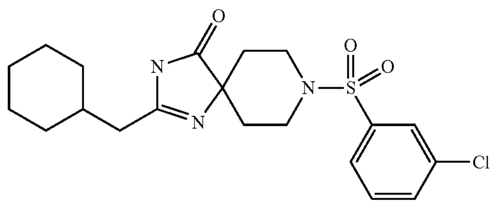 [SMILES: O=C1NC(CC2CCCCC2)=NC12CCN(S(=O)(=O)c1cccc(Cl)c1)CC2] | LCMS-C-1 | 2.81 | 424 (M + H)+ |
| 29 | 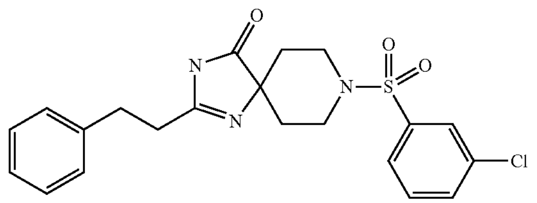 [SMILES: O=C1NC(CCc2ccccc2)=NC12CCN(S(=O)(=O)c1cccc(Cl)c1)CC2] | LCMS-C-1 | 2.65 | 432 (M + H)+ |
| 30 | 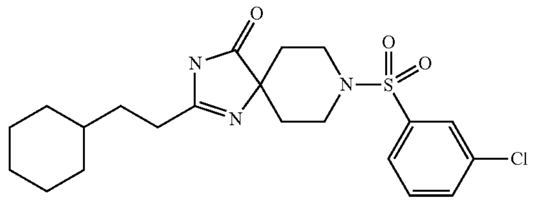 [SMILES: O=C1NC(CCC2CCCCC2)=NC12CCN(S(=O)(=O)c1cccc(Cl)c1)CC2] | LCMS-A-1 | 2.4 | 438 (M + H)+ |
| 31 | 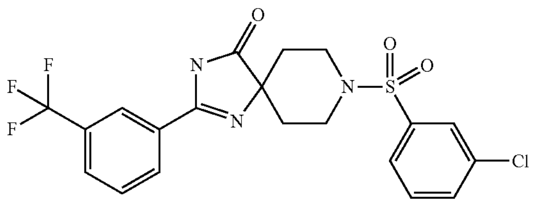 [SMILES: O=C1NC(c2cccc(C(F)(F)F)c2)=NC12CCN(S(=O)(=O)c1cccc(Cl)c1)CC2] | LCMS-A-1 | 2.79 | 472 (M + H)+ |
| 32 | 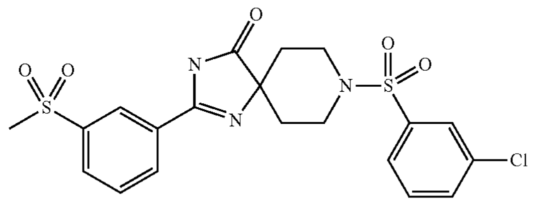 [SMILES: CS(=O)(=O)c1cccc(C2=NC3(CCN(S(=O)(=O)c4cccc(Cl)c4)CC3)C(=O)N2)c1] | LCMS-C-1 | 2.3 | 482 (M + H)+ |
| 33 | 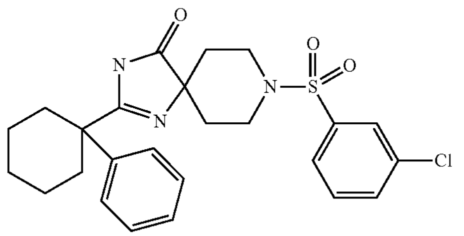 [SMILES: O=C1NC(C2(c3ccccc3)CCCCC2)=NC12CCN(S(=O)(=O)c1cccc(Cl)c1)CC2] | LCMS-C-1 | 3.08 | 486 (M + H)+ |
| 34 | 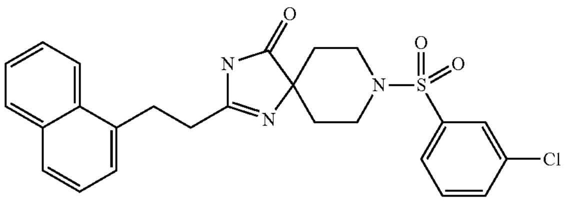 [SMILES: O=C1NC(CCc2cccc3ccccc23)=NC12CCN(S(=O)(=O)c1cccc(Cl)c1)CC2] | LCMS-C-1 | 2.87 | 482 (M + H)+ |

Example 2

8-(2-Naphthalen-1-yl-ethanesulfonyl)-2-(3-trifluoromethyl-phenyl)-1,3,8-triaza-spiro[4.5]dec-1-en-4-one (Compound 35)

(Reaction 2-1)

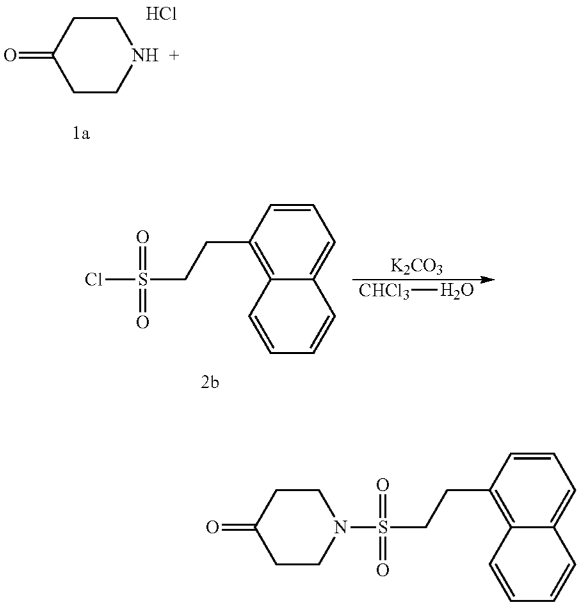

1a

2b

2c 1-(2-Naphthalen-1-yl-ethanesulfonyl)-piperidin-4-one was synthesized by the procedure described in Reaction 1-1 of Example 1 using 2-naphthalen-1-yl-ethanesulfonyl chloride as a reagent.

MS (ESI) m/z=318 (M+H)+.

(Reaction 2-2)

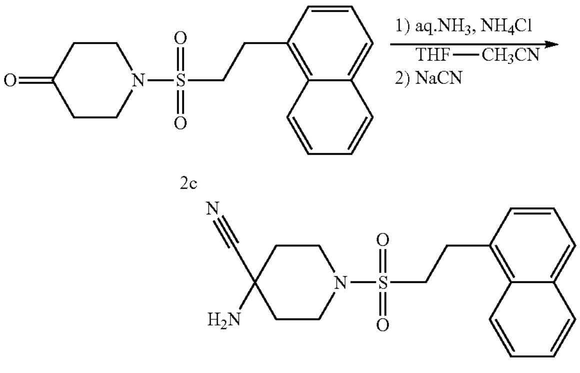

2c

2d

4-Amino-1-(2-naphthalen-1-yl-ethanesulfonyl)-piperidine-4-carbonitrile was synthesized by operations similar to those in Reaction 1-2 of Example 1 using THF-$CH_3CN$ as a solvent and using appropriate reagents and starting material.

MS (ESI) m/z=344 (M+H)+.

(Reaction 2-3)

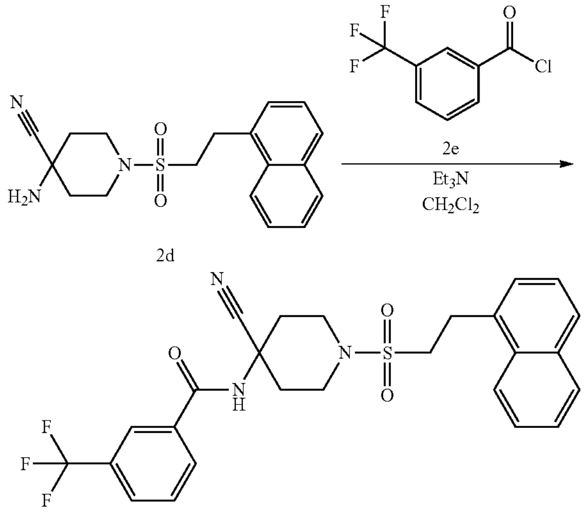

2d

2f

3-Trifluoromethyl-benzoyl chloride (57 μL, 0.378 mmol) was added to a solution of 4-amino-1-(2-naphthalen-1-yl-ethanesulfonyl)-piperidine-4-carbonitrile (100 mg, 0.291 mmol) and $Et_3N$ (61 μL) in $CH_2Cl_2$ (3 mL). The reaction mixture was stirred at room temperature for four hours and then diluted with $CH_2Cl_2$, and the organic layer was washed with water. The organic layer was dried over anhydrous sodium sulfate and then concentrated under reduced pressure. The residue was used in the next step without further purification.

MS (ESI) m/z=516 (M+H)+.

(Reaction 2-4)

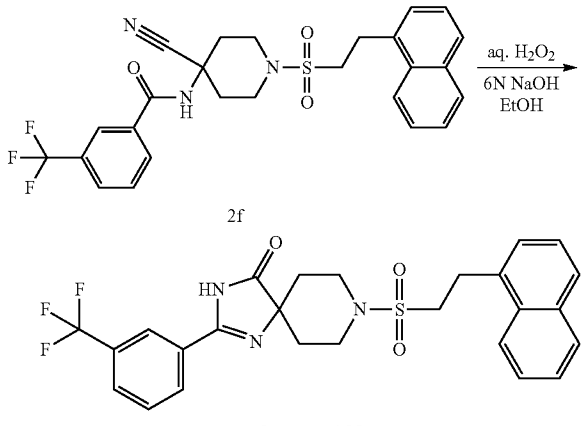

2f

Compound 35

8-(2-Naphthalen-1-yl-ethanesulfonyl)-2-(3-trifluoromethyl-phenyl)-1,3,8-triaza-spiro[4.5]dec-1-en-4-one was synthesized by operations similar to those in Reaction 1-4 of Example 1 using appropriate reagents and starting material.

$^1$H-NMR (400 MHz, $CDCl_3$) δ 1.65-1.75 (2H, m), 2.07-2.16 (2H, m), 3.32-3.38 (2H, m), 3.42-3.55 (2H, m), 3.63-3.70 (2H, m), 3.82-3.90 (2H, m), 7.40-7.47 (2H, m), 7.50-7.55 (1H, m), 7.56-7.65 (2H, m), 7.77-7.7.82 (2H, m), 7.90 (1H, d, J=4.0 Hz), 8.02-8.10 (2H, m), 8.18 (1H, s); MS (ESI) m/z=516 (M+H)+.

The example compounds shown below were synthesized by operations similar to those in Example 2 using appropriate reagents and starting materials.

TABLE 3

| Compound | Structure | LCMS or HPLC condition | Retention time (min) | MS (m/z) |
|---|---|---|---|---|
| 36 | 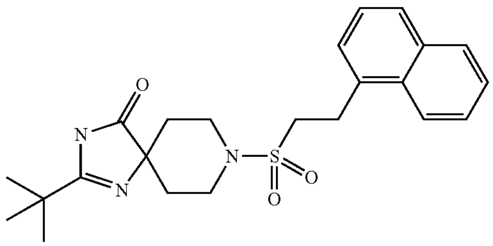 [SMILES: CC(C)(C)C1=NC2(CCN(S(=O)(=O)CCc3cccc4ccccc34)CC2)C(=O)N1] | LCMS-A-1 | 2.24 | 428 (M + H)+ |
| 37 | 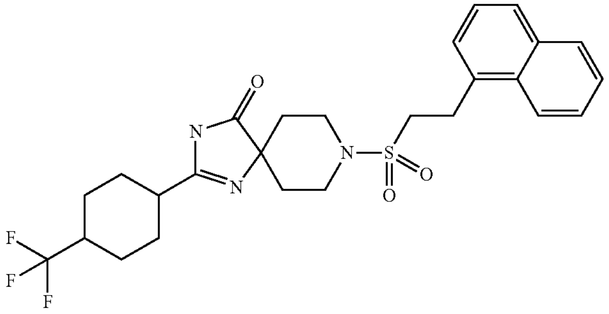 [SMILES: O=C1NC(C2CCC(C(F)(F)F)CC2)=NC12CCN(S(=O)(=O)CCc1cccc3ccccc13)CC2] | LCMS-A-1 | 2.55 | 522 (M + H)+ |

Example 3

3-[8-(2-Naphthalen-1-yl-ethanesulfonyl)-4-oxo-1,3,8-triaza-spiro[4.5]dec-1-en-2-yl]-piperidine-1-carboxylic acid tert-butyl ester (Compound 38)

(Reaction 3-1)

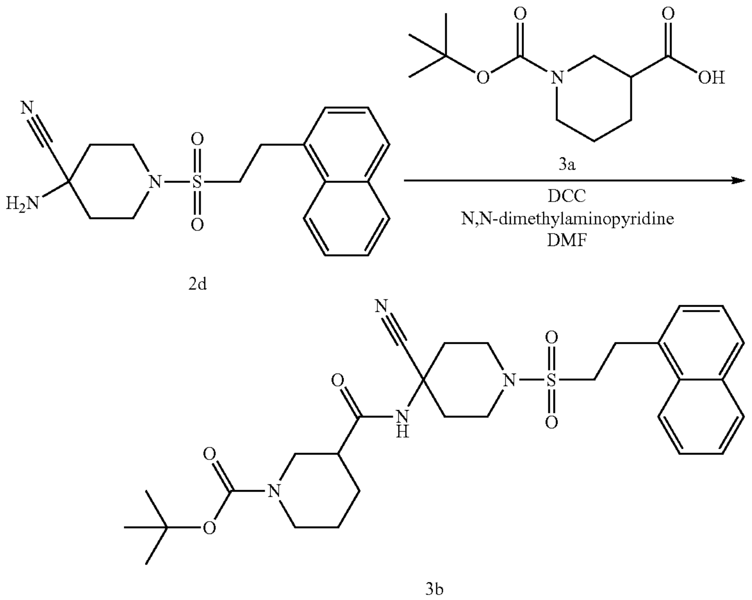

DCC (1.3 eq) and DMAP (5 mol %) were added to a mixture of 4-amino-1-(2-naphthalen-1-yl-ethanesulfonyl)-piperidine-4-carbonitrile and piperidine-1,3-dicarboxylic acid 1-tert-butyl ester (1.3 eq) in DMF, and the mixture was stirred at room temperature overnight. Ethyl acetate was added to the reaction solution, and the organic layer was then sequentially washed with 1 N NaOH, water and saturated brine. The organic layer was dried over anhydrous sodium sulfate and then concentrated under reduced pressure. The residue was used in the next step without further purification.

(Reaction 3-2)

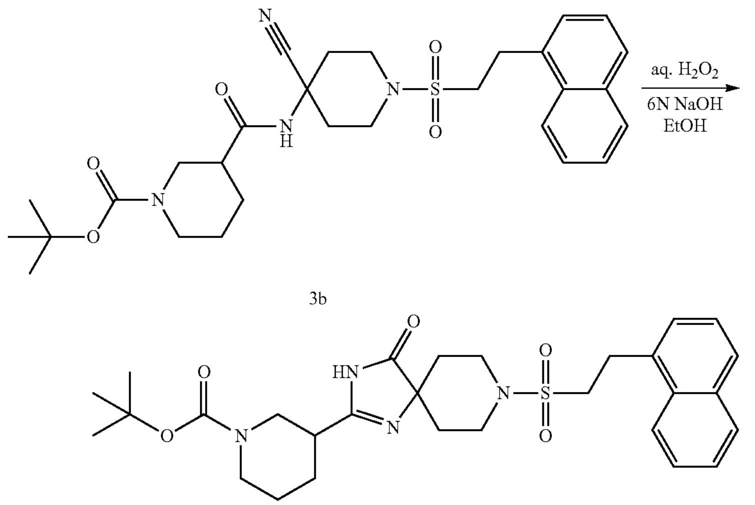

3b

Compound 38

3-[8-(2-Naphthalen-1-yl-ethanesulfonyl)-4-oxo-1,3,8-triaza-spiro[4.5]dec-1-en-2-yl]-piperidine-1-carboxylic acid tert-butyl ester was synthesized by operations similar to those in Reaction 1-4 of Example 1 using appropriate reagents and starting material.

MS (ESI) m/z=555 (M+H)+.

Example 4

8-(2-Naphthalen-1-yl-ethanesulfonyl)-2-[1-(2-naphthalen-1-yl-ethanesulfonyl)-piperidin-3-yl]-1,3,8-triaza-spiro[4.5]dec-1-en-4-one (Compound 39)

(Reaction 4-1)

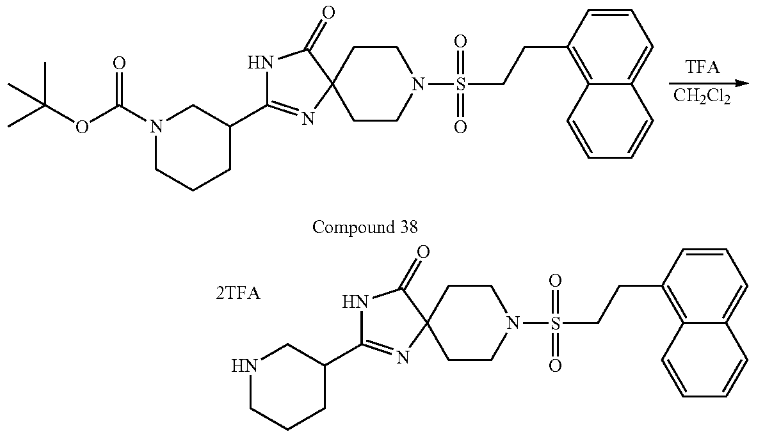

Compound 38

4a

Trifluoroacetic acid (10 eq) was added dropwise to a solution of 3-[8-(2-naphthalen-1-yl-ethanesulfonyl)-4-oxo-1,3,8-triaza-spiro[4.5]dec-1-en-2-yl]-piperidine-1-carboxylic acid tert-butyl ester in $CH_2Cl_2$. The reaction mixture was stirred at room temperature overnight and then concentrated under reduced pressure to give 8-(2-naphthalen-1-yl-ethanesulfonyl)-2-piperidin-3-yl-1,3,8-triaza-spiro[4.5]dec-1-en-4-one ditrifluoroacetate as a pale yellow form (70%).

$^1$H-NMR (400 MHz, CD3OD) δ 0.98 (3H, t), 1.15-1.22 (1H, m), 1.44-1.52 (2H, m), 1.56-1.67 (2H, m), 1.69-1.82 (2H, m), 1.86-2.03 (3H, m), 2.63-2.71 (1H, m), 2.79-2.85 (2H, m), 2.86-3.05 (3H, m), 3.49-3.65 (3H, m), 3.65-3.76 (2H, m), 7.44 (1H, t, J=7.83 Hz), 7.50-7.55 (1H, m), 7.61 (1H, d, J=8.08 Hz), 7.71 (1H, t, J=1.77 Hz). MS (ESI) m/z=517 (M+H)+.

(Reaction 4-2)

2TFA

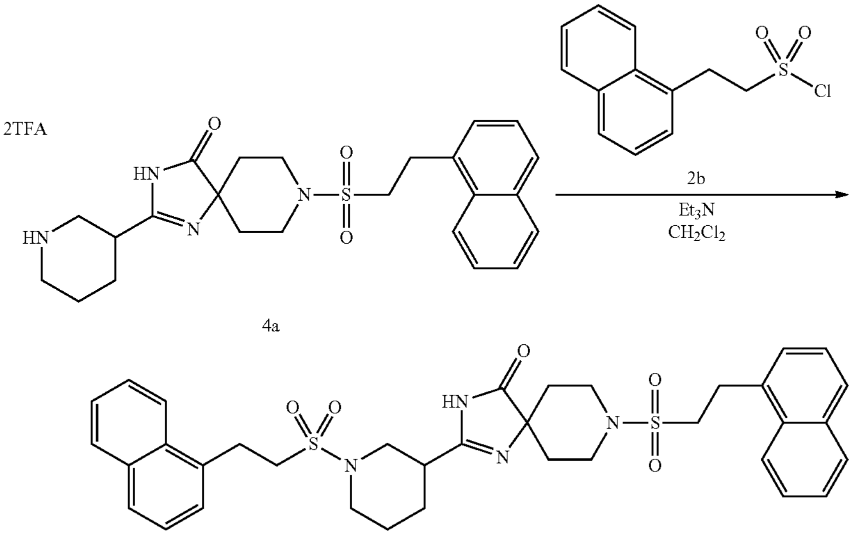

4a

Compound 39

8-(2-Naphthalen-1-yl-ethanesulfonyl)-2-[1-(2-naphthalen-1-yl-ethanesulfonyl)-piperidin-3-yl]-1,3,8-triaza-spiro[4.5]dec-1-en-4-one was synthesized by operations similar to those in Reaction 2-3 of Example 2 using appropriate reagents and starting material.

MS (ESI) m/z=673 (M+H)+.

The example compounds shown below were synthesized by operations similar to those in Example 3 and Example 4 using appropriate reagents and starting materials.

TABLE 4

| Compound | Structure | LCMS or HPLC condition | Retention time (min) | MS (m/z) |
|---|---|---|---|---|
| 40 | 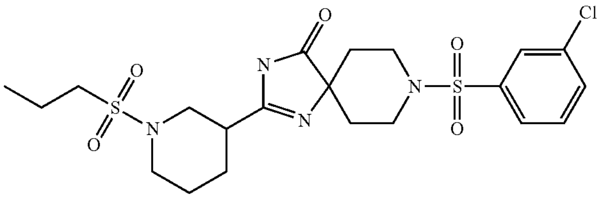 [SMILES: CCCS(=O)(=O)N1CCCC(C2=NC3(CCN(S(=O)(=O)c4cccc(Cl)c4)CC3)C(=O)N2)C1] | LCMS-E-2 | 3.76 | 517 (M + H)+ |
| 41 | 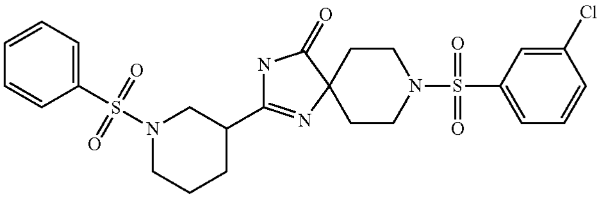 [SMILES: O=C1NC(C2CCCN(S(=O)(=O)c3ccccc3)C2)=NC12CCN(S(=O)(=O)c1cccc(Cl)c1)CC2] | LCMS-E-2 | 4.13 | 551 (M + H)+ |
| 42 | 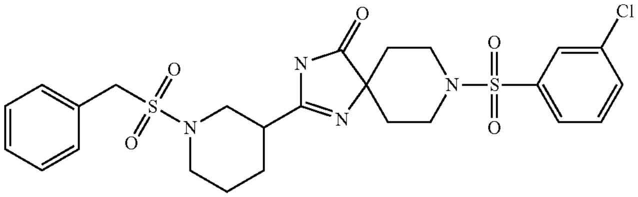 [SMILES: O=C1NC(C2CCCN(S(=O)(=O)Cc3ccccc3)C2)=NC12CCN(S(=O)(=O)c1cccc(Cl)c1)CC2] | LCMS-E-2 | 4.11 | 565 (M + H)+ |

TABLE 4-continued

| Compound | Structure | LCMS or HPLC condition | Retention time (min) | MS (m/z) |
|---|---|---|---|---|
| 43 | 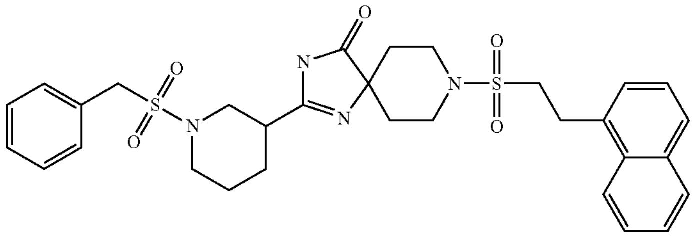 [SMILES: O=C1NC(C2CCCN(S(=O)(=O)Cc3ccccc3)C2)=NC12CCN(S(=O)(=O)CCc1cccc3ccccc13)CC2] | LCMS-E-2 | 3.58 | 609 (M + H)+ |

Example 5

8-(4-Chloro-benzenesulfonyl)-2-(2,4-dichloro-phenyl)-1,3,8-triaza-spiro[4.5]dec-1-en-4-one (Compound 44)

(Reaction 5-1)

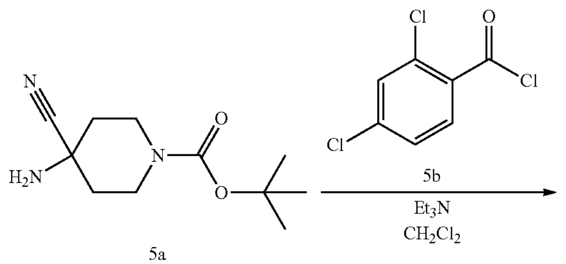

5a

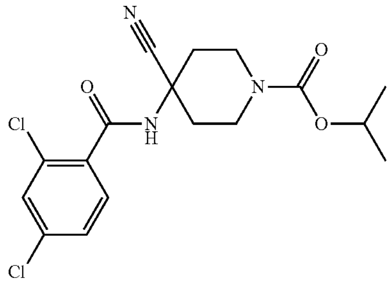

5c

4-Cyano-4-(2,4-dichloro-benzoylamino)-piperidine-1-carboxylic acid tert-butyl ester was synthesized by operations similar to those in Reaction 2-3 of Example 2 using appropriate reagents and starting material.

$^1$H-NMR (400 MHz, $CDCl_3$) δ 1.47 (9H, s), 1.87-1.97 (2H, m), 2.45-2.55 (2H, m), 3.32-3.43 (2H, m), 3.90-4.05 (2H, m), 6.48 (1H, brs), 7.38 (1H, dd, J=8.4, 2.0 Hz), 7.45 (1H, d, J=2.0 Hz), 7.78 (1H, d, J=8.4 Hz).

(Reaction 5-2)

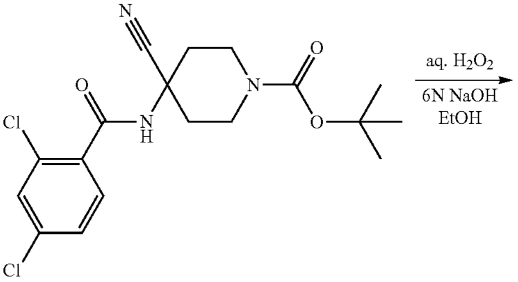

5c

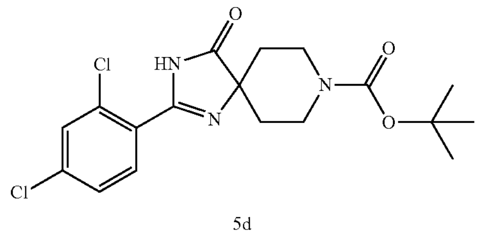

5d 2-(2,4-Dichloro-phenyl)-4-oxo-1,3,8-triaza-spiro[4.5]dec-1-ene-8-carboxylic acid tert-butyl ester was synthesized by operations similar to those in Reaction 1-4 of Example 1 using appropriate reagents and starting material.

MS (ESI) m/z=490 (M+H)+.

(Reaction 5-3)

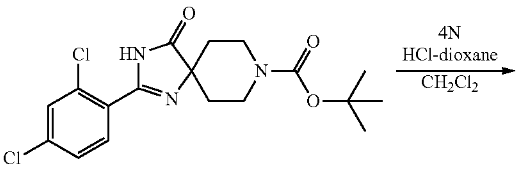

5d

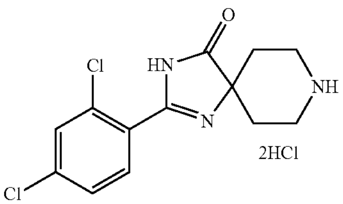

5e

4 N HCl-dioxane (20 ml, 80 mmol) was added to a solution of 2-(2,4-dichloro-phenyl)-4-oxo-1,3,8-triaza-spiro[4.5]dec-1-ene-8-carboxylic acid tert-butyl ester (3.11 g, 7.81 mmol) in $CH_2Cl_2$ (60 mL), and the mixture was stirred at room temperature for four hours. The reaction mixture was diluted with $CH_2Cl_2$-hexane, and the precipitated solid was then filtered. The resulting solid was washed with ethyl acetate and then dried under reduced pressure to give 2-(2,4-dichloro-phenyl)-1,3,8-triaza-spiro[4.5]dec-1-en-4-one dihydrochloride (3.18 g) as a colorless solid.

MS (ESI) m/z=298 (M+H)+.

(Reaction 5-4)

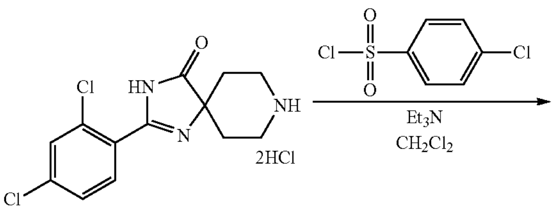

5e

-continued

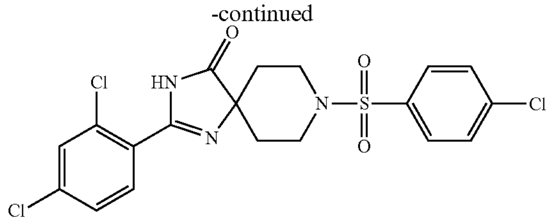

Compound 44

Triethylamine (88 μl, 0.632 mmol) and 4-chlorobenzenesulfonyl chloride (70 mg, 0.332 mmol) were added to a mixed solution of 2-(2,4-dichloro-phenyl)-1,3,8-triaza-spiro[4.5]dec-1-en-4-one dihydrochloride (100 mg, 0.299 mmol) in dichloromethane (3 ml). The reaction solution was stirred at room temperature for 16 hours and then diluted with dichloromethane, and the organic layer was washed with water. The organic layer was dried over sodium sulfate and then concentrated under reduced pressure. The resulting residue was purified by silica gel column chromatography (ethyl acetate:hexane) to give 8-(4-chloro-benzenesulfonyl)-2-(2,4-dichloro-phenyl)-1,3,8-triaza-spiro[4.5]dec-1-en-4-one (70.8 mg, 96%).

$^1$H-NMR (400 MHz, DMSO-d6) δ 1.57-1.67 (2H, m), 1.85-1.95 (2H, m), 2.74-2.83 (2H, m), 3.64-3.72 (2H, m), 7.57-7.60 (1H, m), 7.61-7.65 (1H, m), 7.75-7.79 (2H, m), 7.81-7.86 (3H, m), 11.5 (1H, brs). MS (ESI) m/z=472 (M+H)+.

The example compounds shown below were synthesized by operations similar to those in Example 5 using appropriate reagents and starting materials.

TABLE 5

| Compound | Structure | LCMS or HPLC condition | Retention time (min) | MS (m/z) |
|---|---|---|---|---|
| 45 | 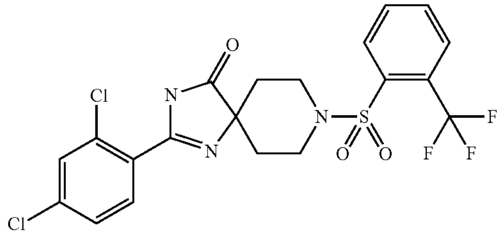 [SMILES: O=C1NC(c2ccc(Cl)cc2Cl)=NC12CCN(S(=O)(=O)c1ccccc1C(F)(F)F)CC2] | LCMS-C-3 | 4.59 | 468, 470 (M + H)+ |
| 46 | 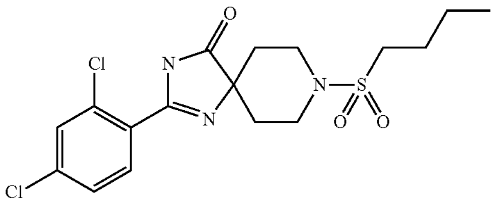 [SMILES: CCCCS(=O)(=O)N1CCC2(CC1)N=C(c1ccc(Cl)cc1Cl)NC2=O] | LCMS-A-1 | 2.45 | 418 (M + H)+ |
| 47 | 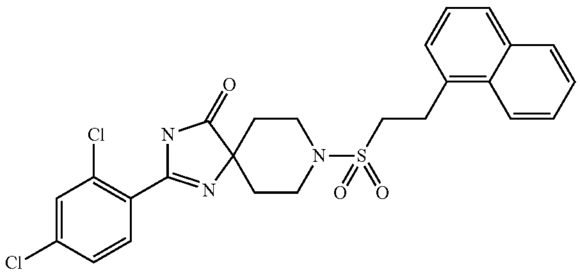 [SMILES: O=C1NC(c2ccc(Cl)cc2Cl)=NC12CCN(S(=O)(=O)CCc1cccc3ccccc13)CC2] | LCMS-A-1 | 2.94 | 516 (M + H)+ |

Example 6

2-(2,4-Dichloro-phenyl)-8-(quinoline-8-sulfonyl)-1,3,8-triaza-spiro[4.5]dec-1-en-4-one (Compound 48)

(Reaction 6-1)

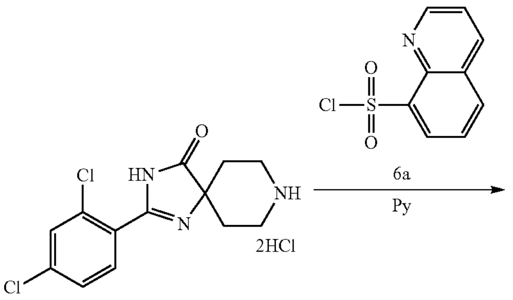

5e

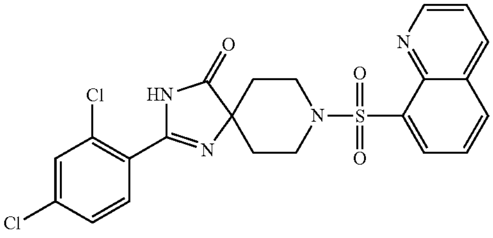

Compound 48

2-(2,4-Dichloro-phenyl)-8-(quinoline-8-sulfonyl)-1,3,8-triaza-spiro[4.5]dec-1-en-4-one was synthesized by operations similar to those in Reaction 4-2 of Example 4 using appropriate reagents and starting material and using pyridine as a base and solvent.

MS (ESI) m/z=490 (M+H)+.

The example compounds shown below were synthesized by operations similar to those in Example 6 using appropriate reagents and starting materials.

Example 7

2-(2-Cyclohexyl-4-oxo-1,3,8-triaza-spiro[4.5]dec-1-ene-8-sulfonyl)-benzoic acid methyl ester (Compound 51)

(Reaction 7-1)

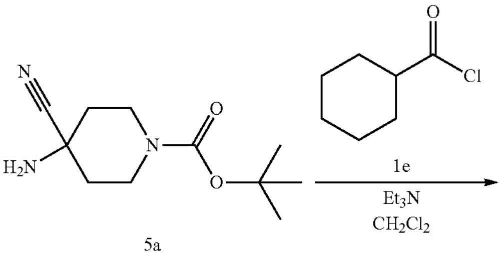

5a

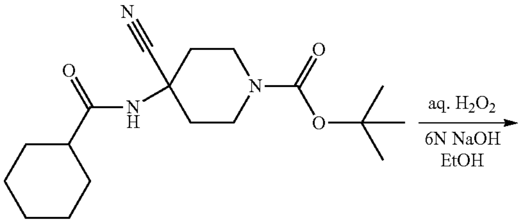

7a

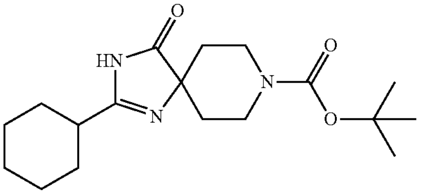

7b

2-Cyclohexyl-4-oxo-1,3,8-triaza-spiro[4.5]dec-1-ene-8-carboxylic acid tert-butyl ester was synthesized by operations similar to those in Reaction 5-1 and Reaction 5-2 of Example 5 using appropriate reagents and starting material.

MS (ESI) m/z=358 (M+Na)+.

TABLE 6

| Compound | Structure | LCMS or HPLC condition | Retention time (min) | MS (m/z) |
|---|---|---|---|---|
| 49 | 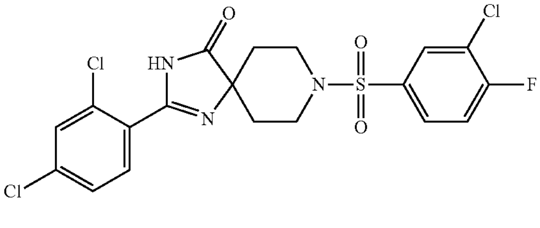 [SMILES: O=C1NC(c2ccc(Cl)cc2Cl)=NC12CCN(S(=O)(=O)c1ccc(F)c(Cl)c1)CC2] | LCMS-C-1 | 9.77 | 490 (M + H)+ |
| 50 | 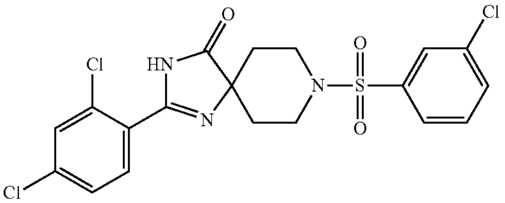 [SMILES: O=C1NC(c2ccc(Cl)cc2Cl)=NC12CCN(S(=O)(=O)c1cccc(Cl)c1)CC2] | LCMS-C-1 | 9.57 | 472 (M + H)+ |

(Reaction 7-2)

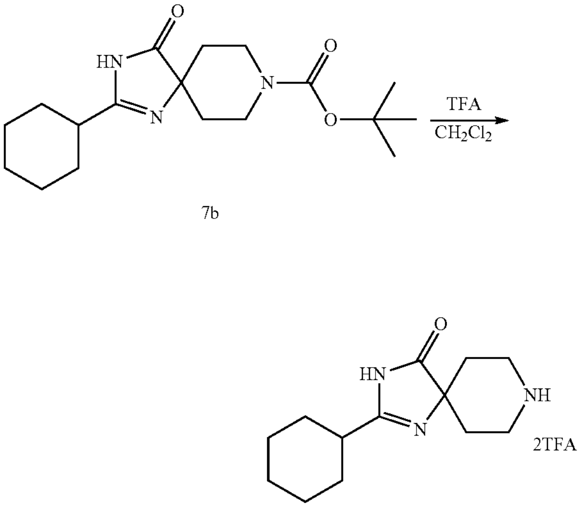

7b

7c

Trifluoroacetic acid (20 ml) was added to a solution of 2-cyclohexyl-4-oxo-1,3,8-triaza-spiro[4.5]dec-1-ene-8-carboxylic acid tert-butyl ester (4.43 g, 13.2 mmol) in dichloromethane, and the mixture was stirred at room temperature for five hours. The reaction mixture was concentrated under reduced pressure, and the residue was then triturated with $CH_2Cl_2$. The resulting solid was collected by filtration and dried under reduced pressure to give 2-cyclohexyl-1,3,8-triaza-spiro[4.5]dec-1-en-4-one ditrifluoroacetate (5.66 g, 92%).

MS (ESI) m/z=236 (M+H)+.

(Reaction 7-3)

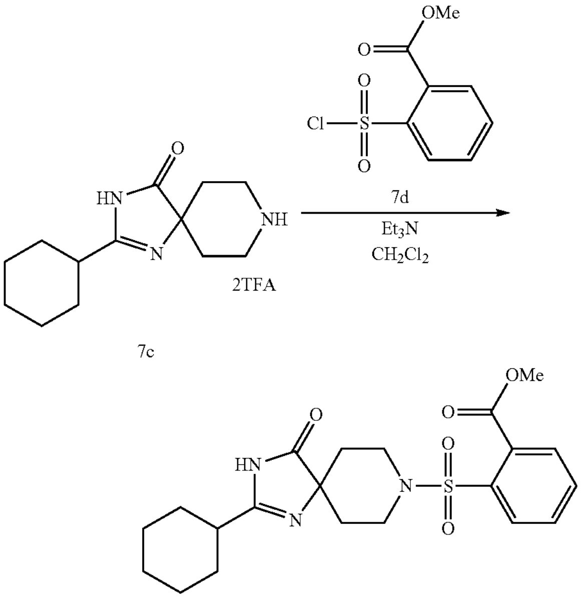

7c

Compound 51

2-(2-Cyclohexyl-4-oxo-1,3,8-triaza-spiro[4.5]dec-1-ene-8-sulfonyl)-benzoic acid methyl ester was synthesized by operations similar to those in Reaction 5-4 of Example 5 using appropriate reagents and starting material.

MS (ESI) m/z=434 (M+H)+.

The example compounds shown below were synthesized by operations similar to those in Example 7 using appropriate reagents and starting materials.

TABLE 7

| Compound | Structure | LCMS or HPLC condition | Retention time (min) | MS (m/z) |
|---|---|---|---|---|
| 52 | 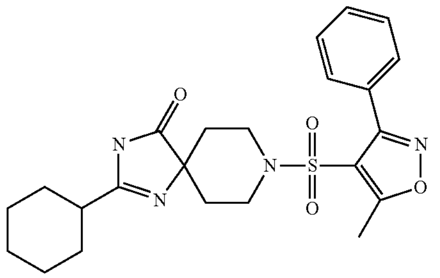 [SMILES: Cc1onc(-c2ccccc2)c1S(=O)(=O)N1CCC2(CC1)N=C(C1CCCCC1)NC2=O] | LCMS-E-1 | 3.584 | 458 (M + H)+ |
| 53 | 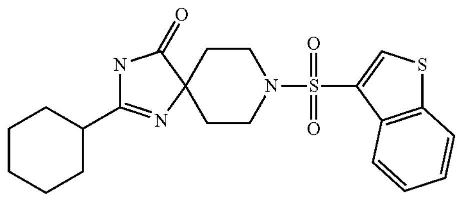 [SMILES: O=C1NC(C2CCCCC2)=NC12CCN(S(=O)(=O)c1csc3ccccc13)CC2] | LCMS-E-1 | 3.587 | 433 (M + H)+ |

TABLE 7-continued
| Compound | Structure | LCMS or HPLC condition | Retention time (min) | MS (m/z) |
|---|---|---|---|---|
| 54 | 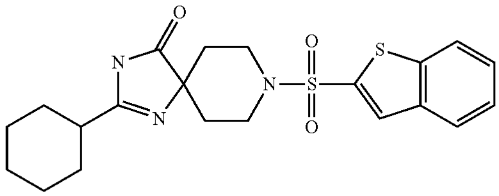 [SMILES: O=C1NC(C2CCCCC2)=NC12CCN(S(=O)(=O)c1cc3ccccc3s1)CC2] | LCMS-E-1 | 3.727 | 433 (M + H)+ |
| 55 | 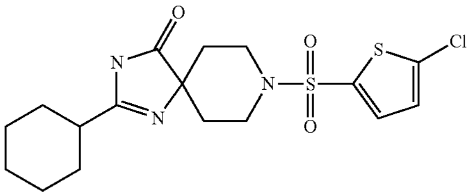 [SMILES: O=C1NC(C2CCCCC2)=NC12CCN(S(=O)(=O)c1ccc(Cl)s1)CC2] | LCMS-E-1 | 3.585 | 416 (M + H)+ |
| 56 | 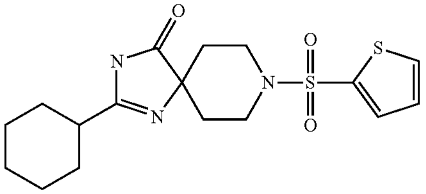 [SMILES: O=C1NC(C2CCCCC2)=NC12CCN(S(=O)(=O)c1cccs1)CC2] | LCMS-E-1 | 3.143 | 382 (M + H)+ |
| 57 | 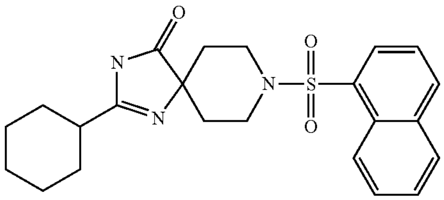 [SMILES: O=C1NC(C2CCCCC2)=NC12CCN(S(=O)(=O)c1cccc3ccccc13)CC2] | LCMS-E-1 | 3.604 | 427 (M + H)+ |
| 58 | 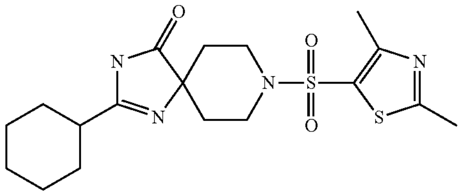 [SMILES: Cc1nc(C)c(S(=O)(=O)N2CCC3(CC2)N=C(C2CCCCC2)NC3=O)s1] | LCMS-E-2 | 1.22 | 411 (M + H)+ |
| 59 | 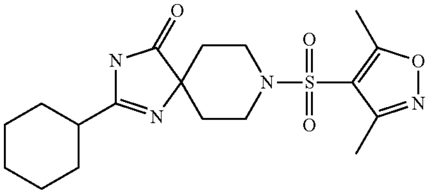 [SMILES: Cc1noc(C)c1S(=O)(=O)N1CCC2(CC1)N=C(C1CCCCC1)NC2=O] | LCMS-E-1 | 3.065 | 396 (M + H)+ |
| 60 | 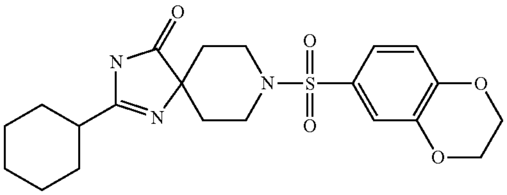 [SMILES: O=C1NC(C2CCCCC2)=NC12CCN(S(=O)(=O)c1ccc3c(c1)OCCO3)CC2] | LCMS-E-1 | 3.141 | 434 (M + H)+ |

TABLE 7-continued
| Compound | Structure | LCMS or HPLC condition | Retention time (min) | MS (m/z) |
|---|---|---|---|---|
| 61 | 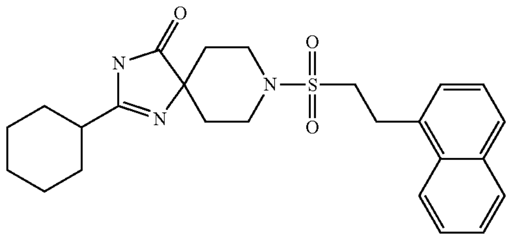 [SMILES: O=C1NC(C2CCCCC2)=NC12CCN(S(=O)(=O)CCc1cccc3ccccc13)CC2] | LCMS-E-1 | 3.782 | 454 (M + H)+ |
| 62 | 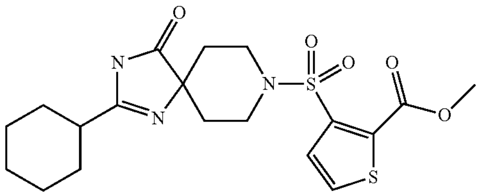 [SMILES: COC(=O)c1sccc1S(=O)(=O)N1CCC2(CC1)N=C(C1CCCCC1)NC2=O] | LCMS-C-1 | 2.35 | 440 (M + H)+ |
| 63 | 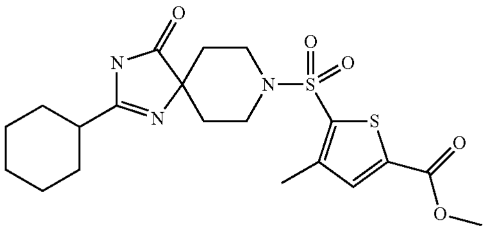 [SMILES: COC(=O)c1cc(C)c(S(=O)(=O)N2CCC3(CC2)N=C(C2CCCCC2)NC3=O)s1] | LCMS-C-1 | 2.64 | 454 (M + H)+ |
| 64 | 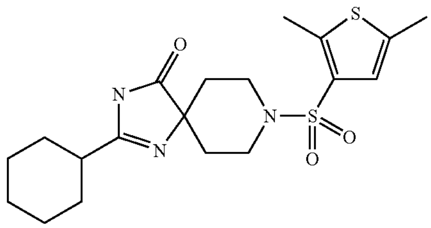 | LCMS-A-1 | 2.00 | 470 (M + H)+ |
| 65 | 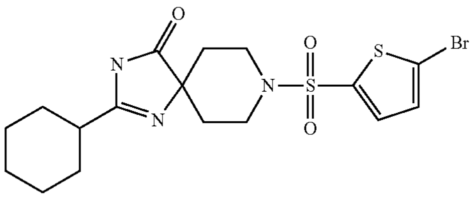 [SMILES: O=C1NC(C2CCCCC2)=NC12CCN(S(=O)(=O)c1ccc(Br)s1)CC2] | LCMS-C-2 | 2.13 | 461 (M + H)+ |

Example 8

8-(5-Chloro-thiophene-2-sulfonyl)-2-(3-trifluoromethyl-phenyl)-1,3,8-triaza-spiro[4.5]dec-1-en-4-one (Compound 66)

(Reaction 8-1)

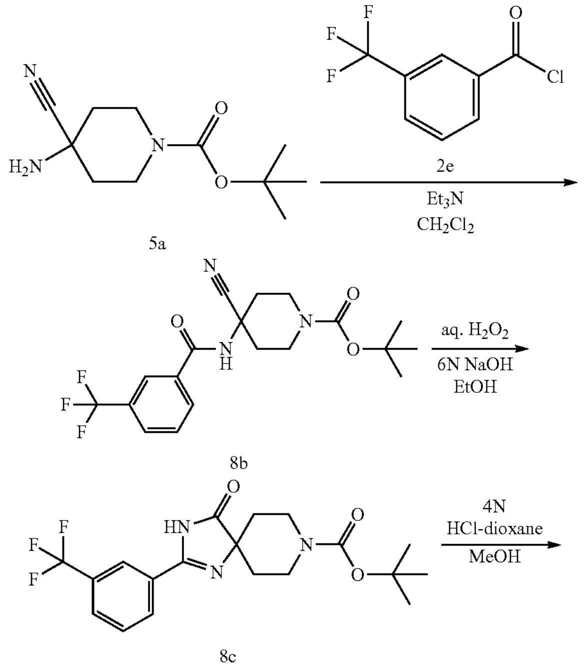

-continued

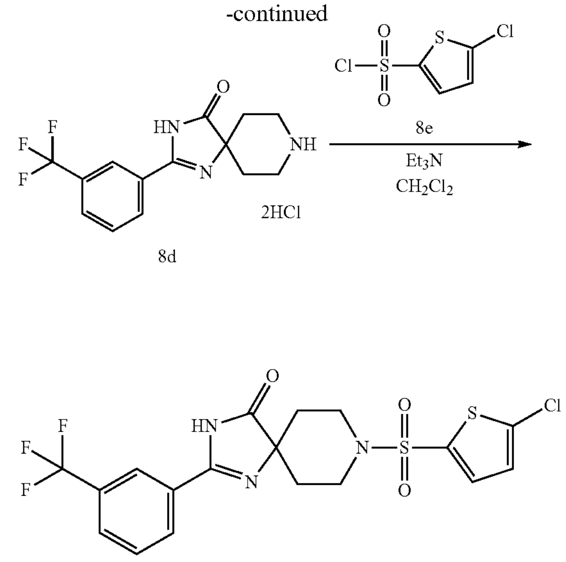

Compound 66

8-(5-Chloro-thiophene-2-sulfonyl)-2-(3-trifluoromethyl-phenyl)-1,3,8-triaza-spiro[4.5]dec-1-en-4-one was synthesized by operations similar to those in Example 5 using appropriate reagents and starting material.

MS (ESI) m/z=478 (M+H)+.

The example compounds shown below were synthesized by operations similar to those in Example 8 using appropriate reagents and starting materials.

TABLE 8

| Compound | Structure | LCMS or HPLC condition | Retention time (min) | MS (m/z) |
|---|---|---|---|---|
| 67 | 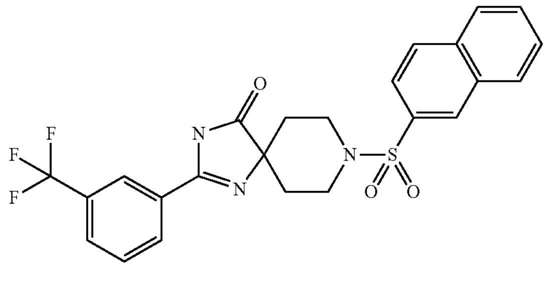 [SMILES: O=C1NC(c2cccc(C(F)(F)F)c2)=NC12CCN(S(=O)(=O)c1ccc3ccccc3c1)CC2] | LCMS-C-1 | 2.90 | 488 (M + H)+ |
| 68 | 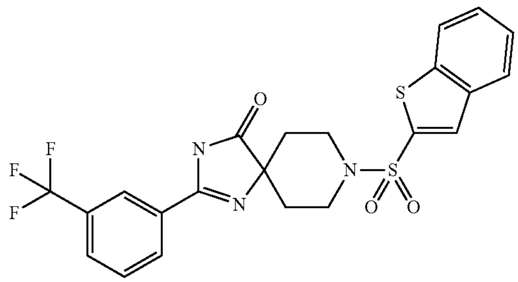 [SMILES: O=C1NC(c2cccc(C(F)(F)F)c2)=NC12CCN(S(=O)(=O)c1cc3ccccc3s1)CC2] | LCMS-C-1 | 2.92 | 494 (M + H)+ |

TABLE 8-continued

| Compound | Structure | LCMS or HPLC condition | Retention time (min) | MS (m/z) |
|---|---|---|---|---|
| 69 | 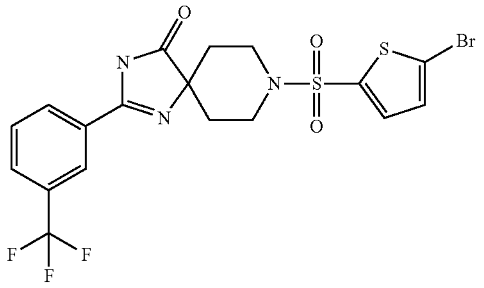 [SMILES: O=C1NC(c2cccc(C(F)(F)F)c2)=NC12CCN(S(=O)(=O)c1ccc(Br)s1)CC2] | LCMS-C-2 | 2.38 | 523 (M + H)+ |

Example 9

8-(3-Chloro-benzenesulfonyl)-2-cyclohexyl-1,3,8-triaza-spiro[4.6]undec-1-en-4-one (Compound 70)

(Reaction 9-1)

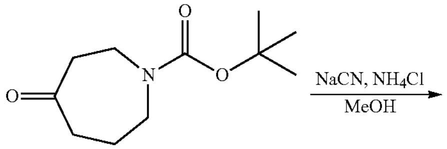

9a

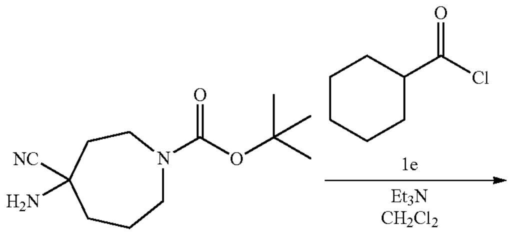

9b

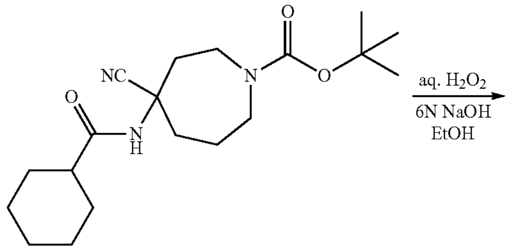

9c

-continued

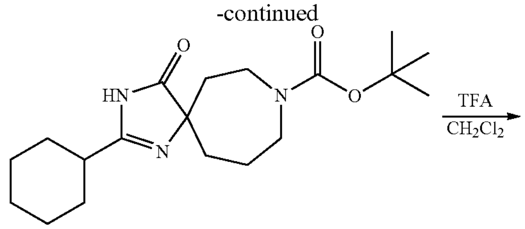

9d

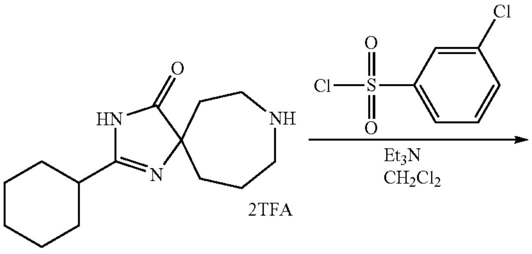

9e

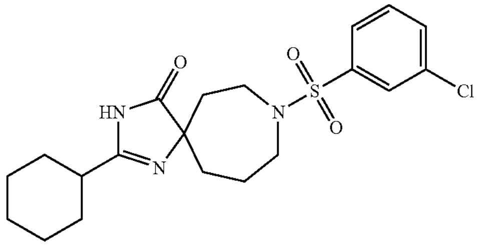

Compound 70

8-(3-Chloro-benzenesulfonyl)-2-cyclohexyl-1,3,8-triaza-spiro[4.6]undec-1-en-4-one was synthesized by operations similar to those in Reaction 1-2 of Example 1 and Example 7 using appropriate reagents and starting material.

MS (ESI) m/z=424 (M+H)+.

The example compounds shown below were synthesized by operations similar to those in Example 9 using appropriate reagents and starting materials.

TABLE 9

| Compound | Structure | LCMS or HPLC condition | Retention time (min) | MS (m/z) |
|---|---|---|---|---|
| 71 | 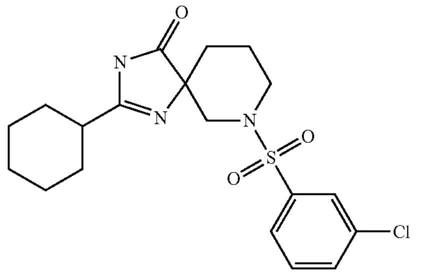 [SMILES: O=C1NC(C2CCCCC2)=NC12CCCN(S(=O)(=O)c1cccc(Cl)c1)C2] | LCMS-E-2 | 2.78 | 410 (M + H)+ |
| 72 | 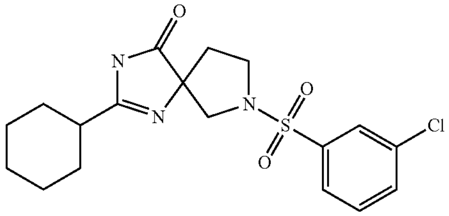 [SMILES: O=C1NC(C2CCCCC2)=NC12CCN(S(=O)(=O)c1cccc(Cl)c1)C2] | LCMS-E-2 | 2.81 | 396 (M + H)+ |

Example 10

4-{2-[2-(2,4-Dichloro-phenyl)-4-oxo-1,3,8-triaza-spiro[4.5]dec-1-ene-8-sulfonyl]-ethyl}-3,N,N-trimethyl-benzamide (Compound 73)

(Reaction 10-1)

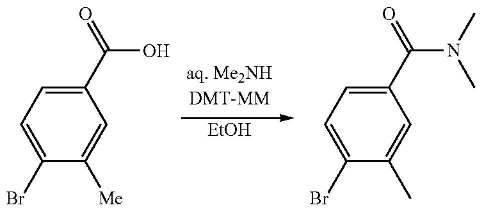

10a 10b 4-(4,6-Dimethoxy-1,3,5-triazin-2-yl)-4-methylmorpholinium chloride n-hydrate (n=about 2.7) (2.42 g, 7.53 mmol) was added to a mixture of 4-bromo-3-methylbenzoic acid (1.58 g, 7.37 mmol), EtOH (26 ml) and a 40% aqueous dimethylamine solution (0.75 ml, 7.4 mmol), and the mixture was stirred at room temperature for 24 hours. The reaction mixture was concentrated under reduced pressure, and the resulting residue was then dissolved in ethyl acetate. The organic layer was washed with water, and then dried over $MgSO_4$ and concentrated under reduced pressure. The resulting residue was purified by silica gel column chromatography (hexane/ethyl acetate=2/1) to give 4-bromo-3,N,N-trimethylbenzamide as a colorless solid (1.16 g, 65%).

$^1$H-NMR (300 MHz) ($CDCl_3$) δ 2.42 (3H, s), 2.98 (3H, br s), 3.10 (3H, br s), 7.08 (1H, dd, J=8.4 and 2.1 Hz), 7.30 (1H, d, J=2.1 Hz), 7.55 (1H, d, J=8.4 Hz). MS (ESI) m/z=243 (M+H)+.

(Reaction 10-2)

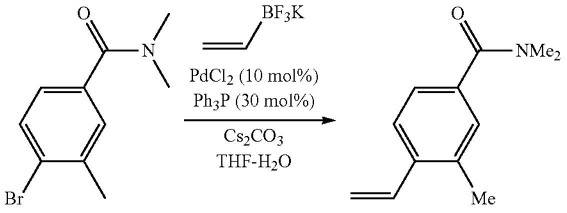

10b 10c

A mixture of 4-bromo-3,N,N-trimethyl-benzamide (798 mg, 3.30 mmol), potassium vinyltrifluoroborate (579 mg, 4.32 mmol), $PdCl_2$ (59.0 mg, 0.333 mmol), $PPh_3$ (265 mg, 1.01 mmol) and $Cs_2CO_3$ (3.22 g, 9.90 mmol) in THF (6.5 ml)-$H_2O$ (0.65 ml) was heated with stirring at 85° C. for 21 hours in a sealed test tube in an $N_2$ atmosphere. The reaction mixture was cooled to room temperature and then extracted with ether. The organic layer was washed with water, and then dried over $MgSO_4$ and concentrated under reduced pressure. The resulting residue was purified by silica gel column chromatography (hexane/ethyl acetate=2/1) to give 3,N,N-trimethyl-4-vinyl-benzamide (565 mg, 90%).

$^1$H-NMR (400 MHz) ($CDCl_3$) δ 2.36 (3H, s), 3.00 (3H, br s), 3.10 (3H, br s), 5.35 (1H, dd, J=11.0 and 1.0 Hz), 5.68 (1H, dd, J=17.5 and 1.0 Hz), 6.93 (1H, dd, J=17.5 and 11.0 Hz), 7.21 (1H, d, J=8.0 Hz), 7.22 (1H, s), 7.48 (1H, d, J=8.0 Hz). MS (ESI) m/z=190 (M+H)+.

(Reaction 10-3)

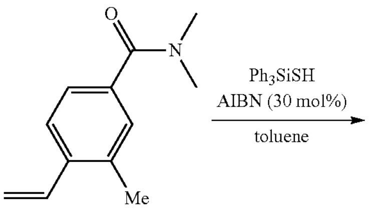

10c

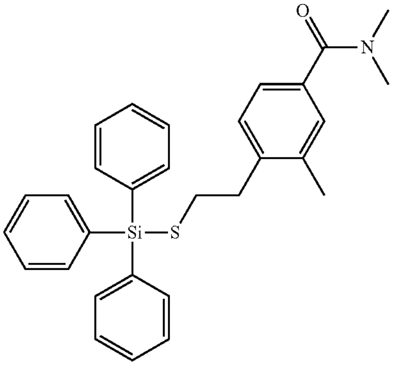

10d

A mixture of 3,N,N-trimethyl-4-vinyl-benzamide (706 mg, 3.73 mmol), triphenylsilanethiol (1.76 g, 6.00 mmol) and AIBN (185 mg, 1.13 mmol) in toluene (16 ml) was heated with stirring at 88° C. for two hours in a sealed test tube in an $N_2$ atmosphere. The reaction mixture was cooled to room temperature and then concentrated under reduced pressure. The resulting residue was purified by silica gel column chromatography (hexane/ethyl acetate=2/1) to give 3,N,N-trimethyl-4-(2-triphenylsilanylsulfanyl-ethyl)-benzamide (1.24 g, 69%).

$^1$H-NMR (400 MHz) ($CDCl_3$) δ 2.08 (3H, s), 2.61 (2H, m), 2.75 (2H, m), 2.95 (3H, br s), 3.07 (3H, br s), 6.89 (1H, d, J=7.8 Hz), 7.08 (1H, d, J=7.8 Hz), 7.12 (1H, s), 7.37-7.47 (9H, m), 7.66-7.69 (6H, m). MS (ESI) m/z=482 (M+H)+.

(Reaction 10-4)

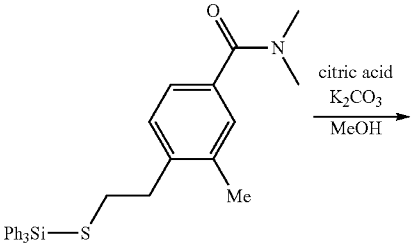

10d

-continued

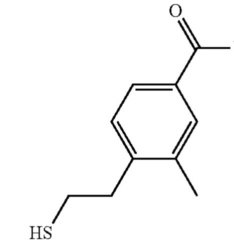

10e

Citric acid monohydrate (110 mg, 0.523 mmol) and potassium carbonate (52.8 mg, 0.382 mmol) were added to a solution of 3,N,N-trimethyl-4-(2-triphenylsilanylsulfanyl-ethyl)-benzamide (767 mg, 1.59 mmol) in MeOH (27 ml) at room temperature, and the mixture was stirred for one hour. The reaction mixture was concentrated under reduced pressure, and the residue was then dissolved in dichloromethane. The organic layer was washed with water, and then dried over $MgSO_4$ and concentrated under reduced pressure. The resulting residue was purified by silica gel column chromatography (hexane/ethyl acetate=2/1) to give 4-(2-mercapto-ethyl)-3,N,N-trimethyl-benzamide (351 mg, 99%).

$^1$H-NMR (400 MHz) ($CDCl_3$) δ 2.33 (3H, s), 2.74 (2H, dt, J=7.5 and 7.5 Hz), 2.94 (2H, t, J=7.5 Hz), 2.99 (3H, br s), 3.10 (3H, br s), 7.16 (1H, d, J=7.8 Hz), 7.18 (1H, d, J=7.8 Hz), 7.23 (1H, s). MS (ESI) m/z=224 (M+H)+.

(Reaction 10-5)

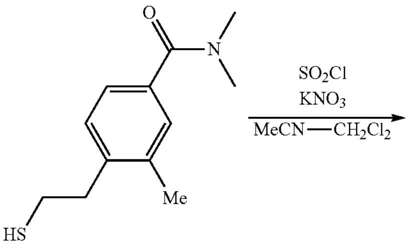

10e

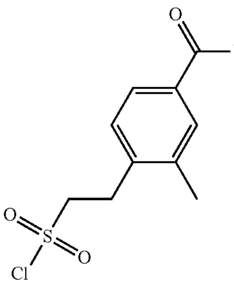

10f

Potassium nitrate (583 mg, 5.77 mmol) was added to a solution of 4-(2-mercapto-ethyl)-3,N,N-trimethyl-benzamide (514 mg, 2.30 mmol) in MeCN (23 ml) at room temperature. The mixture was cooled to −40° C., and sulfuryl chloride (1.68 M solution in dichloromethane, 3.46 ml, 5.81 mmol) was then added dropwise over 15 minutes. After stirring at −40° C. to −20° C. for 2.5 hours, the reaction mixture was diluted with dichloromethane (80 ml) and quenched with a saturated aqueous sodium bicarbonate solution (20 ml). The organic layer and the aqueous layer were separated, and the organic layer was then washed with a saturated aqueous sodium chloride solution (30 ml), dried over $MgSO_4$ and concentrated under reduced pressure. The resulting residue was purified by silica gel column chromatography (hexane/ethyl acetate=1/1→1/2) to give 2-(4-dimethylcarbamoyl-2-methyl-phenyl)-ethanesulfonyl chloride as a colorless solid (491 mg, 74%).

$^1$H-NMR (300 MHz) ($CDCl_3$) δ 2.39 (3H, s), 2.99 (3H, br s), 3.11 (3H, br s), 3.36 (2H, m), 3.83 (2H, m), 7.19 (1H, d, J=7.5 Hz), 7.23 (1H, dd, J=7.5 and 1.5 Hz), 7.28 (1H, d, J=1.5 Hz). MS (ESI) m/z=290 (M+H)+.

(Reaction 10-6)

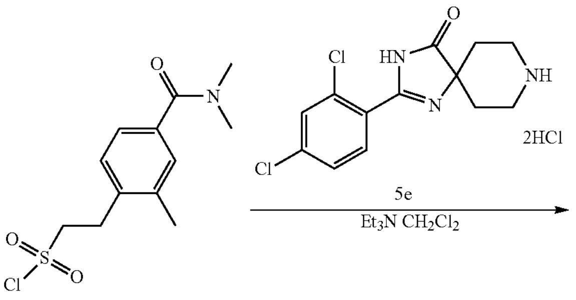

10f

-continued

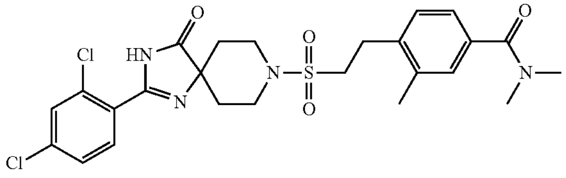

Compound 73

4-{2-[2-(2,4-Dichloro-phenyl)-4-oxo-1,3,8-triaza-spiro[4.5]dec-1-ene-8-sulfonyl]-ethyl}-3,N,N-trimethyl-benzamide was synthesized by operations similar to those in Reaction 5-4 of Example 5 using appropriate reagents and starting material.

MS (ESI) m/z=551 (M+H)+.

The example compounds shown below were synthesized by operations similar to those in Example 10 using appropriate reagents and starting materials.

Compounds 74 to 144

TABLE 10

| Compound | Structure | LCMS or HPLC condition | Retention time (min) | MS (m/z) |
|---|---|---|---|---|
| 74 | 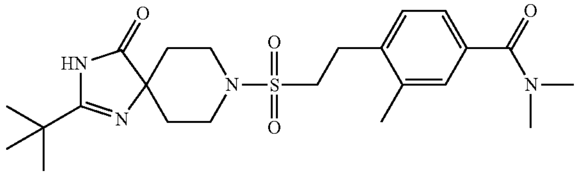 [SMILES: Cc1cc(C(=O)N(C)C)ccc1CCS(=O)(=O)N1CCC2(CC1)N=C(C(C)(C)C)NC2=O] | LCMS-C-2 | 1.57 | 463 (M + H)+ |
| 75 | 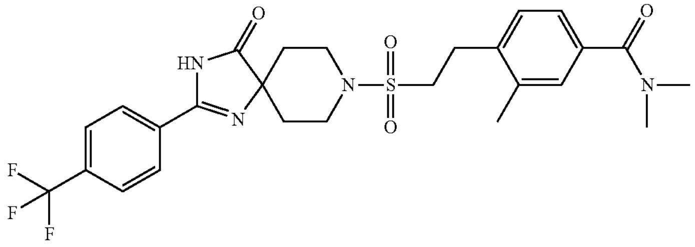 [SMILES: Cc1cc(C(=O)N(C)C)ccc1CCS(=O)(=O)N1CCC2(CC1)N=C(c1ccc(C(F)(F)F)cc1)NC2=O] | LCMS-C-1 | 2.58 | 551 (M + H)+ |
| 76 | 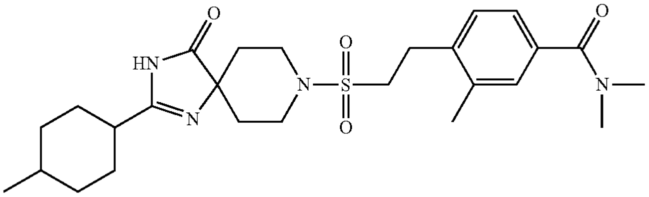 | LCMS-C-1 | 2.50 | 503 (M + H)+ |
| 77 | 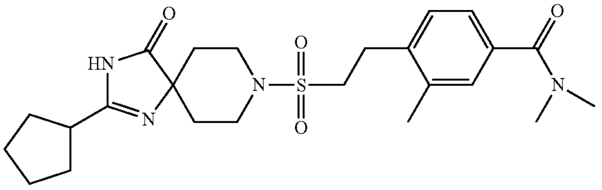 [SMILES: Cc1cc(C(=O)N(C)C)ccc1CCS(=O)(=O)N1CCC2(CC1)N=C(C1CCCC1)NC2=O] | LCMS-C-1 | 2.22 | 475 (M + H)+ |

TABLE 10-continued
| Compound | Structure | LCMS or HPLC condition | Retention time (min) | MS (m/z) |
|---|---|---|---|---|
| 78 | 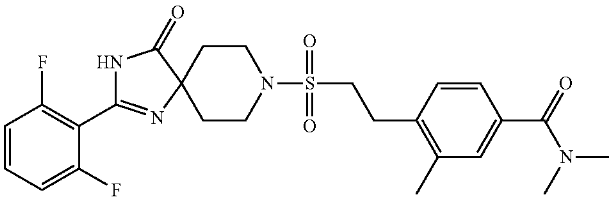 [SMILES: Cc1cc(C(=O)N(C)C)ccc1CCS(=O)(=O)N1CCC2(CC1)N=C(c1c(F)cccc1F)NC2=O] | LCMS-C-1 | 2.13 | 519 (M + H)+ |
| 79 | 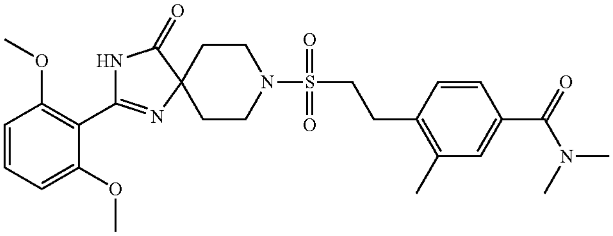 [SMILES: COc1cccc(OC)c1C1=NC2(CCN(S(=O)(=O)CCc3ccc(C(=O)N(C)C)cc3C)CC2)C(=O)N1] | LCMS-A-1 | 1.88 | 543 (M + H)+ |
| 80 | 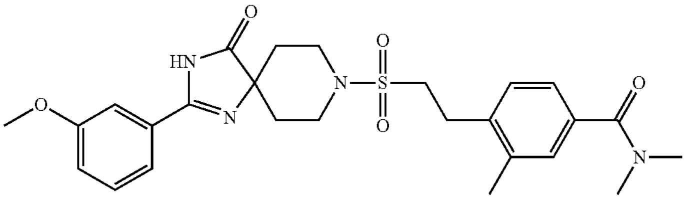 | LCMS-C-1 | 2.32 | 513 (M + H)+ |
| 81 | 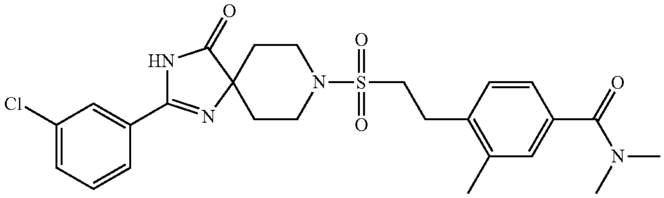 [SMILES: Cc1cc(C(=O)N(C)C)ccc1CCS(=O)(=O)N1CCC2(CC1)N=C(c1cccc(Cl)c1)NC2=O] | LCMS-C-1 | 2.50 | 517 (M + H)+ |
| 82 | 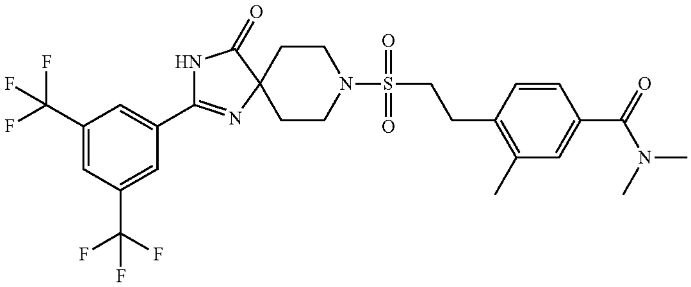 [SMILES: Cc1cc(C(=O)N(C)C)ccc1CCS(=O)(=O)N1CCC2(CC1)N=C(c1cc(C(F)(F)F)cc(C(F)(F)F)c1)NC2=O] | LCMS-A-1 | 2.72 | 619 (M + H)+ |
| 83 | 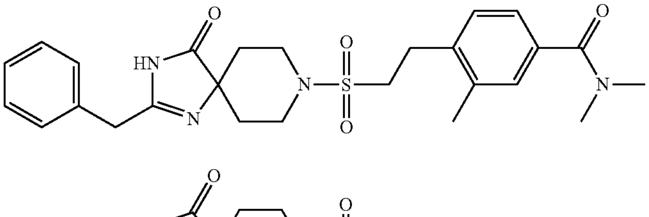 | LCMS-C-1 | 2.23 | 497 (M + H)+ |
| 84 | 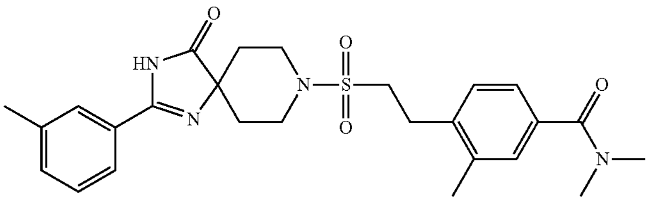 | LCQ-01 | 2.01 | 497 (M + H)+ |

TABLE 10-continued
| Compound | Structure | LCMS or HPLC condition | Retention time (min) | MS (m/z) |
|---|---|---|---|---|
| 85 | 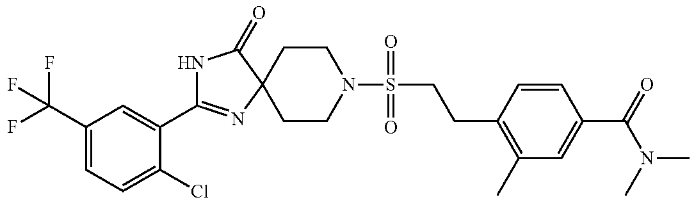 [SMILES: Cc1cc(C(=O)N(C)C)ccc1CCS(=O)(=O)N1CCC2(CC1)N=C(c1cc(C(F)(F)F)ccc1Cl)NC2=O] | LCMS-C-1 | 2.47 | 585 (M + H)+ |
| 86 | 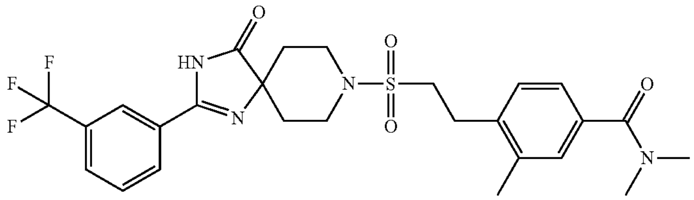 [SMILES: Cc1cc(C(=O)N(C)C)ccc1CCS(=O)(=O)N1CCC2(CC1)N=C(c1cccc(C(F)(F)F)c1)NC2=O] | LCMS-C-1 | 2.57 | 551 (M + H)+ |
| 87 | 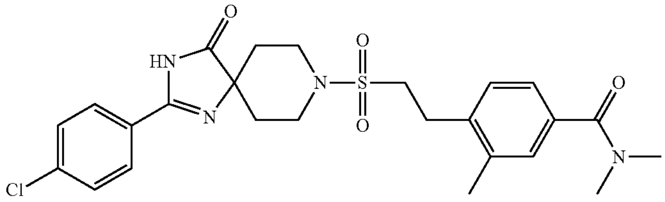 [SMILES: Cc1cc(C(=O)N(C)C)ccc1CCS(=O)(=O)N1CCC2(CC1)N=C(c1ccc(Cl)cc1)NC2=O] | LCMS-C-1 | 2.48 | 517 (M + H)+ |
| 88 | 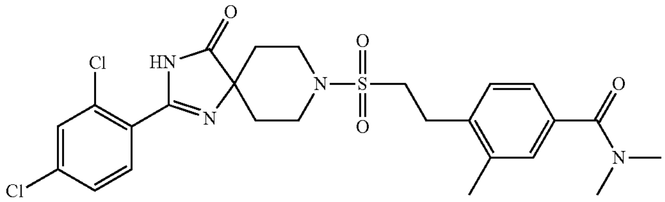 [SMILES: Cc1cc(C(=O)N(C)C)ccc1CCS(=O)(=O)N1CCC2(CC1)N=C(c1ccc(Cl)cc1Cl)NC2=O] | LCMS-C-1 | 2.43 | 551 (M + H)+ |
| 89 | 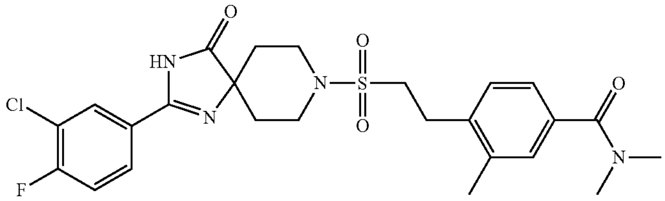 [SMILES: Cc1cc(C(=O)N(C)C)ccc1CCS(=O)(=O)N1CCC2(CC1)N=C(c1ccc(F)c(Cl)c1)NC2=O] | LCMS-C-1 | 2.53 | 535 (M + H)+ |
| 90 | 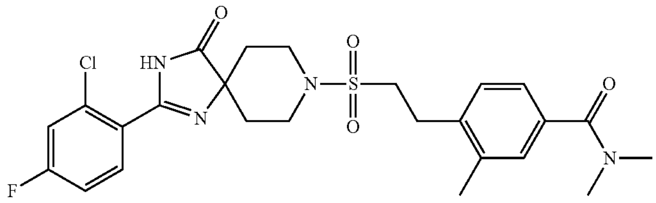 [SMILES: Cc1cc(C(=O)N(C)C)ccc1CCS(=O)(=O)N1CCC2(CC1)N=C(c1ccc(F)cc1Cl)NC2=O] | LCMS-C-1 | 2.30 | 535 (M + H)+ |
| 91 | 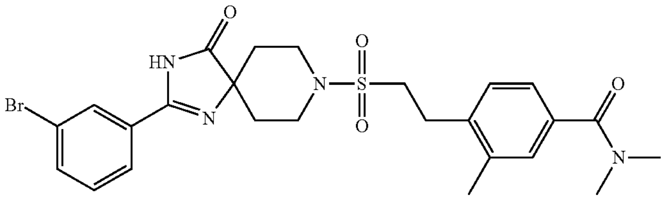 | LCMS-B-1 | 2.01 | 561 (M + H)+ |

TABLE 10-continued
| Compound | Structure | LCMS or HPLC condition | Retention time (min) | MS (m/z) |
|---|---|---|---|---|
| 92 | 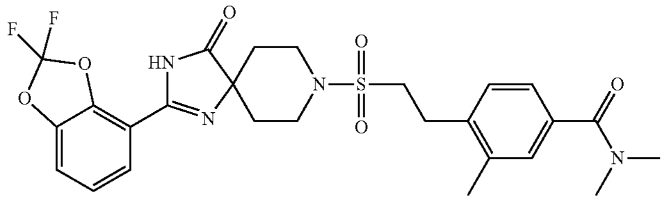 [SMILES: Cc1cc(C(=O)N(C)C)ccc1CCS(=O)(=O)N1CCC2(CC1)N=C(c1cccc3c1OC(F)(F)O3)NC2=O] | LCMS-C-2 | 1.87 | 563 (M + H)+ |
| 93 | 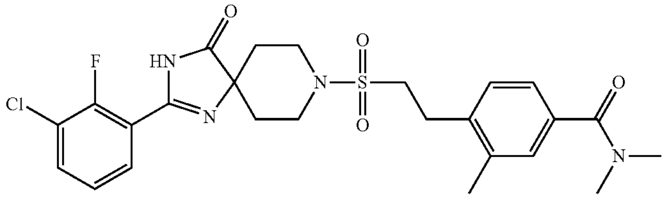 [SMILES: Cc1cc(C(=O)N(C)C)ccc1CCS(=O)(=O)N1CCC2(CC1)N=C(c1cccc(Cl)c1F)NC2=O] | LCMS-B-1 | 1.97 | 535 (M + H)+ |
| 94 | 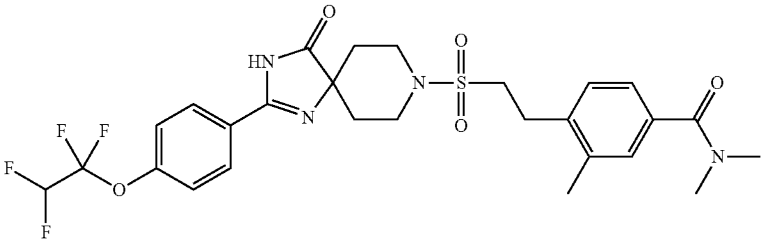 [SMILES: Cc1cc(C(=O)N(C)C)ccc1CCS(=O)(=O)N1CCC2(CC1)N=C(c1ccc(OC(F)(F)C(F)F)cc1)NC2=O] | LCMS-C-1 | 2.52 | 599 (M + H)+ |
| 95 | 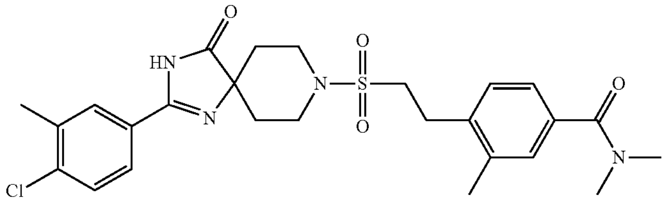 | LCMS-C-1 | 2.60 | 531 (M + H)+ |
| 96 | 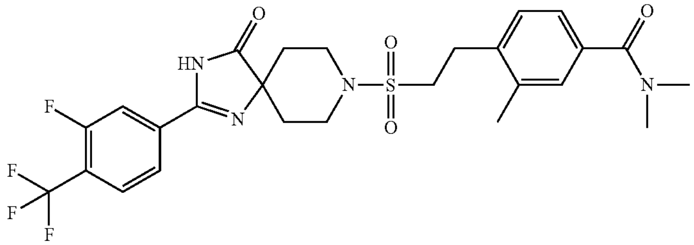 [SMILES: Cc1cc(C(=O)N(C)C)ccc1CCS(=O)(=O)N1CCC2(CC1)N=C(c1ccc(C(F)(F)F)c(F)c1)NC2=O] | LCMS-C-1 | 2.38 | 569 (M + H)+ |
| 97 | 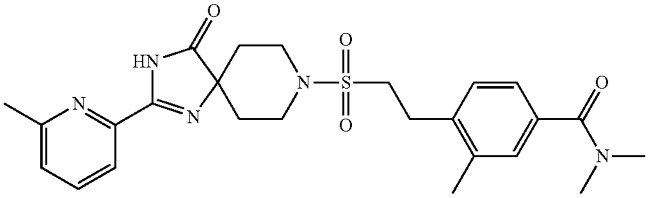 | LCMS-C-1 | 2.22 | 498 (M + H)+ |
| 98 | 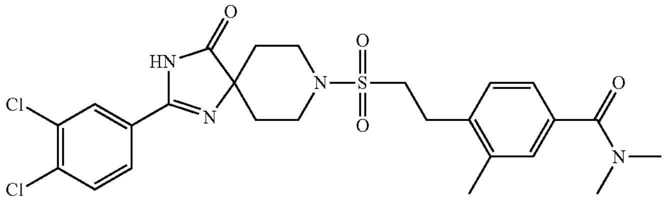 [SMILES: Cc1cc(C(=O)N(C)C)ccc1CCS(=O)(=O)N1CCC2(CC1)N=C(c1ccc(Cl)c(Cl)c1)NC2=O] | LCMS-C-1 | 2.67 | 551 (M + H)+ |

TABLE 10-continued
| Compound | Structure | LCMS or HPLC condition | Retention time (min) | MS (m/z) |
|---|---|---|---|---|
| 99 | 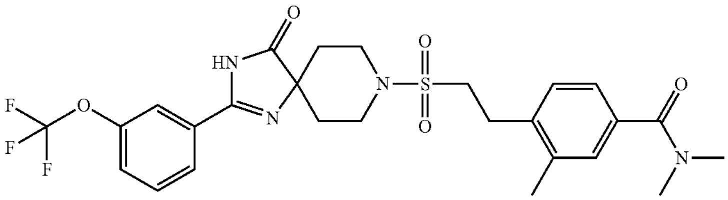 [SMILES: Cc1cc(C(=O)N(C)C)ccc1CCS(=O)(=O)N1CCC2(CC1)N=C(c1cccc(OC(F)(F)F)c1)NC2=O] | LCMS-C-1 | 2.60 | 567 (M + H)+ |
| 100 | 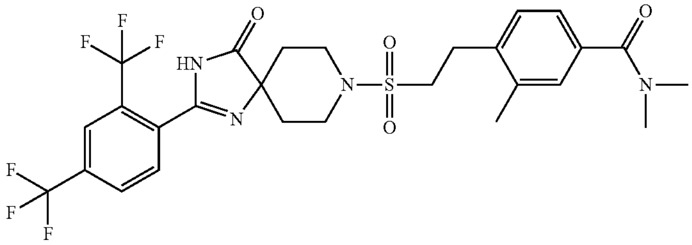 [SMILES: Cc1cc(C(=O)N(C)C)ccc1CCS(=O)(=O)N1CCC2(CC1)N=C(c1ccc(C(F)(F)F)cc1C(F)(F)F)NC2=O] | LCMS-C-1 | 2.63 | 619 (M + H)+ |
| 101 | 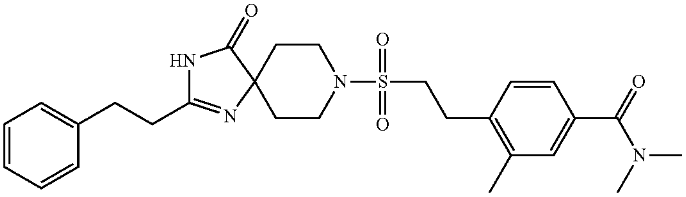 [SMILES: Cc1cc(C(=O)N(C)C)ccc1CCS(=O)(=O)N1CCC2(CC1)N=C(CCc1ccccc1)NC2=O] | LCMS-C-1 | 2.33 | 511 (M + H)+ |
| 102 | 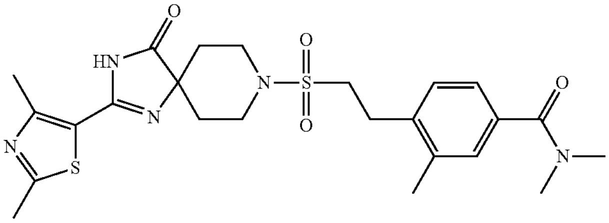 [SMILES: Cc1nc(C)c(C2=NC3(CCN(S(=O)(=O)CCc4ccc(C(=O)N(C)C)cc4C)CC3)C(=O)N2)s1] | LCMS-C-1 | 2.07 | 518 (M + H)+ |
| 103 | 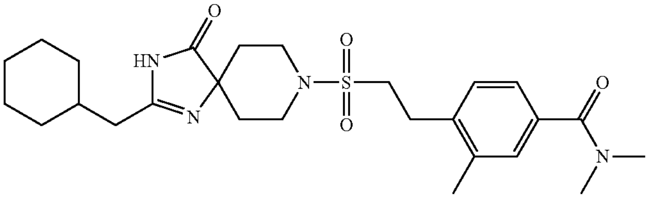 [SMILES: Cc1cc(C(=O)N(C)C)ccc1CCS(=O)(=O)N1CCC2(CC1)N=C(CC1CCCCC1)NC2=O] | LCMS-A-1 | 2.02 | 503 (M + H)+ |
| 104 | 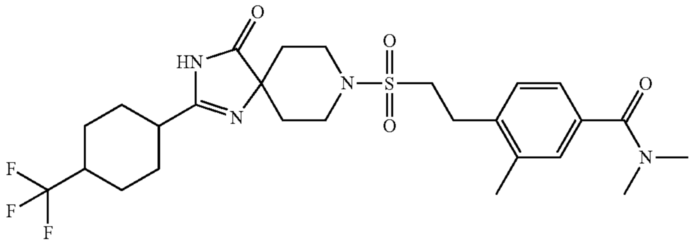 [SMILES: Cc1cc(C(=O)N(C)C)ccc1CCS(=O)(=O)N1CCC2(CC1)N=C(C1CCC(C(F)(F)F)CC1)NC2=O] | LCMS-A-1 | 2.12 | 557 (M + H)+ |
| 105 | 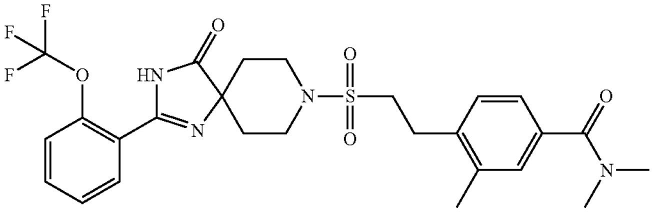 [SMILES: Cc1cc(C(=O)N(C)C)ccc1CCS(=O)(=O)N1CCC2(CC1)N=C(c1ccccc1OC(F)(F)F)NC2=O] | LCMS-C-1 | 2.40 | 567 (M + H)+ |

TABLE 10-continued
| Compound | Structure | LCMS or HPLC condition | Retention time (min) | MS (m/z) |
|---|---|---|---|---|
| 106 | 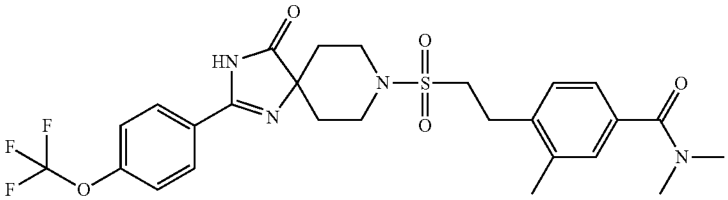 [SMILES: Cc1cc(C(=O)N(C)C)ccc1CCS(=O)(=O)N1CCC2(CC1)N=C(c1ccc(OC(F)(F)F)cc1)NC2=O] | LCMS-C-1 | 2.62 | 567 (M + H)+ |
| 107 | 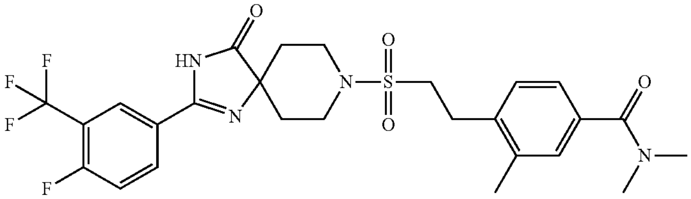 [SMILES: Cc1cc(C(=O)N(C)C)ccc1CCS(=O)(=O)N1CCC2(CC1)N=C(c1ccc(F)c(C(F)(F)F)c1)NC2=O] | LCMS-C-2 | 1.97 | 569 (M + H)+ |
| 108 | 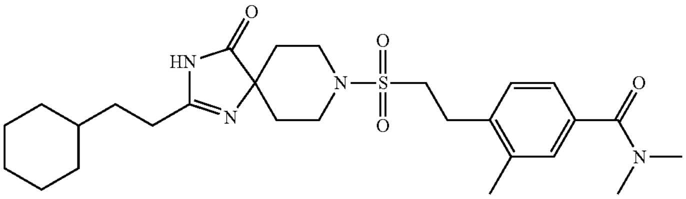 [SMILES: Cc1cc(C(=O)N(C)C)ccc1CCS(=O)(=O)N1CCC2(CC1)N=C(CCC1CCCCC1)NC2=O] | LCMS-C-1 | 2.65 | 517 (M + H)+ |
| 109 | 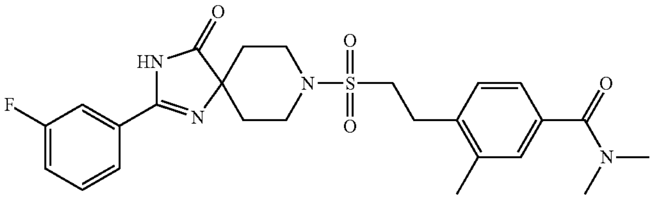 | LCMS-A-1 | 2.10 | 501 (M + H)+ |
| 110 | 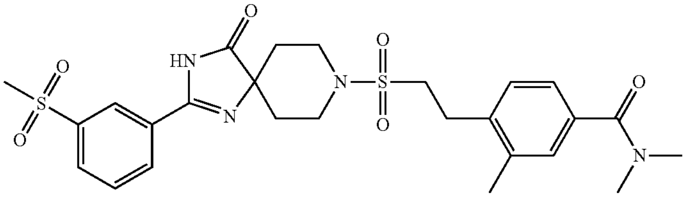 | LCMS-A-1 | 1.96 | 561 (M + H)+ |
| 111 | 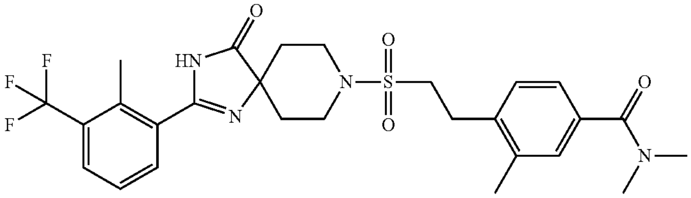 [SMILES: Cc1cc(C(=O)N(C)C)ccc1CCS(=O)(=O)N1CCC2(CC1)N=C(c1cccc(C(F)(F)F)c1C)NC2=O] | LCMS-C-1 | 2.52 | 565 (M + H)+ |
| 112 | 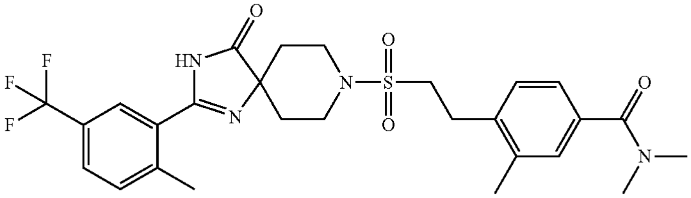 [SMILES: Cc1cc(C(=O)N(C)C)ccc1CCS(=O)(=O)N1CCC2(CC1)N=C(c1cc(C(F)(F)F)ccc1C)NC2=O] | LCMS-C-1 | 2.52 | 565 (M + H)+ |

TABLE 10-continued
| Compound | Structure | LCMS or HPLC condition | Retention time (min) | MS (m/z) |
|---|---|---|---|---|
| 113 | 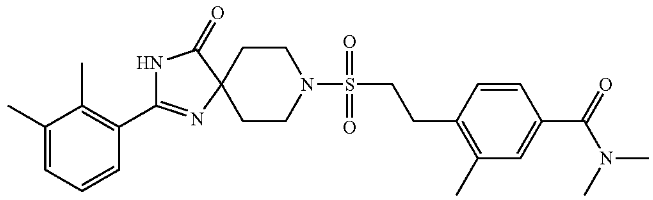 | LCMS-B-1 | 1.78 | 511 (M + H)+ |
| 114 | 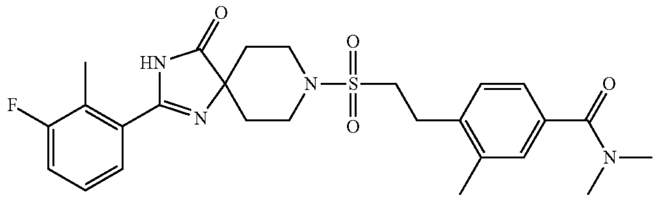 [SMILES: Cc1cc(C(=O)N(C)C)ccc1CCS(=O)(=O)N1CCC2(CC1)N=C(c1cccc(F)c1C)NC2=O] | LCMS-B-1 | 1.87 | 515 (M + H)+ |
| 115 | 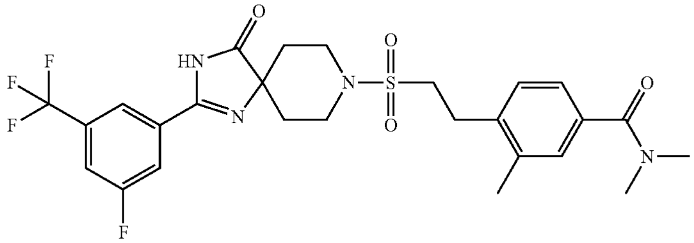 | LCMS-C-1 | 2.67 | 569 (M + H)+ |
| 116 | 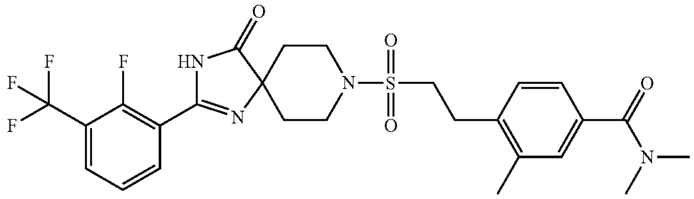 [SMILES: Cc1cc(C(=O)N(C)C)ccc1CCS(=O)(=O)N1CCC2(CC1)N=C(c1cccc(C(F)(F)F)c1F)NC2=O] | LCMS-C-1 | 2.50 | 569 (M + H)+ |
| 117 | 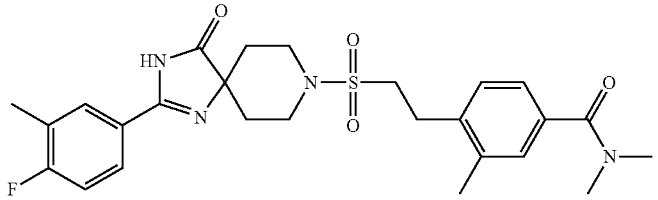 | LCMS-A-1 | 2.12 | 515 (M + H)+ |
| 118 | 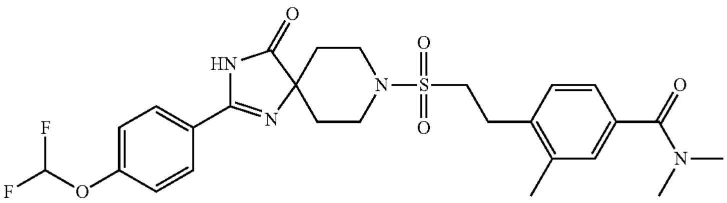 [SMILES: Cc1cc(C(=O)N(C)C)ccc1CCS(=O)(=O)N1CCC2(CC1)N=C(c1ccc(OC(F)F)cc1)NC2=O] | LCMS-C-1 | 2.38 | 549 (M + H)+ |
| 119 | 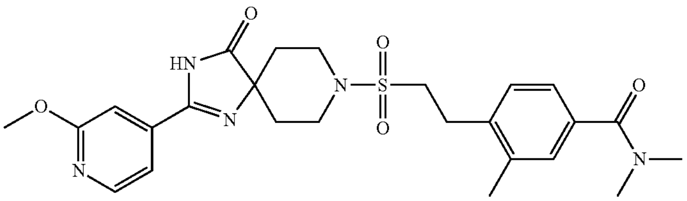 | LCMS-C-1 | 2.27 | 514 (M + H)+ |

TABLE 10-continued
| Compound | Structure | LCMS or HPLC condition | Retention time (min) | MS (m/z) |
|---|---|---|---|---|
| 120 | 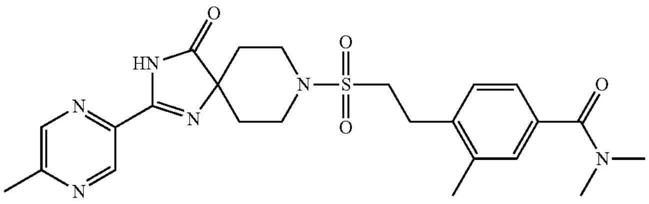 | LCMS-C-1 | 2.10 | 499 (M + H)+ |
| 121 | 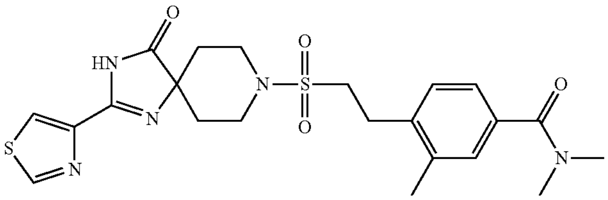 [SMILES: Cc1cc(C(=O)N(C)C)ccc1CCS(=O)(=O)N1CCC2(CC1)N=C(c1cscn1)NC2=O] | LCMS-C-1 | 1.98 | 490 (M + H)+ |
| 122 | 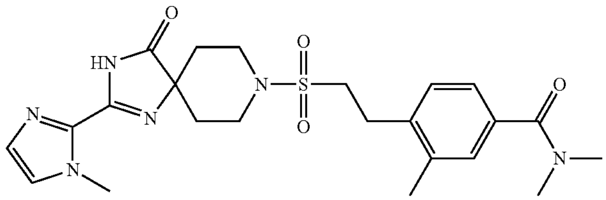 [SMILES: Cc1cc(C(=O)N(C)C)ccc1CCS(=O)(=O)N1CCC2(CC1)N=C(c1nccn1C)NC2=O] | LCMS-C-1 | 2.05 | 487 (M + H)+ |
| 123 | 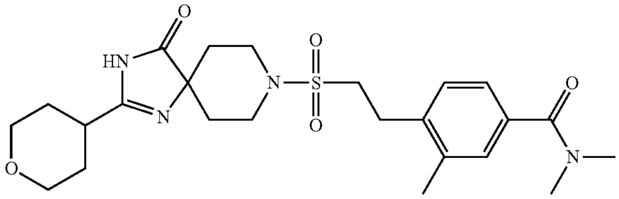 [SMILES: Cc1cc(C(=O)N(C)C)ccc1CCS(=O)(=O)N1CCC2(CC1)N=C(C1CCOCC1)NC2=O] | LCMS-C-1 | 1.95 | 491 (M + H)+ |
| 124 | 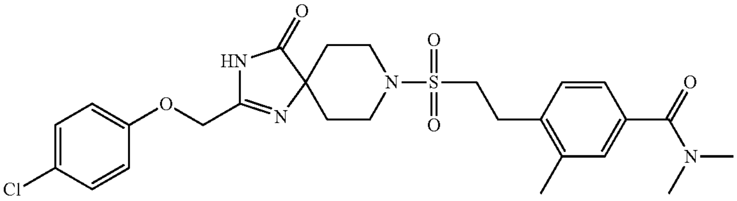 [SMILES: Cc1cc(C(=O)N(C)C)ccc1CCS(=O)(=O)N1CCC2(CC1)N=C(COc1ccc(Cl)cc1)NC2=O] | LCMS-C-1 | 2.48 | 547 (M + H)+ |
| 125 | 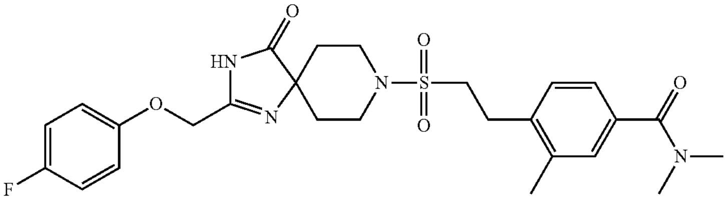 [SMILES: Cc1cc(C(=O)N(C)C)ccc1CCS(=O)(=O)N1CCC2(CC1)N=C(COc1ccc(F)cc1)NC2=O] | LCMS-C-1 | 2.32 | 531 (M + H)+ |
| 126 | 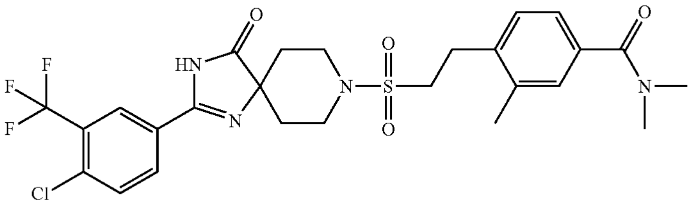 [SMILES: Cc1cc(C(=O)N(C)C)ccc1CCS(=O)(=O)N1CCC2(CC1)N=C(c1ccc(Cl)c(C(F)(F)F)c1)NC2=O] | LCMS-C-1 | 2.72 | 585 (M + H)+ |

TABLE 10-continued
| Compound | Structure | LCMS or HPLC condition | Retention time (min) | MS (m/z) |
|---|---|---|---|---|
| 127 | 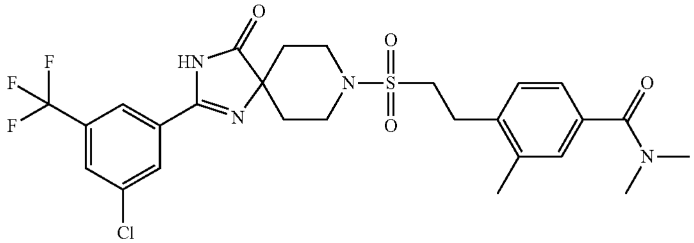 [SMILES: Cc1cc(C(=O)N(C)C)ccc1CCS(=O)(=O)N1CCC2(CC1)N=C(c1cc(Cl)cc(C(F)(F)F)c1)NC2=O] | LCMS-C-1 | 2.78 | 585 (M + H)+ |
| 128 | 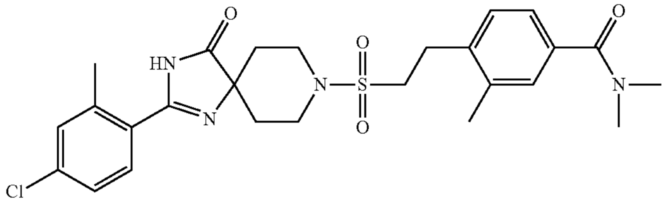 [SMILES: Cc1cc(C(=O)N(C)C)ccc1CCS(=O)(=O)N1CCC2(CC1)N=C(c1ccc(Cl)cc1C)NC2=O] | LCMS-C-1 | 2.42 | 531 (M + H)+ |
| 129 | 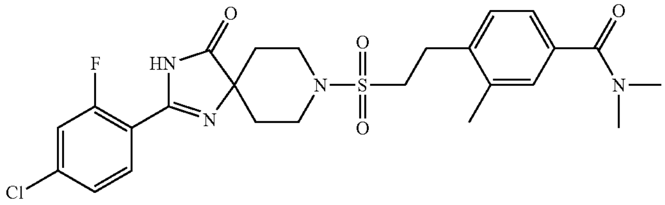 [SMILES: Cc1cc(C(=O)N(C)C)ccc1CCS(=O)(=O)N1CCC2(CC1)N=C(c1ccc(Cl)cc1F)NC2=O] | LCMS-C-1 | 2.42 | 535 (M + H)+ |
| 130 | 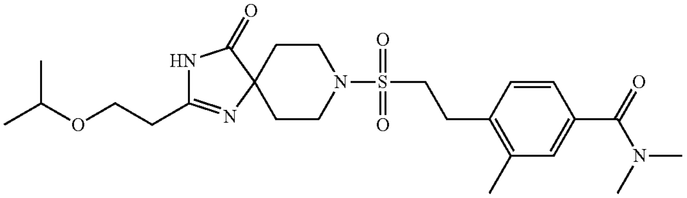 | LCMS-A-1 | 2.19 | 555 (M + H)+ |
| 131 | 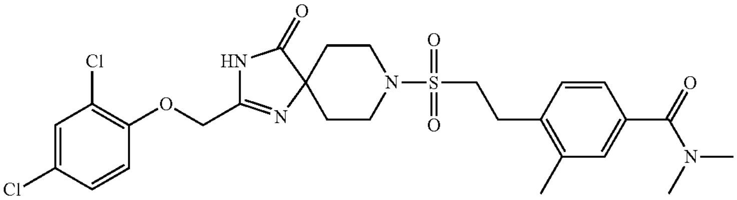 [SMILES: Cc1cc(C(=O)N(C)C)ccc1CCS(=O)(=O)N1CCC2(CC1)N=C(COc1ccc(Cl)cc1Cl)NC2=O] | LCMS-A-1 | 2.45 | 581 (M + H)+ |
| 133 | 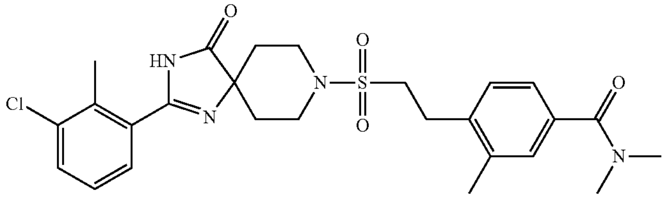 | LCMS-C-1 | 2.45 | 531 (M + H)+ |
| 134 | 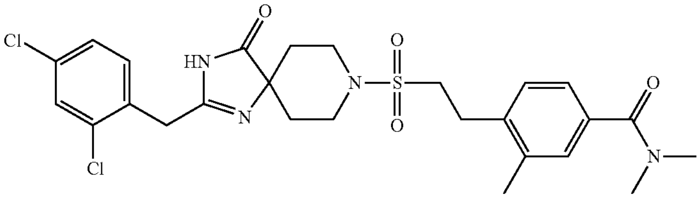 [SMILES: Cc1cc(C(=O)N(C)C)ccc1CCS(=O)(=O)N1CCC2(CC1)N=C(Cc1ccc(Cl)cc1Cl)NC2=O] | LCMS-C-1 | 2.50 | 565 (M + H)+ |

TABLE 10-continued
| Compound | Structure | LCMS or HPLC condition | Retention time (min) | MS (m/z) |
|---|---|---|---|---|
| 135 | 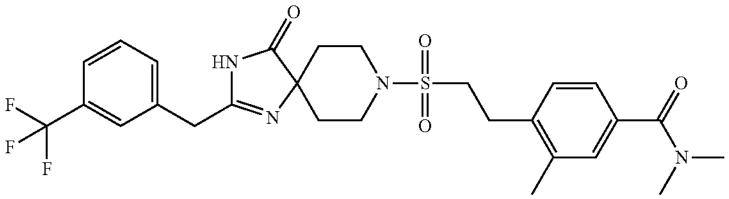 [SMILES: Cc1cc(C(=O)N(C)C)ccc1CCS(=O)(=O)N1CCC2(CC1)N=C(Cc1cccc(C(F)(F)F)c1)NC2=O] | LCMS-C-1 | 2.50 | 565 (M + H)+ |
| 136 | 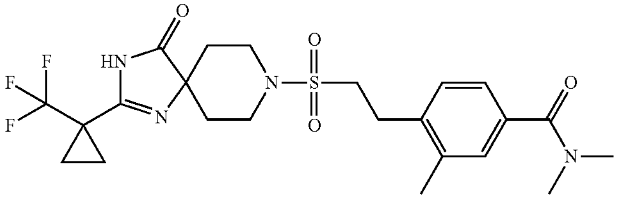 [SMILES: Cc1cc(C(=O)N(C)C)ccc1CCS(=O)(=O)N1CCC2(CC1)N=C(C1(C(F)(F)F)CC1)NC2=O] | LCMS-C-2 | 1.68 | 515 (M + H)+ |
| 137 | 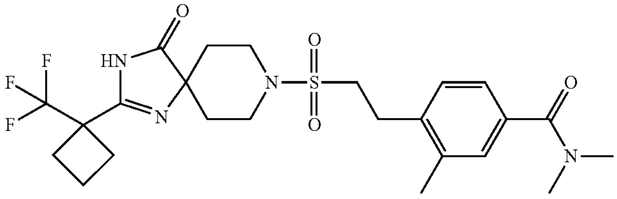 [SMILES: Cc1cc(C(=O)N(C)C)ccc1CCS(=O)(=O)N1CCC2(CC1)N=C(C1(C(F)(F)F)CCC1)NC2=O] | LCMS-C-2 | 1.78 | 529 (M + H)+ |
| 138 | 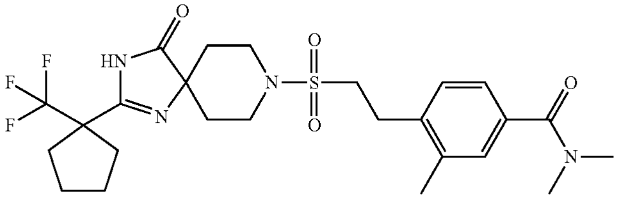 [SMILES: Cc1cc(C(=O)N(C)C)ccc1CCS(=O)(=O)N1CCC2(CC1)N=C(C1(C(F)(F)F)CCCC1)NC2=O] | LCMS-C-2 | 1.98 | 543 (M + H)+ |
| 139 | 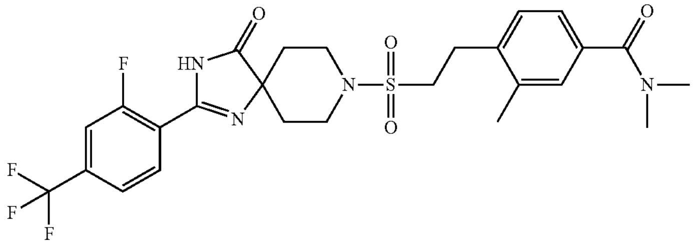 [SMILES: Cc1cc(C(=O)N(C)C)ccc1CCS(=O)(=O)N1CCC2(CC1)N=C(c1ccc(C(F)(F)F)cc1F)NC2=O] | LCMS-C-1 | 2.47 | 569 (M + H)+ |
| 140 | 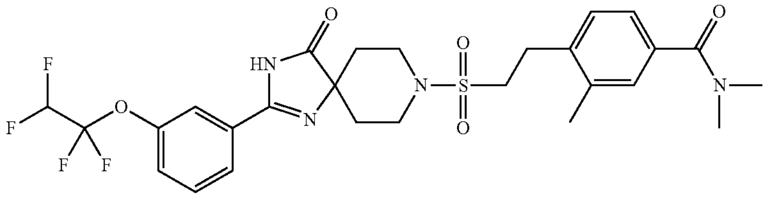 [SMILES: Cc1cc(C(=O)N(C)C)ccc1CCS(=O)(=O)N1CCC2(CC1)N=C(c1cccc(OC(F)(F)C(F)F)c1)NC2=O] | LCMS-A-1 | 2.41 | 599 (M + H)+ |
| 141 | 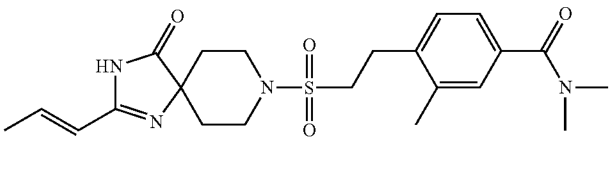 [SMILES: C/C=C/C1=NC2(CCN(S(=O)(=O)CCc3ccc(C(=O)N(C)C)cc3C)CC2)C(=O)N1] | LCMS-C-1 | 2.03 | 447 (M + H)+ |

TABLE 10-continued

| Compound | Structure | LCMS or HPLC condition | Retention time (min) | MS (m/z) |
|---|---|---|---|---|
| 142 | 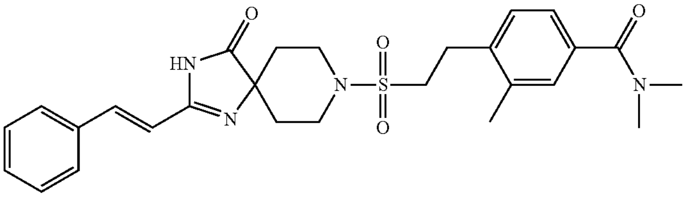 [SMILES: Cc1cc(C(=O)N(C)C)ccc1CCS(=O)(=O)N1CCC2(CC1)N=C(/C=C/c1ccccc1)NC2=O] | LCMS-A-1 | 2.00 | 509 (M + H)+ |
| 143 | 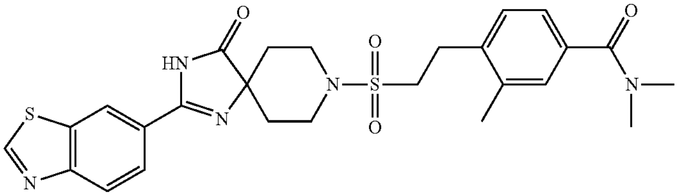 [SMILES: Cc1cc(C(=O)N(C)C)ccc1CCS(=O)(=O)N1CCC2(CC1)N=C(c1ccc3ncsc3c1)NC2=O] | LCMS-C-1 | 2.18 | 540 (M + H)+ |
| 144 | 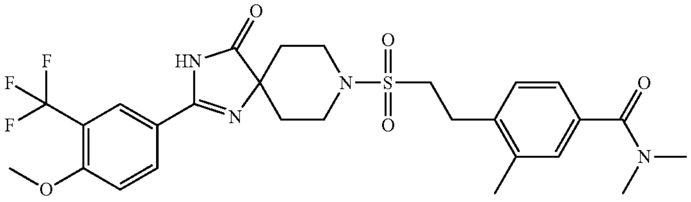 | LCMS-A-1 | 2.26 | 581 (M + H)+ |

The spiroamine reagents used in the synthesis of Compounds 74 to 85 and shown below were synthesized by operations similar to those in Reaction 7-1 and Reaction 7-2 using appropriate reagents and starting materials.

TABLE 11

| Target Compound | Spiroamine reagent | Spiroamine reagent MS (m/z) |
|---|---|---|
| 74 | 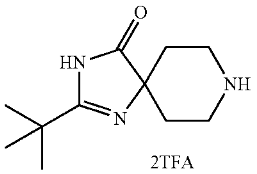 2TFA | This compound was directly used in the next step (Reaction 10-6). |
| 75 | 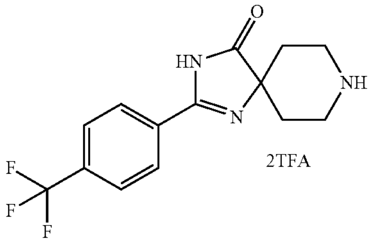 [SMILES: O=C1NC(c2ccc(C(F)(F)F)cc2)=NC12CCNCC2] 2TFA | 298 (M + H)+ |
| 76 | 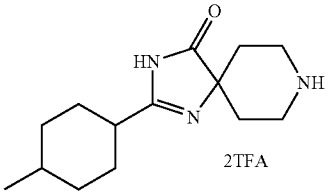 [SMILES: CC1CCC(C2=NC3(CCNCC3)C(=O)N2)CC1] 2TFA | 250 (M + H)+ |

TABLE 11-continued

| Target Compound | Spiroamine reagent | Spiroamine reagent MS (m/z) |
|---|---|---|
| 77 | 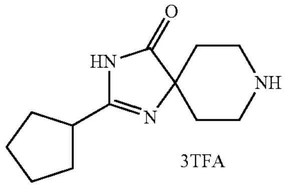 [SMILES: O=C1NC(C2CCCC2)=NC12CCNCC2] 3TFA | 222 (M + H)+ |
| 78 | 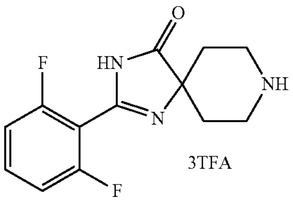 [SMILES: O=C1NC(c2c(F)cccc2F)=NC12CCNCC2] 3TFA | 266 (M + H)+ |
| 79 | 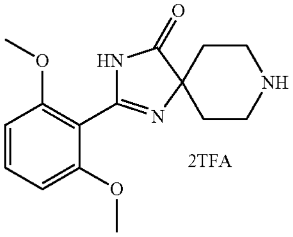 [SMILES: COc1cccc(OC)c1C1=NC2(CCNCC2)C(=O)N1] 2TFA | 290 (M + H)+ |

TABLE 11-continued

| Target Compound | Spiroamine reagent | Spiroamine reagent MS (m/z) |
|---|---|---|
| 80 | 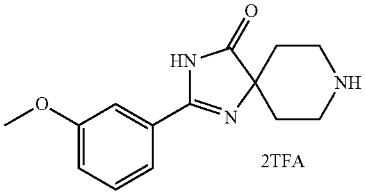 [SMILES: COc1cccc(C2=NC3(CCNCC3)C(=O)N2)c1] 2TFA | 260 (M + H)+ |
| 81 | 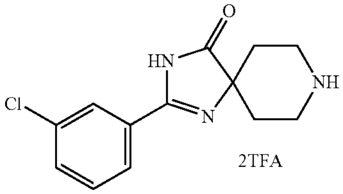 [SMILES: O=C1NC(c2cccc(Cl)c2)=NC12CCNCC2] 2TFA | 264 (M + H)+ |
| 82 | 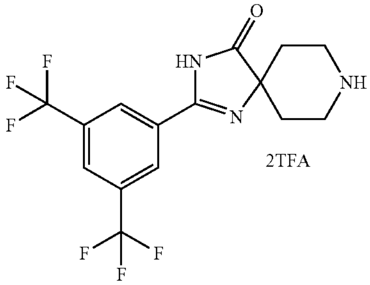 [SMILES: O=C1NC(c2cc(C(F)(F)F)cc(C(F)(F)F)c2)=NC12CCNCC2] 2TFA | 366 (M + H)+ |
| 83 | 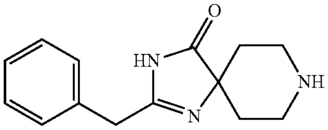 2TFA | 244 (M + H)+ |
| 84 | 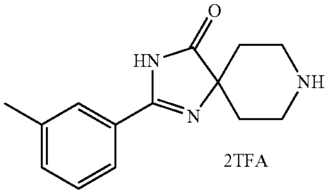 [SMILES: Cc1cccc(C2=NC3(CCNCC3)C(=O)N2)c1] 2TFA | 244 (M + H)+ |
| 85 | 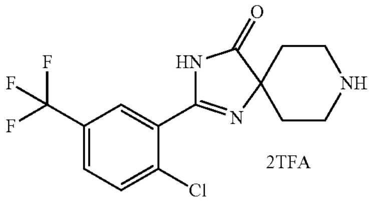 [SMILES: O=C1NC(c2cc(C(F)(F)F)ccc2Cl)=NC12CCNCC2] 2TFA | 332 (M + H)+ |

The spiroamine reagents used in the synthesis of Compounds 86 to 91 and shown below were synthesized by operations similar to those in Example 8 using appropriate reagents and starting materials.

TABLE 12

| Target Compound | Spiroamine reagent | Spiroamine reagent MS (m/z) |
|---|---|---|
| 86 | 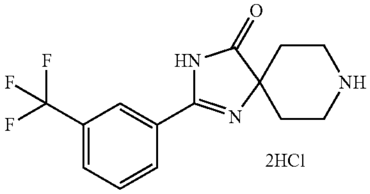 [SMILES: O=C1NC(c2cccc(C(F)(F)F)c2)=NC12CCNCC2] 2HCl | 298 (M + H)+ |
| 87 | 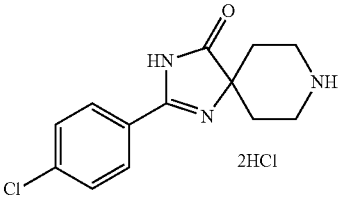 [SMILES: O=C1NC(c2ccc(Cl)cc2)=NC12CCNCC2] 2HCl | 264 (M + H)+ |
| 88 | 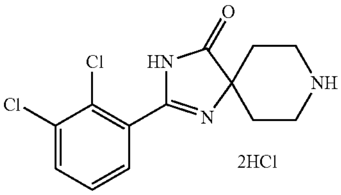 [SMILES: O=C1NC(c2cccc(Cl)c2Cl)=NC12CCNCC2] 2HCl | 298 (M + H)+ |
| 89 | 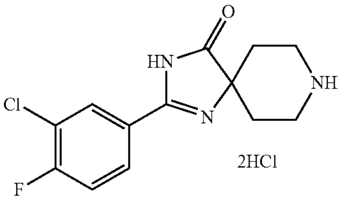 2HCl | 282 (M + H)+ |
| 90 | 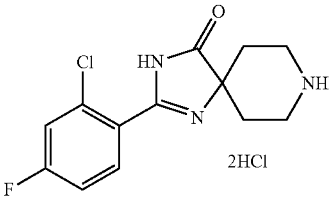 [SMILES: O=C1NC(c2ccc(F)cc2Cl)=NC12CCNCC2] 2HCl | 282 (M + H)+ |
| 91 | 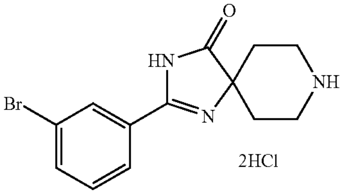 2HCl | 308 (M + H)+ |

The spiroamine reagent used in the synthesis of Compound 92 (2-(2,2-difluoro-benzo[1,3]dioxol-4-yl)-1,3,8-triaza-spiro[4.5]dec-1-en-4-one ditrifluoroacetate) was synthesized as follows.

(Reaction 10-7)

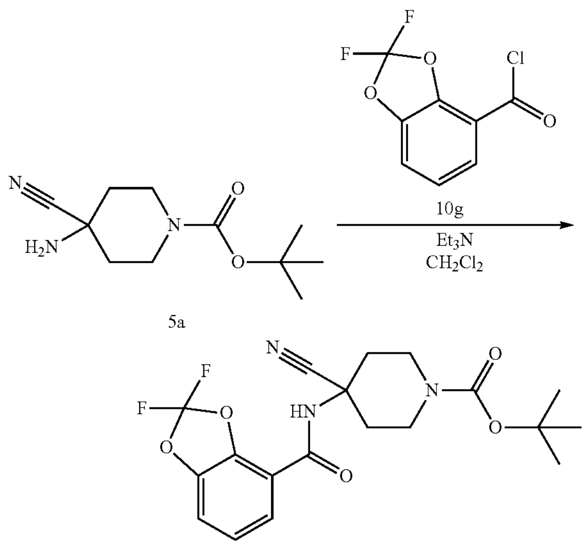

5a

10h

4-Cyano-4-[(2,2-difluoro-benzo[1,3]dioxole-4-carbonyl)-amino]-piperidine-1-carboxylic acid tert-butyl ester was synthesized by operations similar to those in Reaction 2-3 of Example 2 using appropriate reagents and starting material.

MS (ESI) m/z=410 (M+H)+.

(Reaction 10-8)

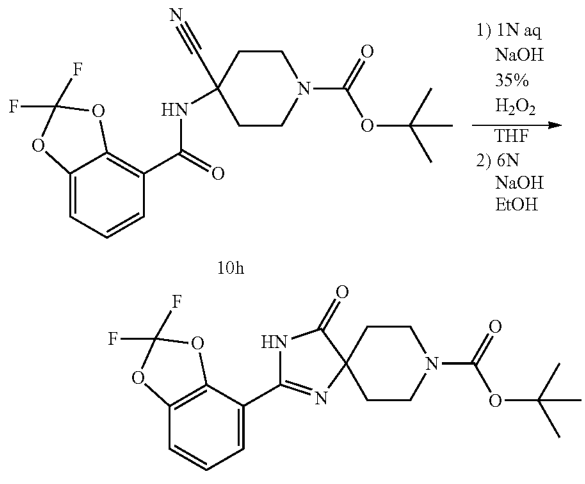

10h

10i

A 1 N aqueous NaOH solution (0.274 ml, 0.274 mmol) and a 35% aqueous $H_2O_2$ solution (0.051 ml, 0.52 mmol) were added to a solution of 4-cyano-4-[(2,2-difluoro-benzo[1,3]dioxole-4-carbonyl)-amino]-piperidine-1-carboxylic acid tert-butyl ester (56.0 mg, 0.137 mmol) in THF (0.23 ml) at room temperature. The reaction mixture was stirred at room temperature for 43 hours, and a 35% aqueous $H_2O_2$ solution (0.030 ml, 0.31 mmol) was then further added at room temperature. After stirring at room temperature for 48 hours, the mixture was quenched with a 1 N aqueous HCl solution (0.2 ml) and concentrated under reduced pressure. A 6 N aqueous NaOH solution (0.33 ml, 2.0 mmol) was added to a suspension of the resulting residue in EtOH (1.2 ml) at room temperature, and the mixture was stirred at room temperature for 24 hours. The reaction mixture was quenched with a saturated aqueous $NH_4Cl$ solution (0.4 ml) and then concentrated under reduced pressure. The resulting residue was dissolved in ethyl acetate and washed with water, and then dried over $MgSO_4$ and concentrated under reduced pressure. The residue was purified by silica gel column chromatography (hexane/ethyl acetate=3/2) to give 2-(2,2-difluoro-benzo[1,3]dioxol-4-yl)-4-oxo-1,3,8-triaza-spiro[4.5]dec-1-ene-8-carboxylic acid tert-butyl ester (51.2 mg, 91%).

$^1$H-NMR (300 MHz) ($CDCl_3$) δ 1.50 (9H, s), 1.55 (2H, m), 1.95 (2H, m), 3.46 (2H, m), 4.02 (2H, br), 7.23-7.25 (2H, m), 7.88-7.94 (1H, m), 8.41 (1H, br s).

(Reaction 10-9)

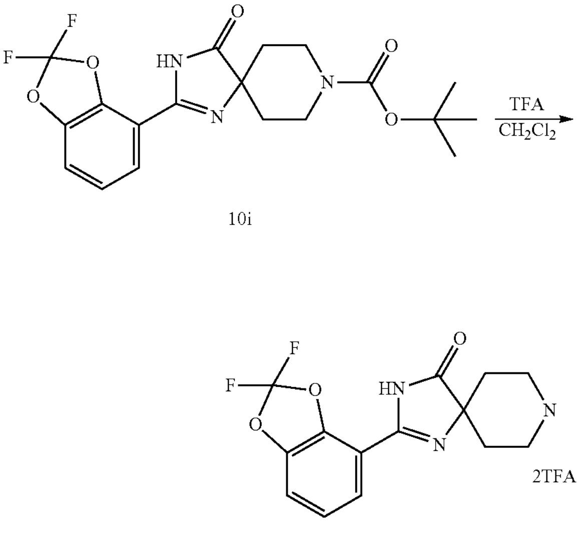

10i

10j 2-(2,2-Difluoro-benzo[1,3]dioxol-4-yl)-1,3,8-triaza-spiro[4.5]dec-1-en-4-one ditrifluoroacetate was synthesized by operations similar to those in Reaction 7-2 of Example 7 using appropriate reagents and starting material. (This compound was directly used in the next reaction.)

The spiroamine reagent used in the synthesis of Compound 93 (2-(3-chloro-2-fluoro-phenyl)-1,3,8-triaza-spiro[4.5]dec-1-en-4-one dihydrochloride) was synthesized as follows.

(Reaction 10-10)

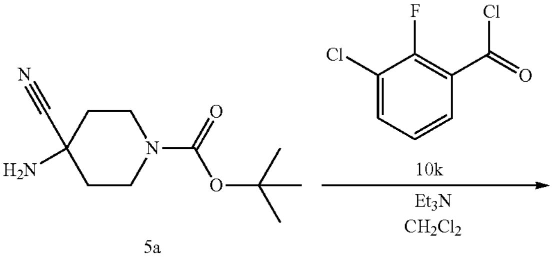

5a

-continued

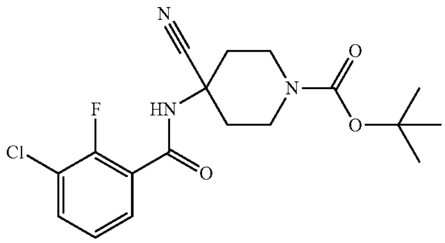

101

4-(3-Chloro-2-fluoro-benzoylamino)-4-cyano-piperidine-1-carboxylic acid tert-butyl ester was synthesized by operations similar to those in Reaction 2-3 of Example 2 using appropriate reagents and starting material.

MS (ESI) m/z=404 (M+Na)+.

(Reaction 10-11)

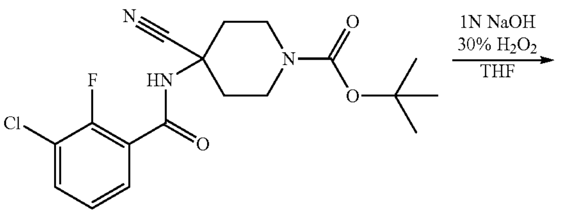

101

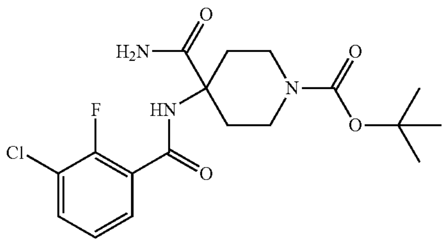

10m

1 N NaOH (8.60 ml, 8.60 mmol) and a 30% $H_2O_2$ solution (4.30 ml) were added to a solution of 4-(3-chloro-2-fluoro-benzoylamino)-4-cyano-piperidine-1-carboxylic acid tert-butyl ester (1.63 g, 4.28 mmol) in THF (8.60 ml) at room temperature, and the mixture was stirred at room temperature for two hours. The reaction mixture was adjusted to pH 6 by adding 2 N HCl and then extracted with ethyl acetate three times. The organic layers were sequentially washed with $H_2O$ (×2) and saturated brine, and then dried over $Na_2SO_4$ and concentrated under reduced pressure. The resulting residue was triturated with $H_2O$, and the solid was collected by filtration. The resulting solid was washed with $Et_2O$ and then dried under reduced pressure to give 4-carbamoyl-4-(3-chloro-2-fluoro-benzoylamino)-piperidine-1-carboxylic acid tert-butyl ester as a white powder (1.30 g, 76%).

MS (ESI) m/z=400 (M+H)+.

(Reaction 10-12)

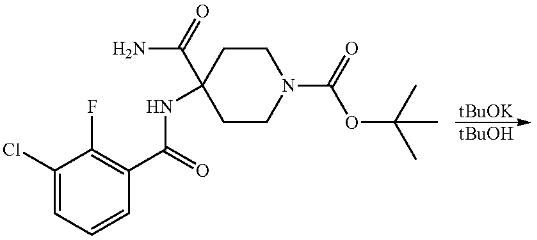

10m

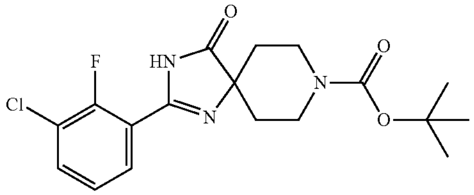

10n

Potassium t-butoxide (1.01 g, 8.97 mmol) was added to a solution of 4-carbamoyl-4-(3-chloro-2-fluoro-benzoylamino)-piperidine-1-carboxylic acid tert-butyl ester (1.20 g, 2.99 mmol) in tBuOH (30.0 ml) at room temperature, and the mixture was stirred at 40° C. for six hours. The reaction mixture was adjusted to pH 6 by adding 2 N HCl and then extracted with AcOEt three times. The organic layers were sequentially washed with $H_2O$ (×2) and saturated brine, and then dried over $Na_2SO_4$ and concentrated under reduced pressure. The residue was purified by column chromatography (hexane/AcOEt=90:10→50:50) to give 2-(3-chloro-2-fluoro-phenyl)-4-oxo-1,3,8-triaza-spiro[4.5]dec-1-ene-8-carboxylic acid tert-butyl ester as a colorless form (1.13 g, 99%).

MS (ESI) m/z=382 (M+H)+.

(Reaction 10-13)

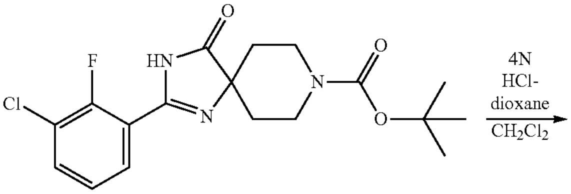

10n

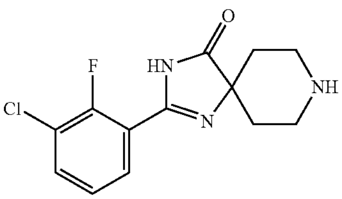

2HCl

10o 2-(3-Chloro-2-fluoro-phenyl)-1,3,8-triaza-spiro[4.5]dec-1-en-4-one dihydrochloride was synthesized by operations similar to those in Reaction 5-3 of Example 5 using appropriate reagents and starting material.

MS (ESI) m/z=282 (M+H)+.

The spiroamine reagent used in the synthesis of Compound 94 (2-[4-(1,1,2,2-tetrafluoro-ethoxy)-phenyl]-1,3,8-triaza-spiro[4.5]dec-1-en-4-one dihydrochloride) was synthesized as follows.

(Reaction 10-14)

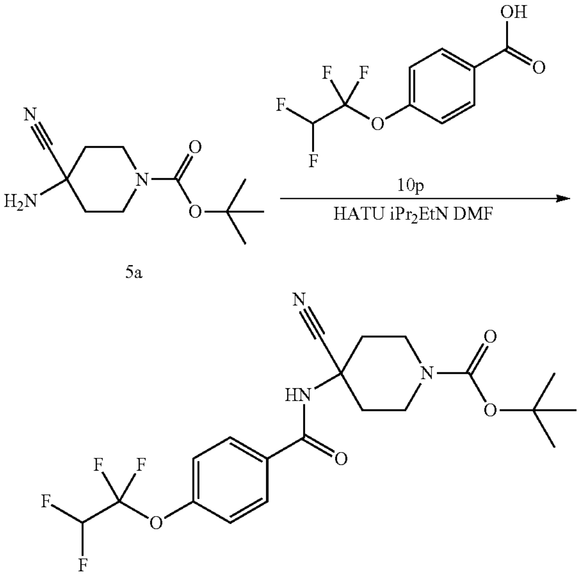

5a

10q

N,N,N',N'-Tetramethyl-O-(7-azabenzotriazol-1-yl)uoronium hexafluorophosphate (1.60 g, 4.20 mmol) was added to a solution of 4-(1,1,2,2-tetrafluoro-ethoxy)-benzoic acid (1.00 g, 4.20 mmol), 4-amino-4-cyano-piperidine-1-carboxylic acid tert-butyl ester (995 mg, 4.42 mmol) and N,N-diisopropylethylamine (1.46 ml, 8.39 mmol) in DMF (8.8 ml) at 0° C. The mixture was gradually warmed to room temperature and stirred for 28.5 hours. An aqueous ammonium chloride solution was added to the reaction mixture, followed by extraction with ethyl acetate three times. The organic layers were sequentially washed with $H_2O$ (×2) and saturated brine, and then dried over $Na_2SO_4$ and concentrated under reduced pressure. The residue was purified by column chromatography (hexane:AcOEt=90:10→30:70) to give 4-cyano-4-[4-(1,1,2,2-tetrafluoro-ethoxy)-benzoylamino]-piperidine-1-carboxylic acid tert-butyl ester as a light brown powder (1.60 g, 86%).

MS (ESI) m/z=446 (M+H)+.

(Reaction 10-15)

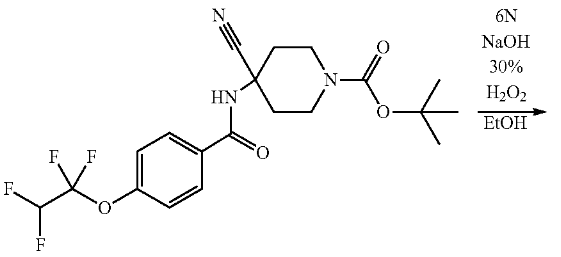

10q

-continued

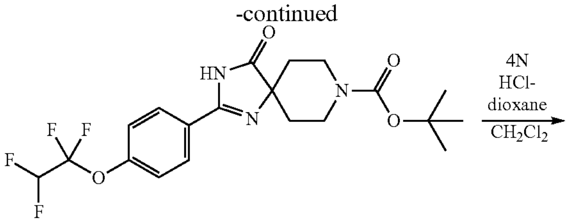

10r

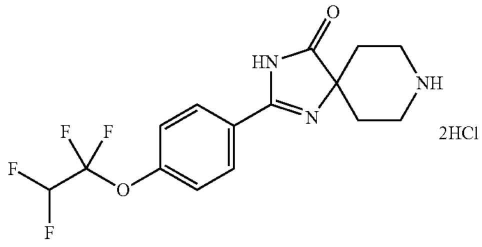

10s

2-[4-(1,1,2,2-Tetrafluoro-ethoxy)-phenyl]-1,3,8-triaza-spiro[4.5]dec-1-en-4-one dihydrochloride was synthesized by operations similar to those in Reaction 5-2 and Reaction 5-3 of Example 5 using appropriate reagents and starting material.

MS (ESI) m/z=346 (M+H)+.

The following spiroamine reagents used in the synthesis of Compounds 95 to 99 were synthesized by operations similar to those in Reaction 10-14 and Reaction 10-15 using appropriate reagents and starting materials.

TABLE 13

| Target Compound | Spiroamine reagent | Spiroamine reagent MS (m/z) |
|---|---|---|
| 95 | 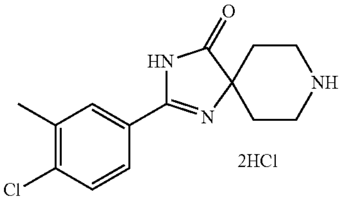 [SMILES: Cc1cc(C2=NC3(CCNCC3)C(=O)N2)ccc1Cl] 2HCl | 278 (M + H)+ |
| 96 | 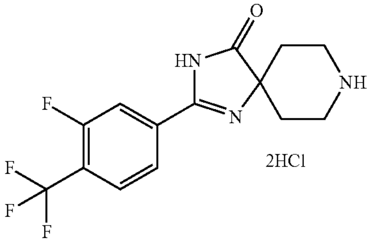 [SMILES: O=C1NC(c2ccc(C(F)(F)F)c(F)c2)=NC12CCNCC2] 2HCl | 316 (M + H)+ |
| 97 | 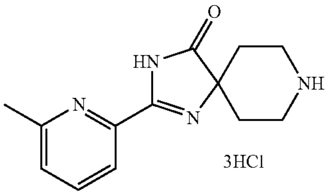 [SMILES: Cc1cccc(C2=NC3(CCNCC3)C(=O)N2)n1] 3HCl | 245 (M + H)+ |

TABLE 13-continued

| Target Compound | Spiroamine reagent | Spiroamine reagent MS (m/z) |
|---|---|---|
| 98 | 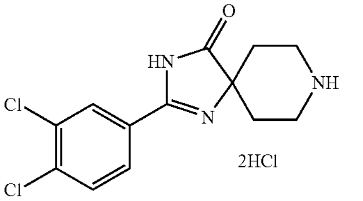 [SMILES: O=C1NC(c2ccc(Cl)c(Cl)c2)=NC12CCNCC2] 2HCl | 298 (M + H)+ |
| 99 | 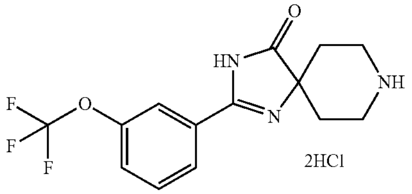 [SMILES: O=C1NC(c2cccc(OC(F)(F)F)c2)=NC12CCNCC2] 2HCl | 314 (M + H)+ |

The following spiroamine reagents used in the synthesis of Compounds 100 to 114 were synthesized by operations similar to those in Reaction 10-14, Reaction 5-2 and Reaction 7-2 using appropriate reagents and starting materials.

TABLE 14

| Target Compound | Spiroamine reagent | Spiroamine reagent MS (m/z) |
|---|---|---|
| 100 | 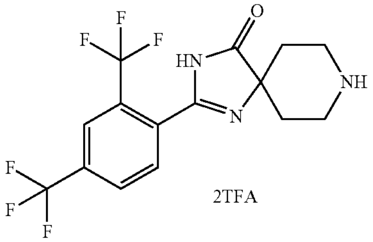 [SMILES: O=C1NC(c2ccc(C(F)(F)F)cc2C(F)(F)F)=NC12CCNCC2] 2TFA | 366 (M + H)+ |
| 101 | 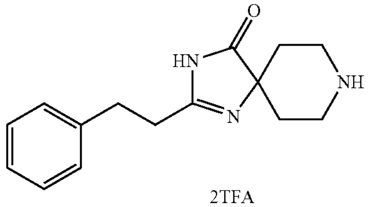 [SMILES: O=C1NC(CCc2ccccc2)=NC12CCNCC2] 2TFA | 258 (M + H)+ |
| 102 | 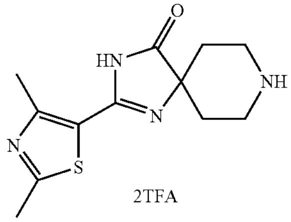 [SMILES: Cc1nc(C)c(C2=NC3(CCNCC3)C(=O)N2)s1] 2TFA | 265 (M + H)+ |

TABLE 14-continued

| Target Compound | Spiroamine reagent | Spiroamine reagent MS (m/z) |
|---|---|---|
| 103 | 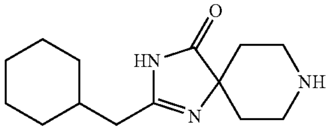 2TFA | 250 (M + H)+ |
| 104 | 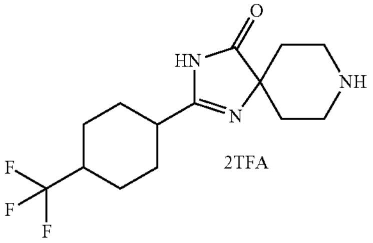 [SMILES: O=C1NC(C2CCC(C(F)(F)F)CC2)=NC12CCNCC2] 2TFA | 304 (M + H)+ |
| 105 | 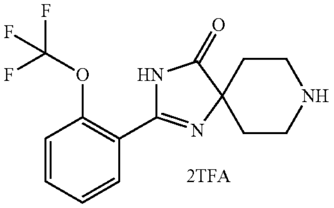 [SMILES: O=C1NC(c2ccccc2OC(F)(F)F)=NC12CCNCC2] 2TFA | 314 (M + H)+ |
| 106 | 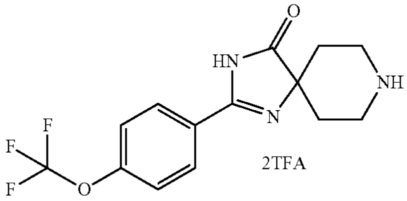 [SMILES: O=C1NC(c2ccc(OC(F)(F)F)cc2)=NC12CCNCC2] 2TFA | 314 (M + H)+ |
| 107 | 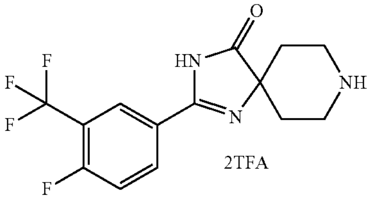 [SMILES: O=C1NC(c2ccc(F)c(C(F)(F)F)c2)=NC12CCNCC2] 2TFA | 315 (M + H)+ |
| 108 | 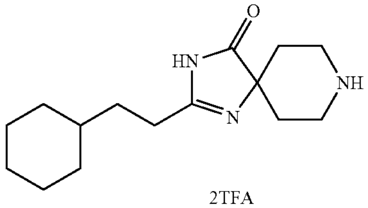 [SMILES: O=C1NC(CCC2CCCCC2)=NC12CCNCC2] 2TFA | 264 (M + H)+ |
| 109 | 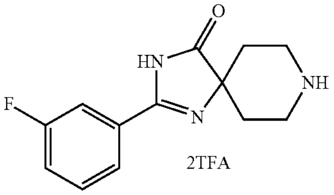 [SMILES: O=C1NC(c2cccc(F)c2)=NC12CCNCC2] 2TFA | 248 (M + H)+ |

TABLE 14-continued

| Target Compound | Spiroamine reagent | Spiroamine reagent MS (m/z) |
|---|---|---|
| 110 | 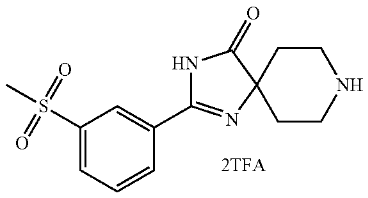 [SMILES: CS(=O)(=O)c1cccc(C2=NC3(CCNCC3)C(=O)N2)c1] 2TFA | 308 (M + H)+ |
| 111 | 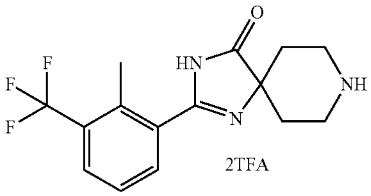 [SMILES: Cc1c(C2=NC3(CCNCC3)C(=O)N2)cccc1C(F)(F)F] 2TFA | 312 (M + H)+ |
| 112 | 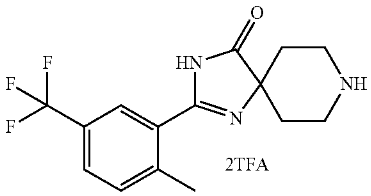 [SMILES: Cc1ccc(C(F)(F)F)cc1C1=NC2(CCNCC2)C(=O)N1] 2TFA | 312 (M + H)+ |
| 113 | 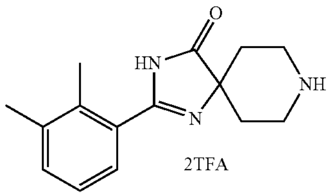 [SMILES: Cc1cccc(C2=NC3(CCNCC3)C(=O)N2)c1C] 2TFA | 258 (M + H)+ |
| 114 | 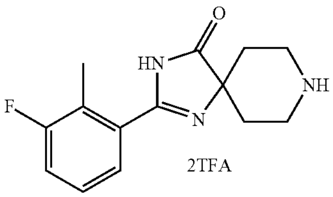 [SMILES: Cc1c(F)cccc1C1=NC2(CCNCC2)C(=O)N1] 2TFA | 262 (M + H)+ |

The following spiroamine reagents used in the synthesis of Compounds 115 to 117 were synthesized by operations similar to those in Reaction 10-14, Reaction 10-8 and Reaction 7-2 using appropriate reagents and starting materials.

TABLE 15

| Target Compound | Spiroamine reagent | Spiroamine reagent MS (m/z) |
|---|---|---|
| 115 | 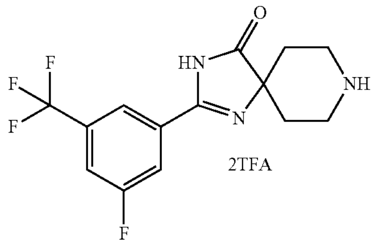 [SMILES: O=C1NC(c2cc(F)cc(C(F)(F)F)c2)=NC12CCNCC2] 2TFA | 315 (M + H)+ |

TABLE 15-continued

| Target Compound | Spiroamine reagent | Spiroamine reagent MS (m/z) |
|---|---|---|
| 116 | 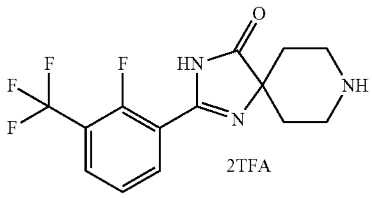 [SMILES: O=C1NC(c2cccc(C(F)(F)F)c2F)=NC12CCNCC2] 2TFA | 315 (M + H)+ |
| 117 | 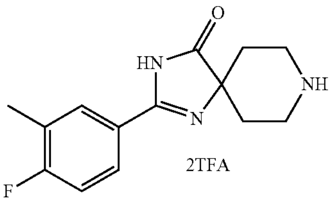 [SMILES: Cc1cc(C2=NC3(CCNCC3)C(=O)N2)ccc1F] 2TFA | 262 (M + H)+ |

The following spiroamine reagent used in the synthesis of Compound 118 (2-(4-difluoromethoxy-phenyl)-1,3,8-triaza-spiro[4.5]dec-1-en-4-one) was synthesized by operations similar to those in Reaction 10-14, Reaction 10-8 and Reaction 5-3 using appropriate reagents and starting material.

TABLE 16

| Target Compound | Spiroamine reagent | Spiroamine reagent MS (m/z) |
|---|---|---|
| 118 | 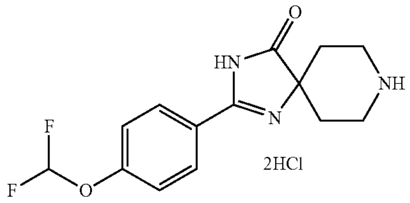 [SMILES: O=C1NC(c2ccc(OC(F)F)cc2)=NC12CCNCC2] 2HCl | 296 (M + H)+ |

The spiroamine reagent used in the synthesis of Compound 119 (2-(2-methoxy-pyridin-4-yl)-1,3,8-triaza-spiro[4.5]dec-1-en-4-one ditrifluoroacetate) was synthesized as follows.

(Reaction 10-16)

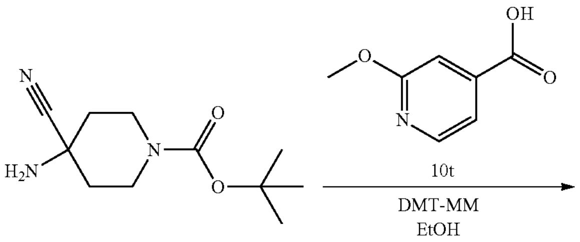

5a

-continued

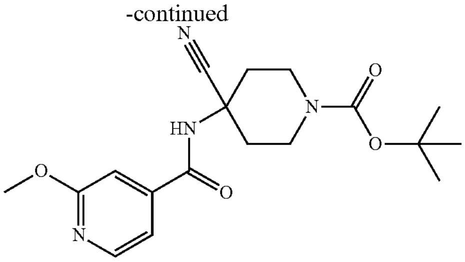

10u 4-(4,6-Dimethoxy-1,3,5-triazin-2-yl)-4-methylmorpholinium chloride 2,7-hydrate (1.06 g, 3.26 mmol) was added to a solution of 2-methoxy-isonicotinic acid (500 mg, 3.26 mmol) and 4-amino-4-cyano-piperidine-1-carboxylic acid tert-butyl ester (669 mg, 2.97 mmol) in EtOH (8.0 ml) at room temperature, and the mixture was stirred for 46.5 hours. An aqueous $NaHCO_3$ solution was added to the reaction mixture, followed by extraction with AcOEt three times. The organic layers were washed with saturated brine, and then dried over anhydrous sodium sulfate and concentrated under reduced pressure. The resulting residue was purified by column chromatography ($CH_2Cl_2$/MeOH=99:1 to 95:5) to give 4-cyano-4-[(2-methoxy-pyridine-4-carbonyl)-amino]-piperidine-1-carboxylic acid tert-butyl ester as a colorless form (901 mg, 84%).

MS (ESI) m/z=361 (M+H)+.

(Reaction 10-17)

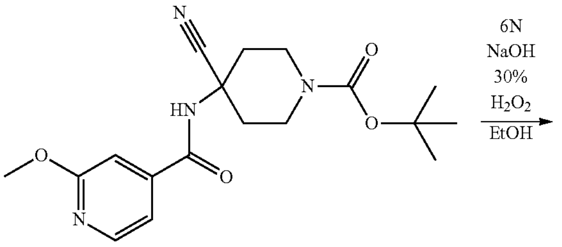

10u

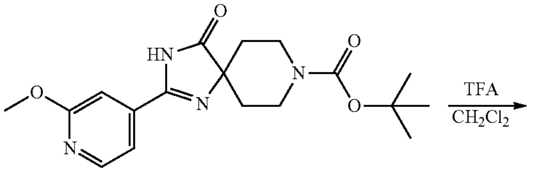

10v

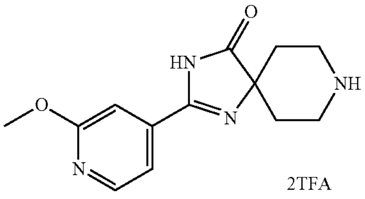

2TFA

10w 2-(2-Methoxy-pyridin-4-yl)-1,3,8-triaza-spiro[4.5]dec-1-en-4-one ditrifluoroacetate was synthesized by operations similar to those in Reaction 5-2 and Reaction 7-2 using appropriate reagents and starting material. (This compound was directly used in the next reaction.)

The following spiroamine reagents used in the synthesis of Compounds 120 to 131 were synthesized by the procedure described in Reaction 10-16 and Reaction 10-17 using appropriate reagents and starting materials.

TABLE 17

| Target Compound | Spiroamine reagent | Spiroamine reagent MS (m/z) |
|---|---|---|
| 120 | 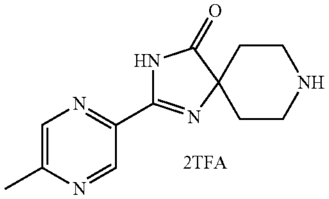 [SMILES: Cc1cnc(C2=NC3(CCNCC3)C(=O)N2)cn1] 2TFA | 246 (M + H)+ |
| 121 | 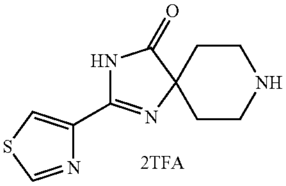 [SMILES: O=C1NC(c2cscn2)=NC12CCNCC2] 2TFA | This compound was directly used in the next step (Reaction 10-6). |
| 122 | 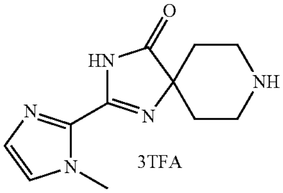 [SMILES: Cn1ccnc1C1=NC2(CCNCC2)C(=O)N1] 3TFA | 234 (M + H)+ |
| 123 | 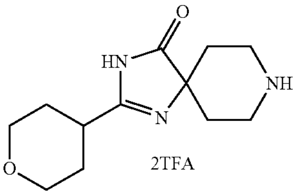 [SMILES: O=C1NC(C2CCOCC2)=NC12CCNCC2] 2TFA | This compound was directly used in the next step (Reaction 10-6). |
| 124 | 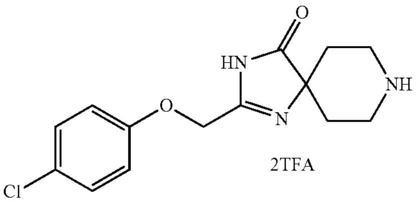 [SMILES: O=C1NC(COc2ccc(Cl)cc2)=NC12CCNCC2] 2TFA | 294 (M + H)+ |
| 125 | 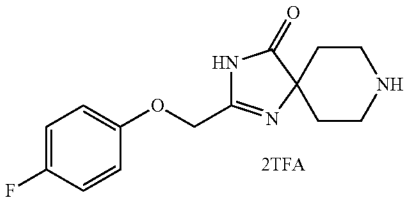 [SMILES: O=C1NC(COc2ccc(F)cc2)=NC12CCNCC2] 2TFA | 278 (M + H)+ |

TABLE 17-continued

| Target Compound | Spiroamine reagent | Spiroamine reagent MS (m/z) |
|---|---|---|
| 126 | 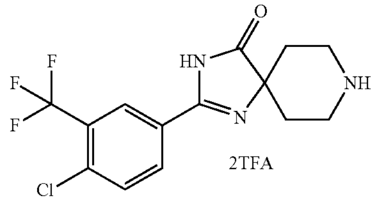 [SMILES: O=C1NC(c2ccc(Cl)c(C(F)(F)F)c2)=NC12CCNCC2] 2TFA | 332 (M + H)+ |
| 127 | 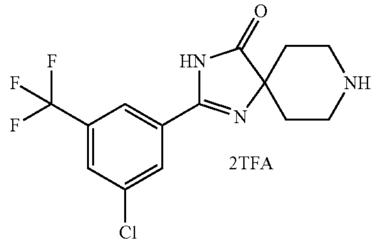 [SMILES: O=C1NC(c2cc(Cl)cc(C(F)(F)F)c2)=NC12CCNCC2] 2TFA | 331 (M + H)+ |
| 128 | 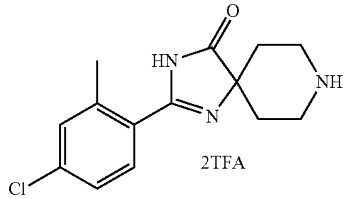 [SMILES: Cc1cc(Cl)ccc1C1=NC2(CCNCC2)C(=O)N1] 2TFA | 278 (M + H)+ |
| 129 | 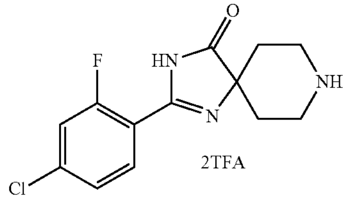 [SMILES: O=C1NC(c2ccc(Cl)cc2F)=NC12CCNCC2] 2TFA | 282 (M + H)+ |
| 130 | 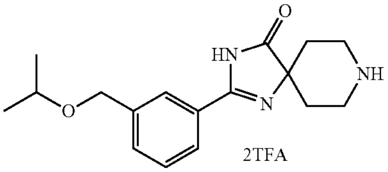 [SMILES: CC(C)OCc1cccc(C2=NC3(CCNCC3)C(=O)N2)c1] 2TFA | 302 (M + H)+ |
| 131 | 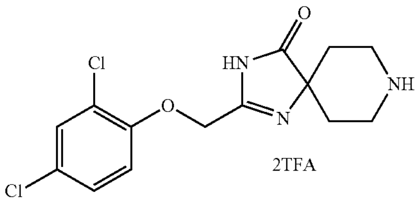 [SMILES: O=C1NC(COc2ccc(Cl)cc2Cl)=NC12CCNCC2] 2TFA | 328 (M + H)+ |

The following spiroamine reagent used in the synthesis of Compound 133 was synthesized by operations similar to those in Reaction 10-16, Reaction 10-8 and Reaction 5-3 using appropriate reagents and starting material.

TABLE 18

| Target Compound | Spiroamine reagent | Spiroamine reagent MS (m/z) |
|---|---|---|
| 133 | 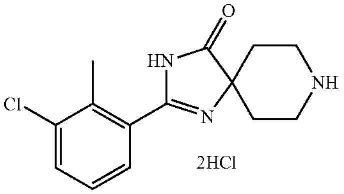 2HCl | 378 (M + H)+ |

The spiroamine reagent used in the synthesis of Compound 134 (2-(2,4-dichloro-benzyl)-1,3,8-triaza-spiro[4.5]dec-1-en-4-one ditrifluoroacetate) was synthesized as follows.

(Reaction 10-18)

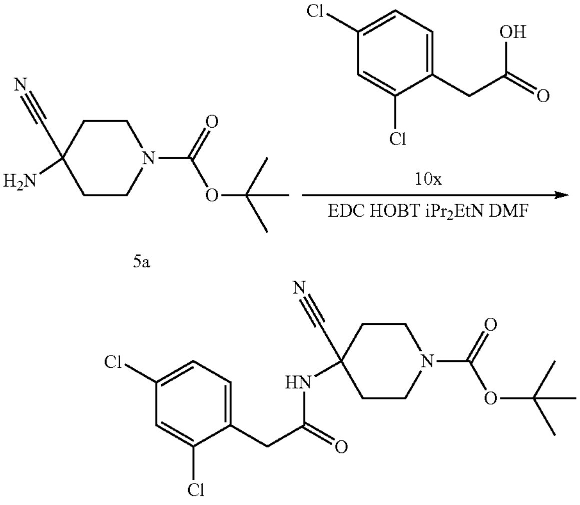

5a

10y (2,4-Dichloro-phenyl)-acetic acid (218 mg, 1.07 mmol), 1-ethyl-3-(3'-dimethylamino-propyl)carbodiimide hydrochloride (255 mg, 1.33 mmol), 1-hydroxybenzotriazole hydrate (136 mg, 0.88 mmol) and N,N-diisopropylethylamine (0.378 ml, 2.22 mmol) were sequentially added to a solution of 4-amino-4-cyano-piperidine-1-carboxylic acid tert-butyl ester (200 mg, 0.888 mmol) in DMF (4 ml) at room temperature, and the mixture was stirred at room temperature for 16 hours. $H_2O$ (20 ml) was added to the reaction mixture, followed by extraction with AcOEt (40 ml and 20 ml). The organic layers were sequentially washed with $H_2O$ (20 ml), 1 N HCl (20 ml), $H_2O$ (20 ml) and saturated brine (20 ml), and then dried over $Na_2SO_4$ and concentrated under reduced pressure. The resulting residue was purified by silica gel column chromatography (n-hexane/AcOEt) to give 4-cyano-4-[2-(2,4-dichloro-phenyl)-acetylamino]-piperidine-1-carboxylic acid tert-butyl ester as a white powder (285 mg, 78%).

$^1$H-NMR (270 MHz, $CDCl_3$) δ 1.45 (9H, s), 1.72 (2H, ddd, J=13.2, 10.7, 3.9 Hz), 2.34-2.37 (2H, m), 3.20-3.27 (2H, m), 3.68 (2H, s), 3.81-3.97 (2H, m), 5.55 (1H, s), 7.28 (1H, dd, J=7.8, 2.0 Hz), 7.30 (1H, d, 7.8 Hz), 7.45 (1H, d, J=2.0 Hz). MS (ESI) m/z=412 (M+H)+.

(Reaction 10-19)

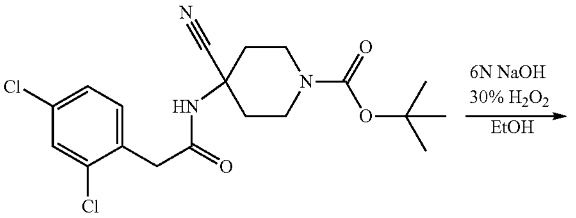

10y

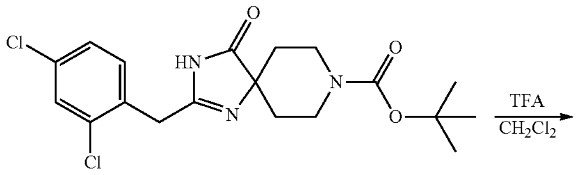

10z

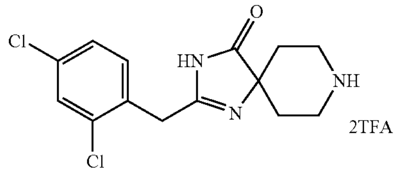

10aa 2-(2,4-Dichloro-benzyl)-1,3,8-triaza-spiro[4.5]dec-1-en-4-one ditrifluoroacetate was synthesized by operations similar to those in Reaction 5-2 and Reaction 7-2 using appropriate reagents and starting material.

MS (ESI) m/z=312 (M+H)+.

The following spiroamine reagent used in the synthesis of Compound 135 was synthesized by operations similar to those in Reaction 10-18 and Reaction 10-19 using appropriate reagents and starting material.

TABLE 19

| Target Compound | Spiroamine reagent | Spiroamine reagent MS (m/z) |
|---|---|---|
| 135 | 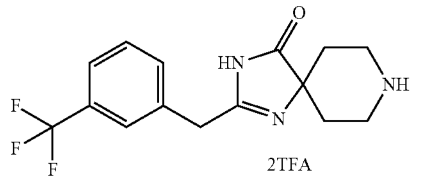 [SMILES: O=C1NC(Cc2cccc(C(F)(F)F)c2)=NC12CCNCC2]  | 312 (M + H)+ |

The spiroamine reagent used in the synthesis of Compound 136 (2-(1-trifluoromethyl-cyclopropyl)-1,3,8-triaza-spiro[4.5]dec-1-en-4-one ditrifluoroacetate) was synthesized as follows.

(Reaction 10-20)

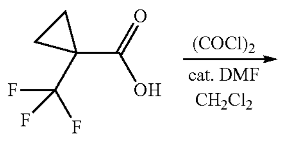

10ab

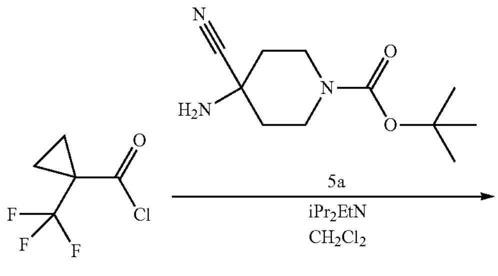

10ac

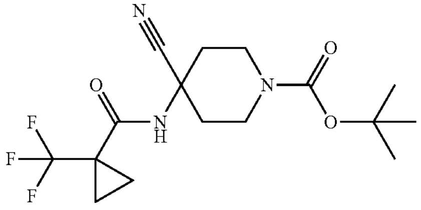

10ad

Oxalyl chloride (0.20 ml, 2.3 mmol) and dimethylformamide (8 μl) were added to a solution of 1-trifluoromethyl-cyclopropanecarboxylic acid (308 mg, 2.00 mmol) in dichloromethane (2.1 ml) at 0° C. The mixture was stirred at 0° C. for 30 minutes and then stirred at room temperature for two hours. The reaction mixture was concentrated under reduced pressure. A solution of the resulting residue in dichloromethane (1.5 ml) was added dropwise to a solution of 4-amino-4-cyanopiperidine-1-carboxylic acid tert-butyl ester (377 mg, 1.67 mmol) and diisopropylethylamine (0.42 ml, 2.4 mmol) in dichloromethane (2.0 ml) over three minutes at 0° C., and the mixture was stirred at room temperature for 13 hours. The reaction mixture was diluted with dichloromethane, and the organic layer was then washed with water, dried over $MgSO_4$ and concentrated under reduced pressure. The resulting residue was purified by silica gel column chromatography (hexane/ethyl acetate=3/1→2/1) to give 4-cyano-4-[(1-trifluoromethyl-cyclopropanecarbonyl)-amino]-piperidine-1-carboxylic acid tert-butyl ester as a colorless solid (519 mg, 86%).

$^1$H-NMR (400 MHz) ($CDCl_3$) δ 1.46 (9H, s), 1.29 (2H, dd, J=7.5 and 4.5 Hz), 1.56 (2H, m), 1.80 (2H, m), 2.40 (2H, m), 3.30 (2H, m), 3.93 (2H, br), 6.07 (1H, br s). Rf=0.62 in TLC (developer; hexane:AcOEt=1:1).

(Reaction 10-21)

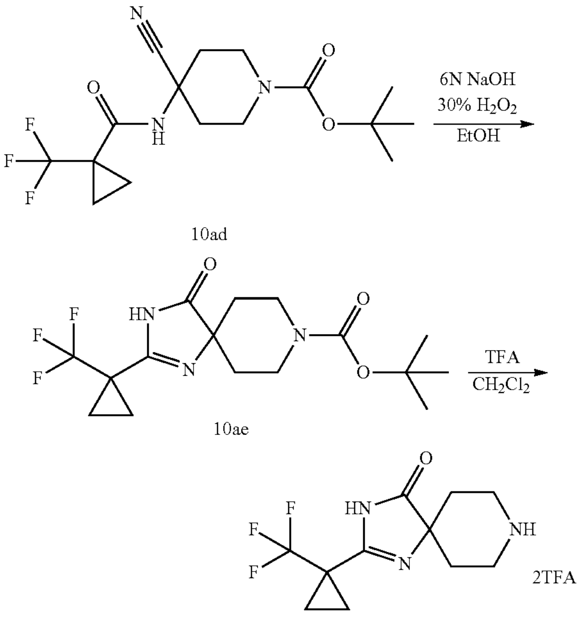

10ad

10ae

10af 2-(1-Trifluoromethyl-cyclopropyl)-1,3,8-triaza-spiro[4.5]dec-1-en-4-one ditrifluoroacetate was synthesized by operations similar to those in Reaction 5-2 and Reaction 7-2 using appropriate reagents and starting material. (This compound was directly used in Reaction 10-6.)

The following spiro-amine reagents used in the synthesis of Compounds 137 to 138 were synthesized by operations similar to those in Reaction 10-20 and Reaction 10-21 using appropriate reagents and starting materials. (These compounds were directly used in Reaction 10-6.)

TABLE 20

| Target Compound | Spiroamine reagent | Spiroamine reagent MS (m/z) |
|---|---|---|
| 137 | 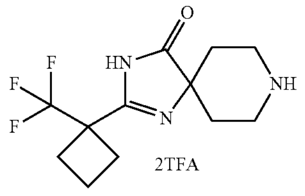 [SMILES: O=C1NC(C2(C(F)(F)F)CCC2)=NC12CCNCC2] 2TFA | This compound was directly used in the next step (Reaction 10-6). |
| 138 | 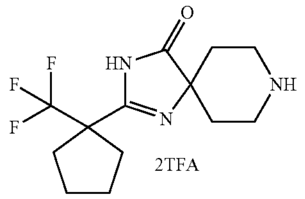 [SMILES: O=C1NC(C2(C(F)(F)F)CCCC2)=NC12CCNCC2] 2TFA | This compound was directly used in the next step (Reaction 10-6). |

The spiroamine reagent used in the synthesis of Compound 139 (2-(2-fluoro-4-trifluoromethyl-phenyl)-1,3,8-triaza-spiro[4.5]dec-1-en-4-one ditrifluoroacetate) was synthesized as follows.

(Reaction 10-22)

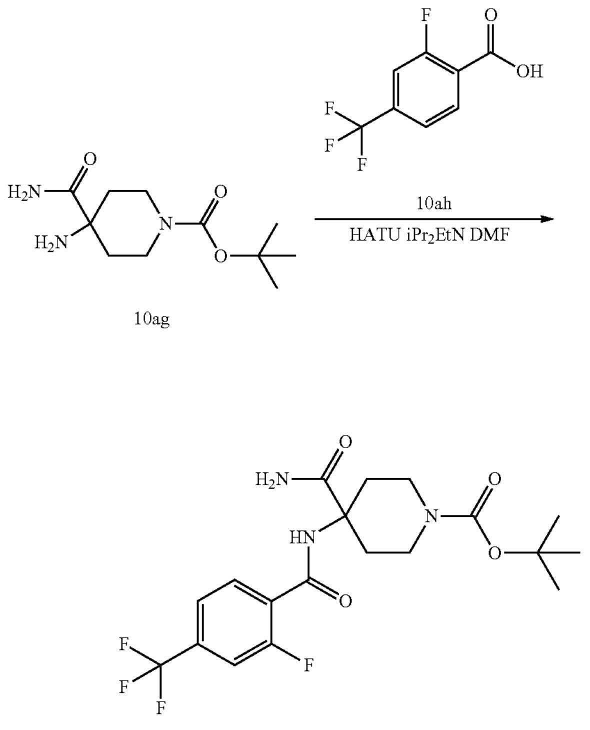

10ag

10ai

HATU (939 mg, 2.47 mmol) and DIPEA (525 μL, 3.09 mmol) were added to a solution of 4-amino-4-carbamoyl-piperidine-1-carboxylic acid tert-butyl ester (500 mg, 2.06 mmol) and 2-fluoro-4-trifluoromethyl-benzoic acid (514 mg, 2.47 mmol) in DMF (10 mL). The mixture was stirred at room temperature for 19 hours and then quenched with a saturated aqueous ammonium chloride solution. The reaction mixture was diluted with EtOAc, and the organic layer was then washed with $H_2O$ and saturated brine, dried over $MgSO_4$ and concentrated under reduced pressure. The resulting residue was triturated with n-hexane and EtOAc and then collected by filtration to give 4-carbamoyl-4-(2-fluoro-4-trifluoromethyl-benzoylamino)-piperidine-1-carboxylic acid tert-butyl ester as a white solid. This was used in the next step without further purification.

(Reaction 10-23)

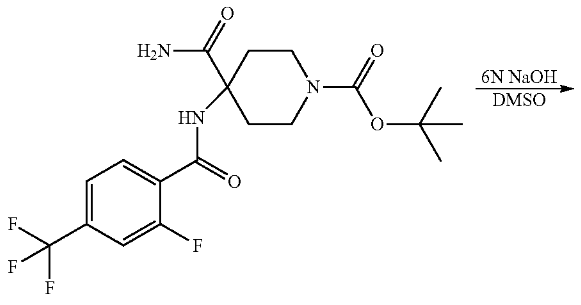

10ai

-continued

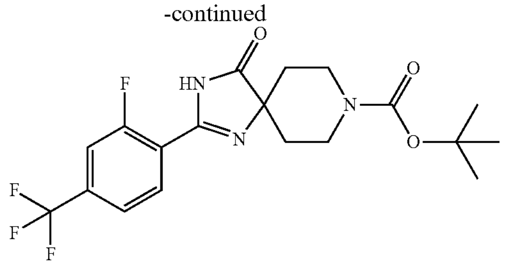

10aj

A 6 N aqueous NaOH solution (54.8 μL, 323 μmol) was added to a solution of 4-carbamoyl-4-(2-fluoro-4-trifluoromethyl-benzoylamino)-piperidine-1-carboxylic acid tert-butyl ester (100 mg, 231 μmol) in DMSO (0.3 mL), and the mixture was stirred at room temperature for 27 hours. The reaction mixture was quenched with a saturated aqueous ammonium chloride solution and then diluted with EtOAc, and the organic layer was sequentially washed with $H_2O$ and saturated brine. The organic layer was dried over $MgSO_4$ and then concentrated under reduced pressure. The resulting residue was purified by column chromatography ($CH_2Cl_2$/MeOH=95:5) to give 2-(2-fluoro-4-trifluoromethyl-phenyl)-4-oxo-1,3,8-triaza-spiro[4.5]dec-1-ene-8-carboxylic acid tert-butyl ester as a white solid (54.5 mg, 57%).

MS (ESI) m/z=438 (M+Na)+.

(Reaction 10-24)

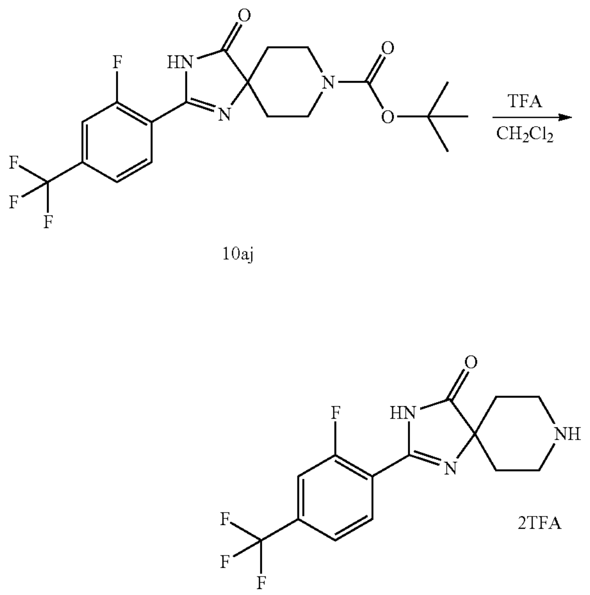

10aj

10ak 2-(2-Fluoro-4-trifluoromethyl-phenyl)-1,3,8-triaza-spiro[4.5]dec-1-en-4-one ditrifluoroacetate was synthesized by operations similar to those in Reaction 7-2 using appropriate reagents and starting material.

MS (ESI) m/z=315 (M+H)+.

The following spiro-amine reagents used in the synthesis of Compounds 140 to 143 were synthesized by operations similar to those in Reaction 10-22, Reaction 10-23 and Reaction 10-24 using appropriate reagents and starting materials.

TABLE 21

| Target Compound | Spiroamine reagent | Spiroamine reagent MS (m/z) |
|---|---|---|
| 140 | 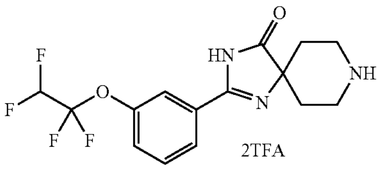 [SMILES: O=C1NC(c2cccc(OC(F)(F)C(F)F)c2)=NC12CCNCC2] 2TFA | 346 (M + H)+ |
| 141 | 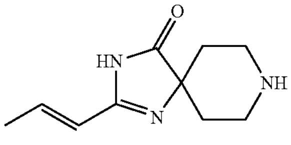 2TFA | 194 (M + H)+ |
| 142 | 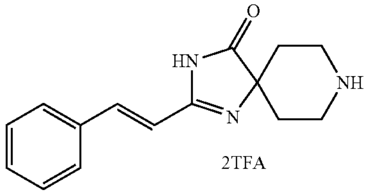 [SMILES: O=C1NC(/C=C/c2ccccc2)=NC12CCNCC2] 2TFA | 256 (M + H)+ |
| 143 | 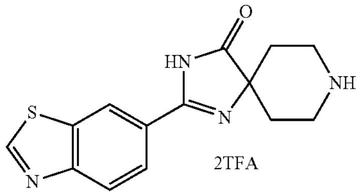 [SMILES: O=C1NC(c2ccc3ncsc3c2)=NC12CCNCC2] 2TFA | 287 (M + H)+ |

The spiroamine reagent used in the synthesis of Compound 144 (2-(4-methoxy-3-trifluoromethyl-phenyl)-1,3,8-triaza-spiro[4.5]dec-1-en-4-one ditrifluoroacetate) was synthesized as follows.

(Reaction 10-25)

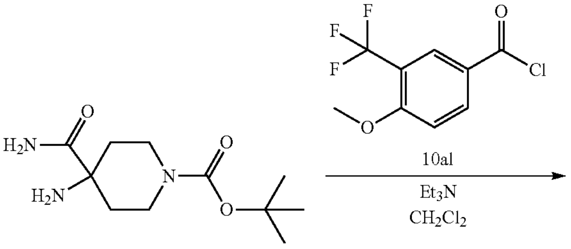

10ag

-continued

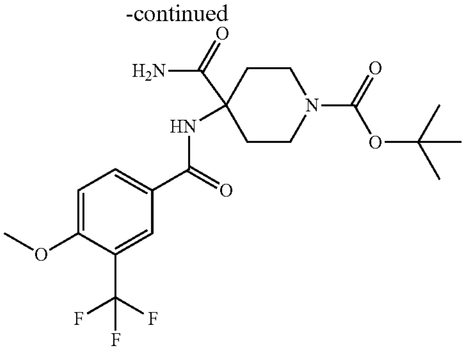

10am

4-Carbamoyl-4-(4-methoxy-3-trifluoromethyl-benzoylamino)-piperidine-1-carboxylic acid tert-butyl ester was synthesized by operations similar to those in Reaction 2-3 using 4-amino-4-carbamoyl-piperidine-1-carboxylic acid tert-butyl ester as a starting material amine.

MS (ESI) m/z=446 (M+H)+.

(Reaction 10-26)

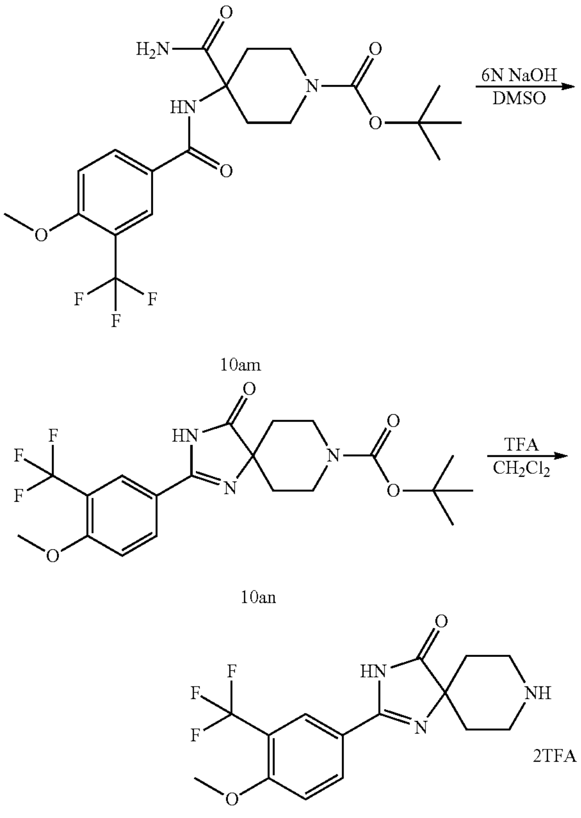

10am

10an

10ao 2-(4-Methoxy-3-trifluoromethyl-phenyl)-1,3,8-triaza-spiro[4.5]dec-1-en-4-one ditrifluoroacetate was synthesized by operations similar to those in Reaction 10-23 and Reaction 7-2 using appropriate reagents and starting material.

MS (ESI) m/z=328 (M+H)+.

Example 11

N-{3-Methyl-4-[2-(4-oxo-2-m-tolyl-1,3,8-triaza-spiro[4.5]dec-1-ene-8-sulfonyl)-ethyl]-phenyl}-acetamide (Compound 145)

(Reaction 11-1)

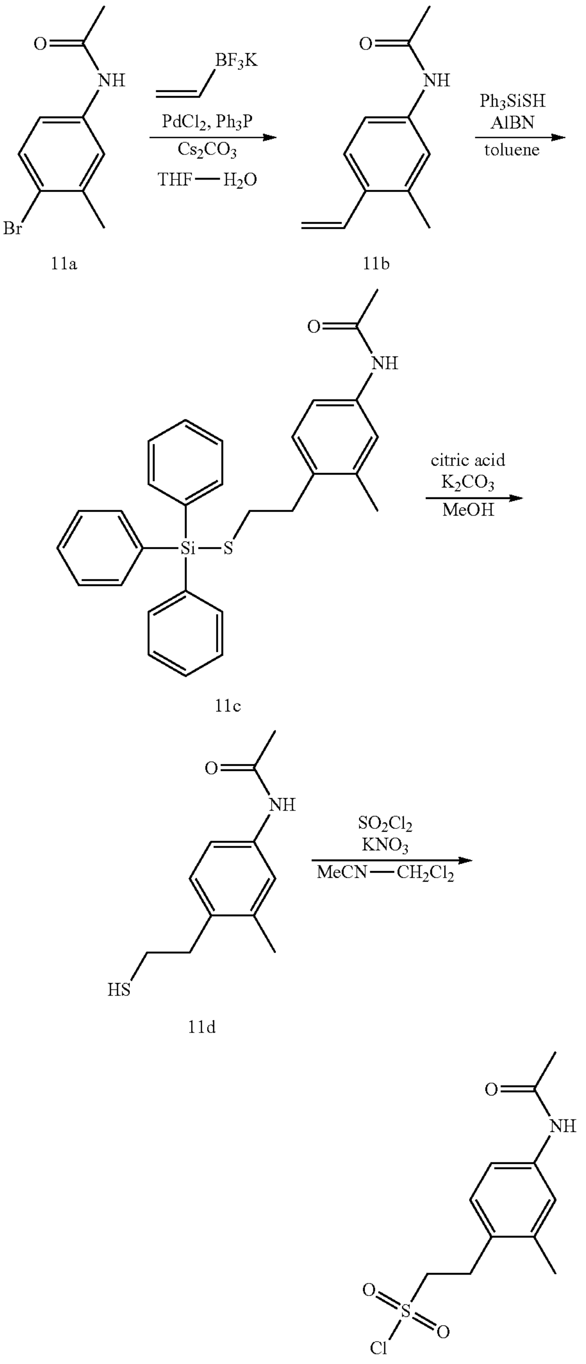

11a

11b

11c

11d

11e 2-(4-Acetylamino-2-methyl-phenyl)-ethanesulfonyl chloride was synthesized by operations similar to those in Reaction 10-2, Reaction 10-3, Reaction 10-4 and Reaction 10-5 using appropriate reagents and starting material.

MS (ESI) m/z=276 (M+H)+.

(Reaction 11-2)

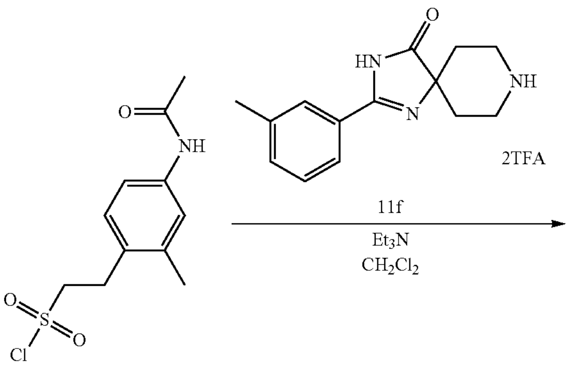

11e

-continued

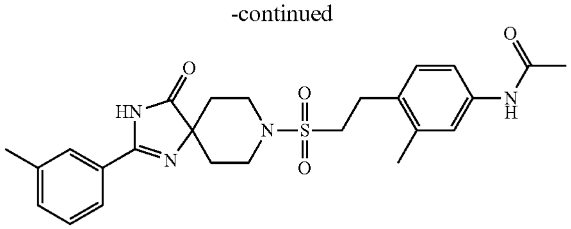

Compound 145

N-{3-Methyl-4-[2-(4-oxo-2-m-tolyl-1,3,8-triaza-spiro[4.5]dec-1-ene-8-sulfonyl)-ethyl]-phenyl}-acetamide was synthesized by operations similar to those in Reaction 5-4 using appropriate reagents and starting material.

MS (ESI) m/z=483 (M+H)+.

The example compounds shown below were synthesized by operations similar to those in Example 11 using appropriate reagents and starting materials.

TABLE 22

| Compound | Structure | LCMS or HPLC condition | Retention time (min) | MS (m/z) |
|---|---|---|---|---|
| 146 | 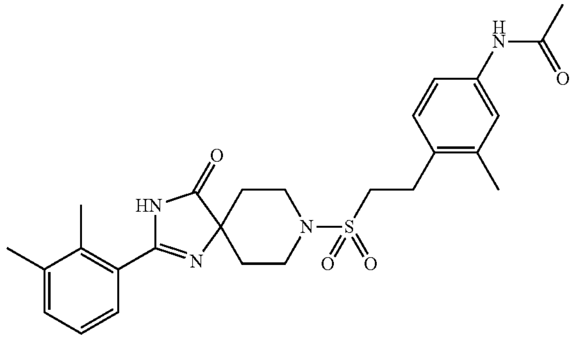 [SMILES: CC(=O)Nc1ccc(CCS(=O)(=O)N2CCC3(CC2)N=C(c2cccc(C)c2C)NC3=O)c(C)c1] | LCMS-C-1 | 2.33 | 497 (M + H)+ |
| 147 | 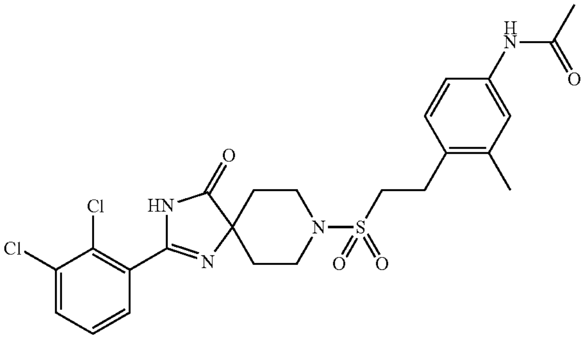 [SMILES: CC(=O)Nc1ccc(CCS(=O)(=O)N2CCC3(CC2)N=C(c2cccc(Cl)c2Cl)NC3=O)c(C)c1] | LCMS-C-1 | 2.40 | 537 (M + H)+ |
| 148 | 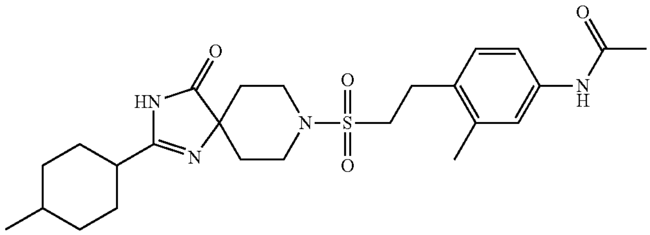 [SMILES: CC(=O)Nc1ccc(CCS(=O)(=O)N2CCC3(CC2)N=C(C2CCC(C)CC2)NC3=O)c(C)c1] | LCMS-C-1 | 2.45 | 489 (M + H)+ |

The spiroamine reagent used in the synthesis of Compound 148 (2-(4-methyl-cyclohexyl)-1,3,8-triaza-spiro[4.5]dec-1-en-4-one dihydrochloride) was synthesized as follows.

(Reaction 11-3)

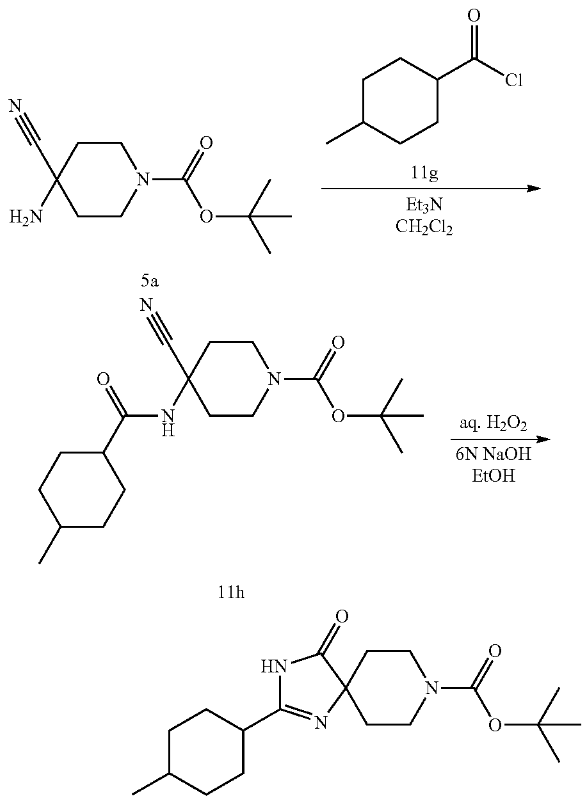

11i 2-(4-Methyl-cyclohexyl)-4-oxo-1,3,8-triaza-spiro[4.5]dec-1-ene-8-carboxylic acid tert-butyl ester was synthesized by operations similar to those in Reaction 5-1 and Reaction 5-2 using appropriate reagents and starting material.

MS (ESI) m/z=372 (M+Na)+.

(Reaction 11-4)

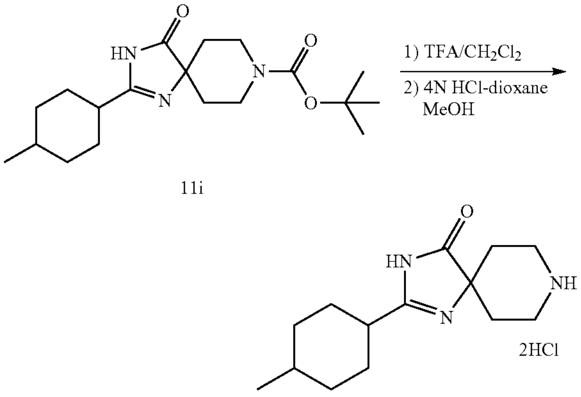

11j 2-(4-Methyl-cyclohexyl)-1,3,8-triaza-spiro[4.5]dec-1-en-4-one dihydrochloride was synthesized by operations similar to those in Reaction 7-2 and Reaction 5-3 using appropriate reagents and starting material.

MS (ESI) m/z=250 (M+H)+.

Example 12

N-(2-Hydroxy-ethyl)-N-(3-methyl-4-{2-[4-oxo-2-(3-trifluoromethoxy-phenyl)-1,3,8-triaza-spiro[4.5]dec-1-ene-8-sulfonyl]-ethyl}-phenyl)-acetamide (Compound 149)

(Reaction 12-1)

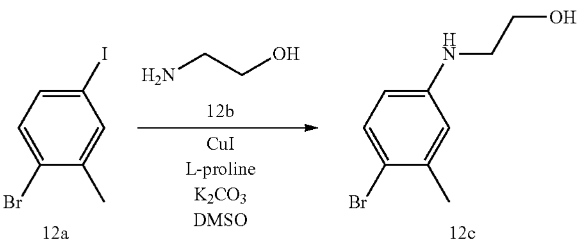

12a 12c

A mixture of 2-bromo-5-iodotoluene (1.60 g, 5.40 mmol), 2-aminoethanol (0.49 mL, 8.14 mmol), CuI (53.3 mg, 0.28 mmol), L-proline (63.4 mg, 0.55 mmol) and $K_2CO_3$ (1.49 g, 10.8 mmol) in DMSO (3.24 mL) was stirred at 60° C. for 12 hours. The reaction mixture was cooled and then diluted with AcOEt, and the organic layer was sequentially washed with $H_2O$ and saturated brine. The organic layer was dried over $Na_2SO_4$ and then concentrated under reduced pressure. The resulting residue was purified by silica gel column chromatography (hexane/AcOEt=1/1) to give 2-(4-bromo-3-methyl-phenylamino)-ethanol as a brown solid (1.00 g, 81%).

MS (ESI) m/z=230, 232 (M+H)+.

(Reaction 12-2)

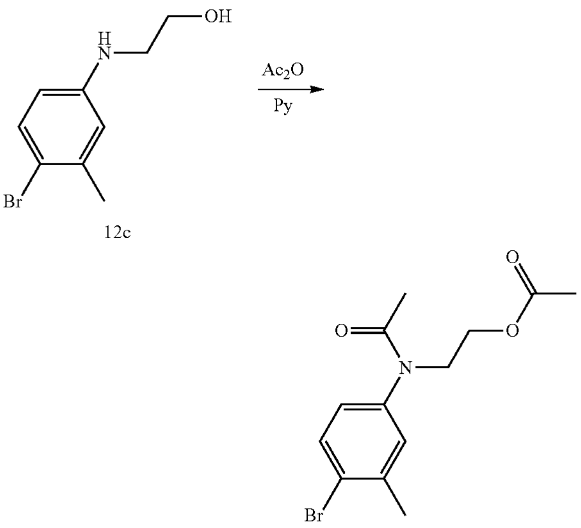

12d

Pyridine (158.4 mL, 1.958 mol) was added to a solution of 2-(4-bromo-3-methyl-phenylamino)-ethanol (19.28 g, 83.788 mmol) in $Ac_2O$ (158.4 mL, 1.676 mol). The mixture was stirred at room temperature for 18 hours and then concentrated under reduced pressure. The resulting residue was purified by silica gel column chromatography ($CH_2Cl_2$/MeOH=100/0 to 95/5) to give acetic acid 2-[acetyl-(4-bromo-3-methyl-phenyl)-amino]-ethyl ester as a brown viscous oil (21.44 g, 81%).

MS (ESI) m/z=314, 316 (M+H)+.

(Reaction 12-3)
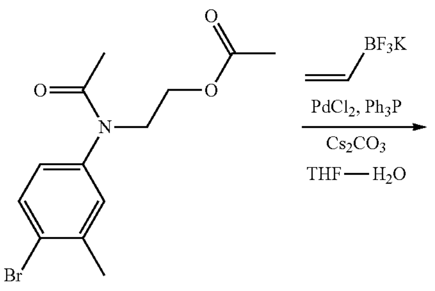
12d
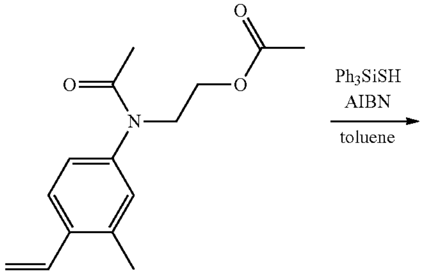
12e
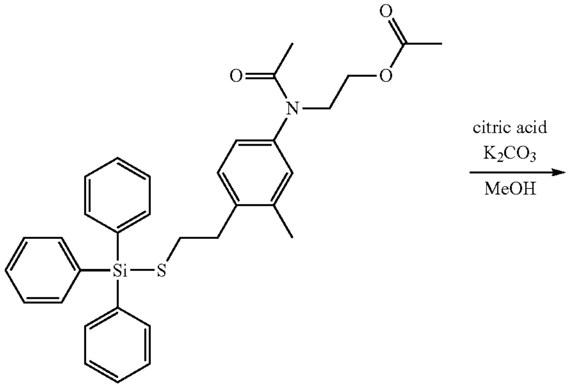
12f
-continued
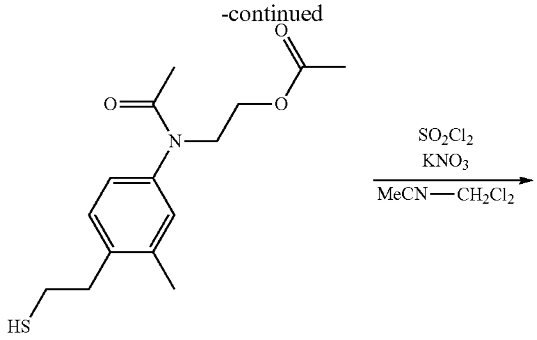
12g
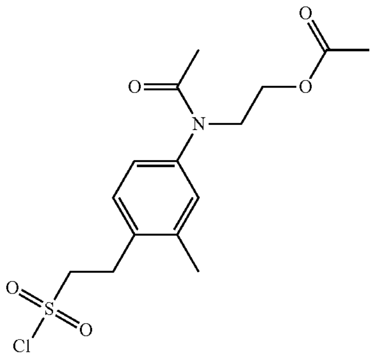
12h
Acetic acid 2-{acetyl-[4-(2-chlorosulfonyl-ethyl)-3-methyl-phenyl]-amino}-ethyl ester was synthesized by operations similar to those in Reaction 10-2, Reaction 10-3, Reaction 10-4 and Reaction 10-5 using appropriate reagents and starting material.
MS (ESI) m/z=362 (M+H)+.
(Reaction 12-4)
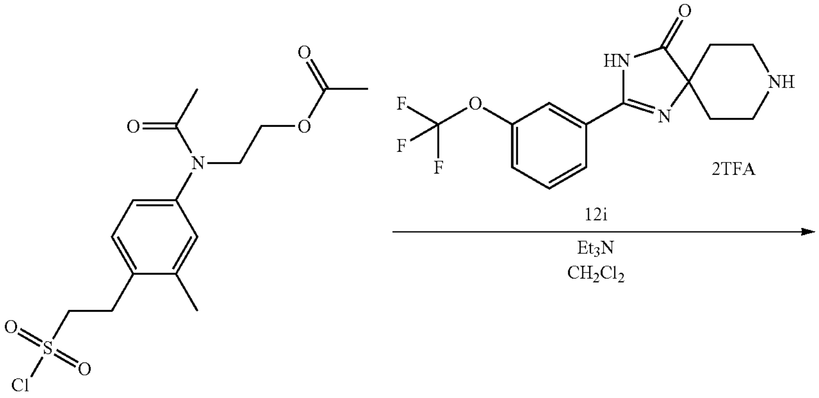
2TFA
12i
12h -continued

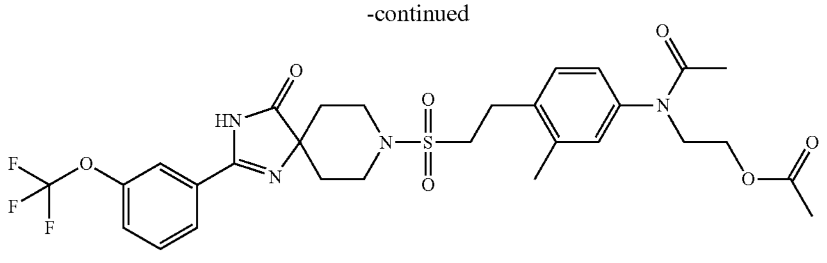

12j

Acetic acid 2-[acetyl-(3-methyl-4-{2-[4-oxo-2-(3-trifluoromethoxy-phenyl)-1,3,8-triaza-spiro[4.5]dec-1-ene-8-sulfonyl]-ethyl}-phenyl)-amino]-ethyl ester was synthesized by operations similar to those in Reaction 5-4 of Example 5 using appropriate reagents and starting material.

MS (ESI) m/z=639 (M+H)+.

(Reaction 12-5)

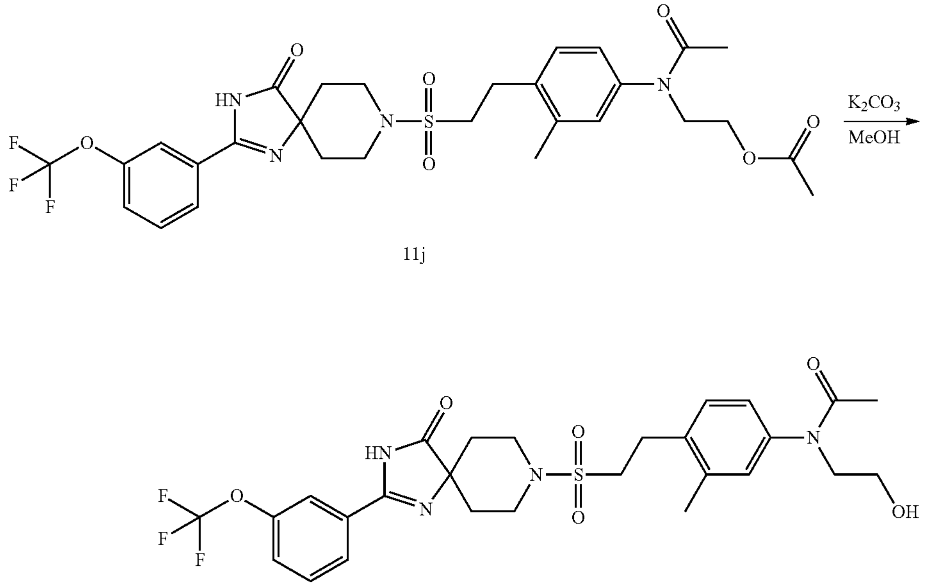

11j

Compound 149

$K_2CO_3$ (9.1 mg, 66.0 μmol) was added to a solution of acetic acid 2-[acetyl-(3-methyl-4-{2-[4-oxo-2-(3-trifluoromethoxy-phenyl)-1,3,8-triaza-spiro[4.5]dec-1-ene-8-sulfonyl]-ethyl}-phenyl)-amino]-ethyl ester (28.1 mg, 44.0 μmol) in MeOH (0.5 mL). The mixture was stirred at room temperature for two hours. $H_2O$ was then added and the mixture was diluted with $CH_2Cl_2$. The organic layer was washed with saturated brine, and then dried over $MgSO_4$ and concentrated under reduced pressure. The resulting residue was purified by column chromatography ($CH_2Cl_2$/MeOH=15/1) to give N-(2-hydroxy-ethyl)-N-(3-methyl-4-{2-[4-oxo-2-(3-trifluoromethoxy-phenyl)-1,3,8-triaza-spiro[4.5]dec-1-ene-8-sulfonyl]-ethyl}-phenyl)-acetamide as a white amorphous (24.0 mg, 92%).

$^1$H-NMR (400 MHz, $CDCL_3$) δ 1.71-1.75 (2H, m), 1.90 (3H, s), 2.09-2.04 (2H, m), 2.40 (3H, s), 3.16-3.24 (5H, m), 3.46-3.53 (4H, m), 3.77-3.87 (4H, m), 7.04-7.06 (2H, m), 7.24-7.26 (1H, m), 7.42-7.44 (1H, m), 7.58 (1H, t, J=8.3 Hz), 7.79-7.81 (1H, m), 7.86 (1H, m). MS (ESI) m/z=597 (M+H)+.

Example 13

Acetic acid (S)-1-acetoxymethyl-2-[acetyl-(3-methyl-4-{2-[4-oxo-2-(3-trifluoromethyl-phenyl)-1,3,8-triaza-spiro[4.5]dec-1-ene-8-sulfonyl]-ethyl}-phenyl)-amino]-ethyl ester (Compound 150)

(Reaction 13-1)

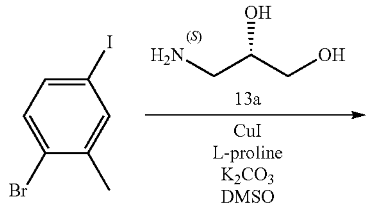

12a

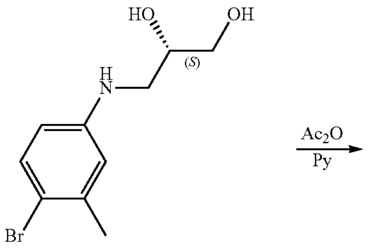

13b

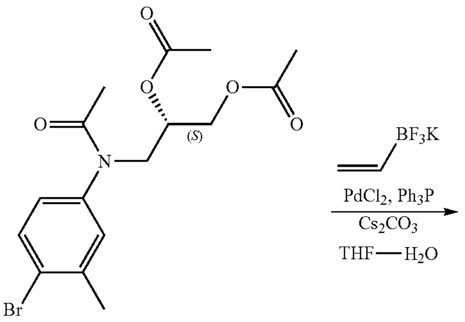

13c

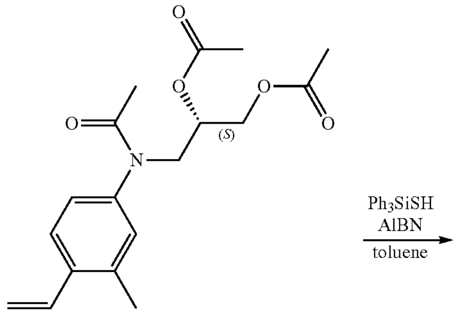

13d

-continued

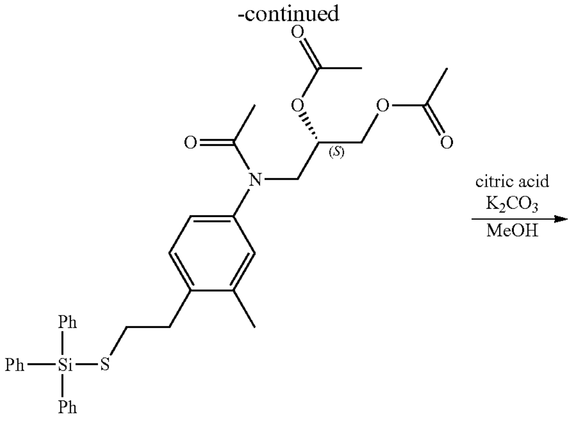

13e

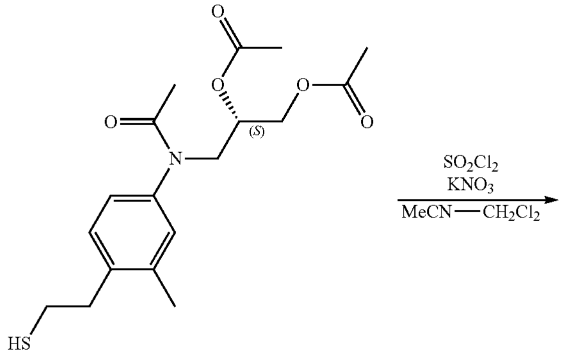

13f

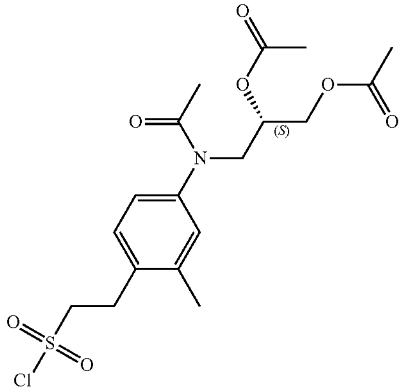

13g

Acetic acid (S)-1-acetoxymethyl-2-{acetyl-[4-(2-chloro-sulfonyl-ethyl)-3-methyl-phenyl]-amino}-ethyl ester was synthesized by operations similar to those in Reaction 12-1, Reaction 12-2, Reaction 10-2, Reaction 10-3, Reaction 10-4 and Reaction 10-5 using appropriate reagents and starting material.

MS (ESI) m/z=434 (M+H)+.

(Reaction 13-2)

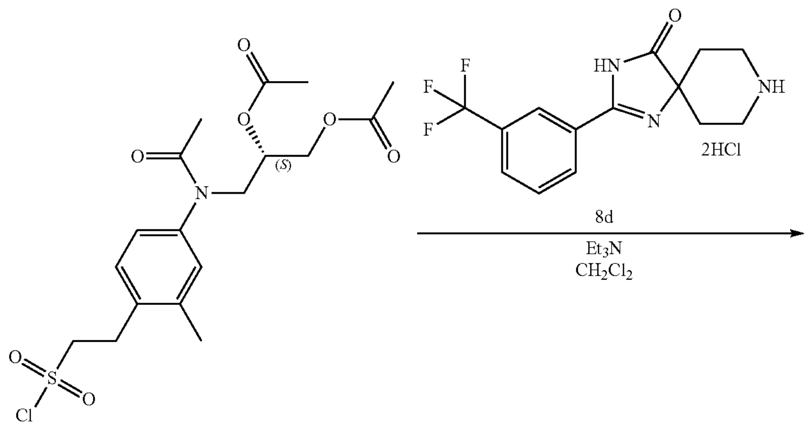

13g

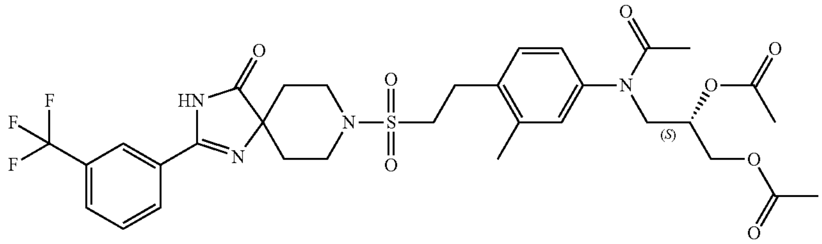

Compound 150

Acetic acid (S)-1-acetoxymethyl-2-[acetyl-(3-methyl-4-{2-[4-oxo-2-(3-trifluoromethyl-phenyl)-1,3,8-triaza-spiro[4.5]dec-1-ene-8-sulfonyl]-ethyl}-phenyl)-amino]-ethyl ester was synthesized by operations similar to those in Reaction 5-4 using appropriate reagents and starting material.

MS (ESI) m/z=695 (M+H)+.

The example compounds shown below were synthesized by operations similar to those in Example 13 using appropriate reagents and starting materials.

TABLE 23

| Compound | Structure | LCMS or HPLC condition | Retention time (min) | MS (m/z) |
|---|---|---|---|---|
| 151 | 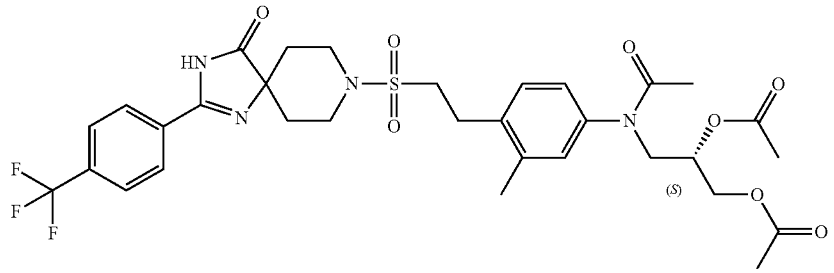 | LCMS-A-1 | 2.53 | 695 (M + H)+ |

TABLE 23-continued
| Compound | Structure | LCMS or HPLC condition | Retention time (min) | MS (m/z) |
|---|---|---|---|---|
| 152 | 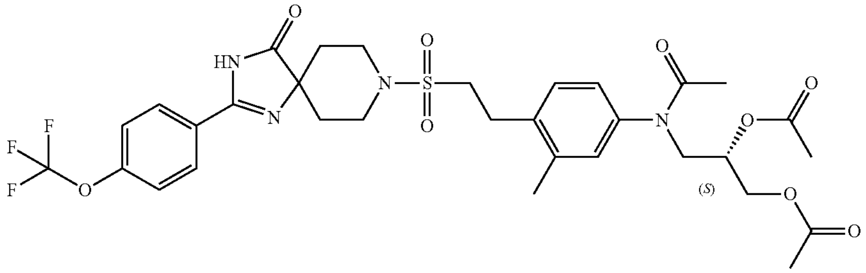 | LCMS-A-1 | 2.50 | 711 (M + H)+ |
| 153 | 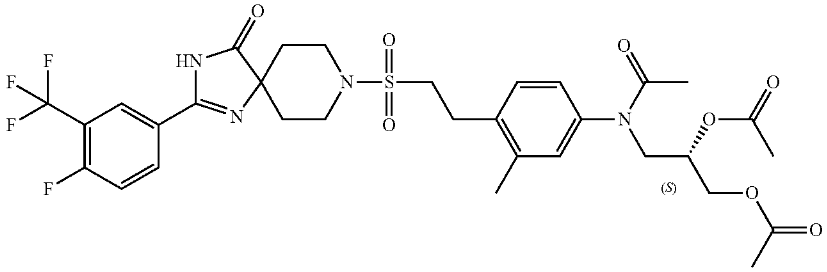 | LCMS-A-1 | 2.57 | 713 (M + H)+ |
Example 14
8-{2-[4-((S)-2,3-Dihydroxy-propylamino)-2-methyl-phenyl]-ethanesulfonyl}-2-(4-trifluoromethyl-phenyl)-1,3,8-triaza-spiro[4.5]dec-1-en-4-one (Compound 154)
(Reaction 14-1)
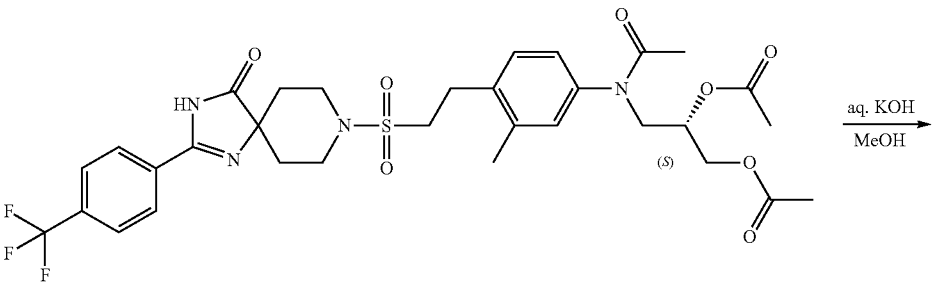
Compound 151
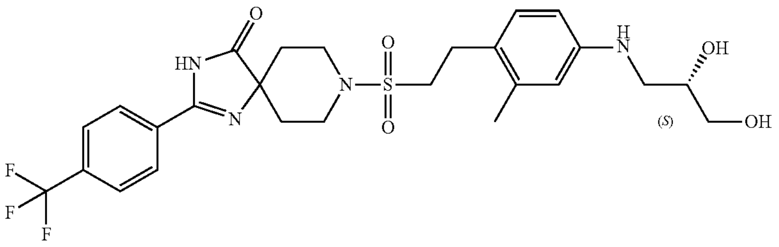
Compound 154

A 1.2 M aqueous KOH solution (0.5 mL) was added to a solution of acetic acid (S)-1-acetoxymethyl-2-[acetyl-(3-methyl-4-{2-[4-oxo-2-(4-trifluoromethyl-phenyl)-1,3,8-triaza-spiro[4.5]dec-1-ene-8-sulfonyl]-ethyl}-phenyl)-amino]-ethyl ester (40.8 mg, 0.0587 mmol) in MeOH (3 mL). The reaction mixture was stirred at 50° C. for 1.5 hours and then cooled to room temperature. Dowex 50W×4 (237.6 mg) was added. The mixture was further stirred at room temperature for two hours and then filtered, and the organic layer was concentrated under reduced pressure. The resulting residue was purified by silica gel column chromatography ($CH_2Cl_2$/MeOH=10/1) to give 8-{2-[4-((S)-2,3-dihydroxy-propylamino)-2-methyl-phenyl]-ethanesulfonyl}-2-(4-trifluoromethyl-phenyl)-1,3,8-triaza-spiro[4.5]dec-1-en-4-one as a white powder (30.3 mg, 91%).

$^1$H-NMR (400 MHz, CD3OD) δ 1.72-1.75 (2H, m), 1.99-2.04 (2H, m), 2.28 (3H, s), 2.98-3.06 (3H, m), 3.19-3.28 (2H, m), 3.46-3.61 (5H, m), 3.77-3.80 (3H, m), 6.49-6.53 (2H, m), 6.98 (1H, d, J=8.3 Hz), 7.85 (2H, d, J=8.3 Hz), 8.12 (2H, d, J=8.3 Hz). MS (ESI) m/z=569 (M+H)+.

The example compound shown below was synthesized by operations similar to those in Example 14 using appropriate reagents and starting material.

TABLE 24

| Compound | Structure | LCMS or HPLC condition | Retention time (min) | MS (m/z) |
|---|---|---|---|---|
| 155 | 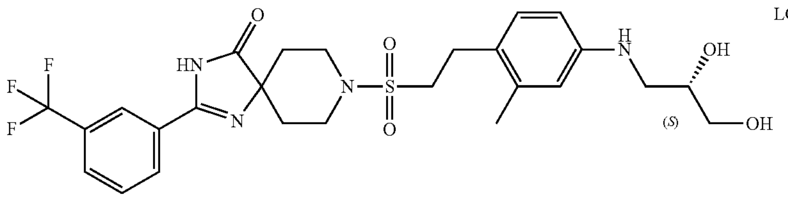 | LCMS-A-1 | 1.93 | 569 (M + H)+ |

Example 15

8-{2-[4-((S)-2,3-Dihydroxy-propylamino)-2-methyl-phenyl]-ethanesulfonyl}-2-(4-trifluoromethoxy-phenyl)-1,3,8-triaza-spiro[4.5]dec-1-en-4-one (Compound 156)

(Reaction 15-1)

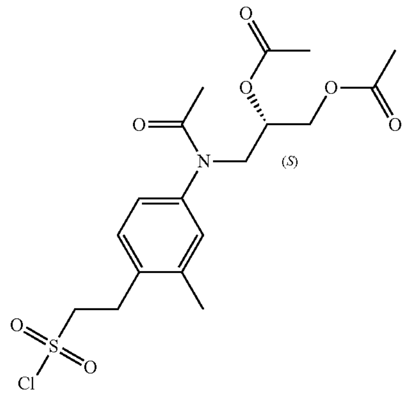

13g

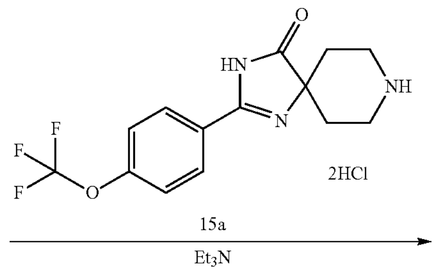

15a $Et_3N$
$CH_2Cl_2$

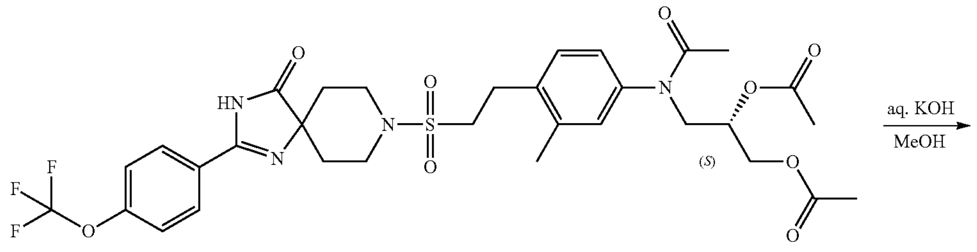

Compound 152

-continued

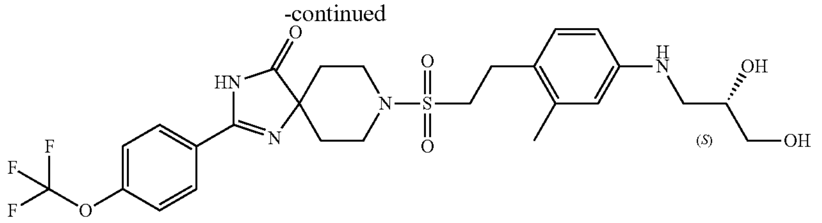

Compound 156

8-{2-[4-((S)-2,3-Dihydroxy-propylamino)-2-methyl-phenyl]-ethanesulfonyl}-2-(4-trifluoromethoxy-phenyl)-1,3,8-triaza-spiro[4.5]dec-1-en-4-one was synthesized by operations similar to those in Reaction 5-4 and Reaction 14-1 using appropriate reagents and starting material.

MS (ESI) m/z=585 (M+H)+.

The example compounds shown below were synthesized by operations similar to those in Example 15 using appropriate reagents and starting materials.

TABLE 25

| Compound | Structure | LCMS or HPLC condition | Retention time (min) | MS (m/z) |
|---|---|---|---|---|
| 157 | 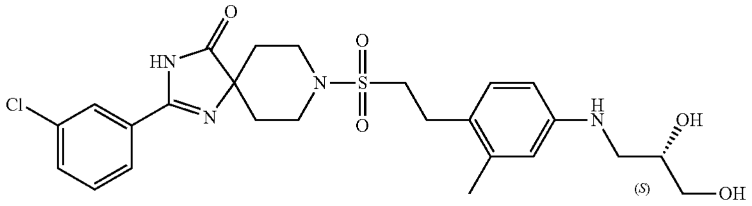 | LCMS-B-1 | 1.54 | 535 (M + H)+ |
| 158 | 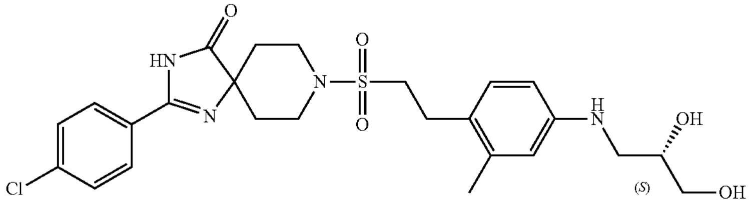 | LCMS-C-1 | 2.35 | 535 (M + H)+ |

Example 16

8-{2-[4-(2-Hydroxy-ethylamino)-2-methyl-phenyl]-ethanesulfonyl}-2-(3-trifluoromethoxy-phenyl)-1,3,8-triaza-spiro[4.5]dec-1-en-4-one (Compound 159)

(Reaction 16-1)

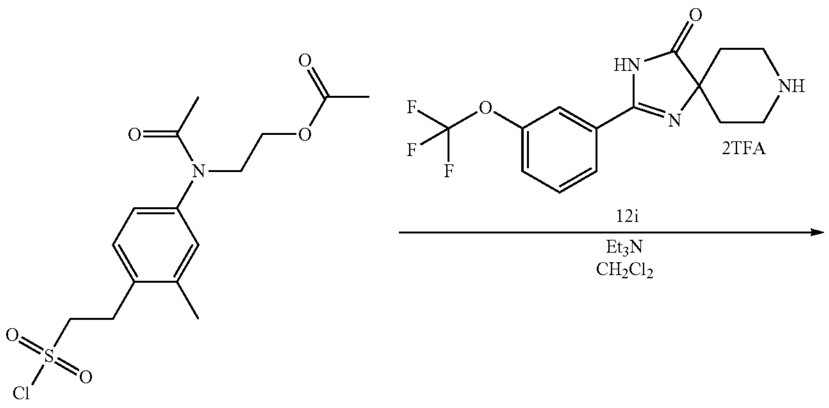

12h

-continued

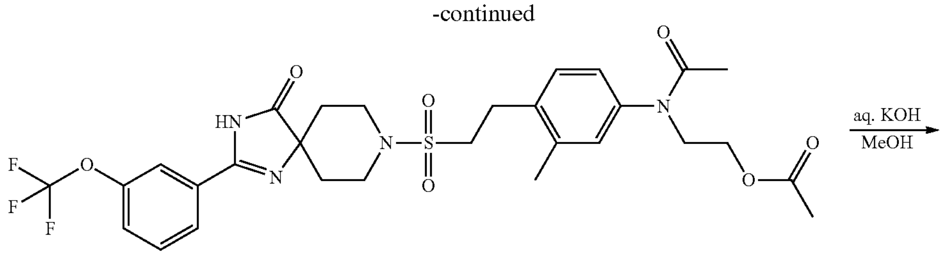

12j

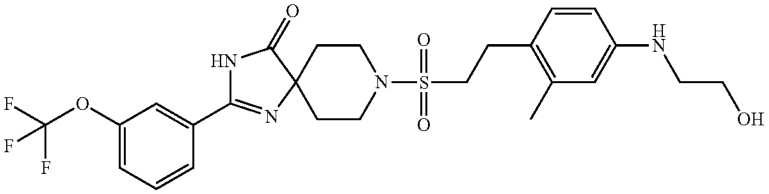

Compound 159

8-{2-[4-(2-Hydroxy-ethylamino)-2-methyl-phenyl]-ethanesulfonyl}-2-(3-trifluoromethoxy-phenyl)-1,3,8-triaza-spiro[4.5]dec-1-en-4-one was synthesized by operations similar to those in Reaction 5-4 and Reaction 14-1 using appropriate reagents and starting material.

MS (ESI) m/z=555 (M+H)+.

The example compounds shown below were synthesized by operations similar to those in Example 16 using appropriate reagents and starting materials.

TABLE 26

| Compound | Structure | LCMS or HPLC condition | Retention time (min) | MS (m/z) |
|---|---|---|---|---|
| 160 | 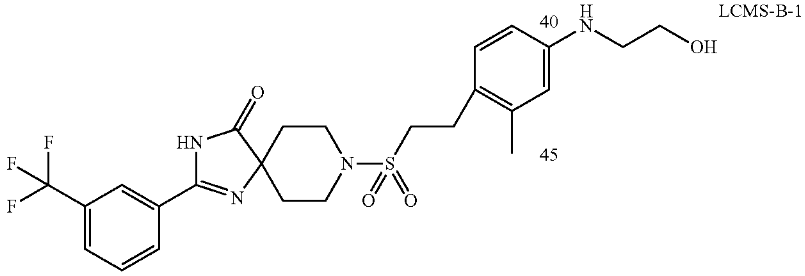 | LCMS-B-1 | 1.73 | 539 (M + H)+ |
| 161 | 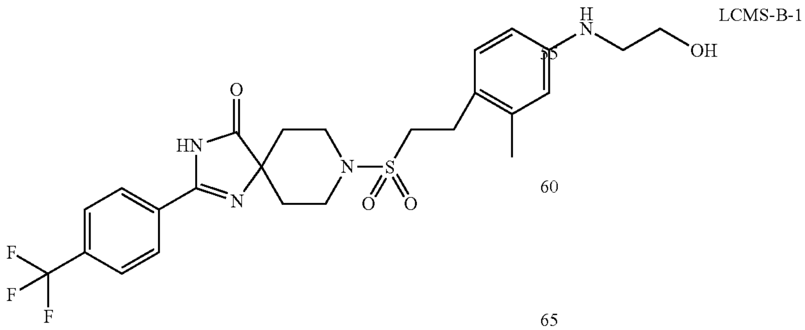 | LCMS-B-1 | 1.47 | 539 (M + H)+ |

Example 17

{4-[2-(2-tert-Butyl-4-oxo-1,3,8-triaza-spiro[4.5]dec-1-ene-8-sulfonyl)-ethyl]-3-methyl-benzyl}-carbamic acid tert-butyl ester (Compound 162)

(Reaction 17-1)

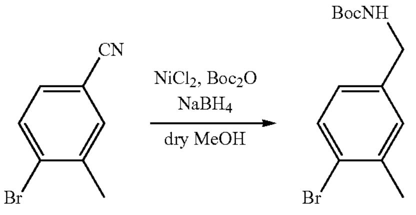

17a 17b $NaBH_4$ (1.45 g, 38.25 mmol) was added in small portions to a mixture of 4-bromo-3-methyl-benzonitrile (2.50 g, 12.8 mmol), $NiCl_2$ (1.65 g, 12.8 mmol) and $Boc_2O$ (5.57 g, 25.5 mmol) in anhydrous MeOH (130 ml) at 0° C. The mixture was stirred at room temperature for two hours and then concentrated under reduced pressure. Ethyl acetate and water were added to the resulting residue, and the mixture was filtered through celite. The two-layer solution was separated, and the aqueous layer was then further extracted with ethyl acetate. The organic layers were combined, dried over $Na_2SO_4$ and concentrated under reduced pressure. The residue was purified by silica gel column chromatography (hexane/ethyl acetate=1/0→4/1) to give (4-bromo-3-methyl-benzyl)-carbamic acid tert-butyl ester as a white solid (2.42 g, 63%).

MS (ESI) m/z=322 (M+Na)+.

(Reaction 17-2)

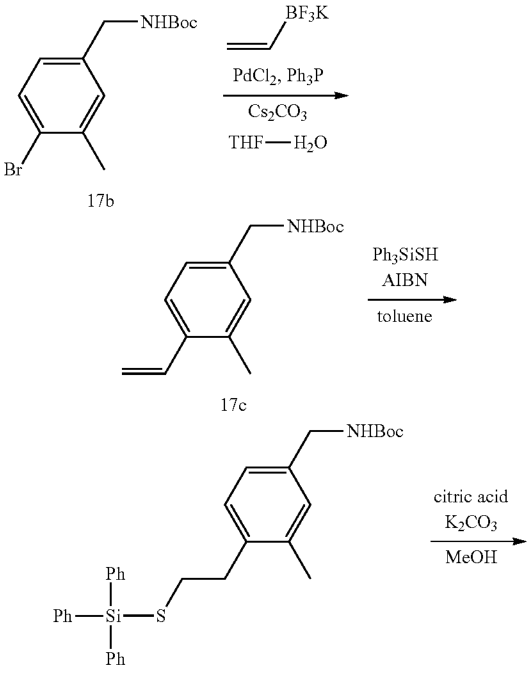

17b 17c 17d

-continued

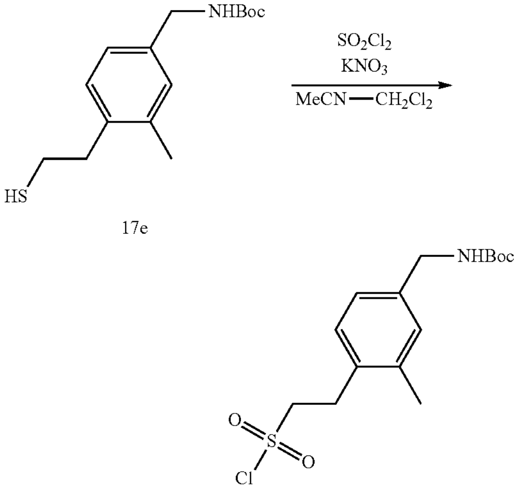

17e 17f

[4-(2-Chlorosulfonyl-ethyl)-3-methyl-benzyl]-carbamic acid tert-butyl ester was synthesized by operations similar to those in Reaction 10-2, Reaction 10-3, Reaction 10-4 and Reaction 10-5 using appropriate reagents and starting material.

MS (ESI) m/z=292 (M-tBu+Hx2)+.

(Reaction 17-3)

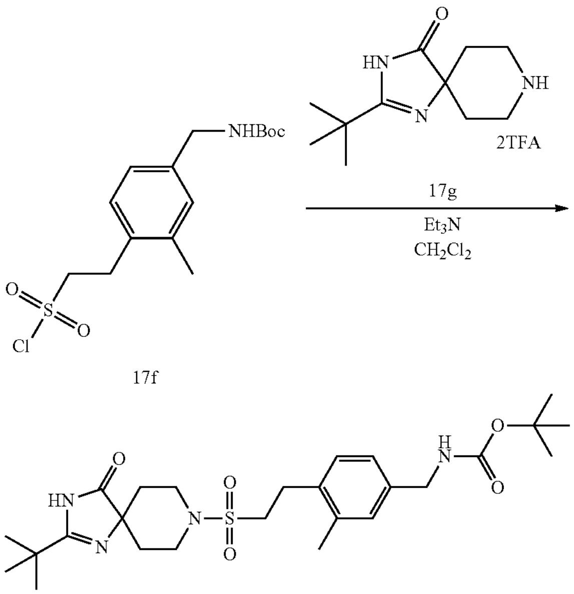

17f

Compound 162

{4-[2-(2-tert-Butyl-4-oxo-1,3,8-triaza-spiro[4.5]dec-1-ene-8-sulfonyl)-ethyl]-3-methyl-benzyl}-carbamic acid tert-butyl ester was synthesized by operations similar to those in Reaction 5-4 using appropriate reagents and starting material.

MS (ESI) m/z=521 (M+H)+.

The example compounds shown below were synthesized by operations similar to those in Example 17 using appropriate reagents and starting materials.

TABLE 27

| Compound | Structure | LCMS or HPLC condition | Retention time (min) | MS (m/z) |
| --- | --- | --- | --- | --- |
| 163 | 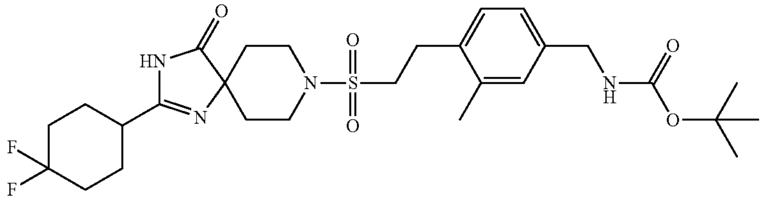 [SMILES: Cc1cc(CNC(=O)OC(C)(C)C)ccc1CCS(=O)(=O)N1CCC2(CC1)N=C(C1CCC(F)(F)CC1)NC2=O] | LCMS-C-1 | 2.67 | 583 (M + H)+ |
| 164 | 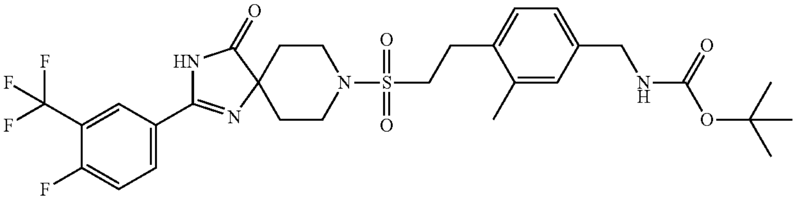 [SMILES: Cc1cc(CNC(=O)OC(C)(C)C)ccc1CCS(=O)(=O)N1CCC2(CC1)N=C(c1ccc(F)c(C(F)(F)F)c1)NC2=O] | LCMS-C-2 | 2.35 | 625 (M + H)+ |
| 165 | 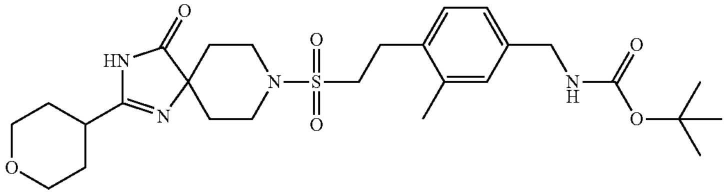 [SMILES: Cc1cc(CNC(=O)OC(C)(C)C)ccc1CCS(=O)(=O)N1CCC2(CC1)N=C(C1CCOCC1)NC2=O] | LCMS-B-1 | 1.92 | 549 (M + H)+ |

The spiroamine reagent used in the synthesis of Compound 163 (2-(4,4-difluoro-cyclohexyl)-1,3,8-triaza-spiro[4.5]dec-1-en-4-one ditrifluoroacetate) was synthesized by operations similar to those in Reaction 10-14, Reaction 5-2 and Reaction 7-2 using appropriate reagents and starting material.

Example 18

8-[2-(3-Amino-phenyl)-ethanesulfonyl]-2-cyclohexyl-1,3,8-triaza-spiro[4.5]dec-1-en-4-one (Compound 166)

(Reaction 18-1)

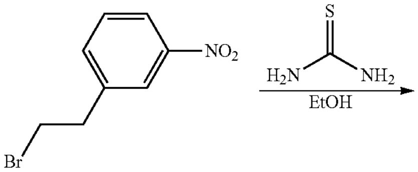

18a

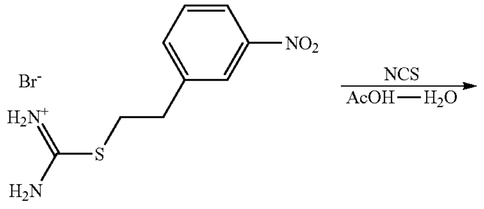

18b

-continued

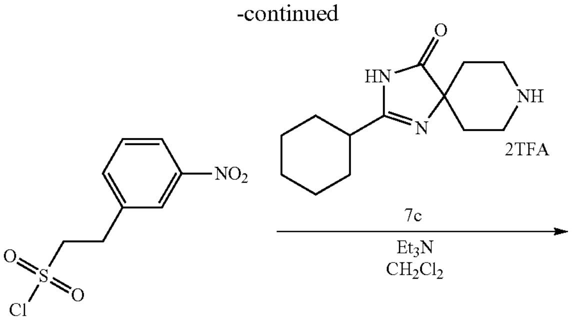

18c

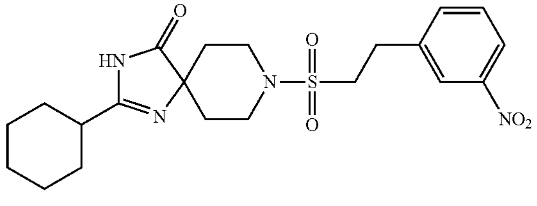

18d

A mixture of 1-(2-bromo-ethyl)-3-nitro-benzene (4 g, 17.4 mmol) and thiourea (1.5 g, 19.1 mmol) in ethanol (20 mL) was heated under reflux for one hour. The reaction mixture was concentrated under reduced pressure to give Compound 18b as a pale yellow solid. Further, NCS (7.66 g, 57.4 mmol) was added to a mixed solution of this solid in acetic acid (43.5 ml) and $H_2O$ (14.5 ml) on an ice bath, and the mixture was stirred at 5 to 10° C. for 50 minutes. The reaction mixture was diluted with $CH_2Cl_2$, and the organic layer was then washed with water, dried over $Na_2SO_4$ and concentrated under reduced pressure. Compound 7c (5.2 g, 11.2 mmol) and $Et_3N$ (6.3 mL, 44.9 mmol) were added to a solution of the resulting Compound 18c in $CH_2Cl_2$, and the mixture was stirred at room temperature for four hours. The reaction mixture was concentrated under reduced pressure, and the residue was then purified by silica gel flash chromatography to give 2-cyclohexyl-8-[2-(3-nitro-phenyl)-ethanesulfonyl]-1,3,8-triaza-spiro[4.5]dec-1-en-4-one (18d) as a white solid (1 g, yield 20% (three steps)). This compound was directly used in the next step.

(Reaction 18-2)

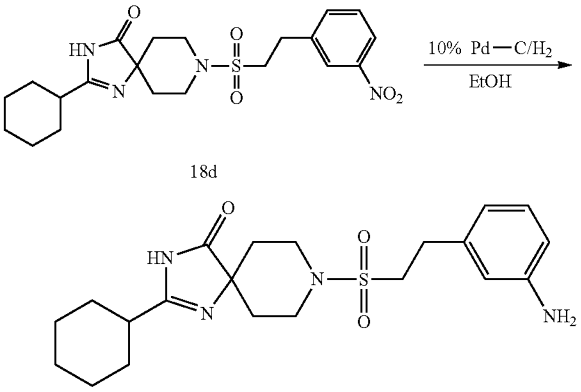

18d

Compound 166

10% Pd—C (1 g) was added to a solution of Compound 18d (1 g, 2.23 mmol) in ethanol (10 ml), and the mixture was stirred at room temperature for two days in an $H_2$ atmosphere. The reaction mixture was filtered, and the filtrate was then concentrated under reduced pressure to give 8-[2-(3-amino-phenyl)-ethanesulfonyl]-2-cyclohexyl-1,3,8-triaza-spiro[4.5]dec-1-en-4-one (920 mg, 98%).

MS (ESI) m/z=419 (M+H)+.

Example 19

N-{4-[2-(2-Cyclohexyl-4-oxo-1,3,8-triaza-spiro[4.5]dec-1-ene-8-sulfonyl)-ethyl]-phenyl}-acetamide (Compound 167)

(Reaction 19-1)

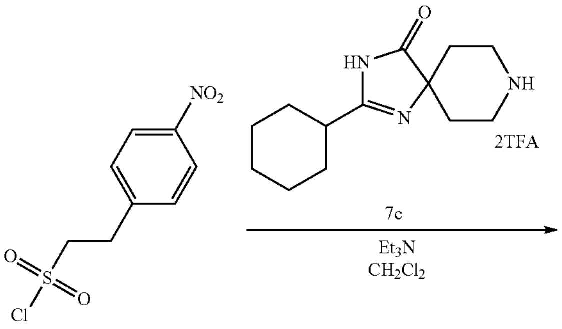

7c

19a

-continued

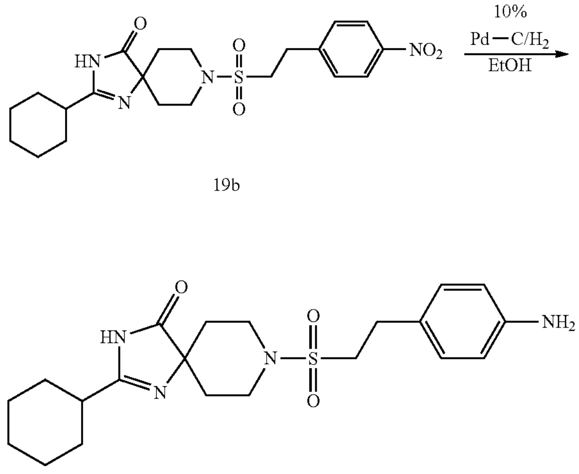

19b

19c

8-[2-(4-Amino-phenyl)-ethanesulfonyl]-2-cyclohexyl-1,3,8-triaza-spiro[4.5]dec-1-en-4-one was synthesized by operations similar to those in Reaction 5-4 and Reaction 18-2 using appropriate reagents and starting material. This compound was directly used in the next step.

(Reaction 19-2)

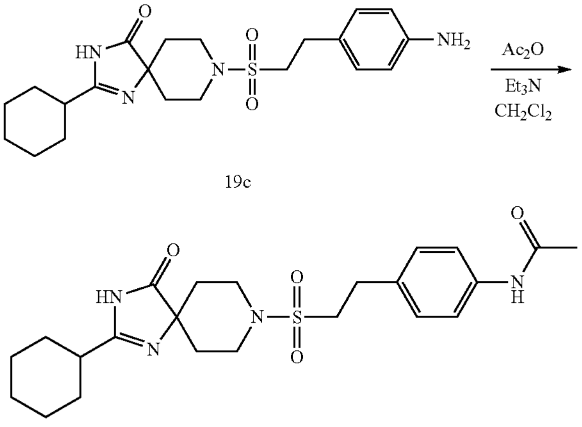

19c

Compound 167

Acetic anhydride (45 mg, 0.44 mmol) was added to a solution of 8-[2-(4-amino-phenyl)-ethanesulfonyl]-2-cyclohexyl-1,3,8-triaza-spiro[4.5]dec-1-en-4-one (92 mg, 0.22 mmol) in $CH_2Cl_2$ (5 mL). Triethylamine (55 mg, 0.5 mmol) was then added on an ice bath, and the mixture was stirred at room temperature for one hour. The reaction mixture was diluted with dichloromethane, and the organic layer was then sequentially washed with water and saturated brine and dried over $Na_2SO_4$. The organic layer was concentrated under reduced pressure, and the resulting residue was then purified by P-TLC to give N-{4-[2-(2-cyclohexyl-4-oxo-1,3,8-triaza-spiro[4.5]dec-1-ene-8-sulfonyl)-ethyl]-phenyl}-acetamide (55 mg, 54.3%).

MS (ESI) m/z=461 (M+H)+.

Example 20

3,N,N-Trimethyl-4-(2-{4-oxo-2-[3-(2,2,2-trifluoro-ethoxymethyl)-phenyl]-1,3,8-triaza-spiro[4.5]dec-1-ene-8-sulfonyl}-ethyl)-benzamide (Compound 168)

(Reaction 20-1)

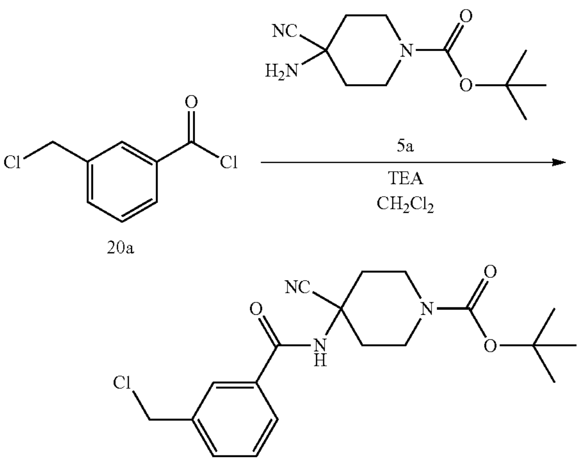

20a

20b 4-(3-Chloromethyl-benzoylamino)-4-cyano-piperidine-1-carboxylic acid tert-butyl ester was synthesized by operations similar to those in Reaction 2-3 using appropriate reagents and starting material.

MS (ESI) m/z=342 (M+H)+.

(Reaction 20-2)

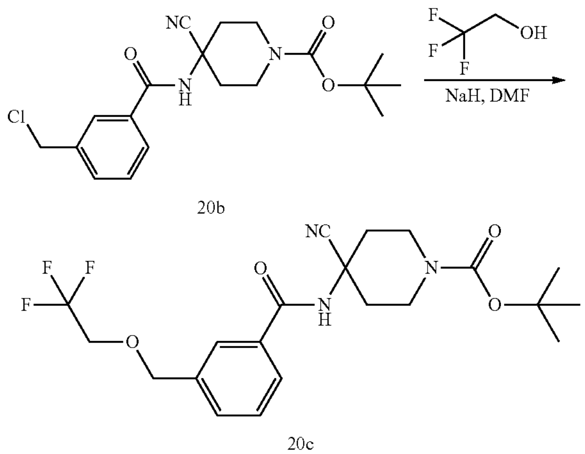

20b

20c

Sodium hydride (60% oil suspension, 191 mg, 4.77 mmol) was added to a solution of 2,2,2-trifluoro-ethanol (347 μl, 4.77 mmol) and 4-(3-chloromethyl-benzoylamino)-4-cyano-piperidine-1-carboxylic acid tert-butyl ester (600 mg, 1.59 mmol) in DMF (8 ml) at 0° C. The mixture was stirred at room temperature overnight, and then quenched with water and diluted with ethyl acetate. The organic layer was sequentially washed with a saturated aqueous $NaHCO_3$ solution, water (×2) and saturated brine, and then dried over $Na_2SO_4$ and concentrated under reduced pressure. The resulting residue was purified by silica gel column chromatography (hexane/ethyl acetate=2/1→1/2) to give 4-cyano-4-[3-(2,2,2-trifluoro-ethoxymethyl)-benzoylamino]-piperidine-1-carboxylic acid tert-butyl ester as a white solid (366 mg, 52%).

MS (ESI) m/z=442 (M+H)+.

(Reaction 20-3)

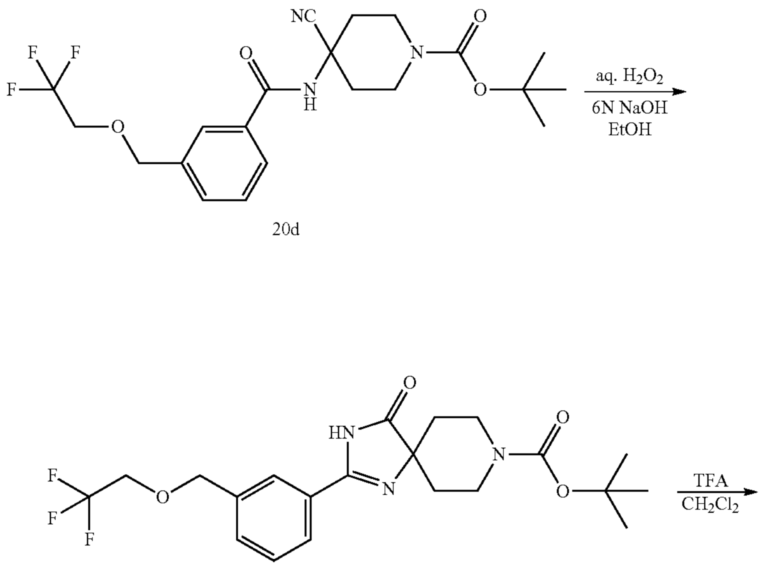

20d

20e

-continued

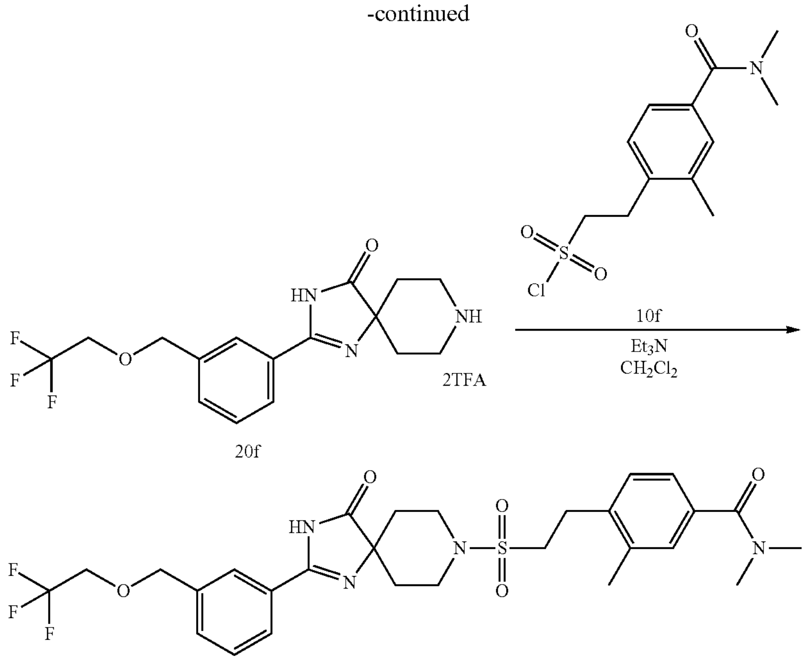

20f

Compound 168

3,N,N-Trimethyl-4-(2-{4-oxo-2-[3-(2,2,2-trifluoro-ethoxymethyl)-phenyl]-1,3,8-triaza-spiro[4.5]dec-1-ene-8-sulfonyl}-ethyl)-benzamide was synthesized by operations similar to those in Reaction 5-2, Reaction 7-2 and Reaction 5-4 using appropriate reagents and starting material.

MS (ESI) m/z=595 (M+H)+.

The example compounds shown below were synthesized by operations similar to those in Example 20 using appropriate reagents and starting materials.

TABLE 28

| Compound | Structure | LCMS or HPLC condition | Retention time (min) | MS (m/z) |
|---|---|---|---|---|
| 169 | 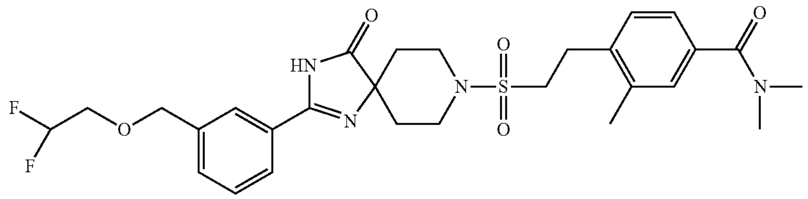 [SMILES: Cc1cc(C(=O)N(C)C)ccc1CCS(=O)(=O)N1CCC2(CC1)N=C(c1cccc(COCC(F)F)c1)NC2=O] | LCMS-C-1 | 2.23 | 577 (M + H)+ |
| 170 | 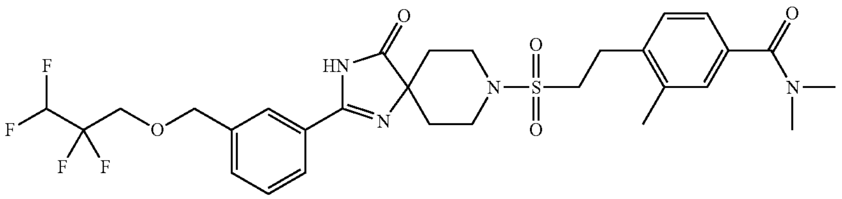 [SMILES: Cc1cc(C(=O)N(C)C)ccc1CCS(=O)(=O)N1CCC2(CC1)N=C(c1cccc(COCC(F)(F)C(F)F)c1)NC2=O] | LCMS-C-1 | 2.53 | 627 (M + H)+ |

Example 21

4-(2-{2-[3-(3,5-Dimethyl-isoxazol-4-yl)-phenyl]-4-oxo-1,3,8-triaza-spiro[4.5]dec-1-ene-8-sulfonyl}-ethyl)-3,N,N-trimethyl-benzamide (Compound 171)

(Reaction 21-1)

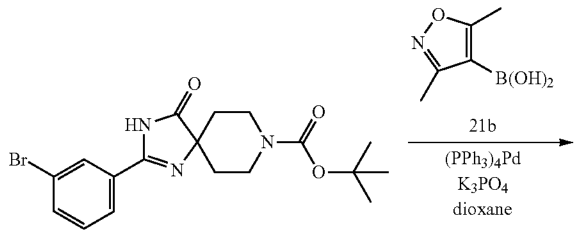

21a

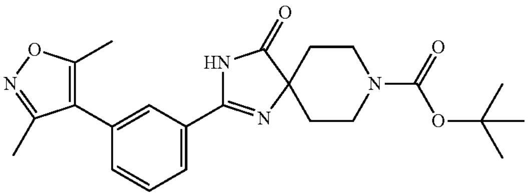

21c

A mixture of 2-(3-bromo-phenyl)-4-oxo-1,3,8-triaza-spiro[4.5]dec-1-ene-8-carboxylic acid tert-butyl ester (100 mg, 0.245 mmol), 3,5-dimethyl-isoxazole-4-boronic acid (51.8 mg, 0.367 mmol), tetrakis-(triphenylphosphine)palladium(0) (28 mg, 0.0245 mmol) and $K_3PO_4$ (104 mg, 0.490 mmol) in dioxane (1.2 mL) was heated with stirring at 100° C. for one hour in a nitrogen atmosphere. The reaction mixture was cooled, and then quenched with water and extracted with ethyl acetate (×3). The organic layers were combined and sequentially washed with water (×2) and saturated brine, and then dried over sodium sulfate and concentrated under reduced pressure. The resulting residue was purified by silica gel column chromatography (n-hexane:ethyl acetate=2:1) to give 2-[3-(3,5-dimethyl-isoxazol-4-yl)-phenyl]-4-oxo-1,3,8-triaza-spiro[4.5]dec-1-ene-8-carboxylic acid tert-butyl ester as a pale yellow solid (88.3 mg, 85%).

$^1$H-NMR (400 MHz, $CDCl_3$) δ 1.51 (9H, s), 1.52-1.63 (2H, m), 1.89-2.27 (2H, m), 2.31 (3H, s), 2.45 (3H, s), 3.38-3.55 (2H, m), 3.94-4.12 (2H, m), 7.45 (1H, d, J=7.8 Hz), 7.61 (1H, dd, J=7.8, 7.8 Hz), 7.85 (1H, s), 7.92 (1H, d, J=7.8 Hz), 10.20 (1H, brs).

(Reaction 21-2)

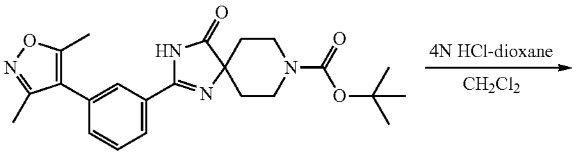

21c

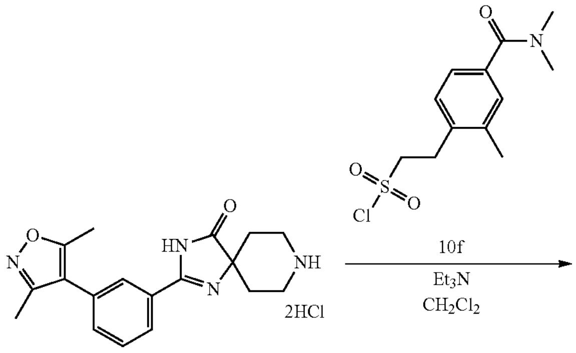

21d

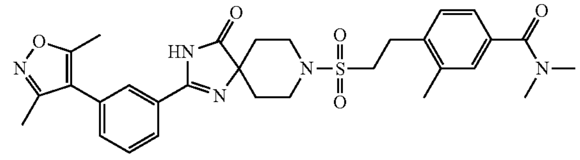

Compound 171

4-(2-{2-[3-(3,5-Dimethyl-isoxazol-4-yl)-phenyl]-4-oxo-1,3,8-triaza-spiro[4.5]dec-1-ene-8-sulfonyl}-ethyl)-3,N,N-trimethyl-benzamide was synthesized by operations similar to those in Reaction 5-3 and Reaction 5-4 using appropriate reagents and starting material.

$^1$H-NMR (400 MHz, CD3OD) δ 1.73-1.82 (2H, m), 1.98-2.07 (2H, m), 2.27 (3H, s), 2.42 (3H, s), 2.43 (3H, s), 3.00 (3H, s), 3.09 (3H, s), 3.14-3.22 (2H, m), 3.32-3.38 (2H, m), 3.45-3.55 (2H, m), 3.75-3.84 (2H, m), 7.23 (1H, d, J=7.8 Hz), 7.26 (1H, s), 7.34 (1H, d, J=7.8 Hz), 7.60 (1H, d, J=7.8 Hz), 7.66 (1H, d, J=7.8 Hz), 7.92 (1H, s), 7.99 (1H, d, J=7.8 Hz). MS (ESI) m/z=578 (M+H)+.

The example compounds shown below were synthesized by operations similar to those in Example 21 using appropriate reagents and starting materials.

TABLE 29

| Compound | Structure | LCMS or HPLC condition | Retention time (min) | MS (m/z) |
|---|---|---|---|---|
| 172 | 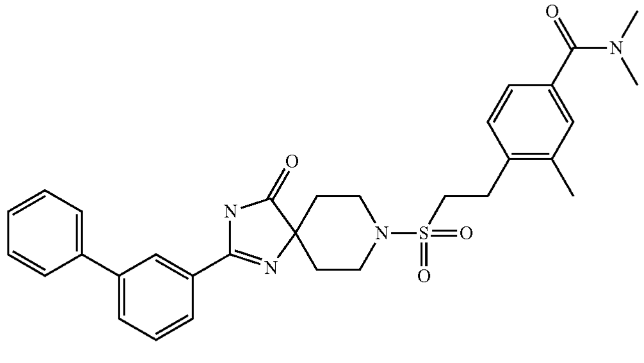 | LCMS-B-1 | 2.11 | 559 (M + H)+ |

TABLE 29-continued

| Compound | Structure | LCMS or HPLC condition | Retention time (min) | MS (m/z) |
|---|---|---|---|---|
| 173 | 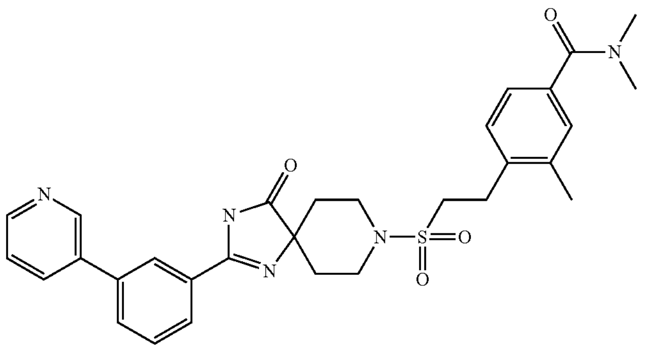 [SMILES: Cc1cc(C(=O)N(C)C)ccc1CCS(=O)(=O)N1CCC2(CC1)N=C(c1cccc(-c3cccnc3)c1)NC2=O] | LCMS-B-1 | 1.50 | 560 (M + H)+ |

Example 22

3-{8-[2-(4-Dimethylcarbamoyl-2-methyl-phenyl)-ethanesulfonyl]-4-oxo-1,3,8-triaza-spiro[4.5]dec-1-en-2-yl}-benzoic acid methyl ester (Compound 174)

(Reaction 22-1)

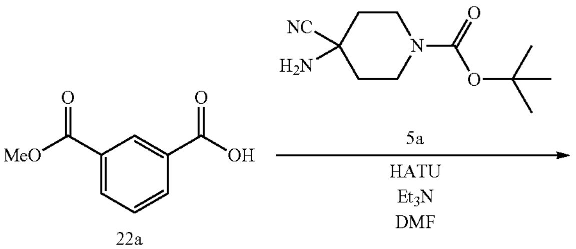

22a

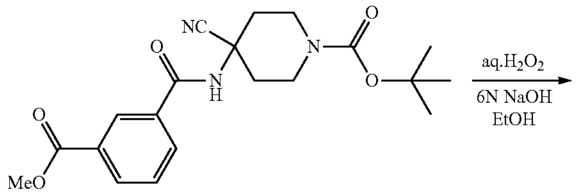

22b

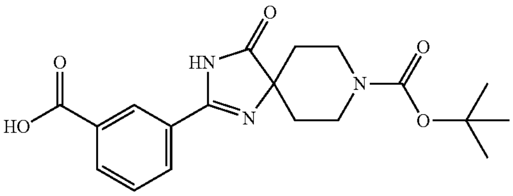

22c 2-(3-Carboxy-phenyl)-4-oxo-1,3,8-triaza-spiro[4.5]dec-1-ene-8-carboxylic acid tert-butyl ester was synthesized by operations similar to those in Reaction 10-14 and Reaction 2-4 using appropriate reagents and starting material.

MS (ESI) m/z=374 (M+H)+.

(Reaction 22-2)

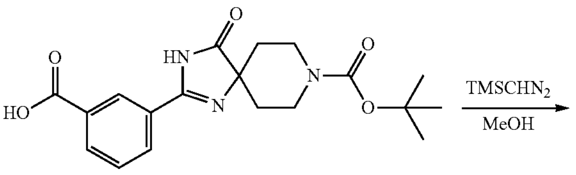

22c

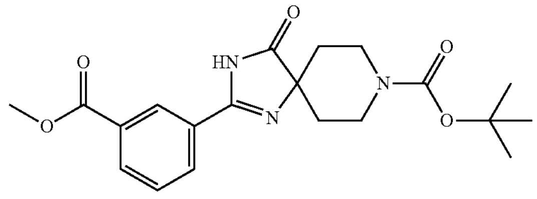

22d (Trimethylsilyl)diazomethane (2.0 M in hexane, 4.0 ml, 8.0 mmol) was added dropwise to a solution of 2-(3-carboxy-phenyl)-4-oxo-1,3,8-triaza-spiro[4.5]dec-1-ene-8-carboxylic acid tert-butyl ester (200 mg, 0.54 mmol) in methanol (10 ml). The mixture was stirred at room temperature for one hour, and (trimethylsilyl)diazomethane (1.0 ml, 2.0 mmol) was then further added, followed by stirring for one hour. The reaction mixture was concentrated under reduced pressure, and the resulting solid was then washed with a solution of hexane/ethyl acetate=5/1 to give 2-(3-methoxycarbonyl-phenyl)-4-oxo-1,3,8-triaza-spiro[4.5]dec-1-ene-8-carboxylic acid tert-butyl ester (91.5 mg, 44%).

MS (ESI) m/z=388 (M+H)+

(Reaction 22-3)

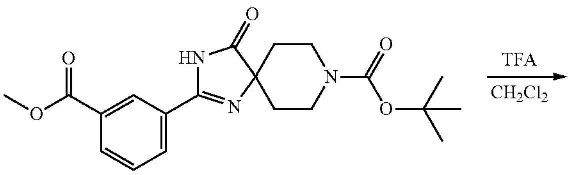

22d

-continued

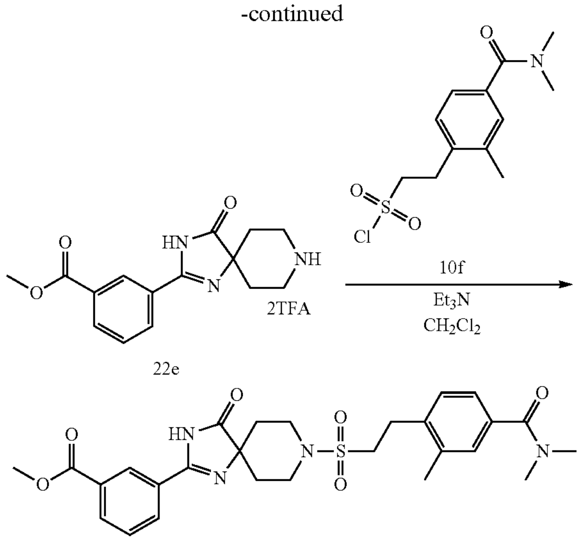

22e

Compound 174

3-{8-[2-(4-Dimethylcarbamoyl-2-methyl-phenyl)-ethanesulfonyl]-4-oxo-1,3,8-triaza-spiro[4.5]dec-1-en-2-yl}-benzoic acid methyl ester was synthesized by operations similar to those in Reaction 4-1 and Reaction 5-4 using appropriate reagents and starting material.

MS (ESI) m/z=541 (M+H)+.

Example 23

4-(2-{2-[1-(2,4-Dichloro-phenoxy)-1-methyl-ethyl]-4-oxo-1,3,8-triaza-spiro[4.5]dec-1-ene-8-sulfonyl}-ethyl)-3,N,N-trimethyl-benzamide (Compound 175)

(Reaction 23-1)

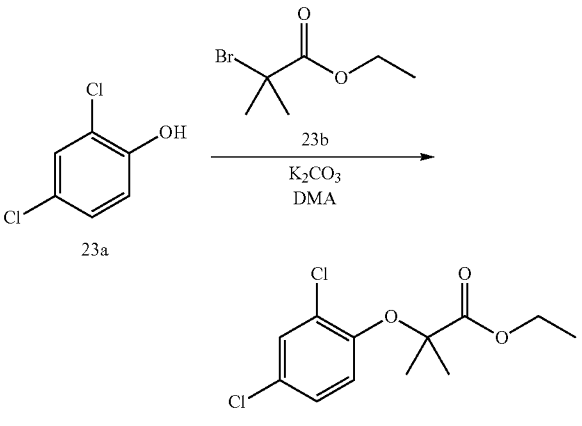

23a

23c 2,4-Dichlorophenol (448 mg, 2.75 mmol) and $K_2CO_3$ (775 mg, 5.61 mmol) were continuously added to 2-bromo-2-methyl-propionic acid ethyl ester (800 mg, 4.10 mmol) in N,N-dimethylacetamide (4 ml) at room temperature. The mixture was stirred at 110° C. for 14 hours, and saturated $NH_4Cl$ and $H_2O$ were then added, followed by extraction with AcOEt (×2). The organic layers were combined and sequentially washed with $H_2O$ and saturated brine, and then dried over $Na_2SO_4$ and concentrated under reduced pressure. The resulting residue was purified by silica gel column chromatography (n-hexane/AcOEt) to give 2-(2,4-dichloro-phenoxy)-2-methyl-propionic acid ethyl ester (389 mg, 50%).

$^1$H-NMR (270 MHz, $CDCl_3$): δ. 1.28 (3H, t, J=7.3 Hz), 1.60 (6H, s), 4.25 (2H, q, J=7.3 Hz), 6.86 (1H, d, J=8.8 Hz), 7.10 (1H, dd, J=8.8, 2.4 Hz), 7.38 (1H, d, J=2.4 Hz).

(Reaction 23-2)

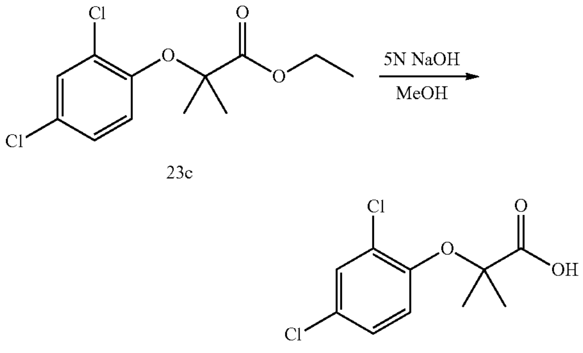

23c

23d

A 5 N aqueous NaOH solution (0.83 ml) was added to a solution of 2-(2,4-dichloro-phenoxy)-2-methyl-propionic acid ethyl ester (383 mg, 1.38 mmol) in MeOH (6 ml) at room temperature. The mixture was stirred at room temperature for four hours, and 1 N HCl (4.5 ml) and $H_2O$ were then added, followed by extraction with AcOEt (×2). The organic layers were combined and sequentially washed with $H_2O$ and saturated brine, and then dried over $Na_2SO_4$ and concentrated under reduced pressure to give 2-(2,4-dichloro-phenoxy)-2-methyl-propionic acid (359 mg).

$^1$H-NMR (270 MHz, DMSO-d6) δ 1.54 (6H, s), 6.94 (1H, d, J=8.8 Hz), 7.35 (1H, dd, J=8.8, 2.9 Hz), 7.60 (1H, d, J=2.4 Hz), 13.29 (1H, br.s).

(Reaction 23-3)

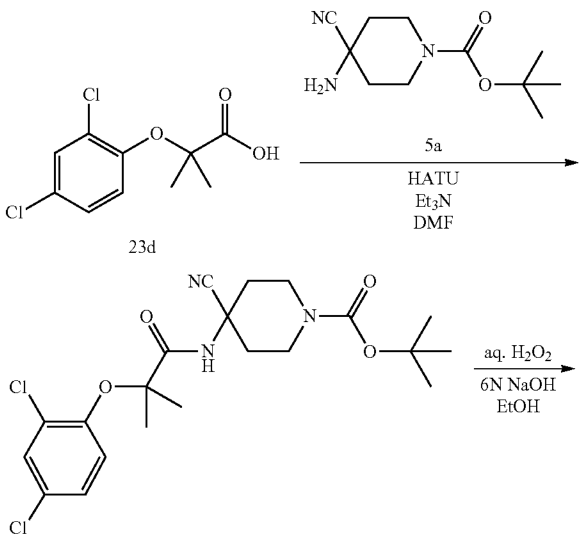

23d

23e

-continued

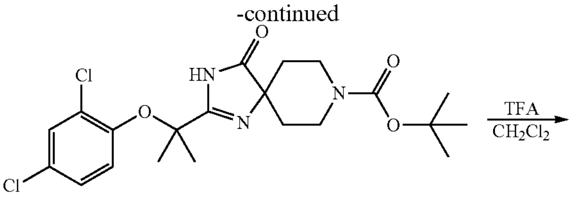

23f

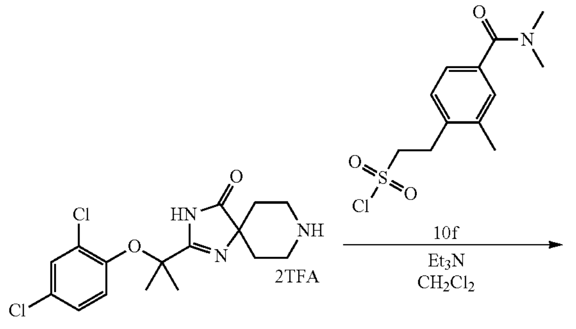

23g

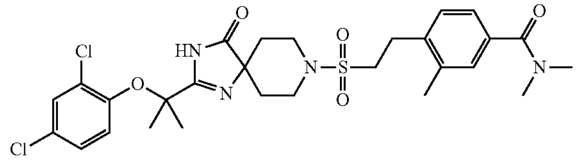

Compound 175

4-(2-{2-[1-(2,4-Dichloro-phenoxy)-1-methyl-ethyl]-4-oxo-1,3,8-triaza-spiro[4.5]dec-1-ene-8-sulfonyl}-ethyl)-3, N,N-trimethyl-benzamide was synthesized by operations similar to those in Reaction 10-14, Reaction 2-4, Reaction 7-2 and Reaction 5-4 using appropriate reagents and starting material.

MS (ESI) m/z=609 (M+H)+.

The example compound shown below was synthesized by operations similar to those in Example 23 using appropriate reagents and starting material.

Example 24

2-Cyclohexyl-4-oxo-1,3,8-triaza-spiro[4.5]dec-1-ene-8-sulfonic (3-ethylphenyl)amide (Compound 177)

(Reaction 24-1)

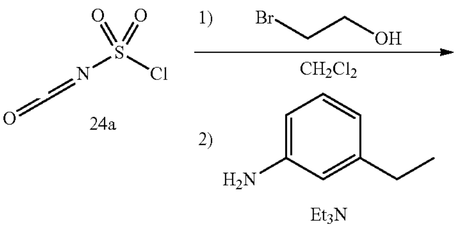

24a

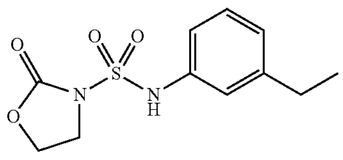

24b

2-Bromoethanol (0.28 mL, 4.00 mmol) was added to a solution of chlorosulfonyl isocyanate (0.35 mL, 4.00 mmol) in dichloromethane (1.8 mL) at 0° C. After stirring for 90 minutes, a solution of 3-ethylaniline (0.55 mL, 4.40 mmol) and triethylamine (1.23 mL, 8.80 mmol) in dichloromethane (3.6 mL) was added. The mixture was stirred for 90 minutes and then quenched with a 2 N aqueous hydrochloric acid solution. The mixed solution was separated, and the aqueous layer was then extracted with ether. The organic layers were combined and washed with water and saturated brine, and then dried over sodium sulfate and concentrated under reduced pressure. The resulting residue was washed with ether (5 mL) to give 2-oxo-oxazolidine-3-sulfonic acid (3-ethylphenyl)amide (LCMS yield 80%).

MS (ESI) m/z=271 (M+H)+.

TABLE 30

| Compound | Structure | LCMS or HPLC condition | Retention time (min) | MS (m/z) |
|---|---|---|---|---|
| 176 | 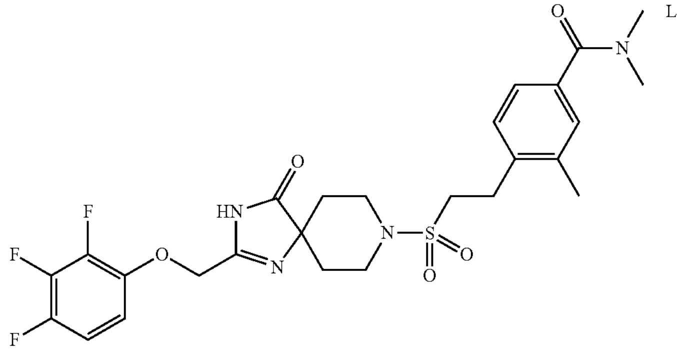 | LCMS-C-1 | 2.42 | 567 (M + H)+ |

(Reaction 24-2)

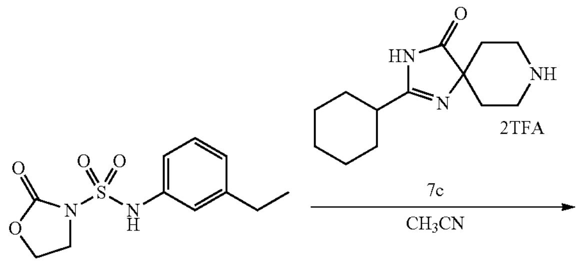

24b

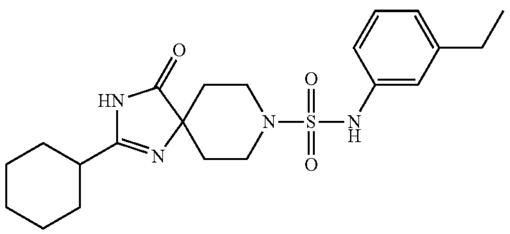

Compound 177

A solution of 2-oxo-oxazolidine-3-sulfonic acid (3-ethylphenyl)amide (92 mg, 0.340 mmol) and 2-cyclohexyl-1,3,8-triaza-spiro[4.5]dec-1-en-4-one ditrifluoroacetate (93 mg, 0.395 mmol) in acetonitrile (0.80 mL) was irradiated with microwaves (150° C., 15 min). The reaction mixture was filtered, and the resulting filtrate was then concentrated under reduced pressure. Further, the resulting residue was purified by silica gel chromatography to give 2-cyclohexyl-4-oxo-1,3,8-triaza-spiro[4.5]dec-1-ene-8-sulfonic acid (3-ethylphenyl)amide as a white amorphous (33 mg, 23%).

$^1$H-NMR (270 MHz, $CDCl_3$) δ 1.24 (3H, t, J=7.8 Hz), 1.31-1.93 (14H, m), 2.36-2.40 (1H, m), 2.64 (2H, q, J=7.8 Hz), 3.34-3.44 (2H, m), 3.69-3.76 (2H, m), 6.54 (1H, s), 6.96-7.02 (3H, m), 7.20-7.24 (1H, m), 8.27 (1H, s).

MS (ESI) m/z=419 (M+H)+.

Example 25

2-Cyclohexyl-8-[(E)-2-(1H-indol-5-yl)-ethenesulfonyl]-1,3,8-triaza-spiro[4.5]dec-1-en-4-one (Compound 178)

(Reaction 25-1)

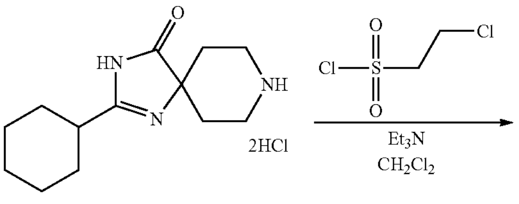

25a

-continued

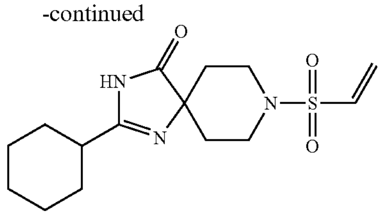

25b

2-Chloro-ethanesulfonyl chloride (440 μl, 4.21 mmol) was added to a solution of 2-cyclohexyl-1,3,8-triaza-spiro[4.5]dec-1-en-4-one dihydrochloride (1.50 g, 3.24 mmol) and triethylamine (2.7 ml, 19.4 mmol) in $CH_2Cl_2$ (30 ml) at room temperature in an $N_2$ atmosphere. The mixture was stirred at room temperature for 30 minutes, and then washed with water, dried over sodium sulfate and concentrated under reduced pressure. The resulting residue was triturated with AcOEt-hexane, and the solid was then collected by filtration and dried to give 2-cyclohexyl-8-ethenesulfonyl-1,3,8-triaza-spiro[4.5]dec-1-en-4-one as a colorless solid (692 mg, 66%).

$^1$H-NMR (400 MHz, $CDCl_3$) δ 1.25-1.45 (6H, m), 1.70-2.05 (8H, m), 2.40-2.47 (1H, m), 3.21-3.30 (2H, m), 3.61-3.69 (2H, m), 6.03 (1H, d, J=8.0 Hz), 6.26 (1H, d, J=16.0 Hz), 6.49 (1H, dd, J=16.0, 8.0 Hz), 8.17 (1H, brs).

MS (ESI) m/z=326 (M+H)+.

(Reaction 25-2)

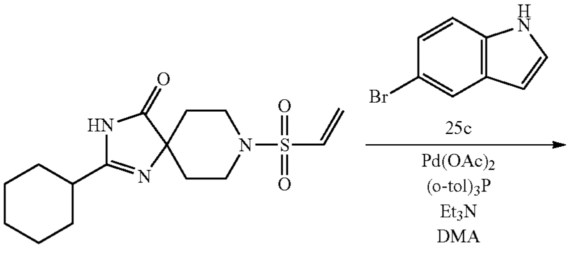

25b

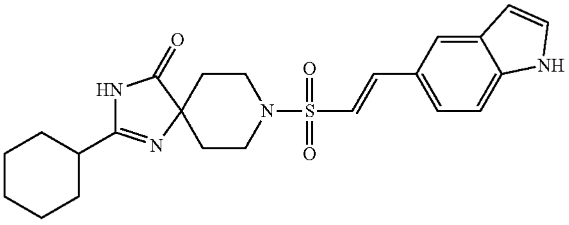

Compound 178

2-Cyclohexyl-8-ethenesulfonyl-1,3,8-triaza-spiro[4.5]dec-1-en-4-one (60.0 mg, 0.184 mmol), 5-bromo-indole (72.0 mg, 0.367 mmol), palladium(II) acetate (4.1 mg, 0.0183 mmol), tris(o-tolyl)phosphine (11.2 mg, 0.0368 mmol), triethylamine (0.077 ml, 0.552 mmol) and DMA (0.6 ml) were mixed in a sealed test tube in an $N_2$ atmosphere. This mixture was irradiated with microwaves (190° C., 20 min). The reaction mixture was cooled, and then quenched with saturated brine and extracted with ethyl acetate three times. The organic layers were combined, sequentially washed with water and saturated brine and concentrated under reduced pressure. The resulting residue was purified by silica gel column chromatography ($CH_2Cl_2$-MeOH) to give 2-cyclohexyl-8-[(E)-2-

(1H-indol-5-yl)-ethenesulfonyl]-1,3,8-triaza-spiro[4.5]dec-1-en-4-one as a yellow form (40.6 mg, 50%).

$^1$H-NMR (270 MHz, $CDCl_3$) δ 1.20-1.45 (5H, m), 1.52-1.95 (7H, m), 1.98-2.11 (2H, m), 2.35-2.48 (1H, m), 3.20-3.31 (2H, m), 3.68-3.79 (2H, m), 6.59-6.63 (1H, m), 6.65 (1H, d, J=16 Hz), 7.25-7.28 (1H, m), 7.33-7.44 (2H, m), 7.60 (1H, d, J=16 Hz), 7.77-7.79 (1H, m), 8.33 (1H, brs), 8.37 (1H, brs). MS (ESI) m/z=441 (M+H)+.

The example compounds shown below were synthesized by operations similar to those in Example 25 using appropriate reagents and starting materials.

Compounds 179 to 203

TABLE 31

| Compound | Structure | LCMS or HPLC condition | Retention time (min) | MS (m/z) |
|---|---|---|---|---|
| 179 | 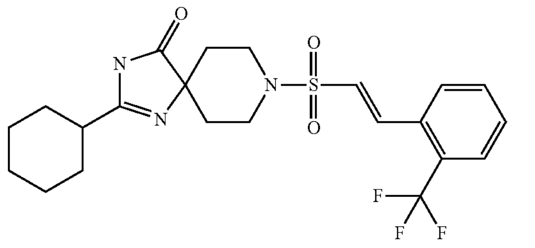 [SMILES: O=C1NC(C2CCCCC2)=NC12CCN(S(=O)(=O)/C=C/c1ccccc1C(F)(F)F)CC2] | LCMS-E-8 | 3.68 | 470 (M + H)+ |
| 180 | 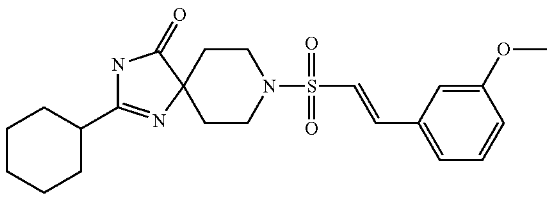 [SMILES: COc1cccc(/C=C/S(=O)(=O)N2CCC3(CC2)N=C(C2CCCCC2)NC3=O)c1] | LCMS-E-5 | 3.14 | 432 (M + H)+ |
| 181 | 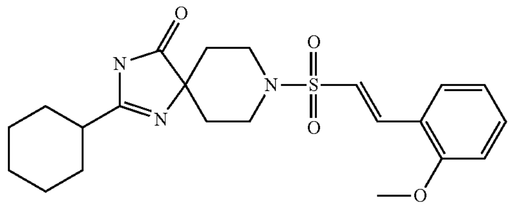 [SMILES: COc1ccccc1/C=C/S(=O)(=O)N1CCC2(CC1)N=C(C1CCCCC1)NC2=O] | LCMS-E-4 | 2.91 | 432 (M + H)+ |
| 182 | 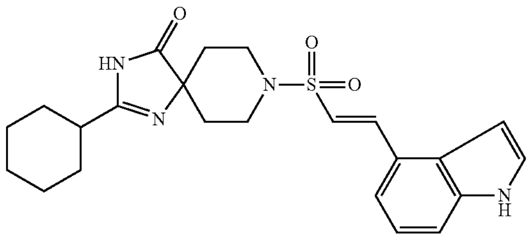 [SMILES: O=C1NC(C2CCCCC2)=NC12CCN(S(=O)(=O)/C=C/c1cccc3[nH]ccc13)CC2] | LCMS-C-1 | 2.48 | 441 (M + H)+ |
| 183 | 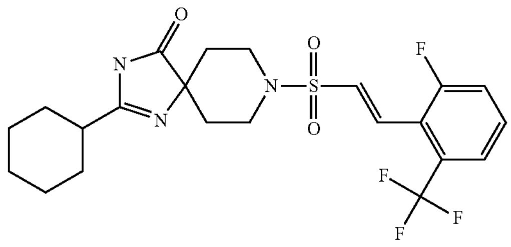 [SMILES: O=C1NC(C2CCCCC2)=NC12CCN(S(=O)(=O)/C=C/c1c(F)cccc1C(F)(F)F)CC2] | LCMS-E-6 | 1.66 | 488 (M + H)+ |
| 184 | 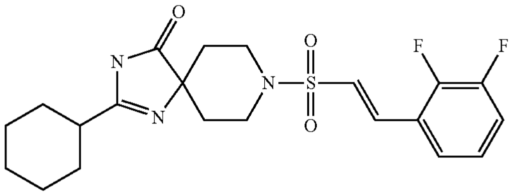 [SMILES: O=C1NC(C2CCCCC2)=NC12CCN(S(=O)(=O)/C=C/c1cccc(F)c1F)CC2] | LCMS-E-6 | 1.53 | 438 (M + H)+ |

TABLE 31-continued
| Compound | Structure | LCMS or HPLC condition | Retention time (min) | MS (m/z) |
|---|---|---|---|---|
| 185 | 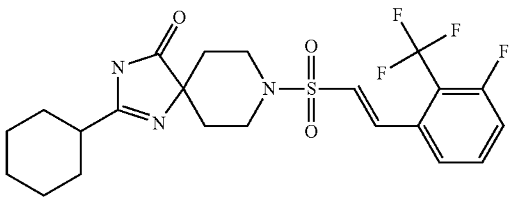 [SMILES: O=C1NC(C2CCCCC2)=NC12CCN(S(=O)(=O)/C=C/c1cccc(F)c1C(F)(F)F)CC2] | LCMS-E-6 | 1.7 | 488 (M + H)+ |
| 186 | 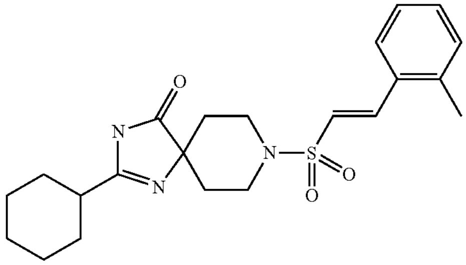 [SMILES: Cc1ccccc1/C=C/S(=O)(=O)N1CCC2(CC1)N=C(C1CCCCC1)NC2=O] | LCMS-C-1 | 2.73 | 416 (M + H)+ |
| 187 | 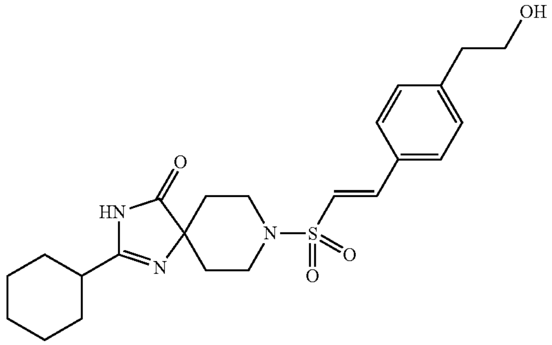 [SMILES: O=C1NC(C2CCCCC2)=NC12CCN(S(=O)(=O)/C=C/c1ccc(CCO)cc1)CC2] | LCMS-C-1 | 2.37 | 446 (M + H)+ |
| 188 | 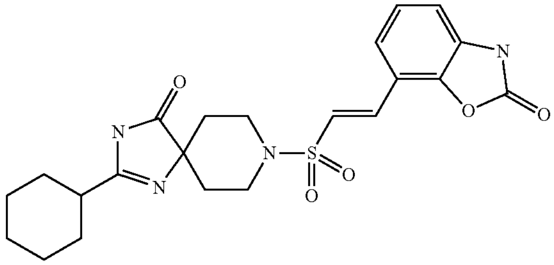 [SMILES: O=C1NC(C2CCCCC2)=NC12CCN(S(=O)(=O)/C=C/c1cccc3[nH]c(=O)oc13)CC2] | LCMS-A-1 | 1.84 | 459 (M + H)+ |
| 189 | 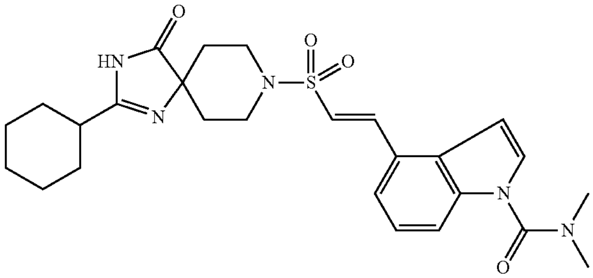 [SMILES: CN(C)C(=O)n1ccc2c(/C=C/S(=O)(=O)N3CCC4(CC3)N=C(C3CCCCC3)NC4=O)cccc21] | LCMS-C-1 | 2.53 | 512 (M + H)+ |

TABLE 31-continued
| Compound | Structure | LCMS or HPLC condition | Retention time (min) | MS (m/z) |
|---|---|---|---|---|
| 190 | 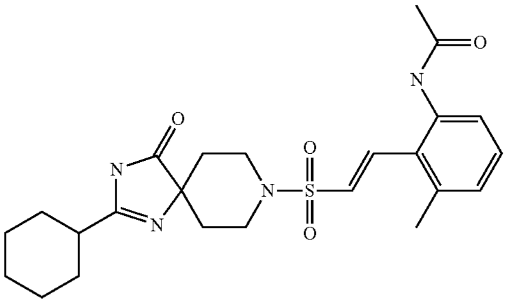 [SMILES: CC(=O)Nc1cccc(C)c1/C=C/S(=O)(=O)N1CCC2(CC1)N=C(C1CCCCC1)NC2=O] | LCMS-A-1 | 1.87 | 473 (M + H)+ |
| 191 | 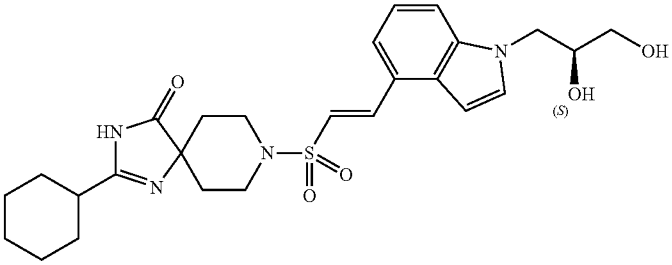 | LCMS-C-1 | 2.35 | 515 (M + H)+ |
| 192 | 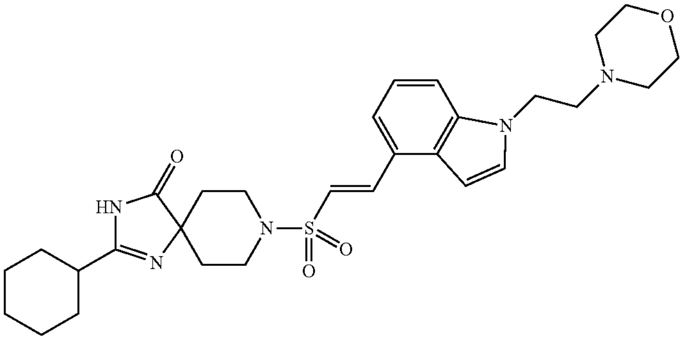 [SMILES: O=C1NC(C2CCCCC2)=NC12CCN(S(=O)(=O)/C=C/c1cccc3c1ccn3CCN1CCOCC1)CC2] | LCMS-C-1 | 2.65 | 554 (M + H)+ |
| 193 | 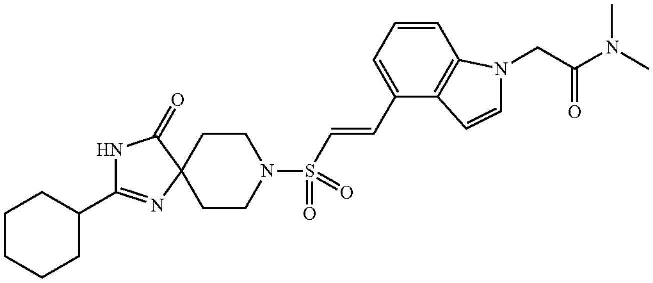 [SMILES: CN(C)C(=O)Cn1ccc2c(/C=C/S(=O)(=O)N3CCC4(CC3)N=C(C3CCCCC3)NC4=O)cccc21] | LCMS-C-1 | 2.37 | 526 (M + H)+ |
| 194 | 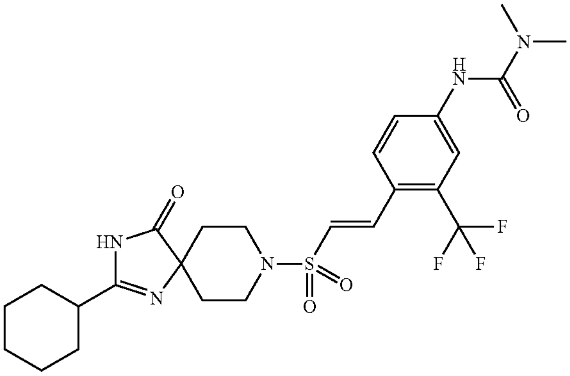 [SMILES: CN(C)C(=O)Nc1ccc(/C=C/S(=O)(=O)N2CCC3(CC2)N=C(C2CCCCC2)NC3=O)c(C(F)(F)F)c1] | LCMS-C-1 | 2.60 | 556 (M + H)+ |

TABLE 31-continued
| Compound | Structure | LCMS or HPLC condition | Retention time (min) | MS (m/z) |
|---|---|---|---|---|
| 195 | 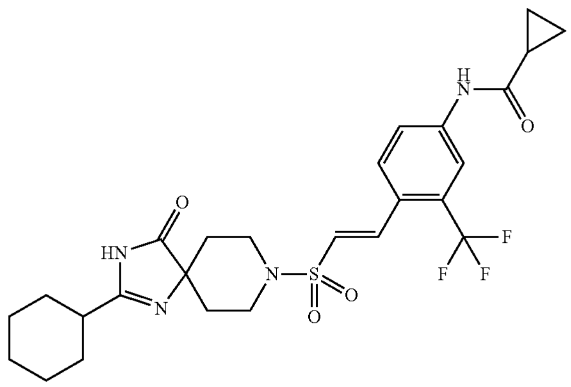 [SMILES: O=C(Nc1ccc(/C=C/S(=O)(=O)N2CCC3(CC2)N=C(C2CCCCC2)NC3=O)c(C(F)(F)F)c1)C1CC1] | LCMS-C-1 | 2.75 | 553 (M + H)+ |
| 196 | 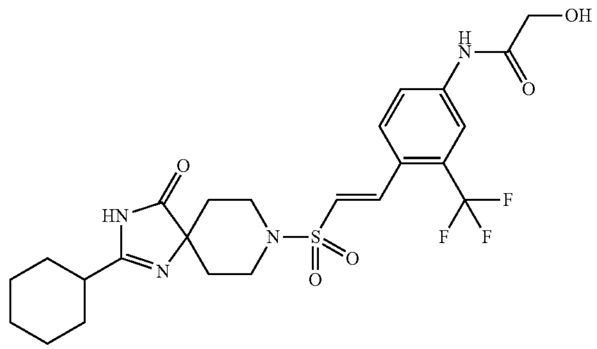 [SMILES: O=C(CO)Nc1ccc(/C=C/S(=O)(=O)N2CCC3(CC2)N=C(C2CCCCC2)NC3=O)c(C(F)(F)F)c1] | LCMS-C-1 | 2.48 | 543 (M + H)+ |
| 197 | 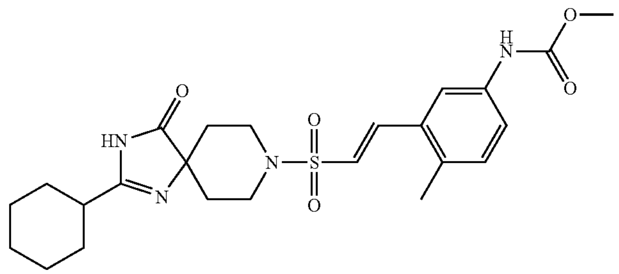 | LCMS-A-1 | 2.19 | 489 (M + H)+ |
| 198 | 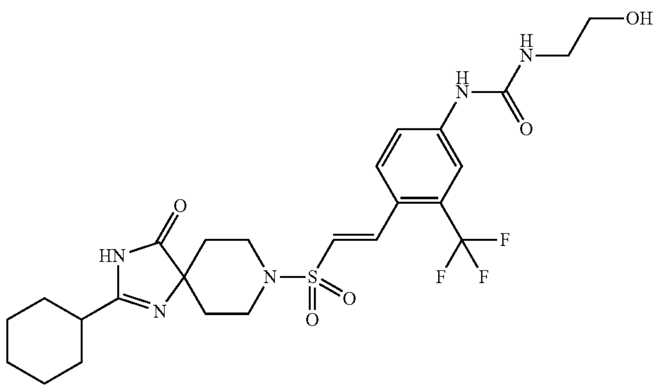 [SMILES: O=C(NCCO)Nc1ccc(/C=C/S(=O)(=O)N2CCC3(CC2)N=C(C2CCCCC2)NC3=O)c(C(F)(F)F)c1] | LCMS-C-1 | 2.48 | 572 (M + H)+ |

TABLE 31-continued
| Compound | Structure | LCMS or HPLC condition | Retention time (min) | MS (m/z) |
|---|---|---|---|---|
| 199 | 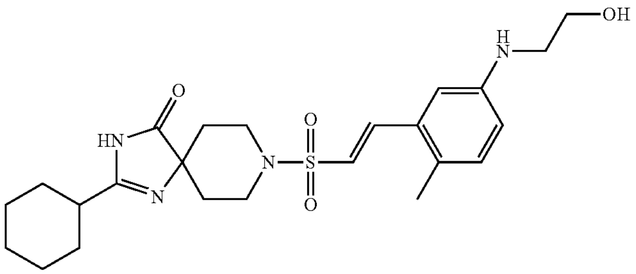 [SMILES: Cc1ccc(NCCO)cc1/C=C/S(=O)(=O)N1CCC2(CC1)N=C(C1CCCCC1)NC2=O] | LCMS-A-1 | 1.89 | 475 (M + H)+ |
| 200 | 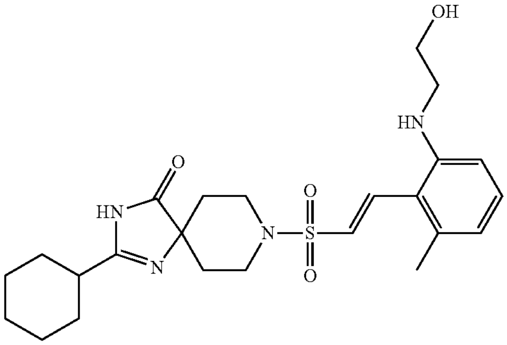 [SMILES: Cc1cccc(NCCO)c1/C=C/S(=O)(=O)N1CCC2(CC1)N=C(C1CCCCC1)NC2=O] | LCMS-A-1 | 2.09 | 475 (M + H)+ |
| 201 | 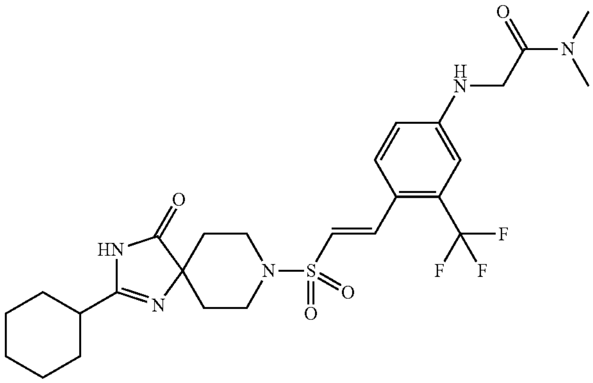 [SMILES: CN(C)C(=O)CNc1ccc(/C=C/S(=O)(=O)N2CCC3(CC2)N=C(C2CCCCC2)NC3=O)c(C(F)(F)F)c1] | LCMS-A-1 | 2.19 | 570 (M + H)+ |
| 202 | 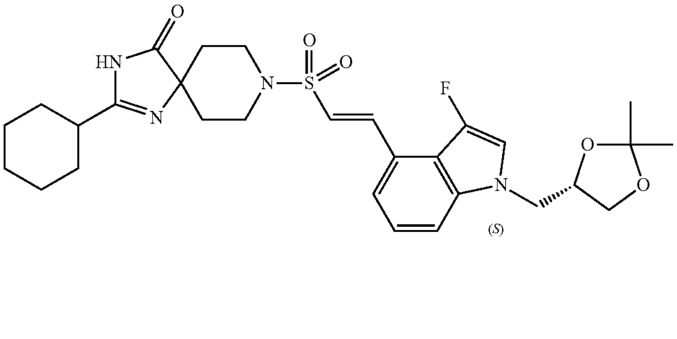 | LCMS-C-1 | 2.44 | 573 (M + H)+ |

TABLE 31-continued

| Compound | Structure | LCMS or HPLC condition | Retention time (min) | MS (m/z) |
|---|---|---|---|---|
| 203 | 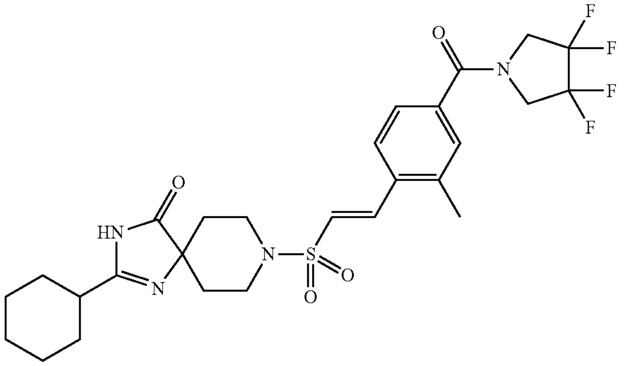 [SMILES: Cc1cc(C(=O)N2CC(F)(F)C(F)(F)C2)ccc1/C=C/S(=O)(=O)N1CCC2(CC1)N=C(C1CCCCC1)NC2=O] | LCMS-A-1 | 2.33 | 585 (M + H)+ |

The aryl bromide reagent used in the synthesis of Compound 191 ((S)-3-(4-bromo-indol-1-yl)-propane-1,2-diol) was synthesized as follows.

(Reaction 25-3)

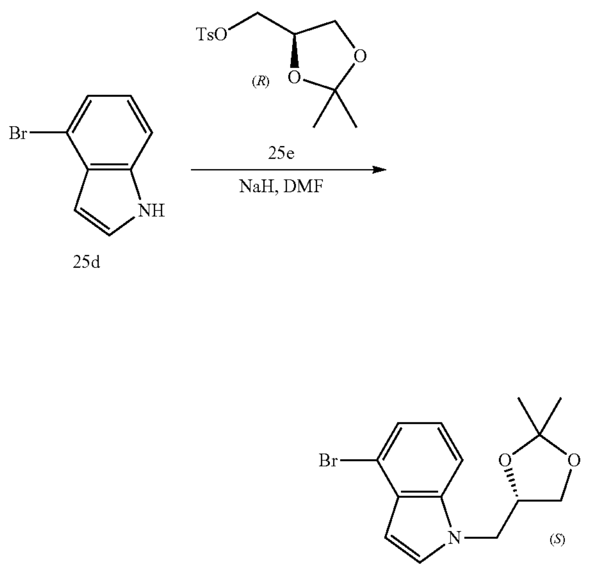

25d

25e

25f

NaH (382 mg, 9.55 mmol, 60% oily suspension) was added to a solution of 4-bromo-indole (1.0 ml, 7.97 mmol) and (R)-(−)-2,2-dimethyl-1,3-dioxolan-4-ylmethyl p-toluenesulfonate (2.74 g, 9.57 mmol) in dimethylformamide (20 ml) at 0° C. The mixture was stirred at 0° C. for two hours and at room temperature for 18 hours. NaH (190 mg, 4.75 mmol, 60% oily suspension) was further added, and the mixture was stirred at room temperature for six hours. The reaction mixture was diluted with AcOEt, and the organic layer was then washed with water (×2), dried over sodium sulfate and concentrated under reduced pressure. The resulting 4-bromo-1-((S)-2,2-dimethyl-[1,3]dioxolan-4-ylmethyl)-1H-indole was used in the next step without further purification.

(Reaction 25-4)

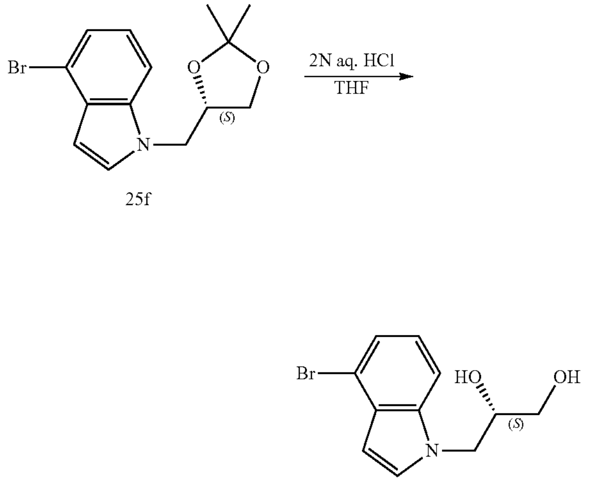

25f

25g

A 2 N aqueous HCl solution (15 ml) was added to a solution of the above mixture (4-bromo-1-((S)-2,2-dimethyl-[1,3]dioxolan-4-ylmethyl)-1H-indole) in tetrahydrofuran (30 ml), and the mixture was stirred at room temperature for eight hours. The reaction mixture was concentrated, and the residue was then diluted with AcOEt. This organic layer was sequentially washed with water (×2) and a saturated aqueous NaCl solution, and then dried and concentrated under reduced pressure. The resulting residue was purified by silica gel column chromatography ($CH_2Cl_2$-MeOH) to give (S)-3-(4-bromo-indol-1-yl)-propane-1,2-diol as a colorless solid (2.05 g, 95%).

MS (ESI) m/z=270, 272 (M+H)+.

The aryl bromide reagent used in the synthesis of Compound 192 (4-bromo-1-(2-morpholin-4-yl-ethyl)-1H-indole) was synthesized as follows.

(Reaction 25-5)

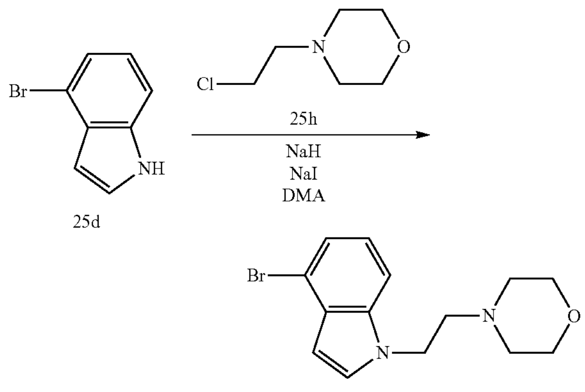

25d

25i

4-Bromo-1-(2-morpholin-4-yl-ethyl)-1H-indole was synthesized by operations similar to those in Reaction 25-3 using appropriate reagents and starting material.

MS (ESI) m/z=309, 311 (M+H)+.

The aryl bromide reagent used in the synthesis of Compound 193 (2-(4-bromo-indol-1-yl)-N,N-dimethyl-acetamide) was synthesized as follows.

(Reaction 25-6)

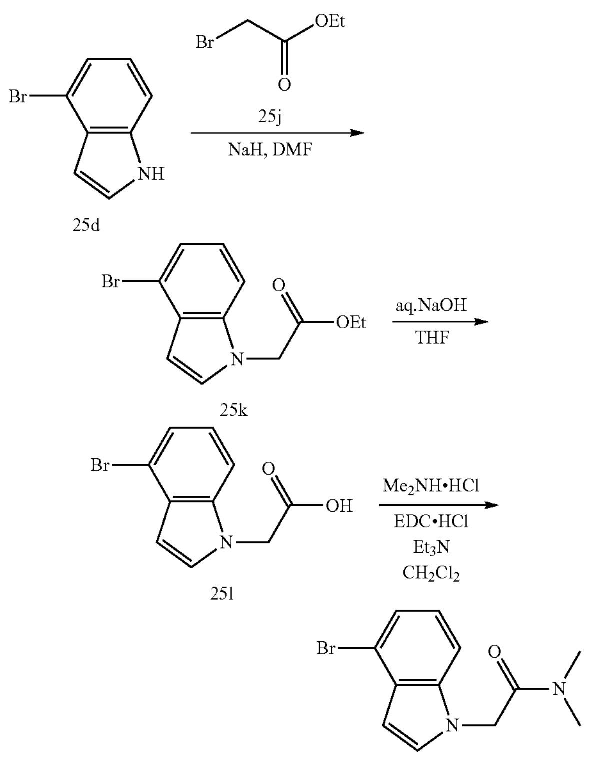

25d

25k

25l

25m 2-(4-Bromo-indol-1-yl)-N,N-dimethyl-acetamide was synthesized by operations similar to those in Reaction 25-3, Reaction 23-2 and Reaction 10-18 using appropriate reagents, solvent and starting material.

MS (ESI) m/z=281, 283 (M+H)+.

The aryl bromide reagent used in the synthesis of Compound 194 (3-(4-bromo-3-trifluoromethyl-phenyl)-1,1-dimethyl-urea) was synthesized as follows.

(Reaction 25-7)

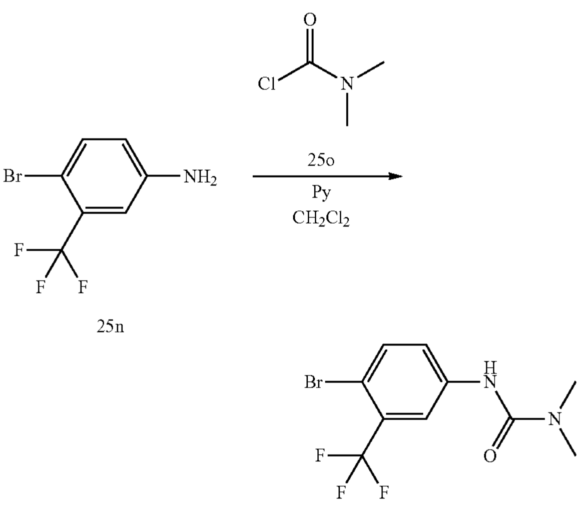

25n

25p 3-(4-Bromo-3-trifluoromethyl-phenyl)-1,1-dimethyl-urea was synthesized by operations similar to those in Reaction 2-3 using appropriate reagents and starting material.

MS (ESI) m/z=311, 313 (M+H)+.

The aryl bromide reagent used in the synthesis of Compound 195 (cyclopropanecarboxylic (4-bromo-3-trifluoromethyl-phenyl)-amide) was synthesized as follows.

(Reaction 25-8)

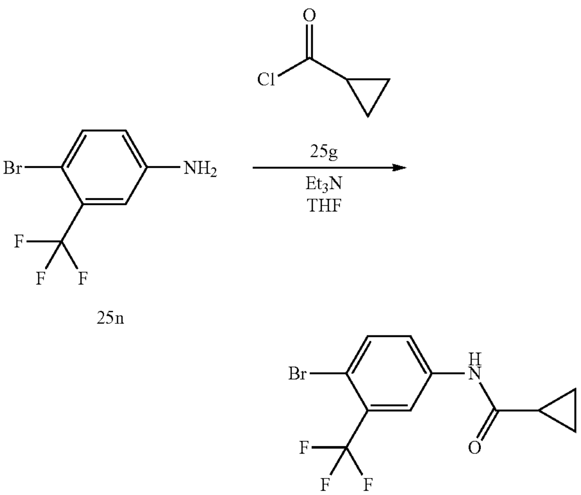

25n

25r

Cyclopropanecarboxylic (4-bromo-3-trifluoromethyl-phenyl)-amide was synthesized by operations similar to those in Reaction 2-3 using appropriate reagents and starting material.

MS (ESI) m/z=308, 310 (M+H)+.

The aryl bromide reagent used in the synthesis of Compound 196 (N-(4-bromo-3-trifluoromethyl-phenyl)-2-hydroxy-acetamide) was synthesized as follows.

(Reaction 25-9)

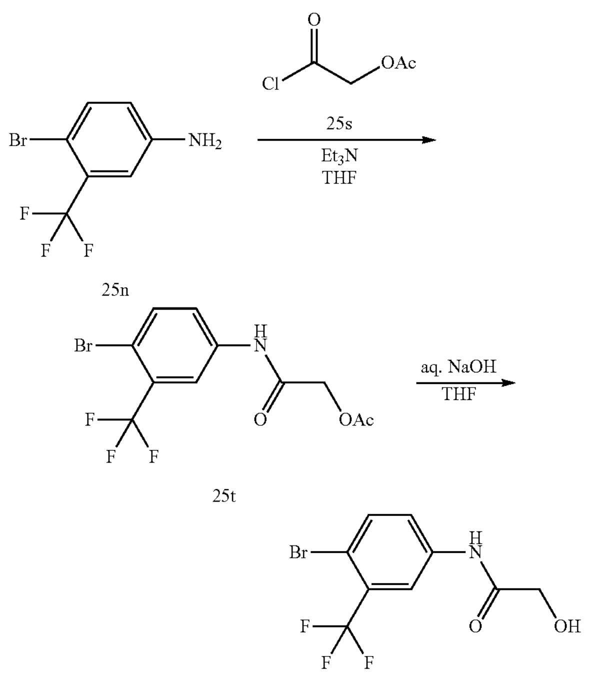

25n

25t

25u

N-(4-Bromo-3-trifluoromethyl-phenyl)-2-hydroxy-acetamide was synthesized by operations similar to those in Reaction 2-3 and Reaction 23-2 using appropriate reagents and starting material.

MS (ESI) m/z=298, 300 (M+H)+.

The aryl bromide reagent used in the synthesis of Compound 197 ((3-bromo-4-methyl-phenyl)-carbamic acid methyl ester) was synthesized as follows.

(Reaction 25-10)

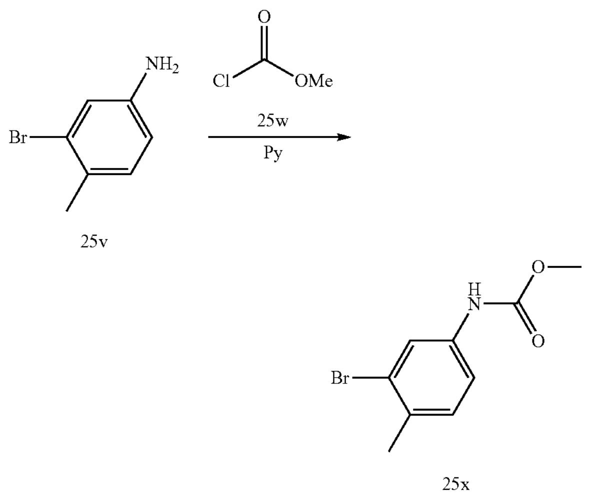

25v

25x

Methyl chloroformate (0.202 ml, 2.62 mmol) was added to a solution of 3-bromo-4-methyl-phenylamine (243 mg, 1.31 mmol) in pyridine (2 ml), and the mixture was stirred at room temperature overnight. $H_2O$ was added to the reaction mixture, followed by extraction with AcOEt (×2). The organic layers were combined and sequentially washed with $H_2O$ and saturated brine, and then dried over $Na_2SO_4$ and concentrated under reduced pressure. The resulting residue was purified by silica gel chromatography (n-hexane/AcOEt) to give (3-bromo-4-methyl-phenyl)-carbamic acid methyl ester (288 mg, 90%).

$^1$H-NMR (270 MHz, $CDCl_3$) δ 2.34 (3H, s), 3.77 (3H, s), 6.51 (1H, br. s), 7.14 (1H, d, J=7.2 Hz), 7.20 (1H, dd, J=7.4, 2.0 Hz), 7.63 (1H, d, J=2.0 Hz).

The aryl bromide reagent used in the synthesis of Compound 198 (1-(4-bromo-3-trifluoromethyl-phenyl)-3-(2-hydroxy-ethyl)-urea) was synthesized as follows.

(Reaction 25-11)

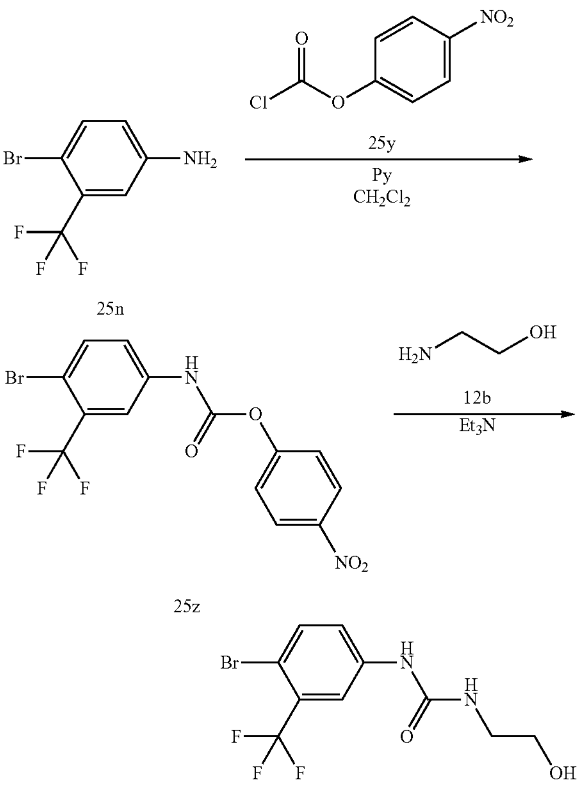

25n

25z

25aa p-Nitrophenyl chloroformate (437 mg, 2.17 mmol) was added to a solution of 4-bromo-3-trifluoromethyl-aniline (400 μl, 1.67 mmol) and pyridine (202 μl, 2.50 mmol) in $CH_2Cl_2$ (6.2 ml) at 0° C. The mixture was stirred at 0° C. for one hour, and 2-amino-ethanol (150 μl, 2.50 mmol) was then added, followed by further stirring at 0° C. for two hours. Triethylamine (210 μl, 1.51 mmol) was added to the mixture, and the mixture was stirred at 0° C. for one hour. 1 N HCl was added to the reaction mixture, followed by extraction with $CH_2Cl_2$/AcOEt. The organic layer was washed with water (×2), and then dried over sodium sulfate and concentrated under reduced pressure. The residue was purified by silica gel column chromatography ($CH_2Cl_2$-MeOH) to give 1-(4- bromo-3-trifluoromethyl-phenyl)-3-(2-hydroxy-ethyl)-urea as a white powder (520 mg, 73%).

MS (ESI) m/z=327, 329 (M+H)+.

The aryl bromide reagent used in the synthesis of Compound 199 (2-(3-bromo-4-methyl-phenylamino)-ethanol) was synthesized as follows.

(Reaction 25-12)

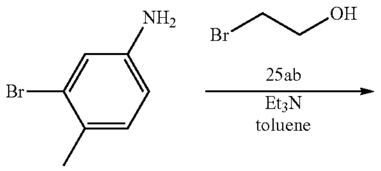

25v

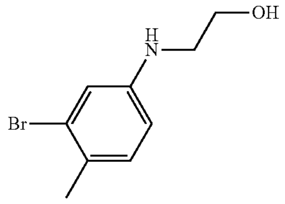

25ac

Triethylamine (0.28 mL, 2.00 mmol) and bromoethanol (0.14 mL, 1.98 mmol) were added to a solution of 3-bromo-4-methyl-phenylamine (240 mg, 1.29 mmol) in toluene (2 ml). The mixture was stirred at 100° C. overnight and $H_2O$ was then added, followed by extraction with AcOEt (×2). The organic layers were combined and sequentially washed with $H_2O$ and saturated brine, and then dried over $Na_2SO_4$ and concentrated under reduced pressure. The resulting residue was purified by silica gel column chromatography (n-hexane/AcOEt) to give 2-(3-bromo-4-methyl-phenylamino)-ethanol (185 mg, 62%).

$^1$H-NMR (270 MHz, $CDCl_3$) δ 1.68 (1H, br, OH), 2.27 (3H, s, Me), 3.26 (2H, dd, J=5.3, 5.1 Hz), 3.82 (2H, dd, J=5.3, 5.1 Hz), 3.90 (1H, br, NH), 6.52 (1H, dd, J=8.2, 2.5 Hz), 6.85 (1H, d, J=2.5 Hz), 7.01 (1H, d, J=8.2 Hz). MS (ESI) m/z=230, 232 (M+H)+.

The aryl bromide reagent used in the synthesis of Compound 200 (2-(2-bromo-3-methyl-phenylamino)-ethanol) was synthesized as follows.

(Reaction 25-13)

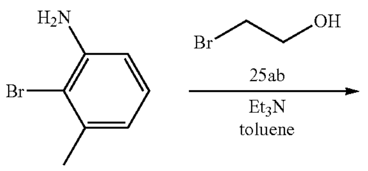

25ad

-continued

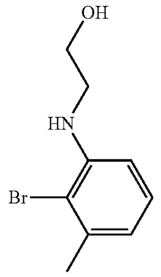

25ae 2-(2-Bromo-3-methyl-phenylamino)-ethanol was synthesized by operations similar to those in Reaction 25-12 using appropriate reagents and starting material.

MS (ESI) m/z=230, 232 (M+H)+.

The aryl bromide reagent used in the synthesis of Compound 201 (2-(4-bromo-3-trifluoromethyl-phenylamino)-N,N-dimethyl-acetamide) was synthesized as follows.

(Reaction 25-14)

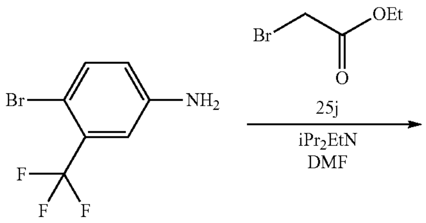

25n

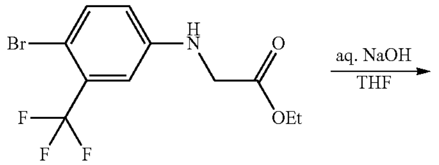

25af

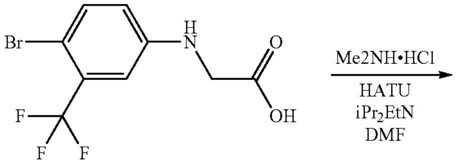

25ag

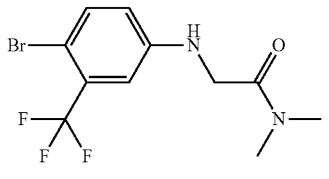

25ah 2-(4-Bromo-3-trifluoromethyl-phenylamino)-N,N-dimethyl-acetamide was synthesized by operations similar to those in Reaction 25-12, Reaction 14-1 and Reaction 10-14 using appropriate reagents and starting material.

MS (ESI) m/z=325, 327 (M+H)+.

The aryl bromide reagent used in the synthesis of Compound 202 (4-bromo-1-((S)-2,2-dimethyl-[1,3]dioxolan-4-ylmethyl)-3-fluoro-1H-indole) was synthesized as follows.

(Reaction 25-15)

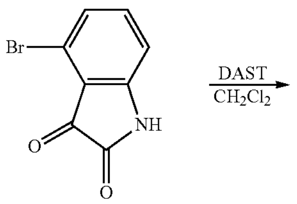

25ai

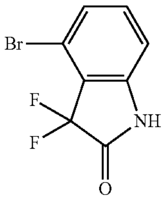

25aj

Diethylaminotrifluorosulfur (1.5 mL, 11.06 mmol) was added to a solution of 4-bromo-1H-indole-2,3-dione (1.0 g, 4.4 mmol) in dichloromethane (44 mL) at 0° C. The mixture was stirred at room temperature for 54 hours and then quenched with methanol-water. The organic layer and the aqueous layer were separated, and the aqueous layer was then extracted with dichloromethane. The organic layers were combined, dried over sodium sulfate and then concentrated under reduced pressure. The resulting residue was purified by silica gel column chromatography to give 4-bromo-3,3-difluoro-1,3-dihydro-indol-2-one as a yellow solid (559 mg, 51%).

MS (ESI) m/z=246 (M−H)−.

(Reaction 25-16)

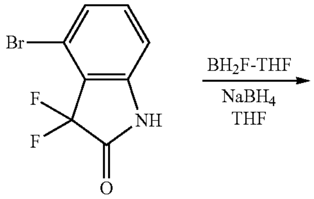

25aj

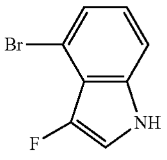

25ak

Synthesis of a 1.3 M solution of $BH_2F$ in tetrahydrofuran (Reagent A): Boron trifluoride etherate (2 mL) was added dropwise to a suspension of sodium borohydride (340 mg, 4.5 mmol) in tetrahydrofuran (12 mL) at 0° C. The mixture was stirred at 0° C. for 90 minutes to give Reagent A.

Reagent A (2.85 mL, 3.709 mmol) was added dropwise to a solution of 4-bromo-3,3-difluoro-1,3-dihydro-indol-2-one (400 mg, 1.61 mmol) in tetrahydrofuran (8.1 mL) at 0° C. The mixture was stirred at 0° C. for 3.5 hours and at room temperature for 16 hours. Further, Reagent A (3.0 mL) was added to the reaction mixture, followed by stirring at room temperature for three hours. The reaction mixture was quenched with 3 M HCl (4.8 mL) and then extracted with ethyl acetate (×2). The organic layers were combined and sequentially washed with water and saturated brine, and then dried over sodium sulfate and concentrated under reduced pressure. The resulting residue was purified by silica gel column chromatography to give 4-bromo-3-fluoro-1H-indole as a yellow oil (132 mg, 38%).

MS (ESI) m/z=212 (M−H)−.

(Reaction 25-17)

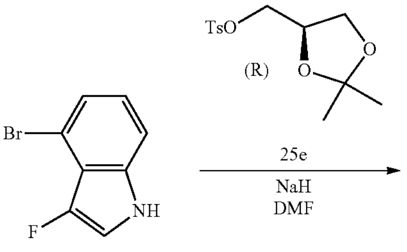

25ak

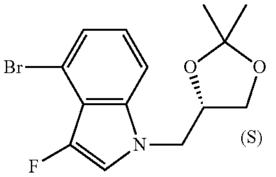

25al

4-Bromo-1-((S)-2,2-dimethyl-[1,3]dioxolan-4-ylmethyl)-3-fluoro-1H-indole was synthesized by operations similar to those in Reaction 25-3 using appropriate reagents and starting material.

$^1$H-NMR (400 MHz, $CDCl_3$) δ 1.33 (3H, s), 1.40 (3H, s), 3.65 (1H, dd, J=5.9, 8.8 Hz), 4.04 (1H, dd, J=6.1, 8.8 Hz), 4.14 (2H, t, J=4.9 Hz), 4.37-4.42 (1H, m), 7.02-7.07 (2H, m), 7.23-7.27 (2H, m).

The aryl bromide reagent used in the synthesis of Compound 203 ((4-bromo-3-methyl-phenyl)-(3,3,4,4-tetrafluoro-pyrrolidin-1-yl)-methanone) was synthesized as follows.

(Reaction 25-18)

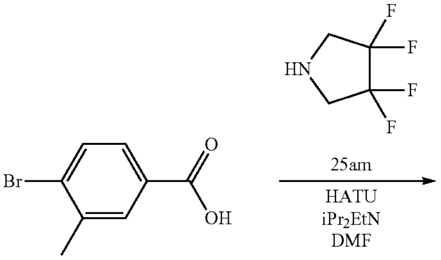

10a

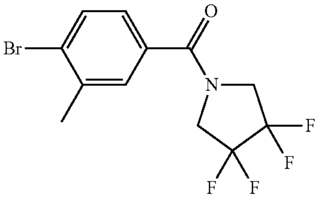

25an (4-Bromo-3-methyl-phenyl)-(3,3,4,4-tetrafluoro-pyrrolidin-1-yl)-methanone was synthesized by operations similar to those in Reaction 10-14 using appropriate reagents and starting material.

MS (ESI) m/z=340, 342 (M+H)+.

Example 26

N-{4-[(E)-2-(2-Cyclohexyl-4-oxo-1,3,8-triaza-spiro[4.5]dec-1-ene-8-sulfonyl)-vinyl]-3,5-dimethyl-phenyl}-acetamide (Compound 204)

(Reaction 26-1)

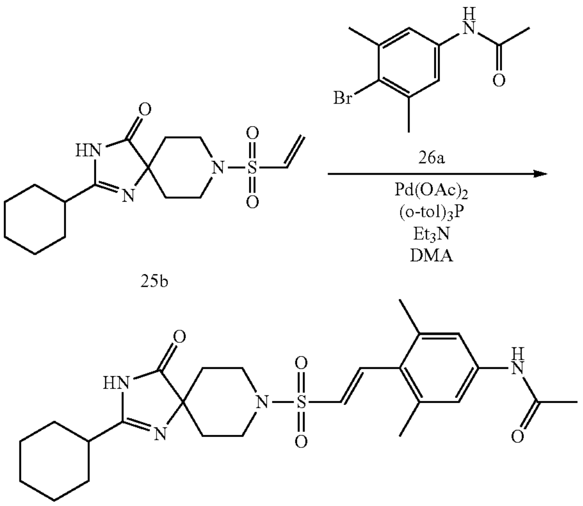

25b

Compound 204

A mixture of 2-cyclohexyl-8-ethenesulfonyl-1,3,8-triaza-spiro[4.5]dec-1-en-4-one (100.0 mg, 0.307 mmol), N-(4-bromo-3,5-dimethyl-phenyl)-acetamide (112. mg, 0.461 mmol), palladium(II) acetate (10 mg, 0.0461 mmol), tris(o-tolyl)phosphine (28 mg, 0.0922 mmol), triethylamine (0.128 ml, 0.922 mmol) and DMA (1.5 ml) was added to a sealed test tube in an $N_2$ atmosphere. This mixture was heated with stirring at 130° C. for 13.5 hours. Palladium(II) acetate (10 mg, 0.0461 mmol), tris(o-tolyl)phosphine (28 mg, 0.0922 mmol) and triethylamine (0.128 ml, 0.922 mmol) were further added to the reaction mixture at room temperature in an $N_2$ atmosphere, and the mixture was heated with stirring at 130° C. for 14 hours. The reaction mixture was cooled and water was then added. The aqueous layer was extracted with ethyl acetate (×3). The organic layers were combined and sequentially washed with water (×2) and saturated brine, and then dried over sodium sulfate and concentrated under reduced pressure. The resulting residue was purified by silica gel column chromatography ($CH_2Cl_2$-MeOH) to give N-{4-[(E)-2-(2-cyclohexyl-4-oxo-1,3,8-triaza-spiro[4.5]dec-1-ene-8-sulfonyl)-vinyl]-3,5-dimethyl-phenyl}-acetamide (61.4 mg, 41%).

$^1$H-NMR (400 MHz, CD3OD) δ 1.20-1.57 (6H, m), 1.59-1.79 (3H, m), 1.80-2.00 (6H, m), 2.12 (3H, s), 2.39 (6H, s), 3.20-3.40 (2H, m), 3.58-3.75 (2H, m), 6.58 (1H, d, J=16 Hz), 7.35 (2H, s), 7.57 (1H, d, J=16 Hz). MS (ESI) m/z=487 (M+H)+.

The example compounds shown below were synthesized by operations similar to those in Example 26 using appropriate reagents and starting materials.

Compounds 205 to 208

TABLE 32

| Compound | Structure | LCMS or HPLC condition | Retention time (min) | MS (m/z) |
|---|---|---|---|---|
| 205 | 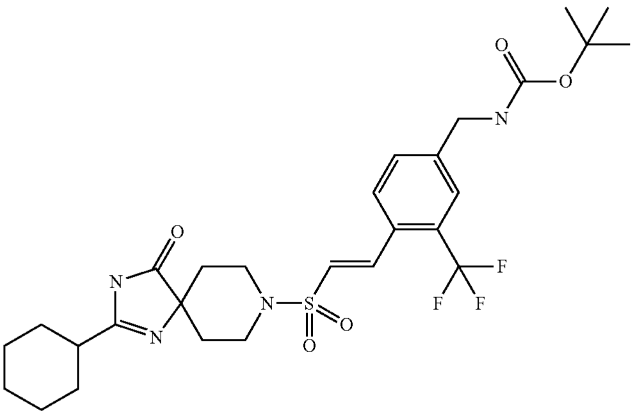 [SMILES: CC(C)(C)OC(=O)NCc1ccc(/C=C/S(=O)(=O)N2CCC3(CC2)N=C(C2CCCCC2)NC3=O)c(C(F)(F)F)c1] | LCMS-C-1 | 2.87 | 599 (M + H)+ |

TABLE 32-continued

| Compound | Structure | LCMS or HPLC condition | Retention time (min) | MS (m/z) |
|---|---|---|---|---|
| 206 | 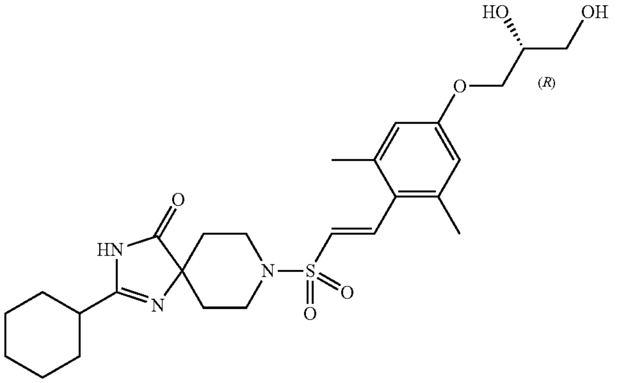 | LCMS-C-1 | 2.38 | 520 (M + H)+ |
| 207 | 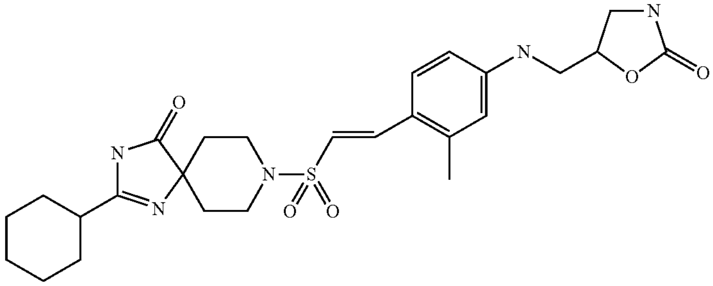 [SMILES: Cc1cc(NCC2CNC(=O)O2)ccc1/C=C/S(=O)(=O)N1CCC2(CC1)N=C(C1CCCCC1)NC2=O] | LCMS-C-1 | 2.23 | 530 (M + H)+ |
| 208 | 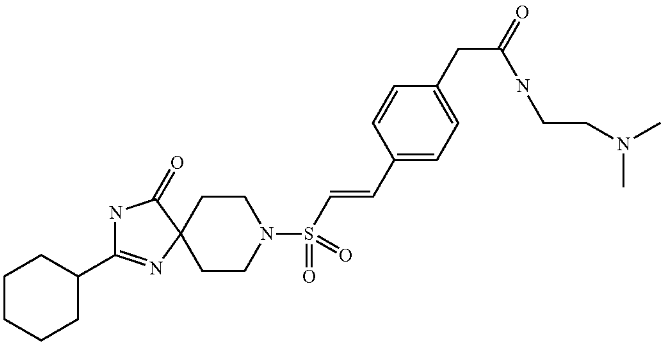 [SMILES: CN(C)CCNC(=O)Cc1ccc(/C=C/S(=O)(=O)N2CCC3(CC2)N=C(C2CCCCC2)NC3=O)cc1] | LCMS-C-1 | 2.12 | 530 (M + H)+ |

The aryl bromide reagent used in the synthesis of Compound 204 (N-(4-bromo-3,5-dimethyl-phenyl)-acetamide) was synthesized as follows.

(Reaction 26-2)

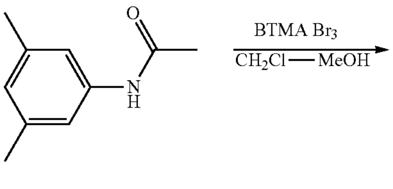

26b

-continued

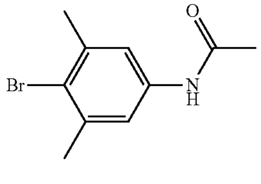

26a

Benzyltrimethylammonium tribromide (BTMA-$Br_3$) (7.8 g, 20.21 mmol) was added to a solution of N-(3,5-dimethyl-phenyl)-acetamide (3.0 g, 18.38 mmol) in $CH_2Cl_2$/MeOH (90 ml/90 ml) at room temperature in an Ar atmosphere. The reaction mixture was stirred at room temperature for 10 minutes. The reaction mixture was concentrated under reduced pressure, and $CH_2Cl_2$ was then added to the resulting residue. The organic layer was washed with $H_2O$, and then dried over anhydrous $Na_2SO_4$ and concentrated under reduced pressure. The residue was purified by silica gel column chromatography (hexane:EtOAc=1:1) to give N-(4-bromo-3,5-dimethyl-phenyl)-acetamide (4.0 g, yield 90%).

MS (ESI+) m/z=242, 244 (M+H)+.

The aryl bromide reagent used in the synthesis of Compound 205 ((4-bromo-3-methyl-benzyl)-carbamic acid tert-butyl ester) was synthesized as follows.

(Reaction 26-3)

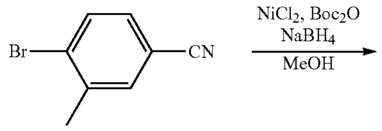

26c

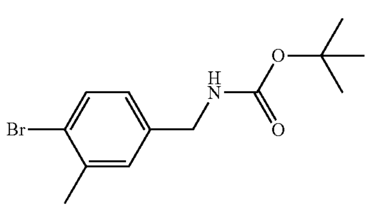

26d $NaBH_4$ (1.45 g, 38.25 mmol) was added in small portions to a mixture of 4-bromo-3-methyl-benzonitrile (2.50 g, 12.8 mmol), $NiCl_2$ (1.65 g, 12.8 mmol) and $Boc_2O$ (5.57 g, 25.5 mmol) in anhydrous MeOH (130 ml) at 0° C. The reaction mixture was stirred at room temperature for two hours and then concentrated under reduced pressure. Ethyl acetate and water were added to the resulting residue, and the mixture was filtered through celite. The organic layer and the aqueous layer were separated, and the aqueous layer was then extracted with ethyl acetate. The organic layers were combined, dried over $Na_2SO_4$ and then concentrated under reduced pressure. The residue was purified by silica gel column chromatography (hexane/ethyl acetate=1/0→4/1) to give (4-bromo-3-methyl-benzyl)-carbamic acid tert-butyl ester as a white solid (2.42 g, 63%).

MS (ESI) m/z=322 (M+Na)+.

The aryl bromide reagent used in the synthesis of Compound 206 ((R)-3-(4-bromo-3,5-dimethyl-phenoxy)-propane-1,2-diol) was synthesized as follows.

(Reaction 26-4)

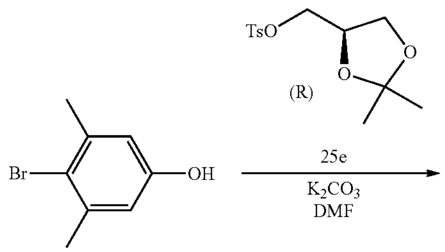

26e

-continued

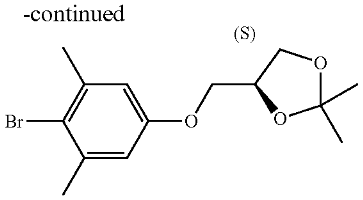

26f

A mixture of 4-bromo-3,5-dimethyl-phenol (500 mg, 2.49 mmol), (R)-(−)-2,2-dimethyl-1,3-dioxolan-4-ylmethyl p-toluenesulfonate (856 mg, 2.99 mmol) and $K_2CO_3$ (1.03 g, 7.45 mmol) in dimethylformamide (5 ml) was stirred at 100° C. for two hours. The reaction mixture was diluted with AcOEt, and the organic layer was then washed with water (×2), dried over sodium sulfate and concentrated under reduced pressure. The resulting residue was purified by silica gel column chromatography (AcOEt-hexane) to give (S)-4-(4-bromo-3,5-dimethyl-phenoxymethyl)-2,2-dimethyl-[1,3]dioxolane as a colorless solid (749 mg, 95%).

$^1$H-NMR (400 MHz, $CDCl_3$) δ 1.40 (3H, s), 1.46 (3H, s), 2.37 (6H, s), 3.85-3.92 (2H, m), 3.98-4.03 (1H, m), 4.13-4.18 (1H, m), 4.42-4.48 (1H, m), 6.66 (2H, s).

(Reaction 26-5)

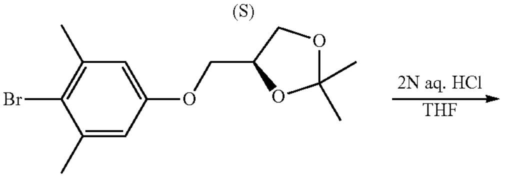

26f

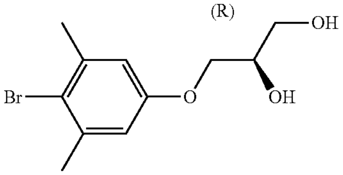

26g (R)-3-(4-Bromo-3,5-dimethyl-phenoxy)-propane-1,2-diol was synthesized by operations similar to those in Reaction 25-4 using appropriate reagents and starting material.

MS (ESI) m/z=275, 277 (M+H)+.

The aryl bromide reagent used in the synthesis of Compound 207 (5-[(4-bromo-3-methyl-phenylamino)-methyl]-oxazolidin-2-one) was synthesized as follows.

(Reaction 26-6)

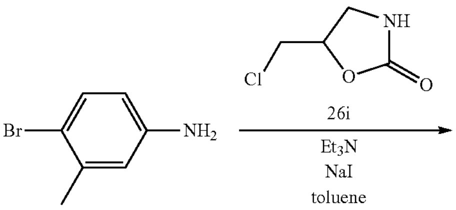

26h

-continued

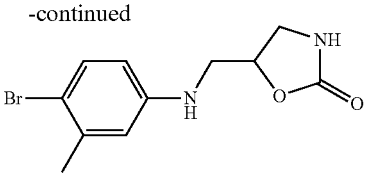

26j

5-[(4-Bromo-3-methyl-phenylamino)-methyl]-oxazolidin-2-one was synthesized by operations similar to those in Reaction 25-12 using appropriate reagents and starting material.

MS (ESI) m/z=285, 287 (M+H)+.

The aryl bromide reagent used in the synthesis of Compound 208 (2-(4-bromo-phenyl)-N-(2-dimethylamino-ethyl) acetamide) was synthesized as follows.

(Reaction 26-7)

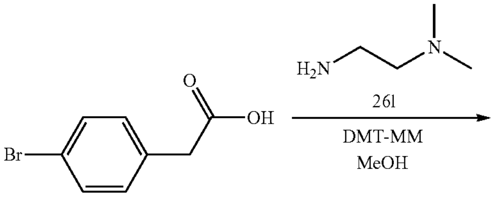

26k

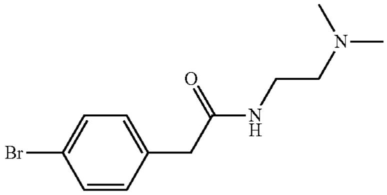

26m 2-(4-Bromo-phenyl)-N-(2-dimethylamino-ethyl)acetamide was synthesized by operations similar to those in Reaction 10-1 using appropriate reagents and starting material.

MS (ESI) m/z=285, 287 (M+H)+.

Example 27

3-{(E)-2-[2-(4-Methyl-cyclohexyl)-4-oxo-1,3,8-triaza-spiro[4.5]dec-1-ene-8-sulfonyl]-vinyl}-benzonitrile (Compound 209)

(Reaction 27-1)

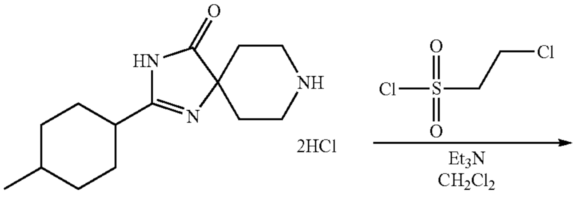

27a

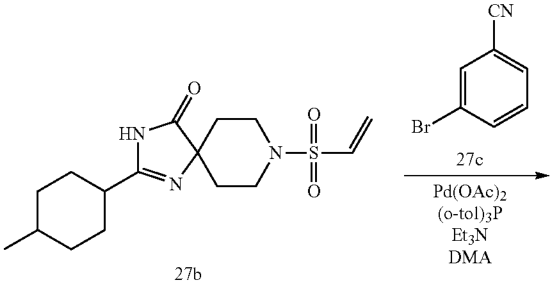

27b

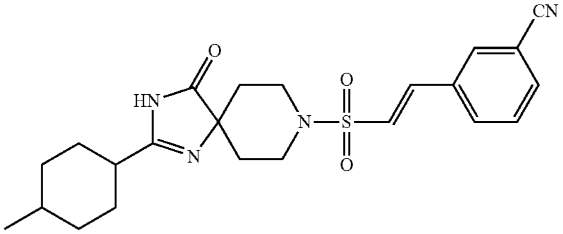

Compound 209

3-{(E)-2-[2-(4-Methyl-cyclohexyl)-4-oxo-1,3,8-triaza-spiro[4.5]dec-1-ene-8-sulfonyl]-vinyl}-benzonitrile was synthesized by operations similar to those in Reaction 25-1 and Reaction 25-2 using appropriate reagents and starting material.

MS (ESI) m/z=441 (M+H)+.

Example 28

8-{(E)-2-[4-(3,4-Dihydroxy-butoxy)-2-methyl-phenyl]-ethenesulfonyl}-2-(3-trifluoromethyl-phenyl)-1,3,8-triaza-spiro[4.5]dec-1-en-4-one (Compound 210)

(Reaction 28-1)

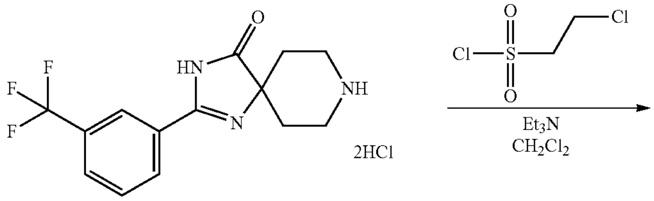

8d

-continued

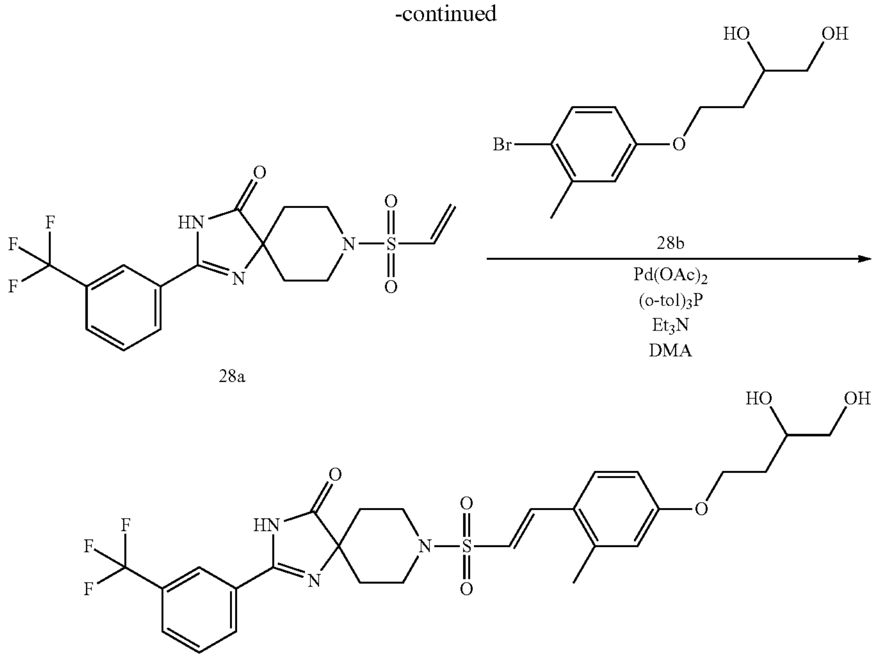

Compound 210

8-{(E)-2-[4-(3,4-Dihydroxy-butoxy)-2-methyl-phenyl]-ethenesulfonyl}-2-(3-trifluoromethyl-phenyl)-1,3,8-triaza-spiro[4.5]dec-1-en-4-one was synthesized by operations similar to those in Reaction 25-1 and Reaction 25-2 using appropriate reagents and starting material.

MS (ESI) m/z=441 (M+H)+.

The example compounds shown below were synthesized by operations similar to those in Example 28 using appropriate reagents and starting materials.

Compounds 211 to 214

TABLE 33

| Compound | Structure | LCMS or HPLC condition | Retention time (min) | MS (m/z) |
|---|---|---|---|---|
| 211 | 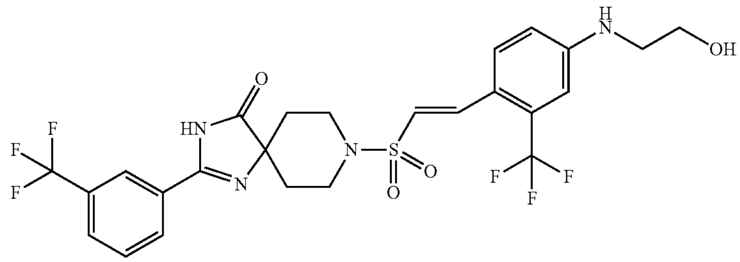 [SMILES: O=C1NC(c2cccc(C(F)(F)F)c2)=NC12CCN(S(=O)(=O)/C=C/c1ccc(NCCO)cc1C(F)(F)F)CC2] | LCMS-C-2 | 2.02 | 591 (M + H)+ |
| 212 | 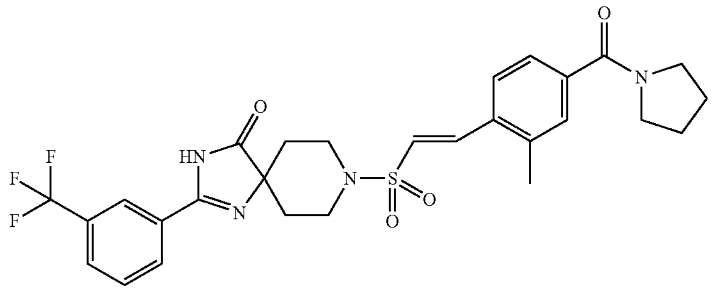 [SMILES: Cc1cc(C(=O)N2CCCC2)ccc1/C=C/S(=O)(=O)N1CCC2(CC1)N=C(c1cccc(C(F)(F)F)c1)NC2=O] | LCMS-B-1 | 2.25 | 575 (M + H)+ |

TABLE 33-continued

| Compound | Structure | LCMS or HPLC condition | Retention time (min) | MS (m/z) |
|---|---|---|---|---|
| 213 | 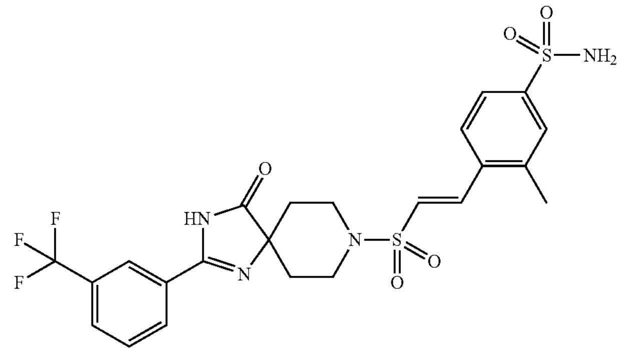 [SMILES: Cc1cc(S(N)(=O)=O)ccc1/C=C/S(=O)(=O)N1CCC2(CC1)N=C(c1cccc(C(F)(F)F)c1)NC2=O] | LCMS-C-1 | 2.37 | 557 (M + H)+ |
| 214 | 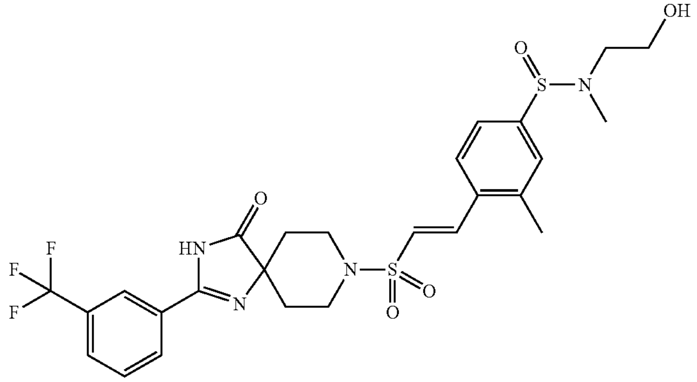 | LCMS-C-1 | 2.42 | 579 (M + H)+ |

The aryl bromide reagent used in the synthesis of Compound 210 (4-(4-bromo-3-methyl-phenoxy)-butane-1,2-diol) was synthesized as follows.

(Reaction 28-2)

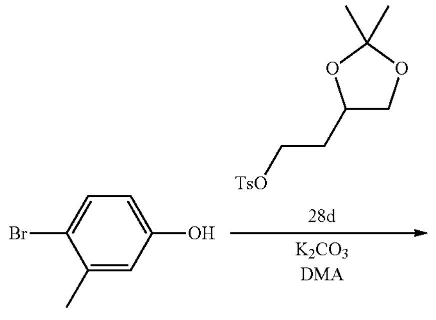

28c

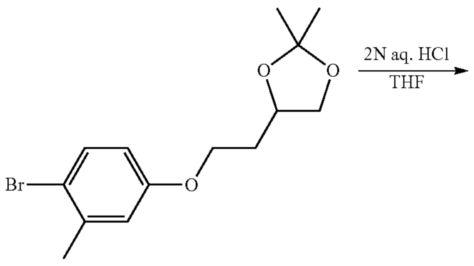

28e

-continued

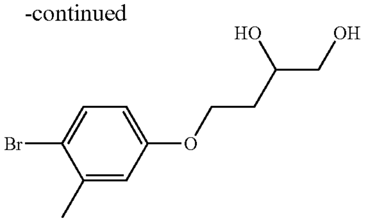

28b 4-(4-Bromo-3-methyl-phenoxy)-butane-1,2-diol was synthesized by operations similar to those in Reaction 26-4 and Reaction 25-4 using appropriate reagents and starting material.

MS (ESI) m/z=275, 277 (M+H)+.

The aryl bromide reagent used in the synthesis of Compound 211 (2-(4-bromo-3-trifluoromethyl-phenylamino)-ethanol) was synthesized as follows.

(Reaction 28-3)

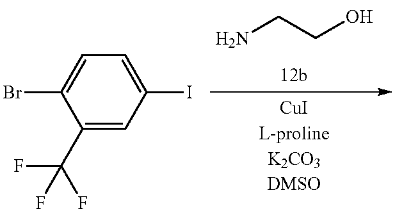

28f

-continued

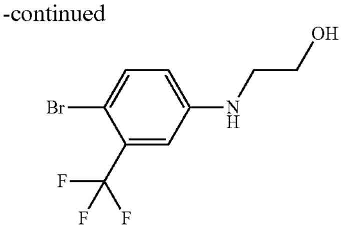

28g 2-(4-Bromo-3-trifluoromethyl-phenylamino)-ethanol was synthesized by operations similar to those in Reaction 12-1 using appropriate reagents and starting material.

MS (ESI) m/z=284, 286 (M+H)+.

The aryl bromide reagent used in the synthesis of Compound 212 ((4-bromo-3-methyl-phenyl)-pyrrolidin-1-yl-methanone) was synthesized as follows.

(Reaction 28-4)

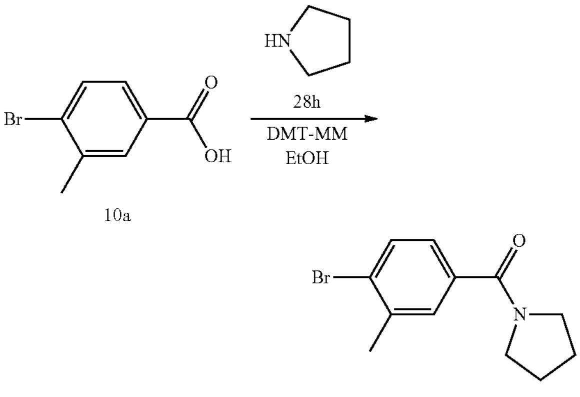

10a

28i (4-Bromo-3-methyl-phenyl)-pyrrolidin-1-yl-methanone was synthesized by operations similar to those in Reaction 10-1 using appropriate reagents and starting material.

MS (ESI) m/z=268, 270 (M+H)+.

The aryl bromide reagent used in the synthesis of Compound 213 (4-bromo-3-methyl-benzenesulfonamide) was synthesized as follows.

(Reaction 28-5)

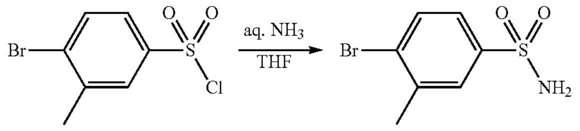

28j 28k

A 28% aqueous $NH_3$ solution (2.0 ml) was added to a solution of 4-bromo-3-methyl-benzenesulfonyl chloride (250 mg, 0.927 mmol) in THF (2.0 ml) at 0° C. The mixture was stirred at 0° C. for 6.5 hours. The reaction mixture was quenched with 1 N HCl and extracted with $CH_2Cl_2$. The organic layer was concentrated under reduced pressure, and the resulting residue was purified by silica gel column chromatography ($CH_2Cl_2$—AcOEt) to give 4-bromo-3-methyl-benzenesulfonamide as a white powder (126 mg, 54%).

MS (ESI) m/z=272, 274 (M+Na)+.

The aryl bromide reagent used in the synthesis of Compound 214 (4-bromo-N-(2-hydroxy-ethyl)-3,N-dimethyl-benzamide) was synthesized as follows.

(Reaction 28-6)

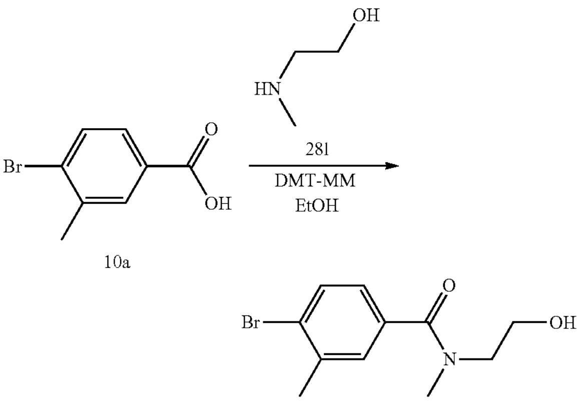

10a

28m

4-Bromo-N-(2-hydroxy-ethyl)-3,N-dimethyl-benzamide was synthesized by operations similar to those in Reaction 10-1 using appropriate reagents and starting material.

MS (ESI) m/z=272, 274 (M+H)+.

Example 29

N-(3-Methyl-4-{(E)-2-[4-oxo-2-(3-trifluoromethyl-phenyl)-1,3,8-triaza-spiro[4.5]dec-1-ene-8-sulfonyl]-vinyl}-phenyl)-acetamide (Compound 215)

(Reaction 29-1)

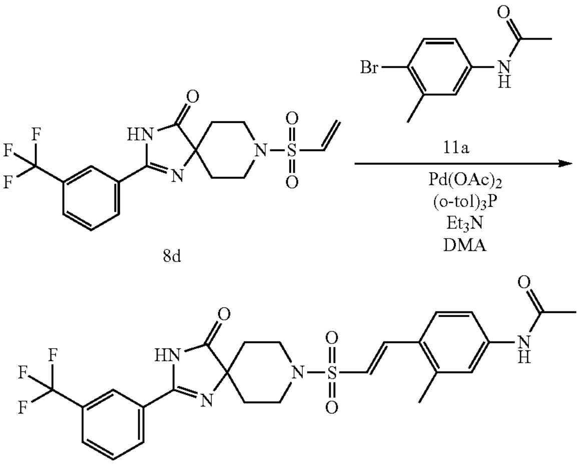

8d

Compound 215

N-(3-Methyl-4-{(E)-2-[4-oxo-2-(3-trifluoromethyl-phenyl)-1,3,8-triaza-spiro[4.5]dec-1-ene-8-sulfonyl]-vinyl}-phenyl)-acetamide was synthesized by operations similar to those in Reaction 26-1 using appropriate reagents and starting material.

MS (ESI) m/z=535 (M+H)+.

The example compounds shown below were synthesized by operations similar to those in Example 29 using appropriate reagents and starting materials.

Compounds 216 to 223
TABLE 34
| Compound | Structure | LCMS or HPLC condition | Retention time (min) | MS (m/z) |
|---|---|---|---|---|
| 216 | 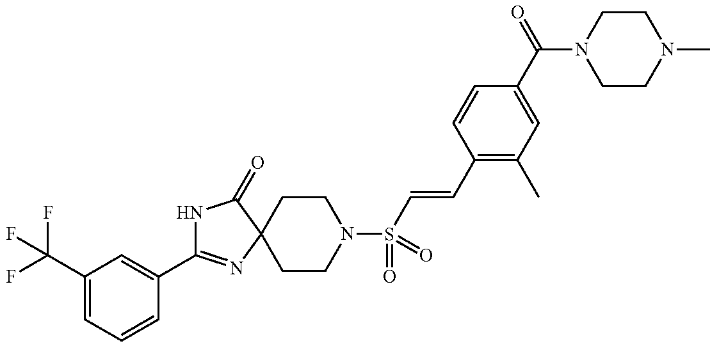 [SMILES: Cc1cc(C(=O)N2CCN(C)CC2)ccc1/C=C/S(=O)(=O)N1CCC2(CC1)N=C(c1cccc(C(F)(F)F)c1)NC2=O] | LCMS-C-1 | 2.55 | 604 (M + H)+ |
| 217 | 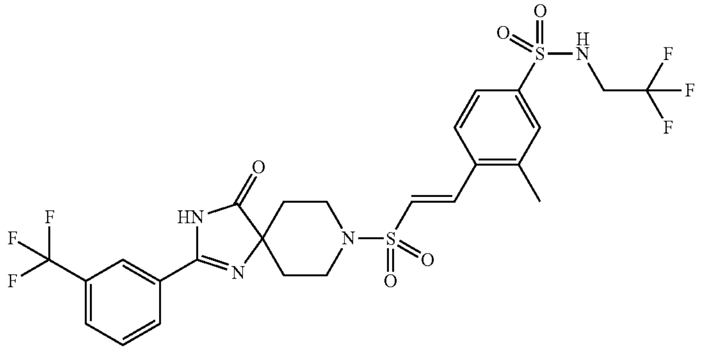 [SMILES: Cc1cc(S(=O)(=O)NCC(F)(F)F)ccc1/C=C/S(=O)(=O)N1CCC2(CC1)N=C(c1cccc(C(F)(F)F)c1)NC2=O] | LCMS-C-1 | 2.70 | 639 (M + H)+ |
| 218 | 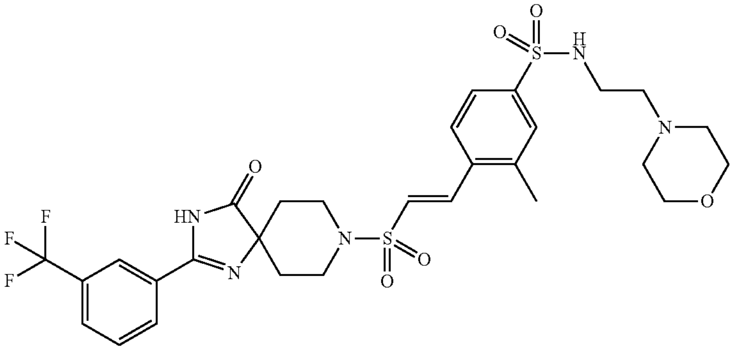 [SMILES: Cc1cc(S(=O)(=O)NCCN2CCOCC2)ccc1/C=C/S(=O)(=O)N1CCC2(CC1)N=C(c1cccc(C(F)(F)F)c1)NC2=O] | LCMS-C-1 | 2.57 | 670 (M + H)+ |
| 219 | 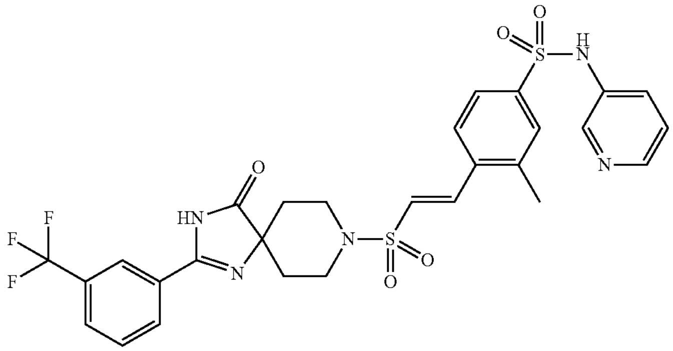 [SMILES: Cc1cc(S(=O)(=O)Nc2cccnc2)ccc1/C=C/S(=O)(=O)N1CCC2(CC1)N=C(c1cccc(C(F)(F)F)c1)NC2=O] | LCMS-C-1 | 1.95 | 634 (M + H)+ |

TABLE 34-continued
| Compound | Structure | LCMS or HPLC condition | Retention time (min) | MS (m/z) |
|---|---|---|---|---|
| 220 | 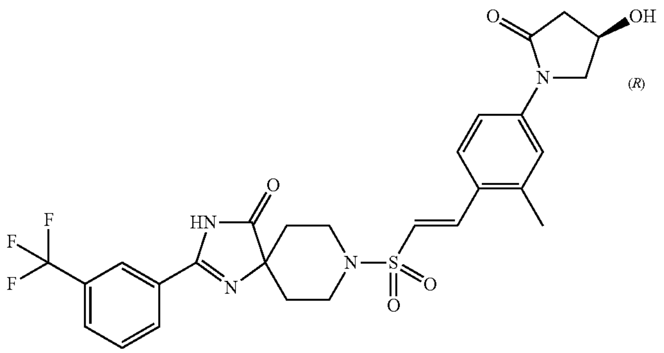 | LCMS-C-1 | 2.42 | 577 (M + H)+ |
| 221 | 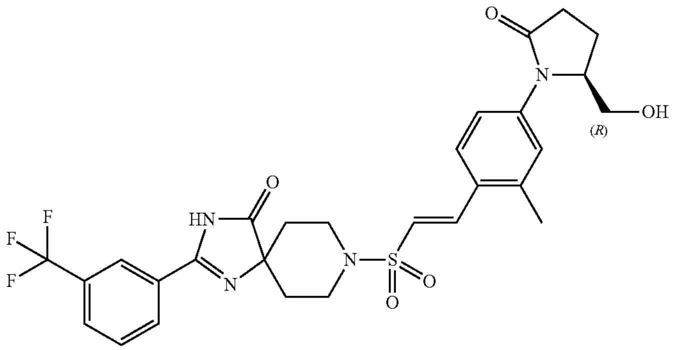 | LCMS-C-1 | 2.42 | 591 (M + H)+ |
| 222 | 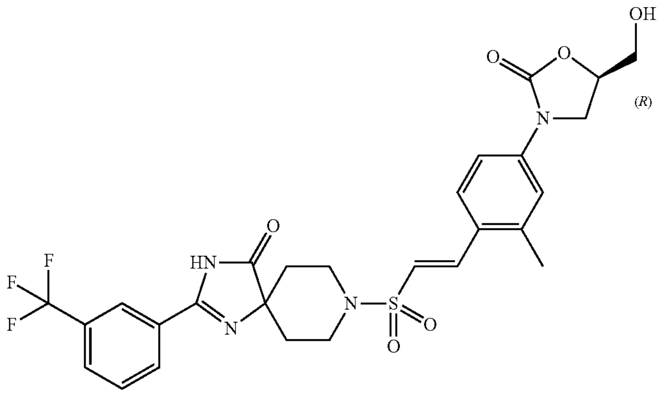 | LCMS-C-1 | 2.45 | 593 (M + H)+ |
| 223 | 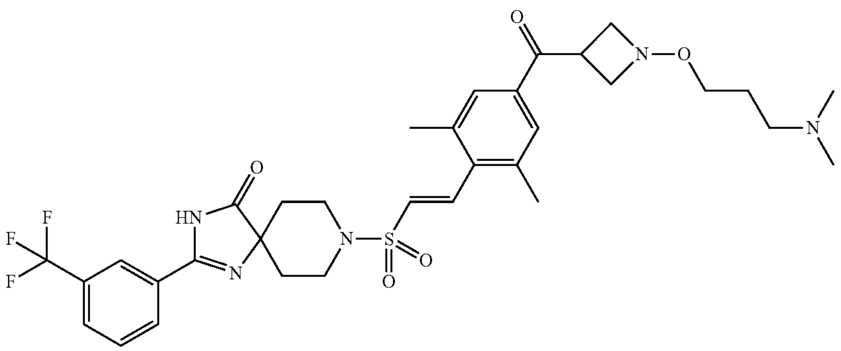 [SMILES: Cc1cc(C(=O)C2CN(OCCCN(C)C)C2)cc(C)c1/C=C/S(=O)(=O)N1CCC2(CC1)N=C(c1cccc(C(F)(F)F)c1)NC2=O] | LCMS-C-1 | 2.50 | 676 (M + H)+ |

The aryl bromide reagent used in the synthesis of Compound 216 ((4-bromo-3-methyl-phenyl)-(4-methyl-piperazin-1-yl)-methanone) was synthesized as follows.

(Reaction 29-2)

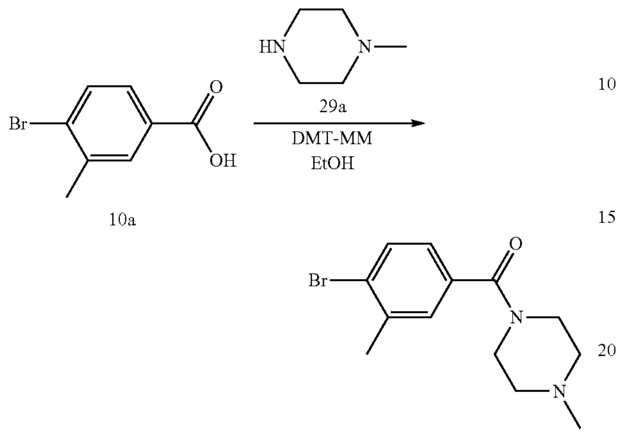

10a

29b (4-Bromo-3-methyl-phenyl)-(4-methyl-piperazin-1-yl)-methanone was synthesized by operations similar to those in Reaction 10-1 using appropriate reagents and starting material.

MS (ESI) m/z=297, 299 (M+H)+.

The aryl bromide reagents used in the synthesis of Compounds 217 to 219 were synthesized by operations similar to those in Reaction 28-5 using appropriate reagents and starting materials.

TABLE 35

| Compound | Structure | Aryl bromide reagent MZ (m/z) |
|---|---|---|
| 217 | 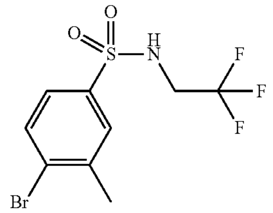 [SMILES: Cc1cc(S(=O)(=O)NCC(F)(F)F)ccc1Br] | 354, 355 (M + Na)+ |
| 218 | 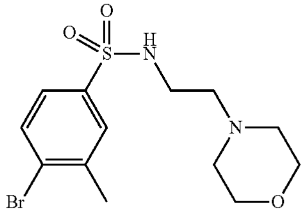 [SMILES: Cc1cc(S(=O)(=O)NCCN2CCOCC2)ccc1Br] | 363, 365 (M + H)+ |
| 219 | 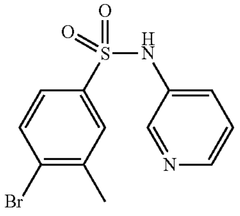 [SMILES: Cc1cc(S(=O)(=O)Nc2cccnc2)ccc1Br] | 327, 329 (M + H)+ |

The aryl bromide reagent used in the synthesis of Compound 220 ((R)-1-(4-bromo-3-methyl-phenyl)-4-hydroxy-pyrrolidin-2-one) was synthesized as follows.

(Reaction 29-3)

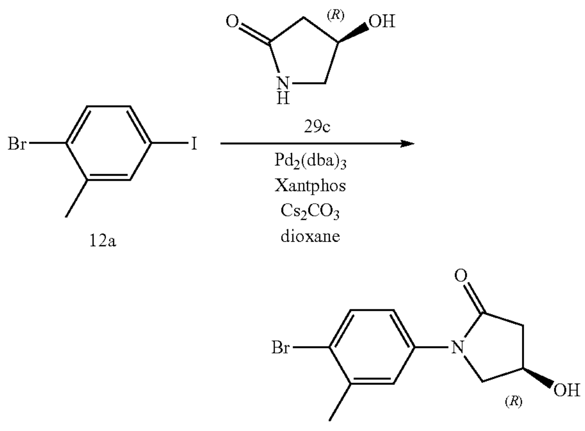

12a

29d

A mixture of 2-bromo-5-iodotoluene (500 mg, 1.68 mmol), (R)-4-hydroxy-pyrrolidinone (204 mg, 2.02 mmol), 4,5-bis(diphenylphosphino)-9,9-dimethylxanthene (58.5 mg, 0.101 mmol), tris(dibenzylideneacetone)-dipalladium (0)-chloroform adduct (35.0 mg, 0.034 mmol) and cesium carbonate (769 mg, 2.36 mmol) in 1,4-dioxane (degassed, 5 ml) was stirred at 110° C. overnight in a nitrogen stream. The reaction mixture was treated with $H_2O$ and extracted with AcOEt (×2). The organic layers were combined and sequentially washed with $H_2O$ and saturated brine, and then dried over $Na_2SO_4$ and concentrated under reduced pressure. The resulting residue was purified by silica gel chromatography (n-hexane/AcOEt) to give (R)-1-(4-bromo-3-methyl-phenyl)-4-hydroxy-pyrrolidin-2-one as a pale brown solid (173 mg, 38%).

$^1$H-NMR (400 MHz, DMSO-d6) δ 2.29 (1H, d, J=17.1 Hz), 2.34 (3H, s), 2.82 (1H, dd, J=17.1, 6.4 Hz), 3.57 (1H, d, J=10.3 Hz), 4.01 (1H, dd, J=10.3, 4.9 Hz), 4.36-4.40 (1H, m), 5.35 (1H, d, J=3.4 Hz, OH), 7.51 (1H, dd, J=8.8, 2.4 Hz), 7.55 (1H, d, J=8.8 Hz), 7.62 (1H, br. s). MS (ESI) m/z=270, 272 (M+H)+.

The aryl bromide reagent used in the synthesis of Compound 221 ((R)-1-(4-bromo-3-methyl-phenyl)-5-hydroxymethyl-pyrrolidin-2-one) was synthesized as follows.

(Reaction 29-4)

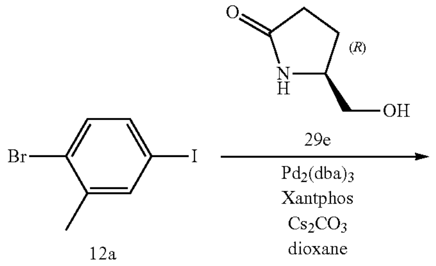

12a

-continued

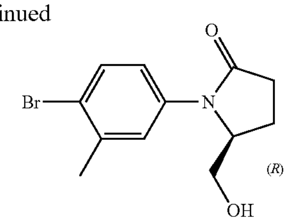

29f (R)-1-(4-Bromo-3-methyl-phenyl)-5-hydroxymethyl-pyrrolidin-2-one was synthesized by operations similar to those in Reaction 29-3 using appropriate reagents and starting material.

MS (ESI) m/z=284, 286 (M+H)+.

The aryl bromide reagent used in the synthesis of Compound 222 ((R)-3-(4-bromo-3-methyl-phenyl)-5-hydroxymethyl-oxazolidin-2-one) was synthesized as follows.

(Reaction 29-5)

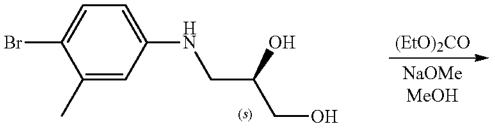

29g

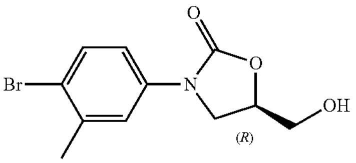

29h

A mixture of (S)-3-(4-bromo-3-methyl-phenylamino)-propane-1,2-diol (202 mg, 0.777 mmol), diethyl carbonate (3 ml), sodium methoxide (28% in MeOH, 0.160 ml) and MeOH (4 ml) was stirred at 130° C. overnight. The reaction mixture was treated with saturated $NH_4Cl$ and $H_2O$ and extracted with AcOEt (×2). The organic layers were combined and sequentially washed with $H_2O$ and saturated brine, and then dried over $Na_2SO_4$ and concentrated under reduced pressure. The resulting residue was purified by silica gel column chromatography (n-hexane/AcOEt) to give (R)-3-(4-bromo-3-methyl-phenyl)-5-hydroxymethyl-oxazolidin-2-one (170 mg, 77%).

$^1$H-NMR (400 MHz, DMSO-d6) δ 2.35 (3H, s), 3.53-3.57 (1H, m), 3.65-3.68 (1H, m), 3.82 (1H, dd, J=8.8, 6.4 Hz), 4.06 (1H, dd, J=9.3, 8.8 Hz), 4.67-4.72 (1H, m), 5.22 (1H, br. s), 7.42 (1H, dd, J=8.8, 2.9 Hz), 7.54 (1H, d, J=2.5 Hz), 7.56 (1H, d, J=8.8 Hz). MS (ESI) m/z=286, 288 (M+H)+.

The aryl bromide reagent used in the synthesis of Compound 223 ((4-bromo-3,5-dimethyl-phenyl)-[3-(3-dimethylamino-propoxy)-azetidin-1-yl]-methanone) was synthesized as follows.

(Reaction 29-6)

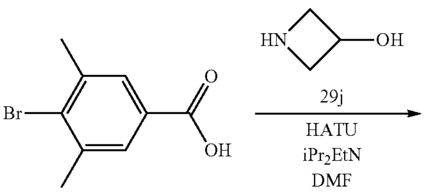

29i

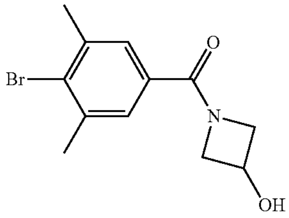

29k (4-Bromo-3,5-dimethyl-phenyl)-(3-hydroxy-azetidin-1-yl)-methanone was synthesized by operations similar to those in Reaction 10-14 using appropriate reagents and starting material.

MS (ESI) m/z=284, 286 (M+H)+.

(Reaction 29-7)

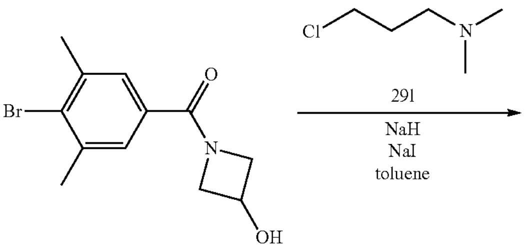

29k

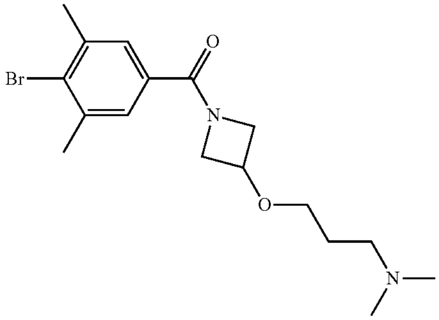

29m

NaH (110 mg, 2.75 mmol, 60% oily suspension) and NaI (274 mg, 1.83 mmol) were added to a solution of (4-bromo-3,5-dimethyl-phenyl)-(3-hydroxy-azetidin-1-yl)-methanone (130 mg, 0.458 mmol) and (3-chloro-propyl)-dimethyl-amine (289 mg, 1.83 mmol) in toluene (1.8 ml). The mixture was stirred at 110° C. for 15 hours. The reaction mixture was diluted with AcOEt, and the organic layer was then sequentially washed with a saturated aqueous $NaHCO_3$ solution, water and a saturated aqueous NaCl solution. Further, the organic layer was dried over sodium sulfate and then concentrated under reduced pressure. The resulting residue was purified by silica gel column chromatography (n-hexane/AcOEt) to give (4-bromo-3,5-dimethyl-phenyl)-[3-(3-dimethylamino-propoxy)-azetidin-1-yl]-methanone (46 mg, 27%).

MS (ESI) m/z=369, 371 (M+H)+.

Example 30

N-(3-Hydroxy-propyl)-3-methyl-4-{(E)-2-[4-oxo-2-(3-trifluoromethoxy-phenyl)-1,3,8-triaza-spiro[4.5]dec-1-ene-8-sulfonyl]-vinyl}-benzenesulfonamide (Compound 224)

(Reaction 30-1)

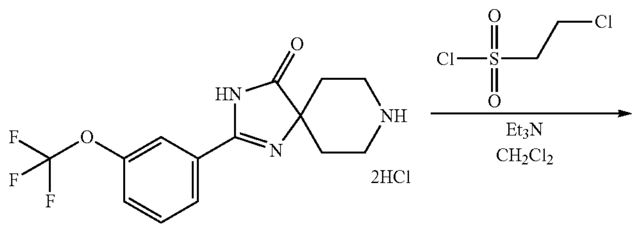

12i

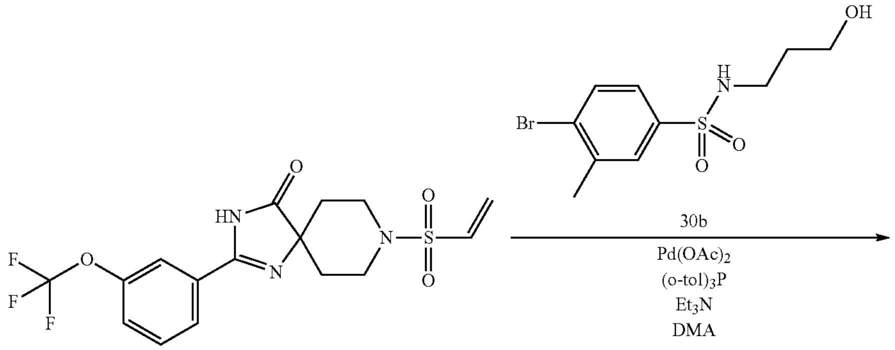

30a

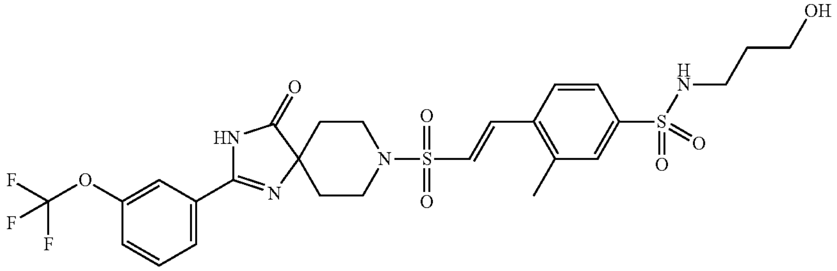

Compound 224

N-(3-Hydroxy-propyl)-3-methyl-4-{(E)-2-[4-oxo-2-(3-trifluoromethoxy-phenyl)-1,3,8-triaza-spiro[4.5]dec-1-ene-8-sulfonyl]-vinyl}-benzenesulfonamide was synthesized by operations similar to those in Reaction 25-1 and Reaction 25-2 using appropriate reagents and starting material.

MS (ESI) m/z=645 (M+H)+.

The example compound shown below was synthesized by operations similar to those in Example 30 using appropriate reagents and starting material.

Compound 225

TABLE 36

| Compound | Structure | LCMS or HPLC condition | Retention time (min) | MS (m/z) |
|---|---|---|---|---|
| 225 | 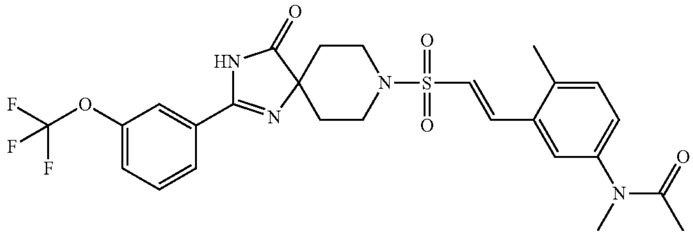 [SMILES: CC(=O)N(C)c1ccc(C)c(/C=C/S(=O)(=O)N2CCC3(CC2)N=C(c2cccc(OC(F)(F)F)c2)NC3=O)c1] | LCMS-D-1 | 3.3 | 567 (M + H)+ |

The aryl bromide reagent used in the synthesis of Compound 224 (4-bromo-N-(3-hydroxy-propyl)-3-methyl-benzenesulfonamide) was synthesized as follows.

(Reaction 30-2)

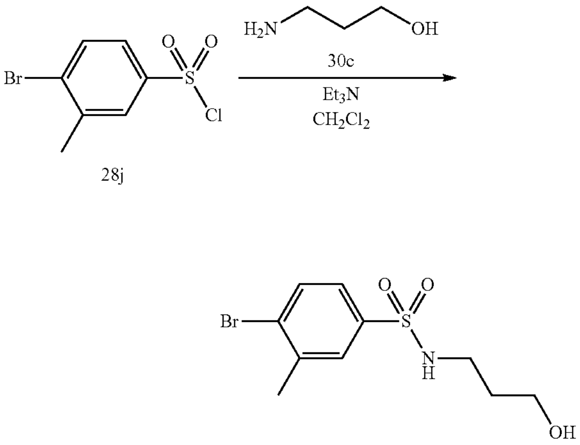

28j

30b

4-Bromo-N-(3-hydroxy-propyl)-3-methyl-benzenesulfonamide was synthesized by operations similar to those in Reaction 5-4 using appropriate reagents and starting material.

MS (ESI) m/z=322, 324 (M+H)+.

The aryl bromide reagent used in the synthesis of Compound 225 (N-(3-bromo-4-methyl-phenyl)-N-methyl-acetamide) was synthesized as follows.

(Reaction 30-3)

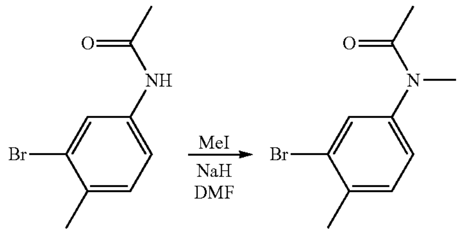

30d

30e

N-(3-Bromo-4-methyl-phenyl)-N-methyl-acetamide was synthesized by operations similar to those in Reaction 25-3 using appropriate reagents and starting material.

MS (ESI) m/z=242, 244 (M+H)+.

Example 31

8-[(E)-2-(3-Hydroxy-2-methyl-phenyl)-ethenesulfonyl]-2-(3-trifluoromethoxy-phenyl)-1,3,8-triaza-spiro[4.5]dec-1-en-4-one (Compound 226)

(Reaction 31-1)

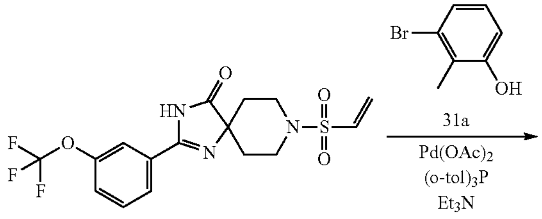

30a

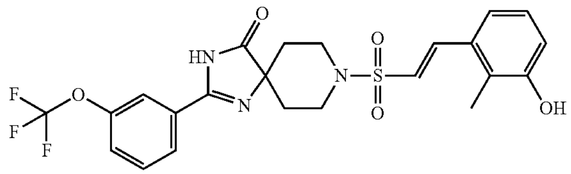

Compound 226

8-[(E)-2-(3-Hydroxy-2-methyl-phenyl)-ethenesulfonyl]-2-(3-trifluoromethoxy-phenyl)-1,3,8-triaza-spiro[4.5]dec-1-en-4-one was synthesized by operations similar to those in Reaction 25-2 using appropriate reagents and starting material.

MS (ESI) m/z=510 (M+H)+.

The example compounds shown below were synthesized by operations similar to those in Example 31 using appropriate reagents and starting materials.

Compounds 227 to 239

TABLE 37

| Compound | Structure | LCMS or HPLC condition | Retention time (min) | MS (m/z) |
|---|---|---|---|---|
| 227 | 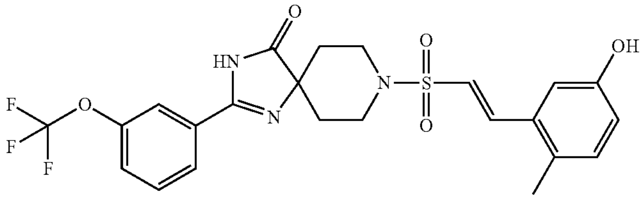 [SMILES: Cc1ccc(O)cc1/C=C/S(=O)(=O)N1CCC2(CC1)N=C(c1cccc(OC(F)(F)F)c1)NC2=O] | HPLC-A-2 | 11.5 | 510 (M + H)+ |

TABLE 37-continued
| Compound | Structure | LCMS or HPLC condition | Retention time (min) | MS (m/z) |
|---|---|---|---|---|
| 228 | 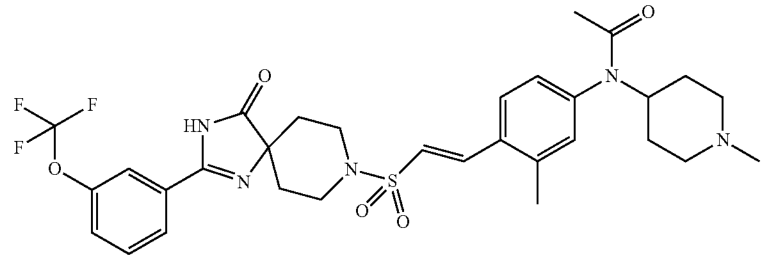 [SMILES: CC(=O)N(c1ccc(/C=C/S(=O)(=O)N2CCC3(CC2)N=C(c2cccc(OC(F)(F)F)c2)NC3=O)c(C)c1)C1CCN(C)CC1] | HPLC-A-1 | 2.12 | 648 (M + H)+ |
| 229 | 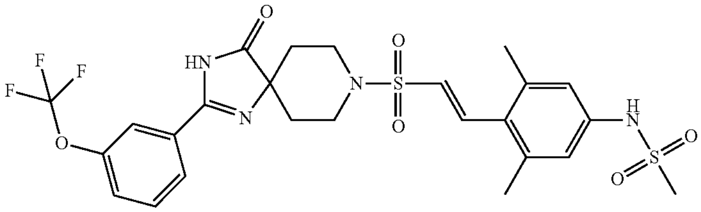 [SMILES: Cc1cc(NS(C)(=O)=O)cc(C)c1/C=C/S(=O)(=O)N1CCC2(CC1)N=C(c1cccc(OC(F)(F)F)c1)NC2=O] | LCMS-D-1 | 3.3 | 601 (M + H)+ |
| 230 | 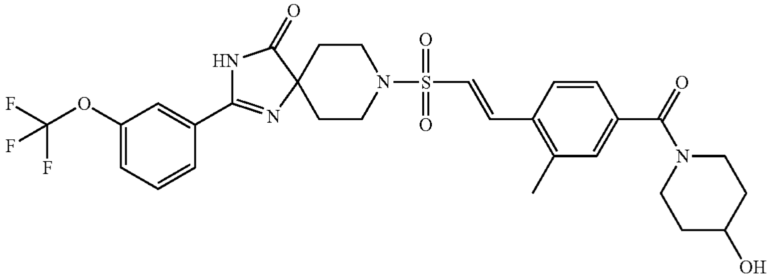 [SMILES: Cc1cc(C(=O)N2CCC(O)CC2)ccc1/C=C/S(=O)(=O)N1CCC2(CC1)N=C(c1cccc(OC(F)(F)F)c1)NC2=O] | LCMS-A-1 | 2.25 | 621 (M + H)+ |
| 231 | 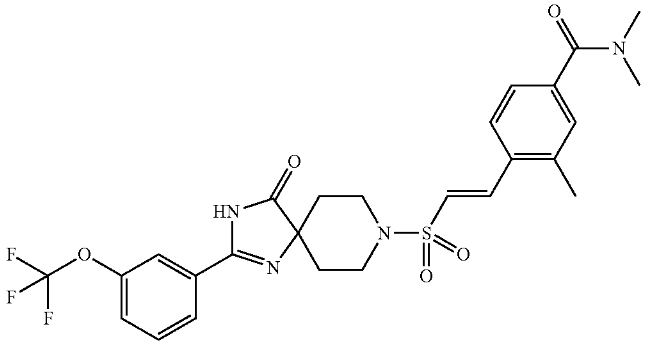 [SMILES: Cc1cc(C(=O)N(C)C)ccc1/C=C/S(=O)(=O)N1CCC2(CC1)N=C(c1cccc(OC(F)(F)F)c1)NC2=O] | LCMS-C-1 | 2.60 | 565 (M + H)+ |
| 232 | 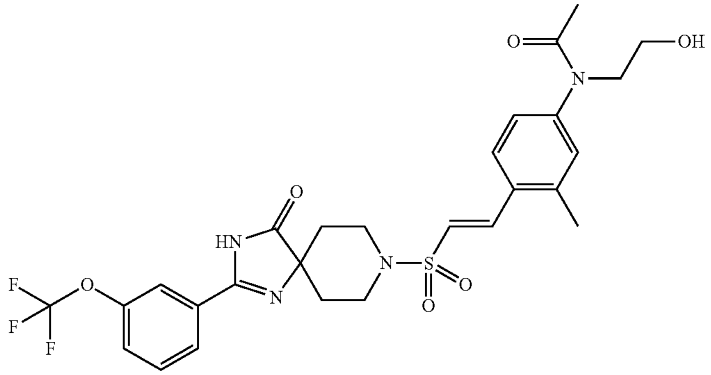 [SMILES: CC(=O)N(CCO)c1ccc(/C=C/S(=O)(=O)N2CCC3(CC2)N=C(c2cccc(OC(F)(F)F)c2)NC3=O)c(C)c1] | LCMS-C-1 | 2.52 | 595 (M + H)+ |

TABLE 37-continued
| Compound | Structure | LCMS or HPLC condition | Retention time (min) | MS (m/z) |
|---|---|---|---|---|
| 233 | 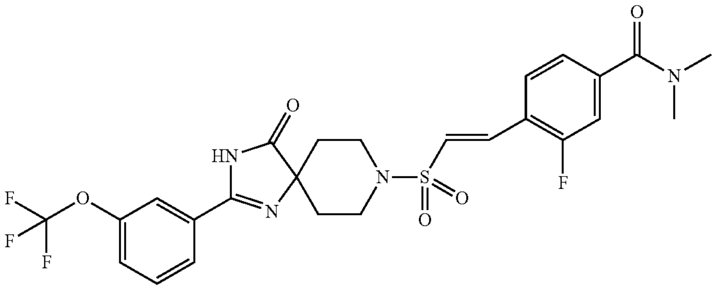 [SMILES: CN(C)C(=O)c1ccc(/C=C/S(=O)(=O)N2CCC3(CC2)N=C(c2cccc(OC(F)(F)F)c2)NC3=O)c(F)c1] | LCMS-C-1 | 2.57 | 567 (M + H)+ |
| 234 | 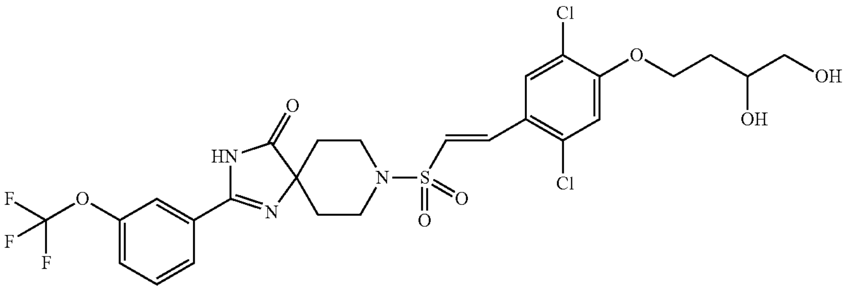 [SMILES: O=C1NC(c2cccc(OC(F)(F)F)c2)=NC12CCN(S(=O)(=O)/C=C/c1cc(Cl)c(OCCC(O)CO)cc1Cl)CC2] | LCMS-C-1 | 2.73 | 652 (M + H)+ |
| 235 | 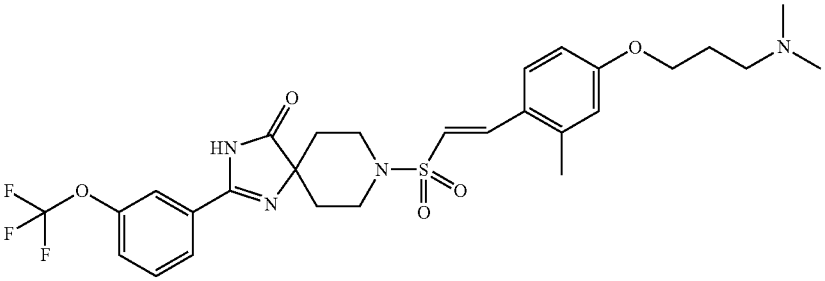 [SMILES: Cc1cc(OCCCN(C)C)ccc1/C=C/S(=O)(=O)N1CCC2(CC1)N=C(c1cccc(OC(F)(F)F)c1)NC2=O] | LCMS-C-1 | 2.67 | 595 (M + H)+ |
| 236 | 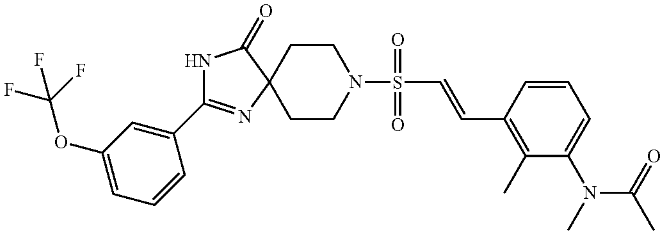 [SMILES: CC(=O)N(C)c1cccc(/C=C/S(=O)(=O)N2CCC3(CC2)N=C(c2cccc(OC(F)(F)F)c2)NC3=O)c1C] | LCMS-D-1 | 3.1 | 565 (M + H)+ |
| 237 | 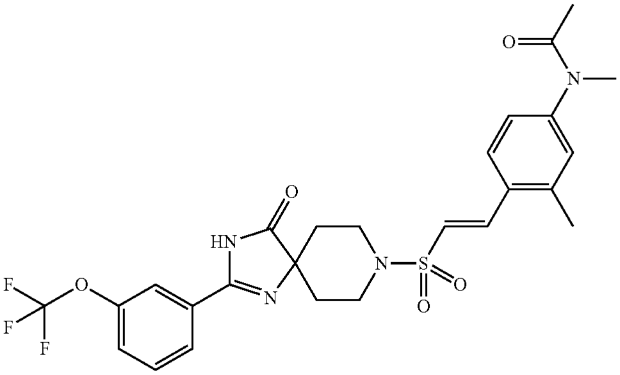 [SMILES: CC(=O)N(C)c1ccc(/C=C/S(=O)(=O)N2CCC3(CC2)N=C(c2cccc(OC(F)(F)F)c2)NC3=O)c(C)c1] | LCMS-C-1 | 2.63 | 565 (M + H)+ |

TABLE 37-continued

| Compound | Structure | LCMS or HPLC condition | Retention time (min) | MS (m/z) |
|---|---|---|---|---|
| 238 | 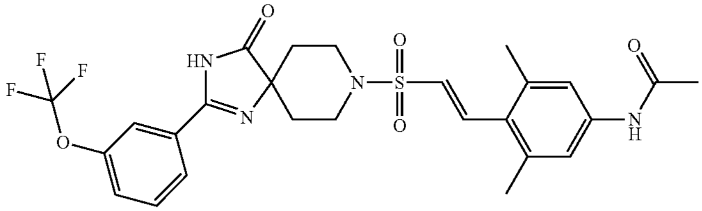 [SMILES: CC(=O)Nc1cc(C)c(/C=C/S(=O)(=O)N2CCC3(CC2)N=C(c2cccc(OC(F)(F)F)c2)NC3=O)c(C)c1] | HPLC-A-2 | 12.8 | 565 (M + H)+ |
| 239 | 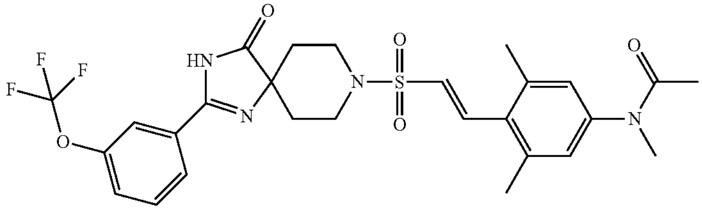 | HPLC-A-2 | 14.0 | 579 (M + H)+ |

The aryl bromide reagent used in the synthesis of Compound 230 ((4-bromo-3-methyl-phenyl)-(4-hydroxy-piperidin-1-yl)-methanone) was synthesized as follows.

(Reaction 31-2)

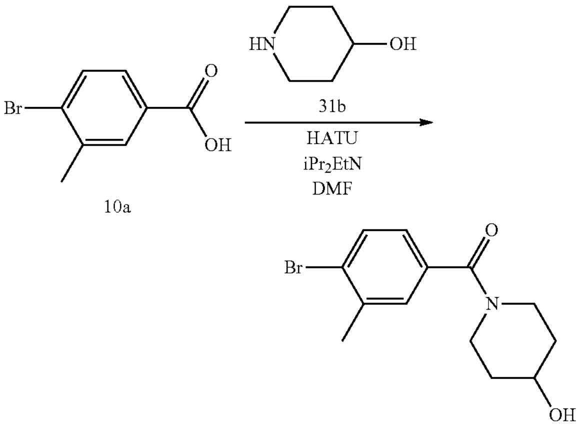

10a

31c (4-Bromo-3-methyl-phenyl)-(4-hydroxy-piperidin-1-yl)-methanone was synthesized by operations similar to those in Reaction 10-14 using appropriate reagents and starting material.

MS (ESI) m/z=298, 300 (M+H)+.

The aryl bromide reagent used in the synthesis of Compound 231 (4-bromo-3,N,N-trimethyl-benzamide) was synthesized as follows.

(Reaction 31-3)

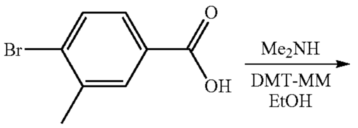

10a

-continued

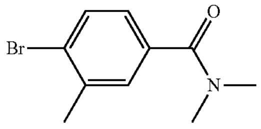

31d

4-Bromo-3,N,N-trimethyl-benzamide was synthesized by operations similar to those in Reaction 10-1 using appropriate reagents and starting material.

MS (ESI) m/z=264, 266 (M+H)+.

The aryl bromide reagent used in the synthesis of Compound 232 (N-(4-bromo-3-methyl-phenyl)-N-(2-hydroxy-ethyl)-acetamide) was synthesized as follows.

(Reaction 31-4)

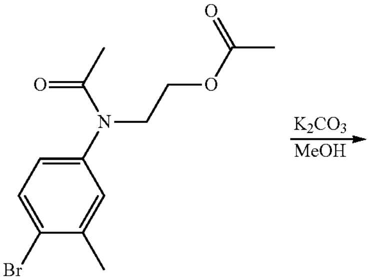

12d

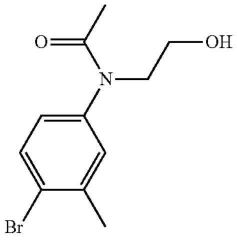

31e

N-(4-Bromo-3-methyl-phenyl)-N-(2-hydroxy-ethyl)-acetamide was synthesized by operations similar to those in Reaction 12-5 using appropriate reagents and starting material.

MS (ESI) m/z=272, 274 (M+H)+.

The aryl bromide reagent used in the synthesis of Compound 233 (4-bromo-3-fluoro-N,N-dimethyl-benzamide) was synthesized as follows.

(Reaction 31-5)

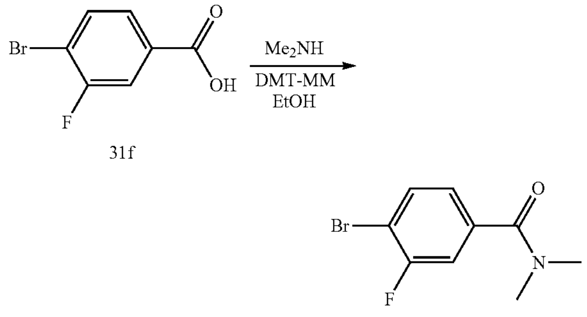

31f

31g

4-Bromo-3-fluoro-N,N-dimethyl-benzamide was synthesized by operations similar to those in Reaction 10-1 using appropriate reagents and starting material.

MS (ESI) m/z=246, 248 (M+H)+.

The aryl bromide reagent used in the synthesis of Compound 234 (4-(4-bromo-2,5-dichloro-phenoxy)-butane-1,2-diol) was synthesized as follows.

(Reaction 31-6)

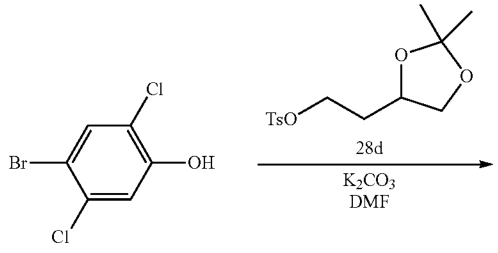

31h

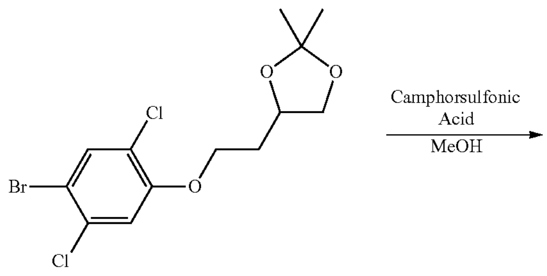

31i

-continued

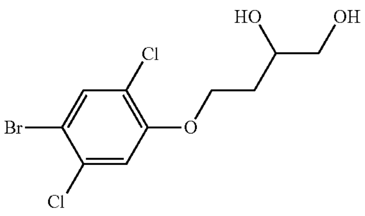

31j 4-(4-Bromo-2,5-dichloro-phenoxy)-butane-1,2-diol was synthesized by operations similar to those in Reaction 26-4 and Reaction 31-6 using appropriate reagents and starting material.

MS (ESI) m/z=351, 353 (M+H)+.

The aryl bromide reagent used in the synthesis of Compound 235 ([3-(4-bromo-3-methyl-phenoxy)-propyl]-dimethyl-amine) was synthesized as follows.

(Reaction 31-7)

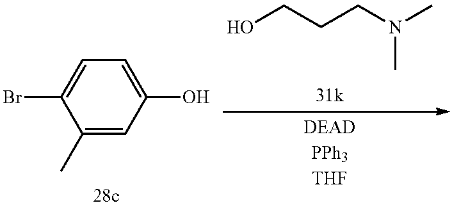

28c

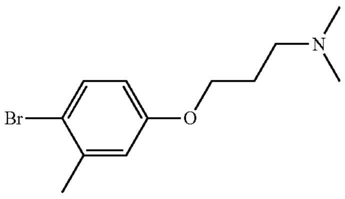

31l

3-Dimethylamino-propan-1-ol (251 μL, 2.14 mmol) and DEAD (973 μL, 2.14 mmol) were added to a solution of 4-bromo-3-methyl-phenol (200 mg, 1.07 mmol) and $PPh_3$ (561 mg, 2.14 mmol) in THF (10 mL) at 0° C. The mixture was stirred for two hours and then concentrated under reduced pressure. The resulting residue was purified by silica gel column chromatography to give [3-(4-bromo-3-methyl-phenoxy)-propyl]-dimethyl-amine (176 mg, 61%).

MS (ESI) m/z=273, 275 (M+H)+.

The aryl bromide reagent used in the synthesis of Compound 236 (N-(3-bromo-2-methyl-phenyl)-N-methyl-acetamide) was synthesized as follows.

(Reaction 31-8)

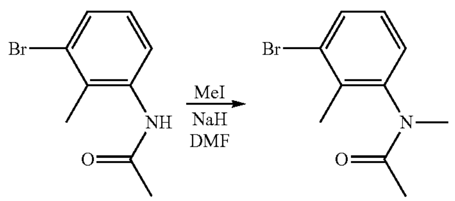

31m 31n

N-(3-Bromo-2-methyl-phenyl)-N-methyl-acetamide was synthesized by operations similar to those in Reaction 25-3 using appropriate reagents and starting material.

MS (ESI) m/z=242, 244 (M+H)+.

The aryl bromide reagent used in the synthesis of Compound 237 (N-(4-bromo-3-methyl-phenyl)-N-methyl-acetamide) was synthesized as follows.

(Reaction 31-9)

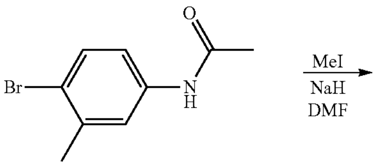

11a

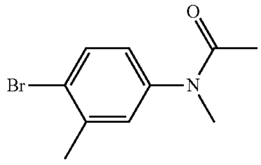

31o

N-(4-Bromo-3-methyl-phenyl)-N-methyl-acetamide was synthesized by operations similar to those in Reaction 25-3 using appropriate reagents and starting material.

MS (ESI) m/z=264, 266 (M+H)+.

The aryl bromide reagent used in the synthesis of Compound 239 (N-(4-bromo-3,5-dimethyl-phenyl)-N-methylacetamide) was synthesized as follows.

(Reaction 31-10)

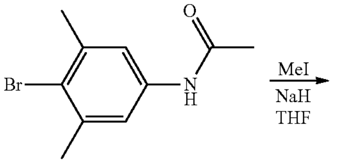

26a

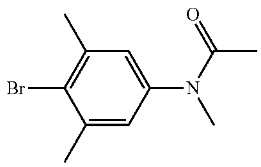

31p

N-(4-Bromo-3,5-dimethyl-phenyl)-N-methyl-acetamide was synthesized by operations similar to those in Reaction 25-3 using appropriate reagents and starting material.

MS (ESI) m/z=256, 258 (M+H)+.

Example 32

2-Cycloheptyl-8-{(E)-2-[1-((S)-2,3-dihydroxy-propyl)-1H-indol-4-yl]-ethenesulfonyl}-1,3,8-triaza-spiro[4.5]dec-1-en-4-one (Compound 240)

(Reaction 32-1)

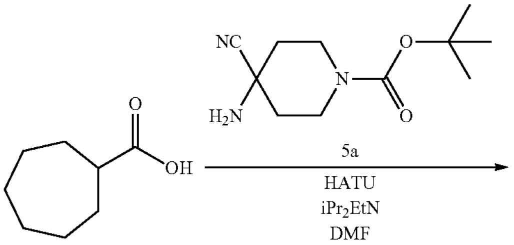

32a

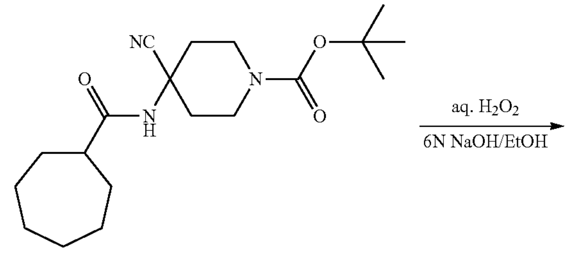

32b

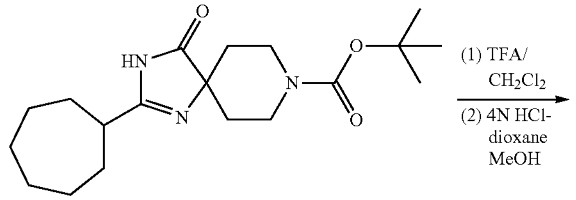

32c

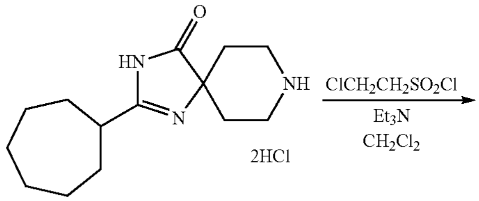

32d

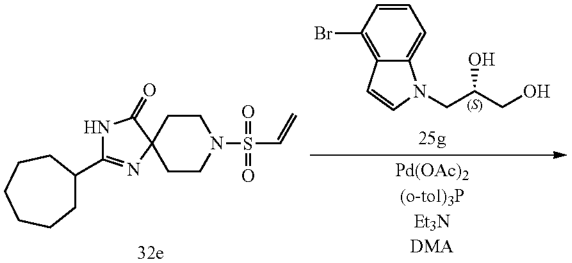

32e

-continued

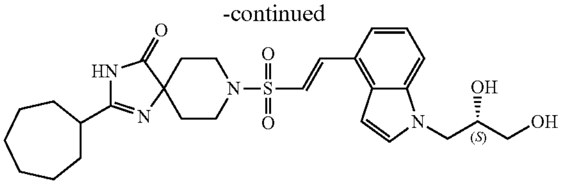

Compound 240

2-Cycloheptyl-8-{(E)-2-[1-((S)-2,3-dihydroxy-propyl)-1H-indol-4-yl]-ethenesulfonyl}- 1,3,8-triaza-spiro[4.5]dec-1-en-4-one was synthesized by operations similar to those in Reaction 10-14, Reaction 1-4, Reaction 11-4, Reaction 25-1 and Reaction 25-2 using appropriate reagents and starting material.

MS (ESI) m/z=529 (M+H)+.

The example compound shown below was synthesized by operations similar to those in Example 32 using appropriate reagents and starting material.

Compound 241

TABLE 38

| Compound | Structure | LCMS or HPLC condition | Retention time (min) | MS (m/z) |
|---|---|---|---|---|
| 241 | 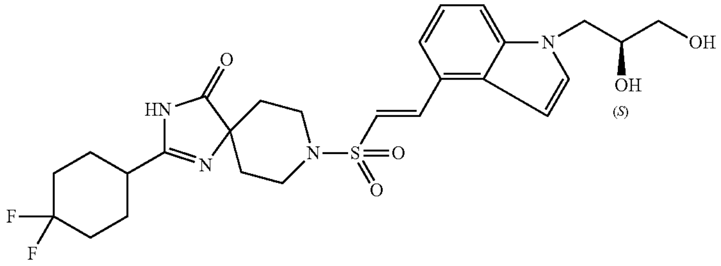 | LCMS-A-1 | 1.90 | 551 (M + H)+ |

Example 33

8-{(E)-2-[4-((R)-2,3-Dihydroxy-propoxy)-2,6-dimethyl-phenyl]-ethenesulfonyl}-2-(4-fluoro-3-trifluoromethyl-phenyl)-1,3,8-triaza-spiro[4.5]dec-1-en-4-one (Compound 242)

(Reaction 33-1)

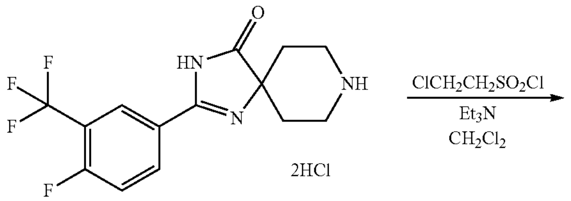

33a

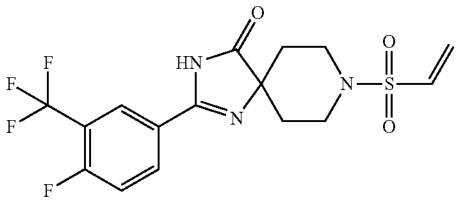

33b

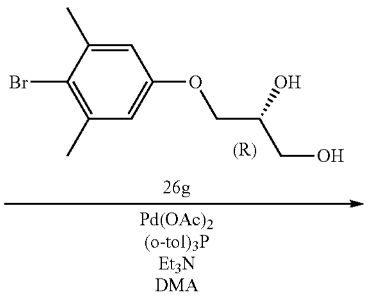

-continued

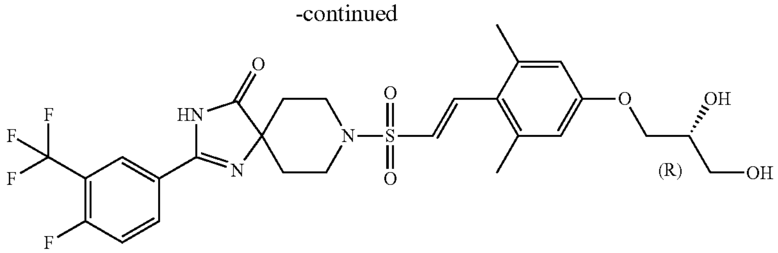

Compouond 242

8-{(E)-2-[4-((R)-2,3-Dihydroxy-propoxy)-2,6-dimethyl-phenyl]-ethenesulfonyl}-2-(4-fluoro-3-trifluoromethyl-phenyl)-1,3,8-triaza-spiro[4.5]dec-1-en-4-one was synthesized by operations similar to those in Reaction 25-1 and Reaction 25-2 using appropriate reagents and starting material.

MS (ESI) m/z=600 (M+H)+.

The example compounds shown below were synthesized by operations similar to those in Example 33 using appropriate reagents and starting materials.

Compounds 243 to 246

TABLE 39

| Compound | Structure | LCMS or HPLC condition | Retention time (min) | MS (m/z) |
|---|---|---|---|---|
| 243 | 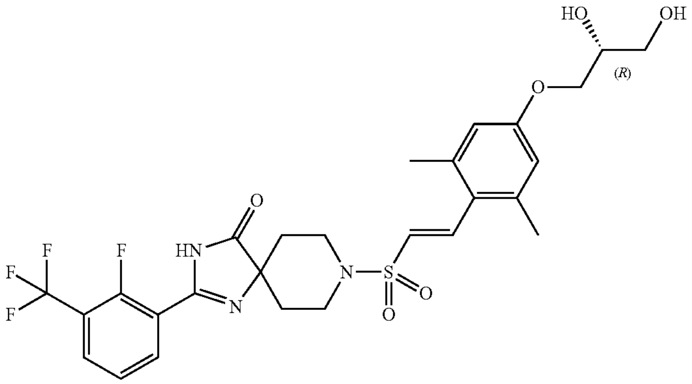 | LCMS-A-1 | 2.36 | 600 (M + H)+ |
| 244 | 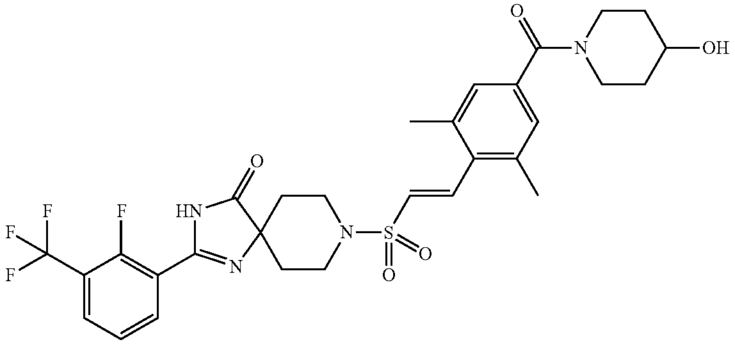 [SMILES: Cc1cc(C(=O)N2CCC(O)CC2)cc(C)c1/C=C/S(=O)(=O)N1CCC2(CC1)N=C(c1cccc(C(F)(F)F)c1F)NC2=O] | LCMS-C-1 | 2.52 | 637 (M + H)+ |
| 245 | 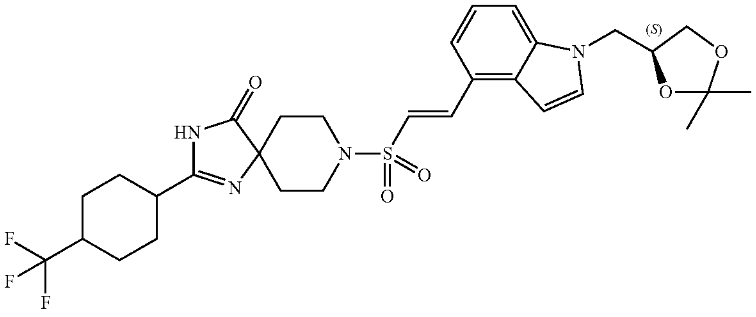 | LCMS-A-1 | 2.92 | 562 (M + H)+ |

TABLE 39-continued

| Compound | Structure | LCMS or HPLC condition | Retention time (min) | MS (m/z) |
|---|---|---|---|---|
| 246 | 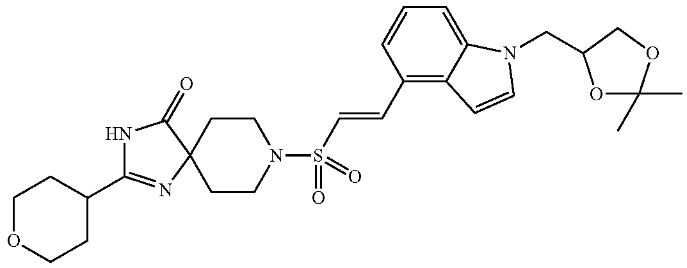 [SMILES: CC1(C)OCC(Cn2ccc3c(/C=C/S(=O)(=O)N4CCC5(CC4)N=C(C4CCOCC4)NC5=O)cccc32)O1] | LCMS-E-4 | 2.82 | 557 (M + H)+ |

The aryl bromide reagent used in the synthesis of Compound 244 ((4-bromo-3,5-dimethyl-phenyl)-(4-hydroxy-piperidin-1-yl)-methanone) was synthesized as follows.

(Reaction 33-2)

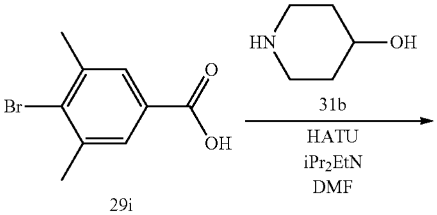

29i

-continued

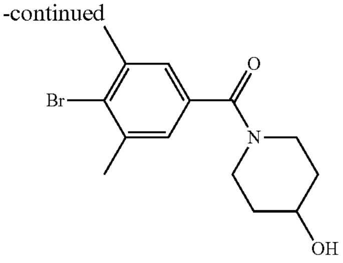

33c (4-Bromo-3,5-dimethyl-phenyl)-(4-hydroxy-piperidin-1-yl)-methanone was synthesized by operations similar to those in Reaction 10-14 using appropriate reagents and starting material.

MS (ESI) m/z=312, 314 (M+H)+.

Example 34

8-{(E)-2-[4-(3,4-Dihydroxy-butoxy)-2-methyl-phenyl]-ethenesulfonyl}-2-(2-fluoro-3-trifluoromethyl-phenyl)-1,3,8-triaza-spiro[4.5]dec-1-en-4-one (Compound 247)

(Reaction 34-1)

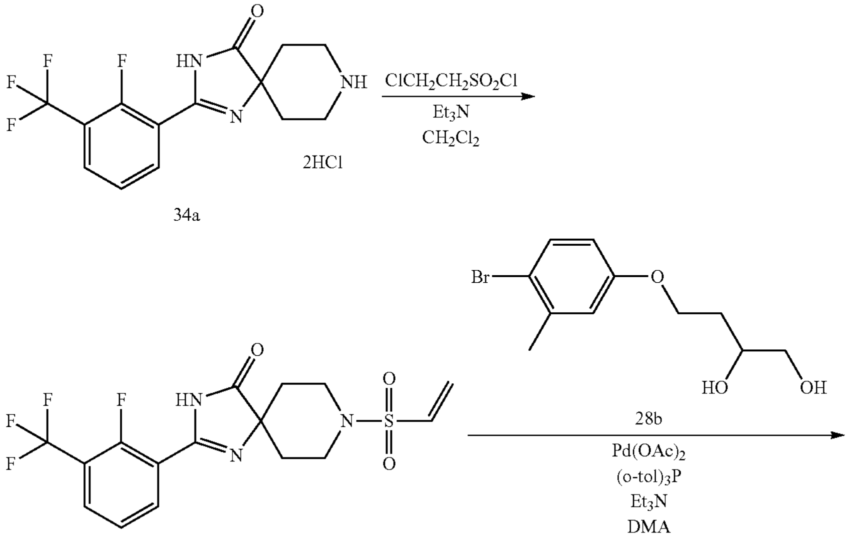

34b

-continued

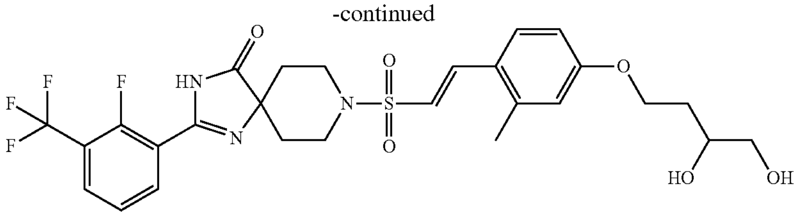

Compound 247

8-{(E)-2-[4-(3,4-Dihydroxy-butoxy)-2-methyl-phenyl]-ethenesulfonyl}-2-(2-fluoro-3-trifluoromethyl-phenyl)-1,3,8-triaza-spiro[4.5]dec-1-en-4-one was synthesized by operations similar to those in Reaction 25-1 and Reaction 26-1 using appropriate reagents and starting material.

MS (ESI) m/z=600 (M+H)+.

The example compounds shown below were synthesized by operations similar to those in Example 34 using appropriate reagents and starting materials.

Compounds 248 to 250

TABLE 40

| Compound | Structure | LCMS or HPLC condition | Retention time (min) | MS (m/z) |
|---|---|---|---|---|
| 248 | 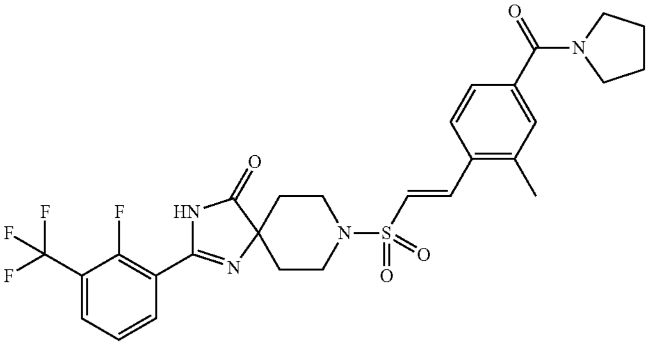 [SMILES: Cc1cc(C(=O)N2CCCC2)ccc1/C=C/S(=O)(=O)N1CCC2(CC1)N=C(c1cccc(C(F)(F)F)c1F)NC2=O] | LCMS-C-1 | 2.62 | 593 (M + H)+ |
| 249 | 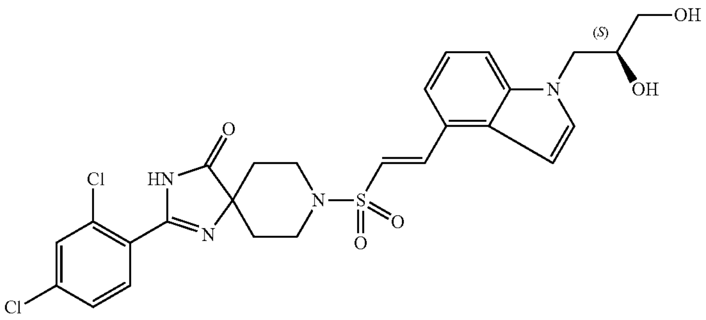 | LCMS-B-1 | 1.96 | 577 (M + H)+ |
| 250 | 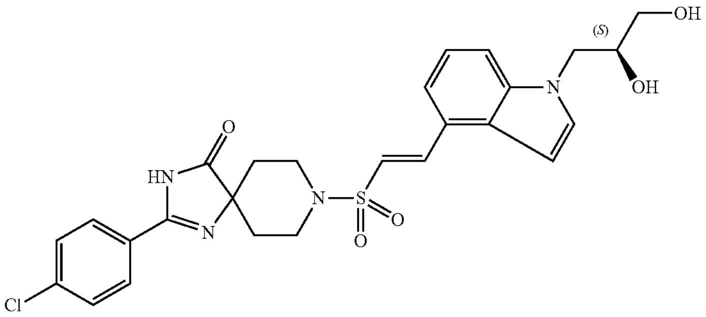 | LCMS-B-1 | 1.85 | 543 (M + H)+ |

Example 35

2-Cyclohexyl-8-[(E)-4-(1H-indol-4-yl)-but-3-ene-1-sulfonyl]-1,3,8-triaza-spiro[4.5]dec-1-en-4-one (Compound 251)

(Reaction 35-1)

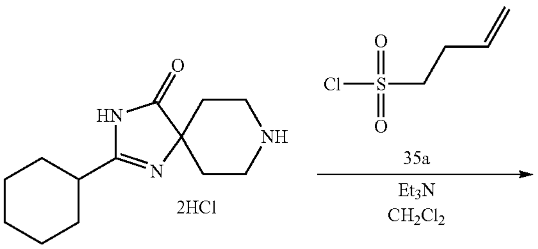

25a

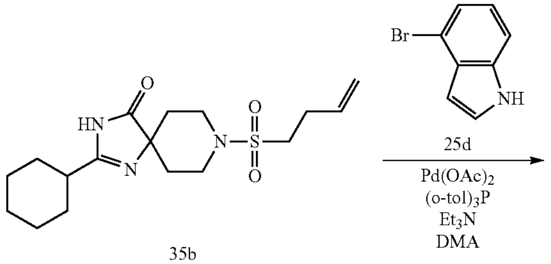

35b

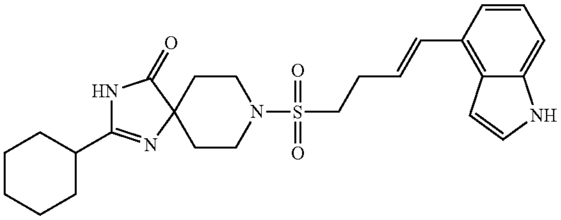

Compound 251

2-Cyclohexyl-8-[(E)-4-(1H-indol-4-yl)-but-3-ene-1-sulfonyl]-1,3,8-triaza-spiro[4.5]dec-1-en-4-one was synthesized by operations similar to those in Reaction 25-1 and Reaction 25-2 using appropriate reagents and starting material.

MS (ESI) m/z=469 (M+H)+.

Example 36

2-Cyclohexyl-8-[(E)-5-(1H-indol-4-yl)-pent-4-ene-1-sulfonyl]-1,3,8-triaza-spiro[4.5]dec-1-en-4-one (Compound 252)

(Reaction 36-1)

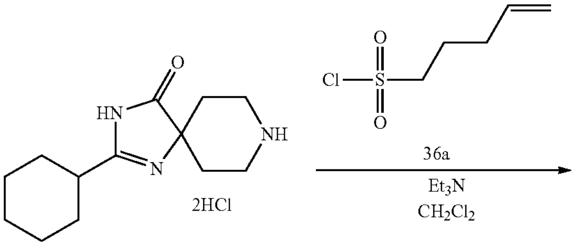

25a

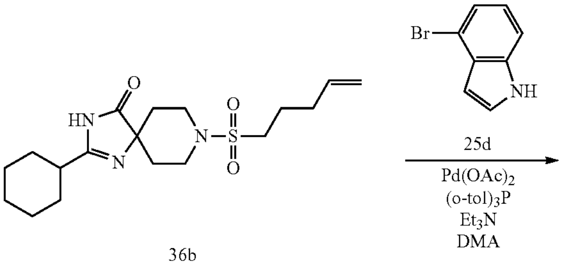

36b

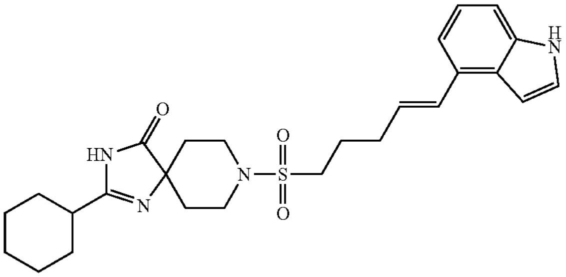

Compound 252

2-Cyclohexyl-8-[(E)-5-(1H-indol-4-yl)-pent-4-ene-1-sulfonyl]-1,3,8-triaza-spiro[4.5]dec-1-en-4-one was synthesized by operations similar to those in Reaction 25-1 and Reaction 25-2 using appropriate reagents and starting material.

MS (ESI) m/z=483 (M+H)+.

Example 37
2-Cyclohexyl-8-{(E)-3-[1-((S)-2,3-dihydroxy-propyl)-1H-indol-4-yl]-prop-2-ene-1-sulfonyl}-1,3,8-triaza-spiro[4.5]dec-1-en-4-one (Compound 253)
(Reaction 37-1)
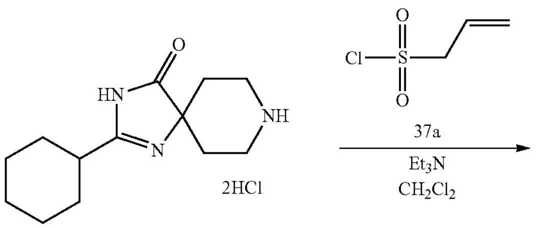
25a
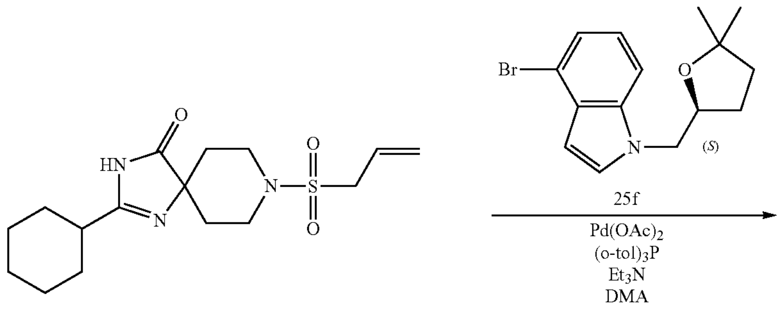
37b
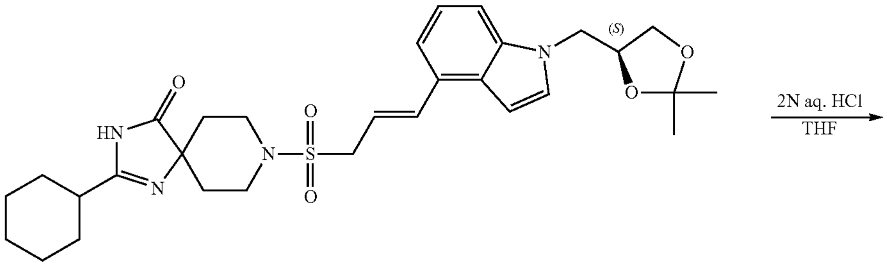
37c
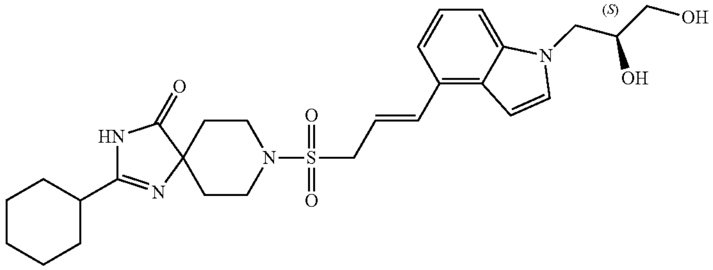
Compound 253

2-Cyclohexyl-8-{(E)-3-[1-((S)-2,3-dihydroxy-propyl)-1H-indol-4-yl]-prop-2-ene-1-sulfonyl}-1,3,8-triaza-spiro[4.5]dec-1-en-4-one was synthesized by operations similar to those in Reaction 25-1, Reaction 25-2 and Reaction 25-4 using appropriate reagents and starting material.

MS (ESI) m/z=529 (M+H)+.

Example 38

8-{(E)-2-[3-(3,4-Dihydroxy-butoxy)-2-methyl-phenyl]-ethenesulfonyl}-2-(3-trifluoromethoxy-phenyl)-1,3,8-triaza-spiro[4.5]dec-1-en-4-one (Compound 254)

tions similar to those in Reaction 31-7, Reaction 26-1 and Reaction 25-4 using appropriate reagents and starting material.

$^1$H-NMR (300 MHz, $CDCl_3$) δ 1.7 (2H, d, J=13.73 Hz), 1.97 (1H, brs), 2.00 (2H, m), 2.18 (2H, dt, J=3.05, 13.73 Hz), 2.30 (3H, s), 2.51 (1H, brs), 3.35 (2H, dt, J=3.05, 11.83 Hz), 3.59 (1H, m), 3.75 (1H, m), 3.80 (2H, d, J=11.83 Hz), 4.06 (1H, brs), 4.18 (2H, m), 6.66 (1H, d, J=15.64 Hz), 6.95 (1H, d, J=7.63 Hz), 7.17 (1H, t, J=7.63 Hz), 7.21 (1H, d, J=7.63 Hz), 7.42 (1H, d, J=8.01 Hz), 7.54 (1H, dd, J=7.63, 8.01 Hz), 7.75 (1H, d, J=7.63 Hz), 7.81 (1H, s), 7.81 (1H, d, J=15.64 Hz), 9.75 (1H, s). MS (ESI) m/z=598 (M+H)+.

(Reaction 38-1)

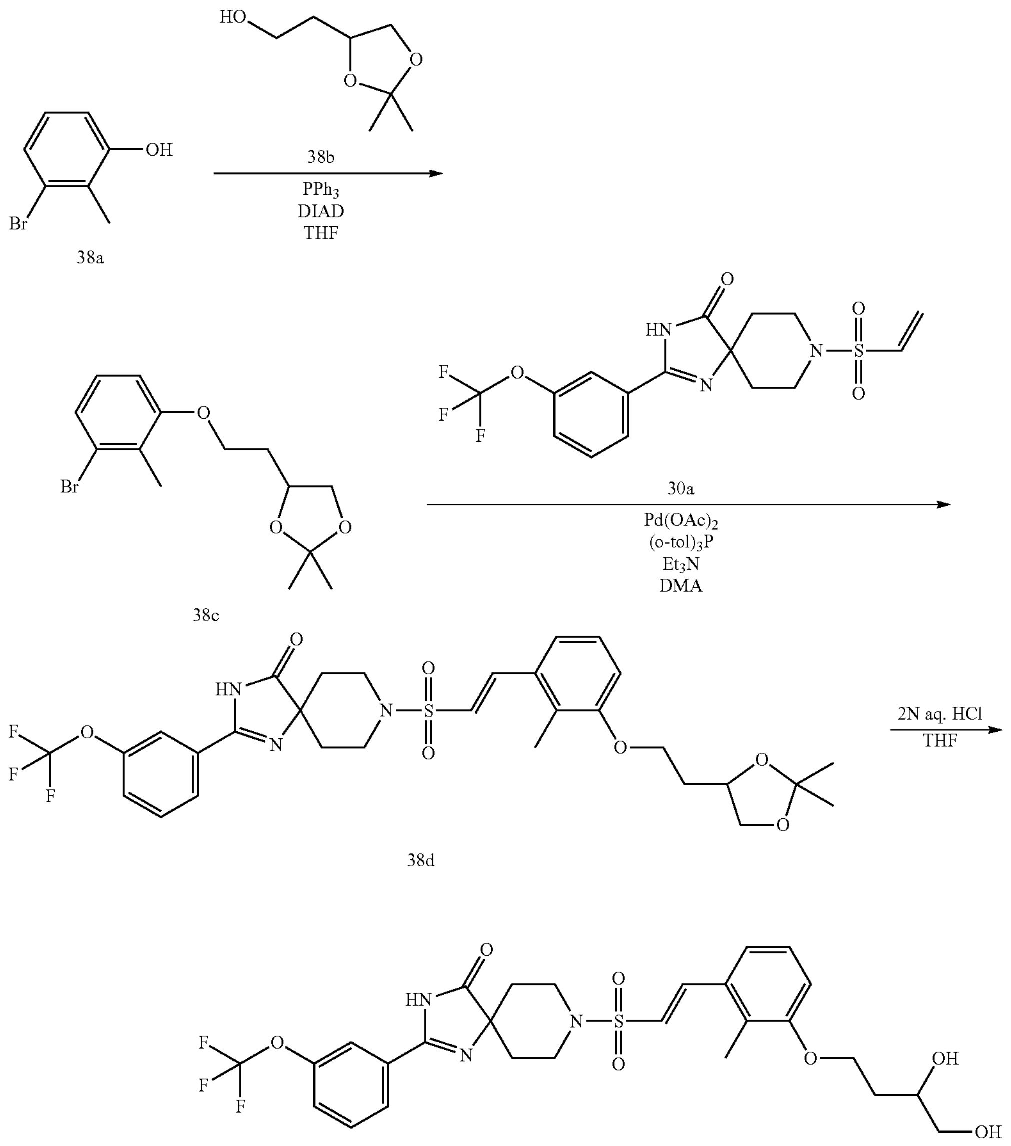

Compound 254

8-{(E)-2-[3-(3,4-Dihydroxy-butoxy)-2-methyl-phenyl]-ethenesulfonyl}-2-(3-trifluoromethoxy-phenyl)-1,3,8-triaza-spiro[4.5]dec-1-en-4-one was synthesized by opera- The example compound shown below was synthesized by operations similar to those in Example 38 using appropriate reagents and starting material.

Compound 255

TABLE 41

| Compound | Structure | LCMS or HPLC condition | Retention time (min) | MS (m/z) |
|---|---|---|---|---|
| 255 | 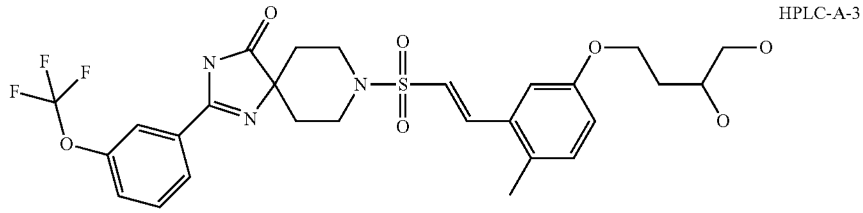 | HPLC-A-3 | 11.56 | 598 (M + H)+ |

Example 39

8-{(E)-2-[3-(2-Hydroxy-ethoxy)-2-methyl-phenyl]-ethenesulfonyl}-2-(3-trifluoromethoxy-phenyl)-1,3,8-triaza-spiro[4.5]dec-1-en-4-one (Compound 256)

(Reaction 39-1)

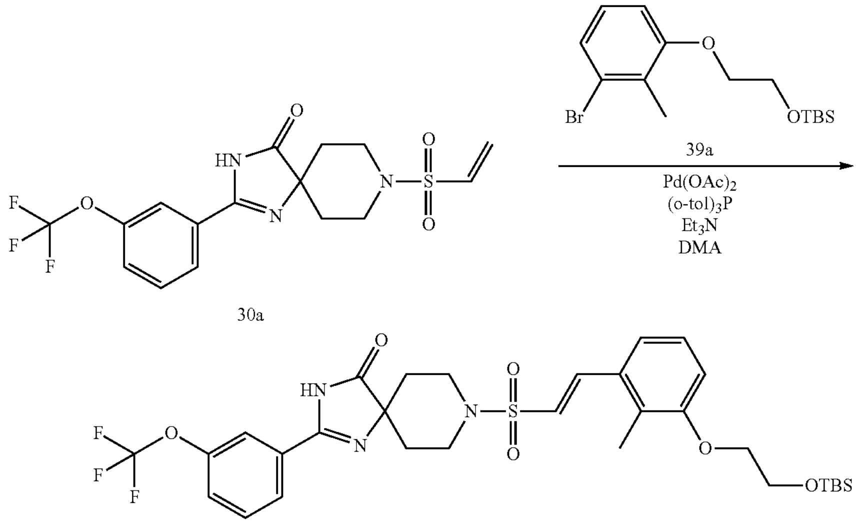

39b 8-((E)-2-{3-[2-(tert-Butyl-dimethyl-silanyloxy)-ethoxy]-2-methyl-phenyl}-ethenesulfonyl)-2-(3-trifluoromethoxy-phenyl)-1,3,8-triaza-spiro[4.5]dec-1-en-4-one was synthesized by operations similar to those in Reaction 26-1 using appropriate reagents and starting material. This compound was used as such in the next step without purification.

(Reaction 39-2)

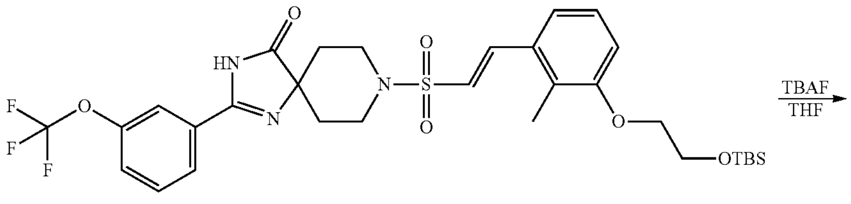

39b

-continued

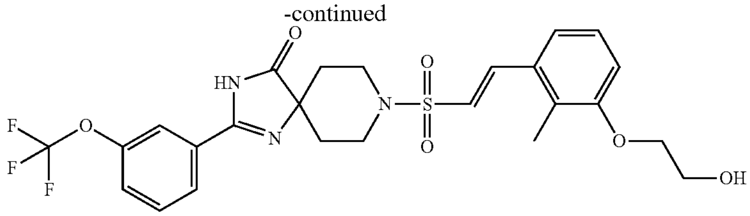

Compound 256

Tetrabutylammonium fluoride (0.11 ml, 0.11 mmol, 1 M in THF) was added to a solution of 8-((E)-2-{3-[2-(tert-Butyl-dimethyl-silanyloxy)-ethoxy]-2-methyl-phenyl}-ethene-sulfonyl)-2-(3-trifluoromethoxy-phenyl)-1,3,8-triaza-spiro[4.5]dec-1-en-4-one obtained above in anhydrous THF (1 ml) at room temperature in an Ar atmosphere. The mixture was stirred at room temperature for two hours and then concentrated under reduced pressure. The resulting residue was purified by silica gel column chromatography (hexane:EtOAc=1:1) to give 8-{(E)-2-[3-(2-hydroxy-ethoxy)-2-methyl-phenyl]-ethenesulfonyl}-2-(3-trifluoromethoxy-phenyl)-1,3,8-triaza-spiro[4.5]dec-1-en-4-one (3.2 mg, yield in two steps: 48%).

$^1$H-NMR (300 MHz, DMSO-d6) δ 11.75 (1H, s), 7.99 (1H, d, J=7.5 Hz), 7.90 (1H, s), 7.63 (3H, m), 7.37 (1H, d, J=7.5 Hz), 7.23 (2H, m), 7.06 (1H, d, J=7.9 Hz), 4.85 (1H, t, J=5.6 Hz), 4.00 (2H, m), 3.74 (2H, m), 3.60 (2H, m), 3.20 (2H, m), 2.27 (3H, s), 1.88 (2H, m), 1.63 (2H, m). MS (ESI+) m/z=554 (M+H)+.

The example compounds shown below were synthesized by operations similar to those in Example 39 using appropriate reagents and starting materials.

Compounds 257 to 258

TABLE 42

| Compound | Structure | LCMS or HPLC condition | Retention time (min) | MS (m/z) |
|---|---|---|---|---|
| 257 | 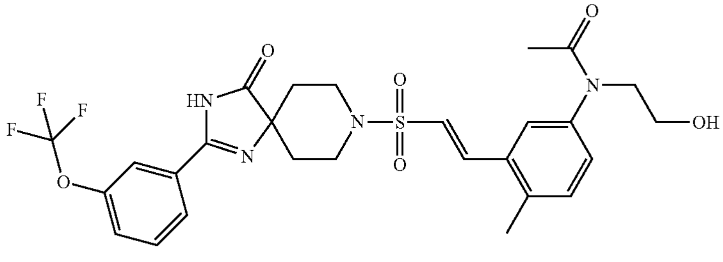 [SMILES: CC(=O)N(CCO)c1ccc(C)c(/C=C/S(=O)(=O)N2CCC3(CC2)N=C(c2cccc(OC(F)(F)F)c2)NC3=O)c1] | LCMS-D-1 | 3.1 | 595 (M + H)+ |
| 258 | 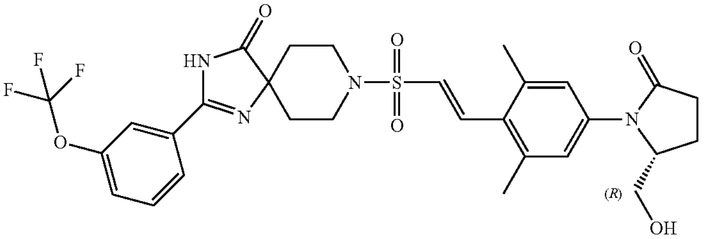 | LCMS-D-1 | 3.10 | 621 (M + H)+ |

The aryl bromide reagent used in the synthesis of Compound 257 (N-(3-bromo-4-methyl-phenyl)-N-[2-(tert-butyl-dimethyl-silanyloxy)-ethyl]-acetamide) was synthesized as follows.

(Reaction 39-3)

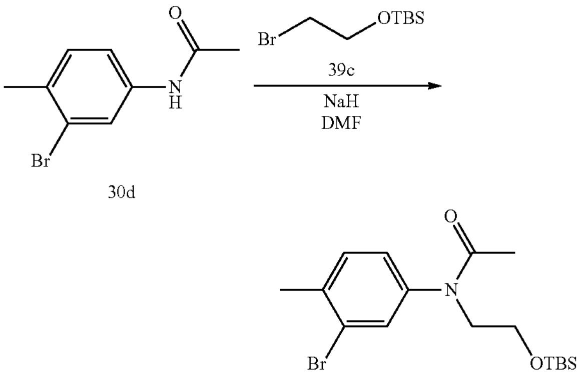

N-(3-Bromo-4-methyl-phenyl)-N-[2-(tert-butyl-dimethyl-silanyloxy)-ethyl]-acetamide was synthesized by operations similar to those in Reaction 25-3 using appropriate reagents and starting material.

MS (ESI) m/z=386, 388 (M+H)+.

The aryl bromide reagent used in the synthesis of Compound 258 ((R)-1-(4-bromo-3,5-dimethyl-phenyl)-5-(tert-butyl-dimethyl-silanyloxymethyl)-pyrrolidin-2-one) was synthesized as follows.

(Reaction 39-4)

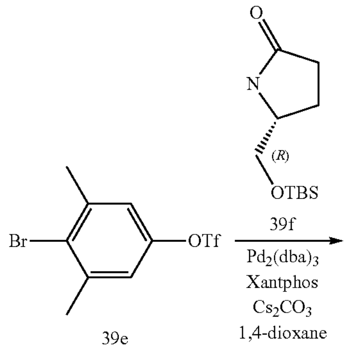

39e

-continued

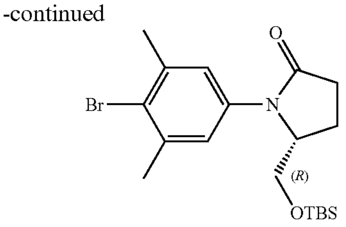

39g (R)-1-(4-Bromo-3,5-dimethyl-phenyl)-5-(tert-butyl-dimethyl-silanyloxymethyl)-pyrrolidin-2-one was synthesized by operations similar to those in Reaction 29-3 using appropriate reagents and starting material.

$^1$H-NMR (300 MHz, $CDCl_3$) δ −0.06 (3H, s), −0.03 (3H, s), 0.86 (9H, s), 2.10 (1H, m), 2.26 (1H, m), 2.40 (6H, s), 2.48 (1H, ddd, J=4.6, 10.3, 16.8 Hz), 2.68 (1H, ddd, J=8.0, 9.9, 17.9 Hz), 3.56 (2H, dq, J=3.8, 10.7 Hz), 4.15 (1H, m), 7.10 (2H, s).

Example 40

N-(4-{(E)-2-[2-(2-Fluoro-3-trifluoromethyl-phenyl)-4-oxo-1,3,8-triaza-spiro[4.5]dec-1-ene-8-sulfonyl]-vinyl}-3-methyl-phenyl)-N-(2-hydroxy-ethyl)-acetamide (Compound 259)

(Reaction 40-1)

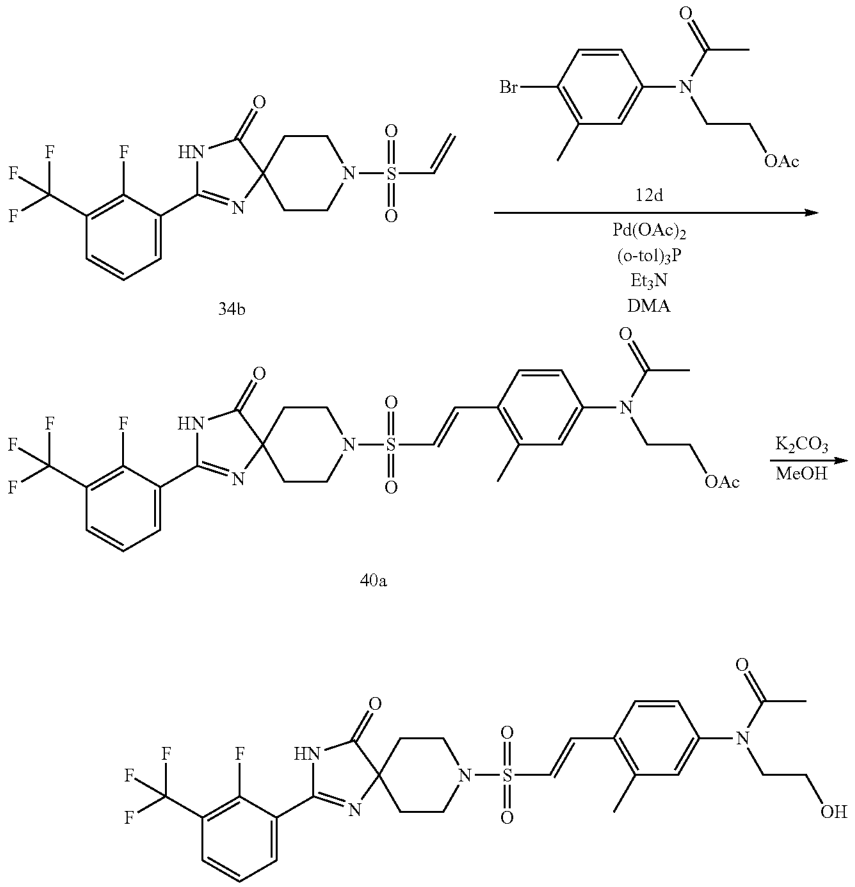

Compound 259

N-(4-{(E)-2-[2-(2-Fluoro-3-trifluoromethyl-phenyl)-4-oxo-1,3,8-triaza-spiro[4.5]dec-1-ene-8-sulfonyl]-vinyl}-3-methyl-phenyl)-N-(2-hydroxy-ethyl)-acetamide was synthesized by operations similar to those in Reaction 26-1 and Reaction 12-5 using appropriate reagents and starting material.

MS (ESI) m/z=597 (M+H)+.

Example 41

N-(3-Methyl-4-{(E)-2-[4-oxo-2-(3-trifluoromethoxy-phenyl)-1,3,8-triaza-spiro[4.5]dec-1-ene-8-sulfonyl]-vinyl}-phenyl)-N-piperidin-4-yl-acetamide (Compound 260)

(Reaction 41-1)

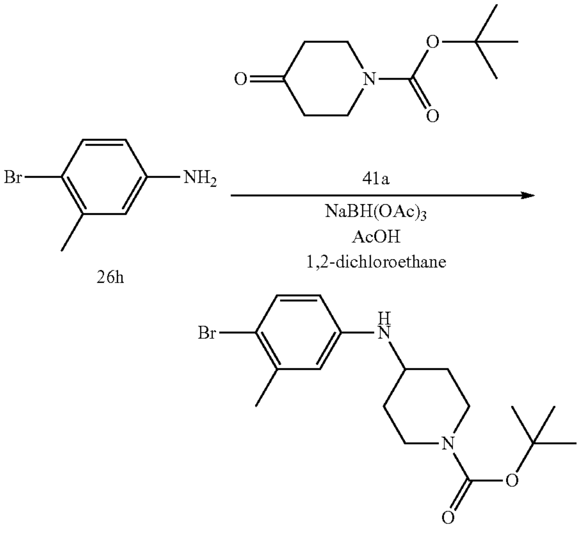

Acetic acid (4.9 eq) and sodium triacetoxyborohydride (2.0 eq) were sequentially added to a solution of 4-bromo-3-methylaniline (246 mg, 1.32 mmol) and 1-(tert-butoxycarbonyl)-4-piperidone (350 mg, 1.76 mmol) in 1,2-dichloroethane (10 ml). The mixture was stirred at room temperature for 3.5 hours and then quenched with a saturated aqueous sodium carbonate solution. The reaction mixture was extracted with dichloromethane, and the organic layer was then concentrated under reduced pressure to 4-(4-bromo-3-methyl-phenylamino)-piperidine-1-carboxylic acid tert-butyl ester as a white solid (586 mg, 100%). This compound was used in the next step without further purification.

$^1$H-NMR (400 MHz, $CDCl_3$) δ 1.32 (m, 2H), 1.42 (s, 9H), 2.01 (d, J=13.2 Hz, 2H), 2.31 (s, 3H), 2.92 (t, J=11.6 Hz, 2H), 3.45 (br, 2H), 4.04 (br, 1H), 6.32 (dd, J=2.4 Hz, 8.4 Hz, 1H), 6.48 (d, J=2.8 Hz, 1H), 7.28 (m, 1H). MS (ESI) m/z=369 (M+H)+.

(Reaction 41-2)

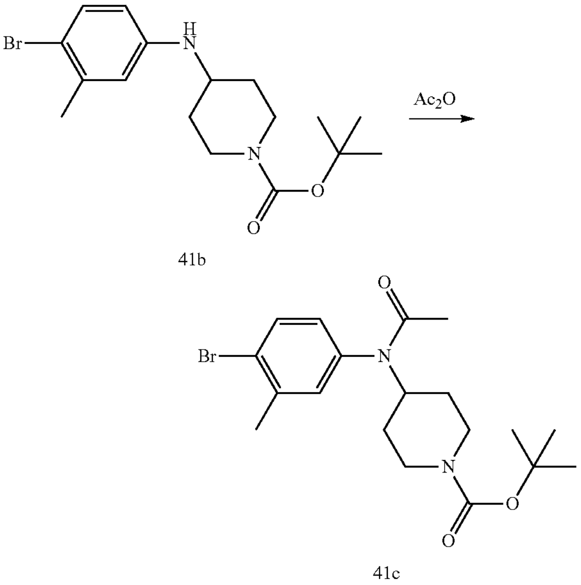

4-[Acetyl-(4-bromo-3-methyl-phenyl)-amino]-piperidine-1-carboxylic acid tert-butyl ester was synthesized by operations similar to those in Reaction 12-2 using the compound obtained above as a starting material.

MS (ESI) m/z=411, 413 (M+H)+.

(Reaction 41-3)

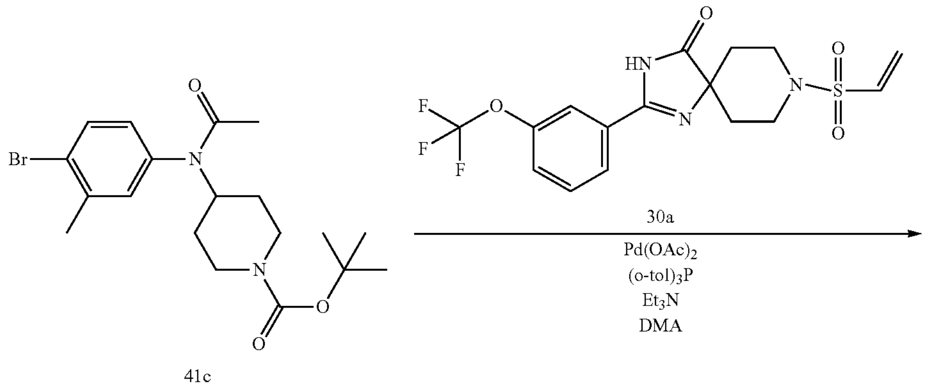

-continued

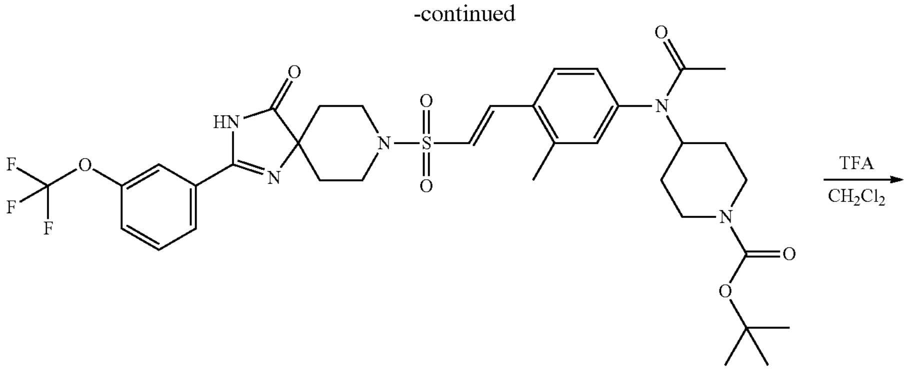

41d

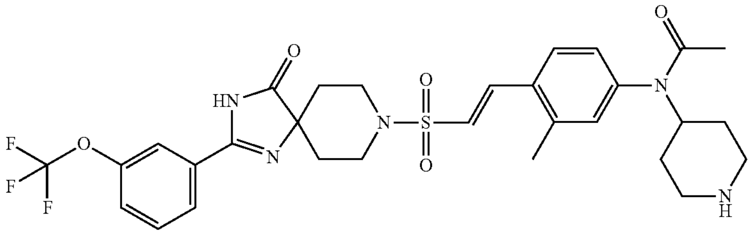

Compound 260

N-(3-Methyl-4-{(E)-2-[4-oxo-2-(3-trifluoromethoxy-phenyl)-1,3,8-triaza-spiro[4.5]dec-1-ene-8-sulfonyl]-vinyl}-phenyl)-N-piperidin-4-yl-acetamide was synthesized by operations similar to those in Reaction 26-1 and Reaction 4-1 using appropriate reagents and starting material.

MS (ESI) m/z=634 (M+H)+.

Example 42

2-Cyclohexyl-8-[2-(2-oxo-2,3-dihydro-benzoxazol-7-yl)-ethanesulfonyl]-1,3,8-triaza-spiro[4.5]dec-1-en-4-one (Compound 261)

(Reaction 42-1)

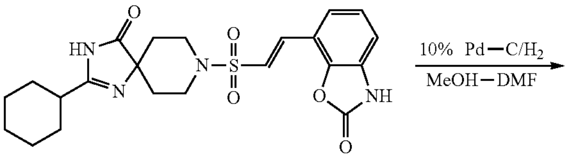

Compound 188

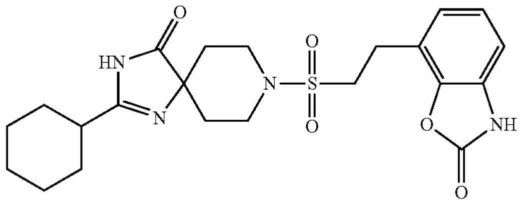

Compound 261

10% Pd—C (28 mg) was added to a solution of 2-cyclohexyl-8-[(E)-2-(2-oxo-2,3-dihydro-benzoxazol-7-yl)-ethenesulfonyl]-1,3,8-triaza-spiro[4.5]dec-1-en-4-one (56.6 mg, 0.123 mmol) in MeOH-DMF (4 ml, 1:1). The mixture was stirred at room temperature overnight in a hydrogen atmosphere. The reaction mixture was filtered through celite, and the filtrate was then concentrated under reduced pressure. The resulting residue was diluted with ethyl acetate, and the organic layer was then washed with water (×2), dried over anhydrous $Na_2SO_4$ and concentrated under reduced pressure. The residue was purified by column chromatography (silica gel, AcOEt-hexane) to give 2-cyclohexyl-8-[2-(2-oxo-2,3-dihydro-benzoxazol-7-yl)-ethanesulfonyl]-1,3,8-triaza-spiro[4.5]dec-1-en-4-one as a colorless foam (46.9 mg, 83%).

$^1$H-NMR (400 MHz, $CDCl_3$) δ 1.21-1.45 (6H, m), 1.50-1.60 (2H, m), 1.65-1.85 (4H, m), 1.90-1.96 (2H, m), 2.38-2.48 (1H, m), 3.25-3.40 (6H, m), 3.65-3.73 (2H, m), 7.01 (2H, d, J=8.0 Hz), 7.13 (1H, t, J=8 Hz), 8.59 (1H, brs), 9.03 (1H, brs). MS (ESI) m/z=461 (M+H)+.

The example compounds shown below were synthesized by operations similar to those in Example 42 using appropriate reagents and starting materials.

Compounds 262 to 267
TABLE 43
| Compound | Structure | LCMS or HPLC condition | Retention time (min) | MS (m/z) |
|---|---|---|---|---|
| 262 | 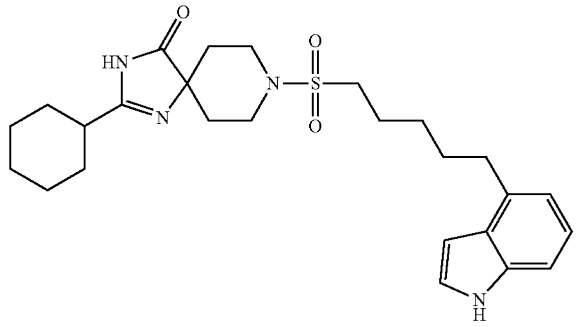 [SMILES: O=C1NC(C2CCCCC2)=NC12CCN(S(=O)(=O)CCCCCc1cccc3[nH]ccc13)CC2] | LCMS-E-5 | 3.3 | 485 (M + H)+ |
| 263 | 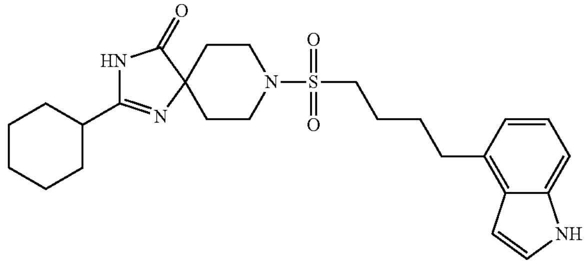 [SMILES: O=C1NC(C2CCCCC2)=NC12CCN(S(=O)(=O)CCCCc1cccc3[nH]ccc13)CC2] | LCMS-E-4 | 2.89 | 471 (M + H)+ |
| 264 | 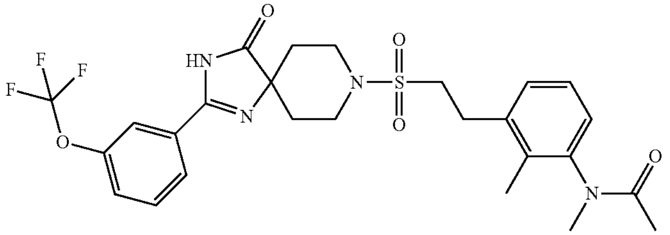 [SMILES: CC(=O)N(C)c1cccc(CCS(=O)(=O)N2CCC3(CC2)N=C(c2cccc(OC(F)(F)F)c2)NC3=O)c1C] | LCMS-D-1 | 3.1 | 567 (M + H)+ |
| 265 | 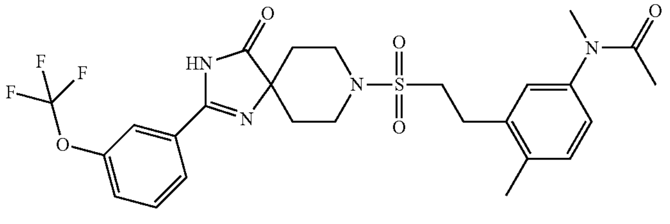 [SMILES: CC(=O)N(C)c1ccc(C)c(CCS(=O)(=O)N2CCC3(CC2)N=C(c2cccc(OC(F)(F)F)c2)NC3=O)c1] | LCMS-D-1 | 3.3 | 567 (M + H)+ |
| 266 | 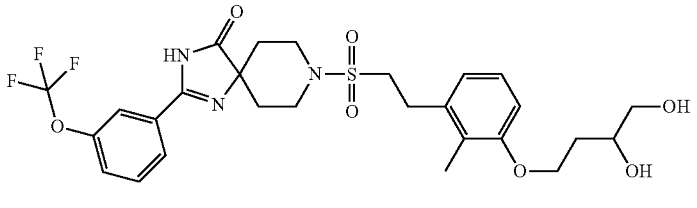 [SMILES: Cc1c(CCS(=O)(=O)N2CCC3(CC2)N=C(c2cccc(OC(F)(F)F)c2)NC3=O)cccc1OCCC(O)CO] | HPLC-A-3 | 11.35 | 600 (M + H)+ |
| 267 | 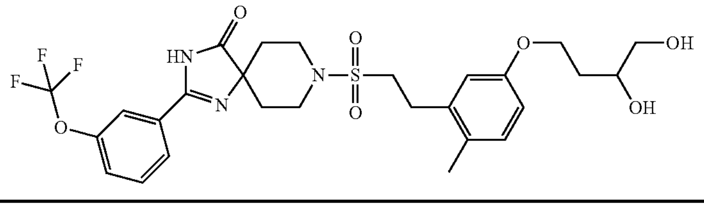 | HPLC-A-3 | 11.03 | 600 (M + H)+ |

Example 43

8-{2-[4-((R)-2-Hydroxymethyl-5-oxo-pyrrolidin-1-yl)-2-methyl-phenyl]-ethanesulfonyl}-2-(3-trifluoromethyl-phenyl)-1,3,8-triaza-spiro[4.5]dec-1-en-4-one (Compound 268)

(Reaction 42-2)

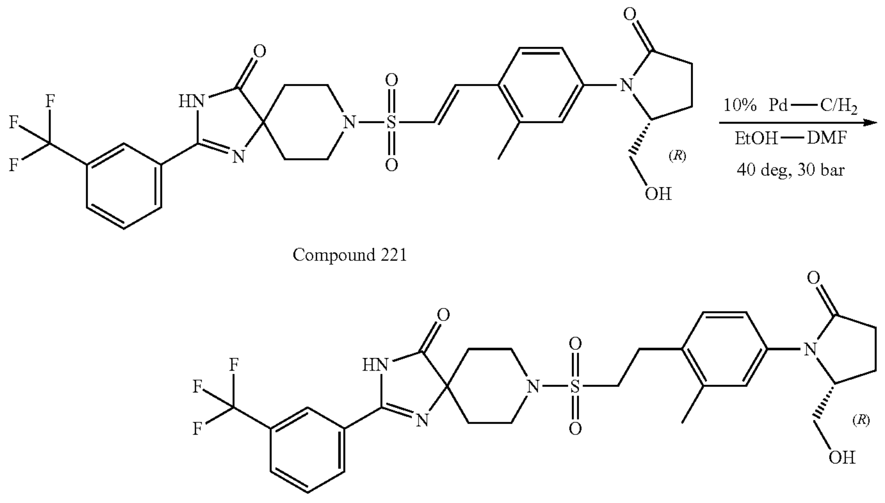

Compound 221

Compound 268

The following reaction was performed by utilizing a continuous-flow hydrogenation reactor H-Cube® Type HC-2 (ThalesNano Nanotechnology Inc.).

8-{(E)-2-[4-((R)-2-Hydroxymethyl-5-oxo-pyrrolidin-1-yl)-2-methyl-phenyl]-ethenesulfonyl}-2-(3-trifluoromethyl-phenyl)-1,3,8-triaza-spiro[4.5]dec-1-en-4-one (28.5 mg, 48.3 µmol) was dissolved in EtOH/DMF 4:1 (concentration 10 mg/ml). The mixture was allowed to pass through 10% Pd/C (CatCart™) at a flow rate of 2 ml/min under the conditions of 30 bar and 40° C. in a hydrogen atmosphere, and was subjected to hydrogenation reaction. The resulting reaction solution was concentrated under reduced pressure. The residue was purified by preparative TLC($CH_2Cl_2$/MeOH=20:1) to give 8-{2-[4-((R)-2-hydroxymethyl-5-oxo-pyrrolidin-1-yl)-2-methyl-phenyl]-ethanesulfonyl}-2-(3-trifluoromethyl-phenyl)-1,3,8-triaza-spiro[4.5]dec-1-en-4-one as a white powder (12.9 mg, 45%).

$^1$H-NMR (270 MHz, $CDCl_3$) δ 1.60-1.63 (2H, m), 1.83-1.89 (2H, m), 1.97-2.04 (1H, m), 2.12-2.22 (1H, m), 2.32 (3H, s), 2.28-2.36 (1H, m), 2.52-2.59 (1H, m), 2.97-3.01 (2H, m), 3.29-3.40 (6H, m), 3.67-3.70 (2H, m), 4.24-4.29 (1H, m), 4.80 (1H, t, J=5.4 Hz), 7.22-7.29 (2H, m), 7.79 (1H, br t, J=7.8 Hz), 7.98 (1H, br. d, J=7.8 Hz), 8.29 (1H, br. d, J=7.3 Hz), 8.33 (1H, br. s), 11.81 (1H, br. s). MS (ESI) m/z=593 (M+H)+.

The example compounds shown below were synthesized by operations similar to those in Example 43 using appropriate reagents and starting materials.

Compounds 269 to 302

TABLE 44

| Compound | Structure | LCMS or HPLC condition | Retention time (min) | MS (m/z) |
|---|---|---|---|---|
| 269 | 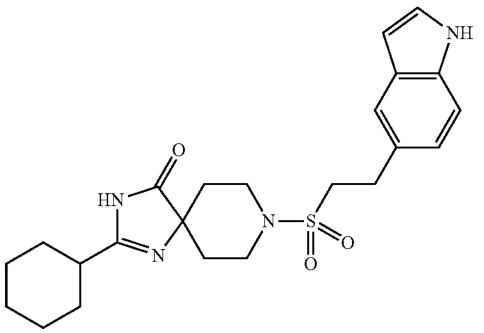 [SMILES: O=C1NC(C2CCCCC2)=NC12CCN(S(=O)(=O)CCc1ccc3[nH]ccc3c1)CC2] | LCMS-A-1 | 2.07 | 443 (M + H)+ |

TABLE 44-continued
| Compound | Structure | LCMS or HPLC condition | Retention time (min) | MS (m/z) |
|---|---|---|---|---|
| 270 | 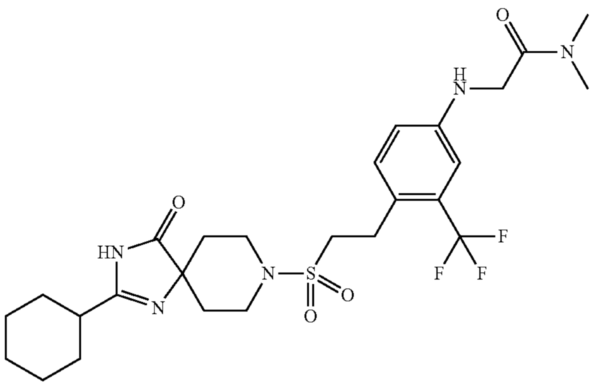 [SMILES: CN(C)C(=O)CNc1ccc(CCS(=O)(=O)N2CCC3(CC2)N=C(C2CCCCC2)NC3=O)c(C(F)(F)F)c1] | LCMS-C-1 | 2.55 | 572 (M + H)+ |
| 271 | 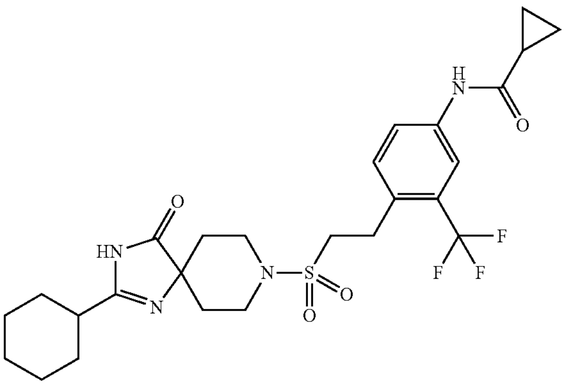 [SMILES: O=C(Nc1ccc(CCS(=O)(=O)N2CCC3(CC2)N=C(C2CCCCC2)NC3=O)c(C(F)(F)F)c1)C1CC1] | LCMS-C-1 | 2.67 | 555 (M + H)+ |
| 272 | 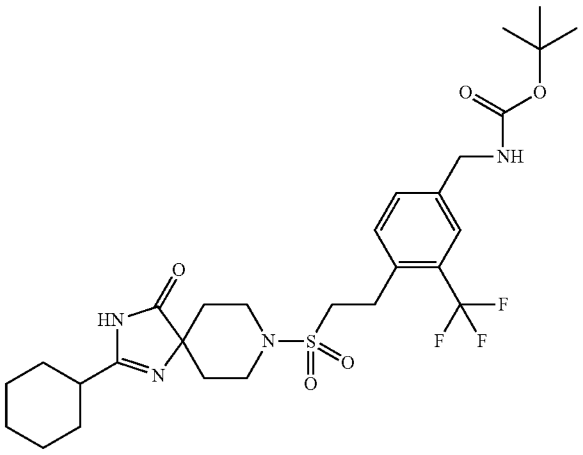 [SMILES: CC(C)(C)OC(=O)NCc1ccc(CCS(=O)(=O)N2CCC3(CC2)N=C(C2CCCCC2)NC3=O)c(C(F)(F)F)c1] | LCMS-C-1 | 2.87 | 601 (M + H)+ |

TABLE 44-continued
| Compound | Structure | LCMS or HPLC condition | Retention time (min) | MS (m/z) |
|---|---|---|---|---|
| 273 | 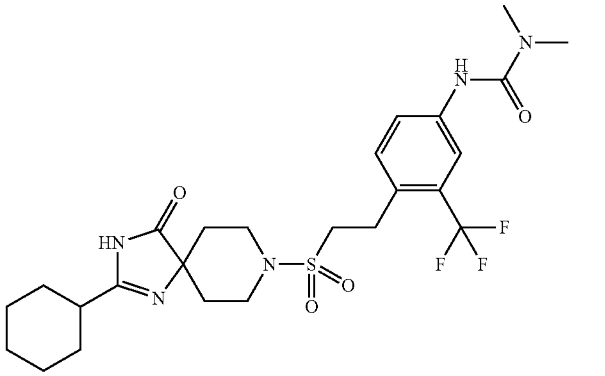 [SMILES: CN(C)C(=O)Nc1ccc(CCS(=O)(=O)N2CCC3(CC2)N=C(C2CCCCC2)NC3=O)c(C(F)(F)F)c1] | LCMS-C-1 | 2.53 | 558 (M + H)+ |
| 274 | 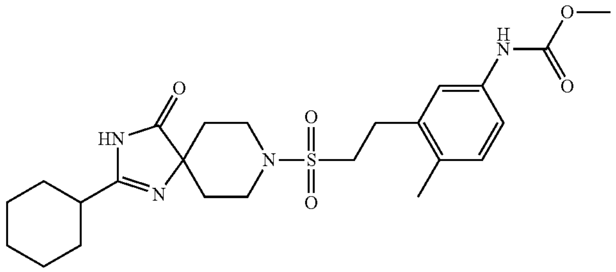 [SMILES: COC(=O)Nc1ccc(C)c(CCS(=O)(=O)N2CCC3(CC2)N=C(C2CCCCC2)NC3=O)c1] | LCMS-C-3 | 1.23 | 491 (M + H)+ |
| 275 | 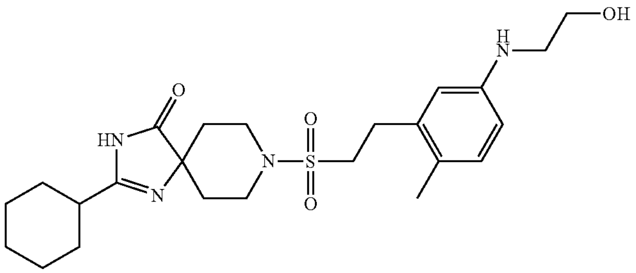 [SMILES: Cc1ccc(NCCO)cc1CCS(=O)(=O)N1CCC2(CC1)N=C(C1CCCCC1)NC2=O] | LCMS-C-3 | 1.06 | 477 (M + H)+ |
| 276 | 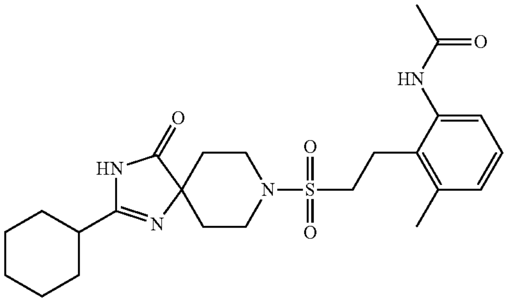 [SMILES: CC(=O)Nc1cccc(C)c1CCS(=O)(=O)N1CCC2(CC1)N=C(C1CCCCC1)NC2=O] | LCMS-C-3 | 0.86 | 475 (M + H)+ |
| 277 | 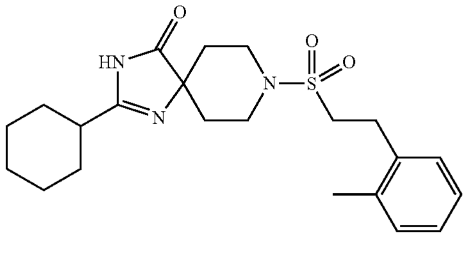 [SMILES: Cc1ccccc1CCS(=O)(=O)N1CCC2(CC1)N=C(C1CCCCC1)NC2=O] | LCMS-C-1 | 2.73 | 418 (M + H)+ |

TABLE 44-continued
| Compound | Structure | LCMS or HPLC condition | Retention time (min) | MS (m/z) |
|---|---|---|---|---|
| 278 | 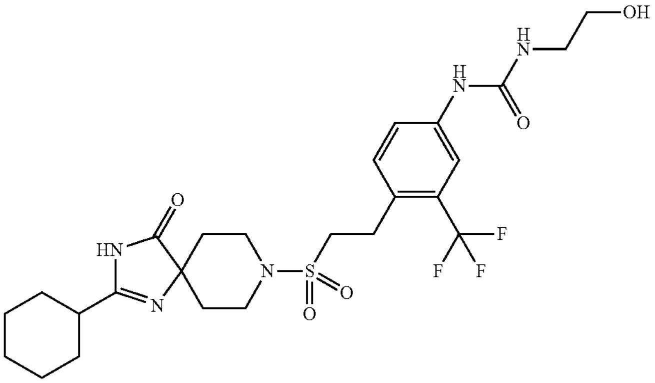 [SMILES: O=C(NCCO)Nc1ccc(CCS(=O)(=O)N2CCC3(CC2)N=C(C2CCCCC2)NC3=O)c(C(F)(F)F)c1] | LCMS-C-1 | 2.42 | 574 (M + H)+ |
| 279 | 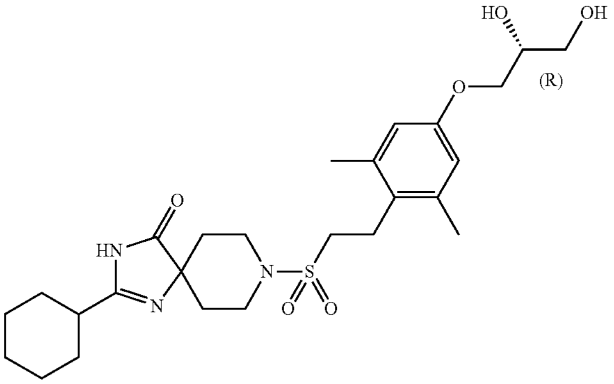 | LCMS-C-1 | 2.37 | 522 (M + H)+ |
| 280 | 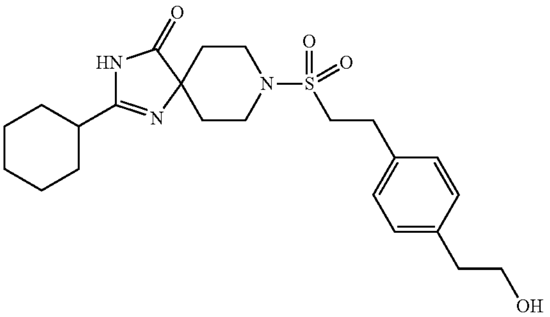 [SMILES: O=C1NC(C2CCCCC2)=NC12CCN(S(=O)(=O)CCc1ccc(CCO)cc1)CC2] | LCMS-C-1 | 2.33 | 448 (M + H)+ |
| 281 | 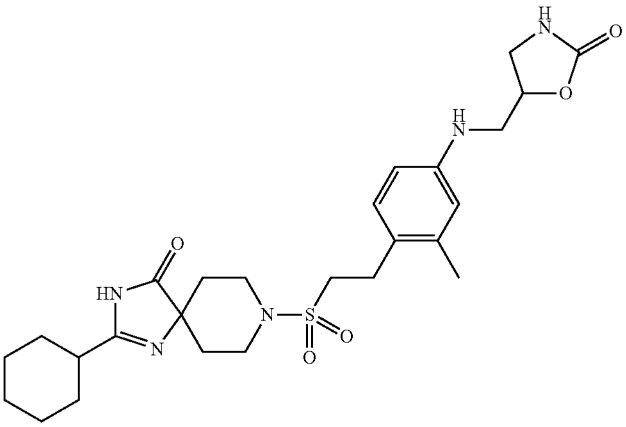 [SMILES: Cc1cc(NCC2CNC(=O)O2)ccc1CCS(=O)(=O)N1CCC2(CC1)N=C(C1CCCCC1)NC2=O] | LCMS-B-1 | 1.45 | 532 (M + H)+ |

TABLE 44-continued
| Compound | Structure | LCMS or HPLC condition | Retention time (min) | MS (m/z) |
|---|---|---|---|---|
| 282 | 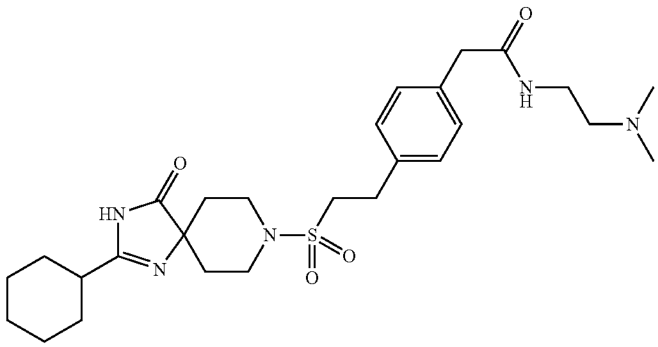 [SMILES: CN(C)CCNC(=O)Cc1ccc(CCS(=O)(=O)N2CCC3(CC2)N=C(C2CCCCC2)NC3=O)cc1] | LCMS-C-1 | 2.12 | 532 (M + H)+ |
| 283 | 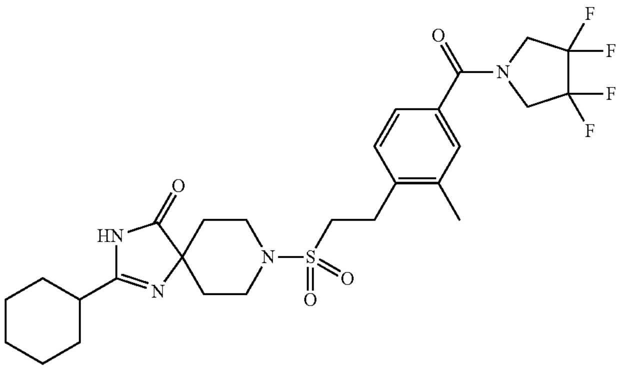 [SMILES: Cc1cc(C(=O)N2CC(F)(F)C(F)(F)C2)ccc1CCS(=O)(=O)N1CCC2(CC1)N=C(C1CCCCC1)NC2=O] | LCMS-C-1 | 2.70 | 587 (M + H)+ |
| 284 | 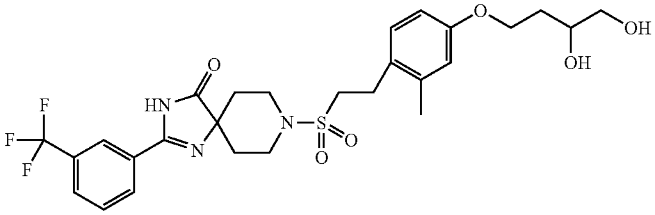 [SMILES: Cc1cc(OCCC(O)CO)ccc1CCS(=O)(=O)N1CCC2(CC1)N=C(c1cccc(C(F)(F)F)c1)NC2=O] | LCMS-C-2 | 1.85 | 584 (M + H)+ |
| 285 | 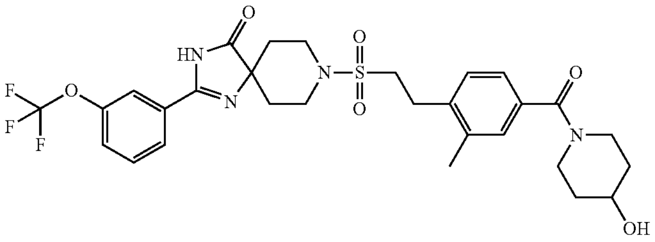 [SMILES: Cc1cc(C(=O)N2CCC(O)CC2)ccc1CCS(=O)(=O)N1CCC2(CC1)N=C(c1cccc(OC(F)(F)F)c1)NC2=O] | LCMS-A-1 | 2.23 | 623 (M + H)+ |
| 286 | 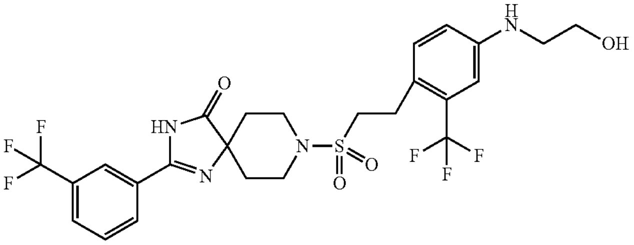 [SMILES: O=C1NC(c2cccc(C(F)(F)F)c2)=NC12CCN(S(=O)(=O)CCc1ccc(NCCO)cc1C(F)(F)F)CC2] | LCMS-C-2 | 2.03 | 593 (M + H)+ |

TABLE 44-continued
| Compound | Structure | LCMS or HPLC condition | Retention time (min) | MS (m/z) |
|---|---|---|---|---|
| 287 | 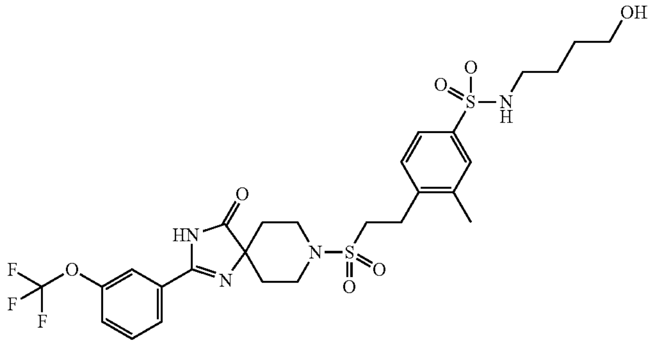 | LCMS-B-1 | 2.10 | 647 (M + H)+ |
| 288 | 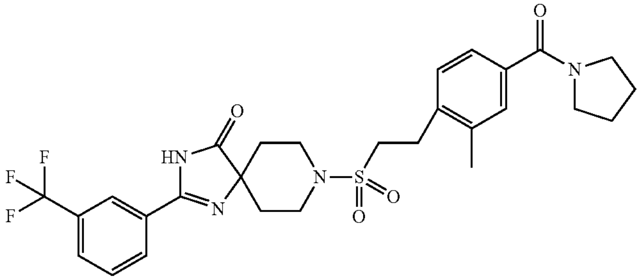 [SMILES: Cc1cc(C(=O)N2CCCC2)ccc1CCS(=O)(=O)N1CCC2(CC1)N=C(c1cccc(C(F)(F)F)c1)NC2=O] | LCMS-C-1 | 2.67 | 577 (M + H)+ |
| 289 | 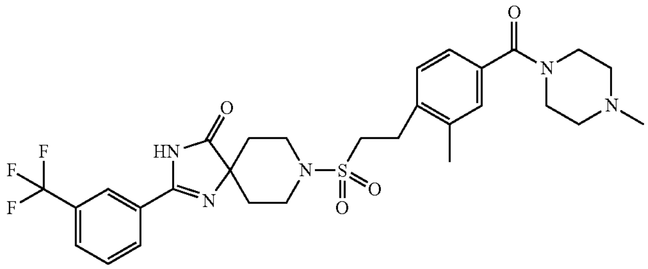 [SMILES: Cc1cc(C(=O)N2CCN(C)CC2)ccc1CCS(=O)(=O)N1CCC2(CC1)N=C(c1cccc(C(F)(F)F)c1)NC2=O] | LCMS-C-1 | 2.55 | 606 (M + H)+ |
| 290 | 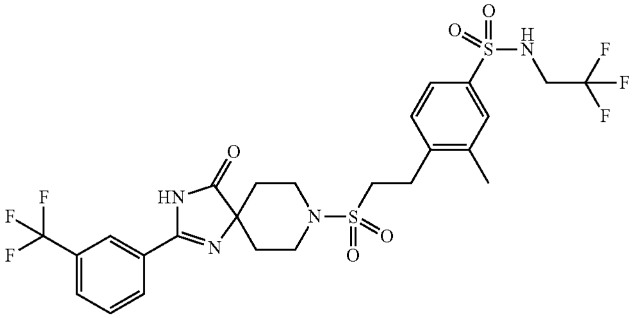 [SMILES: Cc1cc(S(=O)(=O)NCC(F)(F)F)ccc1CCS(=O)(=O)N1CCC2(CC1)N=C(c1cccc(C(F)(F)F)c1)NC2=O] | LCMS-C-1 | 2.65 | 641 (M + H)+ |
| 291 | 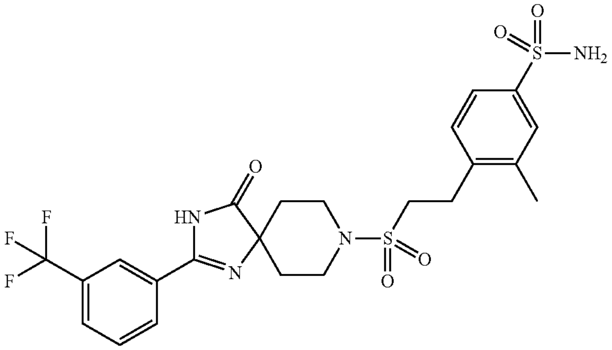 [SMILES: Cc1cc(S(N)(=O)=O)ccc1CCS(=O)(=O)N1CCC2(CC1)N=C(c1cccc(C(F)(F)F)c1)NC2=O] | LCMS-C-1 | 2.35 | 559 (M + H)+ |

TABLE 44-continued
| Compound | Structure | LCMS or HPLC condition | Retention time (min) | MS (m/z) |
|---|---|---|---|---|
| 292 | 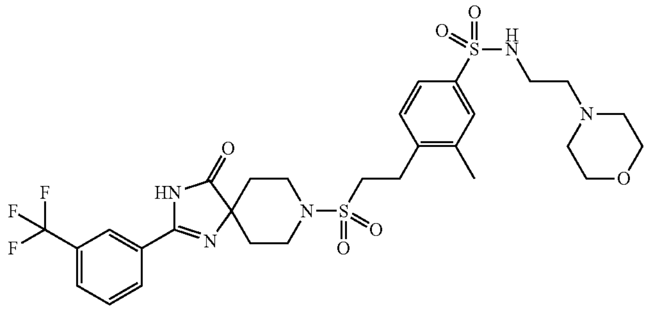 [SMILES: Cc1cc(S(=O)(=O)NCCN2CCOCC2)ccc1CCS(=O)(=O)N1CCC2(CC1)N=C(c1cccc(C(F)(F)F)c1)NC2=O] | LCMS-C-1 | 2.52 | 672 (M + H)+ |
| 293 | 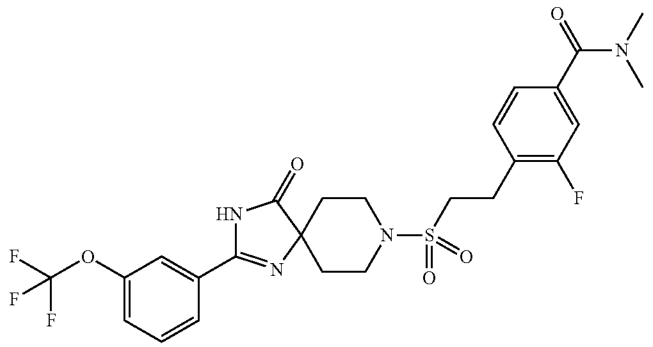 [SMILES: CN(C)C(=O)c1ccc(CCS(=O)(=O)N2CCC3(CC2)N=C(c2cccc(OC(F)(F)F)c2)NC3=O)c(F)c1] | LCMS-C-1 | 2.55 | 571 (M + H)+ |
| 294 | 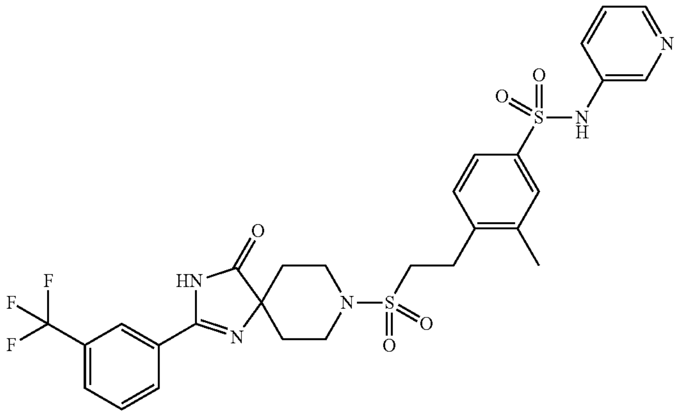 [SMILES: Cc1cc(S(=O)(=O)Nc2cccnc2)ccc1CCS(=O)(=O)N1CCC2(CC1)N=C(c1cccc(C(F)(F)F)c1)NC2=O] | LCMS-A-1 | 2.19 | 636 (M + H)+ |
| 295 | 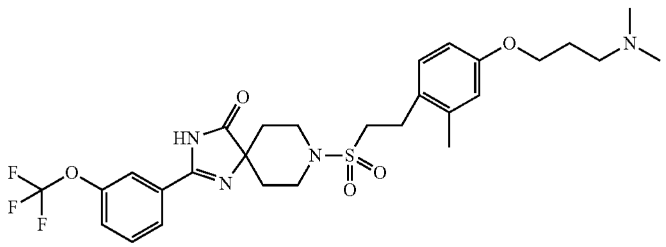 [SMILES: Cc1cc(OCCCN(C)C)ccc1CCS(=O)(=O)N1CCC2(CC1)N=C(c1cccc(OC(F)(F)F)c1)NC2=O] | LCMS-C-1 | 2.67 | 597 (M + H)+ |

TABLE 44-continued
| Compound | Structure | LCMS or HPLC condition | Retention time (min) | MS (m/z) |
|---|---|---|---|---|
| 296 | 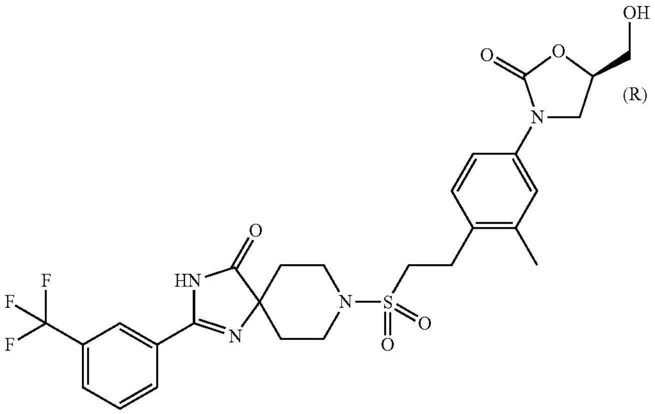 | LCMS-C-1 | 2.45 | 595 (M + H)+ |
| 297 | 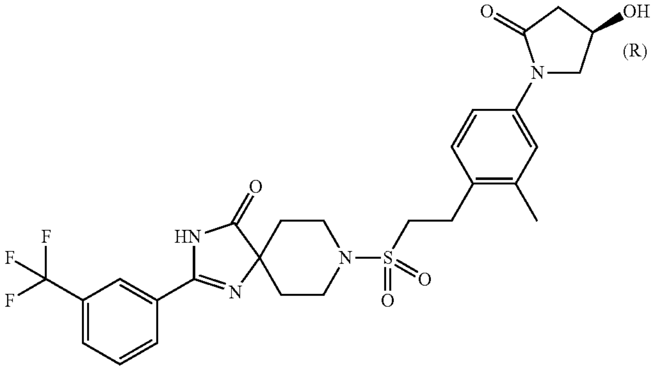 | LCMS-B-1 | 1.91 | 579 (M + H)+ |
| 298 | 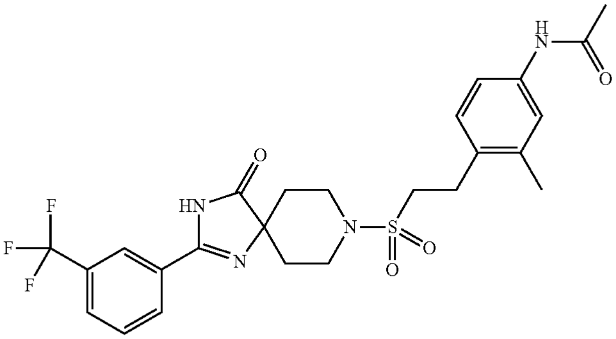 [SMILES: CC(=O)Nc1ccc(CCS(=O)(=O)N2CCC3(CC2)N=C(c2cccc(C(F)(F)F)c2)NC3=O)c(C)c1] | LCMS-C-1 | 2.52 | 537 (M + H)+ |
| 299 | 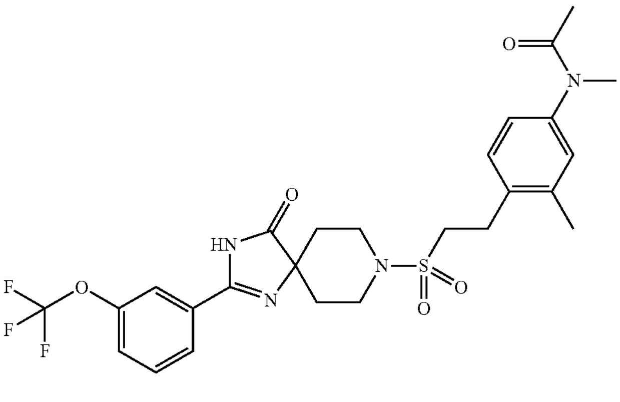 [SMILES: CC(=O)N(C)c1ccc(CCS(=O)(=O)N2CCC3(CC2)N=C(c2cccc(OC(F)(F)F)c2)NC3=O)c(C)c1] | LCMS-C-1 | 2.47 | 567 (M + H)+ |

TABLE 44-continued

| Compound | Structure | LCMS or HPLC condition | Retention time (min) | MS (m/z) |
|---|---|---|---|---|
| 300 | 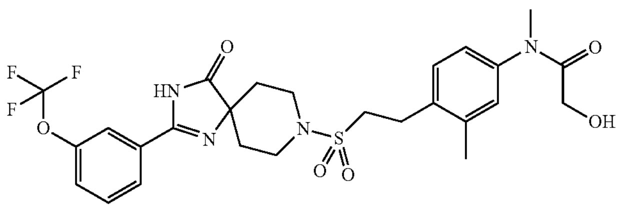 [SMILES: Cc1cc(N(C)C(=O)CO)ccc1CCS(=O)(=O)N1CCC2(CC1)N=C(c1cccc(OC(F)(F)F)c1)NC2=O] | LCMS-A-1 | 2.32 | 583 (M + H)+ |
| 301 | 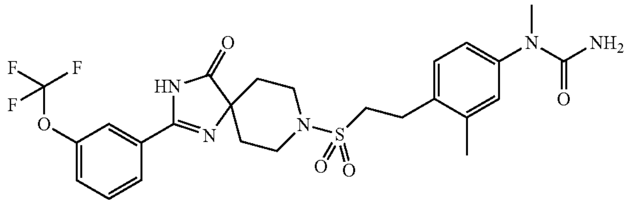 [SMILES: Cc1cc(N(C)C(N)=O)ccc1CCS(=O)(=O)N1CCC2(CC1)N=C(c1cccc(OC(F)(F)F)c1)NC2=O] | LCMS-A-1 | 2.28 | 568 (M + H)+ |
| 302 | 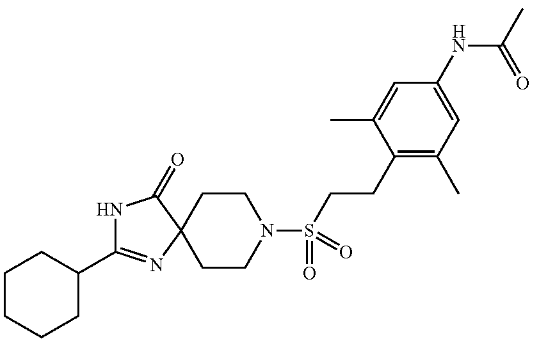 [SMILES: CC(=O)Nc1cc(C)c(CCS(=O)(=O)N2CCC3(CC2)N=C(C2CCCCC2)NC3=O)c(C)c1] | LCMS-B-1 | 1.61 | 489 (M + H)+ |

Example 44

2-Cyclohexyl-8-[2-(1H-indol-4-yl)-ethanesulfonyl]-1,3,8-triaza-spiro[4.5]dec-1-en-4-one (Compound 303)

(Reaction 44-1)

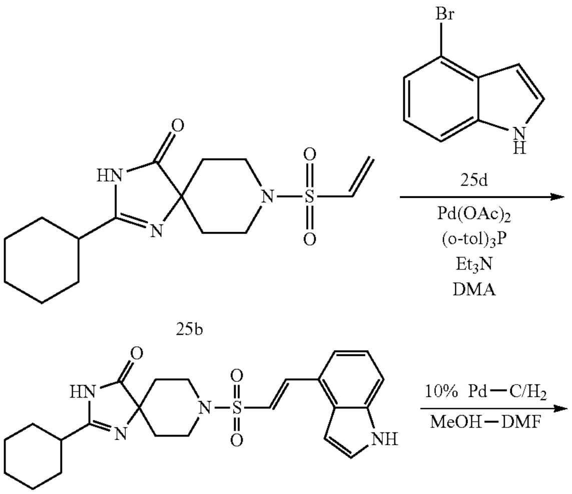

-continued

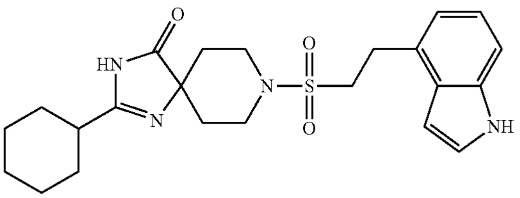

Compound 303

2-Cyclohexyl-8-[2-(1H-indol-4-yl)-ethanesulfonyl]-1,3,8-triaza-spiro[4.5]dec-1-en-4-one was synthesized by operations similar to those in Reaction 25-2 and Reaction 42-1 using appropriate reagents and starting material.

MS (ESI) m/z=443 (M+H)+.

The example compounds shown below were synthesized by operations similar to those in Example 44 using appropriate reagents and starting materials.

Compounds 304 to 320
TABLE 45
| Compound | Structure | LCMS or HPLC condition | Retention time (min) | MS (m/z) |
|---|---|---|---|---|
| 304 | 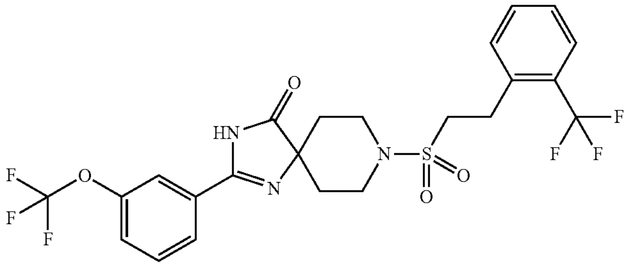 [SMILES: O=C1NC(c2cccc(OC(F)(F)F)c2)=NC12CCN(S(=O)(=O)CCc1ccccc1C(F)(F)F)CC2] | LCMS-A-1 | 2.92 | 550 (M + H)+ |
| 305 | 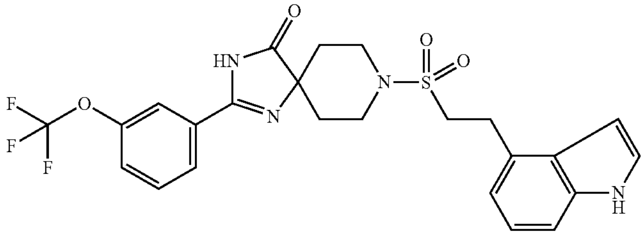 [SMILES: O=C1NC(c2cccc(OC(F)(F)F)c2)=NC12CCN(S(=O)(=O)CCc1cccc3[nH]ccc13)CC2] | LCMS-A-1 | 2.60 | 521 (M + H)+ |
| 306 | 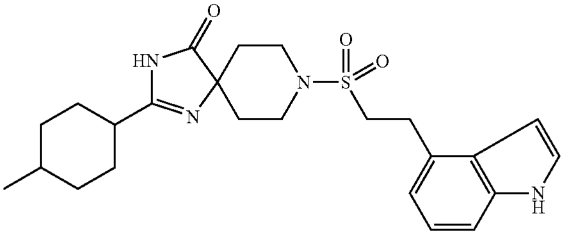 [SMILES: CC1CCC(C2=NC3(CCN(S(=O)(=O)CCc4cccc5[nH]ccc45)CC3)C(=O)N2)CC1] | LCMS-A-1 | 2.15 | 457 (M + H)+ |
| 307 | 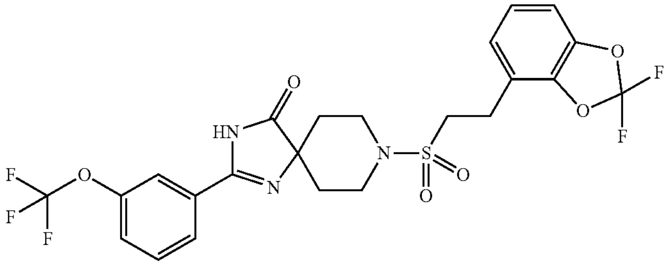 [SMILES: O=C1NC(c2cccc(OC(F)(F)F)c2)=NC12CCN(S(=O)(=O)CCc1cccc3c1OC(F)(F)O3)CC2] | LCMS-A-1 | 2.92 | 562 (M + H)+ |
| 308 | 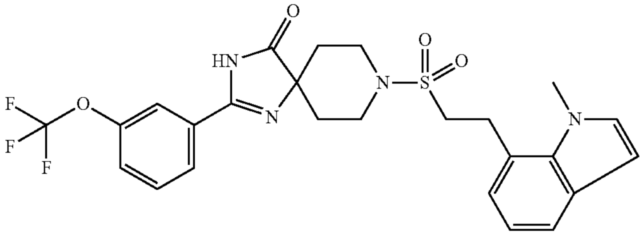 [SMILES: Cn1ccc2cccc(CCS(=O)(=O)N3CCC4(CC3)N=C(c3cccc(OC(F)(F)F)c3)NC4=O)c21] | LCMS-A-1 | 2.89 | 535 (M + H)+ |

TABLE 45-continued
| Compound | Structure | LCMS or HPLC condition | Retention time (min) | MS (m/z) |
|---|---|---|---|---|
| 309 | 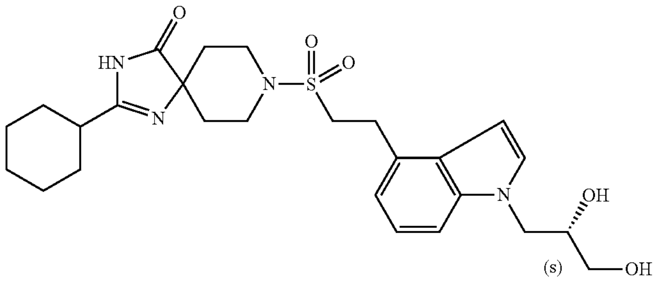 [SMILES: O=C1NC(C2CCCCC2)=NC12CCN(S(=O)(=O)CCc1cccc3c1ccn3C[C@H](O)CO)CC2] | LCMS-C-1 | 2.38 | 517 (M + H)+ |
| 310 | 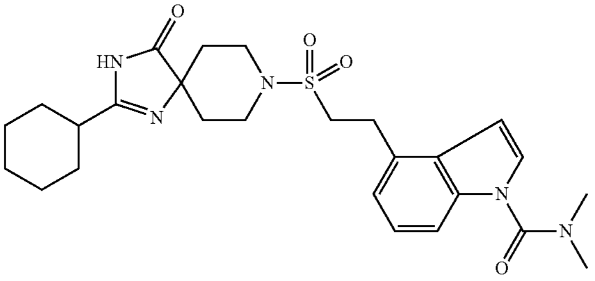 [SMILES: CN(C)C(=O)n1ccc2c(CCS(=O)(=O)N3CCC4(CC3)N=C(C3CCCCC3)NC4=O)cccc21] | LCMS-C-1 | 2.52 | 514 (M + H)+ |
| 311 | 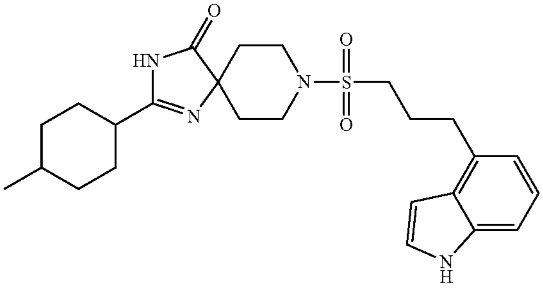 [SMILES: CC1CCC(C2=NC3(CCN(S(=O)(=O)CCCc4cccc5[nH]ccc45)CC3)C(=O)N2)CC1] | LCMS-E-7 | 1.53 | 471 (M + H)+ |
| 312 | 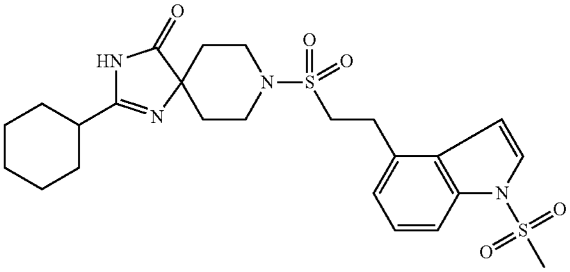 [SMILES: CS(=O)(=O)n1ccc2c(CCS(=O)(=O)N3CCC4(CC3)N=C(C3CCCCC3)NC4=O)cccc21] | LCMS-C-1 | 2.57 | 521 (M + H)+ |
| 313 | 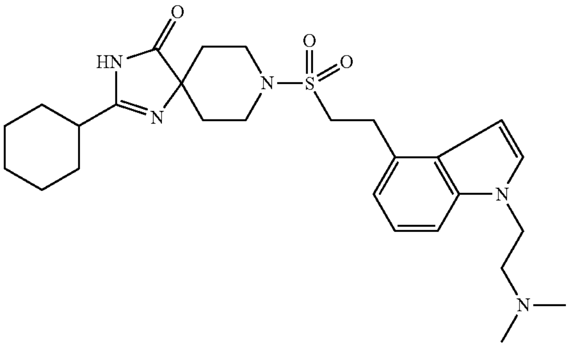 [SMILES: CN(C)CCn1ccc2c(CCS(=O)(=O)N3CCC4(CC3)N=C(C3CCCCC3)NC4=O)cccc21] | LCMS-A-1 | 1.65 | 514 (M + H)+ |

TABLE 45-continued
| Compound | Structure | LCMS or HPLC condition | Retention time (min) | MS (m/z) |
|---|---|---|---|---|
| 314 | 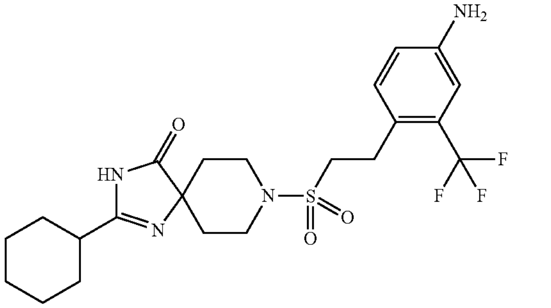 [SMILES: Nc1ccc(CCS(=O)(=O)N2CCC3(CC2)N=C(C2CCCCC2)NC3=O)c(C(F)(F)F)c1] | LCMS-C-1 | 2.48 | 487 (M + H)+ |
| 315 | 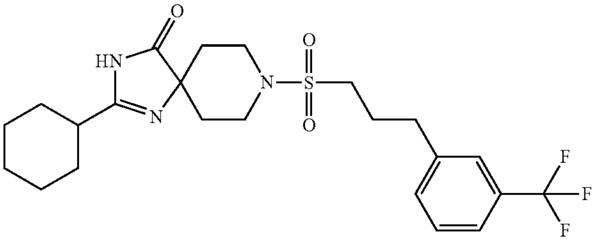 [SMILES: O=C1NC(C2CCCCC2)=NC12CCN(S(=O)(=O)CCCc1cccc(C(F)(F)F)c1)CC2] | HPLC-A-1 | 13.4 | 486 (M + H)+ |
| 316 | 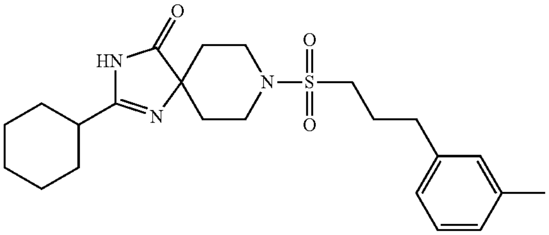 [SMILES: Cc1cccc(CCCS(=O)(=O)N2CCC3(CC2)N=C(C2CCCCC2)NC3=O)c1] | HPLC-A-2 | 11.6 | 432 (M + H)+ |
| 317 | 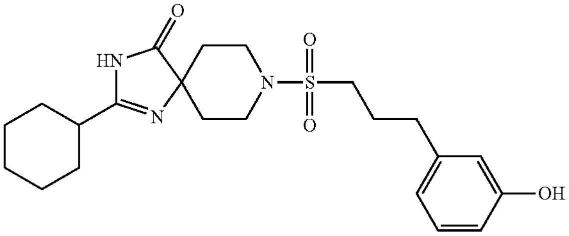 [SMILES: O=C1NC(C2CCCCC2)=NC12CCN(S(=O)(=O)CCCc1cccc(O)c1)CC2] | LCMS-D-1 | 1.8 | 434 (M + H)+ |
| 318 | 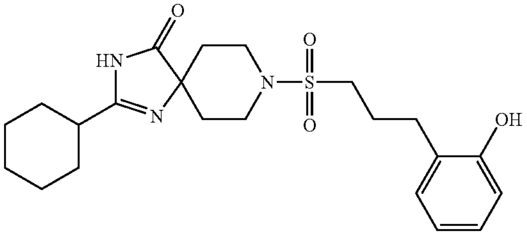 [SMILES: O=C1NC(C2CCCCC2)=NC12CCN(S(=O)(=O)CCCc1ccccc1O)CC2] | LCMS-D-1 | 3.0 | 434 (M + H)+ |
| 319 | 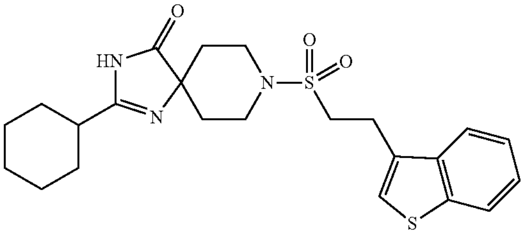 [SMILES: O=C1NC(C2CCCCC2)=NC12CCN(S(=O)(=O)CCc1csc3ccccc13)CC2] | LCMS-C-1 | 2.87 | 460 (M + H)+ |

TABLE 45-continued

| Compound | Structure | LCMS or HPLC condition | Retention time (min) | MS (m/z) |
|---|---|---|---|---|
| 320 | 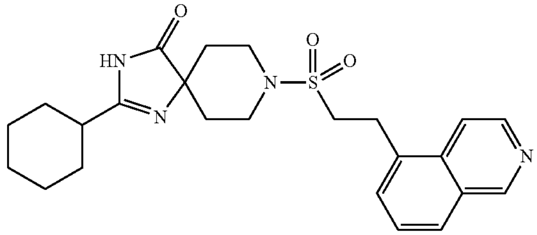 [SMILES: O=C1NC(C2CCCCC2)=NC12CCN(S(=O)(=O)CCc1cccc3cnccc13)CC2] | LCMS-A-1 | 1.49 | 455 (M + H)+ |

The aryl bromide reagent used in the synthesis of Compound 313 ([2-(4-bromo-indol-1-yl)-ethyl]-dimethyl-amine) was synthesized as follows.

(Reaction 44-2)

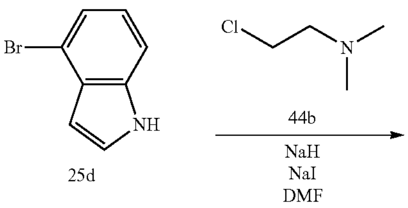

25d

-continued

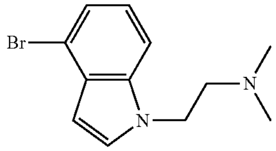

44c

[2-(4-Bromo-indol-1-yl)-ethyl]-dimethyl-amine was synthesized by operations similar to those in Reaction 25-3 using appropriate reagents and starting material.

MS (ESI) m/z=267, 269 (M+H)+.

Example 45

2-Cyclohexyl-8-{2-[4-((S)-2,3-dihydroxy-propylamino)-2-methyl-phenyl]-ethanesulfonyl}-1,3,8-triaza-spiro[4.5]dec-1-en-4-one (Compound 321)

(Reaction 45-1)

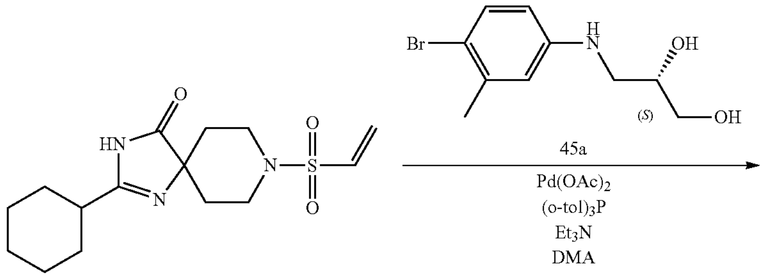

25b

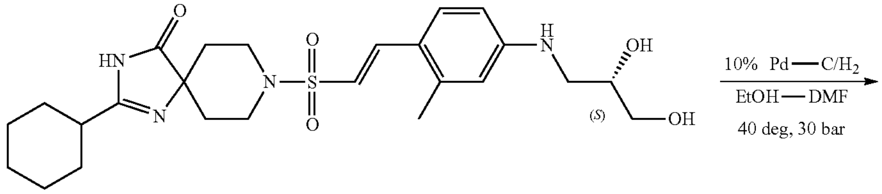

45b

-continued

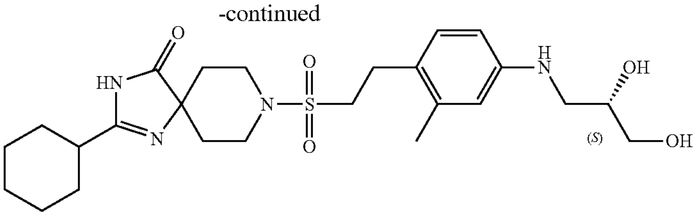

Compound 321

2-Cyclohexyl-8-{2-[4-((S)-2,3-dihydroxy-propylamino)-2-methyl-phenyl]-ethanesulfonyl}-1,3,8-triaza-spiro[4.5]dec-1-en-4-one was synthesized by operations similar to those in Reaction 25-2 and Reaction 42-2 using appropriate reagents and starting material.

MS (ESI) m/z=527 (M+H)+.

The example compound shown below was synthesized by operations similar to those in Example 45 using appropriate reagents and starting material.

Compound 322

-continued

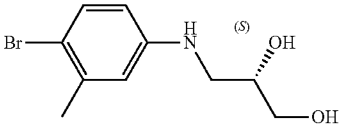

45a (S)-3-(4-Bromo-3-methyl-phenylamino)-propane-1,2-diol was synthesized by operations similar to those in Reaction 26-4 and Reaction 25-4 using appropriate reagents and starting material.

MS (ESI) m/z=260, 262 (M+H)+.

TABLE 46

| Compound | Structure | LCMS or HPLC condition | Retention time (min) | MS (m/z) |
|---|---|---|---|---|
| 322 | 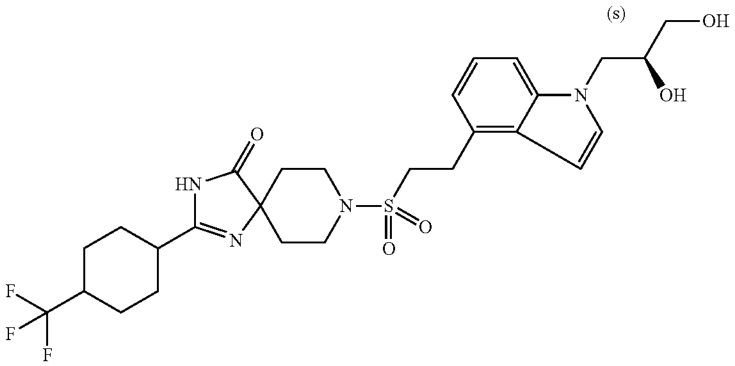 [SMILES: O=C1NC(C2CCC(C(F)(F)F)CC2)=NC12CCN(S(=O)(=O)CCc1cccc3c1ccn3C[C@H](O)CO)CC2] | LCMS-C-1 | 2.48 | 585 (M + H)+ |

The aryl bromide reagent used in the synthesis of Compound 321 ((S)-3-(4-bromo-3-methyl-phenylamino)-propane-1,2-diol) was synthesized as follows.

(Reaction 45-2)

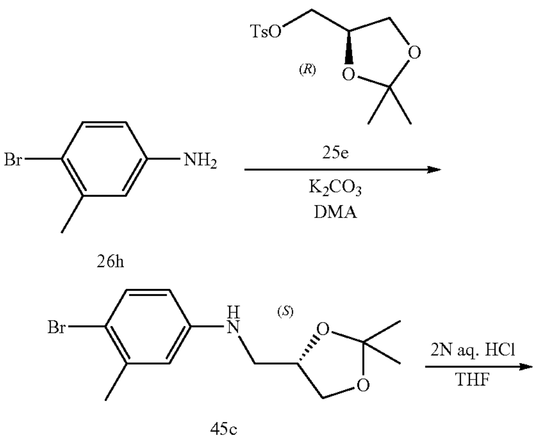

26h

45c

Example 46

2-Cyclohexyl-8-[2-(2-trifluoromethyl-phenyl)-ethanesulfonyl]-1,3,8-triaza-spiro[4.5]dec-1-en-4-one (Compound 323)

(Reaction 46-1)

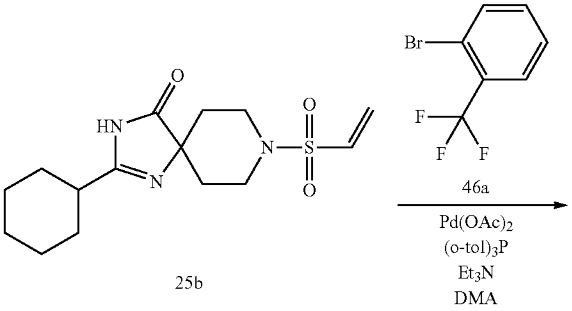

25b

-continued

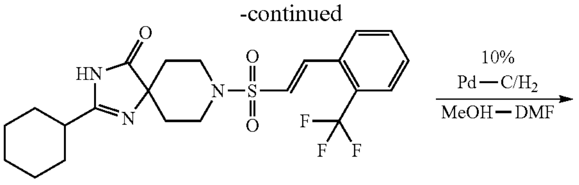

46b

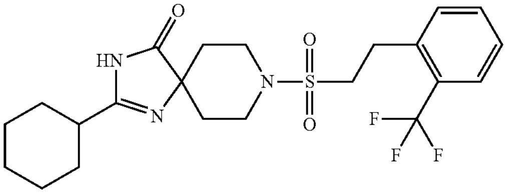

Compound 323

2-Cyclohexyl-8-[2-(2-trifluoromethyl-phenyl)-ethane-sulfonyl]-1,3,8-triaza-spiro[4.5]dec-1-en-4-one was synthesized by operations similar to those in Reaction 26-1 and Reaction 42-1 using appropriate reagents and starting material.

MS (ESI) m/z=472 (M+H)+.

The example compound shown below was synthesized by operations similar to those in Example 46 using appropriate reagents and starting material.

Compound 324

TABLE 47

| Compound | Structure | LCMS or HPLC condition | Retention time (min) | MS (m/z) |
|---|---|---|---|---|
| 324 | 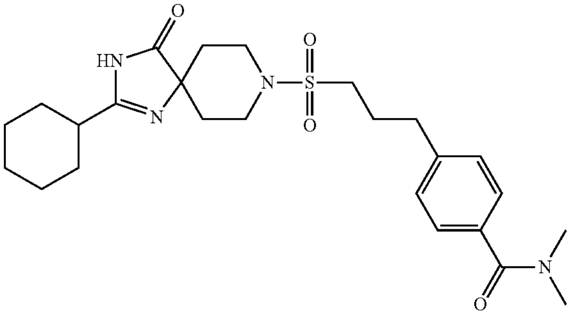 [SMILES: CN(C)C(=O)c1ccc(CCCS(=O)(=O)N2CCC3(CC2)N=C(C2CCCCC2)NC3=O)cc1] | LCMS-D-1 | 2.7 | 489 (M + H)+ |

Example 47

8-{2-[4-((R)-2,3-Dihydroxy-propoxy)-2-methyl-phenyl]-ethanesulfonyl}-2-(3-trifluoromethoxy-phenyl)-1,3,8-triaza-spiro[4.5]dec-1-en-4-one (Compound 325)

(Reaction 47-1)

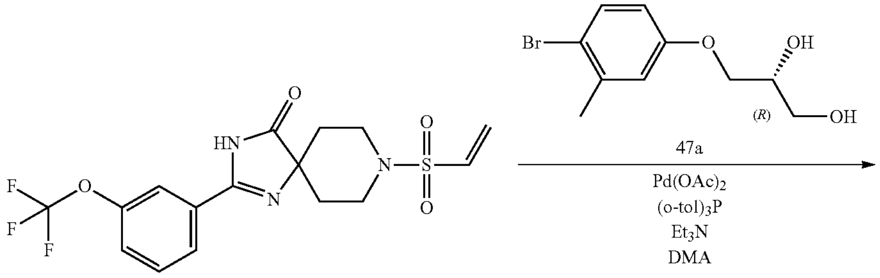

30a

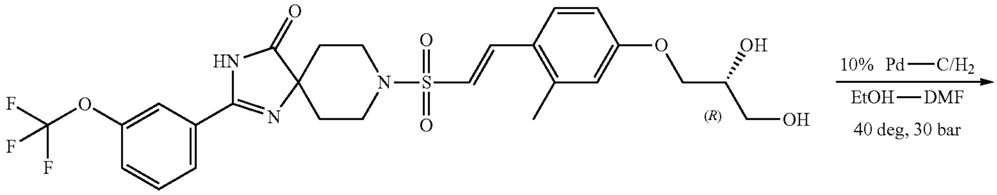

47b

-continued

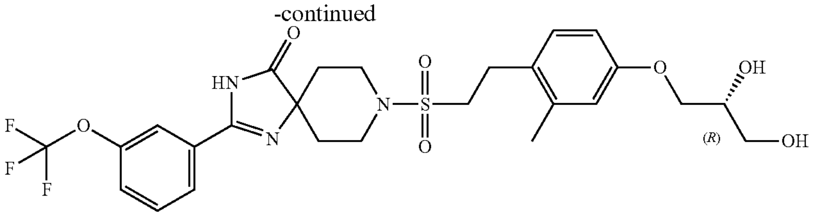

Compound 325

8-{2-[4-((R)-2,3-Dihydroxy-propoxy)-2-methyl-phenyl]-ethanesulfonyl}-2-(3-trifluoromethoxy-phenyl)-1,3,8-triaza-spiro[4.5]dec-1-en-4-one was synthesized by operations similar to those in Reaction 26-1 and Reaction 42-2 using appropriate reagents and starting material.

MS (ESI) m/z=586 (M+H)+.

The aryl bromide reagent used in the synthesis of Compound 325 ((R)-3-(4-bromo-3-methyl-phenoxy)-propane-1,2-diol) was synthesized as follows.

(Reaction 47-2)

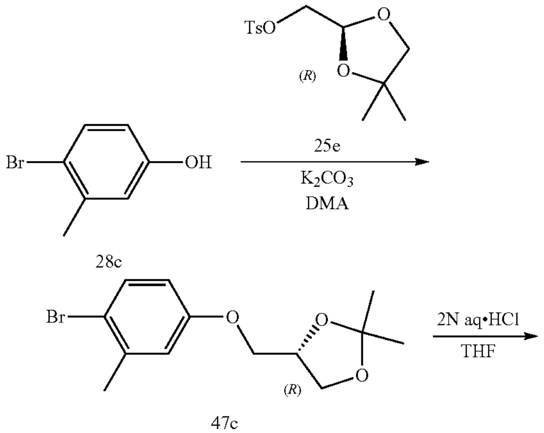

47c

-continued

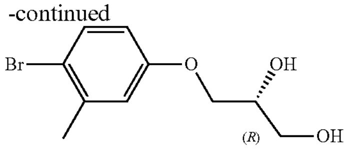

47a (R)-3-(4-Bromo-3-methyl-phenoxy)-propane-1,2-diol was synthesized by operations similar to those in Reaction 26-4 and Reaction 25-4 using appropriate reagents and starting material.

MS (ESI) m/z=283, 285 (M+Na)+.

Example 48

N-(2-Hydroxy-ethyl)-N-(4-methyl-3-{2-[4-oxo-2-(3-trifluoromethoxy-phenyl)-1,3,8-triaza-spiro[4.5]dec-1-ene-8-sulfonyl]-ethyl}-phenyl)-acetamide (Compound 326)

(Reaction 48-1)

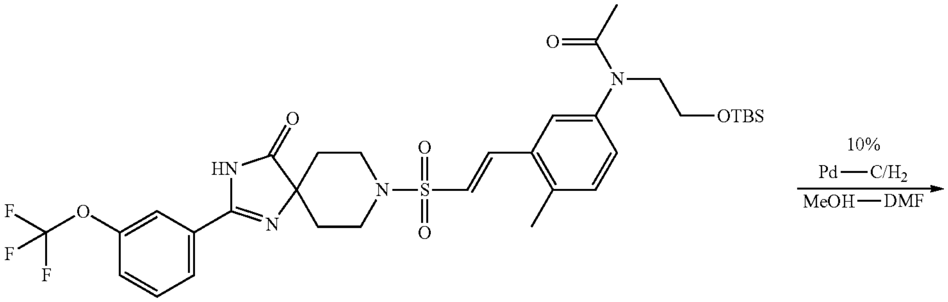

48a

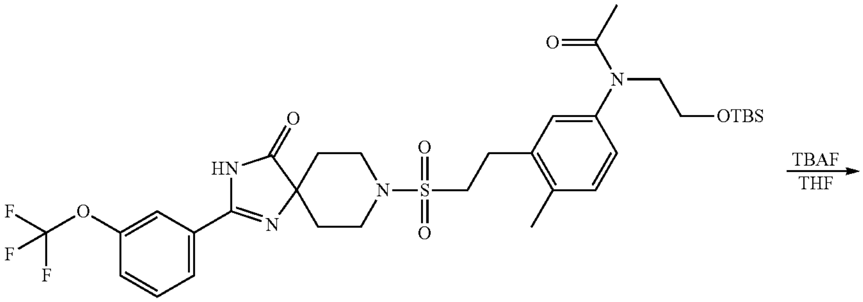

48b

-continued

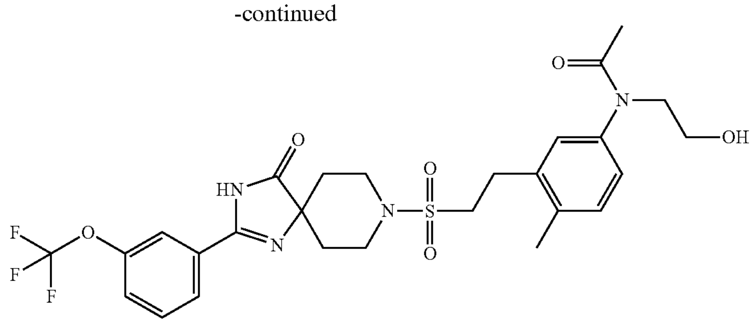

Compound 326

N-(2-Hydroxy-ethyl)-N-(4-methyl-3-{2-[4-oxo-2-(3-trifluoromethoxy-phenyl)-1,3,8-triaza-spiro[4.5]dec-1-ene-8-sulfonyl]-ethyl}-phenyl)-acetamide was synthesized by operations similar to those in Reaction 42-1 and Reaction 39-2 using appropriate reagents and starting material.

MS (ESI) m/z=597 (M+H)+.

Example 49

N-(2-Hydroxy-ethyl)-N-(2-methyl-3-{2-[4-oxo-2-(3-trifluoromethoxy-phenyl)-1,3,8-triaza-spiro[4.5]dec-1-ene-8-sulfonyl]-ethyl}-phenyl)-acetamide (Compound 327)

(Reaction 49-1)

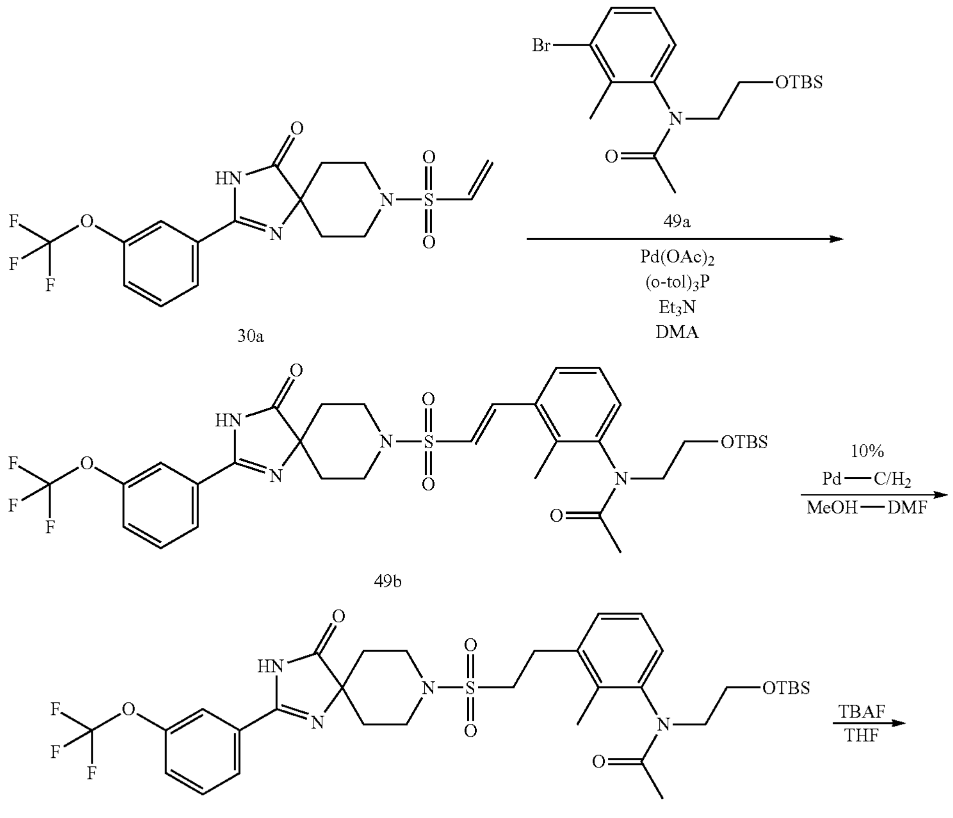

-continued

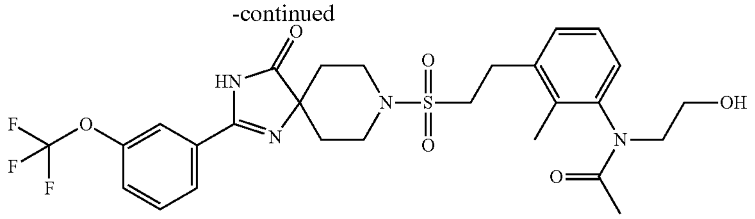

Compound 327

N-(2-Hydroxy-ethyl)-N-(2-methyl-3-{2-[4-oxo-2-(3-trifluoromethoxy-phenyl)-1,3,8-triaza-spiro[4.5]dec-1-ene-8-sulfonyl]-ethyl}-phenyl)-acetamide was synthesized by operations similar to those in Reaction 26-1, Reaction 42-1 and Reaction 39-2 using appropriate reagents and starting material.

MS (ESI) m/z=597 (M+H)+.

The aryl bromide reagent used in the synthesis of Compound 327 (N-(3-bromo-2-methyl-phenyl)-N-[2-(tert-butyl-dimethyl-silanyloxy)-ethyl]-acetamide) was synthesized as follows.

(Reaction 49-2)

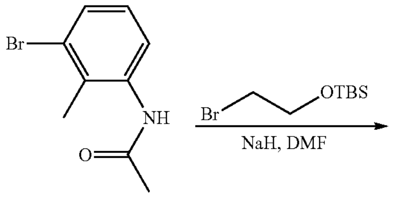

49d

-continued

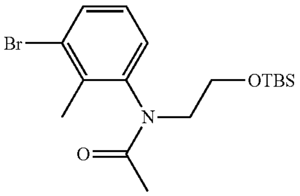

49a

N-(3-Bromo-2-methyl-phenyl)-N-[2-(tert-butyl-dimethyl-silanyloxy)-ethyl]-acetamide was synthesized by operations similar to those in Reaction 25-3 using appropriate reagents and starting material.

MS (ESI) m/z=386, 388 (M+H)+.

Example 50

8-[3-(3-Amino-phenyl)-propane-1-sulfonyl]-2-cyclohexyl-1,3,8-triaza-spiro[4.5]dec-1-en-4-one (Compound 328)

(Reaction 50-1)

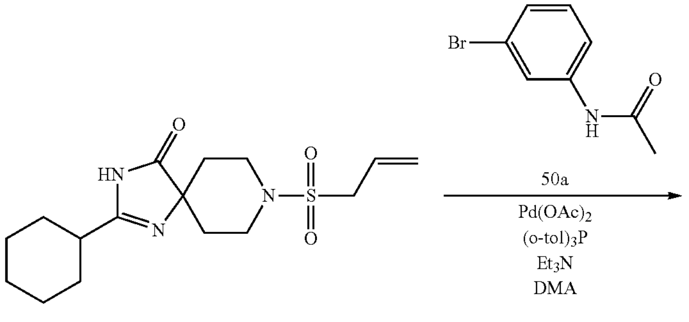

25b

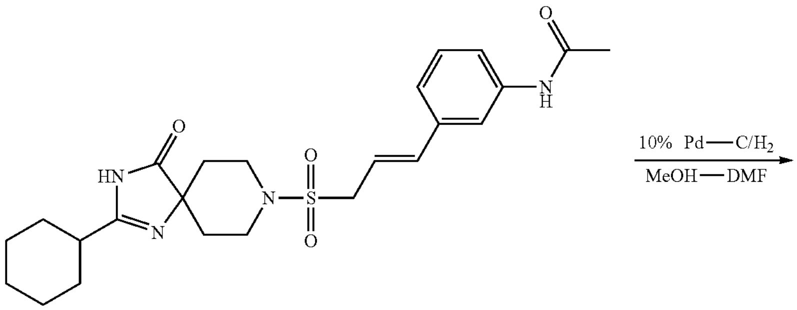

50b

-continued

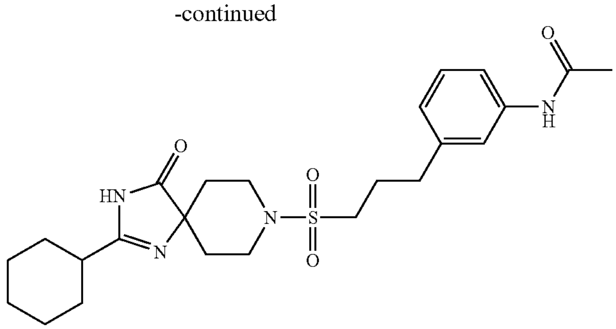

50c

N-{3-[3-(2-Cyclohexyl-4-oxo-1,3,8-triaza-spiro[4.5]dec-1-ene-8-sulfonyl)-propyl]-phenyl}-acetamide was synthesized by operations similar to those in Reaction 26-1 and Reaction 42-1 using appropriate reagents and starting material.

MS (ESI) m/z=475 (M+H)+.

(Reaction 50-2)

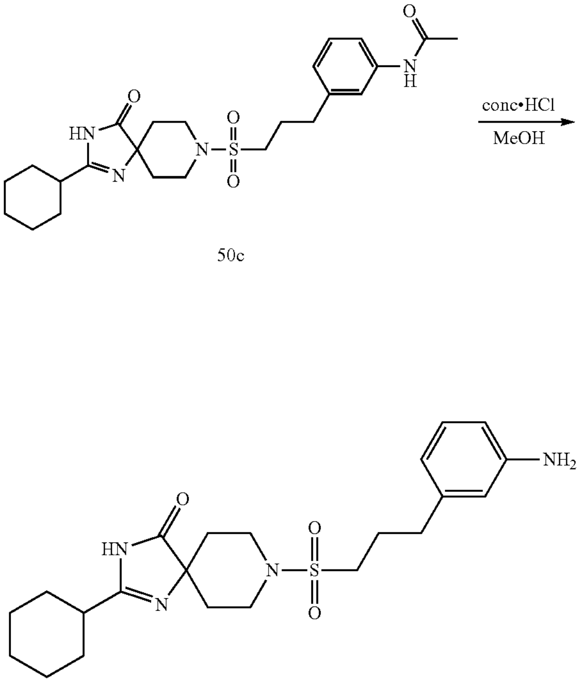

50c

Compound 328

Conc. HCl (0.5 ml) was added to a solution of N-{3-[3-(2-cyclohexyl-4-oxo-1,3,8-triaza-spiro[4.5]dec-1-ene-8-sulfonyl)-propyl]-phenyl}-acetamide (5.0 mg, 0.0105 mmol) in MeOH (1 ml) at room temperature. The mixture was stirred at 30 to 40° C. for four hours. The reaction mixture was concentrated under reduced pressure, and the resulting residue was then purified by preparative TLC ($CH_2Cl_2$:MeOH=10:1) to give 8-[3-(3-amino-phenyl)-propane-1-sulfonyl]-2-cyclohexyl-1,3,8-triaza-spiro[4.5]dec-1-en-4-one (2.5 mg, yield 55%).

Example 51

N,N-Dimethyl-4-{5-[4-oxo-2-(3-trifluoromethyl-phenyl)-1,3,8-triaza-spiro[4.5]dec-1-ene-8-sulfonyl]-thiophen-2-yl}-benzamide (Compound 329)

(Reaction 51-1)

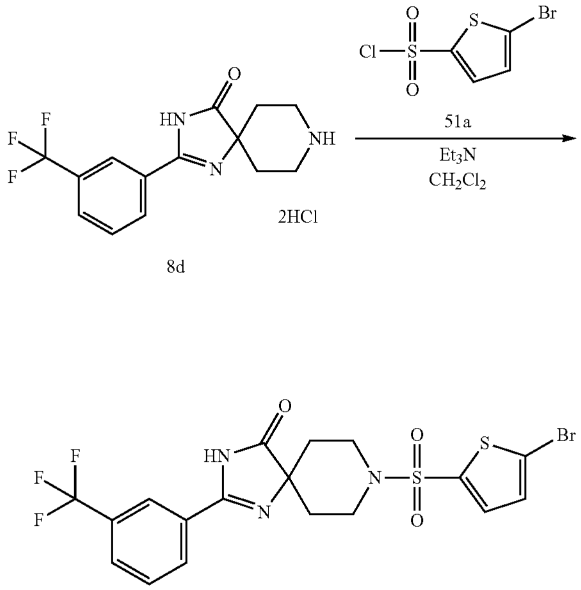

8d

51b 8-(5-Bromo-thiophene-2-sulfonyl)-2-(3-trifluoromethyl-phenyl)-1,3,8-triaza-spiro[4.5]dec-1-en-4-one was synthesized by operations similar to those in Reaction 5-4 using appropriate reagents and starting material.

MS (ESI) m/z=523 (M+H)+.

(Reaction 51-2)

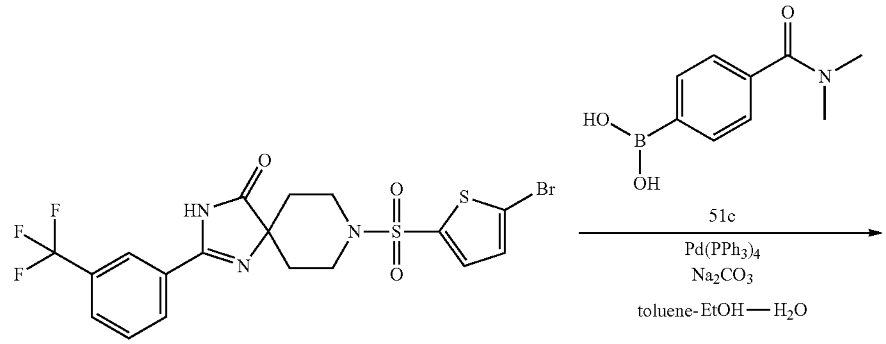

51b

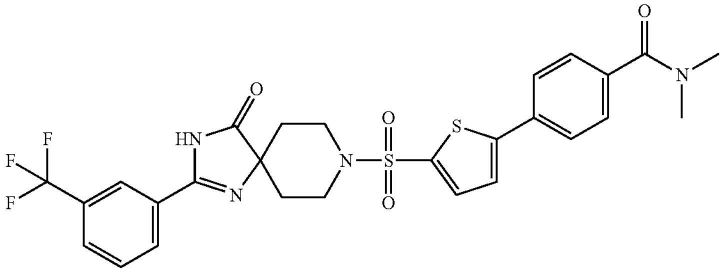

Compound 329

A mixture of 8-(5-bromo-thiophene-2-sulfonyl)-2-(3-trifluoromethyl-phenyl)-1,3,8-triaza-spiro[4.5]dec-1-en-4-one (11.1 mg, 0.0212 mmol), 4-(N,N-dimethylaminocarbonyl) phenylboronic acid (8.0 mg, 0.041 mmol), $Pd(PPh_3)_4$ (3.8 mg, 0.0033 mmol) and $Na_2CO_3$ (22.0 mg, 0.208 mmol) in toluene (0.12 ml)-EtOH (0.12 ml)-$H_2O$ (0.12 ml) was stirred at 85° C. for 20 hours in a sealed test tube in an $N_2$ atmosphere. The reaction mixture was cooled to room temperature and extracted with AcOEt. The organic layer was washed with a saturated aqueous $NH_4Cl$ solution, and then dried over $MgSO_4$ and concentrated under reduced pressure. The resulting residue was purified by silica gel column chromatography (AcOEt) to give N,N-dimethyl-4-{5-[4-oxo-2-(3-trifluoromethyl-phenyl)-1,3,8-triaza-spiro[4.5]dec-1-ene-8-sulfonyl]-thiophen-2-yl}-benzamide (9.7 mg, 77%).

$^1$H-NMR (300 MHz) ($CDCl_3$) δ 1.74 (2H, br d, J=13.5 Hz), 2.21 (2H, ddd, J=13.5, 11.0, and 4.0 Hz), 3.04 (3H, br s), 3.15 (3H, br s), 3.24 (2H, ddd, J=11.5, 11.0, and 3.0 Hz), 3.82 (2H, ddd, J=11.5, 4.0 and 4.0 Hz), 7.38 (1H, d, J=4.0 Hz), 7.50 (2H, d, J=8.4 Hz), 7.57 (1H, d, J=4.0 Hz), 7.60 (1H, t, J=8.1 Hz), 7.66 (2H, d, J=8.4 Hz), 7.78 (1H, d, J=8.1 Hz), 7.99 (1H, d, J=8.1 Hz), 8.12 (1H, s), 9.61 (1H, br s). MS (ESI) m/z=591 (M+H)+.

The example compounds shown below were synthesized by operations similar to those in Example 51 using appropriate reagents and starting materials.

Compounds 330 to 337

TABLE 48

| Compound | Structure | LCMS or HPLC condition | Retention time (min) | MS (m/z) |
|---|---|---|---|---|
| 330 | 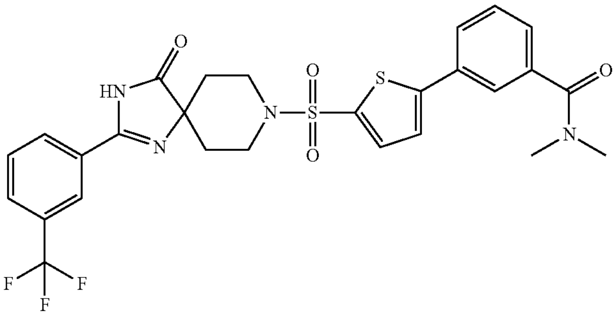 [SMILES: CN(C)C(=O)c1cccc(-c2ccc(S(=O)(=O)N3CCC4(CC3)N=C(c3cccc(C(F)(F)F)c3)NC4=O)s2)c1] | LCMS-C-2 | 2.08 | 591 (M + H)+ |

TABLE 48-continued
| Compound | Structure | LCMS or HPLC condition | Retention time (min) | MS (m/z) |
|---|---|---|---|---|
| 331 | 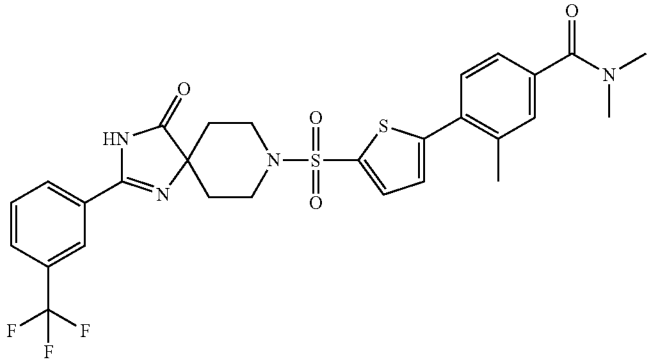 [SMILES: Cc1cc(C(=O)N(C)C)ccc1-c1ccc(S(=O)(=O)N2CCC3(CC2)N=C(c2cccc(C(F)(F)F)c2)NC3=O)s1] | LCMS-C-2 | 2.15 | 605 (M + H)+ |
| 332 | 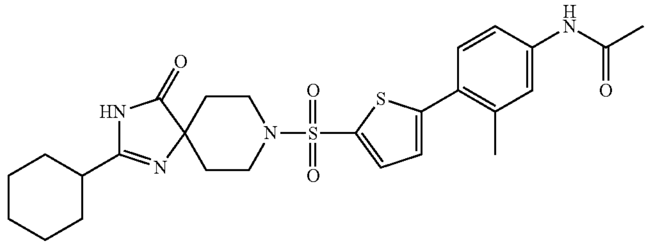 [SMILES: CC(=O)Nc1ccc(-c2ccc(S(=O)(=O)N3CCC4(CC3)N=C(C3CCCCC3)NC4=O)s2)c(C)c1] | LCMS-C-2 | 1.92 | 529 (M + H)+ |
| 333 | 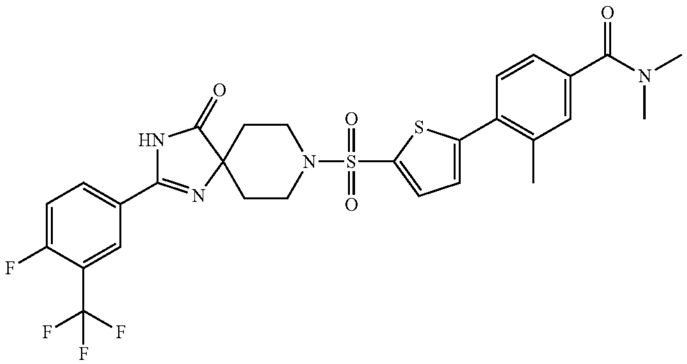 [SMILES: Cc1cc(C(=O)N(C)C)ccc1-c1ccc(S(=O)(=O)N2CCC3(CC2)N=C(c2ccc(F)c(C(F)(F)F)c2)NC3=O)s1] | LCMS-C-2 | 2.20 | 623 (M + H)+ |
| 334 | 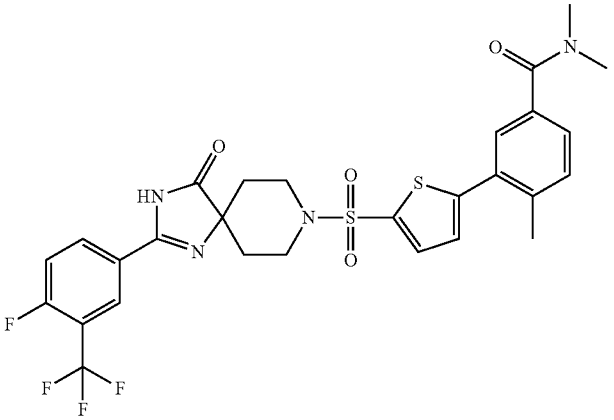 [SMILES: Cc1ccc(C(=O)N(C)C)cc1-c1ccc(S(=O)(=O)N2CCC3(CC2)N=C(c2ccc(F)c(C(F)(F)F)c2)NC3=O)s1] | LCMS-C-2 | 2.20 | 623 (M + H)+ |

TABLE 48-continued

| Compound | Structure | LCMS or HPLC condition | Retention time (min) | MS (m/z) |
|---|---|---|---|---|
| 335 | 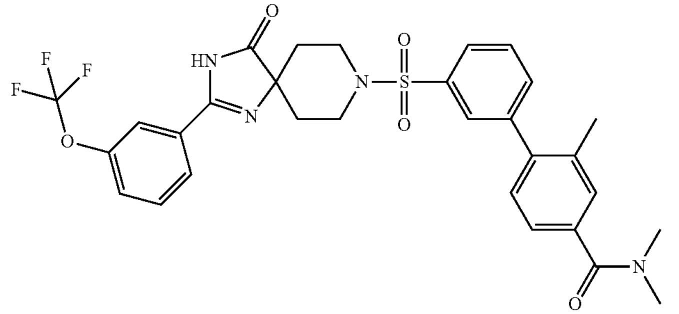 [SMILES: Cc1cc(C(=O)N(C)C)ccc1-c1cccc(S(=O)(=O)N2CCC3(CC2)N=C(c2cccc(OC(F)(F)F)c2)NC3=O)c1] | LCMS-D-1 | 3.37 | 615 (M + H)+ |
| 336 | 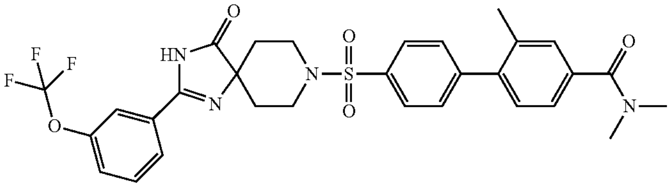 [SMILES: Cc1cc(C(=O)N(C)C)ccc1-c1ccc(S(=O)(=O)N2CCC3(CC2)N=C(c2cccc(OC(F)(F)F)c2)NC3=O)cc1] | LCMS-D-1 | 3.35 | 615 (M + H)+ |
| 337 | 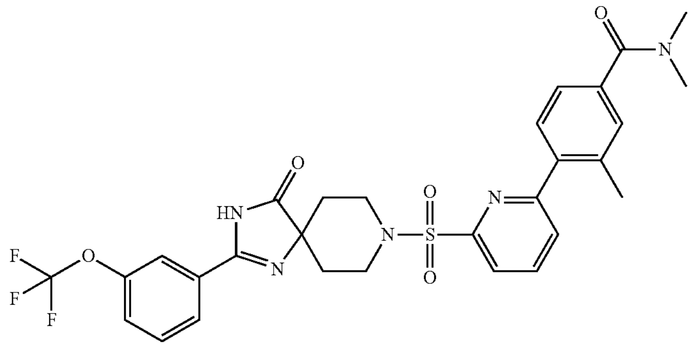 [SMILES: Cc1cc(C(=O)N(C)C)ccc1-c1cccc(S(=O)(=O)N2CCC3(CC2)N=C(c2cccc(OC(F)(F)F)c2)NC3=O)n1] | LCMS-D-1 | 3.27 | 616 (M + H)+ |

The aryl boronate reagent used in the synthesis of Compounds 331, 333, 335, 336 and 337 (3,N,N-trimethyl-4-(4,4,5,5-tetramethyl-[1,3,2]dioxaborolan-2-yl)-benzamide) was synthesized as follows.

(Reaction 51-3)

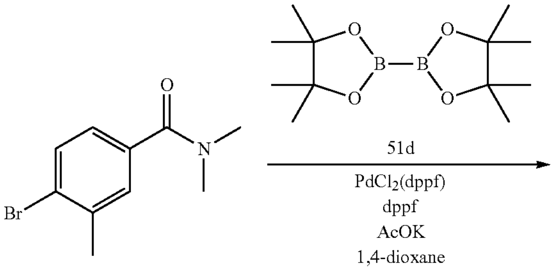

31d

-continued

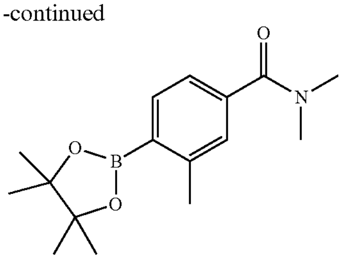

51e

A mixture of 4-bromo-3,N,N-trimethyl-benzamide (203 mg, 0.838 mmol), 1,1'-bis(diphenylphosphino)-ferrocene (dppf) (27.9 mg, 0.0503 mmol), $PdCl_2(dppf)-CH_2Cl_2$ (41.6 mg, 0.0509 mmol), AcOK (245 mg, 2.50 mmol) and bis (pinacolato)diboron (286 mg, 1.13 mmol) in dioxane (5.5 ml) was stirred at 85° C. for six hours in a sealed test tube in an $N_2$ atmosphere. The reaction mixture was cooled to room temperature and extracted with AcOEt. The organic layer was washed with water, and then dried over $MgSO_4$ and concentrated under reduced pressure. The resulting residue was purified by silica gel column chromatography (hexane/ethyl acetate=2/1) to give 3,N,N-trimethyl-4-(4,4,5,5-tetramethyl-[1,3,2]dioxaborolan-2-yl)-benzamide (135 mg, 56%).

MS (ESI) m/z=290 (M+H)+.

The aryl boronate reagent used in the synthesis of Compound 334 (4,N,N-trimethyl-3-(4,4,5,5-tetramethyl-[1,3,2]dioxaborolan-2-yl)-benzamide) was synthesized as follows.

(Reaction 51-4)

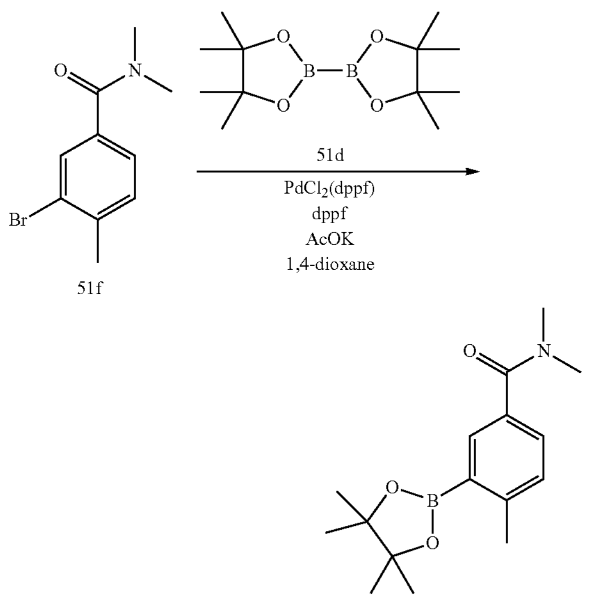

4,N,N-Trimethyl-3-(4,4,5,5-tetramethyl-[1,3,2]dioxaborolan-2-yl)-benzamide was synthesized by operations similar to those in Reaction 51-3 using appropriate reagents and starting material.

MS (ESI) m/z=242 (M+H)+.

The aryl boronate reagent used in the synthesis of Compound 332 (N-[3-methyl-4-(4,4,5,5-tetramethyl-[1,3,2]dioxaborolan-2-yl)-phenyl]-acetamide) was synthesized as follows.

(Reaction 51-5)

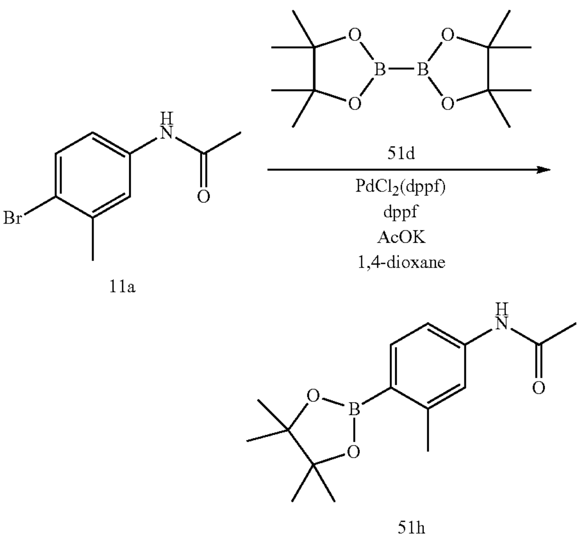

N-[3-Methyl-4-(4,4,5,5-tetramethyl-[1,3,2]dioxaborolan-2-yl)-phenyl]-acetamide was synthesized by operations similar to those in Reaction 51-3 using appropriate reagents and starting material.

MS (ESI) m/z=276 (M+H)+.

The following aryl bromide reagents used in the synthesis of Compounds 332, 333, 334, 335, 336 and 337 were synthesized by operations similar to those in Reaction 51-1 using appropriate reagents and starting materials.

TABLE 49

| Target Compound | Aryl bromide | MS |
|---|---|---|
| 332 | 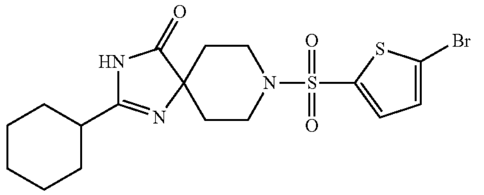 [SMILES: O=C1NC(C2CCCCC2)=NC12CCN(S(=O)(=O)c1ccc(Br)s1)CC2] | 460, 462 (M + H)+ |
| 333<br>334 | 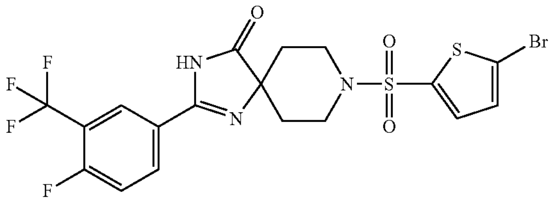 [SMILES: O=C1NC(c2ccc(F)c(C(F)(F)F)c2)=NC12CCN(S(=O)(=O)c1ccc(Br)s1)CC2] | 540, 542 (M + H)+ |
| 335 | 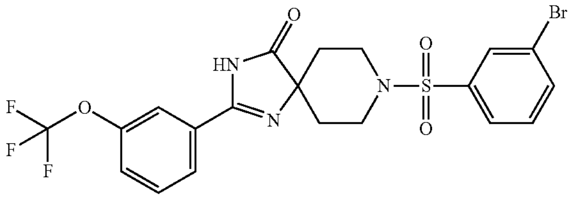 | 532, 534 (M + H)+ |

TABLE 49-continued

| Target Compound | Aryl bromide | MS |
|---|---|---|
| 336 | 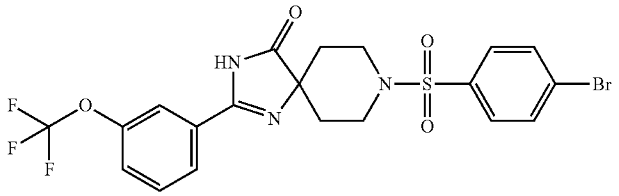 | 532, 534 (M + H)+ |
| 337 | 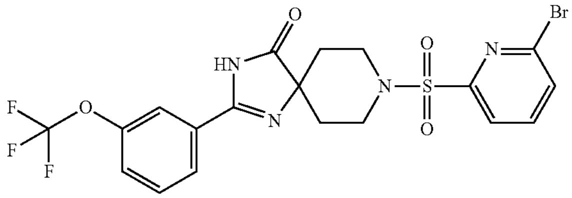 [SMILES: O=C1NC(c2cccc(OC(F)(F)F)c2)=NC12CCN(S(=O)(=O)c1cccc(Br)c1)CC2] | 533, 535 (M + H)+ |

Example 52

2-Cyclohexyl-8-{2-[2-(3,5-dimethyl-isoxazol-4-yl)-phenyl]-ethanesulfonyl}-1,3,8-triaza-spiro[4.5]dec-1-en-4-one (Compound 338)

(Reaction 52-1)

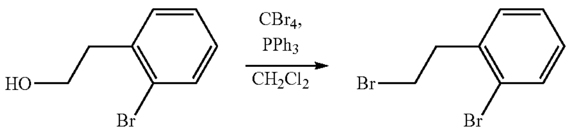

52a 52b

Triphenylphosphine (7.83 g, 29.8 mmol) and carbon tetrabromide (12.4 g, 37.3 mmol) were added to a solution of 2-(2-bromophenyl)ethanol (5.00 g, 24.9 mmol) in dichloromethane (123 mL). The mixture was stirred at room temperature for 15 hours, and a saturated aqueous sodium carbonate solution was then added. The organic layer and the aqueous layer were separated, and the organic layer was then concentrated under reduced pressure. The resulting residue was triturated with ethyl acetate:n-hexane (1:4, 200 mL) and then filtered, and the filtrate was concentrated under reduced pressure. The residue was purified by silica gel column chromatography to give 1-bromo-2-(2-bromoethyl)benzene as a colorless oil (6.23 g, 95%).

$^1$H-NMR (270 MHz, CDCl$_3$) δ 3.30 (2H, t, J=7.6 Hz), 3.60 (2H, t, J=7.3 Hz), 7.10-7.17 (1H, m), 7.26-7.28 (2H, m), 7.55 (1H, d, J=8.1 Hz).

(Reaction 52-2)

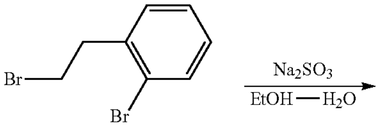

52b

-continued

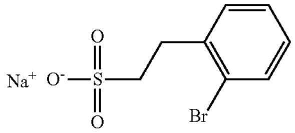

52c

A solution of 1-bromo-2-(2-bromoethyl)benzene (6.23 g, 23.6 mmol) in ethanol (20.5 mL) was added to a solution of sodium sulfite (3.12 g, 24.7 mmol) in water (25.0 mL). The mixture was heated at 100° C. for 24 hours. The reaction mixture was filtered, and the filtrate was then left to stand at 3° C. overnight. The resulting white crystals were collected by filtration and dried to give sodium 2-(2-bromo-phenyl) ethanesulfonate (4.00 g, 59%).

$^1$H-NMR (270 MHz, d$_6$-DMSO) δ 2.60-2.67 (2H, m), 2.94-3.00 (2H, m), 7.09-7.15 (1H, m), 7.25-7.33 (2H, m), 7.55 (1H, d, J=8.6 Hz).

(Reaction 52-3)

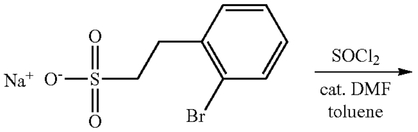

52c

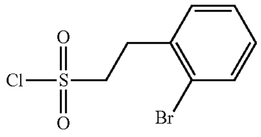

52d

N,N-Dimethylformamide (4.2 mL) and thionyl chloride (5.1 mL, 69.7 mmol) were sequentially added to a suspension of sodium 2-(2-bromo-phenyl)ethanesulfonate (4.00 g, 13.9 mmol) in toluene. The mixture was stirred at 100° C. for 66 hours and then poured into ice water. The organic layer and the aqueous layer were separated, and the aqueous layer was extracted with ether. The organic layers were combined and sequentially washed with water and saturated brine, and then dried over sodium sulfate and concentrated under reduced pressure to give 2-(2-bromophenyl)ethanesulfonyl chloride (4.10 g). This was used in the next step without further purification.

(Reaction 52-4)

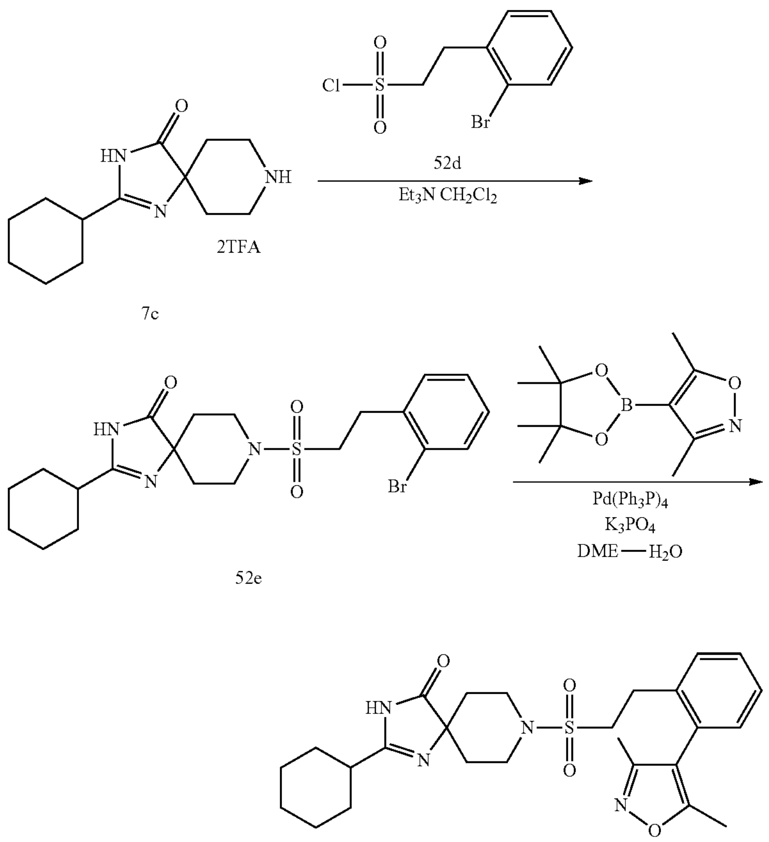

7c

52e

Compound 338

2-Cyclohexyl-8-{2-[2-(3,5-dimethyl-isoxazol-4-yl)-phenyl]-ethanesulfonyl}-1,3,8-triaza-spiro[4.5]dec-1-en-4-one was synthesized by operations similar to those in Reaction 5-4 and Reaction 21-1 using appropriate reagents and starting material.

MS (ESI) m/z=499 (M+H)+.

The example compounds shown below were synthesized by operations similar to those in Example 52 using appropriate reagents and starting materials.

Compounds 339 to 340

TABLE 50

| Compound | Structure | LCMS or HPLC condition | Retention time (min) | MS (m/z) |
|---|---|---|---|---|
| 339 | 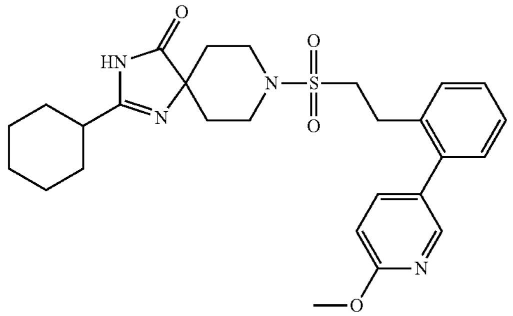 [SMILES: COc1ccc(-c2ccccc2CCS(=O)(=O)N2CCC3(CC2)N=C(C2CCCCC2)NC3=O)cn1] | LCMS-E-5 | 4.26 | 511 (M + H)+ |

TABLE 50-continued

| Compound | Structure | LCMS or HPLC condition | Retention time (min) | MS (m/z) |
|---|---|---|---|---|
| 340 | 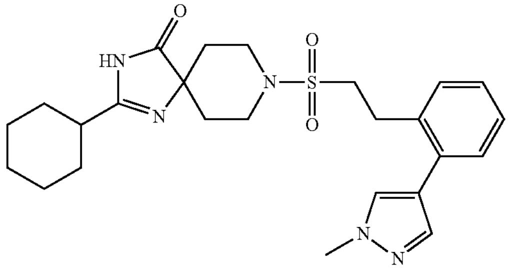 [SMILES: Cn1cc(-c2ccccc2CCS(=O)(=O)N2CCC3(CC2)N=C(C2CCCCC2)NC3=O)cn1] | LCMS-E-5 | 3.73 | 484 (M + H)+ |

Example 53

8-{5-[4-(3,4-Dihydroxy-butoxy)-2-methyl-phenyl]-thiophene-2-sulfonyl}-2-(4-fluoro-3-trifluoromethyl-phenyl)-1,3,8-triaza-spiro[4.5]dec-1-en-4-one (Compound 341)

(Reaction 53-1)

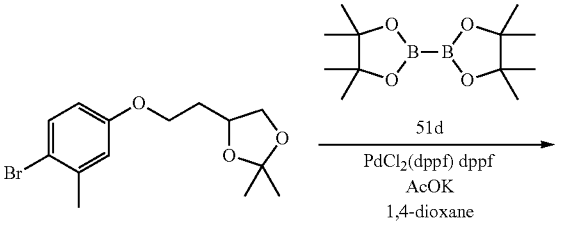

28b

-continued

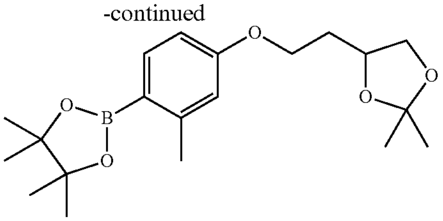

53a

2-{4-[2-(2,2-Dimethyl-[1,3]dioxolan-4-yl)-ethoxy]-2-methyl-phenyl}-4,4,5,5-tetramethyl-[1,3,2]dioxaborolane was synthesized by operations similar to those in Reaction 51-3 using appropriate reagents and starting material.

MS (ESI) m/z=257 ($M-C_3H_6O+H$)+.

(Reaction 53-2)

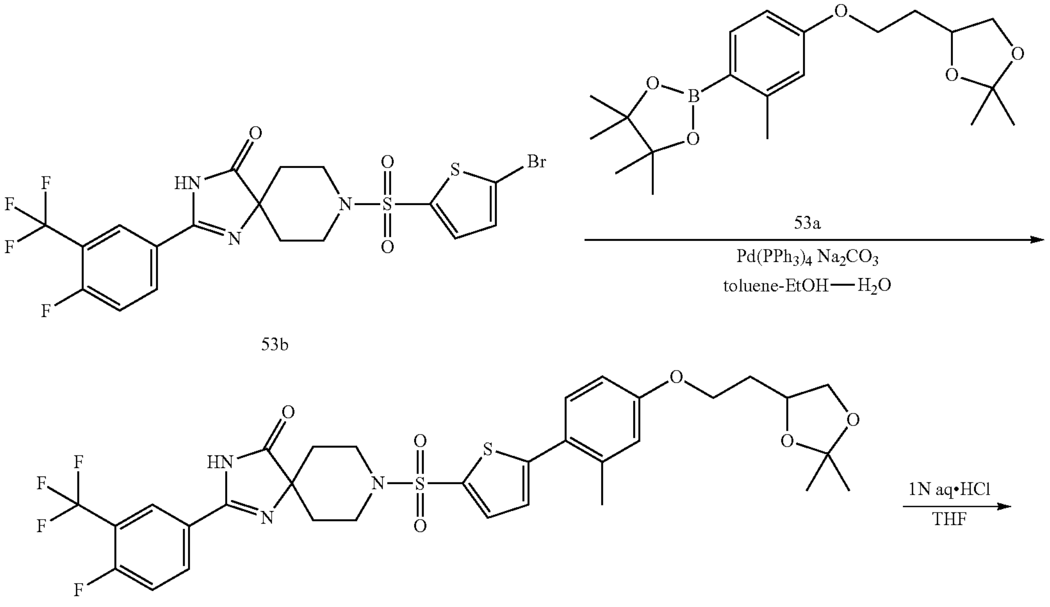

53b

53c

-continued

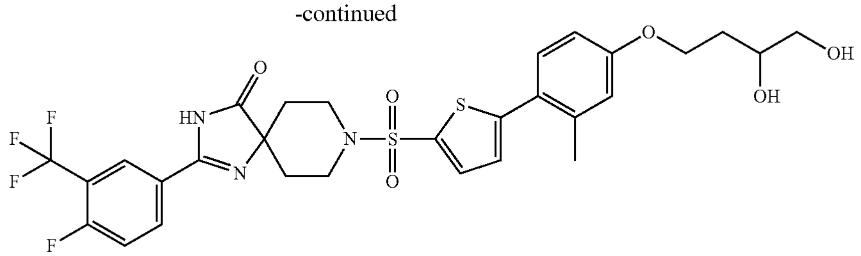

Compound 341

8-{5-[4-(3,4-Dihydroxy-butoxy)-2-methyl-phenyl]-thiophene-2-sulfonyl}-2-(4-fluoro-3-trifluoromethyl-phenyl)-1,3,8-triaza-spiro[4.5]dec-1-en-4-one was synthesized by operations similar to those in Reaction 51-2 and Reaction 25-4 using appropriate reagents and starting material.

MS (ESI) m/z=656 (M+H)+.

Example 54

N-(4-{5-[2-(4-Fluoro-3-trifluoromethyl-phenyl)-4-oxo-1,3,8-triaza-spiro[4.5]dec-1-ene-8-sulfonyl]-thiophen-2-yl}-3-methyl-phenyl)-N-(2-hydroxy-ethyl)-acetamide (Compound 342)

(Reaction 54-1)

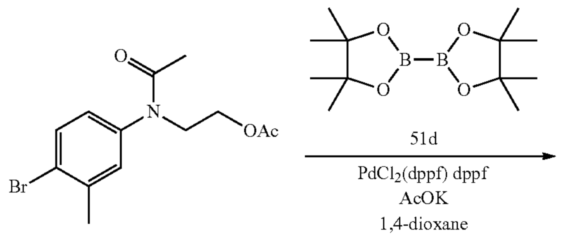

12d

-continued

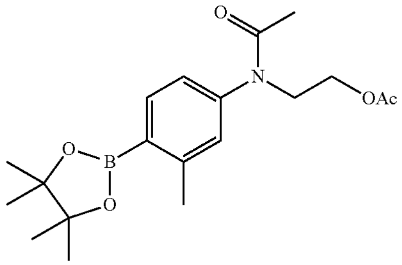

54a

Acetic acid 2-{acetyl-[3-methyl-4-(4,4,5,5-tetramethyl-[1,3,2]dioxaborolan-2-yl)-phenyl]-amino}-ethyl ester was synthesized by operations similar to those in Reaction 51-3 using appropriate reagents and starting material.

MS (ESI) m/z=315 (M+H)+.

(Reaction 54-2)

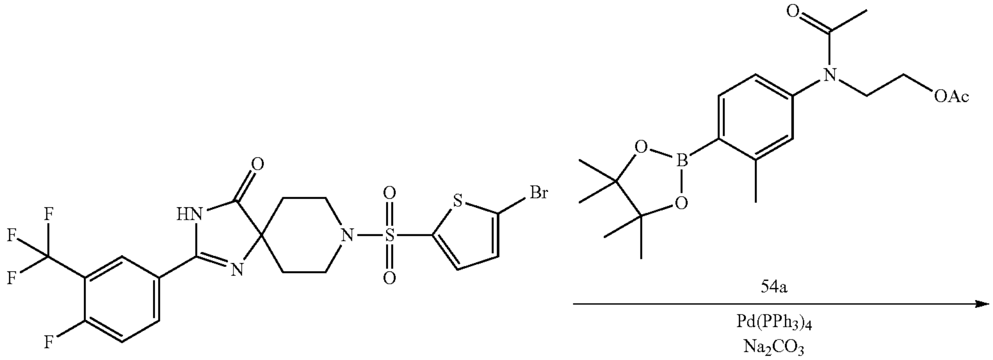

53b

-continued

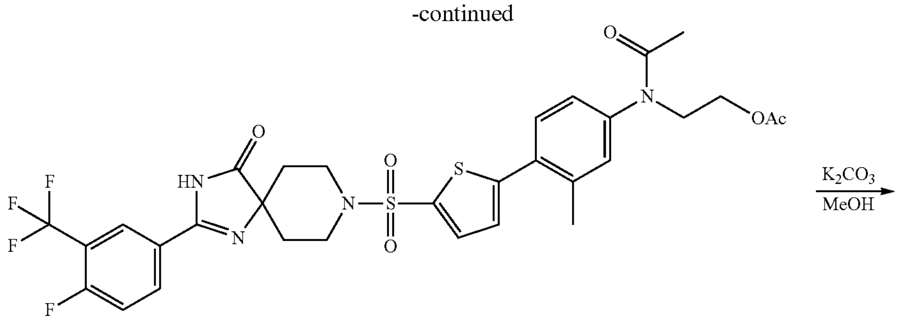

54b

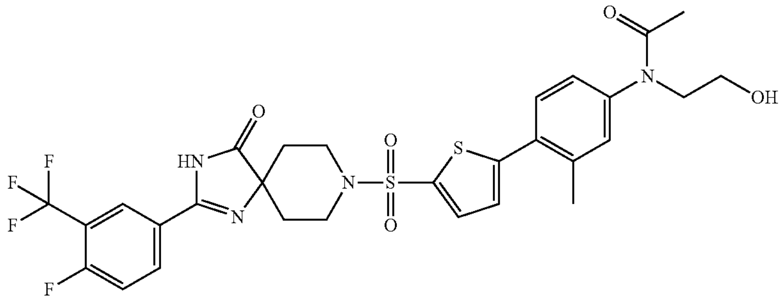

Compound 342

N-(4-{5-[2-(4-Fluoro-3-trifluoromethyl-phenyl)-4-oxo-1,3,8-triaza-spiro[4.5]dec-1-ene-8-sulfonyl]-thiophen-2-yl}-3-methyl-phenyl)-N-(2-hydroxy-ethyl)-acetamide was synthesized by operations similar to those in Reaction 51-2 and Reaction 12-5 using appropriate reagents and starting material.

MS (ESI) m/z=653 (M+H)+.

Example 55

2-Cyclohexyl-8-((E)-2-thiazol-2-yl-ethenesulfonyl)-1,3,8-triaza-spiro[4.5]dec-1-en-4-one (Compound 343)

(Reaction 55-1)

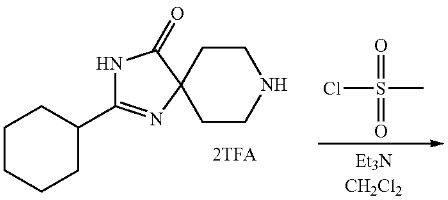

7c

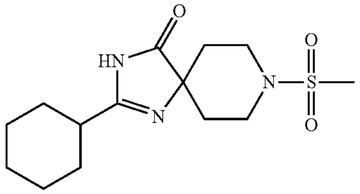

55a

2-Cyclohexyl-8-methanesulfonyl-1,3,8-triaza-spiro[4.5]dec-1-en-4-one was synthesized by operations similar to those in Reaction 5-4 using appropriate reagents and starting material.

MS (ESI) m/z=314 (M+H)+.

(Reaction 55-2)

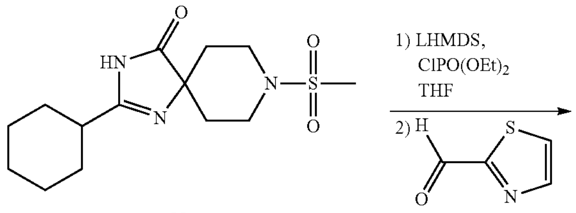

55a

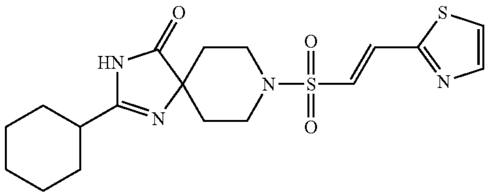

Compound 343

LHMDS (1.1 ml, 1.11 mmol) was added to a solution of 2-cyclohexyl-8-methanesulfonyl-1,3,8-triaza-spiro[4.5]dec-1-en-4-one (100 mg, 0.32 mmol) in THF (3 ml) at −20° C. in an $N_2$ atmosphere. The mixture was stirred at −20° C. for 30 minutes, and diethyl chlorophosphate (48 μl, 0.34 mmol) was then added. Further, the mixture was stirred at −20° C. for 60 minutes, and 2-thiazolecarboxyaldehyde (31 μl, 0.35 mmol) was then added. The reaction mixture was stirred at room temperature for one hour, and ethyl acetate (10 ml) and an aqueous $NH_4Cl$ solution (5 ml) were then added. The organic layer and the aqueous layer were separated, and the aqueous layer was then extracted with ethyl acetate (10 ml). The organic layers were combined and washed with saturated brine, and then dried over $Na_2SO_4$ and concentrated under reduced pressure. The resulting residue was recrystallized from ethyl acetate to give 2-cyclohexyl-8-((E)-2-thiazol-2-yl-ethenesulfonyl)-1,3,8-triaza-spiro[4.5]dec-1-en-4-one (87 mg, yield 67%).

$^1$H-NMR (300 MHz, $CDCl_3$) δ 8.38 (1H, s), 7.94 (1H, d, J=3.4 Hz), 7.57 (1H, d, J=15.3 Hz), 7.51 (1H, d, J=3.3 Hz), 7.11 (1H, d, J=15.3 Hz), 3.75 (2H, m), 3.31 (2H, m), 2.46-2.36 (1H, m), 2.07-1.97 (2H, m), 1.92-1.88 (2H, m), 1.83-1.80 (2H, m), 1.75-1.50 (4H, m), 1.50-1.20 (4H, m).

The example compound shown below was synthesized by operations similar to those in Example 55 using appropriate reagents and starting material.

Compound 344

TABLE 51

| Compound | Structure | LCMS or HPLC condition | Retention time (min) | MS (m/z) |
|---|---|---|---|---|
| 344 | 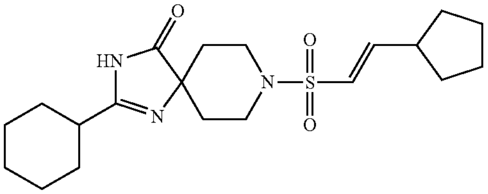 [SMILES: O=C1NC(C2CCCCC2)=NC12CCN(S(=O)(=O)/C=C/C1CCCC1)CC2] | HPLC-A-1 | 13.5 | 394 (M + H)+ |

Example 56

2-Cyclohexyl-8-(2-thiazol-2-yl-ethanesulfonyl)-1,3,8-triaza-spiro[4.5]dec-1-en-4-one (Compound 345)

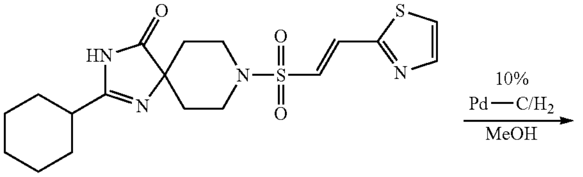

Compound 343

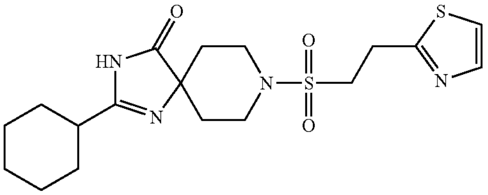

Compound 345

2-Cyclohexyl-8-(2-thiazol-2-yl-ethanesulfonyl)-1,3,8-triaza-spiro[4.5]dec-1-en-4-one was synthesized by operations similar to those in Reaction 42-1 using appropriate reagents and starting material.

$^1$H-NMR (300 MHz, $CDCl_3$) δ 9.04 (1H, s), 7.70 (1H, d, J=3.5 Hz), 7.25 (1H, d, J=3.0 Hz), 3.75 (2H, m), 3.57-3.44 (4H, m), 3.37 (2H, m), 2.46-2.38 (1H, m), 2.01-1.90 (4H, m), 1.84-1.70 (3H, m), 1.56-1.50 (2H, m), 1.48-1.26 (5H, m). MS (ESI) m/z=411 (M+H)+.

Example 57

2-Cyclohexyl-8-[3-(4-methoxy-phenyl)-propane-1-sulfonyl]-1,3,8-triaza-spiro[4.5]dec-1-en-4-one (Compound 346)

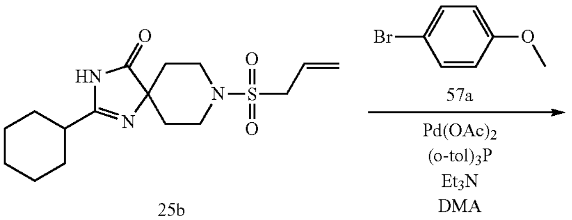

25b

-continued

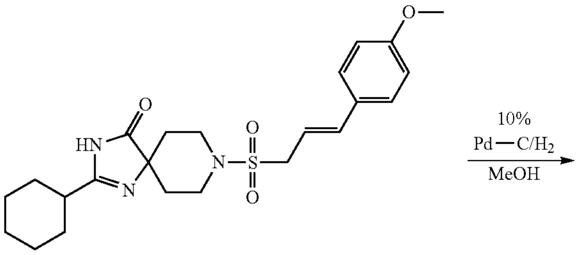

57b

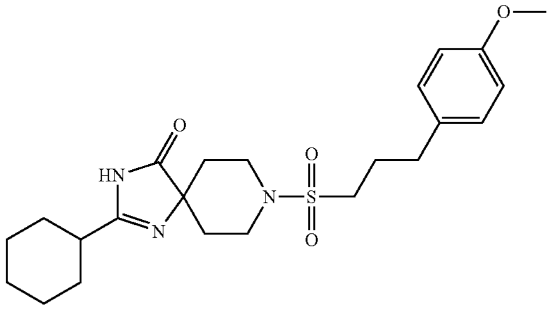

Compound 346

2-Cyclohexyl-8-[3-(4-methoxy-phenyl)-propane-1-sulfonyl]-1,3,8-triaza-spiro[4.5]dec-1-en-4-one was synthesized by operations similar to those in Reaction 25-2 and Reaction 42-1 using appropriate reagents and starting material.

MS (ESI) m/z=448 (M+H)+.

Example 58

N-Benzyl-2-(2-cyclohexyl-4-oxo-1,3,8-triaza-spiro[4.5]dec-1-ene-8-sulfonyl)-benzamide (Compound 347)

(Reaction 58-1)

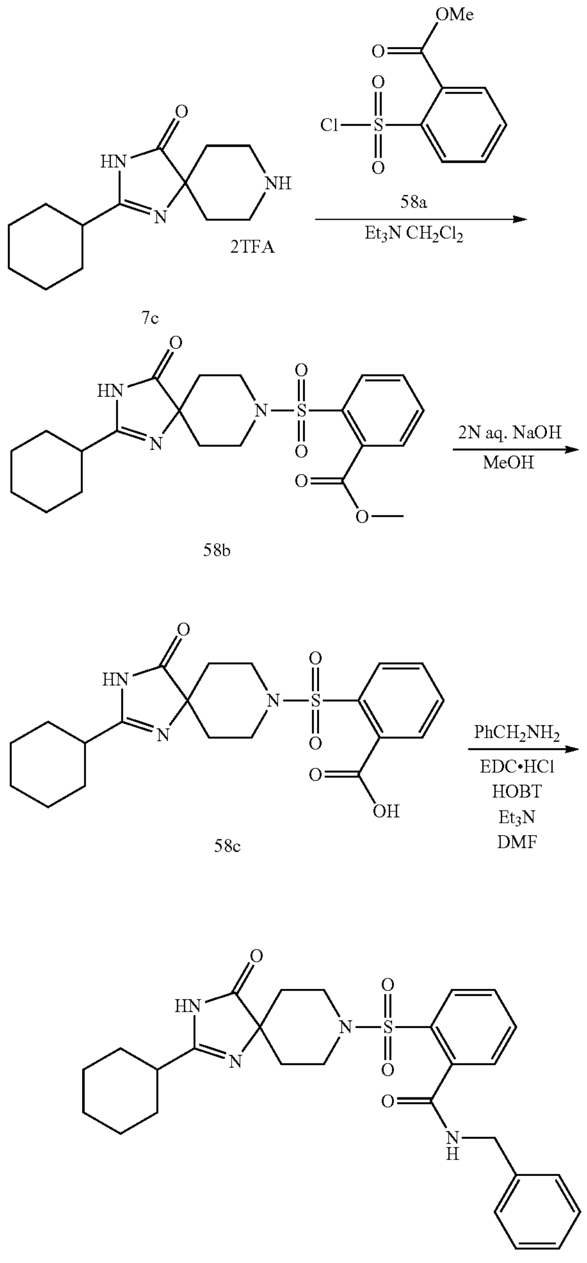

Compound 347

N-Benzyl-2-(2-cyclohexyl-4-oxo-1,3,8-triaza-spiro[4.5]dec-1-ene-8-sulfonyl)-benzamide was synthesized by operations similar to those in Reaction 5-4, Reaction 23-2 and Reaction 10-18 using appropriate reagents and starting material.

MS (ESI) m/z=509 (M+H)+.

Example 59

8-(3-Chloro-benzenesulfonyl)-2-[3-(morpholine-4-carbonyl)-phenyl]-1,3,8-triaza-spiro[4.5]dec-1-en-4-one (Compound 348)

(Reaction 59-1)

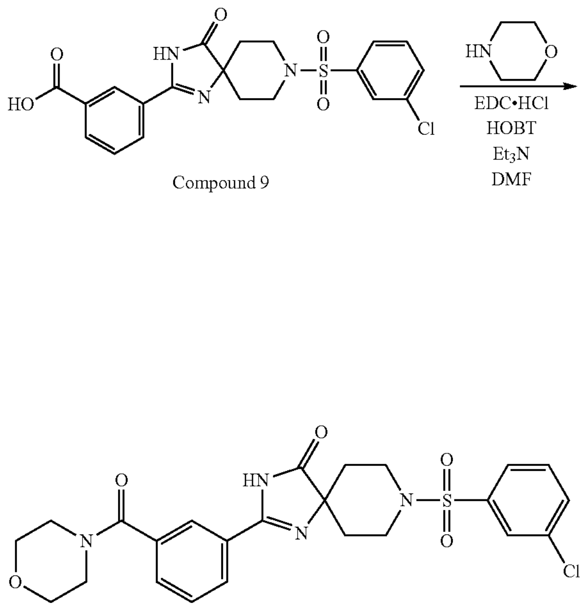

Compound 348

8-(3-Chloro-benzenesulfonyl)-2-[3-(morpholine-4-carbonyl)-phenyl]-1,3,8-triaza-spiro[4.5]dec-1-en-4-one was synthesized by operations similar to those in Reaction 10-18 using appropriate reagents and starting material.

MS (ESI) m/z=517 (M+H)+.

The example compounds shown below were synthesized by operations similar to those in Example 59 using appropriate reagents and starting materials.

Compounds 349 to 351
TABLE 52
| Compound | Structure | LCMS or HPLC condition | Retention time (min) | MS (m/z) |
|---|---|---|---|---|
| 349 | 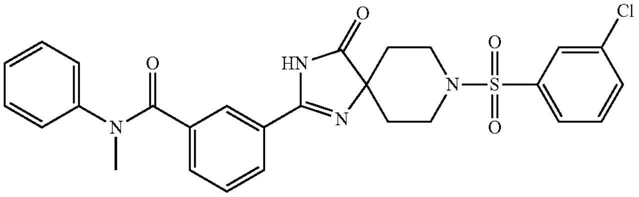 [SMILES: CN(C(=O)c1cccc(C2=NC3(CCN(S(=O)(=O)c4cccc(Cl)c4)CC3)C(=O)N2)c1)c1ccccc1] | LCMS-E-2 | 4.11 | 537 (M + H)+ |
| 350 | 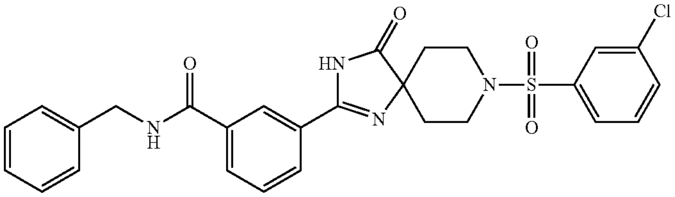 [SMILES: O=C(NCc1ccccc1)c1cccc(C2=NC3(CCN(S(=O)(=O)c4cccc(Cl)c4)CC3)C(=O)N2)c1] | LCMS-E-6 | 1.76 | 537 (M + H)+ |
| 351 | 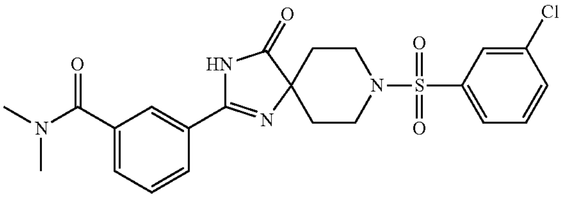 [SMILES: CN(C)C(=O)c1cccc(C2=NC3(CCN(S(=O)(=O)c4cccc(Cl)c4)CC3)C(=O)N2)c1] | LCMS-E-6 | 1.42 | 475 (M + H)+ |
Example 60
8-{2-[4-(4-Methanesulfonyl-piperazine-1-carbonyl)-2-methyl-phenyl]-ethanesulfonyl}-2-(3-trifluoromethyl-phenyl)-1,3,8-triaza-spiro[4.5]dec-1-en-4-one (Compound 352)
(Reaction 60-1)
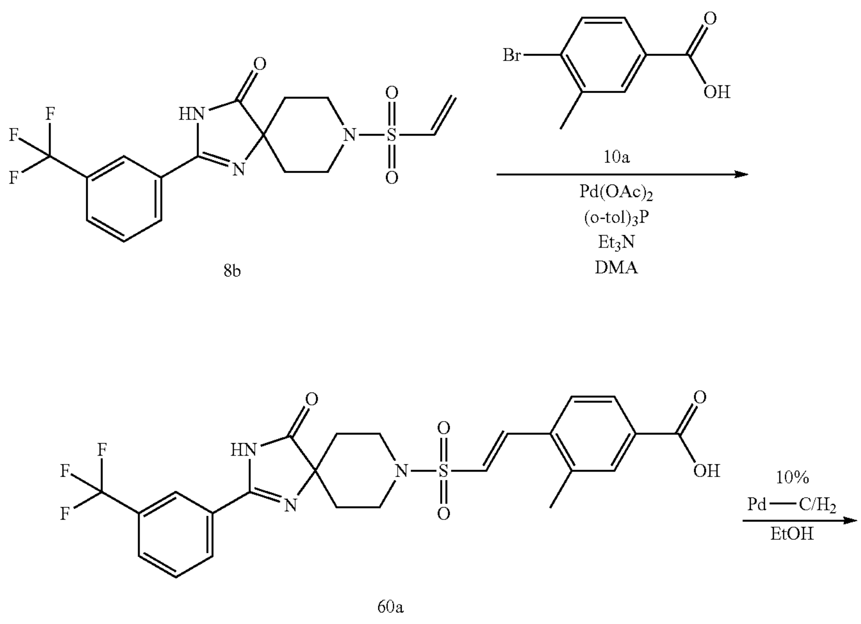

-continued

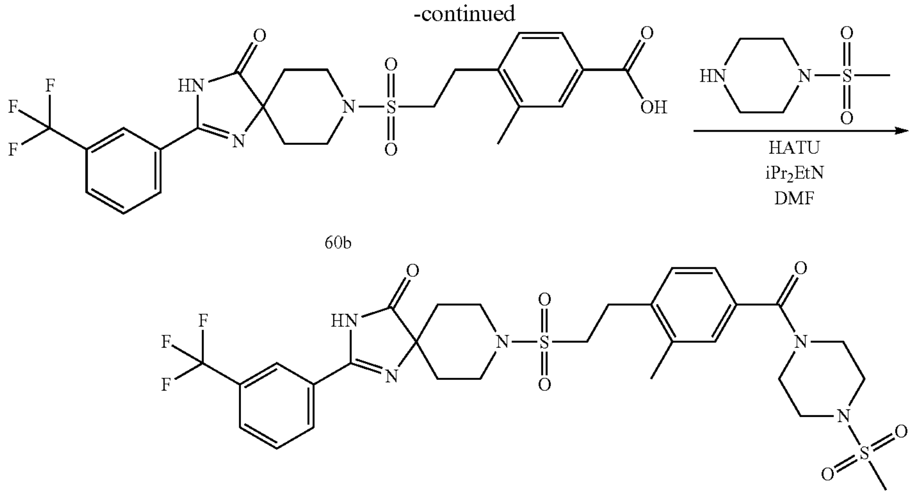

60b

Compound 352

8-{2-[4-(4-Methanesulfonyl-piperazine-1-carbonyl)-2-methyl-phenyl]-ethanesulfonyl}-2-(3-trifluoromethyl-phenyl)-1,3,8-triaza-spiro[4.5]dec-1-en-4-one was synthesized by operations similar to those in Reaction 26-1, Reaction 18-2 and Reaction 10-14 using appropriate reagents and starting material.

MS (ESI) m/z=670 (M+H)+.

The example compounds shown below were synthesized by operations similar to those in Example 60 using appropriate reagents and starting materials.

Compounds 353 to 382

TABLE 53

| Compound | Structure | LCMS or HPLC condition | Retention time (min) | MS (m/z) |
|---|---|---|---|---|
| 353 | 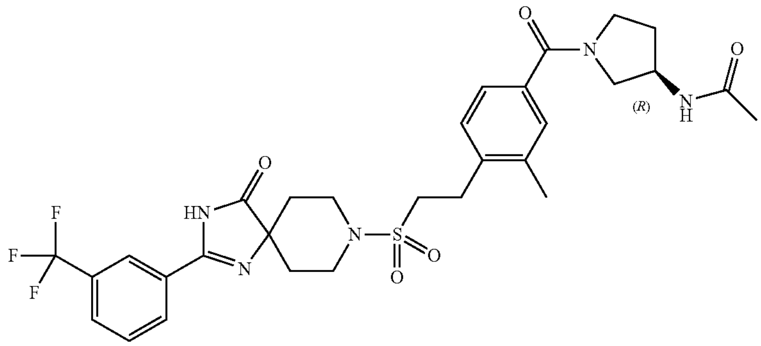 | LCMS-C-1 | 2.43 | 634 (M + H)+ |
| 354 | 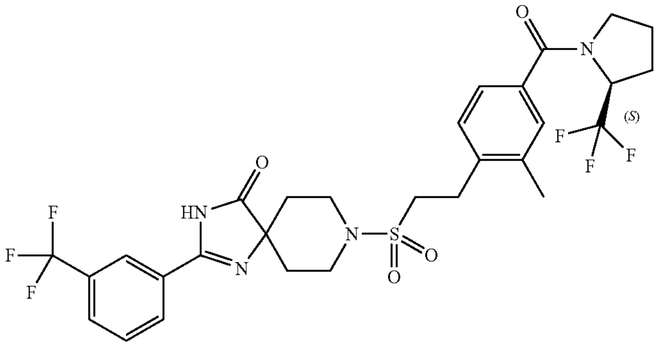 | LCMS-C-1 | 2.85 | 645 (M + H)+ |

TABLE 53-continued
| Compound | Structure | LCMS or HPLC condition | Retention time (min) | MS (m/z) |
|---|---|---|---|---|
| 355 | 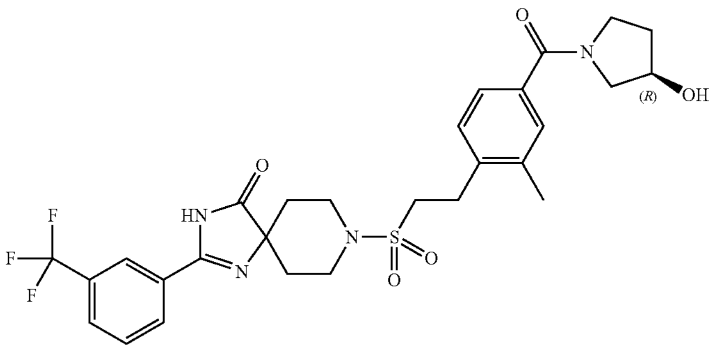 | LCMS-C-1 | 2.45 | 593 (M + H)+ |
| 356 | 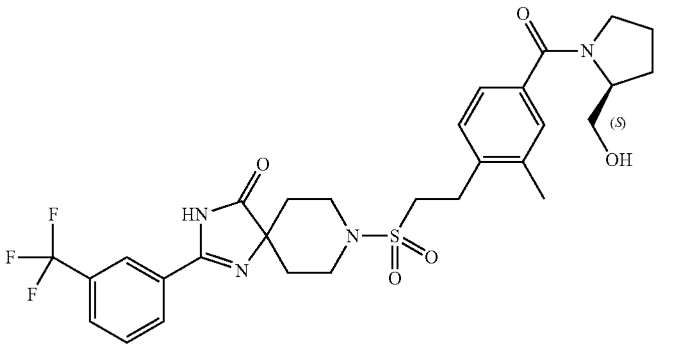 | LCMS-C-1 | 2.58 | 607 (M + H)+ |
| 357 | 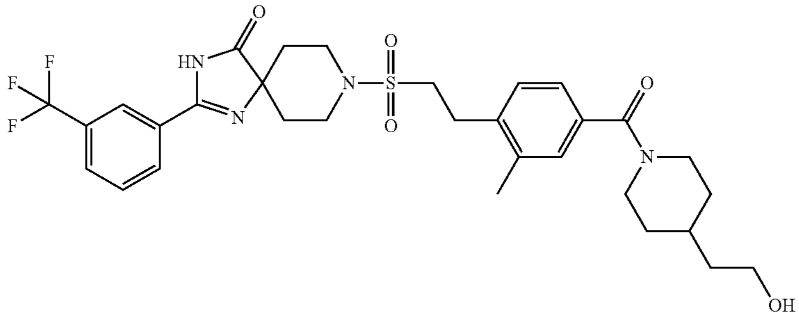 [SMILES: Cc1cc(C(=O)N2CCC(CCO)CC2)ccc1CCS(=O)(=O)N1CCC2(CC1)N=C(c1cccc(C(F)(F)F)c1)NC2=O] | LCMS-A-1 | 2.30 | 635 (M + H)+ |
| 358 | 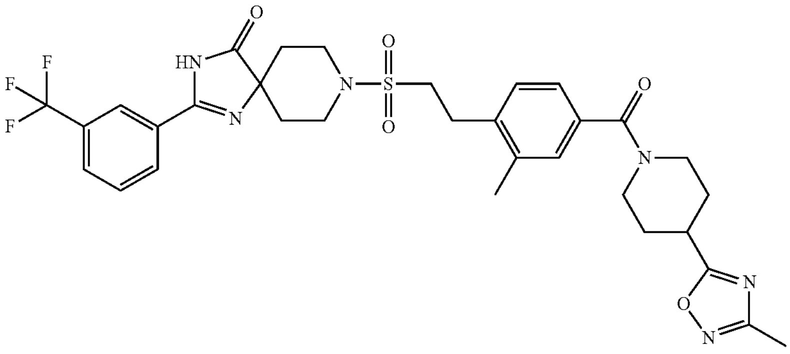 [SMILES: Cc1noc(C2CCN(C(=O)c3ccc(CCS(=O)(=O)N4CCC5(CC4)N=C(c4cccc(C(F)(F)F)c4)NC5=O)c(C)c3)CC2)n1] | LCMS-A-1 | 2.50 | 673 (M + H)+ |

TABLE 53-continued
| Compound | Structure | LCMS or HPLC condition | Retention time (min) | MS (m/z) |
|---|---|---|---|---|
| 359 | 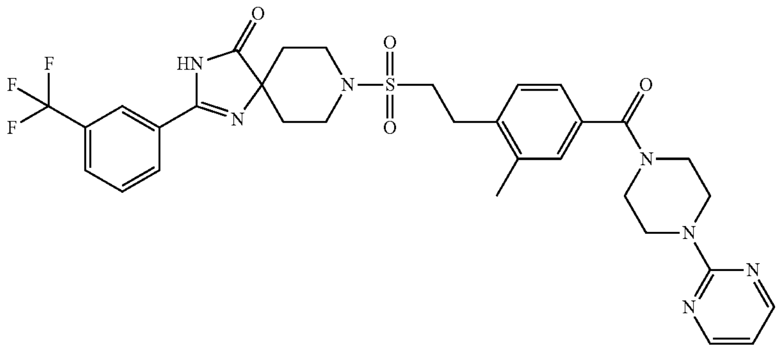 [SMILES: Cc1cc(C(=O)N2CCN(c3ncccn3)CC2)ccc1CCS(=O)(=O)N1CCC2(CC1)N=C(c1cccc(C(F)(F)F)c1)NC2=O] | LCMS-A-1 | 2.45 | 670 (M + H)+ |
| 360 | 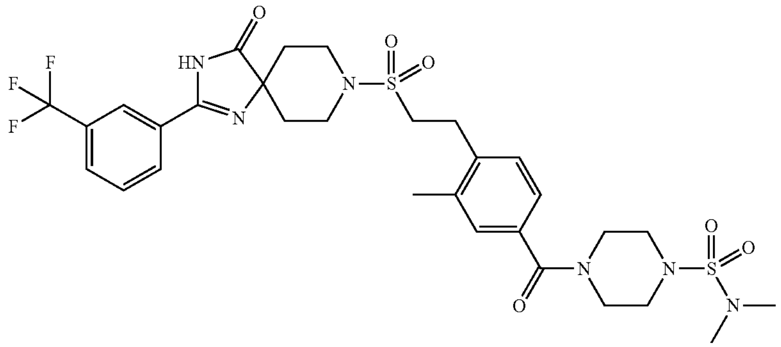 [SMILES: Cc1cc(C(=O)N2CCN(S(=O)(=O)N(C)C)CC2)ccc1CCS(=O)(=O)N1CCC2(CC1)N=C(c1cccc(C(F)(F)F)c1)NC2=O] | LCMS-C-1 | 2.58 | 699 (M + H)+ |
| 361 | 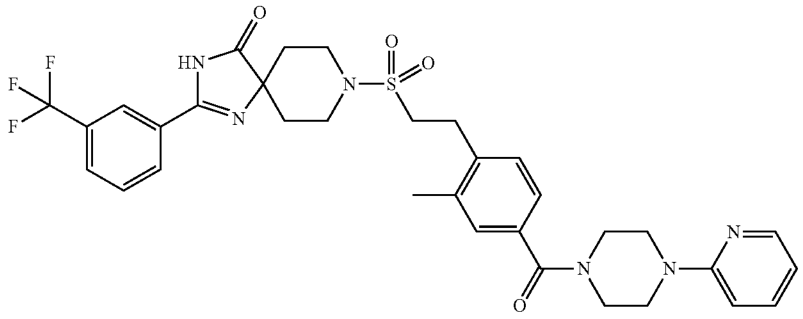 [SMILES: Cc1cc(C(=O)N2CCN(c3ccccn3)CC2)ccc1CCS(=O)(=O)N1CCC2(CC1)N=C(c1cccc(C(F)(F)F)c1)NC2=O] | LCMS-C-1 | 2.78 | 669 (M + H) |
| 362 | 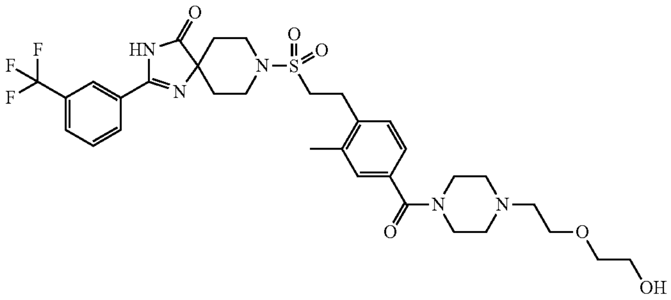 [SMILES: Cc1cc(C(=O)N2CCN(CCOCCO)CC2)ccc1CCS(=O)(=O)N1CCC2(CC1)N=C(c1cccc(C(F)(F)F)c1)NC2=O] | LCMS-C-1 | 2.47 | 680 (M + H)+ |

TABLE 53-continued
| Compound | Structure | LCMS or HPLC condition | Retention time (min) | MS (m/z) |
|---|---|---|---|---|
| 363 | 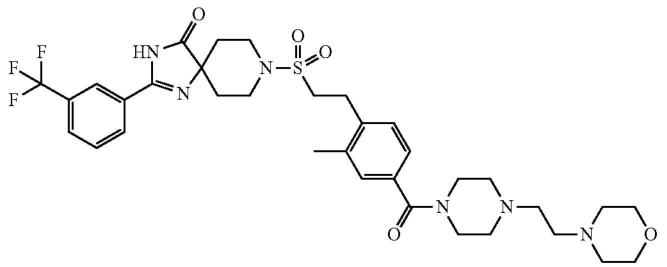 [SMILES: Cc1cc(C(=O)N2CCN(CCN3CCOCC3)CC2)ccc1CCS(=O)(=O)N1CCC2(CC1)N=C(c1cccc(C(F)(F)F)c1)NC2=O] | LCMS-C-1 | 2.53 | 705 (M + H)+ |
| 364 | 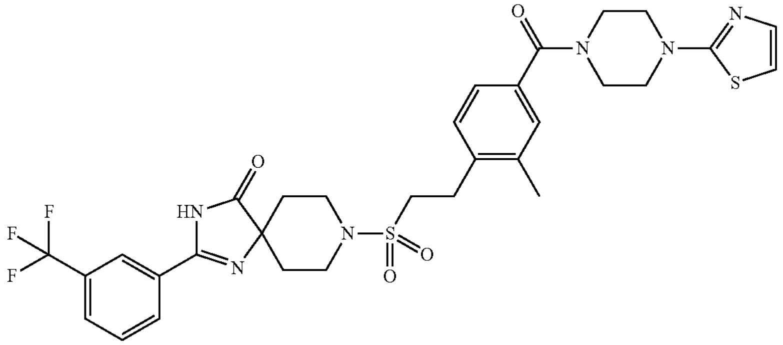 [SMILES: Cc1cc(C(=O)N2CCN(c3nccs3)CC2)ccc1CCS(=O)(=O)N1CCC2(CC1)N=C(c1cccc(C(F)(F)F)c1)NC2=O] | LCMS-C-1 | 2.72 | 675 (M + H)+ |
| 365 | 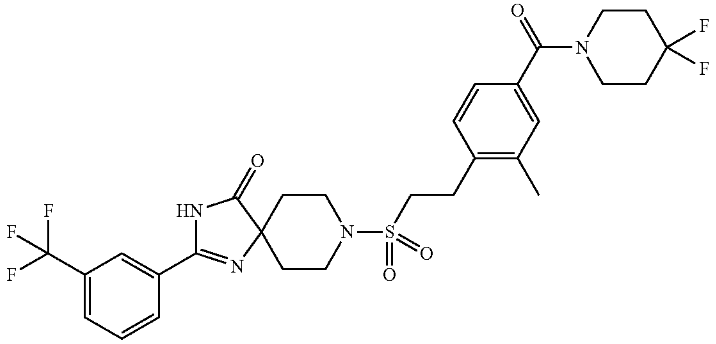 [SMILES: Cc1cc(C(=O)N2CCC(F)(F)CC2)ccc1CCS(=O)(=O)N1CCC2(CC1)N=C(c1cccc(C(F)(F)F)c1)NC2=O] | LCMS-A-1 | 2.67 | 627 (M + H)+ |
| 366 | 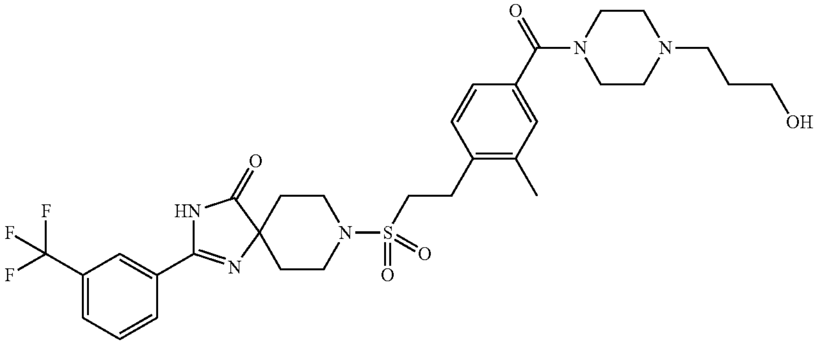 [SMILES: Cc1cc(C(=O)N2CCN(CCCO)CC2)ccc1CCS(=O)(=O)N1CCC2(CC1)N=C(c1cccc(C(F)(F)F)c1)NC2=O] | LCMS-A-1 | 1.95 | 650 (M + H)+ |

TABLE 53-continued
| Compound | Structure | LCMS or HPLC condition | Retention time (min) | MS (m/z) |
|---|---|---|---|---|
| 367 | 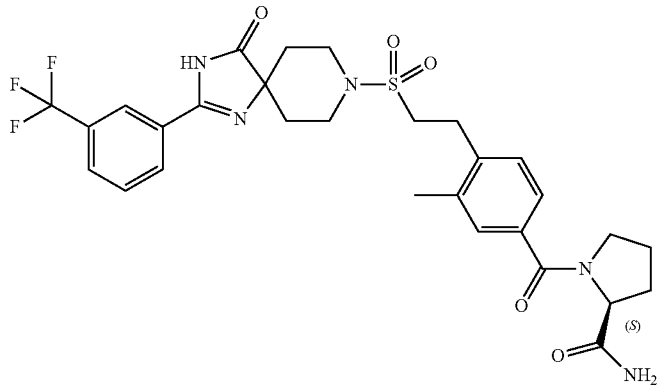 | LCMS-C-1 | 2.42 | 620 (M + H)+ |
| 368 | 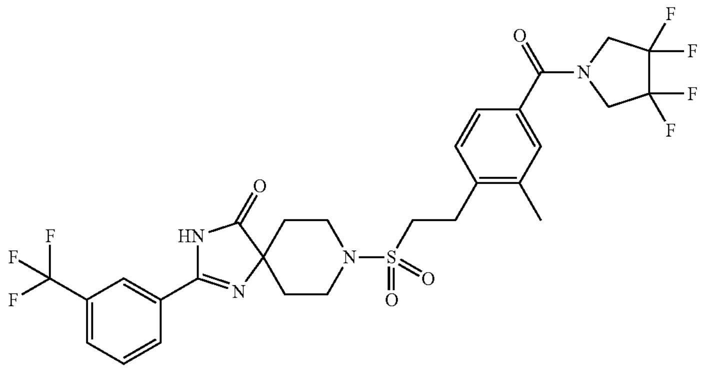 [SMILES: Cc1cc(C(=O)N2CC(F)(F)C(F)(F)C2)ccc1CCS(=O)(=O)N1CCC2(CC1)N=C(c1cccc(C(F)(F)F)c1)NC2=O] | LCMS-A-1 | 2.81 | 649 (M + H)+ |
| 369 | 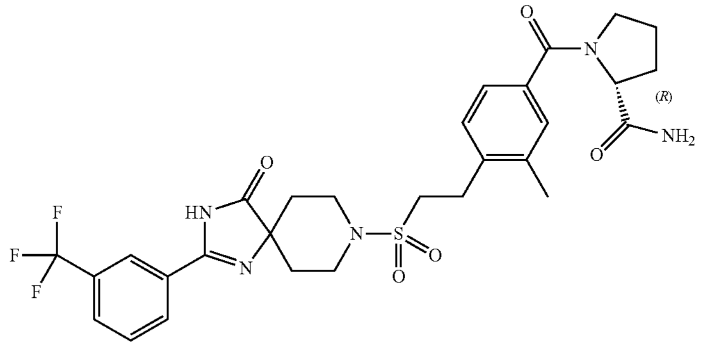 | LCMS-C-1 | 2.42 | 620 (M + H)+ |
| 370 | 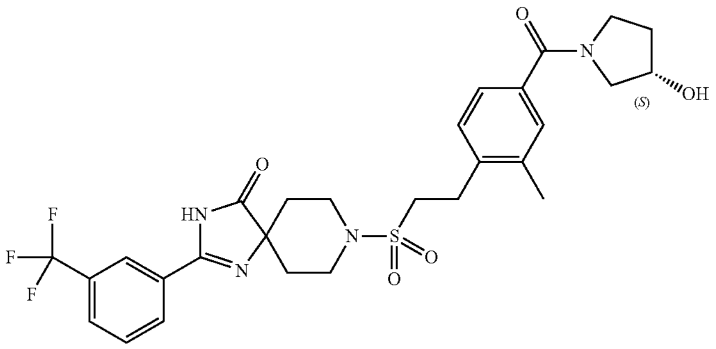 | LCMS-C-1 | 2.42 | 593 (M + H)+ |

TABLE 53-continued
| Compound | Structure | LCMS or HPLC condition | Retention time (min) | MS (m/z) |
|---|---|---|---|---|
| 371 | 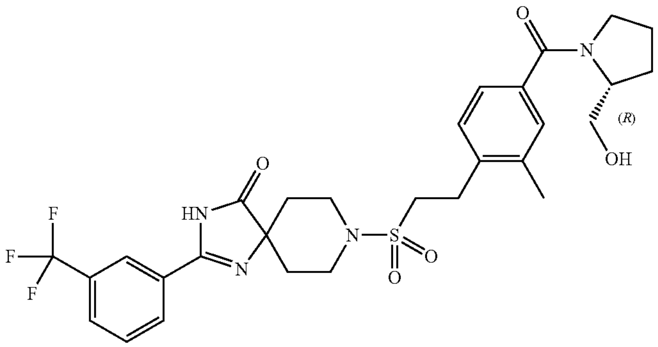 | LCMS-C-1 | 2.55 | 607 (M + H)+ |
| 372 | 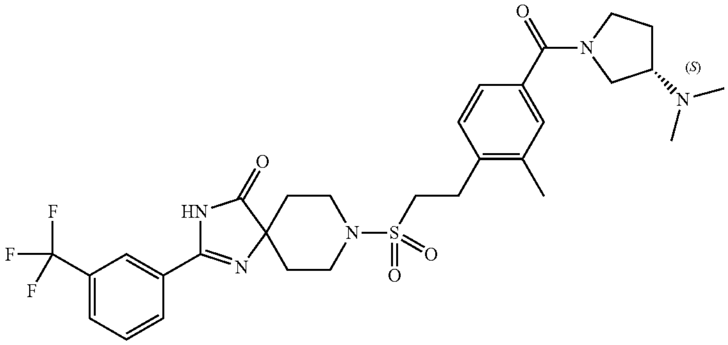 | LCMS-C-1 | 2.57 | 620 (M + H)+ |
| 373 | 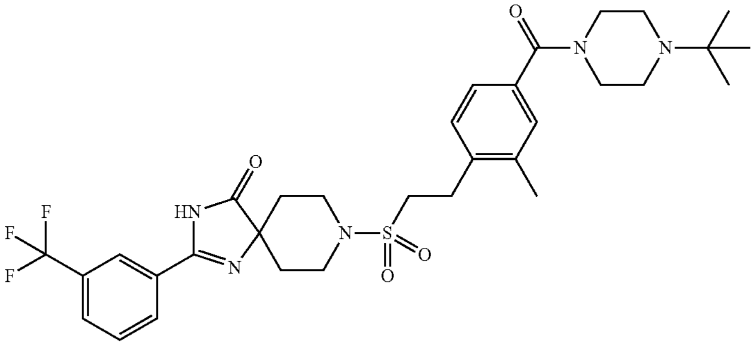 [SMILES: Cc1cc(C(=O)N2CCN(C(C)(C)C)CC2)ccc1CCS(=O)(=O)N1CCC2(CC1)N=C(c1cccc(C(F)(F)F)c1)NC2=O] | LCMS-A-1 | 2.08 | 648 (M + H)+ |
| 374 | 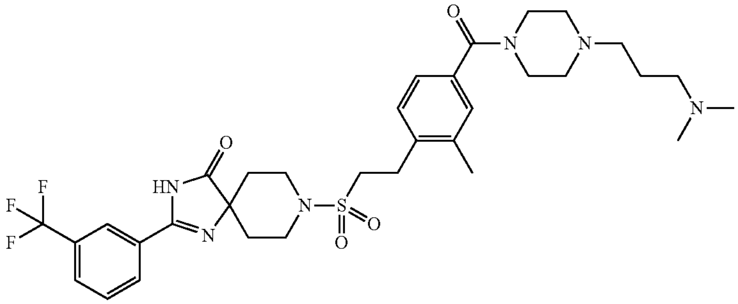 [SMILES: Cc1cc(C(=O)N2CCN(CCCN(C)C)CC2)ccc1CCS(=O)(=O)N1CCC2(CC1)N=C(c1cccc(C(F)(F)F)c1)NC2=O] | LCMS-C-1 | 2.43 | 677 (M + H)+ |

TABLE 53-continued
| Compound | Structure | LCMS or HPLC condition | Retention time (min) | MS (m/z) |
|---|---|---|---|---|
| 375 | 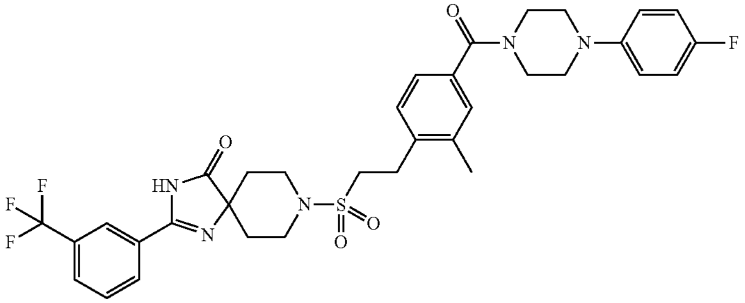 [SMILES: Cc1cc(C(=O)N2CCN(c3ccc(F)cc3)CC2)ccc1CCS(=O)(=O)N1CCC2(CC1)N=C(c1cccc(C(F)(F)F)c1)NC2=O] | LCMS-A-1 | 2.79 | 686 (M + H)+ |
| 376 | 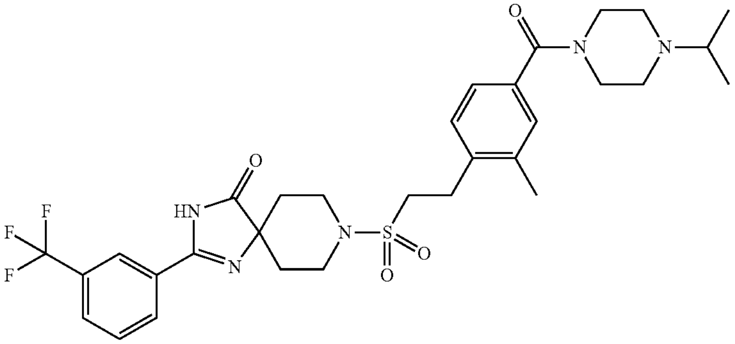 [SMILES: Cc1cc(C(=O)N2CCN(C(C)C)CC2)ccc1CCS(=O)(=O)N1CCC2(CC1)N=C(c1cccc(C(F)(F)F)c1)NC2=O] | LCMS-A-1 | 2.03 | 634 (M + H)+ |
| 377 | 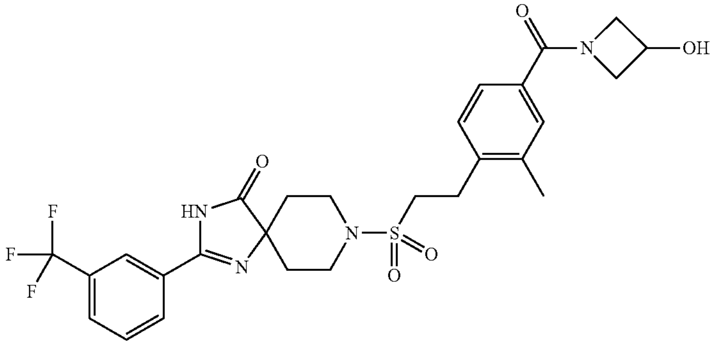 [SMILES: Cc1cc(C(=O)N2CC(O)C2)ccc1CCS(=O)(=O)N1CCC2(CC1)N=C(c1cccc(C(F)(F)F)c1)NC2=O] | LCMS-C-1 | 2.40 | 579 (M + H)+ |
| 378 | 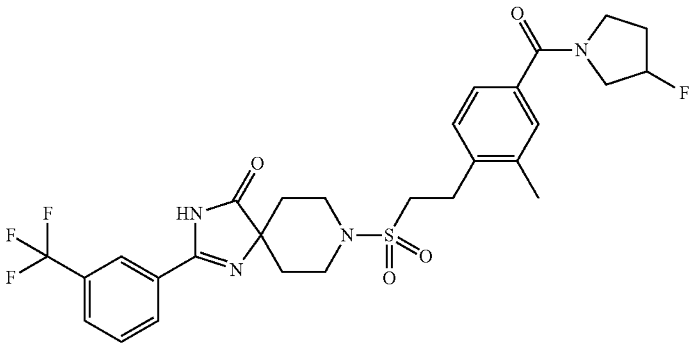 [SMILES: Cc1cc(C(=O)N2CCC(F)C2)ccc1CCS(=O)(=O)N1CCC2(CC1)N=C(c1cccc(C(F)(F)F)c1)NC2=O] | LCMS-B-1 | 2.16 | 595 (M + H)+ |

TABLE 53-continued
| Compound | Structure | LCMS or HPLC condition | Retention time (min) | MS (m/z) |
|---|---|---|---|---|
| 379 | 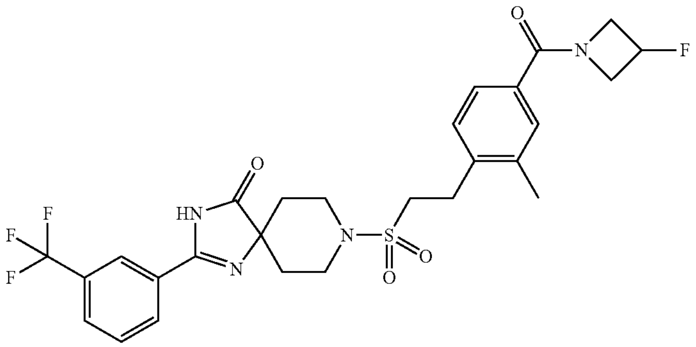 [SMILES: Cc1cc(C(=O)N2CC(F)C2)ccc1CCS(=O)(=O)N1CCC2(CC1)N=C(c1cccc(C(F)(F)F)c1)NC2=O] | LCMS-B-1 | 2.15 | 581 (M + H)+ |
| 380 | 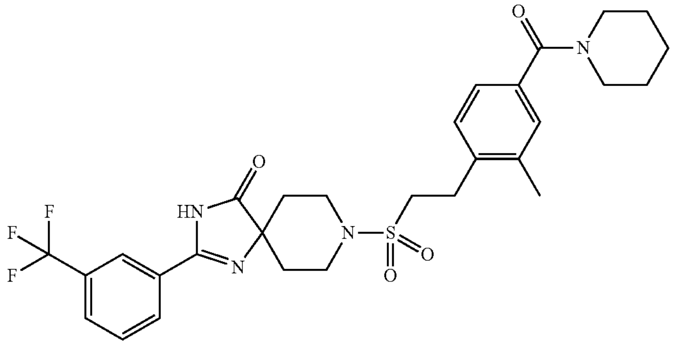 [SMILES: Cc1cc(C(=O)N2CCCCC2)ccc1CCS(=O)(=O)N1CCC2(CC1)N=C(c1cccc(C(F)(F)F)c1)NC2=O] | LCMS-B-1 | 2.38 | 591 (M + H)+ |
| 381 | 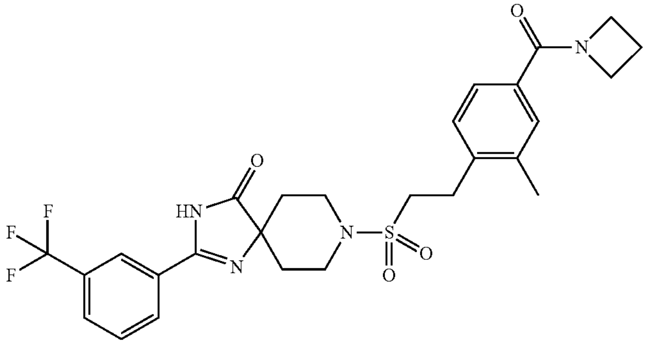 [SMILES: Cc1cc(C(=O)N2CCC2)ccc1CCS(=O)(=O)N1CCC2(CC1)N=C(c1cccc(C(F)(F)F)c1)NC2=O] | LCMS-B-1 | 2.12 | 563 (M + H)+ |
| 382 | 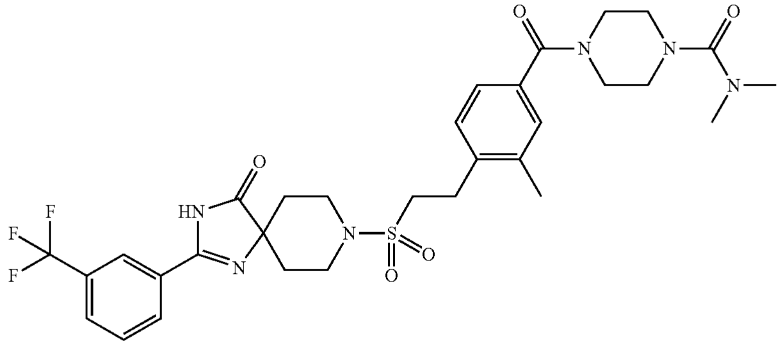 [SMILES: Cc1cc(C(=O)N2CCN(C(=O)N(C)C)CC2)ccc1CCS(=O)(=O)N1CCC2(CC1)N=C(c1cccc(C(F)(F)F)c1)NC2=O] | LCMS-C-1 | 2.52 | 663 (M + H)+ |

Example 61

3,5,N,N-Tetramethyl-4-{(E)-2-[4-oxo-2-(3-trifluoromethyl-phenyl)-1,3,8-triaza-spiro[4.5]dec-1-ene-8-sulfonyl]-vinyl}-benzamide (Compound 383)

(Reaction 61-1)

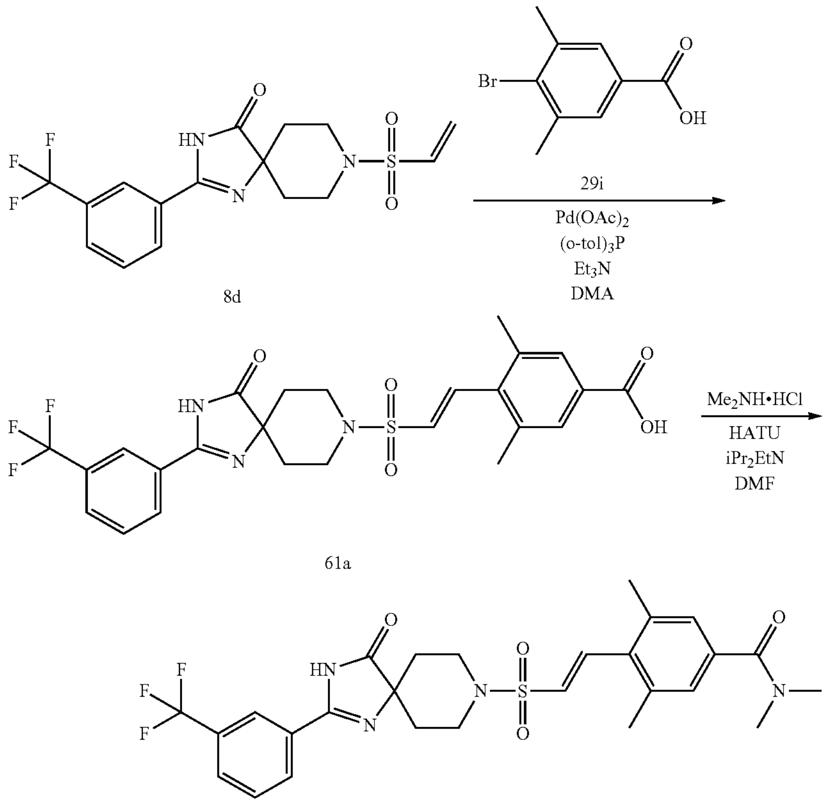

8d

61a

Compound 383

3,5,N,N-Tetramethyl-4-{(E)-2-[4-oxo-2-(3-trifluoromethyl-phenyl)-1,3,8-triaza-spiro[4.5]dec-1-ene-8-sulfonyl]-vinyl}-benzamide was synthesized by operations similar to those in Reaction 26-1 and Reaction 10-14 using appropriate reagents and starting material.

MS (ESI) m/z=563 (M+H)+.

The example compounds shown below were synthesized by operations similar to those in Example 61 using appropriate reagents and starting materials.

Compounds 384 to 393

TABLE 54

| Compound | Structure | LCMS or HPLC condition | Retention time (min) | MS (m/z) |
|---|---|---|---|---|
| 384 | 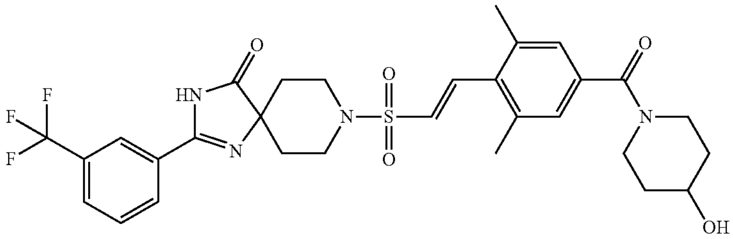 [SMILES: Cc1cc(C(=O)N2CCC(O)CC2)cc(C)c1/C=C/S(=O)(=O)N1CCC2(CC1)N=C(c1cccc(C(F)(F)F)c1)NC2=O] | LCMS-C-1 | 2.53 | 619 (M + H)+ |

TABLE 54-continued
| Compound | Structure | LCMS or HPLC condition | Retention time (min) | MS (m/z) |
|---|---|---|---|---|
| 385 | 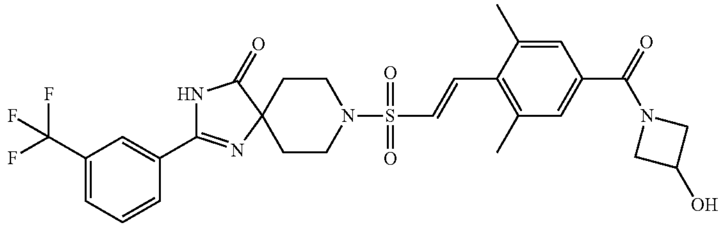 [SMILES: Cc1cc(C(=O)N2CC(O)C2)cc(C)c1/C=C/S(=O)(=O)N1CCC2(CC1)N=C(c1cccc(C(F)(F)F)c1)NC2=O] | LCMS-C-1 | 2.52 | 591 (M + H)+ |
| 386 | 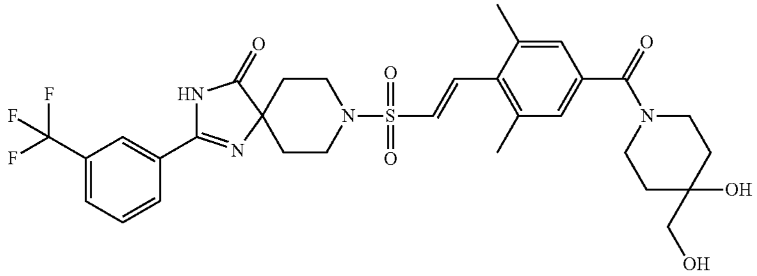 [SMILES: Cc1cc(C(=O)N2CCC(O)(CO)CC2)cc(C)c1/C=C/S(=O)(=O)N1CCC2(CC1)N=C(c1cccc(C(F)(F)F)c1)NC2=O] | LCMS-C-1 | 2.48 | 649 (M + H)+ |
| 387 | 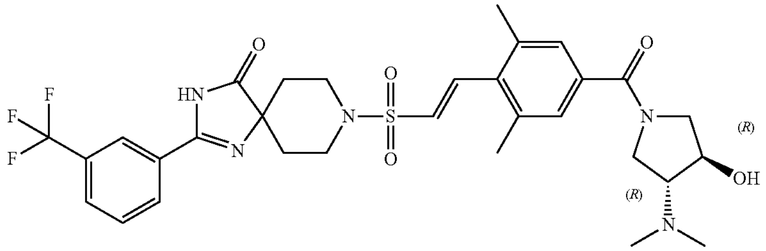 | LCMS-C-1 | 2.50 | 648 (M + H)+ |
| 388 | 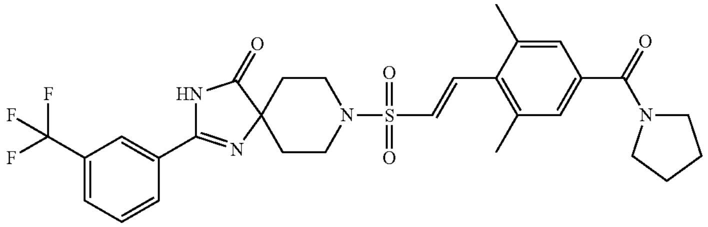 [SMILES: Cc1cc(C(=O)N2CCCC2)cc(C)c1/C=C/S(=O)(=O)N1CCC2(CC1)N=C(c1cccc(C(F)(F)F)c1)NC2=O] | LCMS-C-1 | 2.77 | 589 (M + H)+ |
| 389 | 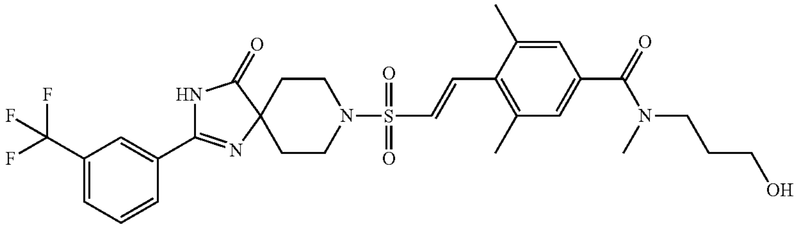 [SMILES: Cc1cc(C(=O)N(C)CCCO)cc(C)c1/C=C/S(=O)(=O)N1CCC2(CC1)N=C(c1cccc(C(F)(F)F)c1)NC2=O] | LCMS-C-1 | 2.53 | 607 (M + H)+ |
| 390 | 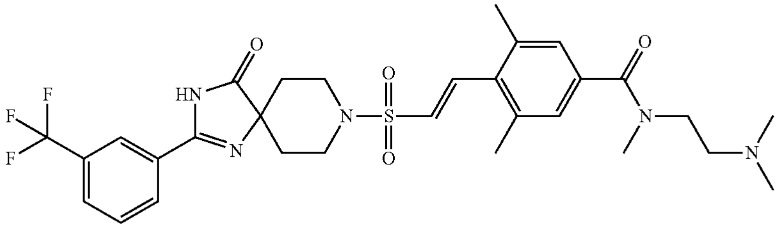 [SMILES: Cc1cc(C(=O)N(C)CCN(C)C)cc(C)c1/C=C/S(=O)(=O)N1CCC2(CC1)N=C(c1cccc(C(F)(F)F)c1)NC2=O] | LCMS-C-1 | 2.60 | 620 (M + H)+ |

TABLE 54-continued
| Compound | Structure | LCMS or HPLC condition | Retention time (min) | MS (m/z) |
|---|---|---|---|---|
| 391 | 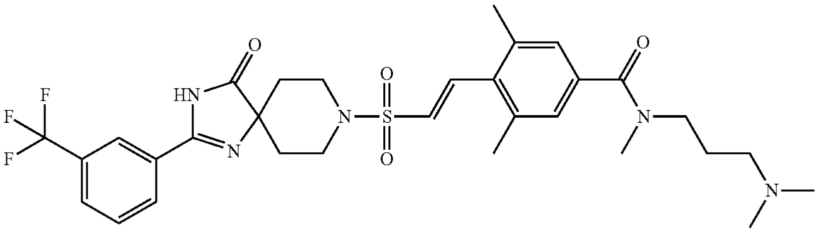 [SMILES: Cc1cc(C(=O)N(C)CCCN(C)C)cc(C)c1/C=C/S(=O)(=O)N1CCC2(CC1)N=C(c1cccc(C(F)(F)F)c1)NC2=O] | LCMS-C-1 | 2.48 | 634 (M + H)+ |
| 392 | 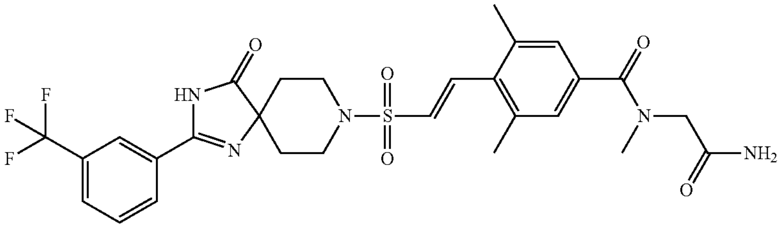 [SMILES: Cc1cc(C(=O)N(C)CC(N)=O)cc(C)c1/C=C/S(=O)(=O)N1CCC2(CC1)N=C(c1cccc(C(F)(F)F)c1)NC2=O] | LCMS-C-1 | 2.28 | 606 (M + H)+ |
| 393 | 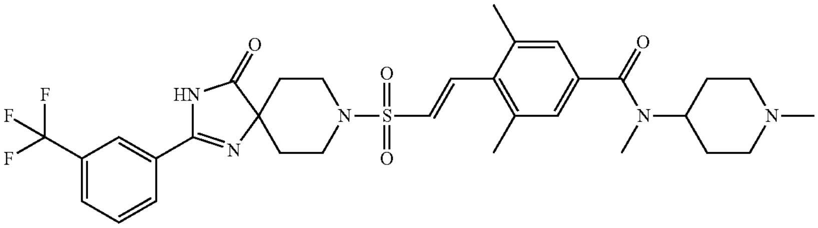 [SMILES: Cc1cc(C(=O)N(C)C2CCN(C)CC2)cc(C)c1/C=C/S(=O)(=O)N1CCC2(CC1)N=C(c1cccc(C(F)(F)F)c1)NC2=O] | LCMS-C-1 | 2.62 | 646 (M + H)+ |
Example 62
8-{(E)-2-[4-(4-Acetyl-piperazine-1-carbonyl)-2,6-dimethyl-phenyl]-ethenesulfonyl}-2-(3-trifluoromethoxy-phenyl)-1,3,8-triaza-spiro[4.5]dec-1-en-4-one (Compound 394)
(Reaction 62-1)
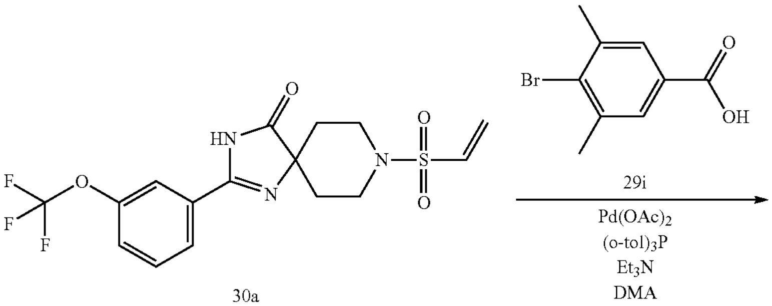
30a -continued

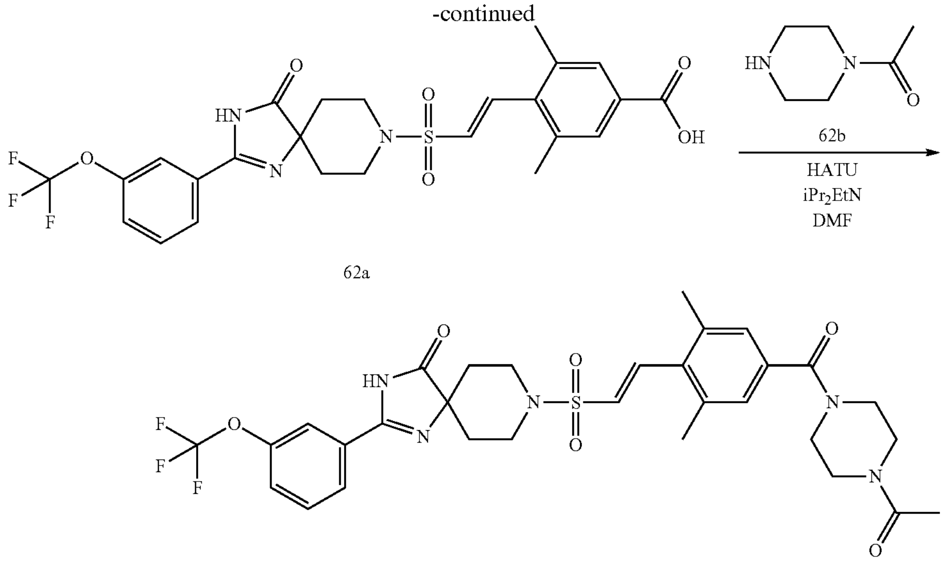

Compound 394

8-{(E)-2-[4-(4-Acetyl-piperazine-1-carbonyl)-2,6-dimethyl-phenyl]-ethenesulfonyl}-2-(3-trifluoromethoxy-phenyl)-1,3,8-triaza-spiro[4.5]dec-1-en-4-one was synthesized by operations similar to those in Reaction 26-1 and Reaction 10-14 using appropriate reagents and starting material.

MS (ESI) m/z=662 (M+H)+.

The example compounds shown below were synthesized by operations similar to those in Example 62 using appropriate reagents and starting materials.

Compounds 395 to 408

TABLE 55

| Compound | Structure | LCMS or HPLC condition | Retention time (min) | MS (m/z) |
|---|---|---|---|---|
| 395 | 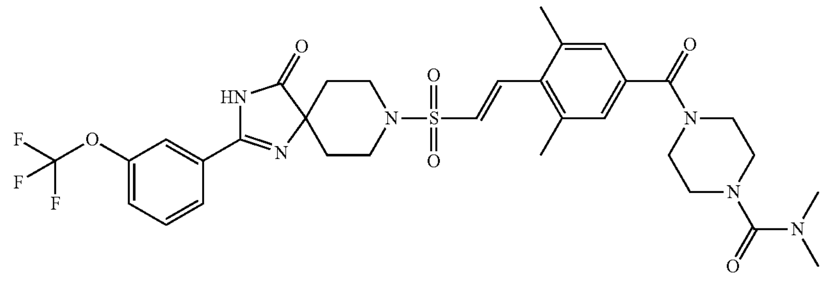 [SMILES: Cc1cc(C(=O)N2CCN(C(=O)N(C)C)CC2)cc(C)c1/C=C/S(=O)(=O)N1CCC2(CC1)N=C(c1cccc(OC(F)(F)F)c1)NC2=O] | LCMS-C-1 | 2.67 | 691 (M + H)+ |
| 396 | 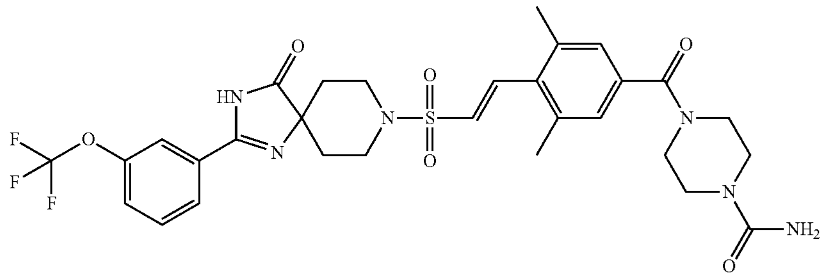 [SMILES: Cc1cc(C(=O)N2CCN(C(N)=O)CC2)cc(C)c1/C=C/S(=O)(=O)N1CCC2(CC1)N=C(c1cccc(OC(F)(F)F)c1)NC2=O] | LCMS-C-1 | 2.52 | 663 (M + H)+ |

TABLE 55-continued
| Compound | Structure | LCMS or HPLC condition | Retention time (min) | MS (m/z) |
| --- | --- | --- | --- | --- |
| 397 | 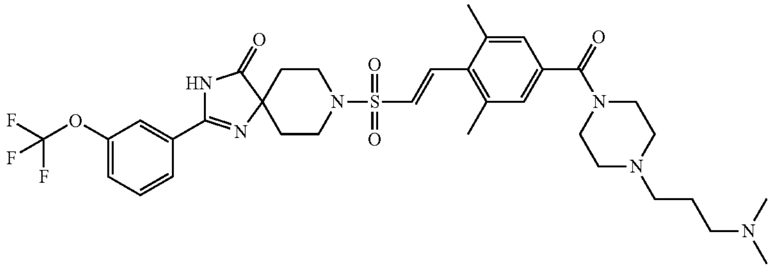 [SMILES: Cc1cc(C(=O)N2CCN(CCCN(C)C)CC2)cc(C)c1/C=C/S(=O)(=O)N1CCC2(CC1)N=C(c1cccc(OC(F)(F)F)c1)NC2=O] | LCMS-C-1 | 2.50 | 705 (M + H)+ |
| 398 | 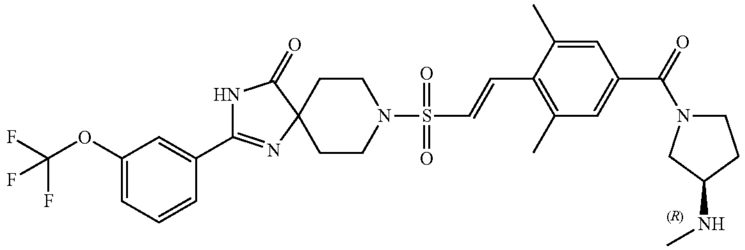 | LCMS-D-1 | 2.7 | 634 (M + H)+ |
| 399 | 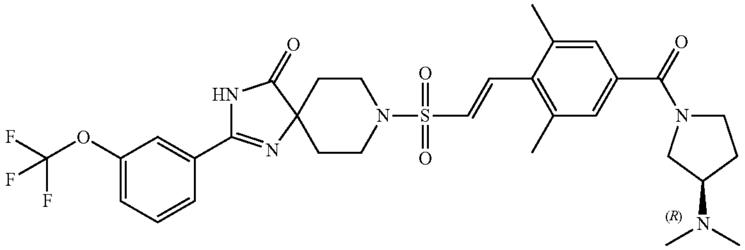 | LCMS-D-1 | 2.7 | 648 (M + H)+ |
| 400 | 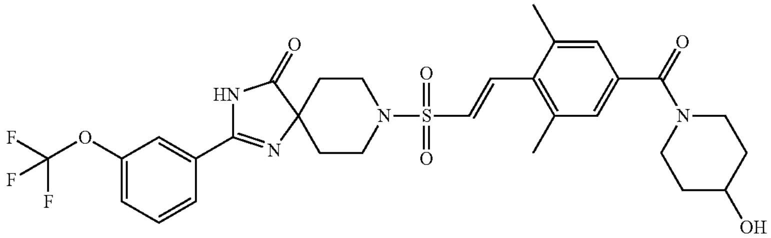 [SMILES: Cc1cc(C(=O)N2CCC(O)CC2)cc(C)c1/C=C/S(=O)(=O)N1CCC2(CC1)N=C(c1cccc(OC(F)(F)F)c1)NC2=O] | LCMS-D-1 | 3.0 | 635 (M + H)+ |
| 401 | 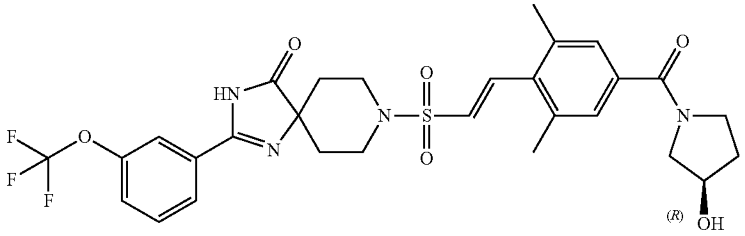 | LCMS-D-1 | 3.0 | 621 (M + H)+ |
| 402 | 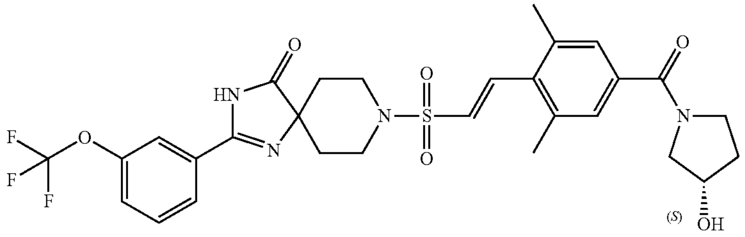 | LCMS-D-1 | 3.0 | 621 (M + H)+ |

TABLE 55-continued
| Compound | Structure | LCMS or HPLC condition | Retention time (min) | MS (m/z) |
|---|---|---|---|---|
| 403 | 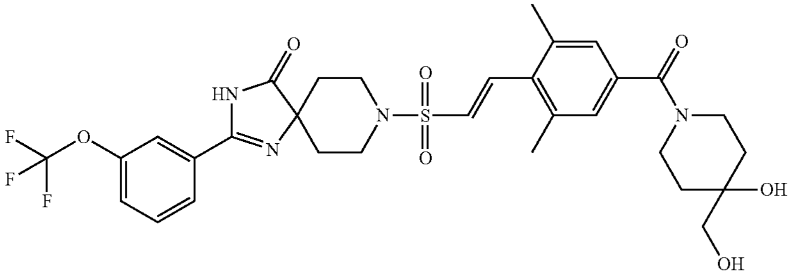 [SMILES: Cc1cc(C(=O)N2CCC(O)(CO)CC2)cc(C)c1/C=C/S(=O)(=O)N1CCC2(CC1)N=C(c1cccc(OC(F)(F)F)c1)NC2=O] | LCMS-D-1 | 2.9 | 665 (M + H)+ |
| 404 | 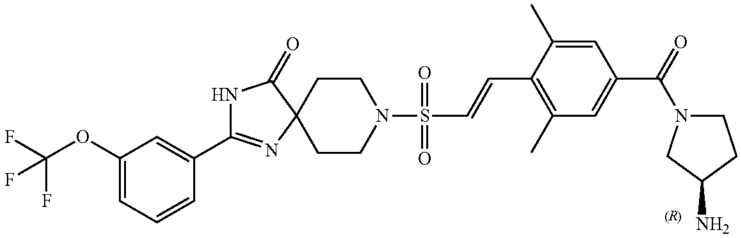 | LCMS-D-1 | 2.7 | 620 (M + H)+ |
| 405 | 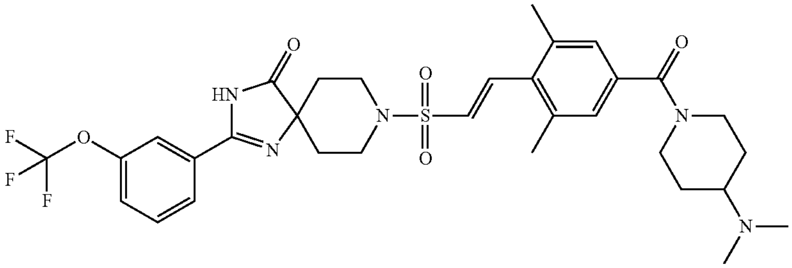 [SMILES: Cc1cc(C(=O)N2CCC(N(C)C)CC2)cc(C)c1/C=C/S(=O)(=O)N1CCC2(CC1)N=C(c1cccc(OC(F)(F)F)c1)NC2=O] | LCMS-D-1 | 2.7 | 662 (M + H)+ |
| 406 | 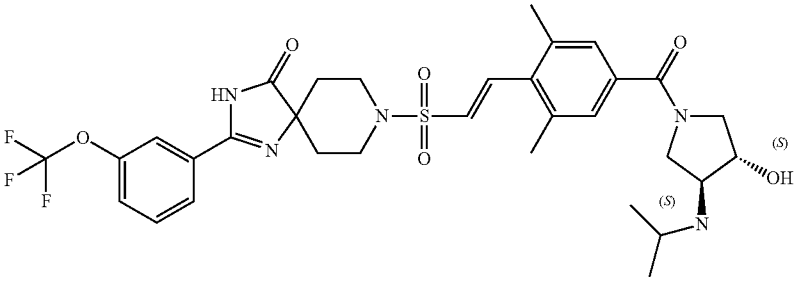 | LCMS-D-1 | 2.7 | 679 (M + H)+ |
| 407 | 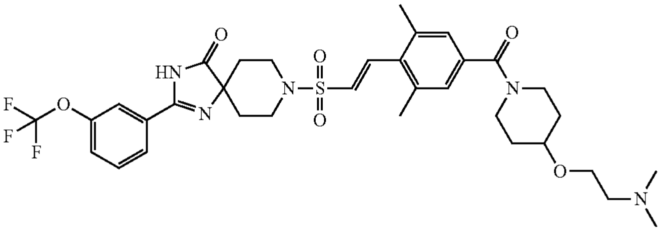 [SMILES: Cc1cc(C(=O)N2CCC(OCCN(C)C)CC2)cc(C)c1/C=C/S(=O)(=O)N1CCC2(CC1)N=C(c1cccc(OC(F)(F)F)c1)NC2=O] | LCMS-D-1 | 2.7 | 707 (M + H)+ |
| 408 | 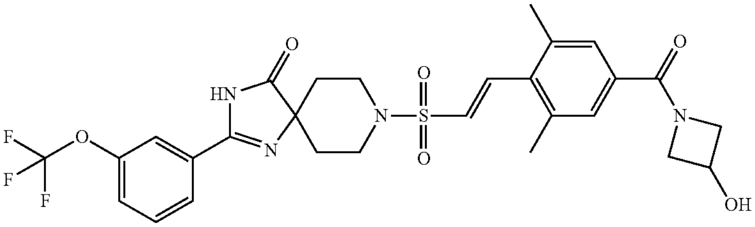 [SMILES: Cc1cc(C(=O)N2CC(O)C2)cc(C)c1/C=C/S(=O)(=O)N1CCC2(CC1)N=C(c1cccc(OC(F)(F)F)c1)NC2=O] | LCMS-D-1 | 3.0 | 607 (M + H)+ |

Example 63

2,N,N-Trimethyl-3-{2-[4-oxo-2-(3-trifluoromethoxy-phenyl)-1,3,8-triaza-spiro[4.5]dec-1-ene-8-sulfonyl]-ethyl}-benzamide (Compound 409)

(Reaction 63-1)

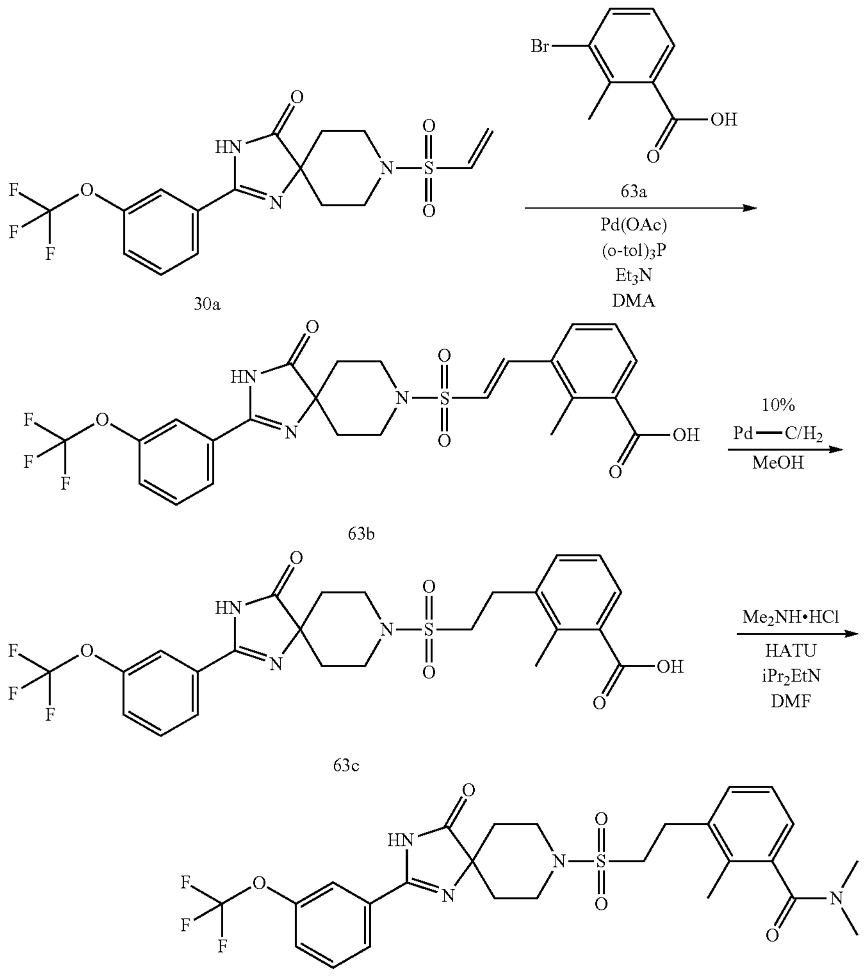

30a, 63b, 63c, Compound 409

2,N,N-Trimethyl-3-{2-[4-oxo-2-(3-trifluoromethoxy-phenyl)-1,3,8-triaza-spiro[4.5]dec-1-ene-8-sulfonyl]-ethyl}-benzamide was synthesized by operations similar to those in Reaction 26-1, Reaction 42-1 and Reaction 10-14 using appropriate reagents and starting material.

MS (ESI) m/z=567 (M+H)+.

The example compounds shown below were synthesized by operations similar to those in Example 63 using appropriate reagents and starting materials.

Compounds 410 to 411

TABLE 56

| Compound | Structure | LCMS or HPLC condition | Retention time (min) | MS (m/z) |
|---|---|---|---|---|
| 410 | 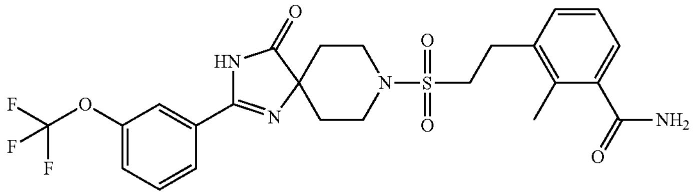 [SMILES: Cc1c(CCS(=O)(=O)N2CCC3(CC2)N=C(c2cccc(OC(F)(F)F)c2)NC3=O)cccc1C(N)=O] | LCMS-D-1 | 2.9 | 539 (M + H)+ |

TABLE 56-continued
| Compound | Structure | LCMS or HPLC condition | Retention time (min) | MS (m/z) |
|---|---|---|---|---|
| 411 | 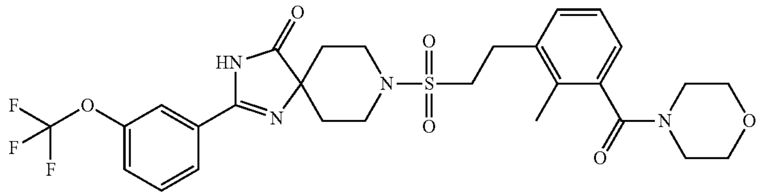 [SMILES: Cc1c(CCS(=O)(=O)N2CCC3(CC2)N=C(c2cccc(OC(F)(F)F)c2)NC3=O)cccc1C(=O)N1CCOCC1] | LCMS-D-1 | 3.1 | 609 (M + H)+ |
Example 64
4,N,N-Trimethyl-3-{2-[4-oxo-2-(3-trifluoromethoxy-phenyl)-1,3,8-triaza-spiro[4.5]dec-1-ene-8-sulfonyl]-ethyl}-benzamide (Compound 412)
(Reaction 64-1)
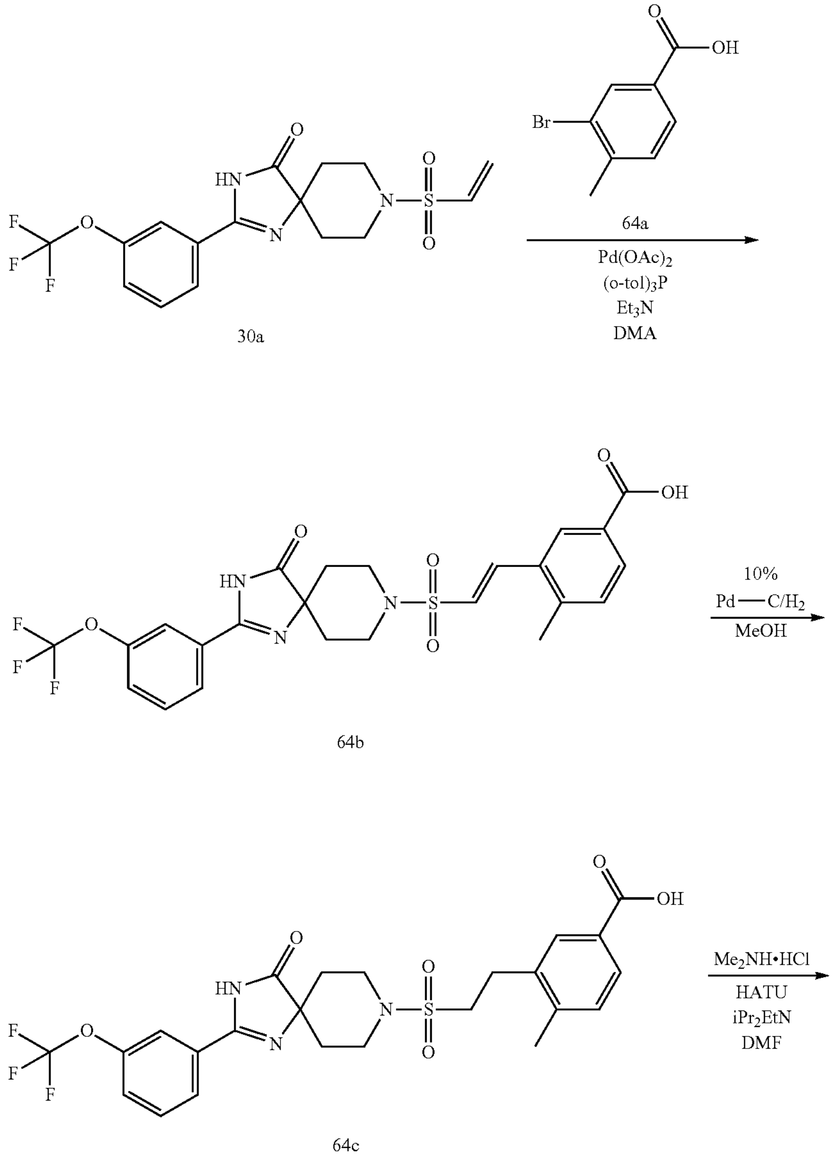

-continued

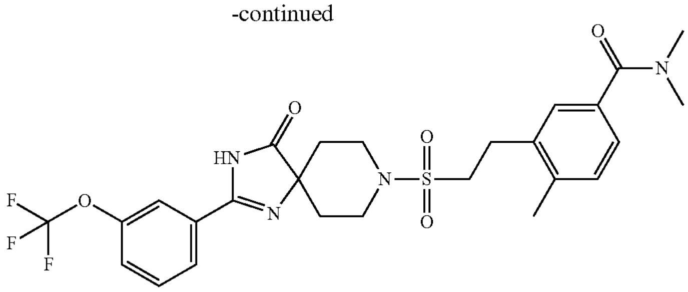

Compound 412

4,N,N-Trimethyl-3-{2-[4-oxo-2-(3-trifluoromethoxy-phenyl)-1,3,8-triaza-spiro[4.5]dec-1-ene-8-sulfonyl]-ethyl}-benzamide was synthesized by operations similar to those in Reaction 26-1, Reaction 42-1 and Reaction 10-14 using appropriate reagents and starting material.

MS (ESI) m/z=567 (M+H)+.

The example compounds shown below were synthesized by operations similar to those in Example 64 using appropriate reagents and starting materials.

Compounds 413 to 415

TABLE 57

| Compound | Structure | LCMS or HPLC condition | Retention time (min) | Ms (m/z) |
|---|---|---|---|---|
| 413 | 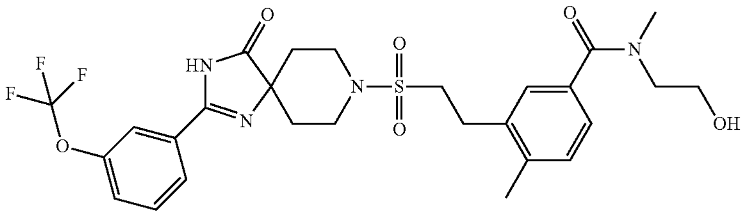 [SMILES: Cc1ccc(C(=O)N(C)CCO)cc1CCS(=O)(=O)N1CCC2(CC1)N=C(c1cccc(OC(F)(F)F)c1)NC2=O] | HPLC-A-1 | 11.5 | 597 (M + H)+ |
| 414 | 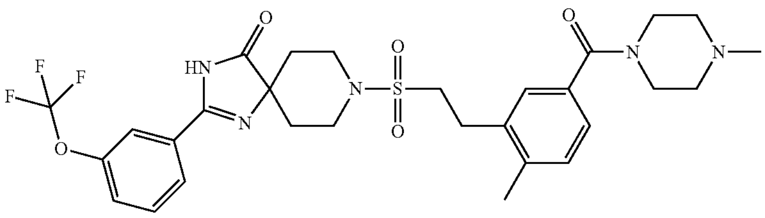 [SMILES: Cc1ccc(C(=O)N2CCN(C)CC2)cc1CCS(=O)(=O)N1CCC2(CC1)N=C(c1cccc(OC(F)(F)F)c1)NC2=O] | HPLC-A-1 | 9.4 | 311 (M + H)+ |
| 415 | 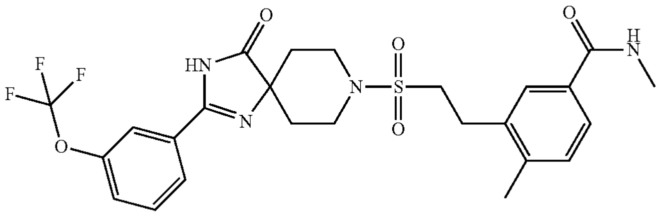 [SMILES: CNC(=O)c1ccc(C)c(CCS(=O)(=O)N2CCC3(CC2)N=C(c2cccc(OC(F)(F)F)c2)NC3=O)c1] | HPLC-A-2 | 9.5 | 553 (M + H)+ |

Example 65
8-(2-{4-[4-(2-Hydroxy-ethyl)-piperazine-1-carbonyl]-2-methyl-phenyl}-ethanesulfonyl)-2-(3-trifluoromethoxy-phenyl)-1,3,8-triaza-spiro[4.5]dec-1-en-4-one (Compound 416)
(Reaction 65-1)
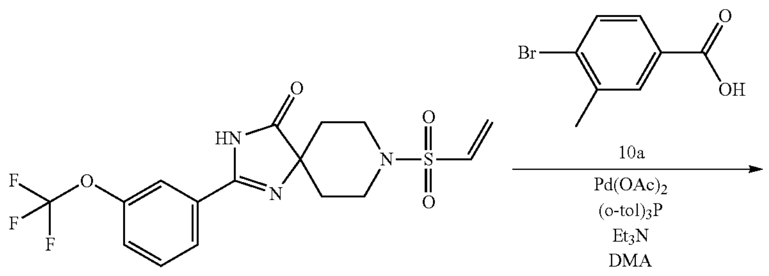
30a
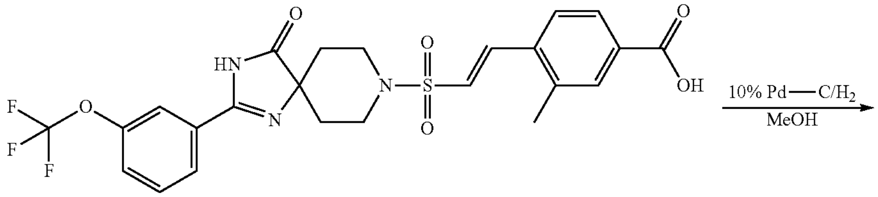
65a
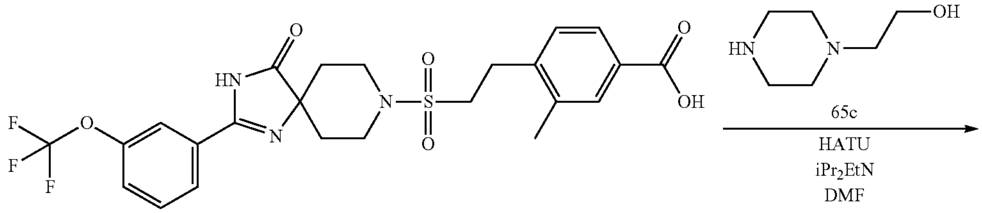
65b
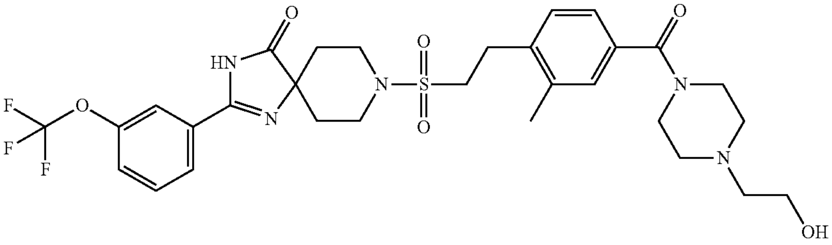
Compound 416

8-(2-{4-[4-(2-Hydroxy-ethyl)-piperazine-1-carbonyl]-2-methyl-phenyl}-ethanesulfonyl)-2-(3-trifluoromethoxy-phenyl)-1,3,8-triaza-spiro[4.5]dec-1-en-4-one was synthesized by operations similar to those in Reaction 26-1, Reaction 42-1 and Reaction 10-14 using appropriate reagents and starting material.

MS (ESI) m/z=652 (M+H)+.

The example compound shown below was synthesized by operations similar to those in Example 64 using appropriate reagents and starting material.

Compound 417

(Reaction 66-2)

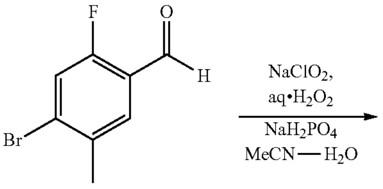

66b

TABLE 58

| Compound | Structure | LCMS or HPLC condition | Retention time (min) | MS (m/z) |
|---|---|---|---|---|
| 417 | 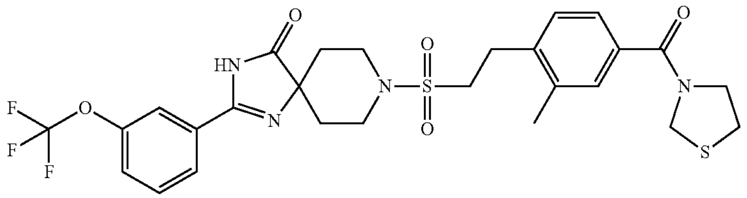 [SMILES: Cc1cc(C(=O)N2CCSC2)ccc1CCS(=O)(=O)N1CCC2(CC1)N=C(c1cccc(OC(F)(F)F)c1)NC2=O] | LCMS-C-2 | 2.31 | 611 (M + H)+ |

Example 66

2-Fluoro-5,N,N-trimethyl-4-{2-[4-oxo-2-(3-trifluoromethyl-phenyl)-1,3,8-triaza-spiro[4.5]dec-1-ene-8-sulfonyl]-ethyl}-benzamide (Compound 418)

(Reaction 66-1)

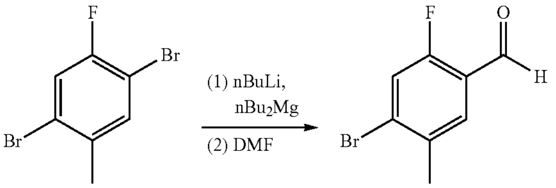

66a 66b n-BuLi (5.0 ml, 8.0 mmol, 1.6 M in hexane) was added dropwise to a solution of n-$Bu_2Mg$ (8.0 ml, 8.0 mmol, 1.0 M in heptane) at room temperature for 10 minutes. The mixture was stirred at room temperature for 15 minutes and then cooled to −10±2° C. A solution of 2,5-dibromo-4-fluorotoluene (5.466 g, 19.59 mmol) in toluene (30 ml)-THF (6 ml) was added dropwise to this mixed reaction solution over 30 minutes, and the mixture was then stirred at 0° C. for one hour. The reaction mixture was added dropwise to a solution cooled to −10° C. of DMF (2.1 ml, 27 mmol) in toluene (7.6 ml) over 15 minutes. Further, this mixture was stirred at −10 to −5° C. for 30 minutes, and then quenched with an aqueous citric acid solution (2.3 M, 16 ml, 37 mmol) and extracted with $Et_2O$. The organic layer was washed with water, and then dried over $MgSO_4$ and concentrated under reduced pressure to give 4-bromo-2-fluoro-5-methyl-benzaldehyde (3.74 g, 88%).

$^1$H-NMR (300 MHz) ($CDCl_3$) δ 2.42 (3H, s), 7.42 (1H, d, J=9.6 Hz), 7.72 (1H, d, J=7.2 Hz), 10.29 (1H, s).

-continued

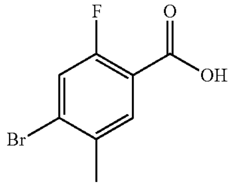

66c $NaH_2PO_4$ (418 mg, 3.48 mmol) in $H_2O$ (17.6 ml), a 35% aqueous $H_2O_2$ solution (2.5 ml, 25.7 mmol) and $NaClO_2$ (2.23 g, 24.7 mmol) in $H_2O$ (34.9 ml) were sequentially added to a mixture of 4-bromo-2-fluoro-5-methyl-benzaldehyde (3.74 g, 17.2 mmol) in MeCN (52 ml) at 0° C. The mixture was stirred at room temperature for 14 hours, and then made acidic (pH 3) with a 10% aqueous HCl solution and extracted with ethyl acetate (3×100 ml). The organic layers were washed with $H_2O$ (70 ml), and then dried over $MgSO_4$ and concentrated under reduced pressure to give 4-bromo-2-fluoro-5-methyl-benzoic acid as a pale orange solid (4.02 g, 100%).

$^1$H-NMR (300 MHz) ($CDCl_3$) δ 2.42 (3H, s), 7.41 (1H, d, J=9.9 Hz), 7.88 (1H, d, J=7.5 Hz). MS (ESI) m/z=231 (M−H)−.

(Reaction 66-3)

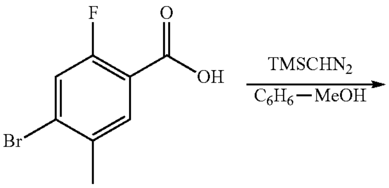

66c

-continued

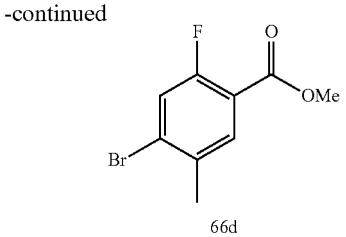

66d (Trimethylsilyl)diazomethane (4.0 ml, 8.0 mmol, 2 M in $Et_2O$) was added dropwise to a solution of 4-bromo-2-fluoro-5-methyl-benzoic acid (1.88 g, 8.05 mmol) in benzene (7.5 ml)-MeOH (5.6 ml) at 10±2° C. over 10 minutes. The mixture was stirred at room temperature for 30 minutes and then concentrated under reduced pressure. The resulting residue was purified by silica gel column chromatography (hexane/ethyl acetate=40/1) to give methyl 4-bromo-2-fluoro-5-methyl-benzoate (1.62 g, 82%).

$^1$H-NMR (300 MHz) ($CDCl_3$) δ 2.40 (3H, s), 3.93 (3H, s), 7.37 (1H, d, J=9.9 Hz), 7.80 (1H, d, J=7.8 Hz).

(Reaction 66-4)

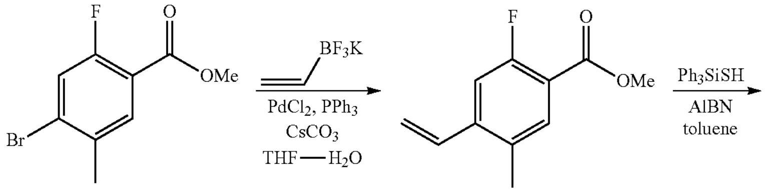

66d 66e

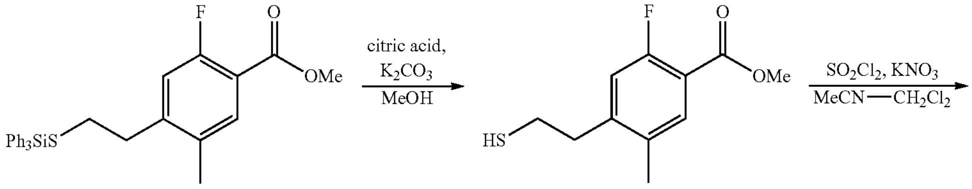

66f 66g

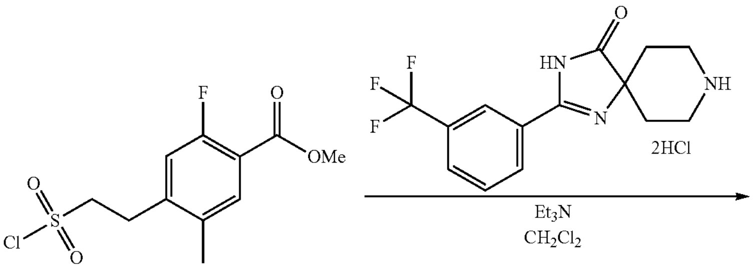

66h

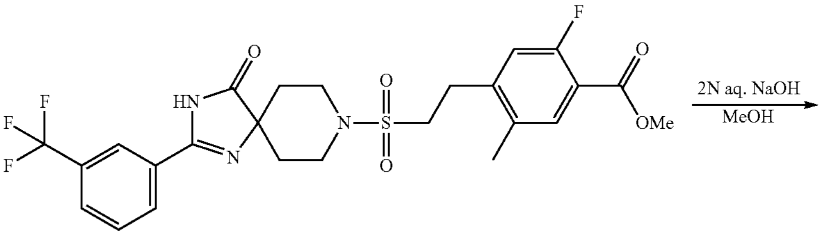

66i

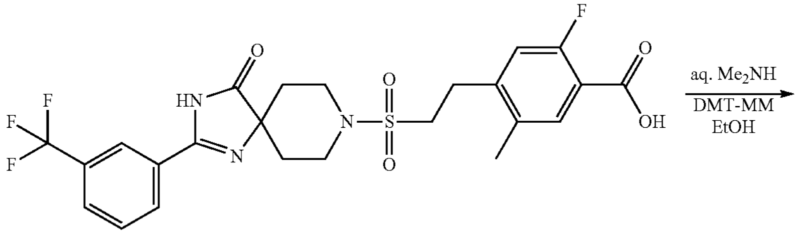

66j

-continued

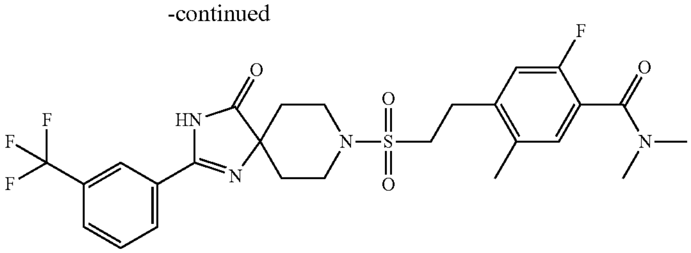

Compound 418

2-Fluoro-5,N,N-trimethyl-4-{2-[4-oxo-2-(3-trifluoromethyl-phenyl)-1,3,8-triaza-spiro[4.5]dec-1-ene-8-sulfonyl]-ethyl}-benzamide was synthesized by operations similar to those in Reaction 10-2, Reaction 10-3, Reaction 10-4, Reaction 10-5, Reaction 5-4, Reaction 23-2 and Reaction 10-1 using appropriate reagents and starting material.

MS (ESI) m/z=569 (M+H)+.

The example compound shown below was synthesized by operations similar to those in Example 66 using appropriate reagents and starting material.

Compound 419

TABLE 59

| Compound | Structure | LCMS or HPLC condition | Retention time (min) | MS (m/z) |
|---|---|---|---|---|
| 419 | 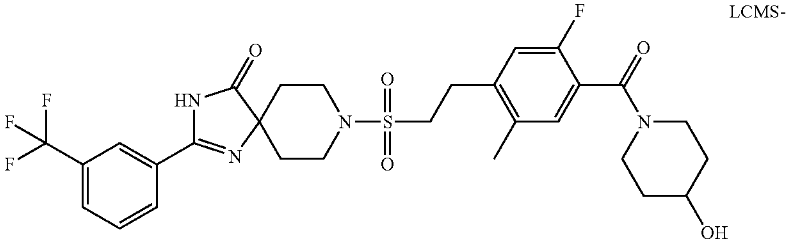 | LCMS-C-2 | 1.78 | 625 (M + H)+ |

-continued

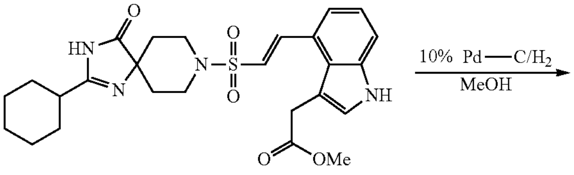

67b

Example 67

N-Benzyl-2-{4-[2-(2-cyclohexyl-4-oxo-1,3,8-triaza-spiro[4.5]dec-1-ene-8-sulfonyl)-ethyl]-1H-indol-3-yl}-acetamide (Compound 420)

(Reaction 67-1)

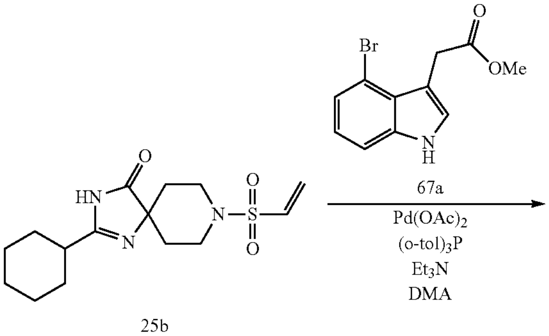

67a

25b

-continued

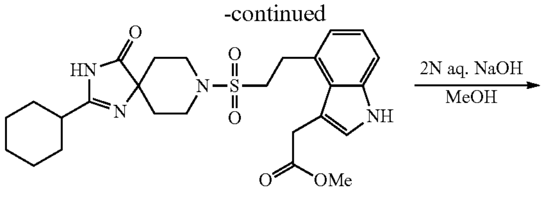

67c

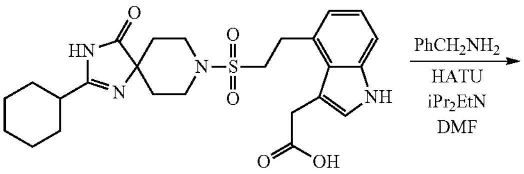

67d

-continued

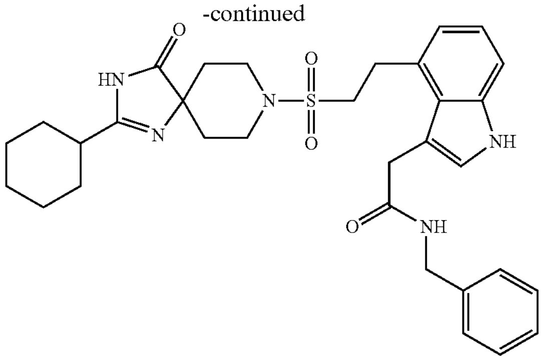

Compound 420

N-Benzyl-2-{4-[2-(2-cyclohexyl-4-oxo-1,3,8-triaza-spiro[4.5]dec-1-ene-8-sulfonyl)-ethyl]-1H-indol-3-yl}-acetamide was synthesized by operations similar to those in Reaction 25-2, Reaction 42-1, Reaction 23-2 and Reaction 10-1 using appropriate reagents and starting material.

MS (ESI) m/z=590 (M+H)+.

Example 68

2-[2-(2-Cyclohexyl-4-oxo-1,3,8-triaza-spiro[4.5]dec-1-ene-8-sulfonyl)-ethyl]-N-methyl-benzamide (Compound 421)

(Reaction 68-1)

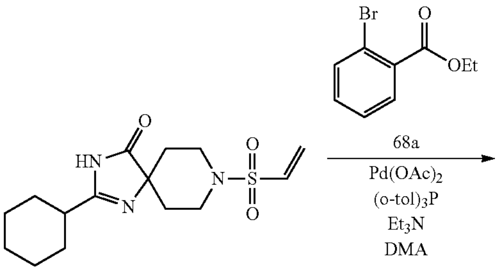

25b

-continued

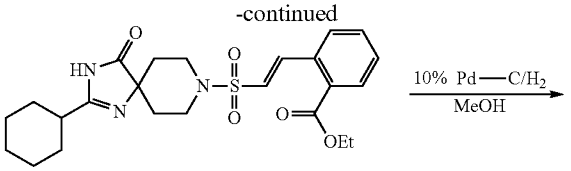

68b

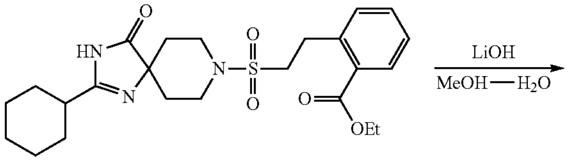

68c

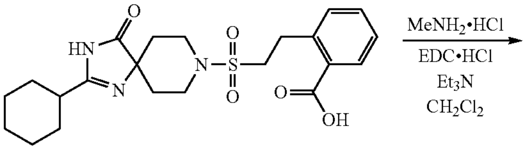

68d

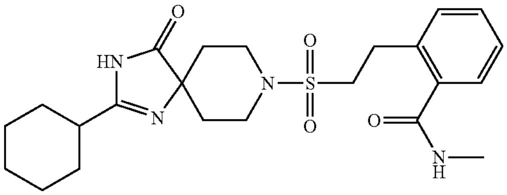

Compound 421

2-[2-(2-Cyclohexyl-4-oxo-1,3,8-triaza-spiro[4.5]dec-1-ene-8-sulfonyl)-ethyl]-N-methyl-benzamide was synthesized by operations similar to those in Reaction 25-2, Reaction 42-1, Reaction 23-2 and Reaction 10-18 using appropriate reagents and starting material.

MS (ESI) m/z=461 (M+H)+.

The example compound shown below was synthesized by operations similar to those in Example 68 using appropriate reagents and starting material.

Compound 422

TABLE 60

| Compound | Structure | LCMS or HPLC condition | Retention time (min) | MS (m/z) |
|---|---|---|---|---|
| 422 | 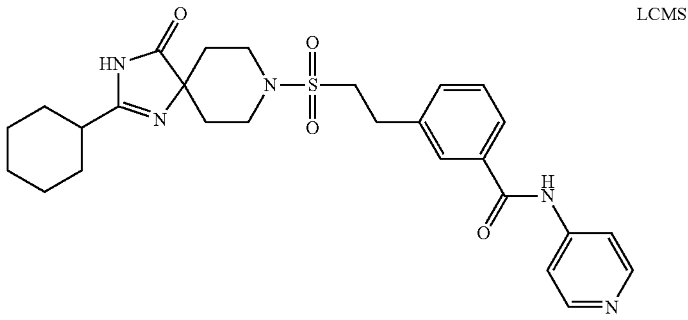 | LCMS-E-6 | 3.33 | 525 (M + H)+ |

Example 69

8-(3-Chloro-benzenesulfonyl)-2-[1-(3,3-dimethyl-butyryl)-piperidin-3-yl]-1,3,8-triaza-spiro[4.5]dec-1-en-4-one (Compound 423)

(Reaction 69-1)

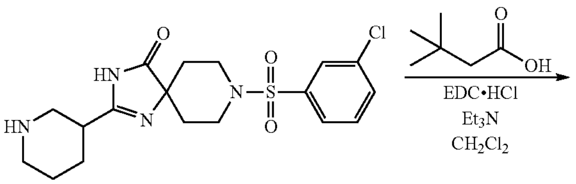

$CF_3CO_2H$

69a

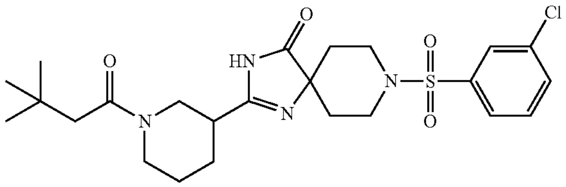

Compound 423

8-(3-Chloro-benzenesulfonyl)-2-[1-(3,3-dimethyl-butyryl)-piperidin-3-yl]-1,3,8-triaza-spiro[4.5]dec-1-en-4-one was synthesized by operations similar to those in Reaction 10-18 using appropriate reagents and starting material.

MS (ESI) m/z=509 (M+H)+.

The example compound shown below was synthesized by operations similar to those in Example 69 using appropriate reagents and starting material.

Compound 424

Example 70

8-(3-Chloro-benzenesulfonyl)-2-[1-(4-chloro-benzoyl)-piperidin-3-yl]-1,3,8-triaza-spiro[4.5]dec-1-en-4-one (Compound 425)

(Reaction 70-1)

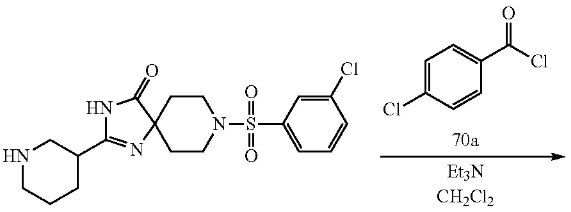

$CF_3CO_2H$

69a

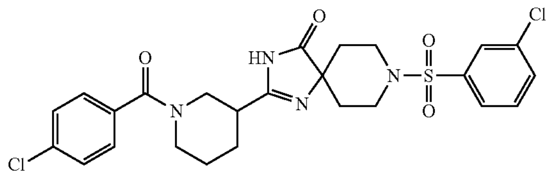

Compound 425

8-(3-Chloro-benzenesulfonyl)-2-[1-(4-chloro-benzoyl)-piperidin-3-yl]-1,3,8-triaza-spiro[4.5]dec-1-en-4-one was synthesized by operations similar to those in Reaction 2-3 using appropriate reagents and starting material.

$^1$H-NMR (400 MHz, $CDCl_3$) δ 1.36-1.67 (m, 5H), 1.84-2.06 (m, 4H), 2.66-2.84 (m, 1H), 2.90-3.10 (m, 2H), 3.16-3.34 (m, 1H), 3.41-3.55 (m, 1H), 3.55-3.67 (m, 2H), 4.04-4.27 (m, 1H), 7.23-7.29 (m, 2H), 7.30-7.37 (m, 2H), 7.43 (t, J=7.83 Hz, 1H), 7.50-7.55 (m, 1H), 7.59-7.65 (m, 1H), 7.72 (t, J=1.77 Hz, 1H). MS (ESI) m/z=549 (M+H)+.

The example compound shown below was synthesized by operations similar to those in Example 70 using appropriate reagents and starting material.

TABLE 61

| Compound | Structure | LCMS or HPLC condition | Retention time (min) | MS (m/z) |
|---|---|---|---|---|
| 424 | 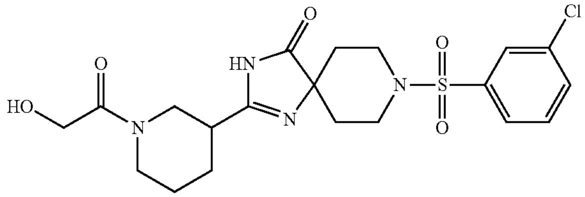 [SMILES: O=C(CO)N1CCCC(C2=NC3(CCN(S(=O)(=O)c4cccc(Cl)c4)CC3)C(=O)N2)C1] | LCMS-E-2 | 2.9 | 469 (M + H)+ |

Compound 426

TABLE 62

| Compound | Structure | LCMS or HPLC condition | Retention time (min) | MS (m/z) |
|---|---|---|---|---|
| 426 | 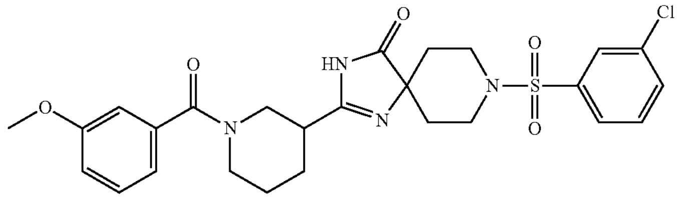 [SMILES: COc1cccc(C(=O)N2CCCC(C3=NC4(CCN(S(=O)(=O)c5cccc(Cl)c5)CC4)C(=O)N3)C2)c1] | LCMS-E-2 | 3.82 | 545 (M + H)+ |

Example 72

2-[1-(1H-Indol-5-carbonyl)-piperidin-3-yl]-8-(2-naphthalen-1-yl-ethanesulfonyl)-1,3,8-triaza-spiro[4.5]dec-1-en-4-one (Compound 428)

(Reaction 72-1)

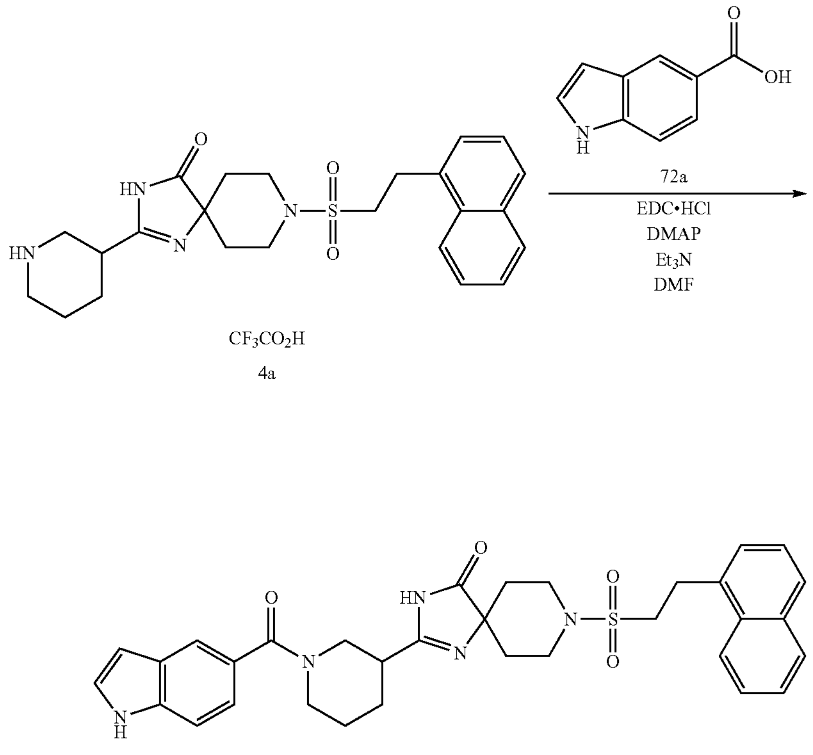

72a $CF_3CO_2H$

4a

Compound 428

2-[1-(1H-Indol-5-carbonyl)-piperidin-3-yl]-8-(2-naphthalen-1-yl-ethanesulfonyl)-1,3,8-triaza-spiro[4.5]dec-1-en-4-one was synthesized by operations similar to those in Reaction 10-18 using appropriate reagents and starting material.

MS (ESI) m/z=598 (M+H)+.

The example compounds shown below were synthesized by operations similar to those in Example 72 using appropriate reagents and starting materials.

Compounds 429 to 439
TABLE 63
| Compound | Structure | LCMS or HPLC condition | Retention time (min) | MS (m/z) |
|---|---|---|---|---|
| 429 | 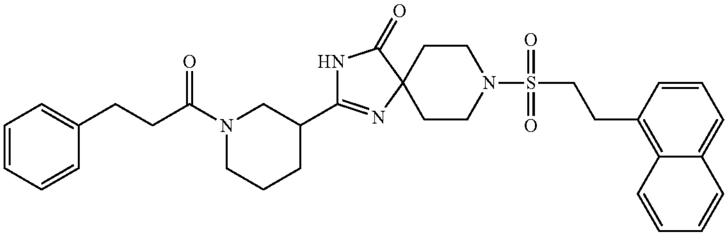 | LCMS-E-3 | 3.5 | 587 (M + H)+ |
| 430 | 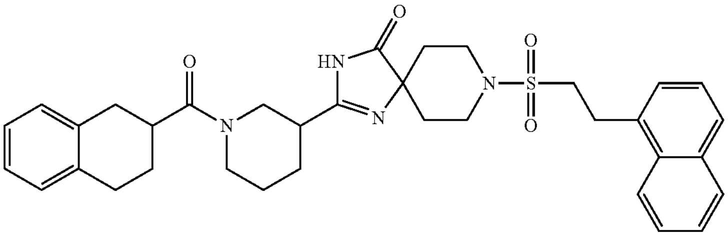 [SMILES: O=C(C1CCc2ccccc2C1)N1CCCC(C2=NC3(CCN(S(=O)(=O)CCc4cccc5ccccc45)CC3)C(=O)N2)C1] | LCMS-E-3 | 3.67 | 613 (M + H)+ |
| 431 | 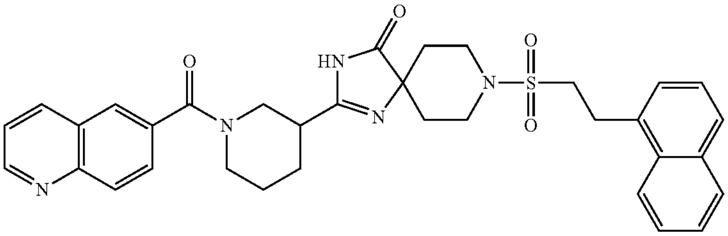 [SMILES: O=C(c1ccc2ncccc2c1)N1CCCC(C2=NC3(CCN(S(=O)(=O)CCc4cccc5ccccc45)CC3)C(=O)N2)C1] | LCMS-E-3 | 1.57 | 610 (M + H)+ |
| 432 | 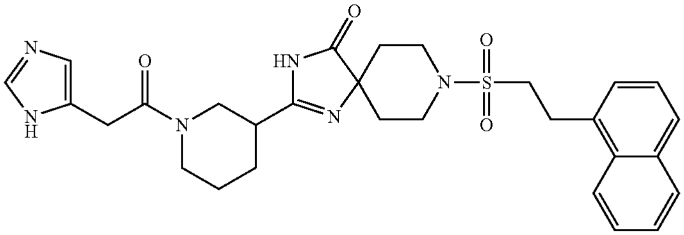 [SMILES: O=C(Cc1cnc[nH]1)N1CCCC(C2=NC3(CCN(S(=O)(=O)CCc4cccc5ccccc45)CC3)C(=O)N2)C1] | LCMS-E-2 | 2.47 | 563 (M + H)+ |
| 433 | 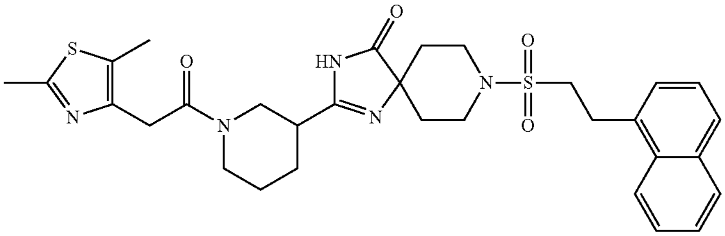 [SMILES: Cc1nc(CC(=O)N2CCCC(C3=NC4(CCN(S(=O)(=O)CCc5cccc6ccccc56)CC4)C(=O)N3)C2)c(C)s1] | LCMS-E-2 | 3.79 | 608 (M + H)+ |
| 434 | 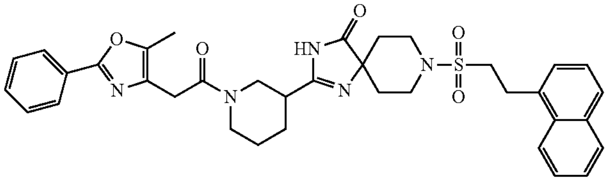 [SMILES: Cc1oc(-c2ccccc2)nc1CC(=O)N1CCCC(C2=NC3(CCN(S(=O)(=O)CCc4cccc5ccccc45)CC3)C(=O)N2)C1] | LCMS-E-2 | 4.49 | 654 (M + H)+ |

TABLE 63-continued
| Compound | Structure | LCMS or HPLC condition | Retention time (min) | MS (m/z) |
|---|---|---|---|---|
| 435 | 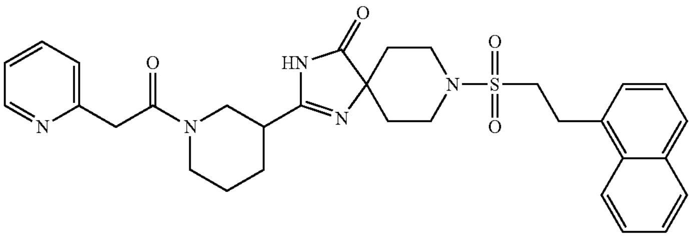 [SMILES: O=C(Cc1ccccn1)N1CCCC(C2=NC3(CCN(S(=O)(=O)CCc4cccc5ccccc45)CC3)C(=O)N2)C1] | LCMS-E-2 | 2.97 | 574 (M + H)+ |
| 436 | 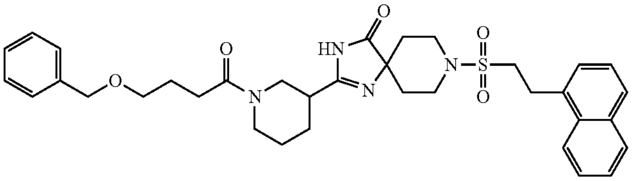 [SMILES: O=C(CCCOCc1ccccc1)N1CCCC(C2=NC3(CCN(S(=O)(=O)CCc4cccc5ccccc45)CC3)C(=O)N2)C1] | LCMS-E-2 | 4.48 | 631 (M + H)+ |
| 437 | 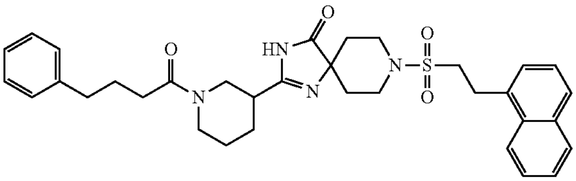 [SMILES: O=C(CCCc1ccccc1)N1CCCC(C2=NC3(CCN(S(=O)(=O)CCc4cccc5ccccc45)CC3)C(=O)N2)C1] | LCMS-E-2 | 4.57 | 601 (M + H)+ |
| 438 | 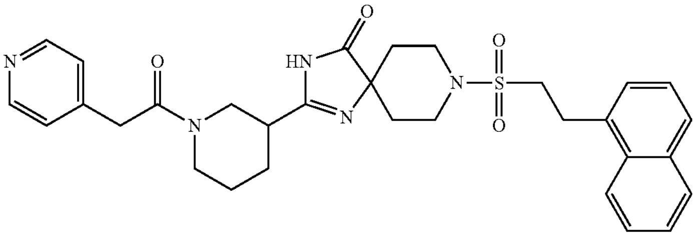 [SMILES: O=C(Cc1ccncc1)N1CCCC(C2=NC3(CCN(S(=O)(=O)CCc4cccc5ccccc45)CC3)C(=O)N2)C1] | LCMS-E-2 | 2.68 | 574 (M + H)+ |
| 439 | 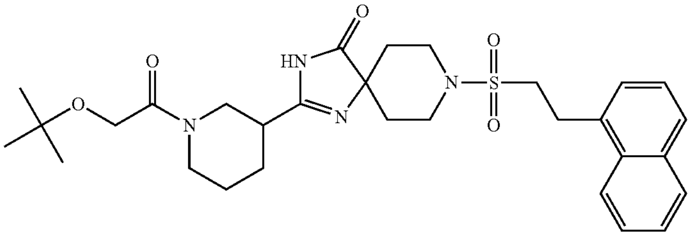 [SMILES: CC(C)(C)OCC(=O)N1CCCC(C2=NC3(CCN(S(=O)(=O)CCc4cccc5ccccc45)CC3)C(=O)N2)C1] | LCMS-E-2 | 4.02 | 569 (M + H)+ |

Example 73

8-(2-Naphthalen-1-yl-ethanesulfonyl)-2-{1-[(E)-(3-phenyl-acryloyl)]-piperidin-3-yl}-1,3,8-triaza-spiro[4.5]dec-1-en-4-one (Compound 441)

(Reaction 73-1)

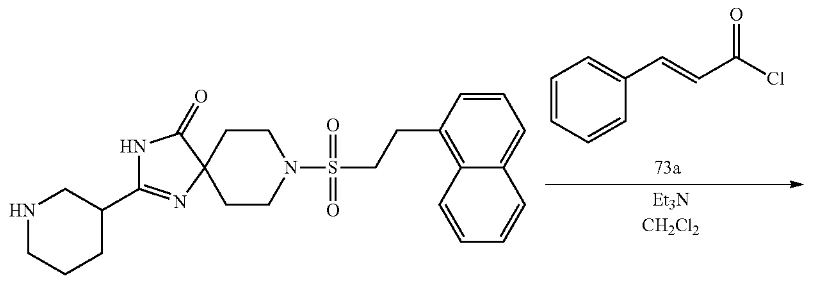

$CF_3CO_2H$

4a

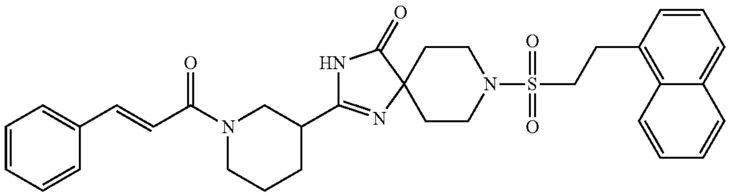

Compound 441

8-(2-Naphthalen-1-yl-ethanesulfonyl)-2-{1-[(E)-(3-phenyl-acryloyl)]-piperidin-3-yl}-1,3,8-triaza-spiro[4.5]dec-1-en-4-one was synthesized by operations similar to those in Reaction 2-3 using appropriate reagents and starting material.

MS (ESI) m/z=585 (M+H)+.

Example 74

2-[1-(2-Amino-acetyl)-piperidin-3-yl]-8-(3-chloro-benzenesulfonyl)-1,3,8-triaza-spiro[4.5]dec-1-en-4-one (Compound 442)

(Reaction 74-1)

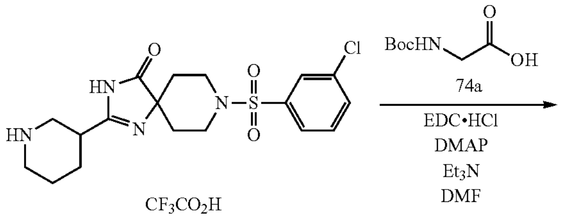

$CF_3CO_2H$

69a

-continued

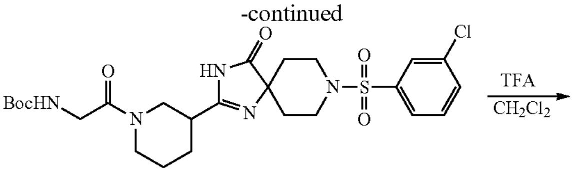

74b

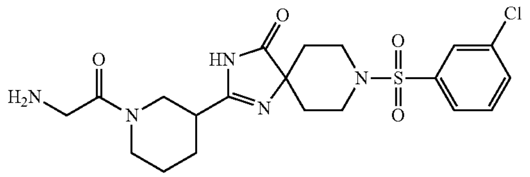

Compound 442

2-[1-(2-Amino-acetyl)-piperidin-3-yl]-8-(3-chloro-benzenesulfonyl)-1,3,8-triaza-spiro[4.5]dec-1-en-4-one was synthesized by operations similar to those in Reaction 10-18 and Reaction 4-1 using appropriate reagents and starting material.

MS (ESI) m/z=468 (M+H)+.

Example 75

8-{2-[2-Methyl-4-(3-methylamino-pyrrolidine-1-carbonyl)-phenyl]-ethanesulfonyl}-2-(3-trifluoromethyl-phenyl)-1,3,8-triaza-spiro[4.5]dec-1-en-4-one (Compound 444)

(Reaction 75-1)

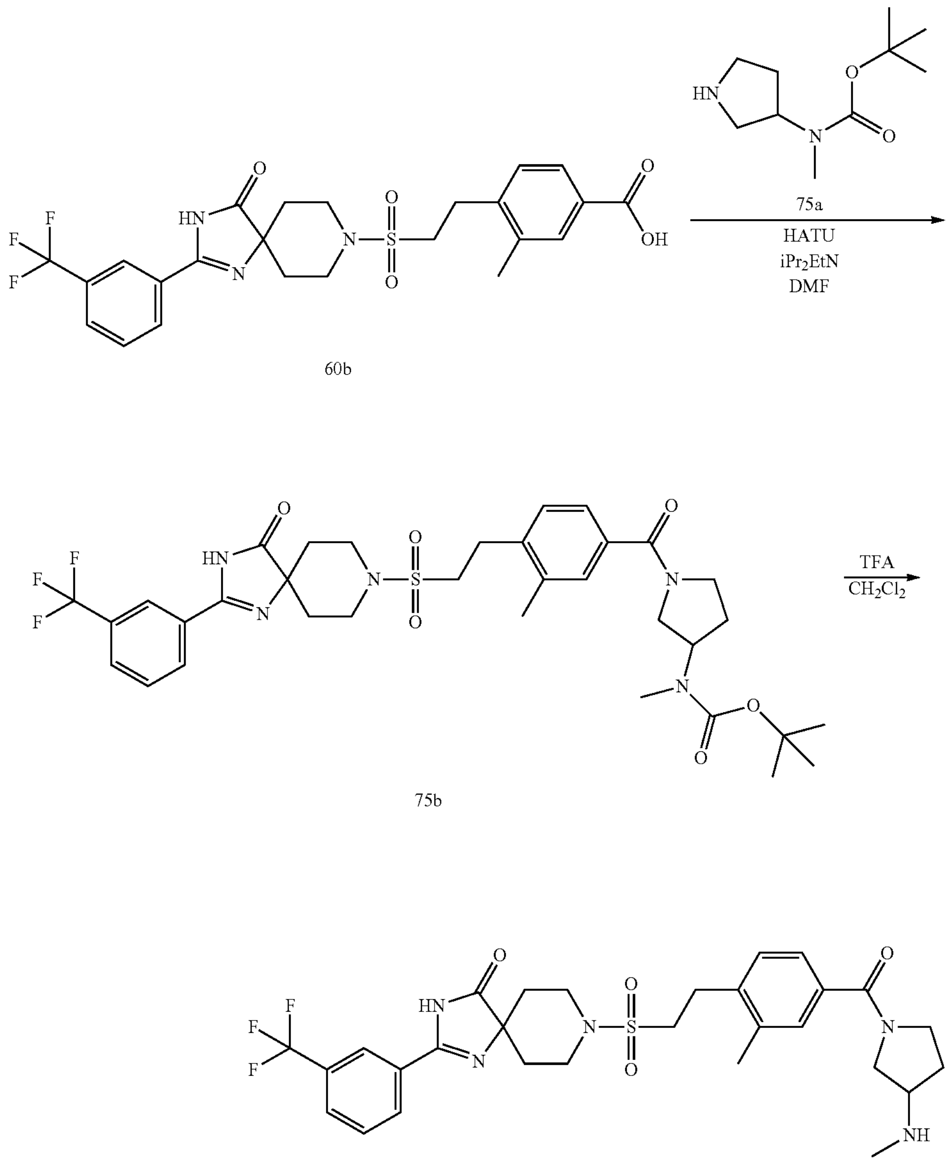

75a

60b

75b

Compound 444

8-{2-[2-Methyl-4-(3-methylamino-pyrrolidine-1-carbonyl)-phenyl]-ethanesulfonyl}-2-(3-trifluoromethyl-phenyl)-1,3,8-triaza-spiro[4.5]dec-1-en-4-one was synthesized by operations similar to those in Reaction 10-14 and Reaction 4-1 using appropriate reagents and starting material.

MS (ESI) m/z=606 (M+H)+.

The example compounds shown below were synthesized by operations similar to those in Example 75 using appropriate reagents and starting materials.

Compounds 445 to 446
TABLE 64
| Compound | Structure | LCMS or HPLC condition | Retention time (min) | MS (m/z) |
|---|---|---|---|---|
| 445 | 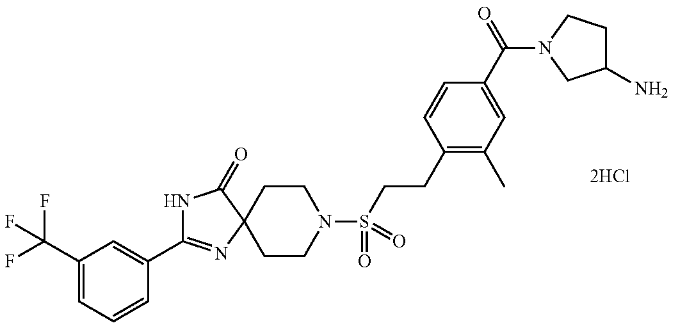 [SMILES: Cc1cc(C(=O)N2CCC(N)C2)ccc1CCS(=O)(=O)N1CCC2(CC1)N=C(c1cccc(C(F)(F)F)c1)NC2=O] 2HCl | LCMS-B-1 | 1.70 | 592 (M + H)+ |
| 446 | 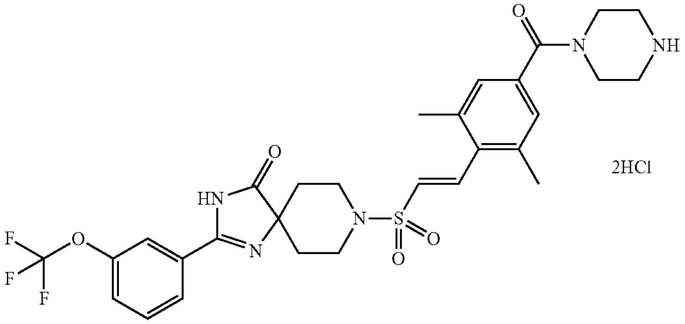 [SMILES: Cc1cc(C(=O)N2CCNCC2)cc(C)c1/C=C/S(=O)(=O)N1CCC2(CC1)N=C(c1cccc(OC(F)(F)F)c1)NC2=O] 2HCl | LCMS-C-1 | 2.50 | 620 (M + H)+ |
Example 76
8-((E)-2-{4-[4-(2-Hydroxy-acetyl)-piperazine-1-carbonyl]-2,6-dimethyl-phenyl}-ethenesulfonyl)-2-(3-trifluoromethoxy-phenyl)-1,3,8-triaza-spiro[4.5]dec-1-en-4-one (Compound 447)
(Reaction 76-1)
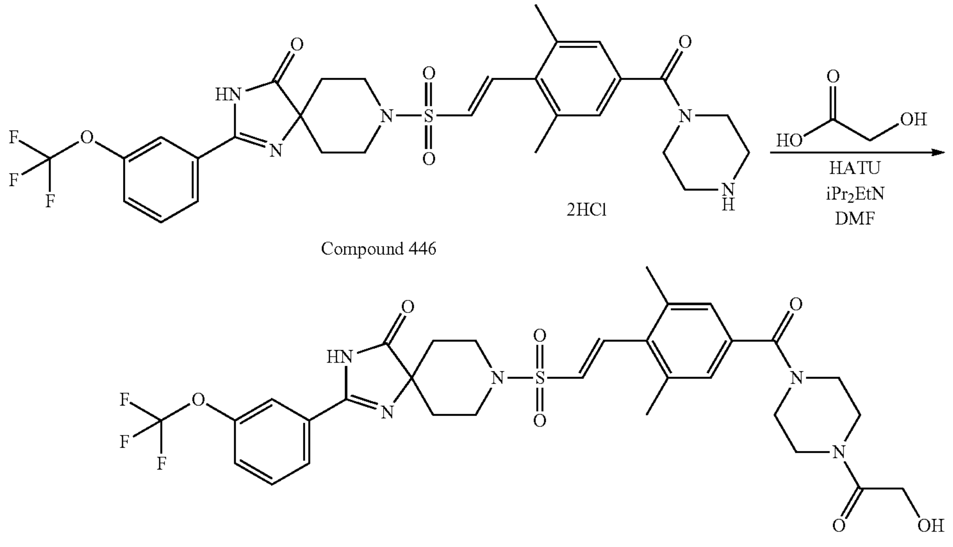
Compound 446
Compound 447

8-((E)-2-{4-[4-(2-Hydroxy-acetyl)-piperazine-1-carbonyl]-2,6-dimethyl-phenyl}-ethenesulfonyl)-2-(3-trifluoromethoxy-phenyl)-1,3,8-triaza-spiro[4.5]dec-1-en-4-one was synthesized by operations similar to those in Reaction 10-14 using appropriate reagents and starting material.

MS (ESI) m/z=678 (M+H)+.

The example compounds shown below were synthesized by operations similar to those in Example 76 using appropriate reagents and starting materials.

Compounds 448 to 449

TABLE 65

| Compound | Structure | LCMS or HPLC condition | Retention time (min) | MS (m/z) |
|---|---|---|---|---|
| 448 | 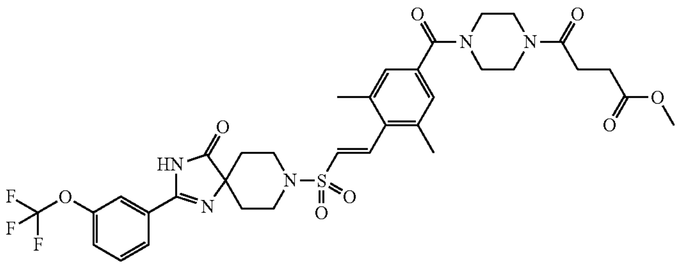 [SMILES: COC(=O)CCC(=O)N1CCN(C(=O)c2cc(C)c(/C=C/S(=O)(=O)N3CCC4(CC3)N=C(c3cccc(OC(F)(F)F)c3)NC4=O)c(C)c2)CC1] | LCMS-C-1 | 2.62 | 734 (M + H)+ |
| 449 | 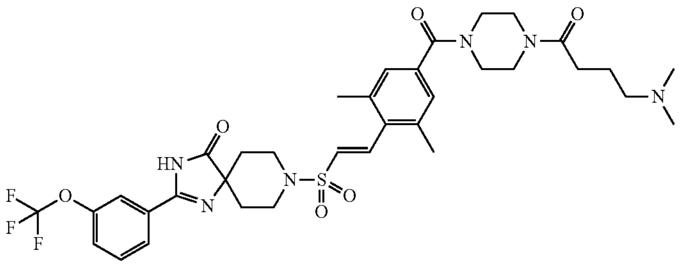 [SMILES: Cc1cc(C(=O)N2CCN(C(=O)CCCN(C)C)CC2)cc(C)c1/C=C/S(=O)(=O)N1CCC2(CC1)N=C(c1cccc(OC(F)(F)F)c1)NC2=O] | LCMS-C-1 | 2.43 | 733 (M + H)+ |

Example 77

2-Methoxy-N-methyl-N-(3-methyl-4-{(E)-2-[4-oxo-2-(3-trifluoromethoxy-phenyl)-1,3,8-triaza-spiro[4.5]dec-1-ene-8-sulfonyl]-vinyl}-phenyl)-acetamide (Compound 450)

(Reaction 77-1)

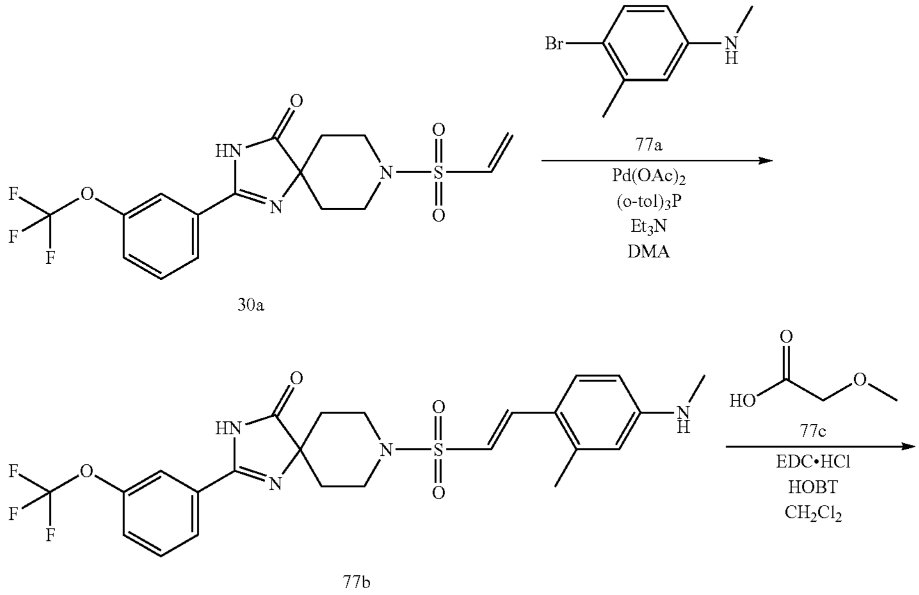

-continued

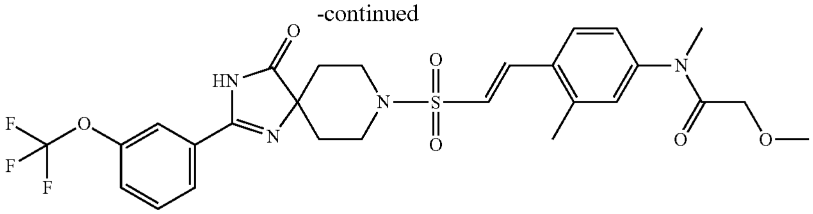

Compound 450

2-Methoxy-N-methyl-N-(3-methyl-4-{(E)-2-[4-oxo-2-(3-trifluoromethoxy-phenyl)-1,3,8-triaza-spiro[4.5]dec-1-ene-8-sulfonyl]-vinyl}-phenyl)-acetamide was synthesized by operations similar to those in Reaction 26-1 and Reaction 10-18 using appropriate reagents and starting material.

MS (ESI) m/z=595 (M+H)+.

Example 78

2-Hydroxy-N-methyl-N-(3-methyl-4-{(E)-2-[4-oxo-2-(3-trifluoromethoxy-phenyl)-1,3,8-triaza-spiro[4.5]dec-1-ene-8-sulfonyl]-vinyl}-phenyl)-acetamide (Compound 451)

(Reaction 78-1)

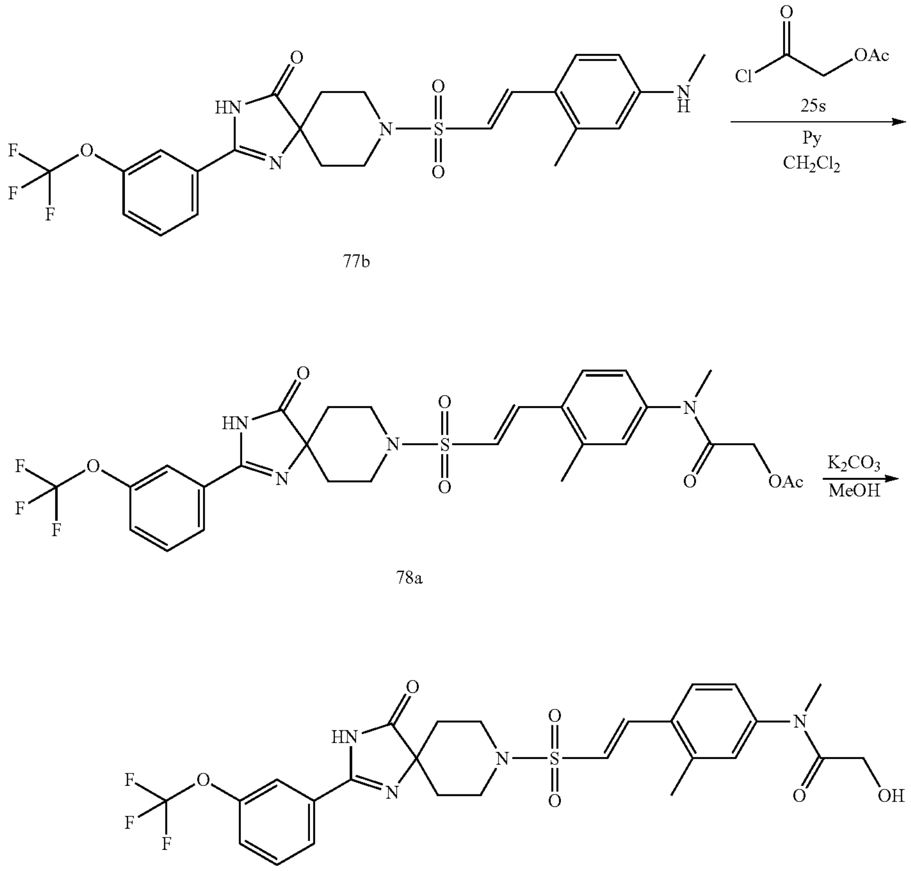

77b

78a

Compound 451

2-Hydroxy-N-methyl-N-(3-methyl-4-{(E)-2-[4-oxo-2-(3-trifluoromethoxy-phenyl)-1,3,8-triaza-spiro[4.5]dec-1-ene-8-sulfonyl]-vinyl}-phenyl)-acetamide was synthesized by operations similar to those in Reaction 2-3 and Reaction 12-5 using appropriate reagents and starting material.

MS (ESI) m/z=581 (M+H)+.

Example 79

[(3,5-Dimethyl-4-{(E)-2-[4-oxo-2-(3-trifluoromethyl-phenyl)-1,3,8-triaza-spiro[4.5]dec-1-ene-8-sulfonyl]-vinyl}-benzoyl)-methyl-amino]-acetic acid (Compound 452)

(Reaction 79-1)

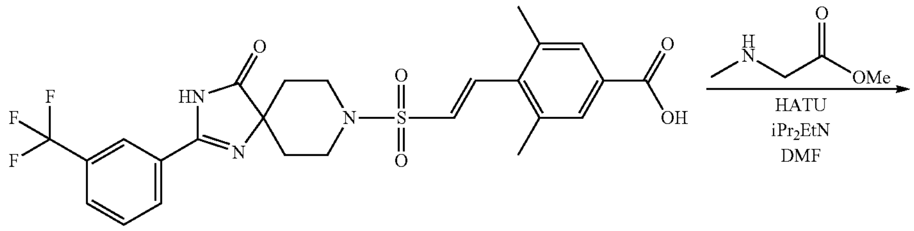

61a

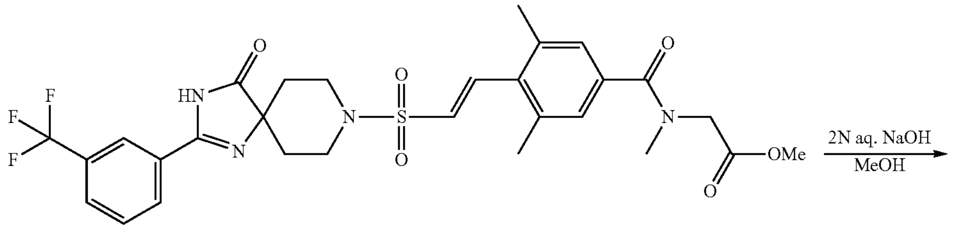

79a

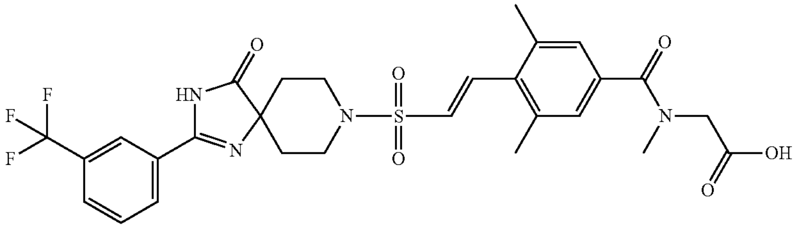

Compound 452

[(3,5-Dimethyl-4-{(E)-2-[4-oxo-2-(3-trifluoromethyl-phenyl)-1,3,8-triaza-spiro[4.5]dec-1-ene-8-sulfonyl]-vinyl}-benzoyl)-methyl-amino]-acetic acid was synthesized by operations similar to those in Reaction 10-14 and Reaction 23-2 using appropriate reagents and starting material.

MS (ESI) m/z=607 (M+H)+.

Example 80

8-(3-Chloro-benzenesulfonyl)-2-[1-(3,3-dimethyl-butyl)-piperidin-3-yl]-1,3,8-triaza-spiro[4.5]dec-1-en-4-one (Compound 453)

(Reaction 80-1)

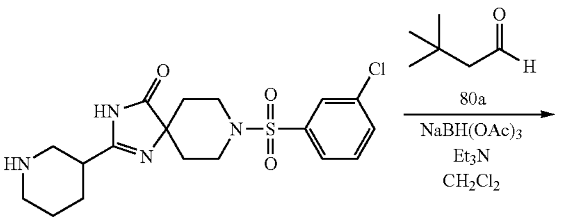

$CF_3CO_2H$

69a

-continued

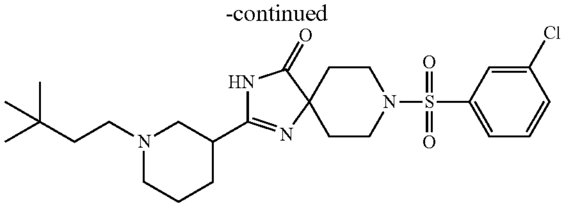

Compound 453

Triethylamine (2 eq), 3,3-dimethyl-butylaldehyde (1 eq) and sodium triacetoxyborohydride (1.5 eq) were added to a solution of 8-(3-chloro-benzenesulfonyl)-2-piperidin-3-yl-1,3,8-triaza-spiro[4.5]dec-1-en-4-one trifluoroacetate (126 mg, 0.24 mmol) in dichloromethane (5 ml). The mixture was stirred at room temperature overnight and then concentrated under reduced pressure. The resulting residue was purified by HPLC to give 8-(3-chloro-benzenesulfonyl)-2-[1-(3,3-dimethyl-butyl)-piperidin-3-yl]-1,3,8-triaza-spiro[4.5]dec-1-en-4-one (35 mg, yield 30%).

$^1$H-NMR (400 MHz, $CDCl_3$) δ 0.85 (s, 9H), 0.87-0.93 (m, 2H), 1.43-1.56 (m, 4H), 1.58-1.70 (m, 3H), 1.75-1.99 (m, 6H), 2.93-3.03 (m, 3H), 3.54-3.63 (m, 3H), 7.43 (t, J=7.83 Hz, 1H), 7.49-7.54 (m, 1H), 7.62 (d, J=7.58 Hz, 1H), 7.72 (t, J=1.77 Hz, 1H). MS (ESI) m/z=495 (M+H)+.

Example 81

3-[8-(3-Chloro-benzenesulfonyl)-4-oxo-1,3,8-triaza-spiro[4.5]dec-1-en-2-yl]-piperidine-1-carboxylic acid tert-butylamide (Compound 454)

(Reaction 81-1)

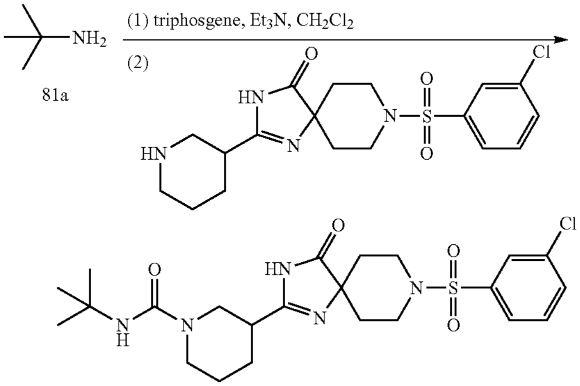

Compound 454

A solution of triphosgene (345 mg, 1.16 mmol) in $CH_2Cl_2$ (7 ml) was added to a solution of tert-butylamine (331 μl, 3.14 mmol) and triethylamine (876 μl, 6.29 mmol) in $CH_2Cl_2$ (10 ml) at −78° C. The mixture was stirred at room temperature for 10 minutes, followed by addition of a solution of 8-(3-chloro-benzenesulfonyl)-2-piperidin-3-yl-1,3,8-triaza-spiro[4.5]dec-1-en-4-one trifluoroacetate (165 mg, 0.314 mmol) and triethylamine (876 μl, 6.29 mmol) in $CH_2Cl_2$ (2 ml). Further, the reaction mixture was stirred at room temperature for 10 minutes and then concentrated under reduced pressure. The resulting residue was purified by silica gel column chromatography to give 3-[8-(3-Chloro-benzenesulfonyl)-4-oxo-1,3,8-triaza-spiro[4.5]dec-1-en-2-yl]-piperidine-1-carboxylic acid tert-butylamide as a colorless oil (40 mg, yield 25%).

$^1$H-NMR (400 MHz, $CDCl_3$) δ 1.25 (s, 9H), 1.47-1.63 (m, 2H), 1.71-1.84 (m, 2H), 1.83-2.07 (m, 6H), 3.02-3.13 (m, 2H), 3.14-3.25 (m, 2H), 3.53-3.65 (m, 2H), 3.84-3.95 (m, 1H), 7.43 (t, J=7.83 Hz, 1H), 7.49-7.55 (m, 1H), 7.61 (d, J=7.83 Hz, 1H), 7.72 (t, J=1.77 Hz, 1H). MS (ESI) m/z=510 (M+H)+.

The example compound shown below was synthesized by operations similar to those in Example 81 using appropriate reagents and starting material.

Compound 455

Example 82

8-(3-Chloro-benzenesulfonyl)-2-[1-(piperidine-1-carbonyl)-piperidin-3-yl]-1,3,8-triaza-spiro[4.5]dec-1-en-4-one (Compound 456)

(Reaction 82-1)

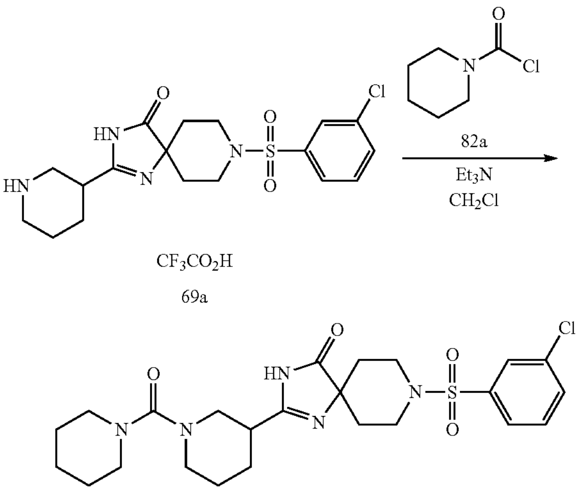

Compound 456

TEA (1.143 mmol, 3 eq) and piperidine-1-carbonyl chloride (0.457 mmol, 1.2 eq) were sequentially added to a mixed solution of 8-(3-chloro-benzenesulfonyl)-2-piperidin-3-yl-1,3,8-triaza-spiro[4.5]dec-1-en-4-one trifluoroacetate (200 mg, 0.38 mmol) in dichloromethane (3 ml). The resulting mixture was stirred at room temperature overnight and then concentrated under reduced pressure. The resulting residue was purified by HPLC to give 8-(3-chloro-benzenesulfonyl)-2-[1-(piperidine-1-carbonyl)-piperidin-3-yl]-1,3,8-triaza-spiro[4.5]dec-1-en-4-one (30 mg, yield 15%).

$^1$H-NMR (400 MHz, $CDCl_3$) δ 1.34-1.48 (m, 2H), 1.49-1.66 (m, 6H), 1.66-1.81 (m, 2H), 1.84-1.96 (m, 1H), 1.97-2.12 (m, 2H), 2.79-2.96 (m, 1H), 2.98-3.25 (m, 8H), 3.25-3.42 (m, 2H), 3.62-3.89 (m, 3H), 7.50 (t, J=7.83 Hz, 1H), 7.57-7.62 (m, 1H), 7.69 (d, J=7.58 Hz, 1H), 7.80 (t, J=1.77 Hz, 1H). MS (ESI) m/z=522 (M+H)+.

TABLE 66

| Compound | Structure | LCMS or HPLC condition | Retention time (min) | MS (m/z) |
|---|---|---|---|---|
| 455 | 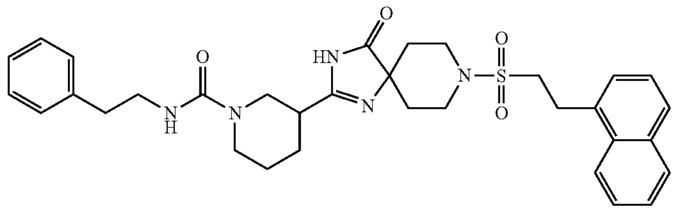 [SMILES: O=C(NCCc1ccccc1)N1CCCC(C2=NC3(CCN(S(=O)(=O)CCc4cccc5ccccc45)CC3)C(=O)N2)C1] | LCMS-E-2 | 3.34 | 602 (M + H)+ |

Example 83

3-(2-Dimethylamino-ethyl)-1-methyl-1-(3-methyl-4-{(E)-2-[4-oxo-2-(3-trifluoromethoxy-phenyl)-1,3,8-triaza-spiro[4.5]dec-1-ene-8-sulfonyl]-vinyl}-phenyl)-urea (Compound 457)

(Reaction 83-1)

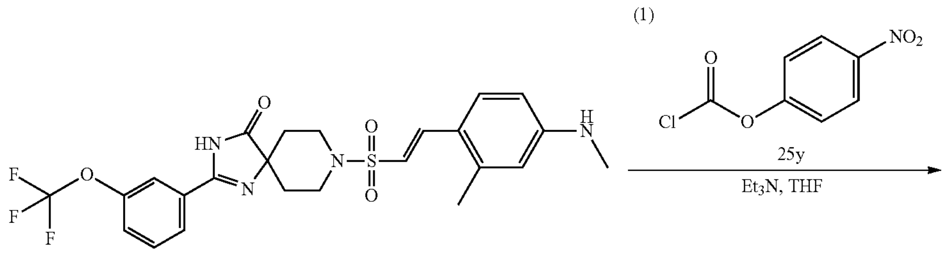

77b

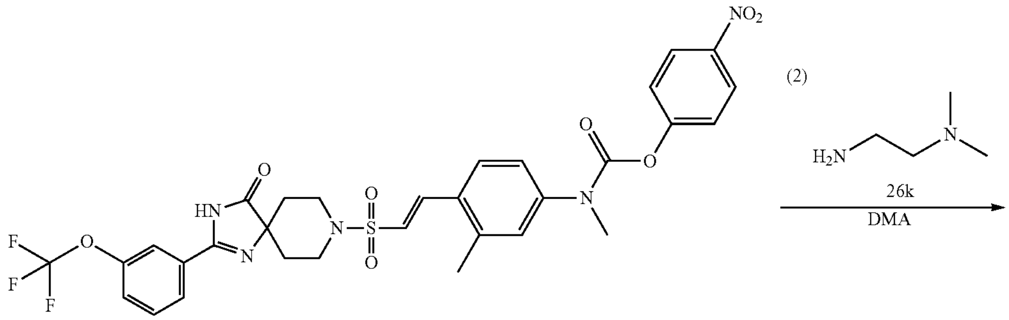

83a

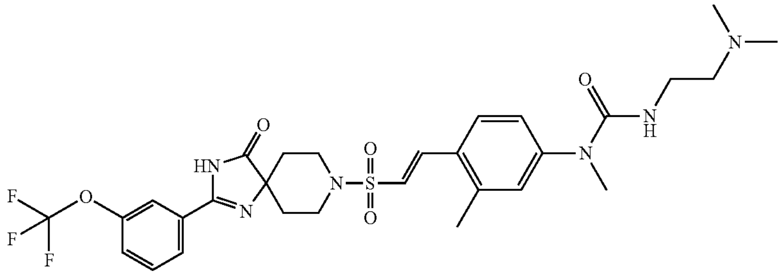

Compound 457

4-Nitrophenyl chloroformate (35 mg, 0.17 mmol) was added to a solution of 8-[(E)-2-(2-methyl-4-methylamino-phenyl)-ethenesulfonyl]-2-(3-trifluoromethoxy-phenyl)-1,3,8-triaza-spiro[4.5]dec-1-en-4-one (80 mg, 0.15 mmol) in THF (1 ml) at room temperature, and the mixture was then stirred at 70° C. for 30 minutes. The reaction mixture was extracted with AcOEt, and then dried over sodium sulfate and concentrated under reduced pressure. The resulting intermediate (83a) (20 mg, 0.029 mmol) was dissolved in DMA (0.1 ml), and N,N-dimethylethylenediamine (0.1 ml, 0.91 mmol) was added. The mixture was then stirred at 140° C. for one hour and at 100° C. for one hour. The resulting reaction mixture was purified by silica gel column chromatography to give 3-(2-dimethylamino-ethyl)-1-methyl-1-(3-methyl-4-{(E)-2-[4-oxo-2-(3-trifluoromethoxy-phenyl)-1,3,8-triaza-spiro[4.5]dec-1-ene-8-sulfonyl]-vinyl}-phenyl)-urea as an amorphous (12 mg, yield 66%).

$^1$H-NMR (400 MHz, DMSO-d6) δ 1.63-1.66 (m, 2H), 1.85-1.90 (m, 2H), 2.09 (s, 6H), 2.28 (t, J=6.8 Hz, 2H), 2.40 (s, 3H), 3.06-3.17 (m, 7H), 3.58-3.61 (m, 2H), 6.18 (t, J=5.8 Hz, 1H), 7.20 (d, J=8.3 Hz, 1H), 7.22 (s, 1H), 7.26 (d, J=15.6 Hz, 1H), 7.55 (d, J=15.6 Hz, 1H), 7.57-7.67 (m, 2H), 7.82 (d, J=8.3 Hz, 1H), 7.91 (br, 1H), 8.01 (br, 1H), 11.8 (br, 1H). MS (ESI) m/z=637 (M+H)+.

The example compound shown below was synthesized by operations similar to those in Example 83 using appropriate reagents and starting material.

Compound 458

TABLE 67

| Compound | Structure | LCMS or HPLC condition | Retention time (min) | MS (m/z) |
|---|---|---|---|---|
| 458 | 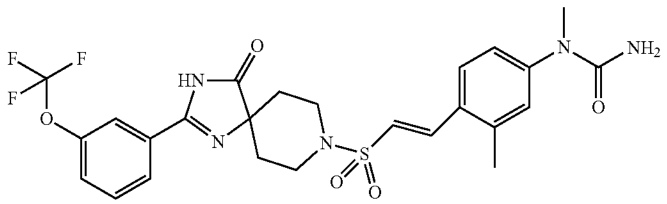 [SMILES: Cc1cc(N(C)C(N)=O)ccc1/C=C/S(=O)(=O)N1CCC2(CC1)N=C(c1cccc(OC(F)(F)F)c1)NC2=O] | LCMS-B-1 | 2.04 | 566 (M + H)+ |

Example 84

1-{3-[2-(2-Cyclohexyl-4-oxo-1,3,8-triaza-spiro[4.5]dec-1-ene-8-sulfonyl)-ethyl]-2-methyl-phenyl}-3-methyl-urea (Compound 459)

(Reaction 84-1)

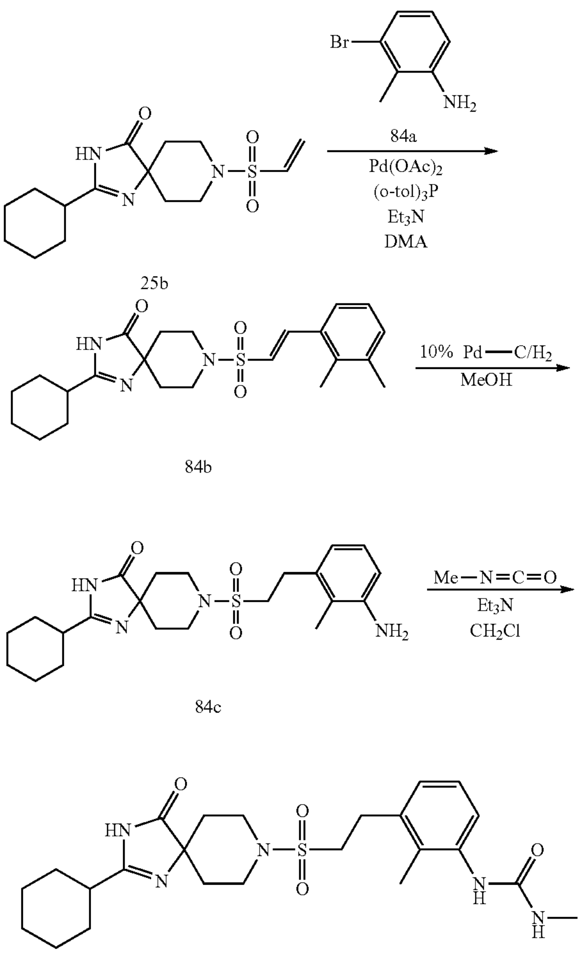

25b

84b

84c

Compound 459

1-{3-[2-(2-Cyclohexyl-4-oxo-1,3,8-triaza-spiro[4.5]dec-1-ene-8-sulfonyl)-ethyl]-2-methyl-phenyl}-3-methyl-urea was synthesized by operations similar to those in Reaction 25-2, Reaction 42-1 and Reaction 84-1 using appropriate reagents and starting material.

MS (ESI) m/z=490 (M+H)+.

Example 85

3-[8-(3-Chloro-benzenesulfonyl)-4-oxo-1,3,8-triaza-spiro[4.5]dec-1-en-2-yl]-piperidine-1-carboxylic acid 2-methoxy-ethyl ester (Compound 460)

(Reaction 85-1)

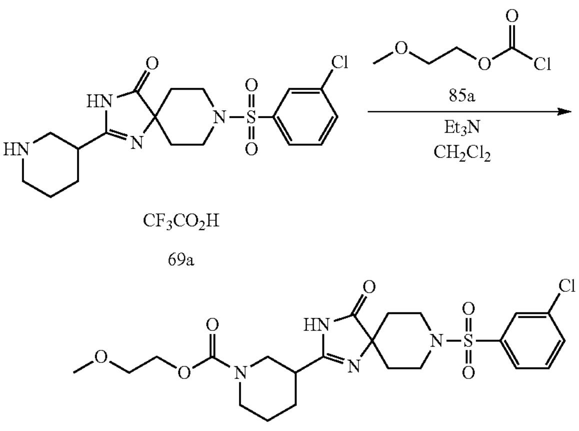

69a

Compound 460

3-[8-(3-Chloro-benzenesulfonyl)-4-oxo-1,3,8-triaza-spiro[4.5]dec-1-en-2-yl]-piperidine-1-carboxylic acid 2-methoxy-ethyl ester was synthesized by operations similar to those in Reaction 2-3 using appropriate reagents and starting material.

$^1$H-NMR (400 MHz, $CDCl_3$) δ 1.21-1.33 (m, 2H), 1.34-1.51 (m, 3H), 1.52-1.71 (m, 2H), 1.73-2.02 (m, 3H), 2.45-2.62 (m, 1H), 2.81-2.95 (m, 3H), 3.26 (s, 3H), 3.43-3.51 (m, 2H), 3.54-3.65 (m, 2H), 3.95-4.04 (m, 1H), 4.05-4.15 (m, 2H), 7.35-7.44 (m, 1H), 7.45-7.51 (m, 1H), 7.56 (d, J=7.83 Hz, 1H), 7.66 (t, J=1.77 Hz, 1H). MS (ESI) m/z=513 (M+H)+.

The example compounds shown below were synthesized by operations similar to those in Example 85 using appropriate reagents and starting materials.

Compounds 461 to 465
TABLE 68
| Compound | Structure | LCMS or HPLC condition | Retention time (min) | MS (m/z) |
|---|---|---|---|---|
| 461 | 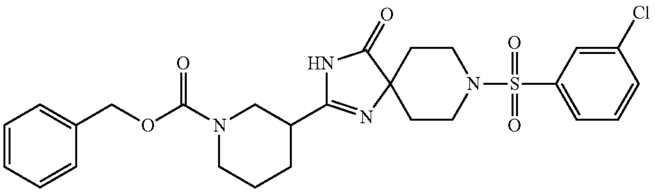 [SMILES: O=C(OCc1ccccc1)N1CCCC(C2=NC3(CCN(S(=O)(=O)c4cccc(Cl)c4)CC3)C(=O)N2)C1] | LCMS-E-6 | 1.86 | 545 (M + H)+ |
| 462 | 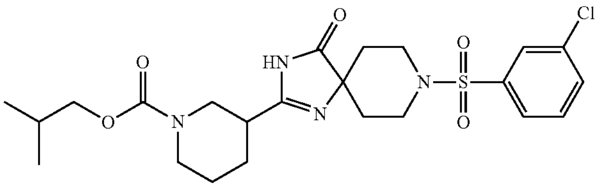 [SMILES: CC(C)COC(=O)N1CCCC(C2=NC3(CCN(S(=O)(=O)c4cccc(Cl)c4)CC3)C(=O)N2)C1] | LCMS-E-6 | 1.84 | 511 (M + H)+ |
| 463 | 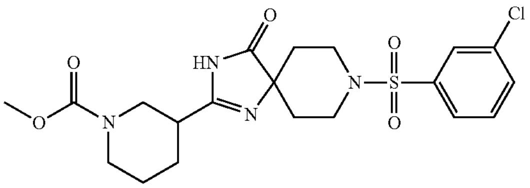 [SMILES: COC(=O)N1CCCC(C2=NC3(CCN(S(=O)(=O)c4cccc(Cl)c4)CC3)C(=O)N2)C1] | LCMS-E-6 | 1.46 | 469 (M + H)+ |
| 464 | 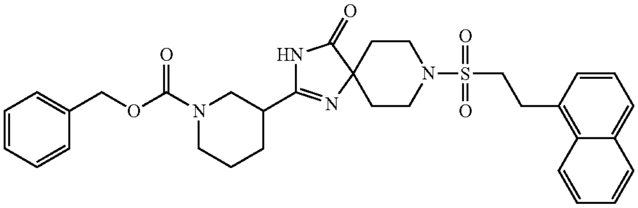 [SMILES: O=C(OCc1ccccc1)N1CCCC(C2=NC3(CCN(S(=O)(=O)CCc4cccc5ccccc45)CC3)C(=O)N2)C1] | LCMS-E-3 | 3.65 | 589 (M + H)+ |
| 465 | 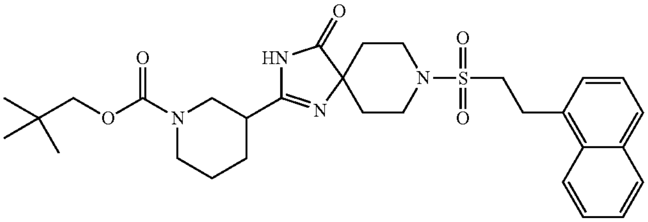 [SMILES: CC(C)(C)COC(=O)N1CCCC(C2=NC3(CCN(S(=O)(=O)CCc4cccc5ccccc45)CC3)C(=O)N2)C1] | LCMS-E-3 | 3.75 | 569 (M + H)+ |

Example 86

Methyl-(3-methyl-4-{(E)-2-[4-oxo-2-(3-trifluoromethoxy-phenyl)-1,3,8-triaza-spiro[4.5]dec-1-ene-8-sulfonyl]-vinyl}-phenyl)-carbamic acid 2-dimethylamino-ethyl ester (Compound 466)

(Reaction 86-1)

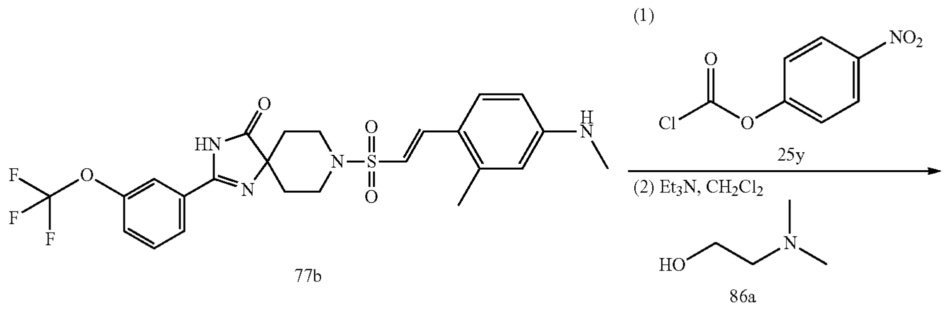

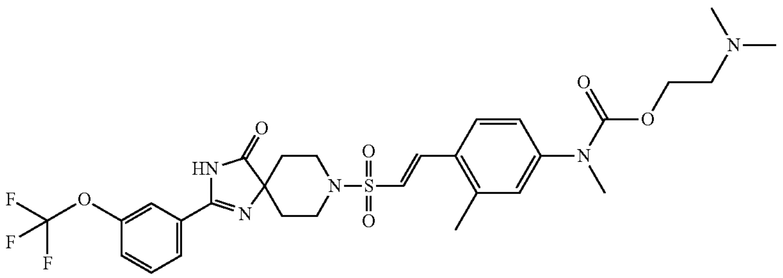

Compound 466

Methyl-(3-methyl-4-{(E)-2-[4-oxo-2-(3-trifluoromethoxy-phenyl)-1,3,8-triaza-spiro[4.5]dec-1-ene-8-sulfonyl]-vinyl}-phenyl)-carbamic acid 2-dimethylamino-ethyl ester was synthesized by operations similar to those in Reaction 83-1 using appropriate reagents and starting material.

MS (ESI) m/z=638 (M+H)+.

The example compound shown below was synthesized by operations similar to those in Example 86 using appropriate reagents and starting material.

Compound 467

TABLE 69

| Compound | Structure | LCMS or HPLC condition | Retention time (min) | MS (m/z) |
|---|---|---|---|---|
| 467 | 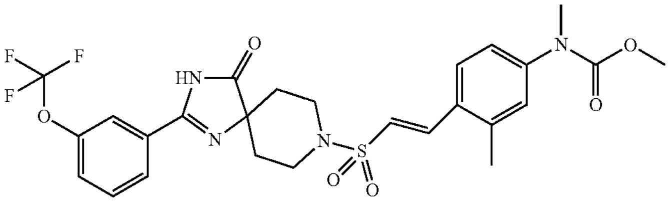 [SMILES: COC(=O)N(C)c1ccc(/C=C/S(=O)(=O)N2CCC3(CC2)N=C(c2cccc(OC(F)(F)F)c2)NC3=O)c(C)c1] | LCMS-A-1 | 2.74 | 581 (M + H)+ |

Example 87

Methyl-(3-methyl-4-{2-[4-oxo-2-(3-trifluoromethoxy-phenyl)-1,3,8-triaza-spiro[4.5]dec-1-ene-8-sulfonyl]-ethyl}-phenyl)-carbamic acid methyl ester (Compound 468)

(Reaction 87-1)

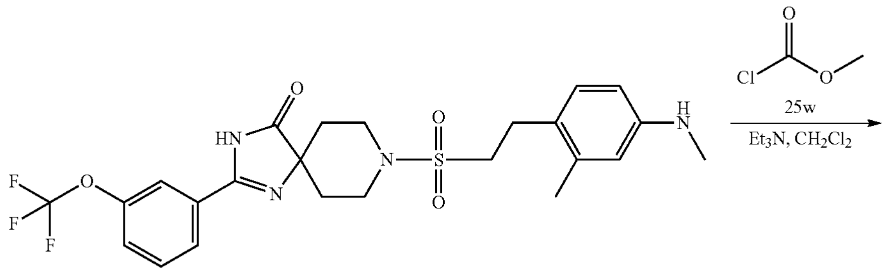

77b

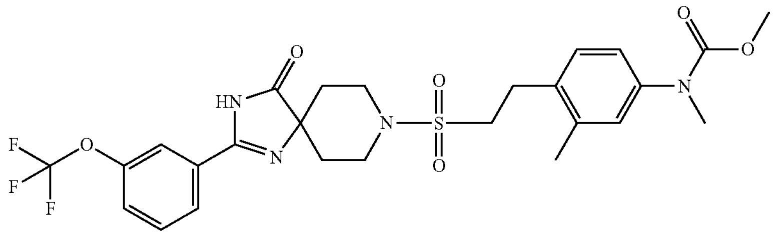

Compound 468

Methyl-(3-methyl-4-{2-[4-oxo-2-(3-trifluoromethoxy-phenyl)-1,3,8-triaza-spiro[4.5]dec-1-ene-8-sulfonyl]-ethyl}-phenyl)-carbamic acid methyl ester was synthesized by operations similar to those in Reaction 2-3 using appropriate reagents and starting material.

MS (ESI) m/z=583 (M+H)+.

Example 88

2-Cyclohexyl-8-(2-o-tolyl-ethanesulfonyl)-1,3,8-triaza-spiro[4.5]dec-1-ene-4-thione (Compound 469)

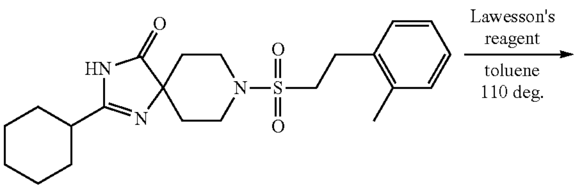

Compound 277

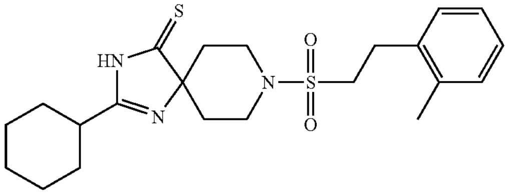

Compound 469

2-Cyclohexyl-8-(2-o-tolyl-ethanesulfonyl)-1,3,8-triaza-spiro[4.5]dec-1-en-4-one (24.2 mg, 0.058 mmol), Lawesson's reagent (48.3 mg, 0.116 mmol) and toluene (1.16 ml) were added to a sealed test tube and stirred at 110° C. overnight. The reaction mixture was cooled to ambient temperature, and the solvent was then distilled off under reduced pressure. The residue was purified by column chromatography (silica gel, $CH_2Cl_2$-MeOH) to give 2-cyclohexyl-8-(2-o-tolyl-ethanesulfonyl)-1,3,8-triaza-spiro[4.5]dec-1-ene-4-thione (11.2 mg, 45%).

$^1$H-NMR (400 MHz, $CD_3OD$) δ 1.29-1.58 (7H, m), 1.73-2.15 (7H, m), 2.36 (3H, s), 2.55 (1H, tt, J=4, 12 Hz), 3.09-3.13 (2H, m), 3.25-3.27 (2H, m), 3.30-3.31 (2H, m), 3.80-3.83 (2H, m), 7.13-7.23 (4H, m). MS (ESI) m/z=434 (M+H)+.

Example 89

1-(3,5-Dimethyl-4-{2-[2-(4-methyl-cyclohexyl)-4-oxo-1,3,8-triaza-spiro[4.5]dec-1-ene-8-sulfonyl]-ethyl}-phenyl)-1-methyl-urea (Compound 470)

(Reaction 89-1)

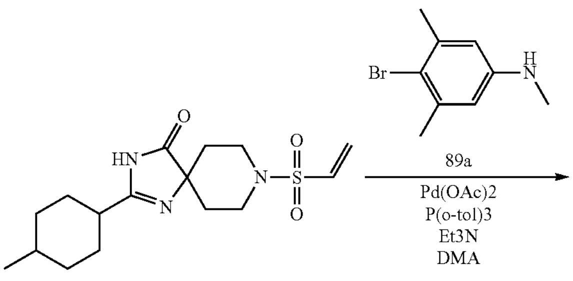

27b

-continued

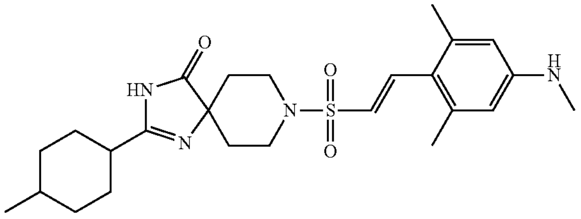

89b

8-[2-(2,6-Dimethyl-4-methylamino-phenyl)-ethanesulfonyl]-2-(4-methyl-cyclohexyl)-1,3,8-triaza-spiro[4.5]dec-1-en-4-one was synthesized by operations similar to those in Reaction 25-2 using appropriate reagents and starting material.

MS (ESI) m/z=473 (M+H)+.

(Reaction 89-2)

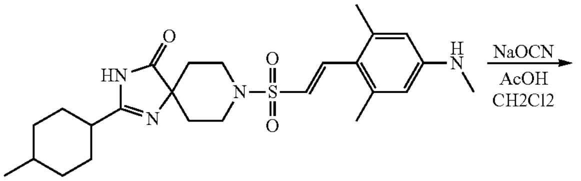

89b

-continued

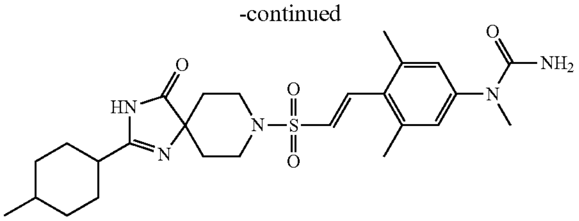

89c

Sodium cyanate (15 mg, 0.243 mmol) was added to a solution of 8-[2-(2,6-dimethyl-4-methylamino-phenyl)-ethanesulfonyl]-2-(4-methyl-cyclohexyl)-1,3,8-triaza-spiro[4.5]dec-1-en-4-one (23 mg, 0.0487 mmol) and acetic acid (1.3 ml) in dichloromethane (0.5 ml) at room temperature, and the mixture was then stirred for two hours. The reaction mixture was diluted with dichloromethane, and the organic layer was then washed with water and a saturated aqueous sodium bicarbonate solution, dried over anhydrous sodium sulfate and concentrated under reduced pressure. The resulting residue was purified by preparative TLC (silica gel, MeOH/AcOEt/$CH_2Cl_2$) to give 1-(3,5-dimethyl-4-{(E)-2-[2-(4-methyl-cyclohexyl)-4-oxo-1,3,8-triaza-spiro[4.5]dec-1-ene-8-sulfonyl]-vinyl}-phenyl)-1-methyl-urea (22.5 mg, 90%).

$^1$H-NMR (400 MHz, $CDCl_3$) δ 0.92 (3H, d, J=4.0 Hz), 0.95-1.1 (2H, m), 1.35-1.50 (3H, m), 1.65-1.75 (2H, m), 1.80-1.85 (2H, m), 1.90-2.00 (4H, m), 2.30-2.40 (1H, m), 2.38 (6H, s), 3.26 (3H, s), 3.35-3.45 (2H, m), 3.60-3.75 (2H, m), 4.54 (2H, brs), 6.39 (1H, d, J=16.0 Hz), 7.03 (2H, s), 7.54 (1H, d, J=16.0 Hz), 8.10 (1H, brs). MS (ESI) m/z=516 (M+H)+.

(Reaction 89-3)

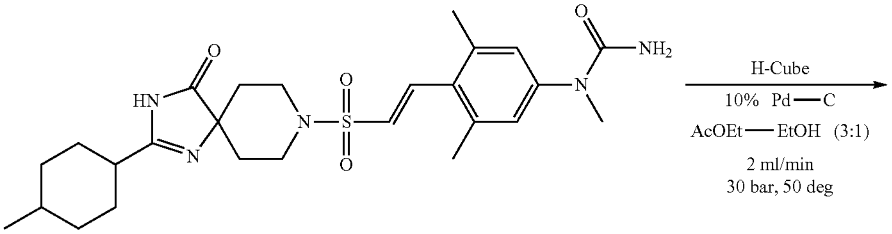

89c

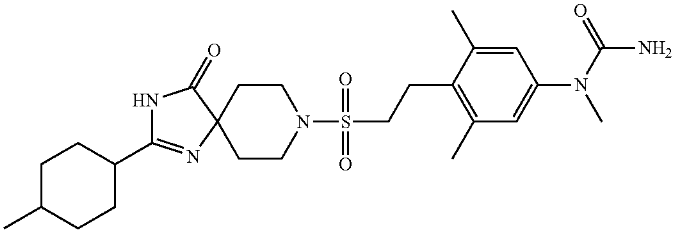

Compound 470

1-(3,5-Dimethyl-4-{2-[2-(4-methyl-cyclohexyl)-4-oxo-1,3,8-triaza-spiro[4.5]dec-1-ene-8-sulfonyl]-ethyl}-phenyl)-1-methyl-urea was synthesized by operations similar to those in Reaction 42-2 using appropriate reagents and starting material.

$^1$H-NMR (400 MHz, $CD_3OD$) δ 0.92 (3H, d, J=8.0 Hz), 0.95-1.06 (2H, m), 1.35-1.50 (3H, m), 1.65-1.75 (2H, m), 1.80-1.86 (2H, m), 1.88-2.00 (4H, m), 2.30-2.40 (1H, m), 2.36 (6H, s), 2.95-3.02 (2H, m), 3.15-3.22 (2H, m), 3.23 (3H, s), 3.45-3.52 (2H, m), 3.68-3.77 (2H, m), 4.47 (2H, brs), 6.95 (2H, s), 8.06 (1H, brs). MS (ESI) m/z=518 (M+H)+.

Example 90
1-(3,5-Dimethyl-4-{(E)-2-[4-oxo-2-(4-trifluoromethyl-cyclohexyl)-1,3,8-triaza-spiro[4.5]dec-1-ene-8-sulfonyl]-vinyl}-phenyl)-1-methyl-urea (Compound 471)
(Reaction 90-1)
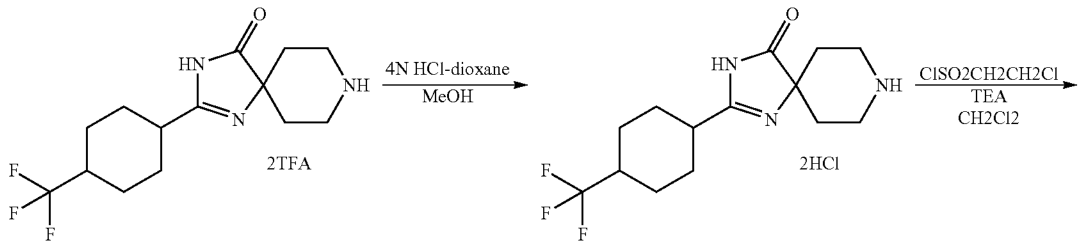
90a 90b
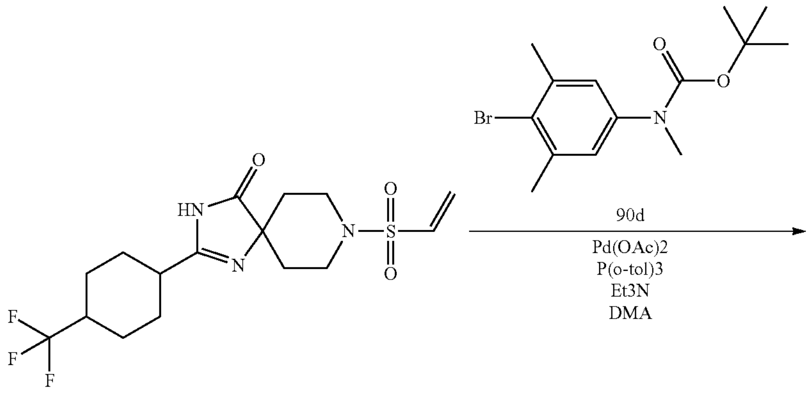
90c
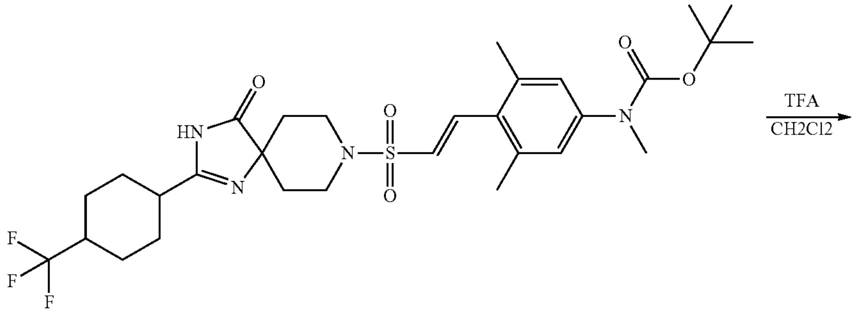
90e
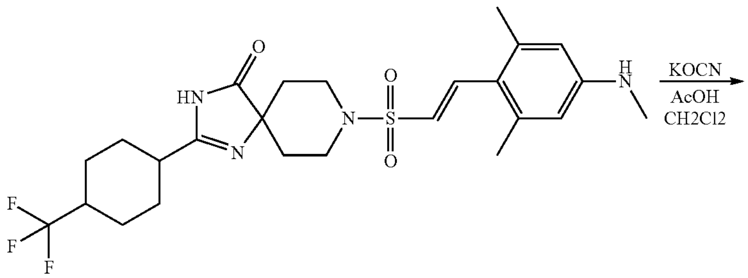
90f -continued

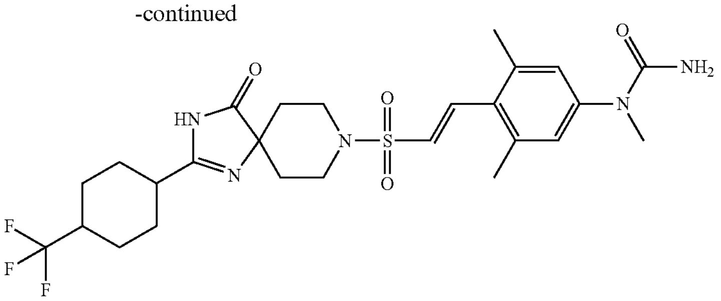

Compound 471

1-(3,5-Dimethyl-4-{(E)-2-[4-oxo-2-(4-trifluoromethyl-cyclohexyl)-1,3,8-triaza-spiro[4.5]dec-1-ene-8-sulfonyl]-vinyl}-phenyl)-1-methyl-urea was synthesized by operations similar to those in Reaction 5-3, Reaction 25-1, Reaction 26-1, Reaction 7-2 and Reaction 89-2 using appropriate reagents and starting material.

MS (ESI) m/z=570 (M+H)+.

Example 91

1-(3,5-Dimethyl-4-{2-[4-oxo-2-(4-trifluoromethyl-cyclohexyl)-1,3,8-triaza-spiro[4.5]dec-1-ene-8-sulfonyl]-ethyl}-phenyl)-1-methyl-urea (Compound 472)

(Reaction 91-1)

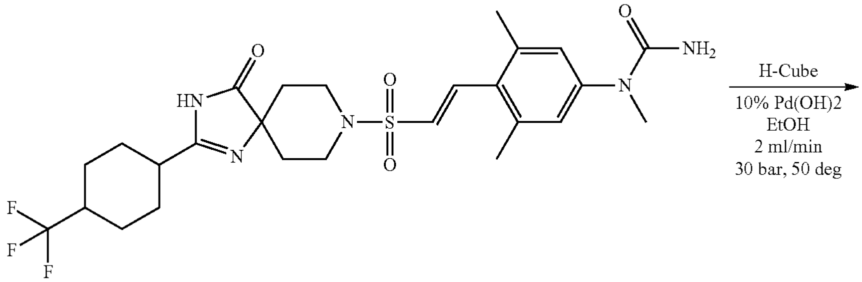

Compound 471

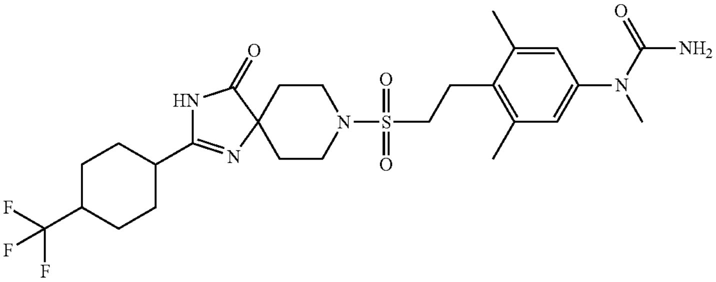

Compound 472

1-(3,5-Dimethyl-4-{2-[4-oxo-2-(4-trifluoromethyl-cyclohexyl)-1,3,8-triaza-spiro[4.5]dec-1-ene-8-sulfonyl]-ethyl}-phenyl)-1-methyl-urea was synthesized by operations similar to those in Reaction 42-2 using appropriate reagents and starting material.

MS (ESI) m/z=572 (M+H)+.

Example 92

(3-Methyl-4-{(E)-2-[4-oxo-2-(3-trifluoromethoxy-phenyl)-1,3,8-triaza-spiro[4.5]dec-1-ene-8-sulfonyl]-vinyl}-phenyl)-sulfamide (Compound 473)

(Reaction 92-1)

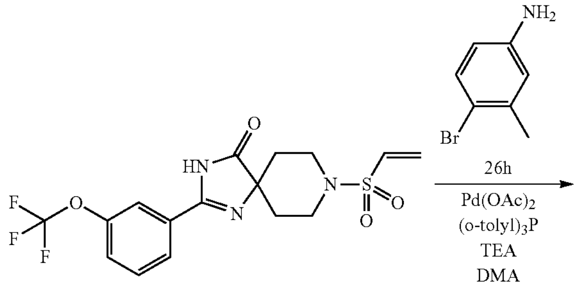

30a

-continued

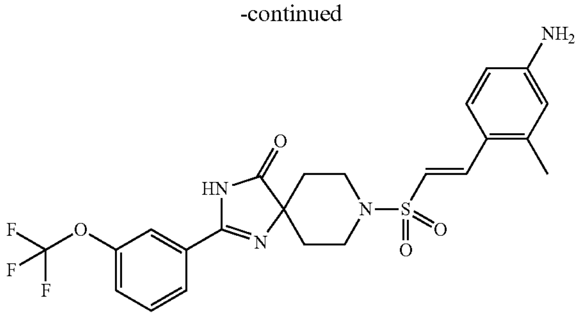

92a

8-[(E)-2-(4-amino-2-methyl-phenyl)-ethenesulfonyl]-2-(3-trifluoromethoxy-phenyl)-1,3,8-triaza-spiro[4.5]dec-1-en-4-one was obtained by operations similar to those in Reaction 26-1 using 8-ethenesulfonyl-2-(3-trifluoromethoxy-phenyl)-1,3,8-triaza-spiro[4.5]dec-1-en-4-one as a starting material.

MS (ESI) m/z=509 (M+H)+.

(Reaction 92-2)

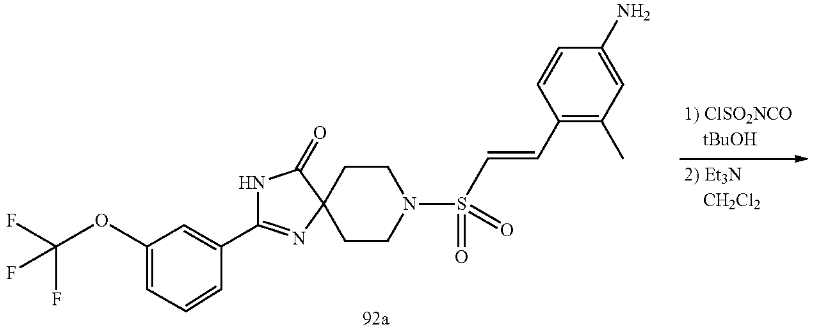

92a

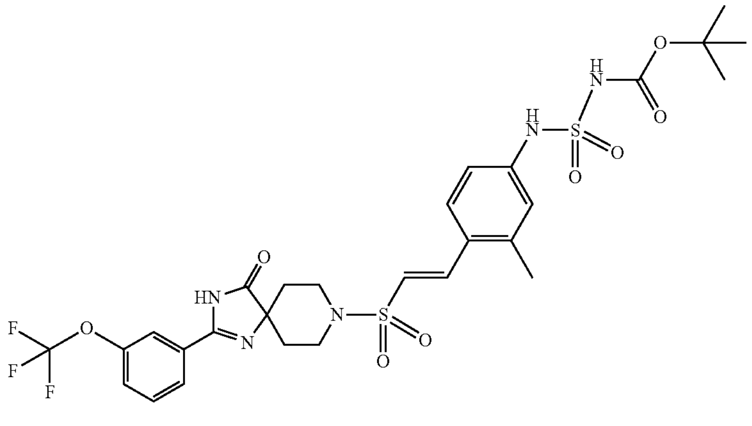

92b

A solution of tert-butanol (71.9 mg, 0.97 mmol) in dichloromethane (1.5 ml) was added to a solution of chlorosulfonyl isocyanate (137 mg, 0.97 mmol) in dichloromethane (3 ml) with stirring under ice-cooling. The mixture was stirred at 0° C. for 10 minutes. A solution of 8-[(E)-2-(4-amino-2-methyl-phenyl)-ethenesulfonyl]-2-(3-trifluoromethoxy-phenyl)-1,3,8-triaza-spiro[4.5]dec-1-en-4-one (400 mg, 0.81 mmol) and triethylamine (164 mg, 1.62 mmol) in dichloromethane (3 ml) was then added, and the mixture was further stirred for one hour. The mixed reaction solution was quenched with water and then extracted with dichloromethane. The organic layer was washed with saturated brine, and then dried over anhydrous magnesium sulfate and concentrated under reduced pressure. The resulting residue was purified by silica gel column chromatography (ethyl acetate-hexane) to give N-(tert-butoxycarbonyl)-N'-(3-methyl-4-{(E)-2-[4-oxo-2-(3-trifluoromethoxy-phenyl)-1,3,8-triaza-spiro[4.5]dec-1-ene-8-sulfonyl]-vinyl}-phenyl)sulfamide (334 mg, 60.0%).

$^1$H-NMR (400 MHz, $CDCl_3$) δ 1.42 (9H, s), 1.78 (2H, dt, J=14.2, 3.9 Hz), 2.04-2.14 (2H, m), 2.40 (3H, s), 3.43 (2H, ddd, J=12.7, 9.8, 2.9 Hz), 3.74 (2H, dt, J=12.2, 4.4 Hz), 6.64 (1H, d, J=15.6 Hz), 7.08-7.11 (2H, m), 7.38 (1H, d, J=8.3 Hz), 7.48-7.54 (2H, m), 7.68 (1H, d, J=15.1 Hz), 7.73 (1H, d, J=7.8 Hz), 7.76 (1H, s), 9.62 (1H, s);

MS (ESI) m/z=688 (M+H)+.

(Reaction 92-3)

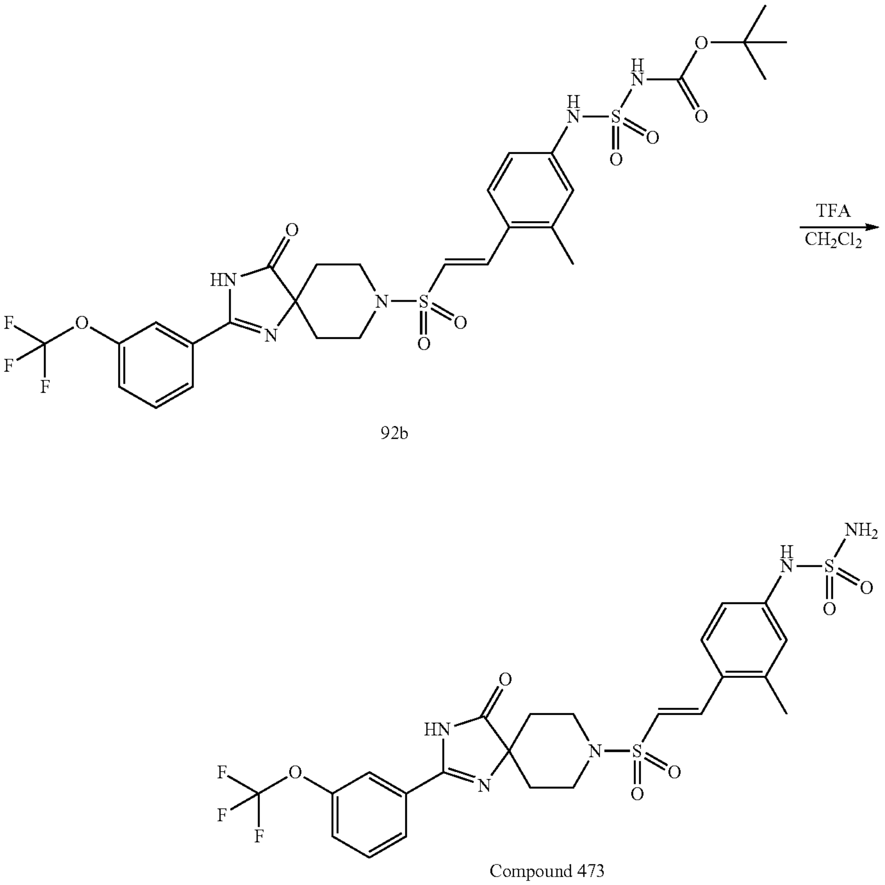

92b

Compound 473

(3-Methyl-4-{(E)-2-[4-oxo-2-(3-trifluoromethoxy-phenyl)-1,3,8-triaza-spiro[4.5]dec-1-ene-8-sulfonyl]-vinyl}-phenyl)-sulfamide was obtained by operations similar to those in Reaction 4-1 using N-(tert-butoxycarbonyl)-N'-(3-methyl-4-{(E)-2-[4-oxo-2-(3-trifluoromethoxy-phenyl)-1,3,8-triaza-spiro[4.5]dec-1-ene-8-sulfonyl]-vinyl}-phenyl)sulfamide as a starting material.

MS (ESI) m/z=588 (M+H)+.

Example 93

1-(3,5-Dimethyl-4-{2-[2-(4-methyl-cyclohexyl)-4-oxo-1,3,8-triaza-spiro[4.5]dec-1-ene-8-sulfonyl]-ethyl}-phenyl)-1-methyl-thiourea (Compound 474)

(Reaction 93-1)

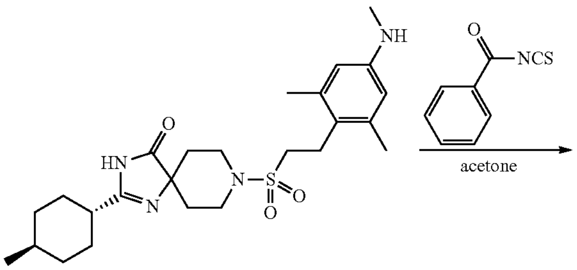

93a

-continued

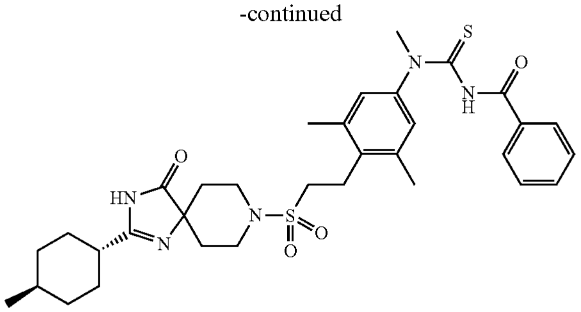

93b

Benzoyl isothiocyanate (37.8 mg, 0.23 mmol) was added to a solution of 8-[2-(2,6-dimethyl-4-methylamino-phenyl)-ethanesulfonyl]-2-(4-methyl-cyclohexyl)-1,3,8-triaza-spiro[4.5]dec-1-en-4-one (100 mg, 0.21 mmol) in acetone (3 ml) in a nitrogen stream. The mixture was heated under reflux for one hour and then concentrated under reduced pressure. The resulting residue was purified by silica gel column chromatography (dichloromethane-methanol) to give 3-benzoyl-1-(3,5-dimethyl-4-{2-[2-(4-methyl-cyclohexyl)-4-oxo-1,3,8-triaza-spiro[4.5]dec-1-ene-8-sulfonyl]-ethyl}-phenyl)-1-methyl-thiourea (140 mg).

$^1$H-NMR (400 MHz, $CDCl_3$) δ 0.92 (3H, d, J=6.8 Hz), 0.94-1.07 (2H, m), 1.32-1.46 (3H, m), 1.52-1.64 (2H, m), 1.82 (2H, dd, J=13.7, 2.4 Hz), 1.90-2.00 (4H, m), 2.28-2.33 (1H, m), 2.35 (6H, s), 2.90-3.00 (2H, m), 3.08-3.16 (2H, m), 3.36-3.45 (2H, m), 3.64-3.78 (5H, m), 7.01 (2H, s), 7.37-7.62 (5H, m);

MS (ESI) m/z=638 (M+H)+.

(Reaction 93-2)

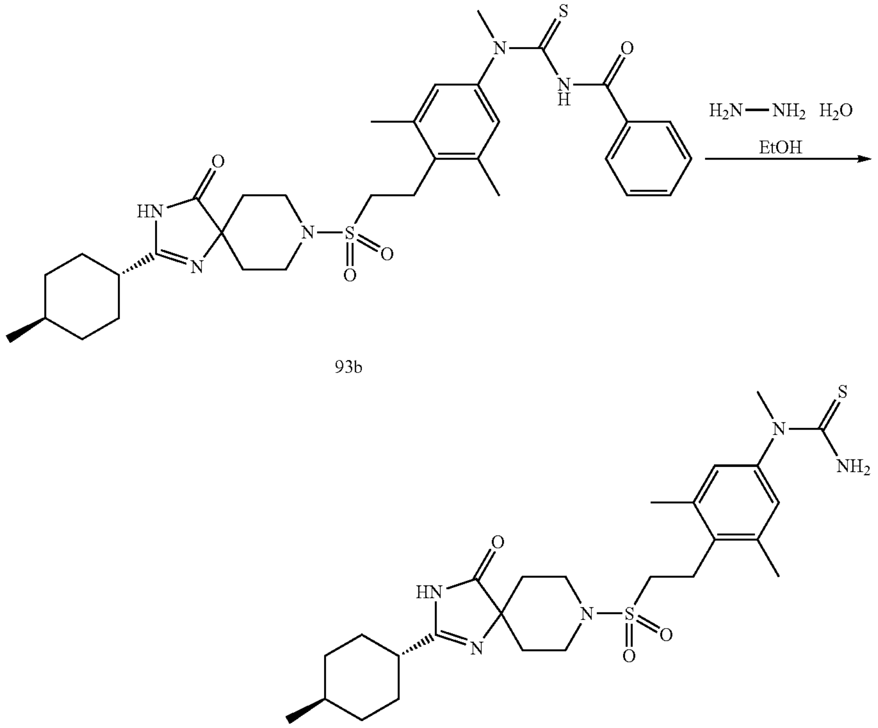

93b

Compound 474

Hydrazine monohydrate (55 mg, 1.1 mmol) was added to a solution of 3-benzoyl-1-(3,5-dimethyl-4-{2-[2-(4-methyl-cyclohexyl)-4-oxo-1,3,8-triaza-spiro[4.5]dec-1-ene-8-sulfonyl]-ethyl}-phenyl)-1-methyl-thiourea (140 mg, 0.22 mmol) in ethanol (7 ml). The mixture was stirred at room temperature for 15 hours and then concentrated under reduced pressure. The resulting residue was purified by silica gel column chromatography (dichloromethane-methanol) to give 1-(3,5-dimethyl-4-{2-[2-(4-methyl-cyclohexyl)-4-oxo-1,3,8-triaza-spiro[4.5]dec-1-ene-8-sulfonyl]-ethyl}-phenyl)-1-methyl-thiourea (119 mg).

$^1$H-NMR (400 MHz, $CDCl_3$) δ 0.92 (3H, d, J=6.3 Hz), 1.00 (2H, ddd, J=25.4, 13.7, 2.9 Hz), 1.32-1.47 (3H, m), 1.59-1.68 (2H, m), 1.82 (2H, dd, J=10.7, 3.4 Hz), 1.90-1.98 (4H, m), 2.28-2.35 (1H, m), 2.35 (6H, s), 2.95-3.02 (2H, m), 3.15-3.22 (2H, m), 3.45 (2H, ddd, J=12.2, 9.3, 3.4 Hz), 3.55 (3H, s), 3.74 (2H, dt, J=13.1, 4.4 Hz), 5.63 (1H, brs), 6.94 (2H, s), 8.14 (1H, s);

MS (ESI) m/z=534 (M+H)+.

Example 94

8-{2-[2,6-Dimethyl-4-(methyl-thiazol-2-yl-amino)-phenyl]-ethanesulfonyl}-2-(4-methyl-cyclohexyl)-1,3,8-triaza-spiro[4.5]dec-1-en-4-one (Compound 475)

(Reaction 94-1)

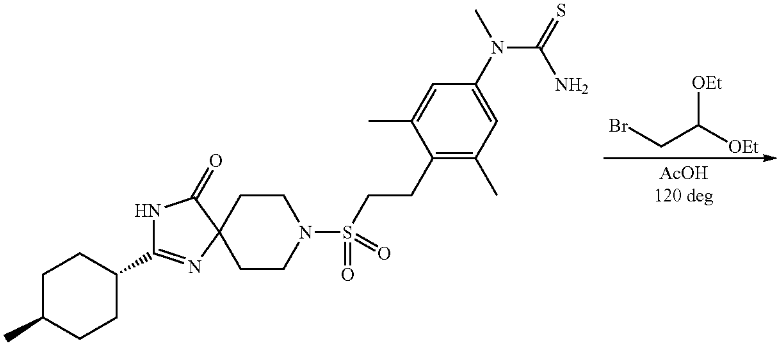

Compound 474

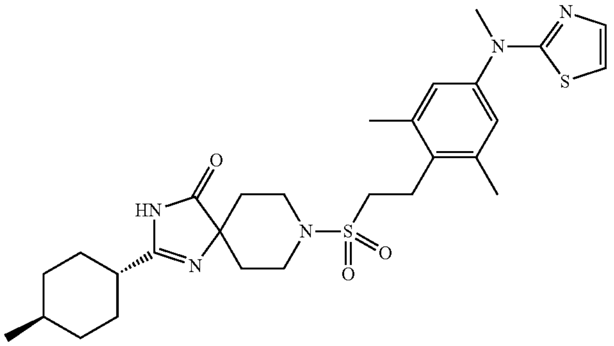

Compound 475

Bromoacetaldehyde diethylacetal (44.2 mg, 0.224 mmol) was added to a solution of 1-(3,5-dimethyl-4-{2-[2-(4-methyl-cyclohexyl)-4-oxo-1,3,8-triaza-spiro[4.5]dec-1-ene-8-sulfonyl]-ethyl}-phenyl)-1-methyl-thiourea (100 mg, 0.187 mmol) in acetic acid (2 ml) in a nitrogen stream. The mixture was heated under reflux for two hours and then concentrated under reduced pressure. The resulting residue was diluted with dichloromethane, and the organic layer was then sequentially washed with a saturated aqueous sodium bicarbonate solution and saturated brine and dried over anhydrous magnesium sulfate. The organic layer was concentrated, and the resulting residue was then purified by silica gel column chromatography (dichloromethane-methanol) to give 8-{2-[2,6-Dimethyl-4-(methyl-thiazol-2-yl-amino)-phenyl]-ethanesulfonyl}-2-(4-methyl-cyclohexyl)-1,3,8-triaza-spiro[4.5]dec-1-en-4-one (7.1 mg).

$^1$H-NMR (400 MHz, $CDCl_3$) δ 0.92 (3H, d, J=6.8 Hz), 0.95-1.07 (2H, m), 1.33-1.48 (3H, m), 1.56-1.67 (2H, m), 1.82 (2H, d, J=11.2 Hz), 1.91-2.03 (4H, m), 2.29-2.35 (1H, m), 2.37 (6H, s), 2.99-3.06 (2H, m), 3.14-3.21 (2H, m), 3.43 (2H, ddd, J=12.7, 9.3, 2.9 Hz), 3.49 (3H, s), 3.77 (2H, dt, J=12.2, 4.4 Hz), 6.48 (1H, d, J=3.4 Hz), 7.06 (2H, s), 7.22 (1H, d, J=3.4 Hz), 8.33 (1H, s);

MS (ESI) m/z=558 (M+H)+.

Example 95

The example compounds shown below were obtained by operations similar to those in Reaction 25-2 using appropriate reagents and starting materials.

Compounds 476 to 503
TABLE 70
| Target Compound | Structure | LCMS condition | Retention time (min) | MS (m/z) |
|---|---|---|---|---|
| 476 | 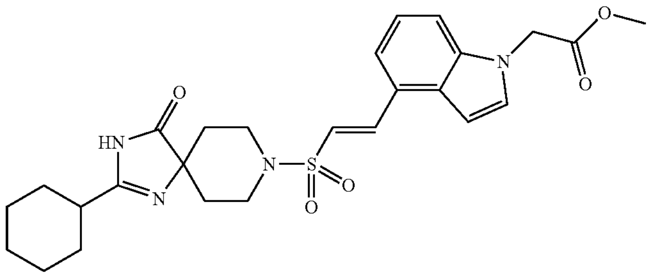 [SMILES: COC(=O)Cn1ccc2c(/C=C/S(=O)(=O)N3CCC4(CC3)N=C(C3CCCCC3)NC4=O)cccc21] | LCMS-C-1 | 2.53 | 513 (M + H)+ |
| 477 | 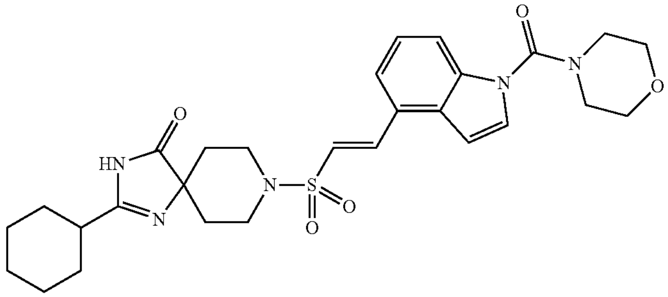 [SMILES: O=C(N1CCOCC1)n1ccc2c(/C=C/S(=O)(=O)N3CCC4(CC3)N=C(C3CCCCC3)NC4=O)cccc21] | LCMS-C-1 | 2.55 | 554 (M + H)+ |
| 478 | 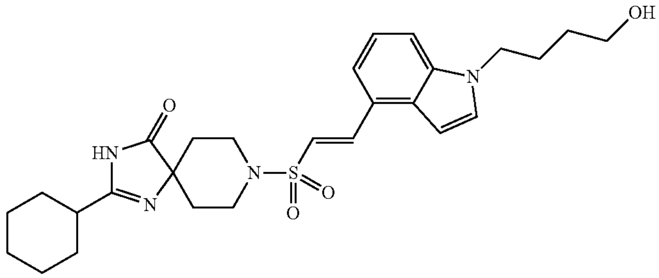 [SMILES: O=C1NC(C2CCCCC2)=NC12CCN(S(=O)(=O)/C=C/c1cccc3c1ccn3CCCCO)CC2] | LCMS-C-1 | 2.62 | 513 (M + H)+ |
| 479 | 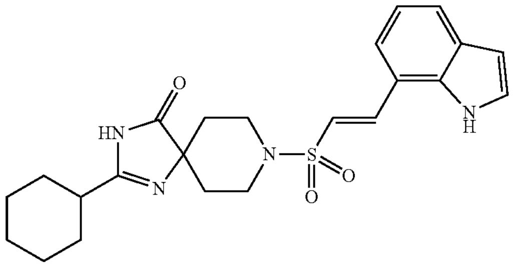 [SMILES: O=C1NC(C2CCCCC2)=NC12CCN(S(=O)(=O)/C=C/c1cccc3cc[nH]c13)CC2] | LCMS-A-1 | 2.25 | 441 (M + H)+ |
| 480 | 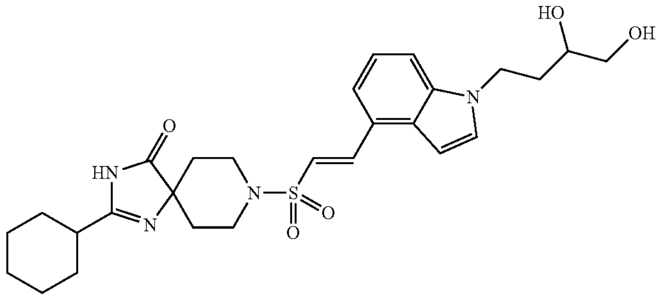 [SMILES: O=C1NC(C2CCCCC2)=NC12CCN(S(=O)(=O)/C=C/c1cccc3c1ccn3CCC(O)CO)CC2] | LCMS-C-1 | 2.42 | 529 (M + H)+ |

TABLE 70-continued
| Target Compound | Structure | LCMS condition | Retention time (min) | MS (m/z) |
|---|---|---|---|---|
| 481 | 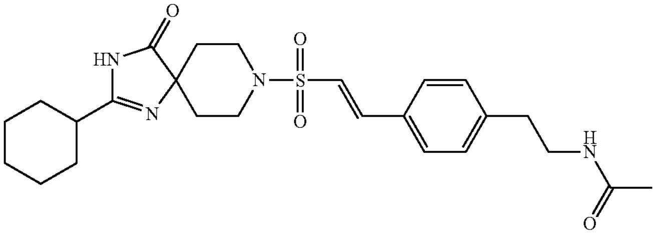 [SMILES: CC(=O)NCCc1ccc(/C=C/S(=O)(=O)N2CCC3(CC2)N=C(C2CCCCC2)NC3=O)cc1] | LCMS-C-1 | 2.30 | 485 (M − H)− |
| 482 | 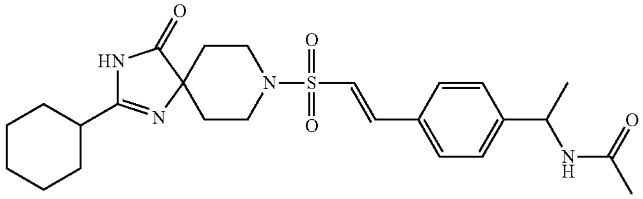 [SMILES: CC(=O)NC(C)c1ccc(/C=C/S(=O)(=O)N2CCC3(CC2)N=C(C2CCCCC2)NC3=O)cc1] | LCMS-C-1 | 2.30 | 485 (M − H)− |
| 483 | 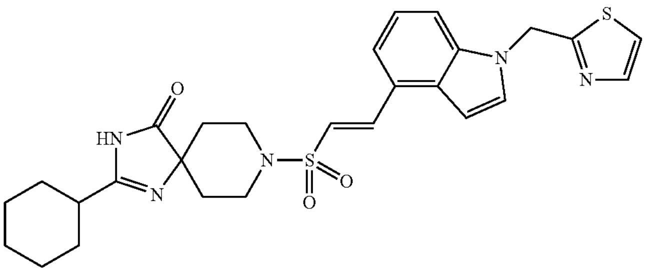 [SMILES: O=C1NC(C2CCCCC2)=NC12CCN(S(=O)(=O)/C=C/c1cccc3c1ccn3Cc1nccs1)CC2] | LCMS-C-1 | 2.62 | 536 (M − H)− |
| 484 | 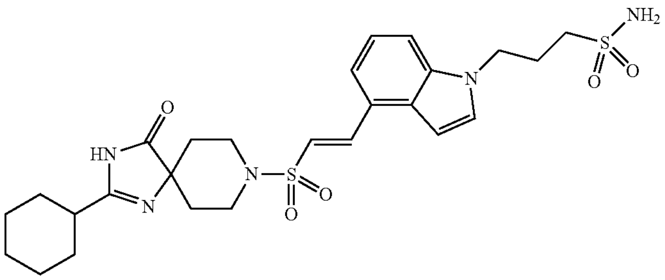 [SMILES: NS(=O)(=O)CCCn1ccc2c(/C=C/S(=O)(=O)N3CCC4(CC3)N=C(C3CCCCC3)NC4=O)cccc21] | LCMS-C-1 | 2.38 | 562 (M + H)+ |
| 485 | 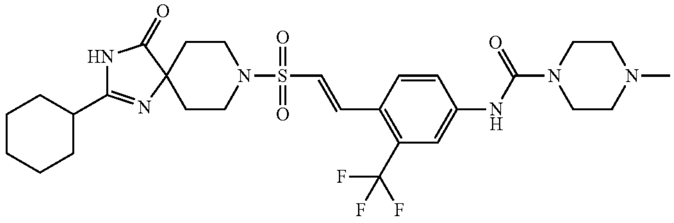 [SMILES: CN1CCN(C(=O)Nc2ccc(/C=C/S(=O)(=O)N3CCC4(CC3)N=C(C3CCCCC3)NC4=O)c(C(F)(F)F)c2)CC1] | LCMS-C-1 | 2.68 | 611 (M + H)+ |
| 486 | 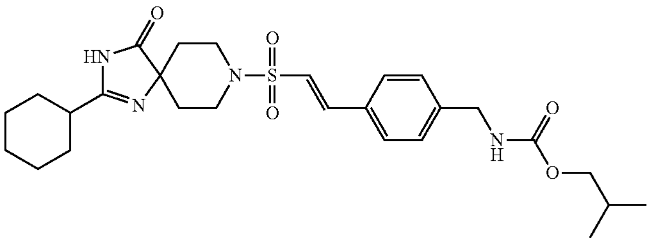 [SMILES: CC(C)COC(=O)NCc1ccc(/C=C/S(=O)(=O)N2CCC3(CC2)N=C(C2CCCCC2)NC3=O)cc1] | LCMS-C-1 | 2.75 | 529 (M − H)− |

TABLE 70-continued
| Target Compound | Structure | LCMS condition | Retention time (min) | MS (m/z) |
|---|---|---|---|---|
| 487 | 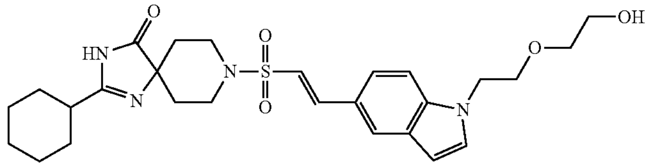 [SMILES: O=C1NC(C2CCCCC2)=NC12CCN(S(=O)(=O)/C=C/c1ccc3c(ccn3CCOCCO)c1)CC2] | LCMS-A-1 | 2.00 | 529 (M + H)+ |
| 488 | 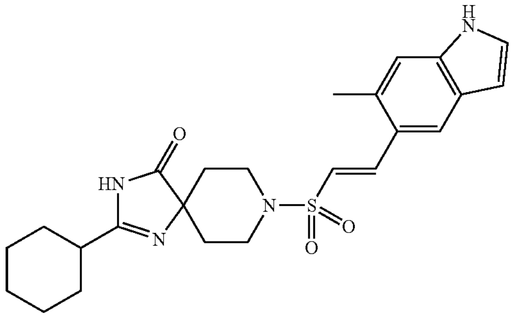 [SMILES: Cc1cc2[nH]ccc2cc1/C=C/S(=O)(=O)N1CCC2(CC1)N=C(C1CCCCC1)NC2=O] | LCMS-A-1 | 2.17 | 455 (M + H)+ |
| 489 | 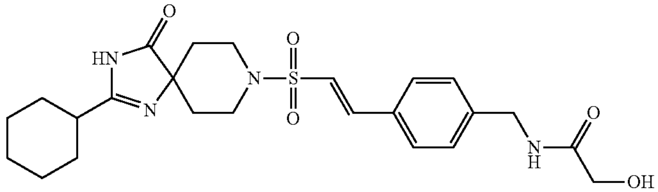 [SMILES: O=C(CO)NCc1ccc(/C=C/S(=O)(=O)N2CCC3(CC2)N=C(C2CCCCC2)NC3=O)cc1] | LCMS-C-1 | 2.30 | 489 (M + H)+ |
| 490 | 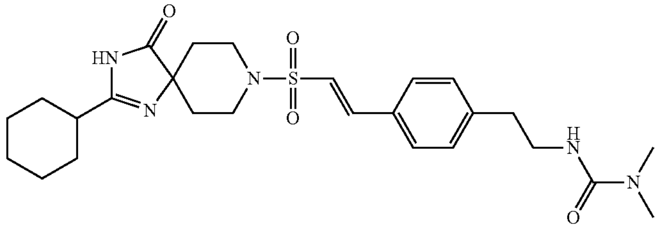 [SMILES: CN(C)C(=O)NCCc1ccc(/C=C/S(=O)(=O)N2CCC3(CC2)N=C(C2CCCCC2)NC3=O)cc1] | LCMS-C-1 | 2.38 | 516 (M + H)+ |
| 491 | 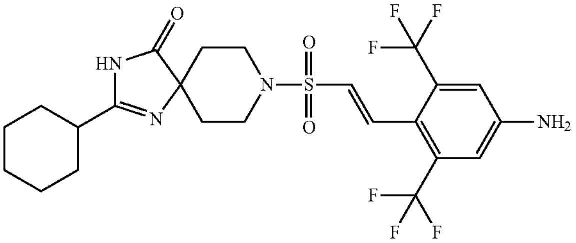 [SMILES: Nc1cc(C(F)(F)F)c(/C=C/S(=O)(=O)N2CCC3(CC2)N=C(C2CCCCC2)NC3=O)c(C(F)(F)F)c1] | LCMS-C-1 | 2.68 | 551 (M − H)− |
| 492 | 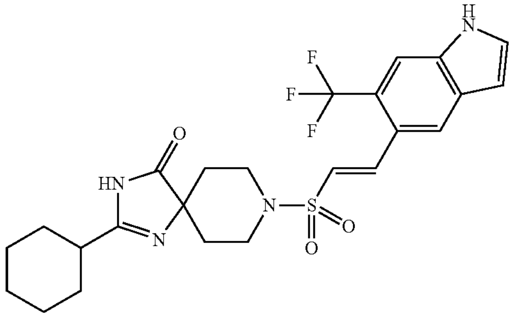 [SMILES: O=C1NC(C2CCCCC2)=NC12CCN(S(=O)(=O)/C=C/c1cc3cc[nH]c3cc1C(F)(F)F)CC2] | LCMS-A-1 | 2.30 | 509 (M + H)+ |

TABLE 70-continued
| Target Compound | Structure | LCMS condition | Retention time (min) | MS (m/z) |
|---|---|---|---|---|
| 493 | 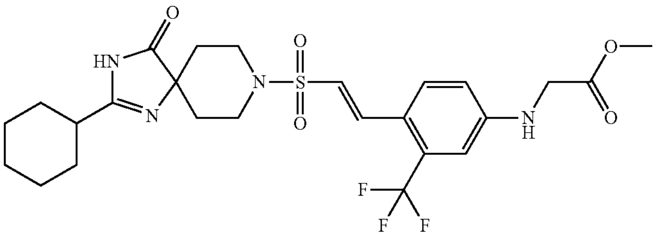 [SMILES: COC(=O)CNc1ccc(/C=C/S(=O)(=O)N2CCC3(CC2)N=C(C2CCCCC2)NC3=O)c(C(F)(F)F)c1] | LCMS-C-1 | 2.65 | 557 (M + H)+ |
| 494 | 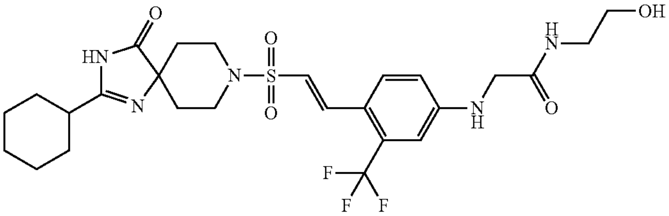 [SMILES: O=C(CNc1ccc(/C=C/S(=O)(=O)N2CCC3(CC2)N=C(C2CCCCC2)NC3=O)c(C(F)(F)F)c1)NCCO] | LCMS-A-1 | 1.90 | 586 (M + H)+ |
| 495 | 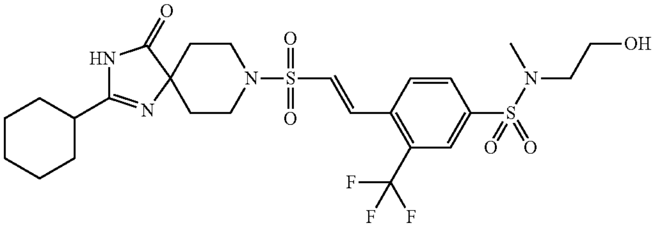 [SMILES: CN(CCO)S(=O)(=O)c1ccc(/C=C/S(=O)(=O)N2CCC3(CC2)N=C(C2CCCCC2)NC3=O)c(C(F)(F)F)c1] | LCMS-C-1 | 2.60 | 607 (M + H)+ |
| 496 | 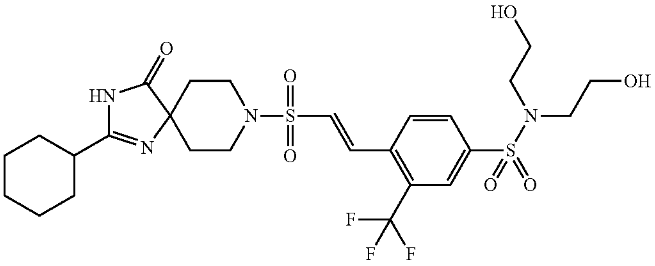 [SMILES: O=C1NC(C2CCCCC2)=NC12CCN(S(=O)(=O)/C=C/c1ccc(S(=O)(=O)N(CCO)CCO)cc1C(F)(F)F)CC2] | LCMS-C-1 | 2.48 | 637 (M + H)+ |
| 497 | 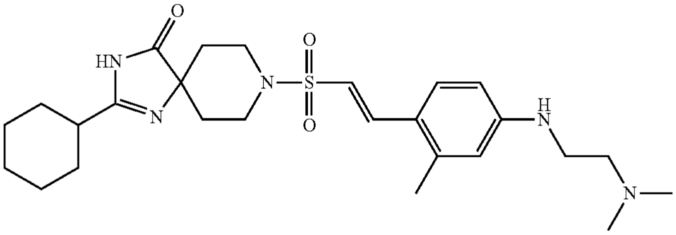 [SMILES: Cc1cc(NCCN(C)C)ccc1/C=C/S(=O)(=O)N1CCC2(CC1)N=C(C1CCCCC1)NC2=O] | LCMS-C-1 | 2.32 | 502 (M + H)+ |
| 498 | 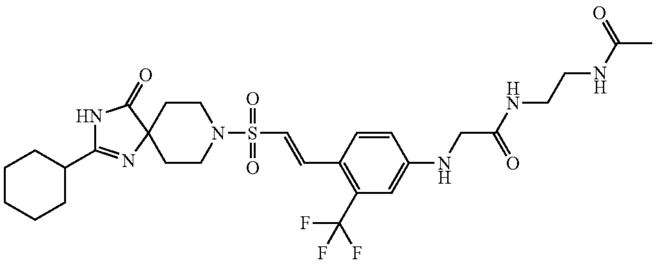 [SMILES: CC(=O)NCCNC(=O)CNc1ccc(/C=C/S(=O)(=O)N2CCC3(CC2)N=C(C2CCCCC2)NC3=O)c(C(F)(F)F)c1] | LCMS-C-1 | 2.37 | 627 (M + H)+ |

TABLE 70-continued
| Target Compound | Structure | LCMS condition | Retention time (min) | MS (m/z) |
|---|---|---|---|---|
| 499 | 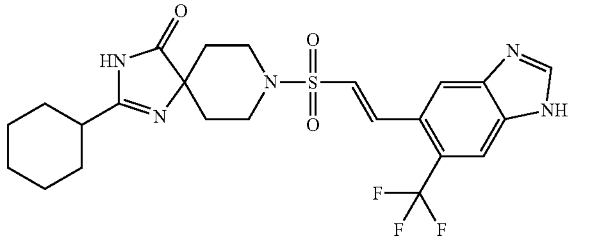 [SMILES: O=C1NC(C2CCCCC2)=NC12CCN(S(=O)(=O)/C=C/c1cc3nc[nH]c3cc1C(F)(F)F)CC2] | LCMS-C-1 | 2.55 | 510 (M + H)+ |
| 500 | 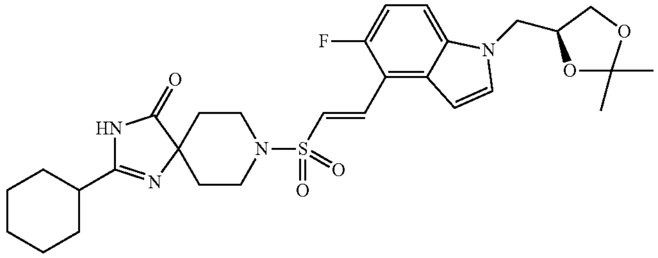 [SMILES: CC1(C)OC[C@H](Cn2ccc3c(/C=C/S(=O)(=O)N4CCC5(CC4)N=C(C4CCCCC4)NC5=O)c(F)ccc32)O1] | LCMS-A-1 | 2.35 | 573 (M + H)+ |
| 501 | 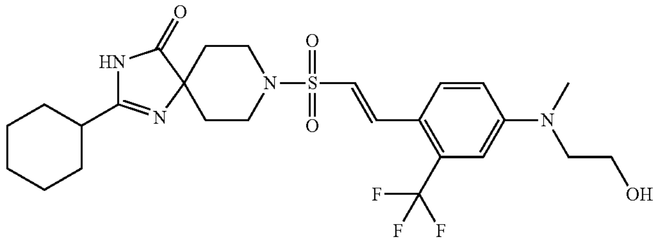 [SMILES: CN(CCO)c1ccc(/C=C/S(=O)(=O)N2CCC3(CC2)N=C(C2CCCCC2)NC3=O)c(C(F)(F)F)c1] | LCMS-A-1 | 2.14 | 543 (M + H)+ |
| 502 | 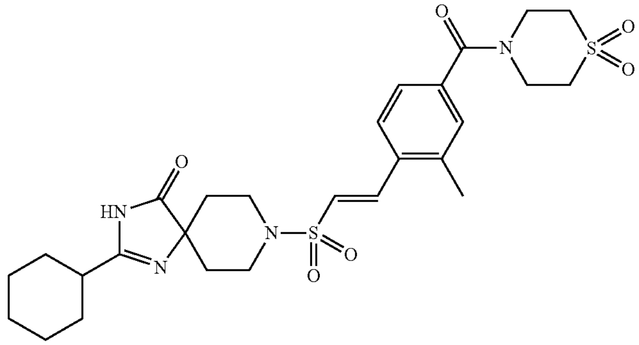 | LCMS-C-1 | 2.18 | 577 (M + H)+ |
| 503 | 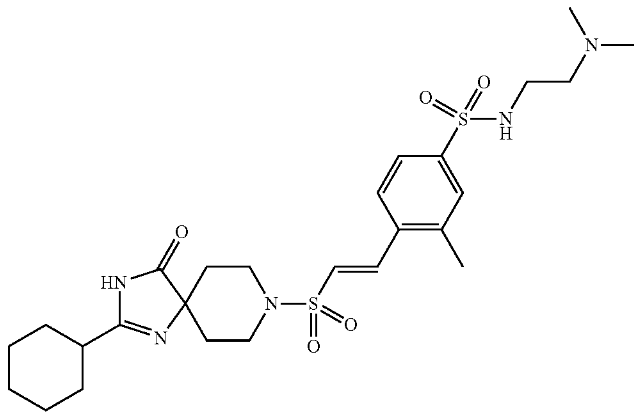 [SMILES: Cc1cc(S(=O)(=O)NCCN(C)C)ccc1/C=C/S(=O)(=O)N1CCC2(CC1)N=C(C1CCCCC1)NC2=O] | LCMS-C-1 | 2.28 | 566 (M + H)+ |

The aryl bromide reagent used in the synthesis of Compound 477 ((4-bromo-indol-1-yl)-morpholin-4-yl-methanone) was synthesized as follows.

(Reaction 95-1)

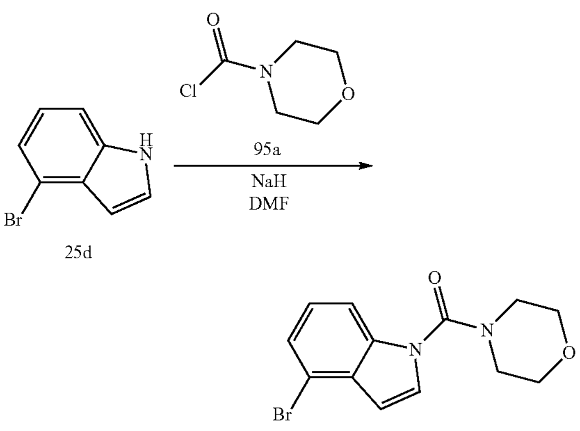

95b (4-Bromo-indol-1-yl)-morpholin-4-yl-methanone was synthesized by operations similar to those in Reaction 25-3 using appropriate reagents and starting material.

$^1$H-NMR (400 MHz, $CDCl_3$) δ 3.61 (4H, t, J=4.8 Hz), 3.78 (4H, t, J=4.8 Hz), 6.69 (1H, d, J=3.6 Hz), 7.17 (1H, t, J=7.9 Hz), 7.35 (2H, d, J=3.6 Hz), 7.38 (2H, d, J=7.9 Hz), 7.65 (1H, d, J=7.9 Hz).

The aryl bromide reagent used in the synthesis of Compound 478 (4-(4-bromo-indol-1-yl)-butan-1-ol) was synthesized as follows.

(Reaction 95-2)

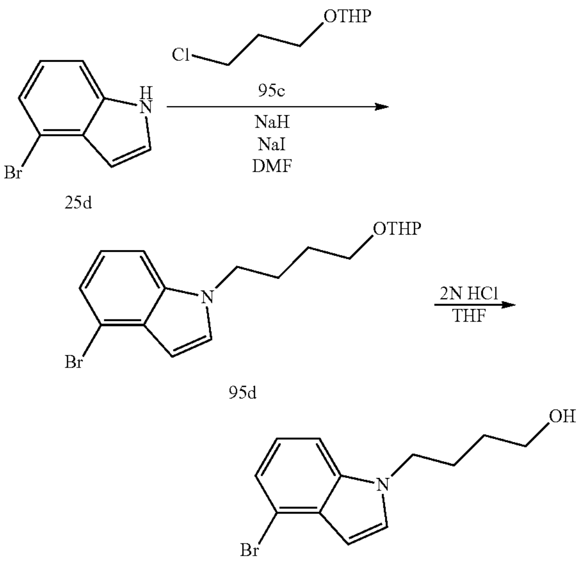

95e 4-(4-Bromo-indol-1-yl)-butan-1-ol was synthesized by operations similar to those in Reaction 29-7 and Reaction 25-4 using appropriate reagents and starting material.

MS (ESI) m/z=268, 270 (M+H)+.

The aryl bromide reagent used in the synthesis of Compound 480 (4-(4-bromo-indol-1-yl)-butane-1,2-diol) was synthesized as follows.

(Reaction 95-3)

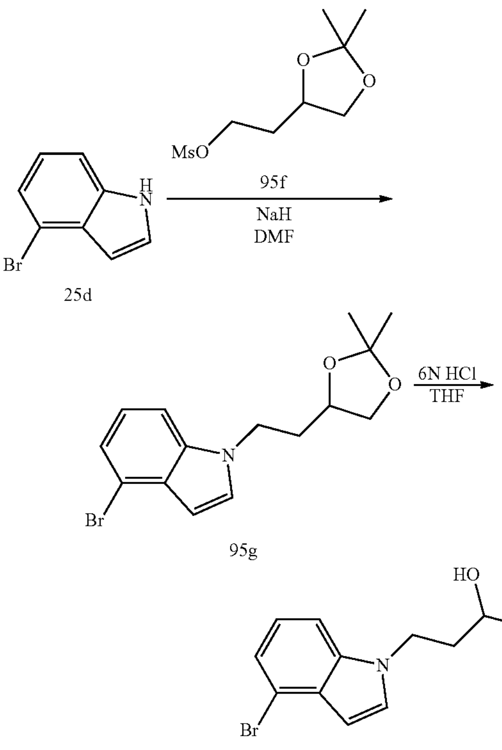

95h 4-(4-Bromo-indol-1-yl)-butane-1,2-diol was synthesized by operations similar to those in Reaction 25-3 and Reaction 25-4 using appropriate reagents and starting material.

MS (ESI) m/z=284, 286 (M+H)+.

The aryl bromide reagent used in the synthesis of Compound 483 (4-bromo-1-thiazol-2-ylmethyl-1H-indole) was synthesized as follows.

(Reaction 95-4)

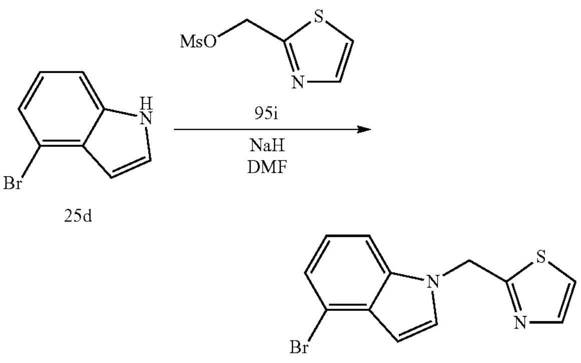

95j

4-Bromo-1-thiazol-2-ylmethyl-1H-indole was synthesized by operations similar to those in Reaction 25-3 using appropriate reagents and starting material.

MS (ESI) m/z=293, 295 (M+H)+.

The aryl bromide reagent used in the synthesis of Compound 484 (3-(4-bromo-indol-1-yl)-propane-1-sulfonic amide) was synthesized as follows.

(Reaction 95-5)

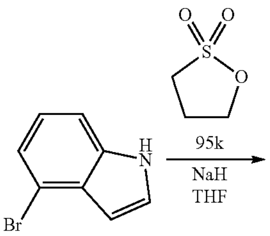

25d

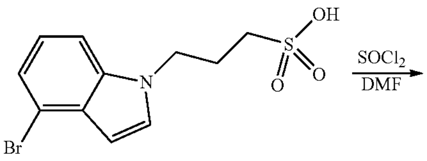

951

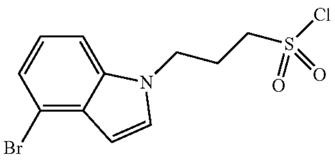

95m 3-(4-Bromo-indol-1-yl)-propane-1-sulfonyl chloride was synthesized as a crude product by operations similar to those in Reaction 25-3 and Reaction 52-3 using 4-bromoindole (0.20 ml, 1.59 mmol) as a starting material and using THF as a solvent.

(Reaction 95-6)

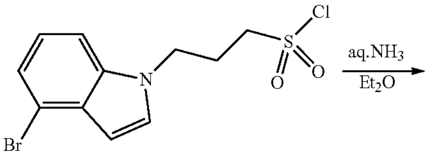

95m

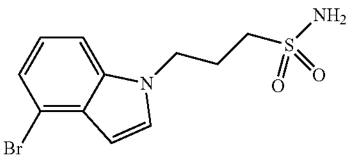

95n 3-(4-Bromo-indol-1-yl)-propane-1-sulfonyl chloride obtained as a crude product was all dissolved in diethyl ether (3.0 ml). A 28% aqueous ammonia solution (3.0 ml) was then added dropwise and the mixture was stirred at room temperature for 2.5 hours. Water was added to the reaction system, followed by extraction with ethyl acetate. The organic layer was washed with water and saturated brine and then concentrated under reduced pressure. The resulting residue was purified by silica gel column chromatography (dichloromethane-ethyl acetate) to give 3-(4-bromo-indol-1-yl)-propane-1-sulfonic amide (55.6 mg, 11% in three steps).

MS (ESI) m/z=317, 319 (M+H)+.

The aryl bromide reagent used in the synthesis of Compound 485 (4-methyl-piperazine-1-carboxylic (4-bromo-3-trifluoromethyl-phenyl)-amide) was synthesized as follows.

(Reaction 95-7)

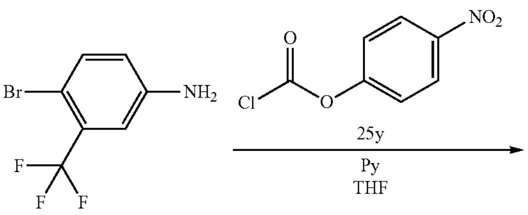

25n

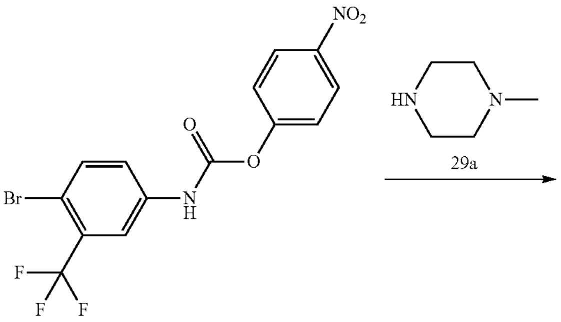

95o

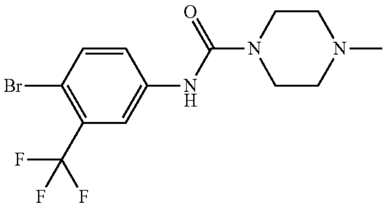

95p

4-Methyl-piperazine-1-carboxylic (4-bromo-3-trifluoromethyl-phenyl)-amide was synthesized by operations similar to those in Reaction 25-11 using appropriate reagents and starting material.

MS (ESI) m/z=366, 368 (M+H)+.

The aryl bromide reagent used in the synthesis of Compound 486 ((4-bromo-benzyl)-carbamic acid isobutyl ester) was synthesized as follows.

(Reaction 95-8)

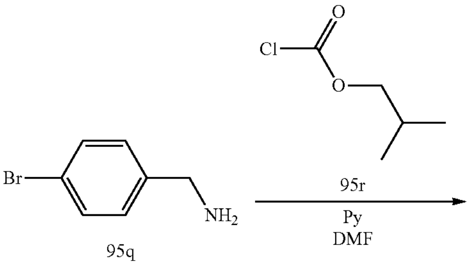

95q

-continued

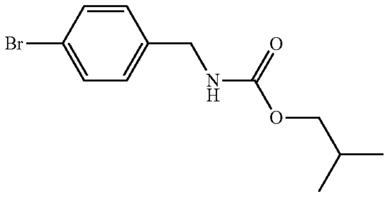

95s (4-Bromo-benzyl)-carbamic acid isobutyl ester was synthesized by operations similar to those in Reaction 25-10 using appropriate reagents and starting material.

MS (ESI) m/z=286, 288 (M+H)+.

The aryl bromide reagent used in the synthesis of Compound 487 (2-[2-(5-bromo-indol-1-yl)-ethoxy]-ethanol) was synthesized as follows.

(Reaction 95-9)

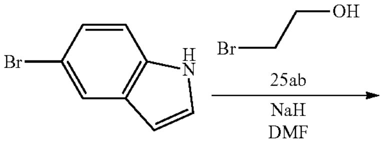

25c

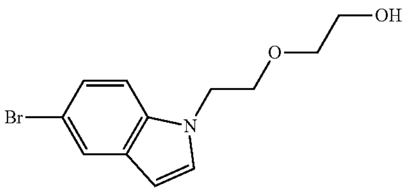

95t

2-[2-(5-Bromo-indol-1-yl)-ethoxy]-ethanol was synthesized by operations similar to those in Reaction 25-3 using appropriate reagents and starting material.

$^1$H-NMR (270 MHz, $CDCl_3$) δ 7.74 (1H, d, J=1.6 Hz), 7.28 (1H, dd, J=8.7, 1.8 Hz), 7.23 (1H, d, J=8.6 Hz), 7.15 (1H, d, J=3.1 Hz), 6.44 (1H, d, J=3.1 Hz), 4.29 (2H, t, J=5.4 Hz), 3.79 (2H, t, J=5.4 Hz), 3.65-3.59 (2H, m), 3.48-3.44 (2H, m), 1.67 (1H, t, J=6.1 Hz).

The aryl bromide reagent used in the synthesis of Compound 488 (5-bromo-6-methyl-1H-indole) was synthesized as follows.

(Reaction 95-10)

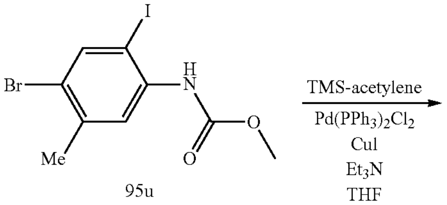

95u

-continued

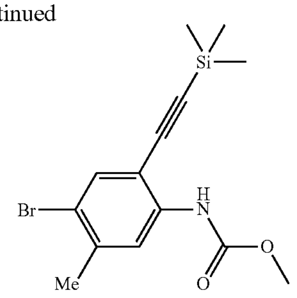

95v (4-Bromo-2-iodo-5-methyl-phenyl)-carbamic acid methyl ester (605 mg, 1.64 mmol) was dissolved in THF (6 ml). (Trimethylsilyl)acetylene (0.70 ml, 4.95 mmol), copper iodide (33.5 mg, 0.175 mmol), $Pd(PPh_3)_2Cl_2$ (56.5 mg, 0.081 mmol) and triethylamine (0.690 ml, 4.95 mmol) were added and the mixture was stirred at room temperature for four hours. Water was added to the reaction system, followed by extraction with ethyl acetate. The organic layer was washed with water and saturated brine, dried over anhydrous sodium sulfate and concentrated under reduced pressure. The resulting residue was purified by silica gel column chromatography (n-hexane-ethyl acetate) to give (4-bromo-5-methyl-2-trimethylsilanylethynyl-phenyl)-carbamic acid methyl ester (548 mg, 98%).

MS (ESI) m/z=340 (M+H)+.

(Reaction 95-11)

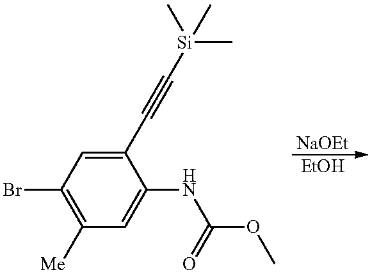

95v

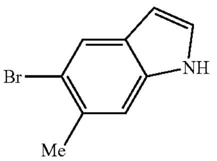

95w (4-Bromo-5-methyl-2-trimethylsilanylethynyl-phenyl)-carbamic acid methyl ester (506 mg, 1.49 mmol) was dissolved in ethanol (6 ml). Sodium ethoxide (20% solution in ethanol, 1.17 ml, 2.97 mmol) was added and the mixture was stirred at 70° C. overnight. The reaction solution was poured into ice water, and 1 N hydrochloric acid and saturated brine were added to this mixture, followed by extraction with ethyl acetate. The organic layer was washed with water and saturated brine, dried over anhydrous sodium sulfate and concentrated under reduced pressure. The resulting residue was purified by silica gel column chromatography (n-hexane-ethyl acetate) to give 5-bromo-6-methyl-1H-indole (207 mg, 66%).

$^1$H-NMR (270 MHz, $CDCl_3$) δ 8.04 (1H, br s), 7.81 (1H, s), 7.27 (1H, s), 7.16-7.14 (1H, m), 6.46-6.43 (1H, m), 2.49 (3H, s).

The aryl bromide reagent used in the synthesis of Compound 489 (N-(4-bromo-benzyl)-2-hydroxy-acetamide) was synthesized as follows.

(Reaction 95-12)

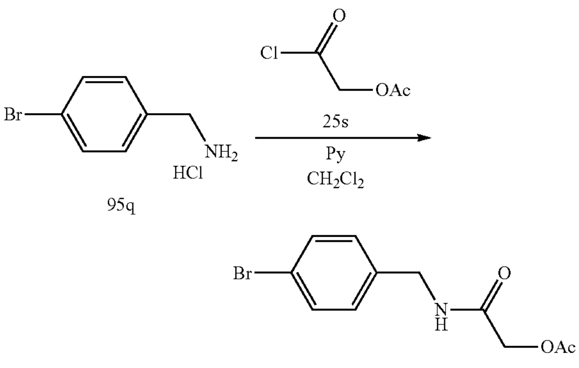

95q

95x

Acetic acid (4-bromo-benzylcarbamoyl)-methyl ester was synthesized as a crude product by operations similar to those in Reaction 2-3 using 4-bromobenzylamine hydrochloride (200 mg, 0.899 mmol) as a starting material and using pyridine as a base.

(Reaction 95-13)

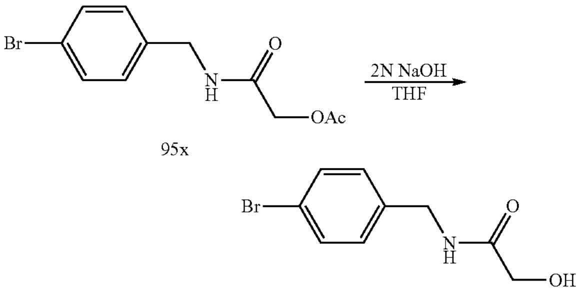

95x

95y

Acetic acid (4-bromo-benzylcarbamoyl)-methyl ester obtained as a crude product was all dissolved in THF (2.0 ml). A 2 N aqueous sodium hydroxide solution (2.0 ml) was then added and the mixture was stirred at room temperature for five hours. Water was added to the reaction system, followed by extraction with ethyl acetate. The organic layer was washed with saturated brine and then concentrated under reduced pressure. The resulting residue was purified by silica gel column chromatography (dichloromethane-methanol) to give N-(4-bromo-benzyl)-2-hydroxy-acetamide (56.0 mg, 25% for two steps).

MS (ESI) m/z=244, 246 (M+H)+.

The aryl bromide reagent used in the synthesis of Compound 490 (3-[2-(4-bromo-phenyl)-ethyl]-1,1-dimethyl-urea) was synthesized as follows.

(Reaction 95-14)

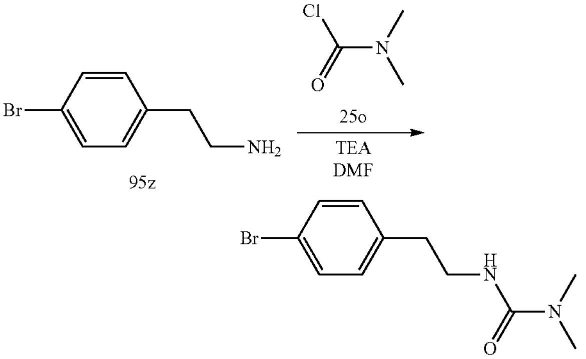

95z

95aa

3-[2-(4-Bromo-phenyl)-ethyl]-1,1-dimethyl-urea was synthesized by operations similar to those in Reaction 82-1 using appropriate reagents and starting material.

MS (ESI) m/z=271, 273 (M+H)+.

The aryl bromide reagent used in the synthesis of Compound 492 (5-bromo-6-trifluoromethyl-1H-indole) was synthesized as follows.

(Reaction 95-15)

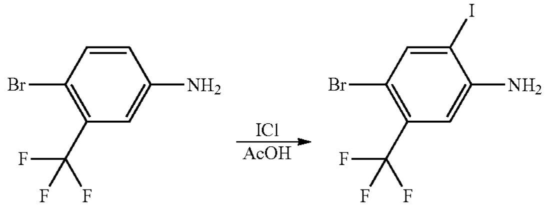

25n

95ab

4-Bromo-3-trifluoromethyl-phenylamine (1.00 g, 4.17 mmol) was dissolved in acetic acid (5 ml). Iodine monochloride (1 M solution in dichloromethane, 5 ml) was added and the mixture was stirred at 60° C. overnight. The reaction solution was poured into a mixture of ice and a saturated aqueous sodium bicarbonate solution and then extracted with ethyl acetate. The organic layer was washed with an aqueous sodium bicarbonate solution, an aqueous sodium thiosulfate solution, water and saturated brine, dried over anhydrous sodium sulfate and concentrated under reduced pressure. The resulting residue was purified by silica gel column chromatography (n-hexane-ethyl acetate) to give 4-bromo-2-iodo-5-trifluoromethyl-phenylamine (889 mg, 58%).

$^1$H-NMR (270 MHz, $CDCl_3$) δ 7.92 (1H, s), 7.00 (1H, s), 4.31 (2H, br s).

(Reaction 95-16)

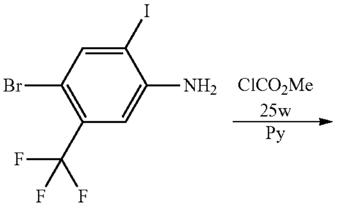

95ab

-continued

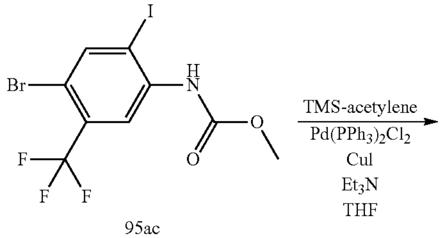

95ac

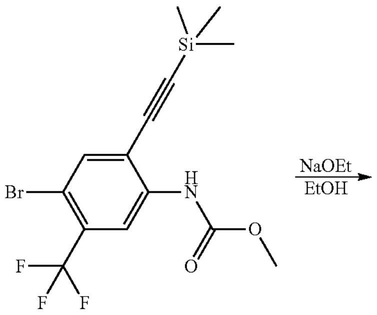

95ad

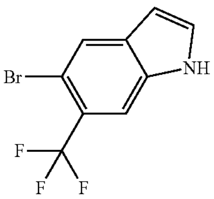

95ae

5-Bromo-6-trifluoromethyl-1H-indole was synthesized by operations similar to those in Reaction 25-10, Reaction 95-10 and Reaction 95-11 using appropriate reagents and starting material.

$^1$H-NMR (270 MHz, $CDCl_3$) δ 8.41 (1H, s), 7.96 (1H, s), 7.78 (1H, s), 7.38-7.36 (1H, m), 6.57-6.54 (1H, m).

The aryl bromide reagent used in the synthesis of Compound 493 ((4-bromo-3-trifluoromethyl-phenylamino)-acetic acid methyl ester) was synthesized as follows.

(Reaction 95-17)

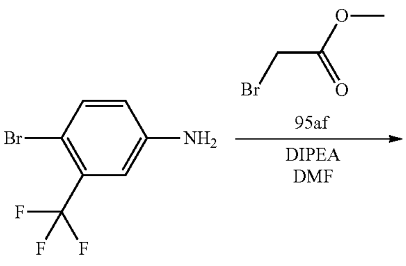

25n

-continued

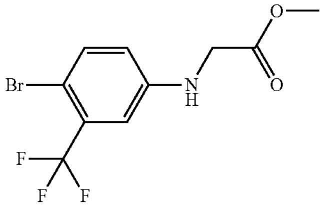

95ag

N,N-Diisopropylethylamine (1.22 ml, 7.00 mmol) and methyl bromoacetate (1.00 g, 6.54 mmol) were sequentially added to a solution of 4-bromo-3-(trifluoromethyl)aniline (1.40 g, 5.83 mmol) in DMF (10 ml), and the mixture was heated with stirring at 80° C. for 25 hours. The reaction mixture was cooled and water was then added, followed by extraction with ethyl acetate. The organic layer was sequentially washed with water and saturated brine, and then dried over $MgSO_4$ and concentrated under reduced pressure. The resulting residue was triturated with hexane:dichloromethane=9:1 to give (4-bromo-3-trifluoromethyl-phenylamino)-acetic acid methyl ester (1.22 g, 67%).

MS (ESI) m/z=312, 314 (M+H)+

The aryl bromide reagent used in the synthesis of Compound 494 (2-(4-bromo-3-trifluoromethyl-phenylamino)-N-(2-hydroxy-ethyl)-acetamide) was synthesized as follows.

(Reaction 95-18)

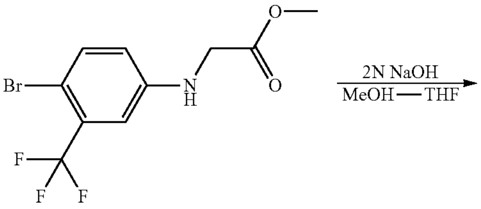

95ag

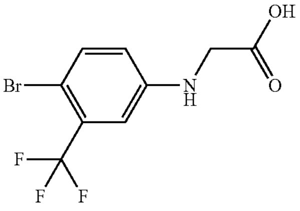

95ah

A 2 N aqueous NaOH solution (15.0 ml, 30.0 mmol) was added to a solution of (4-bromo-3-trifluoromethyl-phenylamino)-acetic acid methyl ester (4.30 g, 13.8 mmol) in methanol-THF (6:1, 35.0 ml), and the mixture was stirred at room temperature for 18 hours. The reaction mixture was made acidic with hydrochloric acid and extracted with ethyl acetate. The organic layer was sequentially washed with water and saturated brine, and then dried over $MgSO_4$ and concentrated under reduced pressure to give (4-bromo-3-trifluoromethyl-phenylamino)-acetic acid (4.03 g, 98%).

MS (ESI) m/z=298, 300 (M+H)+

(Reaction 95-19)

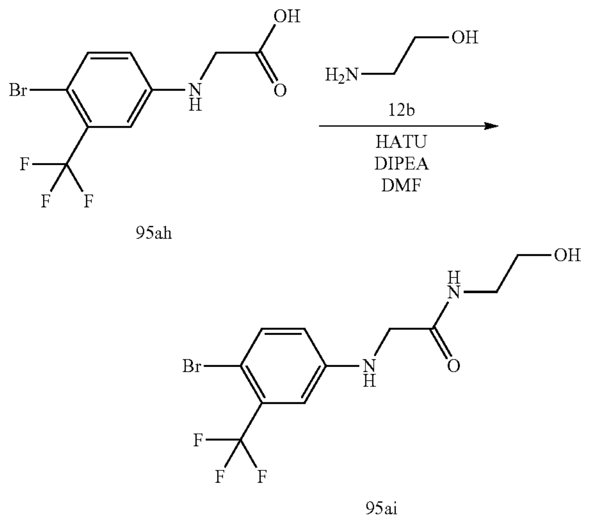

2-(4-Bromo-3-trifluoromethyl-phenylamino)-N-(2-hydroxy-ethyl)-acetamide was synthesized by operations similar to those in Reaction 10-14 using appropriate reagents and starting material.

$^1$H-NMR ($CDCl_3$) δ 2.11 (1H, t, J=5.1 Hz), 3.48 (2H, q, J=5.2 Hz), 3.73 (2H, q, J=5.2 Hz), 3.84 (2H, d, J=5.4 Hz), 4.51-4.57 (1H, m), 6.61 (1H, dd, J=8.7, 2.9 Hz), 6.72 (1H, s), 6.93 (1H, d, J=2.9 Hz), 7.49 (1H, d, J=8.7 Hz).

The aryl bromide reagent used in the synthesis of Compound 495 (4-bromo-N-(2-hydroxy-ethyl)-N-methyl-3-trifluoromethyl-benzenesulfonamide) was synthesized as follows.

(Reaction 95-20)

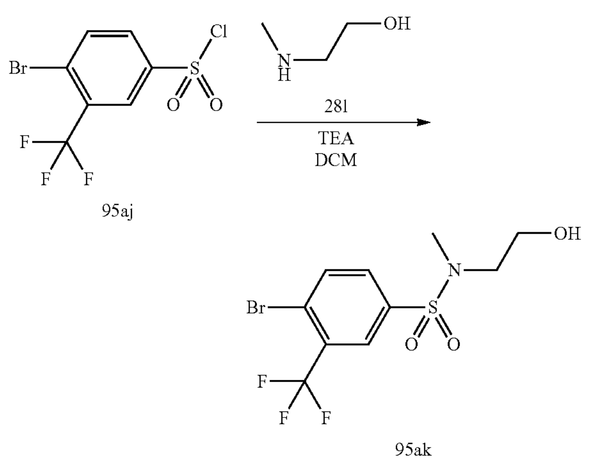

4-Bromo-N-(2-hydroxy-ethyl)-N-methyl-3-trifluoromethyl-benzenesulfonamide was synthesized by operations similar to those in Reaction 5-4 using appropriate reagents and starting material.

MS (ESI) m/z=362, 364 (M+H)+.

The aryl bromide reagent used in the synthesis of Compound 496 (4-bromo-N,N-bis-(2-hydroxy-ethyl)-3-trifluoromethyl-benzenesulfonamide) was synthesized as follows.

(Reaction 95-21)

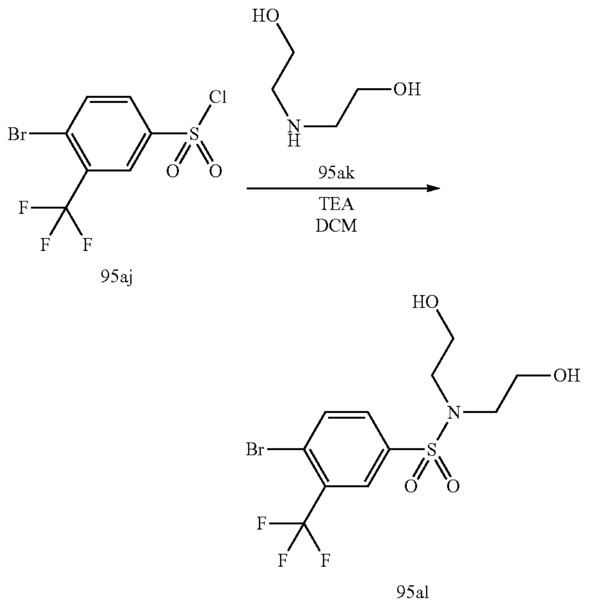

4-Bromo-N,N-bis-(2-hydroxy-ethyl)-3-trifluoromethyl-benzenesulfonamide was synthesized by operations similar to those in Reaction 5-4 using appropriate reagents and starting material.

MS (ESI) m/z=392, 394 (M+H)+.

The aryl bromide reagent used in the synthesis of Compound 497 (N'-(4-bromo-3-methyl-phenyl)-N,N-dimethyl-ethane-1,2-diamine) was synthesized as follows.

(Reaction 95-22)

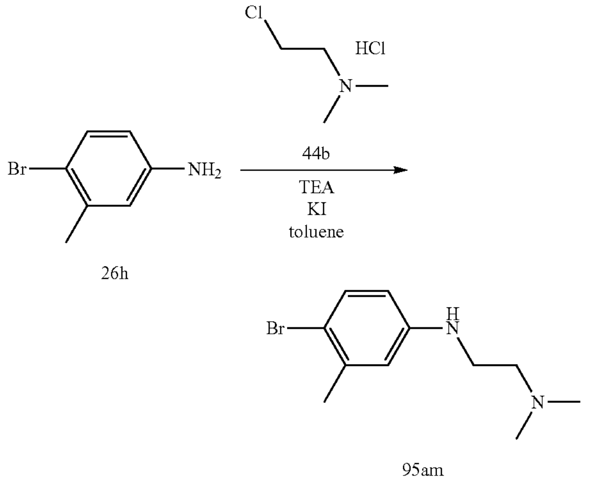

2-Chloro-N,N-dimethylethylamine hydrochloride (372 mg, 2.58 mmol), potassium iodide (428 mg, 2.58 mmol) and triethylamine (0.719 ml, 5.16 mmol) were added to a solution of 4-bromo-3-methylaniline (400 mg, 2.15 mmol) in toluene (5.0 ml), and the mixture was heated with stirring at 110° C. for 17 hours. The reaction mixture was cooled and water was then added, followed by extraction with ethyl acetate. The organic layer was sequentially washed with water and saturated brine and then concentrated under reduced pressure.

The resulting residue was purified by silica gel column chromatography (dichloromethane-methanol) to give N'-(4-bromo-3-methyl-phenyl)-N,N-dimethyl-ethane-1,2-diamine (100 mg, 18%).

MS (ESI) m/z=257, 259 (M+H)+.

The aryl bromide reagent used in the synthesis of Compound 498 (N-(2-acetylamino-ethyl)-2-(4-bromo-3-trifluoromethyl-phenylamino)-acetamide) was synthesized as follows.

(Reaction 95-23)

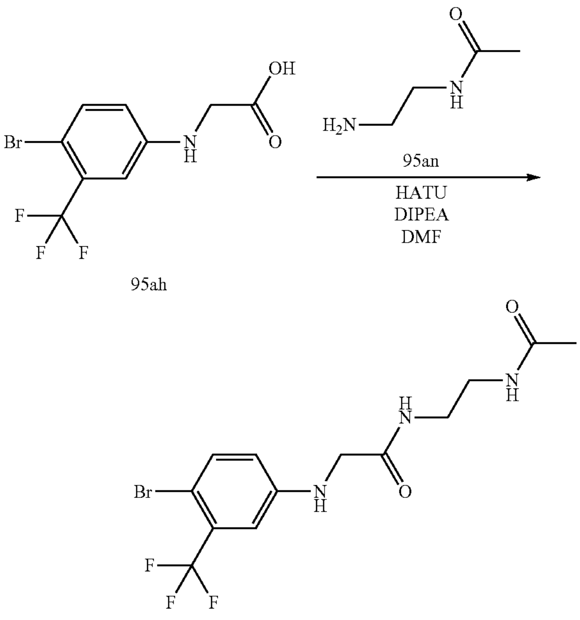

95ah

95an

95ao

N-(2-Acetylamino-ethyl)-2-(4-bromo-3-trifluoromethyl-phenylamino)-acetamide was synthesized by operations similar to those in Reaction 10-14 using appropriate reagents and starting material.

MS (ESI) m/z=382, 384 (M+H)+.

The aryl bromide reagent used in the synthesis of Compound 499 (5-bromo-6-trifluoromethyl-1H-benzimidazole) was synthesized as follows.

(Reaction 95-24)

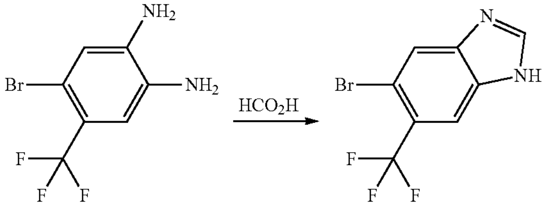

95ap 95aq

4-Bromo-5-trifluoromethyl-benzene-1,2-diamine (200 mg, 0.785 mmol) was dissolved in formic acid (3 ml), and the mixture was stirred at 120° C. for six hours. The reaction solution was concentrated, and water was added to the resulting residue, followed by extraction with ethyl acetate. The organic layer was washed with water and saturated brine, dried over anhydrous sodium sulfate and concentrated under reduced pressure to give 5-bromo-6-trifluoromethyl-1H-benzimidazole (201 mg) as a crude compound.

MS (ESI) m/z=265 (M+H)+.

The aryl bromide reagent used in the synthesis of Compound 500 (4-bromo-1-((S)-2,2-dimethyl-[1,3]dioxolan-4-ylmethyl)-5-fluoro-1H-indole) was synthesized as follows.

(Reaction 95-25)

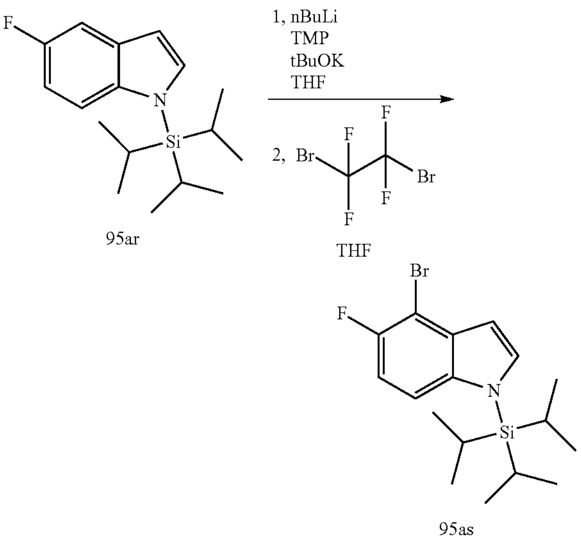

95ar

95as

A solution of n-butyllithium (2.1 mL, 3.39 mmol) in tetrahydrofuran (6.8 mL) was cooled to −78° C., and 2,2,6,6-tetramethylpiperidine (0.57 mL, 3.39 mmol) and a 1.0 M solution of potassium t-butoxide in tetrahydrofuran (3.4 mL, 3.39 mmol) were added. After stirring for 15 minutes, a solution of 5-fluoro-1-triisopropylsilanyl-1H-indole (494 mg, 1.70 mmol) in tetrahydrofuran (5 ml) was added dropwise, and the mixture was stirred at −78° C. for 2.5 hours. 1,2-Dibromo-1,1,2,2-tetrafluoroethane (38 mL, 0.319 mmol) was added, and the mixture was warmed to −40° C. over 35 minutes and further warmed to 22° C. over 12 hours. Silica gel (17 g) was added and the solvent was then distilled off. The residue was subjected to silica gel column chromatography to give a pale yellow oily substance (380 mg) as a mixture of 4-bromo-5-fluoro-1-triisopropylsilanyl-1H-indole:5-fluoro-1-triisopropylsilanyl-1H-indole=1:1.1.

$^1$H-NMR ($CDCl_3$) δ 7.37-7.33 (2H, m), 6.94 (1H, dd, J=9.0, 4.5 Hz), 6.68 (1H, d, J=3.9 Hz), 1.71-1.63 (3H, m), 1.14 (18H, d, J=7.3 Hz).

(Reaction 95-26)

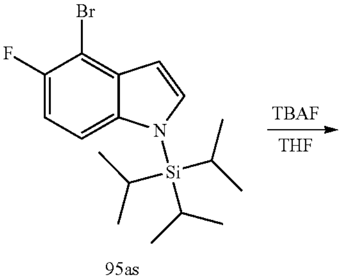

95as

-continued

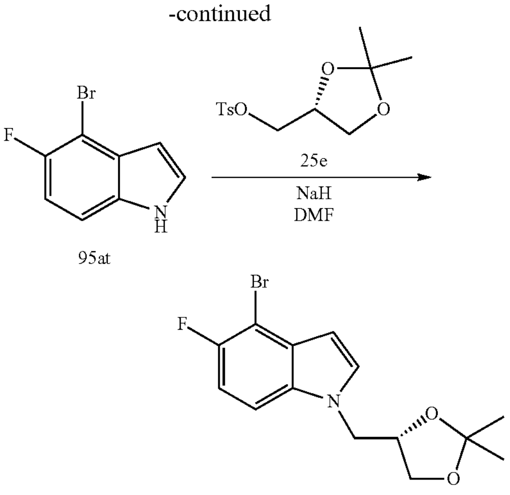

95at

95au

4-Bromo-1-((S)-2,2-dimethyl-[1,3]dioxolan-4-ylmethyl)-5-fluoro-1H-indole was synthesized by operations similar to those in Reaction 39-2 and Reaction 25-3 using appropriate reagents and starting material.

MS (ESI) m/z=328, 330 (M+H)+.

The aryl bromide reagent used in the synthesis of Compound 501 (2-[(4-bromo-3-trifluoromethyl-phenyl)-methyl-amino]-ethanol) was synthesized as follows.

(Reaction 95-27)

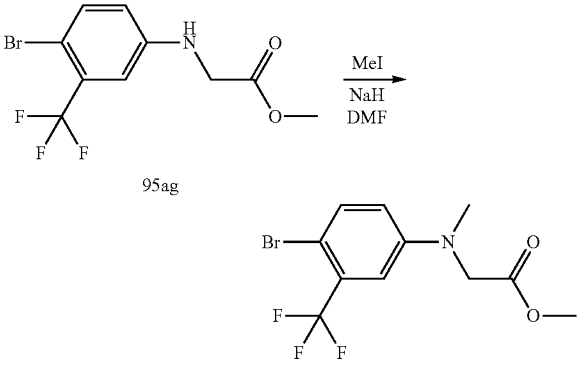

95ag

95av

[(4-Bromo-3-trifluoromethyl-phenyl)-methyl-amino]-acetic acid methyl ester was synthesized by operations similar to those in Reaction 25-3 using appropriate reagents and starting material.

MS (ESI) m/z=326, 328 (M+H)+.

(Reaction 95-28)

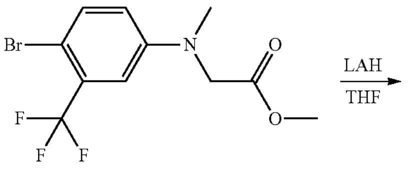

95av

-continued

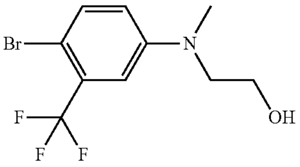

95aw

A solution of [(4-bromo-3-trifluoromethyl-phenyl)-methyl-amino]-acetic acid methyl ester (77.6 mg, 0.238 mmol) in THF (1.0 ml) was added dropwise to a suspension of lithium aluminum hydride (372 mg, 2.58 mmol) in THF (1.5 ml) at 0° C. The mixture was stirred for 14 hours while gradually warming from 0° C. to room temperature. A 2 N aqueous HCl solution was added to the reaction mixture, followed by extraction with ethyl acetate. The organic layer was sequentially washed with water and saturated brine and then concentrated under reduced pressure. The resulting residue was purified by silica gel column chromatography (dichloromethane-ethyl acetate) to give 2-[(4-bromo-3-trifluoromethyl-phenyl)-methyl-amino]-ethanol (58.0 mg, 82%).

MS (ESI) m/z=298, 300 (M+H)+.

The aryl bromide reagent used in the synthesis of Compound 502 ((4-bromo-3-methyl-phenyl)-(1,1-dioxo-1$\lambda^6$-thiomorpholin-4-yl)-methanone) was synthesized as follows.

(Reaction 95-29)

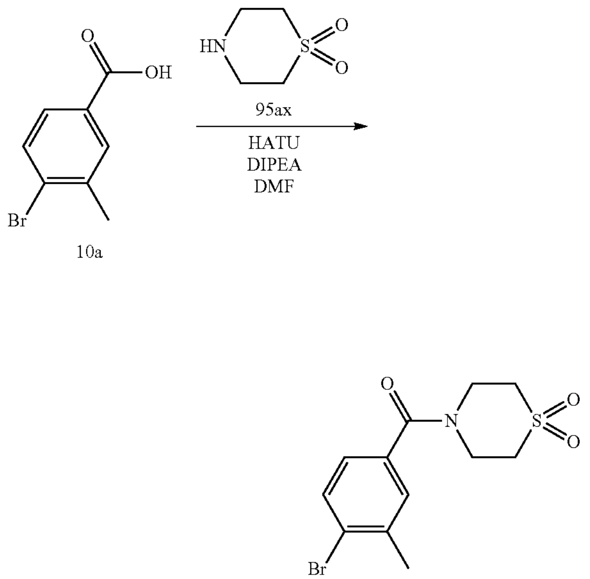

10a

95ay (4-Bromo-3-methyl-phenyl)-(1,1-dioxo-1$\lambda^6$-thiomorpholin-4-yl)-methanone was synthesized by operations similar to those in Reaction 10-14 using appropriate reagents and starting material.

MS (ESI) m/z=332, 334 (M+H)+.

The aryl bromide reagent used in the synthesis of Compound 503 (4-bromo-N-(2-dimethylamino-ethyl)-3-methyl-benzenesulfonamide) was synthesized as follows.

(Reaction 95-30)

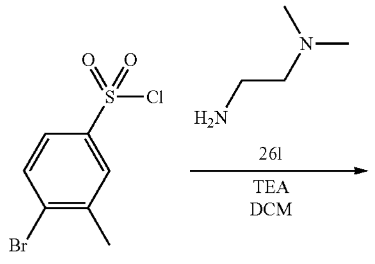

28j

-continued

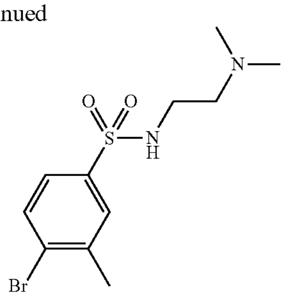

95az

4-Bromo-N-(2-dimethylamino-ethyl)-3-methyl-benzenesulfonamide was synthesized by operations similar to those in Reaction 5-4 using appropriate reagents and starting material.

MS (ESI) m/z=321, 323 (M+H)+.

Example 96

The example compounds shown below were obtained by operations similar to those in Reaction 25-2 using appropriate reagents and starting materials.

Compounds 504 to 523

TABLE 71

| Target Compound | Structure | LCMS condition | Retention time (min) | MS (m/z) |
|---|---|---|---|---|
| 504 | 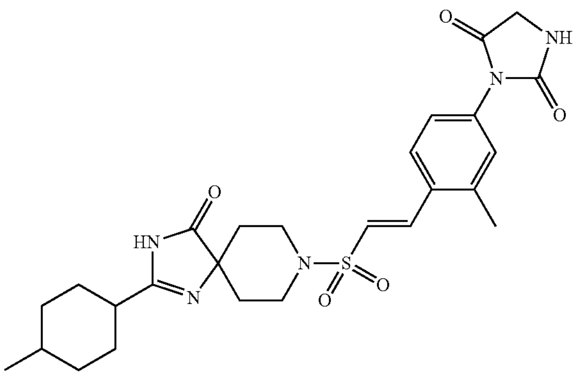 [SMILES: Cc1cc(N2C(=O)CNC2=O)ccc1/C=C/S(=O)(=O)N1CCC2(CC1)N=C(C1CCC(C)CC1)NC2=O] | LCMS-C-1 | 2.4 | 528 (M + H)+ |
| 505 | 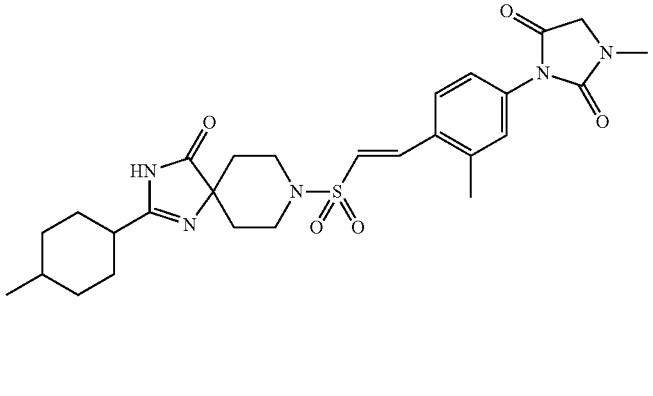 | LCMS-C-1 | 2.47 | 542 (M + H)+ |

TABLE 71-continued
| Target Compound | Structure | LCMS condition | Retention time (min) | MS (m/z) |
|---|---|---|---|---|
| 506 | 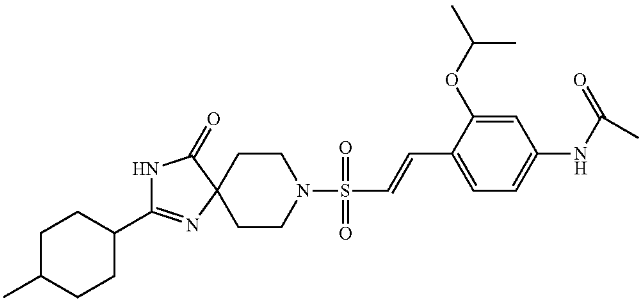 [SMILES: CC(=O)Nc1ccc(/C=C/S(=O)(=O)N2CCC3(CC2)N=C(C2CCC(C)CC2)NC3=O)c(OC(C)C)c1] | LCMS-D-1 | 1.91 | 531 (M + H)+ |
| 507 | 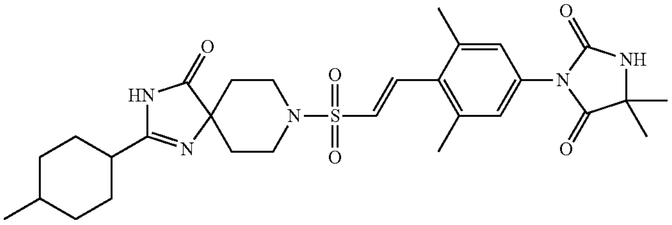 | LCMS-D-1 | 1.9 | 570 (M + H)+ |
| 508 | 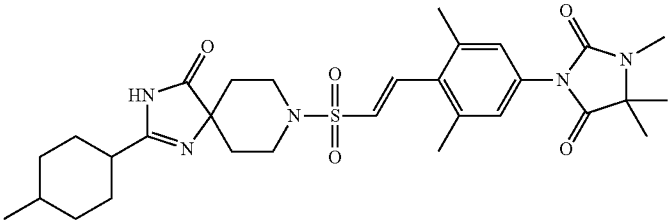 | LCMS-D-1 | 1.98 | 584 (M + H)+ |
| 509 | 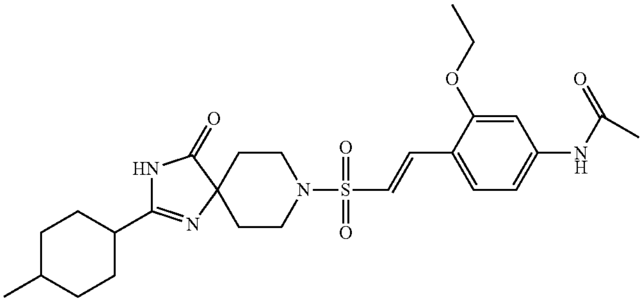 [SMILES: CCOc1cc(NC(C)=O)ccc1/C=C/S(=O)(=O)N1CCC2(CC1)N=C(C1CCC(C)CC1)NC2=O] | LCMS-D-1 | 1.9 | 517 (M + H)+ |
| 510 | 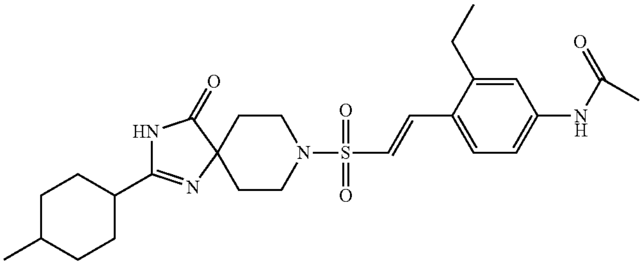 [SMILES: CCc1cc(NC(C)=O)ccc1/C=C/S(=O)(=O)N1CCC2(CC1)N=C(C1CCC(C)CC1)NC2=O] | LCMS-D-1 | 1.82 | 501 (M + H)+ |

TABLE 71-continued
| Target Compound | Structure | LCMS condition | Retention time (min) | MS (m/z) |
|---|---|---|---|---|
| 511 | 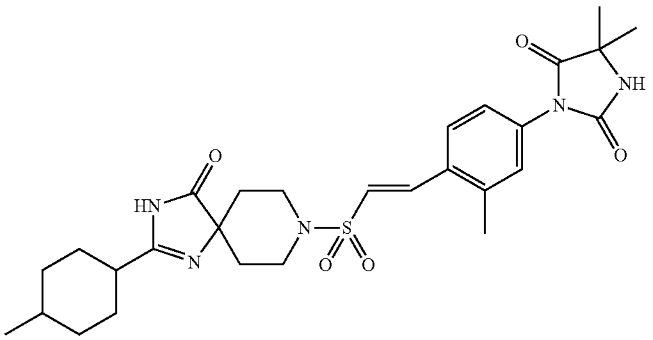 | LCMS-F-1 | 0.92 | 556 (M + H)+ |
| 512 | 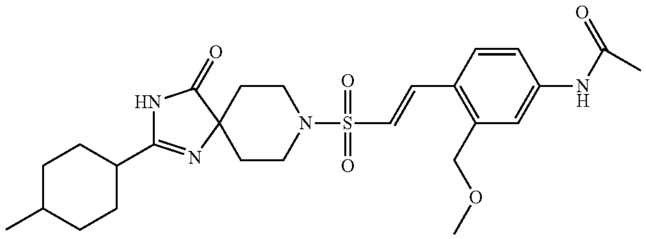 [SMILES: COCc1cc(NC(C)=O)ccc1/C=C/S(=O)(=O)N1CCC2(CC1)N=C(C1CCC(C)CC1)NC2=O] | LCMS-D-1 | 1.84 | 517 (M + H)+ |
| 513 | 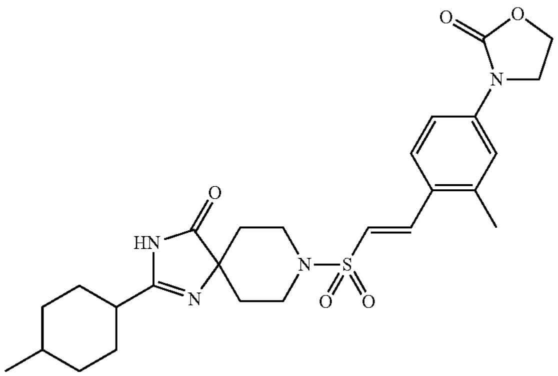 [SMILES: Cc1cc(N2CCOC2=O)ccc1/C=C/S(=O)(=O)N1CCC2(CC1)N=C(C1CCC(C)CC1)NC2=O] | LCMS-C-1 | 2.47 | 515 (M + H)+ |
| 514 | 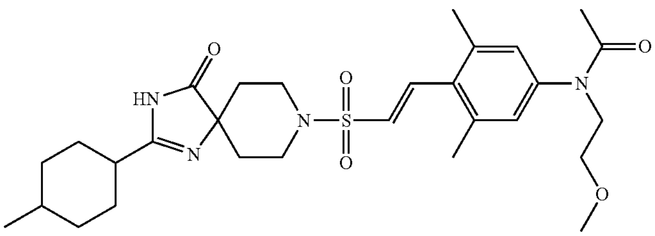 [SMILES: COCCN(C(C)=O)c1cc(C)c(/C=C/S(=O)(=O)N2CCC3(CC2)N=C(C2CCC(C)CC2)NC3=O)c(C)c1] | LCMS-D-1 | 2.09 | 559 (M + H)+ |
| 515 | 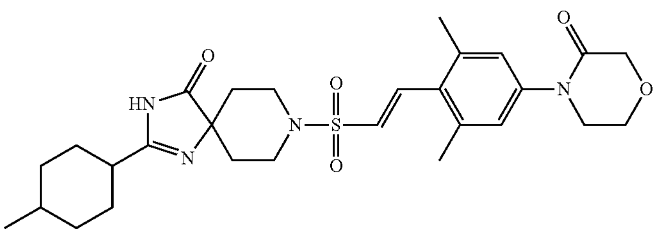 [SMILES: Cc1cc(N2CCOCC2=O)cc(C)c1/C=C/S(=O)(=O)N1CCC2(CC1)N=C(C1CCC(C)CC1)NC2=O] | LCMS-D-1 | 1.83 | 543 (M + H)+ |

TABLE 71-continued
| Target Compound | Structure | LCMS condition | Retention time (min) | MS (m/z) |
|---|---|---|---|---|
| 516 | 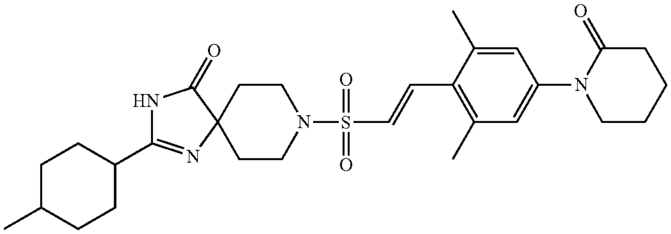 [SMILES: Cc1cc(N2CCCCC2=O)cc(C)c1/C=C/S(=O)(=O)N1CCC2(CC1)N=C(C1CCC(C)CC1)NC2=O] | LCMS-D-1 | 2.22 | 541 (M + H)+ |
| 517 | 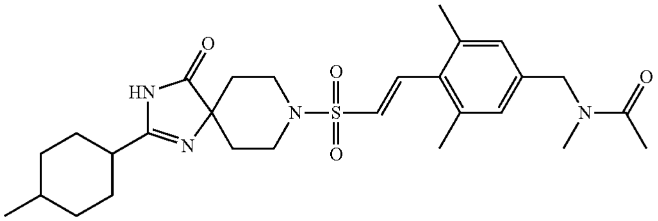 [SMILES: CC(=O)N(C)Cc1cc(C)c(/C=C/S(=O)(=O)N2CCC3(CC2)N=C(C2CCC(C)CC2)NC3=O)c(C)c1] | LCMS-D-1 | 2.23 | 529 (M + H)+ |
| 518 | 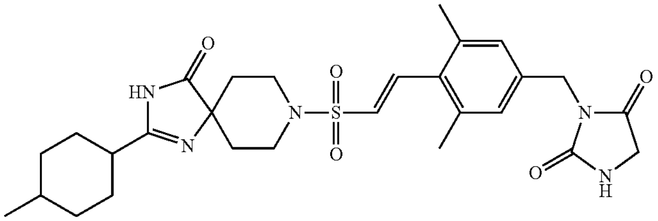 [SMILES: Cc1cc(CN2C(=O)CNC2=O)cc(C)c1/C=C/S(=O)(=O)N1CCC2(CC1)N=C(C1CCC(C)CC1)NC2=O] | LCMS-D-1 | 2.13 | 556 (M + H)+ |
| 519 | 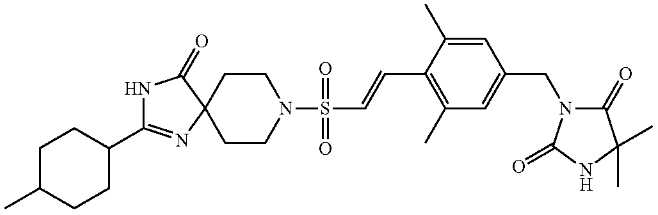 | LCMS-D-1 | 2.4 | 584 (M + H)+ |
| 520 | 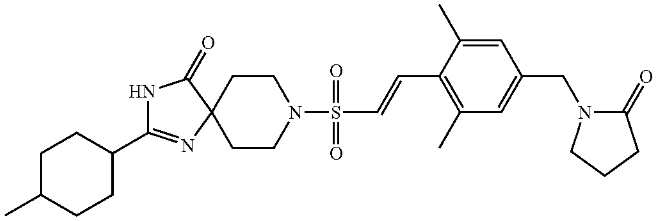 [SMILES: Cc1cc(CN2CCCC2=O)cc(C)c1/C=C/S(=O)(=O)N1CCC2(CC1)N=C(C1CCC(C)CC1)NC2=O] | LCMS-D-1 | 2.28 | 541 (M + H)+ |
| 521 | 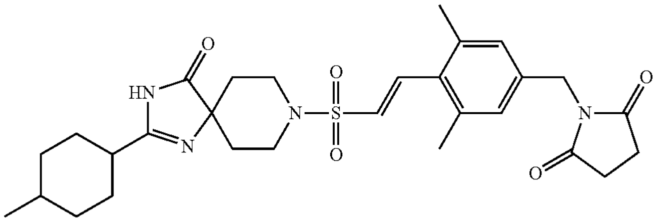 [SMILES: Cc1cc(CN2C(=O)CCC2=O)cc(C)c1/C=C/S(=O)(=O)N1CCC2(CC1)N=C(C1CCC(C)CC1)NC2=O] | LCMS-D-1 | 2.27 | 555 (M + H)+ |

TABLE 71-continued

| Target Compound | Structure | LCMS condition | Retention time (min) | MS (m/z) |
|---|---|---|---|---|
| 522 | 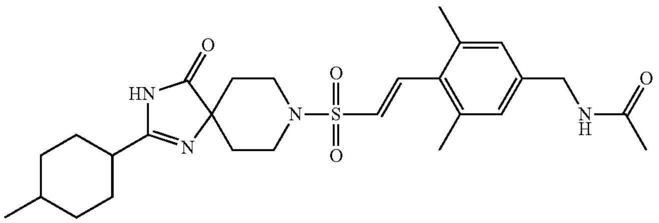 [SMILES: CC(=O)NCc1cc(C)c(/C=C/S(=O)(=O)N2CCC3(CC2)N=C(C2CCC(C)CC2)NC3=O)c(C)c1] | LCMS-D-1 | 2.45 | 515 (M + H)+ |
| 523 | 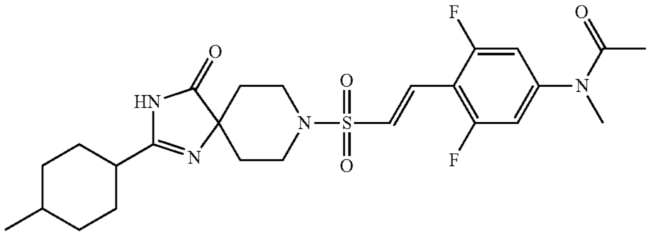 [SMILES: CC(=O)N(C)c1cc(F)c(/C=C/S(=O)(=O)N2CCC3(CC2)N=C(C2CCC(C)CC2)NC3=O)c(F)c1] | LCMS-D-1 | 2.33 | 523 (M + H)+ |

The aryl bromide reagent used in the synthesis of Compound 504 (3-(4-bromo-3-methyl-phenyl)-imidazolidine-2,4-dione) was synthesized as follows.

(Reaction 96-1)

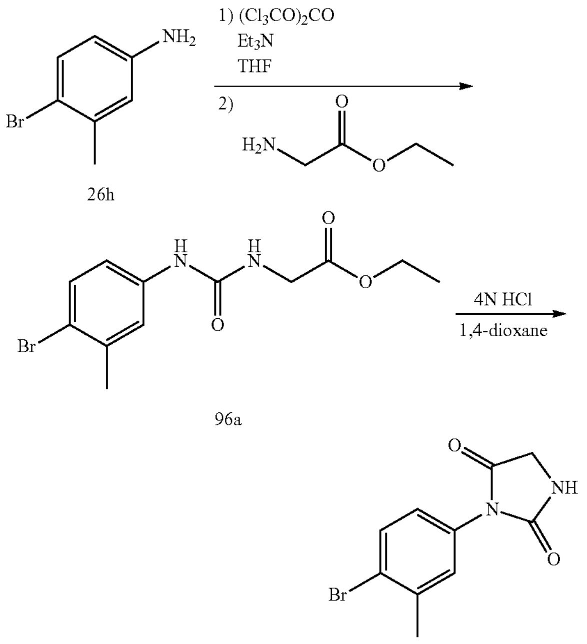

26h

96a

96b

Triethylamine (20 ml, 145 mmol) and 4-bromo-3-methyl-phenylamine (4.49 g, 24.14 mmol) were added to a solution of triphosgene (1.0 ml, 8.05 mmol) in THF (70 ml) at 0° C., and the mixture was stirred at the same temperature for 40 minutes. Further, the reaction mixture was warmed to room temperature and stirred at the same temperature for one hour. Water was added to the reaction solution, and the mixture was then concentrated under reduced pressure, followed by extraction with ethyl acetate. The organic phase was sequentially washed with water and saturated brine and then concentrated under reduced pressure to give [3-(4-bromo-3-methyl-phenyl)-ureido]-acetic acid ethyl ester (5.07 g) as a crude product. This crude product was used in the next reaction without purification.

4 N HCl-dioxane (7.5 ml, 30 mmol) was added to a solution of the crude product [3-(4-bromo-3-methyl-phenyl)-ureido]-acetic acid ethyl ester (5.07 g) in dioxane (60 ml), and the mixture was heated with stirring at 80° C. for 17 hours. The reaction mixture was cooled to room temperature and then concentrated under reduced pressure, and water was added, followed by extraction with ethyl acetate. The organic phase was washed with saturated brine and then concentrated under reduced pressure. The resulting residue was purified by silica gel column chromatography to give 3-(4-bromo-3-methyl-phenyl)-imidazolidine-2,4-dione (2.40 g, 37%).

MS (ESI) m/z=269, 271 (M+H)+.

The aryl bromide reagent used in the synthesis of Compound 505 (3-(4-bromo-3-methyl-phenyl)-1-methyl-imidazolidine-2,4-dione) was synthesized as follows.

(Reaction 96-2)

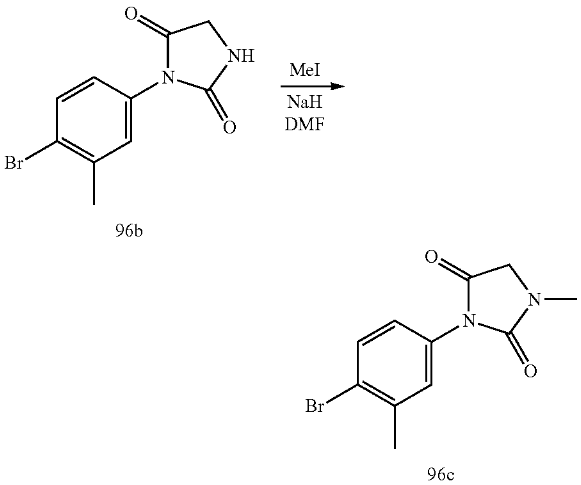

96b

96c (3-(4-Bromo-3-methyl-phenyl)-1-methyl-imidazolidine-2,4-dione was synthesized by operations similar to those in Reaction 25-3 using appropriate reagents and starting material.

MS (ESI) m/z=283, 285 (M+H)+.

The aryl bromide reagent used in the synthesis of Compound 506 (N-(4-bromo-3-isopropoxyphenyl)acetamide) was synthesized as follows.

(Reaction 96-3)

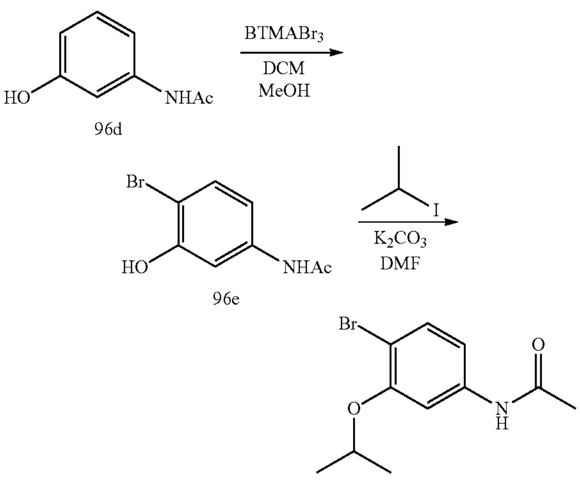

96d

96e

96f

N-(4-Bromo-3-isopropoxyphenyl)acetamide was synthesized by operations similar to those in Reaction 26-2 and Reaction 26-4 using appropriate reagents and starting material.

$^1$H-NMR ($CDCl_3$) δ 7.64 (d, 1H, J=2.29 Hz), 7.42 (d, 1H, J=8.39 Hz), 7.15 (brs, 1H), 6.72 (dd, 1H, J=8.39 Hz, J=2.29 Hz), 4.57 (m, 1H, J=6.1 Hz), 2.17 (s, 3H), 1.38 (d, 6H, J=6.1 Hz).

The aryl bromide reagents used in the synthesis of Compound 507 and Compound 508 (3-(4-bromo-3,5-dimethylphenyl)-5,5-dimethylimidazolidine-2,4-dione and 3-(4-bromo-3,5-dimethylphenyl)-1,5,5-trimethylimidazolidine-2,4-dione) were synthesized as follows.

(Reaction 96-4)

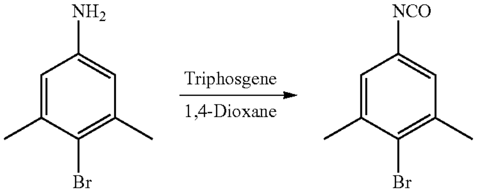

96g

96h

Triphosgene (2.23 g, 7.52 mmol) was added to a solution of 4-bromo-3,5-dimethyl-phenylamine (4.3 g, 21.49 mmol) in dioxane (71 ml). After stirring at 100° C. for 15 hours, water was added to the reaction solution. After extraction with ethyl acetate, the organic phase was sequentially washed with water and saturated brine and concentrated under reduced pressure to give 2-bromo-5-isocyanato-1,3-dimethylbenzene (2.0 g, 41%).

MS (ESI) m/z=226, 228 (M+H)+.

(Reaction 96-5)

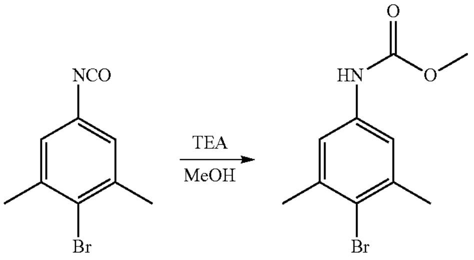

96h

96i

Triethylamine (1.8 ml, 13.27 mmol) was added dropwise to a solution of 2-bromo-5-isocyanato-1,3-dimethylbenzene (2.0 g, 8.84 mmol) in anhydrous methanol (30 ml) at 0° C. The reaction solution was gradually warmed to room temperature and stirred for one hour. The reaction solution was concentrated under reduced pressure, and the residue was diluted with ethyl acetate. The organic layer was then sequentially washed with water and saturated brine and concentrated under reduced pressure. The residue was purified by silica gel column chromatography (hexane-ethyl acetate) to give methyl (4-bromo-3,5-dimethylphenyl)carbamate (1.8 g, 79%).

MS (ESI) m/z=258, 260 (M+H)+.

(Reaction 96-6)

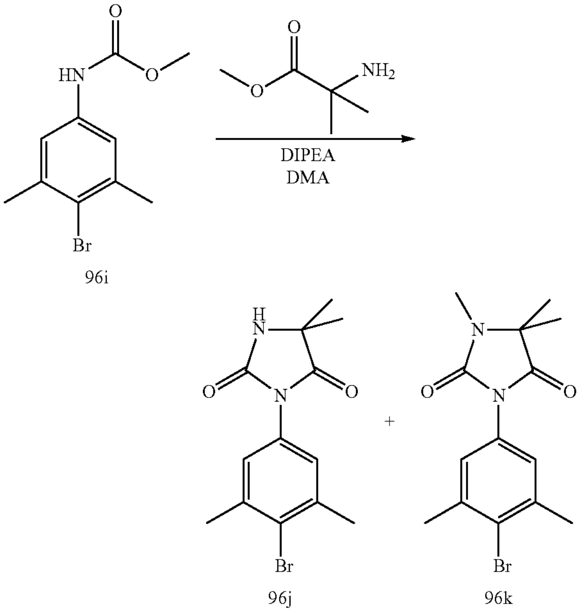

96i

96j

96k

α-Aminoisobutyric acid methyl ester (3.2 g, 20.92 mmol) and N,N-diisopropylethylamine (6.1 ml, 34.86 mmol) were added to a solution of methyl (4-bromo-3,5-dimethylphenyl) carbamate (900 mg, 3.48 mmol) in anhydrous DMA (17.5 ml, 0.2 M). After irradiation with microwaves at 170° C. for 30 minutes, water was added to the reaction solution, followed by extraction with ethyl acetate. The organic phase was sequentially washed with water and saturated brine and concentrated under reduced pressure. The residue was purified by silica gel column chromatography (hexane-ethyl acetate) to give 3-(4-bromo-3,5-dimethylphenyl)-5,5-dimethylimidazolidine-2,4-dione (304 mg, 28%)

MS (ESI) m/z=311, 313 (M+H)+ and 3-(4-bromo-3,5-dimethylphenyl)-1,5,5-trimethylimidazolidine-2,4-dione (245 mg, 23%).

MS (ESI) m/z=325, 327 (M+H)+

The aryl bromide reagent used in the synthesis of Compound 509 (N-(4-bromo-3-ethoxyphenyl)acetamide) was synthesized as follows.

(Reaction 96-7)

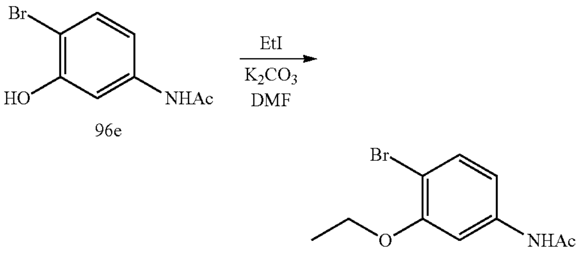

96e

96l

N-(4-Bromo-3-ethoxyphenyl)acetamide was synthesized by operations similar to those in Reaction 26-4 using appropriate reagents and starting material.

$^1$H-NMR ($CDCl_3$) δ 7.48 (d, 1H, J=2.29 Hz), 7.42 (d, 1H, J=8.39 Hz), 7.22 (brs, 1H), 6.72 (dd, 1H, J=8.39 Hz, J=2.29 Hz), 4.10 (q, 2H, J=6.87 Hz), 2.17 (s, 3H), 1.46 (t, 3H, J=6.87 Hz).

The aryl bromide reagent used in the synthesis of Compound 510 (N-(4-bromo-3-ethylphenyl)acetamide) was synthesized as follows.

(Reaction 96-8)

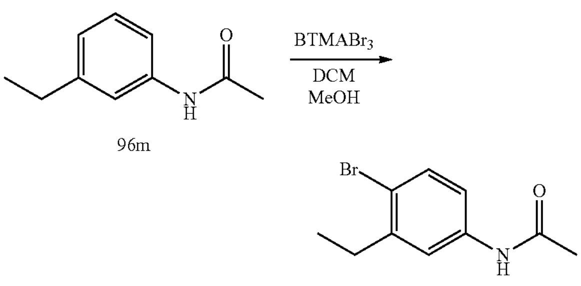

96m

96n

N-(4-Bromo-3-ethylphenyl)acetamide was synthesized by operations similar to those in Reaction 26-2 using appropriate reagents and starting material.

$^1$H-NMR ($CDCl_3$) δ 7.44 (d, 1H, J=8.39 Hz), 7.39 (d, 1H, J=2.29 Hz), 7.23 (dd, 1H, J=8.39 Hz, J=2.29 Hz), 7.17 (brs, 1H), 2.72 (q, 2H, J=7.25 Hz), 2.17 (s, 3H), 1.21 (t, 3H, J=7.25 Hz).

The aryl bromide reagent used in the synthesis of Compound 511 (3-(4-bromo-3-methyl-phenyl)-5,5-dimethyl-imidazolidine-2,4-dione) was synthesized as follows.

(Reaction 96-9)

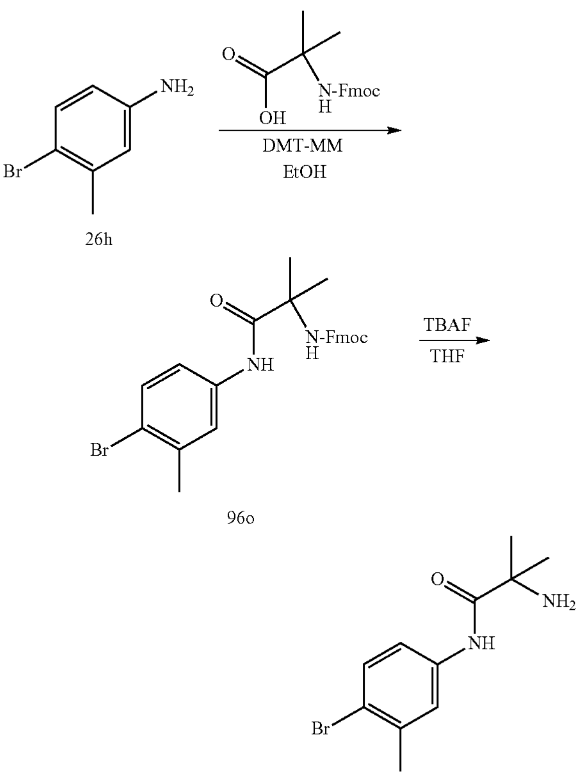

26h

96o

96p

2-Amino-N-(4-bromo-3-methyl-phenyl)-2-methyl-propionamide was synthesized by operations similar to those in Reaction 10-1 and Reaction 39-2 using appropriate reagents and starting material.

$^1$H-NMR ($CDCl_3$) δ 1.46 (6H, s), 2.37 (3H, s), 7.29 (1H, dd, J=8.8, 2.4 Hz), 7.44 (1H, d, J=8.8 Hz), 7.59 (1H, d, J=2.4 Hz), 9.84 (1H, br s).

(Reaction 96-10)

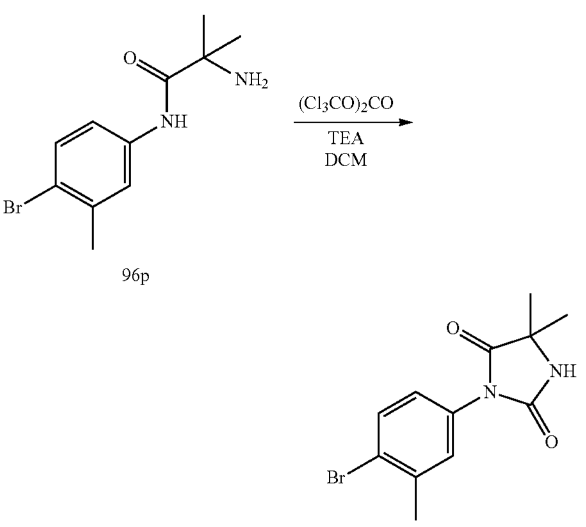

96p

96q

Bis(trichloromethyl) carbonate (50.6 mg, 0.171 mmol) was added to a solution of 2-amino-N-(4-bromo-3-methyl-phenyl)-2-methyl-propionamide (132 mg, 0.487 mmol) and triethylamine (0.204 ml, 1.46 mmol) in dichloromethane (5.0 ml) at 0° C., and the mixture was stirred for 21 hours while gradually warming to room temperature. An aqueous ammonium chloride solution was added to the reaction mixture, followed by extraction with dichloromethane. The resulting residue was purified by silica gel column chromatography (dichloromethane-ethyl acetate) to give 3-(4-bromo-3-methyl-phenyl)-5,5-dimethyl-imidazolidine-2,4-dione (146 mg, 88%).

MS (ESI) m/z=297, 299 (M+H)+.

The aryl bromide reagent used in the synthesis of Compound 512 (N-(4-bromo-3-methoxymethyl-phenyl)-acetamide) was synthesized as follows.

(Reaction 96-11)

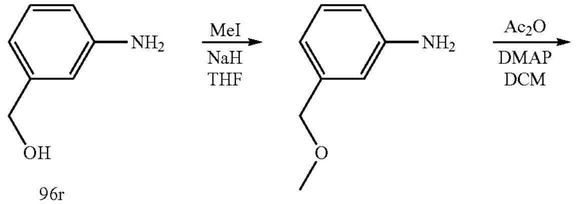

96r

96s

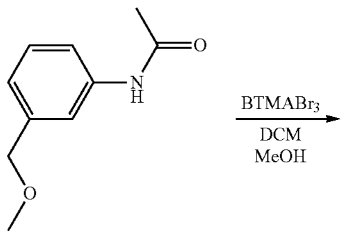

96t

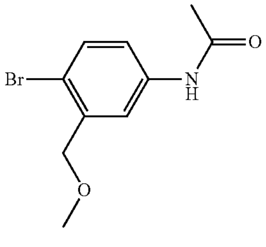

96u

N-(4-Bromo-3-methoxymethyl-phenyl)-acetamide was synthesized by operations similar to those in Reaction 20-2, Reaction 19-2 and Reaction 26-2 using appropriate reagents and starting material.

$^1$H-NMR ($CDCl_3$) δ 7.12 (t, 1H, J=7.8 Hz), 6.70 (m, 2H), 6.60 (dd, 1H, J=7.5 Hz, 2.1 Hz), 4.42 (s, 2H), 3.53 (s, 3H), 2.08 (s, 3H).

The aryl bromide reagent used in the synthesis of Compound 513 (3-(4-bromo-3-methyl-phenyl)-oxazolidin-2-one) was synthesized as follows.

(Reaction 96-12)

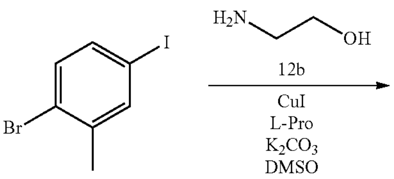

12a

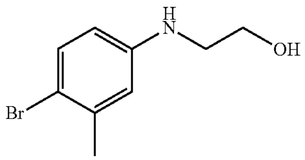

12c 2-(4-Bromo-3-methyl-phenylamino)-ethanol was synthesized by operations similar to those in Reaction 12-1 using appropriate reagents and starting material.

MS (ESI) m/z=230, 232 (M+H)+.

(Reaction 96-13)

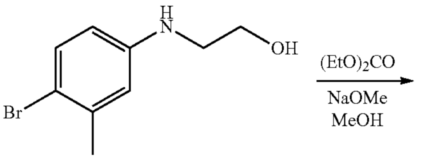

12c

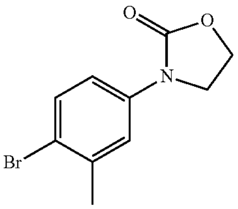

96v

Diethyl carbonate (18 ml) and a 28% solution of sodium methoxide in methanol (1.1 ml, 5.70 mmol) were added to 2-(4-bromo-3-methyl-phenylamino)-ethanol (1.21 g, 5.27 mmol), and the mixture was heated with stirring at 110° C. for 15 hours. Further, methanol (16 ml) was added to the reaction solution, and the mixture was heated with stirring at 110° C. for one hour. An aqueous ammonium chloride solution was added to the reaction mixture, followed by extraction with ethyl acetate. The organic phase was sequentially washed with water and saturated brine and concentrated under reduced pressure. The resulting residue was triturated with hexane to give 3-(4-bromo-3-methyl-phenyl)-oxazolidin-2-one (989 mg, 73%).

MS (ESI) m/z=256, 258 (M+H)+.

The aryl bromide reagent used in the synthesis of Compound 514 (N-(4-bromo-3,5-dimethyl-phenyl)-N-(2-methoxy-ethyl)-acetamide) was synthesized as follows.

(Reaction 96-14)

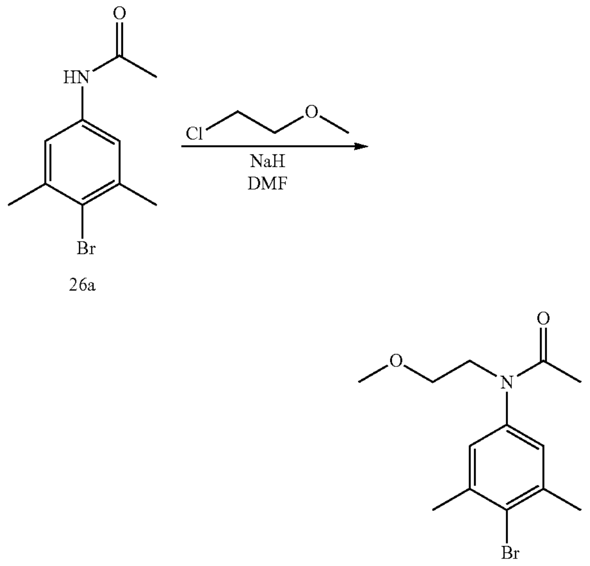

26a

96w

N-(4-Bromo-3,5-dimethyl-phenyl)-N-(2-methoxy-ethyl)-acetamide was synthesized by operations similar to those in Reaction 25-3 using appropriate reagents and starting material.

MS (ESI) m/z=300, 302 (M+H)+.

The aryl bromide reagent used in the synthesis of Compound 515 (4-(4-bromo-3,5-dimethyl-phenyl)-morpholin-3-one) was synthesized as follows.

(Reaction 96-15)

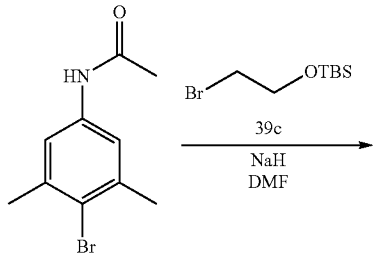

26a

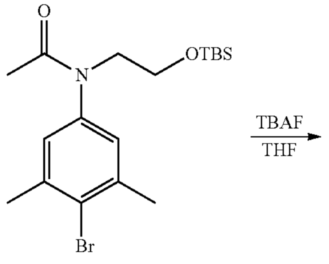

96x

-continued

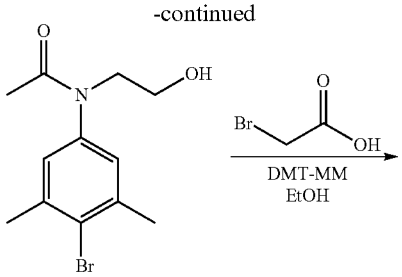

96y

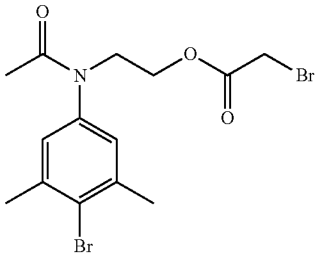

96z

Bromo-acetic acid 2-[acetyl-(4-bromo-3,5-dimethyl-phenyl)-amino]-ethyl ester was synthesized by operations similar to those in Reaction 25-3, Reaction 39-2 and Reaction 10-1 using appropriate reagents and starting material.

$^1$H-NMR ($CDCl_3$) δ 6.95 (s, 2H), 4.04 (s, 2H), 3.86-3.74 (m, 4H), 2.43 (s, 6H), 1.89 (s, 3H).

(Reaction 96-16)

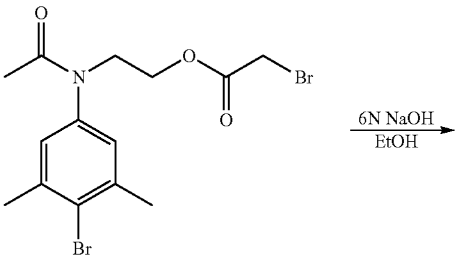

96z

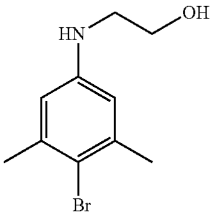

96aa

6 N NaOH (1.5 ml) was added to a solution of bromo-acetic acid 2-[acetyl-(4-bromo-3,5-dimethyl-phenyl)-amino]-ethyl ester (302 mg, 0.74 mmol) in EtOH (6 ml). The reaction solution was heated under reflux overnight, cooled to room temperature and then diluted with ethyl acetate. The organic phase was sequentially washed with water and saturated brine and concentrated under reduced pressure. The resulting residue was purified by silica gel column chromatography (hexane-ethyl acetate) to give 2-(4-bromo-3,5-dimethyl-phenylamino)-ethanol (181 mg, 68%).

$^1$H-NMR ($CDCl_3$) δ 6.41 (s, 2H), 3.82 (t, 2H, J=5.1 Hz), 3.27 (t, 2H, J=5.1 Hz), 2.34 (s, 6H).

(Reaction 96-17)

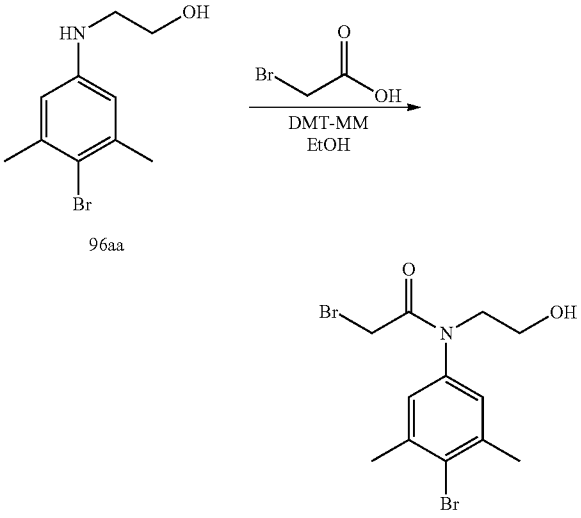

96aa

96ab

2-Bromo-N-(4-bromo-3,5-dimethyl-phenyl)-N-(2-hydroxy-ethyl)acetamide was synthesized by operations similar to those in Reaction 10-1 using appropriate reagents and starting material.

$^1$H-NMR ($CDCl_3$) δ 7.01 (s, 2H), 3.89-3.78 (m, 6H), 2.44 (s, 6H).

(Reaction 96-18)

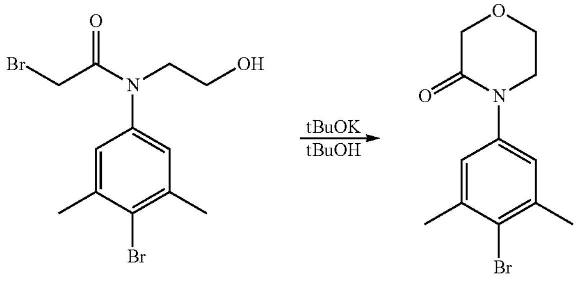

96ab

96ac

Potassium t-butoxide (53 mg, 0.44 mmol) was added to a solution of 2-bromo-N-(4-bromo-3,5-dimethyl-phenyl)-N-(2-hydroxy-ethyl)-acetamide (147 mg, 0.40 mmol) in t-BuOH (2 ml), and the mixture was heated under reflux overnight. The reaction solution was cooled to room temperature and water was then added, followed by extraction with ethyl acetate. The organic phase was washed with saturated brine and then concentrated under reduced pressure. The resulting residue was purified by silica gel column chromatography (hexane-ethyl acetate) to give 4-(4-bromo-3,5-dimethyl-phenyl)-morpholin-3-one (100%).

$^1$H-NMR ($CDCl_3$) δ 7.05 (s, 2H), 4.33 (s, 2H), 4.02 (t, 2H, J=5.0 Hz), 3.72 (t, 2H, J=5.0 Hz), 2.42 (s, 6H).

The aryl bromide reagent used in the synthesis of Compound 516 (1-(4-bromo-3,5-dimethylphenyl)piperidin-2-one) was synthesized as follows.

(Reaction 96-19)

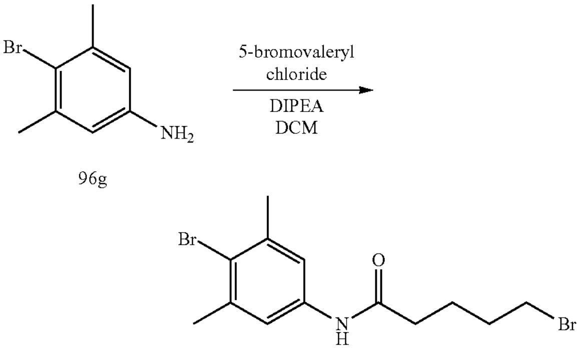

96g

96ad

5-Bromo-pentanoic (4-bromo-3,5-dimethyl-phenyl)-amide was synthesized by operations similar to those in Reaction 2-3 using appropriate reagents and starting material.

$^1$H-NMR ($CDCl_3$) δ 7.25 (s, 2H), 7.19 (brs, 1H), 3.43 (t, 2H, J=6.49 Hz), 2.37 (t, 2H, J=6.87 Hz), 2.37 (s, 6H), 1.9 (m, 4H).

(Reaction 96-20)

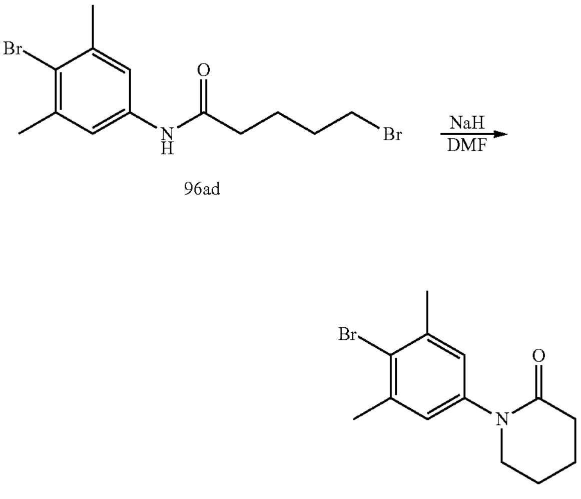

96ad

96ae

Sodium hydride (37 mg, 0.925 mmol) was added to a solution of 5-bromo-pentanoic (4-bromo-3,5-dimethyl-phenyl-amide (320 mg, 0.881 mmol) in DMF (8 ml) at 0° C., and the mixture was stirred at room temperature for two days. The reaction solution was diluted with ethyl acetate, and the organic layer was sequentially washed with water and saturated brine and concentrated under reduced pressure. The resulting residue was purified by silica gel column chromatography (dichloromethane-ethyl acetate) to give 1-(4-bromo-3,5-dimethylphenyl)piperidin-2-one (240 mg, 97%).

$^1$H-NMR ($CDCl_3$) δ 6.97 (s, 2H), 3.58 (t, 2H, J=6.87 Hz), 2.55 (t, 2H, J=6.87 Hz), 2.40 (s, 6H), 1.93 (m, 4H).

The aryl bromide reagent used in the synthesis of Compound 517 (N-(4-bromo-3,5-dimethyl-benzyl)-N-methyl-acetamide) was synthesized as follows.

(Reaction 96-21)

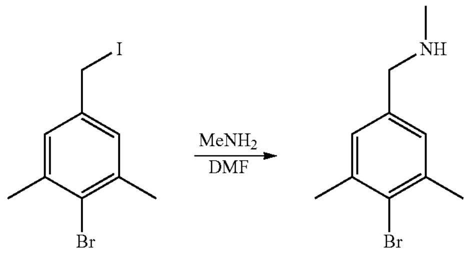

96af 96ag

Methylamine (12.3 ml, 24.60 mmol, 2.0 M solution in methanol) was added dropwise to a solution of 2-bromo-5-iodomethyl-1,3-dimethyl-benzene (400 mg, 1.23 mmol) in anhydrous DMF (12 ml), and the mixture was stirred at room temperature for two days. The reaction solution was concentrated under reduced pressure, and the residue was diluted with ethyl acetate. The organic layer was then sequentially washed with water and saturated brine and concentrated under reduced pressure. The resulting residue was purified by silica gel column chromatography (dichloromethane-methanol) to give 1-(4-bromo-3,5-dimethylphenyl)-N-methyl-methanamine (280 mg, 100%).

MS (ESI) m/z=228, 230 (M+H)+.

(Reaction 96-22)

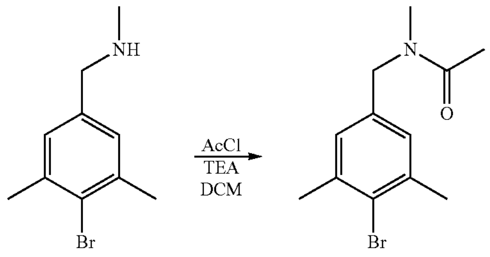

96ag 96ah

N-(4-Bromo-3,5-dimethyl-benzyl)-N-methyl-acetamide was synthesized by operations similar to those in Reaction 2-3 using appropriate reagents and starting material.

MS (ESI) m/z=270, 272 (M+H)+.

The aryl bromide reagent used in the synthesis of Compound 518 (3-(4-bromo-3,5-dimethyl-benzyl)-imidazolidine-2,4-dione) was synthesized as follows.

(Reaction 96-23)

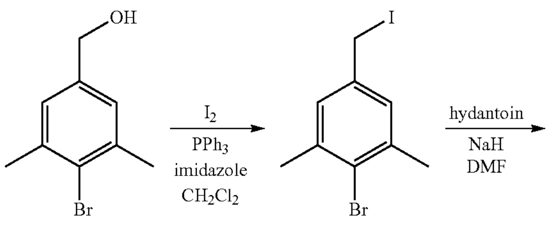

96ai 96af

-continued

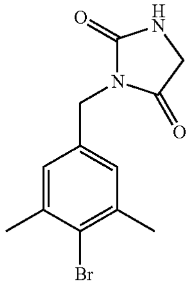

96aj 3-(4-Bromo-3,5-dimethyl-benzyl)-imidazolidine-2,4-dione was synthesized by operations similar to those in Reaction 52-1 (using iodine as a reagent) and Reaction 25-3 using appropriate reagents and starting material.

$^{1}$H-NMR ($CDCl_3$) δ 7.10 (s, 2H), 5.63 (s, 1H), 4.55 (s, 2H), 3.97 (d, 2H, J=1.14 Hz), 2.38 (s, 6H).

The aryl bromide reagent used in the synthesis of Compound 519 (3-(4-bromo-3,5-dimethyl-benzyl)-5,5-dimethyl-imidazolidine-2,4-dione) was synthesized as follows.

(Reaction 96-24)

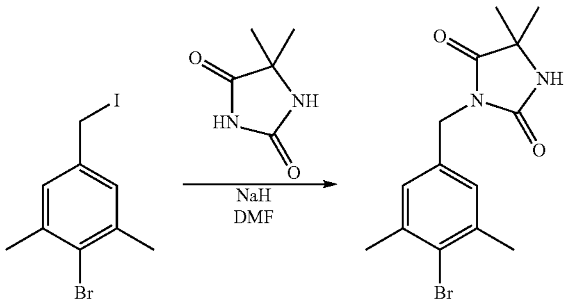

96af 96ak 3-(4-Bromo-3,5-dimethyl-benzyl)-5,5-dimethyl-imidazolidine-2,4-dione was synthesized by operations similar to those in Reaction 25-3 using appropriate reagents and starting material.

MS (ESI) m/z=325, 327 (M+H)+.

The aryl bromide reagent used in the synthesis of Compound 520 (1-(4-bromo-3,5-dimethyl-benzyl)-pyrrolidin-2-one) was synthesized as follows.

(Reaction 96-25)

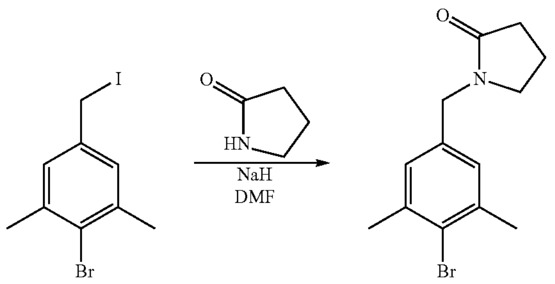

96af 96al 1-(4-Bromo-3,5-dimethyl-benzyl)-pyrrolidin-2-one was synthesized by operations similar to those in Reaction 25-3 using appropriate reagents and starting material.

$^{1}$H-NMR ($CDCl_3$) δ 6.94 (s, 2H), 4.33 (s, 2H), 3.25 (t, 2H, J=7.24 Hz), 2.44 (t, 2H, J=8.01 Hz), 2.38 (s, 6H), 2.04-1.93 (m, 2H).

The aryl bromide reagent used in the synthesis of Compound 521 (1-(4-bromo-3,5-dimethyl-benzyl)-pyrrolidine-2,5-dione) was synthesized as follows.

(Reaction 96-26)

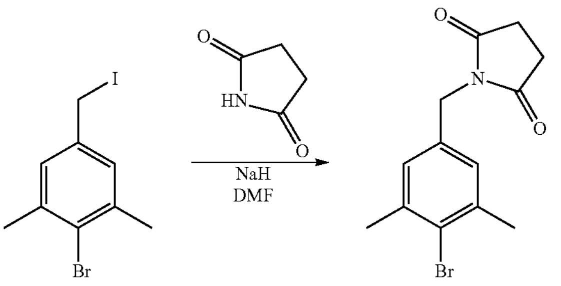

96af 96am 1-(4-Bromo-3,5-dimethyl-benzyl)-pyrrolidine-2,5-dione was synthesized by operations similar to those in Reaction 25-3 using appropriate reagents and starting material.

$^1$H-NMR ($CDCl_3$) δ 7.09 (s, 2H), 4.54 (s, 2H), 2.70 (s, 4H), 2.37 (s, 6H).

The aryl bromide reagent used in the synthesis of Compound 522 (N-(4-bromo-3,5-dimethyl-benzyl)-acetamide) was synthesized as follows.

(Reaction 96-27)

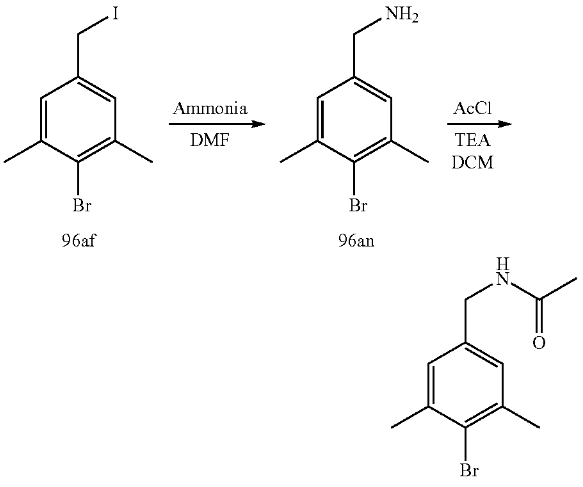

96af 96an 96ao

N-(4-Bromo-3,5-dimethyl-benzyl)-acetamide was synthesized by operations similar to those in Reaction 96-21 and Reaction 2-3 using appropriate reagents and starting material.

MS (ESI) m/z=256, 258 (M+H)+.

The aryl bromide reagent used in the synthesis of Compound 523 (N-(4-bromo-3,5-difluoro-phenyl)-N-methyl-acetamide) was synthesized as follows.

(Reaction 96-28)

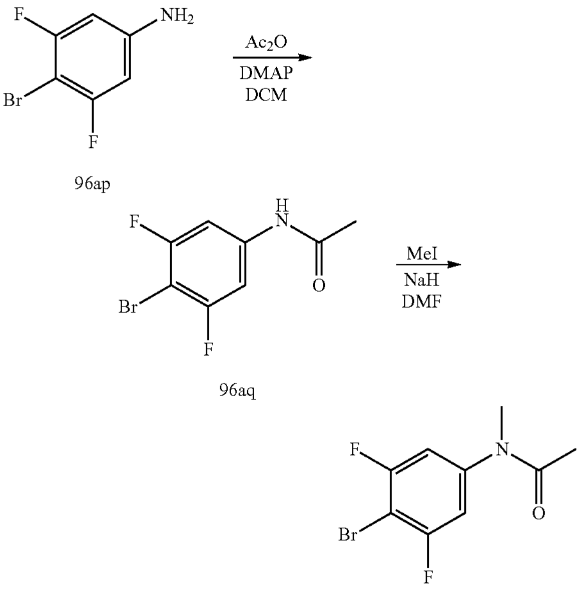

96ap 96aq 96ar

N-(4-Bromo-3,5-difluoro-phenyl)-N-methyl-acetamide was synthesized by operations similar to those in Reaction 19-2 and Reaction 25-3 using appropriate reagents and starting material.

MS (ESI) m/z=264, 266 (M+H)+.

Example 97

The example compounds shown below were obtained by operations similar to those in Reaction 25-2 using appropriate reagents and starting materials.

Compounds 524 to 525

TABLE 72

| Target Compound | Structure | LCMS condition | Retention time (min) | MS (m/z) |
|---|---|---|---|---|
| 524 | 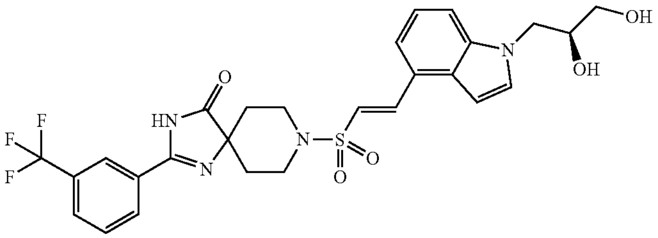 [SMILES: O=C1NC(c2cccc(C(F)(F)F)c2)=NC12CCN(S(=O)(=O)/C=C/c1cccc3c1ccn3C[C@H](O)CO)CC2] | LCMS-B-1 | 2.03 | 577 (M + H)+ |

TABLE 72-continued

| Target Compound | Structure | LCMS condition | Retention time (min) | MS (m/z) |
|---|---|---|---|---|
| 525 | 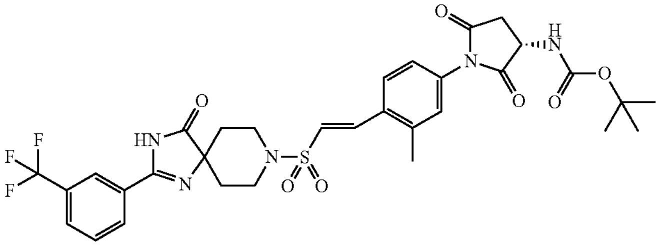 [SMILES: Cc1cc(N2C(=O)C[C@H](NC(=O)OC(C)(C)C)C2=O)ccc1/C=C/S(=O)(=O)N1CCC2(CC1)N=C(c1cccc(C(F)(F)F)c1)NC2=O] | LCMS-F-1 | 0.98 | 690 (M + H)+ |

The aryl bromide reagent used in the synthesis of Compound 525 ([(S)-1-(4-bromo-3-methyl-phenylcarbamoyl)-2-carbamoyl-ethyl]-carbamic acid tert-butyl ester) was synthesized as follows.

(Reaction 97-1)

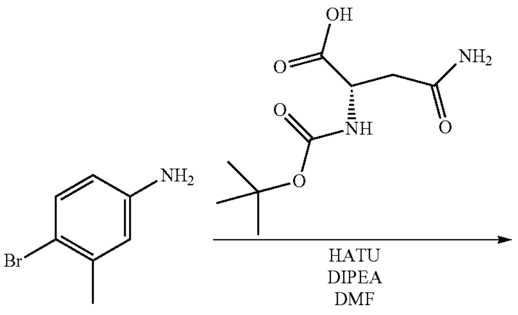

26h

-continued

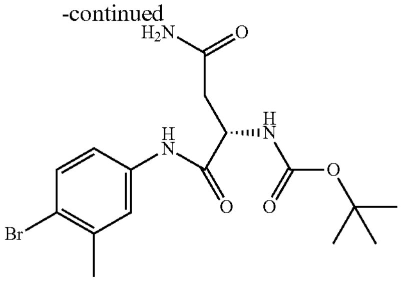

97a

[(S)-1-(4-Bromo-3-methyl-phenylcarbamoyl)-2-carbamoyl-ethyl]-carbamic acid tert-butyl ester was synthesized by operations similar to those in Reaction 10-14 using appropriate reagents and starting material.

MS (ESI) m/z=400 (M+H)+.

Example 98

The example compounds shown below were obtained by operations similar to those in Reaction 25-2 using appropriate reagents and starting materials.

Compounds 526 to 534

TABLE 73

| Target Compound | Structure | LCMS condition | Retention time (min) | MS (m/z) |
|---|---|---|---|---|
| 526 | 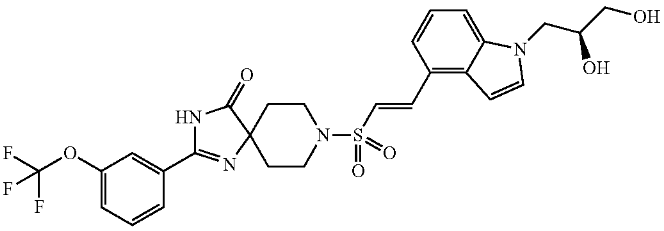 [SMILES: O=C1NC(c2cccc(OC(F)(F)F)c2)=NC12CCN(S(=O)(=O)/C=C/c1cccc3c1ccn3C[C@H](O)CO)CC2] | LCMS-B-1 | 2.5 | 593 (M + H)+ |

TABLE 73-continued
| Target Compound | Structure | LCMS condition | Retention time (min) | MS (m/z) |
|---|---|---|---|---|
| 527 | 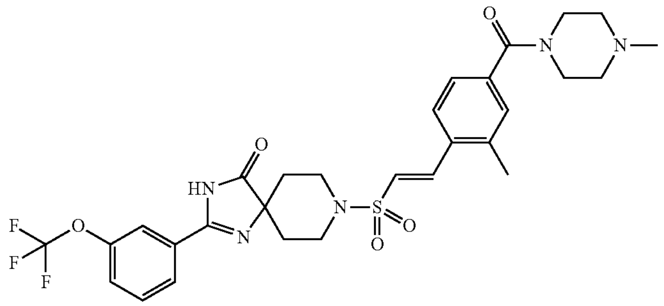 | LCMS-C-1 | 2.6 | 620 (M + H)+ |
| 528 | 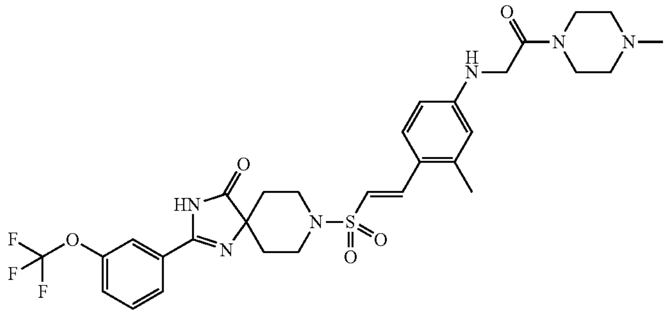 [SMILES: Cc1cc(NCC(=O)N2CCN(C)CC2)ccc1/C=C/S(=O)(=O)N1CCC2(CC1)N=C(c1cccc(OC(F)(F)F)c1)NC2=O] | LCMS-C-1 | 2.65 | 649 (M + H)+ |
| 529 | 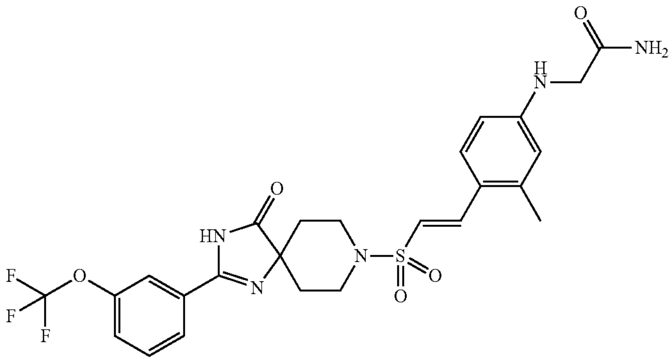 [SMILES: Cc1cc(NCC(N)=O)ccc1/C=C/S(=O)(=O)N1CCC2(CC1)N=C(c1cccc(OC(F)(F)F)c1)NC2=O] | LCMS-C-1 | 2.45 | 566 (M + H)+ |
| 530 | 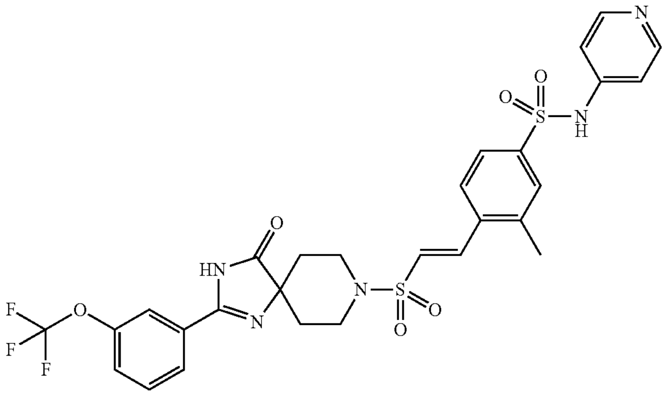 [SMILES: Cc1cc(S(=O)(=O)Nc2ccncc2)ccc1/C=C/S(=O)(=O)N1CCC2(CC1)N=C(c1cccc(OC(F)(F)F)c1)NC2=O] | LCMS-C-1 | 2.38 | 650 (M + H)+ |

TABLE 73-continued

| Target Compound | Structure | LCMS condition | Retention time (min) | MS (m/z) |
|---|---|---|---|---|
| 531 | 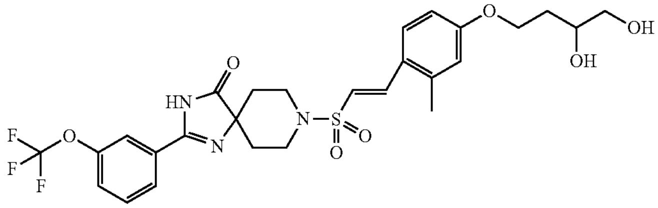 [SMILES: Cc1cc(OCCC(O)CO)ccc1/C=C/S(=O)(=O)N1CCC2(CC1)N=C(c1cccc(OC(F)(F)F)c1)NC2=O] | LCMS-C-1 | 2.63 | 598 (M + H)+ |
| 532 | 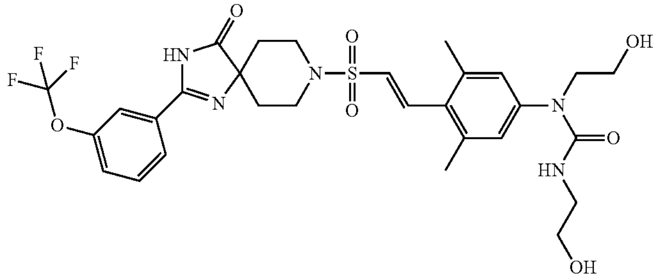 [SMILES: Cc1cc(N(CCO)C(=O)NCCO)cc(C)c1/C=C/S(=O)(=O)N1CCC2(CC1)N=C(c1cccc(OC(F)(F)F)c1)NC2=O] | LCMS-D-1 | 2.16 | 654 (M + H)+ |
| 533 | 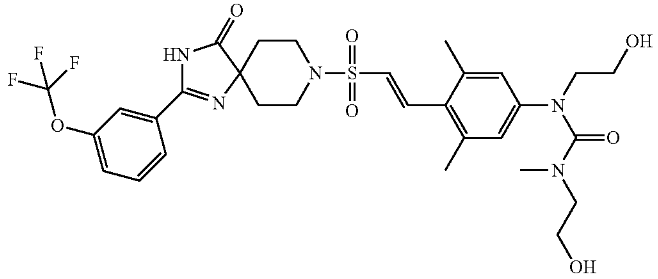 [SMILES: Cc1cc(N(CCO)C(=O)N(C)CCO)cc(C)c1/C=C/S(=O)(=O)N1CCC2(CC1)N=C(c1cccc(OC(F)(F)F)c1)NC2=O] | LCMS-D-1 | 2.35 | 668 (M + H)+ |
| 534 | 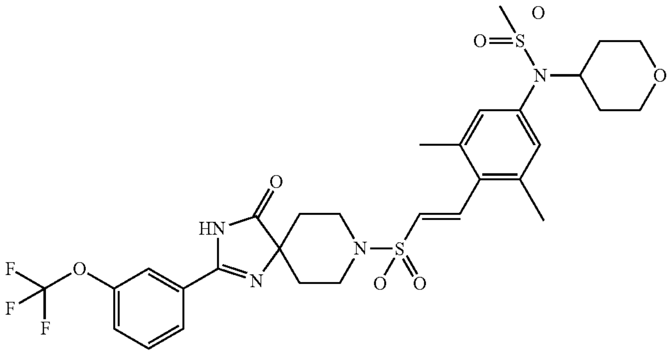 | LCMS-D-1 | 3.1 | 685 (M + H)+ |

The aryl bromide reagent used in the synthesis of Compound 528 (2-(4-bromo-3-methyl-phenylamino)-1-(4-methyl-piperazin-1-yl)-ethanone) was synthesized as follows.

(Reaction 98-1)

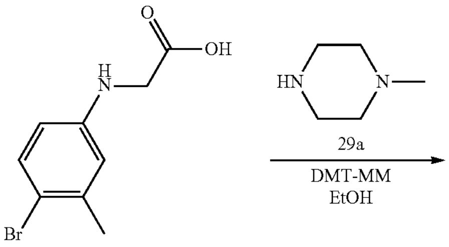

98a

-continued

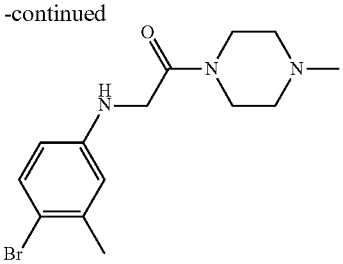

98b 2-(4-Bromo-3-methyl-phenylamino)-1-(4-methyl-piperazin-1-yl)-ethanone was synthesized by operations similar to those in Reaction 10-1 using appropriate reagents and starting material.

MS (ESI) m/z=326 (M+H)+.

The aryl bromide reagent used in the synthesis of Compound 529 (2-(4-bromo-3-methyl-phenylamino)-acetamide) was synthesized as follows.

(Reaction 98-2)

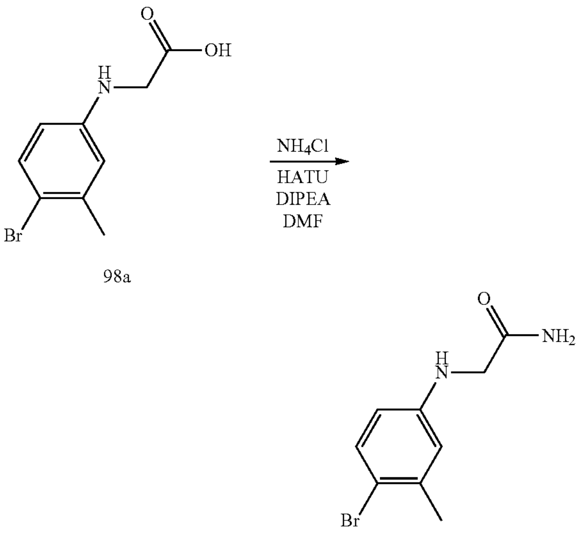

98a

98c 2-(4-Bromo-3-methyl-phenylamino)-acetamide was synthesized by operations similar to those in Reaction 10-14 using appropriate reagents and starting material.

MS (ESI) m/z=243 (M+H)+.

The aryl bromide reagent used in the synthesis of Compound 530 (4-bromo-3-methyl-N-pyridin-4-yl-benzenesulfonamide) was synthesized as follows.

(Reaction 98-3)

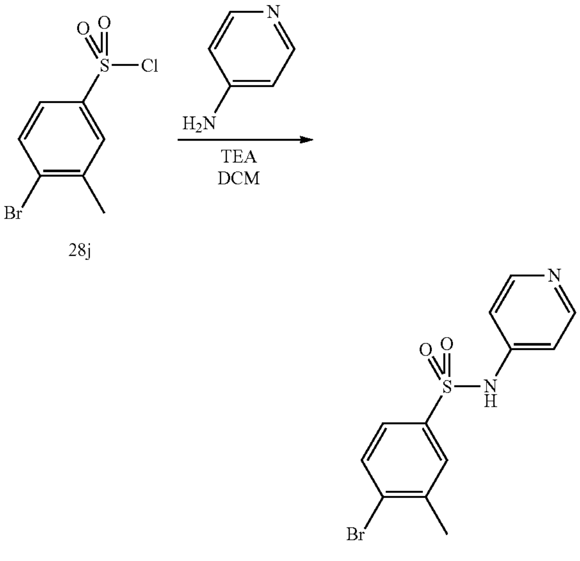

28j

98d

4-Bromo-3-methyl-N-pyridin-4-yl-benzenesulfonamide was synthesized by operations similar to those in Reaction 5-4 using appropriate reagents and starting material.

MS (ESI) m/z=327 (M+H)+.

The aryl bromide reagent used in the synthesis of Compound 532 (1-(4-bromo-3,5-dimethylphenyl)-1,3-bis(2-hydroxyethyl)urea) was synthesized as follows.

(Reaction 98-4)

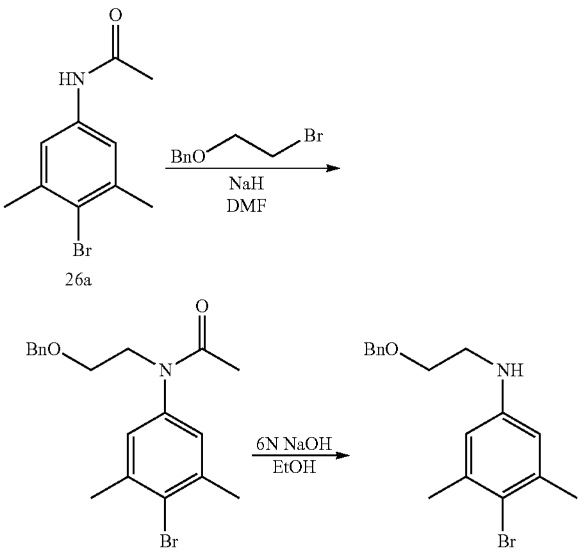

26a

98e

98f

N-(2-(Benzyloxy)ethyl)-4-bromo-3,5-dimethylaniline was synthesized by operations similar to those in Reaction 25-3 and Reaction 96-16 using appropriate reagents and starting material.

$^1$H-NMR (300 MHz, $CDCl_3$) δ 2.32 (s, 6H), 3.27 (t, J=5.39 Hz, 2H), 3.68 (t, J=5.37 Hz, 2H), 3.95 (brs, 1H), 4.54 (s, 2H), 6.37 (s, 2H), 7.25-7.38 (m, 5H).

(Reaction 98-5)

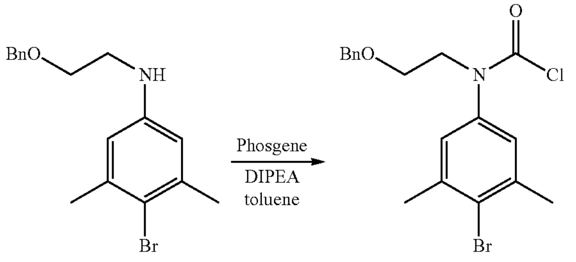

98f

98g

Phosgene (3.5 ml, 6.64 mmol, 20% solution in toluene) and N,N-diisopropylethylamine (1.2 ml, 6.64 mmol) were added to a solution of N-(2-(benzyloxy)ethyl)-4-bromo-3,5-dimethylaniline (740 mg, 2.21 mmol) in anhydrous toluene (11 ml) at 0° C. The reaction solution was gradually warmed to room temperature and stirred at the same temperature for three hours. Water was added to the reaction mixture, followed by extraction with ethyl acetate. The organic phase was sequentially washed with water and saturated brine and concentrated under reduced pressure. The resulting residue was purified by silica gel column chromatography (dichloromethane) to give N-(2-(benzyloxy)ethyl)-N-(4-bromo-3,5-dimethylphenyl)carbamic acid chloride (860 mg, 98%).

$^1$H-NMR (300 MHz, $CDCl_3$) δ 2.36 (s, 6H), 3.67 (t, J=5.42 Hz, 2H), 3.89 (t, J=4.95 Hz, 2H), 4.50 (s, 2H), 6.95 (s, 2H), 7.27-7.38 (m, 5H).

(Reaction 98-6)

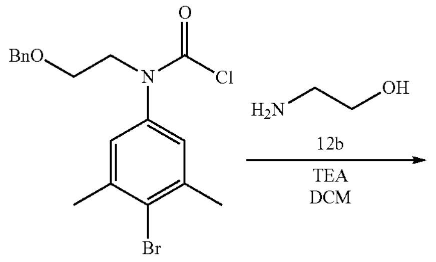

98g

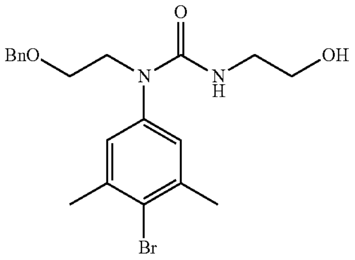

98h 1-(2-(Benzyloxy)ethyl)-1-(4-bromo-3,5-dimethylphenyl)-3-(2-hydroxyethyl)urea was synthesized by operations similar to those in Reaction 82-1 using appropriate reagents and starting material.

MS (ESI) m/z=421, 423 (M+H)+.

(Reaction 98-7)

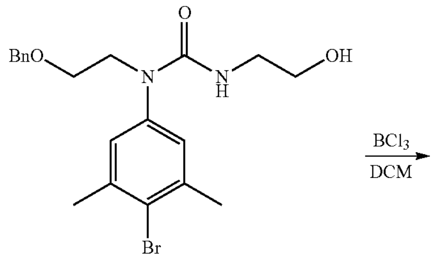

98h

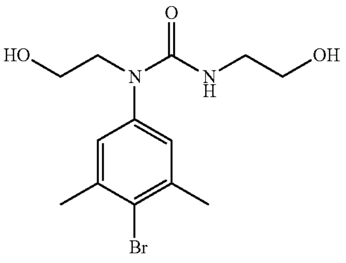

98i

Boron trichloride (0.93 ml, 0.93 mmol, 1.0 M solution in dichloromethane) was added to a solution of 1-(2-(benzyloxy)ethyl)-1-(4-bromo-3,5-dimethylphenyl)-3-(2-hydroxyethyl)urea (98 mg, 0.23 mmol) in anhydrous dichloromethane (4.6 ml) at −78° C., and the mixture was stirred at the same temperature for two hours. A saturated aqueous sodium bicarbonate solution was added to the reaction mixture, followed by extraction with ethyl acetate. The organic phase was sequentially washed with water and saturated brine and concentrated under reduced pressure. The resulting residue was purified by silica gel column chromatography (dichloromethane-methanol) to give 1-(4-bromo-3,5-dimethylphenyl)-1,3-bis(2-hydroxyethyl)urea (64 mg, 83%).

$^1$H-NMR (300 MHz, $CDCl_3$) δ 2.43 (s, 6H), 2.94 (t, J=5.11 Hz, 1H), 3.33 (q, J=5.23 Hz, 2H), 3.60 (t, J=4.78 Hz, 1H), 3.66 (q, J=4.91 Hz, 2H), 3.71-3.81 (m, 4H), 4.73 (brs, 1H), 7.01 (s, 2H).

The aryl bromide reagent used in the synthesis of Compound 533 (1-(4-bromo-3,5-dimethyl-phenyl)-1,3-bis-(2-hydroxy-ethyl)-3-methyl-urea) was synthesized as follows.

(Reaction 98-8)

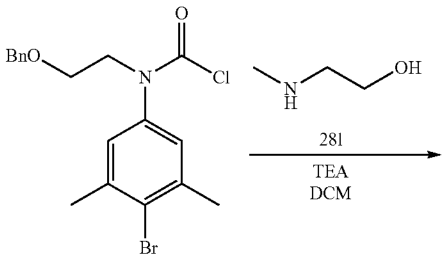

98g

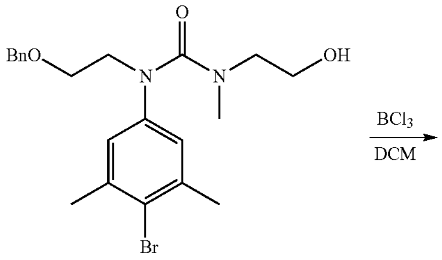

98j

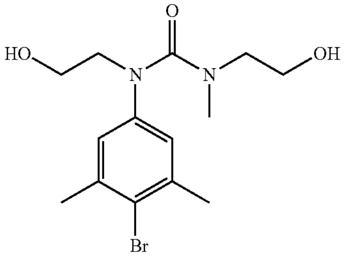

98k 1-(4-Bromo-3,5-dimethyl-phenyl)-1,3-bis-(2-hydroxy-ethyl)-3-methyl-urea was synthesized by operations similar to those in Reaction 82-1 and Reaction 98-7 using appropriate reagents and starting material.

MS (ESI) m/z=345, 347 (M+H)+.-

The aryl bromide reagent used in the synthesis of Compound 534 (N-(4-bromo-3,5-dimethyl-phenyl)-N-(tetrahydro-pyran-4-yl)-methanesulfonamide) was synthesized as follows.

(Reaction 98-9)

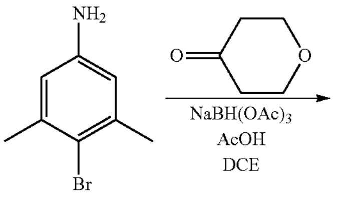

96g

-continued

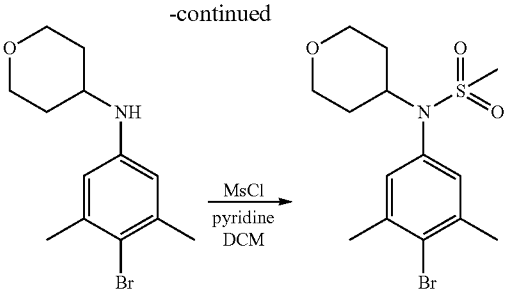

981 98m

N-(4-Bromo-3,5-dimethyl-phenyl)-N-(tetrahydro-pyran-4-yl)-methanesulfonamide was synthesized by operations similar to those in Reaction 41-1 and Reaction 6-1 using appropriate reagents and starting material.

MS (ESI) m/z=362, 364 (M+H)+.

Example 99

The example compound shown below was obtained by operations similar to those in Reaction 25-2 using appropriate reagents and starting material.

Compound 535

TABLE 74

| Target Compound | Structure | LCMS condition | Retention time (min) | MS (m/z) |
|---|---|---|---|---|
| 535 | 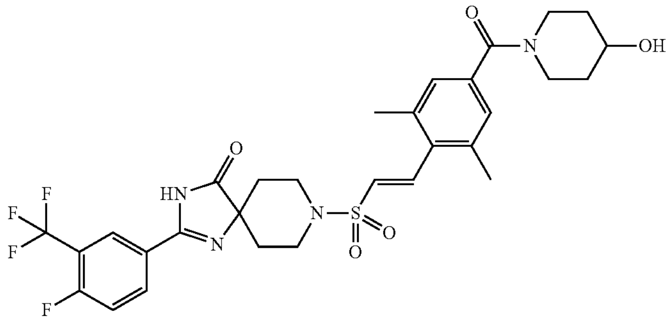 [SMILES: Cc1cc(C(=O)N2CCC(O)CC2)cc(C)c1/C=C/S(=O)(=O)N1CCC2(CC1)N=C(c1ccc(F)c(C(F)(F)F)c1)NC2=O] | LCMS-C-1 | 2.52 | 637 (M + H)+ |

Example 100

3-{3-Methyl-4-[(E)-2-(2-nonyl-4-oxo-1,3,8-triaza-spiro[4.5]dec-1-ene-8-sulfonyl)-vinyl]-phenyl}-imidazolidine-2,4-dione (Compound 536)

(Reaction 100-1)

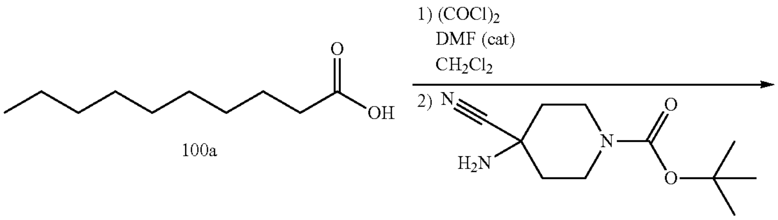

100a

5a

Et3N, CH2Cl2

-continued
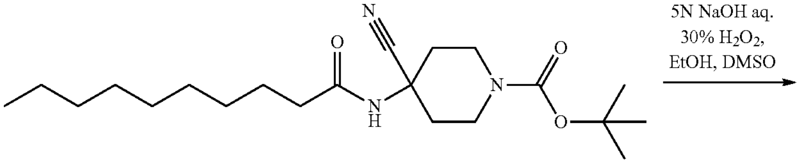
100b
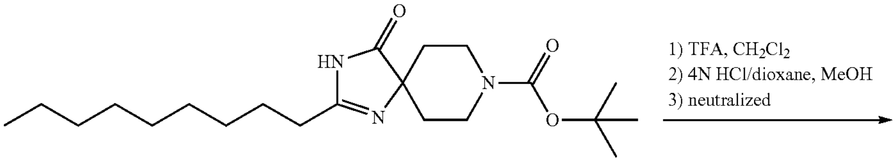
100c
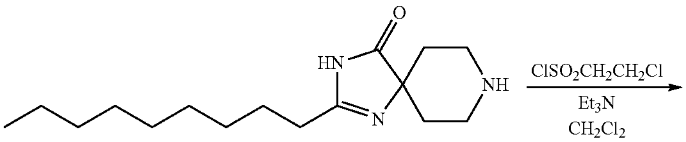
100d
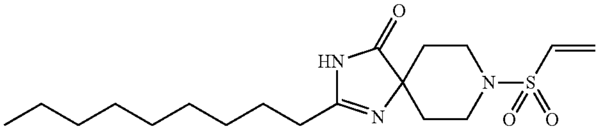
100e
8-Ethenesulfonyl-2-nonyl-1,3,8-triaza-spiro[4.5]dec-1-en-4-one was synthesized by operations similar to those in Reaction 10-20, Reaction 1-4, Reaction 4-1, Reaction 5-3 and reaction 25-1 using appropriate reagents and starting material.
MS (ESI) m/z=370 (M+H)+.
(Reaction 100-2)
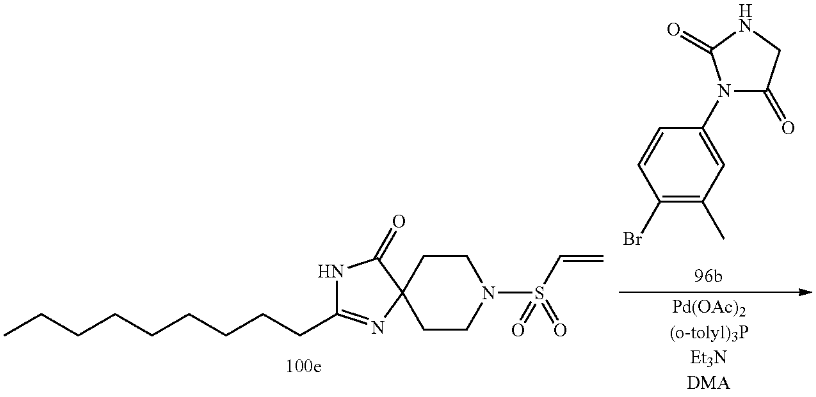
100e -continued

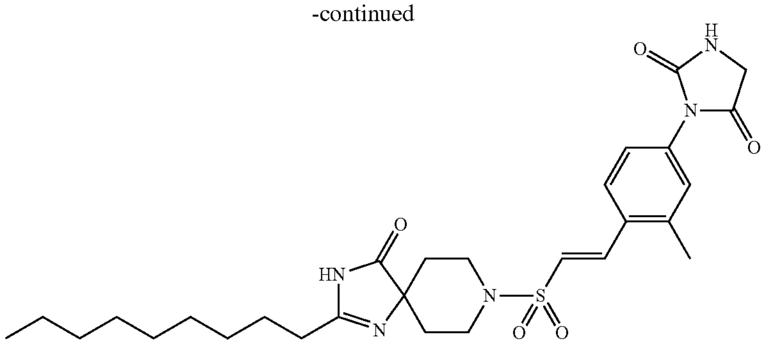

Compound 536

3-{3-Methyl-4-[(E)-2-(2-nonyl-4-oxo-1,3,8-triaza-spiro[4.5]dec-1-ene-8-sulfonyl)-vinyl]-phenyl}-imidazolidine-2,4-dione was synthesized by operations similar to those in Reaction 25-2 using appropriate reagents and starting material.

MS (ESI) m/z=558 (M+H)+.

The example compounds shown below were synthesized by operations similar to those in Reaction 100-2 using appropriate reagents and starting materials.

Compounds 537 to Compound 539

TABLE 75

| Target Compound | Structure | LCMS condition | Retention time (min) | MS (m/z) |
|---|---|---|---|---|
| 537 | 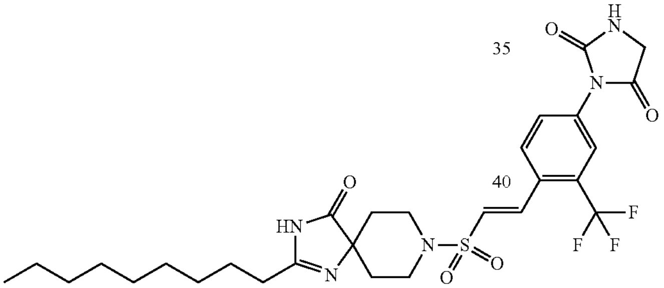 [SMILES: CCCCCCCCCC1=NC2(CCN(S(=O)(=O)/C=C/c3ccc(N4C(=O)CNC4=O)cc3C(F)(F)F)CC2)C(=O)N1] | LCMS-A-1 | 2.63 | 612 (M + H)+ |
| 538 | 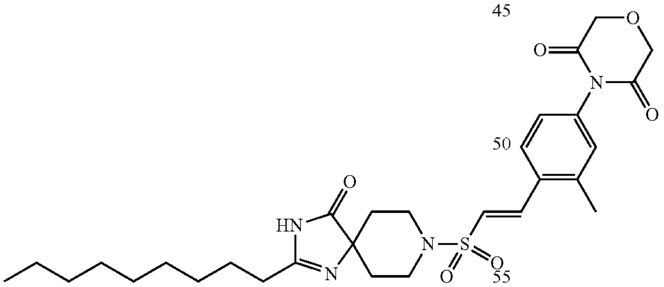 | LCMS-A-1 | 2.6 | 573 (M + H)+ |
| 539 | 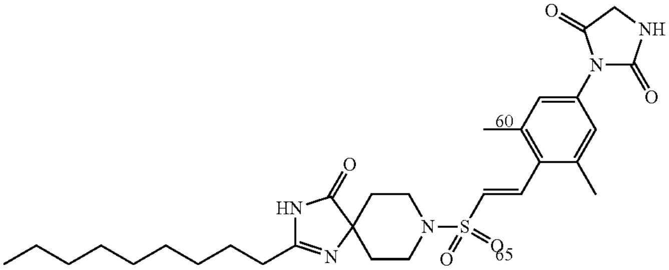 [SMILES: CCCCCCCCCC1=NC2(CCN(S(=O)(=O)/C=C/c3c(C)cc(N4C(=O)CNC4=O)cc3C)CC2)C(=O)N1] | LCMS-A-1 | 2.43 | 572 (M + H)+ |

The aryl bromide reagent used in the synthesis of Compound 537 (3-(4-bromo-3-trifluoromethyl-phenyl)-imidazolidine-2,4-dione) was synthesized as follows.

(Reaction 100-3)

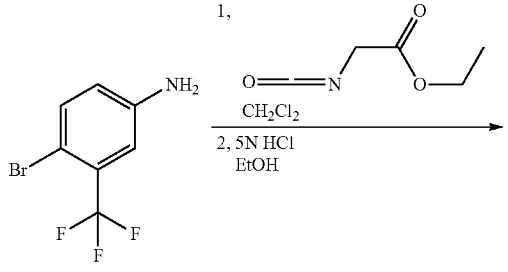

25n

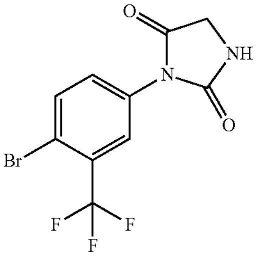

100f 3-(4-Bromo-3-trifluoromethyl-phenyl)-imidazolidine-2,4-dione was synthesized by operations similar to those in Reaction 84-1 and Reaction 96-1 using appropriate reagents and starting material.

MS (ESI) m/z=321 (M−H)−.

The aryl bromide reagent used in the synthesis of Compound 538 (4-(4-bromo-3-methyl-phenyl)-morpholine-3,5-dione) was synthesized as follows.

(Reaction 100-4)

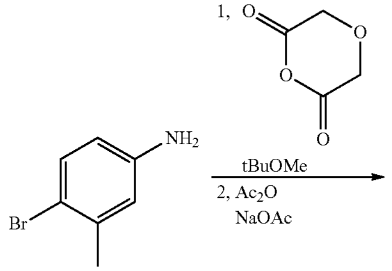

26h

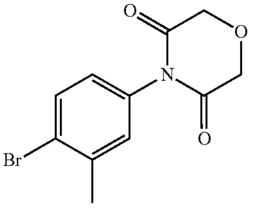

100g

[1,4]Dioxane-2,6-dione (312 mg, 2.69 mmol) was added to a solution of 4-bromo-3-methyl-phenylamine (500 mg, 2.69 mmol) in tBuOMe (7.0 ml), and the mixture was stirred at room temperature overnight. The reaction solution was concentrated under reduced pressure. Acetic anhydride (4.0 ml, 42.3 mmol) and sodium acetate (35 mg, 0.427 mmol) were added to the resulting residue, and the mixture was heated with stirring at 60° C. for three hours. Water was added to the reaction solution, and collection by filtration and trituration with water gave 4-(4-bromo-3-methyl-phenyl)-morpholine-3,5-dione (577 mg, 73%).

MS (ESI) m/z=284, 286 (M+H)+.

The aryl bromide reagent used in the synthesis of Compound 539 (3-(4-bromo-3,5-dimethyl-phenyl)-imidazolidine-2,4-dione) was synthesized as follows.

(Reaction 100-5)

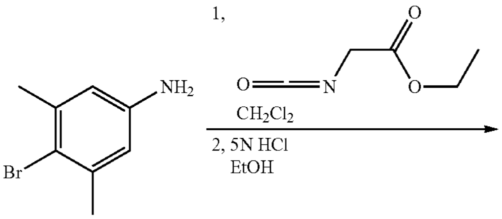

96g

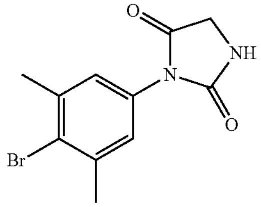

100h 3-(4-Bromo-3,5-dimethyl-phenyl)-imidazolidine-2,4-dione was synthesized by operations similar to those in Reaction 84-1 and Reaction 96-1 using appropriate reagents and starting material.

MS (ESI) m/z=283, 285 (M+H)+.

Example 101

5,5-Dimethyl-3-[3-methyl-4-((E)-2-{4-oxo-2-[4-(3,3,3-trifluoro-propyl)-cyclohexyl]-1,3,8-triaza-spiro[4.5]dec-1-ene-8-sulfonyl}-vinyl)-phenyl]-imidazolidine-2,4-dione (Compound 540)

(Reaction 101-1)

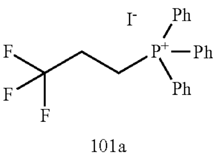

101a

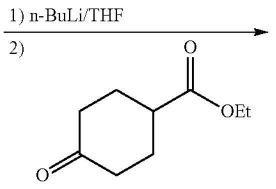

101b

THF

-continued

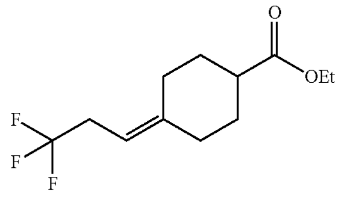

101c n-Butyllithium (1.6 M solution in hexane, 26 ml, 41.6 mmol) was added to a solution of triphenyl-(3,3,3-trifluoro-propyl)-phosphonium iodide (20.25 g, 41.64 mmol) in THF (141 ml) at −78° C. over 13 minutes, and the mixture was stirred at the same temperature for 20 minutes. A solution of 4-oxo-cyclohexanecarboxylic acid ethyl ester (6.56 g, 38.54 mmol) in THF (22 ml) was added to the reaction solution at −78° C. over 17 minutes, and the mixture was stirred at the same temperature for one hour. A 50% saturated aqueous ammonium chloride solution was added, followed by extraction with dichloromethane. The organic layer was then dried over $MgSO_4$ and concentrated under reduced pressure. The resulting residue was purified by silica gel column chromatography (hexane-ethyl acetate) to give ethyl 4-(3,3,3-trifluoro-propylidene)-cyclohexanecarboxylate (9.25 g, 96%).

$^1$H-NMR (400 MHz, $CDCl_3$) δ 1.25 (3H, t, J=7.1 Hz), 1.57 (2H, m), 1.90 (1H, m), 2.01 (2H, m), 2.11 (1H, m), 2.31 (1H, m), 2.49 (2H, m), 2.80 (2H, m), 4.13 (2H, t, J=7.1 Hz), 5.15 (1H, t, J=7.6 Hz).

(Reaction 101-2)

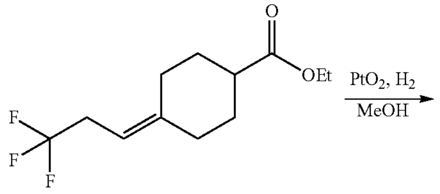

101c

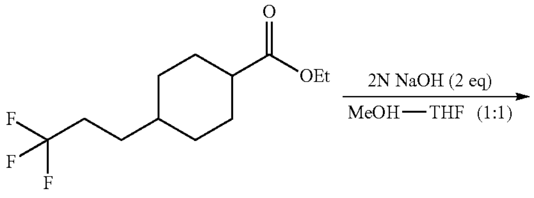

101d
trans:cis = 3:2

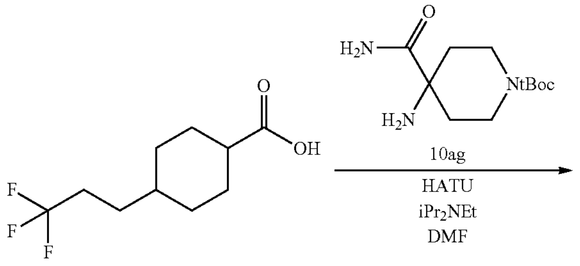

101e

-continued

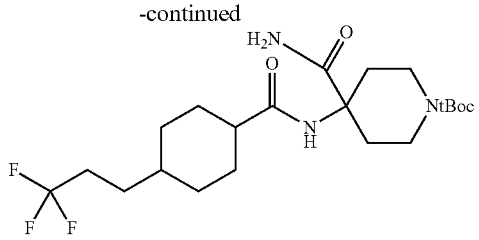

101f

4-Carbamoyl-4-{[4-(3,3,3-trifluoro-propyl)-cyclohexanecarbonyl]-amino}-piperidine-1-carboxylic acid tert-butyl ester was synthesized by operations similar to those in Reaction 18-2 (using $PtO_2$ as a catalyst), Reaction 95-18 and Reaction 10-14 using appropriate reagents and starting material.

$^1$H-NMR (400 MHz, $CDCl_3$) δ 0.98 (2H, m), 1.25-1.70 (9H, m), 1.45 (9H, s), 1.88 (4H, m), 2.10 (3H, m), 3.08 (2H, m), 3.81 (2H, m), 5.30 (1H, br), 5.40 (1H, s), 7.15 (1H, br).

(Reaction 101-3)

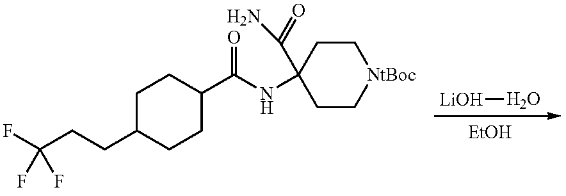

101f

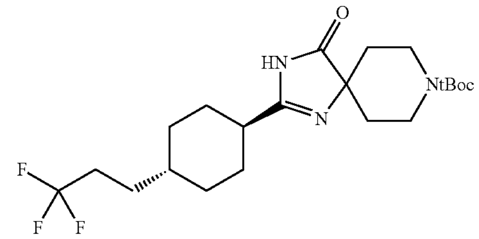

101g

LiOH.$H_2O$ (1.55 g, 36.9 mmol) was added to a solution of 4-carbamoyl-4-{[4-(3,3,3-trifluoro-propyl)-cyclohexanecarbonyl]-amino}-piperidine-1-carboxylic acid tert-butyl ester (5.53 g, 12.3 mmol) in ethanol (123 mL), and the mixture was stirred at 85° C. for two hours. A 50% saturated aqueous ammonium chloride solution was added to the reaction mixture, followed by extraction with ethyl acetate. The organic layer was then dried over $MgSO_4$ and concentrated under reduced pressure. The resulting residue was purified by reprecipitation with hexane-ethyl acetate=3:1 to give 4-oxo-2-[4-(3,3,3-trifluoro-propyl)-cyclohexyl]-1,3,8-triaza-spiro[4.5]dec-1-ene-8-carboxylic acid tert-butyl ester (4.88 g, 92%).

$^1$H-NMR (400 MHz, $CDCl_3$) δ 1.05 (2H, m,), 1.25-1.60 (7H, m), 1.45 (9H, s), 1.81 (2H, m), 1.90 (2H, m), 2.02 (2H, m), 2.11 (2H, m), 2.36 (1H, m), 3.40 (2H, m), 3.90 (2H, m), 8.10 (1H, br).

(Reaction 101-4)
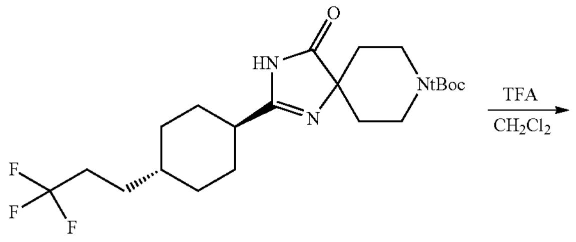
101g
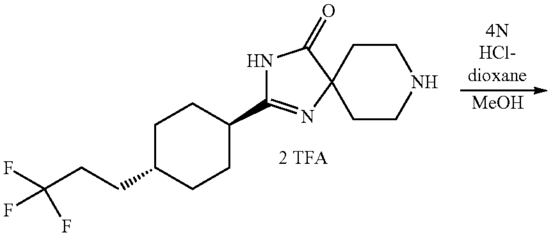
101h
-continued
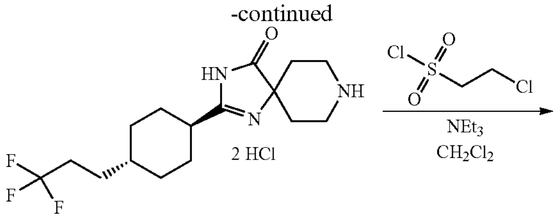
101i
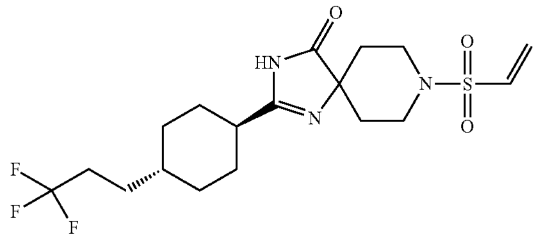
101j
8-Ethenesulfonyl-2-[4-(3,3,3-trifluoro-propyl)-cyclohexyl]-1,3,8-triaza-spiro[4.5]dec-1-en-4-one was synthesized by operations similar to those in Reaction 4-1, Reaction 5-3 and Reaction 25-1 using appropriate reagents and starting material.
$^1$H-NMR (400 MHz, $CDCl_3$) δ 1.05 (2H, m,), 1.25-1.70 (7H, m), 1.89 (2H, m), 2.00 (4H, m), 2.11 (2H, m), 2.39 (1H, m), 3.25 (2H, m), 3.67 (2H, m), 6.03 (1H, d, J=10.0 Hz), 6.26 (1H, d, J=16.0 Hz), 6.03 (1H, dd, J=16.0 and 10.0 Hz), 8.50 (1H, br).
(Reaction 101-5)
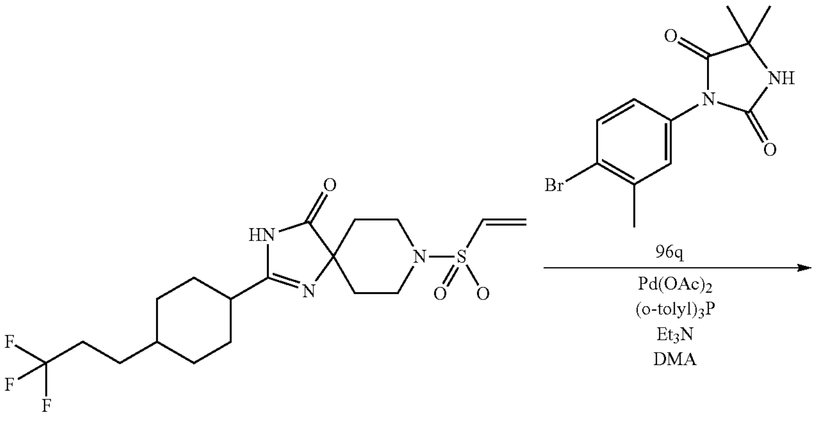
101j
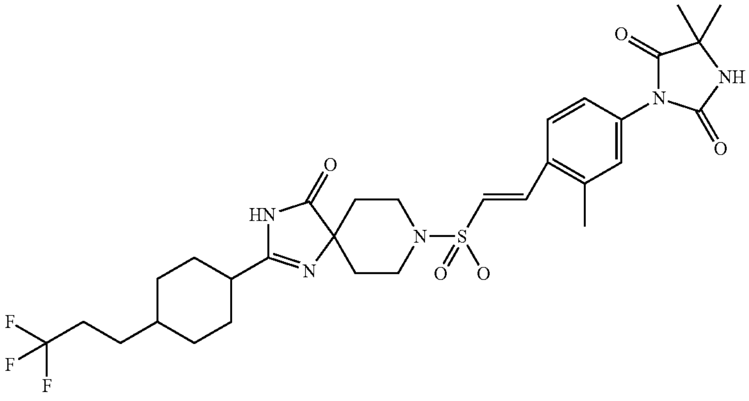
Compound 540

5,5-Dimethyl-3-[3-methyl-4-((E)-2-{4-oxo-2-[4-(3,3,3-trifluoro-propyl)-cyclohexyl]-1,3,8-triaza-spiro[4.5]dec-1-ene-8-sulfonyl}-vinyl)-phenyl]-imidazolidine-2,4-dione was synthesized by operations similar to those in Reaction 25-2 using appropriate reagents and starting material.

MS (ESI) m/z=638 (M+H)+.

The example compounds shown below were synthesized by operations similar to those in Example 101 using appropriate reagents and starting materials.

Compounds 541 to Compound 559

TABLE 76

| Target Compound | Structure | LCMS condition | Retention time (min) | MS (m/z) |
|---|---|---|---|---|
| 541 | 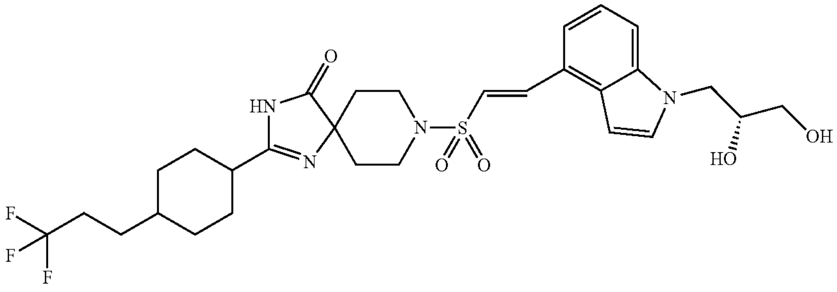 [SMILES: O=C1NC(C2CCC(CCC(F)(F)F)CC2)=NC12CCN(S(=O)(=O)/C=C/c1cccc3c1ccn3C[C@@H](O)CO)CC2] | LCMS-F-1 | 0.94 | 611 (M + H)+ |
| 542 | 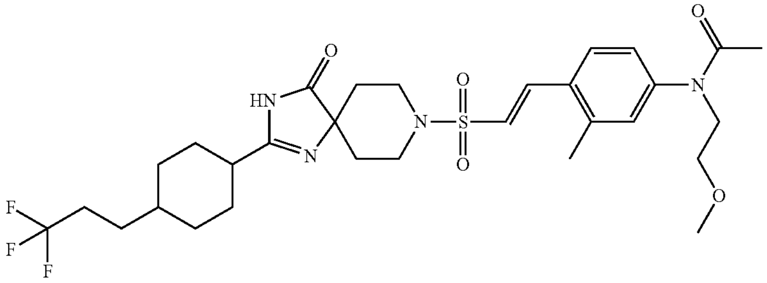 [SMILES: COCCN(C(C)=O)c1ccc(/C=C/S(=O)(=O)N2CCC3(CC2)N=C(C2CCC(CCC(F)(F)F)CC2)NC3=O)c(C)c1] | LCMS-D-1 | 2.30 | 627 (M + H)+ |
| 543 | 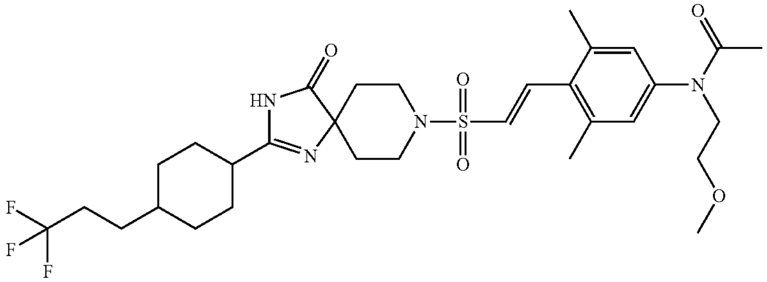 [SMILES: COCCN(C(C)=O)c1cc(C)c(/C=C/S(=O)(=O)N2CCC3(CC2)N=C(C2CCC(CCC(F)(F)F)CC2)NC3=O)c(C)c1] | LCMS-D-1 | 2.42 | 641 (M + H)+ |
| 544 | 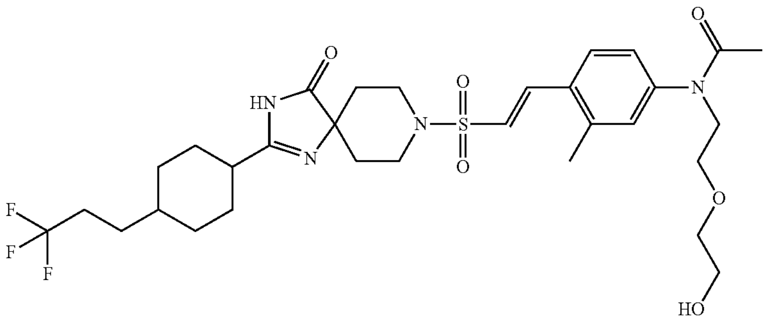 [SMILES: CC(=O)N(CCOCCO)c1ccc(/C=C/S(=O)(=O)N2CCC3(CC2)N=C(C2CCC(CCC(F)(F)F)CC2)NC3=O)c(C)c1] | LCMS-D-1 | 2.11 | 657 (M + H)+ |

TABLE 76-continued
| Target Compound | Structure | LCMS condition | Retention time (min) | MS (m/z) |
| --- | --- | --- | --- | --- |
| 545 | 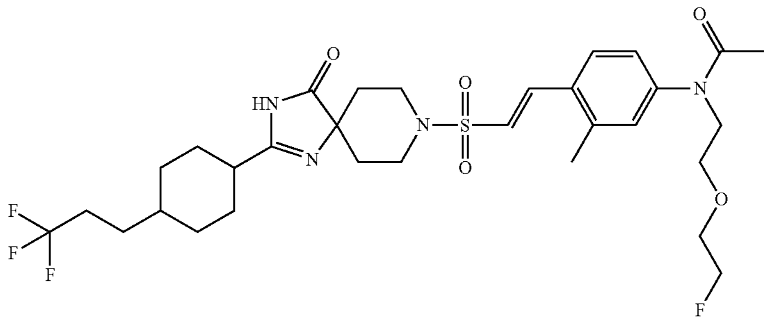 [SMILES: CC(=O)N(CCOCCF)c1ccc(/C=C/S(=O)(=O)N2CCC3(CC2)N=C(C2CCC(CCC(F)(F)F)CC2)NC3=O)c(C)c1] | LCMS-D-1 | 2.30 | 659 (M + H)+ |
| 546 | 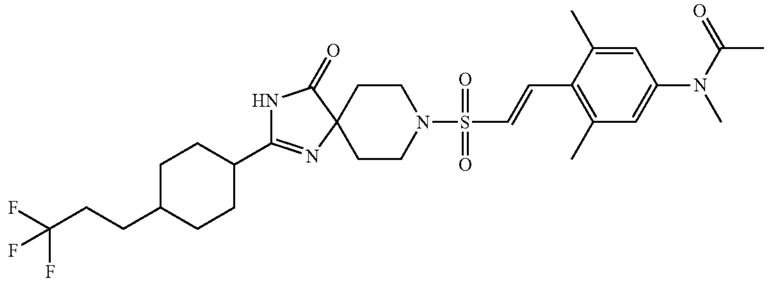 [SMILES: CC(=O)N(C)c1cc(C)c(/C=C/S(=O)(=O)N2CCC3(CC2)N=C(C2CCC(CCC(F)(F)F)CC2)NC3=O)c(C)c1] | LCMS-D-1 | 1.56 | 597 (M + H)+ |
| 547 | 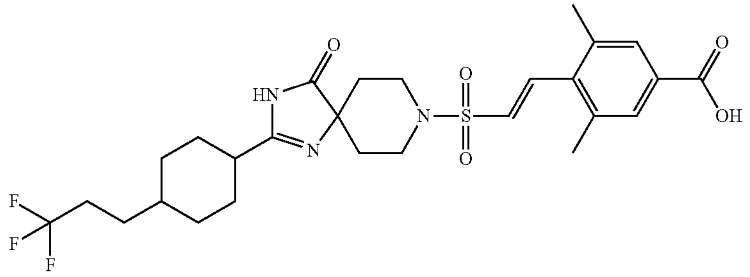 [SMILES: Cc1cc(C(=O)O)cc(C)c1/C=C/S(=O)(=O)N1CCC2(CC1)N=C(C1CCC(CCC(F)(F)F)CC1)NC2=O] | LCMS-D-1 | 2.45 | 570 (M + H)+ |
| 548 | 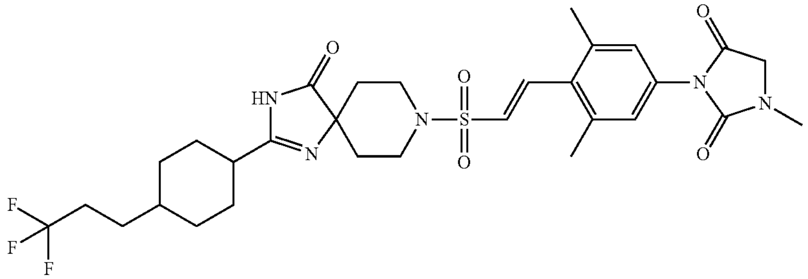 [SMILES: Cc1cc(N2C(=O)CN(C)C2=O)cc(C)c1/C=C/S(=O)(=O)N1CCC2(CC1)N=C(C1CCC(CCC(F)(F)F)CC1)NC2=O] | LCMS-D-1 | 2.13 | 638 (M + H)+ |
| 549 | 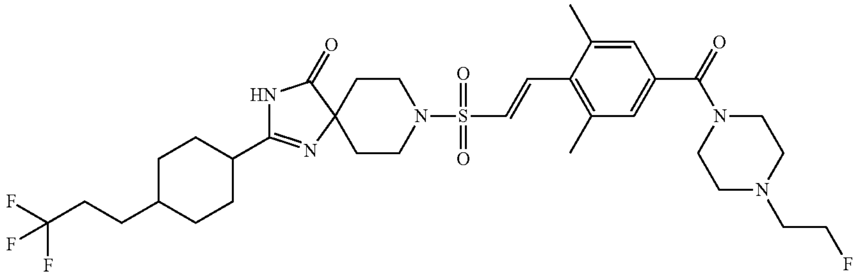 [SMILES: Cc1cc(C(=O)N2CCN(CCF)CC2)cc(C)c1/C=C/S(=O)(=O)N1CCC2(CC1)N=C(C1CCC(CCC(F)(F)F)CC1)NC2=O] | LCMS-D-1 | 1.63 | 684 (M + H)+ |

TABLE 76-continued
| Target Compound | Structure | LCMS condition | Retention time (min) | MS (m/z) |
|---|---|---|---|---|
| 550 | 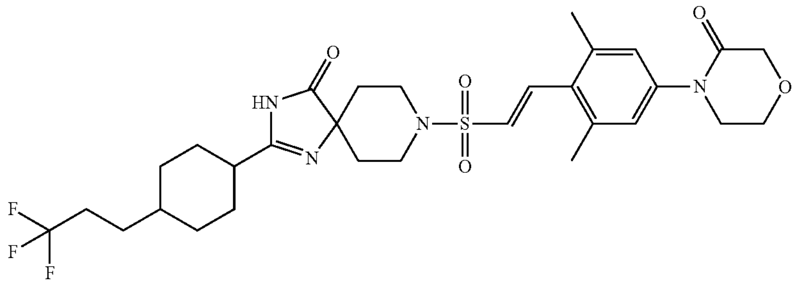 [SMILES: Cc1cc(N2CCOCC2=O)cc(C)c1/C=C/S(=O)(=O)N1CCC2(CC1)N=C(C1CCC(CCC(F)(F)F)CC1)NC2=O] | LCMS-D-1 | 2.23 | 625 (M + H)+ |
| 551 | 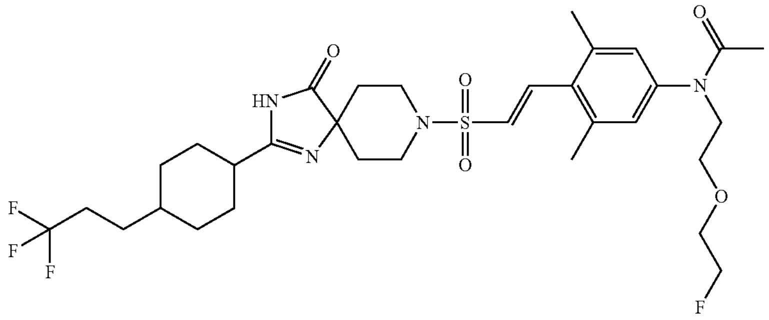 [SMILES: CC(=O)N(CCOCCF)c1cc(C)c(/C=C/S(=O)(=O)N2CCC3(CC2)N=C(C2CCC(CCC(F)(F)F)CC2)NC3=O)c(C)c1] | LCMS-D-1 | 2.55 | 673 (M + H)+ |
| 552 | 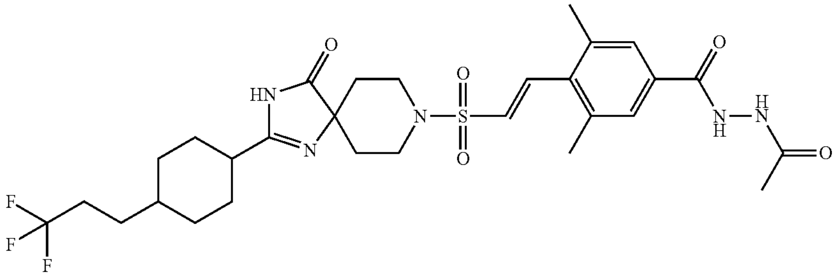 [SMILES: CC(=O)NNC(=O)c1cc(C)c(/C=C/S(=O)(=O)N2CCC3(CC2)N=C(C2CCC(CCC(F)(F)F)CC2)NC3=O)c(C)c1] | LCMS-D-1 | 2.02 | 626 (M + H)+ |
| 553 | 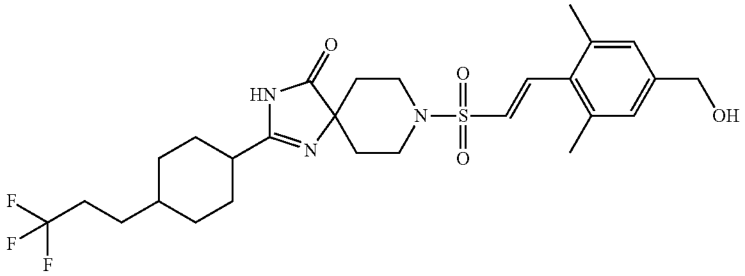 [SMILES: Cc1cc(CO)cc(C)c1/C=C/S(=O)(=O)N1CCC2(CC1)N=C(C1CCC(CCC(F)(F)F)CC1)NC2=O] | LCMS-D-1 | 2.40 | 556 (M + H)+ |
| 554 | 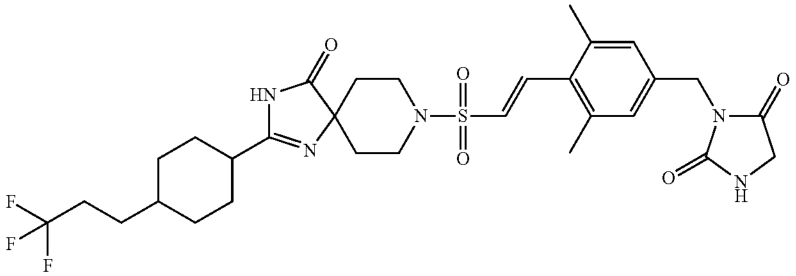 | LCMS-D-1 | 2.45 | 638 (M + H)+ |

TABLE 76-continued
| Target Compound | Structure | LCMS condition | Retention time (min) | MS (m/z) |
|---|---|---|---|---|
| 555 | 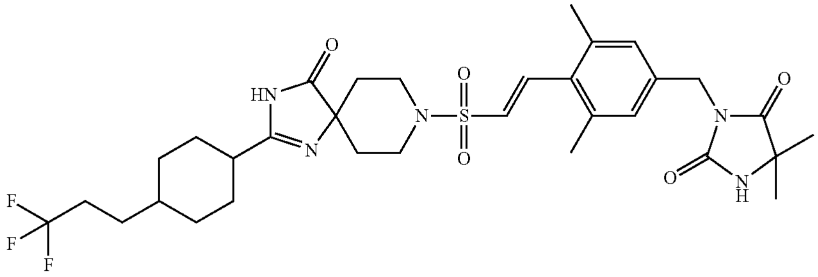 [SMILES: Cc1cc(CN2C(=O)NC(C)(C)C2=O)cc(C)c1/C=C/S(=O)(=O)N1CCC2(CC1)N=C(C1CCC(CCC(F)(F)F)CC1)NC2=O] | LCMS-D-1 | 2.67 | 666 (M + H)+ |
| 556 | 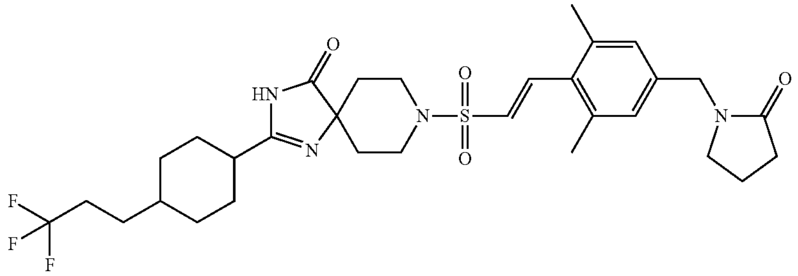 [SMILES: Cc1cc(CN2CCCC2=O)cc(C)c1/C=C/S(=O)(=O)N1CCC2(CC1)N=C(C1CCC(CCC(F)(F)F)CC1)NC2=O] | LCMS-D-1 | 2.58 | 623 (M + H)+ |
| 557 | 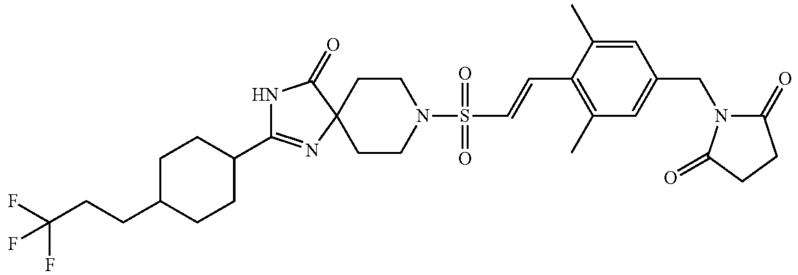 [SMILES: Cc1cc(CN2C(=O)CCC2=O)cc(C)c1/C=C/S(=O)(=O)N1CCC2(CC1)N=C(C1CCC(CCC(F)(F)F)CC1)NC2=O] | LCMS-D-1 | 2.42 | 637 (M + H)+ |
| 558 | 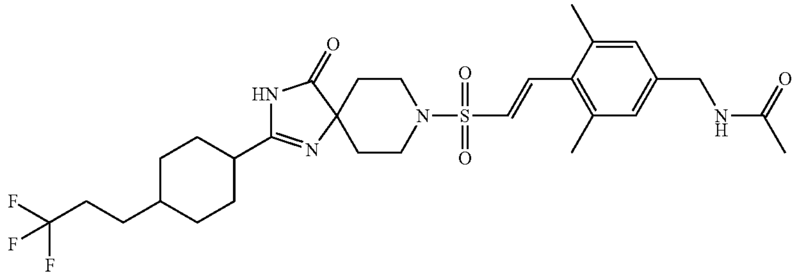 | LCMS-D-1 | 2.78 | 597 (M + H)+ |
| 559 | 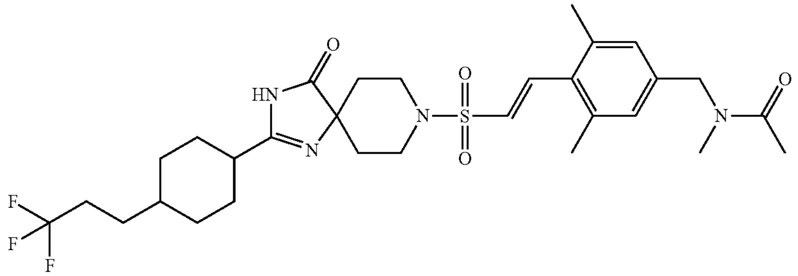 [SMILES: CC(=O)N(C)Cc1cc(C)c(/C=C/S(=O)(=O)N2CCC3(CC2)N=C(C2CCC(CCC(F)(F)F)CC2)NC3=O)c(C)c1] | LCMS-D-1 | 2.45 | 611 (M + H)+ |

The aryl bromide reagent used in the synthesis of Compound 542 (N-(4-bromo-3-methyl-phenyl)-N-(2-methoxy-ethyl)-acetamide) was synthesized as follows.

(Reaction 101-6)

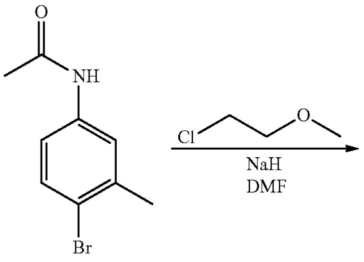

11a

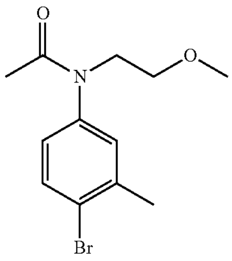

101k (N-(4-Bromo-3-methyl-phenyl)-N-(2-methoxy-ethyl)-acetamide was synthesized by operations similar to those in Reaction 25-3 using appropriate reagents and starting material.

MS (ESI) m/z=286, 288 (M+H)+.

The aryl bromide reagent used in the synthesis of Compound 543 (N-(4-bromo-3,5-dimethyl-phenyl)-N-(2-methoxy-ethyl)-acetamide) was synthesized as follows.

(Reaction 101-7)

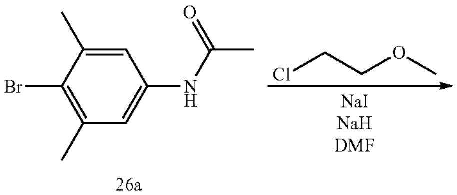

26a

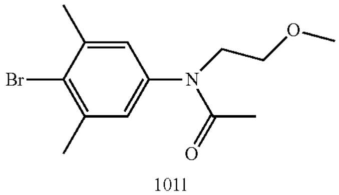

101l

N-(4-Bromo-3,5-dimethyl-phenyl)-N-(2-methoxy-ethyl)-acetamide was synthesized by operations similar to those in Reaction 25-3 using appropriate reagents and starting material.

$^1$H-NMR ($CDCl_3$) δ 6.93 (s, 2H), 3.82 (t, 2H, J=5.7 Hz), 3.49 (t, 2H, J=5.7 Hz), 3.30 (s, 2H), 2.42 (s, 6H), 1.85 (s, 3H).

The aryl bromide reagent used in the synthesis of Compound 544 (N-(4-bromo-3-methyl-phenyl)-N-[2-(2-hydroxy-ethoxy)-ethyl]-acetamide) was synthesized as follows.

(Reaction 101-8)

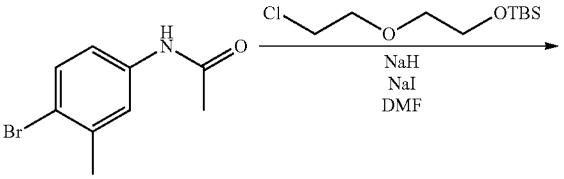

11a

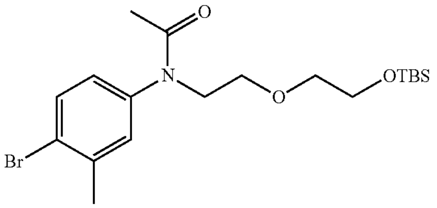

101m

Sodium hydride (60% oil suspension, 100 mg, 2.63 mmol) was added to a solution of 4-bromo-3-methylphenylacetamide (500 mg, 2.19 mmol), tert-butyl-[2-(2-chloro-ethoxy)-ethoxy]-dimethyl-silane (excess) and sodium iodide (324 mg, 2.19 mmol) in dimethylformamide (20 ml). The mixture was heated with stirring at 100° C. for 17 hours. The reaction solution was cooled and then concentrated. The resulting residue was purified by silica gel column chromatography (ethyl acetate-hexane) to give N-(4-bromo-3-methyl-phenyl)-N-{2-[2-(tert-butyl-dimethyl-silanyloxy)-ethoxy]-ethyl}-acetamide (555 mg, 65%).

$^1$H-NMR ($CDCl_3$) δ 0.04 (s, 6H), 0.87 (s, 9H), 1.83 (s, 3H), 2.39 (s, 3H), 3.40-3.50 (m, 2H), 3.49-3.66 (m, 2H), 3.63-3.77 (m, 2H), 3.73-3.89 (m, 2H), 6.76-7.00 (m, 1H), 6.98-7.16 (m, 1H), 7.38-7.63 (m, 1H).

(Reaction 101-9)

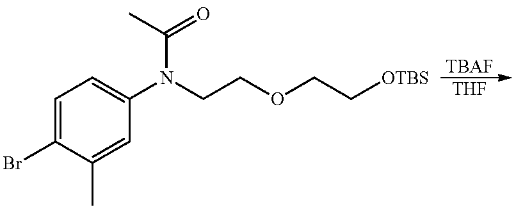

101m

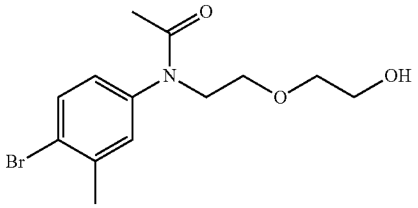

101n

N-(4-Bromo-3-methyl-phenyl)-N-[2-(2-hydroxy-ethoxy)-ethyl]-acetamide was synthesized by operations similar to those in Reaction 39-2 using appropriate reagents and starting material.

MS (ESI) m/z=316, 318 (M+H)+.

The aryl bromide reagent used in the synthesis of Compound 545 (N-(4-bromo-3-methyl-phenyl)-N-[2-(2-fluoro-ethoxy)-ethyl]-acetamide) was synthesized as follows.

(Reaction 101-10)

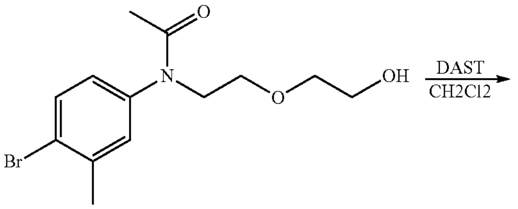

101n

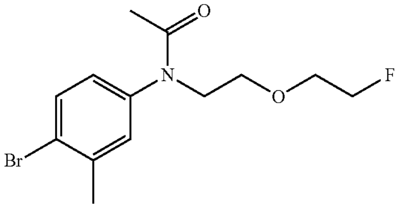

101o

N-(4-Bromo-3-methyl-phenyl)-N-[2-(2-fluoro-ethoxy)-ethyl]-acetamide was synthesized by operations similar to those in Reaction 25-15 using appropriate reagents and starting material.

MS (ESI) m/z=318, 320 (M+H)+.

The aryl bromide reagent used in the synthesis of Compound 548 (3-(4-bromo-3,5-dimethyl-phenyl)-1-methyl-imidazolidine-2,4-dione) was synthesized as follows.

(Reaction 101-11)

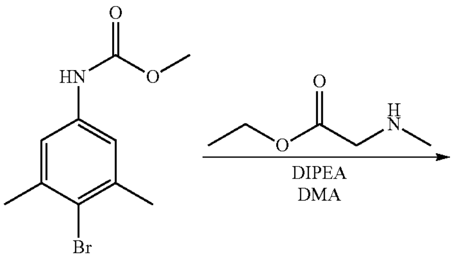

96i

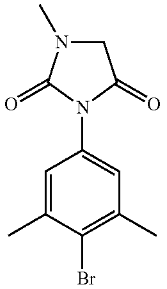

101p 3-(4-Bromo-3,5-dimethyl-phenyl)-1-methyl-imidazolidine-2,4-dione was synthesized by operations similar to those in Reaction 96-6 using appropriate reagents and starting material.

MS (ESI) m/z=297, 299 (M+H)+.

The aryl bromide reagent used in the synthesis of Compound 549 ((4-bromo-3,5-dimethyl-phenyl)-[4-(2-fluoro-ethyl)-piperazin-1-yl]-methanone) was synthesized as follows.

(Reaction 101-12)

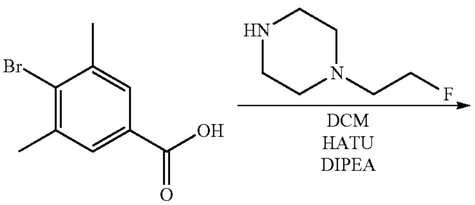

29i

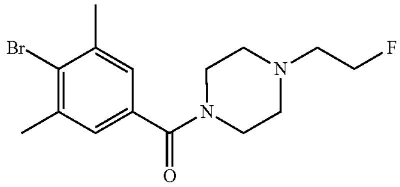

101q (4-Bromo-3,5-dimethyl-phenyl)-[4-(2-fluoro-ethyl)-piperazin-1-yl]-methanone was synthesized by operations similar to those in Reaction 10-14 using appropriate reagents and starting material.

$^1$H-NMR ($CDCl_3$) δ 7.10 (s, 2H), 4.66 (t, 1H, J=4.96 Hz), 4.51 (t, 1H, J=4.96 Hz), 3.79 (s, 2H), 3.47 (s, 2H), 2.79 (t, 1H, J=4.96 Hz), 2.70 (t, 1H, J=4.96 Hz), 2.56 (brs, 4H), 2.43 (s, 6H).

The aryl bromide reagent used in the synthesis of Compound 551 (N-(4-bromo-3,5-dimethyl-phenyl)-N-[2-(2-fluoroethoxy)ethyl]acetamide) was synthesized as follows.

(Reaction 101-13)

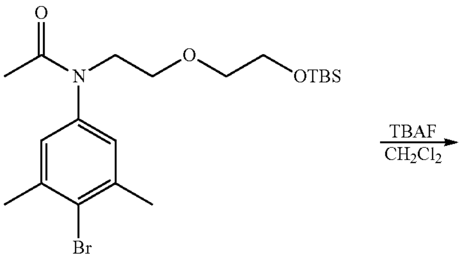

101r

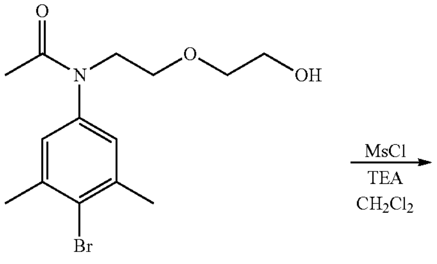

101s

-continued

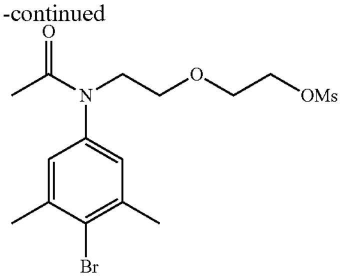

101t

2-[2-[Acetyl-(4-bromo-3,5-dimethyl-phenyl)amino]ethoxy]ethyl methanesulfonate was synthesized by operations similar to those in Reaction 39-2 and Reaction 5-4 using appropriate reagents and starting material.

MS (ESI) m/z=408, 410 (M+H)+.

(Reaction 101-14)

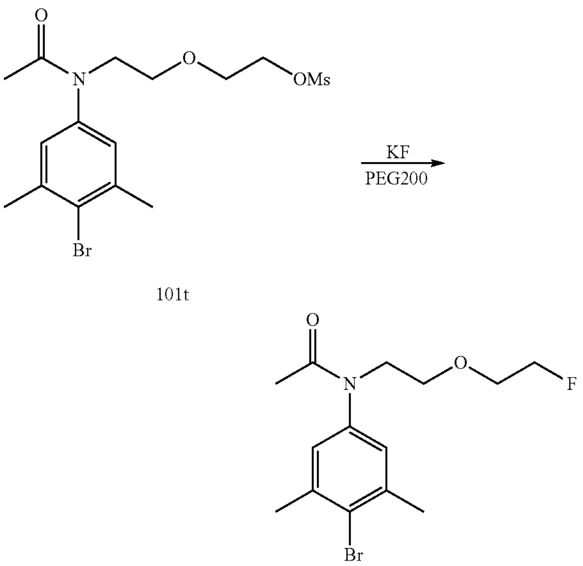

101t

101u

Potassium fluoride (180 mg, 3.11 mmol) was added to a solution of 2-[2-[acetyl-(4-bromo-3,5-dimethyl-phenyl)amino]ethoxy]ethyl methanesulfonate (254 mg, 0.622 mmol) in PEG200 (2 ml), and the mixture was irradiated with microwaves at 100° C. for 10 minutes. The reaction solution was diluted with ethyl acetate, and the organic layer was sequentially washed with water and saturated brine and concentrated under reduced pressure. The resulting residue was purified by silica gel column chromatography (hexane-ethyl acetate) to give N-(4-bromo-3,5-dimethyl-phenyl)-N-[2-(2-fluoroethoxy)ethyl]acetamide (144 mg, 70%).

MS (ESI) m/z=332, 334 (M+H)+.

The aryl bromide reagent used in the synthesis of Compound 552 (N'-(4-bromo-3,5-dimethyl-benzoyl)-hydrazinecarboxylic acid tert-butyl ester) was synthesized as follows.

(Reaction 101-15)

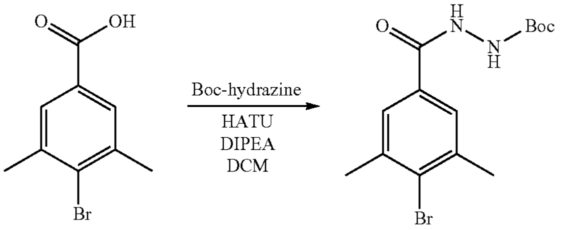

29i

101v

N'-(4-Bromo-3,5-dimethyl-benzoyl)-hydrazinecarboxylic acid tert-butyl ester was synthesized by operations similar to those in Reaction 10-14 using appropriate reagents and starting material.

MS (ESI) m/z=343, 345 (M+H)+.

Example 102

3-(4-{(E)-2-[2-(4-Butyl-cyclohexyl)-4-oxo-1,3,8-triaza-spiro[4.5]dec-1-ene-8-sulfonyl]-vinyl}-3-methyl-phenyl)-imidazolidine-2,4-dione (Compound 560)

(Reaction 102-1)

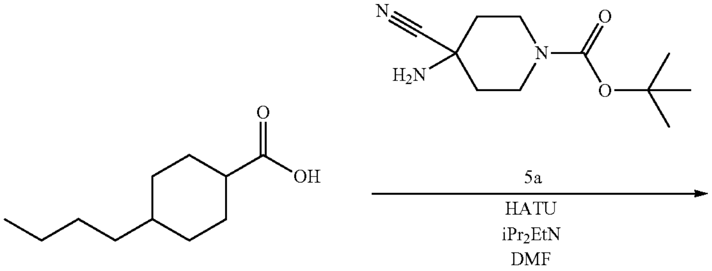

102a

-continued
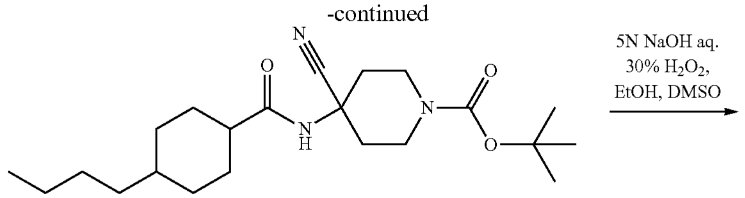
102b
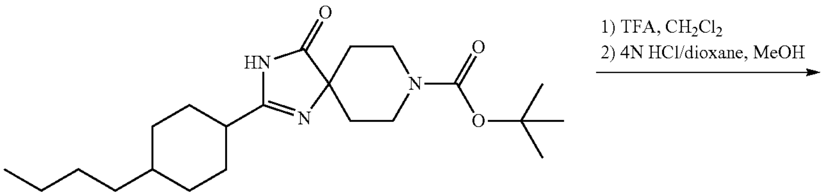
102c
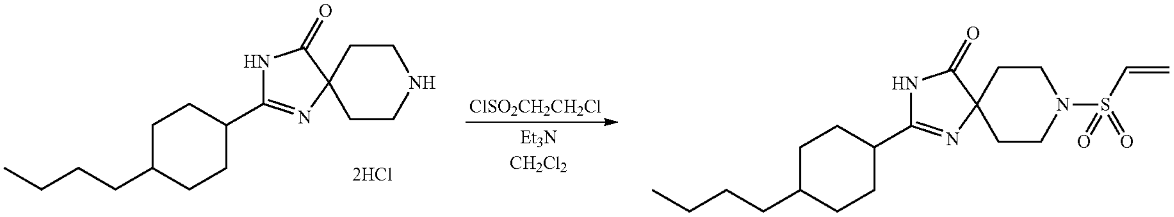
102d
102e
2-(4-Butyl-cyclohexyl)-8-ethenesulfonyl-1,3,8-triaza-spiro[4.5]dec-1-en-4-one was synthesized by operations similar to those in Reaction 10-14, Reaction 1-4, Reaction 4-1, Reaction 5-3 and Reaction 25-1 using appropriate reagents and starting material.
MS (ESI) m/z=382 (M+H)+.
(Reaction 102-2)
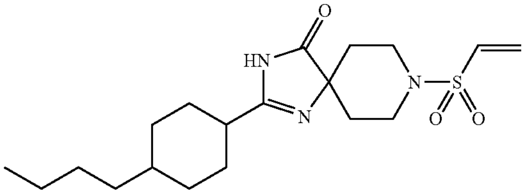
102e
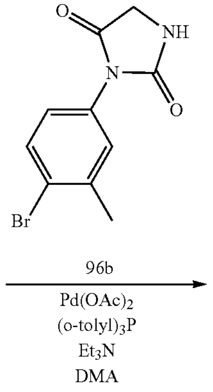

-continued

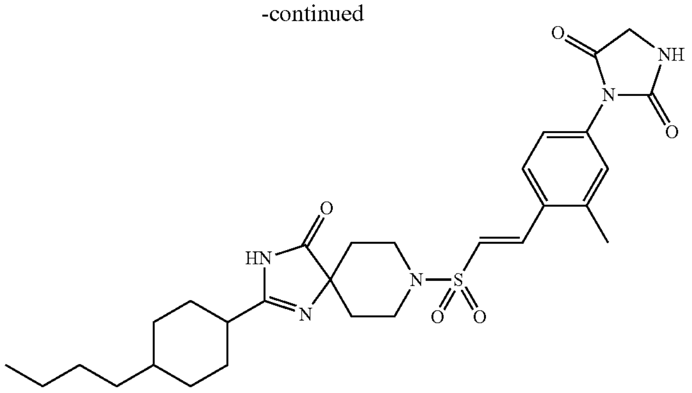

Compound 560

3-(4-{(E)-2-[2-(4-Butyl-cyclohexyl)-4-oxo-1,3,8-triaza-spiro[4.5]dec-1-ene-8-sulfonyl]-vinyl}-3-methyl-phenyl)-imidazolidine-2,4-dione was synthesized by operations similar to those in Reaction 25-2 using appropriate reagents and starting material.

MS (ESI) m/z=570 (M+H)+.

The example compounds shown below were synthesized by operations similar to those in Reaction 102-2 using appropriate reagents and starting materials.

Compounds 561 to Compound 562

The aryl bromide reagent used in the synthesis of Compound 561 (N-(4-bromo-3,5-dimethyl-phenyl)-N-[2-(2-methoxy-ethoxy)-ethyl]-acetamide) was synthesized as follows.

(Reaction 102-3)

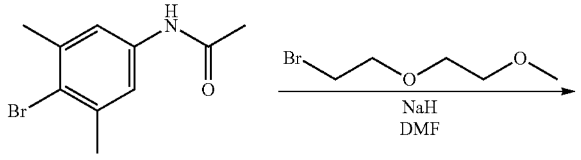

26a

TABLE 77

| Target Compound | Structure | LCMS condition | Retention time (min) | MS (m/z) |
|---|---|---|---|---|
| 561 | 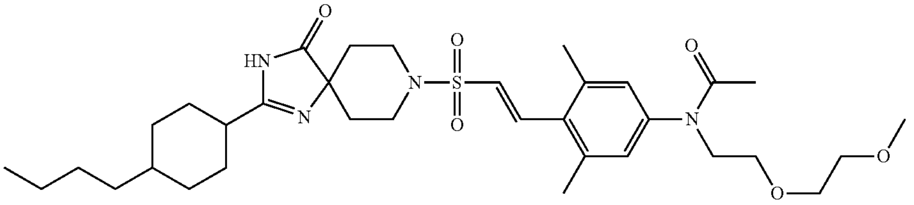 [SMILES: CCCCC1CCC(C2=NC3(CCN(S(=O)(=O)/C=C/c4c(C)cc(N(CCOCCOC)C(C)=O)cc4C)CC3)C(=O)N2)CC1] | LCMS-D-1 | 2.17 | 645 (M + H)+ |
| 562 | 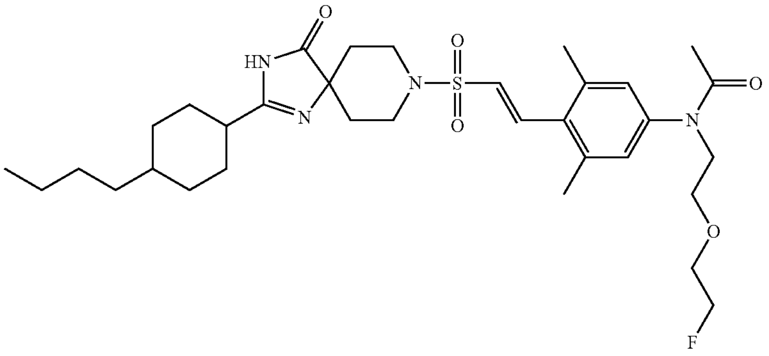 [SMILES: CCCCC1CCC(C2=NC3(CCN(S(=O)(=O)/C=C/c4c(C)cc(N(CCOCCF)C(C)=O)cc4C)CC3)C(=O)N2)CC1] | LCMS-D-1 | 3.25 | 633 (M + H)+ |

-continued

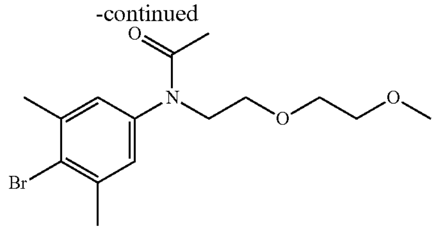

102f

N-(4-Bromo-3,5-dimethyl-phenyl)-N-[2-(2-methoxy-ethoxy)-ethyl]-acetamide was synthesized by operations similar to those in Reaction 25-3 using appropriate reagents and starting material.

MS (ESI) m/z=334, 336 (M+H)+.

Example 103

3-(4-{(E)-2-[2-(4-Isopropyl-cyclohexyl)-4-oxo-1,3,8-triaza-spiro[4.5]dec-1-ene-8-sulfonyl]-vinyl}-3-methyl-phenyl)-imidazolidine-2,4-dione (Compound 563)

(Reaction 103-1)

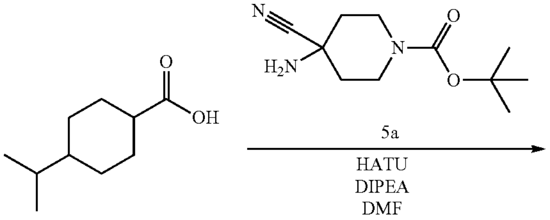

103a

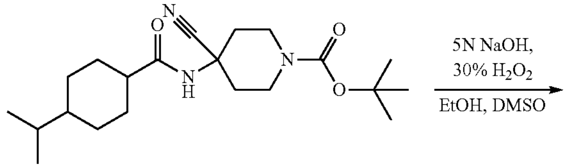

103b

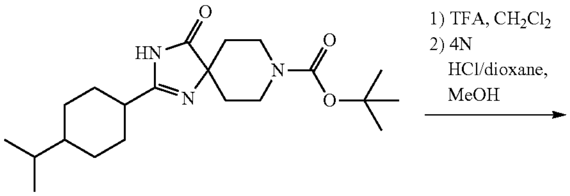

103c

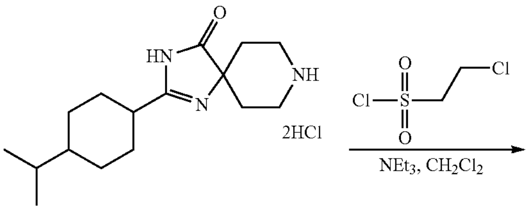

103d

-continued

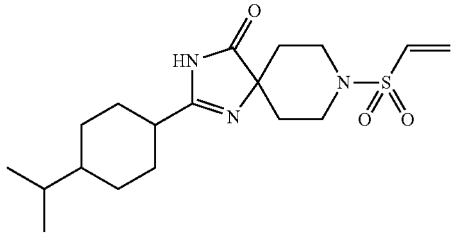

103e

8-Ethenesulfonyl-2-(4-isopropyl-cyclohexyl)-1,3,8-triaza-spiro[4.5]dec-1-en-4-one was synthesized by operations similar to those in Reaction 10-14, Reaction 1-4, Reaction 4-1, Reaction 5-3 and Reaction 25-1 using appropriate reagents and starting material.

MS (ESI) m/z=368 (M+H)+.

(Reaction 103-2)

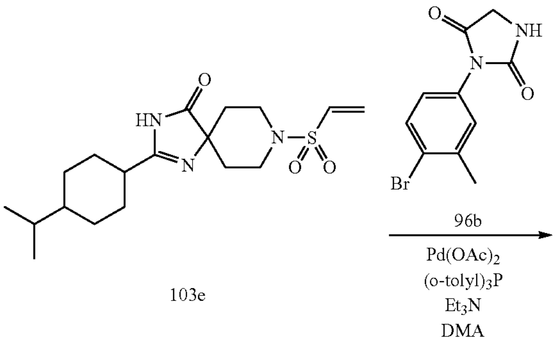

103e

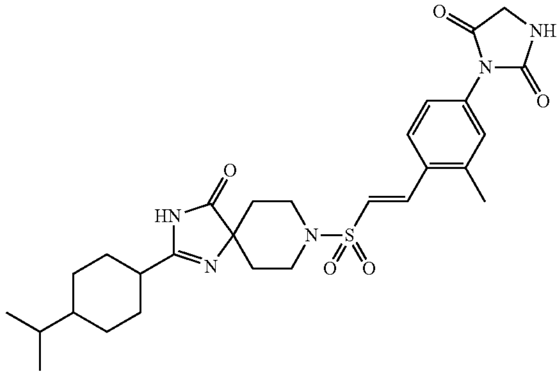

Compound 563

3-(4-{(E)-2-[2-(4-Isopropyl-cyclohexyl)-4-oxo-1,3,8-triaza-spiro[4.5]dec-1-ene-8-sulfonyl]-vinyl}-3-methyl-phenyl)-imidazolidine-2,4-dione was synthesized by operations similar to those in Reaction 25-2 using appropriate reagents and starting material.

MS (ESI) m/z=556 (M+H)+.

The example compound shown below was synthesized by operations similar to those in Reaction 103-2 using appropriate reagents and starting material.

Compound 564
TABLE 78
| Target Compound | Structure | LCMS condition | Retention time (min) | MS (m/z) |
|---|---|---|---|---|
| 564 | 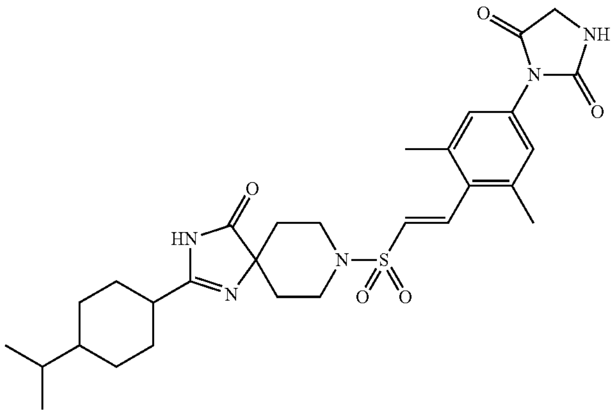 [SMILES: Cc1cc(N2C(=O)CNC2=O)cc(C)c1/C=C/S(=O)(=O)N1CCC2(CC1)N=C(C1CCC(C(C)C)CC1)NC2=O] | LCMS-C-1 | 2.72 | 570 (M + H)+ |
Example 104
The example compounds shown below were obtained by operations similar to those in Reaction 26-1 using appropriate reagents and starting materials.
Compounds 565 to 574
TABLE 79
| Target Compound | Structure | LCMS condition | Retention time (min) | MS (m/z) |
|---|---|---|---|---|
| 565 | 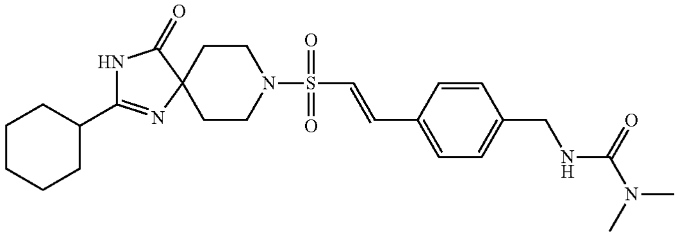 [SMILES: CN(C)C(=O)NCc1ccc(/C=C/S(=O)(=O)N2CCC3(CC2)N=C(C2CCCCC2)NC3=O)cc1] | LCMS-C-1 | 2.25 | 502 (M + H)+ |
| 566 | 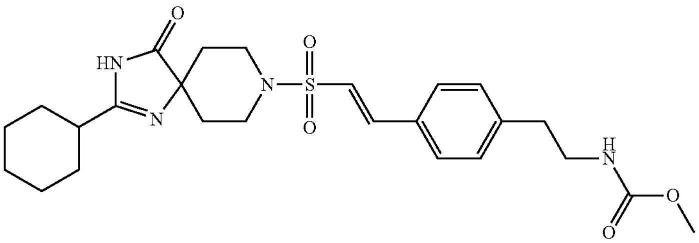 [SMILES: COC(=O)NCCc1ccc(/C=C/S(=O)(=O)N2CCC3(CC2)N=C(C2CCCCC2)NC3=O)cc1] | LCMS-C-1 | 2.47 | 503 (M + H)+ |

TABLE 79-continued
| Target Compound | Structure | LCMS condition | Retention time (min) | MS (m/z) |
|---|---|---|---|---|
| 567 | 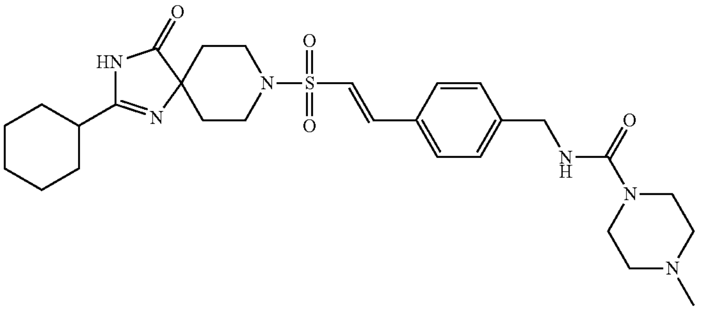 [SMILES: CN1CCN(C(=O)NCc2ccc(/C=C/S(=O)(=O)N3CCC4(CC3)N=C(C3CCCCC3)NC4=O)cc2)CC1] | LCMS-C-1 | 2.28 | 555 (M − H)− |
| 568 | 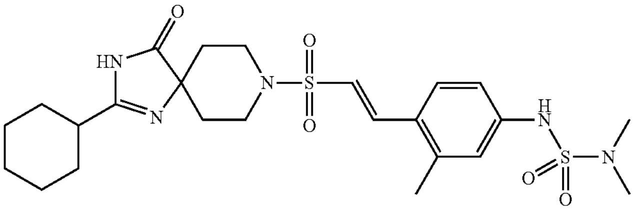 [SMILES: Cc1cc(NS(=O)(=O)N(C)C)ccc1/C=C/S(=O)(=O)N1CCC2(CC1)N=C(C1CCCCC1)NC2=O] | LCMS-C-1 | 2.43 | 538 (M + H)+ |
| 569 | 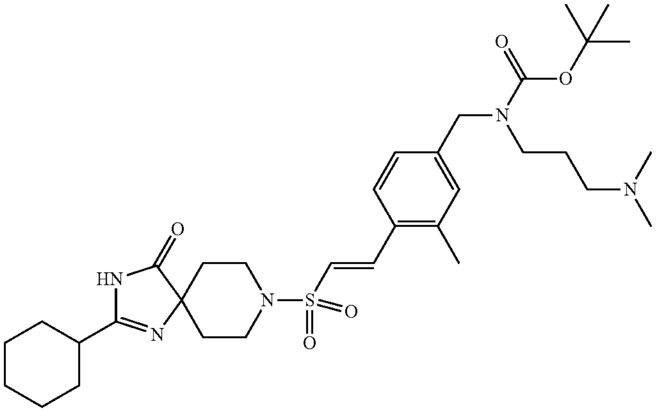 [SMILES: Cc1cc(CN(CCCN(C)C)C(=O)OC(C)(C)C)ccc1/C=C/S(=O)(=O)N1CCC2(CC1)N=C(C1CCCCC1)NC2=O] | LCMS-C-1 | 2.8 | 628 (M − H)− |
| 570 | 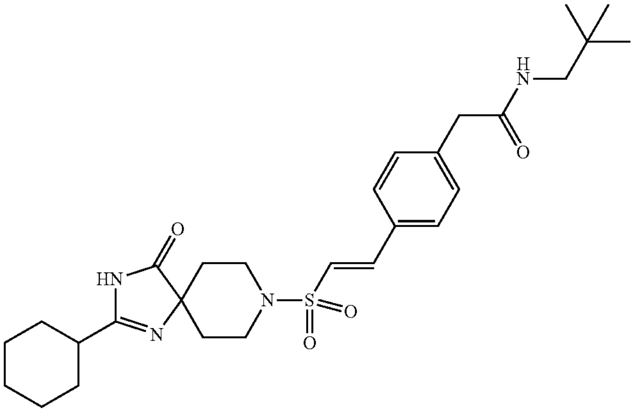 [SMILES: CC(C)(C)CNC(=O)Cc1ccc(/C=C/S(=O)(=O)N2CCC3(CC2)N=C(C2CCCCC2)NC3=O)cc1] | LCMS-C-1 | 2.6 | 527 (M − H)− |

TABLE 79-continued
| Target Compound | Structure | LCMS condition | Retention time (min) | MS (m/z) |
|---|---|---|---|---|
| 571 | 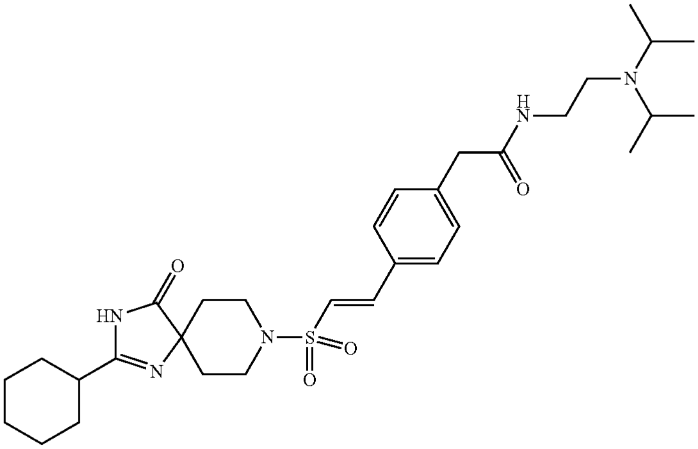 [SMILES: CC(C)N(CCNC(=O)Cc1ccc(/C=C/S(=O)(=O)N2CCC3(CC2)N=C(C2CCCCC2)NC3=O)cc1)C(C)C] | LCMS-C-1 | 2.17 | 584 (M − H)− |
| 572 | 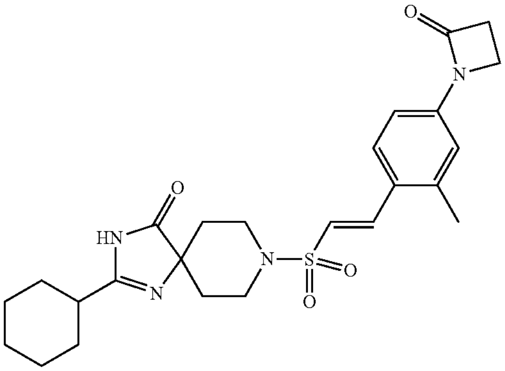 [SMILES: Cc1cc(N2CCC2=O)ccc1/C=C/S(=O)(=O)N1CCC2(CC1)N=C(C1CCCCC1)NC2=O] | LCMS-C-1 | 2.47 | 485 (M + H)+ |
| 573 | 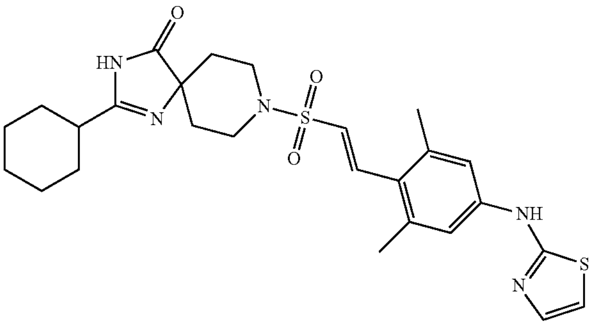 [SMILES: Cc1cc(Nc2nccs2)cc(C)c1/C=C/S(=O)(=O)N1CCC2(CC1)N=C(C1CCCCC1)NC2=O] | LCMS-D-1 | 2.82 | 528 (M + H)+ |
| 574 | 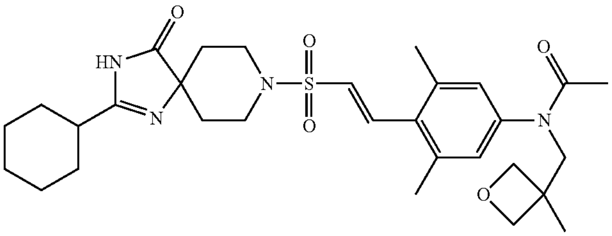 [SMILES: CC(=O)N(CC1(C)COC1)c1cc(C)c(/C=C/S(=O)(=O)N2CCC3(CC2)N=C(C2CCCCC2)NC3=O)c(C)c1] | LCMS-D-1 | 2.82 | 571 (M + H)+ |

The aryl bromide reagent used in the synthesis of Compound 567 (4-methyl-piperazine-1-carboxylic acid 4-bromo-benzylamide) was synthesized as follows.

(Reaction 104-1)

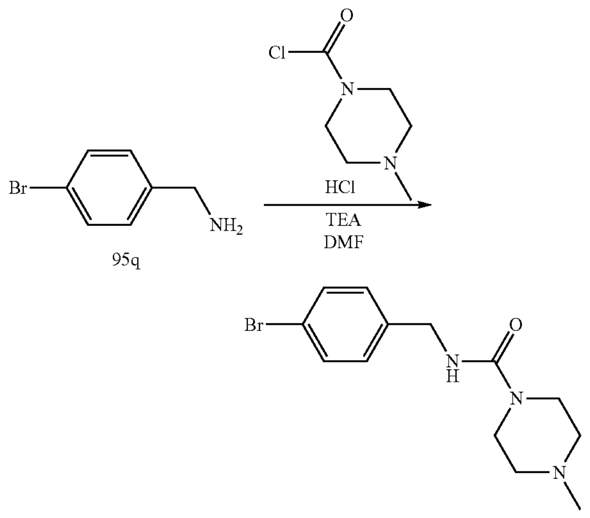

95q

104a

4-Methyl-piperazine-1-carboxylic acid 4-bromo-benzylamide was synthesized by operations similar to those in Reaction 82-1 using appropriate reagents and starting material.

MS (ESI) m/z=312 (M+H)+.

The aryl bromide reagent used in the synthesis of Compound 568 (N'-(4-bromo-3-methyl-phenyl)-N,N-dimethyl-sulfamide) was synthesized as follows.

(Reaction 104-2)

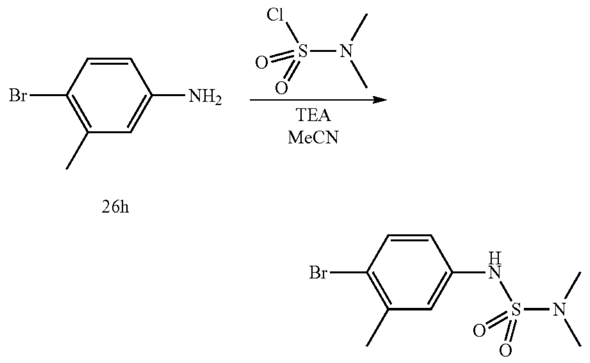

26h

104b

N'-(4-Bromo-3-methyl-phenyl)-N,N-dimethyl-sulfamide was synthesized by operations similar to those in Reaction 82-1 using appropriate reagents and starting material.

MS (ESI) m/z=293 (M+H)+.

The aryl bromide reagent used in the synthesis of Compound 569 ((4-bromo-3-methyl-benzyl)-(3-dimethylamino-propyl)-carbamic acid tert-butyl ester) was synthesized as follows.

(Reaction 104-3)

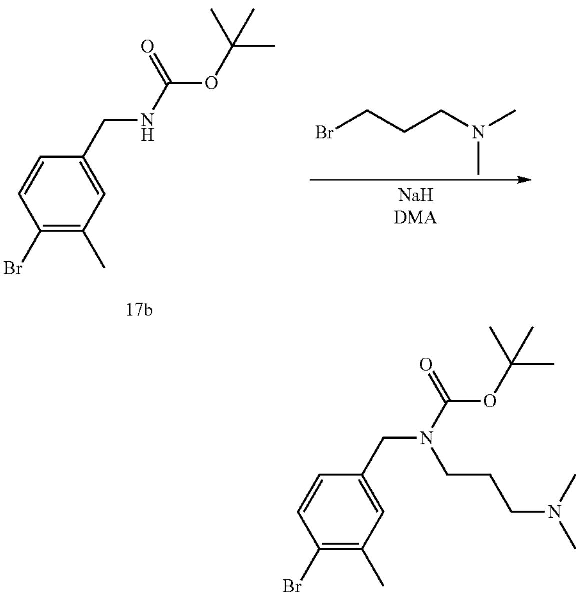

17b

104c (4-Bromo-3-methyl-benzyl)-(3-dimethylamino-propyl)-carbamic acid tert-butyl ester was synthesized by operations similar to those in Reaction 25-3 using appropriate reagents and starting material.

MS (ESI) m/z=385, 387 (M+H)+.

The aryl bromide reagent used in the synthesis of Compound 570 (2-(4-bromo-phenyl)-N-(2,2-dimethyl-propyl)-acetamide) was synthesized as follows.

(Reaction 104-4)

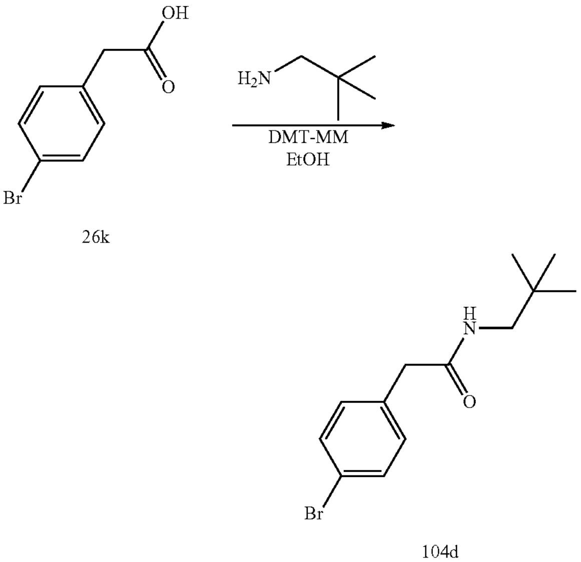

26k

104d 2-(4-Bromo-phenyl)-N-(2,2-dimethyl-propyl)-acetamide was synthesized by operations similar to those in Reaction 10-1 using appropriate reagents and starting material.

MS (ESI) m/z=285, 287 (M+H)+.

The aryl bromide reagent used in the synthesis of Compound 571 (2-(4-bromo-phenyl)-N-(2-diisopropylamino-ethyl)acetamide) was synthesized as follows.

(Reaction 104-5)

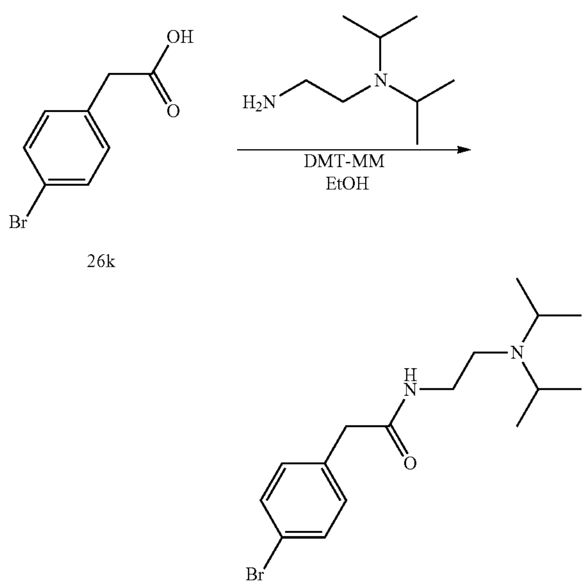

26k

104e 2-(4-Bromo-phenyl)-N-(2-diisopropylamino-ethyl)acetamide was synthesized by operations similar to those in Reaction 10-1 using appropriate reagents and starting material.

MS (ESI) m/z=342, 344 (M+H)+.

The aryl bromide reagent used in the synthesis of Compound 572 (1-(4-bromo-3-methyl-phenyl)-azetidin-2-one) was synthesized as follows.

(Reaction 104-6)

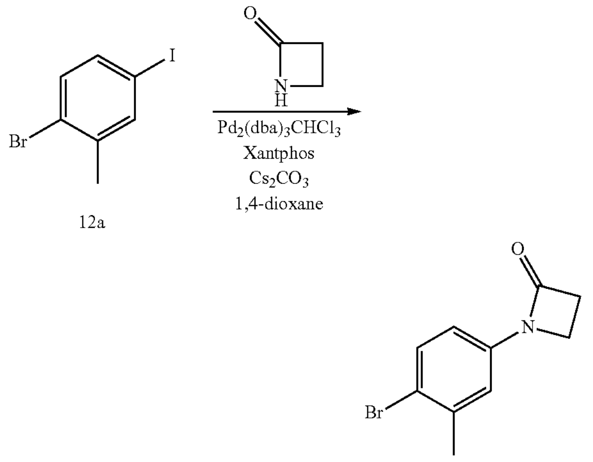

12a

104f 1-(4-Bromo-3-methyl-phenyl)-azetidin-2-one was synthesized by operations similar to those in Reaction 29-3 using appropriate reagents and starting material.

MS (ESI) m/z=240, 242 (M+H)+.

The aryl bromide reagent used in the synthesis of Compound 573 ((4-bromo-3,5-dimethyl-phenyl)-thiazol-2-yl-amine) was synthesized as follows.

(Reaction 104-7)

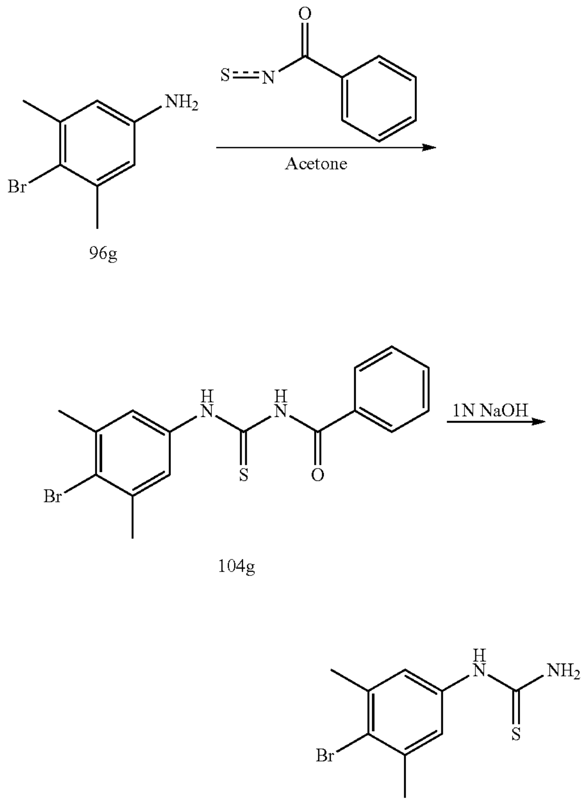

96g

104g

104h

A solution of 4-bromo-3,5-dimethyl-phenylamine (200 mg) and benzoyl isothiocyanate (0.14 ml) in acetone (2 ml) was heated under reflux for 30 minutes. After cooling the reaction solution, a 1 N aqueous sodium hydroxide solution (2.19 ml) was added and the mixture was stirred at 50° C. for 12 hours. The mixture was extracted with dichloromethane, and the organic layer was then dried over anhydrous sodium sulfate and concentrated under reduced pressure. The resulting residue was triturated with hexane to give (4-bromo-3,5-dimethyl-phenyl)-thiourea (146 mg, 57%).

$^1$H-NMR (300 MHz, DMSO-d6) δ 9.62 (1H, s), 7.8-7.2 (2H, br), 7.19 (2H, s), 2.32 (6H, s).

(Reaction 104-8)

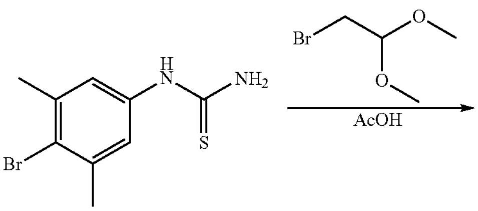

104h

-continued

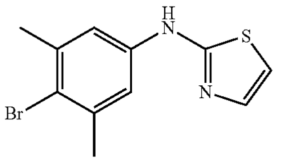

104i (4-Bromo-3,5-dimethyl-phenyl)-thiazol-2-yl-amine was synthesized by operations similar to those in Reaction 94-1 using appropriate reagents and starting material.

MS (ESI) m/z=285 (M+H)+.

The aryl bromide reagent used in the synthesis of Compound 574 (N-(4-bromo-3,5-dimethyl-phenyl)-N-(3-methyl-oxetan-3-ylmethyl)-acetamide) was synthesized as follows.

(Reaction 104-9)

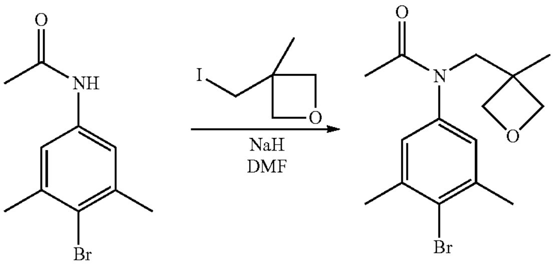

26a 104j

N-(4-Bromo-3,5-dimethyl-phenyl)-N-(3-methyl-oxetan-3-ylmethyl)-acetamide was synthesized by operations similar to those in Reaction 25-3 using appropriate reagents and starting material.

MS (ESI) m/z=326, 328 (M+H)+.

Example 105

3-(3,5-Dimethyl-4-{(E)-2-[2-(4-methyl-cyclohexyl)-4-oxo-1,3,8-triaza-spiro[4.5]dec-1-ene-8-sulfonyl]-vinyl}-phenyl)-imidazolidine-2,4-dione (Compound 575)

(Reaction 105-1)

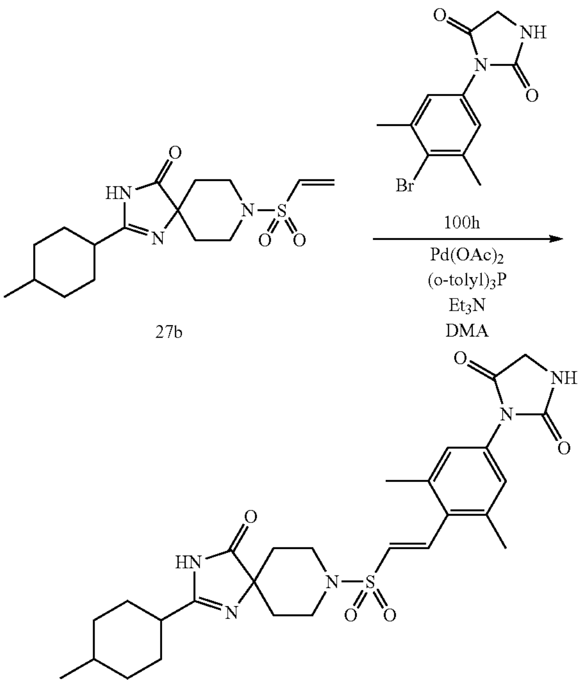

Compound 575

3-(3,5-Dimethyl-4-{(E)-2-[2-(4-methyl-cyclohexyl)-4-oxo-1,3,8-triaza-spiro[4.5]dec-1-ene-8-sulfonyl]-vinyl}-phenyl)-imidazolidine-2,4-dione was synthesized by operations similar to those in Reaction 26-1 using appropriate reagents and starting material.

MS (ESI) m/z=542 (M+H)+.

The example compounds shown below were synthesized by operations similar to those in Example 105 using appropriate reagents and starting materials.

Compounds 576 to Compound 589

TABLE 80

| Target Compound | Structure | LCMS condition | Retention time (min) | MS (m/z) |
|---|---|---|---|---|
| 576 | 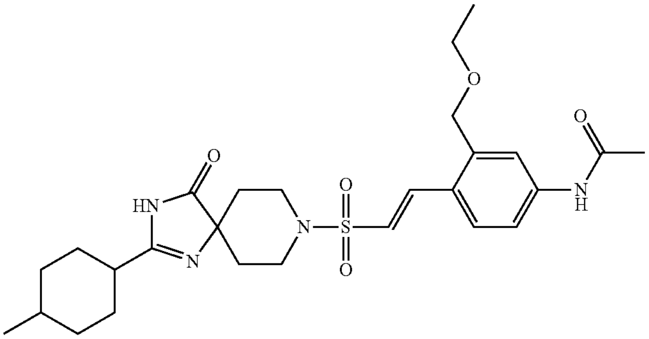 [SMILES: CCOCc1cc(NC(C)=O)ccc1/C=C/S(=O)(=O)N1CCC2(CC1)N=C(C1CCC(C)CC1)NC2=O] | LCMS-D-1 | 2.82 | 531 (M + H)+ |

TABLE 80-continued
| Target Compound | Structure | LCMS condition | Retention time (min) | MS (m/z) |
|---|---|---|---|---|
| 577 | 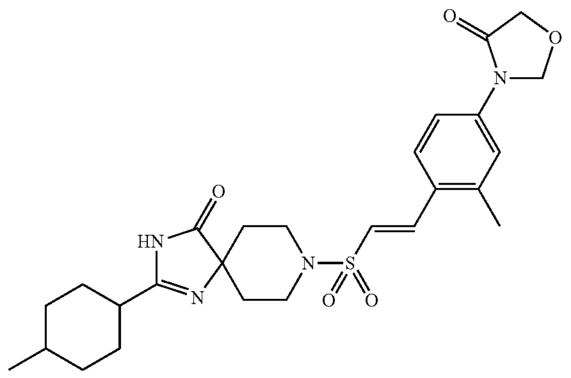 [SMILES: Cc1cc(N2COCC2=O)ccc1/C=C/S(=O)(=O)N1CCC2(CC1)N=C(C1CCC(C)CC1)NC2=O] | LCMS-C-1 | 2.62 | 515 (M + H)+ |
| 578 | 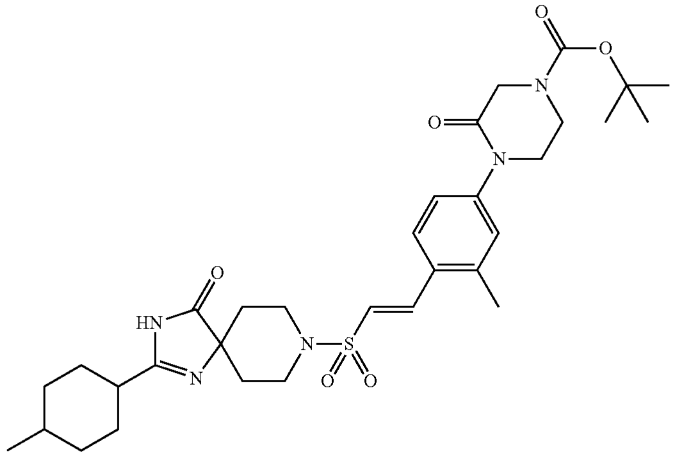 [SMILES: Cc1cc(N2CCN(C(=O)OC(C)(C)C)CC2=O)ccc1/C=C/S(=O)(=O)N1CCC2(CC1)N=C(C1CCC(C)CC1)NC2=O] | LCMS-A-1 | 2.44 | 628 (M + H)+ |
| 579 | 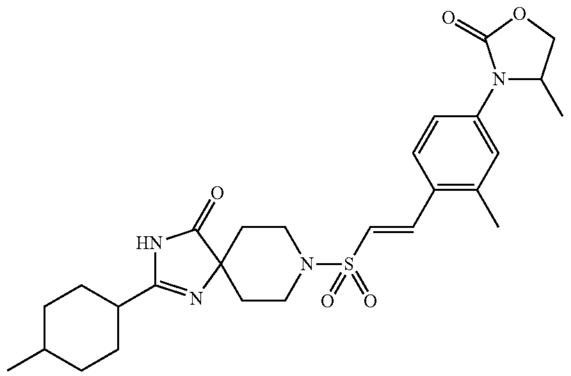 | LCMS-A-1 | 2.23 | 529 (M + H)+ |
| 580 | 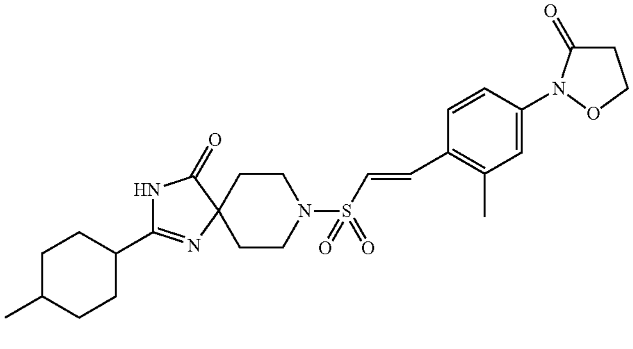 [SMILES: Cc1cc(N2OCCC2=O)ccc1/C=C/S(=O)(=O)N1CCC2(CC1)N=C(C1CCC(C)CC1)NC2=O] | LCMS-C-1 | 2.72 | 515 (M + H)+ |

TABLE 80-continued
| Target Compound | Structure | LCMS condition | Retention time (min) | MS (m/z) |
|---|---|---|---|---|
| 581 | 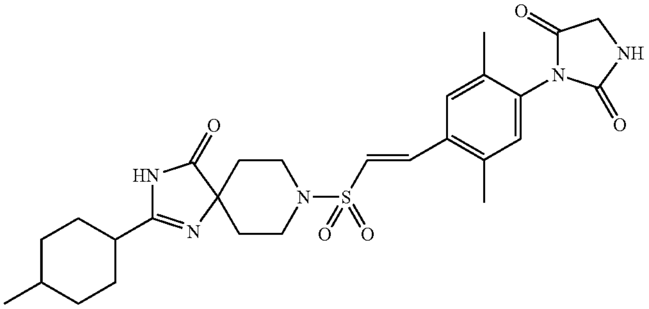 [SMILES: Cc1cc(N2C(=O)CNC2=O)c(C)cc1/C=C/S(=O)(=O)N1CCC2(CC1)N=C(C1CCC(C)CC1)NC2=O] | LCMS-C-1 | 2.42 | 542 (M + H)+ |
| 582 | 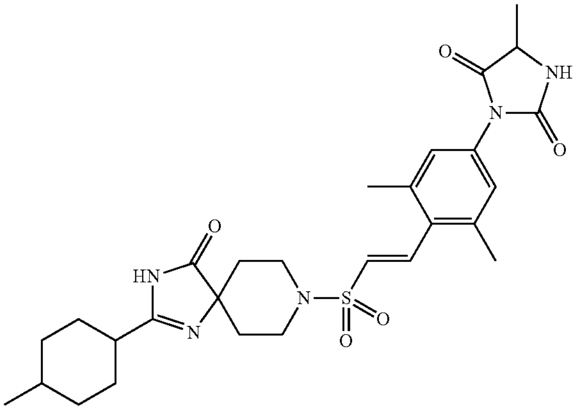 [SMILES: Cc1cc(N2C(=O)NC(C)C2=O)cc(C)c1/C=C/S(=O)(=O)N1CCC2(CC1)N=C(C1CCC(C)CC1)NC2=O] | LCMS-A-1 | 2.05 | 556 (M + H)+ |
| 583 | 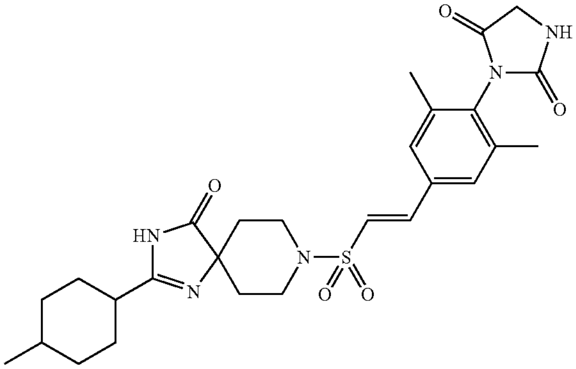 [SMILES: Cc1cc(/C=C/S(=O)(=O)N2CCC3(CC2)N=C(C2CCC(C)CC2)NC3=O)cc(C)c1N1C(=O)CNC1=O] | LCMS-A-1 | 1.95 | 542 (M + H)+ |
| 584 | 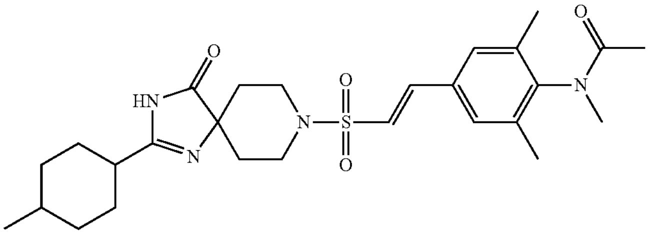 [SMILES: CC(=O)N(C)c1c(C)cc(/C=C/S(=O)(=O)N2CCC3(CC2)N=C(C2CCC(C)CC2)NC3=O)cc1C] | LCMS-D-1 | 1.93 | 515 (M + H)+ |
| 585 | 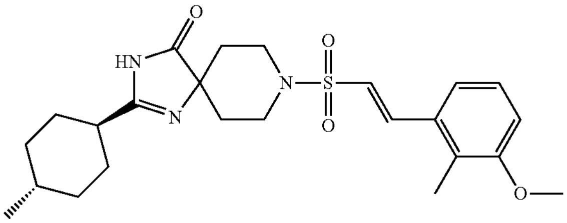 | LCMS-F-1 | 1.05 | 460 (M + H)+ |

TABLE 80-continued
| Target Compound | Structure | LCMS condition | Retention time (min) | MS (m/z) |
| --- | --- | --- | --- | --- |
| 586 | 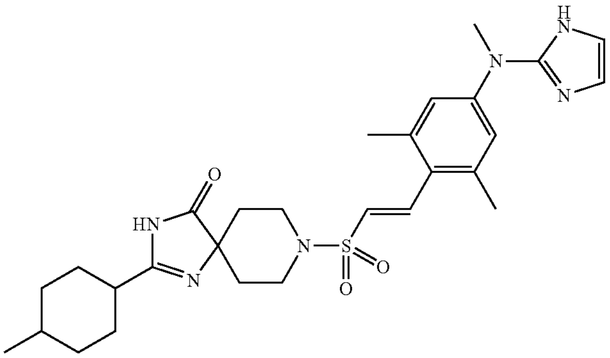 [SMILES: Cc1cc(N(C)c2ncc[nH]2)cc(C)c1/C=C/S(=O)(=O)N1CCC2(CC1)N=C(C1CCC(C)CC1)NC2=O] | LCMS-A-1 | 1.83 | 539 (M + H)+ |
| 587 | 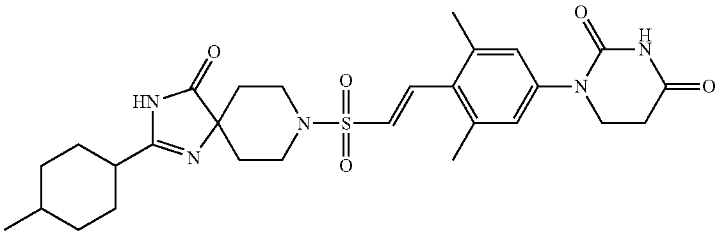 | LCMS-D-1 | 2.02 | 556 (M + H)+ |
| 588 | 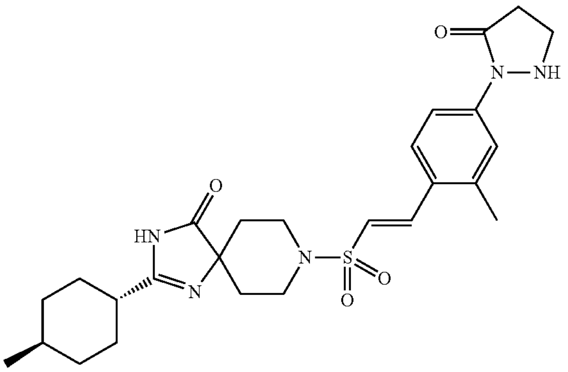 [SMILES: Cc1cc(N2NCCC2=O)ccc1/C=C/S(=O)(=O)N1CCC2(CC1)N=C([C@H]1CC[C@H](C)CC1)NC2=O] | LCMS-C-1 | 2.53 | 515 (M + H)+ |
| 589 | 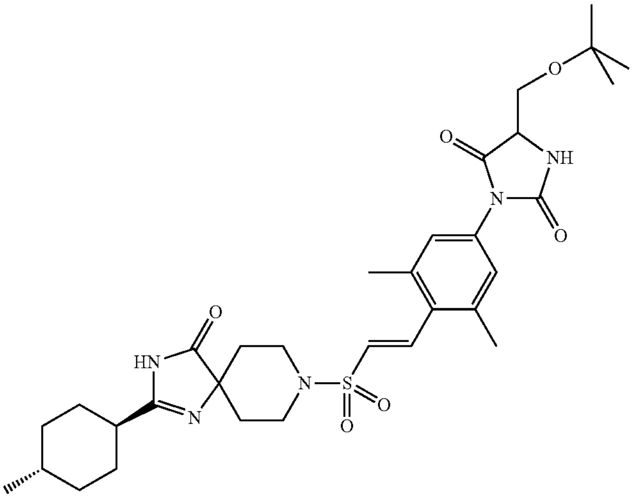 [SMILES: Cc1cc(N2C(=O)NC(COC(C)(C)C)C2=O)cc(C)c1/C=C/S(=O)(=O)N1CCC2(CC1)N=C([C@H]1CC[C@H](C)CC1)NC2=O] | LCMS-C-1 | 2.83 | 628 (M + H)+ |

The aryl bromide reagent used in the synthesis of Compound 577 (3-(4-bromo-3-methyl-phenyl)-oxazolidin-4-one) was synthesized as follows.

(Reaction 105-2)

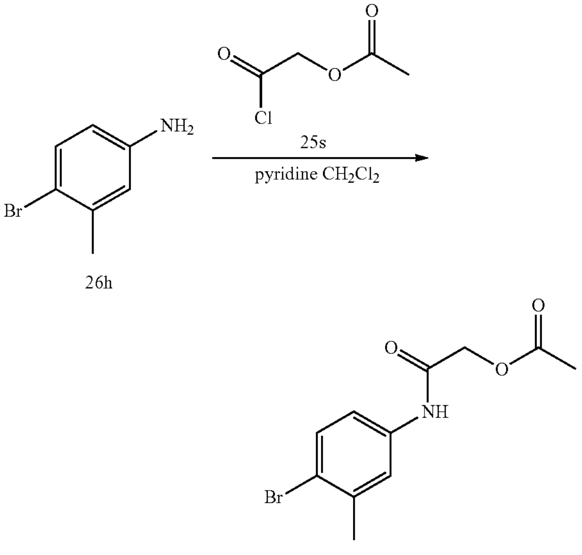

26h

105a

Acetic acid chlorocarbonylmethyl ester (1.73 ml) was added to a solution of 4-bromo-3-methyl-phenylamine (2.0 g, 10.7 mmol) and pyridine (5.21 ml) in dichloromethane (20 ml), and the mixture was stirred at 40° C. for 2.5 hours. The mixture was cooled, and then quenched with water and extracted with dichloromethane. The organic layer was sequentially washed with water and saturated brine, and then dried over anhydrous sodium sulfate and concentrated under reduced pressure to give acetic acid (4-bromo-3-methyl-phenylcarbamoyl)-methyl ester (3.19 g).

$^1$H-NMR (400 MHz, $CDCl_3$) δ 2.24 (3H, s), 2.39 (3H, s), 4.68 (2H, s), 7.22-7.25 (1H, m), 7.46-7.50 (2H, m), 7.70 (1H, brs).

(Reaction 105-3)

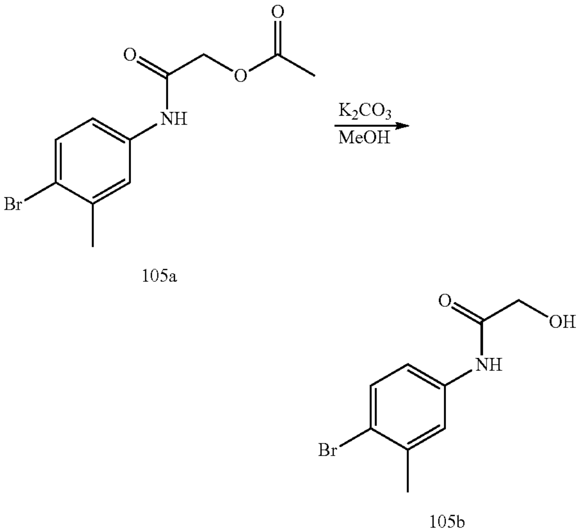

105a

105b

N-(4-Bromo-3-methyl-phenyl)-2-hydroxy-acetamide was synthesized by operations similar to those in Reaction 12-5 using appropriate reagents and starting material.

MS (ESI) m/z=244, 246 (M+H)+.

(Reaction 105-4)

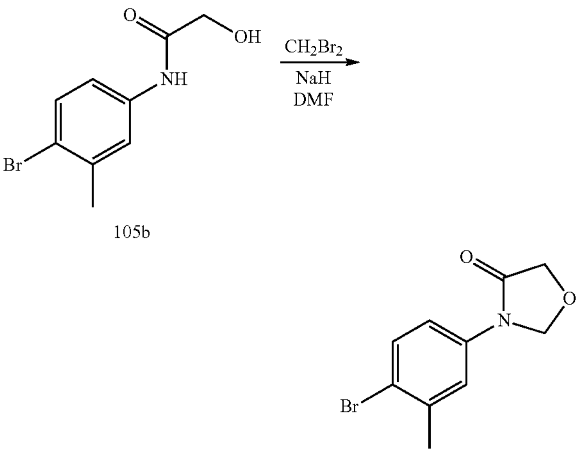

105b

105c

Sodium hydride (81 mg, 1.80 mmol) was added to a solution of N-(4-bromo-3-methyl-phenyl)-2-hydroxy-acetamide (200 mg, 0.819 mmol) in DMF (4.0 ml), and the mixture was stirred at room temperature for 50 minutes. Further, dibromomethane (0.114 ml, 1.64 mmol) was added to the reaction solution, and the mixture was heated with stirring at 110° C. for two hours. Cooling to room temperature and subsequent purification by silica gel column chromatography (hexane-ethyl acetate) gave 3-(4-bromo-3-methyl-phenyl)-oxazolidin-4-one (45 mg, 21%).

MS (ESI) m/z=256, 258 (M+H)+.

The aryl bromide reagent used in the synthesis of Compound 578 (4-(4-bromo-3-methyl-phenyl)-3-oxo-piperazine-1-carboxylic acid tert-butyl ester) was synthesized as follows.

(Reaction 105-5)

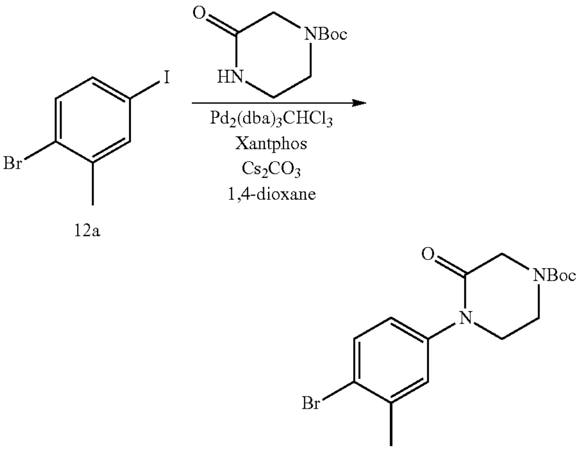

12a

105d 4-(4-Bromo-3-methyl-phenyl)-3-oxo-piperazine-1-carboxylic acid tert-butyl ester was synthesized by operations similar to those in Reaction 29-3 using appropriate reagents and starting material.

MS (ESI) m/z=369, 371 (M+H)+.

The aryl bromide reagent used in the synthesis of Compound 579 (3-(4-bromo-3-methyl-phenyl)-4-methyl-oxazolidin-2-one) was synthesized as follows.

(Reaction 105-6)

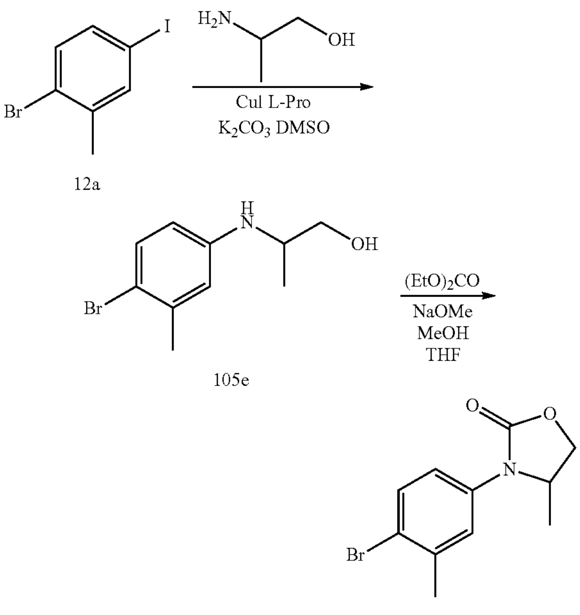

12a

105e

105f 3-(4-Bromo-3-methyl-phenyl)-4-methyl-oxazolidin-2-one was synthesized by operations similar to those in Reaction 12-1 and Reaction 96-13 using appropriate reagents and starting material.

MS (ESI) m/z=270, 272 (M+H)+.

The aryl bromide reagent used in the synthesis of Compound 580 (2-(4-bromo-3-methyl-phenyl)-isoxazolidin-3-one) was synthesized as follows.

(Reaction 105-7)

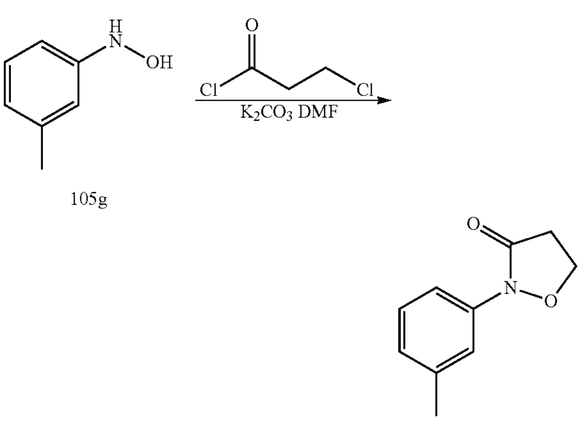

105g

105h

3-Chloro-propionyl (157 μL, 1.65 mmol) was added to a mixture of N-m-tolyl-hydroxylamine (235 mg, 1.69 mmol) and potassium carbonate (223 mg, 1.69 mmol) in N,N-dimethylformamide (1.7 mL) at −10° C. The mixture was stirred at room temperature for 2.5 hours, and water and ethyl acetate were then added. The organic layer and the aqueous layer were separated, and the aqueous layer was repeatedly extracted with ethyl acetate three times. The organic layers were combined, washed with water twice and saturated brine, and then concentrated under reduced pressure. The resulting residue was purified by silica gel column chromatography to give 2-m-tolyl-isoxazolidin-3-one as a pale yellow solid (213 mg, 73%).

MS (ESI) m/z=178 (M+H)+.

(Reaction 105-8)

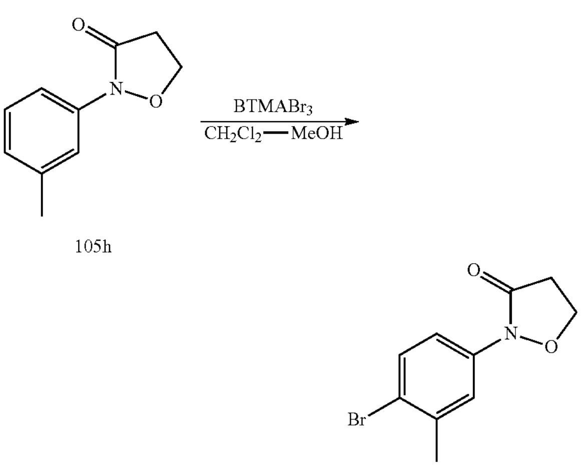

105h

105i 2-(4-Bromo-3-methyl-phenyl)-isoxazolidin-3-one was synthesized by operations similar to those in Reaction 26-2 using appropriate reagents and starting material.

MS (ESI) m/z=297, 299 (M+H)+.

The aryl iodide reagent used in the synthesis of Compound 581 (3-(4-iodo-2,5-dimethyl-phenyl)-imidazolidine-2,4-dione) was synthesized as follows.

(Reaction 105-9)

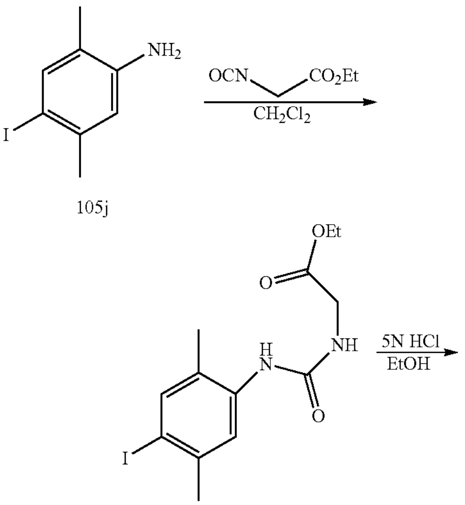

105j

105k

-continued

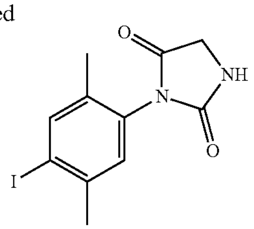

1051

3-(4-Iodo-2,5-dimethyl-phenyl)-imidazolidine-2,4-dione was synthesized by operations similar to those in Reaction 84-1 and Reaction 96-1 using appropriate reagents and starting material.

MS (ESI) m/z=331 (M+H)+.

The aryl bromide reagent used in the synthesis of Compound 582 (3-(4-bromo-3,5-dimethyl-phenyl)-5-methyl-imidazolidine-2,4-dione) was synthesized as follows.

(Reaction 105-10)

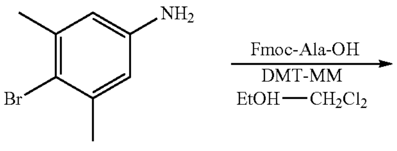

96g

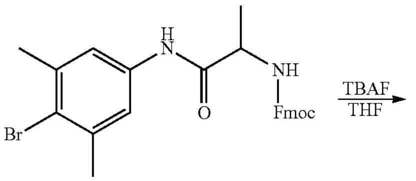

105m

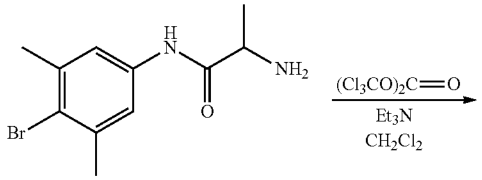

105n

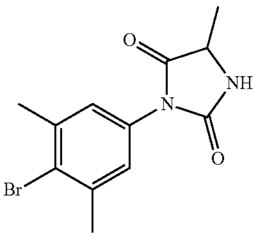

105o 3-(4-Bromo-3,5-dimethyl-phenyl)-5-methyl-imidazolidine-2,4-dione was synthesized by operations similar to those in Reaction 10-1, Reaction 39-2 and Reaction 96-10 using appropriate reagents and starting material.

MS (ESI) m/z=297, 299 (M+H)+.

The aryl bromide reagent used in the synthesis of Compound 583 (3-(4-bromo-2,6-dimethyl-phenyl)-imidazolidine-2,4-dione) was synthesized as follows.

(Reaction 105-11)

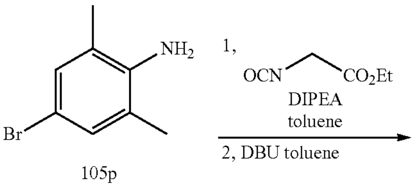

105p

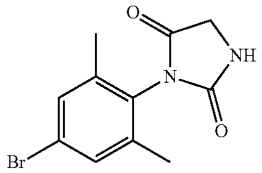

105q

Ethyl isocyanatoacetate (581 mg, 4.50 mmol) and N,N-diisopropylethylamine (426 mg, 1.65 mmol) were added to a solution of 4-bromo-2,6-dimethylaniline (600 mg, 3.00 mmol) in toluene (6 ml) with stirring in a nitrogen stream, and the mixture was heated with stirring at 120° C. After 30 minutes, the reaction solution was brought to room temperature, and the precipitate was collected by filtration, washed with toluene and then dried under reduced pressure. The resulting solid was suspended in toluene (6 ml). DBU (68.4 mg, 2.25 mmol) was added and the mixture was heated with stirring at 120° C. After 30 minutes, the reaction solution was brought to room temperature and diluted with ethyl acetate, and the organic layer was washed with a 1 N aqueous hydrochloric acid solution and saturated brine. The organic layer was dried over anhydrous magnesium sulfate, and the magnesium sulfate was then removed by filtration. The filtrate was concentrated under reduced pressure. The residue was subjected to column chromatography (hexane-ethyl acetate) to give 3-(4-bromo-2,6-dimethyl-phenyl)-imidazolidine-2,4-dione (570 mg, 67%).

MS (ESI) m/z=283, 285 (M+H)+.

The aryl bromide reagent used in the synthesis of Compound 584 (N-(4-bromo-2,6-dimethyl-phenyl)-N-methyl-acetamide) was synthesized as follows.

(Reaction 105-12)

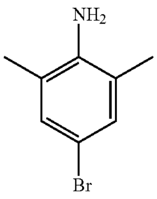

105p

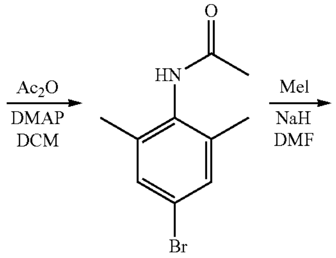

105r

-continued

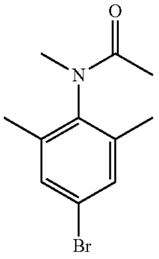

105s

N-(4-Bromo-2,6-dimethyl-phenyl)-N-methyl-acetamide was synthesized by operations similar to those in Reaction 19-2 (using DMAP as a base) and Reaction 25-3 using appropriate reagents and starting material.

MS (ESI) m/z=256, 258 (M+H)+.

The aryl bromide reagent used in the synthesis of Compound 586 ((4-bromo-3,5-dimethyl-phenyl)-(1H-imidazol-2-yl)-methyl-amine) was synthesized as follows.

(Reaction 105-13)

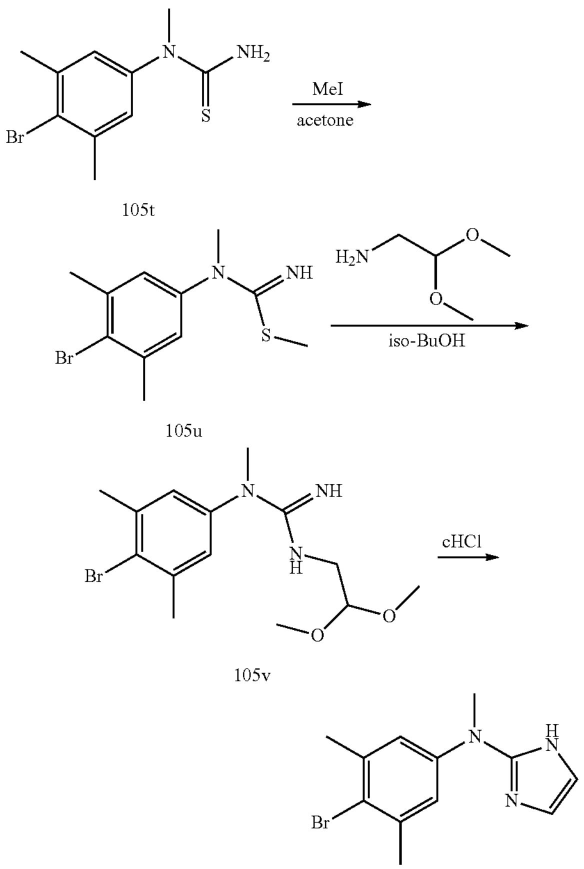

105t, 105u, 105v, 105w

Iodomethane (260 mg, 9.15 mmol) was added to a solution of 1-(4-bromo-3,5-dimethyl-phenyl)-1-methyl-thiourea (500 mg, 1.83 mmol) in acetone (10 ml) with stirring in a nitrogen stream, and the mixture was heated with stirring at 50° C. for two hours. The reaction solution was concentrated under reduced pressure, and a mixture of the resulting residue and aminoacetaldehyde dimethylacetal (250 mg, 2.38 mmol) in iso-BuOH (8.3 ml) was then heated under reflux for four hours. The reaction mixture was concentrated under reduced pressure. Concentrated hydrochloric acid (3 ml) was then added to the resulting residue, and the mixture was heated with stirring at 90° C. for 30 minutes. The reaction mixture was cooled and then adjusted to pH 10 with a 2 N aqueous sodium hydroxide solution, followed by extraction with dichloromethane. The organic layer was dried over anhydrous magnesium sulfate and then concentrated under reduced pressure. The residue was purified by silica gel column chromatography (dichloromethane-methanol) to give (4-bromo-3,5-dimethyl-phenyl)-(1H-imidazol-2-yl)-methyl-amine (145 mg, 28%).

$^1$H-NMR (400 MHz, DMSO-d6) δ 2.30 (6H, s), 3.25 (3H, s), 6.71 (1H, s), 6.83 (2H, s), 6.87 (1H, s).

MS (ESI) m/z=280 (M+H)+.

The aryl bromide reagent used in the synthesis of Compound 587 (1-(4-bromo-3,5-dimethyl-phenyl)-dihydro-pyrimidine-2,4-dione) was synthesized as follows.

(Reaction 105-14)

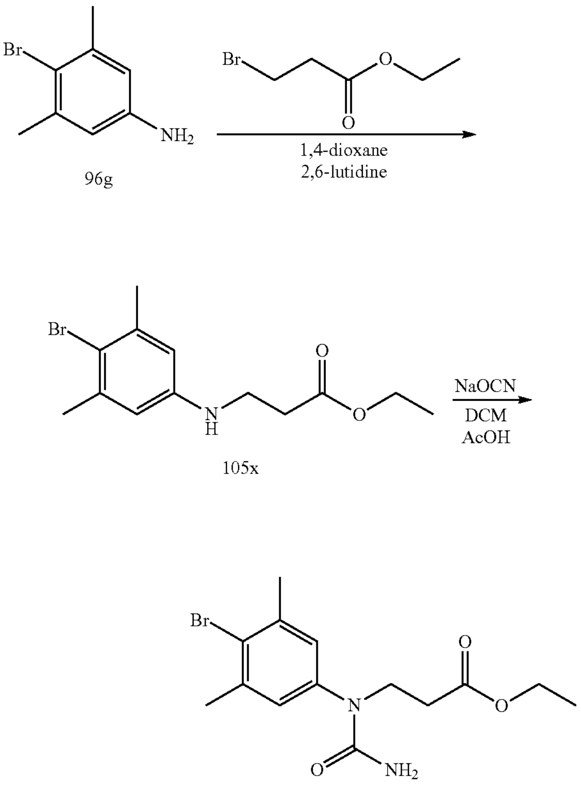

96g, 105x, 105y

3-[1-(4-Bromo-3,5-dimethyl-phenyl)-ureido]-propionic acid ethyl ester was synthesized by operations similar to those in Reaction 25-12 (using 1,4-dioxane as a solvent and 2,6-lutidine as a base) and Reaction 89-2 using appropriate reagents and starting material.

$^1$H-NMR ($CDCl_3$) δ 6.99 (s, 2H), 4.43 (brs, 2H), 4.05 (q, 2H, J=7.25 Hz), 3.94 (t, 2H, J=7.25 Hz), 2.57 (t, 2H, J=7.25 Hz), 2.42 (s, 6H), 1.20 (t, 3H, J=7.25 Hz).

(Reaction 105-15)

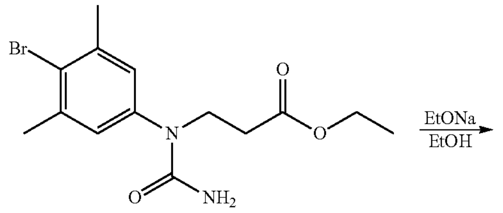

105y

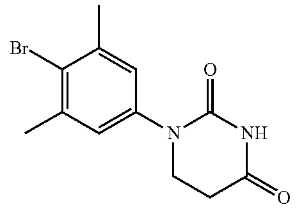

105z

A solution of sodium ethoxide (15.7 mg, 0.033 mmol) in ethanol (0.1 ml) was added to a solution of 3-[1-(4-bromo-3, 5-dimethyl-phenyl)-ureido]-propionic acid ethyl ester (11.4 mg, 0.033 mmol) in ethanol (0.9 ml), and the mixture was stirred at room temperature for 24 hours. The mixture was adjusted to pH 4 with 1 N hydrochloric acid and then extracted with dichloromethane. The organic layer was dried over anhydrous magnesium sulfate and then concentrated under reduced pressure. The resulting residue was purified by silica gel column chromatography (dichloromethane-ethyl acetate) to give 1-(4-bromo-3,5-dimethyl-phenyl)-dihydro-pyrimidine-2,4-dione (9.8 mg, 99%).

$^1$H-NMR ($CDCl_3$) δ 7.59 (s, 1H), 7.03 (s, 2H), 3.83 (t, 2H, J=6.49 Hz), 2.83 (t, 2H, J=6.49 Hz), 2.42 (s, 6H).

The aryl bromide reagent used in the synthesis of Compound 588 (2-(4-bromo-3-methyl-phenyl)-pyrazolidin-3-one) was synthesized as follows.

(Reaction 105-16)

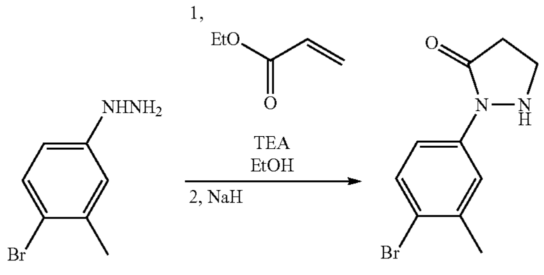

105aa 105ab

Triethylamine (625 μL, 13.1 mmol) and acrylic acid ethyl ester (1.82 mL, 5.74 mmol) were added to a solution of (4-bromo-3-methyl-phenyl)-hydrazine (1.05 g, 5.22 mmol) in EtOH (26.1 mL) at room temperature in a nitrogen atmosphere, and the mixture was stirred at 80° C. for 18 hours. The reaction solution was cooled, and 50% NaH (501 mg, 10.4 mmol) was then added to the reaction solution at 0° C. The mixture was stirred at 0° C. for 30 minutes, and 50% NaH (251 mg, 5.20 mmol) was then further added, followed by further stirring for 30 minutes. The reaction mixture was quenched with a saturated aqueous ammonium chloride solution and extracted with ethyl acetate three times. The organic layers were combined and washed with a mixed solution of water:saturated brine (1:1). After separation, the organic layer was dried over sodium sulfate and concentrated under reduced pressure. The resulting residue was purified by silica gel column chromatography (hexane-ethyl acetate) to give 2-(4-bromo-3-methyl-phenyl)-pyrazolidin-3-one as a brown form (684 mg, 60%).

MS (ESI) m/z=255, 257 (M+H)+.

The aryl bromide reagent used in the synthesis of Compound 589 (3-(4-bromo-3,5-dimethyl-phenyl)-5-tert-butoxymethyl-imidazolidine-2,4-dione) was synthesized as follows.

(Reaction 105-17)

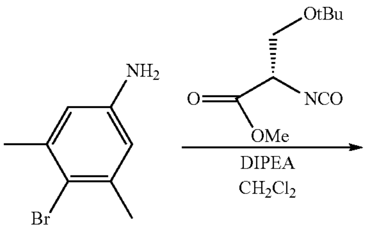

96g

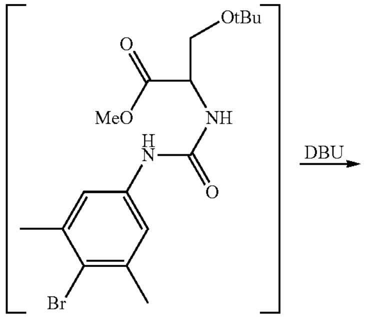

105ac

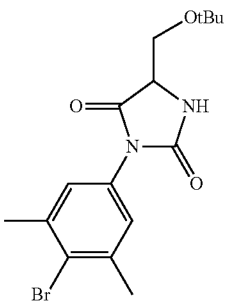

105ad 3-(4-Bromo-3,5-dimethyl-phenyl)-5-tert-butoxymethyl-imidazolidine-2,4-dione was synthesized by operations similar to those in Reaction 105-11 using appropriate reagents and starting material.

MS (ESI) m/z=367, 369 (M−H)−.

Example 106

N,N-Dimethyl-2-(3-methyl-4-{(E)-2-[4-oxo-2-(3-trifluoromethyl-phenyl)-1,3,8-triaza-spiro[4.5]dec-1-ene-8-sulfonyl]-vinyl}-benzenesulfonylamino)-acetamide (Compound 590)

(Reaction 106-1)

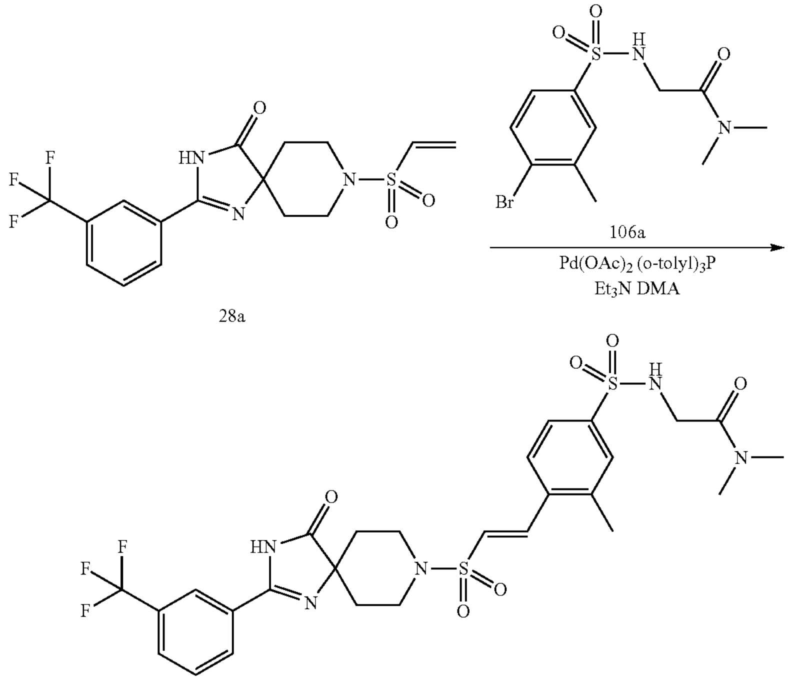

106a

28a

Compound 590

N,N-Dimethyl-2-(3-methyl-4-{(E)-2-[4-oxo-2-(3-trifluoromethyl-phenyl)-1,3,8-triaza-spiro[4.5]dec-1-ene-8-sulfonyl]-vinyl}-benzenesulfonylamino)-acetamide was synthesized by operations similar to those in Reaction 26-1 using appropriate reagents and starting material.

MS (ESI) m/z=642 (M+H)+.

The example compounds shown below were synthesized by operations similar to those in Example 106 using appropriate reagents and starting materials.

Compounds 591 to Compound 595

TABLE 81

| Target Compound | Structure | LCMS condition | Retention time (min) | MS (m/z) |
|---|---|---|---|---|
| 591 | 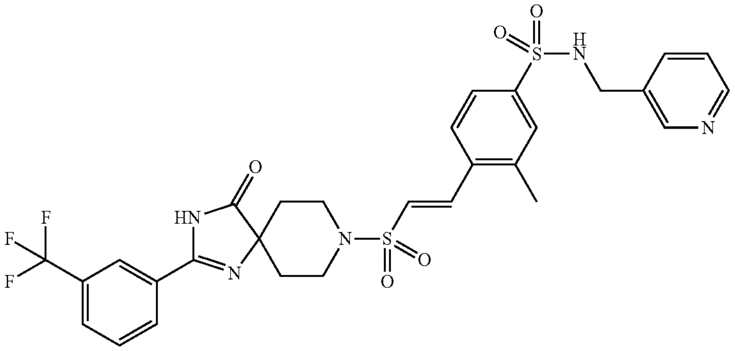 [SMILES: Cc1cc(S(=O)(=O)NCc2cccnc2)ccc1/C=C/S(=O)(=O)N1CCC2(CC1)N=C(c1cccc(C(F)(F)F)c1)NC2=O] | LCMS-C-1 | 2.57 | 648 (M + H)+ |

TABLE 81-continued
| Target Compound | Structure | LCMS condition | Retention time (min) | MS (m/z) |
|---|---|---|---|---|
| 592 | 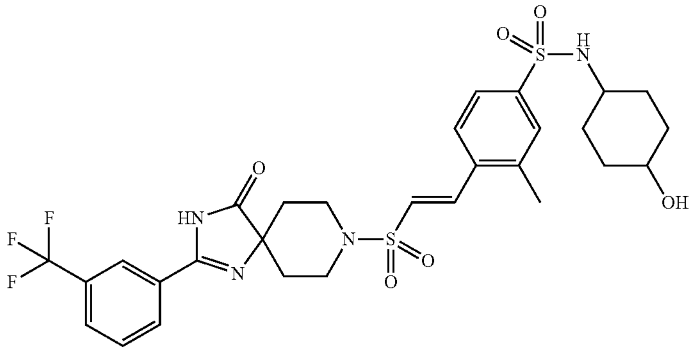 [SMILES: Cc1cc(S(=O)(=O)NC2CCC(O)CC2)ccc1/C=C/S(=O)(=O)N1CCC2(CC1)N=C(c1cccc(C(F)(F)F)c1)NC2=O] | LCMS-C-1 | 2.48 | 655 (M + H)+ |
| 593 | 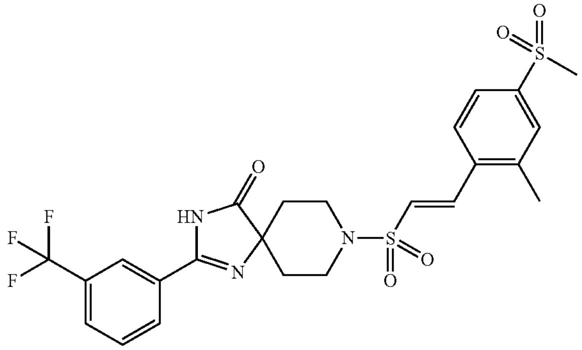 [SMILES: Cc1cc(S(C)(=O)=O)ccc1/C=C/S(=O)(=O)N1CCC2(CC1)N=C(c1cccc(C(F)(F)F)c1)NC2=O] | LCMS-C-1 | 2.48 | 556 (M + H)+ |
| 594 | 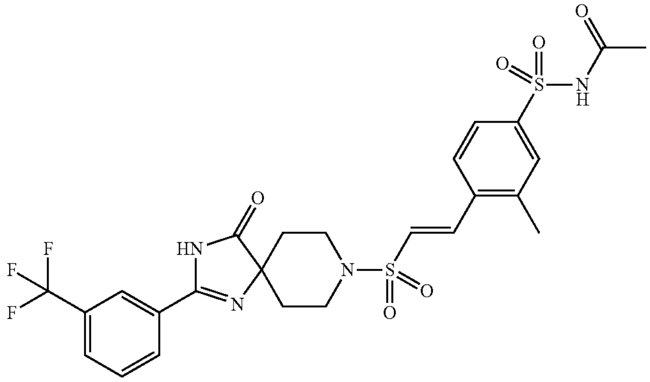 [SMILES: CC(=O)NS(=O)(=O)c1ccc(/C=C/S(=O)(=O)N2CCC3(CC2)N=C(c2cccc(C(F)(F)F)c2)NC3=O)c(C)c1] | LCMS-A-1 | 2.43 | 599 (M + H)+ |
| 595 | 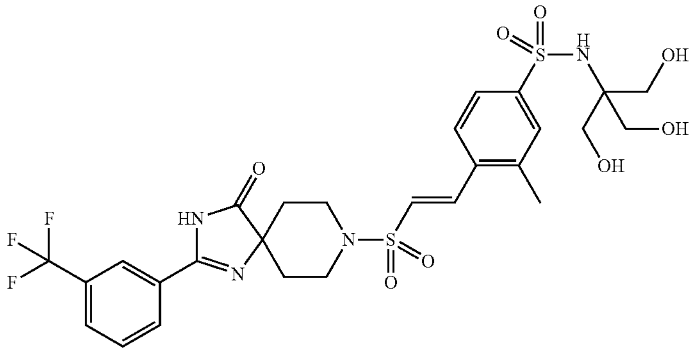 [SMILES: Cc1cc(S(=O)(=O)NC(CO)(CO)CO)ccc1/C=C/S(=O)(=O)N1CCC2(CC1)N=C(c1cccc(C(F)(F)F)c1)NC2=O] | LCMS-C-1 | 2.35 | 661 (M + H)+ |

The aryl bromide reagent used in the synthesis of Compound 590 (2-(4-bromo-3-methyl-benzenesulfonylamino)-N,N-dimethyl-acetamide) was synthesized as follows.

(Reaction 106-2)

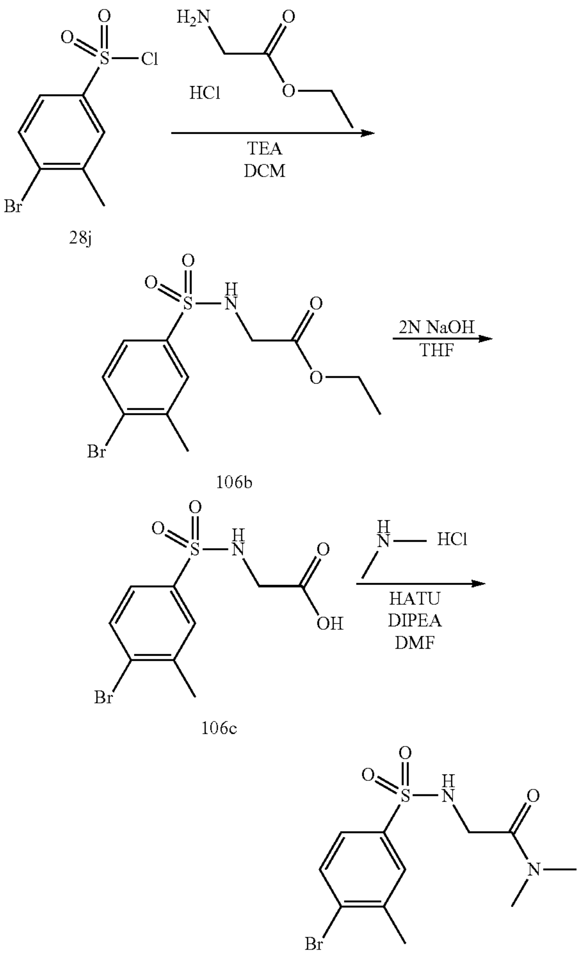

28j

106b

106c

106a 2-(4-Bromo-3-methyl-benzenesulfonylamino)-N,N-dimethyl-acetamide was synthesized by operations similar to those in Reaction 5-4, Reaction 95-18 and Reaction 10-14 using appropriate reagents and starting material.

MS (ESI) m/z=335, 337 (M+H)+.

The aryl bromide reagent used in the synthesis of Compound 591 (4-bromo-3-methyl-N-pyridin-3-ylmethyl-benzenesulfonamide) was synthesized as follows.

(Reaction 106-3)

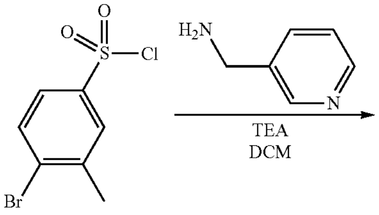

28j

-continued

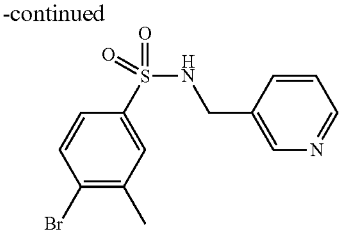

106d

4-Bromo-3-methyl-N-pyridin-3-ylmethyl-benzenesulfonamide was synthesized by operations similar to those in Reaction 5-4 using appropriate reagents and starting material.

MS (ESI) m/z=341, 343 (M+H)+.

The aryl bromide reagent used in the synthesis of Compound 592 (4-bromo-N-(4-hydroxy-cyclohexyl)-3-methyl-benzenesulfonamide) was synthesized as follows.

(Reaction 106-4)

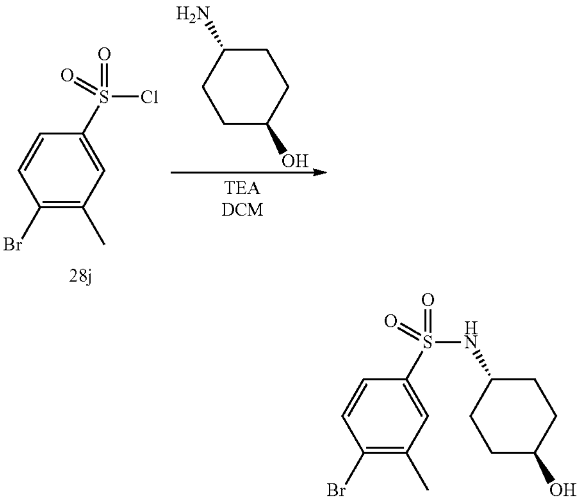

28j

106e

4-Bromo-N-(4-hydroxy-cyclohexyl)-3-methyl-benzenesulfonamide was synthesized by operations similar to those in Reaction 5-4 using appropriate reagents and starting material.

MS (ESI) m/z=348, 350 (M+H)+.

The aryl bromide reagent used in the synthesis of Compound 594 (N-acetyl-4-bromo-3-methyl-benzenesulfonamide) was synthesized as follows.

(Reaction 106-5)

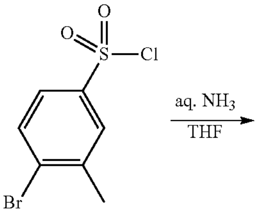

28j

-continued

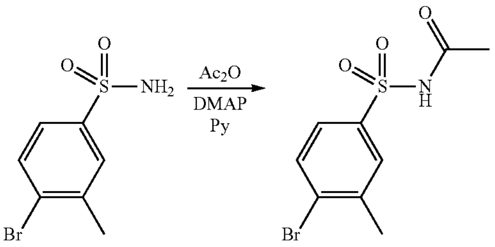

28k 106f (Reaction 106-6)

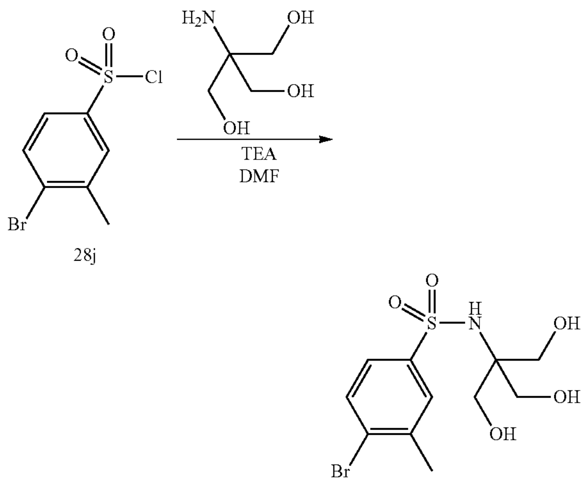

28j

106g

N-Acetyl-4-bromo-3-methyl-benzenesulfonamide was synthesized by operations similar to those in Reaction 95-6 and Reaction 12-2 using appropriate reagents and starting material.

MS (ESI) m/z=292, 294 (M+H)+.

The aryl bromide reagent used in the synthesis of Compound 595 (4-bromo-N-(2-hydroxy-1,1-bis-hydroxymethyl-ethyl)-3-methyl-benzenesulfonamide) was synthesized as follows.

4-Bromo-N-(2-hydroxy-1,1-bis-hydroxymethyl-ethyl)-3-methyl-benzenesulfonamide was synthesized by operations similar to those in Reaction 5-4 using appropriate reagents and starting material.

MS (ESI) m/z=354, 356 (M+H)+.

Example 107

N-(1-Benzyl-piperidin-4-yl)-3-methyl-4-{(E)-2-[4-oxo-2-(3-trifluoromethoxy-phenyl)-1,3,8-triaza-spiro[4.5]dec-1-ene-8-sulfonyl]-vinyl}-benzenesulfonamide (Compound 596)

(Reaction 107-1)

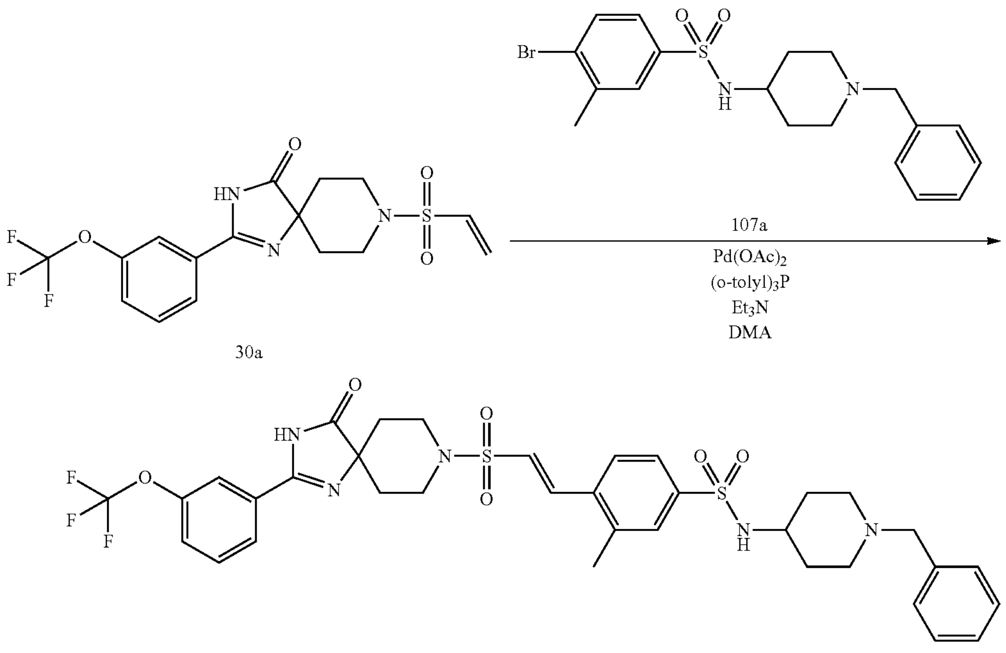

30a

Compound 596

N-(1-Benzyl-piperidin-4-yl)-3-methyl-4-{(E)-2-[4-oxo-2-(3-trifluoromethoxy-phenyl)-1,3,8-triaza-spiro[4.5]dec-1-ene-8-sulfonyl]-vinyl}-benzenesulfonamide was synthesized by operations similar to those in Reaction 26-1 using appropriate reagents and starting material.

MS (ESI) m/z=746 (M+H)+.

The example compounds shown below were synthesized by operations similar to those in Example 107 using appropriate reagents and starting materials.

Compounds 597 to Compound 618

TABLE 82

| Target Compound | Structure | LCMS condition | Retention time (min) | MS (m/z) |
|---|---|---|---|---|
| 597 | 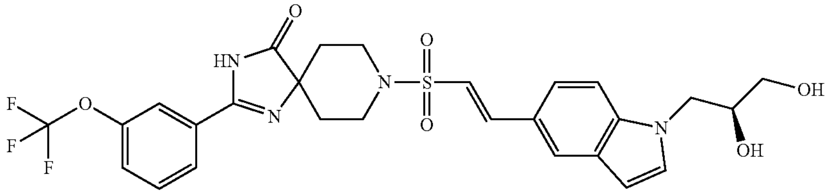 [SMILES: O=C1NC(c2cccc(OC(F)(F)F)c2)=NC12CCN(S(=O)(=O)/C=C/c1ccc3c(ccn3C[C@H](O)CO)c1)CC2] | LCMS-C-1 | 2.58 | 593 (M + H)+ |
| 598 | 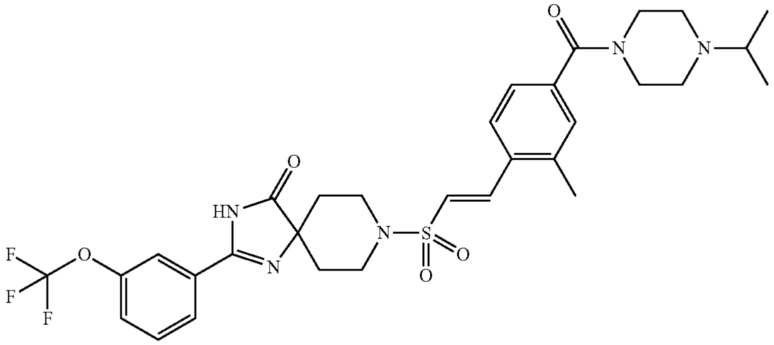 [SMILES: Cc1cc(C(=O)N2CCN(C(C)C)CC2)ccc1/C=C/S(=O)(=O)N1CCC2(CC1)N=C(c1cccc(OC(F)(F)F)c1)NC2=O] | LCMS-C-1 | 2.77 | 648 (M + H)+ |
| 599 | 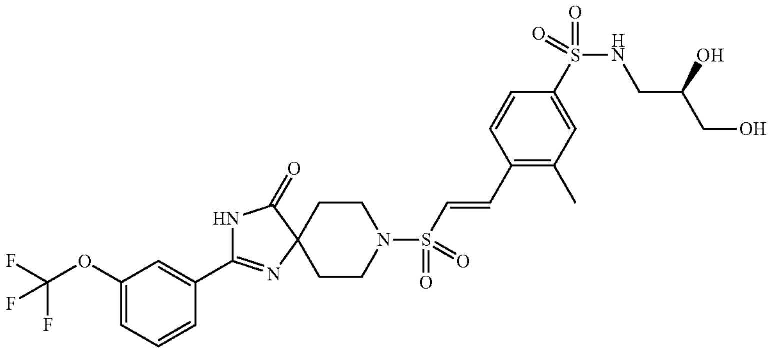 [SMILES: Cc1cc(S(=O)(=O)NC[C@@H](O)CO)ccc1/C=C/S(=O)(=O)N1CCC2(CC1)N=C(c1cccc(OC(F)(F)F)c1)NC2=O] | LCMS-C-1 | 2.45 | 647 (M + H)+ |
| 600 | 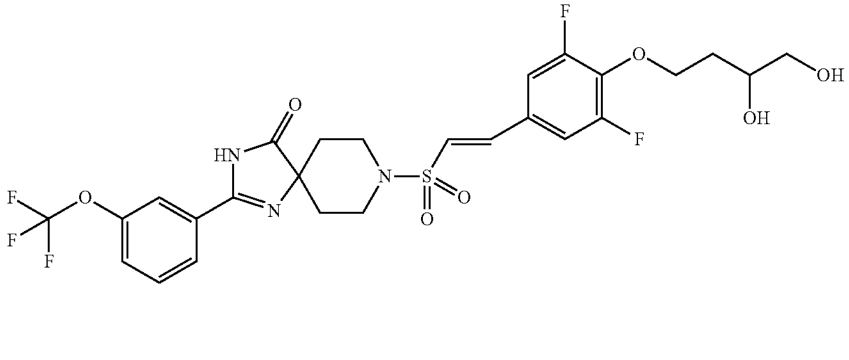 [SMILES: O=C1NC(c2cccc(OC(F)(F)F)c2)=NC12CCN(S(=O)(=O)/C=C/c1cc(F)c(OCCC(O)CO)c(F)c1)CC2] | LCMS-C-1 | 2.6 | 620 (M + H)+ |

TABLE 82-continued
| Target Compound | Structure | LCMS condition | Retention time (min) | MS (m/z) |
|---|---|---|---|---|
| 601 | 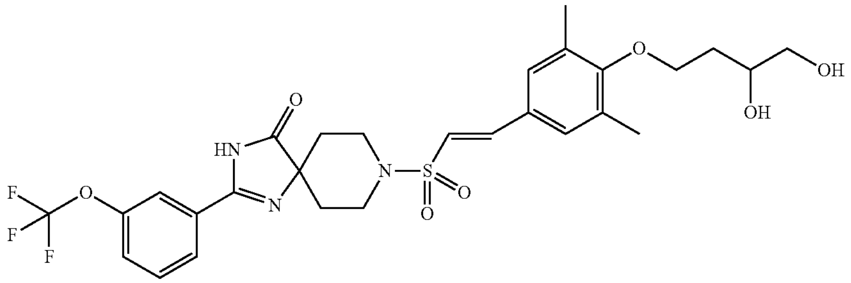 [SMILES: Cc1cc(/C=C/S(=O)(=O)N2CCC3(CC2)N=C(c2cccc(OC(F)(F)F)c2)NC3=O)cc(C)c1OCCC(O)CO] | LCMS-C-1 | 2.67 | 612 (M + H)+ |
| 602 | 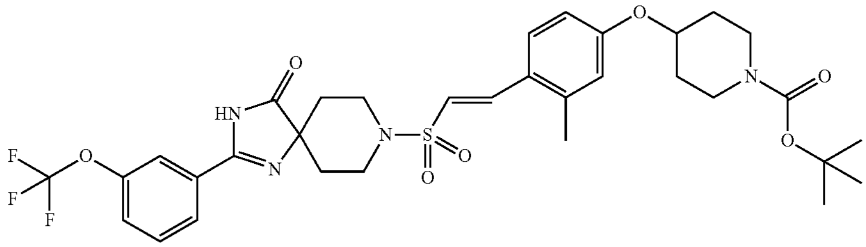 [SMILES: Cc1cc(OC2CCN(C(=O)OC(C)(C)C)CC2)ccc1/C=C/S(=O)(=O)N1CCC2(CC1)N=C(c1cccc(OC(F)(F)F)c1)NC2=O] | LCMS-C-1 | 3.17 | 693 (M + H)+ |
| 603 | 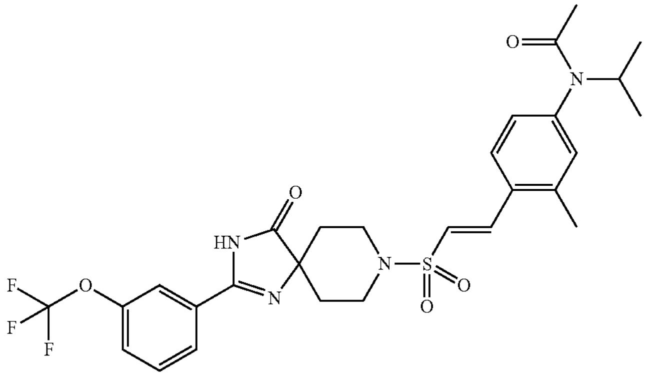 [SMILES: CC(=O)N(c1ccc(/C=C/S(=O)(=O)N2CCC3(CC2)N=C(c2cccc(OC(F)(F)F)c2)NC3=O)c(C)c1)C(C)C] | LCMS-B-1 | 2.4 | 593 (M + H)+ |
| 604 | 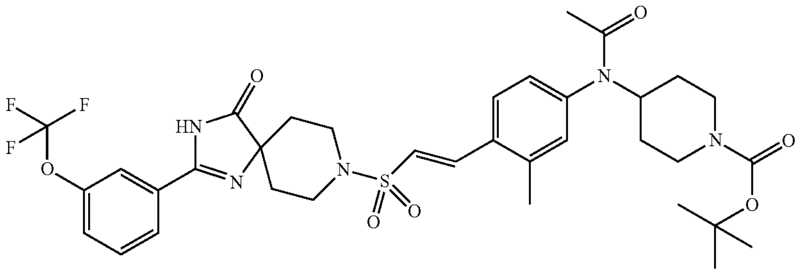 [SMILES: CC(=O)N(c1ccc(/C=C/S(=O)(=O)N2CCC3(CC2)N=C(c2cccc(OC(F)(F)F)c2)NC3=O)c(C)c1)C1CCN(C(=O)OC(C)(C)C)CC1] | LCMS-A-1 | 2.85 | 734 (M + H)+ |
| 605 | 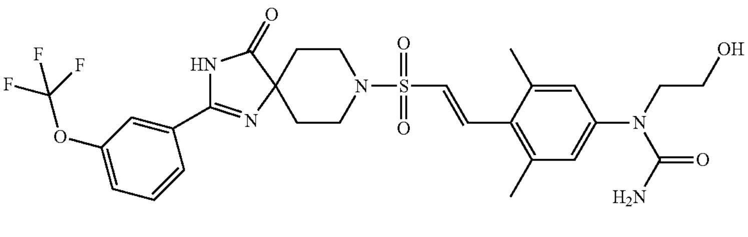 [SMILES: Cc1cc(N(CCO)C(N)=O)cc(C)c1/C=C/S(=O)(=O)N1CCC2(CC1)N=C(c1cccc(OC(F)(F)F)c1)NC2=O] | LCMS-D-1 | 2.97 | 610 (M + H)+ |

TABLE 82-continued
| Target Compound | Structure | LCMS condition | Retention time (min) | MS (m/z) |
|---|---|---|---|---|
| 606 | 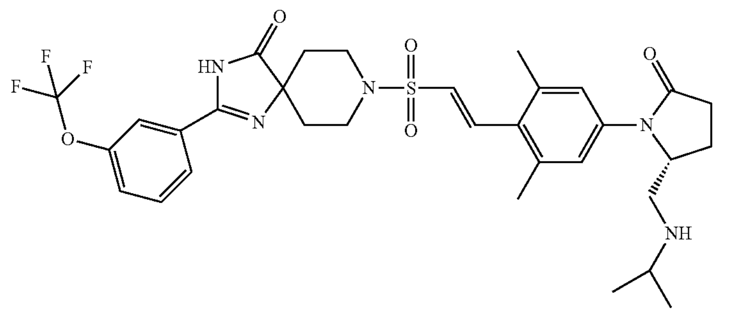 [SMILES: Cc1cc(N2C(=O)CC[C@@H]2CNC(C)C)cc(C)c1/C=C/S(=O)(=O)N1CCC2(CC1)N=C(c1cccc(OC(F)(F)F)c1)NC2=O] | LCMS-D-1 | 1.8 | 662 (M + H)+ |
| 607 | 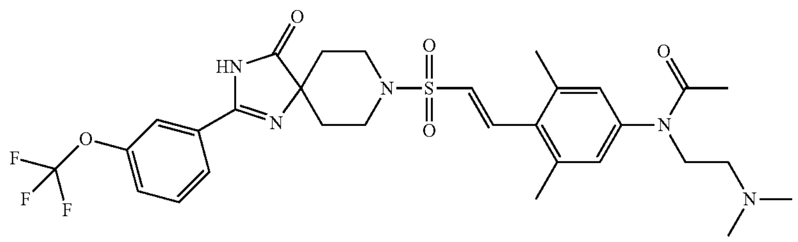 [SMILES: CC(=O)N(CCN(C)C)c1cc(C)c(/C=C/S(=O)(=O)N2CCC3(CC2)N=C(c2cccc(OC(F)(F)F)c2)NC3=O)c(C)c1] | LCMS-D-1 | 2.32 | 636 (M + H)+ |
| 608 | 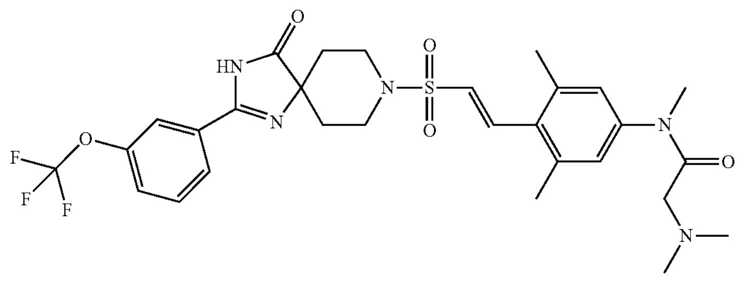 [SMILES: Cc1cc(N(C)C(=O)CN(C)C)cc(C)c1/C=C/S(=O)(=O)N1CCC2(CC1)N=C(c1cccc(OC(F)(F)F)c1)NC2=O] | LCMS-D-1 | 2.78 | 622 (M + H)+ |
| 609 | 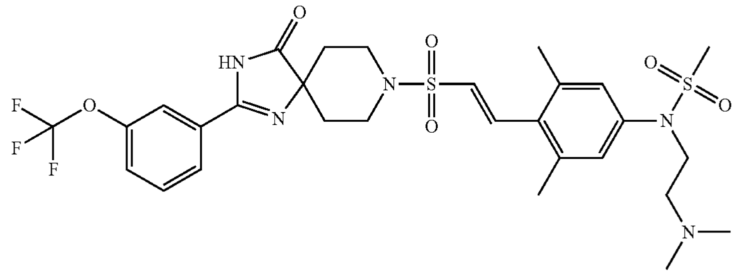 [SMILES: Cc1cc(N(CCN(C)C)S(C)(=O)=O)cc(C)c1/C=C/S(=O)(=O)N1CCC2(CC1)N=C(c1cccc(OC(F)(F)F)c1)NC2=O] | LCMS-D-1 | 1.82 | 672 (M + H)+ |
| 610 | 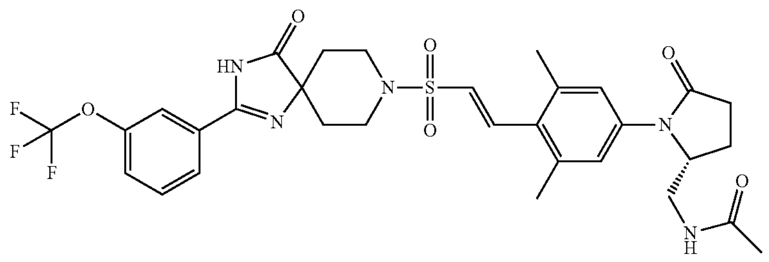 [SMILES: CC(=O)NC[C@H]1CCC(=O)N1c1cc(C)c(/C=C/S(=O)(=O)N2CCC3(CC2)N=C(c2cccc(OC(F)(F)F)c2)NC3=O)c(C)c1] | LCMS-D-1 | 3.03 | 662 (M + H)+ |

TABLE 82-continued
| Target Compound | Structure | LCMS condition | Retention time (min) | MS (m/z) |
| --- | --- | --- | --- | --- |
| 611 | 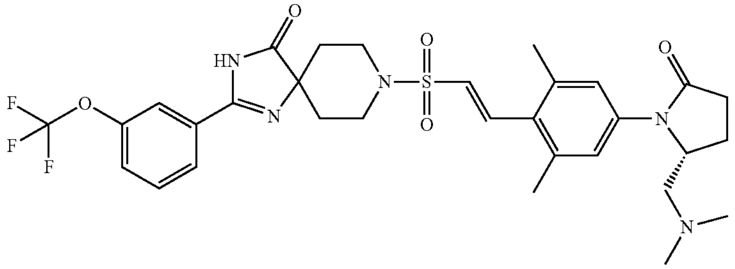 [SMILES: Cc1cc(N2C(=O)CC[C@@H]2CN(C)C)cc(C)c1/C=C/S(=O)(=O)N1CCC2(CC1)N=C(c1cccc(OC(F)(F)F)c1)NC2=O] | LCMS-D-1 | 2.7 | 648 (M + H)+ |
| 612 | 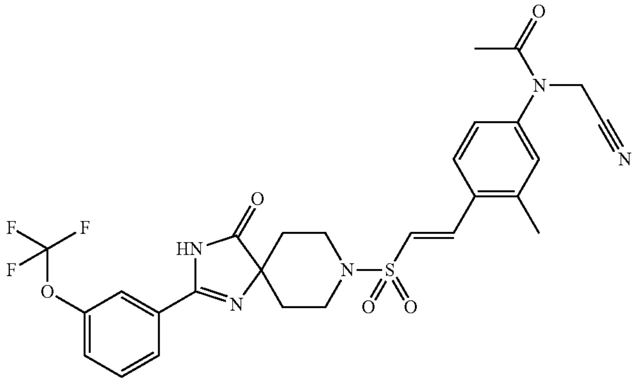 [SMILES: CC(=O)N(CC#N)c1ccc(/C=C/S(=O)(=O)N2CCC3(CC2)N=C(c2cccc(OC(F)(F)F)c2)NC3=O)c(C)c1] | LCMS-C-1 | 2.55 | 590 (M + H)+ |
| 613 | 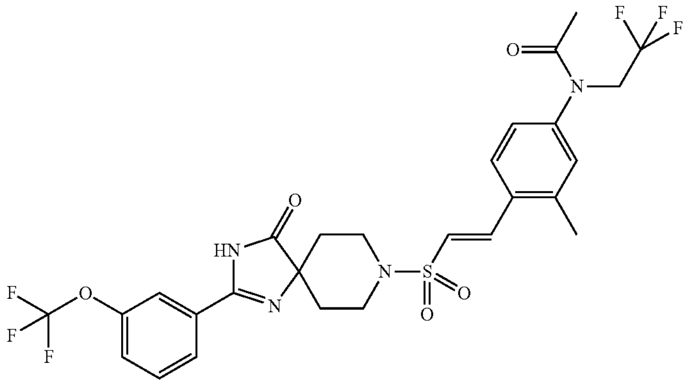 [SMILES: CC(=O)N(CC(F)(F)F)c1ccc(/C=C/S(=O)(=O)N2CCC3(CC2)N=C(c2cccc(OC(F)(F)F)c2)NC3=O)c(C)c1] | LCMS-C-1 | 2.8 | 633 (M + H)+ |
| 614 | 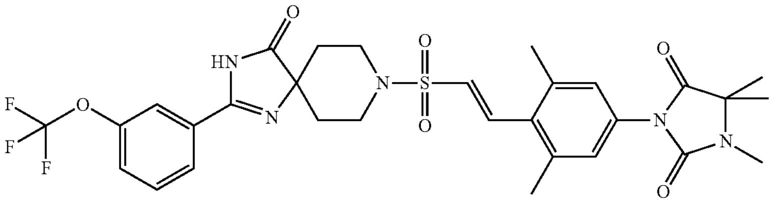 [SMILES: Cc1cc(N2C(=O)N(C)C(C)(C)C2=O)cc(C)c1/C=C/S(=O)(=O)N1CCC2(CC1)N=C(c1cccc(OC(F)(F)F)c1)NC2=O] | LCMS-D-1 | 3.43 | 648 (M + H)+ |
| 615 | 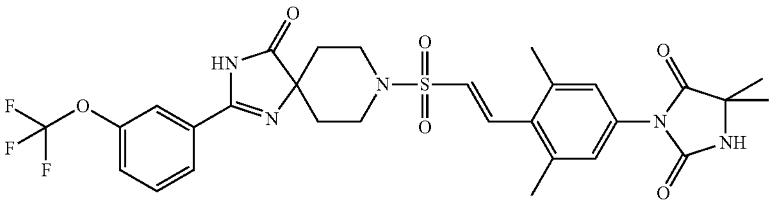 [SMILES: Cc1cc(N2C(=O)NC(C)(C)C2=O)cc(C)c1/C=C/S(=O)(=O)N1CCC2(CC1)N=C(c1cccc(OC(F)(F)F)c1)NC2=O] | LCMS-D-1 | 3.27 | 634 (M + H)+ |

TABLE 82-continued

| Target Compound | Structure | LCMS condition | Retention time (min) | MS (m/z) |
|---|---|---|---|---|
| 616 | 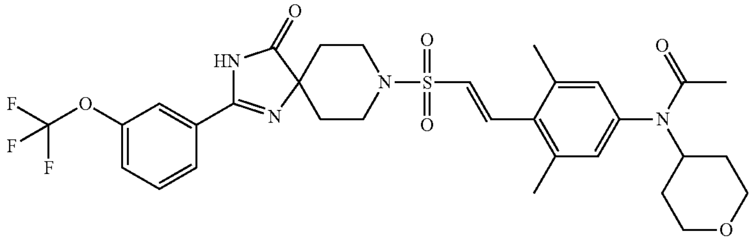 [SMILES: CC(=O)N(c1cc(C)c(/C=C/S(=O)(=O)N2CCC3(CC2)N=C(c2cccc(OC(F)(F)F)c2)NC3=O)c(C)c1)C1CCOCC1] | LCMS-D-1 | 2.15 | 649 (M + H)+ |
| 617 | 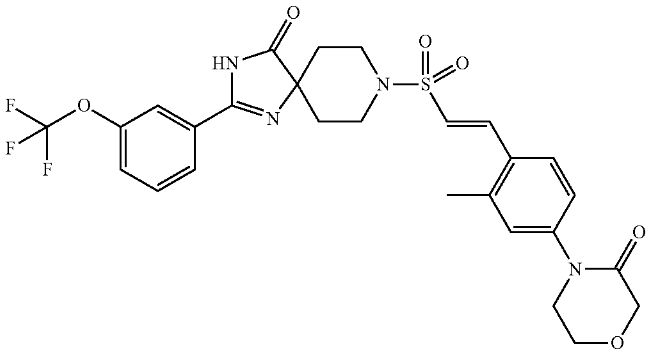 [SMILES: Cc1cc(N2CCOCC2=O)ccc1/C=C/S(=O)(=O)N1CCC2(CC1)N=C(c1cccc(OC(F)(F)F)c1)NC2=O] | LCMS-F-1 | 0.93 | 593 (M + H)+ |
| 618 | 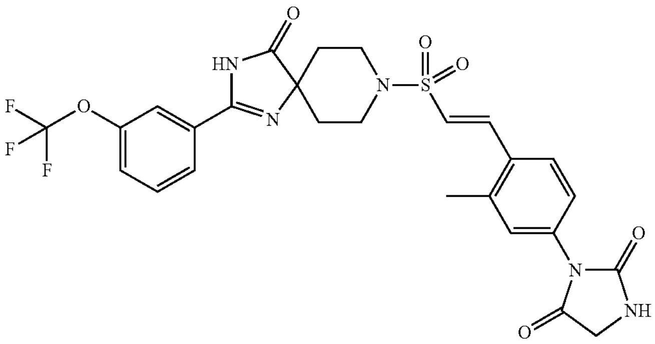 [SMILES: Cc1cc(N2C(=O)CNC2=O)ccc1/C=C/S(=O)(=O)N1CCC2(CC1)N=C(c1cccc(OC(F)(F)F)c1)NC2=O] | LCMS-F-1 | 0.9 | 592 (M + H)+ |

The aryl bromide reagent used in the synthesis of Compound 596 (N-(1-benzyl-piperidin-4-yl)-4-bromo-3-methyl-benzenesulfonamide) was synthesized as follows.

(Reaction 107-2)

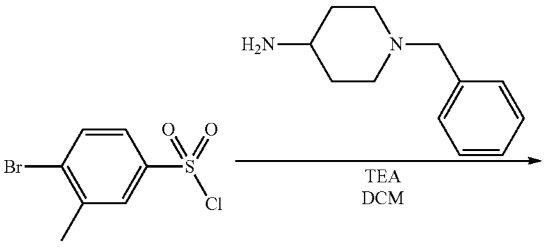

28j

-continued

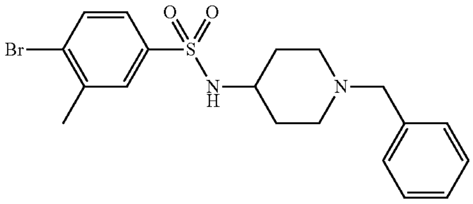

107a

N-(1-Benzyl-piperidin-4-yl)-4-bromo-3-methyl-benzenesulfonamide was synthesized by operations similar to those in Reaction 5-4 using appropriate reagents and starting material.

MS (ESI) m/z=423, 425 (M+H)+.

The aryl bromide reagent used in the synthesis of Compound 597 ((S)-3-(5-bromo-indol-1-yl)-propane-1,2-diol) was synthesized as follows.

(Reaction 107-3)

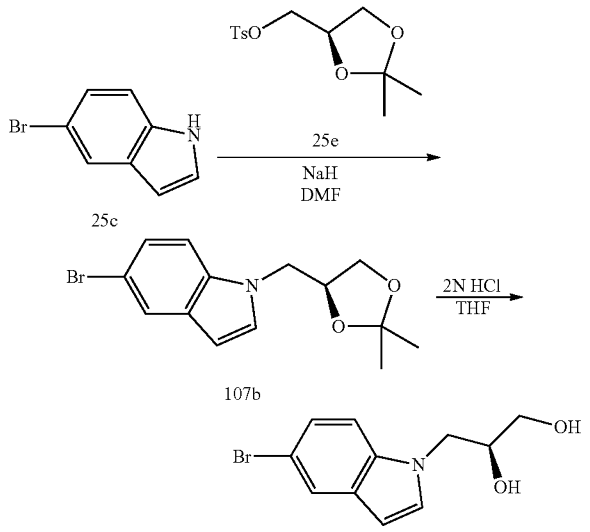

25c

107b

107c (S)-3-(5-Bromo-indol-1-yl)-propane-1,2-diol was synthesized by operations similar to those in Reaction 25-3 and Reaction 25-4 using appropriate reagents and starting material.

MS (ESI) m/z=270, 272 (M+H)+.

The aryl bromide reagent used in the synthesis of Compound 598 ((4-bromo-3-methyl-phenyl)-(4-isopropyl-piperazin-1-yl)-methanone) was synthesized as follows.

(Reaction 107-4)

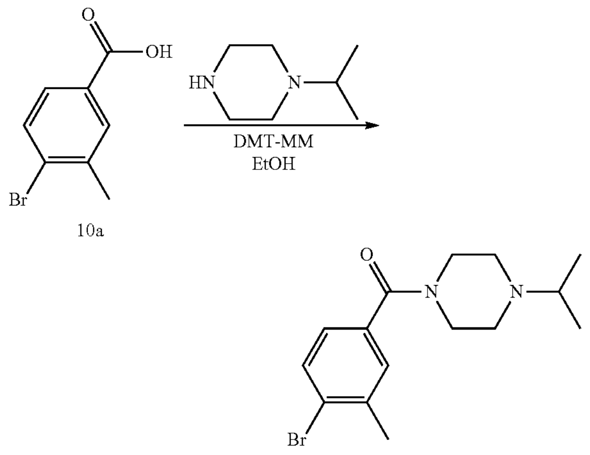

10a

107d (4-Bromo-3-methyl-phenyl)-(4-isopropyl-piperazin-1-yl)-methanone was synthesized by operations similar to those in Reaction 10-1 using appropriate reagents and starting material.

MS (ESI) m/z=325, 327 (M+H)+.

The aryl bromide reagent used in the synthesis of Compound 599 (4-bromo-N—((R)-2,3-dihydroxy-propyl)-3-methyl-benzenesulfonamide) was synthesized as follows.

(Reaction 107-5)

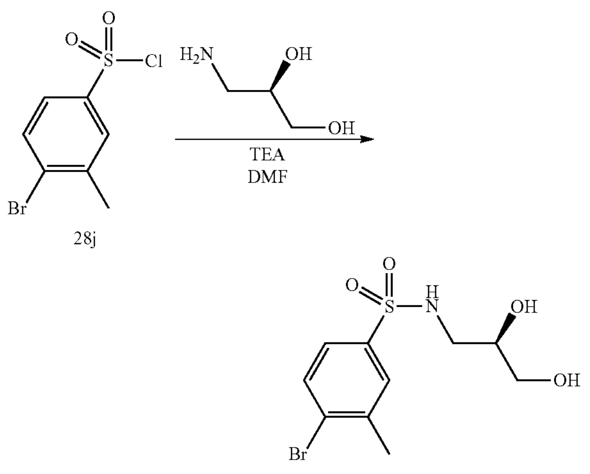

28j

107e

4-Bromo-N—((R)-2,3-dihydroxy-propyl)-3-methyl-benzenesulfonamide was synthesized by operations similar to those in Reaction 5-4 using appropriate reagents and starting material.

MS (ESI) m/z=324, 326 (M+H)+.

The aryl bromide reagent used in the synthesis of Compound 600 (4-(4-bromo-2,6-difluoro-phenoxy)-butane-1,2-diol) was synthesized as follows.

(Reaction 107-6)

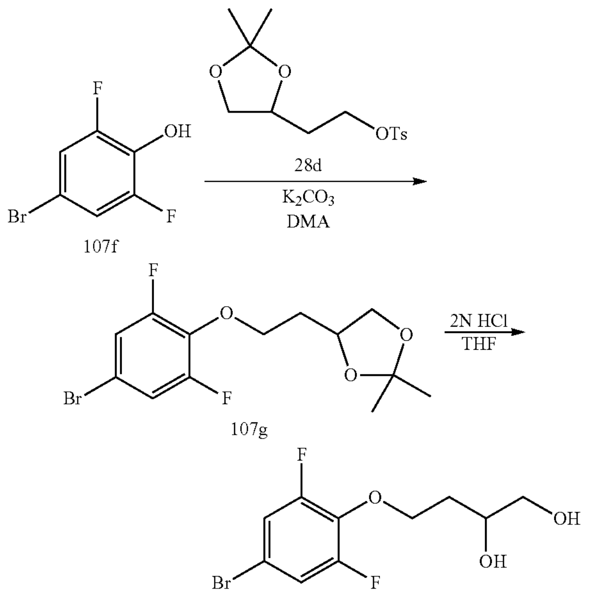

107f

107g

107h 4-(4-Bromo-2,6-difluoro-phenoxy)-butane-1,2-diol was synthesized by operations similar to those in Reaction 23-1 and Reaction 25-4 using appropriate reagents and starting material.

$^1$H-NMR (400 MHz, $CDCl_3$) δ 1.90-1.94 (2H, m), 3.57 (1H, dd, J=12.0, 8.0 Hz), 3.74 (1H, dd, J=12.0, 4.0 Hz), 4.06-4.26 (1H, m), 4.26-4.33 (2H, m), 7.07-7.12 (2H, m).

The aryl bromide reagent used in the synthesis of Compound 601 (4-(4-bromo-2,6-dimethyl-phenoxy)-butane-1,2-diol) was synthesized as follows.

(Reaction 107-7)

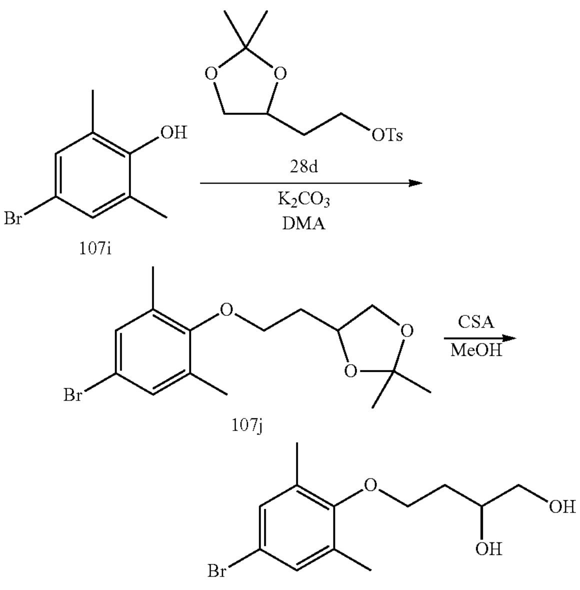

107i

107j

107k 4-(4-Bromo-2,6-dimethyl-phenoxy)-butane-1,2-diol was synthesized by operations similar to those in Reaction 23-1 and Reaction 31-6 using appropriate reagents and starting material.

$^1$H-NMR (400 MHz, $CD_3OD$) δ 1.77-1.82 (1H, m), 2.00-2.09 (1H, m), 2.45 (6H, s), 3.50-3.54 (2H, m) 3.84-3.95 (3H, m).

The aryl bromide reagent used in the synthesis of Compound 602 (4-(4-bromo-3-methyl-phenoxy)-piperidine-1-carboxylic acid tert-butyl ester) was synthesized as follows.

(Reaction 107-8)

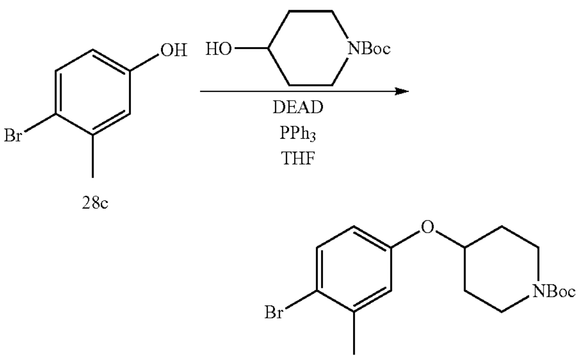

28c

107l 4-(4-Bromo-3-methyl-phenoxy)-piperidine-1-carboxylic acid tert-butyl ester was synthesized by operations similar to those in Reaction 31-7 using appropriate reagents and starting material.

$^1$H-NMR (400 MHz, $CDCl_3$) δ 1.50 (9H, s), 1.68-1.76 (2H, m), 1.87-1.92 (2H, m), 2.35 (1H, s), 3.30-3.36 (2H, m), 3.64-3.71 (2H, m), 4.38-4.43 (1H, m), 6.61 (1H, dd, J=8.0, 4.0 Hz), 6.81 (1H, d, J=4.0 Hz), 7.39 (1H, d, J=8.0 Hz).

The aryl bromide reagent used in the synthesis of Compound 603 (N-(4-bromo-3-methyl-phenyl)-N-isopropyl-acetamide) was synthesized as follows.

(Reaction 107-9)

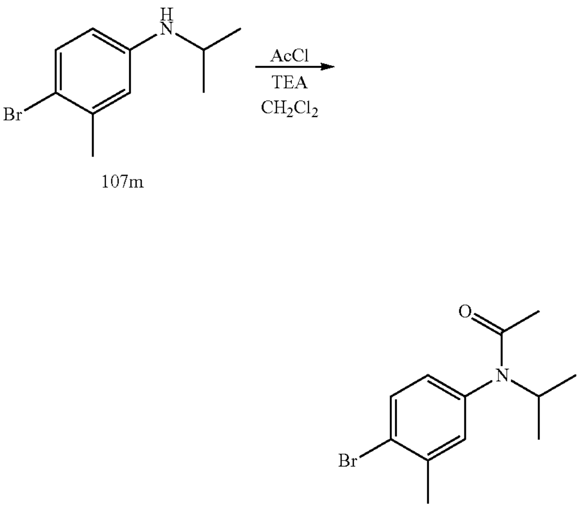

107m

107n

N-(4-Bromo-3-methyl-phenyl)-N-isopropyl-acetamide was synthesized by operations similar to those in Reaction 2-3 using appropriate reagents and starting material.

MS (ESI) m/z=270, 272 (M+H)+.

The aryl bromide reagent used in the synthesis of Compound 604 (4-[acetyl-(4-bromo-3-methyl-phenyl)-amino]-piperidine-1-carboxylic acid tert-butyl ester) was synthesized as follows.

(Reaction 107-10)

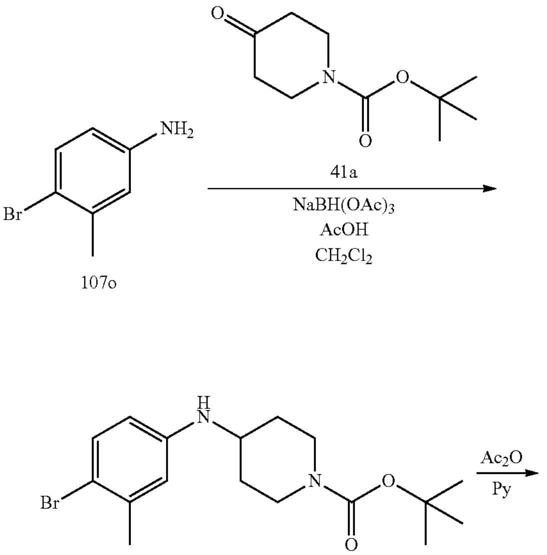

107o

107p

-continued

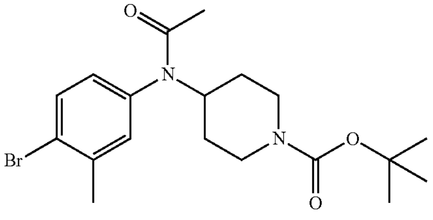

107q

4-[Acetyl-(4-bromo-3-methyl-phenyl)-amino]-piperidine-1-carboxylic acid tert-butyl ester was synthesized by operations similar to those in Reaction 41-1 and Reaction 12-2 using appropriate reagents and starting material.

$^1$H-NMR (400 MHz, $CDCl_3$) δ 1.13-1.30 (2H, m), 1.40 (9H, s), 1.70-1.80 (2H, m), 1.76 (3H, s), 2.42 (3H, s), 2.72-2.84 (2H, m), 4.07-4.20 (2H, m), 4.70-4.80 (1H, m), 6.77 (1H, dd, J=2.8, 8.4 Hz), 6.94 (1H, d, J=2.8 Hz), 7.57 (1H, d, J=8.4 Hz).

The aryl bromide reagent used in the synthesis of Compound 605 (1-(4-bromo-3,5-dimethyl-phenyl)-1-(2-hydroxy-ethyl)-urea) was synthesized as follows.

(Reaction 107-11)

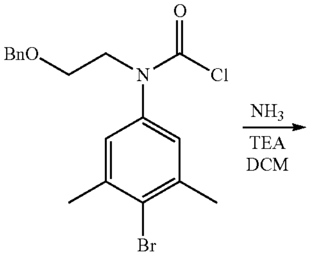

98g

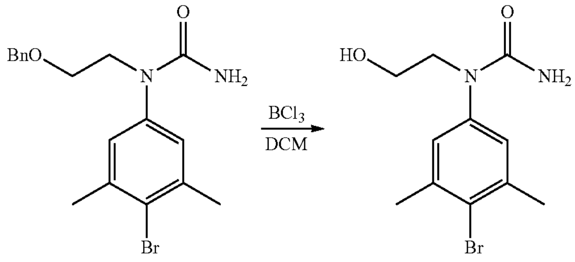

107r

107s 1-(4-Bromo-3,5-dimethyl-phenyl)-1-(2-hydroxy-ethyl)-urea was synthesized by operations similar to those in Reaction 82-1 and Reaction 98-7 using appropriate reagents and starting material.

MS (ESI) m/z=287, 289 (M+H)+.

The aryl bromide reagent used in the synthesis of Compound 606 ((R)-1-(4-bromo-3,5-dimethyl-phenyl)-5-(isopropylamino-methyl)-pyrrolidin-2-one) was synthesized as follows.

(Reaction 107-12)

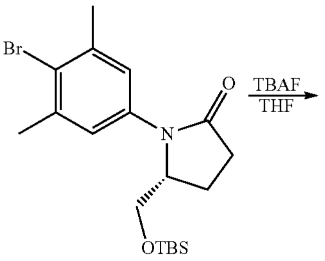

39g

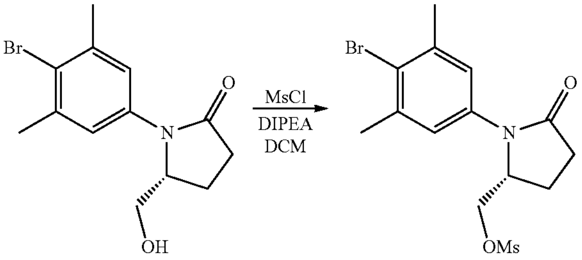

107t

107u

Methanesulfonic acid (R)-1-(4-bromo-3,5-dimethyl-phenyl)-5-oxo-pyrrolidin-2-ylmethyl ester was synthesized by operations similar to those in Reaction 39-2 and Reaction 5-4 using appropriate reagents and starting material.

$^1$H-NMR ($CDCl_3$) δ 7.12 (s, 2H), 4.43 (m, 1H), 4.19 (m, 2H), 2.93 (s, 3H), 2.70 (m, 1H), 2.60 (m, 1H), 2.41 (s, 6H), 2.40 (m, 1H), 2.16 (m, 1H).

(Reaction 107-13)

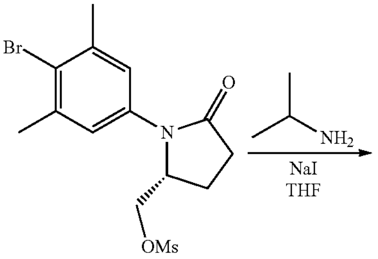

107u

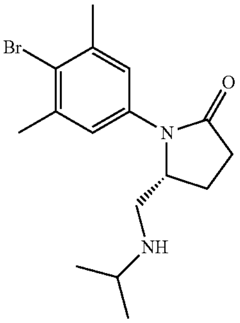

107v

Sodium iodide (catalytic amount) and isopropylamine (1.37 g, 23 mmol) were added to a solution of methanesulfonic acid (R)-1-(4-bromo-3,5-dimethyl-phenyl)-5-oxo-pyrrolidin-2-ylmethyl ester (150 mg, 0.399 mmol) in THF (3 ml) at room temperature, and the mixture was heated with stirring at 70° C. for 1.5 days. After cooling to room temperature, the reaction solution was concentrated under reduced pressure. The resulting residue was purified by silica gel column chromatography (dichloromethane-methanol) to give (R)-1-(4-bromo-3,5-dimethyl-phenyl)-5-(isopropylamino-methyl)-pyrrolidin-2-one (83 mg, 61%).

$^1$H-NMR ($CDCl_3$) δ 7.12 (s, 2H), 4.23 (m, 1H), 2.67 (m, 4H), 2.53 (m, 1H), 2.41 (s, 6H), 2.30 (m, 1H), 2.03 (m, 1H), 0.97 (dd, 6H, J=2.67 Hz, J=6.1 Hz).

The aryl bromide reagent used in the synthesis of Compound 607 (N-(4-bromo-3,5-dimethyl-phenyl)-N-(2-dimethylamino-ethyl)-acetamide) was synthesized as follows.

(Reaction 107-14)

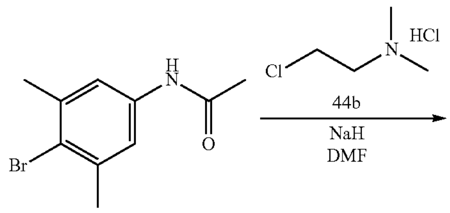

26a

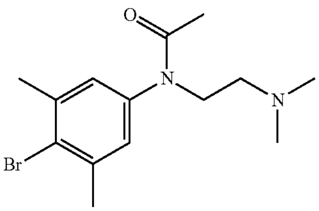

107w

N-(4-Bromo-3,5-dimethyl-phenyl)-N-(2-dimethylamino-ethyl)-acetamide was synthesized by operations similar to those in Reaction 25-3 using appropriate reagents and starting material.

MS (ESI) m/z=313, 315 (M+H)+.

The aryl bromide reagent used in the synthesis of Compound 608 (N-(4-bromo-3,5-dimethyl-phenyl)-2-dimethylamino-N-methyl-acetamide) was synthesized as follows.

(Reaction 107-15)

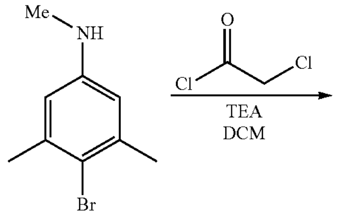

89a

-continued

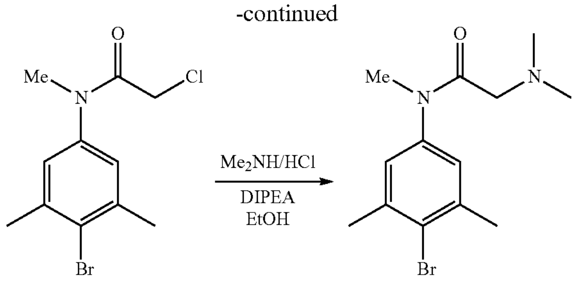

107x 107y

N-(4-Bromo-3,5-dimethyl-phenyl)-2-dimethylamino-N-methyl-acetamide was synthesized by operations similar to those in Reaction 2-3 and Reaction 95-17 using appropriate reagents and starting material.

MS (ESI) m/z=299, 301 (M+H)+.

The aryl bromide reagent used in the synthesis of Compound 609 (N-(4-bromo-3,5-dimethyl-phenyl)-N-(2-dimethylamino-ethyl)-methanesulfonamide) was synthesized as follows.

(Reaction 107-16)

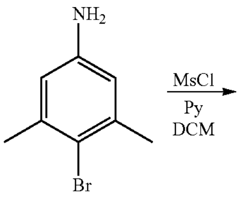

96g

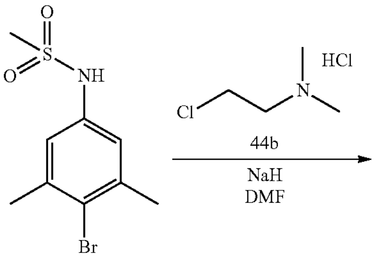

107z

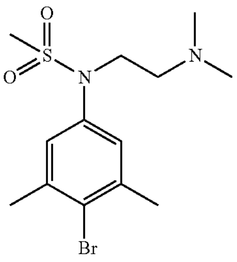

107aa

N-(4-Bromo-3,5-dimethyl-phenyl)-N-(2-dimethylamino-ethyl)-methanesulfonamide was synthesized by operations similar to those in Reaction 6-1 and Reaction 25-3 using appropriate reagents and starting material.

MS (ESI) m/z=349, 351 (M+H)+.

The aryl bromide reagent used in the synthesis of Compound 610 ((R)-5-(aminomethyl)-1-(4-bromo-3,5-dimethylphenyl)pyrrolidin-2-one) was synthesized as follows.

(Reaction 107-17)

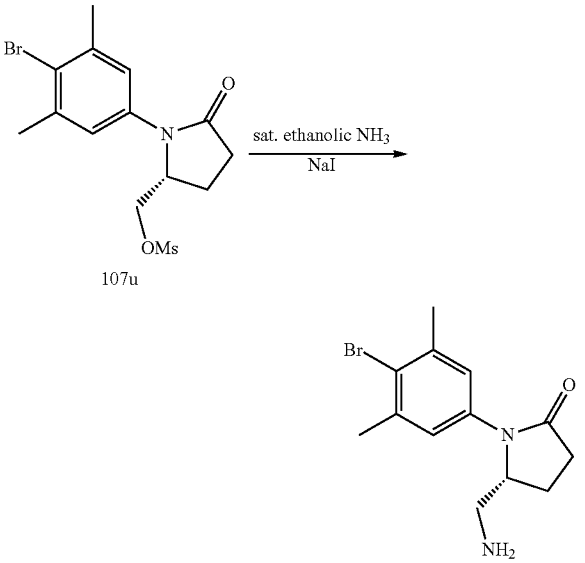

107u

107ab (R)-5-(Aminomethyl)-1-(4-bromo-3,5-dimethylphenyl) pyrrolidin-2-one was synthesized by operations similar to those in Reaction 107-13 using appropriate reagents and starting material.

$^1$H-NMR ($CDCl_3$) δ 7.10 (s, 2H), 4.20 (m, 1H), 2.80 (m, 2H), 2.60 (m, 2H), 2.41 (s, 6H), 2.30 (m, 1H), 2.03 (m, 1H).

The aryl bromide reagent used in the synthesis of Compound 611 ((R)-1-(4-bromo-3,5-dimethyl-phenyl)-5-dimethylaminomethyl-pyrrolidin-2-one) was synthesized as follows.

(Reaction 107-18)

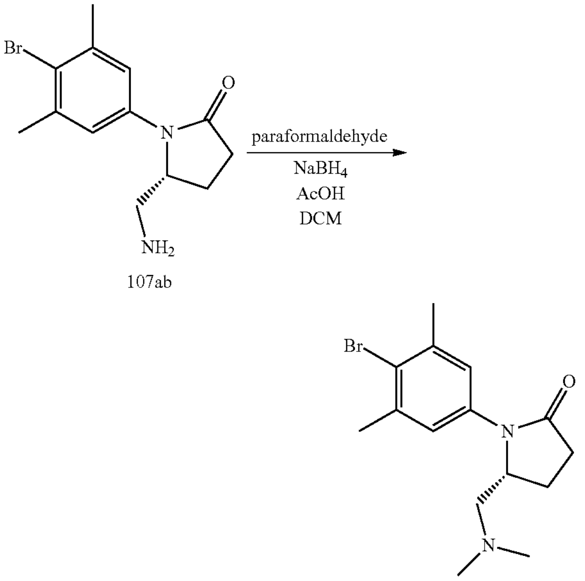

107ab

107ac (R)-1-(4-Bromo-3,5-dimethyl-phenyl)-5-dimethylaminomethyl-pyrrolidin-2-one was synthesized by operations similar to those in Reaction 80-1 using appropriate reagents and starting material.

$^1$H-NMR ($CDCl_3$) δ 7.14 (s, 2H), 4.22 (m, 1H), 2.58 (m, 2H), 2.4 (s, 6H), 2.37 (m, 2H), 2.28 (m, 1H), 2.23 (s, 6H), 2.10 (m, 1H).

The aryl bromide reagent used in the synthesis of Compound 612 (N-(4-bromo-3-methyl-phenyl)-N-cyanomethyl-acetamide) was synthesized as follows.

(Reaction 107-19)

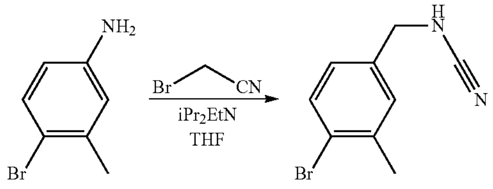

26h

107ad (4-Bromo-3-methyl-phenylamino)-acetonitrile was synthesized by operations similar to those in Reaction 95-17 using appropriate reagents and starting material.

$^1$H-NMR ($CDCl_3$) δ 2.36 (3H, s), 3.86-3.93 (1H, m), 4.09 (2H, d, J=7.8 Hz), 6.43 (1H, dd, J=8.8, 3.8 Hz), 6.60 (1H, d, J=3.8 Hz), 7.38 (1H, d, J=8.8 Hz).

(Reaction 107-20)

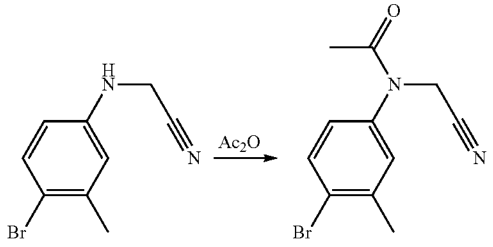

107ae

107af

Acetic anhydride (4.99 ml) was added to (4-bromo-3-methyl-phenylamino)-acetonitrile (594 mg, 2.64 mmol), and the mixture was heated with stirring at 115° C. for one hour. The reaction solution was cooled and then concentrated under reduced pressure. The resulting residue was purified by silica gel column chromatography (hexane-ethyl acetate) to give N-(4-bromo-3-methyl-phenyl)-N-cyanomethyl-acetamide (697 mg, 99%).

MS (ESI) m/z=267, 269 (M+H)+.

The aryl bromide reagent used in the synthesis of Compound 613 (N-(4-bromo-3-methyl-phenyl)-N-(2,2,2-trifluoro-ethyl)-acetamide) was synthesized as follows.

(Reaction 107-21)

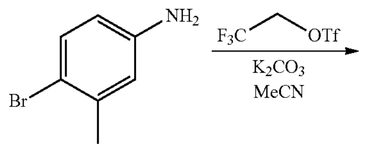

26h

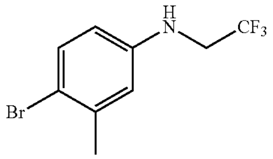

107ag

Potassium carbonate (2.50 g, 18.1 mmol) and trifluoromethanesulfonic acid 2,2,2-trifluoro-ethyl ester (2.36 ml, 16.4 mmol) were added to a solution of 4-bromo-3-methylaniline (1.68 g, 9.03 mmol) in MeCN (39.0 ml) at room temperature, and the mixture was stirred at 80° C. overnight. The reaction mixture was concentrated under reduced pressure, and the resulting residue was then purified by silica gel column chromatography (hexane-ethyl acetate) to give (4-bromo-3-methyl-phenyl)-(2,2,2-trifluoro-ethyl)-amine (2.20 g, 91%).

MS (ESI) m/z=268, 270 (M+H)+.

(Reaction 107-22)

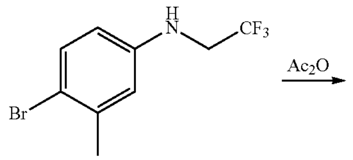

107ag

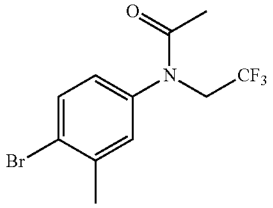

107ah

N-(4-Bromo-3-methyl-phenyl)-N-(2,2,2-trifluoro-ethyl)-acetamide was synthesized by operations similar to those in Reaction 107-20 using appropriate reagents and starting material.

MS (ESI) m/z=310, 312 (M+H)+.

The aryl bromide reagent used in the synthesis of Compound 616 (N-(4-bromo-3,5-dimethyl-phenyl)-N-(tetrahydro-pyran-4-yl)-acetamide) was synthesized as follows.

(Reaction 107-23)

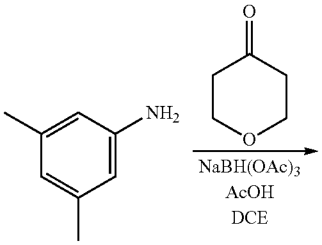

107ai

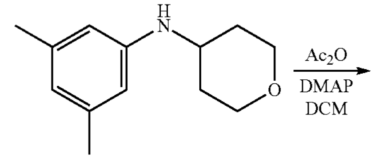

107aj

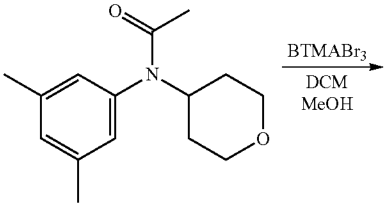

107ak

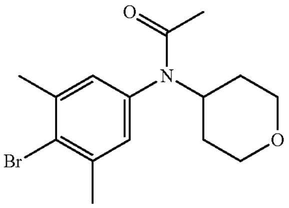

107al

N-(4-Bromo-3,5-dimethyl-phenyl)-N-(tetrahydro-pyran-4-yl)-acetamide was synthesized by operations similar to those in Reaction 41-1, Reaction 19-2 (using DMAP as a base) and Reaction 26-2 using appropriate reagents and starting material.

MS (ESI) m/z=326, 328 (M+H)+.

The aryl bromide reagent used in the synthesis of Compound 617 (4-(4-bromo-3-methyl-phenyl)-morpholin-3-one) was synthesized as follows.

(Reaction 107-24)

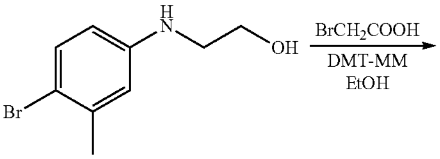

12c

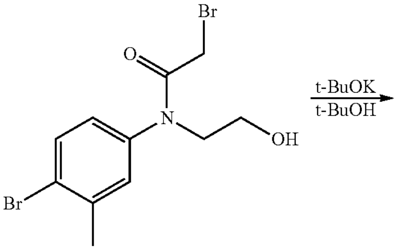

107am

-continued

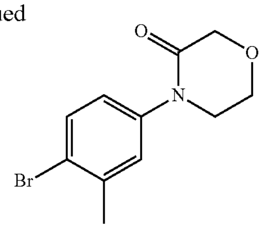

107an 4-(4-Bromo-3-methyl-phenyl)-morpholin-3-one was synthesized by operations similar to those in Reaction 10-1 and Reaction 96-18 using appropriate reagents and starting material.

MS (ESI) m/z=270, 272 (M+H)+.

Example 108

2-(4-Fluoro-3-trifluoromethyl-phenyl)-8-{(E)-2-[2-methyl-4-(pyrrolidine-1-carbonyl)-phenyl]-ethene-sulfonyl}-1,3,8-triaza-spiro[4.5]dec-1-en-4-one (Compound 619)

(Reaction 108-1)

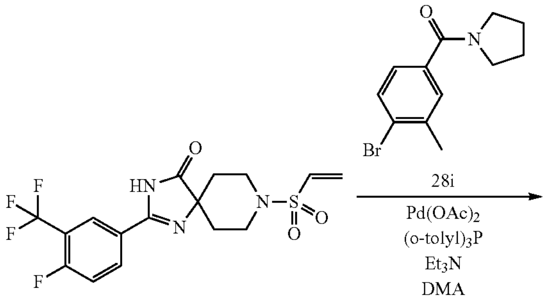

33b

-continued

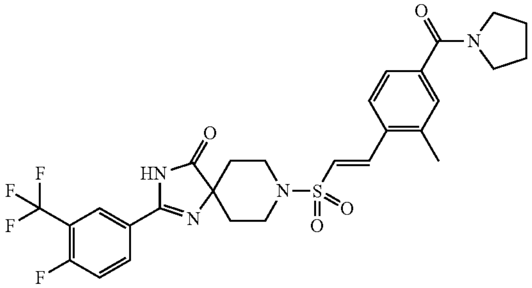

Compound 619

2-(4-Fluoro-3-trifluoromethyl-phenyl)-8-{(E)-2-[2-methyl-4-(pyrrolidine-1-carbonyl)-phenyl]-ethenesulfonyl}-1,3,8-triaza-spiro[4.5]dec-1-en-4-one was synthesized by operations similar to those in Reaction 26-1 using appropriate reagents and starting material.

MS (ESI) m/z=593 (M+H)+.

The example compounds shown below were synthesized by operations similar to those in Example 108 using appropriate reagents and starting materials.

Compounds 620 to Compound 621

TABLE 83

| Target Compound | Structure | LCMS condition | Retention time (min) | MS (m/z) |
|---|---|---|---|---|
| 620 | 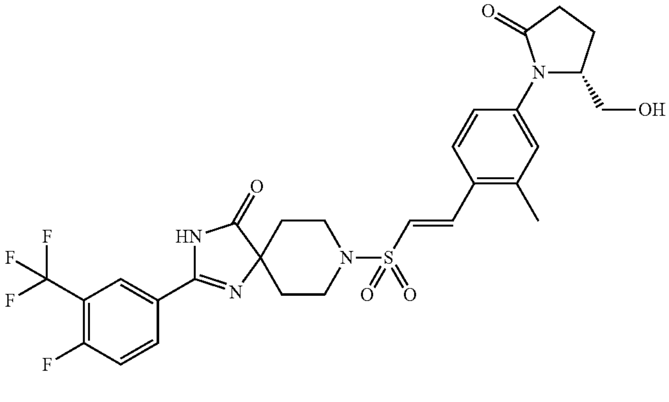 [SMILES: Cc1cc(N2C(=O)CC[C@@H]2CO)ccc1/C=C/S(=O)(=O)N1CCC2(CC1)N=C(c1ccc(F)c(C(F)(F)F)c1)NC2=O] | LCMS-C-1 | 2.48 | 609 (M + H)+ |

TABLE 83-continued

| Target Compound | Structure | LCMS condition | Retention time (min) | MS (m/z) |
|---|---|---|---|---|
| 621 | 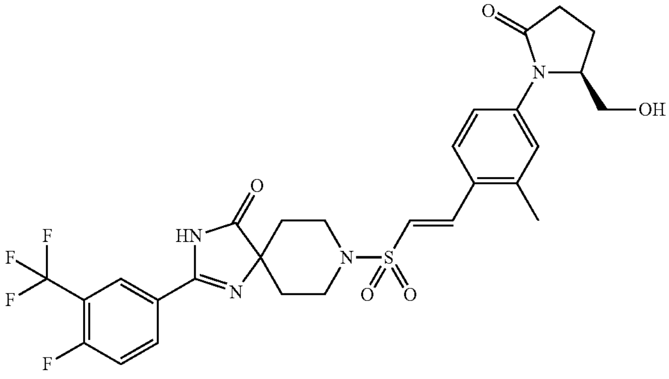 [SMILES: Cc1cc(N2C(=O)CC[C@H]2CO)ccc1/C=C/S(=O)(=O)N1CCC2(CC1)N=C(c1ccc(F)c(C(F)(F)F)c1)NC2=O] | LCMS-C-1 | 2.43 | 609 (M + H)+ |

The aryl bromide reagent used in the synthesis of Compound 621 ((S)-1-(4-bromo-3-methyl-phenyl)-5-hydroxymethyl-pyrrolidin-2-one) was synthesized as follows.

(Reaction 108-2)

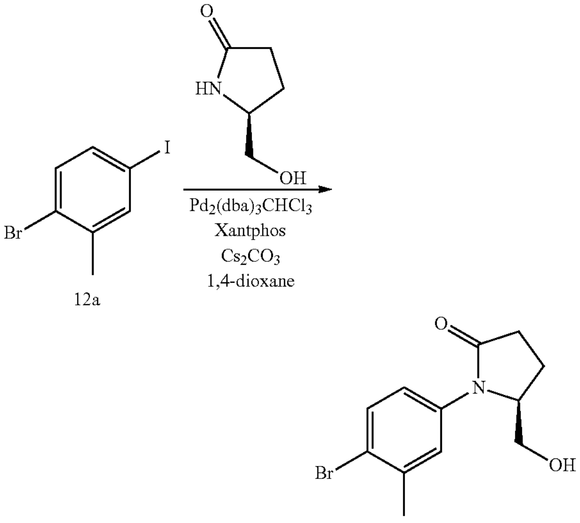

12a

108a (S)-1-(4-Bromo-3-methyl-phenyl)-5-hydroxymethyl-pyrrolidin-2-one was synthesized by operations similar to those in Reaction 29-3 using appropriate reagents and starting material.

MS (ESI) m/z=284 (M+H)+.

Example 109

8-{(E)-2-[1-((S)-2,3-Dihydroxy-propyl)-1H-indol-4-yl]-ethenesulfonyl}-2-(9,9,9-trifluoro-nonyl)-1,3,8-triaza-spiro[4.5]dec-1-en-4-one (Compound 622)

(Reaction 109-1)

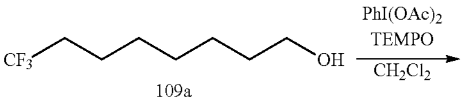

109a

-continued

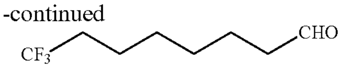

109b 2,2,6,6-Tetramethylpiperidine 1-oxyl (202 mg, 1.29 mmol) and (diacetoxyiodo)benzene (3.33 g, 10.4 mmol) were added to a solution of 8,8,8-trifluoro-octanol (~8.63 mmol) in dichloromethane (34.5 mL) at 0° C. in an $N_2$ atmosphere, and the mixture was stirred at 0° C. for five minutes and at room temperature for 1.5 hours. The reaction solution was diluted with dichloromethane (200 mL), and the organic layer was sequentially washed with a saturated aqueous sodium sulfite solution (100 mL), a saturated aqueous sodium bicarbonate solution (100 mL) and saturated brine (100 mL). The organic layer was dried over sodium sulfate and then concentrated under reduced pressure. The resulting residue was purified by silica gel column chromatography (hexane-ethyl acetate) to give 8,8,8-trifluoro-octanal as a colorless oily substance (310 mg, two steps, 20%).

$^1$H-NMR (400 MHz, $CDCl_3$) δ 1.35-1.50 (4H, br-m), 1.58-1.62 (2H, br-m), 1.68-1.73 (2H, br-m), 2.05-2.17 (2H, br-m), 2.49 (2H, t, J=7.1 Hz), 9.82 (1H, s).

$^{19}$F-NMR (376 MHz, $CDCl_3$) δ −66.3 (3F, s).

(Reaction 109-2)

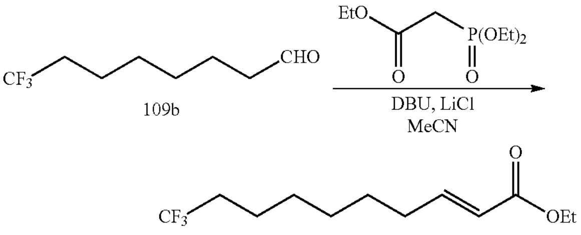

109b

109c 1,8-Diazabicyclo[5.4.0]undec-7-ene (436 μL, 2.92 mmol) was added to a solution of (diethoxy-phosphoryl)-acetic acid ethyl ester (633 μL, 2.43 mmol) and lithium chloride (144 mg, 3.41 mmol) in acetonitrile (20.0 mL) at 0° C., and the mixture was stirred at 0° C. for 10 minutes. A solution of 8,8,8-trifluoro-octanal (2.43 mmol) in acetonitrile (4.3 mL) was added dropwise to the reaction solution at 0° C., and the mixture was stirred for 10 minutes. Thereafter, the reaction mixture was stirred at room temperature for one hour and diluted with methyl tert-butyl ether (200 mL). The organic layer was sequentially washed with a saturated aqueous ammonium chloride solution (30 mL), $H_2O$ (30 mL) and saturated brine (30 mL), dried over sodium sulfate and concentrated under reduced pressure. The resulting residue was purified by silica gel column chromatography (hexane-ethyl acetate) to give (E)-10,10,10-trifluoro-dec-2-enoic acid ethyl ester as a colorless oily substance (426.6 mg, 70%).

$^1$H-NMR (400 MHz, $CDCl_3$) δ 1.29 (3H, t, J=7.2 Hz), 1.31-1.41 (4H, m), 1.41-1.49 (2H, m), 1.51-1.59 (2H, m), 1.99-2.12 (2H, m), 2.20 (2H, ddd, J=14.5, 7.2, 1.5 Hz), 4.18 (2H, q, J=7.1 Hz), 5.81 (1H, dt, J=15.7, 1.6 Hz), 6.95 (1H, dt, J=15.6, 7.0 Hz).

$^{19}$F-NMR (376 MHz, $CDCl_3$) δ -66.4 (3F, s).

(Reaction 109-3)

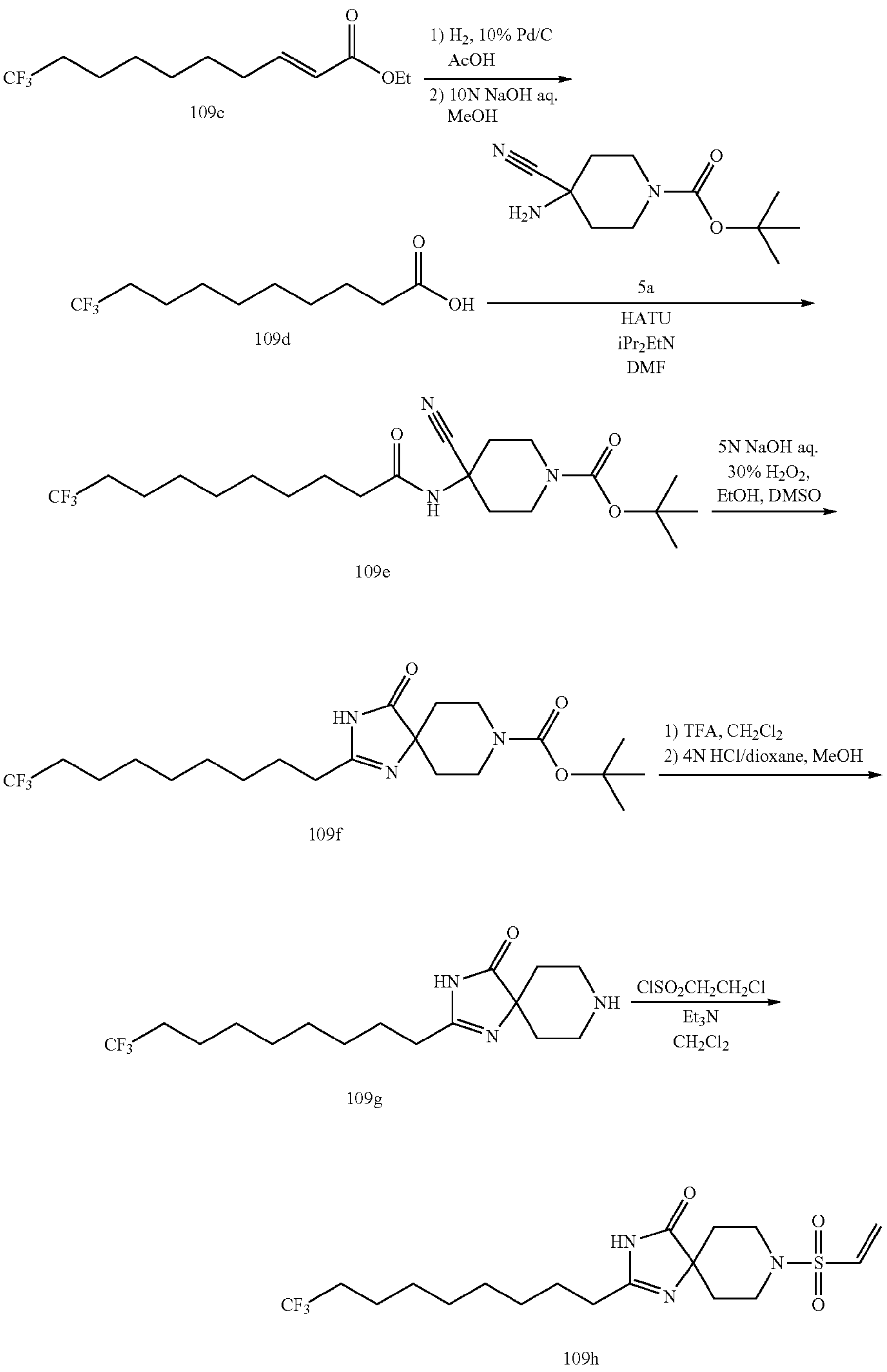

8-Ethenesulfonyl-2-(9,9,9-trifluoro-nonyl)-1,3,8-triaza-spiro[4.5]dec-1-en-4-one was synthesized by operations similar to those in Reaction 18-2, Reaction 23-2, Reaction 10-14, Reaction 1-4, Reaction 4-1, Reaction 5-3 and Reaction 25-1 using appropriate reagents and starting material.

MS (ESI) m/z=424 (M+H)+.

(Reaction 109-4)

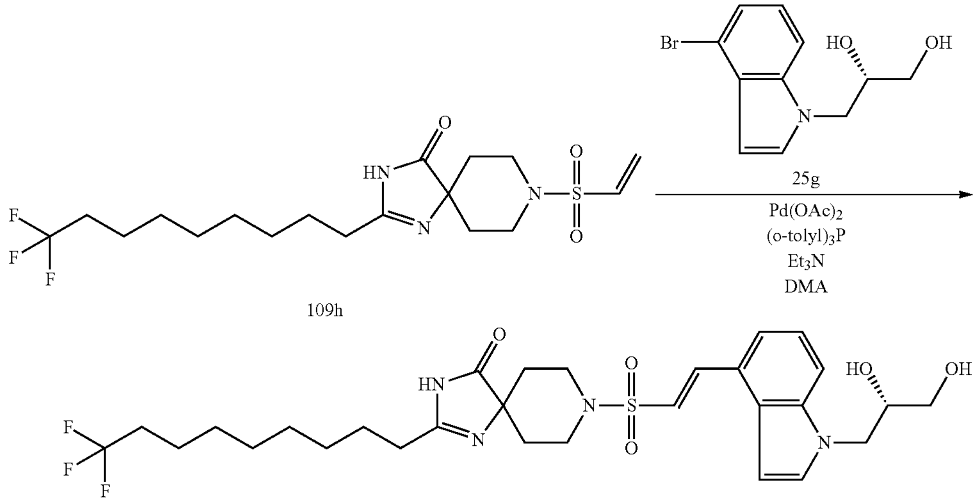

109h

Compound 622

8-{(E)-2-[1-((S)-2,3-Dihydroxy-propyl)-1H-indol-4-yl]-ethenesulfonyl}-2-(9,9,9-trifluoro-nonyl)-1,3,8-triaza-spiro[4.5]dec-1-en-4-one was synthesized by operations similar to those in Reaction 26-1 using appropriate reagents and starting material.

MS (ESI) m/z=613 (M+H)+.

Example 110

8-{(E)-2-[1-((S)-2,3-Dihydroxy-propyl)-1H-indol-4-yl]-ethenesulfonyl}-2-(8,8,9,9,9-pentafluoro-nonyl)-1,3,8-triaza-spiro[4.5]dec-1-en-4-one (Compound 623)

(Reaction 110-1)

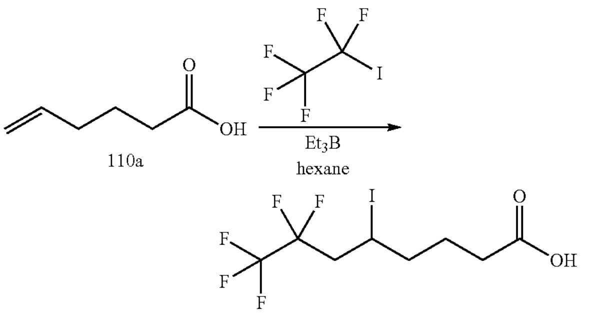

110a

110b

Triethylborane (43.8 mL, 438 mmol) and 1,1,1,2,2-pentafluoro-2-iodo-ethane (8.52 mL, 657 mmol) were added to a solution of hex-5-enoic acid (5.21 mL, 438 mmol) in hexane (219 mL) at room temperature, and the mixture was stirred at room temperature for five days. The reaction solution was concentrated under reduced pressure, and the resulting residue was purified by silica gel column chromatography (hexane-ethyl acetate) to give 7,7,8,8,8-pentafluoro-5-iodo-octanoic acid (purity 80%) as a colorless oily substance (2.63 g, 17%).

$^1$H-NMR (400 MHz, $CDCl_3$) δ 1.72-1.82 (1H, m), 1.83-1.92 (2H, m), 1.86-1.98 (1H, m), 2.36-2.46 (2H, m), 2.67-2.96 (2H, m), 4.65-4.34 (1H, m).

(Reaction 110-2)

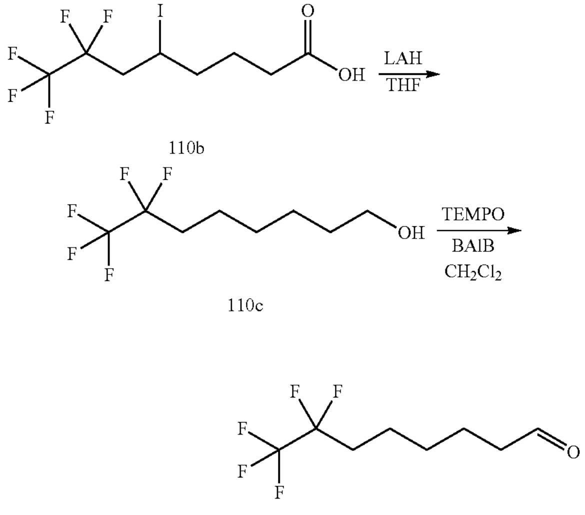

110b

110c

110d 7,7,8,8,8-Pentafluoro-octanal was synthesized by operations similar to those in Reaction 95-28 and Reaction 109-1 using appropriate reagents and starting material. This was used in the next reaction without complete purification.

(Reaction 110-3)

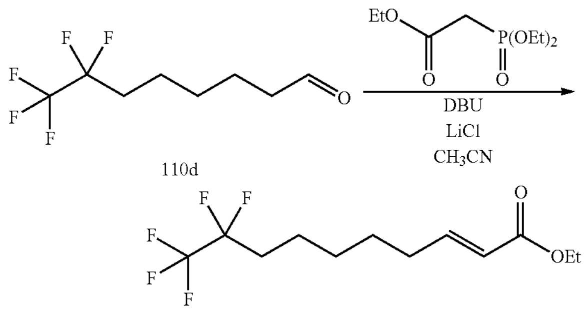

110d

110e 1,8-Diazabicyclo[5.4.0]undec-7-ene (1.08 mL, 7.26 mmol) was added to a solution of (diethoxy-phosphoryl)-acetic acid ethyl ester (1.57 mL, 7.87 mmol) and lithium chloride (359 mg, 8.47 mmol) in acetonitrile (60.5 mL) at 0° C., and the mixture was stirred at 0° C. for 10 minutes. A solution of 7,7,8,8,8-pentafluoro-octanal (1.32 g, 6.05 mmol) in acetonitrile (20.5 mL) was added dropwise to the reaction solution at 0° C., and the mixture was stirred for 10 minutes. Thereafter, the reaction mixture was stirred at room temperature for one hour and diluted with methyl tert-butyl ether (300 mL). The organic layer was sequentially washed with 2 N hydrochloric acid (50 mL), $H_2O$ (50 mL) and saturated brine (50 mL), dried over sodium sulfate and concentrated under reduced pressure. The resulting residue was purified by silica gel column chromatography (hexane-ethyl acetate) to give (E)-9,9,10,10,10-pentafluoro-dec-2-enoic acid ethyl ester (purity 80%) as a colorless oily substance (49.7 mg, 47%).

$^1$H-NMR (400 MHz, $CDCl_3$) δ 1.29 (3H, t, J=7.2 Hz), 1.37-1.44 (1H, m), 1.46-1.52 (1H, m), 1.56-1.68 (2H, m), 1.93-2.08 (2H, m), 2.18-2.26 (2H, m), 4.19 (2H, q, J=7.2 Hz), 5.79-5.86 (1H, m), 6.88-6.98 (1H, m).

(Reaction 110-4)

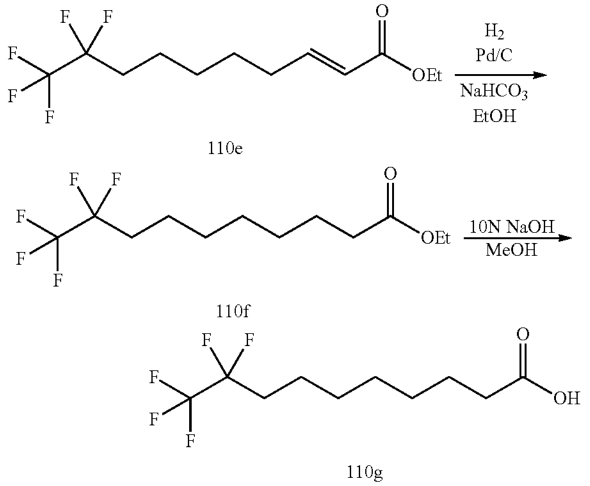

110e

110f

110g 9,9,10,10,10-Pentafluoro-decanoic acid was synthesized by operations similar to those in Reaction 18-2 and Reaction 95-18 using appropriate reagents and starting material.

$^1$H-NMR (400 MHz, $CDCl_3$) δ 1.31-1.44 (6H, br-m), 1.53-1.68 (4H, m), 1.92-2.08 (2H, br-m), 2.36 (2H, t, J=7.6 Hz).

(Reaction 110-5)

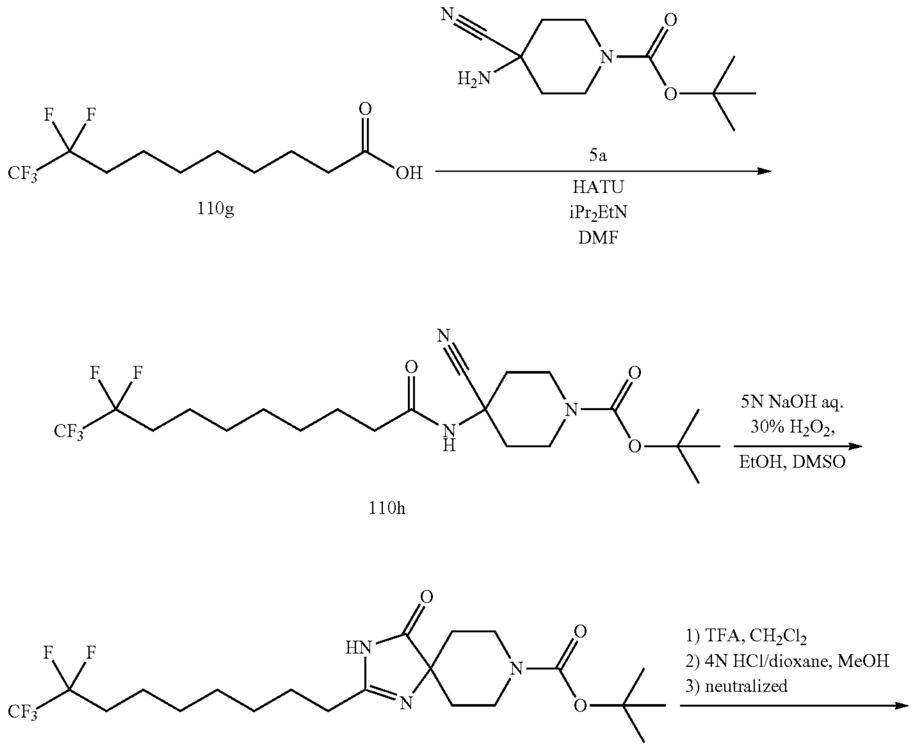

110g

110h

110i

-continued
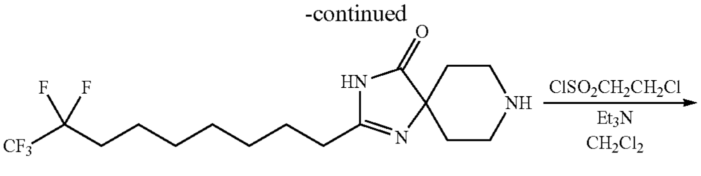
110j
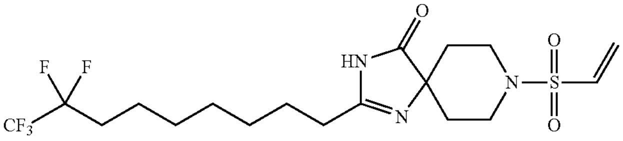
110k
8-Ethenesulfonyl-2-(8,8,9,9,9-pentafluoro-nonyl)-1,3,8-triaza-spiro[4.5]dec-1-en-4-one was synthesized by operations similar to those in Reaction 10-14, Reaction 1-4, Reaction 4-1, Reaction 5-3 and Reaction 25-1 using appropriate reagents and starting material.
MS (ESI) m/z=460 (M+H)+.
(Reaction 110-6)
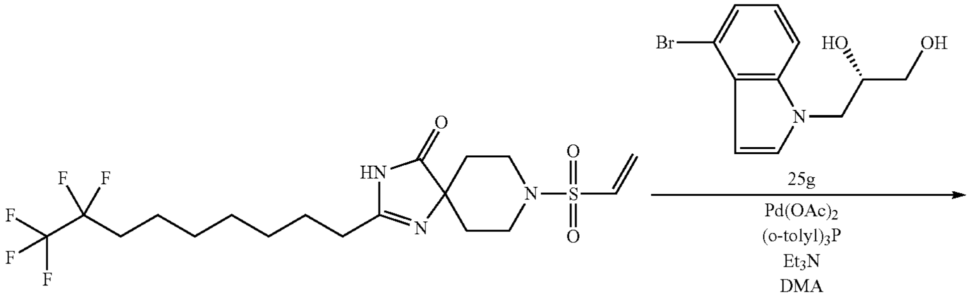
110k
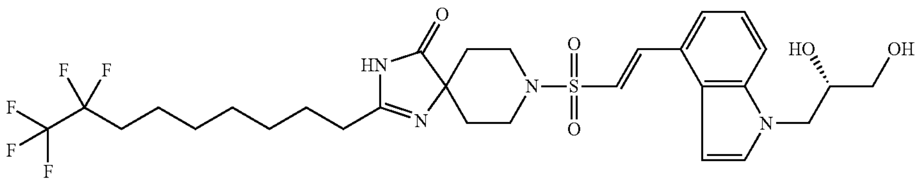
Compound 623

8-{(E)-2-[1-((S)-2,3-Dihydroxy-propyl)-1H-indol-4-yl]-ethenesulfonyl}-2-(8,8,9,9,9-pentafluoro-nonyl)-1,3,8-triaza-spiro[4.5]dec-1-en-4-one was synthesized by operations similar to those in Reaction 26-1 using appropriate reagents and starting material.

MS (ESI) m/z=649 (M+H)+.

Example 111

1-(4-{(E)-2-[2-(4-Ethyl-cyclohexyl)-4-oxo-1,3,8-triaza-spiro[4.5]dec-1-ene-8-sulfonyl]-vinyl}-3-methyl-phenyl)-imidazolidine-2,4-dione (Compound 624)

(Reaction 111-1)

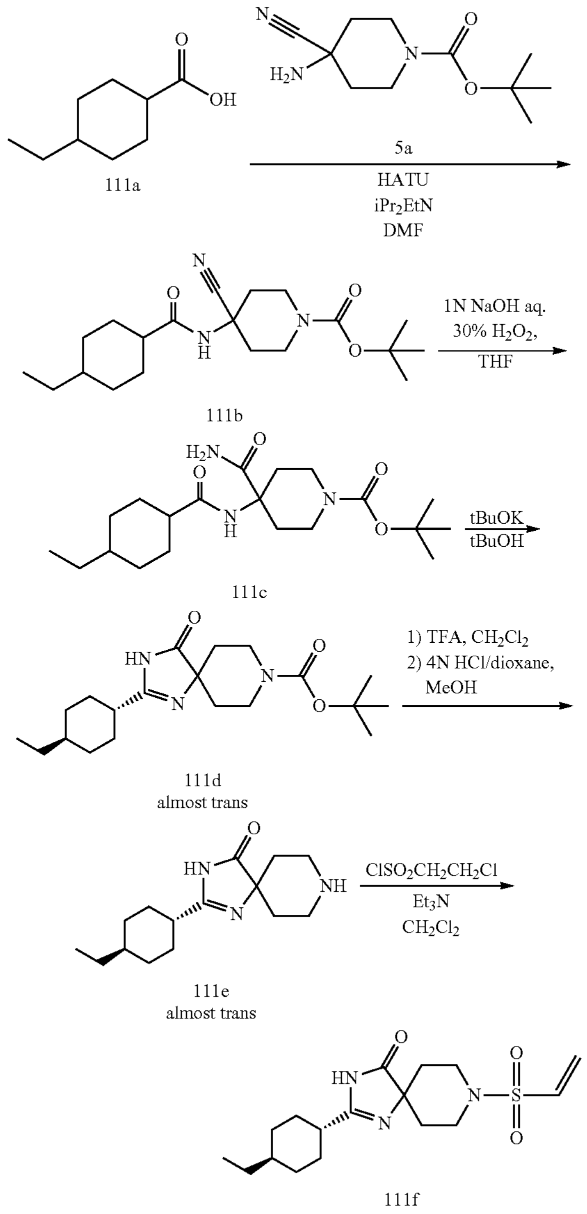

111f
almost trans

8-Ethenesulfonyl-2-(4-ethyl-cyclohexyl)-1,3,8-triaza-spiro[4.5]dec-1-en-4-one was synthesized by operations similar to those in Reaction 10-14, Reaction 10-11, Reaction 10-12, Reaction 4-1, Reaction 5-3 and Reaction 25-1 using appropriate reagents and starting material.

MS (ESI) m/z=352 (M−H)−.

(Reaction 111-2)

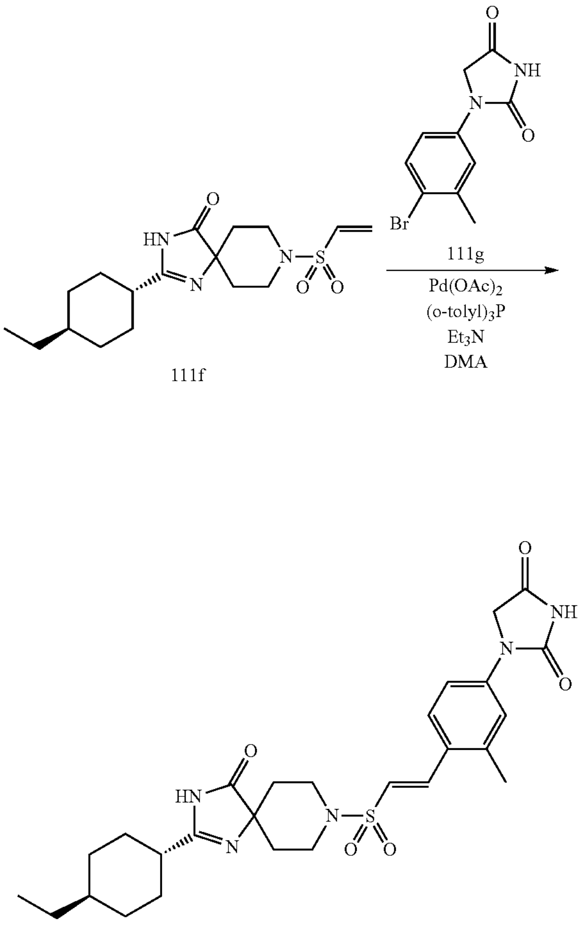

Compound 624

1-(4-{(E)-2-[2-(4-Ethyl-cyclohexyl)-4-oxo-1,3,8-triaza-spiro[4.5]dec-1-ene-8-sulfonyl]-vinyl}-3-methyl-phenyl)-imidazolidine-2,4-dione was synthesized by operations similar to those in Reaction 26-1 using appropriate reagents and starting material.

MS (ESI) m/z=542 (M+H)+.

The example compounds shown below were synthesized by operations similar to those in Reaction 111-2 using appropriate reagents and starting materials.

Compounds 625 to Compound 626

TABLE 84

| Target Compound | Structure | LCMS condition | Retention time (min) | MS (m/z) |
|---|---|---|---|---|
| 625 | 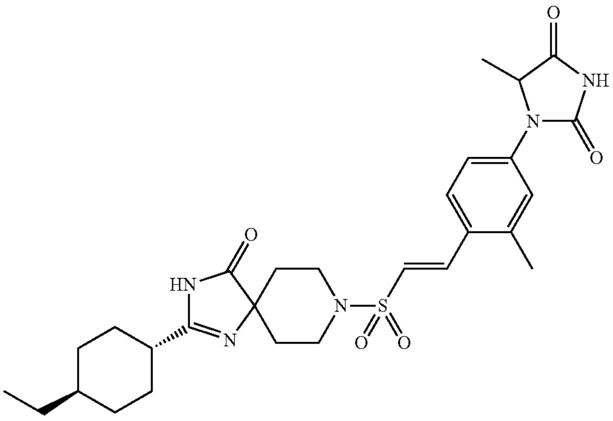 [SMILES: CC[C@H]1CC[C@H](C2=NC3(CCN(S(=O)(=O)/C=C/c4ccc(N5C(=O)NC(=O)C5C)cc4C)CC3)C(=O)N2)CC1] | LCMS-C-1 | 2.7 | 556 (M + H)+ |
| 626 | 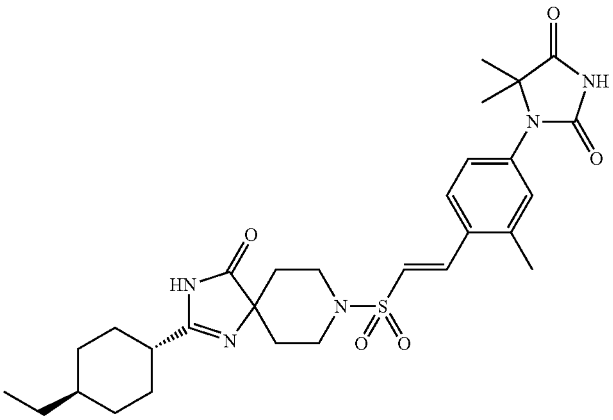 [SMILES: CC[C@H]1CC[C@H](C2=NC3(CCN(S(=O)(=O)/C=C/c4ccc(N5C(=O)NC(=O)C5(C)C)cc4C)CC3)C(=O)N2)CC1] | LCMS-C-1 | 2.73 | 571 (M + H)+ |

The aryl bromide reagent used in the synthesis of Compound 624 (1-(4-bromo-3-methyl-phenyl)-imidazolidine-2,4-dione) was synthesized as follows.

(Reaction 111-3)

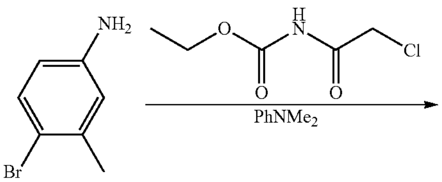

26h

-continued

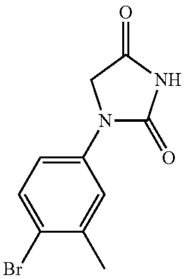

111g (2-Chloro-acetyl)-carbamic acid ethyl ester (356 mg, 2.15 mmol) was added to 4-bromo-3-methyl-phenylamine (400 mg, 2.15 mmol) and dimethylphenylamine (273 μL, 2.15 mmol) at room temperature. The mixture was stirred at 130° C. for five hours, and the reaction solution was then cooled. The precipitate was collected by filtration and washed with $CH_3CN$ to give 1-(4-bromo-3-methyl-phenyl)-imidazolidine-2,4-dione as a colorless solid (314 mg, 54%).

MS (ESI) m/z=267, 269 (M+H)+.

The aryl bromide reagent used in the synthesis of Compound 625 (1-(4-bromo-3-methyl-phenyl)-5-methyl-imidazolidine-2,4-dione) was synthesized as follows.

(Reaction 111-4)

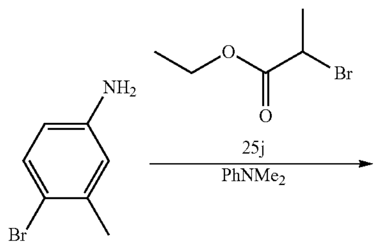

26h

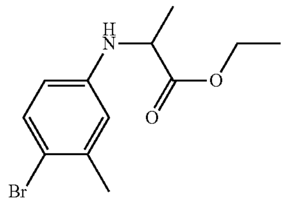

111h

2-Bromo-propionic acid ethyl ester (973 mg, 5.22 mmol) was added to 4-bromo-3-methyl-phenylamine (1.00 g, 5.37 mmol) and dimethylphenylamine (682 μL, 5.37 mmol) at room temperature, and the mixture was stirred at 60° C. for 15 hours. The reaction solution was then cooled and concentrated under reduced pressure. The resulting residue was purified by silica gel column chromatography (hexane-ethyl acetate) to give 2-(4-bromo-3-methyl-phenylamino)-propionic acid ethyl ester as a yellow form (1.38 g, 90%).

MS (ESI) m/z=286, 288 (M+H)+.

(Reaction 111-5)

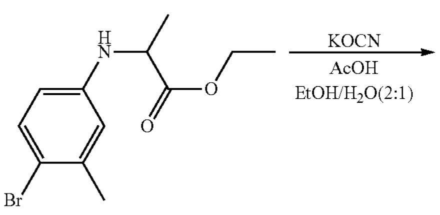

111h

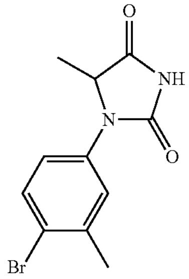

111i

KOCN (326 mg, 4.02 mmol) was added to a mixed solution of 2-(4-bromo-3-methyl-phenylamino)-propionic acid ethyl ester (383 mg, 1.34 mmol) in EtOH (5.30 mL) and $H_2O$ (2.68 mL). The mixture was stirred at room temperature for three hours and at 60° C. for 11 hours, and AcOH (1 mL) was then added, followed by further stirring for two hours. KOCN (163 mg, 2.01 mmol) was added, followed by further stirring for three hours. The reaction solution was cooled. $H_2O$ (50 mL) was added to the reaction solution at room temperature, and this aqueous layer was then extracted with ethyl acetate (20 mL×3). The organic layers were concentrated under reduced pressure, and the resulting residue was purified by silica gel column chromatography (dichloromethane-methanol) to give 1-(4-bromo-3-methyl-phenyl)-5-methyl-imidazolidine-2,4-dione as a yellow form (134 mg, 35%).

MS (ESI) m/z=283, 285 (M+H)+.

The aryl bromide reagent used in the synthesis of Compound 626 (1-(4-bromo-3-methyl-phenyl)-5,5-dimethyl-imidazolidine-2,4-dione) was synthesized as follows.

(Reaction 111-6)

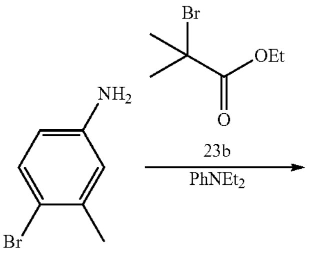

26h

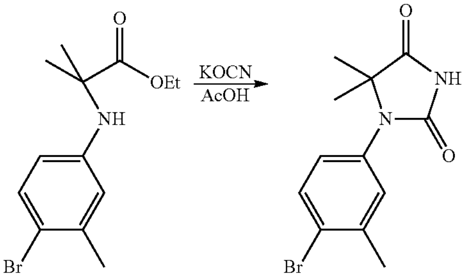

111j 111k 1-(4-Bromo-3-methyl-phenyl)-5,5-dimethyl-imidazolidine-2,4-dione was synthesized by operations similar to those in Reaction 111-4 and Reaction 111-5 using appropriate reagents and starting material.

MS (ESI) m/z=297, 299 (M+H)+.

Example 112

8-{(E)-2-[4-(3,4-Dihydroxy-butoxy)-2,6-dimethyl-phenyl]-ethenesulfonyl}-2-nonyl-1,3,8-triaza-spiro [4.5]dec-1-en-4-one (Compound 627)

(Reaction 112-1)

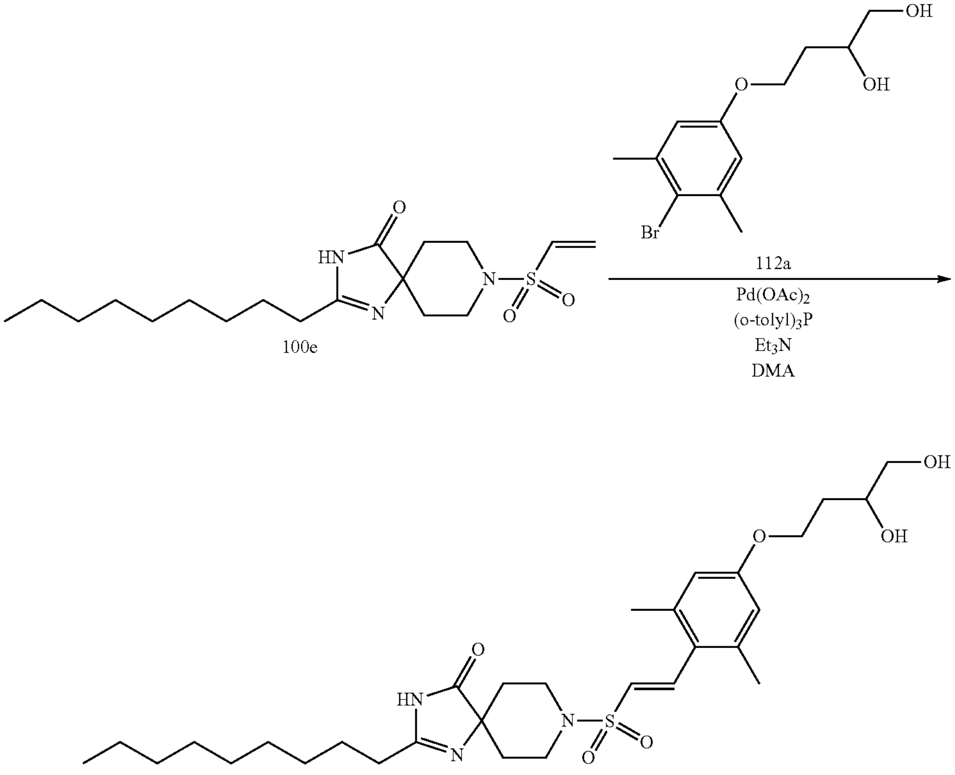

Compound 627

8-{(E)-2-[4-(3,4-Dihydroxy-butoxy)-2,6-dimethyl-phenyl]-ethenesulfonyl}-2-nonyl-1,3,8-triaza-spiro[4.5]dec-1-en-4-one was synthesized by operations similar to those in Reaction 26-1 using appropriate reagents and starting material.

MS (ESI) m/z=578 (M+H)+.

The example compound shown below was synthesized by operations similar to those in Example 112 using appropriate reagents and starting material.

Compound 628

TABLE 85

| Target Compound | Structure | LCMS condition | Retention time (min) | MS (m/z) |
|---|---|---|---|---|
| 628 | 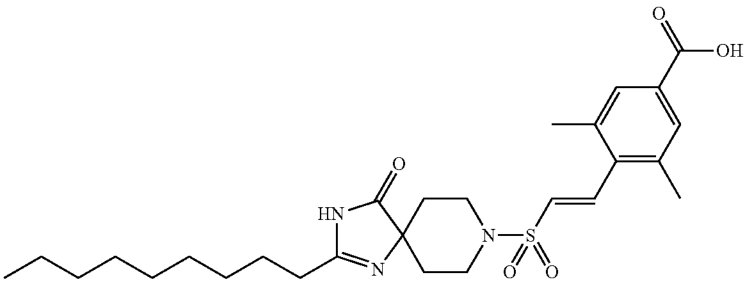 [SMILES: CCCCCCCCCC1=NC2(CCN(S(=O)(=O)/C=C/c3c(C)cc(C(=O)O)cc3C)CC2)C(=O)N1] | LCMS-F-1 | 0.96 | 518 (M + H)+ |

Example 113

3,5-Dimethyl-4-((E)-2-{4-oxo-2-[4-(3,3,3-trifluoro-propyl)-cyclohexyl]-1,3,8-triaza-spiro[4.5]dec-1-ene-8-sulfonyl}-vinyl)-benzoic acid trimethylhydrazide (Compound 629)

(Reaction 113-1)

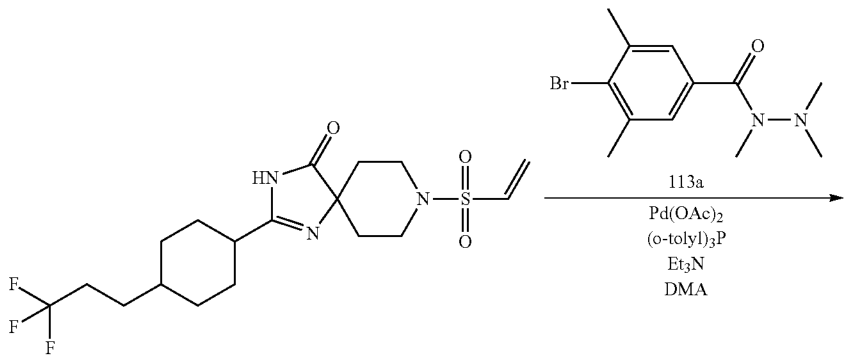

101j

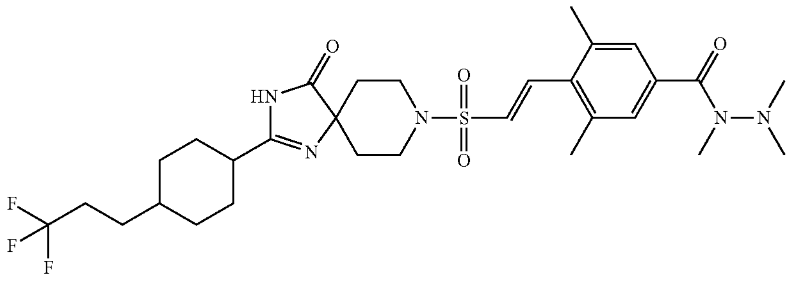

Compound 629

3,5-Dimethyl-4-((E)-2-{4-oxo-2-[4-(3,3,3-trifluoro-propyl)-cyclohexyl]-1,3,8-triaza-spiro[4.5]dec-1-ene-8-sulfonyl}-vinyl)-benzoic acid trimethylhydrazide was synthesized by operations similar to those in Reaction 26-1 using appropriate reagents and starting material.

MS (ESI) m/z=626 (M+H)+.

The example compound shown below was synthesized by operations similar to those in Example 113 using appropriate reagents and starting material.

Compound 630

TABLE 86

| Target Compound | Structure | LCMS condition | Retention time (min) | MS (m/z) |
|---|---|---|---|---|
| 630 | 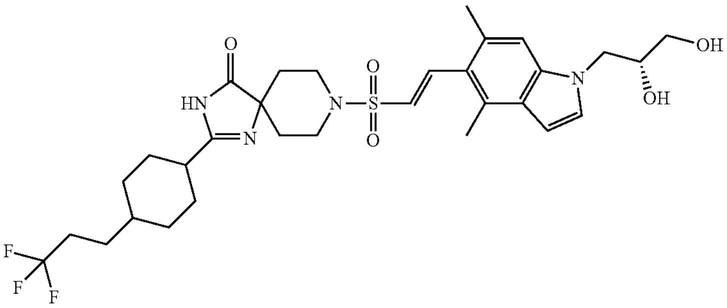 [SMILES: Cc1cc2c(ccn2C[C@@H](O)CO)c(C)c1/C=C/S(=O)(=O)N1CCC2(CC1)N=C(C1CCC(CCC(F)(F)F)CC1)NC2=O] | LCMS-D-1 | 2.37 | 639 (M + H)+ |

The aryl bromide reagent used in the synthesis of Compound 629 (4-bromo-3,5-dimethyl-benzoic acid trimethylhydrazide) was synthesized as follows.

(Reaction 113-2)

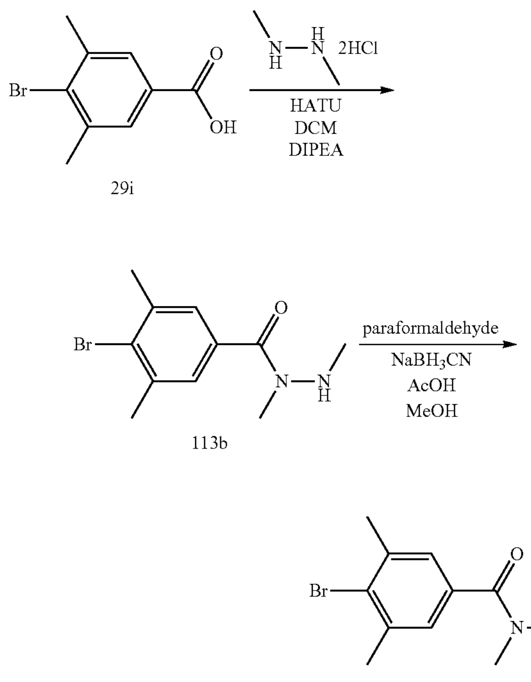

29i

113b

113a

4-Bromo-3,5-dimethyl-benzoic acid trimethylhydrazide was synthesized by operations similar to those in Reaction 10-14 and Reaction 41-1 using appropriate reagents and starting material.

$^1$H-NMR ($CDCl_3$) δ 7.20 (s, 2H), 3.02 (s, 2H), 2.48 (s, 6H), 2.42 (s, 6H).

The aryl bromide reagent used in the synthesis of Compound 630 ((R)-3-(5-bromo-4,6-dimethyl-indol-1-yl)-propane-1,2-diol) was synthesized as follows.

(Reaction 113-3)

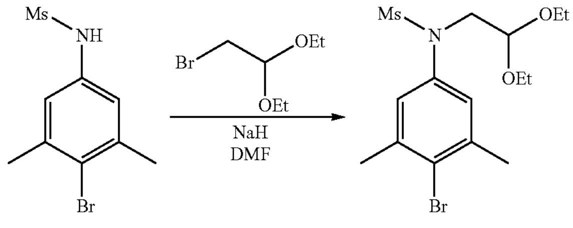

107z

113c

N-(4-Bromo-3,5-dimethyl-phenyl)-N-(2,2-diethoxy-ethyl)-methanesulfonamide was synthesized by operations similar to those in Reaction 25-3 using appropriate reagents and starting material.

$^1$H-NMR ($CDCl_3$) δ 7.06 (s, 2H), 4.57 (t, 1H, J=5.72 Hz), 3.71 (d, 2H, J=5.72 Hz), 3.64 (m, 2H), 3.49 (m, 2H), 2.95 (s, 3H), 2.40 (s, 6H), 1.15 (t, 6H, J=7.24 Hz).

(Reaction 113-4)

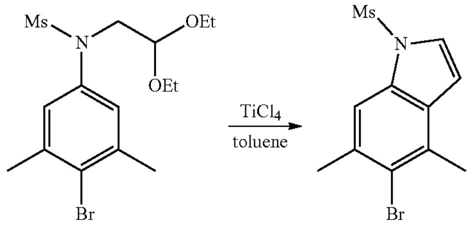

113c

113d

A 1 M solution of titanium(IV) chloride in dichloroethane (5.3 ml, 5.3 mmol) was added to a solution of N-(4-bromo-3,5-dimethyl-phenyl)-N-(2,2-diethoxy-ethyl)-methanesulfonamide (2.09 g, 5.3 mmol) in toluene (17 ml) at room temperature, and the mixture was heated with stirring at 100° C. for two hours. An aqueous sodium bicarbonate solution was added to the reaction solution, followed by extraction with ethyl acetate. The organic phase was washed with saturated brine and concentrated under reduced pressure. The resulting residue was purified by silica gel column chromatography (hexane-ethyl acetate) to give 5-bromo-4,6-dimethyl-1-methanesulfonyl-indole (1.28 g, 80%).

$^1$H-NMR ($CDCl_3$) δ 7.66 (s, 1H), 7.37 (d, 1H, J=3.81 Hz), 6.69 (dd, 1H, J=3.81, 0.76 Hz), 3.07 (s, 3H), 2.57 (d, 6H, J=13.73 Hz).

(Reaction 113-5)

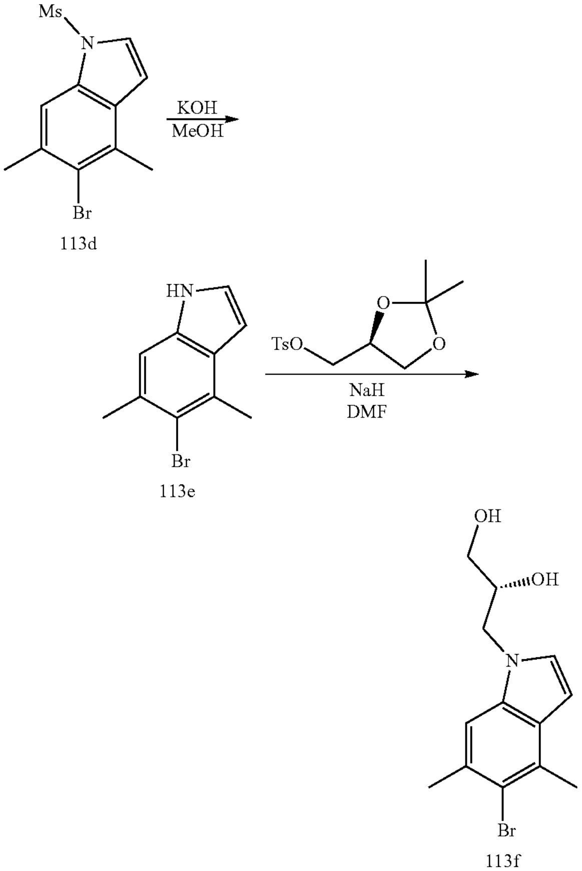

113d

113e

113f (R)-3-(5-Bromo-4,6-dimethyl-indol-1-yl)-propane-1,2-diol was synthesized by operations similar to those in Reaction 14-1 and Reaction 25-3 using appropriate reagents and starting material.

MS (ESI) m/z=298, 300 (M+H)+.

Example 114

3-(4-{(E)-2-[2-(4-Butyl-cyclohexyl)-4-oxo-1,3,8-triaza-spiro[4.5]dec-1-ene-8-sulfonyl]-vinyl}-3,5-dimethyl-phenyl)-imidazolidine-2,4-dione (Compound 631)

(Reaction 114-1)

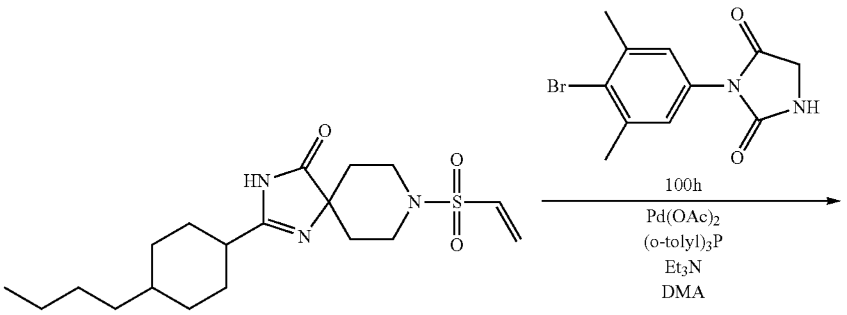

102e

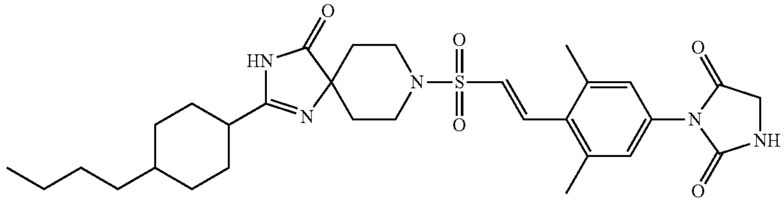

Compound 631

3-(4-{(E)-2-[2-(4-Butyl-cyclohexyl)-4-oxo-1,3,8-triaza-spiro[4.5]dec-1-ene-8-sulfonyl]-vinyl}-3,5-dimethyl-phenyl)-imidazolidine-2,4-dione was synthesized by operations similar to those in Reaction 26-1 using appropriate reagents and starting material.

MS (ESI) m/z=584 (M+H)+.

The example compound shown below was synthesized by operations similar to those in Example 114 using appropriate reagents and starting material.

Compound 632

TABLE 87

| Target Compound | Structure | LCMS condition | Retention time (min) | MS (m/z) |
|---|---|---|---|---|
| 632 | 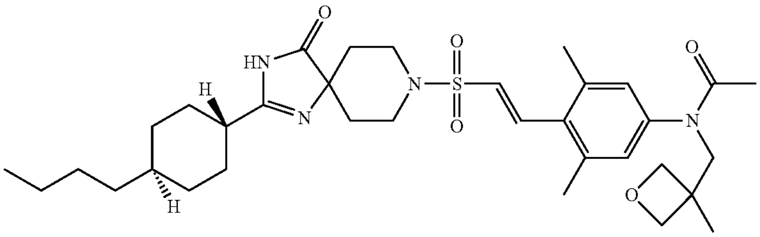 [SMILES: CCCC[C@H]1CC[C@H](C2=NC3(CCN(S(=O)(=O)/C=C/c4c(C)cc(N(CC5(C)COC5)C(C)=O)cc4C)CC3)C(=O)N2)CC1] | LCMS-D-1 | 3.22 | 627 (M + H)+ |

Example 115

2-Cyclohexyl-8-((E)-2-quinolin-8-yl-ethenesulfonyl)-1,3,8-triaza-spiro[4.5]dec-1-en-4-one (Compound 633)

(Reaction 115-1)

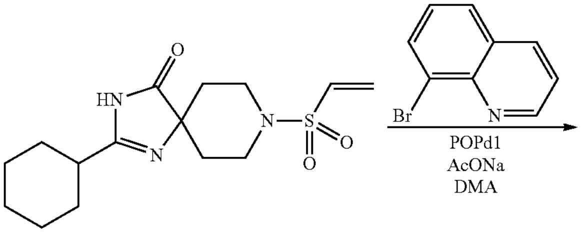

25b

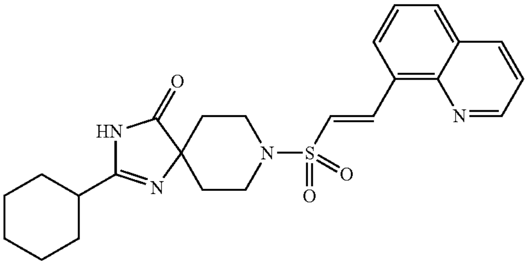

Compound 633

2-Cyclohexyl-8-ethenesulfonyl-1,3,8-triaza-spiro[4.5]dec-1-en-4-one (20 mg, 61.5 μmol), 8-bromoquinoline (19 mg, 91.3 μmol), POPd1 (Combiphos, 2.9 mg, 3.1 μmol) and sodium acetate (7.6 mg, 92.6 μmol) in dimethylacetamide (0.6 ml) were mixed in a sealed vessel in a nitrogen atmosphere. This mixture was irradiated in a microwave apparatus (190° C., 40 min). The reaction mixture was cooled, and then quenched with water and extracted with ethyl acetate. The organic layer was washed with saturated brine, and then dried over anhydrous sodium sulfate and concentrated under reduced pressure. The resulting residue was purified by silica gel column chromatography to give 2-cyclohexyl-8-((E)-2-quinolin-8-yl-ethenesulfonyl)-1,3,8-triaza-spiro[4.5]dec-1-en-4-one (15.3 mg, 16%).

MS (ESI) m/z=453 (M+H)+.

The example compound shown below was synthesized by operations similar to those in Example 115 using appropriate reagents and starting material.

Compound 634

TABLE 88

| Target Compound | Structure | LCMS condition | Retention time (min) | MS (m/z) |
|---|---|---|---|---|
| 634 | 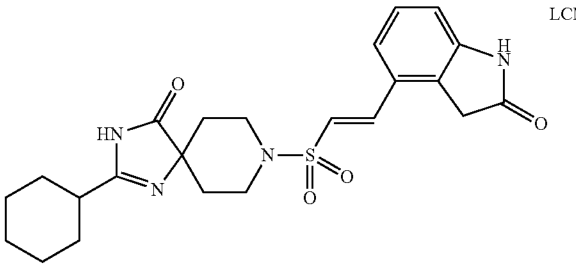 | LCMS-C-1 | 2.3 | 457 (M + H)+ |

Example 116

3-(3,5-Dimethyl-4-{(E)-2-[4-oxo-2-(3-trifluoromethoxy-phenyl)-1,3,8-triaza-spiro[4.5]dec-1-ene-8-sulfonyl]-vinyl}-phenyl)-imidazolidine-2,4-dione (Compound 635)

(Reaction 116-1)

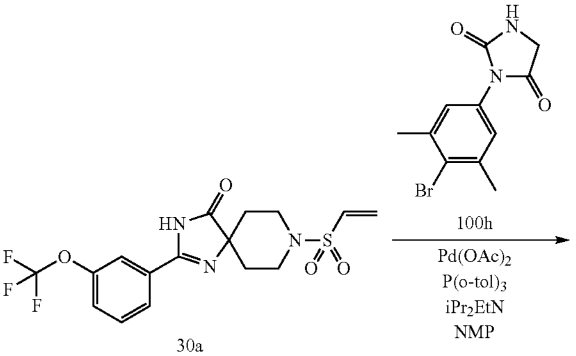

30a

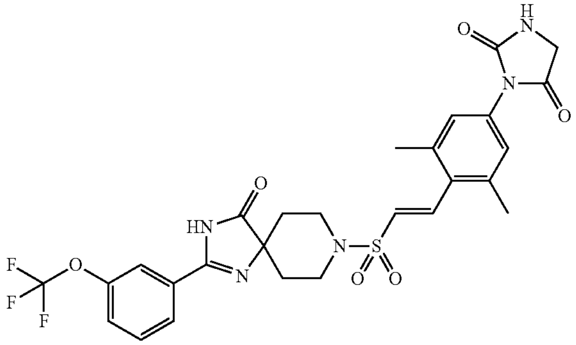

Compound 635

3-(3,5-Dimethyl-4-{(E)-2-[4-oxo-2-(3-trifluoromethoxy-phenyl)-1,3,8-triaza-spiro[4.5]dec-1-ene-8-sulfonyl]-vinyl}-phenyl)-imidazolidine-2,4-dione was synthesized by operations similar to those in Reaction 26-1 (using NMP as a solvent) using appropriate reagents and starting material.

MS (ESI) m/z=606 (M+H)+.

Example 117

3-(4-{(E)-2-[2-(4-Fluoro-3-trifluoromethyl-phenyl)-4-oxo-1,3,8-triaza-spiro[4.5]dec-1-ene-8-sulfonyl]-vinyl}-3,5-dimethyl-phenyl)-imidazolidine-2,4-dione (Compound 636)

(Reaction 117-1)

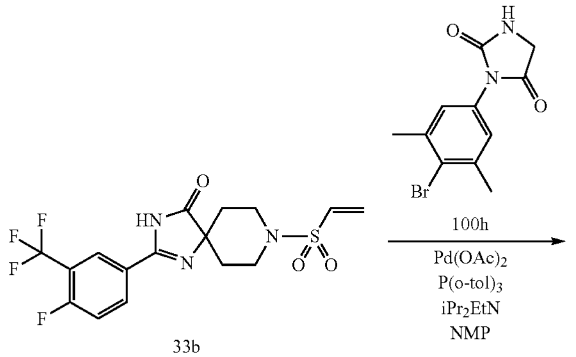

33b

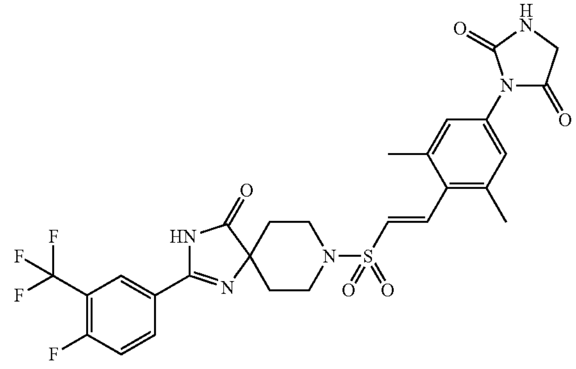

Compound 636

3-(4-{(E)-2-[2-(4-Fluoro-3-trifluoromethyl-phenyl)-4-oxo-1,3,8-triaza-spiro[4.5]dec-1-ene-8-sulfonyl]-vinyl}-3,5-dimethyl-phenyl)-imidazolidine-2,4-dione was synthesized by operations similar to those in Reaction 26-1 (using NMP as a solvent) using appropriate reagents and starting material.

MS (ESI) m/z=608 (M+H)+.

Example 118

2-Cyclohexyl-8-[(E)-2-(2-methyl-1H-indol-4-yl)-ethenesulfonyl]-1,3,8-triaza-spiro[4.5]dec-1-en-4-one (Compound 637)

(Reaction 118-1)

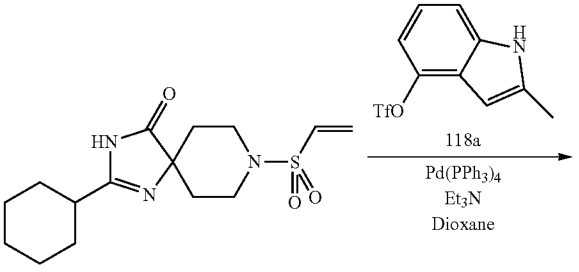

25b

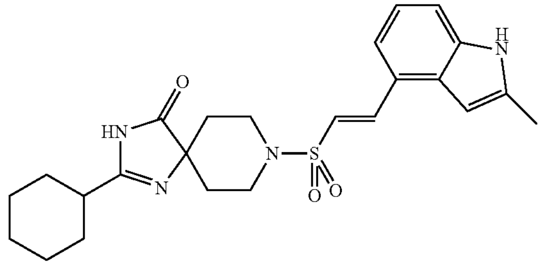

Compound 637

A mixture of 2-cyclohexyl-8-ethenesulfonyl-1,3,8-triaza-spiro[4.5]dec-1-en-4-one (100 mg, 0.307 mmol), trifluoro-methanesulfonic acid 2-methyl-1H-indol-4-yl ester (129 mg, 0.462 mmol), tetrakistriphenylphosphine palladium(0) (35 mg, 30.2 μmol) and triethylamine (130 μL, 0.933 mmol) in 1,4-dioxane (1.5 ml) was heated with stirring at 100° C. for 18 hours. The reaction mixture was cooled, and then quenched with water and extracted with ethyl acetate. The organic layer was washed with saturated brine, and then dried over anhydrous sodium sulfate and concentrated under reduced pressure. The resulting residue was purified by silica gel column chromatography to give 2-cyclohexyl-8-[(E)-2-(2-methyl-1H-indol-4-yl)-ethenesulfonyl]-1,3,8-triaza-spiro[4.5]dec-1-en-4-one (19.3 mg, 14%).

MS (ESI) m/z=455 (M+H)+.

The example compound shown below was synthesized by operations similar to those in Example 118 using appropriate reagents and starting material.

Compound 638

TABLE 89

| Target Compound | Structure | LCMS condition | Retention time (min) | MS (m/z) |
|---|---|---|---|---|
| 638 | 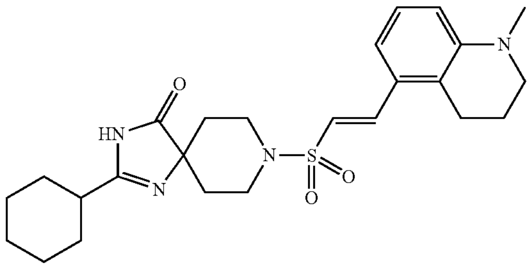 [SMILES: CN1CCCc2c(/C=C/S(=O)(=O)N3CCC4(CC3)N=C(C3CCCCC3)NC4=O)cccc21] | LCMS-A-1 | 1.99 | 471 (M + H)+ |

Toluene-4-sulfonic acid 1-methyl-1,2,3,4-tetrahydro-quinolin-5-yl ester used in the synthesis of Compound 638 was synthesized as follows.

(Reaction 118-2)

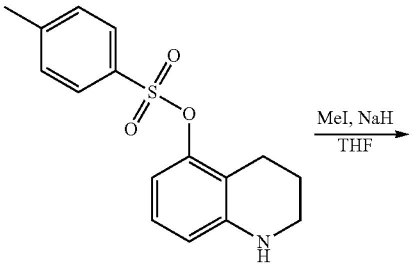

118b

-continued

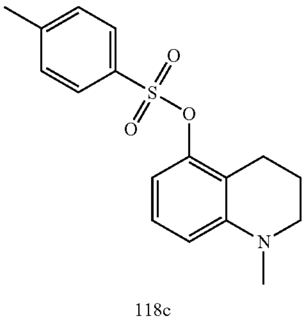

118c

Toluene-4-sulfonic acid 1-methyl-1,2,3,4-tetrahydro-quinolin-5-yl ester was synthesized by operations similar to those in Reaction 25-3 using appropriate reagents and starting material.

$^1$H-NMR (270 MHz, $CDCl_3$) δ 1.92-2.02 (2H, m), 2.75-2.82 (2H, m), 2.92 (3H, s), 3.22-3.28 (2H, m), 6.50-6.55 (2H, m), 7.03-7.10 (1H, dd, J=8.1, 8.1 Hz).

Example 119

8-{(E)-2-[4-(3,4-Dihydroxy-butoxy)-2,6-dimethyl-phenyl]-ethenesulfonyl}-2-(4-fluoro-3-trifluoromethyl-phenyl)-1,3,8-triaza-spiro[4.5]dec-1-en-4-one (Compound 639)

(Reaction 119-1)

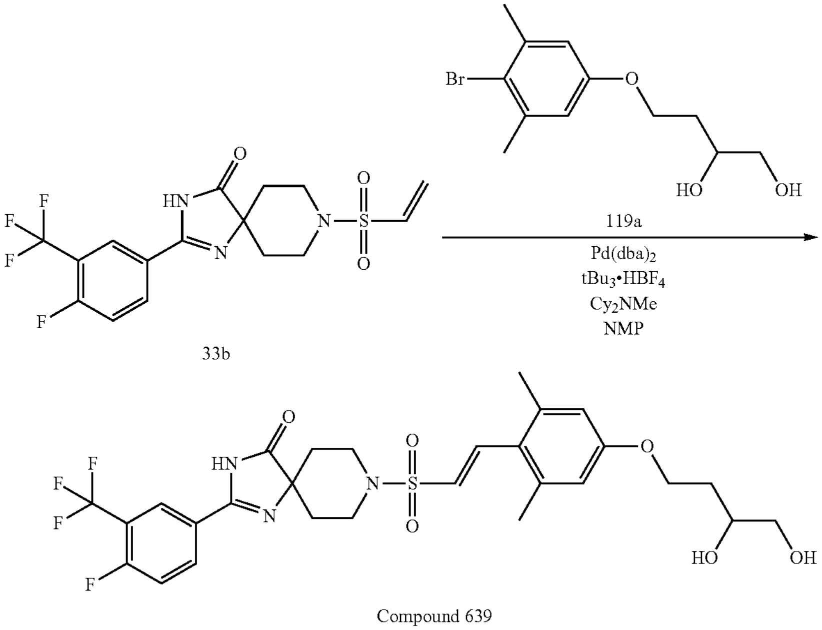

8-Ethenesulfonyl-2-(4-fluoro-3-trifluoromethyl-phenyl)-1,3,8-triaza-spiro[4.5]dec-1-en-4-one (57.6 mg, 0.142 mmol), 4-(4-bromo-3,5-dimethyl-phenoxy)-butane-1,2-diol (49.3 mg, 0.170 mmol), bis(dibenzylideneacetone)palladium (0) (8 mg, 0.014 mmol) and tri-tert-butylphosphine tetrafluoroborate (4 mg, 0.014 mmol) were placed in a vial. NMP (0.5 ml) and N-methyldicyclohexylamine (36.1 μl, 0.170 mmol) were sequentially added in a nitrogen atmosphere, and the mixture was heated with stirring at 100° C. for 2.5 hours. A saturated aqueous $NH_4Cl$ solution was added to the reaction mixture, followed by extraction with ethyl acetate. The organic layer was sequentially washed with water and saturated brine and then concentrated under reduced pressure. The resulting residue was purified by thin layer chromatography (ethyl acetate:dichloromethane:methanol=10:10:1) togive 8-{(E)-2-[4-(3,4-dihydroxy-butoxy)-2,6-dimethyl-phenyl]-ethenesulfonyl}-2-(4-fluoro-3-trifluoromethyl-phenyl)-1,3,8-triaza-spiro[4.5]dec-1-en-4-one (42.8 mg, 49%).

MS (ESI) m/z=614 (M+H)+.

The example compounds shown below were synthesized by operations similar to those in Example 119 using appropriate reagents and starting materials.

Compounds 640 to Compound 644

TABLE 90

| Target Compound | Structure | LCMS condition | Retention time (min) | MS (m/z) |
|---|---|---|---|---|
| 640 | 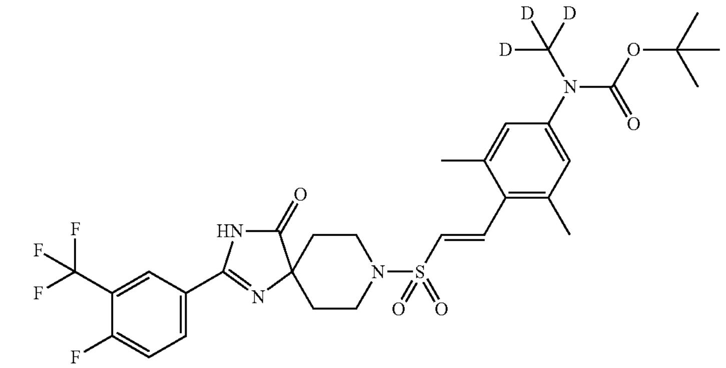 [SMILES: [2H]C([2H])([2H])N(C(=O)OC(C)(C)C)c1cc(C)c(/C=C/S(=O)(=O)N2CCC3(CC2)N=C(c2ccc(F)c(C(F)(F)F)c2)NC3=O)c(C)c1] | LCMS-F-1 | 1.13 | 642 (M + H)+ |
| 641 | 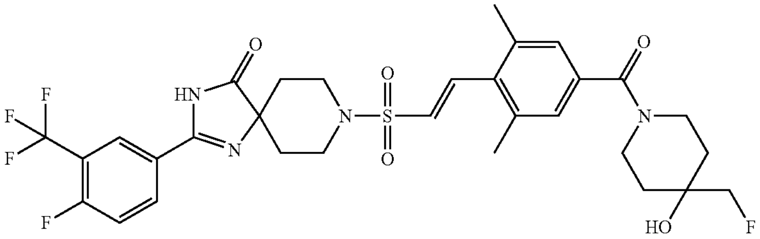 [SMILES: Cc1cc(C(=O)N2CCC(O)(CF)CC2)cc(C)c1/C=C/S(=O)(=O)N1CCC2(CC1)N=C(c1ccc(F)c(C(F)(F)F)c1)NC2=O] | LCMS-F-1 | 0.99 | 669 (M + H)+ |
| 642 | 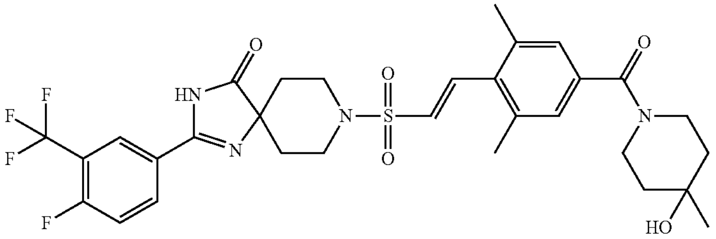 [SMILES: Cc1cc(C(=O)N2CCC(C)(O)CC2)cc(C)c1/C=C/S(=O)(=O)N1CCC2(CC1)N=C(c1ccc(F)c(C(F)(F)F)c1)NC2=O] | LCMS-C-1 | 2.7 | 651 (M + H)+ |
| 643 | 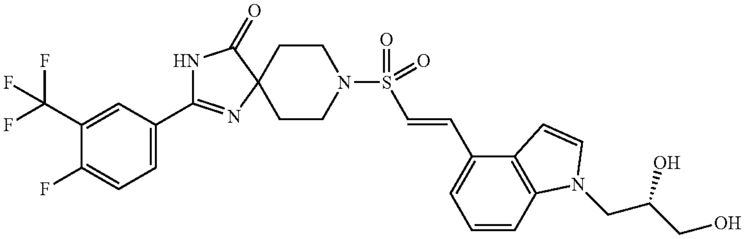 [SMILES: O=C1NC(c2ccc(F)c(C(F)(F)F)c2)=NC12CCN(S(=O)(=O)/C=C/c1cccc3c1ccn3C[C@H](O)CO)CC2] | LCMS-C-1 | 2.6 | 595 (M + H)+ |
| 644 | 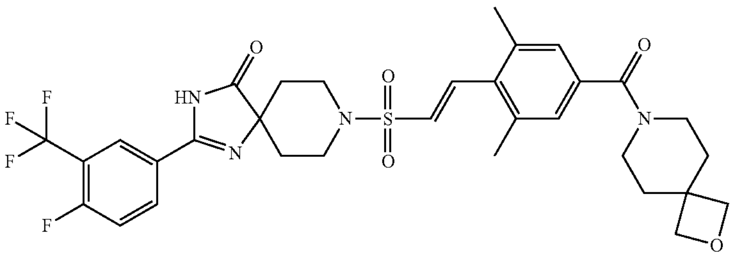 [SMILES: Cc1cc(C(=O)N2CCC3(CC2)COC3)cc(C)c1/C=C/S(=O)(=O)N1CCC2(CC1)N=C(c1ccc(F)c(C(F)(F)F)c1)NC2=O] | LCMS-F-1 | 1 | 663 (M + H)+ |

The aryl bromide reagent used in the synthesis of Compound 640 ((4-bromo-3,5-dimethyl-phenyl)-[1,1,1-$^2H_3$]methyl-carbamic acid tert-butyl ester) was synthesized as follows.

(Reaction 119-2)

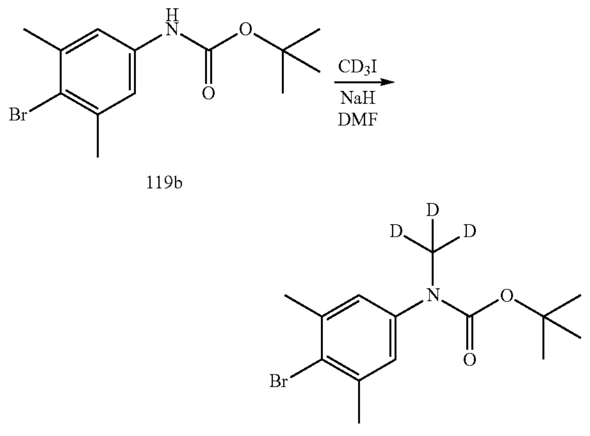

119b

119c (4-Bromo-3,5-dimethyl-phenyl)-[1,1,1-$^2H_3$] methyl-carbamic acid tert-butyl ester was synthesized by operations similar to those in Reaction 25-3 using appropriate reagents and starting material.

MS (ESI) m/z=317 (M+H)+.

The aryl bromide reagent used in the synthesis of Compound 641 ((4-bromo-3,5-dimethyl-phenyl)-(4-fluoromethyl-4-hydroxy-piperidin-1-yl)-methanone) was synthesized as follows.

(Reaction 119-3)

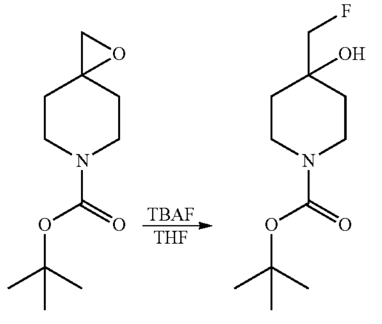

119d 119e

Tetrabutylammonium fluoride (1.0 M in THF, 5.6 ml, 5.6 mmol) was added to a solution of 1-oxa-6-aza-spiro[2.5]octane-6-carboxylic acid tert-butyl ester (400 mg, 1.87 mmol) in tetrahydrofuran (5 ml), and the mixture was heated under reflux for 36 hours. The reaction solution was cooled and then concentrated under reduced pressure. The resulting residue was purified by silica gel column chromatography (ethyl acetate-hexane) to give 4-fluoromethyl-4-hydroxy-piperidine-1-carboxylic acid tert-butyl ester (87 mg, 19%).

$^1$H-NMR ($CDCl_3$) δ 1.46 (s, 9H), 2.93-3.31 (m, 2H), 3.69-3.94 (m, 2H), 4.14 (s, 1H), 4.30 (s, 1H).

(Reaction 119-4)

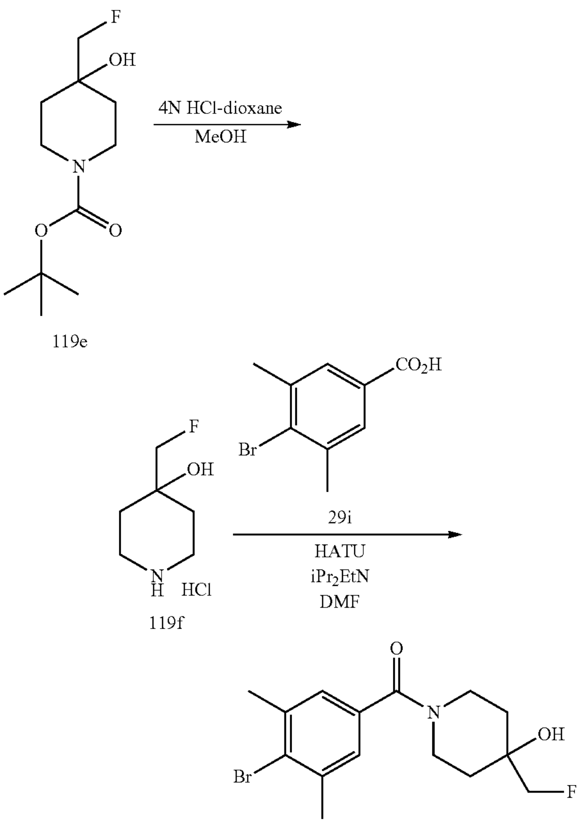

119e

119f

29i

119g (4-Bromo-3,5-dimethyl-phenyl)-(4-fluoromethyl-4-hydroxy-piperidin-1-yl)-methanone was synthesized by operations similar to those in Reaction 5-3 and Reaction 10-14 using appropriate reagents and starting material.

MS (ESI) m/z=344, 346 (M+H)+.

The aryl bromide reagent used in the synthesis of Compound 642 ((4-bromo-3,5-dimethyl-phenyl)-(4-hydroxy-4-methyl-piperidin-1-yl)-methanone) was synthesized as follows.

(Reaction 119-5)

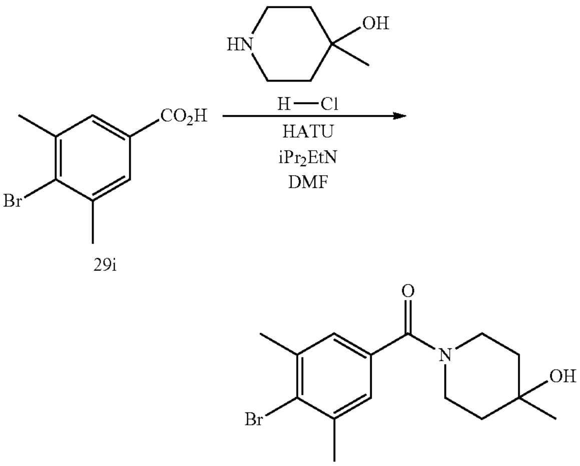

29i

119h (4-Bromo-3,5-dimethyl-phenyl)-(4-hydroxy-4-methyl-piperidin-1-yl)-methanone was synthesized by operations similar to those in Reaction 10-14 using appropriate reagents and starting material.

MS (ESI) m/z=326, 328 (M+H)+.

The aryl bromide reagent used in the synthesis of Compound 644 ((4-bromo-3,5-dimethyl-phenyl)-(2-oxa-7-aza-spiro[3.5]non-7-yl)-methanone) was synthesized as follows.

(Reaction 119-6)

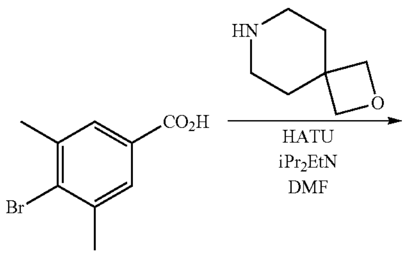

29i

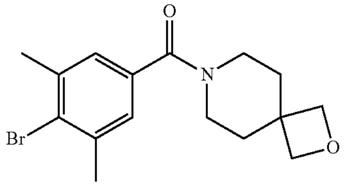

119i (4-Bromo-3,5-dimethyl-phenyl)-(2-oxa-7-aza-spiro[3.5]non-7-yl)-methanone was synthesized by operations similar to those in Reaction 10-14 using appropriate reagents and starting material.

MS (ESI) m/z=338, 340 (M+H)+.

Example 120

2-Cyclohexyl-8-[2-(1,2,3,4-tetrahydro-quinolin-5-yl)-ethanesulfonyl]-1,3,8-triaza-spiro[4.5]dec-1-en-4-one (Compound 645)

(Reaction 120-1)

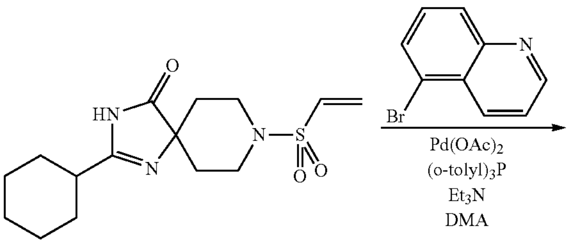

25b

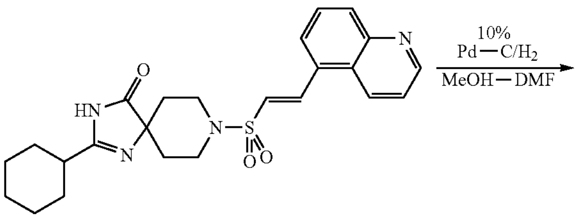

120a

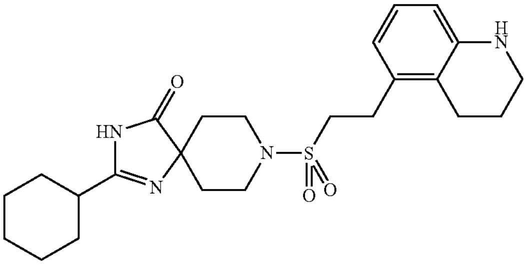

Compound 645

2-Cyclohexyl-8-[2-(1,2,3,4-tetrahydro-quinolin-5-yl)-ethanesulfonyl]-1,3,8-triaza-spiro[4.5]dec-1-en-4-one was synthesized by operations similar to those in Reaction 25-2 and Reaction 42-1 using appropriate reagents and starting material.

MS (ESI) m/z=459 (M+H)+.

The example compounds shown below were synthesized by operations similar to those in Example 120 using appropriate reagents and starting materials.

Compounds 646 to Compound 652

TABLE 91

| Target Compound | Structure | LCMS condition | Retention time (min) | MS (m/z) |
|---|---|---|---|---|
| 646 | 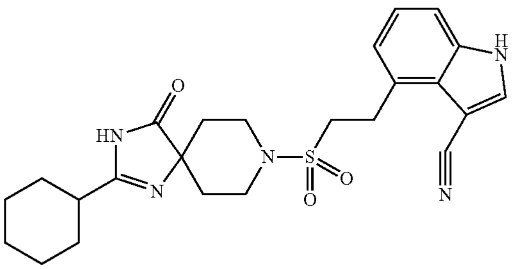 [SMILES: N#Cc1c[nH]c2cccc(CCS(=O)(=O)N3CCC4(CC3)N=C(C3CCCCC3)NC4=O)c12] | LCMS-C-1 | 2.42 | 468 (M + H)+ |

TABLE 91-continued
| Target Compound | Structure | LCMS condition | Retention time (min) | MS (m/z) |
|---|---|---|---|---|
| 647 | 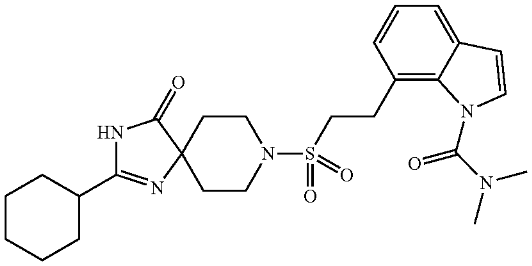 [SMILES: CN(C)C(=O)n1ccc2cccc(CCS(=O)(=O)N3CCC4(CC3)N=C(C3CCCCC3)NC4=O)c21] | LCMS-C-1 | 2.60 | 514 (M + H)+ |
| 648 | 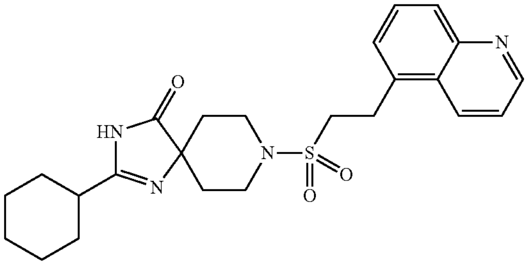 [SMILES: O=C1NC(C2CCCCC2)=NC12CCN(S(=O)(=O)CCc1cccc3ncccc13)CC2] | LCMS-C-1 | 2.47 | 455 (M + H)+ |
| 649 | 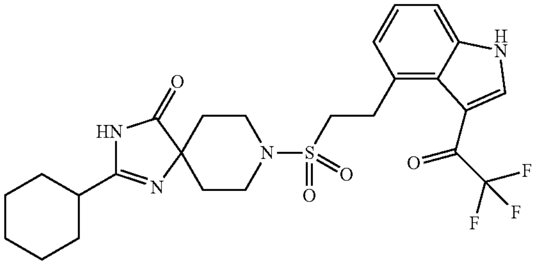 [SMILES: O=C(c1c[nH]c2cccc(CCS(=O)(=O)N3CCC4(CC3)N=C(C3CCCCC3)NC4=O)c12)C(F)(F)F] | LCMS-C-1 | 2.70 | 539 (M + H)+ |
| 650 | 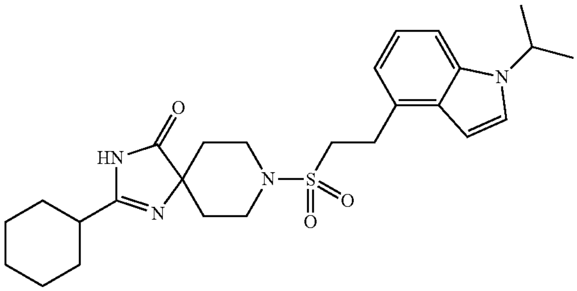 [SMILES: CC(C)n1ccc2c(CCS(=O)(=O)N3CCC4(CC3)N=C(C3CCCCC3)NC4=O)cccc21] | LCMS-C-1 | 2.88 | 485 (M + H)+ |
| 651 | 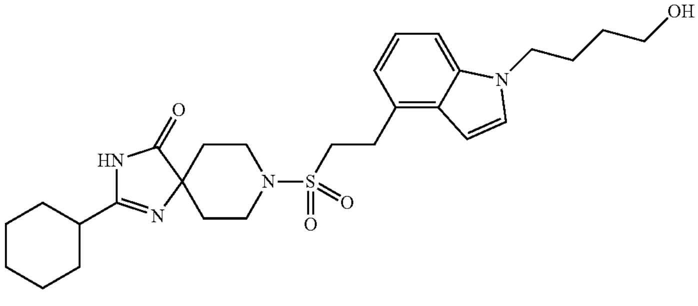 [SMILES: O=C1NC(C2CCCCC2)=NC12CCN(S(=O)(=O)CCc1cccc3c1ccn3CCCCO)CC2] | LCMS-A-1 | 2.05 | 515 (M + H)+ |

TABLE 91-continued

| Target Compound | Structure | LCMS condition | Retention time (min) | MS (m/z) |
|---|---|---|---|---|
| 652 | 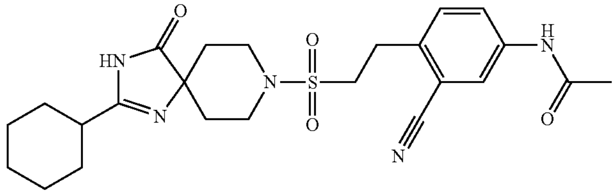 [SMILES: CC(=O)Nc1ccc(CCS(=O)(=O)N2CCC3(CC2)N=C(C2CCCCC2)NC3=O)c(C#N)c1] | LCMS-D-1 | 2.07 | 486 (M + H)+ |

The aryl bromide reagent used in the synthesis of Compound 647 ((7-bromo-indole-1-carboxylic acid dimethylamide) was synthesized as follows.

(Reaction 120-2)

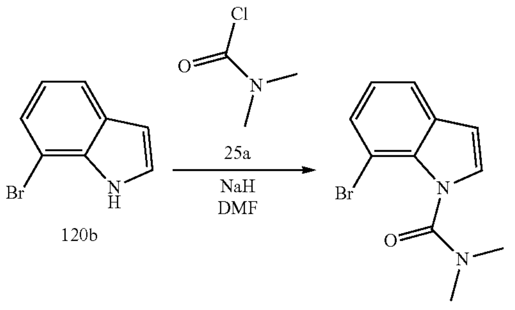

120b

120c

7-Bromo-indole-1-carboxylic acid dimethylamide was synthesized by operations similar to those in Reaction 25-3 using appropriate reagents and starting material.

MS (ESI) m/z=267, 269 (M+H)+.

The aryl bromide reagent used in the synthesis of Compound 649 (1-(4-bromo-1H-indol-3-yl)-2,2,2-trifluoro-ethanone) was synthesized as follows.

(Reaction 120-3)

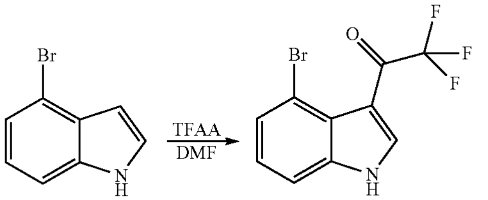

25d

120d

Trifluoroacetic anhydride (850 μL, 6.12 mmol) was added to a solution of 4-bromoindole (1.00 g, 5.10 mmol) in N,N-dimethylformamide (2.0 mL), and the mixture was stirred at room temperature for 1.5 hours. Water was added, followed by extraction with a mixed solvent of ethyl acetate:hexane=4:1. The organic layers were combined, washed with a saturated aqueous sodium bicarbonate solution, water and saturated brine and dried over sodium sulfate, and the solvent was then distilled off. The residue was purified by silica gel column chromatography to give 1-(4-bromo-1H-indol-3-yl)-2,2,2-trifluoro-ethanone (353 mg, 24%).

MS (ESI) m/z=292 (M+H)+.

The aryl bromide reagent used in the synthesis of Compound 650 (4-bromo-1-isopropyl-1H-indole) was synthesized as follows.

(Reaction 120-4)

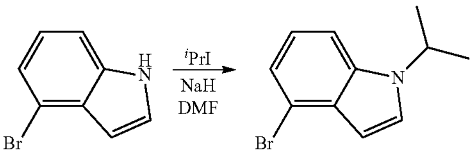

25d

120e

4-Bromo-1-isopropyl-1H-indole was synthesized by operations similar to those in Reaction 25-3 using appropriate reagents and starting material.

MS (ESI) m/z=238, 240 (M+H)+.

The aryl bromide reagent used in the synthesis of Compound 651 (4-(4-bromo-indol-1-yl)-butan-1-ol) was synthesized as follows.

(Reaction 120-5)

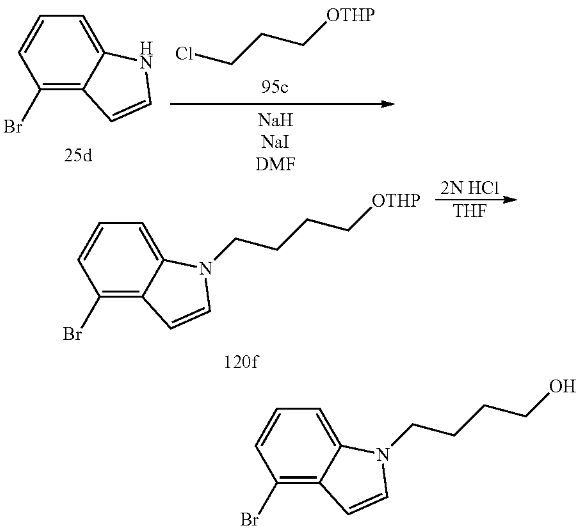

25d

120f

120g 4-(4-Bromo-indol-1-yl)-butan-1-ol was synthesized by operations similar to those in Reaction 25-3 and Reaction 25-4 using appropriate reagents and starting material.

MS (ESI) m/z=268, 270 (M+H)+.

The aryl bromide reagent used in the synthesis of Compound 652 (N-(4-bromo-3-cyano-phenyl)-acetamide) was synthesized as follows.

(Reaction 120-6)

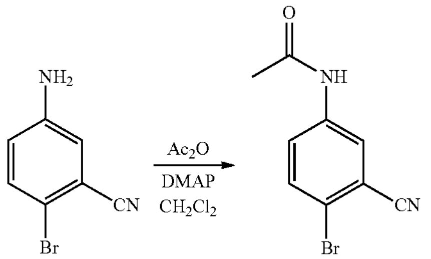

120h 120i

N-(4-Bromo-3-cyano-phenyl)-acetamide was synthesized by operations similar to those in Reaction 19-2 (using DMAP as a base) using appropriate reagents and starting material.

$^1$H-NMR (DMSO-d6) δ 10.39 (s, 1H), 8.18 (d, 1H, J=2.28 Hz), 7.79 (d, 1H, J=8.74 Hz), 7.70 (dd, 1H, J=9.15, 2.67 Hz), 2.07 (s, 3H).

Example 121

8-(2-Isoquinolin-5-yl-ethanesulfonyl)-2-(3-trifluoromethoxy-phenyl)-1,3,8-triaza-spiro[4.5]dec-1-en-4-one (Compound 653)

(Reaction 121-1)

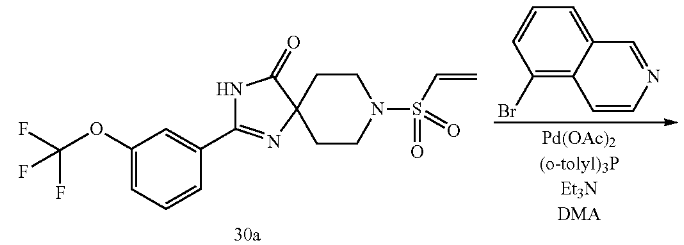

30a

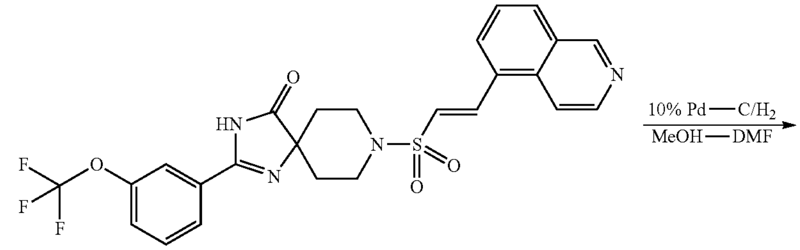

121a

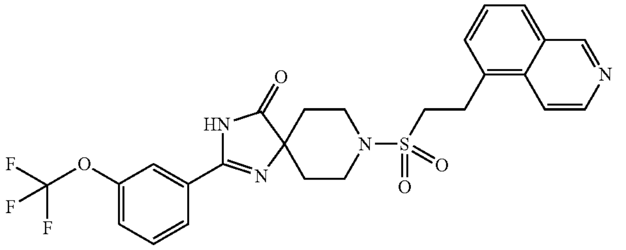 [SMILES: O=C1NC(c2cccc(OC(F)(F)F)c2)=NC12CCN(S(=O)(=O)CCc1cccc3ncccc13)CC2]

Compound 653

8-(2-Isoquinolin-5-yl-ethanesulfonyl)-2-(3-trifluoromethoxy-phenyl)-1,3,8-triaza-spiro[4.5]dec-1-en-4-one was synthesized by operations similar to those in Reaction 25-2 and Reaction 42-1 using appropriate reagents and starting material.

MS (ESI) m/z=533 (M+H)+.

The example compound shown below was synthesized by operations similar to those in Example 121 using appropriate reagents and starting material.

Compound 654

TABLE 92

| Target Compound | Structure | LCMS condition | Retention time (min) | MS (m/z) |
|---|---|---|---|---|
| 654 | 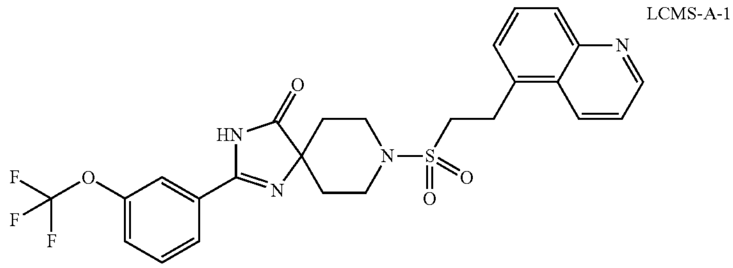 | LCMS-A-1 | 2.02 | 533 (M + H)+ |

Example 122

N-(3-Methoxy-4-{2-[2-(4-methyl-cyclohexyl)-4-oxo-1,3,8-triaza-spiro[4.5]dec-1-ene-8-sulfonyl]-ethyl}-phenyl)-acetamide (Compound 655)

(Reaction 122-1)

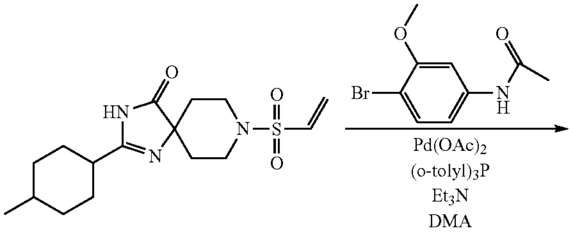

27b

-continued

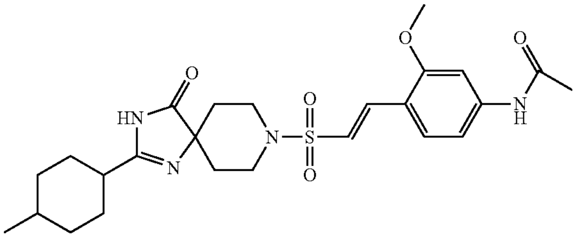

122a

N-(3-Methoxy-4-{(E)-2-[2-(4-methyl-cyclohexyl)-4-oxo-1,3,8-triaza-spiro[4.5]dec-1-ene-8-sulfonyl]-vinyl}-phenyl)-acetamide was synthesized by operations similar to those in Reaction 25-2 using appropriate reagents and starting material.

MS (ESI) m/z=503 (M+H)+.

(Reaction 122-2)

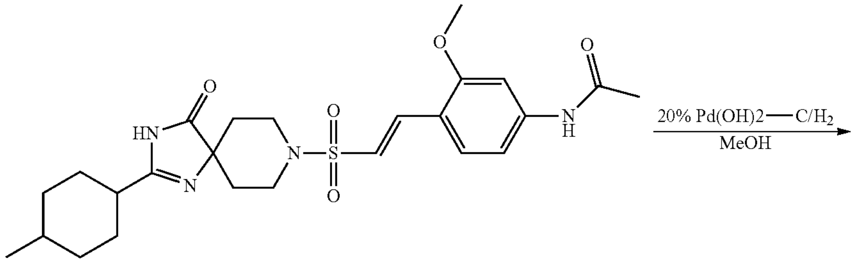

122a

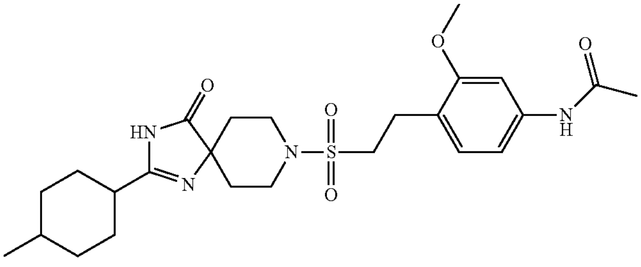

Compound 655

20% $Pd(OH)_2$—C (30 mg) was placed into a solution of N-(3-methoxy-4-{(E)-2-[2-(4-methyl-cyclohexyl)-4-oxo-1,3,8-triaza-spiro[4.5]dec-1-ene-8-sulfonyl]-vinyl}-phenyl)-acetamide (31 mg, 0.0617 mmol) in methanol (5 ml), and the atmosphere was replaced with hydrogen. The mixture was stirred at room temperature for 16 hours. The reaction mixture was filtered, and the filtrate was then concentrated under reduced pressure. The resulting residue was purified by silica gel column chromatography (dichloromethane-ethyl acetate) to give N-(3-methoxy-4-{2-[2-(4-methyl-cyclohexyl)-4-oxo-1,3,8-triaza-spiro[4.5]dec-1-ene-8-sulfonyl]-ethyl}-phenyl)-acetamide (20 mg).

MS (ESI) m/z=505 (M+H)+.

The example compound shown below was synthesized by operations similar to those in Example 122 using appropriate reagents and starting material.

resulting residue was purified by silica gel column chromatography (hexane-ethyl acetate) to give ethyl 2-[(4-bromo-3,5-dimethyl-phenyl)amino]-2-methyl-propanoate (230 mg, 29%).

MS (ESI) m/z=314, 316 (M+H)+.

(Reaction 122-4)

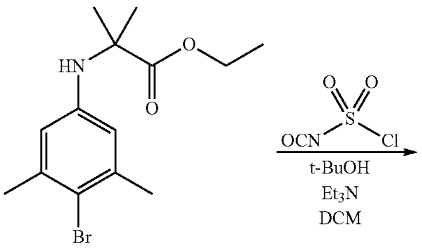

122b

Compound 656

TABLE 93

| Target Compound | Structure | LCMS condition | Retention time (min) | MS (m/z) |
|---|---|---|---|---|
| 656 | 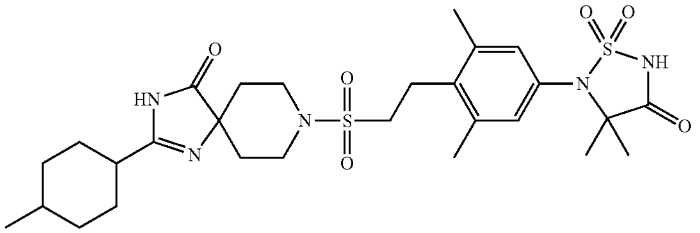 [SMILES: Cc1cc(N2C(C)(C)C(=O)NS2(=O)=O)cc(C)c1CCS(=O)(=O)N1CCC2(CC1)N=C(C1CCC(C)CC1)NC2=O] | LCMS-D-1 | 1.7 | 608 (M + H)+ |

The aryl bromide reagent used in the synthesis of Compound 656 (5-(4-bromo-3,5-dimethyl-phenyl)-4,4-dimethyl-1,1-dioxo-1λ$^6$-[1,2,5]thiadiazolidin-3-one) was synthesized as follows.

(Reaction 122-3)

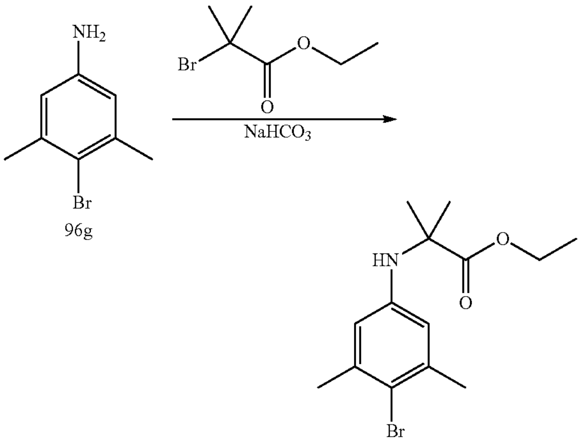

96g

122b

Ethyl-2-bromoisobutyric acid (3.7 ml, 24.99 mmol) and sodium bicarbonate (630 mg, 7.49 mmol) were added to 4-bromo-3,5-dimethyl-aniline (500 mg, 2.49 mmol), and the mixture was irradiated with microwaves at 130° C. for 15 minutes. The reaction mixture was diluted with ethyl acetate, and the organic layer was sequentially washed with water and saturated brine and concentrated under reduced pressure. The -continued

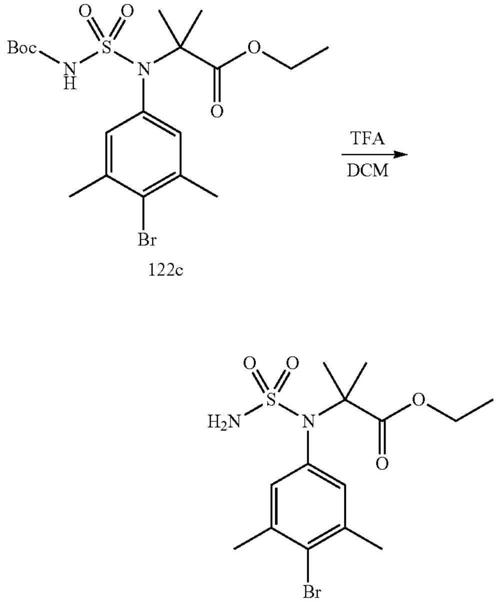

122c

122d

Ethyl 2-[N-(4-bromo-3,5-dimethyl-phenyl)-N-sulfamoyl-amino]-2-methyl-propanoate was synthesized by operations similar to those in Reaction 92-2 and Reaction 7-2 using appropriate reagents and starting material.

MS (ESI) m/z=505 (M+H)+.

(Reaction 122-5)

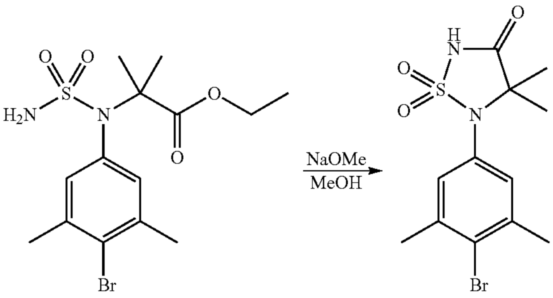

122d

122e

A 2 M solution of sodium methoxide in methanol (4 ml, 8 mmol) was added to a solution of ethyl 2-[N-(4-bromo-3,5-dimethyl-phenyl)-N-sulfamoyl-amino]-2-methyl-propanoate (100 mg, 0.254 mmol) in methanol (12 ml), and the mixture was irradiated with microwaves at 65° C. for 10 minutes. The reaction mixture was diluted with ethyl acetate, and the organic layer was sequentially washed with water and saturated brine and concentrated under reduced pressure to give 5-(4-bromo-3,5-dimethyl-phenyl)-4,4-dimethyl-1,1-di-oxo-1λ$^6$-[1,2,5]thiadiazolidin-3-one (80 mg, 90%).

$^1$H-NMR ($CDCl_3$) δ 7.23 (s, 2H), 2.48 (s, 6H), 1.31 (s, 6H).

Example 123

8-{2-[2-Methyl-4-(3-oxo-morpholin-4-yl)-phenyl]-ethanesulfonyl}-2-nonyl-1,3,8-triaza-spiro[4.5]dec-1-en-4-one (Compound 657)

(Reaction 123-1)

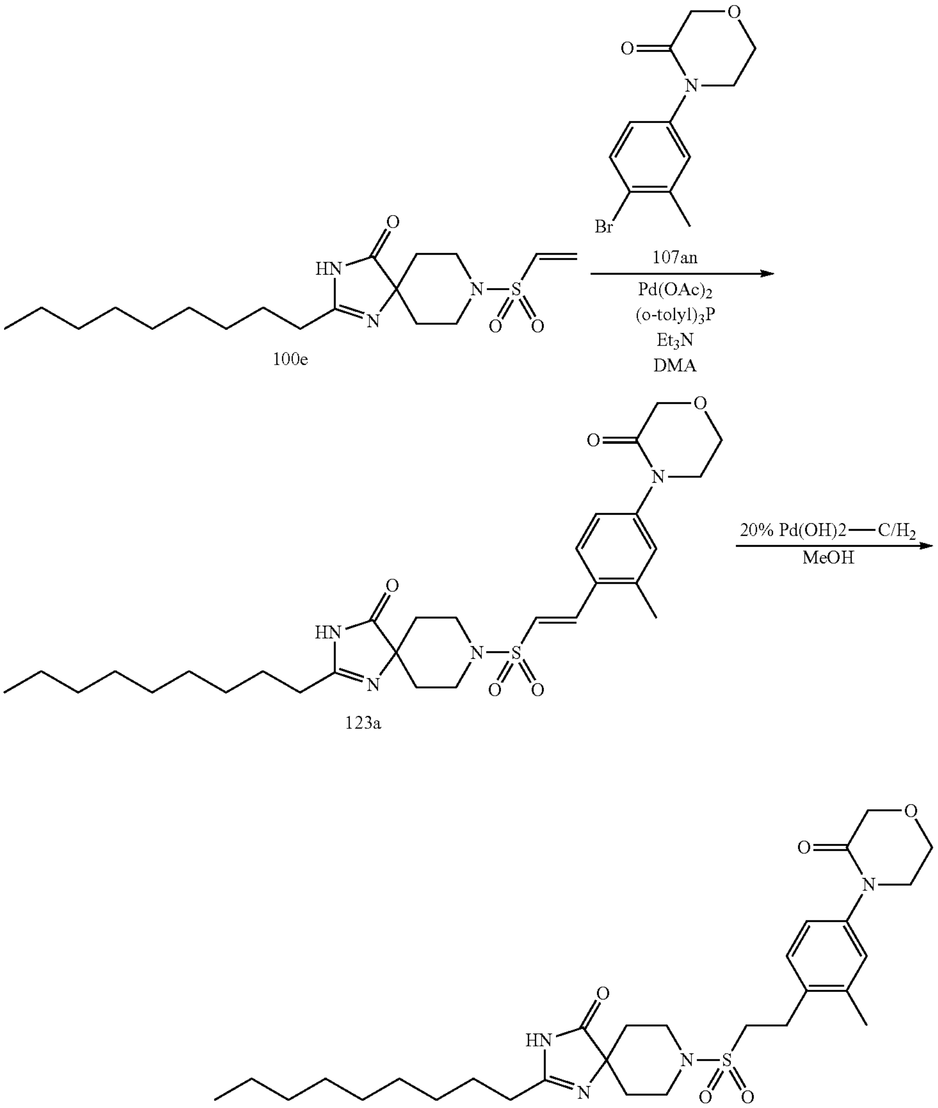

100e

123a

Compound 657

8-{2-[2-Methyl-4-(3-oxo-morpholin-4-yl)-phenyl]-ethanesulfonyl}-2-nonyl-1,3,8-triaza-spiro[4.5]dec-1-en-4-one was synthesized by operations similar to those in Reaction 25-2 and Reaction 122-2 using appropriate reagents and starting material.

MS (ESI) m/z=561 (M+H)+.

Example 124

{4-[2-(2-Cyclohexyl-4-oxo-1,3,8-triaza-spiro[4.5]dec-1-ene-8-sulfonyl)-ethyl]-benzyl}-carbamic acid isobutyl ester (Compound 658)

{4-[2-(2-Cyclohexyl-4-oxo-1,3,8-triaza-spiro[4.5]dec-1-ene-8-sulfonyl)-ethyl]-benzyl}-carbamic acid isobutyl ester was synthesized by operations similar to those in Reaction 25-2 and Reaction 42-2 using appropriate reagents and starting material.

MS (ESI) m/z=533 (M+H)+.

The example compounds shown below were synthesized by operations similar to those in Example 124 using appropriate reagents and starting materials.

(Reaction 124-1)

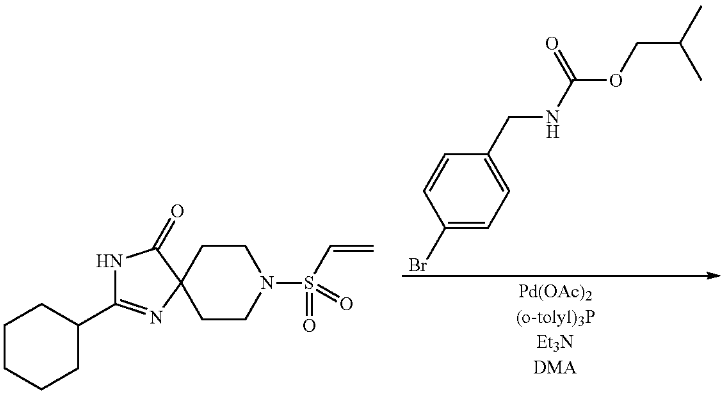

25b

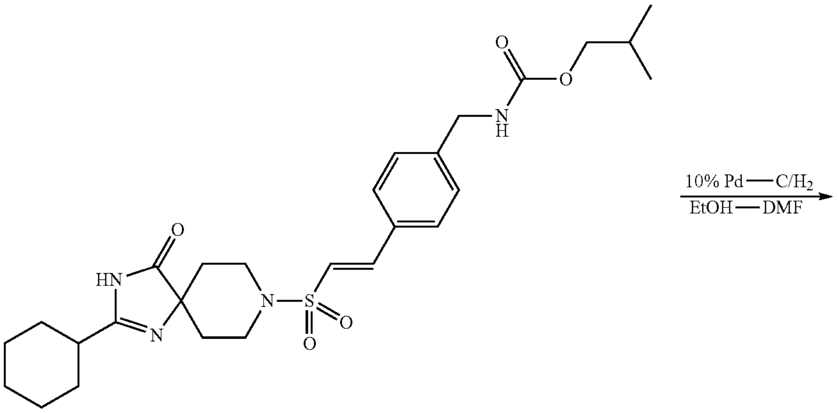

124a

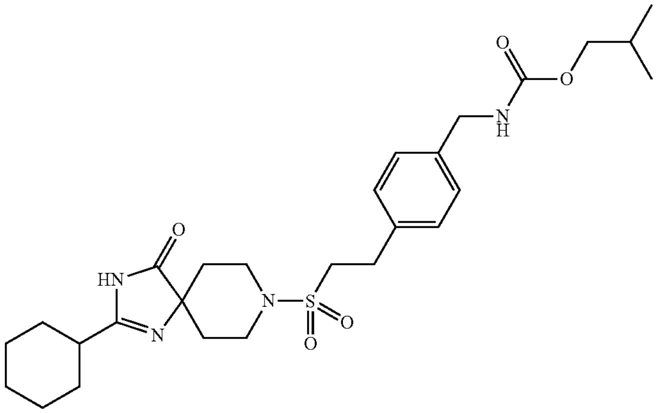

Compound 658

Compounds 659 to Compound 664
TABLE 94
| Target Compound | Structure | LCMS condition | Retention time (min) | MS (m/z) |
| --- | --- | --- | --- | --- |
| 659 | 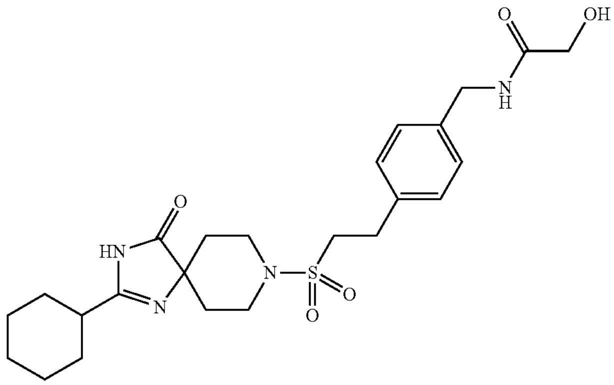 [SMILES: O=C(CO)NCc1ccc(CCS(=O)(=O)N2CCC3(CC2)N=C(C2CCCCC2)NC3=O)cc1] | LCMS-A-1 | 1.62 | 491 (M + H)+ |
| 660 | 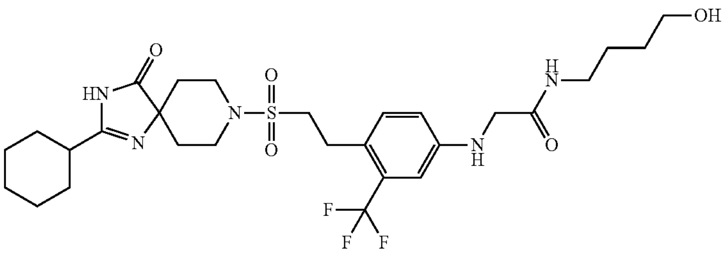 [SMILES: O=C(CNc1ccc(CCS(=O)(=O)N2CCC3(CC2)N=C(C2CCCCC2)NC3=O)c(C(F)(F)F)c1)NCCCCO] | LCMS-C-1 | 2.40 | 616 (M + H)+ |
| 661 | 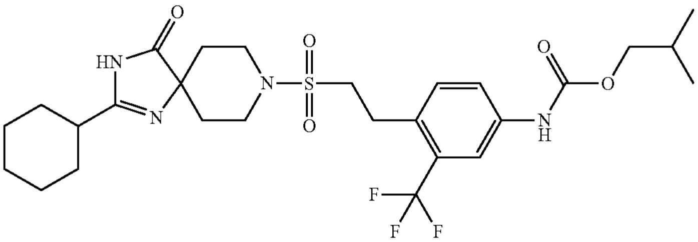 [SMILES: CC(C)COC(=O)Nc1ccc(CCS(=O)(=O)N2CCC3(CC2)N=C(C2CCCCC2)NC3=O)c(C(F)(F)F)c1] | LCMS-C-1 | 2.98 | 587 (M + H)+ |
| 662 | 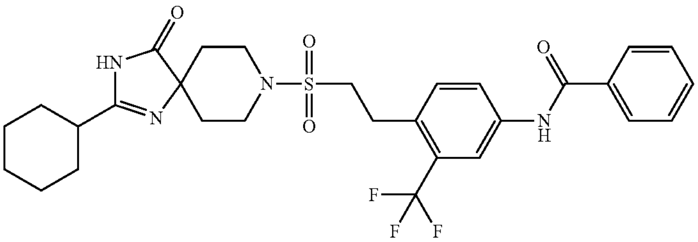 [SMILES: O=C(Nc1ccc(CCS(=O)(=O)N2CCC3(CC2)N=C(C2CCCCC2)NC3=O)c(C(F)(F)F)c1)c1ccccc1] | LCMS-C-1 | 2.82 | 591 (M + H)+ |
| 663 | 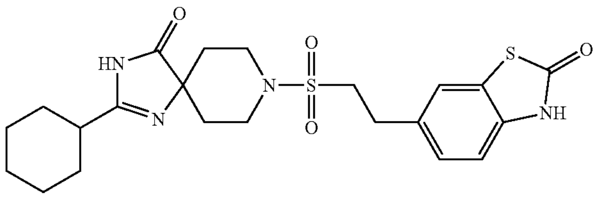 [SMILES: O=C1NC(C2CCCCC2)=NC12CCN(S(=O)(=O)CCc1ccc3[nH]c(=O)sc3c1)CC2] | LCMS-C-1 | 2.37 | 477 (M + H)+ |

TABLE 94-continued

| Target Compound | Structure | LCMS condition | Retention time (min) | MS (m/z) |
|---|---|---|---|---|
| 664 | 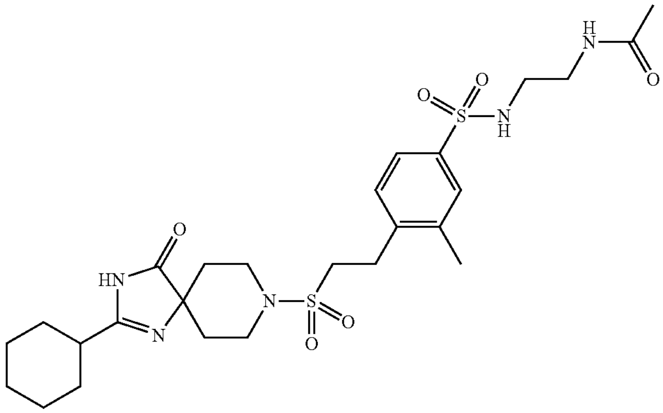 [SMILES: CC(=O)NCCNS(=O)(=O)c1ccc(CCS(=O)(=O)N2CCC3(CC2)N=C(C2CCCCC2)NC3=O)c(C)c1] | LCMS-C-1 | 2.20 | 582 (M + H)+ |

The aryl bromide reagent used in the synthesis of Compound 658 ((4-bromo-benzyl)-carbamic acid isobutyl ester) was synthesized as follows.

(Reaction 124-2)

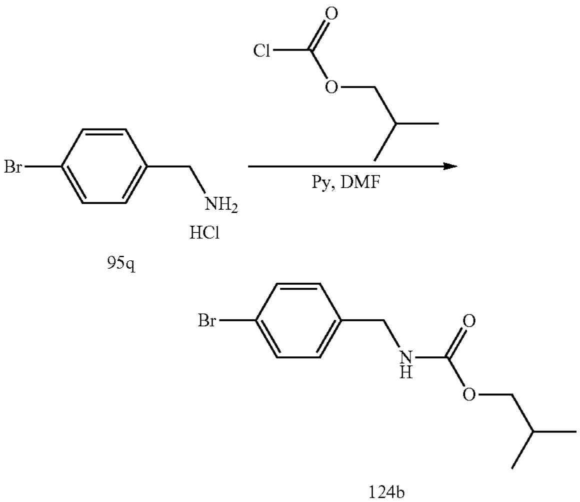

Isobutyl chloroformate (0.152 ml, 1.17 mmol) was added to a solution of 4-bromo-benzylamine hydrochloride (200 mg, 0.899 mmol) and pyridine (0.182 ml, 2.25 mmol) in DMF (2.0 ml), and the mixture was stirred at room temperature for 1.5 hours. A 1 N aqueous HCl solution was added to the reaction mixture, followed by extraction with ethyl acetate. The organic layer was sequentially washed with water and saturated brine and then concentrated under reduced pressure. The resulting residue was purified by silica gel column chromatography (dichloromethane-ethyl acetate) to give (4-bromo-benzyl)-carbamic acid isobutyl ester (180 mg, 70%).

MS (ESI) m/z=286, 288 (M+H)+.

The aryl bromide reagent used in the synthesis of Compound 660 (2-(4-bromo-3-trifluoromethyl-phenylamino)-N-(4-hydroxy-butyl)-acetamide) was synthesized as follows.

(Reaction 124-3)

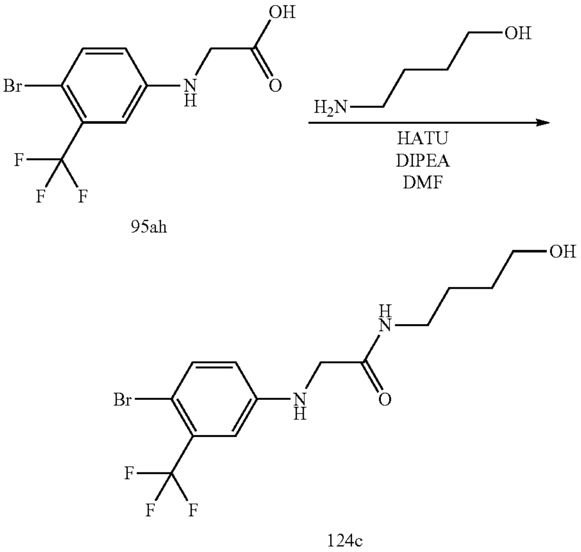

2-(4-Bromo-3-trifluoromethyl-phenylamino)-N-(4-hydroxy-butyl)-acetamide was synthesized by operations similar to those in Reaction 10-14 using appropriate reagents and starting material.

MS (ESI) m/z=369 (M+H)+.

The aryl bromide reagent used in the synthesis of Compound 661 ((4-bromo-3-trifluoromethyl-phenyl)-carbamic acid isobutyl ester) was synthesized as follows.

(Reaction 124-4)

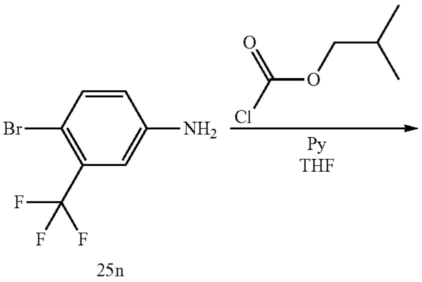

-continued

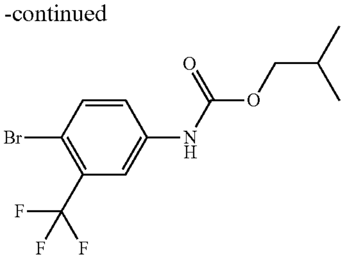

124d (4-Bromo-3-trifluoromethyl-phenyl)-carbamic acid isobutyl ester was synthesized by operations similar to those in Reaction 124-2 using appropriate reagents and starting material.

MS (ESI) m/z=338 (M−H)−.

The aryl bromide reagent used in the synthesis of Compound 662 (N-(4-bromo-3-trifluoromethyl-phenyl)-benzamide) was synthesized as follows.

(Reaction 124-5)

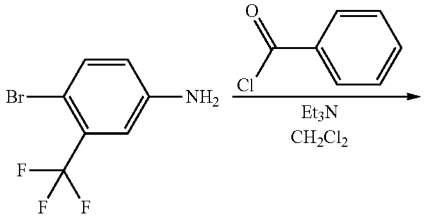

25n

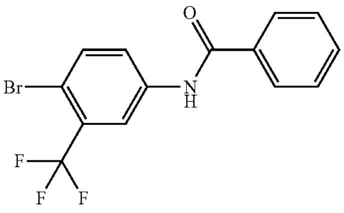

124e

N-(4-Bromo-3-trifluoromethyl-phenyl)-benzamide was synthesized by operations similar to those in Reaction 2-3 using appropriate reagents and starting material.

MS (ESI) m/z=344 (M+H)+.

The aryl bromide reagent used in the synthesis of Compound 664 (N-[2-(4-bromo-3-methyl-benzenesulfonylamino)-ethyl]-acetamide) was synthesized as follows.

(Reaction 124-6)

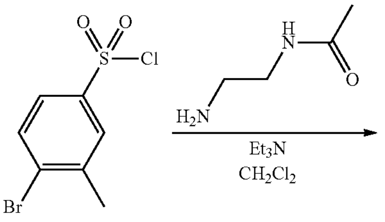

28j

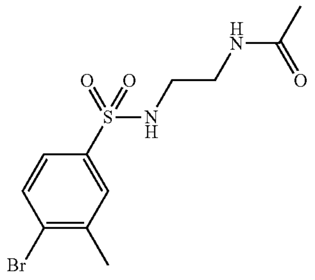

124f

N-[2-(4-Bromo-3-methyl-benzenesulfonylamino)-ethyl]-acetamide was synthesized by operations similar to those in Reaction 5-4 using appropriate reagents and starting material.

MS (ESI) m/z=335 (M+H)+.

Example 125

N-(2-Dimethylamino-ethyl)-2-(3-methyl-4-{2-[4-oxo-2-(3-trifluoromethoxy-phenyl)-1,3,8-triaza-spiro[4.5]dec-1-ene-8-sulfonyl]-ethyl}-phenylamino)-acetamide (Compound 665)

(Reaction 125-1)

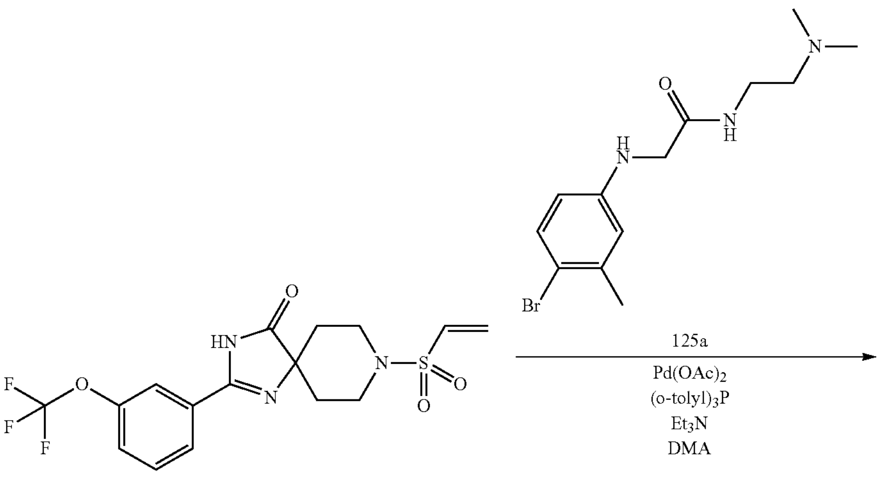

30a

-continued

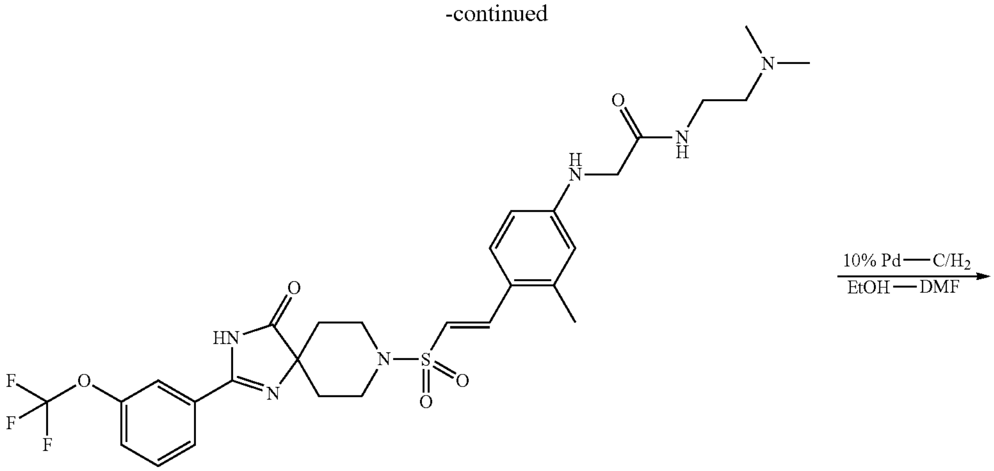

125b

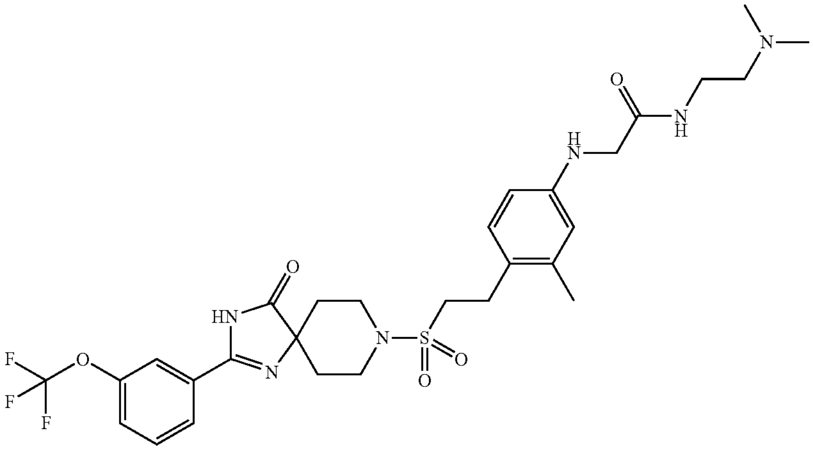

Compound 665

N-(2-Dimethylamino-ethyl)-2-(3-methyl-4-{2-[4-oxo-2-(3-trifluoromethoxy-phenyl)-1,3,8-triaza-spiro[4.5]dec-1-ene-8-sulfonyl]-ethyl}-phenylamino)-acetamide was synthesized by operations similar to those in Reaction 25-2 and Reaction 42-2 using appropriate reagents and starting material.

MS (ESI) m/z=639 (M+H)+.

The example compound shown below was synthesized by operations similar to those in Example 125 using appropriate reagents and starting material.

Compound 666

TABLE 95

| Target Compound | Structure | LCMS condition | Retention time (min) | MS (m/z) |
|---|---|---|---|---|
| 666 | 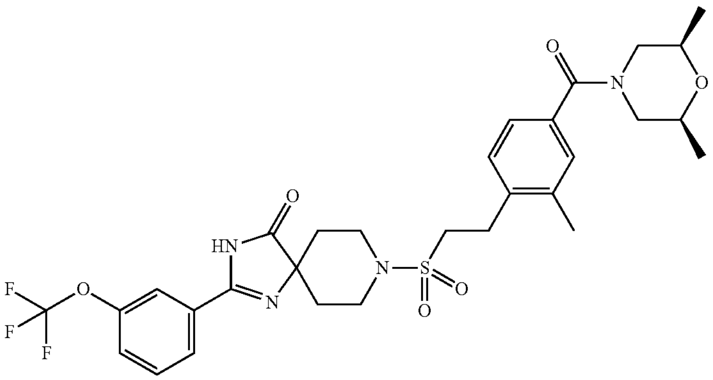 [SMILES: Cc1cc(C(=O)N2C[C@@H](C)O[C@@H](C)C2)ccc1CCS(=O)(=O)N1CCC2(CC1)N=C(c1cccc(OC(F)(F)F)c1)NC2=O] | LCMS-A-1 | 2.60 | 637 (M + H)+ |

The aryl bromide reagent used in the synthesis of Compound 666 ((4-bromo-3-methyl-phenyl)-(cis-2,6-dimethyl-morpholin-4-yl)-methanone) was synthesized as follows.

(Reaction 125-2)

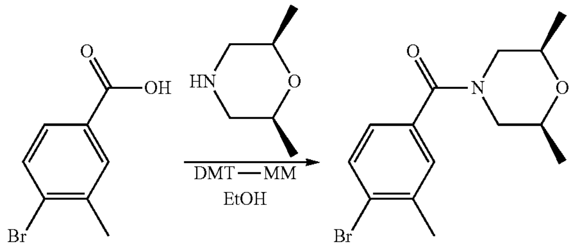

10a

125c (4-Bromo-3-methyl-phenyl)-(cis-2,6-dimethyl-morpholin-4-yl)-methanone was synthesized by operations similar to those in Reaction 10-1 using appropriate reagents and starting material.

MS (ESI) m/z=312, 314 (M+H)+.

Example 126

N-(2,2,3,3,4,4,4-Heptafluoro-butyl)-3-methyl-4-{2-[4-oxo-2-(3-trifluoromethyl-phenyl)-1,3,8-triaza-spiro[4.5]dec-1-ene-8-sulfonyl]-ethyl}-benzene-sulfonamide (Compound 667)

(Reaction 126-1)

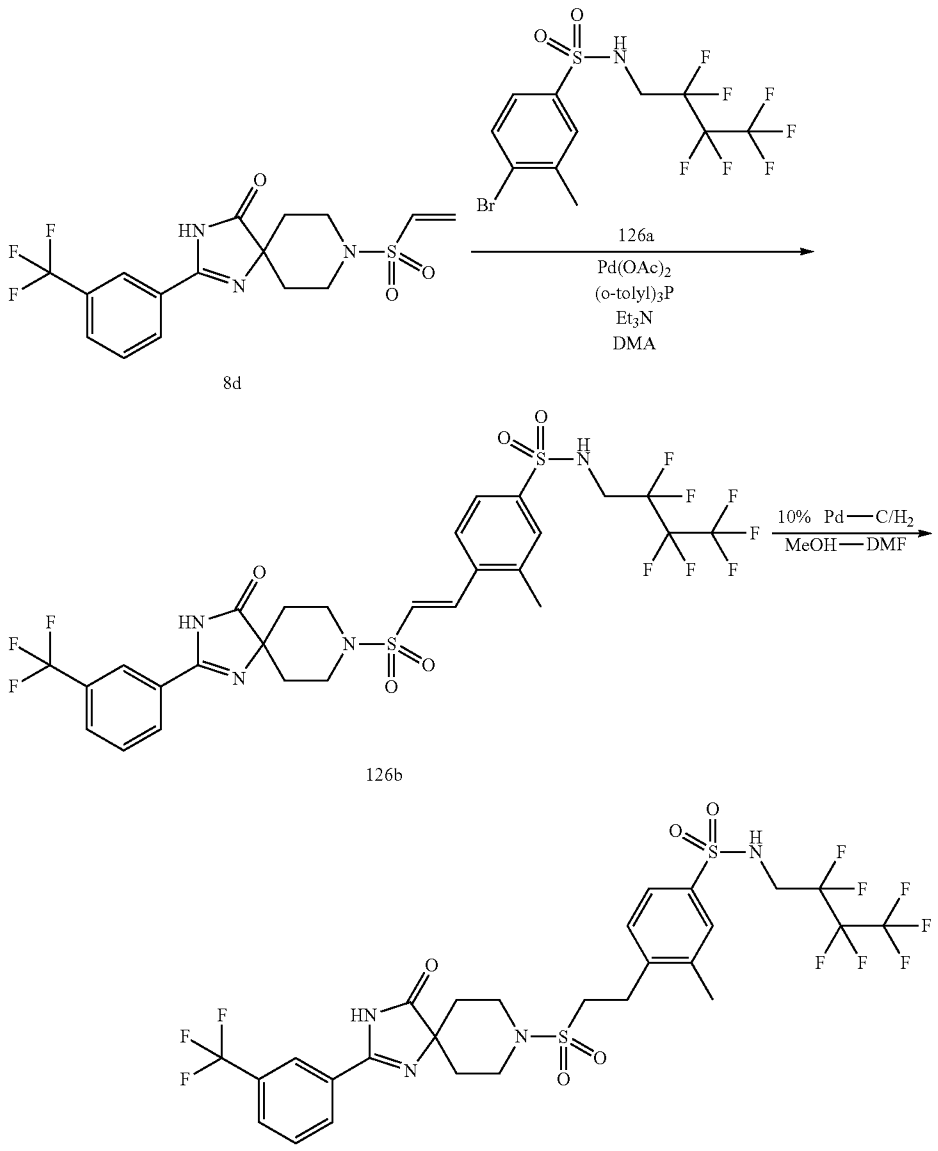

8d

126b

Compound 667

N-(2,2,3,3,4,4,4-Heptafluoro-butyl)-3-methyl-4-{2-[4-oxo-2-(3-trifluoromethyl-phenyl)-1,3,8-triaza-spiro[4.5]dec-1-ene-8-sulfonyl]-ethyl}-benzenesulfonamide was synthesized by operations similar to those in Reaction 26-1 and Reaction 42-1 using appropriate reagents and starting material.

MS (ESI) m/z=741 (M+H)+.

The aryl bromide reagent used in the synthesis of Compound 667 (4-bromo-N-(2,2,3,3,4,4,4-heptafluoro-butyl)-3-methyl-benzenesulfonamide) was synthesized as follows.

(Reaction 126-2)

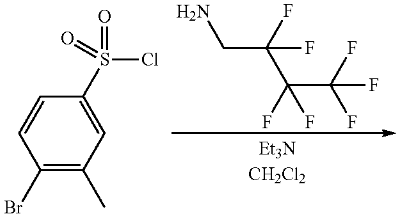

28j

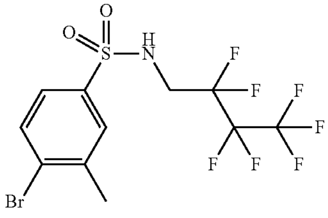

126a

4-Bromo-N-(2,2,3,3,4,4,4-heptafluoro-butyl)-3-methyl-benzenesulfonamide was synthesized by operations similar to those in Reaction 5-4 using appropriate reagents and starting material.

MS (ESI) m/z=454, 456 (M+Na)+.

Example 127

8-[2-(3-Methoxy-2-methyl-phenyl)-ethanesulfonyl]-2-(4-methyl-cyclohexyl)-1,3,8-triaza-spiro[4.5]dec-1-en-4-one (Compound 668)

(Reaction 127-1)

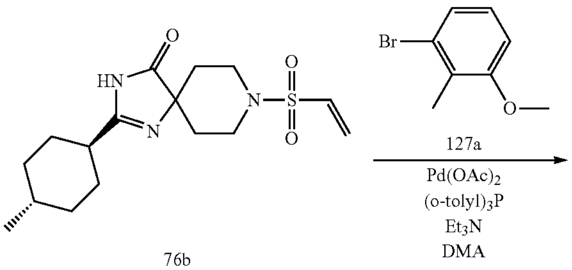

76b

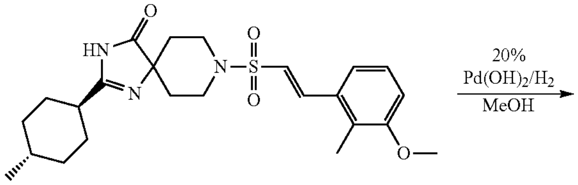

127b

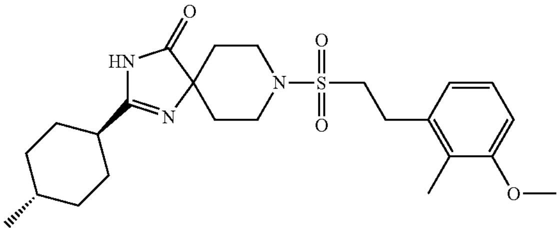

Compound 668

8-[2-(3-Methoxy-2-methyl-phenyl)-ethanesulfonyl]-2-(4-methyl-cyclohexyl)-1,3,8-triaza-spiro[4.5]dec-1-en-4-one was synthesized by operations similar to those in Reaction 26-1 and Reaction 122-2 using appropriate reagents and starting material.

MS (ESI) m/z=462 (M+H)+.

The example compound shown below was synthesized by operations similar to those in Example 127 using appropriate reagents and starting material.

Compound 669

TABLE 96

| Target Compound | Structure | LCMS condition | Retention time (min) | MS (m/z) |
|---|---|---|---|---|
| 669 | 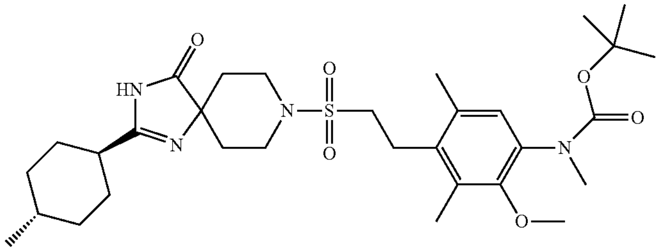 [SMILES: COc1c(N(C)C(=O)OC(C)(C)C)cc(C)c(CCS(=O)(=O)N2CCC3(CC2)N=C([C@H]2CC[C@H](C)CC2)NC3=O)c1C] | LCMS-F-1 | 1.1 | 605 (M + H)+ |

The aryl bromide reagent used in the synthesis of Compound 669 ((4-bromo-2-methoxy-3,5-dimethyl-phenyl)-methyl-carbamic acid tert-butyl ester) was synthesized as follows.

(Reaction 127-2)

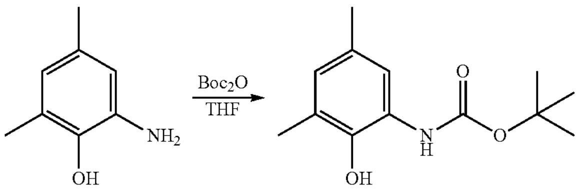

127c 127d

Di-tert-butyl dicarbonate (1.32 ml, 5.75 mmol) was added to a solution of 2-amino-4,6-dimethyl-phenol (731.8 mg, 5.335 mmol) in THF (3.7 ml), and the mixture was stirred at room temperature for five hours. The reaction mixture was concentrated under reduced pressure, and the resulting residue was then purified by silica gel column chromatography (hexane-ethyl acetate) to give (2-hydroxy-3,5-dimethyl-phenyl)-carbamic acid tert-butyl ester as a red purple solid (1.234 g, 97%).

$^1$H-NMR (300 MHz, $CDCl_3$) δ 1.52 (9H, s), 2.21 (3H, s), 2.24 (3H, s), 6.54 (1H, br), 6.71 (1H, s), 6.76 (1H, s), 7.74 (1H, br).

(Reaction 127-3)

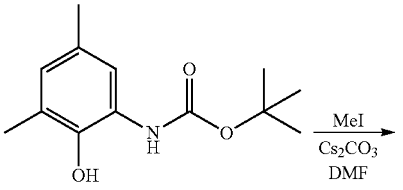

127d

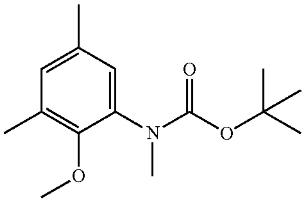

127e (2-Methoxy-3,5-dimethyl-phenyl)-methyl-carbamic acid tert-butyl ester was synthesized by operations similar to those in Reaction 26-4 (using cesium carbonate as a base) using appropriate reagents and starting material.

$^1$H-NMR (400 MHz, $CDCl_3$) δ 1.30-1.56 (9H, br), 2.24 (3H, s), 2.25 (3H, s), 3.16 (3H, s), 3.69 (3H, s), 6.76 (1H, br), 6.87 (1H, s).

(Reaction 127-4)

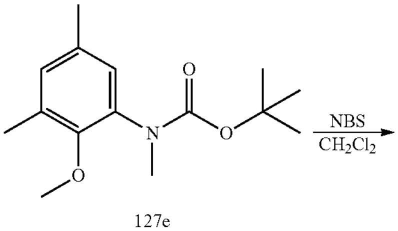

127e

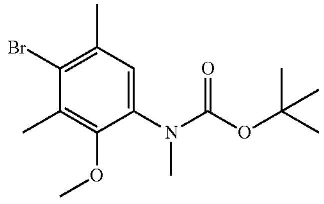

127f

N-Bromosuccinimide (326 mg, 1.83 mmol) was added to a solution of (2-methoxy-3,5-dimethyl-phenyl)-methyl-carbamic acid tert-butyl ester (456 mg, 1.72 mmol) in dichloromethane (1.8 ml) at 0° C., and the mixture was stirred at room temperature for 50 minutes. The reaction mixture was diluted with dichloromethane and adjusted to pH 9 and washed with water and a 1 N aqueous NaOH solution (1 ml), and the organic layer was dried over $MgSO_4$ and concentrated under reduced pressure. The resulting residue was purified by silica gel column chromatography (hexane-ethyl acetate) to give (4-bromo-2-methoxy-3,5-dimethyl-phenyl)-methyl-carbamic acid tert-butyl ester as a colorless solid (545 mg, 92%).

$^1$H-NMR (400 MHz, $CDCl_3$) δ 1.30-1.56 (9H, br), 2.35 (3H, s), 2.37 (3H, s), 3.14 (3H, s), 3.69 (3H, s), 6.82-7.07 (1H, br).

Example 128

8-{2-[4-((S)-2-Hydroxymethyl-5-oxo-pyrrolidin-1-yl)-2-methyl-phenyl]-ethanesulfonyl}-2-nonyl-1,3,8-triaza-spiro[4.5]dec-1-en-4-one (Compound 670)

(Reaction 128-1)

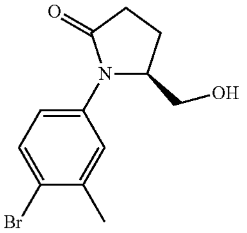

108a

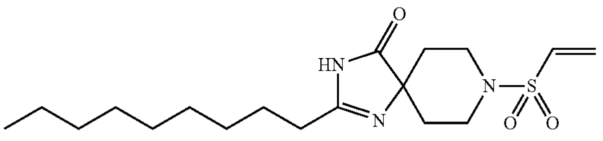

100e

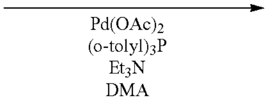

-continued

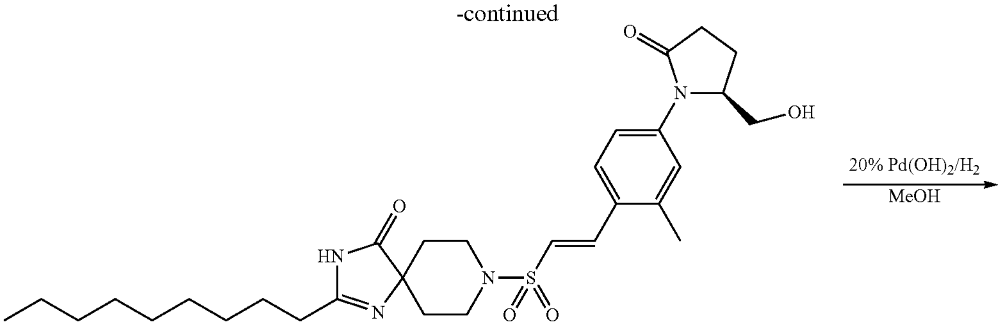

128a

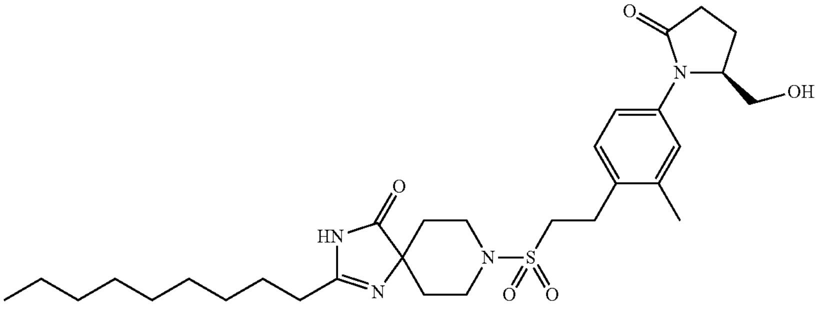

Compound 670

8-{2-[4-((S)-2-Hydroxymethyl-5-oxo-pyrrolidin-1-yl)-2-methyl-phenyl]-ethanesulfonyl}-2-nonyl-1,3,8-triaza-spiro[4.5]dec-1-en-4-one was synthesized by operations similar to those in Reaction 26-1 and Reaction 122-2 using appropriate reagents and starting material.

MS (ESI) m/z=575 (M+H)+.

Example 129

8-[2-(5,7-Dimethyl-2-oxo-2,3-dihydro-benzoxazol-6-yl)-ethanesulfonyl]-2-(4-methyl-cyclohexyl)-1,3,8-triaza-spiro[4.5]dec-1-en-4-one (Compound 671)

(Reaction 129-1)

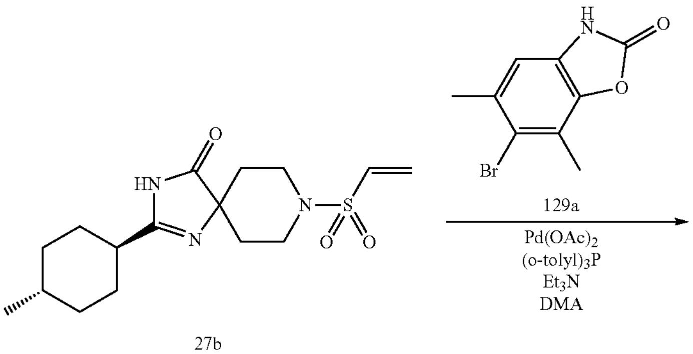

27b

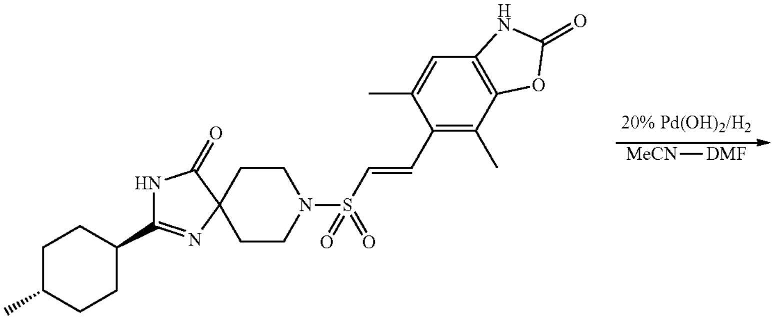

129b

-continued

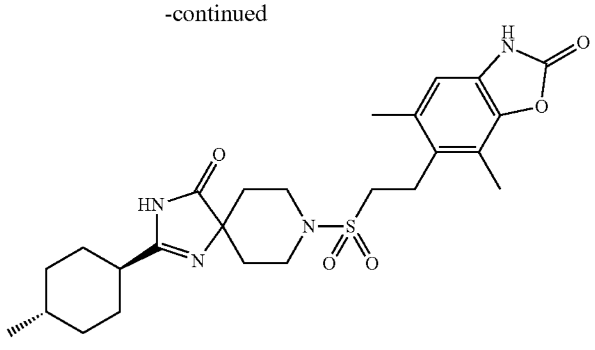

Compound 671

8-[2-(5,7-Dimethyl-2-oxo-2,3-dihydro-benzoxazol-6-yl)-ethanesulfonyl]-2-(4-methyl-cyclohexyl)-1,3,8-triaza-spiro[4.5]dec-1-en-4-one was synthesized by operations similar to those in Reaction 26-1 and Reaction 122-2 (using MeCN-DMF as a solvent) using appropriate reagents and starting material.

MS (ESI) m/z=503 (M+H)+.

The aryl bromide reagent used in the synthesis of Compound 129 (6-bromo-5,7-dimethyl-3H-benzoxazol-2-one) was synthesized as follows.

(Reaction 129-2)

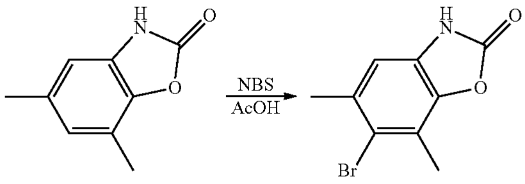

129c 129a

6-Bromo-5,7-dimethyl-3H-benzoxazol-2-one was synthesized by operations similar to those in Reaction 127-4 (using acetic acid as a solvent) using appropriate reagents and starting material.

MS (ESI) m/z=242, 244 (M+H)+.

Example 130

(2-{4-[2-(2-Cyclohexyl-4-oxo-1,3,8-triaza-spiro[4.5]dec-1-ene-8-sulfonyl)-ethyl]-phenyl}-ethyl)-carbamic acid methyl ester (Compound 672)

(Reaction 130-1)

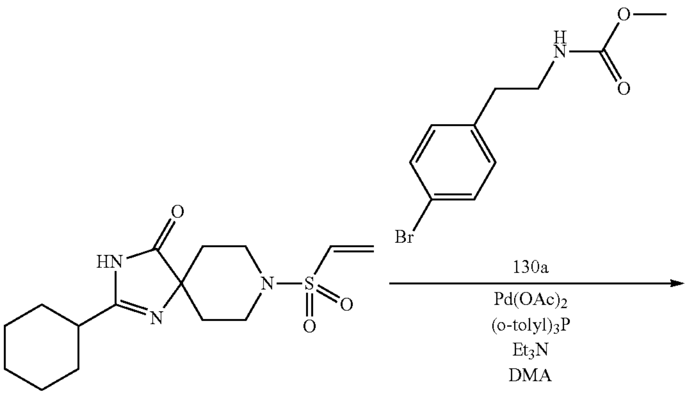

25b

-continued

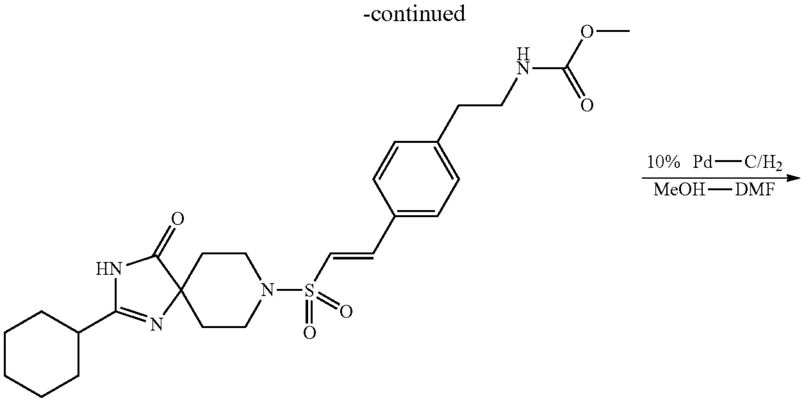

130b

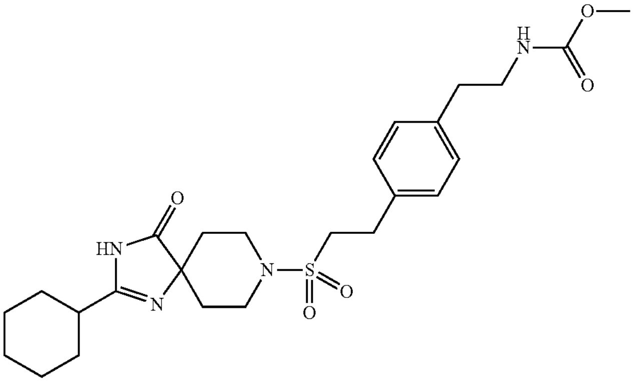

Compound 672

(2-{4-[2-(2-Cyclohexyl-4-oxo-1,3,8-triaza-spiro[4.5]dec-1-ene-8-sulfonyl)-ethyl]-phenyl}-ethyl)-carbamic acid methyl ester was synthesized by operations similar to those in Reaction 26-1 and Reaction 42-2 using appropriate reagents and starting material.

MS (ESI) m/z=505 (M+H)+.

The example compound shown below was synthesized by operations similar to those in Example 130 using appropriate reagents and starting material.

Compound 673

TABLE 97

| Target Compound | Structure | LCMS condition | Retention time (min) | MS (m/z) |
|---|---|---|---|---|
| 673 | 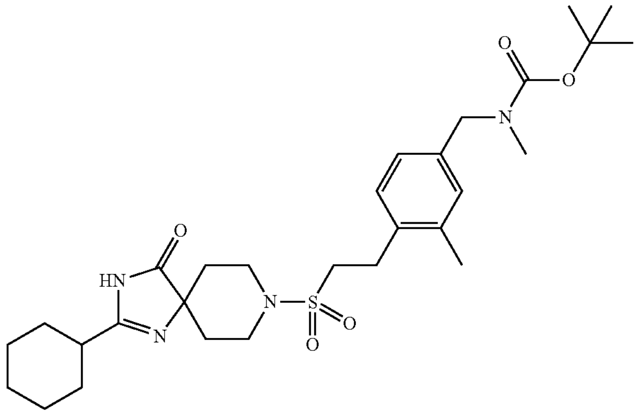 [SMILES: Cc1cc(CN(C)C(=O)OC(C)(C)C)ccc1CCS(=O)(=O)N1CCC2(CC1)N=C(C1CCCCC1)NC2=O] | LCMS-C-1 | 2.93 | 559 (M − H)− |

The aryl bromide reagent used in the synthesis of Compound 673 ((4-bromo-3-methyl-benzyl)-methyl-carbamic acid tert-butyl ester) was synthesized as follows.

(Reaction 130-2)

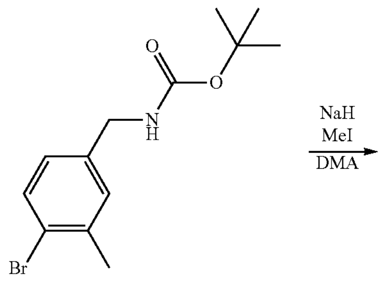

17b

-continued

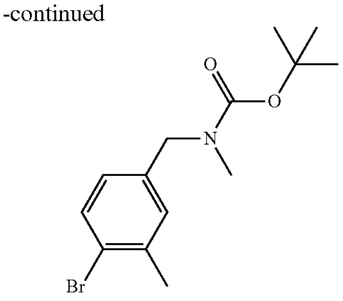

130c (4-Bromo-3-methyl-benzyl)-methyl-carbamic acid tert-butyl ester was synthesized by operations similar to those in Reaction 25-3 using appropriate reagents and starting material.

MS (ESI) m/z=336, 338 (M+Na)+.

Example 131

8-(2-{4-[3-(2-Hydroxy-ethyl)-2-oxo-imidazolidin-1-yl]-2-methyl-phenyl}-ethanesulfonyl)-2-(3-trifluoromethyl-phenyl)-1,3,8-triaza-spiro[4.5]dec-1-en-4-one (Compound 674)

(Reaction 131-1)

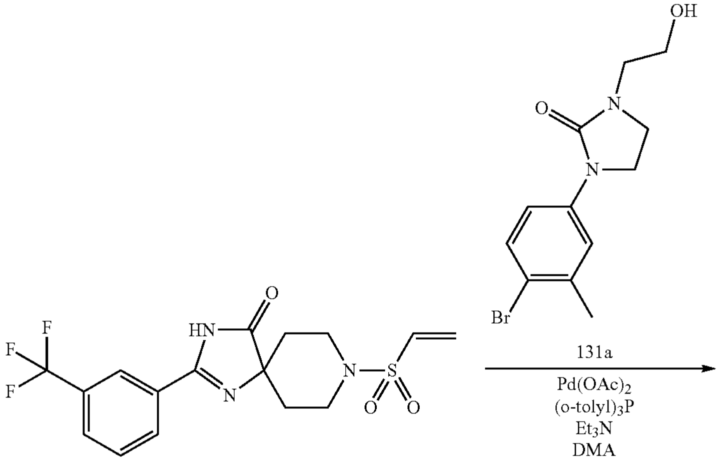

8d

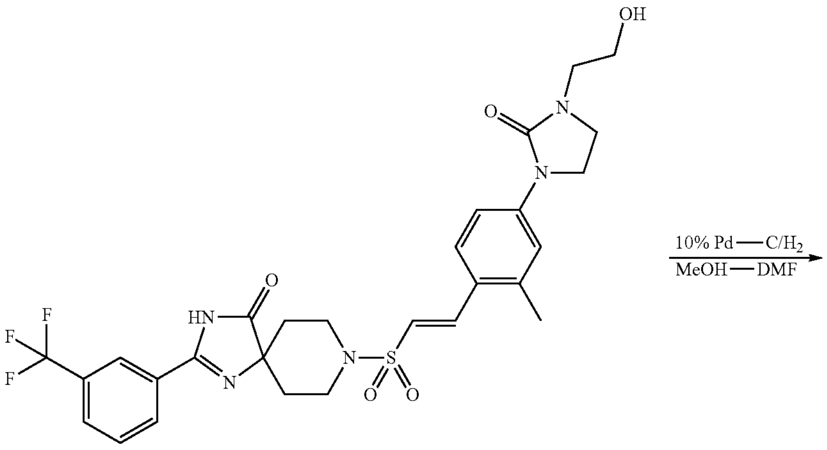

131b

-continued

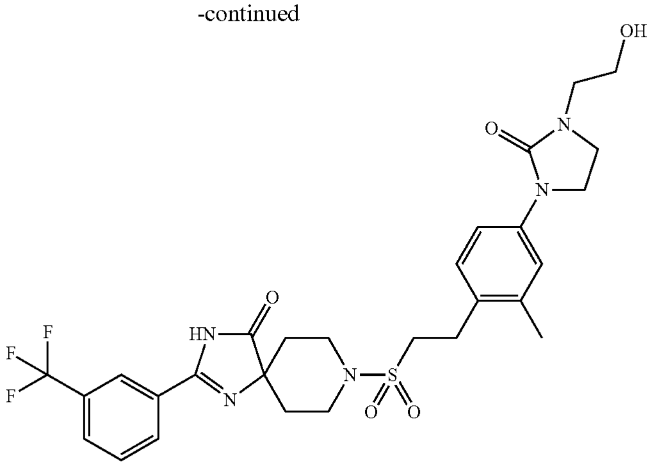

Compound 674

8-(2-{4-[3-(2-Hydroxy-ethyl)-2-oxo-imidazolidin-1-yl]-2-methyl-phenyl}-ethanesulfonyl)-2-(3-trifluoromethyl-phenyl)-1,3,8-triaza-spiro[4.5]dec-1-en-4-one was synthesized by operations similar to those in Reaction 26-1 and Reaction 42-2 using appropriate reagents and starting material.

MS (ESI) m/z=608 (M+H)+.

The aryl bromide reagent used in the synthesis of Compound 674 (1-(4-bromo-3-methyl-phenyl)-3-(2-hydroxy-ethyl)-imidazolidin-2-one) was synthesized as follows.

(Reaction 131-2)

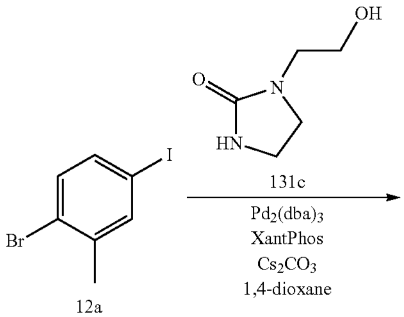

12a

-continued

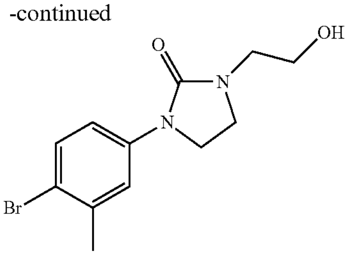

131a 1-(4-Bromo-3-methyl-phenyl)-3-(2-hydroxy-ethyl)-imidazolidin-2-one was synthesized by operations similar to those in Reaction 29-3 using appropriate reagents and starting material.

MS (ESI) m/z=299, 301 (M+H)+.

Example 132

2-(3-Methyl-4-{2-[4-oxo-2-(3-trifluoromethoxy-phenyl)-1,3,8-triaza-spiro[4.5]dec-1-ene-8-sulfonyl]-ethyl}-benzenesulfonylamino)-acetamide (Compound 675)

(Reaction 132-1)

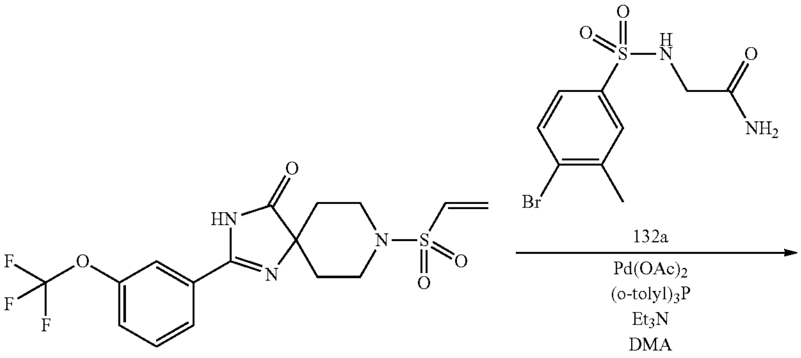

30a

-continued

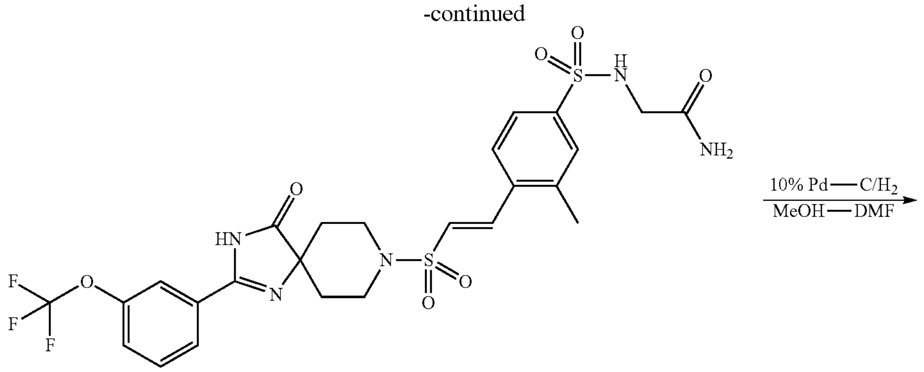

132b

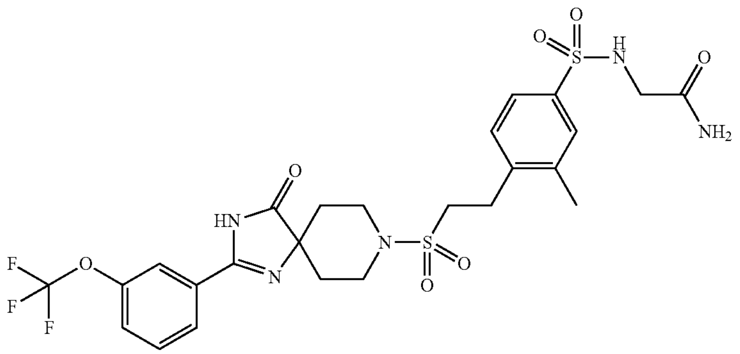

Compound 675

2-(3-Methyl-4-{2-[4-oxo-2-(3-trifluoromethoxy-phenyl)-1,3,8-triaza-spiro[4.5]dec-1-ene-8-sulfonyl]-ethyl}-benzenesulfonylamino)-acetamide was synthesized by operations similar to those in Reaction 26-1 and Reaction 42-2 using appropriate reagents and starting material.

MS (ESI) m/z=632 (M+H)+.

The example compound shown below was synthesized by operations similar to those in Example 132 using appropriate reagents and starting material.

Compound 676

TABLE 98

| Target Compound | Structure | LCMS condition | Retention time (min) | MS (m/z) |
|---|---|---|---|---|
| 676 | 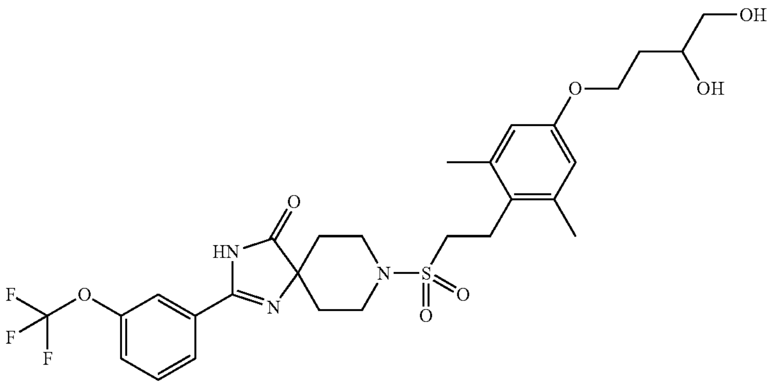 [SMILES: Cc1cc(OCCC(O)CO)cc(C)c1CCS(=O)(=O)N1CCC2(CC1)N=C(c1cccc(OC(F)(F)F)c1)NC2=O] | LCMS-C-1 | 2.70 | 614 (M + H)+ |

The aryl bromide reagent used in the synthesis of Compound 675 (2-(4-bromo-3-methyl-benzenesulfonylamino)-acetamide) was synthesized as follows.

(Reaction 132-2)

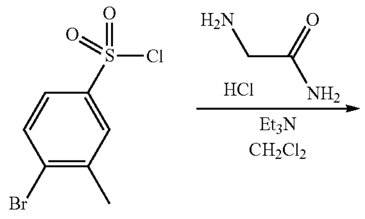

28j

-continued

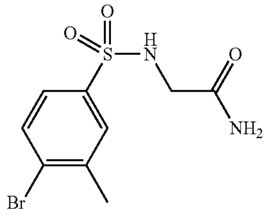

132a 2-(4-Bromo-3-methyl-benzenesulfonylamino)-acetamide was synthesized by operations similar to those in Reaction 5-4 using appropriate reagents and starting material.

MS (ESI) m/z=307, 309 (M+H)+.

Example 133

3-(4-{2-[2-(4-Butyl-cyclohexyl)-4-oxo-1,3,8-triaza-spiro[4.5]dec-1-ene-8-sulfonyl]-ethyl}-3,5-dimethyl-phenyl)-imidazolidine-2,4-dione (Compound 677)

(Reaction 133-1)

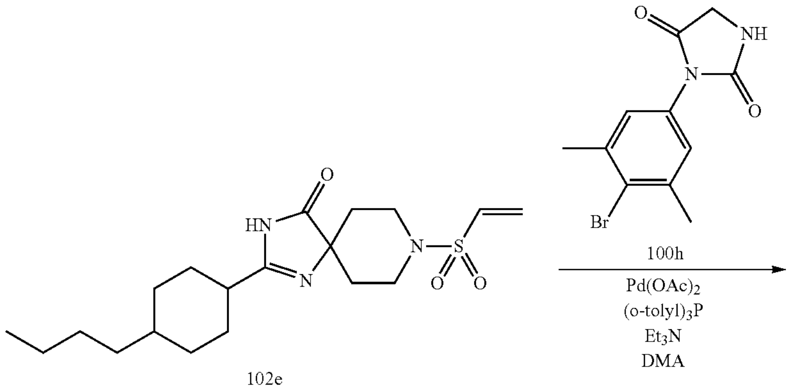

102e

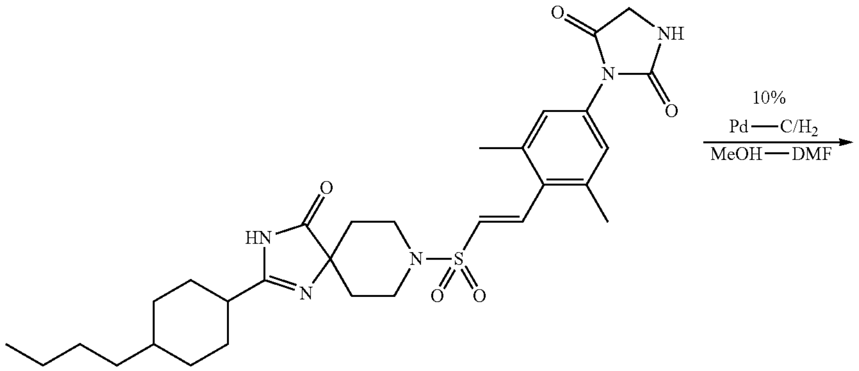

133a

-continued

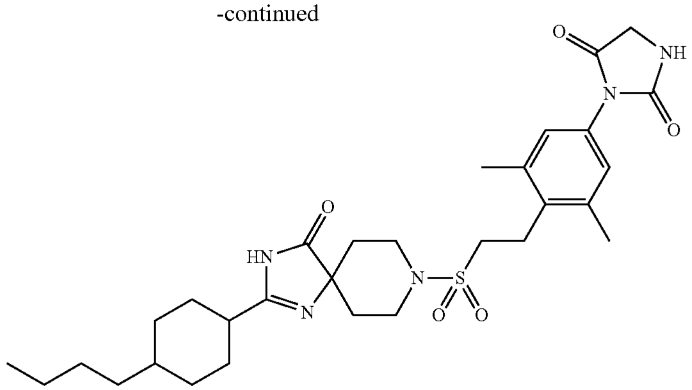

Compound 667

3-(4-{2-[2-(4-Butyl-cyclohexyl)-4-oxo-1,3,8-triaza-spiro[4.5]dec-1-ene-8-sulfonyl]-ethyl}-3,5-dimethyl-phenyl)-imidazolidine-2,4-dione was synthesized by operations similar to those in Reaction 26-1 and Reaction 42-2 using appropriate reagents and starting material.

MS (ESI) m/z=586 (M+H)+.

Example 134

N-Cyclopentyl-N-(3-methyl-4-{2-[4-oxo-2-(3-trifluoromethoxy-phenyl)-1,3,8-triaza-spiro[4.5]dec-1-ene-8-sulfonyl]-ethyl}-phenyl)-acetamide (Compound 678)

(Reaction 134-1)

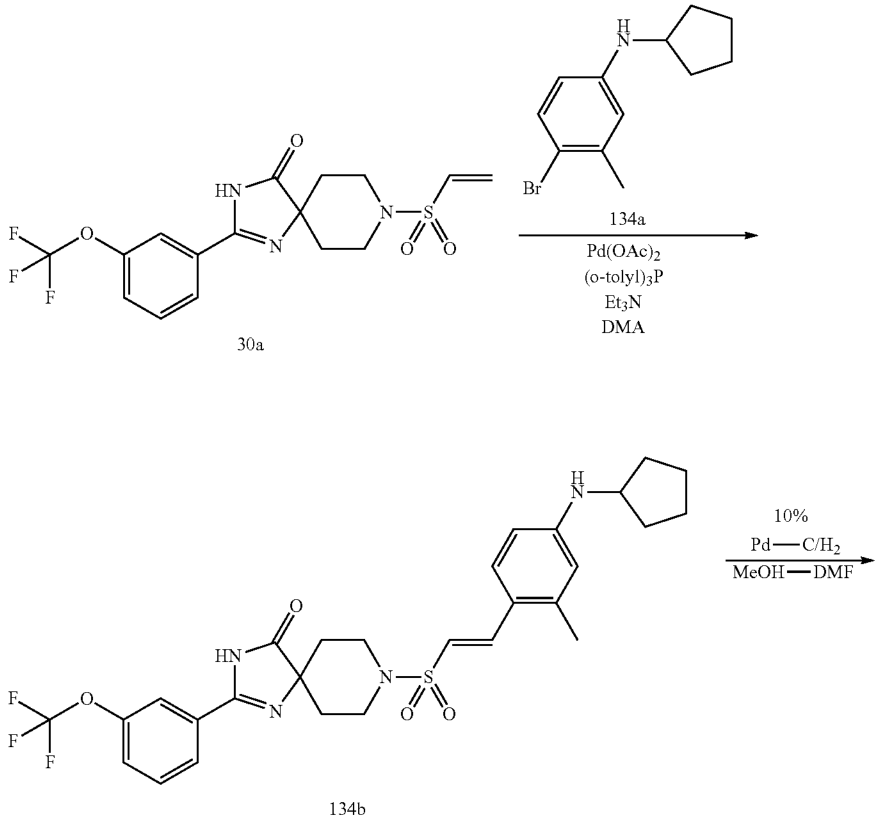

-continued

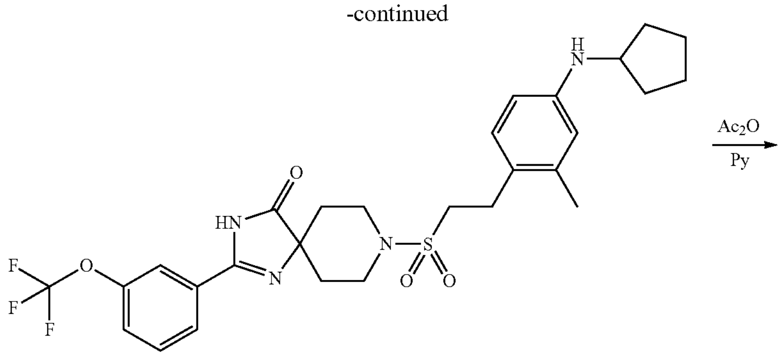

134c

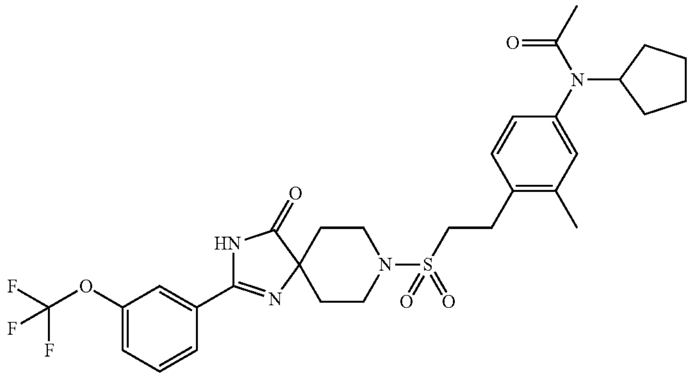

Compound 678

N-Cyclopentyl-N-(3-methyl-4-{2-[4-oxo-2-(3-trifluoromethoxy-phenyl)-1,3,8-triaza-spiro[4.5]dec-1-ene-8-sulfonyl]-ethyl}-phenyl)-acetamide was synthesized by operations similar to those in Reaction 26-1, Reaction 42-2 and Reaction 12-2 using appropriate reagents and starting material.

MS (ESI) m/z=621 (M+H)+.

The aryl bromide reagent used in the synthesis of Compound 678 ((4-bromo-3-methyl-phenyl)-cyclopentyl-amine) was synthesized as follows.

(Reaction 134-2)

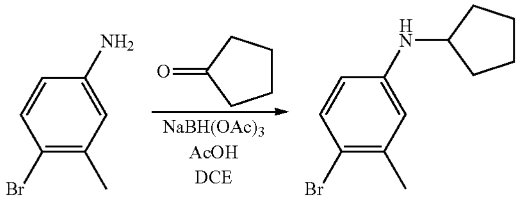

26h 134a (4-Bromo-3-methyl-phenyl)-cyclopentyl-amine was synthesized by operations similar to those in Reaction 41-1 using appropriate reagents and starting material.

MS (ESI) m/z=254, 256 (M+H)+.

Example 135

1-(2,3-Dimethyl-4-{2-[2-(4-methyl-cyclohexyl)-4-oxo-1,3,8-triaza-spiro[4.5]dec-1-ene-8-sulfonyl]-ethyl}-phenyl)-1-methyl-urea (Compound 679)

(Reaction 135-1)

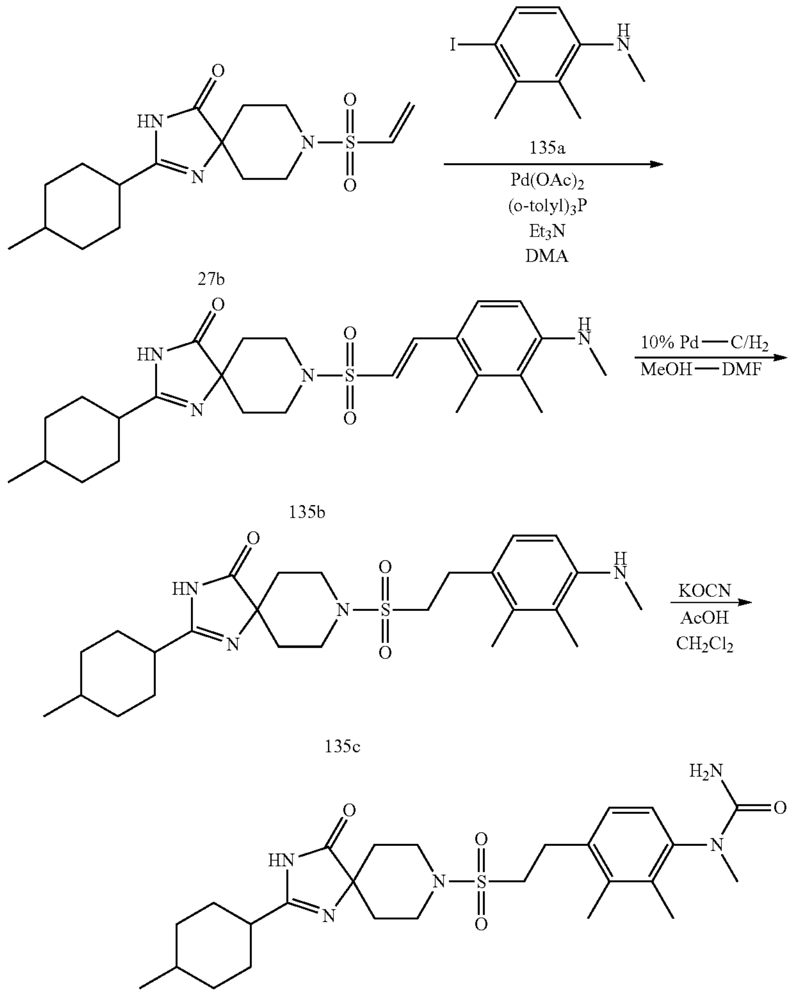

27b

135b

135c

Compound 679

1-(2,3-Dimethyl-4-{2-[2-(4-methyl-cyclohexyl)-4-oxo-1,3,8-triaza-spiro[4.5]dec-1-ene-8-sulfonyl]-ethyl}-phenyl)-1-methyl-urea was synthesized by operations similar to those in Reaction 26-1, Reaction 42-2 and Reaction 89-2 using appropriate reagents and starting material.

MS (ESI) m/z=518 (M+H)+.

The example compound shown below was synthesized by operations similar to those in Example 135 using appropriate reagents and starting material.

Compound 680

TABLE 99

| Target Compound | Structure | LCMS condition | Retention time (min) | MS (m/z) |
| --- | --- | --- | --- | --- |
| 680 | 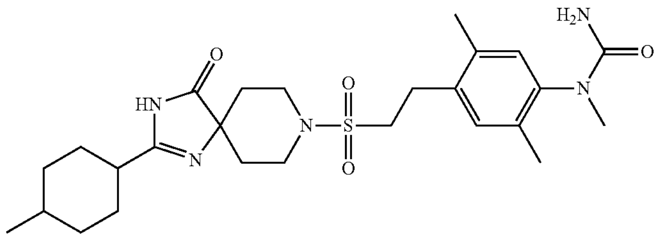 [SMILES: Cc1cc(N(C)C(N)=O)c(C)cc1CCS(=O)(=O)N1CCC2(CC1)N=C(C1CCC(C)CC1)NC2=O] | LCMS-C-1 | 2.58 | 518 (M + H)+ |

The aryl iodide reagent used in the synthesis of Compound 679 (4-iodo-N,2,3-trimethyl-aniline) was synthesized as follows.

(Reaction 135-2)

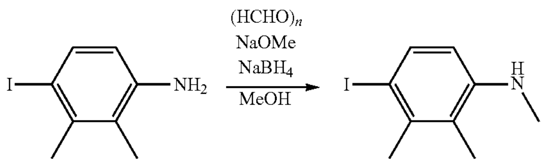

135d 135a

A 28% solution of sodium methoxide in methanol (0.694 ml, 6.07 mmol) was added to a solution of 4-iodo-2,3-dimethyl-aniline (500 mg, 2.02 mmol) and paraformaldehyde (121 mg, 4.05 mmol) in methanol (8.0 ml), and the mixture was stirred at room temperature for 17 hours. Sodium borohydride (153 mg, 4.05 mmol) was further added, and the mixture was stirred at room temperature for four hours. A 1 N aqueous NaOH solution was added to the reaction mixture, followed by extraction with dichloromethane. The resulting residue was purified by silica gel column chromatography (hexane-ethyl acetate) to give 4-iodo-N,2,3-trimethyl-aniline (146 mg, 88%).

MS (ESI) m/z=262 (M+H)+.

The aryl iodide reagent used in the synthesis of Compound 680 ((4-iodo-2,5-dimethyl-phenyl)-methyl-amine) was synthesized as follows.

(Reaction 135-3)

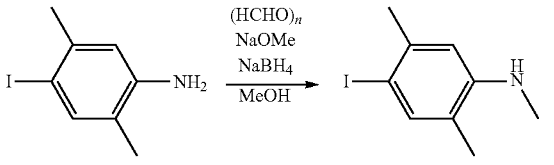

135e 135f (4-Iodo-2,5-dimethyl-phenyl)-methyl-amine was synthesized by operations similar to those in Reaction 135-2 using appropriate reagents and starting material.

MS (ESI) m/z=262 (M+H)+.

Example 136

{4-[2-(2-Cyclohexyl-4-oxo-1,3,8-triaza-spiro[4.5]dec-1-ene-8-sulfonyl)-ethyl]-3-methyl-benzyl}-(2-hydroxy-ethyl)-carbamic acid tert-butyl ester (Compound 681)

(Reaction 136-1)

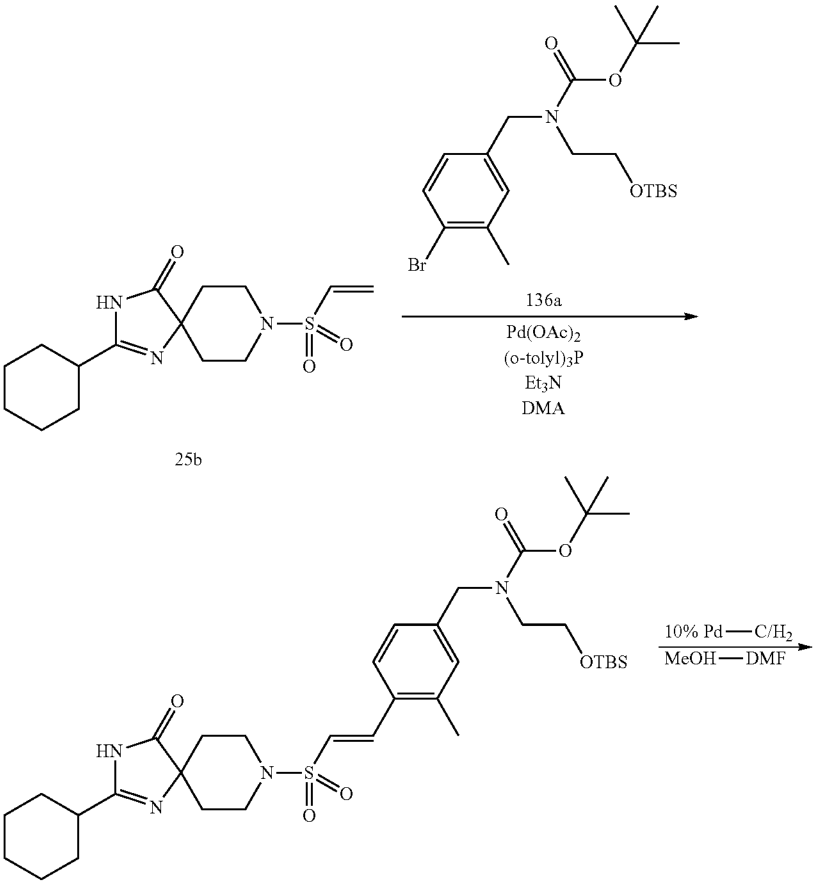

25b

136b

-continued

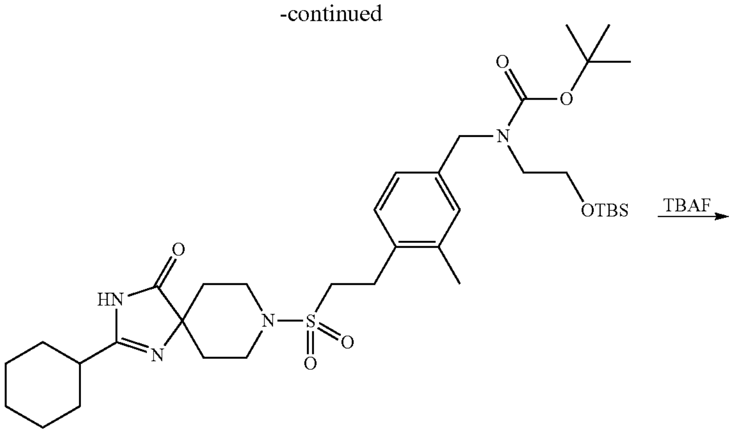

136c

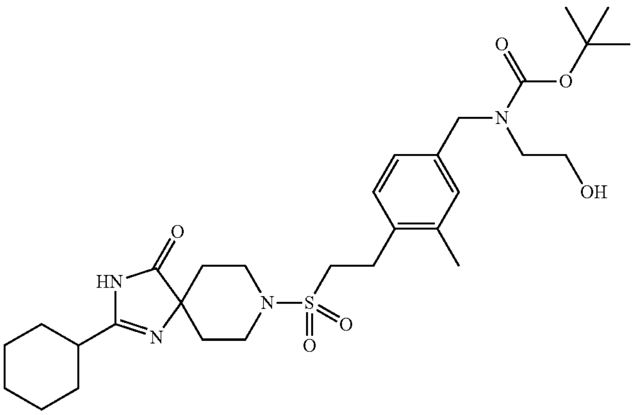

Compound 681

{4-[2-(2-Cyclohexyl-4-oxo-1,3,8-triaza-spiro[4.5]dec-1-ene-8-sulfonyl)-ethyl]-3-methyl-benzyl}-(2-hydroxy-ethyl)-carbamic acid tert-butyl ester was synthesized by operations similar to those in Reaction 26-1, Reaction 42-2 and Reaction 39-2 using appropriate reagents and starting material.

MS (ESI) m/z=589 (M−H)−.

The aryl bromide reagent used in the synthesis of Compound 681 ((4-bromo-3-methyl-benzyl)-[2-(tert-butyl-dimethyl-silanyloxy)-ethyl]-carbamic acid tert-butyl ester) was synthesized as follows.

(Reaction 136-2)

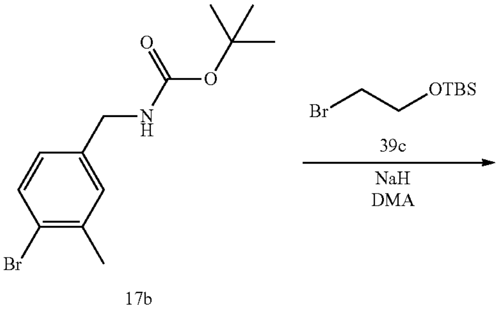

17b

-continued

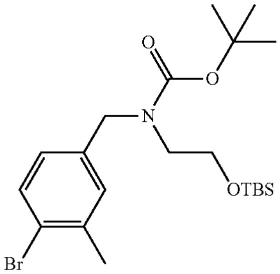

136a (4-Bromo-3-methyl-benzyl)-[2-(tert-butyl-dimethyl-silanyloxy)-ethyl]-carbamic acid tert-butyl ester was synthesized by operations similar to those in Reaction 25-3 using appropriate reagents and starting material.

MS (ESI) m/z=472, 474 (M+H)+.

Example 137
1-(3-Methoxy-5-methyl-4-{2-[2-(4-methyl-cyclohexyl)-4-oxo-1,3,8-triaza-spiro[4.5]dec-1-ene-8-sulfonyl]-ethyl}-phenyl)-1-methyl-urea (Compound 682)
(Reaction 137-1)
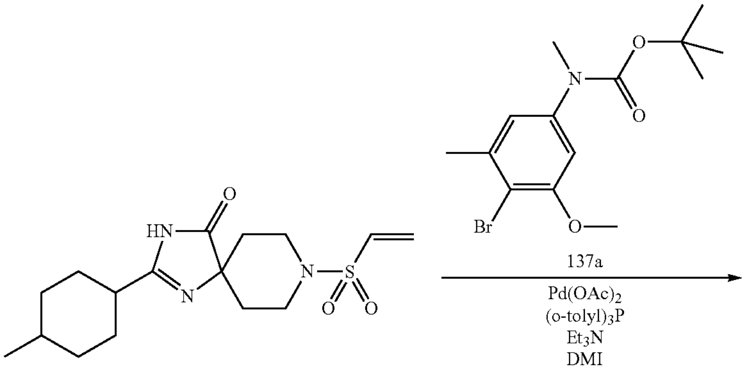
27b
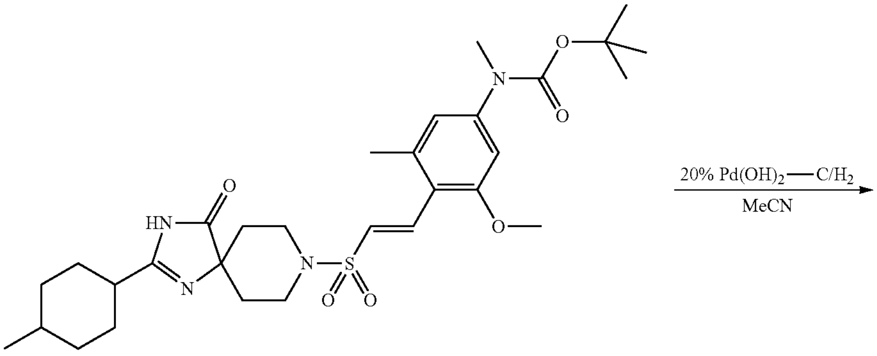
137b
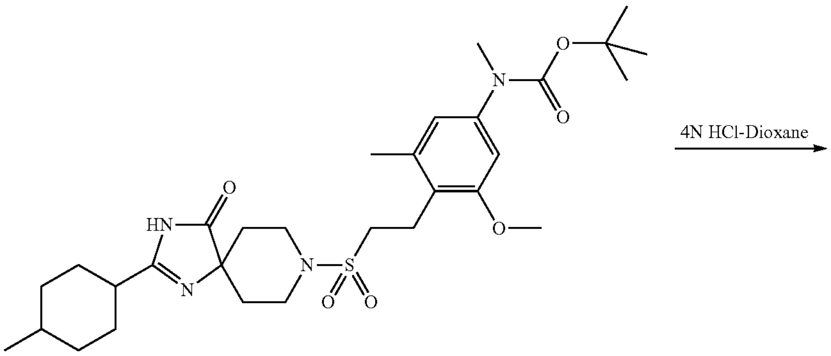
137c -continued

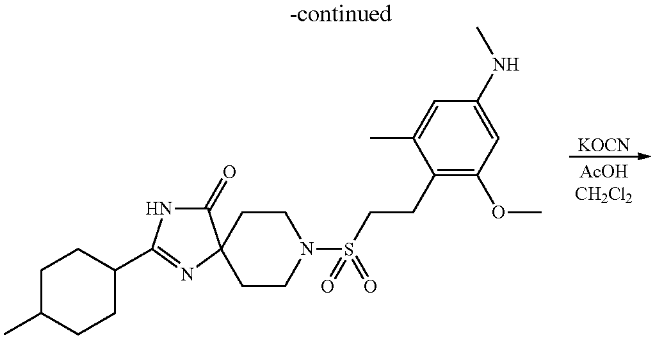

137d

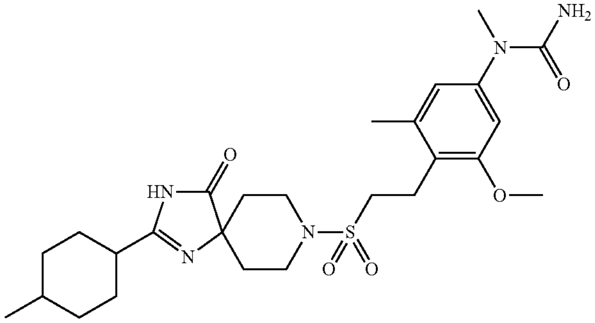

Compound 682

1-(3-Methoxy-5-methyl-4-{2-[2-(4-methyl-cyclohexyl)-4-oxo-1,3,8-triaza-spiro[4.5]dec-1-ene-8-sulfonyl]-ethyl}-phenyl)-1-methyl-urea was synthesized by operations similar to those in Reaction 26-1 (using DMI as a solvent), Reaction 122-2 (using acetonitrile as a solvent), Reaction 5-3 and Reaction 89-2 (using KOCN as a reagent) using appropriate reagents and starting material.

MS (ESI) m/z=534 (M+H)+.

The aryl bromide reagent used in the synthesis of Compound 682 ((4-bromo-3-methoxy-5-methyl-phenyl)-methyl-carbamic acid tert-butyl ester) was synthesized as follows.

(Reaction 137-2)

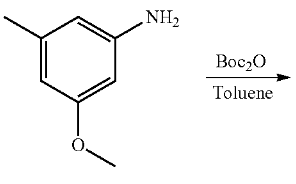

137e

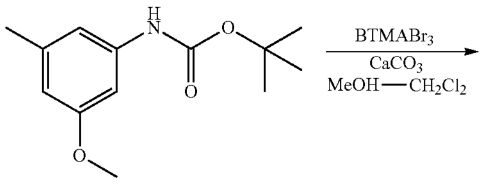

137f

-continued

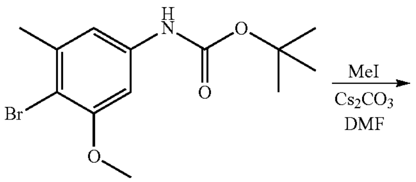

137g

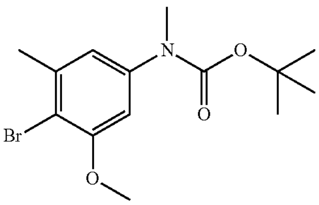

137a (4-Bromo-3-methoxy-5-methyl-phenyl)-methyl-carbamic acid tert-butyl ester was synthesized by operations similar to those in Reaction 127-2 (using toluene as a solvent), Reaction 26-2 and Reaction 26-4 (using cesium carbonate as a base) using appropriate reagents and starting material.

$^1$H-NMR (400 MHz, $CDCl_3$) δ 1.50 (9H, s), 2.42 (3H, s), 3.26 (3H, s), 3.90 (3H, s), 6.71 (1H, d, J=4.0 Hz), 6.77 (1H, J=4.0 Hz).

Example 138
1-(3-Chloro-5-methyl-4-{2-[2-(4-methyl-cyclohexyl)-4-oxo-1,3,8-triaza-spiro[4.5]dec-1-ene-8-sulfonyl]-ethyl}-phenyl)-1-methyl-urea (Compound 683)
(Reaction 138-1)
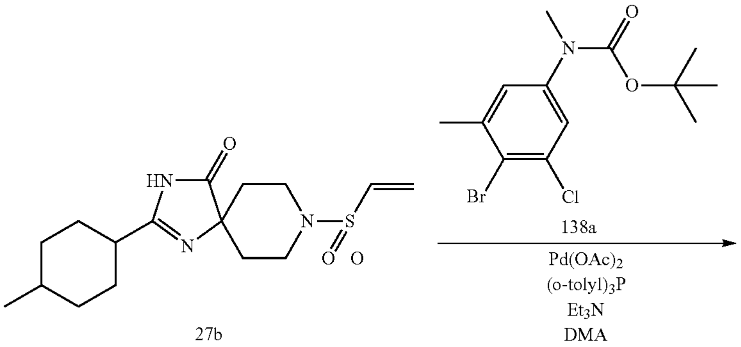
27b
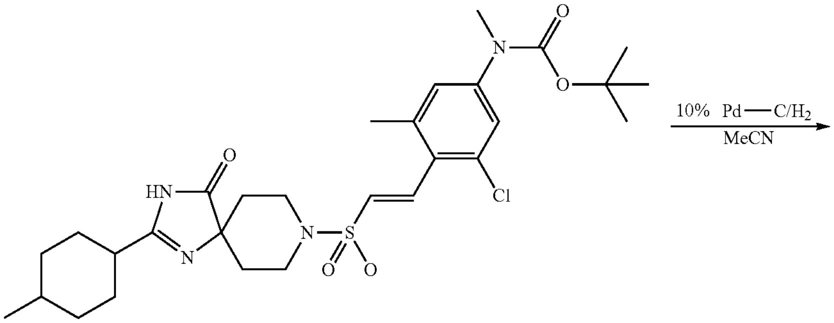
138b
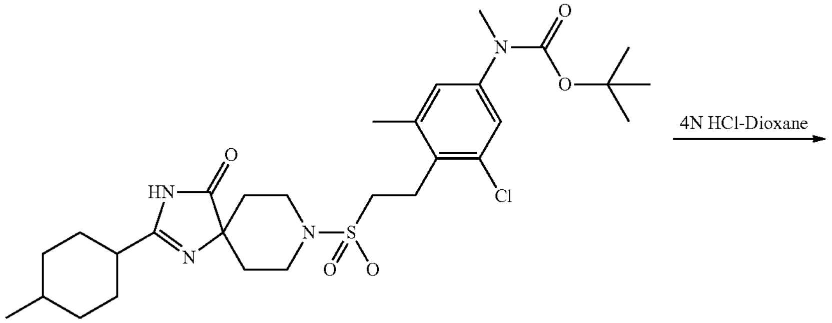
138c
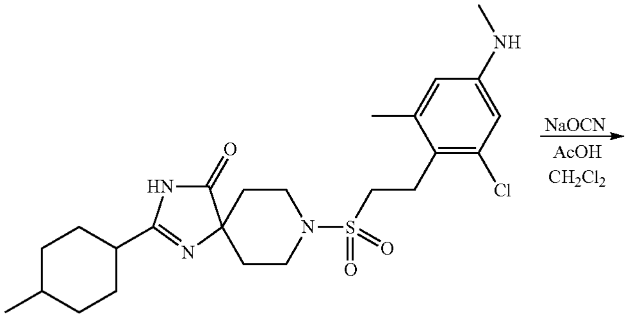
138d -continued

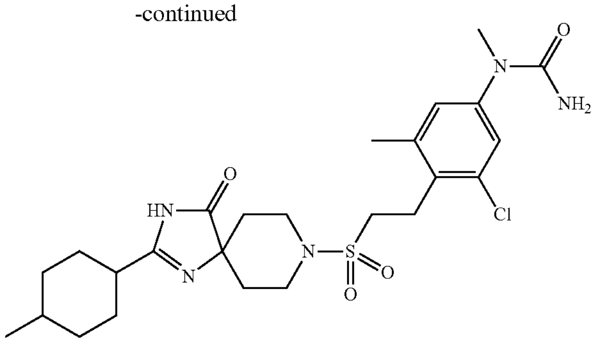

Compound 683

1-(3-Chloro-5-methyl-4-{2-[2-(4-methyl-cyclohexyl)-4-oxo-1,3,8-triaza-spiro[4.5]dec-1-ene-8-sulfonyl]-ethyl}-phenyl)-1-methyl-urea was synthesized by operations similar to those in Reaction 26-1, Reaction 42-1, Reaction 5-3 and Reaction 89-2 using appropriate reagents and starting material.

MS (ESI) m/z=538 (M+H)+.

The aryl bromide reagent used in the synthesis of Compound 683 ((4-bromo-3-chloro-5-methyl-phenyl)-methyl-carbamic acid tert-butyl ester) was synthesized as follows.

(Reaction 138-2)

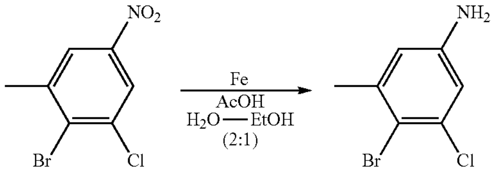

138e 138f

Iron (2.34 g, 41.8 mmol) and acetic acid (0.80 mL, 14.0 mmol) were added to a mixed solution of 2-bromo-1-chloro-3-methyl-5-nitro-benzene (3.50 g, 14.0 mmol) in ethanol (15 mL)-water (31 mL) at room temperature. The mixture was stirred at 100° C. for one hour, and a saturated aqueous sodium bicarbonate solution was then added at 0° C. The mixture was filtered through celite, and the filtrate was washed with ethyl acetate and water. The filtrate was concentrated under reduced pressure. Ethyl acetate was then added, and the organic layer and the aqueous layer were separated. The aqueous layer was repeatedly extracted with ethyl acetate three times, and the organic layers were then dried over sodium sulfate. The resulting residue was concentrated under reduced pressure to give 4-bromo-3-chloro-5-methyl-phenylamine as a pale brown solid (3.01 g, 98%).

MS (ESI) m/z=220, 222 (M+H)+.

(Reaction 138-3)

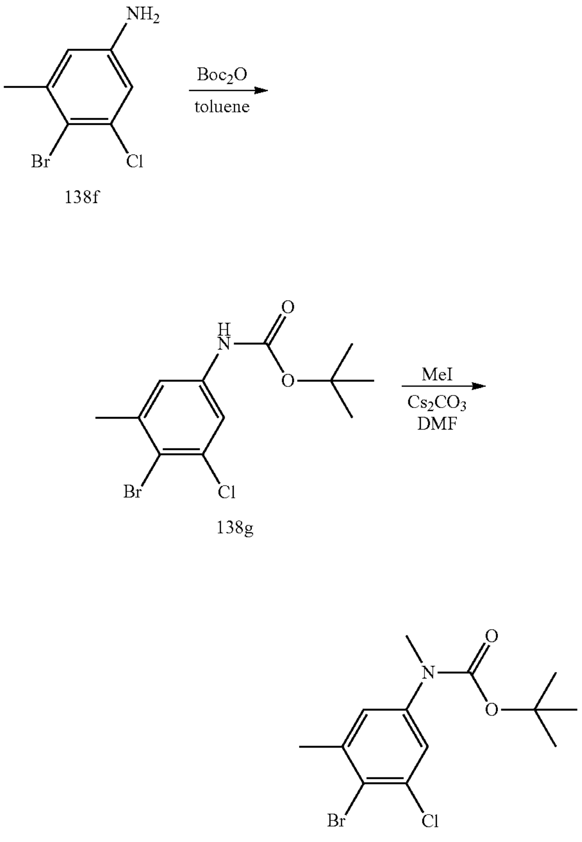

138f 138g 138a (4-Bromo-3-chloro-5-methyl-phenyl)-methyl-carbamic acid tert-butyl ester was synthesized by operations similar to those in Reaction 127-2 (using toluene as a solvent) and Reaction 26-4 (using cesium carbonate as a base) using appropriate reagents and starting material.

$^1$H-NMR (400 MHz, $CDCl_3$) δ 1.46 (9H, s), 2.44 (3H, s), 3.22 (3H, s), 7.06 (1H, d, J=2.4 Hz), 7.23 (1H, d, J=2.4 Hz).

The example compound shown below was synthesized by operations similar to those in Example 138 using appropriate reagents and starting material.

Compound 684

TABLE 100

| Target Compound | Structure | LCMS condition | Retention time (min) | MS (m/z) |
|---|---|---|---|---|
| 684 | 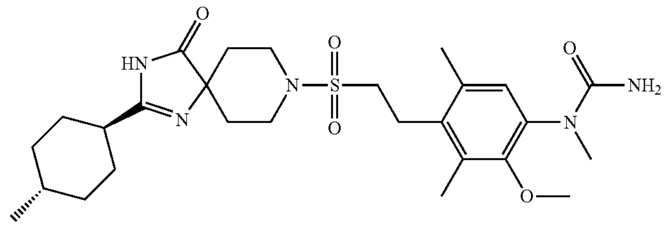 [SMILES: COc1c(N(C)C(N)=O)cc(C)c(CCS(=O)(=O)N2CCC3(CC2)N=C([C@H]2CC[C@H](C)CC2)NC3=O)c1C] | LCMS-F-1 | 0.94 | 548 (M + H)+ |

Example 139

5,7-Dimethyl-6-{2-[2-(4-methyl-cyclohexyl)-4-oxo-1,3,8-triaza-spiro[4.5]dec-1-ene-8-sulfonyl]-ethyl}-1H-quinazoline-2,4-dione (Compound 685)

(Reaction 139-1)

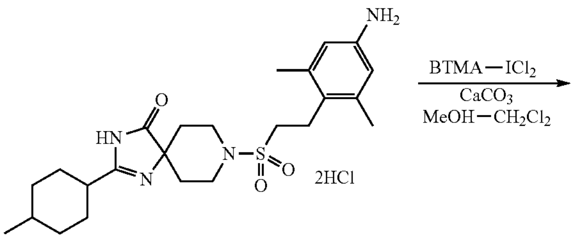

139a

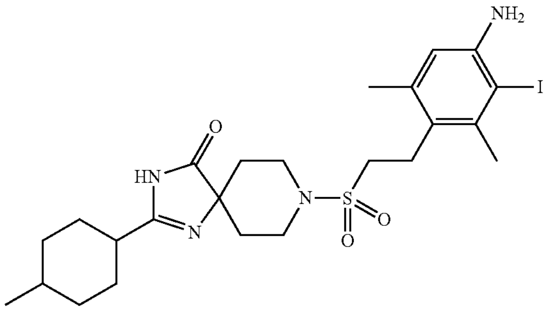

139b

Benzyltrimethylammonium dichloroiodate (324 mg, 0.930 mmol) was added to a mixture of 8-[2-(4-amino-2,6-dimethyl-phenyl)-ethanesulfonyl]-2-(4-methyl-cyclohexyl)-1,3,8-triaza-spiro[4.5]dec-1-en-4-one dihydrochloride (530 mg, 1.03 mmol) and calcium carbonate (517 mg, 5.17 mmol) in methanol (6 mL)-dichloromethane (15 mL) at room temperature. The mixture was stirred at room temperature for 22 hours, and an aqueous sodium bicarbonate solution and ethyl acetate were then added. The organic layer and the aqueous layer were separated, and the aqueous layer was repeatedly extracted with ethyl acetate three times. The organic layers were combined and washed with saturated brine, and the insoluble matter was then filtered off through celite. The filtrate was concentrated under reduced pressure, and the resulting residue was purified by silica gel column chromatography to give 8-[2-(4-amino-3-iodo-2,6-dimethyl-phenyl)-ethanesulfonyl]-2-(4-methyl-cyclohexyl)-1,3,8-triaza-spiro[4.5]dec-1-en-4-one as a pale yellow solid (337 mg, 62%).

MS (ESI) m/z=587 (M+H)+.

(Reaction 139-2)

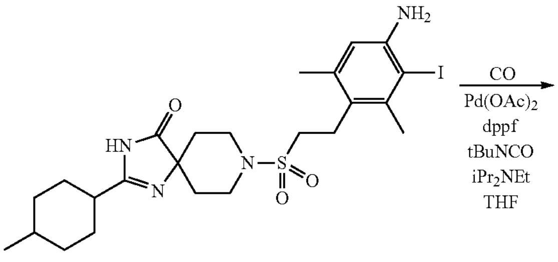

139b

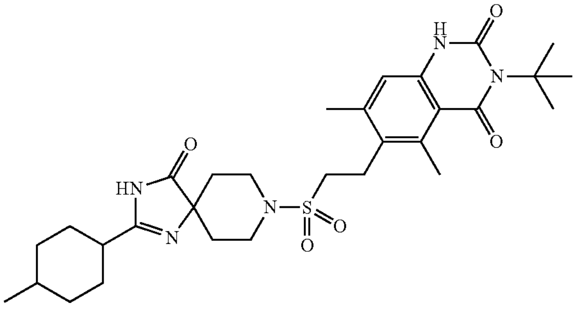

139c

A mixture of 8-[2-(4-amino-3-iodo-2,6-dimethyl-phenyl)-ethanesulfonyl]-2-(4-methyl-cyclohexyl)-1,3,8-triaza-spiro[4.5]dec-1-en-4-one (15 mg, 0.0256 mmol), palladium acetate (1.1 mg, 5.11 μmol), 1,1'-bis(diphenylphosphino)ferrocene (2.2 mg, 5.11 μmol), tert-butyl isocyanate (12 μL, 0.0767 mmol) and N,N-diisopropylethylamine (13 μL, 0.0767 mmol) in tetrahydrofuran (1 mL) was heated with stirring for 12 hours in a pressure bottle sealed under the conditions of 4 atm and 80° C. in a carbon monoxide atmosphere. After returning to room temperature, palladium acetate (2.2 mg, 10.22 μmol), 1,1'-bis(diphenylphosphino) ferrocene (4.4 mg, 10.22 μmol), tert-butyl isocyanate (24 μL, 0.153 mmol) and N,N-diisopropylethylamine (26 μL, 0.153 mmol) were added to the reaction solution, and the mixture was heated with stirring for 14 hours in a pressure bottle sealed under the conditions of 4 atm and 80° C. in a carbon monoxide atmosphere. After returning to room temperature, the reaction solution was concentrated under reduced pressure, and the resulting residue was purified by preparative TLC to give 3-tert-butyl-5,7-dimethyl-6-{2-[2-(4-methyl-cyclohexyl)-4-oxo-1,3,8-triaza-spiro[4.5]dec-1-ene-8-sulfonyl]-ethyl}-1H-quinazoline-2,4-dione as a pale yellow solid (3.3 mg, 22%).

MS (ESI) m/z=586 (M+H)+.

(Reaction 139-3)

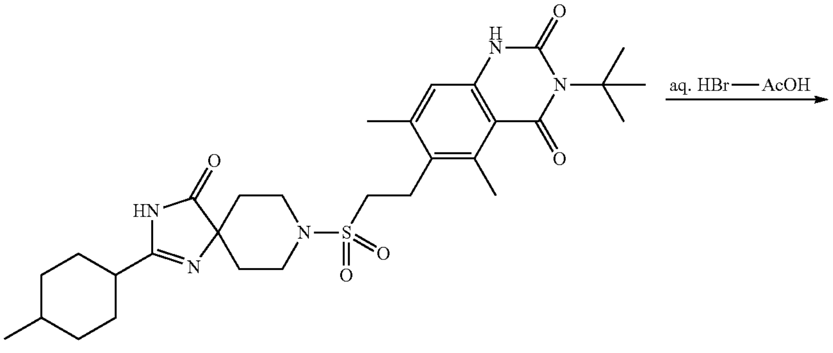

139c

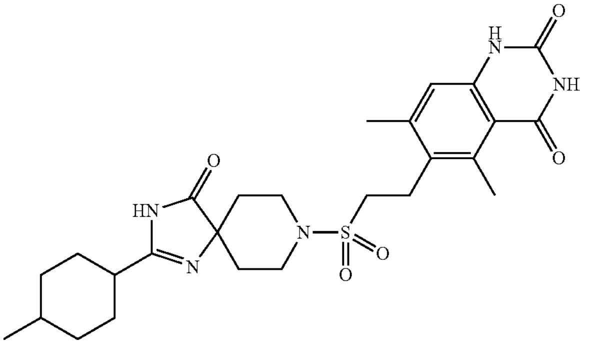

Compound 685

An aqueous hydrogen bromide solution (80 μL) was added to a mixed solution of 3-tert-butyl-5,7-dimethyl-6-{2-[2-(4-methyl-cyclohexyl)-4-oxo-1,3,8-triaza-spiro[4.5]dec-1-ene-8-sulfonyl]-ethyl}-1H-quinazoline-2,4-dione (3.3 mg, 3.41 μmol) in acetic acid (80 μL), and the mixture was heated with stirring at 100° C. for one hour. The reaction solution was returned to room temperature and then concentrated under reduced pressure, and the resulting residue was purified by preparative TLC to give 5,7-dimethyl-6-{2-[2-(4-methyl-cyclohexyl)-4-oxo-1,3,8-triaza-spiro[4.5]dec-1-ene-8-sulfonyl]-ethyl}-1H-quinazoline-2,4-dione as a pale yellow solid (1.2 mg, 44%).

MS (ESI) m/z=530 (M+H)+.

Example 140

8-{(E)-2-[1-(2-Amino-ethyl)-1H-indol-4-yl]-ethenesulfonyl}-2-cyclohexyl-1,3,8-triaza-spiro[4.5]dec-1-en-4-one (Compound 686)

(Reaction 140-1)

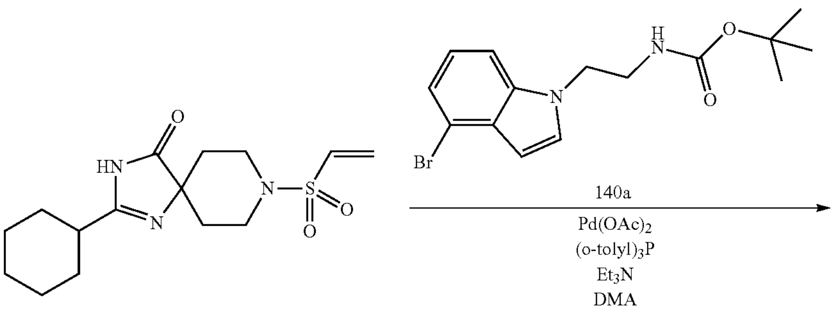

25b

-continued

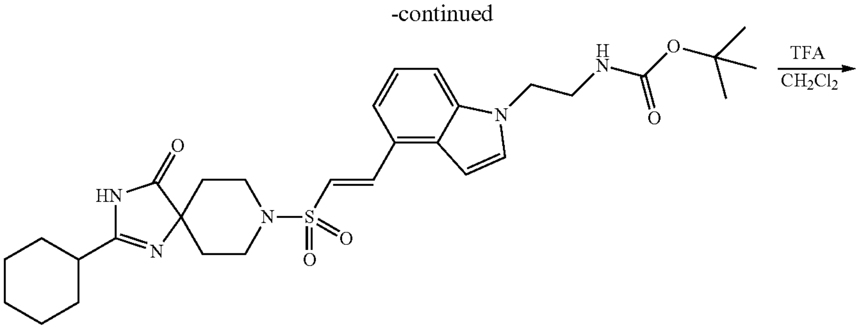

140b

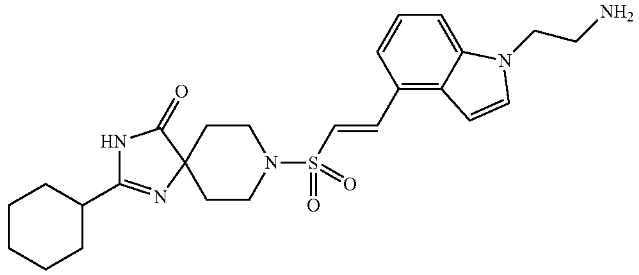

Compound 686

8-{(E)-2-[1-(2-Amino-ethyl)-1H-indol-4-yl]-ethenesulfonyl}-2-cyclohexyl-1,3,8-triaza-spiro[4.5]dec-1-en-4-one was synthesized by operations similar to those in Reaction 25-2 and Reaction 7-2 using appropriate reagents and starting material.

MS (ESI) m/z=484 (M+H)+.

The aryl bromide reagent used in the synthesis of Compound 686 ([2-(4-bromo-indol-1-yl)-ethyl]-carbamic acid tert-butyl ester) was synthesized as follows.

(Reaction 140-2)

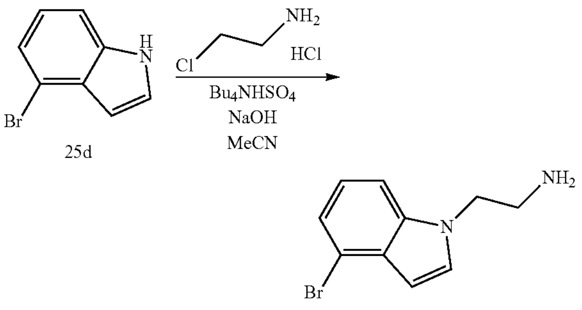

140c

Tetrabutylammonium hydrogen sulfate (41.0 mg, 0.121 mmol) and sodium hydroxide (210 mg, 5.25 mmol) were added to a solution of 4-bromo-1H-indole (0.30 ml, 2.39 mmol) in acetonitrile (0.80 mL), and the mixture was stirred at room temperature for 20 minutes. Subsequently, 2-chloroethylamine hydrochloride (334 mg, 2.88 mmol) was added and the mixture was heated with stirring at 100° C. for seven hours. After cooling, water was added to the reaction mixture, followed by extraction with ethyl acetate. The organic layer was sequentially washed with water and saturated brine and then concentrated under reduced pressure. The resulting residue was purified by silica gel column chromatography (dichloromethane-methanol) to give 2-(4-bromo-indol-1-yl)-ethylamine (222 mg, 39%).

MS (ESI) m/z=239, 241 (M+H)+.

(Reaction 140-3)

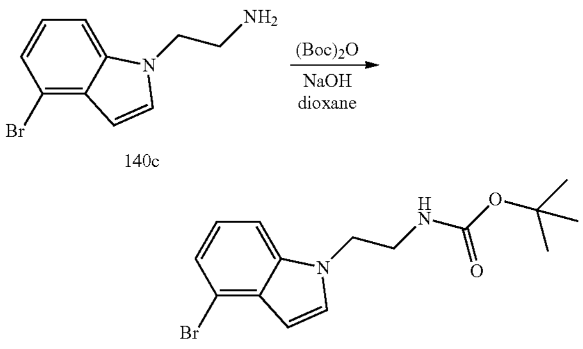

140a

A 2 N aqueous NaOH solution (0.47 ml, 0.94 mmol) and di-tert-butyl dicarbonate (223 mg, 1.02 mmol) were sequentially added to a solution of 2-(4-bromo-indol-1-yl)-ethylamine (222 mg, 0.928 mmol) in dioxane (0.47 ml), and the mixture was stirred at room temperature for 19 hours. Water was added to the reaction mixture, followed by extraction with ethyl acetate. The organic layer was washed with saturated brine and then concentrated under reduced pressure. The resulting residue was purified by silica gel column chromatography (dichloromethane only) to give [2-(4-bromo-indol-1-yl)-ethyl]-carbamic acid tert-butyl ester (292 mg, 93%).

MS (ESI) m/z=361, 363 (M+Na)+.

The example compound shown below was synthesized by operations similar to those in Example 140 using appropriate reagents and starting material.

Compound 687
TABLE 101
| Target Compound | Structure | LCMS condition | Retention time (min) | MS (m/z) |
|---|---|---|---|---|
| 687 | 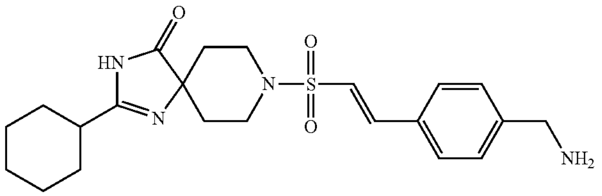 2TFA | LCMS-C-1 | 1.98 | 431 (M + H)+ |
Example 141
(S)-2-Amino-3-hydroxy-N-(3-methyl-4-{(E)-2-[4-oxo-2-(3-trifluoromethyl-phenyl)-1,3,8-triaza-spiro[4.5]dec-1-ene-8-sulfonyl]-vinyl}-phenyl)-propionamide (Compound 688)
(Reaction 141-1)
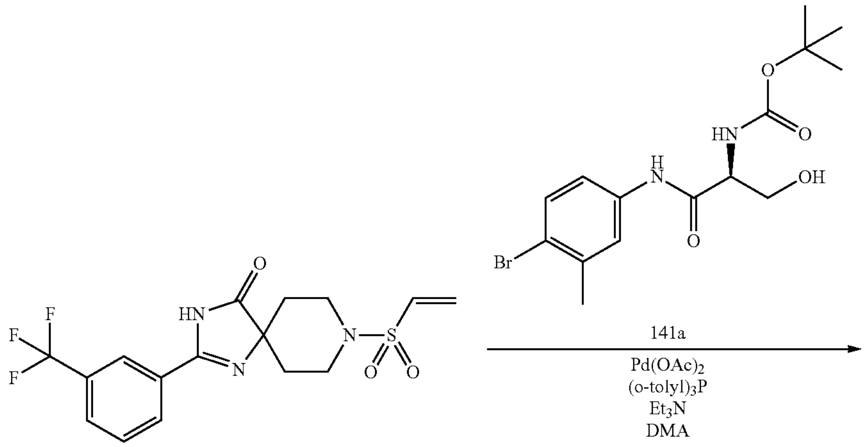
8d
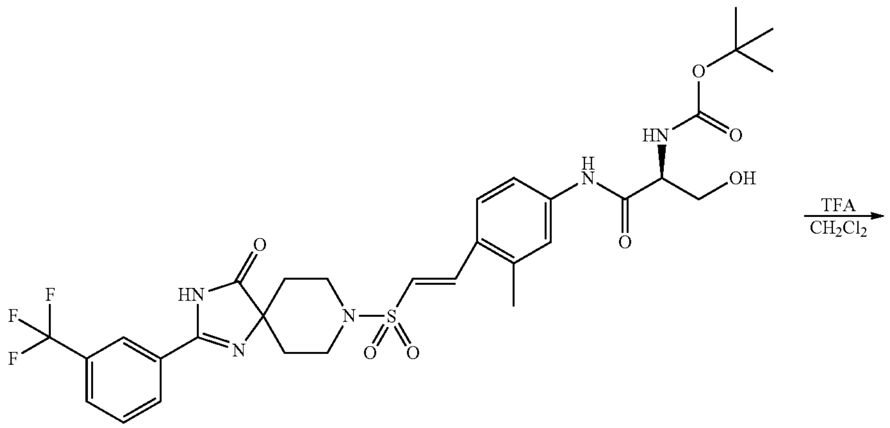
141b -continued

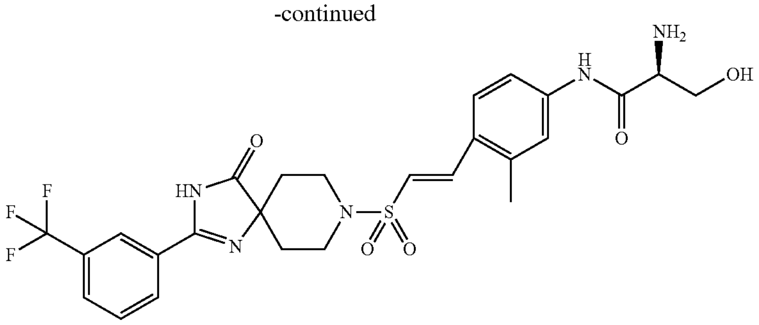

Compound 688

(S)-2-Amino-3-hydroxy-N-(3-methyl-4-{(E)-2-[4-oxo-2-(3-trifluoromethyl-phenyl)-1,3,8-triaza-spiro[4.5]dec-1-ene-8-sulfonyl]-vinyl}-phenyl)-propionamide was synthesized by operations similar to those in Reaction 25-2 and Reaction 7-2 using appropriate reagents and starting material.

MS (ESI) m/z=580 (M+H)+.

The aryl bromide reagent used in the synthesis of Compound 688 ([(S)-1-(4-bromo-3-methyl-phenylcarbamoyl)-2-hydroxy-ethyl]-carbamic acid tert-butyl ester) was synthesized as follows.

(Reaction 141-2)

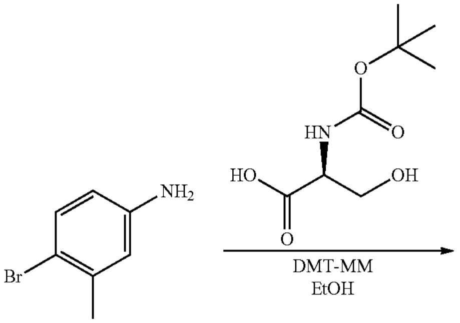

26h

-continued

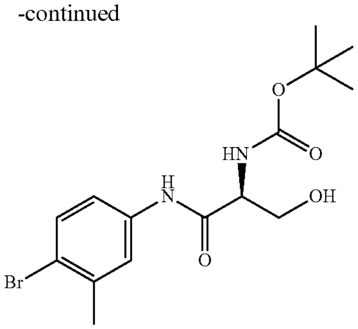

141a

[(S)-1-(4-Bromo-3-methyl-phenylcarbamoyl)-2-hydroxy-ethyl]-carbamic acid tert-butyl ester was synthesized by operations similar to those in Reaction 10-1 using appropriate reagents and starting material.

MS (ESI) m/z=317, 219 (M-tBu+H+H)+.

Example 142

N-(3,5-Dimethyl-4-{(E)-2-[4-oxo-2-(3-trifluoromethoxy-phenyl)-1,3,8-triaza-spiro[4.5]dec-1-ene-8-sulfonyl]-vinyl}-phenyl)-N-piperidin-4-yl-methanesulfonamide (Compound 689)

(Reaction 142-1)

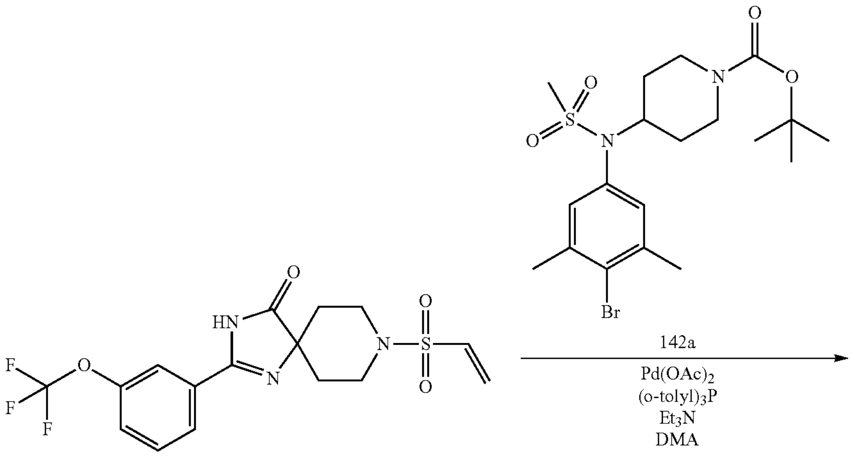

30a

-continued

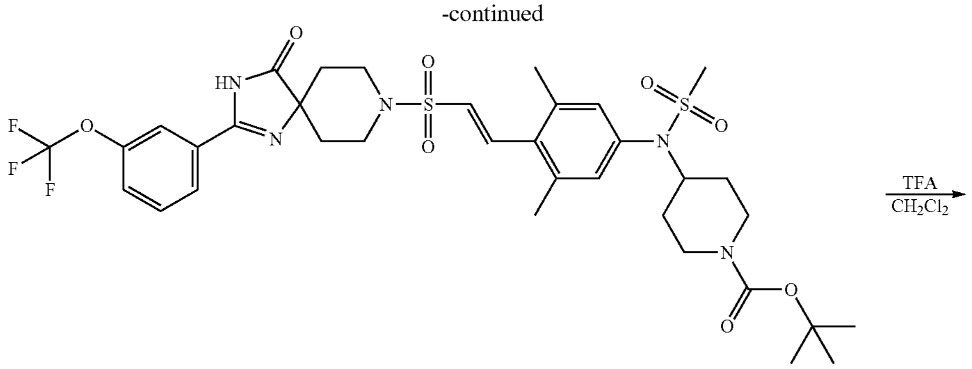

142b

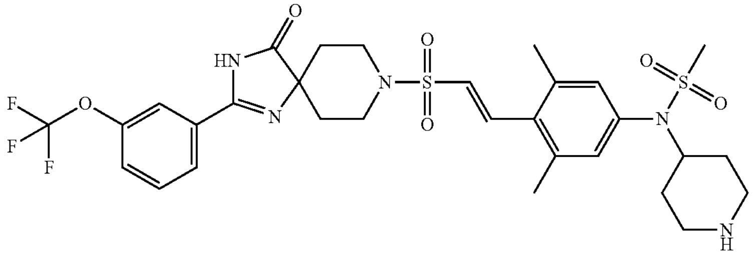

Compound 689

N-(3,5-Dimethyl-4-{(E)-2-[4-oxo-2-(3-trifluoromethoxy-phenyl)-1,3,8-triaza-spiro[4.5]dec-1-ene-8-sulfonyl]-vinyl}-phenyl)-N-piperidin-4-yl-methanesulfonamide was synthesized by operations similar to those in Reaction 26-1 and Reaction 7-2 using appropriate reagents and starting material.

MS (ESI) m/z=684 (M+H)+.

The aryl bromide reagent used in the synthesis of Compound 142 (4-[(4-bromo-3,5-dimethyl-phenyl)-methane-sulfonyl-amino]-piperidine-1-carboxylic acid tert-butyl ester) was synthesized as follows.

(Reaction 142-2)

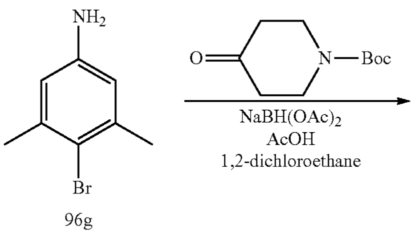

96g

-continued

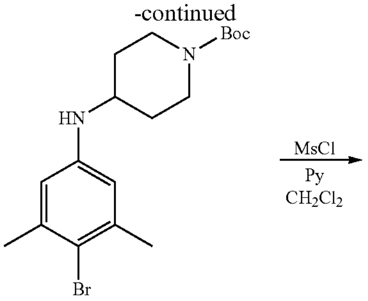

142c

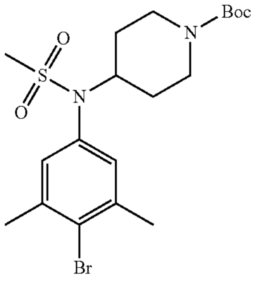

142a

4-[(4-Bromo-3,5-dimethyl-phenyl)-methanesulfonyl-amino]-piperidine-1-carboxylic acid tert-butyl ester was synthesized by operations similar to those in Reaction 41-1 and Reaction 6-1 using appropriate reagents and starting material.

MS (ESI) m/z=461, 463 (M+H)+.

Example 143

8-[(E)-2-(2,6-Dimethyl-4-methylamino-phenyl)-ethenesulfonyl]-2-(9,9,9-trifluoro-nonyl)-1,3,8-triaza-spiro[4.5]dec-1-en-4-one (Compound 690)

(Reaction 143-1)

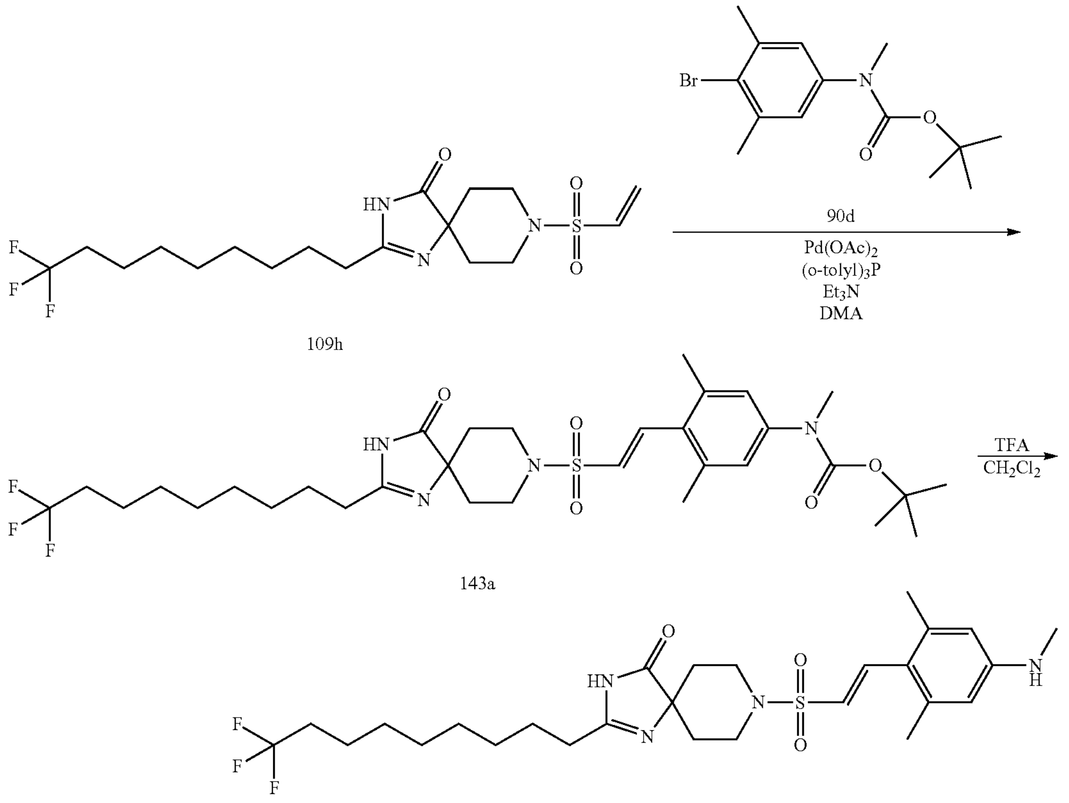

109h

143a

Compound 690

8-[(E)-2-(2,6-Dimethyl-4-methylamino-phenyl)-ethenesulfonyl]-2-(9,9,9-trifluoro-nonyl)-1,3,8-triaza-spiro[4.5]dec-1-en-4-one was synthesized by operations similar to those in Reaction 26-1 and Reaction 7-2 using appropriate reagents and starting material.

MS (ESI) m/z=557 (M+H)+.

The aryl bromide reagent used in the synthesis of Compound 690 ((4-bromo-3,5-dimethyl-phenyl)-methyl-carbamic acid tert-butyl ester) was synthesized as follows.

(Reaction 143-2)

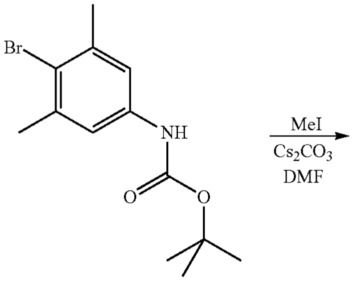

119b

-continued

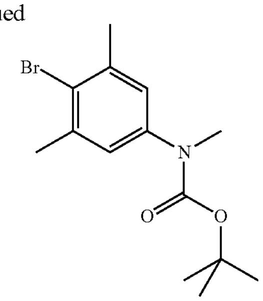

90d

Iodomethane (20.5 ml, 329 mmol) was added to a solution of (4-bromo-3,5-dimethyl-phenyl)-carbamic acid tert-butyl ester (47.5 g, 158 mmol) and cesium carbonate (80.6 g, 247 mmol) in DMF (165 ml) at room temperature, and the mixture was stirred for 27 hours. Further, cesium carbonate (26.9 g, 82.6 mmol) and iodomethane (20.5 ml, 329 mmol) were added at room temperature, and the mixture was further stirred for three days. An aqueous ammonium chloride solution was added to the reaction mixture, followed by extraction with ethyl acetate. The organic layer was sequentially washed with water and saturated brine and then concentrated under reduced pressure. The resulting residue was purified by silica gel column chromatography (hexane-ethyl acetate) to give (4-bromo-3,5-dimethyl-phenyl)-methyl-carbamic acid tert-butyl ester (9.34 g, 92%).

MS (ESI) m/z=258, 260 (M-tBu+H+H)+.

Example 144

8-[(E)-2-(2,6-Dimethyl-4-methylamino-phenyl)-ethenesulfonyl]-2-(8,8,9,9,9-pentafluoro-nonyl)-1,3,8-triaza-spiro[4.5]dec-1-en-4-one (Compound 691)

(Reaction 144-1)

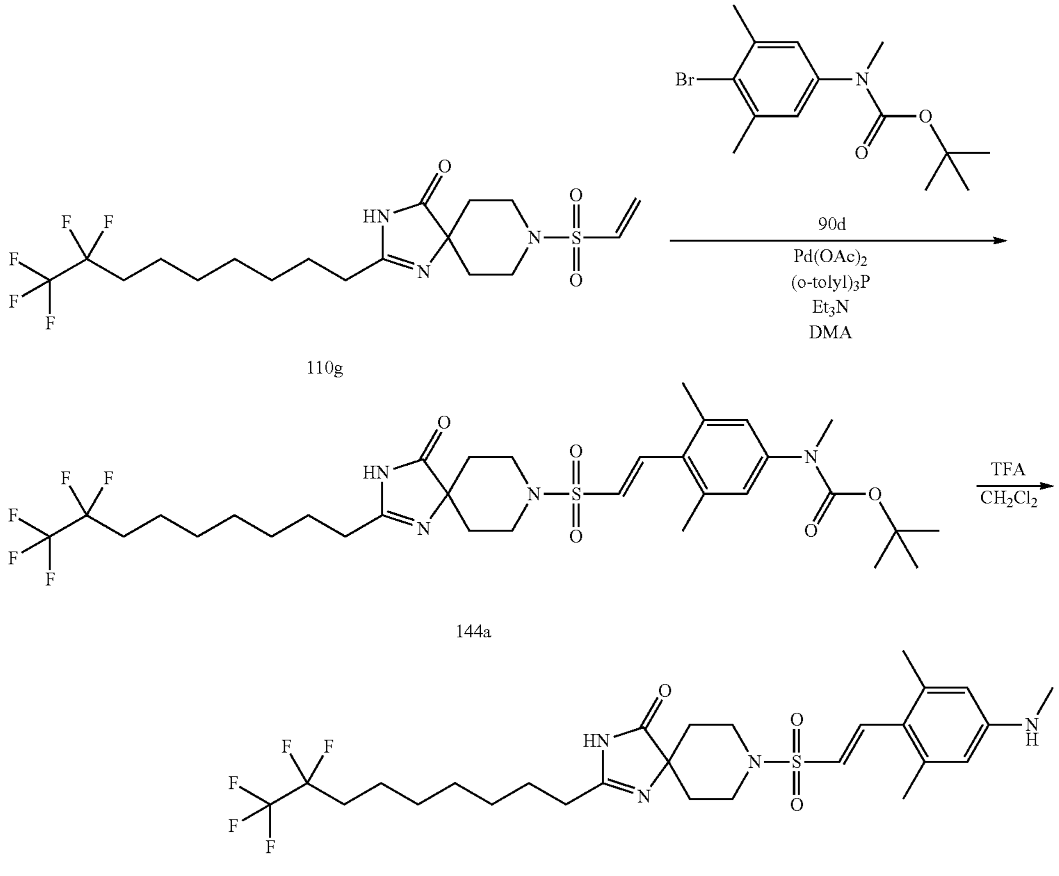

110g

144a

Compound 691

8-[(E)-2-(2,6-Dimethyl-4-methylamino-phenyl)-ethenesulfonyl]-2-(8,8,9,9,9-pentafluoro-nonyl)-1,3,8-triaza-spiro[4.5]dec-1-en-4-one was synthesized by operations similar to those in Reaction 26-1 and Reaction 7-2 using appropriate reagents and starting material.

MS (ESI) m/z=593 (M+H)+.

Example 145

1-{3,5-Dimethyl-4-[(E)-2-(2-nonyl-4-oxo-1,3,8-triaza-spiro[4.5]dec-1-ene-8-sulfonyl)-vinyl]-phenyl}-1-methyl-urea (Compound 692)

(Reaction 145-1)

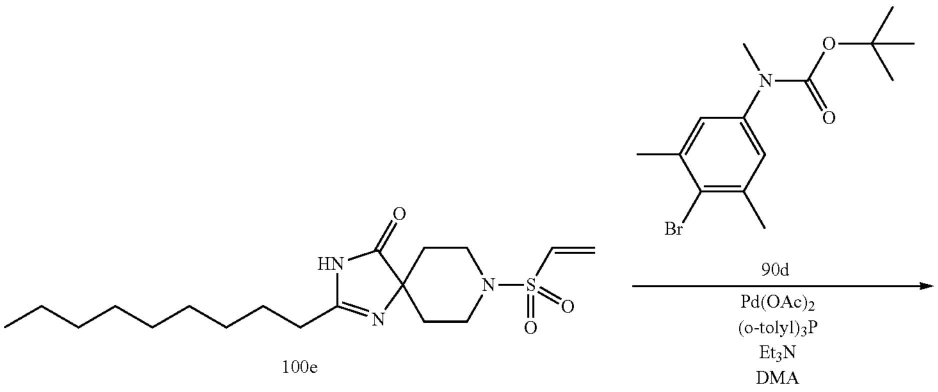

100e

-continued

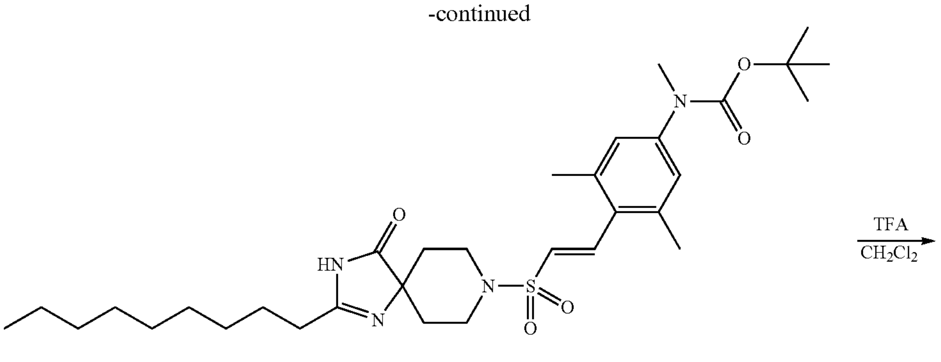

145a

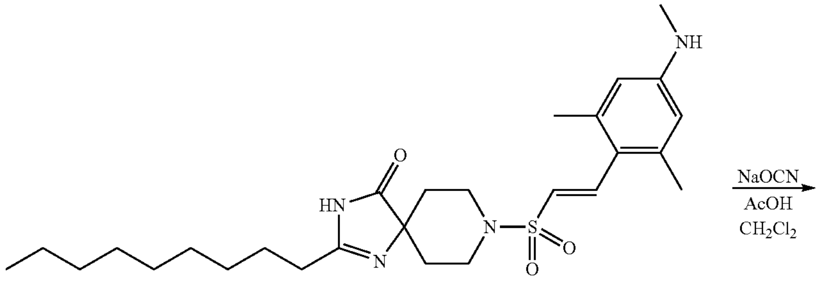

145b

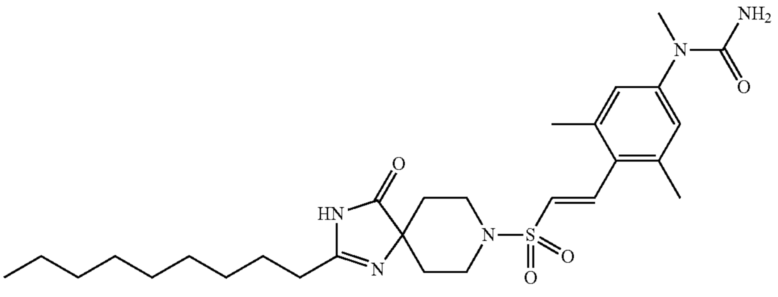

Compound 692

1-{3,5-Dimethyl-4-[(E)-2-(2-nonyl-4-oxo-1,3,8-triaza-spiro[4.5]dec-1-ene-8-sulfonyl)-vinyl]-phenyl}-1-methyl-urea was synthesized by operations similar to those in Reaction 25-2, Reaction 7-2 and Reaction 89-2 using appropriate reagents and starting material.

MS (ESI) m/z=546 (M+H)+.

Example 146

1-(2-Methoxy-3,5-dimethyl-4-{(E)-2-[2-(4-methyl-cyclohexyl)-4-oxo-1,3,8-triaza-spiro[4.5]dec-1-ene-8-sulfonyl]-vinyl}-phenyl)-1-methyl-urea (Compound 693)

(Reaction 146-1)

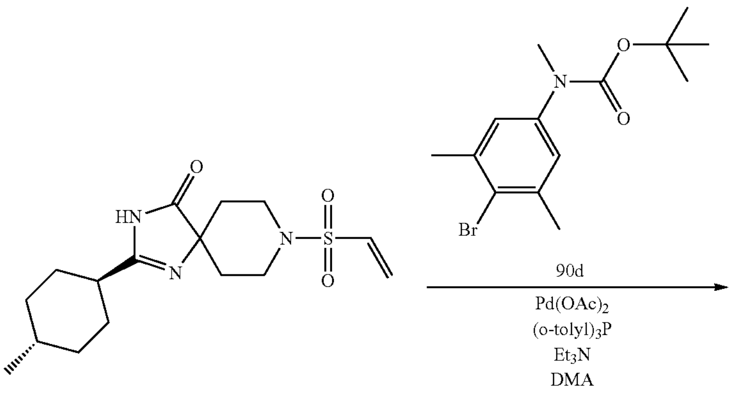

27b

-continued

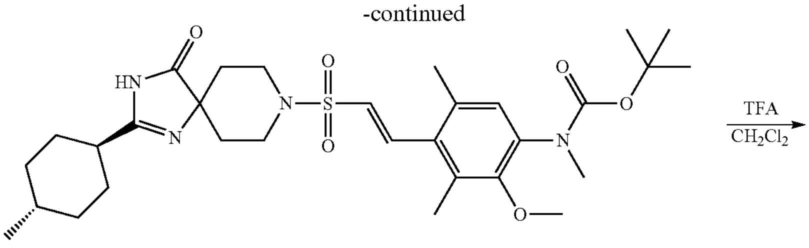

146a

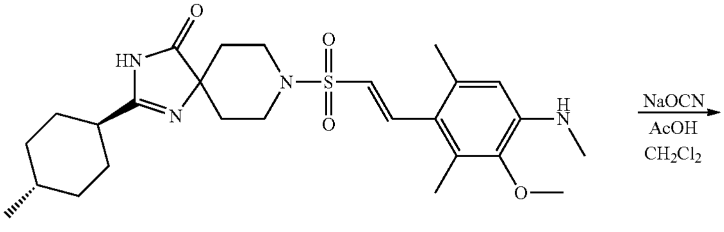

146b

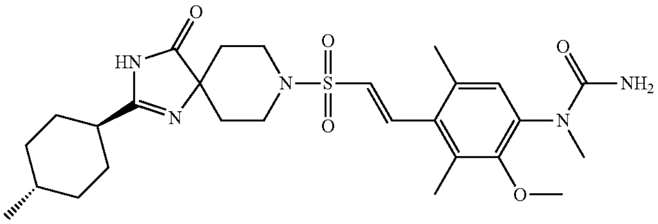

Compound 693

1-(2-Methoxy-3,5-dimethyl-4-{(E)-2-[2-(4-methyl-cyclohexyl)-4-oxo-1,3,8-triaza-spiro[4.5]dec-1-ene-8-sulfonyl]-vinyl}-phenyl)-1-methyl-urea was synthesized by operations similar to those in Reaction 26-1, Reaction 7-2 and Reaction 89-2 using appropriate reagents and starting material.

MS (ESI) m/z=546 (M+H)+.

Example 147

1-[3,5-Dimethyl-4-((E)-2-{4-oxo-2-[4-(3,3,3-trifluoro-propyl)-cyclohexyl]-1,3,8-triaza-spiro[4.5]dec-1-ene-8-sulfonyl}-vinyl)-phenyl]-1-(2-fluoro-ethyl)-urea (Compound 694)

(Reaction 147-1)

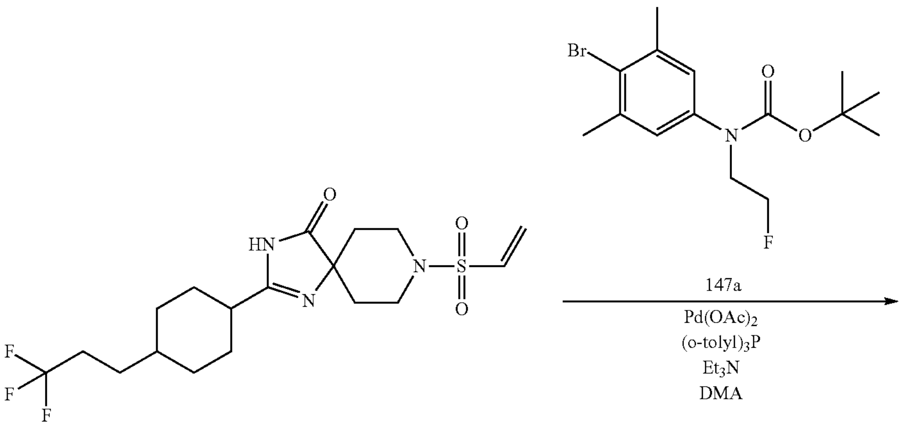

101j

-continued

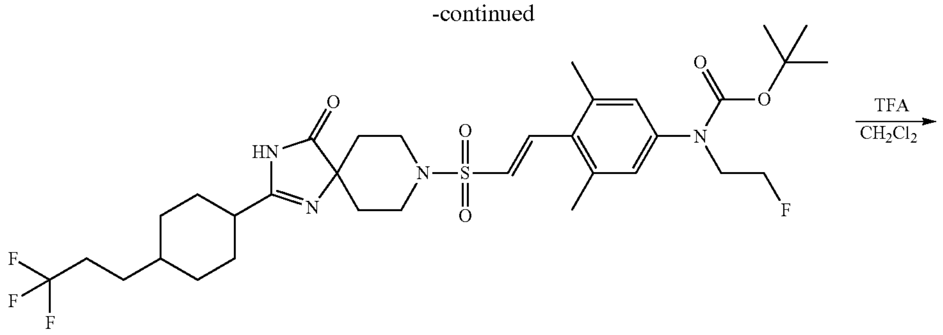

147b

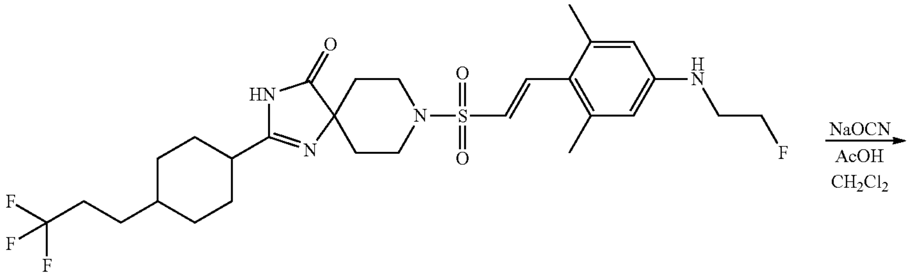

147c

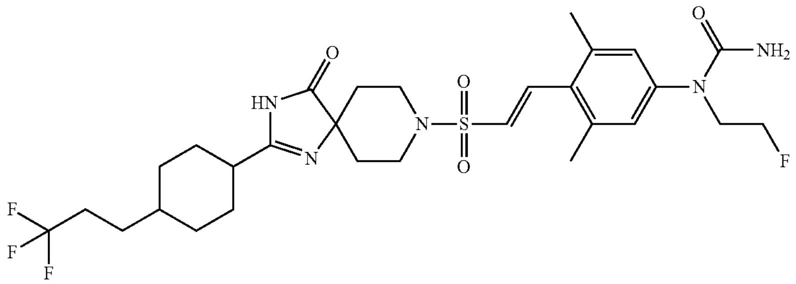

Compound 694

1-[3,5-Dimethyl-4-((E)-2-{4-oxo-2-[4-(3,3,3-trifluoro-propyl)-cyclohexyl]-1,3,8-triaza-spiro[4.5]dec-1-ene-8-sulfonyl}-vinyl)-phenyl]-1-(2-fluoro-ethyl)-urea was synthesized by operations similar to those in Reaction 26-1, Reaction 7-2 and Reaction 89-2 using appropriate reagents and starting material.

MS (ESI) m/z=630 (M+H)+.

The aryl bromide reagent used in the synthesis of Compound 694 ((4-bromo-3,5-dimethyl-phenyl)-(2-fluoro-ethyl)-carbamic acid tert-butyl ester) was synthesized as follows.

(Reaction 147-2)

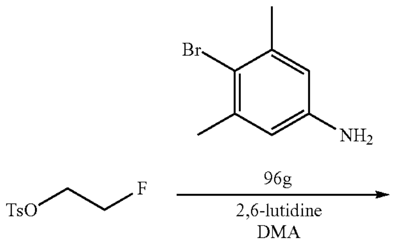

147d

-continued

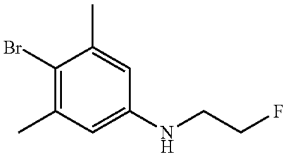

147e

A solution of 4-bromo-3,5-dimethyl-phenylamine (400 mg, 2 mmol), toluene-4-sulfonic acid 2-fluoro-ethyl ester (567 mg, 2.6 mmol) and 2,6-lutidine (429 mg, 4.0 mmol) in DMA (5 ml) was heated with stirring at 120° C. for four hours. The mixture was quenched with water and then extracted with ethyl acetate. The organic layer was sequentially washed with water and saturated brine and then concentrated under reduced pressure. The resulting residue was purified by silica gel column chromatography (ethyl acetate-hexane) to give (4-bromo-3,5-dimethyl-phenyl)-(2-fluoro-ethyl)-amine (262 mg, 53%).

$^1$H-NMR ($CDCl_3$) δ 6.39 (s, 2H), 4.68 (t, 1H, J=4.96 Hz), 4.52 (t, 1H, J=4.96 Hz), 3.92 (brd, 1H), 3.45 (t, 1H, J=4.96 Hz), 3.36 (t, 1H, J=4.96 Hz), 2.34 (s, 3H).

(Reaction 147-3)

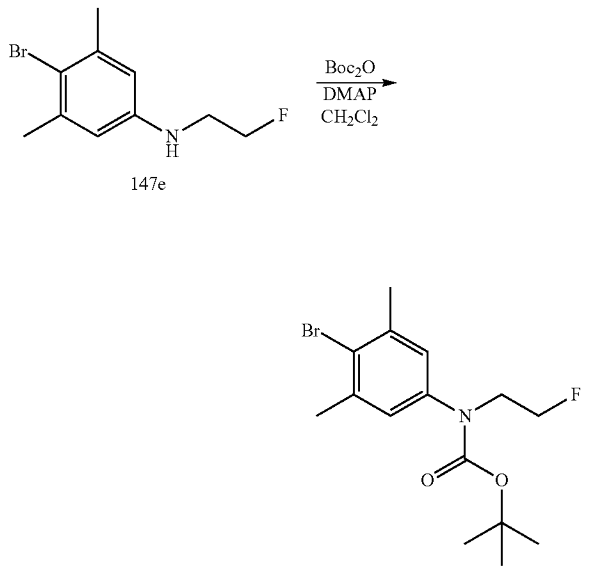

147e

147a (4-Bromo-3,5-dimethyl-phenyl)-(2-fluoro-ethyl)-carbamic acid tert-butyl ester was synthesized by operations similar to those in Reaction 19-2 (using DMAP as a base) using appropriate reagents and starting material.

$^1$H-NMR ($CDCl_3$) δ 6.97 (s, 2H), 4.64 (t, 1H, J=4.96 Hz), 4.48 (t, 1H, J=4.96 Hz), 3.9 (t, 1H, J=4.96 Hz), 3.82 (t, 1H, J=4.96 Hz), 2.39 (s, 6H), 1.45 (s, 9H).

Example 148

1-(3-Chloro-5-methyl-4-{(E)-2-[2-(4-methyl-cyclohexyl)-4-oxo-1,3,8-triaza-spiro[4.5]dec-1-ene-8-sulfonyl]-vinyl}-phenyl)-1-methyl-urea (Compound 695)

(Reaction 148-1)

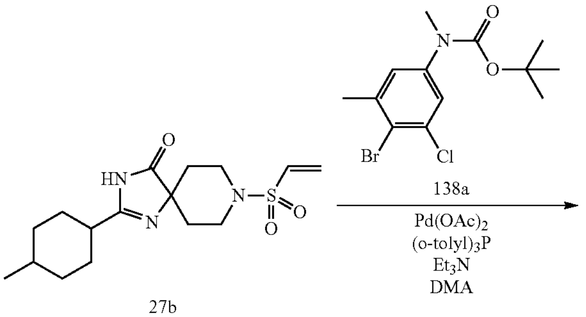

138a

27b

-continued

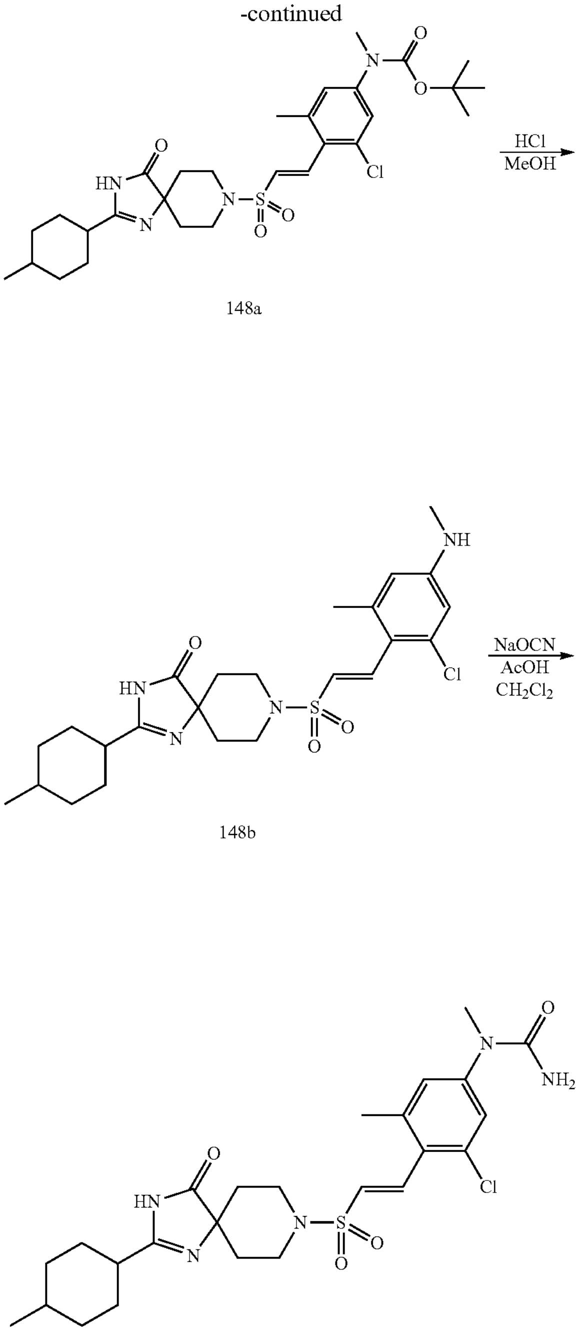

148a

148b

Compound 695

1-(3-Chloro-5-methyl-4-{(E)-2-[2-(4-methyl-cyclohexyl)-4-oxo-1,3,8-triaza-spiro[4.5]dec-1-ene-8-sulfonyl]-vinyl}-phenyl)-1-methyl-urea was synthesized by operations similar to those in Reaction 26-1, Reaction 50-2 and Reaction 89-2 using appropriate reagents and starting material.

MS (ESI) m/z=630 (M+H)+.

Example 149
1-[3,5-Dimethyl-4-(2-{4-oxo-2-[4-(3,3,3-trifluoro-propyl)-cyclohexyl]-1,3,8-triaza-spiro[4.5]dec-1-ene-8-sulfonyl}-ethyl)-phenyl]-1-methyl-urea (Compound 696) (Reaction 149-1)
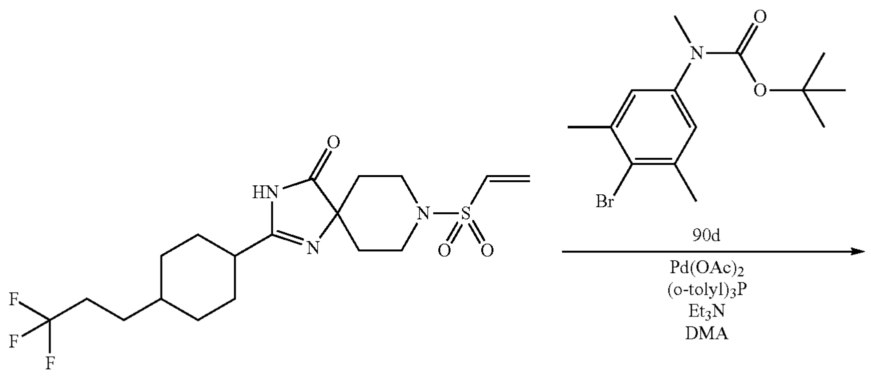
101j
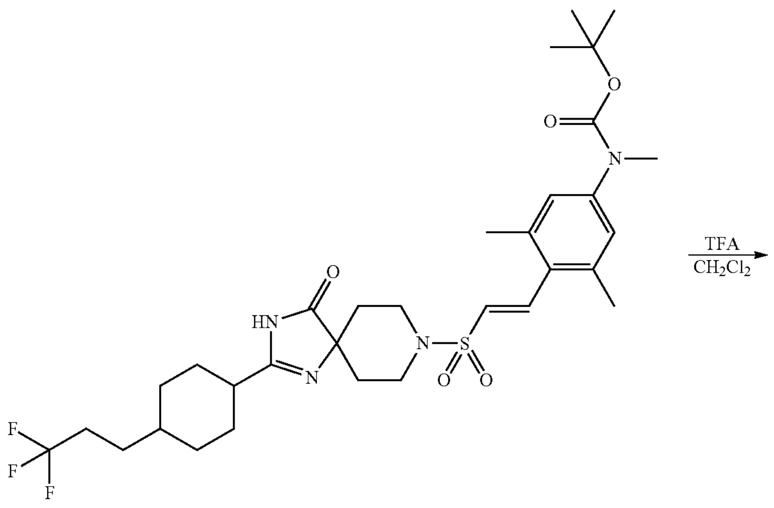
149a
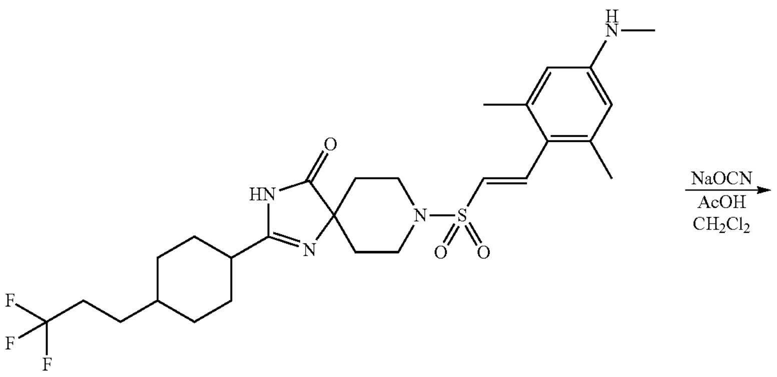
149b -continued

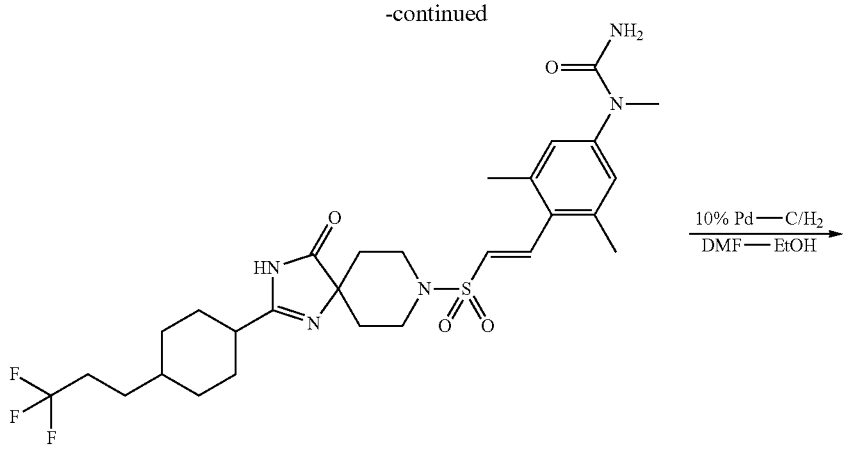

149c

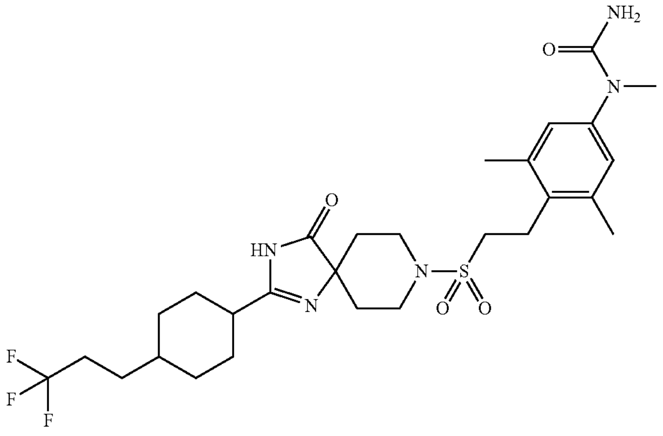

Compound 696

1-[3,5-Dimethyl-4-(2-{4-oxo-2-[4-(3,3,3-trifluoro-propyl)-cyclohexyl]-1,3,8-triaza-spiro[4.5]dec-1-ene-8-sulfonyl}-ethyl)-phenyl]-1-methyl-urea was synthesized by operations similar to those in Reaction 25-2, Reaction 7-2, Reaction 89-2 and Reaction 42-2 using appropriate reagents and starting material.

MS (ESI) m/z=600 (M+H)+.

Example 150

8-{(E)-2-[4-((R)-2,3-Dihydroxy-propoxy)-2,6-dimethyl-phenyl]-ethenesulfonyl}-2-[4-(3,3,3-trifluoro-propyl)-cyclohexyl]-1,3,8-triaza-spiro[4.5]dec-1-en-4-one (Compound 697)

(Reaction 150-1)

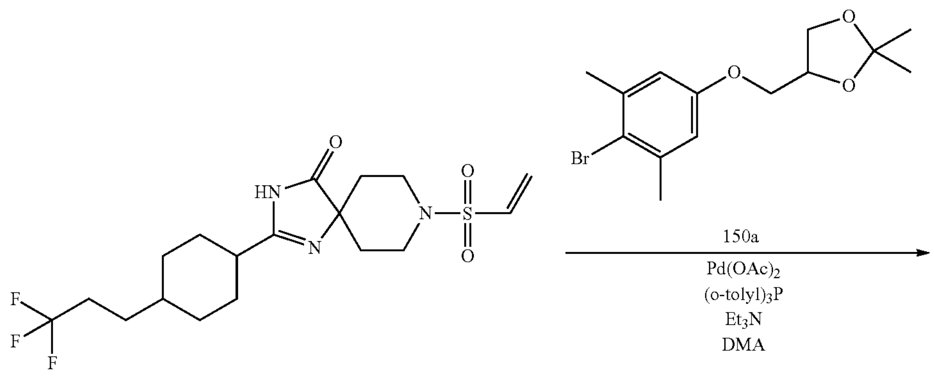

101j

-continued

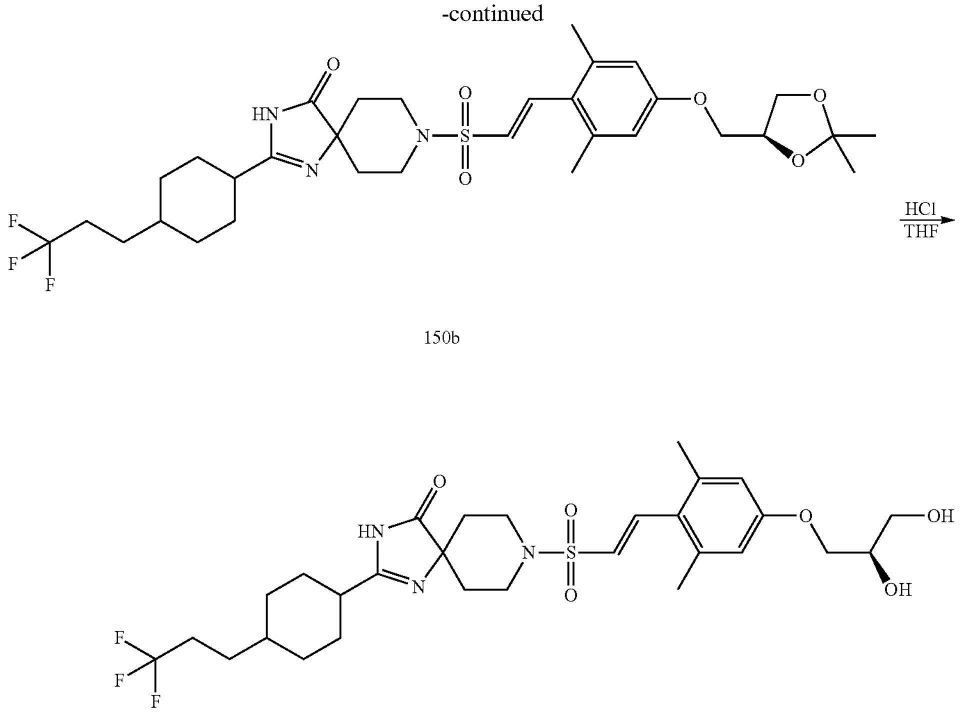

150b

Compound 697

8-{(E)-2-[4-((R)-2,3-Dihydroxy-propoxy)-2,6-dimethyl-phenyl]-ethenesulfonyl}-2-[4-(3,3,3-trifluoro-propyl)-cyclohexyl]-1,3,8-triaza-spiro[4.5]dec-1-en-4-one was synthesized by operations similar to those in Reaction 25-2 and Reaction 25-4 using appropriate reagents and starting material.

MS (ESI) m/z=616 (M+H)+.

The example compound shown below was synthesized by operations similar to those in Example 150 using appropriate reagents and starting material.

Compound 698

TABLE 102

| Target Compound | Structure | LCMS condition | Retention time (min) | MS (m/z) |
| --- | --- | --- | --- | --- |
| 698 | 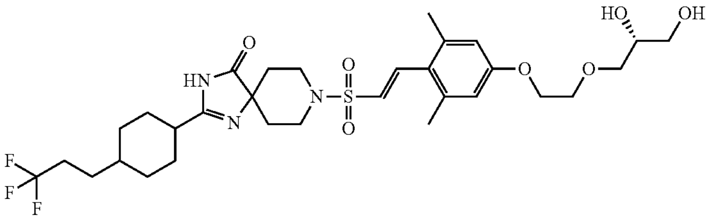 [SMILES: Cc1cc(OCCOC[C@H](O)CO)cc(C)c1/C=C/S(=O)(=O)N1CCC2(CC1)N=C(C1CCC(CCC(F)(F)F)CC1)NC2=O] | LCMS-D-1 | 2.56 | 660 (M + H)+ |

Example 151
N-[3,5-Dimethyl-4-((E)-2-{4-oxo-2-[4-(3,3,3-trifluoro-propyl)-cyclohexyl]-1,3,8-triaza-spiro[4.5]dec-1-ene-8-sulfonyl}-vinyl)-phenyl]-N-[2-(2-hydroxy-ethoxy)-ethyl]-acetamide (Compound 699)
(Reaction 151-1)
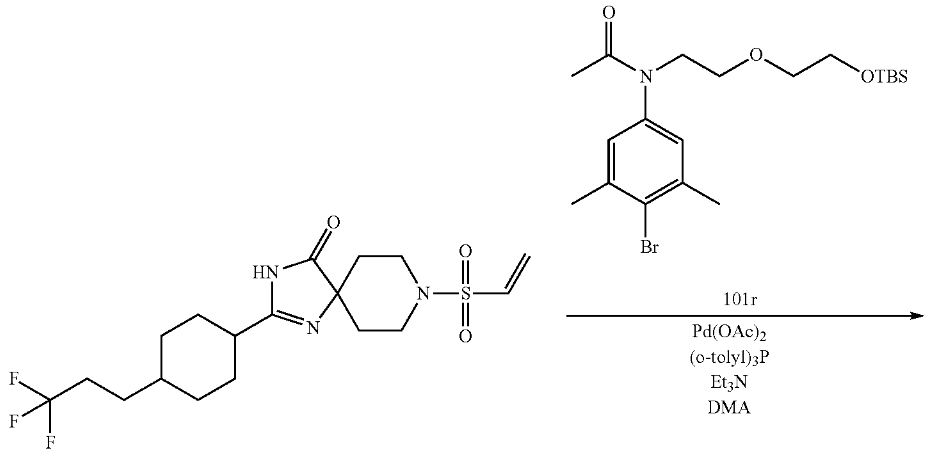
101j
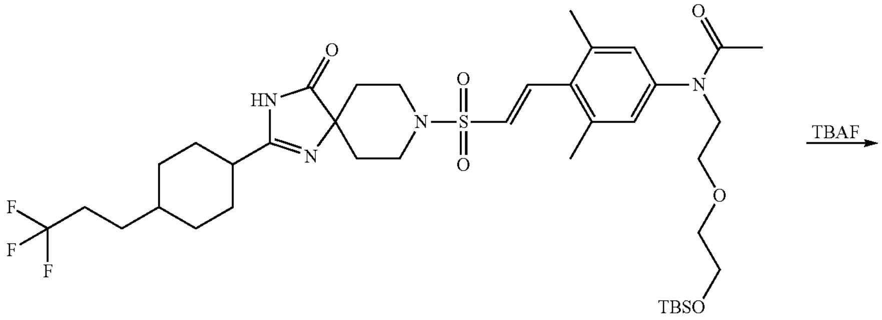
151a
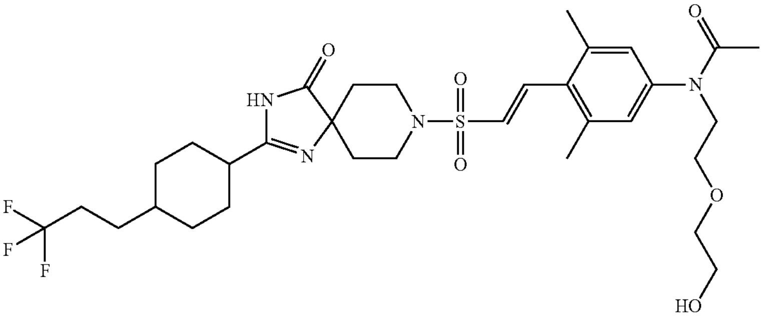
Compound 699

N-[3,5-Dimethyl-4-((E)-2-{4-oxo-2-[4-(3,3,3-trifluoro-propyl)-cyclohexyl]-1,3,8-triaza-spiro[4.5]dec-1-ene-8-sulfonyl}-vinyl)-phenyl]-N-[2-(2-hydroxy-ethoxy)-ethyl]-acetamide was synthesized by operations similar to those in Reaction 25-2 and Reaction 39-2 using appropriate reagents and starting material.

MS (ESI) m/z=671 (M+H)+.

The aryl bromide reagent used in the synthesis of Compound 699 (N-(4-bromo-3,5-dimethyl-phenyl)-N-{2-[2-(tert-butyl-dimethyl-silanyloxy)-ethoxy]-ethyl}-acetamide) was synthesized as follows.

(Reaction 151-2)

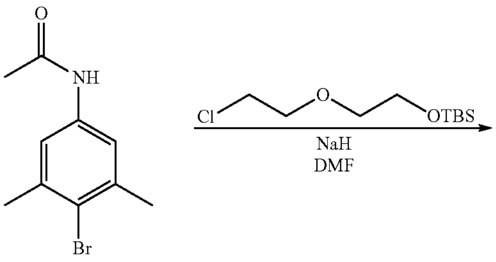

26a

-continued

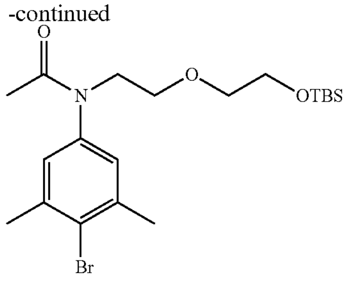

101r

N-(4-Bromo-3,5-dimethyl-phenyl)-N-{2-[2-(tert-butyl-dimethyl-silanyloxy)-ethoxy]-ethyl}-acetamide was synthesized by operations similar to those in Reaction 25-3 using appropriate reagents and starting material.

$^1$H-NMR ($CDCl_3$) δ 6.95 (s, 2H), 3.81 (dd, 2H, J=6.10, 5.72 Hz), 3.70 (dd, 2H, J=4.95, 5.34 Hz), 3.58 (dd, 2H, J=5.72, 6.10 Hz), 3.46 (dd, 2H, J=5.72, 4.95 Hz), 2.41 (s, 6H), 1.83 (s, 3H), 0.86 (s, 9H).

Example 152

N-[2-(2-Hydroxy-ethoxy)-ethyl]-N-{3-methyl-4-[(E)-2-(2-nonyl-4-oxo-1,3,8-triaza-spiro[4.5]dec-1-ene-8-sulfonyl)-vinyl]-phenyl}-acetamide (Compound 700)

(Reaction 152-1)

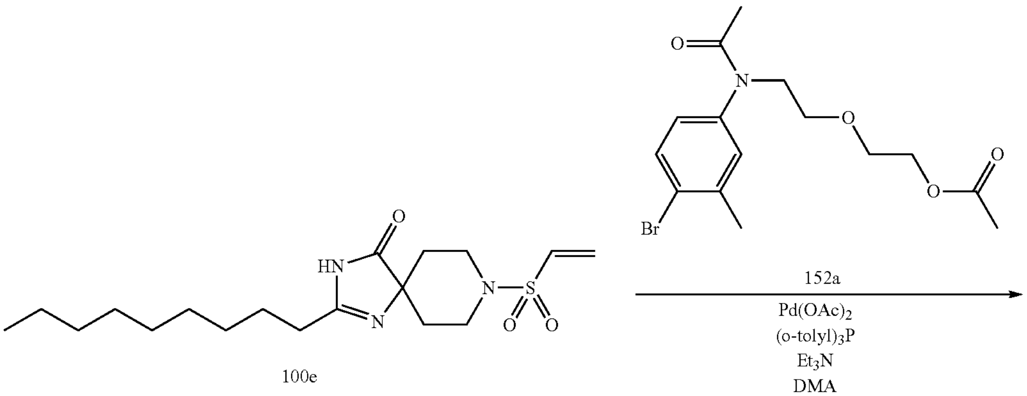

100e

152a

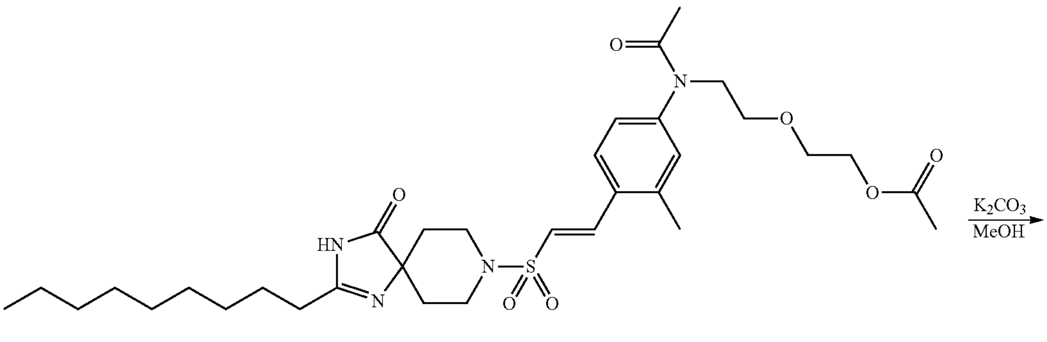

152b

-continued

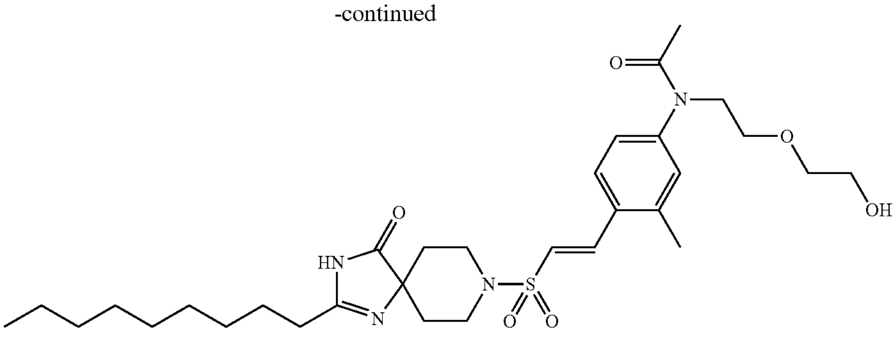

Compound 700

N-[2-(2-Hydroxy-ethoxy)-ethyl]-N-{3-methyl-4-[(E)-2-(2-nonyl-4-oxo-1,3,8-triaza-spiro[4.5]dec-1-ene-8-sulfonyl)-vinyl]-phenyl}-acetamide was synthesized by operations similar to those in Reaction 25-2 and Reaction 12-5 using appropriate reagents and starting material.

MS (ESI) m/z=605 (M+H)+.

The example compound shown below was synthesized by operations similar to those in Example 152 using appropriate reagents and starting material.

Compound 701

TABLE 103

| Target Compound | Structure | LCMS condition | Retention time (min) | MS (m/z) |
|---|---|---|---|---|
| 701 | 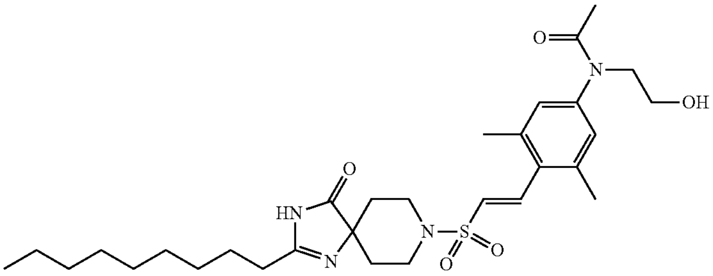 [SMILES: CCCCCCCCCC1=NC2(CCN(S(=O)(=O)/C=C/c3c(C)cc(N(CCO)C(C)=O)cc3C)CC2)C(=O)N1] | LCMS-A-1 | 2.44 | 575 (M + H)+ |

The aryl bromide reagent used in the synthesis of Compound 701 (acetic acid 2-[acetyl-(4-bromo-3,5-dimethyl-phenyl)-amino]-ethyl ester) was synthesized as follows.

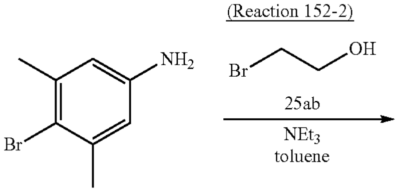

96g

-continued

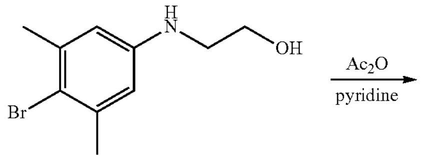

152c

-continued

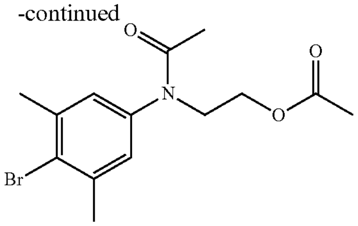

152d

Acetic acid 2-[acetyl-(4-bromo-3,5-dimethyl-phenyl)-amino]-ethyl ester was synthesized by operations similar to those in Reaction 25-12 and Reaction 12-2 using appropriate reagents and starting material.

MS (ESI) m/z=328, 330 (M+H)+.

Example 153

2-Cyclohexyl-8-{(E)-2-[1-((S)-2,3-dihydroxy-propyl)-1H-indol-5-yl]-ethenesulfonyl}-1,3,8-triaza-spiro[4.5]dec-1-en-4-one (Compound 702)

(Reaction 153-1)

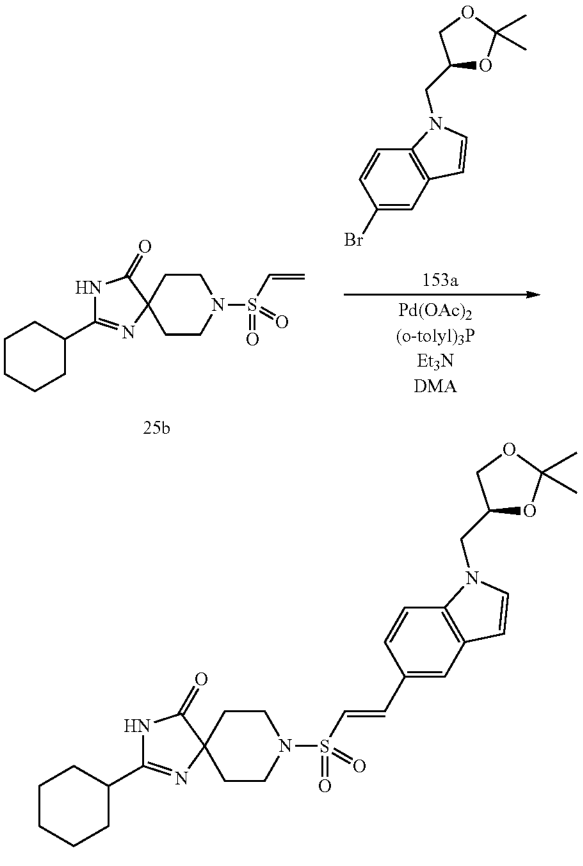

25b

153b

2-Cyclohexyl-8-{(E)-2-[1-((S)-2,2-dimethyl-[1,3]dioxolan-4-ylmethyl)-1H-indol-5-yl]-ethenesulfonyl}-1,3,8-triaza-spiro[4.5]dec-1-en-4-one was synthesized by operations similar to those in Reaction 25-2 using appropriate reagents and starting material.

MS (ESI) m/z=555 (M+H)+.

(Reaction 153-2)

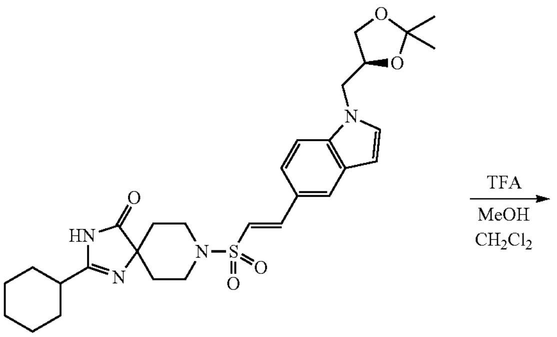

153b

-continued

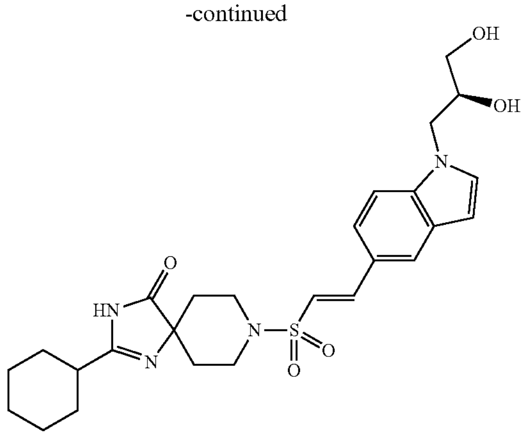

Compound 702

2-Cyclohexyl-8-{(E)-2-[1-((S)-2,2-dimethyl-[1,3]dioxolan-4-ylmethyl)-1H-indol-5-yl]-ethenesulfonyl}-1,3,8-triaza-spiro[4.5]dec-1-en-4-one (41.9 mg, 0.0755 mmol) was dissolved in a methylene chloride-methanol mixed solution (1:1, 1.5 ml). Trifluoroacetic acid (0.35 ml) was added and the mixture was stirred for two days. A saturated aqueous sodium bicarbonate solution and water were added to the reaction solution, followed by extraction with ethyl acetate. The organic layer was washed with water and saturated brine, dried over anhydrous sodium sulfate and concentrated under reduced pressure. The resulting residue was purified by P-TLC (ethyl acetate-methanol) to give 2-cyclohexyl-8-{(E)-2-[1-((S)-2,3-dihydroxy-propyl)-1H-indol-5-yl]-ethenesulfonyl}-1,3,8-triaza-spiro[4.5]dec-1-en-4-one (33.4 mg, 86%).

MS (ESI) m/z=515 (M+H)+.

The aryl bromide reagent used in the synthesis of Compound 702 (5-bromo-1-((S)-2,2-dimethyl-[1,3]dioxolan-4-ylmethyl)-1H-indole) was synthesized as follows.

(Reaction 153-3)

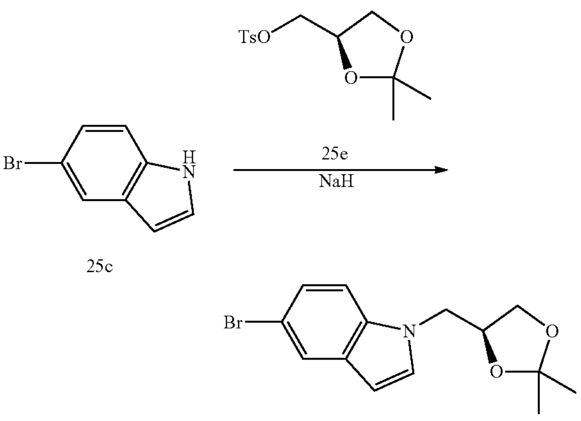

25c

153a

5-Bromo-1-((S)-2,2-dimethyl-[1,3]dioxolan-4-ylmethyl)-1H-indole was synthesized by operations similar to those in Reaction 25-3 using appropriate reagents and starting material.

MS (ESI) m/z=310 (M+H)+.

Example 154

8-((E)-2-{1-[2-((S)-2,3-Dihydroxy-propoxy)-ethyl]-1H-indol-4-yl}-ethenesulfonyl)-2-[4-(3,3,3-trifluoro-propyl)-cyclohexyl]-1,3,8-triaza-spiro[4.5]dec-1-en-4-one (Compound 704)

(Reaction 154-1)

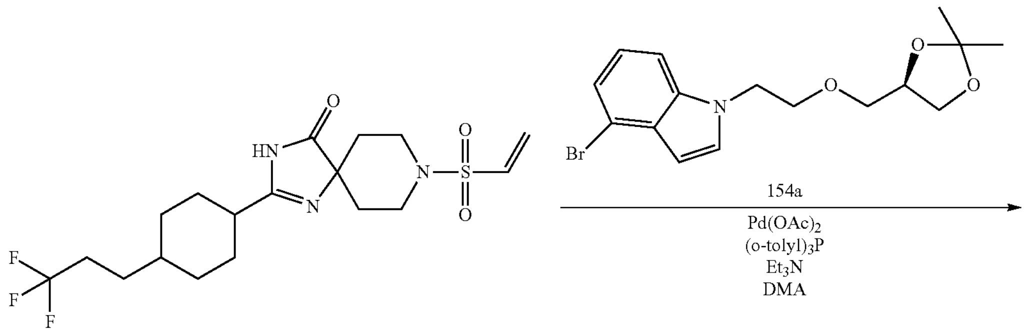

101j

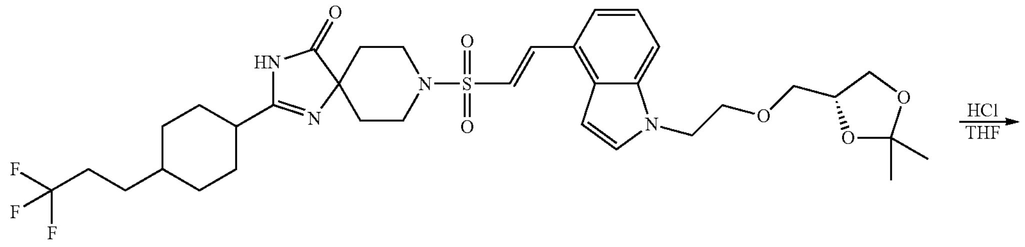

154b

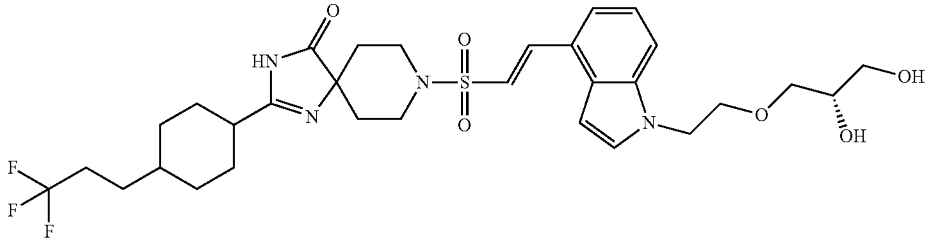

Compound 704

8-((E)-2-{1-[2-((S)-2,3-Dihydroxy-propoxy)-ethyl]-1H-indol-4-yl}-ethenesulfonyl)-2-[4-(3,3,3-trifluoro-propyl)-cyclohexyl]-1,3,8-triaza-spiro[4.5]dec-1-en-4-one was synthesized by operations similar to those in Reaction 26-1 and Reaction 25-4 using appropriate reagents and starting material.

MS (ESI) m/z=655 (M+H)+.

The example compounds shown below were synthesized by operations similar to those in Example 154 using appropriate reagents and starting materials.

Compounds 705 to Compound 706

TABLE 104

| Target Compound | Structure | LCMS condition | Retention time (min) | MS (m/z) |
|---|---|---|---|---|
| 705 | 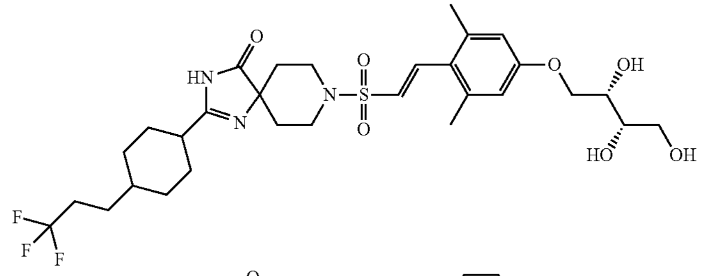 | LCMS-D-1 | 2.14 | 646 (M + H)+ |
| 706 | 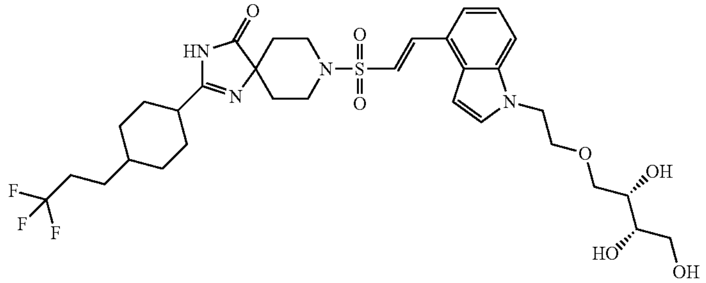 [SMILES: O=C1NC(C2CCC(CCC(F)(F)F)CC2)=NC12CCN(S(=O)(=O)/C=C/c1cccc3c1ccn3CCOC[C@H](O)[C@@H](O)CO)CC2] | LCMS-D-1 | 2.15 | 685 (M + H)+ |

The aryl bromide reagent used in the synthesis of Compound 704 (4-bromo-1-[2-((R)-2,2-dimethyl-[1,3]dioxolan-4-ylmethoxy)-ethyl]-1H-indole) was synthesized as follows.

(Reaction 154-2)

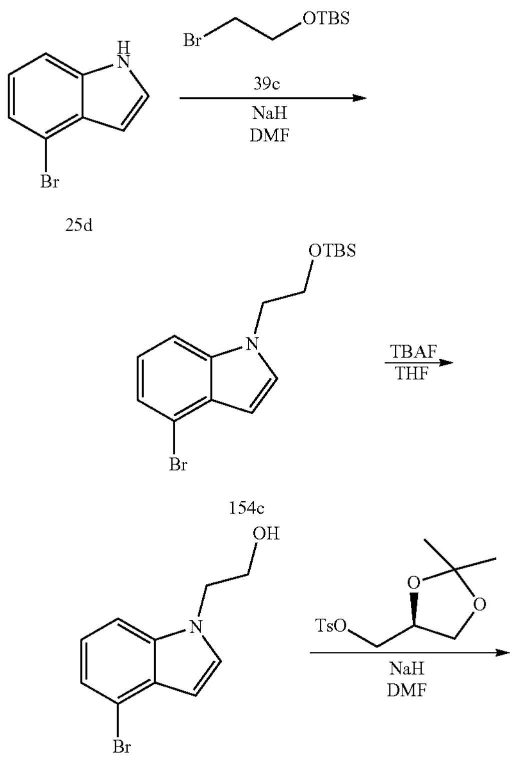

25d

154c

154d

-continued

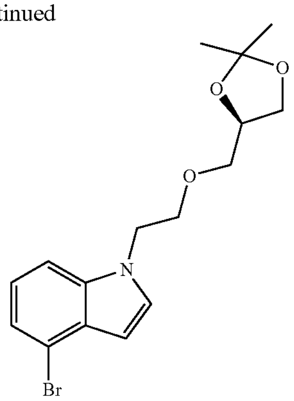

154a

4-Bromo-1-[2-((R)-2,2-dimethyl-[1,3]dioxolan-4-ylmethoxy)-ethyl]-1H-indole was synthesized by operations similar to those in Reaction 25-3, Reaction 39-2 and Reaction 20-2 using appropriate reagents and starting material.

MS (ESI) m/z=354,356 (M+H)+.

The aryl bromide reagent used in the synthesis of Compound 705 ([(4S,5S)-5-(4-bromo-3,5-dimethyl-phenoxymethyl)-2,2-dimethyl-[1,3]dioxolan-4-ylmethoxy]-tert-butyl-dimethyl-silane) was synthesized as follows.

(Reaction 154-3)

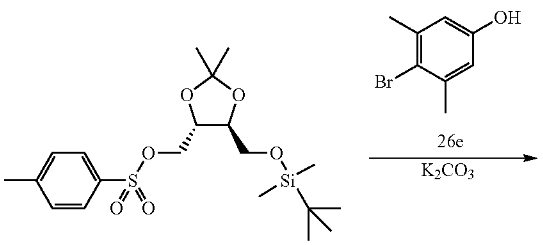

154e

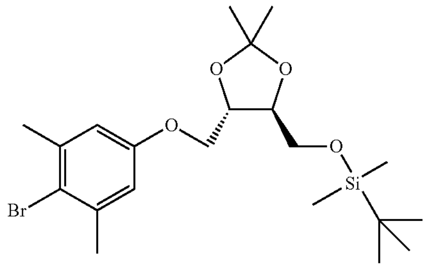

154f

[(4S,5S)-5-(4-Bromo-3,5-dimethyl-phenoxymethyl)-2,2-dimethyl-[1,3]dioxolan-4-ylmethoxy]-tert-butyl-dimethyl-silane was synthesized by operations similar to those in Reaction 26-4 using appropriate reagents and starting material.

$^1$H-NMR ($CDCl_3$) δ 6.67 (s, 2H), 4.27 (m, 1H), 4.13-3.73 (m, 5H), 2.36 (s, 6H), 1.44 (s, 3H), 1.43 (s, 3H), 0.88 (s, 9H), 0.06 (s, 6H).

The aryl bromide reagent used in the synthesis of Compound 706 ({(4S,5S)-5-[2-(4-bromo-indol-1-yl)-ethoxymethyl]-2,2-dimethyl-[1,3]dioxolan-4-yl}-methanol) was synthesized as follows.

(Reaction 154-4)

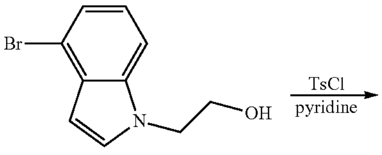

154d

-continued

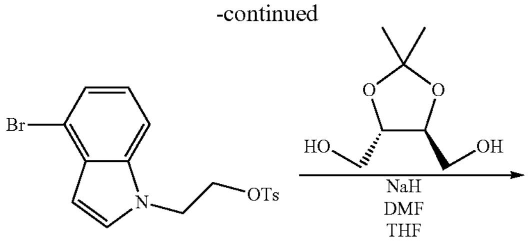

154g

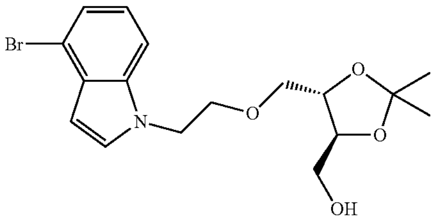

154h

{(4S,5S)-5-[2-(4-Bromo-indol-1-yl)-ethoxymethyl]-2,2-dimethyl-[1,3]dioxolan-4-yl}-methanol was synthesized by operations similar to those in Reaction 6-1 and Reaction 20-2 using appropriate reagents and starting material.

$^1$H-NMR ($CDCl_3$) δ 7.28 (m, 2H), 7.20 (d, 1H, J=3.3 Hz), 7.06 (t, 1H, J=7.8 Hz), 6.55 (d, 1H, J=3.0 Hz), 4.30 (t, 2H, J=5.4 Hz), 3.94 (m, 1H), 3.84-3.41 (m, 7H), 1.91 (br s, 1H), 1.39 (s, 3H), 1.36 (s, 3H).

Example 155

N—((S)-2,3-Dihydroxy-propyl)-N-(3,5-dimethyl-4-{(E)-2-[4-oxo-2-(9,9,9-trifluoro-nonyl)-1,3,8-triaza-spiro[4.5]dec-1-ene-8-sulfonyl]-vinyl}-phenyl)-acetamide (Compound 707)

(Reaction 155-1)

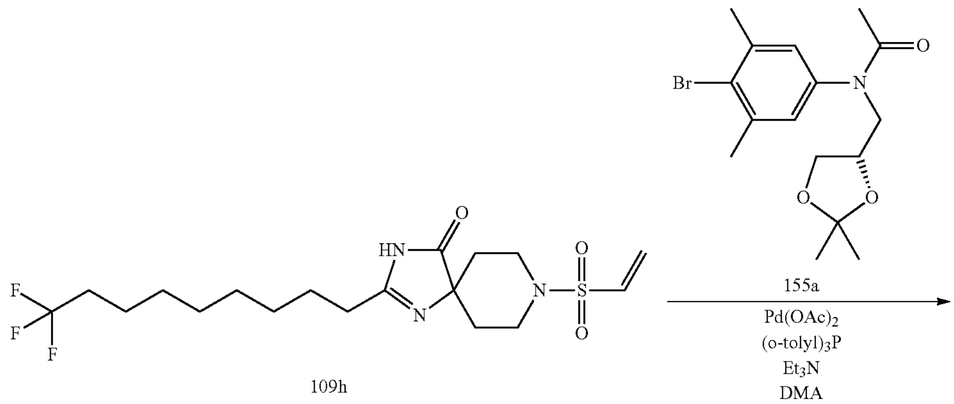

109h

-continued

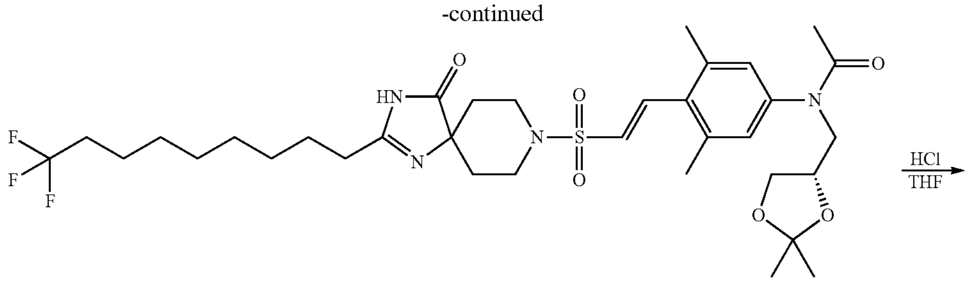

155b

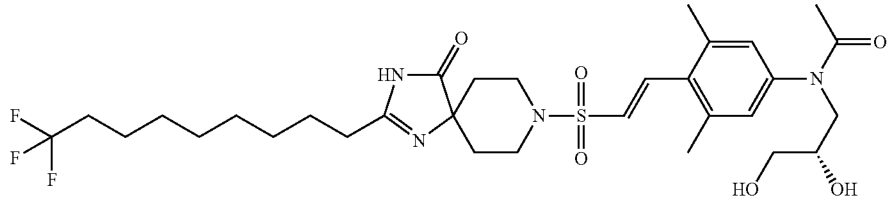

Compound 707

N—((S)-2,3-Dihydroxy-propyl)-N-(3,5-dimethyl-4-{(E)-2-[4-oxo-2-(9,9,9-trifluoro-nonyl)-1,3,8-triaza-spiro[4.5]dec-1-ene-8-sulfonyl]-vinyl}-phenyl)-acetamide was synthesized by operations similar to those in Reaction 26-1 and reaction 25-4 using appropriate reagents and starting material.

MS (ESI) m/z=659 (M+H)+.

Example 156

{4-[(E)-2-(2-Cyclohexyl-4-oxo-1,3,8-triaza-spiro[4.5]dec-1-ene-8-sulfonyl)-vinyl]-3-methyl-benzyl}-(2-hydroxy-ethyl)-carbamic acid tert-butyl ester (Compound 708)

(Reaction 156-1)

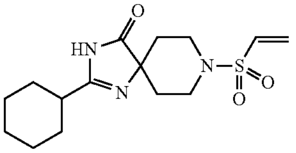

25b

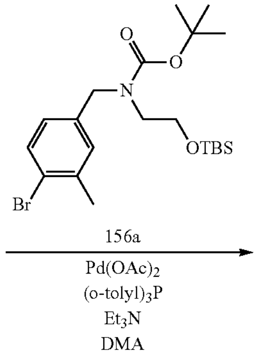

-continued

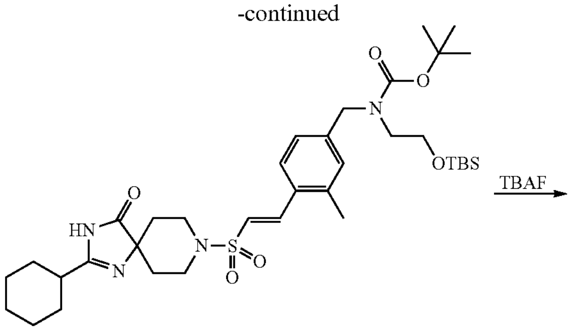

156b

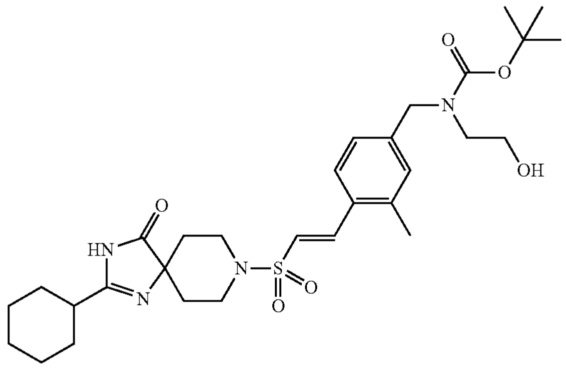

Compound 708

{4-[(E)-2-(2-Cyclohexyl-4-oxo-1,3,8-triaza-spiro[4.5]dec-1-ene-8-sulfonyl)-vinyl]-3-methyl-benzyl}-(2-hydroxy-ethyl)-carbamic acid tert-butyl ester was synthesized by operations similar to those in Reaction 26-1 and Reaction 39-2 using appropriate reagents and starting material.

MS (ESI) m/z=589 (M+H)+.

The example compounds shown below were synthesized by operations similar to those in Example 156 using appropriate reagents and starting materials.

Compounds 709 to Compound 710

TABLE 105

| Target Compound | Structure | LCMS condition | Retention time (min) | MS (m/z) |
|---|---|---|---|---|
| 709 | 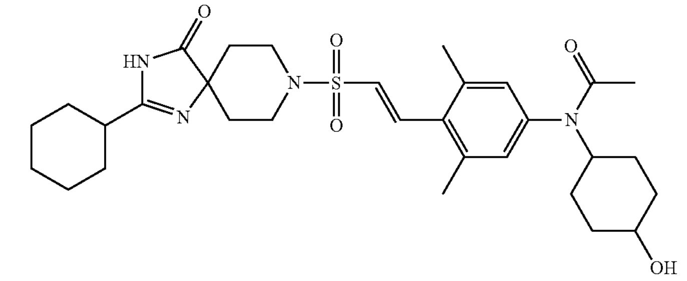 [SMILES: CC(=O)N(c1cc(C)c(/C=C/S(=O)(=O)N2CCC3(CC2)N=C(C2CCCCC2)NC3=O)c(C)c1)C1CCC(O)CC1] | LCMS-D-1 | 2.34 | 585 (M + H)+ |
| 710 | 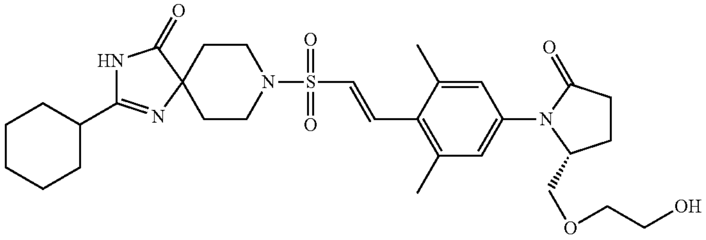 [SMILES: Cc1cc(N2C(=O)CC[C@@H]2COCCO)cc(C)c1/C=C/S(=O)(=O)N1CCC2(CC1)N=C(C1CCCCC1)NC2=O] | LCMS-D-1 | 2.53 | 587 (M + H)+ |

The aryl bromide reagent used in the synthesis of Compound 708 ((4-bromo-3-methyl-benzyl)-[2-(tert-butyl-dimethyl-silanyloxy)-ethyl]-carbamic acid tert-butyl ester) was synthesized as follows.

(Reaction 156-2)

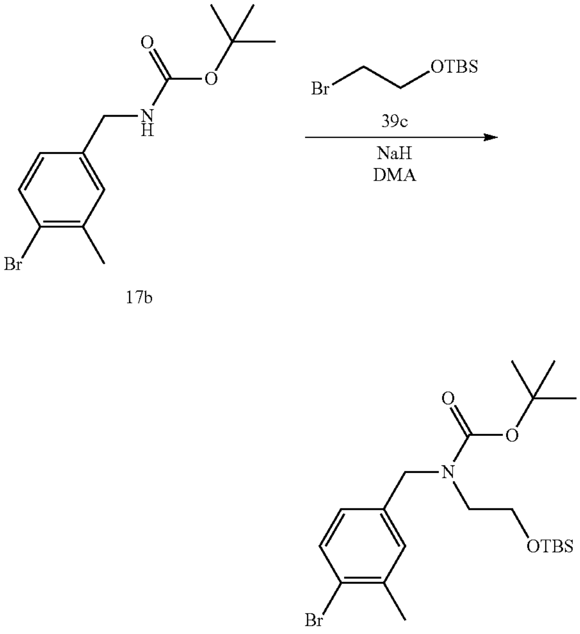

17b

156a (4-Bromo-3-methyl-benzyl)-[2-(tert-butyl-dimethyl-silanyloxy)-ethyl]-carbamic acid tert-butyl ester was synthesized by operations similar to those in Reaction 25-3 using appropriate reagents and starting material.

MS (ESI) m/z=472, 474 (M+H)+.

The aryl bromide reagent used in the synthesis of Compound 709 (N-(4-bromo-3,5-dimethyl-phenyl)-N-[4-(tert-butyl-dimethyl-silanyloxy)-cyclohexyl]-acetamide) was synthesized as follows.

(Reaction 156-3)

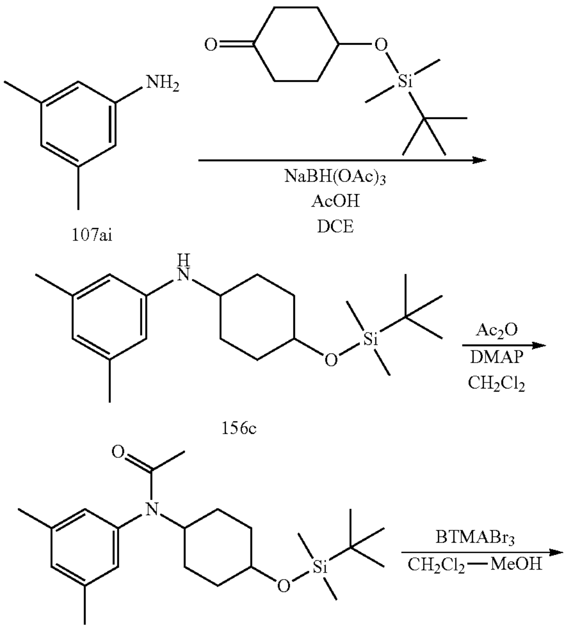

107ai

156c

156d

-continued

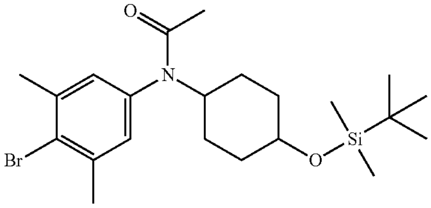

156e

N-(4-Bromo-3,5-dimethyl-phenyl)-N-[4-(tert-butyl-dimethyl-silanyloxy)-cyclohexyl]-acetamide was synthesized by operations similar to those in Reaction 41-1, Reaction 19-2 (using DMAP as a base) and Reaction 26-2 using appropriate reagents and starting material.

MS (ESI) m/z=454, 456 (M+H)+.

The aryl bromide reagent used in the synthesis of Compound 710 ((R)-1-(4-bromo-3,5-dimethyl-phenyl)-5-[2-(tert-butyl-dimethyl-silanyloxy)-ethoxymethyl]-pyrrolidin-2-one) was synthesized as follows.

(Reaction 156-4)

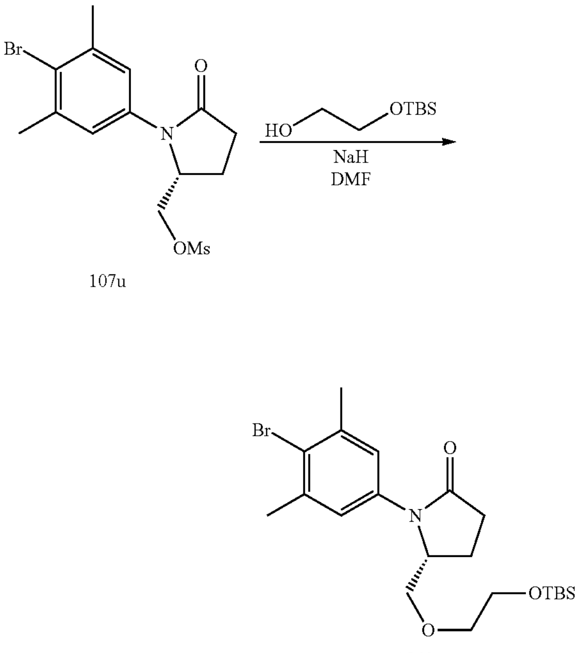

107u

156f (R)-1-(4-Bromo-3,5-dimethyl-phenyl)-5-[2-(tert-butyl-dimethyl-silanyloxy)-ethoxymethyl]-pyrrolidin-2-one was synthesized by operations similar to those in Reaction 20-2 using appropriate reagents and starting material.

$^1$H-NMR ($CDCl_3$) δ 7.07 (s, 2H), 4.19 (m, 1H), 3.64 (t, 2H, J=4.96 Hz), 3.44 (m, 2H), 3.40 (t, 2H, J=4.96 Hz), 2.52 (m, 2H), 2.36 (s, 6H), 2.17 (m, 2H), 0.87 (s, 9H), 0.04 (s, 6H).

Example 157

N-(2-Hydroxy-ethyl)-N-(3-methyl-4-{(E)-2-[4-oxo-2-(3-trifluoromethoxy-phenyl)-1,3,8-triaza-spiro[4.5]dec-1-ene-8-sulfonyl]-vinyl}-phenyl)-isobutylamide (Compound 711)

(Reaction 157-1)

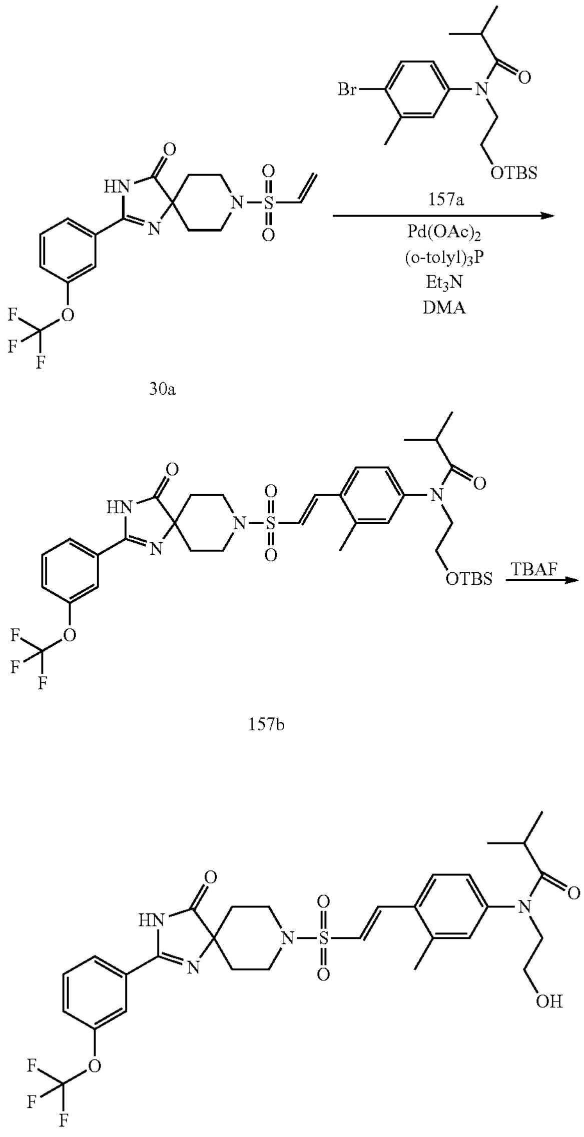

30a

157b

Compound 711

N-(2-Hydroxy-ethyl)-N-(3-methyl-4-{(E)-2-[4-oxo-2-(3-trifluoromethoxy-phenyl)-1,3,8-triaza-spiro[4.5]dec-1-ene-8-sulfonyl]-vinyl}-phenyl)-isobutylamide was synthesized by operations similar to those in Reaction 26-1 and Reaction 39-2 using appropriate reagents and starting material.

MS (ESI) m/z=623 (M+H)+.

The example compounds shown below were synthesized by operations similar to those in Example 157 using appropriate reagents and starting materials.

Compounds 712 to Compound 715

TABLE 106

| Target Compound | Structure | LCMS condition | Retention time (min) | MS (m/z) |
|---|---|---|---|---|
| 712 | 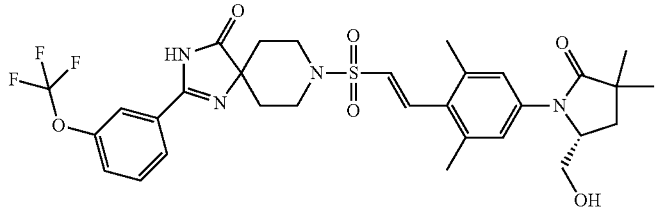 [SMILES: Cc1cc(N2C(=O)C(C)(C)C[C@@H]2CO)cc(C)c1/C=C/S(=O)(=O)N1CCC2(CC1)N=C(c1cccc(OC(F)(F)F)c1)NC2=O] | LCMS-D-1 | 2.90 | 649 (M + H)+ |
| 713 | 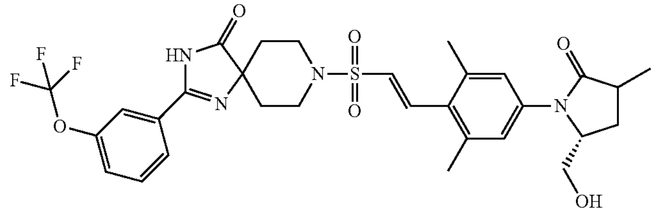 [SMILES: Cc1cc(N2C(=O)C(C)C[C@@H]2CO)cc(C)c1/C=C/S(=O)(=O)N1CCC2(CC1)N=C(c1cccc(OC(F)(F)F)c1)NC2=O] | LCMS-D-1 | 2.90 | 635 (M + H)+ |
| 714 | 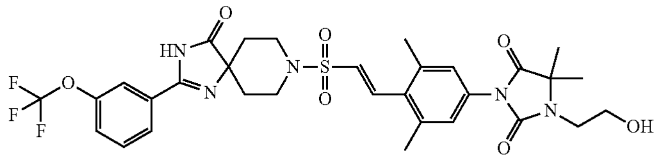 [SMILES: Cc1cc(N2C(=O)N(CCO)C(C)(C)C2=O)cc(C)c1/C=C/S(=O)(=O)N1CCC2(CC1)N=C(c1cccc(OC(F)(F)F)c1)NC2=O] | LCMS-D-1 | 3.20 | 678 (M + H)+ |
| 715 | 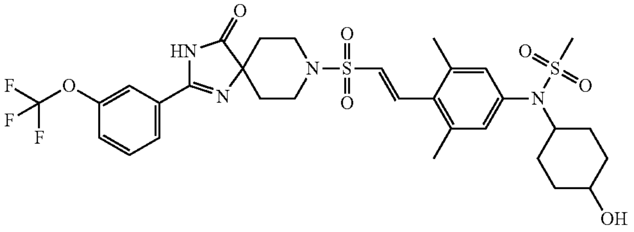 [SMILES: Cc1cc(N(C2CCC(O)CC2)S(C)(=O)=O)cc(C)c1/C=C/S(=O)(=O)N1CCC2(CC1)N=C(c1cccc(OC(F)(F)F)c1)NC2=O] | LCMS-D-1 | 3.30 | 699 (M + H)+ |

The aryl bromide reagent used in the synthesis of Compound 711 (N-(4-bromo-3-methyl-phenyl)-N-[2-(tert-butyl-dimethyl-silanyloxy)-ethyl]-isobutylamide) was synthesized as follows.

(Reaction 157-2)

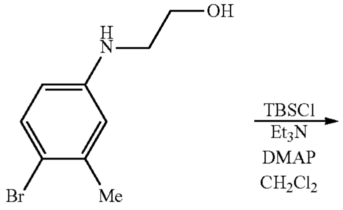

12c

-continued

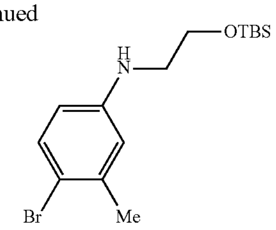

157c

Triethylamine (0.39 ml, 2.80 mmol), dimethylaminopyridine (13 mg, 0.11 mmol) and tert-butyl-dimethyl-chloro-silane (319 mg, 2.11 mmol) were added to a solution of 2-(4-bromo-3-methyl-phenylamino)-ethanol (430 mg, 1.87 mmol) in dichloromethane (3.8 ml) at room temperature, and the mixture was stirred at room temperature for 24 hours. The reaction mixture was diluted with dichloromethane, and the organic layer was washed with water, dried over $MgSO_4$ and concentrated under reduced pressure. The resulting residue was purified by silica gel column chromatography (hexane-ethyl acetate) to give (4-bromo-3-methyl-phenyl)-[2-(tert-butyl-dimethyl-silanyloxy)-ethyl]-amine (629 mg, 98%).

$^1H$-NMR (300 MHz, $CDCl_3$) δ 0.08 (6H, s), 0.91 (9H, s), 2.32 (3H, s), 3.18 (2H, dd, J=5.7 and 5.1 Hz), 3.80 (2H, t, J=5.1 Hz), 4.01 (1H, dull t, J=5.7 Hz), 6.34 (1H, dd, J=8.7, 2.5 Hz), 6.51 (1H, d, J=2.5 Hz), 7.27 (1H, d, J=8.7 Hz).

(Reaction 157-3)

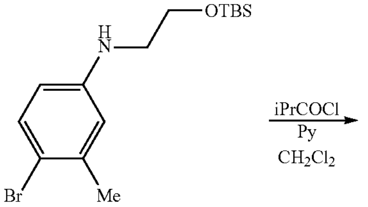

157c

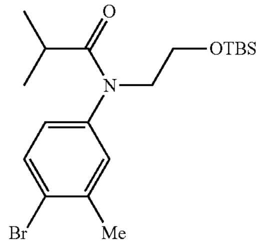

157a

N-(4-Bromo-3-methyl-phenyl)-N-[2-(tert-butyl-dimethyl-silanyloxy)-ethyl]-isobutylamide was synthesized by operations similar to those in Reaction 105-2 using appropriate reagents and starting material.

$^1$H-NMR (300 MHz, $CDCl_3$) δ 0.04 (6H, s), 0.87 (9H, s), 1.02 (6H, d, J=6.6 Hz), 2.41 (3H, s), 2.47 (1H, sept, J=6.6 Hz), 3.74 (4H, s), 6.92 (1H, dd, J=8.4, 2.3 Hz), 7.13 (1H, d, J=2.3 Hz), 7.53 (1H, d, J=8.4 Hz).

The aryl bromide reagents used in the synthesis of Compound 712 and Compound 713 ((R)-1-(4-bromo-3,5-dimethylphenyl)-5-(tert-butyl-dimethyl-silanyloxymethyl)-3,3-dimethylpyrrolidin-2-one and (R)-1-(4-bromo-3,5-dimethyl-phenyl)-5-(tert-butyl-dimethyl-silanyloxymethyl)-3-methyl-pyrrolidin-2-one) were synthesized as follows.

(Reaction 157-4)

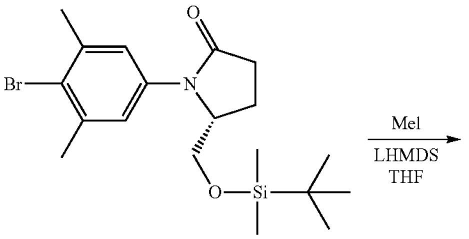

39g

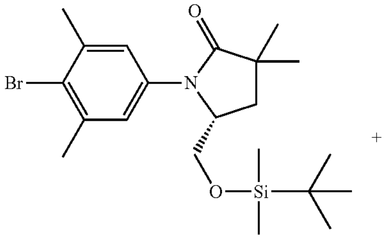

157d

-continued

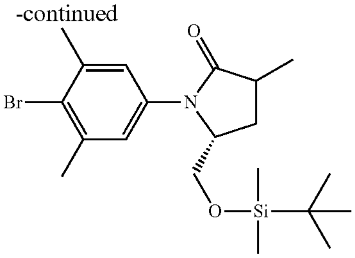

157e

1 M LHMDS (0.61 ml, 0.61 mmol) was added dropwise to a solution of (R)-1-(4-bromo-3,5-dimethylphenyl)-5-(((tert-butyldimethylsilyl)oxy)-methyl)pyrrolidin-2-one (119 mg, 0.29 mmol) in THF (2.4 ml) at −78° C. in a nitrogen atmosphere, and the mixture was stirred at −78° C. for 15 minutes. A solution of iodomethane (38 μL, 0.62 mmol) in THF (0.5 ml) was added at −78° C., and the mixture was stirred at −78° C. for 15 minutes, warmed to room temperature and further stirred for three hours. A saturated aqueous ammonium chloride solution was added to the reaction mixture, and the mixture was diluted with dichloromethane. The organic layer was washed with saturated brine, and then dried over $MgSO_4$ and concentrated under reduced pressure. The resulting residue was purified by silica gel column chromatography (hexane-ethyl acetate) to give a mixture of (R)-1-(4-bromo-3,5-dimethylphenyl)-5-(tert-butyl-dimethyl-silanyloxymethyl)-3,3-dimethylpyrrolidin-2-one (minor) and (R)-1-(4-bromo-3,5-dimethyl-phenyl)-5-(tert-butyl-dimethyl-silanyloxymethyl)-3-methyl-pyrrolidin-2-one (major) (629 mg, 98%). This was used in Heck reaction without complete separation and purification.

The aryl bromide reagent used in the synthesis of Compound 714 ((3-(4-bromo-3,5-dimethyl-phenyl)-1-[2-(tert-butyl-dimethyl-silanyloxy)-ethyl]-5,5-dimethyl-imidazolidine-2,4-dione) was synthesized as follows.

(Reaction 157-5)

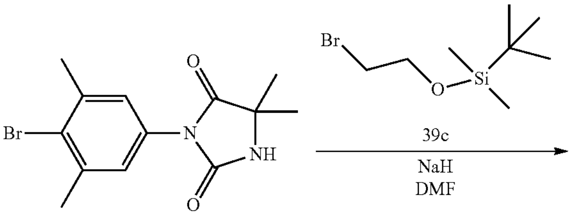

96j

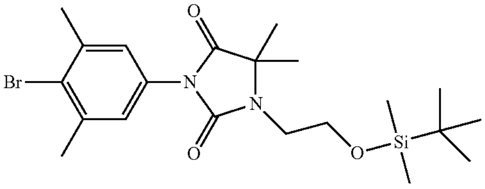

157f (3-(4-Bromo-3,5-dimethyl-phenyl)-1-[2-(tert-butyl-dimethyl-silanyloxy)-ethyl]-5,5-dimethyl-imidazolidine-2,4-dione was synthesized by operations similar to those in Reaction 25-3 using appropriate reagents and starting material.

$^1$H-NMR ($CDCl_3$) δ 7.11 (s, 2H), 3.85 (t, 2H, d=6.0 Hz), 3.43 (t, 2H, d=6.0 Hz), 2.42 (s, 6H), 1.49 (s, 6H), 0.90 (s, 9H), 0.07 (s, 6H).

The aryl bromide reagent used in the synthesis of Compound 715 (N-(4-bromo-3,5-dimethyl-phenyl)-N-[4-(tert-butyl-dimethyl-silanyloxy)-cyclohexyl]-methanesulfonamide) was synthesized as follows.

(Reaction 157-6)

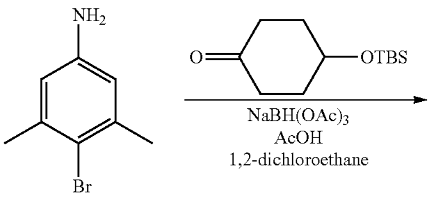

96g

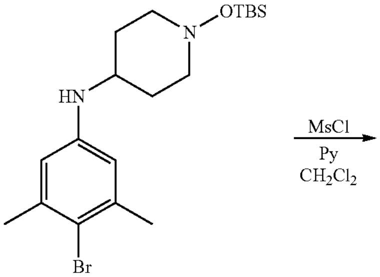

157g

-continued

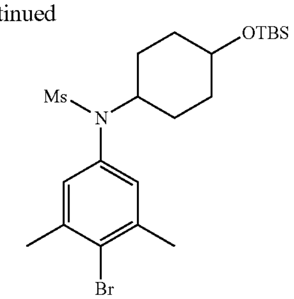

157h

N-(4-Bromo-3,5-dimethyl-phenyl)-N-[4-(tert-butyl-dimethyl-silanyloxy)-cyclohexyl]-methanesulfonamide was synthesized by operations similar to those in Reaction 41-1 and Reaction 6-1 using appropriate reagents and starting material.

MS (ESI) m/z=490, 492 (M+H)+.

Example 158

N-(4-{(E)-2-[2-(4-Butyl-cyclohexyl)-4-oxo-1,3,8-triaza-spiro[4.5]dec-1-ene-8-sulfonyl]-vinyl}-3,5-dimethyl-phenyl)-N-[2-(2-hydroxy-ethoxy)-ethyl]-acetamide (Compound 716)

(Reaction 158-1)

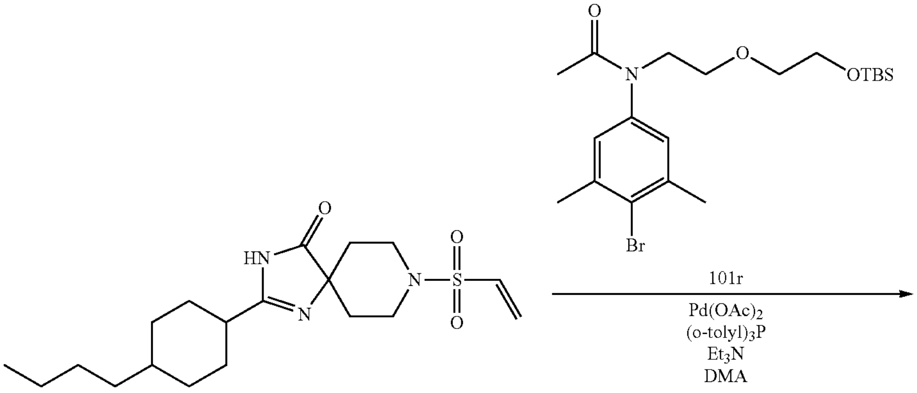

102e

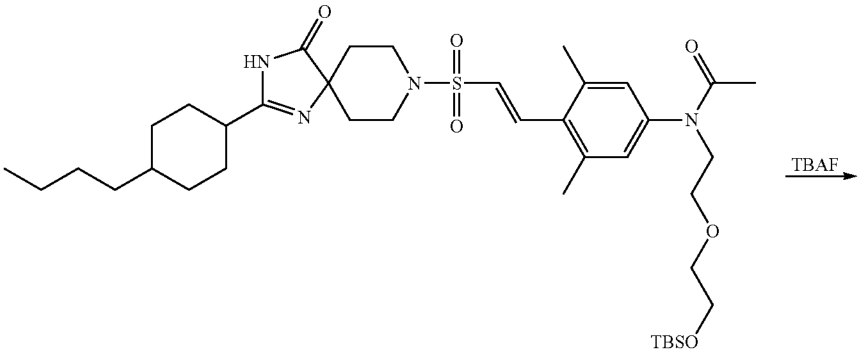

158a

-continued

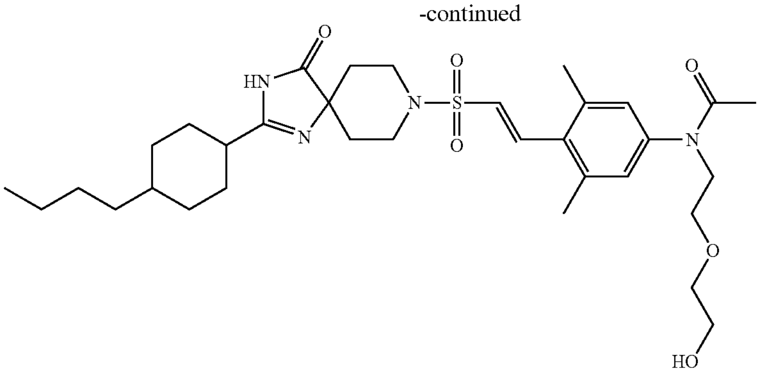

Compound 716

N-(4-{(E)-2-[2-(4-Butyl-cyclohexyl)-4-oxo-1,3,8-triaza-spiro[4.5]dec-1-ene-8-sulfonyl]-vinyl}-3,5-dimethyl-phenyl)-N-[2-(2-hydroxy-ethoxy)-ethyl]-acetamide was synthesized by operations similar to those in Reaction 26-1 and Reaction 39-2 using appropriate reagents and starting material.

MS (ESI) m/z=631 (M+H)+.

The aryl bromide reagent used in the synthesis of Compound 716 (N-(4-bromo-3,5-dimethyl-phenyl)-N-{2-[2-(tert-butyl-dimethyl-silanyloxy)-ethoxy]-ethyl}-acetamide) was synthesized as follows.

(Reaction 158-2)

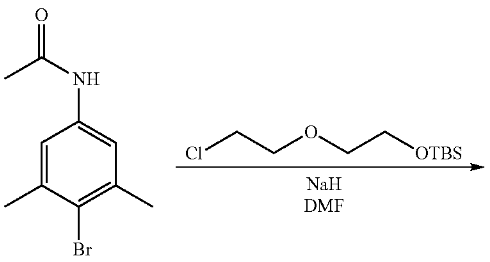

26a

-continued

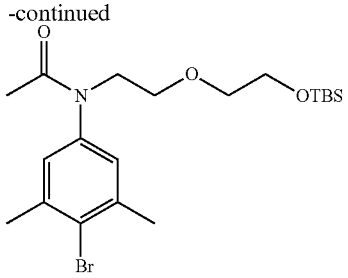

101r

N-(4-Bromo-3,5-dimethyl-phenyl)-N-{2-[2-(tert-butyl-dimethyl-silanyloxy)-ethoxy]-ethyl}-acetamide was synthesized by operations similar to those in Reaction 25-3 using appropriate reagents and starting material.

$^1$H-NMR ($CDCl_3$) δ 6.95 (s, 2H), 3.81 (dd, 2H, J=6.10, 5.72 Hz), 3.70 (dd, 2H, J=4.95, 5.34 Hz), 3.58 (dd, 2H, J=5.72, 6.10 Hz), 3.46 (dd, 2H, J=5.72, 4.95 Hz), 2.41 (s, 6H), 1.83 (s, 3H), 0.86 (s, 9H).

Example 159

N-(2-Fluoro-5-methyl-4-{(E)-2-[4-oxo-2-(3-trifluoromethoxy-phenyl)-1,3,8-triaza-spiro[4.5]dec-1-ene-8-sulfonyl]-vinyl}-phenyl)-N-(2-hydroxy-ethyl)-acetamide (Compound 717)

(Reaction 159-1)

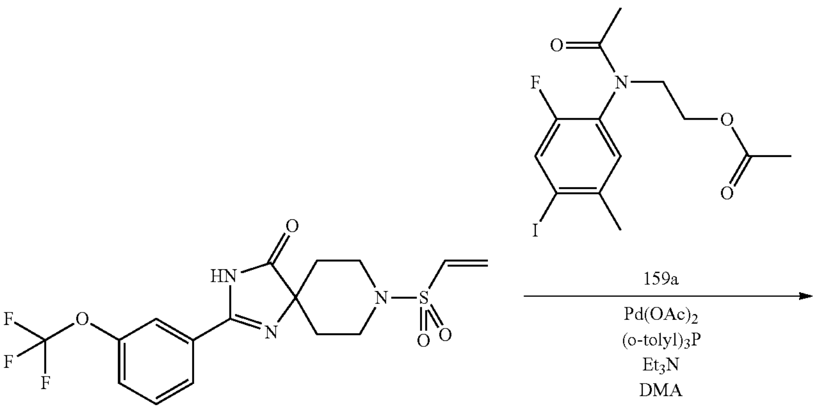

30a

-continued

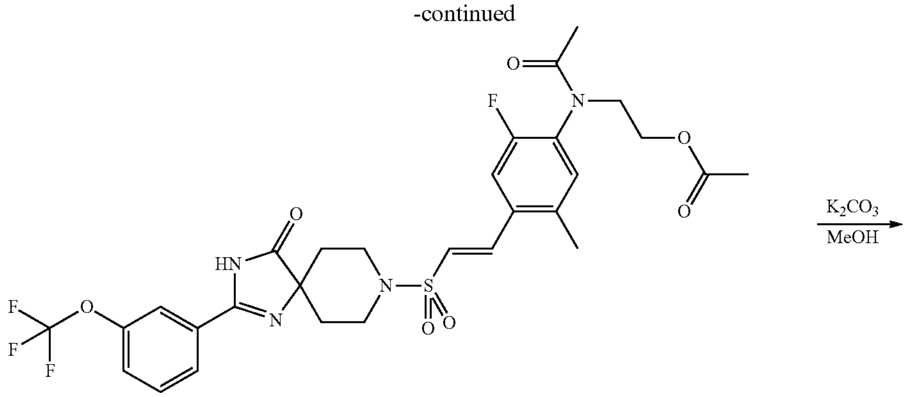

159b

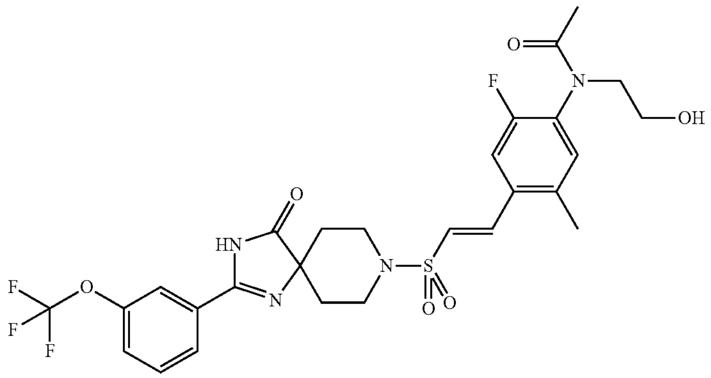

Compound 717

N-(2-Fluoro-5-methyl-4-{(E)-2-[4-oxo-2-(3-trifluoromethoxy-phenyl)-1,3,8-triaza-spiro[4.5]dec-1-ene-8-sulfonyl]-vinyl}-phenyl)-N-(2-hydroxy-ethyl)-acetamide was synthesized by operations similar to those in Reaction 26-1 and Reaction 12-5 using appropriate reagents and starting material.

MS (ESI) m/z=613 (M+H)+.

The aryl iodide reagent used in the synthesis of Compound 717 (acetic acid 2-[acetyl-(2-fluoro-4-iodo-5-methyl-phenyl)-amino]-ethyl ester) was synthesized as follows.

(Reaction 159-2)

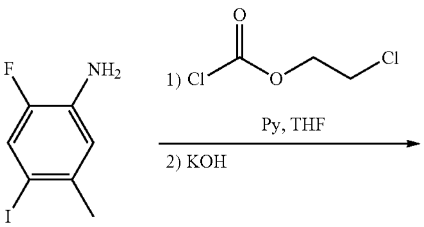

159c

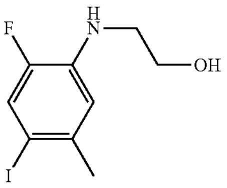

159d

Pyridine (0.87 mL, 10.78 mmol) was added to a solution of 2-fluoro-4-iodo-5-methyl-phenylamine (1082.9 mg, 4.314 mmol) in THF (10.8 mL). 2-Chloroethyl chloroformate (0.47 mL, 4.53 mmol) was then added dropwise and the mixture was stirred overnight.

Potassium hydroxide (968.2 mg, 17.25 mmol) and ethanol (10.8 mL) were subsequently added, and the mixture was heated under reflux overnight. The reaction mixture was then quenched by adding a saturated aqueous ammonium chloride solution and extracted with ethyl acetate. The organic layer was sequentially washed with water and saturated brine, and then dried over anhydrous $Na_2SO_4$ and concentrated under reduced pressure. The resulting residue was purified by silica gel column chromatography to give 2-(2-fluoro-4-iodo-5-methyl-phenylamino)-ethanol as a pale brown solid (1217.0 mg, 96%).

MS (ESI) m/z=296 (M+H)+.

(Reaction 159-3)

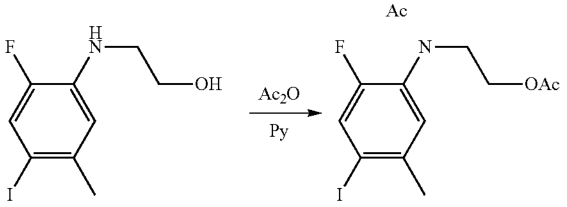

159d 159a

Acetic acid 2-[acetyl-(2-fluoro-4-iodo-5-methyl-phenyl)-amino]-ethyl ester was synthesized by operations similar to those in Reaction 12-2 using appropriate reagents and starting material.
MS (ESI) m/z=402 (M+Na)+.
Example 160
N-(4-{(E)-2-[2-(4-Fluoro-3-trifluoromethyl-phenyl)-4-oxo-1,3,8-triaza-spiro[4.5]dec-1-ene-8-sulfonyl]-vinyl}-3,5-dimethyl-phenyl)-N-(2-hydroxy-ethyl)-acetamide (Compound 718)
(Reaction 160-1)
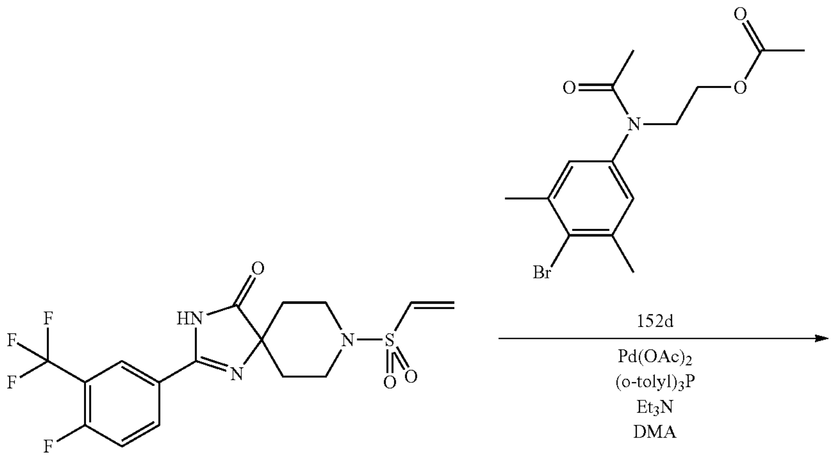
30b
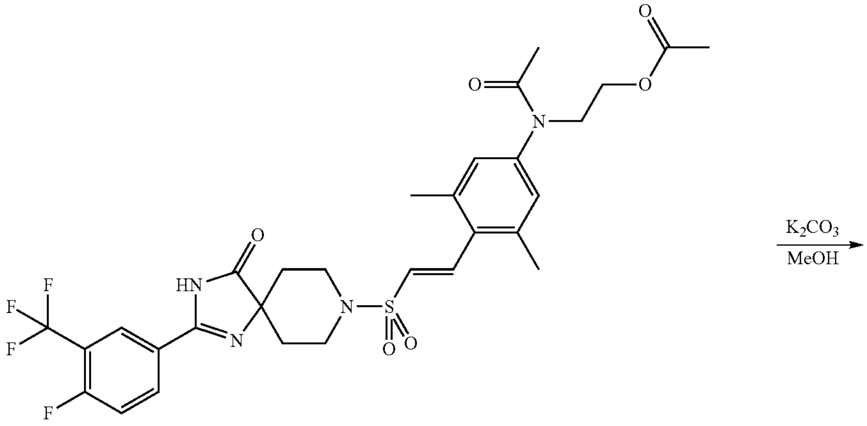
160a
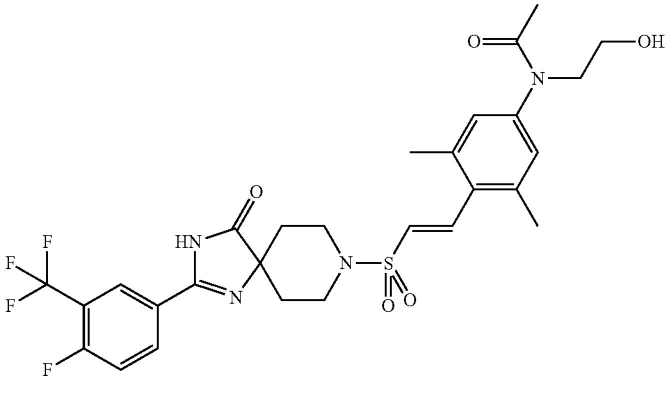
Compound 718

N-(4-{(E)-2-[2-(4-Fluoro-3-trifluoromethyl-phenyl)-4-oxo-1,3,8-triaza-spiro[4.5]dec-1-ene-8-sulfonyl]-vinyl}-3,5-dimethyl-phenyl)-N-(2-hydroxy-ethyl)-acetamide was synthesized by operations similar to those in Reaction 26-1 and Reaction 12-5 using appropriate reagents and starting material.

MS (ESI) m/z=611 (M+H)+.

Example 161

N-(2-Hydroxy-ethyl)-N-(3-methyl-4-{(E)-2-[4-oxo-2-(3-trifluoromethoxy-phenyl)-1,3,8-triaza-spiro[4.5]dec-1-ene-8-sulfonyl]-vinyl}-phenyl)-methanesulfonamide (Compound 719)

(Reaction 161-1)

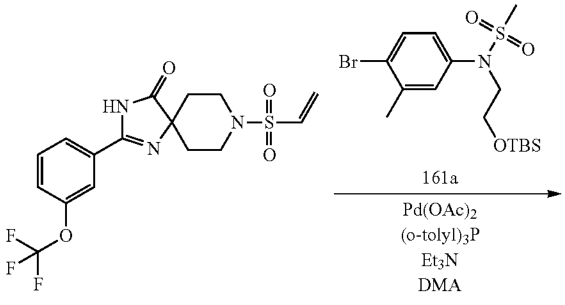

30a

-continued

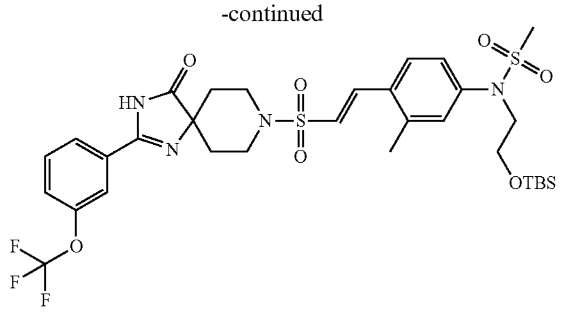

161b

N-[2-(tert-Butyl-dimethyl-silanyloxy)-ethyl]-N-(3-methyl-4-{(E)-2-[4-oxo-2-(3-trifluoromethoxy-phenyl)-1,3,8-triaza-spiro[4.5]dec-1-ene-8-sulfonyl]-vinyl}-phenyl)-methanesulfonamide was synthesized by operations similar to those in Reaction 26-1 using appropriate reagents and starting material.

$^1$H-NMR (300 MHz, $CDCl_3$) δ 0.04 (6H, s), 0.87 (9H, s), 1.70 (2H, m), 2.21 (2H, m), 2.44 (3H, s), 3.02 (3H, s), 3.32 (2H, m), 3.71 (2H, t, J=5.7 Hz), 3.81 (4H, m), 6.67 (1H, J=15.3 Hz), 7.27 (2H, m), 7.42 (1H, m), 7.56 (2H, m), 7.71 (1H, d, J=15.3 Hz), 7.80 (1H, d, J=8.0 Hz), 7.84 (1H, s), 10.24 (1H, brs).

(Reaction 161-2)

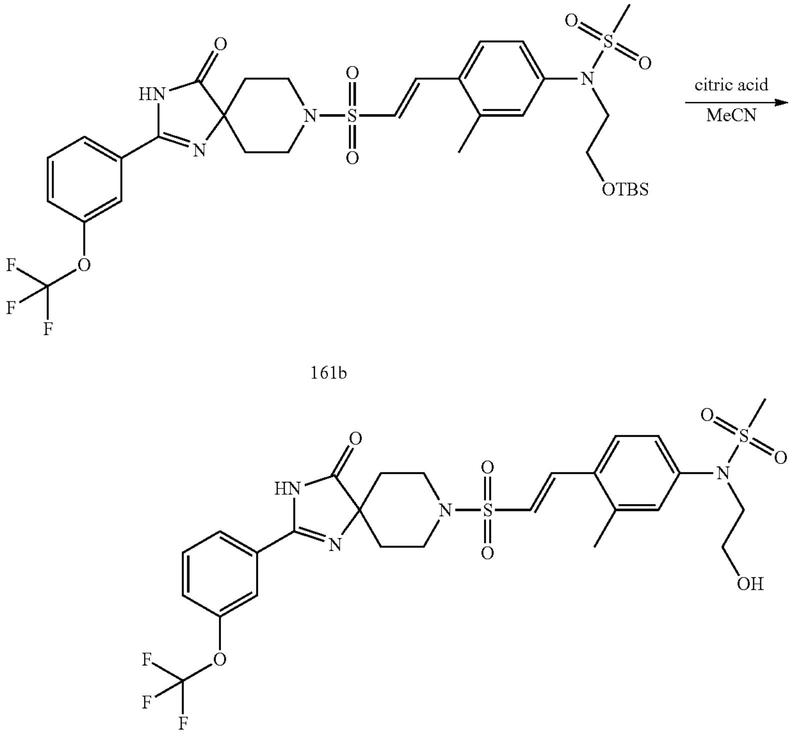

161b

Compound 719

A 10% aqueous citric acid solution (0.14 ml, 0.067 mmol) was added to a solution of N-[2-(tert-butyl-dimethyl-silanyloxy)-ethyl]-N-(3-methyl-4-{(E)-2-[4-oxo-2-(3-trifluoromethoxy-phenyl)-1,3,8-triaza-spiro[4.5]dec-1-ene-8-sulfonyl]-vinyl}-phenyl)-methanesulfonamide (14.3 mg, 0.0192 mmol) in acetonitrile (0.2 ml), and the mixture was stirred at 60° C. for 2.5 hours. The reaction mixture was diluted with ethyl acetate, and the organic layer was washed with an aqueous sodium bicarbonate solution, dried over $MgSO_4$ and concentrated under reduced pressure. The resulting residue was purified by silica gel column chromatography (ethyl acetate) to give N-(2-hydroxy-ethyl)-N-(3-methyl-4-{(E)-2-[4-oxo-2-(3-trifluoromethoxy-phenyl)-1,3,8-triaza-spiro[4.5]dec-1-ene-8-sulfonyl]-vinyl}-phenyl)-methanesulfonamide (12.5 mg, 100%).

MS (ESI) m/z=631 (M+H)+.

The aryl bromide reagent used in the synthesis of Compound 719 (N-(4-bromo-3-methyl-phenyl)-N-[2-(tert-butyl-dimethyl-silanyloxy)-ethyl]-methanesulfonamide) was synthesized as follows.

(Reaction 161-3)

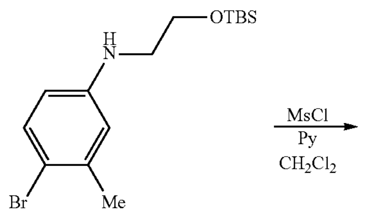

157c

-continued

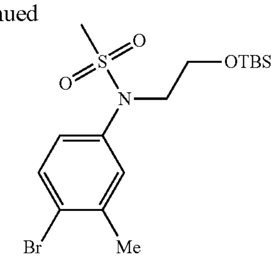

161a

N-(4-Bromo-3-methyl-phenyl)-N-[2-(tert-butyl-dimethyl-silanyloxy)-ethyl]-methanesulfonamide was synthesized by operations similar to those in Reaction 6-1 using appropriate reagents and starting material.

$^1H$-NMR (300 MHz, $CDCl_3$) δ 0.04 (6H, s), 0.87 (9H, s), 2.40 (3H, s), 2.96 (3H, s), 3.68 (2H, m), 3.75 (2H, m), 7.05 (1H, ddd, J=8.5, 2.5, 0.6 Hz), 7.25 (1H, d, J=2.5 Hz), 7.54 (1H, d, J=8.5 Hz).

Example 162

N-(2-Hydroxy-ethyl)-N-{3-methyl-4-[2-(2-nonyl-4-oxo-1,3,8-triaza-spiro[4.5]dec-1-ene-8-sulfonyl)-ethyl]-phenyl}-methanesulfonamide (Compound 720)

(Reaction 162-1)

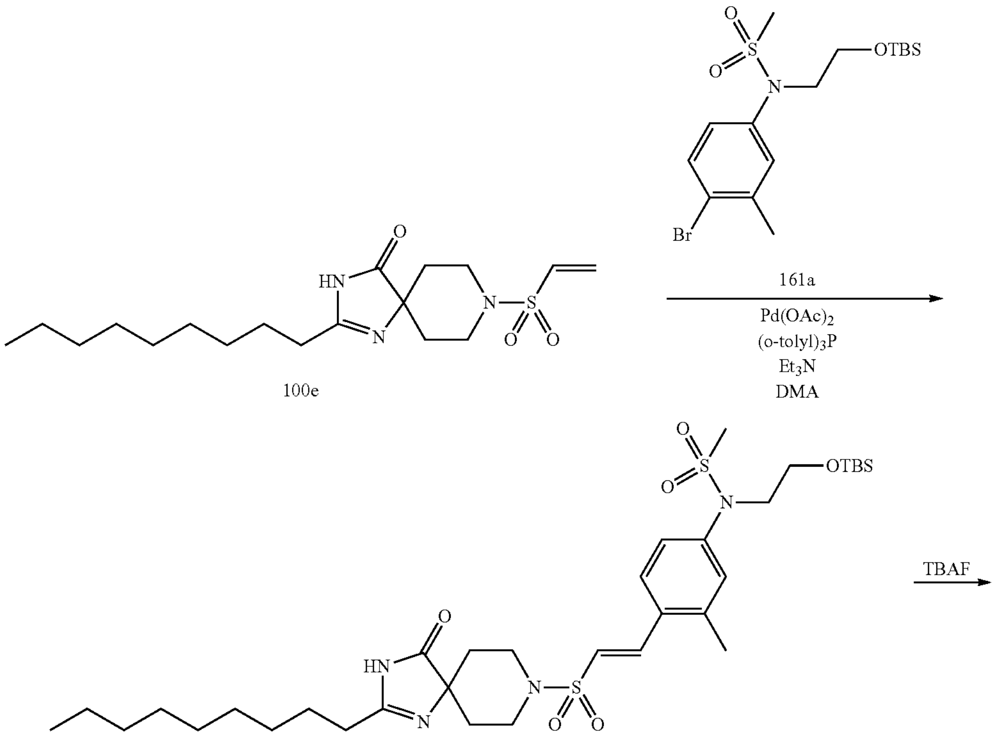

100e

162a

-continued

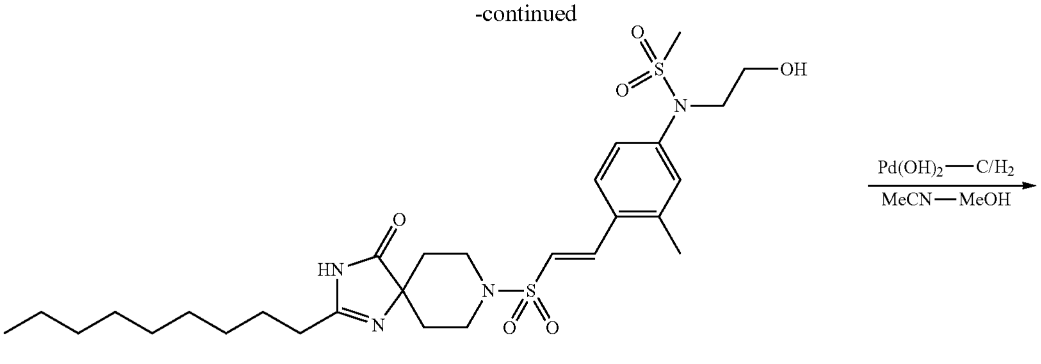

162b

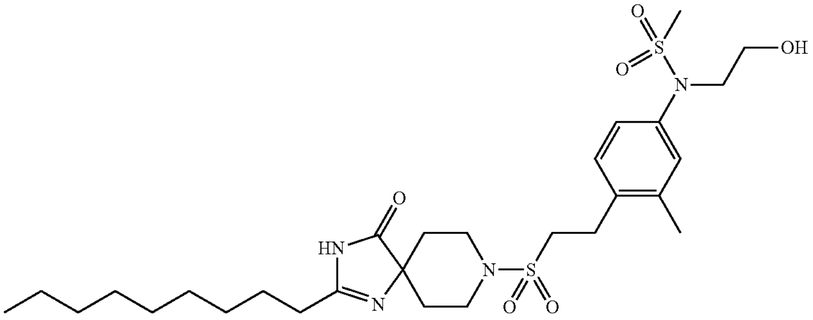

Compound 720

N-(2-Hydroxy-ethyl)-N-{3-methyl-4-[2-(2-nonyl-4-oxo-1,3,8-triaza-spiro[4.5]dec-1-ene-8-sulfonyl)-ethyl]-phenyl}-methanesulfonamide was synthesized by operations similar to those in Reaction 26-1, Reaction 39-2 and Reaction 122-2 using appropriate reagents and starting material.

MS (ESI) m/z=599 (M+H)+.

Example 163

N-(4-{2-[2-(4-Fluoro-3-trifluoromethyl-phenyl)-4-oxo-1,3,8-triaza-spiro[4.5]dec-1-ene-8-sulfonyl]-ethyl}-3-methyl-phenyl)-N-(2-hydroxy-ethyl)-acetamide (Compound 721)

(Reaction 163-1)

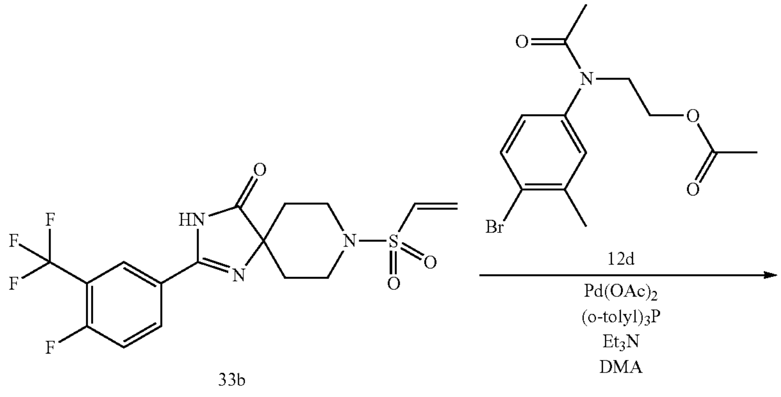

33b

-continued
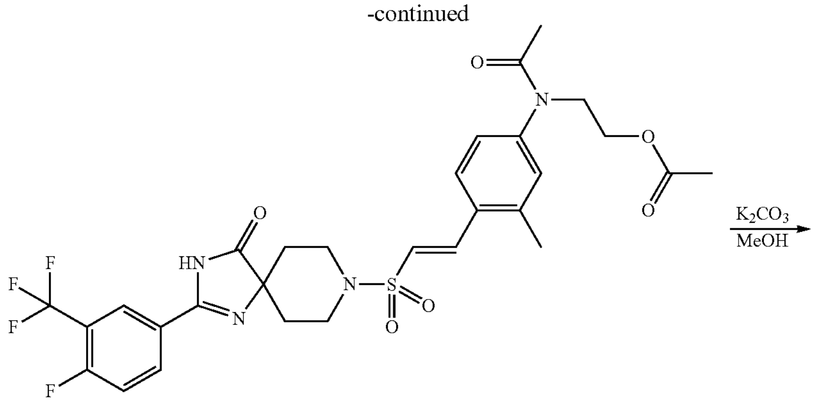
163a
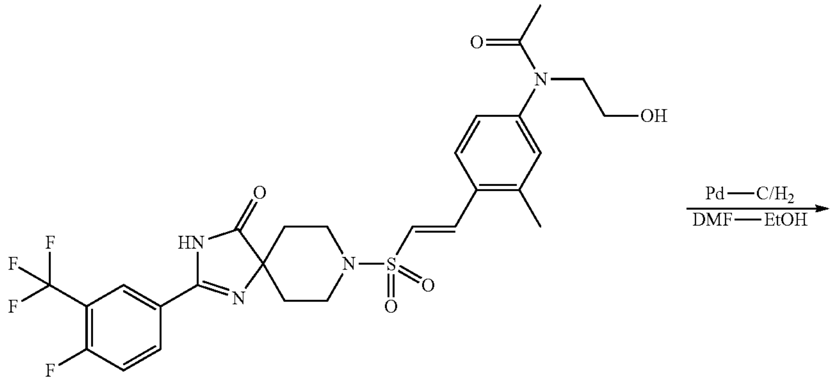
163b
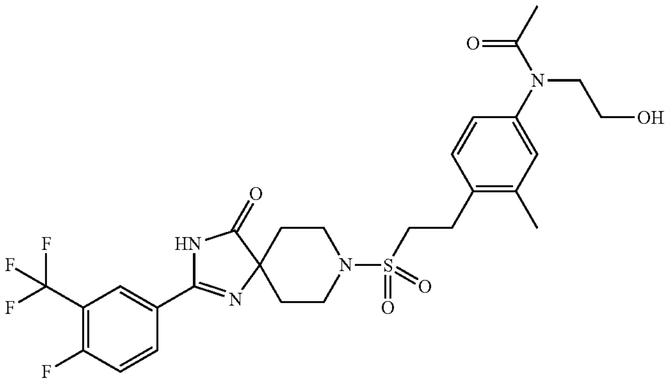
Compound 721
N-(4-{2-[2-(4-Fluoro-3-trifluoromethyl-phenyl)-4-oxo-1,3,8-triaza-spiro[4.5]dec-1-ene-8-sulfonyl]-ethyl}-3-methyl-phenyl)-N-(2-hydroxy-ethyl)-acetamide was synthesized by operations similar to those in Reaction 26-1, Reaction 12-5 and Reaction 42-2 using appropriate reagents and starting material.
MS (ESI) m/z=599 (M+H)+.

Example 164
2-Hydroxy-N-(2-hydroxy-ethyl)-N-(3-methyl-4-{(E)-2-[4-oxo-2-(3-trifluoromethoxy-phenyl)-1,3,8-triaza-spiro[4.5]dec-1-ene-8-sulfonyl]-vinyl}-phenyl)-acetamide (Compound 722)
(Reaction 164-1)
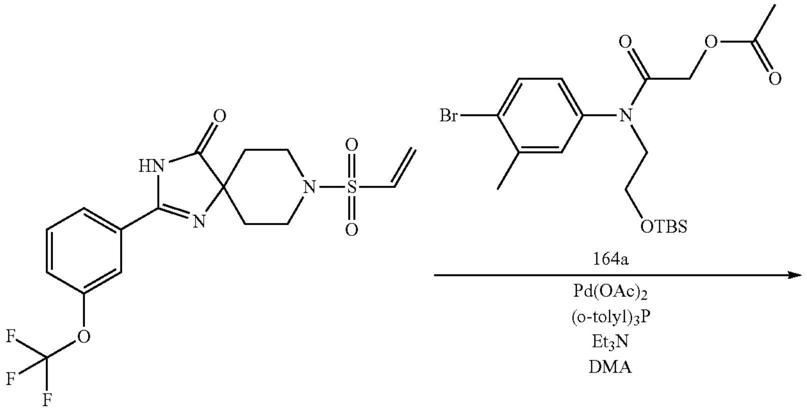
30a
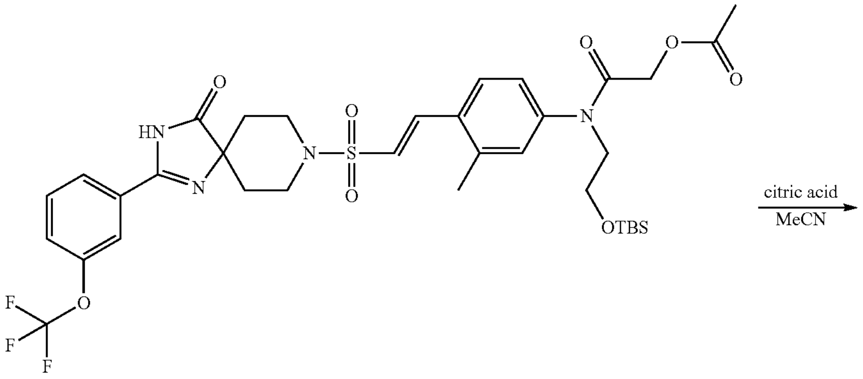
164b
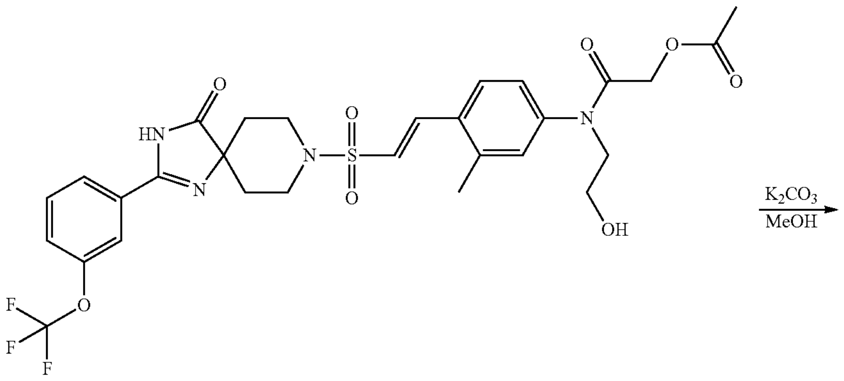
164c -continued

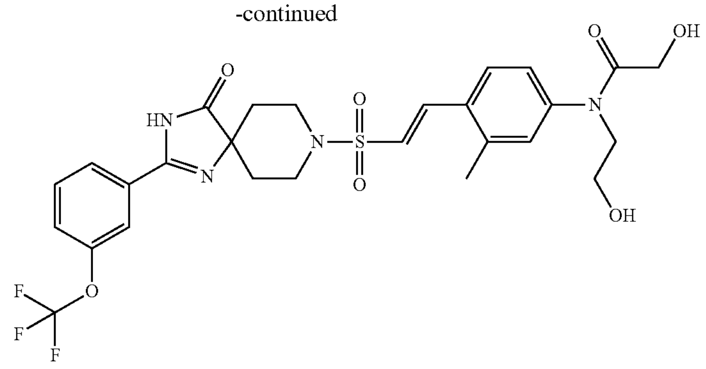

Compound 722

2-Hydroxy-N-(2-hydroxy-ethyl)-N-(3-methyl-4-{(E)-2-[4-oxo-2-(3-trifluoromethoxy-phenyl)-1,3,8-triaza-spiro[4.5]dec-1-ene-8-sulfonyl]-vinyl}-phenyl)-acetamide was synthesized by operations similar to those in Reaction 26-1, Reaction 161-2 and Reaction 12-5 using appropriate reagents and starting material.

MS (ESI) m/z=611 (M+H)+.

The aryl bromide reagent used in the synthesis of Compound 722 (acetic acid {(4-bromo-3-methyl-phenyl)-[2-(tert-butyl-dimethyl-silanyloxy)-ethyl]-carbamoyl}-methyl ester) was synthesized as follows.

(Reaction 164-2)

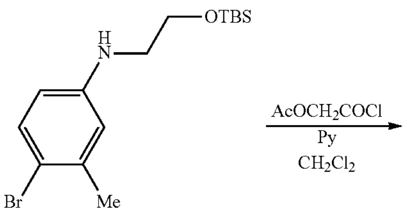

157c

-continued

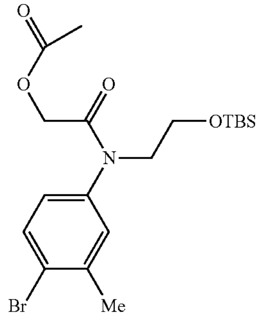

164a

Acetic acid {(4-bromo-3-methyl-phenyl)-[2-(tert-butyl-dimethyl-silanyloxy)-ethyl]-carbamoyl}-methyl ester was synthesized by operations similar to those in Reaction 105-2 using appropriate reagents and starting material.

$^1$H-NMR (300 MHz, $CDCl_3$) δ 0.03 (6H, s), 0.86 (9H, s), 2.13 (3H, s), 2.41 (3H, s), 3.76 (4H, s), 4.36 (2H, s), 6.99 (1H, dd, J=8.4, 2.4 Hz), 7.19 (1H, d, J=2.4 Hz), 7.56 (1H, d, J=8.4 Hz).

Example 165

1-[3,5-Dimethyl-4-((E)-2-{4-oxo-2-[4-(3,3,3-trifluoro-propyl)-cyclohexyl]-1,3,8-triaza-spiro[4.5]dec-1-ene-8-sulfonyl}-vinyl)-phenyl]-1-methyl-urea (Compound 723)

(Reaction 165-1)

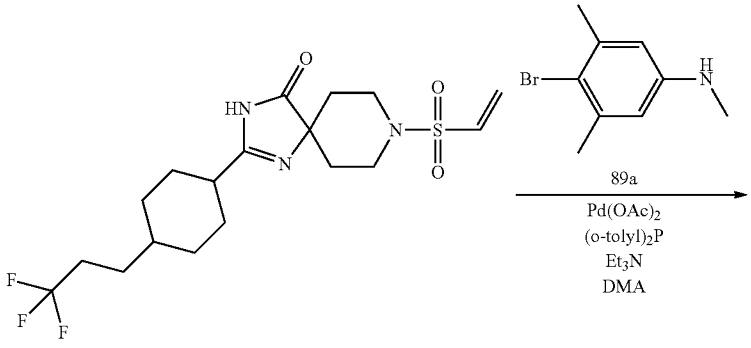

101j

-continued

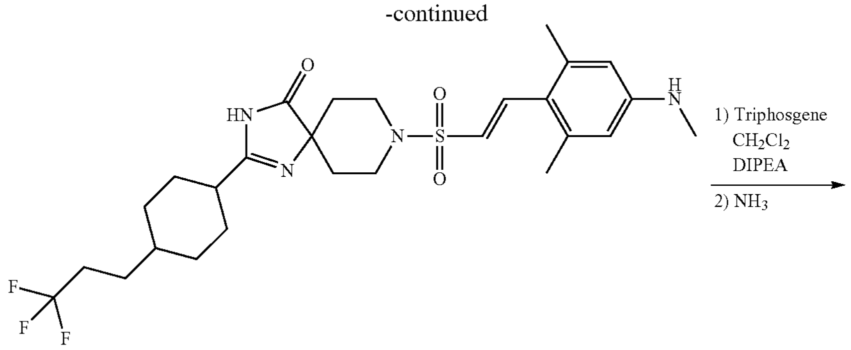

165a

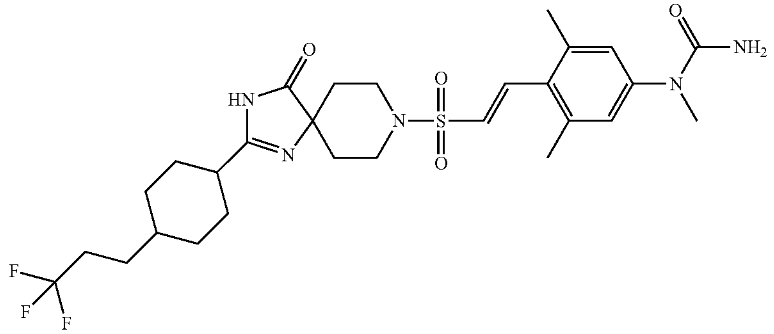

Compound 723

1-[3,5-Dimethyl-4-((E)-2-{4-oxo-2-[4-(3,3,3-trifluoro-propyl)-cyclohexyl]-1,3,8-triaza-spiro[4.5]dec-1-ene-8-sulfonyl}-vinyl)-phenyl]-1-methyl-urea was synthesized by operations similar to those in Reaction 26-1 and Reaction 81-1 using appropriate reagents and starting material.

MS (ESI) m/z=598 (M+H)+.

Example 166

1-[3,5-Dimethyl-4-((E)-2-{4-oxo-2-[4-(3,3,3-trifluoro-propyl)-cyclohexyl]-1,3,8-triaza-spiro[4.5]dec-1-ene-8-sulfonyl}-vinyl)-phenyl]-1-[2-(2-hydroxy-ethoxy)-ethyl]-urea (Compound 724)

(Reaction 166-1)

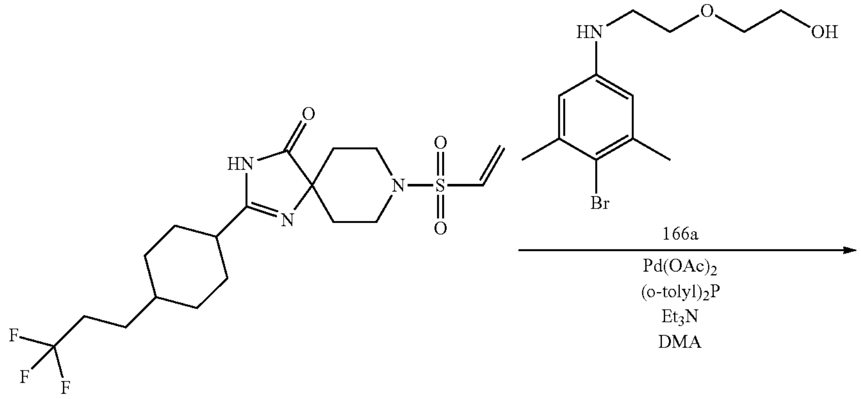

101j

-continued

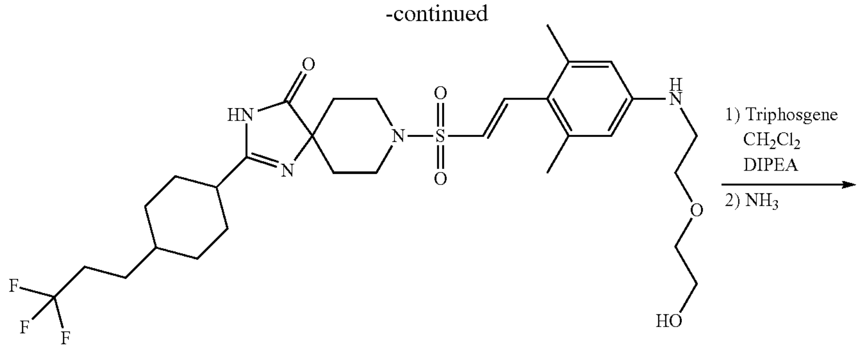

166b

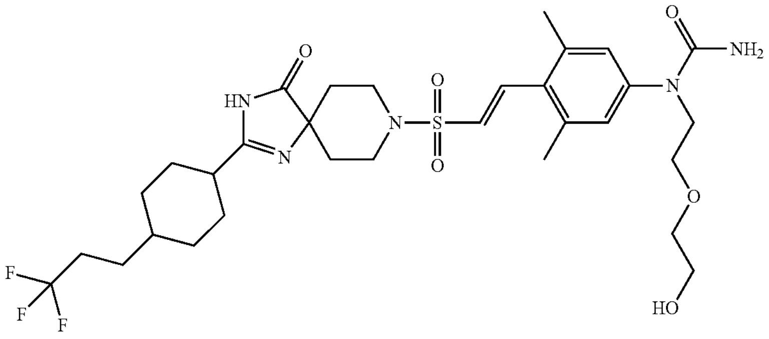

Compound 724

1-[3,5-Dimethyl-4-((E)-2-{4-oxo-2-[4-(3,3,3-trifluoro-propyl)-cyclohexyl]-1,3,8-triaza-spiro[4.5]dec-1-ene-8-sulfonyl}-vinyl)-phenyl]-1-[2-(2-hydroxy-ethoxy)-ethyl]-urea was synthesized by operations similar to those in Reaction 25-2 and Reaction 81-1 using appropriate reagents and starting material.

MS (ESI) m/z=672 (M+H)+.

The example compound shown below was synthesized by operations similar to those in Example 166 using appropriate reagents and starting material.

Compound 725

TABLE 107

| Target Compound | Structure | LCMS condition | Retention time (min) | MS (m/z) |
| --- | --- | --- | --- | --- |
| 725 | 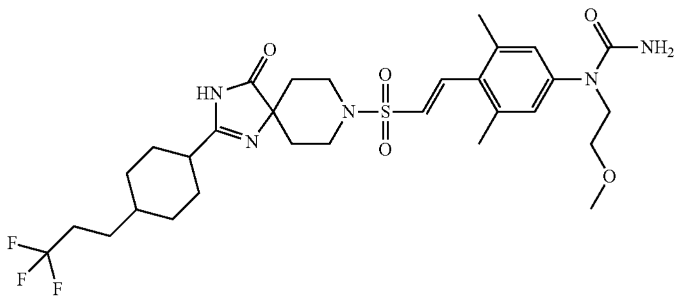 [SMILES: COCCN(C(N)=O)c1cc(C)c(/C=C/S(=O)(=O)N2CCC3(CC2)N=C(C2CCC(CCC(F)(F)F)CC2)NC3=O)c(C)c1] | LCMS-D-1 | 2.32 | 642 (M + H)+ |

The aryl bromide reagent used in the synthesis of Compound 724 (2-[2-(4-bromo-3,5-dimethyl-phenylamino)-ethoxy]-ethanol) was synthesized as follows.

(Reaction 166-2)

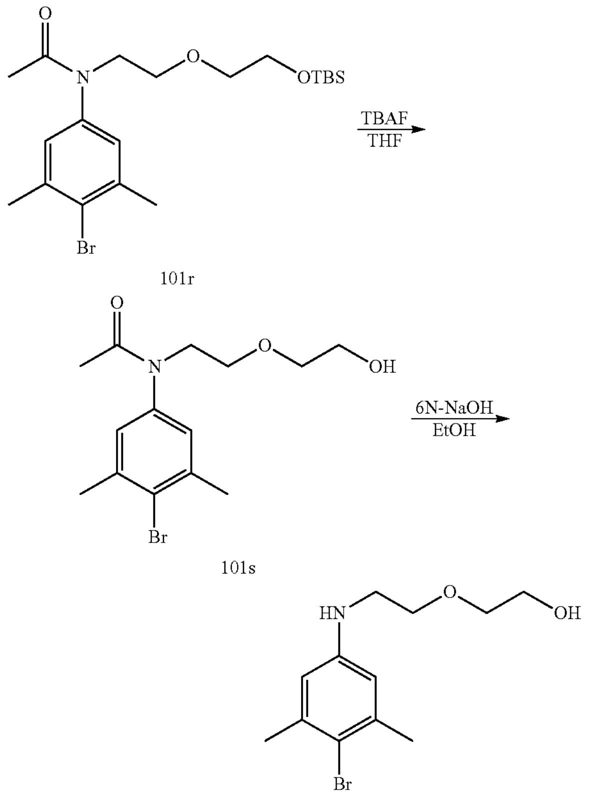

101r

101s

166a

2-[2-(4-Bromo-3,5-dimethyl-phenylamino)-ethoxy]-ethanol was synthesized by operations similar to those in Reaction 39-2 and Reaction 96-16 using appropriate reagents and starting material.

MS (ESI) m/z=288, 290 (M+H)+.

The aryl bromide reagent used in the synthesis of Compound 725 ((4-bromo-3,5-dimethyl-phenyl)-(2-methoxy-ethyl)-amine) was synthesized as follows.

(Reaction 166-3)

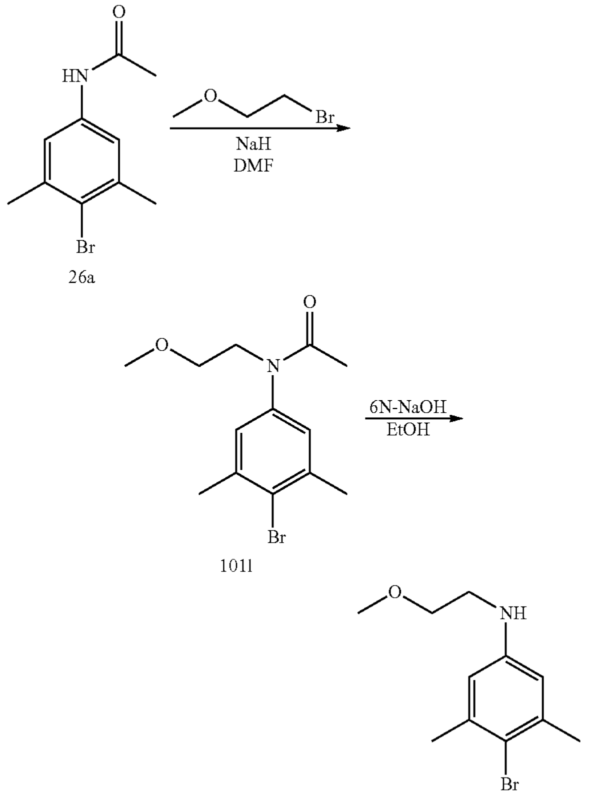

26a

1011

166c (4-Bromo-3,5-dimethyl-phenyl)-(2-methoxy-ethyl)-amine was synthesized by operations similar to those in Reaction 25-3 and Reaction 96-16 using appropriate reagents and starting material.

MS (ESI) m/z=258, 260 (M+H)+.

Example 167

1-(3,5-Dimethyl-4-{(E)-2-[2-(4-methyl-cyclohexyl)-4-oxo-1,3,8-triaza-spiro[4.5]dec-1-ene-8-sulfonyl]-vinyl}-phenyl)-1-isopropyl-urea (Compound 726)

(Reaction 167-1)

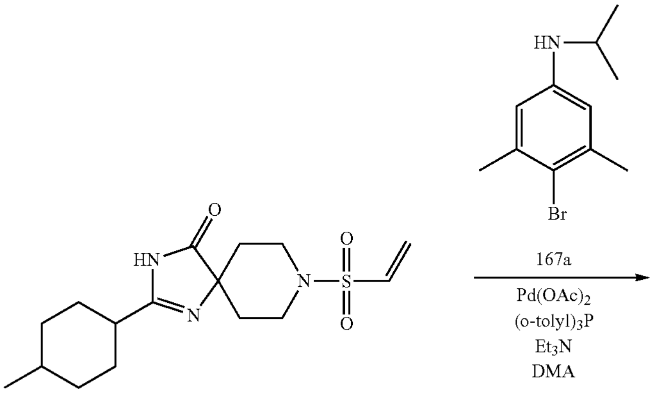

27b

-continued

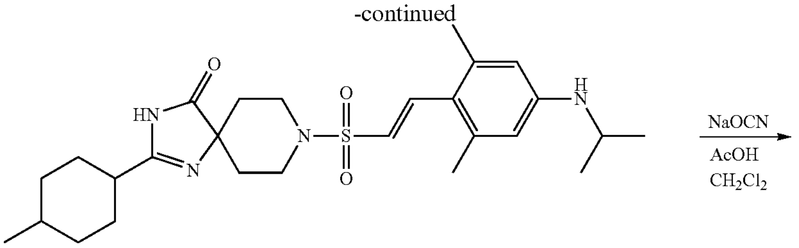

167b

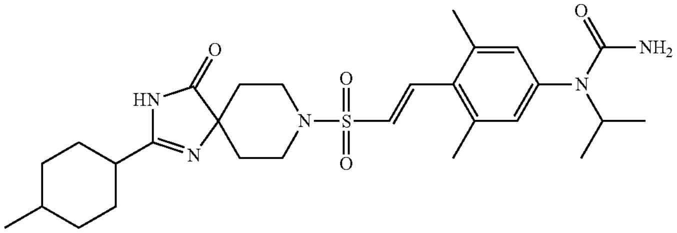

Compound 726

1-(3,5-Dimethyl-4-{(E)-2-[2-(4-methyl-cyclohexyl)-4-oxo-1,3,8-triaza-spiro[4.5]dec-1-ene-8-sulfonyl]-vinyl}-phenyl)-1-isopropyl-urea was synthesized by operations similar to those in Reaction 25-2 and Reaction 89-2 using appropriate reagents and starting material.

MS (ESI) m/z=544 (M+H)+.

The example compound shown below was synthesized by operations similar to those in Example 167 using appropriate reagents and starting material.

Compound 727

(4-Bromo-3,5-dimethyl-phenyl)-isopropyl-amine was synthesized by operations similar to those in Reaction 41-1 using appropriate reagents and starting material.

$^1$H-NMR ($CDCl_3$) δ 6.33 (s, 2H), 3.57 (q, 1H, J=6.6 Hz), 2.32 (s, 6H), 1.18 (d, 6H, J=6.6 Hz).

The aryl bromide reagent used in the synthesis of Compound 727 ((4-bromo-3-ethyl-phenyl)-methyl-amine) was synthesized as follows.

TABLE 108

| Target Compound | Structure | LCMS condition | Retention time (min) | MS (m/z) |
|---|---|---|---|---|
| 727 | 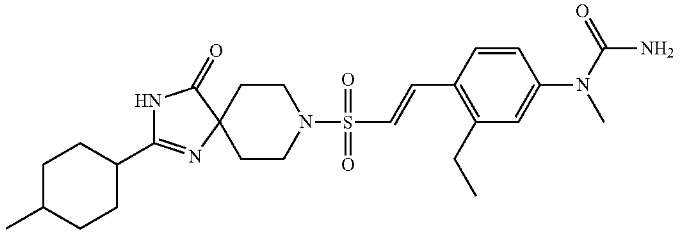 | LCMS-D-1 | 2.68 | 516 (M + H)+ |

The aryl bromide reagent used in the synthesis of Compound 726 ((4-bromo-3,5-dimethyl-phenyl)-isopropyl-amine) was synthesized as follows.

(Reaction 167-2)

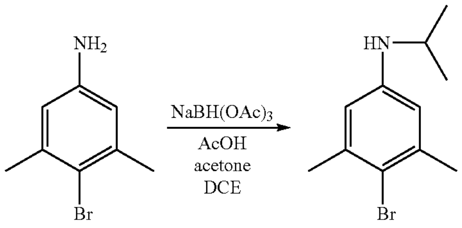

96g 167a (Reaction 167-3)

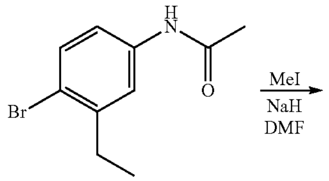

96n

-continued
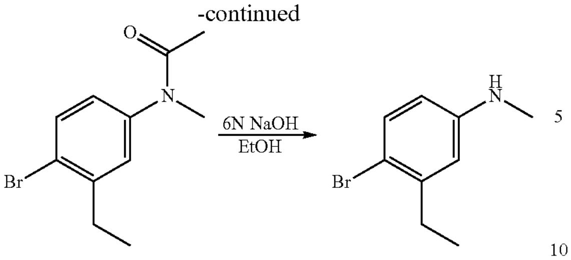
167c 167d
(4-Bromo-3-ethyl-phenyl)-methyl-amine was synthesized by operations similar to those in Reaction 25-3 and Reaction 96-16 using appropriate reagents and starting material.
MS (ESI) m/z=214, 216 (M+H)+.
Example 168
1-(3-Methoxy-5-methyl-4-{(E)-2-[2-(4-methyl-cyclohexyl)-4-oxo-1,3,8-triaza-spiro[4.5]dec-1-ene-8-sulfonyl]-vinyl}-phenyl)-1-methyl-urea (Compound 728)
(Reaction 168-1)
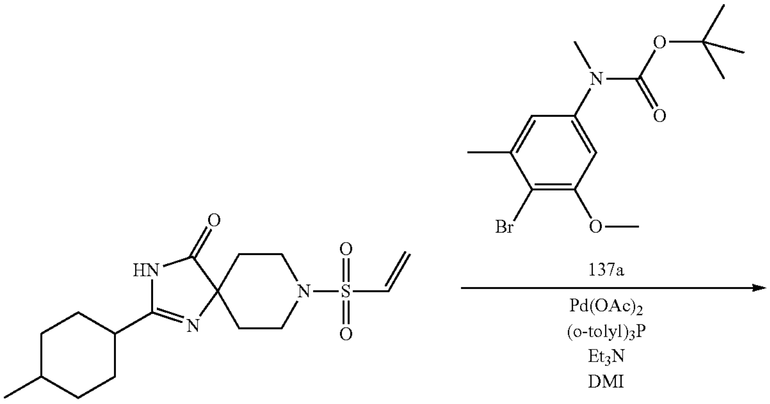
27b
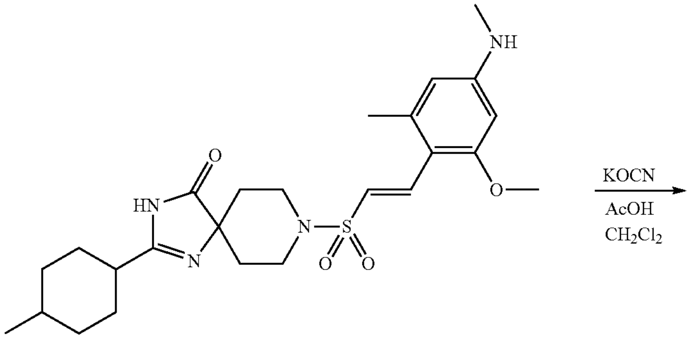
168a
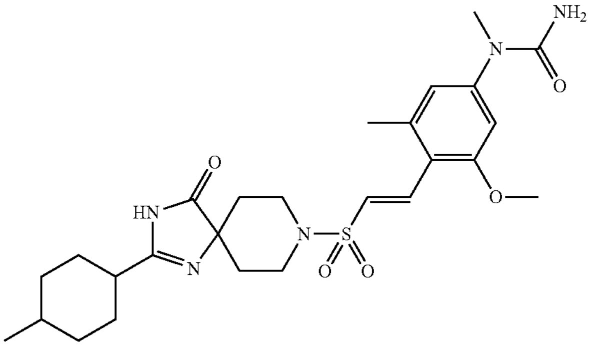
Compound 728

1-(3-Methoxy-5-methyl-4-{(E)-2-[2-(4-methyl-cyclohexyl)-4-oxo-1,3,8-triaza-spiro[4.5]dec-1-ene-8-sulfonyl]-vinyl}-phenyl)-1-methyl-urea was synthesized by operations similar to those in Reaction 26-1 (using DMI as a solvent) and Reaction 89-2 (using KOCN as a reagent) using appropriate reagents and starting material.

MS (ESI) m/z=532 (M+H)+.

Example 169

1-Cyanomethyl-1-(3-methyl-4-{(E)-2-[4-oxo-2-(3-trifluoromethoxy-phenyl)-1,3,8-triaza-spiro[4.5]dec-1-ene-8-sulfonyl]-vinyl}-phenyl)-urea (Compound 729)

(Reaction 169-1)

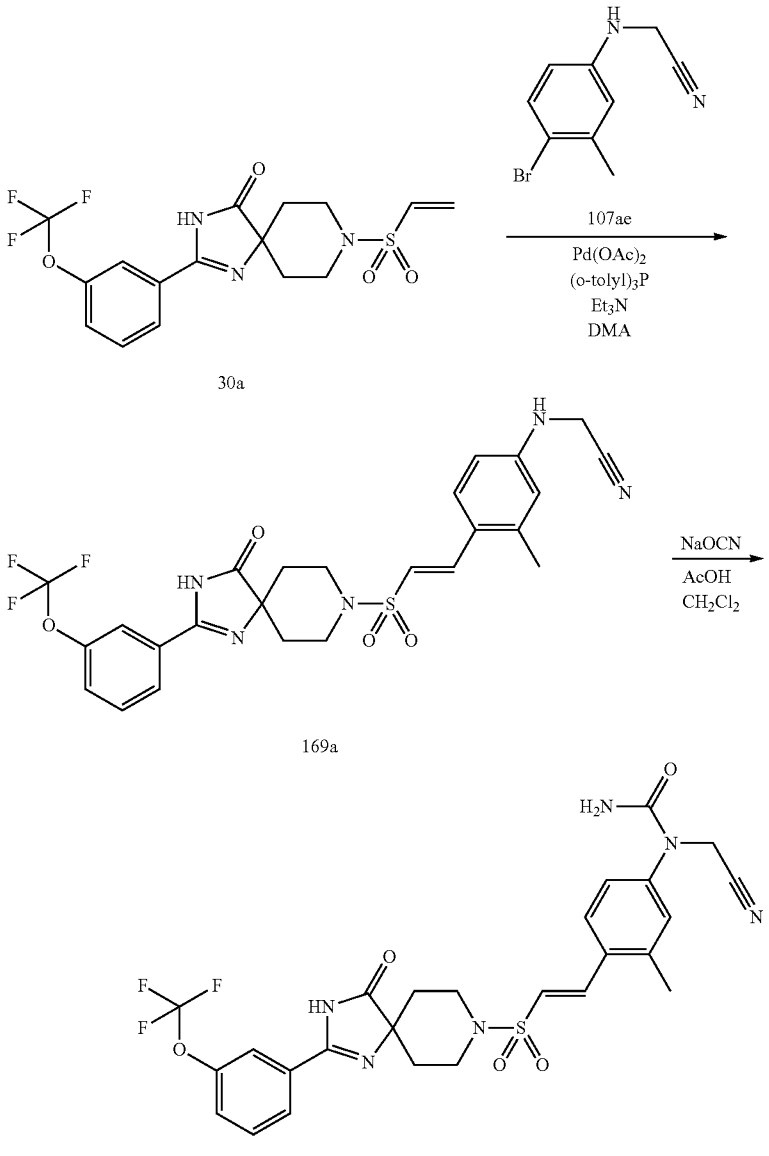

30a

169a

Compound 729

1-Cyanomethyl-1-(3-methyl-4-{(E)-2-[4-oxo-2-(3-trifluoromethoxy-phenyl)-1,3,8-triaza-spiro[4.5]dec-1-ene-8-sulfonyl]-vinyl}-phenyl)-urea was synthesized by operations similar to those in Reaction 26-1 and Reaction 89-2 using appropriate reagents and starting material.

MS (ESI) m/z=591 (M+H)+.

The example compound shown below was synthesized by operations similar to those in Example 169 using appropriate reagents and starting material.

Compound 730
TABLE 109
| Target Compound | Structure | LCMS condition | Retention time (min) | MS (m/z) |
|---|---|---|---|---|
| 730 | 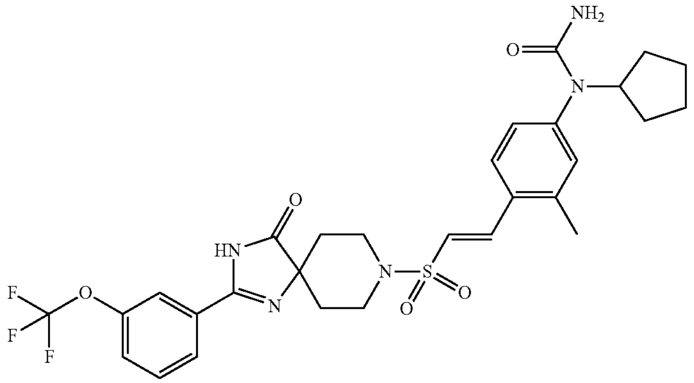 [SMILES: Cc1cc(N(C(N)=O)C2CCCC2)ccc1/C=C/S(=O)(=O)N1CCC2(CC1)N=C(c1cccc(OC(F)(F)F)c1)NC2=O] | LCMS-B-1 | 2.36 | 620 (M + H)+ |
Example 170
1-(3-Methyl-4-{(E)-2-[4-oxo-2-(3-trifluoromethoxy-phenyl)-1,3,8-triaza-spiro[4.5]dec-1-ene-8-sulfonyl]-vinyl}-phenyl)-1-(2,2,2-trifluoro-ethyl)-urea (Compound 731)
(Reaction 170-1)
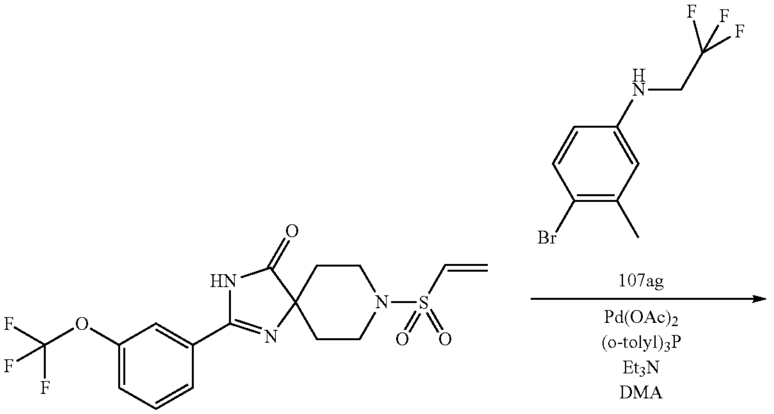
30a
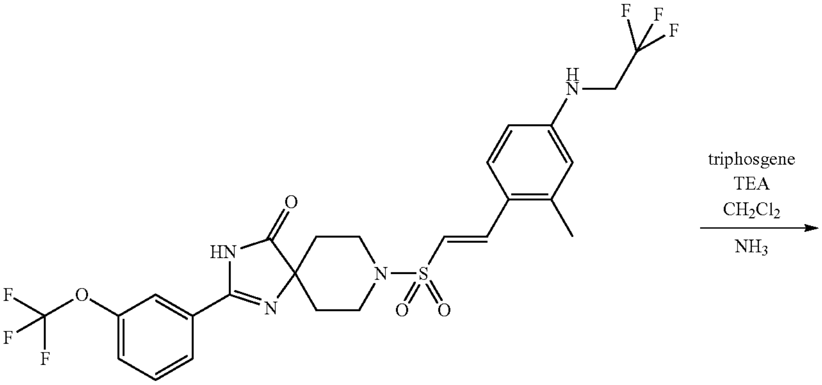
170a -continued

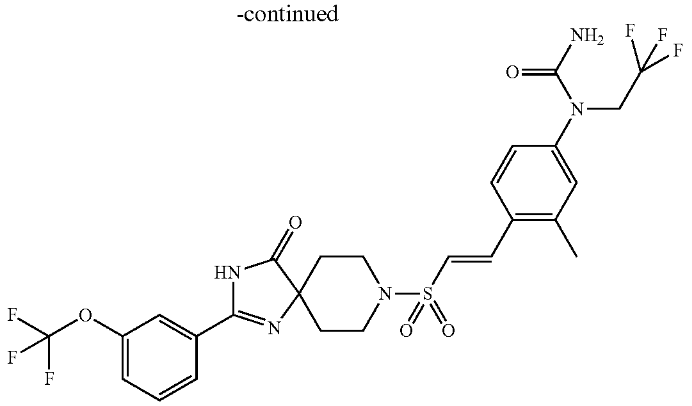

Compound 731

1-(3-Methyl-4-{(E)-2-[4-oxo-2-(3-trifluoromethoxy-phenyl)-1,3,8-triaza-spiro[4.5]dec-1-ene-8-sulfonyl]-vinyl}-phenyl)-1-(2,2,2-trifluoro-ethyl)-urea was synthesized by operations similar to those in Reaction 26-1 and Reaction 81-1 using appropriate reagents and starting material.

MS (ESI) m/z=634 (M+H)+.

Example 171

1-(4-{2-[2-(4-Ethyl-cyclohexyl)-4-oxo-1,3,8-triaza-spiro[4.5]dec-1-ene-8-sulfonyl]-ethyl}-3,5-dimethyl-phenyl)-1-methyl-urea (Compound 732)

(Reaction 171-1)

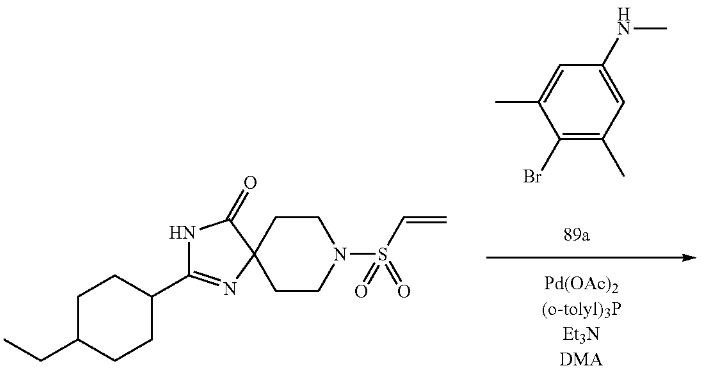

111f

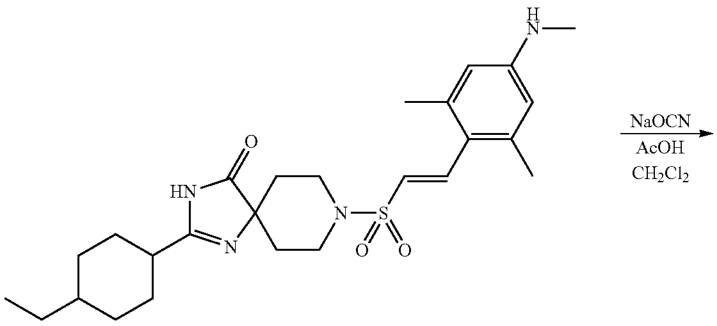

171a

-continued

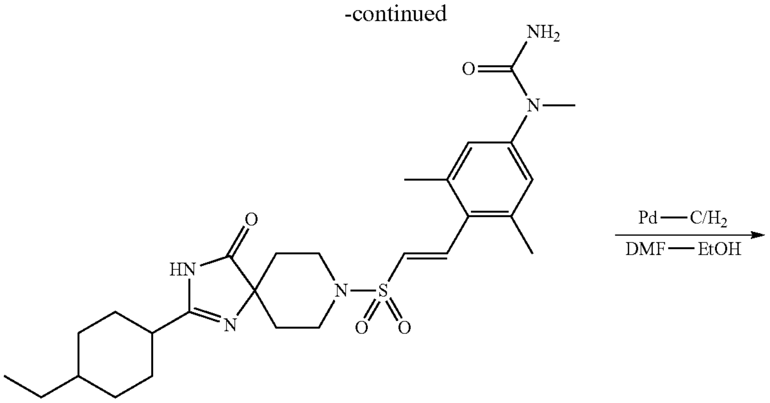

171b

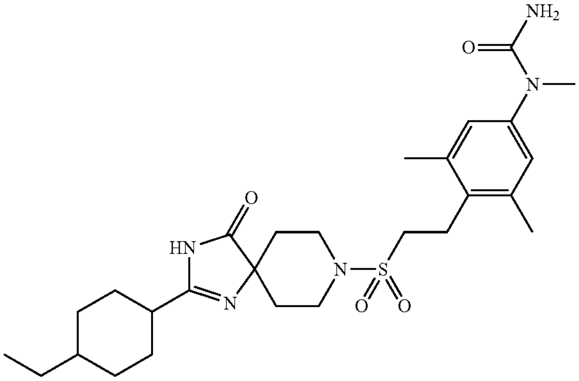

Compound 732

1-(4-{2-[2-(4-Ethyl-cyclohexyl)-4-oxo-1,3,8-triaza-spiro[4.5]dec-1-ene-8-sulfonyl]-ethyl}-3,5-dimethyl-phenyl)-1-methyl-urea was synthesized by operations similar to those in Reaction 25-2, Reaction 89-2 and Reaction 42-2 using appropriate reagents and starting material.

MS (ESI) m/z=532 (M+H)+.

Example 172

1-((S)-2,3-Dihydroxy-propyl)-1-(3,5-dimethyl-4-{(E)-2-[2-(4-methyl-cyclohexyl)-4-oxo-1,3,8-triaza-spiro[4.5]dec-1-ene-8-sulfonyl]-vinyl}-phenyl)-urea (Compound 733)

(Reaction 172-1)

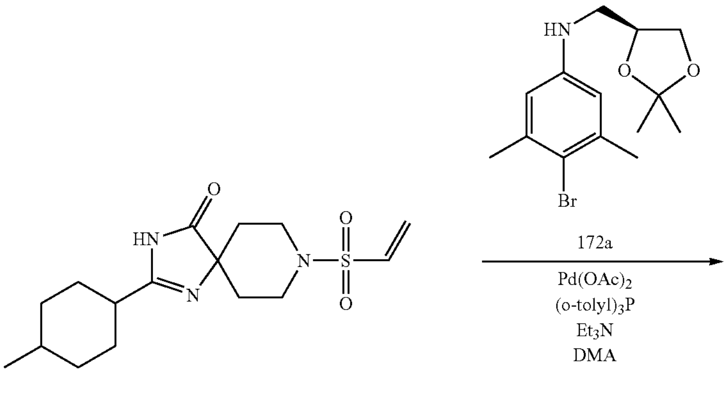

27b

-continued

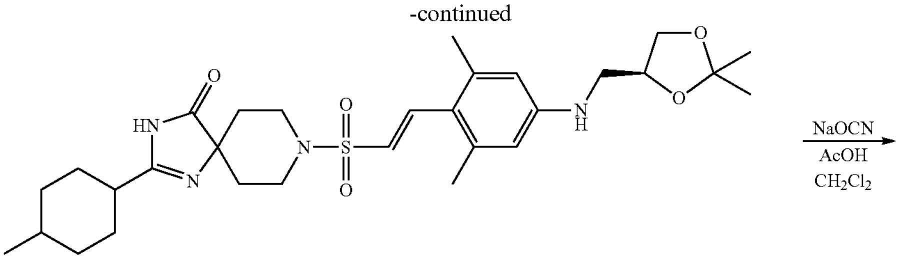

172b

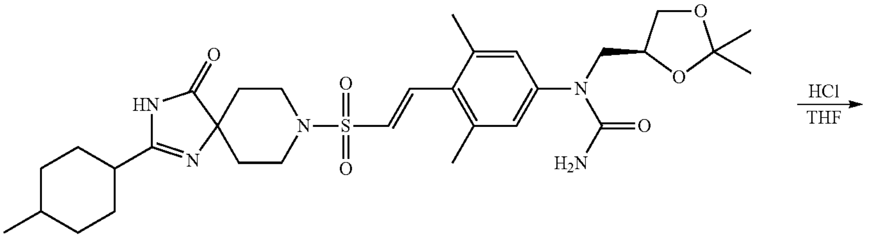

172e

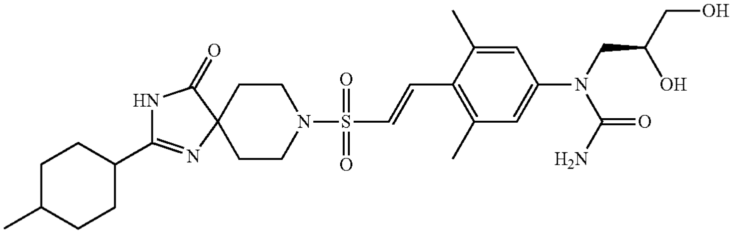

Compound 733

1-((S)-2,3-Dihydroxy-propyl)-1-(3,5-dimethyl-4-{(E)-2-[2-(4-methyl-cyclohexyl)-4-oxo-1,3,8-triaza-spiro[4.5]dec-1-ene-8-sulfonyl]-vinyl}-phenyl)-urea was synthesized by operations similar to those in Reaction 25-2, Reaction 89-2 and Reaction 25-4 using appropriate reagents and starting material.

MS (ESI) m/z=576 (M+H)+.

The aryl bromide reagent used in the synthesis of Compound 733 ((4-bromo-3,5-dimethyl-phenyl)-((S)-2,2-dimethyl-[1,3]dioxolan-4-ylmethyl)-amine) was synthesized as follows.

(Reaction 172-2)

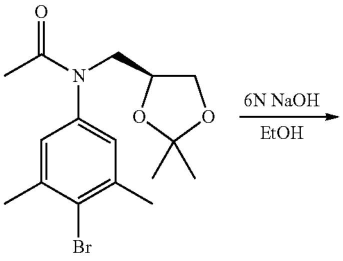

155a

-continued

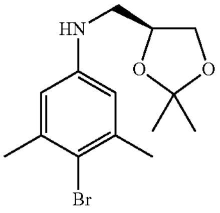

172a (4-Bromo-3,5-dimethyl-phenyl)-((S)-2,2-dimethyl-[1,3]dioxolan-4-ylmethyl)-amine was synthesized by operations similar to those in Reaction 96-16 using appropriate reagents and starting material.

$^1$H-NMR ($CDCl_3$) δ 6.39 (s, 2H), 4.34 (m, 1H), 4.09 (dd, 1H, J=8.2, 6.3 Hz), 3.75 (dd, 1H, J=8.2, 6.3 Hz), 3.29-3.11 (m, 2H), 2.33 (s, 6H), 1.45 (s, 3H), 1.37 (s, 3H).

Example 173

N-{4-[(E)-2-(2-Cyclohexyl-4-oxo-1,3,8-triaza-spiro[4.5]dec-1-ene-8-sulfonyl)-vinyl]-3-methyl-phenyl}-N-cyclopentyl-acetamide trifluoroacetate (Compound 734)

(Reaction 173-1)

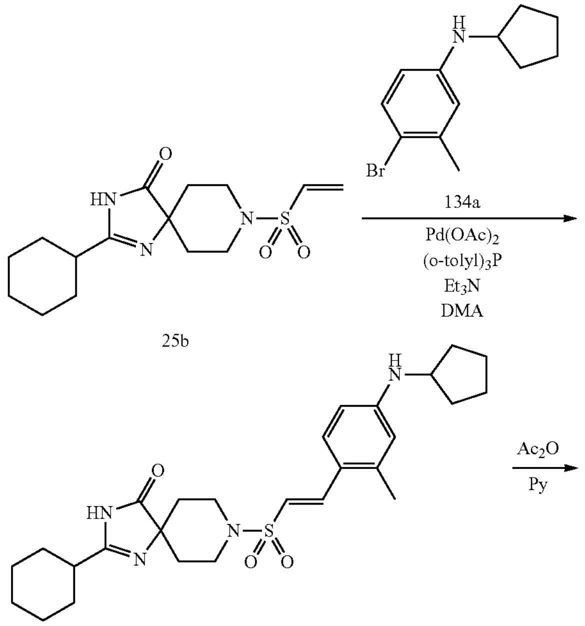

25b

173a

-continued

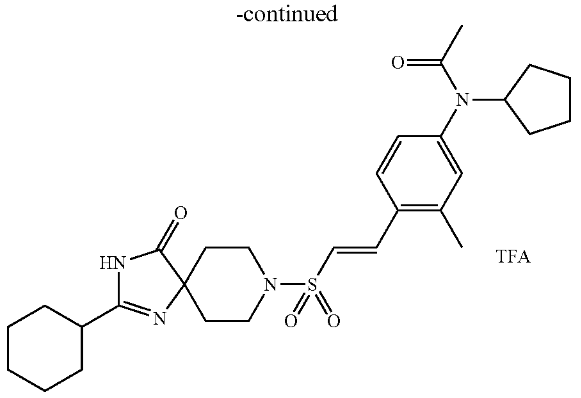

Compound 734

N-{4-[(E)-2-(2-Cyclohexyl-4-oxo-1,3,8-triaza-spiro[4.5]dec-1-ene-8-sulfonyl)-vinyl]-3-methyl-phenyl}-N-cyclopentyl-acetamide trifluoroacetate was synthesized by operations similar to those in Reaction 26-1 and Reaction 12-2 (using HPLC for purification) using appropriate reagents and starting material.

MS (ESI) m/z=541 (M+H)+.

Example 174

(S)-2-Amino-N-{4-[(E)-2-(2-cyclohexyl-4-oxo-1,3,8-triaza-spiro[4.5]dec-1-ene-8-sulfonyl)-vinyl]-3,5-dimethyl-phenyl}-3-methyl-butylamide (Compound 735)

(Reaction 174-1)

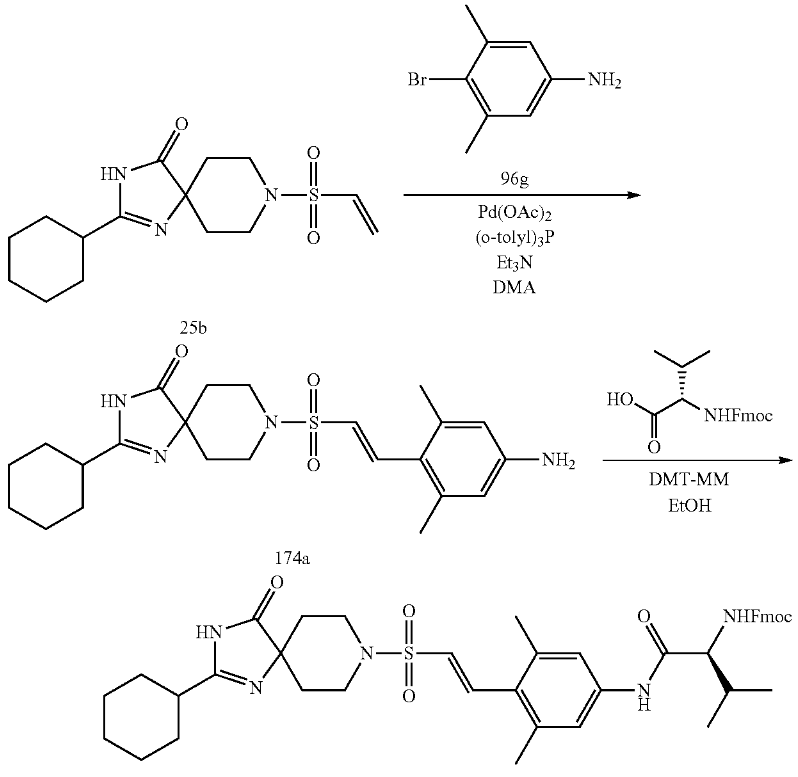

25b

174a

174b ((S)-1-{4-[(E)-2-(2-Cyclohexyl-4-oxo-1,3,8-triaza-spiro[4.5]dec-1-ene-8-sulfonyl)-vinyl]-3,5-dimethyl-phenylcarbamoyl}-2-methyl-propyl)-carbamic acid 9H-fluoren-9-ylmethyl ester was synthesized by operations similar to those in Reaction 26-1 and Reaction 10-1 using appropriate reagents and starting material.

MS (ESI) m/z=766 (M+H)+.

(Reaction 174-2)

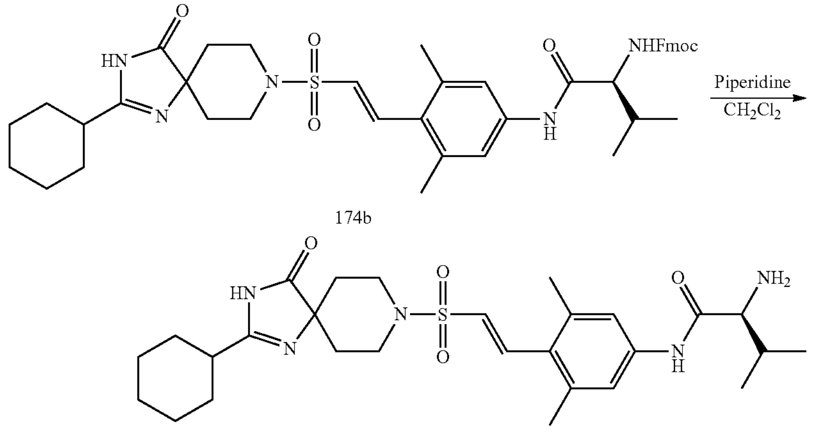

174b

Compound 735

Piperidine (1 ml) was added to a solution of ((S)-1-{4-[(E)-2-(2-cyclohexyl-4-oxo-1,3,8-triaza-spiro[4.5]dec-1-ene-8-sulfonyl)-vinyl]-3,5-dimethyl-phenylcarbamoyl}-2-methyl-propyl)-carbamic acid 9H-fluoren-9-ylmethyl ester (84 mg, 0.11 mmol) in dichloromethane (4 ml), and the mixture was stirred at room temperature for three hours. The reaction mixture was quenched with water and then extracted with ethyl acetate. The organic layer was sequentially washed with water and saturated brine, and then dried over anhydrous magnesium sulfate and concentrated under reduced pressure. The resulting residue was purified by silica gel column chromatography to give (S)-2-amino-N-{4-[(E)-2-(2-cyclohexyl-4-oxo-1,3,8-triaza-spiro[4.5]dec-1-ene-8-sulfonyl)-vinyl]-3,5-dimethyl-phenyl}-3-methyl-butylamide (20 mg, 33%).

MS (ESI) m/z=544 (M+H)+.

Example 175

2-{4-[(E)-2-(2-Cyclohexyl-4-oxo-1,3,8-triaza-spiro[4.5]dec-1-ene-8-sulfonyl)-vinyl]-indol-1-yl}-N-pyridin-4-yl-acetamide (Compound 736)

(Reaction 175-1)

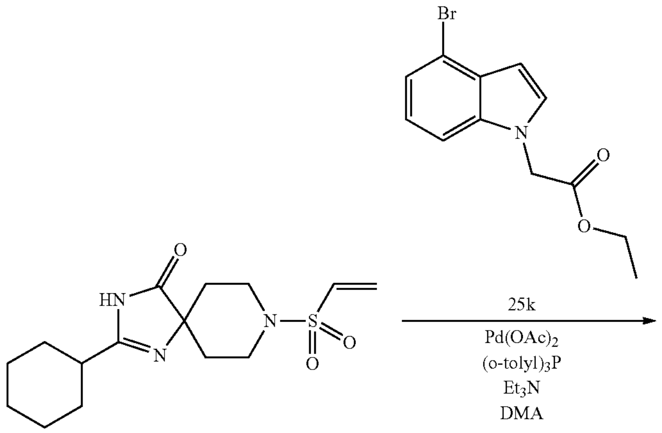

25b

-continued

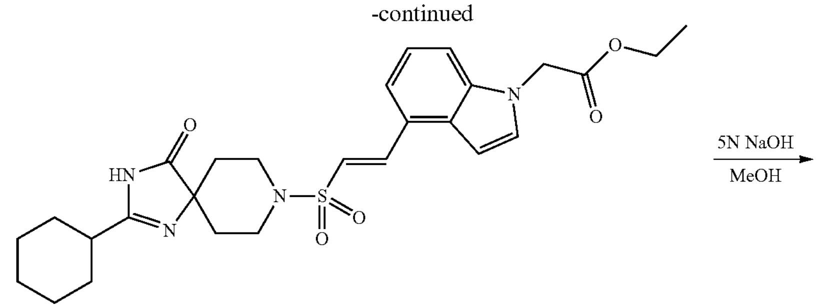

175a

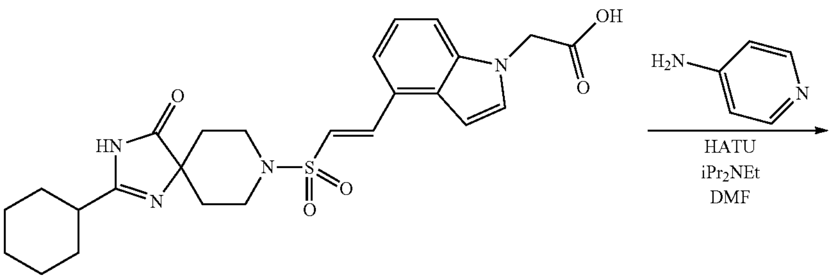

175b

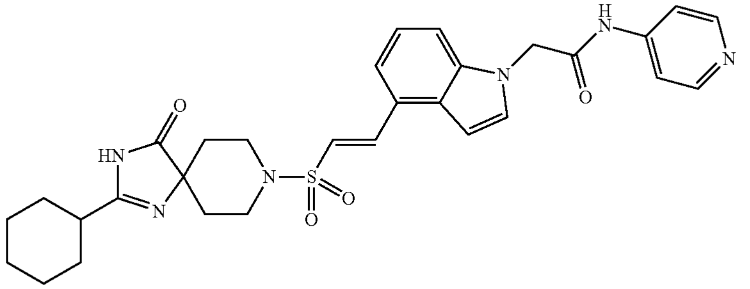

Compound 736

2-{4-[(E)-2-(2-Cyclohexyl-4-oxo-1,3,8-triaza-spiro[4.5]dec-1-ene-8-sulfonyl)-vinyl]-indol-1-yl}-N-pyridin-4-yl-acetamide was synthesized by operations similar to those in Reaction 25-2, Reaction 23-2 and Reaction 10-22 using appropriate reagents and starting material.

MS (ESI) m/z=575 (M+H)+.

The aryl bromide reagent used in the synthesis of Compound 736 ((4-bromo-indol-1-yl)-acetic acid ethyl ester) was synthesized as follows.

(Reaction 175-2)

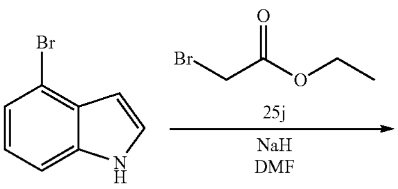

25d

-continued

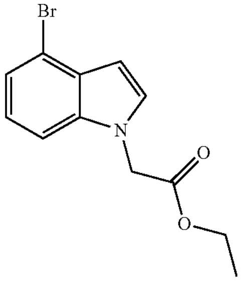

25k (4-Bromo-indol-1-yl)-acetic acid ethyl ester was synthesized by operations similar to those in Reaction 25-3 using appropriate reagents and starting material.

MS (ESI) m/z=282 (M+H)+.

Example 176

2-(3-Methyl-4-{(E)-2-[2-(4-methyl-cyclohexyl)-4-oxo-1,3,8-triaza-spiro[4.5]dec-1-ene-8-sulfonyl]-vinyl}-phenyl)-acetamide (Compound 737)

(Reaction 176-1)

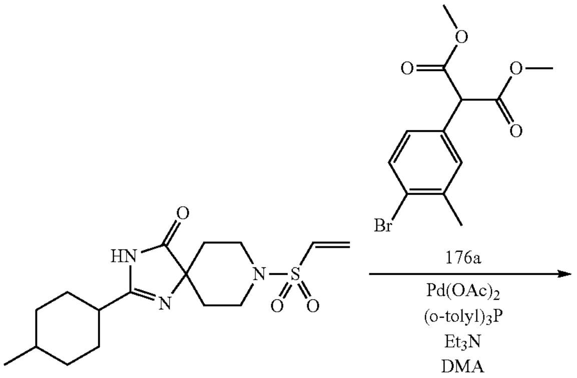

27b

-continued

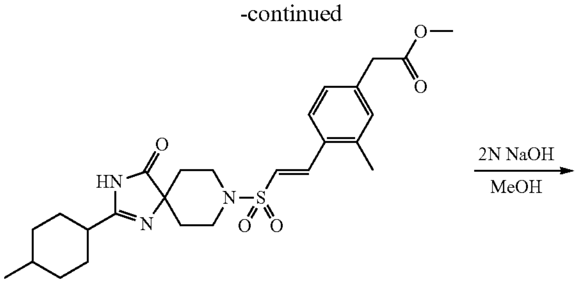

176b

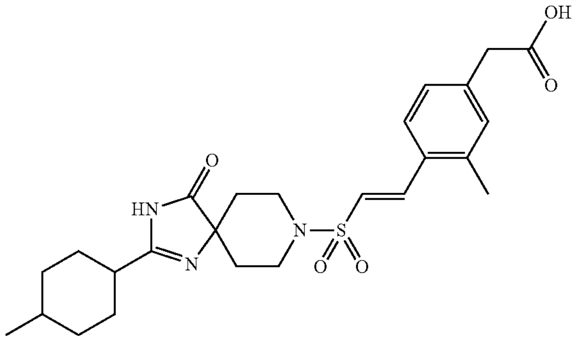

176c (3-Methyl-4-{(E)-2-[2-(4-methyl-cyclohexyl)-4-oxo-1,3,8-triaza-spiro[4.5]dec-1-ene-8-sulfonyl]-vinyl}-phenyl)-acetic acid was synthesized by operations similar to those in Reaction 25-2 and Reaction 23-2 using appropriate reagents and starting material.

MS (ESI) m/z=488 (M+H)+.

(Reaction 176-2)

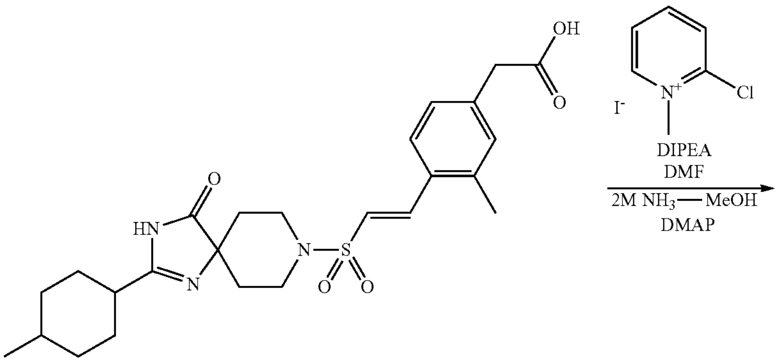

176c

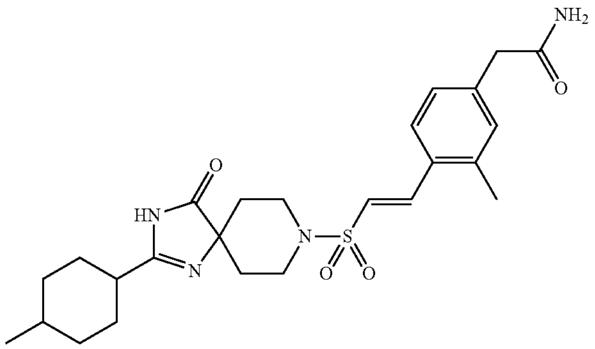

Compound 737

N,N-Diisopropylethylamine (31.4 μL, 0.185 mmol) and 2-chloro-1-methylpyridinium iodide (18.9 mg, 0.074 mmol) were added to a solution of (3-methyl-4-{(E)-2-[2-(4-methyl-cyclohexyl)-4-oxo-1,3,8-triaza-spiro[4.5]dec-1-ene-8-sulfonyl]-vinyl}-phenyl)-acetic acid (30.0 mg, 0.062 mmol) in dichloromethane (0.5 mL) and DMF (0.1 mL), and the mixture was stirred for 10 minutes. A 2.0 M ammonia-methanol solution (0.15 mL, 0.308 mmol) and DMAP (0.8 mg, 0.006 mmol) were then added, and the mixture was stirred overnight. The reaction mixture was then quenched by adding a saturated aqueous ammonium chloride solution and extracted with ethyl acetate. The organic layer was sequentially washed with water and saturated brine, and then dried over anhydrous $Na_2SO_4$ and concentrated under reduced pressure. The resulting residue was purified by silica gel column chromatography to give 2-(3-methyl-4-{(E)-2-[2-(4-methyl-cyclohexyl)-4-oxo-1,3,8-triaza-spiro[4.5]dec-1-ene-8-sulfonyl]-vinyl}-phenyl)-acetamide as a white powder (18.3 mg, 61%).

MS (ESI) m/z=487 (M+H)+.

The aryl bromide reagent used in the synthesis of Compound 737 (2-(4-bromo-3-methyl-phenyl)-malonic acid dimethyl ester) was synthesized as follows.

(Reaction 176-3)

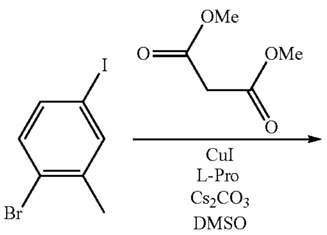

12a

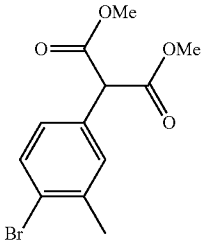

176a 2-(4-Bromo-3-methyl-phenyl)-malonic acid dimethyl ester was synthesized by operations similar to those in Reaction 12-1 using appropriate reagents and starting material.

MS (ESI) m/z=302 (M+H)+.

Example 177

2-Cyclohexyl-8-{(E)-2-[4-(4,5-dihydro-thiazol-2-ylamino)-2,6-dimethyl-phenyl]-ethenesulfonyl}-1,3,8-triaza-spiro[4.5]dec-1-en-4-one (Compound 738)

(Reaction 177-1)

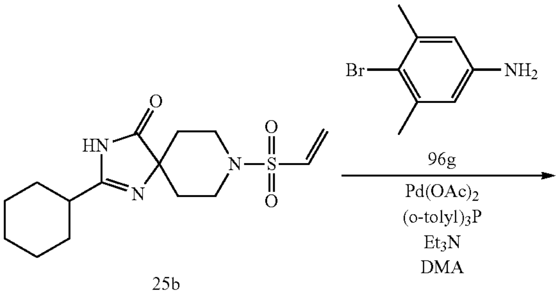

25b

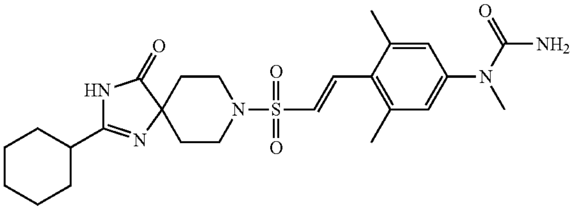

177a

8-[(E)-2-(4-Amino-2,6-dimethyl-phenyl)vinyl]sulfonyl-3-cyclohexyl-2,4,8-triazaspiro[4.5]dec-3-en-1-one was synthesized by operations similar to those in Reaction 26-1 using appropriate reagents and starting material.

MS (ESI) m/z=445 (M+H)+.

(Reaction 177-2)

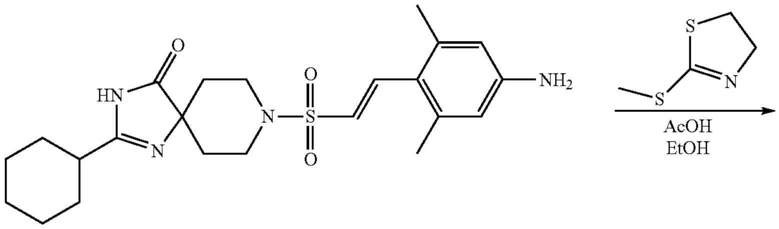

177a

-continued

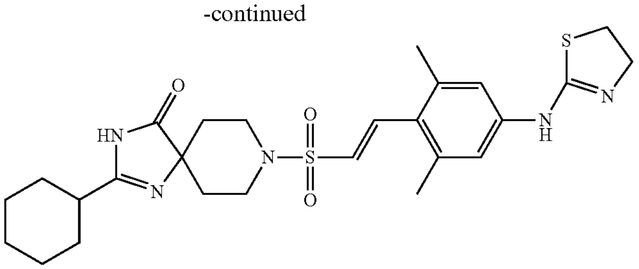

Compound 738

2-(Methylthio)-2-thiazoline (19 μL, 0.17 mmol) and acetic acid (1.2 ml) were added to a solution of 8-[(E)-2-(4-amino-2,6-dimethyl-phenyl)vinyl]sulfonyl-3-cyclohexyl-2,4,8-triazaspiro[4.5]dec-3-en-1-one (74 mg, 0.16 mmol) in EtOH (2.5 ml) at room temperature, and the mixture was heated with stirring at 80° C. for 16 hours. The reaction solution was diluted with ethyl acetate, and the organic layer was then sequentially washed with water and saturated brine and concentrated under reduced pressure. The residue was purified by silica gel column chromatography (ethyl acetate) to give 2-cyclohexyl-8-{(E)-2-[4-(4,5-dihydro-thiazol-2-ylamino)-2,6-dimethyl-phenyl]-ethenesulfonyl}-1,3,8-triaza-spiro[4.5]dec-1-en-4-one (46.1 mg, 52%).

MS (ESI) m/z=530 (M+H)+.

Example 178

2-Cyclohexyl-8-{(E)-2-[2-methyl-4-(3-methyl-oxetan-3-ylmethoxy)-phenyl]-ethenesulfonyl}-1,3,8-triaza-spiro[4.5]dec-1-en-4-one (Compound 739)

(Reaction 178-1)

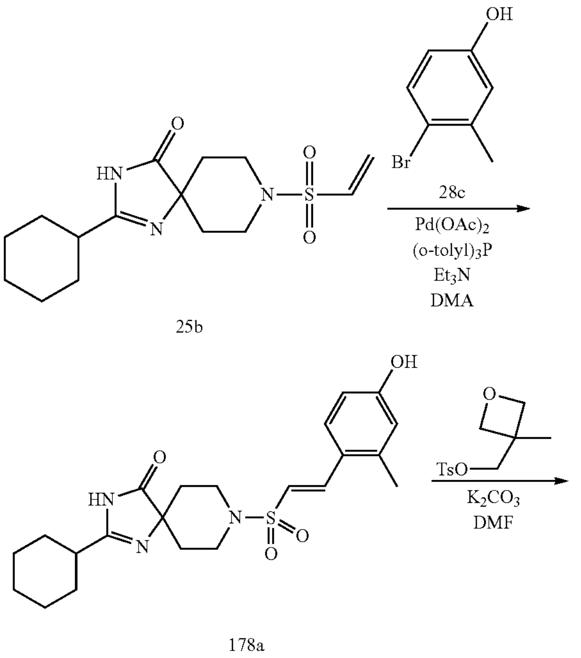

-continued

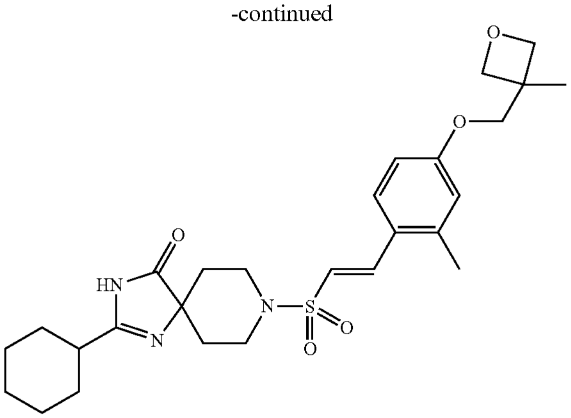

Compound 739

2-Cyclohexyl-8-{(E)-2-[2-methyl-4-(3-methyl-oxetan-3-ylmethoxy)-phenyl]-ethenesulfonyl}-1,3,8-triaza-spiro[4.5]dec-1-en-4-one was synthesized by operations similar to those in Reaction 25-2 and Reaction 26-4 using appropriate reagents and starting material.

MS (ESI) m/z=516 (M+H)+.

Example 179

1-(3,5-Dimethyl-4-{2-[2-(4-methyl-cyclohexyl)-4-oxo-1,3,8-triaza-spiro[4.5]dec-1-ene-8-sulfonyl]-cyclopropyl}-phenyl)-1-methyl-urea (Compound 740) and

1-(3,5-dimethyl-4-{1-methyl-2-[2-(4-methyl-cyclohexyl)-4-oxo-1,3,8-triaza-spiro[4.5]dec-1-ene-8-sulfonyl]-vinyl}-phenyl)-1-methyl-urea (Compound 741)

(Reaction 179-1)

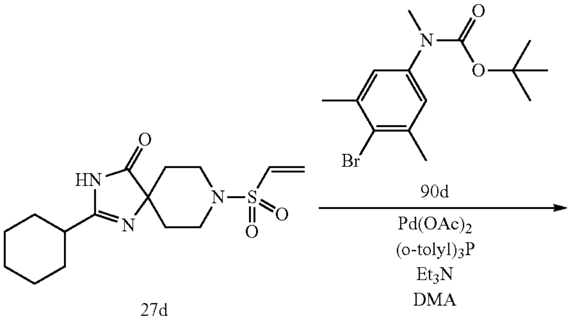

-continued

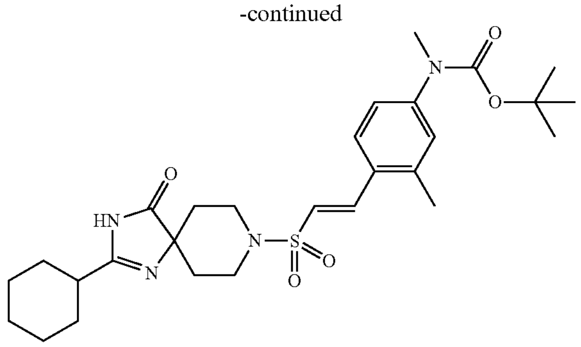

179a (3,5-Dimethyl-4-{(E)-2-[2-(4-methyl-cyclohexyl)-4-oxo-1,3,8-triaza-spiro[4.5]dec-1-ene-8-sulfonyl]-vinyl}-phenyl)-methyl-carbamic acid tert-butyl ester was synthesized by operations similar to those in Reaction 26-1 using appropriate reagents and starting material.

MS (ESI) m/z=573 (M+H)+.

A 1 M solution of sodium bis(trimethylsilyl)amide in tetrahydrofuran (0.31 mL, 0.306 mmol) was added to a mixture of trimethylsulfoxonium iodide (29 mg, 0.131 mmol) in 1,3-dimethyl-2-imidazolidinone (2 mL) at room temperature. The reaction solution was stirred at room temperature for 0.5 hour. A mixed solution of (3,5-dimethyl-4-{(E)-2-[2-(4-methyl-cyclohexyl)-4-oxo-1,3,8-triaza-spiro[4.5]dec-1-ene-8-sulfonyl]-vinyl}-phenyl)-methyl-carbamic acid tert-butyl ester (50 mg, 0.0873 mmol) in 1,3-dimethyl-2-imidazolidinone (2 mL) was then added at room temperature, and the mixture was heated with stirring at 50° C. for 15 hours. After returning to room temperature, an aqueous ammonium chloride solution and ethyl acetate were added to the reaction solution. The organic layer and the aqueous layer were separated, and the aqueous layer was repeatedly extracted with ethyl acetate three times. The organic layers were combined, washed with water twice and saturated brine, and then concentrated under reduced pressure. The resulting residue was purified by silica gel column chromatography to give a mixture of (3,5-dimethyl-4-{2-[2-(4-methyl-cyclohexyl)-4-oxo-1,3,8-triaza-spiro[4.5]dec-1-ene-8-sulfonyl]-cyclopropyl}-phenyl)-methyl-carbamic acid tert-butyl ester. This mixture was used in the next reaction as such without further purification.

MS (ESI) m/z=587 (M+H)+.

(Reaction 179-2)

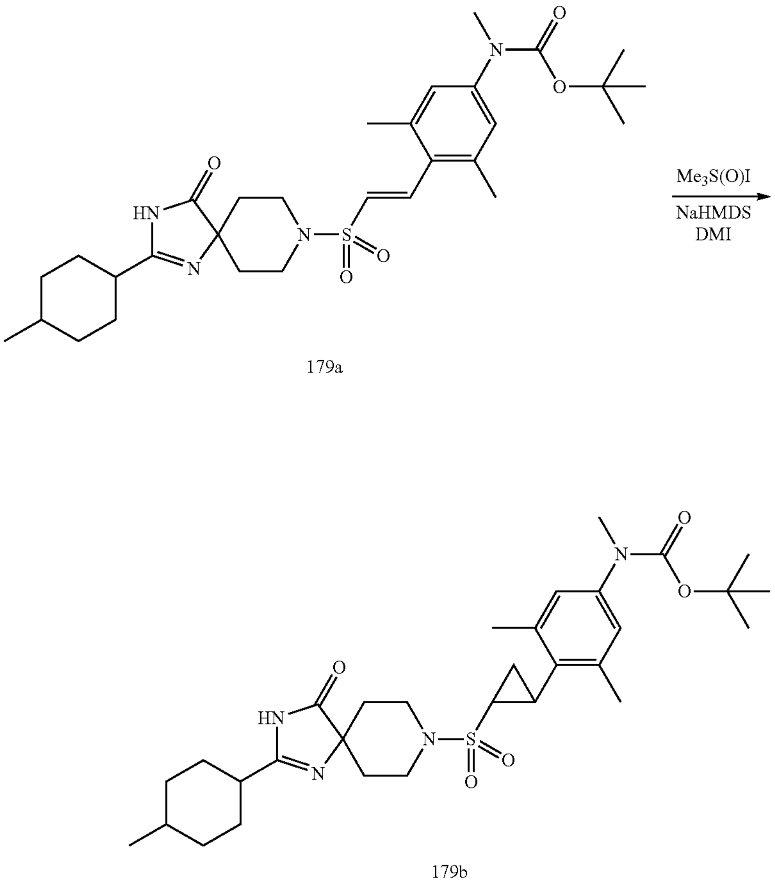

179a

179b (Reaction 179-3)

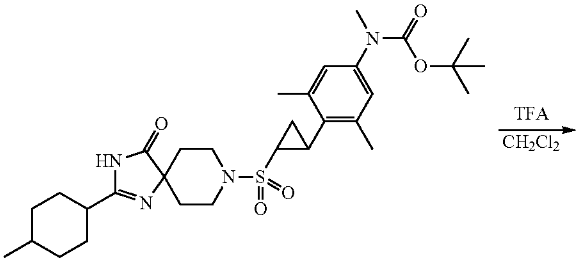

179b

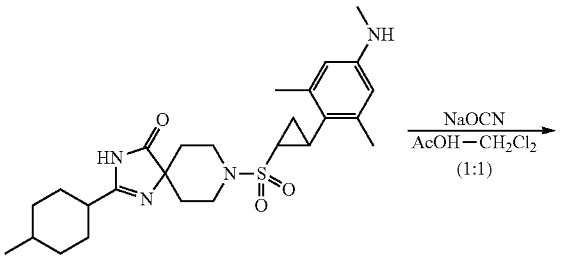

179c

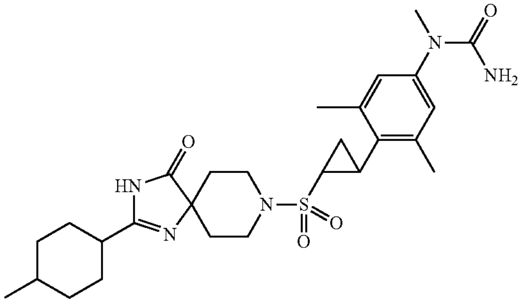

Compound 740

+

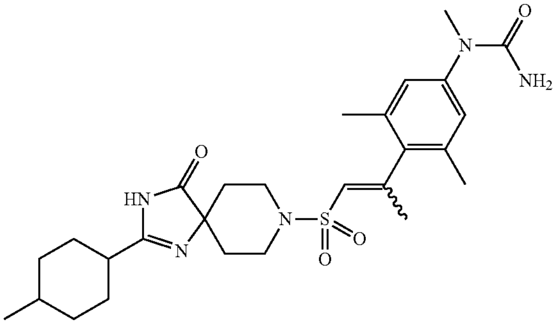

Compound 741

1-(3,5-Dimethyl-4-{2-[2-(4-methyl-cyclohexyl)-4-oxo-1,3,8-triaza-spiro[4.5]dec-1-ene-8-sulfonyl]-cyclopropyl}-phenyl)-1-methyl-urea MS (ESI) m/z=530 (M+H)+ and 1-(3,5-dimethyl-4-{1-methyl-2-[2-(4-methyl-cyclohexyl)-4-oxo-1,3,8-triaza-spiro[4.5]dec-1-ene-8-sulfonyl]-vinyl}-phenyl)-1-methyl-urea MS (ESI) m/z=530 (M+H)+ were synthesized by operations similar to those in Reaction 7-2 and Reaction 89-2 using appropriate reagents and starting material.

Example 180

N-(3-Methyl-4-{(E)-2-[4-oxo-2-(3-trifluoromethoxy-phenyl)-1,3,8-triaza-spiro[4.5]dec-1-ene-8-sulfonyl]-vinyl}-phenyl)-sulfamide (Compound 742)

(Reaction 180-1)

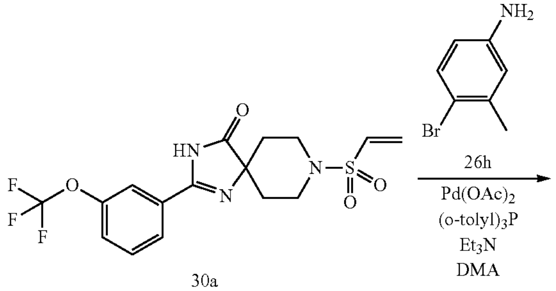

30a

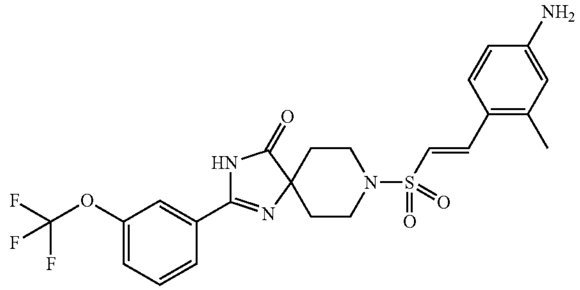

180a

8-[(E)-2-(4-Amino-2-methyl-phenyl)-ethenesulfonyl]-2-(3-trifluoromethoxy-phenyl)-1,3,8-triaza-spiro[4.5]dec-1-en-4-one was synthesized by operations similar to those in Reaction 26-1 using appropriate reagents and starting material.

MS (ESI) m/z=509 (M+H)+

(Reaction 180-2)

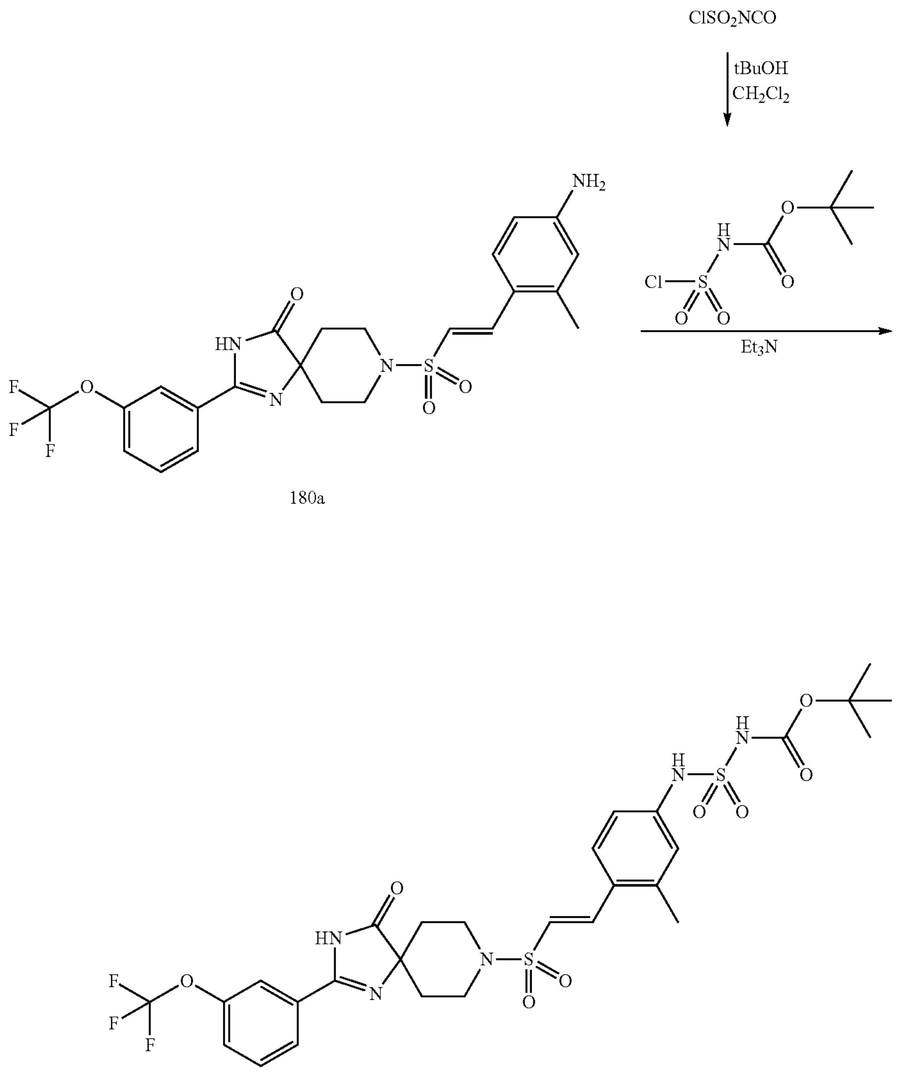

180a

180b

A solution of tBuOH (71.9 mg, 0.97 mmol) in dichloromethane (1.5 ml) was added to a solution of chlorosulfonyl isocyanate (137 mg, 0.97 mmol) in dichloromethane (3 ml) with stirring under ice-cooling. The mixture was stirred at 0° C. for 10 minutes and then added to a solution of 8-[(E)-2-(4-amino-2-methyl-phenyl)-ethenesulfonyl]-2-(3-trifluoromethoxy-phenyl)-1,3,8-triaza-spiro[4.5]dec-1-en-4-one (400 mg, 0.81 mmol) and triethylamine (164 mg, 1.62 mmol) in dichloromethane (3 ml). The mixture was stirred for one hour, and then quenched with water and extracted with dichloromethane. The organic layer was washed with saturated brine, and then dried over anhydrous magnesium sulfate and concentrated under reduced pressure. The resulting residue was purified by silica gel column chromatography (ethyl acetate-hexane) to give N-tert-butoxycarbonyl-N'-(3-methyl-4-{(E)-2-[4-oxo-2-(3-trifluoromethoxy-phenyl)-1,3,8-triaza-spiro[4.5]dec-1-ene-8-sulfonyl]-vinyl}-phenyl)-sulfamide (334 mg, 60%).

$^1$H-NMR (400 MHz, $CDCl_3$) δ 1.42 (9H, s), 1.78 (2H, dt, J=14.2, 3.9 Hz), 2.04-2.14 (2H, m), 2.40 (3H, s), 3.43 (2H, ddd, J=12.7, 9.8, 2.9 Hz), 3.74 (2H, dt, J=12.2, 4.4 Hz), 6.64 (1H, d, J=15.6 Hz), 7.08-7.11 (2H, m), 7.38 (1H, d, J=8.3 Hz), 7.48-7.54 (2H, m), 7.68 (1H, d, J=15.1 Hz), 7.73 (1H, d, J=7.8 Hz), 7.76 (1H, s), 9.62 (1H, s);

MS (ESI) m/z=668 (M+H)+.

(Reaction 180-3)

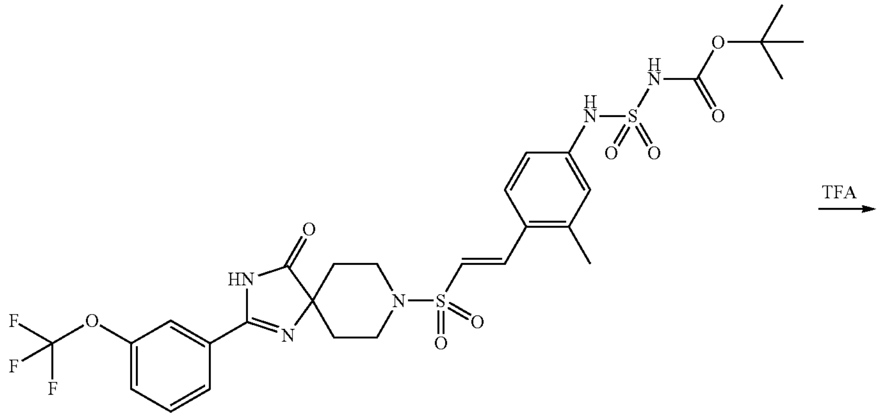

180b

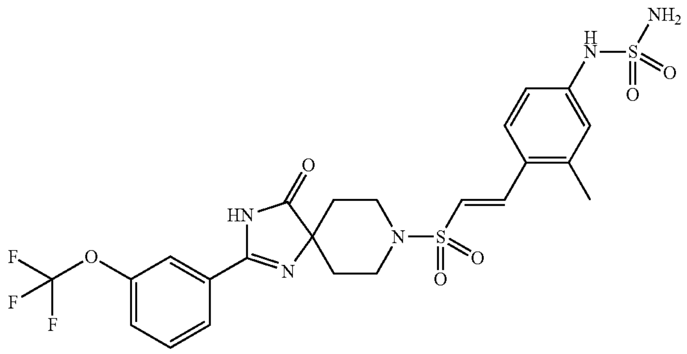

Compound 742

N-(3-Methyl-4-{(E)-2-[4-oxo-2-(3-trifluoromethoxy-phenyl)-1,3,8-triaza-spiro[4.5]dec-1-ene-8-sulfonyl]-vinyl}-phenyl)-sulfamide was synthesized by operations similar to those in Reaction 4-1 using appropriate reagents and starting material.

MS (ESI) m/z=588 (M+H)+.

Example 181

N-(3-Hydroxy-propyl)-N'-(3-methyl-4-{(E)-2-[4-oxo-2-(3-trifluoromethoxy-phenyl)-1,3,8-triaza-spiro[4.5]dec-1-ene-8-sulfonyl]-vinyl}-phenyl)-sulfamide (Compound 743)

(Reaction 181-1)

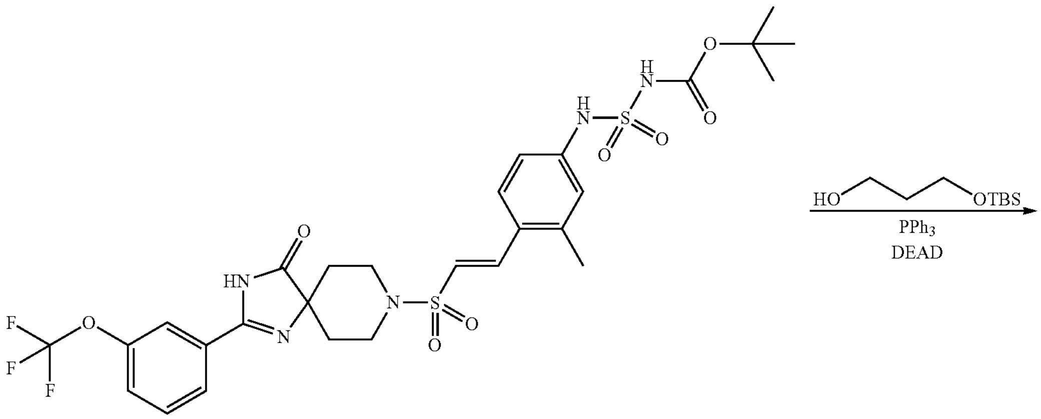

180b

-continued
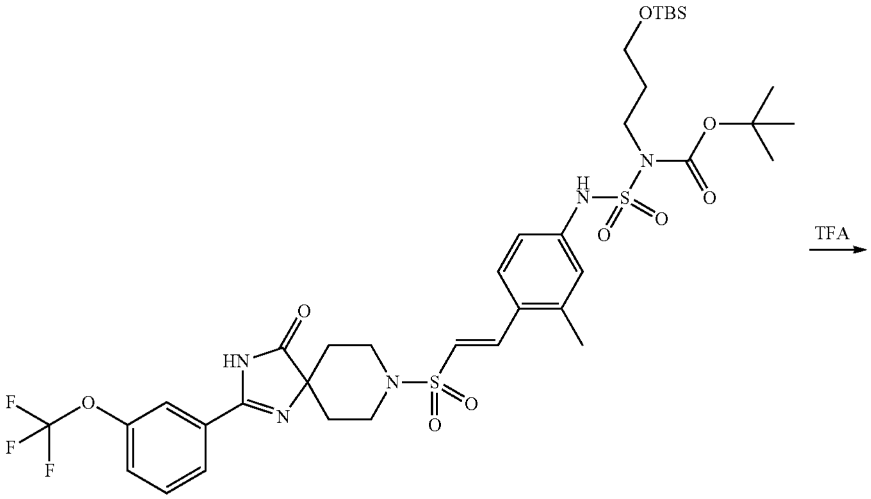
181a
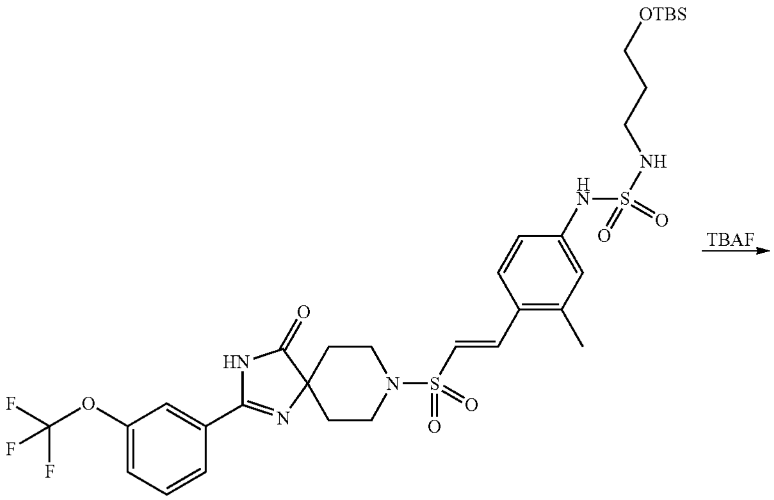
181b
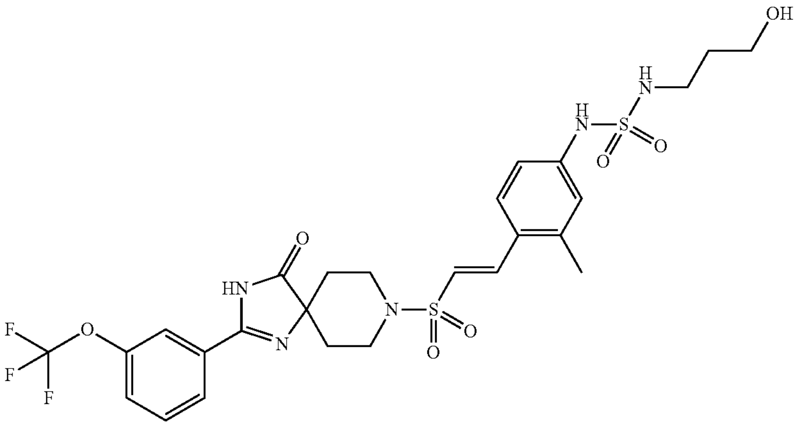
Compound 743

N-(3-Hydroxy-propyl)-N'-(3-methyl-4-{(E)-2-[4-oxo-2-(3-trifluoromethoxy-phenyl)-1,3,8-triaza-spiro[4.5]dec-1-ene-8-sulfonyl]-vinyl}-phenyl)-sulfamide was synthesized by operations similar to those in Reaction 31-7, Reaction 4-1 and Reaction 39-2 using appropriate reagents and starting material.

MS (ESI) m/z=646 (M+H)+.

Example 182

N-Methyl-N-(3-methyl-4-{(E)-3-[2-(4-methyl-cyclohexyl)-4-oxo-1,3,8-triaza-spiro[4.5]dec-1-ene-8-sulfonyl]-propenyl}-phenyl)-acetamide (Compound 744)

(Reaction 182-1)

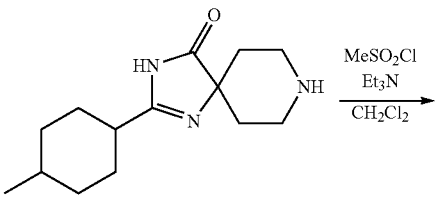

11j

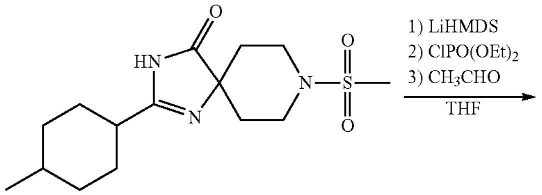

182a

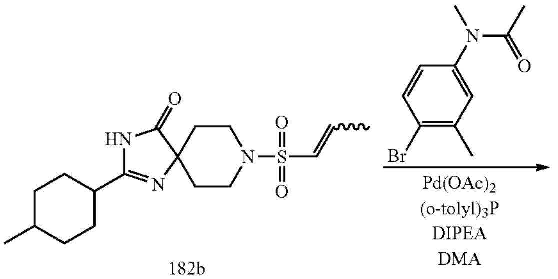

182b

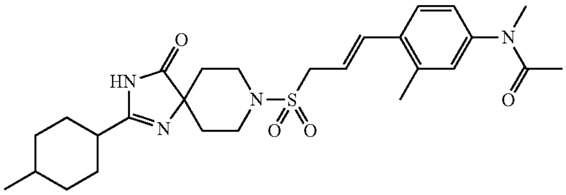

Compound 744

N-Methyl-N-(3-methyl-4-{(E)-3-[2-(4-methyl-cyclohexyl)-4-oxo-1,3,8-triaza-spiro[4.5]dec-1-ene-8-sulfonyl]-propenyl}-phenyl)-acetamide was synthesized by operations similar to those in Reaction 5-4, Reaction 55-2 and Reaction 26-1 using appropriate reagents and starting material.

MS (ESI) m/z=515 (M+H)+.

Example 183

2-Cyclohexyl-8-[2-(2-methyl-1H-indol-4-yl)-ethanesulfonyl]-1,3,8-triaza-spiro[4.5]dec-1-en-4-one (Compound 745)

(Reaction 183-1)

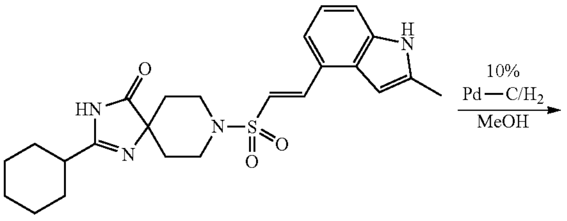

Compound 637

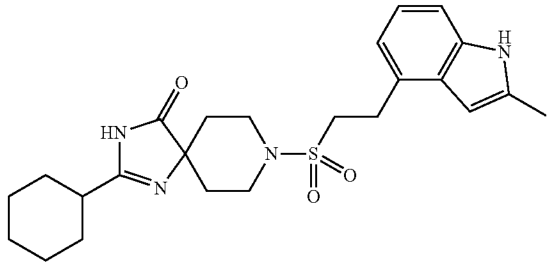

Compound 745

2-Cyclohexyl-8-[2-(2-methyl-1H-indol-4-yl)-ethanesulfonyl]-1,3,8-triaza-spiro[4.5]dec-1-en-4-one (Compound 745) was obtained by operations similar to those in Reaction 18-2 using Compound 637 as a starting material.

MS (ESI) m/z=457 (M+H)+.

The example compounds shown below were obtained by operations similar to those in Example 183 using appropriate solvents (methanol or dimethylformamide or a methanol-dimethylformamide mixed solution) and starting compounds.

Compounds 746 to Compound 749
TABLE 110
| Starting Compound | Target Compound | Structure | LCMS condition | Retention time (min) | MS (m/z) |
|---|---|---|---|---|---|
| 526 | 746 | 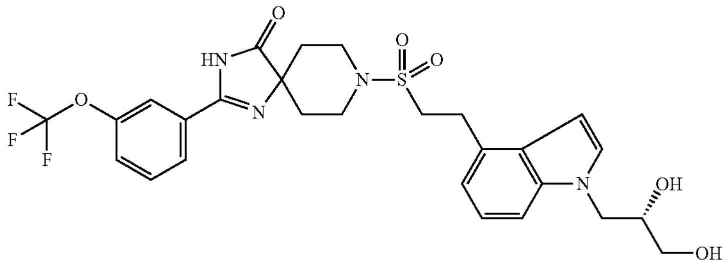 [SMILES: O=C1NC(c2cccc(OC(F)(F)F)c2)=NC12CCN(S(=O)(=O)CCc1cccc3c1ccn3C[C@H](O)CO)CC2] | LCMS-C-1 | 2.58 | 595 (M + H)+ |
| 638 | 747 | 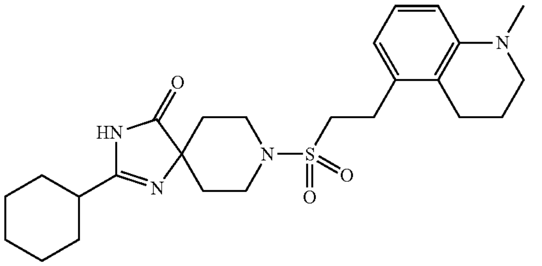 [SMILES: CN1CCCc2c(CCS(=O)(=O)N3CCC4(CC3)N=C(C3CCCCC3)NC4=O)cccc21] | LCMS-A-1 | 1.40 | 473 (M + H)+ |
| 480 | 748 | 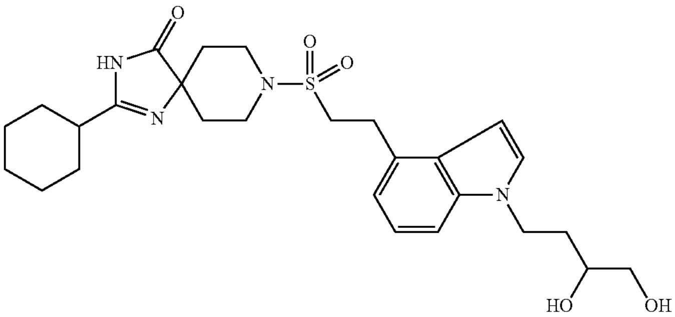 [SMILES: O=C1NC(C2CCCCC2)=NC12CCN(S(=O)(=O)CCc1cccc3c1ccn3CCC(O)CO)CC2] | LCMS-C-1 | 2.43 | 531 (M + H)+ |
| 583 | 749 | 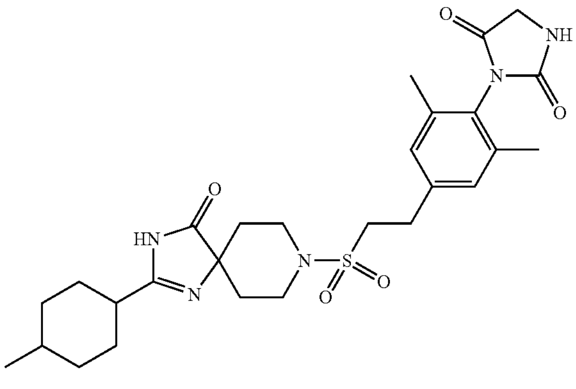 [SMILES: Cc1cc(CCS(=O)(=O)N2CCC3(CC2)N=C(C2CCC(C)CC2)NC3=O)cc(C)c1N1C(=O)CNC1=O] | LCMS-A-1 | 1.91 | 544 (M + H)+ |

Example 184

2-(3-Methyl-4-{2-[2-(4-methyl-cyclohexyl)-4-oxo-1,3,8-triaza-spiro[4.5]dec-1-ene-8-sulfonyl]-ethyl}-phenyl)-acetamide (Compound 750)

(Reaction 184-1)

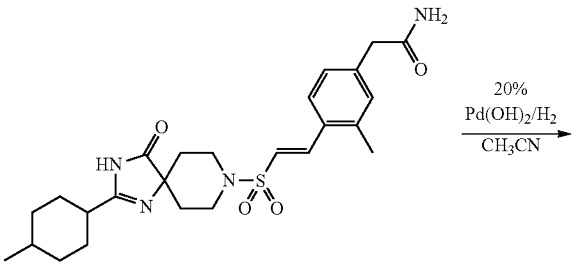

Compound 737

-continued

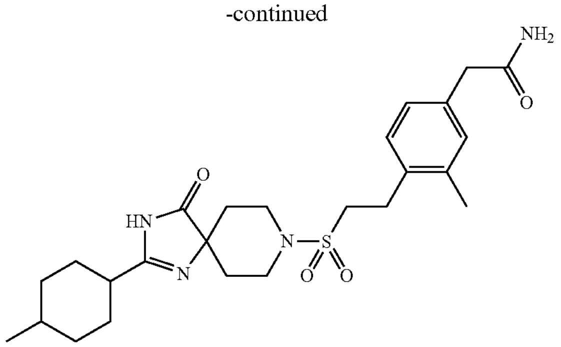

Compound 750

20% palladium hydroxide (7.4 mg) was added to a solution of Compound 737 (14.7 mg, 0.030 mmol) in acetonitrile (1.0 mL), and the mixture was stirred at room temperature for one hour in a hydrogen atmosphere. The reaction mixture was filtered through celite, and the filtrate was concentrated under reduced pressure. The resulting residue was then purified by silica gel column chromatography to give 2-(3-methyl-4-{2-[2-(4-methyl-cyclohexyl)-4-oxo-1,3,8-triaza-spiro[4.5]dec-1-ene-8-sulfonyl]-ethyl}-phenyl)-acetamide (Compound 750) as a white powder (10.6 mg, 72%).

The example compounds shown below were obtained by operations similar to those in Example 184 using appropriate solvents (acetonitrile or methanol or an acetonitrile-methanol mixed solution) and starting compounds.

Compounds 751 to Compound 834

TABLE 111

| Starting Compound | Target Compound | Structure | LCMS condition | Retention time (min) | MS (m/z) |
|---|---|---|---|---|---|
| 509 | 751 | 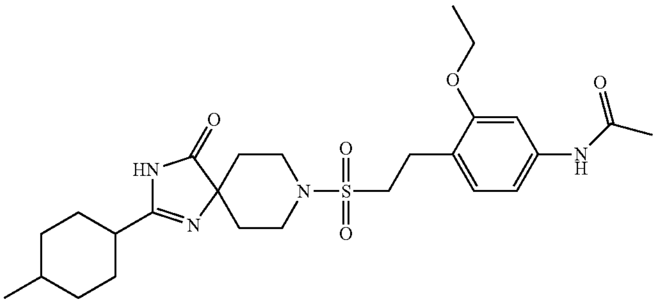 [SMILES: CCOc1cc(NC(C)=O)ccc1CCS(=O)(=O)N1CCC2(CC1)N=C(C1CCC(C)CC1)NC2=O] | LCMS-D-1 | 2.57 | 519 (M + H)+ |
| 510 | 752 | 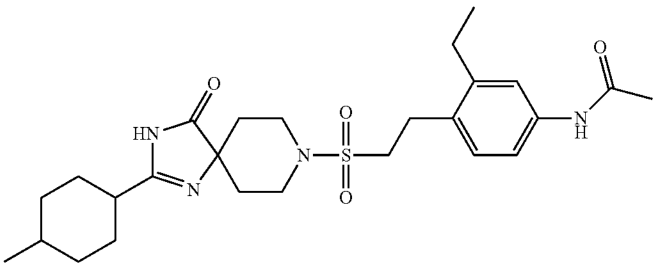 [SMILES: CCc1cc(NC(C)=O)ccc1CCS(=O)(=O)N1CCC2(CC1)N=C(C1CCC(C)CC1)NC2=O] | LCMS-D-1 | 2.53 | 503 (M + H)+ |

TABLE 111-continued
| Starting Compound | Target Compound | Structure | LCMS condition | Retention time (min) | MS (m/z) |
|---|---|---|---|---|---|
| 576 | 753 | 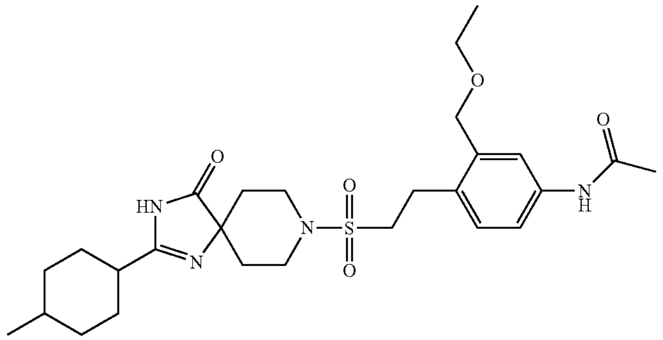 [SMILES: CCOCc1cc(NC(C)=O)ccc1CCS(=O)(=O)N1CCC2(CC1)N=C(C1CCC(C)CC1)NC2=O] | LCMS-D-1 | 2.48 | 533 (M + H)+ |
| 512 | 754 | 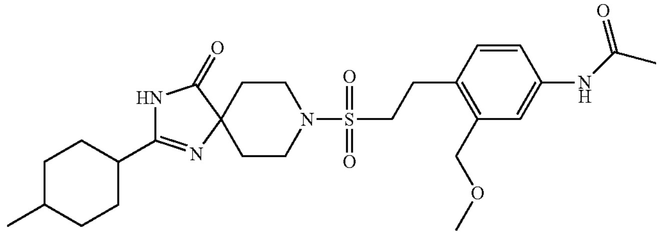 [SMILES: COCc1cc(NC(C)=O)ccc1CCS(=O)(=O)N1CCC2(CC1)N=C(C1CCC(C)CC1)NC2=O] | LCMS-D-1 | 2.33 | 519 (M + H)+ |
| 542 | 755 | 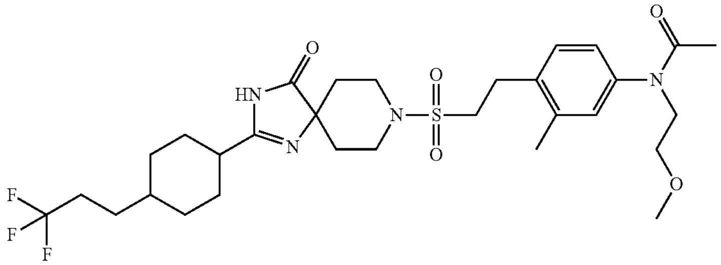 [SMILES: COCCN(C(C)=O)c1ccc(CCS(=O)(=O)N2CCC3(CC2)N=C(C2CCC(CCC(F)(F)F)CC2)NC3=O)c(C)c1] | LCMS-D-1 | 2.30 | 629 (M + H)+ |
| 543 | 756 | 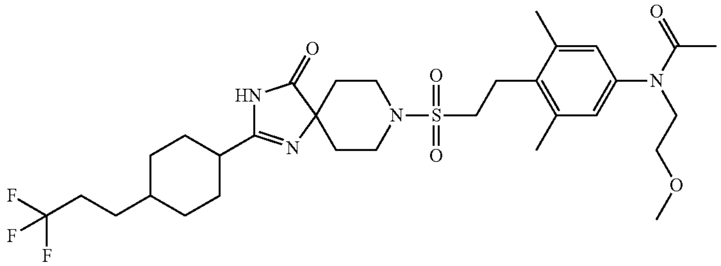 [SMILES: COCCN(C(C)=O)c1cc(C)c(CCS(=O)(=O)N2CCC3(CC2)N=C(C2CCC(CCC(F)(F)F)CC2)NC3=O)c(C)c1] | LCMS-D-1 | 2.43 | 643 (M + H)+ |
| 545 | 757 | 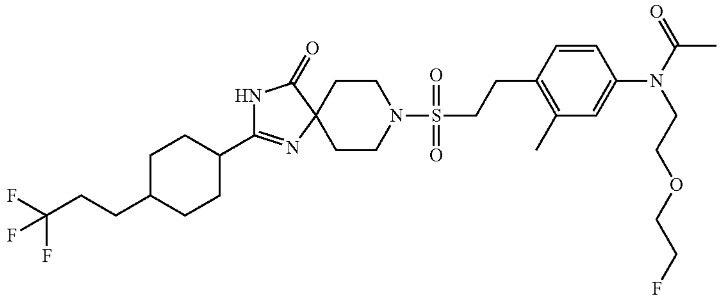 [SMILES: CC(=O)N(CCOCCF)c1ccc(CCS(=O)(=O)N2CCC3(CC2)N=C(C2CCC(CCC(F)(F)F)CC2)NC3=O)c(C)c1] | LCMS-D-1 | 2.30 | 661 (M + H)+ |

TABLE 111-continued
| Starting Compound | Target Compound | Structure | LCMS condition | Retention time (min) | MS (m/z) |
|---|---|---|---|---|---|
| 544 | 758 | 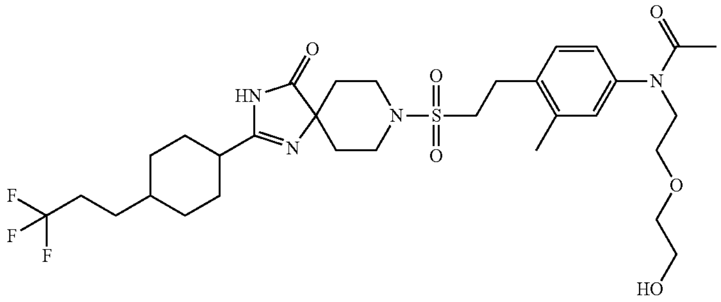 [SMILES: CC(=O)N(CCOCCO)c1ccc(CCS(=O)(=O)N2CCC3(CC2)N=C(C2CCC(CCC(F)(F)F)CC2)NC3=O)c(C)c1] | LCMS-D-1 | 2.11 | 659 (M + H)+ |
| 546 | 759 | 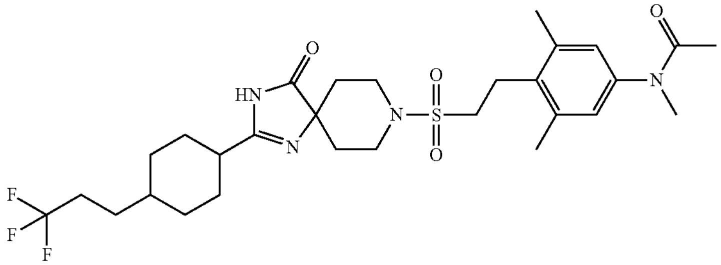 [SMILES: CC(=O)N(C)c1cc(C)c(CCS(=O)(=O)N2CCC3(CC2)N=C(C2CCC(CCC(F)(F)F)CC2)NC3=O)c(C)c1] | LCMS-D-1 | 1.56 | 599 (M + H)+ |
| 548 | 760 | 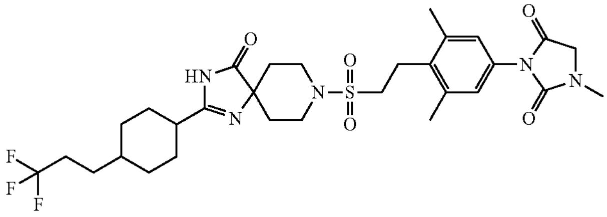 [SMILES: Cc1cc(N2C(=O)CN(C)C2=O)cc(C)c1CCS(=O)(=O)N1CCC2(CC1)N=C(C1CCC(CCC(F)(F)F)CC1)NC2=O] | LCMS-D-1 | 2.08 | 640 (M + H)+ |
| 549 | 761 | 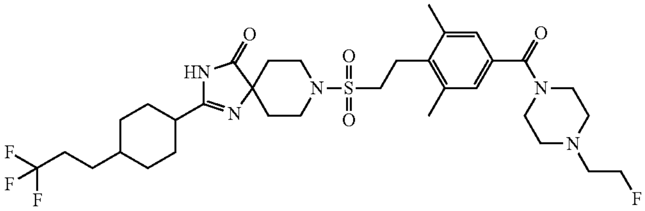 [SMILES: Cc1cc(C(=O)N2CCN(CCF)CC2)cc(C)c1CCS(=O)(=O)N1CCC2(CC1)N=C(C1CCC(CCC(F)(F)F)CC1)NC2=O] | LCMS-D-1 | 1.62 | 686 (M + H)+ |
| 550 | 764 | 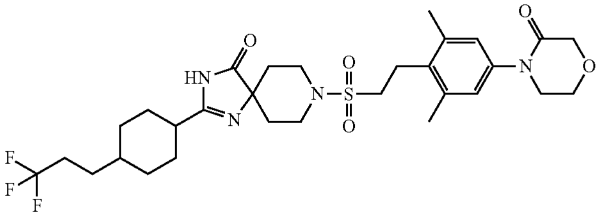 [SMILES: Cc1cc(N2CCOCC2=O)cc(C)c1CCS(=O)(=O)N1CCC2(CC1)N=C(C1CCC(CCC(F)(F)F)CC1)NC2=O] | LCMS-D-1 | 2.22 | 627 (M + H)+ |
| 515 | 765 | 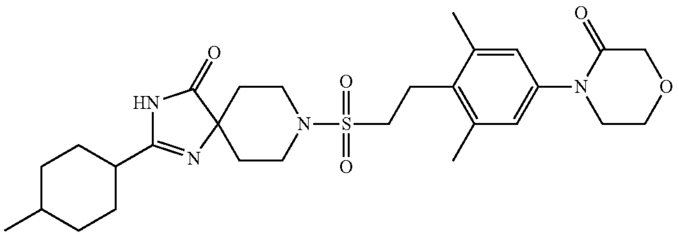 [SMILES: Cc1cc(N2CCOCC2=O)cc(C)c1CCS(=O)(=O)N1CCC2(CC1)N=C(C1CCC(C)CC1)NC2=O] | LCMS-D-1 | 1.80 | 545 (M + H)+ |

TABLE 111-continued
| Starting Com-pound | Target Com-pound | Structure | LCMS condition | Reten-tion time (min) | MS (m/z) |
|---|---|---|---|---|---|
| 551 | 766 | 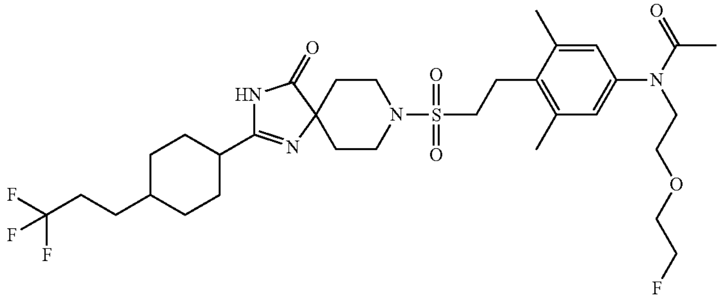 [SMILES: CC(=O)N(CCOCCF)c1cc(C)c(CCS(=O)(=O)N2CCC3(CC2)N=C(C2CCC(CCC(F)(F)F)CC2)NC3=O)c(C)c1] | LCMS-D-1 | 2.42 | 675 (M + H)+ |
| 582 | 767 | 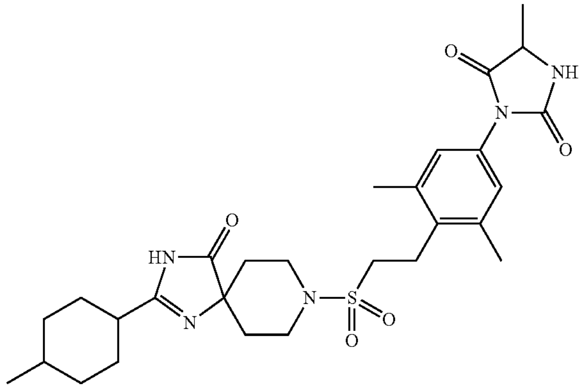 [SMILES: Cc1cc(N2C(=O)NC(C)C2=O)cc(C)c1CCS(=O)(=O)N1CCC2(CC1)N=C(C1CCC(C)CC1)NC2=O] | LCMS-A-1 | 2.03 | 558 (M + H)+ |
| 547 | 768 | 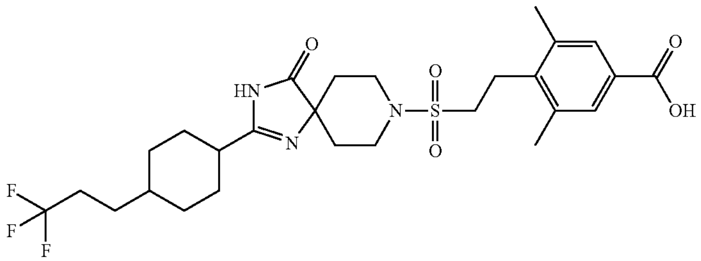 [SMILES: Cc1cc(C(=O)O)cc(C)c1CCS(=O)(=O)N1CCC2(CC1)N=C(C1CCC(CCC(F)(F)F)CC1)NC2=O] | LCMS-D-1 | 2.57 | 572 (M + H)+ |
| 552 | 769 | 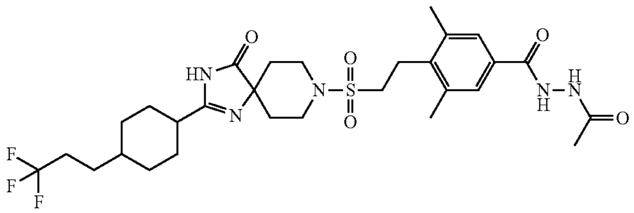 [SMILES: CC(=O)NNC(=O)c1cc(C)c(CCS(=O)(=O)N2CCC3(CC2)N=C(C2CCC(CCC(F)(F)F)CC2)NC3=O)c(C)c1] | LCMS-D-1 | 2.03 | 628 (M + H)+ |
| 553 | 770 | 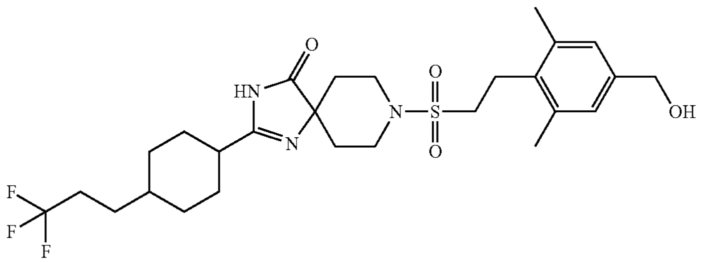 [SMILES: Cc1cc(CO)cc(C)c1CCS(=O)(=O)N1CCC2(CC1)N=C(C1CCC(CCC(F)(F)F)CC1)NC2=O] | LCMS-D-1 | 2.38 | 558 (M + H)+ |

TABLE 111-continued
| Starting Compound | Target Compound | Structure | LCMS condition | Retention time (min) | MS (m/z) |
|---|---|---|---|---|---|
| 516 | 771 | 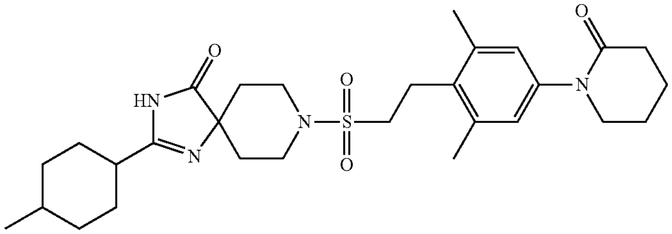 [SMILES: Cc1cc(N2CCCCC2=O)cc(C)c1CCS(=O)(=O)N1CCC2(CC1)N=C(C1CCC(C)CC1)NC2=O] | LCMS-D-1 | 2.58 | 543 (M + H)+ |
| 554 | 772 | 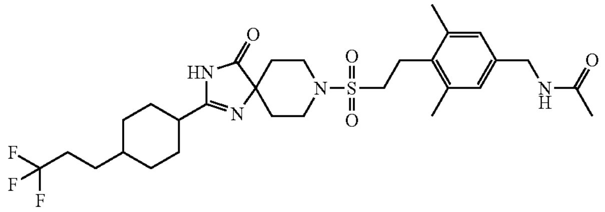 [SMILES: CC(=O)NCc1cc(C)c(CCS(=O)(=O)N2CCC3(CC2)N=C(C2CCC(CCC(F)(F)F)CC2)NC3=O)c(C)c1] | LCMS-D-1 | 2.47 | 599 (M + H)+ |
| 552 | 773 | 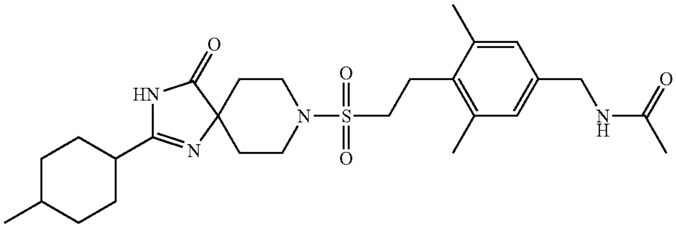 [SMILES: CC(=O)NCc1cc(C)c(CCS(=O)(=O)N2CCC3(CC2)N=C(C2CCC(C)CC2)NC3=O)c(C)c1] | LCMS-D-1 | 2.08 | 517 (M + H)+ |
| 554 | 774 | 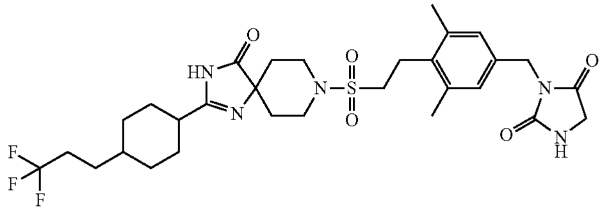 [SMILES: Cc1cc(CN2C(=O)CNC2=O)cc(C)c1CCS(=O)(=O)N1CCC2(CC1)N=C(C1CCC(CCC(F)(F)F)CC1)NC2=O] | LCMS-D-1 | 2.32 | 640 (M + H)+ |
| 555 | 775 | 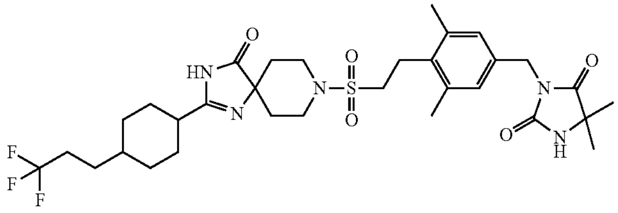 [SMILES: Cc1cc(CN2C(=O)NC(C)(C)C2=O)cc(C)c1CCS(=O)(=O)N1CCC2(CC1)N=C(C1CCC(CCC(F)(F)F)CC1)NC2=O] | LCMS-D-1 | 2.57 | 668 (M + H)+ |
| 556 | 776 | 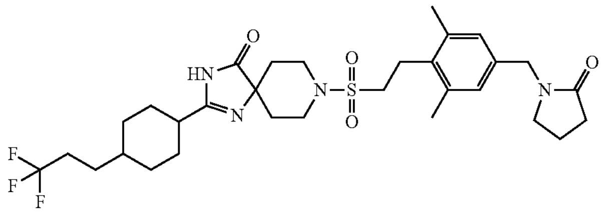 [SMILES: Cc1cc(CN2CCCC2=O)cc(C)c1CCS(=O)(=O)N1CCC2(CC1)N=C(C1CCC(CCC(F)(F)F)CC1)NC2=O] | LCMS-D-1 | 2.50 | 625 (M + H)+ |

TABLE 111-continued
| Starting Compound | Target Compound | Structure | LCMS condition | Retention time (min) | MS (m/z) |
|---|---|---|---|---|---|
| 557 | 777 | 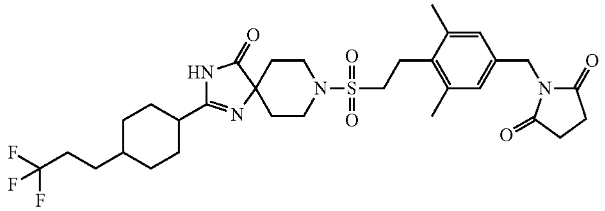 [SMILES: Cc1cc(CN2C(=O)CCC2=O)cc(C)c1CCS(=O)(=O)N1CCC2(CC1)N=C(C1CCC(CCC(F)(F)F)CC1)NC2=O] | LCMS-D-1 | 2.45 | 639 (M + H)+ |
| 581 | 778 | 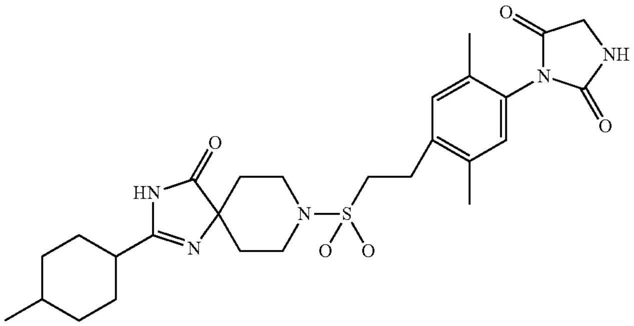 [SMILES: Cc1cc(N2C(=O)CNC2=O)c(C)cc1CCS(O)(O)N1CCC2(CC1)N=C(C1CCC(C)CC1)NC2=O] | LCMS-C-1 | 2.42 | 544 (M + H)+ |
| 518 | 779 | 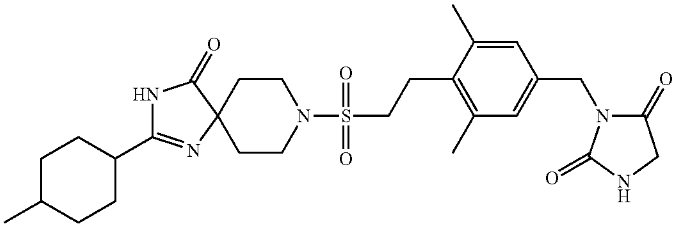 | LCMS-D-1 | 1.93 | 558 (M + H)+ |
| 519 | 780 | 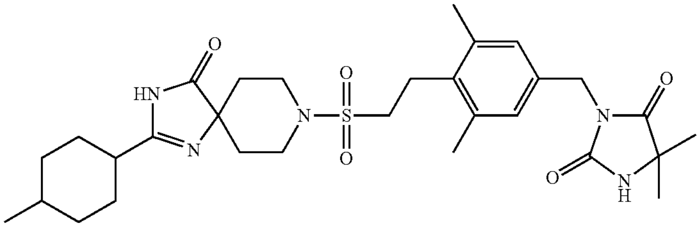 | LCMS-D-1 | 2.20 | 586 (M + H)+ |
| 520 | 781 | 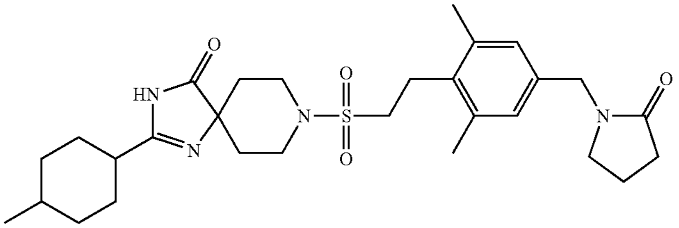 [SMILES: Cc1cc(CN2CCCC2=O)cc(C)c1CCS(=O)(=O)N1CCC2(CC1)N=C(C1CCC(C)CC1)NC2=O] | LCMS-D-1 | 2.10 | 543 (M + H)+ |
| 557 | 782 | 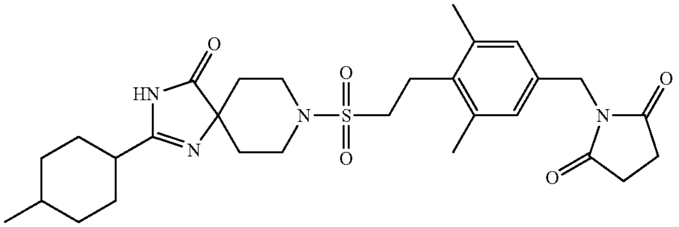 [SMILES: Cc1cc(CN2C(=O)CCC2=O)cc(C)c1CCS(=O)(=O)N1CCC2(CC1)N=C(C1CCC(C)CC1)NC2=O] | LCMS-D-1 | 1.98 | 557 (M + H)+ |

TABLE 111-continued
| Starting Compound | Target Compound | Structure | LCMS condition | Retention time (min) | MS (m/z) |
|---|---|---|---|---|---|
| 584 | 783 | 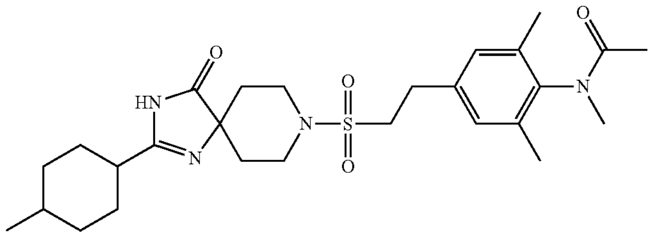 [SMILES: CC(=O)N(C)c1c(C)cc(CCS(=O)(=O)N2CCC3(CC2)N=C(C2CCC(C)CC2)NC3=O)cc1C] | LCMS-D-1 | 1.96 | 517 (M + H)+ |
| 559 | 784 | 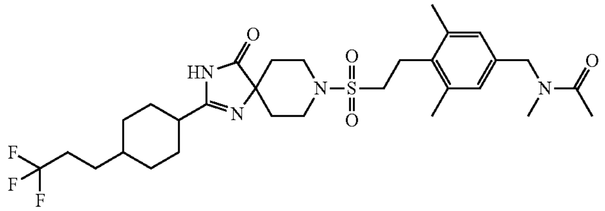 [SMILES: CC(=O)N(C)Cc1cc(C)c(CCS(=O)(=O)N2CCC3(CC2)N=C(C2CCC(CCC(F)(F)F)CC2)NC3=O)c(C)c1] | LCMS-D-1 | 2.47 | 613 (M + H)+ |
| 517 | 785 | 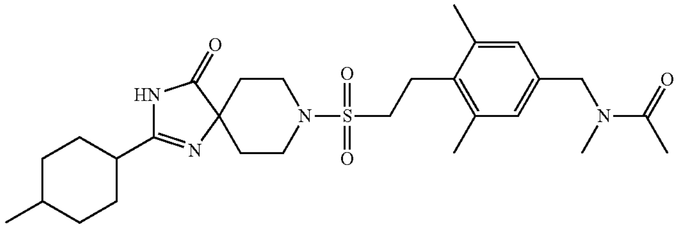 | LCMS-D-1 | 2.10 | 531 (M + H)+ |
| 587 | 786 | 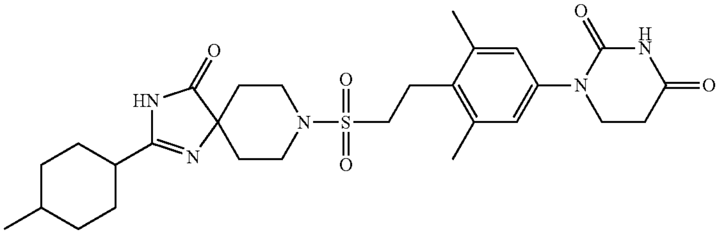 [SMILES: Cc1cc(N2CCC(=O)NC2=O)cc(C)c1CCS(=O)(=O)N1CCC2(CC1)N=C(C1CCC(C)CC1)NC2=O] | LCMS-D-1 | 1.72 | 558 (M + H)+ |
| 629 | 787 | 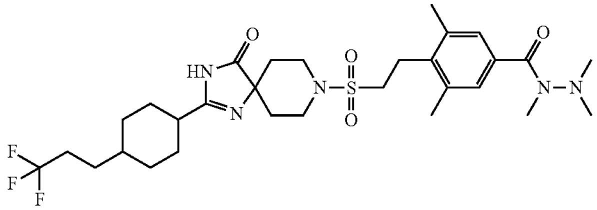 [SMILES: Cc1cc(C(=O)N(C)N(C)C)cc(C)c1CCS(=O)(=O)N1CCC2(CC1)N=C(C1CCC(CCC(F)(F)F)CC1)NC2=O] | LCMS-D-1 | 2.40 | 628 (M + H)+ |
| 623 | 788 | 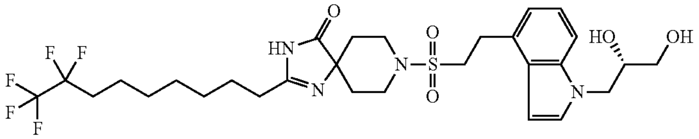 [SMILES: O=C1NC(CCCCCCCC(F)(F)C(F)(F)F)=NC12CCN(S(=O)(=O)CCc1cccc3c1ccn3C[C@H](O)CO)CC2] | LCMS-C-1 | 2.85 | 651 (M + H)+ |
| 622 | 789 | 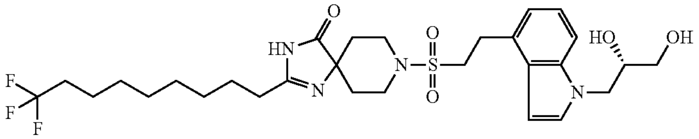 [SMILES: O=C1NC(CCCCCCCCC(F)(F)F)=NC12CCN(S(=O)(=O)CCc1cccc3c1ccn3C[C@H](O)CO)CC2] | LCMS-C-1 | 2.80 | 615 (M + H)+ |

TABLE 111-continued
| Starting Compound | Target Compound | Structure | LCMS condition | Retention time (min) | MS (m/z) |
|---|---|---|---|---|---|
| 536 | 790 | 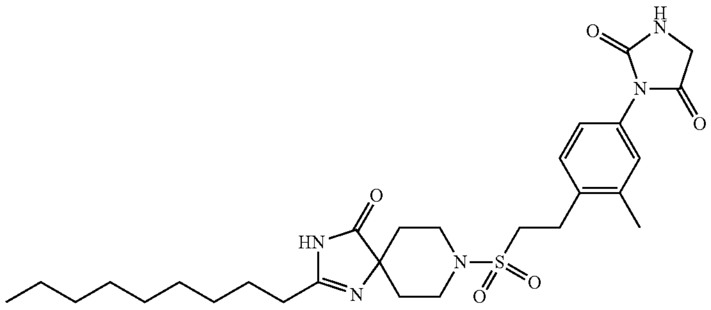 [SMILES: CCCCCCCCCC1=NC2(CCN(S(=O)(=O)CCc3ccc(N4C(=O)CNC4=O)cc3C)CC2)C(=O)N1] | LCMS-C-1 | 2.82 | 560 (M + H)+ |
| 630 | 791 | 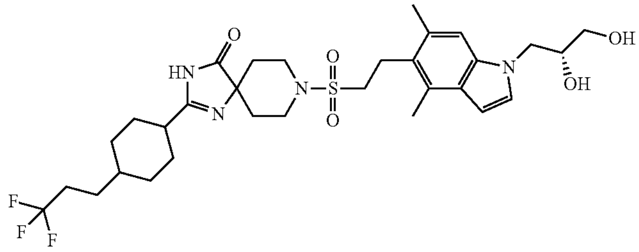 [SMILES: Cc1cc2c(ccn2C[C@@H](O)CO)c(C)c1CCS(=O)(=O)N1CCC2(CC1)N=C(C1CCC(CCC(F)(F)F)CC1)NC2=O] | LCMS-D-1 | 2.45 | 641 (M + H)+ |
| 618 | 792 | 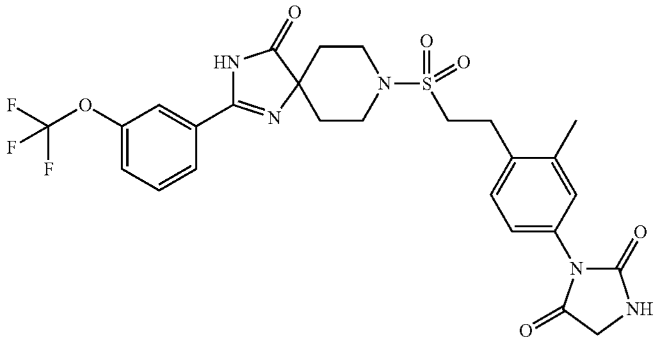 [SMILES: Cc1cc(N2C(=O)CNC2=O)ccc1CCS(=O)(=O)N1CCC2(CC1)N=C(c1cccc(OC(F)(F)F)c1)NC2=O] | LCMS-F-1 | 0.89 | 594 (M + H)+ |
| 617 | 793 | 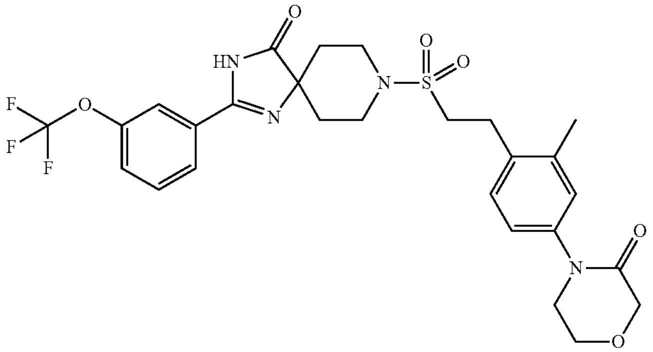 [SMILES: Cc1cc(N2CCOCC2=O)ccc1CCS(=O)(=O)N1CCC2(CC1)N=C(c1cccc(OC(F)(F)F)c1)NC2=O] | LCMS-F-1 | 0.93 | 595 (M + H)+ |

TABLE 111-continued
| Starting Compound | Target Compound | Structure | LCMS condition | Retention time (min) | MS (m/z) |
|---|---|---|---|---|---|
| 718 | 794 | 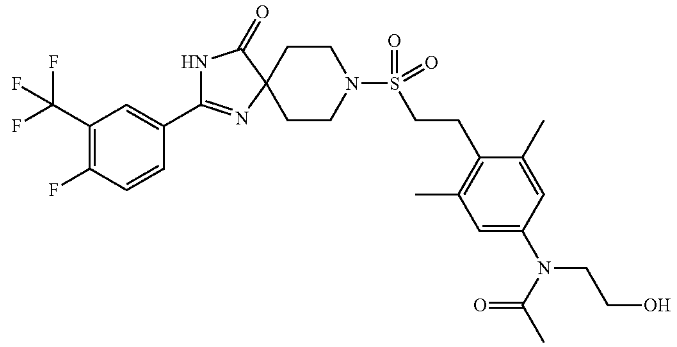 [SMILES: CC(=O)N(CCO)c1cc(C)c(CCS(=O)(=O)N2CCC3(CC2)N=C(c2ccc(F)c(C(F)(F)F)c2)NC3=O)c(C)c1] | LCMS-F-1 | 0.94 | 613 (M + H)+ |
| 537 | 795 | 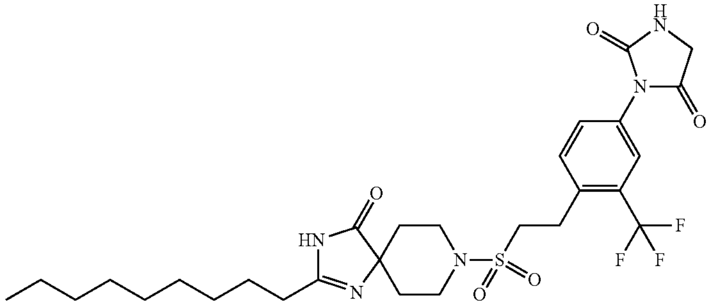 [SMILES: CCCCCCCCCC1=NC2(CCN(S(=O)(=O)CCc3ccc(N4C(=O)CNC4=O)cc3C(F)(F)F)CC2)C(=O)N1] | LCMS-A-1 | 2.53 | 614 (M + H)+ |
| 628 | 796 | 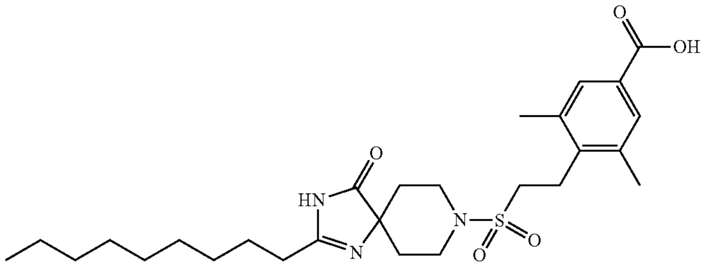 [SMILES: CCCCCCCCCC1=NC2(CCN(S(=O)(=O)CCc3c(C)cc(C(=O)O)cc3C)CC2)C(=O)N1] | LCMS-F-1 | 0.96 | 520 (M + H)+ |
| 535 | 797 | 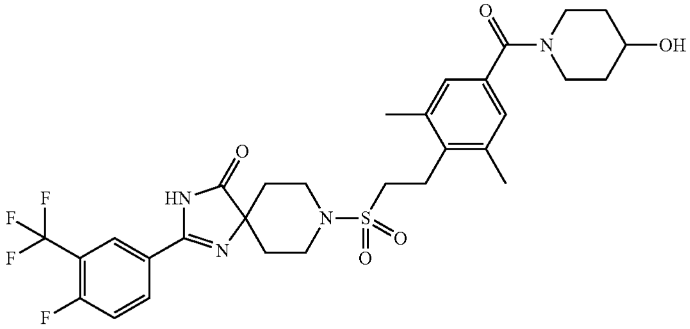 [SMILES: Cc1cc(C(=O)N2CCC(O)CC2)cc(C)c1CCS(=O)(=O)N1CCC2(CC1)N=C(c1ccc(F)c(C(F)(F)F)c1)NC2=O] | LCMS-F-1 | 0.94 | 639 (M + H)+ |
| 627 | 798 | 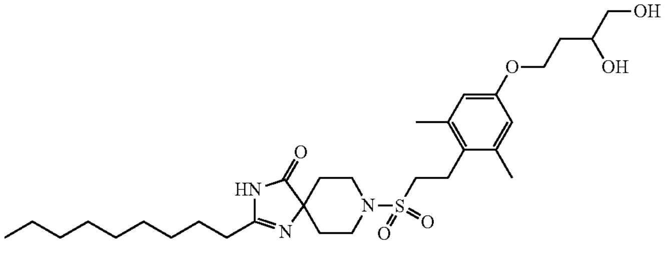 [SMILES: CCCCCCCCCC1=NC2(CCN(S(=O)(=O)CCc3c(C)cc(OCCC(O)CO)cc3C)CC2)C(=O)N1] | LCMS-A-1 | 2.43 | 580 (M + H)+ |

TABLE 111-continued
| Starting Compound | Target Compound | Structure | LCMS condition | Retention time (min) | MS (m/z) |
|---|---|---|---|---|---|
| 635 | 799 | 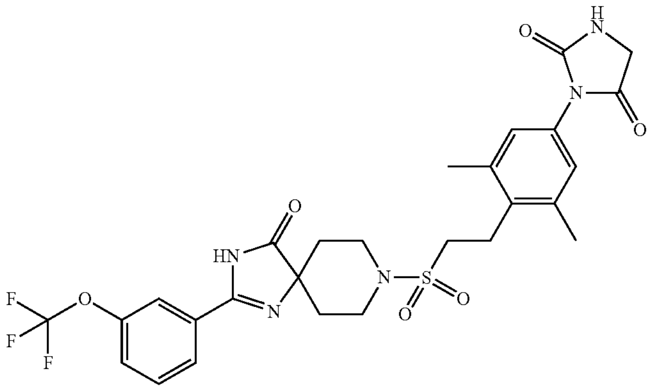 [SMILES: Cc1cc(N2C(=O)CNC2=O)cc(C)c1CCS(=O)(=O)N1CCC2(CC1)N=C(c1cccc(OC(F)(F)F)c1)NC2=O] | LCMS-F-1 | 0.91 | 608 (M + H)+ |
| 636 | 800 | 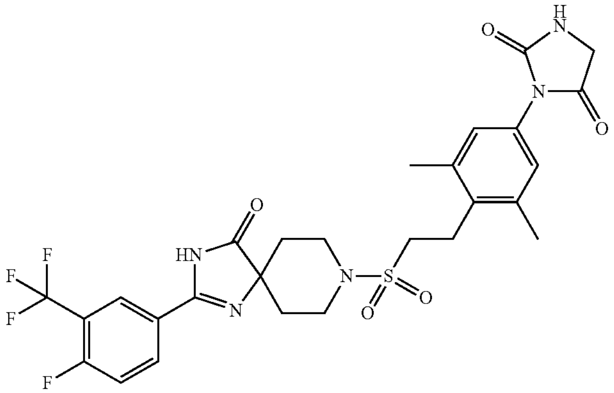 [SMILES: Cc1cc(N2C(=O)CNC2=O)cc(C)c1CCS(=O)(=O)N1CCC2(CC1)N=C(c1ccc(F)c(C(F)(F)F)c1)NC2=O] | LCMS-F-1 | 0.91 | 610 (M + H)+ |
| 639 | 801 | 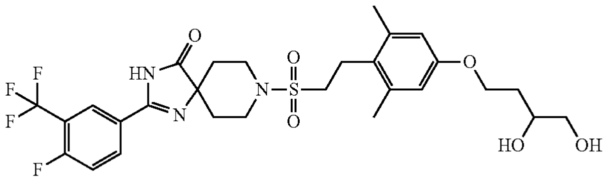 [SMILES: Cc1cc(OCCC(O)CO)cc(C)c1CCS(=O)(=O)N1CCC2(CC1)N=C(c1ccc(F)c(C(F)(F)F)c1)NC2=O] | LCMS-F-1 | 0.99 | 616 (M + H)+ |
| 641 | 802 | 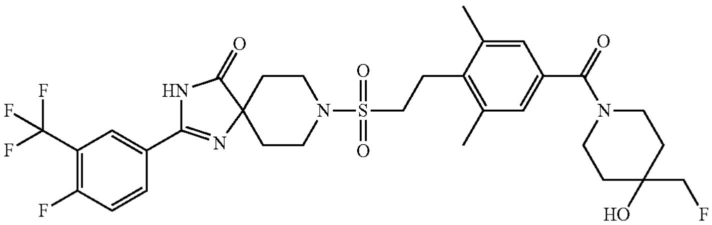 [SMILES: Cc1cc(C(=O)N2CCC(O)(CF)CC2)cc(C)c1CCS(=O)(=O)N1CCC2(CC1)N=C(c1ccc(F)c(C(F)(F)F)c1)NC2=O] | LCMS-F-1 | 0.99 | 671 (M + H)+ |
| 642 | 803 | 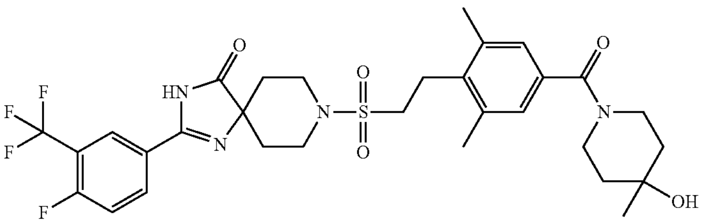 [SMILES: Cc1cc(C(=O)N2CCC(C)(O)CC2)cc(C)c1CCS(=O)(=O)N1CCC2(CC1)N=C(c1ccc(F)c(C(F)(F)F)c1)NC2=O] | LCMS-F-1 | 1.00 | 653 (M + H)+ |

TABLE 111-continued
| Starting Compound | Target Compound | Structure | LCMS condition | Retention time (min) | MS (m/z) |
|---|---|---|---|---|---|
| 644 | 804 | 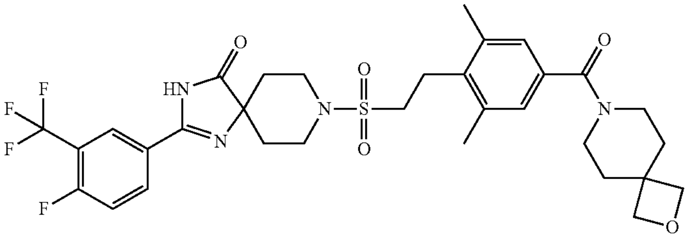 | LCMS-F-1 | 1.00 | 665 (M + H)+ |
| 506 | 812 | 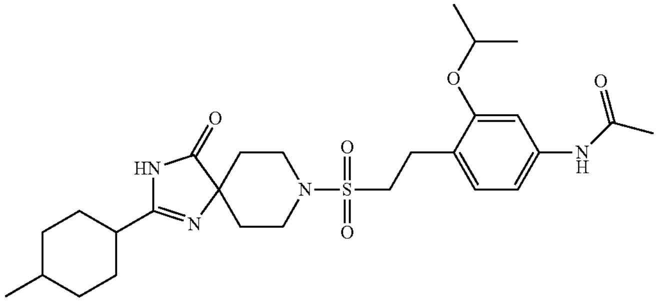 [SMILES: CC(=O)Nc1ccc(CCS(=O)(=O)N2CCC3(CC2)N=C(C2CCC(C)CC2)NC3=O)c(OC(C)C)c1] | LCMS-D-1 | 2.20 | 533 (M + H)+ |
| 692 | 817 | 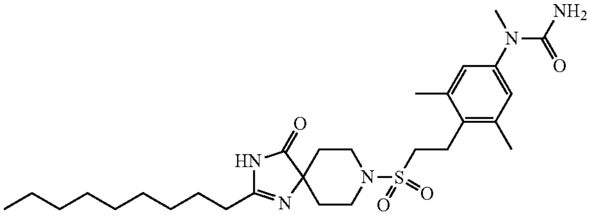 [SMILES: CCCCCCCCCC1=NC2(CCN(S(=O)(=O)CCc3c(C)cc(N(C)C(N)=O)cc3C)CC2)C(=O)N1] | LCMS-A-1 | 2.47 | 548 (M + H)+ |
| 694 | 818 | 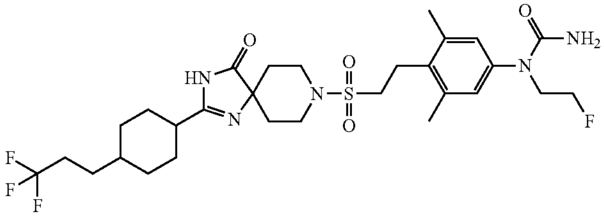 [SMILES: Cc1cc(N(CCF)C(N)=O)cc(C)c1CCS(=O)(=O)N1CCC2(CC1)N=C(C1CCC(CCC(F)(F)F)CC1)NC2=O] | LCMS-D-1 | 2.37 | 632 (M + H)+ |
| 699 | 820 | 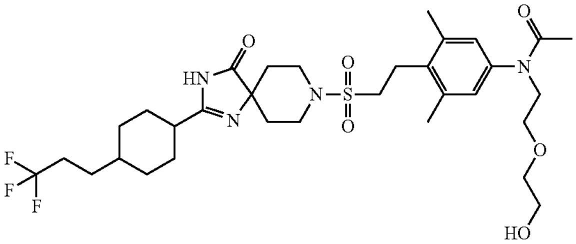 [SMILES: CC(=O)N(CCOCCO)c1cc(C)c(CCS(=O)(=O)N2CCC3(CC2)N=C(C2CCC(CCC(F)(F)F)CC2)NC3=O)c(C)c1] | LCMS-D-1 | 2.25 | 673 (M + H)+ |
| 697 | 821 | 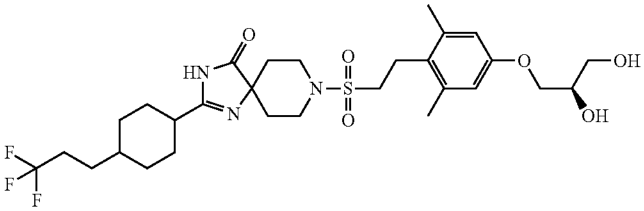 [SMILES: Cc1cc(OC[C@H](O)CO)cc(C)c1CCS(=O)(=O)N1CCC2(CC1)N=C(C1CCC(CCC(F)(F)F)CC1)NC2=O] | LCMS-D-1 | 2.21 | 618 (M + H)+ |

TABLE 111-continued
| Starting Compound | Target Compound | Structure | LCMS condition | Retention time (min) | MS (m/z) |
| --- | --- | --- | --- | --- | --- |
| 704 | 822 | 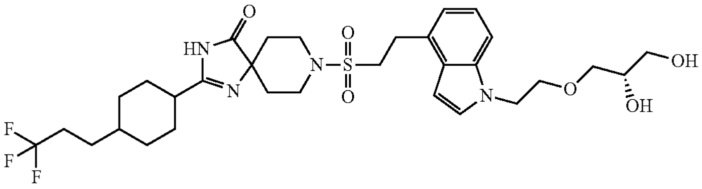 [SMILES: O=C1NC(C2CCC(CCC(F)(F)F)CC2)=NC12CCN(S(=O)(=O)CCc1cccc3c1ccn3CCOC[C@@H](O)CO)CC2] | LCMS-D-1 | 2.28 | 657 (M + H)+ |
| 706 | 823 | 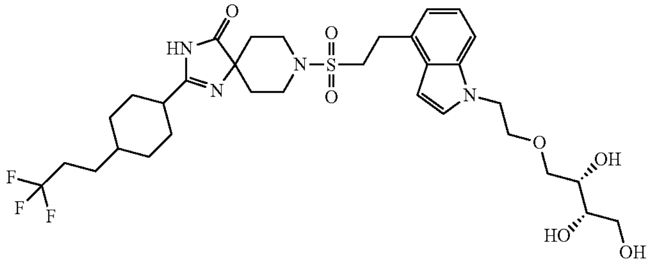 [SMILES: O=C1NC(C2CCC(CCC(F)(F)F)CC2)=NC12CCN(S(=O)(=O)CCc1cccc3c1ccn3CCOC[C@H](O)[C@@H](O)CO)CC2] | LCMS-D-1 | 2.25 | 687 (M + H)+ |
| 707 | 824 | 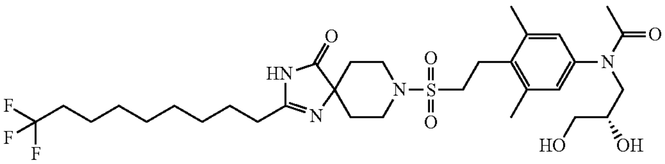 [SMILES: CC(=O)N(C[C@H](O)CO)c1cc(C)c(CCS(=O)(=O)N2CCC3(CC2)N=C(CCCCCCCCC(F)(F)F)NC3=O)c(C)c1] | LCMS-D-1 | 2.40 | 661 (M + H)+ |
| 700 | 825 | 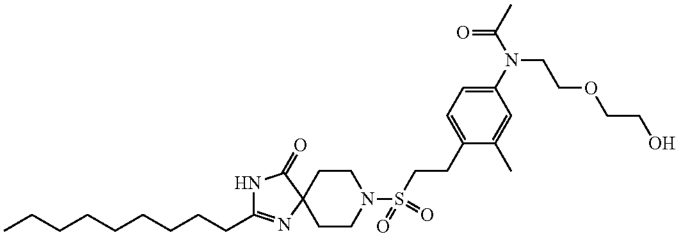 [SMILES: CCCCCCCCCC1=NC2(CCN(S(=O)(=O)CCc3ccc(N(CCOCCO)C(C)=O)cc3C)CC2)C(=O)N1] | LCMS-A-1 | 2.35 | 607 (M + H)+ |
| 724 | 826 | 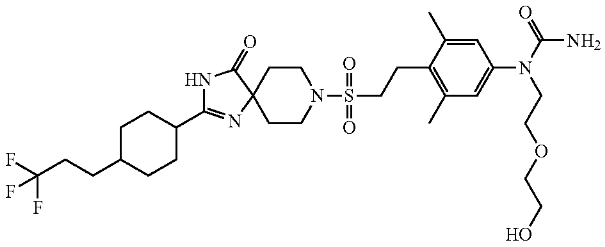 [SMILES: Cc1cc(N(CCOCCO)C(N)=O)cc(C)c1CCS(=O)(=O)N1CCC2(CC1)N=C(C1CCC(CCC(F)(F)F)CC1)NC2=O] | LCMS-D-1 | 2.12 | 674 (M + H)+ |
| 725 | 827 | 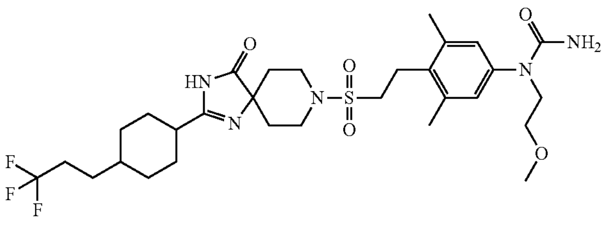 [SMILES: COCCN(C(N)=O)c1cc(C)c(CCS(=O)(=O)N2CCC3(CC2)N=C(C2CCC(CCC(F)(F)F)CC2)NC3=O)c(C)c1] | LCMS-D-1 | 2.37 | 644 (M + H)+ |

TABLE 111-continued
| Starting Compound | Target Compound | Structure | LCMS condition | Retention time (min) | MS (m/z) |
|---|---|---|---|---|---|
| 726 | 828 | 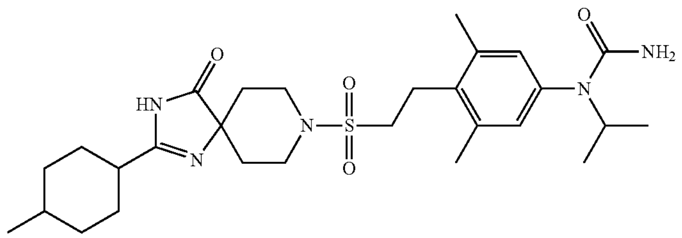 [SMILES: Cc1cc(N(C(N)=O)C(C)C)cc(C)c1CCS(=O)(=O)N1CCC2(CC1)N=C(C1CCC(C)CC1)NC2=O] | LCMS-D-1 | 2.32 | 546 (M + H)+ |
| 727 | 829 | 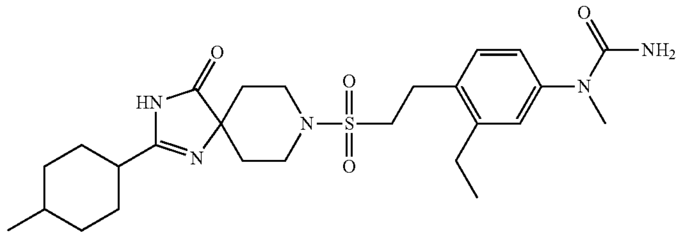 [SMILES: CCc1cc(N(C)C(N)=O)ccc1CCS(=O)(=O)N1CCC2(CC1)N=C(C1CCC(C)CC1)NC2=O] | LCMS-D-1 | 2.68 | 518 (M + H)+ |
| 733 | 830 | 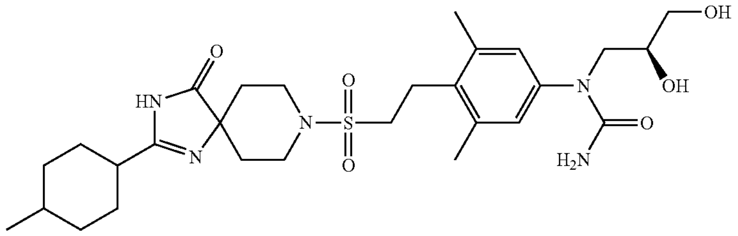 [SMILES: Cc1cc(N(C[C@H](O)CO)C(N)=O)cc(C)c1CCS(=O)(=O)N1CCC2(CC1)N=C(C1CCC(C)CC1)NC2=O] | LCMS-D-1 | 1.52 | 578 (M + H)+ |
| 403 | 831 | 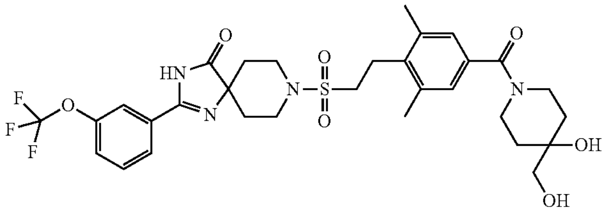 [SMILES: Cc1cc(C(=O)N2CCC(O)(CO)CC2)cc(C)c1CCS(=O)(=O)N1CCC2(CC1)N=C(c1cccc(OC(F)(F)F)c1)NC2=O] | LCMS-F-1 | 0.91 | 667 (M + H)+ |
| 539 | 832 | 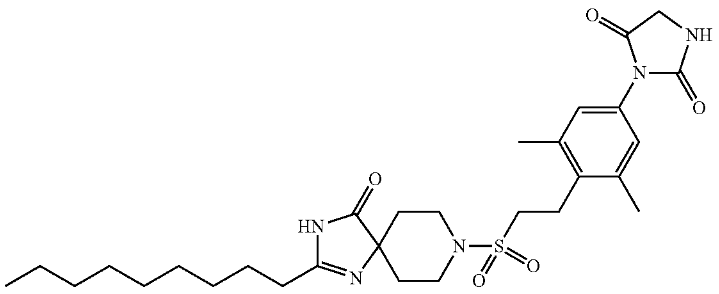 [SMILES: CCCCCCCCCC1=NC2(CCN(S(=O)(=O)CCc3c(C)cc(N4C(=O)CNC4=O)cc3C)CC2)C(=O)N1] | LCMS-A-1 | 2.43 | 574 (M + H)+ |

TABLE 111-continued

| Starting Compound | Target Compound | Structure | LCMS condition | Retention time (min) | MS (m/z) |
|---|---|---|---|---|---|
| 589 | 833 | 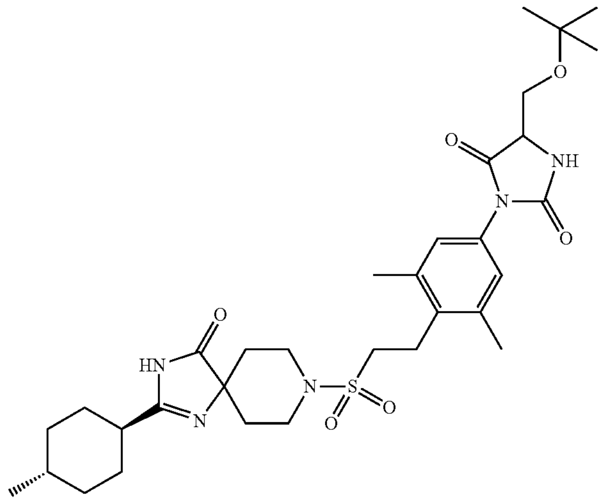 [SMILES: Cc1cc(N2C(=O)NC(COC(C)(C)C)C2=O)cc(C)c1CCS(=O)(=O)N1CCC2(CC1)N=C([C@H]1CC[C@H](C)CC1)NC2=O] | LCMS-B-2 | 4.38 | 631 (M + H)+ |
| 588 | 834 | 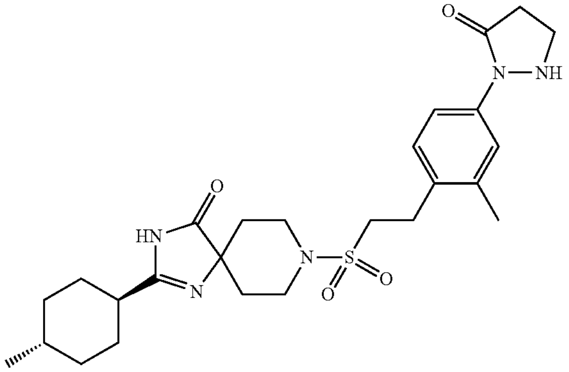 [SMILES: Cc1cc(N2NCCC2=O)ccc1CCS(=O)(=O)N1CCC2(CC1)N=C([C@H]1CC[C@H](C)CC1)NC2=O] | LCMS-C-1 | 2.47 | 517 (M + H)+ |

Example 185

2-Cyclohexyl-8-[2-(1H-indol-7-yl)-ethanesulfonyl]-1,3,8-triaza-spiro[4.5]dec-1-en-4-one (Compound 835)

(Reaction 185-1)

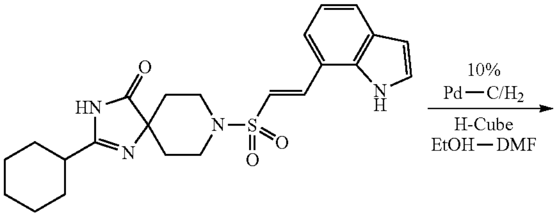

Compound 479

-continued

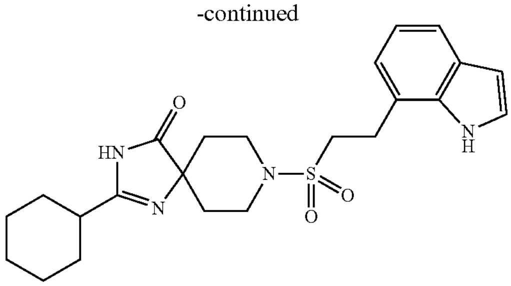

Compound 835

2-Cyclohexyl-8-[2-(1H-indol-7-yl)-ethanesulfonyl]-1,3,8-triaza-spiro[4.5]dec-1-en-4-one (Compound 835) was obtained by operations similar to those in Reaction 42-2 using Compound 479 as a starting material.

MS (ESI) m/z=443 (M+H)+.

The example compounds shown below were obtained by operations similar to those in Example 185 using appropriate solvents (an ethanol-dimethylformamide mixed solution or ethanol) and starting compounds.

Compounds 836 to Compound 879
TABLE 112
| Starting Compound | Target Compound | Structure | LCMS condition | Retention time (min) | MS (m/z) |
|---|---|---|---|---|---|
| 492 | 836 | 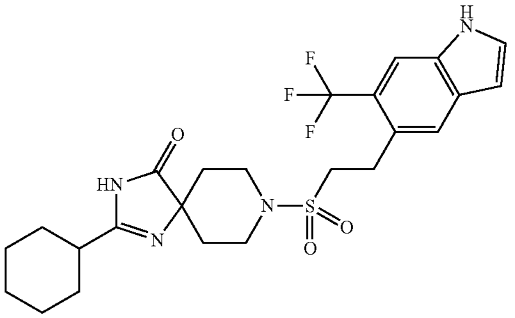 | LCMS-A-1 | 2.25 | 511 (M + H)+ |
| 488 | 837 | 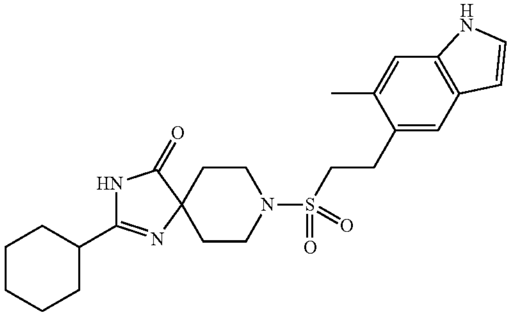 [SMILES: Cc1cc2[nH]ccc2cc1CCS(=O)(=O)N1CCC2(CC1)N=C(C1CCCCC1)NC2=O] | LCMS-A-1 | 2.12 | 457 (M + H)+ |
| 487 | 838 | 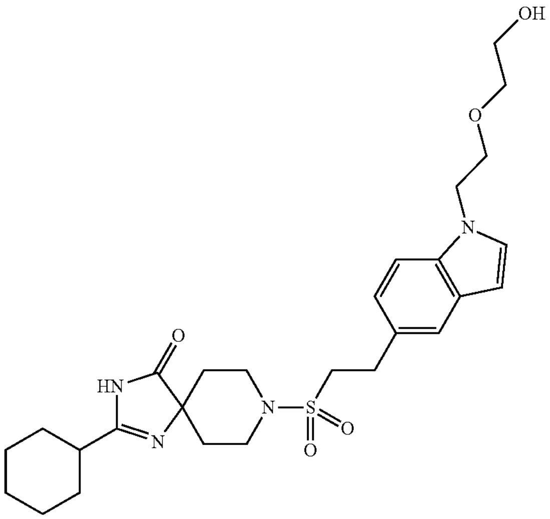 [SMILES: O=C1NC(C2CCCCC2)=NC12CCN(S(=O)(=O)CCc1ccc3c(ccn3CCOCCO)c1)CC2] | LCMS-A-1 | 1.95 | 531 (M + H)+ |
| 499 | 839 | 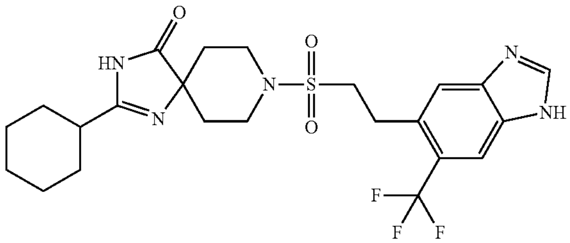 [SMILES: O=C1NC(C2CCCCC2)=NC12CCN(S(=O)(=O)CCc1cc3nc[nH]c3cc1C(F)(F)F)CC2] | LCMS-A-1 | 1.66 | 512 (M + H)+ |

TABLE 112-continued
| Starting Compound | Target Compound | Structure | LCMS condition | Retention time (min) | MS (m/z) |
|---|---|---|---|---|---|
| 524 | 840 | 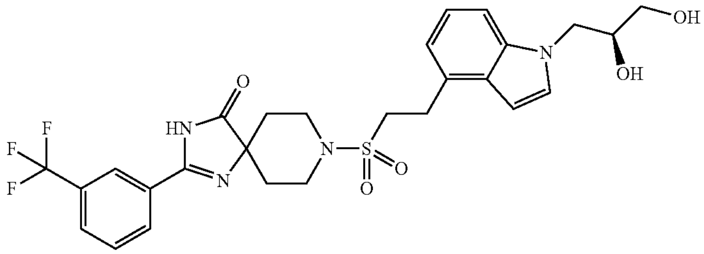 [SMILES: O=C1NC(c2cccc(C(F)(F)F)c2)=NC12CCN(S(=O)(=O)CCc1cccc3c1ccn3C[C@H](O)CO)CC2] | LCMS-A-1 | 2.25 | 579 (M + H)+ |
| 502 | 841 | 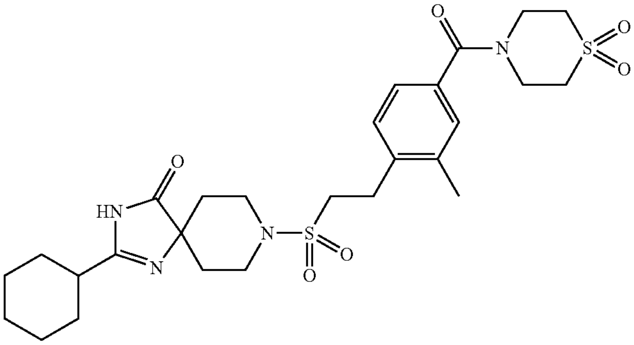 [SMILES: Cc1cc(C(=O)N2CCS(=O)(=O)CC2)ccc1CCS(=O)(=O)N1CCC2(CC1)N=C(C1CCCCC1)NC2=O] | LCMS-C-1 | 2.15 | 579 (M + H)+ |
| 497 | 842 | 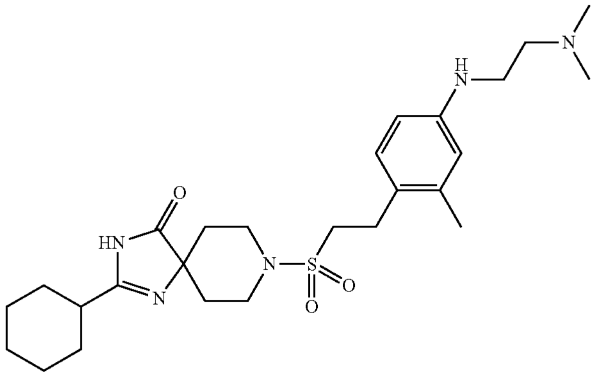 [SMILES: Cc1cc(NCCN(C)C)ccc1CCS(=O)(=O)N1CCC2(CC1)N=C(C1CCCCC1)NC2=O] | LCMS-C-1 | 2.22 | 504 (M + H)+ |
| 527 | 843 | 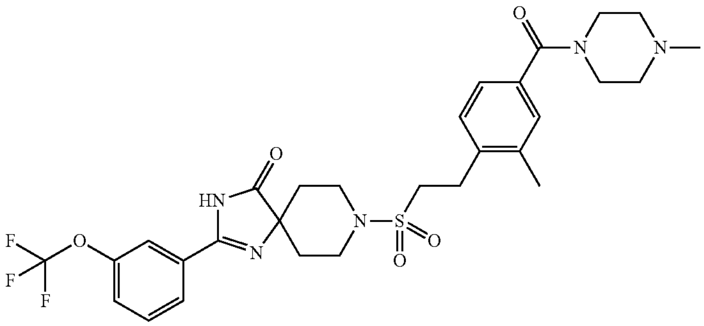 [SMILES: Cc1cc(C(=O)N2CCN(C)CC2)ccc1CCS(=O)(=O)N1CCC2(CC1)N=C(c1cccc(OC(F)(F)F)c1)NC2=O] | LCMS-C-1 | 2.63 | 622 (M + H)+ |

TABLE 112-continued
| Starting Compound | Target Compound | Structure | LCMS condition | Retention time (min) | MS (m/z) |
| --- | --- | --- | --- | --- | --- |
| 844 | 844 | 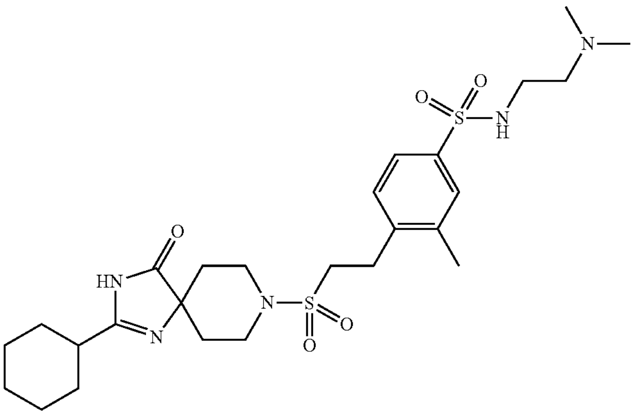 [SMILES: Cc1cc(S(=O)(=O)NCCN(C)C)ccc1CCS(=O)(=O)N1CCC2(CC1)N=C(C1CCCCC1)NC2=O] | LCMS-C-1 | 2.20 | 568 (M + H)+ |
| 528 | 845 | 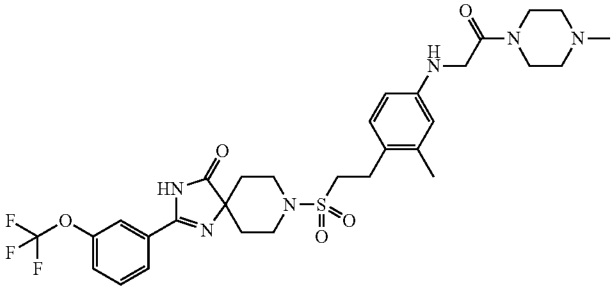 | LCMS-C-1 | 2.58 | 651 (M + H)+ |
| 530 | 846 | 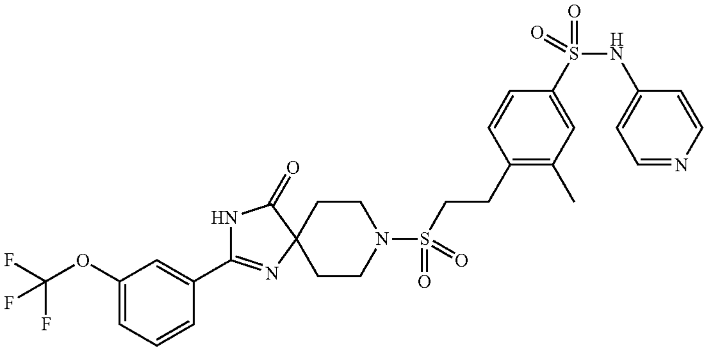 [SMILES: Cc1cc(S(=O)(=O)Nc2ccncc2)ccc1CCS(=O)(=O)N1CCC2(CC1)N=C(c1cccc(OC(F)(F)F)c1)NC2=O] | LCMS-C-1 | 2.37 | 652 (M + H)+ |
| 529 | 847 | 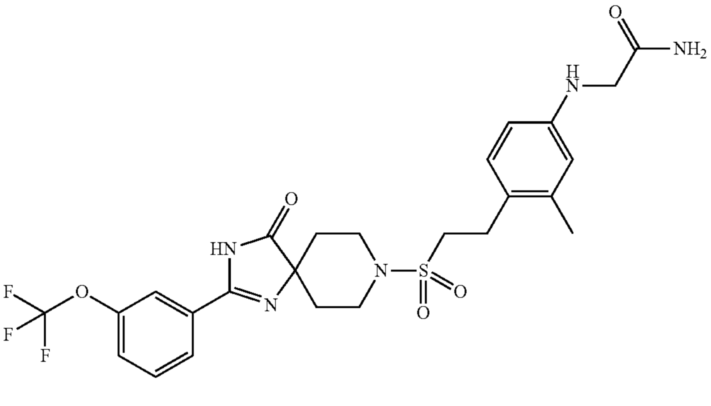 [SMILES: Cc1cc(NCC(N)=O)ccc1CCS(=O)(=O)N1CCC2(CC1)N=C(c1cccc(OC(F)(F)F)c1)NC2=O] | LCMS-C-1 | 2.48 | 568 (M + H)+ |

TABLE 112-continued
| Starting Compound | Target Compound | Structure | LCMS condition | Retention time (min) | MS (m/z) |
|---|---|---|---|---|---|
| 596 | 848 | 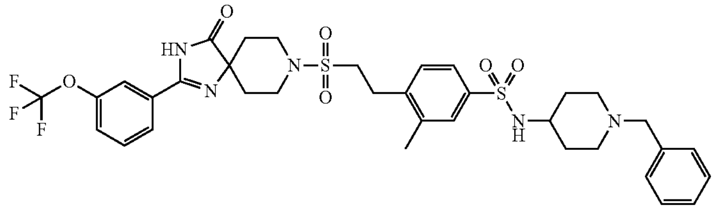 [SMILES: Cc1cc(S(=O)(=O)NC2CCN(Cc3ccccc3)CC2)ccc1CCS(=O)(=O)N1CCC2(CC1)N=C(c1cccc(OC(F)(F)F)c1)NC2=O] | LCMS-C-1 | 2.90 | 748 (M + H)+ |
| 598 | 849 | 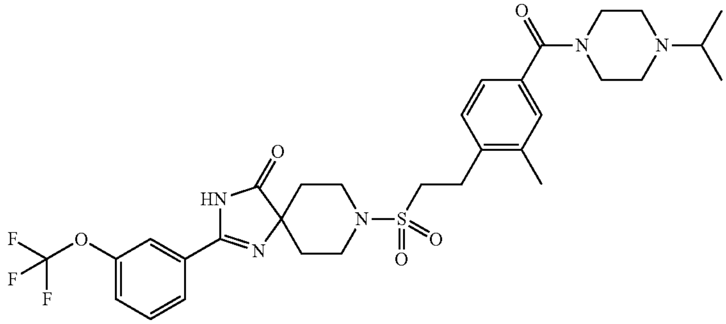 [SMILES: Cc1cc(C(=O)N2CCN(C(C)C)CC2)ccc1CCS(=O)(=O)N1CCC2(CC1)N=C(c1cccc(OC(F)(F)F)c1)NC2=O] | LCMS-C-1 | 2.77 | 650 (M + H)+ |
| 597 | 850 | 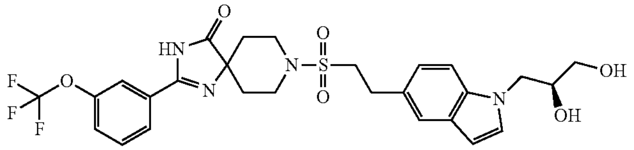 [SMILES: O=C1NC(c2cccc(OC(F)(F)F)c2)=NC12CCN(S(=O)(=O)CCc1ccc3c(ccn3C[C@H](O)CO)c1)CC2] | LCMS-C-1 | 2.58 | 595 (M + H)+ |
| 599 | 851 | 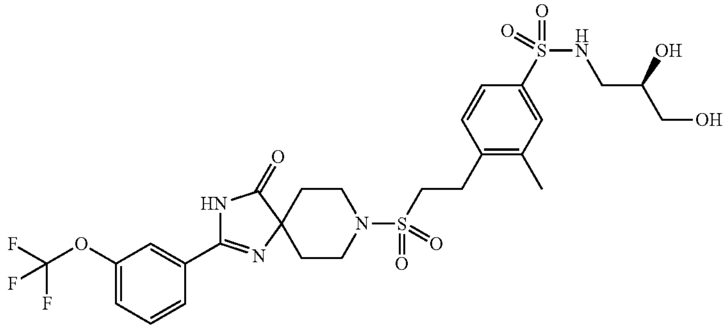 [SMILES: Cc1cc(S(=O)(=O)NC[C@@H](O)CO)ccc1CCS(=O)(=O)N1CCC2(CC1)N=C(c1cccc(OC(F)(F)F)c1)NC2=O] | LCMS-C-1 | 2.42 | 649 (M + H)+ |
| 591 | 852 | 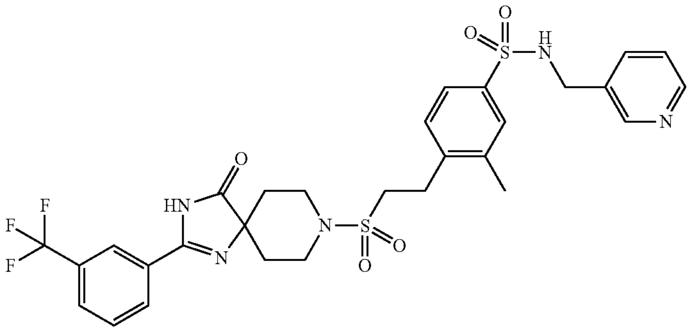 [SMILES: Cc1cc(S(=O)(=O)NCc2cccnc2)ccc1CCS(=O)(=O)N1CCC2(CC1)N=C(c1cccc(C(F)(F)F)c1)NC2=O] | LCMS-C-1 | 2.53 | 650 (M + H)+ |

TABLE 112-continued
| Starting Compound | Target Compound | Structure | LCMS condition | Retention time (min) | MS (m/z) |
|---|---|---|---|---|---|
| 592 | 853 | 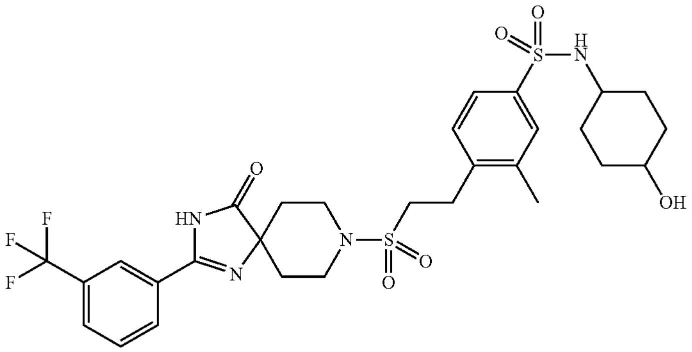 [SMILES: Cc1cc(S(=O)(=O)NC2CCC(O)CC2)ccc1CCS(=O)(=O)N1CCC2(CC1)N=C(c1cccc(C(F)(F)F)c1)NC2=O] | LCMS-C-1 | 2.43 | 657 (M + H)+ |
| 595 | 854 | 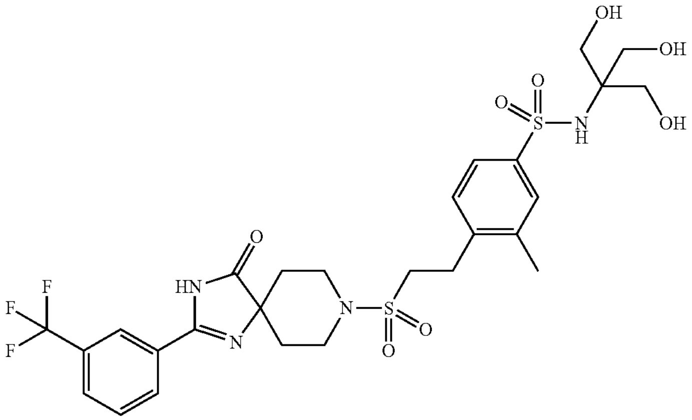 [SMILES: Cc1cc(S(=O)(=O)NC(CO)(CO)CO)ccc1CCS(=O)(=O)N1CCC2(CC1)N=C(c1cccc(C(F)(F)F)c1)NC2=O] | LCMS-C-1 | 2.35 | 663 (M + H)+ |
| 601 | 855 | 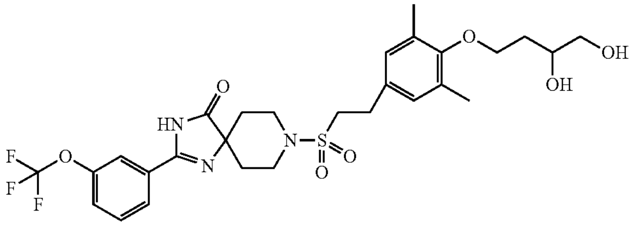 [SMILES: Cc1cc(CCS(=O)(=O)N2CCC3(CC2)N=C(c2cccc(OC(F)(F)F)c2)NC3=O)cc(C)c1OCCC(O)CO] | LCMS-C-1 | 2.68 | 614 (M + H)+ |
| 619 | 856 | 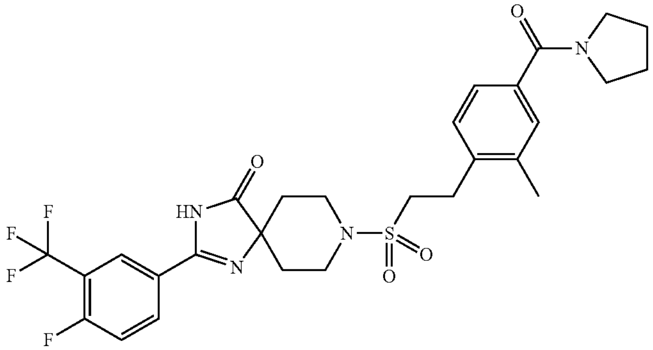 [SMILES: Cc1cc(C(=O)N2CCCC2)ccc1CCS(=O)(=O)N1CCC2(CC1)N=C(c1ccc(F)c(C(F)(F)F)c1)NC2=O] | LCMS-C-1 | 2.72 | 595 (M + H)+ |

TABLE 112-continued
| Starting Compound | Target Compound | Structure | LCMS condition | Retention time (min) | MS (m/z) |
|---|---|---|---|---|---|
| 620 | 857 | 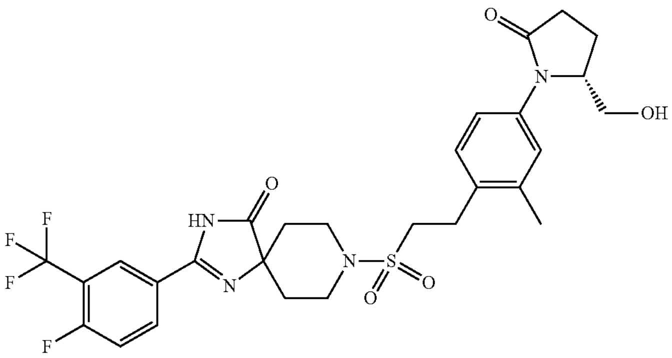 [SMILES: Cc1cc(N2C(=O)CC[C@@H]2CO)ccc1CCS(=O)(=O)N1CCC2(CC1)N=C(c1ccc(F)c(C(F)(F)F)c1)NC2=O] | LCMS-B-1 | 1.95 | 611 (M + H)+ |
| 621 | 858 | 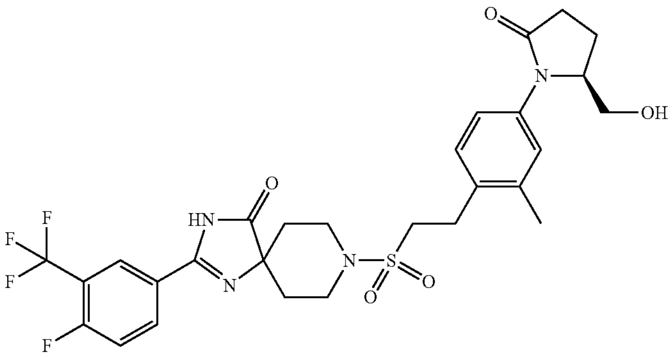 [SMILES: Cc1cc(N2C(=O)CC[C@H]2CO)ccc1CCS(=O)(=O)N1CCC2(CC1)N=C(c1ccc(F)c(C(F)(F)F)c1)NC2=O] | LCMS-C-1 | 2.47 | 611 (M + H)+ |
| 602 | 859 | 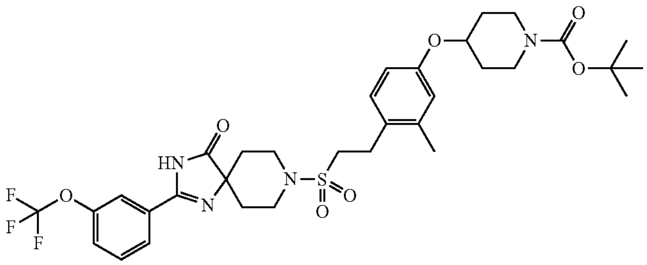 [SMILES: Cc1cc(OC2CCN(C(=O)OC(C)(C)C)CC2)ccc1CCS(=O)(=O)N1CCC2(CC1)N=C(c1cccc(OC(F)(F)F)c1)NC2=O] | LCMS-C-1 | 3.15 | 695 (M + H)+ |
| 600 | 860 | 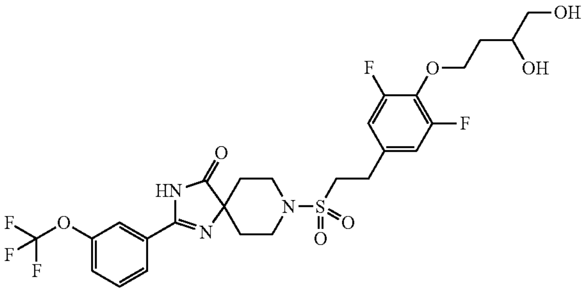 [SMILES: O=C1NC(c2cccc(OC(F)(F)F)c2)=NC12CCN(S(=O)(=O)CCc1cc(F)c(OCCC(O)CO)c(F)c1)CC2] | LCMS-C-1 | 2.58 | 622 (M + H)+ |

TABLE 112-continued
| Starting Compound | Target Compound | Structure | LCMS condition | Retention time (min) | MS (m/z) |
|---|---|---|---|---|---|
| 572 | 861 | 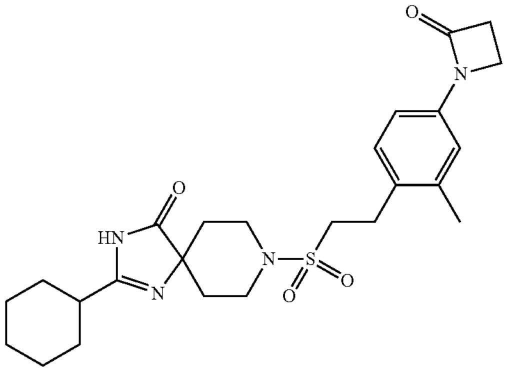 [SMILES: Cc1cc(N2CCC2=O)ccc1CCS(=O)(=O)N1CCC2(CC1)N=C(C1CCCCC1)NC2=O] | LCMS-C-1 | 2.47 | 487 (M + H)+ |
| 505 | 862 | 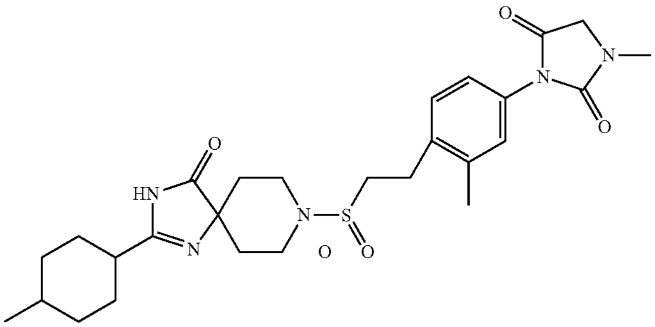 | LCMS-C-1 | 2.45 | 544 (M + H)+ |
| 511 | 863 | 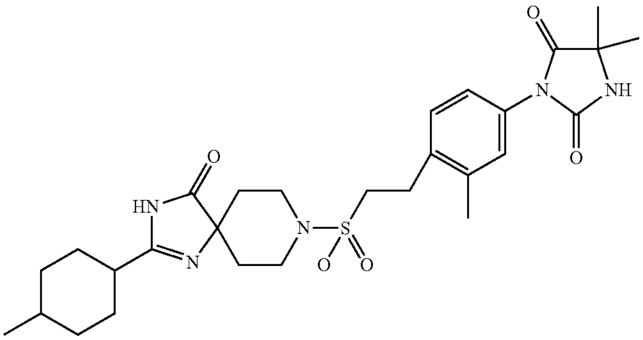 | LCMS-F-1 | 0.93 | 558 (M + H)+ |
| 540 | 864 | 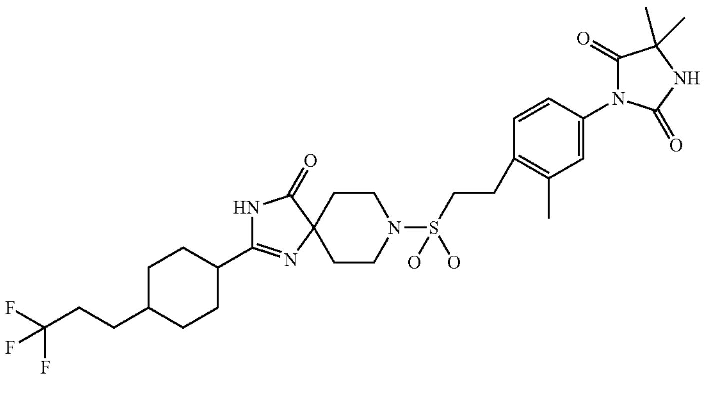 [SMILES: Cc1cc(N2C(=O)NC(C)(C)C2=O)ccc1CCS(O)(O)N1CCC2(CC1)N=C(C1CCC(CCC(F)(F)F)CC1)NC2=O] | LCMS-F-1 | 0.96 | 640 (M + H)+ |

TABLE 112-continued
| Starting Com-pound | Target Com-pound | Structure | LCMS condition | Reten-tion time (min) | MS (m/z) |
|---|---|---|---|---|---|
| 513 | 865 | 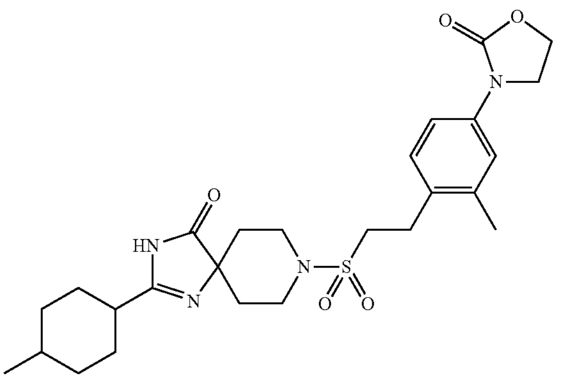 [SMILES: Cc1cc(N2CCOC2=O)ccc1CCS(=O)(=O)N1CCC2(CC1)N=C(C1CCC(C)CC1)NC2=O] | LCMS-C-1 | 2.55 | 517 (M + H)+ |
| 577 | 866 | 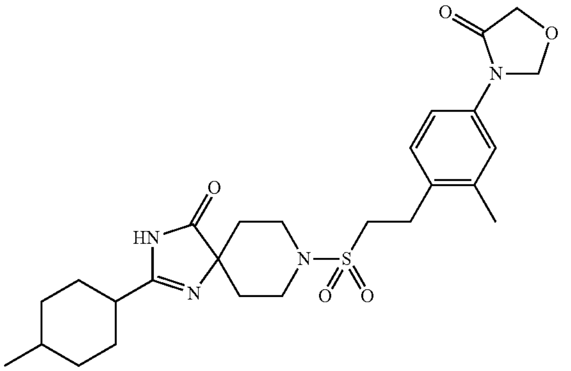 [SMILES: Cc1cc(N2COCC2=O)ccc1CCS(=O)(=O)N1CCC2(CC1)N=C(C1CCC(C)CC1)NC2=O] | LCMS-C-1 | 2.60 | 517 (M + H)+ |
| 541 | 867 | 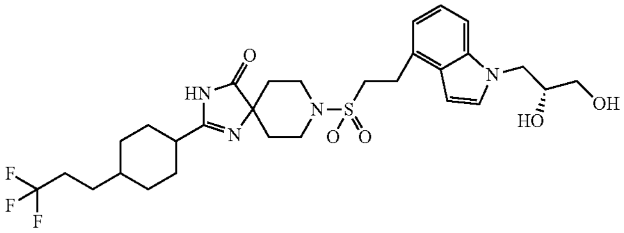 | LCMS-F-1 | 0.96 | 613 (M + H)+ |
| 586 | 868 | 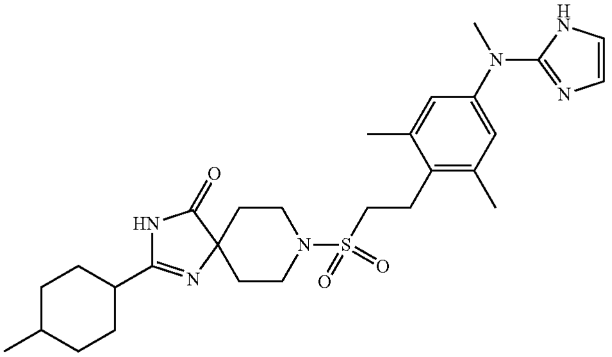 [SMILES: Cc1cc(N(C)c2ncc[nH]2)cc(C)c1CCS(=O)(=O)N1CCC2(CC1)N=C(C1CCC(C)CC1)NC2=O] | LCMS-A-1 | 1.84 | 541 (M + H)+ |

TABLE 112-continued
| Starting Compound | Target Compound | Structure | LCMS condition | Retention time (min) | MS (m/z) |
|---|---|---|---|---|---|
| 507 | 869 | 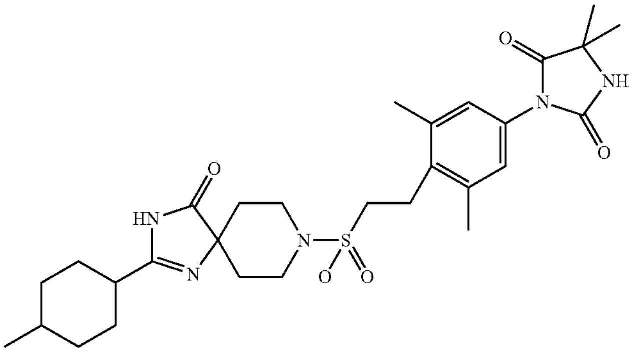 | LCMS-F-1 | 0.96 | 572 (M + H)+ |
| 1185 | 870 | 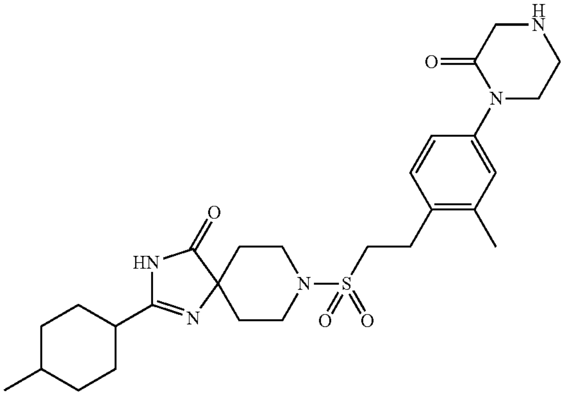 [SMILES: Cc1cc(N2CCNCC2=O)ccc1CCS(=O)(=O)N1CCC2(CC1)N=C(C1CCC(C)CC1)NC2=O] | LCMS-A-1 | 1.65 | 530 (M + H)+ |
| 702 | 872 | 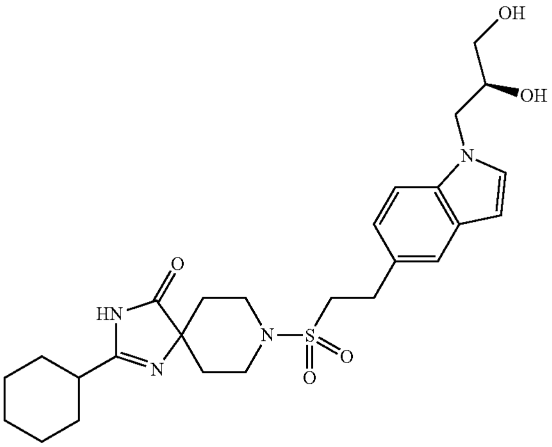 [SMILES: O=C1NC(C2CCCCC2)=NC12CCN(S(=O)(=O)CCc1ccc3c(ccn3C[C@H](O)CO)c1)CC2] | LCMS-C-1 | 2.30 | 517 (M + H)+ |

TABLE 112-continued
| Starting Compound | Target Compound | Structure | LCMS condition | Retention time (min) | MS (m/z) |
|---|---|---|---|---|---|
| 717 | 873 | 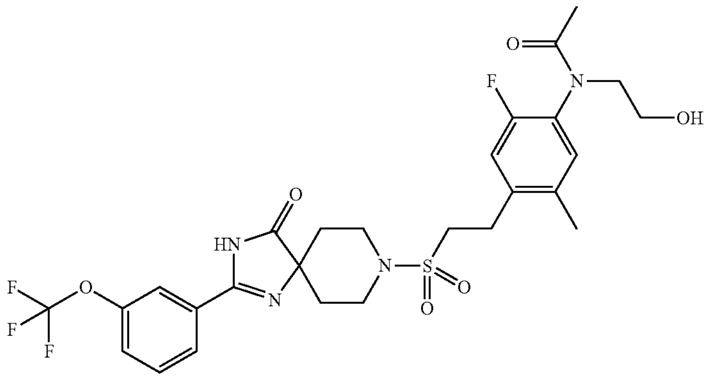 [SMILES: CC(=O)N(CCO)c1cc(C)c(CCS(=O)(=O)N2CCC3(CC2)N=C(c2cccc(OC(F)(F)F)c2)NC3=O)cc1F] | LCMS-B-1 | 2.04 | 615 (M + H)+ |
| 473 | 874 | 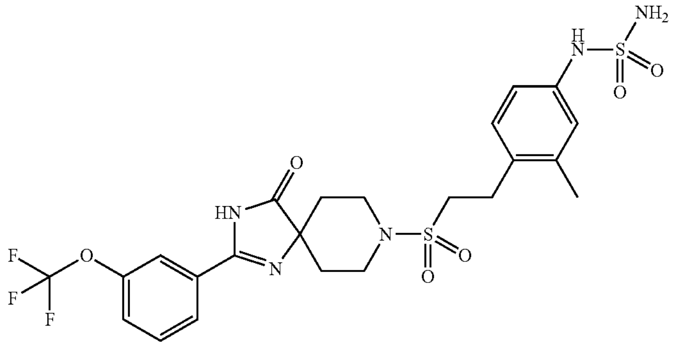 [SMILES: Cc1cc(NS(N)(=O)=O)ccc1CCS(=O)(=O)N1CCC2(CC1)N=C(c1cccc(OC(F)(F)F)c1)NC2=O] | LCMS-C-1 | 2.42 | 590 (M + H)+ |
| 743 | 875 | 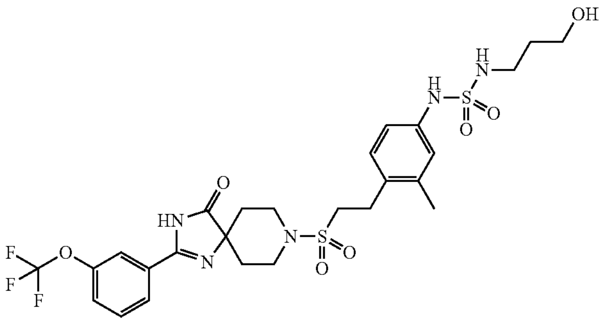 [SMILES: Cc1cc(NS(=O)(=O)NCCCO)ccc1CCS(=O)(=O)N1CCC2(CC1)N=C(c1cccc(OC(F)(F)F)c1)NC2=O] | LCMS-C-1 | 2.43 | 648 (M + H)+ |
| 729 | 876 | 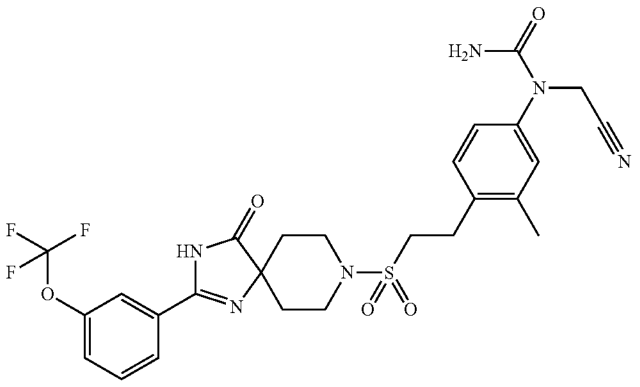 | LCMS-C-1 | 2.20 | 580 (M + H)+ |

TABLE 112-continued
| Starting Compound | Target Compound | Structure | LCMS condition | Retention time (min) | MS (m/z) |
|---|---|---|---|---|---|
| 731 | 877 | 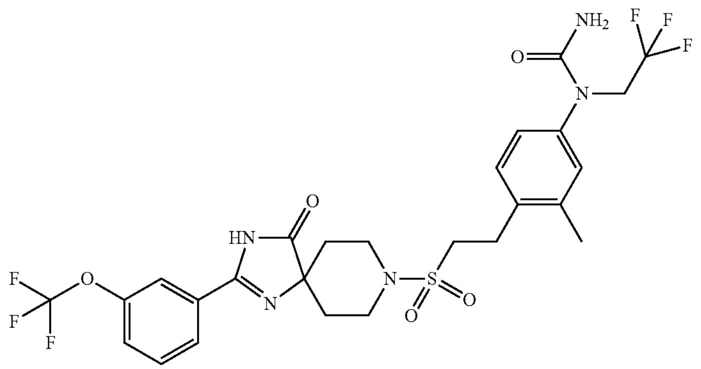 [SMILES: Cc1cc(N(CC(F)(F)F)C(N)=O)ccc1CCS(=O)(=O)N1CCC2(CC1)N=C(c1cccc(OC(F)(F)F)c1)NC2=O] | LCMS-C-1 | 2.70 | 636 (M + H)+ |
| 624 | 878 | 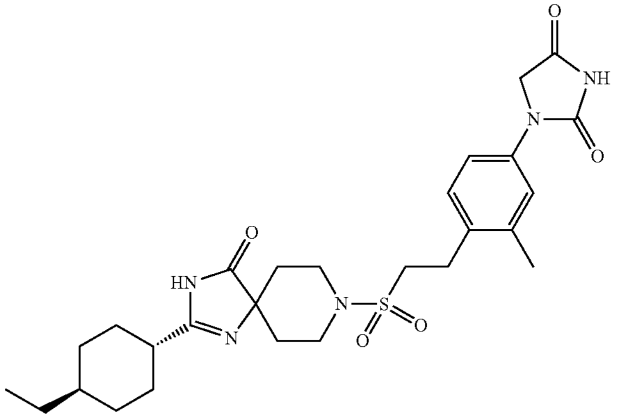 [SMILES: CC[C@H]1CC[C@H](C2=NC3(CCN(S(=O)(=O)CCc4ccc(N5CC(=O)NC5=O)cc4C)CC3)C(=O)N2)CC1] | LCMS-C-1 | 2.65 | 544 (M + H)+ |
| 625 | 879 | 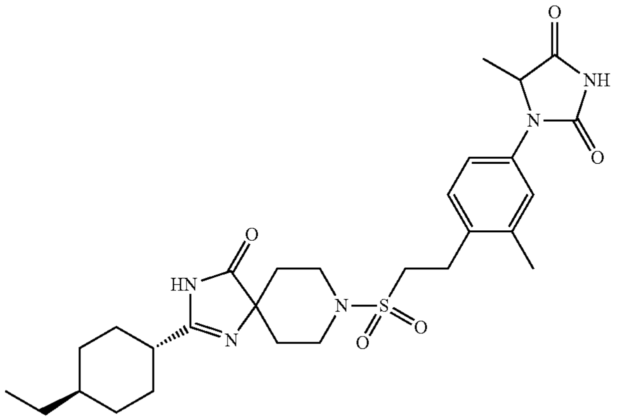 [SMILES: CC[C@H]1CC[C@H](C2=NC3(CCN(S(=O)(=O)CCc4ccc(N5C(=O)NC(=O)C5C)cc4C)CC3)C(=O)N2)CC1] | LCMS-C-1 | 2.68 | 558 (M + H)+ |

Example 186

3-(4-{2-[2-(4-Butyl-cyclohexyl)-4-oxo-1,3,8-triaza-spiro[4.5]dec-1-ene-8-sulfonyl]-ethyl}-3-methyl-phenyl)-imidazolidine-2,4-dione (Compound 880)

(Reaction 186-1)

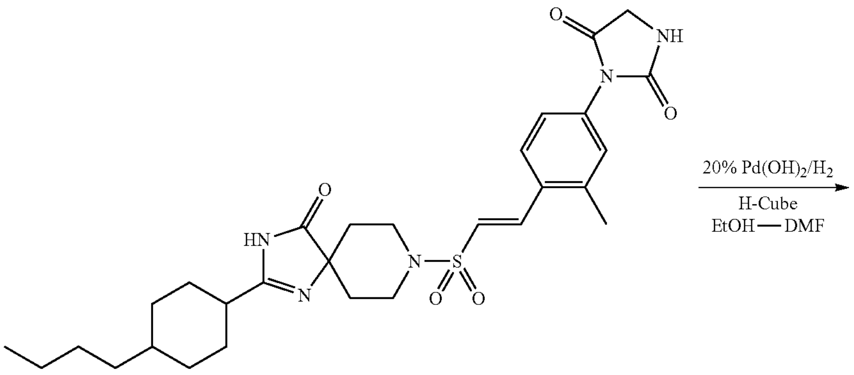

Compound 560

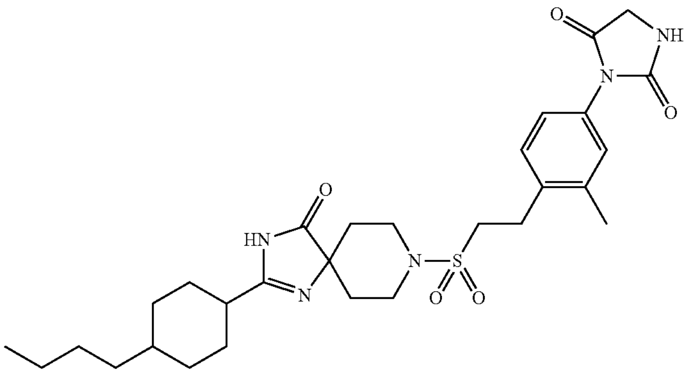

Compound 880

3-(4-{2-[2-(4-Butyl-cyclohexyl)-4-oxo-1,3,8-triaza-spiro[4.5]dec-1-ene-8-sulfonyl]-ethyl}-3-methyl-phenyl)-imidazolidine-2,4-dione (Compound 880) was obtained by operations similar to those in Reaction 91-1 using Compound 560 as a starting material.

MS (ESI) m/z=572 (M+H)+.

The example compounds shown below were obtained by operations similar to those in Example 186 using appropriate solvents (an ethanol-dimethylformamide mixed solution or ethanol) and starting compounds.

Compounds 881 to Compound 887
TABLE 113
| Starting Compound | Target Compound | Structure | LCMS condition | Retention time (min) | MS (m/z) |
|---|---|---|---|---|---|
| 504 | 881 | 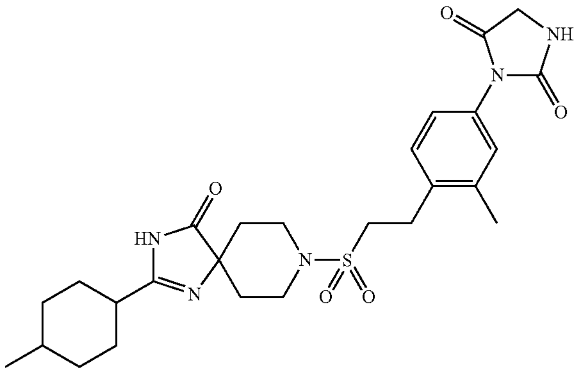 [SMILES: Cc1cc(N2C(=O)CNC2=O)ccc1CCS(=O)(=O)N1CCC2(CC1)N=C(C1CCC(C)CC1)NC2=O] | LCMS-C-1 | 2.33 | 530 (M + H)+ |
| 563 | 882 | 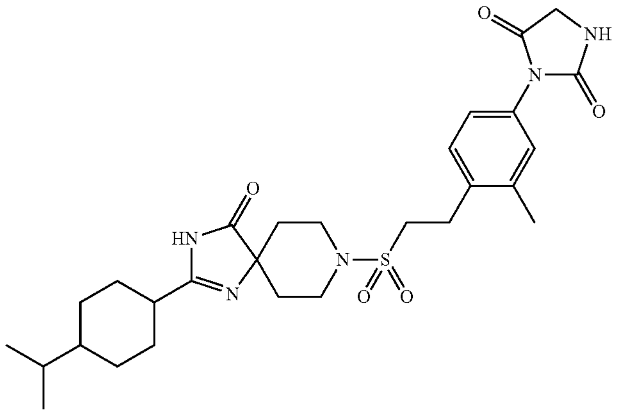 [SMILES: Cc1cc(N2C(=O)CNC2=O)ccc1CCS(=O)(=O)N1CCC2(CC1)N=C(C1CCC(C(C)C)CC1)NC2=O] | LCMS-C-1 | 2.67 | 558 (M + H)+ |
| 575 | 883 | 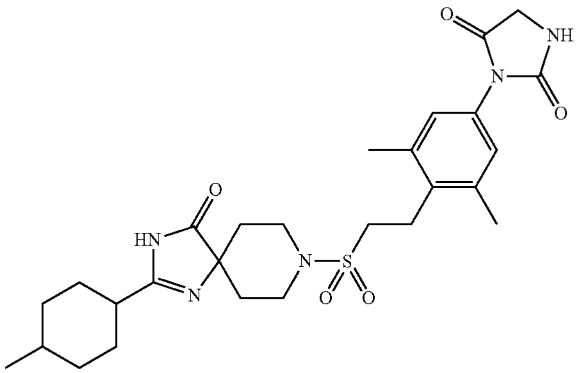 [SMILES: Cc1cc(N2C(=O)CNC2=O)cc(C)c1CCS(=O)(=O)N1CCC2(CC1)N=C(C1CCC(C)CC1)NC2=O] | LCMS-C-1 | 2.43 | 544 (M + H)+ |

TABLE 113-continued
| Starting Compound | Target Compound | Structure | LCMS condition | Retention time (min) | MS (m/z) |
|---|---|---|---|---|---|
| 564 | 884 | 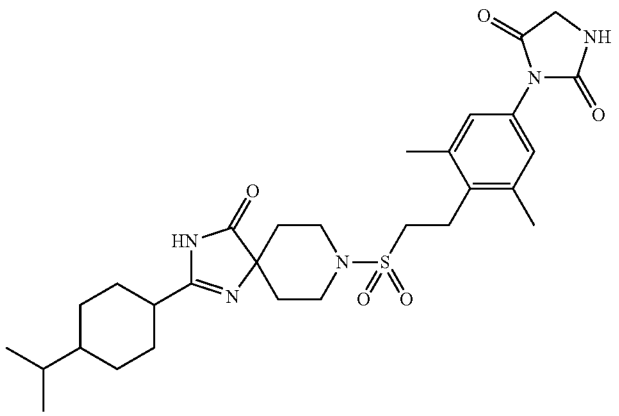 [SMILES: Cc1cc(N2C(=O)CNC2=O)cc(C)c1CCS(=O)(=O)N1CCC2(CC1)N=C(C1CCC(C(C)C)CC1)NC2=O] | LCMS-C-1 | 2.70 | 572 (M + H)+ |
| 508 | 885 | 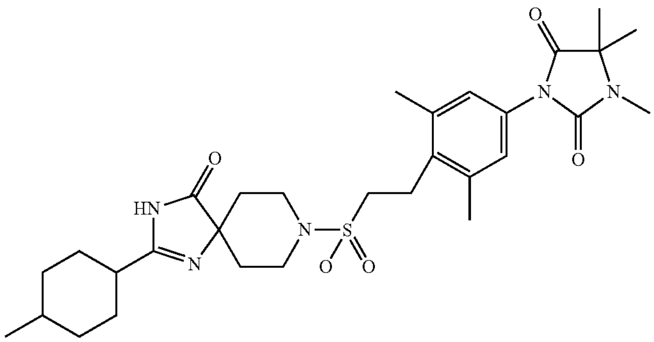 | LCMS-F-1 | 0.97 | 586 (M + H)+ |
| 688 | 886 | 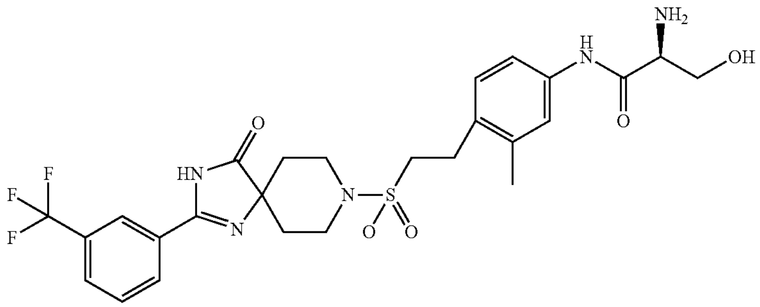 | LCMS-F-1 | 0.86 | 582 (M + H)+ |
| 626 | 887 | 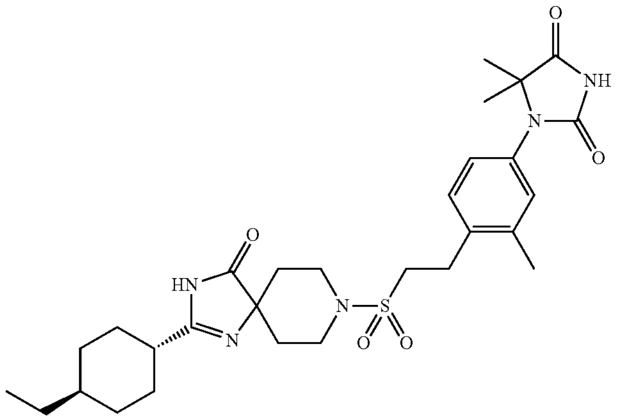 [SMILES: CC[C@H]1CC[C@H](C2=NC3(CCN(S(=O)(=O)CCc4ccc(N5C(=O)NC(=O)C5(C)C)cc4C)CC3)C(=O)N2)CC1] | LCMS-C-1 | 2.70 | 572 (M + H)+ |

Example 187

3,5-Dimethyl-4-(2-{4-oxo-2-[4-(3,3,3-trifluoro-propyl)-cyclohexyl]-1,3,8-triaza-spiro[4.5]dec-1-ene-8-sulfonyl}-ethyl)-benzoic acid N,N'-dimethyl-hydrazide (Compound 888)

(Reaction 187-1)

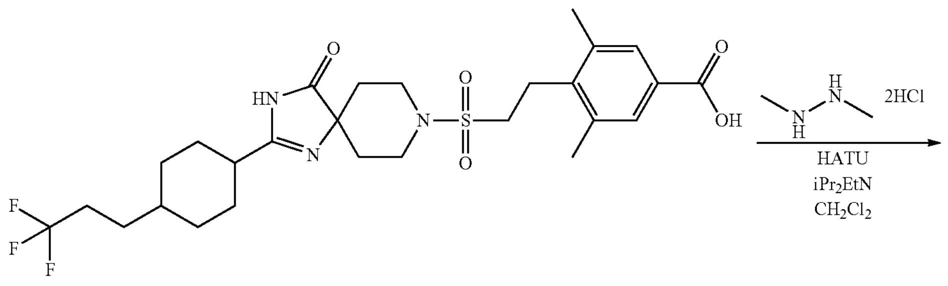

Compound 768

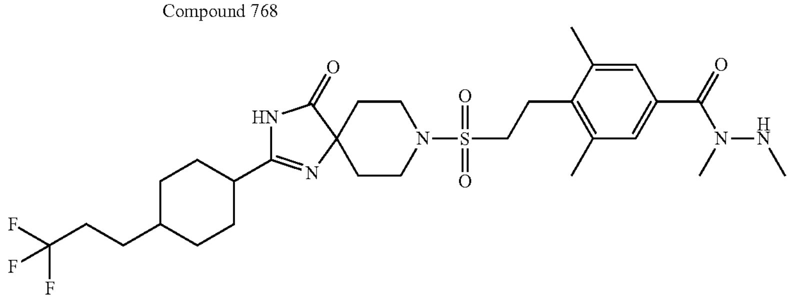

Compound 888

3,5-Dimethyl-4-(2-{4-oxo-2-[4-(3,3,3-trifluoro-propyl)-cyclohexyl]-1,3,8-triaza-spiro[4.5]dec-1-ene-8-sulfonyl}-ethyl)-benzoic acid N,N'-dimethyl-hydrazide (Compound 888) was obtained by operations similar to those in Reaction 10-14 using Compound 768 as a starting material and using dichloromethane as a solvent.

MS (ESI) m/z=614 (M+H)+.

Example 188

8-{2-[2-Methyl-4-(piperidin-4-yloxy)-phenyl]-ethanesulfonyl}-2-(3-trifluoromethoxy-phenyl)-1,3,8-triaza-spiro[4.5]dec-1-en-4-one hydrochloride (Compound 889)

(Reaction 188-1)

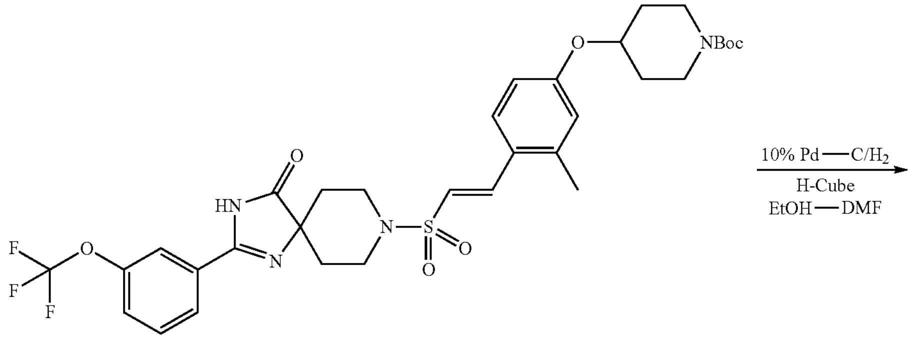

Compound 602

-continued

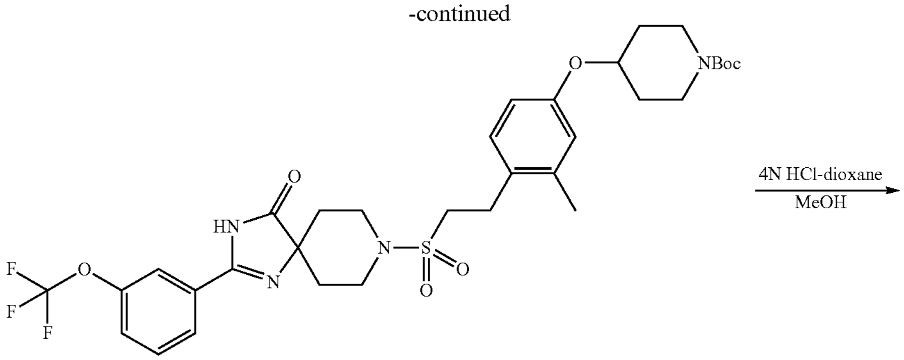

188a

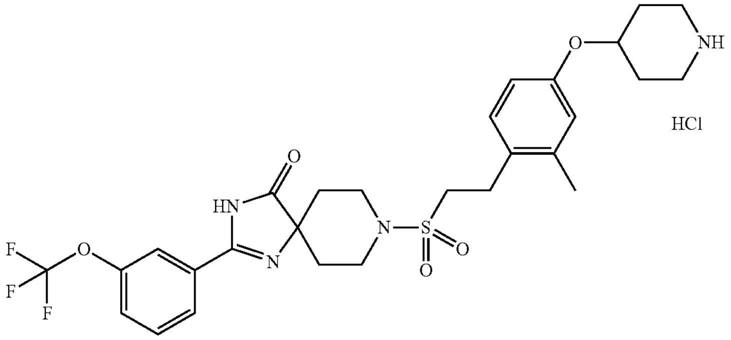

Compound 889

8-{2-[2-Methyl-4-(piperidin-4-yloxy)-phenyl]-ethane-sulfonyl}-2-(3-trifluoromethoxy-phenyl)-1,3,8-triaza-spiro[4.5]dec-1-en-4-one hydrochloride (Compound 889) was obtained by operations similar to those in Reaction 42-2 and Reaction 5-3 using Compound 602 as a starting material.

MS (ESI) m/z=595 (M+H)+.

Example 189

4-{2-[2-(4,4-Difluoro-cyclohexyl)-4-oxo-1,3,8-triaza-spiro[4.5]dec-1-ene-8-sulfonyl]-ethyl}-3,N,N-trimethyl-benzamide (Compound 890)

(Reaction 189-1)

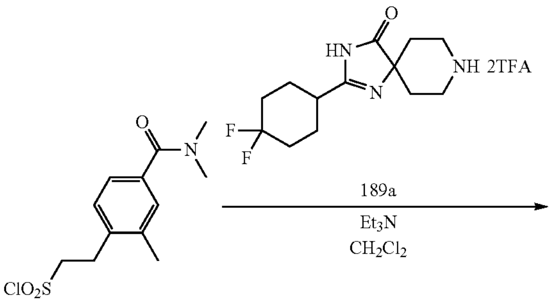

10f

-continued

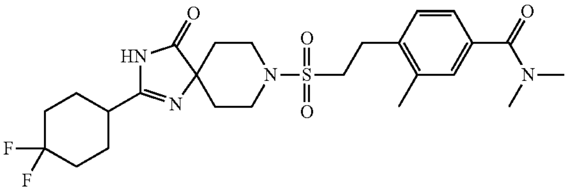

Compound 890

4-{2-[2-(4,4-Difluoro-cyclohexyl)-4-oxo-1,3,8-triaza-spiro[4.5]dec-1-ene-8-sulfonyl]-ethyl}-3,N,N-trimethyl-benzamide was synthesized by operations similar to those in Reaction 5-4 using appropriate reagents and starting material.

MS (ESI) m/z=523 (M−H)−.

The example compounds shown below were synthesized by operations similar to those in Reaction 189-1 using appropriate reagents and starting materials.

Compounds 891 to 901
TABLE 114
| Compound | Structure | LCMS condition | Retention time (min) | MS (m/z) |
|---|---|---|---|---|
| 891 | 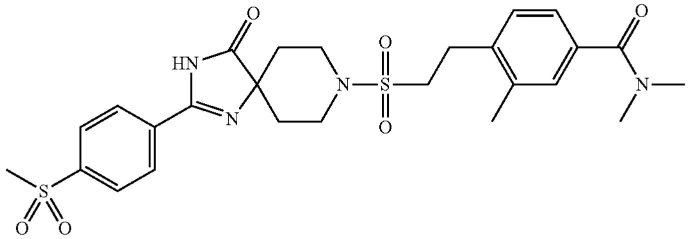 | LCMS-C-1 | 2.07 | 561 (M + H)+ |
| 892 | 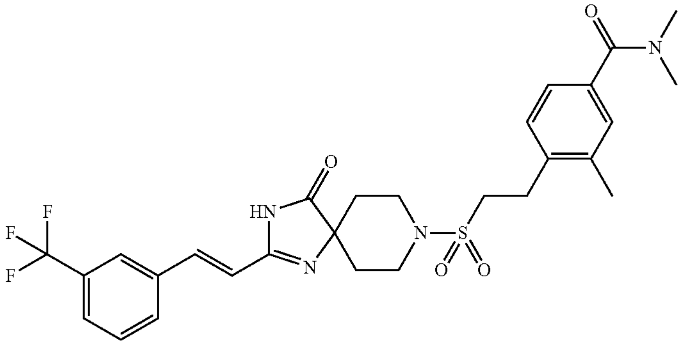 [SMILES: Cc1cc(C(=O)N(C)C)ccc1CCS(=O)(=O)N1CCC2(CC1)N=C(/C=C/c1cccc(C(F)(F)F)c1)NC2=O] | LCMS-A-1 | 2.28 | 577 (M + H)+ |
| 893 | 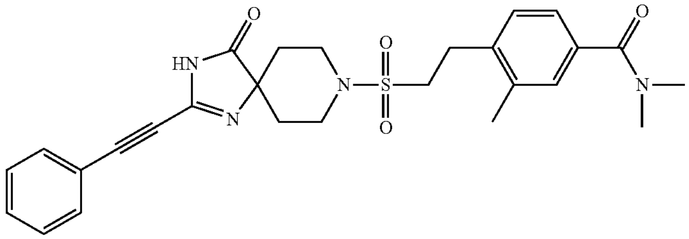 [SMILES: Cc1cc(C(=O)N(C)C)ccc1CCS(=O)(=O)N1CCC2(CC1)N=C(C#Cc1ccccc1)NC2=O] | LCMS-C-1 | 2.42 | 507 (M + H)+ |
| 894 | 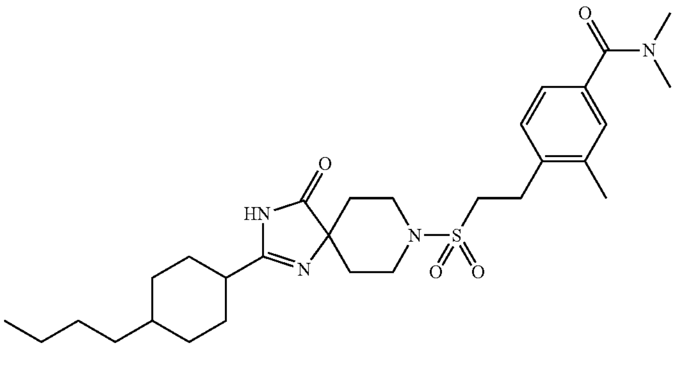 [SMILES: CCCCC1CCC(C2=NC3(CCN(S(=O)(=O)CCc4ccc(C(=O)N(C)C)cc4C)CC3)C(=O)N2)CC1] | LCMS-C-1 | 2.93 | 545 (M + H)+ |

TABLE 114-continued
| Compound | Structure | LCMS condition | Retention time (min) | MS (m/z) |
| --- | --- | --- | --- | --- |
| 895 | 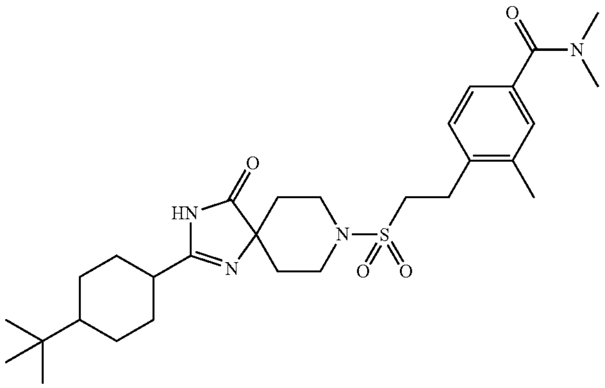 [SMILES: Cc1cc(C(=O)N(C)C)ccc1CCS(=O)(=O)N1CCC2(CC1)N=C(C1CCC(C(C)(C)C)CC1)NC2=O] | LCMS-C-1 | 2.85 | 545 (M + H)+ |
| 896 | 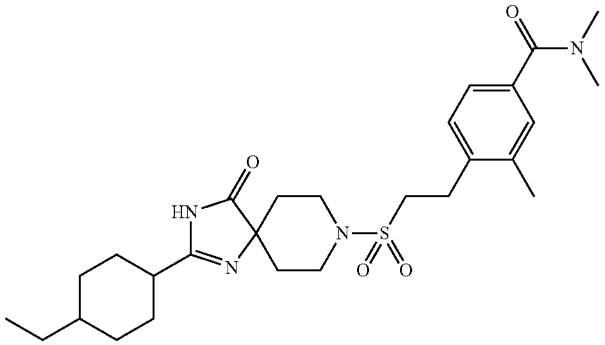 [SMILES: CCC1CCC(C2=NC3(CCN(S(=O)(=O)CCc4ccc(C(=O)N(C)C)cc4C)CC3)C(=O)N2)CC1] | LCMS-C-1 | 2.63 | 517 (M + H)+ |
| 897 | 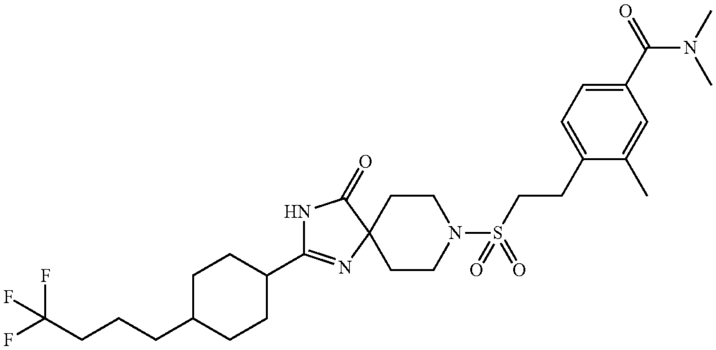 [SMILES: Cc1cc(C(=O)N(C)C)ccc1CCS(=O)(=O)N1CCC2(CC1)N=C(C1CCC(CCCC(F)(F)F)CC1)NC2=O] | LCMS-B-2 | 4.91 | 599 (M + H)+ |
| 898 | 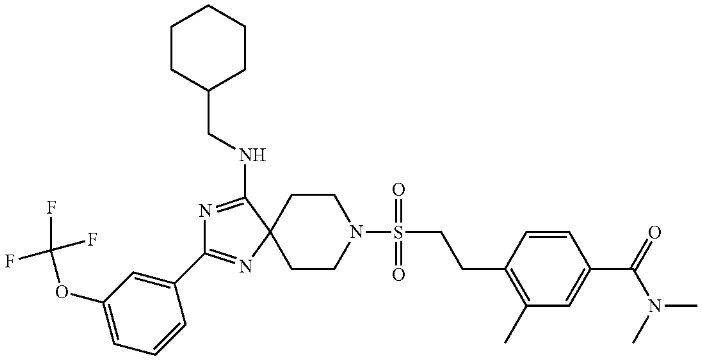 [SMILES: Cc1cc(C(=O)N(C)C)ccc1CCS(=O)(=O)N1CCC2(CC1)N=C(c1cccc(OC(F)(F)F)c1)N=C2NCC1CCCCC1] | LCMS-C-2 | 2.88 | 660 (M − H)− |

TABLE 114-continued

| Compound | Structure | LCMS condition | Retention time (min) | MS (m/z) |
|---|---|---|---|---|
| 899 | 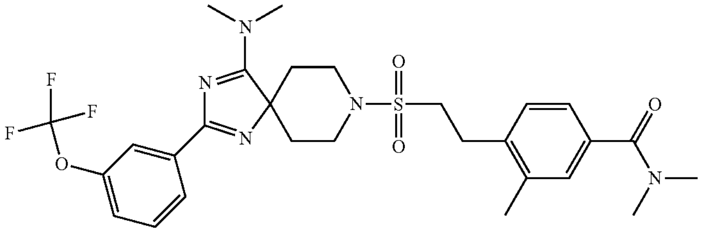 [SMILES: Cc1cc(C(=O)N(C)C)ccc1CCS(=O)(=O)N1CCC2(CC1)N=C(c1cccc(OC(F)(F)F)c1)N=C2N(C)C] | LCMS-A-1 | 2.24 | 594 (M + H)+ |
| 900 | 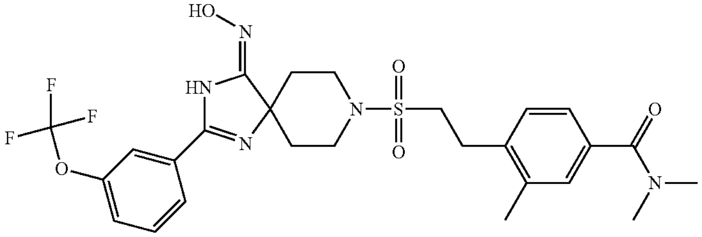 [SMILES: Cc1cc(C(=O)N(C)C)ccc1CCS(=O)(=O)N1CCC2(CC1)N=C(c1cccc(OC(F)(F)F)c1)N/C2=N\O] | LCMS-C-2 | 1.93 | 582 (M + H)+ |
| 901 | 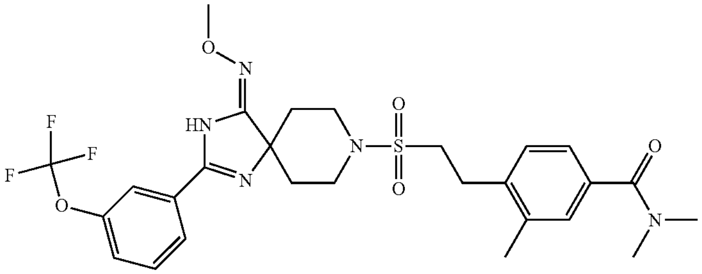 [SMILES: CO/N=C1\NC(c2cccc(OC(F)(F)F)c2)=NC12CCN(S(=O)(=O)CCc1ccc(C(=O)N(C)C)cc1C)CC2] | LCMS-C-2 | 2.33 | 594 (M − H)− |

The spiroamine reagents used in the synthesis of Compounds 890, 891, 895 and 897 and shown below were synthesized by operations similar to those in Reaction 10-14, Reaction 1-4 and Reaction 4-1 using appropriate reagents and Compound 5a as a starting material.

TABLE 115

| Target Compound | Spiroamine reagent | Spiroamine reagent MS (m/z) |
|---|---|---|
| 890 | 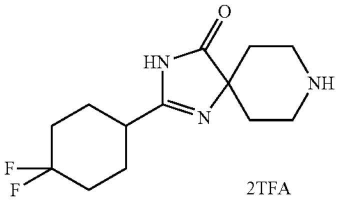 [SMILES: O=C1NC(C2CCC(F)(F)CC2)=NC12CCNCC2 ; "2TFA"] 2TFA | 272 (M + H)+ |
| 891 | 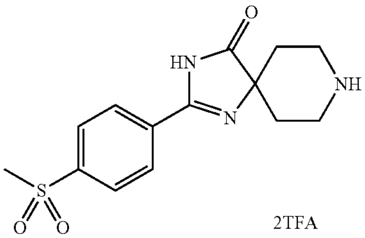 [SMILES: CS(=O)(=O)c1ccc(C2=NC3(CCNCC3)C(=O)N2)cc1 ; "2TFA"] 2TFA | 308 (M + H)+ |

TABLE 115-continued

| Target Compound | Spiroamine reagent | Spiroamine reagent MS (m/z) |
| --- | --- | --- |
| 895 | 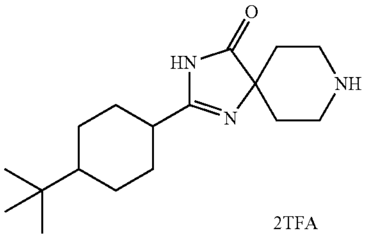 [SMILES: CC(C)(C)C1CCC(C2=NC3(CCNCC3)C(=O)N2)CC1 ; "2TFA"] 2TFA | 292 (M + H)+ |
| 897 | 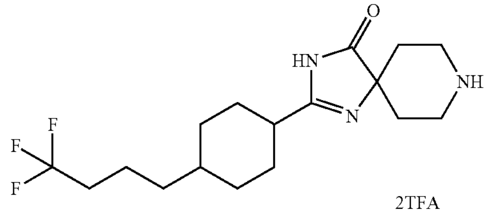 [SMILES: O=C1NC(C2CCC(CCCC(F)(F)F)CC2)=NC12CCNCC2 ; "2TFA"] 2TFA | 346 (M + H)+ |

The carboxylic acid necessary for the synthesis of the spiroamine reagent used for Compound 897 (4-(4,4,4-trifluoro-but-1-enyl)-cyclohexanecarboxylic acid methyl ester) was synthesized by the method shown below.

(Reaction 189-2)

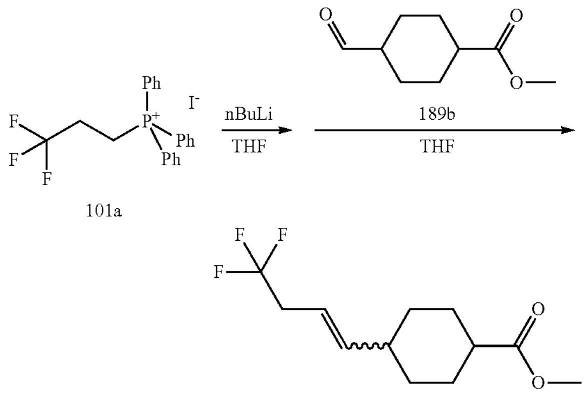

101a 189b 189c

A 1.6 M solution of n-butyllithium in hexane (2.5 mL) was added dropwise to a suspension of triphenyl-(3,3,3-trifluoro-propyl)-phosphonium iodide (1.90 g, 3.91 mmol) in tetrahydrofuran (14 mL) at 0° C. The mixture was stirred at 0° C. for 35 minutes, and a solution of 4-formyl-cyclohexanecarboxylic acid methyl ester (605 mg, 3.55 mmol) in tetrahydrofuran (8.0 mL) was then added dropwise to the reaction solution at −78° C. The mixture was stirred for 45 minutes, and a saturated aqueous ammonium chloride solution was then added, followed by extraction with tert-butyl methyl ether. The organic layer was washed with water and a saturated aqueous sodium chloride solution and washed with sodium sulfate. After concentration, the residue was purified by silica gel column chromatography to give 4-(4,4,4-trifluoro-but-1-enyl)-cyclohexanecarboxylic acid methyl ester (657 mg, 67%) as a colorless oily substance and geometric isomer mixture.

$^1$H-NMR ($CDCl_3$) δ 5.69 (1.0H, t, J=10.4 Hz), 5.51 (0.2H, dt, J=13.7, 2.9 Hz), 5.32 (1.2H, tt, J=9.2, 3.3 Hz), 3.69 (2.8H, dd, J=3.0, 2.6 Hz), 3.67 (0.6H, d, J=0.6 Hz), 2.90-2.78 (2.5H, m), 2.59-2.54 (1.0H, m), 2.40-2.31 (1.0H, m), 2.25-2.20 (0.5H, m), 2.06-1.98 (2.6H, m), 1.75-1.13 (8.0H, m).

(Reaction 189-3)

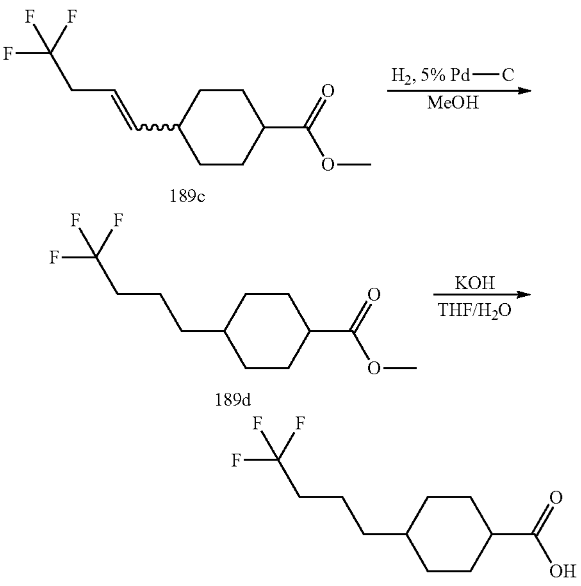

189c 189d 189e 4-(4,4,4-Trifluorobutyl)-cyclohexanecarboxylic acid was synthesized by operations similar to those in Reaction 18-2 and Reaction 95-18 (using potassium hydroxide as a base) using appropriate reagents and starting material. This was used as such in the next reaction.

The spiroamine reagent used in the synthesis of Compound 892 (2-[(E)-2-(3-trifluoromethyl-phenyl)-vinyl]-1,3,8-triaza-spiro[4.5]dec-1-en-4-one dihydrochloride) was synthesized by the method shown below.

(Reaction 189-4)

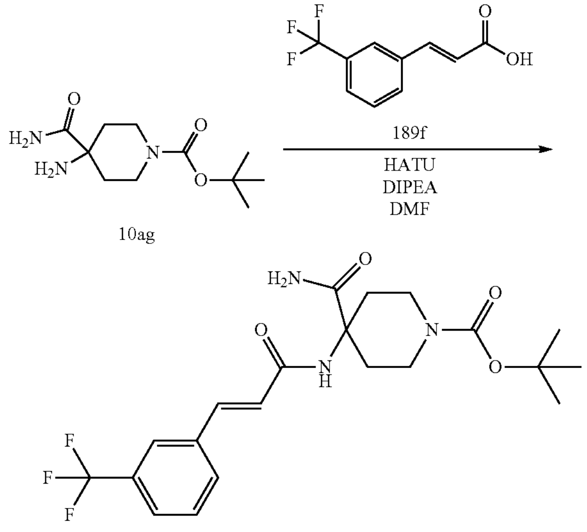

10ag

189g

4-Carbamoyl-4-[(E)-3-(3-trifluoromethyl-phenyl)-acryloylamino]-piperidine-1-carboxylic acid tert-butyl ester was synthesized by operations similar to those in Reaction 10-14 using appropriate reagents and starting material.

MS (ESI) m/z=440 (M−H)−.

(Reaction 189-5)

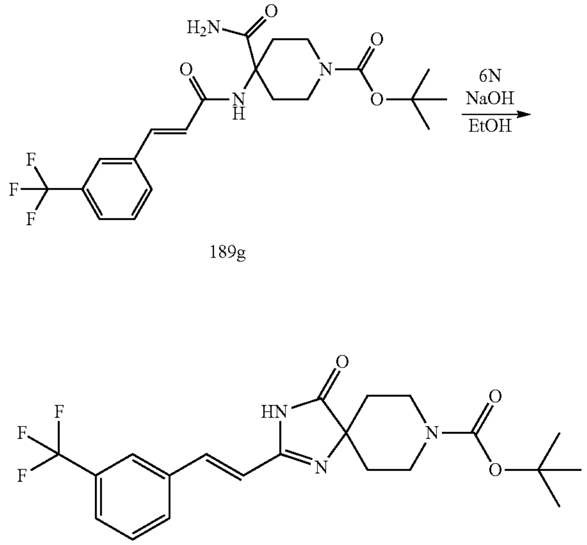

189g

189h

A 6 N aqueous sodium hydroxide solution was added to a solution of 4-carbamoyl-4-[(E)-3-(3-trifluoromethyl-phenyl)-acryloylamino]-piperidine-1-carboxylic acid tert-butyl ester (961 mg, 2.27 mmol) in ethanol (20 ml), and the mixture was stirred at room temperature for 22 hours. The reaction solution was quenched with saturated ammonium chloride and then extracted with ethyl acetate. The organic layer was sequentially washed with water and saturated brine, and then dried over anhydrous magnesium sulfate and concentrated under reduced pressure. The resulting residue was purified by silica gel column chromatography to give 4-oxo-2-[(E)-2-(3-trifluoromethyl-phenyl)-vinyl]-1,3,8-triaza-spiro[4.5]dec-1-ene-8-carboxylic acid tert-butyl ester (706 mg, 73%).

MS (ESI) m/z=422 (M−H)−.

(Reaction 189-6)

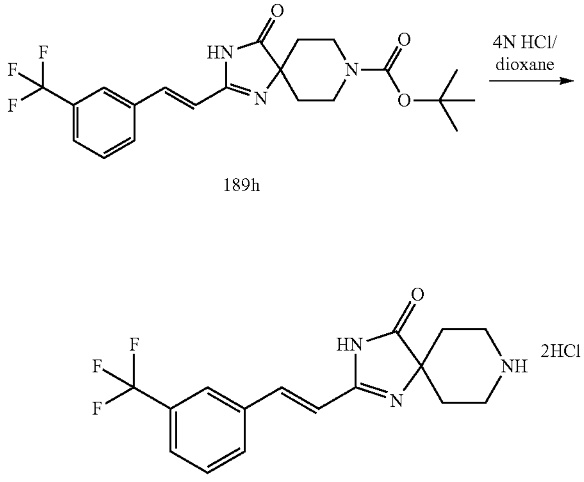

189h

189i

2-[(E)-2-(3-Trifluoromethyl-phenyl)-vinyl]-1,3,8-triaza-spiro[4.5]dec-1-en-4-one dihydrochloride was synthesized by operations similar to those in Reaction 5-3 using appropriate reagents and starting material.

MS (ESI) m/z=324 (M+H)+.

The spiroamine reagent used in the synthesis of Compound 893 (2-phenylethynyl-1,3,8-triaza-spiro[4.5]dec-1-en-4-one ditrifluoroacetate) was synthesized by the method shown below.

(Reaction 189-7)

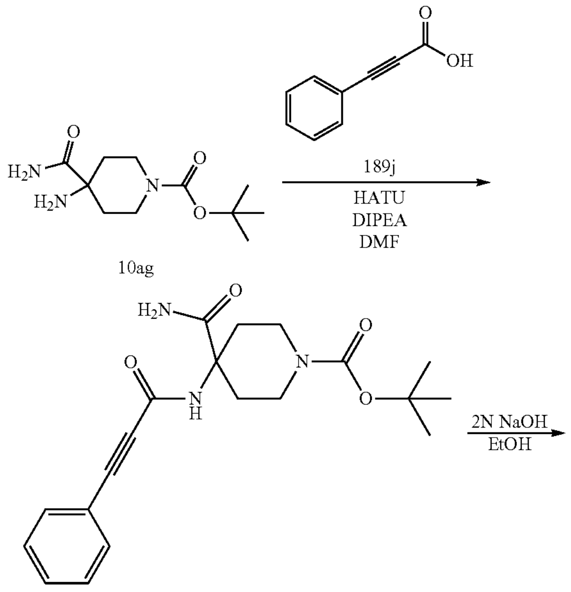

10ag

189k

-continued

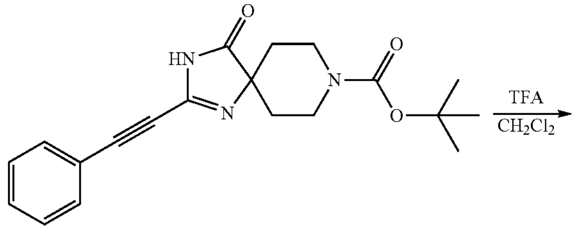

189l

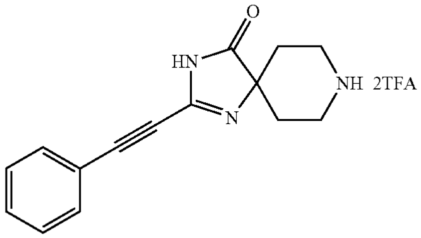

189m

2-Phenylethynyl-1,3,8-triaza-spiro[4.5]dec-1-en-4-one ditrifluoroacetate was synthesized by operations similar to those in Reaction 10-14, Reaction 189-5 and Reaction 4-1 using appropriate reagents and starting material.

MS (ESI) m/z=254 (M+H)+.

The spiroamine reagent used in the synthesis of Compound 898 (cyclohexylmethyl-[2-(3-trifluoromethoxy-phenyl)-1,3,8-triaza-spiro[4.5]deca-1,3-dien-4-yl]-amine ditrifluoroacetate) was synthesized as follows.

(Reaction 189-8)

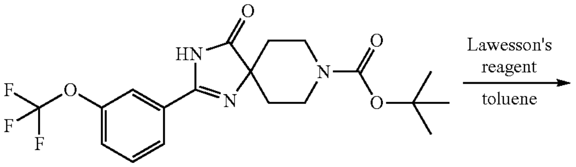

189n

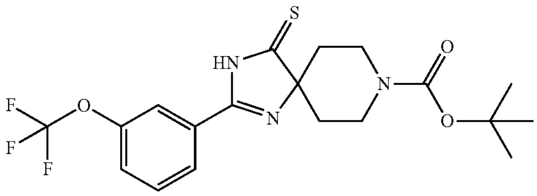

189o

4-Thioxo-2-(3-trifluoromethoxy-phenyl)-1,3,8-triaza-spiro[4.5]dec-1-ene-8-carboxylic acid tert-butyl ester was synthesized by operations similar to those in Reaction 88-1 using appropriate reagents and starting material.

$^1$H-NMR (400 MHz, $CDCl_3$) δ 1.42 (2H, dull d, J=16.0 Hz), 1.50 (9H, s), 2.14 (2H, td, J=16.0, 4.0 Hz), 3.33 (2H, br), 4.18 (2H, br), 7.44 (1H, m), 7.58 (1H, t, J=8.0 Hz), 7.79 (1H, d, J=8.0 Hz), 7.82 (1H, s), 10.30 (1H, br).

(Reaction 189-9)

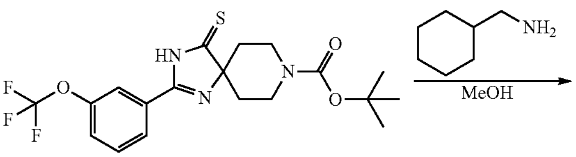

189o

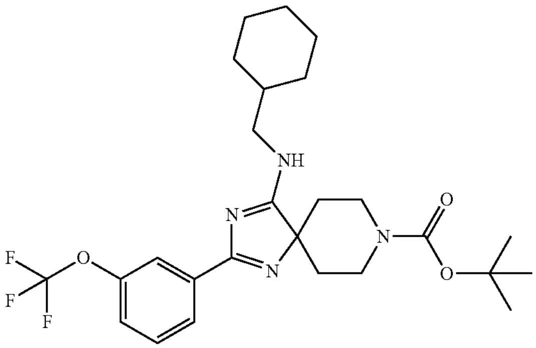

189p

Cyclohexyl-methylamine (0.044 ml, 0.34 mmol) was added to a solution of 4-thioxo-2-(3-trifluoromethoxy-phenyl)-1,3,8-triaza-spiro[4.5]dec-1-ene-8-carboxylic acid tert-butyl ester (14.6 mg, 0.0340 mmol) in methanol (0.1 ml), and the mixture was stirred at 60° C. for 24 hours and at 70° C. for 11 hours. The reaction mixture was concentrated under reduced pressure, and the resulting residue was purified by silica gel column chromatography (hexane-ethyl acetate) to give 4-(cyclohexylmethyl-amino)-2-(3-trifluoromethoxy-phenyl)-1,3,8-triaza-spiro[4.5]deca-1,3-diene-8-carboxylic acid tert-butyl ester (16.3 mg, 94%).

$^1$H-NMR (400 MHz, $CDCl_3$) δ 1.02 (2H, m), 1.24 (3H, m), 1.44 (2H, d, J=13.2 Hz), 1.50 (9H, s), 1.65 (4H, m), 1.76 (4H, m), 3.40 (4H, m), 4.17 (2H, br), 5.12 (1H, br), 7.28 (1H, m), 7.44 (1H, t, J=8.0 Hz), 7.08 (1H, dull s), 8.16 (1H, m).

(Reaction 189-10)

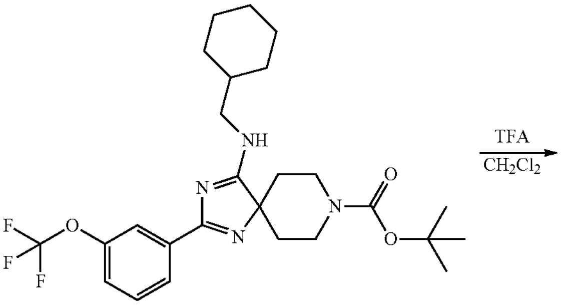

189p

-continued

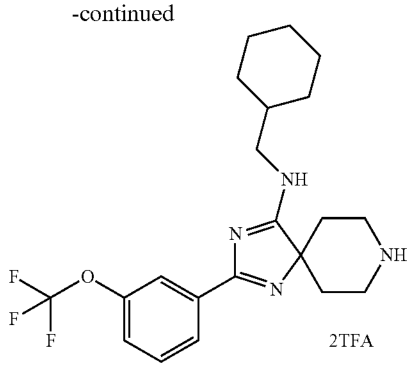

189q

Cyclohexylmethyl-[2-(3-trifluoromethoxy-phenyl)-1,3,8-triaza-spiro[4.5]deca-1,3-dien-4-yl]-amine ditrifluoroacetate was synthesized by operations similar to those in Reaction 4-1 using appropriate reagents and starting material.

MS (ESI) m/z=255 (M+H)+.

The spiroamine reagents used in the synthesis of Compounds 899 to 901 and shown below were synthesized by operations similar to those in Reaction 189-9 and Reaction 189-10 using appropriate reagents and starting materials.

TABLE 116

| Target Compound | Spiroamine reagent | Spiroamine reagent $^1$H-NMR |
|---|---|---|
| 899 | 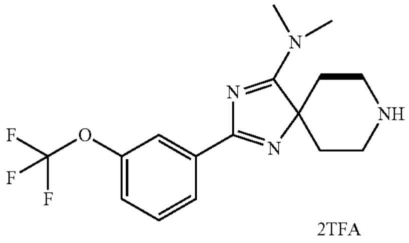 | $^1$H NMR (400 MHz, $CDCl_3$) δ: 2.06 (4H, m), 3.24 (2H, m), 3.60 (3H, s), 3.70 (3H, s), 4.10 (2H, br), 7.60 (1H, d, J = 8 Hz), 7.65 (1H, t, J = 8 Hz), 8.32 (1H, s), 8.49 (1H, d, J = 8 Hz). |
| 900 | 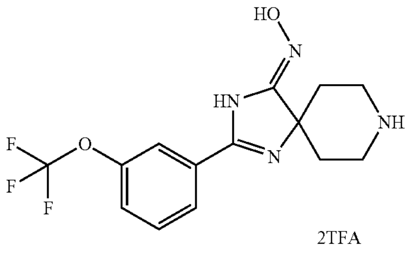 [SMILES: O/N=C1\NC(c2cccc(OC(F)(F)F)c2)=NC12CCNCC2 ; "2TFA"] | This was used in the next reaction without purification. |
| 901 | 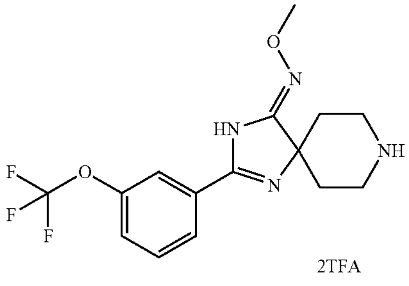 [SMILES: CO/N=C1\NC(c2cccc(OC(F)(F)F)c2)=NC12CCNCC2 ; "2TFA"] | This was used in the next reaction without purification. |

Example 190

4-(2-{2-[4-(2-Methoxy-ethyl)-cyclohexyl]-4-oxo-1,3,8-triaza-spiro[4.5]dec-1-ene-8-sulfonyl}-ethyl)-3,N,N-trimethyl-benzamide (Compound 902)

(Reaction 190-1)

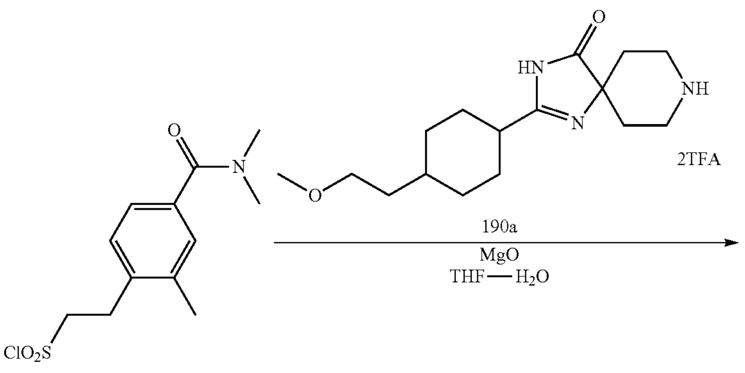

10f

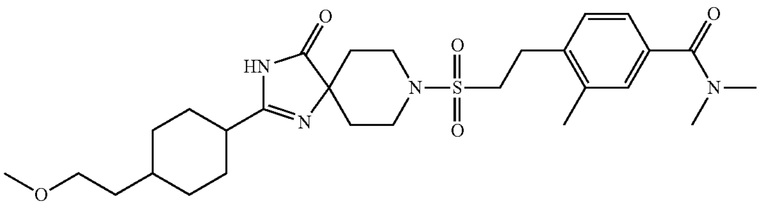

Compound 902

2-(4-Dimethylcarbamoyl-2-methyl-phenyl)-ethanesulfonyl chloride (22.2 mg) was added to a solution of 2-[4-(2-methoxy-ethyl)-cyclohexyl]-1,3,8-triaza-spiro[4.5]dec-1-en-4-one ditrifluoroacetate (63.9 μmol) and magnesium oxide (20 mg) in tetrahydrofuran-water (4:1 (v/v), 640 μL), and the mixture was stirred at room temperature for 30 minutes. 2-(4-Dimethylcarbamoyl-2-methyl-phenyl)-ethanesulfonyl chloride (22.2 mg) was further added and the mixture was stirred for one hour. The reaction mixture was quenched with water and extracted with dichloromethane. The organic layer was concentrated, and the resulting residue was purified by silica gel column chromatography (ethyl acetate-hexane) to give 4-(2-{2-[4-(2-methoxy-ethyl)-cyclohexyl]-4-oxo-1,3,8-triaza-spiro[4.5]dec-1-ene-8-sulfonyl}-ethyl)-3,N,N-trimethyl-benzamide (32.7 mg, 94%).

MS (ESI) m/z=547 (M+H)+.

The spiroamine reagent used in the synthesis of Compound 902 and shown below (2-[4-(2-methoxy-ethyl)-cyclohexyl]-1,3,8-triaza-spiro[4.5]dec-1-en-4-one ditrifluoroacetate) was synthesized by operations similar to those in Reaction 10-14, Reaction 1-4 and Reaction 4-1 using appropriate reagents and Compound 5a as a starting material.

TABLE 117

| Target Compound | Spiroamine reagent | Spiroamine reagent MS (m/z) |
|---|---|---|
| 902 | 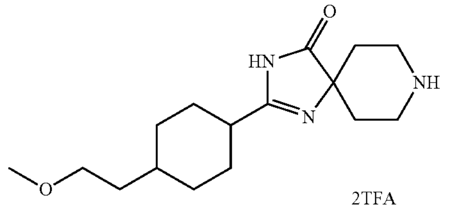 [SMILES: COCCC1CCC(C2=NC3(CCNCC3)C(=O)N2)CC1 ; "2TFA"] | 294 (M + H)+ |

The carboxylic acid (4-(2-methoxy-ethyl)-cyclohexanecarboxylic acid) necessary for the synthesis of the spiroamine reagent used for Compound 902 (2-[4-(2-methoxy-ethyl)-cyclohexyl]-1,3,8-triaza-spiro[4.5]dec-1-en-4-one ditrifluoroacetate) was synthesized by the method shown below.

(Reaction 190-2)

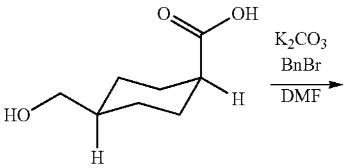

cis/trans (2.9:1)
190b

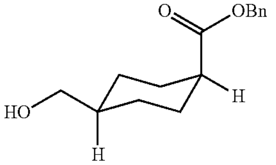

cis/trans (3.5:1)
190c

Potassium carbonate (2.61 g, 18.9 mmol) and benzyl bromide (2.24 mL, 18.9 mmol) were added to a solution of 4-hydroxymethyl-cyclohexanecarboxylic acid (cis-trans=2.9:1 mixture) (2.49 g, 15.7 mmol) in DMF (31.5 mL) at room temperature, and the mixture was stirred at 60° C. for one hour. The reaction solution was cooled, and $H_2O$ (60 mL) was then added to the reaction solution, followed by extraction with hexane:ethyl acetate (2:1) (300 mL) twice. The organic layers were dried over sodium sulfate and concentrated under reduced pressure. The resulting residue was purified by silica gel column chromatography (hexane-ethyl acetate) to give 4-hydroxymethyl-cyclohexanecarboxylic acid benzyl ester (cis-trans=3.5:1 mixture) as a colorless oily substance (3.79 g, 97%).

MS (ESI) m/z=249 (M+H)+.

(Reaction 190-3)

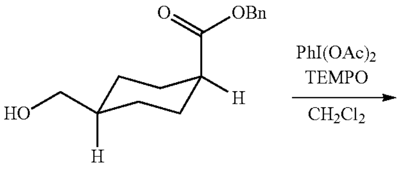

cis/trans (4:1)
190c

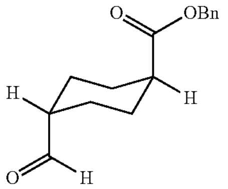

cis/trans (4:1)
190d 2,2,6,6-Tetramethylpiperidine 1-oxyl (309 mg, 1.98 mmol) and (diacetoxyiodo)benzene (7.01 g, 21.8 mmol) were added to a solution of 4-hydroxymethyl-cyclohexanecarboxylic acid benzyl ester (cis-trans=4:1 mixture) (4.91 g, 19.8 mmol) at 0° C. in an $N_2$ atmosphere, and the mixture was stirred at 0° C. for one hour and at room temperature for seven hours. The reaction solution was diluted with dichloromethane (200 mL), and the organic layer was sequentially washed with a saturated aqueous sodium sulfite solution (100 mL), a saturated aqueous sodium bicarbonate solution (100 mL) and saturated brine (100 mL). The organic layer was dried over sodium sulfate and then concentrated under reduced pressure. The resulting residue was purified by silica gel column chromatography (hexane-ethyl acetate) to give 4-formyl-cyclohexanecarboxylic acid benzyl ester (cis-trans=4:1 mixture) as a colorless oily substance (4.44 g, 91%).

MS (ESI) m/z=247 (M+H)+.

(Reaction 190-4)

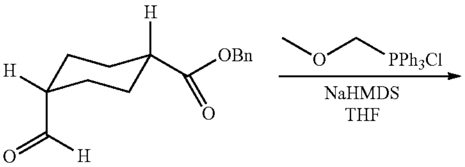

cis/trans (4:1)
190d

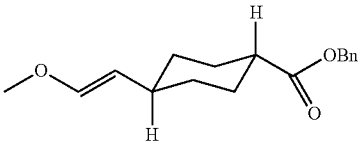

trans:cis (4:1), E/Z (2:1)
190e

NaHMDS (1.0 M in THF) (466 μL, 466 μmol) was added to a solution of methoxymethyltriphenylphosphonium chloride (160 mg, 466 μmol) in tetrahydrofuran (3.88 mL) at 0° C. in an $N_2$ atmosphere, and the mixture was stirred at 0° C. for one hour. A solution of 4-formyl-cyclohexanecarboxylic acid benzyl ester (cis-trans=4:1 mixture) (95.6 mg, 388 μmol) in tetrahydrofuran (2.00 mL) was added dropwise to the reaction solution at 0° C., and the mixture was stirred for 30 minutes. Thereafter, the reaction mixture was stirred at room temperature for 20 hours and quenched with a saturated aqueous ammonium chloride solution (5 mL). $H_2O$ (20 mL) was then added, followed by extraction with dichloromethane (50 mL). The organic layer was dried over sodium sulfate and concentrated under reduced pressure. The resulting residue was purified by silica gel column chromatography (hexane-ethyl acetate) to give 4-(2-methoxy-vinyl)-cyclohexanecarboxylic acid benzyl ester (trans-cis=4:1 and E-Z=2:1 mixture) as a yellow oily substance (49.7 mg, 47%).

MS (ESI) m/z=275 (M+H)+.

(Reaction 190-5)

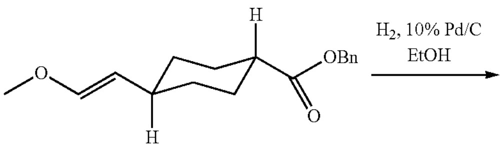

trans:cis (4:1),
E/Z (2:1)
190e

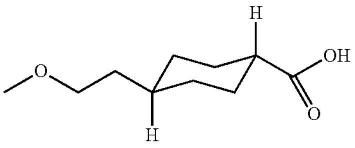

cis/trans (1:5.4)
190f 4-(2-Methoxy-ethyl)-cyclohexanecarboxylic acid was synthesized by operations similar to those in Reaction 18-2 using appropriate reagents and starting material.

$^1$H-NMR (400 MHz, $CDCl_3$) δ 0.89-1.02 (2H, ddd, J=3.8, 13.2, 24.9 Hz), 1.30-1.62 (5H, m), 1.79-1.85 (2H, br-m), 1.92-2.04 (2H, br-m), 2.25 (0.8H, tt, J=3.4, 12.2 Hz), 2.58 (0.2H, quintet, J=4.9 Hz), 3.32 (0.6H, s), 3.33 (2.4H, s), 3.41 (2H, t, J=6.8 Hz).

Example 191

N-{4-[2-(2-Cyclopentyl-4-oxo-1,3,8-triaza-spiro[4.5]dec-1-ene-8-sulfonyl)-ethyl]-3-methyl-phenyl}-acetamide (Compound 903)

(Reaction 191-1)

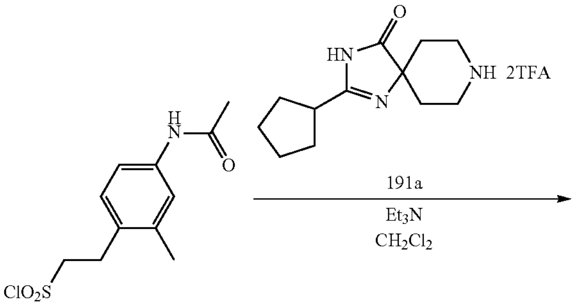

11e

-continued

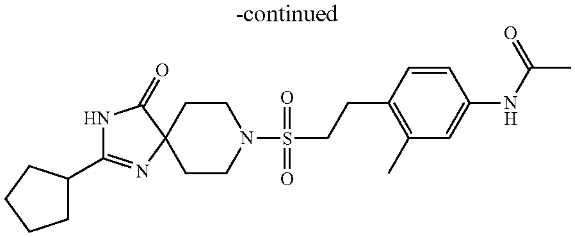

Compound 903

N-{4-[2-(2-Cyclopentyl-4-oxo-1,3,8-triaza-spiro[4.5]dec-1-ene-8-sulfonyl)-ethyl]-3-methyl-phenyl}-acetamide was synthesized by operations similar to those in Reaction 5-4 using appropriate reagents and starting material.

MS (ESI) m/z=461 (M+H)+.

The example compounds shown below were synthesized by operations similar to those in Reaction 191-1 using appropriate reagents and starting materials.

Compounds 904 to 916

TABLE 118

| Compound | Structure | LCMS condition | Retention time (min) | MS (m/z) |
|---|---|---|---|---|
| 904 | 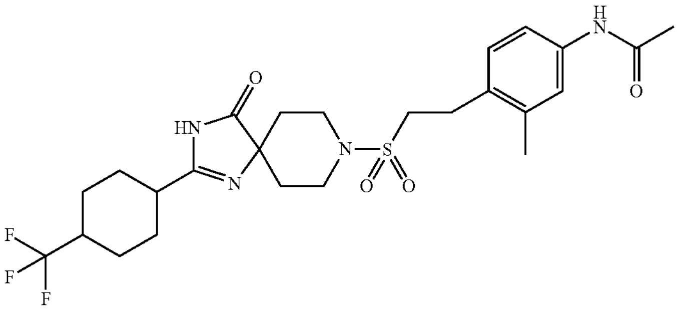 [SMILES: CC(=O)Nc1ccc(CCS(=O)(=O)N2CCC3(CC2)N=C(C2CCC(C(F)(F)F)CC2)NC3=O)c(C)c1] | LCMS-C-1 | 2.45 | 543 (M + H)+ |
| 905 | 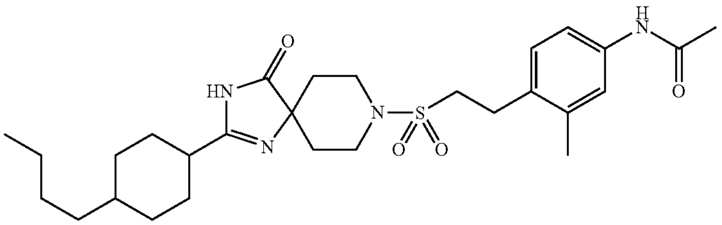 [SMILES: CCCCC1CCC(C2=NC3(CCN(S(=O)(=O)CCc4ccc(NC(C)=O)cc4C)CC3)C(=O)N2)CC1] | LCMS-C-1 | 2.85 | 531 (M + H)+ |

TABLE 118-continued
| Compound | Structure | LCMS condition | Retention time (min) | MS (m/z) |
|---|---|---|---|---|
| 906 | 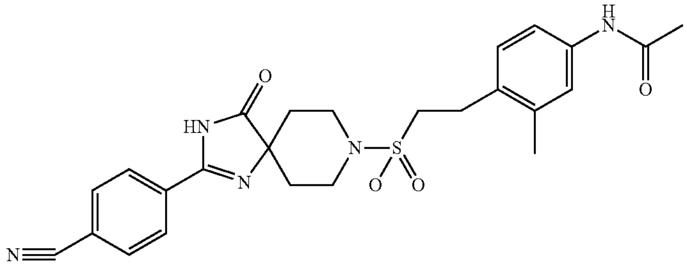 | LCMS-A-1 | 2.05 | 494 (M + H)+ |
| 907 | 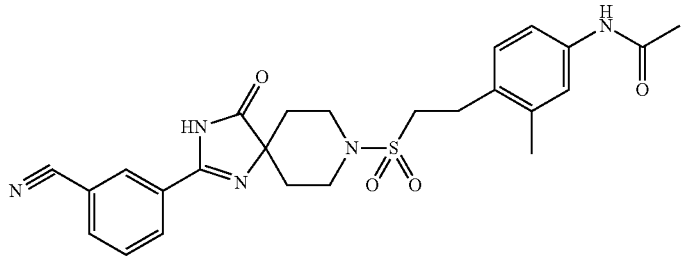 [SMILES: CC(=O)Nc1ccc(CCS(=O)(=O)N2CCC3(CC2)N=C(c2cccc(C#N)c2)NC3=O)c(C)c1] | LCMS-A-1 | 2.05 | 494 (M + H)+ |
| 908 | 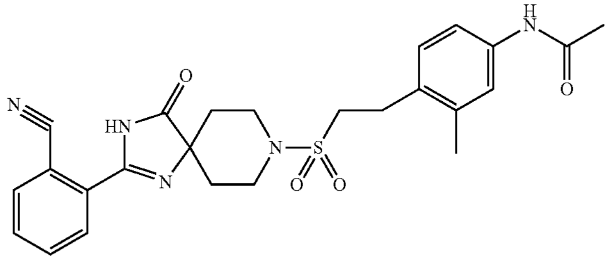 [SMILES: CC(=O)Nc1ccc(CCS(=O)(=O)N2CCC3(CC2)N=C(c2ccccc2C#N)NC3=O)c(C)c1] | LCMS-A-1 | 1.99 | 494 (M + H)+ |
| 909 | 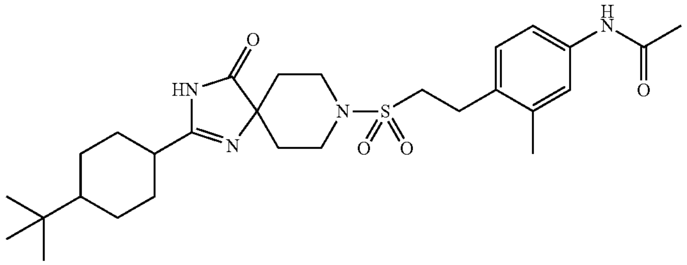 [SMILES: CC(=O)Nc1ccc(CCS(=O)(=O)N2CCC3(CC2)N=C(C2CCC(C(C)(C)C)CC2)NC3=O)c(C)c1] | LCMS-C-1 | 2.85 | 531 (M + H)+ |
| 910 | 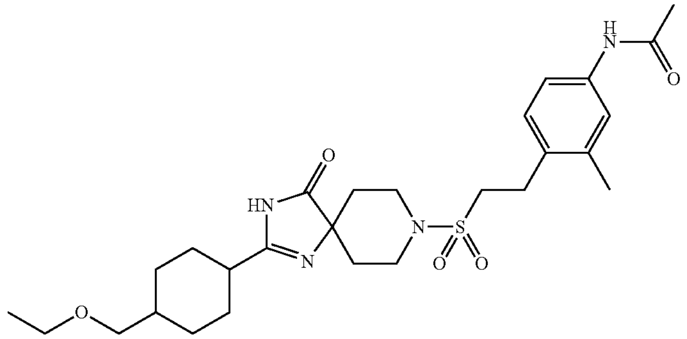 [SMILES: CCOCC1CCC(C2=NC3(CCN(S(=O)(=O)CCc4ccc(NC(C)=O)cc4C)CC3)C(=O)N2)CC1] | LCMS-C-1 | 2.38 | 533 (M + H)+ |

TABLE 118-continued
| Compound | Structure | LCMS condition | Retention time (min) | MS (m/z) |
| --- | --- | --- | --- | --- |
| 911 | 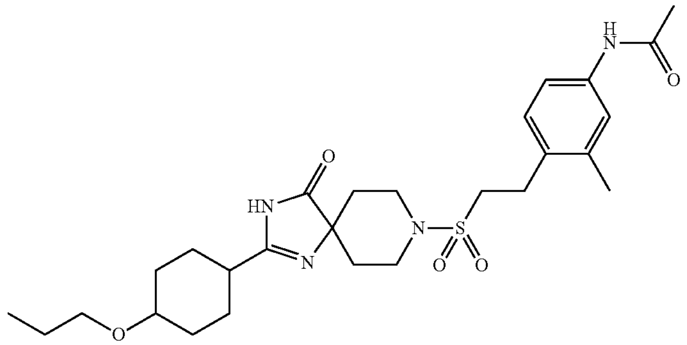 [SMILES: CCCOC1CCC(C2=NC3(CCN(S(=O)(=O)CCc4ccc(NC(C)=O)cc4C)CC3)C(=O)N2)CC1] | LCMS-C-1 | 2.48 | 533 (M + H)+ |
| 912 | 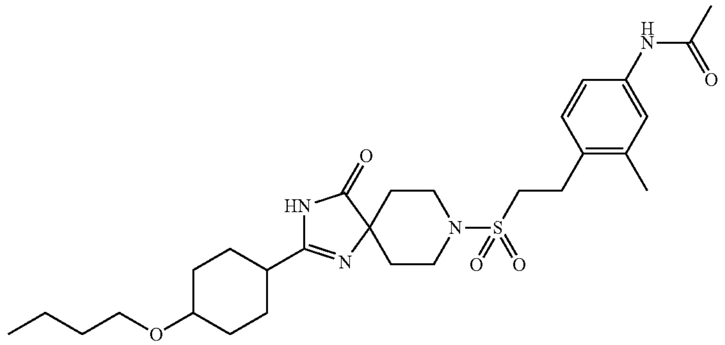 [SMILES: CCCCOC1CCC(C2=NC3(CCN(S(=O)(=O)CCc4ccc(NC(C)=O)cc4C)CC3)C(=O)N2)CC1] | LCMS-C-1 | 2.6 | 547 (M + H)+ |
| 913 | 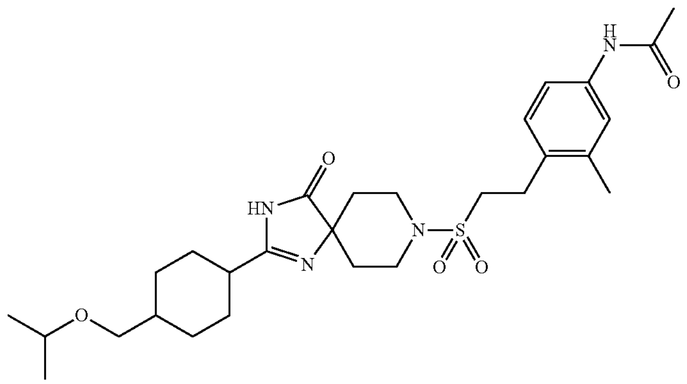 [SMILES: CC(=O)Nc1ccc(CCS(=O)(=O)N2CCC3(CC2)N=C(C2CCC(COC(C)C)CC2)NC3=O)c(C)c1] | LCMS-C-1 | 2.52 | 547 (M + H)+ |
| 914 | 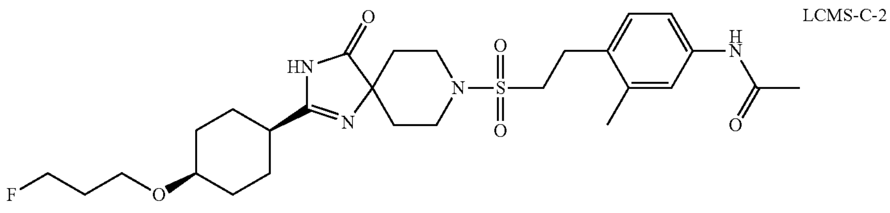 | LCMS-C-2 | 1.68 | 551 (M + H)+ |
| 915 | 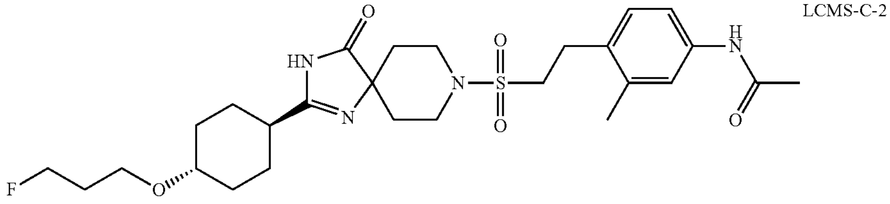 | LCMS-C-2 | 1.65 | 551 (M + H)+ |

TABLE 118-continued

| Compound | Structure | LCMS condition | Retention time (min) | MS (m/z) |
|---|---|---|---|---|
| 916 | 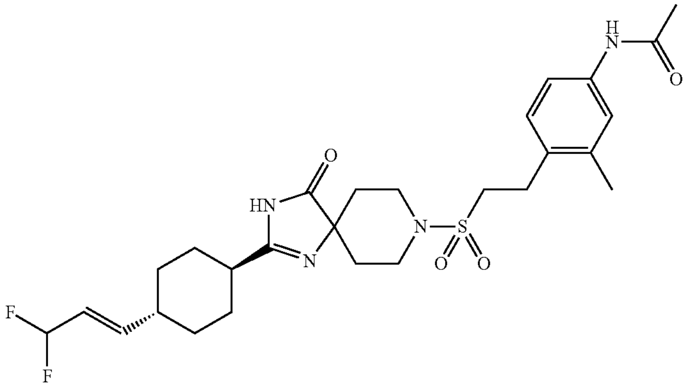 [SMILES: CC(=O)Nc1ccc(CCS(=O)(=O)N2CCC3(CC2)N=C([C@H]2CC[C@H](/C=C/C(F)F)CC2)NC3=O)c(C)c1] | LCMS-C-2 | 1.85 | 551 (M + H)+ |

The spiroamine reagent used in the synthesis of Compound 906 (4-(4-oxo-1,3,8-triaza-spiro[4.5]dec-1-en-2-yl)-benzonitrile dihydrochloride) was synthesized by the following method.

(Reaction 191-2)

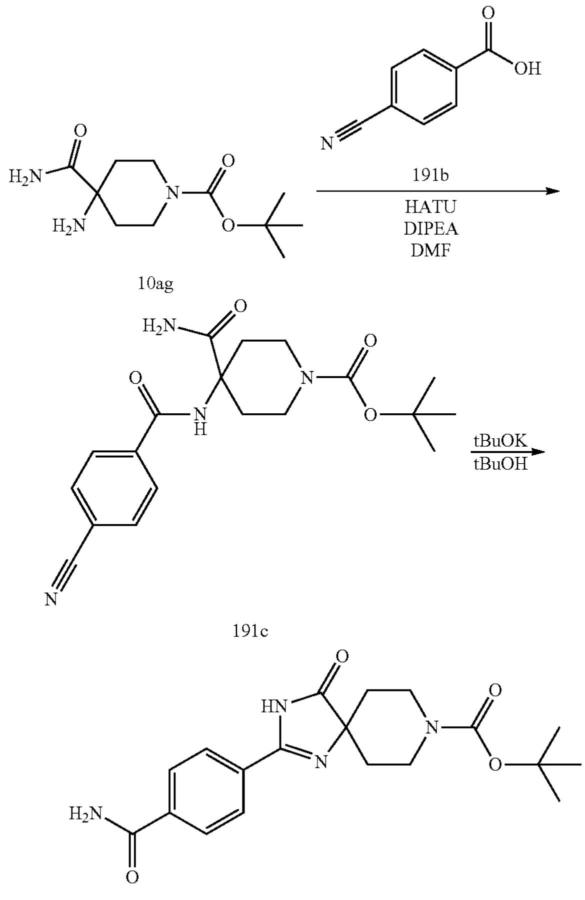

10ag

191b

191c

191d 2-(4-Carbamoyl-phenyl)-4-oxo-1,3,8-triaza-spiro[4.5]dec-1-ene-8-carboxylic acid tert-butyl ester was synthesized by operations similar to those in Reaction 10-14 and Reaction 10-12 using appropriate reagents and starting material.

MS (ESI) m/z=373 (M+H)+.

(Reaction 191-3)

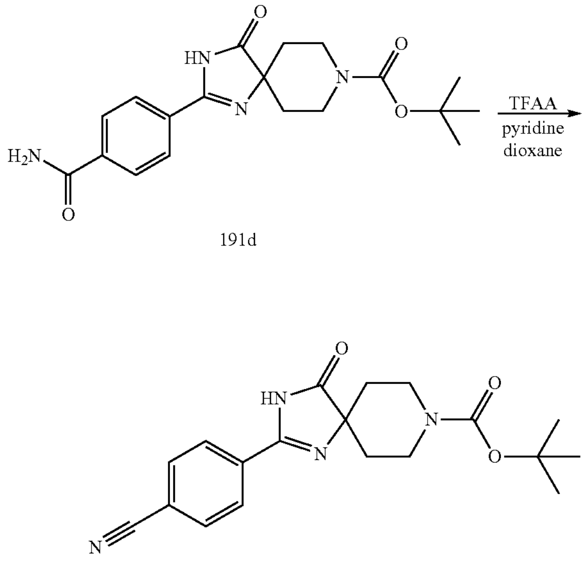

191d

191e

Trifluoroacetic anhydride (0.287 ml, 2.07 mmol) was added to a solution of 2-(4-carbamoyl-phenyl)-4-oxo-1,3,8-triaza-spiro[4.5]dec-1-ene-8-carboxylic acid tert-butyl ester (350 mg, 0.94 mmol) and pyridine (0.303 ml) in dioxane (1.1 ml) at 0° C. The mixture was stirred for 30 minutes and then stirred at room temperature for one hour. An aqueous $NaHCO_3$ solution was added to the reaction mixture, followed by extraction with dichloromethane. The organic layer was concentrated under reduced pressure, and the resulting residue was purified by silica gel column chromatography (dichloromethane-ethyl acetate) to give 2-(4-cyano-phenyl)-4-oxo-1,3,8-triaza-spiro[4.5]dec-1-ene-8-carboxylic acid tert-butyl ester as a white powder (235 mg, 71%).

MS (ESI) m/z=353 (M−H)−.

(Reaction 191-4)

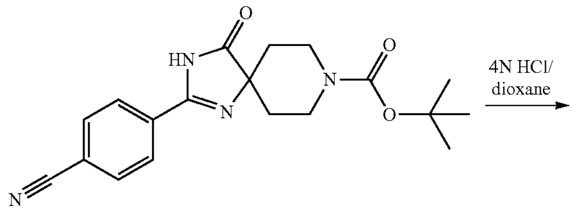

191e

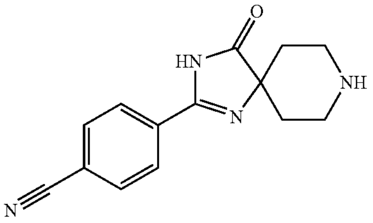 2HCl

191f 4-(4-Oxo-1,3,8-triaza-spiro[4.5]dec-1-en-2-yl)-benzonitrile dihydrochloride was synthesized by operations similar to those in Reaction 5-3 using appropriate reagents and starting material.

MS (ESI) m/z=255 (M+H)+.

The spiroamine reagents used in the synthesis of Compounds 907 to 908 and shown below were synthesized by operations similar to those in Reaction 10-14, Reaction 10-12 and Reaction 5-3 using appropriate reagents and Compound 10ag as a starting material.

TABLE 119

| Target Compound | Spiroamine reagent | Spiroamine reagent MS (m/z) |
|---|---|---|
| 907 | 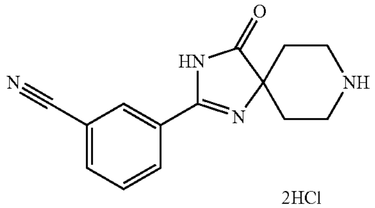 [SMILES: N#Cc1cccc(C2=NC3(CCNCC3)C(=O)N2)c1 ; "2HCl"] 2HCl | 255 (M + H)+ |
| 908 | 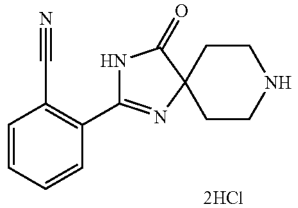 [SMILES: N#Cc1ccccc1C1=NC2(CCNCC2)C(=O)N1 ; "2HCl"] 2HCl | 255 (M + H)+ |

The spiroamine reagents used in the synthesis of Compounds 910, 911, 912 and 913 and shown below were synthesized by operations similar to those in Reaction 10-14, Reaction 1-4 and Reaction 4-1 using appropriate reagents and Compound 5a as a starting material.

TABLE 120

| Target Compound | Spiroamine reagent | Spiroamine reagent MS (m/z) or $^1$H-NMR |
|---|---|---|
| 910 | 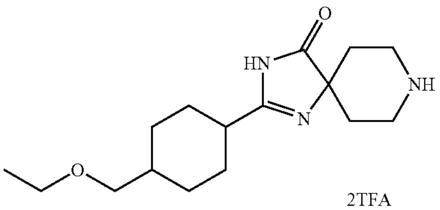 [SMILES: CCOCC1CCC(C2=NC3(CCNCC3)C(=O)N2)CC1 ; "2TFA"] 2TFA | 292 (M − H)− |
| 911 | 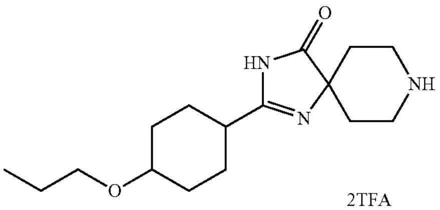 [SMILES: CCCOC1CCC(C2=NC3(CCNCC3)C(=O)N2)CC1 ; "2TFA"] 2TFA | 292 (M − H)− |
| 912 | 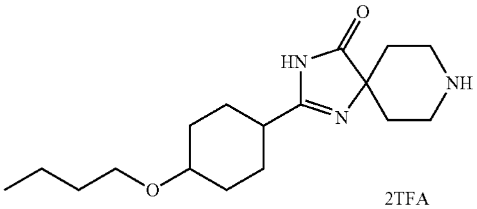 [SMILES: CCCCOC1CCC(C2=NC3(CCNCC3)C(=O)N2)CC1 ; "2TFA"] 2TFA | 306 (M − H)− |

TABLE 120-continued

| Target Compound | Spiroamine reagent | Spiroamine reagent MS (m/z) or $^1$H-NMR |
|---|---|---|
| 913 | 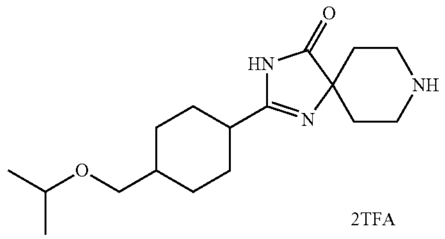 [SMILES: CC(C)OCC1CCC(C2=NC3(CCNCC3)C(=O)N2)CC1 ; "2TFA"] 2TFA | 306 (M − H)− |
| 916 | 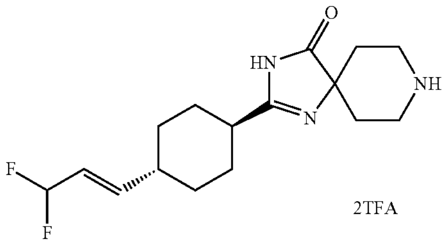 [SMILES: O=C1NC([C@H]2CC[C@H](/C=C/C(F)F)CC2)=NC12CCNCC2 ; "2TFA"] 2TFA | $^1$H-NMR (400 MHz, $CD_3OD$) δ 1.24-1.33 (2H, m), 1.56-1.64 (2H, m), 1.93-1.96 (4H, m), 2.06-2.13 (5H, m), 2.50-2.70 (1H, m), 3.34-3.42 (2H, m), 3.51-3.57 (2H, m), 5.61-5.70 (1H, m), 5.96-6.25 (2H, m) |

The carboxylic acid necessary for the synthesis of the spiroamine reagent used for Compound 910 (4-ethoxymethyl-cyclohexanecarboxylic acid) was synthesized by the method shown below.

(Reaction 191-5)

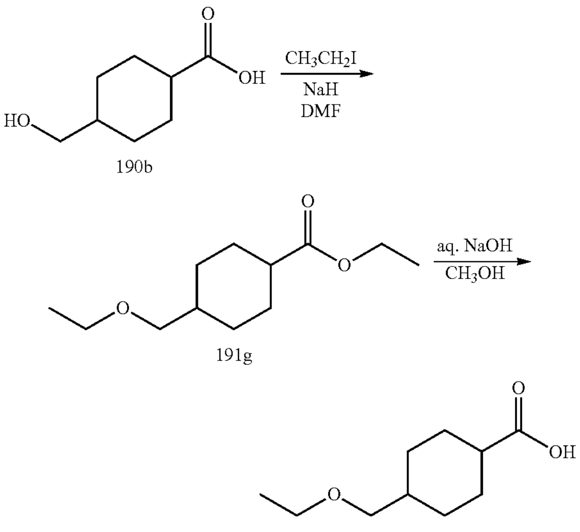

190b

191g

191h

4-Ethoxymethyl-cyclohexanecarboxylic acid was synthesized by operations similar to those in Reaction 20-2 and Reaction 95-18 using appropriate reagents and starting material. This was used as such in the next reaction.

The carboxylic acid necessary for the synthesis of the spiroamine reagent used for Compound 911 (4-propoxy-cyclohexanecarboxylic acid) was synthesized by the method shown below.

(Reaction 191-6)

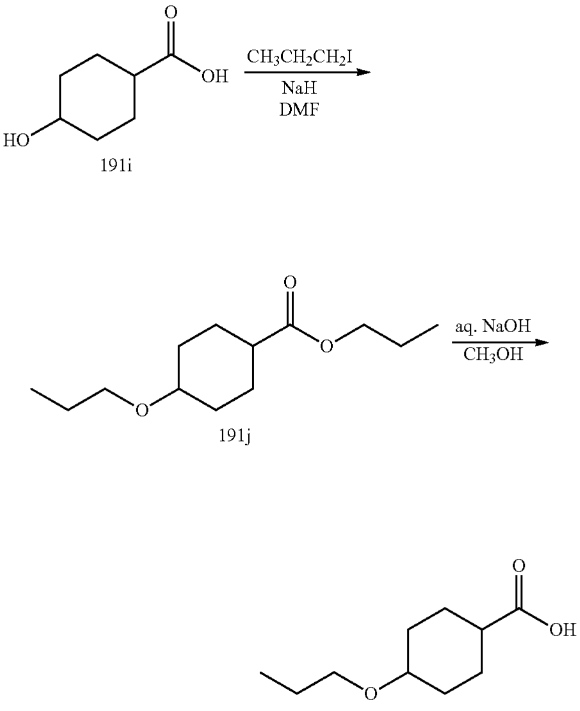

191i

191j

191k

4-Propoxy-cyclohexanecarboxylic acid was synthesized by operations similar to those in Reaction 20-2 and Reaction 95-18 using appropriate reagents and starting material. This was used as such in the next reaction.

The carboxylic acid necessary for the synthesis of the spiroamine reagent used for Compound 912 (4-butoxy-cyclohexanecarboxylic acid) was synthesized by the method shown below.

(Reaction 191-7)

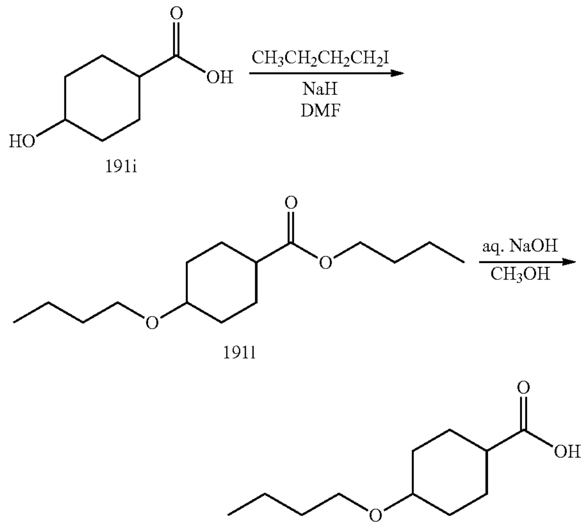

191i

191l

191m

4-Butoxy-cyclohexanecarboxylic acid was synthesized by operations similar to those in Reaction 20-2 and Reaction 95-18 using appropriate reagents and starting material. This was used as such in the next reaction.

The carboxylic acid necessary for the synthesis of the spiroamine reagent used for Compound 913 (4-isopropoxymethyl-cyclohexanecarboxylic acid) was synthesized by the method shown below.

(Reaction 191-8)

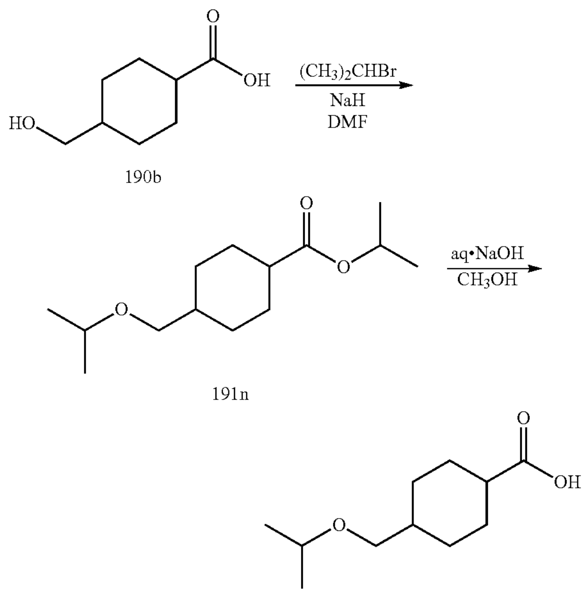

190b

191n

191o

4-Isopropoxymethyl-cyclohexanecarboxylic acid was synthesized by operations similar to those in Reaction 20-2 and Reaction 95-18 using appropriate reagents and starting material. This was used as such in the next reaction.

The spiroamine reagent used in the synthesis of Compound 914 (2-[4-(3-fluoro-propoxy)-cyclohexyl]-1,3,8-triaza-spiro[4.5]dec-1-en-4-one ditrifluoroacetate) was synthesized by the following method.

(Reaction 191-9)

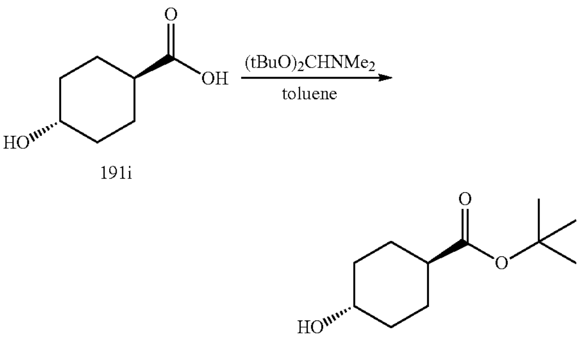

191i

191p

N,N-Dimethylformamide di-tert-butyl acetal (7.4 ml, 31 mmol) was added to a solution of trans-4-hydroxy-cyclohexanecarboxylic acid (1.484 g, 10.29 mmol) in toluene (8.5 ml), and the mixture was stirred at 80° C. for 25 hours. The reaction mixture was diluted with ether, and the organic layer was sequentially washed with water, an aqueous sodium bicarbonate solution and saturated brine, dried over $MgSO_4$ and concentrated under reduced pressure. The resulting residue was purified by silica gel column chromatography (hexane-ethyl acetate) to give trans-4-hydroxy-cyclohexanecarboxylic acid tert-butyl ester as a colorless solid (838 m, 41%).

$^1$H-NMR (400 MHz, $CDCl_3$) δ 1.28 (2H, m), 1.43 (9H, s), 1.45 (2H, m), 1.99 (4H, m), 2.14 (1H, m), 3.60 (1H, m).

(Reaction 191-10)

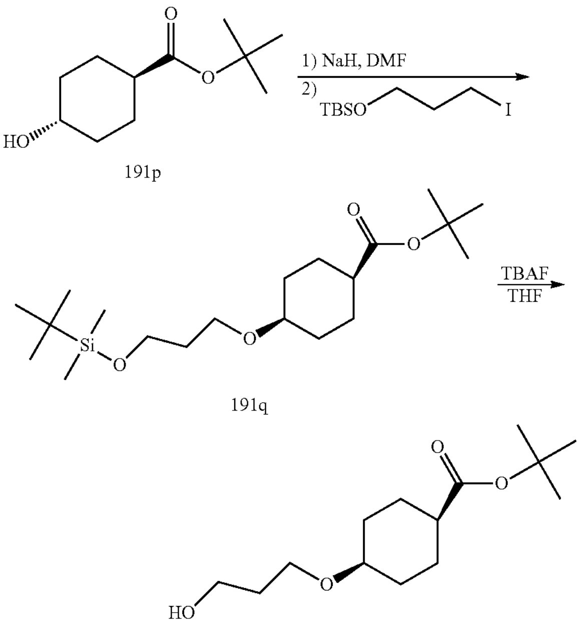

191p

191q

191r cis-4-(3-Hydroxy-propoxy)-cyclohexanecarboxylic acid tert-butyl ester was obtained by operations similar to those in Reaction 20-2 and Reaction 39-2 using the compound obtained above and appropriate reagents.

$^1$H-NMR (400 MHz, $CDCl_3$) δ 1.43 (9H, s), 1.53 (2H, m), 1.62 (2H, m), 1.83 (6H, m), 2.25 (1H, m), 2.60 (1H, t, J=5.4 Hz), 3.46 (1H, m), 3.61 (2H, t, J=5.9 Hz), 3.79 (2H, q, J=5.4 Hz).

(Reaction 191-11)

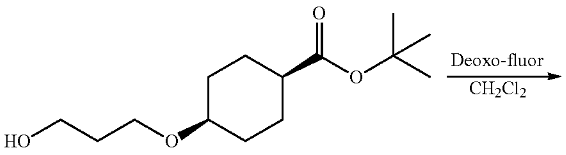

191r

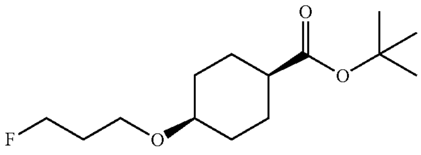

191s

Deoxo-Fluor (5 mg, 0.02 mmol) was added to a solution of cis-4-(3-hydroxy-propoxy)-cyclohexanecarboxylic acid tert-butyl ester (3.9 mg, 0.015 mmol) in dichloromethane (0.1 ml), and the mixture was stirred at room temperature for two hours. An aqueous sodium bicarbonate solution was added to the reaction mixture, followed by extraction with dichloromethane. The organic layer was then dried over $MgSO_4$ and concentrated under reduced pressure. The resulting residue was purified by silica gel column chromatography (hexane-ethyl acetate) to give cis-4-(3-fluoro-propoxy)-cyclohexanecarboxylic acid tert-butyl ester (3.1 mg, 79%).

$^1$H-NMR (400 MHz, $CDCl_3$) δ 1.44 (9H, s), 1.51 (2H, m), 1.60 (2H, m), 1.79 (2H, m), 1.94 (2H, m), 2.25 (1H, m), 2.60 (1H, t, J=5.4 Hz), 3.43 (1H, m), 3.51 (2H, t, J=6.1 Hz), 4.56 (2H, dt, J=47.4, 5.9 Hz).

(Reaction 191-12)

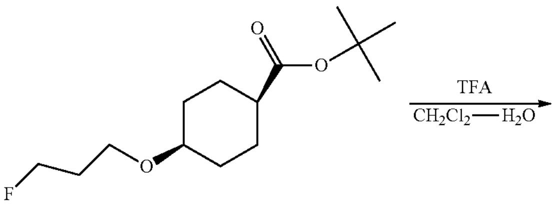

191s

-continued

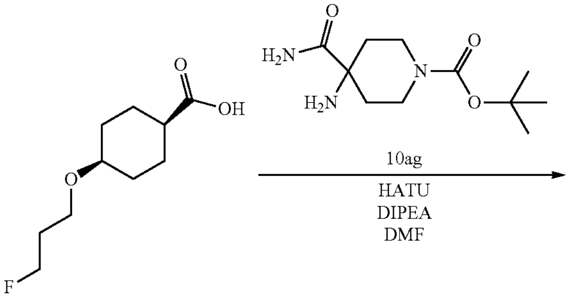

191t

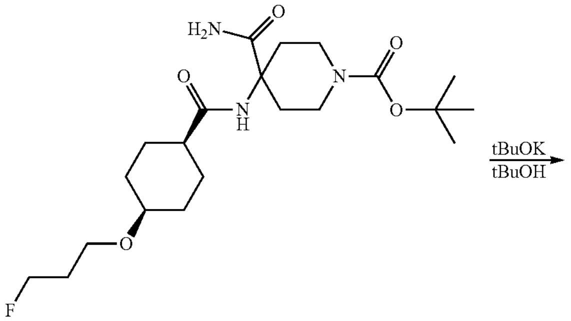

191u

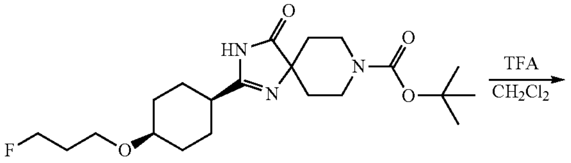

191v

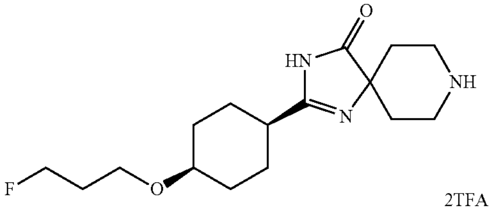

191w

2-[4-(3-Fluoro-propoxy)-cyclohexyl]-1,3,8-triaza-spiro[4.5]dec-1-en-4-one ditrifluoroacetate was synthesized by operations similar to those in Reaction 4-1 (further adding water), Reaction 10-14, Reaction 10-12 and Reaction 4-1 using appropriate reagents and starting material. This was used as such in the next reaction.

The spiroamine reagent used in the synthesis of Compound 915 and shown below was synthesized by operations similar to those in Reaction 10-14, Reaction 10-12 and Reaction 4-1 using appropriate reagents and Compound 10ag as a starting material.

TABLE 121

| Target Compound | Spiroamine reagent | Spiroamine reagent $^1$H-NMR |
|---|---|---|
| 915 | 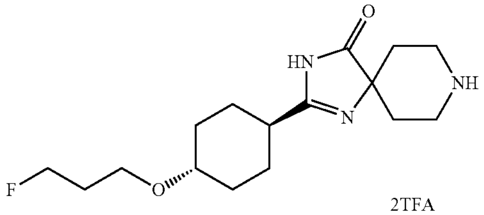 [SMILES: O=C1NC([C@H]2CC[C@H](OCCCF)CC2)=NC12CCNCC2 ; "2TFA"] 2TFA | This was used as such in the next reaction. |

The carboxylic acid necessary for the synthesis of the spiroamine reagent used for Compound 915 (4-(3-fluoro-propoxy)-cyclohexanecarboxylic acid) was synthesized by the method shown below.

(Reaction 191-13)

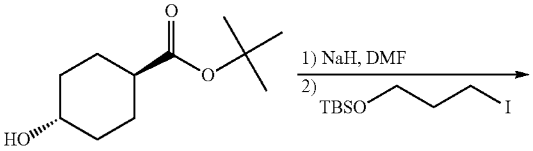

trans only
191p

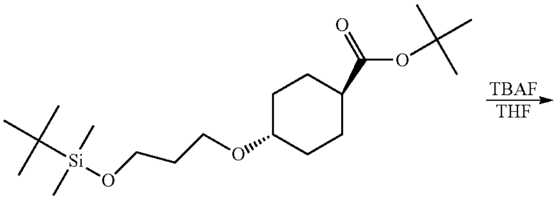

191x

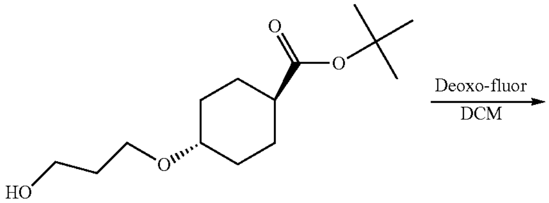

191y

-continued

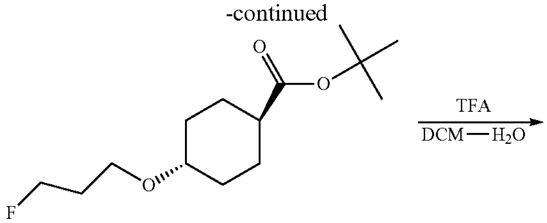

191z

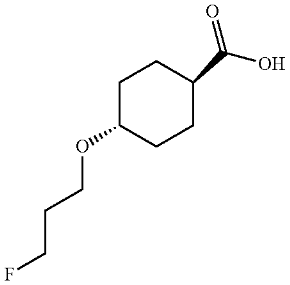

191aa 4-(3-Fluoro-propoxy)-cyclohexanecarboxylic acid was synthesized by operations similar to those in Reaction 20-2, Reaction 39-2, Reaction 191-11 and Reaction 4-1 (further adding water) using appropriate reagents and starting material. This was used as such in the next reaction.

The spiroamine reagent used in the synthesis of Compound 916 and shown below was synthesized by operations similar to those in Reaction 10-14, Reaction 1-4 and Reaction 4-1 using appropriate reagents and Compound 5a as a starting material.

TABLE 122

| Target Compound | Spiroamine reagent | Spiroamine reagent $^1$H-NMR |
|---|---|---|
| 916 | 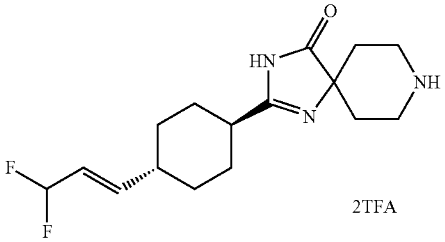 [SMILES: O=C1NC([C@H]2CC[C@H](/C=C/C(F)F)CC2)=NC12CCNCC2 ; "2TFA"] 2TFA | $^1$H-NMR (400 MHz, $CD_3OD$) δ 1.24-1.33 (2H, m), 1.56-1.64 (2H, m), 1.93-1.96 (4H, m), 2.06-2.13 (5H, m), 2.50-2.70 (1H, m), 3.34-3.42 (2H, m), 3.51-3.57 (2H, m), 5.61-5.70 (1H, m), 5.96-6.25 (2H, m) |

The carboxylic acid necessary for the synthesis of the spiroamine reagent used for Compound 916 (4-((E)-3,3-difluoro-propenyl)-cyclohexanecarboxylic acid) was synthesized by the method shown below.

(Reaction 191-14)

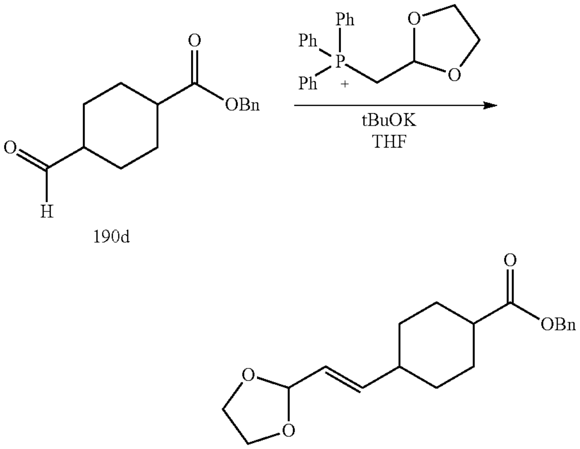

190d

191ab

Potassium t-butoxide (68.3 mg, 609 μmol) was added to a solution of (1,3-dioxolan-2-ylmethyl)-triphenylphosphonium bromide (267 mg, 609 μmol) in THF (2.0 ml) at 0° C., and the mixture was stirred at 0° C. for 1.5 hours in an $N_2$ atmosphere. A solution of 4-formyl-cyclohexanecarboxylic acid benzyl ester (50.0 mg, 203 μmol) in THF (1.5 ml) was added to the reaction mixture at 0° C., and the mixture was stirred at room temperature for 1.5 hours. Thereafter, the reaction mixture was quenched by adding a saturated aqueous ammonium chloride solution at 0° C. and then extracted with ethyl acetate three times. The organic layers were sequentially washed with $H_2O$ (×2) and saturated brine, and then dried over $MgSO_4$ and concentrated under reduced pressure. The residue was used in the next step without further purification.

(Reaction 191-15)

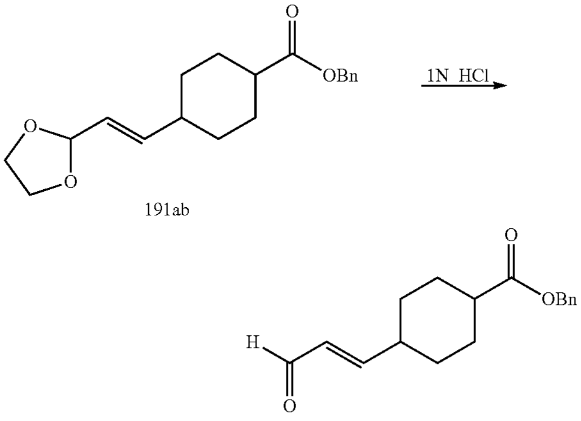

191ab

191ac

1 N hydrochloric acid (406 μl, 406 μl) was added to a solution of the residue obtained in Reaction 191-14 in THF (2.0 ml) at 0° C., and the mixture was stirred at room temperature for 4.5 hours. The reaction solution was quenched by adding a saturated aqueous sodium bicarbonate solution at 0° C. and then extracted with ethyl acetate three times. The organic layers were sequentially washed with $H_2O$ (×2) and saturated brine, and then dried over $MgSO_4$ and concentrated under reduced pressure. The residue was purified by column chromatography (hexane-ethyl acetate) to give 4-((E)-3-oxo-propenyl)-cyclohexanecarboxylic acid benzyl ester as a colorless oil (38.2 mg, 69%).

MS (ESI) m/z=273 (M+H)+.

(Reaction 191-16)

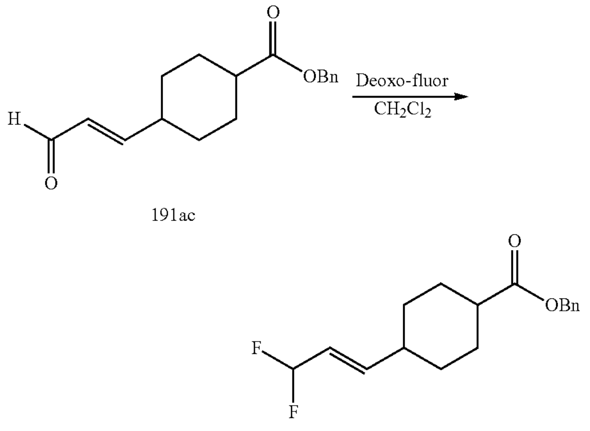

191ac

191ad 4-((E)-3,3-Difluoro-propenyl)-cyclohexanecarboxylic acid benzyl ester was synthesized by operations similar to those in Reaction 191-11 using appropriate reagents and starting material.

$^1$H-NMR (400 MHz, $CDCl_3$) δ 1.46-1.52 (2H, m), 1.61-1.67 (3H, m), 1.88-2.30 (4H, m), 2.60-2.70 (1H, m), 5.58-5.64 (1H, m), 5.88-6.17 (2H, m).

(Reaction 191-17)

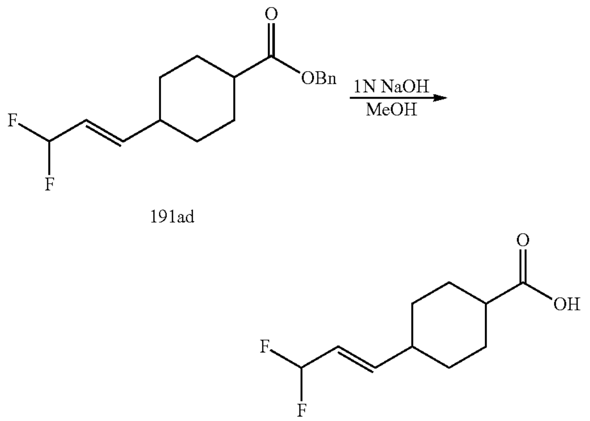

191ad

191ae 4-((E)-3,3-Difluoro-propenyl)-cyclohexanecarboxylic acid was synthesized by operations similar to those in Reaction 95-18 using appropriate reagents and starting material.

$^1$H-NMR (400 MHz, $CDCl_3$) δ 1.46-1.52 (2H, m), 1.61-1.67 (3H, m), 1.88-2.30 (4H, m), 2.60-2.70 (1H, m), 5.58-5.64 (1H, m), 5.88-6.17 (2H, m).

Example 192

N-{4-[2-(2-Cycloheptyl-4-oxo-1,3,8-triaza-spiro[4.5]dec-1-ene-8-sulfonyl)-ethyl]-3-methyl-phenyl}-acetamide (Compound 917)

(Reaction 192-1)

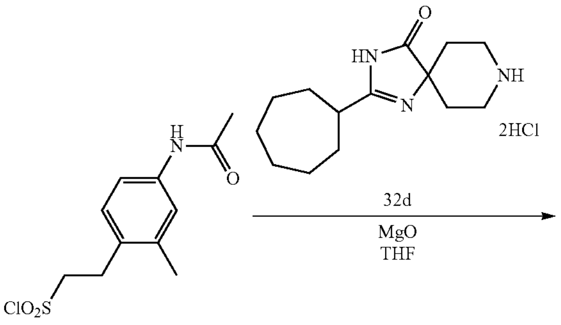

11e

-continued

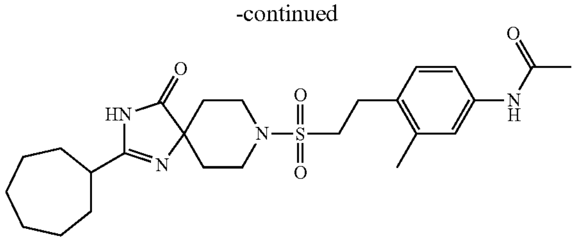

Compound 917

N-{4-[2-(2-Cycloheptyl-4-oxo-1,3,8-triaza-spiro[4.5]dec-1-ene-8-sulfonyl)-ethyl]-3-methyl-phenyl}-acetamide was synthesized by operations similar to those in Reaction 190-1 using appropriate reagents and starting material.

MS (ESI) m/z=489 (M+H)+.

The example compounds shown below were synthesized by operations similar to those in Reaction 192-1 using appropriate reagents and starting materials.

Compounds 918 to 919

TABLE 123

| Compound | Structure | LCMS condition | Retention time (min) | MS (m/z) |
|---|---|---|---|---|
| 918 | 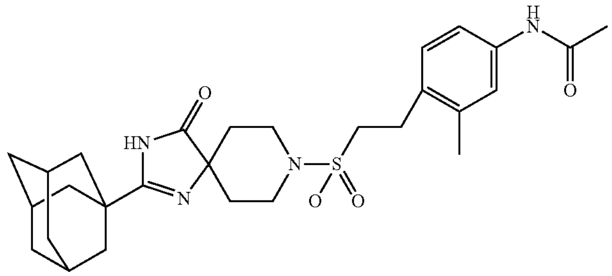 | LCMS-C-1 | 2.65 | 527 (M + H)+ |
| 919 | 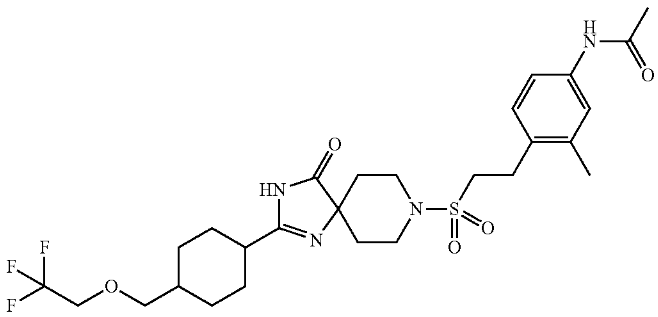 [SMILES: CC(=O)Nc1ccc(CCS(=O)(=O)N2CCC3(CC2)N=C(C2CCC(COCC(F)(F)F)CC2)NC3=O)c(C)c1] | LCMS-B-1 | 2.03 | 587 (M + H)+ |

The spiroamine reagent used in the synthesis of Compound 918 (2-adamantan-1-yl-1,3,8-triaza-spiro[4.5]dec-1-en-4-one ditrifluoroacetate) was synthesized by the following method.

(Reaction 192-2)

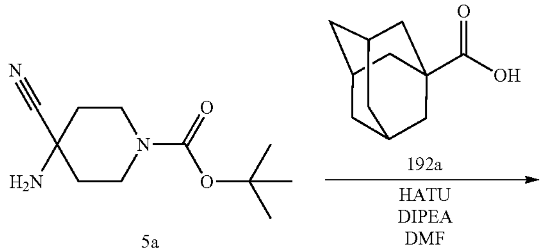

5a

-continued

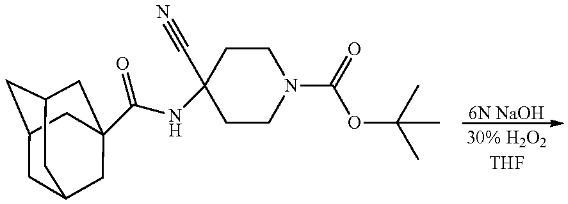

192b

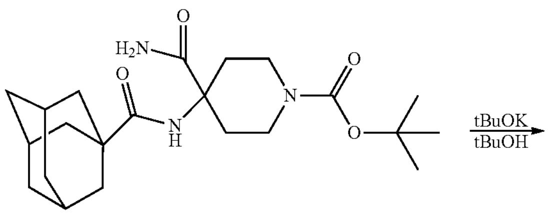

192c

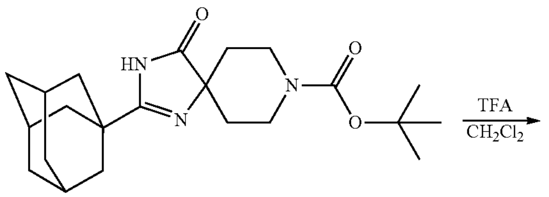

192d

-continued

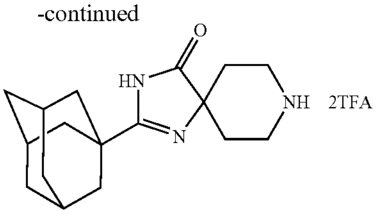

192e

2-Adamantan-1-yl-1,3,8-triaza-spiro[4.5]dec-1-en-4-one ditrifluoroacetate was synthesized by operations similar to those in Reaction 10-14, Reaction 10-11, Reaction 10-12 and Reaction 4-1 using appropriate reagents and starting material.

MS (ESI) m/z=288 (M+H)+.

The spiroamine reagent used in the synthesis of Compound 919 was synthesized by operations similar to those in Reaction 10-14, Reaction 1-4 and Reaction 4-1 using appropriate reagents and Compound 5a as a starting material.

TABLE 124

| Target Compound | Spiroamine reagent | Spiroamine reagent MS (m/z) |
|---|---|---|
| 919 | 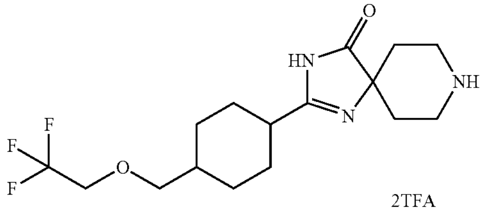 [SMILES: O=C1NC(C2CCC(COCC(F)(F)F)CC2)=NC12CCNCC2 ; "2TFA"] 2TFA | 348 (M + H)+ |

The carboxylic acid necessary for the synthesis of the spiroamine reagent used for Compound 919 (4-(2,2,2-trifluoro-ethoxymethyl)-cyclohexanecarboxylic acid) was synthesized by the method shown below.

(Reaction 192-3)

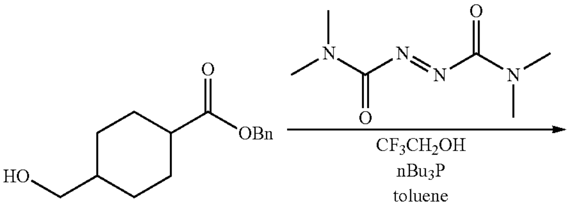

190c

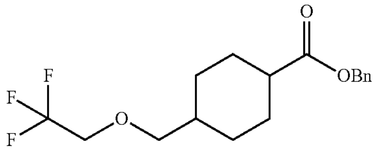

192f 2,2,2-Trifluoro-ethanol (288 μL, 4.03 mmol) was added to a mixed solution of 4-hydroxymethyl-cyclohexanecarboxylic acid benzyl ester (100 mg, 0.403 mmol), 1,1'-azobis(N,N-dimethylformamide) (139 mg, 0.805 mmol) and tributylphosphine (199 μL, 0.805 mmol) in toluene (1.2 mL) at 0° C. The mixture was stirred at 65° C. for 1.5 hours and then concentrated under reduced pressure. The resulting residue was purified by silica gel column chromatography to give 4-(2,2,2-trifluoro-ethoxymethyl)-cyclohexanecarboxylic acid benzyl ester as a colorless liquid (126 mg, 95%).

$^1$H-NMR (400 MHz, $CDCl_3$) δ 0.94-1.06 (0.4H, m), 1.23-1.47 (1.8H, m), 1.40-1.52 (0.4H, m), 1.55-1.68 (3.2H, m), 1.69-1.80 (0.8H, m), 1.82-1.91 (0.4H, m), 1.97-2.08 (2H, m), 2.25-2.34 (0.2H, m), 2.58-2.65 (0.8H, m) 3.41 (0.4H, d, J=6.8 Hz), 3.43 (1.6H, d, J=6.8 Hz), 3.78 (2H, q, J=8.8 Hz), 5.11 (0.4H, s), 5.13 (1.6H, s), 7.29-7.40 (5H, m).

(Reaction 192-4)

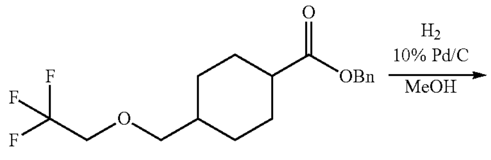

192f

-continued

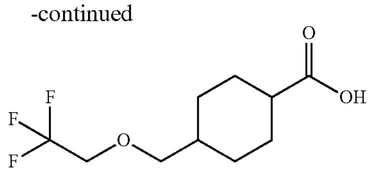

192g 4-(2,2,2-Trifluoro-ethoxymethyl)-cyclohexanecarboxylic acid was synthesized by operations similar to those in Reaction 18-2 using appropriate reagents and starting material.

$^1$H-NMR (400 MHz, $CDCl_3$) δ 0.96-2.23 (9H, m), 2.30-2.90 (1H, m), 3.37-3.49 (2H, m), 3.79 (2H, q, J=8.8 Hz), 9.56 (1H, brs).

Example 193

N-[4-(2-{2-[4-(4-Chloro-phenyl)-cyclohexyl]-4-oxo-1,3,8-triaza-spiro[4.5]dec-1-ene-8-sulfonyl}-ethyl)-3-methyl-phenyl]-acetamide (Compound 920)

(Reaction 193-1)

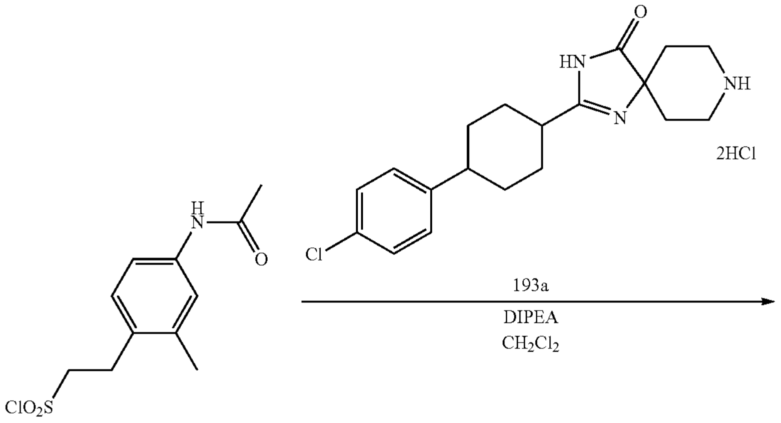

11e

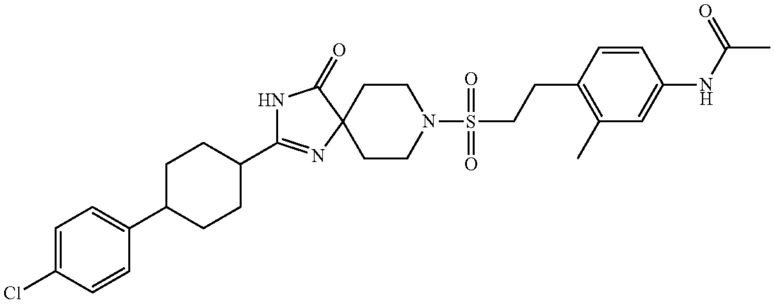

Compound 920

N-[4-(2-{2-[4-(4-Chloro-phenyl)-cyclohexyl]-4-oxo-1,3,8-triaza-spiro[4.5]dec-1-ene-8-sulfonyl}-ethyl)-3-methyl-phenyl]-acetamide was synthesized by operations similar to those in Reaction 5-4 using appropriate reagents and starting material.

MS (ESI) m/z=586 (M+H)+.

The example compounds shown below were synthesized by operations similar to those in Reaction 193-1 using appropriate reagents and starting materials.

Compounds 921 to 926
TABLE 125
| Compound | Structure | LCMS condition | Retention time (min) | MS (m/z) |
|---|---|---|---|---|
| 921 | 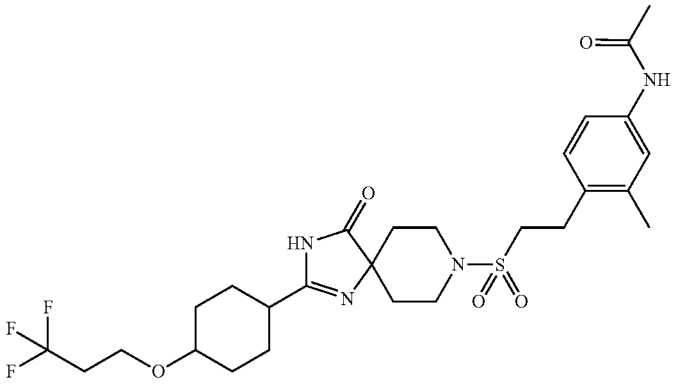 [SMILES: CC(=O)Nc1ccc(CCS(=O)(=O)N2CCC3(CC2)N=C(C2CCC(OCCC(F)(F)F)CC2)NC3=O)c(C)c1] | LCMS-B-1 | 1.79 | 587 (M + H)+ |
| 922 | 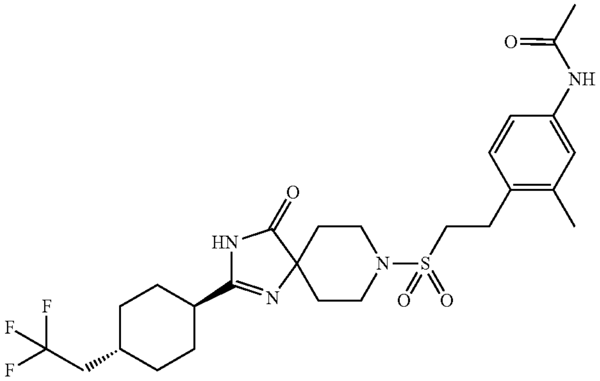 [SMILES: CC(=O)Nc1ccc(CCS(=O)(=O)N2CCC3(CC2)N=C([C@H]2CC[C@H](CC(F)(F)F)CC2)NC3=O)c(C)c1] | LCMS-C-1 | 2.53 | 557 (M + H)+ |
| 923 | 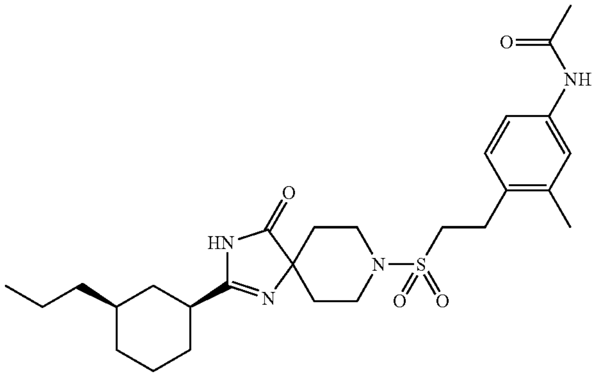 [SMILES: CCC[C@@H]1CCC[C@H](C2=NC3(CCN(S(=O)(=O)CCc4ccc(NC(C)=O)cc4C)CC3)C(=O)N2)C1] | LCMS-C-1 | 2.78 | 517 (M + H)+ |
| 924 | 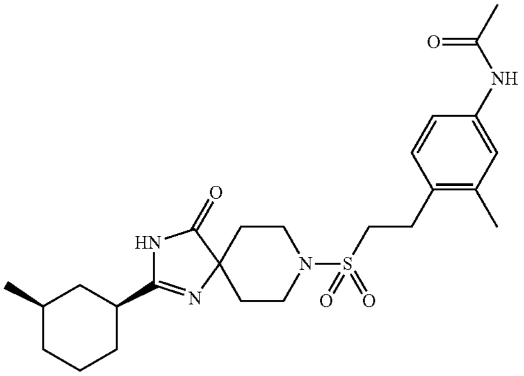 [SMILES: CC(=O)Nc1ccc(CCS(=O)(=O)N2CCC3(CC2)N=C([C@H]2CCC[C@@H](C)C2)NC3=O)c(C)c1] | LCMS-C-1 | 2.48 | 489 (M + H)+ |

TABLE 125-continued

| Compound | Structure | LCMS condition | Retention time (min) | MS (m/z) |
| --- | --- | --- | --- | --- |
| 925 | 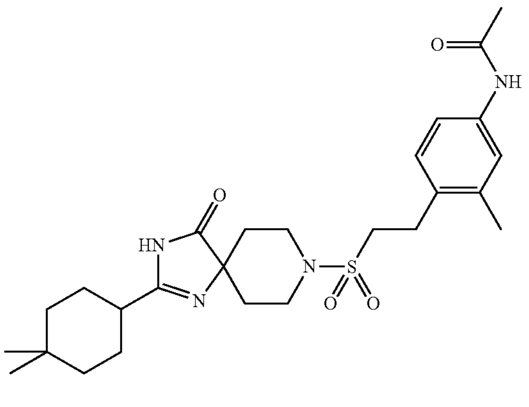 [SMILES: CC(=O)Nc1ccc(CCS(=O)(=O)N2CCC3(CC2)N=C(C2CCC(C)(C)CC2)NC3=O)c(C)c1] | LCMS-C-1 | 2.63 | 503 (M + H)+ |
| 926 | 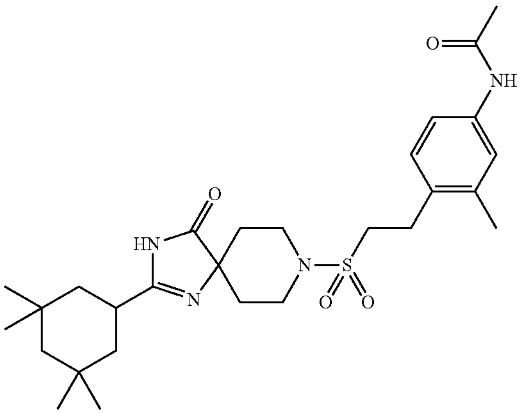 [SMILES: CC(=O)Nc1ccc(CCS(=O)(=O)N2CCC3(CC2)N=C(C2CC(C)(C)CC(C)(C)C2)NC3=O)c(C)c1] | LCMS-C-1 | 2.85 | 531 (M + H)+ |

The spiroamine reagents used in the synthesis of Compounds 920 and 921 and shown below were synthesized by operations similar to those in Reaction 10-14, Reaction 1-4 and Reaction 4-1 using appropriate reagents and Compound 5a as a starting material.

TABLE 126

| Target Compound | Spiroamine reagent | Spiroamine reagent MS (m/z) |
| --- | --- | --- |
| 920 | 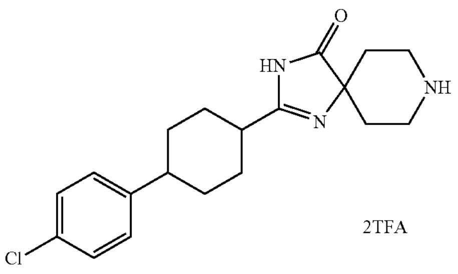 [SMILES: O=C1NC(C2CCC(c3ccc(Cl)cc3)CC2)=NC12CCNCC2 ; "2TFA"] 2TFA | 346 (M + H)+ |

TABLE 126-continued

| Target Compound | Spiroamine reagent | Spiroamine reagent MS (m/z) |
|---|---|---|
| 921 | 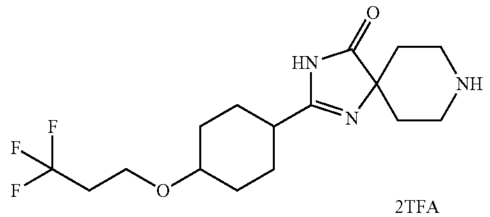 [SMILES: O=C1NC(C2CCC(OCCC(F)(F)F)CC2)=NC12CCNCC2 ; "2TFA"] 2TFA | 348 (M + H)+ |

The carboxylic acid necessary for the synthesis of the spiroamine reagent used for Compound 921 (4-(3,3,3-trifluoro-propoxy)-cyclohexanecarboxylic acid) was synthesized by the method shown below.

(Reaction 193-2)

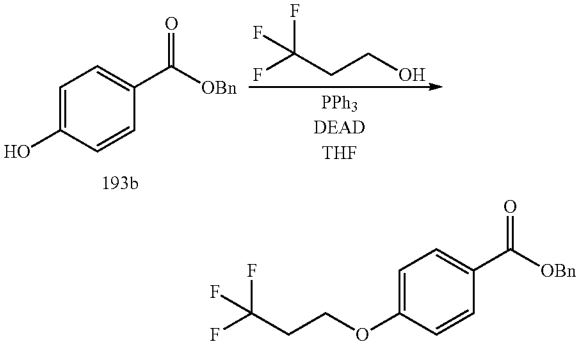

193b

193c 4-(3,3,3-Trifluoro-propoxy)-benzoic acid benzyl ester was synthesized by operations similar to those in Reaction 31-7 using appropriate reagents and starting material.

$^1$H-NMR (400 MHz, $CDCl_3$) δ 2.63 (2H, qt, J=10.4, 6.8 Hz), 4.23 (2H, t, J=6.0 Hz), 5.32 (2H, s), 6.90 (1H, d, J=8.8 Hz), 7.30-7.43 (5H, m), 8.02 (1H, d, J=8.8 Hz).

(Reaction 193-3)

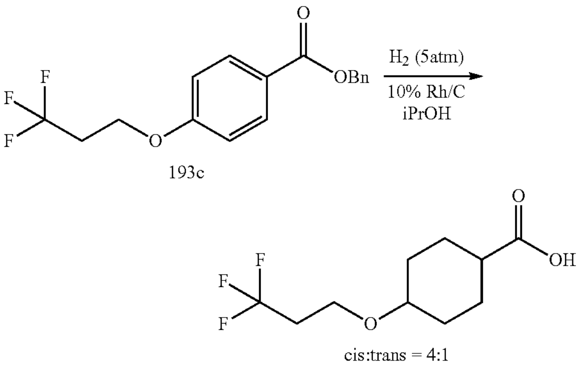

193c cis:trans = 4:1
193d

10% Rh—C (14.7 mg) was added to a solution of 4-(3,3,3-trifluoro-propoxy)-benzoic acid benzyl ester (147.3 mg, 0.454 mmol) in iPrOH (1.5 mL). The hydrogen pressure was adjusted to 5 atm, and the mixture was then heated with stirring at 80° C. overnight. The reaction mixture was filtered through celite, and the filtrate was then diluted with ethyl acetate. A saturated aqueous sodium bicarbonate solution was added, and the organic layer and the aqueous layer were separated. The aqueous layer was adjusted to pH 1 with 1 N hydrochloric acid and then extracted with ethyl acetate. The organic layers were sequentially washed with water and saturated brine, and then dried over anhydrous $Na_2SO_4$ and concentrated under reduced pressure to give 4-(3,3,3-trifluoro-propoxy)-cyclohexanecarboxylic acid as a colorless transparent oily substance (70.2 mg, 64%).

$^1$H-NMR (400 MHz, $CDCl_3$) δ 1.19-2.08 (8H, m), 2.27-2.43 (3H, m), 3.23 (0.2H, tt, J=11.2, 4.0 Hz), 3.45-3.49 (0.8H, m), 3.59 (1.6H, t, J=6.8 Hz), 3.66 (0.4H, t, J=6.8 Hz).

The spiroamine reagent used in the synthesis of Compound 922 (2-[4-(2,2,2-trifluoro-ethyl)-cyclohexyl]-1,3,8-triaza-spiro[4.5]dec-1-en-4-one ditrifluoroacetate) was synthesized by the method shown below.

(Reaction 193-4)

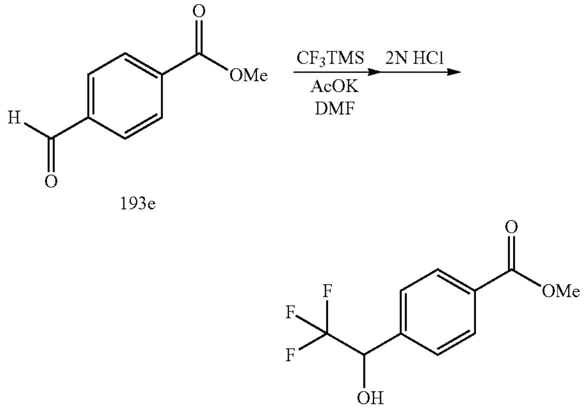

193e

193f

DMF (10 mL) was added to a reaction vessel containing 4-formyl-benzoic acid methyl ester (501.1 mg, 3.053 mmol) and potassium acetate (15.0 mg, 0.153 mmol), and the mixture was cooled to 0° C. Trimethyl(trifluoromethyl)silane (0.96 mL, 6.105 mmol) was added dropwise and the mixture was stirred for 50 minutes. 2 N hydrochloric acid (10 mL) was then added to the reaction mixture, and the mixture was stirred at room temperature overnight and then diluted with ethyl acetate. A saturated aqueous sodium bicarbonate solution was added, and the organic layer and the aqueous layer were separated. The organic layer was sequentially washed with water and saturated brine, and then dried over anhydrous $Na_2SO_4$ and concentrated under reduced pressure. The resulting residue was purified by silica gel column chromatography to give 4-(2,2,2-trifluoro-1-hydroxy-ethyl)-benzoic acid methyl ester (680.8 mg, 95%).

$^1$H-NMR (400 MHz, $CDCl_3$) δ 2.63 (1H, d, J=5.2 Hz), 3.92 (3H, s), 5.06-5.12 (1H, m), 7.55 (2H, d, J=8.4 Hz), 8.07 (2H, d, J=8.4 Hz).

(Reaction 193-5)

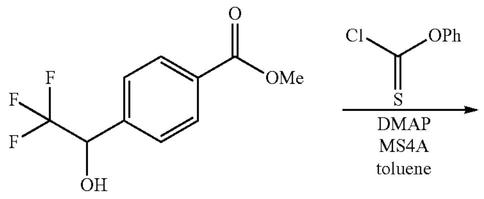

193f

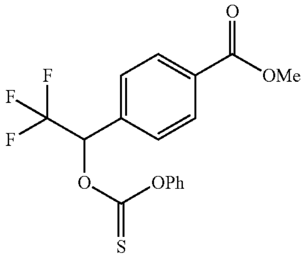

193g

Toluene (26 mL) was added to a reaction vessel containing 4-(2,2,2-trifluoro-1-hydroxy-ethyl)-benzoic acid methyl ester (607.2 mg, 2.593 mmol), DMAP (633.6 mg, 5.186 mmol) and Molecular Sieve 4A (916.1 mg). Phenyl chlorothioxoformate (0.54 mL, 3.889 mmol) was added dropwise and the mixture was stirred overnight. The reaction mixture was filtered through celite, and the filtrate was then concentrated under reduced pressure. The resulting residue was purified by silica gel column chromatography to give 4-(2,2,2-trifluoro-1-phenoxythiocarbonyloxy-ethyl)-benzoic acid methyl ester as a colorless oily substance (900.5 mg, 94%).

$^1$H-NMR (400 MHz, $CDCl_3$) δ 3.93 (3H, s), 6.62 (1H, q, J=6.4 Hz), 7.06-7.09 (2H, m), 7.27-7.31 (1H, m), 7.38-7.42 (2H, m), 7.60 (2H, d, J=8.4 Hz), 8.11 (2H, d, J=8.4 Hz).

(Reaction 193-6)

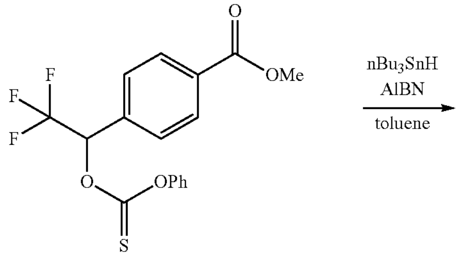

193g

-continued

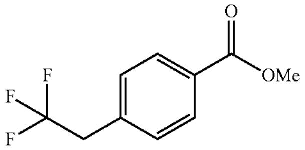

193h 4-(2,2,2-Trifluoro-1-phenoxythiocarbonyloxy-ethyl)-benzoic acid methyl ester (462.8 mg, 1.25 mmol) and AIBN (41.0 mg, 0.25 mmol) were dissolved in ultrasonically degassed toluene (12.5 mL). Tri-n-butyltin hydride (0.50 mL, 1.874 mmol) was added and the mixture was heated with stirring at 80° C. for two hours. The reaction solution was concentrated under reduced pressure, and the resulting residue was purified by silica gel column chromatography to give 4-(2,2,2-trifluoro-ethyl)-benzoic acid methyl ester as white crystals (254.6 mg, 93%).

$^1$H-NMR (400 MHz, $CDCl_3$) δ 3.41 (2H, q, J=10.8 Hz), 3.91 (3H, s), 7.36 (2H, d, J=8.4 Hz), 8.02 (2H, d, J=8.4 Hz).

(Reaction 193-7)

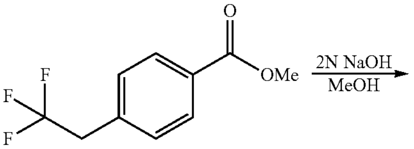

193h

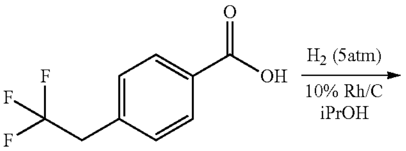

193i

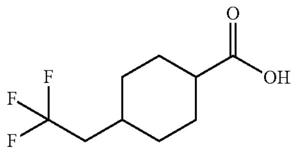

193j 4-(2,2,2-Trifluoro-ethyl)-cyclohexanecarboxylic acid was synthesized by operations similar to those in Reaction 95-18 and Reaction 193-3 using appropriate reagents and starting material.

$^1$H-NMR (400 MHz, $CDCl_3$) δ 1.03-2.08 (11H, m), 2.28 (0.33H, tt, J=12.0, 3.2 Hz), 2.61-2.64 (0.66H, m).

(Reaction 193-8)

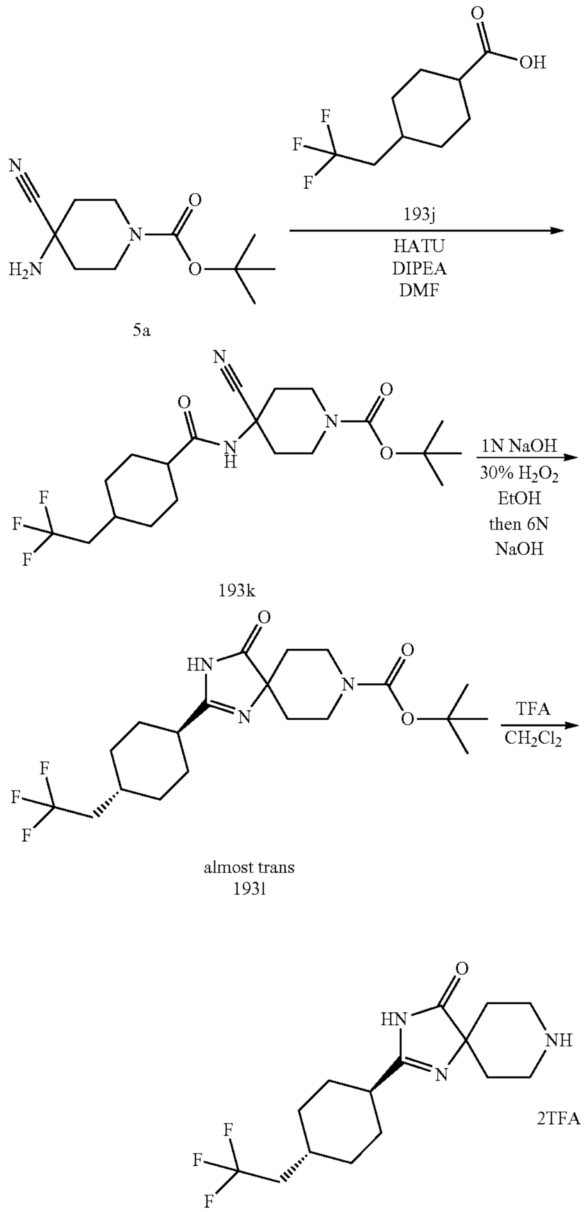

5a

193k almost trans
1931 almost trans
193m

2-[4-(2,2,2-Trifluoro-ethyl)-cyclohexyl]-1,3,8-triaza-spiro[4.5]dec-1-en-4-one ditrifluoroacetate was synthesized by operations similar to those in Reaction 10-14, Reaction 10-8 and Reaction 4-1 using appropriate reagents and starting material.

MS (ESI) m/z=318 (M+H)+.

The spiroamine reagent used in the synthesis of Compound 923 and shown below was synthesized by operations similar to those in Reaction 10-14, Reaction 10-8 and Reaction 4-1 using appropriate reagents and Compound 5a as a starting material.

TABLE 127

| Target Compound | Spiroamine reagent | Spiroamine reagent MS (m/z) |
|---|---|---|
| 923 | 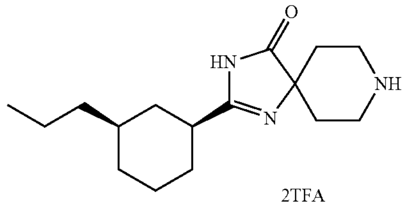 [SMILES: CCC[C@@H]1CCC[C@H](C2=NC3(CCNCC3)C(=O)N2)C1 ; "2TFA"] 2TFA | 278 (M + H)+ |

The carboxylic acid necessary for the synthesis of the spiroamine reagent used for Compound 923 (3-propyl-cyclohexanecarboxylic acid) was synthesized by the method shown below.

(Reaction 193-9)

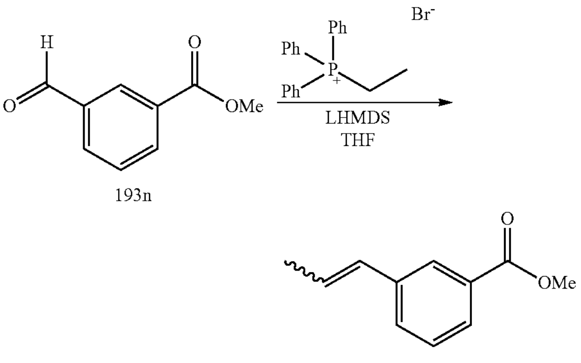

193n

193o

A suspension solution of ethyltriphenylphosphonium bromide (1079.3 mg, 2.907 mmol) in THF (10 mL) was cooled to 0° C. LHMDS (2.781 mL, 2.781 mmol, 1.0 M in THF) was added dropwise, and the mixture was stirred for 30 minutes. A solution of 3-formyl-benzoic acid methyl ester (415.0 mg, 2.528 mmol) in THF (2.5 mL) was then added dropwise, and the mixture was stirred for 10 minutes and then stirred at room temperature overnight. The reaction mixture was quenched by adding a saturated aqueous ammonium chloride solution and then extracted with ethyl acetate. The organic layer was sequentially washed with water and saturated brine, and then dried over anhydrous $Na_2SO_4$ and concentrated under reduced pressure. The resulting residue was purified by silica gel column chromatography to give 3-propenyl-benzoic acid methyl ester as a yellow transparent oily substance (218.2 mg, 49%).

$^1$H-NMR (400 MHz, $CDCl_3$) δ 1.89-1.92 (3H, m), 3.92 (1H, s), 3.93 (2H, s), 5.86 (0.66H, dq, J=11.6, 7.2 Hz), 6.32 (0.33H, dq, J=15.6, 6.4 Hz), 6.41-6.47 (1H, m), 7.34-7.43 (1H, m), 7.47-7.51 (1H, m), 7.84-7.90 (1H, m), 7.97-8.01 (1H, m).

(Reaction 193-10)

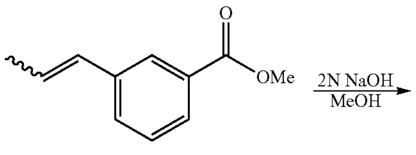

193o

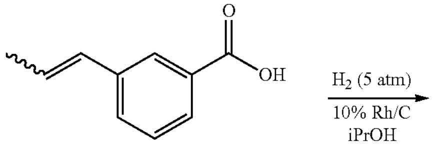

193p

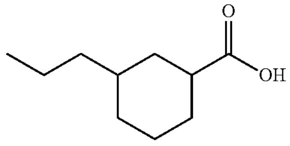

193q

3-Propyl-cyclohexanecarboxylic acid was synthesized by operations similar to those in Reaction 95-18 and Reaction 193-3 using appropriate reagents and starting material.

$^1$H-NMR (400 MHz, $CDCl_3$) δ 0.80-2.05 (16H, m), 2.33 (0.6H, tt, J=12.4, 3.2 Hz), 2.67-2.70 (0.4H, m).

The spiroamine reagent used in the synthesis of Compound 924 (2-(3-methyl-cyclohexyl)-1,3,8-triaza-spiro[4.5]dec-1-en-4-one ditrifluoroacetate) was synthesized by the method shown below.

(Reaction 193-11)

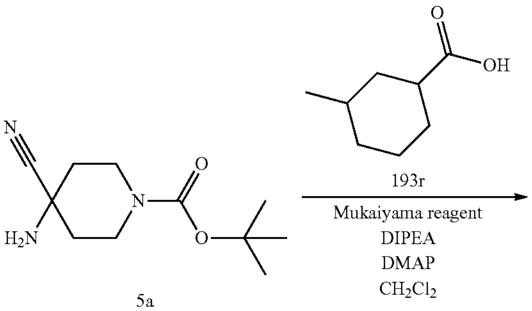

5a

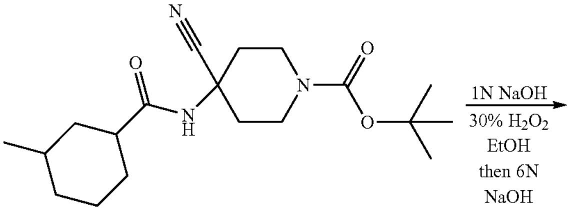

193s

-continued

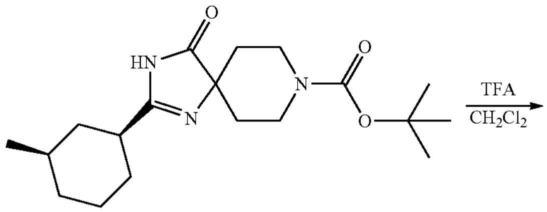

almost cis
193t

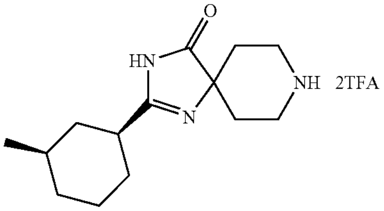

almost cis
193u 2-(3-Methyl-cyclohexyl)-1,3,8-triaza-spiro[4.5]dec-1-en-4-one ditrifluoroacetate was synthesized by operations similar to those in Reaction 176-2, Reaction 10-8 and Reaction 4-1 using appropriate reagents and starting material.

MS (ESI) m/z=250 (M+H)+.

The spiroamine reagents used in the synthesis of Compounds 925 and 926 and shown below were synthesized by operations similar to those in Reaction 10-14, Reaction 10-8 and Reaction 4-1 using appropriate reagents and starting materials.

TABLE 128

| Target Compound | Spiroamine reagent | Spiroamine reagent MS (m/z) |
|---|---|---|
| 925 | 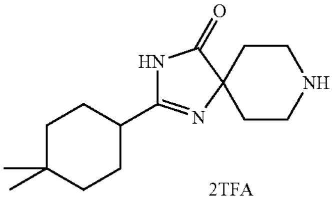 [SMILES: CC1(C)CCC(C2=NC3(CCNCC3)C(=O)N2)CC1 ; "2TFA"] 2TFA | 264 (M + H)+ |
| 926 | 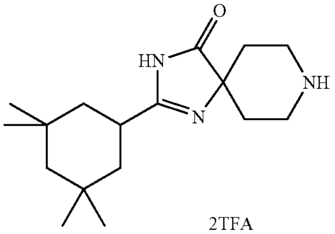 [SMILES: CC1(C)CC(C2=NC3(CCNCC3)C(=O)N2)CC(C)(C)C1 ; "2TFA"] 2TFA | 292 (M + H)+ |

The carboxylic acid necessary for the synthesis of the spiroamine reagent used for Compound 926 (3,3,5,5-tetramethyl-cyclohexanecarboxylic acid) was synthesized by the method shown below.

(Reaction 193-12)

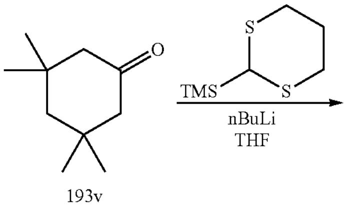

193v

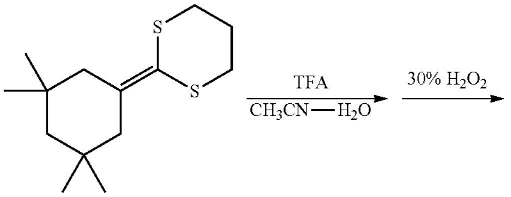

193w

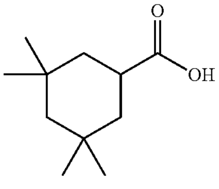

193x

A solution of [1,3]dithian-2-yl-trimethyl-silane (566.4 mg, 2.944 mmol) in THF (6 mL) was cooled to 0° C. nBuLi (1.78 mL, 2.845 mmol, 1.6 M in n-hexane) was added dropwise and then the mixture was stirred for 10 minutes. The reaction solution was cooled to −78° C. A solution of 3,3,5,5-tetramethyl-cyclohexanone (302.7 mg, 1.962 mmol) in THF (2 mL) was then added dropwise, and the mixture was stirred for two hours. The reaction mixture was quenched by adding a saturated aqueous ammonium chloride solution and extracted with ethyl acetate. The organic layer was sequentially washed with water and saturated brine, and then dried over anhydrous $Na_2SO_4$ and concentrated under reduced pressure.

The resulting residue was dissolved in acetonitrile (2.1 mL). Water (0.52 mL) and trifluoroacetic acid (0.51 mL) were added and the mixture was heated with stirring at 65° C. for three hours. The reaction solution was cooled to room temperature. A 30% aqueous hydrogen peroxide solution (3.2 mL) was then added and the mixture was heated with stirring at 80° C. for one hour. The reaction solution was cooled to room temperature, and a 5 M aqueous sodium hydroxide solution (15.7 mL) was then added, followed by extraction with ether. A saturated aqueous sodium bicarbonate solution was added, and the organic layer and the aqueous layer were separated. The aqueous layer was adjusted to pH 1 with 2 N hydrochloric acid and then extracted with ethyl acetate. The organic layers were sequentially washed with water and saturated brine, and then dried over anhydrous $Na_2SO_4$ and concentrated under reduced pressure to give 3,3,5,5-tetramethyl-cyclohexanecarboxylic acid as a white powder (342.3 mg, 95% in two steps).

$^1$H-NMR (400 MHz, $CDCl_3$) δ 0.93 (6H, s), 1.01 (6H, s), 1.06-1.28 (4H, m), 1.68-1.71 (2H, m), 2.65 (1H, tt, J=12.8, 3.2 Hz).

Example 194

N-[4-(2-{2-[4-(2-Methoxy-ethyl)-cyclohexyl]-4-oxo-1,3,8-triaza-spiro[4.5]dec-1-ene-8-sulfonyl}-ethyl)-3-methyl-phenyl]-acetamide (Compound 927)

(Reaction 194-1)

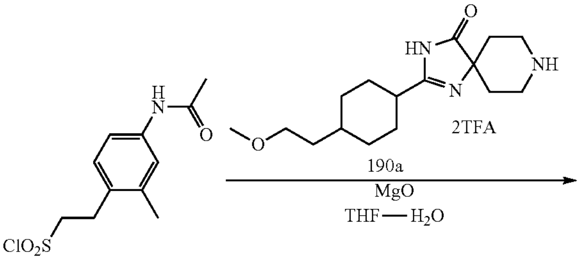

11e

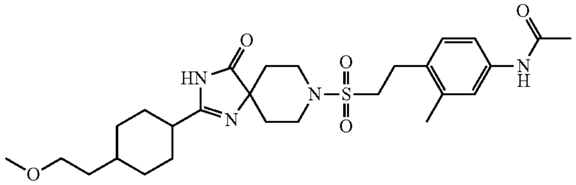

Compound 927

N-[4-(2-{2-[4-(2-Methoxy-ethyl)-cyclohexyl]-4-oxo-1,3,8-triaza-spiro[4.5]dec-1-ene-8-sulfonyl}-ethyl)-3-methyl-phenyl]-acetamide was synthesized by operations similar to those in Reaction 190-1 using appropriate reagents and starting material.

MS (ESI) m/z=533 (M+H)+.

Example 195

[3-Methyl-4-(2-{4-oxo-2-[4-(3,3,3-trifluoro-propyl)-cyclohexyl]-1,3,8-triaza-spiro[4.5]dec-1-ene-8-sulfonyl}-ethyl)-benzyl]-carbamic acid tert-butyl ester (Compound 928)

(Reaction 195-1)

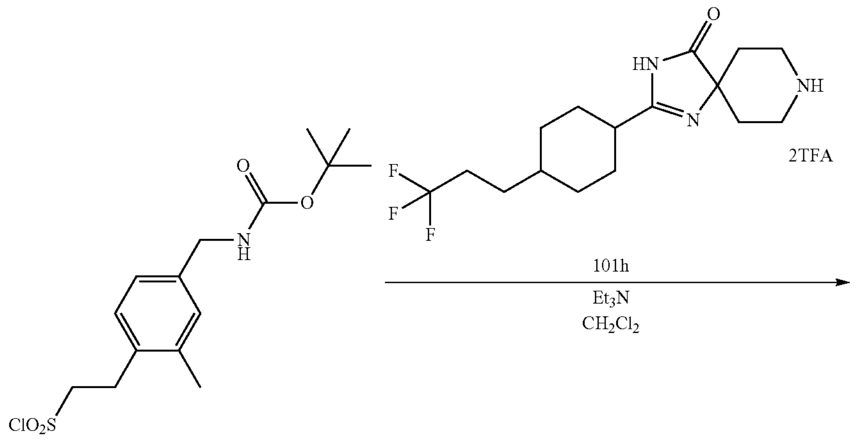

17f

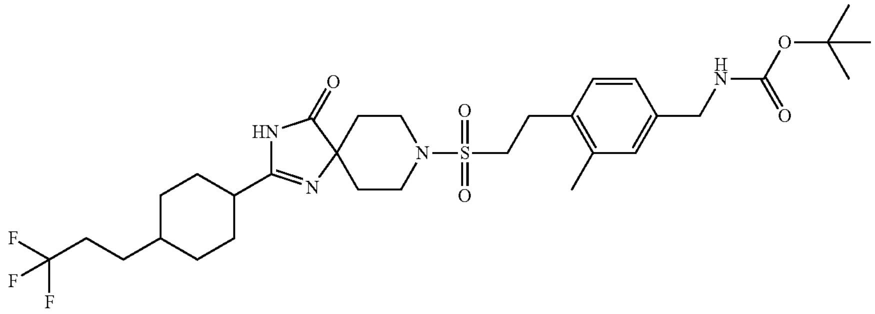

Compound 928

[3-Methyl-4-(2-{4-oxo-2-[4-(3,3,3-trifluoro-propyl)-cyclohexyl]-1,3,8-triaza-spiro[4.5]dec-1-ene-8-sulfonyl}-ethyl)-benzyl]-carbamic acid tert-butyl ester was synthesized by operations similar to those in Reaction 5-4 using appropriate reagents and starting material.

MS (ESI) m/z=643 (M+H)+.

Example 196

N-(2-Hydroxy-ethyl)-N-(3-methyl-4-{2-[4-oxo-2-(3-trifluoromethoxy-phenyl)-1,3,8-triaza-spiro[4.5]dec-1-ene-8-sulfonyl]-ethyl}-phenyl)-isobutylamide (Compound 929)

(Reaction 196-1)

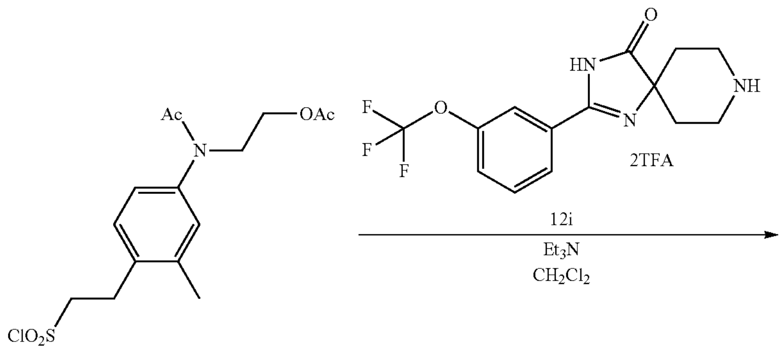

12h

-continued
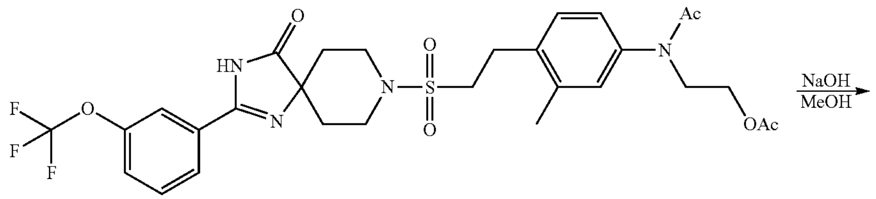
196a
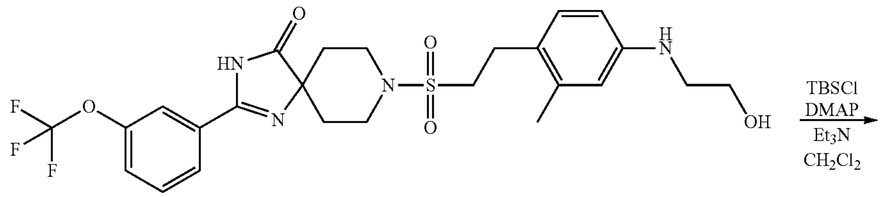
196b
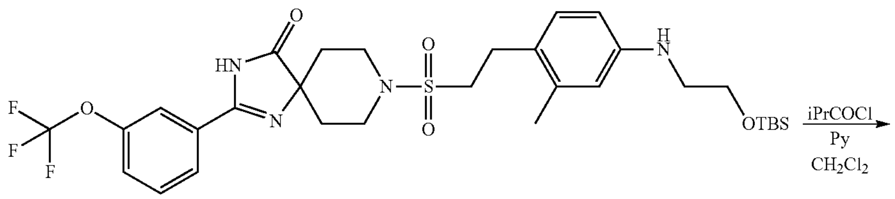
196c
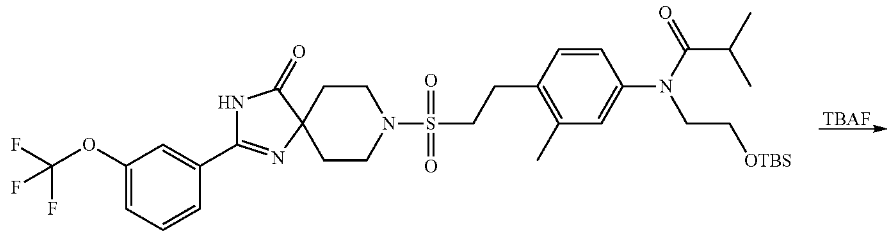
196d
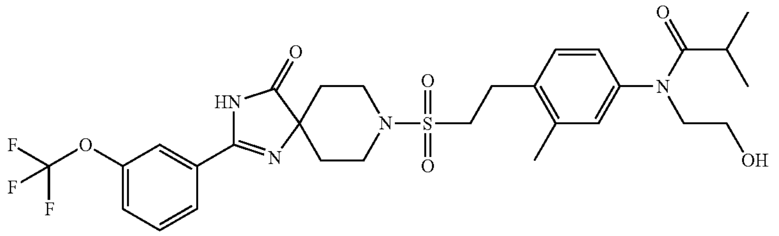
Compound 929

N-(2-Hydroxy-ethyl)-N-(3-methyl-4-{2-[4-oxo-2-(3-trifluoromethoxy-phenyl)-1,3,8-triaza-spiro[4.5]dec-1-ene-8-sulfonyl]-ethyl}-phenyl)-isobutylamide was synthesized by operations similar to those in Reaction 5-4, Reaction 96-16, Reaction 157-2, Reaction 105-2 and Reaction 39-2 using appropriate reagents and starting material.

MS (ESI) m/z=625 (M+H)+.

Example 197

2-Hydroxy-N-(2-hydroxy-ethyl)-N-(3-methyl-4-{2-[4-oxo-2-(3-trifluoromethoxy-phenyl)-1,3,8-triaza-spiro[4.5]dec-1-ene-8-sulfonyl]-ethyl}-phenyl)-acetamide (Compound 930)

(Reaction 197-1)

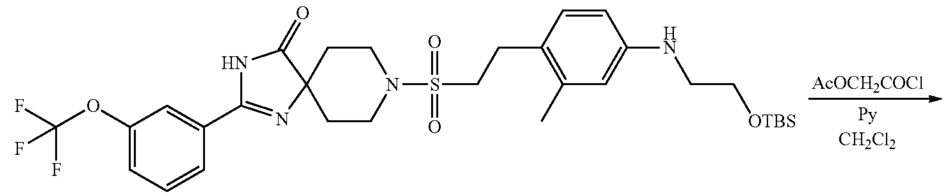

196c

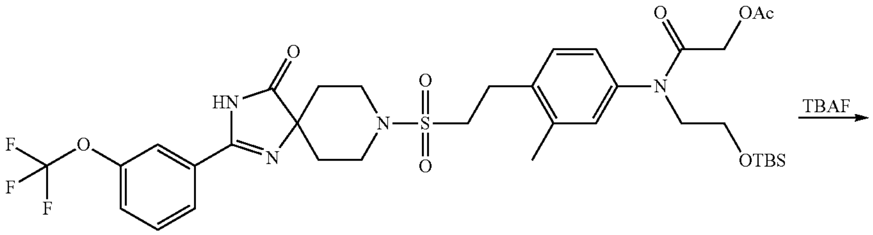

197a

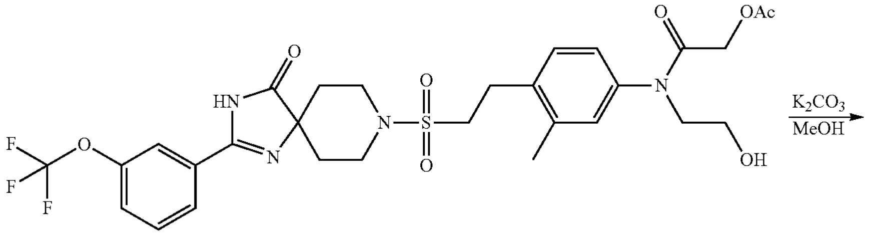

197b

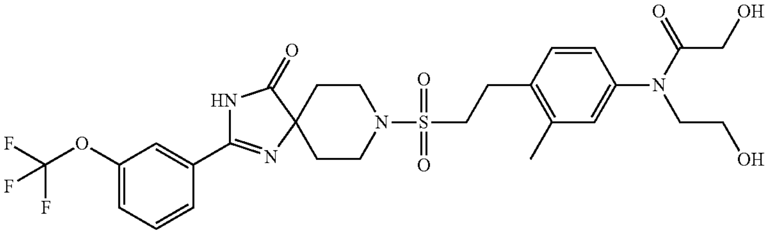

Compound 930

2-Hydroxy-N-(2-hydroxy-ethyl)-N-(3-methyl-4-{2-[4-oxo-2-(3-trifluoromethoxy-phenyl)-1,3,8-triaza-spiro[4.5]dec-1-ene-8-sulfonyl]-ethyl}-phenyl)-acetamide was synthesized by operations similar to those in Reaction 105-2, Reaction 39-2 and Reaction 12-5 using appropriate reagents and starting material.

MS (ESI) m/z=613 (M+H)+.

Example 198

N-(3,5-Dimethyl-4-{2-[2-(4-methyl-cyclohexyl)-4-oxo-1,3,8-triaza-spiro[4.5]dec-1-ene-8-sulfonyl]-ethyl}-phenyl)-2,2,2-trifluoro-N-methyl-acetamide (Compound 931)

(Reaction 198-1)

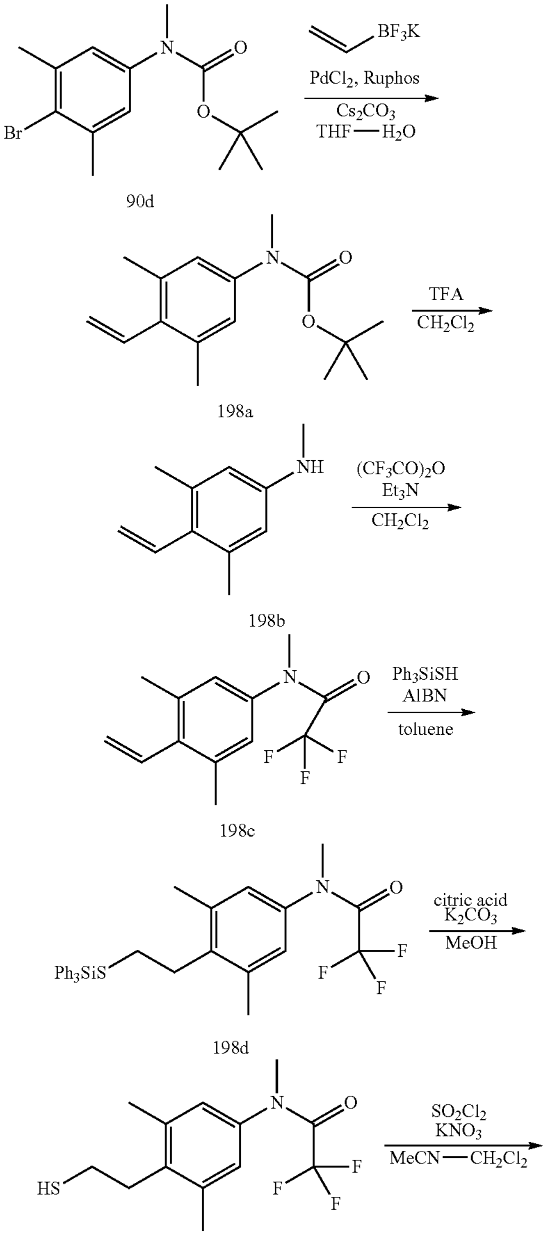

198e

-continued

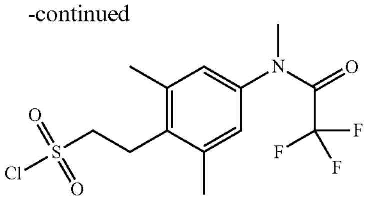

198f

2-{2,6-Dimethyl-4-[methyl-(2,2,2-trifluoro-acetyl)-amino]-phenyl}-ethanesulfonyl chloride was synthesized by operations similar to those in Reaction 10-2, Reaction 4-1, Reaction 19-2, Reaction 10-3, Reaction 10-4 and Reaction 10-5 using appropriate reagents and starting material.

MS (ESI) m/z=358 (M+H)+.

(Reaction 198-2)

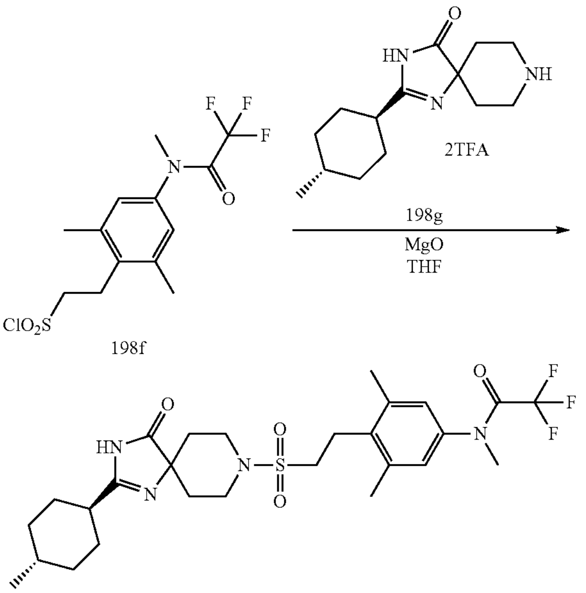

Compound 931

N-(3,5-Dimethyl-4-{2-[2-(4-methyl-cyclohexyl)-4-oxo-1,3,8-triaza-spiro[4.5]dec-1-ene-8-sulfonyl]-ethyl}-phenyl)-2,2,2-trifluoro-N-methyl-acetamide was synthesized by operations similar to those in Reaction 190-1 using appropriate reagents and starting material.

MS (ESI) m/z=571 (M+H)+.

Example 199

N-(3,5-Dimethyl-4-{2-[2-(3-methyl-cyclohexyl)-4-oxo-1,3,8-triaza-spiro[4.5]dec-1-ene-8-sulfonyl]-ethyl}-phenyl)-2,2,2-trifluoro-N-methyl-acetamide (Compound 932)

(Reaction 199-1)

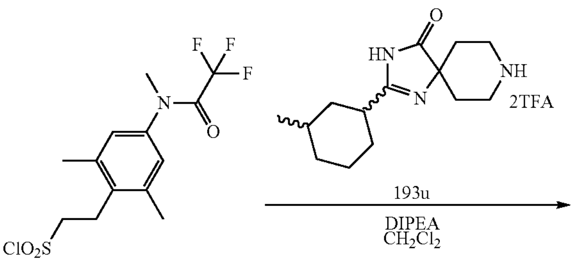

198f

-continued

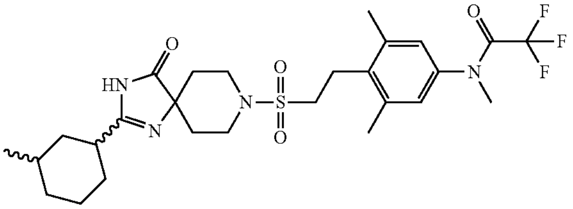

Compound 932

N-(3,5-Dimethyl-4-{2-[2-(3-methyl-cyclohexyl)-4-oxo-1,3,8-triaza-spiro[4.5]dec-1-ene-8-sulfonyl]-ethyl}-phenyl)-2,2,2-trifluoro-N-methyl-acetamide was synthesized by operations similar to those in Reaction 5-4 using appropriate reagents and starting material.

MS (ESI) m/z=571 (M+H)+.

The example compound shown below was synthesized by operations similar to those in Reaction 199-1 using appropriate reagents and starting material.

Compound 933

TABLE 129

| Compound | Structure | LCMS condition | Retention time (min) | MS (m/z) |
|---|---|---|---|---|
| 933 | 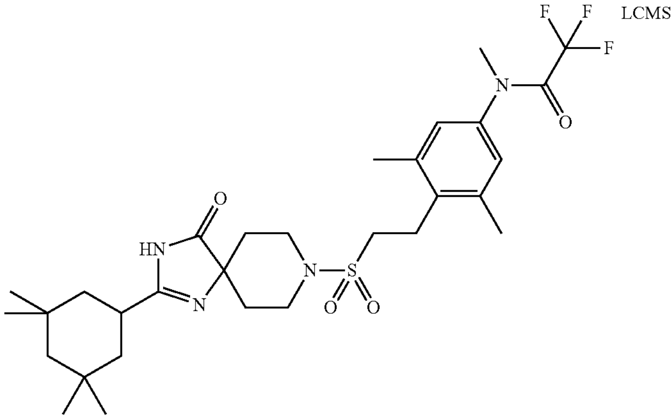 | LCMS-C-1 | 3.13 | 613 (M + H)+ |

Example 200

1-{4-[2-(2-Cycloheptyl-4-oxo-1,3,8-triaza-spiro[4.5]dec-1-ene-8-sulfonyl)-ethyl]-3,5-dimethyl-phenyl}-1-methyl-urea (Compound 934)

(Reaction 200-1)

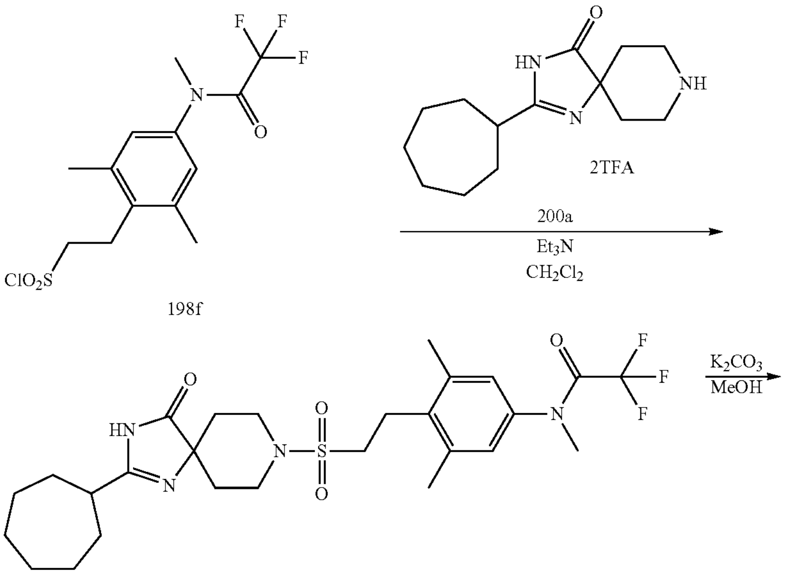

198f

200b

-continued

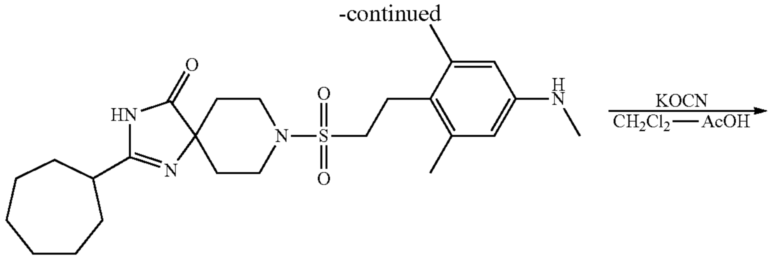

200c

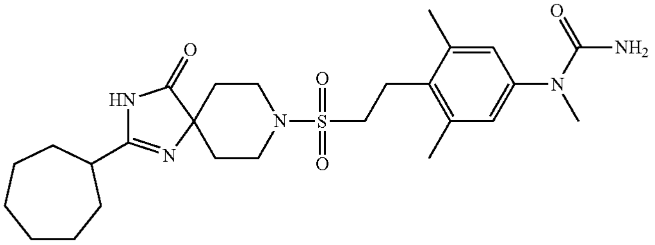

Compound 934

1-{4-[2-(2-Cycloheptyl-4-oxo-1,3,8-triaza-spiro[4.5]dec-1-ene-8-sulfonyl)-ethyl]-3,5-dimethyl-phenyl}-1-methyl-urea was synthesized by operations similar to those in Reaction 5-4, Reaction 12-5 and Reaction 89-2 (using KOCN) using appropriate reagents and starting material.

MS (ESI) m/z=518 (M+H)+.

The example compounds shown below were synthesized by operations similar to those in Reaction 200-1 using appropriate reagents and starting materials.

Compounds 935, 938 and 941

TABLE 130

| Compound | Structure | LCMS condition | Retention time (min) | MS (m/z) |
|---|---|---|---|---|
| 935 | 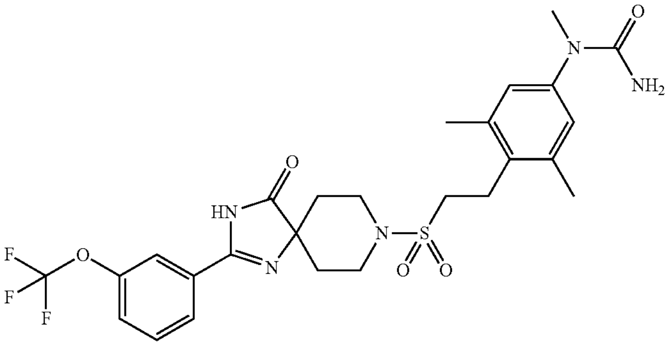 [SMILES: Cc1cc(N(C)C(N)=O)cc(C)c1CCS(=O)(=O)N1CCC2(CC1)N=C(c1cccc(OC(F)(F)F)c1)NC2=O] | LCMS-A-1 | 2.35 | 582 (M + H)+ |
| 938 | 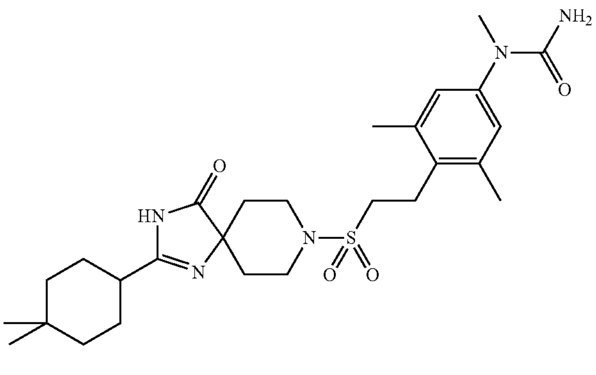 [SMILES: Cc1cc(N(C)C(N)=O)cc(C)c1CCS(=O)(=O)N1CCC2(CC1)N=C(C1CCC(C)(C)CC1)NC2=O] | LCMS-C-1 | 2.70 | 532 (M + H)+ |

TABLE 130-continued

| Compound | Structure | LCMS condition | Retention time (min) | MS (m/z) |
|---|---|---|---|---|
| 941 | 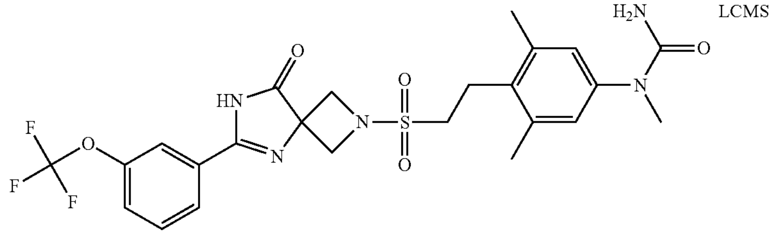 | LCMS-F-1 | 0.93 | 554 (M + H)+ |

The spiroamine reagent used in the synthesis of Compound 941 (6-(3-trifluoromethoxy-phenyl)-2,5,7-triaza-spiro[3.4]oct-5-en-8-one ditrifluoroacetate) was synthesized as follows.

(Reaction 200-2)

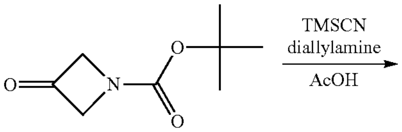

200d

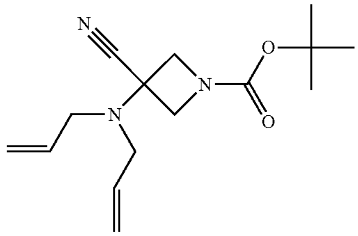

200e

Diallylamine (0.31 ml, 2.5 mmol) and trimethylsilylnitrile (0.155 ml, 1.25 mmol) were added to a solution of 3-oxo-azetidine-1-carboxylic acid tert-butyl ester (171 mg, 1.00 mmol) in acetic acid (1.7 ml, 30 mmol), and the mixture was stirred at 60° C. for four hours. A Saturated aqueous sodium bicarbonate solution (11.5 ml) was added to the reaction mixture, followed by extraction with ethyl acetate. The organic layer was then dried over $MgSO_4$ and concentrated under reduced pressure. The resulting residue was purified by silica gel column chromatography (hexane-ethyl acetate) to give 3-cyano-3-diallylamino-azetidine-1-carboxylic acid tert-butyl ester (212 mg, 76%).

$^1$H-NMR (400 MHz, $CDCl_3$) δ 1.45 (9H, s), 3.10 (4H, d, J=7.0 Hz), 4.01 (2H, d, J=8.6 Hz), 4.09 (2H, d, J=8.6 Hz), 5.19 (1H, d, J=10.2 Hz), 5.30 (1H, d, J=17.0 Hz), 5.82 (1H, m).

(Reaction 200-3)

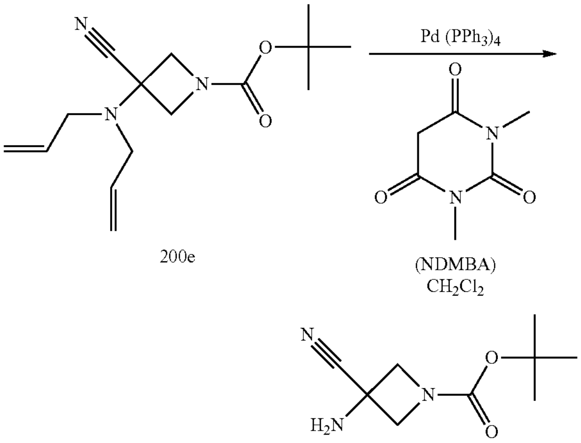

200e

200f

A solution of 3-cyano-3-diallylamino-azetidine 1-carboxylic acid tert-butyl ester (143.5 mg, 0.5174 mmol), 1,3-dimethylbarbituric acid (242.5 mg, 1.553 mmol) and tetrakis (triphenylphosphine)palladium(0) (30.3 mg, 0.0262 mmol) in dichloromethane (1.3 ml) was stirred at 40° C. for five hours. A saturated aqueous sodium bicarbonate solution was added to the reaction mixture, followed by extraction with ethyl acetate. The organic layer was then dried over $MgSO_4$ and concentrated under reduced pressure. The resulting residue was purified by silica gel column chromatography (hexane-ethyl acetate) to give 3-amino-3-cyano-azetidine-1-carboxylic acid tert-butyl ester (98 mg, 96%).

$^1$H-NMR (400 MHz, $CDCl_3$) δ 1.44 (9H, s), 2.03 (2H, br), 3.88 (2H, d, J=8.8 Hz), 4.34 (2H, d, J=8.8 Hz).

(Reaction 200-4)

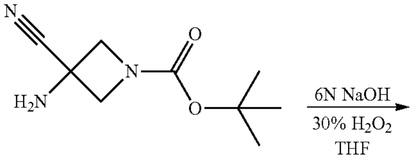

200f

-continued

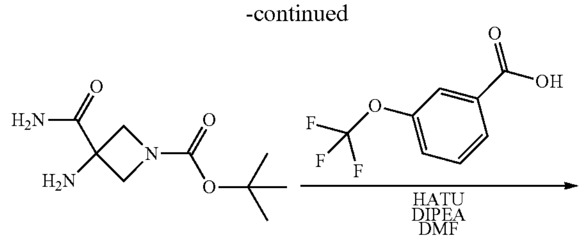

200g

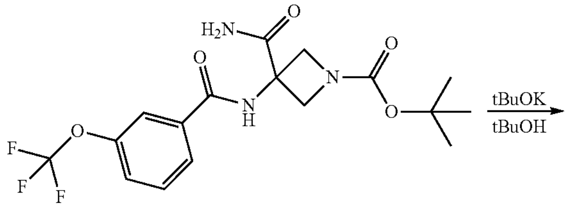

200h

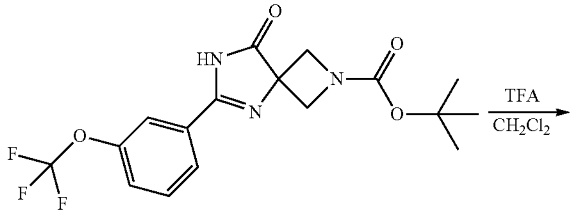

200i

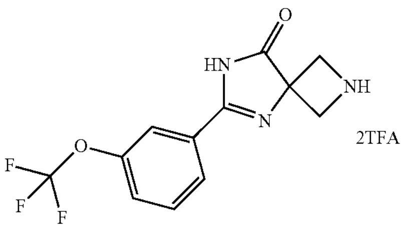

200j 6-(3-Trifluoromethoxy-phenyl)-2,5,7-triaza-spiro[3.4]oct-5-en-8-one ditrifluoroacetate was synthesized by operations similar to those in Reaction 10-11, Reaction 10-14, Reaction 10-12 and Reaction 4-1 using appropriate reagents and starting material.

$^1$H-NMR (400 MHz, $CDCl_3$) δ 4.31 (2H, d, J=12.0 Hz), 4.40 (2H, d, J=12.0 Hz), 7.56 (1H, d, J=8.2 Hz), 7.66 (1H, t, J=8.2 Hz), 7.95 (1H, d, J=8.2 Hz), 7.96 (1H, s).

Example 201

1-[3,5-Dimethyl-4-(2-{4-oxo-2-[4-(2,2,2-trifluoro-ethyl)-cyclohexyl]-1,3,8-triaza-spiro[4.5]dec-1-ene-8-sulfonyl}-ethyl)-phenyl]-1-methyl-urea (Compound 936) and 1-[2-chloro-3,5-dimethyl-4-(2-{4-oxo-2-[4-(2,2,2-trifluoro-ethyl)-cyclohexyl]-1,3,8-triaza-spiro[4.5]dec-1-ene-8-sulfonyl}-ethyl)-phenyl]-1-methyl-urea (Compound 937)

(Reaction 201-1)

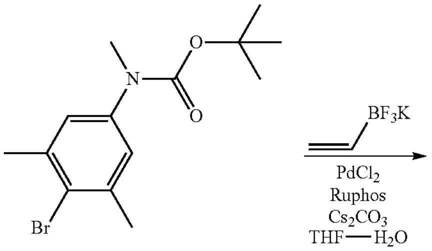

90d

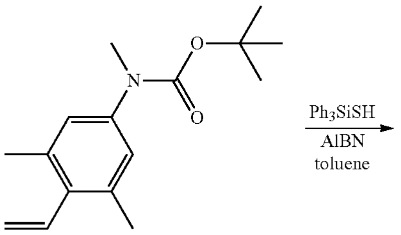

201a

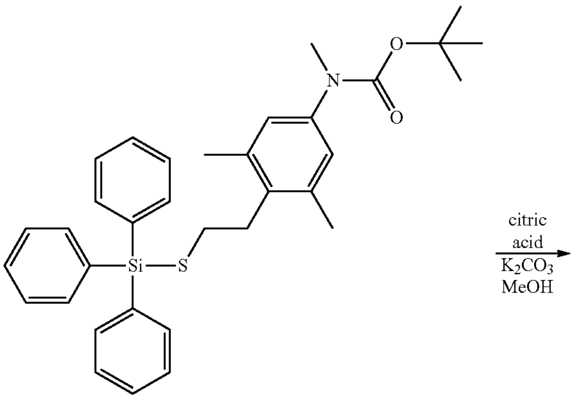

201b

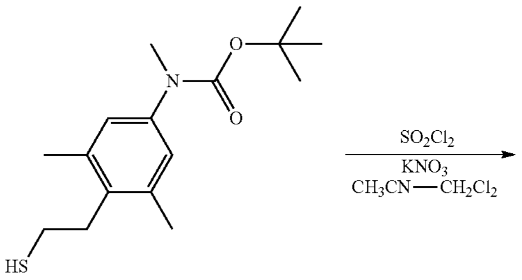

201c

-continued

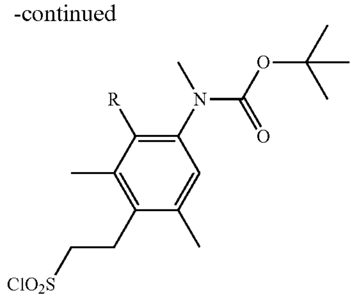

201d
Mixture (R = H or Cl)

A mixture of [4-(2-chlorosulfonyl-ethyl)-3,5-dimethyl-phenyl]-methyl-carbamic acid tert-butyl ester and [2-chloro-4-(2-chlorosulfonyl-ethyl)-3,5-dimethyl-phenyl]-methyl-carbamic acid tert-butyl ester was synthesized by operations similar to those in Reaction 10-2 (using RuPhos as a ligand), Reaction 10-3, Reaction 10-4 and Reaction 10-5 using appropriate reagents and starting material.

(R=H:R=Cl=0.6:0.4)

$^1$H-NMR (400 MHz, $CDCl_3$) δ 1.32-1.54 (9H, m), 2.32-2.47 (6H, m), 3.08-3.25 (3H, m), 3.29-3.44 (2H, m), 3.60-3.74 (2H, m), 6.96 (1.6H, m).

(Reaction 201-2)

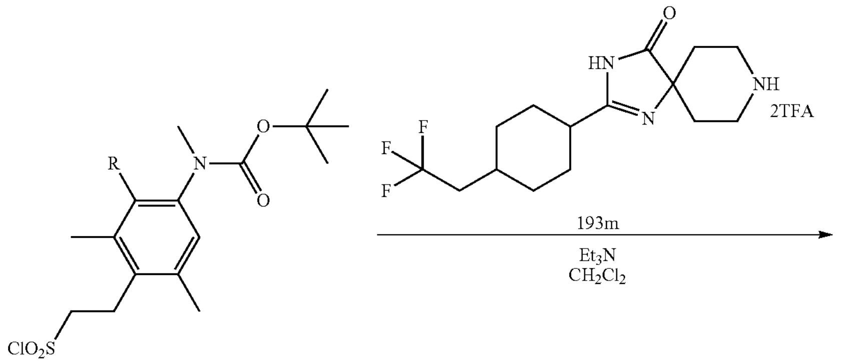

201d
Mixture (R = H or Cl)

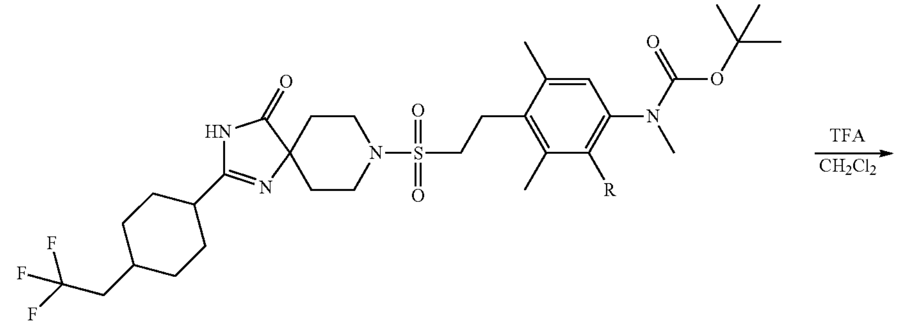

201e
Mixture (R = H or Cl)

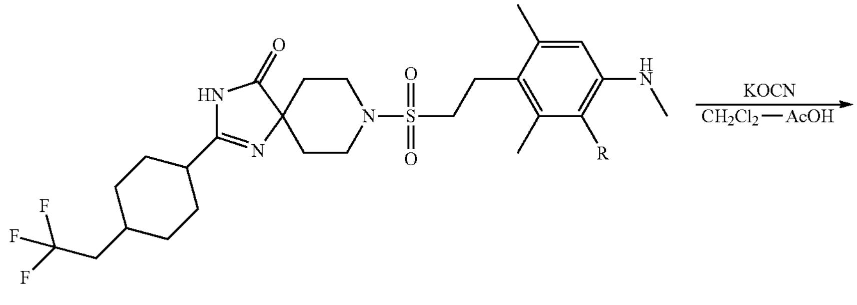

201f
Mixture (R = H or Cl)

-continued

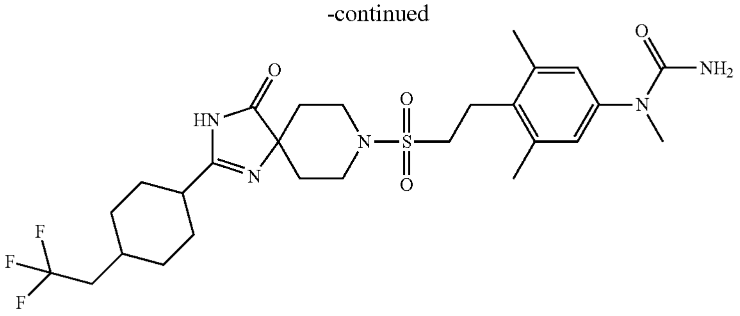

Compound 936

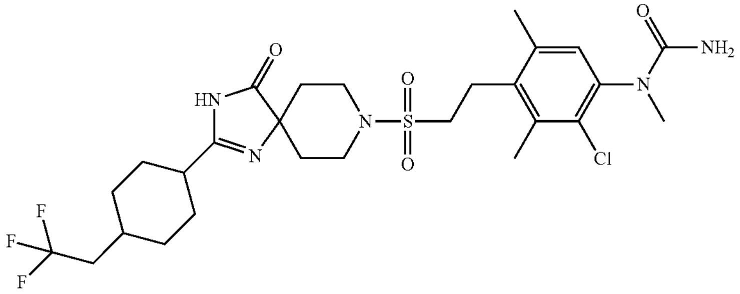

Compound 937

1-[3,5-Dimethyl-4-(2-{4-oxo-2-[4-(2,2,2-trifluoro-ethyl)-cyclohexyl]-1,3,8-triaza-spiro[4.5]dec-1-ene-8-sulfonyl}-ethyl)-phenyl]-1-methyl-urea MS (ESI) m/z=586 (M+H)+ and 1-[2-chloro-3,5-dimethyl-4-(2-{4-oxo-2-[4-(2,2,2-trifluoro-ethyl)-cyclohexyl]-1,3,8-triaza-spiro[4.5]dec-1-ene-8-sulfonyl}-ethyl)-phenyl]-1-methyl-urea MS (ESI) m/z=620 (M+H)+ were obtained by operations similar to those in Reaction 5-4, Reaction 4-1 and Reaction 89-2 (using KOCN) using the starting material obtained above and appropriate reagents.

Example 202

1-[3,5-Dimethyl-4-(2-{4-oxo-2-[4-(3,3,3-trifluoro-propylidene)-cyclohexyl]-1,3,8-triaza-spiro[4.5]dec-1-ene-8-sulfonyl}-ethyl)-phenyl]-1-methyl-urea (Compound 939)

(Reaction 202-1)

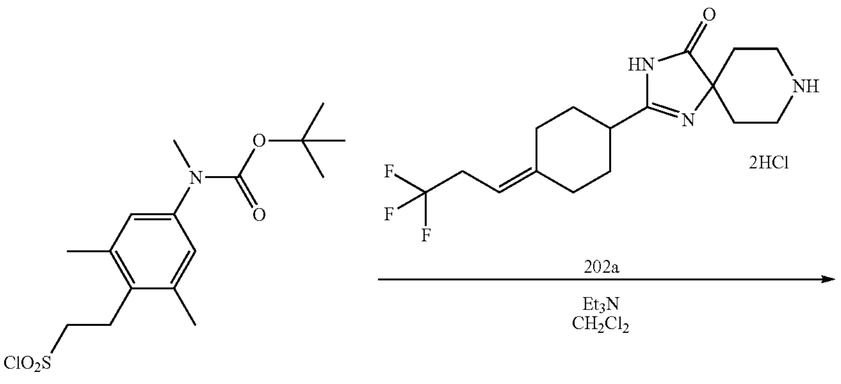

201d

-continued

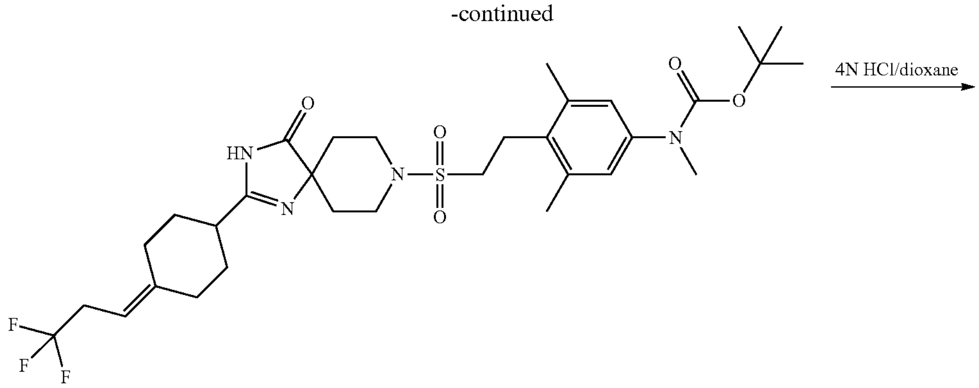

202b

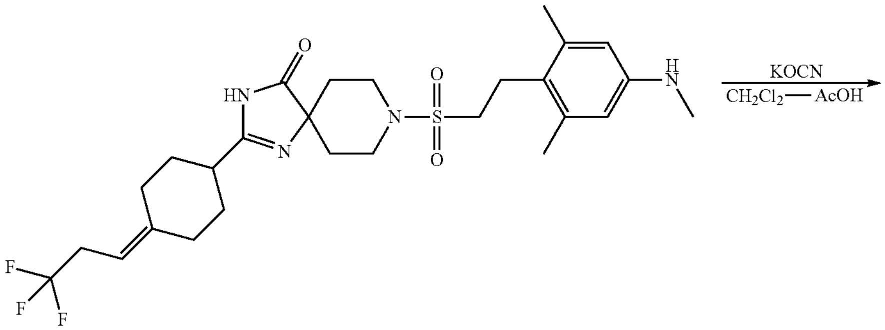

202c

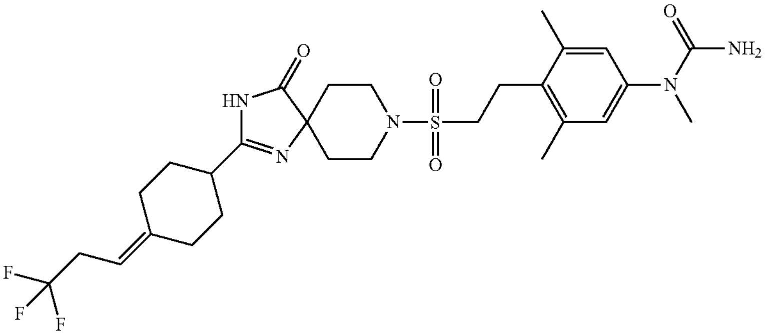

Compound 939

1-[3,5-Dimethyl-4-(2-{4-oxo-2-[4-(3,3,3-trifluoro-propylidene)-cyclohexyl]-1,3,8-triaza-spiro[4.5]dec-1-ene-8-sulfonyl}-ethyl)-phenyl]-1-methyl-urea was synthesized by operations similar to those in Reaction 5-4, Reaction 5-3 and Reaction 89-2 (using KOCN) using appropriate reagents and starting material.

MS (ESI) m/z=598 (M+H)+.

The example compound shown below was synthesized by operations similar to those in Reaction 202-1 using appropriate reagents and starting material.

Compound 940

TABLE 131

| Compound | Structure | LCMS condition | Retention time (min) | MS (m/z) |
|---|---|---|---|---|
| 940 | 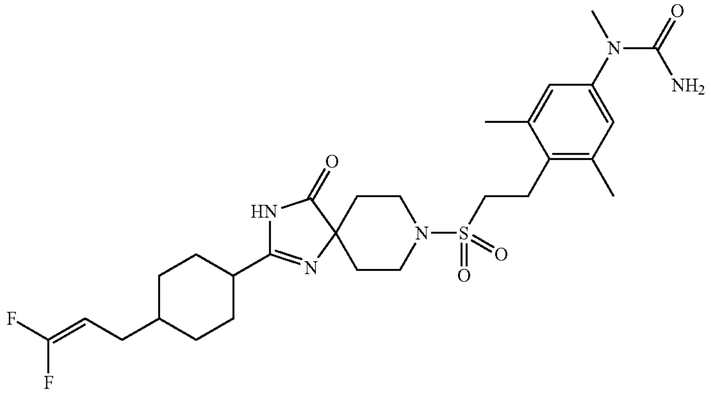 [SMILES: Cc1cc(N(C)C(N)=O)cc(C)c1CCS(=O)(=O)N1CCC2(CC1)N=C(C1CCC(CC=C(F)F)CC1)NC2=O] | LCMS-B-1 | 1.91 | 580 (M + H)+ |

The spiroamine reagent used in the synthesis of Compound 939 (2-[4-(3,3,3-trifluoro-propylidene)-cyclohexyl]-1,3,8-triaza-spiro[4.5]dec-1-en-4-one dihydrochloride) was synthesized as follows.

(Reaction 202-2)

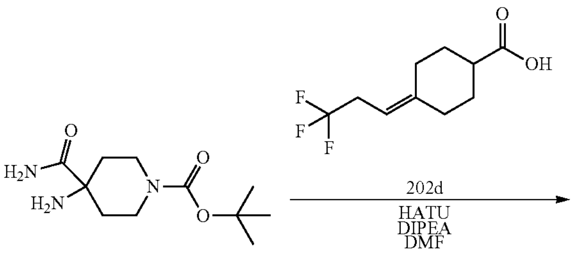

10ag

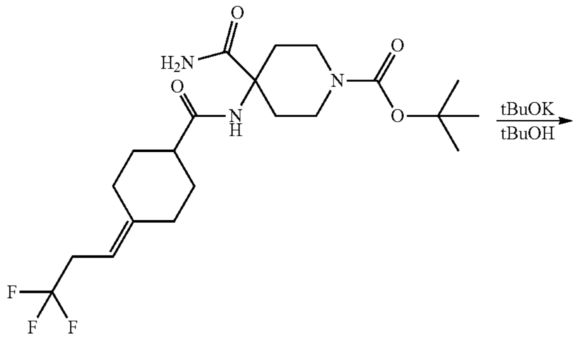

202e

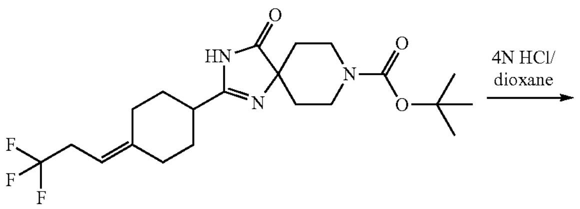

202f

-continued

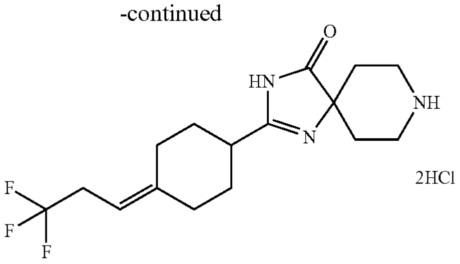

202a

2-[4-(3,3,3-Trifluoro-propylidene)-cyclohexyl]-1,3,8-triaza-spiro[4.5]dec-1-en-4-one dihydrochloride was synthesized by operations similar to those in Reaction 10-14, Reaction 10-12 and Reaction 5-3 using appropriate reagents and starting material.

MS (ESI) m/z=330 (M+H)+.

The spiroamine reagent used in the synthesis of Compound 940 and shown below was synthesized by operations similar to those in Reaction 10-14, Reaction 10-12 and Reaction 5-3 using appropriate reagents and Compound 10ag as a starting material.

TABLE 132

| Target Compound | Spiroamine reagent | Spiroamine reagent MS (m/z) |
|---|---|---|
| 940 | 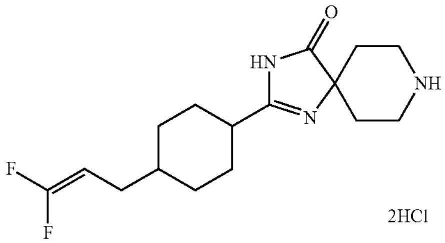 [SMILES: O=C1NC(C2CCC(CC=C(F)F)CC2)=NC12CCNCC2 ; "2HCl"] 2HCl | 312 (M + H)+ |

(Reaction 202-3)

The carboxylic acid derivative necessary for the synthesis of the spiroamine reagent used in the synthesis of Compound 940 (4-(3,3-difluoro-allyl)-cyclohexanecarboxylic acid) was synthesized in the following manner.

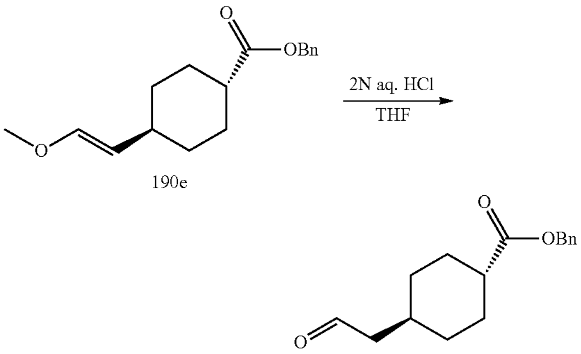

190e 202g
trans:cis = 4:1

4-(2-Oxo-ethyl)-cyclohexanecarboxylic acid benzyl ester (trans:cis=4:1) was synthesized by operations similar to those in Reaction 25-4 using appropriate reagents and starting material.

$^1$H-NMR (400 MHz, $CDCl_3$) δ 1.04 (1.6H, m), 1.30 (0.4H, m), 1.51 (1.6H, m), 1.62 (0.8H, m), 1.84 (1.6H, m), 1.89 (0.8H, m), 2.10 (2.2H, m), 2.32 (2.8H, m), 2.60 (0.2H, m), 5.11 (1.6H, s), 5.13 (0.4H, s), 7.35 (5H, m), 9.75 (0.2H, t, J=2.0 Hz), 9.76 (0.8H, t, J=2.0 Hz).

(Reaction 202-4)

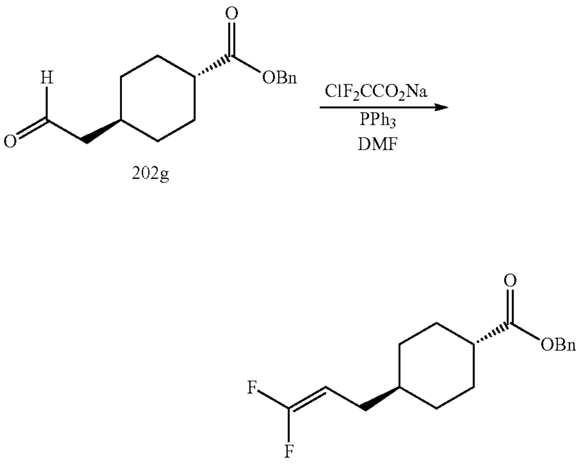

202g

202h

A solution of 4-(2-oxo-ethyl)-cyclohexanecarboxylic acid benzyl ester (trans:cis=4:1) (21.4 mg, 0.082 mmol) in dimethylformamide (0.3 ml) was added to a solution of sodium chlorodifluoroacetate (34.1 mg, 0.224 mmol) and triphenylphosphine (59.9 mg, 0.228 mmol) in dimethylformamide (0.41 ml) at 90 to 95° C. over five minutes, and the mixture was stirred at 130° C. for four hours. Sodium chlorodifluoroacetate (34.0 mg, 0.22 mmol) was then added to the reaction mixture at the same temperature, and the mixture was further stirred for two hours. The reaction mixture was diluted with ether, and the organic layer was washed with water, dried over $MgSO_4$ and concentrated under reduced pressure. The resulting residue was purified by silica gel column chromatography (hexane-ethyl acetate) to give 4-(3,3-difluoro-allyl)-cyclohexanecarboxylic acid benzyl ester (trans:cis=4:1) (14.1 m, 58%).

$^1$H-NMR (400 MHz, $CDCl_3$) δ 0.95 (1.6H, m), 1.26 (0.4H, m), 1.44 (1.6H, m), 1.55 (0.8H, m), 1.81 (1.6H, m), 1.87 (2.2H, m), 2.20 (2H, m), 2.28 (0.8H, m), 2.60 (0.2H, m), 4.09 (0.2H, dtd, J=25.4, 8.3, 2.9 Hz), 4.12 (0.8H, dtd, J=25.4, 7.8, 2.9 Hz), 5.11 (1.6H, s), 5.13 (0.4H, s), 7.34 (5H, m).

(Reaction 202-5)

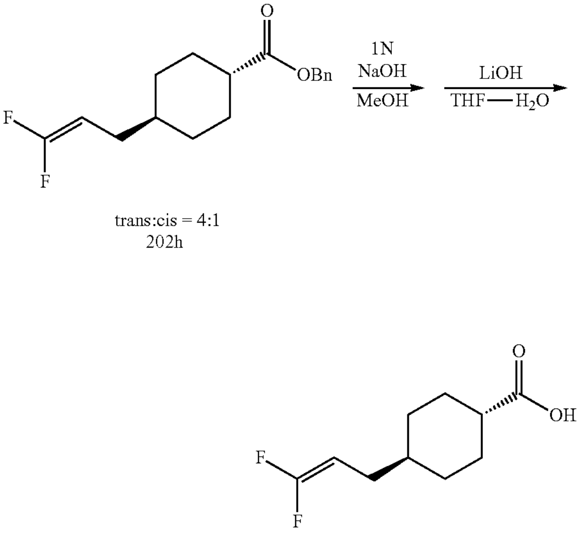

trans:cis = 4:1
202h trans:cis = 8.6:1
202i

A 1 N aqueous NaOH solution (0.084 ml, 0.084 mmol) was added to a solution of 4-(3,3-difluoro-allyl)-cyclohexanecarboxylic acid benzyl ester (trans:cis=4:1) (14.1 mg, 0.0478 mmol) in methanol (1.0 mL). The mixture was stirred at room temperature for 1.5 hours, and then adjusted to pH 6 with a 1 N aqueous HCl solution and concentrated under reduced pressure. The resulting residue was adjusted to pH 3 with dilute hydrochloric acid and extracted with dichloromethane, and the organic layer was dried over $MgSO_4$ and concentrated under reduced pressure. The resulting residue was dissolved in THF (0.2 ml)-$H_2O$ (0.2 ml), and $LiOH.H_2O$ (7.7 mg, 0.18 mmol) was added. The mixture was stirred at room temperature for three hours, and then adjusted to pH 3 with a 1 N aqueous HCl solution and extracted with dichloromethane. The organic layer was then dried over $MgSO_4$ and concentrated under reduced pressure. The resulting residue was purified by column chromatography (hexane-ethyl acetate) to give 4-(3,3-difluoro-allyl)-cyclohexanecarboxylic acid (8.3 g, 86%).

$^1$H-NMR (400 MHz, $CDCl_3$) δ 0.97 (1.8H, m), 1.27 (0.4H, m), 1.43 (1.8H, m), 1.58 (1H, m), 1.82 (2H, m), 1.88 (2H, m), 2.03 (2H, m), 2.25 (0.9H, m), 2.61 (0.1H, m), 4.13 (1H, dtd, J=25.4, 7.8, 2.9 Hz).

Example 203

N-(4-{(E)-1-Fluoro-2-[2-(4-methyl-cyclohexyl)-4-oxo-1,3,8-triaza-spiro[4.5]dec-1-ene-8-sulfonyl]-vinyl}-3-methyl-phenyl)-N-methyl-acetamide (Compound 942)

(Reaction 203-1)

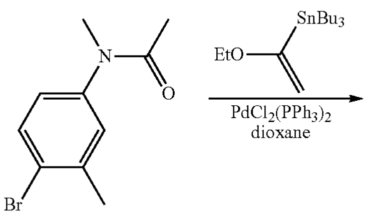

31o

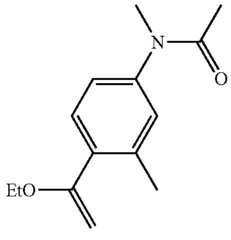

203a

Tributyl(1-ethoxyvinyl)tin (1.07 mmol, 3.18 mmol) and dichlorobis(triphenylphosphine)palladium(II) (101 mg, 0.145 mmol) were added to a solution of N-(4-bromo-3-methylphenyl)-N-methylacetamide (700 mg, 2.89 mmol) in 1,4-dioxane (7 mL), and the mixture was heated with stirring at 90° C. for 12 hours in a nitrogen stream. The reaction mixture was cooled and then filtered through celite. The solution was concentrated under reduced pressure, and the residue was then silica gel column chromatography (hexane-ethyl acetate) to give N-[4-(1-ethoxy-vinyl)-3-methyl-phenyl]-N-methyl-acetamide (440 mg, 65%).

MS (ESI) m/z=234 (M+H)+.

(Reaction 203-2)

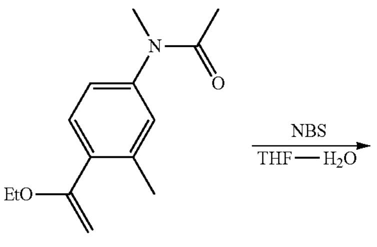

203a

-continued

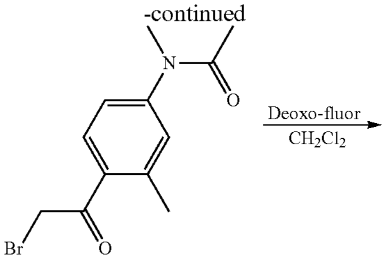

203b

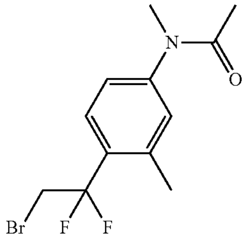

203c

N-[4-(2-Bromo-1,1-difluoroethyl)-3-methylphenyl]-N-methylacetamide was synthesized by operations similar to those in Reaction 127-4 and Reaction 191-11 using appropriate reagents and starting material.

MS (ESI) m/z=306, 308 (M+H)+.

(Reaction 203-3)

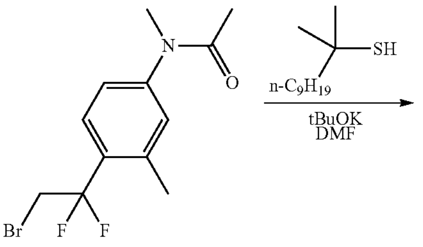

203c

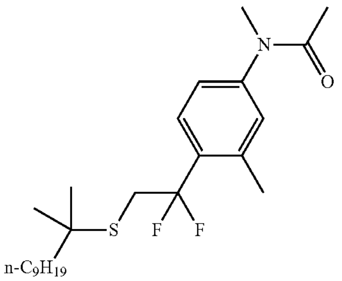

203d t-Dodecanethiol (0.227 mL, 0.96 mmol) was added to a solution of potassium t-butoxide (108 mg, 0.96 mmol) in DMF (2 mL), and the mixture was stirred at room temperature. A solution of N-[4-(2-bromo-1,1-difluoroethyl)-3-methylphenyl]-N-methylacetamide (245 mg, 0.800 mmol) in DMF (2 mL) was added to the mixture which was then stirred at room temperature for one hour. Saturated $NH_4Cl$ was added to the reaction mixture, followed by extraction with ethyl acetate. The organic layer was washed with saturated brine, and then dried over $MgSO_4$ and concentrated under reduced pressure. The resulting residue was purified by silica gel column chromatography (hexane-ethyl acetate) to give N-{4-[2-(1,1-dimethyldecylsulfanyl)-1,1-difluoro-ethyl]-3-methylphenyl}-N-methylacetamide (287 mg, 84%).

MS (ESI) m/z=428 (M+H)+.

(Reaction 203-4)

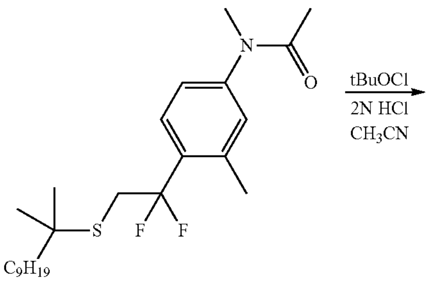

203d

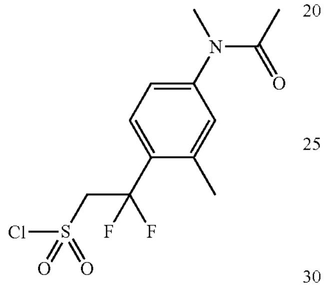

203e

2 N HCl (0.4 mL) was added to a solution of N-{4-[2-(1,1-dimethyldecylsulfanyl)-1,1-difluoro-ethyl]-3-methylphenyl}-N-methylacetamide (102 mg, 0.239 mmol) in MeCN (1 mL) at 0° C. After stirring for five minutes, t-butyl hypochlorite (0.135 mL, 1.20 mmol) was added in small portions at −10° C. The mixture was stirred for 15 minutes, and saturated $NH_4Cl$ was then added, followed by extraction with ethyl acetate. The organic layer was washed with saturated brine. The organic layer was dried over $MgSO_4$ and then concentrated under reduced pressure to give a mixture containing 2-[4-(acetylmethylamino)-2-methylphenyl]-2,2-difluoroethanesulfonyl chloride (121 mg).

$^1$H-NMR (400 MHz, $CDCl_3$) δ 7.72 (1H, s), 7.62 (1H, m), 7.30 (1H, m), 4.47-4.57 (2H, m), 3.18 (3H, s), 2.49-2.53 (3H, m), 1.80 and 1.82 (3H, s).

(Reaction 203-5)

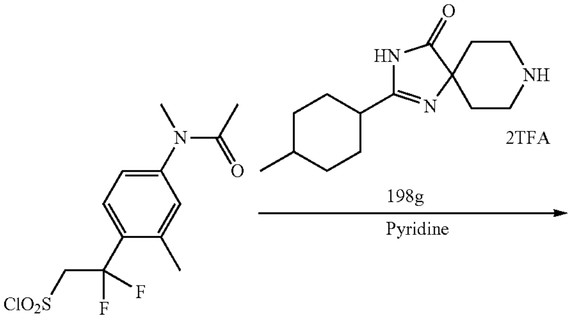

203e

-continued

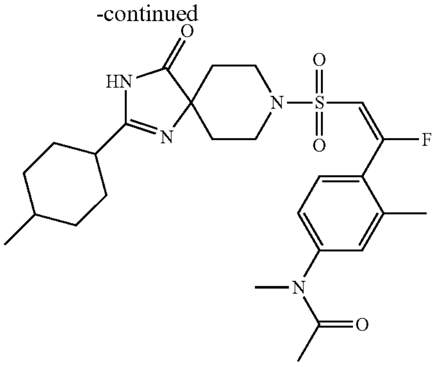

Compound 942

N-(4-{(E)-1-Fluoro-2-[2-(4-methyl-cyclohexyl)-4-oxo-1,3,8-triaza-spiro[4.5]dec-1-ene-8-sulfonyl]-vinyl}-3-methyl-phenyl)-N-methyl-acetamide was synthesized by operations similar to those in Reaction 6-1 using appropriate reagents and the starting material obtained above.

MS (ESI) m/z=519 (M+H)+.

Example 204

3-[3-Methyl-4-(2-{4-oxo-2-[4-(3,3,3-trifluoro-propyl)-cyclohexyl]-1,3,8-triaza-spiro[4.5]dec-1-ene-8-sulfonyl}-ethyl)-phenyl]-imidazolidine-2,4-dione (Compound 943)

(Reaction 204-1)

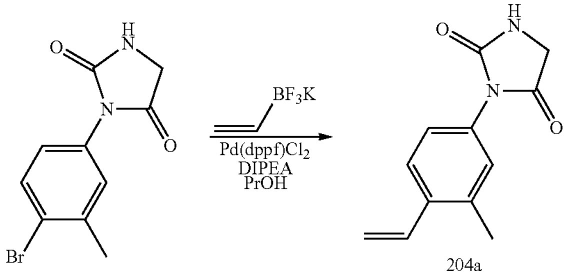

96b

204a

Potassium vinyltrifluoroborate (356 mg, 242 μmol), ethyldiisopropylamine (48 μL, 279 μmol) and [1,1'-bis(diphenylphosphino)ferrocene]dichloropalladium dichloromethane adduct (15.1 mg, 18.6 μmol) were added to a solution of 3-(4-bromo-3-methyl-phenyl)-imidazolidine-2,4-dione (50 mg, 186 μmol) in n-PrOH (372 μL) at room temperature in an $N_2$ atmosphere. The mixture was stirred at 100° C. for 1.5 hours, and the reaction solution was then cooled. The reaction solution was concentrated under reduced pressure. The resulting residue was purified by silica gel column chromatography (dichloromethane-methanol) to give 3-(3-methyl-4-vinyl-phenyl)-imidazolidine-2,4-dione as a yellow brown form (33 mg, 82%).

MS (ESI) m/z=217 (M+H)+.

(Reaction 204-2)
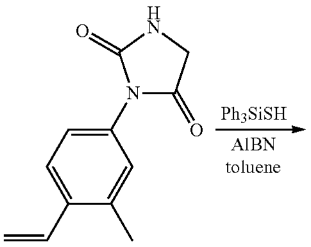
204a
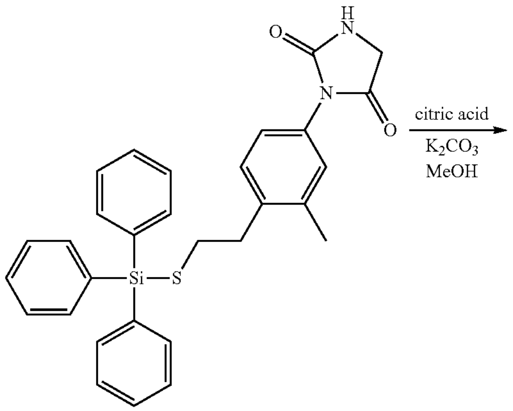
204b
-continued
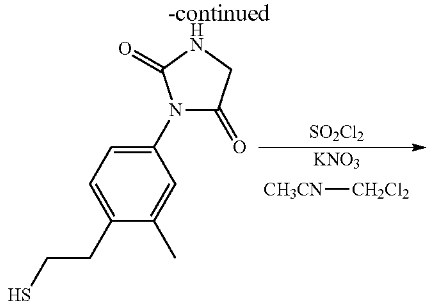
204c
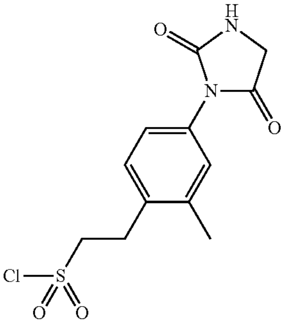
204d
2-[4-(2,5-Dioxo-imidazolidin-1-yl)-2-methyl-phenyl]-ethanesulfonyl chloride was synthesized by operations similar to those in Reaction 10-3, Reaction 10-4 and Reaction 10-5 using appropriate reagents and starting material.
MS (ESI) m/z=317, 319 (M+H)+.
(Reaction 204-3)
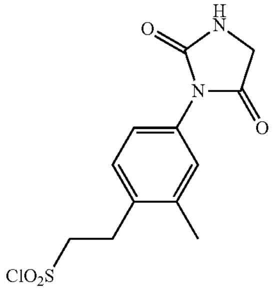
204d
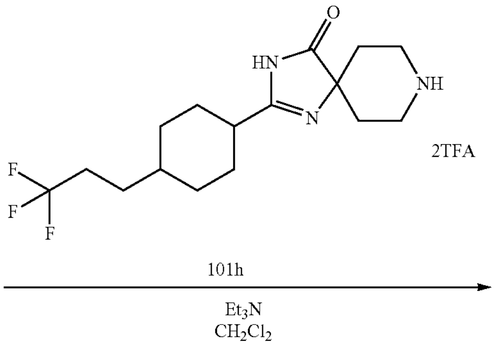
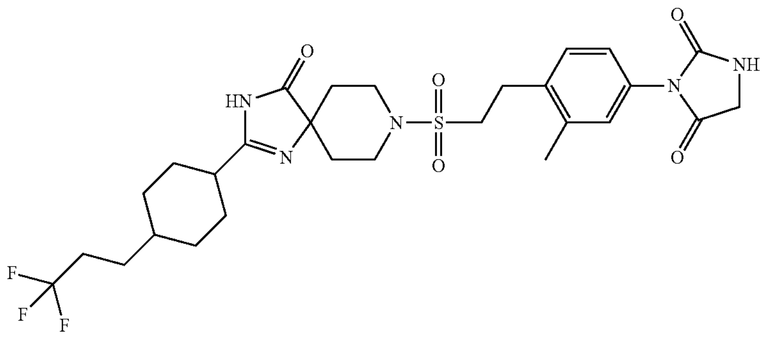
Compound 943

3-[3-Methyl-4-(2-{4-oxo-2-[4-(3,3,3-trifluoro-propyl)-cyclohexyl]-1,3,8-triaza-spiro[4.5]dec-1-ene-8-sulfonyl}-ethyl)-phenyl]-imidazolidine-2,4-dione was synthesized by operations similar to those in Reaction 5-4 using appropriate reagents and the starting material obtained above.

MS (ESI) m/z=612 (M+H)+.

The example compounds shown below were synthesized by operations similar to those in Reaction 204-3 using appropriate reagents and starting materials.

Compounds 944 to 947

TABLE 133

| Compound | Structure | LCMS condition | Retention time (min) | MS (m/z) |
|---|---|---|---|---|
| 944 | 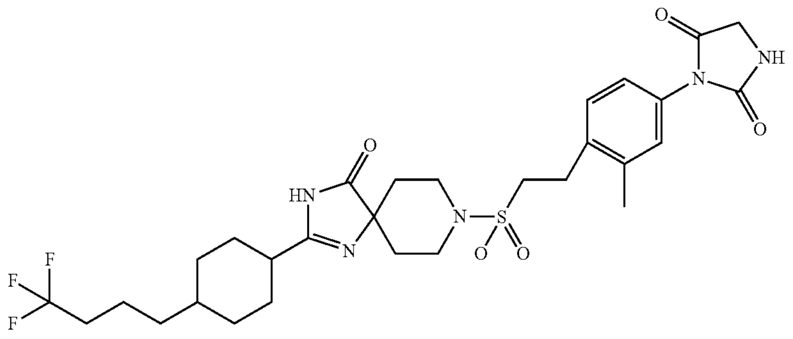 | LCMS-F-1 | 0.95 | 626 (M + H)+ |
| 945 | 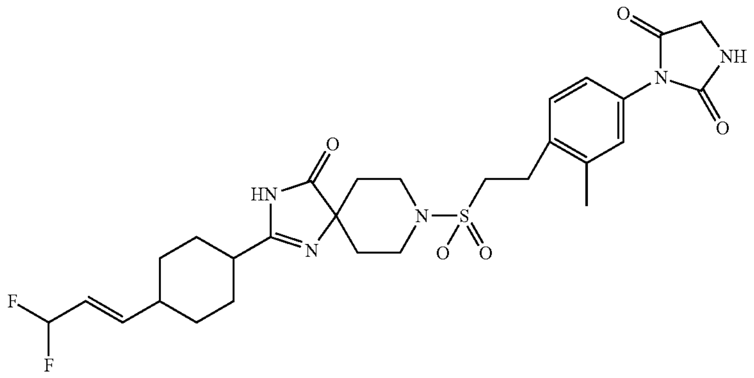 | LCMS-F-1 | 0.85 | 592 (M + H)+ |
| 946 | 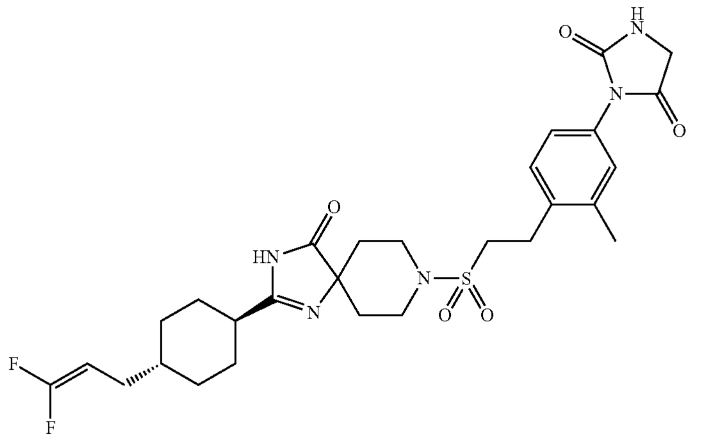 [SMILES: Cc1cc(N2C(=O)CNC2=O)ccc1CCS(=O)(=O)N1CCC2(CC1)N=C([C@H]1CC[C@H](CC=C(F)F)CC1)NC2=O] | LCMS-B-1 | 1.85 | 592 (M + H)+ |

TABLE 133-continued

| Compound | Structure | LCMS condition | Retention time (min) | MS (m/z) |
|---|---|---|---|---|
| 947 | 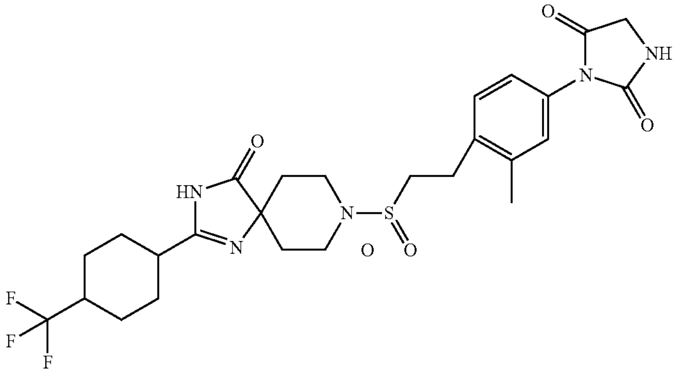 | LCMS-F-1 | 0.84 | 584 (M + H)+ |

Example 205

3-[3-Methyl-4-(2-{4-oxo-2-[4-(2,2,2-trifluoro-ethyl)-cyclohexyl]-1,3,8-triaza-spiro[4.5]dec-1-ene-8-sulfonyl}-ethyl)-phenyl]-imidazolidine-2,4-dione (Compound 948)

(Reaction 205-1)

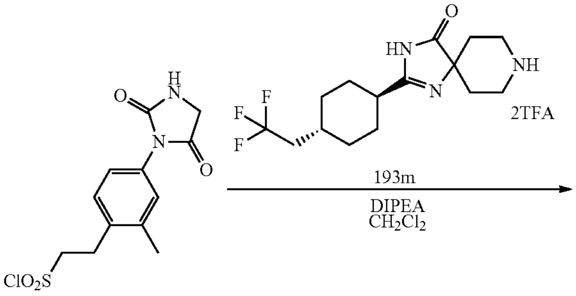

204d

-continued

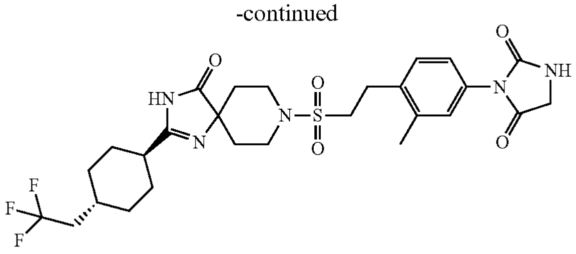

Compound 948

3-[3-Methyl-4-(2-{4-oxo-2-[4-(2,2,2-trifluoro-ethyl)-cyclohexyl]-1,3,8-triaza-spiro[4.5]dec-1-ene-8-sulfonyl}-ethyl)-phenyl]-imidazolidine-2,4-dione was synthesized by operations similar to those in Reaction 5-4 using appropriate reagents and starting material.

MS (ESI) m/z=598 (M+H)+.

The example compounds shown below were synthesized by operations similar to those in Reaction 205-1 using appropriate reagents and starting materials.

Compounds 949 to 952

TABLE 134

| Compound | Structure | LCMS condition | Retention time (min) | MS (M/z) |
|---|---|---|---|---|
| 949 | 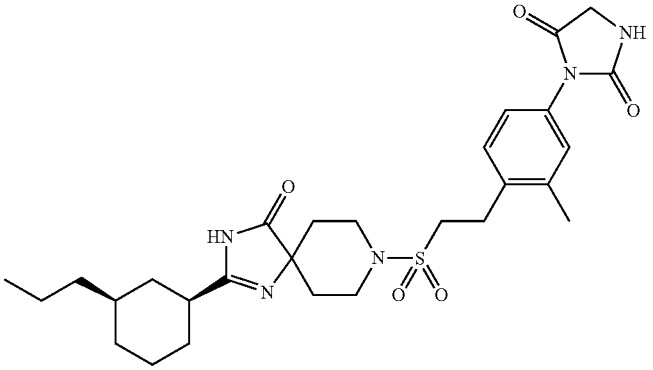 [SMILES: CCC[C@@H]1CCC[C@H](C2=NC3(CCN(S(=O)(=O)CCc4ccc(N5C(=O)CNC5=O)cc4C)CC3)C(=O)N2)C1] | LCMS-A-1 | 2.16 | 558 (M + H)+ |

TABLE 134-continued
| Compound | Structure | LCMS condition | Retention time (min) | MS (M/z) |
|---|---|---|---|---|
| 950 | 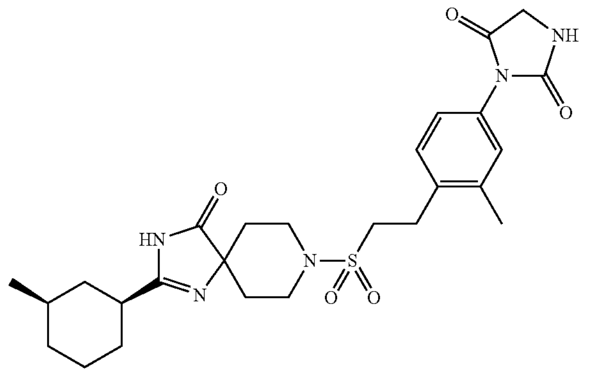 [SMILES: Cc1cc(N2C(=O)CNC2=O)ccc1CCS(=O)(=O)N1CCC2(CC1)N=C([C@H]1CCC[C@@H](C)C1)NC2=O] | LCMS-C-1 | 2.35 | 530 (M + H)+ |
| 951 | 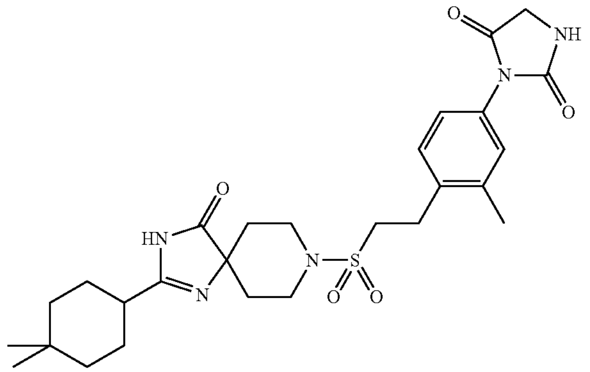 [SMILES: Cc1cc(N2C(=O)CNC2=O)ccc1CCS(=O)(=O)N1CCC2(CC1)N=C(C1CCC(C)(C)CC1)NC2=O] | LCMS-C-1 | 2.52 | 544 (M + H)+ |
| 952 | 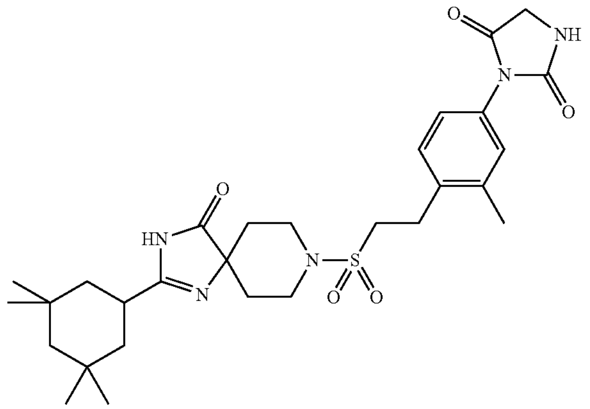 [SMILES: Cc1cc(N2C(=O)CNC2=O)ccc1CCS(=O)(=O)N1CCC2(CC1)N=C(C1CC(C)(C)CC(C)(C)C1)NC2=O] | LCMS-C-1 | 2.73 | 572 (M + H)+ |

Example 206

N-(2-Chloro-4-{2-[2-(4-ethyl-cyclohexyl)-4-oxo-1,3,8-triaza-spiro[4.5]dec-1-ene-8-sulfonyl]-ethyl}-5-methyl-phenyl)-acetamide (Compound 953) and N-(2-chloro-4-{2-[2-(4-ethyl-cyclohexyl)-4-oxo-1,3,8-triaza-spiro[4.5]dec-1-ene-8-sulfonyl]-ethyl}-3-methyl-phenyl)-acetamide (Compound 954)

(Reaction 206-1)

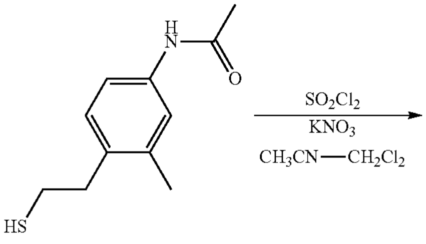

11d

-continued

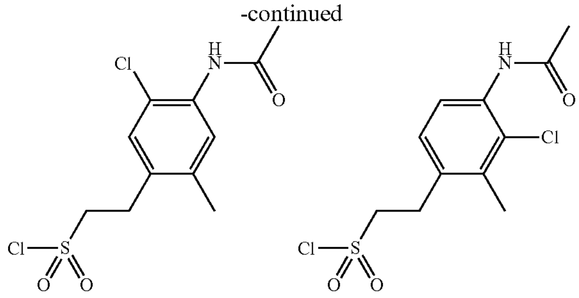

Mixture
206a

A sulfonyl chloride reagent (a mixture of 2-(4-acetylamino-5-chloro-2-methyl-phenyl)-ethanesulfonyl chloride and 2-(4-acetylamino-3-chloro-2-methyl-phenyl)-ethanesulfonyl chloride) was synthesized by operations similar to those in Reaction 10-5 using appropriate reagents and starting material.

MS (ESI) m/z=310, 312, 314 (M+H)+.

(Reaction 206-2)

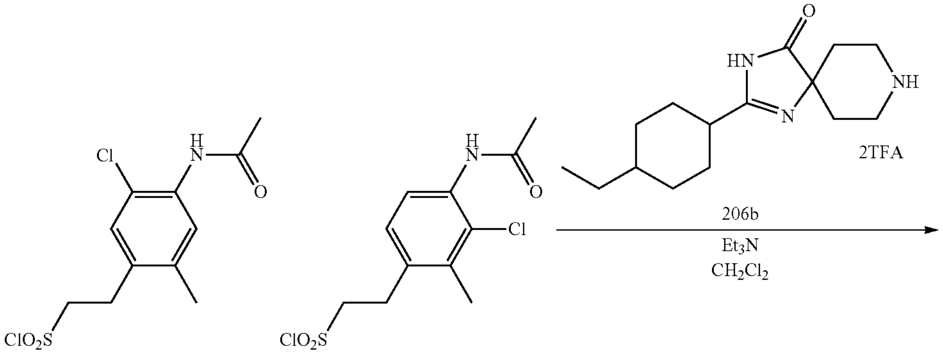

Mixture
206a

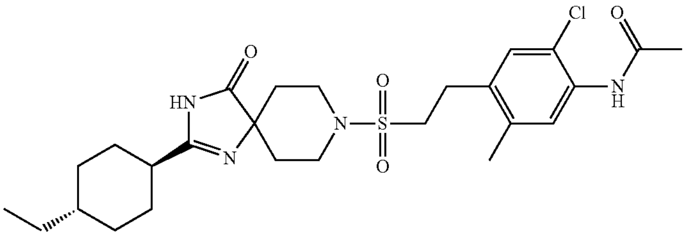

Compound 953

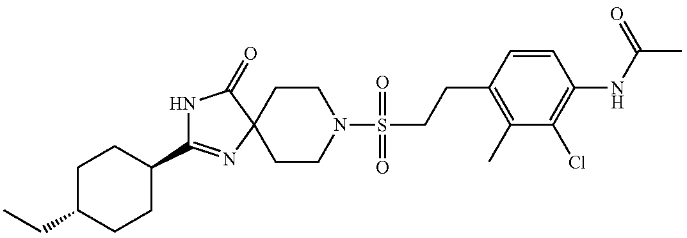

Compound 954

N-(2-Chloro-4-{2-[2-(4-ethyl-cyclohexyl)-4-oxo-1,3,8-triaza-spiro[4.5]dec-1-ene-8-sulfonyl]-ethyl}-5-methyl-phenyl)-acetamide MS (ESI) m/z=537 (M+H)+ and N-(2-chloro-4-{2-[2-(4-ethyl-cyclohexyl)-4-oxo-1,3,8-triaza-spiro[4.5]dec-1-ene-8-sulfonyl]-ethyl}-3-methyl-phenyl)-acetamide MS (ESI) m/z=537 (M+H)+ were obtained by operations similar to those in Reaction 5-4 using appropriate reagents and the starting material obtained above.

Example 207

N-[4-(2-{2-[4-(3,3-Difluoro-propyl)-cyclohexyl]-4-oxo-1,3,8-triaza-spiro[4.5]dec-1-ene-8-sulfonyl}-ethyl)-3-methyl-phenyl]-acetamide (Compound 955)

(Reaction 207-1)

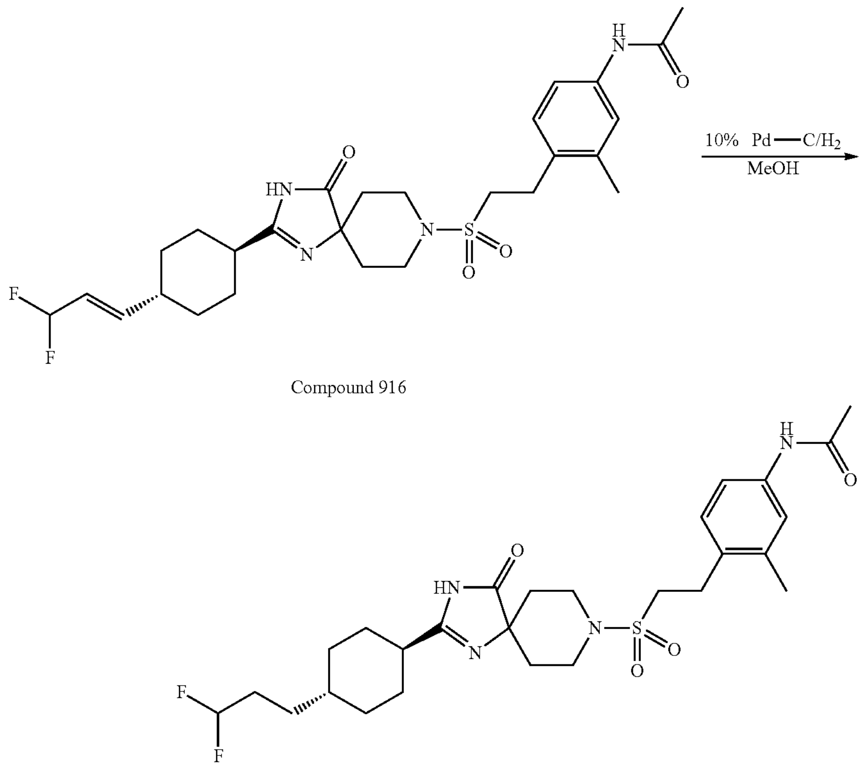

Compound 916

Compound 955

N-[4-(2-{2-[4-(3,3-Difluoro-propyl)-cyclohexyl]-4-oxo-1,3,8-triaza-spiro[4.5]dec-1-ene-8-sulfonyl}-ethyl)-3-methyl-phenyl]-acetamide (Compound 955) was obtained by operations similar to those in Reaction 18-2 using Compound as a starting material.

MS (ESI) m/z=553 (M+H)+.

The example compound shown below was obtained by operations similar to those in Reaction 207-1 using an appropriate starting compound.

Compound 956

TABLE 135

| Raw material Compound | Target Compound | Structure | LCMS condition | Retention time (min) | MS (m/z ) |
|---|---|---|---|---|---|
| 945 | 956 | 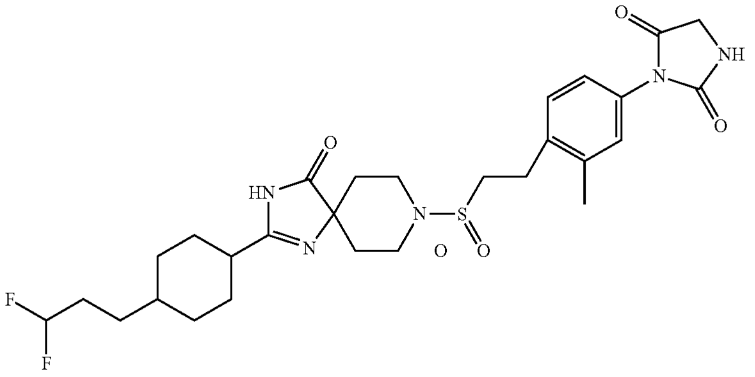 | LCMS-F-1 | 0.87 | 594 (M + H)+ |

Example 208

2-(2-Cyclohexyl-4-oxo-1,3,8-triaza-spiro[4.5]dec-1-ene-8-sulfonyl)-N-phenyl-benzamide (Compound 957)

(Reaction 208-1)

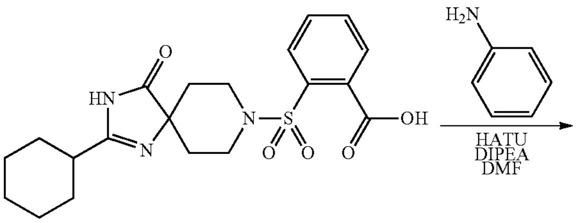

58c

-continued

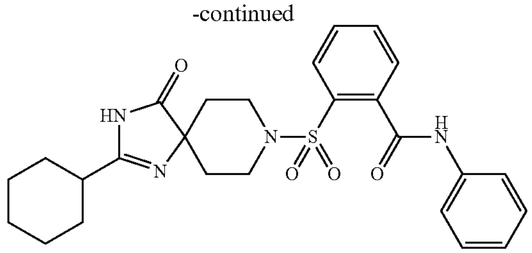

Compound 957

2-(2-Cyclohexyl-4-oxo-1,3,8-triaza-spiro[4.5]dec-1-ene-8-sulfonyl)-N-phenyl-benzamide was synthesized by operations similar to those in Reaction 10-14 using appropriate reagents and starting material.

MS (ESI) m/z=495 (M+H)+.

Example 209

8-(2-{2-Methyl-4-[4-(1-methyl-piperidin-4-yl)-piperazine-1-carbonyl]-phenyl}-ethanesulfonyl-2-(3-trifluoromethyl-phenyl)-1,3,8-triaza-spiro[4.5]dec-1-en-4-one (Compound 958)

(Reaction 209-1)

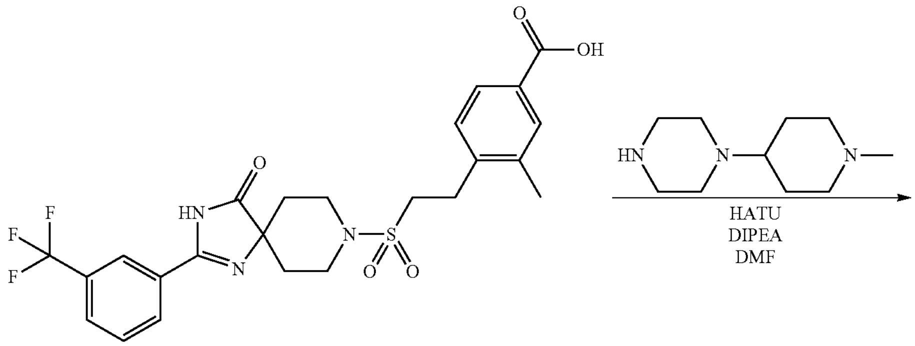

60b

-continued

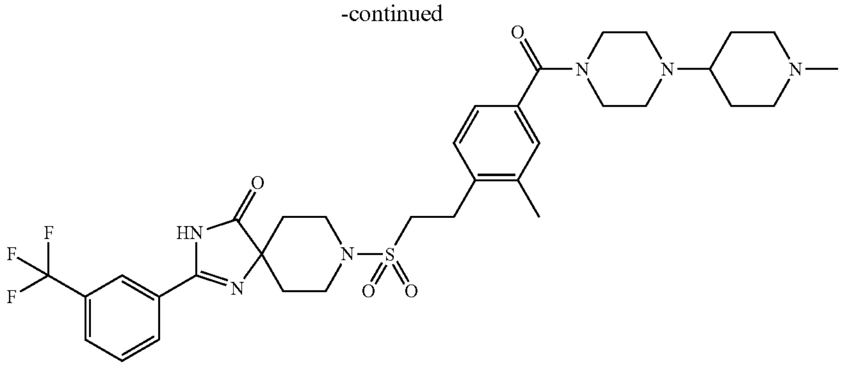

Compound 958

8-(2-{2-Methyl-4-[4-(1-methyl-piperidin-4-yl)-piperazine-1-carbonyl]-phenyl}-ethanesulfonyl-2-(3-trifluoromethyl-phenyl)-1,3,8-triaza-spiro[4.5]dec-1-en-4-one was synthesized by operations similar to those in Reaction 10-14 using appropriate reagents and starting material.

MS (ESI) m/z=689 (M+H)+.

Example 210

8-{(E)-2-[4-((R)-3-Fluoro-pyrrolidine-1-carbonyl)-2,6-dimethyl-phenyl]-ethenesulfonyl}-2-(3-trifluoromethoxy-phenyl)-1,3,8-triaza-spiro[4.5]dec-1-en-4-one (Compound 959)

(Reaction 210-1)

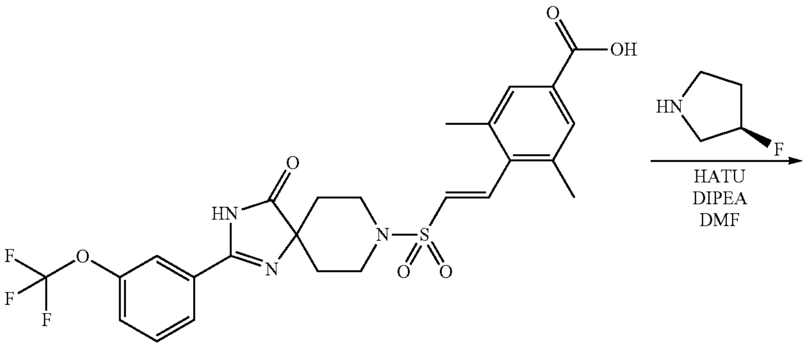

62a

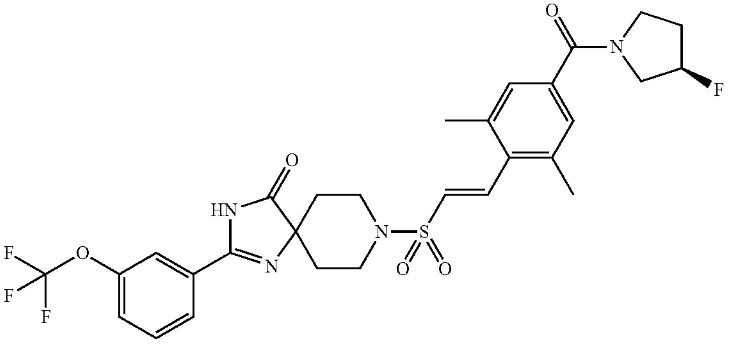

Compound 959

8-{(E)-2-[4-((R)-3-Fluoro-pyrrolidine-1-carbonyl)-2,6-dimethyl-phenyl]-ethenesulfonyl}-2-(3-trifluoromethoxy-phenyl)-1,3,8-triaza-spiro[4.5]dec-1-en-4-one was synthesized by operations similar to those in Reaction 10-14 using appropriate reagents and starting material.

MS (ESI) m/z=623 (M+H)+.

The example compounds shown below were synthesized by operations similar to those in Reaction 210-1 using appropriate reagents and starting materials.

Compounds 960 to 962
TABLE 136
| Compound | Structure | LCMS condition | Retention time (min) | MS (m/z) |
|---|---|---|---|---|
| 960 | 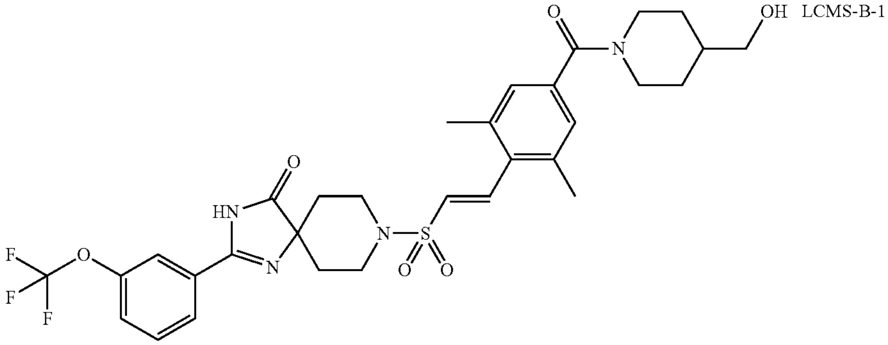 | LCMS-B-1 | 2.15 | 649 (M + H)+ |
| 961 | 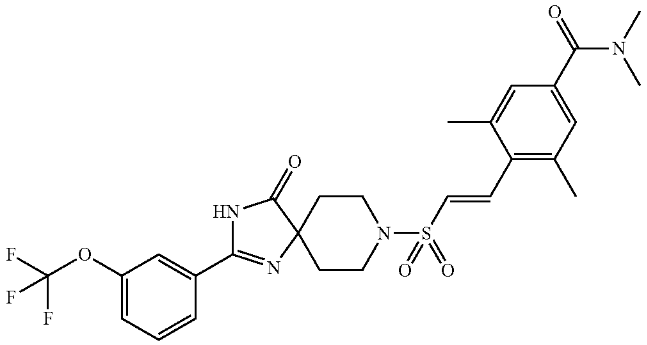 [SMILES: Cc1cc(C(=O)N(C)C)cc(C)c1/C=C/S(=O)(=O)N1CCC2(CC1)N=C(c1cccc(OC(F)(F)F)c1)NC2=O] | LCMS-C-1 | 2.72 | 579 (M + H)+ |
| 962 | 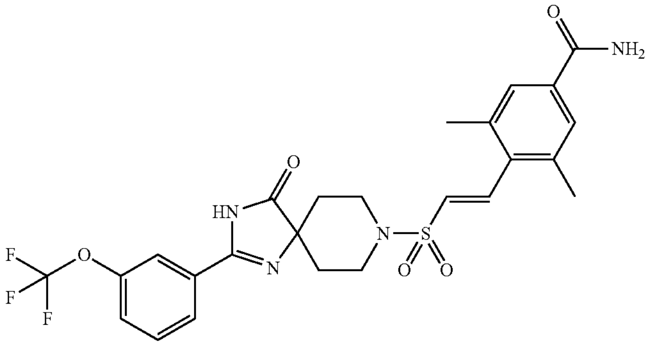 [SMILES: Cc1cc(C(N)=O)cc(C)c1/C=C/S(=O)(=O)N1CCC2(CC1)N=C(c1cccc(OC(F)(F)F)c1)NC2=O] | LCMS-C-1 | 2.62 | 551 (M + H)+ |

Example 211

8-{(E)-2-[4-(3-Fluoro-azetidine-1-carbonyl)-2,6-dimethyl-phenyl]-ethenesulfonyl}-2-(3-trifluoromethoxy-phenyl)-1,3,8-triaza-spiro[4.5]dec-1-en-4-one (Compound 963)

(Reaction 211-1)

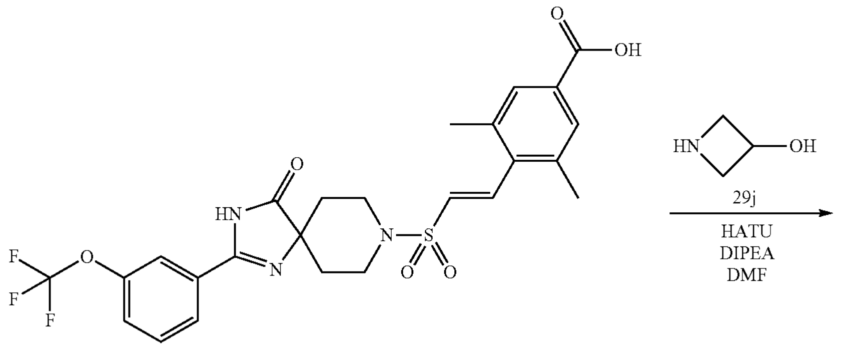

62a

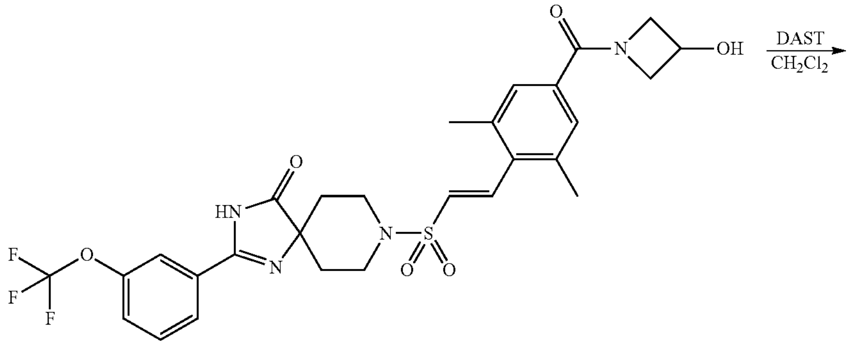

211a

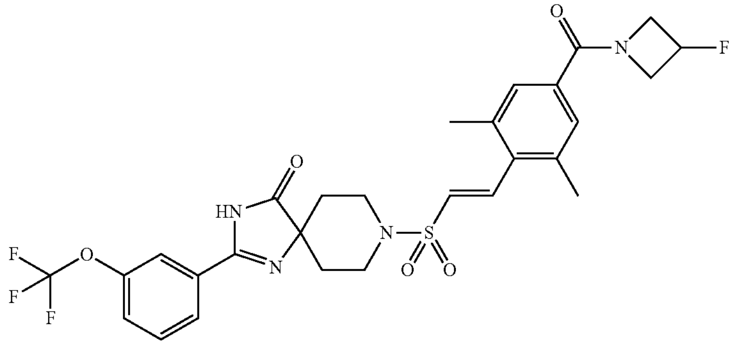

Compound 963

8-{(E)-2-[4-(3-Fluoro-azetidine-1-carbonyl)-2,6-dimethyl-phenyl]-ethenesulfonyl}-2-(3-trifluoromethoxy-phenyl)-1,3,8-triaza-spiro[4.5]dec-1-en-4-one was synthesized by operations similar to those in Reaction 10-14 and Reaction 25-15 using appropriate reagents and starting material.

MS (ESI) m/z=609 (M+H)+.

Example 212

8-{2-[4-(4-Hydroxy-piperidine-1-carbonyl)-2,6-dimethyl-phenyl]-ethanesulfonyl}-2-(3-trifluoromethoxy-phenyl)-1,3,8-triaza-spiro[4.5]dec-1-en-4-one (Compound 964)

(Reaction 212-1)

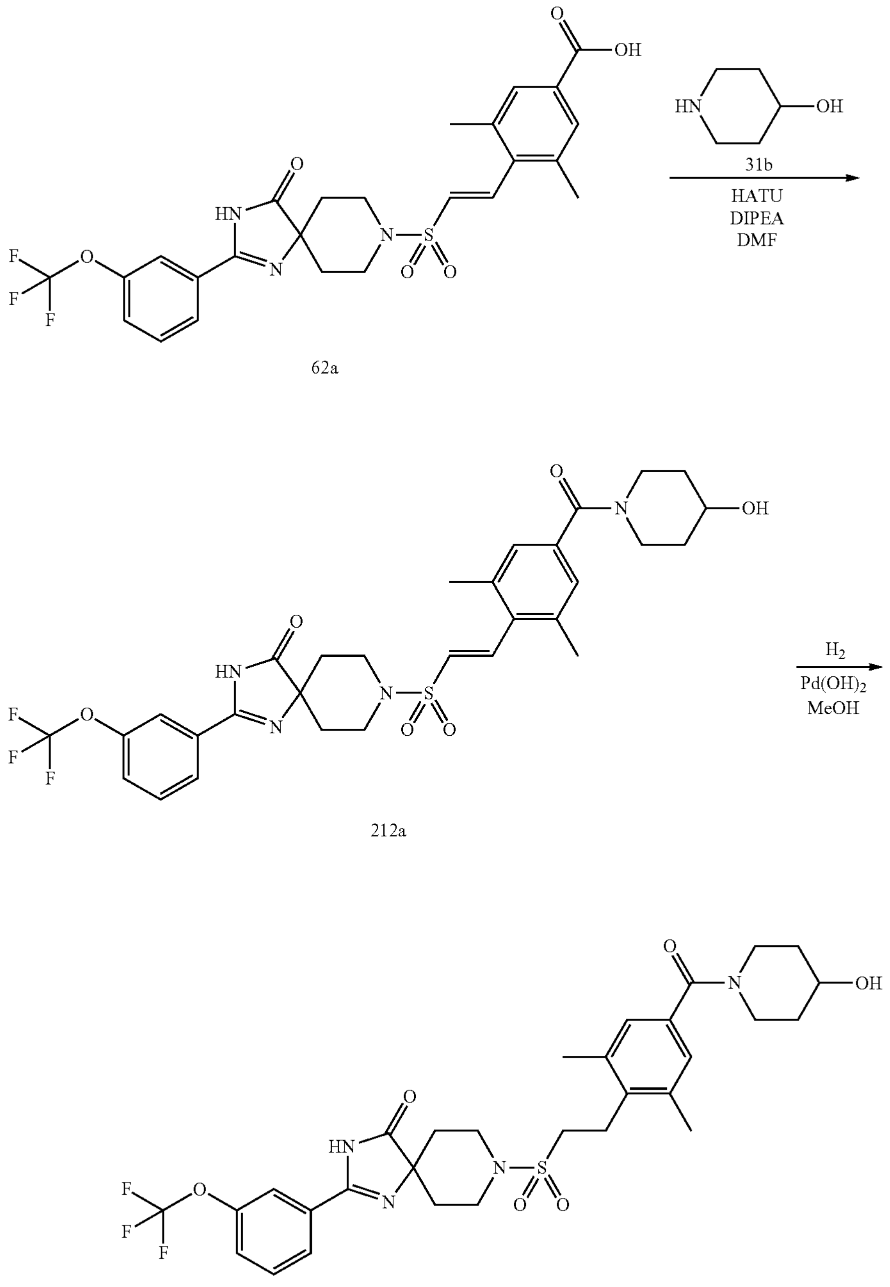

Compound 964

8-{2-[4-(4-Hydroxy-piperidine-1-carbonyl)-2,6-dimethyl-phenyl]-ethanesulfonyl}-2-(3-trifluoromethoxy-phenyl)-1,3,8-triaza-spiro[4.5]dec-1-en-4-one was synthesized by operations similar to those in Reaction 10-14 and Reaction 122-2 using appropriate reagents and starting material.

MS (ESI) m/z=637 (M+H)+.

The example compounds shown below were synthesized by operations similar to those in Reaction 212-1 using appropriate reagents and starting materials.

Compounds 965 to 966

TABLE 137

| Compound | Structure | LCMS condition | Retention time (min) | MS (m/z) |
|---|---|---|---|---|
| 965 | 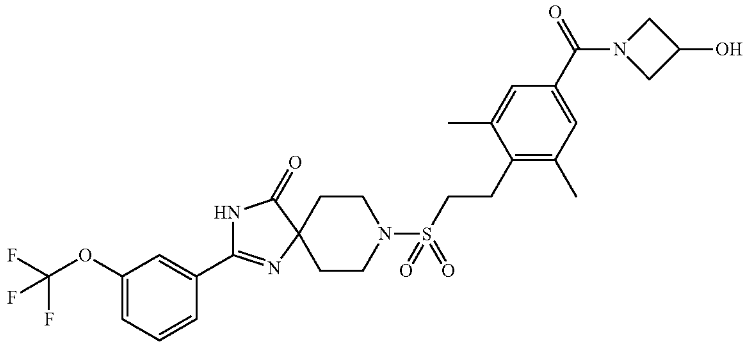 [SMILES: Cc1cc(C(=O)N2CC(O)C2)cc(C)c1CCS(=O)(=O)N1CCC2(CC1)N=C(c1cccc(OC(F)(F)F)c1)NC2=O] | LCMS-F-1 | 0.91 | 609 (M + H)+ |
| 966 | 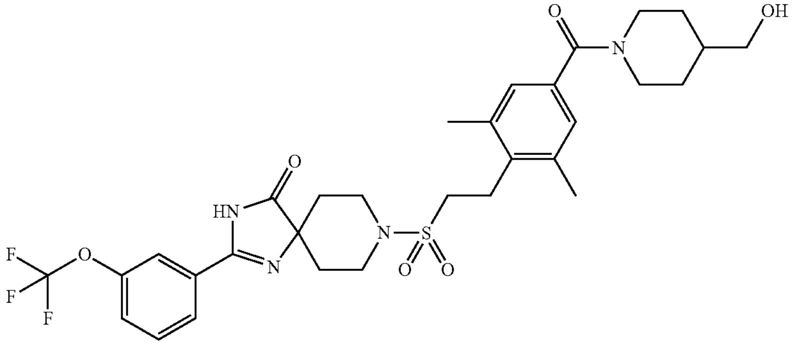 [SMILES: Cc1cc(C(=O)N2CCC(CO)CC2)cc(C)c1CCS(=O)(=O)N1CCC2(CC1)N=C(c1cccc(OC(F)(F)F)c1)NC2=O] | LCMS-F-1 | 0.94 | 651 (M + H)+ |

Example 213

8-{(E)-2-[2,6-Dimethyl-4-(2-oxa-6-aza-spiro[3.3]heptane-6-carbonyl)-phenyl]-ethenesulfonyl}-2-(4-fluoro-3-trifluoromethyl-phenyl)-1,3,8-triaza-spiro[4.5]dec-1-en-4-one (Compound 967)

(Reaction 213-1)

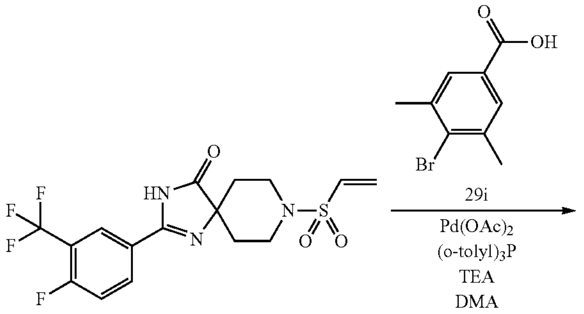

33b

-continued

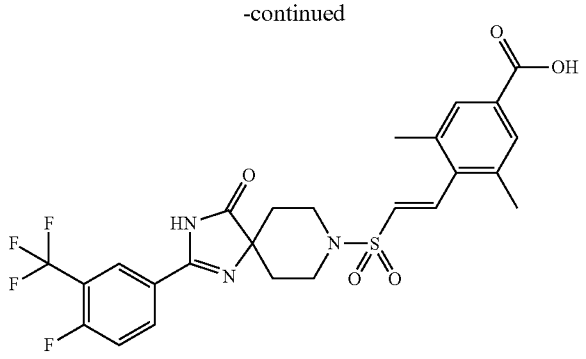

213a

4-{(E)-2-[2-(4-Fluoro-3-trifluoromethyl-phenyl)-4-oxo-1,3,8-triaza-spiro[4.5]dec-1-ene-8-sulfonyl]-vinyl}-3,5-dimethyl-benzoic acid was synthesized by operations similar to those in Reaction 26-1 using appropriate reagents and starting material.

MS (ESI) m/z=554 (M+H)+.

(Reaction 213-2)

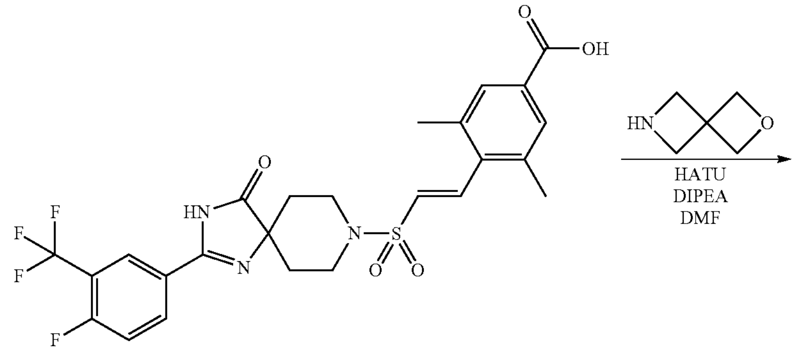

213a

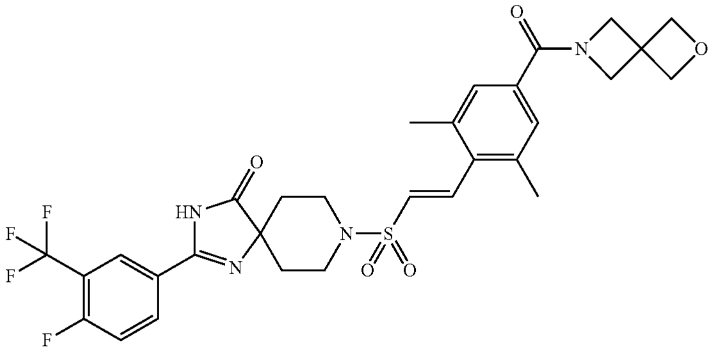

Compound 967

8-{(E)-2-[2,6-Dimethyl-4-(2-oxa-6-aza-spiro[3.3]heptane-6-carbonyl)-phenyl]-ethenesulfonyl}-2-(4-fluoro-3-trifluoromethyl-phenyl)-1,3,8-triaza-spiro[4.5]dec-1-en-4-one was synthesized by operations similar to those in Reaction 10-14 using appropriate reagents and starting material.

MS (ESI) m/z=635 (M+H)+.

Example 214

8-{(E)-2-[2,6-Dimethyl-4-(3-oxo-piperazine-1-carbonyl)-phenyl]-ethenesulfonyl}-2-(4-fluoro-3-trifluoromethyl-phenyl)-1,3,8-triaza-spiro[4.5]dec-1-en-4-one (Compound 968)

(Reaction 214-1)

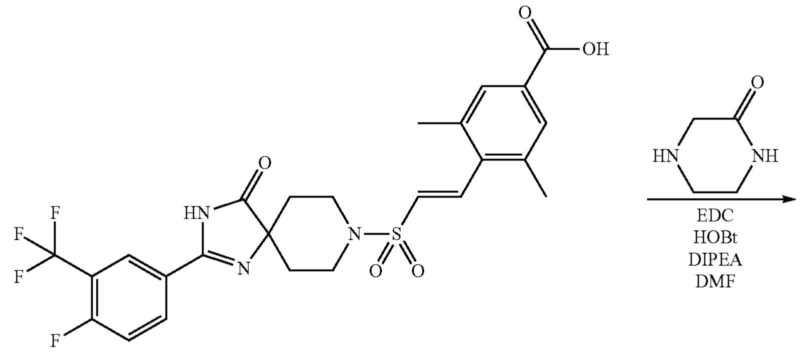

213a

-continued

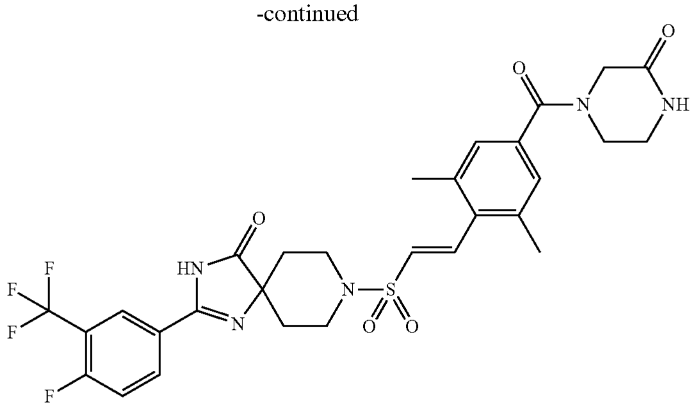

Compound 968

8-{(E)-2-[2,6-Dimethyl-4-(3-oxo-piperazine-1-carbonyl)-phenyl]-ethenesulfonyl}-2-(4-fluoro-3-trifluoromethyl-phenyl)-1,3,8-triaza-spiro[4.5]dec-1-en-4-one was synthesized by operations similar to those in Reaction 10-18 using appropriate reagents and starting material.

MS (ESI) m/z=636 (M+H)+.

The example compounds shown below were synthesized by operations similar to those in Reaction 214-1 using appropriate reagents and starting materials.

Compounds 969 to 972

TABLE 138

| Compound | Structure | LCMS condition | Retention time (min) | MS (m/z) |
|---|---|---|---|---|
| 969 | 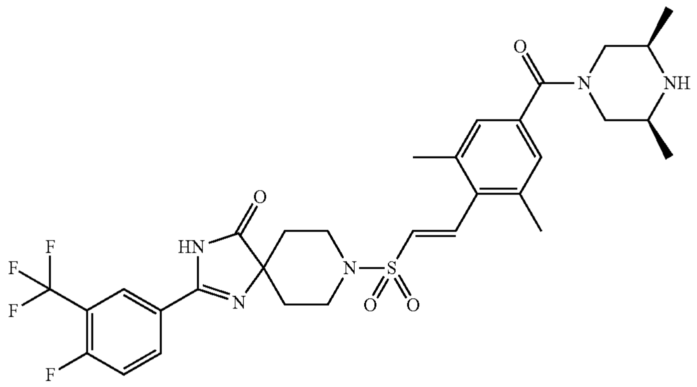 [SMILES: Cc1cc(C(=O)N2C[C@@H](C)N[C@@H](C)C2)cc(C)c1/C=C/S(=O)(=O)N1CCC2(CC1)N=C(c1ccc(F)c(C(F)(F)F)c1)NC2=O] | LCMS-C-1 | 2.67 | 650 (M + H)+ |
| 970 | 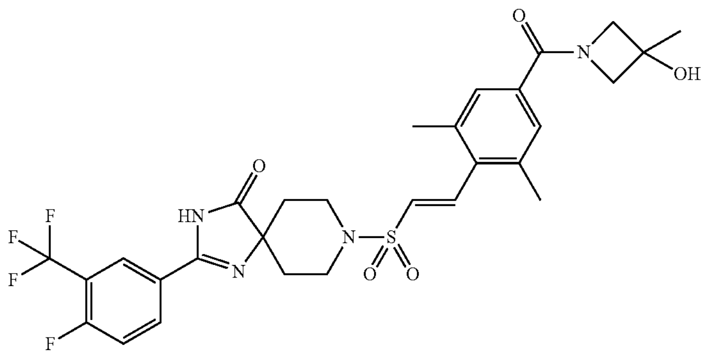 [SMILES: Cc1cc(C(=O)N2CC(C)(O)C2)cc(C)c1/C=C/S(=O)(=O)N1CCC2(CC1)N=C(c1ccc(F)c(C(F)(F)F)c1)NC2=O] | LCMS-C-1 | 2.67 | 623 (M + H)+ |

TABLE 138-continued

| Compound | Structure | LCMS condition | Retention time (min) | MS (m/z) |
|---|---|---|---|---|
| 971 | 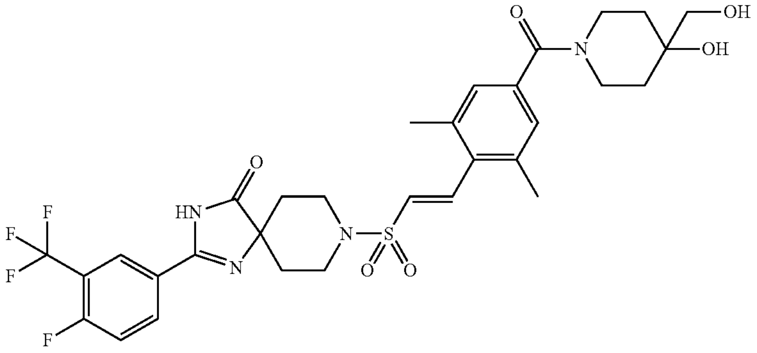 [SMILES: Cc1cc(C(=O)N2CCC(O)(CO)CC2)cc(C)c1/C=C/S(=O)(=O)N1CCC2(CC1)N=C(c1ccc(F)c(C(F)(F)F)c1)NC2=O] | LCMS-C-1 | 2.55 | 667 (M + H)+ |
| 972 | 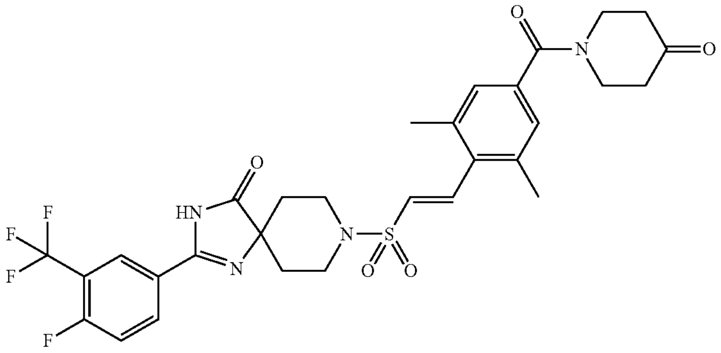 [SMILES: Cc1cc(C(=O)N2CCC(=O)CC2)cc(C)c1/C=C/S(=O)(=O)N1CCC2(CC1)N=C(c1ccc(F)c(C(F)(F)F)c1)NC2=O] | LCMS-G-1 | 1.10 | 635 (M + H)+ |

Example 215

2-[4-(3,3-Difluoro-allyl)-cyclohexyl]-8-{2-[4-(4-fluoro-4-hydroxymethyl-piperidine-1-carbonyl)-2-methyl-phenyl}-ethanesulfonyl]-1,3,8-triaza-spiro[4.5]dec-1-en-4-one (Compound 973)

(Reaction 215-1)

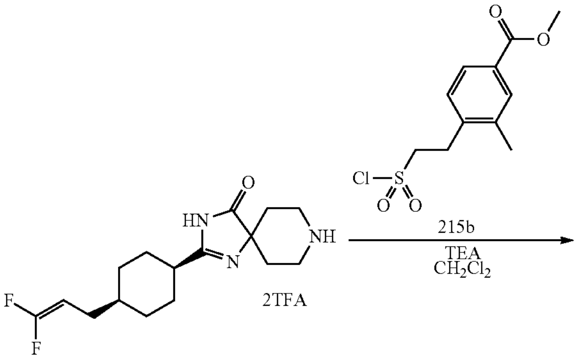

215a

-continued

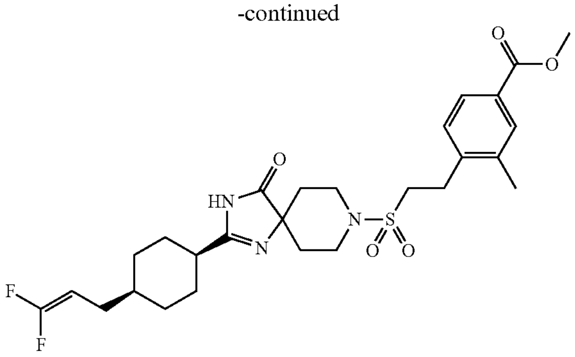

215c 4-(2-{2-[4-(3,3-Difluoro-allyl)-cyclohexyl]-4-oxo-1,3,8-triaza-spiro[4.5]dec-1-ene-8-sulfonyl}-ethyl)-3-methyl-benzoic acid methyl ester was synthesized by operations similar to those in Reaction 5-4 using appropriate reagents and starting material.

MS (ESI) m/z=552 (M+H)+.

(Reaction 215-2)

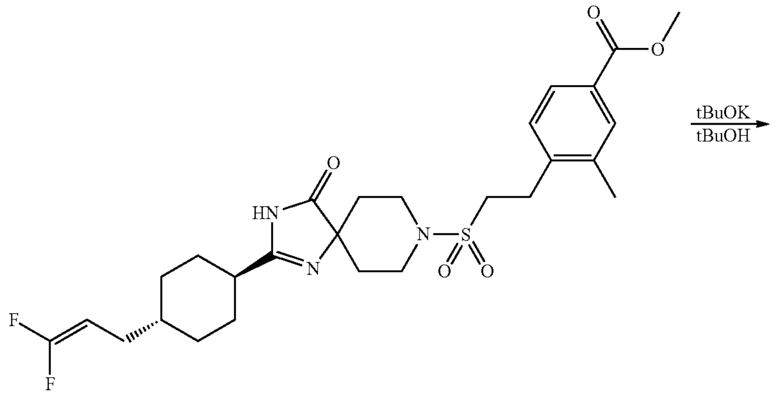

215c

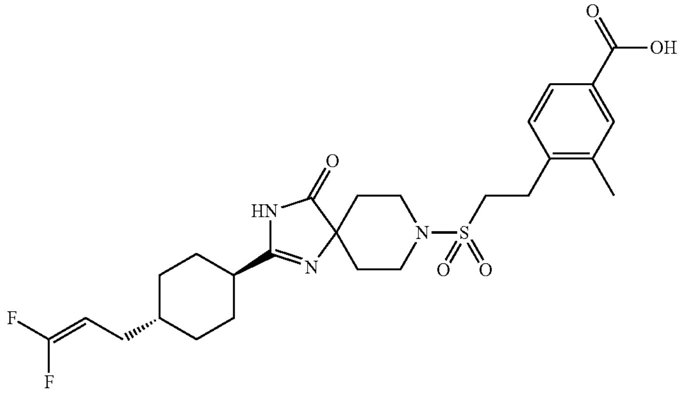

215d

Potassium t-butoxide (15.6 mg) was added to a solution of 4-(2-{2-[4-(3,3-difluoro-allyl)-cyclohexyl]-4-oxo-1,3,8-triaza-spiro[4.5]dec-1-ene-8-sulfonyl}-ethyl)-3-methyl-benzoic acid methyl ester (25.6 mg, 46.4 μmol) in t-butanol (464 μL) and tetrahydrofuran (464 μL), and the mixture was stirred at room temperature for two days. The reaction mixture was diluted with tert-butyl methyl ether and then adjusted to pH 1 with 2 N hydrochloric acid, followed by extraction with ethyl acetate. The organic layer was concentrated under reduced pressure, and the resulting residue was then dried to give 4-(2-{2-[4-(3,3-difluoro-allyl)-cyclohexyl]-4-oxo-1,3,8-triaza-spiro[4.5]dec-1-ene-8-sulfonyl}-ethyl)-3-methyl-benzoic acid (27.5 mg, 91%).

MS (ESI) m/z=538 (M+H)+.

(Reaction 215-3)

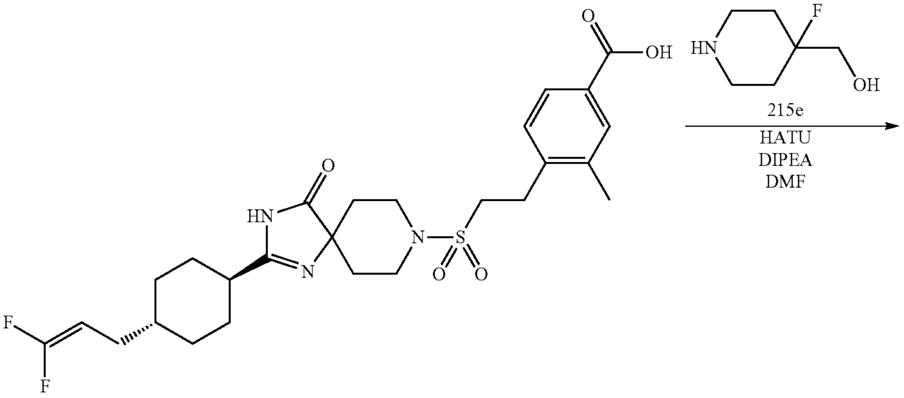

215d

-continued

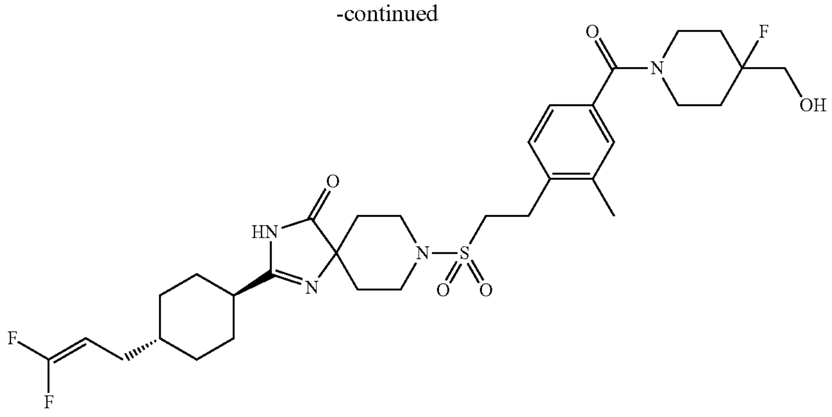

Compound 973

2-[4-(3,3-Difluoro-allyl)-cyclohexyl]-8-{2-[4-(4-fluoro-4-hydroxymethyl-piperidine-1-carbonyl)-2-methyl-phenyl]-ethanesulfonyl}-1,3,8-triaza-spiro[4.5]dec-1-en-4-one was synthesized by operations similar to those in Reaction 10-14 using appropriate reagents and starting material.

MS (ESI) m/z=653 (M+H)+.

The example compound shown below was synthesized by operations similar to those in Reaction 215-3 using appropriate reagents and starting material.

Compound 974

TABLE 139

| Compound | Structure | LCMS condition | Retention time (min) | MS (m/z) |
|---|---|---|---|---|
| 974 | 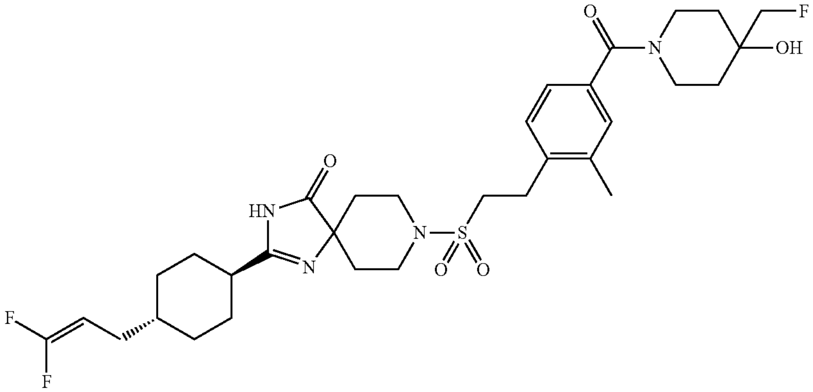 [SMILES: Cc1cc(C(=O)N2CCC(O)(CF)CC2)ccc1CCS(=O)(=O)N1CCC2(CC1)N=C([C@H]1CC[C@H](CC=C(F)F)CC1)NC2=O] | LCMS-B-1 | 1.93 | 653 (M + H)+ |

The amine reagent used for Compound 973 ((4-fluoro-piperidin-4-yl)-methanol hydrochloride) was synthesized by the following method.

(Reaction 215-4)

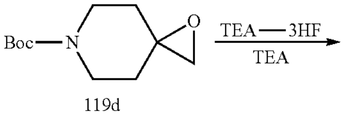

119d

-continued

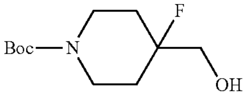

215f

1-Oxa-6-aza-spiro[2.5]octane-6-carboxylic acid tert-butyl ester (144 mg, 679 μmol), triethylamine (1.10 mL, 6.79 mmol) and triethylamine trihydrofluoride (2.85 mL, 20.4 mmol) were mixed in a sealed test tube. This mixture was stirred at 120° C. for 6.5 hours. The reaction mixture was cooled, and then quenched with a 2 N aqueous NaOH solution and extracted with ethyl acetate three times. The organic layers were combined, washed with saturated brine, dried over sodium sulfate and concentrated under reduced pressure. The resulting residue was purified by silica gel column chromatography (hexane-AcOEt) to give 4-fluoro-4-hydroxymethyl-piperidine-1-carboxylic acid tert-butyl ester (24.9 mg, 16%).

$^1$H-NMR (400 MHz, $CDCl_3$) δ 1.44-1.64 (2H, m), 1.82-1.96 (2H, m), 3.04-3.17 (2H, m), 3.61 (2H, d, J=20.0 Hz), 3.84-3.98 (2H, br-m).

(Reaction 215-5)

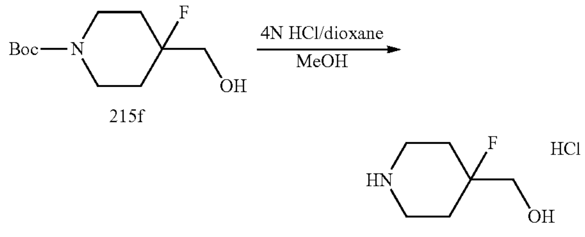

215f

215e

A 4 N solution of hydrochloric acid in 1,4-dioxane (213 μL) was added to a solution of 4-fluoro-4-hydroxymethyl-piperidine-1-carboxylic acid tert-butyl ester (24.9 mg, 0.107 μmol) in MeOH (213 μL) at room temperature, and the mixture was stirred at room temperature for two hours. The reaction solution was concentrated under reduced pressure to give (4-fluoro-piperidin-4-yl)-methanol hydrochloride as a brown form (19.6 mg).

$^1$H-NMR (400 MHz, $CD_3OD$) δ 1.80-2.08 (2H, m), 2.10-2.20 (2H, m), 3.17-3.30 (2H, m), 3.30-3.45 (2H, m), 3.63 (2H, d, J=19.6 Hz).

The sulfonyl chloride reagent used for Compound 973 (4-(2-chlorosulfonyl-ethyl)-3-methyl-benzoic acid methyl ester) was synthesized by the following method.

(Reaction 215-6)

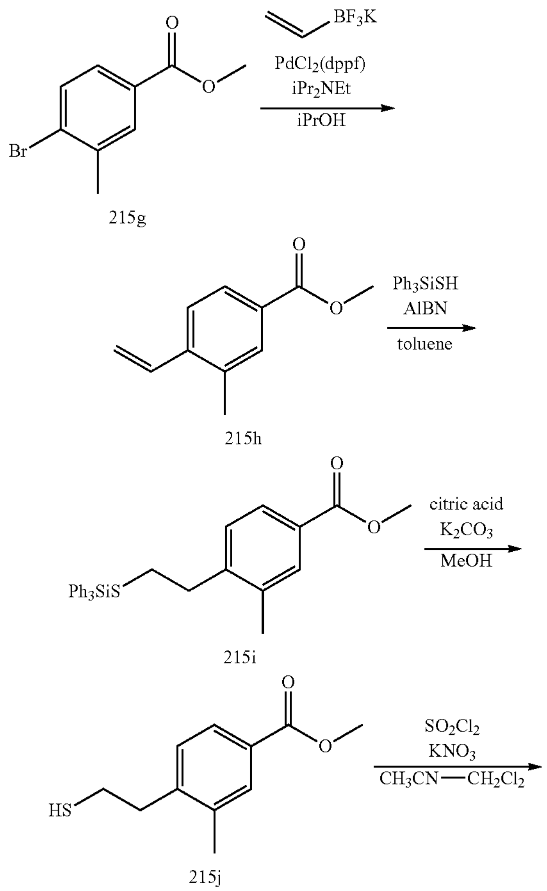

215g

215h

215i

215j

-continued

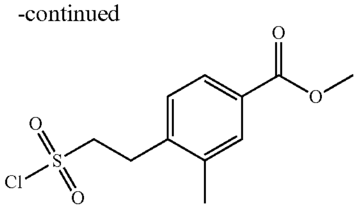

215b 4-(2-Chlorosulfonyl-ethyl)-3-methyl-benzoic acid methyl ester was synthesized by operations similar to those in Reaction 10-2, Reaction 10-3, Reaction 10-4 and Reaction 10-5 using appropriate reagents and starting material.

MS (ESI) m/z=299 (M+Na)+.

Example 216

2-(4-Ethyl-cyclohexyl)-8-(2-{4-[4-(2-fluoro-ethyl)-piperazine-1-carbonyl]-2-methyl-phenyl}-ethane-sulfonyl)-1,3,8-triaza-spiro[4.5]dec-1-en-4-one (Compound 975)

(Reaction 216-1)

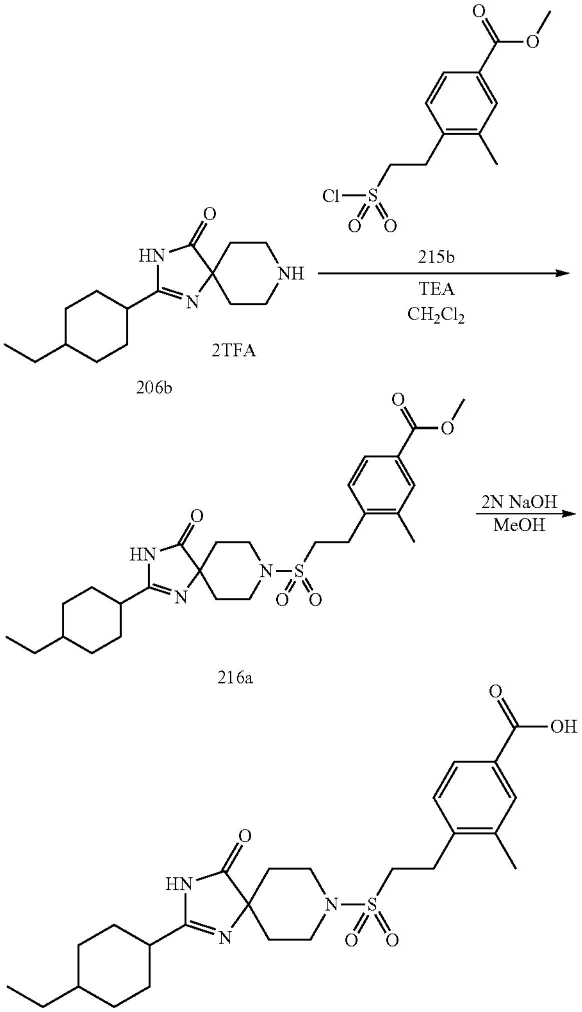

206b

216a

216b

4-{2-[2-(4-Ethyl-cyclohexyl)-4-oxo-1,3,8-triaza-spiro[4.5]dec-1-ene-8-sulfonyl]-ethyl}-3-methyl-benzoic acid was synthesized by operations similar to those in Reaction 5-4 and Reaction 95-18 using appropriate reagents and starting material.

MS (ESI) m/z=490 (M+H)+.

(Reaction 216-2)

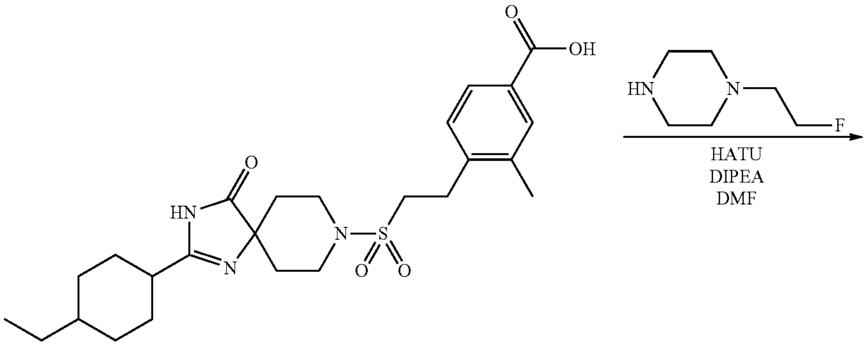

216b

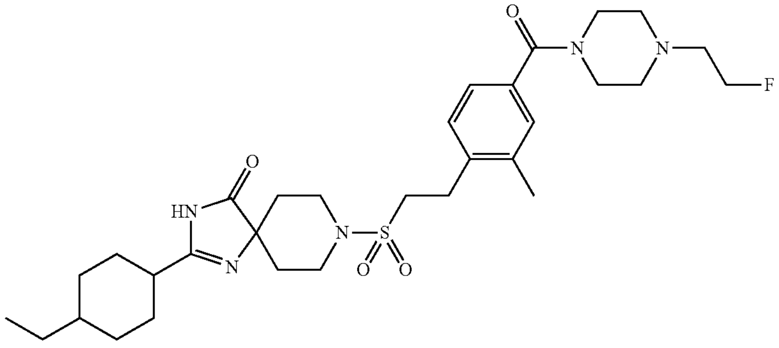

Compound 975

2-(4-Ethyl-cyclohexyl)-8-(2-{4-[4-(2-fluoro-ethyl)-piperazine-1-carbonyl]-2-methyl-phenyl}-ethanesulfonyl)-1,3,8-triaza-spiro[4.5]dec-1-en-4-one was synthesized by operations similar to those in Reaction 10-14 using appropriate reagents and starting material.

MS (ESI) m/z=604 (M+H)+.

The example compound shown below was synthesized by operations similar to those in Reaction 216-2 using appropriate reagents and starting material.

Compound 976

TABLE 140

| Compound | Structure | LCMS condition | Retention time (min) | MS (m/z) |
|---|---|---|---|---|
| 976 | 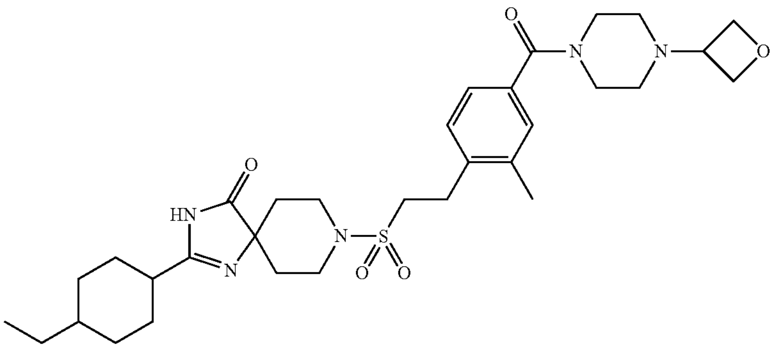 [SMILES: CCC1CCC(C2=NC3(CCN(S(=O)(=O)CCc4ccc(C(=O)N5CCN(C6COC6)CC5)cc4C)CC3)C(=O)N2)CC1] | LCMS-A-1 | 1.81 | 614 (M + H)+ |

The amine reagent used for Compound 976 (1-oxetan-3-yl-piperazine) was synthesized by the following method.

(Reaction 216-3)

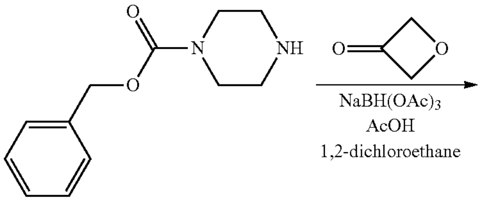

216c

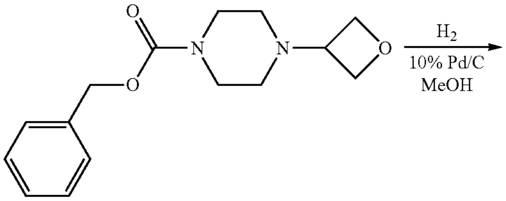

216d

-continued

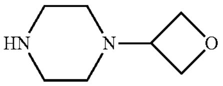

216e

1-Oxetan-3-yl-piperazine was synthesized by operations similar to those in Reaction 41-1 and Reaction 18-2 using appropriate reagents and starting material.

$^1$H-NMR (400 MHz, $CDCl_3$) δ 2.27 (4H, br s), 2.89-2.91 (4H, m), 3.42-3.48 (1H, m), 4.58-4.65 (4H, m).

Example 217

8-{2-[2-Methyl-4-(pyrrolidine-1-carbonyl)-phenyl]-ethanesulfonyl}-2-nonyl-1,3,8-triaza-spiro[4.5]dec-1-en-4-one (Compound 977)

(Reaction 217-1)

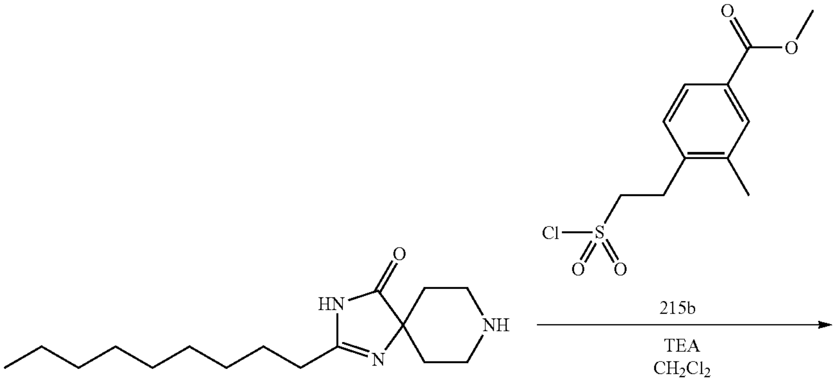

217a

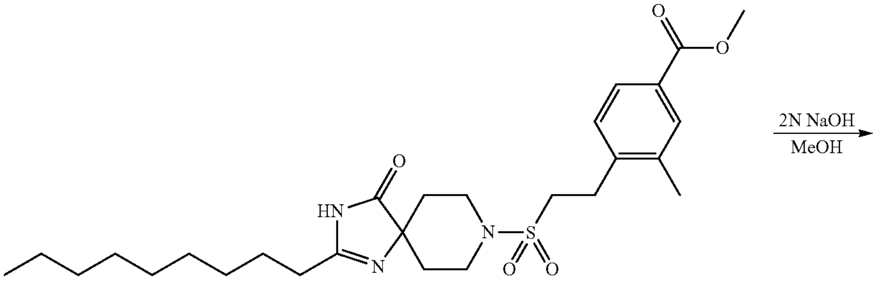

217b

-continued

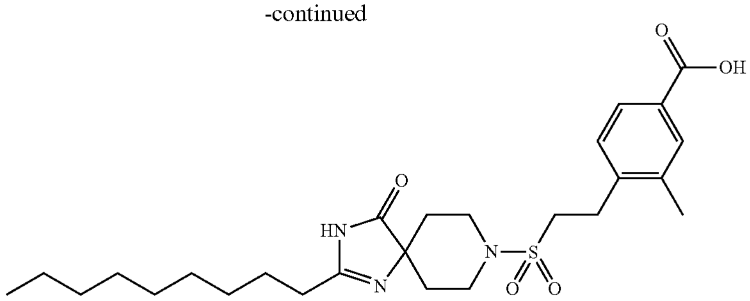

217c

3-Methyl-4-[2-(2-nonyl-4-oxo-1,3,8-triaza-spiro[4.5]dec-1-ene-8-sulfonyl)-ethyl]-benzoic acid was synthesized by operations similar to those in Reaction 5-4 and Reaction 95-18 using appropriate reagents and starting material.

MS (ESI) m/z=506 (M+H)+.

(Reaction 217-2)

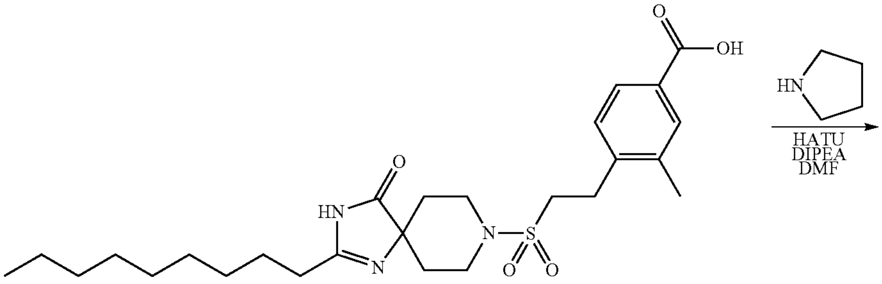

217c

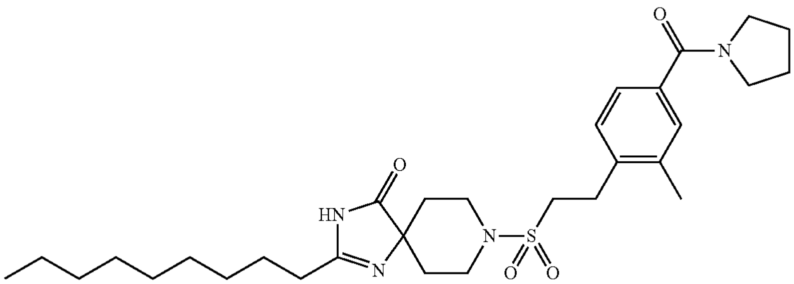

Compound 977

8-{2-[2-Methyl-4-(pyrrolidine-1-carbonyl)-phenyl]-ethanesulfonyl}-2-nonyl-1,3,8-triaza-spiro[4.5]dec-1-en-4-one was synthesized by operations similar to those in Reaction 10-14 using appropriate reagents and starting material.

MS (ESI) m/z=559 (M+H)+.

The example compounds shown below were synthesized by operations similar to those in Reaction 217-2 using appropriate reagents and starting materials.

Compounds 978 to 979
TABLE 141
| Compound | Structure | LCMS condition | Retention time (min) | MS (m/z) |
|---|---|---|---|---|
| 978 | 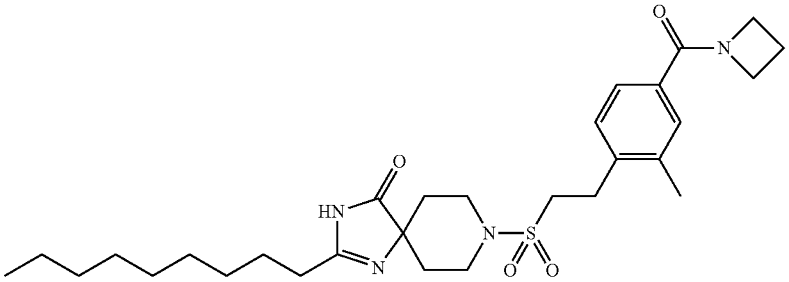 [SMILES: CCCCCCCCCC1=NC2(CCN(S(=O)(=O)CCc3ccc(C(=O)N4CCC4)cc3C)CC2)C(=O)N1] | LCMS-A-1 | 2.47 | 545 (M + H)+ |
| 979 | 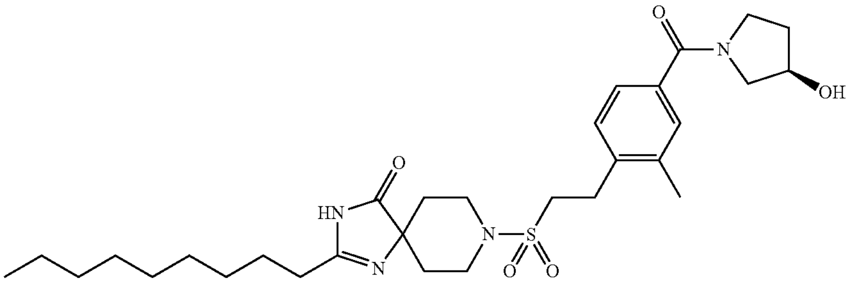 [SMILES: CCCCCCCCCC1=NC2(CCN(S(=O)(=O)CCc3ccc(C(=O)N4CC[C@@H](O)C4)cc3C)CC2)C(=O)N1] | LCMS-A-1 | 2.29 | 575 (M + H)+ |
Example 218
8-{2-[2,6-Dimethyl-4-(pyrrolidine-1-carbonyl)-phenyl]-ethanesulfonyl}-2-nonyl-1,3,8-triaza-spiro[4.5]dec-1-en-4-one (Compound 980)
(Reaction 218-1)
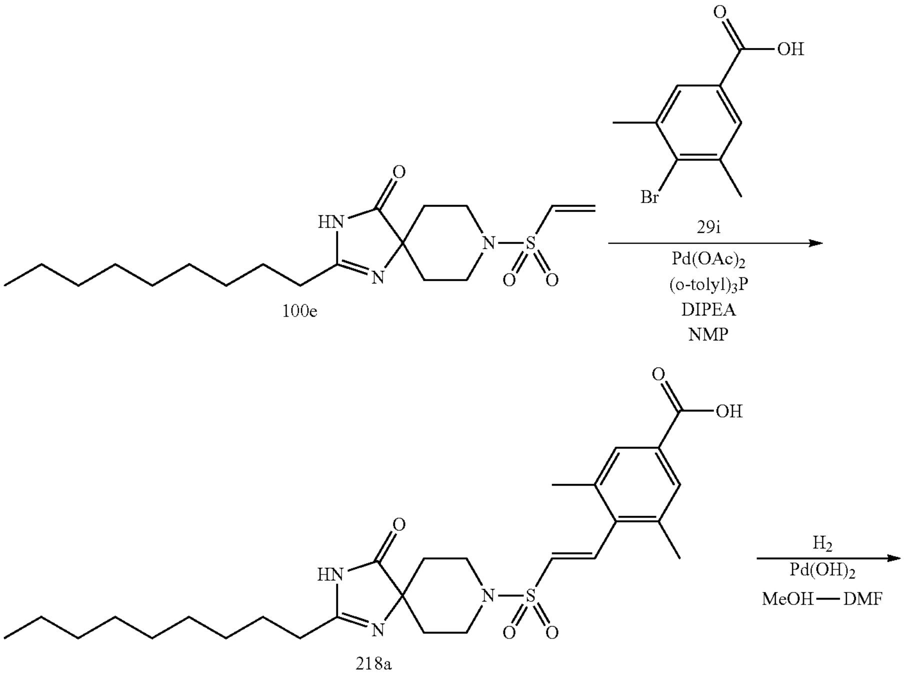

-continued

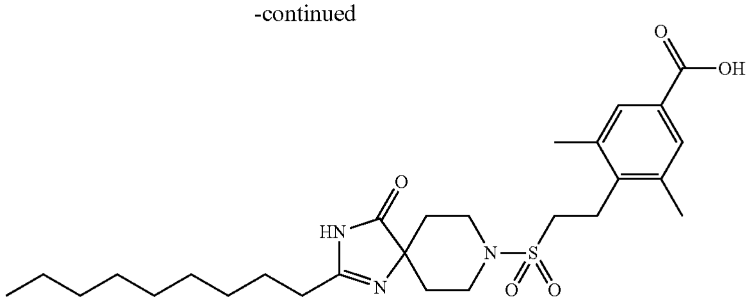

218b 3,5-Dimethyl-4-[2-(2-nonyl-4-oxo-1,3,8-triaza-spiro[4.5]dec-1-ene-8-sulfonyl)-ethyl]-benzoic acid was synthesized by operations similar to those in Reaction 26-1 and Reaction 122-2 using appropriate reagents and starting material.

MS (ESI) m/z=520 (M+H)+.

(Reaction 218-2)

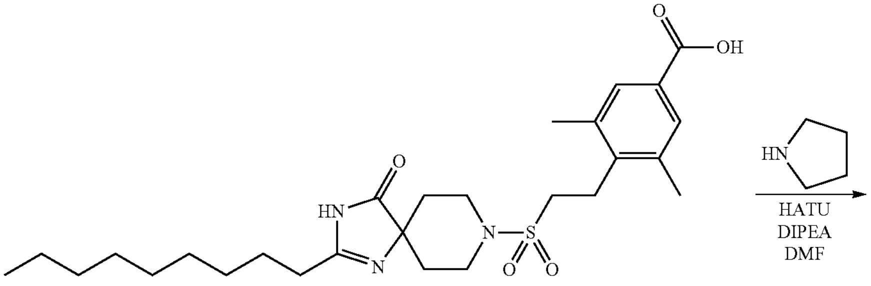

218b

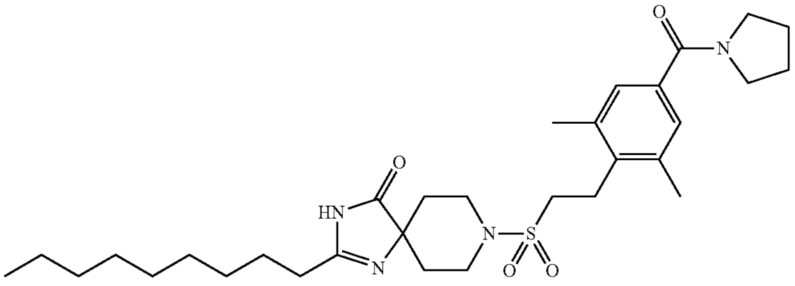

Compound 980

8-{2-[2,6-Dimethyl-4-(pyrrolidine-1-carbonyl)-phenyl]-ethanesulfonyl}-2-nonyl-1,3,8-triaza-spiro[4.5]dec-1-en-4-one was synthesized by operations similar to those in Reaction 10-14 using appropriate reagents and starting material.

MS (ESI) m/z=573 (M+H)+.

The example compounds shown below were synthesized by operations similar to those in Reaction 218-2 using appropriate reagents and starting materials.

Compounds 981 to 986
TABLE 142
| Compound | Structure | LCMS condition | Retention time (min) | MS (m/z) |
|---|---|---|---|---|
| 981 | 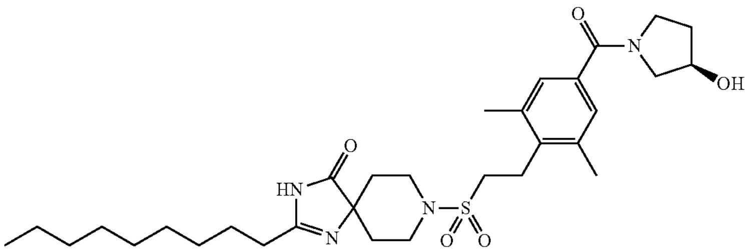 [SMILES: CCCCCCCCCC1=NC2(CCN(S(=O)(=O)CCc3c(C)cc(C(=O)N4CC[C@@H](O)C4)cc3C)CC2)C(=O)N1] | LCMS-F-1 | 1.03 | 589 (M + H)+ |
| 982 | 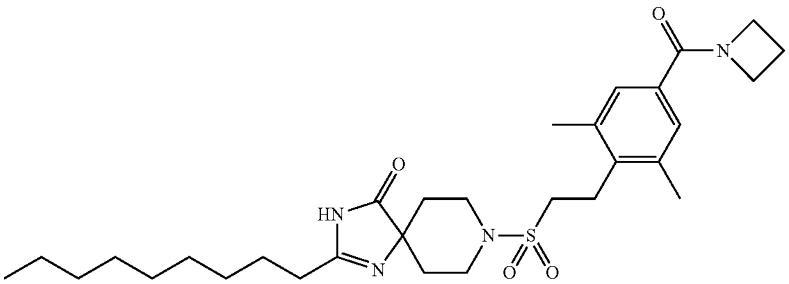 [SMILES: CCCCCCCCCC1=NC2(CCN(S(=O)(=O)CCc3c(C)cc(C(=O)N4CCC4)cc3C)CC2)C(=O)N1] | LCMS-F-1 | 1.09 | 559 (M + H)+ |
| 983 | 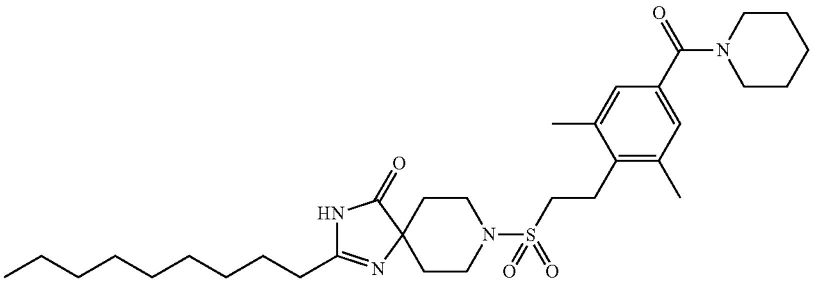 [SMILES: CCCCCCCCCC1=NC2(CCN(S(=O)(=O)CCc3c(C)cc(C(=O)N4CCCCC4)cc3C)CC2)C(=O)N1] | LCMS-F-1 | 1.13 | 587 (M + H)+ |
| 984 | 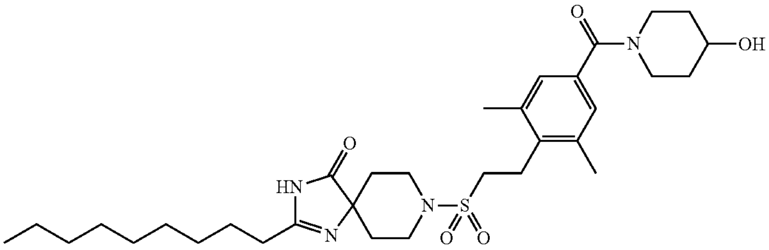 [SMILES: CCCCCCCCCC1=NC2(CCN(S(=O)(=O)CCc3c(C)cc(C(=O)N4CCC(O)CC4)cc3C)CC2)C(=O)N1] | LCMS-F-1 | 1.04 | 603 (M + H)+ |
| 985 | 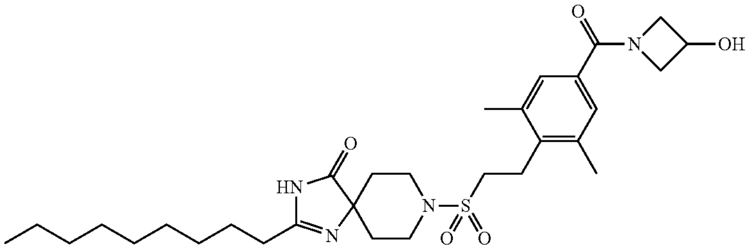 [SMILES: CCCCCCCCCC1=NC2(CCN(S(=O)(=O)CCc3c(C)cc(C(=O)N4CC(O)C4)cc3C)CC2)C(=O)N1] | LCMS-F-1 | 1.03 | 575 (M + H)+ |

TABLE 142-continued

| Compound | Structure | LCMS condition | Retention time (min) | MS (m/z) |
|---|---|---|---|---|
| 986 | 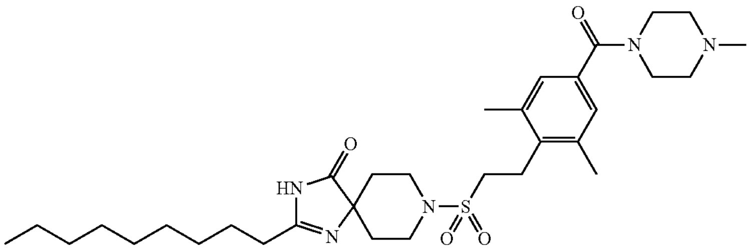 [SMILES: CCCCCCCCCC1=NC2(CCN(S(=O)(=O)CCc3c(C)cc(C(=O)N4CCN(C)CC4)cc3C)CC2)C(=O)N1] | LCMS-F-1 | 1.08 | 602 (M + H)+ |

Example 219

N,N-Dimethyl-2-(3-methyl-4-{(E)-2-[2-(4-methyl-cyclohexyl)-4-oxo-1,3,8-triaza-spiro[4.5]dec-1-ene-8-sulfonyl]-vinyl}-phenyl)-acetamide (Compound 987)

(Reaction 219-1)

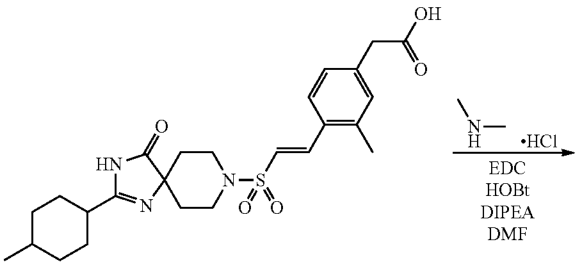

176c

-continued

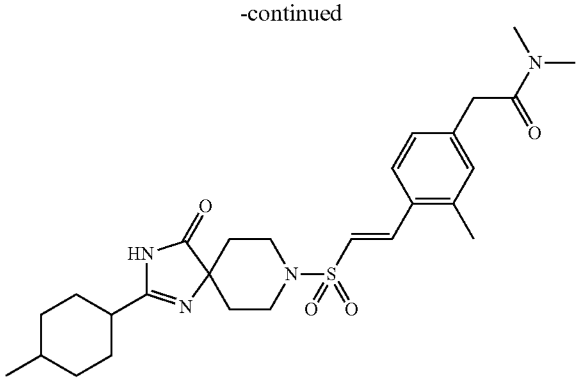

Compound 987

N,N-Dimethyl-2-(3-methyl-4-{(E)-2-[2-(4-methyl-cyclohexyl)-4-oxo-1,3,8-triaza-spiro[4.5]dec-1-ene-8-sulfonyl]-vinyl}-phenyl)-acetamide was synthesized by operations similar to those in Reaction 10-18 using appropriate reagents and starting material.

MS (ESI) m/z=515 (M+H)+.

The example compound shown below was synthesized by operations similar to those in Reaction 219-1 using appropriate reagents and starting material.

Compound 988

TABLE 143

| Compound | Structure | LCMS condition | Retention time (min) | MS (m/z) |
|---|---|---|---|---|
| 988 | 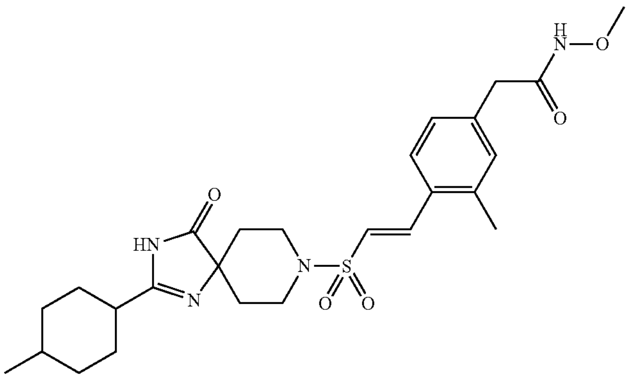 | LCMS-C-1 | 2.47 | 517 (M + H)+ |

Example 220

8-{(E)-2-[4-(4-Hydroxy-4-methyl-piperidine-1-carbonyl)-2,6-dimethyl-phenyl]-ethenesulfonyl}-2-[4-(3,3,3-trifluoro-propyl)-cyclohexyl]-1,3,8-triaza-spiro[4.5]dec-1-en-4-one (Compound 989)

(Reaction 220-1)

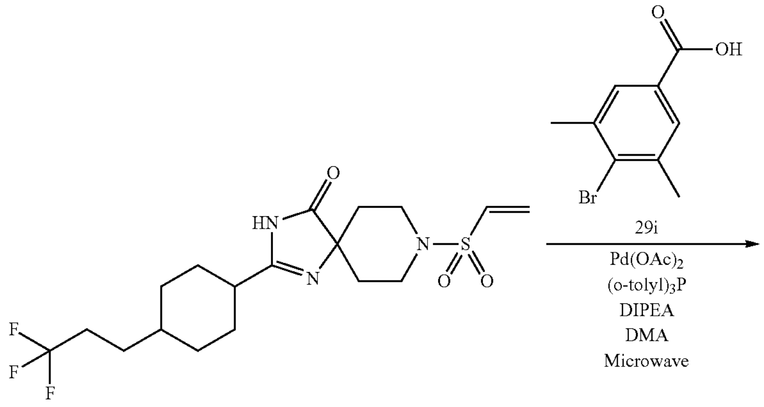

101j

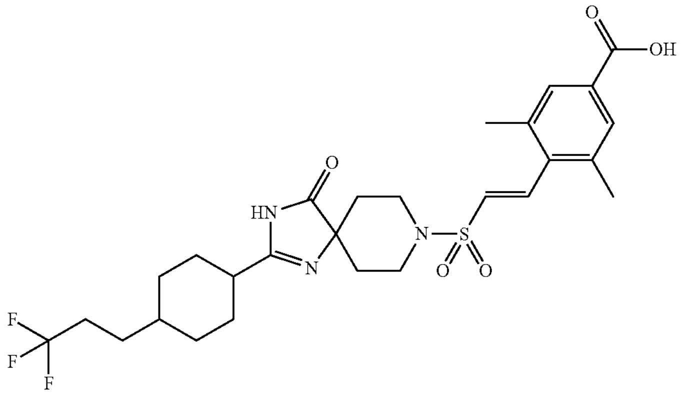

220a 3,5-Dimethyl-4-((E)-2-{4-oxo-2-[4-(3,3,3-trifluoro-propyl)-cyclohexyl]-1,3,8-triaza-spiro[4.5]dec-1-ene-8-sulfonyl}-vinyl)-benzoic acid was synthesized by operations similar to those in Reaction 25-2 using appropriate reagents and starting material.

MS (ESI) m/z=570 (M+H)+.

(Reaction 220-2)

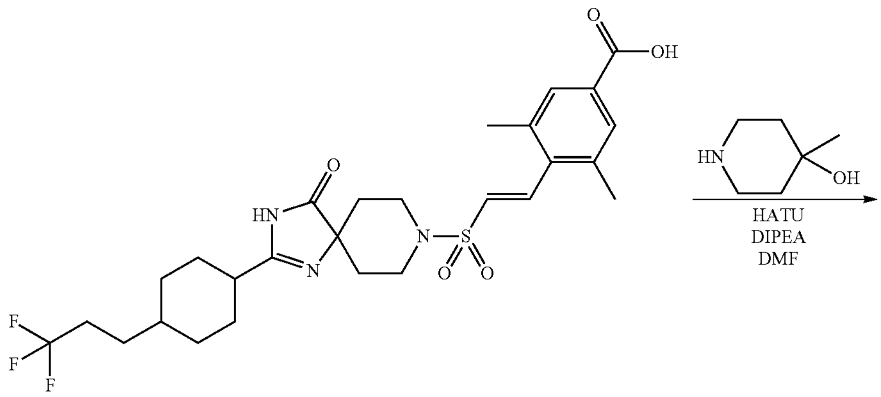

220a

-continued

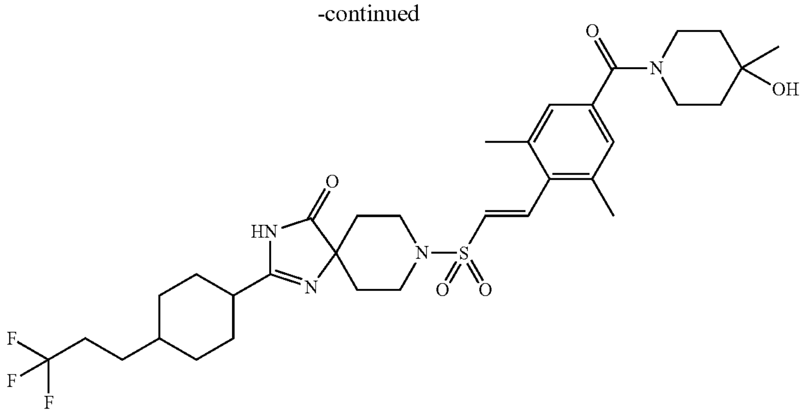

Compound 989

8-{(E)-2-[4-(4-Hydroxy-4-methyl-piperidine-1-carbonyl)-2,6-dimethyl-phenyl]-ethenesulfonyl}-2-[4-(3,3,3-trifluoro-propyl)-cyclohexyl]-1,3,8-triaza-spiro[4.5]dec-1-en-4-one was synthesized by operations similar to those in Reaction 10-14 using appropriate reagents and starting material.

MS (ESI) m/z=667 (M+H)+.

The example compounds shown below were synthesized by operations similar to those in Reaction 220-2 using appropriate reagents and starting materials.

Compounds 990 to 994

TABLE 144

| Compound | Structure | LCMS condition | Retention time (min) | MS (m/z) |
|---|---|---|---|---|
| 990 | 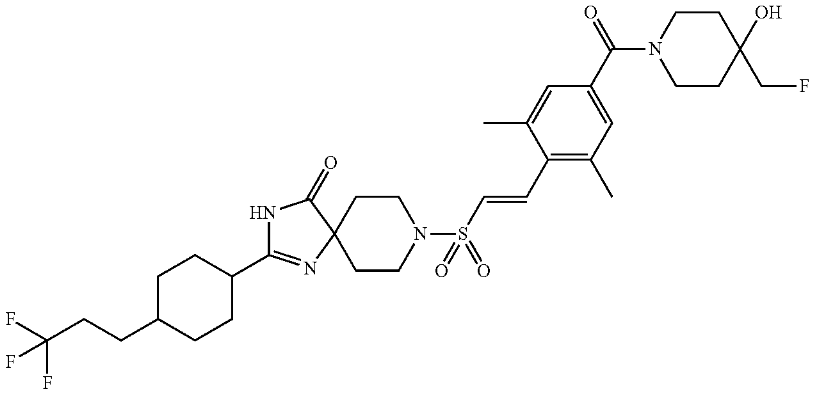 [SMILES: Cc1cc(C(=O)N2CCC(O)(CF)CC2)cc(C)c1/C=C/S(=O)(=O)N1CCC2(CC1)N=C(C1CCC(CCC(F)(F)F)CC1)NC2=O] | LCMS-D-1 | 2.28 | 685 (M + H)+ |
| 991 | 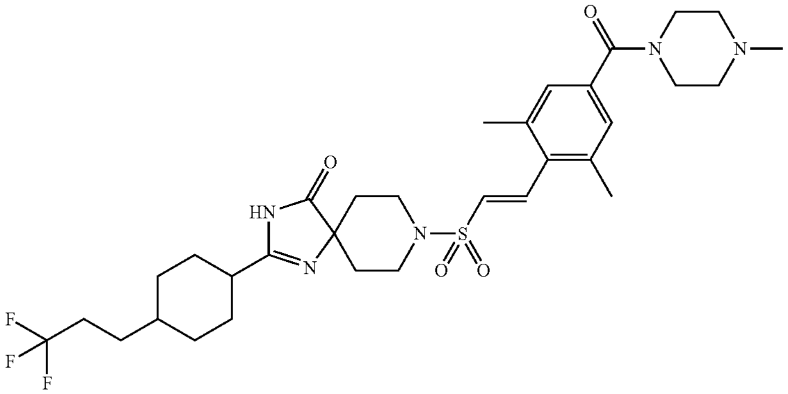 [SMILES: Cc1cc(C(=O)N2CCN(C)CC2)cc(C)c1/C=C/S(=O)(=O)N1CCC2(CC1)N=C(C1CCC(CCC(F)(F)F)CC1)NC2=O] | LCMS-D-1 | 1.60 | 652 (M + H)+ |

TABLE 144-continued

| Compound | Structure | LCMS condition | Retention time (min) | MS (m/z) |
| --- | --- | --- | --- | --- |
| 992 | 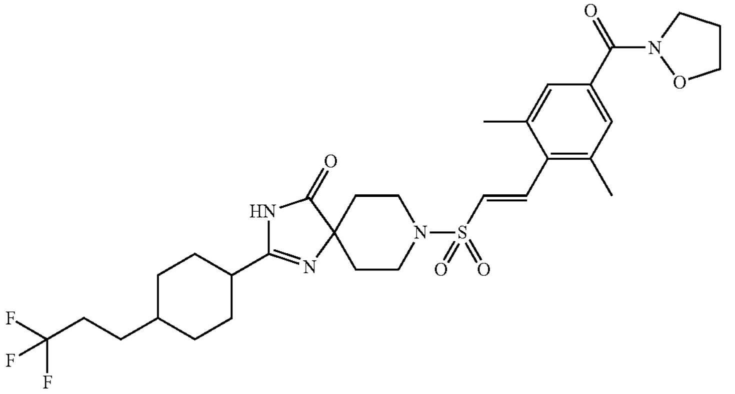 [SMILES: Cc1cc(C(=O)N2CCCO2)cc(C)c1/C=C/S(=O)(=O)N1CCC2(CC1)N=C(C1CCC(CCC(F)(F)F)CC1)NC2=O] | LCMS-D-1 | 2.57 | 625 (M + H)+ |
| 993 | 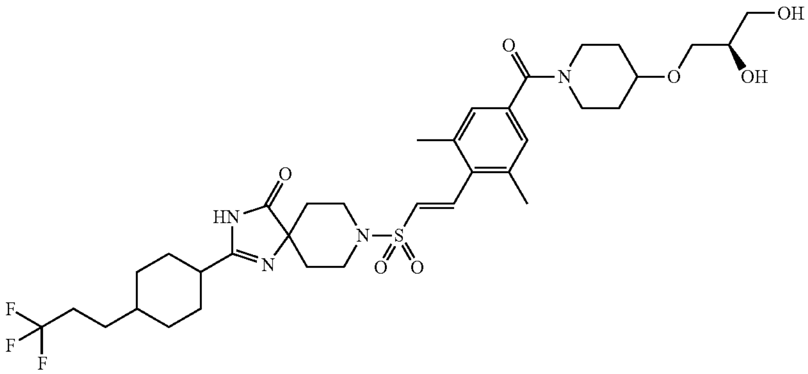 [SMILES: Cc1cc(C(=O)N2CCC(OC[C@H](O)CO)CC2)cc(C)c1/C=C/S(=O)(=O)N1CCC2(CC1)N=C(C1CCC(CCC(F)(F)F)CC1)NC2=O] | LCMS-D-1 | 1.88 | 727 (M + H)+ |
| 994 | 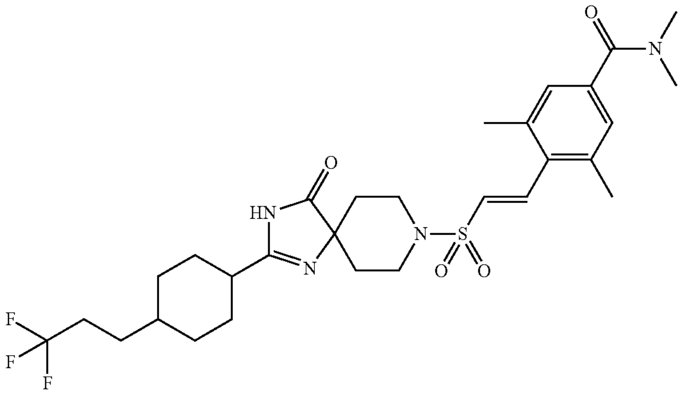 [SMILES: Cc1cc(C(=O)N(C)C)cc(C)c1/C=C/S(=O)(=O)N1CCC2(CC1)N=C(C1CCC(CCC(F)(F)F)CC1)NC2=O] | LCMS-D-1 | 1.87 | 597 (M + H)+ |

The amine reagent used for Compound 993 ((R)-3-(piperidin-4-yloxy)-propane-1,2-diol hydrochloride) was synthesized by the following method.

(Reaction 220-3)

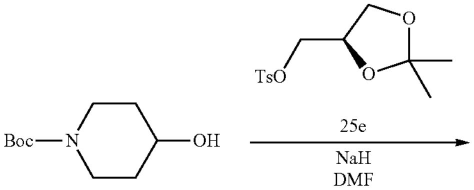

220b

-continued

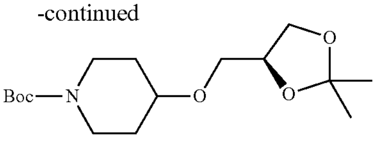

220c 4-((S)-2,2-Dimethyl-[1,3]dioxolan-4-ylmethoxy)-piperidine-1-carboxylic acid tert-butyl ester was synthesized by operations similar to those in Reaction 25-3 using appropriate reagents and starting material.

$^1$H-NMR ($CDCl_3$) δ 1.35 (s, 3H), 1.41 (s, 3H), 1.44 (s, 9H), 1.48-1.53 (m, 2H), 1.75-1.87 (m, 2H), 2.95-3.15 (m, 2H), 3.39-3.50 (m, 2H), 3.51-3.58 (m, 2H), 3.67-3.80 (m, 2H), 4.00-4.09 (m, 1H), 4.17-4.32 (m, 1H).

(Reaction 220-4)

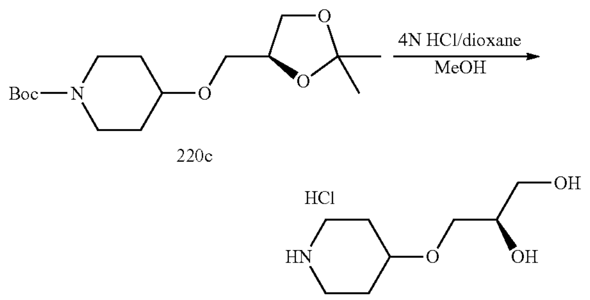

220c

220d (R)-3-(Piperidin-4-yloxy)-propane-1,2-diol hydrochloride was synthesized by operations similar to those in Reaction 5-3 using appropriate reagents and starting material. This was used in the next reaction without purification.

Example 221

8-{2-[2,6-Dimethyl-4-(4-methyl-piperazine-1-carbonyl)-phenyl]-ethanesulfonyl}-2-[4-(3,3,3-trifluoro-propyl)-cyclohexyl]-1,3,8-triaza-spiro[4.5]dec-1-en-4-one (Compound 995)

(Reaction 221-1)

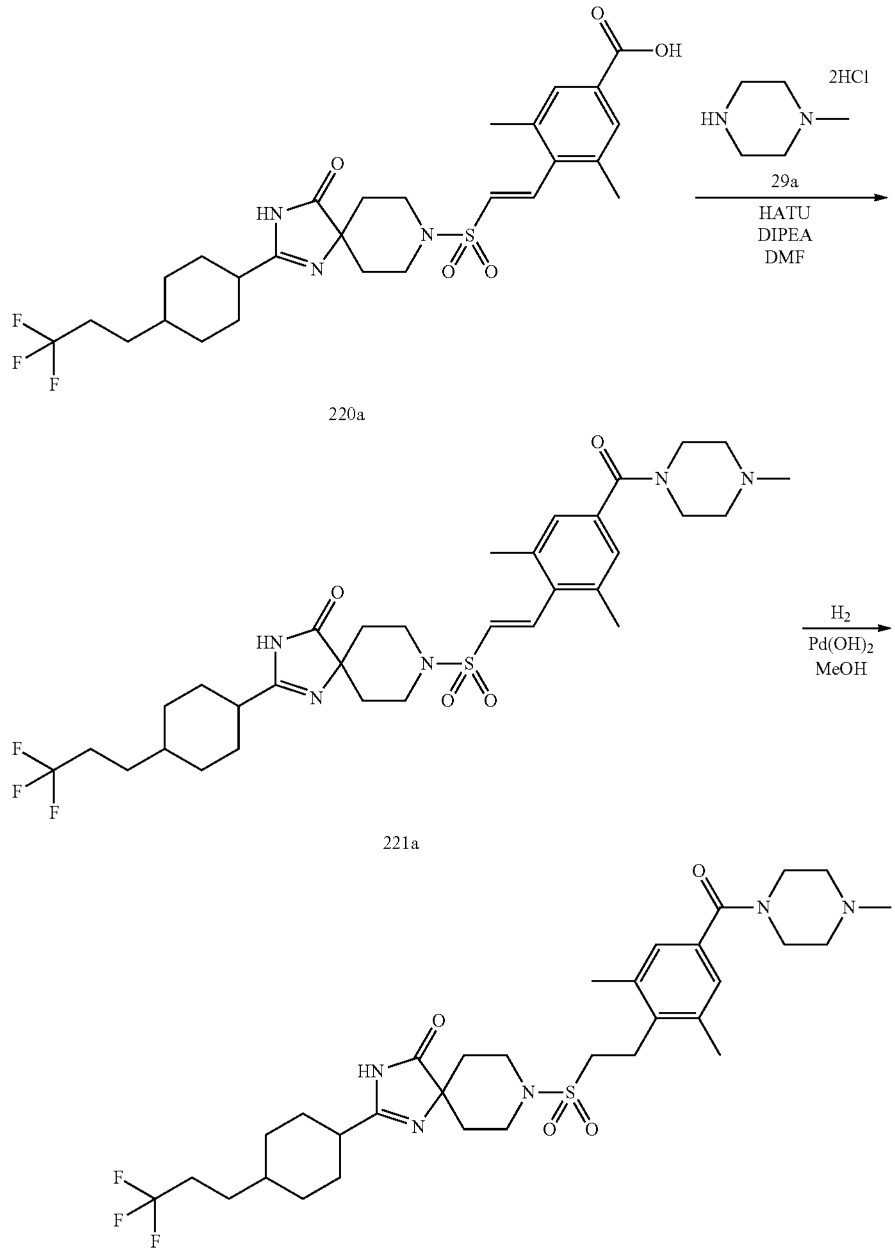

220a

221a

Compound 995

8-{2-[2,6-Dimethyl-4-(4-methyl-piperazine-1-carbonyl)-phenyl]-ethanesulfonyl}-2-[4-(3,3,3-trifluoro-propyl)-cyclohexyl]-1,3,8-triaza-spiro[4.5]dec-1-en-4-one was synthesized by operations similar to those in Reaction 10-14 and Reaction 122-2 using appropriate reagents and starting material.

MS (ESI) m/z=654 (M+H)+.

Example 222

3,5-Dimethyl-4-((E)-2-{4-oxo-2-[4-(3,3,3-trifluoro-propyl)-cyclohexyl]-1,3,8-triaza-spiro[4.5]dec-1-ene-8-sulfonyl}-vinyl)-benzoic acid hydrazide (Compound 996)

(Reaction 222-1)

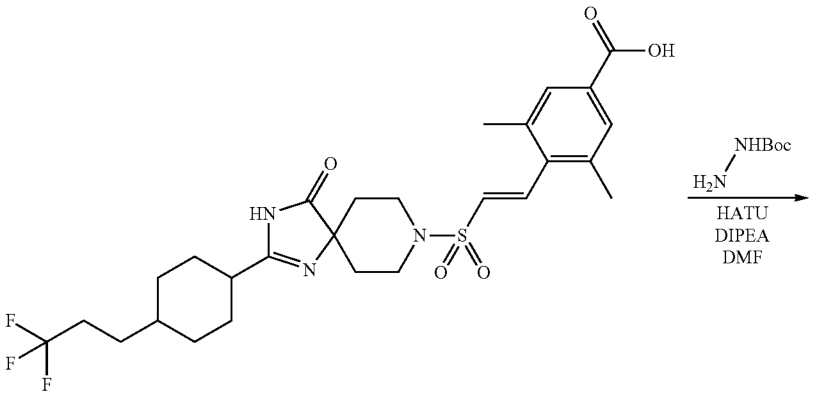

220a

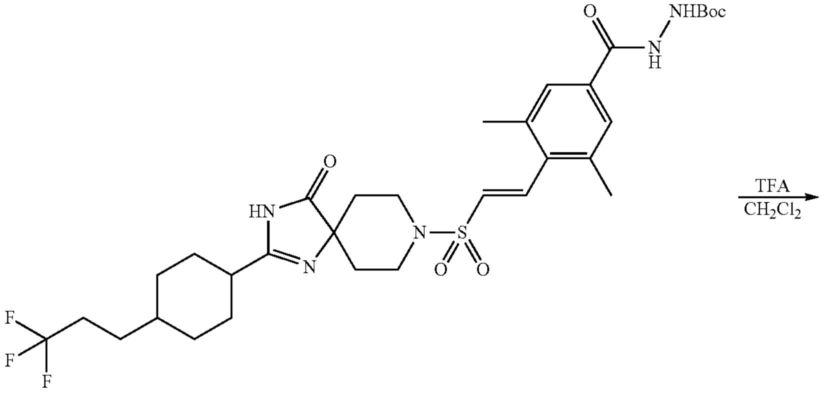

222a

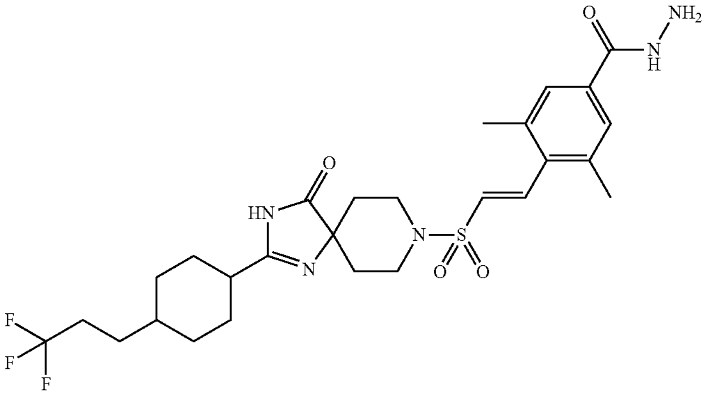

Compound 996

3,5-Dimethyl-4-((E)-2-{4-oxo-2-[4-(3,3,3-trifluoro-propyl)-cyclohexyl]-1,3,8-triaza-spiro[4.5]dec-1-ene-8-sulfonyl}-vinyl)-benzoic acid hydrazide was synthesized by operations similar to those in Reaction 10-14 and Reaction 4-1 using appropriate reagents and starting material.

MS (ESI) m/z=584 (M+H)+.

The example compound shown below was synthesized by operations similar to those in Reaction 222-1 using appropriate reagents and starting material.

Compound 997

TABLE 145

| Compound | Structure | LCMS condition | Retention time (min) | MS (m/z) |
|---|---|---|---|---|
| 997 | 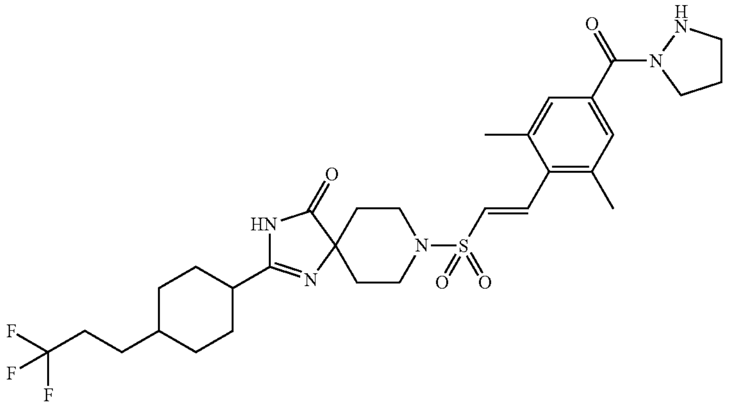 [SMILES: Cc1cc(C(=O)N2CCCN2)cc(C)c1/C=C/S(=O)(=O)N1CCC2(CC1)N=C(C1CCC(CCC(F)(F)F)CC1)NC2=O] | LCMS-D-1 | 2.12 | 624 (M + H)+ |

Example 223

N-Methoxy-3,5,N-trimethyl-4-{(E)-2-[2-(4-methyl-cyclohexyl)-4-oxo-1,3,8-triaza-spiro[4.5]dec-1-ene-8-sulfonyl]-vinyl}-benzamide (Compound 998)

(Reaction 223-1)

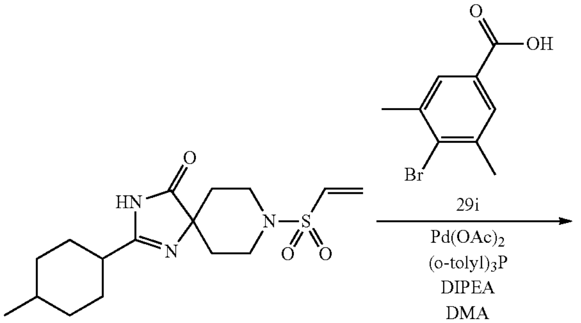

27b

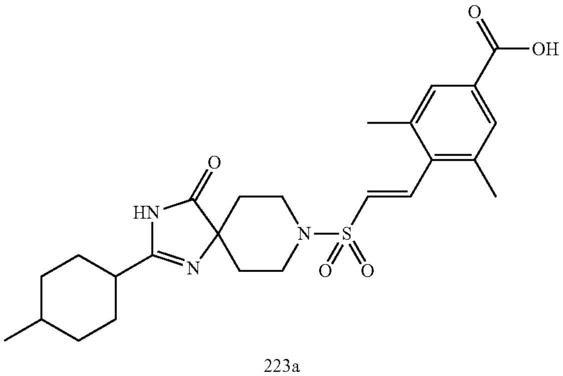

223a 3,5-Dimethyl-4-{(E)-2-[2-(4-methyl-cyclohexyl)-4-oxo-1,3,8-triaza-spiro[4.5]dec-1-ene-8-sulfonyl]-vinyl}-benzoic acid was synthesized by operations similar to those in Reaction 26-1 using appropriate reagents and starting material.

MS (ESI) m/z=488 (M+H)+.

(Reaction 223-2)

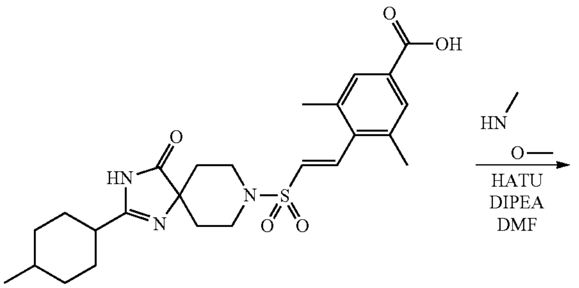

223a

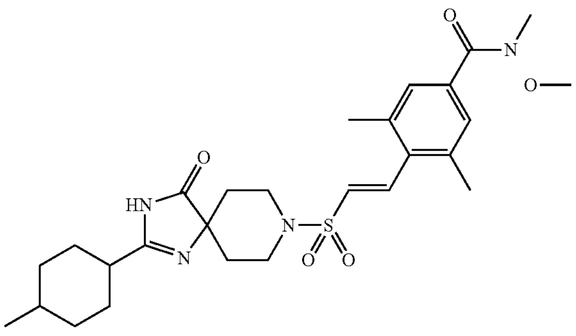

Compound 998

N-Methoxy-3,5,N-trimethyl-4-{(E)-2-[2-(4-methyl-cyclohexyl)-4-oxo-1,3,8-triaza-spiro[4.5]dec-1-ene-8-sulfonyl]-vinyl}-benzamide was synthesized by operations similar to those in Reaction 10-14 using appropriate reagents and starting material.

MS (ESI) m/z=531 (M+H)+.

The example compounds shown below were synthesized by operations similar to those in Reaction 223-2 using appropriate reagents and starting materials.

Compounds 999 to 1003

TABLE 146

| Compound | Structure | LCMS condition | Retention time (min) | MS (m/z) |
|---|---|---|---|---|
| 999 | 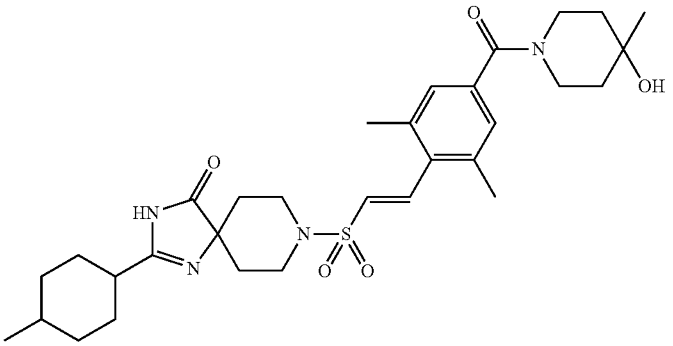 | LCMS-D-1 | 1.99 | 585 (M + H)+ |
| 1000 | 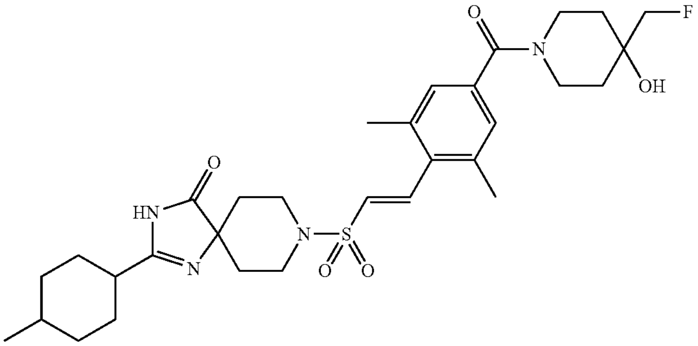 [SMILES: Cc1cc(C(=O)N2CCC(O)(CF)CC2)cc(C)c1/C=C/S(=O)(=O)N1CCC2(CC1)N=C(C1CCC(C)CC1)NC2=O] | LCMS-D-1 | 1.96 | 603 (M + H)+ |
| 1001 | 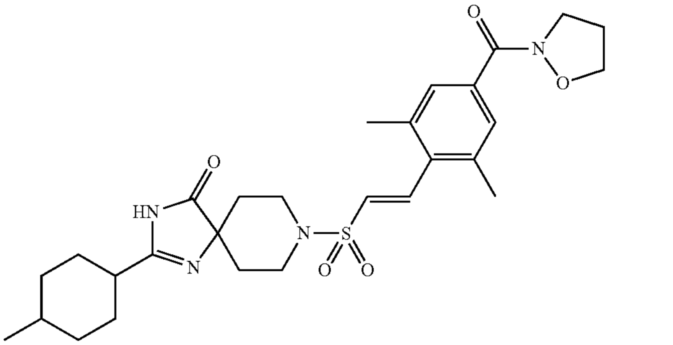 [SMILES: Cc1cc(C(=O)N2CCCO2)cc(C)c1/C=C/S(=O)(=O)N1CCC2(CC1)N=C(C1CCC(C)CC1)NC2=O] | LCMS-D-1 | 2.48 | 543 (M + H)+ |
| 1002 | 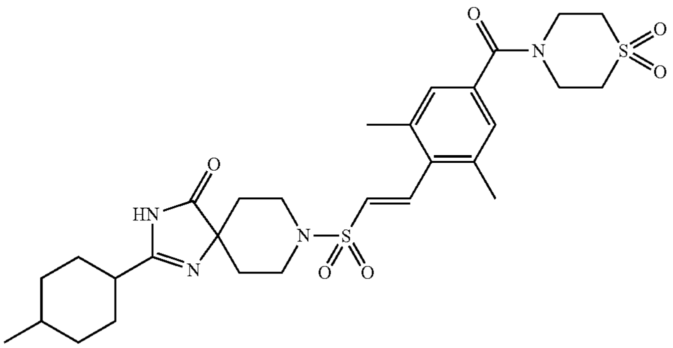 [SMILES: Cc1cc(C(=O)N2CCS(=O)(=O)CC2)cc(C)c1/C=C/S(=O)(=O)N1CCC2(CC1)N=C(C1CCC(C)CC1)NC2=O] | LCMS-D-1 | 1.67 | 605 (M + H)+ |

TABLE 146-continued

| Compound | Structure | LCMS condition | Retention time (min) | MS (m/z) |
| --- | --- | --- | --- | --- |
| 1003 | 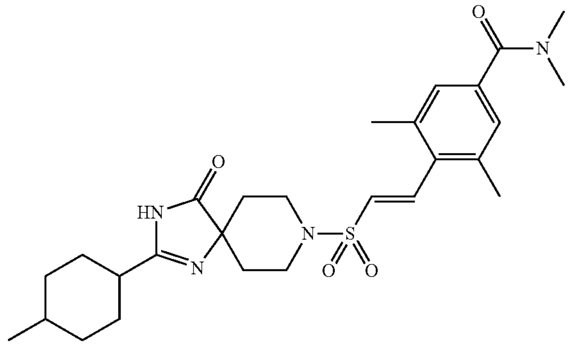 | LCMS-D-1 | 1.91 | 515 (M + H)+ |

Example 224

8-{2-[2,6-Dimethyl-4-(pyrazolidine-1-carbonyl)-phenyl]-ethanesulfonyl}-2-(4-methyl-cyclohexyl)-1,3,8-triaza-spiro[4.5]dec-1-en-4-one (Reaction 224-1)

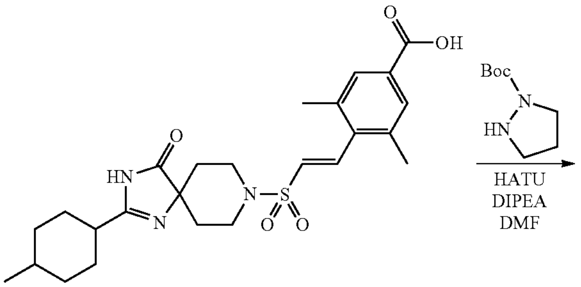

223a

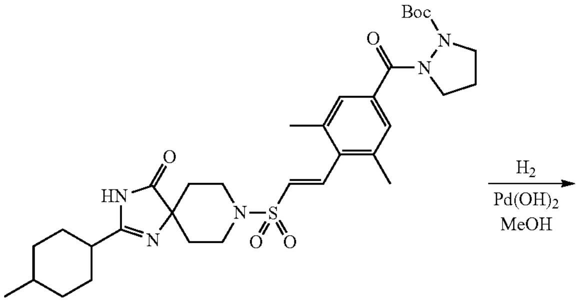

224a

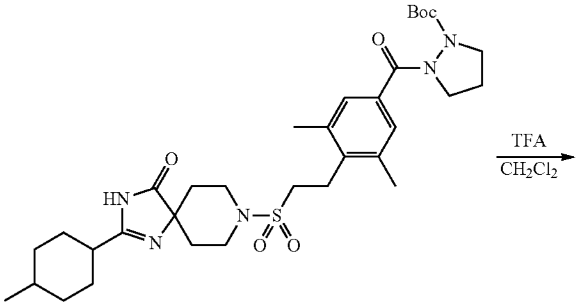

224b

-continued

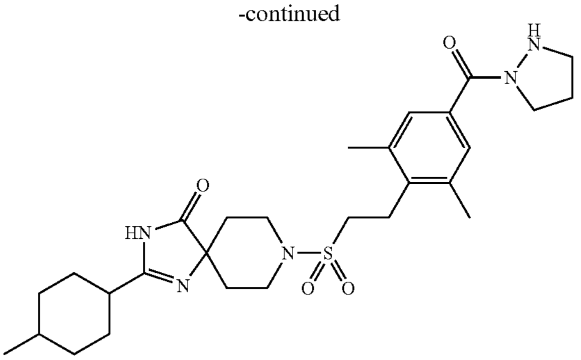

224c

8-{2-[2,6-Dimethyl-4-(pyrazolidine-1-carbonyl)-phenyl]-ethanesulfonyl}-2-(4-methyl-cyclohexyl)-1,3,8-triaza-spiro[4.5]dec-1-en-4-one was synthesized by operations similar to those in Reaction 10-14, Reaction 122-2 and Reaction 4-1 using appropriate reagents and starting material.

MS (ESI) m/z=544 (M+H)+.

Example 225

8-{(E)-2-[2,6-Dimethyl-4-(pyrazolidine-1-carbonyl)-phenyl]-ethenesulfonyl}-2-(4-methyl-cyclohexyl)-1,3,8-triaza-spiro[4.5]dec-1-en-4-one (Reaction 225-1)

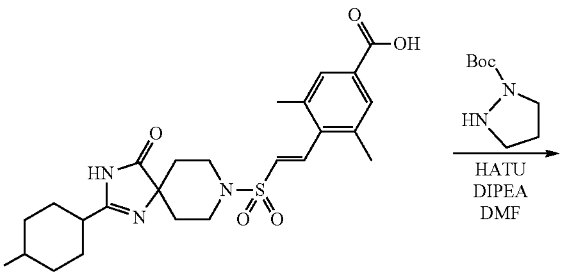

223a

-continued

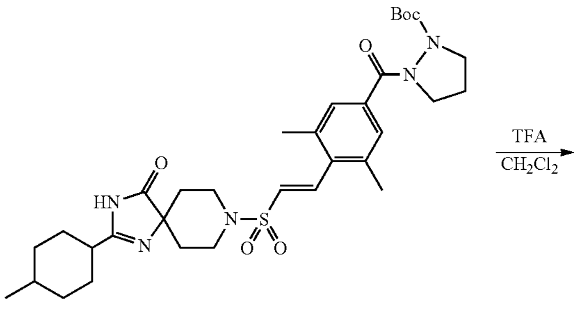

225a

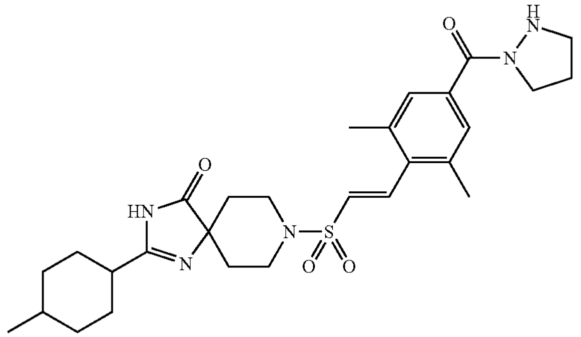

225b

8-{(E)-2-[2,6-Dimethyl-4-(pyrazolidine-1-carbonyl)-phenyl]-ethenesulfonyl}-2-(4-methyl-cyclohexyl)-1,3,8-triaza-spiro[4.5]dec-1-en-4-one was synthesized by operations similar to those in Reaction 10-14 and Reaction 4-1 using appropriate reagents and starting material.

MS (ESI) m/z=542 (M+H)+.

Example 226

2-Cyclohexyl-8-{(E)-2-[4-(4-hydroxy-4-trifluoromethyl-piperidine-1-carbonyl)-2,6-dimethyl-phenyl]-ethenesulfonyl}-1,3,8-triaza-spiro[4.5]dec-1-en-4-one (Compound 1006)

(Reaction 226-1)

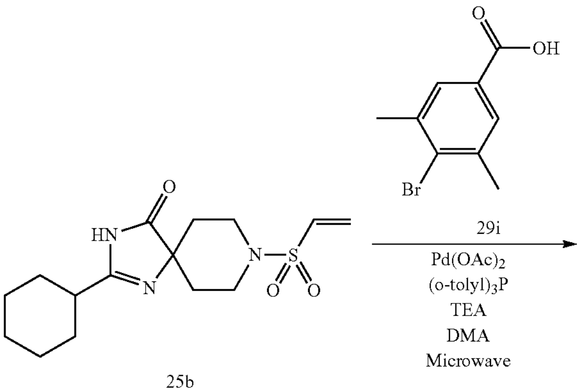

25b

-continued

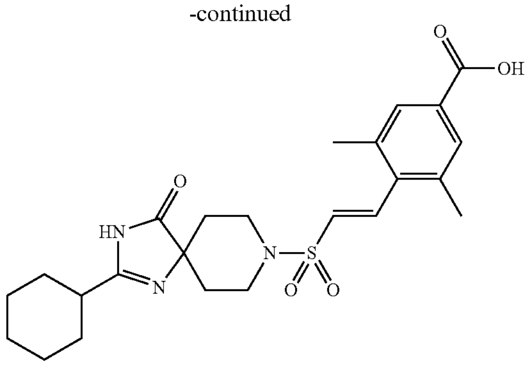

226a

4-[(E)-2-(2-Cyclohexyl-4-oxo-1,3,8-triaza-spiro[4.5]dec-1-ene-8-sulfonyl)-vinyl]-3,5-dimethyl-benzoic acid was synthesized by operations similar to those in Reaction 25-2 using appropriate reagents and starting material.

MS (ESI) m/z=474 (M+H)+.

(Reaction 226-2)

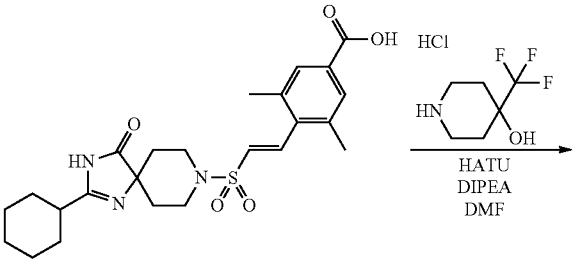

226a

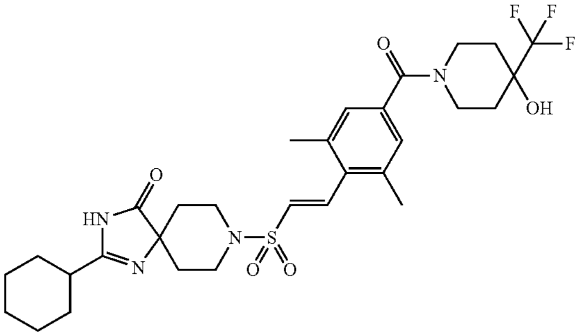

Compound 1006

2-Cyclohexyl-8-{(E)-2-[4-(4-hydroxy-4-trifluoromethyl-piperidine-1-carbonyl)-2,6-dimethyl-phenyl]-ethenesulfonyl}-1,3,8-triaza-spiro[4.5]dec-1-en-4-one was synthesized by operations similar to those in Reaction 10-14 using appropriate reagents and starting material.

MS (ESI) m/z=625 (M+H)+.

Example 227

2-Cyclohexyl-8-{(E)-2-[2,6-dimethyl-4-(2-oxo-oxazolidine-3-carbonyl)-phenyl]-ethenesulfonyl}-1,3,8-triaza-spiro[4.5]dec-1-en-4-one (Compound 1007)

(Reaction 227-1)

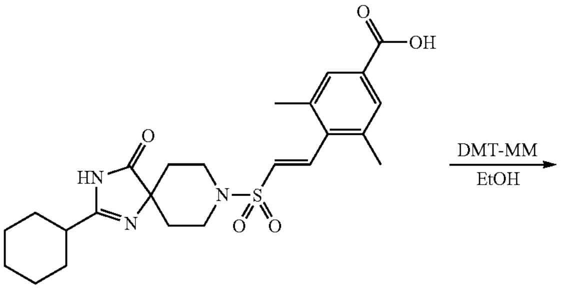

226a

-continued

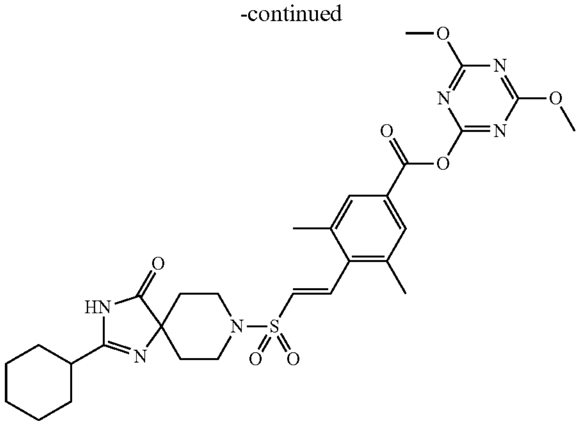

227a

DMT-MM (181 mg, 0.50 mmol) was added to a solution of 4-[(E)-2-(2-cyclohexyl-4-oxo-1,3,8-triaza-spiro[4.5]dec-1-ene-8-sulfonyl)-vinyl]-3,5-dimethyl-benzoic acid (160 mg, 0.33 mmol) in anhydrous ethanol (3.3 ml), and the mixture was stirred at room temperature for 15 hours. The mixture was concentrated under reduced pressure, and the resulting residue was then purified by silica gel column chromatography (dichloromethane-methanol) to give 4-[(E)-2-(2-cyclohexyl-4-oxo-1,3,8-triaza-spiro[4.5]dec-1-ene-8-sulfonyl)-vinyl]-3,5-dimethyl-benzoic acid 4,6-dimethoxy-[1,3,5]triazin-2-yl ester (109 mg, 53%).

MS (ESI) m/z=613 (M+H)+.

(Reaction 227-2)

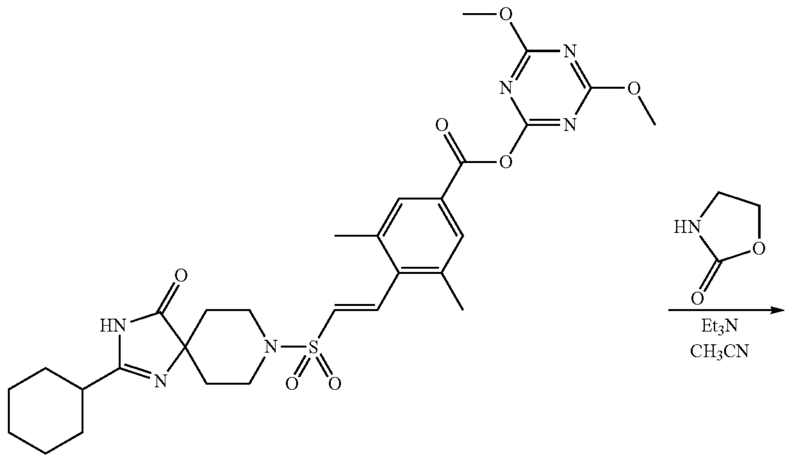

227a

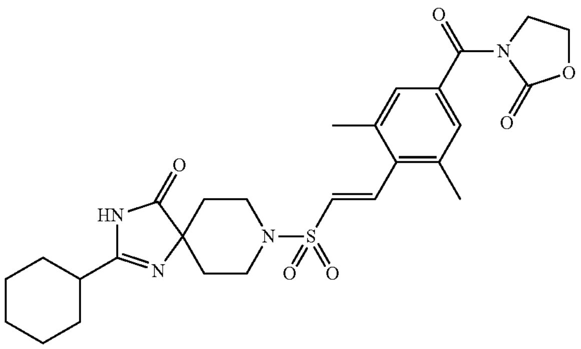

Compound 1007

Oxazolidin-2-one (47 mg, 0.53 mmol) was added to a solution of 4-[(E)-2-(2-cyclohexyl-4-oxo-1,3,8-triaza-spiro[4.5]dec-1-ene-8-sulfonyl)-vinyl]-3,5-dimethyl-benzoic acid 4,6-dimethoxy-[1,3,5]triazin-2-yl ester (109 mg, 0.17 mmol) and triethylamine (0.12 ml, 0.88 mmol) in anhydrous acetonitrile (1 ml), and the mixture was heated with stirring at 80° C. for 15 hours. The mixture was cooled and water was then added, followed by extraction with ethyl acetate. The organic layer was washed with water and saturated brine, and then dried over anhydrous magnesium sulfate and concentrated under reduced pressure. The resulting residue was purified by silica gel column chromatography (dichloromethane-methanol) to give 2-cyclohexyl-8-{(E)-2-[2,6-dimethyl-4-(2-oxo-oxazolidine-3-carbonyl)-phenyl]-ethenesulfonyl}-1,3,8-triaza-spiro[4.5]dec-1-en-4-one (31 mg, 32%).

MS (ESI) m/z=543 (M+H)+.

Example 228

2-(4-Butyl-cyclohexyl)-8-((E)-2-{4-[4-(2-hydroxy-ethoxy)-piperidine-1-carbonyl]-2,6-dimethyl-phenyl}-ethenesulfonyl)-1,3,8-triaza-spiro[4.5]dec-1-en-4-one (Compound 1008)

(Reaction 228-1)

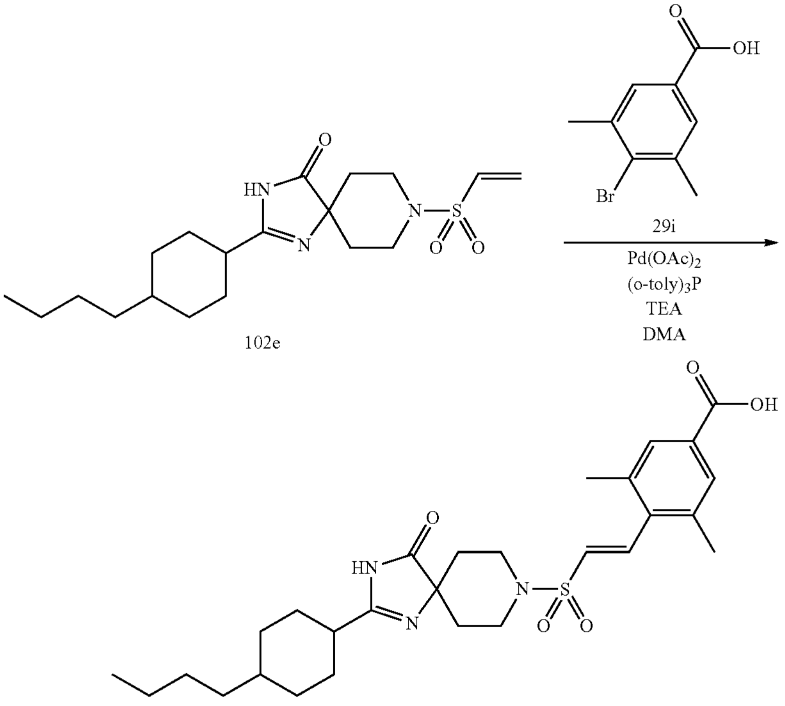

102e

228a

4-{(E)-2-[2-(4-Butyl-cyclohexyl)-4-oxo-1,3,8-triaza-spiro[4.5]dec-1-ene-8-sulfonyl]-vinyl}-3,5-dimethyl-benzoic acid was synthesized by operations similar to those in Reaction 26-1 using appropriate reagents and starting material.

MS (ESI) m/z=530 (M+H)+.

(Reaction 228-2)

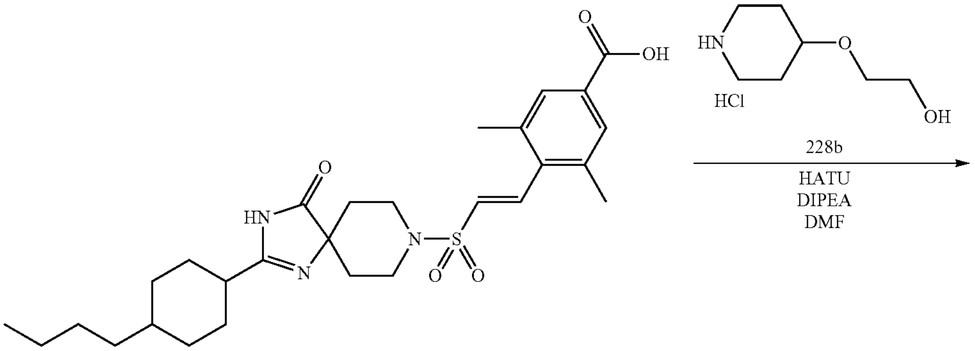

228a

-continued

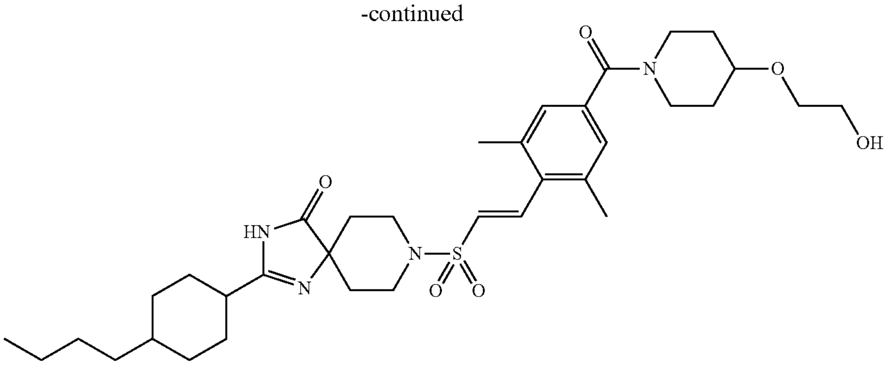

Compound 1008

2-(4-Butyl-cyclohexyl)-8-((E)-2-{4-[4-(2-hydroxy-ethoxy)-piperidine-1-carbonyl]-2,6-dimethyl-phenyl}-ethenesulfonyl)-1,3,8-triaza-spiro[4.5]dec-1-en-4-one was synthesized by operations similar to those in Reaction 10-14 using appropriate reagents and starting material.

MS (ESI) m/z=657 (M+H)+.

The amine reagent used for Compound 1008 (2-(piperidin-4-yloxy)-ethanol hydrochloride) was synthesized by the following method.

(Reaction 228-3)

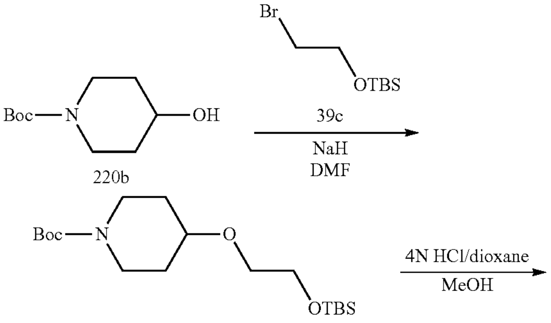

220b

228c

-continued

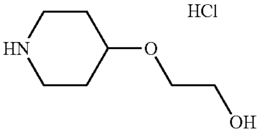

228b 2-(Piperidin-4-yloxy)-ethanol hydrochloride was synthesized by operations similar to those in Reaction 20-2 and Reaction 5-3 using appropriate reagents and starting material.

$^1$H-NMR (300 MHz, DMSO-d6) δ 1.50-1.62 (m, 2H), 1.80-1.89 (m, 2H), 2.87-2.93 (m, 2H), 3.10-3.16 (m, 2H), 3.69-3.76 (m, 1H), 5.00 (s, 1H), 8.74-8.90 (m, 2H).

The example compound shown below was synthesized by operations similar to those in Reaction 228-2 using appropriate reagents and starting material.

Compound 1009

TABLE 147

| Compound | Structure | LCMS condition | Retention time (min) | MS (m/z) |
| --- | --- | --- | --- | --- |
| 1009 | 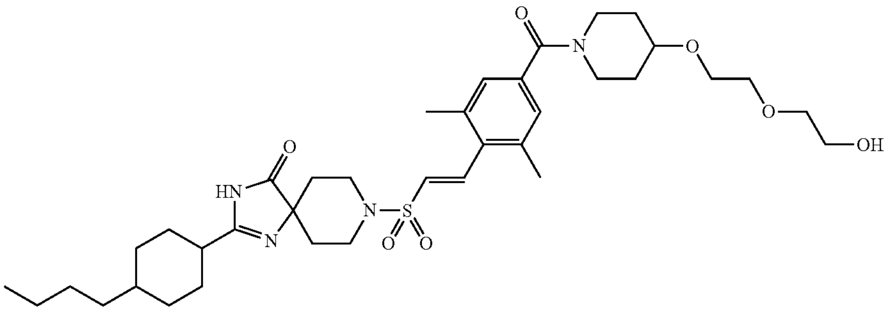 [SMILES: CCCCC1CCC(C2=NC3(CCN(S(=O)(=O)/C=C/c4c(C)cc(C(=O)N5CCC(OCCOCCO)CC5)cc4C)CC3)C(=O)N2)CC1] | LCMS-D-1 | 2.42 | 701 (M + H)+ |

The amine reagent used for Compound 1009 (2-[2-(piperidin-4-yloxy)-ethoxy]-ethanol hydrochloride) was synthesized by the following method.

(Reaction 228-4)

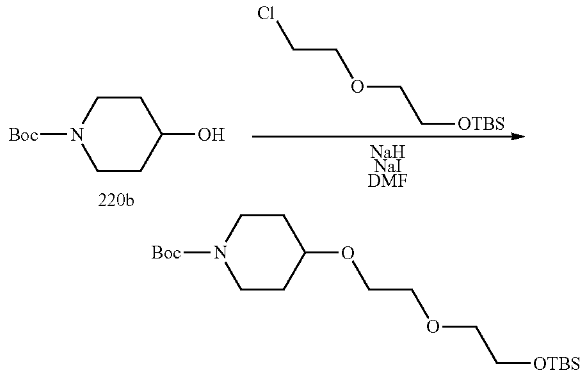

220b

228d

4-{2-[2-(tert-Butyl-dimethyl-silanyloxy)-ethoxy]-ethoxy}-piperidine-1-carboxylic acid tert-butyl ester was synthesized by operations similar to those in Reaction 20-2 using appropriate reagents and starting material.

$^1$H-NMR (300 MHz, $CDCl_3$) δ 0.07 (s, 6H), 0.89 (s, 9H), 1.43-1.59 (m, 11H), 1.79-1.88 (m, 2H), 2.99-3.13 (m, 2H), 3.44-3.52 (m, 1H), 3.54-3.59 (m, 2H), 3.60-3.68 (s, 4H), 3.72-3.84 (m, 4H).

(Reaction 228-5)

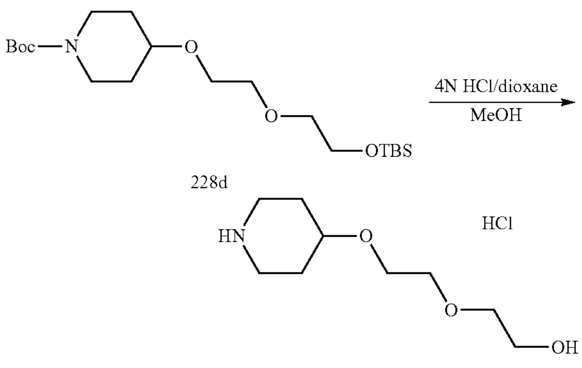

228d

228e

2-[2-(Piperidin-4-yloxy)-ethoxy]-ethanol hydrochloride was synthesized by operations similar to those in Reaction 5-3 using appropriate reagents and starting material. This was used in the next reaction without purification.

Example 229

8-((E)-2-{4-[4-((R)-2,3-Dihydroxy-propoxy)-piperidine-1-carbonyl]-2,6-dimethyl-phenyl}-ethenesulfonyl)-2-(9,9,9-trifluoro-nonyl)-1,3,8-triaza-spiro[4.5]dec-1-en-4-one (Compound 1010)

(Reaction 229-1)

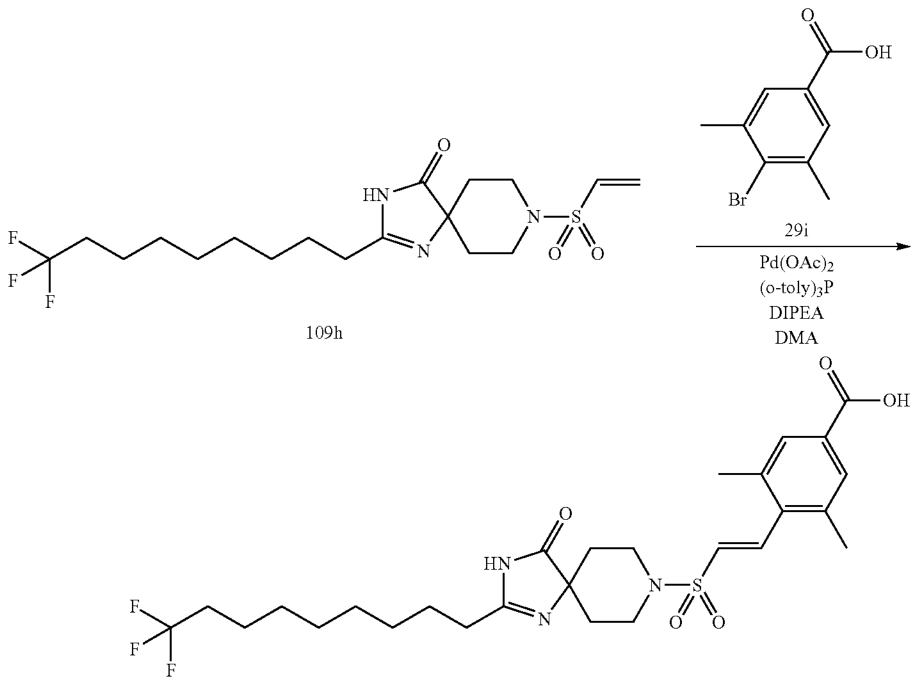

29i

109h

229a 3,5-Dimethyl-4-((E)-2-{4-oxo-2-[4-(9,9,9-trifluoro-nonyl)-cyclohexyl]-1,3,8-triaza-spiro[4.5]dec-1-ene-8-sulfonyl}-vinyl)-benzoic acid was synthesized by operations similar to those in Reaction 26-1 using appropriate reagents and starting material.

MS (ESI) m/z=572 (M+H)+.

(Reaction 229-2)

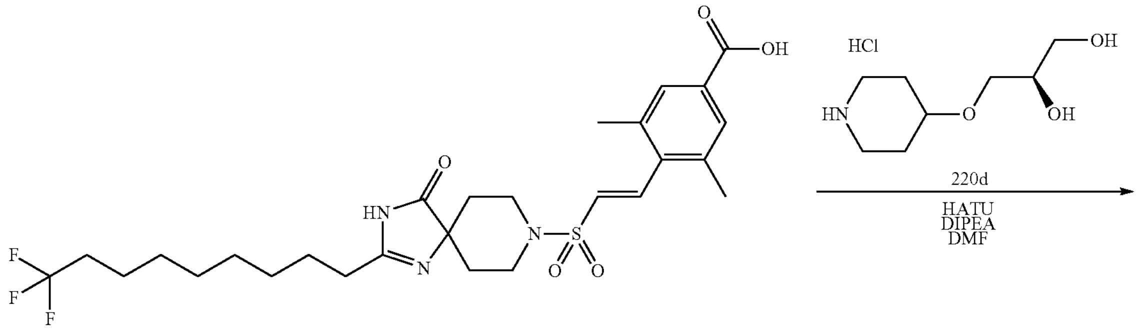

229a

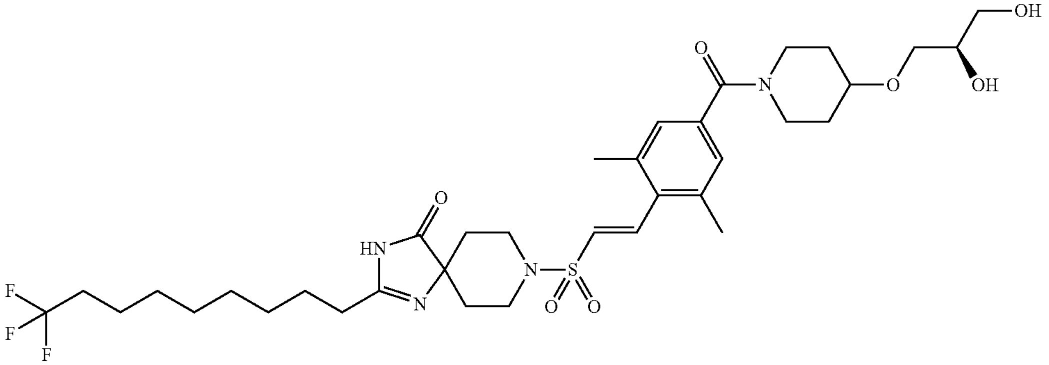

Compound 1010

8-((E)-2-{4-[4-((R)-2,3-Dihydroxy-propoxy)-piperidine-1-carbonyl]-2,6-dimethyl-phenyl}-ethenesulfonyl)-2-(9,9,9-trifluoro-nonyl)-1,3,8-triaza-spiro[4.5]dec-1-en-4-one was synthesized by operations similar to those in Reaction 10-14 using appropriate reagents and starting material.

MS (ESI) m/z=729 (M+H)+.

Example 230

2-Amino-N-(3,5-dimethyl-4-{(E)-2-[4-oxo-2-(3-trifluoromethoxy-phenyl)-1,3,8-triaza-spiro[4.5]dec-1-ene-8-sulfonyl]-vinyl}-phenyl)-N-methyl-acetamide (Compound 1011)

(Reaction 230-1)

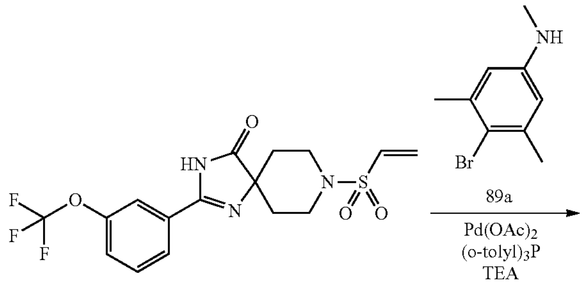

30a

-continued

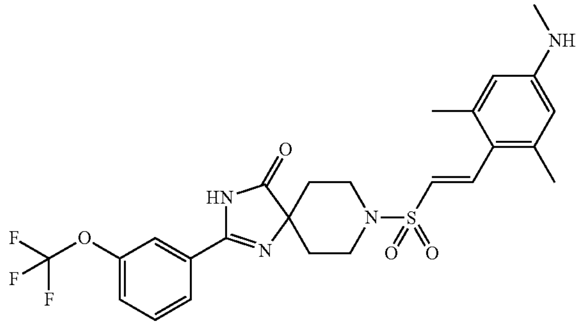

230a

8-[(E)-2-(2,6-Dimethyl-4-methylamino-phenyl)-ethenesulfonyl]-2-(3-trifluoromethoxy-phenyl)-1,3,8-triaza-spiro[4.5]dec-1-en-4-one was synthesized by operations similar to those in Reaction 26-1 using appropriate reagents and starting material.

MS (ESI) m/z=537 (M+H)+.

(Reaction 230-2)
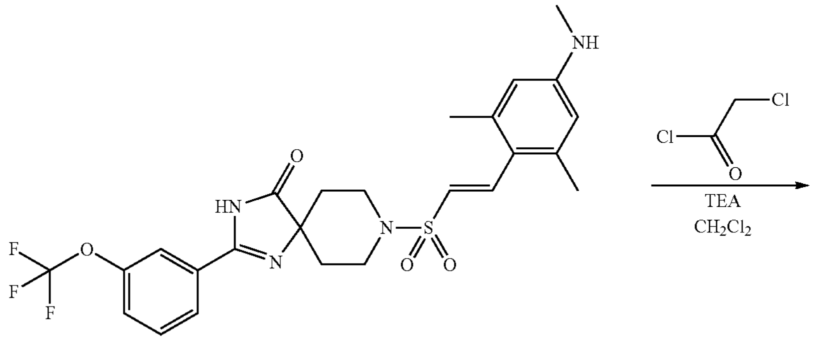
230a
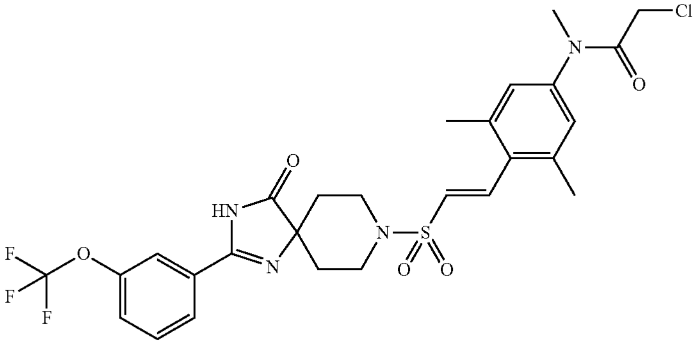
230b
2-Chloro-N-(3,5-dimethyl-4-{(E)-2-[4-oxo-2-(3-trifluoromethoxy-phenyl)-1,3,8-triaza-spiro[4.5]dec-1-ene-8-sulfonyl]-vinyl}-phenyl)-N-methyl-acetamide was synthesized by operations similar to those in Reaction 2-3 using appropriate reagents and starting material.
MS (ESI) m/z=613 (M+H)+.
(Reaction 230-3)
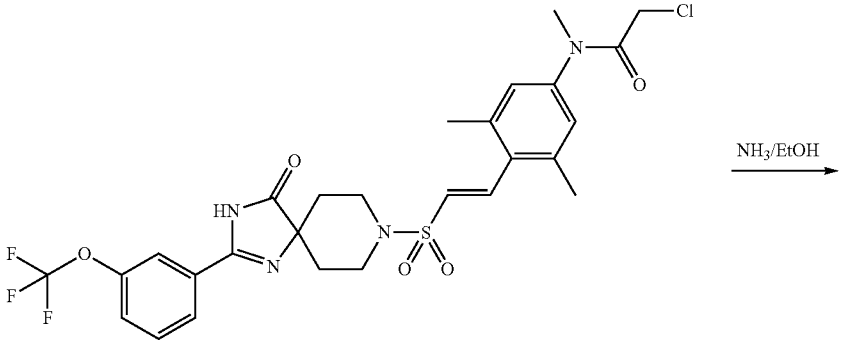
230b -continued

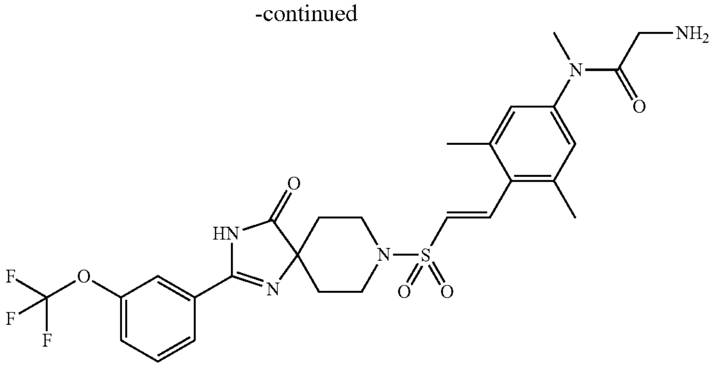

Compound 1011

Ammonia (6 N solution in ethanol, 0.3 ml) was added to a solution of 2-chloro-N-(3,5-dimethyl-4-{(E)-2-[4-oxo-2-(3-trifluoromethoxy-phenyl)-1,3,8-triaza-spiro[4.5]dec-1-ene-8-sulfonyl]-vinyl}-phenyl)-N-methyl-acetamide (38 mg, 0.06 mmol) in anhydrous ethanol (0.5 ml), and the mixture was stirred at 50 to 60° C. for five hours. The mixed solution was concentrated under reduced pressure, and the resulting residue was then purified by silica gel column chromatography (dichloromethane) to give 2-amino-N-(3,5-dimethyl-4-{(E)-2-[4-oxo-2-(3 -trifluoromethoxy-phenyl)-1,3,8-triaza-spiro[4.5]dec-1-ene-8-sulfonyl]-vinyl}-phenyl)-N-methyl-acetamide (11 mg, 31%).

MS (ESI) m/z=594 (M+H)+.

Example 231

(3,5-Dimethyl-4-{(E)-2-[4-oxo-2-(3-trifluoromethoxy-phenyl)-1,3,8-triaza-spiro[4.5]dec-1-ene-8-sulfonyl]-vinyl}-phenyl)-methyl-carbamic acid 2-hydroxy-ethyl ester (Compound 1012)

(Reaction 231-1)

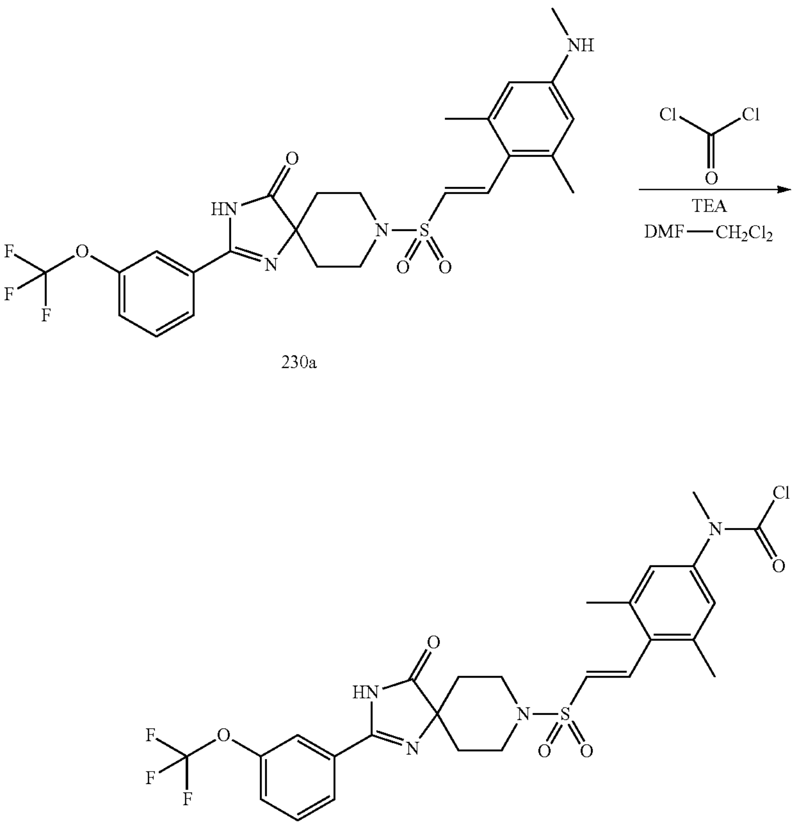

230a

231a

Phosgene (20% solution in toluene, 35 μL, 67 μmol) was added to a mixed solution of 8-[(E)-2-(2,6-dimethyl-4-methylamino-phenyl)-ethenesulfonyl]-2-(3-trifluoromethoxy-phenyl)-1,3,8-triaza-spiro[4.5]dec-1-en-4-one (30 mg, 56 μmol) and triethylamine (15 μL, 84 μmol) in dichloromethane (1.5 ml) and dimethylformamide (0.5 ml) at 0° C. The mixture was stirred at room temperature for three hours, and then quenched with water and extracted with ethyl acetate. The organic layer was sequentially washed with water and saturated brine, and then dried over anhydrous sodium sulfate and concentrated under reduced pressure. The resulting residue was purified by silica gel column chromatography (dichloromethane-ethyl acetate) to give N-(3,5-dimethyl-4-{(E)-2-[4-oxo-2-(3-trifluoromethoxy-phenyl)-1,3,8-triaza-spiro[4.5]dec-1-ene-8-sulfonyl]-vinyl}-phenyl)-N-methyl-chloroformamide (28 mg, 85%).

MS (ESI) m/z=599 (M+H)+.

(Reaction 231-2)

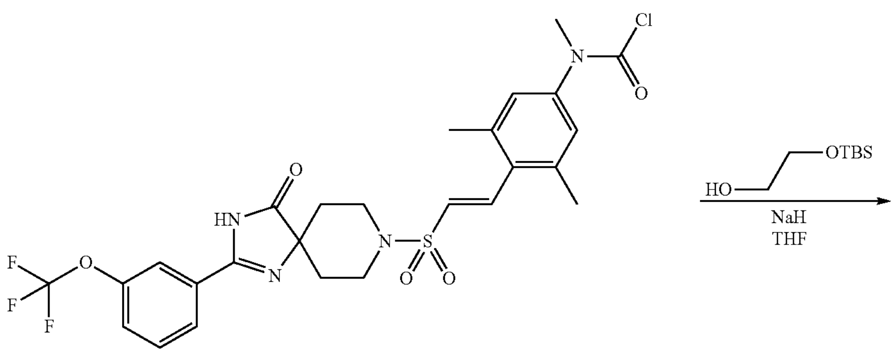

231a

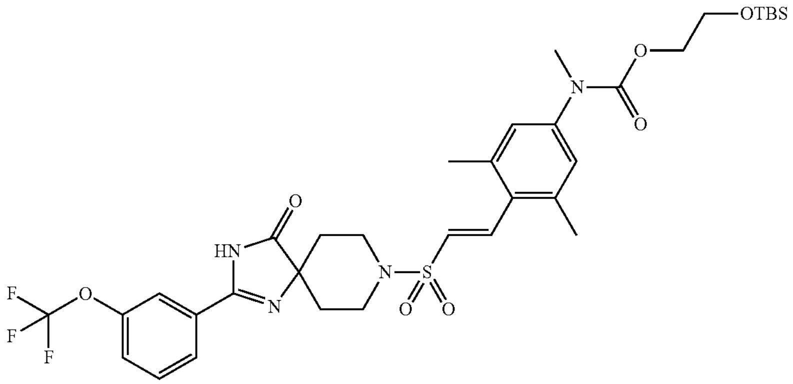

231b

Sodium hydride (60% oil suspension, 5.6 mg, 0.14 mmol) was added to a solution of N-(3,5-dimethyl-4-{(E)-2-[4-oxo-2-(3-trifluoromethoxy-phenyl)-1,3,8-triaza-spiro[4.5]dec-1-ene-8-sulfonyl]-vinyl}-phenyl)-N-methyl-chloroformamide (30 mg, 50.1 μmol) in tetrahydrofuran (1.0 ml) at 0° C., and the mixture was stirred for 15 minutes. 2-(tert-Butyl-dimethyl-silanyloxy)-ethanol (30 μL, 0.14 mmol) was then added and the mixture was stirred at 40° C. for two hours. The mixture was cooled, and then quenched with water and extracted with ethyl acetate. The organic layer was sequentially washed with water and saturated brine, and then dried over anhydrous sodium sulfate and concentrated under reduced pressure. The resulting residue was purified by silica gel column chromatography (dichloromethane-ethyl acetate) to give (3,5-dimethyl-4-{(E)-2-[4-oxo-2-(3-trifluoromethoxy-phenyl)-1,3,8-triaza-spiro[4.5]dec-1-ene-8-sulfonyl]-vinyl}-phenyl)-methyl-carbamic acid 2-(tert-butyl-dimethyl-silanyloxy)-ethyl ester (29 mg, 78%).

MS (ESI) m/z=739 (M+H)+.

(Reaction 231-3)

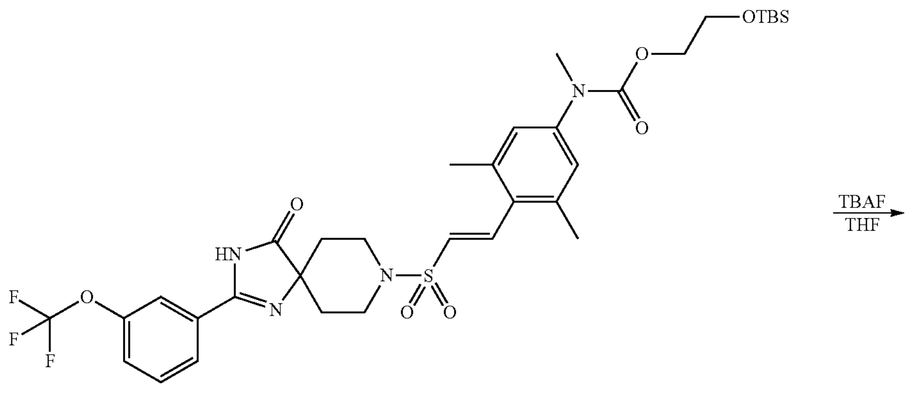

231b

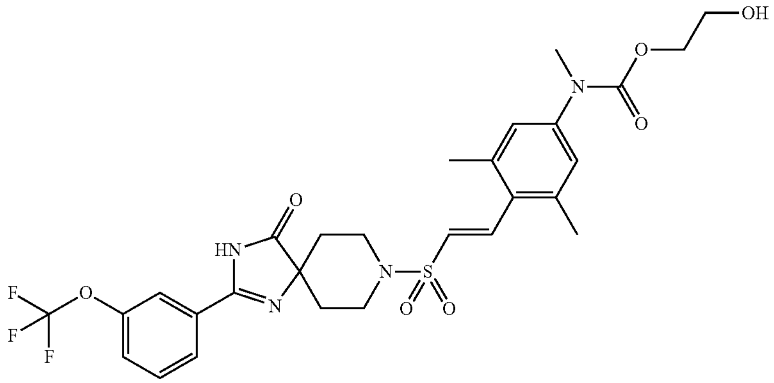

Compound 1012

(3,5-Dimethyl-4-{(E)-2-[4-oxo-2-(3-trifluoromethoxy-phenyl)-1,3,8-triaza-spiro[4.5]dec-1-ene-8-sulfonyl]-vinyl}-phenyl)-methyl-carbamic acid 2-hydroxy-ethyl ester was synthesized by operations similar to those in Reaction 39-2 using appropriate reagents and starting material.

MS (ESI) m/z=625 (M+H)+.

Example 232

1-(3,5-Dimethyl-4-{(E)-2-[4-oxo-2-(3-trifluoromethoxy-phenyl)-1,3,8-triaza-spiro[4.5]dec-1-ene-8-sulfonyl]-vinyl}-phenyl)-1,3,3-trimethyl-urea (Compound 1013)

(Reaction 232-1)

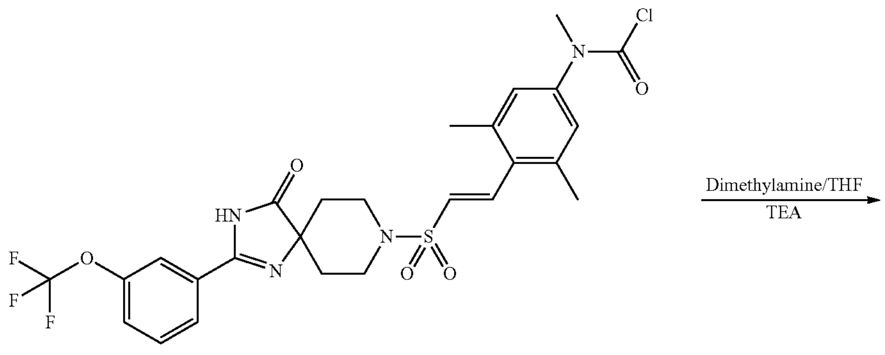

231a

-continued

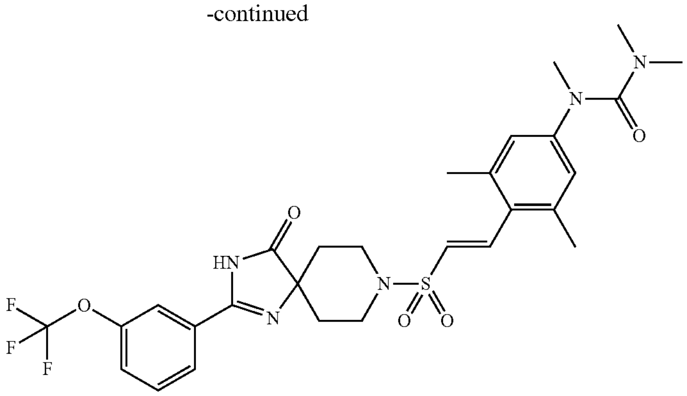

Compound 1013

1-(3,5-Dimethyl-4-{(E)-2-[4-oxo-2-(3-trifluoromethoxy-phenyl)-1,3,8-triaza-spiro[4.5]dec-1-ene-8-sulfonyl]-vinyl}-phenyl)-1,3,3-trimethyl-urea was synthesized by operations similar to those in Reaction 231-2 using appropriate reagents and starting material.

MS (ESI) m/z=608 (M+H)+.

The example compounds shown below were synthesized by operations similar to those in Reaction 232-1 using appropriate reagents and starting materials.

Compounds 1014 to 1015

TABLE 148

| Compound | Structure | LCMS condition | Retention time (min) | MS (m/z) |
|---|---|---|---|---|
| 1014 | 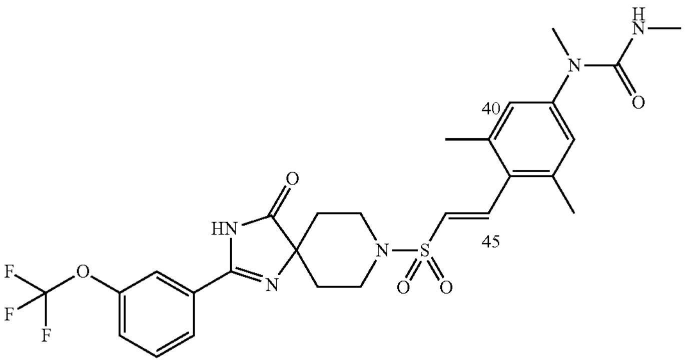 [SMILES: CNC(=O)N(C)c1cc(C)c(/C=C/S(=O)(=O)N2CCC3(CC2)N=C(c2cccc(OC(F)(F)F)c2)NC3=O)c(C)c1] | LCMS-D-1 | 3.02 | 594 (M + H)+ |
| 1015 | 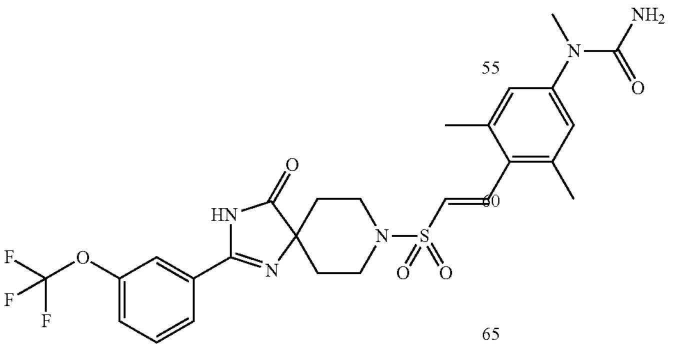 [SMILES: Cc1cc(N(C)C(N)=O)cc(C)c1/C=C/S(=O)(=O)N1CCC2(CC1)N=C(c1cccc(OC(F)(F)F)c1)NC2=O] | LCMS-D-1 | 2.92 | 580 (M + H)+ |

Example 233

8-[(E)-2-(2,6-Dimethyl-4-methylamino-phenyl)-ethenesulfonyl]-2-(3-trifluoromethylsulfanyl-phenyl)-1,3,8-triaza-spiro[4.5]dec-1-en-4-one (Compound 1016)

(Reaction 233-1)

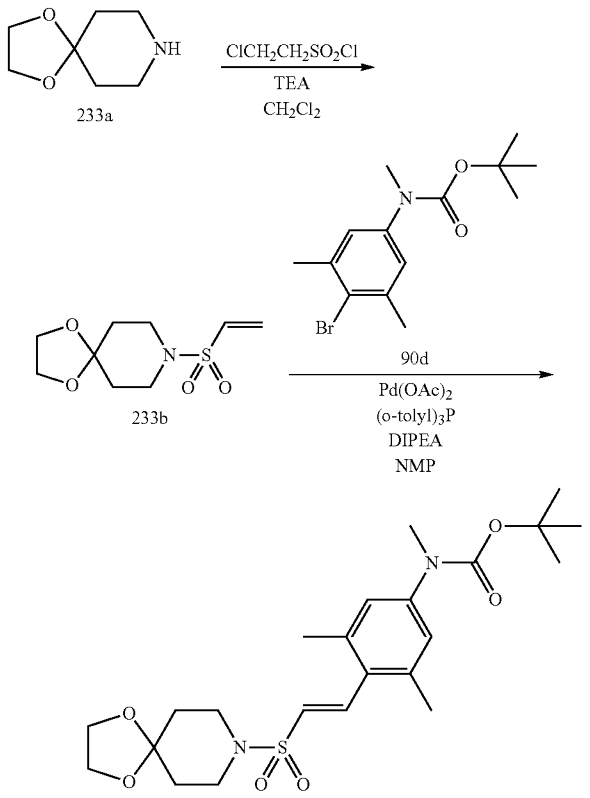

233a

90d

233b

233c

{4-[(E)-2-(1,4-Dioxa-8-aza-spiro[4.5]decane-8-sulfonyl)-vinyl]-3,5-dimethyl-phenyl}-methyl-carbamic acid tert-butyl ester was synthesized by operations similar to those in Reaction 25-1 and Reaction 26-1 using appropriate reagents and starting material.

MS (ESI) m/z=467 (M+H)+.

(Reaction 233-2)

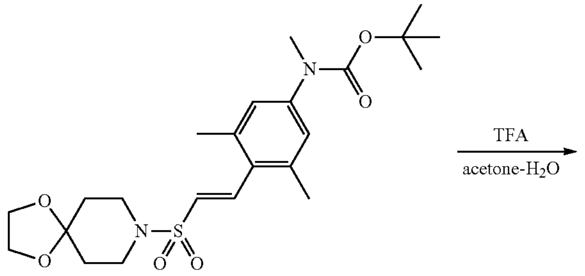

233c

-continued

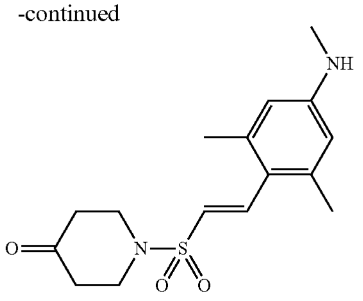

233d

Trifluoroacetic acid (5.3 ml, 71.79 mmol) was added to a solution of {4-[(E)-2-(1,4-dioxa-8-aza-spiro[4.5]decane-8-sulfonyl)-vinyl]-3,5-dimethyl-phenyl}-methyl-carbamic acid tert-butyl ester (670 mg, 1.43 mmol) in acetone-water (8.0 ml-8.0 ml) at room temperature, and the mixture was heated with stirring at 50° C. for 18 hours. The mixed reaction solution was cooled and then concentrated under reduced pressure. The residue was neutralized by adding a saturated aqueous sodium bicarbonate solution and extracted with ethyl acetate. The organic layer was sequentially washed with water and saturated brine, and then dried over $Na_2SO_4$ and concentrated under reduced pressure. The resulting residue was purified by silica gel column chromatography (ethyl acetate-hexane) to give 1-[(E)-2-(N,2,6-trimethylaniline)-ethenesulfonyl]-piperidin-4-one (364 mg, 78%).

MS (ESI) m/z=323 (M+H)+.

(Reaction 233-3)

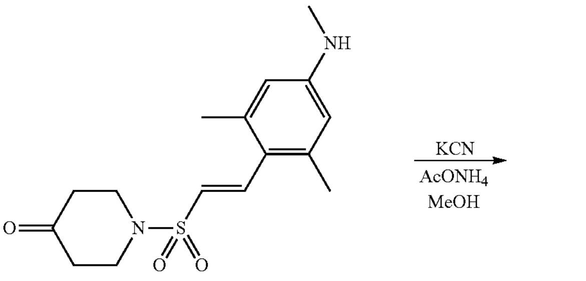

233d

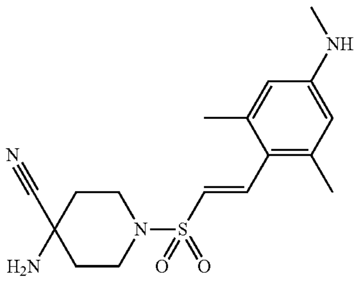

233e

Ammonium acetate (686 mg, 8.91 mmol) and potassium cyanide (541 mg, 8.31 mmol) were added to a solution of 1-[(E)-2-(2,6-dimethyl-4-methylamino-phenyl)-ethene-sulfonyl]-piperidin-4-one (1.91 g, 5.94 mmol) in MeOH (20 ml), and the mixture was heated with stirring at 60° C. for three hours. The mixed reaction solution was cooled and a saturated aqueous $NaHCO_3$ solution was then added, followed by extraction with ethyl acetate. The organic layer was sequentially washed with water and saturated brine, and then dried over $Na_2SO_4$ and concentrated under reduced pressure. The resulting residue was triturated with hexane:$CH_2Cl_2$=7:3 to give 4-amino-1-[(E)-2-(2,6-dimethyl-4-methylamino-phenyl)-ethenesulfonyl]-piperidine-4-carbonitrile (1.86 g, 89%).

MS (ESI) m/z=349 (M+H)+.

(Reaction 233-4)

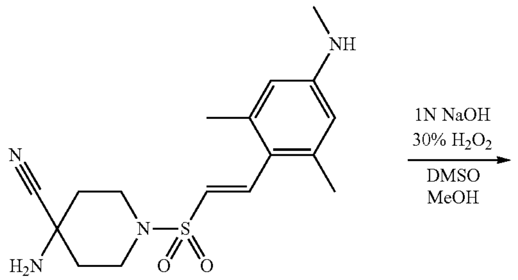

233e

-continued

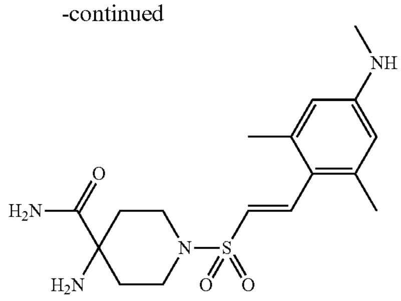

233f

DMSO (0.9 ml, 12.8 mmol), a 1 N aqueous NaOH solution (1.06 ml, 1.06 mmol) and 30% aqueous hydrogen peroxide (0.72 ml, 6.40 mmol) were sequentially added to a solution of 4-amino-1-[(E)-2-(2,6-dimethyl-4-methylamino-phenyl)-ethenesulfonyl]-piperidine-4-carbonitrile (1.85 g, 5.33 mmol) in MeOH (30 ml) at 0° C., and the mixture was stirred at room temperature for 2.5 hours. A saturated $Na_2S_2O_3$ solution was added to the reaction mixture, and the precipitated solid was obtained by suction filtration. The resulting solid was washed with water, dissolved in a $CH_2Cl_2$-MeOH (3:2) solution, dried over $Na_2SO_4$ and concentrated under reduced pressure. The resulting residue was triturated with hexane: $CH_2Cl_2$=4:1 to give 4-amino-1-[(E)-2-(2,6-dimethyl-4-methylamino-phenyl)-ethenesulfonyl]-piperidine-4-carboxylic amide (1.36 g, 70%).

MS (ESI) m/z=367 (M+H)+.

(Reaction 233-5)

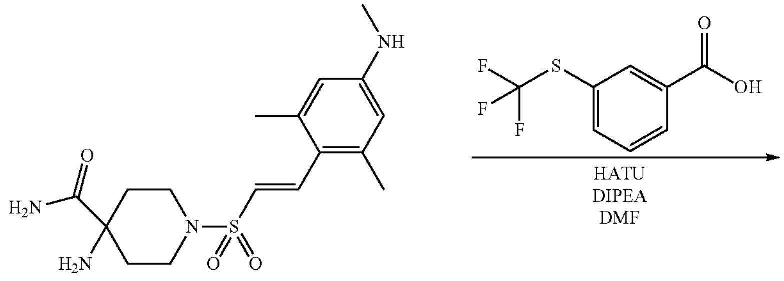

233f

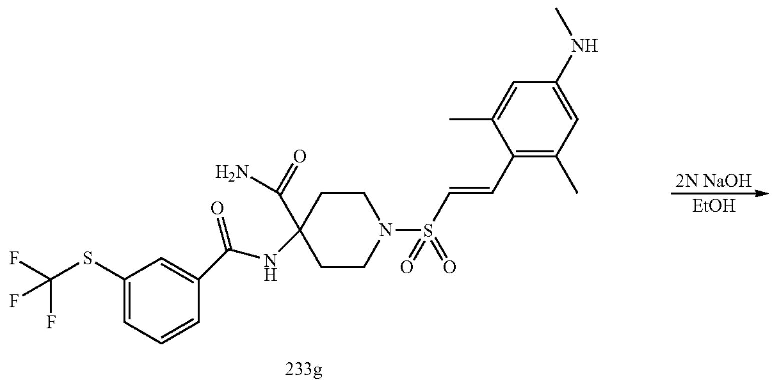

233g

-continued

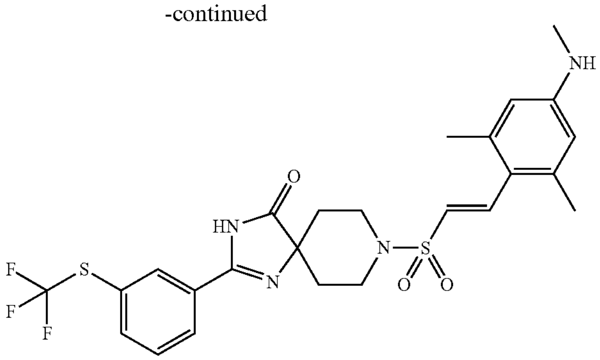

Compound 1016

8-[(E)-2-(2,6-Dimethyl-4-methylamino-phenyl)-ethene-sulfonyl]-2-(3-trifluoromethylsulfanyl-phenyl)-1,3,8-triaza-spiro[4.5]dec-1-en-4-one was synthesized by operations similar to those in Reaction 10-14 and Reaction 189-5 using appropriate reagents and starting material.

MS (ESI) m/z=553 (M+H)+.

Example 234

1-(4-{(E)-2-[2-(4-Fluoro-3-trifluoromethyl-phenyl)-4-oxo-1,3,8-triaza-spiro[4.5]dec-1-ene-8-sulfonyl]-vinyl}-3,5-dimethyl-phenyl)-1-methyl-urea (Compound 1017)

(Reaction 234-1)

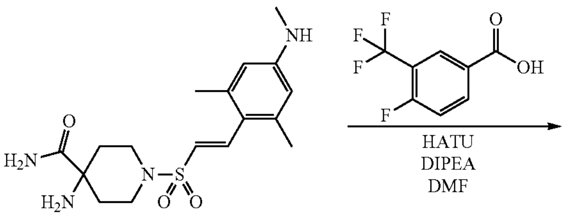

233f

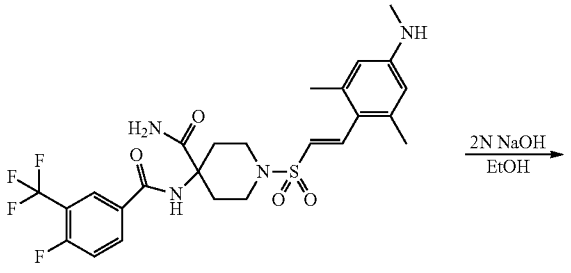

234a

-continued

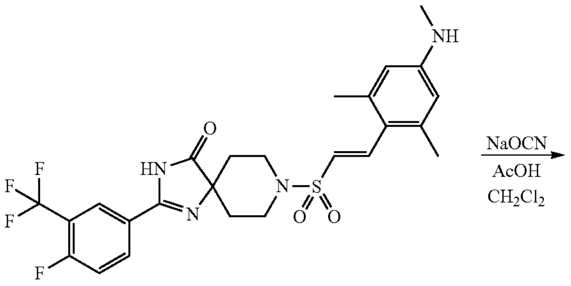

234b

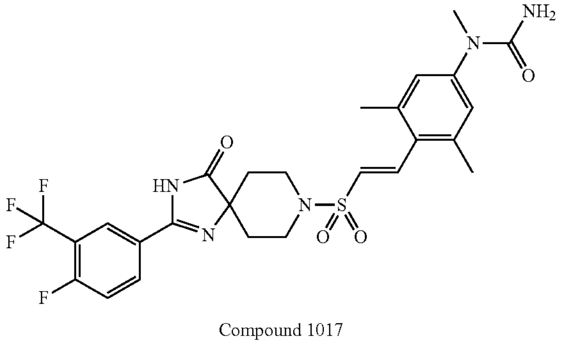

Compound 1017

1-(4-{(E)-2-[2-(4-Fluoro-3-trifluoromethyl-phenyl)-4-oxo-1,3,8-triaza-spiro[4.5]dec-1-ene-8-sulfonyl]-vinyl}-3,5-dimethyl-phenyl)-1-methyl-urea was synthesized by operations similar to those in Reaction 10-14, Reaction 189-5 and Reaction 89-2 using appropriate reagents and starting material.

MS (ESI) m/z=582 (M+H)+.

The example compounds shown below were synthesized by operations similar to those in Reaction 234-1 using appropriate reagents and starting materials.

Compounds 1018 to 1021
TABLE 149
| Compound | Structure | LCMS condition | Retention time (min) | MS (m/z) |
| --- | --- | --- | --- | --- |
| 1018 | 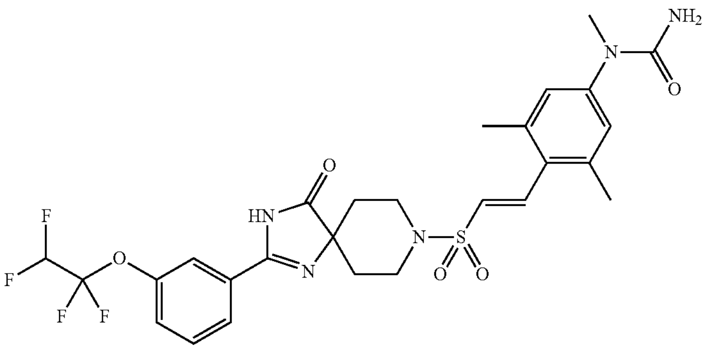 [SMILES: Cc1cc(N(C)C(N)=O)cc(C)c1/C=C/S(=O)(=O)N1CCC2(CC1)N=C(c1cccc(OC(F)(F)C(F)F)c1)NC2=O] | LCMS-F-1 | 0.95 | 612 (M + H)+ |
| 1019 | 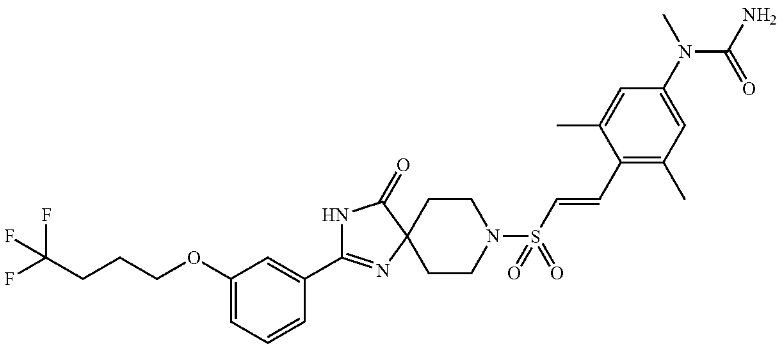 [SMILES: Cc1cc(N(C)C(N)=O)cc(C)c1/C=C/S(=O)(=O)N1CCC2(CC1)N=C(c1cccc(OCCCC(F)(F)F)c1)NC2=O] | LCMS-F-1 | 0.99 | 622 (M + H)+ |
| 1020 | 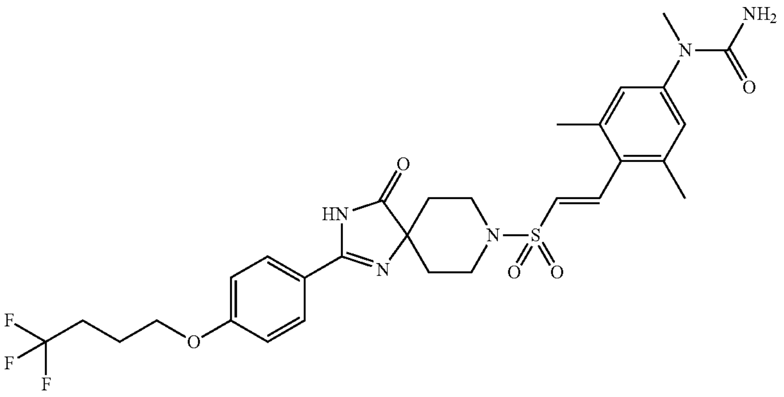 [SMILES: Cc1cc(N(C)C(N)=O)cc(C)c1/C=C/S(=O)(=O)N1CCC2(CC1)N=C(c1ccc(OCCCC(F)(F)F)cc1)NC2=O] | LCMS-F-1 | 0.97 | 622 (M + H)+ |
| 1021 | 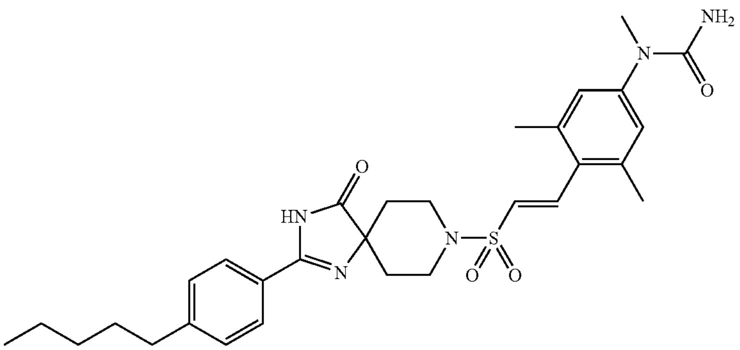 [SMILES: CCCCCc1ccc(C2=NC3(CCN(S(=O)(=O)/C=C/c4c(C)cc(N(C)C(N)=O)cc4C)CC3)C(=O)N2)cc1] | LCMS-F-1 | 1.04 | 566 (M + H)+ |

The carboxylic acid reagent used in the synthesis of Compound 1019 (3-(4,4,4-trifluoro-butoxy)-benzoic acid) was synthesized by the following method.

(Reaction 234-2)

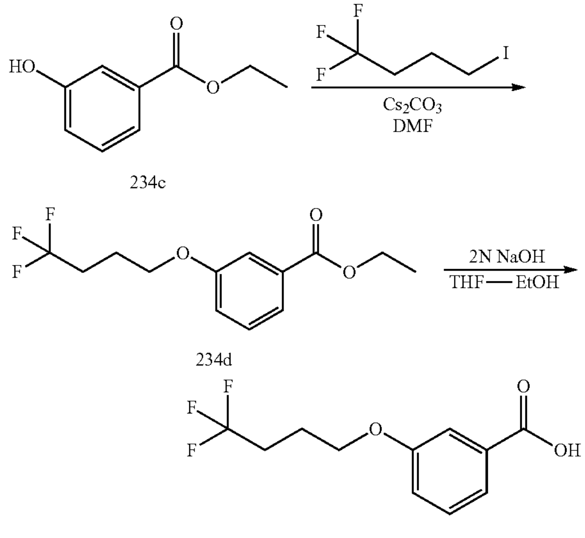

234c

234d

234e 3-(4,4,4-Trifluoro-butoxy)-benzoic acid was synthesized by operations similar to those in Reaction 26-4 (using $Cs_2CO_3$ as a base) and Reaction 189-5 using appropriate reagents and starting material.

MS (ESI) m/z=247 (M−H)−.

The carboxylic acid reagent used in the synthesis of Compound 1020 (4-(4,4,4-trifluoro-butoxy)-benzoic acid) was synthesized by the following method.

(Reaction 234-3)

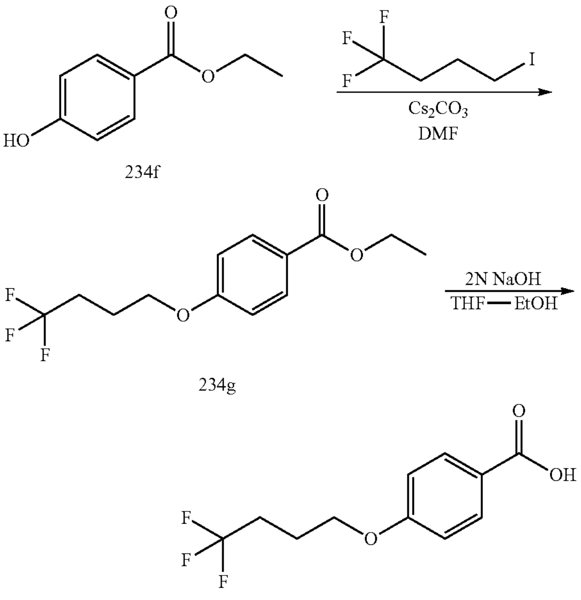

234f

234g

234h 4-(4,4,4-Trifluoro-butoxy)-benzoic acid was synthesized by operations similar to those in Reaction 26-4 (using $Cs_2CO_3$ as a base) and Reaction 189-5 using appropriate reagents and starting material.

MS (ESI) m/z=249 (M+H)+.

Example 235

1-(3,5-Dimethyl-4-{(E)-2-[2-(7-methylsulfanyl-heptyl)-4-oxo-1,3,8-triaza-spiro[4.5]dec-1-ene-8-sulfonyl]-vinyl}-phenyl)-1-methyl-urea (Compound 1022)

(Reaction 235-1)

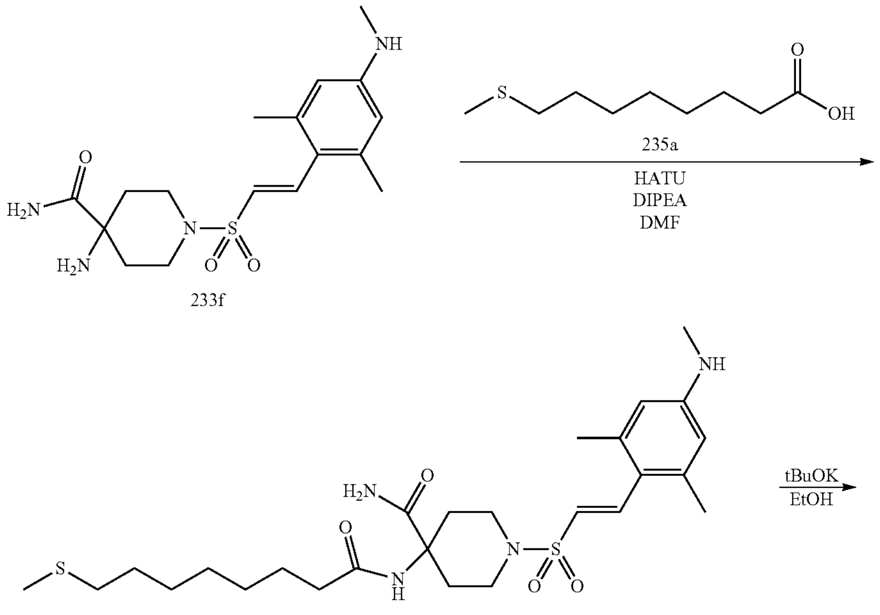

235a

233f

235b

-continued

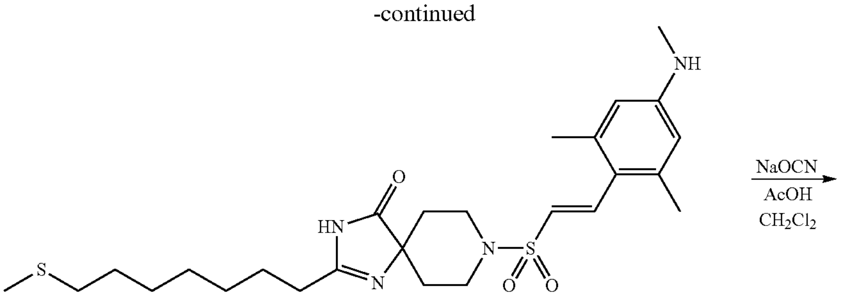

235c

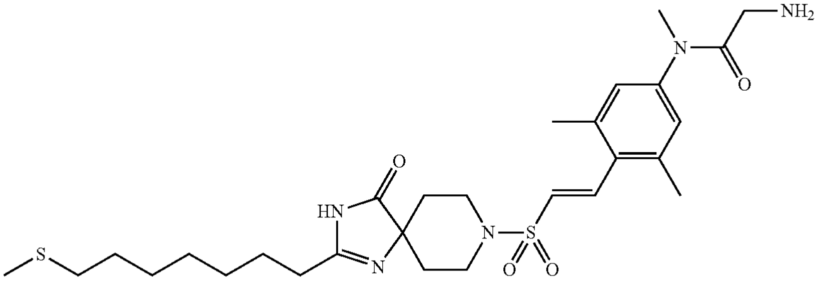

Compound 1022

1-(3,5-Dimethyl-4-{(E)-2-[2-(7-methylsulfanyl-heptyl)-4-oxo-1,3,8-triaza-spiro[4.5]dec-1-ene-8-sulfonyl]-vinyl}-phenyl)-1-methyl-urea was synthesized by operations similar to those in Reaction 10-14, Reaction 10-12 and Reaction 89-2 using appropriate reagents and starting material.

MS (ESI) m/z=564 (M+H)+.

The carboxylic acid reagent used in the synthesis of Compound 1022 (8-(methylthio)octanoic acid) was synthesized by the following method.

(Reaction 235-2)

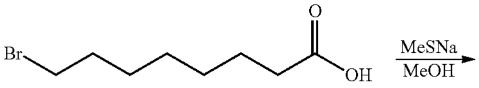

235d

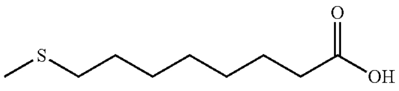

235a

Sodium thiomethoxide (942 mg, 13.44 mmol) was added to a solution of 8-bromooctanoic acid (500 mg, 2.24 mmol) in methanol (5.6 mL), and the mixture was heated under reflux overnight. The reaction mixture was concentrated under reduced pressure, adjusted to pH 1 by adding 1 N hydrochloric acid and then extracted with ethyl acetate. The organic layer was washed with saturated brine, and then dried over $MgSO_4$ and concentrated under reduced pressure. The resulting residue was purified by silica gel column chromatography (dichloromethane:methanol=20:1) to give 8-(methylthio)octanoic acid as a colorless oily substance (426.5 mg, 100%).

$^1$H-NMR (300 MHz, $CDCl_3$) δ 1.31-1.41 (m, 6H), 1.54-1.66 (m, 4H), 2.09 (s, 3H), 2.35 (t, 2H, J=7.2 Hz), 2.48 (t, 2H, J=7.2 Hz).

Example 236

1-[3,5-Dimethyl-4-((E)-2-{2-[8-(3-methyl-oxetan-3-yl)-octyl]-4-oxo-1,3,8-triaza-spiro[4.5]dec-1-ene-8-sulfonyl}-vinyl)-phenyl]-1-methyl-urea (Compound 1023)

(Reaction 236-1)

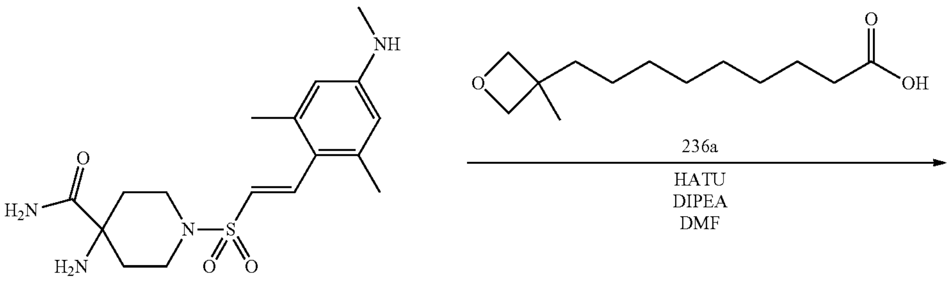

233f

-continued

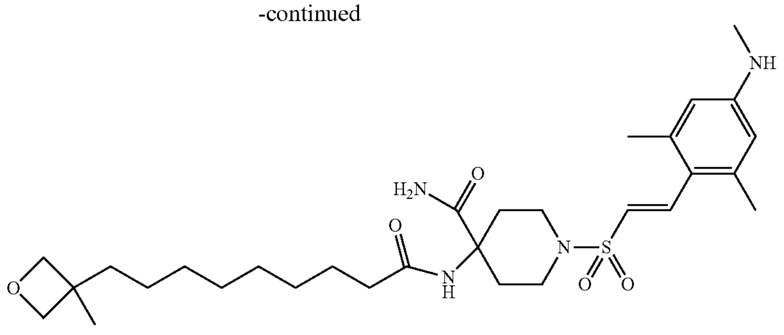

236b

1-[(E)-2-(2,6-Dimethyl-4-methylamino-phenyl)-ethenesulfonyl]-4-[9-(3-methyl-oxetan-3-yl)-nonanoylamino]-piperidine-4-carboxylic amide was synthesized by operations similar to those in Reaction 10-14 using appropriate reagents and starting material. This was used in the next reaction without purification.

(Reaction 236-2)

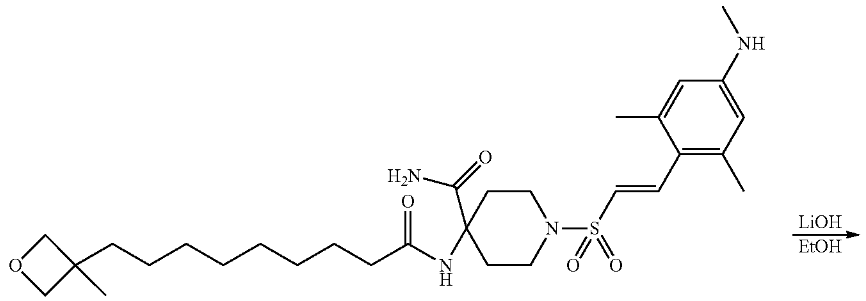

236b

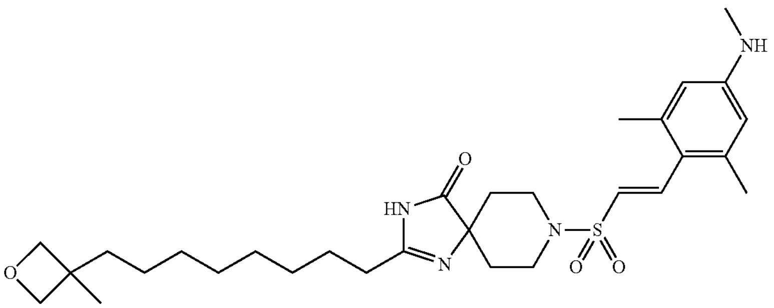

236c

LiOH.$H_2O$ (16.6 mg, 0.396 mmol) was added to a solution of 1-[(E)-2-(2,6-dimethyl-4-methylamino-phenyl)-ethenesulfonyl]-4-[9-(3-methyl-oxetan-3-yl)-nonanoylamino]-piperidine-4-carboxylic amide (96 mg, 0.098 mmol) in ethanol (1.0 mL), and the mixture was stirred at 50° C. for two hours. A 50% saturated aqueous ammonium chloride solution was added to the reaction mixture, followed by extraction with ethyl acetate. The organic layer was then dried over $MgSO_4$ and concentrated under reduced pressure. The resulting residue was purified by silica gel column chromatography (ethyl acetate) to give 8-[(E)-2-(2,6-Dimethyl-4-methylamino-phenyl)-ethenesulfonyl]-2-[8-(3-methyl-oxetan-3-yl)-octyl]-1,3,8-triaza-spiro[4.5]dec-1-en-4-one (54.8 mg, 100%).

$^1$H-NMR (400 MHz, $CD_3OD$) δ 1.26 (3H, s), 1.34 (10H, m), 1.63 (6H, m), 1.95 (2H, m), 2.37 (6H, s), 2.44 (2H, m), 2.77 (3H, s), 3.15 (2H, m), 3.63 (2H, m), 4.31 (2H, d, J=5.6 Hz), 4.40 (2H, d, J=5.6 Hz), 6.34 (1H, d, J=15.6 Hz), 6.34 (2H, s), 7.63 (1H, d, J=15.6 Hz).

(Reaction 236-3)

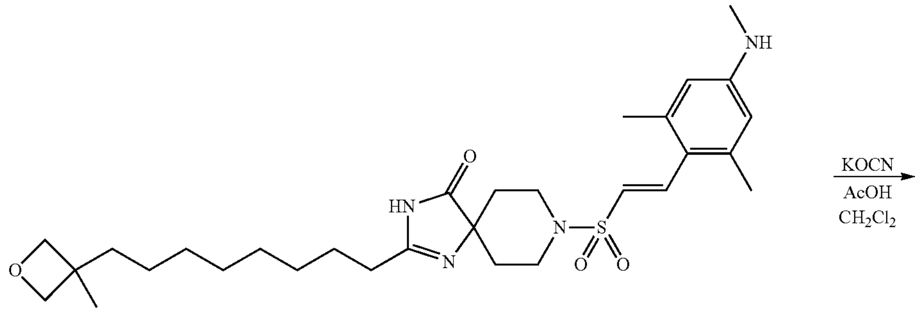

236c

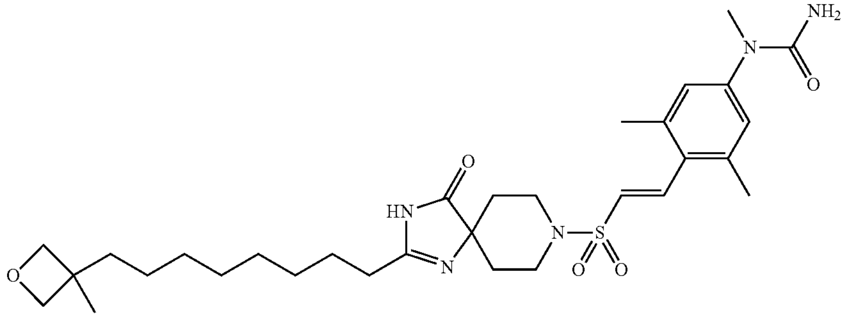

Compound 1023

1-[3,5-Dimethyl-4-((E)-2-{2-[8-(3-methyl-oxetan-3-yl)-octyl]-4-oxo-1,3,8-triaza-spiro[4.5]dec-1-ene-8-sulfonyl}-vinyl)-phenyl]-1-methyl-urea was synthesized by operations similar to those in Reaction 89-2 (using KOCN) using appropriate reagents and starting material.

MS (ESI) m/z=602 (M+H)+.

The carboxylic acid reagent used in the synthesis of Compound 1023 (9-(3-methyl-oxetan-3-yl)-nonanoic acid) was synthesized by the following method.

(Reaction 236-4)

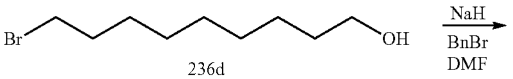

236d

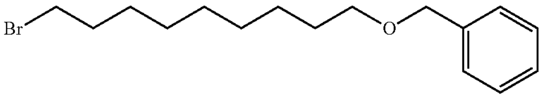

236e (9-Bromo-nonyloxymethyl)-benzene was synthesized by operations similar to those in Reaction 20-2 using appropriate reagents and starting material.

$^1$H-NMR (400 MHz, $CDCl_3$) δ 1.25-1.45 (10H, m), 1.61 (2H, m), 1.85 (2H, m), 3.40 (2H, t, J=6.8 Hz), 3.46 (2H, t, J=6.8 Hz), 4.50 (2H, s), 7.27-7.35 (5H, m).

(Reaction 236-5)

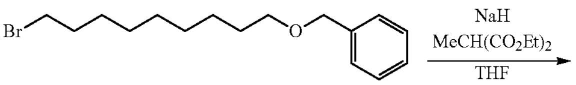

236e

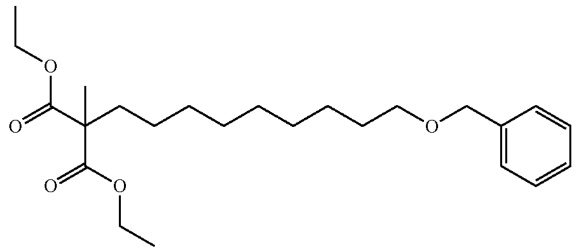

236f

Methyl-malonic acid diethyl ester (0.850 ml, 4.99 mmol) was added to a suspension of sodium hydride (55% oily suspension, 139.5 mg, 3.197 mmol) in THF (0.8 ml) over seven minutes under ice-cooling, and the mixture was stirred until foaming was terminated at room temperature (for about 25 minutes). A solution of (9-bromo-nonyloxymethyl)-benzene (593 mg, 1.89 mmol) in THF (0.12 ml) was added to the reaction solution at room temperature over 15 minutes, and the mixture was then stirred at 90° C. for five hours. The reaction mixture was diluted with ether and water was then added, followed by extraction with ether. The organic layer was dried over $MgSO_4$ and concentrated under reduced pressure. The resulting residue was purified by silica gel column chromatography (hexane/ethyl acetate=30/1→20/1) to give 2-(9-benzyloxy-nonyl)-2-methyl-malonic acid diethyl ester (735 mg, 96%).

$^1$H-NMR (400 MHz, $CDCl_3$) δ 1.24 (6H, t, J=6.8 Hz), 1.27 (12H, m), 1.39 (3H, s), 1.60 (2H, m), 1.83 (2H, m), 3.46 (2H, t, J=6.8 Hz), 4.20 (4H, m), 4.50 (2H, s), 7.27-7.34 (5H, m).

(Reaction 236-6)

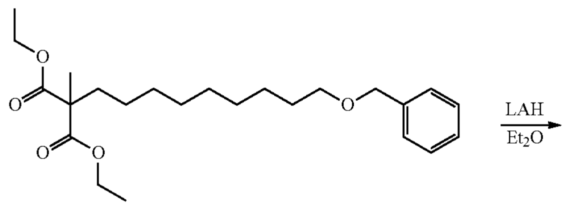

236f

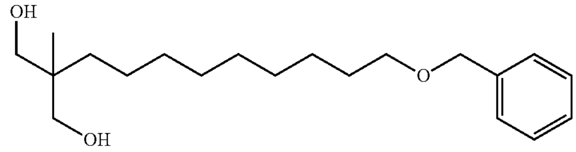

236g 2-(9-Benzyloxy-nonyl)-2-methyl-propane-1,3-diol was synthesized by operations similar to those in Reaction 95-28 using appropriate reagents and starting material.

$^1$H-NMR (400 MHz, $CDCl_3$) δ 0.82 (3H, s), 1.28 (14H, m), 1.61 (2H, m), 2.14 (2H, t, J=4.2 Hz), 3.46 (2H, t, J=6.6 Hz), 3.54 (4H, m), 4.50 (2H, s), 7.27-7.35 (5H, m).

(Reaction 236-7)

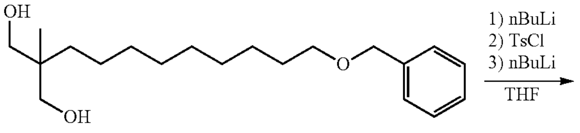

236g

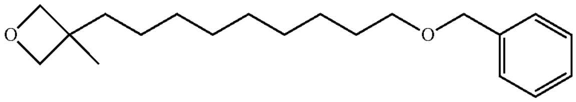

236h n-Butyllithium (2.6 M solution in hexane, 0.295 ml, 0.767 mmol) was added to a solution of 2-(9-benzyloxy-nonyl)-2-methyl-propane-1,3-diol (221 mg, 0.686 mmol) in THF (5.1 ml) at 0° C. over three minutes, and the mixture was then stirred at the same temperature for 30 minutes. A solution of TsCl (138 mg, 0.723 mmol) in THF (0.91 ml) was added to the reaction solution at 0° C. over eight minutes, and the mixture was then stirred at the same temperature for one hour. n-Butyllithium (2.6 M solution in hexane, 0.295 ml, 0.767 mmol) was added dropwise to the reaction mixture at 0° C., and the mixture was then stirred at 60° C. for six hours. The reaction mixture was diluted with ether and water was then added, followed by extraction with ether. The organic layer was dried over $MgSO_4$ and concentrated under reduced pressure. The resulting residue was purified by silica gel column chromatography (hexane/ethyl acetate=15/1) to give 3-(9-benzyloxy-nonyl)-3-methyl-oxetane (188 mg, 90%).

$^1$H-NMR (400 MHz, $CDCl_3$) δ 1.27 (3H, s), 1.29 (12H, m), 1.61 (4H, m), 3.47 (2H, t, J=6.6 Hz), 4.32 (2H, d, J=5.4 Hz), 4.41 (2H, d, J=5.4 Hz), 4.50 (2H, s), 7.27-7.35 (5H, m).

(Reaction 236-8)

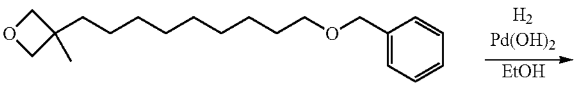

236h

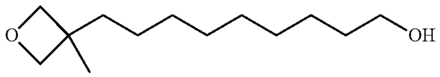

236i 9-(3-Methyl-oxetan-3-yl)-nonan-1-ol was synthesized by operations similar to those in Reaction 122-2 using appropriate reagents and starting material.

$^1$H-NMR (400 MHz, $CDCl_3$) δ 1.27 (3H, s), 1.29 (12H, m), 1.59 (4H, m), 3.64 (2H, t, J=6.6 Hz), 4.33 (2H, d, J=5.8 Hz), 4.41 (2H, d, J=5.8 Hz).

(Reaction 236-9)

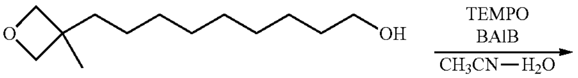

236i

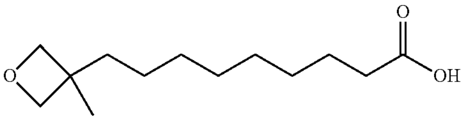

236a

TEMPO (3.4 mg, 0.022 mmol) and iodobenzene diacetate (69.7 mg, 0.216 mmol) were added to a solution of 9-(3-methyl-oxetan-3-yl)-nonan-1-ol (21 mg, 0.098 mmol) in acetonitrile (0.2 ml)-water (0.1 ml) at room temperature, and the mixture was stirred at the same temperature for two hours. Water (0.1 ml) was then added to the reaction mixture at room temperature, and the mixture was stirred at the same temperature for one hour. A 10% aqueous citric acid solution (0.45 ml) was added to the reaction mixture, followed by extraction with ethyl acetate. The organic layer was sequentially washed with water, a 10% aqueous sodium thiosulfate solution and saturated brine, dried over $MgSO_4$ and concentrated under reduced pressure to give 9-(3-methyl-oxetan-3-yl)-nonanoic acid (22 mg, 100%).

$^1$H-NMR (400 MHz, $CDCl_3$) δ 1.27 (3H, s), 1.31 (10H, m), 1.63 (4H, m), 2.35 (2H, t, J=7.6 Hz), 4.33 (2H, d, J=5.4 Hz), 4.42 (2H, d, J=5.4 Hz).

The example compounds shown below were synthesized by operations similar to those in Reaction 236-1, Reaction 236-2 and Reaction 236-3 using appropriate reagents and starting materials.

Compounds 1024 to 1027
TABLE 150
| Compound | Structure | LCMS condition | Retention time (min) | MS (m/z) |
|---|---|---|---|---|
| 1024 | 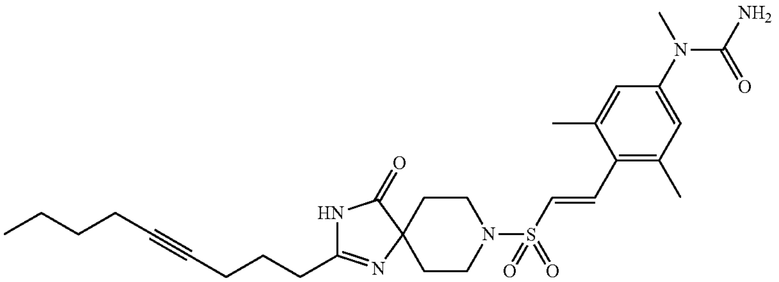 [SMILES: CCCCC#CCCCC1=NC2(CCN(S(=O)(=O)/C=C/c3c(C)cc(N(C)C(N)=O)cc3C)CC2)C(=O)N1] | LCMS-C-2 | 1.97 | 542 (M + H)+ |
| 1025 | 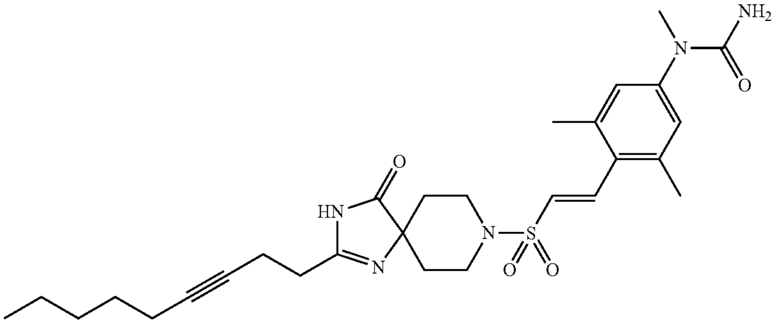 [SMILES: CCCCCC#CCCC1=NC2(CCN(S(=O)(=O)/C=C/c3c(C)cc(N(C)C(N)=O)cc3C)CC2)C(=O)N1] | LCMS-F-1 | 1.01 | 542 (M + H)+ |
| 1026 | 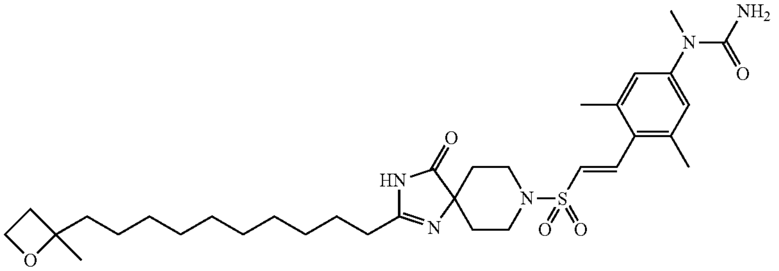 [SMILES: Cc1cc(N(C)C(N)=O)cc(C)c1/C=C/S(=O)(=O)N1CCC2(CC1)N=C(CCCCCCCCCCC1(C)CCO1)NC2=O] | LCMS-C-2 | 2.13 | 630 (M + H)+ |
| 1027 | 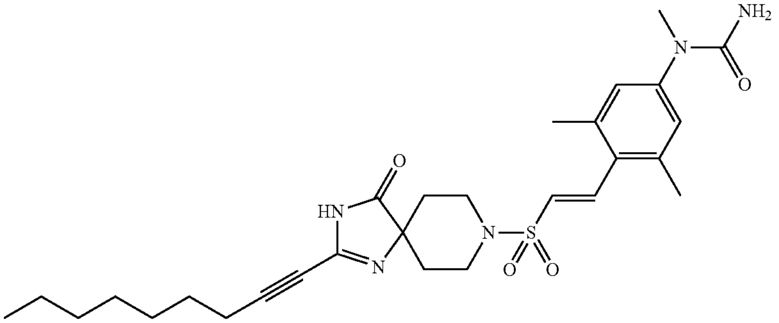 [SMILES: CCCCCCCC#CC1=NC2(CCN(S(=O)(=O)/C=C/c3c(C)cc(N(C)C(N)=O)cc3C)CC2)C(=O)N1] | LCMS-C-2 | 2.22 | 540 (M − H)− |
The carboxylic acid reagent used in the synthesis of Compound 1024 (dec-5-ynoic acid) was synthesized by the following method.
(Reaction 236-10)
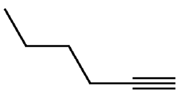
236j
+
-continued
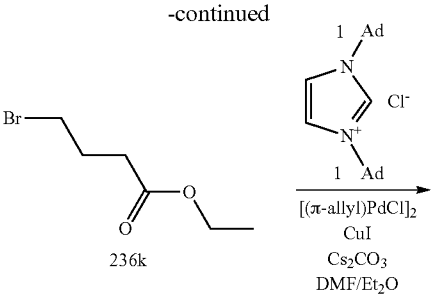
236k -continued

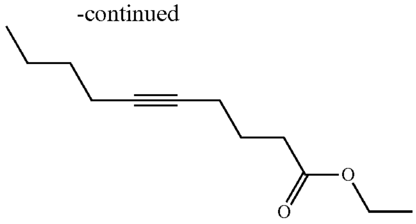

236l

1-Hexyne (43 μl, 0.38 mmol) and ethyl 4-bromobutyrate (40 μl, 0.28 mmol) were added to a suspension of 1,3-bis(1-adamantyl)imidazolium chloride (5.2 mg, 0.014 mmol), copper iodide (4.1 mg, 0.022 mmol), allylpalladium(II) chloride dimer (2.6 mg, 0.071 mmol) and cesium carbonate (127 mg, 0.390 mmol) in anhydrous ether (0.37 ml)-anhydrous DMF (0.185 ml) at room temperature in a nitrogen stream, and the mixture was stirred at 45° C. for 17 hours. The reaction mixture was extracted with pentane. The insoluble matter was removed by filtration, and the filtrate was then concentrated under reduced pressure. The resulting residue was purified by silica gel column chromatography (hexane/ether=50/1) to give dec-5-ynoic acid ethyl ester (40 mg, 73%).

$^1$H-NMR (400 MHz, $CDCl_3$) δ 0.90 (3H, t, J=7.2 Hz), 1.26 (3H, t, J=7.2 Hz), 1.42 (4H, m), 1.80 (2H, m), 2.14 (2H, m), 2.22 (2H, m), 2.42 (2H, t, J=7.6 Hz), 4.13 (2H, q, J=7.2 Hz).

(Reaction 236-11)

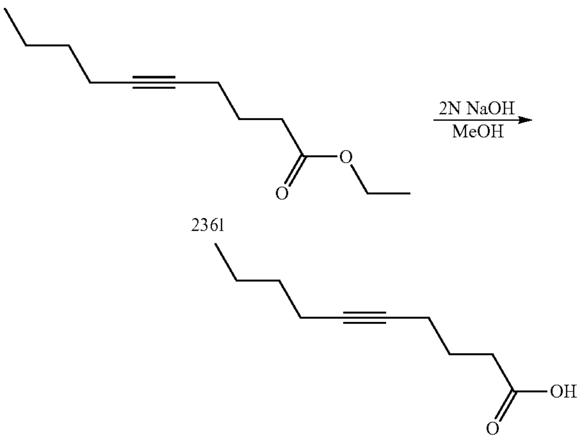

236l

236m

Dec-5-ynoic acid was synthesized by operations similar to those in Reaction 189-5 using appropriate reagents and starting material.

$^1$H-NMR (400 MHz, $CDCl_3$) δ 0.91 (3H, t, J=7.2 Hz), 1.43 (4H, m), 1.82 (2H, m), 2.15 (2H, m), 2.25 (2H, m), 2.50 (2H, t, J=7.2 Hz).

The carboxylic acid reagent used in the synthesis of Compound 1025 (dec-4-ynoic acid) was synthesized by the following method.

(Reaction 236-12)

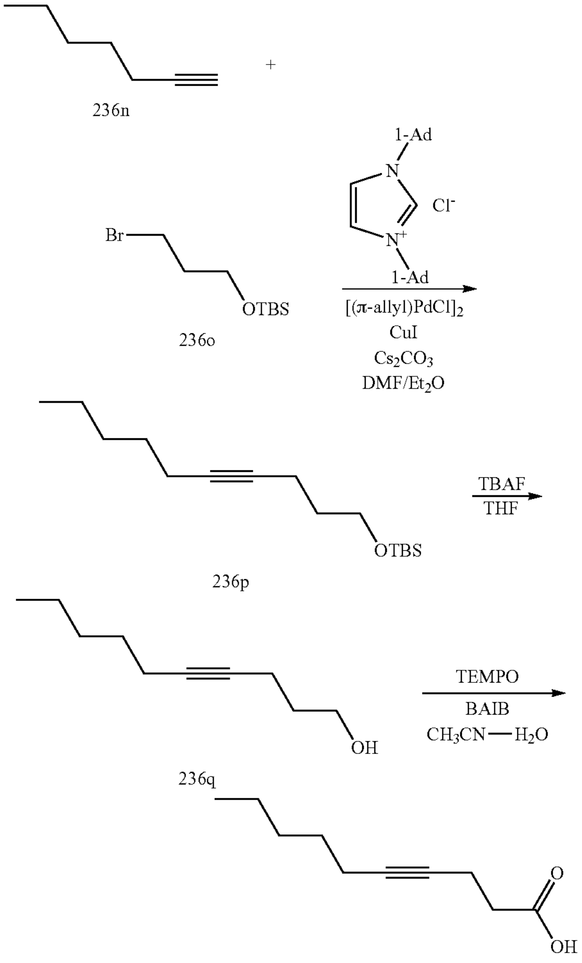

236n

236o

236p

236q

236r

Dec-4-ynoic acid was synthesized by operations similar to those in Example 236-10, Reaction 39-2 and Reaction 236-9 using appropriate reagents and starting material.

$^1$H-NMR (400 MHz, $CDCl_3$) δ 0.89 (3H, t, J=6.8 Hz), 1.32 (4H, m), 1.47 (2H, m), 2.13 (2H, m), 2.49 (2H, m), 2.57 (2H, m).

The carboxylic acid reagent used in the synthesis of Compound 1026 (11-(3-methyl-oxetan-3-yl)-undecanoic acid) was synthesized by the following method.

(Reaction 236-13)

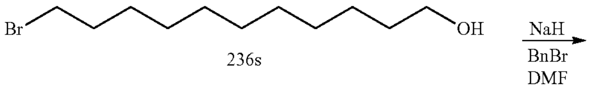

236s

-continued

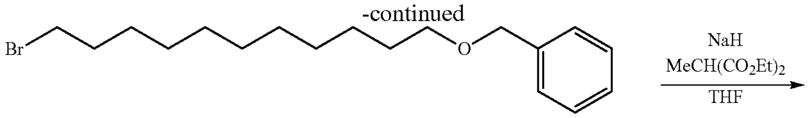

236t

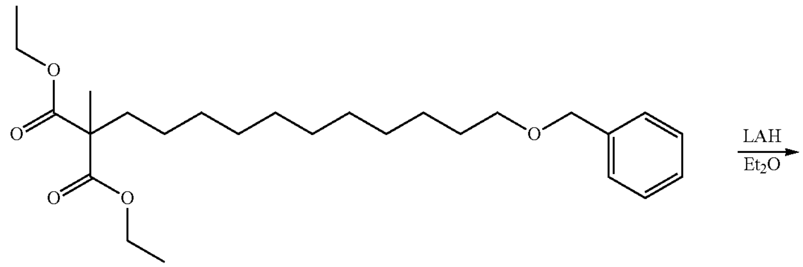

236u

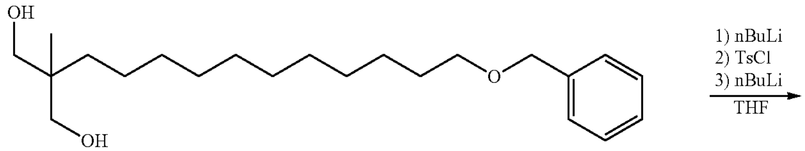

236v

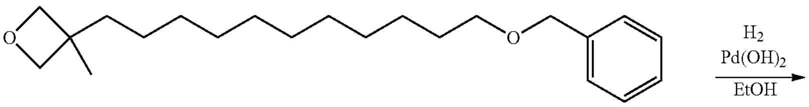

236w

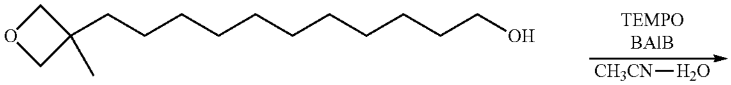

236x

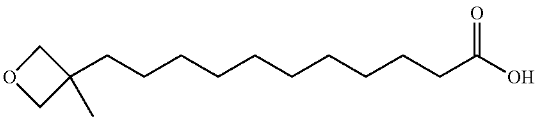

236y 11-(3-Methyl-oxetan-3-yl)-undecanoic acid was synthesized by operations similar to those in Reaction 20-2, Reaction 236-5, Reaction 95-28, Reaction 236-7, Reaction 122-2 and Reaction 236-9 using appropriate reagents and starting material.

$^1$H-NMR (400 MHz, $CDCl_3$) δ 1.27 (3H, s), 1.28 (14H, m), 1.62 (4H, m), 2.35 (2H, t, J=7.6 Hz), 4.34 (2H, d, J=5.6 Hz), 4.43 (2H, d, J=5.6 Hz).

The carboxylic acid reagent used in the synthesis of Compound 1027 (dec-2-ynoic acid) was synthesized by the following method.

(Reaction 236-14)

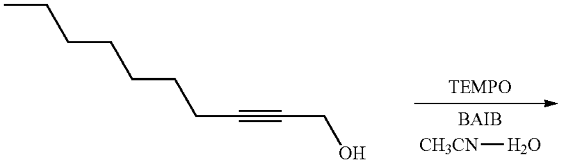

236z

-continued

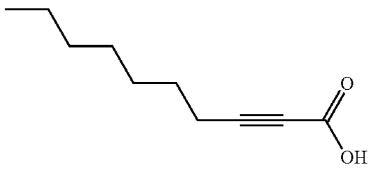

236aa

Dec-2-ynoic acid was synthesized by operations similar to those in Reaction 236-9 using appropriate reagents and starting material.

$^1$H-NMR (400 MHz, $CDCl_3$) δ 0.88 (3H, t, J=7.2 Hz), 1.28 (6H, m), 1.40 (2H, m), 1.59 (2H, m), 2.35 (2H, t, J=7.2 Hz).

Example 237
1-(4-{2-[2-(4-Fluoro-3-trifluoromethoxy-phenyl)-4-oxo-1,3,8-triaza-spiro[4.5]dec-1-ene-8-sulfonyl]-ethyl}-3,5-dimethyl-phenyl)-1-methyl-urea (Compound 1028)
(Reaction 237-1)
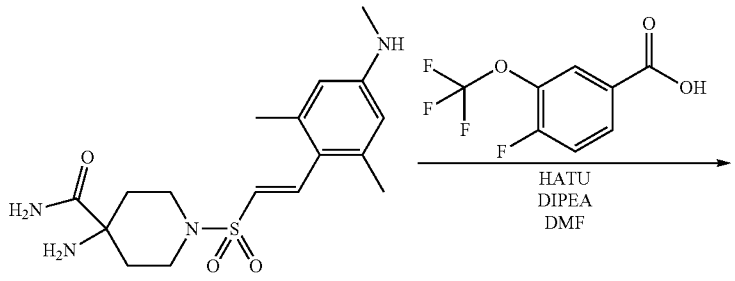
233f
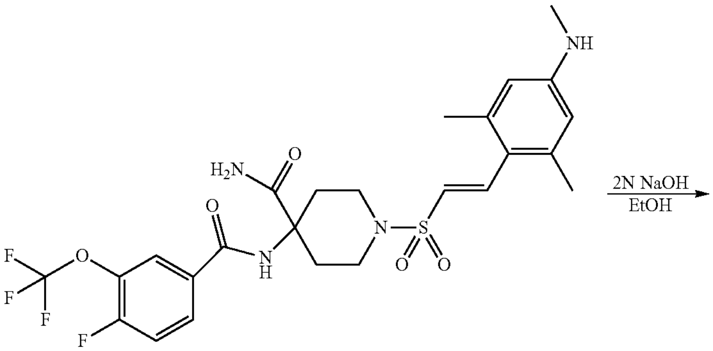
237a
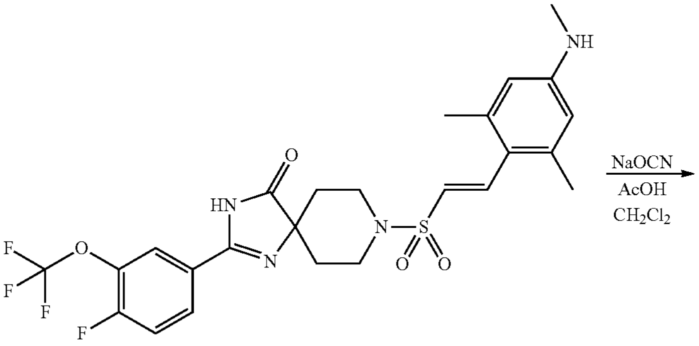
237b
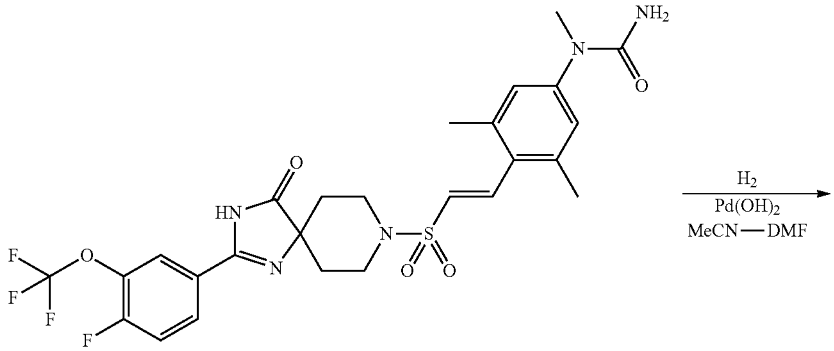
237c -continued

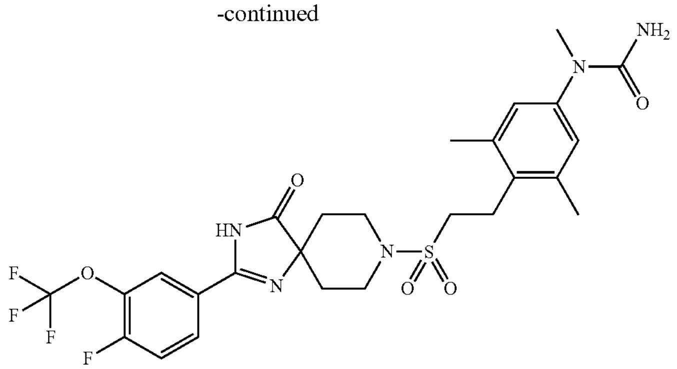

Compound 1028

1-(4-{2-[2-(4-Fluoro-3-trifluoromethoxy-phenyl)-4-oxo-1,3,8-triaza-spiro[4.5]dec-1-ene-8-sulfonyl]-ethyl}-3,5-dimethyl-phenyl)-1-methyl-urea was synthesized by operations similar to those in Reaction 10-14, Reaction 189-5, Reaction 89-2 and Reaction 184-1 using appropriate reagents and starting material.

MS (ESI) m/z=600 (M+H)+.

The example compounds shown below were synthesized by operations similar to those in Reaction 237-1 using appropriate reagents and starting materials.

Compounds 1029 to 1030

TABLE 151

| Compound | Structure | LCMS condition | Retention time (min) | MS (m/z) |
|---|---|---|---|---|
| 1029 | 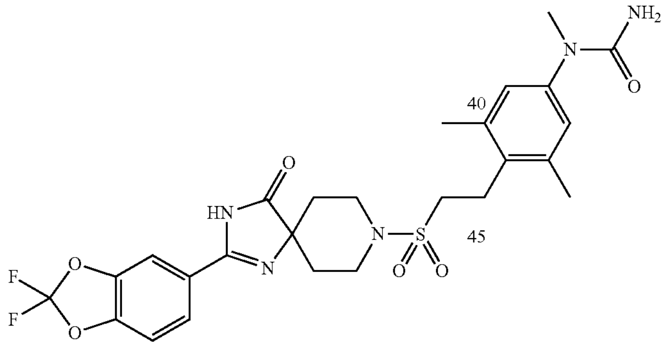 [SMILES: Cc1cc(N(C)C(N)=O)cc(C)c1CCS(=O)(=O)N1CCC2(CC1)N=C(c1ccc3c(c1)OC(F)(F)O3)NC2=O] | LCMS-F-1 | 0.95 | 578 (M + H)+ |
| 1030 | 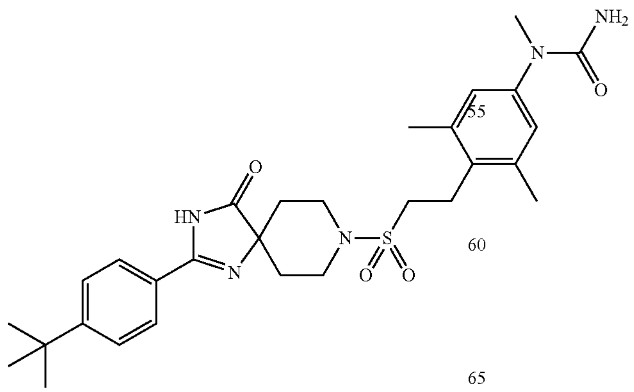 [SMILES: Cc1cc(N(C)C(N)=O)cc(C)c1CCS(=O)(=O)N1CCC2(CC1)N=C(c1ccc(C(C)(C)C)cc1)NC2=O] | LCMS-F-1 | 0.99 | 554 (M + H)+ |

Example 238

1-[3,5-Dimethyl-4-(2-{2-[8-(3-methyl-oxetan-3-yl)-octyl]-4-oxo-1,3,8-triaza-spiro[4.5]dec-1-ene-8-sulfonyl}-ethyl)-phenyl]-1-methyl-urea (Compound 1031)

(Reaction 238-1)

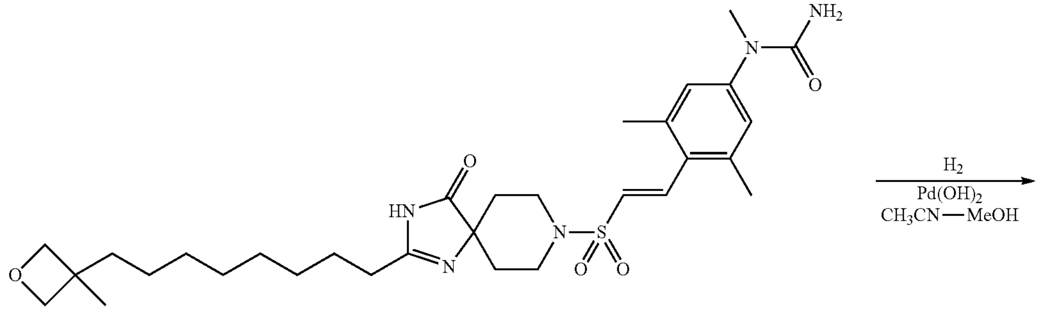

Compound 1023

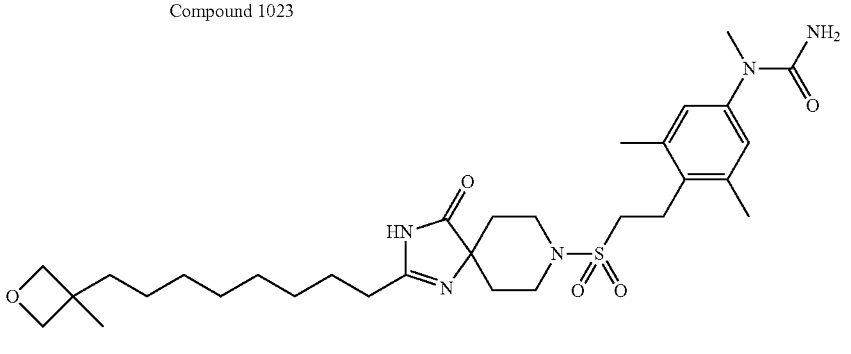

Compound 1031

1-[3,5-Dimethyl-4-(2-{2-[8-(3-methyl-oxetan-3-yl)-octyl]-4-oxo-1,3,8-triaza-spiro[4.5]dec-1-ene-8-sulfonyl}-ethyl)-phenyl]-1-methyl-urea was synthesized by operations similar to those in Reaction 184-1 using appropriate reagents and starting material.

MS (ESI) m/z=604 (M+H)+.

The example compound shown below was synthesized by operations similar to those in Reaction 238-1 using appropriate reagents and starting material.

Compound 1032

TABLE 152

| Compound | Structure | LCMS condition | Retention time (min) | MS (m/z) |
| --- | --- | --- | --- | --- |
| 1032 | 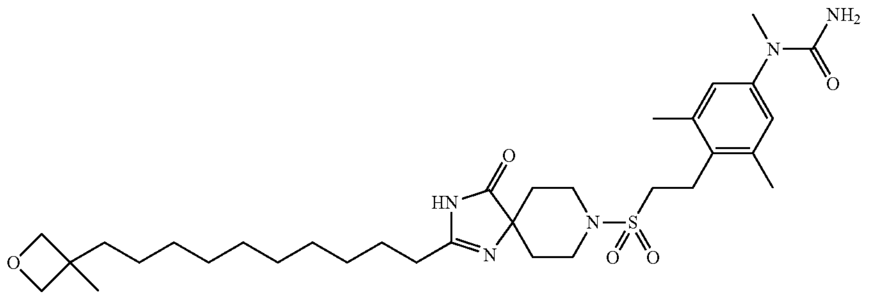 [SMILES: Cc1cc(N(C)C(N)=O)cc(C)c1CCS(=O)(=O)N1CCC2(CC1)N=C(CCCCCCCCCCC1(C)COC1)NC2=O] | LCMS-C-2 | 2.13 | 630 (M − H)− |

Example 239

2-(8-{2-[4-(tert-Butoxycarbonyl-methyl-amino)-2,6-dimethyl-phenyl]-ethanesulfonyl}-4-oxo-1,3,8-triaza-spiro[4.5]dec-1-en-2-yl)-pyrrolidine-1-carboxylic acid tert-butyl ester (Compound 1033)

(Reaction 239-1)

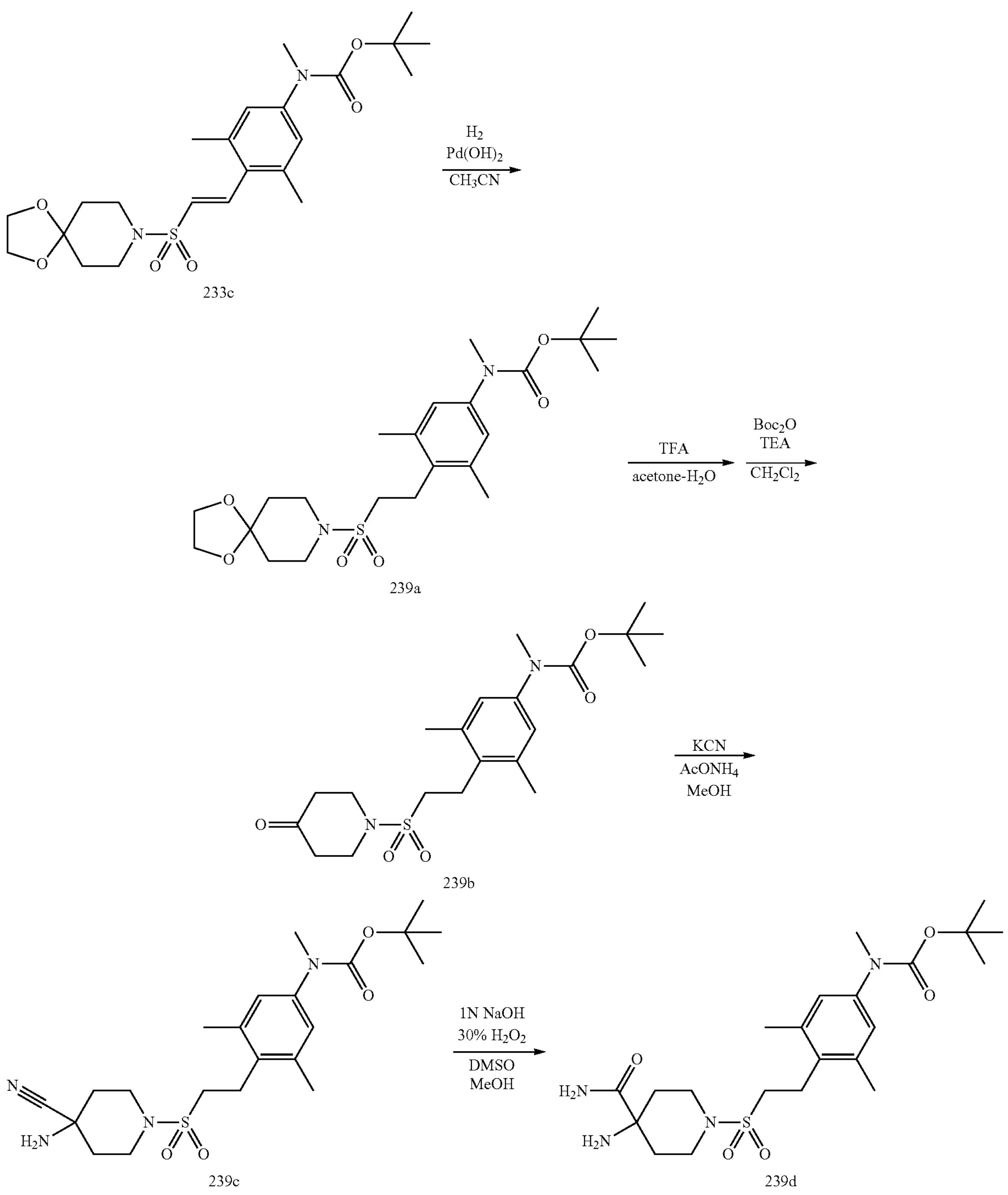

{4-[2-(4-Amino-4-carbamoyl-piperidine-1-sulfonyl)-ethyl]-3,5-dimethyl-phenyl}-methyl-carbamic acid tert-butyl ester was synthesized by operations similar to those in Reaction 184-1, Reaction 233-2, Reaction 19-2, Reaction 233-3 and Reaction 233-4 using appropriate reagents and starting material.

MS (ESI) m/z=469 (M+H)+.

(Reaction 239-2)
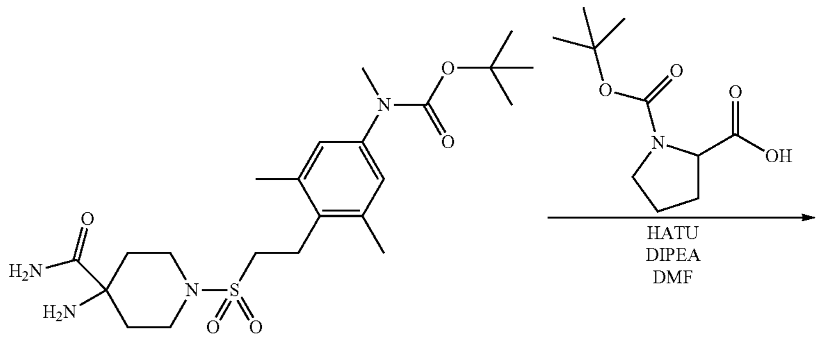
239d
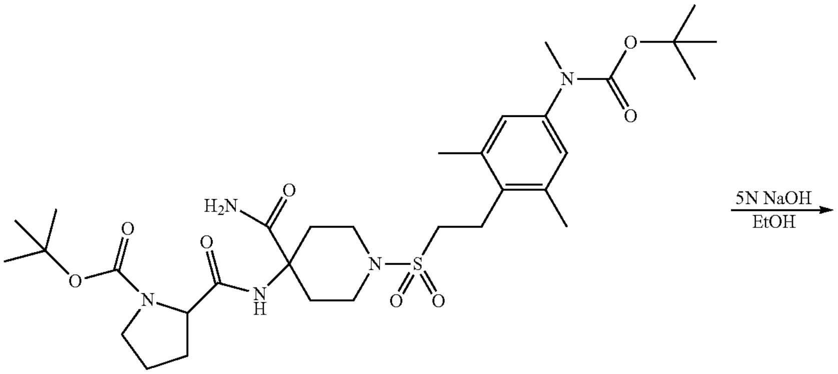
239e
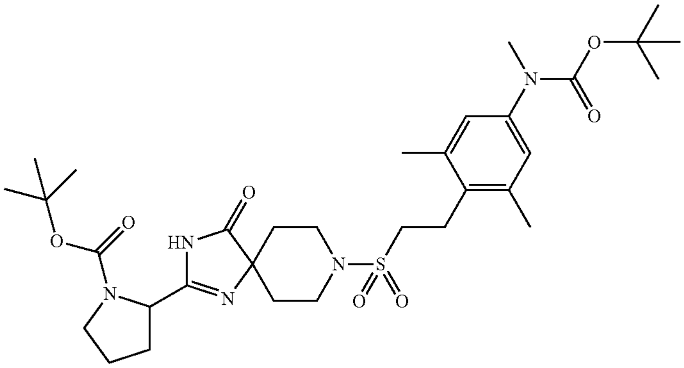
Compound 1033

2-(8-{2-[4-(tert-Butoxycarbonyl-methyl-amino)-2,6-dimethyl-phenyl]-ethanesulfonyl}-4-oxo-1,3,8-triaza-spiro[4.5]dec-1-en-2-yl)-pyrrolidine-1-carboxylic acid tert-butyl ester was synthesized by operations similar to those in Reaction 10-14 and Reaction 189-5 using appropriate reagents and starting material.

MS (ESI) m/z=648 (M+H)+.

The example compound shown below was synthesized by operations similar to those in Reaction 239-2 using appropriate reagents and starting material.

Compound 1034

TABLE 153

| Compound | Structure | LCMS condition | Retention time (min) | MS (m/z) |
|---|---|---|---|---|
| 1034 | 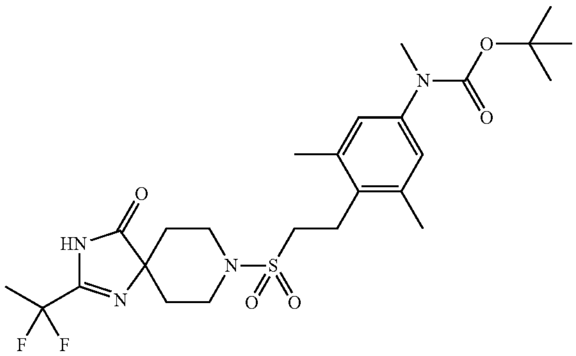 [SMILES: Cc1cc(N(C)C(=O)OC(C)(C)C)cc(C)c1CCS(=O)(=O)N1CCC2(CC1)N=C(C(C)(F)F)NC2=O] | LCMS-F-1 | 1.01 | 541 (M − H)− |

Example 240

8-[2-(2,6-Dimethyl-4-methylamino-phenyl)-ethanesulfonyl]-2-(8,8,9,9,9-pentafluoro-nonyl)-1,3,8-triaza-spiro[4.5]dec-1-en-4-one (Compound 1035)

(Reaction 240-1)

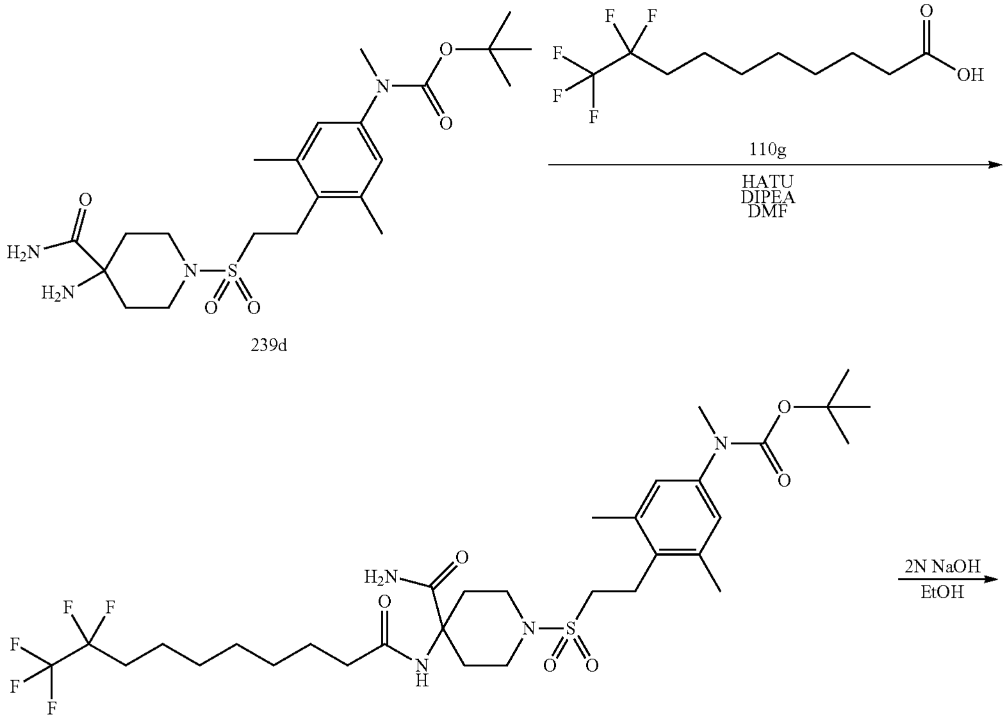

239d

240a

-continued

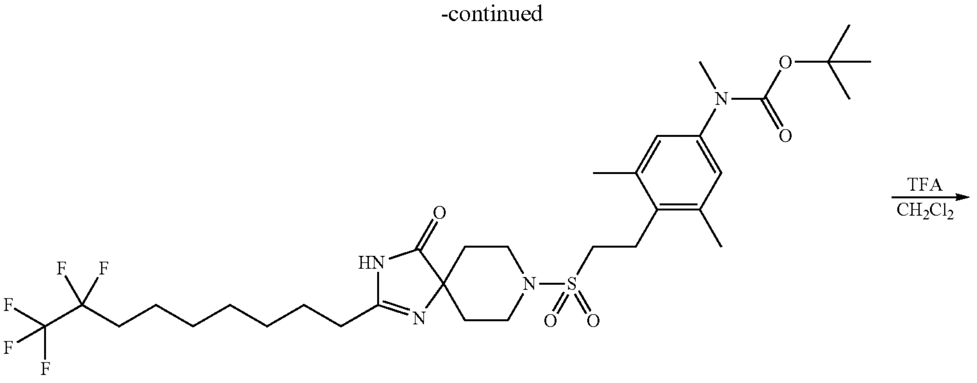

240b

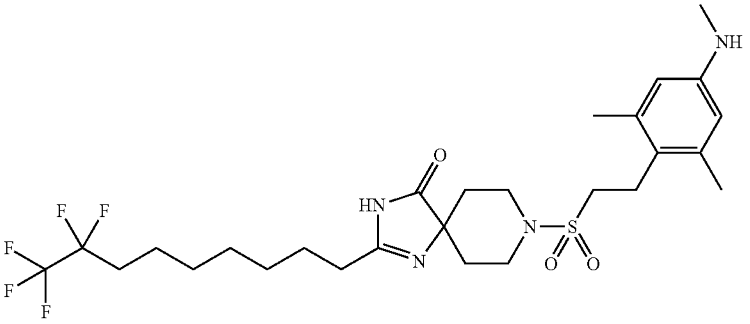

Compound 1035

8-[2-(2,6-Dimethyl-4-methylamino-phenyl)-ethanesulfonyl]-2-(8,8,9,9,9-pentafluoro-nonyl)-1,3,8-triaza-spiro[4.5]dec-1-en-4-one was synthesized by operations similar to those in Reaction 10-14, Reaction 189-5 and Reaction 4-1 using appropriate reagents and starting material.

MS (ESI) m/z=595 (M+H)+.

The example compound shown below was synthesized by operations similar to those in Reaction 240-1 using appropriate reagents and starting material.

Compound 1036

TABLE 154

| Compound | Structure | LCMS condition | Retention time (min) | MS (m/z) |
|---|---|---|---|---|
| 1036 | 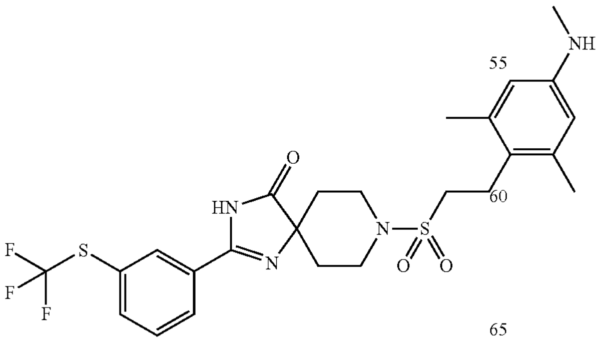 [SMILES: CNc1cc(C)c(CCS(=O)(=O)N2CCC3(CC2)N=C(c2cccc(SC(F)(F)F)c2)NC3=O)c(C)c1] | LCMS-C-1 | 2.93 | 555 (M + H)+ |

Example 241

8-[2-(2,6-Dimethyl-4-methylamino-phenyl)-ethane-sulfonyl]-2-(4-isopropylidene-cyclohexyl)-1,3,8-triaza-spiro[4.5]dec-1-en-4-one (Compound 1037)

(Reaction 241-1)

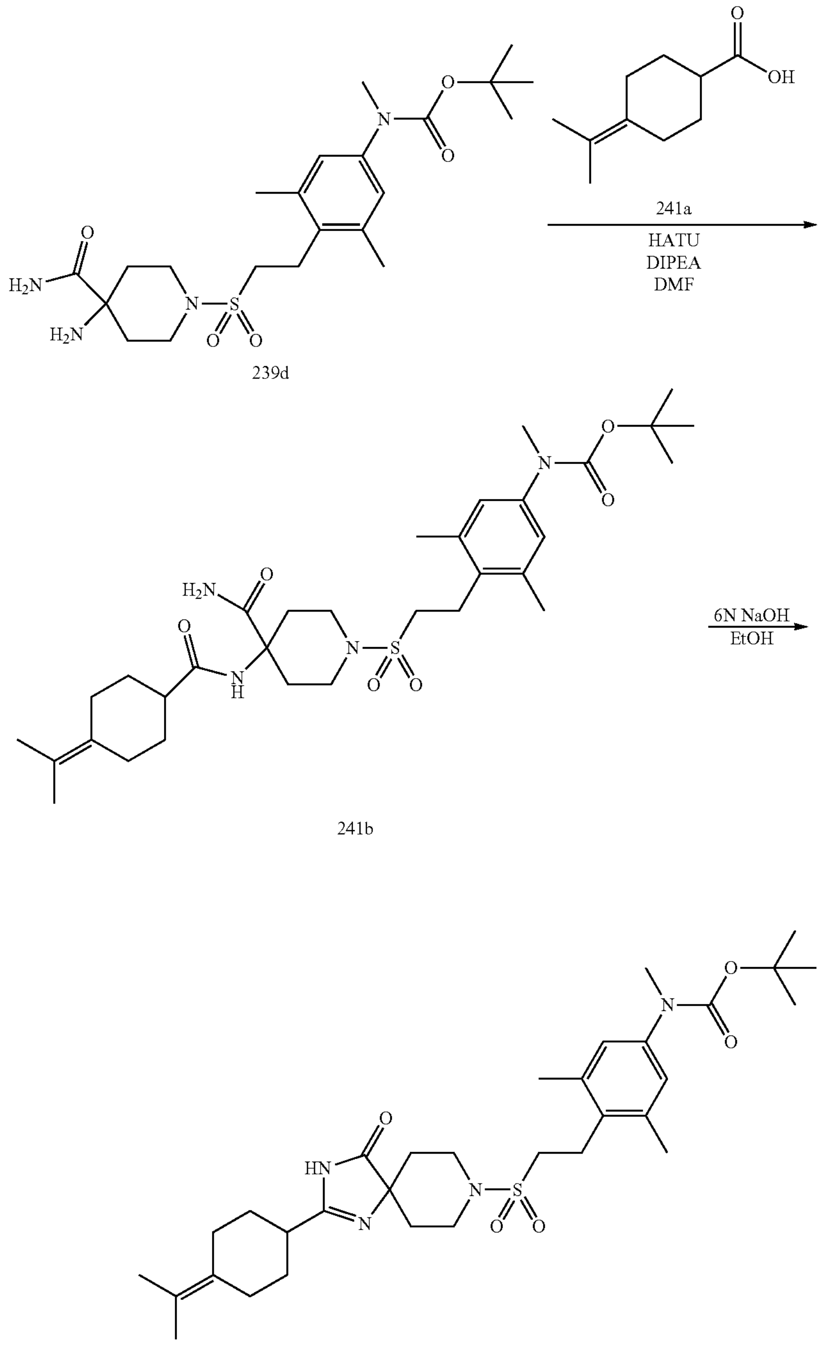

241c (4-{2-[2-(4-Isopropylidene-cyclohexyl)-4-oxo-1,3,8-triaza-spiro[4.5]dec-1-ene-8-sulfonyl]-ethyl}-3,5-dimethyl-phenyl)-methyl-carbamic acid tert-butyl ester was synthesized by operations similar to those in Reaction 10-14 and Reaction 189-5 using appropriate reagents and starting material.

MS (ESI) m/z=601 (M+H)+.

(Reaction 241-2)

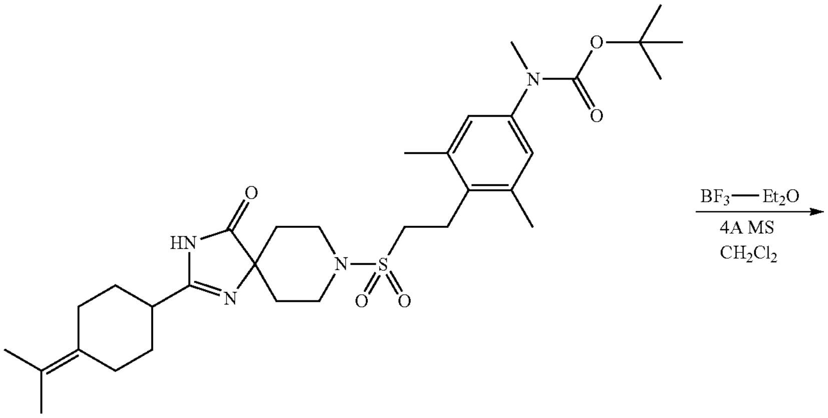

241c

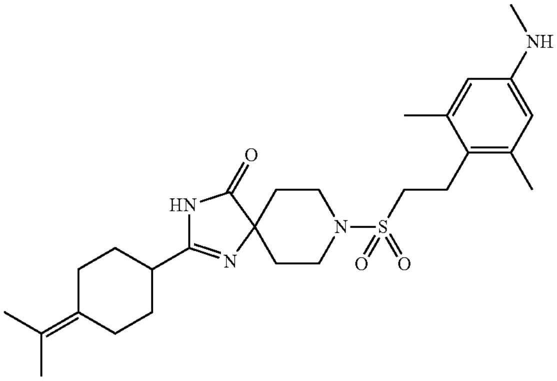

Compound 1037

About 40 4AMS beads were added to a solution of (4-{2-[2-(4-isopropylidene-cyclohexyl)-4-oxo-1,3,8-triaza-spiro[4.5]dec-1-ene-8-sulfonyl]-ethyl}-3,5-dimethyl-phenyl)-methyl-carbamic acid tert-butyl ester (85.7 mg, 143 μmol) in dichloromethane (1.4 ml), and the mixture was stirred at room temperature for 10 minutes. Thereafter, $BF_3.Et_2O$ (90.2 μl, 715 μmol) was added to the reaction mixture at 0° C., and the mixture was stirred at room temperature for three hours. The reaction mixture was quenched by adding triethylamine and diluted with ethyl acetate. The organic layer was then washed with a saturated aqueous sodium bicarbonate solution and water, and then dried over $MgSO_4$ and concentrated under reduced pressure. The resulting residue was purified by silica gel column chromatography (dichloromethane/methanol=100/0→92/8) to give 8-[2-(2,6-dimethyl-4-methylamino-phenyl)-ethanesulfonyl]-2-(4-isopropylidene-cyclohexyl)-1,3,8-triaza-spiro[4.5]dec-1-en-4-one (66.0 mg, 92%).

MS (ESI) m/z=501 (M+H)+.

The carboxylic acid reagent used in the synthesis of Compound 1037 (4-isopropylidene-cyclohexanecarboxylic acid) was synthesized by the following method.

(Reaction 241-3)

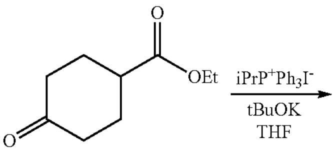

101b

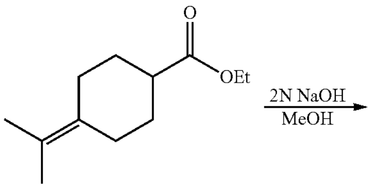

241d

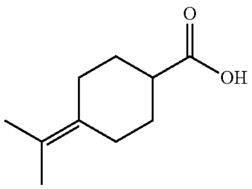

241a

4-Isopropylidene-cyclohexanecarboxylic acid was synthesized by operations similar to those in Reaction 191-14 and Reaction 189-5 using appropriate reagents and starting material.
MS (ESI) m/z=169 (M+H)+.
Example 242
1-[3,5-Dimethyl-4-(2-{4-oxo-2-[3-(1,1,2,2-tetrafluoro-ethoxy)-phenyl]-1,3,8-triaza-spiro[4.5]dec-1-ene-8-sulfonyl}-ethyl)-phenyl]-1-methyl-urea (Compound 1038)
(Reaction 242-1)
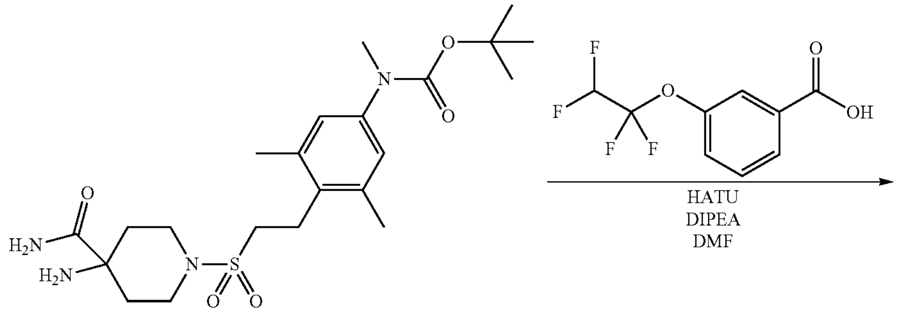
239d
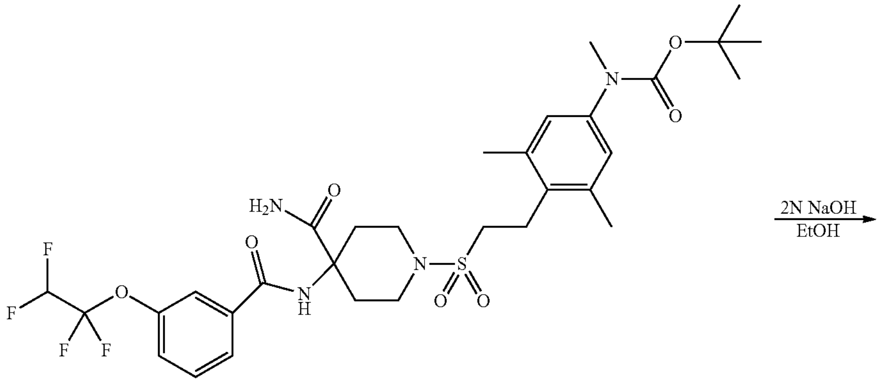
242a
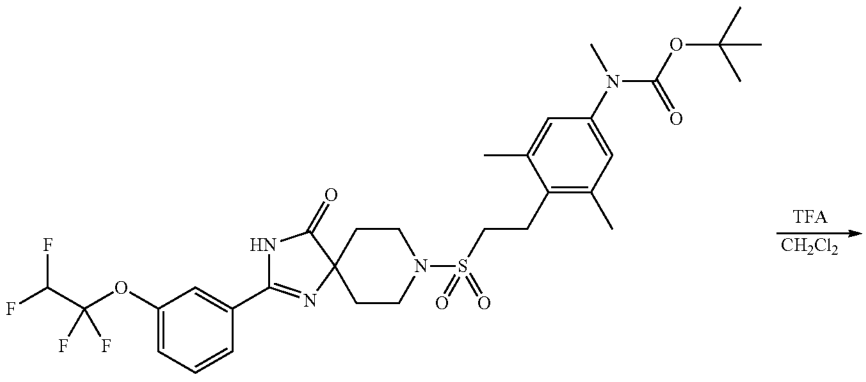
242b -continued

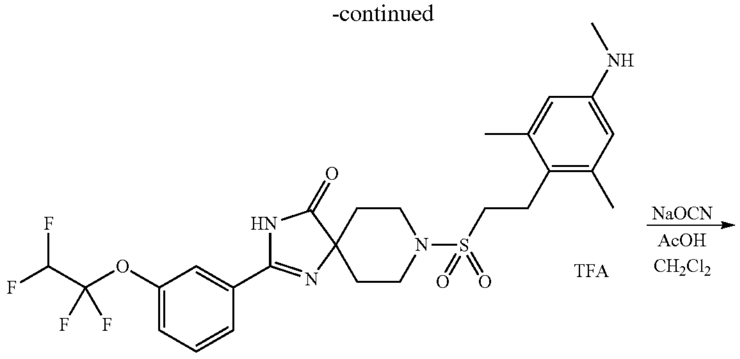

242c

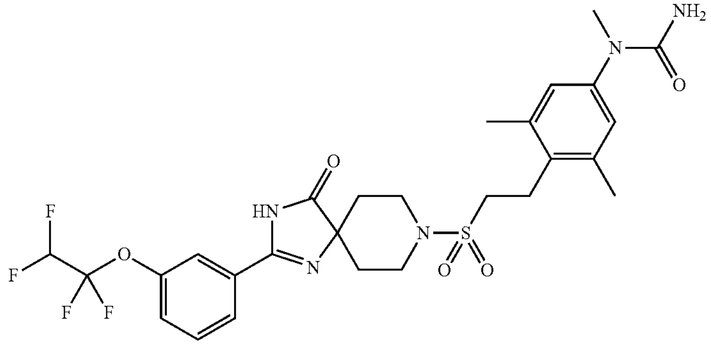

Compound 1038

1-[3,5-Dimethyl-4-(2-{4-oxo-2-[3-(1,1,2,2-tetrafluoro-ethoxy)-phenyl]-1,3,8-triaza-spiro[4.5]dec-1-ene-8-sulfonyl}-ethyl)-phenyl]-1-methyl-urea was synthesized by operations similar to those in Reaction 10-14, Reaction 189-5, Reaction 4-1 and Reaction 89-2 using appropriate reagents and starting material.

MS (ESI) m/z=614 (M+H)+.

Example 243

1-(3,5-Dimethyl-4-{2-[4-oxo-2-(5,6,7,8-tetrahydro-naphthalen-2-yl)-1,3,8-triaza-spiro[4.5]dec-1-ene-8-sulfonyl]-ethyl}-phenyl)-1-methyl-urea (Compound 1039)

(Reaction 243-1)

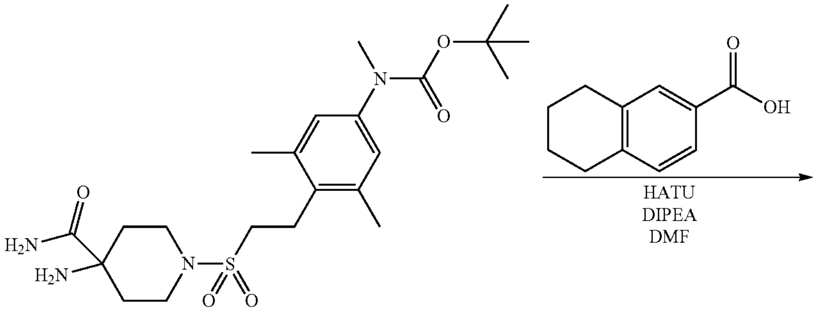

239d

-continued
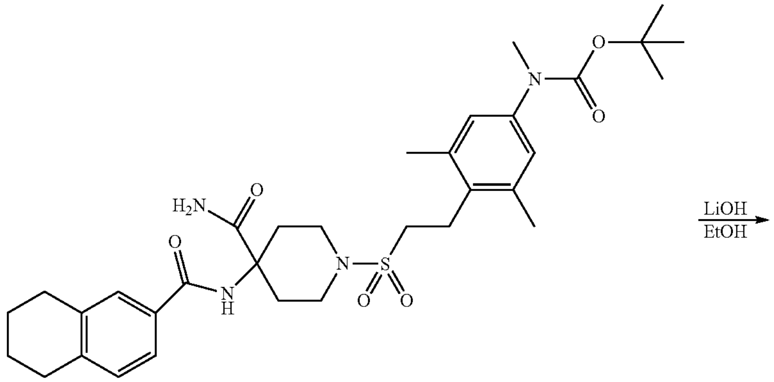
243a
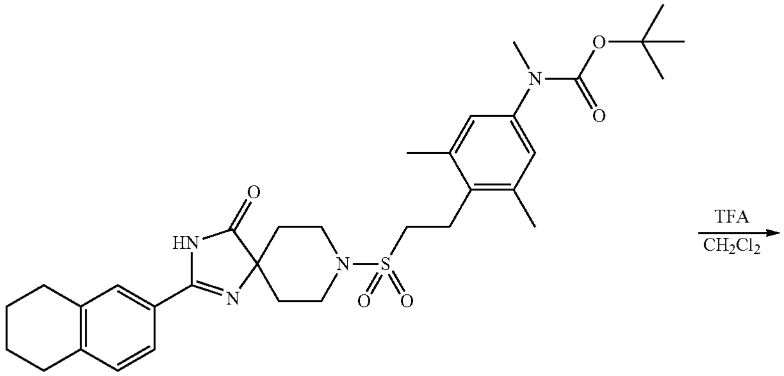
243b
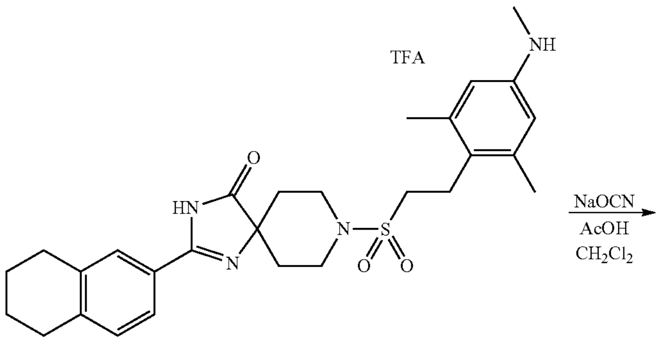
243c
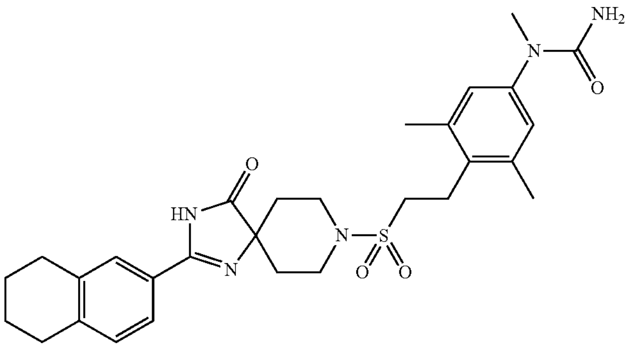
Compound 1039

1-(3,5-Dimethyl-4-{2-[4-oxo-2-(5,6,7,8-tetrahydro-naphthalen-2-yl)-1,3,8-triaza-spiro[4.5]dec-1-ene-8-sulfonyl]-ethyl}-phenyl)-1-methyl-urea was synthesized by operations similar to those in Reaction 10-14, Reaction 236-2, Reaction 4-1 and Reaction 89-2 using appropriate reagents and starting material.

MS (ESI) m/z=552 (M+H)+.

The example compounds shown below were synthesized by operations similar to those in Reaction 243-1 using appropriate reagents and starting materials.

Compounds 1040 to 1042

TABLE 155

| Compound | Structure | LCMS condition | Retention time (min) | MS (m/z) |
|---|---|---|---|---|
| 1040 | 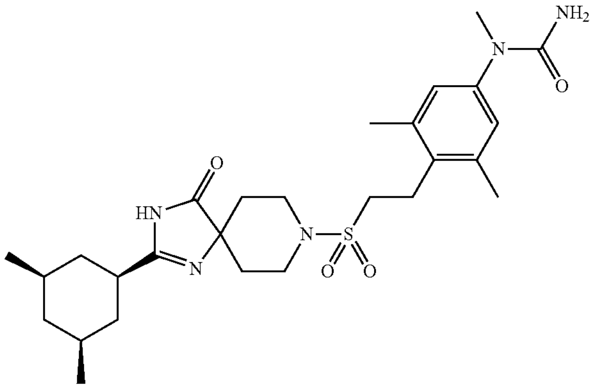 [SMILES: Cc1cc(N(C)C(N)=O)cc(C)c1CCS(=O)(=O)N1CCC2(CC1)N=C([C@@H]1C[C@H](C)C[C@H](C)C1)NC2=O] | LCMS-A-1 | 2.06 | 532 (M + H)+ |
| 1041 | 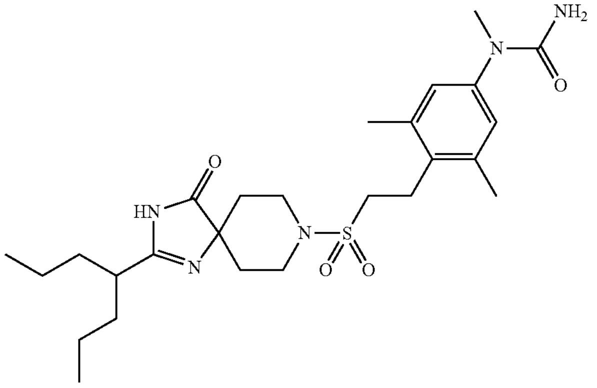 [SMILES: CCCC(CCC)C1=NC2(CCN(S(=O)(=O)CCc3c(C)cc(N(C)C(N)=O)cc3C)CC2)C(=O)N1] | LCMS-A-1 | 2.00 | 520 (M + H)+ |
| 1042 | 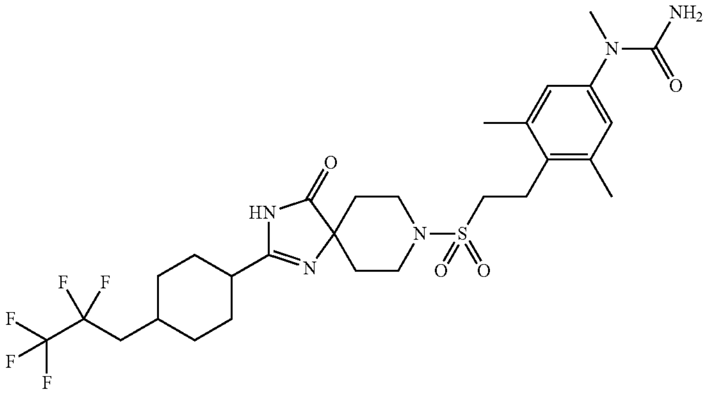 [SMILES: Cc1cc(N(C)C(N)=O)cc(C)c1CCS(=O)(=O)N1CCC2(CC1)N=C(C1CCC(CC(F)(F)C(F)(F)F)CC1)NC2=O] | LCMS-A-1 | 2.26 | 636 (M + H)+ |

The carboxylic acid reagent used in the synthesis of Compound 1042 (4-(2,2,3,3,3-pentafluoro-propyl)-cyclohexanecarboxylic acid) was synthesized by the following method.

(Reaction 243-2)

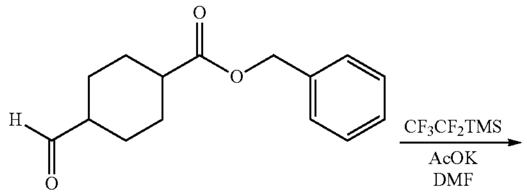

190d

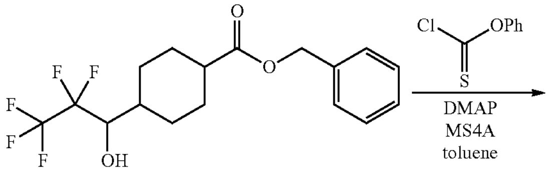

243d

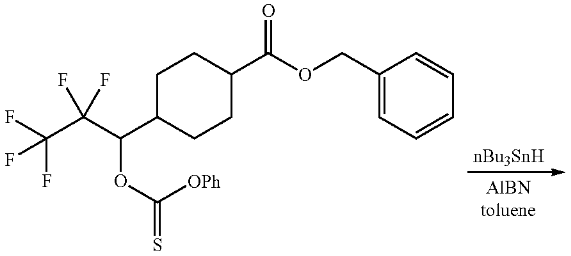

243e

-continued

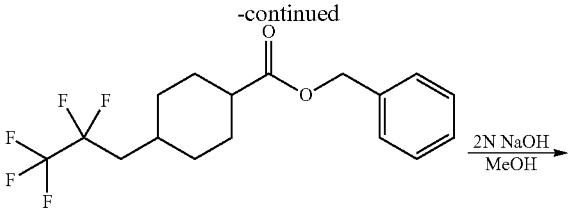

243f

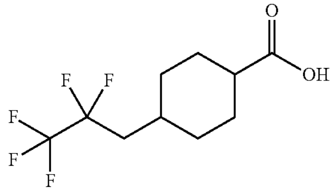

243g 4-(2,2,3,3,3-Pentafluoro-propyl)-cyclohexanecarboxylic acid was synthesized by operations similar to those in Reaction 193-4, Reaction 193-5, Reaction 193-6 and Reaction 95-18 using appropriate reagents and starting material.

$^1$H-NMR (400 MHz, $CDCl_3$) δ 2.64 (0.6H, qui, J=4.9 Hz), 2.29 (0.4H, tt, J=12.2, 3.4 Hz), 2.09-1.06 (11H, m). (cis/trans=ca 6:4)

Example 244

1-(3,5-Dimethyl-4-{2-[4-oxo-2-(6,6,7,7,7-pentafluoro-heptyl)-1,3,8-triaza-spiro[4.5]dec-1-ene-8-sulfonyl]-ethyl}-phenyl)-1-methyl-urea (Compound 1043)

(Reaction 244-1)

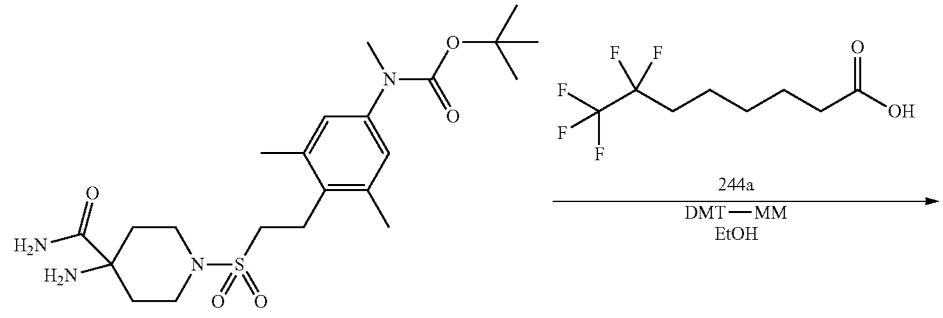

239d

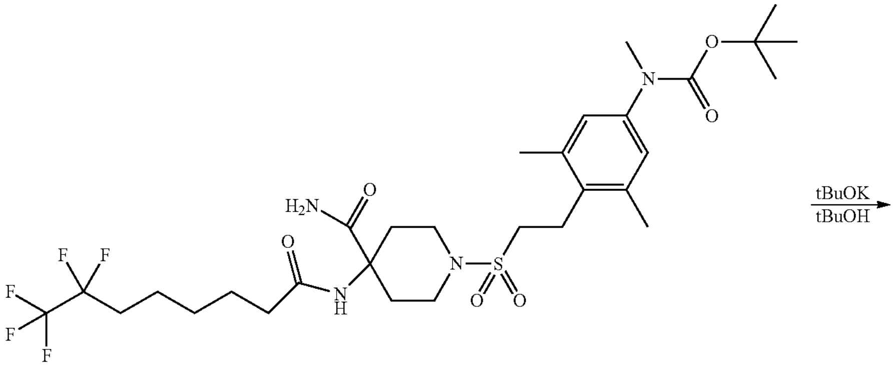

244b

-continued

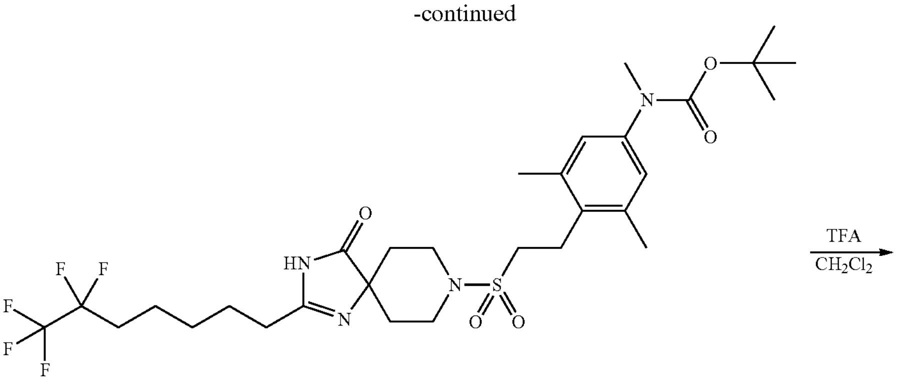

244c

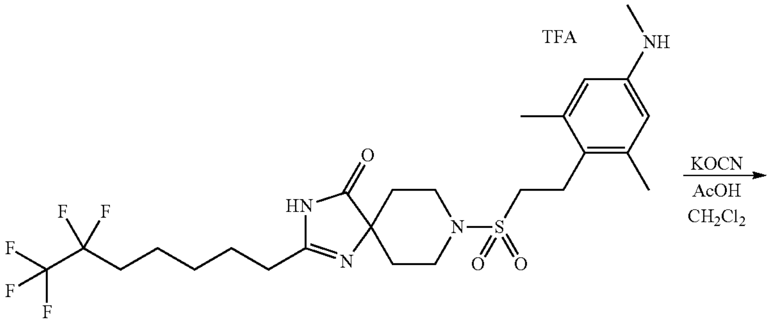

244d

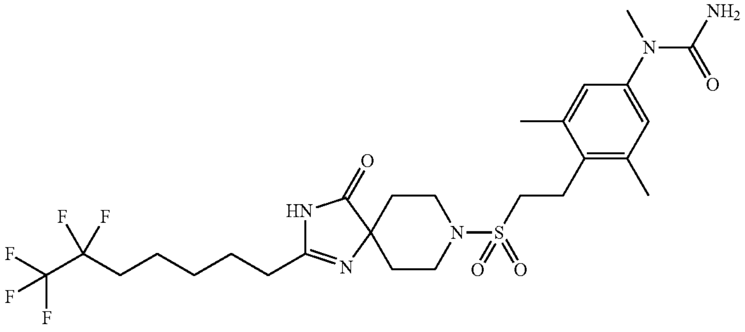

Compound 1043

1-(3,5-Dimethyl-4-{2-[4-oxo-2-(6,6,7,7,7-pentafluoro-heptyl)-1,3,8-triaza-spiro[4.5]dec-1-ene-8-sulfonyl]-ethyl}-phenyl)-1-methyl-urea was synthesized by operations similar to those in Reaction 10-1, Reaction 10-12, Reaction 4-1 and Reaction 89-2 (using KOCN) using appropriate reagents and starting material.

MS (ESI) m/z=610 (M+H)+.

The carboxylic acid reagent used in the synthesis of Compound 1043 (7,7,8,8,8-pentafluoro-octanoic acid) was synthesized by the following method.

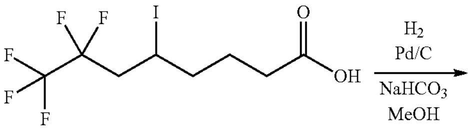

110b

-continued

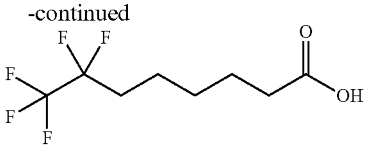

244a 7,7,8,8,8-Pentafluoro-octanoic acid was synthesized by operations similar to those in Reaction 18-2 using appropriate reagents and starting material.

$^1$H-NMR (400 MHz, $CDCl_3$) δ 1.42-1.48 (2H, m), 1.57-1.73 (4H, m), 2.03 (2H, tt, J=6.8, 18.2 Hz), 2.39 (2H, t, J=7.4 Hz).

Example 245
N-(3,5-Dimethyl-4-{2-[4-oxo-2-(7,7,7-trifluoro-heptyl)-1,3,8-triaza-spiro[4.5]dec-1-ene-8-sulfonyl]-ethyl}-phenyl)-N-methyl-acetamide (Compound 1044) and 1-(3,5-dimethyl-4-{2-[4-oxo-2-(7,7,7-trifluoro-heptyl)-1,3,8-triaza-spiro[4.5]dec-1-ene-8-sulfonyl]-ethyl}-phenyl)-1-methyl-urea (Compound 1045)
(Reaction 245-1)
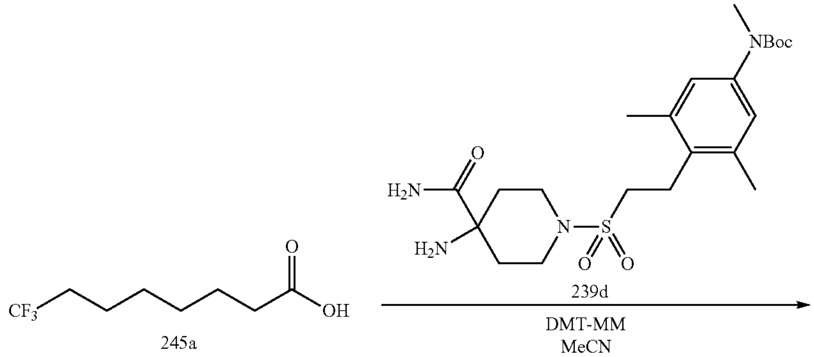
245a 239d
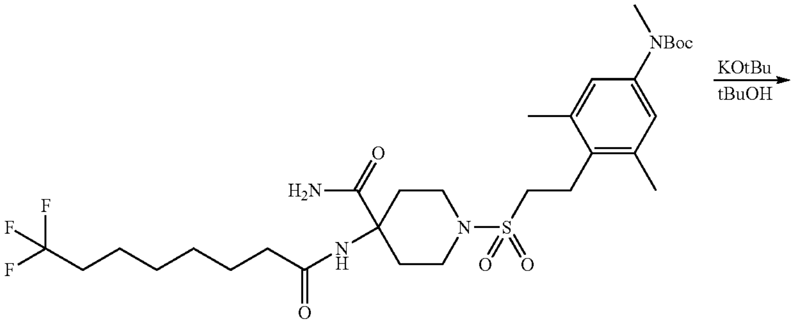
245b
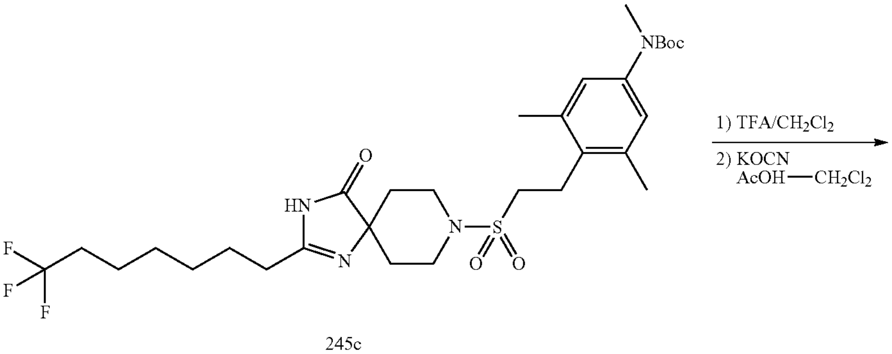
245c -continued

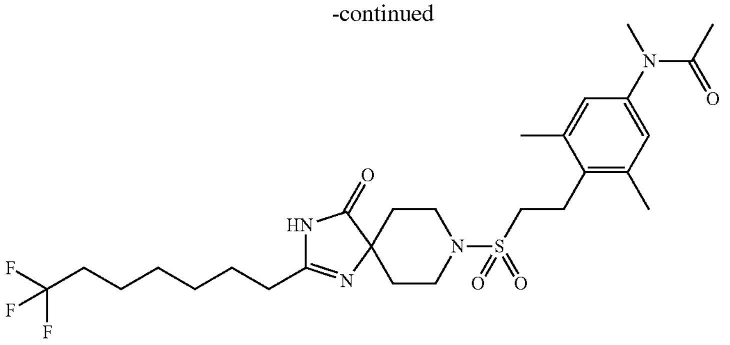

+

Compound 1044

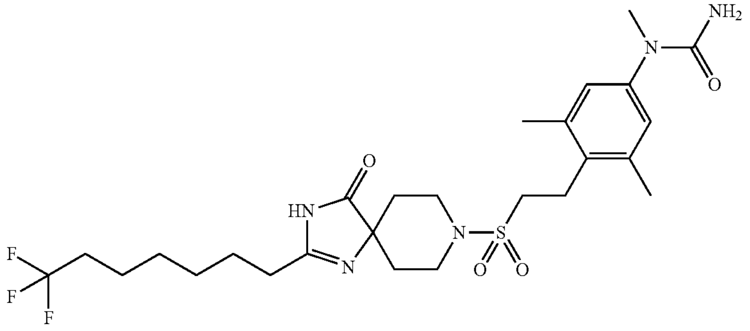

Compound 1045

N-(3,5-Dimethyl-4-{2-[4-oxo-2-(7,7,7-trifluoro-heptyl)-1,3,8-triaza-spiro[4.5]dec-1-ene-8-sulfonyl]-ethyl}-phenyl)-N-methyl-acetamide MS (ESI) m/z=573 (M+H)+ and 1-(3,5-dimethyl-4-{2-[4-oxo-2-(7,7,7-trifluoro-heptyl)-1,3,8-triaza-spiro[4.5]dec-1-ene-8-sulfonyl]-ethyl}-phenyl)-1-methyl-urea MS (ESI) m/z=574 (M+H)+ were synthesized by operations similar to those in Reaction 10-1, Reaction 10-12, Reaction 4-1 and Reaction 89-2 (using KOCN) using appropriate reagents and starting material.

The carboxylic acid reagent used in the synthesis of Compound 1044 and Compound 1045 (8,8,8-trifluoro-octanoic acid) was synthesized by the following method.

(Reaction 245-2)

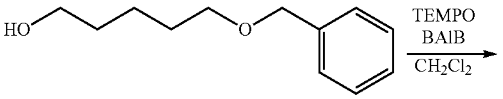

245d

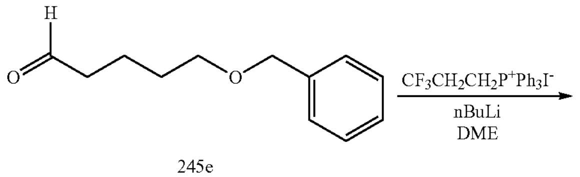

245e

-continued

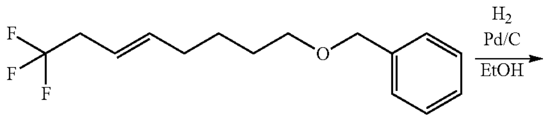

245f

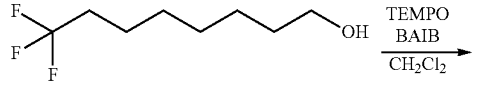

245g

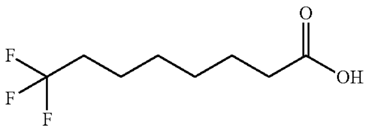

245a 8,8,8-Trifluoro-octanoic acid was synthesized by operations similar to those in Reaction 109-1, Reaction 101-1, Reaction 18-2 and Reaction 109-1 using appropriate reagents and starting material.

$^1$H-NMR (400 MHz, $CDCl_3$) δ 1.32-1.46 (4H, br-m), 1.52-1.68 (2H, m), 1.66-1.72 (2H, m), 2.00-2.14 (2H, m), 2.38 (2H, t, J=7.2 Hz).

The example compounds shown below were synthesized by operations similar to those in Reaction 245-1 using appropriate reagents and starting materials.

Compounds 1046 to Compound 1047
TABLE 156
| Compound | Structure | LCMS condition | Retention time (min) | MS (m/z) |
|---|---|---|---|---|
| 1046 | 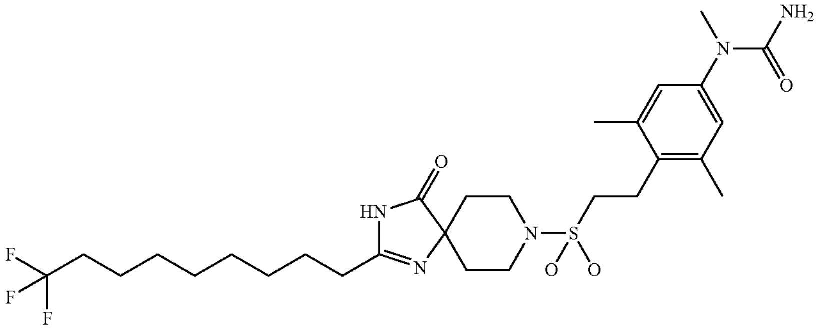 [SMILES: Cc1cc(N(C)C(N)=O)cc(C)c1CCS(O)(O)N1CCC2(CC1)N=C(CCCCCCCCC(F)(F)F)NC2=O] | LCMS-B-1 | 2.03 | 602 (M + H)+ |
| 1047 | 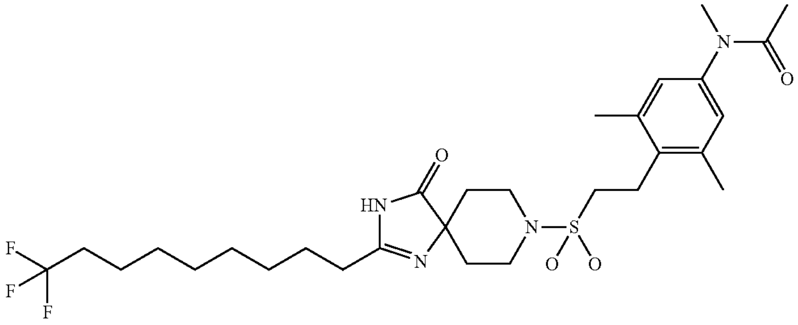 [SMILES: CC(=O)N(C)c1cc(C)c(CCS(O)(O)N2CCC3(CC2)N=C(CCCCCCCCC(F)(F)F)NC3=O)c(C)c1] | LCMS-B-1 | 2.16 | 601 (M + H)+ |
Example 246
1-[3,5-Dimethyl-4-(2-{4-oxo-2-[1-(4,4,4-trifluoro-butyl)-cyclopropyl]-1,3,8-triaza-spiro[4.5]dec-1-ene-8-sulfonyl}-ethyl)-phenyl]-1-methyl-urea (Compound 1048)
(Reaction 246-1)
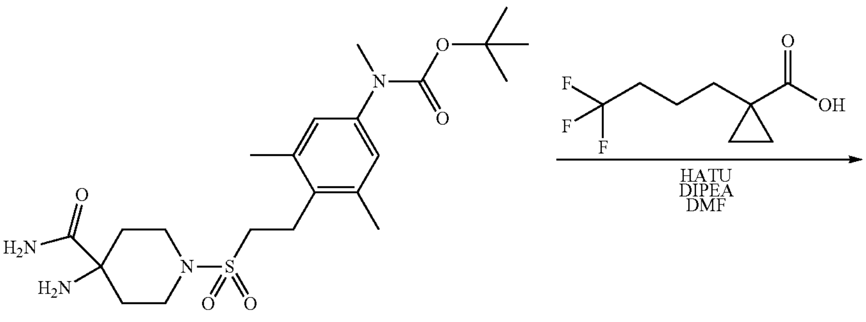
239d -continued
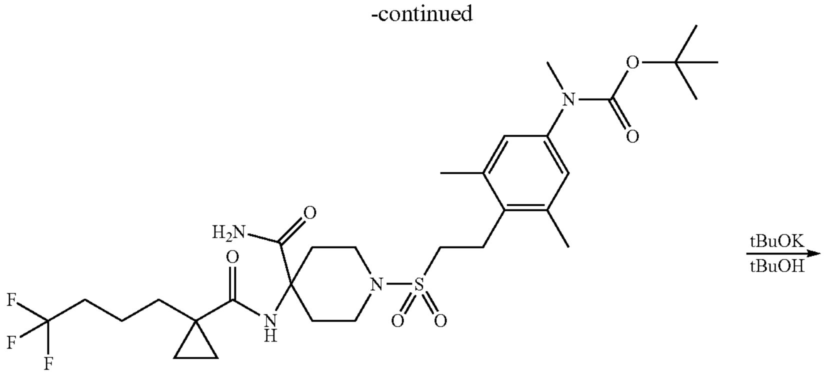
246a
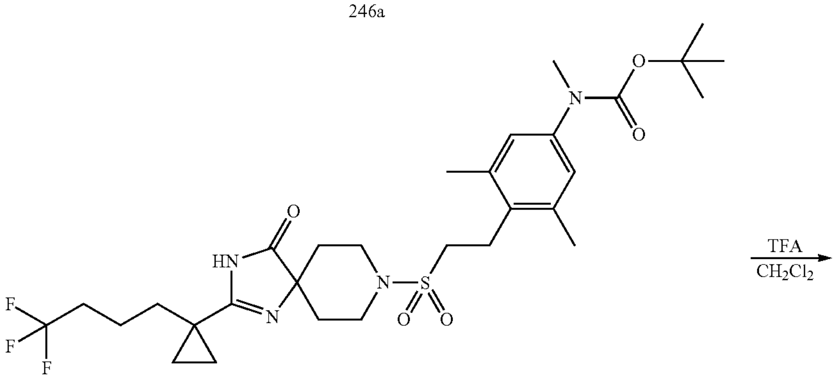
246b
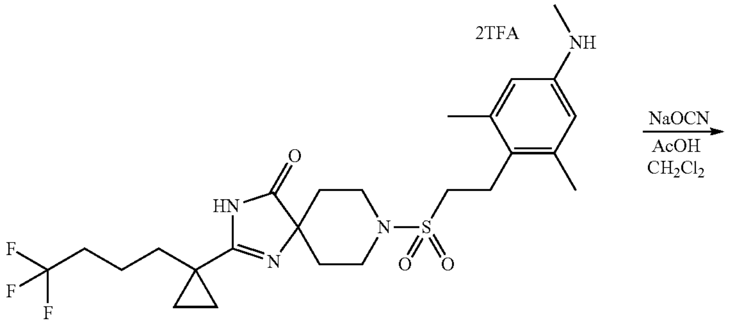
246c
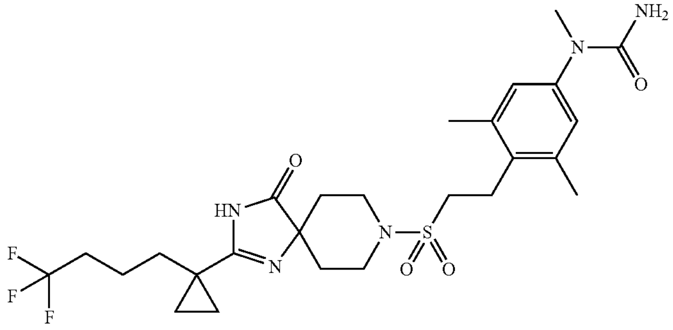
Compound 1048
1-[3,5-Dimethyl-4-(2-{4-oxo-2-[1-(4,4,4-trifluoro-butyl)-cyclopropyl]-1,3,8-triaza-spiro[4.5]dec-1-ene-8-sulfonyl}-ethyl)-phenyl]-1-methyl-urea was synthesized by operations similar to those in Reaction 10-14, Reaction 10-12, Reaction 4-1 and Reaction 89-2 (using KOCN) using appropriate reagents and starting material.
MS (ESI) m/z=572 (M+H)+.

Example 247
1-(3,5-Dimethyl-4-{2-[4-oxo-2-(3-trifluoromethyl-cyclohexyl)-1,3,8-triaza-spiro[4.5]dec-1-ene-8-sulfonyl]-ethyl}-phenyl)-1-methyl-urea (Compound 1050)
(Reaction 247-1)
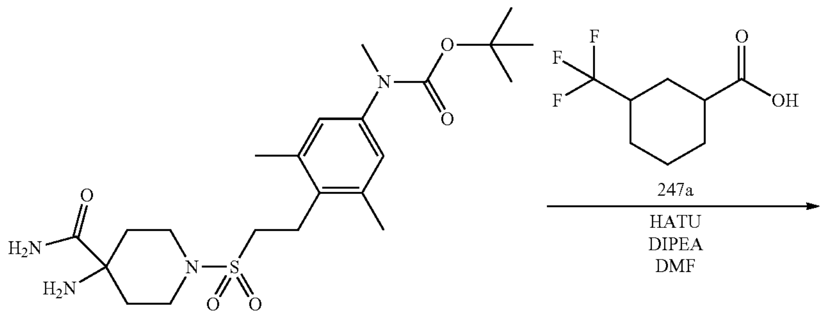
239d
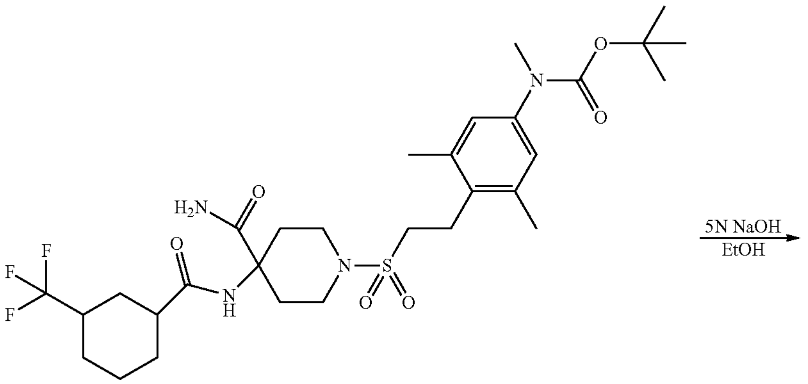
247b
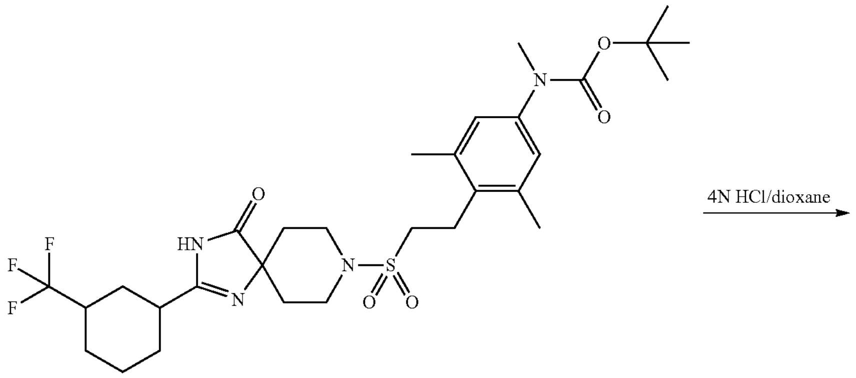
247c -continued

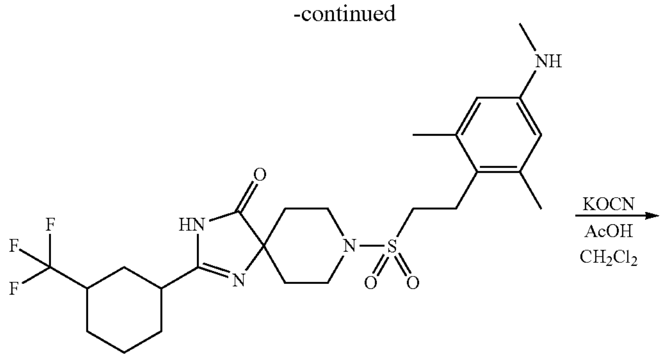

247d

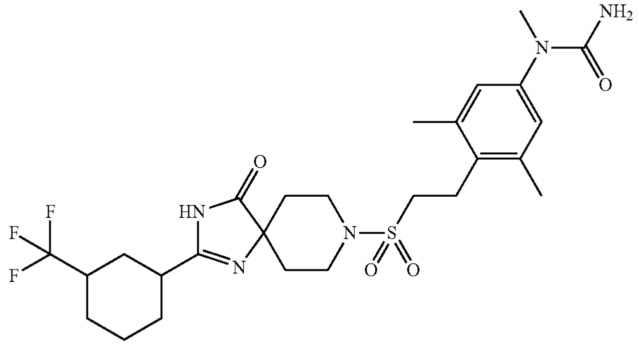

Compound 1050

1-(3,5-Dimethyl-4-{2-[4-oxo-2-(3-trifluoromethyl-cyclohexyl)-1,3,8-triaza-spiro[4.5]dec-1-ene-8-sulfonyl]-ethyl}-phenyl)-1-methyl-urea was synthesized by operations similar to those in Reaction 10-14, Reaction 189-5, Reaction 5-3 and Reaction 89-2 using appropriate reagents and starting material.

MS (ESI) m/z=572 (M+H)+.

The carboxylic acid reagent used in the synthesis of Compound 1050 (3-trifluoromethyl-cyclohexanecarboxylic acid) was synthesized by the following method.

(Reaction 247-2)

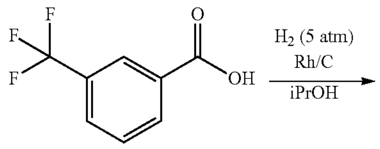

247e

-continued

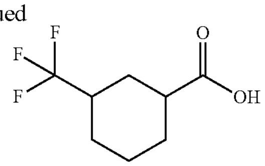

247a

3-Trifluoromethyl-cyclohexanecarboxylic acid was synthesized by operations similar to those in Reaction 193-3 using appropriate reagents and starting material.

$^1$H-NMR (400 MHz, $CDCl_3$) δ 1.22-2.40 (9.57H, m), 2.88 (0.43H, m) (cis:trans=1.3:1)

The example compounds shown below were synthesized by operations similar to those in Reaction 247-1 using appropriate reagents and starting materials.

Compounds 1051 to 1058
TABLE 157
| Compound | Structure | LCMS condition | Retention time (min) | MS (m/z) |
|---|---|---|---|---|
| 1051 | 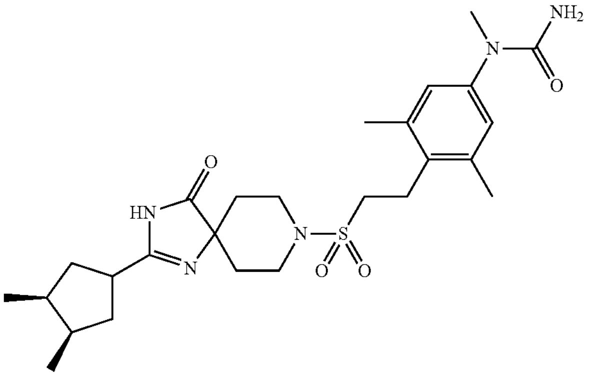 [SMILES: Cc1cc(N(C)C(N)=O)cc(C)c1CCS(=O)(=O)N1CCC2(CC1)N=C(C1C[C@@H](C)[C@@H](C)C1)NC2=O] | LCMS-F-1 | 0.93 | 518 (M + H)+ |
| 1052 | 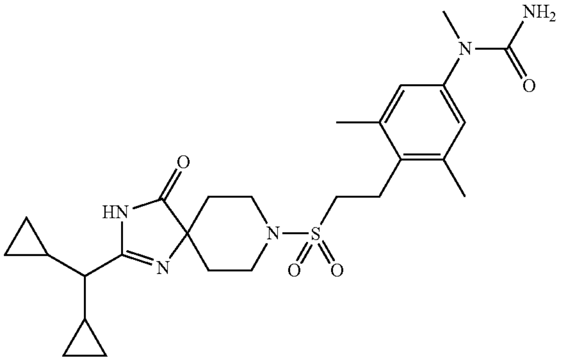 [SMILES: Cc1cc(N(C)C(N)=O)cc(C)c1CCS(=O)(=O)N1CCC2(CC1)N=C(C(C1CC1)C1CC1)NC2=O] | LCMS-F-1 | 0.87 | 516 (M + H)+ |
| 1053 | 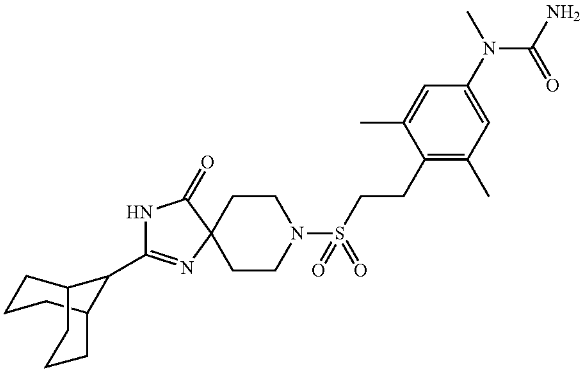 [SMILES: Cc1cc(N(C)C(N)=O)cc(C)c1CCS(=O)(=O)N1CCC2(CC1)N=C(C1C3CCCC1CCC3)NC2=O] | LCMS-F-1 | 0.99 | 544 (M + H)+ |
| 1054 | 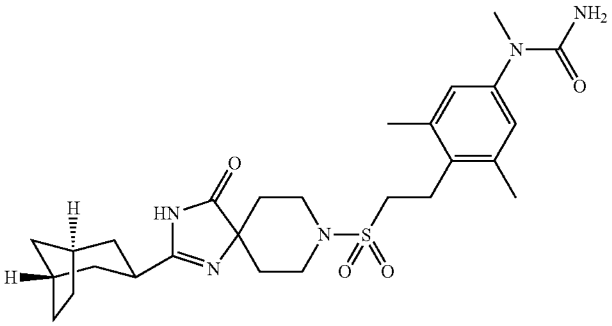 [SMILES: Cc1cc(N(C)C(N)=O)cc(C)c1CCS(=O)(=O)N1CCC2(CC1)N=C(C1C[C@H]3CC[C@@H](C1)C3)NC2=O] | LCMS-F-1 | 0.93 | 530 (M + H)+ |

TABLE 157-continued
| Compound | Structure | LCMS condition | Retention time (min) | MS (m/z) |
|---|---|---|---|---|
| 1055 | 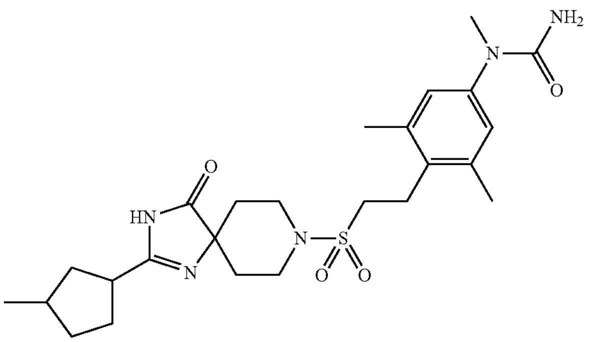 [SMILES: Cc1cc(N(C)C(N)=O)cc(C)c1CCS(=O)(=O)N1CCC2(CC1)N=C(C1CCC(C)C1)NC2=O] | LCMS-F-1 | 0.89 | 504 (M + H)+ |
| 1056 | 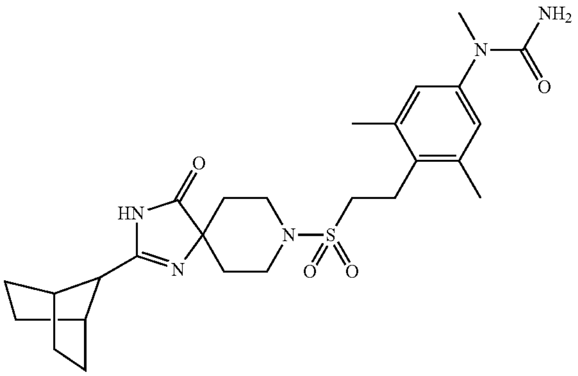 [SMILES: Cc1cc(N(C)C(N)=O)cc(C)c1CCS(=O)(=O)N1CCC2(CC1)N=C(C1C3CCC1CC3)NC2=O] | LCMS-F-1 | 0.91 | 516 (M + H)+ |
| 1057 | 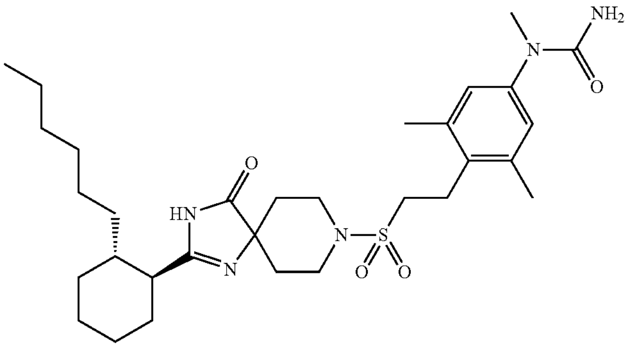 [SMILES: CCCCCC[C@H]1CCCC[C@@H]1C1=NC2(CCN(S(=O)(=O)CCc3c(C)cc(N(C)C(N)=O)cc3C)CC2)C(=O)N1] | LCMS-F-1 | 1.08 | 588 (M + H)+ |
| 1058 | 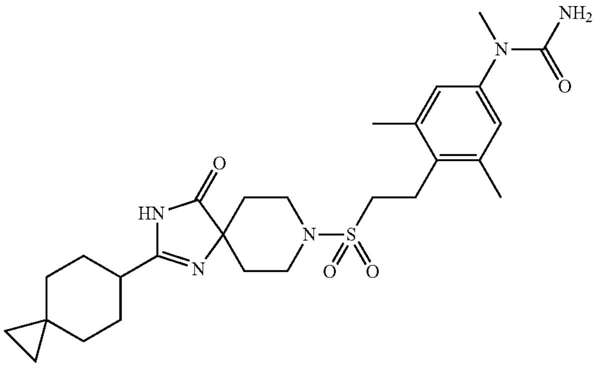 [SMILES: Cc1cc(N(C)C(N)=O)cc(C)c1CCS(=O)(=O)N1CCC2(CC1)N=C(C1CCC3(CC1)CC3)NC2=O] | LCMS-F-1 | 0.94 | 530 (M + H)+ |

The carboxylic acid reagent used in the synthesis of Compound 1051 (cis-3,4-dimethyl-cyclopentanecarboxylic acid) was synthesized by the following method.

(Reaction 247-3)

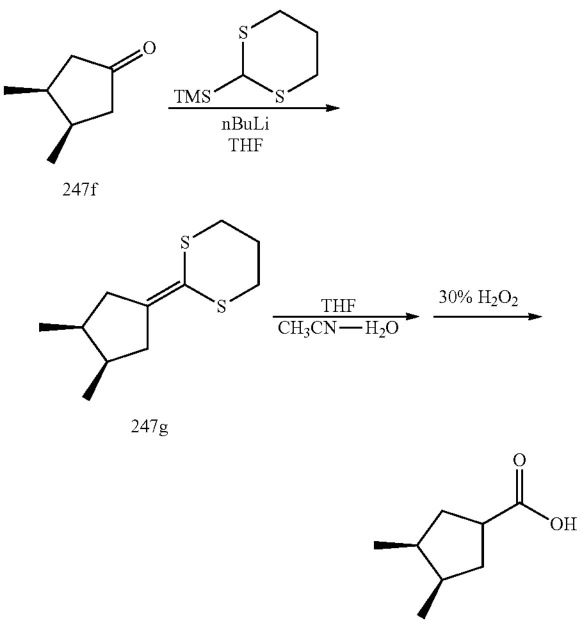

247f

247g

247h cis-3,4-Dimethyl-cyclopentanecarboxylic acid was synthesized by operations similar to those in Reaction 193-12 using appropriate reagents and starting material.

$^1$H-NMR (400 MHz, $CDCl_3$) δ 0.85 (3H, d, J=7.0 Hz), 0.89 (3H, d, J=7.0 Hz), 1.58-1.68 (2H, m), 2.00-2.15 (4H, m), 2.78 (0.4H, dd, J=17.2, 8.8 Hz), 2.92-3.00 (0.6H, m) (cis:trans=6:4).

The carboxylic acid reagent used in the synthesis of Compound 1052 (dicyclopropyl-acetic acid) was synthesized by the following method.

(Reaction 247-4)

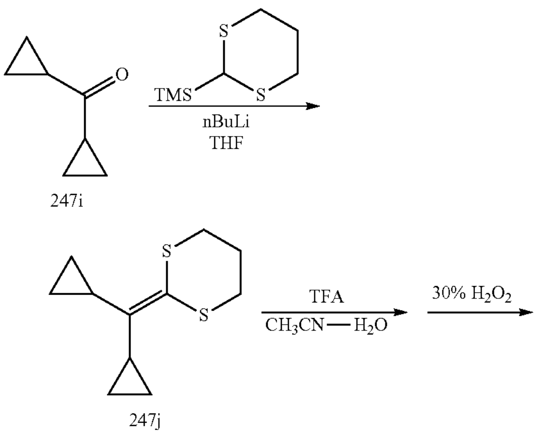

247i

247j

-continued

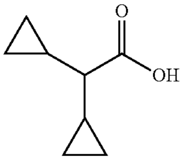

247k

Dicyclopropyl-acetic acid was synthesized by operations similar to those in Reaction 193-12 using appropriate reagents and starting material.

$^1$H-NMR (400 MHz, $CDCl_3$) δ0.24-0.33 (4H, m), 0.48-0.52 (2H, m), 0.58-0.62 (2H, m), 1.05-1.10 (3H, m).

The carboxylic acid reagent used in the synthesis of Compound 1053 (bicyclo[3.3.1]nonane-9-carboxylic acid) was synthesized by the following method.

(Reaction 247-5)

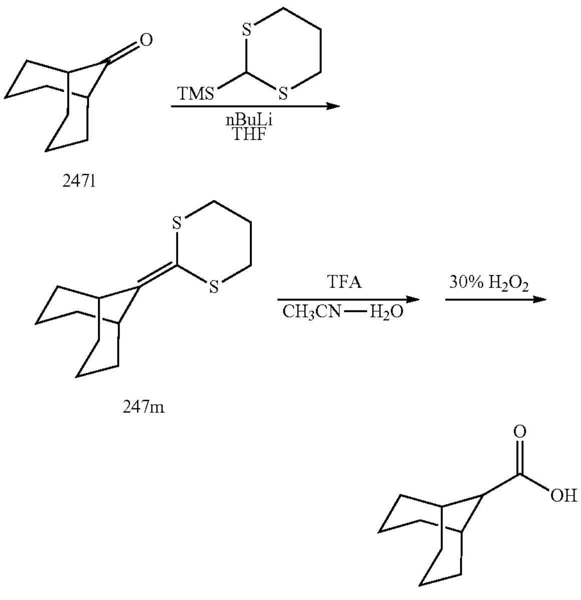

247l

247m

247n

Bicyclo[3.3.1]nonane-9-carboxylic acid was synthesized by operations similar to those in Reaction 193-12 using appropriate reagents and starting material.

$^1$H-NMR (400 MHz, $CDCl_3$) δ1.48-1.63 (4H, m), 1.70-1.80 (2H, m), 1.83-1.96 (6H, m), 2.33 (2H, br), 2.46 (1H, br).

The carboxylic acid reagent used in the synthesis of Compound 1057 (2-hexyl-cyclohexanecarboxylic acid) was synthesized by the following method.

(Reaction 247-6)

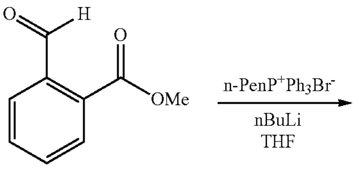

247o

-continued

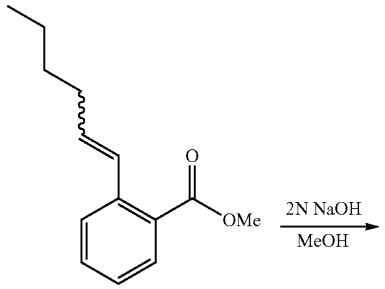

247p

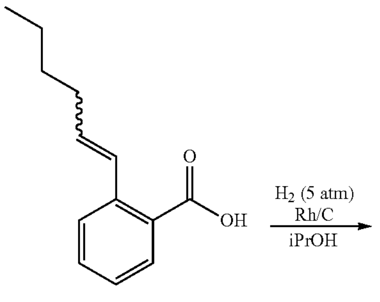

247q

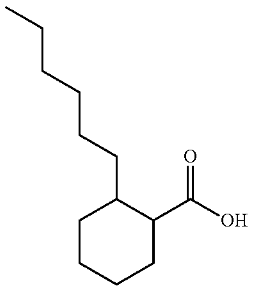

247r

2-Hexyl-cyclohexanecarboxylic acid was synthesized by operations similar to those in Reaction 101-1, Reaction 95-18 and Reaction 193-3 using appropriate reagents and starting material.

$^1$H-NMR (400 MHz, $CDCl_3$) δ 0.88 (3H, t, J=7.2 Hz), 1.20-1.55 (13H, m), 1.60-1.90 (6H, m), 2.56-2.59 (1H, m).

The carboxylic acid reagent used in the synthesis of Compound 1058 (spiro[2.5]octane-6-carboxylic acid) was synthesized by the following method.

(Reaction 247-7)

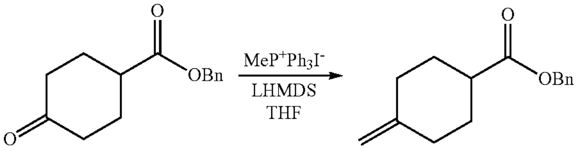

247s 247t

4-Methylene-cyclohexanecarboxylic acid benzyl ester was synthesized by operations similar to those in Reaction 193-9 using appropriate reagents and starting material.

MS (ESI) m/z=231 (M+H)+.

(Reaction 247-8)

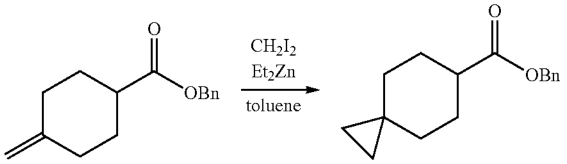

247t 247u $Et_2Zn$ (1.08 M solution in hexane, 5.23 ml, 5.65 mmol) was added to a solution of 4-methylene-cyclohexanecarboxylic acid benzyl ester (86.3 mg, 375 μmol) in toluene (1.4 ml), and the mixture was stirred at room temperature for 30 minutes. $CH_2I_2$ (500 μl, 6.22 mmol) was added to the reaction mixture at 0° C., and the mixture was stirred at 60° C. for 28 hours. Thereafter, $Et_2Zn$ (1.08 M solution in hexane, 2.60 ml, 2.22 mmol) and $CH_2I_2$ (260 μl, 3.23 mmol) were added to the reaction mixture, and the mixture was stirred at 60° C. for four days. Further, $Et_2Zn$ (1.08 M solution in hexane, 2.60 ml, 2.22 mmol) and $CH_2I_2$ (500 μl, 6.22 mmol) were added to the reaction mixture, and the mixture was stirred at 60° C. for one day. The reaction mixture was quenched by adding a 1% aqueous HCl solution and diluted with ethyl acetate and $Et_2O$. The organic layer was then washed with a 1% aqueous HCl solution, a saturated aqueous sodium bicarbonate solution and saturated brine, and then dried over $MgSO_4$ and concentrated under reduced pressure. The resulting residue was purified by silica gel column chromatography (hexane/ethyl acetate=100/0→65/35) to give spiro[2.5]octane-6-carboxylic acid benzyl ester (70.6 mg, 77%).

$^1$H-NMR (400 MHz, $CDCl_3$) δ 0.19-0.22 (2H, m), 0.26-0.30 (2H, m), 0.94-1.00 (2H, m), 1.60-1.72 (4H, m), 1.90-1.95 (2H, m), 2.37-2.42 (1H, m), 5.12 (2H, s), 7.30-7.38 (5H, m).

(Reaction 247-9)

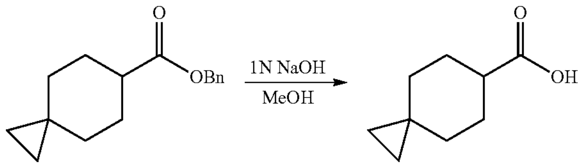

247u 247v

Spiro[2.5]octane-6-carboxylic acid was synthesized by operations similar to those in Reaction 95-18 using appropriate reagents and starting material.

$^1$H-NMR (400 MHz, $CDCl_3$) δ 0.19-0.24 (2H, m), 0.28-0.30 (2H, m), 0.97-1.03 (2H, m), 1.60-1.72 (4H, m), 1.92-1.95 (2H, m), 2.35-2.42 (1H, m).

Example 248
1-(4-{2-[2-(4-Difluoromethylene-cyclohexyl)-4-oxo-1,3,8-triaza-spiro[4.5]dec-1-ene-8-sulfonyl]-ethyl}-3,5-dimethyl-phenyl)-1-methyl-urea (Compound 1059)
(Reaction 248-1)
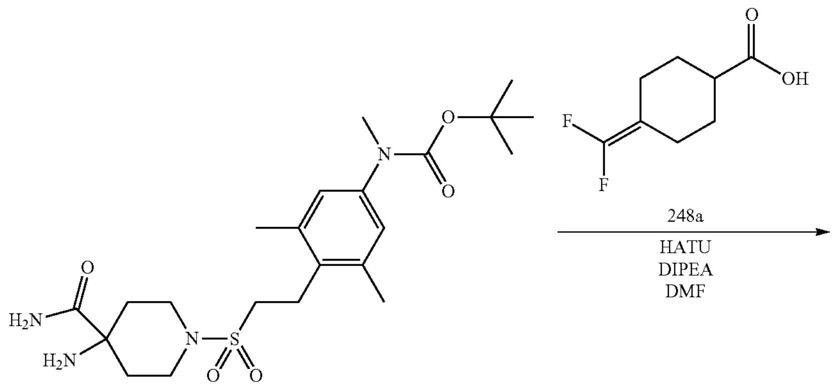
239d
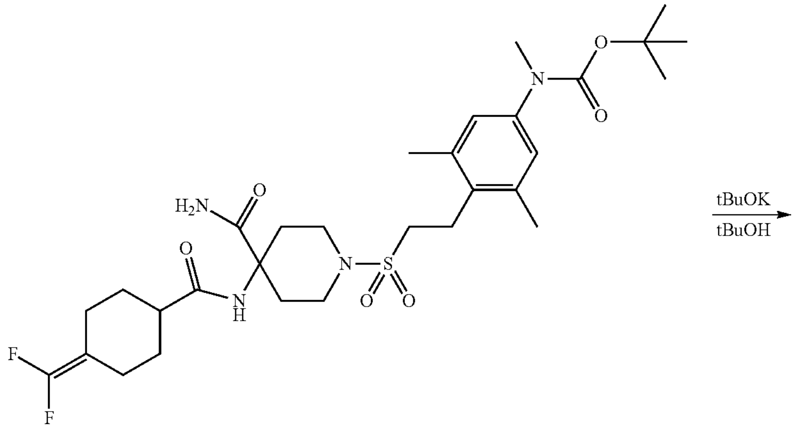
248b
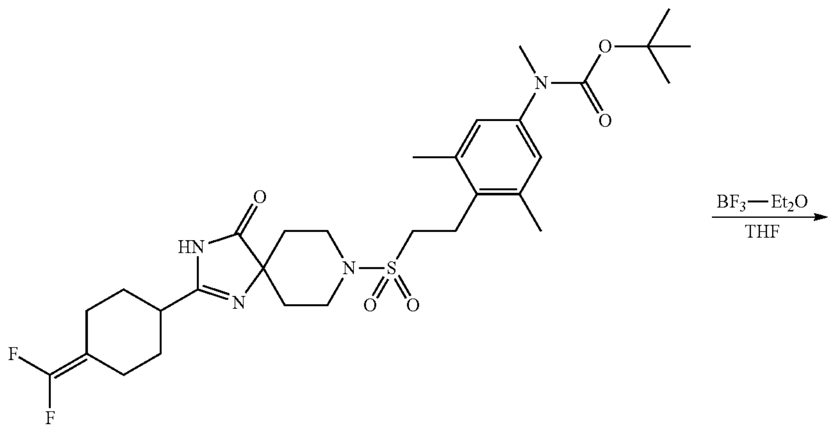
248c -continued

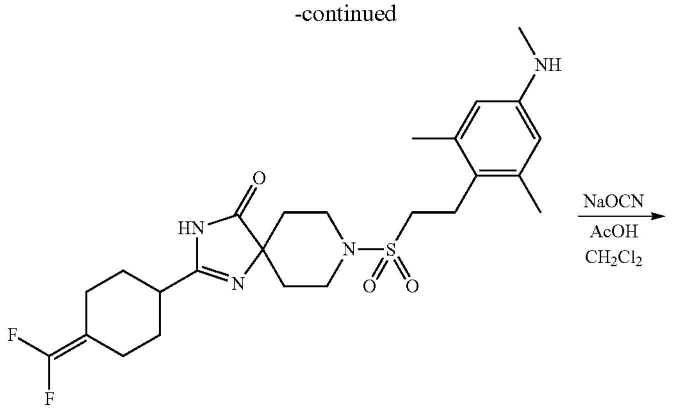

248d

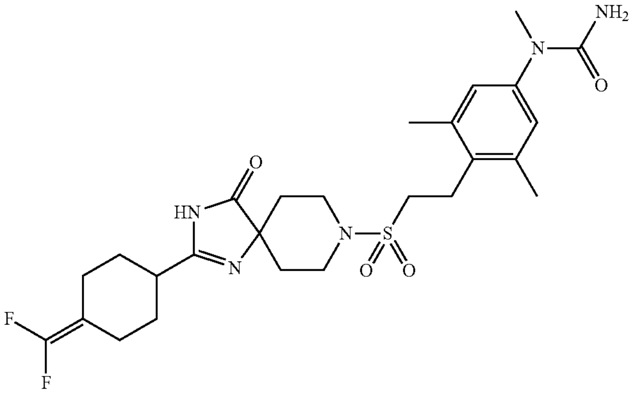

Compound 1059

1-(4-{2-[2-(4-Difluoromethylene-cyclohexyl)-4-oxo-1,3,8-triaza-spiro[4.5]dec-1-ene-8-sulfonyl]-ethyl}-3,5-dimethyl-phenyl)-1-methyl-urea was synthesized by operations similar to those in Reaction 10-14, Reaction 10-12, Reaction 241-2 and Reaction 89-2 using appropriate reagents and starting material.

MS (ESI) m/z=552 (M+H)+.

The carboxylic acid reagent used in the synthesis of Compound 1059 (4-difluoromethylene-cyclohexanecarboxylic acid) was synthesized by the following method.

(Reaction 248-2)

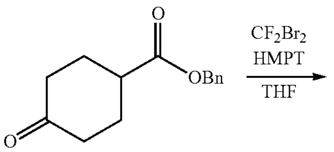

247s

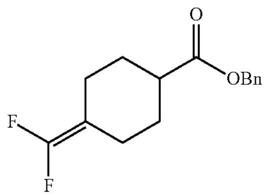

248e

HMPT (7.40 ml, 39.5 mmol) was added to a solution of 4-oxo-cyclohexanecarboxylic acid benzyl ester (1.50 g, 6.59 mmol) and $CF_2Br_2$ (1.8 ml, 19.8 mmol) in THF (30 ml) at 0° C., and the reaction mixture was stirred at room temperature for 22 hours. Water was added, followed by extraction with ethyl acetate. The organic layer was then dried over $MgSO_4$ and concentrated under reduced pressure. The resulting residue was purified by silica gel column chromatography (hexane/ethyl acetate=100/0→75/25) to give 4-difluoromethylene-cyclohexanecarboxylic acid benzyl ester (166 mg, 9%).

$^1$H-NMR (400 MHz, $CDCl_3$) δ 1.57 (2H, ddd, J=12, 12, 4 Hz), 1.80-1.90 (2H, m), 1.97-2.05 (2H, m), 2.43-2.49 (3H, m), 5.12 (2H, s), 7.32-7.40 (5H, m).

(Reaction 248-3)

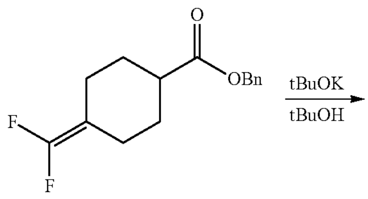

248e

-continued

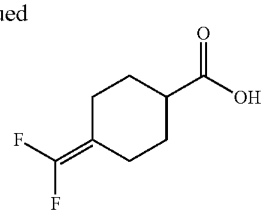

248a

4-Difluoromethylene-cyclohexanecarboxylic acid was synthesized by operations similar to those in Reaction 215-2 using appropriate reagents and starting material.

$^1$H-NMR (400 MHz, $CDCl_3$) δ 1.52-1.63 (2H, m), 1.85-1.94 (2H, m), 1.97-2.05 (2H, m), 2.43-2.49 (3H, m).

Example 249

N-[4-(2-{2-[4-(2,2-Difluoro-ethyl)-cyclohexyl]-4-oxo-1,3,8-triaza-spiro[4.5]dec-1-ene-8-sulfonyl}-ethyl)-3-methyl-phenyl]-acetamide (Compound 1060)

(Reaction 249-1)

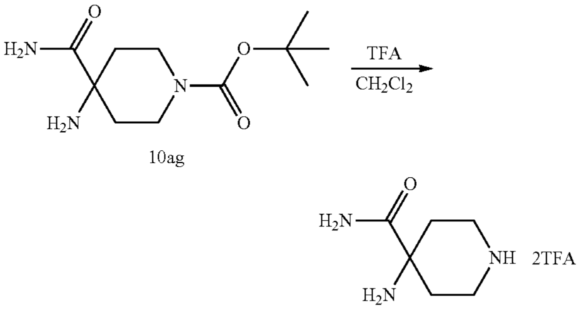

249a

Trifluoroacetic acid (6.17 mL, 83.0 mmol) was added to a solution of 4-amino-4-carbamoyl-piperidine-1-carboxylic acid tert-butyl ester (2.02 g, 8.30 mmol) in dichloromethane (16.6 mL), and the mixture was stirred at room temperature for 1.5 hours. The reaction solution was concentrated under reduced pressure. The residue was dissolved in methanol (2.00 mL), repeatedly concentrated under reduced pressure twice and dried under reduced pressure to give 4-amino-piperidine-4-carboxylic amide 2TFA salt as a colorless substance (3.25 g).

$^1$H-NMR (400 MHz, $CD_3OD$) δ 2.10-2.19 (2H, br-m), 2.56-2.65 (2H, m), 3.34-3.45 (4H, m).

(Reaction 249-2)

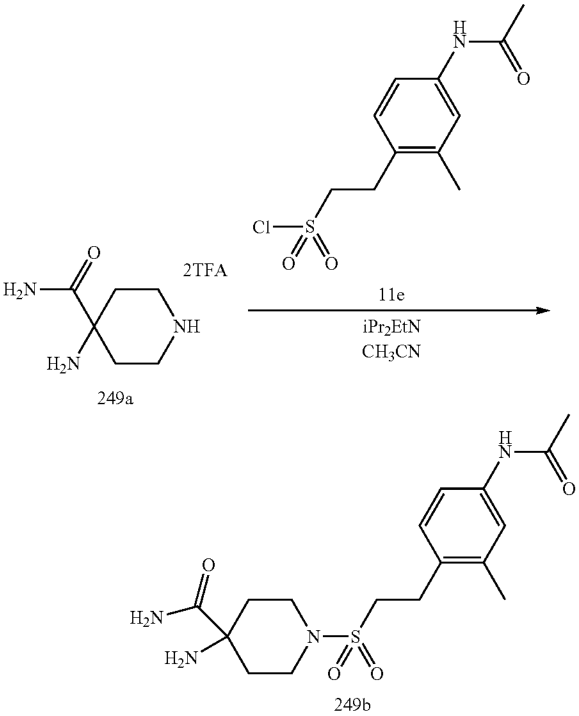

1-[2-(4-Acetylamino-2-methyl-phenyl)-ethanesulfonyl]-4-amino-piperidine-4-carboxylic amide was synthesized by operations similar to those in Reaction 5-4 using appropriate reagents and starting material.

MS (ESI) m/z=383 (M+H)+.

(Reaction 249-3)

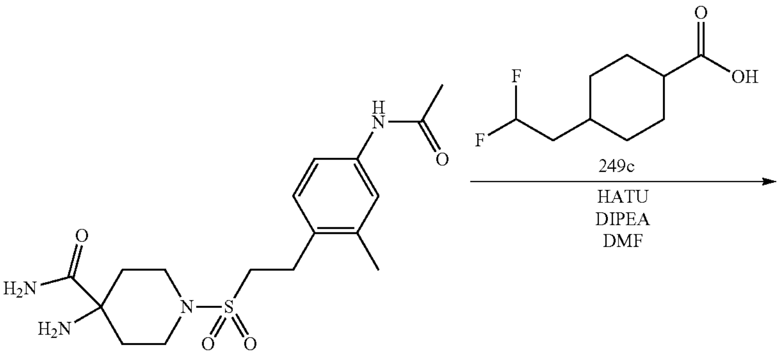

249b

-continued

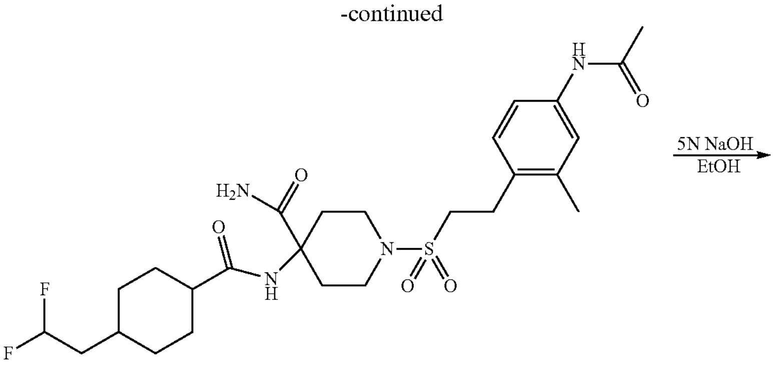

249d

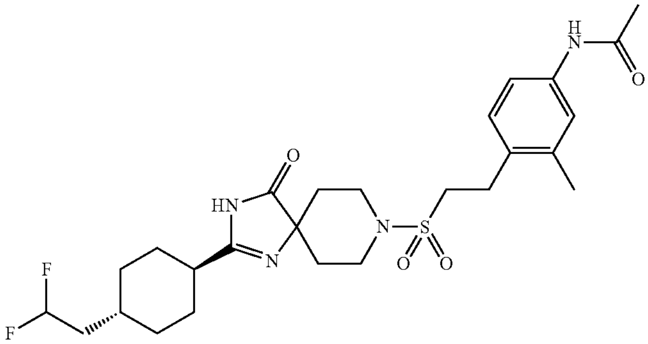

Compound 1060

N-[4-(2-{2-[4-(2,2-Difluoro-ethyl)-cyclohexyl]-4-oxo-1,3,8-triaza-spiro[4.5]dec-1-ene-8-sulfonyl}-ethyl)-3-methyl-phenyl]-acetamide was synthesized by operations similar to those in Reaction 10-14 and Reaction 189-5 using appropriate reagents and starting material.

MS (ESI) m/z=539 (M+H)+.

The carboxylic acid reagent used in the synthesis of Compound 1060 (4-(2,2-difluoro-ethyl)-cyclohexanecarboxylic acid) was synthesized by the following method.

(Reaction 249-4)

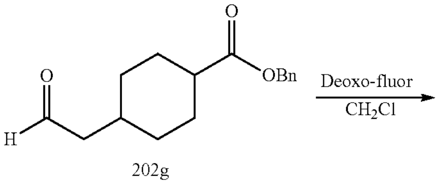

202g

-continued

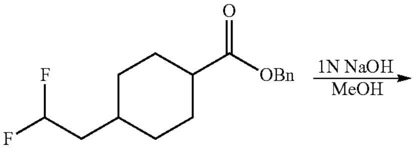

249e

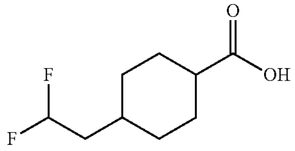

249c 4-(2,2-Difluoro-ethyl)-cyclohexanecarboxylic acid was synthesized by operations similar to those in Reaction 191-11 and Reaction 95-18 using appropriate reagents and starting material.

$^1$H-NMR (400 MHz, $CDCl_3$) δ 1.00-2.04 (11H, m), 2.27 (0.25H, tt, J=12.4, 3.2 Hz), 2.60-2.64 (0.75H, m), 5.68-6.01 (1H, m) (cis:trans=3:1).

The example compounds shown below were synthesized by operations similar to those in Reaction 249-3 using appropriate reagents and starting materials.

Compounds 1061 to 1063

TABLE 158

| Compound | Structure | LCMS condition | Retention time (min) | MS (m/z) |
|---|---|---|---|---|
| 1061 | 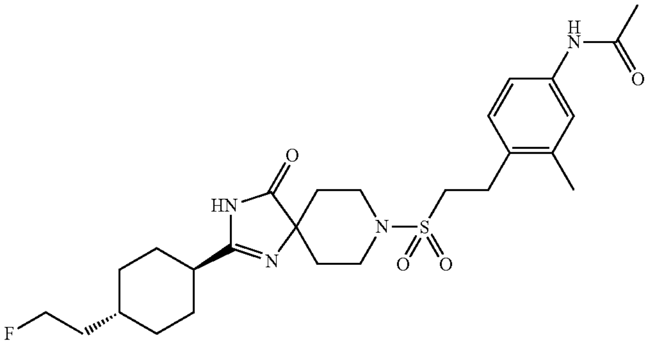 [SMILES: CC(=O)Nc1ccc(CCS(=O)(=O)N2CCC3(CC2)N=C([C@H]2CC[C@H](CCF)CC2)NC3=O)c(C)c1] | LCMS-C-1 | 2.40 | 521 (M + H)+ |
| 1062 | 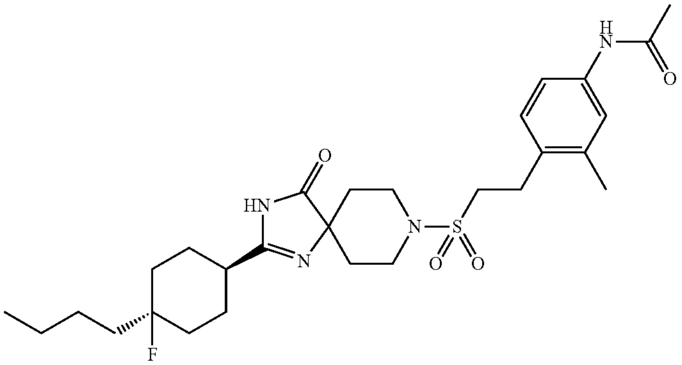 [SMILES: CCCC[C@]1(F)CC[C@@H](C2=NC3(CCN(S(=O)(=O)CCc4ccc(NC(C)=O)cc4C)CC3)C(=O)N2)CC1] | LCMS-B-1 | 1.98 | 549 (M + H)+ |
| 1063 | 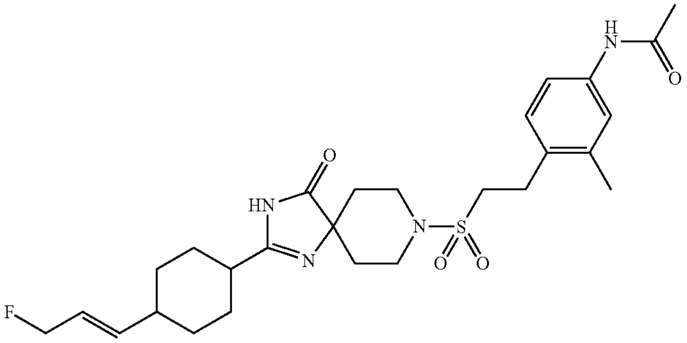 [SMILES: CC(=O)Nc1ccc(CCS(=O)(=O)N2CCC3(CC2)N=C(C2CCC(/C=C/CF)CC2)NC3=O)c(C)c1] | LCMS-B-1 | 1.76 | 533 (M + H)+ |

The carboxylic acid reagent used in the synthesis of Compound 1061 (4-(2-fluoro-ethyl)-cyclohexanecarboxylic acid) was synthesized by the following method.

(Reaction 249-5)

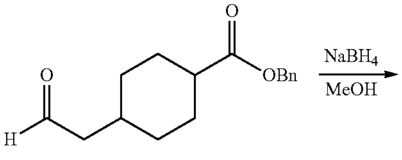

202g

-continued

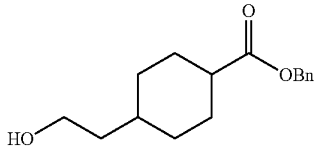

249f

Sodium borohydride (89 mg, 2.35 mmol) was added to a solution of 4-(2-oxo-ethyl)-cyclohexanecarboxylic acid benzyl ester (306 mg, 1.18 mmol) in methanol (6 ml) at 0° C. The mixture was stirred at 0° C. for one hour, and then quenched with a saturated aqueous ammonium chloride solution and extracted with ethyl acetate. The organic layer was sequentially washed with water and saturated brine, and then dried over anhydrous sodium sulfate and concentrated under reduced pressure. The resulting residue was purified by silica gel column chromatography to give 4-(2-hydroxy-ethyl)-cyclohexanecarboxylic acid benzyl ester (299 mg).

$^1$H-NMR (400 MHz, $CDCl_3$) δ 1.20-1.32 (2H, m), 1.40-1.63 (9H, m), 1.95-2.05 (2H, m), 2.25-2.33 (0.2H, m), 2.55-2.62 (0.8H, m), 3.67 (1.6H, t, J=6.8 Hz), 3.69 (0.4H, t, J=6.4 Hz), 7.30-7.40 (5H, m) (cis:trans=4:1).

(Reaction 249-6)

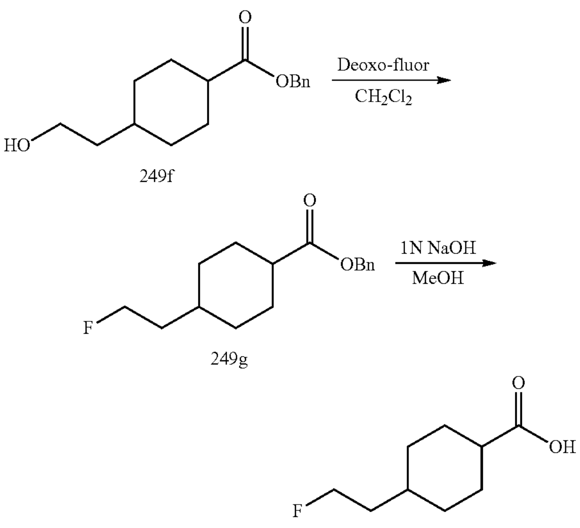

249f

249g

249h 4-(2-Fluoro-ethyl)-cyclohexanecarboxylic acid was synthesized by operations similar to those in Reaction 191-11 and Reaction 95-18 using appropriate reagents and starting material.

$^1$H-NMR (400 MHz, $CDCl_3$) δ 0.93-2.03 (11H, m), 2.26 (0.2H, tt, J=12.0, 3.2 Hz), 2.57-2.62 (0.8H, m), 4.39-4.56 (2H, m) (cis:trans=4:1).

The carboxylic acid reagent used in the synthesis of Compound 1062 (4-butyl-4-fluoro-cyclohexanecarboxylic acid) was synthesized by the following method.

(Reaction 249-7)

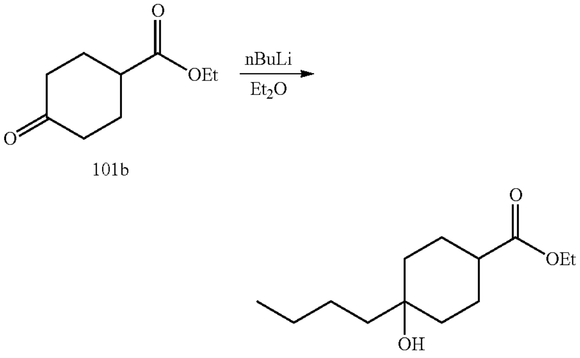

101b

249i

A 2.6 M solution of n-BuLi in THF (681 μl, 1.77 mmol) was added to a solution of 4-oxo-cyclohexanecarboxylic acid ethyl ester (186 μl, 1.18 mmol) in $Et_2O$ (4.0 ml) at −60° C. in an $N_2$ atmosphere, and the mixture was stirred at −60° C. for four hours. The reaction mixture was quenched by adding water and then diluted with ethyl acetate. The organic layer was washed with water, and then dried over $MgSO_4$ and concentrated under reduced pressure. The resulting residue was used in the next step without purification.

(Reaction 249-8)

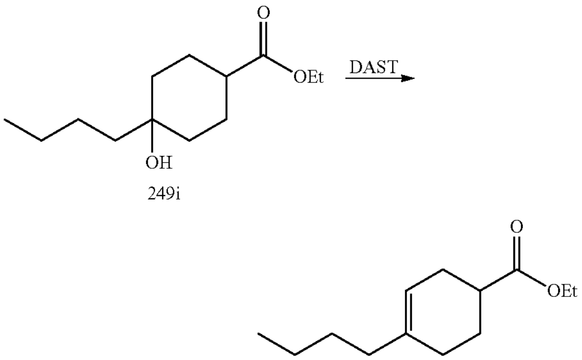

249i

249j

4-Butyl-cyclohex-3-enecarboxylic acid ethyl ester was synthesized by operations similar to those in Reaction 25-15 using appropriate reagents and starting material.

MS (ESI) m/z=211 (M+H)+.

(Reaction 249-9)

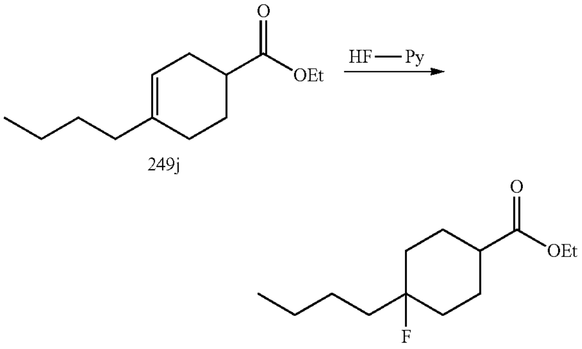

249j

249k

HF.Py (0.5 ml) was added to 4-butyl-cyclohex-3-enecarboxylic acid ethyl ester (43.0 mg, 205 μmol) at room temperature, and the reaction mixture was stirred at room temperature for two hours. The reaction mixture was diluted by adding dichloromethane and then quenched by adding a saturated aqueous sodium bicarbonate solution and solid sodium bicarbonate at 0° C. The organic layer was washed with 2 N HCl, and then dried over $MgSO_4$ and concentrated under reduced pressure. The resulting residue was purified by silica gel column chromatography (hexane/ethyl acetate=100/0→97/3) to give 4-butyl-4-fluoro-cyclohexanecarboxylic acid ethyl ester (22.5 mg, 48%, cis:trans=1:3).

$^1$H-NMR (400 MHz, $CDCl_3$) δ 0.91 (3H, t, J=8.0 Hz), 1.25 (3H, t, J=8.0 Hz), 1.28-1.38 (6H, m), 1.51-1.84 (6H, m), 1.84-2.00 (2H, m), 2.20-2.26 (0.75H, m), 2.48-2.54 (0.25H, m), 4.10-4.16 (2H, m).

(Reaction 249-10)

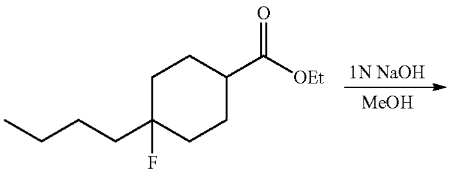

249k

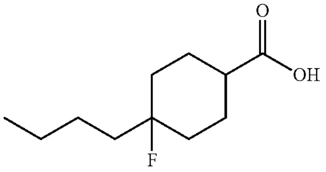

2491

4-Butyl-4-fluoro-cyclohexanecarboxylic acid was synthesized by operations similar to those in Reaction 95-18 using appropriate reagents and starting material.

$^1$H-NMR (400 MHz, $CDCl_3$) δ 0.91 (3H, t, J=7.0 Hz), 1.25-1.46 (6H, m), 1.50-1.62 (2H, m), 1.69-2.05 (6H, m), 2.25-2.35 (0.75H, m), 2.58-2.70 (0.25H, m).

The carboxylic acid reagent used in the synthesis of Compound 1063 (4-((E)-3-fluoro-propenyl)-cyclohexanecarboxylic acid) was synthesized by the following method.

(Reaction 249-11)

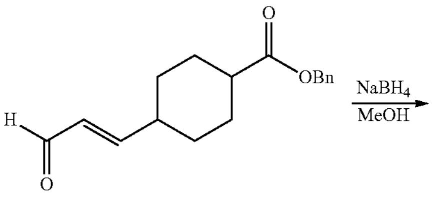

191ac

-continued

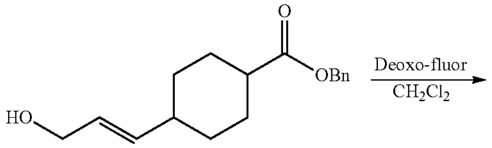

249m

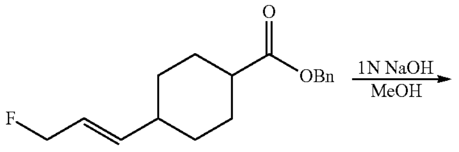

249n

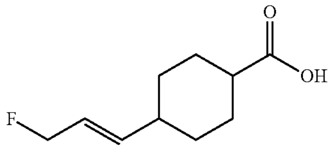

249o 4-((E)-3-Fluoro-propenyl)-cyclohexanecarboxylic acid was synthesized by operations similar to those in Reaction 249-5, Reaction 191-11 and Reaction 95-18 using appropriate reagents and starting material. This was used in the next step without complete purification.

Example 250

N-[4-(2-{2-[4-(3-Fluoro-propyl)-cyclohexyl]-4-oxo-1,3,8-triaza-spiro[4.5]dec-1-ene-8-sulfonyl}-ethyl)-3-methyl-phenyl]-acetamide (Compound 1064) and N-[4-(2-{2-[4-(3-chloro-propyl)-cyclohexyl]-4-oxo-1,3,8-triaza-spiro[4.5]dec-1-ene-8-sulfonyl}-ethyl)-3-methyl-phenyl]-acetamide (Compound 1065)

(Reaction 250-1)

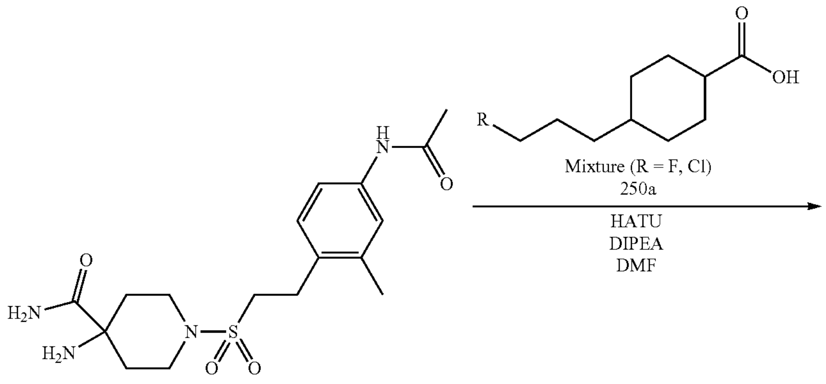

249b

-continued

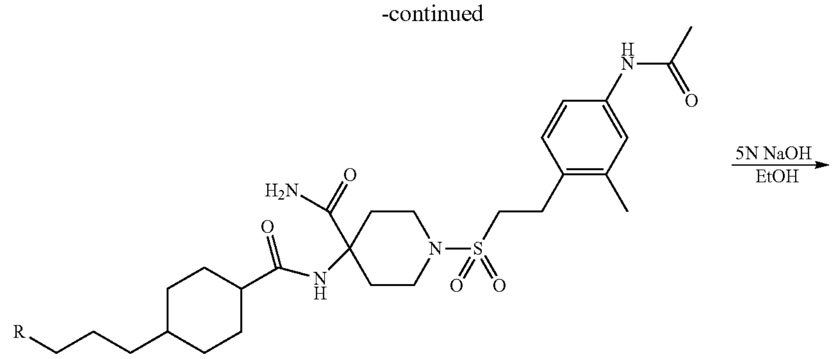

Mixture (R = F, Cl)
250b

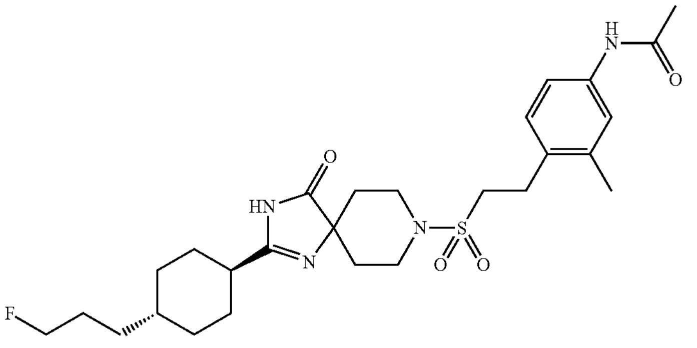

Compound 1064

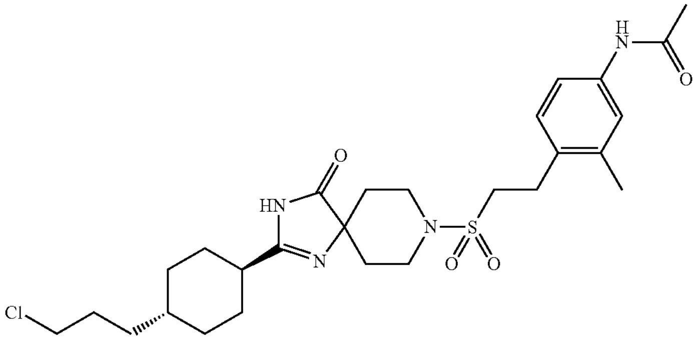

Compound 1065

N-[4-(2-{2-[4-(3-Fluoro-propyl)-cyclohexyl]-4-oxo-1,3,8-triaza-spiro[4.5]dec-1-ene-8-sulfonyl}-ethyl)-3-methyl-phenyl]-acetamide MS (ESI) m/z=535 (M+H)+ and N-[4-(2-{2-[4-(3-chloro-propyl)-cyclohexyl]-4-oxo-1,3,8-triaza-spiro[4.5]dec-1-ene-8-sulfonyl}-ethyl)-3-methyl-phenyl]-acetamide MS (ESI) m/z=551 (M+H)+ were synthesized by operations similar to those in Reaction 10-14 and Reaction 189-5 using appropriate reagents and starting material.

The carboxylic acid reagent used in the synthesis of Compound 1064 and Compound 1065 (a mixture of 4-(3-fluoro-propyl)-cyclohexanecarboxylic acid and 4-(3-chloro-propyl)-cyclohexanecarboxylic acid) was synthesized by the following method.

(Reaction 250-2)

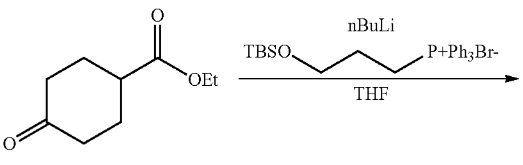

101b

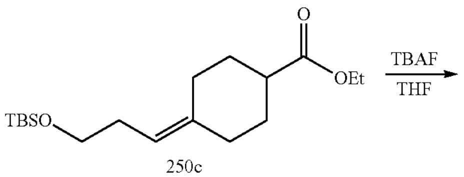

250c

-continued

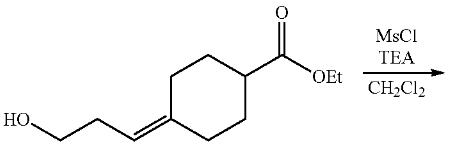

250d

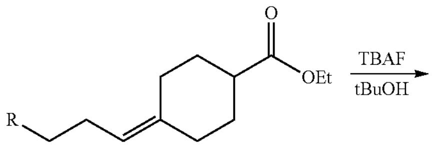

Mixture
(R = OMs, Cl)

250e

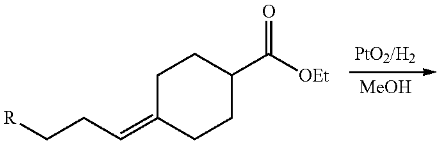

Mixture
(R = F, Cl)

250f

-continued

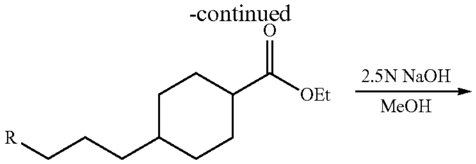

Mixture
(R = F, Cl)

250g

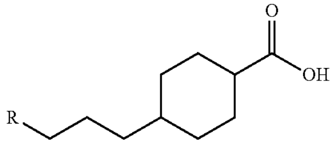

Mixture
(R = F, Cl)

250a

A mixture of 4-(3-fluoro-propyl)-cyclohexanecarboxylic acid and 4-(3-chloro-propyl)-cyclohexanecarboxylic acid was synthesized by operations similar to those in Reaction 101-1, Reaction 39-2, Reaction 5-4, Reaction 119-3, Reaction 18-2 (using platinum oxide) and Reaction 95-18 using appropriate reagents and starting material. This was used in the next step without complete purification.

Example 251

N-[4-(2-{2-[4-(3-Fluoro-propylidene)-cyclohexyl]-4-oxo-1,3,8-triaza-spiro[4.5]dec-1-ene-8-sulfonyl}-ethyl)-3-methyl-phenyl]-acetamide (Compound 1066)

(Reaction 251-1)

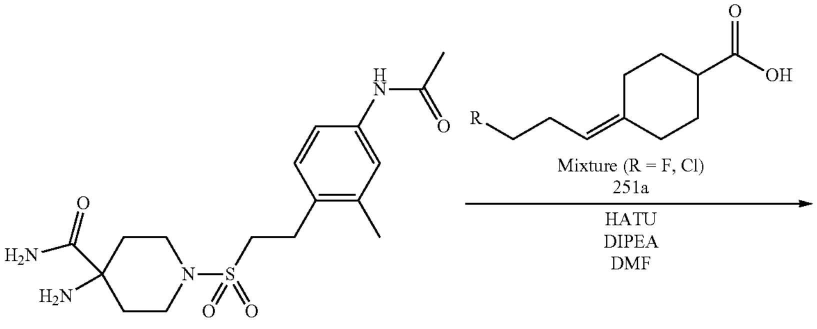

Mixture (R = F, Cl)
251a

249b

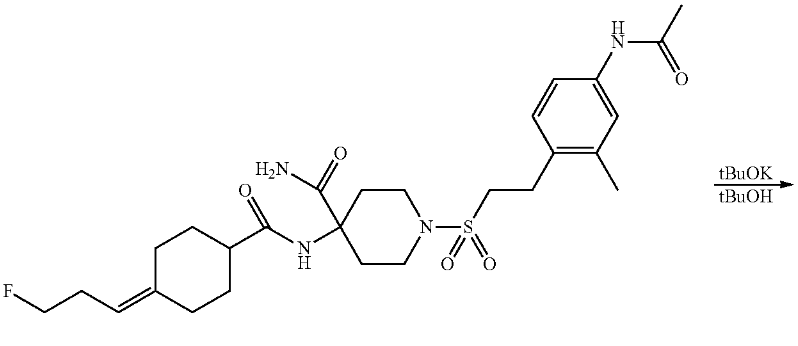

251b

-continued

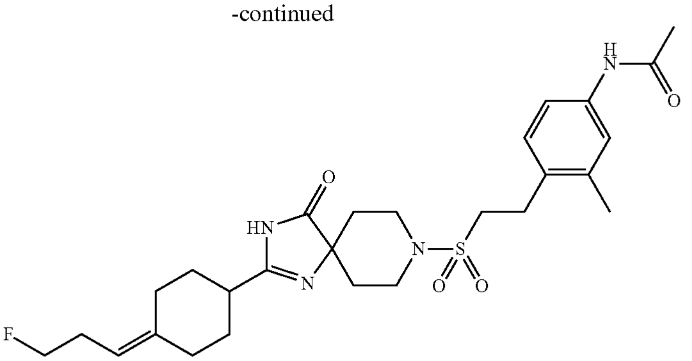

Compound 1066

N-[4-(2-{2-[4-(3-Fluoro-propylidene)-cyclohexyl]-4-oxo-1,3,8-triaza-spiro[4.5]dec-1-ene-8-sulfonyl}-ethyl)-3-methyl-phenyl]-acetamide was synthesized by operations similar to those in Reaction 10-14 and Reaction 10-12 using appropriate reagents and starting material.

MS (ESI) m/z=533 (M+H)+.

The example compounds shown below were synthesized by operations similar to those in Reaction 251-1 using appropriate reagents and starting materials.

Compounds 1067 to 1077

TABLE 159

| Compound | Structure | LCMS condition | Retention time (min) | MS (m/z) |
|---|---|---|---|---|
| 1067 | 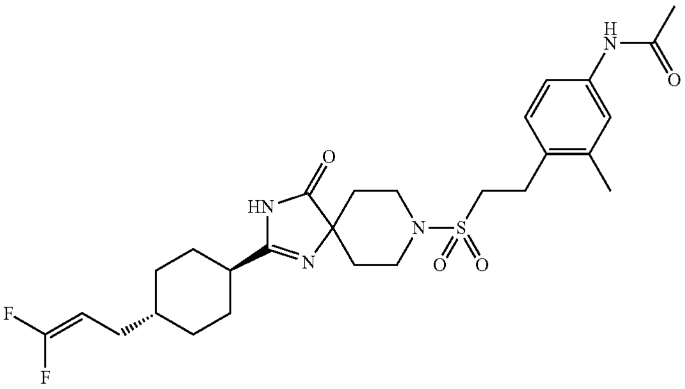 [SMILES: CC(=O)Nc1ccc(CCS(=O)(=O)N2CCC3(CC2)N=C([C@H]2CC[C@H](CC=C(F)F)CC2)NC3=O)c(C)c1] | LCMS-C-2 | 2.00 | 551 (M + H)+ |
| 1068 | 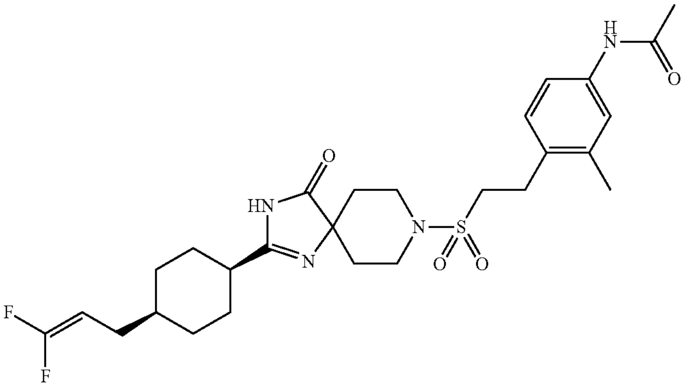 [SMILES: CC(=O)Nc1ccc(CCS(=O)(=O)N2CCC3(CC2)N=C([C@H]2CC[C@@H](CC=C(F)F)CC2)NC3=O)c(C)c1] | LCMS-C-2 | 2.03 | 551 (M + H)+ |

TABLE 159-continued
| Compound | Structure | LCMS condition | Retention time (min) | MS (m/z) |
|---|---|---|---|---|
| 1069 | 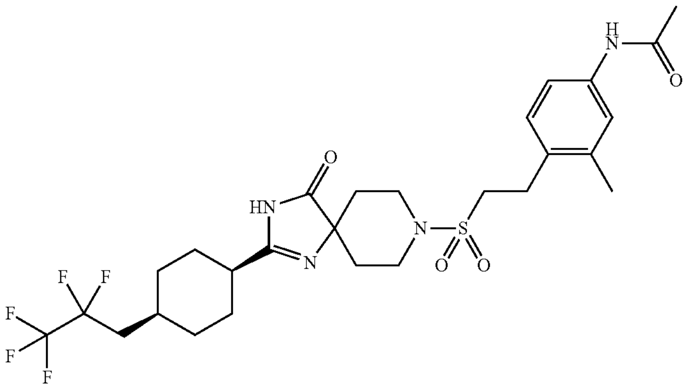 [SMILES: CC(=O)Nc1ccc(CCS(=O)(=O)N2CCC3(CC2)N=C([C@H]2CC[C@@H](CC(F)(F)C(F)(F)F)CC2)NC3=O)c(C)c1] | LCMS-C-2 | 2.08 | 607 (M + H)+ |
| 1070 | 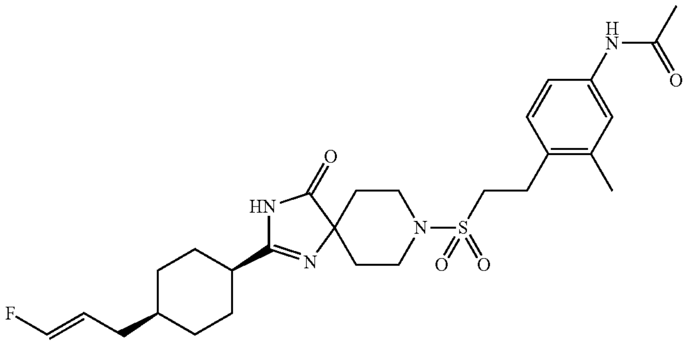 [SMILES: CC(=O)Nc1ccc(CCS(=O)(=O)N2CCC3(CC2)N=C([C@H]2CC[C@@H](C/C=C/F)CC2)NC3=O)c(C)c1] | LCMS-B-1 | 1.84 | 533 (M + H)+ |
| 1071 | 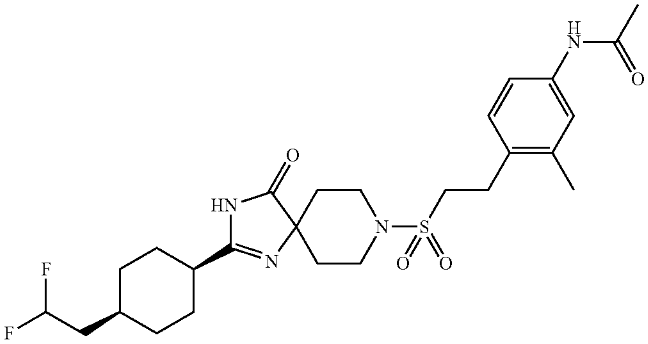 [SMILES: CC(=O)Nc1ccc(CCS(=O)(=O)N2CCC3(CC2)N=C([C@H]2CC[C@@H](CC(F)F)CC2)NC3=O)c(C)c1] | LCMS-C-1 | 2.43 | 539 (M + H)+ |
| 1072 | 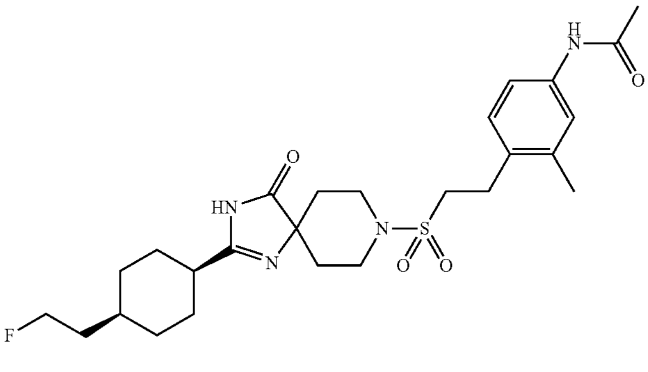 [SMILES: CC(=O)Nc1ccc(CCS(=O)(=O)N2CCC3(CC2)N=C([C@H]2CC[C@@H](CCF)CC2)NC3=O)c(C)c1] | LCMS-C-1 | 2.40 | 521 (M + H)+ |

TABLE 159-continued
| Compound | Structure | LCMS condition | Retention time (min) | MS (m/z) |
|---|---|---|---|---|
| 1073 | 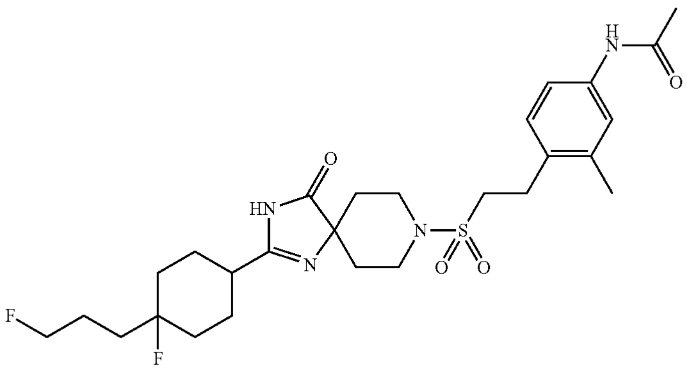 [SMILES: CC(=O)Nc1ccc(CCS(=O)(=O)N2CCC3(CC2)N=C(C2CCC(F)(CCCF)CC2)NC3=O)c(C)c1] | LCMS-F-1 | 0.87 | 553 (M + H)+ |
| 1074 | 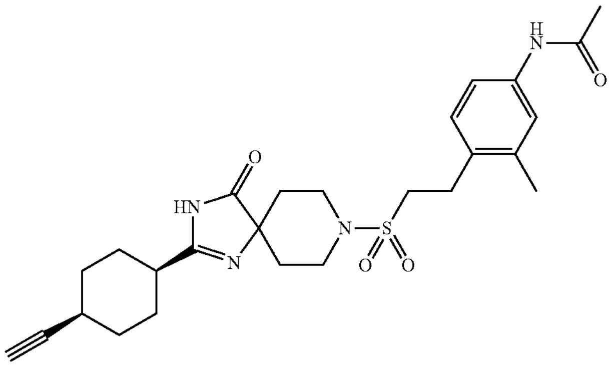 [SMILES: C#C[C@H]1CC[C@@H](C2=NC3(CCN(S(=O)(=O)CCc4ccc(NC(C)=O)cc4C)CC3)C(=O)N2)CC1] | LCMS-B-1 | 1.63 | 499 (M + H)+ |
| 1075 | 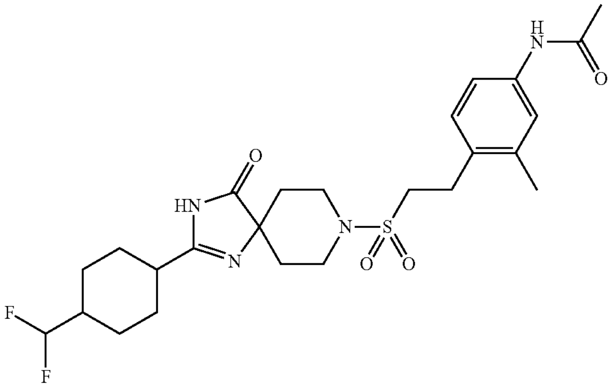 [SMILES: CC(=O)Nc1ccc(CCS(=O)(=O)N2CCC3(CC2)N=C(C2CCC(C(F)F)CC2)NC3=O)c(C)c1] | LCMS-F-1 | 0.85 | 525 (M + H)+ |
| 1076 | 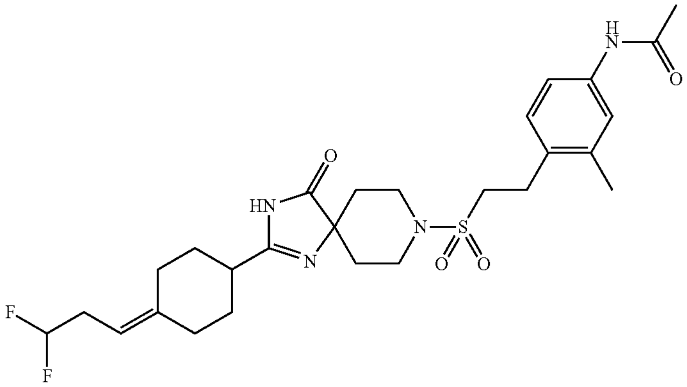 [SMILES: CC(=O)Nc1ccc(CCS(=O)(=O)N2CCC3(CC2)N=C(C2CCC(=CCC(F)F)CC2)NC3=O)c(C)c1] | LCMS-B-1 | 1.79 | 551 (M + H)+ |

TABLE 159-continued

| Compound | Structure | LCMS condition | Retention time (min) | MS (m/z) |
|---|---|---|---|---|
| 1077 | 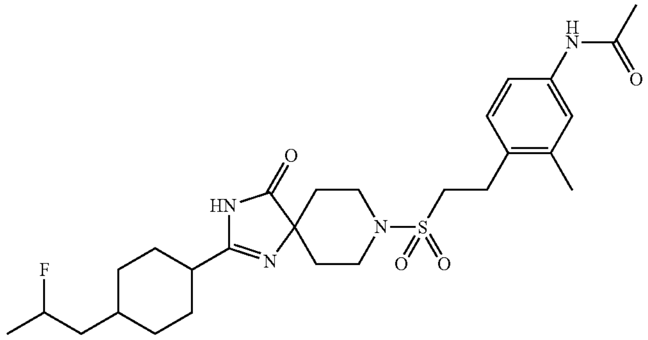 [SMILES: CC(=O)Nc1ccc(CCS(=O)(=O)N2CCC3(CC2)N=C(C2CCC(CC(C)F)CC2)NC3=O)c(C)c1] | LCMS-F-1 | 0.91 | 535 (M + H)+ |

The carboxylic acid reagent used in the synthesis of Compound 1066 (a mixture of 4-(3-fluoro-propylidene)-cyclohexanecarboxylic acid and 4-(3-chloro-propylidene)-cyclohexanecarboxylic acid) was synthesized by the following method.

(Reaction 251-2)

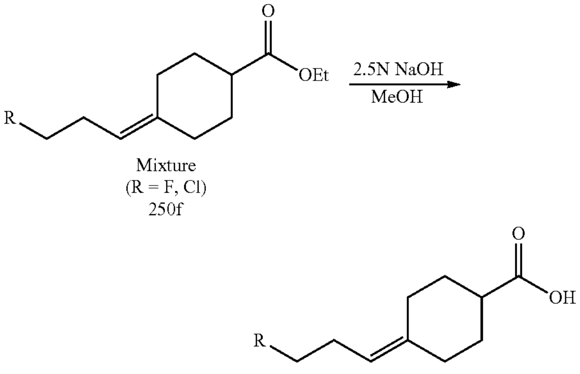

Mixture
(R = F, Cl)
250f

Mixture
(R = F, Cl)
251a

A mixture of 4-(3-fluoro-propylidene)-cyclohexanecarboxylic acid and 4-(3-chloro-propylidene)-cyclohexanecarboxylic acid was synthesized by operations similar to those in Reaction 95-18 using appropriate reagents and starting material. This was used in the next step without complete purification.

The carboxylic acid reagent used in the synthesis of Compound 1069 (4-(2,2,3,3,3-pentafluoro-propyl)-cyclohexanecarboxylic acid) was synthesized by the following method.

(Reaction 251-3)

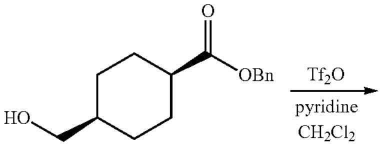

190c

-continued

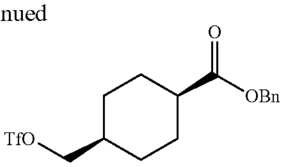

251c

4-Trifluoromethanesulfonyloxymethyl-cyclohexanecarboxylic acid benzyl ester (cis:trans=4:1) was synthesized by operations similar to those in Reaction 12-2 using appropriate reagents and starting material.

$^1$H-NMR (400 MHz, $CDCl_3$) δ 1.10 (0.4H, m), 1.34 (1.6H, m), 1.44-1.72 (4H, m), 1.83 (0.2H, m), 1.92 (0.8H, m), 2.11 (2H, m), 2.32 (0.2H, m), 2.68 (0.8H, m), 4.33 (1.6H, d, J=6.8 Hz), 4.39 (0.4H, d, J=5.8 Hz), 5.12 (0.4H, s), 5.14 (1.6H, s), 7.35 (5H, m).

(Reaction 251-4)

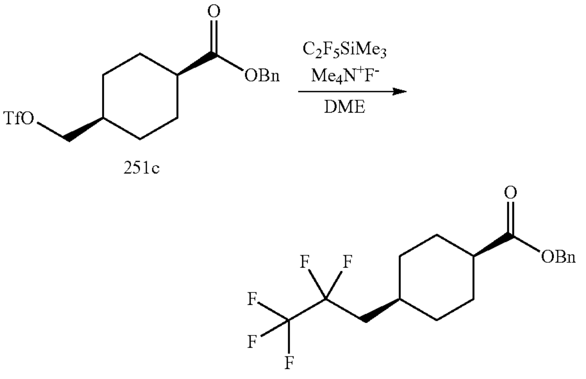

251c

251d (Pentafluoroethyl)trimethylsilane (105 mg, 0.548 mmol) was added to a solution of 4-trifluoromethanesulfonyloxymethyl-cyclohexanecarboxylic acid benzyl ester (cis: trans=4:1) (67.0 mg, 0.176 mmol) in DME (0.88 ml) at −30° C., and tetramethylammonium fluoride (21 mg, 0.22 mmol) was then added at −30 to −27° C. over one hour. The mixture was stirred for four hours while warming from −30° C. to 0° C. and further stirred at 0° C. for one hour. Water was added to the reaction mixture, followed by extraction with dichloromethane. The organic layer was then dried over $MgSO_4$ and concentrated under reduced pressure. The resulting residue was purified by silica gel column chromatography (hexane/ethyl acetate=150/1) to give 4-(2,2,3,3,3-pentafluoro-propyl)-cyclohexanecarboxylic acid benzyl ester (cis:trans=11:1) (11.4 mg, 18%).

$^1$H-NMR (400 MHz, $CDCl_3$) δ 1.32-1.75 (6H, m), 1.80-2.10 (5H, m), 2.26 (0.08H, m), 2.61 (0.92H, m), 5.13 (2H, s), 7.35 (5H, m).

(Reaction 251-5)

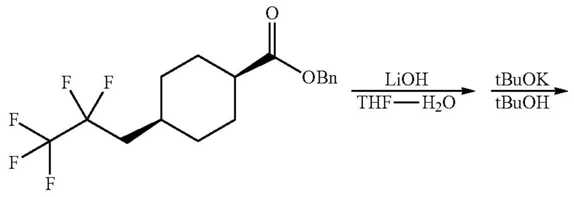

251d

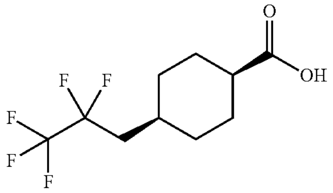

251e

LiOH.$H_2O$ (3.8 mg, 0.091 mmol) was added to a solution of 4-(2,2,3,3,3-pentafluoro-propyl)-cyclohexanecarboxylic acid benzyl ester (cis:trans=11:1) (11.4 mg, 0.0325 mmol) in THF (0.15 ml)-$H_2O$ (0.15 mL). The mixture was stirred at room temperature for 16 hours, and then adjusted to pH 2 with a 1 N aqueous HCl solution and extracted with dichloromethane. The organic layer was dried over $MgSO_4$ and concentrated under reduced pressure. The resulting residue was dissolved in tert-butanol (0.4 ml), and potassium tert-butoxide (10 mg, 0.089 mmol) was added. The mixture was stirred at room temperature for two hours, and then adjusted to pH 3 with a 1 N aqueous HCl solution and extracted with dichloromethane. The organic layer was then dried over $MgSO_4$ and concentrated under reduced pressure. The resulting residue was purified by column chromatography (hexane/ethyl acetate=5/1) to give 4-(2,2,3,3,3-pentafluoro-propyl)-cyclohexanecarboxylic acid (cis:trans=9:1) (8.5 mg, 100%).

$^1$H-NMR (400 MHz, $CDCl_3$) δ 1.11 (0.2H, m), 1.30-1.78 (5.8H, m), 1.83-2.10 (5H, m), 2.26 (0.1H, m), 2.64 (0.9H, m).

The carboxylic acid reagent used in the synthesis of Compound 1070 (4-((E)-3-fluoro-allyl)-cyclohexanecarboxylic acid) was synthesized by the following method.

(Reaction 251-6)

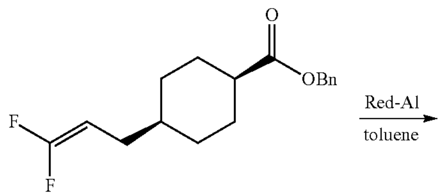

202h

-continued

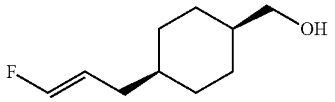

251f

A 3.3 M Red-Al solution in toluene (0.25 ml, 0.82 mmol) was added to a solution of 4-(3,3-difluoro-allyl)-cyclohexanecarboxylic acid benzyl ester (cis:trans=5.4:1) (42.8 mg, 0.145 mmol) in toluene (0.12 mL), and the mixture was stirred at 85° C. for 17 hours. The reaction mixture was poured into ice water, adjusted to pH 3 with a 4 N aqueous $H_2SO_4$ solution and extracted with ether. The organic layer was dried over $MgSO_4$ and concentrated under reduced pressure to give [4-((E)-3-fluoro-allyl)-cyclohexyl]-methanol (25.0 mg, 100%).

$^1$H-NMR (400 MHz, $CDCl_3$) δ 0.92 (0.84H, m), 1.20-1.84 (9.16H, m), 1.87 (1.68H, dd, J=7.8, 6.8 Hz), 2.10 (0.32H, t, J=7.3 Hz), 3.45 (0.32H, d, J=5.8 Hz), 3.54 (1.68H, d, J=6.8 Hz), 5.31 (1H, m), 6.47 (1H, dd, J=86.0, 11.0 Hz).

(Reaction 251-7)

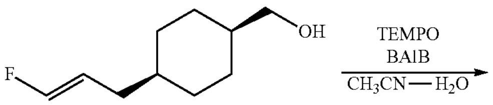

251f

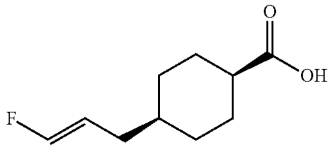

251g 4-((E)-3-Fluoro-allyl)-cyclohexanecarboxylic acid was synthesized by operations similar to those in Reaction 109-1 using appropriate reagents and starting material.

$^1$H-NMR (400 MHz, $CDCl_3$) δ 0.80-2.10 (11H, m), 2.26 (0.15H, m), 2.61 (0.85H, m), 4.71 (0.16H, dm, J=40.6 Hz), 5.30 (0.84H, m), 6.47 (1H, dd, J=86.0, 11.0 Hz) (cis:trans=85:15).

The carboxylic acid reagent used in the synthesis of Compound 1073 (4-fluoro-4-(3-fluoro-propyl)-cyclohexanecarboxylic acid) was synthesized by the following method.

(Reaction 251-8)

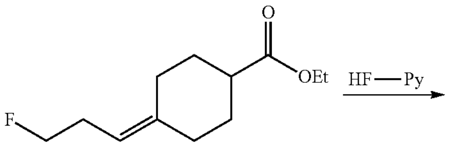

250f

-continued

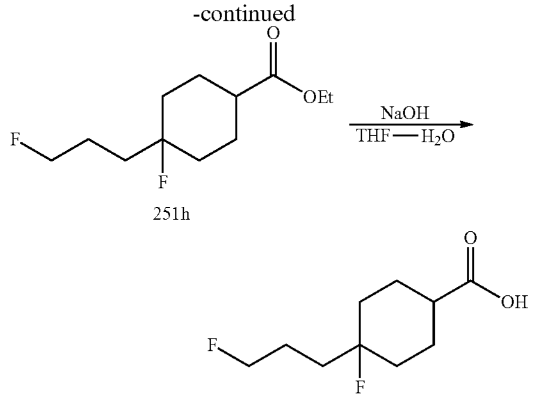

251h

251i

4-Fluoro-4-(3-fluoro-propyl)-cyclohexanecarboxylic acid was synthesized by operations similar to those in Reaction 249-9 and Reaction 95-18 using appropriate reagents and starting material.

$^1$H-NMR (400 MHz, $CDCl_3$) δ 2.36-2.17 (3H, m), 2.05-1.66 (8H, m), 1.47-1.25 (2H, m).

The carboxylic acid reagent used in the synthesis of Compound 1074 (4-ethynyl-cyclohexanecarboxylic acid) was synthesized by the following method.

(Reaction 251-9)

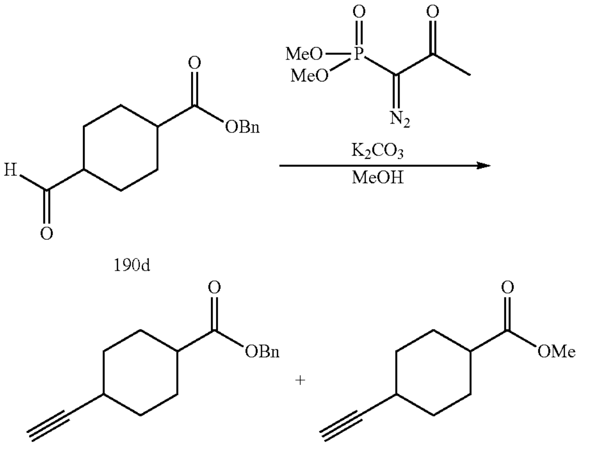

190d

251j

251k

Dimethyl (1-diazo-2-oxopropyl)phosphonate (Bestmann reagent) (450 mg, 2.34 mmol) was added to a mixture of 4-formyl-cyclohexanecarboxylic acid benzyl ester (390 mg, 1.58 mmol) and potassium carbonate (323 mg, 2.34 mmol) in methanol (10 mL) at 0° C. and the mixture was stirred for five hours. Further, the reaction solution was stirred at room temperature for two hours. A saturated aqueous ammonium chloride solution and ethyl acetate were then added at 0° C., and the organic layer and the aqueous layer were separated. The aqueous layer was repeatedly extracted with ethyl acetate three times, and the organic layers were then combined, washed with saturated brine and then concentrated under reduced pressure. The resulting residue was purified by silica gel column chromatography to give a mixture of 4-ethynyl-cyclohexanecarboxylic acid methyl ester and 4-ethynyl-cyclohexanecarboxylic acid benzyl ester as a colorless liquid (220 mg, 78%).

$^1$H-NMR (400 MHz, $CDCl_3$) δ 1.34-1.48 (1.6H, m), 1.48-1.62 (1H, m), 1.65-1.87 (2.6H, m), 1.87-2.10 (3.8H, m), 2.20-2.42 (1.4H, m), 2.65-2.75 (0.6H, m), 3.66 (1.1H, s), 3.68 (1.4H, s), 5.10 (0.05H, s), 5.13 (0.3H, s), 7.29-7.40 (0.9H, m) (Me:Bn=0.85:0.15, cis:trans=0.6:0.4).

(Reaction 251-10)

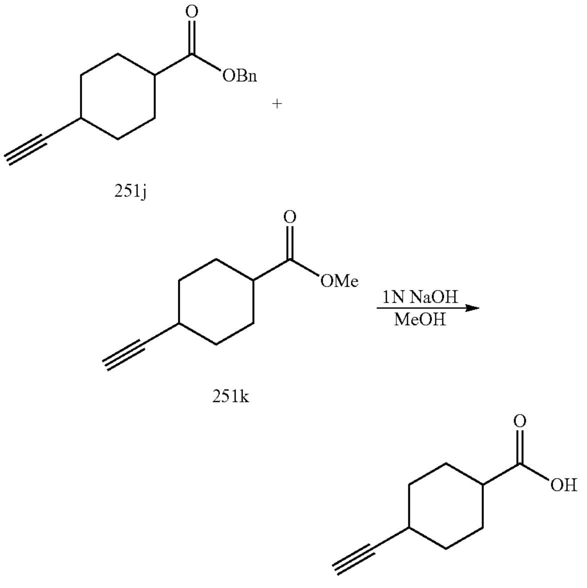

251j

251k

251l

4-Ethynyl-cyclohexanecarboxylic acid was synthesized by operations similar to those in Reaction 95-18 using appropriate reagents and starting material.

$^1$H-NMR (400 MHz, $CD_3OD$) δ 1.37-1.50 (1.3H, m), 1.53-1.67 (1.6H, m), 1.67-1.82 (2.8H, m), 1.82-2.05 (2.5H, m), 2.18-2.38 (2.1H, m), 2.62-2.73 (0.7H, m).

The carboxylic acid reagent used in the synthesis of Compound 1077 (4-(2-fluoro-propyl)-cyclohexanecarboxylic acid) was synthesized by the following method.

(Reaction 251-11)

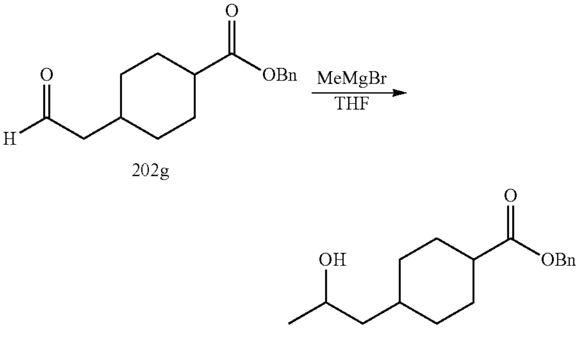

202g

251m

Methylmagnesium bromide (1 M solution in THF, 0.526 ml, 0.526 mmol) was added dropwise to 4-(2-oxo-ethyl)-cyclohexanecarboxylic acid benzyl ester (114 mg, 0.439 mmol) in THF (2.2 mL) at −78° C., and the mixture was stirred at the same temperature for 30 minutes. Water was added to the reaction mixture at the same temperature and extracted with ethyl acetate. The organic layer was sequentially washed with a saturated aqueous ammonium chloride solution, water and saturated brine and then concentrated under reduced pressure. The resulting residue was purified by silica gel column chromatography (hexane-ethyl acetate) to give 4-(2-hydroxy-propyl)-cyclohexanecarboxylic acid benzyl ester (80.7 mg, 67%).

$^1$H-NMR (300 MHz, $CDCl_3$) δ 1.18 (3H, d, J=6.1 Hz), 1.22-1.49 (5H, m), 1.50-1.67 (6H, m), 1.95-2.05 (2H, m), 2.58 (1H, dt, J=9.1, 4.9 Hz), 3.82-3.94 (1H, m), 5.13 (2H, s), 7.29-7.39 (5H, m);

MS (ESI) m/z=259 (M−$H_2$O+H)+.

(Reaction 251-12)

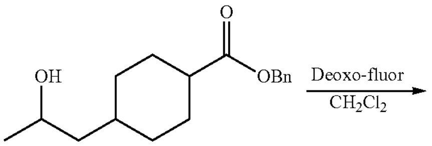

251m

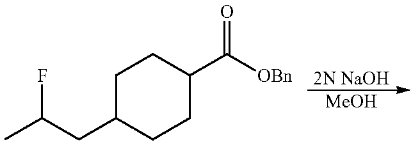

251n

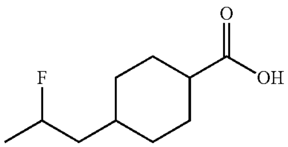

251o 4-(2-Fluoro-propyl)-cyclohexanecarboxylic acid was synthesized by operations similar to those in Reaction 191-11 and Reaction 95-18 using appropriate reagents and starting material.

$^1$H-NMR (400 MHz, $CDCl_3$) δ 1.23-2.07 (11H, m), 1.31 (3H, dd, J=23.9, 7.0 Hz), 2.55-2.64 (1H, m), 4.63-4.87 (1H, m).

Example 252

N-[4-(2-{2-[4-(1-Fluoro-1-methyl-ethyl)-cyclohexyl]-4-oxo-1,3,8-triaza-spiro[4.5]dec-1-ene-8-sulfonyl}-ethyl)-3-methyl-phenyl]-acetamide (Compound 1078)

(Reaction 252-1)

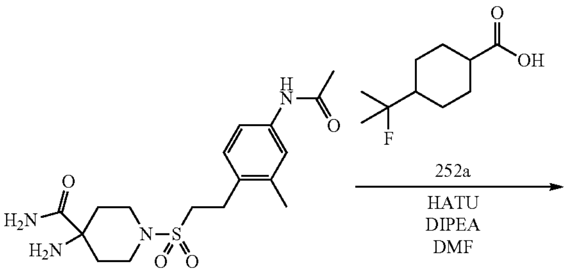

249b

-continued

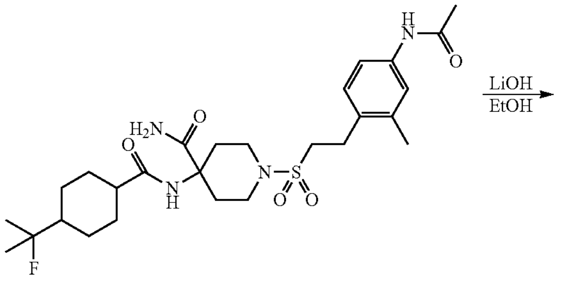

252b

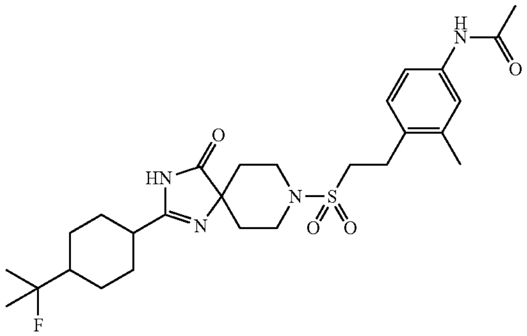

Compound 1078

N-[4-(2-{2-[4-(1-Fluoro-1-methyl-ethyl)-cyclohexyl]-4-oxo-1,3,8-triaza-spiro[4.5]dec-1-ene-8-sulfonyl}-ethyl)-3-methyl-phenyl]-acetamide was synthesized by operations similar to those in Reaction 10-14 and Reaction 101-3 using appropriate reagents and starting material.

MS (ESI) m/z=535 (M+H)+.

The carboxylic acid reagent used in the synthesis of Compound 1078 (4-(1-fluoro-1-methyl-ethyl)-cyclohexanecarboxylic acid) was synthesized by the following method.

(Reaction 252-2)

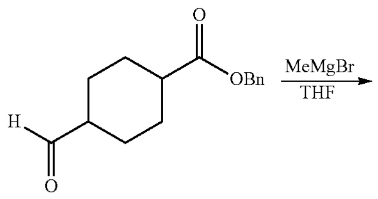

190d

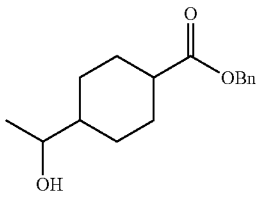

252c 4-(1-Hydroxy-ethyl)-cyclohexanecarboxylic acid benzyl ester was synthesized by operations similar to those in Reaction 251-11 using appropriate reagents and starting material.

MS (ESI) m/z=263 (M+H)+.

(Reaction 252-3)

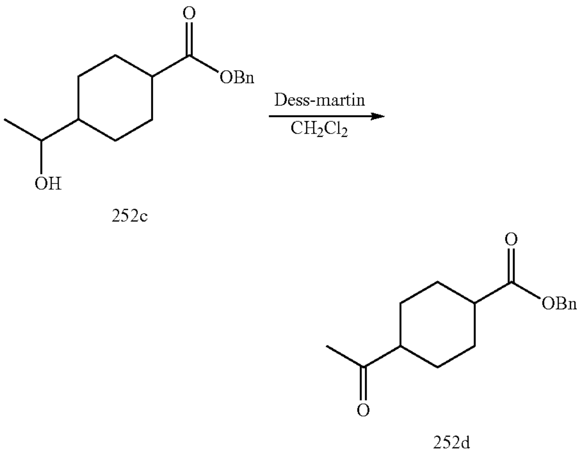

252c

252d

Dess-Martin reagent (151 mg, 0.355 mmol) was added to a solution of 4-(1-hydroxy-ethyl)-cyclohexanecarboxylic acid benzyl ester (71.6 mg, 0.273 mmol) in anhydrous dichloromethane (0.91 ml) at 0° C. The mixture was stirred at the same temperature for 10 minutes, and further warmed to room temperature and stirred for 4.5 hours. An aqueous sodium thiosulfate solution was added to the reaction solution, followed by extraction with dichloromethane. The organic phase was concentrated under reduced pressure, and the resulting residue was purified by silica gel column chromatography (hexane-ethyl acetate) to give 4-acetyl-cyclohexanecarboxylic acid benzyl ester (60.2 mg, 85%).

MS (ESI) m/z=261 (M+H)+.

(Reaction 252-4)

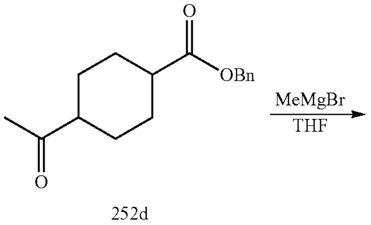

252d

-continued

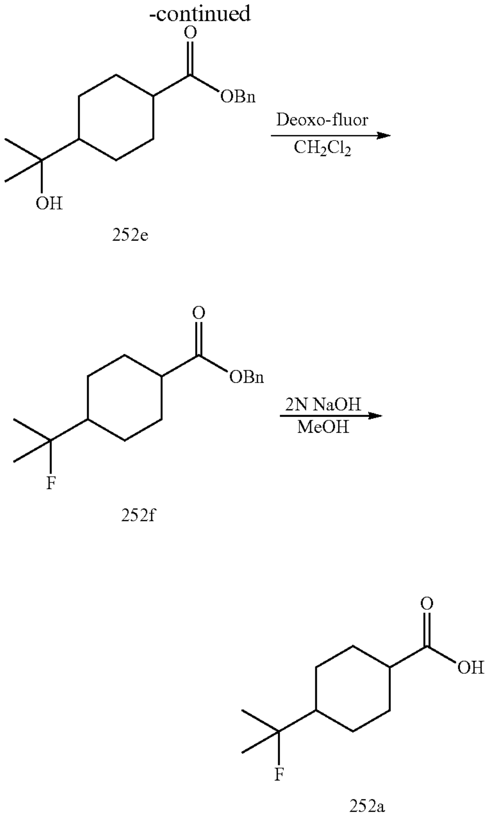

252e

252f

252a 4-(1-Fluoro-1-methyl-ethyl)-cyclohexanecarboxylic acid was synthesized by operations similar to those in Reaction 251-11, Reaction 191-11 and Reaction 95-18 using appropriate reagents and starting material.

$^1$H-NMR (300 MHz, $CD_3OD$) δ 1.20-1.32 (2H, m), 1.24 (6H, d, J=21.9 Hz), 1.45-1.58 (3H, m), 1.62-1.70 (2H, m), 2.17-2.26 (2H, m), 2.60-2.65 (1H, m).

Example 253

N-(4-{2-[2-(4-Butylidene-cyclohexyl)-4-oxo-1,3,8-triaza-spiro[4.5]dec-1-ene-8-sulfonyl]-ethyl}-3-methyl-phenyl)-acetamide (Compound 1079)

(Reaction 253-1)

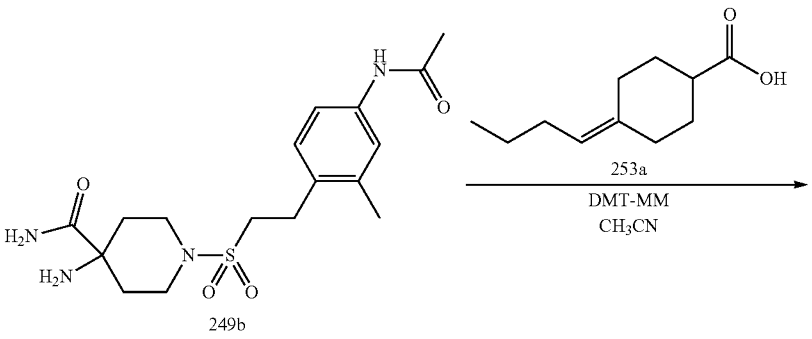

253a

249b

-continued

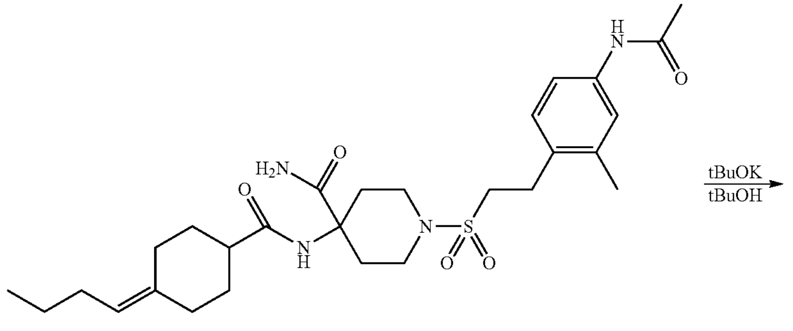

253b

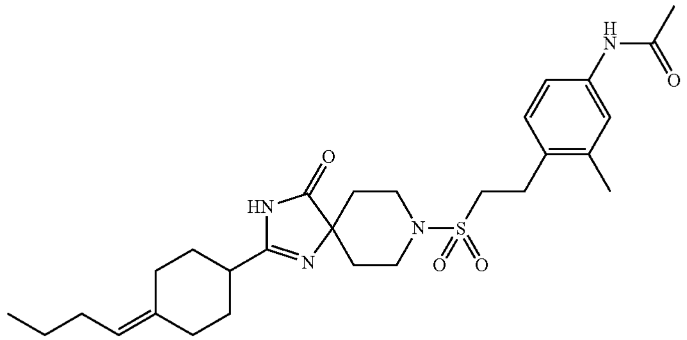

Compound 1079

N-(4-{2-[2-(4-Butylidene-cyclohexyl)-4-oxo-1,3,8-triaza-spiro[4.5]dec-1-ene-8-sulfonyl]-ethyl}-3-methyl-phenyl)-acetamide was synthesized by operations similar to those in Reaction 10-1 and Reaction 10-12 using appropriate reagents and starting material.

MS (ESI) m/z=529 (M+H)+.

The carboxylic acid reagent used in the synthesis of Compound 1079 (4-butylidene-cyclohexanecarboxylic acid) was synthesized by the following method.

(Reaction 253-2)

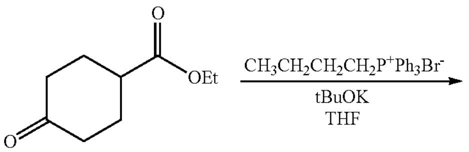

101b

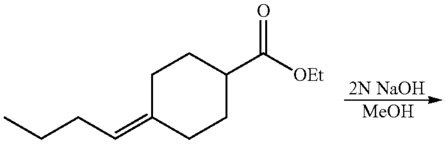

253c

-continued

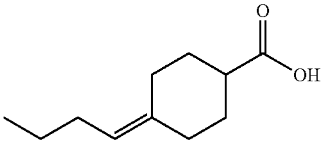

253a

4-Butylidene-cyclohexanecarboxylic acid was synthesized by operations similar to those in Reaction 191-14 and Reaction 95-18 using appropriate reagents and starting material.

$^1H$-NMR (400 MHz, $CDCl_3$) δ 0.88 (3H, t, J=7.3 Hz), 1.28-1.40 (2H, m), 1.42-1.62 (2H, m), 1.77-1.88 (1H, m), 1.89-2.12 (5H, m), 2.20-2.29 (1H, m), 2.46-2.55 (1H, m), 2.55-2.63 (1H, m), 5.14 (1H, t, J=7.3 Hz).

Example 254
N-[3-Methyl-4-(2-{4-oxo-2-[4-(2,2,3,3,3-pentafluoro-propyl)-cyclohexyl]-1,3,8-triaza-spiro[4.5]dec-1-ene-8-sulfonyl}-ethyl)-phenyl]-acetamide (Compound 1080)
(Reaction 254-1)
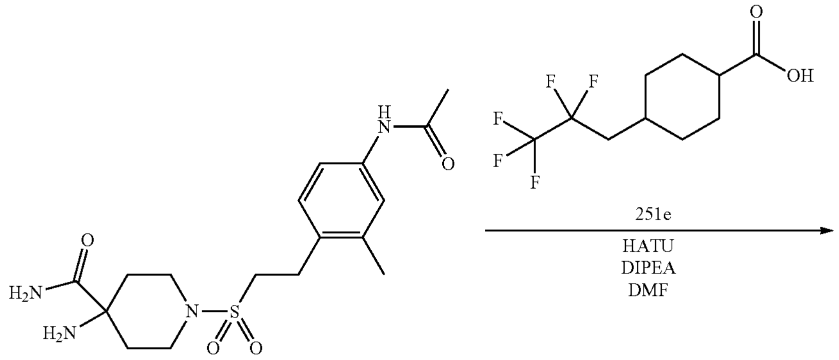
249b
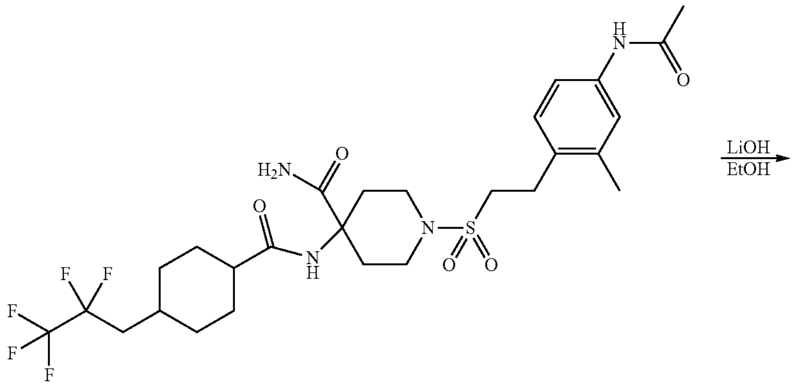
254a
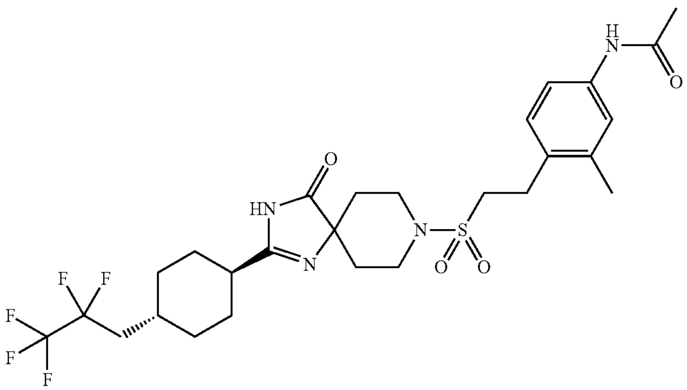
Compound 1080

N-[3-Methyl-4-(2-{4-oxo-2-[4-(2,2,3,3,3-pentafluoro-propyl)-cyclohexyl]-1,3,8-triaza-spiro[4.5]dec-1-ene-8-sulfonyl}-ethyl)-phenyl]-acetamide was synthesized by operations similar to those in Reaction 10-14 and Reaction 101-3 using appropriate reagents and starting material.

MS (ESI) m/z=607 (M+H)+.

Example 255

1-{3,5-Dimethyl-4-[2-(2-non-4-ynyl-4-oxo-1,3,8-triaza-spiro[4.5]dec-1-ene-8-sulfonyl)-ethyl]-phenyl}-1-methyl-urea (Compound 1081)

(Reaction 255-1)

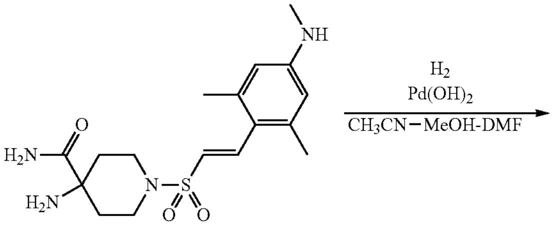

233f

-continued

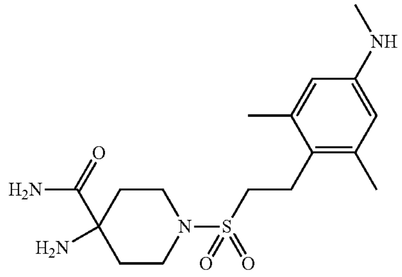

255a

4-Amino-1-[2-(2,6-dimethyl-4-methylamino-phenyl)-ethanesulfonyl]-piperidine-4-carboxylic amide was synthesized by operations similar to those in Reaction 184-1 using appropriate reagents and starting material.

MS (ESI) m/z=369 (M+H)+.

(Reaction 255-2)

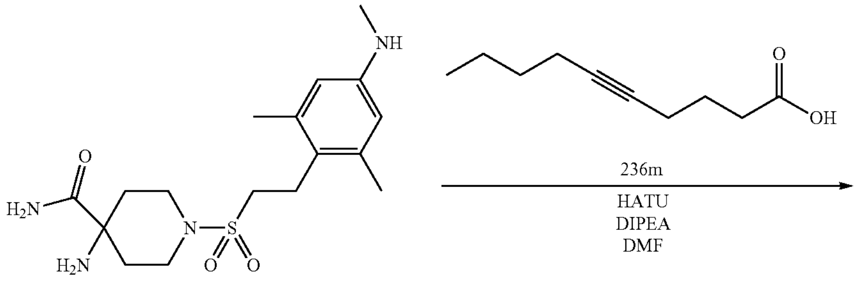

255a

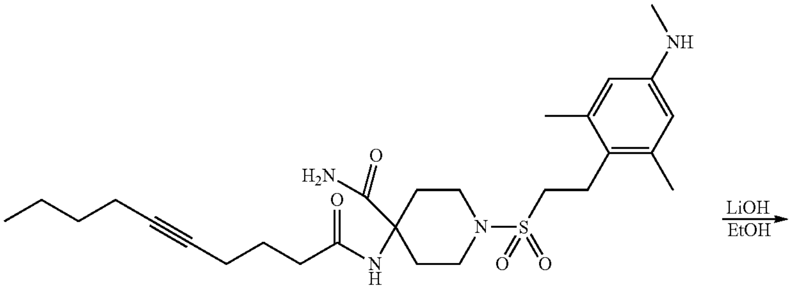

255b

-continued

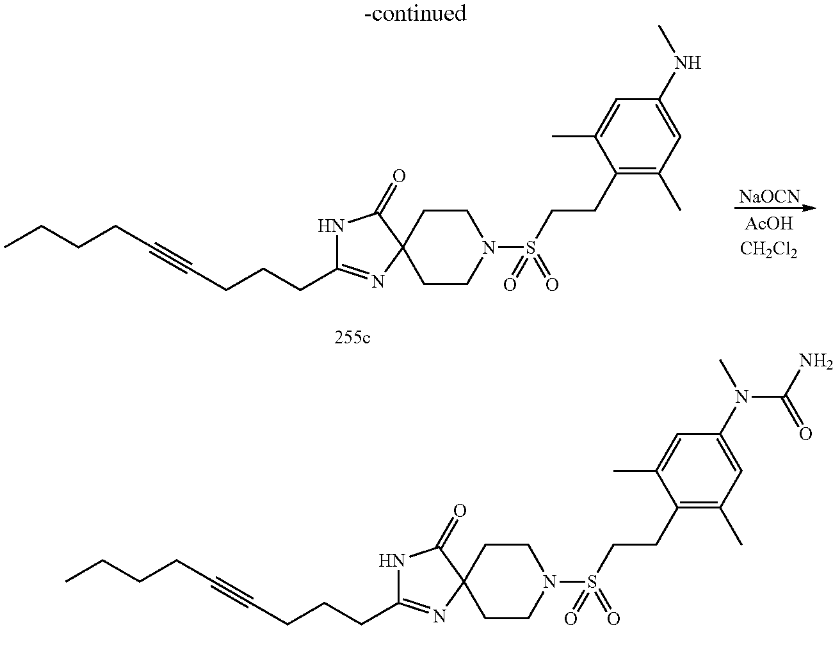

255c

Compound 1081

1-{3,5-Dimethyl-4-[2-(2-non-4-ynyl-4-oxo-1,3,8-triaza-spiro[4.5]dec-1-ene-8-sulfonyl)-ethyl]-phenyl}-1-methyl-urea was synthesized by operations similar to those in Reaction 10-14, Reaction 101-3 and Reaction 89-2 using appropriate reagents and starting material.

MS (ESI) m/z=544 (M+H)+.

The example compounds shown below were synthesized by operations similar to those in Reaction 255-2 using appropriate reagents and starting materials.

Compounds 1082 to 1083

TABLE 160

| Compound | Structure | LCMS condition | Retention time (min) | MS (m/z) |
|---|---|---|---|---|
| 1082 | 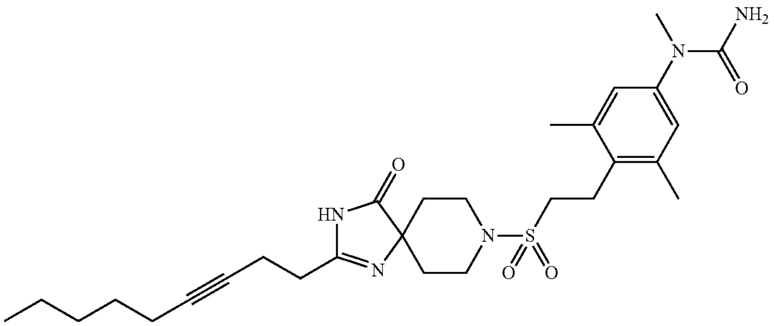 [SMILES: CCCCCC#CCCC1=NC2(CCN([S@TB17](=O)(=O)CCc3c(C)cc(N(C)C(N)=O)cc3C)CC2)C(=O)N1] | LCMS-F-1 | 1.01 | 544 (M + H)+ |
| 1083 | 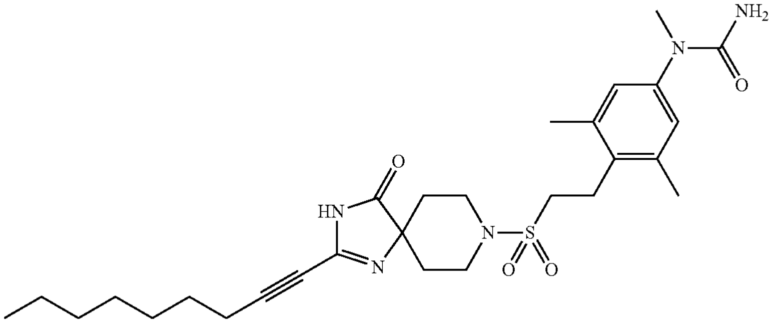 [SMILES: CCCCCCCC#CC1=NC2(CCN([S@TB17](=O)(=O)CCc3c(C)cc(N(C)C(N)=O)cc3C)CC2)C(=O)N1] | LCMS-C-2 | 2.27 | 544 (M + H)+ |

Example 256

1-(3,5-Dimethyl-4-{1-[4-oxo-2-(3-trifluoromethoxy-phenyl)-1,3,8-triaza-spiro[4.5]dec-1-ene-8-sulfonyl]-cyclopropylmethyl}-phenyl)-1-methyl-urea (Compound 1084)

(Reaction 256-1)

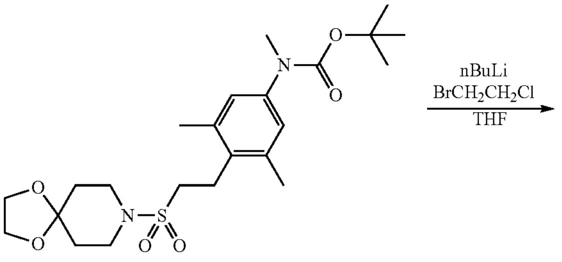

239a

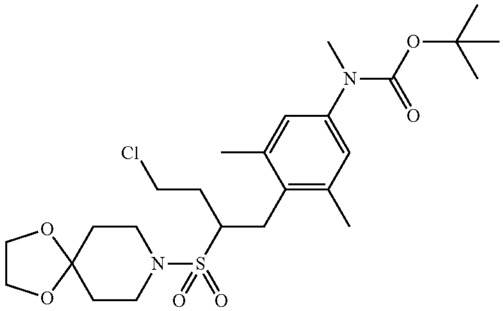

256a n-Butyllithium (1.6 M solution in hexane, 0.58 ml, 0.93 mmol) was added to a solution of {4-[2-(1,4-dioxa-8-aza-spiro[4.5]decane-8-sulfonyl)-ethyl]-3,5-dimethyl-phenyl}-methyl-carbamic acid tert-butyl ester (195.7 mg, 0.4176 mmol) in THF (4.2 ml) at −78° C. over six minutes, and the mixture was stirred at the same temperature for 20 minutes. 1-Bromo-2-chloro-ethane (105 μl, 1.26 mmol) was added to the reaction solution at −78° C. within 10 minutes. The mixture was then stirred while warming from −78° C. to 0° C. over one hour, and further stirred at room temperature for one hour. A 50% saturated aqueous ammonium chloride solution was added, followed by extraction with ethyl acetate. The organic layer was then dried over $MgSO_4$ and concentrated under reduced pressure. The resulting residue was purified by silica gel column chromatography (hexane/ethyl acetate=5/2) to give {4-[4-chloro-2-(1,4-dioxa-8-aza-spiro[4.5]decane-8-sulfonyl)-butyl]-3,5-dimethyl-phenyl}-methyl-carbamic acid tert-butyl ester (133 mg, 60%).

$^1$H-NMR (400 MHz, $CDCl_3$) δ 1.44 (9H, s), 1.80 (4H, t, J=6.0 Hz), 1.85 (1H, m), 2.28 (1H, m), 2.33 (6H, s), 3.00 (1H, dd, J=14.0, 11.6 Hz), 3.18 (1H, dd, J=14.0, 4.4 Hz), 3.22 (3H, s), 3.33 (1H, m), 3.52 (4H, t, J=6.0 Hz), 3.60 (2H, m), 3.98 (4H, s), 6.92 (2H, s).

(Reaction 256-2)

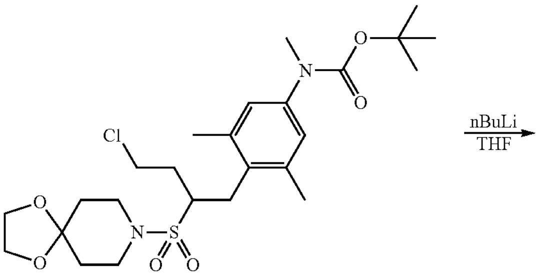

256a

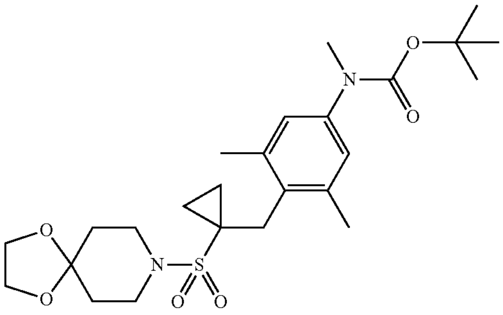

256b

+

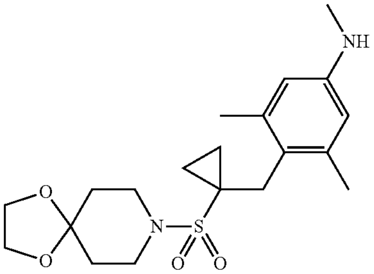

256c n-Butyllithium (1.6 M solution in hexane, 345 μl, 0.552 mmol) was added to a solution of {4-[4-chloro-2-(1,4-dioxa-8-aza-spiro[4.5]decane-8-sulfonyl)-butyl]-3,5-dimethyl-phenyl}-methyl-carbamic acid tert-butyl ester (115.0 mg, 0.2165 mmol) in THF (3.0 ml) at −78° C. over three minutes. The mixture was stirred at the same temperature for five minutes, and then warmed and further stirred at room temperature for one hour. A 50% saturated aqueous ammonium chloride solution was added, followed by extraction with ethyl acetate. The organic layer was then dried over $MgSO_4$ and concentrated under reduced pressure. The resulting residue was purified by silica gel column chromatography (hexane/ethyl acetate=2/1) to give {4-[1-(1,4-dioxa-8-aza-spiro[4.5]decane-8-sulfonyl)-cyclopropylmethyl]-3,5-dimethyl-phenyl}-methyl-carbamic acid tert-butyl ester and {4-[1-(1,4-dioxa-8-aza-spiro[4.5]decane-8-sulfonyl)-cyclopropylmethyl]-3,5-dimethyl-phenyl}-methyl-amine as a mixture (46.0 mg, 43% and 19.6 mg, 23%). This was used in the next reaction without complete purification.

(Reaction 256-3)

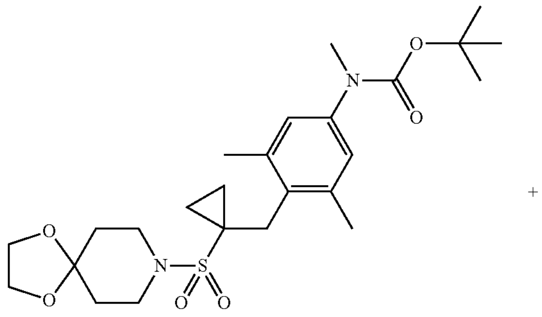

256b

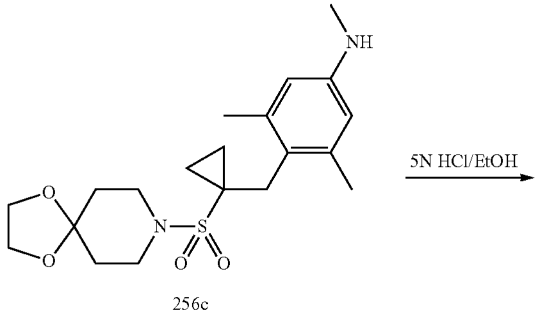

256c

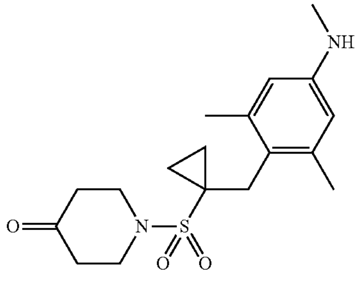

256d

A 5 N aqueous HCl solution (2.0 ml, 10 mmol) was added to a solution of a mixture of 4-[1-(1,4-dioxa-8-aza-spiro[4.5]decane-8-sulfonyl)-cyclopropylmethyl]-3,5-dimethyl-phenyl}-methyl-carbamic acid tert-butyl ester (54.7 mg, 0.111 mmol) and {4-[1-(1,4-dioxa-8-aza-spiro[4.5]decane-8-sulfonyl)-cyclopropylmethyl]-3,5-dimethyl-phenyl}-methyl-amine (23.1 mg, 0.0585 mmol) in EtOH (2.0 mL), and the mixture was stirred at 80° C. for two hours. The reaction mixture was neutralized by adding a 5 N aqueous NaOH solution (1.9 ml) and then extracted with ethyl acetate. The organic layer was dried over $MgSO_4$ and concentrated under reduced pressure to give 1-[1-(2,6-dimethyl-4-methylamino-benzyl)-cyclopropanesulfonyl]-4-piperidinone (58.8 mg, 99%).

$^1$H-NMR (400 MHz, $CDCl_3$) δ 0.44 (2H, m), 1.21 (2H, m), 2.22 (6H, s), 2.60 (4H, t, J=6.0 Hz), 2.79 (3H, s), 3.27 (2H, s), 3.78 (4H, t, J=6.0 Hz), 3.99 (4H, s), 6.28 (2H, s).

(Reaction 256-4)

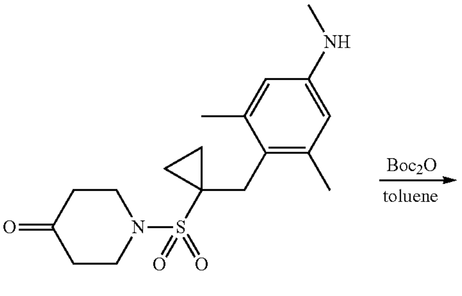

256d

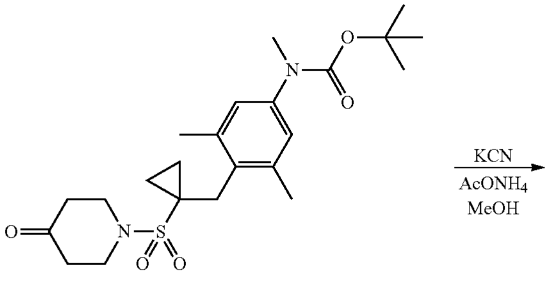

256e

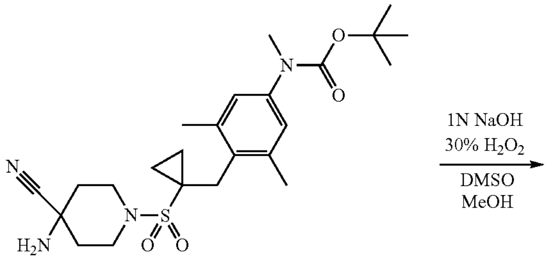

256f

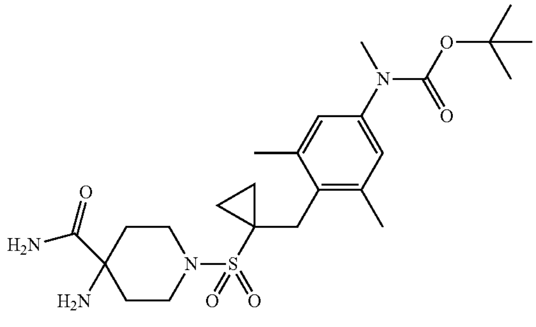

256g

{4-[1-(4-Amino-4-carbamoyl-piperidine-1-sulfonyl)-cyclopropylmethyl]-3,5-dimethyl-phenyl}-methyl-carbamic acid tert-butyl ester was synthesized by operations similar to those in Reaction 127-2 (using toluene as a solvent), Reaction 233-3 and Reaction 233-4 using appropriate reagents and starting material.

$^1$H-NMR (400 MHz, $CDCl_3$) δ 0.37 (2H, m), 1.19 (2H, m), 1.45 (9H, s), 1.59 (2H, m), 2.24 (2H, m), 2.30 (6H, s), 3.20 (3H, s), 3.36 (2H, s), 3.43 (2H, ddd, J=13.0, 9.6 and 3.2 Hz), 3.77 (2H, ddd, J=13.0, 5.2 and 4.8 Hz), 5.39 (1H, br), 6.89 (2H, s), 7.27 (1H, br).

(Reaction 256-5)
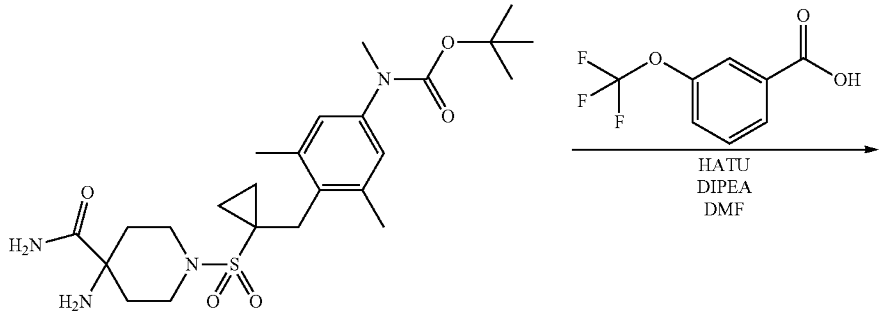
256g
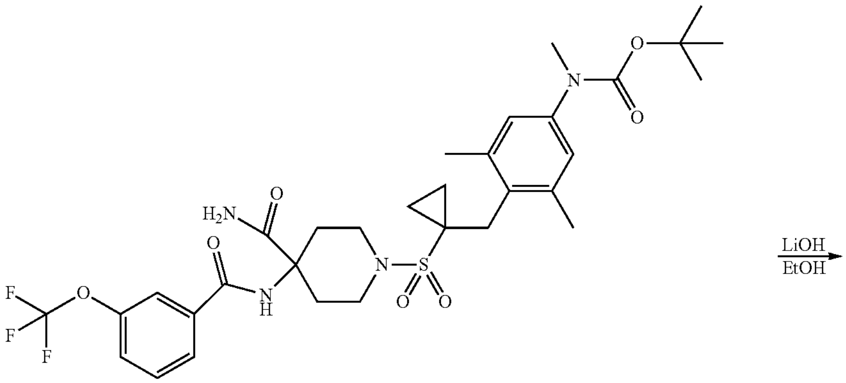
256h
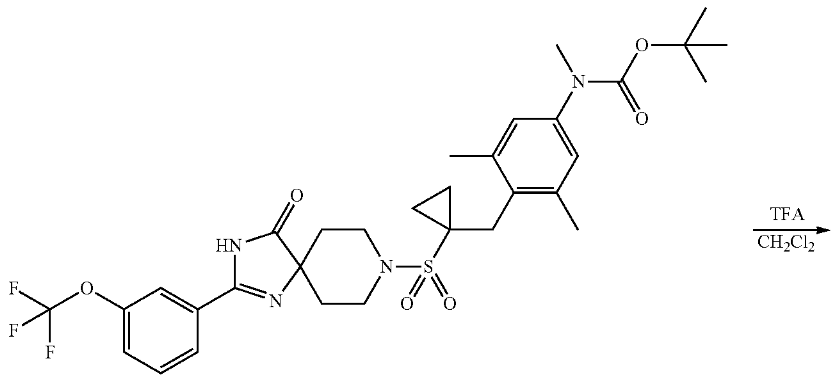
256i
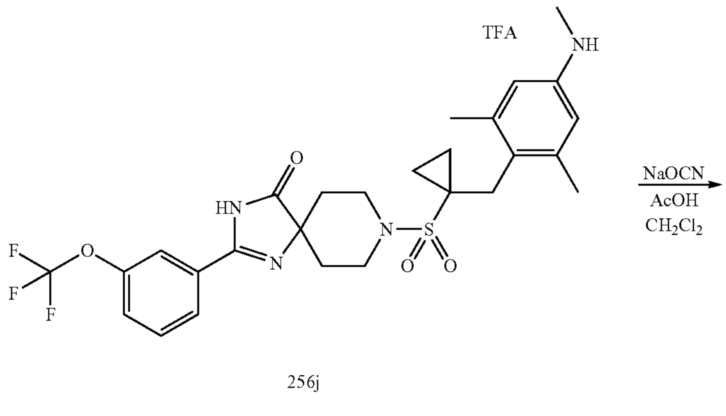
256j -continued

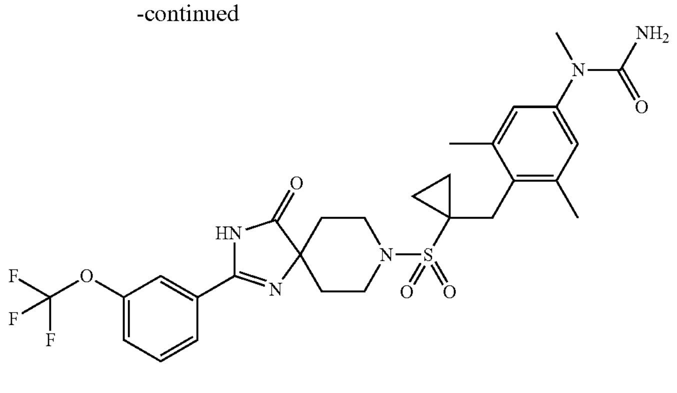

Compound 1084

1-(3,5-Dimethyl-4-{1-[4-oxo-2-(3-trifluoromethoxy-phenyl)-1,3,8-triaza-spiro[4.5]dec-1-ene-8-sulfonyl]-cyclopropylmethyl}-phenyl)-1-methyl-urea was synthesized by operations similar to those in Reaction 10-14, Reaction 101-3, Reaction 4-1 and Reaction 89-2 using appropriate reagents and starting material.

MS (ESI) m/z=608 (M+H)+.

Example 257

1-(4-{2,2-Difluoro-2-[4-oxo-2-(3-trifluoromethoxy-phenyl)-1,3,8-triaza-spiro[4.5]dec-1-ene-8-sulfonyl]-ethyl}-3,5-dimethyl-phenyl)-1-methyl-urea (Compound 1085)

(Reaction 257-1)

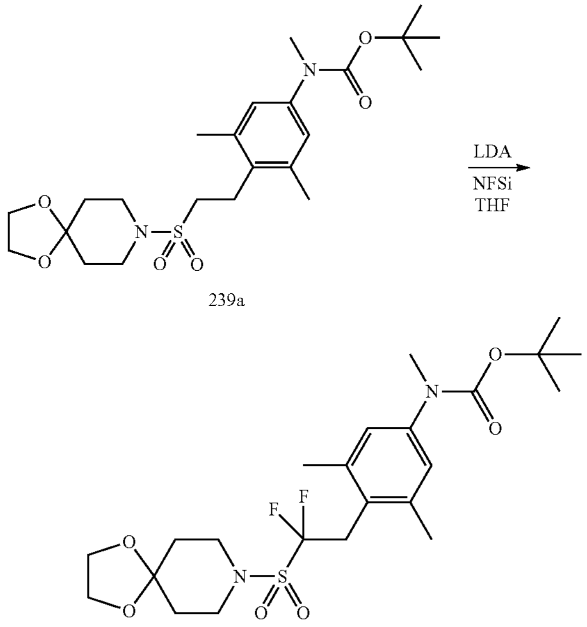

239a

257a n-Butyllithium (1.54 M solution in hexane, 5.6 ml, 8.67 mmol) was added to a solution of diisopropyl-amine (1.45 mL, 10.4 mmol) in tetrahydrofuran (30 mL) at 0° C., and the mixture was stirred for 20 minutes. The reaction solution was brought to −78° C., and a solution of {4-[2-(1,4-dioxa-8-aza-spiro[4.5]decane-8-sulfonyl)-ethyl]-3,5-dimethyl-phenyl}-methyl-carbamic acid tert-butyl ester (2.71 g, 5.78 mmol) in tetrahydrofuran (10 mL) was then added dropwise slowly. The reaction solution was stirred at −78° C. for 0.5 hour, and N-fluorobenzenesulfonimide (2.73 g, 8.67 mmol) was then added at −78° C., followed by stirring for one hour. A saturated aqueous ammonium chloride solution was added to the reaction solution at −78° C., and the mixture was brought to room temperature. Ethyl acetate was then added, and the organic layer and the aqueous layer were separated. The aqueous layer was repeatedly extracted with ethyl acetate three times. The organic layers were then combined and washed with saturated brine, and then dried over sodium sulfate and concentrated under reduced pressure. The resulting residue was purified by silica gel column chromatography to give {4-[2-(1,4-dioxa-8-aza-spiro[4.5]decane-8-sulfonyl)-2,2-difluoro-ethyl]-3,5-dimethyl-phenyl}-methyl-carbamic acid tert-butyl ester as a white foamy solid (205 mg, 7%).

MS (ESI) m/z=505 (M+H)+.

(Reaction 257-2)

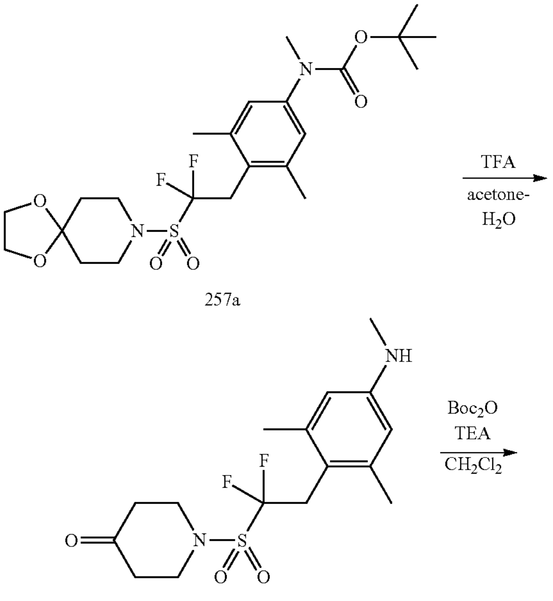

257a

257b

-continued
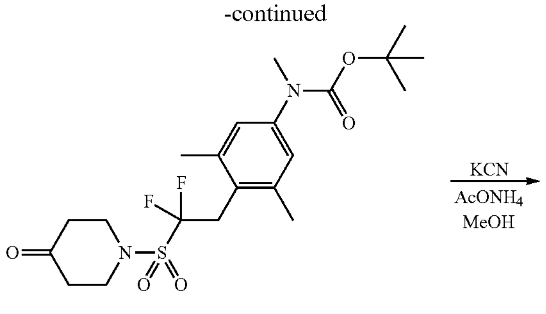
257c
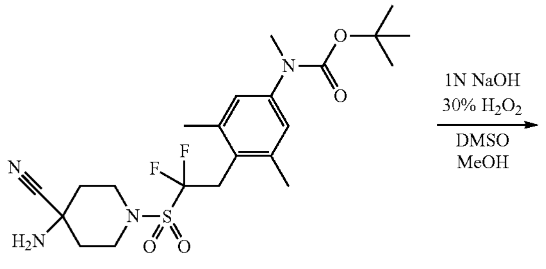
257d
-continued
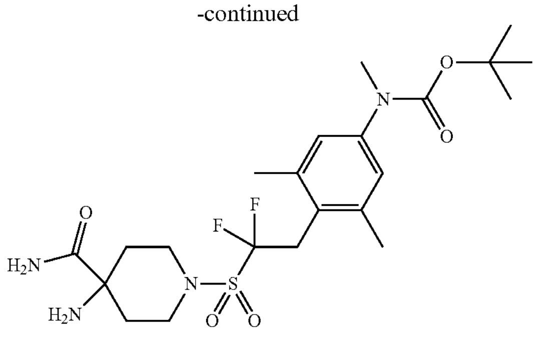
257e
{4-[2-(4-Amino-4-carbamoyl-piperidine-1-sulfonyl)-2,2-difluoro-ethyl]-3,5-dimethyl-phenyl}-methyl-carbamic acid tert-butyl ester was synthesized by operations similar to those in Reaction 233-2, Reaction 19-2, Reaction 233-3 and Reaction 233-4 using appropriate reagents and starting material.
MS (ESI) m/z=505 (M+H)+.
(Reaction 257-3)
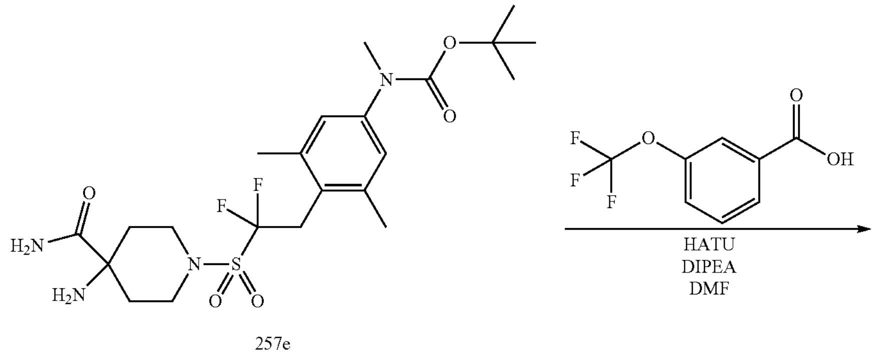
257e
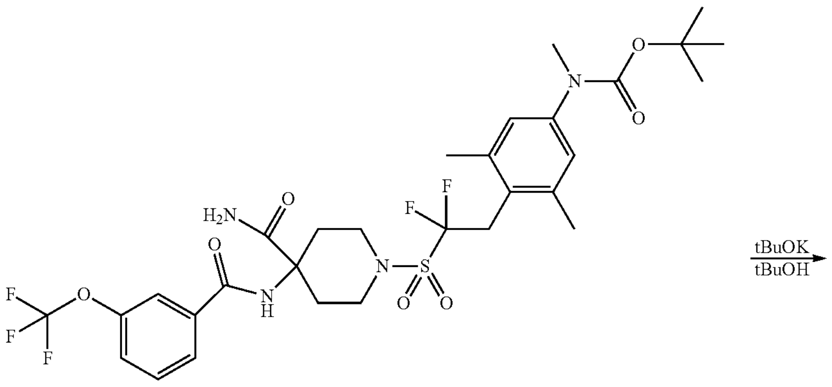
257f -continued
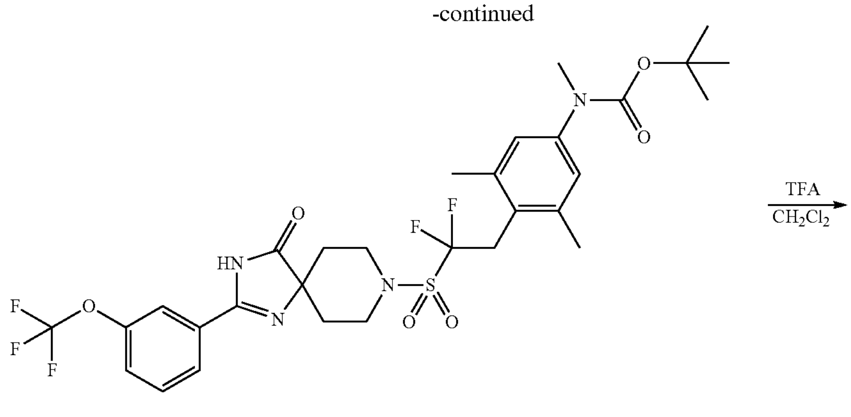
257g
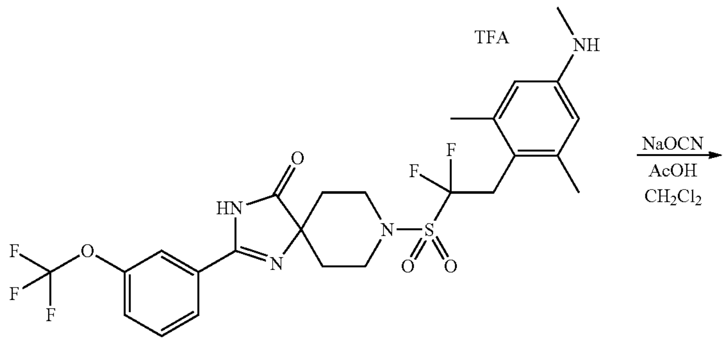
257h
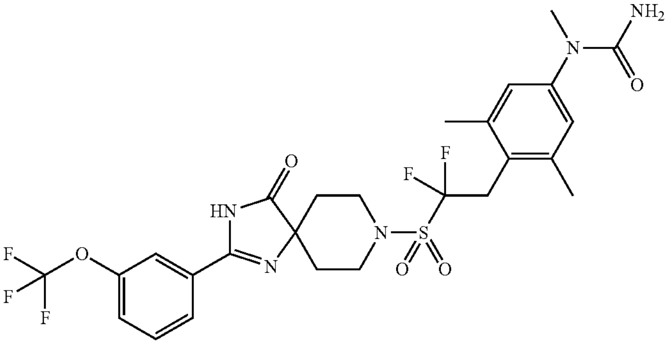
Compound 1085
1-(4-{2,2-Difluoro-2-[4-oxo-2-(3-trifluoromethoxy-phenyl)-1,3,8-triaza-spiro[4.5]dec-1-ene-8-sulfonyl]-ethyl}-3,5-dimethyl-phenyl)-1-methyl-urea was synthesized by operations similar to those in Reaction 10-14, Reaction 10-12, Reaction 4-1 and Reaction 89-2 using appropriate reagents and starting material.
MS (ESI) m/z=618 (M+H)+.

Example 258
1-{4-[2,2-Difluoro-2-(2-nonyl-4-oxo-1,3,8-triaza-spiro[4.5]dec-1-ene-8-sulfonyl)-ethyl]-3,5-dimethyl-phenyl}-1-methyl-urea (Compound 1086)
(Reaction 258-1)
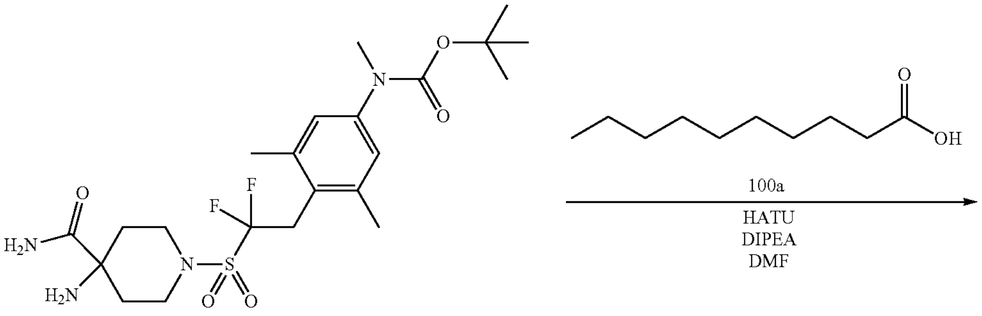
257e
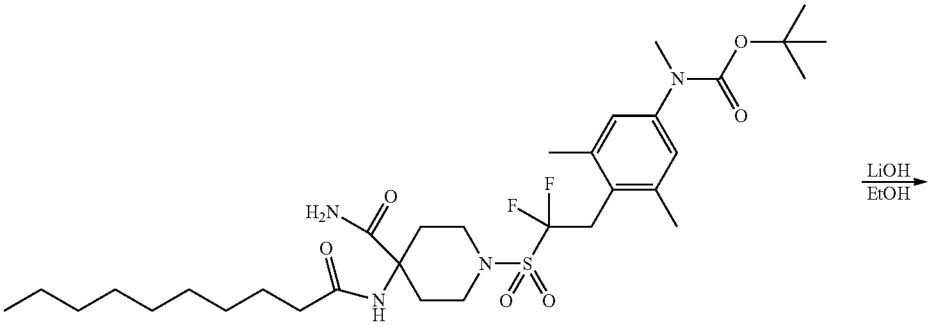
258a
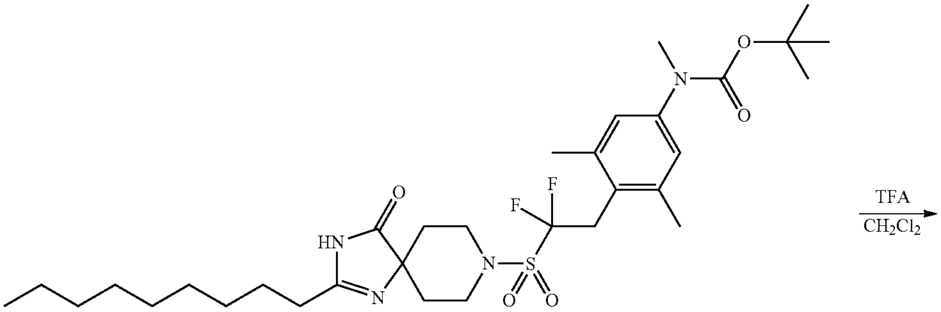
258b
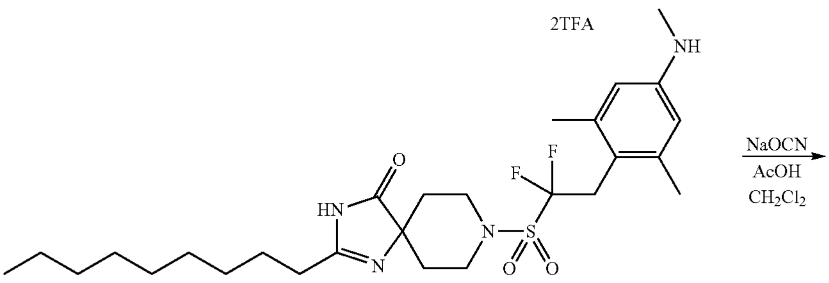
258c -continued

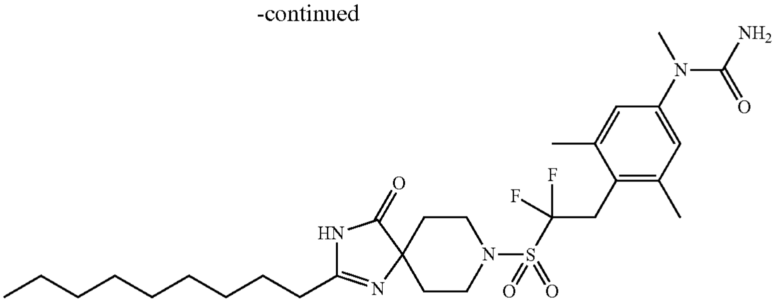

Compound 1086

1-{4-[2,2-Difluoro-2-(2-nonyl-4-oxo-1,3,8-triaza-spiro[4.5]dec-1-ene-8-sulfonyl)-ethyl]-3,5-dimethyl-phenyl}-1-methyl-urea was synthesized by operations similar to those in Reaction 10-14, Reaction 101-3, Reaction 4-1 and Reaction 89-2 using appropriate reagents and starting material.

MS (ESI) m/z=584 (M+H)+.

Example 259

1-{3,5-Dimethyl-4-[2-(4-oxo-2-[1,1';2',1"]terphenyl-3-yl-1,3,8-triaza-spiro[4.5]dec-1-ene-8-sulfonyl)-ethyl]-phenyl}-1-methyl-urea (Compound 1087)

(Reaction 259-1)

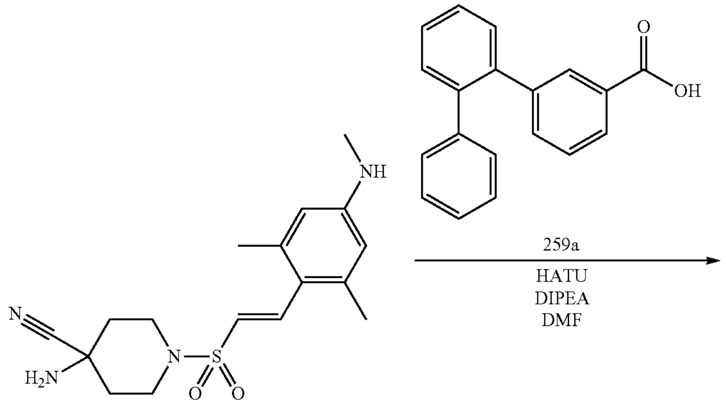

233e

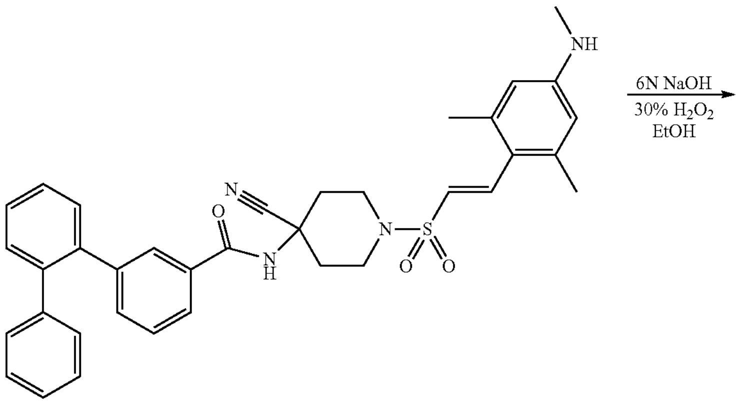

259b

-continued
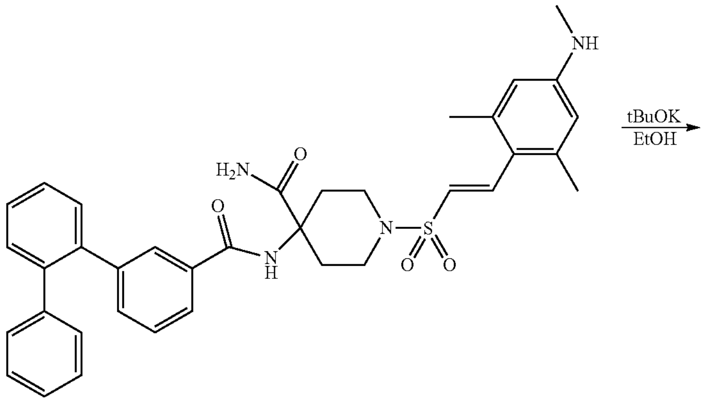
259c
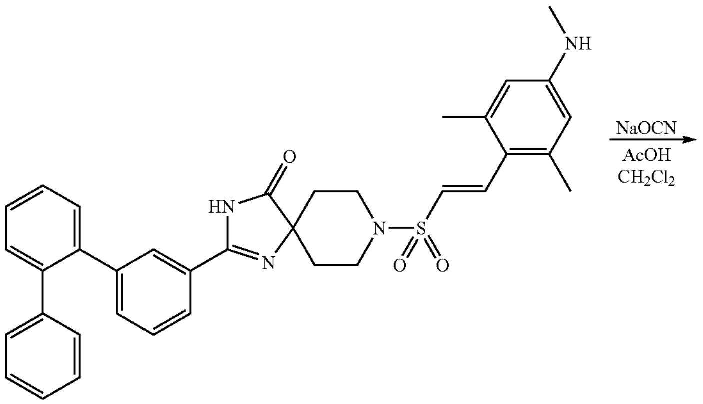
259d
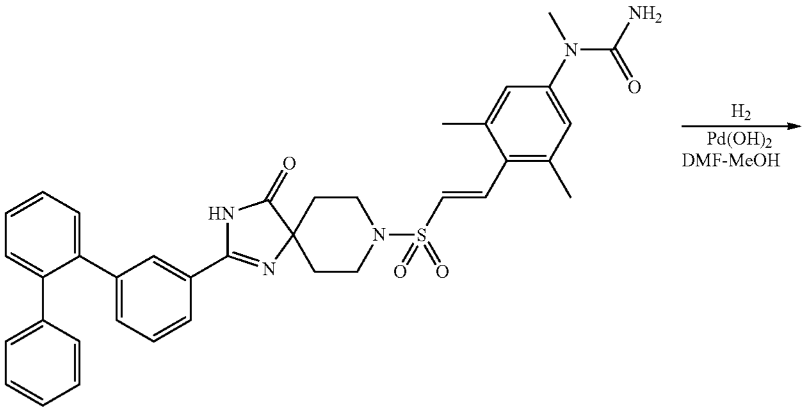
259e

-continued

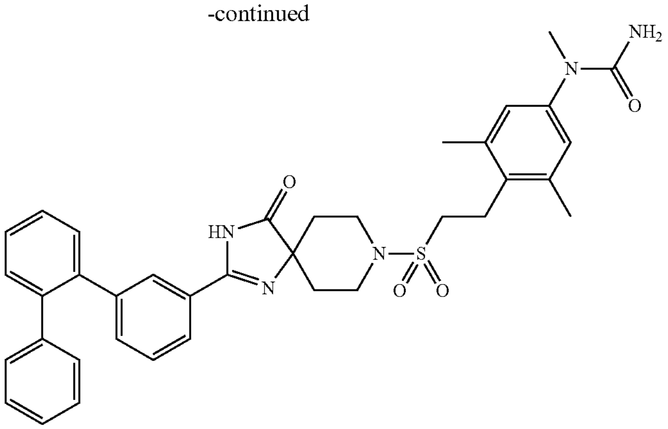

Compound 1087

1-{3,5-Dimethyl-4-[2-(4-oxo-2-[1,1';2',1"]terphenyl-3-yl-1,3,8-triaza-spiro[4.5]dec-1-ene-8-sulfonyl)-ethyl]-phenyl}-1-methyl-urea was synthesized by operations similar to those in Reaction 10-14, Reaction 10-11, Reaction 10-12 (using ethanol as a solvent), Reaction 89-2 and Reaction 122-2 using appropriate reagents and starting material.

MS (ESI) m/z=650 (M+H)+.

The carboxylic acid reagent used in the synthesis of Compound 1087 ([1,1';2',1"]terphenyl-3"-carboxylic acid) was synthesized by the following method.

(Reaction 259-2)

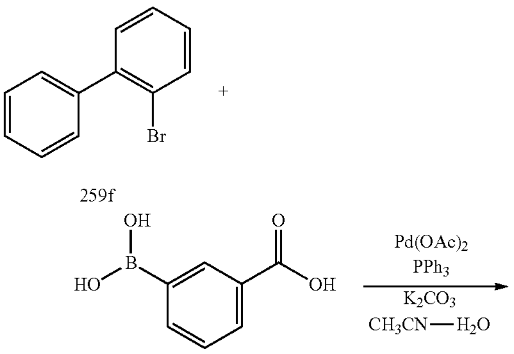

259f

259g

-continued

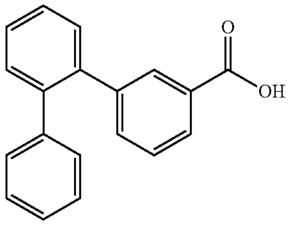

259a

3-Boronobenzoic acid (300 mg, 1.81 mmol), palladium acetate (40.4 mg, 0.18 mmol), triphenylphosphine (94.6 mg, 0.36 mmol) and potassium carbonate (374.6 mg, 2.71 mmol) were added to a solution of 2-bromo-1,1'-biphenyl (0.3 ml, 1.81 mmol) in acetonitrile (10 mL)-water (2.5 ml), and the mixture was heated with stirring at 100° C. overnight. The reaction mixture was cooled and then filtered through celite, and the filtrate was concentrated under reduced pressure. The resulting residue was purified by silica gel column chromatography (hexane:ethyl acetate=1:1) to give [1,1';2',1"]terphenyl-3"-carboxylic acid (191 mg, 39%).

MS (ESI) m/z=275 (M+H)+.

Example 260

1-[3,5-Dimethyl-4-((E)-2-{4-oxo-2-[4-(4,4,4-trifluoro-butyl)-phenyl]-1,3,8-triaza-spiro[4.5]dec-1-ene-8-sulfonyl}-vinyl)-phenyl]-1-methyl-urea (Compound 1088)

(Reaction 260-1)

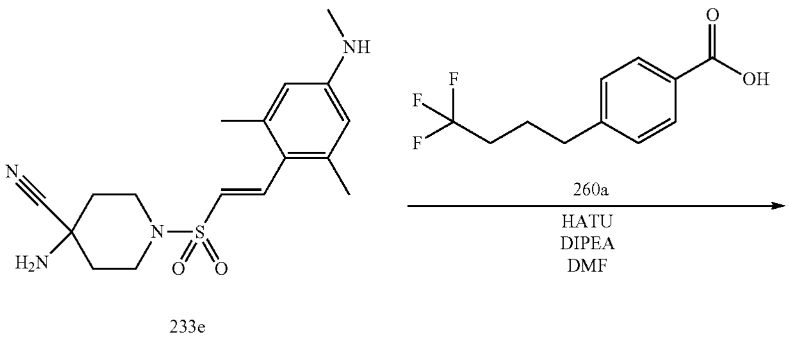

260a

233e

-continued

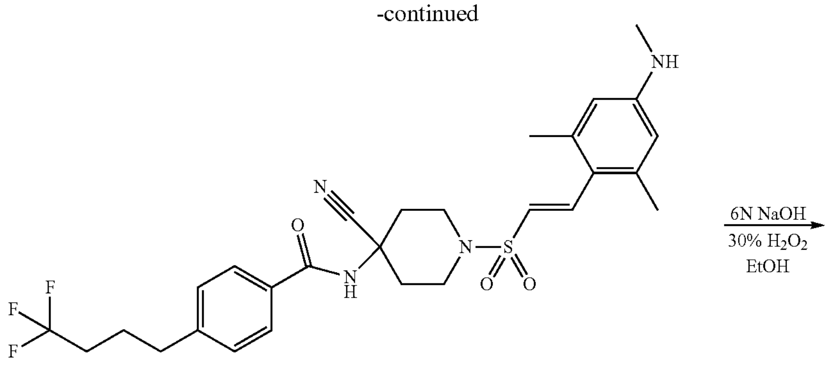

260b

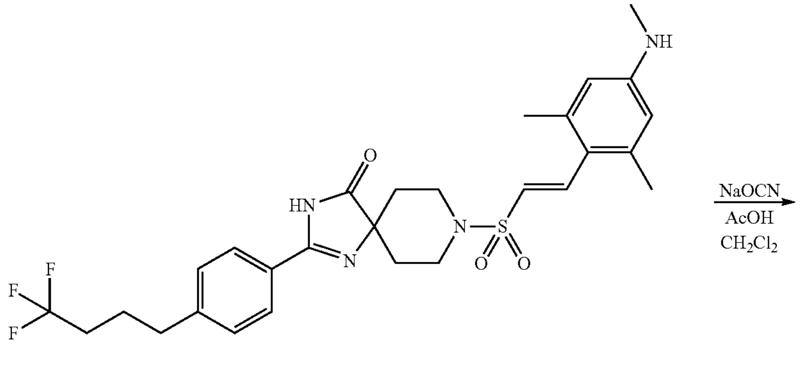

260c

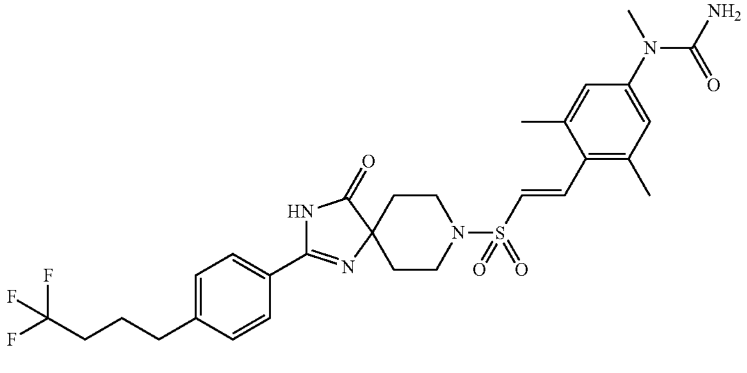

Compound 1088

1-[3,5-Dimethyl-4-((E)-2-{4-oxo-2-[4-(4,4,4-trifluoro-butyl)-phenyl]-1,3,8-triaza-spiro[4.5]dec-1-ene-8-sulfonyl}-vinyl)-phenyl]-1-methyl-urea was synthesized by operations similar to those in Reaction 10-14, Reaction 1-4 and Reaction 89-2 using appropriate reagents and starting material.

MS (ESI) m/z=606 (M+H)+.

The carboxylic acid reagent used in the synthesis of Compound 1088 (4-(4,4,4-trifluoro-butyl)-benzoic acid) was synthesized by the following method.

(Reaction 260-2)

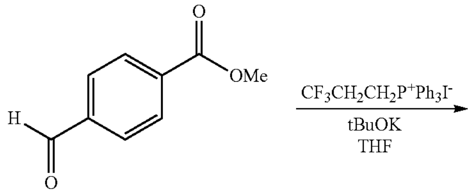

193e

-continued

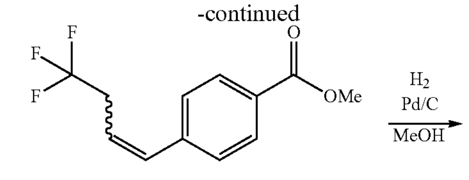

260d

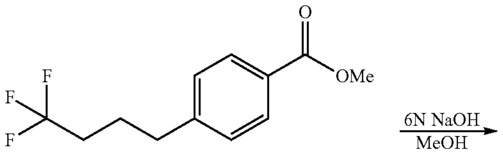

260e

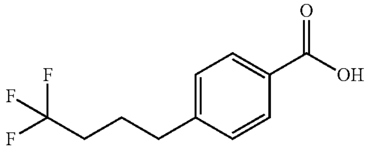

260a 4-(4,4,4-Trifluoro-butyl)-benzoic acid was synthesized by operations similar to those in Reaction 191-14, Reaction 18-2 and Reaction 95-18 using appropriate reagents and starting material.

MS (ESI) m/z=233 (M+H)+.

The example compound shown below was synthesized by operations similar to those in Reaction 260-1 using appropriate reagents and starting material.

Compound 1089

The carboxylic acid reagent used in the synthesis of Compound 1089 (3-(4,4,4-trifluoro-butyl)-benzoic acid) was synthesized by the following method.

(Reaction 260-3)

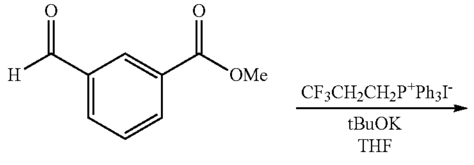

193n

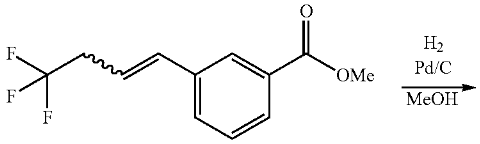

260f

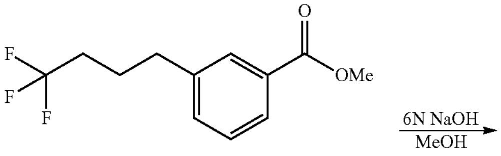

260g

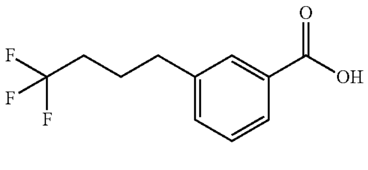

260h

TABLE 161

| Compound | Structure | LCMS condition | Retention time (min) | MS (m/z) |
|---|---|---|---|---|
| 1089 | 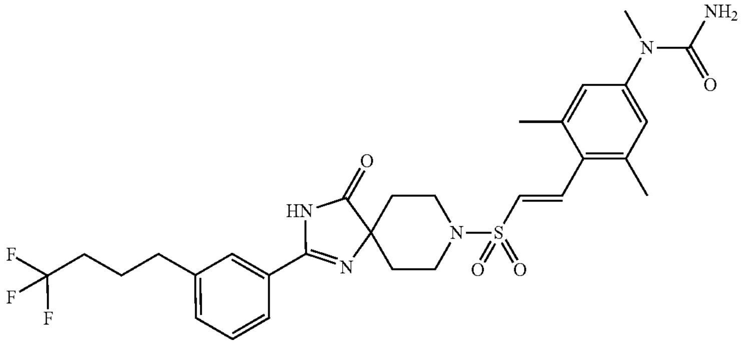 [SMILES: Cc1cc(N(C)C(N)=O)cc(C)c1/C=C/[S@TB4](=O)(=O)N1CCC2(CC1)N=C(c1cccc(CCCC(F)(F)F)c1)NC2=O] | LCMS-D-1 | 2.63 | 606 (M + H)+ |

3-(4,4,4-Trifluoro-butyl)-benzoic acid was synthesized by operations similar to those in Reaction 191-14, Reaction 18-2 and Reaction 95-18 using appropriate reagents and starting material.

MS (ESI) m/z=233 (M+H)+.

Example 261

1-(3,5-Dimethyl-4-{2-[4-oxo-2-(3-trifluoromethoxy-phenyl)-1,3,8-triaza-spiro[4.5]dec-1-ene-8-sulfonyl]-propyl}-phenyl)-1-methyl-urea (Compound 1090)

(Reaction 261-1)

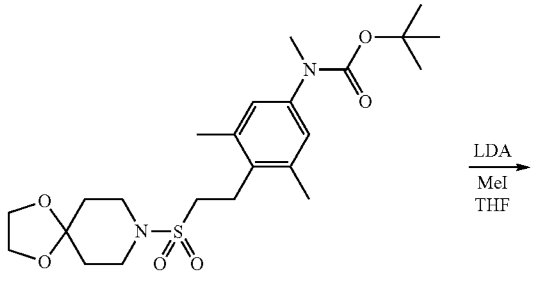

239a

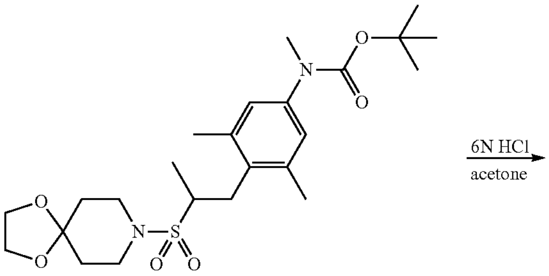

261a

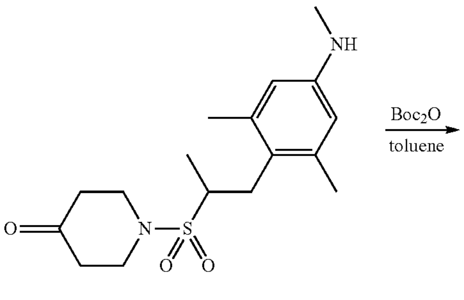

261b

-continued

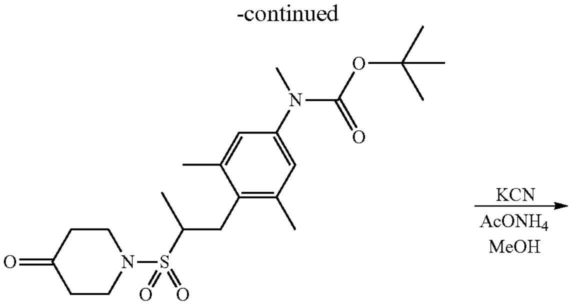

261c

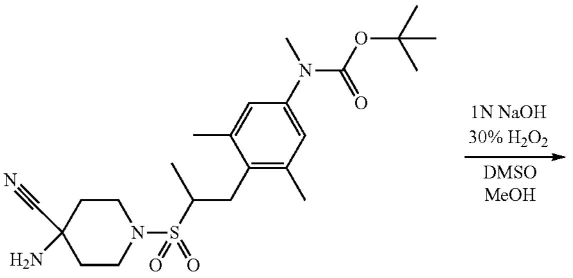

261d

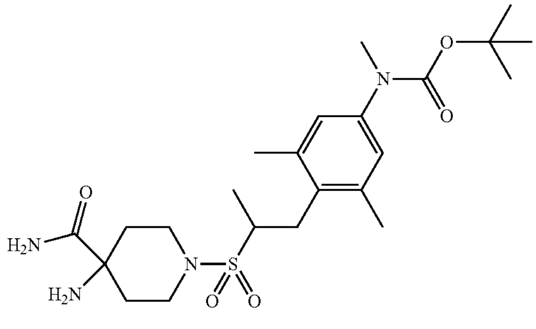

261e

{4-[2-(4-Amino-4-carbamoyl-piperidine-1-sulfonyl)-propyl]-3,5-dimethyl-phenyl}-methyl-carbamic acid tert-butyl ester was synthesized by operations similar to those in Reaction 256-1 (using LDA as a base), Reaction 233-2 (using hydrochloric acid as an acid), Reaction 127-2, Reaction 233-3 and Reaction 233-4 using appropriate reagents and starting material.

$^1$H-NMR (400 MHz, $CDCl_3$) δ 1.21 (3H, d, J=6.4 Hz), 1.46 (9H, s), 1.57 (2H, m), 2.19 (2H, m), 2.32 (6H, s), 2.90 (1H, dd, J=14.2 and 12.2 Hz), 3.21 (3H, s), 3.26 (2H, m), 3.40 (2H, m), 3.68 (2H, m), 5.33 (1H, br), 6.91 (2H, s), 7.23 (1H, br).

(Reaction 261-2)
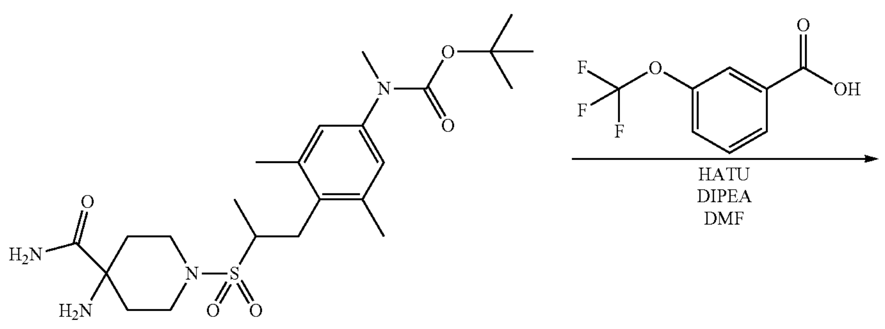
261e
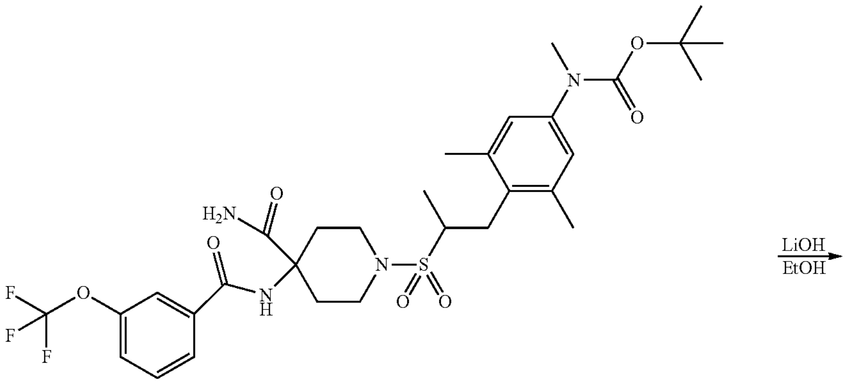
261f
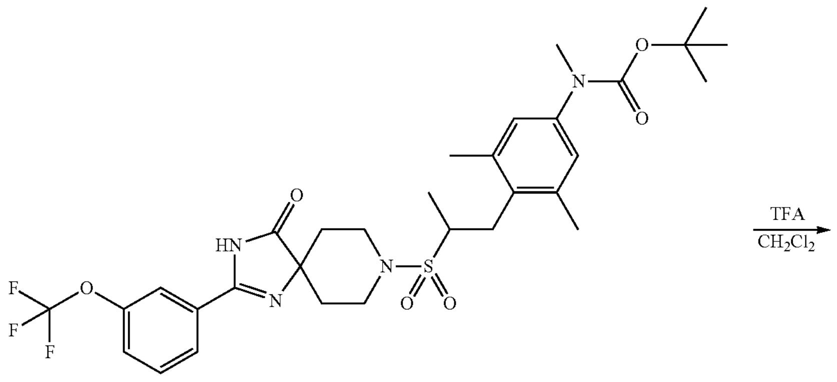
261g
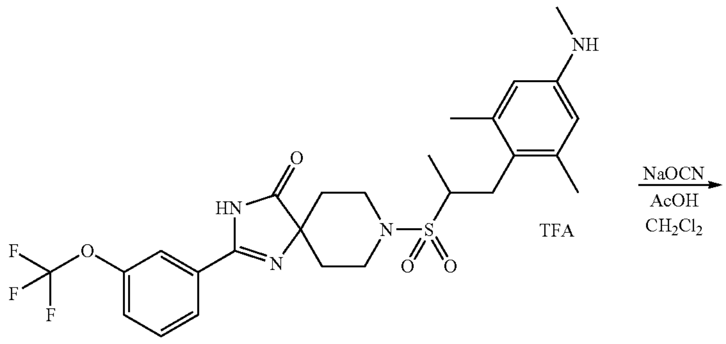
261h -continued

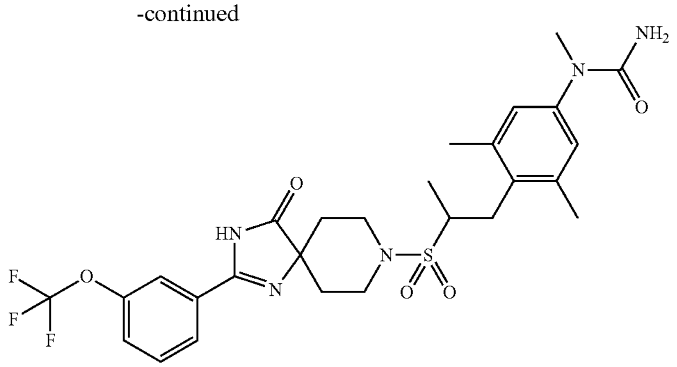

Compound 1090

1-(3,5-Dimethyl-4-{2-[4-oxo-2-(3-trifluoromethoxy-phenyl)-1,3,8-triaza-spiro[4.5]dec-1-ene-8-sulfonyl]-propyl}-phenyl)-1-methyl-urea was synthesized by operations similar to those in Reaction 10-14, Reaction 101-3, Reaction 4-1 and Reaction 89-2 using appropriate reagents and starting material.

MS (ESI) m/z=596 (M+H)+.

Example 262

2-[4-Fluoro-3-(4,4,5,5,5-pentafluoro-pentyloxy)-phenyl]-8-{(E)-2-[4-(4-hydroxy-piperidine-1-carbonyl)-2,6-dimethyl-phenyl]-ethenesulfonyl}-1,3,8-triaza-spiro[4.5]dec-1-en-4-one (Compound 1091)

(Reaction 262-1)

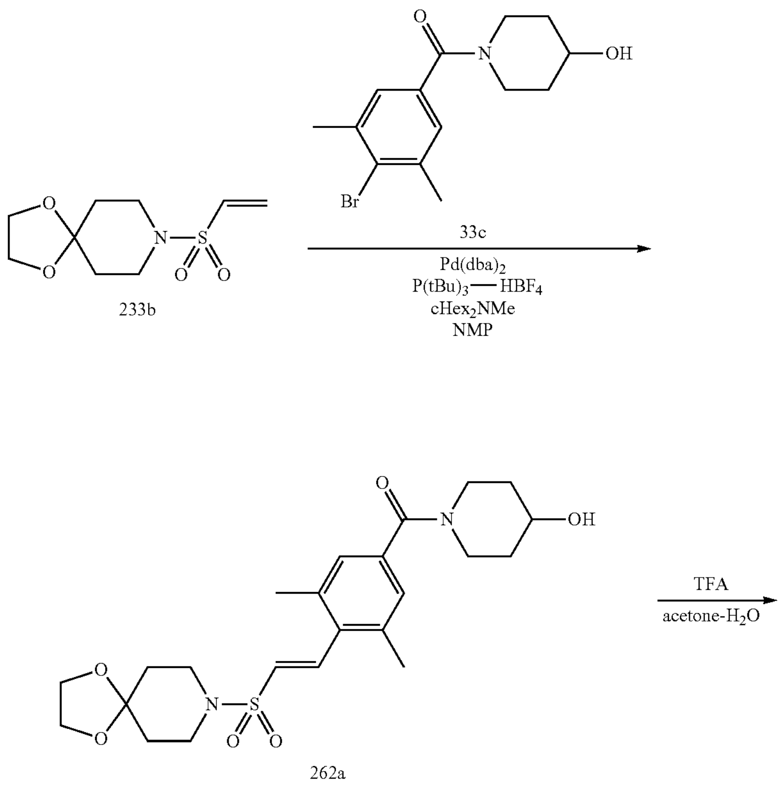

-continued
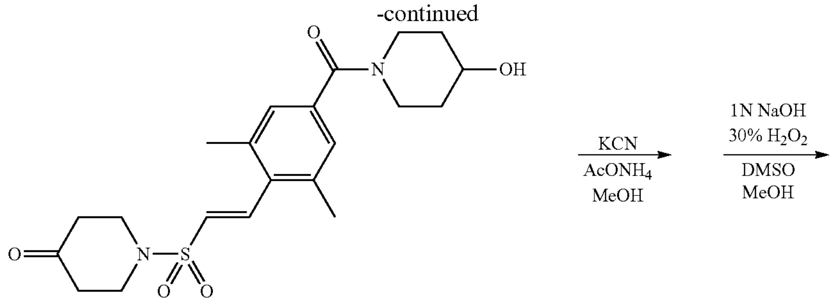
262b
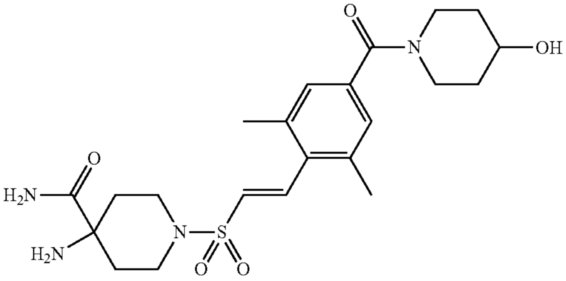
262c
4-Amino-1-{(E)-2-[4-(4-hydroxy-piperidine-1-carbonyl)-2,6-dimethyl-phenyl]-ethenesulfonyl}-piperidine-4-carboxylic amide was synthesized by operations similar to those in Reaction 119-1, Reaction 233-2, Reaction 233-3 and Reaction 233-4 using appropriate reagents and starting material.
MS (ESI) m/z=465 (M+H)+.
(Reaction 262-2)
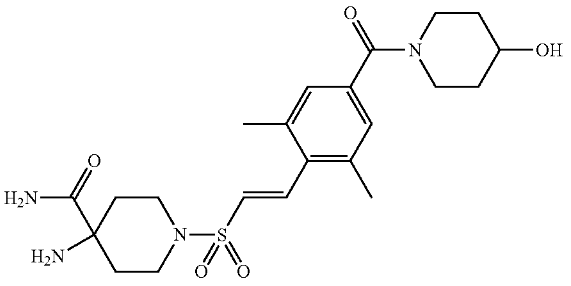
262c
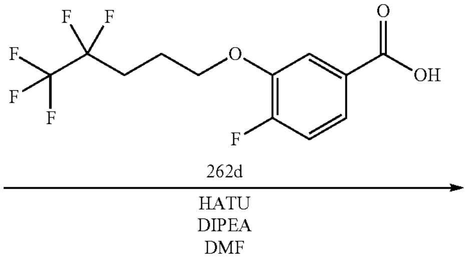
262d
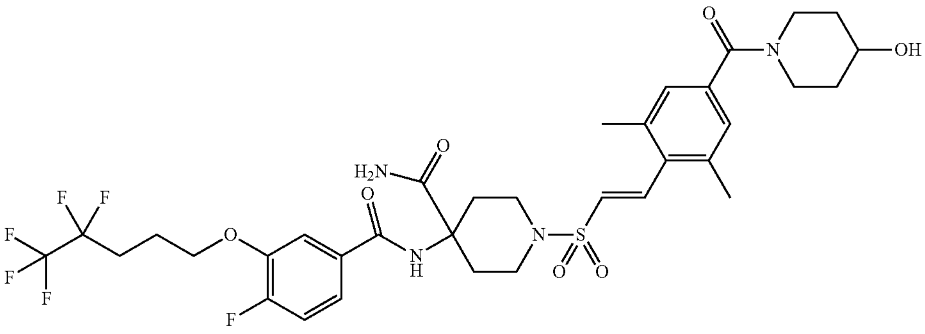
262e
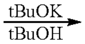

-continued

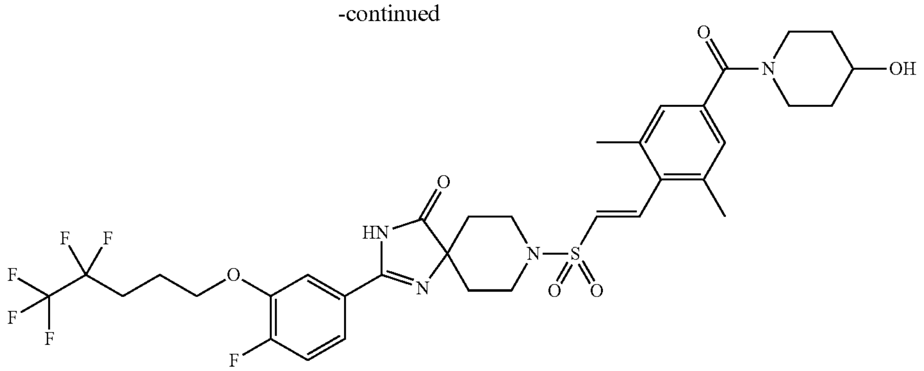

Compound 1091

2-[4-Fluoro-3-(4,4,5,5,5-pentafluoro-pentyloxy)-phenyl]-8-{(E)-2-[4-(4-hydroxy-piperidine-1-carbonyl)-2,6-dimethyl-phenyl]-ethenesulfonyl}-1,3,8-triaza-spiro[4.5]dec-1-en-4-one was synthesized by operations similar to those in Reaction 10-14 and Reaction 10-12 using appropriate reagents and starting material.

MS (ESI) m/z=745 (M+H)+.

The carboxylic acid reagent used in the synthesis of Compound 1091 (4-fluoro-3-(4,4,5,5,5-pentafluoro-pentyloxy)-benzoic acid) was synthesized by the following method.

(Reaction 262-3)

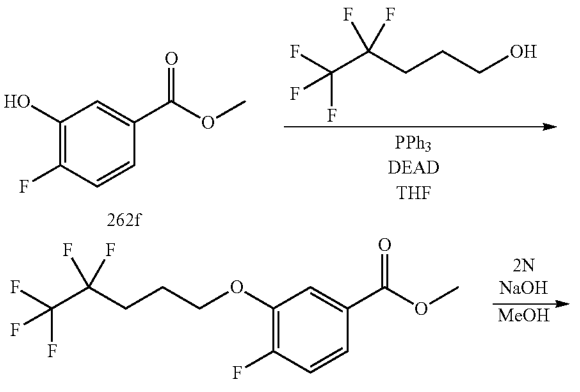

262f

262g

-continued

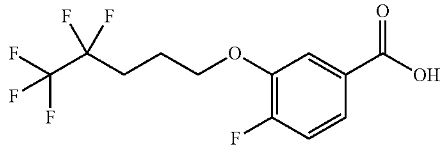

262d

4-Fluoro-3-(4,4,5,5,5-pentafluoro-pentyloxy)-benzoic acid was synthesized by operations similar to those in Reaction 31-7 and Reaction 95-18 using appropriate reagents and starting material.

$^1$H-NMR (400 MHz, $CD_3OD$) δ 0.21-0.14 (2H, m), 2.30-2.42 (2H, m), 4.19 (2H, t, J=6.0 Hz), 7.20 (1H, dd, J=10.8, 8.4 Hz), 7.64-7.68 (1H, m), 7.72 (1H, dd, J=8.4, 2.0 Hz).

Example 263

2-[4-Fluoro-3-(4,4,5,5,5-pentafluoro-pentyloxy)-phenyl]-8-{(E)-2-[4-(4-hydroxy-4-methyl-piperidine-1-carbonyl)-2,6-dimethyl-phenyl}-ethenesulfonyl]-1,3,8-triaza-spiro[4.5]dec-1-en-4-one (Compound 1092)

(Reaction 263-1)

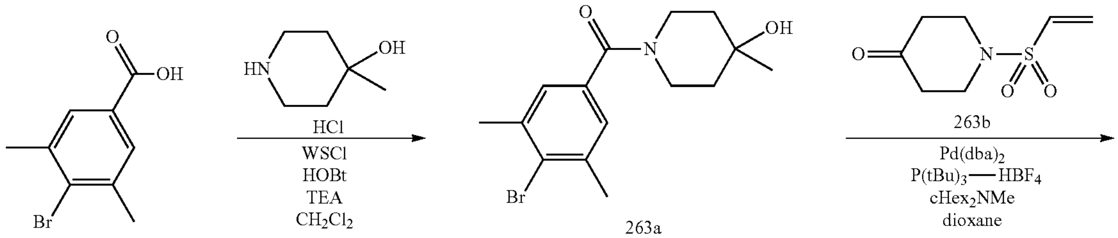

29i

263a

-continued
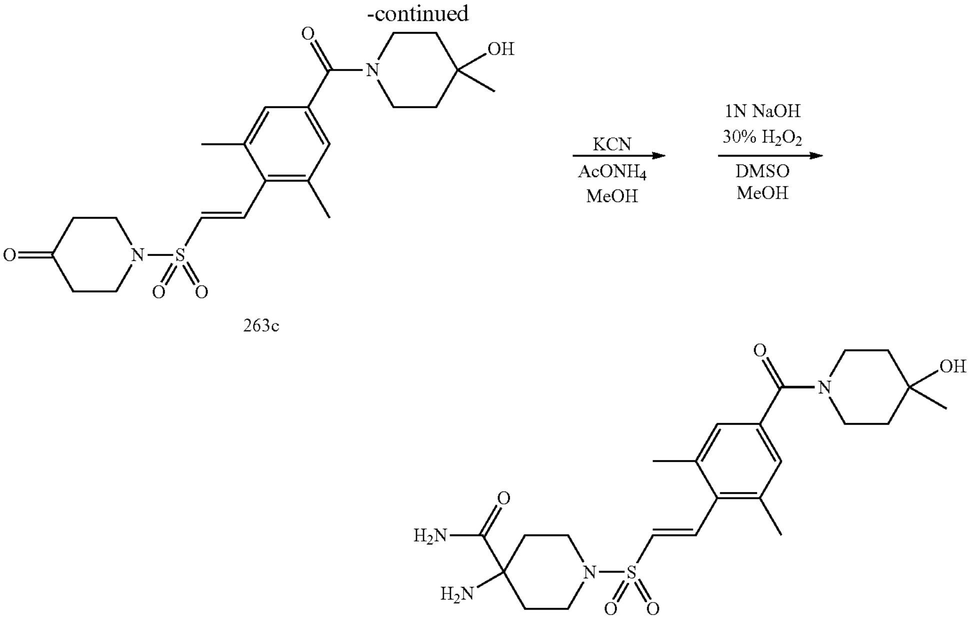
263c
263d
4-Amino-1-{(E)-2-[4-(4-hydroxy-4-methyl-piperidine-1-carbonyl)-2,6-dimethyl-phenyl]-ethenesulfonyl}-piperidine-4-carboxylic amide was synthesized by operations similar to those in Reaction 10-18, Reaction 119-1, Reaction 233-3 and Reaction 233-4 using appropriate reagents and starting material.
MS (ESI) m/z=479 (M+H)+.
(Reaction 263-2)
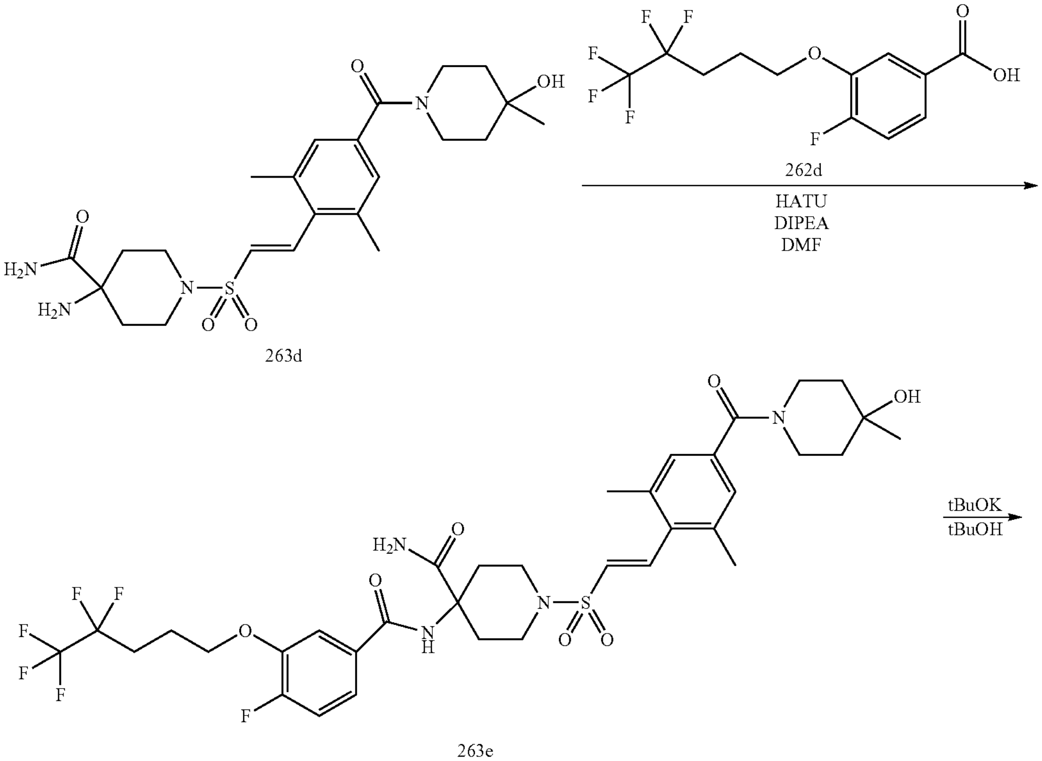
263d
262d
263e -continued

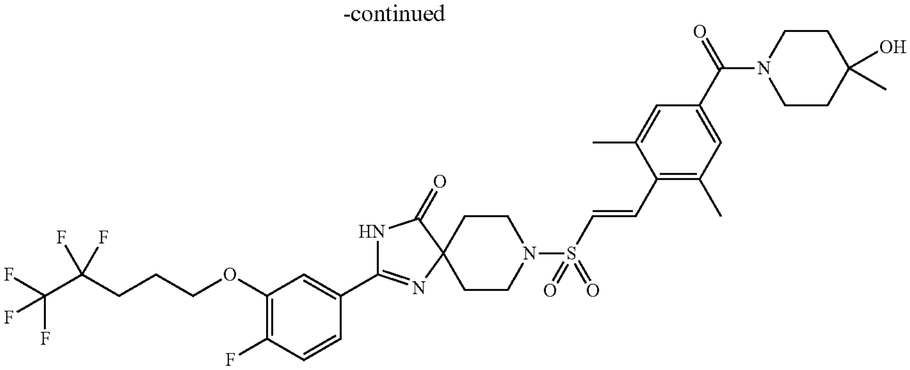

Compound 1092

2-[4-Fluoro-3-(4,4,5,5,5-pentafluoro-pentyloxy)-phenyl]-8-{(E)-2-[4-(4-hydroxy-4-methyl-piperidine-1-carbonyl)-2,6-dimethyl-phenyl]-ethenesulfonyl}-1,3,8-triaza-spiro[4.5]dec-1-en-4-one was synthesized by operations similar to those in Reaction 10-14 and Reaction 10-12 using appropriate reagents and starting material.

MS (ESI) m/z=759 (M+H)+.

The example compounds shown below were synthesized by operations similar to those in Reaction 263-2 using appropriate reagents and starting materials.

Compounds 1093 to 1099

TABLE 162

| Compound | Structure | LCMS condition | Retention time (min) | MS (m/z) |
|---|---|---|---|---|
| 1093 | 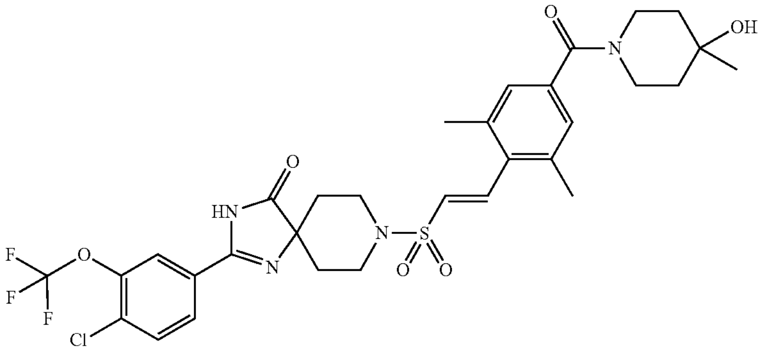 | LCMS-F-1 | 1.03 | 683 (M + H)+ |
| 1094 | 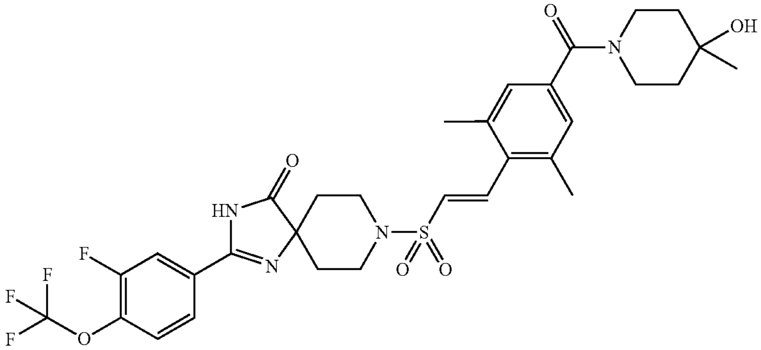 [SMILES: Cc1cc(C(=O)N2CCC(C)(O)CC2)cc(C)c1/C=C/[S@TB4](=O)(=O)N1CCC2(CC1)N=C(c1ccc(OC(F)(F)F)c(F)c1)NC2=O] | LCMS-F-1 | 1.01 | 667 (M + H)+ |

TABLE 162-continued
| Compound | Structure | LCMS condition | Retention time (min) | MS (m/z) |
|---|---|---|---|---|
| 1095 | 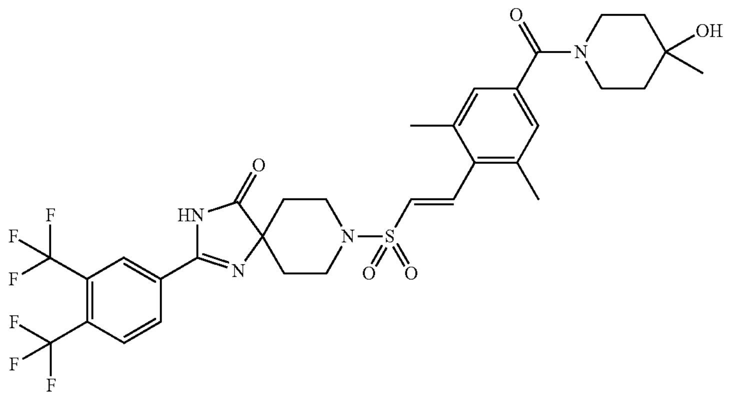 [SMILES: Cc1cc(C(=O)N2CCC(C)(O)CC2)cc(C)c1/C=C/[S@TB4](=O)(=O)N1CCC2(CC1)N=C(c1ccc(C(F)(F)F)c(C(F)(F)F)c1)NC2=O] | LCMS-F-1 | 1.03 | 701 (M + H)+ |
| 1096 | 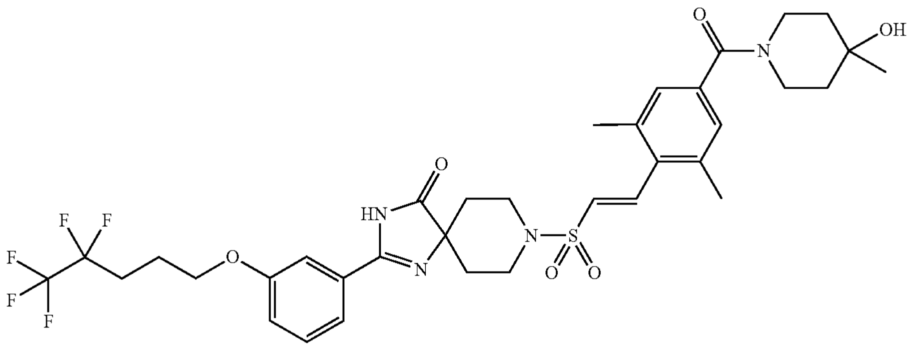 [SMILES: Cc1cc(C(=O)N2CCC(C)(O)CC2)cc(C)c1/C=C/[S@TB4](=O)(=O)N1CCC2(CC1)N=C(c1cccc(OCCCC(F)(F)C(F)(F)F)c1)NC2=O] | LCMS-F-1 | 1.05 | 741 (M + H)+ |
| 1097 | 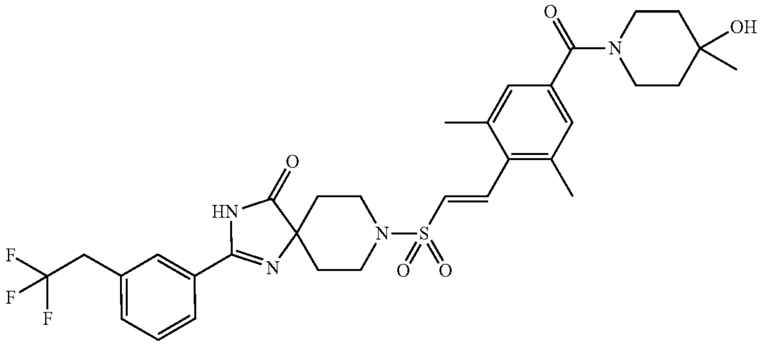 [SMILES: Cc1cc(C(=O)N2CCC(C)(O)CC2)cc(C)c1/C=C/[S@TB4](=O)(=O)N1CCC2(CC1)N=C(c1cccc(CC(F)(F)F)c1)NC2=O] | LCMS-C-1 | 2.60 | 647 (M + H)+ |
| 1098 | 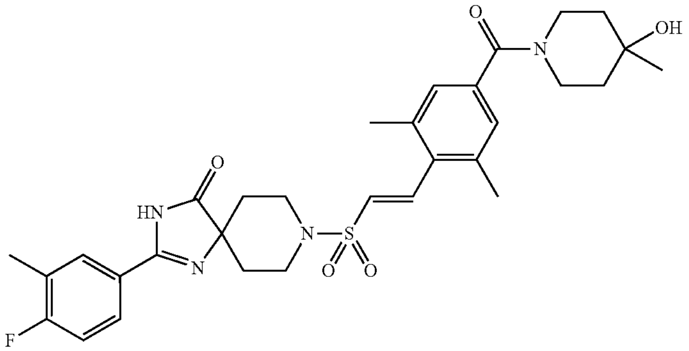 [SMILES: Cc1cc(C2=NC3(CCN([S@TB17](=O)(=O)/C=C/c4c(C)cc(C(=O)N5CCC(C)(O)CC5)cc4C)CC3)C(=O)N2)ccc1F] | LCMS-C-1 | 2.60 | 597 (M + H)+ |

TABLE 162-continued

| Compound | Structure | LCMS condition | Retention time (min) | MS (m/z) |
|---|---|---|---|---|
| 1099 | 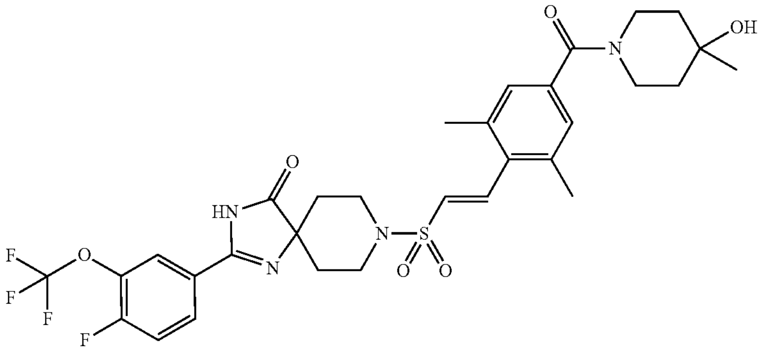 [SMILES: Cc1cc(C(=O)N2CCC(C)(O)CC2)cc(C)c1/C=C/[S@TB4](=O)(=O)N1CCC2(CC1)N=C(c1ccc(F)c(OC(F)(F)F)c1)NC2=O] | LCMS-F-1 | 1.01 | 667 (M + H)+ |

The carboxylic acid reagent used in the synthesis of Compound 1096 (3-(4,4,5,5,5-pentafluoro-pentyloxy)-benzoic acid) was synthesized by the following method.

(Reaction 263-3)

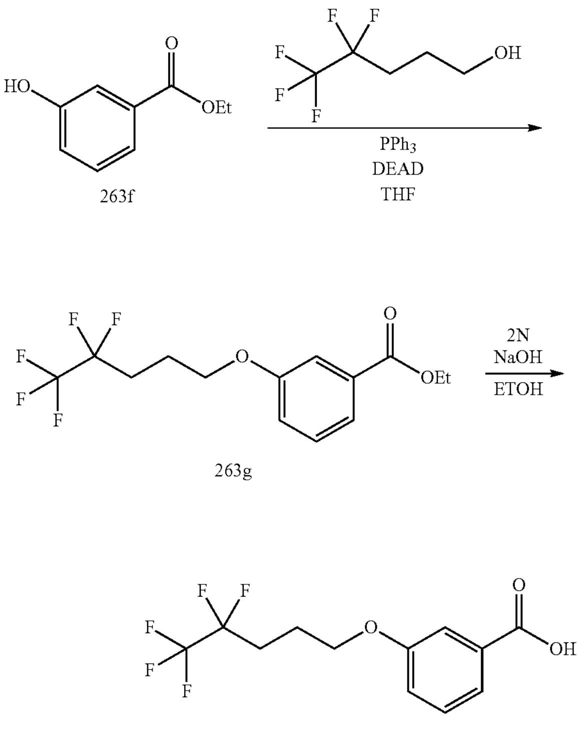

3-(4,4,5,5,5-Pentafluoro-pentyloxy)-benzoic acid was synthesized by operations similar to those in Reaction 31-7 and Reaction 95-18 using appropriate reagents and starting material.

MS (ESI) m/z=297 (M−H)−.

The carboxylic acid reagent used in the synthesis of Compound 1097 (3-(2,2,2-trifluoro-ethyl)-benzoic acid) was synthesized by the following method.

(Reaction 263-4)

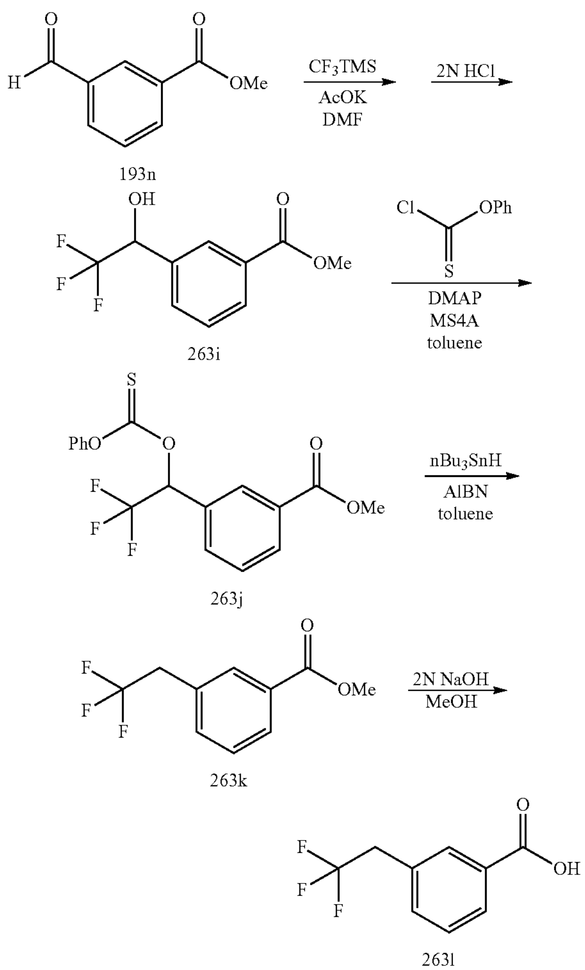

3-(2,2,2-Trifluoro-ethyl)-benzoic acid was synthesized by operations similar to those in Reaction 193-4, Reaction 193-5, Reaction 193-6 and Reaction 95-18 using appropriate reagents and starting material.

$^1$H-NMR (400 MHz, $CDCl_3$) δ 3.43 (2H, q, J=10.8 Hz), 3.93 (3H, s), 7.43-7.51 (2H, m), 7.99-8.04 (2H, m).

Example 264
8-{(E)-2-[4-(4-Hydroxy-4-methyl-piperidine-1-carbonyl)-2,6-dimethyl-phenyl]-ethenesulfonyl}-2-[3-(1,1,2,2-tetrafluoro-ethoxy)-phenyl]-1,3,8-triaza-spiro[4.5]dec-1-en-4-one (Compound 1100)
(Reaction 264-1)
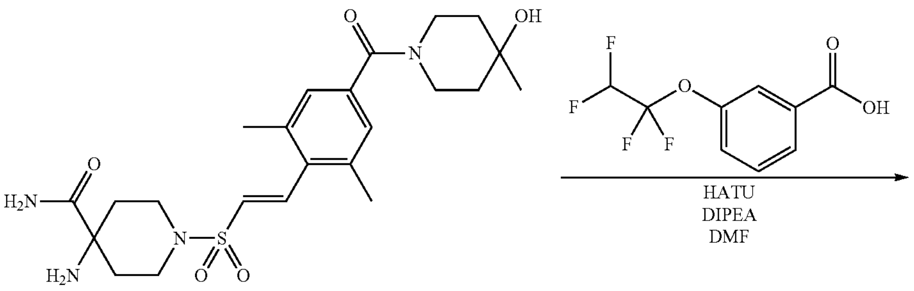
263d
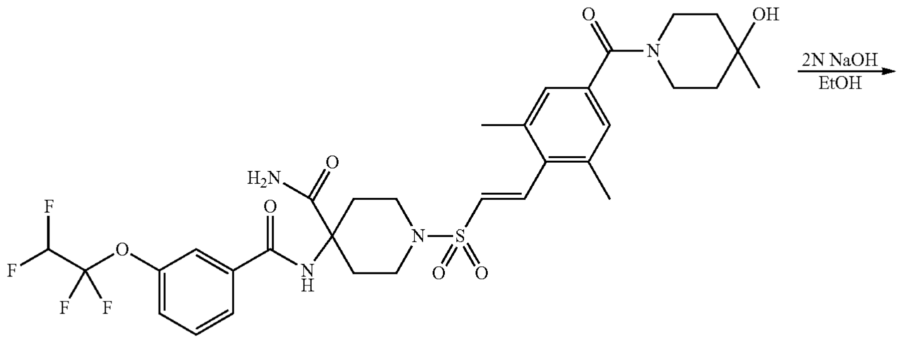
264a
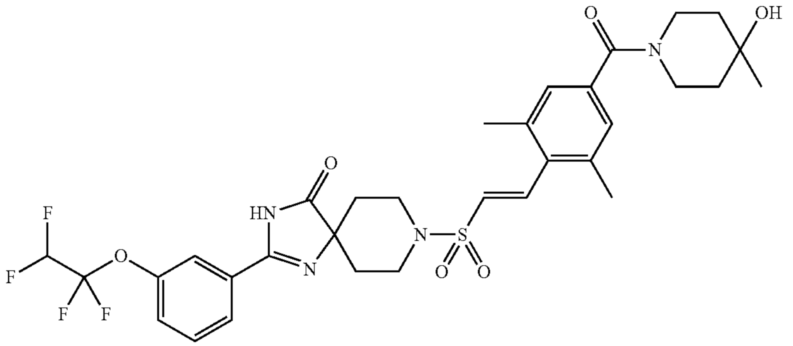
Compound 1100

8-{(E)-2-[4-(4-Hydroxy-4-methyl-piperidine-1-carbonyl)-2,6-dimethyl-phenyl]-ethenesulfonyl}-2-[3-(1,1,2,2-tetrafluoro-ethoxy)-phenyl]-1,3,8-triaza-spiro[4.5]dec-1-en-4-one was synthesized by operations similar to those in Reaction 10-14 and Reaction 189-5 using appropriate reagents and starting material.

MS (ESI) m/z=681 (M+H)+.

Example 265

8-{1,1-Difluoro-2-[4-(4-hydroxy-piperidine-1-carbonyl)-2,6-dimethyl-phenyl]-ethanesulfonyl}-2-(3-trifluoromethoxy-phenyl)-1,3,8-triaza-spiro[4.5]dec-1-en-4-one (Compound 1101)

(Reaction 265-1)

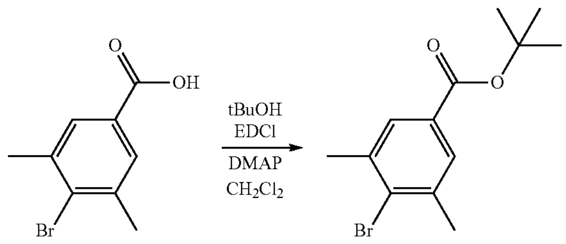

29i 265a

Dehydrated tert-butanol (0.19 ml, 2.0 mmol), 4-dimethylaminopyridine (81 mg, 0.67 mmol) and EDCI (255 mg, 1.33 mmol) were added to a solution of 4-bromo-3,5-dimethyl-benzoic acid (123 mg, 0.535 mmol) in dichloromethane (1.0 ml) at 0° C., and the mixture was stirred at room temperature for 25 hours. The reaction mixture was diluted with dichloromethane, and the organic layer was washed with water, dried over $MgSO_4$ and concentrated under reduced pressure. The resulting residue was purified by silica gel column chromatography (hexane/ethyl acetate=100/1→50/1) to give 4-bromo-3,5-dimethyl-benzoic acid tert-butyl ester (106 mg, 70%).

$^1$H-NMR (400 MHz, $CDCl_3$) δ 1.58 (9H, s), 2.45 (6H, s), 7.66 (2H, s).

(Reaction 265-2)

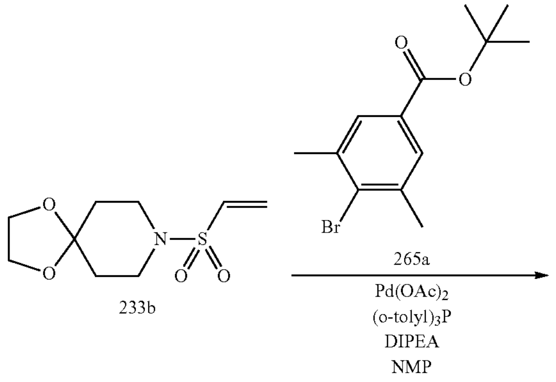

233b

-continued

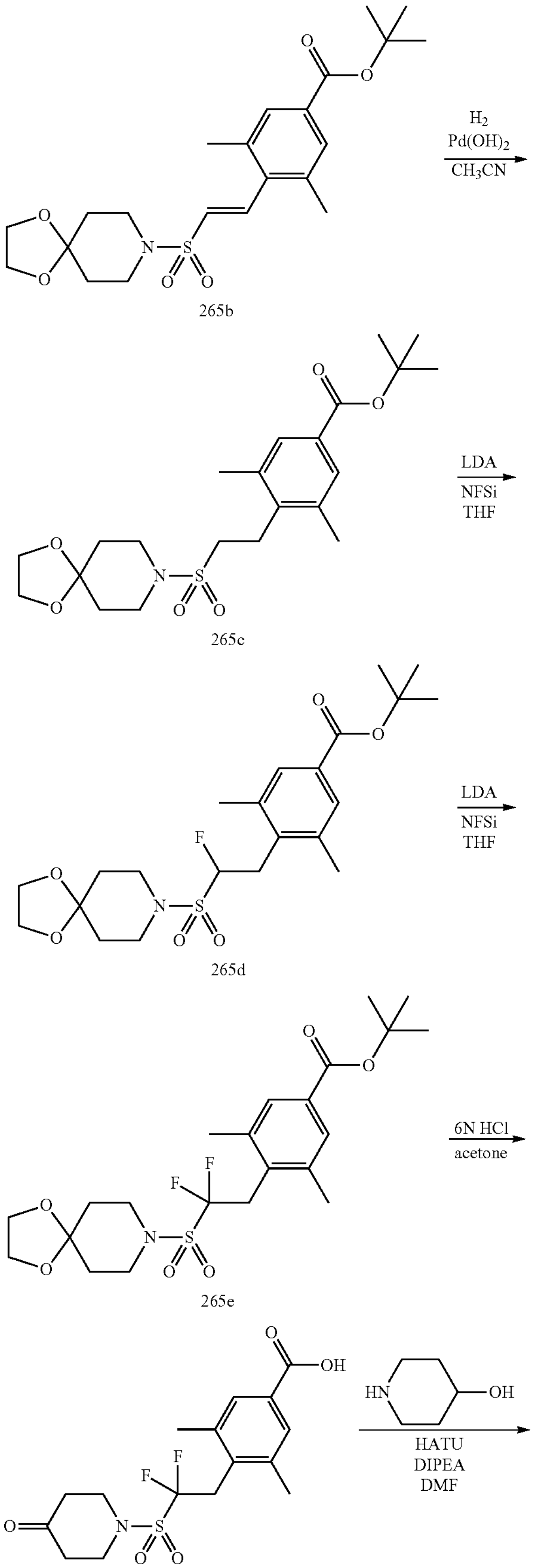

265b

265c

265d

265e

265f

-continued

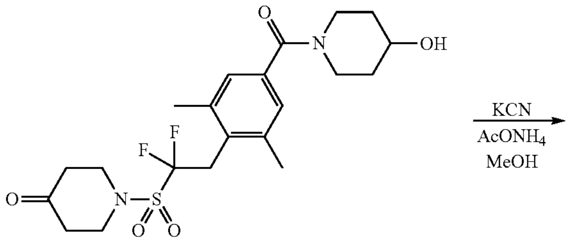

265g

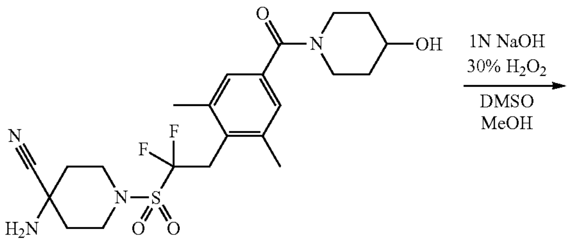

265h

-continued

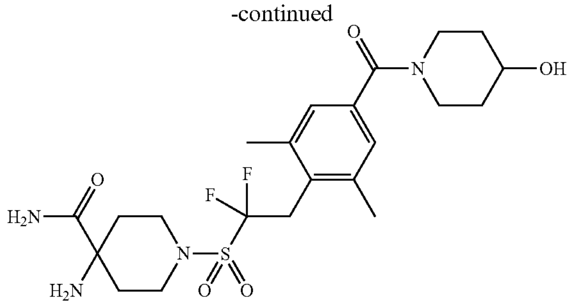

265i

4-Amino-1-{1,1-difluoro-2-[4-(4-hydroxy-piperidine-1-carbonyl)-2,6-dimethyl-phenyl]-ethanesulfonyl}-piperidine-4-carboxylic amide was synthesized by operations similar to those in Reaction 26-1, Reaction 184-1, Reaction 257-1, Reaction 257-1, Reaction 233-2, Reaction 10-14, Reaction 233-3 and Reaction 233-4 using appropriate reagents and starting material.

$^1$H-NMR (400 MHz, $CDCl_3$) δ 1.07 (2H, br), 1.53 (2H, m), 1.84 and 1.95 (each 1H, br), 2.21 (2H, m), 2.36 (6H, s), 3.21 and 3.33 (each 1H, br), 3.48 (2H, m), 3.68 (2H, dd, J=20.4 and 18.4 Hz), 3.70 (1H, br), 3.86 (2H, m), 3.97 (1H, m), 4.20 (1H, br), 5.33 (1H, br), 7.07 (2H, s), 7.19 (1H, br).

(Reaction 265-3)

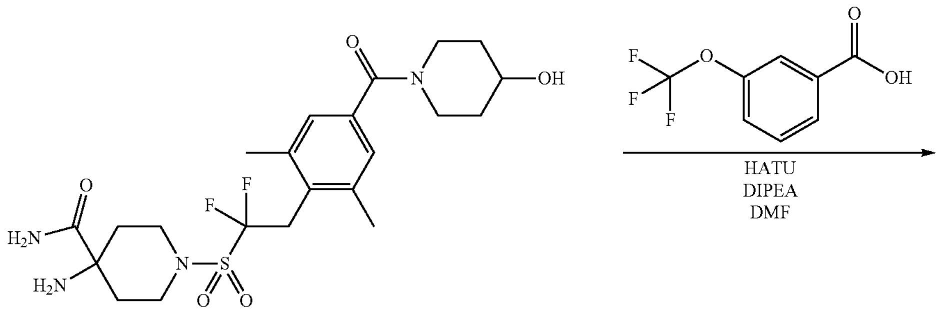

265i

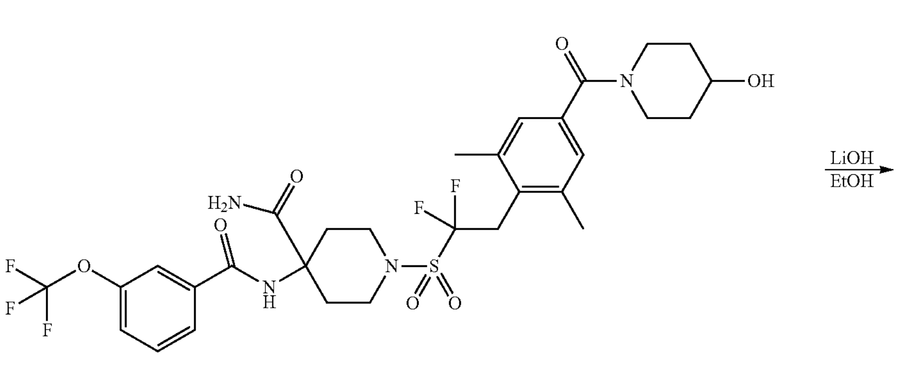

265j

-continued

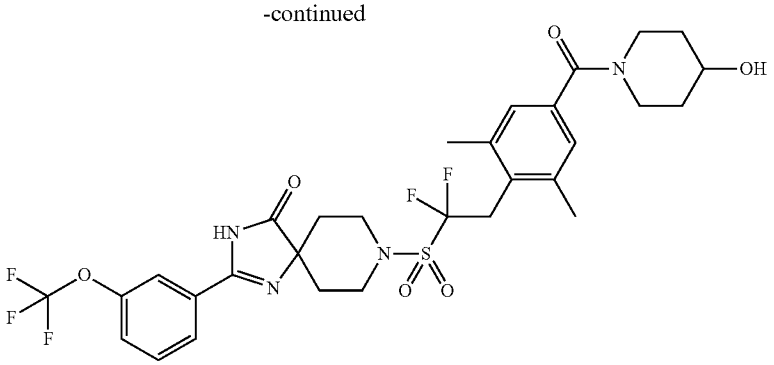

Compound 1101

8-{1,1-Difluoro-2-[4-(4-hydroxy-piperidine-1-carbonyl)-2,6-dimethyl-phenyl]-ethanesulfonyl}-2-(3-trifluoromethoxy-phenyl)-1,3,8-triaza-spiro[4.5]dec-1-en-4-one was synthesized by operations similar to those in Reaction 10-14 and Reaction 101-3 using appropriate reagents and starting material.

MS (ESI) m/z=673 (M+H)+.

Example 266

2-(4-Fluoro-3-trifluoromethoxy-phenyl)-8-{(E)-2-[4-(3-hydroxy-azetidine-1-carbonyl)-2,6-dimethyl-phenyl]-ethenesulfonyl}-1,3,8-triaza-spiro[4.5]dec-1-en-4-one (Compound 1102)

(Reaction 266-1)

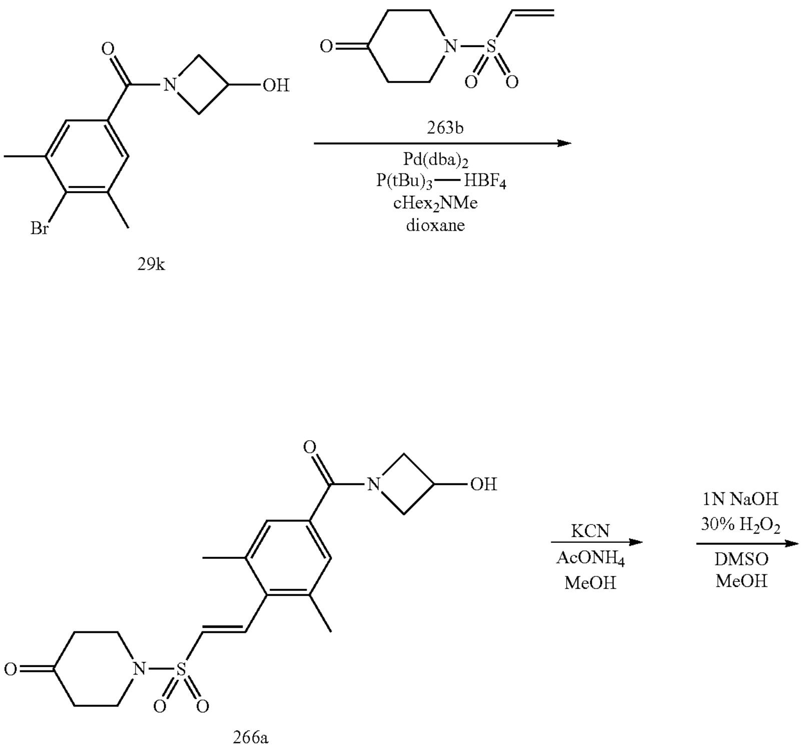

-continued

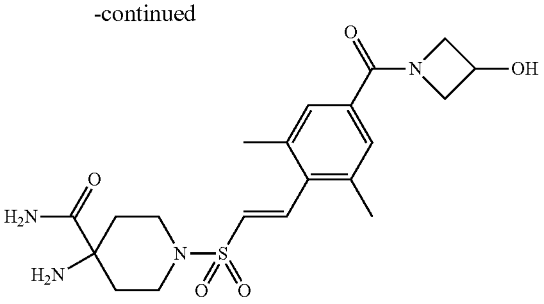

266b

4-Amino-1-{(E)-2-[4-(3-hydroxy-azetidine-1-carbonyl)-2,6-dimethyl-phenyl]-ethenesulfonyl}-piperidine-4-carboxylic amide was synthesized by operations similar to those in Reaction 119-1, Reaction 233-3 and Reaction 233-4 using appropriate reagents and starting material.

MS (ESI) m/z=437 (M+H)+.

2-(4-Fluoro-3-trifluoromethoxy-phenyl)-8-{(E)-2-[4-(3-hydroxy-azetidine-1-carbonyl)-2,6-dimethyl-phenyl]-ethenesulfonyl}-1,3,8-triaza-spiro[4.5]dec-1-en-4-one was synthesized by operations similar to those in Reaction 10-14 and Reaction 10-12 using appropriate reagents and starting material.

MS (ESI) m/z=625 (M+H)+.

(Reaction 266-2)

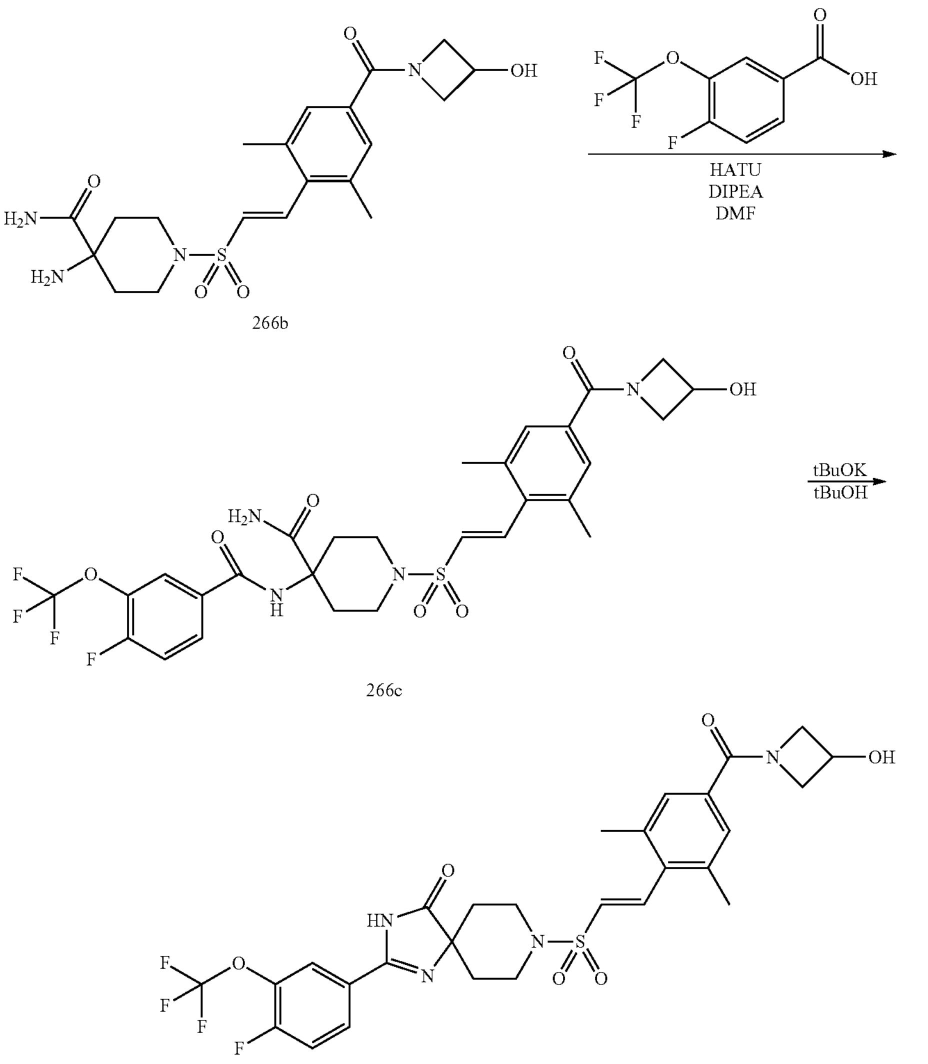

Compound 1102

Example 267

8-{(E)-2-[4-((R)-2,3-Dihydroxy-propoxy)-2,6-dimethyl-phenyl]-ethenesulfonyl}-2-[3-(4,4,5,5,5-pentafluoro-pentyloxy)-phenyl]-1,3,8-triaza-spiro[4.5]dec-1-en-4-one (Compound 1103)

(Reaction 267-1)

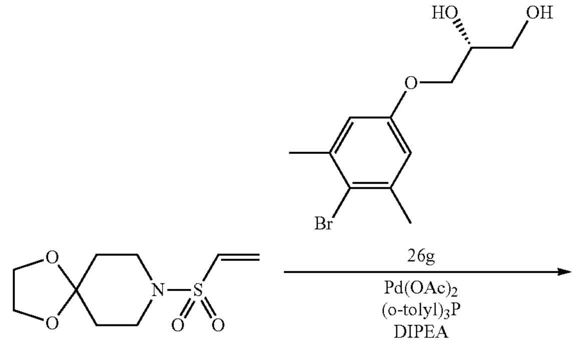

233b

26g

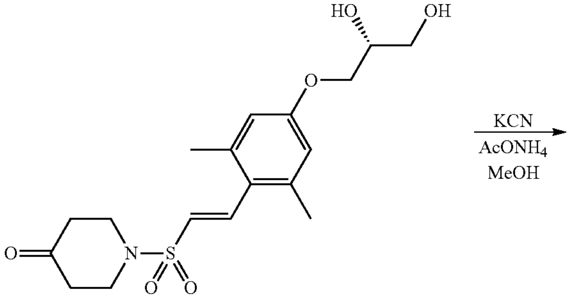

267a

-continued

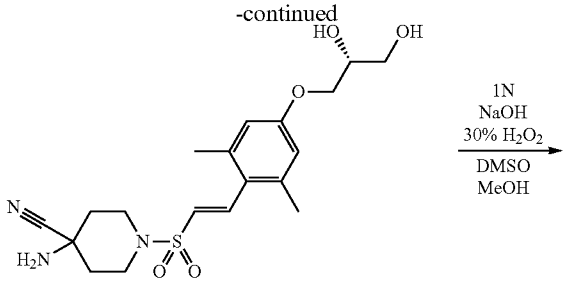

267b

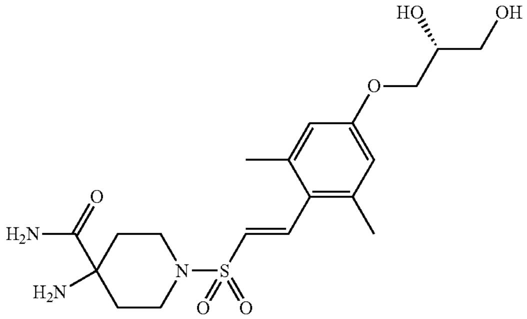

267c

4-Amino-1-{(E)-2-[4-((R)-2,3-dihydroxy-propoxy)-2,6-dimethyl-phenyl]-ethenesulfonyl}-piperidine-4-carboxylic amide was synthesized by operations similar to those in Reaction 26-1, Reaction 233-3 and Reaction 233-4 using appropriate reagents and starting material.

MS (ESI) m/z=428 (M+H)+.

(Reaction 267-2)

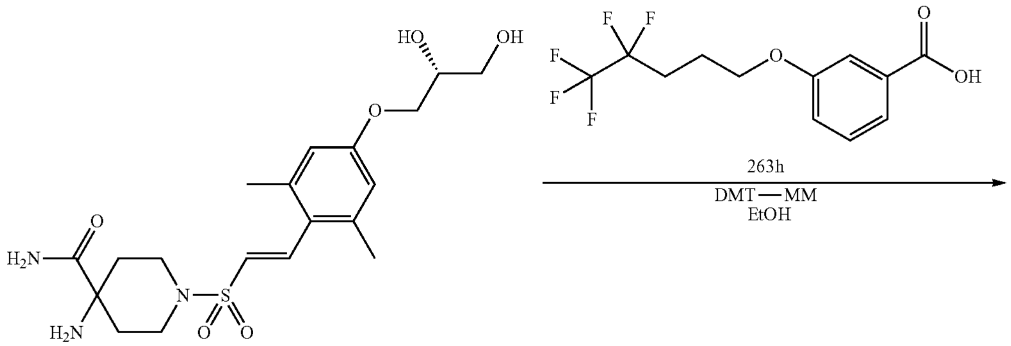

263h

267c

-continued

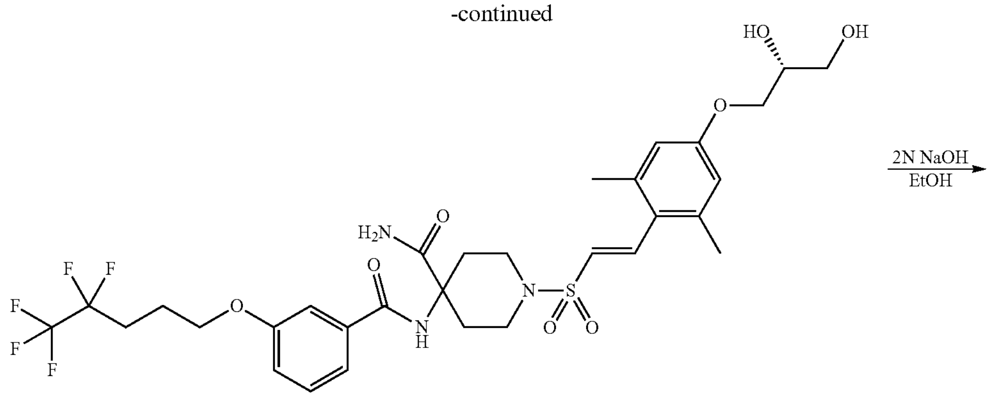

267d

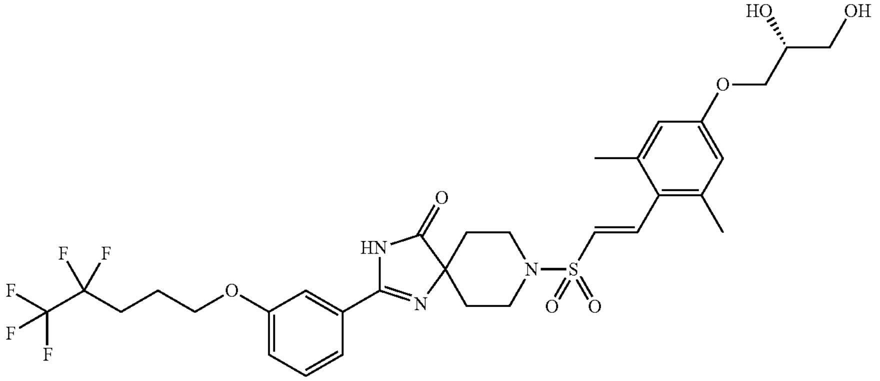

Compound 1103

8-{(E)-2-[4-((R)-2,3-Dihydroxy-propoxy)-2,6-dimethyl-phenyl]-ethenesulfonyl}-2-[3-(4,4,5,5,5-pentafluoro-pentyloxy)-phenyl]-1,3,8-triaza-spiro[4.5]dec-1-en-4-one was synthesized by operations similar to those in Reaction 10-1 and Reaction 189-5 using appropriate reagents and starting material.

MS (ESI) m/z=690 (M+H)+.

Example 268

6-(4-Methyl-cyclohexyl)-2-(2-naphthalen-1-yl-ethanesulfonyl)-2,5,7-triaza-spiro[3.4]oct-5-en-8-one (Compound 1104)

(Reaction 268-1)

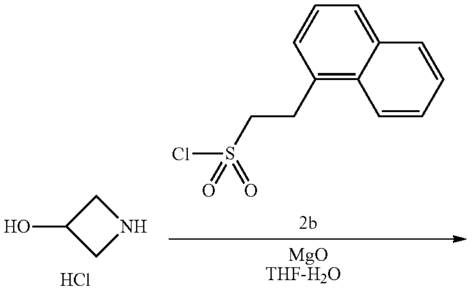

HCl

29j

-continued

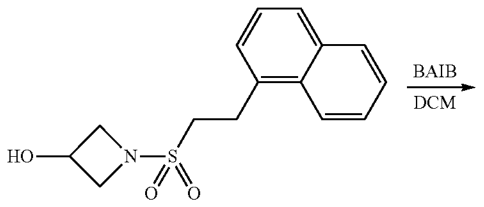

268a

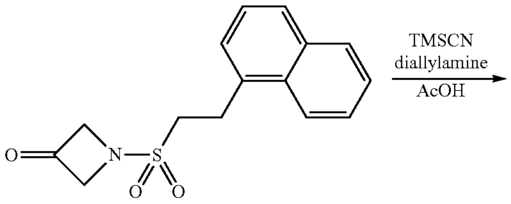

268b

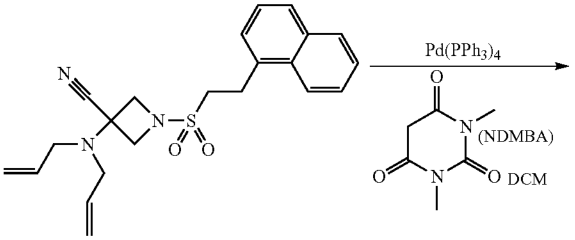

268c

-continued

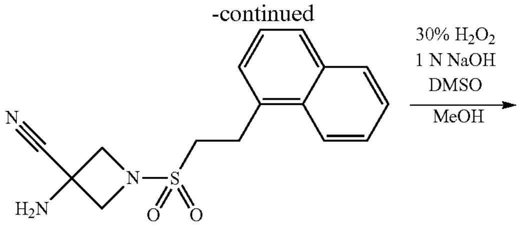

268d

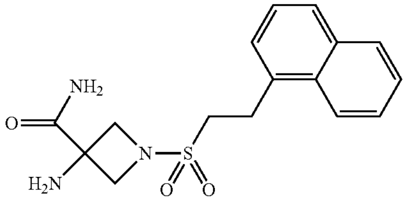

268e

3-Amino-1-(2-naphthalen-1-yl-ethanesulfonyl)-azetidine-3-carboxylic amide was synthesized by operations similar to those in Reaction 190-1, Reaction 109-1, Reaction 200-2, Reaction 200-3 and Reaction 233-4 using appropriate reagents and starting material.

MS (ESI) m/z=334 (M+H)+.

(Reaction 268-2)

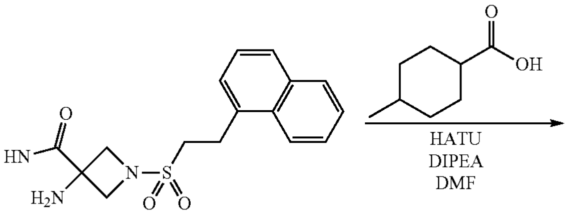

268e

-continued

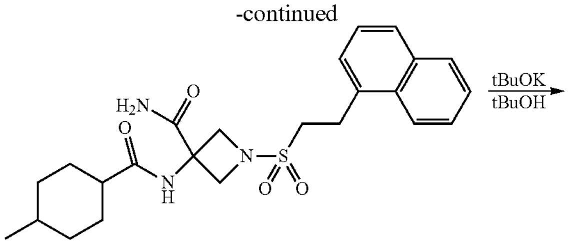

268f

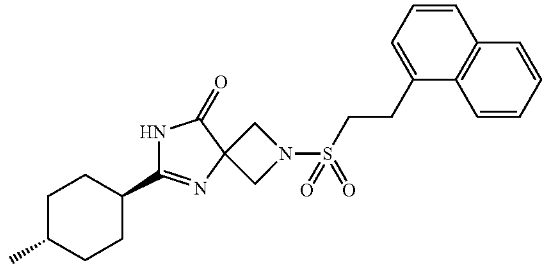

Compound 1104

6-(4-Methyl-cyclohexyl)-2-(2-naphthalen-1-yl-ethanesulfonyl)-2,5,7-triaza-spiro[3.4]oct-5-en-8-one was synthesized by operations similar to those in Reaction 10-14 and Reaction 10-12 using appropriate reagents and starting material.

MS (ESI) m/z=440 (M+H)+.

Example 269

8-[(E)-2-(2,6-Dimethyl-4-methylamino-phenyl)-ethenesulfonyl]-2-(11-hydroxy-undecyl)-1,3,8-triaza-spiro[4.5]dec-1-en-4-one (Reaction 269-1)

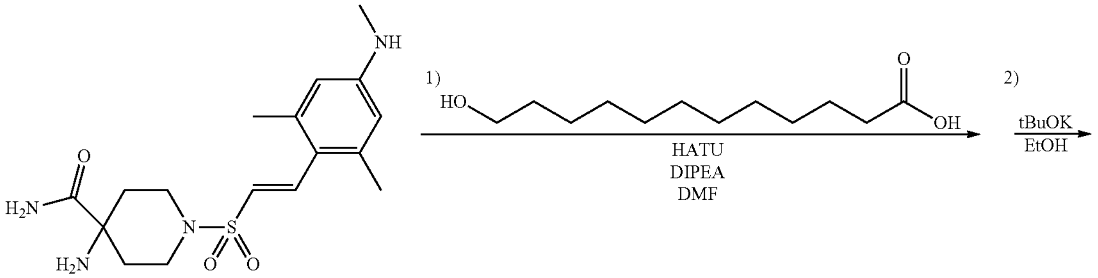

233f

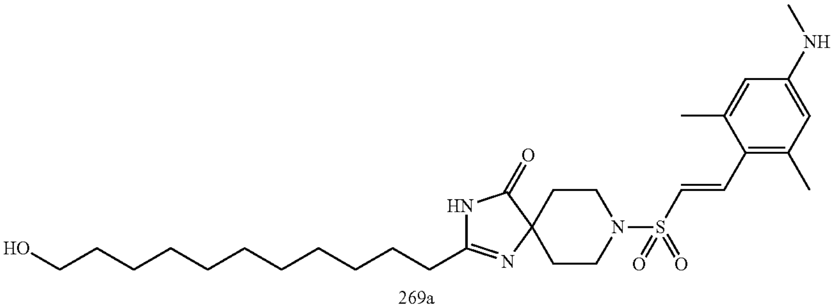

269a

HATU (57 mg, 0.149 mmol) was added to a solution of 12-hydroxy-dodecanoic acid (33 mg, 0.149 mol), 4-amino-1-[(E)-2-(2,6-dimethyl-4-methylamino-phenyl)-ethene-sulfonyl]-piperidine-4-carboxylic amide (50 mg, 0.136 mmol) and diisopropylethylamine (71 μL, 0.47 mmol) in DMF (1.3 ml) at 0° C., and the mixture was stirred at room temperature for 1.5 hours. Ethanol (2.6 ml) and potassium t-butoxide (76 mg, 0.678 mmol) were added to the reaction mixture, and the mixture was heated with stirring at 70° C. for three hours. The reaction mixture was quenched with a saturated aqueous ammonium chloride solution, and water was then added, followed by extraction with ethyl acetate. The organic layer was sequentially washed with water and saturated brine, and then dried over anhydrous sodium sulfate and concentrated under reduced pressure. The resulting residue was purified by silica gel column chromatography (dichloromethane-methanol) to give 8-[(E)-2-(2,6-dimethyl-4-methylamino-phenyl)-ethenesulfonyl]-2-(11-hydroxy-undecyl)-1,3,8-triaza-spiro[4.5]dec-1-en-4-one (58.7 mg, 79%).

MS (ESI) m/z=547 (M+H)+.

The example compounds shown below were synthesized by operations similar to those in Reaction 269-1 using appropriate reagents and starting materials.

Compounds 1106 to 1107

TABLE 163

| Compound | Structure | LCMS condition | Retention time (min) | MS (m/z) |
|---|---|---|---|---|
| 1106 | 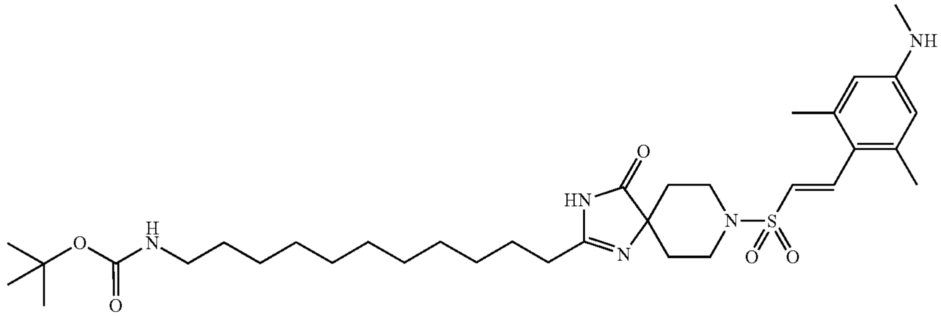 [SMILES: CNc1cc(C)c(/C=C/[S@TB3](=O)(=O)N2CCC3(CC2)N=C(CCCCCCCCCCCNC(=O)OC(C)(C)C)NC3=O)c(C)c1] | LCMS-C-1 | 3.12 | 646 (M + H)+ |
| 1107 | 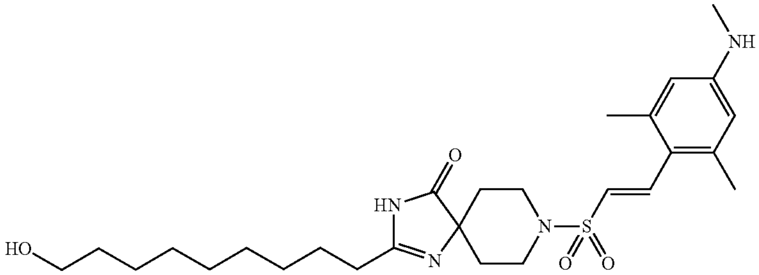 [SMILES: CNc1cc(C)c(/C=C/[S@TB3](=O)(=O)N2CCC3(CC2)N=C(CCCCCCCCCO)NC3=O)c(C)c1] | LCMS-G-1 | 0.93 | 519 (M + H)+ |

Example 270

1-(3,5-Dimethyl-4-{(E)-2-[4-oxo-2-((1S,3R)-3-propyl-cyclohexyl)-1,3,8-triaza-spiro[4.5]dec-1-ene-8-sulfonyl]-vinyl}-phenyl)-1-methyl-urea (Compound 1108)

(Reaction 270-1)

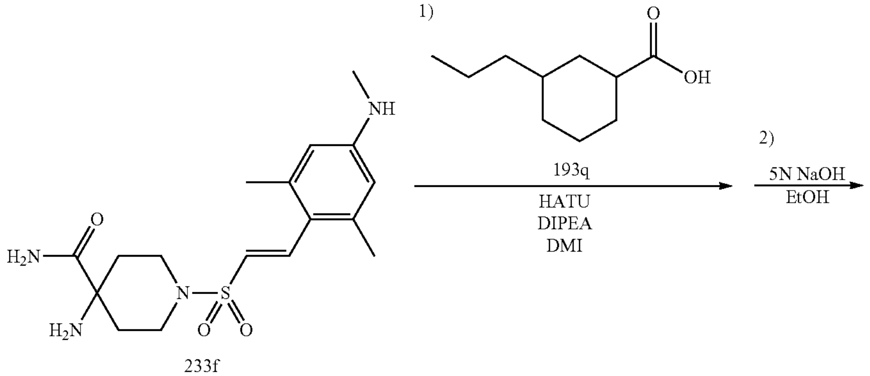

233f

-continued

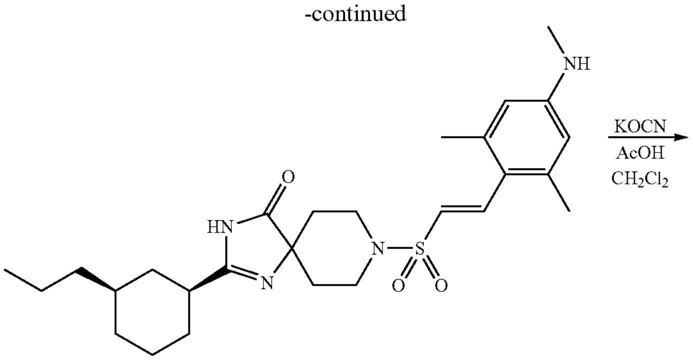

270a

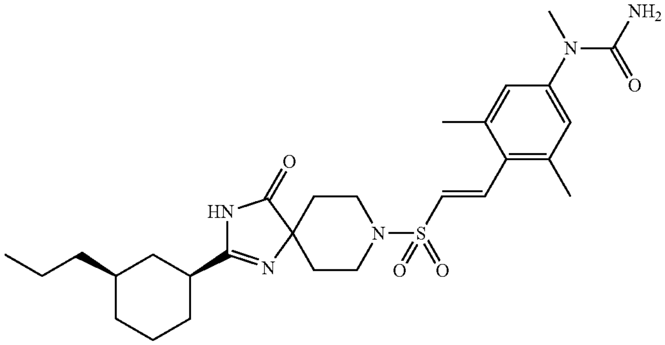

Compound 1108

1-(3,5-Dimethyl-4-{(E)-2-[4-oxo-2-((1S,3R)-3-propyl-cyclohexyl)-1,3,8-triaza-spiro[4.5]dec-1-ene-8-sulfonyl]-vinyl}-phenyl)-1-methyl-urea was synthesized by operations similar to those in Reaction 269-1 and Reaction 89-2 (using KOCN) using appropriate reagents and starting material.

MS (ESI) m/z=544 (M+H)+.

The example compounds shown below were synthesized by operations similar to those in Reaction 270-1 using appropriate reagents and starting materials.

Compounds 1109 to 1113

TABLE 164

| Compound | Structure | LCMS condition | Retention time (min) | MS (m/z) |
|---|---|---|---|---|
| 1109 | 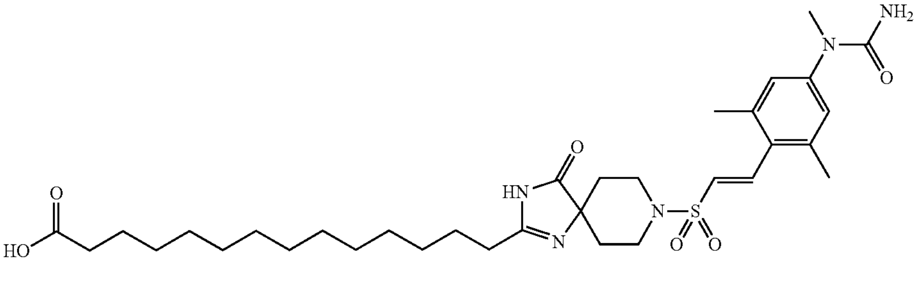 [SMILES: Cc1cc(N(C)C(N)=O)cc(C)c1/C=C/[S@TB4](=O)(=O)N1CCC2(CC1)N=C(CCCCCCCCCCCCCC(=O)O)NC2=O] | LCMS-C-1 | 2.72 | 646 (M + H)+ |

TABLE 164-continued
| Compound | Structure | LCMS condition | Retention time (min) | MS (m/z) |
|---|---|---|---|---|
| 1110 | 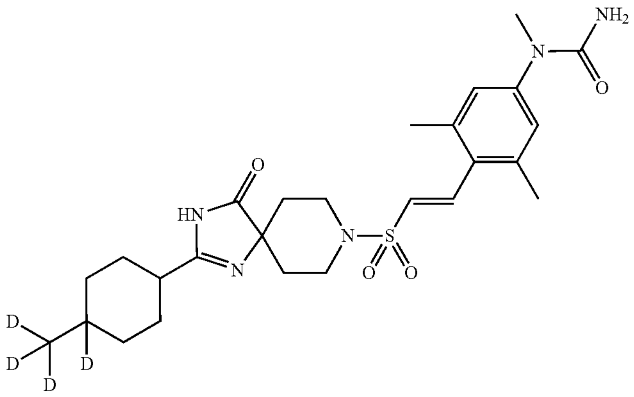 [SMILES: [2H]C([2H])([2H])C1([2H])CCC(C2=NC3(CCN([S@TB18](=O)(=O)/C=C/c4c(C)cc(N(C)C(N)=O)cc4C)CC3)C(=O)N2)CC1] | LCMS-F-1 | 0.93 | 520 (M + H)+ |
| 1111 | 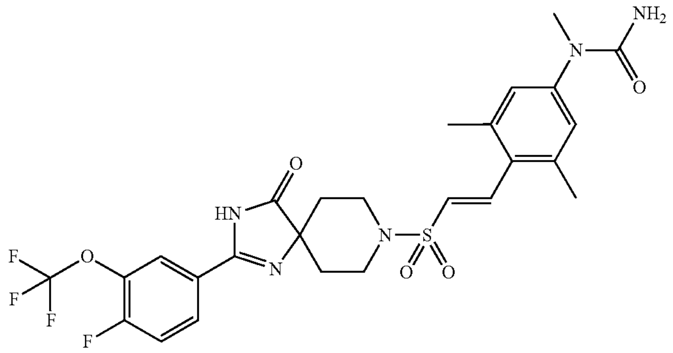 [SMILES: Cc1cc(N(C)C(N)=O)cc(C)c1/C=C/[S@TB3](=O)(=O)N1CCC2(CC1)N=C(c1ccc(F)c(OC(F)(F)F)c1)NC2=O] | LCMS-F-1 | 0.93 | 598 (M + H)+ |
| 1112 | 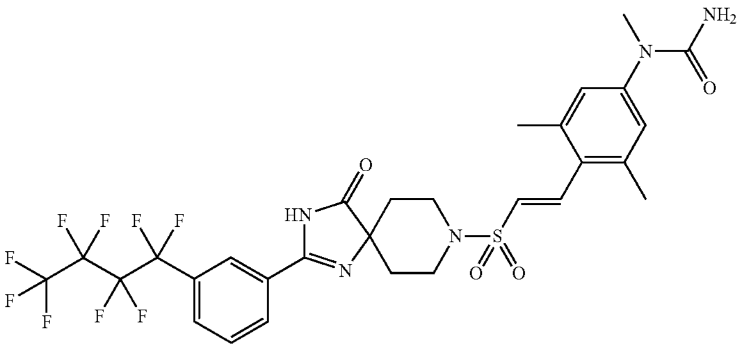 [SMILES: Cc1cc(N(C)C(N)=O)cc(C)c1/C=C/[S@TB3](=O)(=O)N1CCC2(CC1)N=C(c1cccc(C(F)(F)C(F)(F)C(F)(F)C(F)(F)F)c1)NC2=O] | LCMS-F-1 | 1.03 | 714 (M + H)+ |
| 1113 | 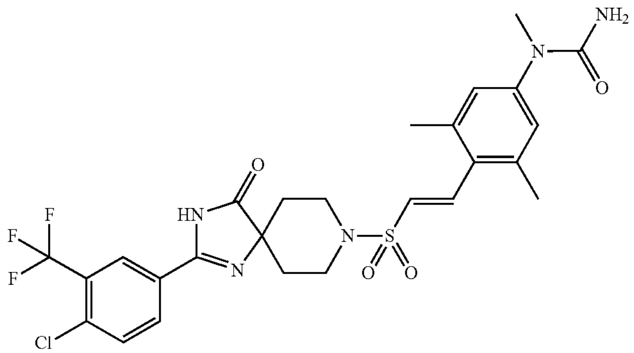 [SMILES: Cc1cc(N(C)C(N)=O)cc(C)c1/C=C/[S@TB3](=O)(=O)N1CCC2(CC1)N=C(c1ccc(Cl)c(C(F)(F)F)c1)NC2=O] | LCMS-F-1 | 0.99 | 598 (M + H)+ |

The carboxylic acid reagent used in the synthesis of Compound 1110 (4-[1,1,1-$^2H_3$]methyl-[4-$^2H_1$]cyclohexanecarboxylic acid) was synthesized by the following method.

(Reaction 270-2)

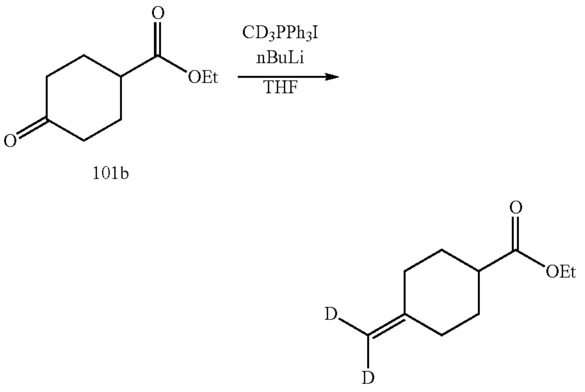

101b

270b

4-[1,1,1-$^2H_3$]Methylene-cyclohexanecarboxylic acid ethyl ester was synthesized by operations similar to those in Reaction 101-1 using appropriate reagents and starting material.

$^1$H-NMR (400 MHz, $CDCl_3$) δ 1.25 (3H, t, J=7.2 Hz), 1.52-1.64 (2H, m), 1.95-2.10 (4H, m), 2.34 (2H, ddd, J=13.6, 4.4, 4.4 Hz), 2.44 (1H, dddd, J=10.8, 10.8, 3.6, 3.6 Hz), 4.13 (2H, q, J=7.6 Hz).

(Reaction 270-3)

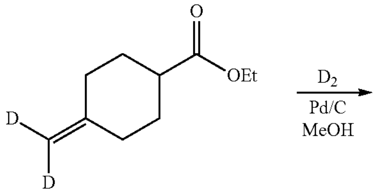

270b

-continued

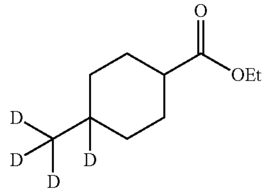

270c

20% w/w Pd/C (2.6 mg) was added to a solution of 4-[1,1,1-$^2H_3$]methylene-cyclohexanecarboxylic acid ethyl ester (26.0 mg, 153 μmol) in MeOH (1 ml) in an $N_2$ atmosphere. After deuterium substitution, the reaction mixture was stirred at room temperature for one hour. The reaction mixture was filtered through celite, and the filtrate was concentrated under reduced pressure to give 4-[1,1,1-$^2H_3$] methyl-[4-$^2H_1$]cyclohexanecarboxylic acid ethyl ester. This was used in the next step without further purification.

(Reaction 270-4)

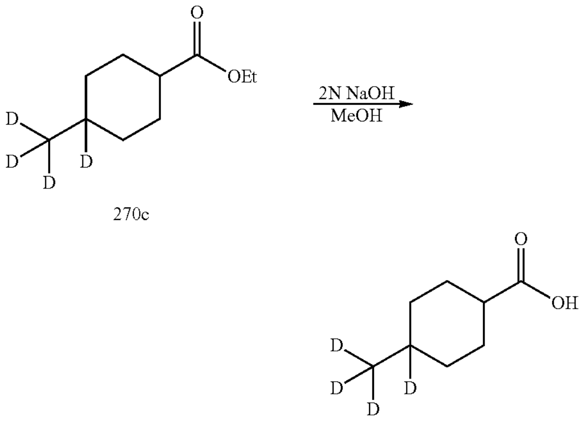

270c

270d

4-[1,1,1-$^2H_3$]Methyl-[4-$^2H_1$]cyclohexanecarboxylic acid was synthesized by operations similar to those in Reaction 95-18 using appropriate reagents and starting material. This was used in the next step without further purification.

Example 271

1-(3,5-Dimethyl-4-{(E)-2-[4-oxo-2-(4'-propyl-biphenyl-3-yl)-1,3,8-triaza-spiro[4.5]dec-1-ene-8-sulfonyl]-vinyl}-phenyl)-1-methyl-urea (Compound 1114)

(Reaction 271-1)

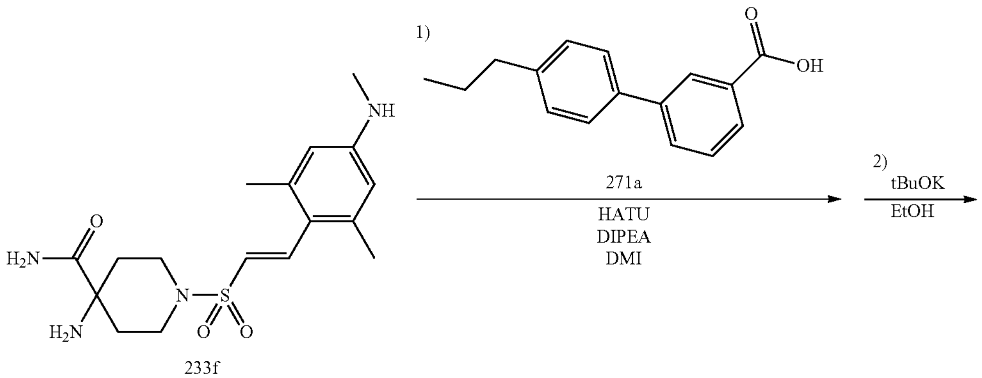

233f

-continued

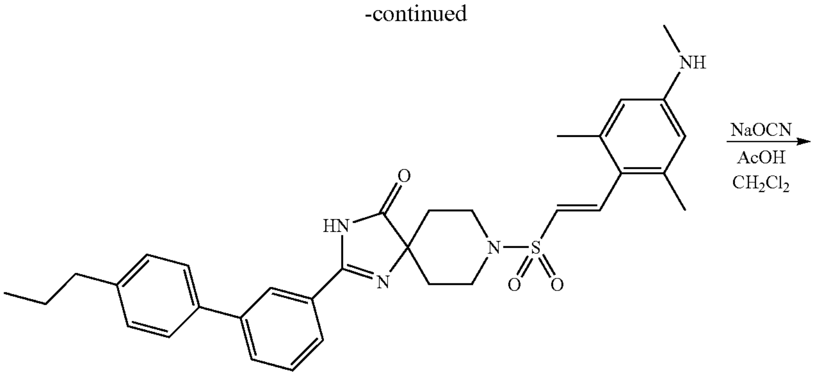

271b

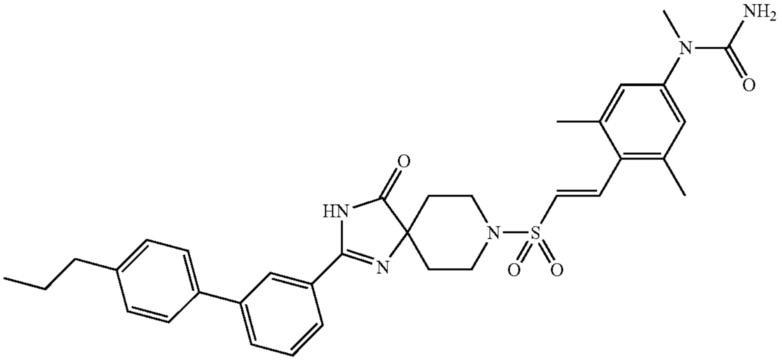

Compound 1114

1-(3,5-Dimethyl-4-{(E)-2-[4-oxo-2-(4'-propyl-biphenyl-3-yl)-1,3,8-triaza-spiro[4.5]dec-1-ene-8-sulfonyl]-vinyl}-phenyl)-1-methyl-urea was synthesized by operations similar to those in Reaction 269-1 and Reaction 89-2 using appropriate reagents and starting material.

MS (ESI) m/z=614 (M+H)+.

The carboxylic acid reagent used in the synthesis of Compound 1114 (4'-propyl-biphenyl-3-carboxylic acid) was synthesized by the following method.

(Reaction 271-2)

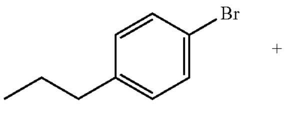

271c

-continued

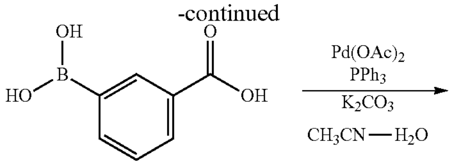

259g

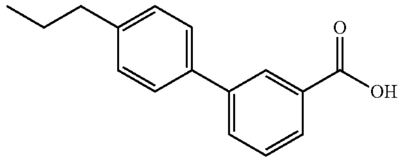

271a

4'-Propyl-biphenyl-3-carboxylic acid was synthesized by operations similar to those in Reaction 259-2 using appropriate reagents and starting material.

MS (ESI) m/z=241 (M+H)+.

The example compounds shown below were synthesized by operations similar to those in Reaction 259-1 using appropriate reagents and starting materials.

Compounds 1115 to 1130
TABLE 165
| Compound | Structure | LCMS condition | Retention time (min) | MS (m/z) |
|---|---|---|---|---|
| 1115 | 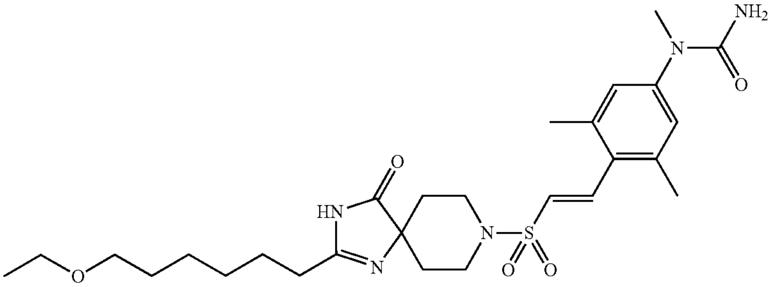 [SMILES: CCOCCCCCCC1=NC2(CCN([S@TB18](=O)(=O)/C=C/c3c(C)cc(N(C)C(N)=O)cc3C)CC2)C(=O)N1] | LCMS-D-1 | 1.84 | 548 (M + H)+ |
| 1116 | 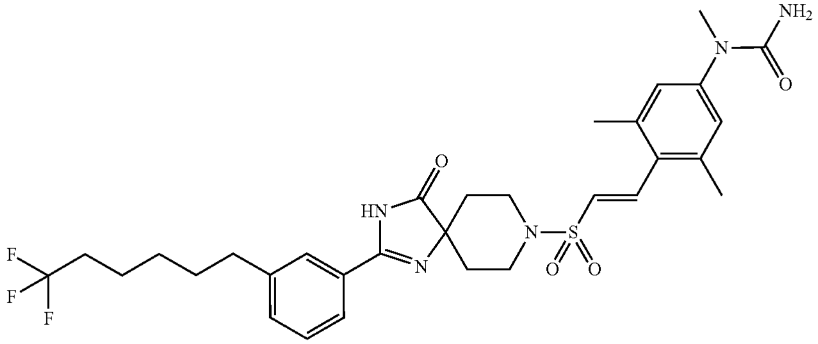 [SMILES: Cc1cc(N(C)C(N)=O)cc(C)c1/C=C/[S@TB3](=O)(=O)N1CCC2(CC1)N=C(c1cccc(CCCCCC(F)(F)F)c1)NC2=O] | LVMS-D-1 | 2.82 | 634 (M + H)+ |
| 1117 | 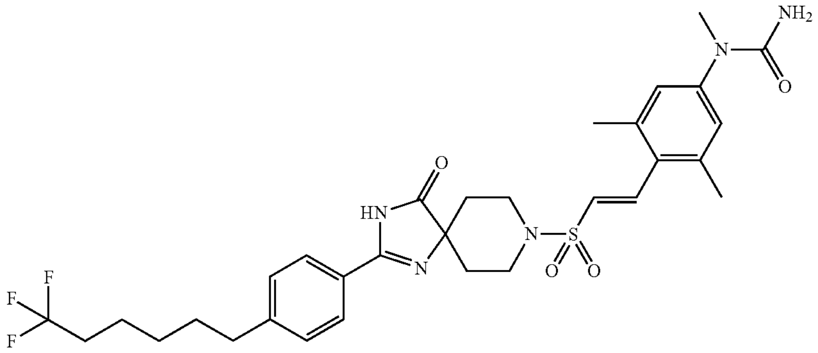 [SMILES: Cc1cc(N(C)C(N)=O)cc(C)c1/C=C/[S@TB3](=O)(=O)N1CCC2(CC1)N=C(c1ccc(CCCCCC(F)(F)F)cc1)NC2=O] | LCMS-D-1 | 2.75 | 634 (M + H)+ |
| 1118 | 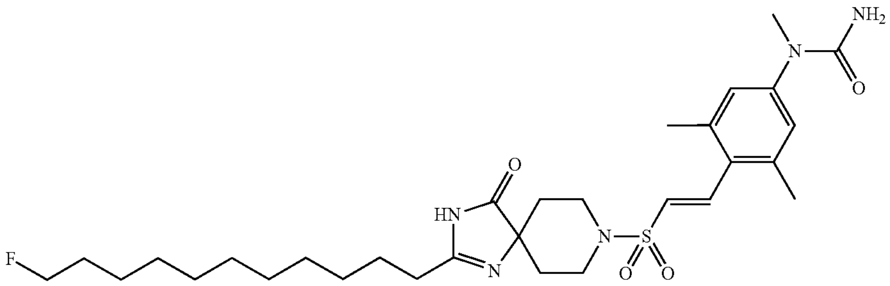 [SMILES: Cc1cc(N(C)C(N)=O)cc(C)c1/C=C/[S@TB4](=O)(=O)N1CCC2(CC1)N=C(CCCCCCCCCCCF)NC2=O] | LCMS-F-1 | 1.07 | 592 (M + H)+ |

TABLE 165-continued
| Compound | Structure | LCMS condition | Retention time (min) | MS (m/z) |
| --- | --- | --- | --- | --- |
| 1119 | 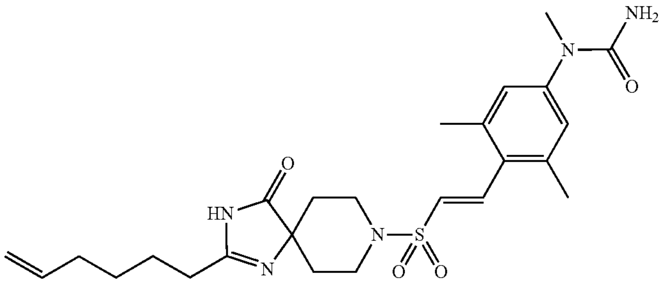 [SMILES: C=CCCCCC1=NC2(CCN([S@TB17](=O)(=O)/C=C/c3c(C)cc(N(C)C(N)=O)cc3C)CC2)C(=O)N1] | LCMS-F-1 | 0.92 | 502 (M + H)+ |
| 1120 | 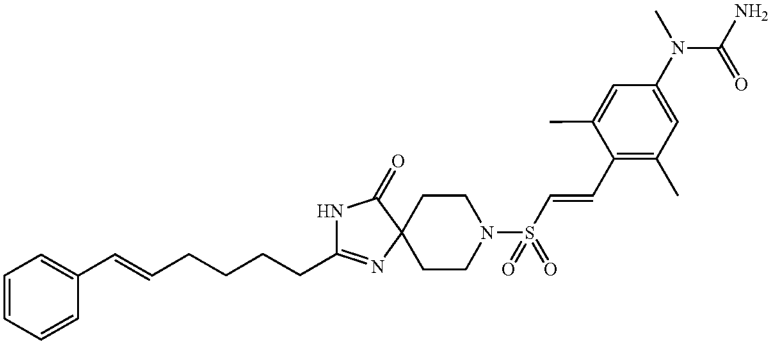 [SMILES: Cc1cc(N(C)C(N)=O)cc(C)c1/C=C/[S@TB3](=O)(=O)N1CCC2(CC1)N=C(CCCC/C=C/c1ccccc1)NC2=O] | LCMS-F-1 | 1.02 | 578 (M + H)+ |
| 1121 | 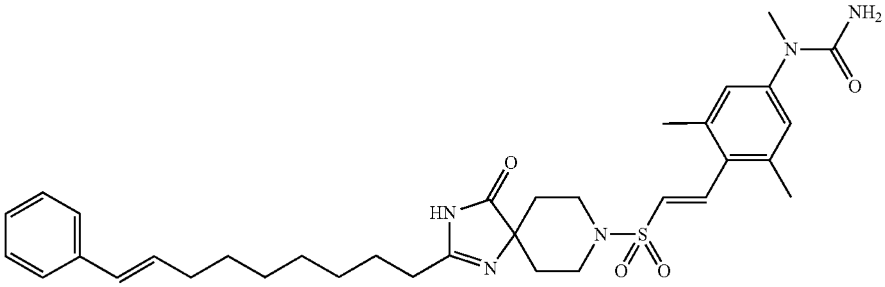 [SMILES: Cc1cc(N(C)C(N)=O)cc(C)c1/C=C/[S@TB3](=O)(=O)N1CCC2(CC1)N=C(CCCCCCC/C=C/c1ccccc1)NC2=O] | LCMS-F-1 | 1.11 | 620 (M + H)+ |
| 1122 | 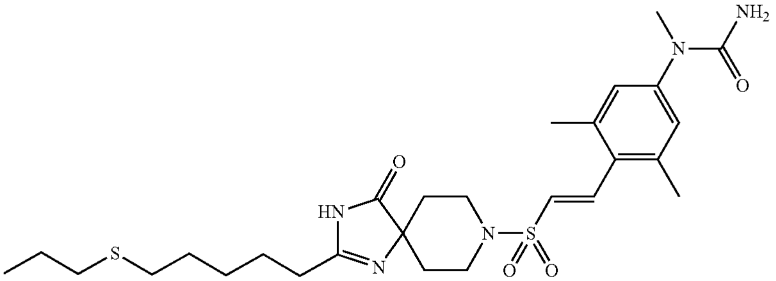 [SMILES: CCCSCCCCCC1=NC2(CCN([S@TB17](=O)(=O)/C=C/c3c(C)cc(N(C)C(N)=O)cc3C)CC2)C(=O)N1] | LCMS-D-1 | 1.75 | 564 (M + H)+ |
| 1123 | 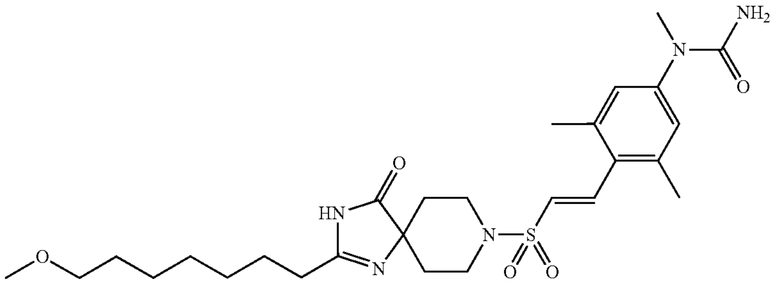 [SMILES: COCCCCCCCC1=NC2(CCN([S@TB18](=O)(=O)/C=C/c3c(C)cc(N(C)C(N)=O)cc3C)CC2)C(=O)N1] | LCMS-D-1 | 1.81 | 548 (M + H)+ |

TABLE 165-continued
| Compound | Structure | LCMS condition | Retention time (min) | MS (m/z) |
|---|---|---|---|---|
| 1124 | 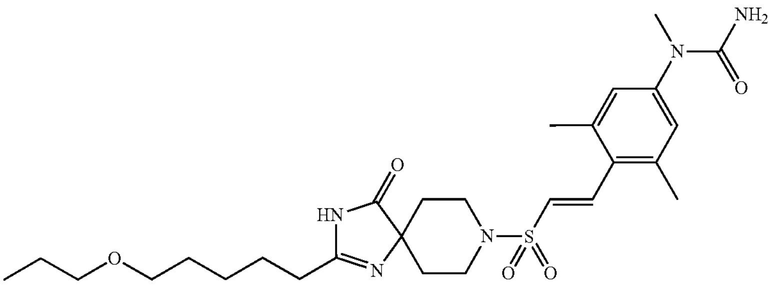 [SMILES: CCCOCCCCCC1=NC2(CCN([S@TB18](=O)(=O)/C=C/c3c(C)cc(N(C)C(N)=O)cc3C)CC2)C(=O)N1] | LCMS-D-1 | 1.98 | 548 (M + H)+ |
| 1125 | 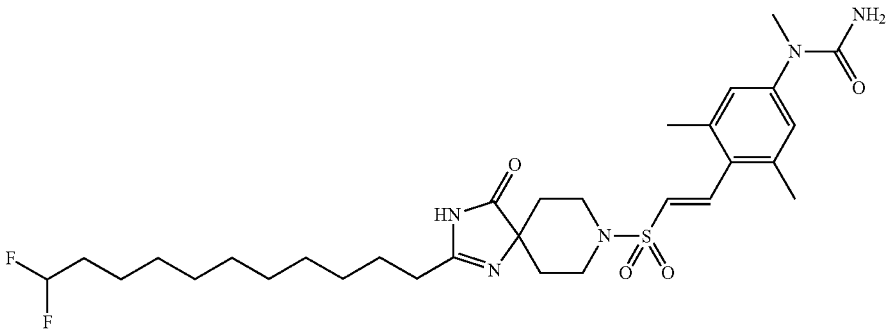 [SMILES: Cc1cc(N(C)C(N)=O)cc(C)c1/C=C/[S@TB4](=O)(=O)N1CCC2(CC1)N=C(CCCCCCCCCCC(F)F)NC2=O] | LCMS-F-1 | 1.05 | 610 (M + H)+ |
| 1126 | 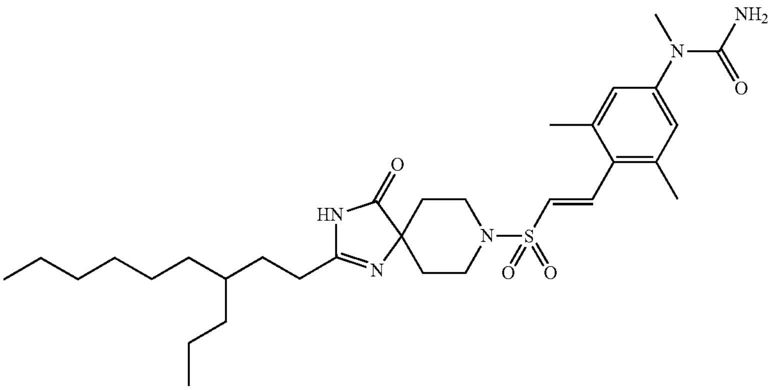 [SMILES: CCCCCCC(CCC)CCC1=NC2(CCN([S@TB18](=O)(=O)/C=C/c3c(C)cc(N(C)C(N)=O)cc3C)CC2)C(=O)N1] | LCMS-D-1 | 2.48 | 588 (M + H)+ |
| 1127 | 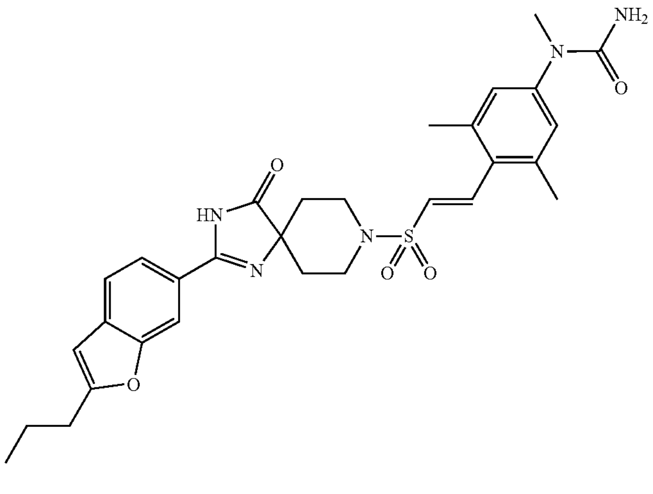 [SMILES: CCCc1cc2ccc(C3=NC4(CCN([S@TB18](=O)(=O)/C=C/c5c(C)cc(N(C)C(N)=O)cc5C)CC4)C(=O)N3)cc2o1] | LCMS-D-1 | 2.12 | 578 (M + H)+ |

TABLE 165-continued

| Compound | Structure | LCMS condition | Retention time (min) | MS (m/z) |
|---|---|---|---|---|
| 1128 | 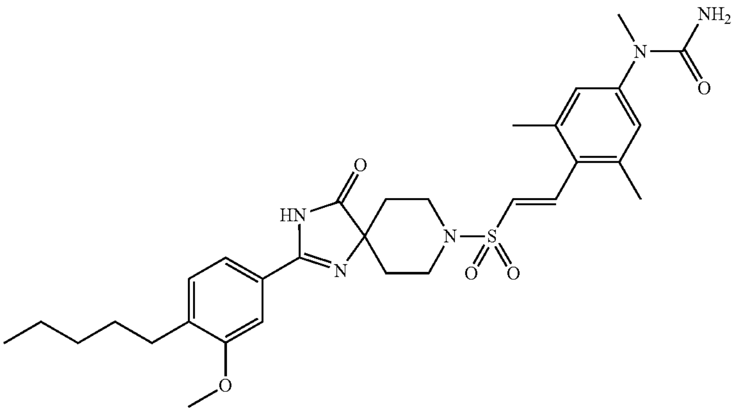 [SMILES: CCCCCc1ccc(C2=NC3(CCN([S@TB18](=O)(=O)/C=C/c4c(C)cc(N(C)C(N)=O)cc4C)CC3)C(=O)N2)cc1OC] | LCMS-D-1 | 2.98 | 596 (M + H)+ |
| 1129 | 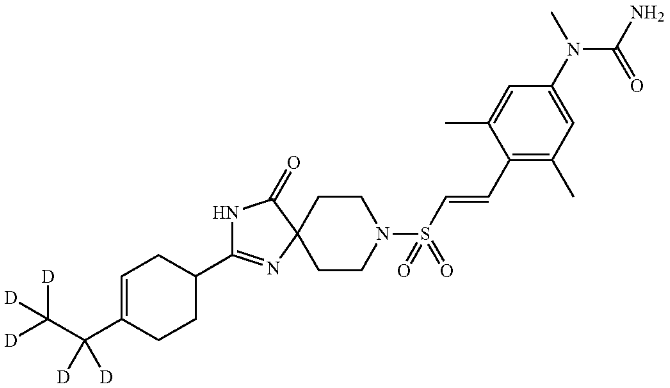 [SMILES: [2H]C([2H])([2H])C([2H])([2H])C1=CC[C@H](C2=NC3(CCN([S@TB18](=O)(=O)/C=C/c4c(C)cc(N(C)C(N)=O)cc4C)CC3)C(=O)N2)CC1] | LCMS-F-1 | 0.95 | 533 (M + H)+ |
| 1130 | 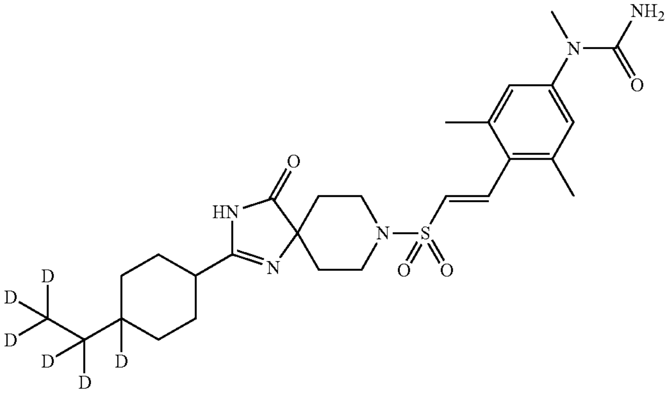 [SMILES: [2H]C([2H])([2H])C([2H])([2H])C1([2H])CCC(C2=NC3(CCN([S@TB18](=O)(=O)/C=C/c4c(C)cc(N(C)C(N)=O)cc4C)CC3)C(=O)N2)CC1] | LCMS-F-1 | 0.97 | 536 (M + H)+ |

The carboxylic acid reagent used in the synthesis of Compound 1115 (7-ethoxy-heptanoic acid) was synthesized by the following method.

(Reaction 271-3)

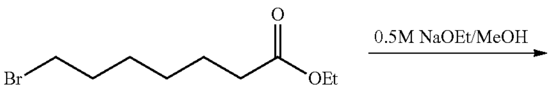

271d

-continued

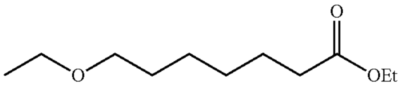

271e 0.5 M sodium ethoxide (1.6 ml, 4.31 mmol) was added to a solution of ethyl 7-bromoheptanoate (300 mg, 1.44 mmol) in ethanol (7.0 ml), and the mixture was heated under reflux for two hours. The reaction mixture was concentrated under reduced pressure, and the resulting residue was then purified by silica gel column chromatography (hexane:ethyl acetate=10:1) to give ethyl 7-ethoxyheptanoate (102.4 mg, 40%).

$^{1}$H-NMR (300 MHz, DMSO-d6) δ 1.18 (t, 3H, J=7.3 Hz), 1.24 (t, 3H, J=7.3 Hz), 1.29-1.38 (m, 4H), 1.52-1.68 (m, 4H), 2.28 (t, 2H, J=7.6 Hz), 3.45-3.51 (m, 4H), 4.05-4.17 (m, 2H).

(Reaction 271-4)

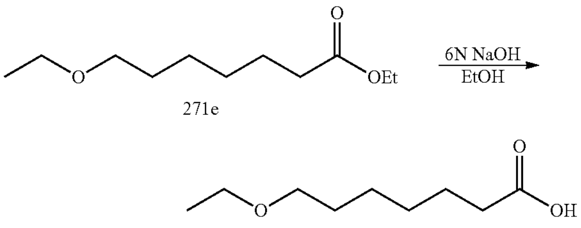

271e

271f

7-Ethoxy-heptanoic acid was synthesized by operations similar to those in Reaction 95-18 using appropriate reagents and starting material.

$^{1}$H-NMR (300 MHz, DMSO-d6) δ 1.13 (m, 3H), 1.35 (m, 4H), 1.58 (m, 4H), 2.23 (m, 2H), 3.49 (m, 4H), 12.36 (s, 1H).

The carboxylic acid reagent used in the synthesis of Compound 1116 (3-(6,6,6-trifluoro-hexyl)-benzoic acid) was synthesized by the following method.

(Reaction 271-5)

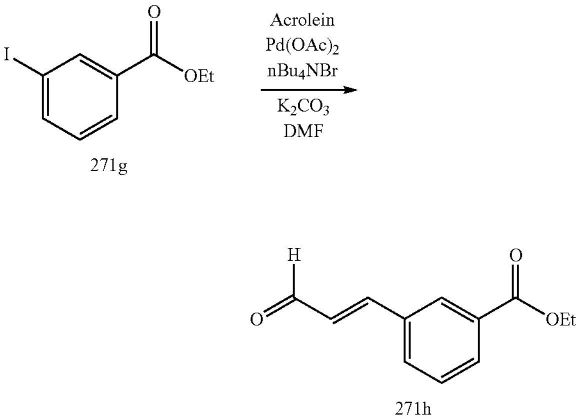

271g

271h

Acrolein (180 μl, 2.71 mmol), tetrabutylammonium bromide (385 mg, 1.19 mmol), palladium acetate (5 mmol %) and potassium carbonate (450 mg, 3.26 mmol) were added to a solution of methyl 3-iodobenzoate (300 mg, 1.08 mmol) in DMF (6.0 ml), and the mixture was heated with stirring at 80° C. for two hours. The reaction mixture was cooled to room temperature and then diluted with ethyl acetate, and the organic layer was washed with water and saturated brine. The organic layer was concentrated under reduced pressure, and the resulting residue was then purified by silica gel column chromatography (hexane:ethyl acetate=8:1) to give ethyl 3-(3-oxoprop-1-en-1-yl)benzoate as a white solid (280 mg, 96%).

MS (ESI) m/z=205 (M+H)+.

(Reaction 271-6)

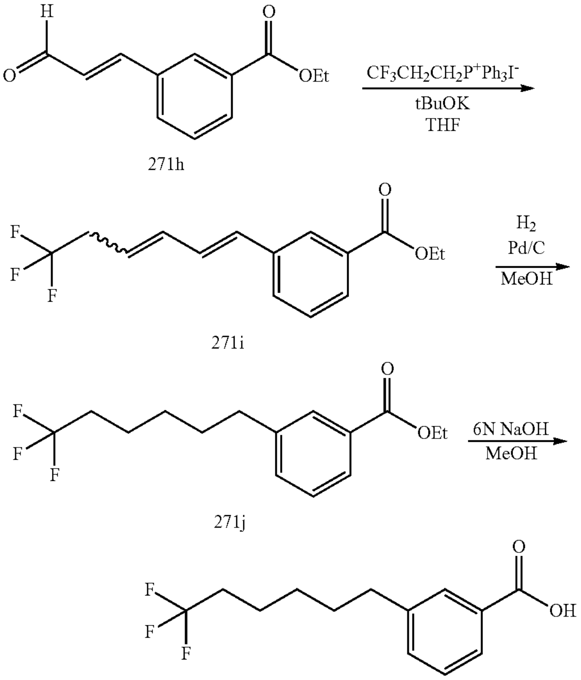

271h

271i

271j

271k 3-(6,6,6-Trifluoro-hexyl)-benzoic acid was synthesized by operations similar to those in Reaction 191-14, Reaction 18-2 and Reaction 95-18 using appropriate reagents and starting material.

MS (ESI) m/z=261 (M+H)+.

The carboxylic acid reagent used in the synthesis of Compound 1117 (4-(6,6,6-trifluoro-hexyl)-benzoic acid) was synthesized by the following method.

(Reaction 271-7)

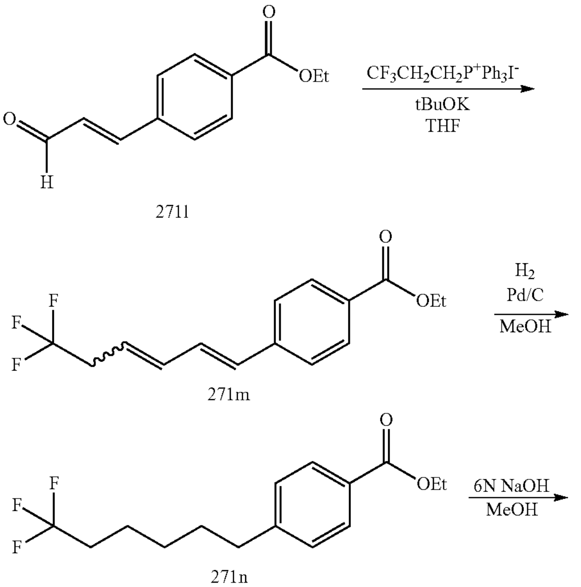

271l

271m

271n

-continued

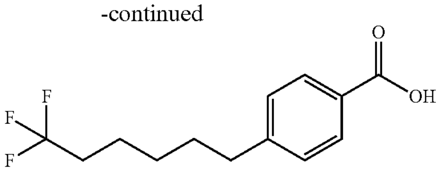

271o 4-(6,6,6-Trifluoro-hexyl)-benzoic acid was synthesized by operations similar to those in Reaction 191-14, Reaction 18-2 and Reaction 95-18 using appropriate reagents and starting material.

MS (ESI) m/z=261 (M+H)+.

The carboxylic acid reagent used in the synthesis of Compound 1120 ((E)-7-phenyl-hept-6-enoic acid) was synthesized by the following method.

(Reaction 271-8)

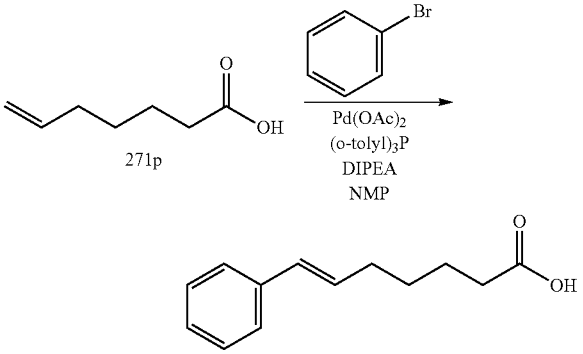

271p

271q (E)-7-Phenyl-hept-6-enoic acid was synthesized by operations similar to those in Reaction 26-1 (using NMP as a solvent) using appropriate reagents and starting material.

MS (ESI) m/z=203 (M−H)−.

The carboxylic acid reagent used in the synthesis of Compound 1121 ((E)-10-phenyl-dec-9-enoic acid) was synthesized by the following method.

(Reaction 271-9)

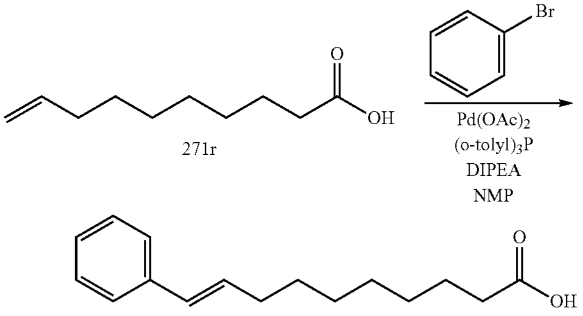

271r

271s (E)-10-Phenyl-dec-9-enoic acid was synthesized by operations similar to those in Reaction 26-1 (using NMP as a solvent) using appropriate reagents and starting material.

MS (ESI) m/z=245 (M−H)−.

The carboxylic acid reagent used in the synthesis of Compound 1122 (6-propylsulfanyl-hexanoic acid) was synthesized by the following method.

(Reaction 271-10)

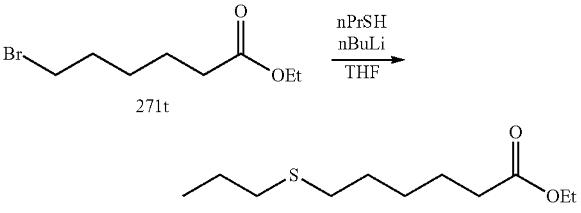

271t

271u

A solution of propanethiol (0.609 ml, 6.72 mmol) in anhydrous THF (10 ml) was cooled to −10° C. in a nitrogen atmosphere. 2 M nBuLi (4.03 ml, 8.07 mmol) was added dropwise and the mixture was then stirred for 10 minutes. A solution of ethyl 6-bromohexanoate in anhydrous THF (5 ml) was then added and the mixture was stirred for 40 minutes. The reaction mixture was quenched by adding water and then extracted with ethyl acetate. The organic layer was washed with water and saturated brine and dried over sodium sulfate. The organic layer was concentrated under reduced pressure, and the resulting residue was then purified by silica gel column chromatography (hexane:ethyl acetate=15:1) to give ethyl 6-(propylthio)hexanoate as a colorless oily substance (1.46 g, 100%).

$^{1}$H-NMR (300 MHz, $CDCl_3$) δ 0.98 (t, 3H, J=7.6 Hz), 1.25 (t, 3H, J=7.2 Hz), 1.46-1.36 (m, 2H), 1.69-1.54 (m, 6H), 2.30 (t, 2H, J=7.2 Hz), 2.49 (dd, 4H, J=7.2, 14.3 Hz), 4.12 (dd, 2H, J=7.2, 14.1 Hz).

(Reaction 271-11)

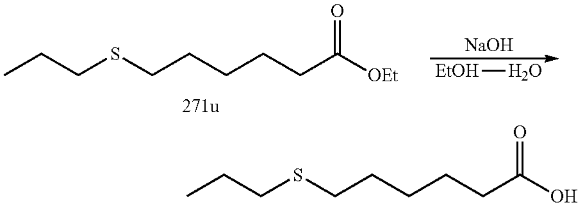

271u

271v

6-Propylsulfanyl-hexanoic acid was synthesized by operations similar to those in Reaction 95-18 using appropriate reagents and starting material.

$^{1}$H-NMR (300 MHz, DMSO-d6) δ 0.92 (m, 3H), 1.34 (m, 2H), 1.51 (m, 6H), 2.19 (m, 2H), 2.45 (m, 4H).

The carboxylic acid reagent used in the synthesis of Compound 1123 (8-methoxy-octanoic acid) was synthesized by the following method.

(Reaction 271-12)

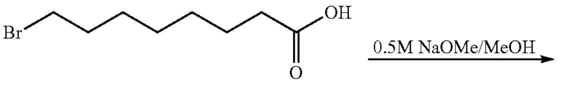

271w

-continued

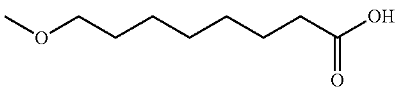

271x

8-Methoxy-octanoic acid was synthesized by operations similar to those in Reaction 271-3 using appropriate reagents and starting material.

$^{1}$H-NMR (300 MHz, $CDCl_3$) δ 1.39 (m, 6H), 1.69 (m, 4H), 2.13 (s, 1H), 2.42 (m, 2H), 3.33 (s, 3H), 3.39 (m, 2H).

The carboxylic acid reagent used in the synthesis of Compound 1124 (6-propoxy-hexanoic acid) was synthesized by the following method.

(Reaction 271-13)

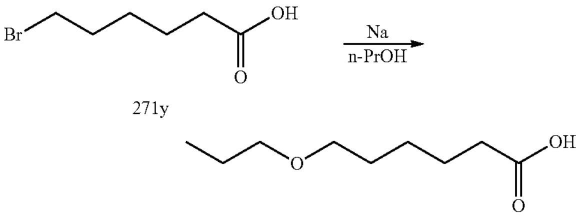

271y

271z

Sodium (354 mg, 15.38 mmol) was added to a solution of 6-bromohexanoic acid (300 mg, 1.54 mmol) in propyl alcohol (15 ml), and the mixture was heated under reflux for two hours. The reaction mixture was cooled to room temperature and then concentrated under reduced pressure. The resulting residue was purified by silica gel column chromatography (dichloromethane:methanol=30:1) to give 6-propoxy-hexanoic acid (209 mg, 78%).

$^{1}$H-NMR (300 MHz, $CDCl_3$) δ 0.88 (m, 3H), 1.37 (m, 2H), 1.62 (m, 6H), 2.44 (m, 2H), 3.52 (m, 4H).

The carboxylic acid reagent used in the synthesis of Compound 1126 (4-propyl-decanoic acid) was synthesized by the following method.

(Reaction 271-14)

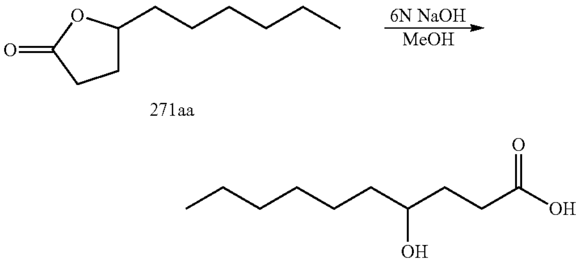

271aa

271ab

4-Hydroxy-decanoic acid was synthesized by operations similar to those in Reaction 95-18 using appropriate reagents and starting material. This was used in the next step without complete purification.

(Reaction 271-15)

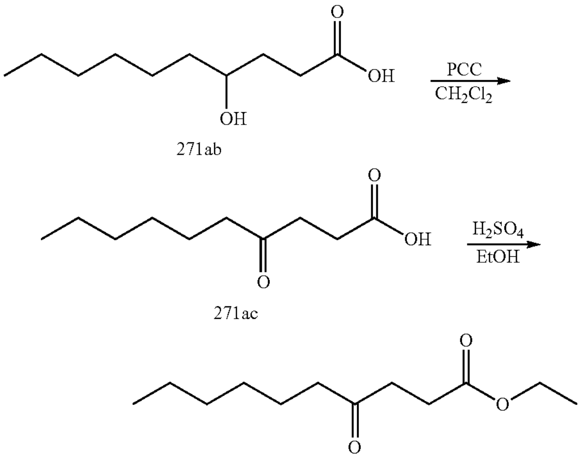

271ab

271ac

271ad

PCC (1.2 g, 2.71 mmol) was added to a solution of 4-hydroxydecanoic acid (830 mg, 4.4 mmol) in dichloromethane (30 ml), and the mixture was stirred at room temperature for five hours. The reaction mixture was adjusted to pH 1 by adding 1 N hydrochloric acid and then extracted with ethyl acetate. The organic layer was washed with water and saturated brine and then concentrated under reduced pressure. The resulting residue was then dissolved in ethanol (15 ml). Five drops of sulfuric acid were added and the mixture was stirred at 80° C. for 18 hours. The reaction mixture was concentrated under reduced pressure, and the resulting residue was purified by silica gel column chromatography (hexane:ethyl acetate=2:1) to give ethyl 4-oxodecanoate (440 mg, 46% in two steps).

$^{1}$H-NMR (300 MHz, $CDCl_3$) δ 0.86 (t, 3H, J=7.2 Hz), 1.26 (m, 9H), 1.57 (m, 2H), 2.43 (t, 2H, J=7.2 Hz), 2.56 (m, 2H), 2.70 (m, 2H), 4.11 (dt, 2H, J=7.2, 7.2 Hz).

(Reaction 271-16)

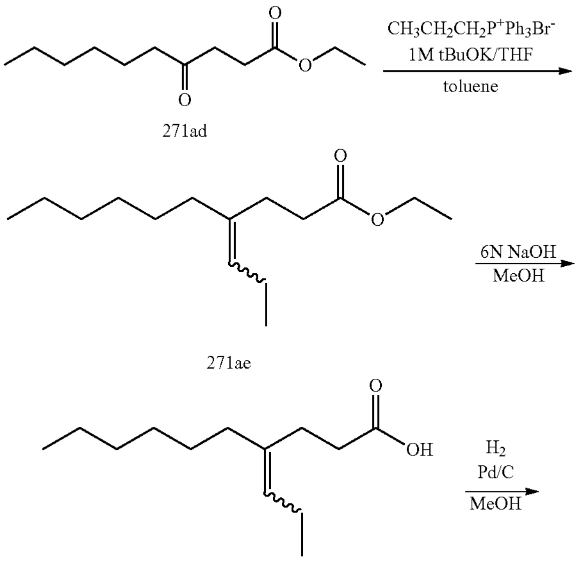

271ad

271ae

271af

-continued

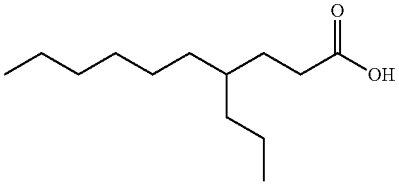

271ag

4-Propyl-decanoic acid was synthesized by operations similar to those in Reaction 191-14, Reaction 95-18 and Reaction 18-2 using appropriate reagents and starting material.

$^1$H-NMR (300 MHz, $CDCl_3$) δ 0.88 (m, 6H), 1.27 (m, 15H), 2.38 (m, 2H), 2.61 (m, 2H), 8.91 (br, 1H).

The carboxylic acid reagent used in the synthesis of Compound 1127 (2-propyl-benzofuran-6-carboxylic acid) was synthesized by the following method.

(Reaction 271-17)

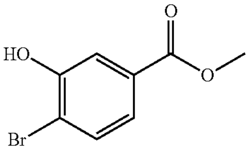

271ah

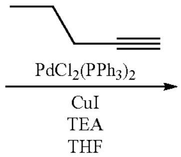

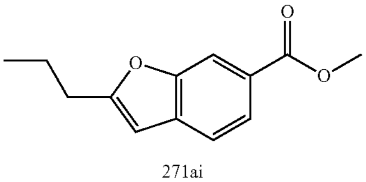

271ai

NaOH
EtOH—H2O

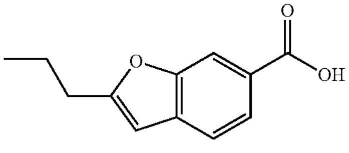

271aj

2-Propyl-benzofuran-6-carboxylic acid was synthesized by operations similar to those in Reaction 95-10 (using $PdCl_2(PPh_3)_2$ as a catalyst) and Reaction 95-18 using appropriate reagents and starting material.

$^1$H-NMR (300 MHz, $CDCl_3$) δ 1.02 (m, 3H), 1.80 (m, 2H), 2.79 (m, 2H), 6.46 (s, 1H), 7.53 (m, 1H), 7.96 (m, 1H), 8.16 (s, 1H).

The carboxylic acid reagent used in the synthesis of Compound 1128 (3-methoxy-4-pentyl-benzoic acid) was synthesized by the following method.

(Reaction 271-18)

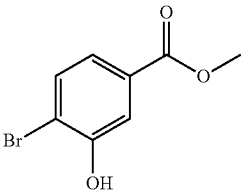

271ak

MeI
K2CO3
DMF

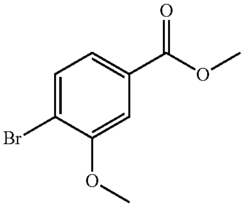

271al

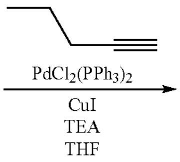

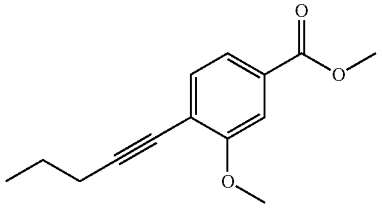

271am

H2
Pd(OH)2
EtOH

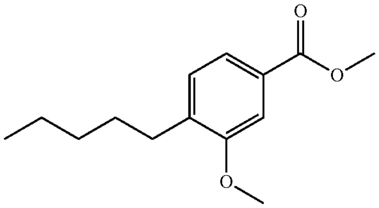

271an

6N NaOH
EtOH

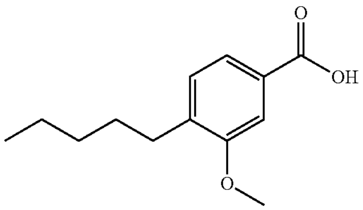

271ao

3-Methoxy-4-pentyl-benzoic acid was synthesized by operations similar to those in Reaction 26-4, Reaction 95-10 (using $PdCl_2(PPh_3)_2$ as a catalyst), Reaction 122-2 and Reaction 95-18 using appropriate reagents and starting material.

MS (ESI) m/z=223 (M+H)+.

A mixture of the carboxylic acid reagent used in the synthesis of the compound 1129 (4-([1,1,2,2,2-$^2H_5$]ethyl)-cyclohex-3-en-ecarboxylic acid)

and the carboxylic acid reagent used in the synthesis of the compound 1130 (4-([1,1,2,2,2-$^2H_5$]ethyl)-[4-$^2$H]-cyclohex-anecarboxylic acid)

was synthesized by the following method.

(Reaction 271-19)

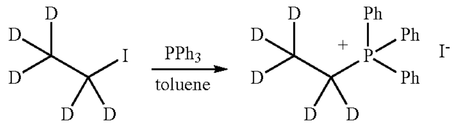

271ap 271aq

A solution of iodo-ethane-d5 (3.00 g, 18.6 mmol) and triphenylphosphine (14.6 mg, 55.8 mmol) in toluene (15 ml) was stirred at 110° C. for 21 hours. The reaction mixture was filtered, and the solid was washed with toluene and dried to give [1,1,2,2,2-$^2H_5$]ethyltriphenylphosphonium iodide as a white solid (7.85 g, 100%). This was used in the next reaction without complete purification.

(Reaction 271-20)

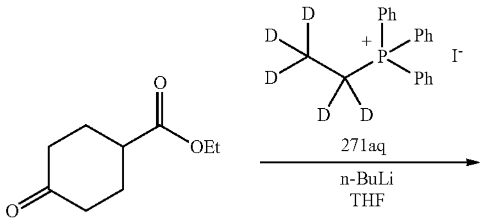

101b

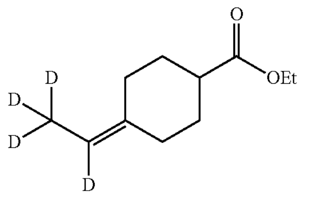

271ar

+

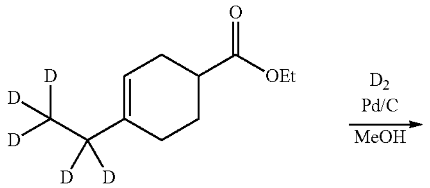

271as
Mixture = 10:1

-continued

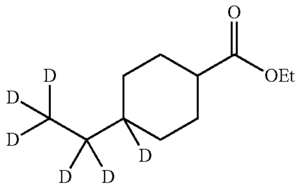

271at

+

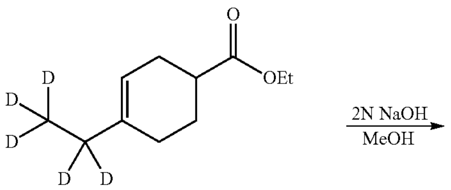

271au
Mixture = 3:1

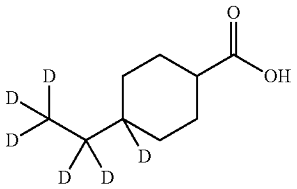

271av

+

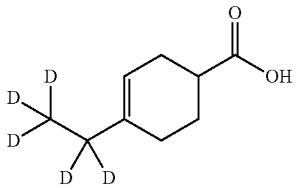

271aw
Mixture = 3:1

4-([1,1,2,2,2-$^2H_5$]Ethyl)-cyclohex-3-enecarboxylic acid and 4-([1,1,2,2,2-$^2H_5$]ethyl)-[4-$^2$H]-cyclohexanecarboxylic acid were synthesized as a mixture by operations similar to those in Reaction 101-1, Reaction 18-2 and Reaction 95-18 using appropriate reagents and starting material. This was used in the next step without complete purification.

Example 272
12-(8-{(E)-2-[2,6-Dimethyl-4-(1-methyl-ureido)-phenyl]-ethenesulfonyl}-4-oxo-1,3,8-triaza-spiro[4.5]dec-1-en-2-yl)-dodecanoic acid (Compound 1131)
and 12-(8-{(E)-2-[2,6-dimethyl-4-(1-methyl-ureido)-phenyl]-ethenesulfonyl}-4-oxo-1,3,8-triaza-spiro[4.5]dec-1-en-2-yl)-dodecanoic acid ethyl ester (Compound 1132)
(Reaction 272-1)
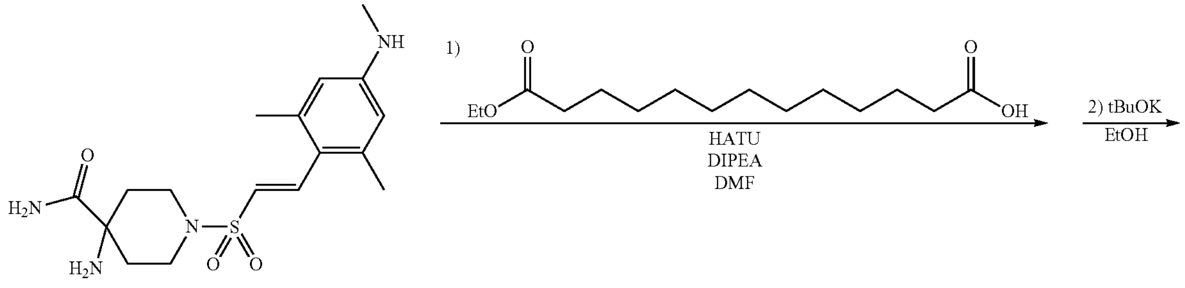
233f
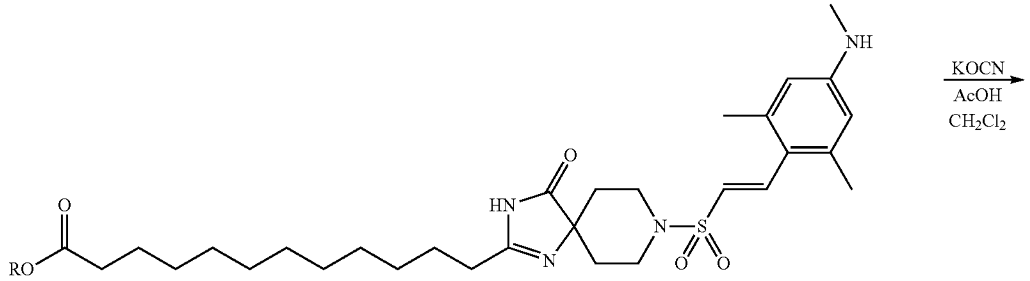
R = Et and H
272a
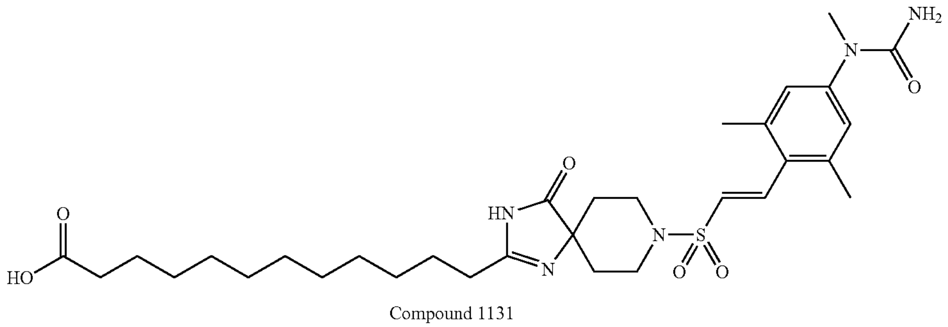
Compound 1131
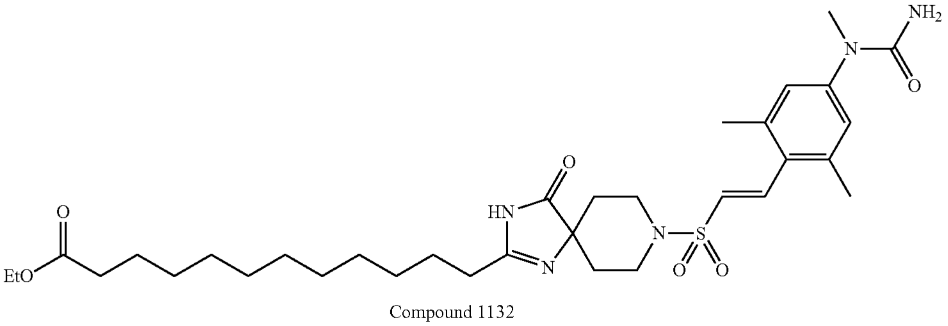
Compound 1132

12-(8-{(E)-2-[2,6-Dimethyl-4-(1-methyl-ureido)-phenyl]-ethenesulfonyl}-4-oxo-1,3,8-triaza-spiro[4.5]dec-1-en-2-yl)-dodecanoic acid MS (ESI) m/z=618 (M+H)+ and 12-(8-{(E)-2-[2,6-dimethyl-4-(1-methyl-ureido)-phenyl]-ethenesulfonyl}-4-oxo-1,3,8-triaza-spiro[4.5]dec-1-en-2-yl)-dodecanoic acid ethyl ester MS (ESI) m/z=646 (M+H)+ were synthesized by operations similar to those in Reaction 269-1 and Reaction 89-2 (using KOCN) using appropriate reagents and starting material.

Example 273

1-(3,5-Dimethyl-4-{(E)-2-[4-oxo-2-(5-phenyl-pentyl)-1,3,8-triaza-spiro[4.5]dec-1-ene-8-sulfonyl]-vinyl}-phenyl)-1-methyl-urea trifluoroacetate (Compound 1133) and 1-(3,5-dimethyl-4-{(Z)-2-[4-oxo-2-(5-phenyl-pentyl)-1,3,8-triaza-spiro[4.5]dec-1-ene-8-sulfonyl]-vinyl}-phenyl)-1-methyl-urea trifluoroacetate (Compound 1134)

(Reaction 273-1)

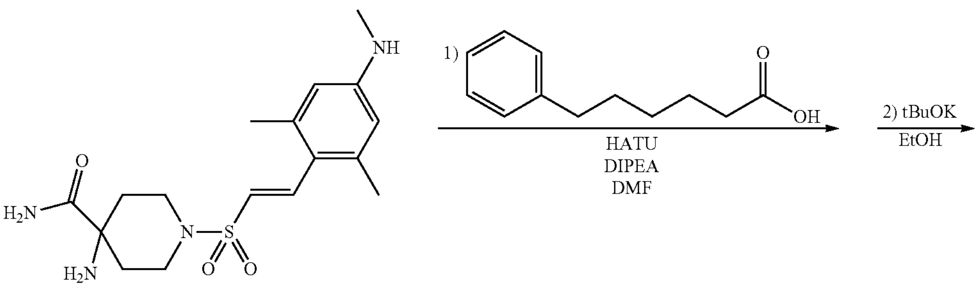

233f

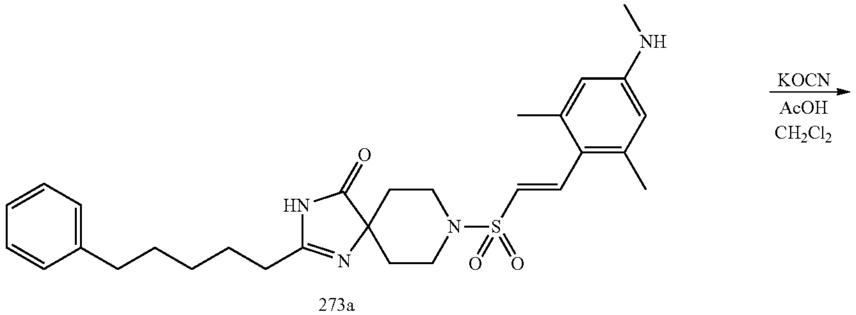

273a

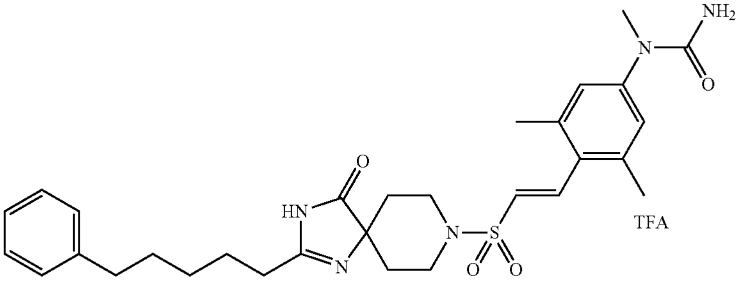

TFA

Compound 1133

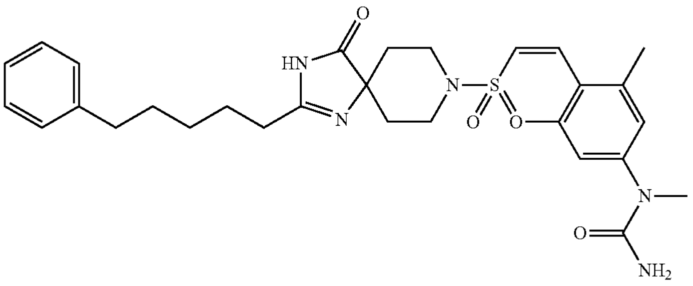

TFA

Compound 1134

1-(3,5-Dimethyl-4-{(E)-2-[4-oxo-2-(5-phenyl-pentyl)-1,3,8-triaza-spiro[4.5]dec-1-ene-8-sulfonyl]-vinyl}-phenyl)-1-methyl-urea trifluoroacetate MS (ESI) m/z=566 (M+H)+ and 1-(3,5-dimethyl-4-{(Z)-2-[4-oxo-2-(5-phenyl-pentyl)-1,3,8-triaza-spiro[4.5]dec-1-ene-8-sulfonyl]-vinyl}-phenyl)-1-methyl-urea trifluoroacetate MS (ESI) m/z=566 (M+H)+ were synthesized by operations similar to those in Reaction 269-1 and Reaction 89-2 (using KOCN) using appropriate reagents and starting material.

Example 274

1-[3,5-Dimethyl-4-(2-{4-oxo-2-[3-(4,4,5,5,5-pentafluoro-pentyloxy)-phenyl]-1,3,8-triaza-spiro[4.5]dec-1-ene-8-sulfonyl}-ethyl)-phenyl]-1-methyl-urea (Compound 1135)

(Reaction 274-1)

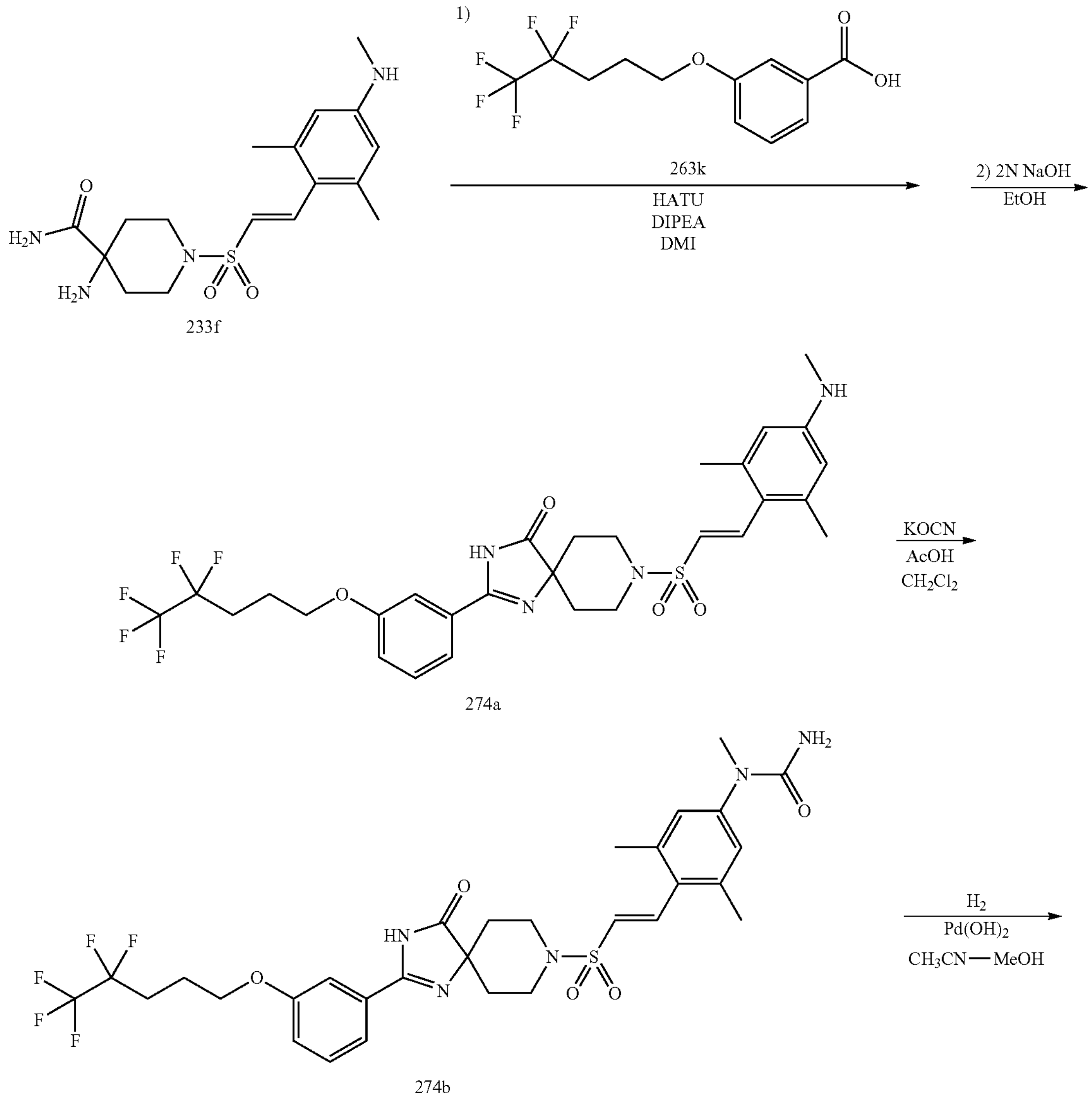

233f

263k

274a

274b

-continued

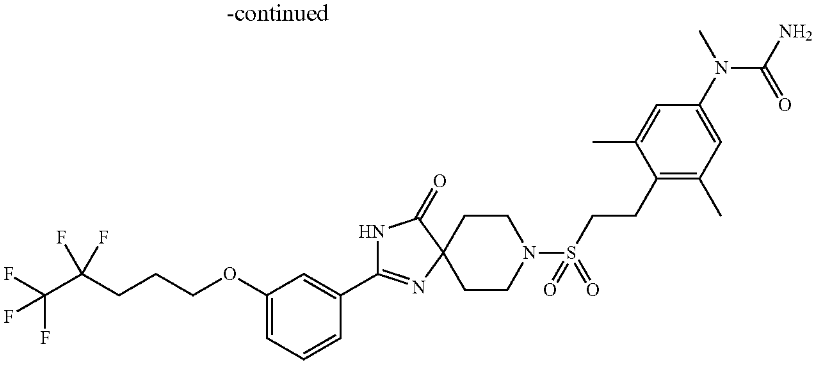

Compound 1135

1-[3,5-Dimethyl-4-(2-{4-oxo-2-[3-(4,4,5,5,5-pentafluoro-pentyloxy)-phenyl]-1,3,8-triaza-spiro[4.5]dec-1-ene-8-sulfonyl}-ethyl)-phenyl]-1-methyl-urea was synthesized by operations similar to those in Reaction 269-1, Reaction 89-2 (using KOCN) and Reaction 184-1 using appropriate reagents and starting material.

MS (ESI) m/z=674 (M+H)+.

Example 275

1-(3,5-Dimethyl-4-{2-[4-oxo-2-(3'-propyl-biphenyl-3-yl)-1,3,8-triaza-spiro[4.5]dec-1-ene-8-sulfonyl]-ethyl}-phenyl)-1-methyl-urea (Compound 1136)

(Reaction 275-1)

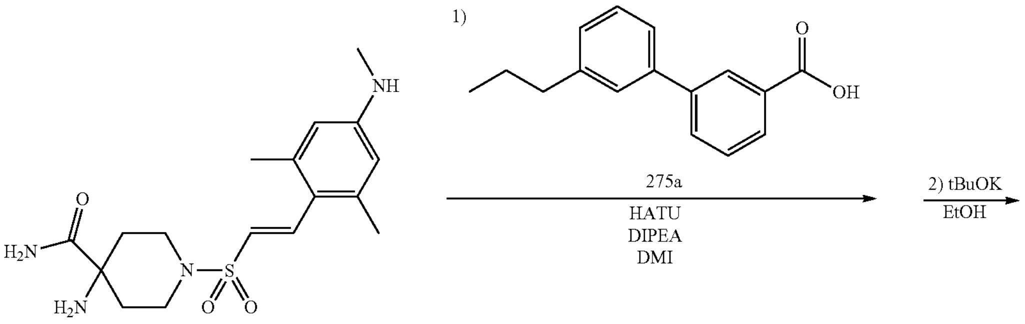

233f

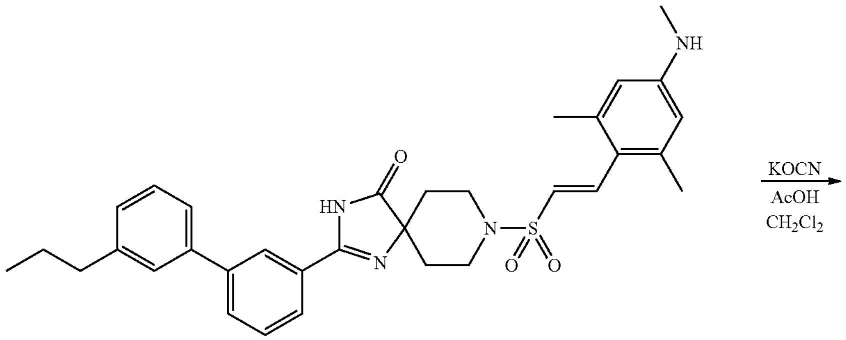

275b

-continued

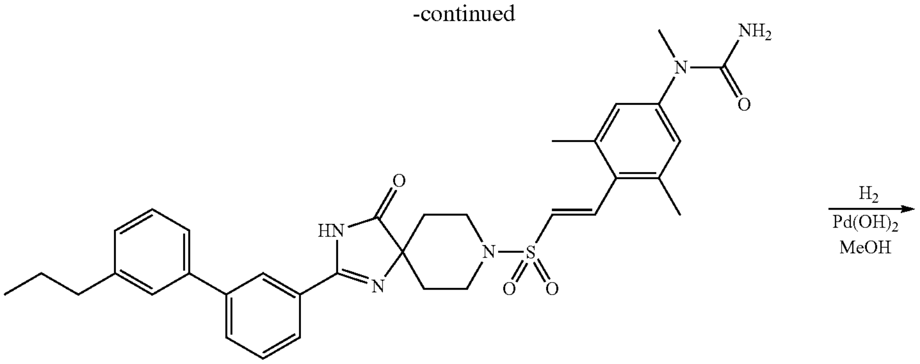

275c

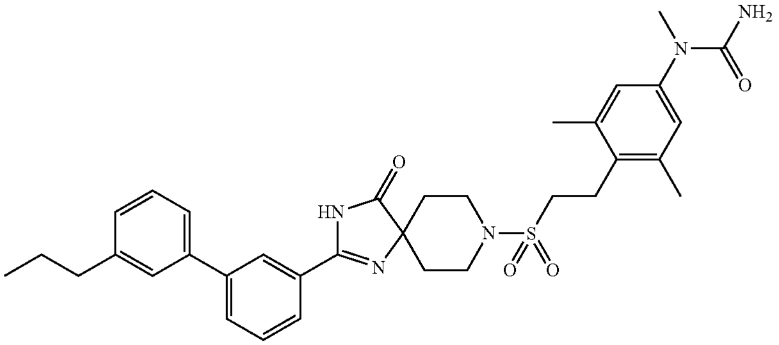

Compound 1136

1-(3,5-Dimethyl-4-{2-[4-oxo-2-(3'-propyl-biphenyl-3-yl)-1,3,8-triaza-spiro[4.5]dec-1-ene-8-sulfonyl]-ethyl}-phenyl)-1-methyl-urea was synthesized by operations similar to those in Reaction 269-1, Reaction 89-2 (using KOCN) and Reaction 184-1 using appropriate reagents and starting material.

MS (ESI) m/z=616 (M+H)+.

The carboxylic acid reagent used in the synthesis of Compound 1136 (3'-propyl-biphenyl-3-carboxylic acid) was synthesized by the following method.

(Reaction 275-2)

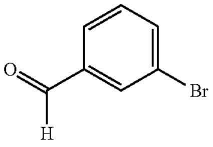

275d

+

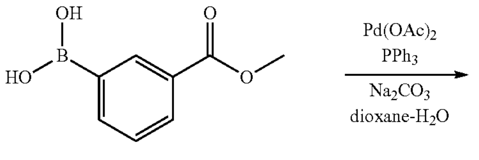

275e

-continued

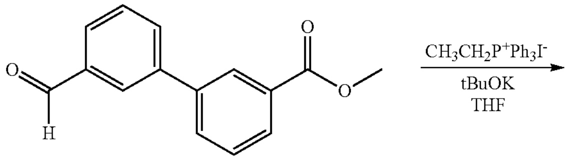

275f

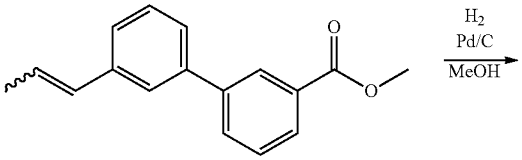

275g

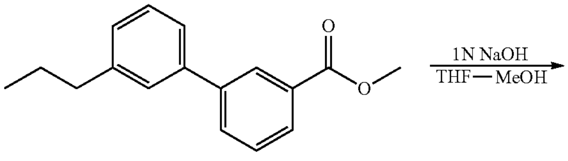

275h

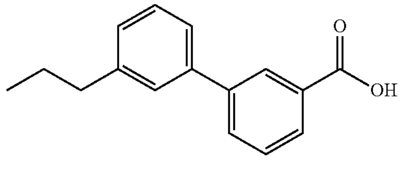

275a

3'-Propyl-biphenyl-3-carboxylic acid was synthesized by operations similar to those in Reaction 259-2, Reaction 191-

14, Reaction 18-2 and Reaction 95-18 using appropriate reagents and starting material.
$^{1}$H-NMR (300 MHz, $CDCl_3$) δ 8.36 (t, 1H, J=1.5 Hz), 8.10 (dt, 1H, J=7.6, 1.5 Hz), 7.85 (dt, 1H, J=7.6, 1.5 Hz), 7.56 (t, 1H, J=7.6 Hz), 7.46 (dt, 1H, J=7.3, 1.5 Hz), 7.45 (d, 1H, J=7.3 Hz), 7.39 (t, 1H, J=7.3 Hz), 7.23 (dt, 1H, J=7.3, 1.5 Hz), 2.68 (t, 2H, J=7.6 Hz), 1.71 (m, 2H), 0.99 (t, 3H, J=7.6 Hz).
Example 276
1-(3,5-Dimethyl-4-{2-[4-oxo-2-(4-trimethylsilanyl-cyclohexyl)-1,3,8-triaza-spiro[4.5]dec-1-ene-8-sulfonyl]-ethyl}-phenyl)-1-methyl-urea (Compound 1137)
(Reaction 276-1)
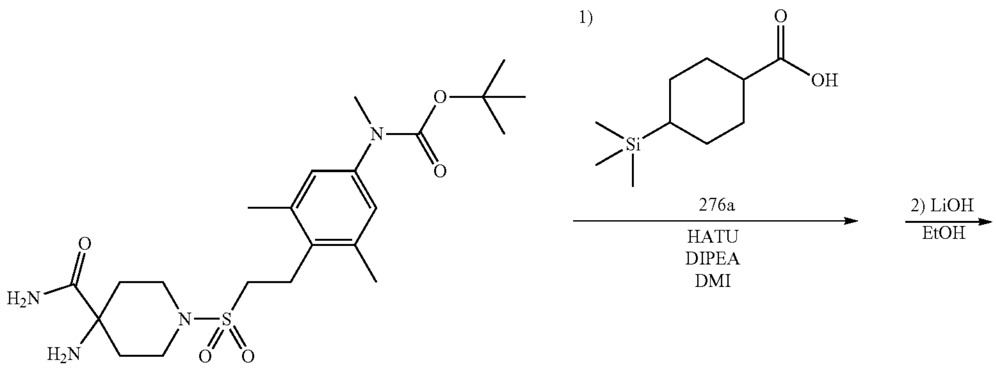
239d
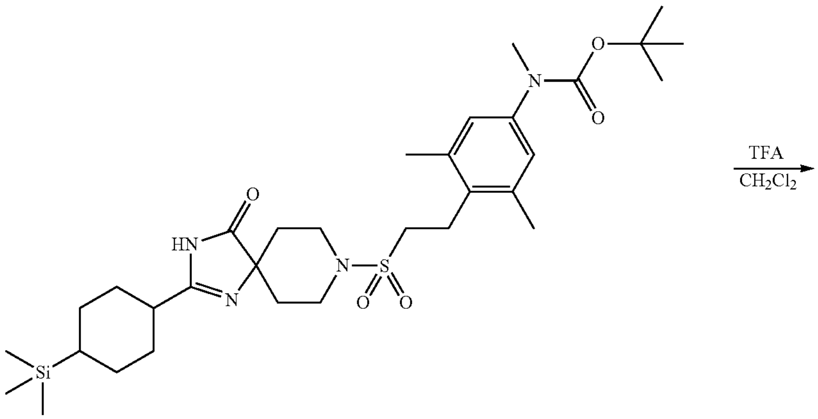
276b
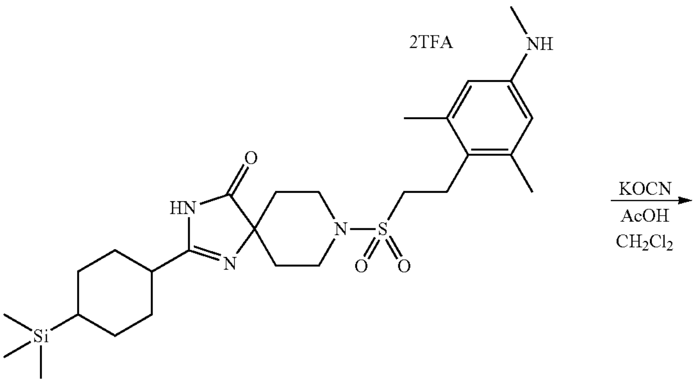
276c -continued

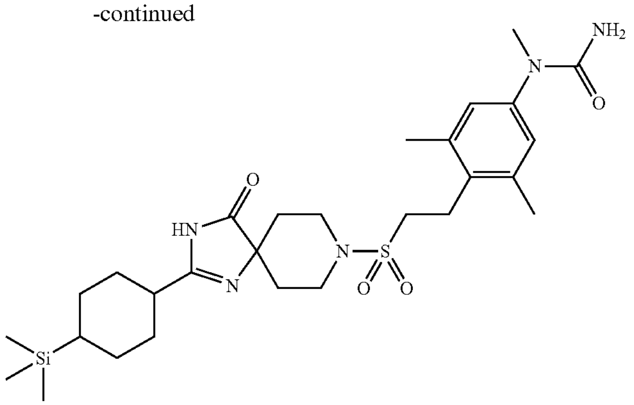

Compound 1137

1-(3,5-Dimethyl-4-{2-[4-oxo-2-(4-trimethylsilanyl-cyclohexyl)-1,3,8-triaza-spiro[4.5]dec-1-ene-8-sulfonyl]-ethyl}-phenyl)-1-methyl-urea was synthesized by operations similar to those in Reaction 269-1 (using LiOH), Reaction 4-1 and Reaction 89-2 (using KOCN) using appropriate reagents and starting material.

MS (ESI) m/z=576 (M+H)+.

The carboxylic acid reagent used in the synthesis of Compound 1137 (4-trimethylsilanyl-cyclohexanecarboxylic acid) was synthesized by the following method.

(Reaction 276-2)

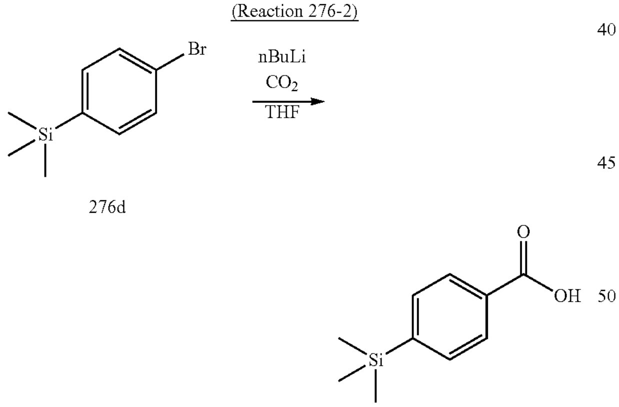

276d

276e

1-Bromo-4-trimethylsilyl-benzene (0.426 ml, 2.18 mmol) was dissolved in THF (20 ml), and n-butyllithium (1.59 M solution in n-hexane, 1.51 ml, 1.40 mmol) was added dropwise at −78° C. After stirring for 20 minutes, crushed dry ice (excess) was added. The reaction solution was stirred at room temperature for one hour, and 1 M hydrochloric acid and water were then added, followed by extraction with ethyl acetate. The organic layer was washed with water and saturated brine, dried over anhydrous sodium sulfate and concentrated under reduced pressure. The resulting residue was purified by silica gel column chromatography (n-hexane/ethyl acetate) to give 4-trimethylsilanyl-benzoic acid (363 mg, 86%).

$^1$H-NMR (400 MHz, DMSO-$D_6$) δ 12.93 (1H, br s), 7.91 (2H, d, J=8.3 Hz), 7.65 (2H, d, J=7.8 Hz), 0.27 (9H, t, J=3.4 Hz).

(Reaction 276-3)

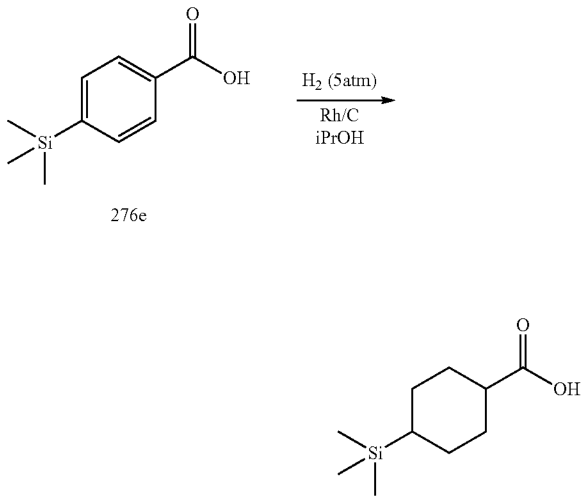

276e

276a

4-Trimethylsilanyl-cyclohexanecarboxylic acid was synthesized by operations similar to those in Reaction 193-3 using appropriate reagents and starting material.

$^1$H-NMR (400 MHz, $CDCl_3$) δ 2.73-2.66 (0.6H, m), 2.33 (0.4H, tt, J=11.0, 3.7 Hz), 2.15-0.58 (8H, m), −0.06 (9H, s) (cis:trans=ca 6:4).

The example compounds shown below were synthesized by operations similar to those in Reaction 276-1 using appropriate reagents and starting materials.

Compounds 1138 to 1142
TABLE 166
| Compound | Structure | LCMS condition | Retention time (min) | MS (m/z) |
|---|---|---|---|---|
| 1138 | 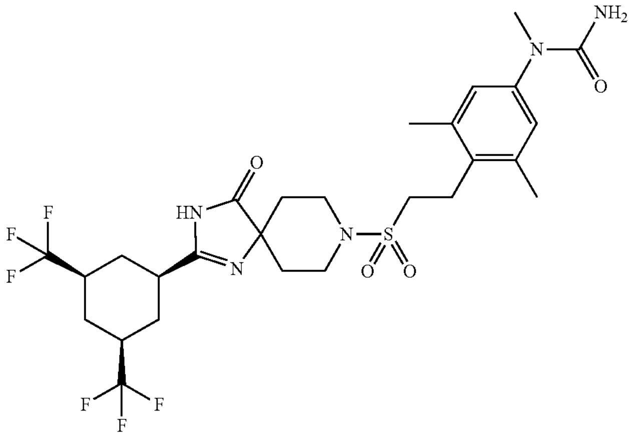 | LCMS-A-1 | 2.44 | 640 (M + H)+ |
| 1139 | 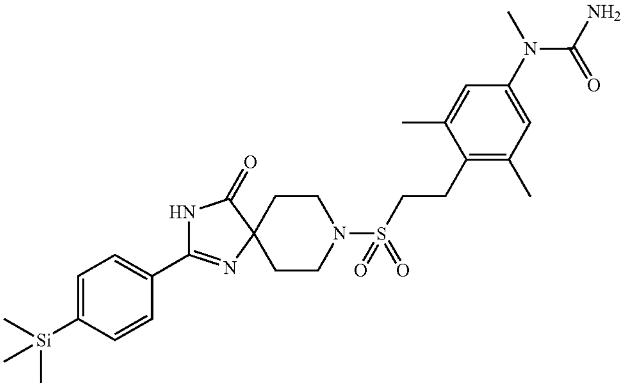 [SMILES: Cc1cc(N(C)C(N)=O)cc(C)c1CC[S@TB4](=O)(=O)N1CCC2(CC1)N=C(c1ccc([Si](C)(C)C)cc1)NC2=O] | LCMS-A-1 | 2.47 | 570 (M + H)+ |
| 1140 | 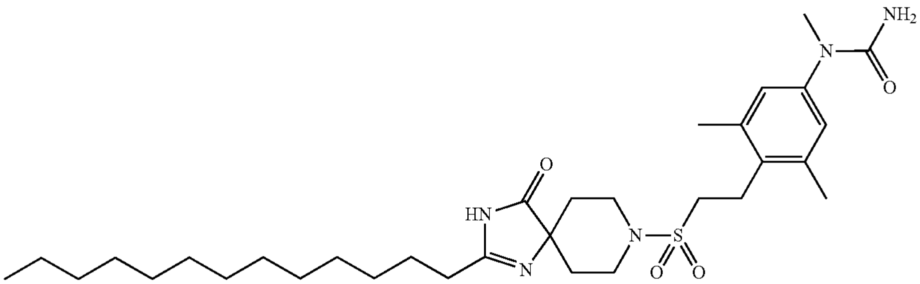 [SMILES: CCCCCCCCCCCCCC1=NC2(CCN([S@TB18](=O)(=O)CCc3c(C)cc(N(C)C(N)=O)cc3C)CC2)C(=O)N1] | LCMS-A-1 | 2.94 | 604 (M + H)+ |
| 1141 | 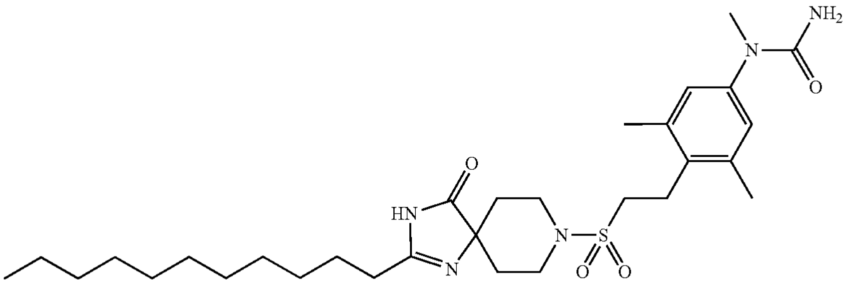 [SMILES: CCCCCCCCCCCC1=NC2(CCN([S@TB17](=O)(=O)CCc3c(C)cc(N(C)C(N)=O)cc3C)CC2)C(=O)N1] | LCMS-A-1 | 2.66 | 576 (M + H)+ |

TABLE 166-continued

| Compound | Structure | LCMS condition | Retention time (min) | MS (m/z) |
|---|---|---|---|---|
| 1142 | 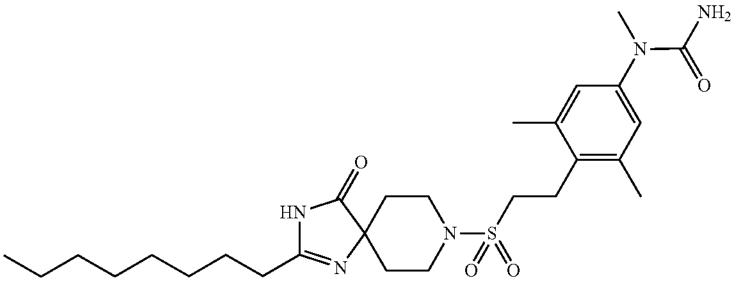 [SMILES: CCCCCCCCC1=NC2(CCN([S@TB17](=O)(=O)CCc3c(C)cc(N(C)C(N)=O)cc3C)CC2)C(=O)N1] | LCMS-A-1 | 2.31 | 534 (M + H)+ |

The carboxylic acid reagent used in the synthesis of Compound 1138 (3,5-bis-trifluoromethyl-cyclohexanecarboxylic acid) was synthesized by the following method.

(Reaction 276-4)

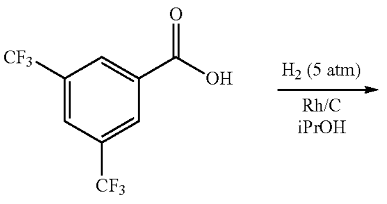

276f

-continued

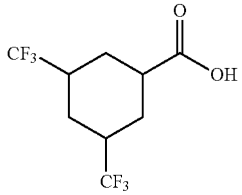

276g 3,5-Bis-trifluoromethyl-cyclohexanecarboxylic acid was synthesized by operations similar to those in Reaction 193-3 using appropriate reagents and starting material.

$^1$H-NMR (400 MHz, $CDCl_3$) δ 2.51-2.41 (1H, m), 2.35-2.27 (2H, m), 2.24-2.12 (3H, m), 1.52-1.42 (2H, m), 1.41-1.30 (1H, m).

Example 277

1-(4-{2-[2-((1S,3R)-3-Hexyl-cyclohexyl)-4-oxo-1,3,8-triaza-spiro[4.5]dec-1-ene-8-sulfonyl]-ethyl}-3,5-dimethyl-phenyl)-1-methyl-urea (Compound 1143)

(Reaction 277-1)

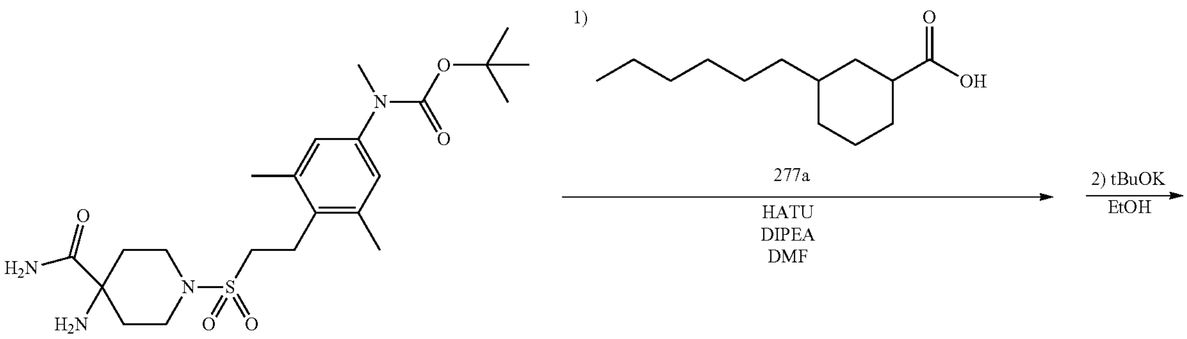

239d

-continued

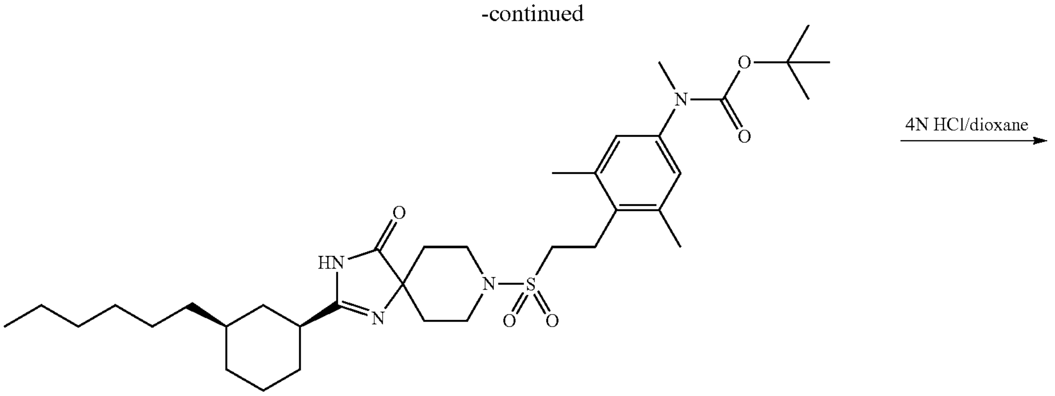

277b

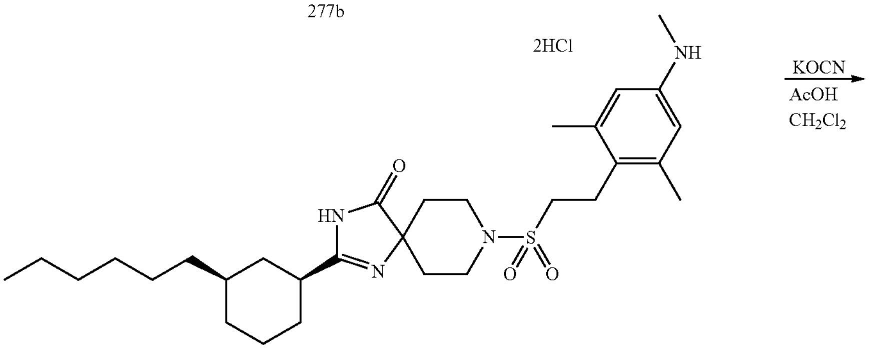

277c

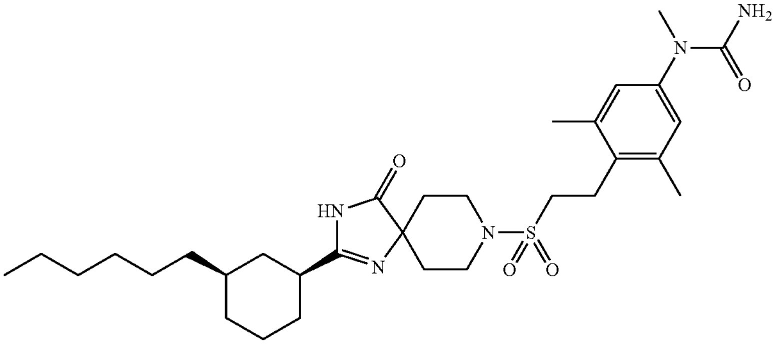

Compound 1143

1-(4-{2-[2-((1S,3R)-3-Hexyl-cyclohexyl)-4-oxo-1,3,8-triaza-spiro[4.5]dec-1-ene-8-sulfonyl]-ethyl}-3,5-dimethyl-phenyl)-1-methyl-urea was synthesized by operations similar to those in Reaction 269-1, Reaction 5-3 and Reaction 89-2 (using KOCN) using appropriate reagents and starting material.

MS (ESI) m/z=588 (M+H)+.

The carboxylic acid reagent used in the synthesis of Compound 1143 (3-hexyl-cyclohexanecarboxylic acid) was synthesized by the following method.

(Reaction 277-2)

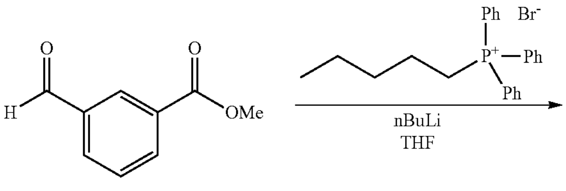

193n

-continued

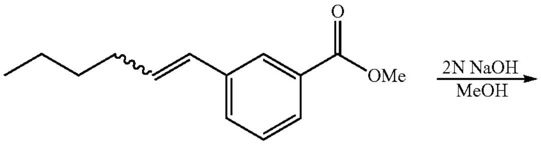

277d

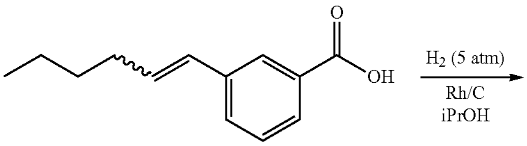

277e

-continued

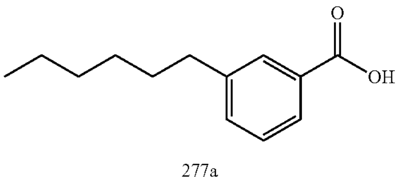

277a

3-Hexyl-cyclohexanecarboxylic acid was synthesized by operations similar to those in Reaction 101-1, Reaction 95-18 and Reaction 193-3 using appropriate reagents and starting material.

$^1$H-NMR (400 MHz, $CDCl_3$) δ 0.84-2.03 (22H, m), 2.32 (0.6H, tt, J=11.6, 2.8 Hz), 2.67-2.68 (0.4H, m) (cis:trans=3:2).

The example compounds shown below were synthesized by operations similar to those in Reaction 277-1 using appropriate reagents and starting materials.

Compounds 1144 to 1149

TABLE 167

| Compound | Structure | LCMS condition | Retention time (min) | MS (m/z) |
|---|---|---|---|---|
| 1144 | 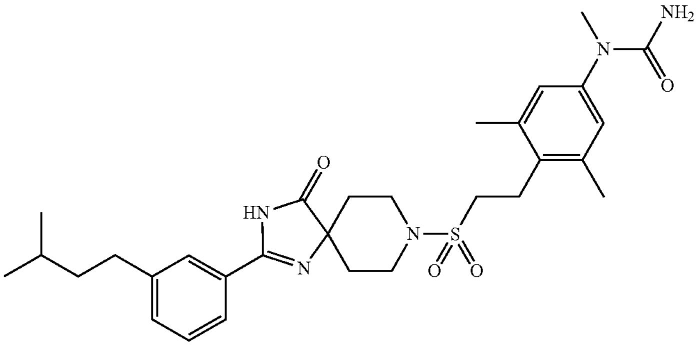 [SMILES: Cc1cc(N(C)C(N)=O)cc(C)c1CC[S@TB3](=O)(=O)N1CCC2(CC1)N=C(c1cccc(CCC(C)C)c1)NC2=O] | LCMS-C-1 | 2.93 | 568 (M + H)+ |
| 1145 | 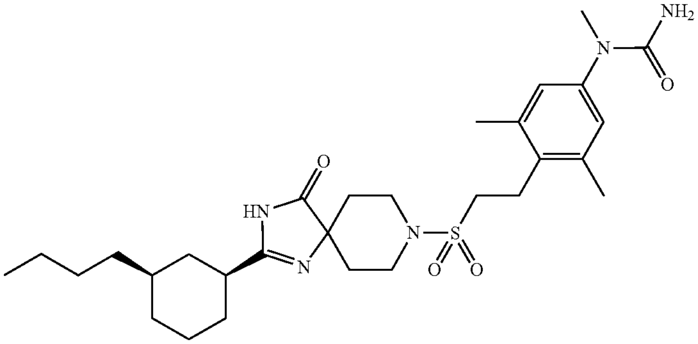 | LCMS-C-1 | 2.93 | 560 (M + H)+ |
| 1146 | 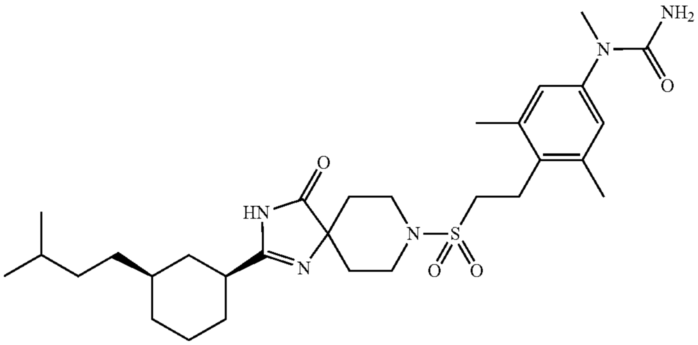 | LCMS-C-1 | 3.03 | 574 (M + H)+ |

TABLE 167-continued
| Compound | Structure | LCMS condition | Retention time (min) | MS (m/z) |
|---|---|---|---|---|
| 1147 | 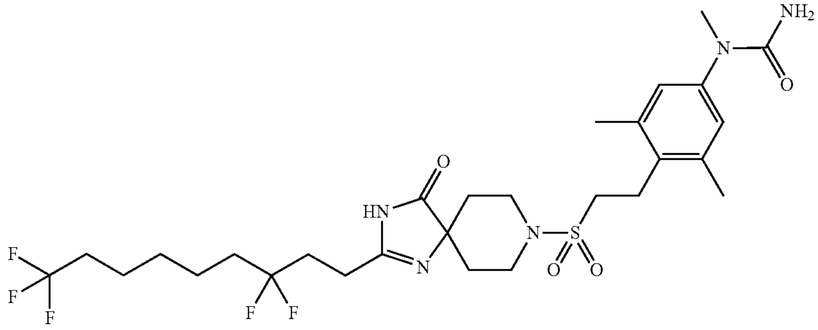 [SMILES: Cc1cc(N(C)C(N)=O)cc(C)c1CC[S@TB4](=O)(=O)N1CCC2(CC1)N=C(CCC(F)(F)CCCCCC(F)(F)F)NC2=O] | LCMS-F-1 | 0.98 | 638 (M + H)+ |
| 1148 | 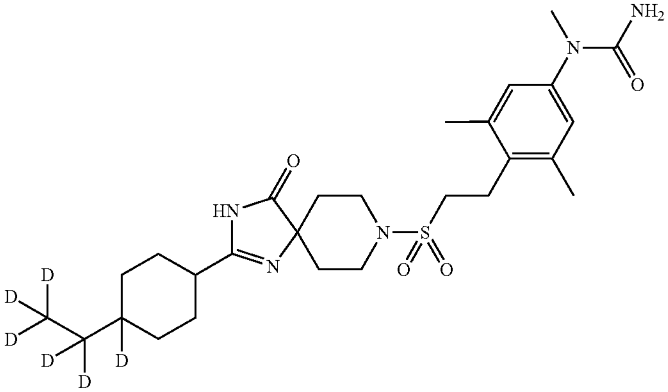 [SMILES: [2H]C([2H])([2H])C([2H])([2H])C1([2H])CCC(C2=NC3(CCN([S@TB18](=O)(=O)CCc4c(C)cc(N(C)C(N)=O)cc4C)CC3)C(=O)N2)CC1] | LCMS-F-1 | 0.97 | 538 (M + H)+ |
| 1149 | 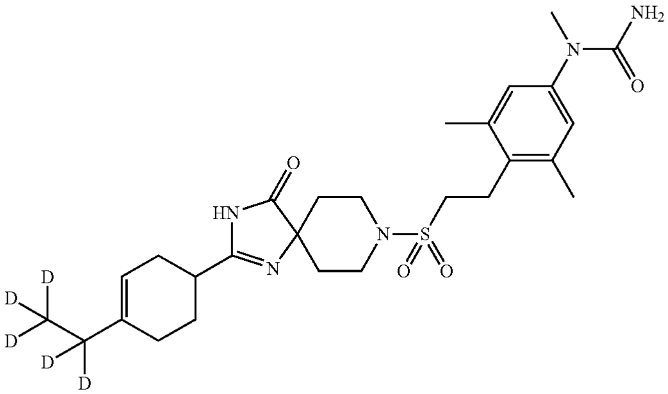 [SMILES: [2H]C([2H])([2H])C([2H])([2H])C1=CC[C@H](C2=NC3(CCN([S@TB18](=O)(=O)CCc4c(C)cc(N(C)C(N)=O)cc4C)CC3)C(=O)N2)CC1] | LCMS-F-1 | 0.95 | 535 (M + H)+ |
The carboxylic acid reagent used in the synthesis of Compound 1144 (3-(3-methyl-butyl)-benzoic acid) was synthesized by the following method.
(Reaction 277-3)
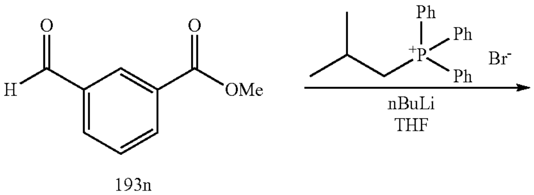
193n
-continued
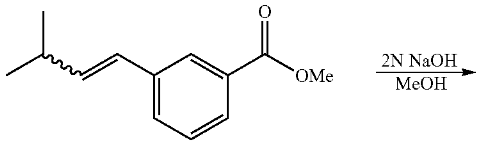
277f
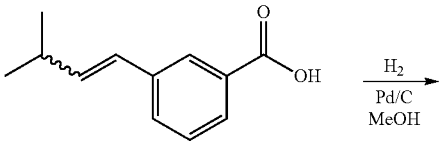
277g -continued

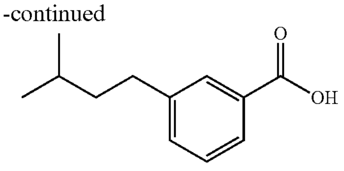

277h 3-(3-Methyl-butyl)-benzoic acid was synthesized by operations similar to those in Reaction 101-1, Reaction 95-18 and Reaction 18-2 using appropriate reagents and starting material.

MS (ESI) m/z=191 (M−H)−.

The carboxylic acid reagent used in the synthesis of Compound 1145 (3-butyl-cyclohexanecarboxylic acid) was synthesized by the following method.

(Reaction 277-4)

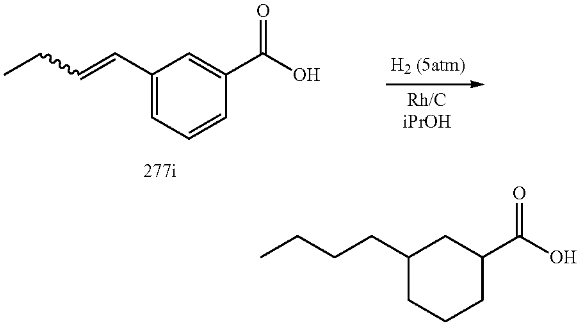

277i

277j

3-Butyl-cyclohexanecarboxylic acid was synthesized by operations similar to those in Reaction 193-3 using appropriate reagents and starting material.

$^1$H-NMR (400 MHz, $CDCl_3$) δ 0.84-2.03 (18H, m), 2.33 (0.6H, m), 2.68 (0.4H, m) (cis:trans=3:2).

The carboxylic acid reagent used in the synthesis of Compound 1146 (3-(3-methyl-butyl)-cyclohexanecarboxylic acid) was synthesized by the following method.

(Reaction 277-5)

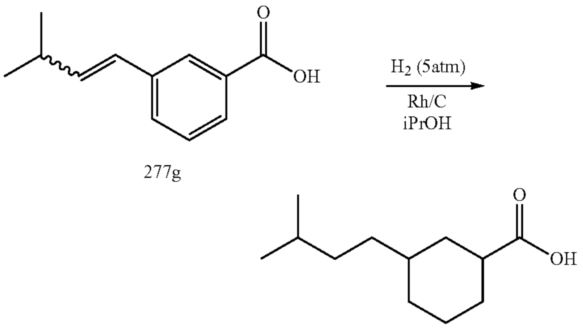

277g

277k 3-(3-Methyl-butyl)-cyclohexanecarboxylic acid was synthesized by operations similar to those in Reaction 193-3 using appropriate reagents and starting material.

$^1$H-NMR (400 MHz, $CDCl_3$) δ 0.81-2.04 (20H, m), 2.33 (0.66H, tt, J=12.0, 3.2 Hz), 2.67-2.68 (0.33H, m) (cis:trans=2:1).

The carboxylic acid reagent used in the synthesis of Compound 1147 (4,4,10,10,10-pentafluoro-decanoic acid) was synthesized by the following method.

(Reaction 277-6)

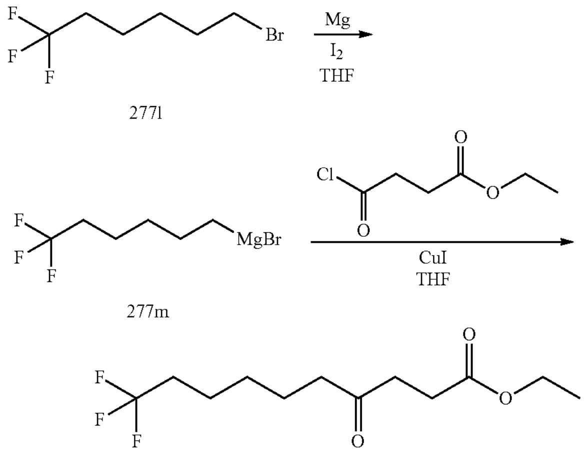

277l

277m

277n

One piece of $I_2$ was added to a solution of magnesium (204 mg, 8.40 mmol) in THF (5 ml) in a nitrogen atmosphere, and the reaction mixture was stirred at 45° C. for 20 minutes. A solution of 6-bromo-1,1,1-trifluoro-hexane (1.53 g, 7.00 mmol) in THF (2 ml) was added and the reaction mixture was stirred at 45° C. for one hour to give Compound 277m (0.875 M solution in THF).

This Compound 277m (0.875 M solution in THF, 5.71 ml, 5.00 mmol) was added dropwise to succinylethyl chloride (1.00 g, 5.00 mmol) and CuI (57.9 mg, 304 μmol) in THF (17 ml) at 0° C. The reaction mixture was stirred at 0° C. for 30 minutes. The reaction mixture was quenched with a saturated aqueous ammonium chloride solution and diluted with ethyl acetate. The organic layer was then washed with a saturated aqueous sodium bicarbonate solution, water and saturated brine, and then dried over $MgSO_4$ and concentrated under reduced pressure. The resulting residue was purified by silica gel column chromatography (hexane/ethyl acetate=100/0→80/20) to give 10,10,10-trifluoro-4-oxo-decanoic acid ethyl ester (926 mg, 69%).

MS (ESI) m/z=269 (M+H)+.

(Reaction 277-7)

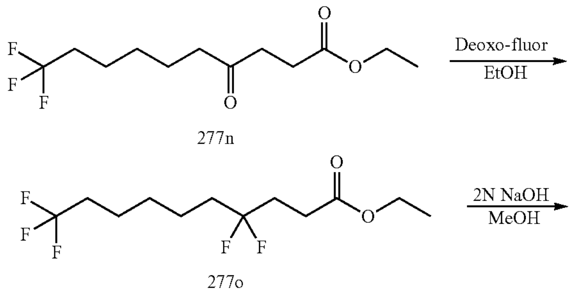

277n

277o

-continued
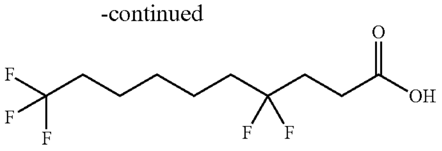
277p
4,4,10,10,10-Pentafluoro-decanoic acid was synthesized by operations similar to those in Reaction 191-11 and Reaction 95-18 using appropriate reagents and starting material.
$^1$H-NMR (400 MHz, $CDCl_3$) δ 1.41-1.45 (2H, m), 1.50-1.64 (4H, m), 1.79-1.92 (2H, m), 2.02-2.25 (4H, m), 2.58-2.62 (2H, m).
Example 278
1-(4-{2-[2-(4-Chloro-3-trifluoromethyl-phenyl)-4-oxo-1,3,8-triaza-spiro[4.5]dec-1-ene-8-sulfonyl]-ethyl}-3,5-dimethyl-phenyl)-1-methyl-urea (Compound 1150)
(Reaction 278-1)
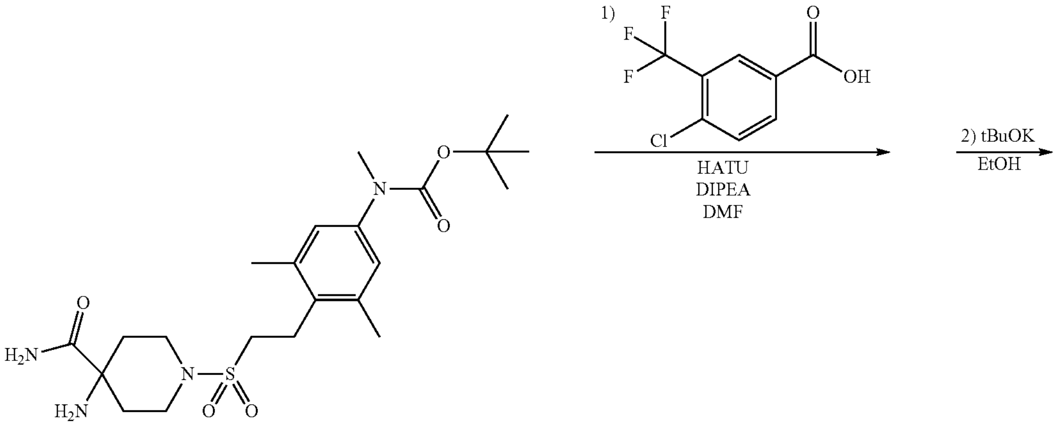
239d
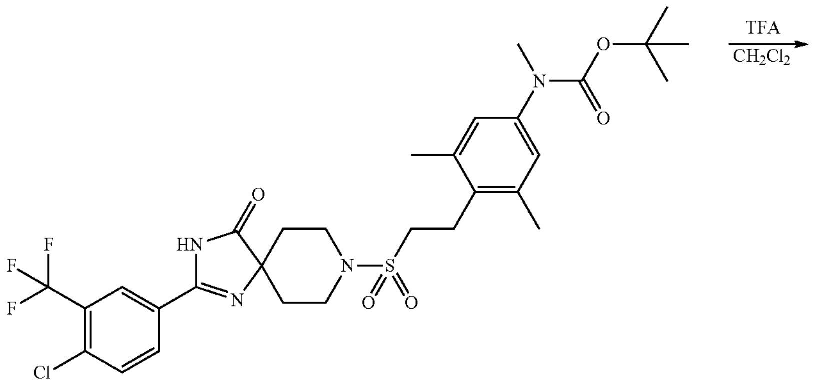
278a
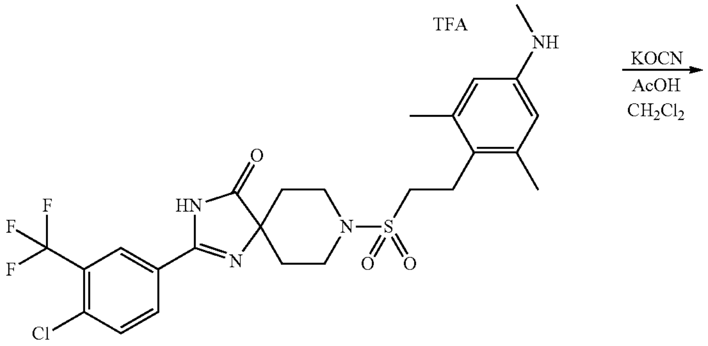
278b -continued

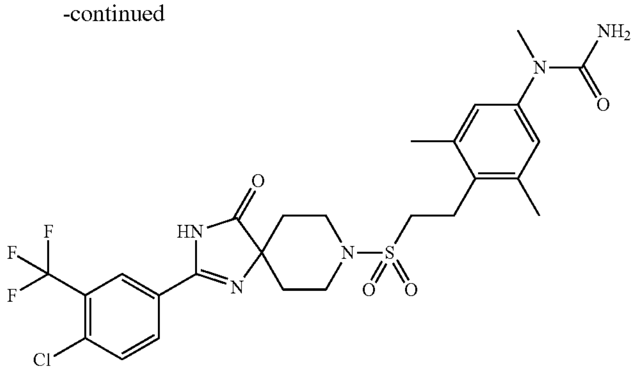

Compound 1150

1-(4-{2-[2-(4-Chloro-3-trifluoromethyl-phenyl)-4-oxo-1,3,8-triaza-spiro[4.5]dec-1-ene-8-sulfonyl]-ethyl}-3,5-dimethyl-phenyl)-1-methyl-urea was synthesized by operations similar to those in Reaction 269-1, Reaction 4-1 and Reaction 89-2 (using KOCN) using appropriate reagents and starting material.

MS (ESI) m/z=600 (M+H)+.

Example 279

1-(3,5-Dimethyl-4-{2-[4-oxo-2-(1,9,9,9-tetrafluoro-nonyl)-1,3,8-triaza-spiro[4.5]dec-1-ene-8-sulfonyl]-ethyl}-phenyl)-1-methyl-urea (Compound 1151)

(Reaction 279-1)

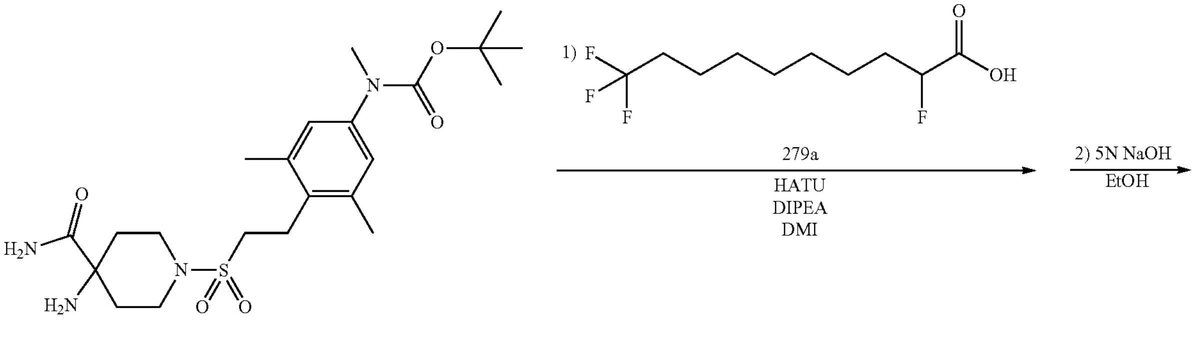

239a

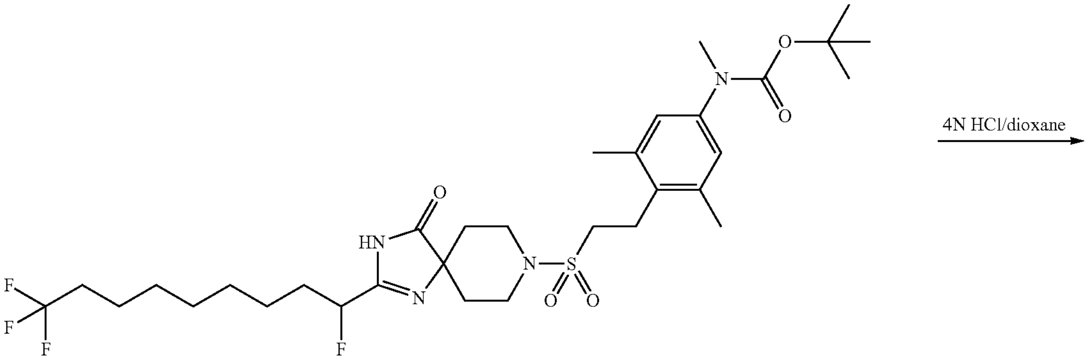

279b

-continued

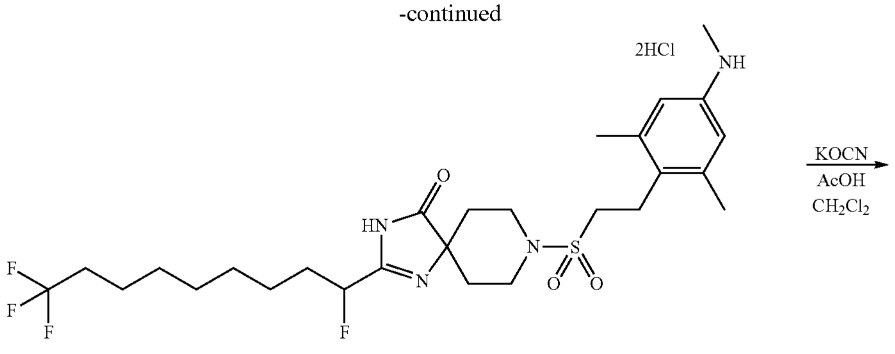

279c

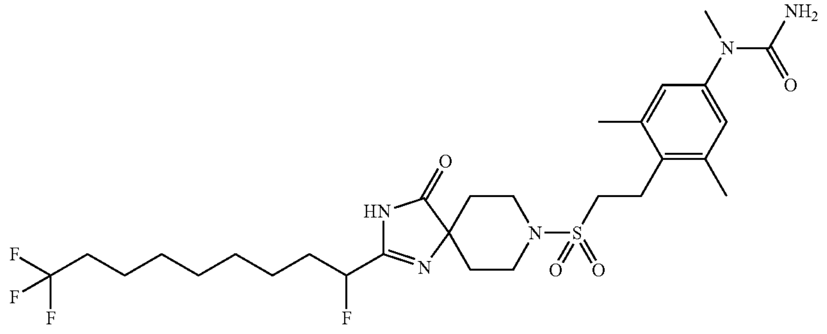

Compound 1151

1-(3,5-Dimethyl-4-{2-[4-oxo-2-(1,9,9,9-tetrafluoro-nonyl)-1,3,8-triaza-spiro[4.5]dec-1-ene-8-sulfonyl]-ethyl}-phenyl)-1-methyl-urea was synthesized by operations similar to those in Reaction 269-1, Reaction 5-3 and Reaction 89-2 (using KOCN) using appropriate reagents and starting material.

MS (ESI) m/z=620 (M+H)+.

The carboxylic acid reagent used in the synthesis of Compound 1151 (2,10,10,10-tetrafluoro-decanoic acid) was synthesized by the following method.

(Reaction 279-2)

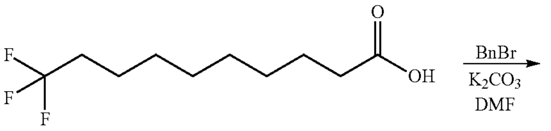

109d

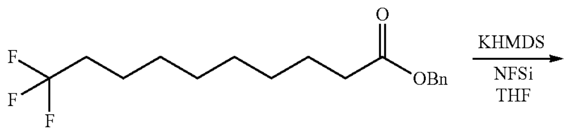

279d

-continued

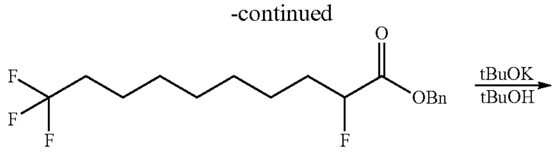

279e

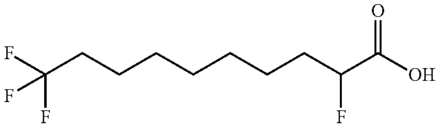

279a 2,10,10,10-Tetrafluoro-decanoic acid was synthesized by operations similar to those in Reaction 26-4, Reaction 257-1 (using KHMDS as a base) and Reaction 215-2 using appropriate reagents and starting material.

$^1$H-NMR (400 MHz, $CDCl_3$) δ 1.30-1.40 (6H, m), 1.49-1.57 (4H, m), 1.90-2.13 (4H, m), 4.97 (1H, ddd, J=48.8, 5.2, 5.2 Hz).

Example 280

1-(3,5-Dimethyl-4-{2-[4-oxo-2-(4'-propyl-biphenyl-3-yl)-1,3,8-triaza-spiro[4.5]dec-1-ene-8-sulfonyl]-ethyl}-phenyl)-1-methyl-urea (Compound 1152)

(Reaction 280-1)

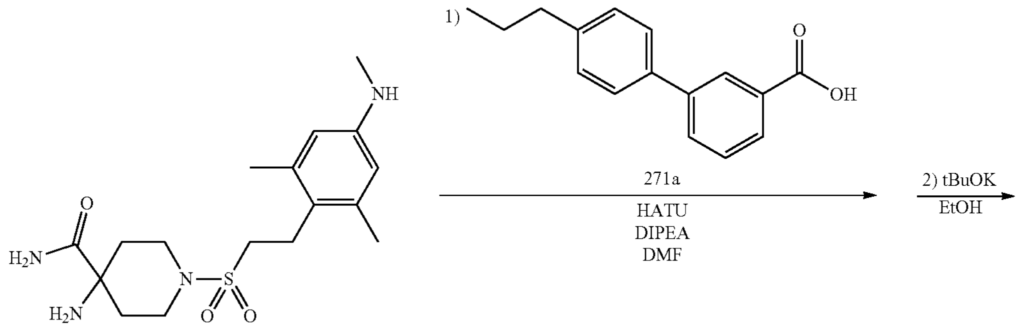

255a

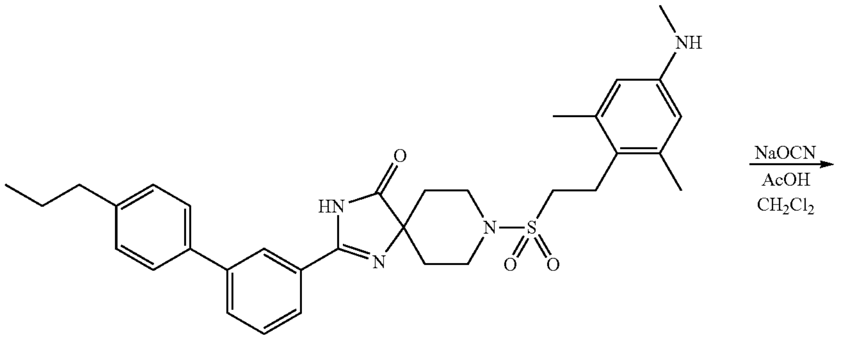

280a

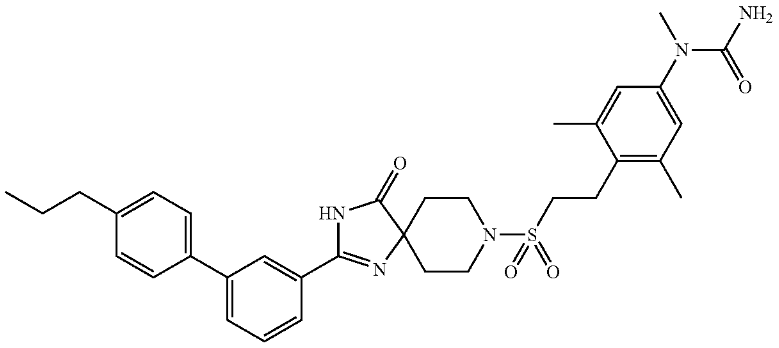

Compound 1152

1-(3,5-Dimethyl-4-{2-[4-oxo-2-(4'-propyl-biphenyl-3-yl)-1,3,8-triaza-spiro[4.5]dec-1-ene-8-sulfonyl]-ethyl}-phenyl)-1-methyl-urea was synthesized by operations similar to those in Reaction 269-1 and Reaction 89-2 using appropriate reagents and starting material.

MS (ESI) m/z=616 (M+H)+.

The example compounds shown below were synthesized by operations similar to those in Reaction 280-1 using appropriate reagents and starting materials.

Compounds 1153 to 1156
TABLE 168
| Compound | Structure | LCMS condition | Retention time (min) | MS (m/z) |
| --- | --- | --- | --- | --- |
| 1153 | 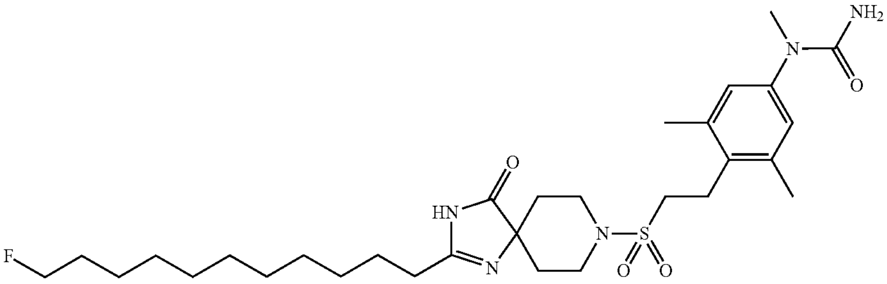 [SMILES: Cc1cc(N(C)C(N)=O)cc(C)c1CC[S@TB4](=O)(=O)N1CCC2(CC1)N=C(CCCCCCCCCCCF)NC2=O] | LCMS-F-1 | 1.08 | 594 (M + H)+ |
| 1154 | 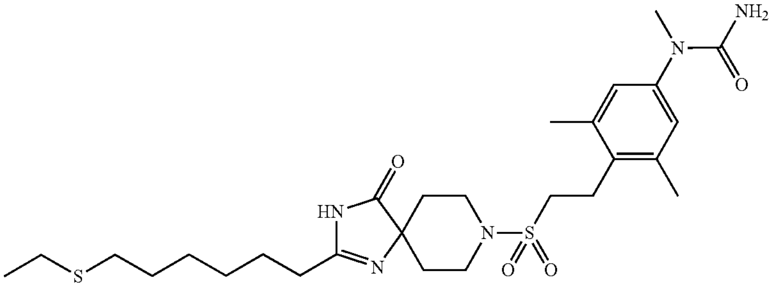 | LCMS-D-1 | 1.72 | 566 (M + H)+ |
| 1155 | 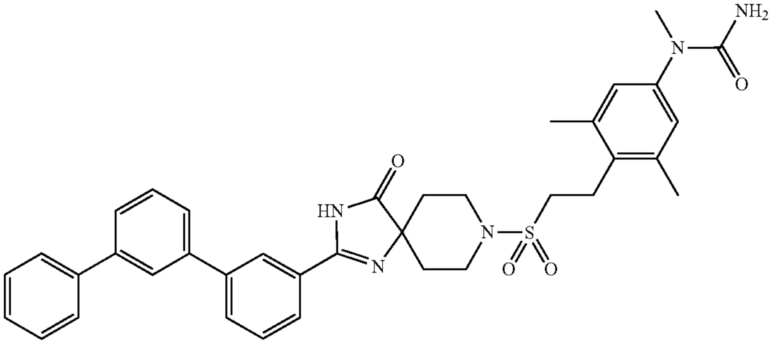 [SMILES: Cc1cc(N(C)C(N)=O)cc(C)c1CC[S@TB4](=O)(=O)N1CCC2(CC1)N=C(c1cccc(-c3cccc(-c4ccccc4)c3)c1)NC2=O] | LCMS-D-1 | 3.12 | 650 (M + H)+ |
| 1156 | 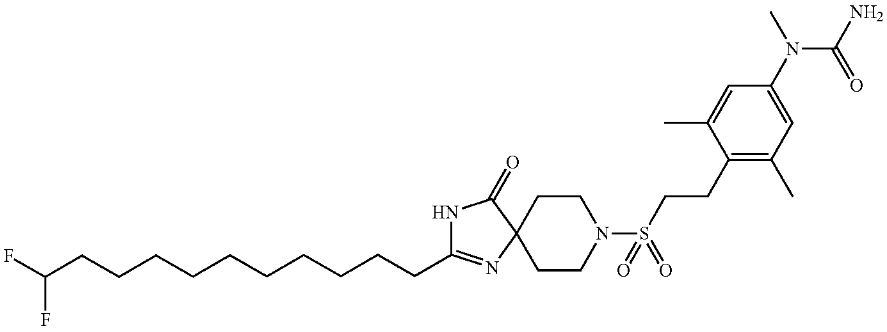 [SMILES: Cc1cc(N(C)C(N)=O)cc(C)c1CC[S@TB4](=O)(=O)N1CCC2(CC1)N=C(CCCCCCCCCCC(F)F)NC2=O] | LCMS-F-1 | 1.05 | 612 (M + H)+ |

The carboxylic acid reagent used in the synthesis of Compound 1154 (7-ethylsulfanyl-heptanoic acid) was synthesized by the following method.

(Reaction 280-2)

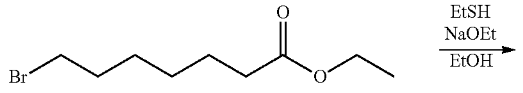

271d

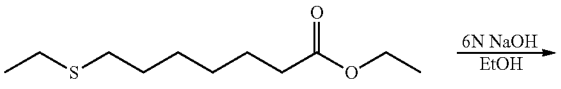

280b

-continued

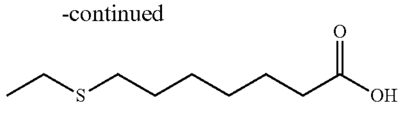

280c

7-Ethylsulfanyl-heptanoic acid was synthesized by operations similar to those in Reaction 271-10 (using NaOEt as a base) and Reaction 95-18 using appropriate reagents and starting material.

$^1$H-NMR (300 MHz, DMSO-d6) δ 1.24 (m, 3H), 1.39 (m, 4H), 1.56 (m, 4H), 2.24 (m, 2H), 2.49 (m, 4H), 12.05 (s, 1H).

Example 281

1-{3,5-Dimethyl-4-[(E)-2-(4-oxo-2-[1,1';3',1"]terphenyl-3-yl-1,3,8-triaza-spiro[4.5]dec-1-ene-8-sulfonyl)-vinyl]-phenyl}-1-methyl-urea (Compound 1157)

(Reaction 281-1)

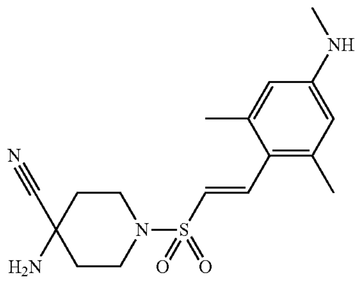

233e

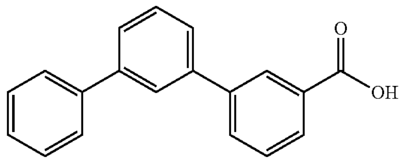

281a

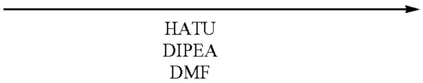

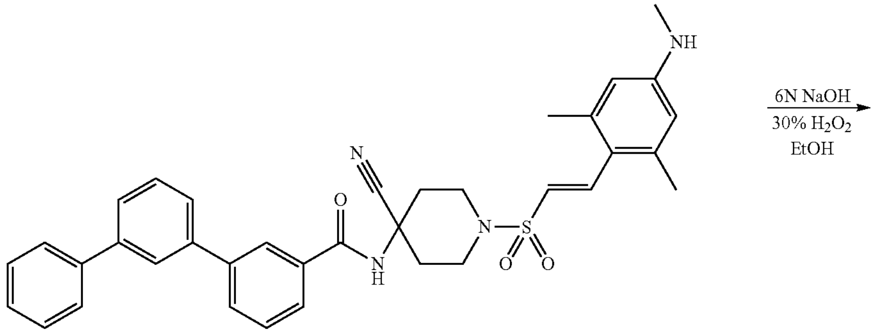

281b

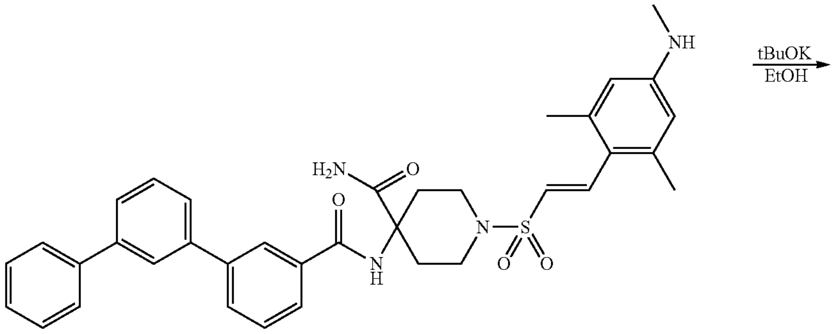

281c

-continued

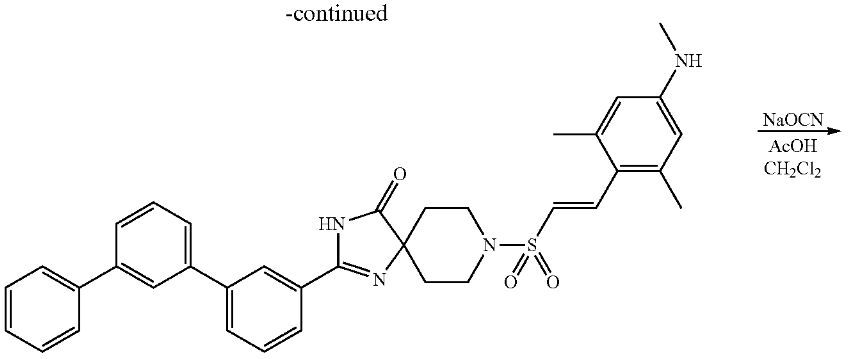

281d

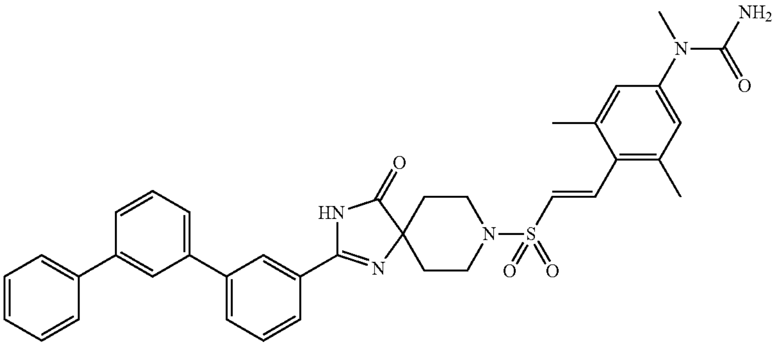

Compound 1157

1-{3,5-Dimethyl-4-[(E)-2-(4-oxo-2-[1,1';3',1"]terphenyl-3-yl-1,3,8-triaza-spiro[4.5]dec-1-ene-8-sulfonyl)-vinyl]-phenyl}-1-methyl-urea was synthesized by operations similar to those in Reaction 10-14, Reaction 10-11, Reaction 10-12 (using ethanol as a solvent) and Reaction 89-2 using appropriate reagents and starting material.

MS (ESI) m/z=648 (M+H)+.

The carboxylic acid reagent used in the synthesis of Compound 1157 ([1,1';3',1"]terphenyl-3-carboxylic acid) was synthesized by the following method.

(Reaction 281-2)

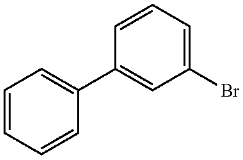

281e

+

-continued

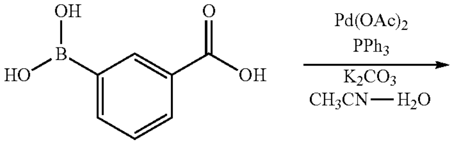

259g

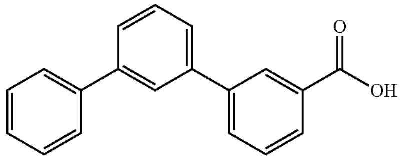

281a

[1,1';3',1"]Terphenyl-3-carboxylic acid was synthesized by operations similar to those in Reaction 259-2 using appropriate reagents and starting material.

MS (ESI) m/z=275 (M+H)+.

Example 282

8-{(E)-2-[4-(4-Hydroxy-piperidine-1-carbonyl)-2,6-dimethyl-phenyl]-ethenesulfonyl}-2-[3-(4,4,5,5,5-pentafluoro-pentyloxy)-phenyl]-1,3,8-triaza-spiro[4.5]dec-1-en-4-one (Compound 1158)

(Reaction 282-1)

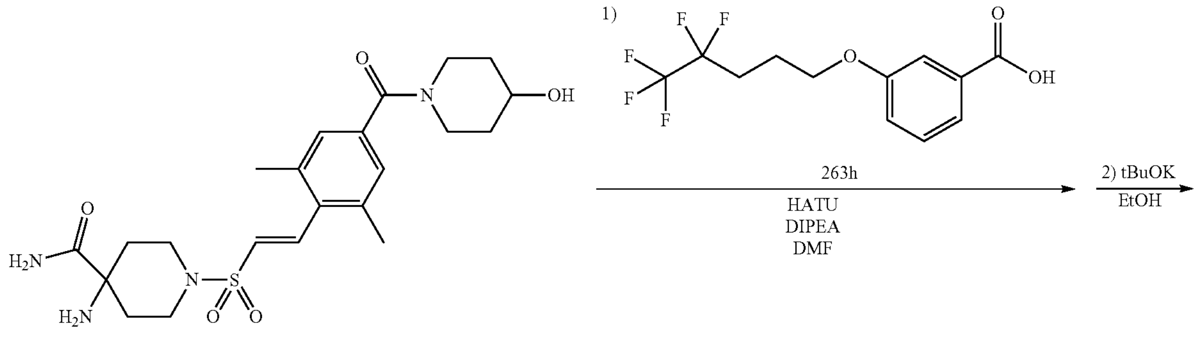

262c

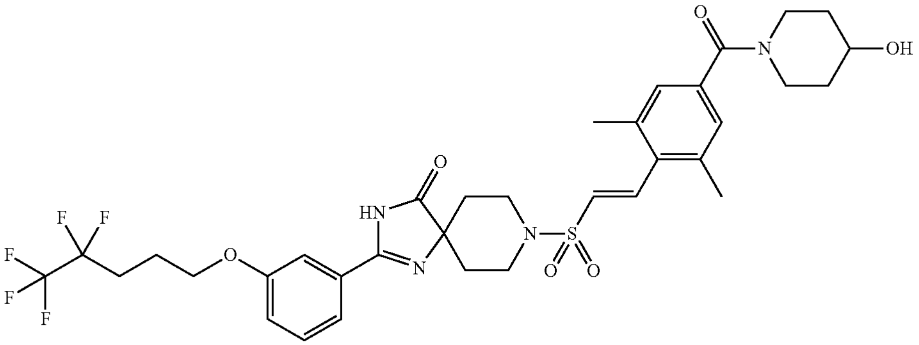

Compound 1158

8-{(E)-2-[4-(4-Hydroxy-piperidine-1-carbonyl)-2,6-dimethyl-phenyl]-ethenesulfonyl}-2-[3-(4,4,5,5,5-pentafluoro-pentyloxy)-phenyl]-1,3,8-triaza-spiro[4.5]dec-1-en-4-one was synthesized by operations similar to those in Reaction 269-1 using appropriate reagents and starting material.

MS (ESI) m/z=727 (M+H)+.

The example compounds shown below were synthesized by operations similar to those in Reaction 282-1 using appropriate reagents and starting materials.

Compounds 1159 to 1160

TABLE 169

| Compound | Structure | LCMS condition | Retention time (min) | MS (m/z) |
|---|---|---|---|---|
| 1159 | 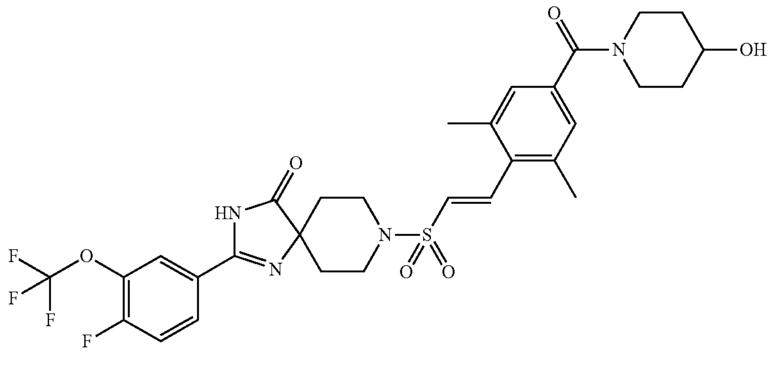 [SMILES: Cc1cc(C(=O)N2CCC(O)CC2)cc(C)c1/C=C/[S@TB4](=O)(=O)N1CCC2(CC1)N=C(c1ccc(F)c(OC(F)(F)F)c1)NC2=O] | LCMS-B-1 | 2.16 | 653 (M + H)+ |

TABLE 169-continued
| Compound | Structure | LCMS condition | Retention time (min) | MS (m/z) |
|---|---|---|---|---|
| 1160 | 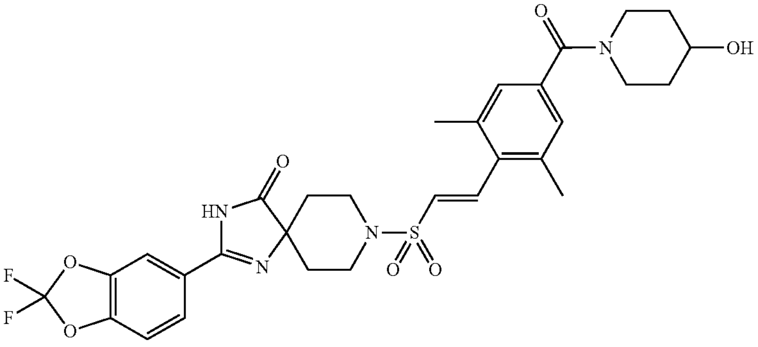 [SMILES: Cc1cc(C(=O)N2CCC(O)CC2)cc(C)c1/C=C/[S@TB4](=O)(=O)N1CCC2(CC1)N=C(c1ccc3c(c1)OC(F)(F)O3)NC2=O] | LCMS-B-1 | 2.02 | 631 (M + H)+ |
Example 283
2-(4-Fluoro-3-trifluoromethoxy-phenyl)-8-{(E)-2-[4-(4-hydroxymethyl-piperidine-1-carbonyl)-2,6-dimethyl-phenyl]-ethenesulfonyl}-1,3,8-triaza-spiro[4.5]dec-1-en-4-one (Compound 1161)
(Reaction 283-1)
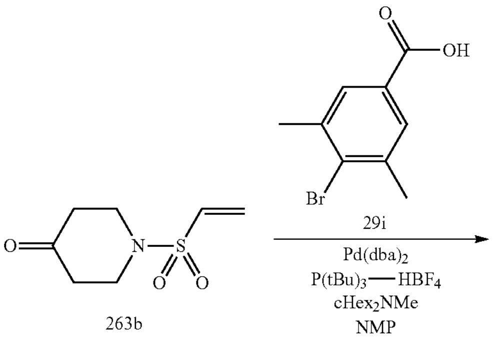
263b
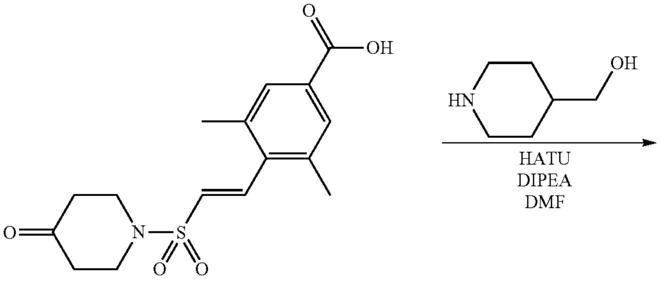
283a -continued
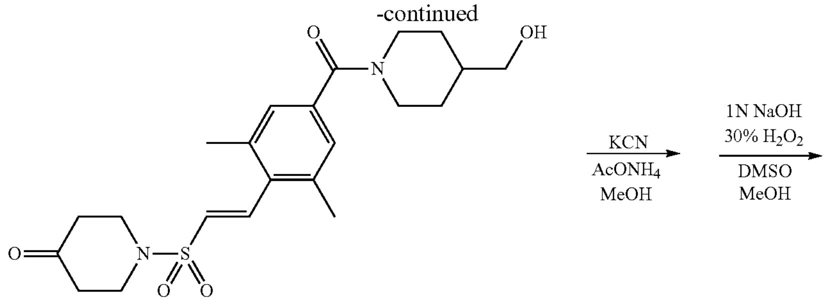
283b
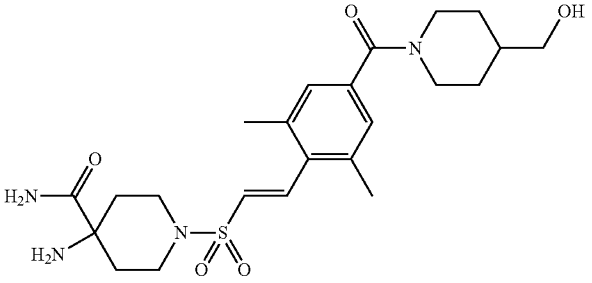
283c
4-Amino-1-{(E)-2-[4-(4-hydroxymethyl-piperidine-1-carbonyl)-2,6-dimethyl-phenyl]-ethenesulfonyl}-piperidine-4-carboxylic amide was synthesized by operations similar to those in Reaction 119-1, Reaction 10-14, Reaction 233-3 and Reaction 233-4 using appropriate reagents and starting material.
MS (ESI) m/z=479 (M+H)+.
(Reaction 283-2)
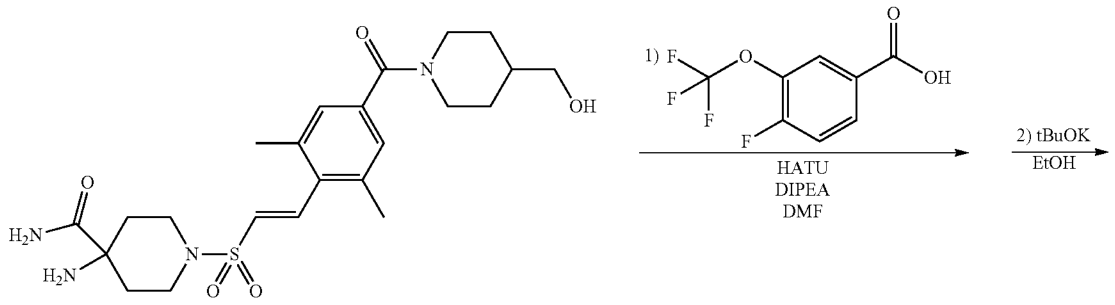
283c
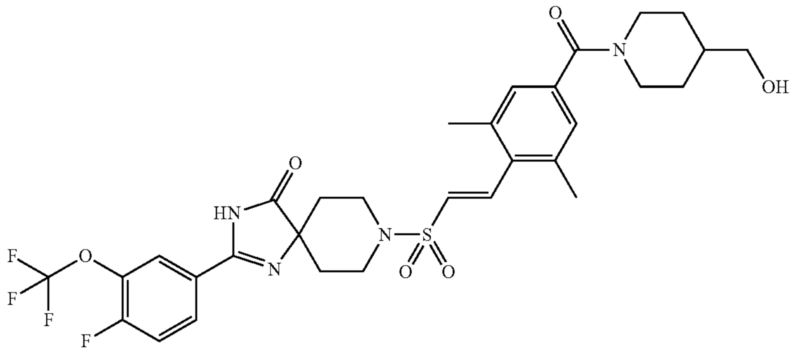
Compound 1161

2-(4-Fluoro-3-trifluoromethoxy-phenyl)-8-{(E)-2-[4-(4-hydroxymethyl-piperidine-1-carbonyl)-2,6-dimethyl-phenyl]-ethenesulfonyl}-1,3,8-triaza-spiro[4.5]dec-1-en-4-one was synthesized by operations similar to those in Reaction 269-1 using appropriate reagents and starting material.

MS (ESI) m/z=667 (M+H)+.

The example compound shown below was synthesized by operations similar to those in Reaction 283-2 using appropriate reagents and starting material.

Compound 1162

TABLE 170

| Compound | Structure | LCMS condition | Retention time (min) | MS (m/z) |
|---|---|---|---|---|
| 1162 | 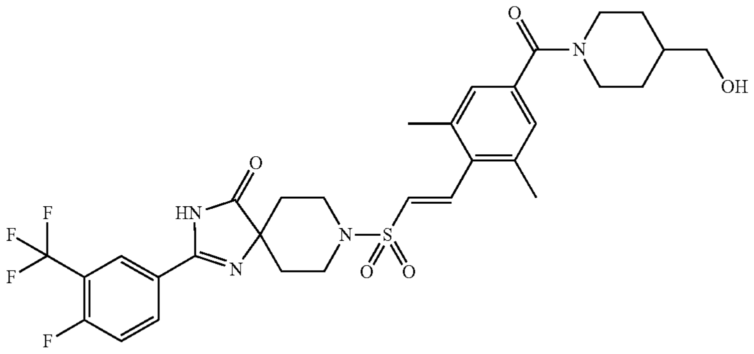 [SMILES: Cc1cc(C(=O)N2CCC(CO)CC2)cc(C)c1/C=C/[S@TB4](=O)(=O)N1CCC2(CC1)N=C(c1ccc(F)c(C(F)(F)F)c1)NC2=O] | LCQ-A-1 | 2.51 | 651 (M + H)+ |

Example 284

2-(2,2-Difluoro-benzo[1,3]dioxol-5-yl)-8-{(E)-2-[4-(4-hydroxy-4-methyl-piperidine-1-carbonyl)-2,6-dimethyl-phenyl]-ethenesulfonyl}-1,3,8-triaza-spiro[4.5]dec-1-en-4-one (Compound 1163)

(Reaction 284-1)

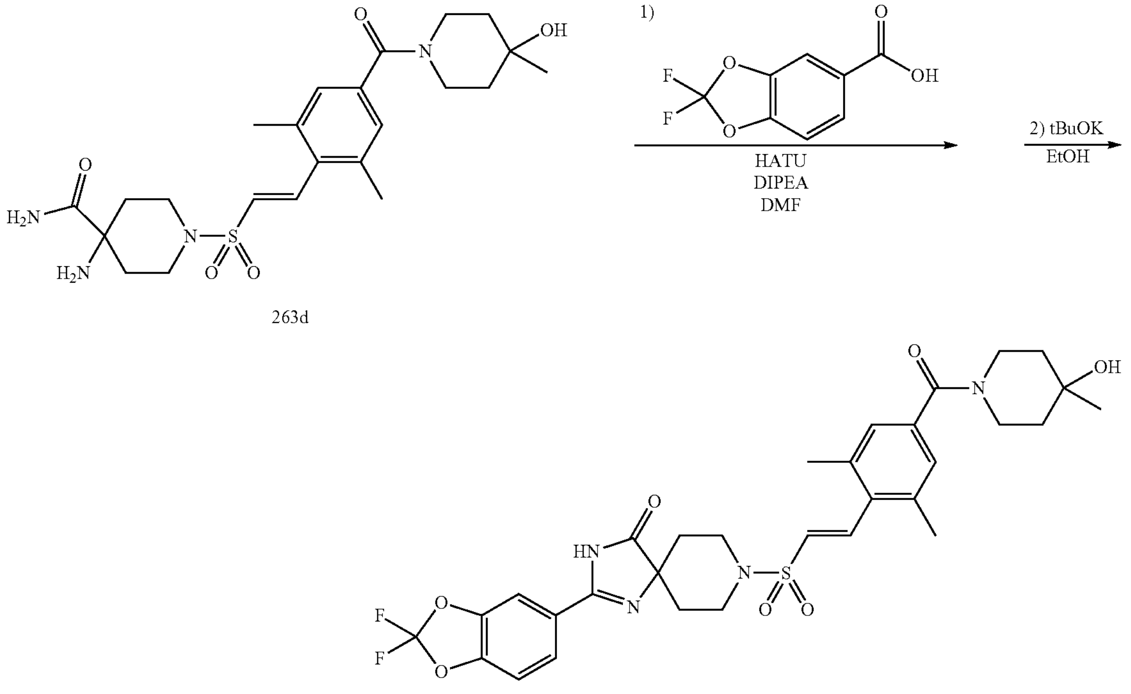

263d

Compound 1163

2-(2,2-Difluoro-benzo[1,3]dioxol-5-yl)-8-{(E)-2-[4-(4-hydroxy-4-methyl-piperidine-1-carbonyl)-2,6-dimethyl-phenyl]-ethenesulfonyl}-1,3,8-triaza-spiro[4.5]dec-1-en-4-one was synthesized by operations similar to those in Reaction 269-1 using appropriate reagents and starting material.

MS (ESI) m/z=645 (M+H)+.

Example 285

8-{(E)-2-[4-((R)-2,3-Dihydroxy-propoxy)-2,6-dimethyl-phenyl]-ethenesulfonyl}-2-(4-fluoro-3-trifluoromethoxy-phenyl)-1,3,8-triaza-spiro[4.5]dec-1-en-4-one (Compound 1164)

(Reaction 285-1)

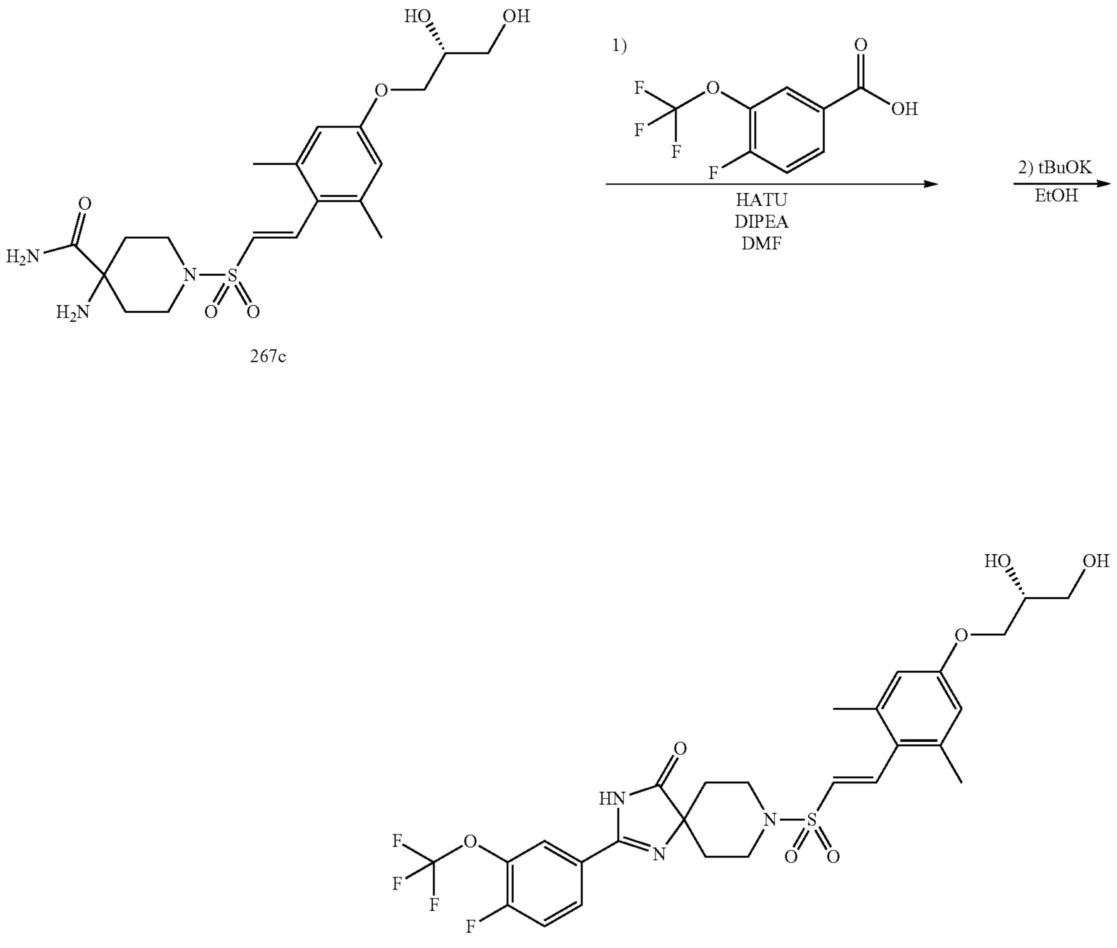

267c

Compound 1164

8-{(E)-2-[4-((R)-2,3-Dihydroxy-propoxy)-2,6-dimethyl-phenyl]-ethenesulfonyl}-2-(4-fluoro-3-trifluoromethoxy-phenyl)-1,3,8-triaza-spiro[4.5]dec-1-en-4-one was synthesized by operations similar to those in Reaction 269-1 using appropriate reagents and starting material.

MS (ESI) m/z=616 (M+H)+.

The example compound shown below was synthesized by operations similar to those in Reaction 285-1 using appropriate reagents and starting material.

Compound 1165

TABLE 171

| Compound | Structure | LCMS condition | Retention time (min) | MS (m/z) |
|---|---|---|---|---|
| 1165 | 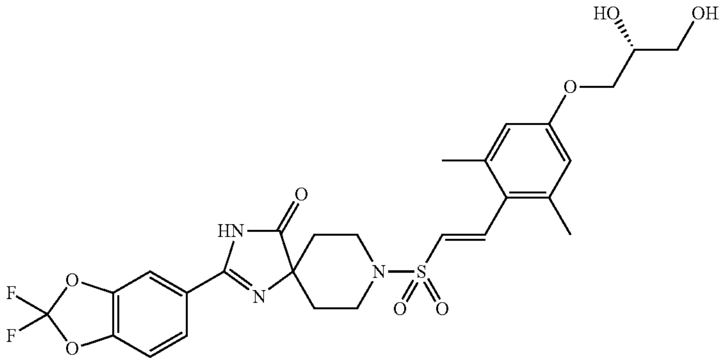 [SMILES: Cc1cc(OC[C@H](O)CO)cc(C)c1/C=C/S(=O)(=O)N1CCC2(CC1)N=C(c1ccc3c(c1)OC(F)(F)O3)NC2=O] | LCMS-F-1 | 0.94 | 594 (M + H)+ |

Example 286

8-{(E)-2-[4-(3,4-Dihydroxy-butoxy)-2-methyl-phenyl]-ethenesulfonyl}-2-(4-fluoro-3-trifluoromethoxy-phenyl)-1,3,8-triaza-spiro[4.5]dec-1-en-4-one (Compound 1166)

(Reaction 286-1)

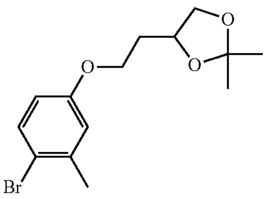

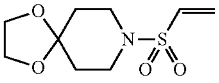

233b

28e

Pd(OAc)$_2$
(o-tolyl)$_3$P
DIPEA
DMA

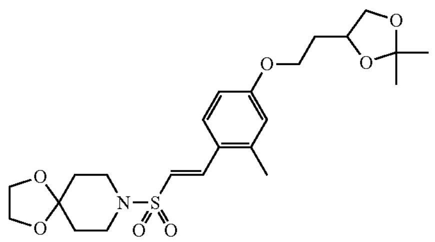

286a

TFA
acetone-$H_2O$

-continued

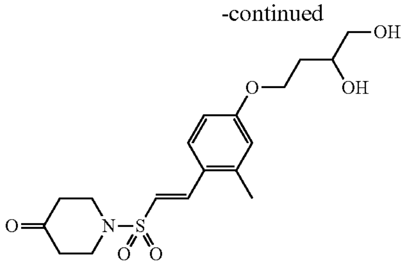

KCN
$AcONH_4$
MeOH

286b

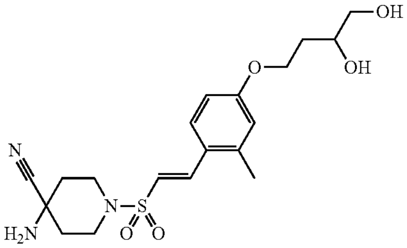

1N NaOH
30% $H_2O_2$
DMSO
MeOH

286c

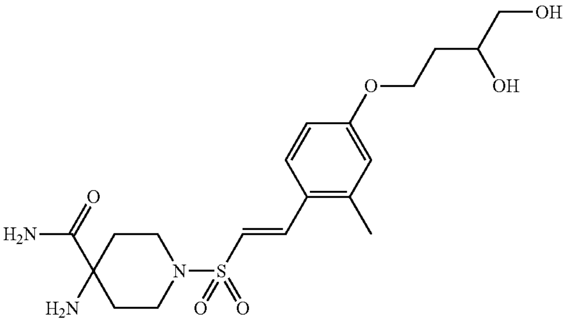

286d

4-Amino-1-{(E)-2-[4-(3,4-dihydroxy-butoxy)-2-methyl-phenyl]-ethenesulfonyl}-piperidine-4-carboxylic amide was synthesized by operations similar to those in Reaction 26-1, Reaction 233-2, Reaction 233-3 and Reaction 233-4 using appropriate reagents and starting material.

MS (ESI) m/z=428 (M+H)+.

(Reaction 286-2)

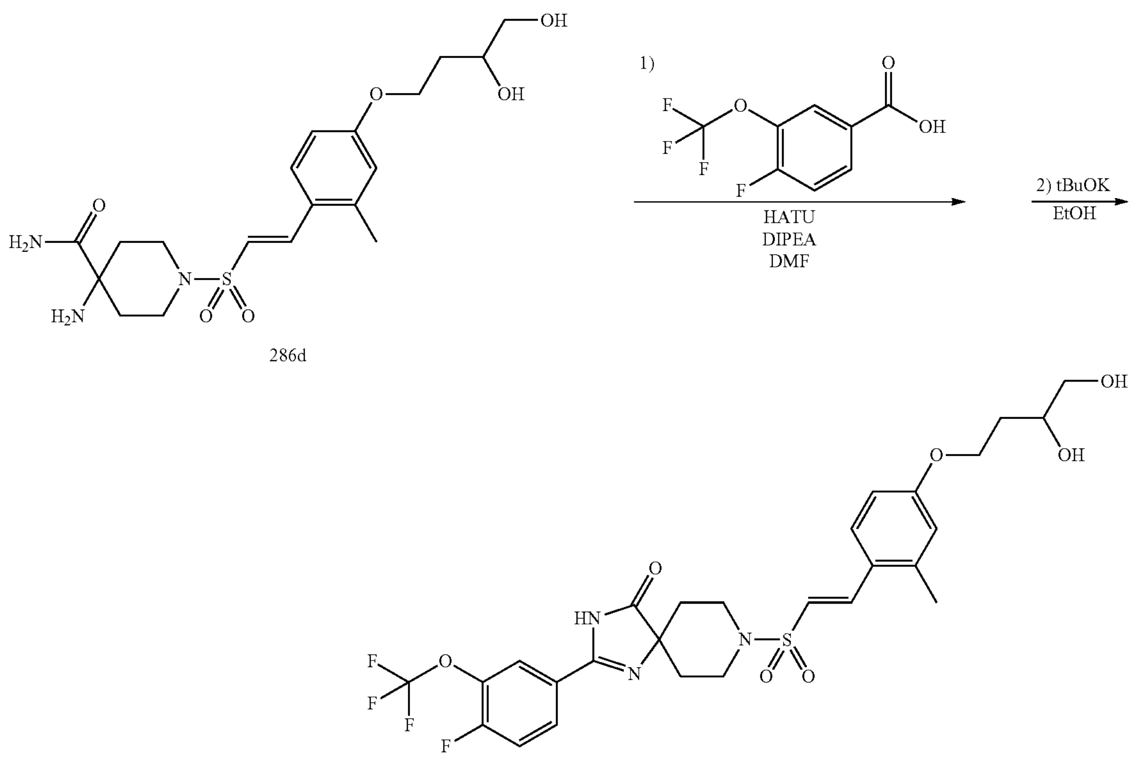

286d

Compound 1166

8-{(E)-2-[4-(3,4-Dihydroxy-butoxy)-2-methyl-phenyl]-ethenesulfonyl}-2-(4-fluoro-3-trifluoromethoxy-phenyl)-1,3,8-triaza-spiro[4.5]dec-1-en-4-one was synthesized by operations similar to those in Reaction 269-1 using appropriate reagents and starting material.

MS (ESI) m/z=616 (M+H)+.

The example compounds shown below were synthesized by operations similar to those in Reaction 286-2 using appropriate reagents and starting materials.

Compound 1167

TABLE 172

| Compound | Structure | LCMS condition | Retention time (min) | MS (m/z) |
|---|---|---|---|---|
| 1167 | 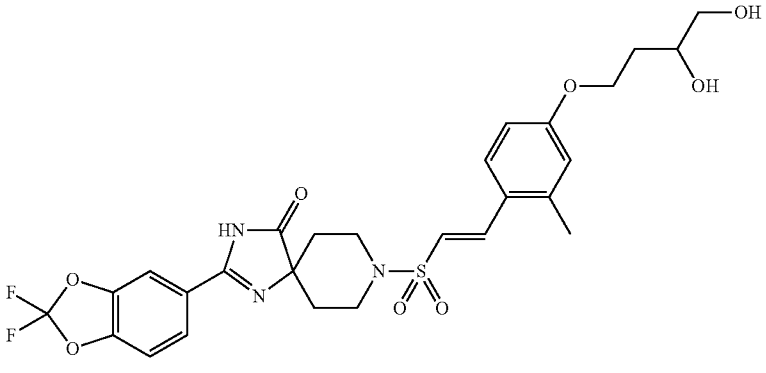 [SMILES: Cc1cc(OCCC(O)CO)ccc1/C=C/S(=O)(=O)N1CCC2(CC1)N=C(c1ccc3c(c1)OC(F)(F)O3)NC2=O] | LCMS-C-1 | 2.60 | 594 (M + H)+ |

Example 287

{4-[(E)-2-(2-Cyclohexyl-4-oxo-1,3,8-triaza-spiro[4.5]dec-1-ene-8-sulfonyl)-vinyl]-indol-1-yl}-acetic acid (Compound 1168)

(Reaction 287-1)

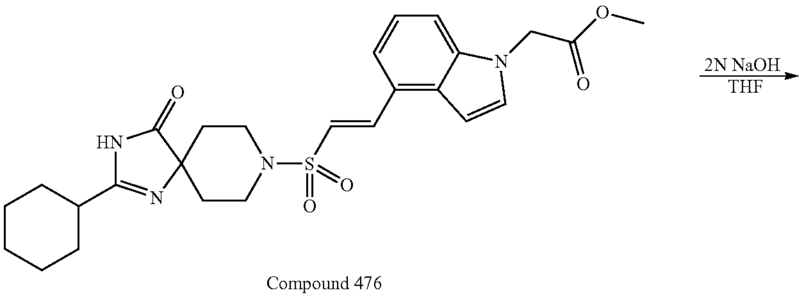

Compound 476

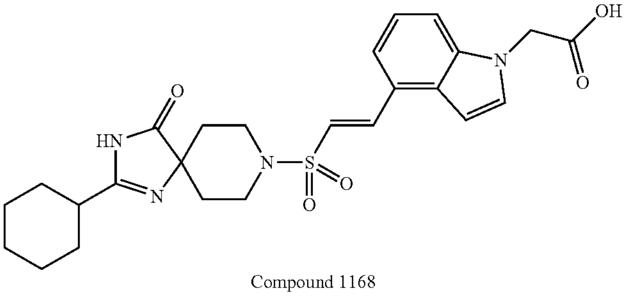

Compound 1168

{4-[(E)-2-(2-Cyclohexyl-4-oxo-1,3,8-triaza-spiro[4.5]dec-1-ene-8-sulfonyl)-vinyl]-indol-1-yl}-acetic acid (Compound 1168) was obtained by operations similar to those in Reaction 95-18 using Compound 476 as a starting material.

MS (ESI) m/z=499 (M+H)+.

The example compounds shown below were obtained by operations similar to those in Reaction 287-1 using appropriate starting compounds.

TABLE 173

| Raw material Compound | Target Compound | Structure | LCMS condition | Retention time (min) | MS (m/z) |
|---|---|---|---|---|---|
| 504 | 1169 | 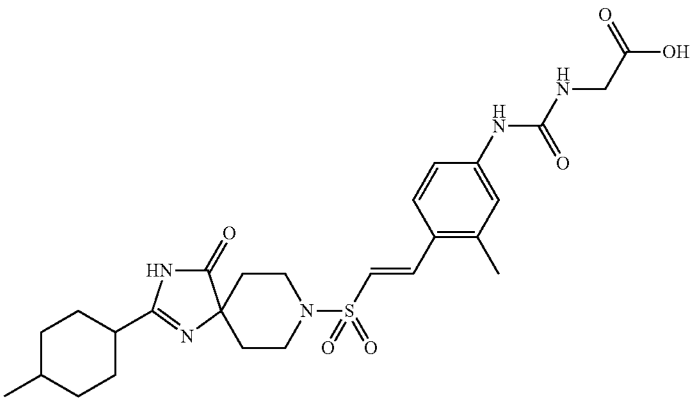 [SMILES: Cc1cc(NC(=O)NCC(=O)O)ccc1/C=C/S(=O)(=O)N1CCC2(CC1)N=C(C1CCC(C)CC1)NC2=O] | LCMS-A-1 | 1.94 | 546 (M + H)+ |

TABLE 173-continued
| Raw material Compound | Target Compound | Structure | LCMS condition | Retention time (min) | MS (m/z) |
|---|---|---|---|---|---|
| 1347 | 1170 | 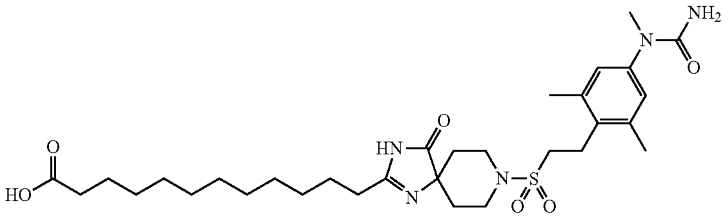 [SMILES: Cc1cc(N(C)C(N)=O)cc(C)c1CCS(=O)(=O)N1CCC2(CC1)N=C(CCCCCCCCCCCC(=O)O)NC2=O] | LCMS-C-1 | 2.52 | 620 (M + H)+ |
Example 288
10-(8-{(E)-2-[2,6-Dimethyl-4-(1-methyl-ureido)-phenyl]-ethenesulfonyl}-4-oxo-1,3,8-triaza-spiro[4.5]dec-1-en-2-yl)-decanoic acid (Compound 1171)
(Reaction 288-1)
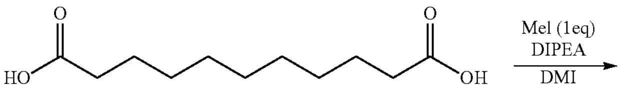
288a
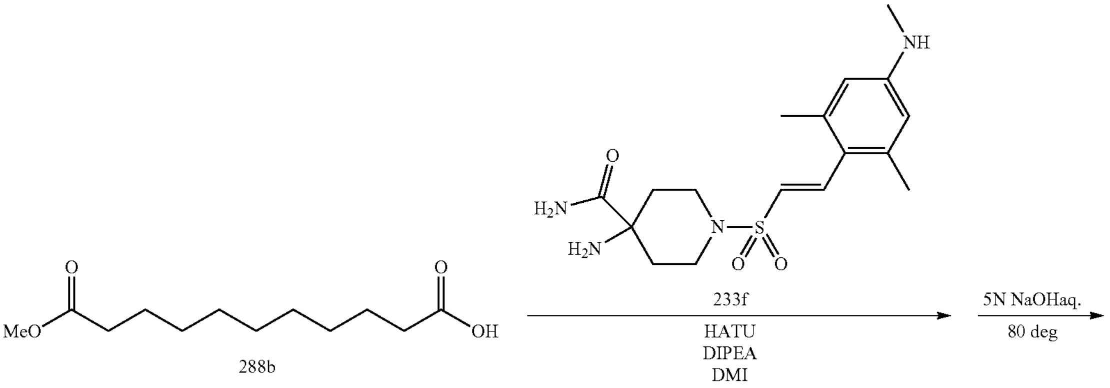
288b
233f
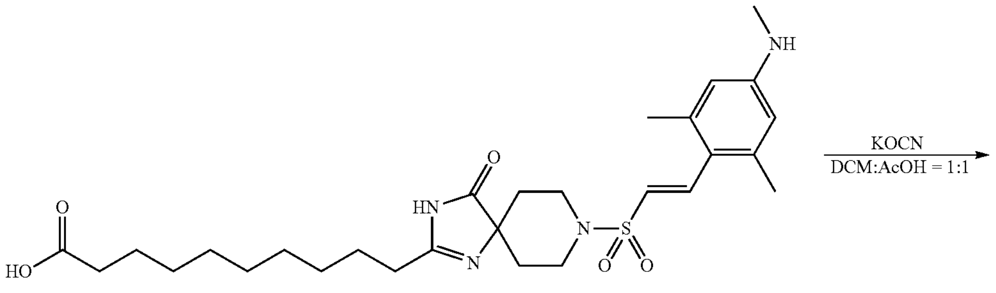
288c -continued

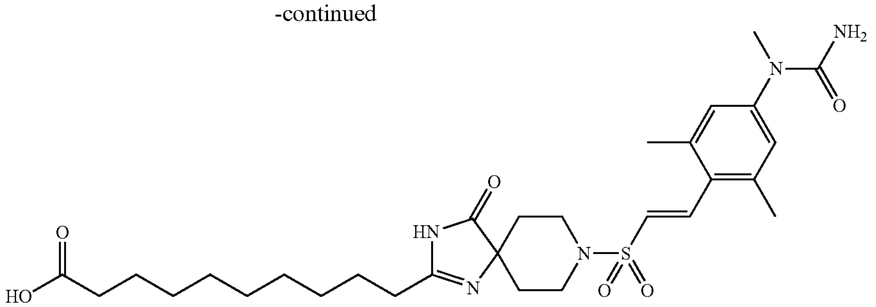

Compound 1171

10-(8-{(E)-2-[2,6-Dimethyl-4-(1-methyl-ureido)-phenyl]-ethenesulfonyl}-4-oxo-1,3,8-triaza-spiro[4.5]dec-1-en-2-yl)-decanoic acid (Compound 1171) was obtained by operations similar to those in Reaction 95-17 (using DMI as a solvent), Reaction 269-1 and Reaction 89-2 (using KOCN as a reagent) using appropriate reagents and starting material.

MS (ESI) m/z=590 (M+H)+.

Example 289

10-(8-{(E)-2-[2,6-Dimethyl-4-(1-methyl-ureido)-phenyl]-ethenesulfonyl}-4-oxo-1,3,8-triaza-spiro[4.5]dec-1-en-2-yl)-decanoic amide (Compound 1172)

(Reaction 289-1)

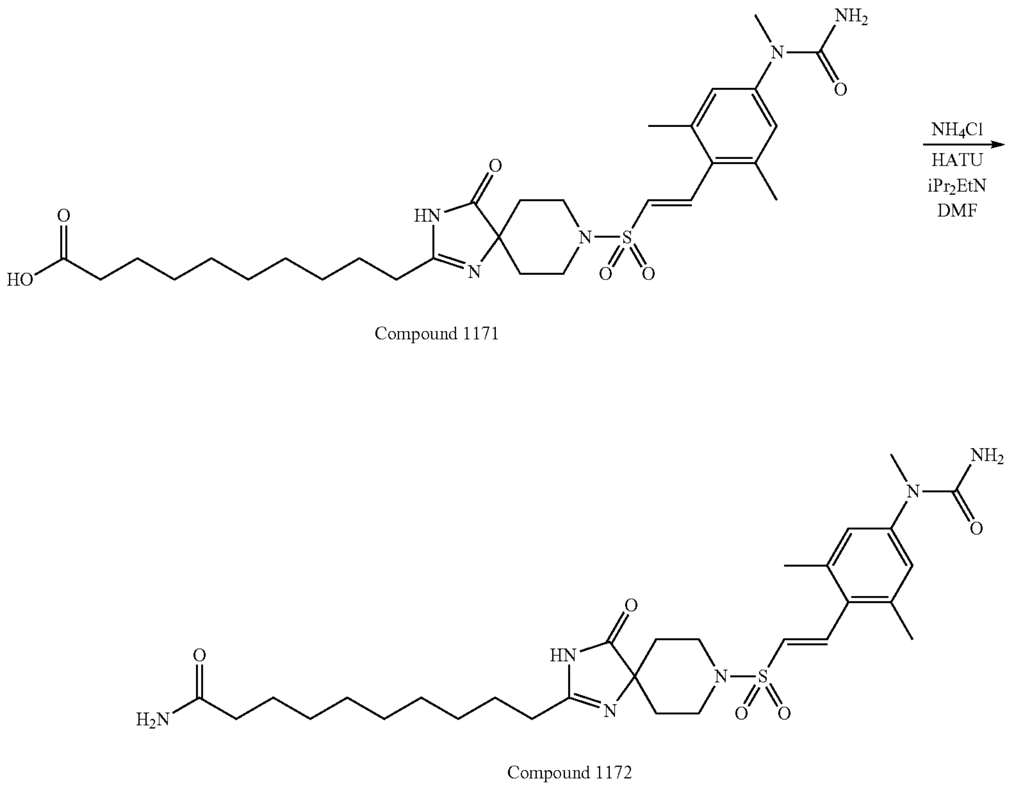

Compound 1171

Compound 1172

10-(8-{(E)-2-[2,6-Dimethyl-4-(1-methyl-ureido)-phenyl]-ethenesulfonyl}-4-oxo-1,3,8-triaza-spiro[4.5]dec-1-en-2-yl)-decanoic amide was obtained by operations similar to those in Reaction 10-14 using Compound 1171 as a starting material.

MS (ESI) m/z=589 (M+H)+.

The example compounds shown below were obtained by operations similar to those in Reaction 289-1 using appropriate starting compounds.

TABLE 174
| Raw material Compound | Target Compound | Structure | LCMS condition | Retention time (min) | MS (m/z) |
|---|---|---|---|---|---|
| 1131 | 1173 | 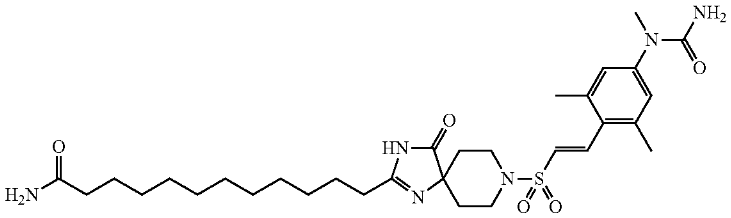 [SMILES: Cc1cc(N(C)C(N)=O)cc(C)c1/C=C/S(=O)(=O)N1CCC2(CC1)N=C(CCCCCCCCCCCC(N)=O)NC2=O] | LCMS-A-1 | 2.12 | 617 (M + H)+ |
| 1170 | 1174 | 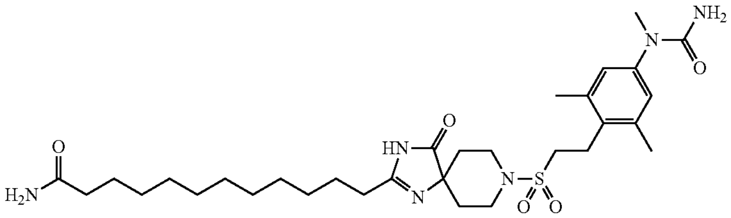 [SMILES: Cc1cc(N(C)C(N)=O)cc(C)c1CCS(=O)(=O)N1CCC2(CC1)N=C(CCCCCCCCCCCC(N)=O)NC2=O] | LCMS-A-1 | 2.10 | 619 (M + H)+ |
| 1109 | 1175 | 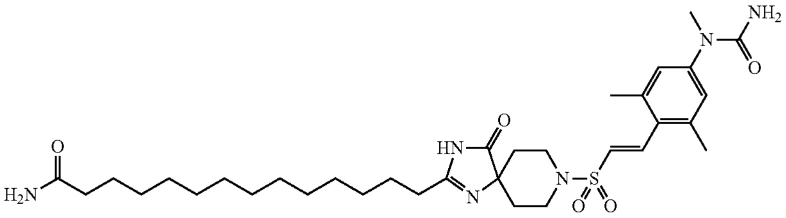 [SMILES: Cc1cc(N(C)C(N)=O)cc(C)c1/C=C/S(=O)(=O)N1CCC2(CC1)N=C(CCCCCCCCCCCCCC(N)=O)NC2=O] | LCMS-C-1 | 2.82 | 645 (M + H)+ |
| 1350 | 1176 | 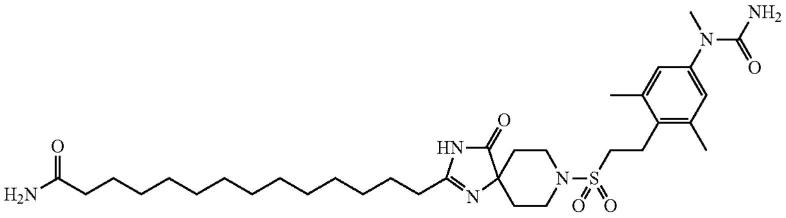 [SMILES: Cc1cc(N(C)C(N)=O)cc(C)c1CCS(=O)(=O)N1CCC2(CC1)N=C(CCCCCCCCCCCCCC(N)=O)NC2=O] | LCMS-C-1 | 2.80 | 647 (M + H)+ |
Example 290
8-[2-(2-Amino-5,7-dimethyl-benzoxazol-6-yl)-ethanesulfonyl]-2-(4-methyl-cyclohexyl)-1,3,8-triaza-spiro[4.5]dec-1-en-4-one (Compound 1178)
(Reaction 290-1)
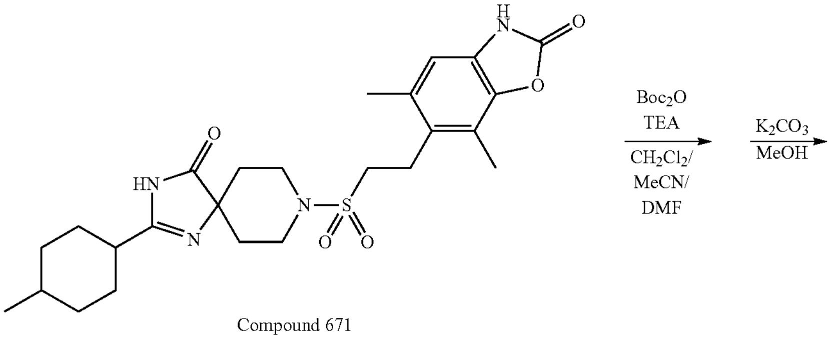
Compound 671

-continued

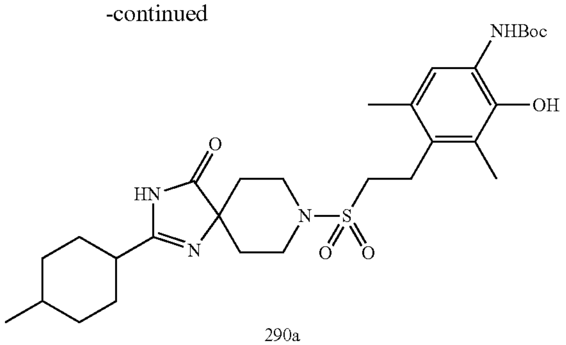

290a

Triethylamine (34.7 μL, 249 μmol) and di-tert-butyl dicarbonate (32.6 mg, 149 μmol) were added to a solution of 8-[2-(5,7-dimethyl-2-oxo-2,3-dihydro-benzoxazol-6-yl)-ethanesulfonyl]-2-(4-methyl-cyclohexyl)-1,3,8-triaza-spiro[4.5]dec-1-en-4-one (25 mg, 49.7 μmol) in dichloromethane/acetonitrile/DMF (1:1:1) (1.0 mL) at room temperature, and the mixture was stirred at room temperature for three hours. The reaction solution was concentrated under reduced pressure, and the resulting residue was dissolved in methanol (1.0 mL) without purification. Potassium carbonate (34.3 mg, 249 μmol) was added to the solution, and the mixture was stirred at room temperature for two hours. $H_2O$ (3 mL) was added, followed by extraction with dichloromethane (10 mL) twice. The organic layers were dried over sodium sulfate and concentrated under reduced pressure. The resulting residue was purified by PTLC ($CH_2Cl_2$-MeOH) to give (2-hydroxy-3,5-dimethyl-4-{2-[2-(4-methyl-cyclohexyl)-4-oxo-1,3,8-triaza-spiro[4.5]dec-1-ene-8-sulfonyl]-ethyl}-phenyl)-carbamic acid tert-butyl ester as a yellow substance (7.0 mg, 24%).

MS (ESI) m/z=577, 579 (M+H)+.

A mixed solution of (2-hydroxy-3,5-dimethyl-4-{2-[2-(4-methyl-cyclohexyl)-4-oxo-1,3,8-triaza-spiro[4.5]dec-1-ene-8-sulfonyl]-ethyl}-phenyl)-carbamic acid tert-butyl ester (7.0 mg, 12.1 μmol) and dichloromethane/TFA (2:1) (750 μL) was prepared and stirred at room temperature for one hour. The reaction solution was concentrated under reduced pressure, and the resulting residue was dissolved in ethanol (1.00 mL) without purification. Bromocyanide (3.9 mg, 36.3 μmol) and sodium bicarbonate (6.1 mg, 72.6 μmol) were added to the solution, and the mixture was stirred at room temperature for five hours. $H_2O$ (2 mL) were added, followed by extraction with ethyl acetate (10 mL) twice. The organic layers were dried over sodium sulfate and concentrated under reduced pressure. The resulting residue was purified by PTLC ($CH_2Cl_2$-MeOH-DMF) to give 8-[2-(2-amino-5,7-dimethyl-benzoxazol-6-yl)-ethanesulfonyl]-2-(4-methyl-cyclohexyl)-1,3,8-triaza-spiro[4.5]dec-1-en-4-one as a yellow substance (0.7 mg, 9%).

$^1$H-NMR (400 MHz, $CDCl_3$) δ 0.87 (3H, d, J=8.0 Hz), 0.85-1.01 (2H, m), 1.20-1.52 (5H, m), 1.68-1.78 (4H, br-m), 1.82-1.90 (2H, br-m), 2.24 (1H, tt, J=3.6, 12.0 Hz), 2.31 (3H, s), 2.33 (3H, s), 2.90-3.06 (2H, br-m), 3.11-3.19 (2H, br-m), 3.20-3.38 (2H, br-m), 3.60-3.68 (2H, br-m), 6.87 (1H, s), 7.24 (2H, s), 10.83 (1H, s).

(Reaction 290-2)

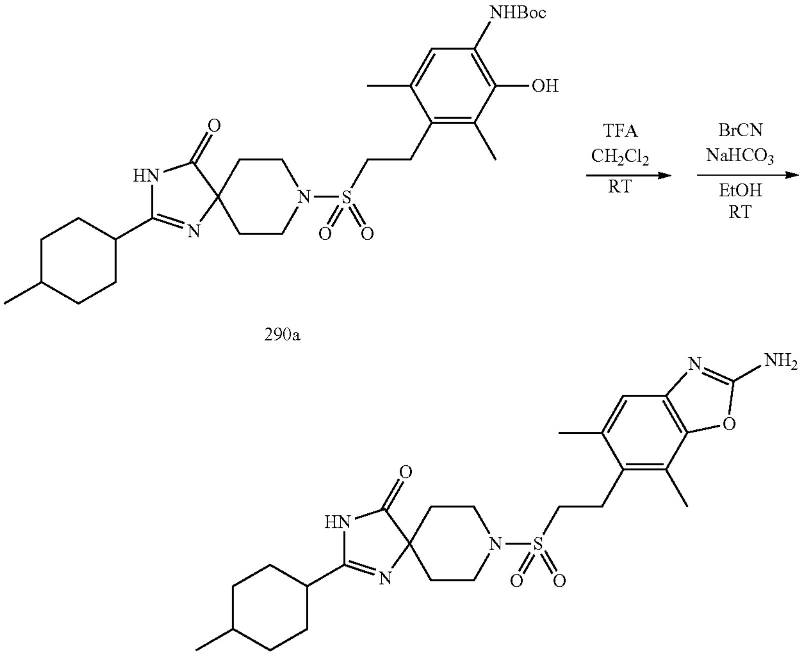

Compound 1178

Example 291

2-Cyclohexyl-8-{2-[2,6-dimethyl-4-(2-oxo-oxazolidine-3-carbonyl)-phenyl]-ethanesulfonyl}-1,3,8-triaza-spiro[4.5]dec-1-en-4-one (Compound 1179)

(Reaction 291-1)

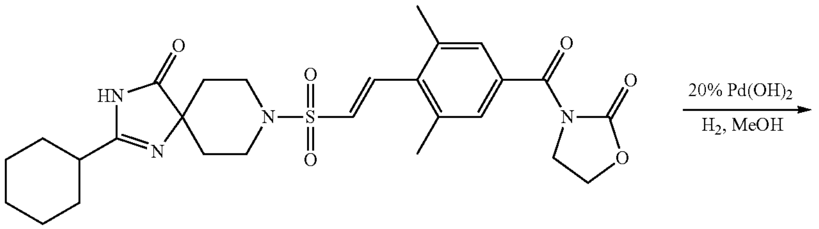

Compound 1007

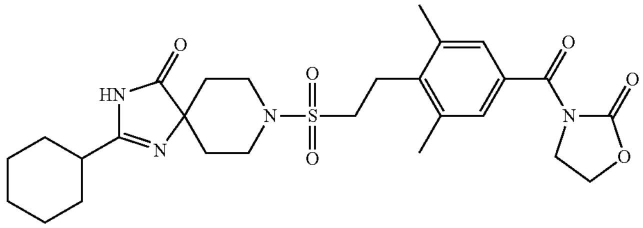

Compound 1179

2-Cyclohexyl-8-{2-[2,6-dimethyl-4-(2-oxo-oxazolidine-3-carbonyl)-phenyl]-ethanesulfonyl}-1,3,8-triaza-spiro[4.5]dec-1-en-4-one (Compound 1179) was obtained by operations similar to those in Reaction 122-2 using Compound as a starting material.

MS (ESI) m/z=545 (M+H)+.

The example compounds shown below were obtained by operations similar to those in Reaction 291-1 using appropriate solvents (acetonitrile or methanol or an acetonitrile-methanol mixed solution) and starting compounds.

TABLE 175

| Raw material Compound | Target Compound | Structure | LCMS condition | Retention time (min) | MS (m/z) |
|---|---|---|---|---|---|
| 998 | 1180 | 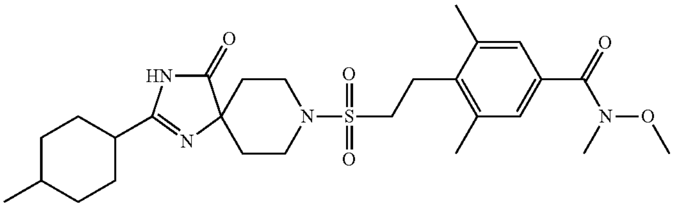 | LCMS-D-1 | 2.02 | 533 (M + H)+ |
| 992 | 1181 | 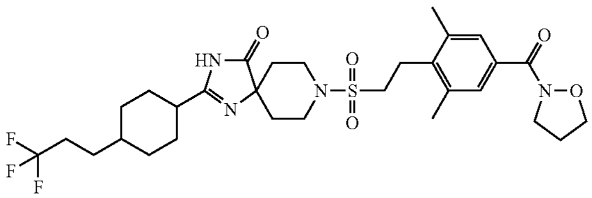 [SMILES: Cc1cc(C(=O)N2CCCO2)cc(C)c1CCS(=O)(=O)N1CCC2(CC1)N=C(C1CCC(CCC(F)(F)F)CC1)NC2=O] | LCMS-D-1 | 2.77 | 627 (M + H)+ |
| 1001 | 1182 | 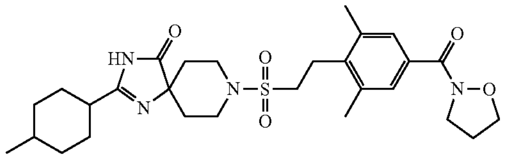 [SMILES: Cc1cc(C(=O)N2CCCO2)cc(C)c1CCS(=O)(=O)N1CCC2(CC1)N=C(C1CCC(C)CC1)NC2=O] | LCMS-D-1 | 1.93 | 545 (M + H)+ |

TABLE 175-continued

| Raw material Compound | Target Compound | Structure | LCMS condition | Retention time (min) | MS (m/z) |
|---|---|---|---|---|---|
| 1002 | 1183 | 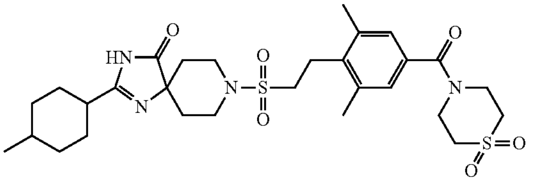 [SMILES: Cc1cc(C(=O)N2CCS(=O)(=O)CC2)cc(C)c1CCS(=O)(=O)N1CCC2(CC1)N=C(C1CCC(C)CC1)NC2=O] | LCMS-D-1 | 1.72 | 607 (M + H)+ |
| 1010 | 1184 | TFA 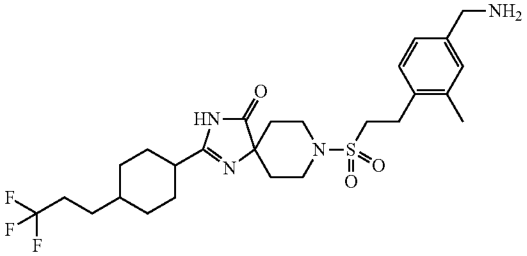 | LCMS-D-1 | 2.31 | 731 (M + H)+ |

Example 292

2-(3,4-Dichloro-phenyl)-8-{(E)-2-[4-(4-hydroxy-4-methyl-piperidine-1-carbonyl)-2,6-dimethyl-phenyl]-ethenesulfonyl}-1,3,8-triaza-spiro[4.5]dec-1-en-4-one (Compound 1185)

(Reaction 292-1)

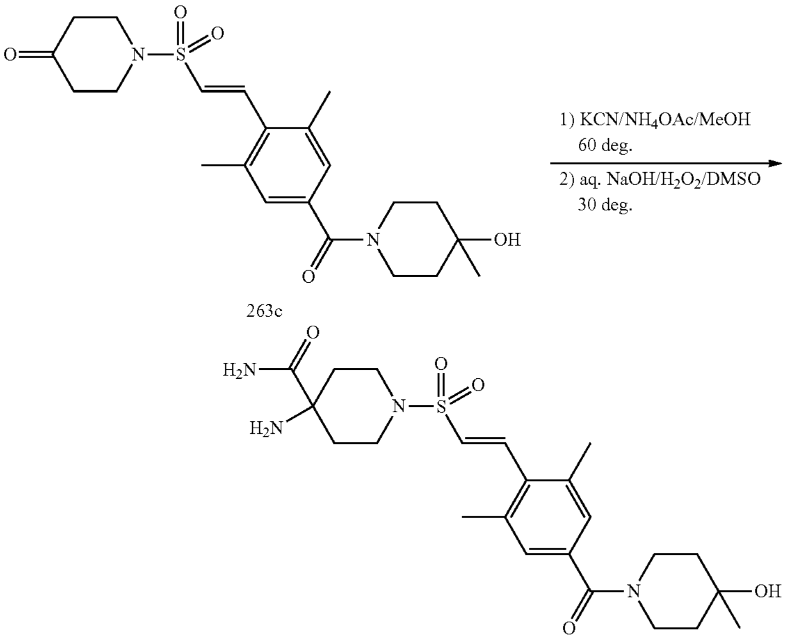

263c

263d

4-Amino-1-{(E)-2-[4-(4-hydroxy-4-methyl-piperidine-1-carbonyl)-2,6-dimethyl-phenyl]-ethenesulfonyl}-piperidine-4-carboxylic amide was obtained by operations similar to those in Reaction 233-3 and Reaction 233-4 using appropriate reagents and starting material.

MS (ESI) m/z=479 (M+H)+.

(Reaction 292-2)

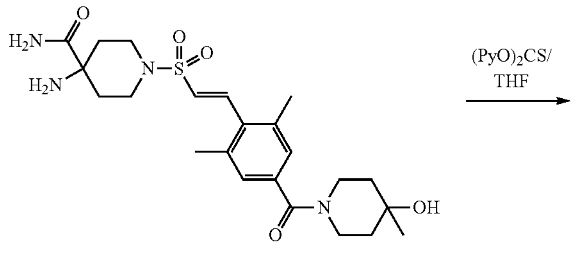

263d

Di(2-pyridyl)thionocarbonate (0.97 g, 4.2 mmol) was added to a solution of 4-amino-1-{(E)-2-[4-(4-hydroxy-4-methyl-piperidine-1-carbonyl)-2,6-dimethyl-phenyl]-ethenesulfonyl}-piperidine-4-carboxylic amide (1.82 g, 3.8 mmol) in THF (7.6 ml), and the mixture was stirred at 50° C. for one hour. The reaction mixture was purified by column chromatography (amine-loaded silica gel, dichloromethane/methanol=99:1→88:12) to give 8-{(E)-2-[4-(4-hydroxy-4-methyl-piperidine-1-carbonyl)-2,6-dimethyl-phenyl]-ethenesulfonyl}-2-thioxo-1,3,8-triaza-spiro[4.5]decan-4-one as a colorless solid (1.55 g, 78%).

MS (ESI) m/z=521 (M+H)+.

(Reaction 292-3)

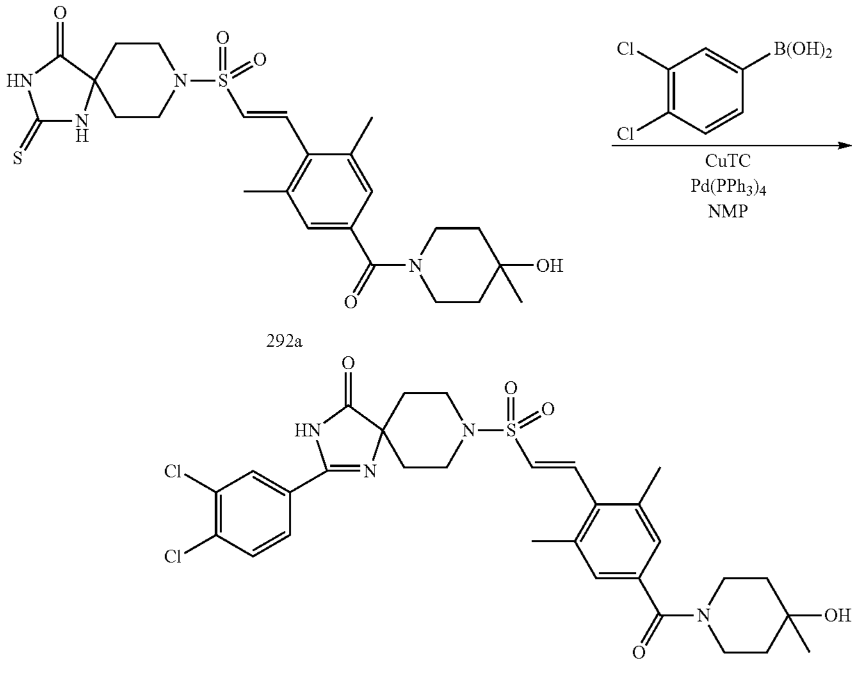

292a

Compound 1185

-continued

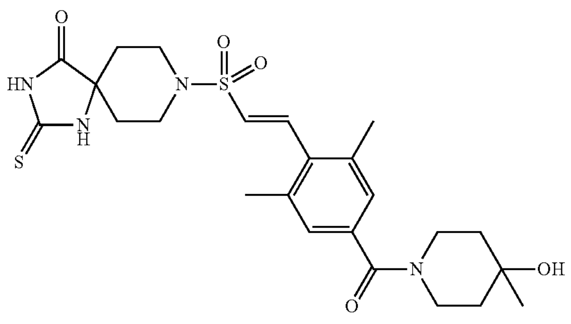

292a

A solution of 8-{(E)-2-[4-(4-hydroxy-4-methyl-piperidine-1-carbonyl)-2,6-dimethyl-phenyl]-ethenesulfonyl}-2-thioxo-1,3,8-triaza-spiro[4.5]decan-4-one (25 mg, 0.048 mmol), 3,4-dichlorophenylboronic acid (27.5 mg, 0.144 mmol), palladium tetrakistriphenylphosphine (11.1 mg, 0.0096 mmol) and CuTC (36.8 mg, 0.192 mmol) in NMP (0.1 mL) was heated with stirring at 80° C. for 30 minutes in a nitrogen atmosphere. After cooling to room temperature, N-acetylcysteine (33 mg, 0.2 mmol) was added to the reaction mixture. The reaction mixture was purified by silica gel column chromatography (NH silica gel, methylene chloride: methanol=100:0→90:10) to give 2-(3,4-dichloro-phenyl)-8-{(E)-2-[4-(4-hydroxy-4-methyl-piperidine-1-carbonyl)-2,6-dimethyl-phenyl]-ethenesulfonyl}-1,3,8-triaza-spiro[4.5]dec-1-en-4-one as a white solid (13.4 mg, 44%).

MS (ESI) m/z=633 (M+H)+.

The example compounds shown below were obtained by operations similar to those in Reaction 292-3 using appropriate starting compounds.

Compounds 1186 to Compound 1238
TABLE 176
| Target Compound | Structure | LCMS condition | Retention time (min) | MS (m/z) |
| --- | --- | --- | --- | --- |
| 1186 | 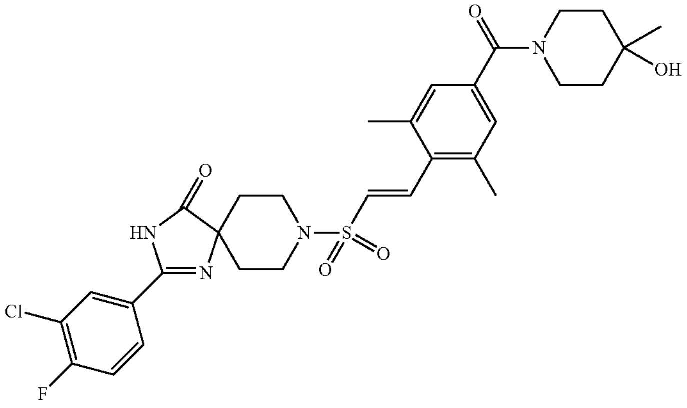 [SMILES: Cc1cc(C(=O)N2CCC(C)(O)CC2)cc(C)c1/C=C/S(=O)(=O)N1CCC2(CC1)N=C(c1ccc(F)c(Cl)c1)NC2=O] | LCMS-F-2 | 0.72 | 617 (M + H)+ |
| 1187 | 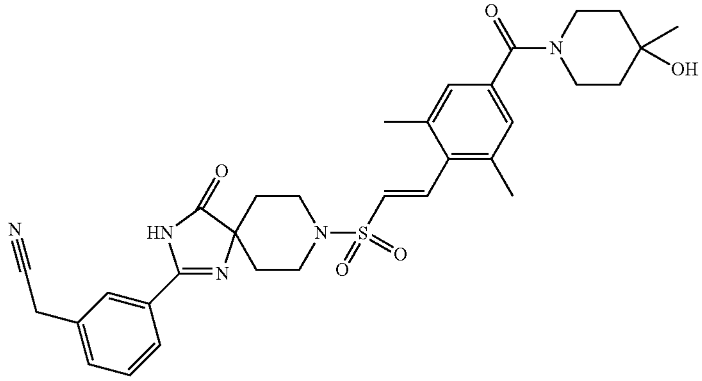 [SMILES: Cc1cc(C(=O)N2CCC(C)(O)CC2)cc(C)c1/C=C/S(=O)(=O)N1CCC2(CC1)N=C(c1cccc(CC#N)c1)NC2=O] | LCMS-F-2 | 0.63 | 604 (M + H)+ |
| 1188 | 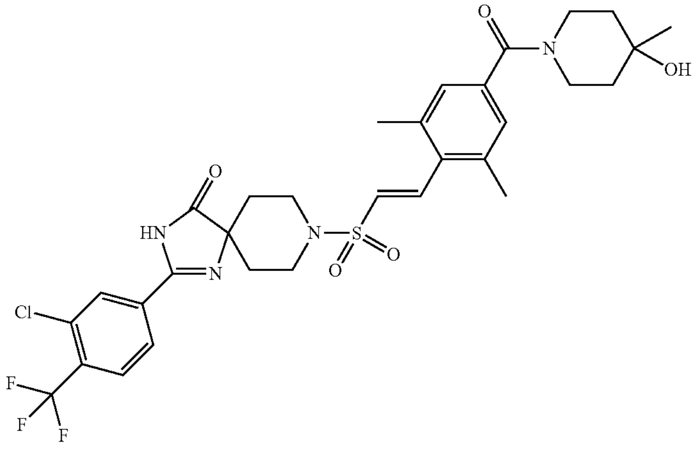 [SMILES: Cc1cc(C(=O)N2CCC(C)(O)CC2)cc(C)c1/C=C/S(=O)(=O)N1CCC2(CC1)N=C(c1ccc(C(F)(F)F)c(Cl)c1)NC2=O] | LCMS-F-2 | 0.79 | 667 (M + H)+ |

TABLE 176-continued
| Target Compound | Structure | LCMS condition | Retention time (min) | MS (m/z) |
|---|---|---|---|---|
| 1189 | 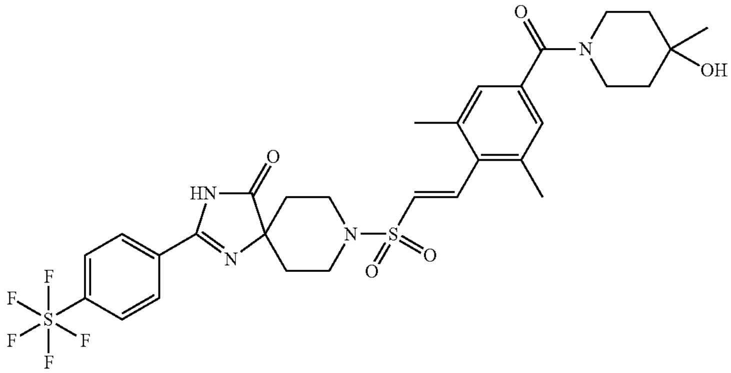 [SMILES: Cc1cc(C(=O)N2CCC(C)(O)CC2)cc(C)c1/C=C/S(=O)(=O)N1CCC2(CC1)N=C(c1ccc(S(F)(F)(F)(F)F)cc1)NC2=O] | LCMS-F-2 | 0.77 | 691 (M + H)+ |
| 1190 | 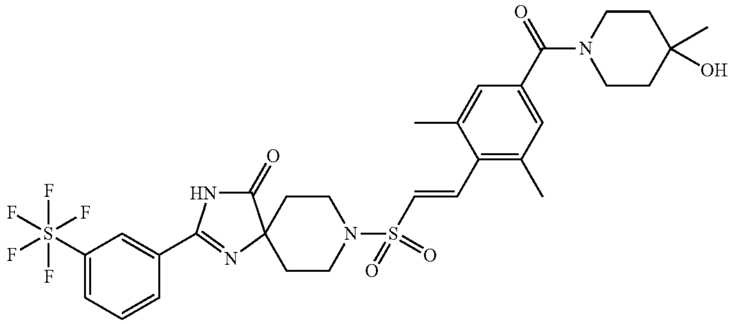 [SMILES: Cc1cc(C(=O)N2CCC(C)(O)CC2)cc(C)c1/C=C/S(=O)(=O)N1CCC2(CC1)N=C(c1cccc(S(F)(F)(F)(F)F)c1)NC2=O] | LCMS-F-2 | 0.76 | 691 (M + H)+ |
| 1191 | 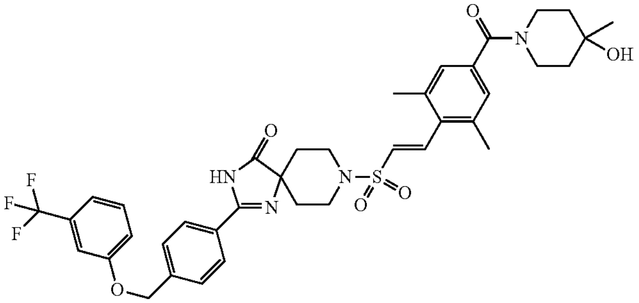 [SMILES: Cc1cc(C(=O)N2CCC(C)(O)CC2)cc(C)c1/C=C/S(=O)(=O)N1CCC2(CC1)N=C(c1ccc(COc3cccc(C(F)(F)F)c3)cc1)NC2=O] | LCMS-F-2 | 0.84 | 739 (M + H)+ |
| 1192 | 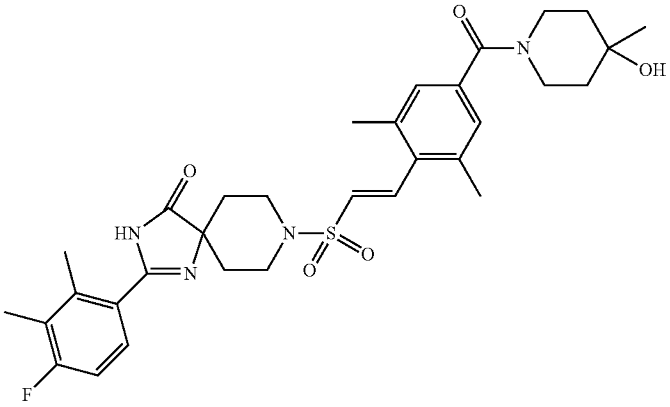 [SMILES: Cc1cc(C(=O)N2CCC(C)(O)CC2)cc(C)c1/C=C/S(=O)(=O)N1CCC2(CC1)N=C(c1ccc(F)c(C)c1C)NC2=O] | LCMS-F-2 | 0.69 | 611 (M + H)+ |

TABLE 176-continued
| Target Compound | Structure | LCMS condition | Retention time (min) | MS (m/z) |
|---|---|---|---|---|
| 1193 | 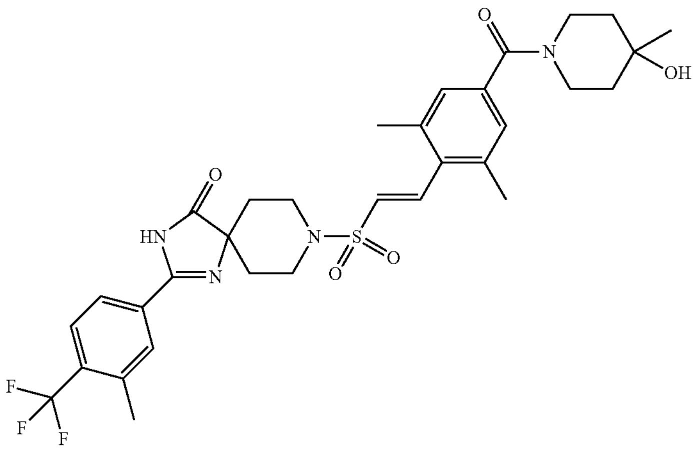 [SMILES: Cc1cc(C2=NC3(CCN(S(=O)(=O)/C=C/c4c(C)cc(C(=O)N5CCC(C)(O)CC5)cc4C)CC3)C(=O)N2)ccc1C(F)(F)F] | LCMS-F-2 | 0.78 | 647 (M + H)+ |
| 1194 | 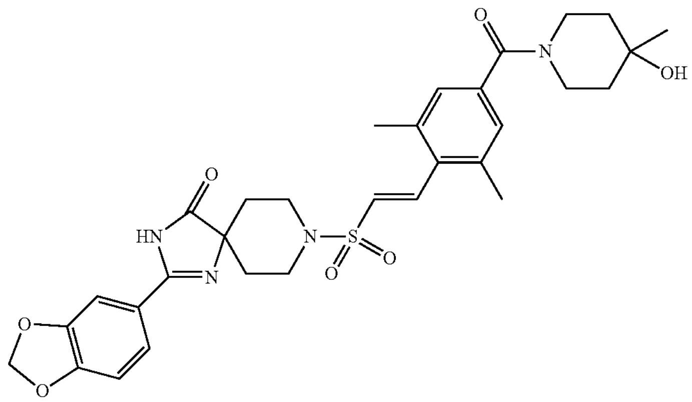 [SMILES: Cc1cc(C(=O)N2CCC(C)(O)CC2)cc(C)c1/C=C/S(=O)(=O)N1CCC2(CC1)N=C(c1ccc3c(c1)OCO3)NC2=O] | LCMS-F-2 | 0.61 | 609 (M + H)+ |
| 1195 | 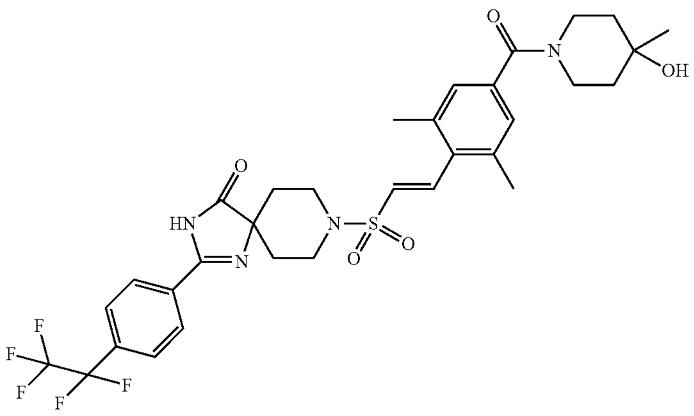 [SMILES: Cc1cc(C(=O)N2CCC(C)(O)CC2)cc(C)c1/C=C/S(=O)(=O)N1CCC2(CC1)N=C(c1ccc(C(F)(F)C(F)(F)F)cc1)NC2=O] | LCMS-F-2 | 0.79 | 683 (M + H)+ |

TABLE 176-continued
| Target Compound | Structure | LCMS condition | Retention time (min) | MS (m/z) |
|---|---|---|---|---|
| 1196 | 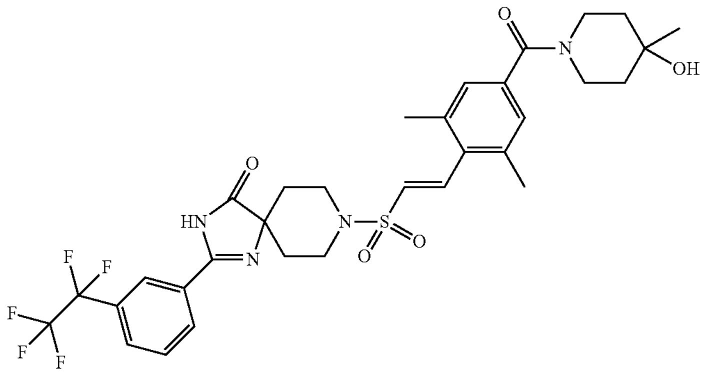 [SMILES: Cc1cc(C(=O)N2CCC(C)(O)CC2)cc(C)c1/C=C/S(=O)(=O)N1CCC2(CC1)N=C(c1cccc(C(F)(F)C(F)(F)F)c1)NC2=O] | LCMS-F-2 | 0.78 | 683 (M + H)+ |
| 1197 | 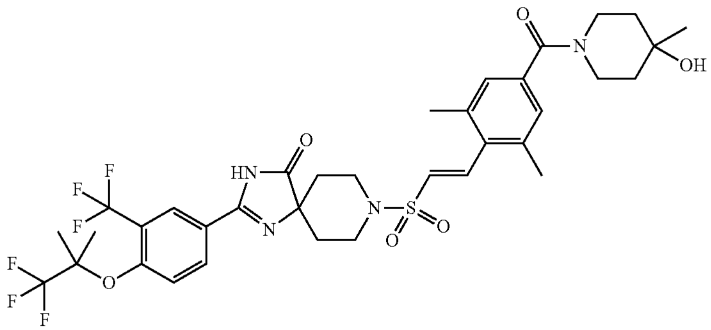 [SMILES: Cc1cc(C(=O)N2CCC(C)(O)CC2)cc(C)c1/C=C/S(=O)(=O)N1CCC2(CC1)N=C(c1ccc(OC(C)(C)C(F)(F)F)c(C(F)(F)F)c1)NC2=O] | LCMS-F-2 | 0.84 | 759 (M + H)+ |
| 1198 | 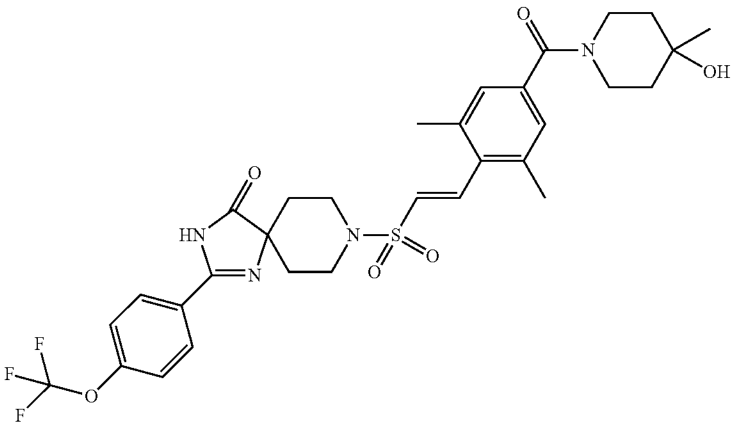 [SMILES: Cc1cc(C(=O)N2CCC(C)(O)CC2)cc(C)c1/C=C/S(=O)(=O)N1CCC2(CC1)N=C(c1ccc(OC(F)(F)F)cc1)NC2=O] | LCMS-G-1 | 1.11 | 649 (M + H)+ |
| 1199 | 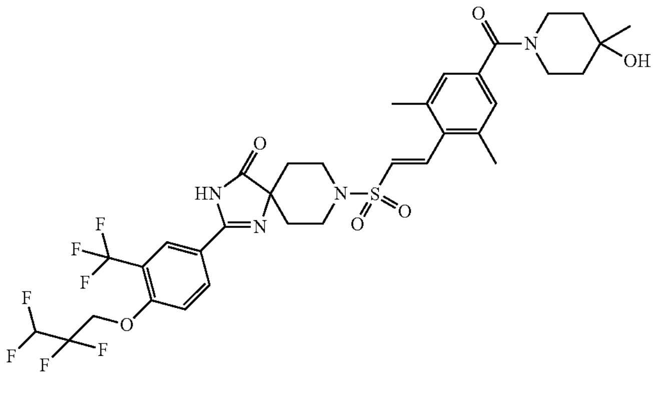 [SMILES: Cc1cc(C(=O)N2CCC(C)(O)CC2)cc(C)c1/C=C/S(=O)(=O)N1CCC2(CC1)N=C(c1ccc(OCC(F)(F)C(F)F)c(C(F)(F)F)c1)NC2=O] | LCMS-G-1 | 1.10 | 763 (M + H)+ |

TABLE 176-continued
| Target Compound | Structure | LCMS condition | Retention time (min) | MS (m/z) |
|---|---|---|---|---|
| 1200 | 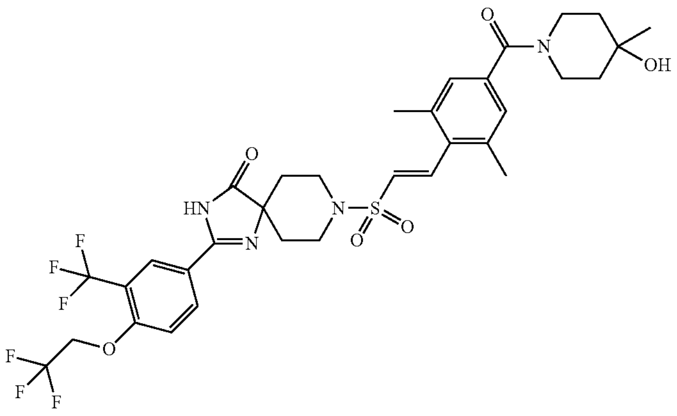 [SMILES: Cc1cc(C(=O)N2CCC(C)(O)CC2)cc(C)c1/C=C/S(=O)(=O)N1CCC2(CC1)N=C(c1ccc(OCC(F)(F)F)c(C(F)(F)F)c1)NC2=O] | LCMS-G-1 | 1.10 | 731 (M + H)+ |
| 1201 | 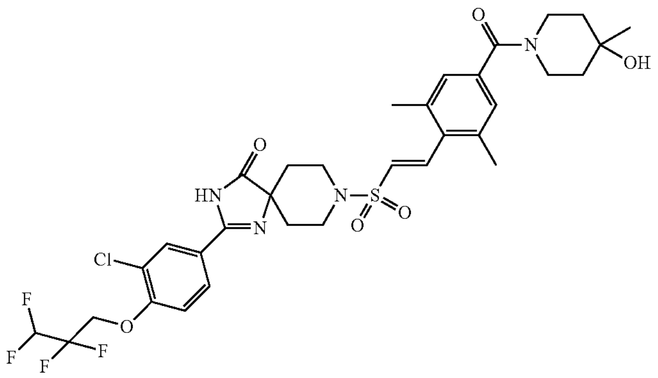 [SMILES: Cc1cc(C(=O)N2CCC(C)(O)CC2)cc(C)c1/C=C/S(=O)(=O)N1CCC2(CC1)N=C(c1ccc(OCC(F)(F)C(F)F)c(Cl)c1)NC2=O] | LCMS-G-1 | 1.13 | 729 (M + H)+ |
| 1202 | 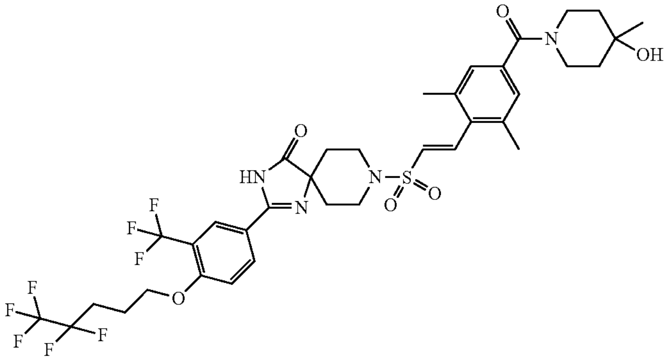 [SMILES: Cc1cc(C(=O)N2CCC(C)(O)CC2)cc(C)c1/C=C/S(=O)(=O)N1CCC2(CC1)N=C(c1ccc(OCCCC(F)(F)C(F)(F)F)c(C(F)(F)F)c1)NC2=O] | LCMS-G-1 | 1.15 | 809 (M + H)+ |
| 1203 | 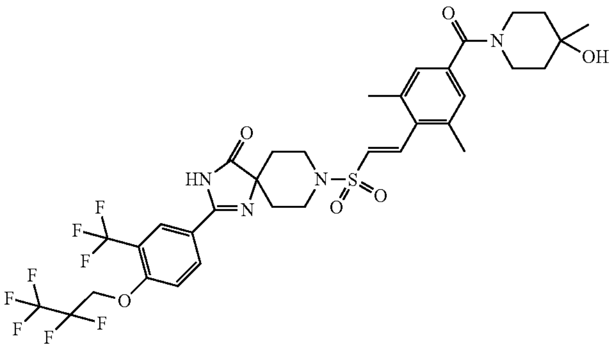 [SMILES: Cc1cc(C(=O)N2CCC(C)(O)CC2)cc(C)c1/C=C/S(=O)(=O)N1CCC2(CC1)N=C(c1ccc(OCC(F)(F)C(F)(F)F)c(C(F)(F)F)c1)NC2=O] | LCMS-G-1 | 1.17 | 781 (M + H)+ |

TABLE 176-continued
| Target Compound | Structure | LCMS condition | Retention time (min) | MS (m/z) |
|---|---|---|---|---|
| 1204 | 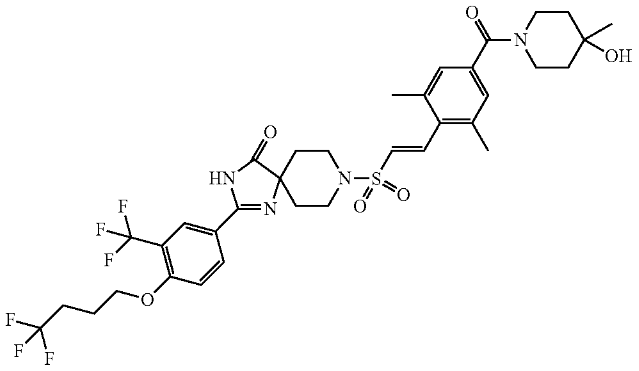 [SMILES: Cc1cc(C(=O)N2CCC(C)(O)CC2)cc(C)c1/C=C/S(=O)(=O)N1CCC2(CC1)N=C(c1ccc(OCCCC(F)(F)F)c(C(F)(F)F)c1)NC2=O] | LCMS-G-1 | 1.15 | 759 (M + H)+ |
| 1205 | 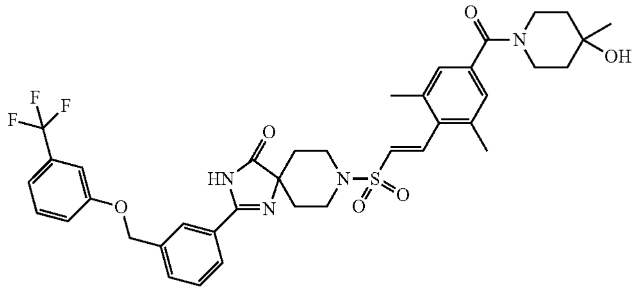 [SMILES: Cc1cc(C(=O)N2CCC(C)(O)CC2)cc(C)c1/C=C/S(=O)(=O)N1CCC2(CC1)N=C(c1cccc(COc3cccc(C(F)(F)F)c3)c1)NC2=O] | LCMS-G-1 | 1.13 | 739 (M + H)+ |
| 1206 | 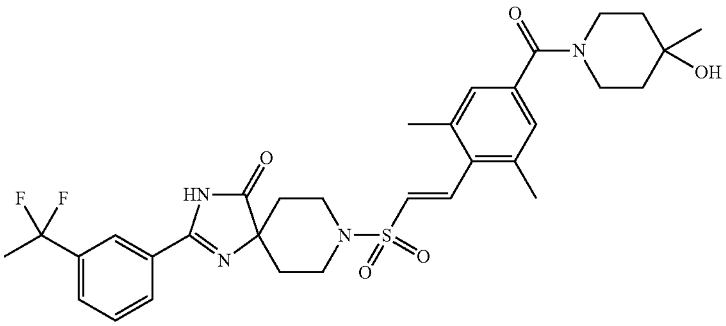 [SMILES: Cc1cc(C(=O)N2CCC(C)(O)CC2)cc(C)c1/C=C/S(=O)(=O)N1CCC2(CC1)N=C(c1cccc(C(C)(F)F)c1)NC2=O] | LCMS-G-1 | 1.09 | 629 (M + H)+ |
| 1207 | 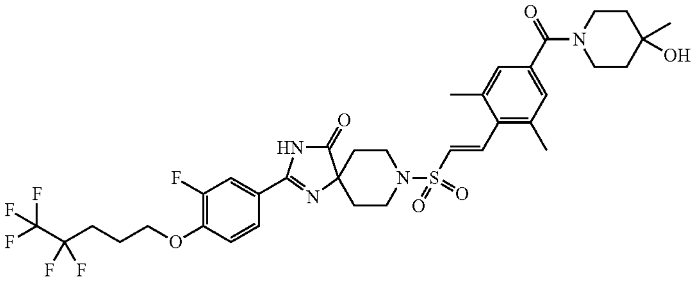 [SMILES: Cc1cc(C(=O)N2CCC(C)(O)CC2)cc(C)c1/C=C/S(=O)(=O)N1CCC2(CC1)N=C(c1ccc(OCCCC(F)(F)C(F)(F)F)c(F)c1)NC2=O] | LCMS-G-1 | 1.17 | 759 (M + H)+ |

TABLE 176-continued
| Target Compound | Structure | LCMS condition | Retention time (min) | MS (m/z) |
|---|---|---|---|---|
| 1208 | 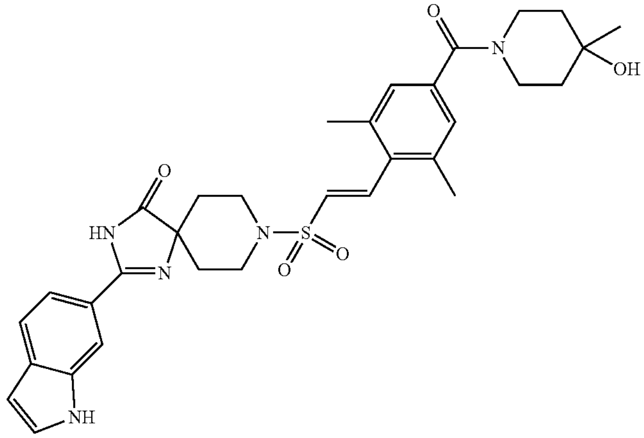 [SMILES: Cc1cc(C(=O)N2CCC(C)(O)CC2)cc(C)c1/C=C/S(=O)(=O)N1CCC2(CC1)N=C(c1ccc3cc[nH]c3c1)NC2=O] | LCMS-F-2 | 0.57 | 604 (M + H)+ |
| 1209 | 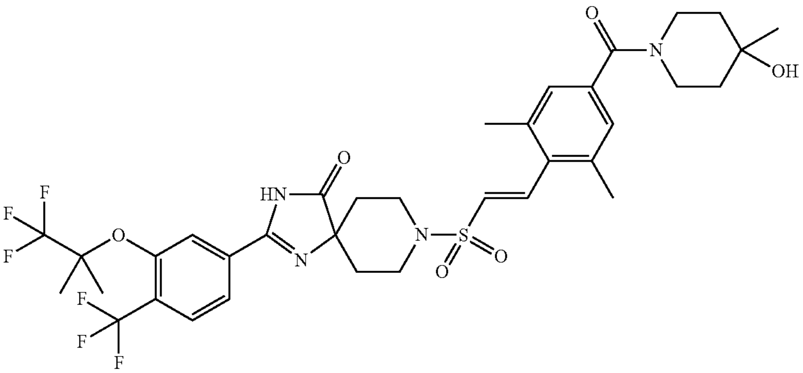 [SMILES: Cc1cc(C(=O)N2CCC(C)(O)CC2)cc(C)c1/C=C/S(=O)(=O)N1CCC2(CC1)N=C(c1ccc(C(F)(F)F)c(OC(C)(C)C(F)(F)F)c1)NC2=O] | LCMS-F-2 | 0.86 | 759 (M + H)+ |
| 1210 | 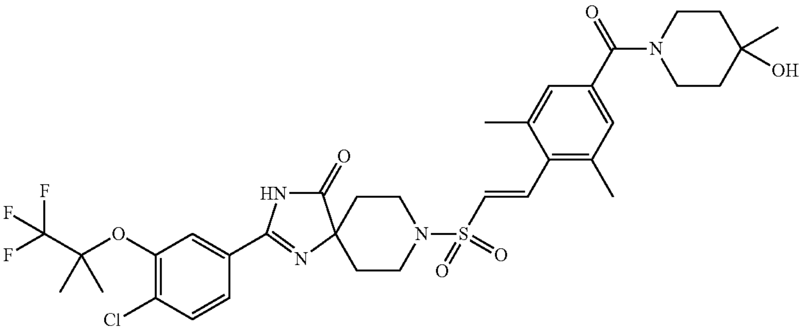 [SMILES: Cc1cc(C(=O)N2CCC(C)(O)CC2)cc(C)c1/C=C/S(=O)(=O)N1CCC2(CC1)N=C(c1ccc(Cl)c(OC(C)(C)C(F)(F)F)c1)NC2=O] | LCMS-F-2 | 0.83 | 725 (M + H)+ |
| 1211 | 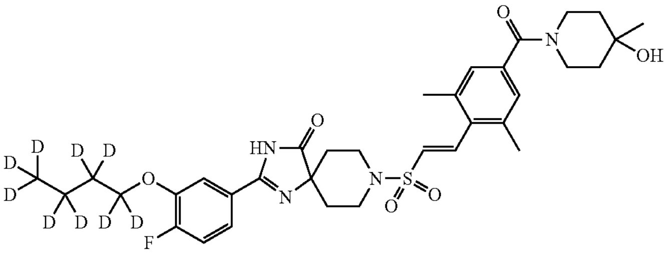 | LCMS-F-2 | 0.80 | 664 (M + H)+ |

TABLE 176-continued
| Target Compound | Structure | LCMS condition | Retention time (min) | MS (m/z) |
|---|---|---|---|---|
| 1212 | 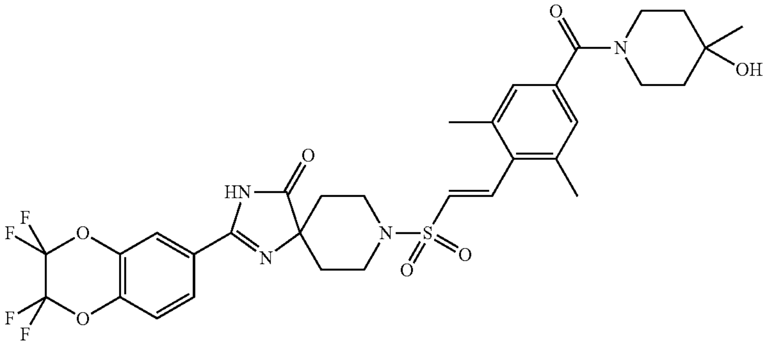 [SMILES: Cc1cc(C(=O)N2CCC(C)(O)CC2)cc(C)c1/C=C/S(=O)(=O)N1CCC2(CC1)N=C(c1ccc3c(c1)OC(F)(F)C(F)(F)O3)NC2=O] | LCMS-F-2 | 0.81 | 695 (M + H)+ |
| 1213 | 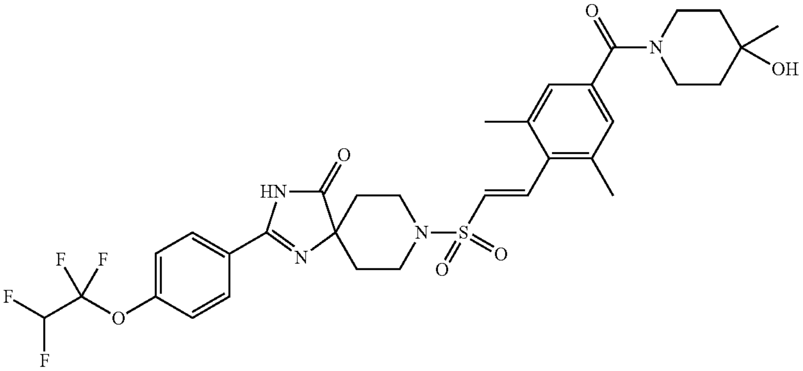 [SMILES: Cc1cc(C(=O)N2CCC(C)(O)CC2)cc(C)c1/C=C/S(=O)(=O)N1CCC2(CC1)N=C(c1ccc(OC(F)(F)C(F)F)cc1)NC2=O] | LCMS-F-2 | 0.74 | 681 (M + H)+ |
| 1214 | 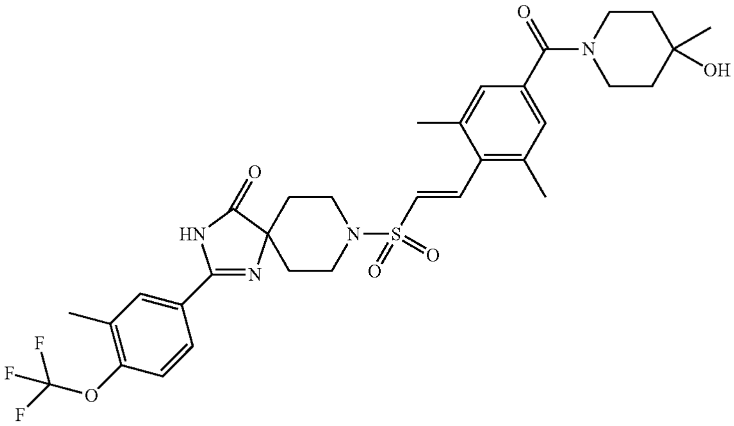 [SMILES: Cc1cc(C2=NC3(CCN(S(=O)(=O)/C=C/c4c(C)cc(C(=O)N5CCC(C)(O)CC5)cc4C)CC3)C(=O)N2)ccc1OC(F)(F)F] | LCMS-F-2 | 0.79 | 663 (M + H)+ |
| 1215 | 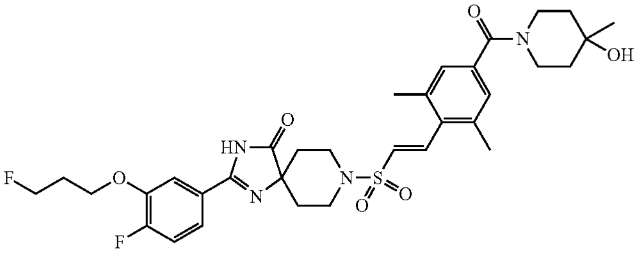 [SMILES: Cc1cc(C(=O)N2CCC(C)(O)CC2)cc(C)c1/C=C/S(=O)(=O)N1CCC2(CC1)N=C(c1ccc(F)c(OCCCF)c1)NC2=O] | LCMS-F-2 | 0.72 | 659 (M + H)+ |

TABLE 176-continued
| Target Compound | Structure | LCMS condition | Retention time (min) | MS (m/z) |
| --- | --- | --- | --- | --- |
| 1216 | 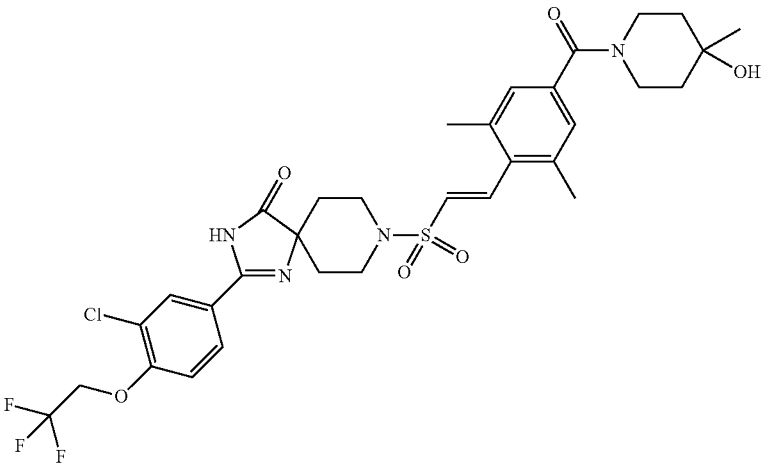 [SMILES: Cc1cc(C(=O)N2CCC(C)(O)CC2)cc(C)c1/C=C/S(=O)(=O)N1CCC2(CC1)N=C(c1ccc(OCC(F)(F)F)c(Cl)c1)NC2=O] | LCMS-G-1 | 1.09 | 697 (M + H)+ |
| 1217 | 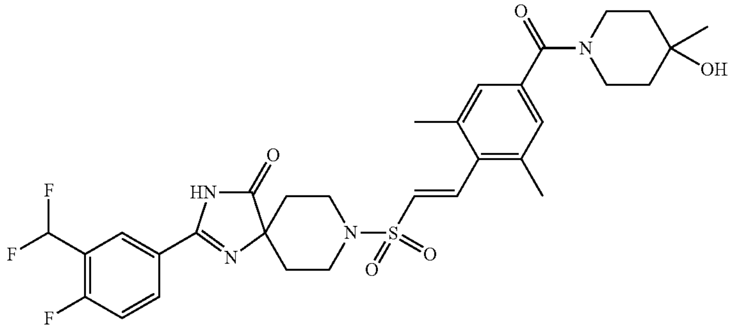 [SMILES: Cc1cc(C(=O)N2CCC(C)(O)CC2)cc(C)c1/C=C/S(=O)(=O)N1CCC2(CC1)N=C(c1ccc(F)c(C(F)F)c1)NC2=O] | LCMS-F-2 | 0.72 | 633 (M + H)+ |
| 1218 | 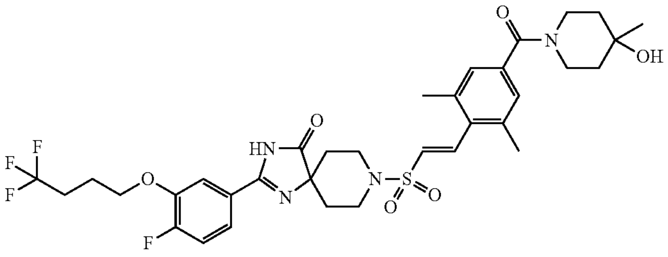 [SMILES: Cc1cc(C(=O)N2CCC(C)(O)CC2)cc(C)c1/C=C/S(=O)(=O)N1CCC2(CC1)N=C(c1ccc(F)c(OCCCC(F)(F)F)c1)NC2=O] | LCMS-F-2 | 0.79 | 709 (M + H)+ |
| 1219 | 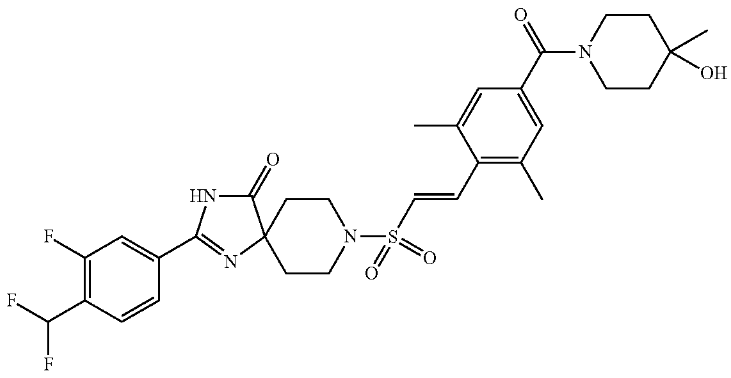 [SMILES: Cc1cc(C(=O)N2CCC(C)(O)CC2)cc(C)c1/C=C/S(=O)(=O)N1CCC2(CC1)N=C(c1ccc(C(F)F)c(F)c1)NC2=O] | LCMS-F-2 | 0.72 | 633 (M + H)+ |

TABLE 176-continued
| Target Compound | Structure | LCMS condition | Retention time (min) | MS (m/z) |
|---|---|---|---|---|
| 1220 | 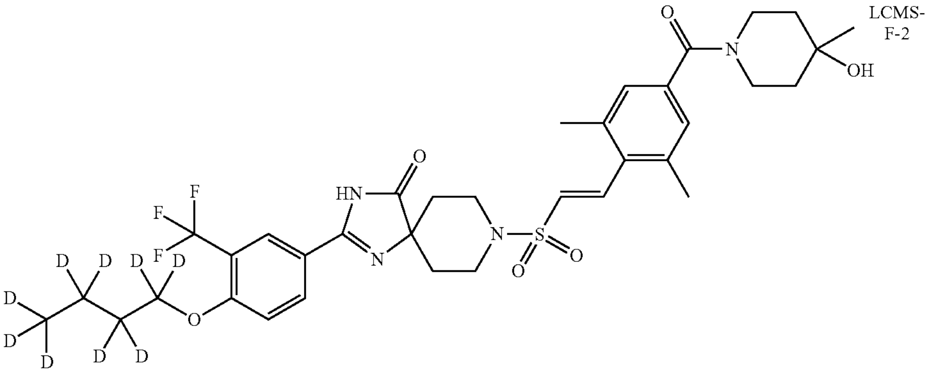 | LCMS-F-2 | 0.86 | 714 (M + H)+ |
| 1221 | 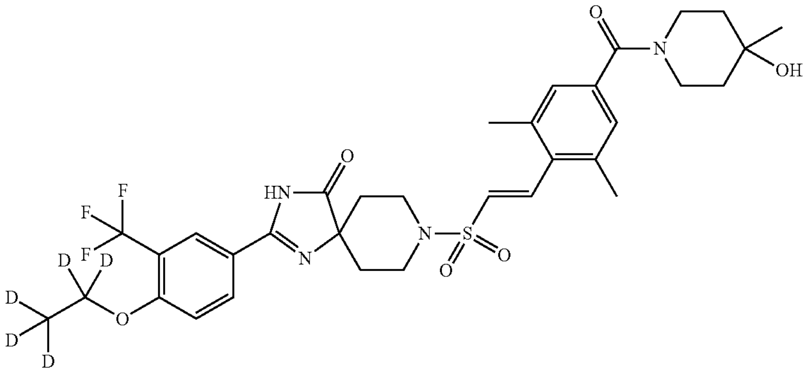 [SMILES: [2H]C([2H])([2H])C([2H])([2H])Oc1ccc(C2=NC3(CCN(S(=O)(=O)/C=C/c4c(C)cc(C(=O)N5CCC(C)(O)CC5)cc4C)CC3)C(=O)N2)cc1C(F)(F)F] | LCMS-F-2 | 0.76 | 682 (M + H)+ |
| 1222 | 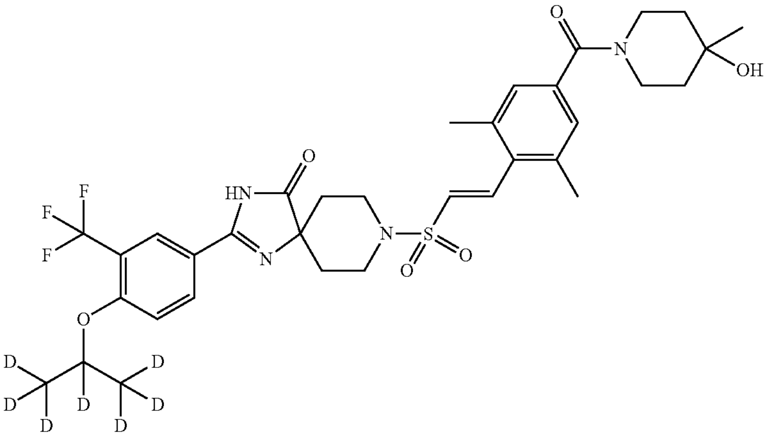 [SMILES: [2H]C([2H])([2H])C([2H])(Oc1ccc(C2=NC3(CCN(S(=O)(=O)/C=C/c4c(C)cc(C(=O)N5CCC(C)(O)CC5)cc4C)CC3)C(=O)N2)cc1C(F)(F)F)C([2H])([2H])[2H]] | LCMS-F-2 | 0.80 | 698 (M + H)+ |

TABLE 176-continued
| Target Compound | Structure | LCMS condition | Retention time (min) | MS (m/z) |
|---|---|---|---|---|
| 1223 | 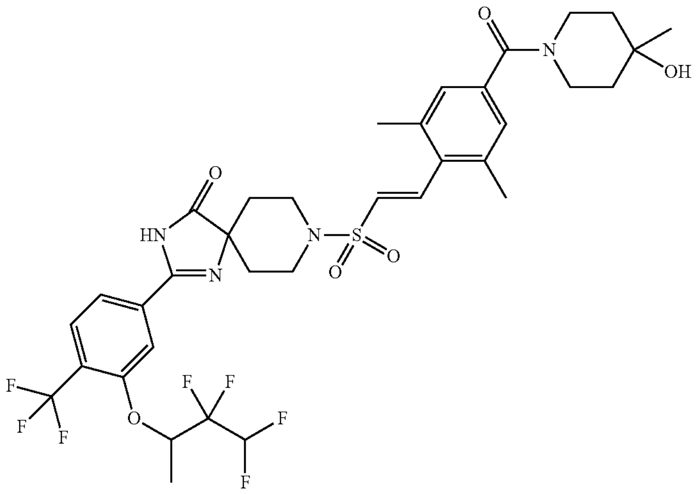 | LCMS-F-2 | 0.83 | 763 (M + H)+ |
| 1224 | 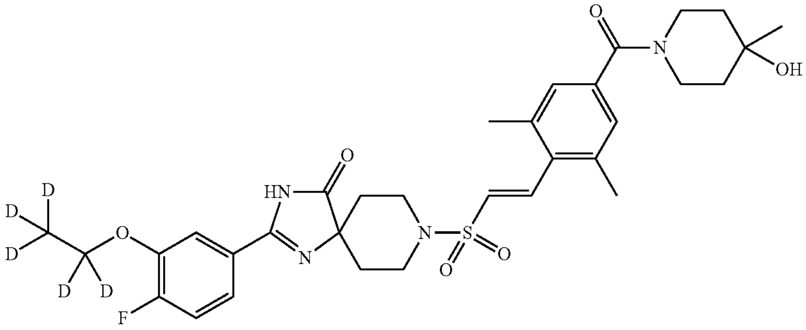 [SMILES: [2H]C([2H])([2H])C([2H])([2H])Oc1cc(C2=NC3(CCN(S(=O)(=O)/C=C/c4c(C)cc(C(=O)N5CCC(C)(O)CC5)cc4C)CC3)C(=O)N2)ccc1F] | LCMS-F-2 | 0.71 | 632 (M + H)+ |
| 1225 | 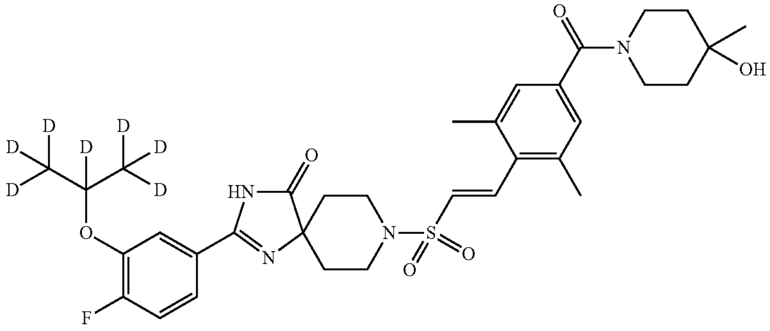 [SMILES: [2H]C([2H])([2H])C([2H])(Oc1cc(C2=NC3(CCN(S(=O)(=O)/C=C/c4c(C)cc(C(=O)N5CCC(C)(O)CC5)cc4C)CC3)C(=O)N2)ccc1F)C([2H])([2H])[2H]] | LCMS-F-2 | 0.74 | 648 (M + H)+ |
| 1226 | 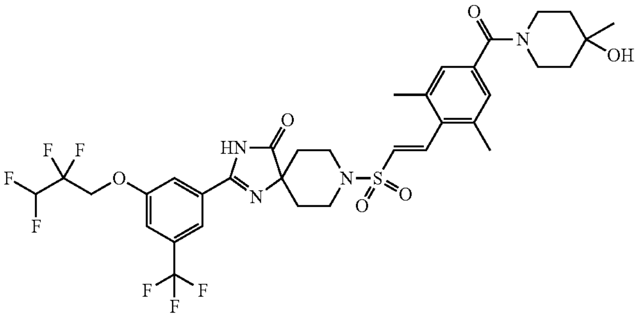 [SMILES: Cc1cc(C(=O)N2CCC(C)(O)CC2)cc(C)c1/C=C/S(=O)(=O)N1CCC2(CC1)N=C(c1cc(OCC(F)(F)C(F)F)cc(C(F)(F)F)c1)NC2=O] | LCMS-F-2 | 0.83 | 763 (M + H)+ |

TABLE 176-continued
| Target Compound | Structure | LCMS condition | Retention time (min) | MS (m/z) |
|---|---|---|---|---|
| 1227 | 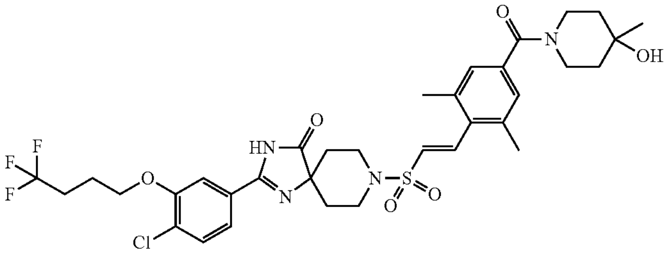 | LCMS-F-2 | 0.8 | 725 (M + H)+ |
| 1228 | 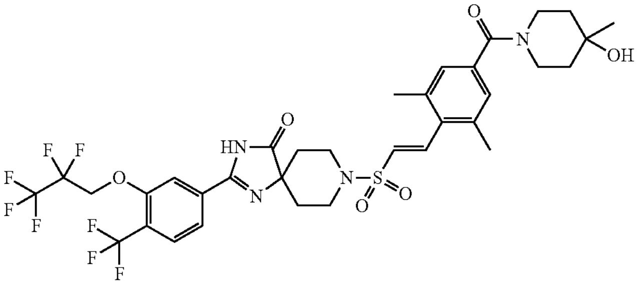 [SMILES: Cc1cc(C(=O)N2CCC(C)(O)CC2)cc(C)c1/C=C/S(=O)(=O)N1CCC2(CC1)N=C(c1ccc(C(F)(F)F)c(OCC(F)(F)C(F)(F)F)c1)NC2=O] | LCMS-F-2 | 0.87 | 781 (M + H)+ |
| 1229 | 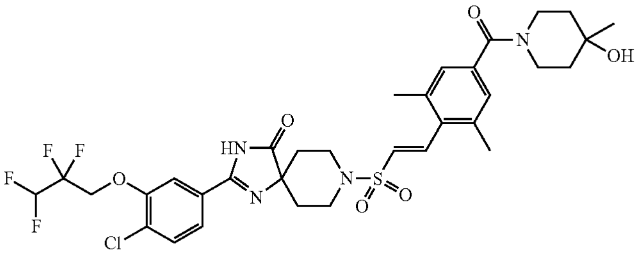 [SMILES: Cc1cc(C(=O)N2CCC(C)(O)CC2)cc(C)c1/C=C/S(=O)(=O)N1CCC2(CC1)N=C(c1ccc(Cl)c(OCC(F)(F)C(F)F)c1)NC2=O] | LCMS-F-2 | 0.79 | 729 (M + H)+ |
| 1230 | 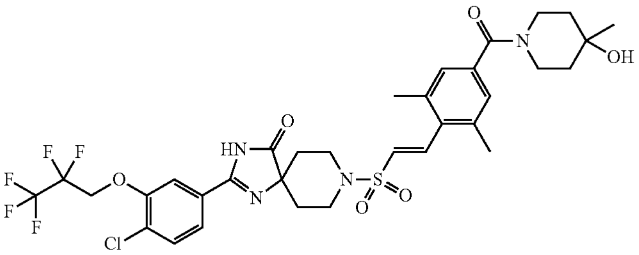 [SMILES: Cc1cc(C(=O)N2CCC(C)(O)CC2)cc(C)c1/C=C/S(=O)(=O)N1CCC2(CC1)N=C(c1ccc(Cl)c(OCC(F)(F)C(F)(F)F)c1)NC2=O] | LCMS-F-2 | 0.84 | 747 (M + H)+ |
| 1231 | 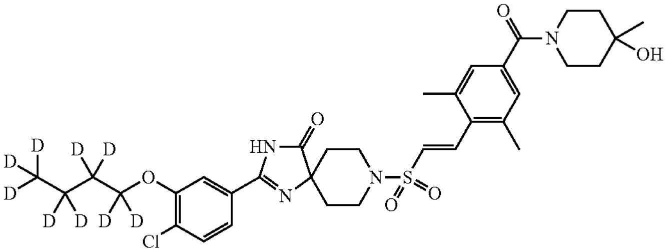 | LCMS-F-2 | 0.85 | 681 (M + H)+ |

TABLE 176-continued
| Target Compound | Structure | LCMS condition | Retention time (min) | MS (m/z) |
|---|---|---|---|---|
| 1232 | 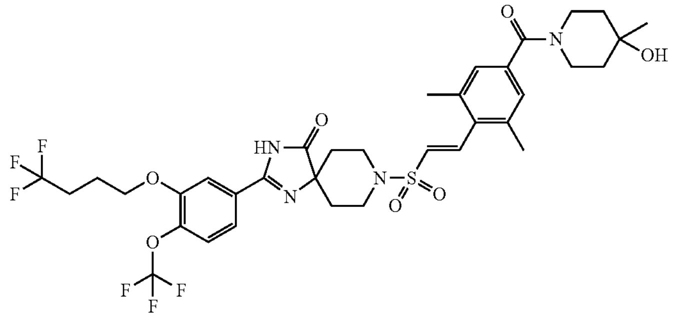 [SMILES: Cc1cc(C(=O)N2CCC(C)(O)CC2)cc(C)c1/C=C/S(=O)(=O)N1CCC2(CC1)N=C(c1ccc(OC(F)(F)F)c(OCCCC(F)(F)F)c1)NC2=O] | LCMS-F-2 | 0.87 | 775 (M + H)+ |
| 1233 | 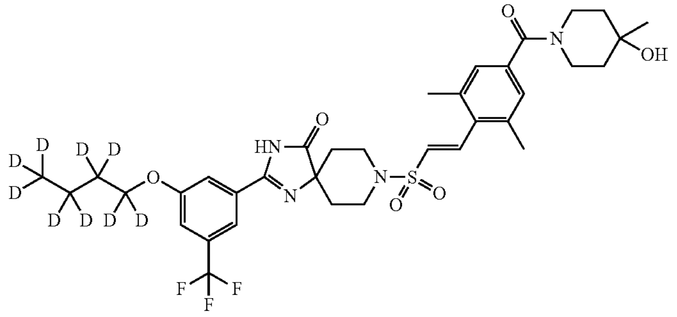 [SMILES: [2H]C([2H])([2H])C([2H])([2H])C([2H])([2H])C([2H])([2H])Oc1cc(C2=NC3(CCN(S(=O)(=O)/C=C/c4c(C)cc(C(=O)N5CCC(C)(O)CC5)cc4C)CC3)C(=O)N2)cc(C(F)(F)F)c1] | LCMS-F-2 | 0.90 | 714 (M + H)+ |
| 1234 | 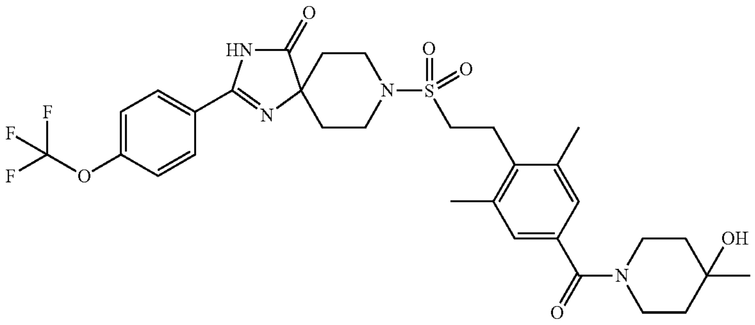 [SMILES: Cc1cc(C(=O)N2CCC(C)(O)CC2)cc(C)c1CCS(=O)(=O)N1CCC2(CC1)N=C(c1ccc(OC(F)(F)F)cc1)NC2=O] | LCMS-G-1 | 1.10 | 651 (M + H)+ |
| 1235 | 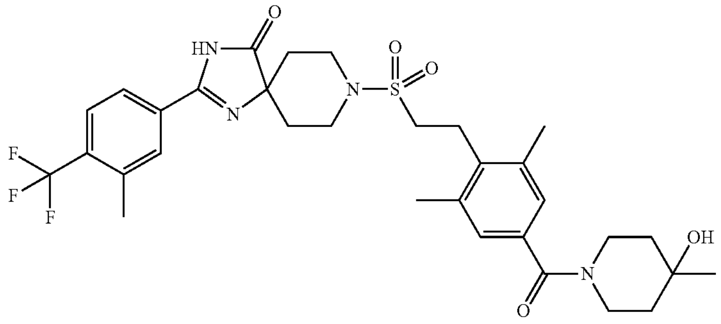 [SMILES: Cc1cc(C2=NC3(CCN(S(=O)(=O)CCc4c(C)cc(C(=O)N5CCC(C)(O)CC5)cc4C)CC3)C(=O)N2)ccc1C(F)(F)F] | LCMS-G-1 | 1.13 | 649 (M + H)+ |

TABLE 176-continued

| Target Compound | Structure | LCMS condition | Retention time (min) | MS (m/z) |
|---|---|---|---|---|
| 1236 | 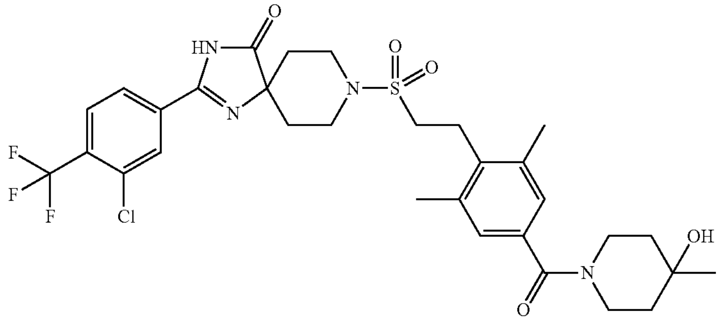 [SMILES: Cc1cc(C(=O)N2CCC(C)(O)CC2)cc(C)c1CCS(=O)(=O)N1CCC2(CC1)N=C(c1ccc(C(F)(F)F)c(Cl)c1)NC2=O] | LCMS-G-1 | 1.15 | 669 (M + H)+ |
| 1237 | 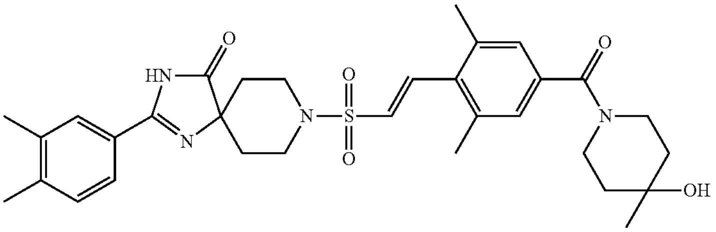 [SMILES: Cc1ccc(C2=NC3(CCN(S(=O)(=O)/C=C/c4c(C)cc(C(=O)N5CCC(C)(O)CC5)cc4C)CC3)C(=O)N2)cc1C] | LCMS-C-1 | 2.63 | 593 (M + H)+ |
| 1238 | 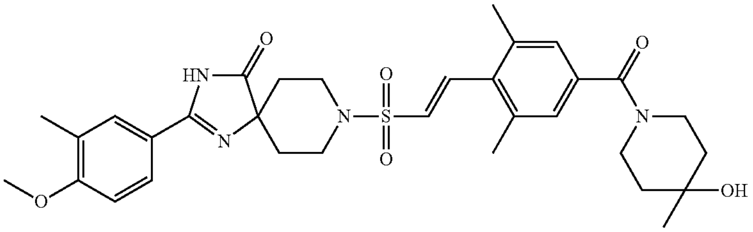 [SMILES: COc1ccc(C2=NC3(CCN(S(=O)(=O)/C=C/c4c(C)cc(C(=O)N5CCC(C)(O)CC5)cc4C)CC3)C(=O)N2)cc1C] | LCMS-C-1 | 2.58 | 609 (M + H)+ |

The arylboronic acid reagent used in the synthesis of Compound 1195 (4-pentafluoroethylphenylboronic acid) was synthesized by the following method.

(Reaction 292-4)

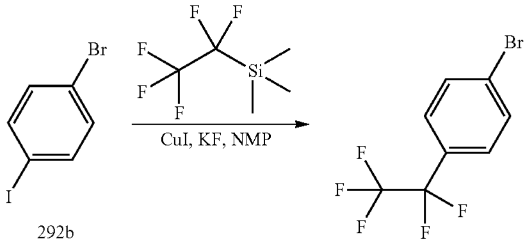

292b 292c

A solution of 4-bromo-iodobenzene (500 mg, 1.77 mmol), trimethylsilylpentafluoroethane (679 mg, 3.53 mmol), copper iodide (672 mg, 3.53 mmol) and potassium fluoride (205 mg, 3.53 mmol) in N-methylpyrolidone (1.0 mL) was heated with stirring at 100° C. for three hours in a sealed reaction vessel. After cooling to room temperature, the reaction mixture was purified by silica gel column chromatography (hexane:ethyl acetate=20:1) to give 1-bromo-4-pentafluoroethylbenzene as a colorless liquid (253 mg, 52%).

$^1$H-NMR (270 MHz, $CDCl_3$) δ 7.46 (2H, d, J=8.6 Hz), 7.65 (2H, d, J=8.6 Hz).

(Reaction 292-5)

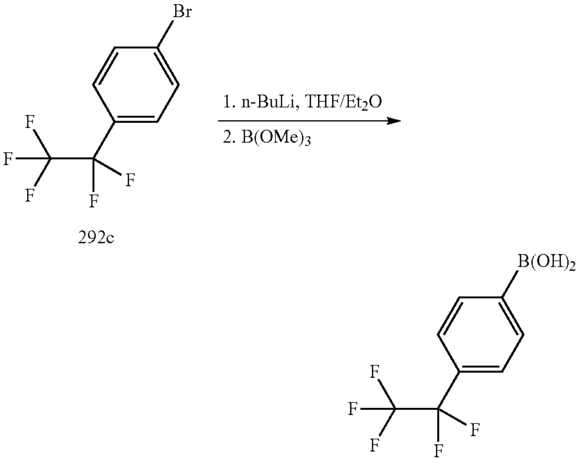

292c

292d

A 1.5 M solution of n-butyllithium in tetrahydrofuran (0.57 mL) was added to a solution of 1-bromo-4-pentafluoroethylbenzene (180 mg, 0.65 mmol) in diethyl ether (1.0 mL) at −78° C., and the mixture was stirred for 20 minutes. Thereafter, trimethyl borate (101 mg, 3.28 mmol) was added and the mixture was stirred at −78° C. for 10 minutes and at room temperature for 30 minutes. 6 N aqueous hydrochloric acid (200 μL) was added to the reaction mixture, and the reaction was terminated. The mixture was then purified by silica gel column chromatography to give 4-pentafluoroethylphenylboronic acid as a white solid (111 mg, 71%).

$^1$H-NMR (400 MHz, $CDCl_3$) δ 7.87 (2H, d, J=8.0 Hz), 7.64 (2H, d, J=8.0 Hz), 4.61 (s, 2H).

The arylboronic acid reagent used in the synthesis of Compound 1196 (3-pentafluoroethylphenylboronic acid) was synthesized by the following method.

(Reaction 292-6)

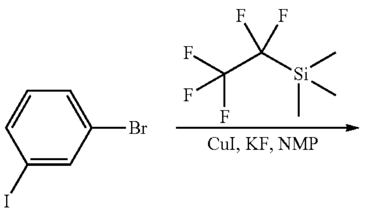

292e

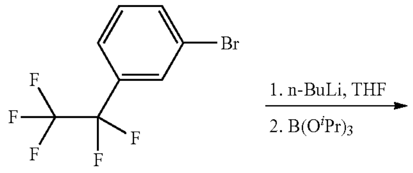

292f

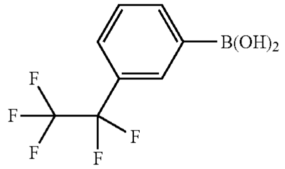

292g

3-Pentafluoroethylphenylboronic acid was obtained by operations similar to those in Reaction 292-4 and Reaction 292-5 using 1-bromo-3-iodo-benzene as a starting material.

MS (ESI) m/z=239 (M−H)−.

The arylboronic acid reagent used in the synthesis of Compound 1197 (4-(2,2,2-trifluoro-1,1-dimethyl-ethoxy)-3-trifluoromethylphenylboronic acid) was synthesized by the following method.

(Reaction 292-7)

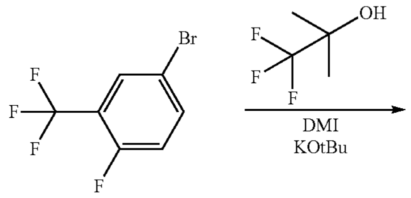

292h

-continued

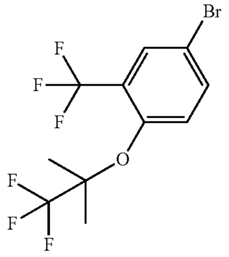

292i

Potassium tert-butoxide (236 mg, 2.1 mmol) was added to a solution of 5-bromo-2-fluorobenzotrifluoride (485 mg, 2.0 mmol) and 2-trifluoromethyl-2-propanol (0.24 mL, 2.2 mmol) in DMI (0.5 mL) at room temperature, and the mixture was stirred at 100° C. for two hours. The reaction solution was purified by silica gel column chromatography to give 4-bromo-1-(2,2,2-trifluoro-1,1-dimethyl-ethoxy)-2-trifluoromethyl-benzene (349 mg, 50%).

$^1$H-NMR (400 MHz, $CDCl_3$) δ 7.73 (1H, d, J=2.4 Hz), 7.59 (1H, dd, J=2.4, 8.9 Hz), 7.14 (1H, d, J=8.9 Hz), 1.53 (s, 6H).

(Reaction 292-8)

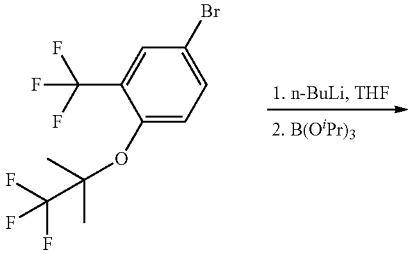

292i

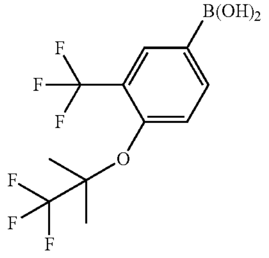

292j 4-(2,2,2-Trifluoro-1,1-dimethyl-ethoxy)-3-trifluoromethylphenylboronic acid was obtained by operations similar to those in Reaction 292-5 using 4-bromo-1-(2,2,2-trifluoro-1,1-dimethyl-ethoxy)-2-trifluoromethyl-benzene as a starting material.

MS (ESI) m/z=315 (M−H)−.

The arylboronic acid reagents shown below were synthesized by operations similar to those in Reaction 292-7 and Reaction 292-5 using appropriate starting compounds and used in the synthesis of the compounds in Table 176.

TABLE 177
| Target Compound | Raw material | Arylboronic acid structure | MS (m/z) |
|---|---|---|---|
| 1199 | 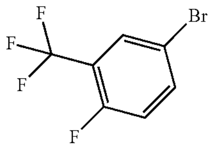 [SMILES: Fc1ccc(Br)cc1C(F)(F)F] | 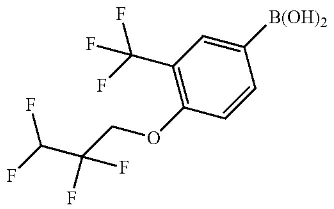 [SMILES: OB(O)c1ccc(OCC(F)(F)C(F)F)c(C(F)(F)F)c1] | 319 (M − H)− |
| 1200 | 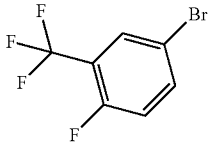 | 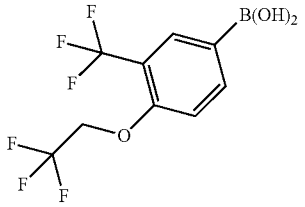 [SMILES: OB(O)c1ccc(OCC(F)(F)F)c(C(F)(F)F)c1] | 287 (M − H)− |
| 1201 | 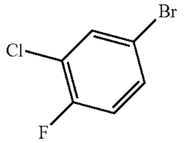 | 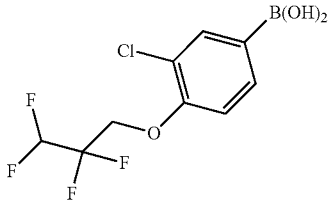 [SMILES: OB(O)c1ccc(OCC(F)(F)C(F)F)c(Cl)c1] | 285 (M − H)− |
| 1202 | 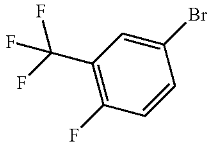 [SMILES: Fc1ccc(Br)cc1C(F)(F)F] | 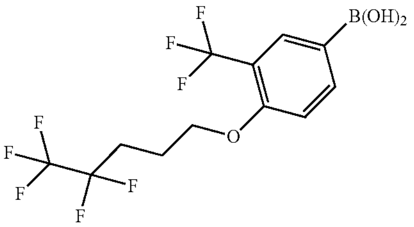 [SMILES: OB(O)c1ccc(OCCCC(F)(F)C(F)(F)F)c(C(F)(F)F)c1] | 365 (M − H)− |
| 1203 | 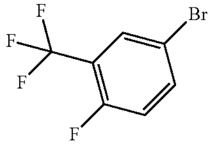 [SMILES: Fc1ccc(Br)cc1C(F)(F)F] | 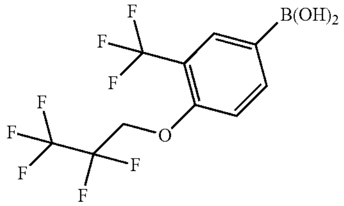 [SMILES: OB(O)c1ccc(OCC(F)(F)C(F)(F)F)c(C(F)(F)F)c1] | 337 (M − H)− |
| 1204 | 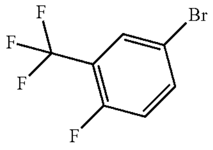 [SMILES: Fc1ccc(Br)cc1C(F)(F)F] | 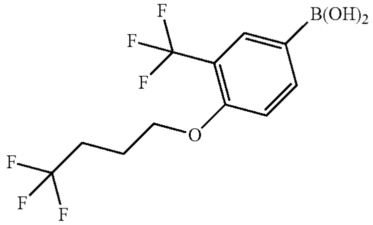 [SMILES: OB(O)c1ccc(OCCCC(F)(F)F)c(C(F)(F)F)c1] | 315 (M − H)− |
| 1216 | 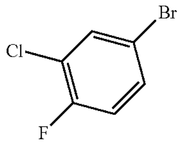 | 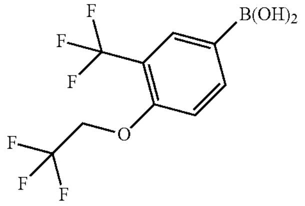 [SMILES: OB(O)c1ccc(OCC(F)(F)F)c(C(F)(F)F)c1] | 253 (M − H)− |

TABLE 177-continued

| Target Compound | Raw material | Arylboronic acid structure | MS (m/z) |
|---|---|---|---|
| 1220 | 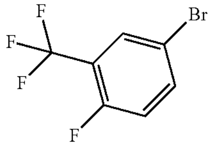 | 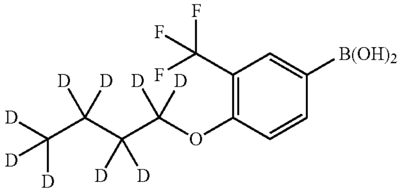 [SMILES: [2H]C([2H])([2H])C([2H])([2H])C([2H])([2H])C([2H])([2H])Oc1ccc(B(O)O)cc1C(F)(F)F] | 270 (M − H)− |
| 1221 | 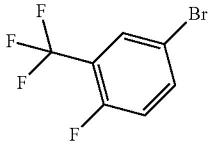 [SMILES: Fc1ccc(Br)cc1C(F)(F)F] | 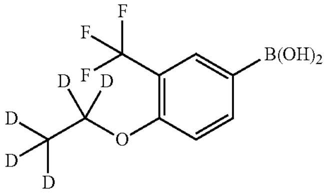 [SMILES: [2H]C([2H])([2H])C([2H])([2H])Oc1ccc(B(O)O)cc1C(F)(F)F] | 238 (M − H)− |
| 1222 | 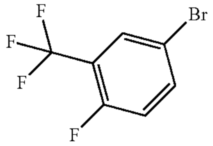 | 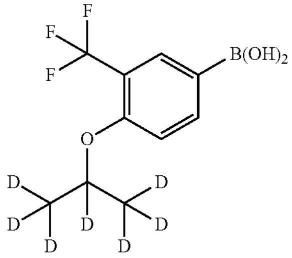 [SMILES: [2H]C([2H])([2H])C([2H])(Oc1ccc(B(O)O)cc1C(F)(F)F)C([2H])([2H])[2H]] | 254 (M − H)− |
| 1232 | 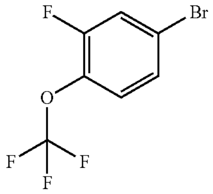 [SMILES: Fc1cc(Br)ccc1OC(F)(F)F] | 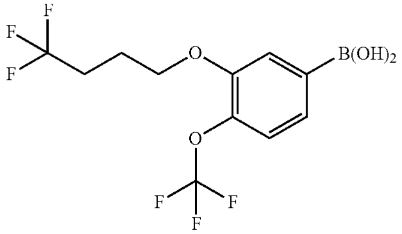 [SMILES: OB(O)c1ccc(OC(F)(F)F)c(OCCCC(F)(F)F)c1] | 331 (M − H)− |

The arylboronic acid reagents shown below were synthesized by operations similar to those in Reaction 292-5 using appropriate starting compounds and used in the synthesis of the compounds in Table 176.

TABLE 178

| Target Compound | Raw material | Arylboronic acid structure | MS (m/z) |
|---|---|---|---|
| 1214 | 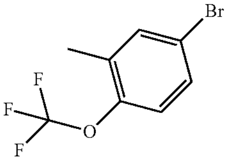 | 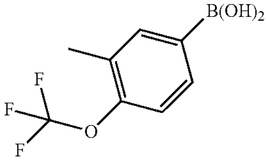 | 219 (M − H)− |
| 1217 | 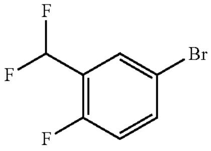 [SMILES: Fc1ccc(Br)cc1C(F)F] | 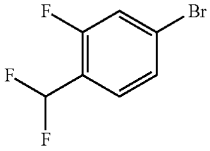 [SMILES: Fc1cc(Br)ccc1C(F)F] | 189 (M − H)− |

TABLE 178-continued

| Target Compound | Raw material | Arylboronic acid structure | MS (m/z) |
|---|---|---|---|
| 1219 | 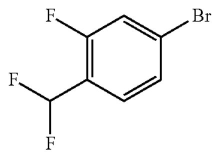 [SMILES: Fc1cc(Br)ccc1C(F)F] | 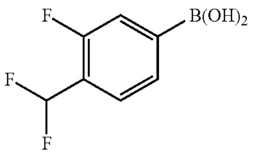 [SMILES: OB(O)c1ccc(C(F)F)c(F)c1] | 189 (M − h)− |

The arylboronic acid reagent used in the synthesis of Compound 1229 (4-chloro-3-(2,2,3,3-tetrafluoro-propoxy)-phenylboronic acid) was synthesized by the following method.

(Reaction 292-9)

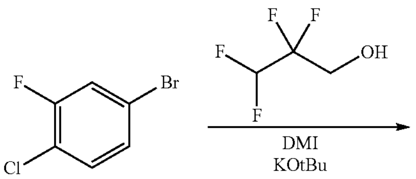

292k

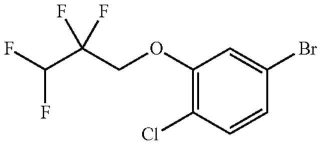

292l

4-Bromo-1-chloro-2-(2,2,3,3-tetrafluoro-propoxy)-benzene was obtained by operations similar to those in Reaction 292-7 using appropriate starting compound and reagents.

$^1$H-NMR (400 MHz, $CDCl_3$) δ 7.27 (1H, d, J=8.3 Hz), 7.15 (1H, dd, J=2.0, 8.3 Hz), 7.07 (1H, d, J=2.0 Hz), 6.15 (1H, dt, J=5.4, 53.2 Hz), 4.39 (2H, t, J=11.2 Hz).

(Reaction 292-10)

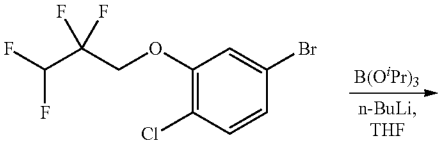

292l

-continued

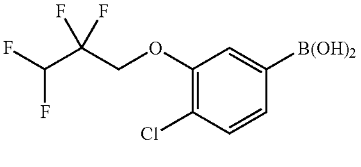

292m

A 1.5 M solution of n-butyllithium in tetrahydrofuran (0.99 mL) was added to a solution of 4-bromo-1-chloro-2-(2,2,3,3-tetrafluoro-propoxy)-benzene (434 mg, 1.35 mmol) and triisopropyl borate (382 mg, 2.03 mmol) in anhydrous tetrahydrofuran (2.0 mL) at −78° C., and the mixture was stirred for 10 minutes. The reaction mixture was warmed to room temperature and stirred for 30 minutes. 6 N aqueous hydrochloric acid was then added to the reaction mixture, and the reaction was terminated, followed by extraction with ethyl acetate. The organic layer was dried over anhydrous sodium sulfate and concentrated under reduced pressure. The residue was treated with a mixed solution of dichloromethane and hexane to give 4-chloro-3-(2,2,3,3-tetrafluoro-propoxy)-phenylboronic acid as a white solid (246 mg, 64%).

MS (ESI) m/z=285 (M−H)−.

The arylboronic acid reagents shown below were synthesized by operations similar to those in Reaction 292-7 and Reaction 292-10 using appropriate starting compounds and used in the synthesis of the compounds in Table 176.

TABLE 179

| Target Compound | Raw material | Arylboronic acid structure | MS (m/z) |
|---|---|---|---|
| 1226 | 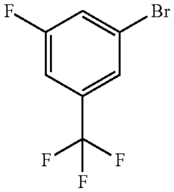 | 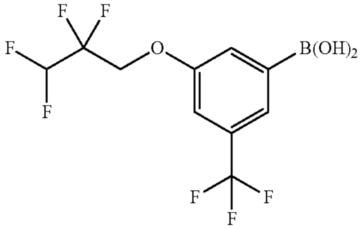 [SMILES: OB(O)c1cc(OCC(F)(F)C(F)F)cc(C(F)(F)F)c1] | 319 (M − H)− |

TABLE 179-continued

| Target Compound | Raw material | Arylboronic acid structure | MS (m/z) |
|---|---|---|---|
| 1227 | 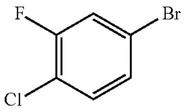 | 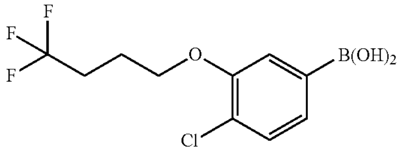 [SMILES: OB(O)c1ccc(Cl)c(OCCCC(F)(F)F)c1] | 281 (M − H)− |
| 1228 | 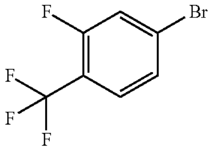 | 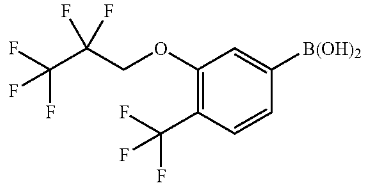 [SMILES: OB(O)c1ccc(C(F)(F)F)c(OCC(F)(F)C(F)(F)F)c1] | 337 (M − H)− |
| 1230 | 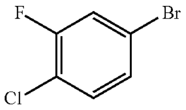 | 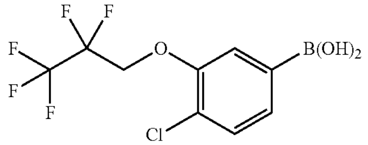 [SMILES: OB(O)c1ccc(Cl)c(OCC(F)(F)C(F)(F)F)c1] | 303 (M − H)− |
| 1231 | 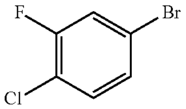 | 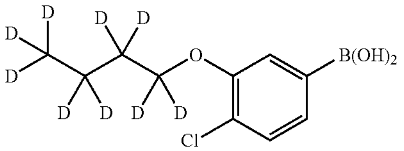 [SMILES: [2H]C([2H])([2H])C([2H])([2H])C([2H])([2H])C([2H])([2H])Oc1cc(B(O)O)ccc1Cl] | 236 (M − H)− |
| 1233 | 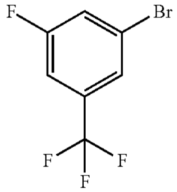 | 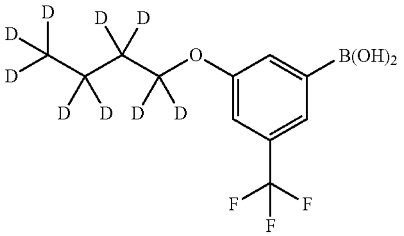 [SMILES: [2H]C([2H])([2H])C([2H])([2H])C([2H])([2H])C([2H])([2H])Oc1cc(B(O)O)cc(C(F)(F)F)c1] | 270 ( M − H)− |

The arylboronic acid reagent used in the synthesis of Compound 1213 (4-(1,1,2,2-tetrafluoro-ethoxy)phenylboronic acid) was synthesized by the following method.

(Reaction 292-11)

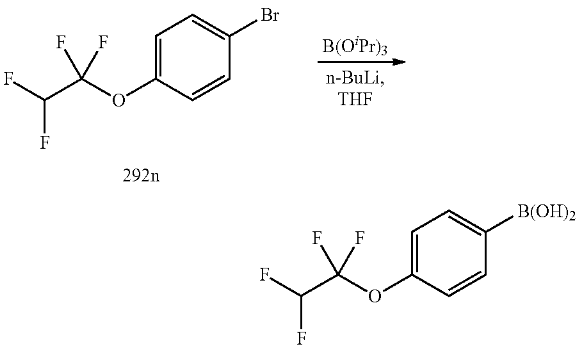

292n

292o 4-(1,1,2,2-Tetrafluoro-ethoxy)phenylboronic acid was obtained by operations similar to those in Reaction 292-10 using appropriate starting compound and reagents.

MS (ESI) m/z=237 (M−H)−.

The arylboronic acid reagent used in the synthesis of Compound 1223 (3-(2,2,3,3-tetrafluoro-propoxy)-4-trifluoromethylphenylboronic acid) was synthesized by the following method.

(Reaction 292-12)

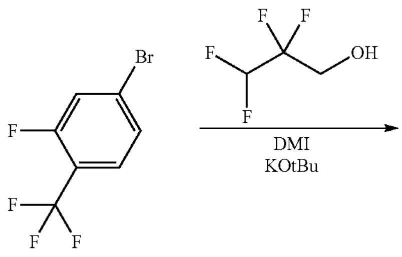

292p

-continued

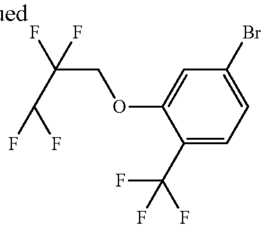

292q

-continued

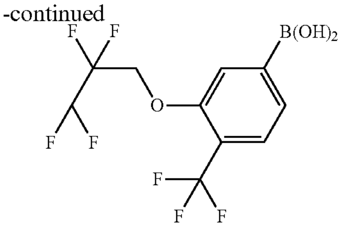

292r

4-Bromo-2-(2,2,3,3-tetrafluoro-propoxy)-1-trifluoromethyl-benzene was obtained by operations similar to those in Reaction 292-7 using appropriate starting compound and reagents.

$^1$H-NMR (400 MHz, $CDCl_3$) δ 7.74 (1H, d, J=2.4 Hz), 7.65 (1H, dd, J=2.4, 8.8 Hz), 6.88 (1H, d, J=8.8 Hz), 6.06 (1H, dt, J=5.4, 53.2 Hz), 4.40 (2H, t, J=11.2 Hz).

(Reaction 292-13)

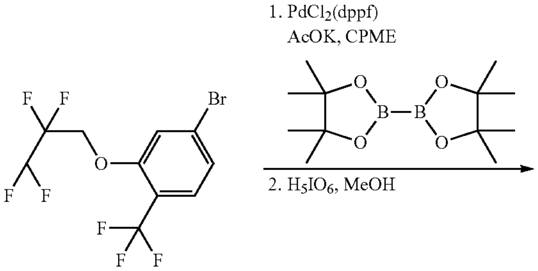

292q

A solution of 4-bromo-2-(2,2,3,3-tetrafluoro-propoxy)-1-trifluoromethyl-benzene (482 mg, 1.36 mmol), pinacol diborane (379 mg, 1.49 mmol), palladium dichloride-diphenylphosphinoferrocene (111 mg, 0.136 mmol) and potassium acetate (400 mg, 4.08 mmol) in cyclopentyl methyl ether (2.41 mL) was heated with stirring at 115° C. for one hour in a nitrogen atmosphere. After cooling to room temperature, water (1 mL) was added to the reaction mixture, and the upper cyclopentyl methyl ether layer was extracted. Methanol (1 mL) was added to the organic layer. Periodic acid (1.24 g, 5.44 mmol) was added at 0° C., and the mixture was warmed to room temperature and stirred for one hour. Water was added to the reaction mixture, followed by extraction with ethyl acetate. The organic layer was dried over anhydrous sodium sulfate and concentrated under reduced pressure. The residue was purified by silica gel column chromatography (hexane:ethyl acetate=3:1→1:1) and further treated with hexane to give 3-(2,2,3,3-tetrafluoro-propoxy)-4-trifluoromethylphenylboronic acid as a pale brown solid (260 mg, 60%).

MS (ESI) m/z=319 (M−H)−.

The arylboronic acid reagents shown below were synthesized by operations similar to those in Reaction 292-7 and Reaction 292-13 using appropriate starting compounds and used in the synthesis of the compounds in Table 176.

TABLE 180

| Target Compound | Raw material | Arylboronic acid structure | MS (m/z) |
|---|---|---|---|
| 1209 | 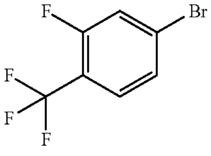 [SMILES: Fc1cc(Br)ccc1C(F)(F)F] | 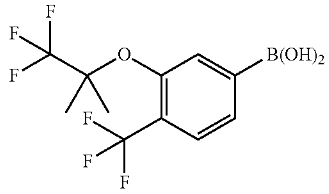 [SMILES: CC(C)(Oc1cc(B(O)O)ccc1C(F)(F)F)C(F)(F)F] | 315 (M − H)− |
| 1210 | 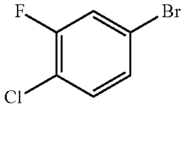 | 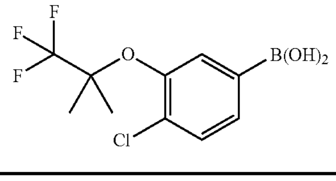 | 281 (M − H)− |

The arylboronic acid reagent used in the synthesis of Compound 1224 (4-bromo-3-[1,1,2,2,2-$^2H_5$]ethoxy-1-fluorophenylboronic acid) was synthesized by the following method.

(Reaction 292-14)

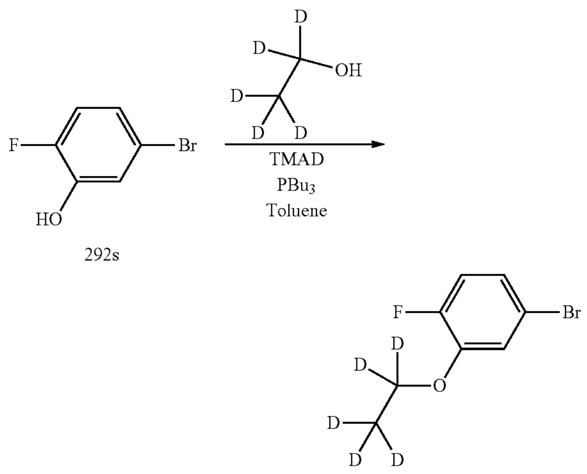

292s

292t

Toluene was added to a mixture of 5-bromo-2-fluorophenol (382 mg, 2.0 mmol), ethanol-$d^5$ (0.104 mL, 2.0 mmol) and N,N,N',N'-tetramethylazodicarboxamide (465 mg, 2.7 mmol). Tributylphosphine (0.622 mL, 2.5 mmol) was added at 0° C. and the mixture was stirred for 14 hours. The reaction solution was purified by silica gel column chromatography to give 4-bromo-2-[1,1,2,2,2-$^2H_5$]ethoxy-1-fluoro-benzene (416 mg, 93%).

$^1$H-NMR (400 MHz, $CDCl_3$) δ 7.07 (1H, dd, J=2.1, 7.4 Hz), 7.00 (1H, ddd, J=2.1, 4.1, 8.4 Hz), 6.94 (1H, dd, J=8.4, 10.7 Hz).

(Reaction 292-15)

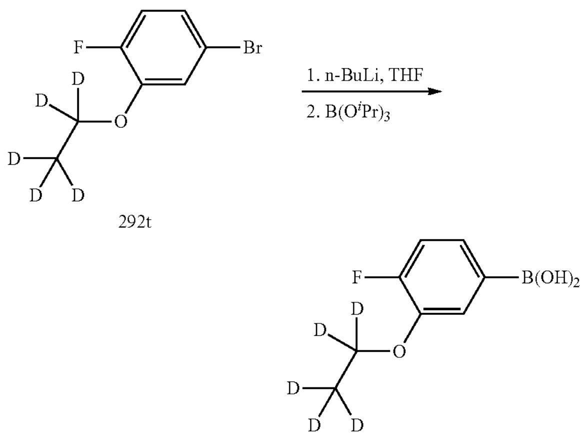

292t

292u

4-Bromo-3-[1,1,2,2,2-$^2H_5$]ethoxy-1-fluorophenylboronic acid was obtained by operations similar to those in Reaction 292-5 using 4-bromo-2-[1,1,2,2,2-$^2H_5$]ethoxy-1-fluoro-benzene as a starting material.

MS (ESI) m/z=188 (M−H)−.

The arylboronic acid reagents shown below were synthesized by operations similar to those in Reaction 292-14 and Reaction 292-5 using appropriate starting compounds and used in the synthesis of the compounds in Table 176.

TABLE 181

| Target Compound | Raw material | Arylboronic acid structure | MS (m/z) |
| --- | --- | --- | --- |
| 1207 | 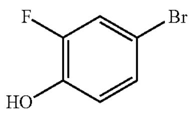 | 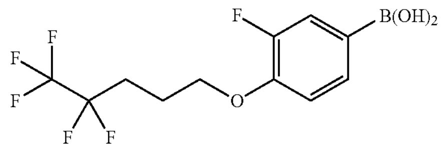 [SMILES: OB(O)c1ccc(OCCCC(F)(F)C(F)(F)F)c(F)c1] | 315 (M − H)− |
| 1211 | 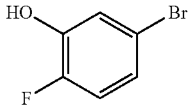 | 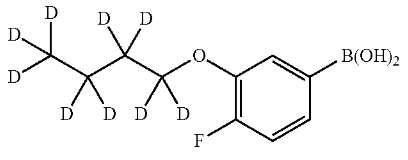 [SMILES: [2H]C([2H])([2H])C([2H])([2H])C([2H])([2H])C([2H])([2H])Oc1cc(B(O)O)ccc1F] | 220 (M − H)− |
| 1218 | 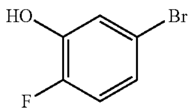 | 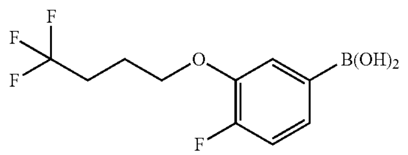 [SMILES: OB(O)c1ccc(F)c(OCCCC(F)(F)F)c1] | 265 (M − H)− |

TABLE 181-continued

| Target Compound | Raw material | Arylboronic acid structure | MS (m/z) |
|---|---|---|---|
| 1225 | 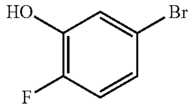 | 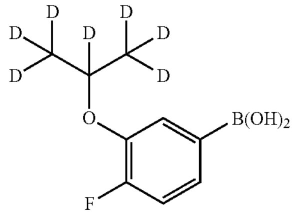 [SMILES: [2H]C([2H])([2H])C([2H])(Oc1cc(B(O)O)ccc1F)C([2H])([2H])[2H]] | 204 (M − H)− |

The arylboronic acid reagent used in the synthesis of Compound 1215 (3-fluoro-4-(3-fluoro-propoxy)phenylboronic acid) was synthesized by the following method.

(Reaction 292-16)

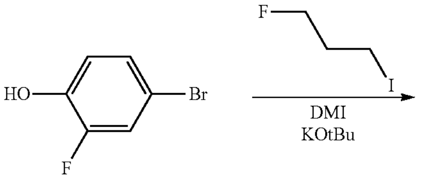

292v

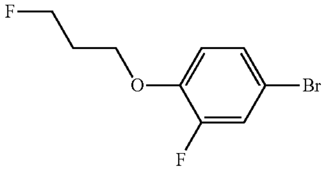

292w

4-Bromo-2-fluorophenol (382 mg, 2.0 mmol) was dissolved in DMI (0.5 mL), and potassium tert-butoxide (224 mg, 2.0 mmol) was added at room temperature. 1-Iodo-3-fluoropropane (376 mg, 2.0 mmol) was added to the reaction solution, and the mixture was heated to 60° C. and stirred for six hours. The reaction solution was purified by silica gel column chromatography to give 4-bromo-2-fluoro-1-(3-fluoro-propoxy)-benzene (410 mg, 82%).

$^1$H-NMR (400 MHz, $CDCl_3$) δ 7.10 (1H, dd, J=2.1, 7.4 Hz), 7.03 (1H, ddd, J=2.4, 3.9, 8.6 Hz), 6.95 (1H, dd, J=8.7, 10.7 Hz), 4.66 (2H, dt, J=5.6, 46.9 Hz), 4.15 (2H, t, J=6.1 Hz), 2.20 (2H, ddt, J=5.8, 5.8, 26.1 Hz).

(Reaction 292-17)

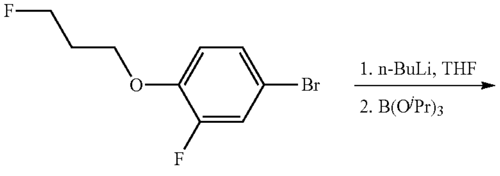

292w

-continued

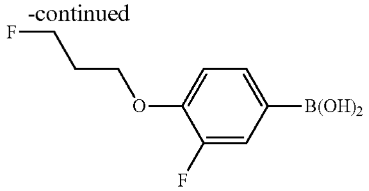

292x

3-Fluoro-4-(3-fluoro-propoxy)phenylboronic acid was obtained by operations similar to those in Reaction 292-5 using 4-bromo-2-fluoro-1-(3-fluoro-propoxy)-benzene as a starting material.

MS (ESI) m/z=215 (M−H)−.

The arylboronic acid reagent used in the synthesis of Compound 1212 (2,2,3,3-tetrafluoro-2,3-dihydro-benzo[1,4]dioxin-6-yl-boronic acid) was synthesized by the following method.

(Reaction 292-18)

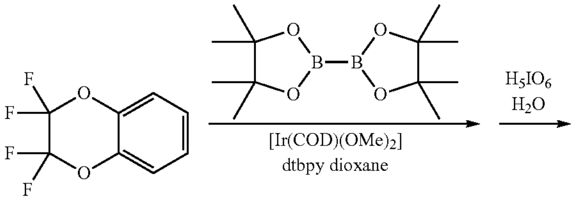

292y

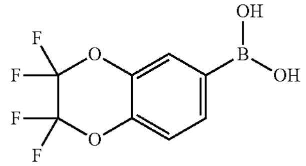

292z 2,2,3,3-Tetrafluoro-1,4-benzodioxane (484 mg), bis(pinacolato)diboron (295 mg), $[Ir(COD)(OMe)]_2$ (15.4 mg) and 4,4'di-tert-butyl-2,2'-dipyridyl (12.5 mg) were mixed. 1,4-Dioxane (0.5 mL) was added in a nitrogen atmosphere and stirred at 100° C. for two hours. MeOH (0.5 mL) was added to the reaction solution, and metaperiodic acid (1.06 g) was added in four portions under ice-cooling. Water was added to the reaction solution, followed by extraction with ethyl acetate and concentration. The resulting mixture was purified by silica gel column chromatography to give 2,2,3,3-tetrafluoro-2,3-dihydro-benzo[1,4]dioxin-6-yl-boronic acid (230 mg, 39%).

MS (ESI) m/z=251 (M−H)−.

Example 293

2-(4-Fluoro-2,5-dimethyl-phenyl)-8-{(E)-2-[4-(4-fluoromethyl-4-hydroxy-piperidine-1-carbonyl)-2,6-dimethyl-phenyl]-ethenesulfonyl}-1,3,8-triaza-spiro[4.5]dec-1-en-4-one (Compound 1239)

(Reaction 293-1)

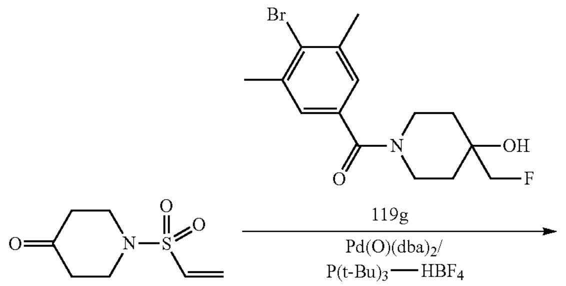

119g

263b

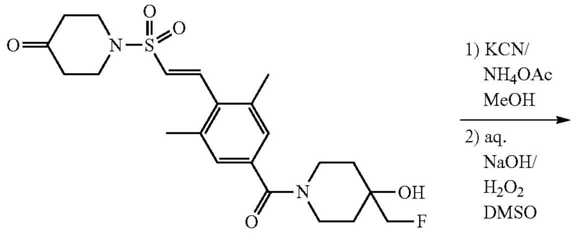

293a

-continued

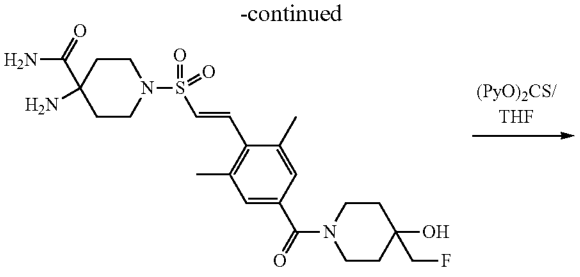

293b

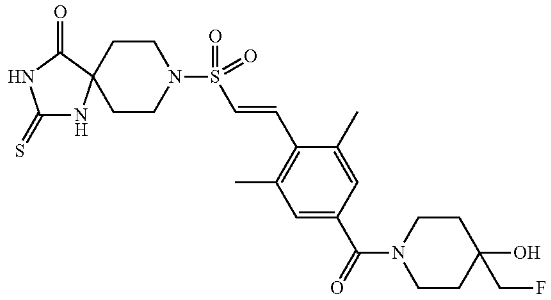

293c

8-{(E)-2-[4-(4-Fluoromethyl-4-hydroxy-piperidine-1-carbonyl)-2,6-dimethyl-phenyl]-ethenesulfonyl}-2-thioxo-1,3,8-triaza-spiro[4.5]decan-4-one was obtained by operations similar to those in Reaction 119-1, Reaction 233-3, Reaction 233-4 and Reaction 292-2 using 1-ethenesulfonyl-piperidin-4-one as a starting material.

MS (ESI) m/z=539 (M+H)+.

(Reaction 293-2)

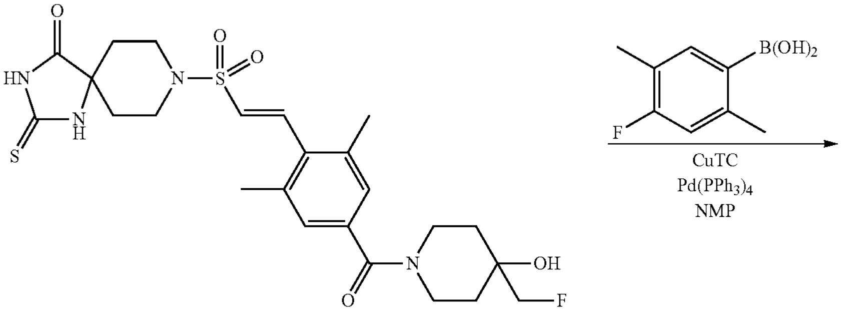

293c

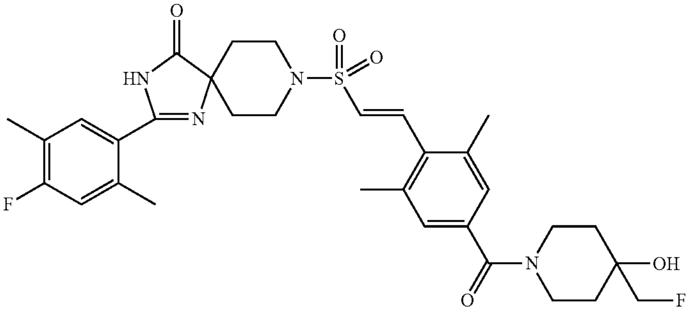

Compound 1239

2-(4-Fluoro-2,5-dimethyl-phenyl)-8-{(E)-2-[4-(4-fluoromethyl-4-hydroxy-piperidine-1-carbonyl)-2,6-dimethyl-phenyl]-ethenesulfonyl}-1,3,8-triaza-spiro[4.5]dec-1-en-4-one was obtained by operations similar to those in Reaction using 8-{(E)-2-[4-(4-fluoromethyl-4-hydroxy-piperidine-1-carbonyl)-2,6-dimethyl-phenyl]-ethenesulfonyl}-2-thioxo-1,3,8-triaza-spiro[4.5]decan-4-one as a starting material.

MS (ESI) m/z=629 (M+H)+.

The example compounds shown below were obtained by operations similar to those in Reaction 293-2 using appropriate starting compounds.

Compounds 1240 to 1281

TABLE 182

| Target Compound | Structure | LCMS condition | Retention time (min) | MS (m/z) |
|---|---|---|---|---|
| 1240 | 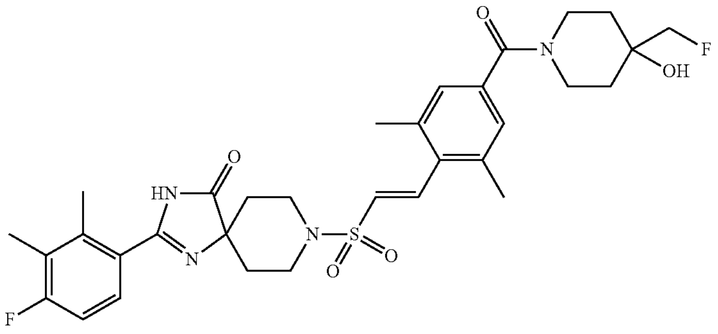 [SMILES: Cc1cc(C(=O)N2CCC(O)(CF)CC2)cc(C)c1/C=C/S(=O)(=O)N1CCC2(CC1)N=C(c1ccc(F)c(C)c1C)NC2=O] | LCMS-F-1 | 0.94 | 629 (M + H)+ |
| 1241 | 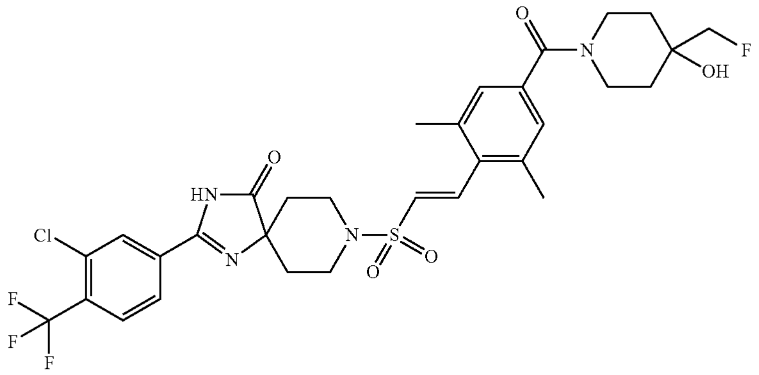 | LCMS-B-1 | 2.38 | 686 (M + H)+ |
| 1242 | 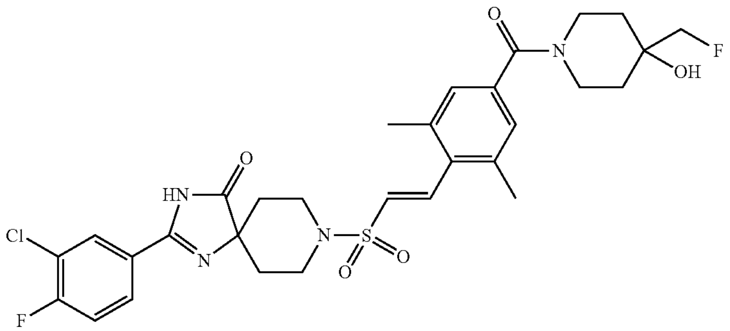 | LCMS-F-1 | 0.73 | 636 (M + H)+ |
| 1243 | 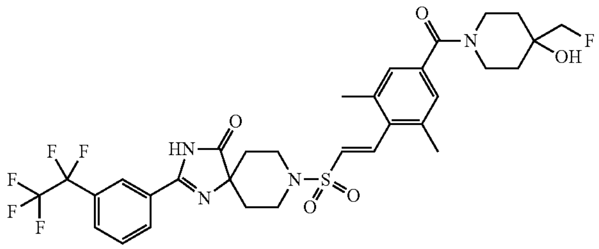 [SMILES: Cc1cc(C(=O)N2CCC(O)(CF)CC2)cc(C)c1/C=C/S(=O)(=O)N1CCC2(CC1)N=C(c1cccc(C(F)(F)C(F)(F)F)c1)NC2=O] | LCMS-F-1 | 1.01 | 701 (M + H)+ |

TABLE 182-continued
| Target Compound | Structure | LCMS condition | Retention time (min) | MS (m/z) |
|---|---|---|---|---|
| 1244 | 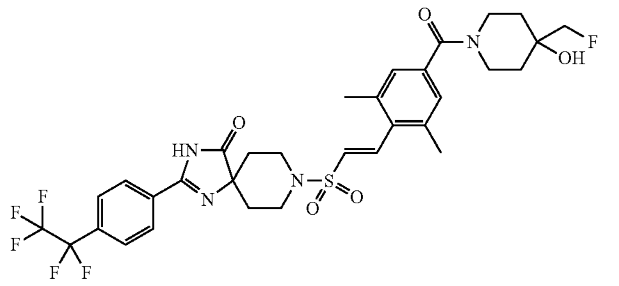 [SMILES: Cc1cc(C(=O)N2CCC(O)(CF)CC2)cc(C)c1/C=C/S(=O)(=O)N1CCC2(CC1)N=C(c1ccc(C(F)(F)C(F)(F)F)cc1)NC2=O] | LCMS-F-1 | 1.02 | 701 (M + H)+ |
| 1245 | 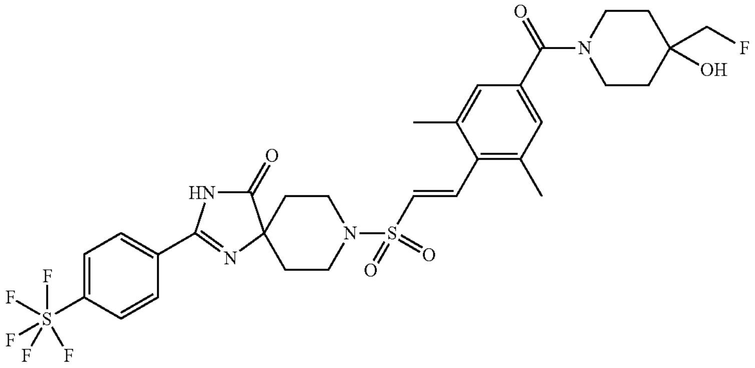 [SMILES: Cc1cc(C(=O)N2CCC(O)(CF)CC2)cc(C)c1/C=C/S(=O)(=O)N1CCC2(CC1)N=C(c1ccc(S(F)(F)(F)(F)F)cc1)NC2=O] | LCMS-F-1 | 1.01 | 709 (M + H)+ |
| 1246 | 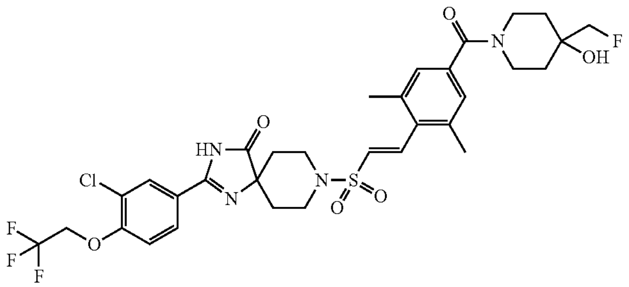 [SMILES: Cc1cc(C(=O)N2CCC(O)(CF)CC2)cc(C)c1/C=C/S(=O)(=O)N1CCC2(CC1)N=C(c1ccc(OCC(F)(F)F)c(Cl)c1)NC2=O] | LCMS-F-1 | 1.00 | 715 (M + H)+ |
| 1247 | 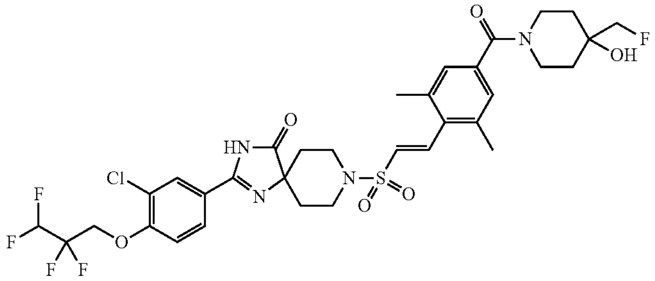 [SMILES: Cc1cc(C(=O)N2CCC(O)(CF)CC2)cc(C)c1/C=C/S(=O)(=O)N1CCC2(CC1)N=C(c1ccc(OCC(F)(F)C(F)F)c(Cl)c1)NC2=O] | LCMS-F-1 | 1.01 | 747 (M + H)+ |
| 1248 | 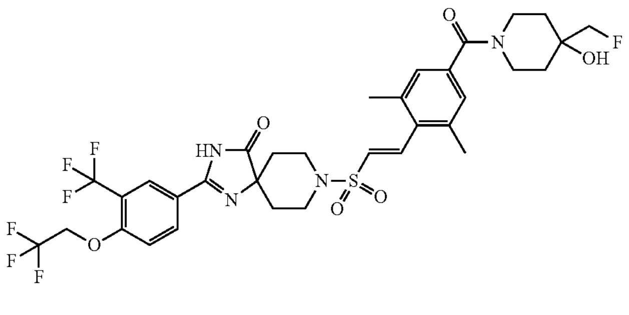 [SMILES: Cc1cc(C(=O)N2CCC(O)(CF)CC2)cc(C)c1/C=C/S(=O)(=O)N1CCC2(CC1)N=C(c1ccc(OCC(F)(F)F)c(C(F)(F)F)c1)NC2=O] | LCMS-F-1 | 1.01 | 749 (M + H)+ |

TABLE 182-continued
| Target Compound | Structure | LCMS condition | Retention time (min) | MS (m/z) |
| --- | --- | --- | --- | --- |
| 1249 | 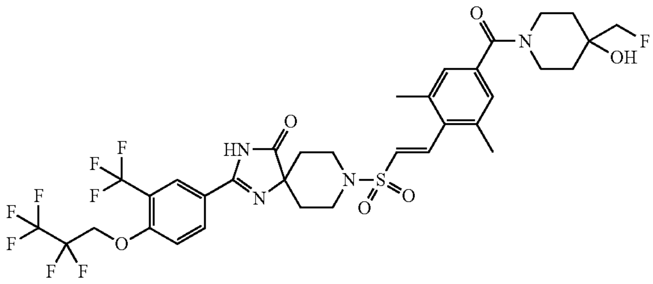 [SMILES: Cc1cc(C(=O)N2CCC(O)(CF)CC2)cc(C)c1/C=C/S(=O)(=O)N1CCC2(CC1)N=C(c1ccc(OCC(F)(F)C(F)(F)F)c(C(F)(F)F)c1)NC2=O] | LCMS-B-1 | 2.48 | 799 (M + H)+ |
| 1250 | 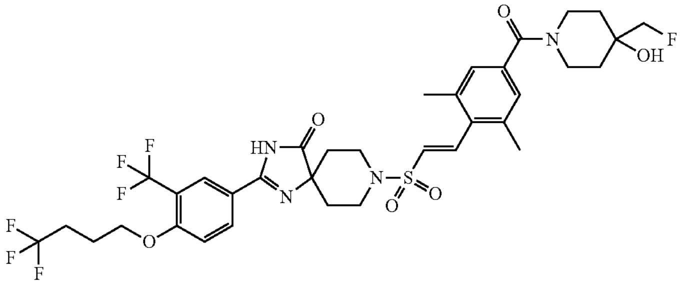 [SMILES: Cc1cc(C(=O)N2CCC(O)(CF)CC2)cc(C)c1/C=C/S(=O)(=O)N1CCC2(CC1)N=C(c1ccc(OCCCC(F)(F)F)c(C(F)(F)F)c1)NC2=O] | LCMS-B-1 | 2.41 | 777 (M + H)+ |
| 1251 | 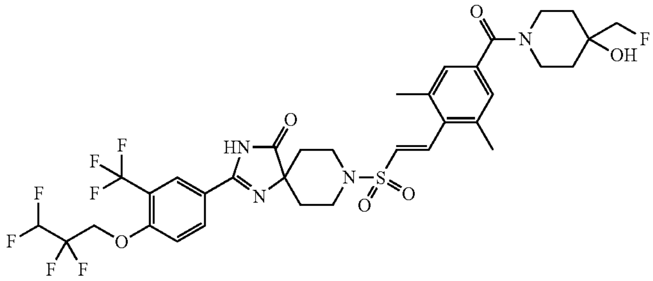 [SMILES: Cc1cc(C(=O)N2CCC(O)(CF)CC2)cc(C)c1/C=C/S(=O)(=O)N1CCC2(CC1)N=C(c1ccc(OCC(F)(F)C(F)F)c(C(F)(F)F)c1)NC2=O] | LCMS-F-1 | 1.00 | 781 (M + H)+ |
| 1252 | 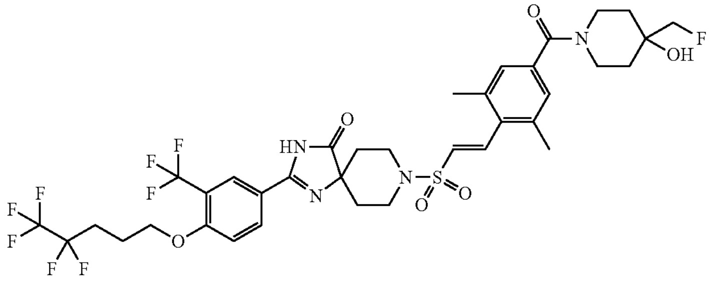 [SMILES: Cc1cc(C(=O)N2CCC(O)(CF)CC2)cc(C)c1/C=C/S(=O)(=O)N1CCC2(CC1)N=C(c1ccc(OCCCC(F)(F)C(F)(F)F)c(C(F)(F)F)c1)NC2=O] | LCMS-F-1 | 1.06 | 827 (M + H)+ |
| 1253 | 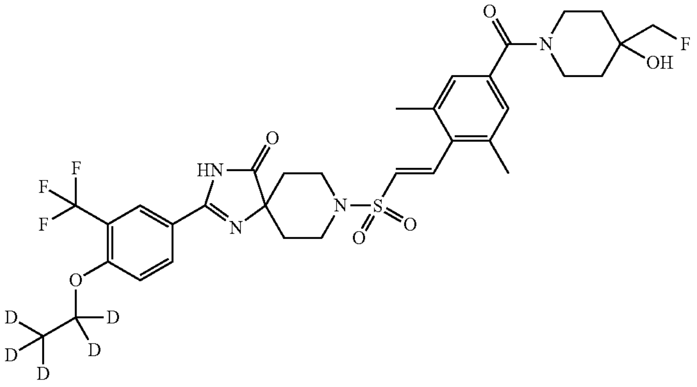 | LCMS-F-1 | 0.99 | 700 (M + H)+ |

TABLE 182-continued
| Target Compound | Structure | LCMS condition | Retention time (min) | MS (m/z) |
|---|---|---|---|---|
| 1254 | 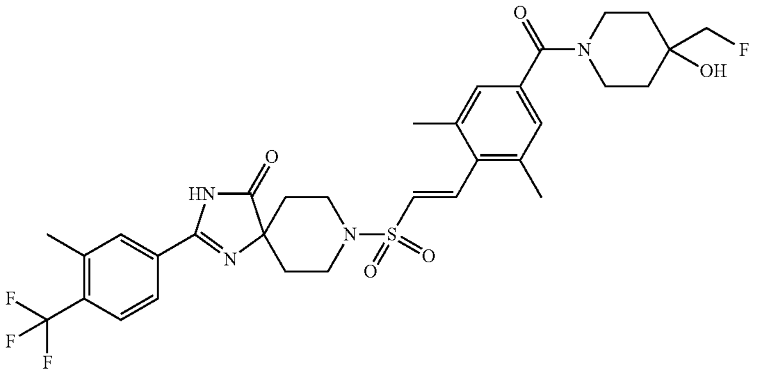 [SMILES: Cc1cc(C2=NC3(CCN(S(=O)(=O)/C=C/c4c(C)cc(C(=O)N5CCC(O)(CF)CC5)cc4C)CC3)C(=O)N2)ccc1C(F)(F)F] | LCMS-F-1 | 1.00 | 665 (M + H)+ |
| 1255 | 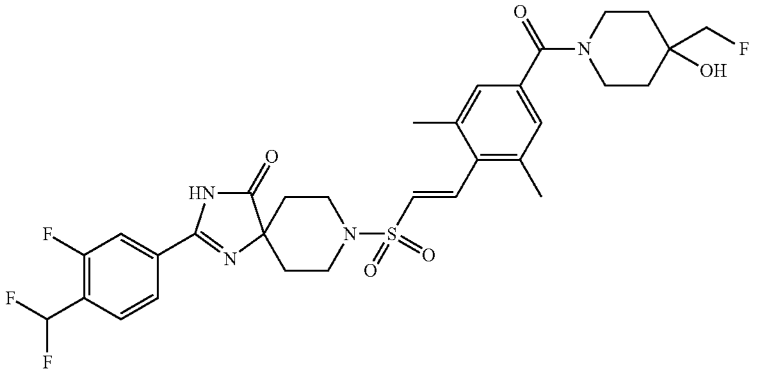 [SMILES: Cc1cc(C(=O)N2CCC(O)(CF)CC2)cc(C)c1/C=C/S(=O)(=O)N1CCC2(CC1)N=C(c1ccc(C(F)F)c(F)c1)NC2=O] | LCMS-F-1 | 0.93 | 651 (M + H)+ |
| 1256 | 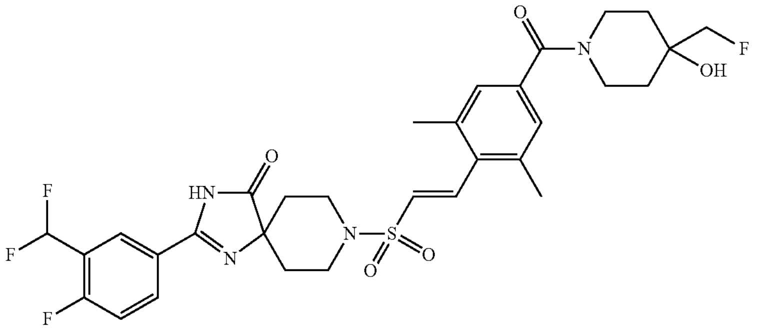 [SMILES: Cc1cc(C(=O)N2CCC(O)(CF)CC2)cc(C)c1/C=C/S(=O)(=O)N1CCC2(CC1)N=C(c1ccc(F)c(C(F)F)c1)NC2=O] | LCMS-F-1 | 0.82 | 651 (M + H)+ |
| 1257 | 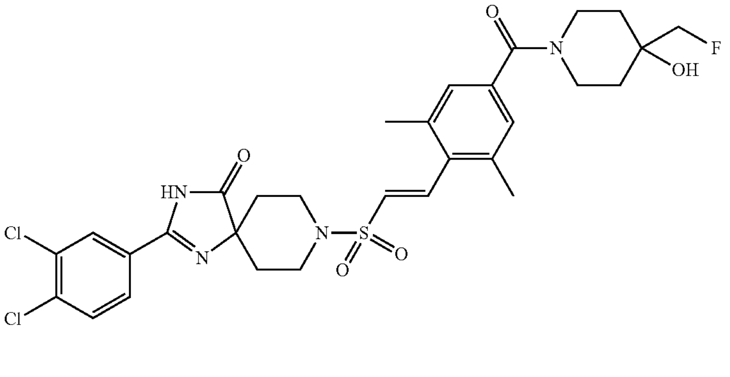 [SMILES: Cc1cc(C(=O)N2CCC(O)(CF)CC2)cc(C)c1/C=C/S(=O)(=O)N1CCC2(CC1)N=C(c1ccc(Cl)c(Cl)c1)NC2=O] | LCMS-F-1 | 1.00 | 651 (M + H)+ |

TABLE 182-continued
| Target Compound | Structure | LCMS condition | Retention time (min) | MS (m/z) |
|---|---|---|---|---|
| 1258 | 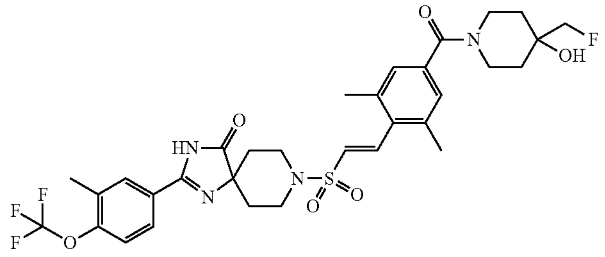 [SMILES: Cc1cc(C2=NC3(CCN(S(=O)(=O)/C=C/c4c(C)cc(C(=O)N5CCC(O)(CF)CC5)cc4C)CC3)C(=O)N2)ccc1OC(F)(F)F] | LCMS-F-1 | 1.01 | 681 (M + H)+ |
| 1259 | 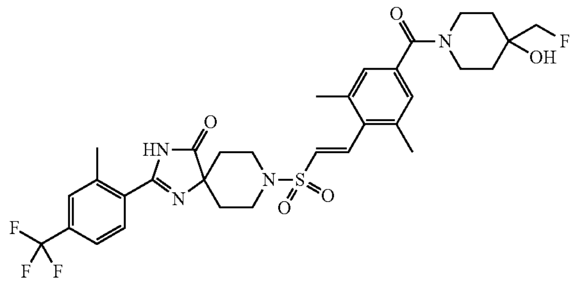 [SMILES: Cc1cc(C(F)(F)F)ccc1C1=NC2(CCN(S(=O)(=O)/C=C/c3c(C)cc(C(=O)N4CCC(O)(CF)CC4)cc3C)CC2)C(=O)N1] | LCMS-F-1 | 0.96 | 665 (M + H)+ |
| 1260 | 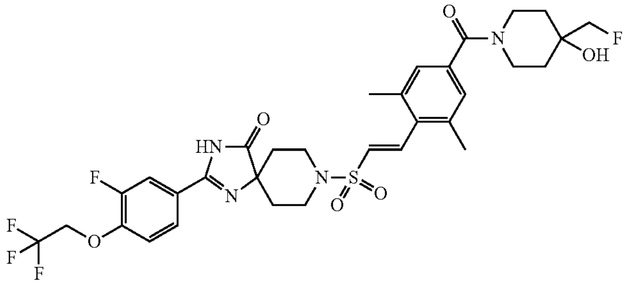 [SMILES: Cc1cc(C(=O)N2CCC(O)(CF)CC2)cc(C)c1/C=C/S(=O)(=O)N1CCC2(CC1)N=C(c1ccc(OCC(F)(F)F)c(F)c1)NC2=O] | LCMS-F-1 | 0.95 | 699 (M + H)+ |
| 1261 | 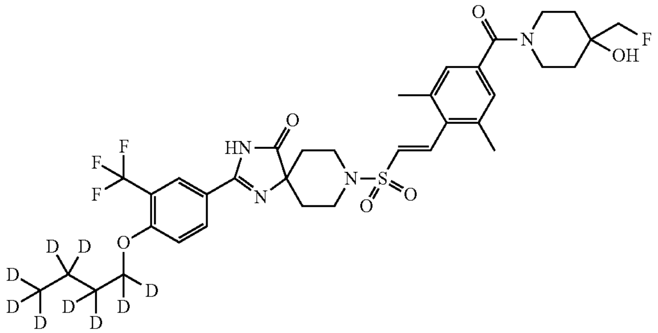 [SMILES: [2H]C([2H])([2H])C([2H])([2H])C([2H])([2H])C([2H])([2H])Oc1ccc(C2=NC3(CCN(S(=O)(=O)/C=C/c4c(C)cc(C(=O)N5CCC(O)(CF)CC5)cc4C)CC3)C(=O)N2)cc1C(F)(F)F] | LCMS-F-1 | 1.04 | 732 (M + H)+ |
| 1262 | 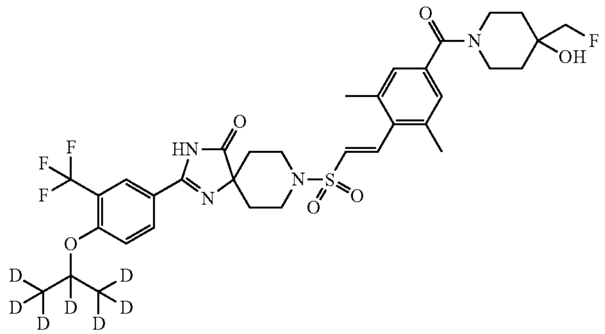 [SMILES: [2H]C([2H])([2H])C([2H])(Oc1ccc(C2=NC3(CCN(S(=O)(=O)/C=C/c4c(C)cc(C(=O)N5CCC(O)(CF)CC5)cc4C)CC3)C(=O)N2)cc1C(F)(F)F)C([2H])([2H])[2H]] | LCMS-F-1 | 1.01 | 716 (M + H)+ |

TABLE 182-continued
| Target Compound | Structure | LCMS condition | Retention time (min) | MS (m/z) |
|---|---|---|---|---|
| 1263 | 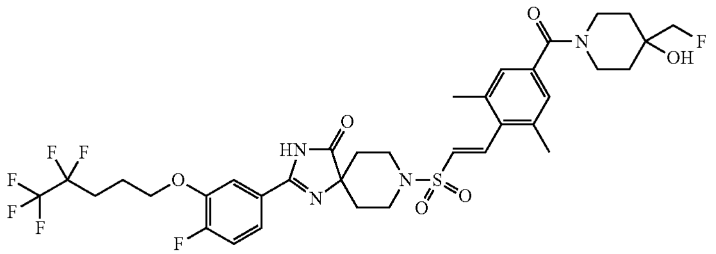 [SMILES: Cc1cc(C(=O)N2CCC(O)(CF)CC2)cc(C)c1/C=C/S(=O)(=O)N1CCC2(CC1)N=C(c1ccc(F)c(OCCCC(F)(F)C(F)(F)F)c1)NC2=O] | LCMS-F-1 | 1.05 | 777 (M + H)+ |
| 1264 | 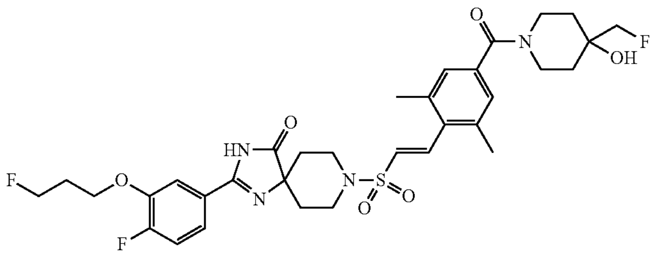 [SMILES: Cc1cc(C(=O)N2CCC(O)(CF)CC2)cc(C)c1/C=C/S(=O)(=O)N1CCC2(CC1)N=C(c1ccc(F)c(OCCCF)c1)NC2=O] | LCMS-F-1 | 0.95 | 677 (M + H)+ |
| 1265 | 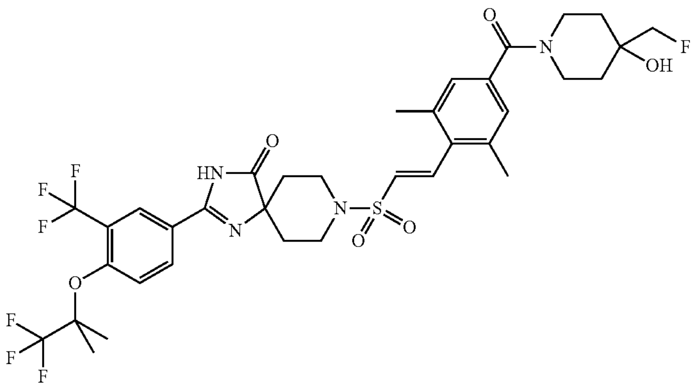 [SMILES: Cc1cc(C(=O)N2CCC(O)(CF)CC2)cc(C)c1/C=C/S(=O)(=O)N1CCC2(CC1)N=C(c1ccc(OC(C)(C)C(F)(F)F)c(C(F)(F)F)c1)NC2=O] | LCMS-F-1 | 1.04 | 777 (M + H)+ |
| 1266 | 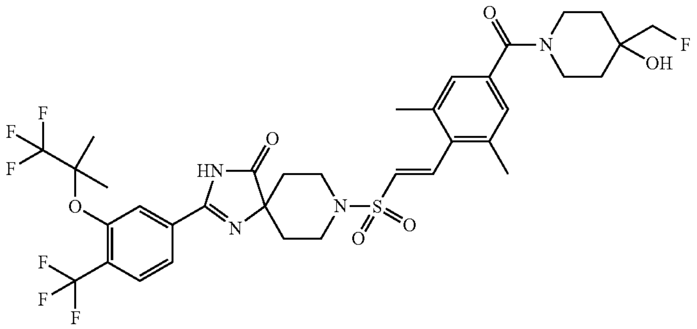 [SMILES: Cc1cc(C(=O)N2CCC(O)(CF)CC2)cc(C)c1/C=C/S(=O)(=O)N1CCC2(CC1)N=C(c1ccc(C(F)(F)F)c(OC(C)(C)C(F)(F)F)c1)NC2=O] | LCMS-F-1 | 1.04 | 777 (M + H)+ |
| 1267 | 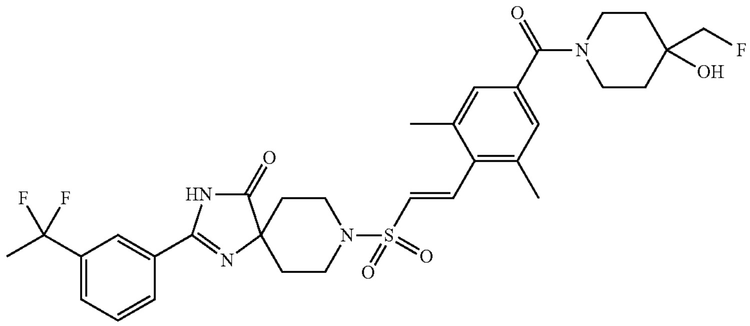 [SMILES: Cc1cc(C(=O)N2CCC(O)(CF)CC2)cc(C)c1/C=C/S(=O)(=O)N1CCC2(CC1)N=C(c1cccc(C(C)(F)F)c1)NC2=O] | LCMS-F-1 | 0.93 | 647 (M + H)+ |

TABLE 182-continued
| Target Compound | Structure | LCMS condition | Retention time (min) | MS (m/z) |
|---|---|---|---|---|
| 1268 | 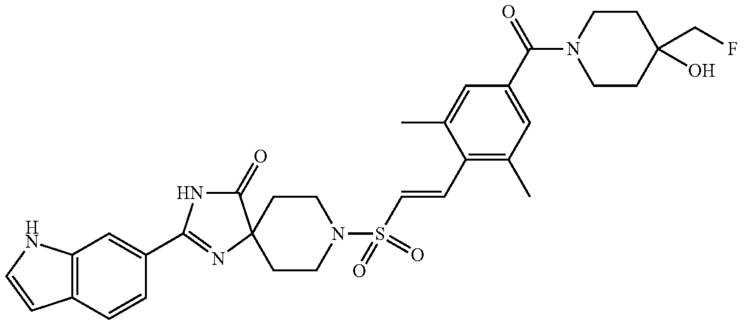 [SMILES: Cc1cc(C(=O)N2CCC(O)(CF)CC2)cc(C)c1/C=C/S(=O)(=O)N1CCC2(CC1)N=C(c1ccc3cc[nH]c3c1)NC2=O] | LCMS-F-1 | 0.88 | 622 (M + H)+ |
| 1269 | 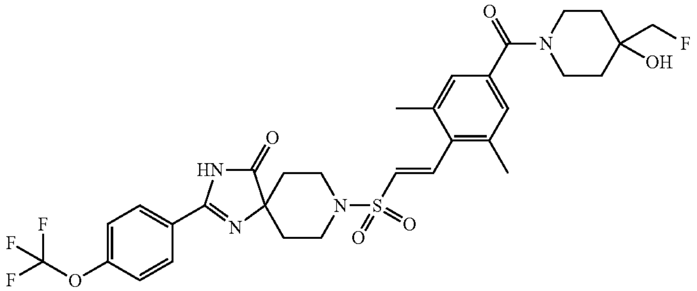 [SMILES: Cc1cc(C(=O)N2CCC(O)(CF)CC2)cc(C)c1/C=C/S(=O)(=O)N1CCC2(CC1)N=C(c1ccc(OC(F)(F)F)cc1)NC2=O] | LCMS-F-1 | 0.98 | 667 (M + H)+ |
| 1270 | 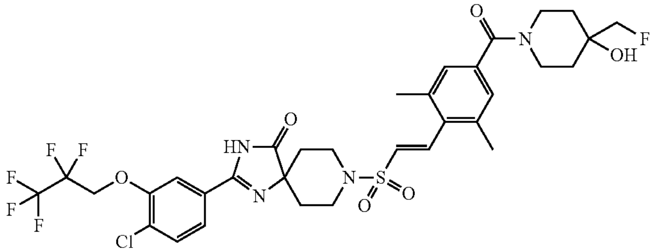 [SMILES: Cc1cc(C(=O)N2CCC(O)(CF)CC2)cc(C)c1/C=C/S(=O)(=O)N1CCC2(CC1)N=C(c1ccc(Cl)c(OCC(F)(F)C(F)(F)F)c1)NC2=O] | LCMS-F-1 | 1.04 | 765 (M + H)+ |
| 1271 | 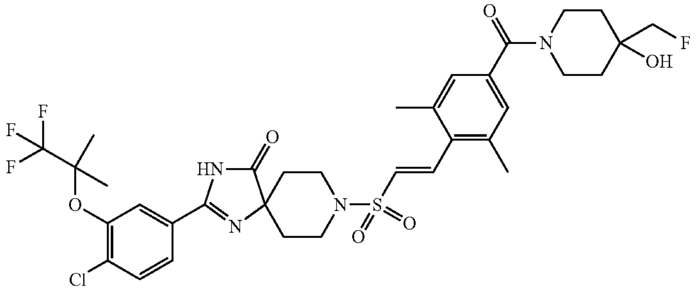 [SMILES: Cc1cc(C(=O)N2CCC(O)(CF)CC2)cc(C)c1/C=C/S(=O)(=O)N1CCC2(CC1)N=C(c1ccc(Cl)c(OC(C)(C)C(F)(F)F)c1)NC2=O] | LCMS-F-1 | 1.04 | 743 (M + H)+ |
| 1272 | 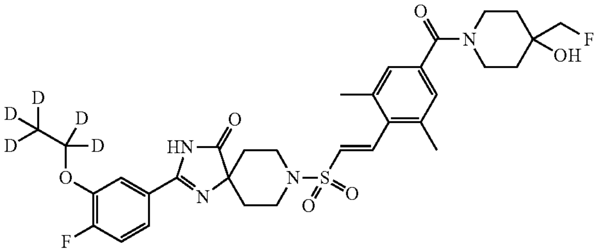 [SMILES: [2H]C([2H])([2H])C([2H])([2H])Oc1cc(C2=NC3(CCN(S(=O)(=O)/C=C/c4c(C)cc(C(=O)N5CCC(O)(CF)CC5)cc4C)CC3)C(=O)N2)ccc1F] | LCMS-F-1 | 0.95 | 650 (M + H)+ |

TABLE 182-continued
| Target Compound | Structure | LCMS condition | Retention time (min) | MS (m/z) |
|---|---|---|---|---|
| 1273 | 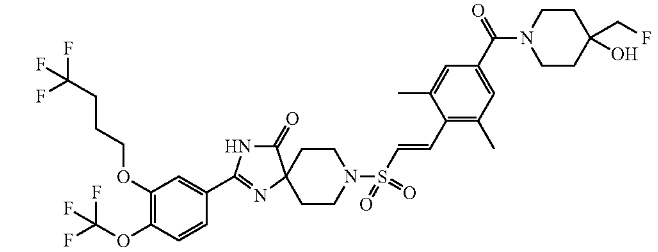 [SMILES: Cc1cc(C(=O)N2CCC(O)(CF)CC2)cc(C)c1/C=C/S(=O)(=O)N1CCC2(CC1)N=C(c1ccc(OC(F)(F)F)c(OCCCC(F)(F)F)c1)NC2=O] | LCMS-F-1 | 1.06 | 793 (M + H)+ |
| 1274 | 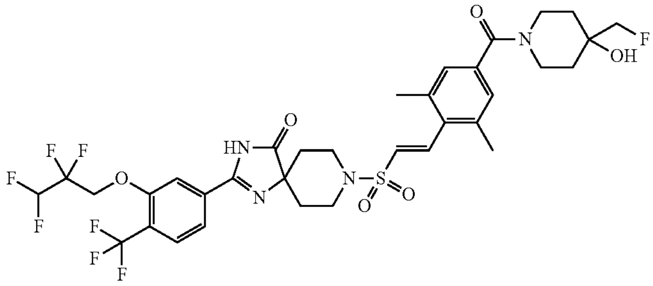 [SMILES: Cc1cc(C(=O)N2CCC(O)(CF)CC2)cc(C)c1/C=C/S(=O)(=O)N1CCC2(CC1)N=C(c1ccc(C(F)(F)F)c(OCC(F)(F)C(F)F)c1)NC2=O] | LCMS-F-1 | 1.02 | 781 (M + H)+ |
| 1275 | 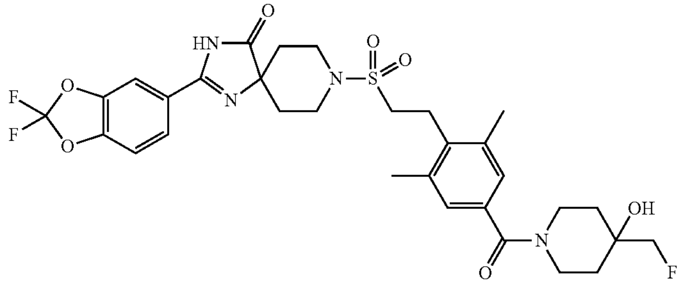 [SMILES: Cc1cc(C(=O)N2CCC(O)(CF)CC2)cc(C)c1CCS(=O)(=O)N1CCC2(CC1)N=C(c1ccc3c(c1)OC(F)(F)O3)NC2=O] | LCMS-G-1 | 1.11 | 665 (M + H)+ |
| 1276 | 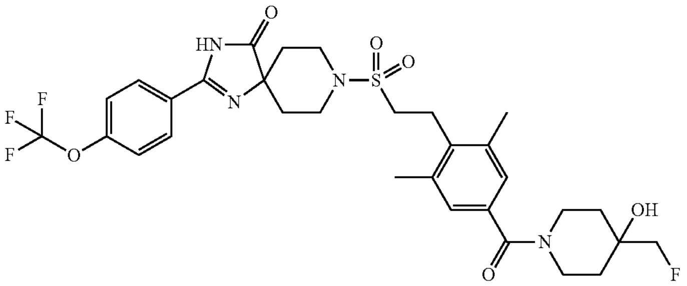 [SMILES: Cc1cc(C(=O)N2CCC(O)(CF)CC2)cc(C)c1CCS(=O)(=O)N1CCC2(CC1)N=C(c1ccc(OC(F)(F)F)cc1)NC2=O] | LCMS-G-1 | 1.11 | 669 (M + H)+ |
| 1277 | 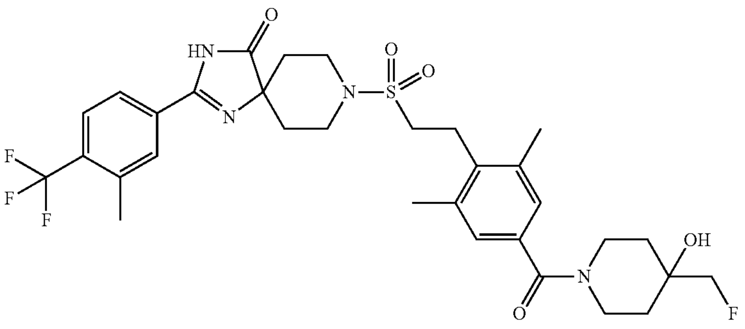 [SMILES: Cc1cc(C2=NC3(CCN(S(=O)(=O)CCc4c(C)cc(C(=O)N5CCC(O)(CF)CC5)cc4C)CC3)C(=O)N2)ccc1C(F)(F)F] | LCMS-G-1 | 1.13 | 667 (M + H)+ |

TABLE 182-continued
| Target Compound | Structure | LCMS condition | Retention time (min) | MS (m/z) |
| --- | --- | --- | --- | --- |
| 1278 | 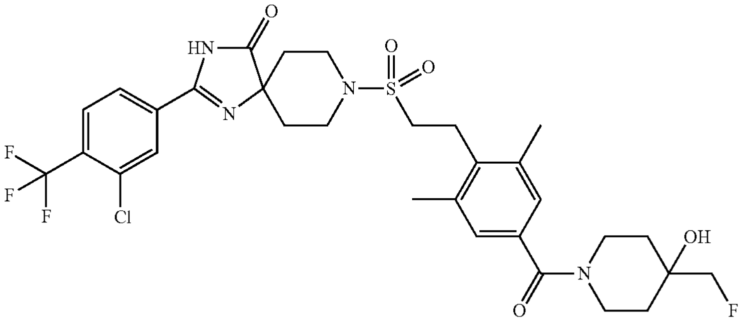 [SMILES: Cc1cc(C(=O)N2CCC(O)(CF)CC2)cc(C)c1CCS(=O)(=O)N1CCC2(CC1)N=C(c1ccc(C(F)(F)F)c(Cl)c1)NC2=O] | LCMS-G-1 | 1.16 | 687 (M + H)+ |
| 1279 | 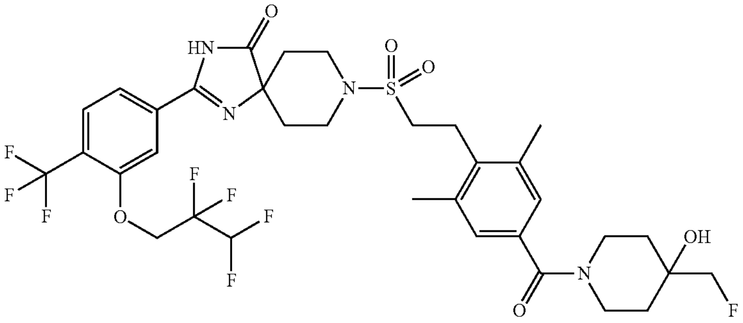 [SMILES: Cc1cc(C(=O)N2CCC(O)(CF)CC2)cc(C)c1CCS(=O)(=O)N1CCC2(CC1)N=C(c1ccc(C(F)(F)F)c(OCC(F)(F)C(F)F)c1)NC2=O] | LCMS-G-1 | 1.17 | 783 (M + H)+ |
| 1280 | 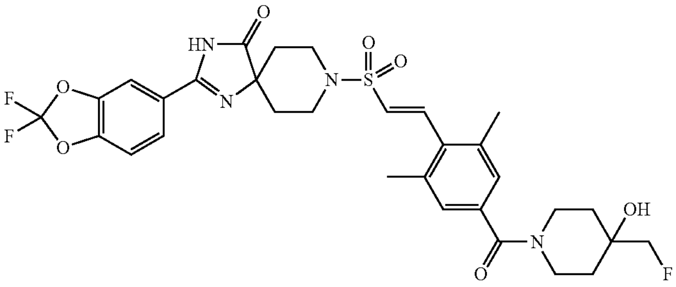 [SMILES: Cc1cc(C(=O)N2CCC(O)(CF)CC2)cc(C)c1/C=C/S(=O)(=O)N1CCC2(CC1)N=C(c1ccc3c(c1)OC(F)(F)O3)NC2=O] | LCMS-G-1 | 1.11 | 663 (M + H)+ |
| 1281 | 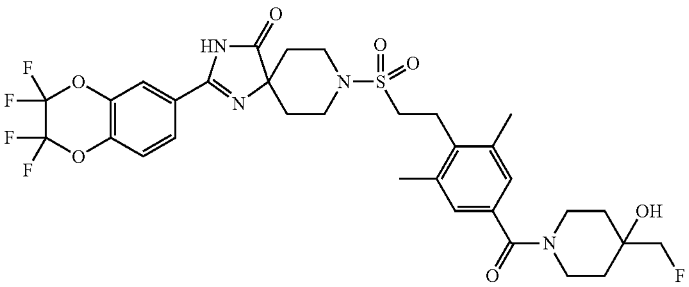 [SMILES: Cc1cc(C(=O)N2CCC(O)(CF)CC2)cc(C)c1CCS(=O)(=O)N1CCC2(CC1)N=C(c1ccc3c(c1)OC(F)(F)C(F)(F)O3)NC2=O] | LCMS-F-1 | 1.03 | 715 (M + H)+ |

Example 294

[3-(8-{(E)-2-[4-(4-Hydroxy-piperidine-1-carbonyl)-2,6-dimethyl-phenyl]-ethenesulfonyl}-4-oxo-1,3,8-triaza-spiro[4.5]dec-1-en-2-yl)-phenyl]-acetonitrile (Compound 1282)

(Reaction 294-1)

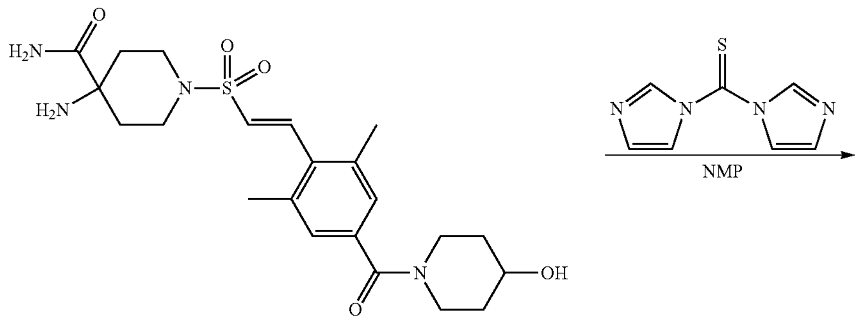

262c

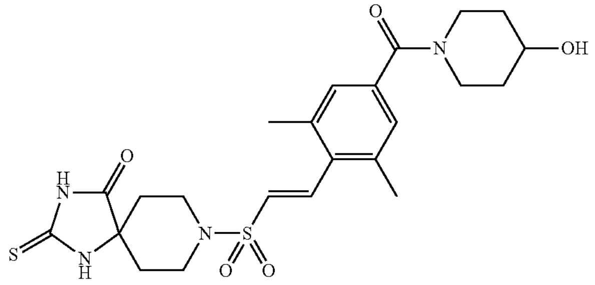

294a

8-{(E)-2-[4-(4-Hydroxy-piperidine-1-carbonyl)-2,6-dimethyl-phenyl]-ethenesulfonyl}-2-thioxo-1,3,8-triaza-spiro[4.5]decan-4-one was obtained by operations similar to those in Reaction 292-2 (using 1,1'-thiocarbonyldiimidazole) using appropriate reagents and starting material.

MS (ESI) m/z=507 (M+H)+.

(Reaction 294-2)

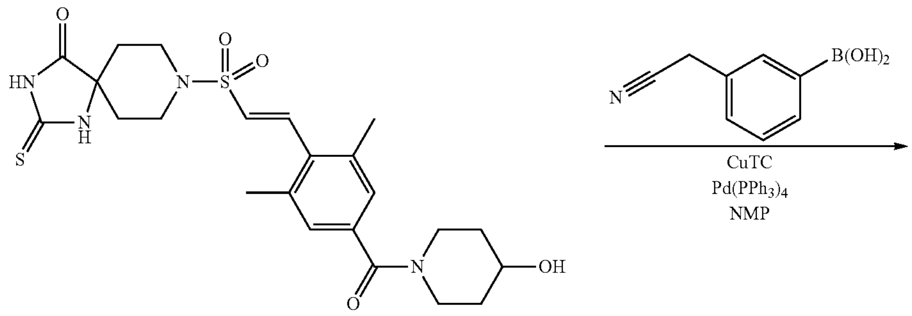

294a

-continued

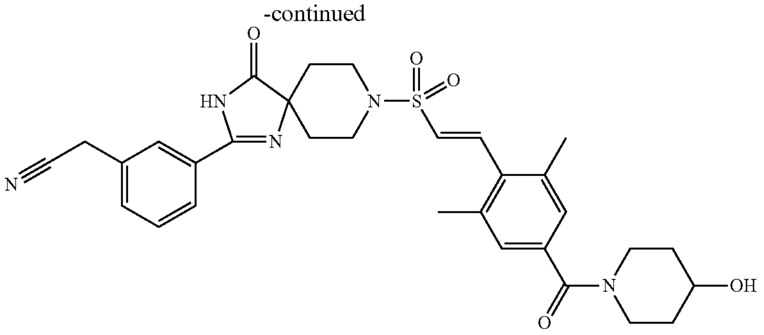

Compound 1282

[3-(8-{(E)-2-[4-(4-Hydroxy-piperidine-1-carbonyl)-2,6-dimethyl-phenyl]-ethenesulfonyl}-4-oxo-1,3,8-triaza-spiro[4.5]dec-1-en-2-yl)-phenyl]-acetonitrile was obtained by operations similar to those in Reaction 292-3 using 8-{(E)-2-[4-(4-hydroxy-piperidine-1-carbonyl)-2,6-dimethyl-phenyl]-ethenesulfonyl}-2-thioxo-1,3,8-triaza-spiro[4.5]decan-4-one as a starting material.

MS (ESI) m/z=590 (M+H)+.

Example 295

8-{(E)-2-[2-Methyl-4-(piperidin-4-yloxy)-phenyl]-ethenesulfonyl}-2-(3-trifluoromethoxy-phenyl)-1,3,8-triaza-spiro[4.5]dec-1-en-4-one trifluoroacetate (Compound 1283)

(Reaction 295-1)

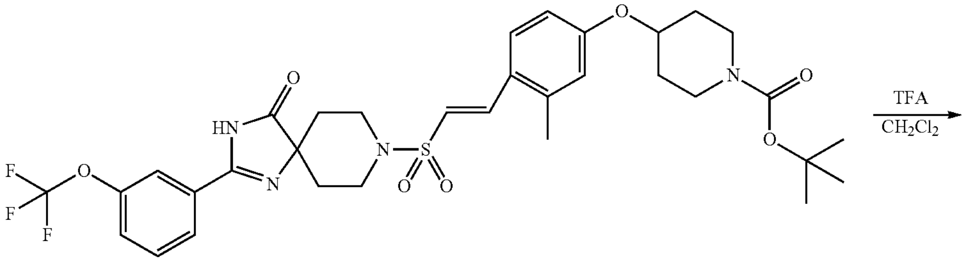

Compound 602

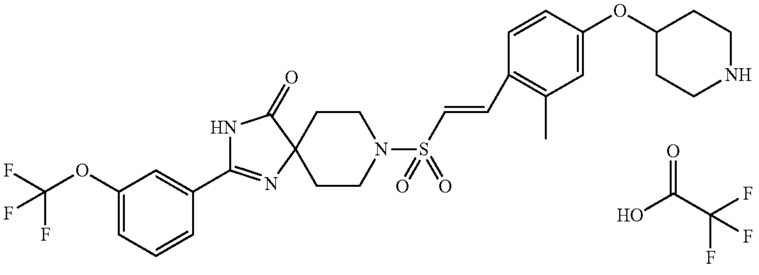

Compound 1283

8-{(E)-2-[2-Methyl-4-(piperidin-4-yloxy)-phenyl]-ethenesulfonyl}-2-(3-trifluoromethoxy-phenyl)-1,3,8-triaza-spiro[4.5]dec-1-en-4-one trifluoroacetate (Compound 1283) was obtained by operations similar to those in Reaction 4-1 using Compound 602 as a starting material.

MS (ESI) m/z=593 (M+H)+.

The example compounds shown below were obtained by operations similar to those in Reaction 295-1 using appropriate starting compounds. Compound 1285 was obtained as a free form by desalination post-treatment.

Compounds 1284 to Compound 1285
TABLE 183
| Starting Compound | Target Compound | Structure | LCMS condition | Retention time (min) | MS (m/z) |
|---|---|---|---|---|---|
| 928 | 1284 | 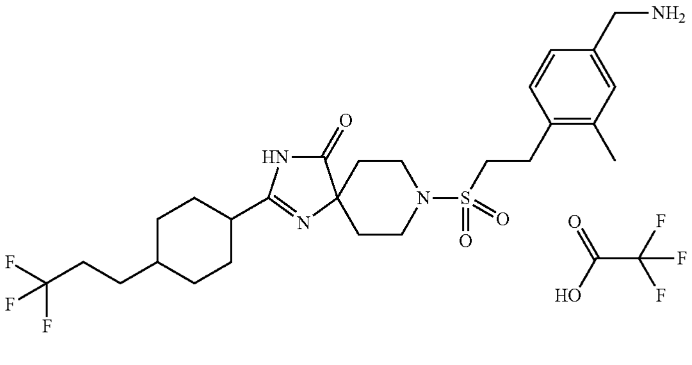 [SMILES: Cc1cc(CN)ccc1CCS(=O)(=O)N1CCC2(CC1)N=C(C1CCC(CCC(F)(F)F)CC1)NC2=O ; O=C(O)C(F)(F)F] | LCMS-B-1 | 1.67 | 543 (M + H)+ |
| 578 | 1285 | 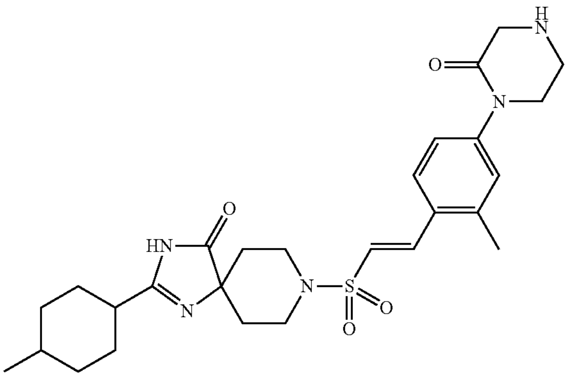 [SMILES: Cc1cc(N2CCNCC2=O)ccc1/C=C/S(=O)(=O)N1CCC2(CC1)N=C(C1CCC(C)CC1)NC2=O] | LCMS-A-1 | 1.69 | 528 (M + H)+ |
Example 296
8-[2-(2,6-Dimethyl-4-methylamino-phenyl)-ethane-sulfonyl]-2-pyrrolidin-2-yl-1,3,8-triaza-spiro[4.5]dec-1-en-4-one dihydrochloride (Compound 1286)
(Reaction 296-1)
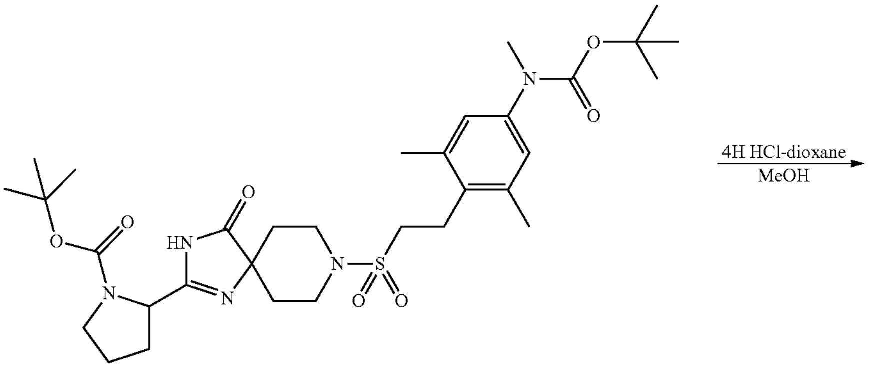
Compound 1033

-continued

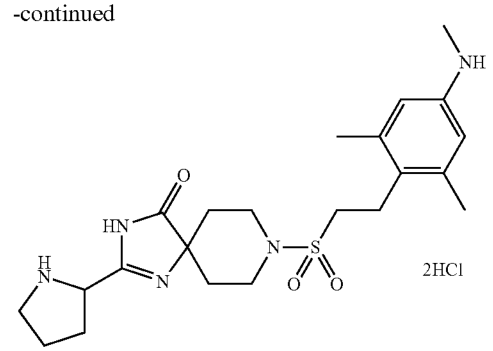

2HCl

Compound 1286

8-[2-(2,6-Dimethyl-4-methylamino-phenyl)-ethanesulfonyl]-2-pyrrolidin-2-yl-1,3,8-triaza-spiro[4.5]dec-1-en-4-one dihydrochloride (Compound 1286) was obtained by operations similar to those in Reaction 5-3 using Compound 1033 as a starting material.

MS (ESI) m/z=448 (M+H)+.

The example compounds shown below were obtained by operations similar to those in Reaction 296-1 using appropriate starting compounds.

Compounds 1287 to Compound 1288

TABLE 184

| Starting Compound | Target Compound | Structure | LCMS condition | Retention time (min) | MS (m/z) |
|---|---|---|---|---|---|
| 1034 | 1287 | HCl 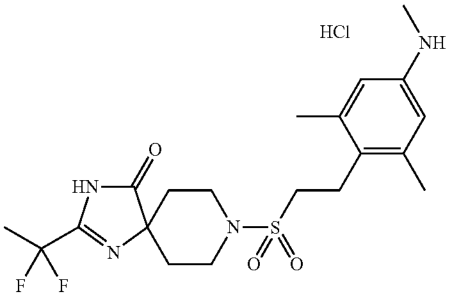 [SMILES: CNc1cc(C)c(CCS(=O)(=O)N2CCC3(CC2)N=C(C(C)(F)F)NC3=O)c(C)c1 ; Cl] | LCMS-B-1 | 1.44 | 443 (M + H)+ |
| 640 | 1288 | 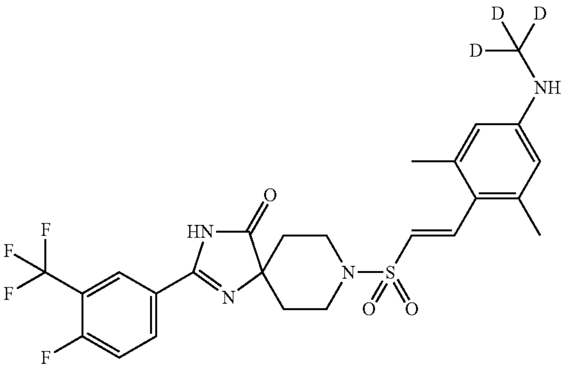 HCl | LCMS-F-1 | 1.05 | 542 (M + H)+ |

Example 297

8-[(E)-2-(2,6-Dimethyl-4-methylaminomethyl-phenyl)-ethenesulfonyl]-2-(4-methyl-cyclohexyl)-1,3,8-triaza-spiro[4.5]dec-1-en-4-one (Compound 1289)

(Reaction 297-1)

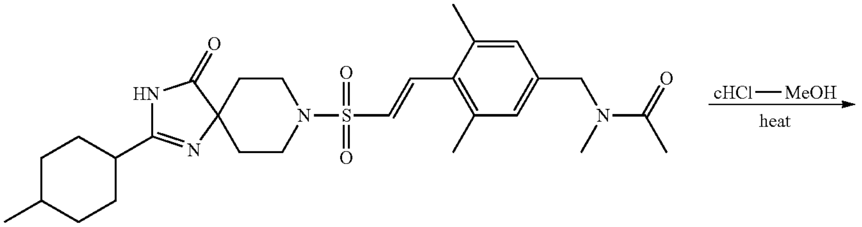

Compound 517

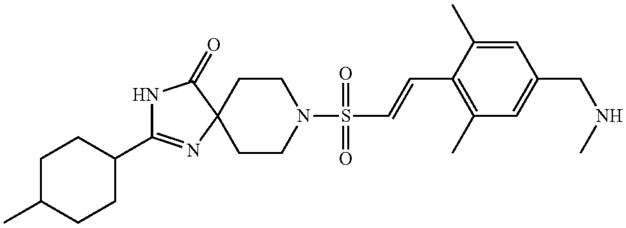

Compound 1289

8-[(E)-2-(2,6-Dimethyl-4-methylaminomethyl-phenyl)-ethenesulfonyl]-2-(4-methyl-cyclohexyl)-1,3,8-triaza-spiro[4.5]dec-1-en-4-one (Compound 1289) was obtained by operations similar to those in Reaction 50-2 (conversion to a free form by post-treatment) using Compound 517 as a starting material.

MS (ESI) m/z=487 (M+H)+.

The example compounds shown below were obtained by operations similar to those in Reaction 297-1 using appropriate starting compounds.

Compounds 1290 to Compound 1292

TABLE 185

| Starting Compound | Target Compound | Structure | LCMS condition | Retention time (min) | MS (m/z) |
|---|---|---|---|---|---|
| 558 | 1290 | 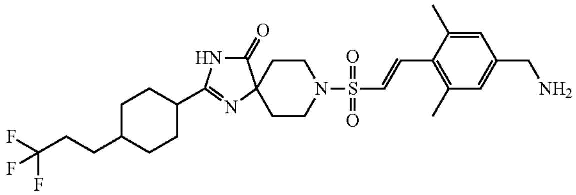 [SMILES: Cc1cc(CN)cc(C)c1/C=C/S(=O)(=O)N1CCC2(CC1)N=C(C1CCC(CCC(F)(F)F)CC1)NC2=O] | LCMS-D-1 | 2.27 | 555 (M + H)+ |
| 522 | 1291 | 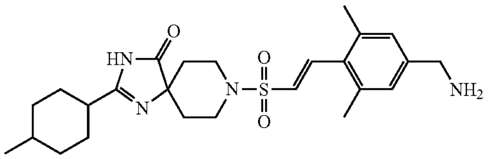 [SMILES: Cc1cc(CN)cc(C)c1/C=C/S(=O)(=O)N1CCC2(CC1)N=C(C1CCC(C)CC1)NC2=O] | LCMS-D-1 | 1.93 | 473 (M + H)+ |
| 559 | 1292 | 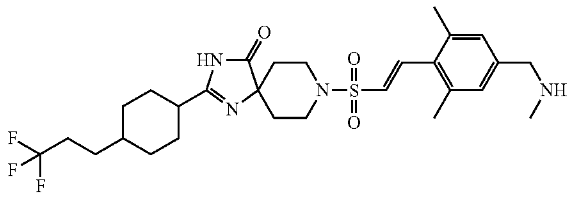 [SMILES: CNCc1cc(C)c(/C=C/S(=O)(=O)N2CCC3(CC2)N=C(C2CCC(CCC(F)(F)F)CC2)NC3=O)c(C)c1] | LCMS-D-1 | 1.77 | 569 (M + H)+ |

Example 298

8-[2-(4-Amino-3-chloro-2-methyl-phenyl)-ethane-sulfonyl]-2-(4-ethyl-cyclohexyl)-1,3,8-triaza-spiro[4.5]dec-1-en-4-one (Compound 1293)

(Reaction 298-1)

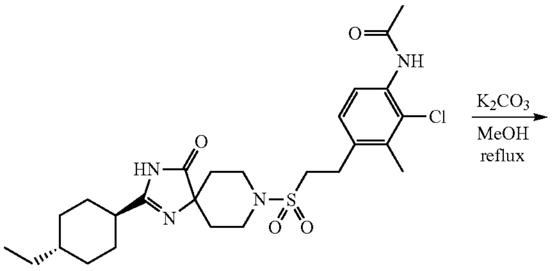

Compound 954

-continued

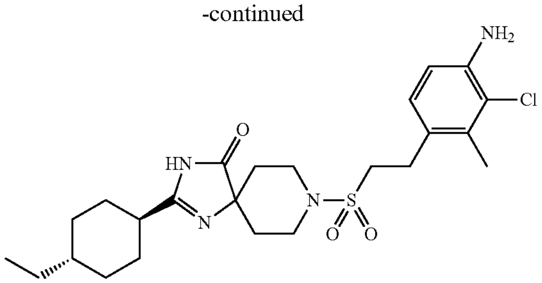

Compound 1293

8-[2-(4-Amino-3-chloro-2-methyl-phenyl)-ethanesulfonyl]-2-(4-ethyl-cyclohexyl)-1,3,8-triaza-spiro[4.5]dec-1-en-4-one (Compound 1293) was obtained by operations similar to those in Reaction 12-5 using Compound 954 as a starting material.

MS (ESI) m/z=495 (M+H)+.

Example 299

N-(1-Acetyl-piperidin-4-yl)-N-(3-methyl-4-{(E)-2-[4-oxo-2-(3-trifluoromethoxy-phenyl)-1,3,8-triaza-spiro[4.5]dec-1-ene-8-sulfonyl]-vinyl}-phenyl)-acetamide (Compound 1294)

(Reaction 299-1)

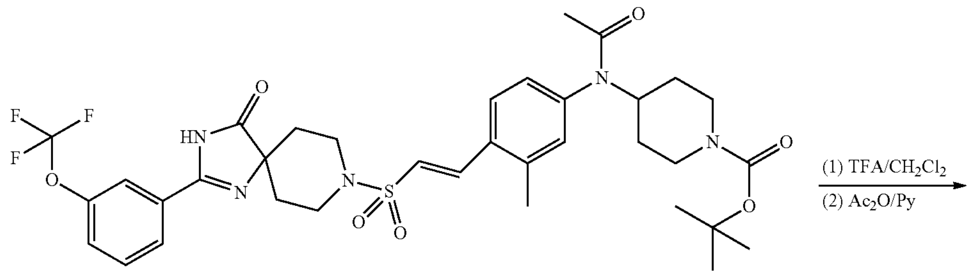

Compound 604

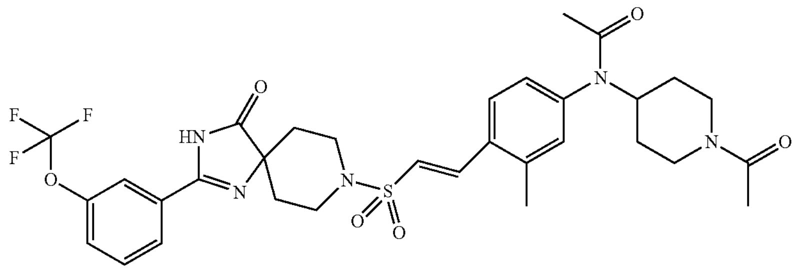

Compound 1294

N-(1-Acetyl-piperidin-4-yl)-N-(3-methyl-4-{(E)-2-[4-oxo-2-(3-trifluoromethoxy-phenyl)-1,3,8-triaza-spiro[4.5]dec-1-ene-8-sulfonyl]-vinyl}-phenyl)-acetamide (Compound 1294) was obtained by operations similar to those in Reaction 4-1 and Reaction 12-2 using Compound 604 as a starting material.

MS (ESI) m/z=676 (M+H)+.

Example 300
8-{2-[4-(4,5-Dihydro-thiazol-2-ylamino)-2-methyl-phenyl]-ethanesulfonyl}-2-(4-ethyl-cyclohexyl)-1,3,8-triaza-spiro[4.5]dec-1-en-4-one (Compound 1295)
(Reaction 300-1)
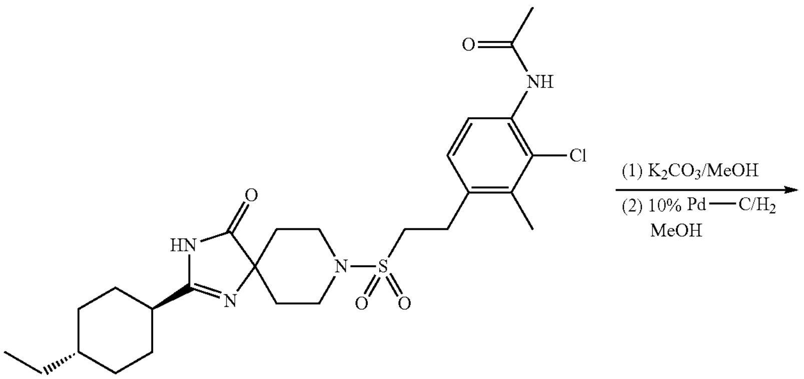
Compound 953
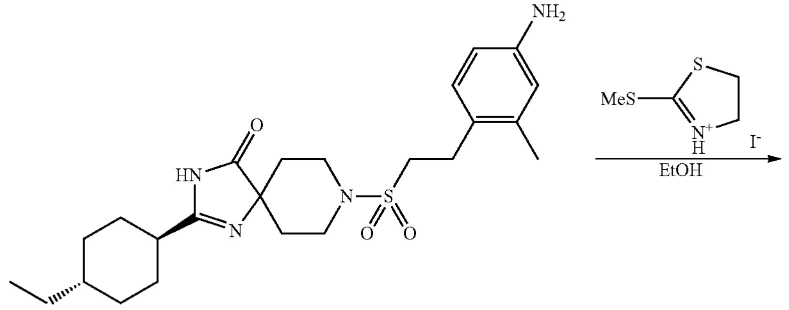
300a
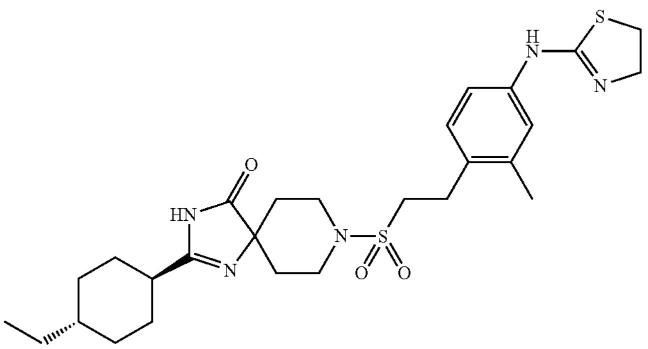
Compound 1295

8-{2-[4-(4,5-Dihydro-thiazol-2-ylamino)-2-methyl-phenyl]-ethanesulfonyl}-2-(4-ethyl-cyclohexyl)-1,3,8-triaza-spiro[4.5]dec-1-en-4-one (Compound 1295) was obtained by operations similar to those in Reaction 12-5, Reaction 18-2 and Reaction 177-2 using Compound 953 as a starting material.

MS (ESI) m/z=546 (M+H)+.

Example 301

N-[4-(2-{2-[4-(4-Fluoro-butyl)-cyclohexyl]-4-oxo-1,3,8-triaza-spiro[4.5]dec-1-ene-8-sulfonyl}-ethyl)-3-methyl-phenyl]-acetamide (Compound 1296)

(Reaction 301-1)

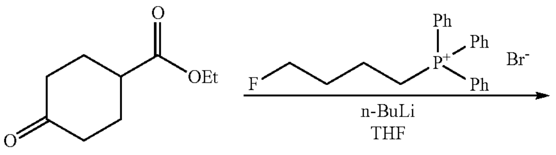

101b

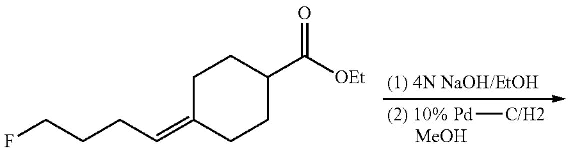

301a

-continued

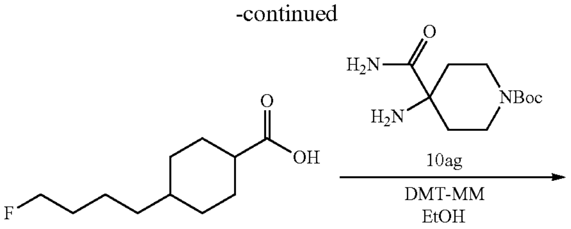

301b

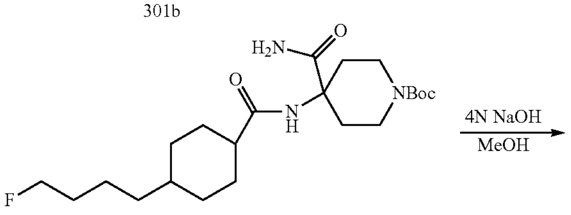

301c

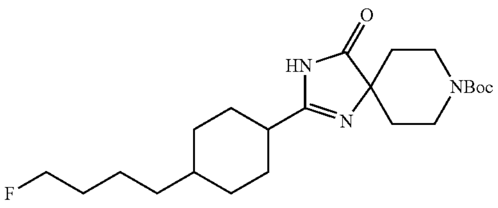

301d

2-[4-(4-Fluoro-butyl)-cyclohexyl]-4-oxo-1,3,8-triaza-spiro[4.5]dec-1-ene-8-carboxylic acid tert-butyl ester was obtained by operations similar to those in Reaction 101-1, Reaction 23-2, Reaction 18-2, Reaction 10-1 and Reaction 189-5 using 4-oxo-cyclohexanecarboxylic acid ethyl ester as a starting material.

$^1$H-NMR (400 MHz, $CDCl_3$) δ 0.97-1.05 (1H, m), 1.23-1.35 (4H, m), 1.35-1.50 (3 μm), 1.47 (9H, s), 1.60-1.75 (4H, m), 1.75-1.85 (2H, m), 1.85-1.95 (2H, m), 1.95-2.05 (2H, m), 2.35-2.45 (1H, m), 3.35-3.45 (2H, m), 3.90-4.05 (2H, m), 4.35-4.42 (1H, m), 4.45-4.52 (1H, m), 8.85 (1H, s).

(Reaction 301-2)

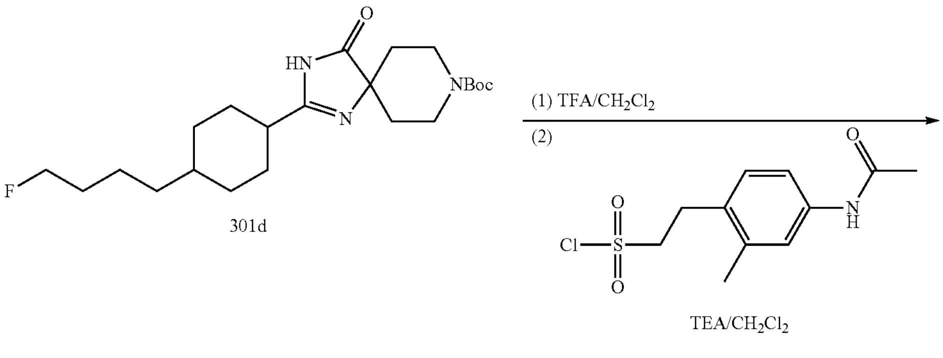

-continued

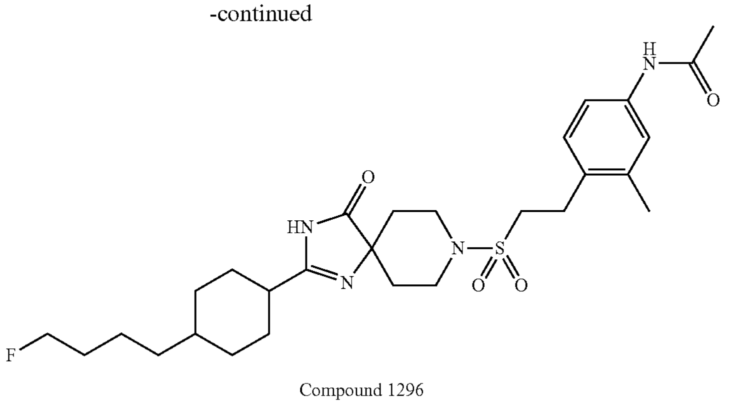

Compound 1296

N-[4-(2-{2-[4-(4-Fluoro-butyl)-cyclohexyl]-4-oxo-1,3,8-triaza-spiro[4.5]dec-1-ene-8-sulfonyl}-ethyl)-3-methyl-phenyl]-acetamide (Compound 1296) was obtained by operations similar to those in Reaction 4-1 and Reaction 5-4 using 2-[4-(4-fluoro-butyl)-cyclohexyl]-4-oxo-1,3,8-triaza-spiro[4.5]dec-1-ene-8-carboxylic acid tert-butyl ester as a starting material.

MS (ESI) m/z=549 (M+H)+.

Example 302

1-(3,5-Dimethyl-4-{2-[2-(3-methyl-cyclohexyl)-4-oxo-1,3,8-triaza-spiro[4.5]dec-1-ene-8-sulfonyl]-ethyl}-phenyl)-1-methyl-urea (Compound 1297)

(Reaction 302-1)

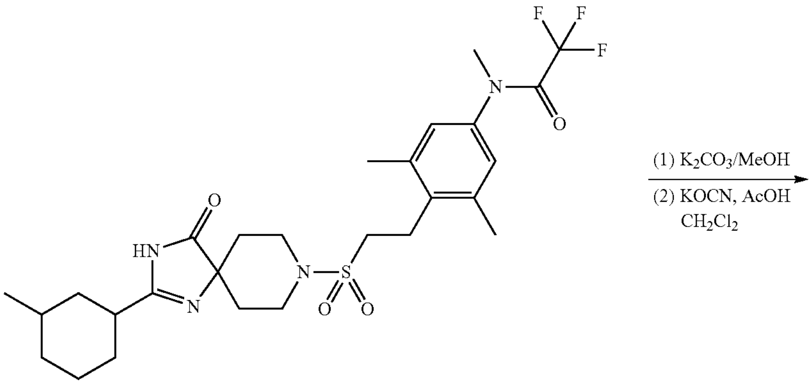

Compound 932

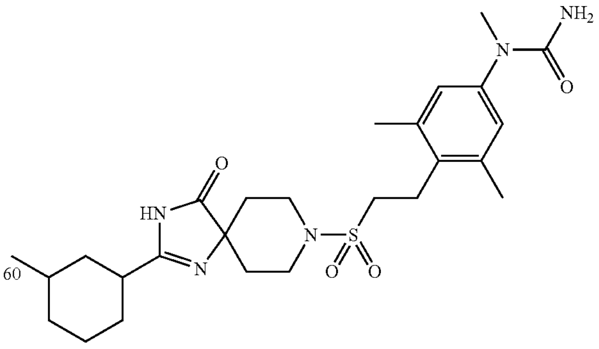

Compound 1297

1-(3,5-Dimethyl-4-{2-[2-(3-methyl-cyclohexyl)-4-oxo-1,3,8-triaza-spiro[4.5]dec-1-ene-8-sulfonyl]-ethyl}-phenyl)-1-methyl-urea (Compound 1297) was obtained by operations similar to those in Reaction 12-5 and Reaction 89-2 (using KOCN) using Compound 932 as a starting material.

MS (ESI) m/z=518 (M+H)+.

Example 303

1-(3,5-Dimethyl-4-{2-[4-oxo-2-(3,3,5,5-tetramethyl-cyclohexyl)-1,3,8-triaza-spiro[4.5]dec-1-ene-8-sulfonyl]-ethyl}-phenyl)-1-methyl-urea (Compound 1298)

(Reaction 303-1)

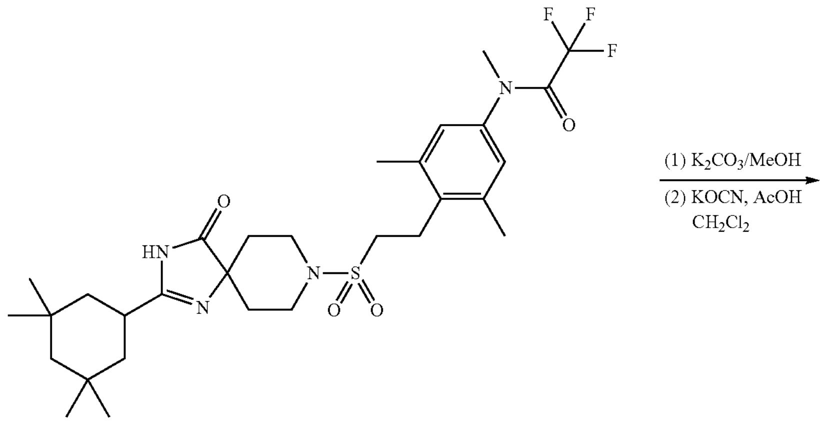

Compound 933

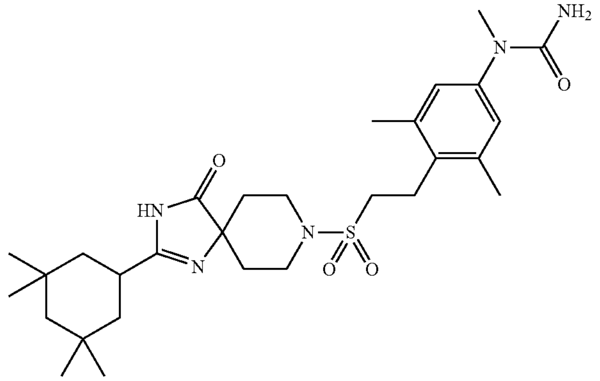

Compound 1298

1-(3,5-Dimethyl-4-{2-[4-oxo-2-(3,3,5,5-tetramethyl-cyclohexyl)-1,3,8-triaza-spiro[4.5]dec-1-ene-8-sulfonyl]-ethyl}-phenyl)-1-methyl-urea (Compound 1298) was obtained by operations similar to those in Reaction 12-5 and Reaction 89-2 (using KOCN) using Compound 933 as a starting material.

MS (ESI) m/z=560 (M+H)+.

Example 304

3-(3,5-Dimethyl-4-{2-[2-(4-methyl-cyclohexyl)-4-oxo-1,3,8-triaza-spiro[4.5]dec-1-ene-8-sulfonyl]-ethyl}-phenyl)-5-hydroxymethyl-imidazolidine-2,4-dione (Compound 1299)

(Reaction 304-1)

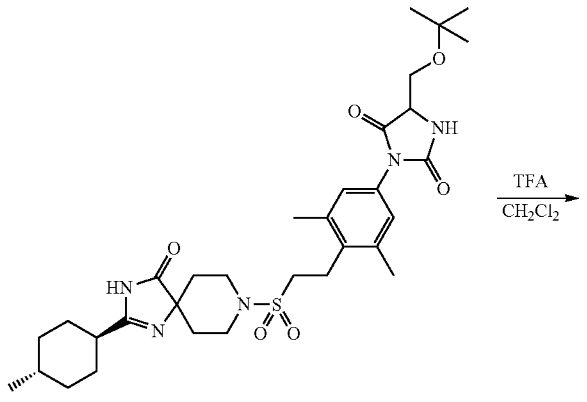

Compound 833

-continued

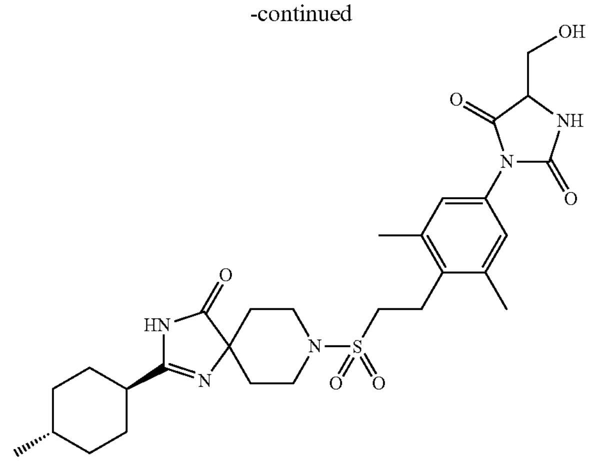

Compound 1299

3-(3,5-Dimethyl-4-{2-[2-(4-methyl-cyclohexyl)-4-oxo-1,3,8-triaza-spiro[4.5]dec-1-ene-8-sulfonyl]-ethyl}-phenyl)-5-hydroxymethyl-imidazolidine-2,4-dione (Compound 1299) was obtained by operations similar to those in Reaction 4-1 using Compound 833 as a starting material.

MS (ESI) m/z=574 (M+H)+.

Example 305

1-[3,5-Dimethyl-4-((E)-2-{4-oxo-2-[4-(3,3,3-trifluoro-propyl)-cyclohexyl]-1,3,8-triaza-spiro[4.5]dec-1-ene-8-sulfonyl}-vinyl)-benzyl]-1-methyl-urea (Compound 1300)

(Reaction 305-1)

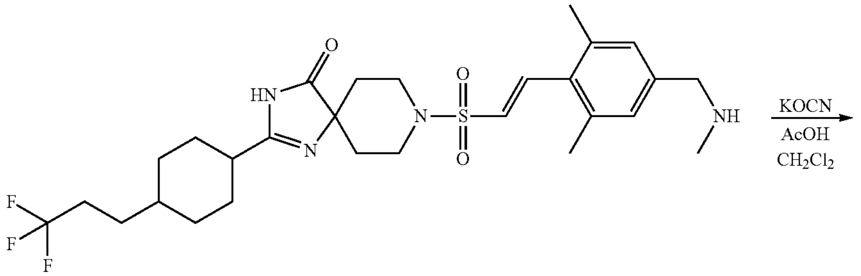

Compound 1193

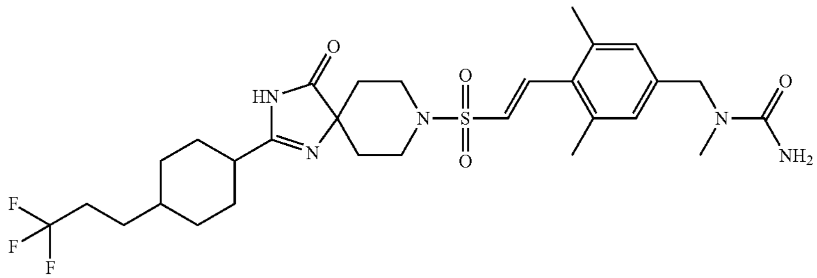

Compound 1300

1-[3,5-Dimethyl-4-((E)-2-{4-oxo-2-[4-(3,3,3-trifluoro-propyl)-cyclohexyl]-1,3,8-triaza-spiro[4.5]dec-1-ene-8-sulfonyl}-vinyl)-benzyl]-1-methyl-urea (Compound 1300) was obtained by operations similar to those in Reaction 89-2 (using KOCN) using Compound 1193 as a starting material.

MS (ESI) m/z=612 (M+H)+.

The example compounds shown below were obtained by operations similar to those in Reaction 305-1 using appropriate starting compounds.

Compounds 1301 to Compound 1312

TABLE 186

| Starting Compound | Target Compound | Structure | LCMS condition | Retention time (min) | MS (m/z) |
|---|---|---|---|---|---|
| 1289 | 1301 | 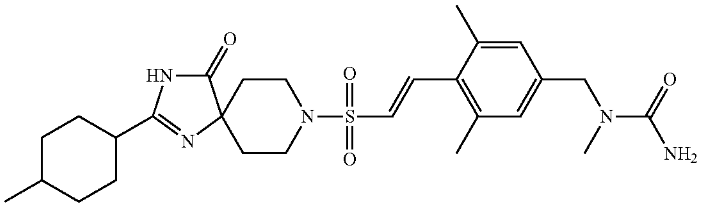 [SMILES: Cc1cc(CN(C)C(N)=O)cc(C)c1/C=C/S(=O)(=O)N1CCC2(CC1)N=C(C1CCC(C)CC1)NC2=O] | LCMS-D-1 | 1.97 | 530 (M + H)+ |
| 1035 | 1302 | 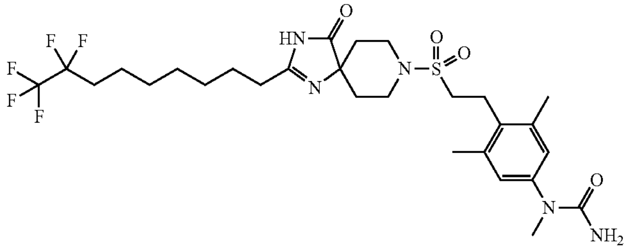 [SMILES: Cc1cc(N(C)C(N)=O)cc(C)c1CCS(=O)(=O)N1CCC2(CC1)N=C(CCCCCCCC(F)(F)C(F)(F)F)NC2=O] | LCMS-F-1 | 1.01 | 638 (M + H)+ |
| 691 | 1303 | 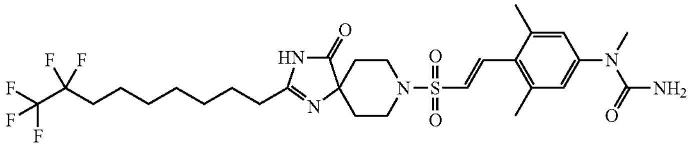 [SMILES: Cc1cc(N(C)C(N)=O)cc(C)c1/C=C/S(=O)(=O)N1CCC2(CC1)N=C(CCCCCCCC(F)(F)C(F)(F)F)NC2=O] | LCMS-F-1 | 1.01 | 636 (M + H)+ |
| 690 | 1304 | 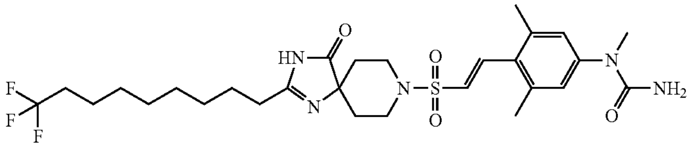 [SMILES: Cc1cc(N(C)C(N)=O)cc(C)c1/C=C/S(=O)(=O)N1CCC2(CC1)N=C(CCCCCCCCC(F)(F)F)NC2=O] | LCMS-F-1 | 1.00 | 600 (M + H)+ |
| 1016 | 1305 | 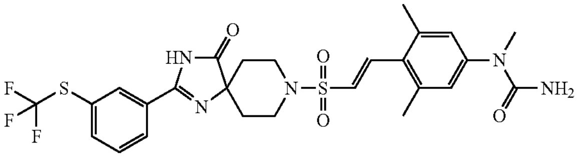 [SMILES: Cc1cc(N(C)C(N)=O)cc(C)c1/C=C/S(=O)(=O)N1CCC2(CC1)N=C(c1cccc(SC(F)(F)F)c1)NC2=O] | LCMS-C-1 | 2.75 | 596 (M + H)+ |
| 1036 | 1306 | 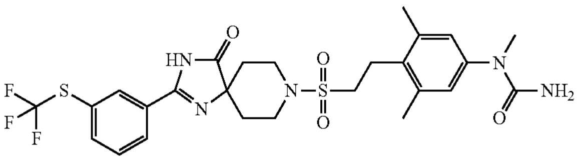 [SMILES: Cc1cc(N(C)C(N)=O)cc(C)c1CCS(=O)(=O)N1CCC2(CC1)N=C(c1cccc(SC(F)(F)F)c1)NC2=O] | LCMS-F-1 | 0.98 | 598 (M + H)+ |
| 1105 | 1307 | 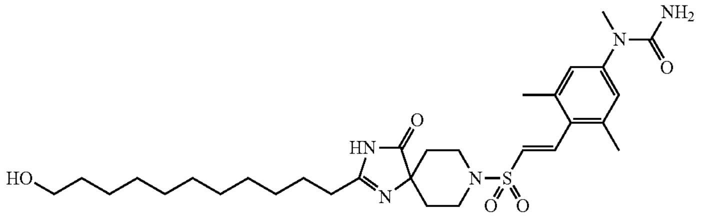 [SMILES: Cc1cc(N(C)C(N)=O)cc(C)c1/C=C/S(=O)(=O)N1CCC2(CC1)N=C(CCCCCCCCCCCO)NC2=O] | LCMS-C-1 | 2.70 | 590 (M + H)+ |

TABLE 186-continued
| Starting Compound | Target Compound | Structure | LCMS condition | Retention time (min) | MS (m/z) |
|---|---|---|---|---|---|
| 1106 | 1308 | 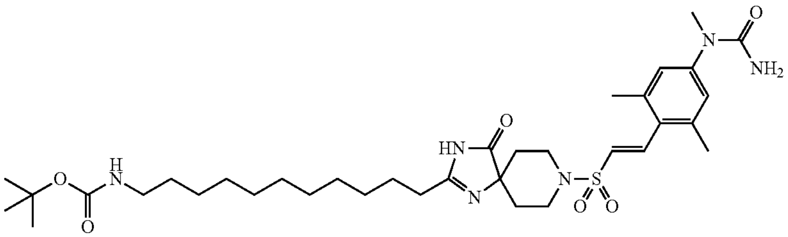 [SMILES: Cc1cc(N(C)C(N)=O)cc(C)c1/C=C/S(=O)(=O)N1CCC2(CC1)N=C(CCCCCCCCCCCNC(=O)OC(C)(C)C)NC2=O] | LCMS-C-1 | 2.98 | 689 (M + H)+ |
| 1107 | 1309 | 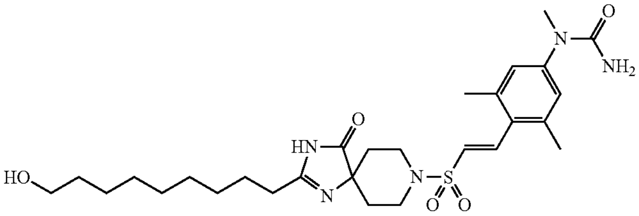 [SMILES: Cc1cc(N(C)C(N)=O)cc(C)c1/C=C/S(=O)(=O)N1CCC2(CC1)N=C(CCCCCCCCCO)NC2=O] | LCMS-F-1 | 0.92 | 562 (M + H)+ |
| 1037 | 1310 | 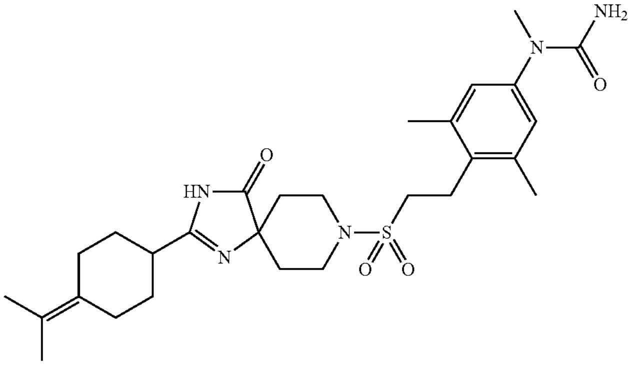 [SMILES: CC(C)=C1CCC(C2=NC3(CCN(S(=O)(=O)CCc4c(C)cc(N(C)C(N)=O)cc4C)CC3)C(=O)N2)CC1] | LCMS-A-1 | 2.10 | 544 (M + H)+ |
| 1287 | 1311 | 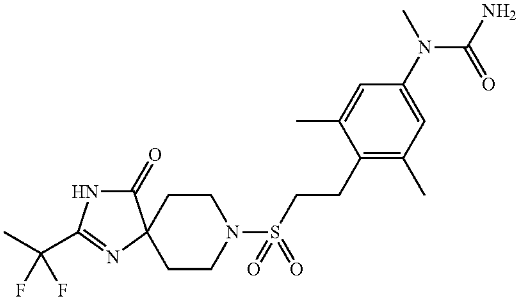 [SMILES: Cc1cc(N(C)C(N)=O)cc(C)c1CCS(=O)(=O)N1CCC2(CC1)N=C(C(C)(F)F)NC2=O] | LCMS-B-1 | 1.71 | 486 (M + H)+ |
| 1288 | 1312 | 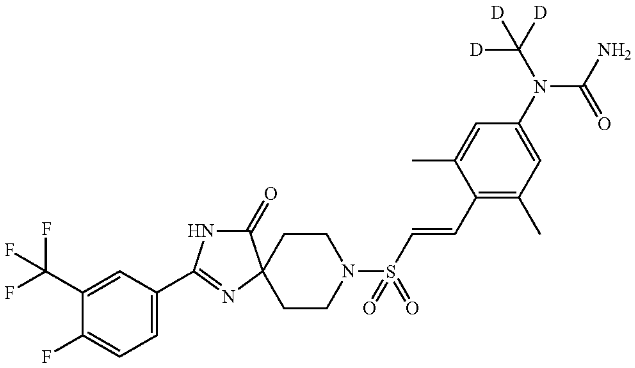 [SMILES: [2H]C([2H])([2H])N(C(N)=O)c1cc(C)c(/C=C/S(=O)(=O)N2CCC3(CC2)N=C(c2ccc(F)c(C(F)(F)F)c2)NC3=O)c(C)c1] | LCMS-F-1 | 0.99 | 585 (M + H)+ |

Example 306

[3,5-Dimethyl-4-(2-{4-oxo-2-[4-(3,3,3-trifluoro-propyl)-cyclohexyl]-1,3,8-triaza-spiro[4.5]dec-1-ene-8-sulfonyl}-ethyl)-benzyl]-urea (Compound 1313)

(Reaction 306-1)

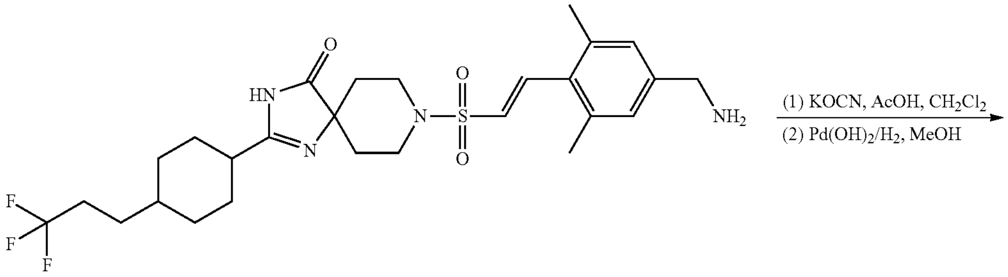

Compound 1290

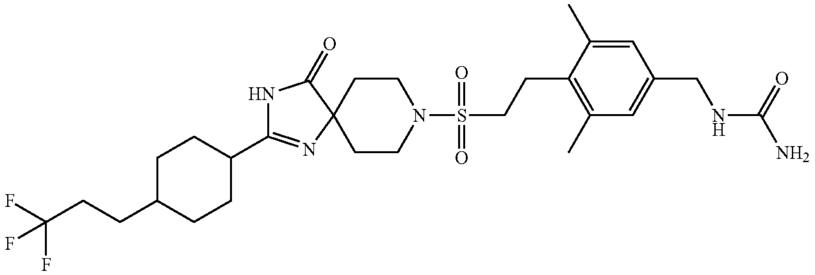

Compound 1313

[3,5-Dimethyl-4-(2-{4-oxo-2-[4-(3,3,3-trifluoro-propyl)-cyclohexyl]-1,3,8-triaza-spiro[4.5]dec-1-ene-8-sulfonyl}-ethyl)-benzyl]-urea (Compound 1313) was obtained by operations similar to those in Reaction 89-2 (using KOCN) and Reaction 122-2 using Compound 1290 as a starting material.

MS (ESI) m/z=600 (M+H)+.

The example compound shown below was obtained by operations similar to those in Reaction 306-1 using an appropriate starting compound.

Compound 1314

TABLE 187

| Starting Compound | Target Compound | Structure | LCMS condition | Retention time (min) | MS (m/z) |
|---|---|---|---|---|---|
| 1291 | 1314 | 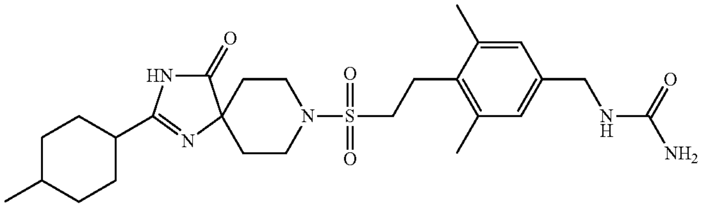 [SMILES: Cc1cc(CNC(N)=O)cc(C)c1CCS(=O)(=O)N1CCC2(CC1)N=C(C1CCC(C)CC1)NC2=O] | LCMS-D-1 | 1.78 | 518 (M + H)+ |

Example 307

1-(4-{(E)-2-[2-(11-Amino-undecyl)-4-oxo-1,3,8-triaza-spiro[4.5]dec-1-ene-8-sulfonyl]-vinyl}-3,5-dimethyl-phenyl)-1-methyl-urea (Compound 1315)

(Reaction 307-1)

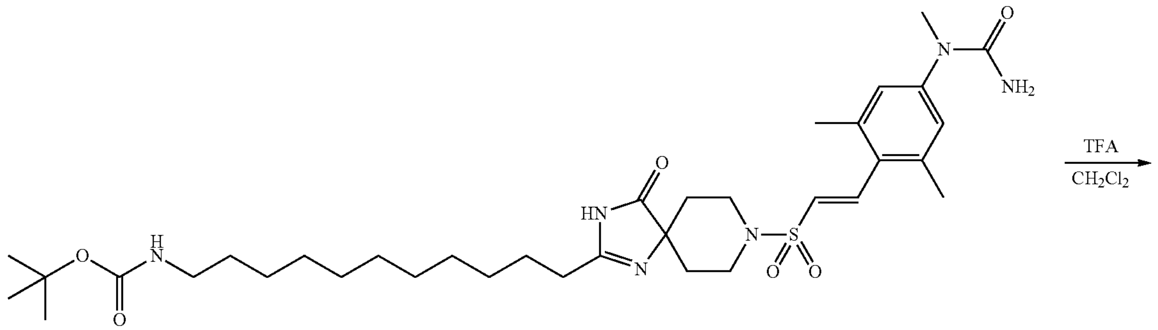

Compound 1209

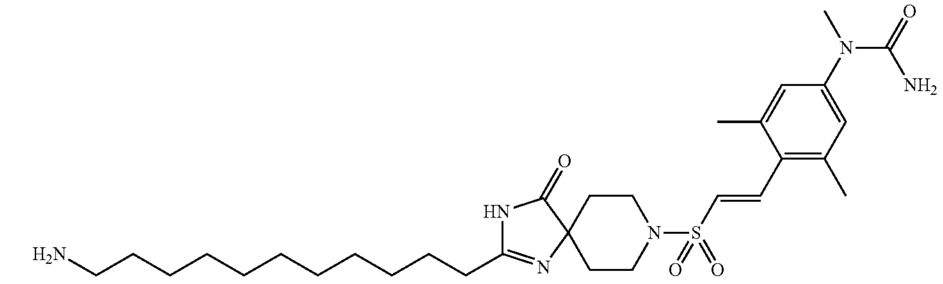

Compound 1315

1-(4-{(E)-2-[2-(11-Amino-undecyl)-4-oxo-1,3,8-triaza-spiro[4.5]dec-1-ene-8-sulfonyl]-vinyl}-3,5-dimethyl-phenyl)-1-methyl-urea (Compound 1315) was obtained by operations similar to those in Reaction 4-1 using Compound 1209 as a starting material.

MS (ESI) m/z=589 (M+H)+.

Example 308

1-[3,5-Dimethyl-4-((E)-2-{4-oxo-2-[5-(propane-1-sulfinyl)-pentyl]-1,3,8-triaza-spiro[4.5]dec-1-ene-8-sulfonyl}-vinyl)-phenyl]-1-methyl-urea (Compound 1316)

(Reaction 308-1)

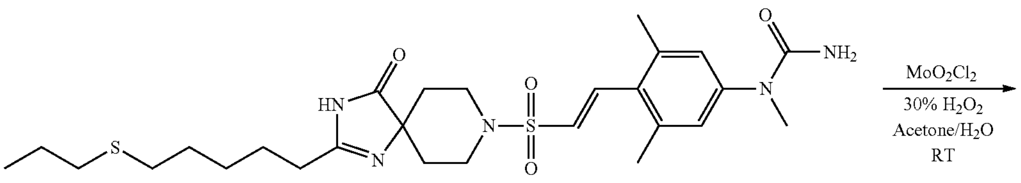

Compound 1122

-continued

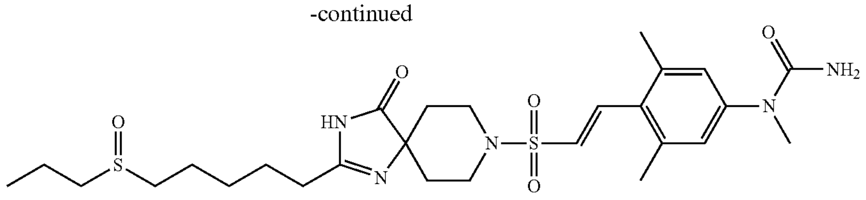

Compound 1316

30% aqueous hydrogen peroxide (0.013 ml) was added to a mixed solution of (E)-1-(3,5-dimethyl-4-(2-((4-oxo-2-(5-(propylthio)pentyl)-1,3,8-triazaspiro[4.5]dec-1-en-8-yl)sulfonyl)vinyl)phenyl)-1-methyl-urea (55 mg) and molybdenum(IV) dichloride dioxide (3 mg) in acetone (1.5 ml)-water (0.5 ml), and the mixture was stirred at room temperature for five minutes in a nitrogen stream. The reaction mixture was quenched with a saturated aqueous sodium bicarbonate solution and then extracted with ethyl acetate. The organic layer was dried over anhydrous sodium sulfate and then concentrated under reduced pressure. The resulting residue was purified by column chromatography (silica gel, $CH_2Cl_2$-MeOH) to give 1-[3,5-dimethyl-4-((E)-2-{4-oxo-2-[5-(propane-1-sulfinyl)-pentyl]-1,3,8-triaza-spiro[4.5]dec-1-ene-8-sulfonyl}-vinyl)-phenyl]-1-methyl-urea (64 mg).

$^1$H-NMR (300 MHz, $CDCl_3$) δ 8.77 (s, 1H), 7.55 (d, 1H, J=15.6 Hz), 7.02 (s, 2H), 6.38 (d, 1H, J=15.6 Hz), 4.50 (s, 2H), 3.71-3.64 (m, 2H), 3.41-3.32 (m, 2H), 3.26 (s, 3H), 2.76-2.54 (m, 4H), 2.52-2.43 (m, 2H), 2.38 (s, 6H), 2.00-1.61 (m, 12H), 1.09 (t, 3H, J=7.4 Hz).

MS (ESI) m/z=580 (M+H)+.

The example compound shown below was obtained by operations similar to those in Reaction 308-1 using an appropriate starting compound.

Compound 1317

TABLE 188

| Starting Compound | Target Compound | Structure | LCMS condition | Retention time (min) | MS (m/z) |
|---|---|---|---|---|---|
| 1154 | 1317 | 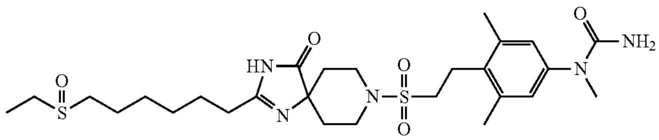 | LCMS-D-1 | 1.42 | 582 (M + H)+ |

Example 309

1-[3,5-Dimethyl-4-((E)-2-{4-oxo-2-[5-(propane-1-sulfonyl)-pentyl]-1,3,8-triaza-spiro[4.5]dec-1-ene-8-sulfonyl}-vinyl)-phenyl]-1-methyl-urea (Compound 1318)

(Reaction 309-1)

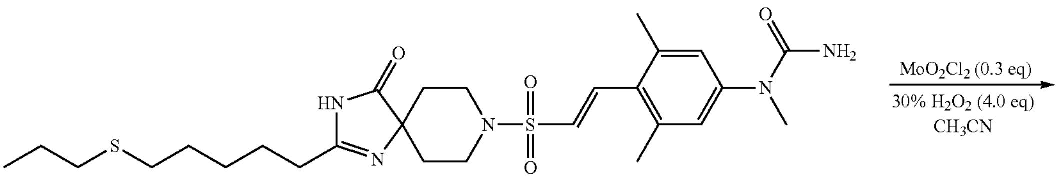

Compound 1122

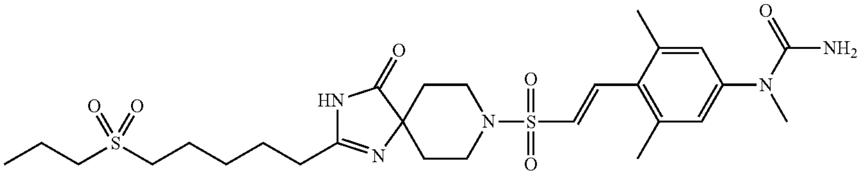

Compound 1318

30% aqueous hydrogen peroxide (0.047 ml) was added to a mixed solution of (E)-1-(3,5-dimethyl-4-(2-((4-oxo-2-(5-(propylthio)pentyl)-1,3,8-triazaspiro[4.5]dec-1-en-8-yl)sulfonyl)vinyl)phenyl)-1-methylurea (61 mg) and molybdenum (IV) dichloride dioxide (6.5 mg) in acetonitrile (1 ml), and the mixture was stirred at room temperature for two hours in a nitrogen stream. The reaction mixture was quenched with a saturated aqueous sodium bicarbonate solution and then extracted with ethyl acetate. The organic layer was dried over anhydrous sodium sulfate and then concentrated under reduced pressure. The resulting residue was purified by column chromatography (silica gel, $CH_2Cl_2$-MeOH) to give 1-[3,5-dimethyl-4-((E)-2-{4-oxo-2-[5-(propane-1-sulfonyl)-pentyl]-1,3,8-triaza-spiro[4.5]dec-1-ene-8-sulfonyl}-vinyl)-phenyl]-1-methyl-urea (64 mg).

$^1$H-NMR (300 MHz, $CDCl_3$) δ 8.96 (s, 1H), 7.54 (d, 1H, J=15.6 Hz), 7.02 (s, 2H), 6.39 (d, 1H, J=15.6 Hz), 4.68 (s, 2H), 3.68-3.61 (m, 2H), 3.45-3.37 (m, 2H), 3.25 (s, 3H), 2.98-2.91 (m, 4H), 2.48 (t, 2H, J=7.4 Hz), 2.37 (s, 6H), 1.98-1.84 (m, 6H), 1.81-1.70 (m, 4H), 1.66-1.57 (m, 2H), 1.09 (t, 3H, J=7.4 Hz).

MS (ESI) m/z=596 (M+H)+.

The example compounds shown below were obtained by operations similar to those in Reaction 309-1 using appropriate starting compounds.

Compounds 1319 to Compound 1320

TABLE 189

| Starting Compound | Target Compound | Structure | LCMS condition | Retention time (min) | MS (m/z ) |
|---|---|---|---|---|---|
| 1022 | 1319 | 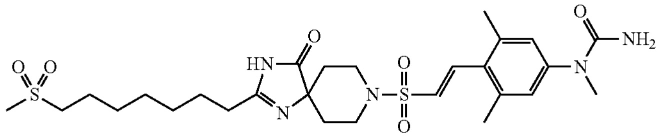 [SMILES: Cc1cc(N(C)C(N)=O)cc(C)c1/C=C/S(=O)(=O)N1CCC2(CC1)N=C(CCCCCCCS(C)(=O)=O)NC2=O] | LCMS-D-1 | 1.52 | 596 (M + H)+ |
| 1154 | 1320 | 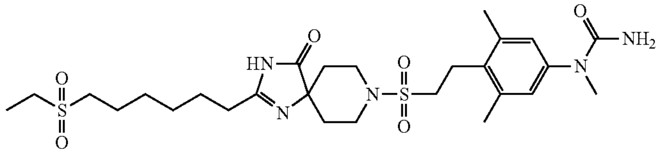 [SMILES: CCS(=O)(=O)CCCCCCC1=NC2(CCN(S(=O)(=O)CCc3c(C)cc(N(C)C(N)=O)cc3C)CC2)C(=O)N1] | LDMS D-1 | 1.49 | 598 (M + H)+ |

Example 310

1-(4-{(E)-2-[2-(9,9-Difluoro-nonyl)-4-oxo-1,3,8-triaza-spiro[4.5]dec-1-ene-8-sulfonyl]-vinyl}-3,5-dimethyl-phenyl)-1-methyl-urea (Compound 1321)

(Reaction 310-1)

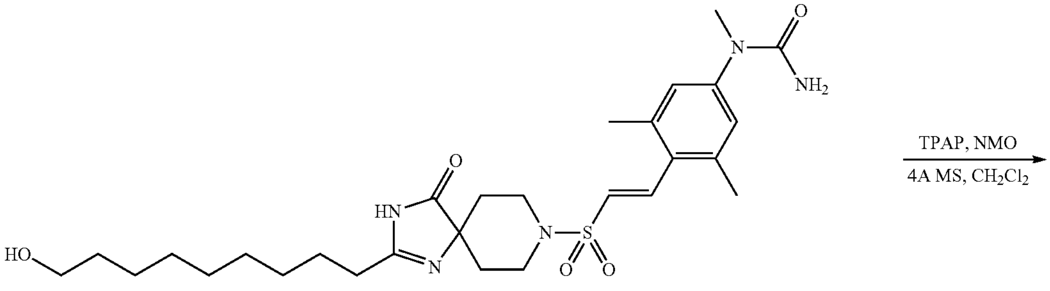

Compound 1210

-continued

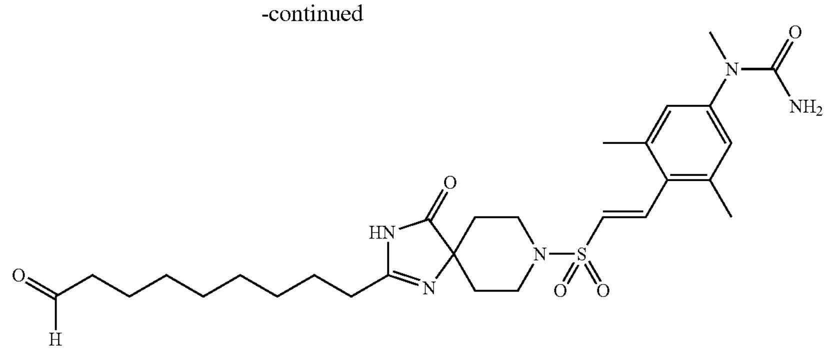

310a

NMO (22.0 mg, 0.192 mmol), Molecular Sieves 4A (25.0 mg) and TPAP (0.700 mg, 0.00213 mmol) were added to a solution of 1-(4-{2-[2-(9-hydroxy-nonyl)-4-oxo-1,3,8-triaza-spiro[4.5]dec-1-ene-8-sulfonyl]-ethyl}-3,5-dimethyl-phenyl)-1-methyl-urea (24.0 mg, 0.0426 mmol) in $CH_2Cl_2$ (850 μl) at room temperature. The mixture was stirred at room temperature for one hour and then filtered through celite, and the filtrate was concentrated under reduced pressure. The residue was purified by silica gel chromatography to give 1-(3,5-dimethyl-4-{(E)-2-[4-oxo-2-(9-oxo-nonyl)-1,3,8-triaza-spiro[4.5]dec-1-ene-8-sulfonyl]-vinyl}-phenyl)-1-methyl-urea (17.0 mg, 71%).

MS (ESI) m/z=562 (M+H)+.

(Reaction 310-2)

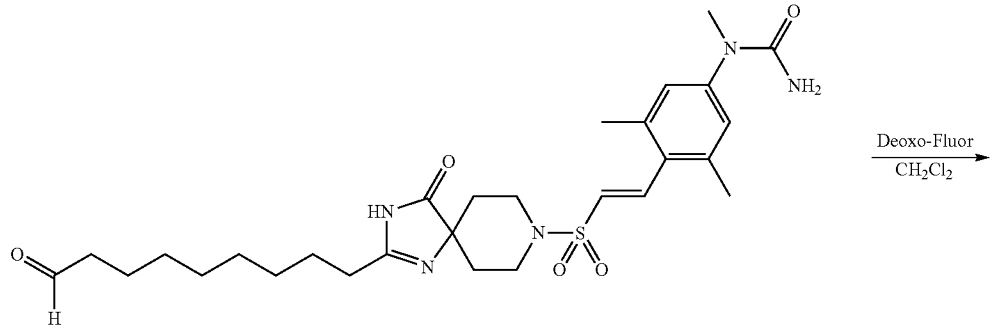

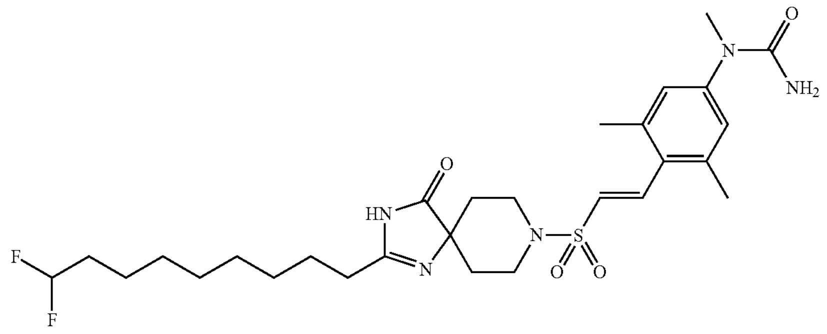

Compound 1321

1-(4-{(E)-2-[2-(9,9-Difluoro-nonyl)-4-oxo-1,3,8-triaza-spiro[4.5]dec-1-ene-8-sulfonyl]-vinyl}-3,5-dimethyl-phenyl)-1-methyl-urea (Compound 1321) was obtained by operations similar to those in Reaction 191-11 using 1-(3,5-dimethyl-4-{(E)-2-[4-oxo-2-(9-oxo-nonyl)-1,3,8-triaza-spiro[4.5]dec-1-ene-8-sulfonyl]-vinyl}-phenyl)-1-methyl-urea as a starting material.

MS (ESI) m/z=582 (M+H)+.

Example 311

1-(4-{2-[2-(9-Hydroxy-nonyl)-4-oxo-1,3,8-triaza-spiro[4.5]dec-1-ene-8-sulfonyl]-ethyl}-3,5-dimethyl-phenyl)-1-methyl-urea (Compound 1322)

(Reaction 311-1)

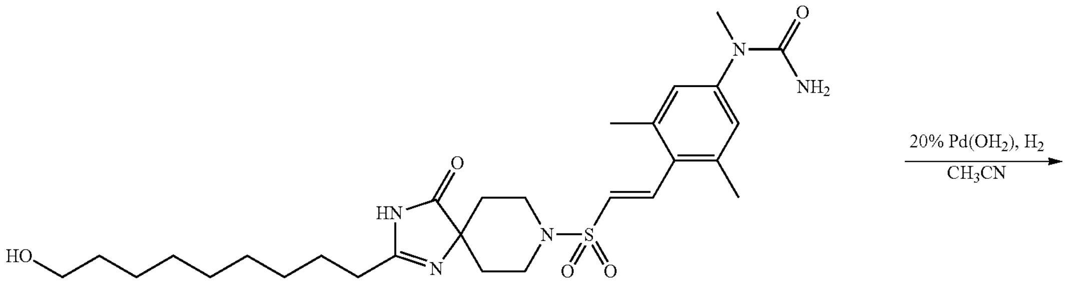

Compound 1210

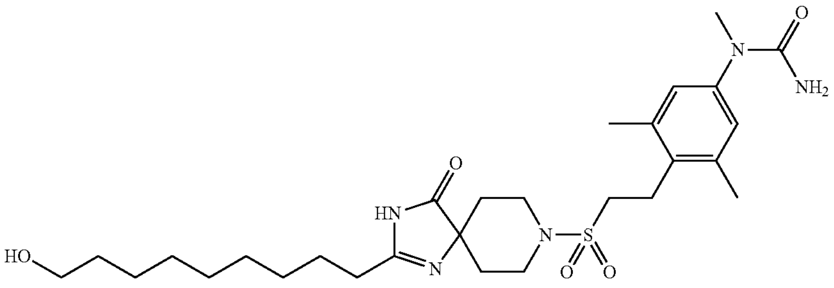

Compound 1322

1-(4-{2-[2-(9-Hydroxy-nonyl)-4-oxo-1,3,8-triaza-spiro[4.5]dec-1-ene-8-sulfonyl]-ethyl}-3,5-dimethyl-phenyl)-1-methyl-urea (Compound 1322) was obtained by operations similar to those in Reaction 184-1 using Compound 1210 as a starting material and acetonitrile as a solvent.

MS (ESI) m/z=564 (M+H)+.

Example 312

1-(4-{2-[2-(9,9-Difluoro-nonyl)-4-oxo-1,3,8-triaza-spiro[4.5]dec-1-ene-8-sulfonyl]-ethyl}-3,5-dimethyl-phenyl)-1-methyl-urea (Compound 1323)

(Reaction 312-1)

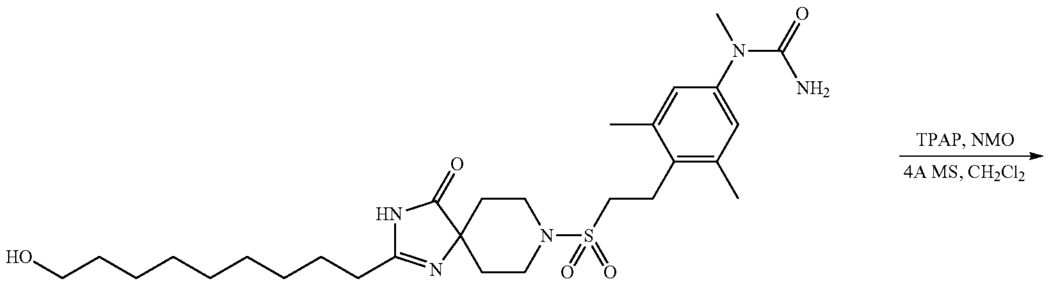

Compound 1260

-continued
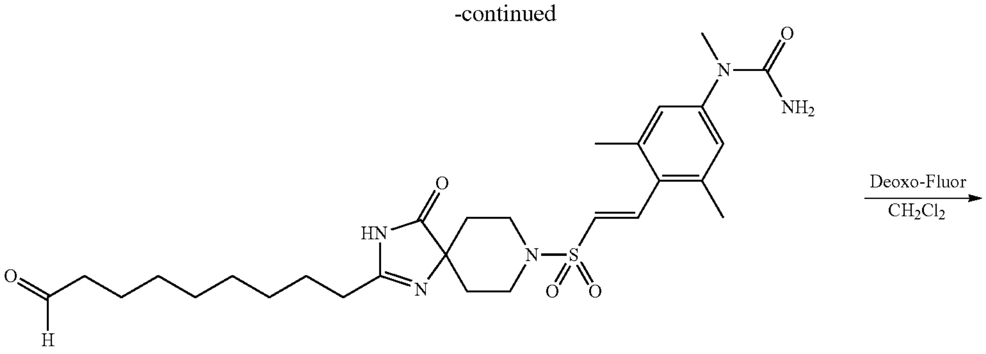
312a
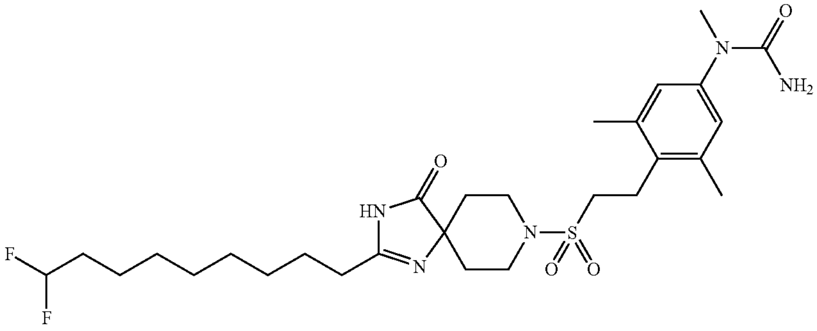
Compound 1323
1-(4-{2-[2-(9,9-Difluoro-nonyl)-4-oxo-1,3,8-triaza-spiro[4.5]dec-1-ene-8-sulfonyl]-ethyl}-3,5-dimethyl-phenyl)-1-methyl-urea (Compound 1323) was obtained by operations similar to those in Reaction 310-1 and Reaction 191-11 using Compound 1260 as a starting material.
MS (ESI) m/z=584 (M+H)+.
Example 313
1-(4-{2-[2-(9-Amino-nonyl)-4-oxo-1,3,8-triaza-spiro[4.5]dec-1-ene-8-sulfonyl]-ethyl}-3,5-dimethyl-phenyl)-1-methyl-urea (Compound 1324)
(Reaction 313-1)
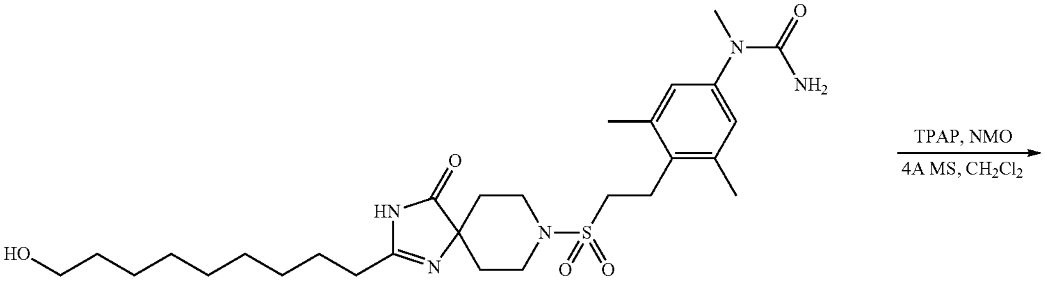
Compound 1260

-continued

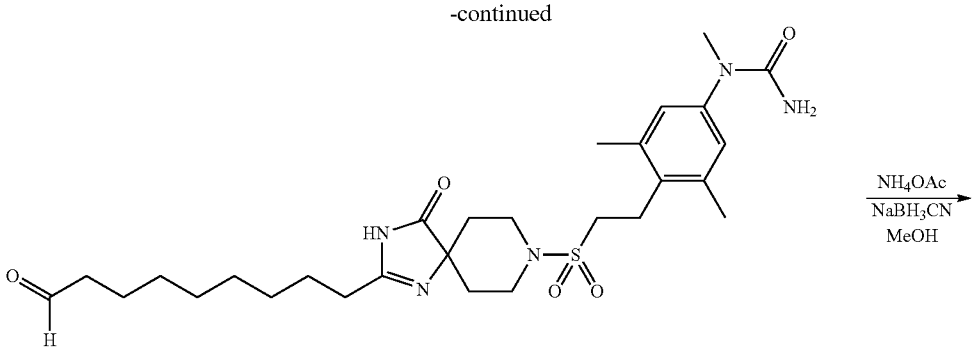

313a

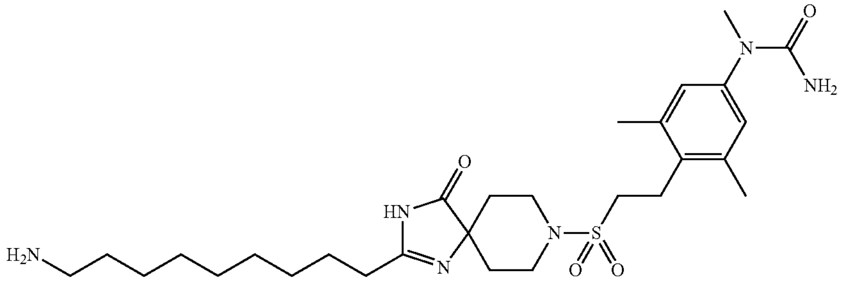

Compound 1324

1-(4-{2-[2-(9-Amino-nonyl)-4-oxo-1,3,8-triaza-spiro[4.5]dec-1-ene-8-sulfonyl]-ethyl}-3,5-dimethyl-phenyl)-1-methyl-urea (Compound 1324) was obtained by operations similar to those in Reaction 310-1 and Reaction 80-1 (using $NaBH_3CN$ as a reducing agent and methanol as a solvent) using Compound 1260 as a starting material.

MS (ESI) m/z=563 (M+H)+.

Example 314

1-(4-{(E)-2-[2-(9-Fluoro-nonyl)-4-oxo-1,3,8-triaza-spiro[4.5]dec-1-ene-8-sulfonyl]-vinyl}-3,5-dimethyl-phenyl)-1-methyl-urea (Compound 1325) and 1-(4-{(Z)-2-[2-(9-fluoro-nonyl)-4-oxo-1,3,8-triaza-spiro[4.5]dec-1-ene-8-sulfonyl]-vinyl}-3,5-dimethyl-phenyl)-1-methyl-urea (Compound 1326)

(Reaction 314-1)

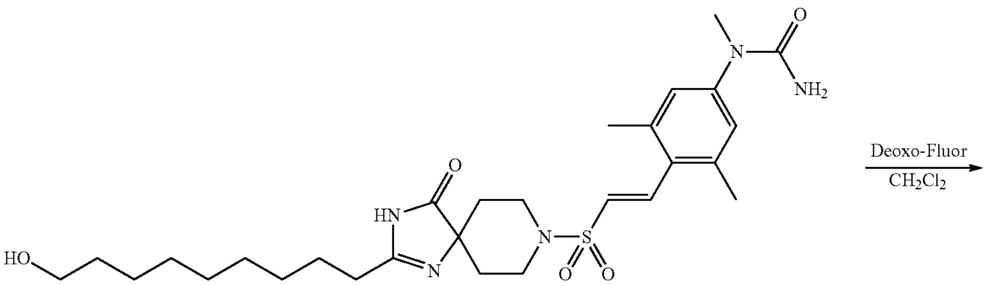

Compound 1260

-continued

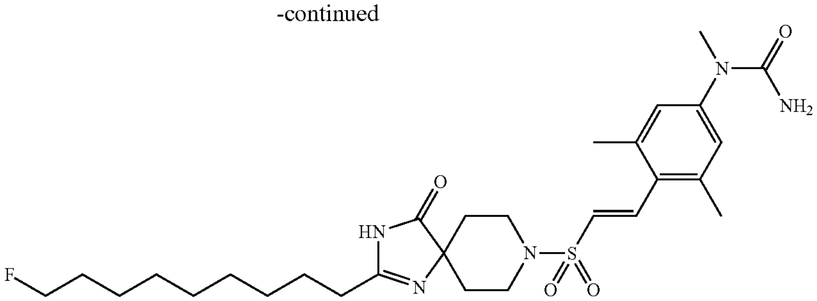

Compound 1325

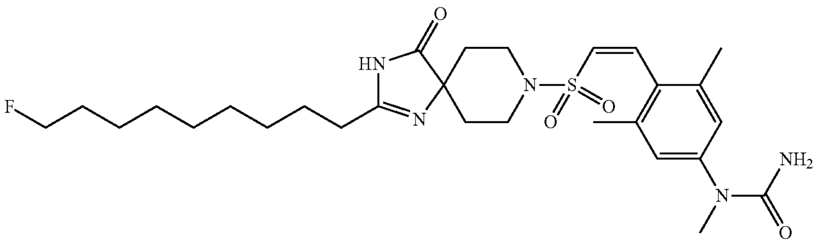

Compound 1326

1-(4-{(E)-2-[2-(9-Fluoro-nonyl)-4-oxo-1,3,8-triaza-spiro[4.5]dec-1-ene-8-sulfonyl]-vinyl}-3,5-dimethyl-phenyl)-1-methyl-urea (Compound 1325)

MS (ESI) m/z=564 (M+H)+ and 1-(4-{(Z)-2-[2-(9-fluoro-nonyl)-4-oxo-1,3,8-triaza-spiro[4.5]dec-1-ene-8-sulfonyl]-vinyl}-3,5-dimethyl-phenyl)-1-methyl-urea (Compound 1326)

MS (ESI) m/z=564 (M+H)+ were obtained by operations similar to those in Reaction 191-11 using Compound 1260 as a starting material.

Example 315

1-(4-{2-[2-(9-Fluoro-nonyl)-4-oxo-1,3,8-triaza-spiro[4.5]dec-1-ene-8-sulfonyl]-ethyl}-3,5-dimethyl-phenyl)-1-methyl-urea (Compound 1327)

(Reaction 315-1)

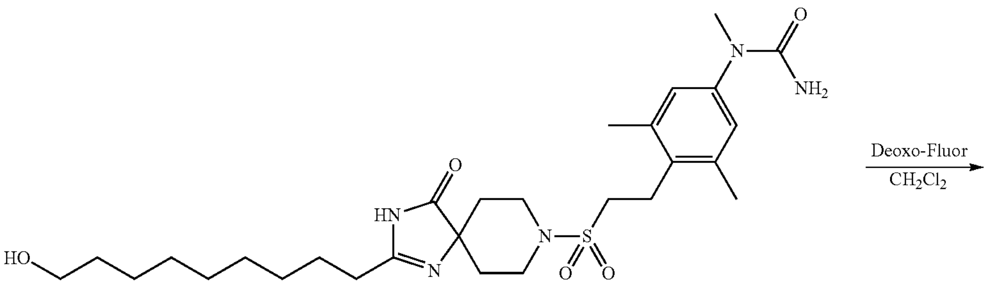

Compound 1260

-continued

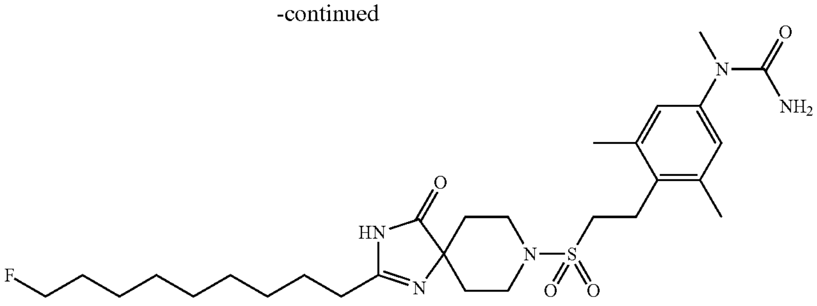

Compound 1326

1-(4-{2-[2-(9-Fluoro-nonyl)-4-oxo-1,3,8-triaza-spiro[4.5]dec-1-ene-8-sulfonyl]-ethyl}-3,5-dimethyl-phenyl)-1-methyl-urea (Compound 1327) was obtained by operations similar to those in Reaction 191-11 using Compound 1260 as a starting material.

MS (ESI) m/z=566 (M+H)+.

Example 316

8-{2-[4-((R)-2,3-Dihydroxy-propoxy)-2,6-dimethyl-phenyl]-ethanesulfonyl}-2-[3-(4,4,5,5,5-pentafluoro-pentyloxy)-phenyl]-1,3,8-triaza-spiro[4.5]dec-1-en-4-one (Compound 1328)

(Reaction 316-1)

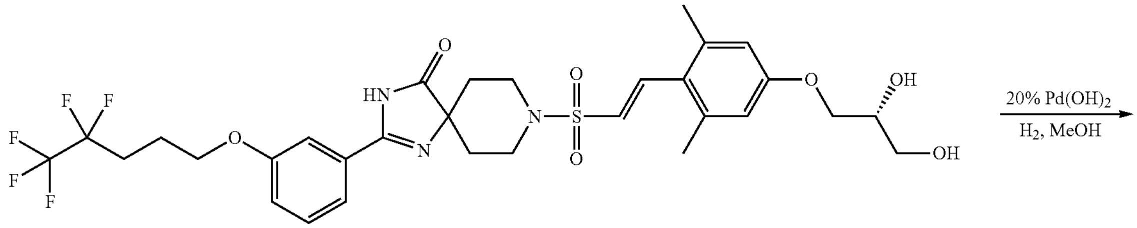

Compound 1003

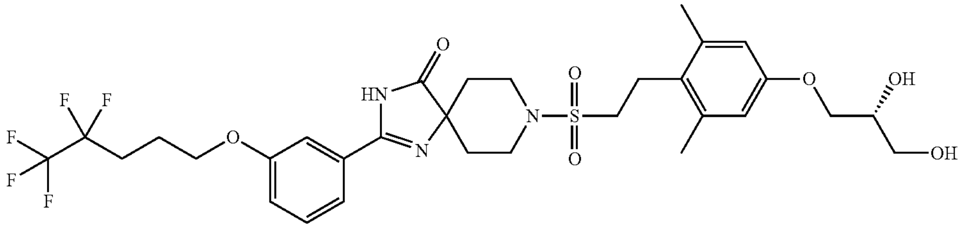

Compound 1328

8-{2-[4-((R)-2,3-Dihydroxy-propoxy)-2,6-dimethyl-phenyl}-ethanesulfonyl]-2-[3-(4,4,5,5,5-pentafluoro-pentyloxy)-phenyl]-1,3,8-triaza-spiro[4.5]dec-1-en-4-one (Compound 1328) was obtained by operations similar to those in Reaction 122-2 using Compound 1003 as a starting material.

MS (ESI) m/z=692 (M+H)+.

The example compounds shown below were obtained by operations similar to those in Reaction 316-1 using appropriate solvents (acetonitrile or methanol or an acetonitrile-methanol mixed solution) and starting compounds.

Compounds 1329 to Compound 1364
TABLE 190
| Starting Compound | Target Compound | Structure | LCMS condition | Retention time (min) | MS (m/z) |
|---|---|---|---|---|---|
| 1164 | 1329 | 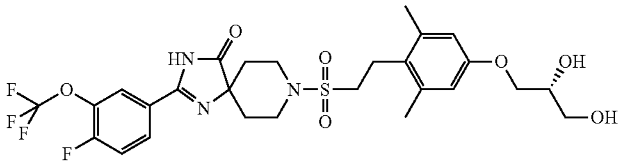 [SMILES: Cc1cc(OC[C@H](O)CO)cc(C)c1CCS(=O)(=O)N1CCC2(CC1)N=C(c1ccc(F)c(OC(F)(F)F)c1)NC2=O] | LCMS-F-1 | 0.95 | 618 (M + H)+ |
| 1165 | 1330 | 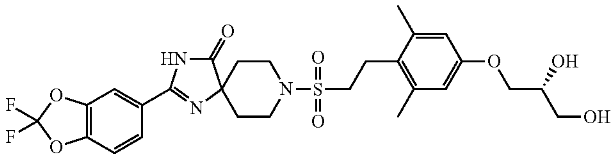 [SMILES: Cc1cc(OC[C@H](O)CO)cc(C)c1CCS(=O)(=O)N1CCC2(CC1)N=C(c1ccc3c(c1)OC(F)(F)O3)NC2=O] | LCMS-F-1 | 0.93 | 596 (M + H)+ |
| 1167 | 1331 | 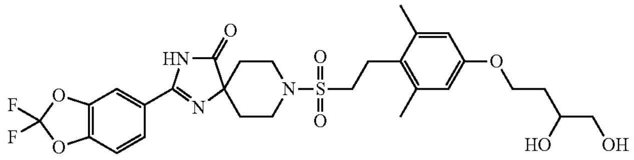 | LCMS-F-1 | 0.94 | 596 (M + H)+ |
| 1166 | 1332 | 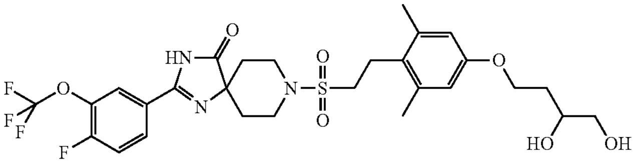 | LCMS-F-1 | 0.96 | 618 (M + H)+ |
| 1160 | 1333 | 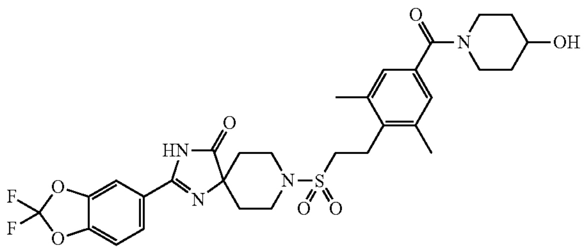 [SMILES: Cc1cc(C(=O)N2CCC(O)CC2)cc(C)c1CCS(=O)(=O)N1CCC2(CC1)N=C(c1ccc3c(c1)OC(F)(F)O3)NC2=O] | LCMS-F-1 | 0.93 | 633 (M + H)+ |
| 1159 | 1334 | 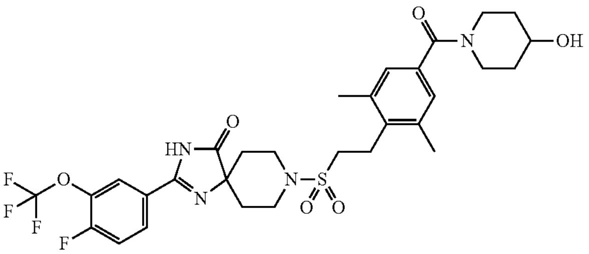 [SMILES: Cc1cc(C(=O)N2CCC(O)CC2)cc(C)c1CCS(=O)(=O)N1CCC2(CC1)N=C(c1ccc(F)c(OC(F)(F)F)c1)NC2=O] | LCMS-F-1 | 0.95 | 655 (M + H)+ |
| 1099 | 1335 | 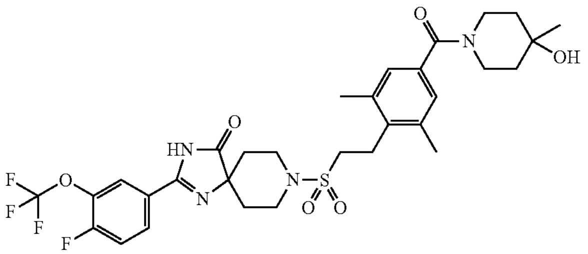 [SMILES: Cc1cc(C(=O)N2CCC(C)(O)CC2)cc(C)c1CCS(=O)(=O)N1CCC2(CC1)N=C(c1ccc(F)c(OC(F)(F)F)c1)NC2=O] | LCMS-F-1 | 1.01 | 669 (M + H)+ |

TABLE 190-continued
| Starting Compound | Target Compound | Structure | LCMS condition | Retention time (min) | MS (m/z) |
| --- | --- | --- | --- | --- | --- |
| 1163 | 1336 | 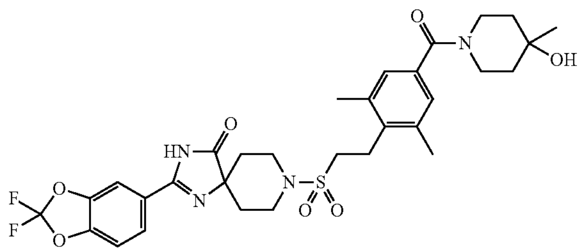 [SMILES: Cc1cc(C(=O)N2CCC(C)(O)CC2)cc(C)c1CCS(=O)(=O)N1CCC2(CC1)N=C(c1ccc3c(c1)OC(F)(F)O3)NC2=O] | LCMS-F-1 | 1.00 | 647 (M + H)+ |
| 1102 | 1337 | 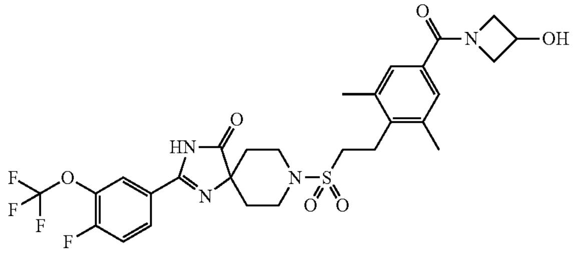 [SMILES: Cc1cc(C(=O)N2CC(O)C2)cc(C)c1CCS(=O)(=O)N1CCC2(CC1)N=C(c1ccc(F)c(OC(F)(F)F)c1)NC2=O] | LCMS-F-1 | 0.96 | 627 (M + H)+ |
| 1019 | 1338 | 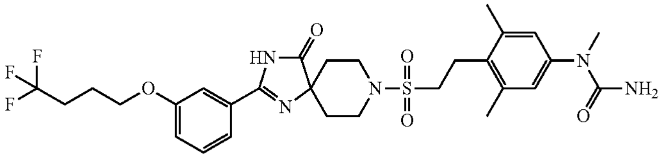 [SMILES: Cc1cc(N(C)C(N)=O)cc(C)c1CCS(=O)(=O)N1CCC2(CC1)N=C(c1cccc(OCCCC(F)(F)F)c1)NC2=O] | LCMS-F-1 | 0.98 | 624 (M + H)+ |
| 1020 | 1339 | 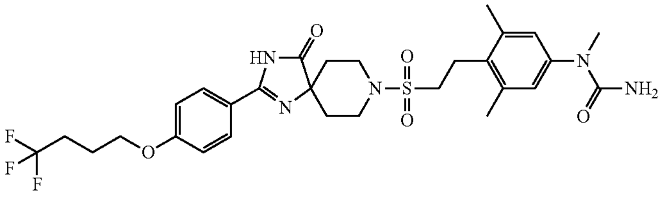 [SMILES: Cc1cc(N(C)C(N)=O)cc(C)c1CCS(=O)(=O)N1CCC2(CC1)N=C(c1ccc(OCCCC(F)(F)F)cc1)NC2=O] | LCMS-F-1 | 0.97 | 624 (M + H)+ |
| 1133 | 1340 | 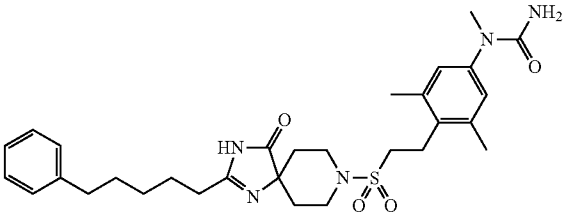 [SMILES: Cc1cc(N(C)C(N)=O)cc(C)c1CCS(=O)(=O)N1CCC2(CC1)N=C(CCCCCc1ccccc1)NC2=O] | LCMS-F-1 | 1.01 | 568 (M + H)+ |
| 1112 | 1341 | 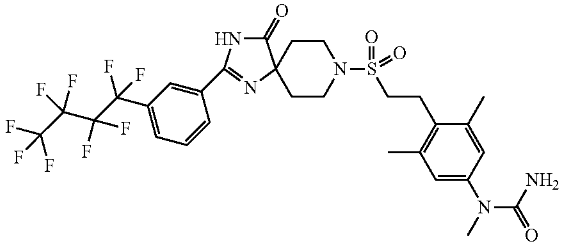 [SMILES: Cc1cc(N(C)C(N)=O)cc(C)c1CCS(=O)(=O)N1CCC2(CC1)N=C(c1cccc(C(F)(F)C(F)(F)C(F)(F)C(F)(F)F)c1)NC2=O] | LCMS-F-1 | 1.07 | 716 (M + H)+ |
| 1021 | 1342 | 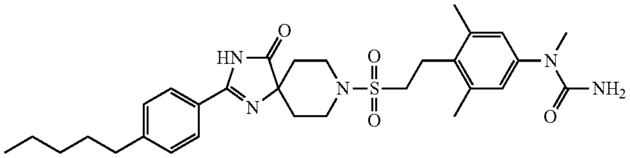 [SMILES: CCCCCc1ccc(C2=NC3(CCN(S(=O)(=O)CCc4c(C)cc(N(C)C(N)=O)cc4C)CC3)C(=O)N2)cc1] | LCMS-F-1 | 1.06 | 568 (M + H)+ |

TABLE 190-continued
| Starting Compound | Target Compound | Structure | LCMS condition | Retention time (min) | MS (m/z) |
|---|---|---|---|---|---|
| 1108 | 1343 | 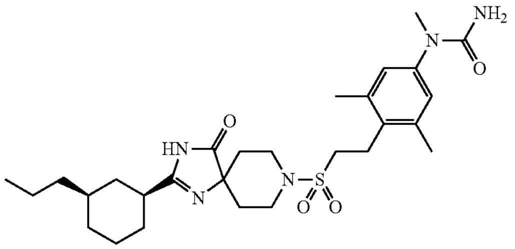 [SMILES: CCC[C@@H]1CCC[C@H](C2=NC3(CCN(S(=O)(=O)CCc4c(C)cc(N(C)C(N)=O)cc4C)CC3)C(=O)N2)C1] | LCMS-F-1 | 1.01 | 546 (M + H)+ |
| 1115 | 1344 | 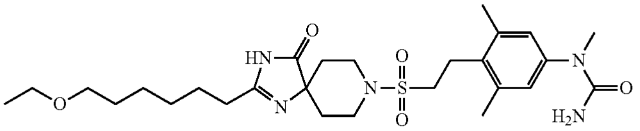 [SMILES: CCOCCCCCCC1=NC2(CCN(S(=O)(=O)CCc3c(C)cc(N(C)C(N)=O)cc3C)CC2)C(=O)N1] | LCMS-D-1 | 1.76 | 550 (M + H)+ |
| 1116 | 1345 | 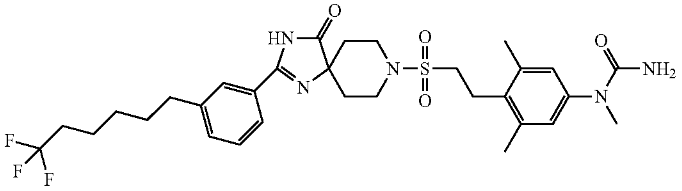 [SMILES: Cc1cc(N(C)C(N)=O)cc(C)c1CCS(=O)(=O)N1CCC2(CC1)N=C(c1cccc(CCCCCC(F)(F)F)c1)NC2=O] | LCMS-D-1 | 2.82 | 636 (M + H)+ |
| 1117 | 1346 | 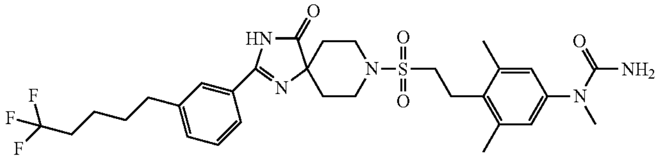 | LCMS-D-1 | 2.73 | 636 (M + H)+ |
| 1132 | 1347 | 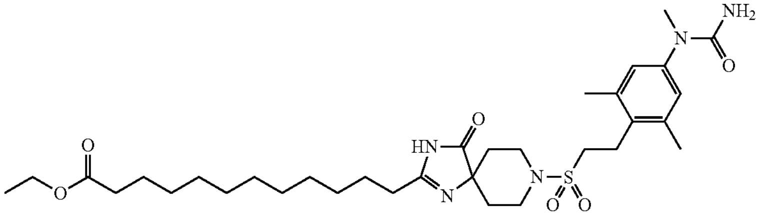 [SMILES: CCOC(=O)CCCCCCCCCCCC1=NC2(CCN(S(=O)(=O)CCc3c(C)cc(N(C)C(N)=O)cc3C)CC2)C(=O)N1] | LCMS-C-1 | 3.02 | 648 (M + H)+ |
| 1121 | 1348 | 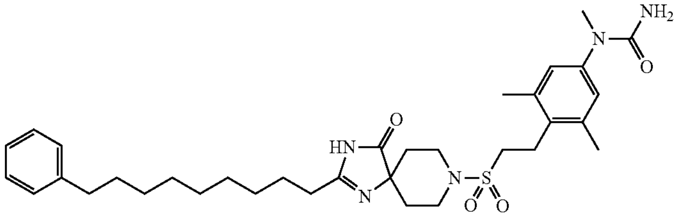 [SMILES: Cc1cc(N(C)C(N)=O)cc(C)c1CCS(=O)(=O)N1CCC2(CC1)N=C(CCCCCCCCCc1ccccc1)NC2=O] | LCMS-C-1 | 3.17 | 624 (M + H)+ |
| 1120 | 1349 | 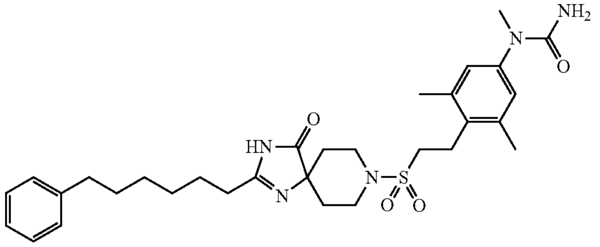 [SMILES: Cc1cc(N(C)C(N)=O)cc(C)c1CCS(=O)(=O)N1CCC2(CC1)N=C(CCCCCCc1ccccc1)NC2=O] | LCMS-C-1 | 2.87 | 582 (M + H)+ |

TABLE 190-continued
| Starting Compound | Target Compound | Structure | LCMS condition | Retention time (min) | MS (m/z) |
|---|---|---|---|---|---|
| 1109 | 1350 | 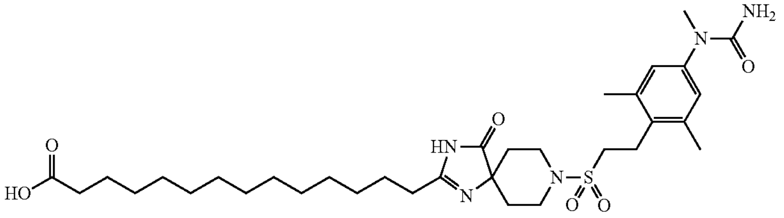 [SMILES: Cc1cc(N(C)C(N)=O)cc(C)c1CCS(=O)(=O)N1CCC2(CC1)N=C(CCCCCCCCCCCCCC(=O)O)NC2=O] | LCMS-C-1 | 2.73 | 648 (M + H)+ |
| 1123 | 1351 | 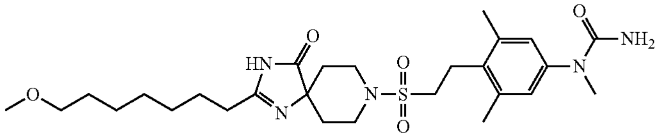 [SMILES: COCCCCCCCC1=NC2(CCN(S(=O)(=O)CCc3c(C)cc(N(C)C(N)=O)cc3C)CC2)C(=O)N1] | LCMS-D-1 | 1.77 | 550 (M + H)+ |
| 1124 | 1352 | 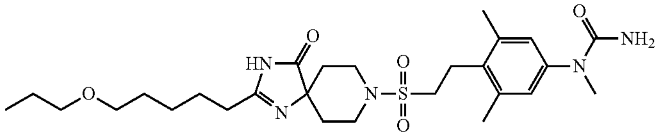 [SMILES: CCCOCCCCCC1=NC2(CCN(S(=O)(=O)CCc3c(C)cc(N(C)C(N)=O)cc3C)CC2)C(=O)N1] | LCMS-D-1 | 1.58 | 550 (M + H)+ |
| 1126 | 1353 | 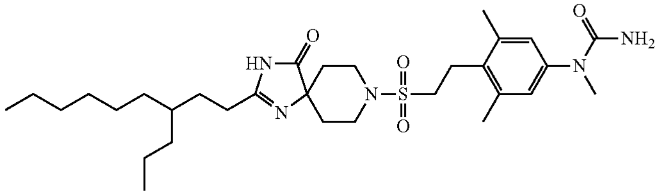 [SMILES: CCCCCCC(CCC)CCC1=NC2(CCN(S(=O)(=O)CCc3c(C)cc(N(C)C(N)=O)cc3C)CC2)C(=O)N1] | LCMS-D-1 | 2.45 | 590 (M + H)+ |
| 1128 | 1354 | 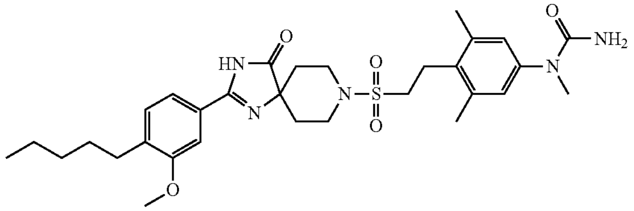 [SMILES: CCCCCc1ccc(C2=NC3(CCN(S(=O)(=O)CCc4c(C)cc(N(C)C(N)=O)cc4C)CC3)C(=O)N2)cc1OC] | LCMS-D-1 | 2.98 | 598 (M + H)+ |
| 1127 | 1355 | 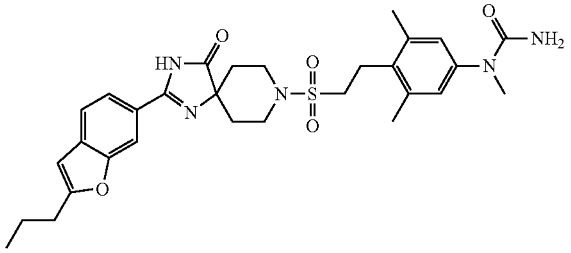 [SMILES: CCCc1cc2ccc(C3=NC4(CCN(S(=O)(=O)CCc5c(C)cc(N(C)C(N)=O)cc5C)CC4)C(=O)N3)cc2o1] | LCMS-D-1 | 2.10 | 580 (M + H)+ |
| 1318 | 1356 | 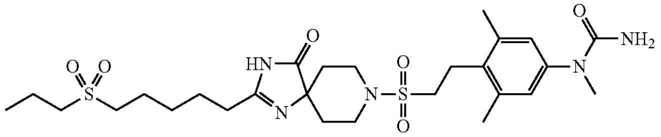 [SMILES: CCCS(=O)(=O)CCCCCC1=NC2(CCN(S(=O)(=O)CCc3c(C)cc(N(C)C(N)=O)cc3C)CC2)C(=O)N1] | LCMS-D-1 | 1.55 | 598 (M + H)+ |
| 1319 | 1357 | 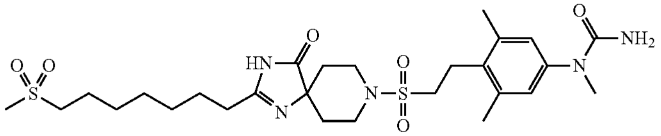 [SMILES: Cc1cc(N(C)C(N)=O)cc(C)c1CCS(=O)(=O)N1CCC2(CC1)N=C(CCCCCCCS(C)(=O)=O)NC2=O] | LCMS-D-1 | 1.52 | 598 (M + H)+ |

TABLE 190-continued
| Starting Compound | Target Compound | Structure | LCMS condition | Retention time (min) | MS (m/z) |
|---|---|---|---|---|---|
| 1088 | 1358 | 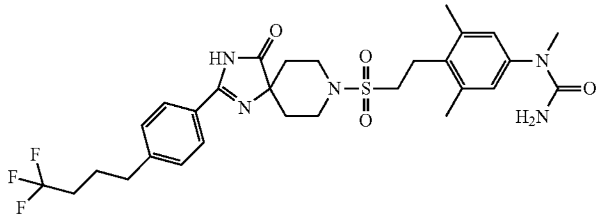 [SMILES: Cc1cc(N(C)C(N)=O)cc(C)c1CCS(=O)(=O)N1CCC2(CC1)N=C(c1ccc(CCCC(F)(F)F)cc1)NC2=O] | LCMS-D-1 | 2.40 | 608 (M + H)+ |
| 1089 | 1359 | 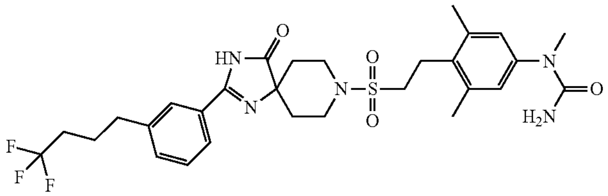 [SMILES: Cc1cc(N(C)C(N)=O)cc(C)c1CCS(=O)(=O)N1CCC2(CC1)N=C(c1cccc(CCCC(F)(F)F)c1)NC2=O] | LCMS-D-1 | 2.48 | 608 (M + H)+ |
| 1308 | 1360 | 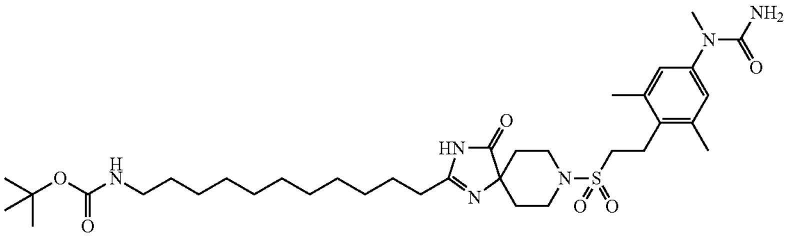 [SMILES: Cc1cc(N(C)C(N)=O)cc(C)c1CCS(=O)(=O)N1CCC2(CC1)N=C(CCCCCCCCCCCNC(=O)OC(C)(C)C)NC2=O] | LCMS-C-1 | 2.98 | 691 (M + H)+ |
| 1307 | 1361 | 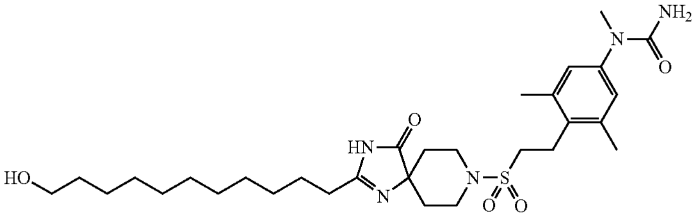 [SMILES: Cc1cc(N(C)C(N)=O)cc(C)c1CCS(=O)(=O)N1CCC2(CC1)N=C(CCCCCCCCCCCO)NC2=O] | LCMS-C-1 | 2.68 | 592 (M + H)+ |
| 1171 | 1362 | 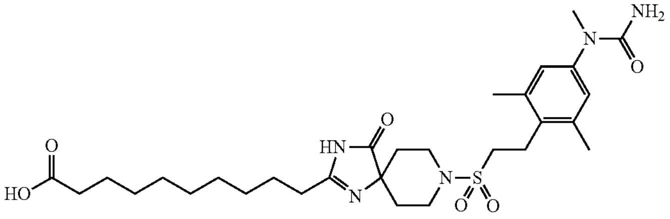 [SMILES: Cc1cc(N(C)C(N)=O)cc(C)c1CCS(=O)(=O)N1CCC2(CC1)N=C(CCCCCCCCCC(=O)O)NC2=O] | LCMS-F-1 | 0.85 | 592 (M + H)+ |
| 1172 | 1363 | 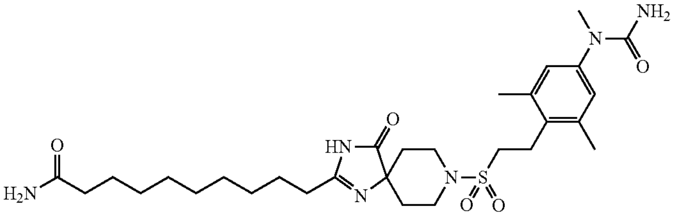 [SMILES: Cc1cc(N(C)C(N)=O)cc(C)c1CCS(=O)(=O)N1CCC2(CC1)N=C(CCCCCCCCCC(N)=O)NC2=O] | LCMS-F-1 | 0.88 | 591 (M + H)+ |

TABLE 190-continued

| Starting Compound | Target Compound | Structure | LCMS condition | Retention time (min) | MS (m/z) |
| --- | --- | --- | --- | --- | --- |
| 1110 | 1364 | 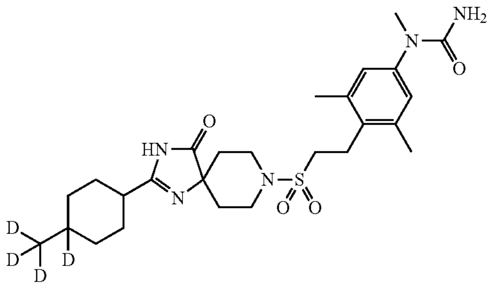 [SMILES: [2H]C([2H])([2H])C1([2H])CCC(C2=NC3(CCN(S(=O)(=O)CCc4c(C)cc(N(C)C(N)=O)cc4C)CC3)C(=O)N2)CC1] | LCMS-F-1 | 0.93 | 522 (M + H)+ |

Example 317

1-(3,5-Dimethyl-4-{(E)-2-[4-oxo-2-(9-phenyl-nonyl)-1,3,8-triaza-spiro[4.5]dec-1-ene-8-sulfonyl]-vinyl}-phenyl)-1-methyl-urea (Compound 1365)

(Reaction 317-1)

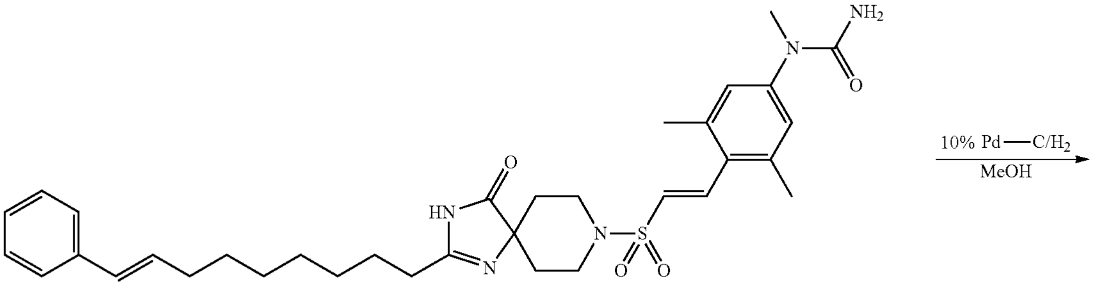

Compound 1121

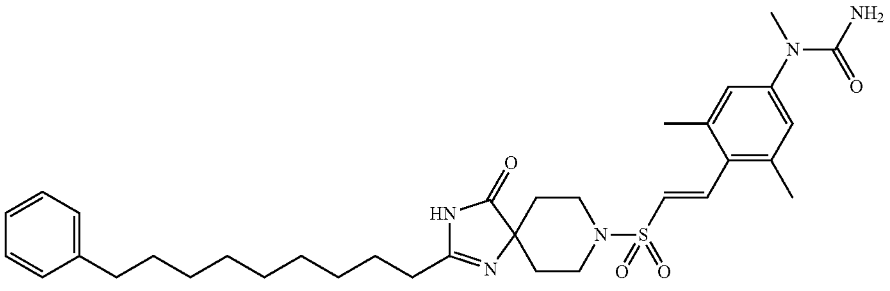

Compound 1365

1-(3,5-Dimethyl-4-{(E)-2-[4-oxo-2-(9-phenyl-nonyl)-1,3,8-triaza-spiro[4.5]dec-1-ene-8-sulfonyl]-vinyl}-phenyl)-1-methyl-urea (Compound 1365) was obtained by operations similar to those in Reaction 18-2 using Compound 1121 as a starting material.

MS (ESI) m/z=622 (M+H)+.

Example 318

1-(4-{2-[2-(11-Amino-undecyl)-4-oxo-1,3,8-triaza-spiro[4.5]dec-1-ene-8-sulfonyl]-ethyl}-3,5-dimethyl-phenyl)-1-methyl-urea (Compound 1366)

(Reaction 318-1)

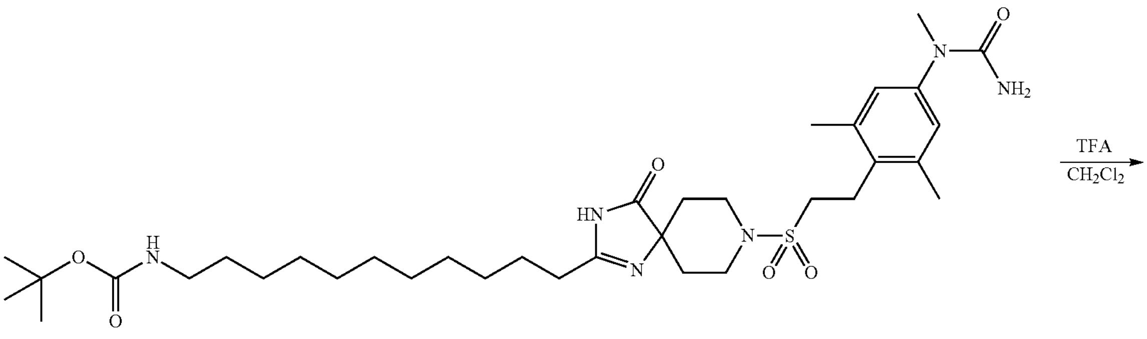

Compound 1360

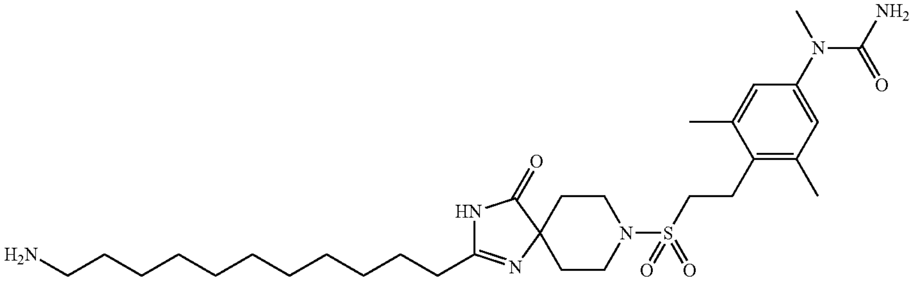

Compound 1366

1-(4-{2-[2-(11-Amino-undecyl)-4-oxo-1,3,8-triaza-spiro[4.5]dec-1-ene-8-sulfonyl]-ethyl}-3,5-dimethyl-phenyl)-1-methyl-urea (Compound 1366) was obtained by operations similar to those in Reaction 4-1 using Compound 1360 as a starting material.

MS (ESI) m/z=591 (M+H)+.

Example 319

3-[(3,5-Dimethyl-4-{2-[2-(4-methyl-cyclohexyl)-4-oxo-1,3,8-triaza-spiro[4.5]dec-1-ene-8-sulfonyl]-ethyl}-phenyl)-methyl-amino]-4-ethoxy-cyclobut-3-ene-1,2-dione (Compound 1367)

(Reaction 319-1)

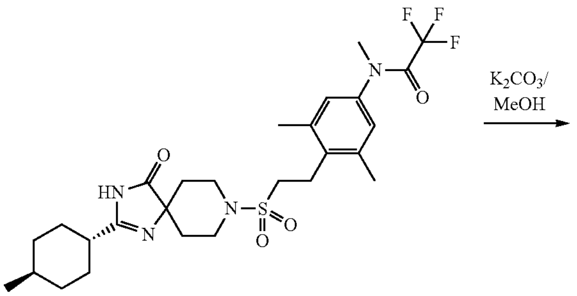

Compound 931

-continued

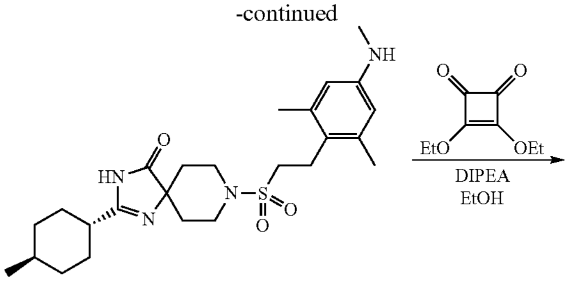

319a

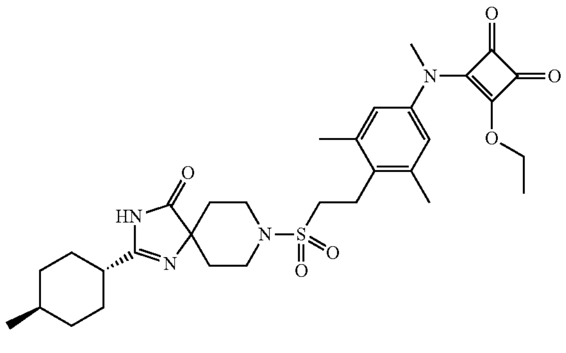

Compound 1367

3-[(3,5-Dimethyl-4-{2-[2-(4-methyl-cyclohexyl)-4-oxo-1,3,8-triaza-spiro[4.5]dec-1-ene-8-sulfonyl]-ethyl}-phenyl)-methyl-amino]-4-ethoxy-cyclobut-3-ene-1,2-dione (Compound 1367) was obtained by operations similar to those in Reaction 12-5 and Reaction 95-17 (using ethanol as a solvent) using N-(3,5-dimethyl-4-{2-[2-(4-methyl-cyclohexyl)-4-oxo-1,3,8-triaza- spiro[4.5]dec-1-ene-8-sulfonyl]-ethyl}-phenyl)-2,2,2-trifluoro-N-methyl-acetamide as a starting material.

MS (ESI) m/z=599 (M+H)+.

Example 320

3-Amino-4-[(3,5-dimethyl-4-{2-[2-(4-methyl-cyclohexyl)-4-oxo-1,3,8-triaza-spiro[4.5]dec-1-ene-8-sulfonyl]-ethyl}-phenyl)-methyl-amino]-cyclobut-3-ene-1,2-dione (Compound 1368)

(Reaction 320-1)

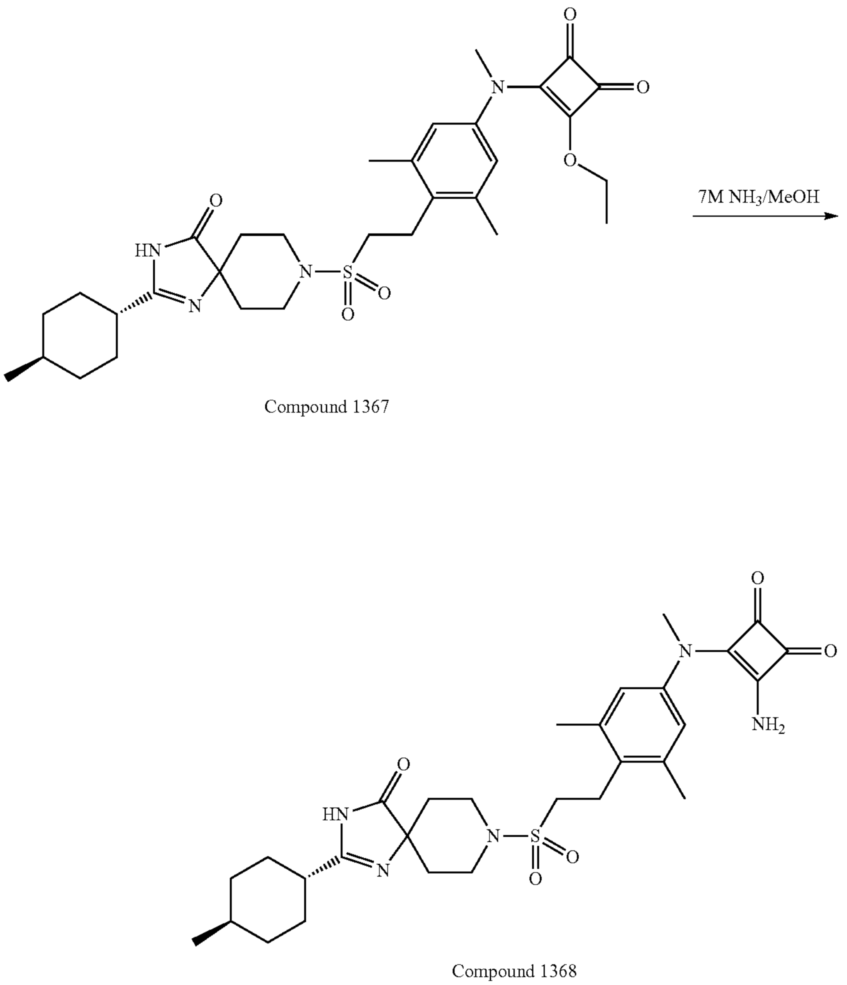

Compound 1367

Compound 1368

3-Amino-4-[(3,5-dimethyl-4-{2-[2-(4-methyl-cyclohexyl)-4-oxo-1,3,8-triaza-spiro[4.5]dec-1-ene-8-sulfonyl]-ethyl}-phenyl)-methyl-amino]-cyclobut-3-ene-1,2-dione (Compound 1368) was obtained by operations similar to those in Reaction 230-3 using Compound 1367 as a starting material.

MS (ESI) m/z=570 (M+H)+.

Example 321

3-Dimethylamino-4-[(3,5-dimethyl-4-{2-[2-(4-methyl-cyclohexyl)-4-oxo-1,3,8-triaza-spiro[4.5]dec-1-ene-8-sulfonyl]-ethyl}-phenyl)-methyl-amino]-cyclobut-3-ene-1,2-dione (Compound 1369)

(Reaction 321-1)

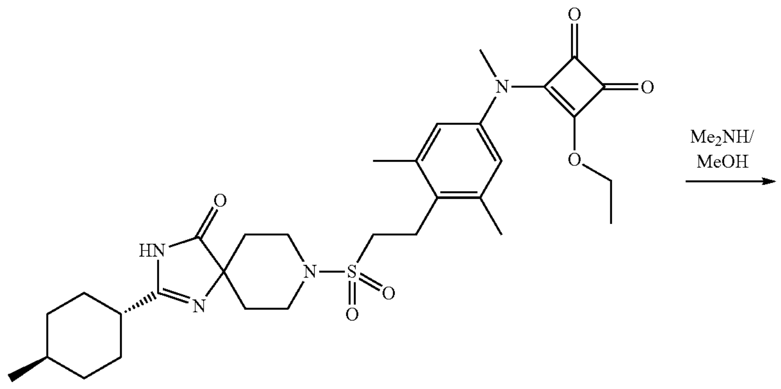

Compound 1367

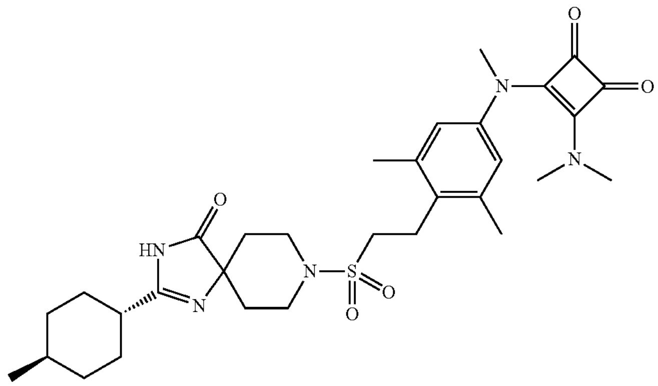

Compound 1369

3-Dimethylamino-4-[(3,5-dimethyl-4-{2-[2-(4-methyl-cyclohexyl)-4-oxo-1,3,8-triaza-spiro[4.5]dec-1-ene-8-sulfonyl]-ethyl}-phenyl)-methyl-amino]-cyclobut-3-ene-1,2-dione (Compound 1369) was obtained by operations similar to those in Reaction 230-3 using Compound 1367 as a starting material.

MS (ESI) m/z=598 (M+H)+.

Example 322

N-(4-{2-[2-(4-Ethynyl-cyclohexyl)-4-oxo-1,3,8-triaza-spiro[4.5]dec-1-ene-8-sulfonyl]-ethyl}-3-methyl-phenyl)-acetamide (Compound 1370)

(Reaction 322-1)

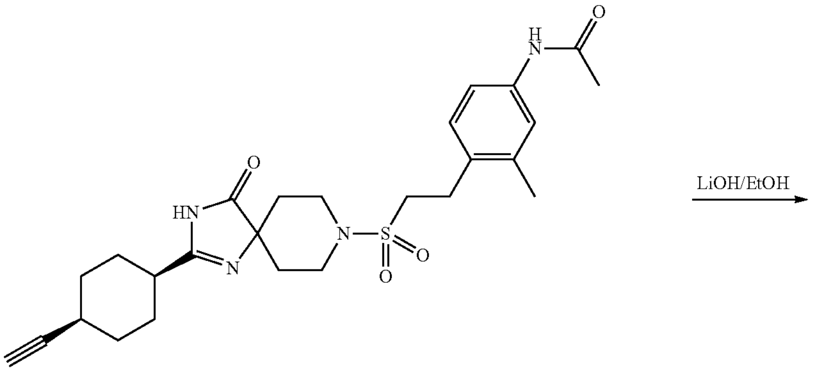

Compound 1074

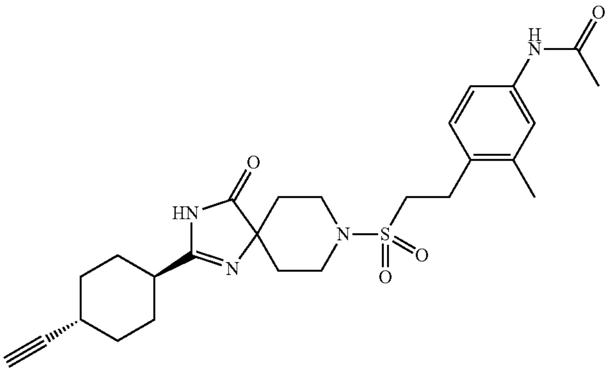

Compound 1370

Lithium hydroxide monohydrate (4.3 mg, 0.102 mmol) was added to a mixed solution of N-(4-{2-[2-(4-ethynyl-cyclohexyl)-4-oxo-1,3,8-triaza-spiro[4.5]dec-1-ene-8-sulfonyl]-ethyl}-3-methyl-phenyl)-acetamide (17 mg, 0.0341 mmol) in ethanol (1.25 mL) at room temperature. The mixture was stirred at 60° C. for 14 hours and then concentrated under reduced pressure. The resulting residue was purified by silica gel column chromatography to give N-(4-{2-[2-(4-ethynyl-cyclohexyl)-4-oxo-1,3,8-triaza-spiro[4.5]dec-1-ene-8-sulfonyl]-ethyl}-3-methyl-phenyl)-acetamide as a white solid (17 mg, 99%).

MS (ESI) m/z=499 (M+H)+.

Example 323
1-(4-{2-[4-[(E)-Hydroxyimino]-2-(4-methyl-cyclohexyl)-1,3,8-triaza-spiro[4.5]dec-1-ene-8-sulfonyl]-ethyl}-3,5-dimethyl-phenyl)-1-methyl-urea (Compound 1371)
(Reaction 323-1)
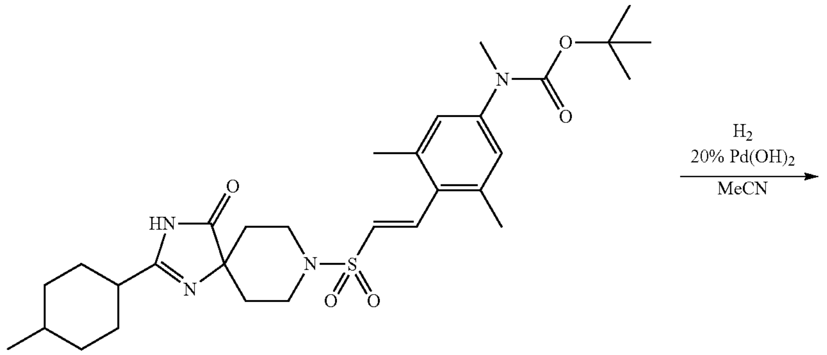
179a
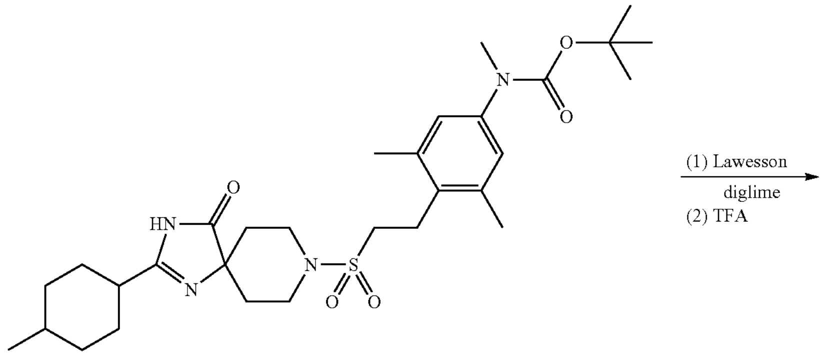
323a
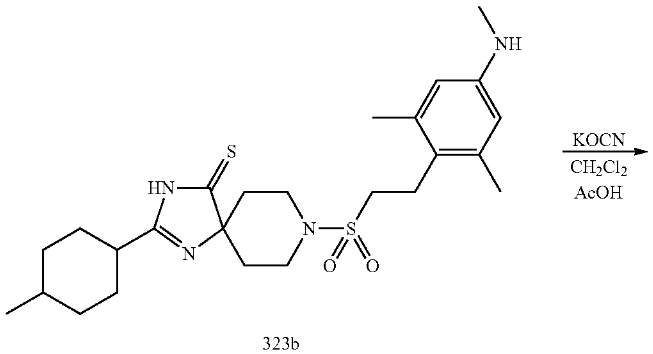
323b -continued

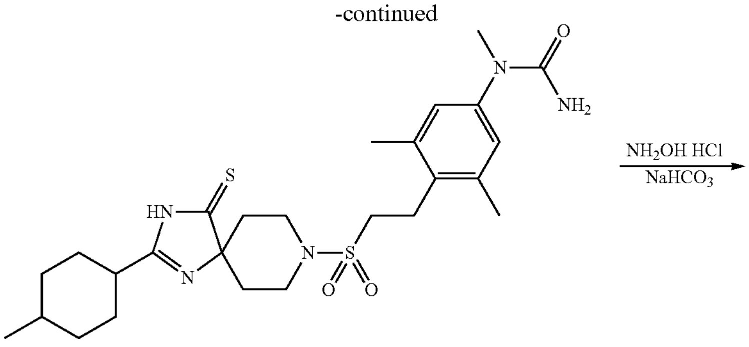

323c

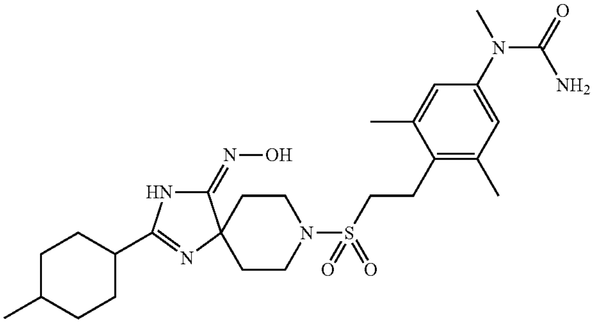

Compound 1371

1-(4-{2-[4-[(E)-Hydroxyimino]-2-(4-methyl-cyclohexyl)-1,3,8-triaza-spiro[4.5]dec-1-ene-8-sulfonyl]-ethyl}-3,5-dimethyl-phenyl)-1-methyl-urea (Compound 1371) was obtained by operations similar to those in Reaction 184-1, Reaction 88-1, Reaction 89-2 (using KOCN) and Reaction 189-9 using 3,5-dimethyl-4-{(E)-2-[2-(4-methyl-cyclohexyl)-4-oxo-1,3,8-triaza-spiro[4.5]dec-1-ene-8-sulfonyl]-vinyl}-phenyl)-methyl-carbamic acid tert-butyl ester as a starting material.

MS (ESI) m/z=533 (M+H)+.

Example 324

2-(4-Methyl-cyclohexyl)-4-oxo-1,3,8-triaza-spiro[4.5]dec-1-ene-8-sulfonic acid 2-methyl-benzylamide (Compound 1372)

(Reaction 324-1)

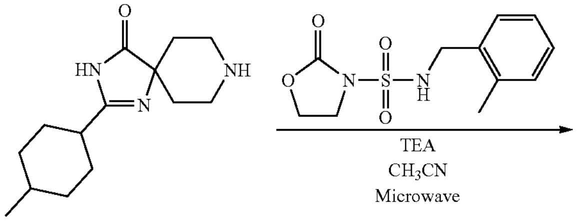

11j

-continued

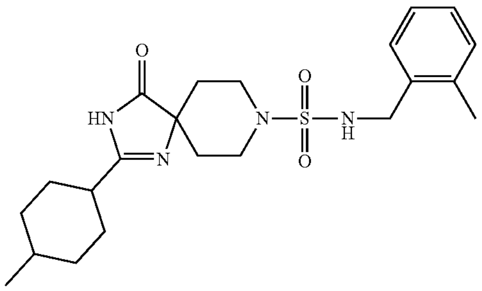

Compound 1372

2-(4-Methyl-cyclohexyl)-4-oxo-1,3,8-triaza-spiro[4.5]dec-1-ene-8-sulfonic acid 2-methyl-benzylamide (Compound 1372) was obtained by operations similar to those in Reaction 24-2 using 2-(4-methyl-cyclohexyl)-1,3,8-triaza-spiro[4.5]dec-1-en-4-one as a starting material.

MS (ESI) m/z=433 (M+H)+.

Example 325

2-(4-Methyl-cyclohexyl)-4-oxo-1,3,8-triaza-spiro[4.5]dec-1-ene-8-sulfonic (2-o-tolyl-ethyl)-amide (Compound 1373)

(Reaction 325-1)

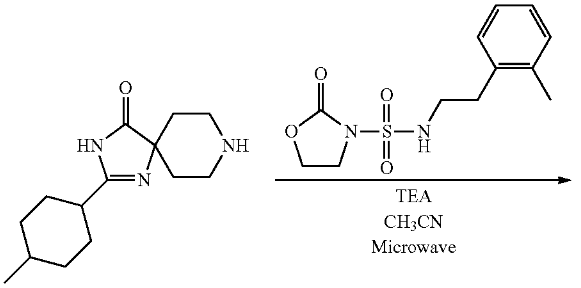

11j

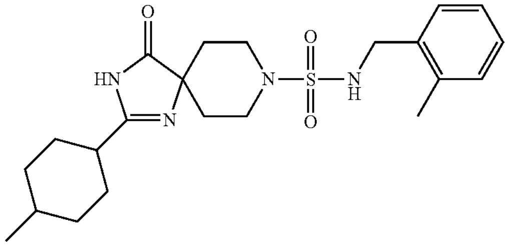

Compound 1373

2-(4-Methyl-cyclohexyl)-4-oxo-1,3,8-triaza-spiro[4.5]dec-1-ene-8-sulfonic (2-o-tolyl-ethyl)-amide (Compound 1373) was obtained by operations similar to those in Reaction 24-2 using 2-(4-methyl-cyclohexyl)-1,3,8-triaza-spiro[4.5]dec-1-en-4-one as a starting material.

MS (ESI) m/z=448 (M+H)+.

Example 326

2-Cyclohexyl-8-{2-[1-((S)-2,3-dihydroxy-propyl)-1H-indol-4-yl]-2-hydroxy-ethanesulfonyl}-1,3,8-triaza-spiro[4.5]dec-1-en-4-one (Compound 1374)

(Reaction 326-1)

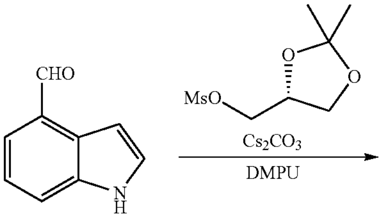

326a

-continued

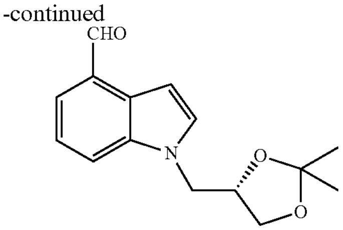

326b

1H-Indole-4-carbaldehyde (1.81 g, 12.5 mmol) and cesium carbonate (8.15 g, 25.0 mmol) were added to a solution of methanesulfonic acid (R)-2,2-dimethyl-[1,3]dioxolan-4-yl methyl ester (3.40 g, 16.1 mmol) in 1,3-dimethyl-3,4,5,6-tetrahydro-2(1H)-pyrimidinone (30.8 mL), and the mixture was stirred at 90° C. for 40 hours. Water was added, followed by extraction with hexane:ethyl acetate (1:4). The organic layer was washed with water four times and then dried over sodium sulfate. After concentration, the residue was purified by silica gel column chromatography to give 1-((S)-2,2-dimethyl-[1,3]dioxolan-4-ylmethyl)-1H-indole-4-carbaldehyde (2.88 g, 88%) as a yellow oily substance.

MS (ESI) m/z=260 (M+H)+.

(Reaction 326-2)

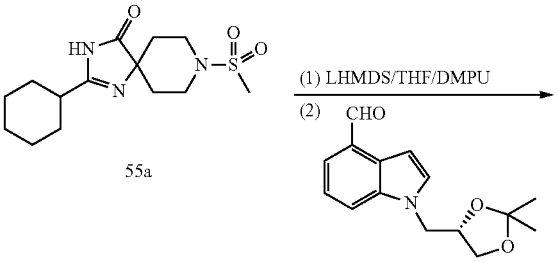

55a

326b

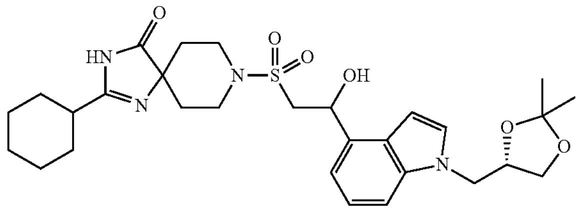

326c

A suspension of 2-cyclohexyl-8-methanesulfonyl-1,3,8-triaza-spiro[4.5]dec-1-en-4-one (100 mg, 0.319 mmol) in 1,3-dimethyl-3,4,5,6-tetrahydro-2(1H)-pyrimidinone (0.66 mL) was cooled to 0° C. A 1 M solution of lithium hexamethyldisilazide in tetrahydrofuran (0.989 ml) was then added and the mixture was stirred at room temperature for 30 minutes. After cooling again to 0° C., a solution of 1-((S)-2,2-dimethyl-[1,3]dioxolan-4-ylmethyl)-1H-indole-4-carbaldehyde (87 mg, 0.335 mmol) in tetrahydrofuran (0.4 mL) was added and the mixture was stirred at 0° C. for five hours. Water was added and the aqueous layer was extracted with ethyl acetate. The organic layer was washed with water and then dried over sodium sulfate. After concentration, the residue was purified by silica gel column chromatography to give 2-cyclohexyl-8-{2-[1-((S)-2,2-dimethyl-[1,3]dioxolan-4-ylmethyl)-1H indol-4-yl]-2-hydroxy-ethanesulfonyl}-1,3,8-triaza-spiro[4.5]dec-1-en-4-one (113 mg, 62%) as a pale yellow solid.

MS (ESI) m/z=573 (M+H)+.

(Reaction 326-3)

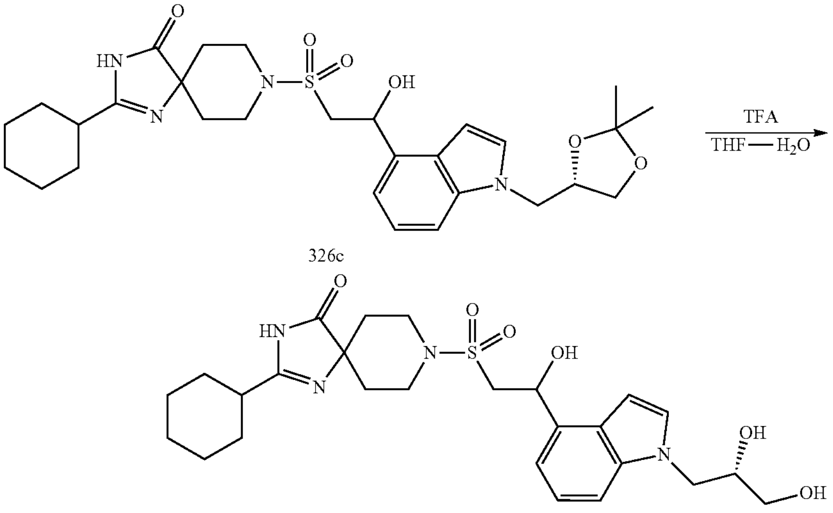

326c

Compound 1374

2-Cyclohexyl-8-{2-[1-((S)-2,3-dihydroxy-propyl)-1H-indol-4-yl]-2-hydroxy-ethanesulfonyl}-1,3,8-triaza-spiro[4.5]dec-1-en-4-one (Compound 1374) was synthesized by operations similar to those in Reaction 4-1 using appropriate reagents and starting material.

MS (ESI) m/z=573, 533 (M+H)+.

Example 327

2-Cyclohexyl-8-(2-oxo-2-o-tolyl-ethanesulfonyl)-1,3,8-triaza-spiro[4.5]dec-1-en-4-one (Compound 1375)

(Reaction 327-1)

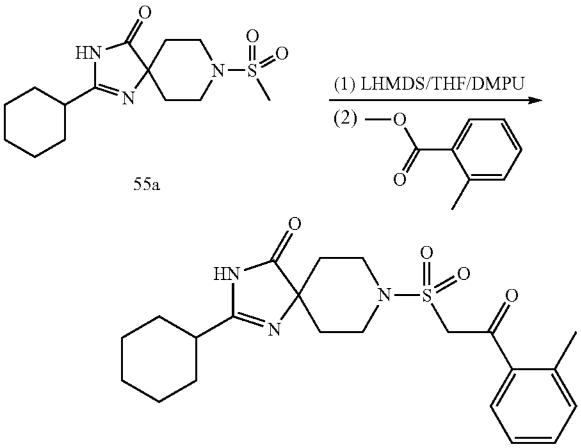

55a

Compound 1375

2-Cyclohexyl-8-(2-oxo-2-o-tolyl-ethanesulfonyl)-1,3,8-triaza-spiro[4.5]dec-1-en-4-one (Compound 1375) was obtained by operations similar to those in Reaction 326-2 using 2-cyclohexyl-8-methanesulfonyl-1,3,8-triaza-spiro[4.5]dec-1-en-4-one as a starting material.

MS (ESI) m/z=432 (M+H)+.

Example 328

2-Cyclohexyl-8-(2-o-tolyl-ethynesulfonyl)-1,3,8-triaza-spiro[4.5]dec-1-en-4-one (Compound 1376)

(Reaction 328-1)

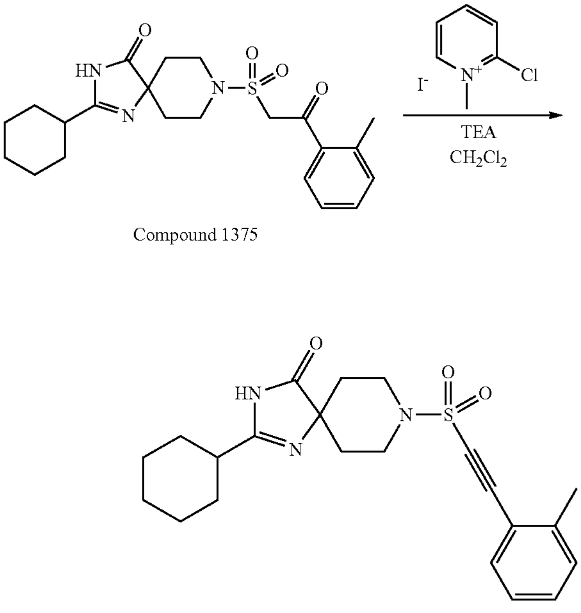

Compound 1375

Compound 1376

2-Chloro-1-methyl-pyridinium iodide (18 mg, 0.070 mmol) and triethylamine (0.28 mL, 1.98 mmol) were added to a solution of 2-cyclohexyl-8-(2-oxo-2-o-tolyl-ethanesulfonyl)-1,3,8-triaza-spiro[4.5]dec-1-en-4-one (20 mg, 0.046 mmol) in methylene chloride (1.0 mL), and the mixture was stirred at room temperature for 19 hours. 2-Chloro-1-methylpyridinium iodide (18 mg, 0.070 mmol) and triethylamine (0.28 mL, 1.98 mmol) were further added, and the mixture was stirred at room temperature for five hours. A 1 M aqueous sodium hydroxide solution was added to the reaction mixture, and the mixture was stirred at room temperature for 20 minutes. The aqueous layer was extracted with methylene chloride, and the organic layer was washed with a 1 M aqueous sodium hydroxide solution, water and saturated brine and dried over sodium sulfate. The organic layer was concentrated, and the residue was then silica gel column chromatography to give 2-cyclohexyl-8-(2-o-tolyl-ethynesulfonyl)-1,3,8-triaza-spiro[4.5]dec-1-en-4-one (15 mg, 79%) as a white solid.

$^1$H-NMR ($CDCl_3$) δ 8.39 (1H, s), 7.60 (1H, dd, J=7.6, 1.2 Hz), 7.38 (1H, td, J=7.6, 1.4 Hz), 7.28-7.16 (2H, m), 3.80-3.75 (2H, m), 3.42-3.36 (2H, m), 2.52 (3H, s), 2.46-2.38 (1H, m), 2.14-2.07 (2H, m), 1.94-1.56 (8H, m), 1.47-1.22 (6H, m); MS (ESI) m/z=414 (M+H)+.

Example 329

2-Cyclohexyl-8-[2-(1H-indol-4-yl)-ethynesulfonyl]-1,3,8-triaza-spiro[4.5]dec-1-en-4-one (Compound 1377)

(Reaction 329-1)

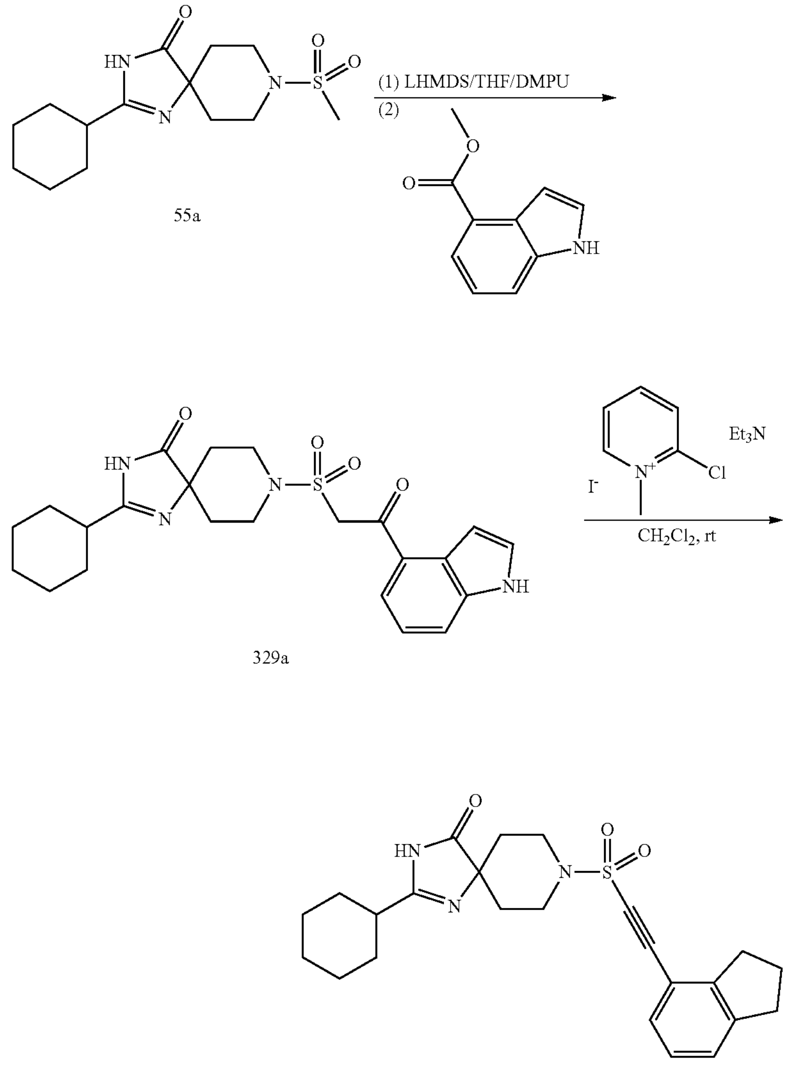

55a

329a

Compound 1377

2-Cyclohexyl-8-[2-(1H-indol-4-yl)-ethynesulfonyl]-1,3,8-triaza-spiro[4.5]dec-1-en-4-one (Compound 1377) was obtained by operations similar to those in Reaction 326-2 and Reaction 328-1 using 2-cyclohexyl-8-methanesulfonyl-1,3,8-triaza-spiro[4.5]dec-1-en-4-one as a starting material.

MS (ESI) m/z=439 (M+H)+.

Example 330

3,5,N,N-Tetramethyl-4-(2-{4-oxo-2-[4-(3,3,3-trifluoro-propyl)-cyclohexyl]-1,3,8-triaza-spiro[4.5]dec-1-ene-8-sulfonyl}-ethyl)-benzamide (Compound 1378)

(Reaction 330-1)

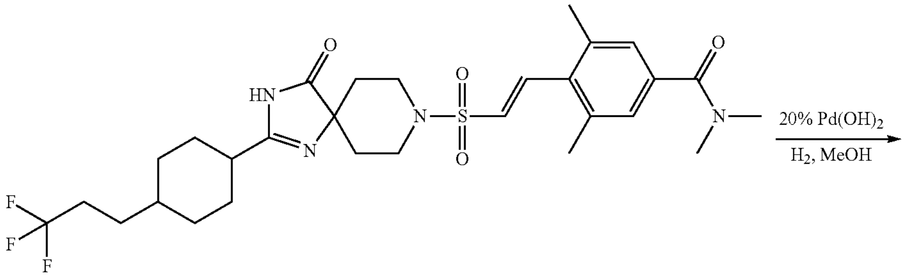

Compound 994

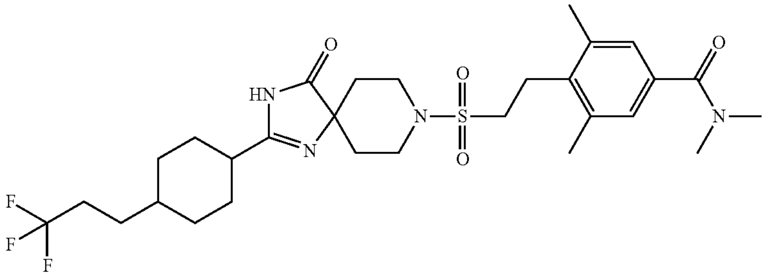

Compound 1378

3,5,N,N-Tetramethyl-4-(2-{4-oxo-2-[4-(3,3,3-trifluoro-propyl)-cyclohexyl]-1,3,8-triaza-spiro[4.5]dec-1-ene-8-sulfonyl}-ethyl)-benzamide (Compound 1378) was obtained by operations similar to those in Reaction 122-2 using Compound 994 as a starting material.

MS (ESI) m/z=599 (M+H)+.

The example compounds shown below were obtained by operations similar to those in Reaction 330-1 using appropriate solvents (acetonitrile or methanol or an acetonitrile-methanol mixed solution) and starting compounds.

Compounds 1379 to Compound 1391

TABLE 191

| Starting Compound | Target Compound | Structure | LCMS condition | Retention time (min) | MS (m/z) |
|---|---|---|---|---|---|
| 1003 | 1379 | 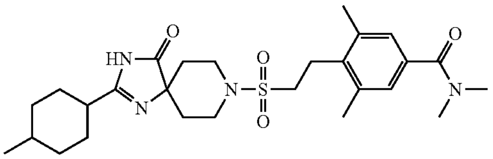 | LDMS D-1 | 1.91 | 517 (M + H)+ |

TABLE 191-continued
| Starting Compound | Target Compound | Structure | LCMS condition | Retention time (min) | MS (m/z) |
|---|---|---|---|---|---|
| 989 | 1380 | 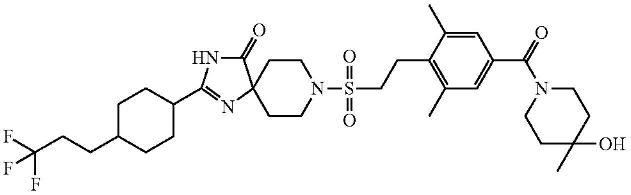 [SMILES: Cc1cc(C(=O)N2CCC(C)(O)CC2)cc(C)c1CCS(=O)(=O)N1CCC2(CC1)N=C(C1CCC(CCC(F)(F)F)CC1)NC2=O] | LDMS D-1 | 2.31 | 669 (M + H)+ |
| 990 | 1381 | 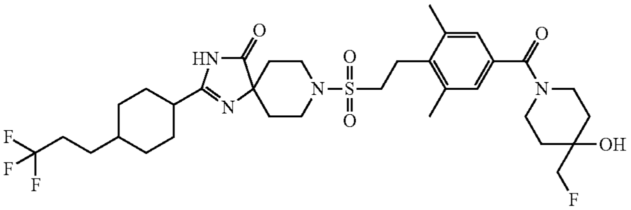 [SMILES: Cc1cc(C(=O)N2CCC(O)(CF)CC2)cc(C)c1CCS(=O)(=O)N1CCC2(CC1)N=C(C1CCC(CCC(F)(F)F)CC1)NC2=O] | LDMS D-1 | 2.26 | 687 (M + H)+ |
| 999 | 1382 | 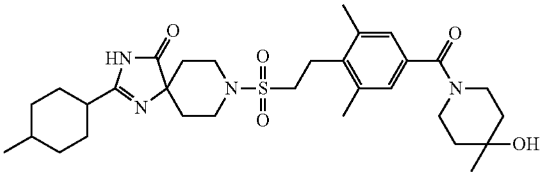 [SMILES: Cc1cc(C(=O)N2CCC(C)(O)CC2)cc(C)c1CCS(=O)(=O)N1CCC2(CC1)N=C(C1CCC(C)CC1)NC2=O] | LDMS C-1 | 2.62 | 585 (M + H)+ |
| 1000 | 1383 | 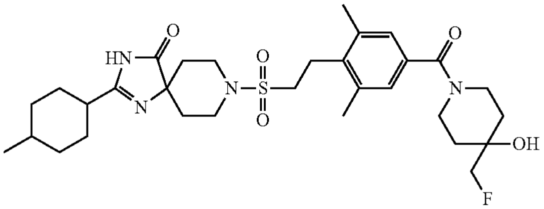 [SMILES: Cc1cc(C(=O)N2CCC(O)(CF)CC2)cc(C)c1CCS(=O)(=O)N1CCC2(CC1)N=C(C1CCC(C)CC1)NC2=O] | LDMS D-1 | 2.88 | 605 (M + H)+ |
| 993 | 1384 | 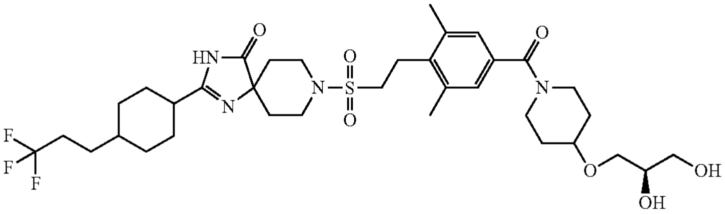 [SMILES: Cc1cc(C(=O)N2CCC(OC[C@H](O)CO)CC2)cc(C)c1CCS(=O)(=O)N1CCC2(CC1)N=C(C1CCC(CCC(F)(F)F)CC1)NC2=O] | LDMS D-1 | 2.17 | 729 (M + H)+ |
| 996 | 1385 | 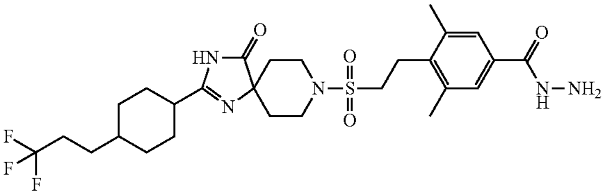 [SMILES: Cc1cc(C(=O)NN)cc(C)c1CCS(=O)(=O)N1CCC2(CC1)N=C(C1CCC(CCC(F)(F)F)CC1)NC2=O] | LDMS D-1 | 1.87 | 586 (M + H)+ |
| 997 | 1386 | 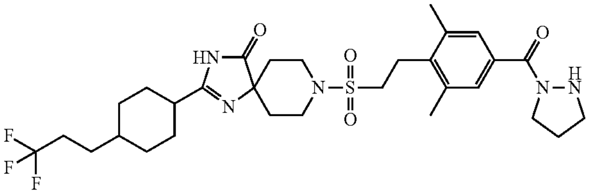 [SMILES: Cc1cc(C(=O)N2CCCN2)cc(C)c1CCS(=O)(=O)N1CCC2(CC1)N=C(C1CCC(CCC(F)(F)F)CC1)NC2=O] | LDMS D-1 | 2.00 | 626 (M + H)+ |

TABLE 191-continued
| Starting Compound | Target Compound | Structure | LCMS condition | Retention time (min) | MS (m/z) |
|---|---|---|---|---|---|
| 987 | 1387 | 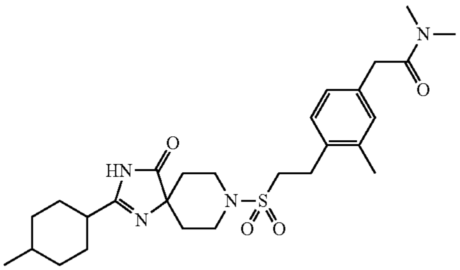 | LDMS F-1 | 0.94 | 517 (M + H)+ |
| 988 | 1388 | 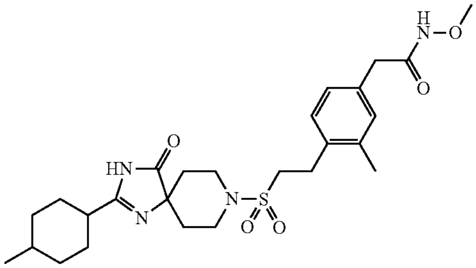 | LDMS F-1 | 0.90 | 519 (M + H)+ |
| 1300 | 1389 | 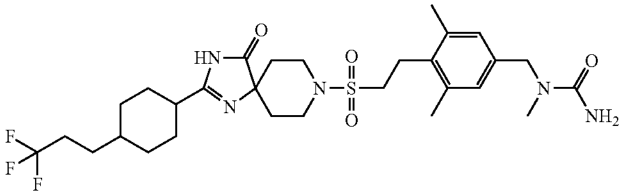 [SMILES: Cc1cc(CN(C)C(N)=O)cc(C)c1CCS(=O)(=O)N1CCC2(CC1)N=C(C1CCC(CCC(F)(F)F)CC1)NC2=O] | LDMS D-1 | 2.37 | 614 (M + H)+ |
| 1301 | 1390 | 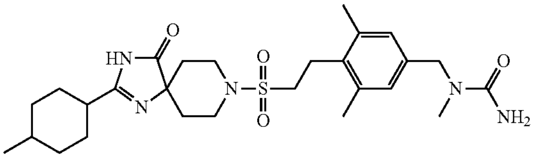 [SMILES: Cc1cc(CN(C)C(N)=O)cc(C)c1CCS(=O)(=O)N1CCC2(CC1)N=C(C1CCC(C)CC1)NC2=O] | LDMS D-1 | 1.95 | 532 (M + H)+ |
| 1312 | 1391 | 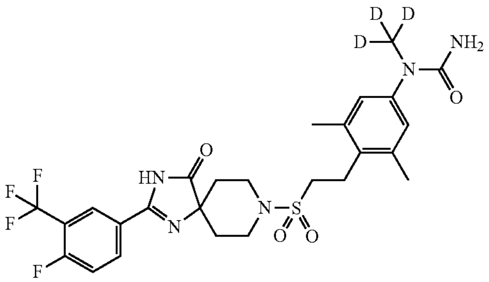 [SMILES: [2H]C([2H])([2H])N(C(N)=O)c1cc(C)c(CCS(=O)(=O)N2CCC3(CC2)N=C(c2ccc(F)c(C(F)(F)F)c2)NC3=O)c(C)c1] | LDMS F-1 | 0.98 | 587 (M + H)+ |

Example 331
2-Cyclohexyl-8-{2-[1-((2S,3S)-2,3,4-trihydroxy-butyl)-1H-indol-4-yl]-ethanesulfonyl}-1,3,8-triaza-spiro[4.5]dec-1-en-4-one (Compound 1392) and 8-{2-[1-((2S,3S)-4-benzyloxy-2,3-dihydroxy-butyl)-1H-indol-4-yl]-ethanesulfonyl}-2-cyclohexyl-1,3,8-triaza-spiro[4.5]dec-1-en-4-one (Compound 1393)
(Reaction 331-1)
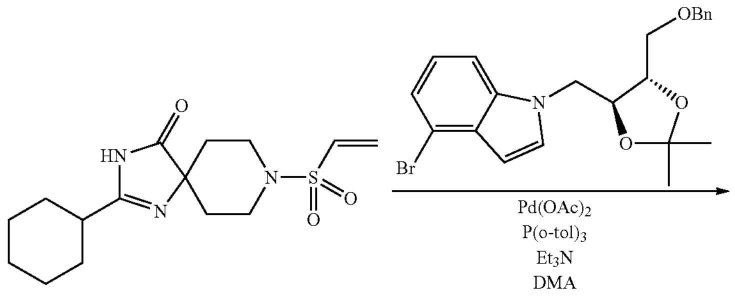
25b
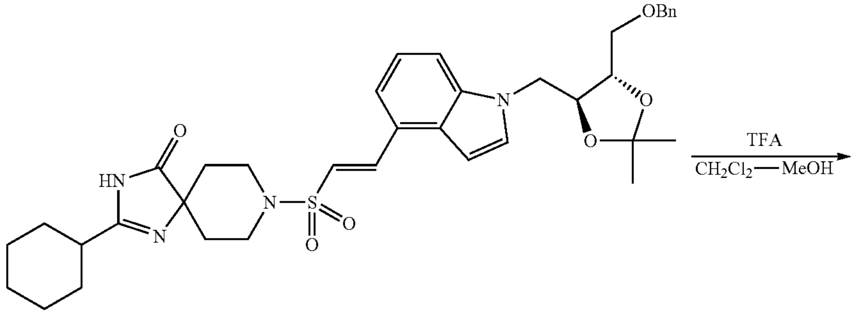
331b
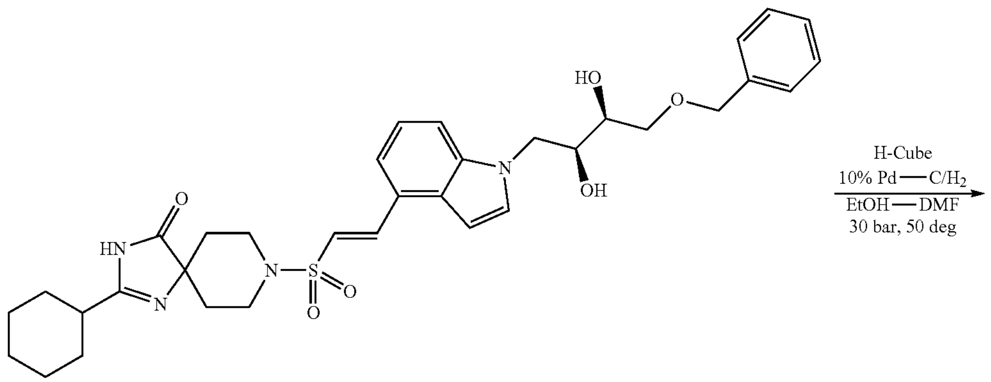
331c -continued

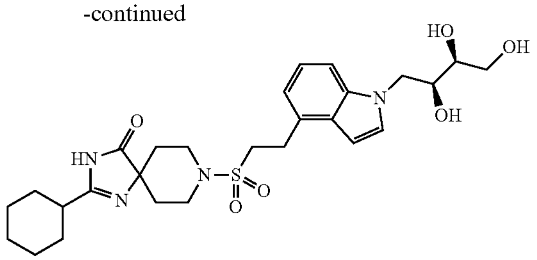

Compound 1392

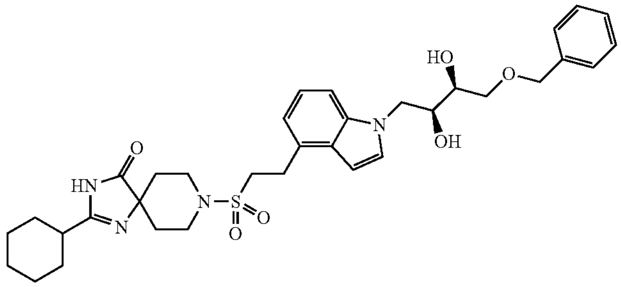

Compound 1393

2-Cyclohexyl-8-{2-[1-((2S,3S)-2,3,4-trihydroxy-butyl)-1H-indol-4-yl]-ethanesulfonyl}-1,3,8-triaza-spiro[4.5]dec-1-en-4-one (Compound 1392)

MS (ESI) m/z=547 (M+H)+ and 8-{2-[1-((2S,3S)-4-benzyloxy-2,3-dihydroxy-butyl)-1H-indol-4-yl]-ethanesulfonyl}-2-cyclohexyl-1,3,8-triaza-spiro[4.5]dec-1-en-4-one (Compound 1393)

MS (ESI) m/z=637 (M+H)+ were obtained by operations similar to those in Reaction 26-1, Reaction 4-1 and Reaction 42-2 using 2-cyclohexyl-8-ethenesulfonyl-1,3,8-triaza-spiro[4.5]dec-1-en-4-one as a starting material.

Example 332

N-[3-Methyl-4-(2-{4-oxo-2-[4-(3,3,3-trifluoro-propyl)-cyclohexyl]-1,3,8-triaza-spiro[4.5]dec-1-ene-8-sulfonyl}-ethyl)-benzyl]-acetamide (Compound 1394)

(Reaction 332-1)

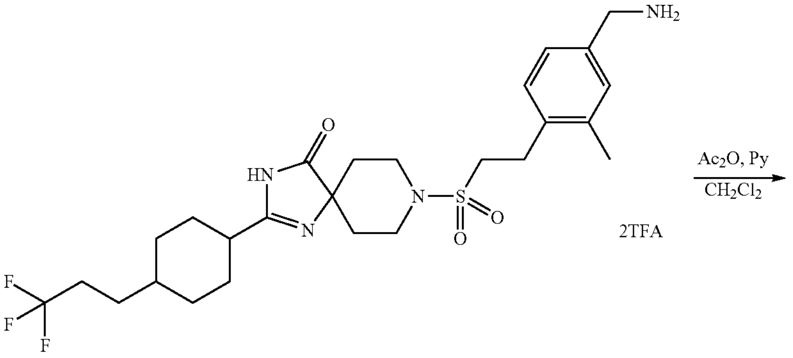

Compound 1284

-continued

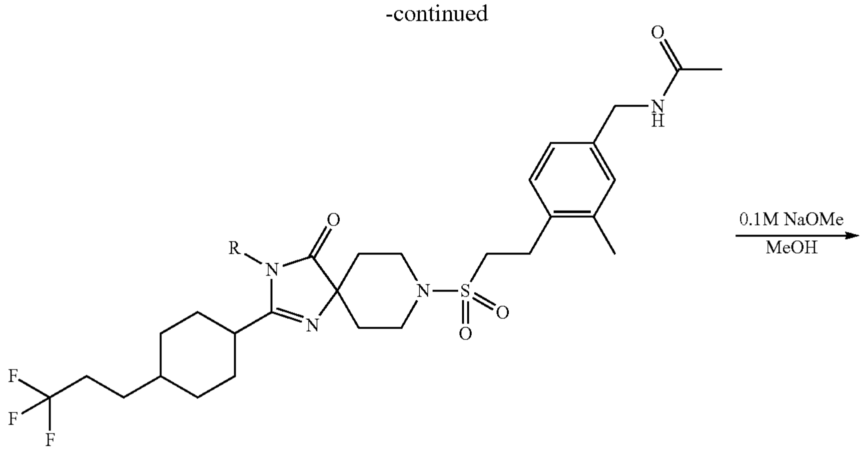

mixture (R = H or Ac)
332a

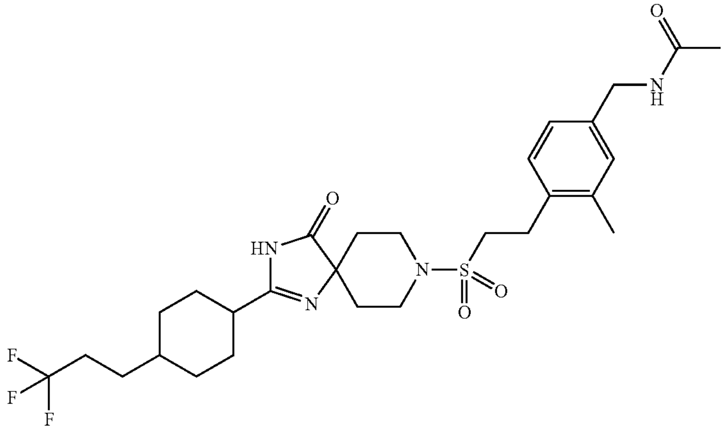

Compound 1394

N-[3-Methyl-4-(2-{4-oxo-2-[4-(3,3,3-trifluoro-propyl)-cyclohexyl]-1,3,8-triaza-spiro[4.5]dec-1-ene-8-sulfonyl}-ethyl)-benzyl]-acetamide (Compound 1394) was obtained by operations similar to those in Reaction 12-2 and Reaction 14-1 (using NaOMe as a base) using Compound 1284 as a starting material.

MS (ESI) m/z=585 (M+H)+.

Example 333

3,N,N-Trimethyl-4-{2-[4-oxo-2-(3-trifluoromethyl-phenylamino)-1,3,8-triaza-spiro[4.5]dec-1-ene-8-sulfonyl]-ethyl}-benzamide (Compound 1395)

(Reaction 333-1)

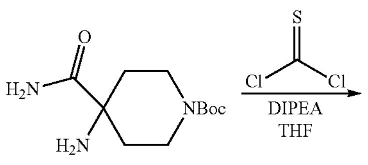

10ag

-continued

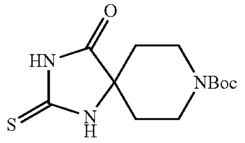

333a

N,N-Diisopropylethylamine (1.67 ml, 9.84 mmol) was added to a solution of 4-amino-4-carbamoyl-piperidine-1-carboxylic acid tert-butyl ester (1.0 g, 4.1 mmol) in THF (10 ml) at 0° C., and thiophosgene (0.376 ml, 4.9 mmol) was further added dropwise slowly. The reaction solution was warmed to room temperature and stirred overnight. A 10% aqueous citric acid solution was added to the reaction mixture, followed by extraction with ethyl acetate. The organic layers were combined and dried over magnesium sulfate, and the solvent was then distilled off. The residue was purified by silica gel column chromatography to give 4-oxo-2-thioxo-1,3,8-triaza-spiro[4.5]decane-8-carboxylic acid tert-butyl ester (944 mg, 81%).

MS (ESI) m/z=284 (M−H)−.

(Reaction 333-2)

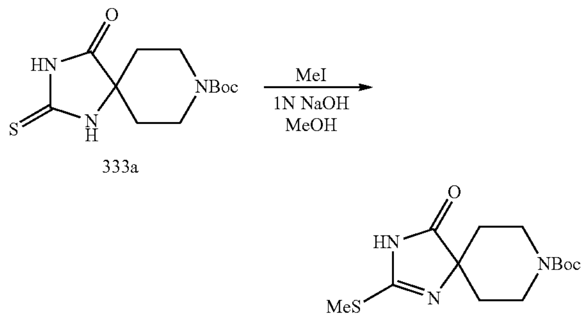

333a

333b

Iodomethane (0.329 ml, 5.28 mmol) and a 1 N aqueous NaOH solution (3.3 ml, 3.3 mmol) were sequentially added to a solution of 4-oxo-2-thioxo-1,3,8-triaza-spiro[4.5]decane-8-carboxylic acid tert-butyl ester (944 mg, 3.3 mmol) in methanol (33 ml) at room temperature, and the mixture was stirred at the same temperature overnight. Water was added to the reaction mixture, followed by extraction with ethyl acetate. The organic layers were combined and dried over magnesium sulfate, and the solvent was then distilled off. The residue was purified by silica gel column chromatography to give 2-methylsulfanyl-4-oxo-1,3,8-triaza-spiro[4.5]dec-1-ene-8-carboxylic acid tert-butyl ester (762 mg, 77%).

MS (ESI) m/z=322 (M+Na)+.

(Reaction 333-3)

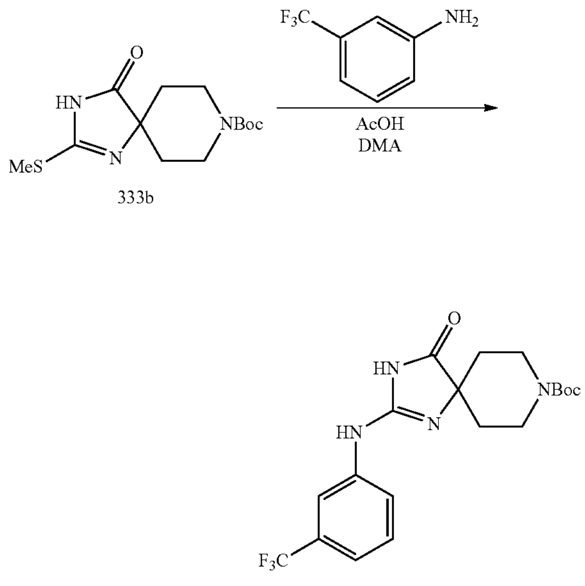

333b

333c

Acetic acid (0.275 ml, 4.8 mmol) was added to a solution of 2-methylsulfanyl-4-oxo-1,3,8-triaza-spiro[4.5]dec-1-ene-8-carboxylic acid tert-butyl ester (72 mg, 0.24 mmol) and m-trifluoromethylaniline (0.150 ml, 1.2 mmol) in DMA (1.0 ml), and the mixture was irradiated with microwaves at 150° C. for 20 minutes. A saturated aqueous sodium bicarbonate solution was added to the reaction mixture, followed by extraction with ethyl acetate. The organic layers were combined, washed with saturated brine and dried over magnesium sulfate, and the solvent was then distilled off. The residue was purified by silica gel column chromatography to give 4-oxo-2-(3-trifluoromethyl-phenylamino)-1,3,8-triaza-spiro[4.5]dec-1-ene-8-carboxylic acid tert-butyl ester (50 mg, 51%).

MS (ESI) m/z=313 (M-(Boc+H)+H)+.

(Reaction 333-4)

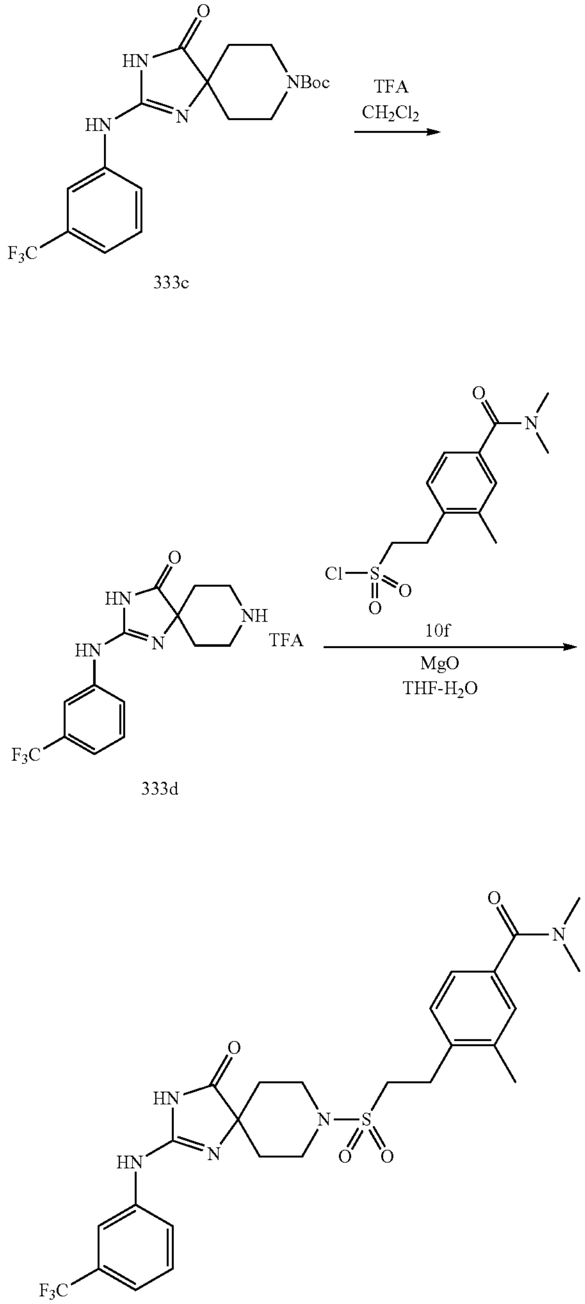

333c

333d

Compound 1395

3,N,N-Trimethyl-4-{2-[4-oxo-2-(3-trifluoromethyl-phenylamino)-1,3,8-triaza-spiro[4.5]dec-1-ene-8-sulfonyl]-ethyl}-benzamide was synthesized by operations similar to those in Reaction 4-1 and Reaction 190-1 using appropriate reagents and starting material.

MS (ESI) m/z=566 (M+H)+.

Example 334

3,N,N-Trimethyl-4-{2-[4-oxo-2-(4-trifluoromethyl-phenylamino)-1,3,8-triaza-spiro[4.5]dec-1-ene-8-sulfonyl]-ethyl}-benzamide (Compound 1396)

(Reaction 334-1)

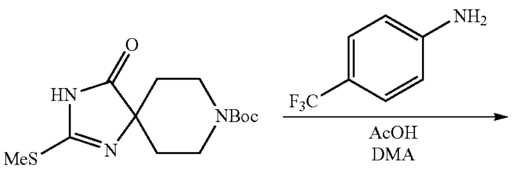

333b

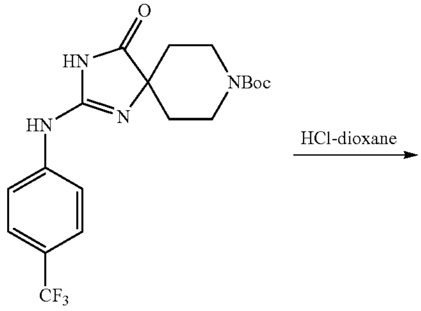

334a

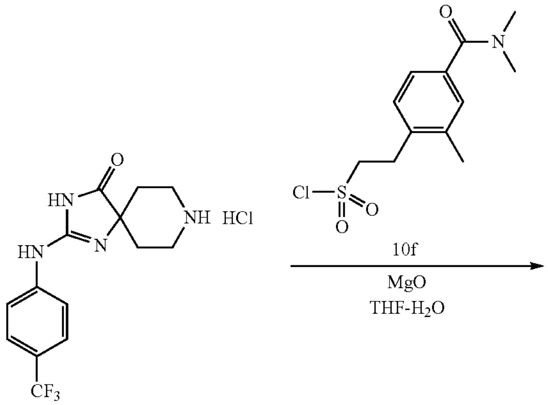

334b

-continued

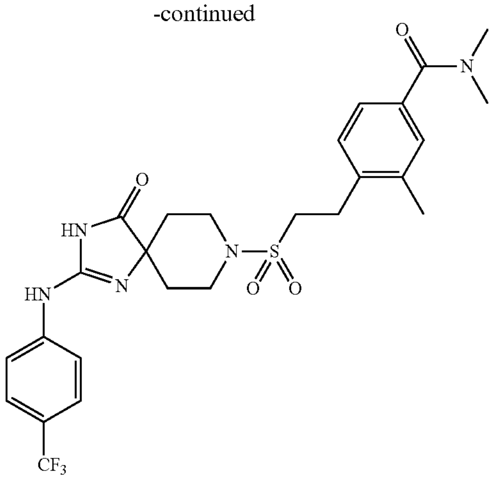

Compound 1396

3,N,N-Trimethyl-4-{2-[4-oxo-2-(4-trifluoromethyl-phenylamino)-1,3,8-triaza-spiro[4.5]dec-1-ene-8-sulfonyl]-ethyl}-benzamide was synthesized by operations similar to those in Reaction 333-3, Reaction 5-3 and Reaction 190-1 using appropriate reagents and starting material.

MS (ESI) m/z=566 (M+H)+.

The example compounds shown below were synthesized by operations similar to those in Reaction 334-1 using appropriate reagents and starting materials.

Compounds 1397 to Compound 1400

TABLE 192

| Target Compound | Structure | LCMS condition | Retention time (min) | MS (m/z) |
|---|---|---|---|---|
| 1397 | 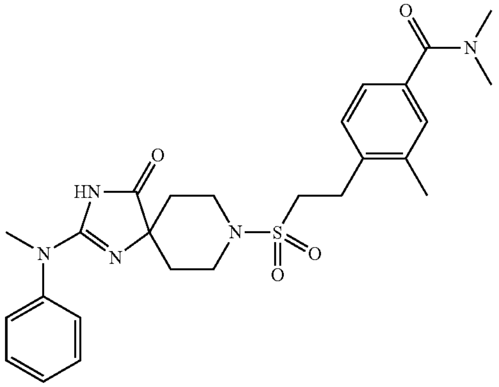 | LCMS-C-1 | 2.08 | 510 (M − H)− |

TABLE 192-continued
| Target Compound | Structure | LCMS condition | Retention time (min) | MS (m/z) |
|---|---|---|---|---|
| 1398 | 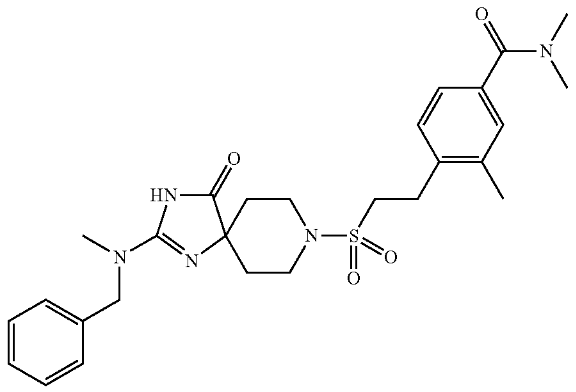 [SMILES: Cc1cc(C(=O)N(C)C)ccc1CCS(=O)(=O)N1CCC2(CC1)N=C(N(C)Cc1ccccc1)NC2=O] | LCMS-C-1 | 2.20 | 524 (M − H)− |
| 1399 | 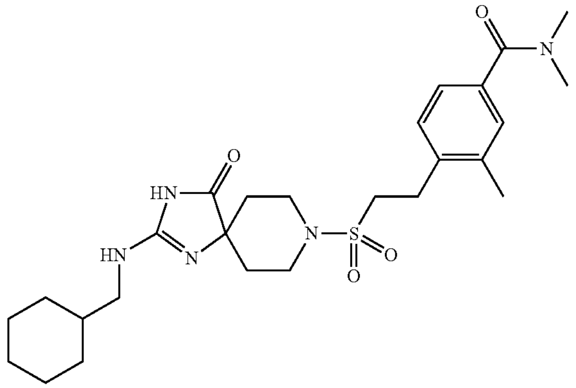 [SMILES: Cc1cc(C(=O)N(C)C)ccc1CCS(=O)(=O)N1CCC2(CC1)N=C(NCC1CCCCC1)NC2=O] | LCMS-C-1 | 2.17 | 518 (M + H)+ |
| 1400 | 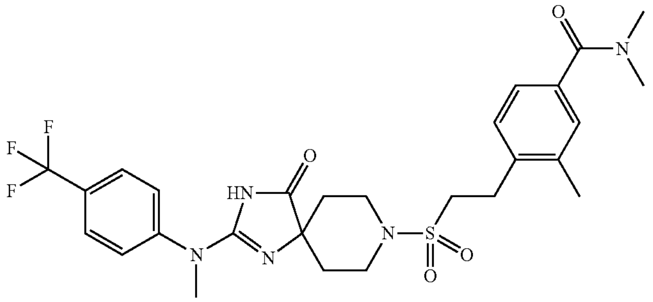 [SMILES: Cc1cc(C(=O)N(C)C)ccc1CCS(=O)(=O)N1CCC2(CC1)N=C(N(C)c1ccc(C(F)(F)F)cc1)NC2=O] | LCMS-B-1 | 1.83 | 580 (M + H)+ |

Example 335

N-(3-Methyl-4-{2-[4-oxo-2-(4-trifluoromethyl-phenylamino)-1,3,8-triaza-spiro[4.5]dec-1-ene-8-sulfonyl]-ethyl}-phenyl)-acetamide (Compound 1401)

(Reaction 335-1)

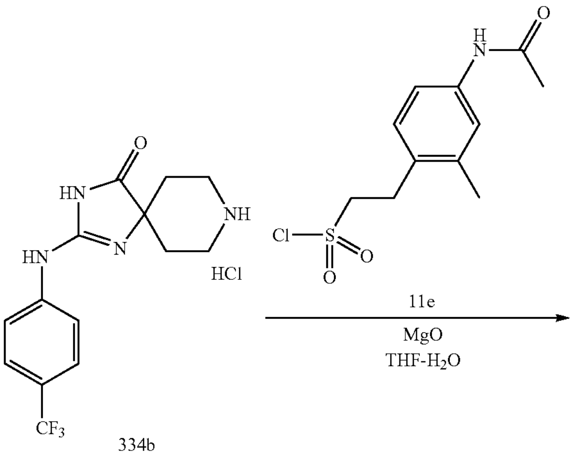

334b

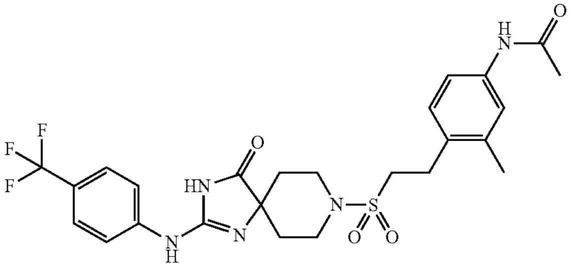

Compound 1401

N-(3-Methyl-4-{2-[4-oxo-2-(4-trifluoromethyl-phenylamino)-1,3,8-triaza-spiro[4.5]dec-1-ene-8-sulfonyl]-ethyl}-phenyl)-acetamide was synthesized by operations similar to those in Reaction 190-1 using appropriate reagents and starting material.

MS (ESI) m/z=552 (M+H)+.

The example compounds shown below were synthesized by operations similar to those in Reaction 335-1 using appropriate reagents and starting materials.

Compound 1402

TABLE 193

| Target Compound | Structure | LCMS condition | Retention time (min) | MS (m/z) |
|---|---|---|---|---|
| 1402 | 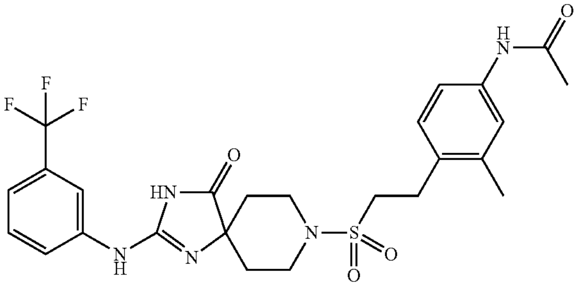 [SMILES: CC(=O)Nc1ccc(CCS(=O)(=O)N2CCC3(CC2)N=C(Nc2cccc(C(F)(F)F)c2)NC3=O)c(C)c1] | LCMS-B-1 | 1.85 | 552 (M + H)+ |

Example 336

4-{2-[2-(4-Butyl-piperidin-1-yl)-4-oxo-1,3,8-triaza-spiro[4.5]dec-1-ene-8-sulfonyl]-ethyl}-3,N,N-trimethyl-benzamide (Compound 1403)

(Reaction 336-1)

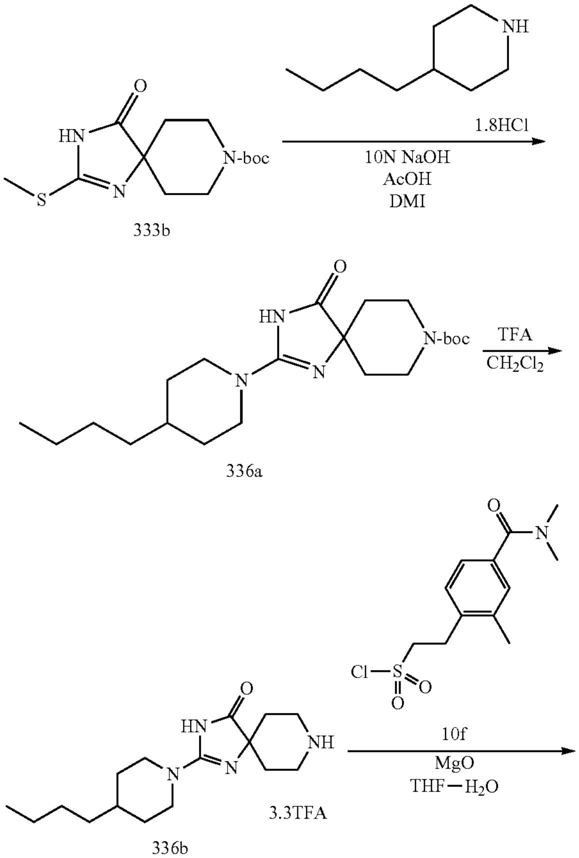

-continued

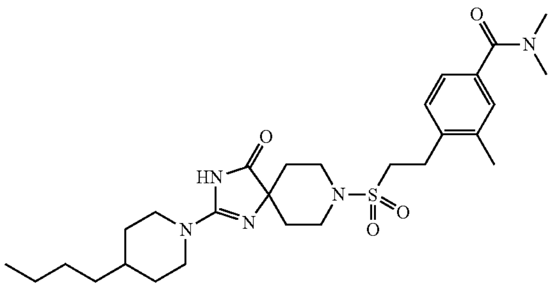

Compound 1403

Acetic acid (0.115 ml, 1.336 mmol) and 2-methylsulfanyl-4-oxo-1,3,8-triaza-spiro[4.5]dec-1-ene-8-carboxylic acid tert-butyl ester (20 mg, 0.0668 mmol) were added to a solution of 4-butyl-piperidine hydrochloride (41 mg, 0.200 mmol) and a 10N aqueous sodium hydroxide solution (0.036 ml, 0.360 mmol) in DMI (0.3 ml), and the mixture was stirred at 110° C. overnight. The reaction mixture was purified by silica gel column chromatography to give a mixture of 2-(4-butyl-piperidin-1-yl)-4-oxo-1,3,8-triaza-spiro[4.5]dec-1-ene-8-carboxylic acid tert-butyl ester (22.3 mg).

4-{2-[2-(4-Butyl-piperidin-1-yl)-4-oxo-1,3,8-triaza-spiro[4.5]dec-1-ene-8-sulfonyl]-ethyl}-3,N,N-trimethyl-benzamide (23.0 mg, 63% in three steps) was synthesized by operations similar to those in Reaction 4-1 and Reaction 190-1 using this mixture as a starting material.

MS (ESI) m/z=546 (M+H)+.

The example compounds shown below were synthesized by operations similar to those in Reaction 336-1 using appropriate reagents and starting materials.

Compound 1404

Example 337

4-{2-[2-(3-But-3-enyloxy-5-trifluoromethyl-phenyl)-4-oxo-1,3,8-triaza-spiro[4.5]dec-1-ene-8-sulfonyl]-ethyl}-3,N-dimethyl-N-pent-4-enyl-benzamide (Compound 1405)

(Reaction 337-1)

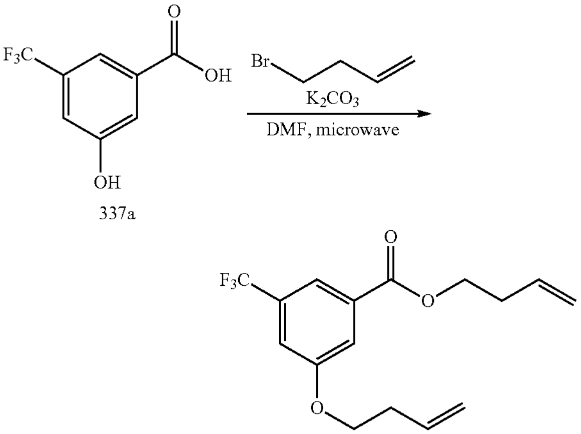

337a

337b

3-Hydroxy-5-trifluoromethyl-benzoic acid (2.17 g, 10.6 mmol), potassium carbonate (8.73 g, 63.2 mmol) and 4-bromo-1-butene (4.34 ml, 43.7 mmol) were dissolved in DMF (21 ml), and this mixture was irradiated in a microwave apparatus (100° C., 60 min). The reaction solution was poured into a cooled aqueous dilute hydrochloric acid solution, followed by extraction with ethyl acetate. The organic layer was washed with water and saturated brine, dried over anhydrous sodium sulfate and then concentrated under reduced pressure. The resulting crude product was purified by silica gel column chromatography to give 3-but-3-enyloxy-5-trifluoromethyl-benzoic acid but-3-enyl ester (2.64 g, 80%).

$^1$H-NMR (400 MHz, $CDCl_3$) δ 7.86 (1H, s), 7.71 (1H, s), 7.31 (1H, s), 5.95-5.81 (2H, m), 5.22-5.11 (4H, m), 4.40 (2H, t, J=6.6 Hz), 4.10 (2H, t, J=6.6 Hz), 2.60-2.51 (4H, m).

TABLE 194

| Target Compound | Structure | LCMS condition | Retention time (min) | MS (m/z) |
|---|---|---|---|---|
| 1404 | 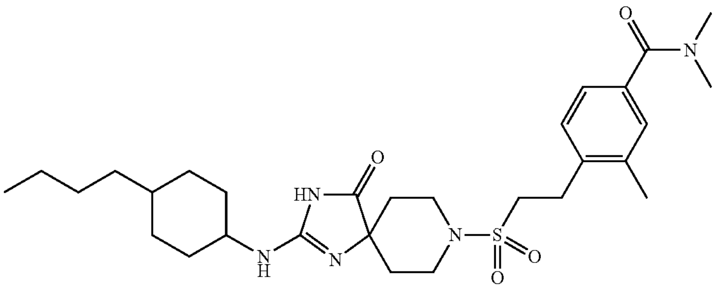 [SMILES: CCCCC1CCC(NC2=NC3(CCN(S(=O)(=O)CCc4ccc(C(=O)N(C)C)cc4C)CC3)C(=O)N2)CC1] | LCMS-B-1 | 2.24 | 560 (M + H)+ |

(Reaction 337-2)

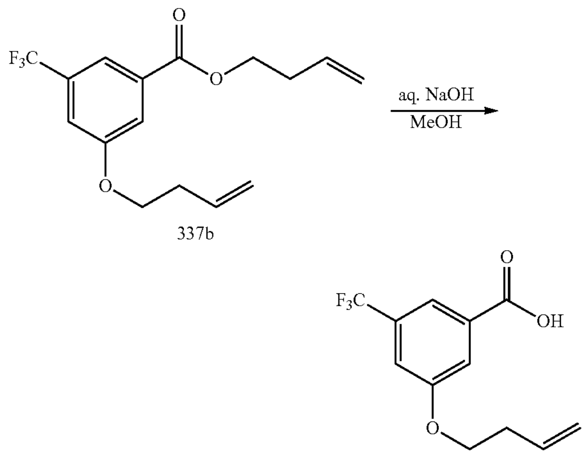

337b

337c

3-But-3-enyloxy-5-trifluoromethyl-benzoic acid but-3-enyl ester (2.64 g, 8.39 mmol) was dissolved in methanol. A 5 N aqueous sodium hydroxide solution (5.1 ml, 25.2 mmol) was added and the mixture was stirred at room temperature for two hours. The reaction solution was cooled, quenched with 2 N hydrochloric acid (20 ml, 40 mmol) and then extracted with ethyl acetate. The organic layer was washed with water and saturated brine, and then dried over anhydrous sodium sulfate and concentrated under reduced pressure. The resulting residue was purified by silica gel column chromatography to give 3-but-3-enyloxy-5-trifluoromethyl-benzoic acid (2.13 g, 98%).

$^1$H-NMR (400 MHz, $CDCl_3$) δ 7.95 (1H, s), 7.78 (1H, s), 7.38 (1H, s), 5.96-5.86 (1H, m), 5.23-5.14 (2H, m), 4.12 (2H, t, J=6.6 Hz), 2.59 (2H, q, J=6.5 Hz).

(Reaction 337-3)

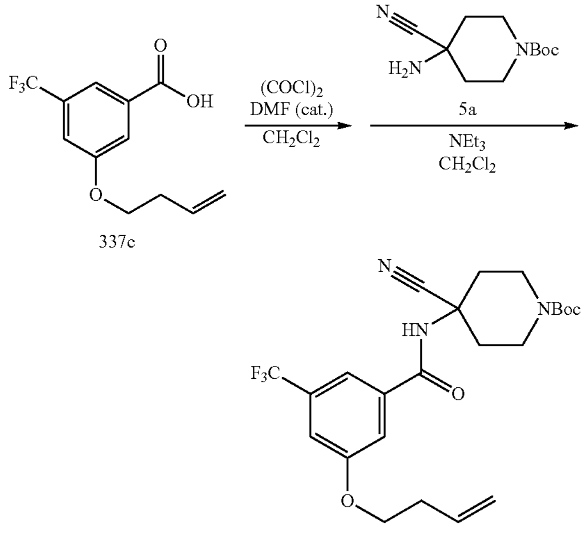

337c

337d

DMF (one drop) was added to a solution of 3-but-3-enyloxy-5-trifluoromethyl-benzoic acid (1.73 g, 6.65 mmol) in methylene chloride (6.8 ml). Oxalyl dichloride (0.566 ml, 6.60 mmol) was then added dropwise under ice-cooling, and the mixture was stirred at room temperature for three hours.

The reaction solution obtained above was added dropwise to a solution of 4-amino-4-cyano-piperidine-1-carboxylic acid tert-butyl ester (1.49 g, 6.65 mmol) and triethylamine (1.85 ml, 13.3 mmol) in methylene chloride (10 ml) under ice-cooling, and the mixture was stirred at room temperature for two hours. The reaction solution was cooled and water and 2 N hydrochloric acid were then sequentially added, followed by extraction with methylene chloride. The organic layer was dried over anhydrous sodium sulfate and then concentrated under reduced pressure to give 4-(3-but-3-enyloxy-5-trifluoromethyl-benzoylamino)-4-cyano-piperidine-1-carboxylic acid tert-butyl ester as a crude product (3.0 g). This compound was used in the next reaction without further purification.

MS (ESI) m/z=368 (M-Boc+H)+;

HPLC retention time: 3.32 min (analysis condition LCMS-A-1).

(Reaction 337-4)

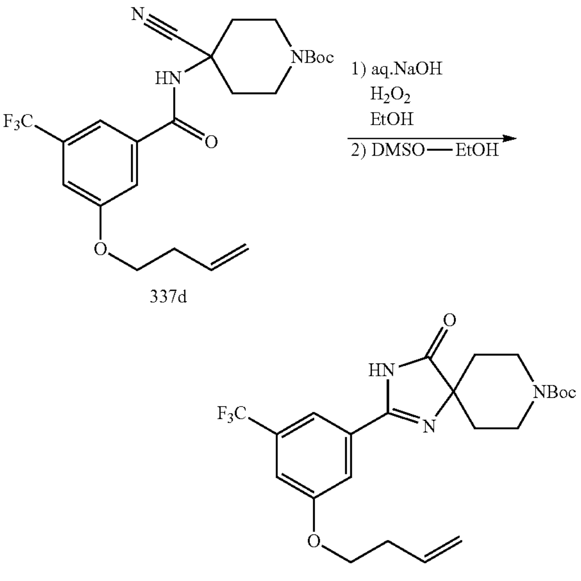

337d

337e 4-(3-But-3-enyloxy-5-trifluoromethyl-benzoylamino)-4-cyano-piperidine-1-carboxylic acid tert-butyl ester (3.0 g) was dissolved in ethanol, and a 5 N aqueous sodium hydroxide solution (6.9 ml, 34.5 mmol) and a 30% aqueous hydrogen peroxide solution (3 ml) were added. After stirring at room temperature for two hours, DMSO (19 ml) was added to the reaction solution, and the mixture was stirred at 50° C. for four hours. The reaction solution was cooled, and then quenched with a saturated aqueous ammonium chloride solution and extracted with ethyl acetate. The organic layer was sequentially washed with a saturated aqueous ammonium chloride solution, water and saturated brine, and then dried over anhydrous sodium sulfate and concentrated under reduced pressure. The resulting residue was purified by silica gel column chromatography to give 2-(3-but-3-enyloxy-5-trifluoromethyl-phenyl)-4-oxo-1,3,8-triaza-spiro[4.5]dec-1-ene-8-carboxylic acid tert-butyl ester (2.39 g, 67% in two steps).

$^1$H-NMR (400 MHz, $CDCl_3$) δ 10.10 (1H, s), 7.76 (1H, s), 7.63 (1H, s), 7.32 (1H, s), 5.96-5.86 (1H, m), 5.24-5.15 (2H, m), 4.15 (2H, t, J=6.6 Hz), 4.01 (2H, s), 3.52 (2H, t, J=11.2 Hz), 2.60 (2H, q, J=6.7 Hz), 1.96-1.89 (2H, m), 1.65-1.55 (2H, m), 1.50 (9H, s);

MS (ESI) m/z=368 (M-Boc+H)+, 412 (M-tBu+H)+.

(Reaction 337-5)

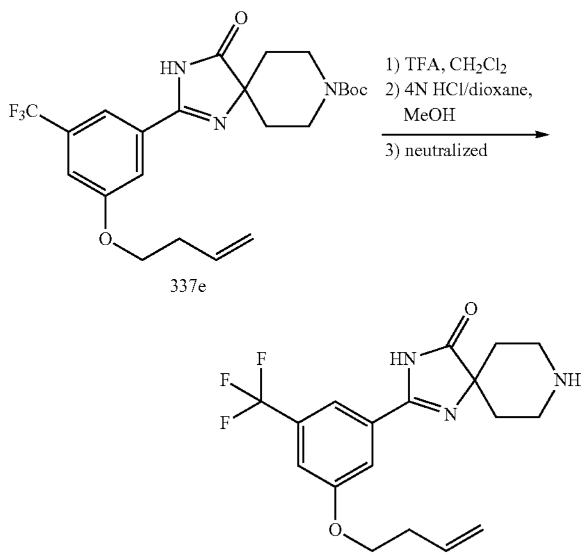

337e

337f

Trifluoroacetic acid (27 ml) was added to a solution of 2-(3-but-3-enyloxy-5-trifluoromethyl-phenyl)-4-oxo-1,3,8-triaza-spiro[4.5]dec-1-ene-8-carboxylic acid tert-butyl ester (2.39 g, 5.12 mmol) in methylene chloride (54 ml), and the mixture was stirred at room temperature for 1.5 hours. The reaction solution was concentrated under reduced pressure with azeotropic distillation with toluene, and the resulting residue (trifluoroacetate) was then dissolved in methanol (50 ml). A 4 N solution of hydrochloric acid in dioxane (16 ml) was added and the mixture was concentrated under reduced pressure. The resulting residue was dissolved in a mixed solution of ethyl acetate (100 ml)-ethanol (5 ml), followed by washing with a 1 N aqueous $K_3PO_4$ solution. The organic layer was dried over anhydrous sodium sulfate and then concentrated under reduced pressure to give 2-(3-but-3-enyloxy-5-trifluoromethyl-phenyl)-1,3,8-triaza-spiro[4.5]dec-1-en-4-one (1.92 g). This compound was used in the next reaction without further purification.

$^1$H-NMR ($CDCl_3$) δ 7.73 (1H, s), 7.63 (1H, s), 7.29 (1H, s), 5.97-5.87 (1H, m), 5.21 (2H, d, J=17.1 Hz), 5.15 (2H, d, J=10.3 Hz), 4.15 (2H, t, J=6.8 Hz), 3.25-3.10 (4H, m), 2.60 (2H, q, J=6.7 Hz), 1.95-1.85 (2H, m), 1.60-1.57 (2H, m);

MS (ESI) m/z=368 (M+H)+.

(Reaction 337-6)

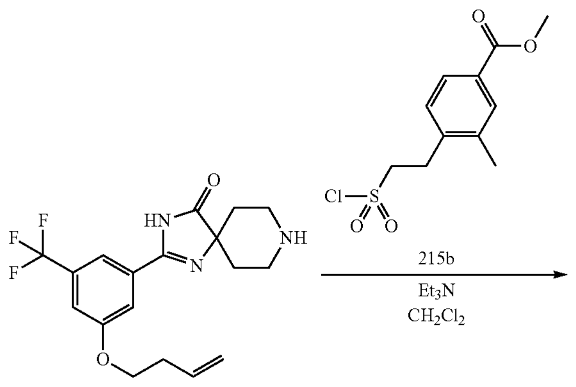

215b

337f

-continued

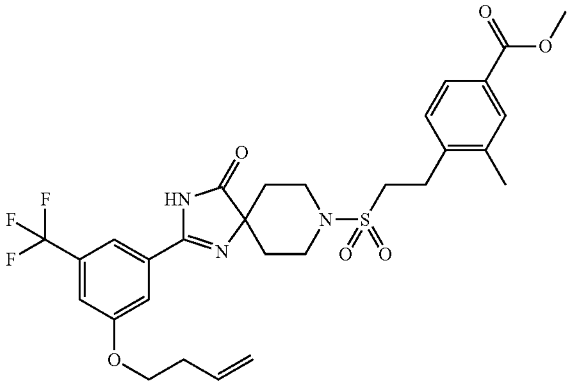

337g

Triethylamine (1.27 ml, 9.11 mmol) and 4-(2-chlorosulfonyl-ethyl)-3-methyl-benzoic acid methyl ester (1.01 g, 3.65 mmol) were added to a solution of 2-(3-but-3-enyloxy-5-trifluoromethyl-phenyl)-1,3,8-triaza-spiro[4.5]dec-1-en-4-one (1.40 g, 3.83 mmol) in methylene chloride (35 ml) at 0° C. The mixture was stirred at room temperature for two hours, and then quenched with a saturated aqueous ammonium chloride solution and extracted with ethyl acetate. The organic layer was washed with water and saturated brine, dried over anhydrous sodium sulfate and then concentrated under reduced pressure to give 4-{2-[2-(3-but-3-enyloxy-5-trifluoromethyl-phenyl)-4-oxo-1,3,8-triaza-spiro[4.5]dec-1-ene-8-sulfonyl]-ethyl}-3-methyl-benzoic acid methyl ester (2.10 g). This compound was used in the next reaction without further purification.

$^1$H-NMR (400 MHz, $CDCl_3$) δ 7.87 (1H, s), 7.85-7.84 (1H, m), 7.68 (1H, s), 7.57 (1H, s), 7.31 (1H, s), 7.26-7.25 (1H, m), 5.96-5.85 (1H, m), 5.22-5.17 (2H, m), 4.14 (2H, t, J=6.6 Hz), 3.91 (3H, s), 3.83 (2H, td, J=8.2, 3.9 Hz), 3.54-3.49 (2H, m), 3.25-3.15 (4H, m), 2.60 (1H, q, J=6.7 Hz), 2.42 (3H, s), 2.13-2.06 (2H, m), 1.77-1.73 (2H, m);

MS (ESI) m/z=608 (M+H)+.

(Reaction 337-7)

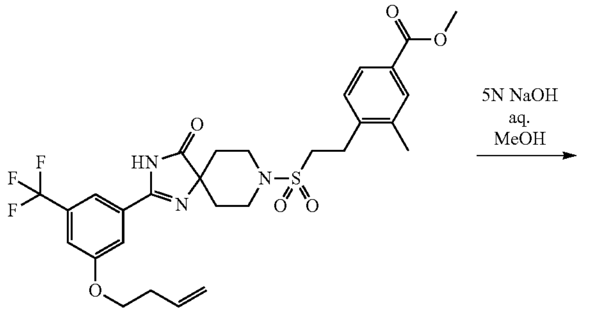

337g

-continued

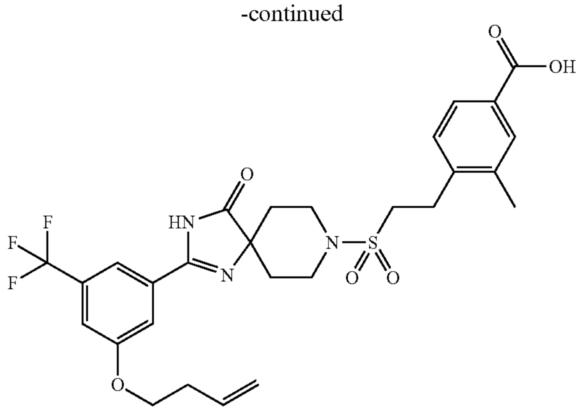

337h

A 5 N aqueous sodium hydroxide solution (6.6 ml, 33 mmol) was added to a solution of 4-{2-[2-(3-but-3-enyloxy- 5-trifluoromethyl-phenyl)-4-oxo-1,3,8-triaza-spiro[4.5]dec-1-ene-8-sulfonyl]-ethyl}-3-methyl-benzoic acid methyl ester (2.10 g) in methanol (22 ml), and the mixture was stirred at room temperature for two hours. The reaction solution was cooled and then quenched with 2 N hydrochloric acid (25 ml), followed by extraction with ethyl acetate. The organic layer was washed with water and saturated brine, dried over anhydrous sodium sulfate and then concentrated under reduced pressure to give 4-{2-[2-(3-but-3-enyloxy-5-trifluoromethyl-phenyl)-4-oxo-1,3,8-triaza-spiro[4.5]dec-1-ene-8-sulfonyl]-ethyl}-3-methyl-benzoic acid (1.78 g).

$^1$H-NMR (400 MHz, $CD_3OD$) δ 7.85-7.74 (3H, m), 7.41-7.32 (3H, m), 5.99-5.89 (1H, m), 5.19 (1H, dd, J=17.3, 1.7 Hz), 5.11 (1H, dd, J=10.3, 2.0 Hz), 4.17 (2H, t, J=6.6 Hz), 3.84-3.76 (2H, m), 3.56-3.46 (2H, m), 3.41-3.17 (4H, m), 2.58 (2H, q, J=6.7 Hz), 2.44 (3H, s), 2.07-1.97 (2H, m), 1.78-1.69 (2H, m);

MS (ESI) m/z=594 (M+H)+.

(Reaction 337-8)

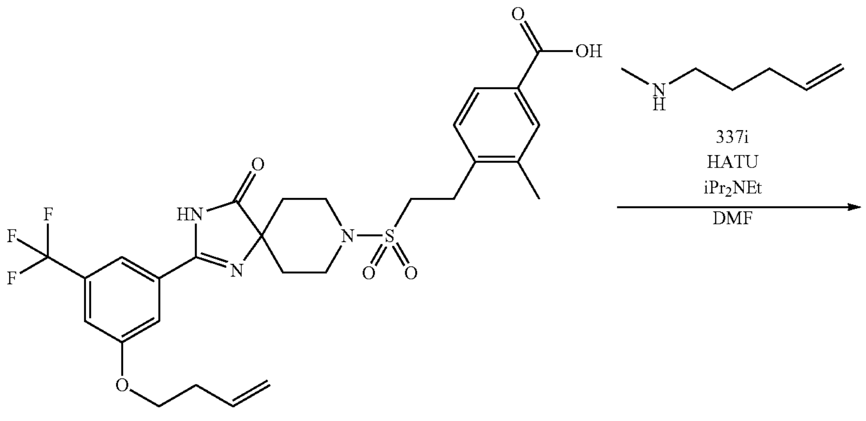

337h

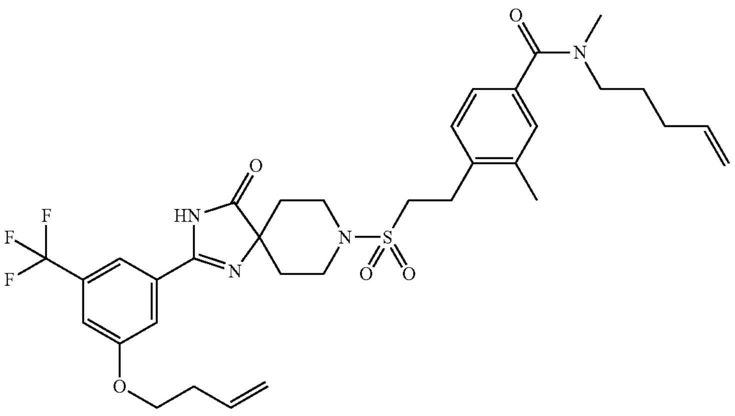

Compound 1405

HATU (194 mg, 0.510 mmol), N,N-diisopropylethylamine (143 μL) and methyl-pent-4-enyl-amine (80 mg) were added to a solution of 4-{2-[2-(3-but-3-enyloxy-5-trifluoromethyl-phenyl)-4-oxo-1,3,8-triaza-spiro[4.5]dec-1-ene-8-sulfonyl]-ethyl}-3-methyl-benzoic acid (200 mg, 0.337 mmol) in DMF (3 ml), and the mixture was stirred at room temperature overnight. A saturated aqueous ammonium chloride solution was added to the reaction solution, followed by extraction with ethyl acetate. The organic layer was washed with water and saturated brine, and then dried over anhydrous sodium sulfate and concentrated under reduced pressure. The resulting residue was purified by silica gel column chromatography to give 4-{2-[2-(3-but-3-enyloxy-5-trifluoromethyl-phenyl)-4-oxo-1,3,8-triaza-spiro[4.5]dec-1-ene-8-sulfonyl]-ethyl}-3,N-dimethyl-N-pent-4-enyl-benzamide (192 mg, 84%).

MS (ESI) m/z=675 (M+H)+;

HPLC retention time: 3.13 min (analysis condition LCMS-A-1).

Methyl-pent-4-enyl-amine used in the above Reaction 337-8 was synthesized by the following method (Angewandte Chemie, International Edition (2004), 43(41), 5542-5546).

(Reaction 337-9)

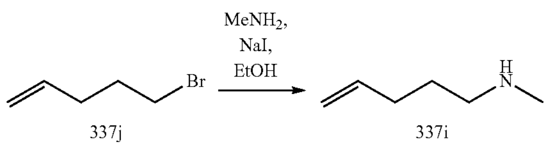

337j 337i

A 40% solution of methylamine in methanol (2.74 ml, 26.8 mmol) and NaI (20 mg, 0.134 mmol) were added to a solution of 5-bromo-1-butene (318 μL, 2.68 mmol) in ethanol (2 ml), and the mixture was stirred at 60° C. overnight in a sealed tube. The reaction solution was cooled and concentrated hydrochloric acid (2.4 ml) was then added. The mixture was concentrated under reduced pressure. The resulting residue was washed with tert-butyl methyl ether and then made basic with a 5 N aqueous sodium hydroxide solution under ice-cooling, followed by extraction with tert-butyl methyl ether (x3). The organic layers were dried over anhydrous sodium sulfate and then concentrated under reduced pressure to give methyl-pent-4-enyl-amine (80 mg, 30% as an object).

$^1$H-NMR (400 MHz, $CDCl_3$) δ 5.88-5.77 (1H, m), 5.05-4.99 (1H, m), 4.98-4.93 (1H, m), 2.58 (2H, t, J=7.1 Hz), 2.43 (3H, s), 2.12-2.03 (2H, m), 1.62-1.49 (2H, m).

Example 338

Compound 1406

(Reaction 338-1)

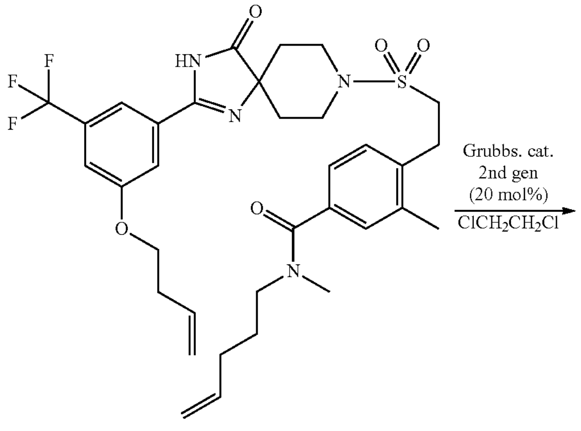

Compound 1405

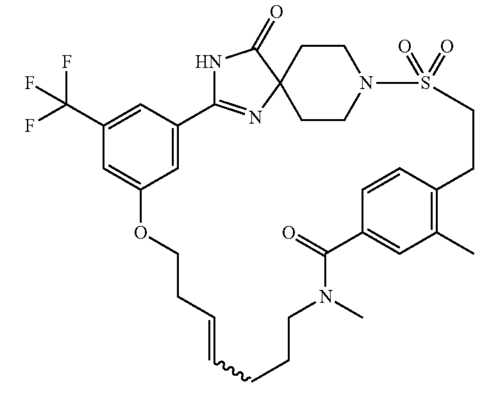

Compound 1406

Grubbs catalyst $2^{nd}$ generation (44 mg, 0.0519 mmol) was added to a solution of 4-{2-[2-(3-but-3-enyloxy-5-trifluoromethyl-phenyl)-4-oxo-1,3,8-triaza-spiro[4.5]dec-1-ene-8-sulfonyl]-ethyl}-3,N-dimethyl-N-pent-4-enyl-benzamide (175 mg, 0.259 mmol) in 1,2-dichloroethane (260 ml), and the mixture was stirred at 40° C. overnight in an argon stream. The reaction solution was concentrated under reduced pressure, and the resulting residue was then purified by silica gel column chromatography to give a macrocyclic olefin compound (Compound 1406) (157 mg, 94%).

$^1$H-NMR (400 MHz, $CDCl_3$) δ 9.76 (0.2H, s), 9.59 (0.8H, s), 8.19 (1H, s), 8.12 (1H, s), 7.35-7.10 (4H, m), 5.61-5.48 (2H, m), 4.20 (0.8H, t, J=5.4 Hz), 4.09 (0.2H, t, J=5.1 Hz), 3.67-3.05 (10H, m), 3.03 (0.6H, s), 2.98 (2.4H, s), 2.65-2.48 (2H, m), 2.47 (2.4H, s), 2.41 (0.6H, s), 2.33-2.18 (2H, m), 1.80-1.22 (6H, m);

MS (ESI) m/z=647 (M+H)+.

Example 339

Compound 1407

(Reaction 339-1)

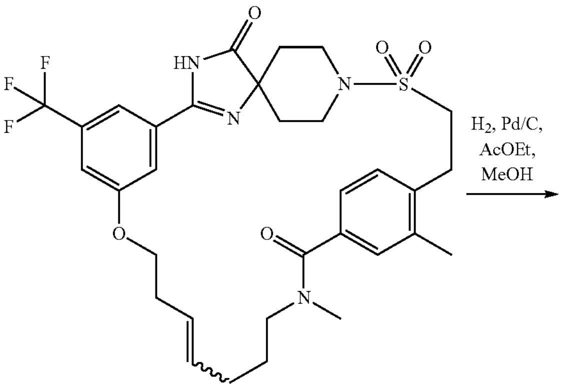

Compound 1406

-continued

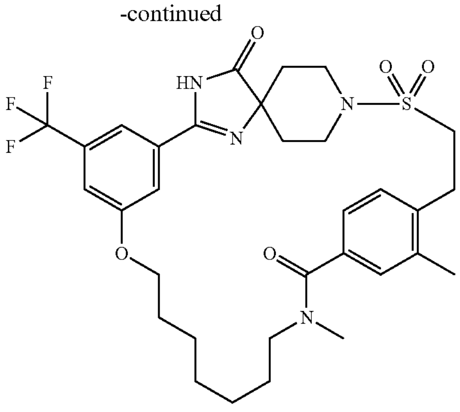

Compound 1407

10% Pd—C (50% wet) (14.4 mg) was added to a macrocyclic olefin compound (Compound 1406) (36 mg, 0.0551 mmol) in a mixed solvent of methanol and ethyl acetate (1:10, 5.5 ml), and the mixture was stirred overnight in a hydrogen atmosphere. The reaction solution was filtered through celite, and the filtrate was then concentrated. The resulting residue was purified by P-TLC($CH_2Cl_2$-MeOH) to give a saturated macrocyclic compound (Compound 1407) (30 mg, 94%).

$^1$H-NMR (400 MHz, $CD_3OD$) δ 7.93 (1H, s), 7.66 (1H, s), 7.40-7.35 (2H, m), 7.26-7.18 (2H, m), 4.07 (2H, t, J=5.4 Hz), 3.81 (2H, br d, J=11.7 Hz), 3.48-3.13 (8H, m), 3.06 (3H, s), 2.44 (3H, s), 2.13-1.10 (14H, m);

MS (ESI) m/z=649 (M+H)+.

Example 340

Compound 1408

(Reaction 340-1)

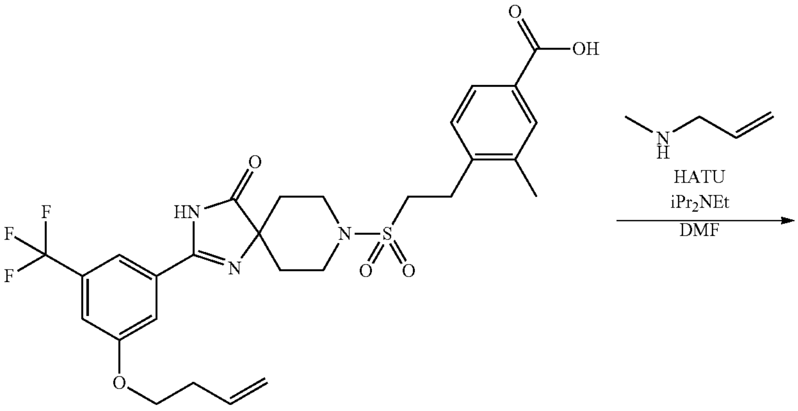

337h

-continued

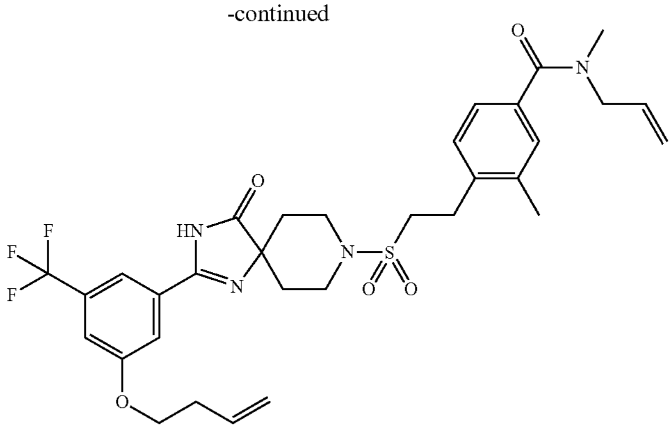

340a

N-Allyl-4-{2-[2-(3-but-3-enyloxy-5-trifluoromethyl-phenyl)-4-oxo-1,3,8-triaza-spiro[4.5]dec-1-ene-8-sulfonyl]-ethyl}-3,N-dimethyl-benzamide was obtained by the same method as in Reaction 337-8 using 4-{2-[2-(3-but-3-enyloxy-5-trifluoromethyl-phenyl)-4-oxo-1,3,8-triaza-spiro[4.5]dec-1-ene-8-sulfonyl]-ethyl}-3-methyl-benzoic acid and allyl-methyl-amine as starting materials.

MS (ESI) m/z=647 (M+H)+;

HPLC retention time: 2.95 min (analysis condition LCMS-A-1).

(Reaction 340-2)

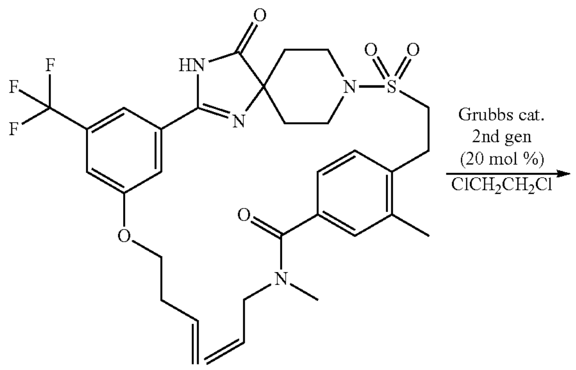

340a

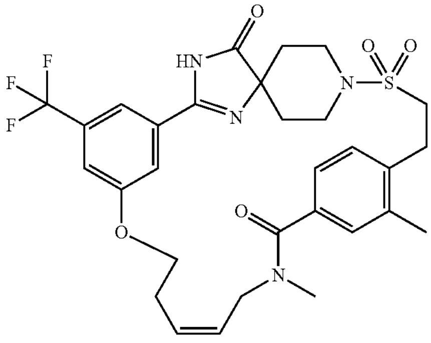

Compound 1408

A macrocyclic olefin compound (Compound 1408) was obtained by the same method as in Reaction 338-1 using N-allyl-4-{2-[2-(3-but-3-enyloxy-5-trifluoromethyl-phenyl)-4-oxo-1,3,8-triaza-spiro[4.5]dec-1-ene-8-sulfonyl]-ethyl}-3,N-dimethyl-benzamide (151 mg, 0.233 mmol) as a starting material.

MS (ESI) m/z=619 (M+H)+;

HPLC retention time: 2.69 min (analysis condition LCMS-A-1).

Example 341

Compound 1409

(Reaction 341-1)

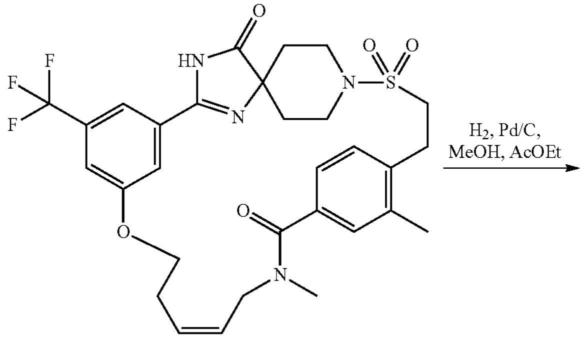

Compound 1408

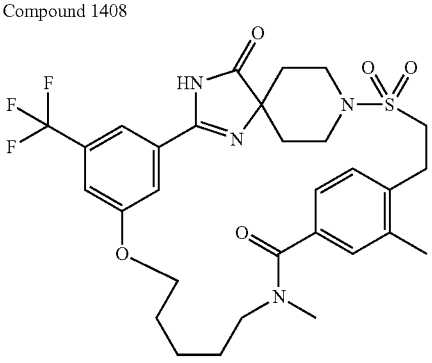

Compound 1409

A saturated macrocyclic compound (Compound 1409) was obtained by the same method as in Reaction 339-1 using a macrocyclic olefin compound (Compound 1408) as a starting material.

MS (ESI) m/z=621 (M+H)+;

HPLC retention time: 2.72 min (analysis condition LCMS-A-1).

Example 342

Compounds 1410 and Compound 1411

(Reaction 342-1)

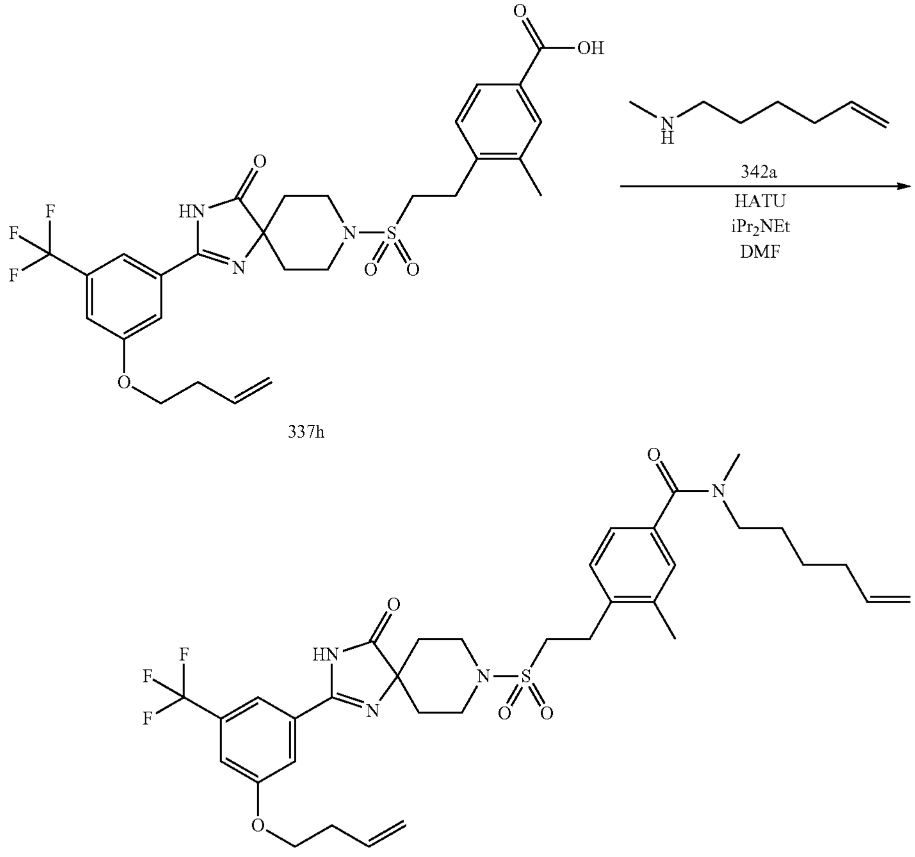

337h

342b

4-{2-[2-(3-But-3-enyloxy-5-trifluoromethyl-phenyl)-4-oxo-1,3,8-triaza-spiro[4.5]dec-1-ene-8-sulfonyl]-ethyl}-N-hex-5-enyl-3,N-dimethyl-benzamide was obtained by the same method as in Reaction 337-8 using 4-{2-[2-(3-but-3-enyloxy-5-trifluoromethyl-phenyl)-4-oxo-1,3,8-triaza-spiro[4.5]dec-1-ene-8-sulfonyl]-ethyl}-3-methyl-benzoic acid and hex-5-enyl-methyl-amine as starting materials.

MS (ESI) m/z=689 (M+H)+;

HPLC retention time: 3.32 min (analysis condition LCMS-A-1).

Hex-5-enyl-methyl-amine used in the above Reaction 342-1 was synthesized in the following manner.

(Reaction 342-2)

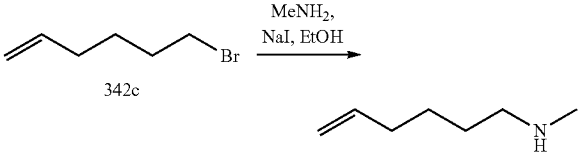

342c

342a

Hex-5-enyl-methyl-amine was obtained by the same method as in Reaction 337-9 using 6-bromo-1-hexene (437 mg, 2.68 mmol) as a raw material.

$^1$H-NMR (400 MHz, $CDCl_3$) δ 5.86-5.76 (1H, m), 5.03-4.93 (2H, m), 2.57 (2H, t, J=7.0 Hz), 2.43 (3H, s), 2.10-2.04 (2H, m), 1.54-1.38 (4H, m).

(Reaction 342-3)

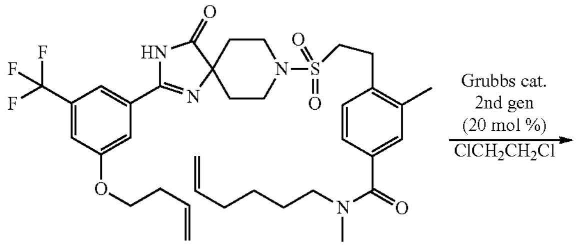

342b

-continued

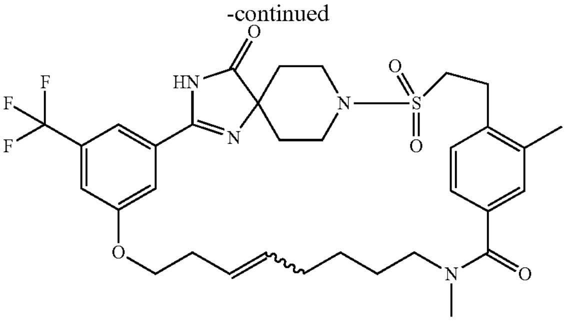

Compound 1410
Compound 1411

A macrocyclic olefin compound (Compound 1410, E/Z=98:2) and a macrocyclic olefin compound (Compound 1411, E/Z=59:41) were obtained by the same method as in Reaction 338-1 using 4-{2-[2-(3-but-3-enyloxy-5-trifluoromethyl-phenyl)-4-oxo-1,3,8-triaza-spiro[4.5]dec-1-ene-8-sulfonyl]-ethyl}-N-hex-5-enyl-3,N-dimethyl-benzamide as a starting material.

Compound 1410

MS (ESI) m/z=661 (M+H)+;

HPLC retention time: 3.09 min (analysis condition LCMS-A-1).

Compound 1411

MS (ESI) m/z=661 (M+H)+;

HPLC retention time: 3.08 min (analysis condition LCMS-A-1).

Example 343

Compound 1412

(Reaction 343-1)

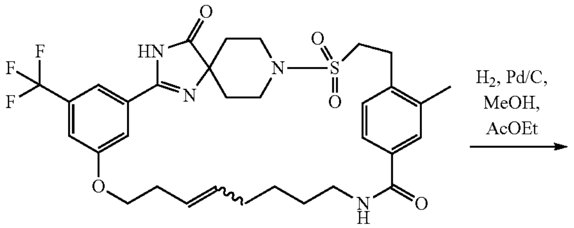

Compound 1411

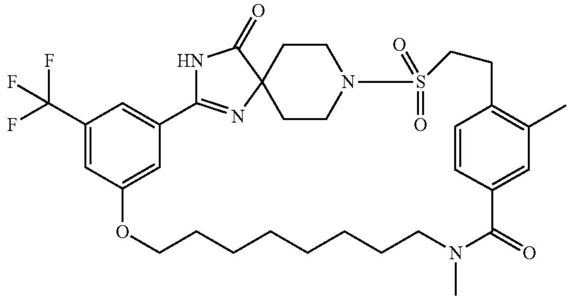

Compound 1412

A saturated macrocyclic compound (Compound 1412) was obtained by the same method as in Reaction 339-1 using a macrocyclic olefin compound (Compound 1411) as a starting material.

MS (ESI) m/z=663 (M+H)+;

HPLC retention time: 3.22 min (analysis condition LCMS-A-1).

Example 344

Compounds 1413 and Compound 1414

(Reaction 344-1)

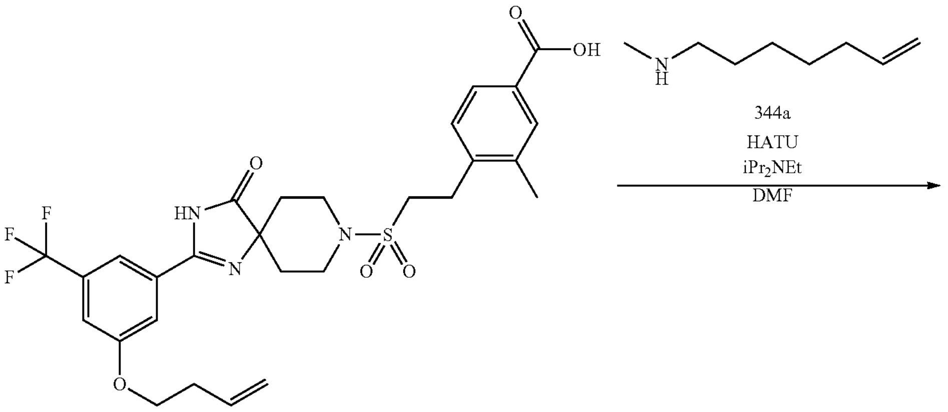

337h

-continued

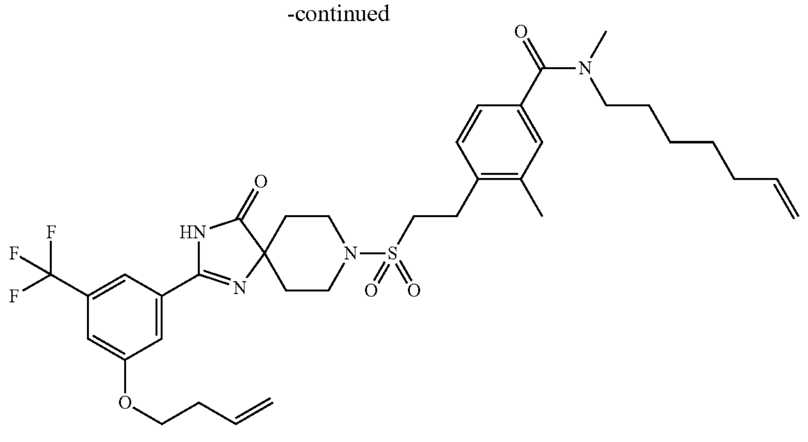

344b

4-{2-[2-(3-But-3-enyloxy-5-trifluoromethyl-phenyl)-4-oxo-1,3,8-triaza-spiro[4.5]dec-1-ene-8-sulfonyl]-ethyl}-N-hept-6-enyl-3,N-dimethyl-benzamide was obtained by the same method as in Reaction 337-8 using 4-{2-[2-(3-but-3-enyloxy-5-trifluoromethyl-phenyl)-4-oxo-1,3,8-triaza-spiro[4.5]dec-1-ene-8-sulfonyl]-ethyl}-3-methyl-benzoic acid and hept-6-enyl-methyl-amine as starting materials.

MS (ESI) m/z=703 (M+H)+;

HPLC retention time: 3.45 min (analysis condition LCMS-A-1).

Hept-6-enyl-methyl-amine used in the above Reaction 344-1 was synthesized as follows.

(Reaction 344-2)

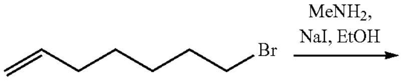

344c

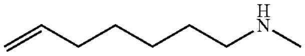

344a

Hept-6-enyl-methyl-amine was obtained by the same method as in Reaction 337-9 using 7-bromo-1-heptene as a raw material.

$^1$H-NMR ($CDCl_3$) δ 5.86-5.76 (1H, m), 5.02-4.97 (1H, m), 4.95-4.92 (1H, m), 2.56 (2H, t, J=7.1 Hz), 2.43 (3H, s), 2.05 (2H, q, J=7.0 Hz), 1.52-1.29 (6H, m).

(Reaction 344-3)

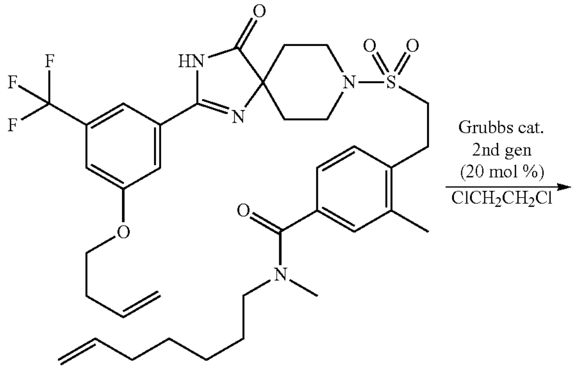

344b

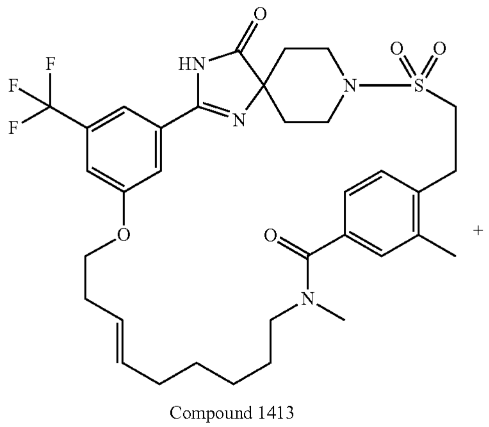

Compound 1413

-continued

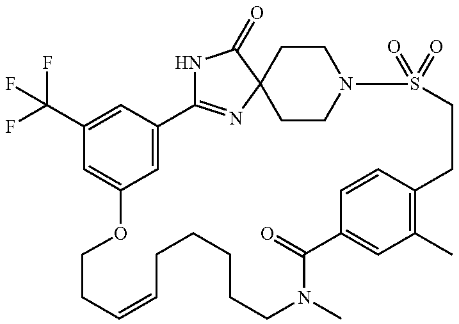

Compound 1414

A macrocyclic olefin compound (E/Z mixture) was obtained by the same method as in Reaction 338-1 using 4-{2-[2-(3-but-3-enyloxy-5-trifluoromethyl-phenyl)-4-oxo-1,3,8-triaza-spiro[4.5]dec-1-ene-8-sulfonyl]-ethyl}-N-hept-6-enyl-3,N-dimethyl-benzamide as a starting material. This mixture was purified by HPLC to give Compound 1413 (E/Z=97:3) and Compound 1414 (E/Z=10:90).

Compound 1413

MS (ESI) m/z=675 (M+H)+;

HPLC retention time: 3.20 min (analysis condition LCMS-A-1).

Compound 1414

MS (ESI) m/z=675 (M+H)+;

HPLC retention time: 3.18 min (analysis condition LCMS-A-1).

Example 345

Compound 1415

(Reaction 345-1)

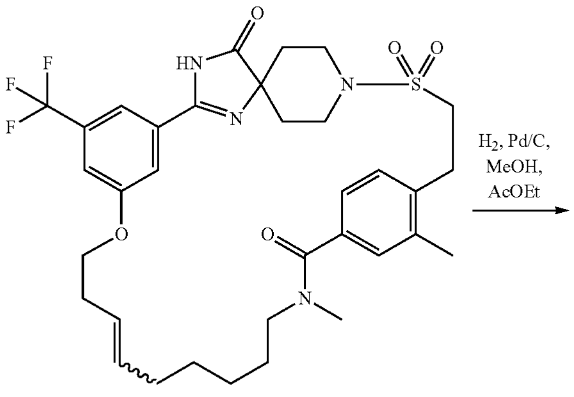

Mixture
(Compound 1413 + Compound 1414)

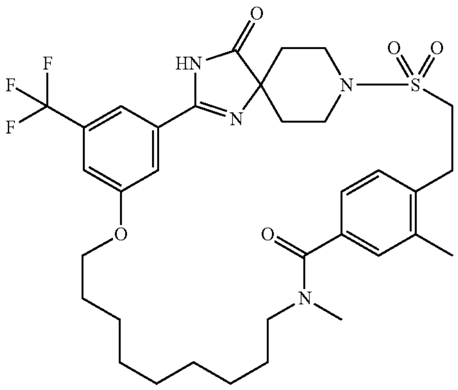

Compound 1415

A saturated macrocyclic compound (Compound 1415) was obtained by the same method as in Reaction 339-1 using a macrocyclic olefin compound (a mixture of Compound 1413 and Compound 1414) as a starting material.

MS (ESI) m/z=677 (M+H)+;

HPLC retention time: 3.34 min (analysis condition LCMS-A-1).

Example 346

Compounds 1416 and Compound 1417

(Reaction 346-1)

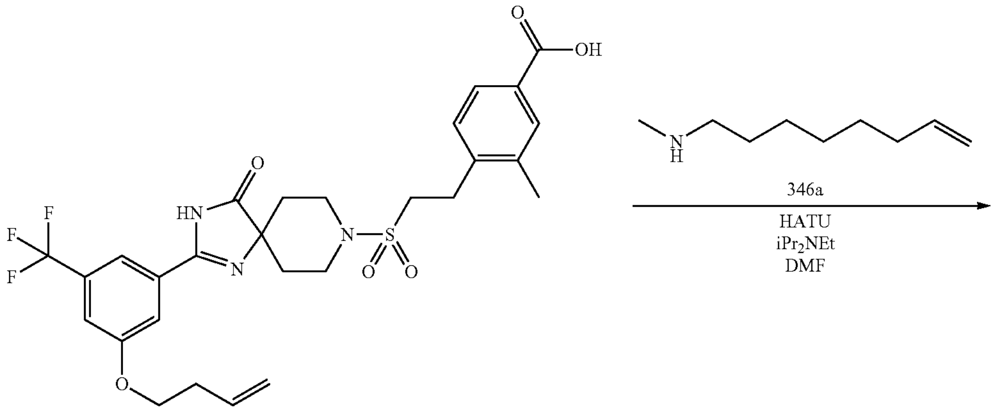

337h

-continued

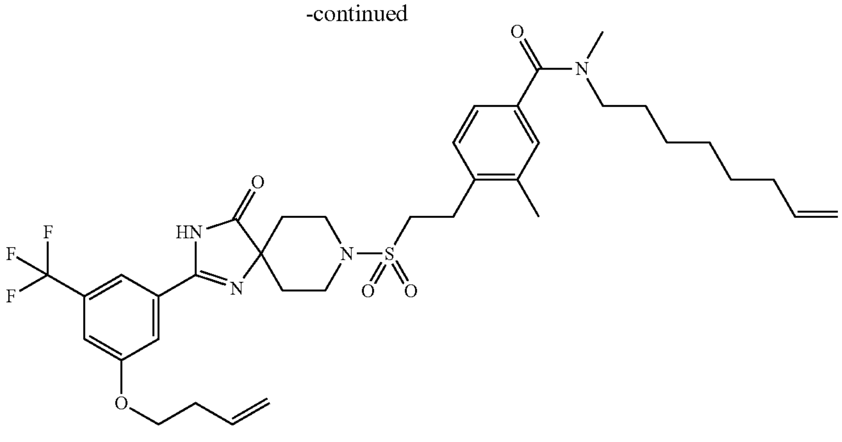

346b

4-{2-[2-(3-But-3-enyloxy-5-trifluoromethyl-phenyl)-4-oxo-1,3,8-triaza-spiro[4.5]dec-1-ene-8-sulfonyl]-ethyl}-3,N-dimethyl-N-oct-7-enyl-benzamide was obtained by the same method as in Reaction 337-8 using 4-{2-[2-(3-but-3-enyloxy-5-trifluoromethyl-phenyl)-4-oxo-1,3,8-triaza-spiro[4.5]dec-1-ene-8-sulfonyl]-ethyl}-3-methyl-benzoic acid and methyl-oct-7-enyl-amine as starting materials.

MS (ESI) m/z=717 (M+H)+;

HPLC retention time: 3.55 min (analysis condition LCMS-A-1)

Methyl-oct-7-enyl-amine used in the above Reaction 346-1 was synthesized as follows.

(Reaction 346-2)

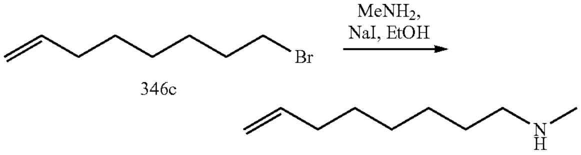

346c

346a

Methyl-oct-7-enyl-amine was obtained by the same method as in Reaction 337-9 using 8-bromo-1-octene as a raw material.

$^1$H-NMR (400 MHz, $CDCl_3$) δ 5.86-5.76 (1H, m), 5.02-4.96 (1H, m), 4.95-4.91 (1H, m), 2.56 (2H, t, J=7.1 Hz), 2.43 (3H, s), 2.07-2.01 (2H, m), 1.50-1.30 (8H, m).

(Reaction 346-3)

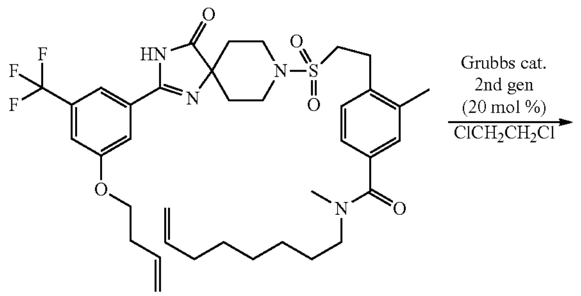

346b

-continued

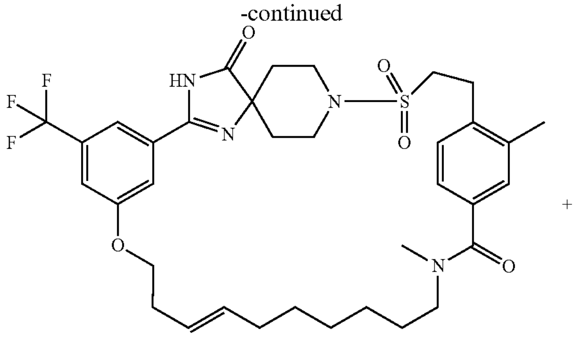

Compound 1416

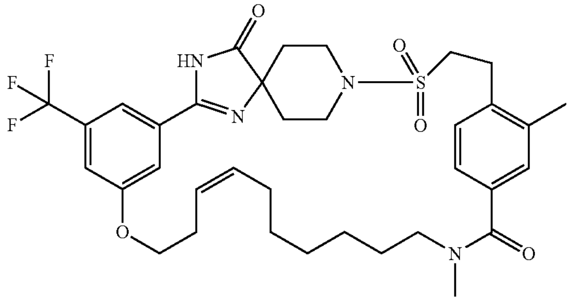

Compound 1417

A macrocyclic olefin compound (E/Z mixture) was obtained by the same method as in Reaction 338-1 using 4-{2-[2-(3-but-3-enyloxy-5-trifluoromethyl-phenyl)-4-oxo-1,3,8-triaza-spiro[4.5]dec-1-ene-8-sulfonyl]-ethyl}-3,N-dimethyl-N-oct-7-enyl-benzamide as a starting material. The resulting mixture was purified by HPLC (MeOH/MeCN/$H_2O$) to give Compound 1416 (E/Z=96:4) and Compound 1417 (E/Z=19:81).

Compound 1416

MS (ESI) m/z=689 (M+H)+;

HPLC retention time: 3.38 min (analysis condition LCMS-A-1).

Compound 1417

MS (ESI) m/z=689 (M+H)+;

HPLC retention time: 3.26 min (analysis condition LCMS-A-1).

Example 347
Compound 1418
(Reaction 347-1)
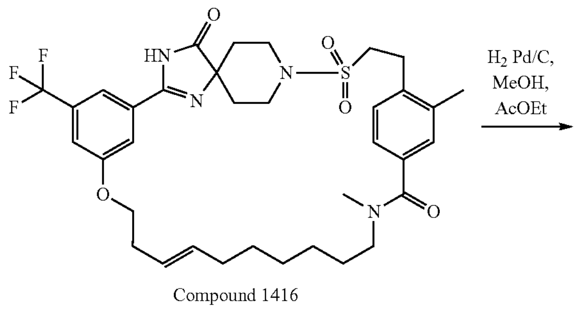
Compound 1416
-continued
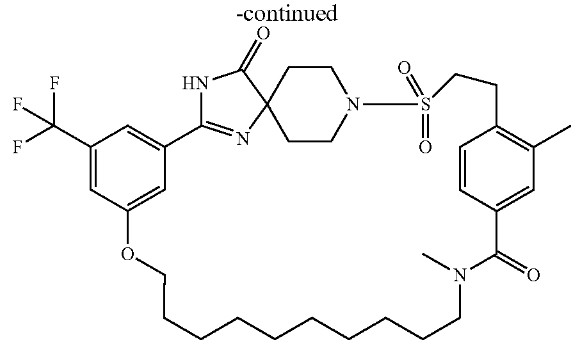
Compound 1418
A saturated macrocyclic compound (Compound 1418) was obtained by the same method as in Reaction 339-1 using a macrocyclic olefin compound (Compound 1416) as a starting material.
MS (ESI) m/z=691 (M+H)+;
HPLC retention time: 3.56 min (analysis condition LCMS-A-1).
Example 348
Compound 1419
(Reaction 348-1)
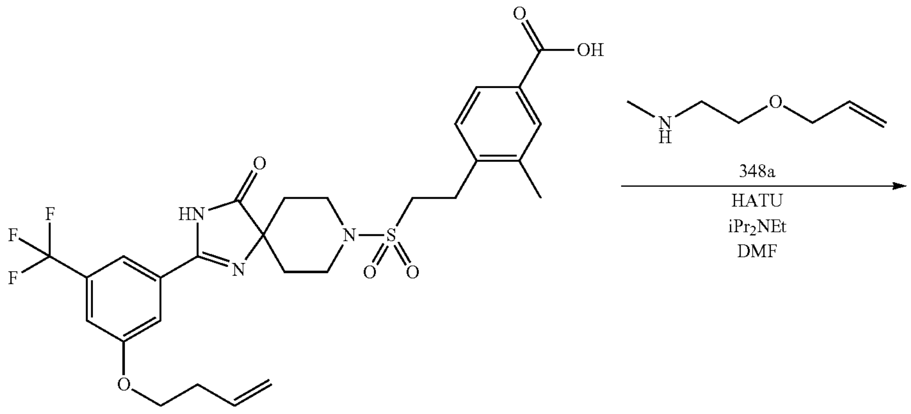
337h
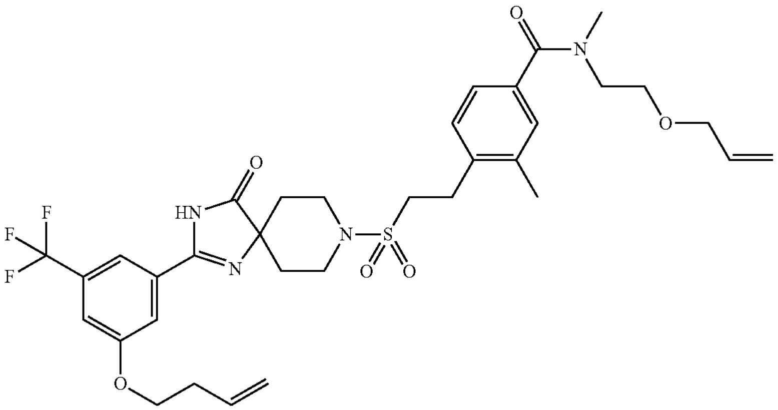
Compound 1419

N-(2-Allyloxy-ethyl)-4-{2-[2-(3-but-3-enyloxy-5-trifluoromethyl-phenyl)-4-oxo-1,3,8-triaza-spiro[4.5]dec-1-ene-8-sulfonyl]-ethyl}-3,N-dimethyl-benzamide was obtained by the same method as in Reaction 337-8 using 4-{2-[2-(3-but-3-enyloxy-5-trifluoromethyl-phenyl)-4-oxo-1,3,8-triaza-spiro[4.5]dec-1-ene-8-sulfonyl]-ethyl}-3-methyl-benzoic acid and (2-allyloxy-ethyl)-methyl-amine as starting materials.

MS (ESI) m/z=691 (M+H)+;

HPLC retention time: 3.08 min (analysis condition LCMS-A-1).

(2-Allyloxy-ethyl)-methyl-amine used in the above Reaction 348-1 was synthesized in the following manner.

(Reaction 348-2)

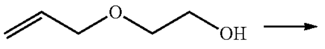

348c

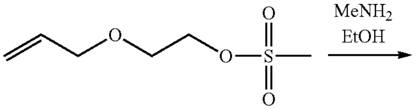

348d

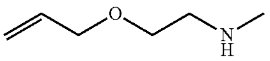

348a (2-Allyloxy-ethyl)-methyl-amine was obtained by the same method as in Reaction 337-9 using, as a starting material, methanesulfonic acid 2-allyloxy-ethyl ester synthesized from 2-allyloxy-ethanol by the method described in Journal of Organic Chemistry (2006), 71(21), 8183-8189.

$^1H$-NMR (400 MHz, $CDCl_3$) δ 5.97-5.87 (1H, m), 5.30-5.24 (1H, m), 5.20-5.17 (1H, m), 4.00 (2H, br d, J=5.9 Hz), 3.55 (2H, t, J=5.4 Hz), 2.76 (2H, t, J=5.1 Hz), 2.45 (3H, s).

Example 349

Compound 1420

(Reaction 349-1)

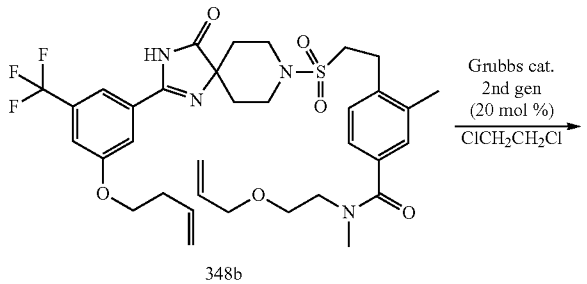

348b

-continued

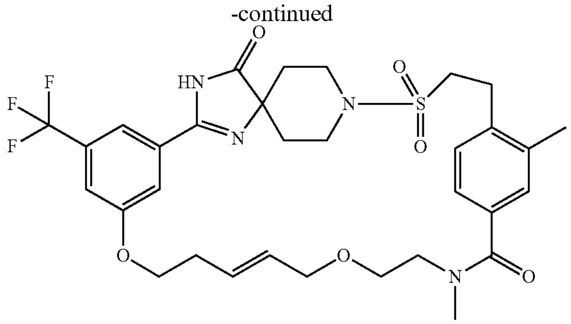

Compound 1420

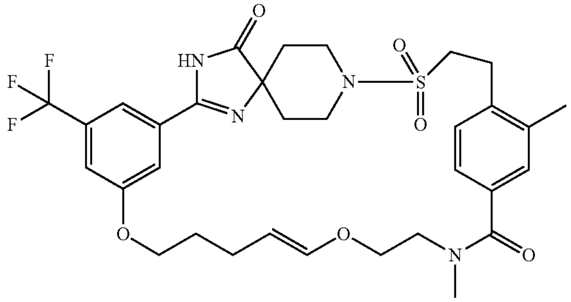

349a

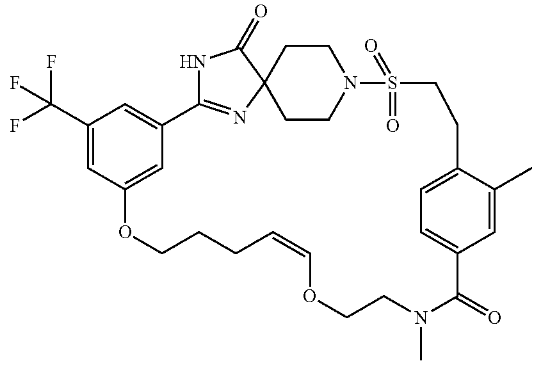

349b

A macrocyclic olefin compound (Compound 1420) and its isomer A (349a) and isomer B (349b) were obtained by the same method as in Reaction 338-1 using N-(2-allyloxy-ethyl)-4-{2-[2-(3-but-3-enyloxy-5-trifluoromethyl-phenyl)-4-oxo-1,3,8-triaza-spiro[4.5]dec-1-ene-8-sulfonyl]-ethyl}-3,N-dimethyl-benzamide as a starting material.

Compound 1420

MS (ESI) m/z=663 (M+H)+;

HPLC retention time: 2.84 min (analysis condition LCMS-A-1).

Isomer A (349a)

MS (ESI) m/z=663 (M+H)+

HPLC retention time: 2.77 min (analysis condition LCMS-A-1).

Isomer B (349b)

MS (ESI) m/z=663 (M+H)+

HPLC retention time: 2.96 min (analysis condition LCMS-A-1).

Example 350
Compound 1421
(Reaction 350-1)
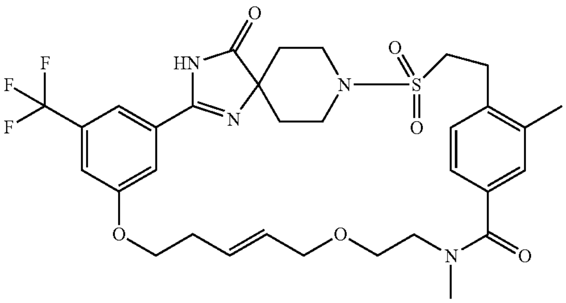
Compound 1420
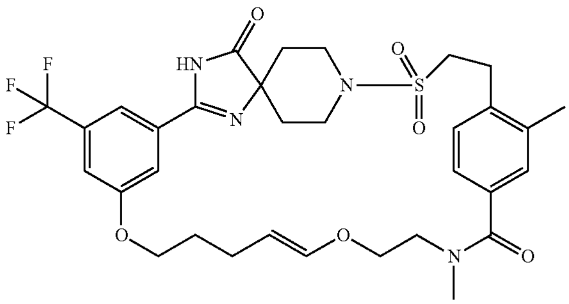
349a
-continued
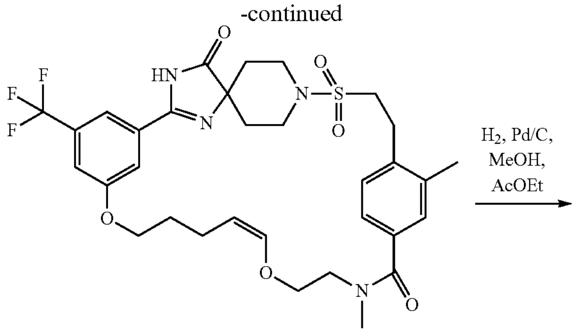
349b
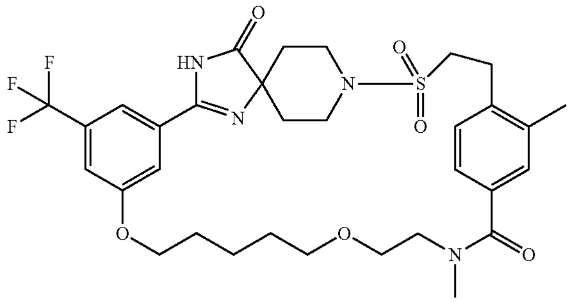
Compound 1421
A saturated macrocyclic compound (Compound 1421) was obtained by the same method as in Reaction 339-1 using macrocyclic olefin mixture (Compounds 1420, 349a and 349b) as a starting material.
MS (ESI) m/z=665 (M+H)+;
HPLC retention time: 2.95 min (analysis condition LCMS-A-1).
Example 351
Compounds 1422 and Compound 1423
(Reaction 351-1)
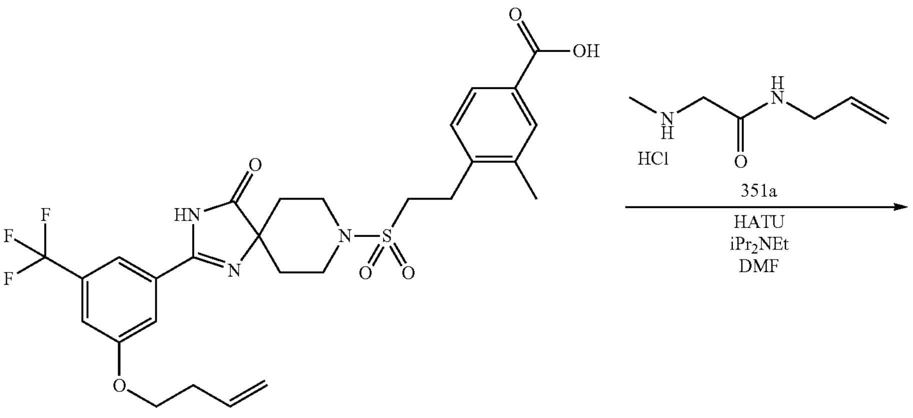
337h -continued

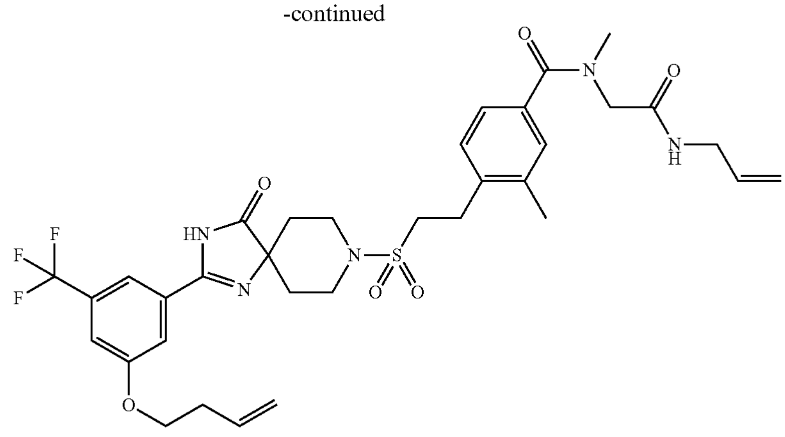

351b

N-Allylcarbamoylmethyl-4-{2-[2-(3-but-3-enyloxy-5-trifluoromethyl-phenyl)-4-oxo-1,3,8-triaza-spiro[4.5]dec-1-ene-8-sulfonyl]-ethyl}-3,N-dimethyl-benzamide was obtained by the same method as in Reaction 337-8 using 4-{2-[2-(3-but-3-enyloxy-5-trifluoromethyl-phenyl)-4-oxo-1,3,8-triaza-spiro[4.5]dec-1-ene-8-sulfonyl]-ethyl}-3-methyl-benzoic acid and N-allyl-2-methylamino-acetamide hydrochloride as starting materials.

MS (ESI) m/z=704 (M+H)+;

HPLC retention time: 2.80 min (analysis condition LCMS-A-1).

N-Allyl-2-methylamino-acetamide hydrochloride used in the above reaction was synthesized by the following method.

(Reaction 351-2)

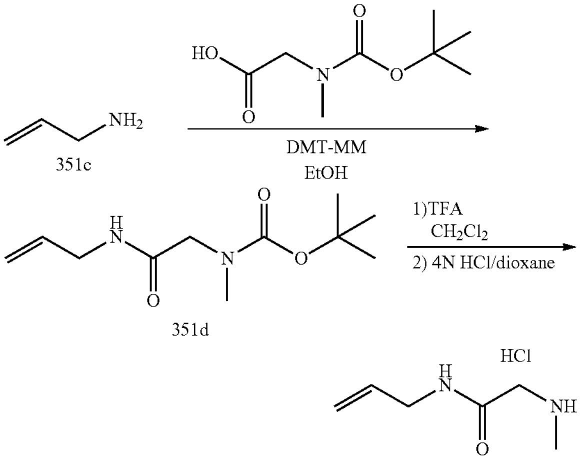

351c

351d

351a

Allylamine (0.377 ml, 5.03 mmol) and 4-(4,6-dimethoxy-1,3,5-triazin-2-yl)-4-methylmorpholinium chloride n-hydrate (DMT-MM) (1.89 g, 6.04 mmol) were added to a solution of Boc-sarcosine (1.0 g, 5.29 mmol) in ethanol, and the mixture was stirred at room temperature for 18 hours. A saturated aqueous sodium bicarbonate solution and water were added to the reaction solution, followed by extraction with ether. The organic layer was washed with water and saturated brine, dried over anhydrous sodium sulfate and then concentrated under reduced pressure to give allylcarbamoylmethyl-methyl-carbamic acid tert-butyl ester (712 mg).

$^1$H-NMR (400 MHz, $CDCl_3$) δ 6.27 (0.5H, br s), 6.02 (0.5H, br s), 5.88-5.79 (1H, m), 5.18 (1H, br d, J=17.6 Hz), 5.15 (1H, br d, J=11.2 Hz), 3.91 (2H, br t, J=5.6 Hz), 3.88 (2H, s), 2.95 (3H, s), 1.47 (9H, s).

Trifluoroacetic acid (7 ml) was added to a solution of the resulting allylcarbamoylmethyl-methyl-carbamic acid tert-butyl ester in methylene chloride (14 ml), and the mixture was stirred at room temperature for three hours. The reaction solution was concentrated under reduced pressure, and 4 N hydrochloric acid-dioxane was then added to the resulting residue. The mixture was concentrated under reduced pressure again to give N-allyl-2-methylamino-acetamide hydrochloride (577 mg). This was used in the next reaction without complete purification.

$^1$H-NMR (400 MHz, DMSO-$d_6$) δ 8.96 (2H, br s), 8.68 (1H, br t, J=5.6 Hz), 5.86-5.76 (1H, m), 5.19 (1H, dq, J=17.1, 1.6 Hz), 5.10 (1H, dq, J=10.4, 1.5 Hz), 3.79-3.75 (2H, m), 3.71 (2H, br s), 2.55 (2H, br s).

(Reaction 351-3)

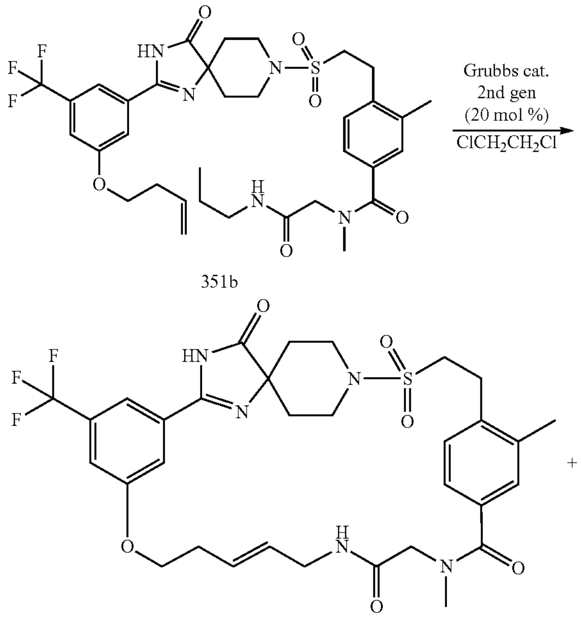

351b

Compound 1422

-continued

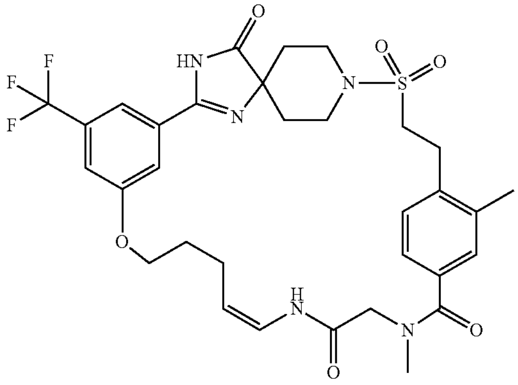

Compound 1423

A macrocyclic olefin compound (Compound 1422) and its isomer (Compound 1423) were obtained by the same method as in Reaction 338-1 using N-allylcarbamoylmethyl-4-{2-[2-(3-but-3-enyloxy-5-trifluoromethyl-phenyl)-4-oxo-1,3,8-triaza-spiro[4.5]dec-1-ene-8-sulfonyl]-ethyl}-3,N-dimethyl-benzamide as a starting material.

Compound 1422

MS (ESI) m/z=676 (M+H)+;
HPLC retention time: 2.47 min (analysis condition LCMS-A-1).

Compound 1423

MS (ESI) m/z=676 (M+H)+;
HPLC retention time: 2.61 min (analysis condition LCMS-A-1).

Example 352

Compound 1424

(Reaction 352-1)

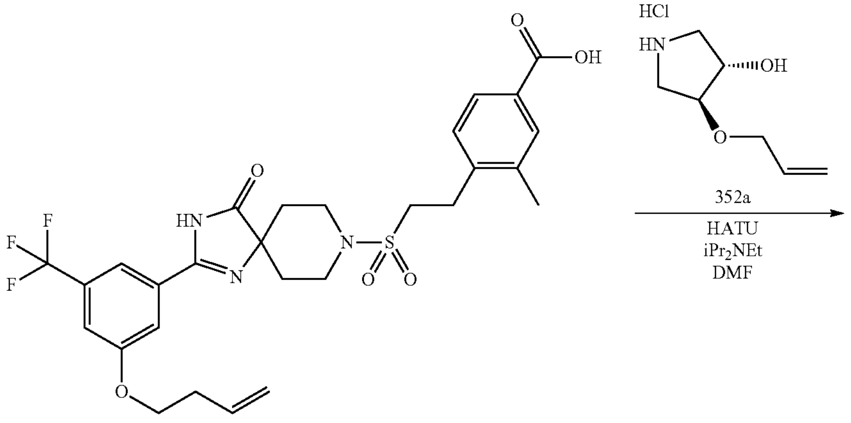

337h

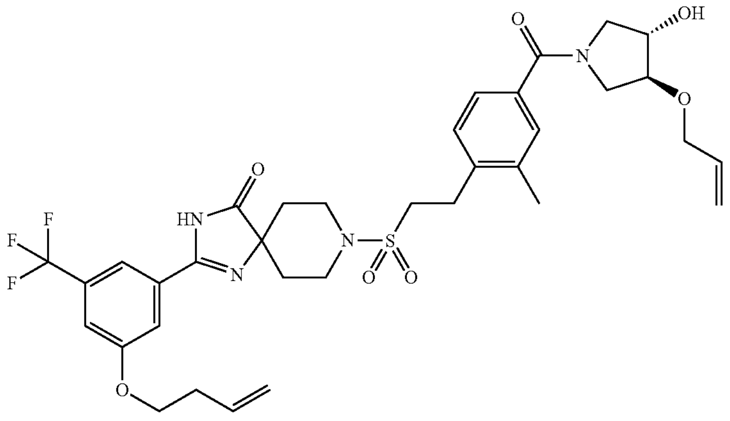

352b

8-{2-[4-((3S,4S)-3-Allyloxy-4-hydroxy-pyrrolidine-1-carbonyl)-2-methyl-phenyl]-ethanesulfonyl}-2-(3-but-3-enyloxy-5-trifluoromethyl-phenyl)-1,3,8-triaza-spiro[4.5]dec-1-en-4-one were obtained by the same method as in Reaction 337-8 using 4-{2-[2-(3-but-3-enyloxy-5-trifluoromethyl-phenyl)-4-oxo-1,3,8-triaza-spiro[4.5]dec-1-ene-8-sulfonyl]-ethyl}-3-methyl-benzoic acid and (3S,4S)-4-allyloxy-pyrrolidin-3-ol hydrochloride as starting materials.

MS (ESI) m/z=719 (M+H)+;

HPLC retention time: 2.81 min (analysis condition LCMS-A-1).

(3S,4S)-4-Allyloxy-pyrrolidin-3-ol hydrochloride used in the above reaction was synthesized by the following method.

(Reaction 352-2)

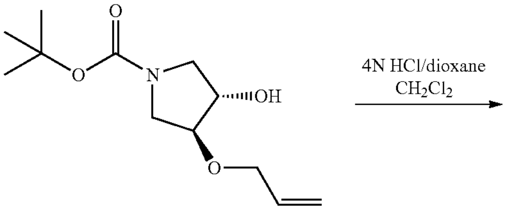

352c

-continued

HCl

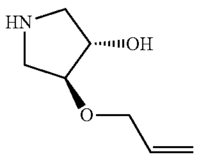

352a (3S,4S)-3-Allyloxy-4-hydroxy-pyrrolidine-1-carboxylic acid tert-butyl ester synthesized by the method described in the patent literature (DE4234330) (139 mg, 0.57 mmol) was dissolved in methylene chloride (2.4 ml). A 4 N solution of hydrochloric acid in dioxane (0.628 ml, 2.45 mmol) was added and the mixture was stirred at room temperature for two hours. The reaction solution was concentrated under reduced pressure to give (3S,4S)-4-allyloxy-pyrrolidin-3-ol hydrochloride (105 mg). This was used in the next reaction without further purification.

$^1$H-NMR (400 MHz, DMSO-$d_6$) δ 9.43 (2H, br s), 5.93-5.83 (1H, m), 5.72 (1H, br d, J=2.4 Hz), 5.28 (1H, dq, J=17.3, 1.8 Hz), 5.17 (1H, dq, J=10.5, 1.5 Hz), 4.26 (1H, br s), 4.04-4.02 (2H, m), 3.95 (1H, d, J=4.4 Hz), 3.32-3.06 (4H, m).

(Reaction 352-3)

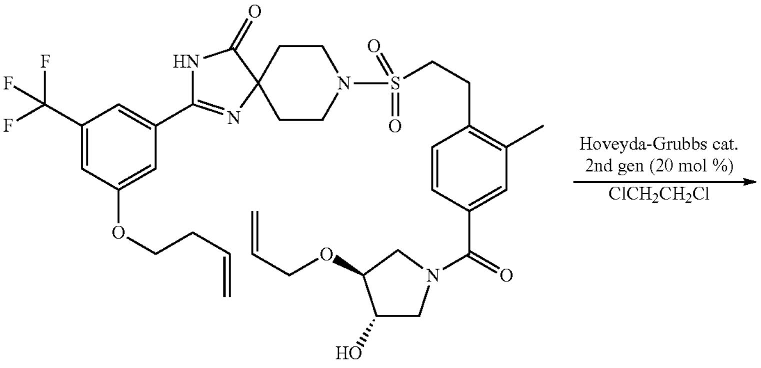

352b

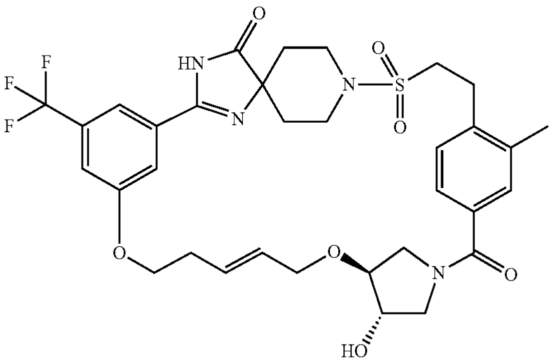

Compound 1424

A macrocyclic olefin compound (Compound 1424) was obtained by the same method as in Reaction 338-1 (using Hoveyda-Grubbs $2^{nd}$ generation as a catalyst) using 8-{2-[4-((3S,4S)-3-allyloxy-4-hydroxy-pyrrolidine-1-carbonyl)-2-methyl-phenyl]-ethanesulfonyl}-2-(3-but-3-enyloxy-5-trifluoromethyl-phenyl)-1,3,8-triaza-spiro[4.5]dec-1-en-4-one (106 mg, 0.148 mmol) as a starting material.

MS (ESI) m/z=691 (M+H)+;

HPLC retention time: 2.48 min (analysis condition LCMS-A-1).

Example 353

Compound 1425

(Reaction 353-1)

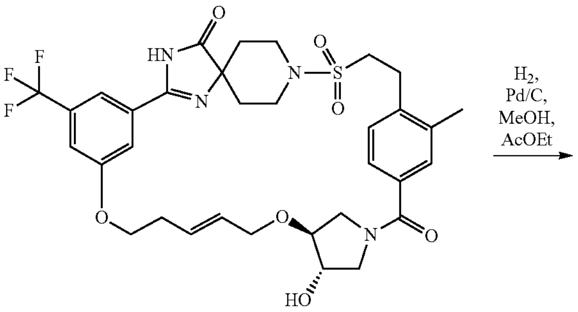

Compound 1424

-continued

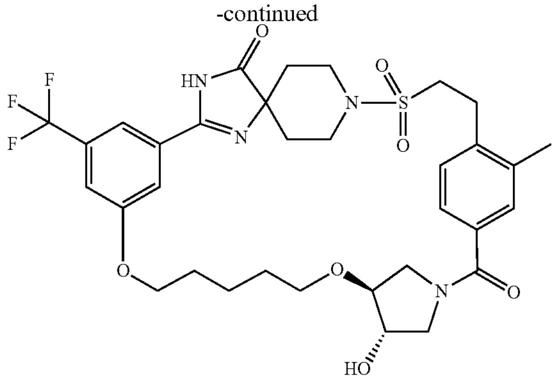

Compound 1425

A saturated macrocyclic compound (Compound 1425) was obtained by the same method as in Reaction 339-1 using a macrocyclic olefin compound (Compound 1424) as a starting material.

MS (ESI) m/z=693 (M+H)+;

HPLC retention time: 2.54 min (analysis condition LCMS-A-1).

Example 354

Compound 1426

(Reaction 354-1)

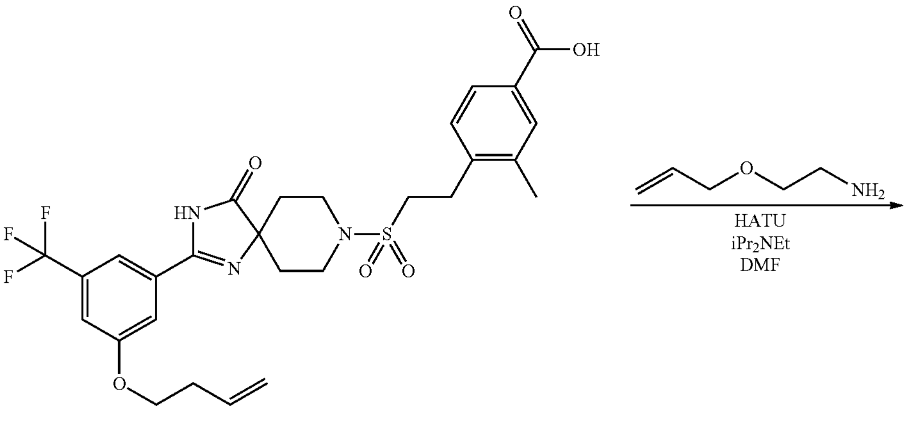

337h

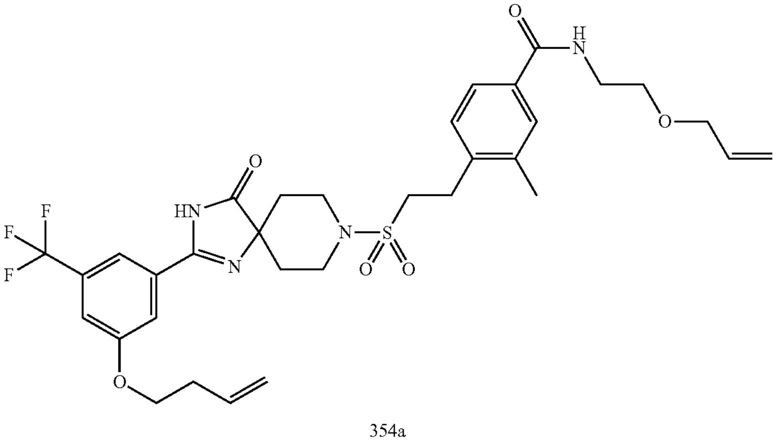

354a

N-(2-Allyloxy-ethyl)-4-{2-[2-(3-but-3-enyloxy-5-trifluoromethyl-phenyl)-4-oxo-1,3,8-triaza-spiro[4.5]dec-1-ene-8-sulfonyl]-ethyl}-3-methyl-benzamide was obtained by the same method as in Reaction 337-8 using 4-{2-[2-(3-but-3-enyloxy-5-trifluoromethyl-phenyl)-4-oxo-1,3,8-triaza-spiro[4.5]dec-1-ene-8-sulfonyl]-ethyl}-3-methyl-benzoic acid and 2-allyloxy-ethylamine as starting materials.

MS (ESI) m/z=677 (M+H)+;

HPLC retention time: 1.08 min (analysis condition LCMS-F-1).

(Reaction 354-2)

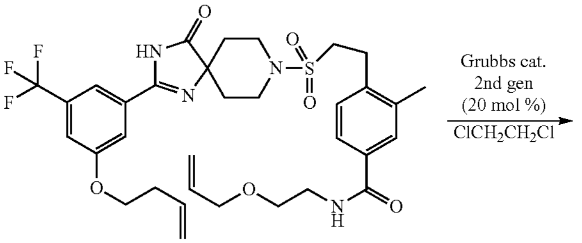

354a

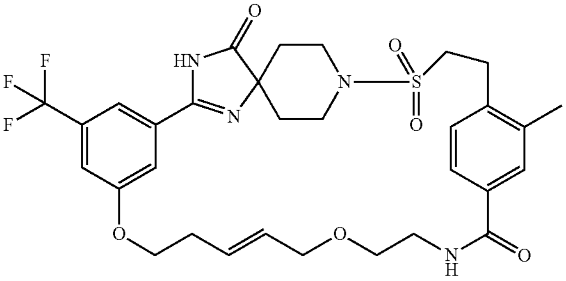

Compound 1426

A macrocyclic olefin compound (Compound 1426) was obtained by the same method as in Reaction 338-1 using N-(2-allyloxy-ethyl)-4-{2-[2-(3-but-3-enyloxy-5-trifluoromethyl-phenyl)-4-oxo-1,3,8-triaza-spiro[4.5]dec-1-ene-8-sulfonyl]-ethyl}-3-methyl-benzamide as a starting material.

MS (ESI) m/z=649 (M+H)+;

HPLC retention time: 2.83 min (analysis condition LCMS-C-1).

Example 355

Compound 1427

(Reaction 355-1)

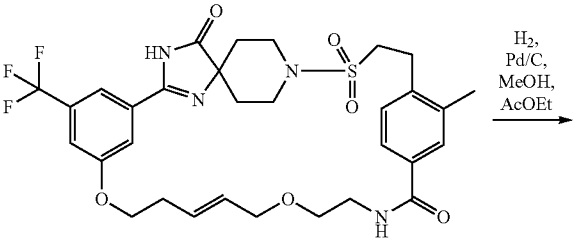

Compound 1426

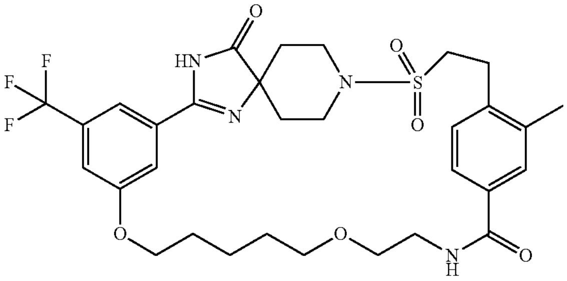

Compound 1427

A saturated macrocyclic compound (Compound 1427) was obtained by the same method as in Reaction 339-1 using a macrocyclic olefin compound (Compound 1426) as a starting material.

MS (ESI) m/z=651 (M+H)+;

HPLC retention time: 1.07 min (analysis condition LCMS-F-1).

Example 356

Compound 1428

(Reaction 356-1)

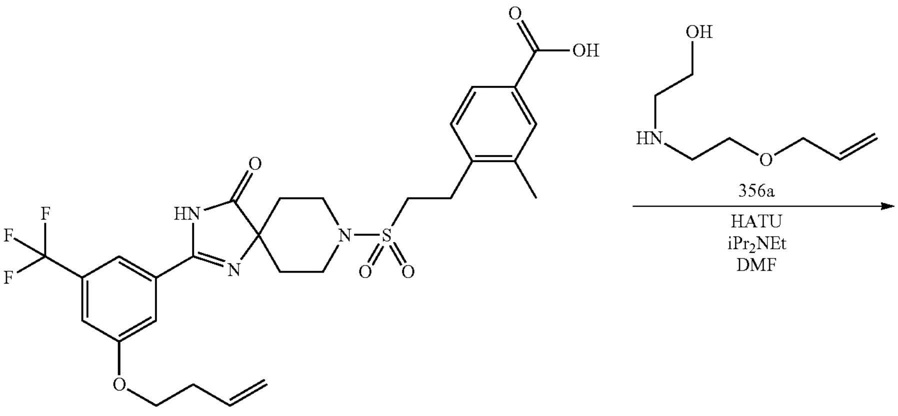

337h

-continued

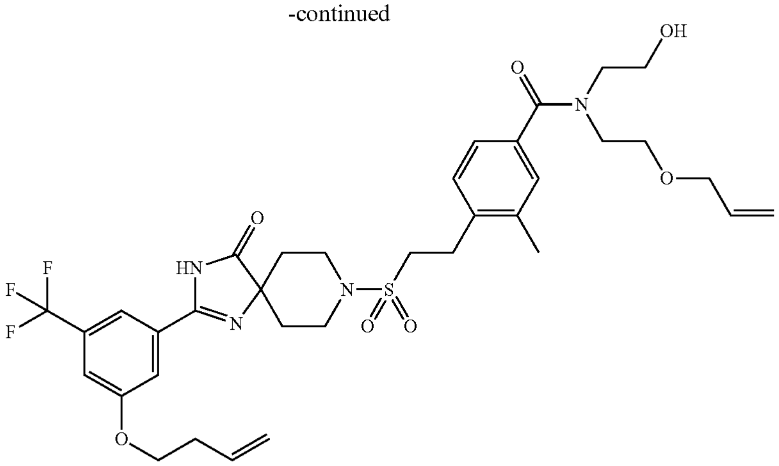

356b

N-(2-Allyloxy-ethyl)-4-{2-[2-(3-but-3-enyloxy-5-trifluoromethyl-phenyl)-4-oxo-1,3,8-triaza-spiro[4.5]dec-1-ene-8-sulfonyl]-ethyl}-N-(2-hydroxy-ethyl)-3-methyl-benzamide was obtained by the same method as in Reaction 337-8 using 4-{2-[2-(3-but-3-enyloxy-5-trifluoromethyl-phenyl)-4-oxo-1,3,8-triaza-spiro[4.5]dec-1-ene-8-sulfonyl]-ethyl}-3-methyl-benzoic acid and 2-(2-allyloxy-ethylamino)-ethanol as starting materials.

MS (ESI) m/z=721 (M+H)+;

HPLC retention time: 1.05 min (analysis condition LCMS-F-1).

2-(2-Allyloxy-ethylamino)-ethanol used in the above Reaction 356-1 was synthesized by the following method.

(Reaction 356-2)

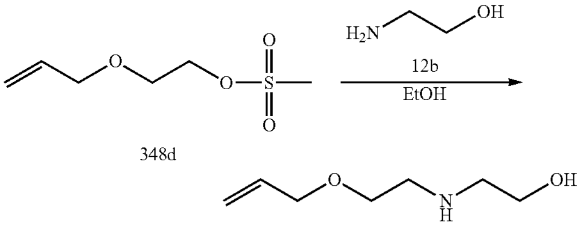

348d

356a 2-(2-Allyloxy-ethylamino)-ethanol was obtained by the same method as in Reaction 337-9 using methanesulfonic acid 2-allyloxy-ethyl ester as a raw material.

(Reaction 356-3)

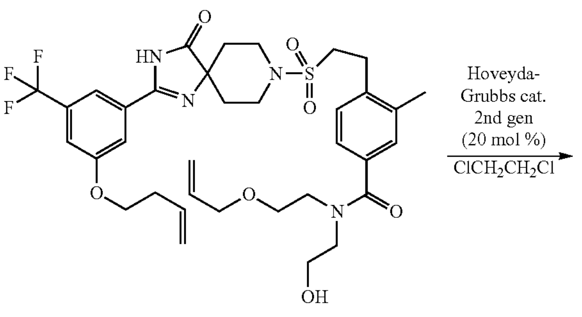

356b

-continued

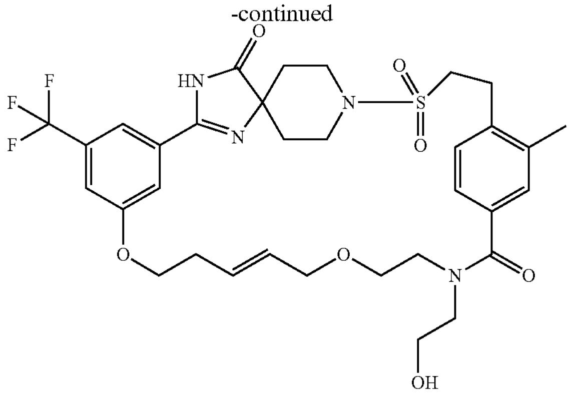

Compound 1428

A macrocyclic olefin compound (Compound 1428) was obtained by the same method as in Reaction 338-1 (using Hoveyda-Grubbs 2$^{nd}$ generation as a catalyst) using N-(2-allyloxy-ethyl)-4-{2-[2-(3-but-3-enyloxy-5-trifluoromethyl-phenyl)-4-oxo-1,3,8-triaza-spiro[4.5]dec-1-ene-8-sulfonyl]-ethyl}-N-(2-hydroxy-ethyl)-3-methyl-benzamide as a starting material.

MS (ESI) m/z=693 (M+H)+;

HPLC retention time: 1.06 min (analysis condition LCMS-F-1).

Example 357

Compound 1429

(Reaction 357-1)

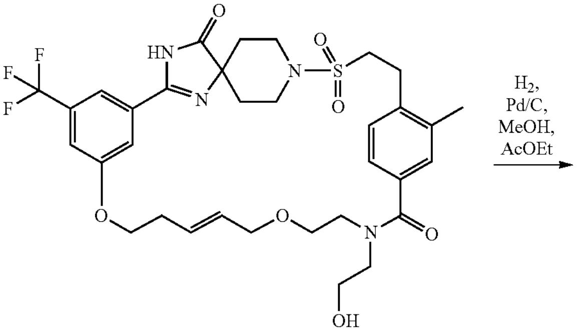

Compound 1428

-continued

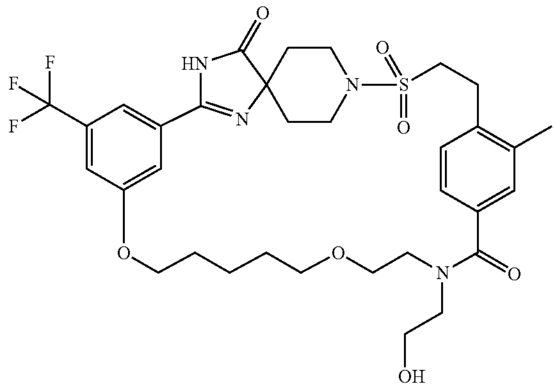

Compound 1429

A saturated macrocyclic compound (Compound 1429) was obtained by the same method as in Reaction 339-1 using a macrocyclic olefin compound (Compound 1428) as a starting material.

MS (ESI) m/z=695 (M+H)+;

HPLC retention time: 1.09 min (analysis condition LCMS-F-1).

Example 358

Compound 1430

(Reaction 358-1)

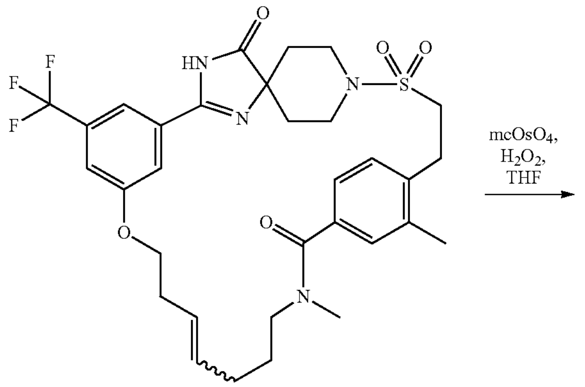

Compound 1406

-continued

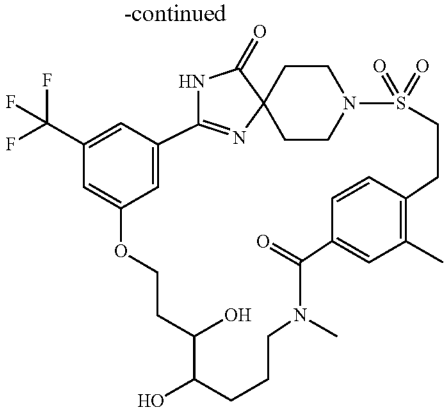

Compound 1430

A macrocyclic olefin compound (Compound 1406) (20 mg, 0.031 mmol) was dissolved in THF (1 ml). Microcapsulated osmium tetroxide (7.1 mg; 0.79 mg, 3.1 μmol as osmium tetroxide) and 30% aqueous hydrogen peroxide (0.028 ml) were added and the mixture was stirred at 0° C. for 4.5 hours and at room temperature for three hours. An aqueous sodium sulfite solution was added to the reaction solution, followed by extraction with ethyl acetate. The organic layer was washed with water and saturated brine, and then dried over anhydrous sodium sulfate and concentrated under reduced pressure. The resulting residue was purified by P-TLC to give a macrocyclic diol compound (Compound 1430, 2 mg, 10%).

MS (ESI) m/z=681 (M+H)+;

HPLC retention time: 2.22 min (analysis condition LCMS-F-1).

Example 359

Compound 1431

(Reaction 359-1)

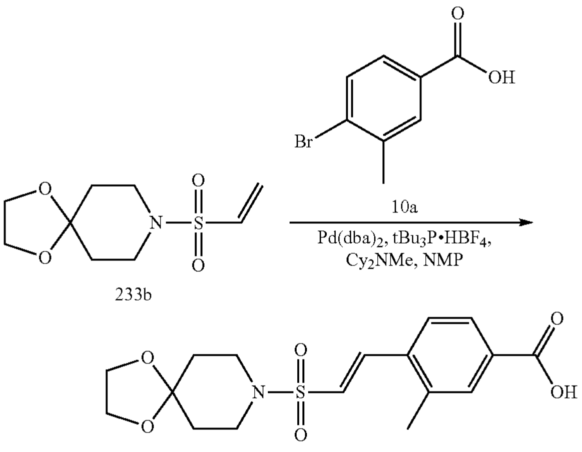

233b

359a

Dicyclohexyl-methyl-amine (34.2 ml, 162.8 mmol) was added to a solution of 8-ethenesulfonyl-1,4-dioxa-8-aza-spiro[4.5]decane (17.3 g, 74.01 mmol), 4-bromo-3-methyl-benzoic acid (19.1 g, 88.82 mmol), $Pd(dba)_2$ (4.26 g, 7.40 mmol) and tri-t-butylphosphonium tetrafluoroborate (2.15 g, 7.40 mmol) in NMP (70.0 ml), and the mixture was stirred at 100° C. for one hour in a nitrogen atmosphere. The reaction solution was cooled to room temperature and then diluted with ethyl acetate, and the organic layer was washed with a 1 M aqueous hydrochloric acid solution and saline. The organic layer was allowed to stand for a while, and the precipitated solid was filtered off. The resulting solid was washed with ethyl acetate to give 4-[(E)-2-(1,4-dioxa-8-aza-spiro[4.5]decane-8-sulfonyl)-vinyl]-3-methyl-benzoic acid as a gray solid (25.6 g, 94.1%).

MS (ESI) m/z=368 (M+H)+;

HPLC retention time: 0.61 min (analysis condition LCMS-F-1).

(Reaction 359-2)

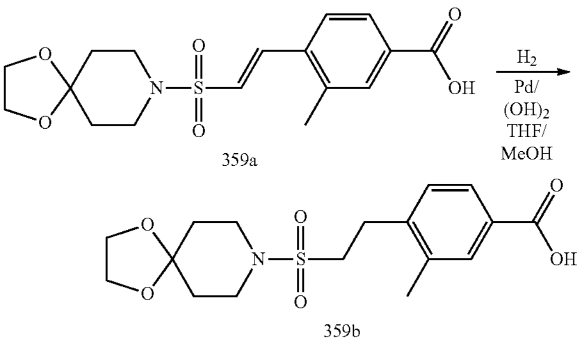

359a

359b $Pd(OH)_2$—C (20.0 g) was added to a solution of 4-[(E)-2-(1,4-dioxa-8-aza-spiro[4.5]decane-8-sulfonyl)-vinyl]-3-methyl-benzoic acid (20.0 g, 54.43 mmol) in THF (600 ml)-methanol (200 ml), and the mixture was stirred at room temperature overnight in a hydrogen atmosphere. The reaction mixture was filtered through celite, and the filtrate was then concentrated under reduced pressure to give 4-[2-(1,4-dioxa-8-aza-spiro[4.5]decane-8-sulfonyl)-ethyl]-3-methyl-benzoic acid as a white solid (18.23 g, 90.7%).

MS (ESI) m/z=370 (M+H)+;

HPLC retention time: 1.85 min (analysis condition LCMS-B-1).

(Reaction 359-3)

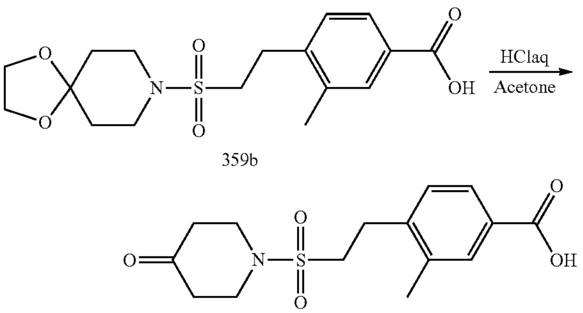

359b

359c

A 6 M aqueous hydrochloric acid solution (217.9 ml, 1307.4 mmol) was slowly added to a suspension of 4-[2-(1,4-dioxa-8-aza-spiro[4.5]decane-8-sulfonyl)-ethyl]-3-methyl-benzoic acid (16.1 g, 43.58 mmol) in acetone (485 ml) at 0° C., and the mixture was warmed to room temperature and stirred overnight. The reaction mixture was filtered off, and the filtrate was then concentrated under reduced pressure. The precipitated solid was filtered off again. The solids filtered off were combined and dried to give 3-methyl-4-[2-(4-oxo-piperidine-1-sulfonyl)-ethyl]-benzoicacid as a white solid (13.62 g, 91.8%).

MS (ESI) m/z=326 (M+H)+;

HPLC retention time: 1.57 min (analysis condition LCMS-B-1).

(Reaction 359-4)

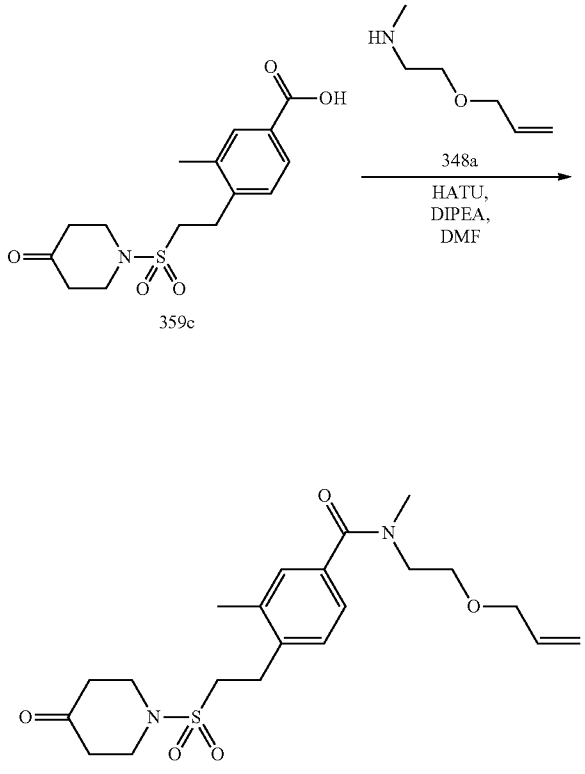

359c

359d

HATU (91 mg, 0.239 mmol) was added to a solution of 3-methyl-4-[2-(4-oxo-piperidine-1-sulfonyl)-ethyl]-benzoic acid (50 mg, 0.154 mmol), (2-allyloxy-ethyl)-methyl-amine (36 mg, 0.312 mmol) and diisopropylethylamine (0.065 ml, 0.384 mmol) in DMF (0.5 ml), and the mixture was stirred at room temperature overnight. Water (12 ml) and 1 N hydrochloric acid (1.5 ml) were added to the reaction solution, followed by extraction with ethyl acetate. The organic layer was sequentially washed with 0.1 N hydrochloric acid, water and saturated brine, and then dried over anhydrous sodium sulfate and concentrated under reduced pressure. The resulting residue was purified by silica gel column chromatography (hexane-ethyl acetate) to give N-(2-allyloxy-ethyl)-3,N-dimethyl-4-[2-(4-oxo-piperidine-1-sulfonyl)-ethyl]-benzamide (76 mg, 100%).

MS (ESI) m/z=423 (M+H)+;

HPLC retention time: 2.15 min (analysis condition LCMS-C1).

(Reaction 359-5)

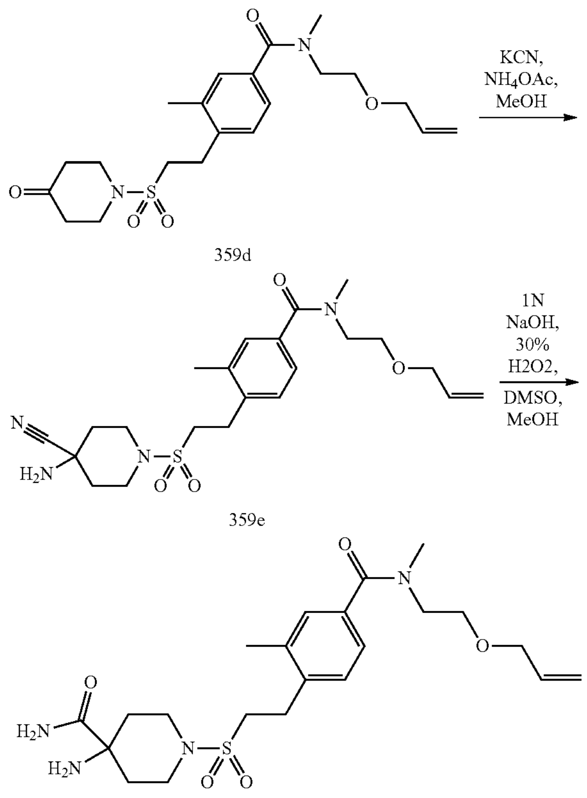

359d

359e

359f (Reaction 359-6)

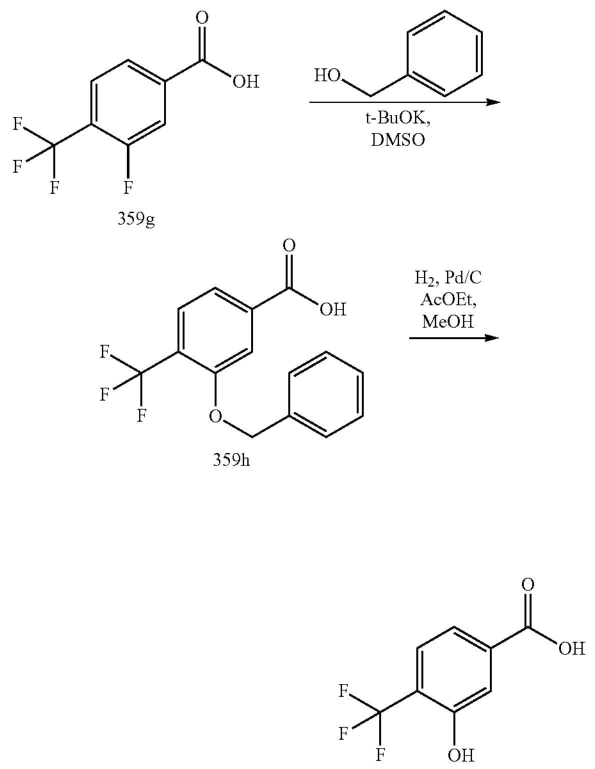

359g

359h

359i

Potassium cyanide (382 mg, 5.87 mmol) and ammonium acetate (513 mg, 6.65 mmol) were added to a solution of N-(2-allyloxy-ethyl)-3,N-dimethyl-4-[2-(4-oxo-piperidine-1-sulfonyl)-ethyl]-benzamide (1.65 g, 3.91 mmol) in methanol (20 ml), and the mixture was stirred at 65° C. for three hours. Sodium bicarbonate (290 mg) was added to the reaction solution, and the mixture was then concentrated under reduced pressure. Water was added to the resulting residue, followed by extraction with methylene chloride. The organic layer was washed with saturated brine, dried over anhydrous sodium sulfate and concentrated under reduced pressure to give N-(2-allyloxy-ethyl)-4-[2-(4-amino-4-cyano-piperidine-1-sulfonyl)-ethyl]-3,N-dimethyl-benzamide (1.57 g) as a crude compound.

A 1 N aqueous sodium hydroxide solution (1.41 ml) and 30% aqueous hydrogen peroxide (0.95 ml) were added to a solution of the resulting N-(2-allyloxy-ethyl)-4-[2-(4-amino-4-cyano-piperidine-1-sulfonyl)-ethyl]-3,N-dimethyl-benzamide in methanol (24 ml)-DMSO (1.3 ml), and the mixture was stirred at room temperature for one hour. A 10% (w/w) aqueous sodium sulfite solution (2.64 ml) was added to the reaction solution, and the mixture was stirred at room temperature for 40 minutes. The precipitated insoluble matter was then removed by filtration. The resulting filtrate was concentrated under reduced pressure to give 1-(2-{4-[(2-allyloxy-ethyl)-methyl-carbamoyl]-2-methyl-phenyl}-ethanesulfonyl)-4-amino-piperidine-4-carboxylic amide (2.13 g). This was used in the next reaction without further purification.

MS (ESI) m/z=467 (M+H)+;

HPLC retention time: 1.59 min (analysis condition LCMS-A-1).

Potassium tert-butoxide (816 mg, 7.28 mmol) was added to a solution of 3-fluoro-4-trifluoromethyl-benzoic acid (682 mg, 3.28 mmol) and benzyl alcohol (471 mg, 4.36 mmol) in DMSO (7.3 ml), and the mixture was stirred at room temperature for 16 hours. The reaction solution was made acidic by adding concentrated hydrochloric acid, and the precipitated insoluble matter was then filtered off. The resulting solid was washed with water and then dried to give 3-benzyloxy-4-trifluoromethyl-benzoic acid as a crude compound.

$^1$H-NMR (400 MHz, $CDCl_3$) δ 7.77-7.70 (3H, m), 7.48-7.32 (5H, m), 5.27 (2H, s);

MS (ESI) m/z=295 (M−H)−;

HPLC retention time: 2.37 min (analysis condition LCMS-C-1).

10% Pd/C (590 mg) was added to 3-benzyloxy-4-trifluoromethyl-benzoic acid in a methanol-ethyl acetate mixed solvent (1:1), and the mixture was stirred at room temperature for two days in a hydrogen atmosphere. The reaction solution was filtered through celite, and the filtrate was then concentrated under reduced pressure. The resulting residue was purified by silica gel column chromatography (n-hexane-ethyl acetate) to give 3-hydroxy-4-trifluoromethyl-benzoic acid (582 mg, 86%).

$^1$H-NMR (400 MHz, DMSO-$d_6$) δ 13.26 (1H, br s), 10.94 (1H, br s), 7.63 (1H, d, J=8.3 Hz), 7.59 (1H, s), 7.46 (1H, d, J=8.8 Hz);

MS (ESI) m/z=205 (M−H)−;

HPLC retention time: 1.15 min (analysis condition LCMS-C-1).

(Reaction 359-7)

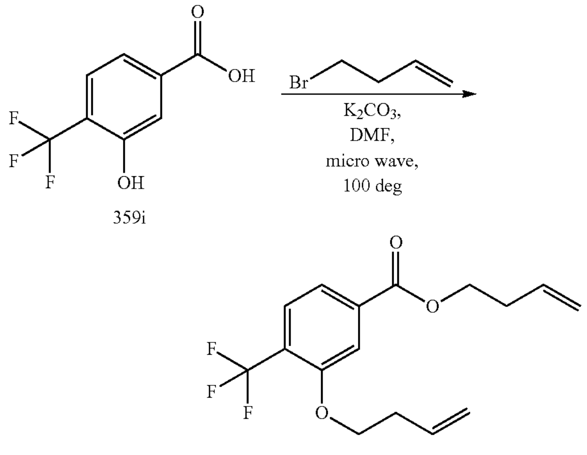

359i

359j (Reaction 359-8)

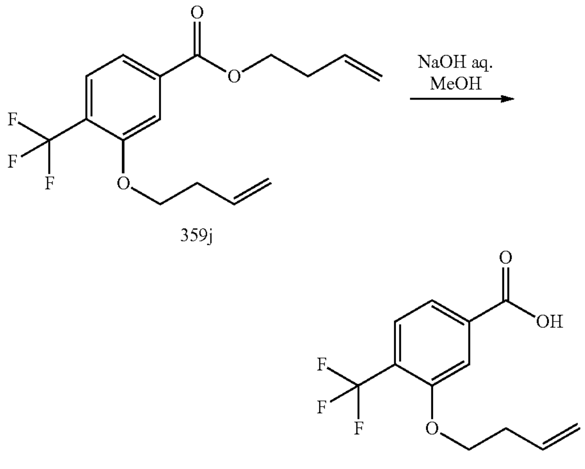

359j

359k

3-But-3-enyloxy-4-trifluoromethyl-benzoic acid but-3-enyl ester was obtained by the same method as in Reaction 337-1 using 3-hydroxy-4-trifluoromethyl-benzoic acid as a raw material.

$^1$H-NMR (400 MHz, $CDCl_3$) δ 7.66-7.61 (3H, m), 5.98-5.81 (2H, m), 5.22-5.15 (2H, m), 5.14-5.10 (2H, m), 4.40 (2H, t, J=6.8 Hz), 4.16 (2H, t, J=6.6 Hz), 2.62-2.51 (4H, m).

3-But-3-enyloxy-4-trifluoromethyl-benzoic acid was obtained by the same method as in Reaction 337-2 using 3-but-3-enyloxy-4-trifluoromethyl-benzoic acid but-3-enyl ester as a raw material.

$^1$H-NMR (400 MHz, $CD_3OD$) δ 7.73 (1H, br s), 7.68 (2H, br s), 6.00-5.90 (1H, m), 5.21-5.15 (1H, m), 5.11-5.08 (1H, m), 4.19 (2H, t, J=6.6 Hz), 2.60-2.55 (2H, m).

(Reaction 359-9)

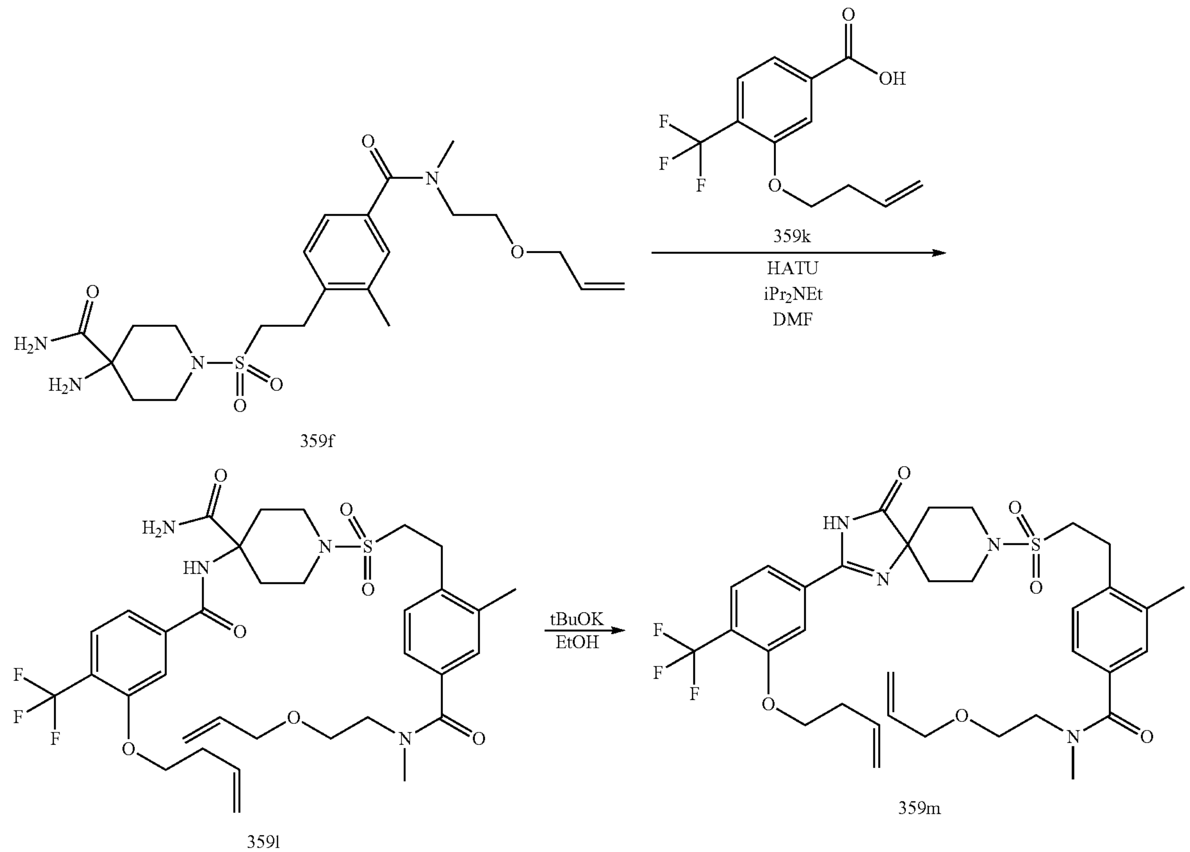

359f

359l

359m

HATU (245 mg, 0.644 mmol) was added to a solution of 1-(2-{4-[(2-allyloxy-ethyl)-methyl-carbamoyl]-2-methyl-phenyl}-ethanesulfonyl)-4-amino-piperidine-4-carboxylic amide (250 mg), 3-but-3-enyloxy-4-trifluoromethyl-benzoic acid (155 mg, 0.596 mmol) and diisopropylethylamine (0.140 ml, 0.812 mmol) in DMF (5 ml), and the mixture was stirred at room temperature for 1.5 hours. Water was added to the reaction solution, followed by extraction with ethyl acetate. The organic layer was washed with water and saturated brine, and then dried over anhydrous sodium sulfate and concentrated under reduced pressure to give 1-(2-{4-[(2-allyloxy-ethyl)-methyl-carbamoyl]-2-methyl-phenyl}-ethanesulfonyl)-4-(3-but-3-enyloxy-4-trifluoromethyl-benzoylamino)-piperidine-4-carboxylic amide as a crude compound (381 mg).

Potassium tert-butoxide (302 mg, 2.69 mmol) was added to a solution of the resulting 1-(2-{4-[(2-allyloxy-ethyl)-methyl-carbamoyl]-2-methyl-phenyl}-ethanesulfonyl)-4-(3-but-3-enyloxy-4-trifluoromethyl-benzoylamino)-piperidine-4-carboxylic amide in ethanol (6 ml), and the mixture was stirred at 80° C. for 30 minutes. A saturated aqueous ammonium chloride solution, water and saturated brine were sequentially added to the reaction solution, followed by extraction with ethyl acetate. The organic layer was washed with saturated brine, and then dried over anhydrous sodium sulfate and concentrated under reduced pressure. The resulting residue was purified by silica gel column chromatography to give N-(2-allyloxy-ethyl)-4-{2-[2-(3-but-3-enyloxy-4-trifluoromethyl-phenyl)-4-oxo-1,3,8-triaza-spiro[4.5]dec-1-ene-8-sulfonyl]-ethyl}-3,N-dimethyl-benzamide (176 mg).

MS (ESI) m/z=691 (M+H)+;

HPLC retention time: 3.03 min (analysis condition LCMS-C1).

(Reaction 359-10)

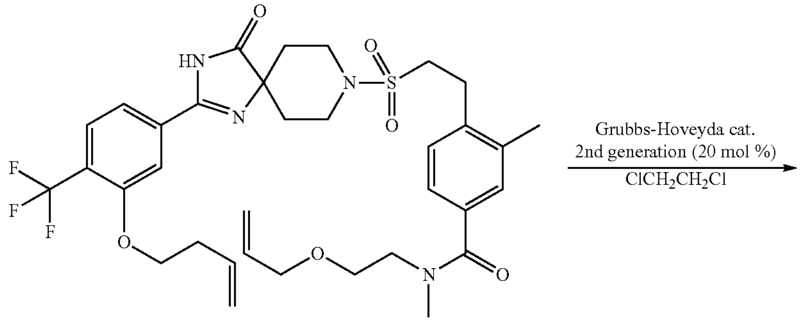

359m

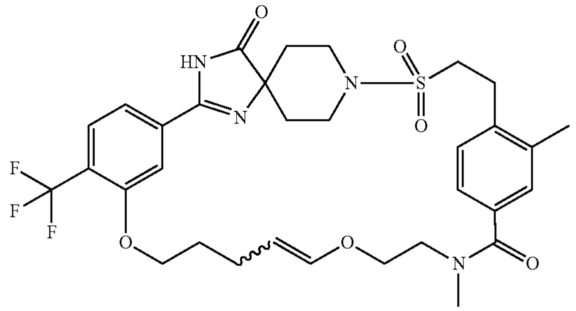

Compound 1431

A macrocyclic olefin compound (Compound 1431) (E/Z=1:2) was obtained by the same method as in Reaction 338-1 (using Hoveyda-Grubbs $2^{nd}$ generation as a catalyst) using N-(2-allyloxy-ethyl)-4-{2-[2-(3-but-3-enyloxy-4-trifluoromethyl-phenyl)-4-oxo-1,3,8-triaza-spiro[4.5]dec-1-ene-8-sulfonyl]-ethyl}-3,N-dimethyl-benzamide as a starting material.

MS (ESI) m/z=663 (M+H)+;

HPLC retention time: 2.90 min (analysis condition LCMS-C-1).

Example 360

Compound 1432

(Reaction 360-1)

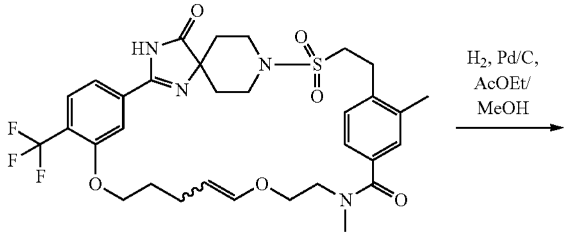

Compound 1431

-continued

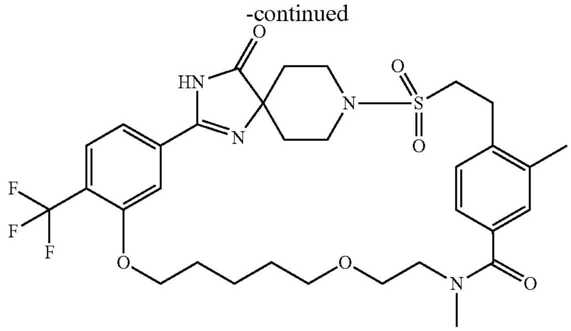

Compound 1432

A saturated macrocyclic compound (Compound 1432) was obtained by the same method as in Reaction 339-1 using a macrocyclic olefin compound (Compound 1431) as a starting material.

MS (ESI) m/z=665 (M+H)+;

HPLC retention time: 1.06 min (analysis condition LCMS-C-1).

Example 361

Compound 1433

(Reaction 361-1)

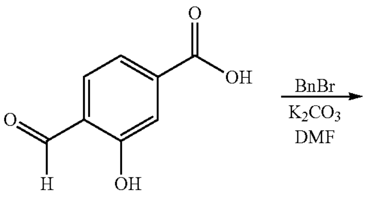

361a

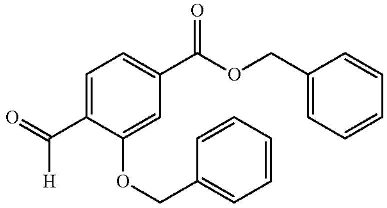

361b

Benzyl bromide (2.17 ml, 18.3 mmol) was added to a solution of 4-formyl-3-hydroxy-benzoic acid (1.01 g, 6.10 mmol) and potassium carbonate (3.37 g, 24.4 mmol) in DMF (10 ml), and the mixture was stirred at 50° C. for five hours. The reaction solution was poured into ice water and extracted with ethyl acetate. The organic layer was washed with water and saturated brine, and then dried over anhydrous sodium sulfate and concentrated under reduced pressure. The resulting residue was purified by silica gel column chromatography (hexane-ethyl acetate) to give 3-benzyloxy-4-formyl-benzoic acid benzyl ester (2.01 g, 95%).

$^1$H-NMR (400 MHz, $CDCl_3$) δ 10.58 (1H, s), 7.89 (1H, d, J=8.3 Hz), 7.78 (1H, d, J=1.5 Hz), 7.73 (1H, br d, J=8.3 Hz), 7.46-7.35 (10H, m), 5.38 (2H, s), 5.24 (2H, s).

(Reaction 361-2)

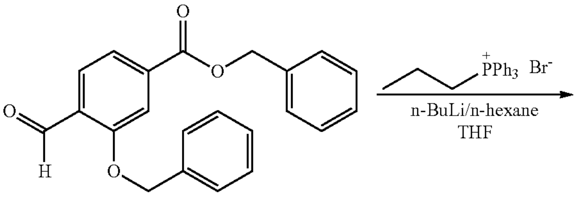

361b

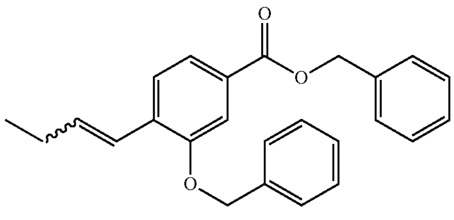

361c n-Butyllithium (1.65 M solution in n-hexane, 4.22 ml, 6.92 mmol) was added dropwise to a solution of triphenyl-n-propyl-phosphonium bromide (2.91 g, 7.54 mmol) in THF (49 ml) at 0° C., and the mixture was stirred for 30 minutes. Further, a solution of 3-benzyloxy-4-formyl-benzoic acid benzyl ester (2.01 g, 5.80 mmol) in THF (4.9 ml) was added dropwise and then the mixture was stirred at 0° C. for 30 minutes and at room temperature for 16 hours. A saturated aqueous ammonium chloride solution, water and saturated brine were added to the reaction solution, and this mixture was extracted with ethyl acetate. The organic layer was washed with water and saturated brine, and then dried over anhydrous sodium sulfate and concentrated under reduced pressure. The resulting residue was purified by silica gel column chromatography (n-hexane-ethyl acetate) to give 3-benzyloxy-4-((E/Z)-but-1-enyl)-benzoic acid benzyl ester (E/Z=2:3, 1.74 g, 80%).

$^1$H-NMR (400 MHz, $CDCl_3$) δ 7.68-7.60 (2H, m), 7.50-7.30 (11H, m), 6.79 (0.4H, d, J=16.1 Hz), 6.57 (0.6H, d, J=11.7 Hz), 6.40 (0.4H, dt, J=16.0, 6.6 Hz), 5.78 (0.6H, dt, J=13.7, 5.9 Hz), 5.36 (1.2H, s), 5.35 (0.8H, s), 5.14 (0.8H, s), 5.14 (1.2H, s), 2.32-2.22 (2H, m), 1.09 (1.2H, t, J=7.3 Hz), 1.04 (1.8H, t, J=7.6 Hz).

(Reaction 361-3)

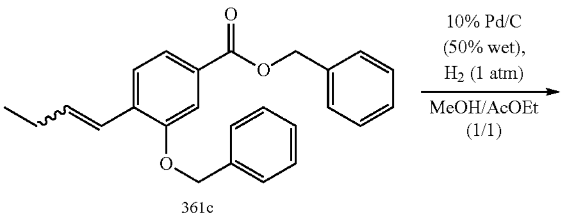

361c

-continued

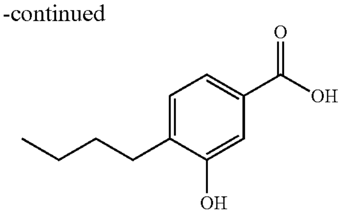

361d

10% Pd/C (174 mg) was added to 3-benzyloxy-4-((E/Z)-but-1-enyl)-benzoic acid benzyl ester (1.74 g, 4.67 mmol) in a methanol-ethyl acetate mixed solvent (1:1), and the mixture was stirred at room temperature for 21 hours in a hydrogen atmosphere. The reaction solution was filtered through celite, and the filtrate was then concentrated under reduced pressure to give 4-butyl-3-hydroxy-benzoic acid (922 mg) as a crude compound.

$^1$H-NMR (400 MHz, $CD_3OD$) δ 7.42-7.39 (2H, m), 7.14-7.11 (1H, m), 2.64 (2H, t, J=7.6 Hz), 1.62-1.54 (2H, m), 1.42-1.33 (2H, m), 0.94 (3H, t, J=7.3 Hz).

(Reaction 361-4)

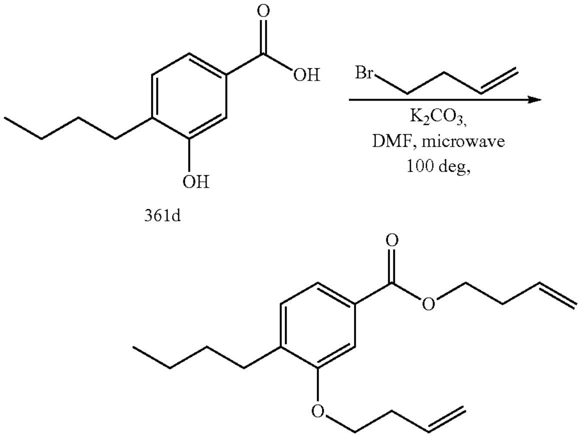

361d

361e

3-But-3-enyloxy-4-butyl-benzoic acid but-3-enyl ester was obtained by the same method as in Reaction 337-1 using 4-butyl-3-hydroxy-benzoic acid as a raw material.

$^1$H-NMR (400 MHz, $CDCl_3$) δ 7.56 (1H, dd, J=7.8, 1.5 Hz), 7.47 (1H, d, J=1.5 Hz), 7.17 (1H, d, J=7.3 Hz), 5.97-5.82 (2H, m), 5.21-5.14 (2H, m), 5.13-5.08 (2H, m), 4.35 (2H, t, J=6.8 Hz), 4.07 (2H, t, J=6.3 Hz), 2.64 (2H, t, J=7.8 Hz), 2.60-2.49 (4H, m), 1.60-1.52 (2H, m), 1.40-1.30 (2H, m), 0.92 (3H, t, J=7.3 Hz).

(Reaction 361-5)

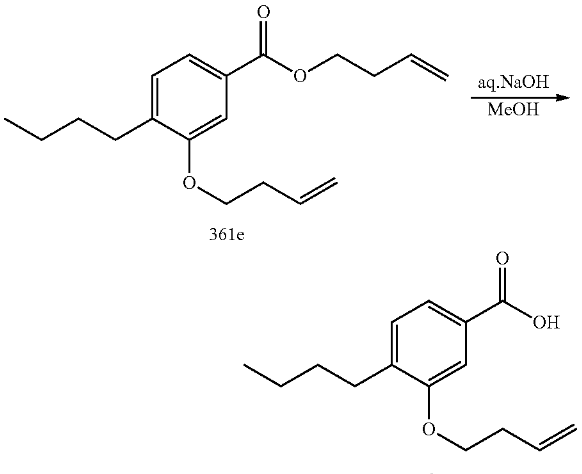

361e

361f

3-But-3-enyloxy-4-butyl-benzoic acid (243 mg, 93%) was obtained by the same method as in Reaction 337-2 using 3-but-3-enyloxy-4-butyl-benzoic acid but-3-enyl ester (318 mg, 1.05 mmol) as a raw material.

$^1$H-NMR (400 MHz, $CD_3OD$) δ 7.53 (1H, dd, J=7.6, 1.7 Hz), 7.50 (1H, d, J=1.5 Hz), 7.19 (1H, d, J=7.8 Hz), 6.01-5.91 (1H, m), 5.21-5.15 (1H, m), 5.11-5.07 (1H, m), 4.08 (2H, t, J=6.1 Hz), 2.65 (2H, t, J=7.6 Hz), 2.59-2.54 (2H, m), 1.61-1.53 (2H, m), 1.40-1.31 (2H, m), 0.94 (3H, t, J=7.3 Hz).

(Reaction 361-6)

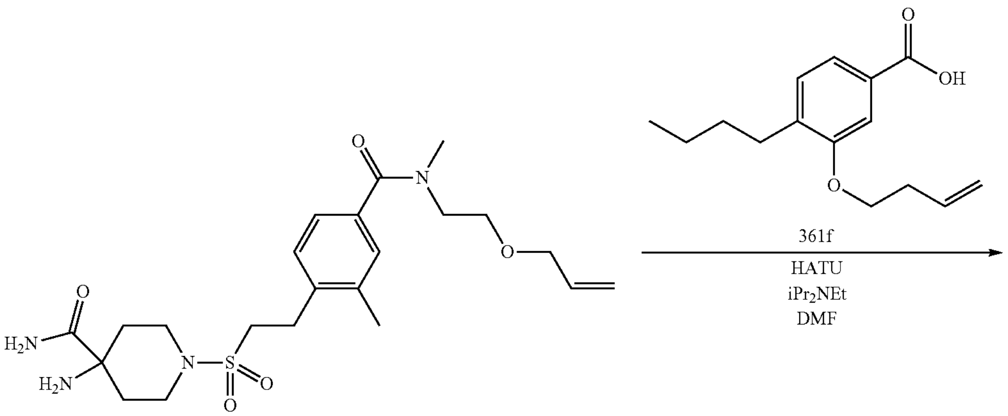

359f

-continued

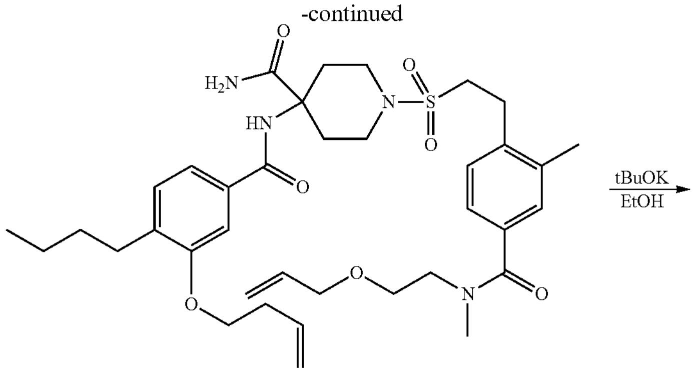

361g

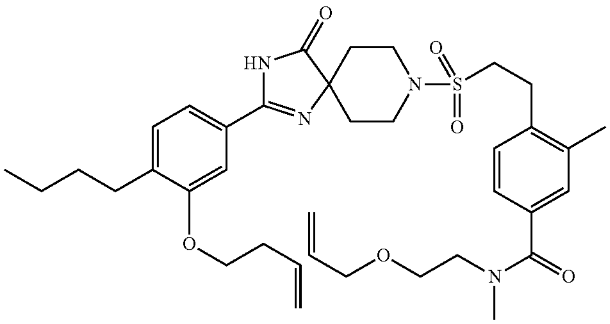

361h

N-(2-Allyloxy-ethyl)-4-{2-[2-(3-but-3-enyloxy-4-butyl-phenyl)-4-oxo-1,3,8-triaza-spiro[4.5]dec-1-ene-8-sulfonyl]-ethyl}-3,N-dimethyl-benzamide was obtained by the same method as in Reaction 359-9 using 3-but-3-enyloxy-4-butyl-benzoic acid (117 mg, 0.471 mmol) and 1-(2-{4-[(2-allyloxy-ethyl)-methyl-carbamoyl]-2-methyl-phenyl}-ethanesulfonyl)-4-amino-piperidine-4-carboxylic amide as starting materials.

MS (ESI) m/z=677 (M−H)−;

HPLC retention time: 3.23 min (analysis condition LCMS-C-1).

(Reaction 361-7)

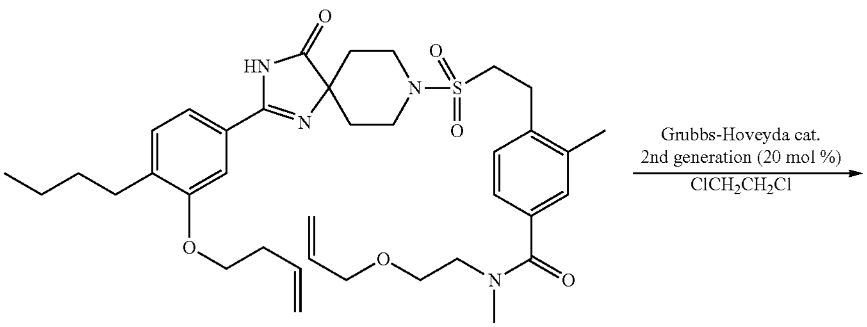

361h

-continued

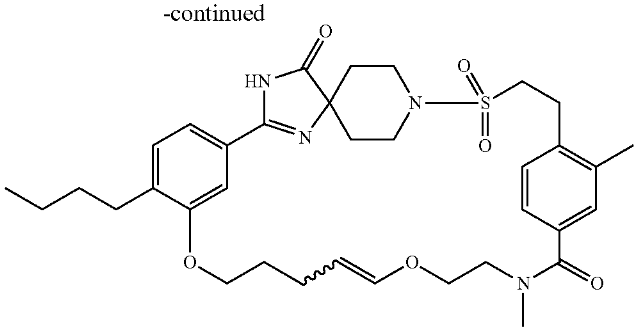

Compound 1433

A macrocyclic olefin compound (Compound 1433) (E/Z=1:2) was obtained by the same method as in Reaction 338-1 (using Hoveyda-Grubbs $2^{nd}$ generation as a catalyst) using N-(2-allyloxy-ethyl)-4-{2-[2-(3-but-3-enyloxy-4-butyl-phenyl)-4-oxo-1,3,8-triaza-spiro[4.5]dec-1-ene-8-sulfonyl]-ethyl}-3,N-dimethyl-benzamide as a starting material.

MS (ESI) m/z=651 (M+H)+;

HPLC retention time: 3.13 min (analysis condition LCMS-C-1).

Example 362

Compound 1434

(Reaction 362-1)

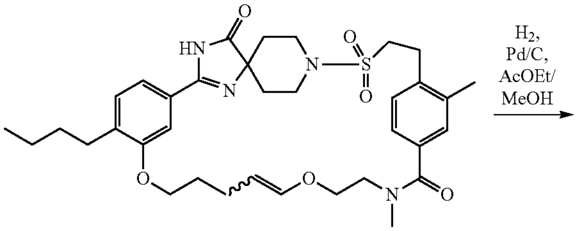

Compound 1433

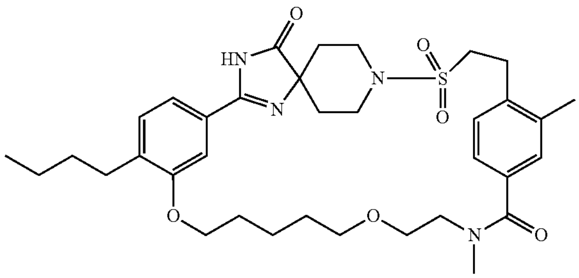

Compound 1434

A saturated macrocyclic compound (Compound 1434) was obtained by the same method as in Reaction 339-1 using a macrocyclic olefin compound (Compound 1433) as a starting material.

MS (ESI) m/z=653 (M+H)+;

HPLC retention time: 1.12 min (analysis condition LCMS-F-1).

Example 363

Compound 1435

(Reaction 363-1)

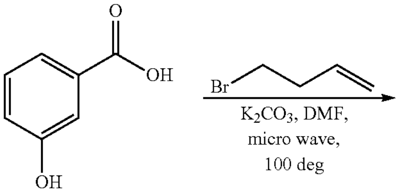

363a

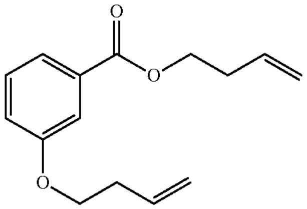

363b

3-But-3-enyloxy-benzoic acid but-3-enyl ester was obtained by the same method as in Reaction 337-1 using 3-hydroxy-benzoic acid as a raw material.

$^1$H-NMR (400 MHz, $CDCl_3$) δ 7.62 (1H, br d, J=7.8 Hz), 7.55 (1H, br s), 7.33 (1H, t, J=8.1 Hz), 7.09 (1H, br d, J=8.3 Hz), 5.96-5.82 (2H, m), 5.20-5.10 (4H, m), 4.37 (2H, t, J=6.8 Hz), 4.06 (2H, t, J=6.8 Hz), 2.60-2.50 (4H, m).

(Reaction 363-2)

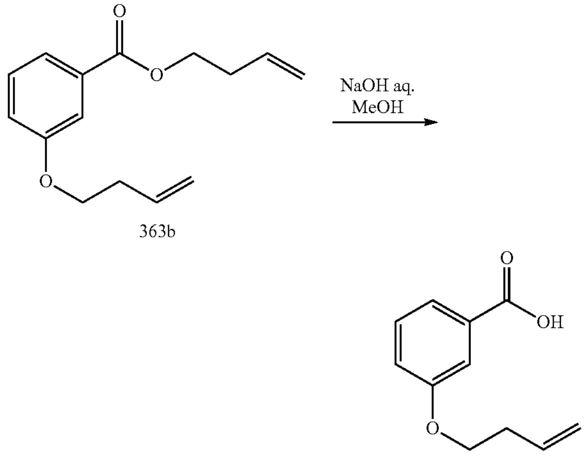

363b

363c

3-But-3-enyloxy-benzoic acid was obtained by the same method as in Reaction 337-2 using 3-but-3-enyloxy-benzoic acid but-3-enyl ester as a raw material.

$^1$H-NMR (400 MHz, $CD_3OD$) δ 7.61-7.58 (1H, m), 7.53-7.52 (1H, m), 7.36 (1H, t, J=8.1 Hz), 7.15-7.12 (1H, m), 5.99-5.88 (1H, m), 5.20-5.14 (1H, m), 5.11-5.07 (1H, m), 4.06 (2H, t, J=6.6 Hz), 2.57-2.51 (2H, m).

N-(2-Allyloxy-ethyl)-4-{2-[2-(3-but-3-enyloxy-phenyl)-4-oxo-1,3,8-triaza-spiro[4.5]dec-1-ene-8-sulfonyl]-ethyl}-3,N-dimethyl-benzamide was obtained by the same method as in Reaction 359-9 using 3-but-3-enyloxy-benzoic acid and 1-(2-{4-[(2-allyloxy-ethyl)-methyl-carbamoyl]-2-methyl-phenyl}-ethanesulfonyl)-4-amino-piperidine-4-carboxylic amide as starting materials.

MS (ESI) m/z=621 (M−H)−;

HPLC retention time: 2.85 min (analysis condition LCMS-C1).

(Reaction 363-4)

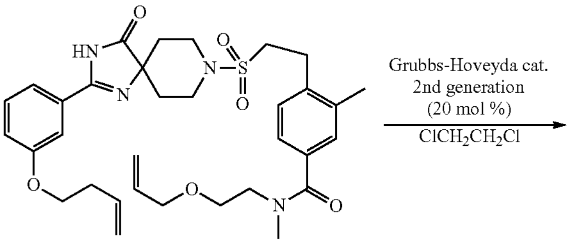

363e (Reaction 363-3)

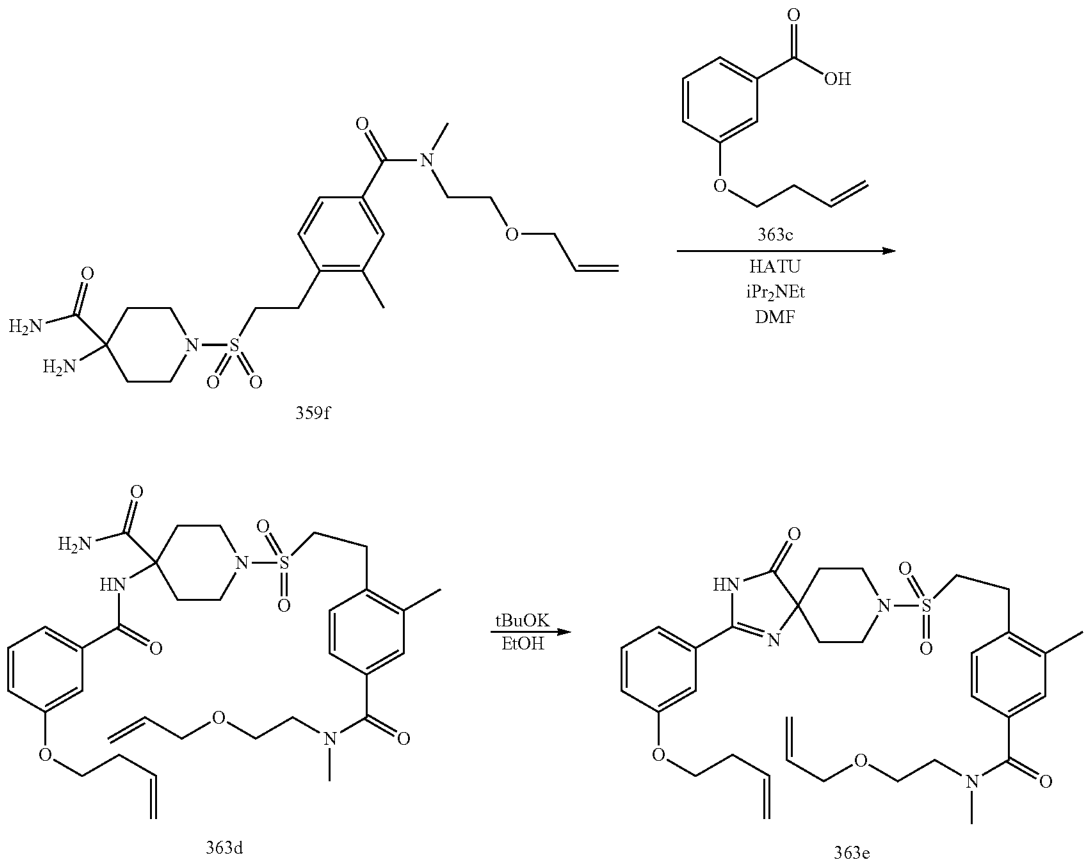

359f

363c

363d

363e

-continued

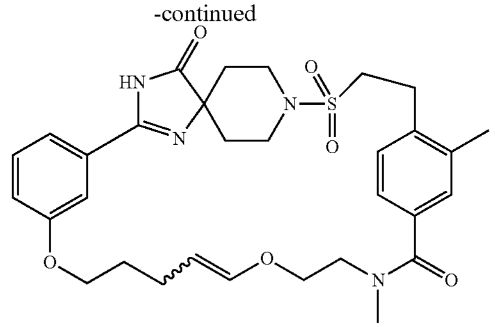

Compound 1435

-continued

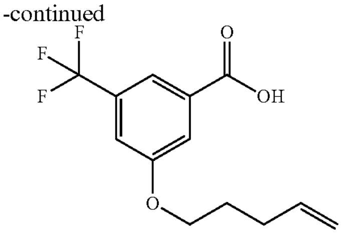

364b

A macrocyclic olefin compound (Compound 1435) E/Z=1:2) was obtained by the same method as in Reaction 338-1 (using Hoveyda-Grubbs 2nd generation as a catalyst) using N-(2-allyloxy-ethyl)-4-{2-[2-(3-but-3-enyloxy-phenyl)-4-oxo-1,3,8-triaza-spiro[4.5]dec-1-ene-8-sulfonyl]-ethyl}-3, N-dimethyl-benzamide as a starting material.

MS (ESI) m/z=595 (M+H)+;

HPLC retention time: 2.70 min (analysis condition LCMS-C-1).

Example 364

Compound 1436

(Reaction 364-1)

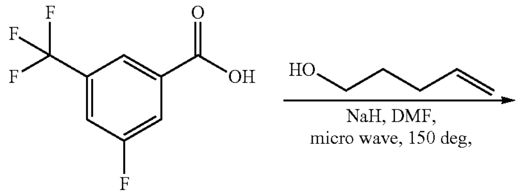

364a

A solution of 3-fluoro-5-trifluoromethyl-benzoic acid (400 mg, 1.92 mmol) in DMF (2 ml) was added dropwise to a suspension of sodium hydride (60% oily, 235 mg, 5.88 mmol) and pent-4-en-1-ol (506 mg, 5.88 mmol) in DMF (12 ml), and the mixture was stirred at 60° C. Further, this mixture was irradiated in a microwave apparatus (150° C., 20 min). The reaction solution was poured into 0.2 N aqueous hydrochloric acid and then extracted with ethyl acetate. The organic layer was washed with saturated brine, and then dried over anhydrous sodium sulfate and concentrated under reduced pressure. The resulting residue was purified by silica gel column chromatography (hexane-ethyl acetate) to give 3-pent-4-enyloxy-5-trifluoromethyl-benzoic acid (290 mg, 55%).

$^1$H-NMR ($CDCl_3$) δ 7.94 (1H, s), 7.77 (1H, s), 7.37 (1H, s), 5.91-5.81 (1H, m), 5.11-5.06 (1H, m), 5.05-5.02 (1H, m), 4.07 (2H, t, J=6.3 Hz), 2.30-2.24 (2H, m), 1.97-1.90 (2H, m);

MS (ESI) m/z=273 (M−H)−;

HPLC retention time: 2.50 min (analysis condition LCMS-C1).

(Reaction 364-2)

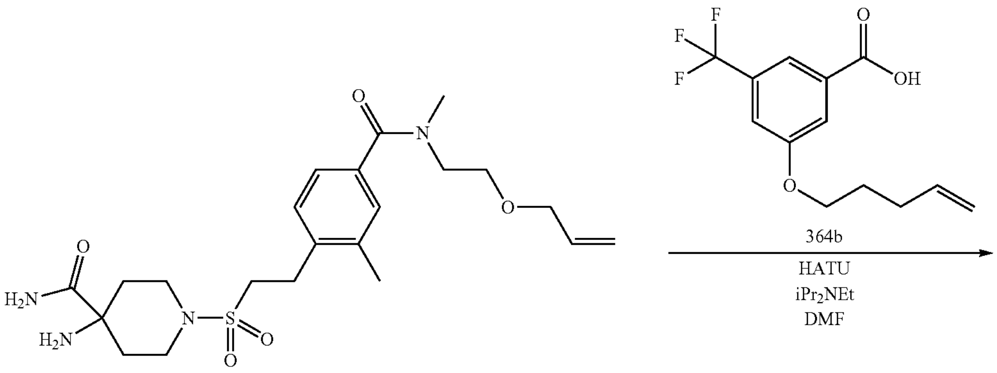

359f

-continued

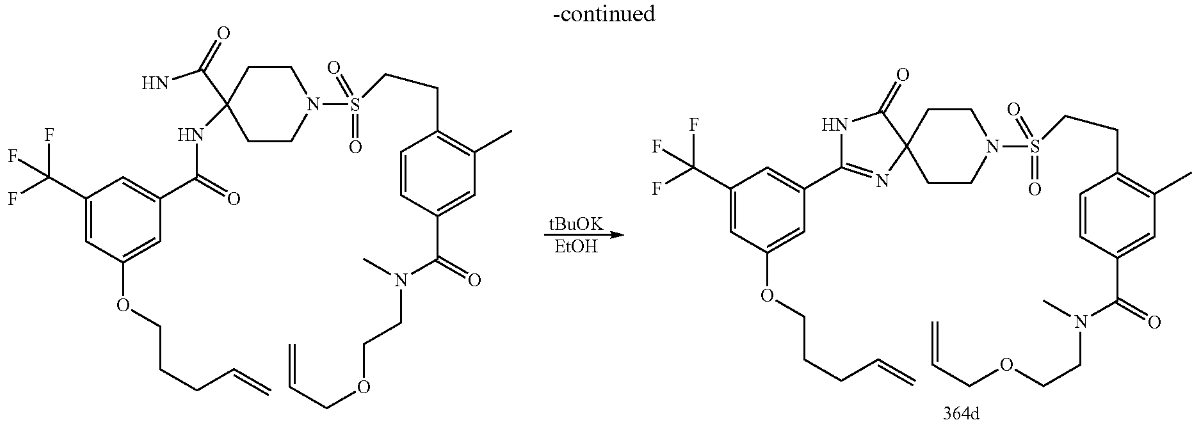

364c

364d

N-(2-Allyloxy-ethyl)-3,N-dimethyl-4-{2-[4-oxo-2-(3-pent-4-enyloxy-5-trifluoromethyl-phenyl)-1,3,8-triaza-spiro[4.5]dec-1-ene-8-sulfonyl]-ethyl}-benzamide was obtained by the same method as in Reaction 359-9 using 3-pent-4-enyloxy-5-trifluoromethyl-benzoic acid and 1-(2-{4-[(2-allyloxy-ethyl)-methyl-carbamoyl]-2-methyl-phenyl}-ethane-sulfonyl)-4-amino-piperidine-4-carboxylic amide as starting materials.

MS (ESI) m/z=705 (M+H)+

HPLC retention time: 1.12 min (analysis condition LCMS-F-1).

(Reaction 364-3)

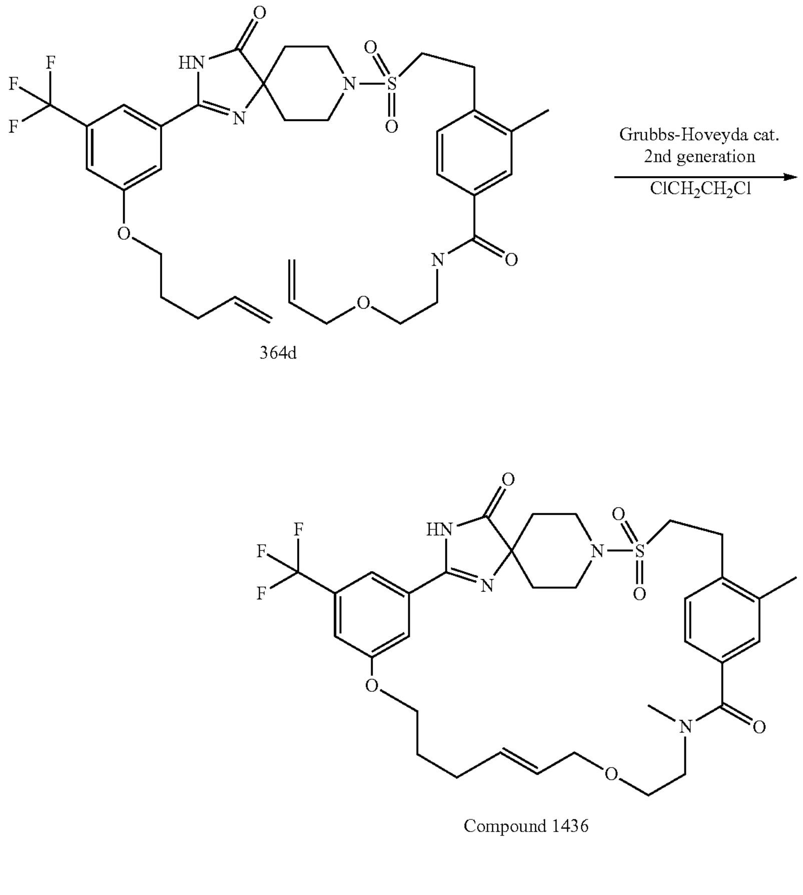

364d

Compound 1436

A macrocyclic olefin compound (Compound 1436) was obtained by the same method as in Reaction 338-1 (using Hoveyda-Grubbs 2$^{nd}$ generation as a catalyst) using N-(2-allyloxy-ethyl)-3,N-dimethyl-4-{2-[4-oxo-2-(3-pent-4-enyloxy-5-trifluoromethyl-phenyl)-1,3,8-triaza-spiro[4.5]dec-1-ene-8-sulfonyl]-ethyl}-benzamide as a starting material.

MS (ESI) m/z=677 (M+H)+;

HPLC retention time: 1.07 min (analysis condition LCMS-F-1).

Example 365

Compound 1437

(Reaction 365-1)

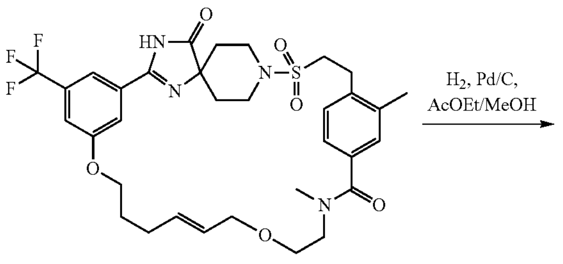

Compound 1436

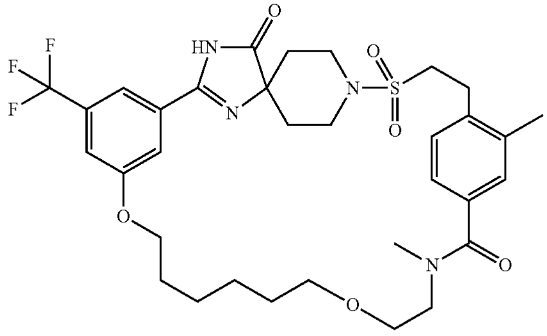

Compound 1437

A saturated macrocyclic compound (Compound 1437) was obtained by the same method as in Reaction 339-1 using a macrocyclic olefin compound (Compound 1436) as a starting material.

MS (ESI) m/z=679 (M+H)+;

HPLC retention time: 1.11 min (analysis condition LCMS-F-1).

Example 366

Compound 1438

(Reaction 366-1)

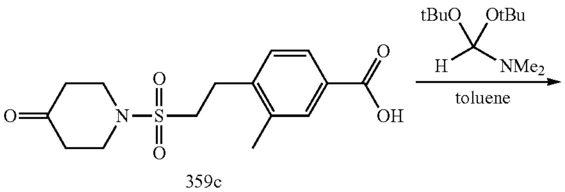

359c

-continued

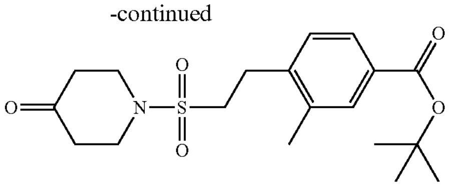

366a

3-Methyl-4-[2-(4-oxo-piperidine-1-sulfonyl)-ethyl]-benzoic acid (1.23 g, 3.78 mmol) was suspended in toluene (20.0 ml). Di-tert-butoxymethyl-dimethyl-amine (3.63 ml, 15.12 mmol) was added and the mixture was stirred at 80° C. for 30 minutes. Thereafter, di-tert-butoxymethyl-dimethyl-amine (2.70 ml, 11.34 mmol) was added again and the mixture was stirred at 80° C. for 30 minutes. After completion of the reaction, the reaction solution was left to cool and diluted with ethyl acetate. The organic layer was then washed with an aqueous sodium bicarbonate solution and saline. The organic layer was dried over anhydrous magnesium sulfate and then concentrated under reduced pressure. The resulting residue was purified by column chromatography (hexane:ethyl acetate) to give 3-methyl-4-[2-(4-oxo-piperidine-1-sulfonyl)-ethyl]-benzoic acid tert-butyl ester as a white solid (1.01 g, 70.0%).

MS (ESI) m/z=382 (M+H)+;

HPLC retention time: 2.54 min (analysis condition LCMS-B-1)

(Reaction 366-2)

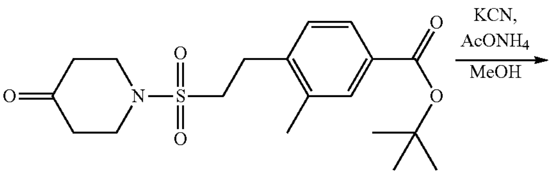

366a

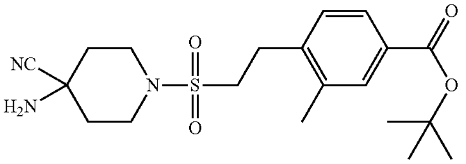

366b

3-Methyl-4-[2-(4-oxo-piperidine-1-sulfonyl)-ethyl]-benzoic acid tert-butyl ester (969.2 mg, 2.54 mmol), ammonium acetate (469.9 mg, 6.10 mmol) and potassium cyanide (330.9 mg, 5.08 mmol) were dissolved in methanol (12.0 ml), and the mixture was stirred at 65° C. for one hour. After completion of the reaction, the mixture was left to cool and an aqueous sodium bicarbonate solution was added, followed by extraction with ethyl acetate. The organic layer was washed with saline, and then dried over anhydrous magnesium sulfate and concentrated under reduced pressure to give 4-[2-(4-amino-4-cyano-piperidine-1-sulfonyl)-ethyl]-3-methyl-benzoic acid tert-butyl ester as an amorphous (1.07 g).

MS (ESI) m/z=408 (M+H)+;

HPLC retention time: 2.54 min (analysis condition LCMS-F-1).

(Reaction 366-3)

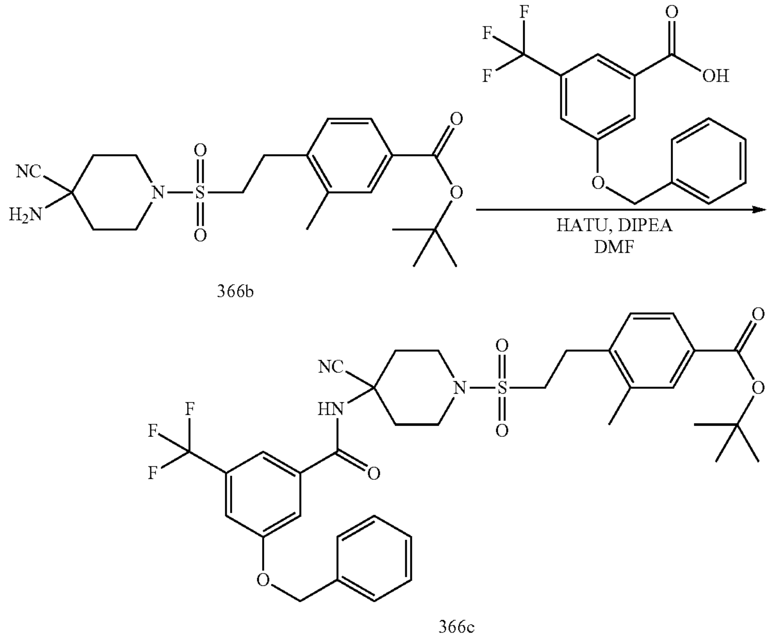

366b

366c

4-[2-(4-Amino-4-cyano-piperidine-1-sulfonyl)-ethyl]-3-methyl-benzoic acid tert-butyl ester (500.0 mg, 1.23 mmol), 3-benzyloxy-5-trifluoromethyl-benzoic acid (436.1 mg, 1.47 mmol) and DIPEA (0.321 ml, 1.85 mmol) were dissolved in DMF (5.50 ml). HATU (561.2 mg, 1.47 mmol) was added and the mixture was stirred at room temperature for one hour. The reaction solution was diluted with diethyl ether, and the organic layer was washed with a 1 M aqueous hydrochloric acid solution, an aqueous sodium bicarbonate solution and saline. The organic layer was dried over anhydrous magnesium sulfate and then concentrated under reduced pressure. The resulting residue was purified by column chromatography (hexane-ethyl acetate) to give 4-{2-[4-(3-benzyloxy-5-trifluoromethyl-benzoylamino)-4-cyano-piperidine-1-sulfonyl]-ethyl}-3-methyl-benzoic acid tert-butyl ester as a yellow amorphous (796.2 mg, 94.4% in two steps).

MS (ESI) m/z=685 (M+H)+;

HPLC retention time: 1.16 min (analysis condition LCMS-F-1).

(Reaction 366-4)

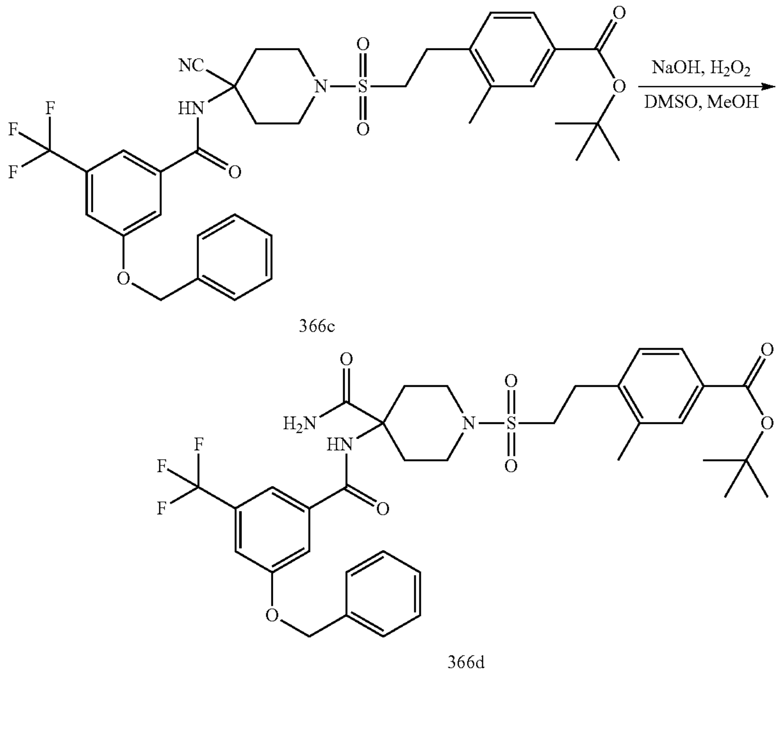

366c

366d

4-{2-[4-(3-Benzyloxy-5-trifluoromethyl-benzoylamino)-4-cyano-piperidine-1-sulfonyl]-ethyl}-3-methyl-benzoic acid tert-butyl ester (1.40 g, 2.04 mmol) was dissolved in DMSO (0.188 ml, 2.65 mmol) and methanol (7.00 ml). A 1 M aqueous sodium hydroxide solution (0.204 ml, 0.204 mmol) and aqueous hydrogen peroxide (30%, 0.265 ml, 2.65 mmol) were added under ice-cooling. The mixture was warmed to room temperature and stirred as such for two hours. After completion of the reaction, an aqueous sodium thiosulfate solution and an aqueous ammonium chloride solution were added, followed by extraction with ethyl acetate. The organic layer was washed with saline, dried over anhydrous magnesium sulfate and then concentrated under reduced pressure to give 4-{2-[4-(3-benzyloxy-5-trifluoromethyl-benzoylamino)-4-carbamoyl-piperidine-1-sulfonyl]-ethyl}-3-methyl-benzoic acid tert-butyl ester as a pale yellow amorphous (1.48 g).

MS (ESI) m/z=704 (M+H)+;

HPLC retention time: 1.15 min (analysis condition LCMS-F-1).

(Reaction 366-5)

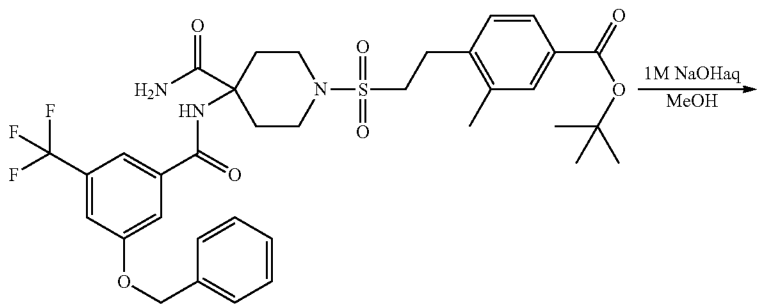

366d

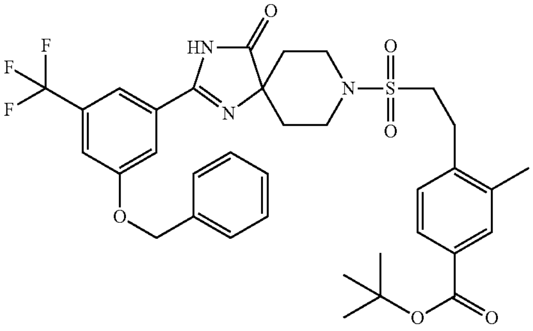

366e

4-{2-[4-(3-Benzyloxy-5-trifluoromethyl-benzoylamino)-4-carbamoyl-piperidine-1-sulfonyl]-ethyl}-3-methyl-benzoic acid tert-butyl ester (1.23 g, 1.75 mmol) was dissolved in methanol (17.5 ml). A 1 M aqueous sodium hydroxide solution (1.75 ml, 1.75 mmol) was added and the mixture was stirred at 60° C. for six hours. After completion of the reaction, the reaction solution was left to cool and an aqueous ammonium chloride solution was added, followed by extraction with ethyl acetate. The organic layer was washed with saline, dried over anhydrous magnesium sulfate and then concentrated under reduced pressure. The residue obtained by concentration was purified by column chromatography (hexane:ethyl acetate) to give 4-{2-[2-(3-benzyloxy-5-trifluoromethyl-phenyl)-4-oxo-1,3,8-triaza-spiro[4.5]dec-1-ene-8-sulfonyl]-ethyl}-3-methyl-benzoic acid tert-butyl ester as a pale yellow amorphous (952.1 mg, yield in two steps: 79.3%).

MS (ESI) m/z=686 (M+H)+;

HPLC retention time: 1.19 min (analysis condition LCMS-F-1).

(Reaction 366-6)

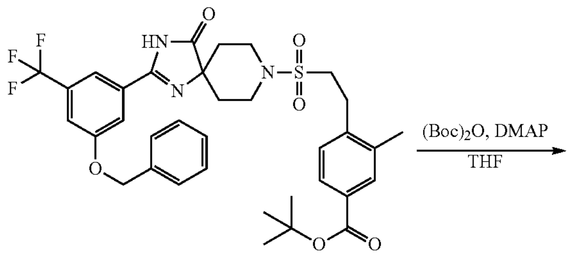

366e

-continued

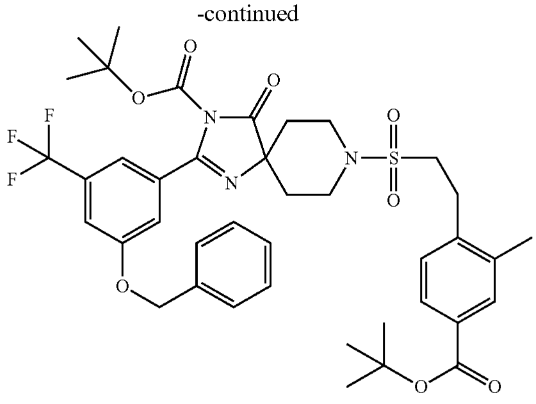

366g

4-{2-[2-(3-Benzyloxy-5-trifluoromethyl-phenyl)-4-oxo-1,3,8-triaza-spiro[4.5]dec-1-ene-8-sulfonyl]-ethyl}-3-methyl-benzoic acid tert-butyl ester (1.14 g, 1.66 mmol) was dissolved in THF (8.0 ml). DMAP (60.8 mg, 0.498 mmol) and di-tert-butyl dicarbonate (725.6 mg, 3.32 mmol) were added and the mixture was stirred at room temperature for one hour. Thereafter, di-tert-butyl dicarbonate (181.0 mg, 0.830 mmol) was further added and the mixture was stirred at room temperature for 30 minutes. After completion of the reaction, the reaction solution was diluted with ethyl acetate, and the organic layer was washed with saline. The organic layer was dried over anhydrous magnesium sulfate and then concentrated under reduced pressure. The resulting residue was purified by column chromatography (hexane:ethyl acetate) to give 2-(3-benzyloxy-5-trifluoromethyl-phenyl)-8-[2-(4-tert-butoxycarbonyl-2-methyl-phenyl)-ethanesulfonyl]-4-oxo-1,3,8-triaza-spiro[4.5]dec-1-ene-3-carboxylic acid tert-butyl ester as a white solid (1.11 g, 85.1%).

MS (ESI) m/z=786 (M+H)+;

HPLC retention time: 1.20 min (analysis condition LCMS-F-1).

(Reaction 366-7)

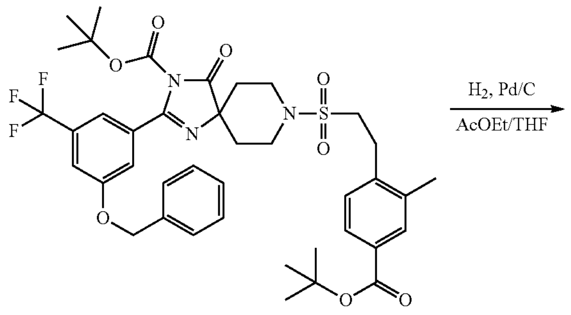

366g

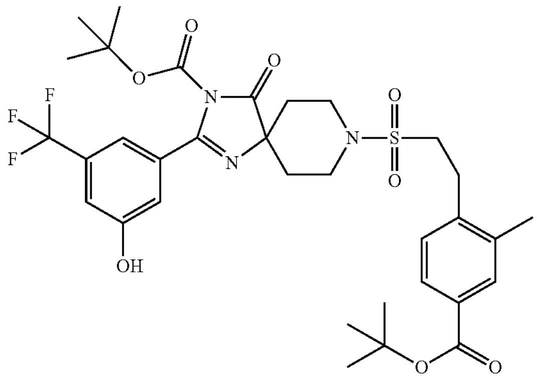

366h 2-(3-Benzyloxy-5-trifluoromethyl-phenyl)-8-[2-(4-tert-butoxycarbonyl-2-methyl-phenyl)-ethanesulfonyl]-4-oxo-1,3,8-triaza-spiro[4.5]dec-1-ene-3-carboxylic acid tert-butyl ester (1.11 g, 1.41 mmol) was dissolved in ethyl acetate (45.0 ml)-THF (15.0 ml). Pd—C (222 mg) was added and the mixture was stirred at room temperature and for one hour in a hydrogen atmosphere. After completion of the reaction, the black solid was filtered off through celite, and the filtrate was concentrated under reduced pressure to give 8-[2-(4-tert-butoxycarbonyl-2-methyl-phenyl)-ethanesulfonyl]-2-(3-hydroxy-5-trifluoromethyl-phenyl)-4-oxo-1,3,8-triaza-spiro[4.5]dec-1-ene-3-carboxylic acid tert-butyl ester as an amorphous (1.01 g, 100%).

$^1$H-NMR (400 MHz, $CDCl_3$) δ 7.80-7.82 (2H, m), 7.22-7.24 (4H, m), 6.83 (1H, br), 3.68-3.74 (2H, m), 3.11-3.27 (6H, m), 2.50 (3H, s), 2.05-2.14 (2H, m), 1.63-1.71 (2H, m), 1.38 (9H, s);

MS (ESI) m/z=696 (M+H)+;

HPLC retention time: 1.13 min (analysis condition LCMS-F-1).

(Reaction 366-8)

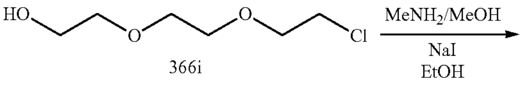

366i

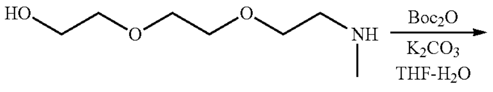

366j

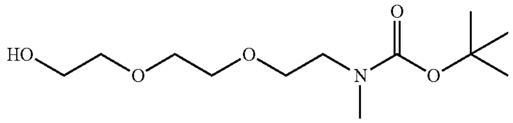

366k

2-[2-(2-Chloro-ethoxy)-ethoxy]-ethanol (2.00 mL, 13.8 mmol) was dissolved in ethanol (14.0 mL). A solution of methylamine in methanol (40%, 14.0 mL, 138 mmol) and sodium iodide (103 mg, 0.67 mmol) were added, and the mixture was stirred at 60° C. for 18 hours and then stirred at 75° C. for seven hours in a nitrogen atmosphere. The reaction solution was concentrated under reduced pressure to give 2-[2-(2-methylamino-ethoxy)-ethoxy]-ethanol as a crude product.

2-[2-(2-Methylamino-ethoxy)-ethoxy]-ethanol was dissolved in THF (6.88 mL)-water (6.88 mL). Di-tert-butyl dicarbonate (9.01 g, 41.3 mmol) and potassium carbonate (5.71 g, 41.3 mmol) were added at 0° C., and the mixture was stirred at room temperature for 15 hours. A 1 M aqueous hydrochloric acid solution was added to the reaction solution, followed by extraction with ethyl acetate. The organic layer was washed with saturated aqueous sodium bicarbonate and saturated brine, and then dried over sodium sulfate and concentrated under reduced pressure. The resulting residue was purified by silica gel column chromatography (hexane-ethyl acetate) to give {2-[2-(2-hydroxy-ethoxy)-ethoxy]-ethyl}-methyl-carbamic acid tert-butyl ester (1.53 g, 42%).

$^1$H-NMR ($CDCl_3$) δ 3.74-3.72 (2H, m), 3.67-3.60 (8H, m), 3.42-3.39 (2H, br m), 2.91 (3H, s), 1.45 (9H, s).

(Reaction 366-9)

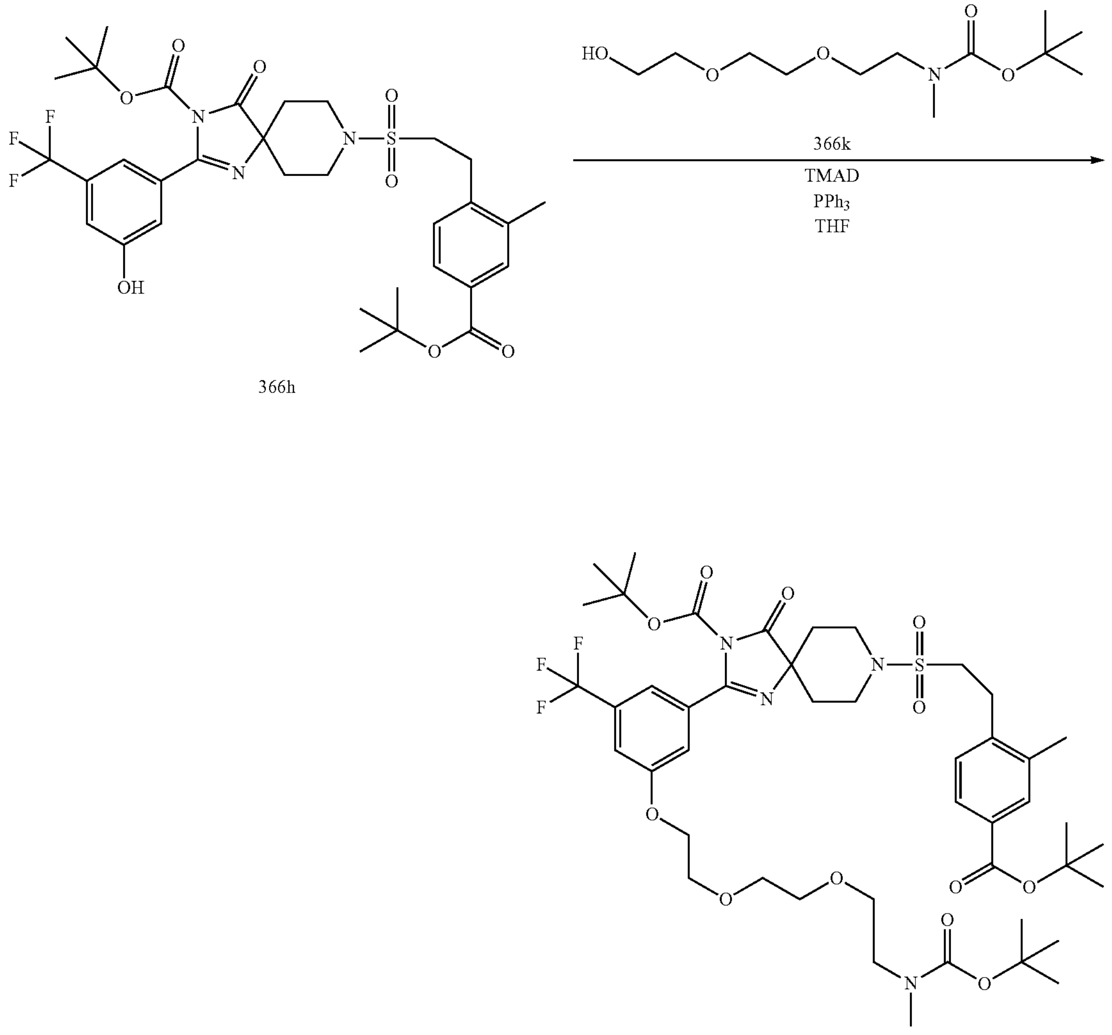

366h

366l

8-[2-(4-tert-Butoxycarbonyl-2-methyl-phenyl)-ethane-sulfonyl]-2-(3-hydroxy-5-trifluoromethyl-phenyl)-4-oxo-1,3,8-triaza-spiro[4.5]dec-1-ene-3-carboxylic acid tert-butyl ester (30.0 mg, 43.1 μmol), {2-[2-(2-hydroxy-ethoxy)-ethoxy]-ethyl}-methyl-carbamic acid tert-butyl ester (22.7 mg, 86.2 μmol) and triphenylphosphine (22.6 mg, 86.2 μmol) were dissolved in THF (0.22 mL). TMAD (14.8 mg, 86.2 μmol) was added and the mixture was stirred at 60° C. for 30 minutes in a nitrogen atmosphere. The reaction solution was concentrated under reduced pressure, and the resulting residue was then purified by silica gel column chromatography (hexane-ethyl acetate) to give 2-[3-(2-{2-[2-(tert-butoxycarbonyl-methyl-amino)-ethoxy]-ethoxy}-ethoxy)-5-trifluoromethyl-phenyl]-8-[2-(4-tert-butoxycarbonyl-2-methyl-phenyl)-ethanesulfonyl]-4-oxo-1,3,8-triaza-spiro[4.5]dec-1-ene-3-carboxylic acid tert-butyl ester (37.4 mg, 86%).

MS (ESI) m/z=941 (M+H)+;

HPLC retention time: 1.18 min (analysis condition LCMS-F-1).

(Reaction 366-10)

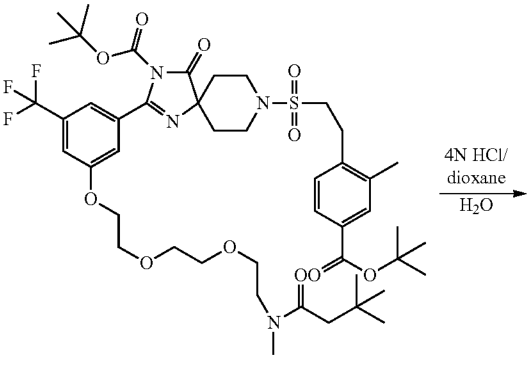

366l

-continued

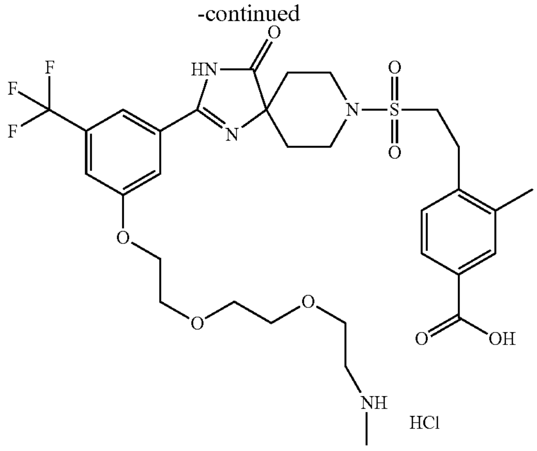

366m

2-[3-(2-{2-[2-(tert-Butoxycarbonyl-methyl-amino)-ethoxy]-ethoxy}-ethoxy)-5-trifluoromethyl-phenyl]-8-[2-(4-tert-butoxycarbonyl-2-methyl-phenyl)-ethanesulfonyl]-4-oxo-1,3,8-triaza-spiro[4.5]dec-1-ene-3-carboxylic acid tert-butyl ester (37.4 mg, 39.7 μmol) was dissolved in 4 N hydrochloric acid-dioxane (0.79 mL). Water (14.3 μL, 795 μmol) was added and the mixture was stirred at room temperature for three hours. The reaction solution was concentrated under reduced pressure to give 3-methyl-4-{2-[2-(3-{2-[2-(2-methylamino-ethoxy)-ethoxy]-ethoxy}-5-trifluoromethyl-phenyl)-4-oxo-1,3,8-triaza-spiro[4.5]dec-1-ene-8-sulfonyl]-ethyl}-benzoic acid hydrochloride (28.0 mg, 98%).

MS (ESI) m/z=685 (M+H)+;

HPLC retention time: 1.88 min (analysis condition LCMS-B-1).

(Reaction 366-11)

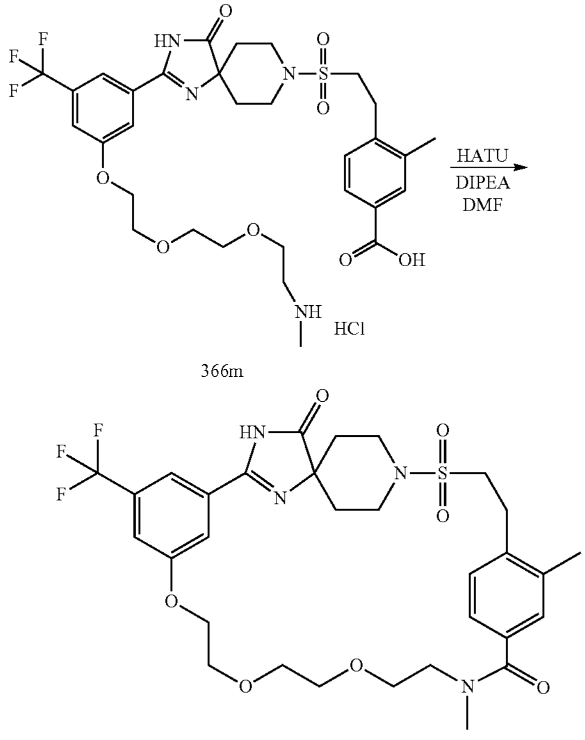

366m

Compound 1438

3-Methyl-4-{2-[2-(3-{2-[2-(2-methylamino-ethoxy)-ethoxy]-ethoxy}-5-trifluoromethyl-phenyl)-4-oxo-1,3,8-triaza-spiro[4.5]dec-1-ene-8-sulfonyl]-ethyl}-benzoic acid hydrochloride (26.0 mg, 36.1 μmol) was dissolved in DMF (7.21 mL). DIPEA (62.8 μL, 361 μmol) and HATU (68.6 mg, 180 μmol) were added and the mixture was stirred at 70° C. for two hours. A 3 M aqueous hydrochloric acid solution was added to the reaction solution, followed by extraction with ethyl acetate. The organic layer was washed with water, saturated aqueous sodium bicarbonate and saturated brine, and then dried over sodium sulfate and concentrated under reduced pressure. The resulting residue was purified by silica gel column chromatography (dichloromethane-ethyl acetate) to give a saturated macrocyclic compound (Compound 1438) (20.8 mg, 87%).

$^1$H-NMR ($CD_3OD$) δ 7.93 (1H, s), 7.88 (1H, s), 7.61 (1H, s), 7.32 (1H, s), 7.25-7.22 (2H, m), 7.14 (1H, d, J=7.4 Hz), 4.15 (2H, t, J=5.4 Hz), 3.78-3.35 (16H, m), 3.11-3.06 (2H, m), 2.97 (3H, s), 2.37 (3H, s), 1.98 (2H, td, J=13.0, 4.0 Hz), 1.56 (2H, d, J=12.9 Hz);

MS (ESI) m/z=667 (M+H)+;

HPLC retention time: 2.25 min (analysis condition LCMS-B-1).

Example 367

Compound 1439

(Reaction 367-1)

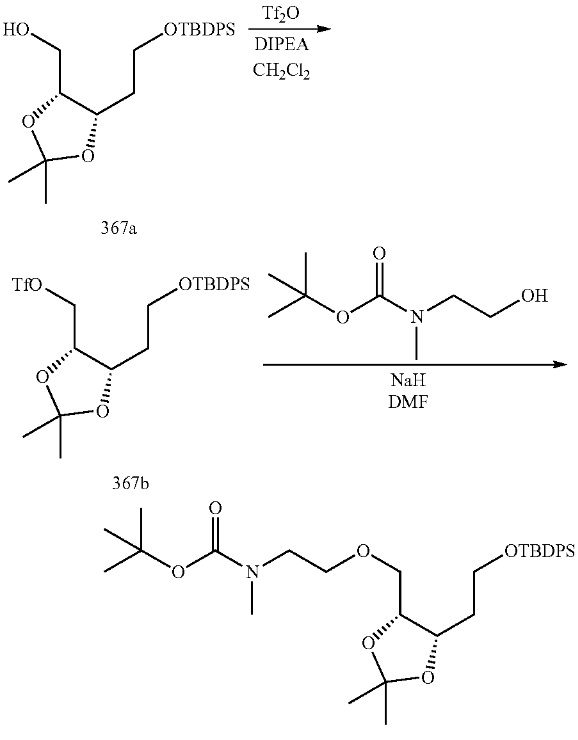

367a

367b

367c

{(4R,5S)-5-[2-(tert-Butyl-diphenyl-silanyloxy)-ethyl]-2,2-dimethyl-[1,3]dioxolan-4-yl}-methanol (159 mg, 0.38 mmol) was dissolved in dichloromethane (1.15 mL). Diisopropylethylamine (200 μL, 1.15 mmol) and $Tf_2O$ (77.4 μL, 0.46 mmol) were added at 0° C., and the mixture was stirred at room temperature for one hour in a nitrogen atmosphere. Saturated aqueous ammonium chloride was added to the reaction solution, followed by extraction with ethyl acetate. The organic layer was washed with saturated aqueous sodium bicarbonate and saturated brine, dried over sodium sulfate and filtered. The filtrate was concentrated under reduced pressure to give trifluoro-methanesulfonic acid (4R,5S)-5-[2-(tert-butyl-diphenyl-silanyloxy)-ethyl]-2,2-dimethyl-[1,3]dioxolan-4-ylmethyl ester as a crude product.

(2-Hydroxy-ethyl)-methyl-carbamic acid tert-butyl ester (73.9 mg, 0.42 mmol) was dissolved in THF (1.15 mL). Sodium hydride (50%, 22.1 mg, 0.46 mmol) was added at 0° C. and the mixture was stirred at 0° C. for 10 minutes in a nitrogen atmosphere. Trifluoro-methanesulfonic acid (4R,5S)-5-[2-(tert-butyl-diphenyl-silanyloxy)-ethyl]-2,2-dimethyl-[1,3]dioxolan-4-ylmethyl ester was added to the reaction solution, and the mixture was stirred at room temperature for two hours in a nitrogen atmosphere. Saturated aqueous ammonium chloride was added to the reaction solution, followed by extraction with ethyl acetate. The organic layer was washed with saturated aqueous sodium bicarbonate and saturated brine, dried over sodium sulfate and filtered, and the filtrate was concentrated under reduced pressure. The resulting residue was purified by silica gel column chromatography (hexane-ethyl acetate) to give (2-{(4R,5S)-5-[2-(tert-butyl-diphenyl-silanyloxy)-ethyl]-2,2-dimethyl-[1,3]dioxolan-4-ylmethoxy}-ethyl)-methyl-carbamic acid tert-butyl ester (82.2 mg, 38%).

MS (ESI) m/z=572 (M+H)+;

HPLC retention time: 1.27 min (analysis condition LCMS-F-1).

(Reaction 367-2)

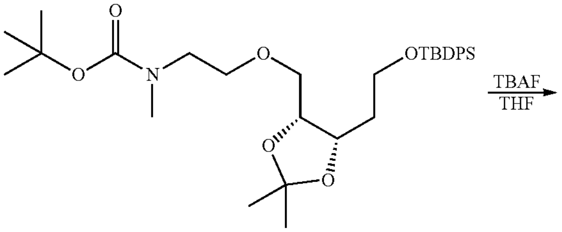

367c

-continued

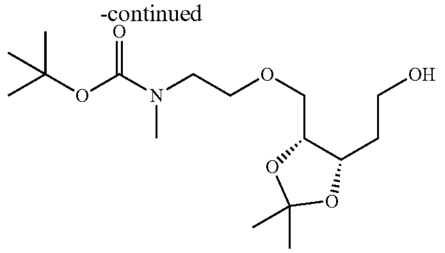

367d (2-{(4R,5S)-5-[2-(tert-Butyl-diphenyl-silanyloxy)-ethyl]-2,2-dimethyl-[1,3]dioxolan-4-ylmethoxy}-ethyl)-methyl-carbamic acid tert-butyl ester (82.2 mg, 0.14 mmol) was dissolved in THF (0.19 mL). TBAF (1.0 M solution in THF, 0.19 mL, 0.19 mmol) was added at 0° C. and the mixture was stirred at room temperature for one hour in a nitrogen atmosphere. Saturated aqueous ammonium chloride was added to the reaction solution, followed by extraction with ethyl acetate. The organic layer was washed with saturated aqueous sodium bicarbonate and saturated brine, and then dried over sodium sulfate and concentrated under reduced pressure. The resulting residue was purified by silica gel column chromatography (hexane-ethyl acetate) to give {2-[(4R,5S)-5-(2-hydroxy-ethyl)-2,2-dimethyl-[1,3]dioxolan-4-ylmethoxy]-ethyl}-methyl-carbamic acid tert-butyl ester (41.7 mg, 88%).

$^1$H-NMR ($CDCl_3$) δ 4.34-4.31 (1H, m), 4.25 (1H, q, J=6.1 Hz), 3.84-3.74 (2H, m), 3.54-3.47 (6H, m), 2.90 (3H, s), 2.46 (1H, dd, J=7.8, 3.3 Hz), 1.82-1.78 (2H, br m), 1.45-1.44 (12H, m), 1.35 (3H, s).

(Reaction 367-3)

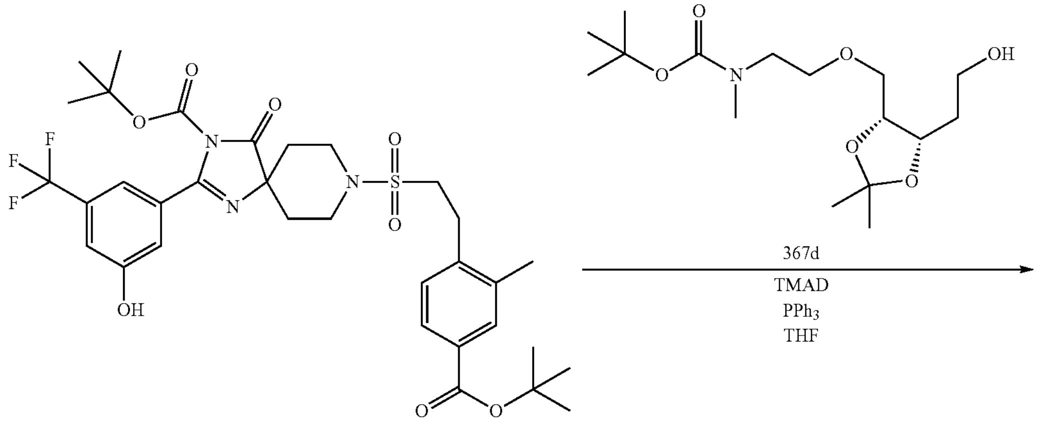

366h

-continued

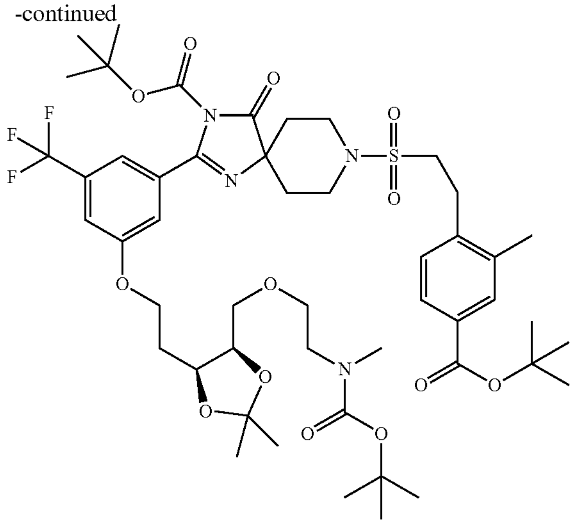

367e 2-(3-(2-((4S,5R)-5-((2-(tert-Butoxycarbonyl(methyl) amino)ethoxy)methyl)-2,2-dimethyl-1,3-dioxolan-4-yl) ethoxy)-5-(trifluoromethyl)phenyl)-8-(4-(tert-butoxycarbonyl)-2-methylphenethylsulfonyl)-4-oxo-1,3,8-triazaspiro [4.5]dec-1-ene-3-carboxylic acid tert-butyl ester was obtained by the same method as in Reaction 366-9 using 8-[2-(4-tert-butoxycarbonyl-2-methyl-phenyl)-ethanesulfonyl]-2-(3-hydroxy-5-trifluoromethyl-phenyl)-4-oxo-1,3,8-triaza-spiro[4.5]dec-1-ene-3-carboxylic acid tert-butyl ester and {2-[(4R,5S)-5-(2-hydroxy-ethyl)-2,2-dimethyl-[1,3]dioxolan-4-ylmethoxy]-ethyl}-methyl-carbamic acid tert-butyl ester as starting materials.

MS (ESI) m/z=1012 (M+H)+;

HPLC retention time: 1.21 min (analysis condition LCMS-F-1).

(Reaction 367-4)

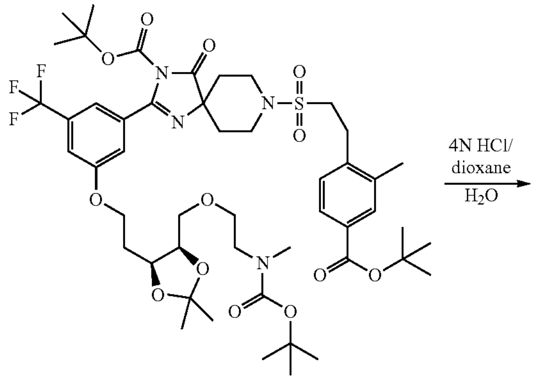

367e

-continued

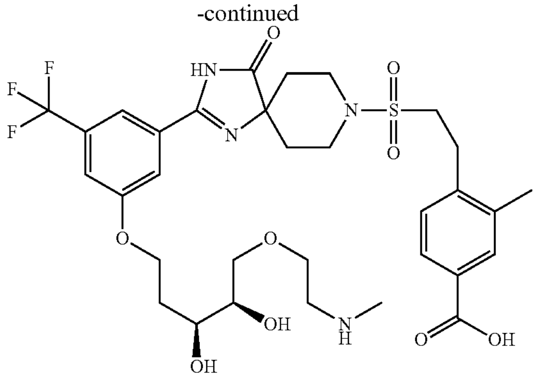

HCl

367f

4-[2-(2-{3-[(3S,4R)-3,4-Dihydroxy-5-(2-methylamino-ethoxy)-pentyloxy]-5-trifluoromethyl-phenyl}-4-oxo-1,3,8-triaza-spiro[4.5]dec-1-ene-8-sulfonyl)-ethyl]-3-methyl-benzoic acid hydrochloride was obtained by the same method as in Reaction 366-10 using 2-(3-(2-((4S,5R)-5-((2-(tert-butoxycarbonyl(methyl)amino)ethoxy)methyl)-2,2-dimethyl-1,3-dioxolan-4-yl)ethoxy)-5-(trifluoromethyl)phenyl)-8-(4-(tert-butoxycarbonyl)-2-methylphenethylsulfonyl)-4-oxo-1,3,8-triazaspiro[4.5]dec-1-ene-3-carboxylic acid tert-butyl ester as a starting material.

MS (ESI) m/z=729 (M+H)+;

HPLC retention time: 0.80 min (analysis condition LCMS-F-1).

(Reaction 367-5)

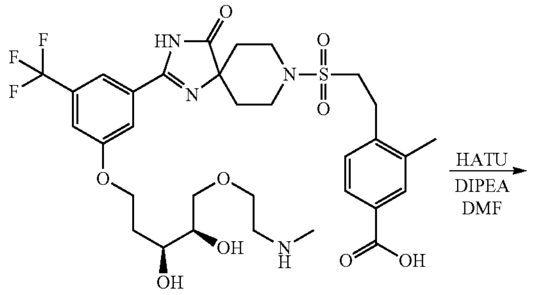

HCl

367f

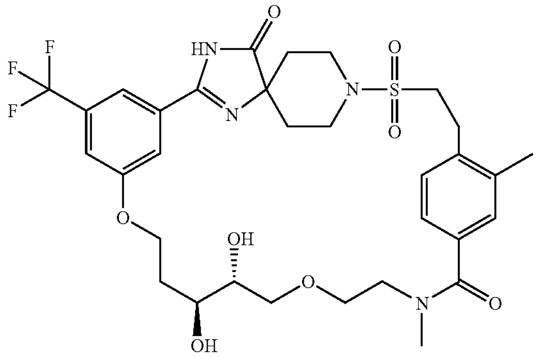

Compound 1439

A saturated macrocyclic compound (Compound 1439) was obtained by the same method as in Reaction 366-11 using 4-[2-(2-{3-[(3S,4R)-3,4-dihydroxy-5-(2-methylamino-ethoxy)-pentyloxy]-5-trifluoromethyl-phenyl}-4-oxo-1,3,8-triaza-spiro[4.5]dec-1-ene-8-sulfonyl)-ethyl]-3-methyl-benzoic acid hydrochloride as a starting material.

MS (ESI) m/z=697 (M+H)+;

HPLC retention time: 0.92 min (analysis condition LCMS-F-1).

Example 368

Compound 1440

(Reaction 368-1)

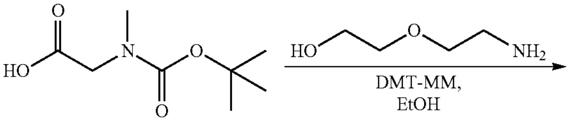

368a

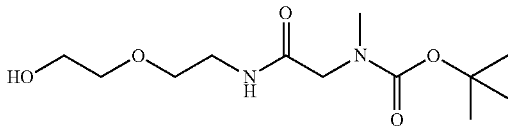

368b

BOC-sarcosine (900 mg, 4.76 mmol) was dissolved in ethanol (10 ml). 2-(2-Aminoethoxy)ethanol (0.477 ml, 4.76 mmol) and 4-(4,6-dimethoxy-1,3,5-triazin-2-yl)-4-methylmorpholinium chloride n-hydrate (DMT-MM) (1.79 g, 5.71 mmol) were added and the mixture was stirred at room temperature overnight. The reaction solution was concentrated under reduced pressure, and water was added to the resulting residue, followed by extraction with ethyl acetate. The organic layer was washed with water and saturated brine, dried over anhydrous sodium sulfate and concentrated under reduced pressure. The resulting residue was subjected to silica gel column chromatography (dichloromethane-methanol) to give {[2-(2-hydroxy-ethoxy)-ethylcarbamoyl]-methyl}-methyl-carbamic acid tert-butyl ester. This was used in the next reaction without complete purification.

(Reaction 368-2)

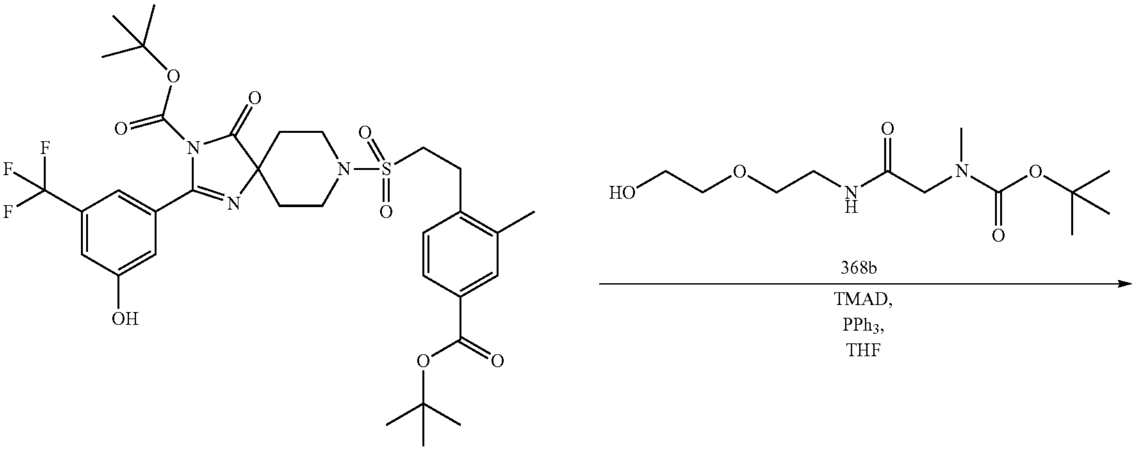

366h

-continued

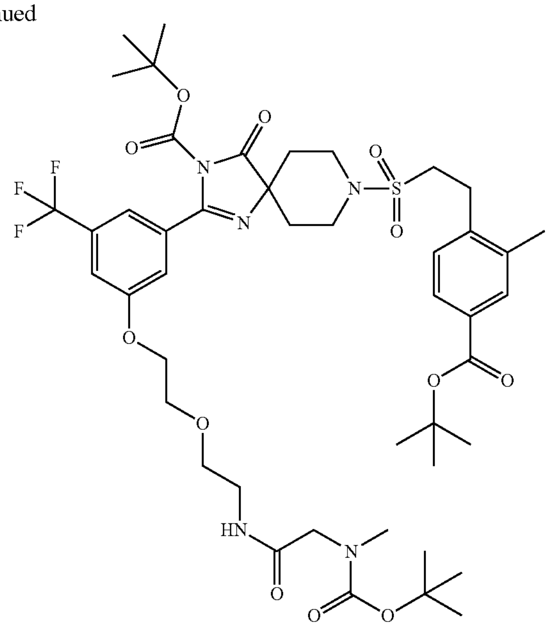

368c

8-[2-(4-tert-Butoxycarbonyl-2-methyl-phenyl)-ethanesulfonyl]-2-[3-(2-{2-[2-(tert-butoxycarbonyl-methyl-amino)-acetylamino]-ethoxy}-ethoxy)-5-trifluoromethyl-phenyl]-4-oxo-1,3,8-triaza-spiro[4.5]dec-1-ene-3-carboxylic acid tert-butyl ester was obtained by the same method as in Reaction 366-9 using 8-[2-(4-tert-butoxycarbonyl-2-methyl-phenyl)-ethanesulfonyl]-2-(3-hydroxy-5-trifluoromethyl-phenyl)-4-oxo-1,3,8-triaza-spiro[4.5]dec-1-ene-3-carboxylic acid tert-butyl ester and {[2-(2-hydroxy-ethoxy)-ethylcarbamoyl]-methyl}-methyl-carbamic acid tert-butyl ester as starting materials. This was used in the next reaction without complete purification.

(Reaction 368-3)

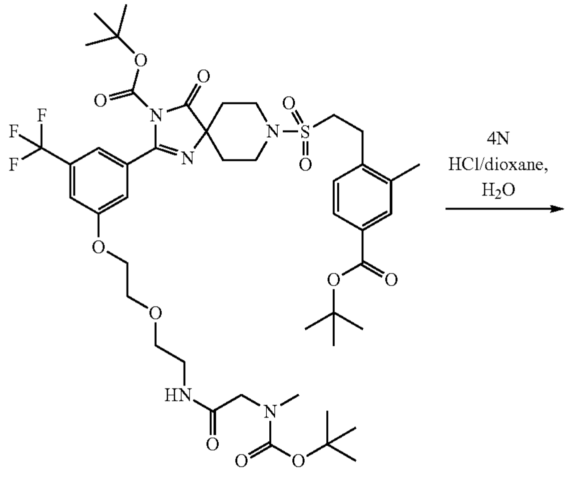

368c

-continued

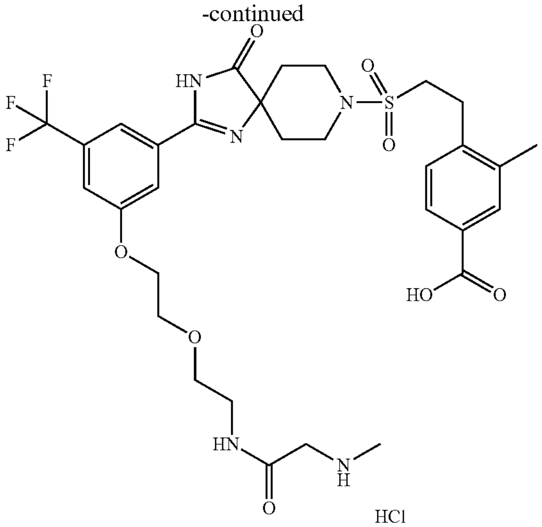

HCl

368d

3-Methyl-4-{2-[2-(3-{2-[2-(2-methylamino-acetylamino)-ethoxy]-ethoxy}-5-trifluoromethyl-phenyl)-4-oxo-1,3,8-triaza-spiro[4.5]dec-1-ene-8-sulfonyl]-ethyl}-benzoic acid hydrochloride was obtained by the same method as in Reaction 366-10 using 8-[2-(4-tert-butoxycarbonyl-2-methyl-phenyl)-ethanesulfonyl]-2-[3-(2-{2-[2-(tert-butoxycarbonyl-methyl-amino)-acetylamino]-ethoxy}-ethoxy)-5-trifluoromethyl-phenyl]-4-oxo-1,3,8-triaza-spiro[4.5]dec-1-ene-3-carboxylic acid tert-butyl ester (13 mg, 0.0136 mmol) as a starting material. This was used in the next reaction without complete purification.

(Reaction 368-4)

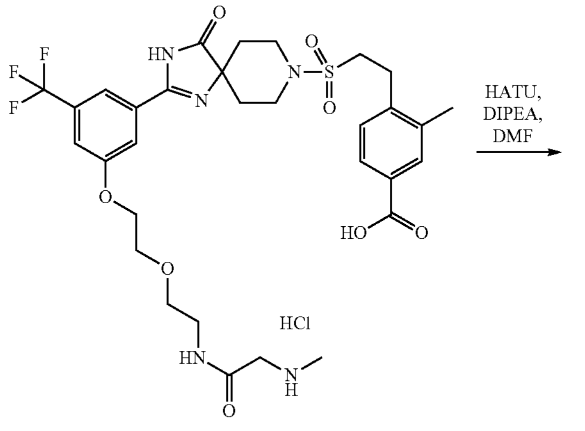

368d

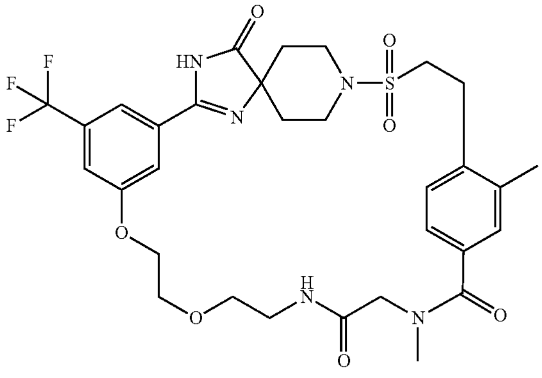

Compound 1440

A saturated macrocyclic compound (Compound 1440) was obtained by the same method as in Reaction 366-11 using 3-methyl-4-{2-[2-(3-{2-[2-(2-methylamino-acetylamino)-ethoxy]-ethoxy}-5-trifluoromethyl-phenyl)-4-oxo-1,3,8-triaza-spiro[4.5]dec-1-ene-8-sulfonyl]-ethyl}-benzoic acid hydrochloride as a starting material.

MS (ESI) m/z=680 (M+H)+;

HPLC retention time: 0.89 min (analysis condition LCMS-F-1).

Example 369

Compound 1441

(Reaction 369-1)

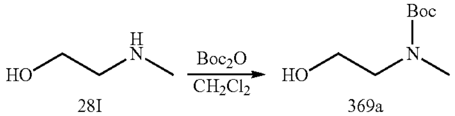

281 369a

A mixture of 2-(methylamino)ethanol (5.2 g, 69.2 mmol) and tert-butyl dicarbonate (15.8 g, 72.7 mmol) in methylene chloride (200 mL) was stirred at room temperature for 16 hours. The reaction mixture was diluted with methylene chloride, and the organic layer was then washed with water, dried over $MgSO_4$ and concentrated under reduced pressure. The resulting residue was purified by silica gel column chromatography to give (2-hydroxyethyl)methylcarbamic acid 1,1-dimethylethyl ester (12.1 g, yield 100%).

$^1$H-NMR (400 MHz, $CDCl_3$) δ 1.47 (9H, m), 2.91 (3H, s), 3.39-3.41 (2H, m), 3.72-3.76 (2H, m).

(Reaction 369-2)

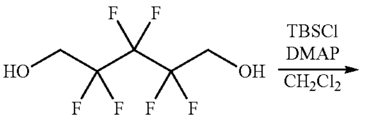

369b

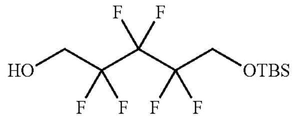

369c

4-Dimethylaminopyridine (634 mg, 5.2 mmol) was added to a solution of 2,2,3,3,4,4-hexafluoro-pentane-1,5-diol (1 g, 4.7 mmol) and tert-butyldimethylsilyl chloride (708 mg, 4.7 mmol) in methylene chloride (10 ml), and the mixture was stirred at room temperature for 16 hours. The reaction mixture was concentrated under reduced pressure, and the residue was then purified by silica gel column chromatography to give 5-(tert-butyl-dimethyl-silanyloxy)-2,2,3,3,4,4-hexafluoro-pentan-1-ol (770 mg, 50%).

$^1$H-NMR (400 MHz, $CDCl_3$) δ 0.10 (6H, s), 0.90 (9H, m), 4.07-4.11 (4H, m).

(Reaction 369-3)

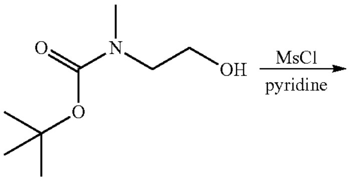

369a

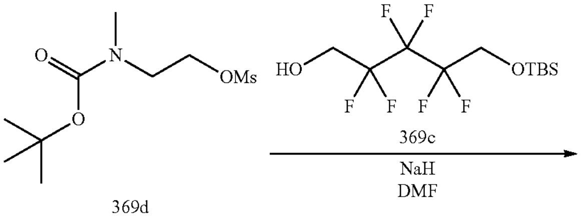

369d

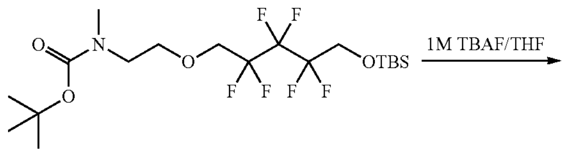

369e

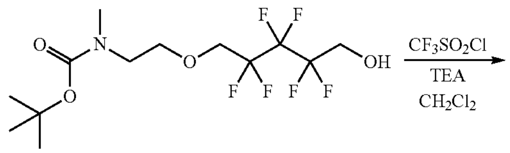

369f

-continued

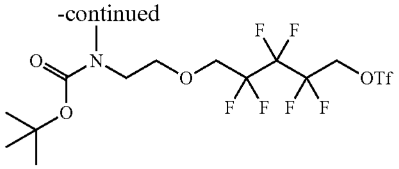

369g (2-Hydroxyethyl)methylcarbamic acid 1,1-dimethylethyl ester (350 mg, 2.0 mmol) was dissolved in pyridine (2 ml). Mesyl chloride (0.229 ml, 2.1 mmol) was added at room temperature, and the mixture was stirred at room temperature for 30 minutes. The reaction mixture was diluted with methylene chloride, and the organic layer was washed with a saturated aqueous sodium bicarbonate solution, dried over $MgSO_4$ and concentrated under reduced pressure to give methanesulfonic acid 2-(tert-butoxycarbonyl-methyl-amino)-ethyl ester. This was used in the next reaction without complete purification.

5-(tert-Butyl-dimethyl-silanyloxy)-2,2,3,3,4,4-hexafluoro-pentan-1-ol (400 mg, 1.23 mmol) was dissolved in dimethylformamide (2 ml). Sodium hydride (51.5 mg, 1.29 mmol) was added at room temperature, and the mixture was stirred at room temperature for 30 minutes. A solution of methanesulfonic acid 2-(tert-butoxycarbonyl-methyl-amino)-ethyl ester obtained above in dimethylformamide (0.5 ml) was then added at room temperature, and the mixture was stirred at room temperature overnight. The reaction mixture was extracted with ethyl acetate, and the organic layer was then washed with water, dried over $MgSO_4$ and concentrated under reduced pressure. The resulting residue was purified by silica gel column chromatography to give {2-[5-(tert-butyl-dimethyl-silanyloxy)-2,2,3,3,4,4-hexafluoro-pentyloxy]-ethyl}-methyl-carbamic acid tert-butyl ester. This was used in the next reaction without complete purification.

{2-[5-(tert-Butyl-dimethyl-silanyloxy)-2,2,3,3,4,4-hexafluoro-pentyloxy]-ethyl}-methyl-carbamic acid tert-butyl ester obtained above was dissolved in a 1 M solution of tetrabutylammonium fluoride in tetrafuran (0.2 mL), and the mixture was reacted at room temperature for one hour. The reaction mixture was concentrated under reduced pressure, and the residue was then purified by silica gel column chromatography to give [2-(2,2,3,3,4,4-hexafluoro-5-hydroxy-pentyloxy)-ethyl]-methyl-carbamic acid tert-butyl ester (70 mg). This was used in the next reaction without complete purification.

[2-(2,2,3,3,4,4-Hexafluoro-5-hydroxy-pentyloxy)-ethyl]-methyl-carbamic acid tert-butyl ester obtained above was dissolved in methylene chloride (0.5 ml). Triethylamine (0.0528 ml, 0.38 mmol) and trifluoromethanesulfonyl chloride (0.0212 ml, 0.20 mmol) were added at room temperature, and the mixture was stirred at room temperature for 64 hours. The reaction mixture was extracted with ethyl acetate, and the organic layer was washed with saturated brine, dried over $MgSO_4$ and concentrated under reduced pressure. The resulting residue was purified by silica gel column chromatography to give Trifluoro-methanesulfonic acid 5-[2-(tert-butoxycarbonyl-methyl-amino)-ethoxy]-2,2,3,3,4,4-hexafluoro-pentyl ester (66 mg).

$^1$H-NMR (400 MHz, $CDCl_3$) δ 1.44 (9H, s), 2.89 (3H, s), 3.35-3.42 (m, 2H), 3.65-3.72 (m, 2H), 3.90-3.94 (m, 2H), 4.73-4.83 (m, 2H).

(Reaction 369-4)

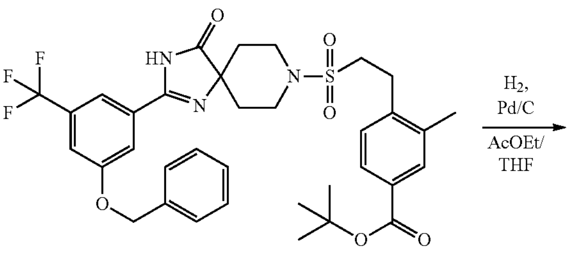

366e

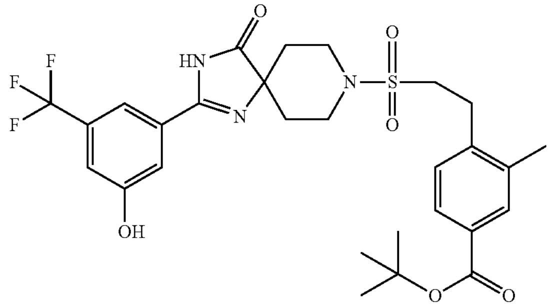

369h

4-{2-[2-(3-Benzyloxy-5-trifluoromethyl-phenyl)-4-oxo-1,3,8-triaza-spiro[4.5]dec-1-ene-8-sulfonyl]-ethyl}-3-methyl-benzoic acid tert-butyl ester (952.0 mg, 1.39 mmol) was dissolved in ethyl acetate (15.0 ml)-THF (5.0 ml). Pd—C (190.4 mg) was added and the mixture was stirred at room temperature for one hour in a hydrogen atmosphere. After completion of the reaction, the precipitated solid was dissolved by adding dichloromethane and methanol, and the remaining black solid was then filtered off through celite. The filtrate was concentrated under reduced pressure to give 4-{2-[2-(3-hydroxy-5-trifluoromethyl-phenyl)-4-oxo-1,3,8-triaza-spiro[4.5]dec-1-ene-8-sulfonyl]-ethyl}-3-methyl-benzoic acid tert-butyl ester as a white solid (776.2 mg, 93.8%).

$^1$H-NMR (400 MHz, DMSO-d6) δ 11.7 (1H, br), 10.6 (1H, br), 7.66-7.80 (4H, m), 7.39 (1H, d, J=8.0 Hz), 7.25 (1H, s), 3.59-3.70 (2H, m), 3.27-3.43 (4H, m), 3.04-3.08 (2H, m), 2.39 (3H, s), 1.79-1.88 (2H, m), 1.59 (2H, m), 1.55 (9H, s);

MS (ESI) m/z=596 (M+H)+;

HPLC retention time: 1.12 min (analysis condition LCMS-F-1).

(Reaction 369-5)

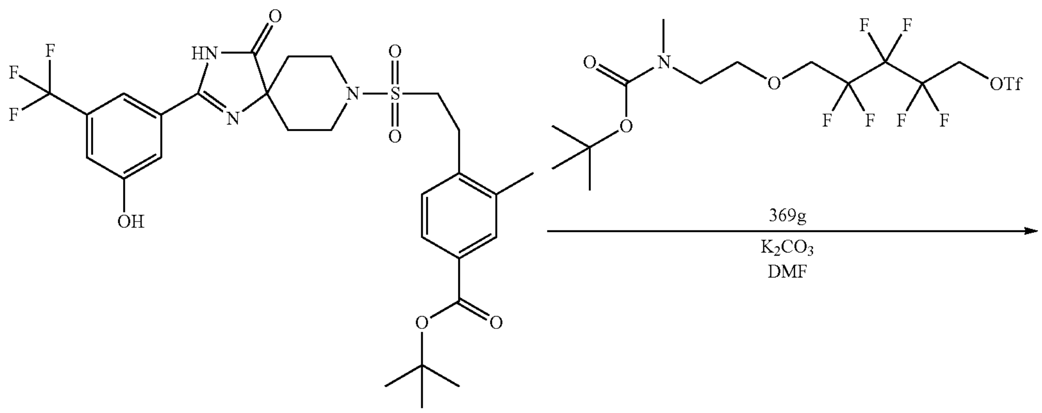

369h

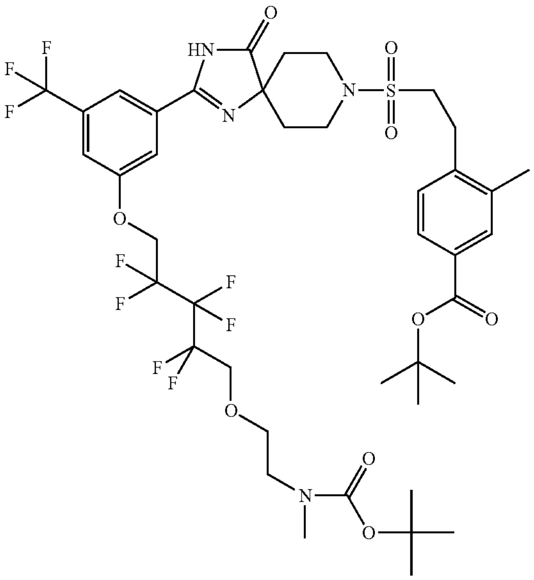

369i

4-{2-[2-(3-Hydroxy-5-trifluoromethyl-phenyl)-4-oxo-1,3,8-triaza-spiro[4.5]dec-1-ene-8-sulfonyl]-ethyl}-3-methyl-benzoic acid tert-butyl ester (77.0 mg, 0.13 mmol) and trifluoro-methanesulfonic acid 5-[2-(tert-butoxycarbonyl-methyl-amino)-ethoxy]-2,2,3,3,4,4-hexafluoro-pentyl ester (58.0 mg, 0.13 mmol) were dissolved in DMF (1 ml). Potassium carbonate (53.8 mg, 0.39 mmol) was added and the mixture was stirred at 60° C. overnight. The reaction mixture was extracted with ethyl acetate, and the organic layer was then washed with saturated brine, dried over $MgSO_4$ and concentrated under reduced pressure. The resulting residue was purified by silica gel column chromatography to give 4-{2-[2-(3-{5-[2-(tert-butoxycarbonyl-methyl-amino)-ethoxy]-2,2,3,3,4,4-hexafluoro-pentyloxy}-5-trifluoromethyl-phenyl)-4-oxo-1,3,8-triaza-spiro[4.5]dec-1-ene-8-sulfonyl]-ethyl}-3-methyl-benzoic acid tert-butyl ester (57 mg, 46%).

MS (ESI) m/z=947 (M+H)+.

(Reaction 369-6)

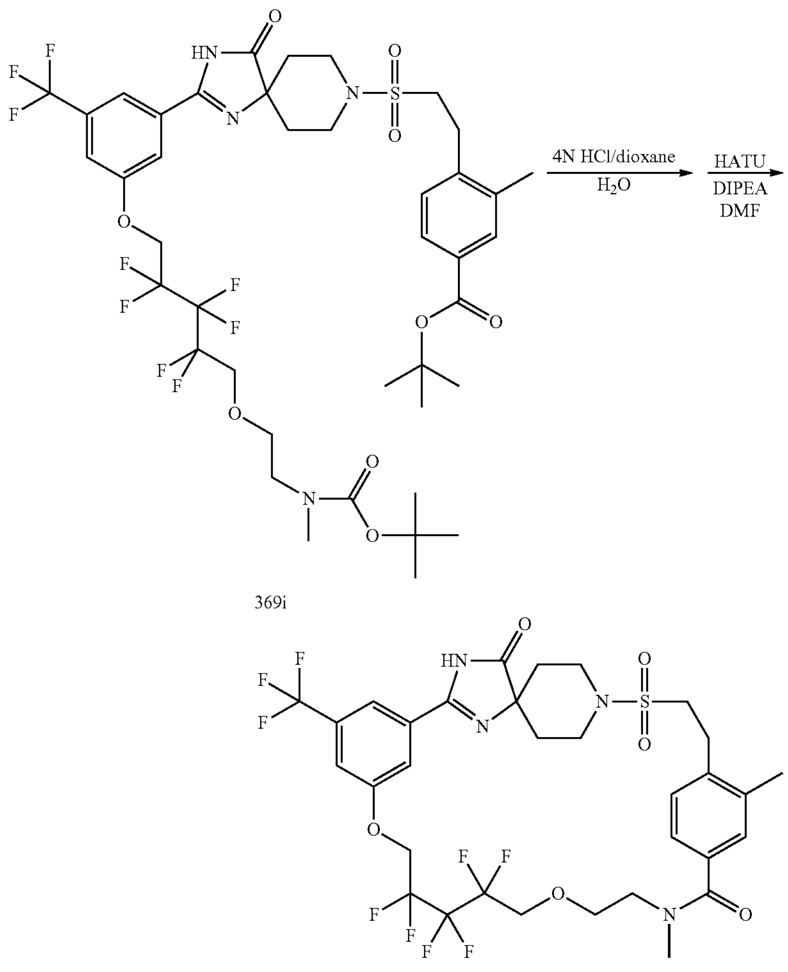

369i

Compound 1441

4-{2-[2-(3-{5-[2-(tert-Butoxycarbonyl-methyl-amino)-ethoxy]-2,2,3,3,4,4-hexafluoro-pentyloxy}-5-trifluoromethyl-phenyl)-4-oxo-1,3,8-triaza-spiro[4.5]dec-1-ene-8-sulfonyl]-ethyl}-3-methyl-benzoic acid tert-butyl ester (56 mg, 0.059 mmol) was dissolved in water (0.1 ml) and 4 N hydrochloric acid-dioxane (1 ml), and the mixture was stirred at room temperature for 30 minutes. The reaction mixture was concentrated under reduced pressure, and the residue was then dissolved in DMF (5 ml). Triethylamine (0.053 ml, 0.384 mmol) and O-(benzotriazol-1-yl)-N,N,N',N'-tetramethyluronium hexafluorophosphate (144 mg, 0.384 mmol) were added at room temperature, and the mixture was heated with stirring at 70° C. for two hours. The reaction mixture was extracted with ethyl acetate, and the organic layer was washed with water, dried over $MgSO_4$ and concentrated under reduced pressure. The resulting residue was purified by silica gel column chromatography to give a saturated macrocyclic compound (Compound 1441) (12 mg, 21%).

MS (ESI) m/z=773 (M+H)+;

HPLC retention time: 6.52 min (analysis condition LCMS-A-2).

Example 370

Compound 1442

(Reaction 370-1)

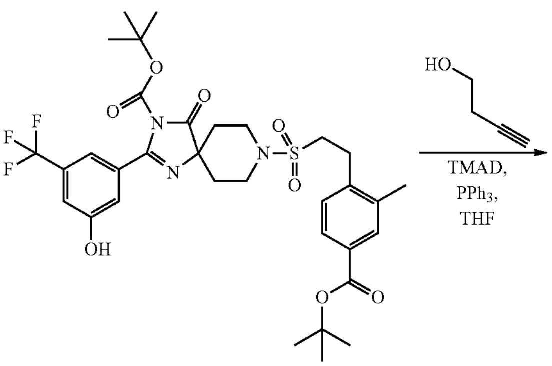

366h

-continued

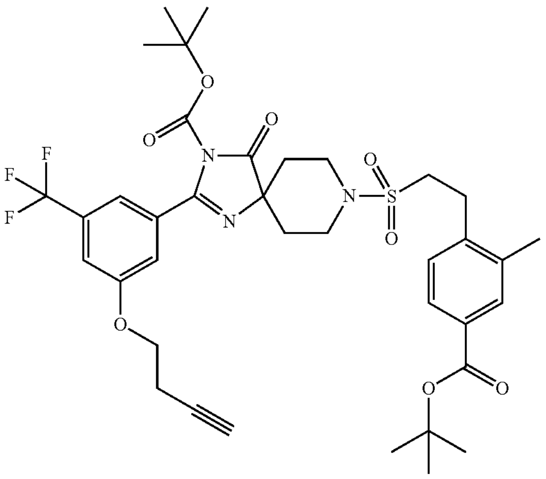

370a (Reaction 370-2)

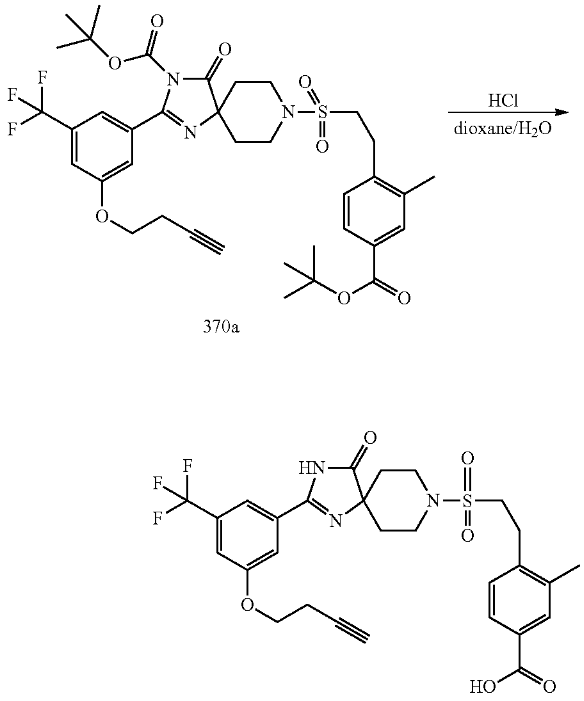

370a

370b

8-[2-(4-tert-Butoxycarbonyl-2-methyl-phenyl)-ethanesulfonyl]-2-(3-but-3-ynyloxy-5-trifluoromethyl-phenyl)-4-oxo-1,3,8-triaza-spiro[4.5]dec-1-ene-3-carboxylic acid tert-butyl ester (37.9 mg, 71%) was obtained by the same method as in Reaction 366-9 using 8-[2-(4-tert-butoxycarbonyl-2-methyl-phenyl)-ethanesulfonyl]-2-(3-hydroxy-5-trifluoromethyl-phenyl)-4-oxo-1,3,8-triaza-spiro[4.5]dec-1-ene-3-carboxylic acid tert-butyl ester and 3-butyn-1-ol as starting materials.

MS (ESI) m/z=592 (M-Boc-tBu)+;

HPLC retention time: 3.79 min (analysis condition LCMS-A-1).

4 M hydrochloric acid-dioxane (1.80 ml) and water (0.0173 ml, 0.960 mmol) were added to 8-[2-(4-tert-butoxycarbonyl-2-methyl-phenyl)-ethanesulfonyl]-2-(3-but-3-ynyloxy-5-trifluoromethyl-phenyl)-4-oxo-1,3,8-triaza-spiro[4.5]dec-1-ene-3-carboxylic acid tert-butyl ester (35.9 mg, 0.048 mmol), and the mixture was stirred at room temperature for five hours. The reaction solution was concentrated under reduced pressure to give 4-{2-[2-(3-but-3-ynyloxy-5-trifluoromethyl-phenyl)-4-oxo-1,3,8-triaza-spiro[4.5]dec-1-ene-8-sulfonyl]-ethyl}-3-methyl-benzoic acid as a white solid.

MS (ESI) m/z=592 (M+H)+;

HPLC retention time: 0.91 min (analysis condition LCMS-F-1).

(Reaction 370-3)

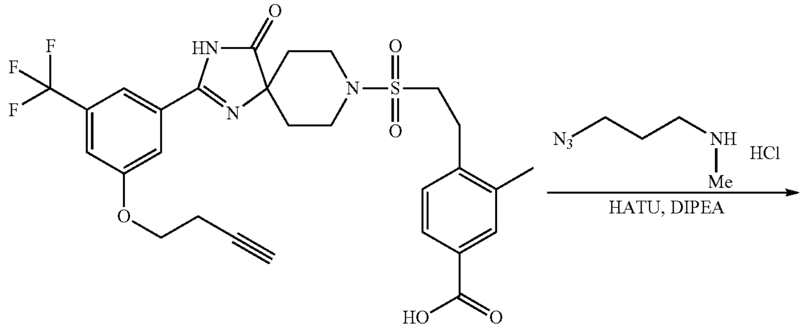

370b

-continued

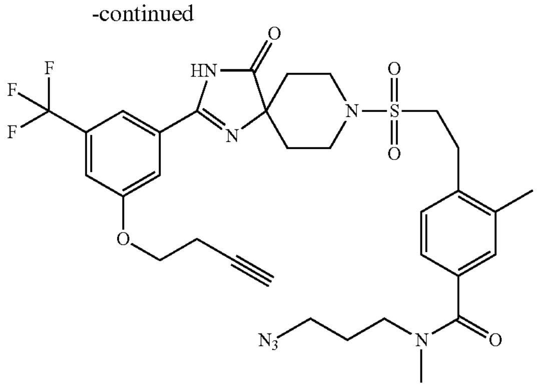

370c

4-{2-[2-(3-But-3-ynyloxy-5-trifluoromethyl-phenyl)-4-oxo-1,3,8-triaza-spiro[4.5]dec-1-ene-8-sulfonyl]-ethyl}-3-methyl-benzoic acid, (3-azido-propyl)-methyl-amine hydrochloride (15.3 mg, 0.101 mmol) and DIPEA (0.044 ml, 0.255 mmol) were dissolved in DMF (0.400 ml). HATU (0.038 mg, 0.101 mmol) was added and the mixture was stirred at room temperature for one hour. The reaction solution was diluted with ethyl acetate, and the organic layer was then washed with a 1 M aqueous hydrochloric acid solution, an aqueous sodium bicarbonate solution and saline. The organic layer was dried over anhydrous magnesium sulfate and then concentrated under reduced pressure. The resulting residue was purified by column chromatography (dichloromethane-ethyl acetate) to give N-(3-azido-propyl)-4-{2-[2-(3-but-3-ynyloxy-5-trifluoromethyl-phenyl)-4-oxo-1,3,8-triaza-spiro[4.5]dec-1-ene-8-sulfonyl]-ethyl}-3,N-dimethyl-benzamide as a colorless oily substance.

MS (ESI) m/z=688 (M+H)+;

HPLC retention time: 1.05 min (analysis condition LCMS-F-1).

(Reaction 370-4)

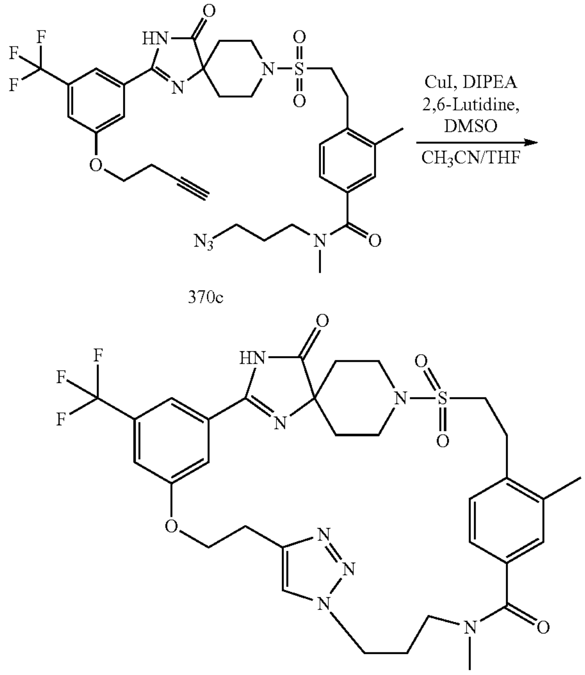

370c

Compound 1442

N-(3-Azido-propyl)-4-{2-[2-(3-but-3-ynyloxy-5-trifluoromethyl-phenyl)-4-oxo-1,3,8-triaza-spiro[4.5]dec-1-ene-8-sulfonyl]-ethyl}-3,N-dimethyl-benzamide was dissolved in acetonitrile (17.0 ml)-THF (4.0 ml). DMSO (0.022 ml), DIPEA (0.012 ml, 0.069 mmol), 2,6-lutidine (0.0053 ml, 0.046 mmol) and copper(I) iodide (13.2 mg, 0.069 mmol) were added, and the mixture was stirred at room temperature overnight. Thereafter, copper(I) iodide (13.2 mg, 0.069 mmol) was further added and the mixture was stirred at room temperature for one hour. The reaction solution was concentrated under reduced pressure. Ethyl acetate was added and the precipitated solid was filtered off. The filtrate was washed with a 1 M aqueous hydrochloric acid solution, an aqueous sodium bicarbonate solution and saline. The organic layer was dried over anhydrous magnesium sulfate and then concentrated under reduced pressure. The resulting residue was purified by column chromatography (dichloromethane-ethyl acetate and dichloromethane-methanol) to give a macrocyclic compound (Compound 1442) as a white solid (3.2 mg, 20.2% in three steps).

MS (ESI) m/z=688 (M+H)+;

HPLC retention time: 0.94 min (analysis condition LCMS-F-1).

Example 371

Compound 1443

(Reaction 371-1)

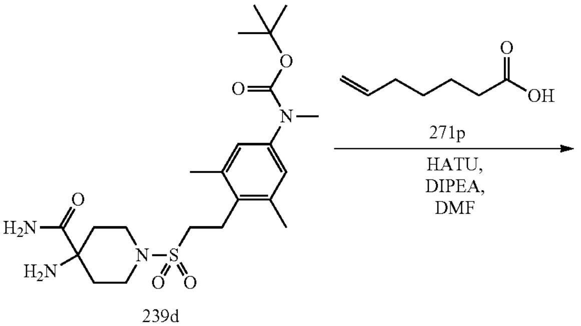

239d

-continued

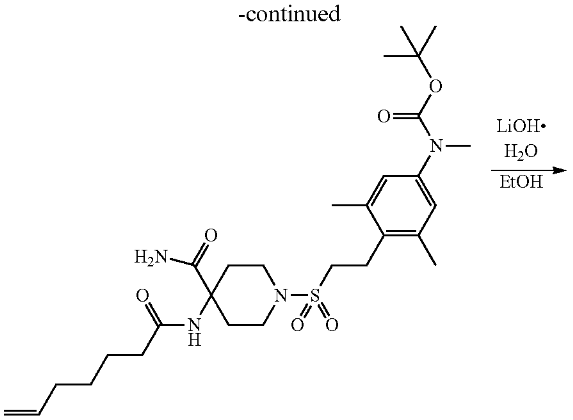

371a

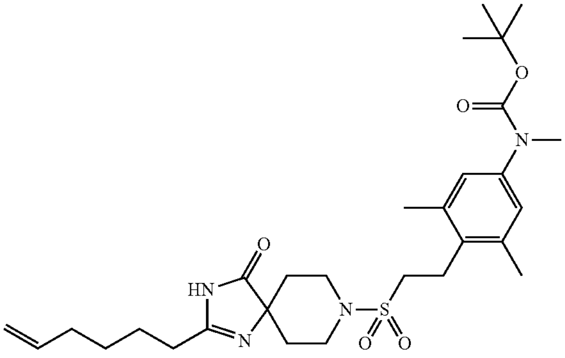

371b

{4-[2-(4-Carbamoyl-4-hept-6-enoylamino-piperidine-1-sulfonyl)-ethyl]-3,5-dimethyl-phenyl}-methyl-carbamic acid tert-butyl ester was obtained as a crude compound by the same method as in Reaction 359-9 using hept-6-enoic acid and {4-[2-(4-amino-4-carbamoyl-piperidine-1-sulfonyl)-ethyl]-3,5-dimethyl-phenyl}-methyl-carbamic acid tert-butyl ester as starting materials.

MS (ESI) m/z=579 (M+H)+;

HPLC retention time: 2.49 min (analysis condition LCMS-B-1).

{4-[2-(4-Carbamoyl-4-hept-6-enoylamino-piperidine-1-sulfonyl)-ethyl]-3,5-dimethyl-phenyl}-methyl-carbamic acid tert-butyl ester obtained above (Crude compound, 1.00 g) was dissolved in ethanol. Lithium hydroxide monohydrate (188 mg, 4.48 mmol) was added and the mixture was stirred at 40° C. for 19 hours. A saturated aqueous ammonium chloride solution and water were added to the reaction solution, followed by extraction with ethyl acetate. The organic layer was washed with water and saturated brine, and then dried over anhydrous sodium sulfate and concentrated under reduced pressure. The resulting residue was purified by silica gel column chromatography to give {4-[2-(2-hex-5-enyl-4-oxo-1,3,8-triaza-spiro[4.5]dec-1-ene-8-sulfonyl)-ethyl]-3,5-dimethyl-phenyl}-methyl-carbamic acid tert-butyl ester (821 mg, 1.47 mmol).

$^1$H-NMR (400 MHz, $CDCl_3$) δ 7.85 (1H, br s), 6.92 (2H, s), 5.83-5.73 (1H, m), 5.04-4.96 (2H, m), 3.80-3.74 (2H, m), 3.45-3.38 (2H, m), 3.22 (3H, s), 3.16-3.12 (2H, m), 3.01-2.97 (2H, m), 2.44 (2H, t, J=7.6 Hz), 2.34 (6H, s), 2.10 (2H, q, J=7.2 Hz), 2.02-1.95 (2H, m), 1.71-1.59 (4H, m), 1.46 (9H, s);

MS (ESI) m/z=561 (M+H)+;

HPLC retention time: 2.61 min (analysis condition LCMS-A-1).

(Reaction 371-2)

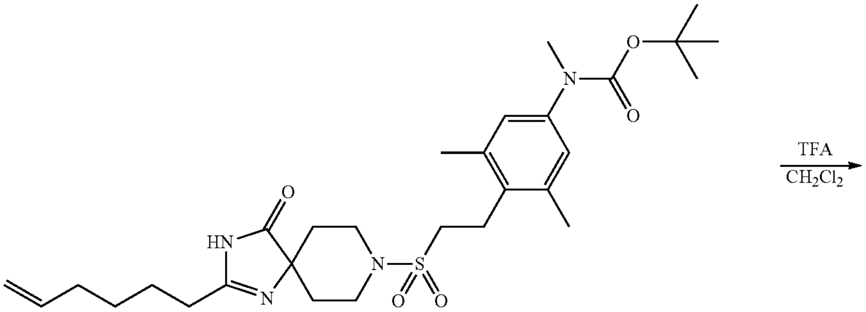

371b

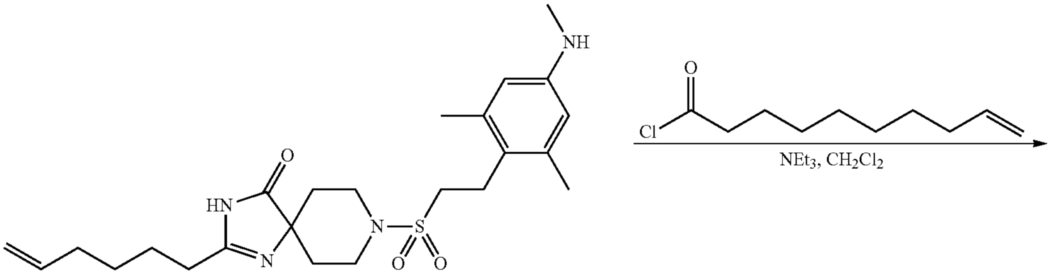

371c

-continued

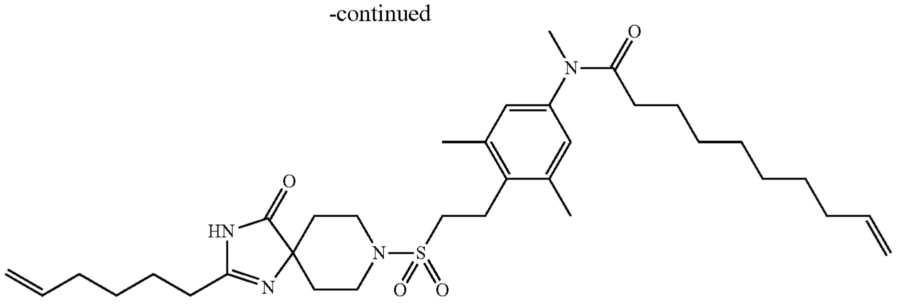

Compound 1443

{4-[2-(2-Hex-5-enyl-4-oxo-1,3,8-triaza-spiro[4.5]dec-1-ene-8-sulfonyl)-ethyl]-3,5-dimethyl-phenyl}-methyl-carbamic acid tert-butyl ester (820 mg, 1.46 mmol) was dissolved in methylene chloride (16 ml). Trifluoroacetic acid (10 ml) was added and the mixture was stirred at room temperature for two hours. The reaction solution was concentrated, and a saturated aqueous sodium bicarbonate solution was added to the residue. This mixture was extracted with methylene chloride. The organic layer was dried over anhydrous sodium sulfate and then concentrated under reduced pressure to give 8-[2-(2,6-dimethyl-4-methylamino-phenyl)-ethanesulfonyl]-2-hex-5-enyl-1,3,8-triaza-spiro[4.5]dec-1-en-4-one (686 mg) as a crude compound.

The resulting crude product 8-[2-(2,6-dimethyl-4-methylamino-phenyl)-ethanesulfonyl]-2-hex-5-enyl-1,3,8-triaza-spiro[4.5]dec-1-en-4-one (160 mg, 0.35 mmol) was dissolved in methylene chloride. 9-Decenoyl chloride (0.35 mmol) (prepared by allowing oxalyl chloride and a catalytic amount of DMF to act on 9-decenoic acid in methylene chloride) and triethylamine (0.195 ml, 1.4 mmol) were added, and the mixture was stirred at room temperature for 17 hours. A saturated aqueous ammonium chloride solution and water were added to the reaction solution, and the resulting mixture was extracted with ethyl acetate. The organic layer was washed with water and saturated brine, dried over anhydrous sodium sulfate and then concentrated under reduced pressure. The resulting residue was purified by silica gel column chromatography to give dec-9-enoic acid {4-[2-(2-hex-5-enyl-4-oxo-1,3,8-triaza-spiro[4.5]dec-1-ene-8-sulfonyl)-ethyl]-3,5-dimethyl-phenyl}-methyl-amide (Compound 1443) (100 mg, 48% in two steps).

MS (ESI) m/z=613 (M+H)+;

HPLC retention time: 5.80 min (analysis condition LCMS-C-1).

Example 372

Compound 1444

(Reaction 372-1)

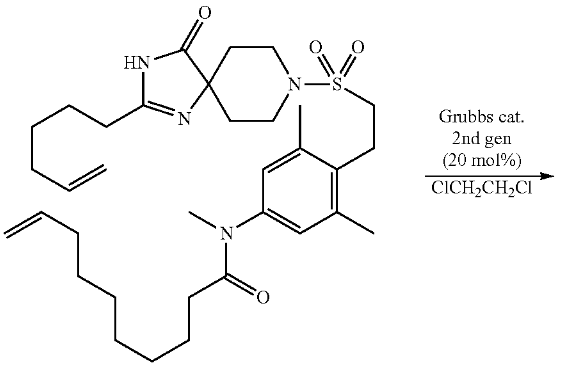

Compound 1443

-continued

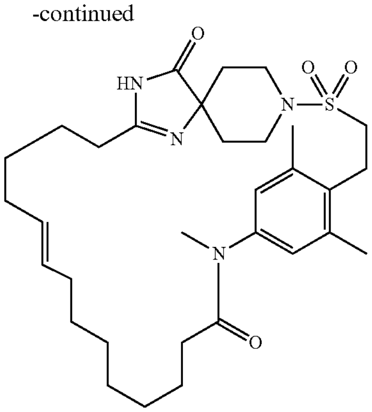

Compound 1444

A macrocyclic olefin compound (Compound 1444) was obtained by the same method as in Reaction 338-1 using dec-9-enoic acid {4-[2-(2-hex-5-enyl-4-oxo-1,3,8-triaza-spiro[4.5]dec-1-ene-8-sulfonyl)-ethyl]-3,5-dimethyl-phenyl}-methyl-amide as a starting material.

MS (ESI) m/z=585 (M+H)+;

HPLC retention time: 5.15 min (analysis condition LCMS-B-2).

Example 373

Compound 1445

(Reaction 373-1)

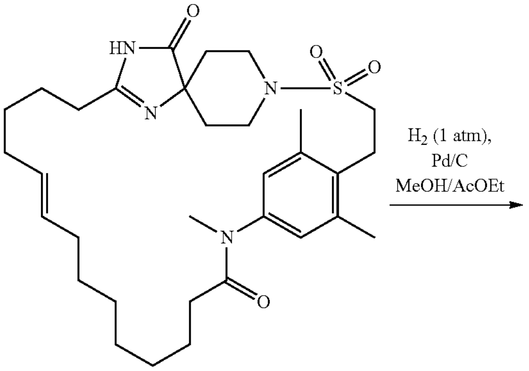

Compound 1444

-continued

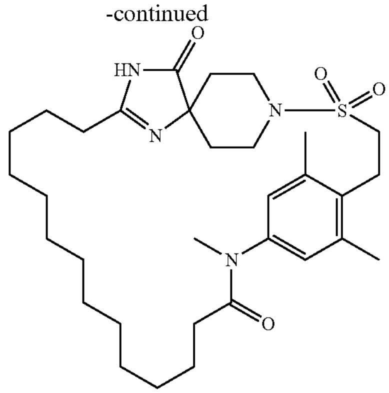

Compound 1445

A saturated macrocyclic compound (Compound 1445) was obtained by the same method as in Reaction 339-1 using a macrocyclic olefin compound (Compound 1444) as a starting material.

MS (ESI) m/z=587 (M+H)+;

HPLC retention time: 2.70 min (analysis condition LCMS-A-1).

Example 374

Compound 1446

(Reaction 374-1)

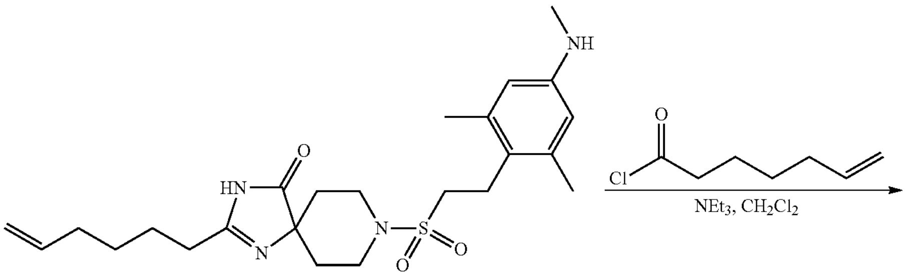

371c

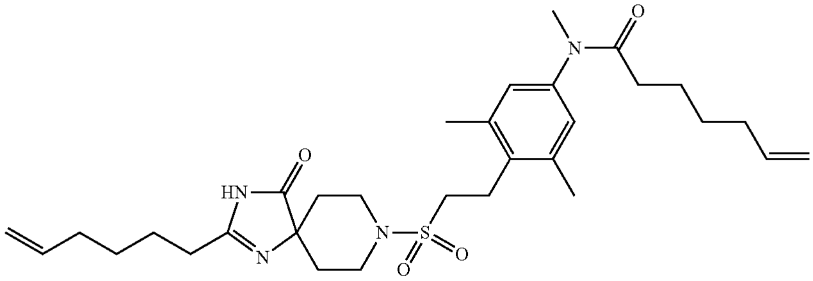

Compound 1446

Hept-6-enoic acid {4-[2-(2-hex-5-enyl-4-oxo-1,3,8-triaza-spiro[4.5]dec-1-ene-8-sulfonyl)-ethyl]-3,5-dimethyl-phenyl}-methyl-amide (Compound 1446) was obtained by the same method as in Reaction 371-2 using 6-heptenoic acid and 8-[2-(2,6-dimethyl-4-methylamino-phenyl)-ethane-sulfonyl]-2-hex-5-enyl-1,3,8-triaza-spiro[4.5]dec-1-en-4-one as starting materials.

MS (ESI) m/z=571 (M+H)+;

HPLC retention time: 2.49 min (analysis condition LCMS-A-1).

Example 375

Compound 1447

(Reaction 375-1)

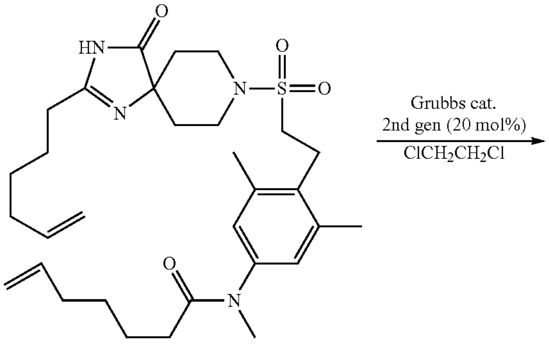

Compound 1446

-continued

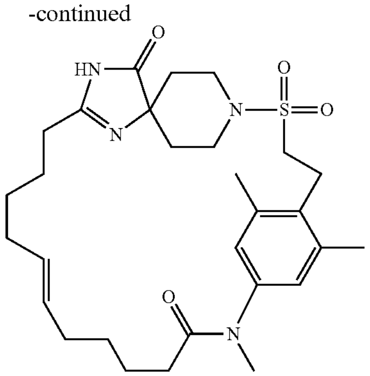

Compound 1447

A macrocyclic olefin compound (Compound 1447) was obtained by the same method as in Reaction 338-1 using hept-6-enoic acid {4-[2-(2-hex-5-enyl-4-oxo-1,3,8-triaza-spiro[4.5]dec-1-ene-8-sulfonyl)-ethyl]-3,5-dimethyl-phenyl}-methyl-amide as a starting material.

MS (ESI) m/z=543 (M+H)+;

HPLC retention time: 2.25 min (analysis condition LCMS-A-1).

Example 376

Compound 1448

(Reaction 376-1)

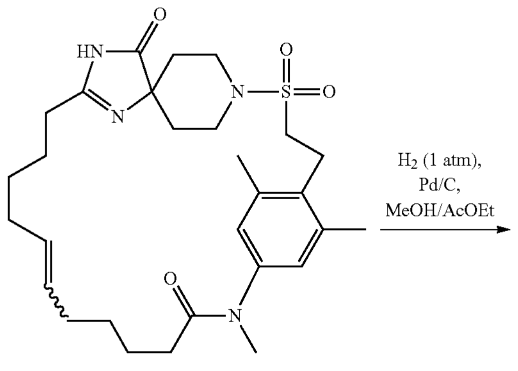

Compound 1447

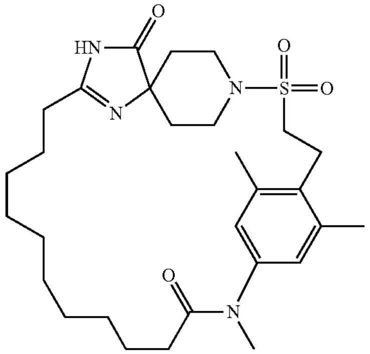

Compound 1448

A saturated macrocyclic compound (Compound 1448) was obtained by the same method as in Reaction 339-1 using a macrocyclic olefin compound (Compound 1447) as a starting material.

MS (ESI) m/z=545 (M+H)+;

HPLC retention time: 2.34 min (analysis condition LCMS-A-1).

Example 377

Compound 1449

(Reaction 377-1)

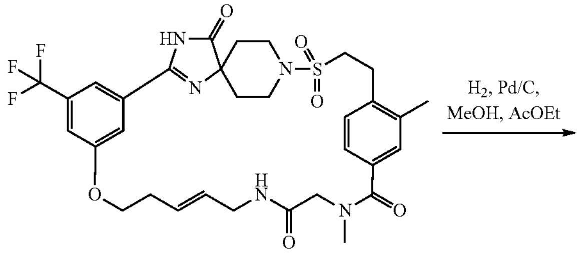

Compound 1422

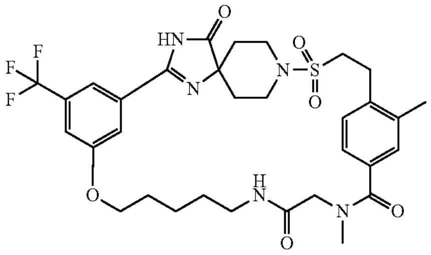

Compound 1449

A saturated macrocyclic compound (Compound 1449) was obtained by the same method as in Reaction 339-1 using a macrocyclic olefin compound (Compound 1422) as a starting material.

MS (ESI) m/z=678 (M+H)+;

HPLC retention time: 2.50 min (analysis condition LCMS-A-1).

Biological Experimental Example

Experimental Example A

In Vitro cAMP Signal Activity of Compounds in Human PTH1 Receptor

Materials and Method (Peptides)

Human PTH(1-34) and calcitonin were purchased from Peptide Institute, Inc. (Osaka, Japan), dissolved in 10 mM acetic acid to 1 mM and stored in a −80° C. freezer.

(Cell Culture)

Cells were cultured in Dulbecco's modified Eagle's medium (DMEM) supplemented with 10% fetal bovine serum (Hyclone), 100 units/ml penicillin G and 100 μg/ml streptomycin sulfate (Invitrogen Corp) at 37° C. in a humidified atmosphere containing 5% $CO_2$.

cAMP signal transduction analysis utilized LLC-PK1 cells not expressing the PTH1 receptor, and HKRK-B7 cells, that is, LLC-PK1 cells overexpressing the human PTH1 receptor at $9.5\times10^5$ receptors/cell (Takasu et al., J. Bone. Miner. Res. 14:11-20, 1999).

(cAMP Stimulation)

HKRK-B7 or LLC-PK1 cells were seeded in a 96-well plate at $1\times10^5$ cells/well and incubated overnight. On the following day, 50 μl of cAMP assay buffer (DMEM, 2 mM IBMX, 0.2 mg/ml bovine serum albumin, 35 mM Hepes-NaOH, pH 7.4) containing human PTH(1-34) or Compound was added and the plate was placed in a 37° C. incubator. The cells were incubated for 20 minutes. After removing the medium, the cells were washed with 100 μl of cAMP assay buffer once. The plate was placed on dry ice powder to freeze the cells and then removed from the dry ice. The cells were lysed with 40 μl of 50 mM HCl and frozen again on dry ice. The amount of intracellular cAMP produced was measured using a commercially available cAMP EIA kit (Biotrack cAMP EIA system, GE health care).

The compounds of the present invention demonstrated a significant cAMP response in HKRK-B7 cells. Table 195 shows percentage values obtained by dividing the amount of cAMP produced by the compound of the present invention in HKRK-B7 cells at $1\times10^{-3}$ M (*at $3\times10^{-4}$ M for Compound 15) by the amount of cAMP produced by hPTH(1-34) as a positive control at 100 nM. The degree of cAMP response in LLC-PK1 cells was lower than the degree in HKRK-B7 cells.

TABLE 195

| Compound | cAMP production activity (%) |
|---|---|
| 1 | 42 |
| 2 | 1.0 |
| 3 | 20 |
| 4 | 11 |
| 5 | 2.5 |
| 6 | 4.2 |
| 7 | 13 |
| 8 | 2.6 |
| 10 | 2.4 |
| 11 | 16 |
| 12 | 12 |
| 13 | 31 |
| 14 | 38 |
| 15 | 1.8* |
| 16 | 41 |
| 17 | 39 |
| 18 | 44 |
| 19 | 35 |
| 20 | 38 |
| 21 | 42 |
| 22 | 43 |
| 23 | 41 |
| 24 | 18 |
| 25 | 18 |
| 26 | 36 |
| 27 | 42 |
| 28 | 31 |
| 29 | 28 |
| 30 | 26 |
| 31 | 41 |
| 32 | 26 |
| 33 | 4.4 |
| 34 | 16 |
| 35 | 56 |
| 36 | 3.5 |
| 37 | 54 |
| 38 | 52 |
| 39 | 25 |
| 40 | 19 |
| 41 | 21 |
| 42 | 27 |
| 43 | 39 |
| 44 | 25 |

TABLE 195-continued

| Compound | cAMP production activity (%) |
|---|---|
| 45 | 22 |
| 46 | 17 |
| 47 | 45 |
| 48 | 25 |
| 49 | 29 |
| 50 | 26 |
| 51 | 38 |
| 52 | 23 |
| 53 | 33 |
| 54 | 35 |
| 55 | 55 |
| 56 | 55 |
| 57 | 35 |
| 58 | 39 |
| 59 | 56 |
| 60 | 34 |
| 61 | 43 |
| 62 | 56 |
| 63 | 51 |
| 64 | 45 |
| 65 | 65 |
| 66 | 57 |
| 67 | 53 |
| 68 | 51 |
| 69 | 61 |
| 70 | 31 |
| 71 | 3.7 |
| 72 | 1.5 |
| 73 | 66 |
| 74 | 48 |
| 75 | 75 |
| 76 | 73 |
| 77 | 69 |
| 78 | 31 |
| 79 | 8.2 |
| 80 | 71 |
| 81 | 57 |
| 82 | 65 |
| 83 | 41 |
| 84 | 51 |
| 85 | 76 |
| 86 | 66 |
| 87 | 6.7 |
| 88 | 97 |
| 89 | 96 |
| 90 | 88 |
| 91 | 73 |
| 92 | 97 |
| 93 | 111 |
| 94 | 62 |
| 95 | 76 |
| 96 | 70 |
| 97 | 4.3 |
| 98 | 75 |
| 99 | 80 |
| 100 | 61 |
| 101 | 49 |
| 102 | 23 |
| 103 | 80 |
| 104 | 79 |
| 105 | 78 |
| 106 | 94 |
| 107 | 110 |
| 108 | 62 |
| 109 | 62 |
| 110 | 25 |
| 111 | 93 |
| 112 | 77 |
| 113 | 111 |
| 114 | 105 |
| 115 | 81 |
| 116 | 94 |
| 117 | 61 |
| 118 | 73 |
| 119 | 60 |
| 120 | 3.1 |
| 121 | 5.8 |

TABLE 195-continued

| Compound | cAMP production activity (%) |
|---|---|
| 122 | 3.0 |
| 123 | 23 |
| 124 | 64 |
| 125 | 62 |
| 126 | 79 |
| 127 | 72 |
| 128 | 57 |
| 129 | 3.7 |
| 130 | 65 |
| 131 | 72 |
| 133 | 82 |
| 134 | 77 |
| 135 | 67 |
| 136 | 72 |
| 137 | 50 |
| 138 | 49 |
| 139 | 64 |
| 140 | 77 |
| 141 | 32 |
| 142 | 63 |
| 143 | 4.5 |
| 144 | 59 |
| 145 | 129 |
| 146 | 122 |
| 147 | 105 |
| 148 | 79 |
| 149 | 56 |
| 150 | 62 |
| 151 | 53 |
| 152 | 47 |
| 153 | 59 |
| 154 | 82 |
| 155 | 45 |
| 156 | 64 |
| 157 | 70 |
| 158 | 62 |
| 159 | 96 |
| 160 | 65 |
| 161 | 69 |
| 162 | 43 |
| 163 | 41 |
| 164 | 45 |
| 165 | 37 |
| 166 | 56 |
| 167 | 44 |
| 168 | 69 |
| 169 | 71 |
| 170 | 77 |
| 171 | 36 |
| 172 | 102 |
| 173 | 71 |
| 174 | 68 |
| 175 | 73 |
| 176 | 74 |
| 177 | 28 |
| 178 | 29 |
| 179 | 49 |
| 180 | 60 |
| 181 | 19 |
| 182 | 38 |
| 183 | 68 |
| 184 | 37 |
| 185 | 33 |
| 186 | 51 |
| 187 | 12 |
| 188 | 70 |
| 189 | 54 |
| 190 | 61 |
| 191 | 57 |
| 192 | 52 |
| 193 | 65 |
| 194 | 56 |
| 195 | 36 |
| 196 | 66 |
| 197 | 41 |
| 198 | 31 |
| 199 | 46 |

TABLE 195-continued

| Compound | cAMP production activity (%) |
|---|---|
| 200 | 37 |
| 201 | 56 |
| 202 | 27 |
| 203 | 25 |
| 204 | 110 |
| 205 | 47 |
| 206 | 70 |
| 207 | 36 |
| 208 | 22 |
| 209 | 24 |
| 210 | 79 |
| 211 | 60 |
| 212 | 59 |
| 213 | 74 |
| 214 | 84 |
| 215 | 81 |
| 216 | 84 |
| 217 | 41 |
| 218 | 72 |
| 219 | 60 |
| 220 | 80 |
| 221 | 103 |
| 222 | 43 |
| 223 | 85 |
| 224 | 54 |
| 225 | 47 |
| 226 | 83 |
| 227 | 87 |
| 228 | 8.3 |
| 229 | 68 |
| 230 | 66 |
| 231 | 96 |
| 232 | 69 |
| 233 | 13 |
| 234 | 78 |
| 235 | 49 |
| 236 | 40 |
| 237 | 74 |
| 238 | 90 |
| 239 | 80 |
| 240 | 49 |
| 241 | 44 |
| 242 | 75 |
| 243 | 80 |
| 244 | 83 |
| 245 | 34 |
| 246 | 39 |
| 247 | 81 |
| 248 | 66 |
| 249 | 71 |
| 250 | 62 |
| 251 | 28 |
| 252 | 28 |
| 253 | 54 |
| 254 | 97 |
| 255 | 64 |
| 256 | 67 |
| 257 | 42 |
| 258 | 87 |
| 259 | 67 |
| 260 | 24 |
| 261 | 70 |
| 262 | 26 |
| 263 | 41 |
| 264 | 69 |
| 265 | 55 |
| 266 | 81 |
| 267 | 42 |
| 268 | 99 |
| 269 | 43 |
| 270 | 55 |
| 271 | 57 |
| 272 | 67 |
| 273 | 55 |
| 274 | 74 |
| 275 | 72 |
| 276 | 63 |

TABLE 195-continued

| Compound | cAMP production activity (%) |
|---|---|
| 277 | 38 |
| 278 | 59 |
| 279 | 67 |
| 280 | 57 |
| 281 | 92 |
| 282 | 29 |
| 283 | 63 |
| 284 | 82 |
| 285 | 65 |
| 286 | 54 |
| 287 | 58 |
| 288 | 82 |
| 289 | 99 |
| 290 | 76 |
| 291 | 66 |
| 292 | 58 |
| 293 | 38 |
| 294 | 106 |
| 295 | 95 |
| 296 | 65 |
| 297 | 91 |
| 298 | 63 |
| 299 | 83 |
| 300 | 73 |
| 301 | 72 |
| 302 | 95 |
| 303 | 76 |
| 304 | 47 |
| 305 | 73 |
| 306 | 45 |
| 307 | 58 |
| 308 | 72 |
| 309 | 72 |
| 310 | 76 |
| 311 | 67 |
| 312 | 49 |
| 313 | 63 |
| 314 | 68 |
| 315 | 26 |
| 316 | 20 |
| 317 | 62 |
| 318 | 52 |
| 319 | 31 |
| 320 | 33 |
| 321 | 55 |
| 322 | 75 |
| 323 | 53 |
| 324 | 30 |
| 325 | 61 |
| 326 | 76 |
| 327 | 84 |
| 328 | 41 |
| 329 | 33 |
| 330 | 23 |
| 331 | 55 |
| 332 | 90 |
| 333 | 87 |
| 334 | 34 |
| 335 | 28 |
| 336 | 28 |
| 337 | 17 |
| 338 | 60 |
| 339 | 66 |
| 340 | 67 |
| 341 | 62 |
| 342 | 93 |
| 343 | 13 |
| 344 | 35 |
| 345 | 21 |
| 346 | 28 |
| 347 | 23 |
| 348 | 5.6 |
| 349 | 11 |
| 350 | 5.5 |
| 351 | 7.4 |
| 352 | 19 |
| 353 | 120 |

TABLE 195-continued

| Compound | cAMP production activity (%) |
|---|---|
| 354 | 27 |
| 355 | 84 |
| 356 | 78 |
| 357 | 78 |
| 358 | 71 |
| 359 | 65 |
| 360 | 62 |
| 361 | 82 |
| 362 | 97 |
| 363 | 67 |
| 364 | 78 |
| 365 | 81 |
| 366 | 85 |
| 367 | 50 |
| 368 | 38 |
| 369 | 43 |
| 370 | 66 |
| 371 | 72 |
| 372 | 51 |
| 373 | 70 |
| 374 | 79 |
| 375 | 57 |
| 376 | 74 |
| 377 | 64 |
| 378 | 60 |
| 379 | 59 |
| 380 | 75 |
| 381 | 72 |
| 382 | 36 |
| 383 | 72 |
| 384 | 61 |
| 385 | 94 |
| 386 | 86 |
| 387 | 97 |
| 388 | 84 |
| 389 | 75 |
| 390 | 22 |
| 391 | 26 |
| 392 | 83 |
| 393 | 44 |
| 394 | 59 |
| 395 | 88 |
| 396 | 85 |
| 397 | 126 |
| 398 | 52 |
| 399 | 64 |
| 400 | 76 |
| 401 | 83 |
| 402 | 85 |
| 403 | 51 |
| 404 | 88 |
| 405 | 7.7 |
| 406 | 100 |
| 407 | 49 |
| 408 | 117 |
| 409 | 55 |
| 410 | 96 |
| 411 | 54 |
| 412 | 54 |
| 413 | 56 |
| 414 | 69 |
| 415 | 56 |
| 416 | 66 |
| 417 | 97 |
| 418 | 84 |
| 419 | 96 |
| 420 | 31 |
| 421 | 68 |
| 422 | 14 |
| 423 | 42 |
| 424 | 2.5 |
| 425 | 17 |
| 426 | 16 |
| 428 | 8.8 |
| 429 | 38 |
| 430 | 23 |
| 431 | 14 |

TABLE 195-continued

| Compound | cAMP production activity (%) |
|---|---|
| 432 | 5.1 |
| 433 | 18 |
| 434 | 25 |
| 435 | 17 |
| 436 | 28 |
| 437 | 45 |
| 438 | 14 |
| 439 | 33 |
| 441 | 24 |
| 442 | 2.5 |
| 444 | 46 |
| 445 | 83 |
| 446 | 49 |
| 447 | 89 |
| 448 | 64 |
| 449 | 94 |
| 450 | 56 |
| 451 | 96 |
| 452 | 58 |
| 453 | 16 |
| 454 | 19 |
| 455 | 31 |
| 456 | 28 |
| 457 | 25 |
| 458 | 77 |
| 459 | 55 |
| 460 | 18 |
| 461 | 51 |
| 462 | 47 |
| 463 | 28 |
| 464 | 54 |
| 465 | 66 |
| 466 | 23 |
| 467 | 60 |
| 468 | 90 |
| 469 | 47 |
| 470 | 90 |
| 471 | 111 |
| 472 | 104 |
| 474 | 89 |
| 475 | 84 |
| 476 | 61 |
| 477 | 31 |
| 478 | 33 |
| 479 | 15 |
| 480 | 44 |
| 481 | 59 |
| 482 | 38 |
| 483 | 41 |
| 484 | 47 |
| 485 | 7.7 |
| 486 | 59 |
| 487 | 49 |
| 488 | 48 |
| 489 | 37 |
| 490 | 26 |
| 491 | 58 |
| 492 | 37 |
| 493 | 50 |
| 494 | 66 |
| 495 | 21 |
| 496 | 24 |
| 497 | 38 |
| 498 | 53 |
| 499 | 40 |
| 500 | 61 |
| 501 | 59 |
| 502 | 14 |
| 503 | 67 |
| 504 | 60 |
| 505 | 61 |
| 506 | 83 |
| 507 | 43 |
| 508 | 24 |
| 509 | 70 |
| 510 | 57 |
| 511 | 29 |

TABLE 195-continued

| Compound | cAMP production activity (%) |
|---|---|
| 512 | 49 |
| 513 | 33 |
| 514 | 75 |
| 515 | 113 |
| 516 | 73 |
| 517 | 58 |
| 518 | 68 |
| 519 | 72 |
| 520 | 28 |
| 521 | 55 |
| 522 | 82 |
| 523 | 89 |
| 524 | 90 |
| 525 | 14 |
| 526 | 83 |
| 527 | 93 |
| 528 | 55 |
| 529 | 68 |
| 530 | 18 |
| 531 | 69 |
| 532 | 80 |
| 533 | 69 |
| 534 | 39 |
| 535 | 83 |
| 536 | 72 |
| 537 | 3.9 |
| 538 | 133 |
| 539 | 80 |
| 540 | 22 |
| 541 | 79 |
| 542 | 66 |
| 543 | 76 |
| 544 | 80 |
| 545 | 86 |
| 546 | 75 |
| 547 | 52 |
| 548 | 88 |
| 549 | 86 |
| 550 | 124 |
| 551 | 92 |
| 552 | 64 |
| 553 | 80 |
| 554 | 82 |
| 555 | 40 |
| 556 | 19 |
| 557 | 50 |
| 558 | 74 |
| 559 | 72 |
| 560 | 66 |
| 561 | 52 |
| 562 | 74 |
| 563 | 69 |
| 564 | 68 |
| 565 | 45 |
| 566 | 19 |
| 567 | 24 |
| 568 | 39 |
| 569 | 4.2 |
| 570 | 66 |
| 571 | 39 |
| 572 | 36 |
| 573 | 35 |
| 574 | 42 |
| 575 | 57 |
| 576 | 95 |
| 577 | 74 |
| 578 | 13 |
| 579 | 55 |
| 580 | 25 |
| 581 | 75 |
| 582 | 104 |
| 583 | 85 |
| 584 | 24 |
| 585 | 39 |
| 586 | 82 |
| 587 | 53 |
| 588 | 77 |

TABLE 195-continued

| Compound | cAMP production activity (%) |
|---|---|
| 589 | 22 |
| 590 | 70 |
| 591 | 34 |
| 592 | 87 |
| 593 | 28 |
| 594 | 69 |
| 595 | 63 |
| 596 | 40 |
| 597 | 51 |
| 598 | 74 |
| 599 | 59 |
| 600 | 67 |
| 601 | 64 |
| 602 | 3.0 |
| 603 | 69 |
| 604 | 21 |
| 605 | 54 |
| 606 | 28 |
| 607 | 6.5 |
| 608 | 20 |
| 609 | 46 |
| 610 | 85 |
| 611 | 82 |
| 612 | 62 |
| 613 | 44 |
| 614 | 25 |
| 615 | 46 |
| 616 | 94 |
| 617 | 96 |
| 618 | 121 |
| 619 | 61 |
| 620 | 112 |
| 621 | 80 |
| 622 | 134 |
| 623 | 123 |
| 624 | 36 |
| 625 | 47 |
| 626 | 53 |
| 627 | 5.3 |
| 628 | 48 |
| 629 | 87 |
| 630 | 4.1 |
| 631 | 65 |
| 632 | 51 |
| 633 | 37 |
| 634 | 29 |
| 635 | 93 |
| 636 | 88 |
| 637 | 38 |
| 638 | 46 |
| 639 | 101 |
| 640 | 26 |
| 641 | 85 |
| 642 | 87 |
| 643 | 94 |
| 644 | 75 |
| 645 | 55 |
| 646 | 99 |
| 647 | 104 |
| 648 | 61 |
| 649 | 40 |
| 650 | 55 |
| 651 | 54 |
| 652 | 63 |
| 653 | 67 |
| 654 | 50 |
| 655 | 74 |
| 656 | 14 |
| 657 | 124 |
| 658 | 84 |
| 659 | 46 |
| 660 | 60 |
| 661 | 45 |
| 662 | 23 |
| 663 | 27 |
| 664 | 77 |
| 665 | 54 |

TABLE 195-continued

| Compound | cAMP production activity (%) |
|---|---|
| 666 | 51 |
| 667 | 40 |
| 668 | 40 |
| 669 | 58 |
| 670 | 123 |
| 671 | 81 |
| 672 | 47 |
| 673 | 27 |
| 674 | 68 |
| 675 | 68 |
| 676 | 69 |
| 677 | 69 |
| 678 | 86 |
| 679 | 65 |
| 680 | 101 |
| 681 | 55 |
| 682 | 81 |
| 683 | 74 |
| 684 | 101 |
| 685 | 46 |
| 686 | 22 |
| 687 | 25 |
| 688 | 55 |
| 689 | 27 |
| 690 | 86 |
| 691 | 69 |
| 692 | 101 |
| 693 | 103 |
| 694 | 77 |
| 695 | 78 |
| 696 | 132 |
| 697 | 60 |
| 698 | 62 |
| 699 | 101 |
| 700 | 121 |
| 701 | 140 |
| 702 | 84 |
| 704 | 68 |
| 705 | 76 |
| 706 | 90 |
| 707 | 124 |
| 708 | 38 |
| 709 | 58 |
| 710 | 76 |
| 711 | 64 |
| 712 | 16 |
| 713 | 55 |
| 714 | 36 |
| 715 | 20 |
| 716 | 62 |
| 717 | 111 |
| 718 | 74 |
| 719 | 77 |
| 720 | 82 |
| 721 | 92 |
| 722 | 60 |
| 723 | 95 |
| 724 | 74 |
| 725 | 58 |
| 726 | 75 |
| 727 | 52 |
| 728 | 87 |
| 729 | 45 |
| 730 | 74 |
| 731 | 54 |
| 732 | 45 |
| 733 | 104 |
| 734 | 47 |
| 735 | 32 |
| 736 | 16 |
| 737 | 96 |
| 738 | 79 |
| 739 | 47 |
| 740 | 123 |
| 741 | 91 |
| 742 | 50 |
| 743 | 54 |

TABLE 195-continued

| Compound | cAMP production activity (%) |
|---|---|
| 744 | 19 |
| 745 | 67 |
| 746 | 120 |
| 747 | 55 |
| 748 | 61 |
| 749 | 77 |
| 750 | 87 |
| 751 | 83 |
| 752 | 79 |
| 753 | 104 |
| 754 | 89 |
| 755 | 74 |
| 756 | 79 |
| 757 | 79 |
| 758 | 98 |
| 759 | 79 |
| 760 | 93 |
| 761 | 104 |
| 764 | 124 |
| 765 | 101 |
| 766 | 88 |
| 767 | 83 |
| 768 | 79 |
| 769 | 55 |
| 770 | 105 |
| 771 | 80 |
| 772 | 69 |
| 773 | 86 |
| 774 | 80 |
| 775 | 70 |
| 776 | 79 |
| 777 | 71 |
| 778 | 57 |
| 779 | 53 |
| 780 | 48 |
| 781 | 30 |
| 782 | 14 |
| 783 | 50 |
| 784 | 84 |
| 785 | 92 |
| 786 | 57 |
| 787 | 81 |
| 788 | 142 |
| 789 | 157 |
| 790 | 88 |
| 791 | 6.1 |
| 792 | 110 |
| 793 | 124 |
| 794 | 76 |
| 795 | 97 |
| 796 | 64 |
| 797 | 88 |
| 798 | 101 |
| 799 | 7.1 |
| 800 | 77 |
| 801 | 103 |
| 802 | 100 |
| 803 | 103 |
| 804 | 78 |
| 812 | 105 |
| 817 | 111 |
| 818 | 79 |
| 820 | 98 |
| 821 | 82 |
| 822 | 99 |
| 823 | 103 |
| 824 | 140 |
| 825 | 114 |
| 826 | 90 |
| 827 | 78 |
| 828 | 92 |
| 829 | 79 |
| 830 | 73 |
| 831 | 4.7 |
| 832 | 84 |
| 833 | 34 |
| 834 | 76 |

TABLE 195-continued

| Compound | cAMP production activity (%) |
|---|---|
| 835 | 50 |
| 836 | 56 |
| 837 | 66 |
| 838 | 75 |
| 839 | 57 |
| 840 | 98 |
| 841 | 45 |
| 842 | 81 |
| 843 | 77 |
| 844 | 86 |
| 845 | 68 |
| 846 | 47 |
| 847 | 71 |
| 848 | 77 |
| 849 | 124 |
| 850 | 82 |
| 851 | 83 |
| 852 | 58 |
| 853 | 63 |
| 854 | 80 |
| 855 | 82 |
| 856 | 81 |
| 857 | 89 |
| 858 | 100 |
| 859 | 26 |
| 860 | 50 |
| 861 | 36 |
| 862 | 55 |
| 863 | 67 |
| 864 | 100 |
| 865 | 8.9 |
| 866 | 47 |
| 867 | 71 |
| 868 | 77 |
| 869 | 65 |
| 870 | 63 |
| 872 | 109 |
| 873 | 77 |
| 874 | 61 |
| 875 | 65 |
| 876 | 22 |
| 877 | 35 |
| 878 | 25 |
| 879 | 70 |
| 880 | 68 |
| 881 | 48 |
| 882 | 70 |
| 883 | 56 |
| 884 | 59 |
| 885 | 58 |
| 886 | 68 |
| 887 | 58 |
| 888 | 86 |
| 889 | 26 |
| 890 | 61 |
| 891 | 8.6 |
| 892 | 51 |
| 893 | 14 |
| 894 | 85 |
| 895 | 90 |
| 896 | 83 |
| 897 | 85 |
| 898 | 4.3 |
| 899 | 12 |
| 900 | 90 |
| 901 | 1.9 |
| 902 | 67 |
| 903 | 56 |
| 904 | 69 |
| 905 | 75 |
| 906 | 78 |
| 907 | 85 |
| 908 | 74 |
| 909 | 78 |
| 910 | 64 |
| 911 | 71 |
| 912 | 98 |

TABLE 195-continued

| Compound | cAMP production activity (%) |
|---|---|
| 913 | 81 |
| 914 | 68 |
| 915 | 61 |
| 916 | 59 |
| 917 | 69 |
| 918 | 63 |
| 919 | 68 |
| 920 | 70 |
| 921 | 59 |
| 922 | 84 |
| 923 | 84 |
| 924 | 76 |
| 925 | 69 |
| 926 | 102 |
| 927 | 80 |
| 928 | 51 |
| 929 | 76 |
| 930 | 92 |
| 931 | 72 |
| 932 | 66 |
| 933 | 60 |
| 934 | 87 |
| 935 | 112 |
| 936 | 98 |
| 937 | 120 |
| 938 | 97 |
| 939 | 111 |
| 940 | 86 |
| 941 | 21 |
| 942 | 31 |
| 943 | 74 |
| 944 | 71 |
| 945 | 77 |
| 946 | 102 |
| 947 | 89 |
| 948 | 68 |
| 949 | 92 |
| 950 | 59 |
| 951 | 93 |
| 952 | 95 |
| 953 | 77 |
| 954 | 81 |
| 955 | 79 |
| 956 | 87 |
| 957 | 17 |
| 958 | 49 |
| 959 | 77 |
| 960 | 84 |
| 961 | 92 |
| 962 | 86 |
| 963 | 16 |
| 964 | 119 |
| 965 | 115 |
| 966 | 82 |
| 967 | 44 |
| 968 | 69 |
| 969 | 45 |
| 970 | 112 |
| 971 | 83 |
| 972 | 89 |
| 973 | 112 |
| 974 | 111 |
| 975 | 74 |
| 976 | 73 |
| 977 | 80 |
| 978 | 91 |
| 979 | 145 |
| 980 | 85 |
| 981 | 106 |
| 982 | 96 |
| 983 | 91 |
| 984 | 133 |
| 985 | 120 |
| 986 | 96 |
| 987 | 54 |
| 988 | 50 |
| 989 | 86 |

TABLE 195-continued

| Compound | cAMP production activity (%) |
|---|---|
| 990 | 87 |
| 991 | 64 |
| 992 | 65 |
| 993 | 64 |
| 994 | 87 |
| 995 | 98 |
| 996 | 85 |
| 997 | 74 |
| 998 | 92 |
| 999 | 61 |
| 1000 | 86 |
| 1001 | 64 |
| 1002 | 50 |
| 1003 | 67 |
| 1006 | 52 |
| 1007 | 20 |
| 1008 | 73 |
| 1009 | 70 |
| 1010 | 96 |
| 1011 | 17 |
| 1012 | 87 |
| 1013 | 48 |
| 1014 | 84 |
| 1015 | 83 |
| 1016 | 92 |
| 1017 | 101 |
| 1018 | 109 |
| 1019 | 72 |
| 1020 | 81 |
| 1021 | 137 |
| 1022 | 105 |
| 1023 | 92 |
| 1024 | 66 |
| 1025 | 114 |
| 1026 | 68 |
| 1027 | 82 |
| 1028 | 75 |
| 1029 | 104 |
| 1030 | 115 |
| 1031 | 111 |
| 1032 | 88 |
| 1033 | 22 |
| 1034 | 54 |
| 1035 | 77 |
| 1036 | 82 |
| 1037 | 87 |
| 1038 | 111 |
| 1039 | 103 |
| 1040 | 111 |
| 1041 | 38 |
| 1042 | 102 |
| 1043 | 99 |
| 1044 | 86 |
| 1045 | 106 |
| 1046 | 101 |
| 1047 | 82 |
| 1048 | 96 |
| 1050 | 92 |
| 1051 | 85 |
| 1052 | 62 |
| 1053 | 70 |
| 1054 | 80 |
| 1055 | 84 |
| 1056 | 94 |
| 1057 | 100 |
| 1058 | 133 |
| 1059 | 116 |
| 1060 | 58 |
| 1061 | 55 |
| 1062 | 65 |
| 1063 | 72 |
| 1064 | 73 |
| 1065 | 83 |
| 1066 | 83 |
| 1067 | 69 |
| 1068 | 68 |
| 1069 | 79 |

TABLE 195-continued

| Compound | cAMP production activity (%) |
|---|---|
| 1070 | 69 |
| 1071 | 60 |
| 1072 | 54 |
| 1073 | 66 |
| 1074 | 66 |
| 1075 | 69 |
| 1076 | 88 |
| 1077 | 74 |
| 1078 | 74 |
| 1079 | 91 |
| 1080 | 81 |
| 1081 | 53 |
| 1082 | 22 |
| 1083 | 113 |
| 1084 | 13 |
| 1085 | 100 |
| 1086 | 151 |
| 1087 | 97 |
| 1088 | 95 |
| 1089 | 99 |
| 1090 | 118 |
| 1091 | 118 |
| 1092 | 89 |
| 1093 | 100 |
| 1094 | 100 |
| 1095 | 105 |
| 1096 | 93 |
| 1097 | 90 |
| 1098 | 88 |
| 1099 | 91 |
| 1100 | 76 |
| 1101 | 110 |
| 1102 | 10 |
| 1103 | 5.4 |
| 1104 | 16 |
| 1106 | 58 |
| 1107 | 24 |
| 1108 | 99 |
| 1109 | 29 |
| 1110 | 92 |
| 1111 | 79 |
| 1112 | 76 |
| 1113 | 99 |
| 1114 | 95 |
| 1115 | 140 |
| 1116 | 106 |
| 1117 | 88 |
| 1118 | 79 |
| 1119 | 136 |
| 1120 | 124 |
| 1121 | 118 |
| 1122 | 150 |
| 1123 | 122 |
| 1124 | 119 |
| 1125 | 93 |
| 1126 | 106 |
| 1127 | 91 |
| 1128 | 119 |
| 1129 | 102 |
| 1130 | 100 |
| 1131 | 96 |
| 1132 | 80 |
| 1133 | 113 |
| 1134 | 50 |
| 1135 | 84 |
| 1136 | 112 |
| 1137 | 82 |
| 1138 | 77 |
| 1139 | 86 |
| 1140 | 55 |
| 1141 | 83 |
| 1142 | 68 |
| 1143 | 78 |
| 1144 | 124 |
| 1145 | 102 |
| 1146 | 107 |
| 1147 | 112 |

TABLE 195-continued

| Compound | cAMP production activity (%) |
|---|---|
| 1148 | 100 |
| 1149 | 98 |
| 1150 | 107 |
| 1151 | 105 |
| 1152 | 0.8 |
| 1153 | 106 |
| 1154 | 115 |
| 1155 | 83 |
| 1156 | 77 |
| 1157 | 44 |
| 1158 | 103 |
| 1159 | 87 |
| 1160 | 84 |
| 1161 | 84 |
| 1162 | 112 |
| 1163 | 101 |
| 1164 | 4.7 |
| 1165 | 4.3 |
| 1166 | 144 |
| 1167 | 115 |
| 1168 | 27 |
| 1169 | 50 |
| 1170 | 24 |
| 1171 | 28 |
| 1172 | 73 |
| 1173 | 85 |
| 1174 | 91 |
| 1175 | 81 |
| 1176 | 82 |
| 1178 | 84 |
| 1179 | 65 |
| 1180 | 73 |
| 1181 | 98 |
| 1182 | 109 |
| 1183 | 90 |
| 1184 | 108 |
| 1185 | 102 |
| 1186 | 110 |
| 1187 | 75 |
| 1188 | 99 |
| 1189 | 104 |
| 1190 | 108 |
| 1191 | 66 |
| 1192 | 100 |
| 1193 | 86 |
| 1194 | 62 |
| 1195 | 82 |
| 1196 | 76 |
| 1197 | 74 |
| 1198 | 88 |
| 1199 | 77 |
| 1200 | 73 |
| 1201 | 77 |
| 1202 | 91 |
| 1203 | 90 |
| 1204 | 83 |
| 1205 | 83 |
| 1206 | 88 |
| 1207 | 112 |
| 1208 | 65 |
| 1209 | 94 |
| 1210 | 86 |
| 1211 | 99 |
| 1212 | 96 |
| 1213 | 80 |
| 1214 | 79 |
| 1215 | 74 |
| 1216 | 61 |
| 1217 | 68 |
| 1218 | 90 |
| 1219 | 67 |
| 1220 | 80 |
| 1221 | 75 |
| 1222 | 77 |
| 1223 | 54 |
| 1224 | 88 |
| 1225 | 90 |

TABLE 195-continued

| Compound | cAMP production activity (%) |
|---|---|
| 1226 | 51 |
| 1227 | 77 |
| 1228 | 68 |
| 1229 | 56 |
| 1230 | 64 |
| 1231 | 88 |
| 1232 | 106 |
| 1233 | 78 |
| 1234 | 114 |
| 1235 | 98 |
| 1236 | 99 |
| 1237 | 96 |
| 1238 | 73 |
| 1239 | 91 |
| 1240 | 95 |
| 1241 | 101 |
| 1242 | 106 |
| 1243 | 77 |
| 1244 | 96 |
| 1245 | 115 |
| 1246 | 85 |
| 1247 | 70 |
| 1248 | 81 |
| 1249 | 62 |
| 1250 | 67 |
| 1251 | 56 |
| 1252 | 72 |
| 1253 | 81 |
| 1254 | 87 |
| 1255 | 66 |
| 1256 | 72 |
| 1257 | 98 |
| 1258 | 116 |
| 1259 | 101 |
| 1260 | 81 |
| 1261 | 99 |
| 1262 | 90 |
| 1263 | 73 |
| 1264 | 77 |
| 1265 | 89 |
| 1266 | 96 |
| 1267 | 74 |
| 1268 | 33 |
| 1269 | 92 |
| 1270 | 61 |
| 1271 | 92 |
| 1272 | 71 |
| 1273 | 81 |
| 1274 | 81 |
| 1275 | 89 |
| 1276 | 140 |
| 1277 | 95 |
| 1278 | 95 |
| 1279 | 113 |
| 1280 | 74 |
| 1281 | 95 |
| 1282 | 63 |
| 1283 | 18 |
| 1284 | 2.5 |
| 1285 | 67 |
| 1286 | 35 |
| 1287 | 64 |
| 1288 | 54 |
| 1289 | 17 |
| 1290 | 6.3 |
| 1291 | 48 |
| 1292 | 14 |
| 1293 | 84 |
| 1294 | 76 |
| 1295 | 73 |
| 1296 | 64 |
| 1297 | 98 |
| 1298 | 117 |
| 1299 | 87 |
| 1300 | 81 |
| 1301 | 49 |
| 1302 | 95 |

TABLE 195-continued

| Compound | cAMP production activity (%) |
|---|---|
| 1303 | 102 |
| 1304 | 107 |
| 1305 | 138 |
| 1306 | 159 |
| 1307 | 116 |
| 1308 | 102 |
| 1309 | 109 |
| 1310 | 104 |
| 1311 | 79 |
| 1312 | 105 |
| 1313 | 87 |
| 1314 | 78 |
| 1315 | 76 |
| 1316 | 2.9 |
| 1317 | 3.4 |
| 1318 | 19 |
| 1319 | 5.8 |
| 1320 | 10 |
| 1321 | 63 |
| 1322 | 80 |
| 1323 | 78 |
| 1324 | 1.0 |
| 1325 | 113 |
| 1326 | 84 |
| 1327 | 92 |
| 1328 | 93 |
| 1329 | 85 |
| 1330 | 9.2 |
| 1331 | 96 |
| 1332 | 119 |
| 1333 | 109 |
| 1334 | 116 |
| 1335 | 97 |
| 1336 | 133 |
| 1337 | 44 |
| 1338 | 84 |
| 1339 | 86 |
| 1340 | 84 |
| 1341 | 83 |
| 1342 | 114 |
| 1343 | 98 |
| 1344 | 94 |
| 1345 | 107 |
| 1346 | 113 |
| 1347 | 87 |
| 1348 | 95 |
| 1349 | 98 |
| 1350 | 22 |
| 1351 | 100 |
| 1352 | 78 |
| 1353 | 111 |
| 1354 | 128 |
| 1355 | 118 |
| 1356 | 14 |
| 1357 | 13 |
| 1358 | 153 |
| 1359 | 165 |
| 1360 | 121 |
| 1361 | 104 |
| 1362 | 48 |
| 1363 | 80 |
| 1364 | 84 |
| 1365 | 108 |
| 1366 | 103 |
| 1367 | 58 |
| 1368 | 83 |
| 1369 | 30 |
| 1370 | 64 |
| 1371 | 84 |
| 1372 | 36 |
| 1373 | 44 |
| 1374 | 33 |
| 1375 | 23 |
| 1376 | 42 |
| 1377 | 35 |
| 1378 | 116 |
| 1379 | 86 |

TABLE 195-continued

| Compound | cAMP production activity (%) |
|---|---|
| 1380 | 109 |
| 1381 | 102 |
| 1382 | 93 |
| 1383 | 96 |
| 1384 | 78 |
| 1385 | 92 |
| 1386 | 92 |
| 1387 | 68 |
| 1388 | 59 |
| 1389 | 67 |
| 1390 | 69 |
| 1391 | 116 |
| 1392 | 89 |
| 1393 | 84 |
| 1394 | 82 |
| 1395 | 68 |
| 1396 | 133 |
| 1397 | 24 |
| 1398 | 77 |
| 1399 | 20 |
| 1400 | 49 |
| 1401 | 73 |
| 1402 | 69 |
| 1403 | 66 |
| 1404 | 64 |
| 1405 | 51 |
| 1406 | 7.3 |
| 1407 | 6.6 |
| 1408 | 5.1 |
| 1409 | 13 |
| 1410 | 51 |
| 1411 | 38 |
| 1412 | 7.2 |
| 1413 | 57 |
| 1414 | 47 |
| 1415 | 49 |
| 1416 | 48 |
| 1417 | 49 |
| 1418 | 36 |
| 1419 | 70 |
| 1420 | 20 |
| 1421 | 49 |
| 1422 | 15 |
| 1423 | 17 |
| 1424 | 29 |
| 1425 | 32 |
| 1426 | 5.4 |
| 1427 | 72 |
| 1428 | 67 |
| 1429 | 8.9 |
| 1430 | 13 |
| 1431 | 15 |
| 1432 | 18 |
| 1433 | 38 |
| 1434 | 54 |
| 1435 | 19 |
| 1436 | 54 |
| 1437 | 57 |
| 1438 | 40 |
| 1439 | 18 |
| 1440 | 10 |
| 1441 | 5.0 |
| 1442 | 9.3 |
| 1443 | 61 |
| 1444 | 12 |
| 1445 | 62 |
| 1446 | 88 |
| 1447 | 15 |
| 1448 | 9.4 |
| 1449 | 18 |

INDUSTRIAL APPLICABILITY

The present invention provides a compound having a PTH-like effect. The present invention also provides a medicine for the prevention and/or treatment of osteoporosis, fracture, osteomalacia, arthritis, thrombocytopenia, hypoparathyroidism, hyperphosphatemia, tumoral calcinosis or the like, or stem cell mobilization.

The invention claimed is:

1. A compound represented by the following general formula (1):

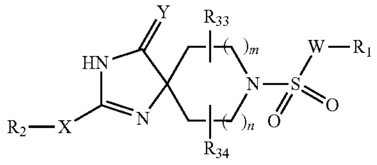

(1)

wherein:

W is selected from:

1) C1-C6 alkylene optionally substituted with a fluorine atom,

2) C2-C6 alkenylene,

X is a single bond,

Y is an oxygen atom, m is 1;

n is 1;

$R_1$ is represented by formula (3) or formula (4):

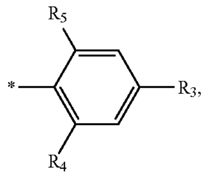

(3)

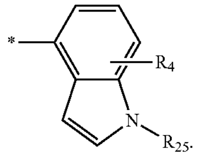

(4)

$R_3$ is selected from:

1) —$CONR_7R_8$,

2) —$OR_9$,

3) —$NR_9R_{10}$,

4) —$N(R_9)COR_{11}$,

5) —$N(R_9)SO_2R_{12}$,

6) —$SO_2R_{15}$,

7) C1-C2 alkyl optionally substituted with a group(s) independently selected from —$COR_{16}$ and —$NR_{13}R_{14}$, $R_4$ is selected from:

1) a halogen atom, 2) cyano,

3) C1-C10 alkyl optionally substituted with a group(s) independently selected from hydroxycarbonyl, C1-C10 alkoxycarbonyl and aminocarbonyl, 4) C1-C10 haloalkyl, 5) C1-C10 alkoxy, $R_5$ is selected from a hydrogen atom, a halogen atom, C1-C10 alkyl, C1-C10 haloalkyl and C1-C10 alkoxy;

$R_7$ is selected from:
1) hydrogen,
2) C1-C10 alkyl optionally substituted with a group(s) independently selected from amino and C1-C10 alkylamino,
3) C1-C10 hydroxyalkyl,
4) C1-C10 haloalkyl,
5) C1-C10 heteroalkyl,
6) C1-C10 heteroalkyl optionally substituted with a group(s) selected from a hydroxyl group, C1-C10 alkylamino and C2-C10 alkenyl,
7) aryl,
8) heteroaryl,
9) aryl C1-C10 alkyl,
10) a heterocycle optionally substituted with C1-C10 alkyl,
11) —$(CH_2)_L COR_{16}$ (wherein L represents an integer of 1 to 4),
12) C1-C10 alkoxy,
13) C2-C10 alkenyl and
14) —$NR_{40}R_{41}$;

$R_{40}$ and $R_{41}$ are independently selected from hydrogen, C1-C10 alkyl and C1-C10 alkylcarbonyl, or $R_{40}$ and $R_{41}$ may be bonded to each other to form a ring selected from azetidinyl, pyrrolidinyl, piperidinyl, piperazinyl and morpholinyl, and the heterocycle is optionally substituted with C1-C10 alkyl;

$R_8$ is selected from hydrogen and C1-C10 alkyl optionally substituted with a halogen atom(s) and/or a hydroxyl group(s);

$R_7$ and $R_8$ may be bonded to form a 4- to 7-membered heterocycle optionally containing an additional element(s) or group(s) independently selected from O, N, S, SO and $SO_2$, and the heterocycle optionally contains carbonyl, and the heterocycle is optionally substituted with a substituent(s) independently selected from:
1) a halogen atom,
2) C1-C10 alkyl optionally having C1-C10 alkylamino as a substituent(s),
3) C1-C10 haloalkyl,
4) a hydroxyl group,
5) C1-C10 hydroxyalkyl,
6) C1-C10 alkoxy optionally substituted with a group(s) independently selected from a halogen atom, a hydroxyl group, amino and C1-C10 alkylamino,
7) aryl optionally substituted with a group(s) selected from a halogen atom, a hydroxyl group, amino and C1-C10 alkylamino,
8) C1-C10 heteroalkyl optionally substituted with a group(s) independently selected from a halogen atom, a hydroxyl group, amino and C1-C10 alkylamino,
9) a heterocycle optionally substituted with C1-C10 alkyl,
10) heteroaryl optionally substituted with C1-C10 alkyl,
11) heterocyclyl C1-C10 alkyl,
12) —$COR_{16}$,
13) —$NR_{19}R_{20}$,
14) —$SO_2R_{21}$,
15) C1-C10 alkoxy-C1-C10 alkyl optionally having a hydroxyl group(s) as a substituent(s) and
16) C1-C10 hydroxyalkyloxy, wherein the hydrogen atom of the hydroxyl group is optionally replaced by C1-C10 hydroxyalkyl, and the heterocycle may further form a spiro ring together with a 4- to 6-membered heterocycle, and the bonded 4- to 6-membered heterocycle optionally contains O and N as ring-forming elements in addition to carbon atoms, and the carbon atom(s) may be oxidized to form carbonyl, and the 4- to 6-membered heterocycle is optionally further substituted with C1-C10 alkyl;

$R_{16}$ is selected from:
1) a hydroxyl group,
2) C1-C10 alkoxy,
3) $NR_{17}R_{18}$ and
4) C1-C10 alkyl optionally substituted with a substituent(s) selected from a halogen atom, a hydroxyl group, C1-C10 alkoxycarbonyl or C1-C10 alkylamino;

$R_{17}$ is selected from:
1) hydrogen,
2) C1-C10 alkyl optionally substituted with a group(s) selected from aryl, amino, C1-C10 alkylamino, C1-C10 alkylcarbonylamino and a hydroxyl group,
3) heteroaryl and
4) C1-C10 alkoxy;

$R_{18}$ is selected from hydrogen, C1-C10 alkyl and C1-C10 hydroxyalkyl;

$R_{17}$ and $R_{18}$ may be bonded to each other to form a ring selected from azetidinyl, pyrrolidinyl, piperidinyl, piperazinyl and morpholinyl, and the ring is optionally substituted with a group(s) selected independently of each other from C1-C10 alkyl, a halogen atom and C1-C10 alkoxycarbonyl;

$R_{19}$ is selected from hydrogen, C1-C10 alkyl, C1-C10 haloalkyl, C1-C10 alkylcarbonyl, C1-C10 hydroxyalkyl, C1-C10 aminoalkyl, C1-C10 alkoxycarbonyl and C1-C10 heteroalkyl;

$R_{20}$ is selected from hydrogen and C1-C10 alkyl;

$R_{19}$ and $R_{20}$ may be bonded to form a ring selected from azetidinyl, pyrrolidinyl, piperidinyl, piperazinyl and morpholinyl, and the ring is optionally substituted with a group(s) selected independently of each other from C1-C10 alkyl and a halogen atom;

$R_{21}$ is selected from:
1) C1-C10 alkyl optionally substituted with aryl,
2) amino,
3) C1-C10 alkylamino and
4) aryl optionally substituted with C1-C10 alkyl;

$R_9$ is selected from:
1) hydrogen,
2) C1-C10 alkyl optionally substituted with a group(s) independently selected from $R_{23}$,
3) cycloalkyl optionally substituted with a halogen atom(s) or a hydroxyl group(s),
4) a heterocycle optionally substituted with a group(s) independently selected from C1-C10 alkyl, C1-C10 alkylcarbonyl, C1-C10 alkoxy, C1-C10 alkoxycarbonyl, amino and a halogen atom,
5) C1-C10 heteroalkyl optionally substituted with a group(s) independently selected from a halogen atom and a hydroxyl group,
6) heteroaryl optionally substituted with a group(s) selected from C1-C10 alkyl, C1-C10 alkylcarbonyl, C1-C10 alkoxycarbonyl and a halogen atom and
7) cycloalkenyl optionally substituted with a group(s) selected from C1-C10 alkoxy, C1-C10 alkylamino, amino, a hydroxyl group and a halogen atom, wherein the cycloalkenyl optionally contains a carbonyl group;

$R_{23}$ is independently selected from:
1) a halogen atom,
2) a hydroxyl group,
3) a C1-C10 alkylcarbonyloxy group,
4) —$COR_{16}$,
5) amino,
6) C1-C10 alkylamino, 7) a heterocycle optionally substituted with a group(s) selected from C1-C10 alkyl, C1-C10 alkylcarbonyl, C1-C10 alkoxycarbonyl and a halogen atom and
8) cyano;
$R_{10}$ is selected from:
1) hydrogen and
2) C1-C10 alkyl optionally substituted with a group(s) selected from a halogen atom, a hydroxyl group and aryl;
$R_9$ and $R_{10}$ may be bonded to form a 4- to 7-membered heterocycle optionally containing an additional element(s) or group(s) independently selected from N, O, S, SO, $SO_2$, carbonyl and thiocarbonyl, and the heterocycle is optionally substituted with a substituent(s) independently selected from $R_{24}$;
$R_{24}$ is independently selected from:
1) a halogen atom,
2) C1-C10 alkyl optionally substituted with a group(s) independently selected from C1-C10 alkylamino and C1-C10 alkylcarbonylamino,
3) C1-C10 haloalkyl,
4) a hydroxyl group,
5) C1-C10 hydroxyalkyl,
6) C1-C10 alkoxy optionally substituted with a group(s) independently selected from a halogen atom, a hydroxyl group, amino and C1-C10 alkylamino,
7) aryl optionally substituted with a group(s) independently selected from a halogen atom, a hydroxyl group, amino and C1-C10 alkylamino,
8) C1-C10 heteroalkyl optionally substituted with 1 to 2 groups independently selected from a halogen atom, a hydroxyl group, amino and C1-C10 alkylamino,
9) —$COR_{16}$, and
10) —$NR_{19}R_{20}$;
$R_{11}$ is selected from:
1) C1-C10 alkyl optionally substituted with 1 to 3 substituents independently selected from:
i) a hydroxyl group,
ii) —$NR_{17}R_{18}$,
iii) a C1-C10 alkoxy group,
iv) a halogen atom,
v) C1-C10 alkoxycarbonyl, and
vi) aminocarbonyl,
2) aryl or aryl C1-C10 alkyl,
3) cycloalkyl optionally substituted with a halogen atom(s),
4) a heterocycle optionally substituted with a group(s) selected from C1-C10 alkyl,
5) C1-C10 alkoxy, wherein the alkyl group is optionally substituted with a group(s) independently selected from C1-C10 alkylcarbonylamino, amino, C1-C10 alkylamino and a hydroxyl group,
6) amino,
7) C1-C10 alkylamino, wherein the alkyl group is optionally substituted with a group(s) independently selected from C1-C10 alkylcarbonylamino, amino, C1-C10 alkylamino, hydroxycarbonyl and a hydroxyl group and
8) C2-C10 alkenyl;
$R_{12}$ is selected from:
1) C1-C10 alkyl,
2) amino and
3) C1-C10 alkylamino, wherein the alkyl group is optionally substituted with a group(s) independently selected from amino, C1-C10 alkylamino and a hydroxyl group;
$R_{13}$ is selected from:
1) hydrogen,
2) C1-C10 alkyl,
3) C1-C10 alkylcarbonyl, wherein the alkyl is optionally substituted with a hydroxyl group(s),
4) C1-C10 alkoxycarbonyl,
5) aminocarbonyl,
6) C1-C10 alkylaminocarbonyl and
7) heterocyclic carbonyl optionally substituted with C1-C10 alkyl;
$R_{14}$ is selected from:
1) hydrogen and
2) C1-C10 alkyl optionally substituted with a group(s) independently selected from a halogen atom, a hydroxyl group, amino and C1-C10 alkylamino;
$R_{13}$ and $R_{14}$ may be bonded to form a 4- to 7-membered heterocycle optionally containing an additional element(s) or group(s) independently selected from O, N, S, SO and $SO_2$, and the heterocycle optionally contains carbonyl, and the heterocycle is optionally substituted with C1-C10 alkyl;
$R_{15}$ is selected from:
1) C1-C10 alkyl and
2) —$NR_{35}R_{36}$;
$R_{35}$ is selected from:
1) hydrogen,
2) C1-C10 alkyl optionally substituted with a group(s) independently selected from:
i) a halogen atom,
ii) a hydroxyl group,
iii) C1-C10 alkylcarbonylamino,
iv) —$COR_{16}$,
v) amino,
vi) C1-C10 alkylamino,
vii) C1-C10 alkoxy optionally substituted with a halogen atom(s),
viii) heteroaryl optionally substituted with a C1-C10 alkyl group(s) and
ix) a heterocycle,
3) aryl optionally substituted with a group(s) independently selected from a halogen atom, a hydroxyl group, amino and C1-C10 alkylamino,
4) cycloalkyl optionally substituted with a group(s) independently selected from a halogen atom and a hydroxyl group,
5) a heterocycle optionally substituted with a group(s) independently selected from C1-C10 alkyl, a halogen atom and aryl C1-C10 alkyl,
6) heteroaryl optionally substituted with C1-C10 alkyl and
7) C1-C10 alkylcarbonyl;
$R_{36}$ is selected from:
1) hydrogen and
2) C1-C10 alkyl optionally substituted with a group(s) independently selected from a halogen atom, a hydroxyl group and aryl;
$R_{35}$ and $R_{36}$ may be bonded to each other to form a ring selected from azetidinyl, pyrrolidinyl, piperidinyl, piperazinyl and morpholinyl, and the ring is optionally substituted with a group(s) selected independently of each other from C1-C10 alkyl and a halogen atom;
$R_{25}$ is selected from:
1) C1-C10 heteroalkyl optionally substituted with a hydroxyl group(s), and
2) C1-C10 alkyl optionally substituted with a hydroxyl group(s),
$R_2$ is selected from:
1) cyclohexyl, and
2) aryl optionally substituted with a group(s) independently selected from $R_{44}$, $R_{44}$ is selected from:

1) a halogen atom, 2) cyano,

3) C1-C10 alkyl optionally substituted with a group(s) independently selected from:

i) a hydroxyl group, ii) —$OR_{26}$, iii) cyano, iv) aryloxy optionally substituted with a group(s) independently selected from a halogen atom, C1-C10 alkyl optionally substituted with a halogen atom(s) or C1-C10 alkoxy optionally substituted with a halogen atom(s), 4) C1-C10 haloalkyl, 5) cycloalkyl optionally substituted with a group(s) independently selected from a halogen atom and C1-C10 haloalkyl, 6) C1-C10 alkoxy optionally substituted with a halogen atom(s) or a C2-C6 alkenyl group(s),

7) —$COR_{30}$,

8) C1-C10 heteroalkyl optionally substituted with a halogen atom(s), 9) aryl optionally substituted with a substituent(s) independently selected from:

i) C1-C10 alkyl, ii) aryl, 10) heteroaryl optionally substituted with a C1-C10 alkyl group(s),

11) —$SO_2R_{43}$,

12) C1-C10 alkylthio optionally substituted with a halogen atom(s),

13) —$Si(R_{43})_3$ and

14) —$SF_5$;

$R_{43}$ represents a C1-C10 alkyl group;

$R_{26}$ is aryl, or C1-C10 alkyl optionally substituted with a halogen atom(s);

$R_{30}$ is selected from a hydroxyl group, C1-C10 alkoxy and —$NR_{31}R_{32}$;

$R_{31}$ and $R_{32}$ are independently selected from:

1) hydrogen,

2) C1-C10 alkyl optionally substituted with aryl and 3) aryl;

$R_{31}$ and $R_{32}$ may be bonded to form a ring selected from azetidinyl, pyrrolidinyl, piperidinyl, piperazinyl and morpholinyl, and the ring is optionally substituted with a group(s) selected independently of each other from C1-C10 alkyl, a halogen atom and C1-C10 alkoxycarbonyl; and $R_{33}$ and $R_{34}$ are hydrogen, or a pharmacologically acceptable salt thereof.

2. The compound or a pharmacologically acceptable salt thereof according to claim 1, wherein $R_1$ is represented by formula (4):

(4)

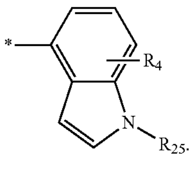

3. A compound according to claim 1 selected from the group consisting of:

(73) 4-{2-[2-(2,4-dichloro-phenyl)-4-oxo-1,3,8-triaza-spiro[4.5]dec-1-ene-8-sulfonyl]-ethyl}-3,N,N-trimethyl-benzamide;

(75) 3,N,N-trimethyl-4-{2-[4-oxo-2-(4-trifluoromethyl-phenyl)-1,3,8-triaza-spiro[4.5]dec-1-ene-8-sulfonyl]-ethyl}-benzamide;

(78) 4-{2-[2-(2,6-difluoro-phenyl)-4-oxo-1,3,8-triaza-spiro[4.5]dec-1-ene-8-sulfonyl]-ethyl}-3,N,N-trimethyl-benzamide;

(79) 4-{2-[2-(2,6-dimethoxy-phenyl)-4-oxo-1,3,8-triaza-spiro[4.5]dec-1-ene-8-sulfonyl]-ethyl}-3,N,N-trimethyl-benzamide;

(80) 4-{2-[2-(3-methoxy-phenyl)-4-oxo-1,3,8-triaza-spiro[4.5]dec-1-ene-8-sulfonyl]-ethyl}-3,N,N-trimethyl-benzamide;

(81) 4-{2-[2-(3-chloro-phenyl)-4-oxo-1,3,8-triaza-spiro[4.5]dec-1-ene-8-sulfonyl]-ethyl}-3,N,N-trimethyl-benzamide;

(82) 4-{2-[2-(3,5-bis-trifluoromethyl-phenyl)-4-oxo-1,3,8-triaza-spiro[4.5]dec-1-ene-8-sulfonyl]-ethyl}-3,N,N-trimethyl-benzamide;

(84) 3,N,N-trimethyl-4-[2-(4-oxo-2-m-tolyl-1,3,8-triaza-spiro[4.5]dec-1-ene-8-sulfonyl)-ethyl]-benzamide;

(85) 4-{2-[2-(2-chloro-5-trifluoromethyl-phenyl)-4-oxo-1,3,8-triaza-spiro[4.5]dec-1-ene-8-sulfonyl]-ethyl}-3,N,N-trimethyl-benzamide;

(86) 3,N,N-trimethyl-4-{2-[4-oxo-2-(3-trifluoromethyl-phenyl)-1,3,8-triaza-spiro[4.5]dec-1-ene-8-sulfonyl]-ethyl}-benzamide;

(87) 4-{2-[2-(4-chloro-phenyl)-4-oxo-1,3,8-triaza-spiro[4.5]dec-1-ene-8-sulfonyl]-ethyl}-3,N,N-trimethyl-benzamide;

(88) 4-{2-[2-(2,3-dichloro-phenyl)-4-oxo-1,3,8-triaza-spiro[4.5]dec-1-ene-8-sulfonyl]-ethyl}-3,N,N-trimethyl-benzamide;

(89) 4-{2-[2-(3-chloro-4-fluoro-phenyl)-4-oxo-1,3,8-triaza-spiro[4.5]dec-1-ene-8-sulfonyl]-ethyl}-3,N,N-trimethyl-benzamide;

(90) 4-{2-[2-(2-chloro-4-fluoro-phenyl)-4-oxo-1,3,8-triaza-spiro[4.5]dec-1-ene-8-sulfonyl]-ethyl}-3,N,N-trimethyl-benzamide;

(91) 4-{2-[2-(3-bromo-phenyl)-4-oxo-1,3,8-triaza-spiro[4.5]dec-1-ene-8-sulfonyl]-ethyl}-3,N,N-trimethyl-benzamide;

(93) 4-{2-[2-(3-chloro-2-fluoro-phenyl)-4-oxo-1,3,8-triaza-spiro[4.5]dec-1-ene-8-sulfonyl]-ethyl}-3,N,N-trimethyl-benzamide;

(94) 3,N,N-trimethyl-4-(2-{4-oxo-2-[4-(1,1,2,2-tetrafluoro-ethoxy)-phenyl]-1,3,8-triaza-spiro[4.5]dec-1-ene-8-sulfonyl}-ethyl)-benzamide;

(95) 4-{2-[2-(4-chloro-3-methyl-phenyl)-4-oxo-1,3,8-triaza-spiro[4.5]dec-1-ene-8-sulfonyl]-ethyl}-3,N,N-trimethyl-benzamide;

(96) 4-{2-[2-(3-fluoro-4-trifluoromethyl-phenyl)-4-oxo-1,3,8-triaza-spiro[4.5]dec-1-ene-8-sulfonyl]-ethyl}-3,N,N-trimethyl-benzamide;

(98) 4-{2-[2-(3,4-dichloro-phenyl)-4-oxo-1,3,8-triaza-spiro[4.5]dec-1-ene-8-sulfonyl]-ethyl}-3,N,N-trimethyl-benzamide;

(99) 3,N,N-trimethyl-4-{2-[4-oxo-2-(3-trifluoromethoxy-phenyl)-1,3,8-triaza-spiro[4.5]dec-1-ene-8-sulfonyl]-ethyl}-benzamide;

(100) 4-{2-[2-(2,4-bis-trifluoromethyl-phenyl)-4-oxo-1,3,8-triaza-spiro[4.5]dec-1-ene-8-sulfonyl]-ethyl}-3,N,N-trimethyl-benzamide;

(105) 3,N,N-trimethyl-4-{2-[4-oxo-2-(2-trifluoromethoxy-phenyl)-1,3,8-triaza-spiro[4.5]dec-1-ene-8-sulfonyl]-ethyl}-benzamide;

(106) 3,N,N-trimethyl-4-{2-[4-oxo-2-(4-trifluoromethoxy-phenyl)-1,3,8-triaza-spiro[4.5]dec-1-ene-8-sulfonyl]-ethyl}-benzamide;

(107) 4-{2-[2-(4-fluoro-3-trifluoromethyl-phenyl)-4-oxo-1,3,8-triaza-spiro[4.5]dec-1-ene-8-sulfonyl]-ethyl}-3,N,N-trimethyl-benzamide;

(109) 4-{2-[2-(3-fluoro-phenyl)-4-oxo-1,3,8-triaza-spiro[4.5]dec-1-ene-8-sulfonyl]-ethyl}-3,N,N-trimethyl-benzamide;

(110) 4-{2-[2-(3-methanesulfonyl-phenyl)-4-oxo-1,3,8-triaza-spiro[4.5]dec-1-ene-8-sulfonyl]-ethyl}-3,N,N-trimethyl-benzamide;

(111) 3,N,N-trimethyl-4-{2-[2-(2-methyl-3-trifluoromethyl-phenyl)-4-oxo-1,3,8-triaza-spiro[4.5]dec-1-ene-8-sulfonyl]-ethyl}-benzamide;

(112) 3,N,N-trimethyl-4-{2-[2-(2-methyl-5-trifluoromethyl-phenyl)-4-oxo-1,3,8-triaza-spiro[4.5]dec-1-ene-8-sulfonyl]-ethyl}-benzamide;

(113) 4-{2-[2-(2,3-dimethyl-phenyl)-4-oxo-1,3,8-triaza-spiro[4.5]dec-1-ene-8-sulfonyl]-ethyl}-3,N,N-trimethyl-benzamide;

(114) 4-{2-[2-(3-fluoro-2-methyl-phenyl)-4-oxo-1,3,8-triaza-spiro[4.5]dec-1-ene-8-sulfonyl]-ethyl}-3,N,N-trimethyl-benzamide;

(115) 4-{2-[2-(3-fluoro-5-trifluoromethyl-phenyl)-4-oxo-1,3,8-triaza-spiro[4.5]dec-1-ene-8-sulfonyl]-ethyl}-3,N,N-trimethyl-benzamide;

(116) 4-{2-[2-(2-fluoro-3-trifluoromethyl-phenyl)-4-oxo-1,3,8-triaza-spiro[4.5]dec-1-ene-8-sulfonyl]-ethyl}-3,N,N-trimethyl-benzamide;

(117) 4-{2-[2-(4-fluoro-3-methyl-phenyl)-4-oxo-1,3,8-triaza-spiro[4.5]dec-1-ene-8-sulfonyl]-ethyl}-3,N,N-trimethyl-benzamide;

(118) 4-{2-[2-(4-difluoromethoxy-phenyl)-4-oxo-1,3,8-triaza-spiro[4.5]dec-1-ene-8-sulfonyl]-ethyl}-3,N,N-trimethyl-benzamide;

(126) 4-{2-[2-(4-chloro-3-trifluoromethyl-phenyl)-4-oxo-1,3,8-triaza-spiro[4.5]dec-1-ene-8-sulfonyl]-ethyl}-3,N,N-trimethyl-benzamide;

(127) 4-{2-[2-(3-chloro-5-trifluoromethyl-phenyl)-4-oxo-1,3,8-triaza-spiro[4.5]dec-1-ene-8-sulfonyl]-ethyl}-3,N,N-trimethyl-benzamide;

(128) 4-{2-[2-(4-chloro-2-methyl-phenyl)-4-oxo-1,3,8-triaza-spiro[4.5]dec-1-ene-8-sulfonyl]-ethyl}-3,N,N-trimethyl-benzamide;

(129) 4-{2-[2-(4-chloro-2-fluoro-phenyl)-4-oxo-1,3,8-triaza-spiro[4.5]dec-1-ene-8-sulfonyl]-ethyl}-3,N,N-trimethyl-benzamide;

(130) 4-{2-[2-(3-isopropoxymethyl-phenyl)-4-oxo-1,3,8-triaza-spiro[4.5]dec-1-ene-8-sulfonyl]-ethyl}-3,N,N-trimethyl-benzamide;

(133) 4-{2-[2-(3-chloro-2-methyl-phenyl)-4-oxo-1,3,8-triaza-spiro[4.5]dec-1-ene-8-sulfonyl]-ethyl}-3,N,N-trimethyl-benzamide;

(139) 4-{2-[2-(2-fluoro-4-trifluoromethyl-phenyl)-4-oxo-1,3,8-triaza-spiro[4.5]dec-1-ene-8-sulfonyl]-ethyl}-3,N,N-trimethyl-benzamide;

(140) 3,N,N-trimethyl-4-(2-{4-oxo-2-[3-(1,1,2,2-tetrafluoro-ethoxy)-phenyl]-1,3,8-triaza-spiro[4.5]dec-1-ene-8-sulfonyl}-ethyl)-benzamide;

(144) 4-{2-[2-(4-methoxy-3-trifluoromethyl-phenyl)-4-oxo-1,3,8-triaza-spiro[4.5]dec-1-ene-8-sulfonyl]-ethyl}-3,N,N-trimethyl-benzamide;

(145) N-{3-methyl-4-[2-(4-oxo-2-m-tolyl-1,3,8-triaza-spiro[4.5]dec-1-ene-8-sulfonyl)-ethyl]-phenyl}-acetamide;

(146) N-(4-{2-[2-(2,3-dimethyl-phenyl)-4-oxo-1,3,8-triaza-spiro[4.5]dec-1-ene-8-sulfonyl]-ethyl}-3-methyl-phenyl)-acetamide;

(147) N-(4-{2-[2-(2,3-dichloro-phenyl)-4-oxo-1,3,8-triaza-spiro[4.5]dec-1-ene-8-sulfonyl]-ethyl}-3-methyl-phenyl)-acetamide;

(149) N-(2-hydroxy-ethyl)-N-(3-methyl-4-{2-[4-oxo-2-(3-trifluoromethoxy-phenyl)-1,3,8-triaza-spiro[4.5]dec-1-ene-8-sulfonyl]-ethyl}-phenyl)-acetamide;

(150) acetic acid (S)-1-acetoxymethyl-2-[acetyl-(3-methyl-4-{2-[4-oxo-2-(3-trifluoromethyl-phenyl)-1,3,8-triaza-spiro[4.5]dec-1-ene-8-sulfonyl]-ethyl}-phenyl)-amino]-ethyl ester;

(151) acetic acid (S)-1-acetoxymethyl-2-[acetyl-(3-methyl-4-{2-[4-oxo-2-(4-trifluoromethyl-phenyl)-1,3,8-triaza-spiro[4.5]dec-1-ene-8-sulfonyl]-ethyl}-phenyl)-amino]-ethyl ester;

(152) acetic acid (S)-1-acetoxymethyl-2-[acetyl-(3-methyl-4-{2-[4-oxo-2-(4-trifluoromethoxy-phenyl)-1,3,8-triaza-spiro[4.5]dec-1-ene-8-sulfonyl]-ethyl}-phenyl)-amino]-ethyl ester;

(153) acetic acid (S)-1-acetoxymethyl-2-[acetyl-(4-{2-[2-(4-fluoro-3-trifluoromethyl-phenyl)-4-oxo-1,3,8-triaza-spiro[4.5]dec-1-ene-8-sulfonyl]-ethyl}-3-methyl-phenyl)-amino]-ethyl ester;

(154) 8-{2-[4-((S)-2,3-dihydroxy-propylamino)-2-methyl-phenyl]-ethanesulfonyl}-2-(4-trifluoromethyl-phenyl)-1,3,8-triaza-spiro[4.5]dec-1-en-4-one;

(155) 8-{2-[4-((S)-2,3-dihydroxy-propylamino)-2-methyl-phenyl]-ethanesulfonyl}-2-(3-trifluoromethyl-phenyl)-1,3,8-triaza-spiro[4.5]dec-1-en-4-one;

(156) 8-{2-[4-((S)-2,3-dihydroxy-propylamino)-2-methyl-phenyl]-ethanesulfonyl}-2-(4-trifluoromethoxy-phenyl)-1,3,8-triaza-spiro[4.5]dec-1-en-4-one;

(157) 2-(3-chloro-phenyl)-8-{2-[4-((S)-2,3-dihydroxy-propylamino)-2-methyl-phenyl]-ethanesulfonyl}-1,3,8-triaza-spiro[4.5]dec-1-en-4-one;

(158) 2-(4-chloro-phenyl)-8-{2-[4-((S)-2,3-dihydroxy-propylamino)-2-methyl-phenyl]-ethanesulfonyl}-1,3,8-triaza-spiro[4.5]dec-1-en-4-one;

(159) 8-{2-[4-(2-hydroxy-ethylamino)-2-methyl-phenyl]-ethanesulfonyl}-2-(3-trifluoromethoxy-phenyl)-1,3,8-triaza-spiro[4.5]dec-1-en-4-one;

(160) 8-{2-[4-(2-hydroxy-ethylamino)-2-methyl-phenyl]-ethanesulfonyl}-2-(3-trifluoromethyl-phenyl)-1,3,8-triaza-spiro[4.5]dec-1-en-4-one;

(161) 8-{2-[4-(2-hydroxy-ethylamino)-2-methyl-phenyl]-ethanesulfonyl}-2-(4-trifluoromethyl-phenyl)-1,3,8-triaza-spiro[4.5]dec-1-en-4-one;

(164) (4-{2-[2-(4-fluoro-3-trifluoromethyl-phenyl)-4-oxo-1,3,8-triaza-spiro[4.5]dec-1-ene-8-sulfonyl]-ethyl}-3-methyl-benzyl)-carbamic acid tert-butyl ester;

(168) 3,N,N-trimethyl-4-(2-{4-oxo-2-[3-(2,2,2-trifluoro-ethoxymethyl)-phenyl]-1,3,8-triaza-spiro[4.5]dec-1-ene-8-sulfonyl}-ethyl)-benzamide;

(169) 4-(2-{2-[3-(2,2-difluoro-ethoxymethyl)-phenyl]-4-oxo-1,3,8-triaza-spiro[4.5]dec-1-ene-8-sulfonyl}-ethyl)-3,N,N-trimethyl-benzamide;

(170) 3,N,N-trimethyl-4-(2-{4-oxo-2-[3-(2,2,3,3-tetrafluoro-propoxymethyl)-phenyl]-1,3,8-triaza-spiro[4.5]dec-1-ene-8-sulfonyl}-ethyl)-benzamide;

(171) 4-(2-{2-[3-(3,5-dimethyl-isoxazol-4-yl)-phenyl]-4-oxo-1,3,8-triaza-spiro[4.5]dec-1-ene-8-sulfonyl}-ethyl)-3,N,N-trimethyl-benzamide;

(172) 4-[2-(2-biphenyl-3-yl-4-oxo-1,3,8-triaza-spiro[4.5]dec-1-ene-8-sulfonyl)-ethyl]-3,N,N-trimethyl-benzamide;

(173) 3,N,N-trimethyl-4-{2-[4-oxo-2-(3-pyridin-3-yl-phenyl)-1,3,8-triaza-spiro[4.5]dec-1-ene-8-sulfonyl]-ethyl}-benzamide;

(174) 3-{8-[2-(4-dimethylcarbamoyl-2-methyl-phenyl)-ethanesulfonyl]-4-oxo-1,3,8-triaza-spiro[4.5]dec-1-en-2-yl}-benzoic acid methyl ester;

(194) 3-{4-[(E)-2-(2-cyclohexyl-4-oxo-1,3,8-triaza-spiro[4.5]dec-1-ene-8-sulfonyl)-vinyl]-3-trifluoromethyl-phenyl}-1,1-dimethyl-urea;

(195) cyclopropanecarboxylic acid {4-[(E)-2-(2-cyclohexyl-4-oxo-1,3,8-triaza-spiro[4.5]dec-1-ene-8-sulfonyl)-vinyl]-3-trifluoromethyl-phenyl}-amide;

(196) N-{4-[(E)-2-(2-cyclohexyl-4-oxo-1,3,8-triaza-spiro[4.5]dec-1-ene-8-sulfonyl)-vinyl]-3-trifluoromethyl-phenyl}-2-hydroxy-acetamide;

(198) 1-{4-[(E)-2-(2-cyclohexyl-4-oxo-1,3,8-triaza-spiro[4.5]dec-1-ene-8-sulfonyl)-vinyl]-3-trifluoromethyl-phenyl}-3-(2-hydroxy-ethyl)-urea;

(201) 2-{4-[(E)-2-(2-cyclohexyl-4-oxo-1,3,8-triaza-spiro[4.5]dec-1-ene-8-sulfonyl)-vinyl]-3-trifluoromethyl-phenylamino}-N,N-dimethyl-acetamide;

(203) 2-cyclohexyl-8-{(E)-2-[2-methyl-4-(3,3,4,4-tetrafluoro-pyrrolidine-1-carbonyl)-phenyl]-ethenesulfonyl}-1,3,8-triaza-spiro[4.5]dec-1-en-4-one;

(204) N-{4-[(E)-2-(2-cyclohexyl-4-oxo-1,3,8-triaza-spiro[4.5]dec-1-ene-8-sulfonyl)-vinyl]-3,5-dimethyl-phenyl}-acetamide;

(205) {4-[(E)-2-(2-cyclohexyl-4-oxo-1,3,8-triaza-spiro[4.5]dec-1-ene-8-sulfonyl)-vinyl]-3-trifluoromethyl-benzyl}-carbamic acid tert-butyl ester;

(206) 2-cyclohexyl-8-{(E)-2-[4-((R)-2,3-dihydroxy-propoxy)-2,6-dimethyl-phenyl]-ethenesulfonyl}-1,3,8-triaza-spiro[4.5]dec-1-en-4-one;

(210) 8-{(E)-2-[4-(3,4-dihydroxy-butoxy)-2-methyl-phenyl]-ethenesulfonyl}-2-(3-trifluoromethyl-phenyl)-1,3,8-triaza-spiro[4.5]dec-1-en-4-one;

(211) 8-{(E)-2-[4-(2-hydroxy-ethylamino)-2-trifluoromethyl-phenyl]-ethenesulfonyl}-2-(3-trifluoromethyl-phenyl)-1,3,8-triaza-spiro[4.5]dec-1-en-4-one;

(212) 8-{(E)-2-[2-methyl-4-(pyrrolidine-1-carbonyl)-phenyl]-ethenesulfonyl}-2-(3-trifluoromethyl-phenyl)-1,3,8-triaza-spiro[4.5]dec-1-en-4-one;

(213) 3-methyl-4-{(E)-2-[4-oxo-2-(3-trifluoromethyl-phenyl)-1,3,8-triaza-spiro[4.5]dec-1-ene-8-sulfonyl]-vinyl}-benzenesulfonamide;

(214) N-(2-hydroxy-ethyl)-3,N-dimethyl-4-{(E)-2-[4-oxo-2-(3-trifluoromethyl-phenyl)-1,3,8-triaza-spiro[4.5]dec-1-ene-8-sulfonyl]-vinyl}-benzamide;

(215) N-(3-methyl-4-{(E)-2-[4-oxo-2-(3-trifluoromethyl-phenyl)-1,3,8-triaza-spiro[4.5]dec-1-ene-8-sulfonyl]-vinyl}-phenyl)-acetamide;

(216) 8-{(E)-2-[2-methyl-4-(4-methyl-piperazine-1-carbonyl)-phenyl]-ethenesulfonyl}-2-(3-trifluoromethyl-phenyl)-1,3,8-triaza-spiro[4.5]dec-1-en-4-one;

(217) 3-methyl-4-{(E)-2-[4-oxo-2-(3-trifluoromethyl-phenyl)-1,3,8-triaza-spiro[4.5]dec-1-ene-8-sulfonyl]-vinyl}-N-(2,2,2-trifluoro-ethyl)-benzenesulfonamide;

(218) 3-methyl-N-(2-morpholin-4-yl-ethyl)-4-{(E)-2-[4-oxo-2-(3-trifluoromethyl-phenyl)-1,3,8-triaza-spiro[4.5]dec-1-ene-8-sulfonyl]-vinyl}-benzenesulfonamide;

(219) 3-methyl-4-{(E)-2-[4-oxo-2-(3-trifluoromethyl-phenyl)-1,3,8-triaza-spiro[4.5]dec-1-ene-8-sulfonyl]-vinyl}-N-pyridin-3-yl-benzenesulfonamide;

(220) 8-{(E)-2-[4-((R)-4-hydroxy-2-oxo-pyrrolidin-1-yl)-2-methyl-phenyl]-ethenesulfonyl}-2-(3-trifluoromethyl-phenyl)-1,3,8-triaza-spiro[4.5]dec-1-en-4-one;

(221) 8-{(E)-2-[4-((R)-2-hydroxymethyl-5-oxo-pyrrolidin-1-yl)-2-methyl-phenyl]-ethenesulfonyl}-2-(3-trifluoromethyl-phenyl)-1,3,8-triaza-spiro[4.5]dec-1-en-4-one;

(222) 8-{(E)-2-[4-((R)-5-hydroxymethyl-2-oxo-oxazolidin-3-yl)-2-methyl-phenyl]-ethenesulfonyl}-2-(3-trifluoromethyl-phenyl)-1,3,8-triaza-spiro[4.5]dec-1-en-4-one;

(223) 8-((E)-2-{4-[3-(3-dimethylamino-propoxy)-azetidine-1-carbonyl]-2,6-dimethyl-phenyl}-ethenesulfonyl)-2-(3-trifluoromethyl-phenyl)-1,3,8-triaza-spiro[4.5]dec-1-en-4-one;

(224) N-(4-hydroxy-butyl)-3-methyl-4-{(E)-2-[4-oxo-2-(3-trifluoromethoxy-phenyl)-1,3,8-triaza-spiro[4.5]dec-1-ene-8-sulfonyl]-vinyl}-benzenesulfonamide;

(228) N-(3-methyl-4-{(E)-2-[4-oxo-2-(3-trifluoromethoxy-phenyl)-1,3,8-triaza-spiro[4.5]dec-1-ene-8-sulfonyl]-vinyl}-phenyl)-N-(1-methyl-piperidin-4-yl)-acetamide;

(229) N-(3,5-dimethyl-4-{(E)-2-[4-oxo-2-(3-trifluoromethoxy-phenyl)-1,3,8-triaza-spiro[4.5]dec-1-ene-8-sulfonyl]-vinyl}-phenyl)-methanesulfonamide;

(230) 8-{(E)-2-[4-(4-hydroxy-piperidine-1-carbonyl)-2-methyl-phenyl]-ethenesulfonyl}-2-(3-trifluoromethoxy-phenyl)-1,3,8-triaza-spiro[4.5]dec-1-en-4-one;

(231) 3,N,N-trimethyl-4-{(E)-2-[4-oxo-2-(3-trifluoromethoxy-phenyl)-1,3,8-triaza-spiro[4.5]dec-1-ene-8-sulfonyl]-vinyl}-benzamide;

(232) N-(2-hydroxy-ethyl)-N-(3-methyl-4-{(E)-2-[4-oxo-2-(3-trifluoromethoxy-phenyl)-1,3,8-triaza-spiro[4.5]dec-1-ene-8-sulfonyl]-vinyl}-phenyl)-acetamide;

(233) 3-fluoro-N,N-dimethyl-4-{(E)-2-[4-oxo-2-(3-trifluoromethoxy-phenyl)-1,3,8-triaza-spiro[4.5]dec-1-ene-8-sulfonyl]-vinyl}-benzamide;

(235) 8-{(E)-2-[4-(3-dimethylamino-propoxy)-2-methyl-phenyl]-ethenesulfonyl}-2-(3-trifluoromethoxy-phenyl)-1,3,8-triaza-spiro[4.5]dec-1-en-4-one;

(237) N-methyl-N-(3-methyl-4-{(E)-2-[4-oxo-2-(3-trifluoromethoxy-phenyl)-1,3,8-triaza-spiro[4.5]dec-1-ene-8-sulfonyl]-vinyl}-phenyl)-acetamide;

(238) N-(3,5-dimethyl-4-{(E)-2-[4-oxo-2-(3-trifluoromethoxy-phenyl)-1,3,8-triaza-spiro[4.5]dec-1-ene-8-sulfonyl]-vinyl}-phenyl)-acetamide;

(239) N-(3,5-dimethyl-4-{(E)-2-[4-oxo-2-(3-trifluoromethoxy-phenyl)-1,3,8-triaza-spiro[4.5]dec-1-ene-8-sulfonyl]-vinyl}-phenyl)-N-methyl-acetamide;

(242) 8-{(E)-2-[4-((R)-2,3-dihydroxy-propoxy)-2,6-dimethyl-phenyl]-ethenesulfonyl}-2-(4-fluoro-3-trifluoromethyl-phenyl)-1,3,8-triaza-spiro[4.5]dec-1-en-4-one;

(243) 8-{(E)-2-[4-((R)-2,3-dihydroxy-propoxy)-2,6-dimethyl-phenyl]-ethenesulfonyl}-2-(2-fluoro-3-trifluoromethyl-phenyl)-1,3,8-triaza-spiro[4.5]dec-1-en-4-one;

(244) 2-(2-fluoro-3-trifluoromethyl-phenyl)-8-{(E)-2-[4-(4-hydroxy-piperidine-1-carbonyl)-2,6-dimethyl-phenyl]-ethenesulfonyl}-1,3,8-triaza-spiro[4.5]dec-1-en-4-one;

(247) 8-{(E)-2-[4-(3,4-dihydroxy-butoxy)-2-methyl-phenyl]-ethenesulfonyl}-2-(2-fluoro-3-trifluoromethyl-phenyl)-1,3,8-triaza-spiro[4.5]dec-1-en-4-one;

(248) 2-(2-fluoro-3-trifluoromethyl-phenyl)-8-{(E)-2-[2-methyl-4-(pyrrolidine-1-carbonyl)-phenyl]-ethenesulfonyl}-1,3,8-triaza-spiro[4.5]dec-1-en-4-one;

(258) 8-{(E)-2-[4-((R)-2-hydroxymethyl-5-oxo-pyrrolidin-1-yl)-2,6-dimethyl-phenyl]-ethenesulfonyl}-2-(3-trifluoromethoxy-phenyl)-1,3,8-triaza-spiro[4.5]dec-1-en-4-one;

(259) N-(4-{(E)-2-[2-(2-fluoro-3-trifluoromethyl-phenyl)-4-oxo-1,3,8-triaza-spiro[4.5]dec-1-ene-8-sulfonyl]-vinyl}-3-methyl-phenyl)-N-(2-hydroxy-ethyl)-acetamide;

(260) N-(3-methyl-4-{(E)-2-[4-oxo-2-(3-trifluoromethoxy-phenyl)-1,3,8-triaza-spiro[4.5]dec-1-ene-8-sulfonyl]-vinyl}-phenyl)-N-piperidin-4-yl-acetamide;

(268) 8-{2-[4-((R)-2-hydroxymethyl-5-oxo-pyrrolidin-1-yl)-2-methyl-phenyl]-ethanesulfonyl}-2-(3-trifluoromethyl-phenyl)-1,3,8-triaza-spiro[4.5]dec-1-en-4-one;

(270) 2-{4-[2-(2-cyclohexyl-4-oxo-1,3,8-triaza-spiro[4.5]dec-1-ene-8-sulfonyl)-ethyl]-3-trifluoromethyl-phenylamino}-N,N-dimethyl-acetamide;

(271) cyclopropanecarboxylic acid {4-[2-(2-cyclohexyl-4-oxo-1,3,8-triaza-spiro[4.5]dec-1-ene-8-sulfonyl)-ethyl]-3-trifluoromethyl-phenyl}-amide;

(272) {4-[2-(2-cyclohexyl-4-oxo-1,3,8-triaza-spiro[4.5]dec-1-ene-8-sulfonyl)-ethyl]-3-trifluoromethyl-benzyl}-carbamic acid tert-butyl ester;

(273) 3-{4-[2-(2-cyclohexyl-4-oxo-1,3,8-triaza-spiro[4.5]dec-1-ene-8-sulfonyl)-ethyl]-3-trifluoromethyl-phenyl}-1,1-dimethyl-urea;

(278) 1-{4-[2-(2-cyclohexyl-4-oxo-1,3,8-triaza-spiro[4.5]dec-1-ene-8-sulfonyl)-ethyl]-3-trifluoromethyl-phenyl}-3-(2-hydroxy-ethyl)-urea;

(279) 2-cyclohexyl-8-{2-[4-((R)-2,3-dihydroxy-propoxy)-2,6-dimethyl-phenyl]-ethanesulfonyl}-1,3,8-triaza-spiro[4.5]dec-1-en-4-one;

(283) 2-cyclohexyl-8-{2-[2-methyl-4-(3,3,4,4-tetrafluoro-pyrrolidine-1-carbonyl)-phenyl]-ethanesulfonyl}-1,3,8-triaza-spiro[4.5]dec-1-en-4-one;

(284) 8-{2-[4-(3,4-dihydroxy-butoxy)-2-methyl-phenyl]-ethanesulfonyl}-2-(3-trifluoromethyl-phenyl)-1,3,8-triaza-spiro[4.5]dec-1-en-4-one;

(285) 8-{2-[4-(4-hydroxy-piperidine-1-carbonyl)-2-methyl-phenyl]-ethanesulfonyl}-2-(3-trifluoromethoxy-phenyl)-1,3,8-triaza-spiro[4.5]dec-1-en-4-one;

(286) 8-{2-[4-(2-hydroxy-ethylamino)-2-trifluoromethyl-phenyl]-ethanesulfonyl}-2-(3-trifluoromethyl-phenyl)-1,3,8-triaza-spiro[4.5]dec-1-en-4-one;

(287) N-(4-hydroxy-butyl)-3-methyl-4-{2-[4-oxo-2-(3-trifluoromethoxy-phenyl)-1,3,8-triaza-spiro[4.5]dec-1-ene-8-sulfonyl]-ethyl}-benzenesulfonamide;

(288) 8-{2-[2-methyl-4-(pyrrolidine-1-carbonyl)-phenyl]-ethanesulfonyl}-2-(3-trifluoromethyl-phenyl)-1,3,8-triaza-spiro[4.5]dec-1-en-4-one;

(289) 8-{2-[2-methyl-4-(4-methyl-piperazine-1-carbonyl)-phenyl]-ethanesulfonyl}-2-(3-trifluoromethyl-phenyl)-1,3,8-triaza-spiro[4.5]dec-1-en-4-one;

(290) 3-methyl-4-{2-[4-oxo-2-(3-trifluoromethyl-phenyl)-1,3,8-triaza-spiro[4.5]dec-1-ene-8-sulfonyl]-ethyl}-N-(2,2,2-trifluoro-ethyl)-benzenesulfonamide;

(291) 3-methyl-4-{2-[4-oxo-2-(3-trifluoromethyl-phenyl)-1,3,8-triaza-spiro[4.5]dec-1-ene-8-sulfonyl]-ethyl}-benzenesulfonamide;

(292) 3-methyl-N-(2-morpholin-4-yl-ethyl)-4-{2-[4-oxo-2-(3-trifluoromethyl-phenyl)-1,3,8-triaza-spiro[4.5]dec-1-ene-8-sulfonyl]-ethyl}-benzenesulfonamide;

(293) 3-fluoro-N,N-dimethyl-4-{2-[4-oxo-2-(3-trifluoromethoxy-phenyl)-1,3,8-triaza-spiro[4.5]dec-1-ene-8-sulfonyl]-ethyl}-benzamide;

(294) 3-methyl-4-{2-[4-oxo-2-(3-trifluoromethyl-phenyl)-1,3,8-triaza-spiro[4.5]dec-1-ene-8-sulfonyl]-ethyl}-N-pyridin-3-yl-benzenesulfonamide;

(295) 8-{2-[4-(3-dimethylamino-propoxy)-2-methyl-phenyl]-ethanesulfonyl}-2-(3-trifluoromethoxy-phenyl)-1,3,8-triaza-spiro[4.5]dec-1-en-4-one;

(296) 8-{2-[4-((R)-5-hydroxymethyl-2-oxo-oxazolidin-3-yl)-2-methyl-phenyl]-ethanesulfonyl}-2-(3-trifluoromethyl-phenyl)-1,3,8-triaza-spiro[4.5]dec-1-en-4-one;

(297) 8-{2-[4-((R)-4-hydroxy-2-oxo-pyrrolidin-1-yl)-2-methyl-phenyl]-ethanesulfonyl}-2-(3-trifluoromethyl-phenyl)-1,3,8-triaza-spiro[4.5]dec-1-en-4-one;

(298) N-(3-methyl-4-{2-[4-oxo-2-(3-trifluoromethyl-phenyl)-1,3,8-triaza-spiro[4.5]dec-1-ene-8-sulfonyl]-ethyl}-phenyl)-acetamide;

(299) N-methyl-N-(3-methyl-4-{2-[4-oxo-2-(3-trifluoromethoxy-phenyl)-1,3,8-triaza-spiro[4.5]dec-1-ene-8-sulfonyl]-ethyl}-phenyl)-acetamide;

(300) 2-hydroxy-N-methyl-N-(3-methyl-4-{2-[4-oxo-2-(3-trifluoromethoxy-phenyl)-1,3,8-triaza-spiro[4.5]dec-1-ene-8-sulfonyl]-ethyl}-phenyl)-acetamide;

(301) 1-methyl-1-(3-methyl-4-{2-[4-oxo-2-(3-trifluoromethoxy-phenyl)-1,3,8-triaza-spiro[4.5]dec-1-ene-8-sulfonyl]-ethyl}-phenyl)-urea;

(302) N-{4-[2-(2-cyclohexyl-4-oxo-1,3,8-triaza-spiro[4.5]dec-1-ene-8-sulfonyl)-ethyl]-3,5-dimethyl-phenyl}-acetamide;

(314) 8-[2-(4-amino-2-trifluoromethyl-phenyl)-ethanesulfonyl]-2-cyclohexyl-1,3,8-triaza-spiro[4.5]dec-1-en-4-one;

(321) 2-cyclohexyl-8-{2-[4-((S)-2,3-dihydroxy-propylamino)-2-methyl-phenyl]-ethanesulfonyl}-1,3,8-triaza-spiro[4.5]dec-1-en-4-one;

(325) 8-{2-[4-((R)-2,3-dihydroxy-propoxy)-2-methyl-phenyl]-ethanesulfonyl}-2-(3-trifluoromethoxy-phenyl)-1,3,8-triaza-spiro[4.5]dec-1-en-4-one;

(352) 8-{2-[4-(4-methanesulfonyl-piperazine-1-carbonyl)-2-methyl-phenyl]-ethanesulfonyl}-2-(3-trifluoromethyl-phenyl)-1,3,8-triaza-spiro[4.5]dec-1-en-4-one;

(353) N—[(R)-1-(3-methyl-4-{2-[4-oxo-2-(3-trifluoromethyl-phenyl)-1,3,8-triaza-spiro[4.5]dec-1-ene-8-sulfonyl]-ethyl}-benzoyl)-pyrrolidin-3-yl]-acetamide;

(354) 8-{2-[2-methyl-4-((S)-2-trifluoromethyl-pyrrolidine-1-carbonyl)-phenyl]-ethanesulfonyl}-2-(3-trifluoromethyl-phenyl)-1,3,8-triaza-spiro[4.5]dec-1-en-4-one;

(355) 8-{2-[4-((R)-3-hydroxy-pyrrolidine-1-carbonyl)-2-methyl-phenyl]-ethanesulfonyl}-2-(3-trifluoromethyl-phenyl)-1,3,8-triaza-spiro[4.5]dec-1-en-4-one;

(356) 8-{2-[4-((S)-2-hydroxymethyl-pyrrolidine-1-carbonyl)-2-methyl-phenyl]-ethanesulfonyl}-2-(3-trifluoromethyl-phenyl)-1,3,8-triaza-spiro[4.5]dec-1-en-4-one;

(357) 8-(2-{4-[4-(2-hydroxy-ethyl)-piperidine-1-carbonyl]-2-methyl-phenyl}-ethanesulfonyl)-2-(3-trifluoromethyl-phenyl)-1,3,8-triaza-spiro[4.5]dec-1-en-4-one;

(358) 8-(2-{2-methyl-4-[4-(3-methyl-[1,2,4]oxadiazol-5-yl)-piperidine-1-carbonyl]-phenyl}-ethanesulfonyl)-2-(3-trifluoromethyl-phenyl)-1,3,8-triaza-spiro[4.5]dec-1-en-4-one;

(359) 8-{2-[2-methyl-4-(4-pyrimidin-2-yl-piperazine-1-carbonyl)-phenyl]-ethanesulfonyl}-2-(3-trifluoromethyl-phenyl)-1,3,8-triaza-spiro[4.5]dec-1-en-4-one;

(360) 4-(3-methyl-4-{2-[4-oxo-2-(3-trifluoromethyl-phenyl)-1,3,8-triaza-spiro[4.5]dec-1-ene-8-sulfonyl]-ethyl}-benzoyl)-piperazine-1-sulfonic acid dimethylamide;

(361) 8-{2-[2-methyl-4-(4-pyridin-2-yl-piperazine-1-carbonyl)-phenyl]-ethanesulfonyl}-2-(3-trifluoromethyl-phenyl)-1,3,8-triaza-spiro[4.5]dec-1-en-4-one;

(362) 8-[2-(4-{4-[2-(2-hydroxy-ethoxy)-ethyl]-piperazine-1-carbonyl}-2-methyl-phenyl)-ethanesulfonyl]-2-(3-trifluoromethyl-phenyl)-1,3,8-triaza-spiro[4.5]dec-1-en-4-one;

(363) 8-(2-{2-methyl-4-[4-(2-morpholin-4-yl-ethyl)-piperazine-1-carbonyl]-phenyl}-ethanesulfonyl)-2-(3-trifluoromethyl-phenyl)-1,3,8-triaza-spiro[4.5]dec-1-en-4-one;

(364) 8-{2-[2-methyl-4-(4-thiazol-2-yl-piperazine-1-carbonyl)-phenyl]-ethanesulfonyl}-2-(3-trifluoromethyl-phenyl)-1,3,8-triaza-spiro[4.5]dec-1-en-4-one;

(365) 8-{2-[4-(4,4-difluoro-piperidine-1-carbonyl)-2-methyl-phenyl]-ethanesulfonyl}-2-(3-trifluoromethyl-phenyl)-1,3,8-triaza-spiro[4.5]dec-1-en-4-one;

(366) 8-(2-{4-[4-(3-hydroxy-propyl)-piperazine-1-carbonyl]-2-methyl-phenyl}-ethanesulfonyl)-2-(3-trifluoromethyl-phenyl)-1,3,8-triaza-spiro[4.5]dec-1-en-4-one;

(367) (S)-1-(3-methyl-4-{2-[4-oxo-2-(3-trifluoromethyl-phenyl)-1,3,8-triaza-spiro[4.5]dec-1-ene-8-sulfonyl]-ethyl}-benzoyl)-pyrrolidine-2-carboxylic acid amide;

(368) 8-{2-[2-methyl-4-(3,3,4,4-tetrafluoro-pyrrolidine-1-carbonyl)-phenyl]-ethanesulfonyl}-2-(3-trifluoromethyl-phenyl)-1,3,8-triaza-spiro[4.5]dec-1-en-4-one;

(369) (R)-1-(3-methyl-4-{2-[4-oxo-2-(3-trifluoromethyl-phenyl)-1,3,8-triaza-spiro[4.5]dec-1-ene-8-sulfonyl]-ethyl}-benzoyl)-pyrrolidine-2-carboxylic acid amide;

(370) 8-{2-[4-((S)-3-hydroxy-pyrrolidine-1-carbonyl)-2-methyl-phenyl]-ethanesulfonyl}-2-(3-trifluoromethyl-phenyl)-1,3,8-triaza-spiro[4.5]dec-1-en-4-one;

(371) 8-{2-[4-((R)-2-hydroxymethyl-pyrrolidine-1-carbonyl)-2-methyl-phenyl]-ethanesulfonyl}-2-(3-trifluoromethyl-phenyl)-1,3,8-triaza-spiro[4.5]dec-1-en-4-one;

(372) 8-{2-[4-((S)-3-dimethylamino-pyrrolidine-1-carbonyl)-2-methyl-phenyl]-ethanesulfonyl}-2-(3-trifluoromethyl-phenyl)-1,3,8-triaza-spiro[4.5]dec-1-en-4-one;

(373) 8-{2-[4-(4-tert-butyl-piperazine-1-carbonyl)-2-methyl-phenyl]-ethanesulfonyl}-2-(3-trifluoromethyl-phenyl)-1,3,8-triaza-spiro[4.5]dec-1-en-4-one;

(374) 8-(2-{4-[4-(3-dimethylamino-propyl)-piperazine-1-carbonyl]-2-methyl-phenyl}-ethanesulfonyl)-2-(3-trifluoromethyl-phenyl)-1,3,8-triaza-spiro[4.5]dec-1-en-4-one;

(375) 8-(2-{4-[4-(4-fluoro-phenyl)-piperazine-1-carbonyl]-2-methyl-phenyl}-ethanesulfonyl)-2-(3-trifluoromethyl-phenyl)-1,3,8-triaza-spiro[4.5]dec-1-en-4-one;

(376) 8-{2-[4-(4-isopropyl-piperazine-1-carbonyl)-2-methyl-phenyl]-ethanesulfonyl}-2-(3-trifluoromethyl-phenyl)-1,3,8-triaza-spiro[4.5]dec-1-en-4-one;

(377) 8-{2-[4-(3-hydroxy-azetidine-1-carbonyl)-2-methyl-phenyl]-ethanesulfonyl}-2-(3-trifluoromethyl-phenyl)-1,3,8-triaza-spiro[4.5]dec-1-en-4-one;

(378) 8-{2-[4-(3-fluoro-pyrrolidine-1-carbonyl)-2-methyl-phenyl]-ethanesulfonyl}-2-(3-trifluoromethyl-phenyl)-1,3,8-triaza-spiro[4.5]dec-1-en-4-one;

(379) 8-{2-[4-(3-fluoro-azetidine-1-carbonyl)-2-methyl-phenyl]-ethanesulfonyl}-2-(3-trifluoromethyl-phenyl)-1,3,8-triaza-spiro[4.5]dec-1-en-4-one;

(380) 8-{2-[2-methyl-4-(piperidine-1-carbonyl)-phenyl]-ethanesulfonyl}-2-(3-trifluoromethyl-phenyl)-1,3,8-triaza-spiro[4.5]dec-1-en-4-one;

(381) 8-{2-[4-(azetidine-1-carbonyl)-2-methyl-phenyl]-ethanesulfonyl}-2-(3-trifluoromethyl-phenyl)-1,3,8-triaza-spiro[4.5]dec-1-en-4-one;

(382) 4-(3-methyl-4-{2-[4-oxo-2-(3-trifluoromethyl-phenyl)-1,3,8-triaza-spiro[4.5]dec-1-ene-8-sulfonyl]-ethyl}-benzoyl)-piperazine-1-carboxylic acid dimethylamide;

(383) 3,5,N,N-tetramethyl-4-{(E)-2-[4-oxo-2-(3-trifluoromethyl-phenyl)-1,3,8-triaza-spiro[4.5]dec-1-ene-8-sulfonyl]-vinyl}-benzamide;

(384) 8-{(E)-2-[4-(4-hydroxy-piperidine-1-carbonyl)-2,6-dimethyl-phenyl]-ethenesulfonyl}-2-(3-trifluoromethyl-phenyl)-1,3,8-triaza-spiro[4.5]dec-1-en-4-one;

(385) 8-{(E)-2-[4-(3-hydroxy-azetidine-1-carbonyl)-2,6-dimethyl-phenyl]-ethenesulfonyl}-2-(3-trifluoromethyl-phenyl)-1,3,8-triaza-spiro[4.5]dec-1-en-4-one;

(386) 8-{(E)-2-[4-(4-hydroxy-4-hydroxymethyl-piperidine-1-carbonyl)-2,6-dimethyl-phenyl]-ethenesulfonyl}-2-(3-trifluoromethyl-phenyl)-1,3,8-triaza-spiro[4.5]dec-1-en-4-one;

(387) 8-{(E)-2-[4-((3R,4R)-3-dimethylamino-4-hydroxy-pyrrolidine-1-carbonyl)-2,6-dimethyl-phenyl]-ethenesulfonyl}-2-(3-trifluoromethyl-phenyl)-1,3,8-triaza-spiro[4.5]dec-1-en-4-one;

(388) 8-{(E)-2-[2,6-dimethyl-4-(pyrrolidine-1-carbonyl)-phenyl]-ethenesulfonyl}-2-(3-trifluoromethyl-phenyl)-1,3,8-triaza-spiro[4.5]dec-1-en-4-one;

(389) N-(3-hydroxy-propyl)-3,5,N-trimethyl-4-{(E)-2-[4-oxo-2-(3-trifluoromethyl-phenyl)-1,3,8-triaza-spiro[4.5]dec-1-ene-8-sulfonyl]-vinyl}-benzamide;

(390) N-(2-dimethylamino-ethyl)-3,5,N-trimethyl-4-{(E)-2-[4-oxo-2-(3-trifluoromethyl-phenyl)-1,3,8-triaza-spiro[4.5]dec-1-ene-8-sulfonyl]-vinyl}-benzamide;

(391) N-(3-dimethylamino-propyl)-3,5,N-trimethyl-4-{(E)-2-[4-oxo-2-(3-trifluoromethyl-phenyl)-1,3,8-triaza-spiro[4.5]dec-1-ene-8-sulfonyl]-vinyl}-benzamide;

(392) N-carbamoylmethyl-3,5,N-trimethyl-4-{(E)-2-[4-oxo-2-(3-trifluoromethyl-phenyl)-1,3,8-triaza-spiro[4.5]dec-1-ene-8-sulfonyl]-vinyl}-benzamide;

(393) 3,5,N-trimethyl-N-(1-methyl-piperidin-4-yl)-4-{(E)-2-[4-oxo-2-(3-trifluoromethyl-phenyl)-1,3,8-triaza-spiro[4.5]dec-1-ene-8-sulfonyl]-vinyl}-benzamide;

(394) 8-{(E)-2-[4-(4-acetyl-piperazine-1-carbonyl)-2,6-dimethyl-phenyl]-ethenesulfonyl}-2-(3-trifluoromethoxy-phenyl)-1,3,8-triaza-spiro[4.5]dec-1-en-4-one;

(395) 4-(3,5-dimethyl-4-{(E)-2-[4-oxo-2-(3-trifluoromethoxy-phenyl)-1,3,8-triaza-spiro[4.5]dec-1-ene-8-sulfonyl]-vinyl}-benzoyl)-piperazine-1-carboxylic acid dimethylamide;

(396) 4-(3,5-dimethyl-4-{(E)-2-[4-oxo-2-(3-trifluoromethoxy-phenyl)-1,3,8-triaza-spiro[4.5]dec-1-ene-8-sulfonyl]-vinyl}-benzoyl)-piperazine-1-carboxylic acid amide;

(397) 8-((E)-2-{4-[4-(3-dimethylamino-propyl)-piperazine-1-carbonyl]-2,6-dimethyl-phenyl}-ethenesulfonyl)-2-(3-trifluoromethoxy-phenyl)-1,3,8-triaza-spiro[4.5]dec-1-en-4-one;

(398) 8-{(E)-2-[2,6-dimethyl-4-((R)-3-methylamino-pyrrolidine-1-carbonyl)-phenyl]-ethenesulfonyl}-2-(3-trifluoromethoxy-phenyl)-1,3,8-triaza-spiro[4.5]dec-1-en-4-one;

(399) 8-{(E)-2-[4-((R)-3-dimethylamino-pyrrolidine-1-carbonyl)-2,6-dimethyl-phenyl]-ethenesulfonyl}-2-(3-trifluoromethoxy-phenyl)-1,3,8-triaza-spiro[4.5]dec-1-en-4-one;

(400) 8-{(E)-2-[4-(4-hydroxy-piperidine-1-carbonyl)-2,6-dimethyl-phenyl]-ethenesulfonyl}-2-(3-trifluoromethoxy-phenyl)-1,3,8-triaza-spiro[4.5]dec-1-en-4-one;

(401) 8-{(E)-2-[4-((R)-3-hydroxy-pyrrolidine-1-carbonyl)-2,6-dimethyl-phenyl]-ethenesulfonyl}-2-(3-trifluoromethoxy-phenyl)-1,3,8-triaza-spiro[4.5]dec-1-en-4-one;

(402) 8-{(E)-2-[4-((S)-3-hydroxy-pyrrolidine-1-carbonyl)-2,6-dimethyl-phenyl]-ethenesulfonyl}-2-(3-trifluoromethoxy-phenyl)-1,3,8-triaza-spiro[4.5]dec-1-en-4-one;

(403) 8-{(E)-2-[4-(4-hydroxy-4-hydroxymethyl-piperidine-1-carbonyl)-2,6-dimethyl-phenyl]-ethenesulfonyl}-2-(3-trifluoromethoxy-phenyl)-1,3,8-triaza-spiro[4.5]dec-1-en-4-one;

(404) 8-{(E)-2-[4-((R)-3-amino-pyrrolidine-1-carbonyl)-2,6-dimethyl-phenyl]-ethenesulfonyl}-2-(3-trifluoromethoxy-phenyl)-1,3,8-triaza-spiro[4.5]dec-1-en-4-one;

(405) 8-{(E)-2-[4-(4-dimethylamino-piperidine-1-carbonyl)-2,6-dimethyl-phenyl]-ethenesulfonyl}-2-(3-trifluoromethoxy-phenyl)-1,3,8-triaza-spiro[4.5]dec-1-en-4-one;

(406) 8-{(E)-2-[4-((3S,4S)-3-hydroxy-4-isopropylamino-pyrrolidine-1-carbonyl)-2,6-dimethyl-phenyl]-ethenesulfonyl}-2-(3-trifluoromethoxy-phenyl)-1,3,8-triaza-spiro[4.5]dec-1-en-4-one;

(407) 8-((E)-2-{4-[4-(2-dimethylamino-ethoxy)-piperidine-1-carbonyl]-2,6-dimethyl-phenyl}-ethenesulfonyl)-2-(3-trifluoromethoxy-phenyl)-1,3,8-triaza-spiro[4.5]dec-1-en-4-one;

(408) 8-{(E)-2-[4-(3-hydroxy-azetidine-1-carbonyl)-2,6-dimethyl-phenyl]-ethenesulfonyl}-2-(3-trifluoromethoxy-phenyl)-1,3,8-triaza-spiro[4.5]dec-1-en-4-one;

(416) 8-(2-{4-[4-(2-hydroxy-ethyl)-piperazine-1-carbonyl]-2-methyl-phenyl}-ethanesulfonyl)-2-(3-trifluoromethoxy-phenyl)-1,3,8-triaza-spiro[4.5]dec-1-en-4-one;

(417) 8-{2-[2-methyl-4-(thiazolidine-3-carbonyl)-phenyl]-ethanesulfonyl}-2-(3-trifluoromethoxy-phenyl)-1,3,8-triaza-spiro[4.5]dec-1-en-4-one;

(444) 8-{2-[2-methyl-4-(3-methylamino-pyrrolidine-1-carbonyl)-phenyl]-ethanesulfonyl}-2-(3-trifluoromethyl-phenyl)-1,3,8-triaza-spiro[4.5]dec-1-en-4-one;

(445) 8-{2-[4-(3-amino-pyrrolidine-1-carbonyl)-2-methyl-phenyl]-ethanesulfonyl}-2-(3-trifluoromethyl-phenyl)-1,3,8-triaza-spiro[4.5]dec-1-en-4-one hydrochloride;

(446) 8-{(E)-2-[2,6-dimethyl-4-(piperazine-1-carbonyl)-phenyl]-ethenesulfonyl}-2-(3-trifluoromethoxy-phenyl)-1,3,8-triaza-spiro[4.5]dec-1-en-4-one hydrochloride;

(447) 8-((E)-2-{4-[4-(2-hydroxy-acetyl)-piperazine-1-carbonyl]-2,6-dimethyl-phenyl}-ethenesulfonyl)-2-(3-trifluoromethoxy-phenyl)-1,3,8-triaza-spiro[4.5]dec-1-en-4-one;

(448) 4-[4-(3,5-dimethyl-4-{(E)-2-[4-oxo-2-(3-trifluoromethoxy-phenyl)-1,3,8-triaza-spiro[4.5]dec-1-ene-8-sulfonyl]-vinyl}-benzoyl)-piperazin-1-yl]-4-oxo-butyric acid methyl ester;

(449) 8-((E)-2-{4-[4-(4-dimethylamino-butyryl)-piperazine-1-carbonyl]-2,6-dimethyl-phenyl}-ethenesulfonyl)-2-(3-trifluoromethoxy-phenyl)-1,3,8-triaza-spiro[4.5]dec-1-en-4-one;

(450) 2-methoxy-N-methyl-N-(3-methyl-4-{(E)-2-[4-oxo-2-(3-trifluoromethoxy-phenyl)-1,3,8-triaza-spiro[4.5]dec-1-ene-8-sulfonyl]-vinyl}-phenyl)-acetamide;

(451) 2-hydroxy-N-methyl-N-(3-methyl-4-{(E)-2-[4-oxo-2-(3-trifluoromethoxy-phenyl)-1,3,8-triaza-spiro[4.5]dec-1-ene-8-sulfonyl]-vinyl}-phenyl)-acetamide;

(452) [(3,5-dimethyl-4-{(E)-2-[4-oxo-2-(3-trifluoromethyl-phenyl)-1,3,8-triaza-spiro[4.5]dec-1-ene-8-sulfonyl]-vinyl}-benzoyl)-methyl-amino]-acetic acid;

(457) 3-(2-dimethylamino-ethyl)-1-methyl-1-(3-methyl-4-{(E)-2-[4-oxo-2-(3-trifluoromethoxy-phenyl)-1,3,8-triaza-spiro[4.5]dec-1-ene-8-sulfonyl]-vinyl}-phenyl)-urea;

(458) 1-methyl-1-(3-methyl-4-{(E)-2-[4-oxo-2-(3-trifluoromethoxy-phenyl)-1,3,8-triaza-spiro[4.5]dec-1-ene-8-sulfonyl]-vinyl}-phenyl)-urea;

(466) methyl-(3-methyl-4-{(E)-2-[4-oxo-2-(3-trifluoromethoxy-phenyl)-1,3,8-triaza-spiro[4.5]dec-1-ene-8-sulfonyl]-vinyl}-phenyl)-carbamic acid 2-dimethylamino-ethyl ester;

(467) methyl-(3-methyl-4-{(E)-2-[4-oxo-2-(3-trifluoromethoxy-phenyl)-1,3,8-triaza-spiro[4.5]dec-1-ene-8-sulfonyl]-vinyl}-phenyl)-carbamic acid methyl ester;

(468) methyl-(3-methyl-4-{2-[4-oxo-2-(3-trifluoromethoxy-phenyl)-1,3,8-triaza-spiro[4.5]dec-1-ene-8-sulfonyl]-ethyl}-phenyl)-carbamic acid methyl ester;

(485) 4-methyl-piperazine-1-carboxylic acid {4-[(E)-2-(2-cyclohexyl-4-oxo-1,3,8-triaza-spiro[4.5]dec-1-ene-8-sulfonyl)-vinyl]-3-trifluoromethyl-phenyl}-amide;

(491) 8-[(E)-2-(4-amino-2,6-bis-trifluoromethyl-phenyl)-ethenesulfonyl]-2-cyclohexyl-1,3,8-triaza-spiro[4.5]dec-1-en-4-one;

(493) {4-[(E)-2-(2-cyclohexyl-4-oxo-1,3,8-triaza-spiro[4.5]dec-1-ene-8-sulfonyl)-vinyl]-3-trifluoromethyl-phenylamino}-acetic acid methyl ester;

(494) 2-{4-[(E)-2-(2-cyclohexyl-4-oxo-1,3,8-triaza-spiro[4.5]dec-1-ene-8-sulfonyl)-vinyl]-3-trifluoromethyl-phenylamino}-N-(2-hydroxy-ethyl)-acetamide;

(495) 4-[(E)-2-(2-cyclohexyl-4-oxo-1,3,8-triaza-spiro[4.5]dec-1-ene-8-sulfonyl)-vinyl]-N-(2-hydroxy-ethyl)-N-methyl-3-trifluoromethyl-benzenesulfonamide;

(496) 4-[(E)-2-(2-cyclohexyl-4-oxo-1,3,8-triaza-spiro[4.5]dec-1-ene-8-sulfonyl)-vinyl]-N,N-bis-(2-hydroxy-ethyl)-3-trifluoromethyl-benzenesulfonamide;

(497) 2-cyclohexyl-8-{(E)-2-[4-(2-dimethylamino-ethylamino)-2-methyl-phenyl]-ethenesulfonyl}-1,3,8-triaza-spiro[4.5]dec-1-en-4-one;

(498) N-(2-acetylamino-ethyl)-2-{4-[(E)-2-(2-cyclohexyl-4-oxo-1,3,8-triaza-spiro[4.5]dec-1-ene-8-sulfonyl)-vinyl]-3-trifluoromethyl-phenylamino}-acetamide;

(501) 2-cyclohexyl-8-((E)-2-{4-[(2-hydroxy-ethyl)-methyl-amino]-2-trifluoromethyl-phenyl}-ethenesulfonyl)-1,3,8-triaza-spiro[4.5]dec-1-en-4-one;

(502) 2-cyclohexyl-8-{(E)-2-[4-(1,1-dioxo-1$\lambda^6$-thiomorpholine-4-carbonyl)-2-methyl-phenyl]-ethenesulfonyl}-1,3,8-triaza-spiro[4.5]dec-1-en-4-one;

(503) 4-[(E)-2-(2-cyclohexyl-4-oxo-1,3,8-triaza-spiro[4.5]dec-1-ene-8-sulfonyl)-vinyl]-N-(2-dimethylamino-ethyl)-3-methyl-benzenesulfonamide;

(525) [(S)-1-(3-methyl-4-{(E)-2-[4-oxo-2-(3-trifluoromethyl-phenyl)-1,3,8-triaza-spiro[4.5]dec-1-ene-8-sulfonyl]-vinyl}-phenyl)-2,5-dioxo-pyrrolidin-3-yl]-carbamic acid tert-butyl ester;

(527) 8-{(E)-2-[2-methyl-4-(4-methyl-piperazine-1-carbonyl)-phenyl]-ethenesulfonyl}-2-(3-trifluoromethoxy-phenyl)-1,3,8-triaza-spiro[4.5]dec-1-en-4-one;

(528) 8-((E)-2-{2-methyl-4-[2-(4-methyl-piperazin-1-yl)-2-oxo-ethylamino]-phenyl}-ethenesulfonyl)-2-(3-trifluoromethoxy-phenyl)-1,3,8-triaza-spiro[4.5]dec-1-en-4-one;

(529) 2-(3-methyl-4-{(E)-2-[4-oxo-2-(3-trifluoromethoxy-phenyl)-1,3,8-triaza-spiro[4.5]dec-1-ene-8-sulfonyl]-vinyl}-phenylamino)-acetamide;

(530) 3-methyl-4-{(E)-2-[4-oxo-2-(3-trifluoromethoxy-phenyl)-1,3,8-triaza-spiro[4.5]dec-1-ene-8-sulfonyl]-vinyl}-N-pyridin-4-yl-benzenesulfonamide;

(531) 8-{(E)-2-[4-(3,4-dihydroxy-butoxy)-2-methyl-phenyl]-ethenesulfonyl}-2-(3-trifluoromethoxy-phenyl)-1,3,8-triaza-spiro[4.5]dec-1-en-4-one;

(532) 1-(3,5-dimethyl-4-{(E)-2-[4-oxo-2-(3-trifluoromethoxy-phenyl)-1,3,8-triaza-spiro[4.5]dec-1-ene-8-sulfonyl]-vinyl}-phenyl)-1,3-bis-(2-hydroxy-ethyl)-urea;

(533) 1-(3,5-dimethyl-4-{(E)-2-[4-oxo-2-(3-trifluoromethoxy-phenyl)-1,3,8-triaza-spiro[4.5]dec-1-ene-8-sulfonyl]-vinyl}-phenyl)-1,3-bis-(2-hydroxy-ethyl)-3-methyl-urea;

(534) N-(3,5-dimethyl-4-{(E)-2-[4-oxo-2-(3-trifluoromethoxy-phenyl)-1,3,8-triaza-spiro[4.5]dec-1-ene-8-sulfonyl]-vinyl}-phenyl)-N-(tetrahydro-pyran-4-yl)-methanesulfonamide;

(535) 2-(4-fluoro-3-trifluoromethyl-phenyl)-8-{(E)-2-[4-(4-hydroxy-piperidine-1-carbonyl)-2,6-dimethyl-phenyl]-ethenesulfonyl}-1,3,8-triaza-spiro[4.5]dec-1-en-4-one;

(568) N-{4-[(E)-2-(2-cyclohexyl-4-oxo-1,3,8-triaza-spiro[4.5]dec-1-ene-8-sulfonyl)-vinyl]-3-methyl-phenyl}-N',N'-dimethyl-sulfamide;

(569) {4-[(E)-2-(2-cyclohexyl-4-oxo-1,3,8-triaza-spiro[4.5]dec-1-ene-8-sulfonyl)-vinyl]-3-methyl-benzyl}-(3-dimethylamino-propyl)-carbamic acid tert-butyl ester;

(572) 2-cyclohexyl-8-{(E)-2-[2-methyl-4-(2-oxo-azetidin-1-yl)-phenyl]-ethenesulfonyl}-1,3,8-triaza-spiro[4.5]dec-1-en-4-one;

(573) 2-cyclohexyl-8-{(E)-2-[2,6-dimethyl-4-(thiazol-2-ylamino)-phenyl]-ethenesulfonyl}-1,3,8-triaza-spiro[4.5]dec-1-en-4-one;

(574) N-{4-[(E)-2-(2-cyclohexyl-4-oxo-1,3,8-triaza-spiro[4.5]dec-1-ene-8-sulfonyl)-vinyl]-3,5-dimethyl-phenyl}-N-(3-methyl-oxetan-3-ylmethyl)-acetamide;

(590) N,N-dimethyl-2-(3-methyl-4-{(E)-2-[4-oxo-2-(3-trifluoromethyl-phenyl)-1,3,8-triaza-spiro[4.5]dec-1-ene-8-sulfonyl]-vinyl}-benzenesulfonylamino)-acetamide;

(591) 3-methyl-4-{(E)-2-[4-oxo-2-(3-trifluoromethyl-phenyl)-1,3,8-triaza-spiro[4.5]dec-1-ene-8-sulfonyl]-vinyl}-N-pyridin-3-ylmethyl-benzenesulfonamide;

(592) N-(4-hydroxy-cyclohexyl)-3-methyl-4-{(E)-2-[4-oxo-2-(3-trifluoromethyl-phenyl)-1,3,8-triaza-spiro[4.5]dec-1-ene-8-sulfonyl]-vinyl}-benzenesulfonamide;

(593) 8-[(E)-2-(4-methanesulfonyl-2-methyl-phenyl)-ethenesulfonyl]-2-(3-trifluoromethyl-phenyl)-1,3,8-triaza-spiro[4.5]dec-1-en-4-one;

(594) N-acetyl-3-methyl-4-{(E)-2-[4-oxo-2-(3-trifluoromethyl-phenyl)-1,3,8-triaza-spiro[4.5]dec-1-ene-8-sulfonyl]-vinyl}-benzenesulfonamide;

(595) N-(2-hydroxy-1,1-bis-hydroxymethyl-ethyl)-3-methyl-4-{(E)-2-[4-oxo-2-(3-trifluoromethyl-phenyl)-1,3,8-triaza-spiro[4.5]dec-1-ene-8-sulfonyl]-vinyl}-benzenesulfonamide;

(596) N-(1-benzyl-piperidin-4-yl)-3-methyl-4-{(E)-2-[4-oxo-2-(3-trifluoromethoxy-phenyl)-1,3,8-triaza-spiro[4.5]dec-1-ene-8-sulfonyl]-vinyl}-benzenesulfonamide;

(598) 8-{(E)-2-[4-(4-isopropyl-piperazine-1-carbonyl)-2-methyl-phenyl]-ethenesulfonyl}-2-(3-trifluoromethoxy-phenyl)-1,3,8-triaza-spiro[4.5]dec-1-en-4-one;

(599) N—((R)-2,3-dihydroxy-propyl)-3-methyl-4-{(E)-2-[4-oxo-2-(3-trifluoromethoxy-phenyl)-1,3,8-triaza-spiro[4.5]dec-1-ene-8-sulfonyl]-vinyl}-benzenesulfonamide;

(602) 4-(3-methyl-4-{(E)-2-[4-oxo-2-(3-trifluoromethoxy-phenyl)-1,3,8-triaza-spiro[4.5]dec-1-ene-8-sulfonyl]-vinyl}-phenoxy)-piperidine-1-carboxylic acid tert-butyl ester;

(603) N-isopropyl-N-(3-methyl-4-{(E)-2-[4-oxo-2-(3-trifluoromethoxy-phenyl)-1,3,8-triaza-spiro[4.5]dec-1-ene-8-sulfonyl]-vinyl}-phenyl)-acetamide;

(604) 4-[acetyl-(3-methyl-4-{(E)-2-[4-oxo-2-(3-trifluoromethoxy-phenyl)-1,3,8-triaza-spiro[4.5]dec-1-ene-8-sulfonyl]-vinyl}-phenyl)-amino]-piperidine-1-carboxylic acid tert-butyl ester;

(605) 1-(3,5-dimethyl-4-{(E)-2-[4-oxo-2-(3-trifluoromethoxy-phenyl)-1,3,8-triaza-spiro[4.5]dec-1-ene-8-sulfonyl]-vinyl}-phenyl)-1-(2-hydroxy-ethyl)-urea;

(606) 8-((E)-2-{4-[(R)-2-(isopropylamino-methyl)-5-oxo-pyrrolidin-1-yl]-2,6-dimethyl-phenyl}-ethenesulfonyl)-2-(3-trifluoromethoxy-phenyl)-1,3,8-triaza-spiro[4.5]dec-1-en-4-one;

(607) N-(2-dimethylamino-ethyl)-N-(3,5-dimethyl-4-{(E)-2-[4-oxo-2-(3-trifluoromethoxy-phenyl)-1,3,8-triaza-spiro[4.5]dec-1-ene-8-sulfonyl]-vinyl}-phenyl)-acetamide;

(608) 2-dimethylamino-N-(3,5-dimethyl-4-{(E)-2-[4-oxo-2-(3-trifluoromethoxy-phenyl)-1,3,8-triaza-spiro[4.5]dec-1-ene-8-sulfonyl]-vinyl}-phenyl)-N-methyl-acetamide;

(609) N-(2-dimethylamino-ethyl)-N-(3,5-dimethyl-4-{(E)-2-[4-oxo-2-(3-trifluoromethoxy-phenyl)-1,3,8-triaza-spiro[4.5]dec-1-ene-8-sulfonyl]-vinyl}-phenyl)-methanesulfonamide;

(610) N—[(R)-1-(3,5-dimethyl-4-{(E)-2-[4-oxo-2-(3-trifluoromethoxy-phenyl)-1,3,8-triaza-spiro[4.5]dec-1-ene-8-sulfonyl]-vinyl}-phenyl)-5-oxo-pyrrolidin-2-ylmethyl]-acetamide;

(611) 8-{(E)-2-[4-((R)-2-dimethylaminomethyl-5-oxo-pyrrolidin-1-yl)-2,6-dimethyl-phenyl]-ethenesulfonyl}-2-(3-trifluoromethoxy-phenyl)-1,3,8-triaza-spiro[4.5]dec-1-en-4-one;

(612) N-cyanomethyl-N-(3-methyl-4-{(E)-2-[4-oxo-2-(3-trifluoromethoxy-phenyl)-1,3,8-triaza-spiro[4.5]dec-1-ene-8-sulfonyl]-vinyl}-phenyl)-acetamide;

(613) N-(3-methyl-4-{(E)-2-[4-oxo-2-(3-trifluoromethoxy-phenyl)-1,3,8-triaza-spiro[4.5]dec-1-ene-8-sulfonyl]-vinyl}-phenyl)-N-(2,2,2-trifluoro-ethyl)-acetamide;

(614) 3-(3,5-dimethyl-4-{(E)-2-[4-oxo-2-(3-trifluoromethoxy-phenyl)-1,3,8-triaza-spiro[4.5]dec-1-ene-8-sulfonyl]-vinyl}-phenyl)-1,5,5-trimethyl-imidazolidine-2,4-dione;

(615) 3-(3,5-dimethyl-4-{(E)-2-[4-oxo-2-(3-trifluoromethoxy-phenyl)-1,3,8-triaza-spiro[4.5]dec-1-ene-8-sulfonyl]-vinyl}-phenyl)-5,5-dimethyl-imidazolidine-2,4-dione;

(616) N-(3,5-dimethyl-4-{(E)-2-[4-oxo-2-(3-trifluoromethoxy-phenyl)-1,3,8-triaza-spiro[4.5]dec-1-ene-8-sulfonyl]-vinyl}-phenyl)-N-(tetrahydro-pyran-4-yl)-acetamide;

(617) 8-{(E)-2-[2-methyl-4-(3-oxo-morpholin-4-yl)-phenyl]-ethenesulfonyl}-2-(3-trifluoromethoxy-phenyl)-1,3,8-triaza-spiro[4.5]dec-1-en-4-one;

(618) 3-(3-methyl-4-{(E)-2-[4-oxo-2-(3-trifluoromethoxy-phenyl)-1,3,8-triaza-spiro[4.5]dec-1-ene-8-sulfonyl]-vinyl}-phenyl)-imidazolidine-2,4-dione;

(619) 2-(4-fluoro-3-trifluoromethyl-phenyl)-8-{(E)-2-[2-methyl-4-(pyrrolidine-1-carbonyl)-phenyl]-ethenesulfonyl}-1,3,8-triaza-spiro[4.5]dec-1-en-4-one;

(620) 2-(4-fluoro-3-trifluoromethyl-phenyl)-8-{(E)-2-[4-((R)-2-hydroxymethyl-5-oxo-pyrrolidin-1-yl)-2-methyl-phenyl]-ethenesulfonyl}-1,3,8-triaza-spiro[4.5]dec-1-en-4-one;

(621) 2-(4-fluoro-3-trifluoromethyl-phenyl)-8-{(E)-2-[4-((S)-2-hydroxymethyl-5-oxo-pyrrolidin-1-yl)-2-methyl-phenyl]-ethenesulfonyl}-1,3,8-triaza-spiro[4.5]dec-1-en-4-one;

(635) 3-(3,5-dimethyl-4-{(E)-2-[4-oxo-2-(3-trifluoromethoxy-phenyl)-1,3,8-triaza-spiro[4.5]dec-1-ene-8-sulfonyl]-vinyl}-phenyl)-imidazolidine-2,4-dione;

(636) 3-(4-{(E)-2-[2-(4-fluoro-3-trifluoromethyl-phenyl)-4-oxo-1,3,8-triaza-spiro[4.5]dec-1-ene-8-sulfonyl]-vinyl}-3,5-dimethyl-phenyl)-imidazolidine-2,4-dione;

(639) 8-{(E)-2-[4-(3,4-dihydroxy-butoxy)-2,6-dimethyl-phenyl]-ethenesulfonyl}-2-(4-fluoro-3-trifluoromethyl-phenyl)-1,3,8-triaza-spiro[4.5]dec-1-en-4-one;

(640) (4-{(E)-2-[2-(4-fluoro-3-trifluoromethyl-phenyl)-4-oxo-1,3,8-triaza-spiro[4.5]dec-1-ene-8-sulfonyl]-vinyl}-3,5-dimethyl-phenyl)-[1,1,1-$^2H_3$]methyl-carbamic acid tert-butyl ester;

(641) 8-{(E)-2-[4-(4-fluoromethyl-4-hydroxy-piperidine-1-carbonyl)-2,6-dimethyl-phenyl]-ethenesulfonyl}-2-(4-fluoro-3-trifluoromethyl-phenyl)-1,3,8-triaza-spiro[4.5]dec-1-en-4-one;

(642) 2-(4-fluoro-3-trifluoromethyl-phenyl)-8-{(E)-2-[4-(4-hydroxy-4-methyl-piperidine-1-carbonyl)-2,6-dimethyl-phenyl]-ethenesulfonyl}-1,3,8-triaza-spiro[4.5]dec-1-en-4-one;

(644) 8-{(E)-2-[2,6-dimethyl-4-(2-oxa-7-aza-spiro[3.5]nonane-7-carbonyl)-phenyl]-ethenesulfonyl}-2-(4-fluoro-3-trifluoromethyl-phenyl)-1,3,8-triaza-spiro[4.5]dec-1-en-4-one;

(652) N-{3-cyano-4-[2-(2-cyclohexyl-4-oxo-1,3,8-triaza-spiro[4.5]dec-1-ene-8-sulfonyl)-ethyl]-phenyl}-acetamide;

(660) 2-{4-[2-(2-cyclohexyl-4-oxo-1,3,8-triaza-spiro[4.5]dec-1-ene-8-sulfonyl)-ethyl]-3-trifluoromethyl-phenylamino}-N-(4-hydroxy-butyl)-acetamide;

(661) {4-[2-(2-cyclohexyl-4-oxo-1,3,8-triaza-spiro[4.5]dec-1-ene-8-sulfonyl)-ethyl]-3-trifluoromethyl-phenyl}-carbamic acid isobutyl ester;

(662) N-{4-[2-(2-cyclohexyl-4-oxo-1,3,8-triaza-spiro[4.5]dec-1-ene-8-sulfonyl)-ethyl]-3-trifluoromethyl-phenyl}-benzamide;

(664) N-(2-{4-[2-(2-cyclohexyl-4-oxo-1,3,8-triaza-spiro[4.5]dec-1-ene-8-sulfonyl)-ethyl]-3-methyl-benzenesulfonylamino}-ethyl)-acetamide;

(665) N-(2-dimethylamino-ethyl)-2-(3-methyl-4-{2-[4-oxo-2-(3-trifluoromethoxy-phenyl)-1,3,8-triaza-spiro[4.5]dec-1-ene-8-sulfonyl]-ethyl}-phenylamino)-acetamide;

(666) 8-{2-[4-((2R,6S)-2,6-dimethyl-morpholine-4-carbonyl)-2-methyl-phenyl]-ethanesulfonyl}-2-(3-trifluoromethoxy-phenyl)-1,3,8-triaza-spiro[4.5]dec-1-en-4-one;

(667) N-(2,2,3,3,4,4,4-heptafluoro-butyl)-3-methyl-4-{2-[4-oxo-2-(3-trifluoromethyl-phenyl)-1,3,8-triaza-spiro[4.5]dec-1-ene-8-sulfonyl]-ethyl}-benzenesulfonamide;

(673) {4-[2-(2-cyclohexyl-4-oxo-1,3,8-triaza-spiro[4.5]dec-1-ene-8-sulfonyl)-ethyl]-3-methyl-benzyl}-methyl-carbamic acid tert-butyl ester;

(674) 8-(2-{4-[3-(2-hydroxy-ethyl)-2-oxo-imidazolidin-1-yl]-2-methyl-phenyl}-ethanesulfonyl)-2-(3-trifluoromethyl-phenyl)-1,3,8-triaza-spiro[4.5]dec-1-en-4-one;

(675) 2-(3-methyl-4-{2-[4-oxo-2-(3-trifluoromethoxy-phenyl)-1,3,8-triaza-spiro[4.5]dec-1-ene-8-sulfonyl]-ethyl}-benzenesulfonylamino)-acetamide;

(676) 8-{2-[4-(3,4-dihydroxy-butoxy)-2,6-dimethyl-phenyl]-ethanesulfonyl}-2-(3-trifluoromethoxy-phenyl)-1,3,8-triaza-spiro[4.5]dec-1-en-4-one;

(678) N-cyclopentyl-N-(3-methyl-4-{2-[4-oxo-2-(3-trifluoromethoxy-phenyl)-1,3,8-triaza-spiro[4.5]dec-1-ene-8-sulfonyl]-ethyl}-phenyl)-acetamide;

(681) {4-[2-(2-cyclohexyl-4-oxo-1,3,8-triaza-spiro[4.5]dec-1-ene-8-sulfonyl)-ethyl]-3-methyl-benzyl}-(2-hydroxy-ethyl)-carbamic acid tert-butyl ester;

(688) (S)-2-amino-3-hydroxy-N-(3-methyl-4-{(E)-2-[4-oxo-2-(3-trifluoromethyl-phenyl)-1,3,8-triaza-spiro[4.5]dec-1-ene-8-sulfonyl]-vinyl}-phenyl)-propionamide;

(689) N-(3,5-dimethyl-4-{(E)-2-[4-oxo-2-(3-trifluoromethoxy-phenyl)-1,3,8-triaza-spiro[4.5]dec-1-ene-8-sulfonyl]-vinyl}-phenyl)-N-piperidin-4-yl-methanesulfonamide;

(708) {4-[(E)-2-(2-cyclohexyl-4-oxo-1,3,8-triaza-spiro[4.5]dec-1-ene-8-sulfonyl)-vinyl]-3-methyl-benzyl}-(2-hydroxy-ethyl)-carbamic acid tert-butyl ester;

(709) N-{4-[(E)-2-(2-cyclohexyl-4-oxo-1,3,8-triaza-spiro[4.5]dec-1-ene-8-sulfonyl)-vinyl]-3,5-dimethyl-phenyl}-N-(4-hydroxy-cyclohexyl)-acetamide;

(710) 2-cyclohexyl-8-((E)-2-{4-[(R)-2-(2-hydroxy-ethoxymethyl)-5-oxo-pyrrolidin-1-yl]-2,6-dimethyl-phenyl}-ethenesulfonyl)-1,3,8-triaza-spiro[4.5]dec-1-en-4-one;

(711) N-(2-hydroxy-ethyl)-N-(3-methyl-4-{(E)-2-[4-oxo-2-(3-trifluoromethoxy-phenyl)-1,3,8-triaza-spiro[4.5]dec-1-ene-8-sulfonyl]-vinyl}-phenyl)-isobutylamide;

(712) 8-{(E)-2-[4-((R)-5-hydroxymethyl-3,3-dimethyl-2-oxo-pyrrolidin-1-yl)-2,6-dimethyl-phenyl]-ethenesulfonyl}-2-(3-trifluoromethoxy-phenyl)-1,3,8-triaza-spiro[4.5]dec-1-en-4-one;

(713) 8-{(E)-2-[4-((R)-5-hydroxymethyl-3-methyl-2-oxo-pyrrolidin-1-yl)-2,6-dimethyl-phenyl]-ethenesulfonyl}-2-(3-trifluoromethoxy-phenyl)-1,3,8-triaza-spiro[4.5]dec-1-en-4-one;

(714) 3-(3,5-dimethyl-4-{(E)-2-[4-oxo-2-(3-trifluoromethoxy-phenyl)-1,3,8-triaza-spiro[4.5]dec-1-ene-8-sulfonyl]-vinyl}-phenyl)-1-(2-hydroxy-ethyl)-5,5-dimethyl-imidazolidine-2,4-dione;

(715) N-(3,5-dimethyl-4-{(E)-2-[4-oxo-2-(3-trifluoromethoxy-phenyl)-1,3,8-triaza-spiro[4.5]dec-1-ene-8-sulfonyl]-vinyl}-phenyl)-N-(4-hydroxy-cyclohexyl)-methanesulfonamide;

(718) N-(4-{(E)-2-[2-(4-fluoro-3-trifluoromethyl-phenyl)-4-oxo-1,3,8-triaza-spiro[4.5]dec-1-ene-8-sulfonyl]-vinyl}-3,5-dimethyl-phenyl)-N-(2-hydroxy-ethyl)-acetamide;

(719) N-(2-hydroxy-ethyl)-N-(3-methyl-4-{(E)-2-[4-oxo-2-(3-trifluoromethoxy-phenyl)-1,3,8-triaza-spiro[4.5]dec-1-ene-8-sulfonyl]-vinyl}-phenyl)-methanesulfonamide;

(721) N-(4-{2-[2-(4-fluoro-3-trifluoromethyl-phenyl)-4-oxo-1,3,8-triaza-spiro[4.5]dec-1-ene-8-sulfonyl]-ethyl}-3-methyl-phenyl)-N-(2-hydroxy-ethyl)-acetamide;

(722) 2-hydroxy-N-(2-hydroxy-ethyl)-N-(3-methyl-4-{(E)-2-[4-oxo-2-(3-trifluoromethoxy-phenyl)-1,3,8-triaza-spiro[4.5]dec-1-ene-8-sulfonyl]-vinyl}-phenyl)-acetamide;

(729) 1-cyanomethyl-1-(3-methyl-4-{(E)-2-[4-oxo-2-(3-trifluoromethoxy-phenyl)-1,3,8-triaza-spiro[4.5]dec-1-ene-8-sulfonyl]-vinyl}-phenyl)-urea;

(730) 1-cyclopentyl-1-(3-methyl-4-{(E)-2-[4-oxo-2-(3-trifluoromethoxy-phenyl)-1,3,8-triaza-spiro[4.5]dec-1-ene-8-sulfonyl]-vinyl}-phenyl)-urea;

(731) 1-(3-methyl-4-{(E)-2-[4-oxo-2-(3-trifluoromethoxy-phenyl)-1,3,8-triaza-spiro[4.5]dec-1-ene-8-sulfonyl]-vinyl}-phenyl)-1-(2,2,2-trifluoro-ethyl)-urea;

(734) N-{4-[(E)-2-(2-cyclohexyl-4-oxo-1,3,8-triaza-spiro[4.5]dec-1-ene-8-sulfonyl)-vinyl]-3-methyl-phenyl}-N-cyclopentyl-acetamide trifluoroacetate;

(735) (S)-2-amino-N-{4-[(E)-2-(2-cyclohexyl-4-oxo-1,3,8-triaza-spiro[4.5]dec-1-ene-8-sulfonyl)-vinyl]-3,5-dimethyl-phenyl}-3-methyl-butylamide;

(738) 2-cyclohexyl-8-{(E)-2-[4-(4,5-dihydro-thiazol-2-ylamino)-2,6-dimethyl-phenyl]-ethenesulfonyl}-1,3,8-triaza-spiro[4.5]dec-1-en-4-one;

(739) 2-cyclohexyl-8-{(E)-2-[2-methyl-4-(3-methyl-oxetan-3-ylmethoxy)-phenyl]-ethenesulfonyl}-1,3,8-triaza-spiro[4.5]dec-1-en-4-one;

(742) N-(3-methyl-4-{(E)-2-[4-oxo-2-(3-trifluoromethoxy-phenyl)-1,3,8-triaza-spiro[4.5]dec-1-ene-8-sulfonyl]-vinyl}-phenyl)-sulfamide;

(743) N-(3-hydroxy-propyl)-N'-(3-methyl-4-{(E)-2-[4-oxo-2-(3-trifluoromethoxy-phenyl)-1,3,8-triaza-spiro[4.5]dec-1-ene-8-sulfonyl]-vinyl}-phenyl)-sulfamide;

(792) 3-(3-methyl-4-{2-[4-oxo-2-(3-trifluoromethoxy-phenyl)-1,3,8-triaza-spiro[4.5]dec-1-ene-8-sulfonyl]-ethyl}-phenyl)-imidazolidine-2,4-dione;

(793) 8-{2-[2-methyl-4-(3-oxo-morpholin-4-yl)-phenyl]-ethanesulfonyl}-2-(3-trifluoromethoxy-phenyl)-1,3,8-triaza-spiro[4.5]dec-1-en-4-one;

(794) N-(4-{2-[2-(4-fluoro-3-trifluoromethyl-phenyl)-4-oxo-1,3,8-triaza-spiro[4.5]dec-1-ene-8-sulfonyl]-ethyl}-3,5-dimethyl-phenyl)-N-(2-hydroxy-ethyl)-acetamide;

(797) 2-(4-fluoro-3-trifluoromethyl-phenyl)-8-{2-[4-(4-hydroxy-piperidine-1-carbonyl)-2,6-dimethyl-phenyl]-ethanesulfonyl}-1,3,8-triaza-spiro[4.5]dec-1-en-4-one;

(799) 3-(3,5-dimethyl-4-{2-[4-oxo-2-(3-trifluoromethoxy-phenyl)-1,3,8-triaza-spiro[4.5]dec-1-ene-8-sulfonyl]-ethyl}-phenyl)-imidazolidine-2,4-dione;

(800) 3-(4-{2-[2-(4-fluoro-3-trifluoromethyl-phenyl)-4-oxo-1,3,8-triaza-spiro[4.5]dec-1-ene-8-sulfonyl]-ethyl}-3,5-dimethyl-phenyl)-imidazolidine-2,4-dione;

(801) 8-{2-[4-(3,4-dihydroxy-butoxy)-2,6-dimethyl-phenyl]-ethanesulfonyl}-2-(4-fluoro-3-trifluoromethyl-phenyl)-1,3,8-triaza-spiro[4.5]dec-1-en-4-one;

(802) 8-{2-[4-(4-fluoromethyl-4-hydroxy-piperidine-1-carbonyl)-2,6-dimethyl-phenyl]-ethanesulfonyl}-2-(4-fluoro-3-trifluoromethyl-phenyl)-1,3,8-triaza-spiro[4.5]dec-1-en-4-one;

(803) 2-(4-fluoro-3-trifluoromethyl-phenyl)-8-{2-[4-(4-hydroxy-4-methyl-piperidine-1-carbonyl)-2,6-dimethyl-phenyl]-ethanesulfonyl}-1,3,8-triaza-spiro[4.5]dec-1-en-4-one;

(804) 8-{2-[2,6-dimethyl-4-(2-oxa-7-aza-spiro[3.5]nonane-7-carbonyl)-phenyl]-ethanesulfonyl}-2-(4-fluoro-3-trifluoromethyl-phenyl)-1,3,8-triaza-spiro[4.5]dec-1-en-4-one;

(831) 8-{2-[4-(4-hydroxy-4-hydroxymethyl-piperidine-1-carbonyl)-2,6-dimethyl-phenyl]-ethanesulfonyl}-2-(3-trifluoromethoxy-phenyl)-1,3,8-triaza-spiro[4.5]dec-1-en-4-one;

(841) 2-cyclohexyl-8-{2-[4-(1,1-dioxo-1$\lambda^6$-thiomorpholine-4-carbonyl)-2-methyl-phenyl]-ethanesulfonyl}-1,3,8-triaza-spiro[4.5]dec-1-en-4-one;

(842) 2-cyclohexyl-8-{2-[4-(2-dimethylamino-ethylamino)-2-methyl-phenyl]-ethanesulfonyl}-1,3,8-triaza-spiro[4.5]dec-1-en-4-one;

(843) 8-{2-[2-methyl-4-(4-methyl-piperazine-1-carbonyl)-phenyl]-ethanesulfonyl}-2-(3-trifluoromethoxy-phenyl)-1,3,8-triaza-spiro[4.5]dec-1-en-4-one;

(844) 4-[2-(2-cyclohexyl-4-oxo-1,3,8-triaza-spiro[4.5]dec-1-ene-8-sulfonyl)-ethyl]-N-(2-dimethylamino-ethyl)-3-methyl-benzenesulfonamide;

(845) 8-(2-{2-methyl-4-[2-(4-methyl-piperazin-1-yl)-2-oxo-ethylamino]-phenyl}-ethanesulfonyl)-2-(3-trifluoromethoxy-phenyl)-1,3,8-triaza-spiro[4.5]dec-1-en-4-one;

(846) 3-methyl-4-{2-[4-oxo-2-(3-trifluoromethoxy-phenyl)-1,3,8-triaza-spiro[4.5]dec-1-ene-8-sulfonyl]-ethyl}-N-pyridin-4-yl-benzenesulfonamide;

(847) 2-(3-methyl-4-{2-[4-oxo-2-(3-trifluoromethoxy-phenyl)-1,3,8-triaza-spiro[4.5]dec-1-ene-8-sulfonyl]-ethyl}-phenylamino)-acetamide;

(848) N-(1-benzyl-piperidin-4-yl)-3-methyl-4-{2-[4-oxo-2-(3-trifluoromethoxy-phenyl)-1,3,8-triaza-spiro[4.5]dec-1-ene-8-sulfonyl]-ethyl}-benzenesulfonamide;

(849) 8-{2-[4-(4-isopropyl-piperazine-1-carbonyl)-2-methyl-phenyl]-ethanesulfonyl}-2-(3-trifluoromethoxy-phenyl)-1,3,8-triaza-spiro[4.5]dec-1-en-4-one;

(851) N—((R)-2,3-dihydroxy-propyl)-3-methyl-4-{2-[4-oxo-2-(3-trifluoromethoxy-phenyl)-1,3,8-triaza-spiro[4.5]dec-1-ene-8-sulfonyl]-ethyl}-benzenesulfonamide;

(852) 3-methyl-4-{2-[4-oxo-2-(3-trifluoromethyl-phenyl)-1,3,8-triaza-spiro[4.5]dec-1-ene-8-sulfonyl]-ethyl}-N-pyridin-3-ylmethyl-benzenesulfonamide;

(853) N-(4-hydroxy-cyclohexyl)-3-methyl-4-{2-[4-oxo-2-(3-trifluoromethyl-phenyl)-1,3,8-triaza-spiro[4.5]dec-1-ene-8-sulfonyl]-ethyl}-benzenesulfonamide;

(854) N-(2-hydroxy-1,1-bis-hydroxymethyl-ethyl)-3-methyl-4-{2-[4-oxo-2-(3-trifluoromethyl-phenyl)-1,3,8-triaza-spiro[4.5]dec-1-ene-8-sulfonyl]-ethyl}-benzenesulfonamide;

(855) 8-{2-[4-(3,4-dihydroxy-butoxy)-3,5-dimethyl-phenyl]-ethanesulfonyl}-2-(3-trifluoromethoxy-phenyl)-1,3,8-triaza-spiro[4.5]dec-1-en-4-one;

(856) 2-(4-fluoro-3-trifluoromethyl-phenyl)-8-{2-[2-methyl-4-(pyrrolidine-1-carbonyl)-phenyl]-ethanesulfonyl}-1,3,8-triaza-spiro[4.5]dec-1-en-4-one;

(857) 2-(4-fluoro-3-trifluoromethyl-phenyl)-8-{2-[4-((R)-2-hydroxymethyl-5-oxo-pyrrolidin-1-yl)-2-methyl-phenyl]-ethanesulfonyl}-1,3,8-triaza-spiro[4.5]dec-1-en-4-one;

(858) 2-(4-fluoro-3-trifluoromethyl-phenyl)-8-{2-[4-((S)-2-hydroxymethyl-5-oxo-pyrrolidin-1-yl)-2-methyl-phenyl]-ethanesulfonyl}-1,3,8-triaza-spiro[4.5]dec-1-en-4-one;

(859) 4-(3-methyl-4-{2-[4-oxo-2-(3-trifluoromethoxy-phenyl)-1,3,8-triaza-spiro[4.5]dec-1-ene-8-sulfonyl]-ethyl}-phenoxy)-piperidine-1-carboxylic acid tert-butyl ester;

(861) 2-cyclohexyl-8-{2-[2-methyl-4-(2-oxo-azetidin-1-yl)-phenyl]-ethanesulfonyl}-1,3,8-triaza-spiro[4.5]dec-1-en-4-one;

(874) N-(3-methyl-4-{2-[4-oxo-2-(3-trifluoromethoxy-phenyl)-1,3,8-triaza-spiro[4.5]dec-1-ene-8-sulfonyl]-ethyl}-phenyl)-sulfamide;

(875) N-(3-hydroxy-propyl)-N'-(3-methyl-4-{2-[4-oxo-2-(3-trifluoromethoxy-phenyl)-1,3,8-triaza-spiro[4.5]dec-1-ene-8-sulfonyl]-ethyl}-phenyl)-sulfamide;

(876) 1-cyanomethyl-1-(3-methyl-4-{2-[4-oxo-2-(3-trifluoromethoxy-phenyl)-1,3,8-triaza-spiro[4.5]dec-1-ene-8-sulfonyl]-ethyl}-phenyl)-urea;

(877) 1-(3-methyl-4-{2-[4-oxo-2-(3-trifluoromethoxy-phenyl)-1,3,8-triaza-spiro[4.5]dec-1-ene-8-sulfonyl]-ethyl}-phenyl)-1-(2,2,2-trifluoro-ethyl)-urea;

(886) (S)-2-amino-3-hydroxy-N-(3-methyl-4-{2-[4-oxo-2-(3-trifluoromethyl-phenyl)-1,3,8-triaza-spiro[4.5]dec-1-ene-8-sulfonyl]-ethyl}-phenyl)-propionamide;

(889) 8-{2-[2-methyl-4-(piperidin-4-yloxy)-phenyl]-ethanesulfonyl}-2-(3-trifluoromethoxy-phenyl)-1,3,8-triaza-spiro[4.5]dec-1-en-4-one hydrochloride;

(891) 4-{2-[2-(4-methanesulfonyl-phenyl)-4-oxo-1,3,8-triaza-spiro[4.5]dec-1-ene-8-sulfonyl]-ethyl}-3,N,N-trimethyl-benzamide;

(906) N-(4-{2-[2-(4-cyano-phenyl)-4-oxo-1,3,8-triaza-spiro[4.5]dec-1-ene-8-sulfonyl]-ethyl}-3-methyl-phenyl)-acetamide;

(907) N-(4-{2-[2-(3-cyano-phenyl)-4-oxo-1,3,8-triaza-spiro[4.5]dec-1-ene-8-sulfonyl]-ethyl}-3-methyl-phenyl)-acetamide;

(908) N-(4-{2-[2-(2-cyano-phenyl)-4-oxo-1,3,8-triaza-spiro[4.5]dec-1-ene-8-sulfonyl]-ethyl}-3-methyl-phenyl)-acetamide;

(929) N-(2-hydroxy-ethyl)-N-(3-methyl-4-{2-[4-oxo-2-(3-trifluoromethoxy-phenyl)-1,3,8-triaza-spiro[4.5]dec-1-ene-8-sulfonyl]-ethyl}-phenyl)-isobutylamide;

(930) 2-hydroxy-N-(2-hydroxy-ethyl)-N-(3-methyl-4-{2-[4-oxo-2-(3-trifluoromethoxy-phenyl)-1,3,8-triaza-spiro[4.5]dec-1-ene-8-sulfonyl]-ethyl}-phenyl)-acetamide;

(935) 1-(3,5-dimethyl-4-{2-[4-oxo-2-(3-trifluoromethoxy-phenyl)-1,3,8-triaza-spiro[4.5]dec-1-ene-8-sulfonyl]-ethyl}-phenyl)-1-methyl-urea;

(958) 8-(2-{2-methyl-4-[4-(1-methyl-piperidin-4-yl)-piperazine-1-carbonyl]-phenyl}-ethanesulfonyl-2-(3-trifluoromethyl-phenyl)-1,3,8-triaza-spiro[4.5]dec-1-en-4-one;

(959) 8-{(E)-2-[4-((R)-3-fluoro-pyrrolidine-1-carbonyl)-2,6-dimethyl-phenyl]-ethenesulfonyl}-2-(3-trifluoromethoxy-phenyl)-1,3,8-triaza-spiro[4.5]dec-1-en-4-one;

(960) 8-{(E)-2-[4-(4-hydroxymethyl-piperidine-1-carbonyl)-2,6-dimethyl-phenyl]-ethenesulfonyl}-2-(3-trifluoromethoxy-phenyl)-1,3,8-triaza-spiro[4.5]dec-1-en-4-one;

(961) 3,5,N,N-tetramethyl-4-{(E)-2-[4-oxo-2-(3-trifluoromethoxy-phenyl)-1,3,8-triaza-spiro[4.5]dec-1-ene-8-sulfonyl]-vinyl}-benzamide;

(962) 3,5-dimethyl-4-{(E)-2-[4-oxo-2-(3-trifluoromethoxy-phenyl)-1,3,8-triaza-spiro[4.5]dec-1-ene-8-sulfonyl]-vinyl}-benzamide;

(963) 8-{(E)-2-[4-(3-fluoro-azetidine-1-carbonyl)-2,6-dimethyl-phenyl]-ethenesulfonyl}-2-(3-trifluoromethoxy-phenyl)-1,3,8-triaza-spiro[4.5]dec-1-en-4-one;

(964) 8-{2-[4-(4-hydroxy-piperidine-1-carbonyl)-2,6-dimethyl-phenyl]-ethanesulfonyl}-2-(3-trifluoromethoxy-phenyl)-1,3,8-triaza-spiro[4.5]dec-1-en-4-one;

(965) 8-{2-[4-(3-hydroxy-azetidine-1-carbonyl)-2,6-dimethyl-phenyl]-ethanesulfonyl}-2-(3-trifluoromethoxy-phenyl)-1,3,8-triaza-spiro[4.5]dec-1-en-4-one;

(966) 8-{2-[4-(4-hydroxymethyl-piperidine-1-carbonyl)-2,6-dimethyl-phenyl]-ethanesulfonyl}-2-(3-trifluoromethoxy-phenyl)-1,3,8-triaza-spiro[4.5]dec-1-en-4-one;

(967) 8-{(E)-2-[2,6-dimethyl-4-(2-oxa-6-aza-spiro[3.3]heptane-6-carbonyl)-phenyl]-ethenesulfonyl}-2-(4-fluoro-3-trifluoromethyl-phenyl)-1,3,8-triaza-spiro[4.5]dec-1-en-4-one;

(968) 8-{(E)-2-[2,6-dimethyl-4-(3-oxo-piperazine-1-carbonyl)-phenyl]-ethenesulfonyl}-2-(4-fluoro-3-trifluoromethyl-phenyl)-1,3,8-triaza-spiro[4.5]dec-1-en-4-one;

(969) 8-{(E)-2-[4-((3R,5S)-3,5-dimethyl-piperazine-1-carbonyl)-2,6-dimethyl-phenyl]-ethenesulfonyl}-2-(4-fluoro-3-trifluoromethyl-phenyl)-1,3,8-triaza-spiro[4.5]dec-1-en-4-one;

(970) 2-(4-fluoro-3-trifluoromethyl-phenyl)-8-{(E)-2-[4-(3-hydroxy-3-methyl-azetidine-1-carbonyl)-2,6-dimethyl-phenyl]-ethenesulfonyl}-1,3,8-triaza-spiro[4.5]dec-1-en-4-one;

(971) 2-(4-fluoro-3-trifluoromethyl-phenyl)-8-{(E)-2-[4-(4-hydroxy-4-hydroxymethyl-piperidine-1-carbonyl)-2,6-dimethyl-phenyl]-ethenesulfonyl}-1,3,8-triaza-spiro[4.5]dec-1-en-4-one;

(972) 8-{(E)-2-[2,6-dimethyl-4-(4-oxo-piperidine-1-carbonyl)-phenyl]-ethenesulfonyl}-2-(4-fluoro-3-trifluoromethyl-phenyl)-1,3,8-triaza-spiro[4.5]dec-1-en-4-one;

(1006) 2-cyclohexyl-8-{(E)-2-[4-(4-hydroxy-4-trifluoromethyl-piperidine-1-carbonyl)-2,6-dimethyl-phenyl]-ethenesulfonyl}-1,3,8-triaza-spiro[4.5]dec-1-en-4-one;

(1007) 2-cyclohexyl-8-{(E)-2-[2,6-dimethyl-4-(2-oxo-oxazolidine-3-carbonyl)-phenyl]-ethenesulfonyl}-1,3,8-triaza-spiro[4.5]dec-1-en-4-one;

(1011) 2-amino-N-(3,5-dimethyl-4-{(E)-2-[4-oxo-2-(3-trifluoromethoxy-phenyl)-1,3,8-triaza-spiro[4.5]dec-1-ene-8-sulfonyl]-vinyl}-phenyl)-N-methyl-acetamide;

(1012) (3,5-dimethyl-4-{(E)-2-[4-oxo-2-(3-trifluoromethoxy-phenyl)-1,3,8-triaza-spiro[4.5]dec-1-ene-8-sulfonyl]-vinyl}-phenyl)-methyl-carbamic acid 2-hydroxy-ethyl ester;

(1013) 1-(3,5-dimethyl-4-{(E)-2-[4-oxo-2-(3-trifluoromethoxy-phenyl)-1,3,8-triaza-spiro[4.5]dec-1-ene-8-sulfonyl]-vinyl}-phenyl)-1,3,3-trimethyl-urea;

(1014) 1-(3,5-dimethyl-4-{(E)-2-[4-oxo-2-(3-trifluoromethoxy-phenyl)-1,3,8-triaza-spiro[4.5]dec-1-ene-8-sulfonyl]-vinyl}-phenyl)-1,3-dimethyl-urea;

(1015) 1-(3,5-dimethyl-4-{(E)-2-[4-oxo-2-(3-trifluoromethoxy-phenyl)-1,3,8-triaza-spiro[4.5]dec-1-ene-8-sulfonyl]-vinyl}-phenyl)-1-methyl-urea;

(1016) 8-[(E)-2-(2,6-dimethyl-4-methylamino-phenyl)-ethenesulfonyl]-2-(3-trifluoromethylsulfanyl-phenyl)-1,3,8-triaza-spiro[4.5]dec-1-en-4-one;

(1017) 1-(4-{(E)-2-[2-(4-fluoro-3-trifluoromethyl-phenyl)-4-oxo-1,3,8-triaza-spiro[4.5]dec-1-ene-8-sulfonyl]-vinyl}-3,5-dimethyl-phenyl)-1-methyl-urea;

(1018) 1-[3,5-dimethyl-4-((E)-2-{4-oxo-2-[3-(1,1,2,2-tetrafluoro-ethoxy)-phenyl]-1,3,8-triaza-spiro[4.5]dec-1-ene-8-sulfonyl}-vinyl)-phenyl]-1-methyl-urea;

(1019) 1-[3,5-dimethyl-4-((E)-2-{4-oxo-2-[3-(4,4,4-trifluoro-butoxy)-phenyl]-1,3,8-triaza-spiro[4.5]dec-1-ene-8-sulfonyl}-vinyl)-phenyl]-1-methyl-urea;

(1020) 1-[3,5-dimethyl-4-((E)-2-{4-oxo-2-[4-(4,4,4-trifluoro-butoxy)-phenyl]-1,3,8-triaza-spiro[4.5]dec-1-ene-8-sulfonyl}-vinyl)-phenyl]-1-methyl-urea;

(1021) 1-(3,5-dimethyl-4-{(E)-2-[4-oxo-2-(4-pentyl-phenyl)-1,3,8-triaza-spiro[4.5]dec-1-ene-8-sulfonyl]-vinyl}-phenyl)-1-methyl-urea;

(1028) 1-(4-{2-[2-(4-fluoro-3-trifluoromethoxy-phenyl)-4-oxo-1,3,8-triaza-spiro[4.5]dec-1-ene-8-sulfonyl]-ethyl}-3,5-dimethyl-phenyl)-1-methyl-urea;

(1030) 1-(4-{2-[2-(4-tert-butyl-phenyl)-4-oxo-1,3,8-triaza-spiro[4.5]dec-1-ene-8-sulfonyl]-ethyl}-3,5-dimethyl-phenyl)-1-methyl-urea;

(1036) 8-[2-(2,6-dimethyl-4-methylamino-phenyl)-ethanesulfonyl]-2-(3-trifluoromethylsulfanyl-phenyl)-1,3,8-triaza-spiro[4.5]dec-1-en-4-one;

(1038) 1-[3,5-dimethyl-4-(2-{4-oxo-2-[3-(1,1,2,2-tetrafluoro-ethoxy)-phenyl]-1,3,8-triaza-spiro[4.5]dec-1-ene-8-sulfonyl}-ethyl)-phenyl]-1-methyl-urea;

(1085) 1-(4-{2,2-difluoro-2-[4-oxo-2-(3-trifluoromethoxy-phenyl)-1,3,8-triaza-spiro[4.5]dec-1-ene-8-sulfonyl]-ethyl}-3,5-dimethyl-phenyl)-1-methyl-urea;

(1087) 1-{3,5-dimethyl-4-[2-(4-oxo-2-[1,1';2',1"]terphenyl-3-yl-1,3,8-triaza-spiro[4.5]dec-1-ene-8-sulfonyl)-ethyl]-phenyl}-1-methyl-urea;

(1088) 1-[3,5-dimethyl-4-((E)-2-{4-oxo-2-[4-(4,4,4-trifluoro-butyl)-phenyl]-1,3,8-triaza-spiro[4.5]dec-1-ene-8-sulfonyl}-vinyl)-phenyl]-1-methyl-urea;

(1089) 1-[3,5-dimethyl-4-((E)-2-{4-oxo-2-[3-(4,4,4-trifluoro-butyl)-phenyl]-1,3,8-triaza-spiro[4.5]dec-1-ene-8-sulfonyl}-vinyl)-phenyl]-1-methyl-urea;

(1090) 1-(3,5-dimethyl-4-{2-[4-oxo-2-(3-trifluoromethoxy-phenyl)-1,3,8-triaza-spiro[4.5]dec-1-ene-8-sulfonyl]-propyl}-phenyl)-1-methyl-urea;

(1091) 2-[4-fluoro-3-(4,4,5,5,5-pentafluoro-pentyloxy)-phenyl]-8-{(E)-2-[4-(4-hydroxy-piperidine-1-carbonyl)-2,6-dimethyl-phenyl]-ethenesulfonyl}-1,3,8-triaza-spiro[4.5]dec-1-en-4-one;

(1092) 2-[4-fluoro-3-(4,4,5,5,5-pentafluoro-pentyloxy)-phenyl]-8-{(E)-2-[4-(4-hydroxy-4-methyl-piperidine-1-carbonyl)-2,6-dimethyl-phenyl]-ethenesulfonyl}-1,3,8-triaza-spiro[4.5]dec-1-en-4-one;

(1093) 2-(4-chloro-3-trifluoromethoxy-phenyl)-8-{(E)-2-[4-(4-hydroxy-4-methyl-piperidine-1-carbonyl)-2,6-dimethyl-phenyl]-ethenesulfonyl}-1,3,8-triaza-spiro[4.5]dec-1-en-4-one;

(1094) 2-(3-fluoro-4-trifluoromethoxy-phenyl)-8-{(E)-2-[4-(4-hydroxy-4-methyl-piperidine-1-carbonyl)-2,6-dimethyl-phenyl]-ethenesulfonyl}-1,3,8-triaza-spiro[4.5]dec-1-en-4-one;

(1095) 2-(3,4-bis-trifluoromethyl-phenyl)-8-{(E)-2-[4-(4-hydroxy-4-methyl-piperidine-1-carbonyl)-2,6-dimethyl-phenyl]-ethenesulfonyl}-1,3,8-triaza-spiro[4.5]dec-1-en-4-one;

(1096) 8-{(E)-2-[4-(4-hydroxy-4-methyl-piperidine-1-carbonyl)-2,6-dimethyl-phenyl]-ethenesulfonyl}-2-[3-(4,4,5,5,5-pentafluoro-pentyloxy)-phenyl]-1,3,8-triaza-spiro[4.5]dec-1-en-4-one;

(1097) 8-{(E)-2-[4-(4-hydroxy-4-methyl-piperidine-1-carbonyl)-2,6-dimethyl-phenyl]-ethenesulfonyl}-2-[3-(2,2,2-trifluoro-ethyl)-phenyl]-1,3,8-triaza-spiro[4.5]dec-1-en-4-one;

(1098) 2-(4-fluoro-3-methyl-phenyl)-8-{(E)-2-[4-(4-hydroxy-4-methyl-piperidine-1-carbonyl)-2,6-dimethyl-phenyl]-ethenesulfonyl}-1,3,8-triaza-spiro[4.5]dec-1-en-4-one;

(1099) 2-(4-fluoro-3-trifluoromethoxy-phenyl)-8-{(E)-2-[4-(4-hydroxy-4-methyl-piperidine-1-carbonyl)-2,6-dimethyl-phenyl]-ethenesulfonyl}-1,3,8-triaza-spiro[4.5]dec-1-en-4-one;

(1100) 8-{(E)-2-[4-(4-hydroxy-4-methyl-piperidine-1-carbonyl)-2,6-dimethyl-phenyl]-ethenesulfonyl}-2-[3-(1,1,2,2-tetrafluoro-ethoxy)-phenyl]-1,3,8-triaza-spiro[4.5]dec-1-en-4-one;

(1101) 8-{1,1-difluoro-2-[4-(4-hydroxy-piperidine-1-carbonyl)-2,6-dimethyl-phenyl]-ethanesulfonyl}-2-(3-trifluoromethoxy-phenyl)-1,3,8-triaza-spiro[4.5]dec-1-en-4-one;

(1102) 2-(4-fluoro-3-trifluoromethoxy-phenyl)-8-{(E)-2-[4-(3-hydroxy-azetidine-1-carbonyl)-2,6-dimethyl-phenyl]-ethenesulfonyl}-1,3,8-triaza-spiro[4.5]dec-1-en-4-one;

(1103) 8-{(E)-2-[4-((R)-2,3-dihydroxy-propoxy)-2,6-dimethyl-phenyl]-ethenesulfonyl}-2-[3-(4,4,5,5,5-pentafluoro-pentyloxy)-phenyl]-1,3,8-triaza-spiro[4.5]dec-1-en-4-one;

(1111) 1-(4-{(E)-2-[2-(4-fluoro-3-trifluoromethoxy-phenyl)-4-oxo-1,3,8-triaza-spiro[4.5]dec-1-ene-8-sulfonyl]-vinyl}-3,5-dimethyl-phenyl)-1-methyl-urea;

(1112) 1-(3,5-dimethyl-4-{(E)-2-[2-(3-nonafluorobutyl-phenyl)-4-oxo-1,3,8-triaza-spiro[4.5]dec-1-ene-8-sulfonyl]-vinyl}-phenyl)-1-methyl-urea;

(1113) 1-(4-{(E)-2-[2-(4-chloro-3-trifluoromethyl-phenyl)-4-oxo-1,3,8-triaza-spiro[4.5]dec-1-ene-8-sulfonyl]-vinyl}-3,5-dimethyl-phenyl)-1-methyl-urea;

(1114) 1-(3,5-dimethyl-4-{(E)-2-[4-oxo-2-(4'-propyl-biphenyl-3-yl)-1,3,8-triaza-spiro[4.5]dec-1-ene-8-sulfonyl]-vinyl}-phenyl)-1-methyl-urea;

(1116) 1-[3,5-dimethyl-4-((E)-2-{4-oxo-2-[3-(6,6,6-trifluoro-hexyl)-phenyl]-1,3,8-triaza-spiro[4.5]dec-1-ene-8-sulfonyl}-vinyl)-phenyl]-1-methyl-urea;

(1117) 1-[3,5-dimethyl-4-((E)-2-{4-oxo-2-[4-(6,6,6-trifluoro-hexyl)-phenyl]-1,3,8-triaza-spiro[4.5]dec-1-ene-8-sulfonyl}-vinyl)-phenyl]-1-methyl-urea;

(1128) 1-(4-{(E)-2-[2-(3-methoxy-4-pentyl-phenyl)-4-oxo-1,3,8-triaza-spiro[4.5]dec-1-ene-8-sulfonyl]-vinyl}-3,5-dimethyl-phenyl)-1-methyl-urea;

(1135) 1-[3,5-dimethyl-4-(2-{4-oxo-2-[3-(4,4,5,5,5-pentafluoro-pentyloxy)-phenyl]-1,3,8-triaza-spiro[4.5]dec-1-ene-8-sulfonyl}-ethyl)-phenyl]-1-methyl-urea;

(1136) 1-(3,5-dimethyl-4-{2-[4-oxo-2-(3'-propyl-biphenyl-3-yl)-1,3,8-triaza-spiro[4.5]dec-1-ene-8-sulfonyl]-ethyl}-phenyl)-1-methyl-urea;

(1139) 1-(3,5-dimethyl-4-{2-[4-oxo-2-(4-trimethylsilanyl-phenyl)-1,3,8-triaza-spiro[4.5]dec-1-ene-8-sulfonyl]-ethyl}-phenyl)-1-methyl-urea;

(1144) 1-[3,5-dimethyl-4-(2-{2-[3-(3-methyl-butyl)-phenyl]-4-oxo-1,3,8-triaza-spiro[4.5]dec-1-ene-8-sulfonyl}-ethyl)-phenyl]-1-methyl-urea;

(1150) 1-(4-{2-[2-(4-chloro-3-trifluoromethyl-phenyl)-4-oxo-1,3,8-triaza-spiro[4.5]dec-1-ene-8-sulfonyl]-ethyl}-3,5-dimethyl-phenyl)-1-methyl-urea;

(1152) 1-(3,5-dimethyl-4-{2-[4-oxo-2-(4'-propyl-biphenyl-3-yl)-1,3,8-triaza-spiro[4.5]dec-1-ene-8-sulfonyl]-ethyl}-phenyl)-1-methyl-urea;

(1155) 1-{3,5-dimethyl-4-[2-(4-oxo-2-[1,1';3',1"]terphenyl-3-yl-1,3,8-triaza-spiro[4.5]dec-1-ene-8-sulfonyl)-ethyl]-phenyl}-1-methyl-urea;

(1157) 1-{3,5-dimethyl-4-[(E)-2-(4-oxo-2-[1,1';3',1"]terphenyl-3-yl-1,3,8-triaza-spiro[4.5]dec-1-ene-8-sulfonyl)-vinyl]-phenyl}-1-methyl-urea;

(1158) 8-{(E)-2-[4-(4-hydroxy-piperidine-1-carbonyl)-2,6-dimethyl-phenyl]-ethenesulfonyl}-2-[3-(4,4,5,5,5-pentafluoro-pentyloxy)-phenyl]-1,3,8-triaza-spiro[4.5]dec-1-en-4-one;

(1159) 2-(4-fluoro-3-trifluoromethoxy-phenyl)-8-{(E)-2-[4-(4-hydroxy-piperidine-1-carbonyl)-2,6-dimethyl-phenyl]-ethenesulfonyl}-1,3,8-triaza-spiro[4.5]dec-1-en-4-one;

(1161) 2-(4-fluoro-3-trifluoromethoxy-phenyl)-8-{(E)-2-[4-(4-hydroxymethyl-piperidine-1-carbonyl)-2,6-dimethyl-phenyl]-ethenesulfonyl}-1,3,8-triaza-spiro[4.5]dec-1-en-4-one;

(1162) 2-(4-fluoro-3-trifluoromethyl-phenyl)-8-{(E)-2-[4-(4-hydroxymethyl-piperidine-1-carbonyl)-2,6-dimethyl-phenyl]-ethenesulfonyl}-1,3,8-triaza-spiro[4.5]dec-1-en-4-one;

(1164) 8-{(E)-2-[4-((R)-2,3-dihydroxy-propoxy)-2,6-dimethyl-phenyl]-ethenesulfonyl}-2-(4-fluoro-3-trifluoromethoxy-phenyl)-1,3,8-triaza-spiro[4.5]dec-1-en-4-one;

(1166) 8-{(E)-2-[4-(3,4-dihydroxy-butoxy)-2-methyl-phenyl]-ethenesulfonyl}-2-(4-fluoro-3-trifluoromethoxy-phenyl)-1,3,8-triaza-spiro[4.5]dec-1-en-4-one;

(1179) 2-cyclohexyl-8-{2-[2,6-dimethyl-4-(2-oxo-oxazolidine-3-carbonyl)-phenyl]-ethanesulfonyl}-1,3,8-triaza-spiro[4.5]dec-1-en-4-one;

(1185) 2-(3,4-dichloro-phenyl)-8-{(E)-2-[4-(4-hydroxy-4-methyl-piperidine-1-carbonyl)-2,6-dimethyl-phenyl]-ethenesulfonyl}-1,3,8-triaza-spiro[4.5]dec-1-en-4-one;

(1186) 2-(3-chloro-4-fluoro-phenyl)-8-{(E)-2-[4-(4-hydroxy-4-methyl-piperidine-1-carbonyl)-2,6-dimethyl-phenyl]-ethenesulfonyl}-1,3,8-triaza-spiro[4.5]dec-1-en-4-one;

(1187) [3-(8-{(E)-2-[4-(4-hydroxy-4-methyl-piperidine-1-carbonyl)-2,6-dimethyl-phenyl]-ethenesulfonyl}-4-oxo-1,3,8-triaza-spiro[4.5]dec-1-en-2-yl)-phenyl]-acetonitrile;

(1188) 2-(3-chloro-4-trifluoromethyl-phenyl)-8-{(E)-2-[4-(4-hydroxy-4-methyl-piperidine-1-carbonyl)-2,6-dimethyl-phenyl]-ethenesulfonyl}-1,3,8-triaza-spiro[4.5]dec-1-en-4-one;

(1189) 8-{(E)-2-[4-(4-hydroxy-4-methyl-piperidine-1-carbonyl)-2,6-dimethyl-phenyl]-ethenesulfonyl}-2-(4-pentafluorosulfanyl-phenyl)-1,3,8-triaza-spiro[4.5]dec-1-en-4-one;

(1190) 8-{(E)-2-[4-(4-hydroxy-4-methyl-piperidine-1-carbonyl)-2,6-dimethyl-phenyl]-ethenesulfonyl}-2-(3-pentafluorosulfanyl-phenyl)-1,3,8-triaza-spiro[4.5]dec-1-en-4-one;

(1191) 8-{(E)-2-[4-(4-hydroxy-4-methyl-piperidine-1-carbonyl)-2,6-dimethyl-phenyl]-ethenesulfonyl}-2-[4-(3-trifluoromethyl-phenoxymethyl)-phenyl]-1,3,8-triaza-spiro[4.5]dec-1-en-4-one;

(1192) 2-(4-fluoro-2,3-dimethyl-phenyl)-8-{(E)-2-[4-(4-hydroxy-4-methyl-piperidine-1-carbonyl)-2,6-dimethyl-phenyl]-ethenesulfonyl}-1,3,8-triaza-spiro[4.5]dec-1-en-4-one;

(1193) 8-{(E)-2-[4-(4-hydroxy-4-methyl-piperidine-1-carbonyl)-2,6-dimethyl-phenyl]-ethenesulfonyl}-2-(3-methyl-4-trifluoromethyl-phenyl)-1,3,8-triaza-spiro[4.5]dec-1-en-4-one;

(1195) 8-{(E)-2-[4-(4-hydroxy-4-methyl-piperidine-1-carbonyl)-2,6-dimethyl-phenyl]-ethenesulfonyl}-2-(4-pentafluoroethyl-phenyl)-1,3,8-triaza-spiro[4.5]dec-1-en-4-one;

(1196) 8-{(E)-2-[4-(4-hydroxy-4-methyl-piperidine-1-carbonyl)-2,6-dimethyl-phenyl]-ethenesulfonyl}-2-(3-pentafluoroethyl-phenyl)-1,3,8-triaza-spiro[4.5]dec-1-en-4-one;

(1197) 8-{(E)-2-[4-(4-hydroxy-4-methyl-piperidine-1-carbonyl)-2,6-dimethyl-phenyl]-ethenesulfonyl}-2-[4-(2,2,2-trifluoro-1,1-dimethyl-ethoxy)-3-trifluoromethyl-phenyl]-1,3,8-triaza-spiro[4.5]dec-1-en-4-one;

(1198) 8-{(E)-2-[4-(4-hydroxy-4-methyl-piperidine-1-carbonyl)-2,6-dimethyl-phenyl]-ethenesulfonyl}-2-(4-trifluoromethoxy-phenyl)-1,3,8-triaza-spiro[4.5]dec-1-en-4-one;

(1199) 8-{(E)-2-[4-(4-hydroxy-4-methyl-piperidine-1-carbonyl)-2,6-dimethyl-phenyl]-ethenesulfonyl}-2-[4-(2,2,3,3-tetrafluoro-propoxy)-3-trifluoromethyl-phenyl]-1,3,8-triaza-spiro[4.5]dec-1-en-4-one;

(1200) 8-{(E)-2-[4-(4-hydroxy-4-methyl-piperidine-1-carbonyl)-2,6-dimethyl-phenyl]-ethenesulfonyl}-2-[4-(2,2,2-trifluoro-ethoxy)-3-trifluoromethyl-phenyl]-1,3,8-triaza-spiro[4.5]dec-1-en-4-one;

(1201) 2-[3-chloro-4-(2,2,3,3-tetrafluoro-propoxy)-phenyl]-8-{(E)-2-[4-(4-hydroxy-4-methyl-piperidine-1-carbonyl)-2,6-dimethyl-phenyl]-ethenesulfonyl}-1,3,8-triaza-spiro[4.5]dec-1-en-4-one;

(1202) 8-{(E)-2-[4-(4-hydroxy-4-methyl-piperidine-1-carbonyl)-2,6-dimethyl-phenyl]-ethenesulfonyl}-2-[4-(4,4,5,5,5-pentafluoro-pentyloxy)-3-trifluoromethyl-phenyl]-1,3,8-triaza-spiro[4.5]dec-1-en-4-one;

(1203) 8-{(E)-2-[4-(4-hydroxy-4-methyl-piperidine-1-carbonyl)-2,6-dimethyl-phenyl]-ethenesulfonyl}-2-[4-(2,2,3,3,3-pentafluoro-propoxy)-3-trifluoromethyl-phenyl]-1,3,8-triaza-spiro[4.5]dec-1-en-4-one;

(1204) 8-{(E)-2-[4-(4-hydroxy-4-methyl-piperidine-1-carbonyl)-2,6-dimethyl-phenyl]-ethenesulfonyl}-2-[4-(4,4,4-trifluoro-butoxy)-3-trifluoromethyl-phenyl]-1,3,8-triaza-spiro[4.5]dec-1-en-4-one;

(1205) 8-{(E)-2-[4-(4-hydroxy-4-methyl-piperidine-1-carbonyl)-2,6-dimethyl-phenyl]-ethenesulfonyl}-2-[3-(3-trifluoromethyl-phenoxymethyl)-phenyl]-1,3,8-triaza-spiro[4.5]dec-1-en-4-one;

(1206) 2-[3-(1,1-difluoro-ethyl)-phenyl]-8-{(E)-2-[4-(4-hydroxy-4-methyl-piperidine-1-carbonyl)-2,6-dimethyl-phenyl]-ethenesulfonyl}-1,3,8-triaza-spiro[4.5]dec-1-en-4-one;

(1207) 2-[3-fluoro-4-(4,4,5,5,5-pentafluoro-pentyloxy)-phenyl]-8-{(E)-2-[4-(4-hydroxy-4-methyl-piperidine-1-carbonyl)-2,6-dimethyl-phenyl]-ethenesulfonyl}-1,3,8-triaza-spiro[4.5]dec-1-en-4-one;

(1209) 8-{(E)-2-[4-(4-hydroxy-4-methyl-piperidine-1-carbonyl)-2,6-dimethyl-phenyl]-ethenesulfonyl}-2-[3-(2,2,2-trifluoro-1,1-dimethyl-ethoxy)-4-trifluoromethyl-phenyl]-1,3,8-triaza-spiro[4.5]dec-1-en-4-one;

(1210) 2-[4-chloro-3-(2,2,2-trifluoro-1,1-dimethyl-ethoxy)-phenyl]-8-{(E)-2-[4-(4-hydroxy-4-methyl-piperidine-1-carbonyl)-2,6-dimethyl-phenyl]-ethenesulfonyl}-1,3,8-triaza-spiro[4.5]dec-1-en-4-one;

(1211) 2-(3-[1,1,2,2,3,3,4,4,4-$^2H_9$]butoxy-4-fluoro-phenyl)-8-{(E)-2-[4-(4-hydroxy-4-methyl-piperidine-1-carbonyl)-2,6-dimethyl-phenyl]-ethenesulfonyl}-1,3,8-triaza-spiro[4.5]dec-1-en-4-one;

(1213) 8-{(E)-2-[4-(4-hydroxy-4-methyl-piperidine-1-carbonyl)-2,6-dimethyl-phenyl]-ethenesulfonyl}-2-[4-(1,1,2,2-tetrafluoro-ethoxy)-phenyl]-1,3,8-triaza-spiro[4.5]dec-1-en-4-one;

(1214) 8-{(E)-2-[4-(4-hydroxy-4-methyl-piperidine-1-carbonyl)-2,6-dimethyl-phenyl]-ethenesulfonyl}-2-(3-methyl-4-trifluoromethoxy-phenyl)-1,3,8-triaza-spiro[4.5]dec-1-en-4-one;

(1215) 2-[4-fluoro-3-(3-fluoro-propoxy)-phenyl]-8-{(E)-2-[4-(4-hydroxy-4-methyl-piperidine-1-carbonyl)-2,6-dimethyl-phenyl]-ethenesulfonyl}-1,3,8-triaza-spiro[4.5]dec-1-en-4-one;

(1216) 2-[3-chloro-4-(2,2,2-trifluoro-ethoxy)-phenyl]-8-{(E)-2-[4-(4-hydroxy-4-methyl-piperidine-1-carbonyl)-2,6-dimethyl-phenyl]-ethenesulfonyl}-1,3,8-triaza-spiro[4.5]dec-1-en-4-one;

(1217) 2-(3-difluoromethyl-4-fluoro-phenyl)-8-{(E)-2-[4-(4-hydroxy-4-methyl-piperidine-1-carbonyl)-2,6-dimethyl-phenyl]-ethenesulfonyl}-1,3,8-triaza-spiro[4.5]dec-1-en-4-one;

(1218) 2-[4-fluoro-3-(4,4,4-trifluoro-butoxy)-phenyl]-8-{(E)-2-[4-(4-hydroxy-4-methyl-piperidine-1-carbonyl)-2,6-dimethyl-phenyl]-ethenesulfonyl}-1,3,8-triaza-spiro[4.5]dec-1-en-4-one;

(1219) 2-(4-difluoromethyl-3-fluoro-phenyl)-8-{(E)-2-[4-(4-hydroxy-4-methyl-piperidine-1-carbonyl)-2,6-dimethyl-phenyl]-ethenesulfonyl}-1,3,8-triaza-spiro[4.5]dec-1-en-4-one;

(1220) 2-(4-[1,1,2,2,3,3,4,4,4-$^2H_9$]butoxy-3-trifluoromethyl-phenyl)-8-{(E)-2-[4-(4-hydroxy-4-methyl-piperidine-1-carbonyl)-2,6-dimethyl-phenyl]-ethenesulfonyl}-1,3,8-triaza-spiro[4.5]dec-1-en-4-one;

(1221) 2-(4-[1,1,2,2,2-$^2H_5$]ethoxy-3-trifluoromethyl-phenyl)-8-{(E)-2-[4-(4-hydroxy-4-methyl-piperidine-1-carbonyl)-2,6-dimethyl-phenyl]-ethenesulfonyl}-1,3,8-triaza-spiro[4.5]dec-1-en-4-one;

(1222) 8-{(E)-2-[4-(4-hydroxy-4-methyl-piperidine-1-carbonyl)-2,6-dimethyl-phenyl]-ethenesulfonyl}-2-(4-[1,2,2,2,2,2,2-$^2H_7$]isopropoxy-3-trifluoromethyl-phenyl)-1,3,8-triaza-spiro[4.5]dec-1-en-4-one;

(1223) 8-{(E)-2-[4-(4-hydroxy-4-methyl-piperidine-1-carbonyl)-2,6-dimethyl-phenyl]-ethenesulfonyl}-2-[3-(2,2,3,3-tetrafluoro-propoxy)-4-trifluoromethyl-phenyl]-1,3,8-triaza-spiro[4.5]dec-1-en-4-one;

(1224) 2-(3-[1,1,2,2,2-$^2H_5$]ethoxy-4-fluoro-phenyl)-8-{(E)-2-[4-(4-hydroxy-4-methyl-piperidine-1-carbonyl)-2,6-dimethyl-phenyl]-ethenesulfonyl}-1,3,8-triaza-spiro[4.5]dec-1-en-4-one;

(1225) 2-(4-fluoro-3-[1,2,2,2,2,2,2-$^2H_7$]isopropoxy-phenyl)-8-{(E)-2-[4-(4-hydroxy-4-methyl-piperidine-1-carbonyl)-2,6-dimethyl-phenyl]-ethenesulfonyl}-1,3,8-triaza-spiro[4.5]dec-1-en-4-one;

(1226) 8-{(E)-2-[4-(4-hydroxy-4-methyl-piperidine-1-carbonyl)-2,6-dimethyl-phenyl]-ethenesulfonyl}-2-[3-(2,2,3,3-tetrafluoro-propoxy)-5-trifluoromethyl-phenyl]-1,3,8-triaza-spiro[4.5]dec-1-en-4-one;

(1227) 2-[4-chloro-3-(4,4,4-trifluoro-butoxy)-phenyl]-8-{(E)-2-[4-(4-hydroxy-4-methyl-piperidine-1-carbonyl)-2,6-dimethyl-phenyl]-ethenesulfonyl}-1,3,8-triaza-spiro[4.5]dec-1-en-4-one;

(1228) 8-{(E)-2-[4-(4-hydroxy-4-methyl-piperidine-1-carbonyl)-2,6-dimethyl-phenyl]-ethenesulfonyl}-2-[3-(2,2,3,3,3-pentafluoro-propoxy)-4-trifluoromethyl-phenyl]-1,3,8-triaza-spiro[4.5]dec-1-en-4-one;

(1229) 2-[4-chloro-3-(2,2,3,3-tetrafluoro-propoxy)-phenyl]-8-{(E)-2-[4-(4-hydroxy-4-methyl-piperidine-1-carbonyl)-2,6-dimethyl-phenyl]-ethenesulfonyl}-1,3,8-triaza-spiro[4.5]dec-1-en-4-one;

(1230) 2-[4-chloro-3-(2,2,3,3,3-pentafluoro-propoxy)-phenyl]-8-{(E)-2-[4-(4-hydroxy-4-methyl-piperidine-1-carbonyl)-2,6-dimethyl-phenyl]-ethenesulfonyl}-1,3,8-triaza-spiro[4.5]dec-1-en-4-one;

(1231) 2-(3-[1,1,2,2,3,3,4,4,4-$^2H_9$]butoxy-4-chloro-phenyl)-8-{(E)-2-[4-(4-hydroxy-4-methyl-piperidine-1-carbonyl)-2,6-dimethyl-phenyl]-ethenesulfonyl}-1,3,8-triaza-spiro[4.5]dec-1-en-4-one;

(1232) 8-{(E)-2-[4-(4-hydroxy-4-methyl-piperidine-1-carbonyl)-2,6-dimethyl-phenyl]-ethenesulfonyl}-2-[3-(4,4,4-trifluoro-butoxy)-4-trifluoromethoxy-phenyl]-1,3,8-triaza-spiro[4.5]dec-1-en-4-one;

(1233) 2-(3-[1,1,2,2,3,3,4,4,4-$^2H_9$]butoxy-5-trifluoromethyl-phenyl)-8-{(E)-2-[4-(4-hydroxy-4-methyl-piperidine-1-carbonyl)-2,6-dimethyl-phenyl]-ethenesulfonyl}-1,3,8-triaza-spiro[4.5]dec-1-en-4-one;

(1234) 8-{2-[4-(4-hydroxy-4-methyl-piperidine-1-carbonyl)-2,6-dimethyl-phenyl]-ethanesulfonyl}-2-(4-trifluoromethoxy-phenyl)-1,3,8-triaza-spiro[4.5]dec-1-en-4-one;

(1235) 8-{2-[4-(4-hydroxy-4-methyl-piperidine-1-carbonyl)-2,6-dimethyl-phenyl]-ethanesulfonyl}-2-(3-methyl-4-trifluoromethyl-phenyl)-1,3,8-triaza-spiro[4.5]dec-1-en-4-one;

(1236) 2-(3-chloro-4-trifluoromethyl-phenyl)-8-{2-[4-(4-hydroxy-4-methyl-piperidine-1-carbonyl)-2,6-dimethyl-phenyl]-ethanesulfonyl}-1,3,8-triaza-spiro[4.5]dec-1-en-4-one;

(1237) 2-(3,4-dimethyl-phenyl)-8-{(E)-2-[4-(4-hydroxy-4-methyl-piperidine-1-carbonyl)-2,6-dimethyl-phenyl]-ethenesulfonyl}-1,3,8-triaza-spiro[4.5]dec-1-en-4-one;

(1238) 8-{(E)-2-[4-(4-hydroxy-4-methyl-piperidine-1-carbonyl)-2,6-dimethyl-phenyl]-ethenesulfonyl}-2-(4-methoxy-3-methyl-phenyl)-1,3,8-triaza-spiro[4.5]dec-1-en-4-one;

(1239) 2-(4-fluoro-2,5-dimethyl-phenyl)-8-{(E)-2-[4-(4-fluoromethyl-4-hydroxy-piperidine-1-carbonyl)-2,6-dimethyl-phenyl]-ethenesulfonyl}-1,3,8-triaza-spiro[4.5]dec-1-en-4-one;

(1240) 2-(4-fluoro-2,3-dimethyl-phenyl)-8-{(E)-2-[4-(4-fluoromethyl-4-hydroxy-piperidine-1-carbonyl)-2,6-dimethyl-phenyl]-ethenesulfonyl}-1,3,8-triaza-spiro[4.5]dec-1-en-4-one;

(1241) 2-(3-chloro-4-trifluoromethyl-phenyl)-8-{(E)-2-[4-(4-fluoromethyl-4-hydroxy-piperidine-1-carbonyl)-2,6-dimethyl-phenyl]-ethenesulfonyl}-1,3,8-triaza-spiro[4.5]dec-1-en-4-one;

(1242) 2-(3-chloro-4-fluoro-phenyl)-8-{(E)-2-[4-(4-fluoromethyl-4-hydroxy-piperidine-1-carbonyl)-2,6-dimethyl-phenyl]-ethenesulfonyl}-1,3,8-triaza-spiro[4.5]dec-1-en-4-one;

(1243) 8-{(E)-2-[4-(4-fluoromethyl-4-hydroxy-piperidine-1-carbonyl)-2,6-dimethyl-phenyl]-ethenesulfonyl}-2-(3-pentafluoroethyl-phenyl)-1,3,8-triaza-spiro[4.5]dec-1-en-4-one;

(1244) 8-{(E)-2-[4-(4-fluoromethyl-4-hydroxy-piperidine-1-carbonyl)-2,6-dimethyl-phenyl]-ethenesulfonyl}-2-(4-pentafluoroethyl-phenyl)-1,3,8-triaza-spiro[4.5]dec-1-en-4-one;

(1245) 8-{(E)-2-[4-(4-fluoromethyl-4-hydroxy-piperidine-1-carbonyl)-2,6-dimethyl-phenyl]-ethenesulfonyl}-2-(4-pentafluorosulfanyl-phenyl)-1,3,8-triaza-spiro[4.5]dec-1-en-4-one;

(1246) 2-[3-chloro-4-(2,2,2-trifluoro-ethoxy)-phenyl]-8-{(E)-2-[4-(4-fluoromethyl-4-hydroxy-piperidine-1-carbonyl)-2,6-dimethyl-phenyl]-ethenesulfonyl}-1,3,8-triaza-spiro[4.5]dec-1-en-4-one;

(1247) 2-[3-chloro-4-(2,2,3,3-tetrafluoro-propoxy)-phenyl]-8-{(E)-2-[4-(4-fluoromethyl-4-hydroxy-piperidine-1-carbonyl)-2,6-dimethyl-phenyl]-ethenesulfonyl}-1,3,8-triaza-spiro[4.5]dec-1-en-4-one;

(1248) 8-{(E)-2-[4-(4-fluoromethyl-4-hydroxy-piperidine-1-carbonyl)-2,6-dimethyl-phenyl]-ethenesulfonyl}-2-[4-(2,2,2-trifluoro-ethoxy)-3-trifluoromethyl-phenyl]-1,3,8-triaza-spiro[4.5]dec-1-en-4-one;

(1249) 8-{(E)-2-[4-(4-fluoromethyl-4-hydroxy-piperidine-1-carbonyl)-2,6-dimethyl-phenyl]-ethenesulfonyl}-2-[4-(2,2,3,3,3-pentafluoro-propoxy)-3-trifluoromethyl-phenyl]-1,3,8-triaza-spiro[4.5]dec-1-en-4-one;

(1250) 8-{(E)-2-[4-(4-fluoromethyl-4-hydroxy-piperidine-1-carbonyl)-2,6-dimethyl-phenyl]-ethenesulfonyl}-2-[4-(4,4,4-trifluoro-butoxy)-3-trifluoromethyl-phenyl]-1,3,8-triaza-spiro[4.5]dec-1-en-4-one;

(1251) 8-{(E)-2-[4-(4-fluoromethyl-4-hydroxy-piperidine-1-carbonyl)-2,6-dimethyl-phenyl]-ethenesulfonyl}-2-[4-(2,2,3,3-tetrafluoro-propoxy)-3-trifluoromethyl-phenyl]-1,3,8-triaza-spiro[4.5]dec-1-en-4-one;

(1252) 8-{(E)-2-[4-(4-fluoromethyl-4-hydroxy-piperidine-1-carbonyl)-2,6-dimethyl-phenyl]-ethenesulfonyl}-2-[4-(4,4,5,5,5-pentafluoro-pentyloxy)-3-trifluoromethyl-phenyl]-1,3,8-triaza-spiro[4.5]dec-1-en-4-one;

(1253) 2-(4-[1,1,2,2,2-$^2H_5$]ethoxy-3-trifluoromethyl-phenyl)-8-{(E)-2-[4-(4-fluoromethyl-4-hydroxy-piperidine-1-carbonyl)-2,6-dimethyl-phenyl]-ethenesulfonyl}-1,3,8-triaza-spiro[4.5]dec-1-en-4-one;

(1254) 8-{(E)-2-[4-(4-fluoromethyl-4-hydroxy-piperidine-1-carbonyl)-2,6-dimethyl-phenyl]-ethenesulfonyl}-2-(3-methyl-4-trifluoromethyl-phenyl)-1,3,8-triaza-spiro[4.5]dec-1-en-4-one;

(1255) 2-(4-difluoromethyl-3-fluoro-phenyl)-8-{(E)-2-[4-(4-fluoromethyl-4-hydroxy-piperidine-1-carbonyl)-2,6-dimethyl-phenyl]-ethenesulfonyl}-1,3,8-triaza-spiro[4.5]dec-1-en-4-one;

(1256) 2-(3-difluoromethyl-4-fluoro-phenyl)-8-{(E)-2-[4-(4-fluoromethyl-4-hydroxy-piperidine-1-carbonyl)-2,6-dimethyl-phenyl]-ethenesulfonyl}-1,3,8-triaza-spiro[4.5]dec-1-en-4-one;

(1257) 2-(3,4-dichloro-phenyl)-8-{(E)-2-[4-(4-fluoromethyl-4-hydroxy-piperidine-1-carbonyl)-2,6-dimethyl-phenyl]-ethenesulfonyl}-1,3,8-triaza-spiro[4.5]dec-1-en-4-one;

(1258) 8-{(E)-2-[4-(4-fluoromethyl-4-hydroxy-piperidine-1-carbonyl)-2,6-dimethyl-phenyl]-ethenesulfonyl}-2-(3-methyl-4-trifluoromethoxy-phenyl)-1,3,8-triaza-spiro[4.5]dec-1-en-4-one;

(1259) 8-{(E)-2-[4-(4-fluoromethyl-4-hydroxy-piperidine-1-carbonyl)-2,6-dimethyl-phenyl]-ethenesulfonyl}-2-(2-methyl-4-trifluoromethyl-phenyl)-1,3,8-triaza-spiro[4.5]dec-1-en-4-one;

(1260) 8-{(E)-2-[4-(4-fluoromethyl-4-hydroxy-piperidine-1-carbonyl)-2,6-dimethyl-phenyl]-ethenesulfonyl}-2-[3-fluoro-4-(2,2,2-trifluoro-ethoxy)-phenyl]-1,3, 8-triaza-spiro[4.5]dec-1-en-4-one;

(1261) 2-(4-[1,1,2,2,3,3,4,4,4-$^2H_9$]butoxy-3-trifluoromethyl-phenyl)-8-{(E)-2-[4-(4-fluoromethyl-4-hydroxy-piperidine-1-carbonyl)-2,6-dimethyl-phenyl]-ethenesulfonyl}-1,3,8-triaza-spiro[4.5]dec-1-en-4-one;

(1262) 8-{(E)-2-[4-(4-fluoromethyl-4-hydroxy-piperidine-1-carbonyl)-2,6-dimethyl-phenyl]-ethenesulfonyl}-2-(4-[1,2,2,2,2',2',2'-$^2H_7$]isopropoxy-3-trifluoromethyl-phenyl)-1,3,8-triaza-spiro[4.5]dec-1-en-4-one;

(1263) 8-{(E)-2-[4-(4-fluoromethyl-4-hydroxy-piperidine-1-carbonyl)-2,6-dimethyl-phenyl]-ethenesulfonyl}-2-[4-fluoro-3-(4,4,5,5,5-pentafluoro-pentyloxy)-phenyl]-1,3,8-triaza-spiro[4.5]dec-1-en-4-one;

(1264) 2-[4-fluoro-3-(3-fluoro-propoxy)-phenyl]-8-{(E)-2-[4-(4-fluoromethyl-4-hydroxy-piperidine-1-carbonyl)-2,6-dimethyl-phenyl]-ethenesulfonyl}-1,3,8-triaza-spiro[4.5]dec-1-en-4-one;

(1265) 8-{(E)-2-[4-(4-fluoromethyl-4-hydroxy-piperidine-1-carbonyl)-2,6-dimethyl-phenyl]-ethenesulfonyl}-2-[4-(2,2,2-trifluoro-1,1-dimethyl-ethoxy)-3-trifluoromethyl-phenyl]-1,3,8-triaza-spiro[4.5]dec-1-en-4-one;

(1266) 8-{(E)-2-[4-(4-fluoromethyl-4-hydroxy-piperidine-1-carbonyl)-2,6-dimethyl-phenyl]-ethenesulfonyl}-2-[3-(2,2,2-trifluoro-1,1-dimethyl-ethoxy)-4-trifluoromethyl-phenyl]-1,3,8-triaza-spiro[4.5]dec-1-en-4-one;

(1267) 2-[3-(1,1-difluoro-ethyl)-phenyl]-8-{(E)-2-[4-(4-fluoromethyl-4-hydroxy-piperidine-1-carbonyl)-2,6-dimethyl-phenyl]-ethenesulfonyl}-1,3,8-triaza-spiro[4.5]dec-1-en-4-one;

(1269) 8-{(E)-2-[4-(4-fluoromethyl-4-hydroxy-piperidine-1-carbonyl)-2,6-dimethyl-phenyl]-ethenesulfonyl}-2-(4-trifluoromethoxy-phenyl)-1,3,8-triaza-spiro[4.5]dec-1-en-4-one;

(1270) 2-[4-chloro-3-(2,2,3,3,3-pentafluoro-propoxy)-phenyl]-8-{(E)-2-[4-(4-fluoromethyl-4-hydroxy-piperidine-1-carbonyl)-2,6-dimethyl-phenyl]-ethenesulfonyl}-1,3,8-triaza-spiro[4.5]dec-1-en-4-one;

(1271) 2-[4-chloro-3-(2,2,2-trifluoro-1,1-dimethyl-ethoxy)-phenyl]-8-{(E)-2-[4-(4-fluoromethyl-4-hydroxy-piperidine-1-carbonyl)-2,6-dimethyl-phenyl]-ethenesulfonyl}-1,3,8-triaza-spiro[4.5]dec-1-en-4-one;

(1272) 2-(3-[1,1,2,2,2-$^2H_5$]ethoxy-4-fluoro-phenyl)-8-{(E)-2-[4-(4-fluoromethyl-4-hydroxy-piperidine-1-carbonyl)-2,6-dimethyl-phenyl]-ethenesulfonyl}-1,3,8-triaza-spiro[4.5]dec-1-en-4-one;

(1273) 8-{(E)-2-[4-(4-fluoromethyl-4-hydroxy-piperidine-1-carbonyl)-2,6-dimethyl-phenyl]-ethenesulfonyl}-2-[3-(4,4,4-trifluoro-butoxy)-4-trifluoromethoxy-phenyl]-1,3,8-triaza-spiro[4.5]dec-1-en-4-one;

(1274) 8-{(E)-2-[4-(4-fluoromethyl-4-hydroxy-piperidine-1-carbonyl)-2,6-dimethyl-phenyl]-ethenesulfonyl}-2-[3-(2,2,3,3-tetrafluoro-propoxy)-4-trifluoromethyl-phenyl]-1,3,8-triaza-spiro[4.5]dec-1-en-4-one;

(1276) 8-{2-[4-(4-fluoromethyl-4-hydroxy-piperidine-1-carbonyl)-2,6-dimethyl-phenyl]-ethanesulfonyl}-2-(4-trifluoromethoxy-phenyl)-1,3,8-triaza-spiro[4.5]dec-1-en-4-one;

(1277) 8-{2-[4-(4-fluoromethyl-4-hydroxy-piperidine-1-carbonyl)-2,6-dimethyl-phenyl]-ethanesulfonyl}-2-(3-methyl-4-trifluoromethyl-phenyl)-1,3,8-triaza-spiro[4.5]dec-1-en-4-one;

(1278) 2-(3-chloro-4-trifluoromethyl-phenyl)-8-{2-[4-(4-fluoromethyl-4-hydroxy-piperidine-1-carbonyl)-2,6-dimethyl-phenyl]-ethanesulfonyl}-1,3,8-triaza-spiro[4.5]dec-1-en-4-one;

(1279) 8-{2-[4-(4-fluoromethyl-4-hydroxy-piperidine-1-carbonyl)-2,6-dimethyl-phenyl]-ethanesulfonyl}-2-[3-(2,2,3,3-tetrafluoro-propoxy)-4-trifluoromethyl-phenyl]-1,3,8-triaza-spiro[4.5]dec-1-en-4-one;

(1282) [3-(8-{(E)-2-[4-(4-hydroxy-piperidine-1-carbonyl)-2,6-dimethyl-phenyl]-ethenesulfonyl}-4-oxo-1,3,8-triaza-spiro[4.5]dec-1-en-2-yl)-phenyl]-acetonitrile;

(1283) 8-{(E)-2-[2-methyl-4-(piperidin-4-yloxy)-phenyl]-ethenesulfonyl}-2-(3-trifluoromethoxy-phenyl)-1,3,8-triaza-spiro[4.5]dec-1-en-4-one trifluoroacetate;

(1288) 8-[(E)-2-(2,6-dimethyl-4-[1,1,1-$^{2}H_{3}$]methylamino-phenyl)-ethenesulfonyl]-2-(4-fluoro-3-trifluoromethyl-phenyl)-1,3,8-triaza-spiro[4.5]dec-1-en-4-one hydrochloride;

(1294) N-(1-acetyl-piperidin-4-yl)-N-(3-methyl-4-{(E)-2-[4-oxo-2-(3-trifluoromethoxy-phenyl)-1,3,8-triaza-spiro[4.5]dec-1-ene-8-sulfonyl]-vinyl}-phenyl)-acetamide;

(1305) 1-(3,5-dimethyl-4-{(E)-2-[4-oxo-2-(3-trifluoromethylsulfanyl-phenyl)-1,3,8-triaza-spiro[4.5]dec-1-ene-8-sulfonyl]-vinyl}-phenyl)-1-methyl-urea;

(1306) 1-(3,5-dimethyl-4-{2-[4-oxo-2-(3-trifluoromethylsulfanyl-phenyl)-1,3,8-triaza-spiro[4.5]dec-1-ene-8-sulfonyl]-ethyl}-phenyl)-1-methyl-urea;

(1312) 1-(4-{(E)-2-[2-(4-fluoro-3-trifluoromethyl-phenyl)-4-oxo-1,3,8-triaza-spiro[4.5]dec-1-ene-8-sulfonyl]-vinyl}-3,5-dimethyl-phenyl)-1-[1,1,1-$^{2}H_{3}$]methyl-urea;

(1328) 8-{2-[4-((R)-2,3-dihydroxy-propoxy)-2,6-dimethyl-phenyl]-ethanesulfonyl}-2-[3-(4,4,5,5,5-pentafluoro-pentyloxy)-phenyl]-1,3,8-triaza-spiro[4.5]dec-1-en-4-one;

(1329) 8-{2-[4-((R)-2,3-dihydroxy-propoxy)-2,6-dimethyl-phenyl]-ethanesulfonyl}-2-(4-fluoro-3-trifluoromethoxy-phenyl)-1,3,8-triaza-spiro[4.5]dec-1-en-4-one;

(1332) 8-{2-[4-(3,4-dihydroxy-butoxy)-2-methyl-phenyl]-ethanesulfonyl}-2-(4-fluoro-3-trifluoromethoxy-phenyl)-1,3,8-triaza-spiro[4.5]dec-1-en-4-one;

(1334) 2-(4-fluoro-3-trifluoromethoxy-phenyl)-8-{2-[4-(4-hydroxy-piperidine-1-carbonyl)-2,6-dimethyl-phenyl]-ethanesulfonyl}-1,3,8-triaza-spiro[4.5]dec-1-en-4-one;

(1335) 2-(4-fluoro-3-trifluoromethoxy-phenyl)-8-{2-[4-(4-hydroxy-4-methyl-piperidine-1-carbonyl)-2,6-dimethyl-phenyl]-ethanesulfonyl}-1,3,8-triaza-spiro[4.5]dec-1-en-4-one;

(1337) 2-(4-fluoro-3-trifluoromethoxy-phenyl)-8-{2-[4-(3-hydroxy-azetidine-1-carbonyl)-2,6-dimethyl-phenyl]-ethanesulfonyl}-1,3,8-triaza-spiro[4.5]dec-1-en-4-one;

(1338) 1-[3,5-dimethyl-4-(2-{4-oxo-2-[3-(4,4,4-trifluoro-butoxy)-phenyl]-1,3,8-triaza-spiro[4.5]dec-1-ene-8-sulfonyl}-ethyl)-phenyl]-1-methyl-urea;

(1339) 1-[3,5-dimethyl-4-(2-{4-oxo-2-[4-(4,4,4-trifluoro-butoxy)-phenyl]-1,3,8-triaza-spiro[4.5]dec-1-ene-8-sulfonyl}-ethyl)-phenyl]-1-methyl-urea;

(1341) 1-(3,5-dimethyl-4-{2-[2-(3-nonafluorobutyl-phenyl)-4-oxo-1,3,8-triaza-spiro[4.5]dec-1-ene-8-sulfonyl]-ethyl}-phenyl)-1-methyl-urea;

(1342) 1-(3,5-dimethyl-4-{2-[4-oxo-2-(4-pentyl-phenyl)-1,3,8-triaza-spiro[4.5]dec-1-ene-8-sulfonyl]-ethyl}-phenyl)-1-methyl-urea;

(1345) 1-[3,5-dimethyl-4-(2-{4-oxo-2-[3-(6,6,6-trifluoro-hexyl)-phenyl]-1,3,8-triaza-spiro[4.5]dec-1-ene-8-sulfonyl}-ethyl)-phenyl]-1-methyl-urea;

(1346) 1-[3,5-dimethyl-4-(2-{4-oxo-2-[4-(6,6,6-trifluoro-hexyl)-phenyl]-1,3,8-triaza-spiro[4.5]dec-1-ene-8-sulfonyl}-ethyl)-phenyl]-1-methyl-urea;

(1354) 1-(4-{2-[2-(3-methoxy-4-pentyl-phenyl)-4-oxo-1,3,8-triaza-spiro[4.5]dec-1-ene-8-sulfonyl]-ethyl}-3,5-dimethyl-phenyl)-1-methyl-urea;

(1358) 1-[3,5-dimethyl-4-(2-{4-oxo-2-[4-(4,4,4-trifluoro-butyl)-phenyl]-1,3,8-triaza-spiro[4.5]dec-1-ene-8-sulfonyl}-ethyl)-phenyl]-1-methyl-urea;

(1359) 1-[3,5-dimethyl-4-(2-{4-oxo-2-[3-(4,4,4-trifluoro-butyl)-phenyl]-1,3,8-triaza-spiro[4.5]dec-1-ene-8-sulfonyl}-ethyl)-phenyl]-1-methyl-urea;

(1391) 1-(4-{2-[2-(4-fluoro-3-trifluoromethyl-phenyl)-4-oxo-1,3,8-triaza-spiro[4.5]dec-1-ene-8-sulfonyl]-ethyl}-3,5-dimethyl-phenyl)-1-[1,1,1-$^{2}H_{3}$]methyl-urea;

(1405) 4-{2-[2-(3-but-3-enyloxy-5-trifluoromethyl-phenyl)-4-oxo-1,3,8-triaza-spiro[4.5]dec-1-ene-8-sulfonyl]-ethyl}-3,N-dimethyl-N-pent-4-enyl-benzamide;

(1419) N-(2-allyloxy-ethyl)-4-{2-[2-(3-but-3-enyloxy-5-trifluoromethyl-phenyl)-4-oxo-1,3,8-triaza-spiro[4.5]dec-1-ene-8-sulfonyl]-ethyl}-3,N-dimethyl-benzamide;

or a pharmacologically acceptable salt thereof.

4. A pharmaceutical composition comprising the compound or a pharmacologically acceptable salt thereof according to claim 1 as an active ingredient.

5. A pharmaceutical composition for activating intracellular cAMP response, comprising the compound or a pharmacologically acceptable salt thereof according to claim 1 as an active ingredient.

* * * * *